US012410212B2

(12) United States Patent
Kawada et al.

(10) Patent No.: US 12,410,212 B2
(45) Date of Patent: Sep. 9, 2025

(54) CYCLIC COMPOUND HAVING SELECTIVE KRAS INHIBITORY EFFECT ON HRAS AND NRAS

(71) Applicant: CHUGAI SEIYAKU KABUSHIKI KAISHA, Tokyo (JP)

(72) Inventors: Hatsuo Kawada, Kamakura (JP); Koji Takano, Kamakura (JP); Tomoya Kotake, Gotemba (JP); Mirai Kage, Gotemba (JP); Satoshi Hashimoto, Gotemba (JP); Minoru Tamiya, Kamakura (JP); Yuma Wakamiya, Kamakura (JP); Ryuji Hayashi, Kamakura (JP); Yuya Morita, Kamakura (JP)

(73) Assignee: CHUGAI SEIYAKU KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 18/829,566

(22) Filed: Sep. 10, 2024

(65) Prior Publication Data
US 2025/0051394 A1 Feb. 13, 2025

Related U.S. Application Data

(63) Continuation of application No. PCT/JP2023/017112, filed on May 2, 2023.

(30) Foreign Application Priority Data

May 6, 2022 (JP) .................................. 2022-076449

(51) Int. Cl.
C07K 9/00 (2006.01)
A61K 38/12 (2006.01)
C07K 7/64 (2006.01)

(52) U.S. Cl.
CPC .............. *C07K 9/006* (2013.01); *A61K 38/12* (2013.01); *C07K 7/64* (2013.01)

(58) Field of Classification Search
None
See application file for complete search history.

(56) References Cited

U.S. PATENT DOCUMENTS

| | | | |
|---|---|---|---|
| 9,409,952 B2 | 8/2016 | Kariyuki et al. | |
| 10,815,489 B2 | 10/2020 | Ohta et al. | |
| 10,829,458 B2 | 11/2020 | Li et al. | |
| 11,492,369 B2 | 11/2022 | Nomura et al. | |
| 11,542,299 B2 | 1/2023 | Nomura et al. | |
| 11,732,002 B2 | 8/2023 | Iwaskai et al. | |
| 11,787,836 B2 | 10/2023 | Nomura et al. | |
| 11,891,457 B2 | 2/2024 | Kariyuki et al. | |
| 12,071,396 B2 | 8/2024 | Wadamoto et al. | |
| 2014/0128572 A1 | 5/2014 | Monnaie et al. | |
| 2015/0080549 A1 | 3/2015 | Kariyuki et al. | |
| 2016/0311858 A1 | 10/2016 | Kariyuki et al. | |
| 2018/0127761 A1 | 5/2018 | Ohta et al. | |
| 2019/0338050 A1 | 11/2019 | Nakano et al. | |
| 2019/0380958 A1 | 12/2019 | Tampo et al. | |
| 2020/0040372 A1 | 2/2020 | Tanaka et al. | |
| 2020/0131669 A1 | 4/2020 | Muraoka et al. | |
| 2020/0277327 A1 | 9/2020 | Nomura et al. | |
| 2020/0339623 A1 | 10/2020 | Nomura et al. | |
| 2021/0024579 A1 | 1/2021 | Shipman | |
| 2021/0061860 A1 | 3/2021 | Kariyuki et al. | |
| 2021/0087572 A1 | 3/2021 | Ohta et al. | |
| 2022/0017456 A1 | 1/2022 | Ishizawa | |
| 2022/0024972 A1 | 1/2022 | Iwasaki et al. | |
| 2022/0096379 A1 | 3/2022 | Tampo et al. | |
| 2022/0144762 A1 | 5/2022 | Wadamoto et al. | |
| 2022/0205009 A1 | 6/2022 | Shinohara et al. | |
| 2022/0411462 A1 | 12/2022 | Hou et al. | |
| 2023/0026641 A1 | 1/2023 | Nomura et al. | |
| 2023/0056969 A1 | 2/2023 | Kondo et al. | |
| 2023/0096766 A1 | 3/2023 | Muraoka et al. | |
| 2023/0108274 A1 | 4/2023 | Kagotani et al. | |
| 2023/0138226 A1 | 5/2023 | Nomura et al. | |
| 2023/0151060 A1 | 5/2023 | Tanada et al. | |
| 2023/0295221 A1 | 9/2023 | Iwasaki et al. | |
| 2023/0303619 A1 | 9/2023 | Iwasaki et al. | |
| 2023/0391818 A1 | 12/2023 | Nomura et al. | |
| 2023/0406879 A1 | 12/2023 | Nomura et al. | |
| 2024/0052340 A1 | 2/2024 | Nishimura et al. | |
| 2024/0067674 A1 | 2/2024 | Sekita et al. | |
| 2024/0124517 A1 | 4/2024 | Morita et al. | |
| 2024/0148821 A1 | 5/2024 | Tanada et al. | |
| 2024/0158446 A1 | 5/2024 | Kawada et al. | |
| 2024/0166689 A1 | 5/2024 | Kariyuki et al. | |

(Continued)

FOREIGN PATENT DOCUMENTS

| | | |
|---|---|---|
| EP | 2813512 A1 | 12/2014 |
| EP | 3636807 A1 | 4/2020 |

(Continued)

OTHER PUBLICATIONS

Bockus, A. T., et al., "Form and Function in Cyclic Peptide Natural Products: A Pharmacokinetic Perspective," Curr Topics Med Chem., 13:821-836 (2013).
Cox, A. D., et al., "Drugging the undruggable RAS: Mission Possible?," Nat Rev Drug Discov., 13(11):828-851 (2014).
Das, M. and Himaja, M. ,"Design, Synthesis and Biological Evaluation of Linear Tetrapepide D-Ala-L-(Gly-Val-Val) (AGVV)," UJPB, 01(02):21-24 (2013).
Eggen, I. F., et al., "A novel method for repetitive peptide synthesis in solution without isolation of intermediates," J Pep Sci., 11:633-641 (2005).
Gracia, S. R., et al., "Synthesis of chemically modified bioactive peptides: recent advances, challenges and developments for medicinal chemistry," Future Med Chem., 1(7):1289-1310 (2009).

(Continued)

*Primary Examiner* — Christina Bradley
(74) *Attorney, Agent, or Firm* — Nixon & Vanderhye P.C.

(57) ABSTRACT

Cyclic compounds that selectively inhibit KRAS were found. Moreover, cyclic compounds were found to interact with an amino acid residue specific to KRAS.

24 Claims, No Drawings
Specification includes a Sequence Listing.

(56) References Cited

U.S. PATENT DOCUMENTS

| | | |
|---|---|---|
| 2024/0239842 A1 | 7/2024 | Hayashi et al. |
| 2024/0366711 A1 | 11/2024 | Ueto et al. |
| 2024/0376044 A1 | 11/2024 | Wadamoto |

FOREIGN PATENT DOCUMENTS

| | | | |
|---|---|---|---|
| EP | 3896056 A1 | 10/2021 | |
| EP | 4043478 A1 | 8/2022 | |
| EP | 4309741 A1 | 1/2024 | |
| EP | 4316503 A1 | 2/2024 | |
| WO | WO2012122059 A1 | 9/2012 | |
| WO | WO2013100132 A1 | 7/2013 | |
| WO | WO2016144635 A1 | 9/2016 | |
| WO | WO2016148044 A1 | 9/2016 | |
| WO | WO2017150732 A1 | 9/2017 | |
| WO | WO2017181061 A1 | 10/2017 | |
| WO | WO2018124162 A1 | 7/2018 | |
| WO | WO2018143145 A1 | 8/2018 | |
| WO | WO2018217651 A1 | 11/2018 | |
| WO | WO2018225851 A1 | 12/2018 | |
| WO | WO2018225864 A1 | 12/2018 | |
| WO | WO2019099524 A1 | 5/2019 | |
| WO | WO2019117274 A1 | 6/2019 | |
| WO | WO2020095983 A1 | 5/2020 | |
| WO | WO2020111238 A1 | 6/2020 | |
| WO | WO2020122182 A1 | 6/2020 | |
| WO | WO2020138336 A1 | 7/2020 | |
| WO | WO2020189540 A1 | 9/2020 | |
| WO | WO-2021090855 A1 * | 5/2021 | ............. A61K 38/12 |
| WO | WO2021090856 A1 | 5/2021 | |
| WO | WO2021132545 A1 | 7/2021 | |
| WO | WO2021132546 A1 | 7/2021 | |
| WO | WO2021246471 A1 | 12/2021 | |
| WO | WO2021261577 A1 | 12/2021 | |
| WO | WO2022097540 A1 | 5/2022 | |
| WO | WO2022138891 A1 | 6/2022 | |
| WO | WO2022145444 A1 | 7/2022 | |
| WO | WO2022234850 A1 | 11/2022 | |
| WO | WO2022234851 A1 | 11/2022 | |
| WO | WO-2022234852 A1 * | 11/2022 | ............. A61K 38/12 |
| WO | WO-2022234853 A1 * | 11/2022 | ............. A61K 38/12 |
| WO | WO2023127869 A1 | 7/2023 | |
| WO | WO2023140329 A1 | 7/2023 | |
| WO | WO2023214577 A1 | 11/2023 | |

OTHER PUBLICATIONS

Isidro-Llobet, A., et al., "Amino Acid-protecting Groups," Chemical Reviews, 109(6):2455-2504 (2009).
Lambert, J.N., et al., "The synthesis of cyclic peptides," J Chem Soc, Perkin Trans., 1:471- 484 (2001).
Niida, A., et al., "Investigation of the Structural Requirements of K-ras(G12d) Selective Inhibitory Peptide Krpep-2d Using Alanine Scans and Cysteine Bridging," Bioorganic & Medicinal Chemistry Letters, 27(12):2757-2761 (2017).
Ostrem, J. M. L. and Shokat, K. M., "Direct small-molecule inhibitors of KRAS: from structural insights to mechanism-based design," Nat Rev Drug Discov., 15(11):771-785 (2016).
Sakamoto, K., et al., "K-Ras(G12D)-selective inhibitory peptides generated by random peptide T7 phage display technology," Biochem Biophys Res Comm., 484:605-611 (2017).
Samatar, A. A. and Poulikakos, P. I., "Targeting RAS-ERK signaling in cancer: promises and challenges," Nat Rev Drug Discov., 13:928-942 (2014).
Sogabe, S., et al., "Crystal Structure of a Human K-Ras G12D Mutant in Complex with GDP and the Cyclic Inhibitory Peptide KRpep-2D," ACS Med Chem Lett., 8:732-736 (2017).
Upadhyaya, P., et al., "Direct Ras inhibitors identified from a structurally rigidified bicyclic peptide library," Tetrahedron, 70:7714-7720 (2014).
U.S. Appl. No. 14/368,564, filed Jun. 25, 2014, Kariyuki et al., related application.
U.S. Appl. No. 15/166,550, filed May 27, 2016, Kariyuki et al., related application.
U.S. Appl. No. 15/557,532, filed Sep. 12, 2017, Ohta et al., related application.
U.S. Appl. No. 16/081,522, filed Jul. 8, 2019, Nakano et al., related application.
U.S. Appl. No. 16/471,837, filed Jun. 20, 2019, Tampo et al., related application.
U.S. Appl. No. 16/479,736, filed Jul. 22, 2019, Tanaka et al., related application.
U.S. Appl. No. 16/619,014, filed Dec. 3, 2019, Muraoka et al., related application.
U.S. Appl. No. 16/619,388, filed Dec. 4, 2019, Nomura et al., related application.
U.S. Appl. No. 16/771,335, filed Jun. 10, 2020, Nomura et al., related application.
U.S. Appl. No. 17/011,815, filed Sep. 3, 2020, Kariyuki et al., related application.
U.S. Appl. No. 17/024,944, filed Sep. 18, 2020, Ohta et al., related application.
U.S. Appl. No. 17/291,099, filed Jun. 3, 2021, Ishizawa, related application.
U.S. Appl. No. 17/297,231, filed May 26, 2021, Iwasaki et al., related application.
U.S. Appl. No. 17/312,296, filed Jun. 9, 2021, Muraoka et al., related application.
U.S. Appl. No. 17/417,822, filed Jun. 24, 2021, Shinohara et al., related application.
U.S. Appl. No. 17/437,535, filed Sep. 9, 2021, Wadamoto et al., related application.
U.S. Appl. No. 17/502,525, filed Oct. 15, 2021, Tampo et al., related application.
U.S. Appl. No. 17/738,283, filed May 6, 2022, Hou et al., related application.
U.S. Appl. No. 17/773,733, filed May 2, 2022, Tanada et al., related application.
U.S. Appl. No. 17/773,734, filed May 2, 2022, Nomura et al., related application.
U.S. Appl. No. 17/787,809, filed Jun. 21, 2022, Kagotani et al., related application.
U.S. Appl. No. 17/788,506, filed Jun. 23, 2022, Kondo et al., related application.
U.S. Appl. No. 17/928,759, filed Nov. 30, 2022, Iwasaki et al., related application.
U.S. Appl. No. 17/976,942, filed Oct. 31, 2022, Nomura et al., related application.
U.S. Appl. No. 18/010,608, filed Dec. 15, 2022, Nishimura et al., related application.
U.S. Appl. No. 18/034,424, filed Apr. 28, 2023, Nomura et al., related application.
U.S. Appl. No. 18/203,371, filed May 30, 2023, Iwasaki et al., related application.
U.S. Appl. No. 18/268,737, filed Jun. 21, 2023, Morita et al., related application.
U.S. Appl. No. 18/269,334, filed Jun. 23, 2023, Sekita et al., related application.
U.S. Appl. No. 18/289,071, filed Oct. 31, 2023, Hayashi et al., related application.
U.S. Appl. No. 18/289,392, filed Nov. 3, 2023, Ueto et al., related application.
U.S. Appl. No. 18/289,451, filed Nov. 3, 2023, Tanada et al., related application.
U.S. Appl. No. 18/289,592, filed Nov. 6, 2023, Kawada et al., related application.
U.S. Appl. No. 18/459,998, filed Sep. 1, 2023, Nomura et al., related application.
U.S. Appl. No. 18/460,300, filed Sep. 1, 2023, Kariyuki et al., related application.
U.S. Appl. No. 18/723,993, filed Jun. 25, 2024, Komiya et al., related application.
U.S. Appl. No. 18/728,922, filed Jul. 15, 2024, Sase et al., related application.

(56) References Cited

OTHER PUBLICATIONS

U.S. Appl. No. 18/773,066, filed Jul. 15, 2024, Tanada et al., related application.
U.S. Appl. No. 18/781,112, filed Jul. 23, 2024, Wadamoto, related application.
U.S. Appl. No. 18/860,859, filed Oct. 28, 2024, Kage et al., related application.

* cited by examiner

CYCLIC COMPOUND HAVING SELECTIVE KRAS INHIBITORY EFFECT ON HRAS AND NRAS

CROSS-REFERENCE TO RELATED APPLICATIONS

This application is a continuation of PCT Application No. PCT/JP2023/017112, filed May 2, 2023, which claims the benefit of Japanese Patent Application No. 2022-076449, filed May 6, 2022, each of which is incorporated herein by reference in its entirety.

REFERENCE TO SEQUENCE LISTING SUBMITTED ELECTRONICALLY

The content of the electronically submitted sequence listing (Name: 6663_0310 Sequence_Listing.xml; Size: 3.94 KB; and Date of Creation: Sep. 9, 2024) filed with the application is incorporated herein by reference in its entirety.

TECHNICAL FIELD

The present invention in one aspect relates to cyclic compounds.

BACKGROUND ART

RAS is a protein belonging to the small GTPase family, and KRAS, NRAS, and HRAS are known. RAS is in an active state or an inactive state according to whether it is bound to GTP or GDP. It is activated by the exchange reaction from GDP to GTP by GEFs (guanine nucleotide exchange factors) and inactivated by the hydrolysis reaction of GTP by GAPs (GTPase-activating proteins)(NPL 1). Activated RAS induces cell proliferation, survival, and differentiation by activating various downstream signals in the MAPK pathway, PI3K/Akt pathway, RAL pathway, and such, and the constitutive activation of RAS plays an important role in the development and progression of cancer. In cancer, it is known that the RAS-RAF-MEK-ERK pathway is activated by the activation of an upstream signal of RAS, constitutive activation of RAS, and/or activating mutations of RAS (NPL 2). These activating mutations of RAS have been found in numerous cancer types. G12, G13, and Q61 are known as hot spots of RAS mutation, and G12 is frequently found mutated in KRAS and Q61 in NRAS. These mutations are also known to be associated with the prognosis of patients (NPL 3).

Meanwhile, when it comes to access to a tough target, as typified by inhibition of a protein-protein interaction, medium sized molecules (having a molecular weight of 500 to 2000 g/mol) may be superior to low molecular weight compounds. Also, medium sized molecules may be superior to antibodies in that they can migrate into cells. Among biologically active medium sized molecules, peptide drugs are highly valuable molecular species, with more than 40 peptide drugs being already commercially available (NPL 4). Representative examples of such peptide drugs include cyclosporin A and polymyxin B, which are peptides containing some non-natural amino acids. A non-natural amino acid refers to an amino acid that is not naturally encoded on mRNA. It is highly interesting that non-natural amino acids are contained in naturally-occurring cyclosporin A and polymyxin B.

Since the discovery of the pharmaceutical utility of naturally-occurring peptides, peptides having pharmacological activity and bioabsorbability have been attracting attention, and those having a molecular weight of about 500 to 2000 g/mol have been actively researched (NPL 5).

There is a report on conditions for medium molecular weight peptides to have increased membrane permeability and metabolic stability, which may contribute to improving their biokinetics (conditions necessary for satisfying drug-likeness)(PTL 1). Moreover, as for the conditions that may contribute to improving the biokinetics of medium molecular weight peptides, conditions necessary for cyclic peptides to satisfy drug-likeness have been shown (PTL 2).

Peptides that bind to RAS have been found, and the binding site between a cyclic peptide and RAS has been studied by X-ray structural analysis (NPL 6, NPL 7, and NPL 8). Also, cyclic peptides that apparently inhibit binding between RAS and SOS have been found (PTL 3). Moreover, a competition assay for binding with RAS has suggested that some cyclic peptides inhibit binding between a particular compound and RAS (PTL 4).

Citation List

Patent Literature

[PTL 1] WO 2013/100132
[PTL 2] WO 2018/225864
[PTL 3] WO 2012/122059
[PTL 4] WO 2017/181061

Non-Patent Literature

[NPL 1] Nat. Rev. Drug Discov. 2014 Nov.; 13 (11): 828-851.
[NPL 2] Nat. Rev. Drug Discov. 2014 Dec.; 13 (12): 928-942.
[NPL 3] Nat. Rev. Drug Discov. 2016 Nov.; 15 (11): 771-785.
[NPL 4] Future Med. Chem. 2009, 1, 1289-1310.
[NPL 5] Current Topics in Medicinal Chemistry, 2013, Vol. 13, No. 7, 821-836.
[NPL 6] Biochem. Biophys. Res. Commun. 2017, 484, 605-611.
[NPL 7] Bioorg. Med. Chem. Lett. 2017, 27, 2757-2761.
[NPL 8] ACS Med. Chem. Lett. 2017, 8, 732-736.

SUMMARY OF INVENTION

Technical Problem

The present invention relates to cyclic compounds effective for RAS-mutant cancer and non-natural amino acids and peptide compounds useful for the production thereof.

PTL 1 and PTL 2 describe drug-like peptides, but do not describe a peptide having an antitumor effect on cancers including RAS-mutant cancer.

PTL 3 describes the inhibition of binding between RAS and SOS, and PTL 4 describes a peptide competing with a compound that binds to RAS. However, none of these documents shows any pharmacological action, especially action on tumor cells. These documents do not describe drug-like peptides, either.

NPL 1 shows the relationship between RAS and cancer in detail. This document describes molecules that bind to RAS. Although their efficacy was shown in preclinical studies, no compound was shown to be effective as a drug specifically on RAS-mutant cancer. Also, no drug-like cyclic peptide is disclosed.

NPL 2 provides detailed descriptions about RAS and the RAF-MEK-ERK pathway, which is downstream of RAS. Although this document suggests the possibility of treating RAS-mutant cancer with RAF, MEK, and ERK inhibitors, it does not show any compound that directly inhibits RAS.

NPL 3 describes a compound that binds to the GTP/GDP binding site of RAS and inhibits the function of RAS, and the mechanism thereof. This document describes the interaction with the GTP/GDP binding site in detail, but does not show pharmacological action, especially action on tumor cells.

NPL 4 describes peptides that are used as drugs, but does not describe a drug-like peptide or a peptide useful for RAS-mutant cancer.

NPL 5 describes the molecular form and pharmacokinetics of cyclic peptides, but does not describe a compound useful for RAS-mutant cancer.

NPLs 6 to 8 describe peptides that bind to RAS, but their action on tumor cells is limited, and, in addition, a drug-like peptide is not described.

Moreover, to the present inventors' knowledge, there is no report of a compound having sufficiently selective inhibitory action on KRAS over HRAS and NRAS.

Solution to Problem

As a result of dedicated research to search for cyclic compounds having selective inhibitory action on KRAS over HRAS and NRAS, the present inventors found cyclic compounds that interact with KRAS selectively as compared to HRAS and NRAS. In addition, the inventors found that the cyclic compounds have pharmacological action of inhibiting the growth of tumor cells having a RAS mutation.

In a specific non-limiting embodiment, the present invention encompasses the following:

A cyclic compound represented by formula (1):

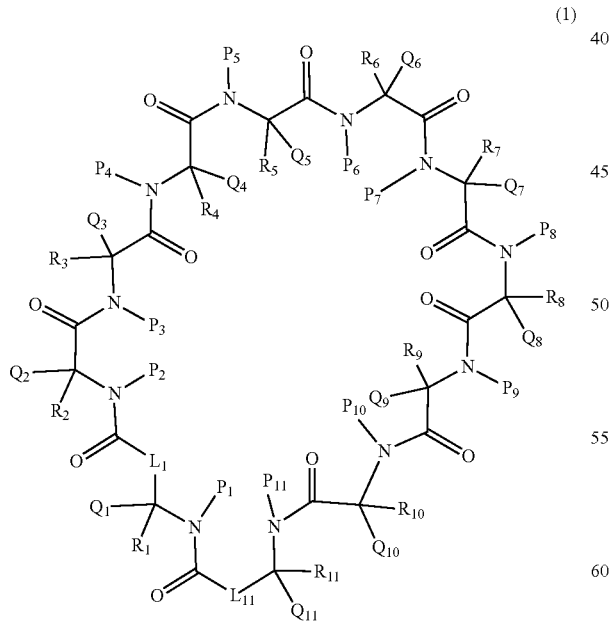

(1)

wherein
$L_1$ is a single bond;
$R_1$ is a $C_1$ to $C_7$ alkyl, or $R_1$ joins together with $R_5$ to form a divalent group, wherein a partial structure: *-$CR_1Q_1$-$L_1$-CO—$NP_2$-$CR_2Q_2$-CO—$NP_3$-$CR_3Q_3$—CO—$NP_4$-$CR_4Q_4$—CO—$NP_5$-$CR_5Q_5$-* in the cyclic compound represented by formula (1) is represented by the following formula:

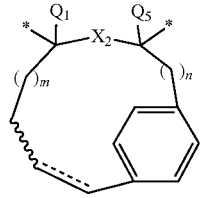

wherein:
$X_2$ is —Li—CO—$NP_2$-$CR_2Q_2$-CO—$NP_3$-$CR_3Q_3$—CO—$NP_4$-$CR_4Q_4$—CO—$NP_5$—, ==== is a single bond or a double bond, ~~~~ may take E or Z configuration, if ==== is a double bond, n is 0, 1 or 2,
m is 0, 1, 2, 3 or 4,
represents an attachment point to an adjacent atom;
$P_1$ is a $C_1$ to $C_6$ alkyl;
$Q_1$ is a hydrogen atom;
$R_2$ is a $C_1$ to $C_6$ alkyl;
$P_2$ is a hydrogen atom;
$Q_2$ is a hydrogen atom;
$R_3$ is a hydrogen atom or $R_3$ joins together with a carbon atom to which $P_3$ and $R_3$ are attached and a nitrogen atom to which $P_3$ is attached, to form a 4 to 7-membered saturated heterocycle;
$P_3$ is a $C_1$ to $C_6$ alkyl or a $C_3$ to $C_8$ cycloalkyl except the case where $R_3$ and $P_3$ form a 4 to 7-membered saturated heterocycle;
$Q_3$ is a hydrogen atom;
$R_4$ joins together with $P_5$ to form a divalent group, wherein a partial structure *-$CR_4Q_4$-CO—$NP_5$—* in the cyclic compound represented by formula (1) is represented by the following formula:

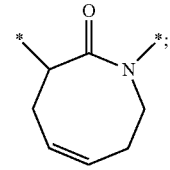

$P_4$ is a $C_1$ to $C_6$ alkyl;
$Q_4$ is a hydrogen atom,
$R_5$ is a benzyl optionally substituted with one or more groups selected from the group consisting of a $C_1$ to $C_6$ alkyl, a $C_1$ to $C_6$ haloalkyl, and a $C_3$ to $C_8$ cycloalkyl except the case where $R_1$ and $R_5$ form a divalent group;
$Q_5$ is a hydrogen atom,
$R_6$ is a hydrogen atom;
$P_6$ is a $C_1$ to $C_6$ alkyl,
$Q_6$ is a hydrogen atom,
$R_7$ is a phenethyl optionally substituted with one or more groups selected from the group consisting of a halogen atom, a $C_1$ to $C_6$ haloalkyl and a $C_1$ to $C_6$ alkoxy;

P₇ is a hydrogen atom,

Q₇ is a hydrogen atom,

R₈ joins together with a carbon atom to which P₈ and R₈ are attached and a nitrogen atom to which P₈ is attached, to form a 4 to 7-membered saturated heterocycle, wherein the 4 to 7-membered saturated heterocycle is optionally substituted with a $C_1$ to $C_6$ alkoxy;

Q₈ is a hydrogen atom,

R₉ joins together with Q₉ and a carbon atom to which R₉ and Q₉ are attached to form a 3 to 8-membered alicyclic ring, wherein the 3 to 8-membered alicyclic ring is optionally substituted with one or more $C_1$ to $C_6$ alkyls;

P₉ is a hydrogen atom or a $C_1$ to $C_6$ alkyl,

R₁₀ is a $C_1$ to $C_6$ alkyl or a $C_3$ to $C_8$ cycloalkyl;

P₁₀ is a $C_1$ to $C_6$ alkyl,

Q₁₀ is a hydrogen atom, and

L₁₁ is —CH₂—,

R₁₁ is a di-$C_1$ to $C_6$ alkylaminocarbonyl or a 4 to 8-membered cyclic aminocarbonyl;

P₁₁ is a $C_1$ to $C_6$ alkyl, and

Q₁₁ is a hydrogen atom, or a salt thereof, or a solvate thereof, wherein the cyclic compound represented by formula (1) is selected from the group consisting of:

PP1574: (2S,8S,12R,14S,20S,23S,27S,30S,36S,38Z)-20-cyclopentyl-8-[2-[3,5-difluoro-4-(trifluoromethyl)phenyl]ethyl]-12-ethoxy-N-ethyl-27-isobutyl-N,4,19,22,26,32,35-heptamethyl-30-[(1 S)-1-methylpropyl]-3,6,9,15,18,21,25,28,31,34,42-undecaoxo-2-[[4-(trifluoromethyl)phenyl]methyl]spiro[1,4,7,10,16,19,22,26,29,32,35-undecazatricyclo[34.5.1.0¹⁰,¹⁴]dotetracont-38-ene-17,1'-cyclopentane]-23-carboxamide, PP1650: (2S,8S,12R,14S,20S,23S,27S,30S,36S,38Z)-20-cyclopentyl-8-[2-[3,5-difluoro-4-(trifluoromethyl)phenyl]ethyl]-12-ethoxy-27-isobutyl-N,N,3',3',4,19,22,26,32,35-decamethyl-30-[(1 S)-1-methylpropyl]-3,6,9,15,18,21,25,28,31,34,42-undecaoxo-2-[[4-(trifluoromethyl)phenyl]methyl]spiro[1,4,7,10,16,19,22,26,29,32,35-undecazatricyclo[34.5.1.0¹⁰,¹⁴]dotetracont-38-ene-17,1'-cyclobutane]-23-carboxamide, PP1827: (1S,7S,11R,13S,19S,22S,26S,29S,35S,37Z,47E)-19-cyclopentyl-7-[2-[3,5-difluoro-4-(trifluoromethyl)phenyl]ethyl]-11-ethoxy-N-ethyl-N,3,18,21,25,31,34-heptamethyl-29-[(1 S)-1-methylpropyl]-2,5,8,14,17,20,24,27,30,33,55-undecaoxo-spiro[3,6,9,15,18,21,25,28,31,34,41-undecazapentacyclo[24.15.11.2⁴³,⁴⁶.1³⁵,⁴¹.0⁹,¹³]pentapentaconta-37,43(54),44,46(53),47-pentaene-16,1'-cyclobutane]-22-carboxamide, PP1830: (1S,7S,11R,13S,19S,22S,26S,29S,35S,37Z,47E)-19-cyclopentyl-11-ethoxy-N-ethyl-7-[2-[3-methoxy-4-(tfifluoromethyl)phenyl]ethyl]-N,3,3',3',18,21,25,31,34-nonamethyl-29-[(1S)-1-methylpropyl]-2,5,8,14,17,20,24,27,30,33,55-undecaoxo-spiro[3,6,9,15,18,21,25,28,31,34,41-undecazapentacyclo[24.15.11.2⁴³,⁴⁶.1³⁵,⁴¹.0⁹,¹³]pentapentaconta-37,43(54),44,46(53),47-pentaene-16,1'-cyclobutane]-22-carboxamide, PP2093: (2S,8S,12R,14S,20S,23S,27S,30S,36S,38Z)-20-cyclopentyl-32-cyclopropyl-8-[2-[3,5-difluoro-4-(trifluoromethyl)phenyl]ethyl]-12-ethoxy-N,N,3',3',4,19,22,26,35-nonamethyl-30-[(1 S)-1-methylpropyl]-3,6,9,15,18,21,25,28,31,34,42-undecaoxo-27-propyl-2-(p-tolylmethyl)spiro[1,4,7,10,16,19,22,26,29,32,35-undecazatricyclo[34.5.1.0¹⁰,¹⁴]dotetracont-38-ene-17,1'-cyclobutane]-23-carboxamide, PP2260: (1S,7S,11R,13S,19S,22S,26S,29S,35S,37Z)-19-cyclopentyl-11-ethoxy-N-ethyl-7-[2-[3-methoxy-4-(trifluoromethyl)phenyl]ethyl]-N,3,3',3',18,21,25,31,34-nonamethyl-29-[(1 S)-1-methylpropyl]-2,5,8,14,17,20,24,27,30,33,55-undecaoxo-spiro[3,6,9,15,18,21,25,28,31,34,41-undecazapentacyclo[24.15.11.2⁴³,⁴⁶.1³⁵,⁴¹.0⁹,¹³]pentapentaconta-37,43(54),44,46(53)-tetraene-16,1'-cyclobutane]-22-carboxamide, PP2316: (2S,8S, 12R, 14S,20S,23S,27S,30S,36S,38Z)-20-cyclopentyl-32-cyclopropyl-12-ethoxy-8-[2-[3-methoxy-4-(trifluoromethyl)phenyl]ethyl]-N,N,4,16,19,22,26,35-octamethyl-30-[(1 S)-1-methylpropyl]-3,6,9,15,18,21,25,28,31,34,42-undecaoxo-27-propyl-2-[[4-(trifluoromethyl)phenyl]methyl]spiro[1,4,7,10,16,19,22,26,29,32,35-undecazatricyclo[34.5.1.0¹⁰,¹⁴]dotetracont-38-ene-17,1'-cyclobutane]-23-carboxamide, PP2320: (1S,4S,10S,13S,17S,20S,26S,28R,32S,38S,42Z)-20-cyclopentyl-28-ethoxy-32-[2-[3-methoxy-4-(trifluoromethyl)phenyl]ethyl]-N, N, 2,14,18,21, 24,36-octamethyl-10-[(1 S)-1-methylpropyl]-3,9,12,15,19,22,25,31,34,37,45-undecaoxo-13-propyl-38-[[4-(trifluoromethyl)phenyl]methyl]spiro[2,8,11,14,18,21,24,30,33,36,39-undecazatetracyclo[37.5.1.0⁴,⁸.0²⁶,³⁰]pentatetracont-42-ene-23,1'-cyclobutane]-17-carboxamide, PP2328: (2S,8S,12R,14S,20S,23S,27S,30S,36S,38Z)-20-cyclopentyl-32-cyclopropyl-12-ethoxy-8-[2-[3-methoxy-4-(trifluoromethyl)phenyl]ethyl]-N,N,4,16,19,22,26,35-octamethyl-30-[(1 S)-1-methylpropyl]-3,6,9,15,18,21,25,28,31,34,42-undecaoxo-27-propyl-2-(p-tolylmethyl)spiro[1,4,7,10,16,19,22,26,29,32,35-undecazatricyclo[34.5.1.0¹⁰,¹⁴]dotetracont-38-ene-17,1'-cyclobutane]-23-carboxamide, PP2574: (1S,7S,11R,13S,19S,22S,26S,29S,35S,37Z,47E)-19-cyclopentyl-7-[2-[3,5-difluoro-4-(trifluoromethyl)phenyl]ethyl]-11-ethoxy-3,3',3',18,21,25,31,34-octamethyl-29-[(1 S)-1-methylpropyl]-22-(pyrrolidine-1-carbonyl)spiro[3,6,9,15,18,21,25,28,31,34,41-undecazapentacyclo[24.15.10.2⁴³,⁴⁶.1³⁵,⁴¹.0⁹,¹³]tetrapentaconta-37,43(53),44,46(52),47-pentaene-16,1'-cyclobutane]-2,5,8,14,17,20,24,27,30,33,54-undecone, PP2576: (1S,7S,11R,13S,19S,22S,26S,29S,35S,37Z,47E)-7-[2-[3,5-difluoro-4-(trifluoromethyl)phenyl]ethyl]-11-ethoxy-19-(1-ethylpropyl)-3,3',3',18,21,25,31,34-octamethyl-29-[(1 S)-1-methylpropyl]-22-(pyrrolidine-1-carbonyl)spiro[3,6,9,15,18,21,25,28,31,34,41-undecazapentacyclo[24.15.10.2⁴³,⁴⁶.1³⁵,⁴¹.0⁹,¹³]tetrapentaconta-37,43(53),44,46(52),47-pentaene-16,1'-cyclobutane]-2,5,8,14,17,20,24,27,30,33,54-undecone, PP2583: (1S,7S,11R,13S,19S,22S,26S,29S,35S,37Z,47E)-19-cyclopentyl-31-cyclopropyl-7-[2-[3,5-difluoro-4-(trifluoromethyl)phenyl]ethyl]-11-ethoxy-3,3',3',18,21,25,34-heptamethyl-29-[(1 S)-1-methylpropyl]-22-(pyrrolidine-1-carbonyl)spiro[3,6,9,15,18,21,25,28,31,34,41-undecazapentacyclo[24.15.10.2⁴³,⁴⁶.1³⁵,⁴¹.0⁹,¹³]tetrapentaconta-37,43(53),44,46(52),47-pentaene-16,1'-cyclobutane]-2,5,8,14,17,20,24,27,30,33,54-undecone, PP2687: (2S,8S,12R,14S,20S,23S,27S,30S,36S,38Z)-20-cyclopentyl-12-ethoxy-2-[(4-ethylphenyl)methyl]-27-isobutyl-8-[2-[3-methoxy-4-(trifluoromethyl)phenyl]ethyl]-N,N,3',3',4,19,22,26,32,35-decamethyl-30-[(1S)-1-methylpropyl]-3,6,9,15,18,21,25,28,31,34,42-undecaoxo-spiro[1,4,7,10,16,19,22,26,29,32,35-undecazatricyclo[34.5.1.0¹⁰,¹⁴]dotetracont-38-ene-17,1'-cyclobutane]-23-carboxamide, PP2691: (2S,8S,12R,14S,20S,23S,27S,30S,36S,38Z)-20-cyclopentyl-2-[(4-cyclopropylphenyl)methyl]-12-ethoxy-27-isobutyl-8-[2-[3-methoxy-4-(trifluoromethyl)phenyl]ethyl]-N,N,3',3',4,19,22,26,32,35-decamethyl-30-[(1 S)-1-methylpropyl]-3,6,9,15,18,21,25,28,31,34,42-undecaoxo-spiro[1,4,7,10,16,19,22,26,29,32,35-undecazatricyclo[34.5.1.0$^{10,14}$]dotetracont-38-ene-17,1'-cyclobutane]-23-carboxamide, PP2957: (1S,7S,11R,13S,19S,22S,26S,29S,35S,37Z,47E)-31-cyclopropyl-7-[2-[3,5-difluoro-4-(trifluoromethyl)phenyl]ethyl]-11-ethoxy-19-(1-ethylpropyl)-3,18,21,25,34-pentamethyl-29-[(1 S)-1-methylpropyl]-22-(pyrrolidine-1-carbonyl)spiro[3,6,9,15,18,21,25,28,31,34,41-undecazapentacyclo[24.15.10.2$^{43,46}$.1$^{35,41}$.0$^{9,13}$]tetrapentaconta-37,43(53),44,46(52),47-pentaene-16,1'-cyclobutane]-2,5,8,14,17,20,24,27,30,33,54-undecone, PP3033: (1S,7S,11R,13S,19S,22S,26S,29S,35S,37Z)-19-cyclopentyl-11-ethoxy-7-[2-[3-methoxy-4-(trifluoromethyl)phenyl]ethyl]-3,18,21,25,31,34-hexamethyl-29-[(1 S)-1-methylpropyl]-22-(piperidine-1-carbonyl)spiro[3,6,9,15,18,21,25,28,31,34,41-undecazapentacyclo[24.15.11.2$^{43,46}$.1$^{35,41}$.0$^{9,13}$]pentapentaconta-37,43(54),44,46(53)-tetraene-16,1'-cyclobutane]-2,5,8,14,17,20,24,27,30,33,55-undecone, PP3034: (1S,7S,11R,13S,19S,22S,26S,29S,35S,37Z)-19-cyclopentyl-11-ethoxy-7-[2-[3-methoxy-4-(trifluoromethyl)phenyl]ethyl]-3,3',3',18,21,25,31,34-octamethyl-29-[(1S)-1-methylpropyl]-22-(pyrrolidine-1-carbonyl)spiro[3,6,9,15,18,21,25,28,31,34,41-undecazapentacyclo[24.15.11.2$^{43,46}$.1$^{35,41}$.0$^{9,13}$]pentapentaconta-37,43(54),44,46(53)-tetraene-16,1'-cyclobutane]-2,5,8,14,17,20,24,27,30,33,55-undecone, PP3036: (1S,7S,11R,13S,19S,22S,26S,29S,35S,37Z)-19-cyclopentyl-11-ethoxy-7-[2-[3-methoxy-4-(trifluoromethyl)phenyl]ethyl]-3,3',3',18,21,25,31,34-octamethyl-294(1S)-1-methylpropyl]-22-(piperidine-1-carbonyl)spiro[3,6,9,15,18,21,25,28,31,34,41-undecazapentacyclo[24.15.10.2$^{43,46}$.1$^{35,41}$.0$^{9,13}$]tetrapentaconta-37,43(53),44,46(52)-tetraene-16,1'-cyclobutane]-2,5,8,14,17,20,24,27,30,33,54-undecone, PP3037: (1S,7S,11R,13S,19S,22S,26S,29S,35S,37Z)-19-cyclopentyl-11-ethoxy-7-[2-[3-methoxy-4-(trifluoromethyl)phenyl]ethyl]-3,3',3',18,21,25,31,34-octamethyl-29-[(1S)-1-methylpropyl]-22-(pyrrolidine-1-carbonyl)spiro[3,6,9,15,18,21,25,28,31,34,41-undecazapentacyclo[24.15.10.2$^{43,46}$.1$^{35,41}$.0$^{9,13}$]tetrapentaconta-37,43(53),44,46(52)-tetraene-16,1'-cyclobutane]-2,5,8,14,17,20,24,27,30,33,54-undecone, PP3047: (1S,7S,IIR,13S,19S,22S,26S,29S,35S,37Z,47E)-7-[2-(3,4-dichlorophenyl)ethyl]-11-ethoxy-19-(I-ethylpropyl)-3,18,21,25,31,34-hexamethyl-29-[(1S)-1-methylpropyl]-22-(pyrrolidine-1-carbonyl)spiro[3,6,9,15,18,21,25,28,31,34,41-undecazapentacyclo[24.15.11.2$^{43,46}$.1$^{35,41}$.0$^{9,13}$]pentapentaconta-37,43(54),44,46(53),47-pentaene-16,1'-cyclobutane]-2,5,8,14,17,20,24,27,30,33,55-undecone, PP3093: (1S,7S,11R,13S,19S,22S,26S,29S,35S,37Z)-19-cyclopentyl-11-ethoxy-7-[2-[3-methoxy-4-(trifluoromethyl)phenyl]ethyl]-3,3',3',18,21,25,31,34-octamethyl-29-[(1S)-1-methylpropyl]-22-(piperidine-1-carbonyl)spiro[3,6,9,15,18,21,25,28,31,34,41-undecazapentacyclo[24.15.9.2$^{43,46}$.1$^{35,41}$.0$^{9,13}$]tripentaconta-37,43(52),44,46(51)-tetraene-16,1'-cyclobutane]-2,5,8,14,17,20,24,27,30,33,53-undecone, PP3094: (1S,7S,11R,13S,19S,22S,26S,29S,35S,37Z)-19-cyclopentyl-7-[2-[3-methoxy-4-(trifluoromethyl)phenyl]ethyl]-3,3',3',18,21,25,31,34-octamethyl-29-[(1 S)-1-methylpropyl]-11-propoxy-22-(pyrrolidine-1-carbonyl)spiro[3,6,9,15,18,21,25,28,31,34,41-undecazapentacyclo[24.15.9.2$^{43,46}$.1$^{35,41}$.0$^{9,13}$]tripentaconta-37,43(52),44,46(51)-tetraene-16,1'-cyclobutane]-2,5,8,14,17,20,24,27,30,33,53-undecone, PP3095: (2S,8S,12R,14S,20S,23S,27S,30S,36S,38Z)-20-cyclopentyl-32-cyclopropyl-12-ethoxy-8-[2-[3-methoxy-4-(trifluoromethyl)phenyl]ethyl]-4,16,19,22,26,35-hexamethyl-30-[(1S)-1-methylpropyl]-23-(piperidine-1-carbonyl)-27-propyl-2-[[4-(trifluoromethyl)phenyl]methyl]spiro[1,4,7,10,16,19,22,26,29,32,35-undecazatricyclo[34.5.1.0$^{10,14}$]dotetracont-38-ene-17,1'-cyclobutane]-3,6,9,15,18,21,25,28,31,34,42-undecone, PP3096: (2S,8S,12R,14S,20S,23S,27S,30S,36S,38Z)-20-cyclopentyl-32-cyclopropyl-12-ethoxy-8-[2-[3-methoxy-4-(trifluoromethyl)phenyl]ethyl]-4,16,19,22,26,35-hexamethyl-30-[(1S)-1-methylpropyl]-23-(piperidine-1-carbonyl)-27-propyl-2-(p-tolylmethyl)spiro[1,4,7,10,16,19,22,26,29,32,35-undecazatricyclo[34.5.1.0$^{10,14}$]dotetracont-38-ene-17,1-cyclobutane]-3,6,9,15,18,21,25,28,31,34,42-undecone, PP3097: (2S,8S,12R,14S,20S,23S,27S,30S,36S,38Z)-20-cyclopentyl-32-cyclopropyl-12-ethoxy-8-[2-[3-methoxy-4-(trifluoromethyl)phenyl]ethyl]-4,16,19,22,26,35-hexamethyl-30-[(1S)-1-methylpropyl]-27-propyl-23-(pyrrolidine-1-carbonyl)-2-[[4-(trifluoromethyl)phenyl]methyl]spiro[1,4,7,10,16,19,22,26,29,32,35-undecazatricyclo[34.5.1.0$^{10,14}$]dotetracont-38-ene-17,1'-cyclobutane]-3,6,9,15,18,21,25,28,31,34,42-undecone, PP3098: (2S,8S,12R,14S,20S,23S,27S,30S,36S,38Z)-20-cyclopentyl-32-cyclopropyl-12-ethoxy-8-[2-[3-methoxy-4-(trifluoromethyl)phenyl]ethyl]-4,16,19,22,26,35-hexamethyl-30-[(1S)-1-methylpropyl]-27-propyl-2-(p-tolylmethyl)-23-(pyrrolidine-l-carbonyl)spiro[1,4,7,10,16,19,22,26,29,32,35-undecazatricyclo[34.5.1.0$^{10,14}$]dotetracont-38-ene-17,1-cyclobutane]-3,6,9,15,18,21,25,28,31,34,42-undecone, PP3099: (1S,4S,10S,13S,17S,20S,26S,28R,32S,38S,42Z)-20-cyclopentyl-28-ethoxy-32-[2-[3-methoxy-4-(trifluoromethyl)phenyl]ethyl]-2,14,18,21,24,36-hexamethyl-10-[(1 S)-1-methylpropyl]-17-(piperidine-1-carbonyl)-13-propyl-38-[[4-(trifluoromethyl)phenyl]methyl]spiro[2,8,11,14,18,21,24,30,33,36,39-undecazatetracyclo[37.5.1.0$^{4,8}$.0$^{26,30}$]pentatetracont-42-ene-23,1'-cyclobutane]-3,9,12,15,19,22,25,31,34,37,45-undecone, PP3100: (1S,4S,1OS,13S,17S,20S,26S,28R,32S,38S,42Z)-20-cyclopentyl-28-ethoxy-32-[2-[3-methoxy-4-(trifluoromethyl)phenyl]ethyl]-2,14,18,21,24,36-hexamethyl-10-[(1 S)-1-methylpropyl]-17-(piperidine-1-carbonyl)-13-propyl-38-(p-tolylmethyl)spiro[2,8,11,14,18,21,24,30,33,36,39-undecazatetracyclo[37.5.1.0$^{4,8}$.0$^{26,30}$]pentatetracont-42-ene-23,1'-cyclobutane]-3,9,12,15,19,22,25,31,34,37,45-undecone, PP3101: (1S,4S,1OS,13S,17S,20S,26S,28R,32S,38S,42Z)-20-cyclopentyl-28-ethoxy-32-[2-[3-methoxy-4-(trifluoromethyl)phenyl]ethyl]-2,14,18,21,24,36-hexamethyl-10-[(1 S)-1-methylpropyl]-13-propyl-17-(pyrrolidine-1-carbonyl)-38-[[4-(trifluoromethyl)phenyl]methyl]spiro[2,8,11,14,18,21,24,30,33,36,39-undecazatetracyclo[37.5.1.0$^{4,8}$.0$^{26,30}$]pentatetracont-42-ene-23,1'-cyclobutane]-3,9,12,15,19,22,25,31,34,37,45-undecone, PP3102: (1S,4S,10S,13S,17S,20S,26S,28R,32S,38S,42Z)-20-cyclopentyl-28-ethoxy-32-[2-[3-methoxy-4-(trifluoromethyl)phenyl]ethyl]-2,14,18,21,24,36-hexamethyl-10-[(1 S)-1-methylpropyl]-13-propyl-38-(p-tolylmethyl)-17-(pyrrolidine-l-carbonyl)spiro[2,8,11,14,18,21,24,30,33,36,39-undecazatetracyclo[37.5.1.0$^{4,8}$.0$^{26,30}$]pentatetracont-42-ene-23,1'-cyclobutane]-3,9,12,15,19,22,25,31,34,37,45-undecone, PP3103: (2S,8S,12R,14S,20S,23S,27S,30S,36S,38Z)-20-cyclopentyl-12-ethoxy-8-[2-[3-methoxy-4-(trifluoromethyl)phenyl]ethyl]-4,16,19,22,26,32,35-heptamethyl-30-

[(1 S)-1-methylpropyl]-23-(piperidine-1-carbonyl)-27-propyl-2-[[4-(trifluoromethyl)phenyl]methyl]spiro[1,4,7,10,16,19,22,26,29,32,35-undecazatricyclo[34.5.1.0$^{10,14}$]dotetracont-38-ene-17,1'-cyclobutane]-3,6,9,15,18,21,25,28,31,34,42-undecone, PP3104: (2S,8S,12R,14S,20S,23S,27S,30S,36S,38Z)-20-cyclopentyl-12-ethoxy-8-[2-[3-methoxy-4-(trifluoromethyl)phenyl]ethyl]-4,16,19,22,26,32,35-heptamethyl-30-[(1S)-1-methylpropyl]-23-(piperidine-l-carbonyl)-27-propyl-2-(p-tolylmethyl)spiro[1,4,7,10,16,19,22,26,29,32,35-undecazatricyclo[34.5.1.0$^{10,14}$]dotetracont-38-ene-17,1-cyclobutane]-3,6,9,15,18,21,25,28,31,34,42-undecone, PP3105: (2S,8S,12R,14S,20S,23S,27S,30S,36S,38Z)-20-cyclopentyl-12-ethoxy-8-[2-[3-methoxy-4-(trifluoromethyl)phenyl]ethyl]-4,16,19,22,26,32,35-heptamethyl-30-[(1 S)-1-methylpropyl]-27-propyl-23-(pyrrolidine-1-carbonyl)-2-[[4-(trifluoromethyl)phenyl]methyl]spiro[1,4,7,10,16,19,22,26,29,32,35-undecazatricyclo[34.5.1.0$^{10,14}$]dotetracont-38-ene-17,1'-cyclobutane]-3,6,9,15,18,21,25,28,31,34,42-undecone, PP3106: (2S,8S,12R,14S,20S,23S,27S,30S,36S,38Z)-20-cyclopentyl-12-ethoxy-8-[2-[3-methoxy-4-(trifluoromethyl)phenyl]ethyl]-4,16,19,22,26,32,35-heptamethyl-30-[(1S)-1-methylpropyl]-27-propyl-2-(p-tolylmethyl)-23-(pyrrolidine-l-carbonyl)spiro[1,4,7,10,16,19,22,26,29,32,35-undecazatricyclo[34.5.1.0$^{10,14}$]dotetracont-38-ene-17,1-cyclobutane]-3,6,9,15,18,21,25,28,31,34,42-undecone, PP3110: (2S,8S,12R,14S,20S,23S,27S,30S,36S,38Z)-20-cyclopentyl-32-cyclopropyl-8-[2-[3,5-difluoro-4-(trifluoromethyl)phenyl]ethyl]-12-ethoxy-4,16,19,22,26,35-hexamethyl-30-11(1S)- 1-methylpropyl]-23-(piperidine-l-carbonyl)-27-propyl-2-11114-(trifluoromethyl)phenyl]methyl]spiro[1,4,7,10,16,19,22,26,29,32,35-undecazatricyclo[34.5.1.0$^{10,14}$]dotetracont-38-ene-17,1'-cyclobutane]-3,6,9,15,18,21,25,28,31,34,42-undecone, PP3111: (2S,8S,12R,14S,20S,23S,27S,30S,36S,38Z)-20-cyclopentyl-32-cyclopropyl-8-[2-[3,5-difluoro-4-(trifluoromethyl)phenyl]ethyl]-12-ethoxy-4,16,19,22,26,35-hexamethyl-30-[(1 S)-1-methylpropyl]-23-(piperidine-l-carbonyl)-27-propyl-2-(p-tolylmethyl)spiro[[1,4,7,10,16,19,22,26,29,32,35-undecazatricyclo[34.5.1.0$^{10,14}$]dotetracont-38-ene-17,1-cyclobutane]-3,6,9,15,18,21,25,28,31,34,42-undecone, PP3112: (2S,8S,12R,14S,20S,23S,27S,30S,36S,38Z)-20-cyclopentyl-32-cyclopropyl-8-[2-[3,5-difluoro-4-(trifluoromethyl)phenyl]ethyl]-12-ethoxy-4,16,19,22,26,35-hexamethyl-30-[(1 S)-1-methylpropyl]-27-propyl-23-(pyrrolidine-1-carbonyl)-2-[[4-(trifluoromethyl)phenyl]methyl]spiro[1,4,7,10,16,19,22,26,29,32,35-undecazatricyclo[34.5.1.0$^{10,14}$]dotetracont-38-ene-17,1'-cyclobutane]-3,6,9,15,18,21,25,28,31,34,42-undecone, PP3113: (2S,8S,12R,14S,20S,23S,27S,30S,36S,38Z)-20-cyclopentyl-32-cyclopropyl-8-[2-[3,5-difluoro-4-(trifluoromethyl)phenyl]ethyl]-12-ethoxy-4,16,19,22,26,35-hexamethyl-30-[(1 S)-1-methylpropyl]-27-propyl-2-(p-tolylmethyl)-23-(pyrrolidine-l-carbonyl)spiro[1,4,7,10,16,19,22,26,29,32,35-undecazatric clo[34.5.1.0$^{10,14}$]dotetracont-38-ene-17,1-cyclobutane]-3,6,9,15,18,21,25,28,31,34,42-undecone, PP3114: (1S,4S,10S,13S,17S,20S,26S,28R,32S,38S,42Z)-20-cyclopentyl-32-[2-[3,5-difluoro-4-(trifluoromethyl)phenyl]ethyl]-28-ethoxy-2,14,18,21,24,36-hexamethyl-10-[(1 S)-1-methylpropyl]-17-(piperidine-1-carbonyl)-13-propyl-38-[[4-(trifluoromethyl)phenyl]methyl]spiro[2,8,11,14,18,21,24,30,33,36,39-undecazatetracyclo[37.5.1.0$^{4,8}$.0$^{26,30}$]pentatetracont-42-ene-23,1'-cyclobutane]-3,9,12,15,19,22,25,31,34,37,45-undecone, PP3115: (1S,4S,1OS,13S,17S,20S,26S,28R,32S,38S,42Z)-20-cyclopentyl-32-[2-[3,5-difluoro-4-(trifluoromethyl)phenyl]ethyl]-28-ethoxy-2,14,18,21,24,36-hexamethyl-10-[(1 S)-1-methylpropyl]-17-(piperidine-1-carbonyl)-13-propyl-38-(p-tolylmethyl)spiro[2,8,11,14,18,21,24,30,33,36,39-undecazatetracyclo[37.5.1.0$^{4,8}$.0$^{26,30}$]pentatetracont-42-ene-23,1'-cyclobutane]-3,9,12,15,19,22,25,31,34,37,45-undecone, PP3116: (1S,4S,1OS,13S,17S,20S,26S,28R,32S,38S,42Z)-20-cyclopentyl-32-[2-[3,5-difluoro-4-(trifluoromethyl)phenyl]ethyl]-28-ethoxy-2,14,18,21,24,36-hexamethyl-10-[(1 S)-1-methylpropyl]-13-propyl-17-(pyrrolidine-1-carbonyl)-38-[[4-(trifluoromethyl)phenyl]methyl]spiro[2,8,11,14,18,21,24,30,33,36,39-undecazatetracyclo[37.5.1.0$^{4,8}$.0$^{26,30}$]pentatetracont-42-ene-23,1'-cyclobutane]-3,9,12,15,19,22,25,31,34,37,45-undecone, PP3117: (1S,4S,1OS,13S,17S,20S,26S,28R,32S,38S,42Z)-20-cyclopentyl-32-[2-[3,5-difluoro-4-(trifluoromethyl)phenyl]ethyl]-28-ethoxy-2,14,18,21,24,36-hexamethyl-10-[(1 S)-1-methylpropyl]-13-propyl-38-(p-tolylmethyl)-17-(pyrrolidine-l-carbonyl)spiro[2,8,11,14,18,21,24,30,33,36,39-undecazatetracyclo[37.5.1.0$^{4,8}$.0$^{26,30}$]pentatetracont-42-ene-23,1'-cyclobutane]-3,9,12,15,19,22,25,31,34,37,45-undecone, PP3118: (2S,8S,12R,14S,20S,23S,27S,30S,36S,38Z)-20-cyclopentyl-8-[2-[3,5-difluoro-4-(trifluoromethyl)phenyl]ethyl]-12-ethoxy-4,16,19,22,26,32,35-heptamethyl-30-[(1 S)-1-methylpropyl]-23-(piperidine-1-carbonyl)-27-propyl-2-[[4-(trifluoromethyl)phenyl]methyl]spiro[1,4,7,10,16,19,22,26,29,32,35-undecazatricyclo[34.5.1.0$^{10,14}$]dotetracont-38-ene-17,1'-cyclobutane]-3,6,9,15,18,21,25,28,31,34,42-undecone, PP3119: (2S,8S,12R,14S,20S,23S,27S,30S,36S,38Z)-20-cyclopentyl-8-[2-[3,5-difluoro-4-(trifluoromethyl)phenyl]ethyl]-12-ethoxy-4,16,19,22,26,32,35-heptamethyl-30-[(1 S)-1-methylpropyl]-23-(piperidine-1-carbonyl)-27-propyl-2-(p-tolylmethyl)spiro[[1,4,7,10,16,19,22,26,29,32,35-undecazatricyclo[34.5.1.0$^{10,14}$]dotetracont-38-ene-17,1-cyclobutane]-3,6,9,15,18,21,25,28,31,34,42-undecone, PP3120: (2S,8S,12R,14S,20S,23S,27S,30S,36S,38Z)-20-cyclopentyl-8-[2-[3,5-difluoro-4-(trifluoromethyl)phenyl]ethyl]-12-ethoxy-4,16,19,22,26,32,35-heptamethyl-30-[(1 S)-1-methylpropyl]-27-propyl-23-(pyrrolidine-1-carbonyl)-2-[[4-(trifluoromethyl)phenyl]methyl]spiro[1,4,7,10,16,19,22,26,29,32,35-undecazatricyclo[34.5.1.0$^{10,14}$]dotetracont-38-ene-17,1'-cyclobutane]-3,6,9,15,18,21,25,28,31,34,42-undecone, PP3121: (2S,8S,12R,14S,20S,23S,27S,30S,36S,38Z)-20-cyclopentyl-8-[2-[3,5-difluoro-4-(trifluoromethyl)phenyl]ethyl]-12-ethoxy-4,16,19,22,26,32,35-heptamethyl-30-[(1 S)-1-methylpropyl]-27-propyl-2-(p-tolylmethyl)-23-(pyrrolidine-l-carbonyl)spiro[1,4,7,10,16,19,22,26,29,32,35-undecazatric clo[34.5.1.0$^{10,14}$]dotetracont-38-ene-17,1-cyclobutane]-3,6,9,15,18,21,25,28,31,34,42-undecone, (1S,7S,11R,13S,19S,22S,26S,29S,35S,37S,47Z)-19-cyclopentyl-7-[2-[3,5-difluoro-4-(trifluoromethyl)phenyl]ethyl]-1I-ethoxy-N-ethyl-N,3,18,21,25,31,34-heptamethyl-29-[(1S)-l-methylpropyl]-2,5,8,14,17,20,24,27,30,33,55-undecaoxo-spiro[3,6,9,15,18,21,25,28,31,34,41-undecazapentacyclo[24.15.11.2$^{43,46}$.1$^{35,41}$.0$^{9,13}$]pentapentaconta-37,43(54),44,46(53),47-pentaene-16,1'-cyclobutane]-22-carboxamide, (1S,7S,11R,13S,19S,22S,26S,29S,35S,37Z,47Z)-19-cyclopentyl-11-ethoxy-N-ethyl-7-[2-[3-methoxy-4-(trifluoromethyl)phenyl]ethyl]-N,3,3',3',18,21,25,31,34-nonamethyl-29-[(1 S)-1-methylpropyl]-2,5,8,14,17,20,24,27,30, 33,55-undecaoxo-spiro[3,6,9,15,18,21,25,28,31,34,41-undecazapentacyclo[24.15.11.2$^{43,46}$.1$^{35,41}$.0$^{9,13}$]pentapentaconta-37,43(54),44,46(53),47-pentaene-16,1'-cyclobutane]-22-carboxamide, (1 S,7S,11 R,13 S,19S,22S,26S,29S,35S,37Z,47Z)-19-cyclopentyl-7-[2-[3,5-difluoro-4-(trifluoromethyl)phenyl]ethyl]-11-ethoxy-3,3',3',18,21,25,31,34-octamethyl-29-[(1 S)-1-methylpropyl]-22-(pyrrolidine-1-carbonyl)spiro[3,6,9,15,18,21,25,28,31,34,41-undecazapentacyclo[24.15.10.2$^{43,46}$.1$^{35,41}$.0$^{9,13}$]tetrapentaconta-37,43(53),44,46(52),47-pentaene-16,1'-cyclobutane]-2,5,8,14,17,20,24,27,30,33,54-undecone, (1S,7S,11R,13S,19S,22S,26S,29S,35S,37Z,47Z)-7-[2-[3,5-difluoro-4-(trifluoromethyl)phenyl]ethyl]-11-ethoxy-19-(1-ethylpropyl)-3,3',3',18,21,25,31,34-octamethyl-29-[(1 S)-1-methylpropyl]-22-(pyrrolidine-1-carbonyl)spiro[3,6,9,15,18,21,25,28,31,34,41-undecazapentacyclo[24.15.10.2$^{43,46}$.1$^{35,41}$.0$^{9,13}$]tetrapentaconta-37,43(53),44,46(52),47-pentaene-16,1'-cyclobutane]-2,5,8,14,17,20,24,27,30,33,54-undecone, (1S,7S,11R,13S,19S,22S,26S,29S,35S,37Z,47Z)-19-cyclopentyl-31-cyclopropyl-7-[2-[3,5-difluoro-4-(trifluoromethyl)phenyl]ethyl]-11-ethoxy-3,3',3',18,21,25 ,34-heptamethyl-29-[(1 S)-1-methylpropyl]-22-(pyrrolidine-1-carbonyl)spiro[3,6,9,15,18,21,25,28,31,34,41-undecazapentacyclo[24.15.10.2$^{43,46}$.1$^{35,41}$.0$^{9,13}$]tetrapentaconta-37,43(53),44,46(52),47-pentaene-16,1'-cyclobutane]-2,5,8,14,17,20,24,27,30,33,54-undecone, (1S,7S,11R,13S,19S,22S,26S,29S,35S,37Z,47Z)-31-cyclopropyl-7-[2-[3,5-difluoro-4-(trifluoromethyl)phenyl]ethyl]-11-ethoxy-19-(1-ethylpropyl)-3,18,21,25,31,34-pentamethyl-29-[(1 S)-1-methylpropyl]-22-(pyrrolidine-1-carbonyl)spiro[3,6,9,15,18,21,25,28,31,34,41-undecazapentacyclo[24.15.10.2$^{43,46}$.1$^{35,41}$.0$^{9,13}$]tetrapentaconta-37,43(53),44,46(52),47-pentaene-16,1'-cyclobutane]-2,5,8,14,17,20,24,27,30,33,54-undecone, and (1S,7S,11R,13S,19S,22S,26S,29S,35S,37Z,47Z)-7-[2-(3,4-dichlorophenyl)ethyl]-11-ethoxy-19-(1-ethylpropyl)-3,18,21,25,31,34-hexamethyl-29-[(1 S)-1-methylpropyl]-22-(pyrrolidine-1-carbonyl)spiro[3,6,9,15,18,21,25,28,31,34,41-undecazapentacyclo[24.15.11.2$^{43,46}$.1$^{35,41}$.0$^{9,13}$]pentapentaconta-37,43(54),44,46(53),47-pentaene-16,1'-cyclobutane]-2,5,8,14,17,20,24,27,30,33,55-undecone.

The cyclic compound or a salt thereof, or a solvate thereof according to [1], wherein the formula (1) is expressed by formula (2):

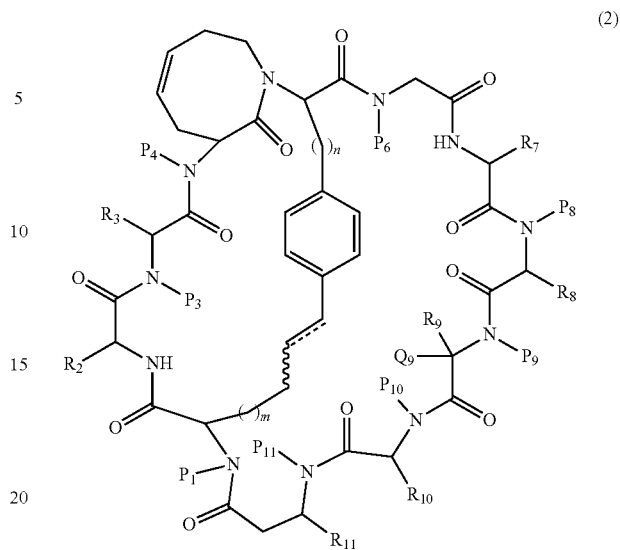

(2)

wherein $=\!=\!=$ , $\sim\!\sim\!\sim$ , n, m, P$_1$, R$_2$, R$_3$, P$_3$, P$_4$, P$_6$, R$_7$, R$_8$, P$_8$, R$_9$, P$_9$, Q$_9$, R$_{10}$, P$_{10}$, R$_{11}$ and P$_{11}$ are the same as defined in [1], the cyclic compound represented by formula (2) is selected from the group consisting of:

PP1827: (1S,7S,11R,13S,19S,22S,26S,29S,35S,37Z,47E)-19-cyclopentyl-7-[2-[3,5-difluoro-4-(trifluoromethyl)phenyl]ethyl]-11-ethoxy-N-ethyl-N,3,18,21,25,31,34-heptamethyl-29-[(1 S)-1-methylpropyl]-2,5,8,14,17,20,24,27,30,33,55-undecaoxo-spiro[3,6,9,15,18,21,25,28,31,34,41-undecazapentacyclo[24.15.11.2$^{43,46}$.1$^{35,41}$.0$^{9,13}$]pentapentaconta-37,43(54),44,46(53),47-pentaene-16,1'-cyclobutane]-22-carboxamide, PP1830: (1S,7S,11R,13S,19S,22S,26S,29S,35S,37Z,47E)-19-cyclopentyl-11-ethoxy-N-ethyl-7-[2-[3-methoxy-4-(trifluoromethyl)phenyl]ethyl]-N,3,3',3',18,21,25,31,34-nonamethyl-29-[(1 S)-1-methylpropyl]-2,5,8,14,17,20,24,27,30,33,55-undecaoxo-spiro[3,6,9,15,18,21,25,28,31,34,41-undecazapentacyclo[24.15.11.2$^{43,46}$.1$^{35,41}$.0$^{9,13}$]pentapentaconta-37,43(54),44,46(53),47-pentaene-16,1'-cyclobutane]-22-carboxamide, PP2260: (1S,7S,11R,13S,19S,22S,26S,29S,35S,37Z)-19-cyclopentyl-11-ethoxy-N-ethyl-7-[2-[3-methoxy-4-(trifluoromethyl)phenyl]ethyl]-N,3,3',3',18,21,25,31,34-nonamethyl-29-[(1 S)-1-methylpropyl]-2,5,8,14,17,20,24,27,30,33,55-undecaoxo-spiro[3,6,9,15,18,21,25,28,31,34,41-undecazapentacyclo[24.15.11.2$^{43,46}$.1$^{35,41}$.0$^{9,13}$]pentapentaconta-37,43(54),44,46(53)-tetraene-16,1'-cyclobutane]-22-carboxamide, PP2574: (1S,7S,11R,13S,19S,22S,26S,29S,35S,37Z,47E)-19-cyclopentyl-7-[2-[3,5-difluoro-4-(trifluoromethyl)phenyl]ethyl]-11-ethoxy-3,3',3',18,21,25,31,34-octamethyl-29-[(1 S)-1-methylpropyl]-22-(pyrrolidine-1-carbonyl)spiro[3,6,9,15,18,21,25,28,31,34,41-undecazapentacyclo[24.15.10.2$^{43,46}$.1$^{35,41}$.0$^{9,13}$]tetrapentaconta-37,43(53),44,46(52),47-pentaene-16,1'-cyclobutane]-2,5,8,14,17,20,24,27,30,33,54-undecone, PP2576: (1S,7S,11R,13S,19S,22S,26S,29S,35S,37Z,47E)-7-[2-[3,5-difluoro-4-(trifluoromethyl)phenyl]ethyl]-11-ethoxy-19-(1-ethylpropyl)-3,3',3',18,21,25,31,34-octamethyl-29-[(1 S)-1-methylpropyl]-22-(pyrrolidine-1-carbonyl)spiro[3,6,9,15,18,21,25,28,31,34,41- undecazapentacyclo[24.15.10.2$^{43,46}$.1$^{35,41}$.0$^{9,13}$]tetrapentaconta-37,43(53),44,46(52),47-pentaene-16,1'-cyclobutane]-2,5,8,14,17,20,24,27,30,33,54-undecone, PP2583: (1S,7S,11R,13S,19S,22S,26S,29S,35S,37Z,47E)-19-cyclopentyl-31-cyclopropyl-7-[2-[3,5-difluoro-4-(trifluoromethyl)phenyl]ethyl]-11-ethoxy-3,3',3',18,21,25,34-heptamethyl-29-[(1S)-1-methylpropyl]-22-(pyrrolidine-1-carbonyl)spiro[3,6,9,15,18,21,25,28,31,34,41-undecazapentacyclo[24.15.10.2$^{43,46}$.1$^{35,41}$.0$^{9,13}$]tetrapentaconta-37,43(53),44,46(52),47-pentaene-16,1'-cyclobutane]-2,5,8,14,17,20,24,27,30,33,54-undecone, PP2957: (1S,7S,11R,13S,19S,22S,26S,29S,35S,37Z,47E)-31-cyclopropyl-7-[2-[3,5-difluoro-4-(trifluoromethyl)phenyl]ethyl]-11-ethoxy-19-(1-ethylpropyl)-3,18,21,25,34-pentamethyl-29-[(1S)-1-methylpropyl]-22-(pyrrolidine-1-carbonyl)spiro[3,6,9,15,18,21,25,28,31,34,41-undecazapentacyclo[24.15.10.2$^{43,46}$.1$^{35,41}$.0$^{9,13}$]tetrapentaconta-37,43(53),44,46(52),47-pentaene-16,1'-cyclobutane]-2,5,8,14,17,20,24,27,30,33,54-undecone, PP3033: (1S,7S,11R,13S,19S,22S,26S,29S,35S,37Z)-19-cyclopentyl-11-ethoxy-7-[2-[3-methoxy-4-(trifluoromethyl)phenyl]ethyl]-3,18,21,25,31,34-hexamethyl-29-[(1S)-1-methylpropyl]-22-(piperidine-1-carbonyl)spiro[3,6,9,15,18,21,25,28,31,34,4l-undecazapentacyclo[24.15.11.2$^{43,46}$.1$^{35,41}$.0$^{9,13}$]pentapentaconta-37,43(54),44,46(53)-tetraene-16,1'-cyclobutane]-2,5,8,14,17,20,24,27,30,33,55-undecone, PP3034: (1S,7S,11R,13S,19S,22S,26S,29S,35S,37Z)-19-cyclopentyl-11-ethoxy-7-[2-[3-methoxy-4-(trifluoromethyl)phenyl]ethyl]-3,3',3',18,21,25,31,34-octamethyl-29-[(1S)-1-methylpropyl]-22-(pyrrolidine-1-carbonyl)spiro[3,6,9,15,18,21,25,28,31,34,41-undecazapentacyclo[24.15.11.2$^{43,46}$.1$^{35,41}$.0$^{9,13}$]pentapentaconta-37,43(54),44,46(53)-tetraene-16,1'-cyclobutane]-2,5,8,14,17,20,24,27,30,33,55-undecone, PP3036: (1S,7S,11R,13S,19S,22S,26S,29S,35S,37Z)-19-cyclopentyl-11-ethoxy-7-[2-[3-methoxy-4-(trifluoromethyl)phenyl]ethyl]-3,3',3',18,21,25,31,34-octamethyl-294(1S)-1-methylpropyl]-22-(piperidine-1-carbonyl)spiro[3,6,9,15,18,21,25,28,31,34,41-undecazapentacyclo[24.15.10.2$^{43,46}$.1$^{35,41}$.0$^{9,13}$]tetrapentaconta-37,43(53),44,46(52)-tetraene-16,1'-cyclobutane]-2,5,8,14,17,20,24,27,30,33,54-undecone, PP3037: (1S,7S,11R,13S,19S,22S,26S,29S,35S,37Z)-19-cyclopentyl-11-ethoxy-7-[2-[3-methoxy-4-(trifluoromethyl)phenyl]ethyl]-3,3',3',18,21,25,31,34-octamethyl-29-[(1S)-1-methylpropyl]-22-(pyrrolidine-1-carbonyl)spiro[3,6,9,15,18,21,25,28,31,34,41-undecazapentacyclo[24.15.10.2$^{43,46}$.1$^{35,41}$.0$^{9,13}$]tetrapentaconta-37,43(53),44,46(52)-tetraene-16,1'-cyclobutane]-2,5,8,14,17,20,24,27,30,33,54-undecone, PP3047: (1S,7S,IIR,13S,19S,22S,26S,29S,35S,37Z,47E)-7-[2-(3,4-dichlorophenyl)ethyl]-I1-ethoxy-19-(I-ethylpropyl)-3,18,21,25,31,34-hexamethyl-29-[(1S)-1-methylpropyl]-22-(pyrrolidine-1-carbonyl)spiro[3,6,9,15,18,21,25,28,31,34,41-undecazapentacyclo[24.15.11.2$^{43,46}$.1$^{35,41}$.0$^{9,13}$]pentapentaconta-37,43(54),44,46(53),47-pentaene-16,1'-cyclobutane]-2,5,8,14,17,20,24,27,30,33,55-undecone, PP3093: (1S,7S,11R,13S,19S,22S,26S,29S,35S,37Z)-19-cyclopentyl-11-ethoxy-7-[2-[3-methoxy-4-(trifluoromethyl)phenyl]ethyl]-3,3',3',18,21,25,31,34-octamethyl-29-[(1S)-1-methylpropyl]-22-(piperidine-1-carbonyl)spiro[3,6,9,15,18,21,25,28,31,34,41-undecazapentacyclo[24.15.9.2$^{43,46}$.1$^{35,41}$.0$^{9,13}$]tripentaconta-37,43(52),44,46(51)-tetraene-16,1'-cyclobutane]-2,5,8,14,17,20,24,27,30,33,53-undecone, PP3094: (1S,7S,11R,13S,19S,22S,26S,29S,35S,37Z)-19-cyclopentyl-7-[2-[3-methoxy-4-(trifluoromethyl)phenyl]ethyl]-3,3',3',18,21,25,31,34-octamethyl-29-[(1S)-1-methylpropyl]-11-propoxy-22-(pyrrolidine-1-carbonyl)spiro[3,6,9,15,18,21,25,28,31,34,41-undecazapentacyclo[24.15.9.2$^{43,46}$.1$^{35,41}$.0$^{9,13}$]tripentaconta-37,43(52),44,46(51)-tetraene-16,1'-cyclobutane]-2,5,8,14,17,20,24,27,30,33,53-undecone, (1S,7S,11R,13S,19S,22S,26S,29S,35S,37Z,47Z)-19-cyclopentyl-7-[2-[3,5-difluoro-4-(trifluoromethyl)phenyl]ethyl]-11-ethoxy-N-ethyl-N,3,18,21,25,31,34-heptamethyl-29-[(1S)-1-methylpropyl]-2,5,8,14,17,20,24,27,30,33,55-undecaoxo-spiro[3,6,9,15,18,21,25,28,31,34,41-undecazapentacyclo[24.15.11.2$^{43,46}$.1$^{35,41}$.0$^{9,13}$]pentapentaconta-37,43(54),44,46(53),47-pentaene-16,1'-cyclobutane]-22-carboxamide, (1S,7S,11R,13S,19S,22S,26S,29S,35S,37Z,47Z)-19-cyclopentyl-11-ethoxy-N-ethyl-7-[2-[3-methoxy-4-(trifluoromethyl)phenyl]ethyl]-N,3,3',3',18,21,25,31,34-nonamethyl-29-[(1S)-1-methylpropyl]-2,5,8,14,17,20,24,27,30,33,55-undecaoxo-spiro[3,6,9,15,18,21,25,28,31,34,41-undecazapentacyclo[24.15.11.2$^{43,46}$.1$^{35,41}$.0$^{9,13}$]pentapentaconta-37,43(54),44,46(53),47-pentaene-16,1'-cyclobutane]-22-carboxamide, (1S,7S,11R,13S,19S,22S,26S,29S,35S,37Z,47Z)-19-cyclopentyl-7-[2-[3,5-difluoro-4-(trifluoromethyl)phenyl]ethyl]-11-ethoxy-3,3',3',18,21,25,31,34-octamethyl-29-[(1S)-1-methylpropyl]-22-(pyrrolidine-1-carbonyl)spiro[3,6,9,15,18,21,25,28,31,34,41-undecazapentacyclo[24.15.10.2$^{43,46}$.1$^{35,41}$.0$^{9,13}$]tetrapentaconta-37,43(53),44,46(52),47-pentaene-16,1'-cyclobutane]-2,5,8,14,17,20,24,27,30,33,54-undecone, (1S,7S,11R,13S,19S,22S,26S,29S,35S,37Z,47Z)-7-[2-[3,5-difluoro-4-(trifluoromethyl)phenyl]ethyl]-11-ethoxy-19-(1-ethylpropyl)-3,3',3',18,21,25,31,34-octamethyl-29-[(1S)-1-methylpropyl]-22-(pyrrolidine-1-carbonyl)spiro[3,6,9,15,18,21,25,28,31,34,41-undecazapentacyclo[24.15.10.2$^{43,46}$.1$^{35,41}$.0$^{9,13}$]tetrapentaconta-37,43(53),44,46(52),47-pentaene-16,1'-cyclobutane]-2,5,8,14,17,20,24,27,30,33,54-undecone, (1S,7S,11R,13S,19S,22S,26S,29S,35S,37Z,47Z)-19-cyclopentyl-31-cyclopropyl-7-[2-[3,5-difluoro-4-(trifluoromethyl)phenyl]ethyl]-11-ethoxy-3,3',3',18,21,25,34-heptamethyl-29-[(1S)-1-methylpropyl]-22-(pyrrolidine-1-carbonyl)spiro[3,6,9,15,18,21,25,28,31,34,41-undecazapentacyclo[24.15.10.2$^{43,46}$.1$^{35,41}$.0$^{9,13}$]tetrapentaconta-37,43(53),44,46(52),47-pentaene-16,1'-cyclobutane]-2,5,8,14,17,20,24,27,30,33,54-undecone, (1S,7S,11R,13S,19S,22S,26S,29S,35S,37Z,47Z)-31-cyclopropyl-7-[2-[3,5-difluoro-4-(trifluoromethyl)phenyl]ethyl]-11-ethoxy-19-(1-ethylpropyl)-3,18,21,25,34-pentamethyl-29-[(1S)-1-methylpropyl]-22-(pyrrolidine-1-carbonyl)spiro[3,6,9,15,18,21,25,28,31,34,41-undecazapentacyclo[24.15.10.2$^{43,46}$.1$^{35,41}$.0$^{9,13}$]tetrapentaconta-37,43(53),44,46(52),47-pentaene-16,1'-cyclobutane]-2,5,8,14,17,20,24,27,30,33,54-undecone, and (1S,7S,11R,13S,19S,22S,26S,29S,35S,37Z,47Z)-7-[2-(3,4-dichlorophenyl)ethyl]-11-ethoxy-19-(1-ethylpropyl)-3,18,21,25,31,34-hexamethyl-29-[(1S)-1-methylpropyl]-22-(pyrrolidine-1-carbonyl)spiro[3,6,9,15,18,21,25,28,31,34,41-undecazapentacyclo[24.15.11.2$^{43,46}$.1$^{35,41}$.0$^{9,13}$]pentapentaconta-37,43(54),44,46(53),47-pentaene-16,1'-cyclobutane]-2,5,8,14,17,20,24,27,30,33,55-undecone.

The cyclic compound or a salt thereof, or a solvate thereof according to [1], wherein the formula (1) is expressed by formula (3):

(3)

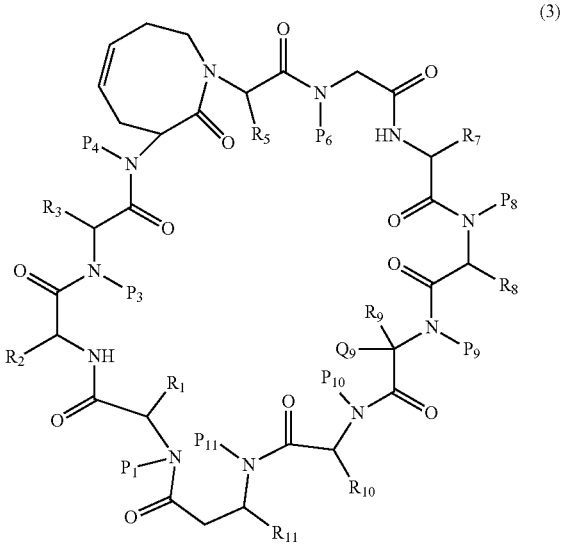

wherein, $R_1$ is a $C_1$ to $C_7$ alkyl;

$R_5$ is benzyl optionally substituted with one or more groups selected from the group consisting of a $C_1$ to $C_6$ alkyl, a $C_1$ to $C_6$ haloalkyl and a $C_3$ to $C_8$ cycloalkyl;

═══, 〰〰, n, m, $P_1$, $R_2$, $R_3$, $P_3$, $P_4$, $P_6$, $R_7$, $R_8$, $P_9$, $R_9$, $P_9$, $Q_9$, $R_{10}$, $P_{10}$, $R_{11}$ and $P_{11}$ are the same as defined in [1], wherein the cyclic compound represented by formula (3) is selected from the group consisting of:

PP1574: (2S,8S,12R,14S,20S,23S,27S,30S,36S,38Z)-20-cyclopentyl-8-[2-[3,5-difluoro-4-(trifluoromethyl)phenyl]ethyl]-12-ethoxy-N-ethyl-27-isobutyl-N,4,19,22,26,32,35-heptamethyl-30-[(1 S)-1-methylpropyl]-3,6,9,15,18,21,25,28,31,34,42-undecaoxo-2-[[4-(trifluoromethyl)phenyl]methyl]spiro[1,4,7,10,16,19,22,26,29,32,35-undecazatricyclo[34.5.1.0$^{10,14}$]1dotetracont-38-ene-17,1'-cyclopentane]-23-carboxamide, PP1650: (2S,8S,12R,14S,20S,23S,27S,30S,36S,38Z)-20-cyclopentyl-8-[2-[3,5-difluoro-4-(trifluoromethyl)phenyl]ethyl]-12-ethoxy-27-isobutyl-N,N,3',3',4,19,22,26,32,35-decamethyl-30-[(1 S)-1-methylpropyl]-3,6,9,15,18,21,25,28,31,34,42-undecaoxo-2-[[4-(trifluoromethyl)phenyl]methyl]spiro[1,4,7,10,16,19,22,26,29,32,35-undecazatricyclo[34.5.1.0$^{10,14}$]1dotetracont-38-ene-17,1'-cyclobutane]-23-carboxamide, PP1827: (1S,7S,11R,13S,19S,22S,26S,29S,35S,37Z,47E)-19-cyclopentyl-7-[2-[3,5-difluoro-4-(trifluoromethyl)phenyl]ethyl]-11-ethoxy-N-ethyl-N,3,18,21,25,31,34-heptamethyl-29-[(1 S)-1-methylpropyl]-2,5,8,14,17,20,24,27,30,33,55-undecaoxo-spiro[3,6,9,15,18,21,25,28,31,34,41-undecazapentacyclo[24.15.11.2$^{43,46}$.1$^{35,41}$.0$^{9,13}$]pentapentaconta-37,43(54),44,46(53),47-pentaene-16,1'-cyclobutane]-22-carboxamide, PP1830: (1S,7S,IIR,13S,19S,22S,26S,29S,35S,37Z,47E)-19-cyclopentyl-11-ethoxy-N-ethyl-7-[2-[3-methoxy-4-(tfifluoromethyl)phenyl]ethyl]-N,3,3',3',18,21,25,31,34-nonamethyl-29-[(1S)-1-methylpropyl]-2,5,8,14,17,20,24,27,30,33,55-undecaoxo-spiro[3,6,9,15,18,21,25,28,31,34,41-undecazapentacyclo[24.15.11.2$^{43,46}$.1$^{35,41}$.0$^{9,13}$]pentapentaconta-37,43(54),44,46(53),47-pentaene-16,1'-cyclobutane]-22-carboxamide, PP2093: (2S,8S,12R,14S,20S,23S,27S,30S,36S,38Z)-20-cyclopentyl-32-cyclopropyl-8-[2-[3,5-difluoro-4-(trifluoromethyl)phenyl]ethyl]-12-ethoxy-N,N,3',3',4,19,22,26,35-nonamethyl-30-[(1 S)-1-methylpropyl]-3,6,9,15,18,21,25,28,31,34,42-undecaoxo-27-propyl-2-(p-tolylmethyl)spiro[[1,4,7,10,16,19,22,26,29,32,35-undecazatric clo[34.5.1.0$^{10,14}$]dotetracont-38-ene-17,1'-cyclobutane]-23-carboxamide, PP2260: (1S,7S,11R,13S,19S,22S,26S,29S,35S,37Z)-19-cyclopentyl-11-ethoxy-N-ethyl-7-[2-[3-methoxy-4-(trifluoromethyl)phenyl]ethyl]-N,3,3',3',18,21,25,31,34-nonamethyl-29-[(1 S)-1-methylpropyl]-2,5,8,14,17,20,24,27,30,33,55-undecaoxo-spiro[3,6,9,15,18,21,25,28,31,34,41-undecazapentacyclo[24.15.11.2$^{43,46}$.1$^{35,41}$.0$^{9,13}$]pentapentaconta-37,43(54),44,46(53)-tetraene-16,1'-cyclobutane]-22-carboxamide, PP2316: (2S,8S, 12R, 14S,20S,23S,27S,30S,36S,38Z)-20-cyclopentyl-32-cyclopropyl-12-ethoxy-8-[2-[3-methoxy-4-(trifluoromethyl)phenyl]ethyl]-N,N,4,16,19,22,26,35-octamethyl-30-[(1 S)-1-methylpropyl]-3,6,9,15,18,21,25,28,31,34,42-undecaoxo-27-propyl-2-[[4-(trifluoromethyl)phenyl]methyl]spiro[1,4,7,10,16,19,22,26,29,32,35-undecazatricyclo[34.5.1.0$^{10,14}$]dotetracont-38-ene-17,1'-cyclobutane]-23-carboxamide, PP2320: (1S,4S,10S,13S,17S,20S,26S,28R,32S,38S,42Z)-20-cyclopentyl-28-ethoxy-32-[2-[3-methoxy-4-(trifluoromethyl)phenyl]ethyl]-N, N, 2,14,18,21, 24,36-octamethyl-10-[(1 S)-1-methylpropyl]-3,9,12,15,19,22,25,31,34,37,45-undecaoxo-13-propyl-38-[[4-(trifluoromethyl)phenyl]methyl]spiro[2,8,11,14,18,21,24,30,33,36,39-undecazatetracyclo[37.5.1.0$^{4,8}$.0$^{26,30}$]pentatetracont-42-ene-23,1'-cyclobutane]-17-carboxamide, PP2328: (2S,8S,12R,14S,20S,23S,27S,30S,36S,38Z)-20-cyclopentyl-32-cyclopropyl-12-ethoxy-8-[2-[3-methoxy-4-(trifluoromethyl)phenyl]ethyl]-N,N,4,16,19,22,26,35-octamethyl-30-[(1 S)-1-methylpropyl]-3,6,9,15,18,21,25,28,31,34,42-undecaoxo-27-propyl-2-(p-tolylmethyl)spiro[[1,4,7,10,16,19,22,26,29,32,35-undecazatricyclo[34.5.1.0$^{10,14}$]dotetracont-38-ene-17,1'-cyclobutane]-23-carboxamide, PP2574: (1S,7S,11R,13S,19S,22S,26S,29S,35S,37Z,47E)-19-cyclopentyl-7-[2-[3,5-difluoro-4-(trifluoromethyl)phenyl]ethyl]-11-ethoxy-3,3',3',18,21,25,31,34-octamethyl-29-[(1 S)-1-methylpropyl]-22-(pyrrolidine-1-carbonyl)spiro[3,6,9,15,18,21,25,28,31,34,41-undecazapentacyclo[24.15.10.2$^{43,46}$.1$^{35,41}$.0$^{9,13}$]tetrapentaconta-37,43(53),44,46(52),47-pentaene-16,1'-cyclobutane]-2,5,8,14,17,20,24,27,30,33,54-undecone, PP2576: (1S,7S,11R,13S,19S,22S,26S,29S,35S,37Z,47E)-7-[2-[3,5-difluoro-4-(trifluoromethyl)phenyl]ethyl]-11-ethoxy-19-(1-ethylpropyl)-3,3',3',18,21,25,31,34-octamethyl-29-[(1 S)-1-methylpropyl]-22-(pyrrolidine-1-carbonyl)spiro[3,6,9,15,18,21,25,28,31,34,41-undecazapentacyclo[24.15.10.2$^{43,46}$.1$^{35,41}$.0$^{9,13}$]tetrapentaconta-37,43(53),44,46(52),47-pentaene-16,1'-cyclobutane]-2,5,8,14,17,20,24,27,30,33,54-undecone, PP2583: (1S,7S,11R,13S,19S,22S,26S,29S,35S,37Z,47E)-19-cyclopentyl-31-cyclopropyl-7-[2-[3,5-difluoro-4-(trifluoromethyl)phenyl]ethyl]-11-ethoxy-3,3',3',18,21,25,34-heptamethyl-29-[(1 S)-1-methylpropyl]-22-(pyrrolidine-1-carbonyl)spiro[3,6,9,15,18,21,25,28,31,34,41-undecazapentacyclo[24.15.10.2$^{43,46}$.1$^{35,41}$.0$^{9,13}$]tetrapentaconta-37,43(53),44,46(52),47-pentaene-16,1'-cyclobutane]-2,5,8,14,17,20,24,27,30,33,54-undecone, PP2687: (2S,8S,12R,14S,20S,23S,27S,30S,36S,38Z)-20-cyclopentyl-12-ethoxy-2-[(4-ethylphenyl)methyl]-27-isobutyl-8-[2-[3-methoxy-4-(trifluoromethyl)phenyl]

ethyl]-N,N,3',3',4,19,22,26,32,35-decamethyl-30-[(1S)-1-methylpropyl]-3,6,9,15,18,21,25,28,31,34,42-undecaoxo-spiro[1,4,7,10,16,19,22,26,29,32,35-undecazatricyclo[34.5.1.0$^{10,14}$]dotetracont-38-ene-17,1'-cyclobutane]-23-carboxamide, PP2691: (2S,8S,12R,14S,20S,23S,27S,30S,36S,38S)-20-cyclopentyl-2-[(4-cyclopropylphenyl)methyl]-12-ethoxy-27-isobutyl-8-[2-[3-methoxy-4-(trifluoromethyl)phenyl]ethyl]-N,N,3',3',4,19,22,26,32,35-decamethyl-30-[(1 S)-1-methylpropyl]-3,6,9,15,18,21,25,28,31,34,42-undecaoxo-spiro[1,4,7,10,16,19,22,26,29,32,35-undecazatricyclo[34.5.1.0$^{10,14}$]dotetracont-38-ene-17,1'-cyclobutane]-23-carboxamide, PP2957: (1S,7S,11R,13S,19S,22S,26S,29S,35S,37Z,47E)-31-cyclopropyl-7-[2-[3,5-difluoro-4-(trifluoromethyl)phenyl]ethyl]-11-ethoxy-19-(1-ethylpropyl)-3,18,21,25,34-pentamethyl-29-[(1 S)-1-methylpropyl]-22-(pyrrolidine-1-carbonyl)spiro[3,6,9,15,18,21,25,28,31,34,41-undecazapentacyclo[24.15.10.2$^{43,46}$.1$^{35,41}$.0$^{9,13}$]tetrapentaconta-37,43(53),44,46(52),47-pentaene-16,1'-cyclobutane]-2,5,8,14,17,20,24,27,30,33,54-undecone, PP3033: (1S,7S,11R,13S,19S,22S,26S,29S,35S,37Z)-19-cyclopentyl-11-ethoxy-7-[2-[3-methoxy-4-(trifluoromethyl)phenyl]ethyl]-3,18,21,25,31,34-hexamethyl-29-[(1 S)-1-methylpropyl]-22-(piperidine-1-carbonyl)spiro[3,6,9,15,18,21,25,28,31,34,41-undecazapentacyclo[24.15.11.2$^{43,46}$.1$^{35,41}$.0$^{9,13}$]pentapentaconta-37,43(54),44,46(53)-tetraene-16,1'-cyclobutane]-2,5,8,14,17,20,24,27,30,33,55-undecone, PP3034: (1S,7S,11R,13S,19S,22S,26S,29S,35S,37Z)-19-cyclopentyl-11-ethoxy-7-[2-[3-methoxy-4-(trifluoromethyl)phenyl]ethyl]-3,3',3',18,21,25,31,34-octamethyl-29-[(1S)-1-methylpropyl]-22-(pyrrolidine-1-carbonyl)spiro[3,6,9,15,18,21,25,28,31,34,41-undecazapentacyclo[24.15.11.2$^{43,46}$.1$^{35,41}$.0$^{9,13}$]pentapentaconta-37,43(54),44,46(53)-tetraene-16,1'-cyclobutane]-2,5,8,14,17,20,24,27,30,33,55-undecone, PP3036: (1S,7S,11R,13S,19S,22S,26S,29S,35S,37Z)-19-cyclopentyl-11-ethoxy-7-[2-[3-methoxy-4-(trifluoromethyl)phenyl]ethyl]-3,3',3',18,21,25,31,34-octamethyl-294(1S)-1-methylpropyl]-22-(piperidine-1-carbonyl)spiro[3,6,9,15,18,21,25,28,31,34,41-undecazapentacyclo[24.15.10.2$^{43,46}$.1$^{35,41}$.0$^{9,13}$]tetrapentaconta-37,43(53),44,46(52)-tetraene-16,1'-cyclobutane]-2,5,8,14,17,20,24,27,30,33,54-undecone, PP3037: (1S,7S,11R,13S,19S,22S,26S,29S,35S,37Z)-19-cyclopentyl-11-ethoxy-7-[2-[3-methoxy-4-(trifluoromethyl)phenyl]ethyl]-3,3',3',18,21,25,31,34-octamethyl-29-[(1S)-1-methylpropyl]-22-(pyrrolidine-1-carbonyl)spiro[3,6,9,15,18,21,25,28,31,34,41-undecazapentacyclo[24.15.10.2$^{43,46}$.1$^{35,41}$.0$^{9,13}$]tetrapentaconta-37,43(53),44,46(52)-tetraene-16,1'-cyclobutane]-2,5,8,14,17,20,24,27,30,33,54-undecone, PP3047: (1S,7S,IIR,13S,19S,22S,26S,29S,35S,37Z,47E)-7-[2-(3,4-dichlorophenyl)ethyl]-I1-ethoxy-19-(I-ethylpropyl)-3,18,21,25,31,34-hexamethyl-29-[(1S)-1-methylpropyl]-22-(pyrrolidine-1-carbonyl)spiro[3,6,9,15,18,21,25,28,31,34,41-undecazapentacyclo[24.15.11.2$^{43,46}$.1$^{35,41}$.0$^{9,13}$]pentapentaconta-37,43(54),44,46(53),47-pentaene-16,1'-cyclobutane]-2,5,8,14,17,20,24,27,30,33,55-undecone, PP3093: (1S,7S,11R,13S,19S,22S,26S,29S,35S,37Z)-19-cyclopentyl-11-ethoxy-7-[2-[3-methoxy-4-(trifluoromethyl)phenyl]ethyl]-3,3',3',18,21,25,31,34-octamethyl-29-[(1S)-1-methylpropyl]-22-(piperidine-1-carbonyl)spiro[3,6,9,15,18,21,25,28,31,34,41-undecazapentacyclo[24.15.9.2$^{43,46}$.1$^{35,41}$.0$^{9,13}$]tripentaconta-37,43(52),44,46(51)-tetraene-16,1'-cyclobutane]-2,5,8,14,17,20,24,27,30,33,53-undecone, PP3094: (1S,7S,11R,13S,19S,22S,26S,29S,35S,37Z)-19-cyclopentyl-7-[2-[3-methoxy-4-(trifluoromethyl)phenyl]ethyl]-3,3',3',18,21,25,31,34-octamethyl-29-[(1 S)-1-methylpropyl]-11-propoxy-22-(pyrrolidine-1-carbonyl)spiro[3,6,9,15,18,21,25,28,31,34,41-undecazapentacyclo[24.15.9.2$^{43,46}$.1$^{35,41}$.0$^{9,13}$]tripentaconta-37,43(52),44,46(51)-tetraene-16,1'-cyclobutane]-2,5,8,14,17,20,24,27,30,33,53-undecone, PP3095: (2S,8S,12R,14S,20S,23S,27S,30S,36S,38Z)-20-cyclopentyl-32-cyclopropyl-12-ethoxy-8-[2-[3-methoxy-4-(trifluoromethyl)phenyl]ethyl]-4,16,19,22,26,35-hexamethyl-30-[(1S)-1-methylpropyl]-23-(piperidine-1-carbonyl)-27-propyl-2-[[4-(trifluoromethyl)phenyl]methyl]spiro[1,4,7,10,16,19,22,26,29,32,35-undecazatricyclo[34.5.1.0$^{10,14}$]dotetracont-38-ene-17,1'-cyclobutane]-3,6,9,15,18,21,25,28,31,34,42-undecone, PP3096: (2S,8S,12R,14S,20S,23S,27S,30S,36S,38Z)-20-cyclopentyl-32-cyclopropyl-12-ethoxy-8-[2-[3-methoxy-4-(trifluoromethyl)phenyl]ethyl]-4,16,19,22,26,35-hexamethyl-30-[(1S)-1-methylpropyl]-23-(piperidine-1-carbonyl)-27-propyl-2-(p-tolylmethyl)spiro[[1,4,7,10,16,19,22,26,29,32,35-undecazatricyclo[34.5.1.0$^{10,14}$]dotetracont-38-ene-17,1-cyclobutane]-3,6,9,15,18,21,25,28,31,34,42-undecone, PP3097: (2S,8S,12R,14S,20S,23S,27S,30S,36S,38Z)-20-cyclopentyl-32-cyclopropyl-12-ethoxy-8-[2-[3-methoxy-4-(trifluoromethyl)phenyl]ethyl]-4,16,19,22,26,35-hexamethyl-30-[(1S)-1-methylpropyl]-27-propyl-23-(pyrrolidine-1-carbonyl)-2-[[4-(trifluoromethyl)phenyl]methyl]spiro[1,4,7,10,16,19,22,26,29,32,35-undecazatricyclo[34.5.1.0$^{10,14}$]dotetracont-38-ene-17,1'-cyclobutane]-3,6,9,15,18,21,25,28,31,34,42-undecone, PP3098: (2S,8S,12R,14S,20S,23S,27S,30S,36S,38Z)-20-cyclopentyl-32-cyclopropyl-12-ethoxy-8-[2-[3-methoxy-4-(trifluoromethyl)phenyl]ethyl]-4,16,19,22,26,35-hexamethyl-30-[(1S)-1-methylpropyl]-27-propyl-2-(p-tolylmethyl)-23-(pyrrolidine-l-carbonyl)spiro[1,4,7,10,16,19,22,26,29,32,35-undecazatricyclo[34.5.1.0$^{10,14}$]dotetracont-38-ene-17,1-cyclobutane]-3,6,9,15,18,21,25,28,31,34,42-undecone, PP3099: (1S,4S,10S,13S,17S,20S,26S,28R,32S,38S,42Z)-20-cyclopentyl-28-ethoxy-32-[2-[3-methoxy-4-(trifluoromethyl)phenyl]ethyl]-2,14,18,21,24,36-hexamethyl-10-[(1 S)-1-methylpropyl]-17-(piperidine-1-carbonyl)-13-propyl-38-[[4-(trifluoromethyl)phenyl]methyl]spiro[2,8,11,14,18,21,24,30,33,36,39-undecazatetracyclo[37.5.1.0$^{4,8}$.0$^{26,30}$]pentatetracont-42-ene-23,1'-cyclobutane]-3,9,12,15,19,22,25,31,34,37,45-undecone, PP3100: (1S,4S,1OS,13S,17S,20S,26S,28R,32S,38S,42Z)-20-cyclopentyl-28-ethoxy-32-[2-[3-methoxy-4-(trifluoromethyl)phenyl]ethyl]-2,14,18,21,24,36-hexamethyl-10-[(1 S)-1-methylpropyl]-17-(piperidine-1-carbonyl)-13-propyl-38-(p-tolylmethyl)spiro[2,8,11,14,18,21,24,30,33,36,39-undecazatetracyclo[37.5.1.0$^{4,8}$.0$^{26,30}$]pentatetracont-42-ene-23,1'-cyclobutane]-3,9,12,15,19,22,25,31,34,37,45-undecone, PP3101: (1S,4S,1OS,13S,17S,20S,26S,28R,32S,38S,42Z)-20-cyclopentyl-28-ethoxy-32-[2-[3-methoxy-4-(trifluoromethyl)phenyl]ethyl]-2,14,18,21,24,36-hexamethyl-10-[(1 S)-1-methylpropyl]-13-propyl-17-(pyrrolidine-1-carbonyl)-38-[[4-(trifluoromethyl)phenyl]methyl]spiro[2,8,11,14,18,21,24,30,33,36,39-undecazatetracyclo[37.5.1.0$^{4,8}$.0$^{26,30}$]pentatetracont-42-ene-23,1'-cyclobutane]-3,9,12,15,19,22,25,31,34,37,45-undecone, PP3102: (1S,4S,10S,13S,17S,20S,26S,28R,32S,38S,42Z)-20-cyclopentyl-28-ethoxy-32-[2-[3-methoxy-4-(trifluoromethyl)phenyl]ethyl]-2,14,18,21,24,36-hexamethyl-10-[(1 S)-1-methylpropyl]-13-propyl-38-(p-tolylmethyl)-17-(pyrrolidine-l-carbonyl)spiro[2,8,11,14,18,21,24,30,33,36,39-undecazatetracyclo[37.5.1.0$^{4,8}$.0$^{26,30}$]pentatetracont-42-ene-23,1'-cyclobutane]-3,9,12,15,19,22,25,31,34,37,45-undecone, PP3103: (2S,8S,12R,14S,20S,23S,27S,30S,36S,38Z)-20-cyclopentyl-12-ethoxy-8-[2-[3-methoxy-4-(trifluoromethyl)phenyl]ethyl]-4,16,19,22,26,32,35-heptamethyl-30-[(1 S)-1-methylpropyl]-23-(piperidine-1-carbonyl)-27-propyl-2-[[4-(trifluoromethyl)phenyl]methyl]spiro[1,4,7,10,16,19,22,26,29,32,35-undecazatricyclo[34.5.1.0$^{10,14}$]dotetracont-38-ene-17,1'-cyclobutane]-3,6,9,15,18,21,25,28,31,34,42-undecone, PP3104: (2S,8S,12R,14S,20S,23S,27S,30S,36S,38Z)-20-cyclopentyl-12-ethoxy-8-[2-[3-methoxy-4-(trifluoromethyl)phenyl]ethyl]-4,16,19,22,26,32,35-heptamethyl-30-[(1S)-1-methylpropyl]-23-(piperidine-l-carbonyl)-27-propyl-2-(p-tolylmethyl)spiro[1,4,7,10,16,19,22,26,29,32,35-undecazatricyclo[34.5.1.0$^{10,14}$]dotetracont-38-ene-17,1'-cyclobutane]-3,6,9,15,18,21,25,28,31,34,42-undecone, PP3105: (2S,8S,12R,14S,20S,23S,27S,30S,36S,38Z)-20-cyclopentyl-12-ethoxy-8-[2-[3-methoxy-4-(trifluoromethyl)phenyl]ethyl]-4,16,19,22,26,32,35-heptamethyl-30-[(1 S)-1-methylpropyl]-27-propyl-23-(pyrrolidine-1-carbonyl)-2-[[4-(trifluoromethyl)phenyl]methyl]spiro[1,4,7,10,16,19,22,26,29,32,35-undecazatricyclo[34.5.1.0$^{10,14}$]dotetracont-38-ene-17,1'-cyclobutane]-3,6,9,15,18,21,25,28,31,34,42-undecone, PP3106: (2S,8S,12R,14S,20S,23S,27S,30S,36S,38Z)-20-cyclopentyl-12-ethoxy-8-[2-[3-methoxy-4-(trifluoromethyl)phenyl]ethyl]-4,16,19,22,26,32,35-heptamethyl-30-[(1S)-1-methylpropyl]-27-propyl-2-(p-tolylmethyl)-23-(pyrrolidine-l-carbonyl)spiro[1,4,7,10,16,19,22,26,29,32,35-undecazatricyclo[34.5.1.0$^{10,14}$]dotetracont-38-ene-17,1-cyclobutane]-3,6,9,15,18,21,25,28,31,34,42-undecone, PP3110: (2S,8S,12R,14S,20S,23S,27S,30S,36S,38Z)-20-cyclopentyl-32-cyclopropyl-8-[2-[3,5-difluoro-4-(trifluoromethyl)phenyl]ethyl]-12-ethoxy-4,16,19,22, 26,35-hexamethyl-30-11(1S)-1-methylpropyl]-23-(piperidine-l-carbonyl)-27-propyl-2-[11114-(trifluoromethyl)phenyl]methyl]spiro[1,4,7,10,16,19,22,26,29,32,35-undecazatricyclo[34.5.1.0$^{10,14}$]dotetracont-38-ene-17,1'-cyclobutane]-3,6,9,15,18,21,25,28,31,34,42-undecone, PP3111: (2S,8S,12R,14S,20S,23S,27S,30S,36S,38Z)-20-cyclopentyl-32-cyclopropyl-8-[2-[3,5-difluoro-4-(trifluoromethyl)phenyl]ethyl]-12-ethoxy-4,16,19,22,26,35-hexamethyl-30-[(1 S)-1-methylpropyl]-23-(piperidine-l-carbonyl)-27-propyl-2-(p-tolylmethyl)spiro[[1,4,7,10,16,19,22,26,29,32,35-undecazatricyclo[34.5.1.0$^{10,14}$]dotetracont-38-ene-17,1-cyclobutane]-3,6,9,15,18,21,25,28,31,34,42-undecone, PP3112: (2S,8S,12R,14S,20S,23S,27S,30S,36S,38Z)-20-cyclopentyl-32-cyclopropyl-8-[2-[3,5-difluoro-4-(trifluoromethyl)phenyl]ethyl]-12-ethoxy-4,16,19,22,26,35-hexamethyl-30-[(1 S)-1-methylpropyl]-27-propyl-23-(pyrrolidine-1-carbonyl)-2-[[4-(trifluoromethyl)phenyl]methyl]spiro[1,4,7,10,16,19,22,26,29,32,35-undecazatricyclo[34.5.1.0$^{10,14}$]dotetracont-38-ene-17,1'-cyclobutane]-3,6,9,15,18,21,25,28,31,34,42-undecone, PP3113: (2S,8S,12R,14S,20S,23S,27S,30S,36S,38Z)-20-cyclopentyl-32-cyclopropyl-8-[2-[3,5-difluoro-4-(trifluoromethyl)phenyl]ethyl]-12-ethoxy-4,16,19,22,26,35-hexamethyl-30-[(1 S)-1-methylpropyl]-27-propyl-2-(p-tolylmethyl)-23-(pyrrolidine-l-carbonyl)spiro[1,4,7,10,16,19,22,26,29,32,35-undecazatric clo[34.5.1.0$^{10,14}$]dotetracont-38-ene-17,1-cyclobutane]-3,6,9,15,18,21,25,28,31,34,42-undecone, PP3114: (1S,4S,10S,13S,17S,20S,26S,28R,32S,38S,42Z)-20-cyclopentyl-32-[2-[3,5-difluoro-4-(trifluoromethyl)phenyl]ethyl]-28-ethoxy-2,14,18,21,24,36-hexamethyl-10-[(1 S)-1-methylpropyl]-17-(piperidine-1-carbonyl)-13-propyl-38-[[4-(trifluoromethyl)phenyl]methyl]spiro[2,8,11,14,18,21,24,30,33,36,39-undecazatetracyclo[37.5.1.0$^{4,8}$.0$^{26,30}$]pentatetracont-42-ene-23,1'-cyclobutane]-3,9,12,15,19,22,25,31,34,37,45-undecone, PP3115: (1S,4S,1OS,13S,17S,20S,26S,28R,32S,38S,42Z)-20-cyclopentyl-32-[2-[3,5-difluoro-4-(trifluoromethyl)phenyl]ethyl]-28-ethoxy-2,14,18,21,24,36-hexamethyl-10-[(1 S)-1-methylpropyl]-17-(piperidine-1-carbonyl)-13-propyl-38-(p-tolylmethyl)spiro[2,8,11,14,18,21,24,30,33,36,39-undecazatetracyclo[37.5.1.0$^{4,8}$.0$^{26,30}$]pentatetracont-42-ene-23,1'-cyclobutane]-3,9,12,15,19,22,25,31,34,37,45-undecone, PP3116: (1S,4S,1OS,13S,17S,20S,26S,28R,32S,38S,42Z)-20-cyclopentyl-32-[2-[3,5-difluoro-4-(trifluoromethyl)phenyl]ethyl]-28-ethoxy-2,14,18,21,24,36-hexamethyl-10-[(1 S)-1-methylpropyl]-13-propyl-17-(pyrrolidine-1-carbonyl)-38-[[4-(trifluoromethyl)phenyl]methyl]spiro[2,8,11,14,18,21,24,30,33,36,39-undecazatetracyclo[37.5.1.0$^{4,8}$.0$^{26,30}$]pentatetracont-42-ene-23,1'-cyclobutane]-3,9,12,15,19,22,25,31,34,37,45-undecone, PP3117: (1S,4S,1OS,13S,17S,20S,26S,28R,32S,38S,42Z)-20-cyclopentyl-32-[2-[3,5-difluoro-4-(trifluoromethyl)phenyl]ethyl]-28-ethoxy-2,14,18,21,24,36-hexamethyl-10-[(1 S)-1-methylpropyl]-13-propyl-38-(p-tolylmethyl)-17-(pyrrolidine-l-carbonyl)spiro[2,8,11,14,18,21,24,30,33,36,39-undecazatetracyclo[37.5.1.0$^{4,8}$.0$^{26,30}$]pentatetracont-42-ene-23,1'-cyclobutane]-3,9,12,15,19,22,25,31,34,37,45-undecone, PP3118: (2S,8S,12R,14S,20S,23S,27S,30S,36S,38Z)-20-cyclopentyl-8-[2-[3,5-difluoro-4-(trifluoromethyl)phenyl]ethyl]-12-ethoxy-4,16,19,22,26,32,35-heptamethyl-30-[(1 S)-1-methylpropyl]-23-(piperidine-1-carbonyl)-27-propyl-2-[[4-(trifluoromethyl)phenyl]methyl]spiro[1,4,7,10,16,19,22,26,29,32,35-undecazatricyclo[34.5.1.0$^{10,14}$]dotetracont-38-ene-17,1'-cyclobutane]-3,6,9,15,18,21,25,28,31,34,42-undecone, PP3119: (2S,8S,12R,14S,20S,23S,27S,30S,36S,38Z)-20-cyclopentyl-8-[2-[3,5-difluoro-4-(trifluoromethyl)phenyl]ethyl]-12-ethoxy-4,16,19,22,26,32,35-heptamethyl-30-[(1 S)-1-methylpropyl]-23-(piperidine-1-carbonyl)-27-propyl-2-(p-tolylmethyl)spiro[[1,4,7,10,16,19,22,26,29,32,35-undecazatricyclo[34.5.1.0$^{10,14}$]dotetracont-38-ene-17,1-cyclobutane]-3,6,9,15,18,21,25,28,31,34,42-undecone, PP3120: (2S,8S,12R,14S,20S,23S,27S,30S,36S,38Z)-20-cyclopentyl-8-[2-[3,5-difluoro-4-(trifluoromethyl)phenyl]ethyl]-12-ethoxy-4,16,19,22,26,32,35-heptamethyl-30-[(1 S)-1-methylpropyl]-27-propyl-23-(pyrrolidine-1-carbonyl)-2-[[4-(trifluoromethyl)phenyl]methyl]spiro[1,4,7,10,16,19,22,26,29,32,35-undecazatricyclo[34.5.1.0$^{10,14}$]dotetracont-38-ene-17,1'-cyclobutane]-3,6,9,15,18,21,25,28,31,34,42-undecone, and PP3121: (2S,8S,12R,14S,20S,23S,27S,30S,36S,38Z)-20-cyclopentyl-8-[2-[3,5-difluoro-4-(trifluoromethyl)phenyl]ethyl]-12-ethoxy-4,16,19,22,26,32,35-heptamethyl-30-[(1 S)-1-methylpropyl]-27-propyl-2-(p-tolylmethyl)-23-(pyrrolidine-l-carbonyl)spiro[1,4,7,10,16,19,22,26,29,32,35-undecazatricyclo[34.5.1.0$^{10,14}$]dotetracont-38-ene-17,1-cyclobutane]-3,6,9,15,18,21,25,28,31,34,42- undecone. [4-1] A cyclic compound which is PP1574: (2S,8S,12R,14S,20S,23S,27S,30S,36S,38Z)-20-cyclopentyl-8-[112-$_{113,5}$-difluoro-4-(trifluoromethyl)phenyl]ethyl]-12-ethoxy-N-ethyl-27-isobutyl-N,4,19,22,26,32, 35-heptamethyl-30-[(1 S)-1-methylpropyl]-3,6,9,15,18, 21,25,28,31,34,42-undecaoxo-2-[[4-(trifluoromethyl)phenyl]methyl]spiro[4,7,10,16,19,22,26,29,32,35-undecazatricyclo[34.5.1.0$^{10,14}$]dotetracont-38-ene-17,1'-cyclopentane]-23-carboxamide, or a salt thereof, or a solvate thereof.

[4-2] A cyclic compound which is PP1650: (2S,8S,12R,14S, 20S,23S,27S,30S,36S,38Z)-20-cyclopentyl-8-[112-$_{113,5}$-difluoro-4-(trifluoromethyl)phenyl]ethyl]-12-ethoxy-27-isobutyl-N,N,3,3,4, 19,22,26,32,35-decamethyl-30-[(1 S)-1-methylpropyl]-3,6,9,15,18,21,25,28,31,34,42-undecaoxo-2-[[4-(trifluoromethyl)phenyl]methyl]spiro[1,4,7, 10,16,19,22,26,29,32,35-undecazatricyclo[34.5.1.0$^{10,14}$]dotetracont-38-ene-17,1'-cyclobutane]-23-carboxamide, or a salt thereof, or a solvate thereof.

[4-3] A cyclic compound which is PP1827: (1S,7S,11R,13S, 19S,22S,26S,29S,35S,37Z,47E)-19-cyclopentyl-7-[2-[3, 5-difluoro-4-(trifluoromethyl)phenyl]ethyl]-11-ethoxy-N-ethyl-N,3,18,21,25,31,34-heptamethyl-29-[(1S)-1-methylpropyl]-2,5,8,14,17,20,24,27,30,33,55-undecaoxo-spiro[3,6,9,15,18,21,25,28,31,34,41-undecazapentacyclo[24.15.11.2$^{43,46}$.1$^{35,41}$.0$^{9,13}$]pentapentaconta-37,43(54),44,46(53),47-pentaene-16,1'-cyclobutane]-22-carboxamide, or a salt thereof, or a solvate thereof.

[4-4] A cyclic compound which is PP1830: (1S,7S,11R,13S, 19S,22S,26S,29S,35S,37Z,47E)-19-cyclopentyl-11-ethoxy-N-ethyl-7-[112-$_{113}$-methoxy-4-(trifluoromethyl)phenyl]ethyl]-N,3,3,3, 18,21,25,31,34-nonamethyl-29-11 (1N,3,3',3',18,21,25,31,34-nonamethyl-29-[(1S)-1-methylpropyl]-2,5,8,14,17,20,24,27,30,33,55-undecaoxo-spiro[3,6,9,15,18,21,25,28,31,34,41-undecazapentacyclo[24.15.11.2$^{43,46}$.1$^{35,41}$.0$^{9,13}$]pentapentaconta-37,43(54),44,46(53),47-pentaene-16,1'-cyclobutane]-22-carboxamide, or a salt thereof, or a solvate thereof.

[4-5] A cyclic compound which is PP2093: (2S,8S,12R,14S, 20S,23S,27S,30S,36S,38Z)-20-cyclopentyl-32-cyclopropyl-8-[112-$_{113,5}$-difluoro-4-(trifluoromethyl)phenyl]ethyl]-12-ethoxy-N,N,3',3',4,19,22,26,35-nonamethyl-30-[(1 S)-1-methylpropyl]-3,6,9,15,18,21,25,28,31,34, 42-undecaoxo-27-propyl-2-(p-tolylmethyl)spiro[1,4,7, 10,16,19,22,26,29,32,35-undecazatricyclo[34.5.1.0$^{10,14}$]dotetracont-38-ene-17,1'-cyclobutane]-23-carboxamide, or a salt thereof, or a solvate thereof.

[4-6] A cyclic compound which is PP2260: (1S,7S,11R,13S, 19S,22S,26S,29S,35S,37Z)-19-cyclopentyl-11-ethoxy-N-ethyl-7-[2-[3-methoxy-4-(trifluoromethyl)phenyl]ethyl]-N,3,3',3',18,21,25,31,34-nonamethyl-29-[(1S)-1-methylpropyl]-2,5,8,14,17,20,24,27,30,33,55-undecaoxo-spiro[3,6,9,15,18,21,25,28,31,34,41-undecazapentacyclo[24.15.11.2$^{43,46}$.1$^{35,41}$.0$^{9,13}$]pentapentaconta-37,43(54),44,46(53)-tetraene-16,1'-cyclobutane]-22-carboxamide, or a salt thereof, or a solvate thereof. [4-7] A cyclic compound which is PP2316: (2S,8S, 12R, 14S,20S,23S,27S,30S,36S,38Z)-20-cyclopentyl-32-cyclopropyl-12-ethoxy-8-[2-[3-methoxy-4-(trifluoromethyl)phenyl]ethyl]-N,N,4,16,19, 22,26,35-octamethyl-30-[(1S)-1-methylpropyl]-3,6,9,15, 18,21,25,28,31,34,42-undecaoxo-27-propyl-2-[[4-(trifluoromethyl)phenyl]methyl]spiro[1,4,7,10,16,19,22, 26,29,32,35-undecazatricyclo[34.5.1.0$^{10,14}$]dotetracont-38-ene-17,1'-cyclobutane]-23-carboxamide, or a salt thereof, or a solvate thereof.

[4-8] A cyclic compound which is PP2320: (1S,4S,10S,13S, 17S,20S,26S,28R,32S,38S,42Z)-20-cyclopentyl-28-ethoxy-32-[2-[3-methoxy-4-(trifluoromethyl)phenyl]ethyl]-N,N,2,14,18,21,24,36-octamethyl-10-[(1 S)-1-methylpropyl]-3,9,12,15,19,22,25,31,34,37,45-undecaoxo-13-propyl-38-[[4-(trifluoromethyl)phenyl]methyl]spiro[2,8,11,14,18,21,24,30,33,36,39-undecazatetracyclo[37.5.1.0$^{4,8}$.0$^{26,30}$]pentatetracont-42-ene-23,1'-cyclobutane]-17-carboxamide, or a salt thereof, or a solvate thereof.

[4-9] A cyclic compound which is PP2328: (2S,8S, 12R, 14S,20S,23S,27S,30S,36S,38Z)-20-cyclopentyl-32-cyclopropyl-12-ethoxy-8-[2-[3-methoxy-4-(trifluoromethyl)phenyl]ethyl]-N,N,4,16,19,22,26,35-octamethyl-30-I1(1 S)-1-methylpropyl]-3,6,9,15,18,21,25,28,31,34, 42-undecaoxo-27-propyl-2-(p-tolylmethyl)spiro[1,4,7, 10,16,19,22,26,29,32,35-undecazatricyclo[34.5.1.0$^{10,14}$]dotetracont-38-ene-17,1'-cyclobutane]-23-carboxamide, or a salt thereof, or a solvate thereof.

[4-10] A cyclic compound which is PP2574: (1S,7S,11R, 13S,19S,22S,26S,29S,35S,37Z,47E)-19-cyclopentyl-7-[2-[3,5-difluoro-4-(trifluoromethyl)phenyl]ethyl]-11-ethoxy-3,3',3',18,21,25,31,34-octamethyl-29-[(1 S)-1-methylpropyl]-22-(pyrrolidine-l-carbonyl)spiro[3,6,9,15, 18,21,25,28,31,34,41-undecazapentacyclo[24.15. 10.2$^{43,46}$.1$^{35,41}$.0$^{9,13}$]tetrapentaconta-37,43(53),44,46 (52),47-pentaene-16,1'-cyclobutane]-2,5,8,14,17,20,24, 27,30,33,54-undecone, or a salt thereof, or a solvate thereof.

[4-11] A cyclic compound which is PP2576: (1S,7S,11R, 13S,19S,22S,26S,29S,35S,37Z,47E)-7-[2-[3,5-difluoro-4-(trifluoromethyl)phenyl]ethyl]-11-ethoxy-19-(1-ethyl-propyl)-3,3',3',18,21,25,31,34-octamethyl-29-[(1 S)-1-methylpropyl]-22-(pyrrolidine-l-carbonyl)spiro[3,6,9,15, 18,21,25,28,31,34,41-undecazapentacyclo[24.15. 10.2$^{43,46}$.1$^{35,41}$.0$^{9,13}$]tetrapentaconta-37,43(53),44,46 (52),47-pentaene-16,1'-cyclobutane]-2,5,8,14,17,20,24, 27,30,33,54-undecone, or a salt thereof, or a solvate thereof.

[4-12] A cyclic compound which is PP2583: (1S,7S,11R, 13S,19S,22S,26S,29S,35S,37Z,47E)-19-cyclopentyl-31-cyclopropyl-7-[2-[3,5-difluoro-4-(trifluoromethyl)phenyl]ethyl]-11-ethoxy-3,3',3',18,21,25,34-heptamethyl-29-[(1 S)-1-methylpropyl]-22-(pyrrolidine-l-carbonyl)spiro[3,6,9,15,18,21,25,28,31,34,41-undecazapentacyclo[24.15.10.2$^{43,46}$.1$^{35,41}$.0$^{9,13}$]tetrapentaconta-37,43(53), 44,46(52),47-pentaene-16,1'-cyclobutane]-2,5,8,14,17, 20,24,27,30,33,54-undecone, or a salt thereof, or a solvate thereof.

[4-13] A cyclic compound which is PP2687: (2S,8S,12R, 14S,20S,23S,27S,30S,36S,38Z)-20-cyclopentyl-12-ethoxy-2-[(4-ethylphenyl)methyl]-27-isobutyl-8-[2-[3-methoxy-4-(trifluoromethyl)phenyl]ethyl]-N,N,3',3',4,19, 22,26,32,35-decamethyl-30-[(1 S)-1-methylpropyl]-3,6, 9,15,18,21,25,28,31,34,42-undecaoxo-spiro[1,4,7,10,16, 19,22,26,29,32,35-undecazatricyclo[34.5.1.0$^{10,14}$]dotetracont-38-ene-17,1'-cyclobutane]-23-carboxamide, or a salt thereof, or a solvate thereof.

[4-14] A cyclic compound which is PP2691: (2S,8S,12R, 14S,20S,23S,27S,30S,36S,38Z)-20-cyclopentyl-2-[(4-cyclopropylphenyl)methyl]-12-ethoxy-27-isobutyl-8-[112-$_{113}$-methoxy-4-(trifluoromethyl)phenyl]ethyl]-N,N, 3,3,4, 19,22,26,32,35-decamethyl-30-i(1 S)-1-methylpropyl]-3,6,9,15,18,21,25,28,31,34,42-undecaoxo-spiro[1,4,7,10,16,19,22,26,29,32,35- undecazatricyclo[34.5.1.0$^{10,14}$]dotetracont-38-ene-17,1'-cyclobutane]-23-carboxamide, or a salt thereof, or a solvate thereof.

[4-15] A cyclic compound which is PP2957: (1S,7S,11R,13S,19S,22S,26S,29S,35S,37Z,47E)-31-cyclopropyl-7-[2-[3,5-difluoro-4-(trifluoromethyl)phenyl]ethyl]-11-ethoxy-19-(1-ethylpropyl)-3,18,21,25,34-pentamethyl-29-[(1 S)-1-methylpropyl]-22-(pyrrolidine-l-carbonyl)spiro[3,6,9,15,18,21,25,28,31,34,41-undecazapentacyclo[24.15.10.2$^{43,46}$.1$^{35,41}$.0$^{9,13}$]tetrapentaconta-37,43(53),44,46(52),47-pentaene-16,1'-cyclobutane]-2,5,8,14,17,20,24,27,30,33,54-undecone, or a salt thereof, or a solvate thereof.

[4-16] A cyclic compound which is PP3033: (1S,7S,1IR,13S,19S,22S,26S,29S,35S,37Z)-19-cyclopentyl-11-ethoxy-7-[2-[3-methoxy-4-(trifluoromethyl)phenyl]ethyl]-3,18,21,25,31,34-hexamethyl-29-[(1S)-1-methylpropyl]-22-(piperidine-l-carbonyl)spiro[3,6,9,15,18,21,25,28,31,34,41-undecazapentacyclo[24.15.11.2$^{43,46}$.1$^{35,41}$.0$^{9,13}$]pentapentaconta-37,43(54),44,46(53)-tetraene-16,1'-cyclobutane]-2,5,8,14,17,20,24,27,30,33,55-undecone, or a salt thereof, or a solvate thereof.

[4-17] A cyclic compound which is PP3034: (1S,7S,1IR,13S,19S,22S,26S,29S,35S,37Z)-19-cyclopentyl-11-ethoxy-7-[2-[3-methoxy-4-(trifluoromethyl)phenyl]ethyl]-3,3',3',18,21,25,31,34-octamethyl-29-[(1S)-1-methylpropyl]-22-(pyrrolidine-l-carbonyl)spiro[3,6,9,15,18,21,25,28,31,34,41-undecazapentacyclo[24.15.11.2$^{43,46}$.1$^{35,41}$.0$^{9,13}$]pentapentaconta-37,43(54),44,46(53)-tetraene-16,1'-cyclobutane]-2,5,8,14,17,20,24,27,30,33,55-undecone, or a salt thereof, or a solvate thereof.

[4-18] A cyclic compound which is PP3036: (1S,7S,11R,13S,19S,22S,26S,29S,35S,37Z)-19-cyclopentyl-11-ethoxy-7-[2-[3-methoxy-4-(trifluoromethyl)phenyl]ethyl]-3,3',3',18,21,25,31,34-octamethyl-29-[(1 S)-1-methylpropyl]-22-(piperidine-l-carbonyl)spiro[3,6,9,15,18,21,25,28,31,34,41-undecazapentacyclo[24.15.10.2$^{43,46}$.1$^{35,41}$.0$^{9,13}$]tetrapentaconta-37,43(53),44,46(52)-tetraene-16,1'-cyclobutane]-2,5,8,14,17,20,24,27,30,33,54-undecone, or a salt thereof, or a solvate thereof.

[4-19] A cyclic compound which is PP3037: (1S,7S,11R,13S,19S,22S,26S,29S,35S,37Z)-19-cyclopentyl-11-ethoxy-7-[2-[3-methoxy-4-(trifluoromethyl)phenyl]ethyl]-3,3',3',18,21,25,31,34-octamethyl-29-[(1 S)-1-methylpropyl]-22-(pyrrolidine-1-carbonyl)spiro[3,6,9,15,18,21,25,28,31,34,41-undecazapentacyclo[24.15.10.2$^{43,46}$.1$^{35,41}$.0$^{9,13}$]tetrapentaconta-37,43(53),44,46(52)-tetraene-16,1'-cyclobutane]-2,5,8,14,17,20,24,27,30,33,54-undecone, or a salt thereof, or a solvate thereof.

[4-20] A cyclic compound which is PP3047: (1S,7S,11R,13S,19S,22S,26S,29S,35S,37Z,47E)-7-[2-(3,4-dichlorophenyl)ethyl]-11-ethoxy-19-(1-ethylpropyl)-3,18,21,25,31,34-hexamethyl-29-[(1 S)-1-methylpropyl]-22-(pyrrolidine-1-carbonyl)Spiro[3,6,9,15,18,21,25,28,31,34,41-undecazapentacyclo[24.15.11.2$^{43,46}$.1$^{35,41}$.0$^{9,13}$]pentapentaconta-37,43(54),44,46(53),47-pentaene-16,1'-cyclobutane]-2,5,8,14,17,20,24,27,30,33,55-undecone, or a salt thereof, or a solvate thereof.

[4-21] A cyclic compound which is PP3093: (1S,7S,11R,13S,19S,22S,26S,29S,35S,37Z)-19-cyclopentyl-11-ethoxy-7-[2-[3-methoxy-4-(trifluoromethyl)phenyl]ethyl]-3,3',3',18,21,25,31,34-octamethyl-29-[(1 S)-1-methylpropyl]-22-(piperidine-1-carbonyl)spiro[3,6,9,15,18,21,25,28,31,34,41-undecazapentacyclo[24.15.9.2$^{43,46}$.1$^{35,41}$.0$^{9,13}$]tripentaconta-37,43(52),44,46(51)-tetraene-16,1'-cyclobutane]-2,5,8,14,17,20,24,27,30,33,53-undecone, or a salt thereof, or a solvate thereof.

[4-22] A cyclic compound which is PP3094: (1S,7S,11R,13S,19S,22S,26S,29S,35S,37Z)-19-cyclopentyl-7-[2-[3-methoxy-4-(trifluoromethyl)phenyl]ethyl]-3,3',3',18,21,25,31,34-octamethyl-29-[(1 S)-1-methylpropyl]-11-propoxy-22-(pyrrolidine-l-carbonyl)spiro[3,6,9,15,18,21,25,28,31,34,41-undecazapentacyclo[24.15.9.2$^{43,46}$.1$^{35,41}$.0$^{9,13}$]tripentaconta-37,43(52),44,46(51)-tetraene-16,1'-cyclobutane]-2,5,8,14,17,20,24,27,30,33,53-undecone, or a salt thereof, or a solvate thereof.

[4-23] A cyclic compound which is PP3095: (2S,8S, 12R,14S,20S,23S,27S,30S,36S,38Z)-20-cyclopentyl-32-cyclopropyl-12-ethoxy-8-[2-[3-methoxy-4-(trifluoromethyl)phenyl]ethyl]-4,16,19,22,26,35-hexamethyl-30-[(1 S)-1-methylpropyl]-23-(piperidine-1-carbonyl)-27-propyl-2-[[4-(trifluoromethyl)phenyl]methyl]spiro[1,4,7,10,16,19,22,26,29,32,35-undecazatricyclo[34.5.1.0$^{10,14}$]dotetracont-38-ene-17,1'-cyclobutane]-3,6,9,15,18,21,25,28,31,34,42-undecone, or a salt thereof, or a solvate thereof.

[4-24] A cyclic compound which is PP3096: (2S,8S,12R,14S,20S,23S,27S,30S,36S,38Z)-20-cyclopentyl-32-cyclopropyl-12-ethoxy-8-[2-[3-methoxy-4-(trifluoromethyl)phenyl]ethyl]-4,16,19,22,26,35-hexamethyl-30-[(1 S)-1-methylpropyl]-23-(piperidine-1-carbonyl)-27-propyl-2-(p-tolylmethyl)spiro[1,4,7,10,16,19,22,26,29,32,35-undecazatricyclo[34.5.1.0$^{10,14}$]dotetracont-38-ene-17,1'-cyclobutane]-3,6,9,15,18,21,25,28,31,34,42-undecone, or a salt thereof, or a solvate thereof.

[4-25] A cyclic compound which is PP3097: (2S,8S,12R,14S,20S,23S,27S,30S,36S,38Z)-20-cyclopentyl-32-cyclopropyl-12-ethoxy-8-[2-[3-methoxy-4-(trifluoromethyl)phenyl]ethyl]-4,16,19,22,26,35-hexamethyl-30-[(1 S)-1-methylpropyl]-27-propyl-23-(pyrrolidine-1-carbonyl)-2-[[4-(trifluoromethyl)phenyl]methyl]spiro[1,4,7,10,16,19,22,26,29,32,35-undecazatricyclo[34.5.1.0$^{10,14}$]dotetracont-38-ene-17,1'-cyclobutane]-3,6,9,15,18,21,25,28,31,34,42-undecone, or a salt thereof, or a solvate thereof.

[4-26] A cyclic compound which is PP3098: (2S,8S,12R,14S,20S,23S,27S,30S,36S,38Z)-20-cyclopentyl-32-cyclopropyl-12-ethoxy-8-[2-[3-methoxy-4-(trifluoromethyl)phenyl]ethyl]-4,16,19,22,26,35-hexamethyl-30-[(1 S)-1-methylpropyl]-27-propyl-2-(p-tolylmethyl)-23-(pyrrolidine-1-carbonyl)spiro[1,4,7,10,16,19,22,26,29,32,35-undecazatricyclo[34.5.1.0$^{10,14}$]dotetracont-38-ene-17,1'-cyclobutane]-3,6,9,15,18,21,25,28,31,34,42-undecone, or a salt thereof, or a solvate thereof.

[4-27] A cyclic compound which is PP3099: (1S,4S,10S,13S,17S,20S,26S,28R,32S,38S,42Z)-20-cyclopentyl-28-ethoxy-32-[112-113-methoxy-4-(trifluoromethyl)phenyl]ethyl]-2, 14,18,21,24,36-hexamethyl-10-[(1 S)-1-methylpropyl]-17-(piperidine-1-carbonyl)-13-propyl-38-[[4-(trifluoromethyl)phenyl]methyl]spiro[2,8,11,14,18,21,24,30,33,36,39-undecazatetracyclo[37.5.1.0$^{4,8}$.0$^{26,30}$]pentatetracont-42-ene-23,1'-cyclobutane]-3,9,12,15,19,22,25,31,34,37,45-undecone, or a salt thereof, or a solvate thereof.

[4-28] A cyclic compound which is PP3100: (1S,4S,10S,13S,17S,20S,26S,28R,32S,38S,42Z)-20-cyclopentyl-28-ethoxy-32-[112-113-methoxy-4-(trifluoromethyl)phenyl]ethyl]-2, 14,18,21,24,36-hexamethyl-10-[(1 S)-1-methylpropyl]-17-(piperidine-1-carbonyl)-13-propyl-38-(p-tolylmethyl)spiro[2,8,11,14,18,21,24,30,33,36,39-undecazatetracyclo[37.5.1.0$^{4,8}$.0$^{26,30}$]pentatetracont-42-ene-23,1'-cyclobutane]-3,9,12,15,19,22,25,31,34,37,45-undecone, or a salt thereof, or a solvate thereof.

[4-29] A cyclic compound which is PP3101: (1S,4S,10S, 13S,17S,20S,26S,28R,32S,38S,42Z)-20-cyclopentyl-28-ethoxy-32-[112-113-methoxy-4-(trifluoromethyl)phenyl] ethyl]-2, 14,18,21,24,36-hexamethyl-10-[(1 S)-1-methylpropyl]-13-propyl-17-(pyrrolidine-1-carbonyl)-38-[[4-(trifluoromethyl)phenyl]methyl]spiro[2,8,11,14, 18,21,24,30,33,36,39-undecazatetracyclo[37.5. 1.0$^{4,8}$.0$^{26,30}$]pentatetracont-42-ene-23,1'-cyclobutane]-3, 9,12,15,19,22,25,31,34,37,45-undecone, or a salt thereof, or a solvate thereof.

[4-30] A cyclic compound which is PP3102: (1S,4S,10S, 13S,17S,20S,26S,28R,32S,38S,42Z)-20-cyclopentyl-28-ethoxy-32-[112-113-methoxy-4-(trifluoromethyl)phenyl] ethyl]-2, 14,18,21,24,36-hexamethyl-10-[(1 S)-1-methylpropyl]-13-propyl-38-(p-tolylmethyl)-17-(pyrrolidine-1-carbonyl)spiro[2,8,11,14,18,21,24,30,33, 36,39-undecazatetracyclo[37.5.1.0$^{4,8}$.0$^{26,30}$] pentatetracont-42-ene-23,1'-cyclobutane]-3,9,12,15,19, 22,25,31,34,37,45-undecone, or a salt thereof, or a solvate thereof.

[4-31] A cyclic compound which is PP3103: (2S,8S,12R, 14S,20S,23S,27S,30S,36S,38Z)-20-cyclopentyl-12-ethoxy-8-[2-[3-methoxy-4-(trifluoromethyl)phenyl] ethyl]-4,16,19,22,26,32,35-heptamethyl-30-[(1 S)-1-methylpropyl]-23-(piperidine-1-carbonyl)-27-propyl-2-[[4-(trifluoromethyl)phenyl]methyl]spiro[1,4,7,10,16,19, 22,26,29,32,35-undecazatricyclo[34.5.1.0$^{10,14}$1 dotetracont-38-ene-17,1'-cyclobutane]-3,6,9,15,18,21,25, 28,31,34,42-undecone, or a salt thereof, or a solvate thereof.

[4-32] A cyclic compound which is PP3104: (2S,8S,12R, 14S,20S,23S,27S,30S,36S,38Z)-20-cyclopentyl-12-ethoxy-8-[2-[3-methoxy-4-(trifluoromethyl)phenyl] ethyl]-4,16,19,22,26,32,35-heptamethyl-30-[(1 S)-1-methylpropyl]-23-(piperidine-1-carbonyl)-27-propyl-2-(p-tolylmethyl)spiro[[1,4,7,10,16,19,22,26,29,32,35-undecazatric clo[34.5.1.0$^{10,14}$]dotetracont-38-ene-17,1'-cyclobutane]-3,6,9,15,18,21,25,28,31,34,42-undecone, or a salt thereof, or a solvate thereof.

[4-33] A cyclic compound which is PP3105: (2S,8S,12R, 14S,20S,23S,27S,30S,36S,38Z)-20-cyclopentyl-12-ethoxy-8-[2-[3-methoxy-4-(trifluoromethyl)phenyl] ethyl]-4,16,19,22,26,32,35-heptamethyl-30-[(1 S)-1-methylpropyl]-27-propyl-23-(pyrrolidine-1-carbonyl)-2-[[4-(trifluoromethyl)phenyl]methyl]spiro[1,4,7,10,16,19, 22,26,29,32,35-undecazatricyclo[34.5.1.0$^{10,14}$1 dotetracont-38-ene-17,1'-cyclobutane]-3,6,9,15,18,21,25, 28,31,34,42-undecone, or a salt thereof, or a solvate thereof.

[4-34] A cyclic compound which is PP3106: (2S,8S,12R, 14S,20S,23S,27S,30S,36S,38Z)-20-cyclopentyl-12-ethoxy-8-[2-[3-methoxy-4-(trifluoromethyl)phenyl] ethyl]-4,16,19,22,26,32,35-heptamethyl-30-[(1 S)-1-methylpropyl]-27-propyl-2-(p-tolylmethyl)-23-(pyrrolidine-1-carbonyl)spiro[1,4,7,10,16,19,22,26,29, 32,35-undecazatric clo[34.5.1.0$^{10,14}$]dotetracont-38-ene-17,1'-cyclobutane]-3,6,9,15,18,21,25,28,31,34,42-undecone, or a salt thereof, or a solvate thereof.

[4-35] A cyclic compound which is PP3110: (2S,8S,12R, 14S,20S,23S,27S,30S,36S,38Z)-20-cyclopentyl-32-cyclopropyl-8-[2-[3,5-difluoro-4-(trifluoromethyl)phenyl] ethyl]-12-ethoxy-4,16,19,22,26,35-hexamethyl-30-[(1 S)-1-methylpropyl]-23-(piperidine-1-carbonyl)-27-propyl-2-[[4-(trifluoromethyl)phenyl]methyl]spiro[1,4,7,10, 16,19,22,26,29,32,35-undecazatricyclo[34.5.1.0$^{10,14}$]dotetracont-38-ene-17,1'-cyclobutane]-3,6,9,15,18,21,25, 28,31,34,42-undecone, or a salt thereof, or a solvate thereof.

[4-36] A cyclic compound which is PP3111: (2S,8S,12R, 14S,20S,23S,27S,30S,36S,38Z)-20-cyclopentyl-32-cyclopropyl-8-[2-[3,5-difluoro-4-(trifluoromethyl)phenyl] ethyl]-12-ethoxy-4,16,19,22,26,35-hexamethyl-30-[(1 S)-1-methylpropyl]-23-(piperidine-1-carbonyl)-27-propyl-2-tolylmethyl)spiro[[1,4,7,10,16,19,22,26,29,32,35-undecazatricyclo[34.5.1.0$^{10,14}$]dotetracont-38-ene-17,1'-cyclobutane]-3,6,9,15,18,21,25,28,31,34,42-undecone, or a salt thereof, or a solvate thereof.

[4-37] A cyclic compound which is PP3112: (2S,8S,12R, 14S,20S,23S,27S,30S,36S,38Z)-20-cyclopentyl-32-cyclopropyl-8-[2-[3,5-difluoro-4-(trifluoromethyl)phenyl] ethyl]-12-ethoxy-4,16,19,22,26,35-hexamethyl-30-[(1 S)-1-methylpropyl]-27-propyl-23-(pyrrolidine-1-carbonyl)-2-[[4-(trifluoromethyl)phenyl]methyl]spiro[1,4,7, 10,16,19,22,26,29,32,35-undecazatricyclo[34.5.1. 0$^{10,14}$1dotetracont-38-ene-17,1'-cyclobutane]-3,6,9,15, 18,21,25,28,31,34,42-undecone, or a salt thereof, or a solvate thereof.

[4-38] A cyclic compound which is PP3113: (2S,8S,12R, 14S,20S,23S,27S,30S,36S,38Z)-20-cyclopentyl-32-cyclopropyl-8-[2-[3,5-difluoro-4-(trifluoromethyl)phenyl] ethyl]-12-ethoxy-4,16,19,22,26,35-hexamethyl-30-[(1 S)-1-methylpropyl]-27-propyl-2-(p-tolylmethyl)-23-(pyrrolidine-1-carbonyl)spiro[1,4,7,10,16,19,22,26,29,32,35-undecazatricyclo[34.5.1.0$^{10,14}$]dotetracont-38-ene-17,1'-cyclobutane]-3,6,9,15,18,21,25,28,31,34,42-undecone, or a salt thereof, or a solvate thereof.

[4-39] A cyclic compound which is PP3114: (1S,4S,10S, 13S,17S,20S,26S,28R,32S,38S,42Z)-20-cyclopentyl-32-[2-[3,5-difluoro-4-(trifluoromethyl)phenyl]ethyl]-28-ethoxy-2,14,18,21,24,36-hexamethyl-10-[(1 S)-1-methylpropyl]-17-(piperidine-1-carbonyl)-13-propyl-38-[[4-(trifluoromethyl)phenyl]methyl]spiro[2,8,11,14,18, 21,24,30,33,36,39-undecazatetracyclo[37.5.1.0$^{4,8}$.0$^{26,30}$] pentatetracont-42-ene-23,1'-cyclobutane]-3,9,12,15,19, 22,25,31,34,37,45-undecone, or a salt thereof, or a solvate thereof.

[4-40] A cyclic compound which is PP3115: (1S,4S,10S, 13S,17S,20S,26S,28R,32S,38S,42Z)-20-cyclopentyl-32-[2-[3,5-difluoro-4-(trifluoromethyl)phenyl]ethyl]-28-ethoxy-2,14,18,21, 24,36-hexamethyl-10-[(1 S)-1-methylpropyl]-17-(piperidine-1-carbonyl)-13-propyl-38-(p-tolylmethyl)spiro[2,8,11,14,18,21,24,30,33,36,39-undecazatetracyclo[37.5.1.0$^{4,8}$.0$^{26,30}$]pentatetracont-42-ene-23,1'-cyclobutane]-3,9,12,15,19,22,25,31,34,37,45-undecone, or a salt thereof, or a solvate thereof.

[4-41] A cyclic compound which is PP3116: (1S,4S,10S, 13S,17S,20S,26S,28R,32S,38S,42Z)-20-cyclopentyl-32-[2-[3,5-difluoro-4-(trifluoromethyl)phenyl]ethyl]-28-ethoxy-2,14,18,21, 24,36-hexamethyl-10-[(1 S)-1-methylpropyl]-13-propyl-17-(pyrrolidine-1-carbonyl)-38-[[4-(trifluoromethyl)phenyl]methyl]spiro[2,8,11,14, 18,21,24,30,33,36,39-undecazatetracyclo[37.5.1. 0$^{4,8}$.0$^{26,30}$]pentatetracont-42-ene-23,1'-cyclobutane]-3,9, 12,15,19,22,25,31,34,37,45-undecone, or a salt thereof, or a solvate thereof.

[4-42] A cyclic compound which is PP3117: (1S,4S,10S, 13S,17S,20S,26S,28R,32S,38S,42Z)-20-cyclopentyl-32-[2-[3,5-difluoro-4-(trifluoromethyl)phenyl]ethyl]-28-ethoxy-2,14,18,21, 24,36-hexamethyl-10-[(1 S)-1-methylpropyl]-13-propyl-38-(p-tolylmethyl)-17-(pyrrolidine-1-carbonyl)spiro[2,8,11,14,18,21,24,30,33, 36,39-undecazatetracyclo[37.5.1.0$^{4,8}$.0$^{26,30}$]

[4-42] ... pentatetracont-42-ene-23,1'-cyclobutane]-3,9,12,15,19, 22,25,31,34,37,45-undecone, or a salt thereof, or a solvate thereof.

[4-43] A cyclic compound which is PP3118: (2S,8S,12R, 14S,20S,23S,27S,30S,36S,38Z)-20-cyclopentyl-8-[2-[3, 5-difluoro-4-(trifluoromethyl)phenyl]ethyl]-12-ethoxy-4, 16,19,22,26,32,35-heptamethyl-30-[(1 S)-1-methylpropyl]-23-(piperidine-1-carbonyl)-27-propyl-2-[[4-(trifluoromethyl)phenyl]methyl]spiro[1,4,7,10,16,19, 22,26,29,32,35-undecazatricyclo[34.5. 1.0$^{10,14}$]dotetracont-38-ene-17,1'-cyclobutane]-3,6,9,15, 18,21,25,28,31,34,42-undecone, or a salt thereof, or a solvate thereof.

[4-44] A cyclic compound which is PP3119: (2S,8S,12R, 14S,20S,23S,27S,30S,36S,38Z)-20-cyclopentyl-8-[2-[3, 5-difluoro-4-(trifluoromethyl)phenyl]ethyl]-12-ethoxy-4, 16,19,22,26,32,35-heptamethyl-30-[(1 S)-1-methylpropyl]-23-(piperidine-1-carbonyl)-27-propyl-2-(p-tolylmethyl)spiro[[1,4,7,10,16,19,22,26,29,32,35-undecazatricyclo[34.5.1.0$^{10,14}$]dotetracont-38-ene-17,1'-cyclobutane]-3,6,9,15,18,21,25,28,31,34,42-undecone, or a salt thereof, or a solvate thereof.

[4-45] A cyclic compound which is PP3120: (2S,8S,12R, 14S,20S,23S,27S,30S,36S,38Z)-20-cyclopentyl-8-[2-[3, 5-difluoro-4-(trifluoromethyl)phenyl]ethyl]-12-ethoxy-4, 16,19,22,26,32,35-heptamethyl-30-[(1 S)-1-methylpropyl]-27-propyl-23-(pyrrolidine-1-carbonyl)-2-[[4-(trifluoromethyl)phenyl]methyl]spiro[1,4,7,10,16,19, 22,26,29,32,35-undecazatricyclo[34.5.1.0$^{10,14}$]1 dotetracont-38-ene-17,1'-cyclobutane]-3,6,9,15,18,21,25, 28,31,34,42-undecone, or a salt thereof, or a solvate thereof.

[4-46] A cyclic compound which is PP3121: (2S,8S,12R, 14S,20S,23S,27S,30S,36S,38Z)-20-cyclopentyl-8-[2-[3, 5-difluoro-4-(trifluoromethyl)phenyl]ethyl]-12-ethoxy-4, 16,19,22,26,32,35-heptamethyl-30-[(1 S)-1-methylpropyl]-27-propyl-2-(p-tolylmethyl)-23-(pyrrolidine-1-carbonyl)spiro[1,4,7,10,16,19,22,26,29,32, 35-undecazatric clo[34.5.1.0$^{10,14}$]dotetracont-38-ene-17, 1'-cyclobutane]-3,6,9,15,18,21,25,28,31,34,42-undecone, or a salt thereof, or a solvate thereof.

[4-47] A cyclic compound which is (1S,7S,11R,13S,19S, 22S,26S,29S,35S,37Z,47Z)-19-cyclopentyl-7-[2-[3,5-difluoro-4-(trifluoromethyl)phenyl]ethyl]-1I-ethoxy-N-ethyl-N,3,18,21,25,31,34-heptamethyl-29-[(1S)-1-methylpropyl]-2,5,8,14,17,20,24,27,30,33,55-undecaoxo-spiro[3,6,9,15,18,21,25,28,31,34,41-undecazapentacyclo[24.15.11.2$^{43,46}$.1$^{35,41}$.0$^{9,13}$] pentapentaconta-37,43(54),44,46(53),47-pentaene-16,1'-cyclobutane]-22-carboxamide, or a salt thereof, or a solvate thereof.

[4-48] A cyclic compound which is (1S,7S,11R,13S,19S, 22S,26S,29S,35S,37Z,47Z)-19-cyclopentyl-11-ethoxy-N-ethyl-7-[112-$_{113}$-methoxy-4-(trifluoromethyl)phenyl] ethyl]-N,3,3,3, 18,21,25,31,34-nonamethyl-29-I1(N,3, 3',3',18,21,25,31,34-nonamethyl-29-[(1S)-1-methylpropyl]-2,5,8,14,17,20,24,27,30,33,55-undecaoxo-spiro[3,6,9,15,18,21,25,28,31,34,41-undecazapentacyclo[24.15.11.2$^{43,46}$.1$^{35,41}$.0$^{9,13}$] pentapentaconta-37,43(54),44,46(53),47-pentaene-16,1'-cyclobutane]-22-carboxamide, or a salt thereof, or a solvate thereof.

[4-49] A cyclic compound which is (1S,7S,11R,13S,19S, 22S,26S,29S,35S,37Z,47Z)-19-cyclopentyl-7-[2-[3,5-difluoro-4-(trifluoromethyl)phenyl]ethyl]-11-ethoxy-3,3', 3',18,21,25,31,34-octamethyl-29-[(1 S)-1-methylpropyl]-22-(pyrrolidine-l-carbonyl)spiro[3,6,9,15,18,21,25,28,31, 34,41-undecazapentacyclo[24.15.10.2$^{43,46}$.1$^{35,41}$.0$^{9,13}$] tetrapentaconta-37,43(53),44,46(52),47-pentaene-16,1'-cyclobutane]-2,5,8,14,17,20,24,27,30,33,54-undecone, or a salt thereof, or a solvate thereof.

[4-50] A cyclic compound which is (1S,7S,11R,13S,19S, 22S,26S,29S,35S,37Z,47Z)-7-[2-[3,5-difluoro-4-(trifluoromethyl)phenyl]ethyl]-11-ethoxy-19-(1-ethylpropyl)-3, 3',3',18,21,25,31,34-octamethyl-29-[(1 S)-1-methylpropyl]-22-(pyrrolidine-l-carbonyl)spiro[3,6,9,15, 18,21,25,28,31,34,41-undecazapentacyclo[24. 15.10.2$^{43,46}$.1$^{35,41}$.0$^{9,13}$]tetrapentaconta-37,43(53),44,46 (52),47-pentaene-16,1'-cyclobutane]-2,5,8,14,17,20,24, 27,30,33,54-undecone, or a salt thereof, or a solvate thereof.

[4-51] A cyclic compound which is (1S,7S,11R,13S,19S, 22S,26S,29S,35S,37Z,47Z)-19-cyclopentyl-31-cyclopropyl-7-[2-[3,5-difluoro-4-(trifluoromethyl)phenyl]ethyl]-11-ethoxy-3,3',3',18,21,25,31,34-heptamethyl-29-[(1 S)-1-methylpropyl]-22-(pyrrolidine-l-carbonyl)spiro[3,6,9,15, 18,21,25,28,31,34,41-undecazapentacyclo[24.15.10. 2$^{43,46}$.1$^{35,41}$.0$^{9,13}$]tetrapentaconta-37,43(53),44,46(52), 47-pentaene-16,1'-cyclobutane]-2,5,8,14,17,20,24,27,30, 33,54-undecone, or a salt thereof, or a solvate thereof.

[4-52] A cyclic compound which is (1S,7S,11R,13S,19S, 22S,26S,29S,35S,37Z,47Z)-31-cyclopropyl-7-[2-[3,5-difluoro-4-(trifluoromethyl)phenyl]ethyl]-11-ethoxy-19-(1-ethylpropyl)-3,18,21,25,31,34-pentamethyl-29-[(1S)-1-methylpropyl]-22-(pyrrolidine-l-carbonyl)spiro[3,6,9,15, 18,21,25,28,31,34,41-undecazapentacyclo[24.15.10. 2$^{43,46}$.1$^{35,41}$.0$^{9,13}$]tetrapentaconta-37,43(53),44,46(52), 47-pentaene-16,1'-cyclobutane]-2,5,8,14,17,20,24,27,30, 33,54-undecone, or a salt thereof, or a solvate thereof.

[4-53] A cyclic compound which is (1S,7S,11R,13S,19S, 22S,26S,29S,35S,37Z,47Z)-7-[2-(3,4-dichlorophenyl) ethyl]-1I-ethoxy-19-(I-ethylpropyl)-3,18,21,25,31,34-hexamethyl-29-[(1S)-l-methylpropyl]-22-(pyrrolidine-1-carbonyl)spiro[3,6,9,15,18,21,25,28,31,34,41-undecazapentacyclo[24.15.11.2$^{43,46}$.1$^{35,41}$.0$^{9,13}$] pentapentaconta-37,43(54),44,46(53),47-pentaene-16,1'-cyclobutane]-2,5,8,14,17,20,24,27,30,33,55-undecone The cyclic compound or a salt thereof according to any one of [1] to [4-53].

The cyclic compound or a solvate thereof according to any one of [1] to [4-53].

A solvate of the cyclic compound or a salt thereof according to any one of [1] to [4-53].

The cyclic compound according to any one of [1] to [4-53].

The cyclic compound or a salt thereof, or a solvate thereof according to any one of [1] to [4-53], which binds to KRAS.

The cyclic compound or a salt thereof, or a solvate thereof according to any one of [1] to [4-53], which inhibits KRAS.

The cyclic compound or a salt thereof, or a solvate thereof according to any one of [1] to [4-53], which has high selectivity for KRAS.

The cyclic compound or a salt thereof, or a solvate thereof according to any one of [1] to [4-53], having KRAS selectivity (KRAS selectivity to NRAS and/or KRAS selectivity to HRAS) higher than PP1820: ((3S,9S,12S, 17S,20S,23S, 27S,30S,36S)-3-[2-[3-chloro-4-(trifluoromethyl)phenyl] ethyl] 30)-cyclopentyl-23-isobutyl-9-(isopentyloxymethyl)-N,N,7,17,18,24,28,31-octamethyl-20-[(1S)-1-methylpropyl]-2,5,8, 11,16,19,22,25,29,32,35-undecaoxo-10-propyl-spiro[1,4,7, 10,15, 18,21,24,28,31,34-undecazatricyclo[34.3.0.012, 15] nonatriacontane-33,l'-cyclobutane]-27-carboxamide).

The cyclic compound or a salt thereof, or a solvate thereof according to any one of [1] to [4-53], which selectively binds to KRAS.

The cyclic compound or a salt thereof, or a solvate thereof according to any one of [1] to [4-53], which selectively inhibits KRAS.

The cyclic compound or a salt thereof, or a solvate thereof according to any one of [1] to [4-53], which has KRAS binding activity that is 3 times or more higher than NRAS binding activity and HRAS binding activity.

The cyclic compound or a salt thereof, or a solvate thereof according to [15], which has KRAS binding activity that is is 5 times, 7 times, 10 times, 15 times, or 20 times or more higher than NRAS binding activity and HRAS binding activity.

The cyclic compound or a salt thereof, or a solvate thereof according to any one of [1] to [4-53], which has KRAS inhibitory activity that is 3 times or more higher than NRAS inhibitory activity and HRAS inhibitory activity.

The cyclic compound or a salt thereof, or a solvate thereof according to [17], which has KRAS inhibitory activity that is is 5 times, 7 times, 10 times, 15 times, or 20 times or more higher than NRAS inhibitory activity and HRAS inhibitory activity.

A pharmaceutical composition comprising the cyclic compound or a salt thereof, or a solvate thereof according to any one of [1] to [4-53].

A pharmaceutical composition for selectively inhibiting KRAS in a subject, the composition comprising the cyclic compound or a salt thereof, or a solvate thereof according to any one of [1] to [4-53].

The pharmaceutical composition according to [20], wherein KRAS inhibitory activity of the compound is 3 times or more higher than NRAS inhibitory activity and HRAS inhibitory activity of the compound.

The pharmaceutical composition according to [21], wherein KRAS inhibitory activity of the compound is 5 times, 7 times, 10 times, 15 times, or 20 times or more higher than NRAS inhibitory activity and HRAS inhibitory activity of the compound.

A pharmaceutical composition for treating or preventing cancer in a subject, the composition comprising an effective amount of the cyclic compound or a salt thereof, or a solvate thereof according to any one of [1] to [4-53].

The pharmaceutical composition according to [23], wherein the cancer is lung cancer.

The pharmaceutical composition of any one of to [24], wherein the subject is a human.

The cyclic compound or a salt thereof, or a solvate thereof according to any one of [1] to [4-53] for use in treatment or prevention of cancer in a subject.

The cyclic compound or a salt thereof, or a solvate thereof according to [26], wherein the cancer is lung cancer.

The cyclic compound or a salt thereof, or a solvate thereof according to any one of [1] to [4-53] for use in selectively inhibiting KRAS in a subject.

The cyclic compound or a salt thereof, or a solvate thereof according to any one of to [28], wherein the subject is a human.

Use of the cyclic compound or a salt thereof, or a solvate thereof according to any one of [1] to [4-53] in the manufacture of a medicament for treating or preventing cancer in a subject. The use according to [30], wherein the cancer is lung cancer.

Use of the cyclic compound or a salt thereof, or a solvate thereof according to any one of [1] to [4-53] in the manufacture of a medicament for selectively inhibiting KRAS in a subject.

The use according to any one of to [32], wherein the subject is a human.

A method for treating or preventing cancer in a subject, the method comprising administering an effective amount of the cyclic compound or a salt thereof, or a solvate thereof according to any one of [1] to [4-53] to a subject in need thereof.

The method according to [34], wherein the cancer is lung cancer.

A method for selectively inhibiting KRAS in a subject, the method comprising administering an effective amount of the cyclic compound or a salt thereof, or a solvate thereof according to any one of [1] to [4-53] to a subject in need thereof.

The method according to any one of to [36], wherein the subject is a human.

Effects of the Invention

The present invention can provide novel cyclic compounds having selective KRAS inhibitory action.

DESCRIPTION OF EMBODIMENTS

Abbreviations

The abbreviations used herein are as follows.
AA: Ammonium acetate
Boc: tert-Butoxycarbonyl
CSA: (+)-10-Camphorsulfonic acid
CPME: Cyclopentyl methyl ether
DAST: (Diethylamino) sulfur trifluoride
DBU: 1,8-Diazabicyclo [5.4.0]-7-undecene
DCM: Dichloromethane
DCE: 1,2-Dichloroethane
DEAD: Diethyl azodicarboxylate
DEPBT: 3-(Diethoxyphosphoryloxy)-1,2,3-benzotriazin-4 (3H)-one
DIAD: Diisopropyl azodicarboxylate
DIC: N,N'-Diisopropylcarbodiimide
DIPEA: N,N-Diisopropylethylamine
DHP: 3,4-Dihydro-2H-pyran
DMA: N,N-Dimethylacetamide
DMAP: N,N-Dimethyl-4-aminopyridine
DMF: N,N-Dimethylformamide
dtbbpy: 4,4'-Di-tert-butyl-2,2'-bipyridine
EDTA: Ethylenediaminetetraacetic acid
FA: Formic acid
Fmoc: 9-Fluorenylmethyloxycarbonyl
NMP: N-Methyl-2-pyrrolidone
TBME: t-Butyl methyl ether
TES: Triethylsilane
TFA: Trifluoroacetic acid
TFE: 2,2,2-Trifluoroethanol
THF: Tetrahydrofuran
THP: Tetrahydropyranyl
TMSCI: Chlorotrimethylsilane
HFIP: 1,1,1,3,3,3-Hexafluoroisopropyl alcohol
HOAt: 1-Hydroxy-7-azabenzotriazole
HOBt: 1-Hydroxybenzotriazole
HOOBt: 3,4-Dihydro-3-hydroxy-4-oxo-1,2,3-benzotriazine
IPAC: Isopropyl acetate oxyma: Ethyl cyano (hydroxyimino)acetate
PPTS: Pyridinium p-toluenesulfonate
Pis: 2-Phenylisopropyl
WSCI·HCl, WSCDI: 1-Ethyl-3-(3-dimethylaminopropyl) carbodiimide hydrochloride
TIPS: Triisopropylsilane
TfOH: Trifluoromethanesulfonic acid
HATU: O-(7-Aza-1H-benzotriazole-1-yl)-N,N,N',N'-tetramethyluronium hexafluorophosphate
DMSO: Dimethylsulfoxide
Fmoc-Cl: (9H-Fluoren-9-yl)methyl carbonochloridate
Fmoc-OSu: 9-Fluorenylmethyl N-succinimidyl carbonate
Ns: o-Nitrobenzenesulfonyl
Trt: Triphenylmethyl
9-BBN: 9-Borabicyclo[3.3.1]nonane
HMDS: 1,1,1,3,3,3-Hexamethyldisilazane
LDA: Lithium diisopropylamide
TMSOTf: Trimethylsilyl trifluoromethanesulfonate
PPA: Polyphosphoric acid Herein, the term "about" when used in combination with a numerical value means a numerical range of +10% and −10% of that numerical value.

Herein, "-" indicating a range includes values at opposite ends of the range. For example, "A-B" means a range of A or more and B or less.

The unit of molecular weight herein is "g/mol" (hereinafter, the unit of molecular weight may be omitted).

The use of the articles "a", "an", and "the" in both the description and the claims are to be construed as covering both the singular and the plural, unless otherwise indicated herein or clearly contradicted by context.

(Definitions of Functional Groups and the Like)

Examples of "halogen atoms" herein include F, Cl, Br, and I.

"Alkyl" herein means a monovalent group derived by removing any one hydrogen atom from an aliphatic hydrocarbon, and has a subset of hydrocarbyl or hydrocarbon group structures not containing either a heteroatom (which refers to an atom other than carbon and hydrogen atoms) or an unsaturated carbon-carbon bond but containing hydrogen and carbon atoms in its backbone. The alkyl includes linear and branched alkyls. Specifically, the alkyl has 1 to 20 carbon atoms ($C_1$-$C_{20}$, hereinafter "$C_p$-$C_q$" means that the number of carbon atoms is p to q), and is preferably $C_1$-$C_{10}$ alkyl, and more preferably $C_1$-$C_6$ alkyl. Specific examples of alkyl include methyl, ethyl, n-propyl, i-propyl, n-butyl, s-butyl, t-butyl, isobutyl(2-methylpropyl), n-pentyl, s-pentyl (1-methylbutyl), t-pentyl(1,1-dimethylpropyl), neopentyl(2,2-dimethylpropyl), isopentyl(3-methylbutyl), 3-pentyl(1-ethylpropyl), 1,2-dimethylpropyl, 2-methylbutyl, n-hexyl, 1,1,2-trimethylpropyl, 1,2,2-trimethylpropyl, 1,1,2,2-tetramethylpropyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, and 2-ethylbutyl.

"Alkenyl" herein means a monovalent group having at least one double bond (two adjacent $SP^2$ carbon atoms). Depending on the configuration of a double bond and a substituent (if present), the geometrical form of the double bond can be entgegen (E) or zusammen (Z) as well as cis or trans configuration. The alkenyl includes linear and branched alkenyls. The alkenyl is preferably $C_2$-$C_{10}$ alkenyl, and more preferably $C_2$-$C_7$ alkenyl or $C_2$-$C_6$ alkenyl, and specific examples include vinyl, allyl, 1-propenyl, 2-propenyl, 1-butenyl, 2-butenyl (including cis and trans forms), 3-butenyl, pentenyl, 3-methyl-2-butenyl, hexenyl, and 6-heptenyl.

"Alkynyl" herein means a monovalent group having at least one triple bond (two adjacent SP carbon atoms). The alkynyl includes linear and branched alkynyls. The alkynyl is preferably $C_2$-$C_{10}$ alkynyl, and more preferably $C_2$-$C_6$ alkynyl, and specific examples include ethynyl, 1-propynyl, propargyl, 3-butynyl, pentynyl, hexynyl, 3-phenyl-2-propynyl, 3-(2'-fluorophenyl)-2-propynyl, 2-hydroxy-2-propynyl, 3-(3-fluorophenyl)-2-propynyl, and 3-methyl-(5-phenyl)-4-pentynyl.

"Cycloalkyl" herein means a saturated or partially saturated cyclic monovalent aliphatic hydrocarbon group and includes a monocyclic ring, a bicyclo ring, and a spiro ring. The cycloalkyl is preferably $C_3$-$C_8$ cycloalkyl, and specific examples include cyclopropyl, cyclobutyl, cyclopentyl, cyclohexyl, cycloheptyl, cyclooctyl, bicyclo[2.2.1]heptyl, and spiro[3.3] heptyl.

"Aryl" herein means a monovalent aromatic hydrocarbon ring, and is preferably C6-C10 aryl. Specific examples of the aryl include phenyl and naphthyl (e.g., 1-naphthyl and 2-naphthyl). Aryl herein includes bicyclic aryl in which the aromatic hydrocarbon ring is condensed with another saturated ring or unsaturated ring, and, for example, includes aryl having a condensed ring structure in which the aromatic hydrocarbon ring is a benzene ring and the saturated ring is a 5-, 6-, or 7-membered saturated hydrocarbon ring or saturated heterocyclic ring. Specific examples include indanyl, 1,2,3,4-tetrahydronaphthyl, and 2,3-dihydrobenzofuran.

"Heterocyclyl" herein means a non-aromatic cyclic monovalent group containing 1 to 5 hetero atoms in addition to carbon atoms. The heterocyclyl may have a double and/or triple bond within the ring, a carbon atom within the ring may be oxidized to form carbonyl, and heterocyclyl may be a monocyclic ring or a condensed ring. The number of atoms constituting the ring is preferably 3 to 10 (3- to 10-membered heterocyclyl) or 4 to 10 (4- to 10-membered heterocyclyl), and more preferably 3 to 7 (3- to 7-membered heterocyclyl) or 4 to 7 (4- to 7-membered heterocyclyl). Specific examples of the heterocyclyl include azetidinyl, oxiranyl, oxetanyl, azetidinyl, dihydrofuryl, tetrahydrofuryl, dihydropyranyl, tetrahydropyranyl, tetrahydropyridyl, tetrahydropyrimidyl, morpholinyl, thiomorpholinyl, pyrrolidinyl, piperidinyl, piperazinyl, pyrazolidinyl, imidazolinyl, imidazolidinyl, oxazolidinyl, isoxazolidinyl, thiazolidinyl, isothiazolidinyl, 1,2-thiazinane, thiadiazolidinyl, azetidinyl, oxazolidone, benzodioxanyl, benzoxazolyl, dioxolanyl, dioxanyl, tetrahydropyrrolo[1,2-c]imidazole, thietanyl, 3,6-diazabicyclo[3.1.1]heptanyl, 2,5-diazabicyclo[2.2.1]heptanyl, 3-oxa-8-azabicyclo[3.2.1]octanyl, sultam, and 2-oxaspiro[3.3] heptyl.

"Protected heterocyclyl" herein means a group in which one or more functional groups, such as an amino group, contained in the above-defined "heterocyclyl" are protected with a protecting group, and is preferably 4- to 7-membered protected heterocyclyl. Specific examples of the protecting group include Boc, Fmoc, Cbz, Troc, and Alloc, and specific examples of the protected heterocyclyl include Boc-protected azetidine.

"Heterocycloalkylidene" herein means a divalent group obtained by removing two hydrogen atoms from one carbon atom of the above-defined "heterocyclyl", in which a free valence forms a part of a double bond. The heterocycloalkylidene is preferably 4- to 7-membered heterocycloalkylidene, and specific examples include tetrahydropyran-4-ylidene and azetidin-3-ylidene.

"Protected heterocycloalkylidene" herein means a group in which one or more functional groups, such as an amino group, contained in the above-defined "heterocycloalkylidene" are protected with a protecting group, and is preferably 4- to 7-membered protected heterocycloalkylidene. Specific examples of the protecting group include Boc, Fmoc, Cbz, Troc, and Alloc, and specific examples of the protected heterocycloalkylidene include Boc-protected azetidin-3-ylidene.

"Heteroaryl" herein means an aromatic cyclic monovalent group containing 1 to 5 heteroatoms in addition to carbon atoms. The ring may be a monocyclic ring, may be a condensed ring formed with another ring, or may be partially saturated. The number of atoms constituting the ring is preferably 5 to 10)(5- to 10-membered heteroaryl) and more preferably 5 to 7 (5- to 7-membered heteroaryl). Specific examples of the heteroaryl include furyl, thienyl, pyrrolyl, imidazolyl, pyrazolyl, thiazolyl, isothiazolyl, oxazolyl, isoxazolyl, oxadiazolyl, thiadiazolyl, triazolyl, tetrazolyl, pyridyl, pyrimidyl, pyridazinyl, pyrazinyl, triazinyl, benzofuranyl, benzothienyl, benzothiadiazolyl, benzothiazolyl, benzoxazolyl, benzoxadiazolyl, benzoimidazolyl, indolyl, isoindolyl, indazolyl, quinolyl, isoquinolyl, cinnolinyl, quinazolinyl, quinoxalinyl, benzodioxolyl, indolizinyl, and imidazopyridyl.

"Alkoxy" herein means an oxy group to which the above-defined "alkyl" is bonded, and is preferably $C_1$-$C_6$ alkoxy. Specific examples of the alkoxy include methoxy, ethoxy, 1-propoxy, 2-propoxy, n-butoxy, i-butoxy, s-butoxy, t-butoxy, pentyloxy, and 3-methylbutoxy.

"Alkylthio" herein means a thiol group to which the above-defined "alkyl" is bonded, and is preferably $C_1$-$C_6$ alkylthio. Specific examples of alkylthio include methylthio, ethylthio, 1-propylthio, 2-propylthio, n-butylthio, i-butylthio, s-butylthio, and t-butylthio. [00] 34]

"Alkenyloxy" herein means an oxy group to which the above-defined "alkenyl" is bonded, and is preferably $C_2$-$C_6$ alkenyloxy. Specific examples of the alkenyloxy include vinyloxy, allyloxy, 1-propenyloxy, 2-propenyloxy, 1-butenyloxy, 2-butenyloxy (including cis and trans forms), 3-butenyloxy, pentenyloxy, and hexenyloxy.

"Cycloalkoxy" herein means an oxy group to which the above-defined "cycloalkyl" is bonded, and is preferably $C_3$-$C_8$ cycloalkoxy. Specific examples of the cycloalkoxy include cyclopropoxy, cyclobutoxy, and cyclopentyloxy.

"Aryloxy" herein means an oxy group to which the above-defined "aryl" is bonded, and is preferably $C_6$-$C_{10}$ aryloxy. Specific examples of the aryloxy include phenoxy, 1-naphthyloxy, and 2-naphthyloxy.

"Amino" herein means-NH2 in a narrow sense and —NRR' in a broad sense, wherein R and R' are independently selected from hydrogen, alkyl, alkenyl, alkynyl, cycloalkyl, heterocyclyl, aryl, or heteroaryl, or R and R', together with the nitrogen atom to which they are attached, form a ring. The amino is preferably-NH2, mono-$C_1$-$C_6$ alkylamino, di-$C_1$-$C_6$ alkylamino, 4- to 8-membered cyclic amino, or the like.

"Monoalkylamino" herein means a group corresponding to the above-defined "amino" wherein R is hydrogen and R' is the above-defined "alkyl", and is preferably mono-$C_1$-$C_6$ alkylamino. Specific examples of the monoalkylamino include methylamino, ethylamino, n-propylamino, i-propylamino, n-butylamino, s-butylamino, and t-butylamino.

"Dialkylamino" herein means a group corresponding to the above-defined "amino" wherein R and R' are independently the above-defined "alkyl", and is preferably di-$C_1$-$C_6$ alkylamino. Specific examples of the dialkylamino include dimethylamino and diethylamino.

"Cyclic amino" herein means a group corresponding to the above-defined "amino" wherein R and R', together with the nitrogen atom to which they are attached, form a ring, and is preferably 4- to 8-membered cyclic amino. Specific examples of the cyclic amino include 1-azetidyl, 1-pyrrolidyl, 1-piperidyl, 1-piperazyl, 4-morpholinyl, 3-oxazolidyl, 1,1-dioxidethiomorpholinyl-4-yl, and 3-oxa-8-azabicyclo[3.2.1]octan-8-yl.

"Protected amino" herein means an amino group protected with any protecting group. Specific examples of the protected amino include amino protected with a protecting group such as Boc, Fmoc, Cbz, Troc, or Alloc.

"Alkylcarbonyl" herein means a carbonyl group to which the above-defined "alkyl" is bonded, and is preferably $C_1$-$C_6$ alkylcarbonyl. Specific examples of alkylcarbonyl include acetyl, propionyl, and butyryl. The number of carbon atoms set forth in the above definition indicates the number of carbon atoms in the alkyl moiety. For example, "$C_1$-$C_6$" in "$C_1$-$C_6$ alkylcarbonyl" indicates that the alkyl moiety has 1 to 6 carbon atoms.

"Aminocarbonyl" herein means a carbonyl group to which the above-defined "amino" is bonded, and is preferably —CONH$_2$, mono-$C_1$-$C_6$ alkylaminocarbonyl, di-$C_1$-$C_6$ alkylaminocarbonyl, and 4- to 8-membered cyclic aminocarbonyl. Specific examples of the aminocarbonyl include —CONH$_2$, dimethylaminocarbonyl, 1-azetidinylcarbonyl, 1-pyrrolidinylcarbonyl, 1-piperidinylcarbonyl, 1-piperazinylcarbonyl, 4-morpholinylcarbonyl, 3-oxazolidinylcarbonyl, 1,1-dioxidethiomorpholinyl-4-ylcarbonyl, and 3-oxa-8-azabicyclo[3.2.1]octan-8-ylcarbonyl.

"Alkenyloxycarbonyl" herein means a carbonyl group to which the above-defined "alkenyloxy" is bonded, and is preferably $C_2$-$C_6$ alkenyloxycarbonyl. Specific examples of the alkenyloxycarbonyl include vinyloxycarbonyl, allyloxycarbonyl, 1-propenyloxycarbonyl, 2-propenyloxycarbonyl, 1-butenyloxycarbonyl, 2-butenyloxycarbonyl (including cis and trans forms), 3-butenyloxycarbonyl, pentenyloxycarbonyl, and hexenyloxycarbonyl. "Alkylsulfonyl" herein means a sulfonyl group to which the above-defined "alkyl" is bonded, and is preferably $C_1$-$C_6$ alkylsulfonyl. Specific examples of the alkylsulfonyl include methylsulfonyl.

"Hydroxyalkyl" herein means a group in which one or more hydrogens of the above-defined "alkyl" are replaced with hydroxyl groups, and is preferably $C_1$-$C_6$ hydroxyalkyl. Specific examples of the hydroxyalkyl include hydroxymethyl, 1-hydroxyethyl, 2-hydroxyethyl, 2-hydroxy-2-methylpropyl, and 5-hydroxypentyl.

"Haloalkyl" herein means a group in which one or more hydrogens of the above-defined "alkyl" are replaced with halogen, and is preferably $C_1$-$C_6$ haloalkyl, and more preferably $C_1$-$C_6$ fluoroalkyl. Specific examples of the haloalkyl include difluoromethyl, trifluoromethyl, 2,2-difluoroethyl, 2,2,2-trifluoroethyl, 3,3-difluoropropyl, 4,4-difluorobutyl, 5,5-difluoropentyl, and 1,1-difluoroethyl.

"Cyanoalkyl" herein means a group in which one or more hydrogens of the above-defined "alkyl" are replaced with cyano, and is preferably $C_1$-$C_6$ cyanoalkyl. Specific examples of the cyanoalkyl include cyanomethyl and 2-cyanoethyl.

"Aminoalkyl" herein means a group in which one or more hydrogens of the above-defined "alkyl" are replaced with the above-defined "amino", and is preferably $C_1$-$C_6$ aminoalkyl. Specific examples of the aminoalkyl include 1-pyridylmethyl, 2-(1-piperidyl)ethyl, 3-(1-piperidyl) propyl, 4-aminobutyl, and 2-aminoethyl.

"Carboxyalkyl" herein means a group in which one or more hydrogens of the above-defined "alkyl" are replaced with carboxy, and is preferably $C_1$-$C_6$ carboxyalkyl or $C_2$-$C_6$ carboxyalkyl. Specific examples of the carboxyalkyl include carboxymethyl. The number of carbon atoms set forth in the above definition indicates the number of carbon atoms in the alkyl moiety. For example, "$C_1$-$C_6$" in "$C_1$-$C_6$ carboxyalkyl" indicates that the alkyl moiety has 1 to 6 carbon atoms.

"Alkenyloxycarbonylalkyl" herein means a group in which one or more hydrogens of the above-defined "alkyl" are replaced with the above-defined "alkenyloxycarbonyl", and is preferably $C_2$-$C_6$ alkenyloxycarbonyl $C_1$-$C_6$ alkyl, and more preferably $C_2$-$C_6$ alkenyloxycarbonyl $C_1$-$C_2$ alkyl. Specific examples of the alkenyloxycarbonylalkyl include allyloxycarbonylmethyl and 2-(allyloxycarbonyl)ethyl.

"Alkoxyalkyl" herein means a group in which one or more hydrogens of the above-defined "alkyl" are replaced with the above-defined "alkoxy", and is preferably $C_1$-$C_6$ alkoxy $C_1$-$C_6$ alkyl, and more preferably $C_1$-$C_6$ alkoxy $C_1$-$C_2$ alkyl. Specific examples of the alkoxyalkyl include methoxymethyl, ethoxymethyl, 1-propoxymethyl, 2-propoxymethyl, n-butoxymethyl, i-butoxymethyl, s-butoxymethyl, t-butoxymethyl, pentyloxymethyl, 3-methylbutoxymethyl, 1-methoxyethyl, 2-methoxyethyl, 2-ethoxyethyl, 1-ethoxyethyl, and 1-n-propyloxyethyl.

"Alkylthioalkyl" herein means a group in which one or more hydrogens of the above-defined "alkyl" are replaced with the above-defined "alkylthio", and is preferably $C_1$-$C_6$ alkylthio$C_1$—$C_6$ alkyl, and more preferably $C_1$-$C_6$ alkylthio$C_1$—$C_2$ alkyl. Specific examples of alkylthioalkyl include methylthiomethyl, ethylthiomethyl, 1-propylthiomethyl, 2-propylthiomethyl, n-butylthiomethyl, i-butylthiomethyl, s-butylthiomethyl, and t-butylthiomethyl.

"Alkenyloxyalkyl" herein means a group in which one or more hydrogens of the above-defined "alkyl" are replaced with the above-defined "alkenyloxy", and is preferably $C_2$-$C_6$ alkenyloxy$C_1$—$C_6$ alkyl, and more preferably $C_1$-$C_6$ alkenyloxy$C_1$—$C_2$ alkyl. Specific examples of alkenyloxyalkyl include vinyloxymethyl and allyloxymethyl.

"Cycloalkylalkyl" herein means a group in which one or more hydrogens of the above-defined "alkyl" are replaced with the above-defined "cycloalkyl", and is preferably $C_3$-$C_8$ cycloalkyl $C_1$-$C_6$ alkyl, and more preferably $C_3$-$C_6$ cycloalkyl $C_1$-$C_2$ alkyl. Specific examples of the cycloalkylalkyl include cyclopropylmethyl, cyclobutylmethyl, cyclopentylmethyl, and cyclohexylmethyl.

"Cycloalkoxyalkyl" herein means a group in which one or more hydrogens of the above-defined "alkyl" are replaced with the above-defined "cycloalkoxy", and is preferably $C_3$-$C_8$ cycloalkoxy $C_1$-$C_6$ alkyl, and more preferably $C_3$-$C_6$ cycloalkoxy $C_1$-$C_2$ alkyl. Specific examples of the cycloalkoxyalkyl include cyclopropoxymethyl and cyclobutoxymethyl.

"Heterocyclylalkyl" herein means a group in which one or more hydrogens of the above-defined "alkyl" are replaced with the above-defined "heterocyclyl", and is preferably 4- to 7-membered heterocyclyl $C_1$-$C_6$ alkyl, and more preferably 4- to 7-membered heterocyclyl $C_1$-$C_2$ alkyl. Specific examples of the heterocyclylalkyl include 2-(tetrahydro-2H-pyran-4-yl)ethyl and 2-(azetidin-3-yl)ethyl.

"Alkylsulfonylalkyl" herein means a group in which one or more hydrogens of the above-defined "alkyl" are replaced with the above-defined "alkylsulfonyl", and is preferably $C_1$-$C_6$ alkylsulfonyl $C_1$-$C_6$ alkyl, and more preferably $C_1$-$C_6$ alkylsulfonyl $C_1$-$C_2$ alkyl. Specific examples of the alkylsulfonylalkyl include methylsulfonylmethyl and 2-(methylsulfonyl)ethyl.

"Aminocarbonylalkyl" herein means a group in which one or more hydrogens of the above-defined "alkyl" are replaced with the above-defined "aminocarbonyl", and is preferably aminocarbonyl $C_1$-$C_6$ alkyl, and more preferably aminocarbonyl $C_1$-$C_4$ alkyl. Specific examples of the aminocarbonylalkyl include methylaminocarbonylmethyl, dimethylaminocarbonylmethyl, t-butylaminocarbonylmethyl, 1-azetidinylcarbonylmethyl, 1-pyrrolidinylcarbonylmethyl, 1-piperidinylcarbonylmethyl, 4-morpholinylcarbonylmethyl, 2-(methylaminocarbonyl)ethyl,2-(dimethylaminocarbonyl)ethyl, 2-(1-azetidinylcarbonyl)ethyl, 2-(1-pyrrolidinylcarbonyl)ethyl, 2-(4-morpholinylcarbonyl)ethyl, 3-(dimethylaminocarbonyl) propyl, and 4-(dimethylaminocarbonyl)butyl.

"Aryloxyalkyl" herein means a group in which one or more hydrogens of the above-defined "alkyl" are replaced with the above-defined "aryloxy", and is preferably $C_6$-$C_{10}$ aryloxy $C_1$-$C_6$ alkyl, and more preferably $C_6$-$C_{10}$ aryloxy $C_1$-$C_2$ alkyl. Specific examples of the aryloxyalkyl include phenoxymethyl and 2-phenoxyethyl.

"Aralkyl(arylalkyl)" herein means a group in which one or more hydrogen atoms of the above-defined "alkyl" are replaced with the above-defined "aryl", and is preferably $C_7$-$C_{14}$ aralkyl, and more preferably $C_7$-$C_{10}$ aralkyl. Specific examples of the aralkyl include benzyl, phenethyl, and 3-phenylpropyl.

"Aralkoxy" herein means an oxy group to which the above-defined "aralkyl" is bonded, and is preferably $C_7$-$C_{14}$ aralkoxy, and more preferably $C_7$-$C_{10}$ aralkoxy. Specific examples of the aralkoxy include benzyloxy, phenethyloxy, and 3-phenylpropoxy.

"Aralkoxyalkyl" herein means a group in which one or more hydrogens of the above-defined "alkyl" are replaced with the above-defined "aralkoxy", and is preferably $C_7$-$C_{14}$ aralkoxy $C_1$-$C_6$ alkyl, and more preferably $C_7$-$C_{14}$ aralkoxy $C_1$-$C_2$ alkyl. Specific examples of the aralkoxyalkyl include benzyloxymethyl and 1-(benzyloxy)ethyl.

"Heteroarylalkyl" herein means a group in which one or more hydrogen atoms of the above-defined "alkyl" are replaced with the above-defined "heteroaryl", and is preferably 5- to 10)-membered heteroaryl $C_1$-$C_6$ alkyl, and more preferably 5- to 10-membered heteroaryl $C_1$-$C_2$ alkyl. Specific examples of the heteroarylalkyl include 3-thienylmethyl, 4-thiazolylmethyl, 2-pyridylmethyl, 3-pyridylmethyl, 4-pyridylmethyl, 2-(2-pyridyl)ethyl, 2-(3-pyridyl)ethyl, 2-(4-pyridyl)ethyl, 2-(6-quinolyl)ethyl, 2-(7-quinolyl)ethyl, 2-(6-indolyl)ethyl, 2-(5-indolyl)ethyl, and 2-(5-benzofuranyl)ethyl.

"Heteroarylalkoxy" herein means an oxy group to which the above-defined "heteroarylalkyl" is bonded, and is preferably 5- to 10-membered heteroaryl $C_1$-$C_6$ alkoxy, and more preferably 5- to 10-membered heteroaryl$C_1$—$C_2$ alkoxy. Specific examples of the heteroarylalkoxy include 3-thienylmethoxy and 3-pyridylmethoxy.

"Heteroarylalkoxyalkyl" herein means a group in which one or more hydrogens of the above-defined "alkyl" are replaced with the above-defined "heteroarylalkoxy", and is preferably 5- to 10-membered heteroaryl $C_1$-$C_6$ alkoxy $C_1$-$C_6$ alkyl, and more preferably 5- to 10-membered heteroaryl $C_1$-$C_2$ alkoxy $C_1$-$C_2$ alkyl. Specific examples of the heteroarylalkoxyalkyl include 3-pyridylmethoxymethyl.

"Heterocycloalkylidenealkyl" herein means a group in which one or more hydrogens of the above-defined "alkyl" are replaced with the above-defined "heterocycloalkylidene", and is preferably 4- to 7-membered heterocycloalkylidene $C_1$-$C_6$ alkyl, and more preferably 4- to 7-membered heterocycloalkylidene $C_1$-$C_2$ alkyl. Specific examples of the heterocycloalkylidenealkyl include tetrahydro-4H-pyran-4-ylidenemethyl and azetidin-3-ylidenemethyl.

"Alkoxyalkenyl" herein means a group in which one or more hydrogens of the above-defined "alkenyl" are replaced with the above-defined "alkoxy", and is preferably $C_1$-$C_6$ alkoxy $C_2$-$C_6$ alkenyl. Specific examples of the alkoxyalkenyl include (E)-4-methoxybut-2-en-1-yl.

"Aminocarbonylalkenyl" herein means a group in which one or more hydrogens of the above-defined "alkenyl" are replaced with the above-defined "aminocarbonyl", and is preferably aminocarbonyl $C_2$-$C_6$ alkenyl. Specific examples of the aminocarbonylalkenyl include (E)-3-(dimethylaminocarbonylcarbonyl)-prop-2-en-1-yl.

"Haloalkoxy" herein means a group in which one or more hydrogens of the above-defined "alkoxy" are replaced with halogen, and is preferably $C_1$-$C_6$ haloalkoxy. Specific examples of the haloalkoxy include difluoromethoxy, trifluoromethoxy, 2,2-difluoroethoxy, and 2,2,2-trifluoroethoxy.

"Alkylene" herein means a divalent group derived by further removing any one hydrogen atom from the above "alkyl", and is preferably $C_4$-$C_8$ alkylene. Specific examples of the alkylene include —$CH_2$—, —$(CH_2)_2$—, —$(CH_2)_3$—, —$CH(CH_3)CH_2$—, —$C(CH_3)_2$—, —$(CH_2)_4$-, —$CH(CH_3)CH_2CH_2$—, —$C(CH_3)_2CH_2$—, —$CH_2CH(CH_3)CH_2$—, —$CH_2C(CH_3)_2$—, —$CH_2CH_2CH(CH_3)$—, —$(CH_2)_5$—, —$(CH_2)_6$—, —$(CH_2)_7$—, and —$(CH_2)_8$—.

"Cycloalkylene" herein means a divalent group derived by further removing any one hydrogen atom from the above "cycloalkyl", and is preferably $C_3$-$C_8$ cycloalkylene. Specific examples of cycloalkylene include cyclopropane-1,2-diyl, cyclobutane-1,2-diyl, cyclopentane-1,2-diyl, and cyclohexane-1,2-diyl.

"Heterocyclylene" herein means a divalent group derived by removing any one hydrogen atom from the above "heterocyclyl", and is preferably 3- to 7-membered heterocyclylene. Specific examples of heterocyclylene include oxylan-2,3-diyl, oxetan-2,3-diyl, tetrahydrofuran-2,5-diyl, and tetrahydropyran-2,6-diyl.

"Alkenylene" herein means a divalent group derived by further removing any one hydrogen atom from the above "alkenyl". Depending on the configuration of a double bond and a substituent (if present), the geometrical form of the double bond can be entgegen (E) or zusammen (Z) as well as cis or trans configuration. Alkenylene may be linear or branched, and is preferably $C_2$-$C_{10}$ alkenylene and more preferably $C_2$-$C_6$ alkenylene.

"Alkynylene" herein means a divalent group derived by further removing any one hydrogen atom from the above "alkynyl". Alkynylene may be linear or branched, and is preferably $C_2$-$C_{10}$ alkynylene and more preferably $C_2$-$C_6$ alkynylene.

"Arylene" herein means a divalent group derived by further removing any one hydrogen atom from the above "aryl". Arylene may be a monocyclic ring or a condensed ring. The number of atoms constituting the ring is not particularly limited, and is preferably 6 to 10 ($C_{6-10}$ arylene). Specific examples of arylene include 1,2-phenylene, 1,3-phenylene, 1,4-phenylene, 1,2-naphthylene, 1,3-naphthylene, and 1,4-naphthylene.

"Spirocycloalkyl" herein means a group formed by sharing of one carbon atom constituting a cycloalkane ring with a carbon atom present in a group to be bonded. Spirocycloalkyl is preferably C3-Cs spirocycloalkyl, and specific examples include spirocyclopropyl, spirocyclobutyl, spirocyclopentyl, spirocyclohexyl, spirocycloheptyl, and spirocyclooctyl.

"Spiroheterocyclyl" herein means a group obtained by replacing one or more carbon atoms in the above "spirocycloalkyl" with heteroatoms. Heterospirocycloalkyl is preferably 4- to 10-membered spiroheterocyclyl.

"Alicyclic ring" herein means a non-aromatic hydrocarbon ring. The alicyclic ring may have an unsaturated bond within the ring, and may be a polycyclic ring having two or more rings. A carbon atom constituting the ring may be oxidized to form carbonyl. The alicyclic ring is preferably a 3- to 8-membered alicyclic ring, and specific examples include a cyclopropane ring, a cyclobutane ring, a cyclopentane ring, a cyclohexane ring, a cycloheptane ring, a cyclooctane ring, and a bicyclo[2.2.1]heptane ring.

"Saturated heterocyclic ring" herein means a non-aromatic heterocyclic ring containing 1 to 5 hetero atoms in addition to carbon atoms and not containing a double bond and/or a triple bond within the ring. The saturated heterocyclic ring may be a monocyclic ring, or may form a condensed ring with another ring, e.g., an aromatic ring such as a benzene ring. The saturated heterocyclic ring is preferably a 4- to 7-membered saturated heterocyclic ring, and specific examples include an azetidine ring, an oxetane ring, a tetrahydrofuran ring, a tetrahydropyran ring, a morpholine ring, a thiomorpholine ring, a pyrrolidine ring, a 4-oxopyrrolidine ring, a piperidine ring, a 4-oxopiperidine ring, a piperazine ring, a pyrazolidine ring, an imidazolidine ring, an oxazolidine ring, an isoxazolidine ring, a thiazolidine ring, an isothiazolidine ring, a thiadiazolidine ring, an oxazolidone ring, a dioxolane ring, a dioxane ring, a thietane ring, an octahydroindole ring, an indoline ring, and an azepane ring.

"Peptide chain" herein refers to a peptide chain in which 1, 2, 3, 4, or more natural amino acids and/or non-natural amino acids are connected by an amide bond and/or an ester bond. The peptide chain is preferably a peptide chain comprising 1 to 4 amino acid residues, and more preferably a peptide chain consisting of 1 to 4 amino acid residues.

"Optionally substituted" herein means that a group may be substituted with any substituent.

"Optionally protected" herein means that a group may be protected with any protecting group.

"One or more" herein means one or two or more. When "one or more" is used in a context relating to the substituent of a group, the phrase means a number encompassing one to the maximum number of substituents permitted by that group. Specific examples of "one or more" include 1, 2, 3, 4, 5, 6, 7, 8, 9, 10, and/or a greater number.

The wavy line in the structural formulae herein can mean that any stereochemistry is permitted. For example, when the asymmetric center is provided with a wavy line, the stereochemistry of the asymmetric center may be in the S configuration or in the R configuration. When a double bond is provided with a wavy line, the stereochemistry of the double bond may be in the E configuration or in the Z configuration.

As used herein, a symbol represented by "PPn$^1$n$^2$n$^3$n$^4$", where $n^1$, $n^2$, $n^3$ and $n^4$ each independently represent an integer of 0) to 9", for example, PP1574 and PP1640, represents the number of a compound.

The compound of the present invention can be a salt thereof, and preferably a chemically or pharmaceutically acceptable salt thereof. Also, the compound of the present invention or a salt thereof can be a solvate thereof, and preferably a chemically or pharmaceutically acceptable solvate thereof. Examples of salts of the compound of the present invention include hydrochloride: hydrobromide: hydroiodide: phosphate: phosphonate: sulfate: sulfonates such as methanesulfonate and p-toluenesulfonate: carboxylates such as acetate, citrate, malate, tartrate, succinate, and salicylate: alkali metal salts such as a sodium salt and a potassium salt: alkaline earth metal salts such as a magnesium salt and a calcium salt; and ammonium salts such as an ammonium salt, an alkylammonium salt, a dialkylammonium salt, a trialkylammonium salt, and a tetraalkylammonium salt. These salts are produced by, for example, bringing the compound into contact with an acid or a base usable in the production of pharmaceutical products. In the present invention, a solvate of a compound refers to one molecular group formed by the compound together with a solvent, and is called a hydrate when the solvent is water. The solvate of the compound of the present invention is preferably a hydrate, and specific examples of such hydrates include mono- to deca-hydrates, preferably mono- to penta-hydrates, and more preferably mono- to tri-hydrates. The solvate of the compound of the present invention includes not only a solvate formed of a single solvent such as water, alcohol (e.g., methanol, ethanol, 1-propanol, or 2-propanol), or dimethylformamide, but also a solvate formed of a plurality of solvents.

The term "amino acid" as used herein includes natural and unnatural amino acids. The term "natural amino acid" as used herein refers to Gly, Ala, Ser, Thr, Val, Leu, Ile, Phe, Tyr, Trp, His, Glu, Asp, Gln, Asn, Cys, Met, Lys, Arg, or Pro. Examples of the unnatural amino acid include, but are not particularly limited to, β-amino acids,-amino acids, D-amino acids, N-substituted amino acids, a, a-disubstituted amino acids, amino acids having side chains that are different from those of natural amino acids, and hydroxycarboxylic acids. Amino acids herein may have any conformation. There is no particular limitation on the selection of amino acid side chain, but in addition to a hydrogen atom, it can be freely selected from, for example, an alkyl group, an alkenyl group, an alkynyl group, an aryl group, a heteroaryl group, an aralkyl group, and a cycloalkyl group. One or two non-adjacent methylene groups in such a group are optionally substituted with an oxygen atom, a carbonyl group (—CO—), or a sulfonyl group (—SO$_2$—). Each group may have a substituent, and there are no limitations on the substituent. For example, one or more substituents may be freely and independently selected from any substituents including a halogen atom, an O atom, an S atom, an N atom, a B atom, an Si atom, or a P atom. Examples include an optionally substituted alkyl group, alkenyl group, alkynyl group, aryl group, heteroaryl group, aralkyl group, and cycloalkyl group. In a non-limiting embodiment, amino acids herein may be compounds having a carboxy group and an amino group in the same molecule (even in this case, imino acids such as proline and hydroxyproline are also included in amino acids).

The main chain amino group of an amino acid may be unsubstituted (an NH$_2$ group) or substituted (i.e., an —NHR group, where R represents alkyl, alkenyl, alkynyl, aryl, heteroaryl, aralkyl, or cycloalkyl which may have a substituent, one or two non-adjacent methylene groups in such a group may be substituted with an oxygen atom, a carbonyl group (—CO—), or a sulfonyl group (—SO$_2$—), and the carbon chain bonded to the N atom and the carbon atom at the position a may form a ring, as in proline). The R substituent is selected as the substituent in the aforementioned amino acid side chain is selected. When the main chain amino group is substituted, the R is included in the "amino acid side chain" as used herein. Such amino acids in which the main chain amino group is substituted are herein called "N-substituted amino acids." Preferred examples of the "N-substituted amino acids" as used herein include, but are not limited to, N-alkylamino acids, N—C$_1$-C$_6$ alkylamino acids, N—C$_1$-C$_4$ alkylamino acids, and N-methylamino acids.

"Amino acids" as used herein which constitute a peptide compound include all isotopes corresponding to each amino acid. The isotope of the "amino acid" refers to one having at least one atom replaced with an atom of the same atomic number (number of protons) and different mass number (total number of protons and neutrons). Examples of isotopes contained in the "amino acid" constituting the peptide compounds of the present invention include a hydrogen atom, a carbon atom, a nitrogen atom, an oxygen atom, a phosphorus atom, a sulfur atom, a fluorine atom, and a chlorine atom, which respectively include $^2$H and $^3$H; $^{13}$C and $^{14}$C; $^{15}$N; $^{17}$O and $^{18}$O; $^{31}$P and $^{32}$P; $^{35}$S; $^{18}$F; and $^{36}$Cl.

Substituents containing a halogen atom as used herein include a halogen-substituted alkyl group, cycloalkyl group, alkenyl group, alkynyl group, aryl group, heteroaryl group, or aralkyl group. More specific examples include fluoroalkyl, difluoroalkyl, and trifluoroalkyl.

Substituents containing an O atom include groups such as hydroxy (—OH), oxy (—OR), carbonyl (—C(═O)—R), carboxy (—CO$_2$H), oxycarbonyl (—C(═O)—OR), carbonyloxy (—O—C(═O)—R), thiocarbonyl (—C(═O)—SR), carbonylthio (—S—C(═O)—R), aminocarbonyl (—C(═O)—NHR), carbonylamino (—NH—C(═O)—R), oxycarbonylamino (—NH—C(═O)—OR), sulfonylamino (—NH—SO$_2$—R), aminosulfonyl (—SO$_2$—NHR), sulfamoylamino (—NH—SO$_2$—NHR), thiocarboxy (—C(═O)—SH), and carboxycarbonyl (—C(═O)—CO$_2$H).

Examples of oxy (—OR) include alkoxy, cycloalkoxy, alkenyloxy, alkynyloxy, aryloxy, heteroaryloxy, and aralkyloxy. Alkoxy is preferably C$_1$-C$_4$ alkoxy or C$_1$-C$_2$ alkoxy, and particularly preferably methoxy or ethoxy.

Examples of carbonyl (—C(═O)—R) include formyl (—C(═O)—H), alkylcarbonyl, cycloalkylcarbonyl, alkenylcarbonyl, alkynylcarbonyl, arylcarbonyl, heteroarylcarbonyl, and aralkylcarbonyl.

Examples of oxycarbonyl (—C(═O)—OR) include alkyloxycarbonyl, cycloalkyloxycarbonyl, alkenyloxycarbonyl, alkynyloxycarbonyl, aryloxycarbonyl, heteroaryloxycarbonyl, and aralkyloxycarbonyl.

Examples of carbonyloxy (—O—C(═O)—R) include alkylcarbonyloxy, cycloalkylcarbonyloxy, alkenylcarbonyloxy, alkynylcarbonyloxy, arylcarbonyloxy, heteroarylcarbonyloxy, and aralkylcarbonyloxy.

Examples of thiocarbonyl (—C(═O)—SR) include alkylthiocarbonyl, cycloalkylthiocarbonyl, alkenylthiocarbonyl, alkynylthiocarbonyl, arylthiocarbonyl, heteroarylthiocarbonyl, and aralkylthiocarbonyl.

Examples of carbonylthio (—S—C(═O)—R) include alkylcarbonylthio, cycloalkylcarbonylthio, alkenylcarbonylthio, alkynylcarbonylthio, arylcarbonylthio, heteroarylcarbonylthio, and aralkylcarbonylthio.

Examples of aminocarbonyl (—C(═O)—NHR) include alkylaminocarbonyl (such as C$_1$-C$_6$ or C$_1$-C$_4$ alkylaminocarbonyl and, in particular, ethylaminocarbonyl and methylaminocarbonyl), cycloalkylaminocarbonyl, alkenylaminocarbonyl, alkynylaminocarbonyl, arylaminocarbonyl, heteroarylaminocarbonyl, and aralkylaminocarbonyl. In addition, examples further include compounds obtained by replacing the H atom bonded to the N atom in —C(═O)—NHR with alkyl, cycloalkyl, alkenyl, alkynyl, aryl, heteroaryl, or aralkyl.

Examples of carbonylamino (—NH—C(═O)—R) include alkylcarbonylamino, cycloalkylcarbonylamino, alkenylcarbonylamino, alkynylcarbonylamino, arylcarbonylamino, heteroarylcarbonylamino, and aralkylcarbonylamino. In addition, examples further include compounds obtained by replacing the H atom bonded to the N atom in —NH—C(=O)—R with alkyl, cycloalkyl, alkenyl, alkynyl, aryl, heteroaryl, or aralkyl.

Examples of oxycarbonylamino (—NH—C(=O)—OR) include alkoxycarbonylamino, cycloalkoxycarbonylamino, alkenyloxycarbonylamino, alkynyloxycarbonylamino, aryloxycarbonylamino, heteroaryloxycarbonylamino, and aralkyloxycarbonylamino. In addition, examples further include compounds obtained by replacing the H atom bonded to the N atom in —NH—C(=O)—OR with alkyl, cycloalkyl, alkenyl, alkynyl, aryl, heteroaryl, or aralkyl.

Examples of sulfonylamino (—NH—SO$_2$—R) include alkylsulfonylamino, cycloalkylsulfonylamino, alkenylsulfonylamino, alkynylsulfonylamino, arylsulfonylamino, heteroarylsulfonylamino, and aralkylsulfonylamino. In addition, examples further include compounds obtained by replacing the H atom bonded to the N atom in —NH—SO$_2$—R with alkyl, cycloalkyl, alkenyl, alkynyl, aryl, heteroaryl, or aralkyl.

Examples of aminosulfonyl (—SO$_2$—NHR) include alkylaminosulfonyl, cycloalkylaminosulfonyl, alkenylaminosulfonyl, alkynylaminosulfonyl, arylaminosulfonyl, heteroarylaminosulfonyl, and aralkylaminosulfonyl. In addition, examples further include compounds obtained by replacing the H atom bonded to the N atom in-SO$_2$—NHR with alkyl, cycloalkyl, alkenyl, alkynyl, aryl, heteroaryl, or aralkyl.

Examples of sulfamoylamino (—NH—SO$_2$—NHR) include alkylsulfamoylamino, cycloalkylsulfamoylamino, alkenylsulfamoylamino, alkynylsulfamoylamino, arylsulfamoylamino, heteroarylsulfamoylamino, and aralkylsulfamoylamino. Moreover, two H atoms bonded to the N atoms in —NH—SO$_2$—NHR may be replaced with substituents independently selected from the group consisting of alkyl, cycloalkyl, alkenyl, alkynyl, aryl, heteroaryl, and aralkyl, and these two substituents may form a ring.

Substituents containing an S atom include groups such as thiol (—SH), thio (—S—R), sulfinyl (—S(=O)—R), sulfonyl (—SO$_2$—R), and sulfo (—SO$_3$H).

Examples of thio (—S—R) are selected from alkylthio, cycloalkylthio, alkenylthio, alkynylthio, arylthio, heteroarylthio, aralkylthio, and the like.

Examples of sulfonyl (—SO$_2$—R) include alkylsulfonyl, cycloalkylsulfonyl, alkenylsulfonyl, alkynylsulfonyl, arylsulfonyl, heteroarylsulfonyl, and aralkylsulfonyl.

Substituents containing an N atom include groups such as azide (—N$_3$, also referred to as an "azido group"), cyano (—CN), primary amino (—NH$_2$), secondary amino (—NH—R; also referred to as mono-substituted amino), tertiary amino (—NR(R'); also referred to as di-substituted amino), amidino (—C(=NH)—NH$_2$), substituted amidino (—C(=NR)—NR'R"), guanidino (—NH—C(=NH)—NH$_2$), substituted guanidino (—NR—C(=NR''')—NR'R"), aminocarbonylamino (—NR—CO—NR'R"), pyridyl, piperidino, morpholino, and azetidinyl.

Examples of secondary amino (—NH—R; mono-substituted amino) include alkylamino, cycloalkylamino, alkenylamino, alkynylamino, arylamino, heteroarylamino, and aralkylamino. Examples of tertiary amino (—NR(R'); di-substituted amino) include amino groups that have any two substituents each independently selected from alkyl, cycloalkyl, alkenyl, alkynyl, aryl, heteroaryl, and aralkyl, such as alkyl(aralkyl) amino, and these two substituents may form a ring. Specific examples include dialkylamino, in particular, $C_1$-$C_6$ dialkylamino, $C_1$-$C_4$ dialkylamino, dimethylamino, and diethylamino. The "$C_p$-$C_q$ dialkylamino group" herein refers to an amino group substituted with two $C_p$-$C_q$ alkyl groups, and the $C_p$-$C_q$ alkyl groups may be the same or different.

Examples of substituted amidino (—C(=NR)—NR'R") include groups in which three substituents R, R', and R" on the N atoms are each independently selected from alkyl, cycloalkyl, alkenyl, alkynyl, aryl, heteroaryl, and aralkyl, such as alkyl(aralkyl)(aryl) amidino.

Examples of substituted guanidino (—NR—C(=NR")—NR'R"') include groups in which R, R', R", and R"' are each independently selected from alkyl, cycloalkyl, alkenyl, alkynyl, aryl, heteroaryl, and aralkyl, and groups in which these substituents form a ring.

Examples of aminocarbonylamino (—NR—CO—NR'R") include groups in which R, R', and R" are each independently selected from a hydrogen atom, alkyl, cycloalkyl, alkenyl, alkynyl, aryl, heteroaryl, and aralkyl, or groups in which these substituents form a ring.

Herein, a "peptide residue" or an "amino acid residue" constituting the peptide compound may be simply referred to as a "peptide" or an "amino acid", respectively.

In the present invention, the meaning of the term "and/or" includes any combination attained by suitably combining "and" and "or". Specifically, for example, "A, B, and/or C" includes the following 7 variations:
(i) A, (ii) B, (iii) C, (iv) A and B, (v) A and C, (vi) B and C, (vii) A, B, and C.

In an embodiment, the present invention relates to a cyclic compound represented by formula (1) below or a salt thereof, or a solvate thereof.

(1)

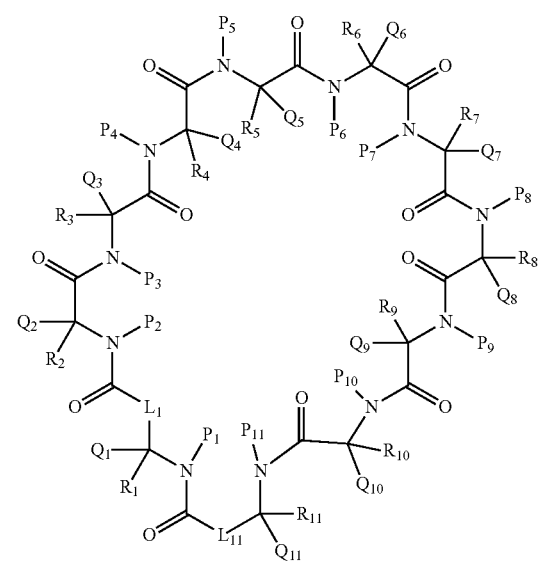

In the cyclic compound of formula (1), the ring is composed of 11 amino acid residues. Herein, the amino acid residue having $P_1$, $Q_1$, $R_1$, and $L_1$ in the formula may be referred to as core 1, the amino acid residue having $P_2$, $Q_2$, and $R_2$ as core 2, the amino acid residue having $P_3$, $Q_3$, and $R_3$ as core 3, the amino acid residue having $P_4$, $Q_4$, and $R_4$ as core 4, the amino acid residue having $P_5$, $Q_5$, and $R_5$ as core 5, the amino acid residue having $P_6$, $Q_6$, and $R_6$ as core 6, the amino acid residue having $P_7$, $Q_7$, and $R_7$ as core 7, the amino acid residue having $P_8$, $Q_8$, and $R_8$ as core 8, the amino acid residue having $P_9$, $Q_9$, and $R_9$ as core 9, the amino acid residue having $P_{10}$, $Q_{10}$, and $R_{10}$ as core 10, and the amino acid residue having $P_{11}$, $Q_1$, $R_{11}$, and $L_{11}$ as core 11.

In an embodiment, in formula (1), $L_1$ is a single bond.

In an embodiment, in formula (1), $R_1$ is a $C_1$ to $C_7$ alkyl, and preferably, a 2-methylpropyl or a n-propyl.

In an embodiment, $R_1$ joins together with $R_5$ to form a divalent group, wherein a partial structure: *-$CR_1Q_1$-$L_1$-CO—$NP_2$-$CR_2Q_2$-CO—$NP_3$-$CR_3Q_3$—CO—$NP_4$-$CR_4Q_4$—CO—$NP_5$-$CR_5Q_5$—* in the cyclic compound represented by formula (1) is represented by the following formula:

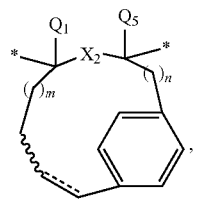

wherein:
$X_2$ is —$L_1$-CO—$NP_2$-$CR_2Q_2$-CO—$NP_3$-$CR_3Q_3$—CO—$NP_4$-$CR_4Q_4$—CO—$NP_5$—, ---- is a single bond or a double bond,
n is 0, 1 or 2,
m is 0, 1, 2, 3 or 4,
* represents an attachment point to an adjacent atom;
wherein
～～ may take E or Z configuration, if
---- is a double bond.
The formula is preferably a formula:

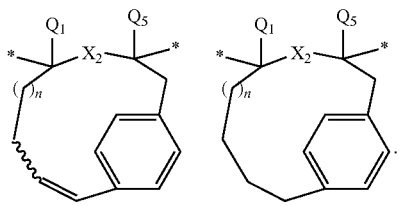

In an embodiment, $P_1$ is a $C_1$ to $C_6$ alkyl, and preferably methyl.

In an embodiment, $Q_1$ is a hydrogen atom.

The amino acid residue of core 1 is, for example, MeLeu or MeNva except the case where a side chain ($R_1$) of core 1 and a side chain ($R_5$) of core 5 join together to form a divalent group.

If a side chain ($R_1$) of core 1 and a side chain ($R_5$) of core 5 join together to form a divalent group, the group at the position corresponding to $R_1$ of MeAhpe (2), MeAocte (2) or MeAhxe (2) and the group at the position corresponding to side chain ($R_5$) of core 5 can be linked by use of a method described, for example, in the "common process" later described.

In an embodiment, in formula (1), $R_2$ is a $C_1$ to $C_6$ alkyl, and preferably 1-methylpropyl.

In an embodiment, $P_2$ is a hydrogen atom.
In an embodiment, $Q_2$ is a hydrogen atom.
The amino acid residue of core 2 is, for example, Ile.

In an embodiment, in formula (1), $R_3$ is a hydrogen atom.

In an embodiment, $R_3$ joins together with a carbon atom to which $P_3$ and $R_3$ are attached and a nitrogen atom to which $P_3$ is attached, to form a 4 to 7-membered saturated heterocycle. The 4 to 7-membered saturated heterocycle is, for example, a pyrrolidine ring.

In an embodiment, $P_3$ is a $C_1$ to $C_6$ alkyl or a $C_3$ to $C_8$ cycloalkyl, and preferably a methyl or a cyclopropyl.

In an embodiment, $Q_3$ is a hydrogen atom.

The amino acid residue of core 3 is, for example, MeGly, Pro or cPrGly.

In an embodiment, $R_4$ joins together with $P_5$ to form a divalent group, wherein a partial structure: *-$CR_4Q_4$—CO—$NP_5$—* of a cyclic compound represented by formula (1) is expressed by the following formula:

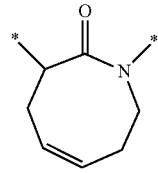

In an embodiment, $P_4$ is a $C_1$ to $C_6$ alkyl, and preferably methyl.

In an embodiment, $Q_4$ is a hydrogen atom.

If a side chain ($R_4$) of core 4 and N substituent ($P_5$) of core 5 join together to form a divalent group, preferably, a group at the position corresponding to $R_4$ of MeAlgly and a group at the position corresponding to N substituent ($P_5$) of core 5 can be linked by use of a method described, for example, in the "common process" later described.

In an embodiment, in formula (1), $R_5$ is a benzyl optionally substituted with one or more groups independently selected from the group consisting of a $C_1$ to $C_6$ alkyl, a $C_1$ to $C_6$ haloalkyl, and a $C_3$ to $C_8$ cycloalkyl, and preferably, 4-cyclopropylbenzyl, 4-(trifluoromethyl)benzyl, 4-methylbenzyl or 4-ethylbenzyl.

In an embodiment, in formula (1), $R_5$ joins together with $R_1$ to form a divalent group. The details of this group are the same as defined in the above.

In an embodiment, $P_5$ joins together with $R_4$ to form a divalent group. The details of this group are the same as defined in the above.

In an embodiment, $Q_5$ is a hydrogen atom.

If a side chain ($R_5$) of core 5 and a side chain ($R_1$) of core 1 join together to form a divalent group, and a N substituent ($P_5$) of core 5 and side chain ($R_4$) of core 4 join together to form a divalent group, more specifically, $R_5$ of ButenylPhe (4—CH═$CH_2$) and a group at the position corresponding to $P_5$, and a side chain ($R_1$) of core 1 and a group at the position corresponding to a side chain ($R_4$) of core 4, can be linked respectively, by use of a method described, for example, in the "common process" later described.

In the case where a side chain ($R_5$) of core 5 and a side chain ($R_1$) of core 1 do not form a divalent group, and a N substituent ($P_5$) of core 5 and a side chain ($R_4$) of core 4 form a divalent group, more specifically, a group at the position corresponding to $P_5$ of ButenylPhe (4-Et), ButenylPhe (4-cPr) or AllylPhe (4—$CF_3$) and a group at the position corresponding to side chain ($R_4$) of core 4 can be linked by use of a method described, for example, in the "common process" later described.

In an embodiment, in formula (1), $R_6$ is a hydrogen atom.

In an embodiment, $P_6$ is a $C_1$ to $C_6$ alkyl, and preferably methyl.

In an embodiment, $Q_6$ is a hydrogen atom.

The amino acid residue of core 6 is, for example, MeGly.

In an embodiment, in formula (1), phenethyl optionally substituted with one or more groups independently selected from the group consisting of halogen, a $C_1$ to $C_6$ haloalkyl and a $C_1$ to $C_6$ alkoxy, is preferably, 3,5-difluoro-4-(trifluoromethyl) phenethyl, 3,4-dichlorophenethyl or 3-methoxy-4-(trifluoromethyl) phenethyl.

In an embodiment, $P_7$ is a hydrogen atom.

In an embodiment, $Q_7$ is a hydrogen atom.

The amino acid residue of core 7 is, for example, Hph (4—CF3-35-F2), Hph(34-C12) or Hph(4—CF3-3-OMe).

In an embodiment, in formula (1), R& joins together with a carbon atom to which $P_8$ and $R_8$ are attached and a nitrogen atom to which P& is attached, to form a 4 to 7-membered saturated heterocycle. The 4 to 7-membered saturated heterocycle is optionally substituted with a $C_1$ to $C_6$ alkoxy, and preferably ethoxy or n-propoxy. The 4 to 7-membered saturated heterocycle is, for example, a pyrrolidine ring.

In an embodiment, $Q_8$ is a hydrogen atom.

The amino acid residue of core 8 is, for example, Hyp (Et) or Hyp (nPr).

In an embodiment, in formula (1), $R_9$ joins together with $Q_9$ and a carbon atom to which $R_9$ and $Q_9$ are attached to form a 3 to 8-membered alicyclic ring. The 3 to 8-membered alicyclic ring is optionally substituted with one or more $C_1$ to $C_6$ alkyls, for example, two methyl groups. The 3 to 8-membered alicyclic ring is, for example, a cyclobutane ring or a cyclopentane ring.

In an embodiment, $P_9$ is a hydrogen atom or a $C_1$ to $C_6$ alkyl, and preferably a hydrogen atom or a methyl.

The amino acid residue of core 9 is, for example, cLeu, cVal, cVal (3-Me2) or Mec Val.

In an embodiment, in formula (1), $R_{10}$ is a $C_1$ to $C_6$ alkyl or a $C_3$ to $C_8$ cycloalkyl, and preferably, a pentan-3-yl or cyclopentyl.

In an embodiment, $P_{10}$ is a $C_1$ to $C_6$ alkyl, and preferably methyl.

In an embodiment, $Q_{10}$ is a hydrogen atom.

The amino acid residue of core 10 is, for example, MeGly (cPent) or MeNva (3-Et).

In an embodiment, in formula (1), $L_{11}$ is —$CH_2$—.

In an embodiment, in formula (1), $R_{11}$ is a di-$C_1$ to $C_6$ alkylaminocarbonyl or a 4 to 8-membered cyclic aminocarbonyl, and preferably, a dimethylaminocarbonyl, a N-ethyl-N-methylaminocarbonyl, a pyrrolidinylcarbonyl or a piperidinylcarbonyl.

In an embodiment, $P_{11}$ is a $C_1$ to $C_6$ alkyl, and preferably, a methyl.

In an embodiment, $Q_{11}$ is a hydrogen atom.

In an embodiment, the compound of the present invention can be one or more compounds selected from the following:

PP1574: (2S,8S,12R,14S,20S,23S,27S,30S,36S,38Z)-20-cyclopentyl-8-[2-[3,5-difluoro-4-(trifluoromethyl)phenyl]ethyl]-12-ethoxy-N-ethyl-27-isobutyl-N,4,19,22,26,32,35-heptamethyl-30-[(1 S)-1-methylpropyl]-3,6,9,15,18,21,25,28,31,34,42-undecaoxo-2-[[4-(trifluoromethyl)phenyl]methyl]spiro[1,4,7,10,16,19,22,26,29,32,35-undecazatricyclo[34.5.1.0$^{10,14}$]dotetracont-38-ene-17,1'-cyclopentane]-23-carboxamide, PP1650: (2S,8S,12R,14S,20S,23S,27S,30S,36S,38Z)-20-cyclopentyl-8-[2-[3,5-difluoro-4-(trifluoromethyl)phenyl]ethyl]-12-ethoxy-27-isobutyl-N,N,3',3',4,19,22,26,32,35-decamethyl-30-[(1 S)-1-methylpropyl]-3,6,9,15,18,21,25,28,31,34,42-undecaoxo-2-[[4-(trifluoromethyl)phenyl]methyl]spiro[1,4,7,10,16,19,22,26,29,32,35-undecazatricyclo[34.5.1.0$^{10,14}$]dotetracont-38-ene-17,1'-cyclobutane]-23-carboxamide, PP1827: (1S,7S,IIR,13S,19S,22S,26S,29S,35S,37Z,47E)-19-cyclopentyl-7-[2-[3,5-difluoro-4-(trifluoromethyl)phenyl]ethyl]-11-ethoxy-N-ethyl-N,3,18,21,25,31,34-heptamethyl-29-[(1 S)-1-methylpropyl]-2,5,8,14,17,20,24,27,30,33,55-undecaoxo-spiro[3,6,9,15,18,21,25,28,31,34,41-undecazapentacyclo[24.15.11.2$^{43,46}$.1$^{35,41}$.0$^{9,13}$]pentapentaconta-37,43(54),44,46(53),47-pentaene-16,1'-cyclobutane]-22-carboxamide, PP1830: (1S,7S,IIR,13S,19S,22S,26S,29S,35S,37Z,47E)-19-cyclopentyl-11-ethoxy-N-ethyl-7-[2-[3-methoxy-4-(trifluoromethyl)phenyl]ethyl]-N,3,3',3',18,21,25,31,34-nonamethyl-29-[(1 S)-1-methylpropyl]-2,5,8,14,17,20,24,27,30,33,55-undecaoxo-spiro[3,6,9,15,18,21,25,28,31,34,41-undecazapentacyclo[24.15.11.2$^{43,46}$.1$^{35,41}$.0$^{9,13}$]pentapentaconta-37,43(54),44,46(53),47-pentaene-16,1'-cyclobutane]-22-carboxamide, PP2093: (2S,8S,12R,14S,20S,23S,27S,30S,36S,38Z)-20-cyclopentyl-32-cyclopropyl-8-[2-[3,5-difluoro-4-(trifluoromethyl)phenyl]ethyl]-12-ethoxy-N,N,3',3',4,19,22,26,35-nonamethyl-30-[(1 S)-1-methylpropyl]-3,6,9,15,18,21,25,28,31,34,42-undecaoxo-27-propyl-2-(p-tolylmethyl)spiro[[1,4,7,10,16,19,22,26,29,32,35-undecazatricyclo[34.5.1.0$^{10,14}$]dotetracont-38-ene-17,1'-cyclobutane]-23-carboxamide, PP2260: (1S,7S,11R,13S,19S,22S,26S,29S,35S,37Z)-19-cyclopentyl-11-ethoxy-N-ethyl-7-[2-[3-methoxy-4-(trifluoromethyl)phenyl]ethyl]-N,3,3',3',18,21,25,31,34-nonamethyl-29-[(1 S)-1-methylpropyl]-2,5,8,14,17,20,24,27,30,33,55-undecaoxo-spiro[3,6,9,15,18,21,25,28,31,34,41-undecazapentacyclo[24.15.11.2$^{43,46}$.1$^{35,41}$.0$^{9,13}$]pentapentaconta-37,43(54),44,46(53)-tetraene-16,1'-cyclobutane]-22-carboxamide, PP2316: (2S,8S, 12R, 14S,20S,23S,27S,30S,36S,38Z)-20-cyclopentyl-32-cyclopropyl-12-ethoxy-8-[2-[3-methoxy-4-(trifluoromethyl)phenyl]ethyl]-N,N,4,16,19,22,26,35-octamethyl-30-[(1 S)-1-methylpropyl]-3,6,9,15,18,21,25,28,31,34,42-undecaoxo-27-propyl-2-[[4-(trifluoromethyl)phenyl]methyl]spiro[1,4,7,10,16,19,22,26,29,32,35-undecazatricyclo[34.5.1.0$^{10,14}$]dotetracont-38-ene-17,1'-cyclobutane]-23-carboxamide, PP2320: (1S,4S,10S,13S,17S,20S,26S,28R,32S,38S,42Z)-20-cyclopentyl-28-ethoxy-32-[2-[3-methoxy-4-(trifluoromethyl)phenyl]ethyl]-N, N, 2,14,18,21, 24,36-octamethyl-10-[(1 S)-1-methylpropyl]-3,9,12,15,19,22,25,31,34,37,45-undecaoxo-13-propyl-38-[[4-(trifluoromethyl)phenyl]methyl]spiro[2,8,11,14,18,21,24,30,33,36,39-undecazatetracyclo[37.5.1.0$^{4,8}$.0$^{26,30}$]pentatetracont-42-ene-23,1'-cyclobutane]-17-carboxamide, PP2328: (2S,8S,12R,14S,20S,23S,27S,30S,36S,38Z)-20-cyclopentyl-32-cyclopropyl-12-ethoxy-8-[2-[3-methoxy-4-(trifluoromethyl)phenyl]ethyl]-N,N,4,16,19,22,26,35-octamethyl-30-[(1 S)-1-methylpropyl]-3,6,9,15,18,21,25,28,31,34,42-undecaoxo-27-propyl-2-(p-tolylmethyl)spiro[[1,4,7,10,16,19,22,26,29,32,35-undecazatricyclo[34.5.1.0$^{10,14}$]dotetracont-38-ene-17,1'-cyclobutane]-23-carboxamide, PP2574: (1S,7S,11R,13S,19S,22S,26S,29S,35S,37Z,47E)-19-cyclopentyl-7-[2-[3,5-difluoro-4-(trifluoromethyl)phenyl]ethyl]-11-ethoxy-3,3',3',18,21,25,31,34-octamethyl-29-[(1 S)-1-methylpropyl]-22-(pyrrolidine-1-carbonyl)spiro[3,6,9,15,18,21,25,28,31,34,41-undecazapentacyclo[24.15.10.2$^{43,46}$.1$^{35,41}$.0$^{9,13}$]tetrapentaconta-37,43(53),44,46(52),47-pentaene-16,1'-cyclobutane]-2,5,8,14,17,20,24,27,30,33,54-undecone, PP2576: (1S,7S,11R,13S,19S,22S,26S,29S,35S,37Z,47E)-7-[2-[3,5-difluoro-4-(trifluoromethyl)phenyl]ethyl]-11-ethoxy-19-(1-ethylpropyl)-3,3',3',18,21,25,31,34-octamethyl-29-[(1 S)-1-methylpropyl]-22-(pyrrolidine-1-carbonyl)spiro[3,6,9,15,18,21,25,28,31,34,41-undecazapentacyclo[24.15.10.2$^{43,46}$.1$^{35,41}$.0$^{9,13}$]tetrapentaconta-37,43(53),44,46(52),47-pentaene-16,1'-cyclobutane]-2,5,8,14,17,20,24,27,30,33,54-undecone, PP2583: (1S,7S,11R,13S,19S,22S,26S,29S,35S,37Z,47E)-19-cyclopentyl-31-cyclopropyl-7-[2-[3,5-difluoro-4-(trifluoromethyl)phenyl]ethyl]-11-ethoxy-3,3',3',18,21,25,34-heptamethyl-29-[(1 S)-1-methylpropyl]-22-(pyrrolidine-1-carbonyl)spiro[3,6,9,15,18,21,25,28,31,34,41-undecazapentacyclo[24.15.10.2$^{43,46}$.1$^{35,41}$.0$^{9,13}$]tetrapentaconta-37,43(53),44,46(52),47-pentaene-16,1'-cyclobutane]-2,5,8,14,17,20,24,27,30,33,54-undecone, PP2687: (2S,8S,12R,14S,20S,23S,27S,30S,36S,38Z)-20-cyclopentyl-12-ethoxy-2-[(4-ethylphenyl)methyl]-27-isobutyl-8-[2-[3-methoxy-4-(trifluoromethyl)phenyl]ethyl]-N,N,3',3',4,19,22,26,32,35-decamethyl-30-[(1S)-1-methylpropyl]-3,6,9,15,18,21,25,28,31,34,42-undecaoxo-spiro[1,4,7,10,16,19,22,26,29,32,35-undecazatricyclo[34.5.1.0$^{10,14}$]dotetracont-38-ene-17,1'-cyclobutane]-23-carboxamide, PP2691: (2S,8S,12R,14S,20S,23S,27S,30S,36S,38Z)-20-cyclopentyl-2-[(4-cyclopropylphenyl)methyl]-12-ethoxy-27-isobutyl-8-[2-[3-methoxy-4-(trifluoromethyl)phenyl]ethyl]-N,N,3',3',4,19,22,26,32,35-decamethyl-30-[(1 S)-1-methylpropyl]-3,6,9,15,18,21,25,28,31,34,42-undecaoxo-spiro[1,4,7,10,16,19,22,26,29,32,35-undecazatricyclo[34.5.1.0$^{10,14}$]dotetracont-38-ene-17,1'-cyclobutane]-23-carboxamide, PP2957: (1S,7S,11R,13S,19S,22S,26S,29S,35S,37Z,47E)-31-cyclopropyl-7-[2-[3,5-difluoro-4-(trifluoromethyl)phenyl]ethyl]-11-ethoxy-19-(1-ethylpropyl)-3,18,21,25,34-pentamethyl-29-[(1 S)-1-methylpropyl]-22-(pyrrolidine-1-carbonyl)spiro[3,6,9,15,18,21,25,28,31,34,41-undecazapentacyclo[24.15.10.2$^{43,46}$.1$^{35,41}$.0$^{9,13}$]tetrapentaconta-37,43(53),44,46(52),47-pentaene-16,1'-cyclobutane]-2,5,8,14,17,20,24,27,30,33,54-undecone, PP3033: (1S,7S,11R,13S,19S,22S,26S,29S,35S,37Z)-19-cyclopentyl-11-ethoxy-7-[2-[3-methoxy-4-(trifluoromethyl)phenyl]ethyl]-3,18,21,25,31,34-hexamethyl-29-[(1 S)-1-methylpropyl]-22-(piperidine-1-carbonyl)spiro[3,6,9,15,18,21,25,28,31,34,4l-undecazapentacyclo[24.15.11.2$^{43,46}$.1$^{35,41}$.0$^{9,13}$]pentapentaconta-37,43(54),44,46(53)-tetraene-16,1'-cyclobutane]-2,5,8,14,17,20,24,27,30,33,55-undecone, PP3034: (1S,7S,11R,13S,19S,22S,26S,29S,35S,37Z)-19-cyclopentyl-11-ethoxy-7-[2-[3-methoxy-4-(trifluoromethyl)phenyl]ethyl]-3,3',3',18,21,25,31,34-octamethyl-29-[(1S)-1-methylpropyl]-22-(pyrrolidine-1-carbonyl)spiro[3,6,9,15,18,21,25,28,31,34,41-undecazapentacyclo[24.15.11.2$^{43,46}$.1$^{35,41}$.0$^{9,13}$]pentapentaconta-37,43(54),44,46(53)-tetraene-16,1'-cyclobutane]-2,5,8,14,17,20,24,27,30,33,55-undecone, PP3036: (1S,7S,11R,13S,19S,22S,26S,29S,35S,37Z)-19-cyclopentyl-11-ethoxy-7-[2-[3-methoxy-4-(trifluoromethyl)phenyl]ethyl]-3,3',3',18,21,25,31,34-octamethyl-29-[(1S)-1-methylpropyl]-22-(piperidine-1-carbonyl)spiro[3,6,9,15,18,21,25,28,31,34,41-undecazapentacyclo[24.15.10.2$^{43,46}$.1$^{35,41}$.0$^{9,13}$]tetrapentaconta-37,43(53),44,46(52)-tetraene-16,1'-cyclobutane]-2,5,8,14,17,20,24,27,30,33,54-undecone, PP3037: (1S,7S,11R,13S,19S,22S,26S,29S,35S,37Z)-19-cyclopentyl-11-ethoxy-7-[2-[3-methoxy-4-(trifluoromethyl)phenyl]ethyl]-3,3',3',18,21,25,31,34-octamethyl-29-[(1S)-1-methylpropyl]-22-(pyrrolidine-1-carbonyl)spiro[3,6,9,15,18,21,25,28,31,34,41-undecazapentacyclo[24.15.10.2$^{43,46}$.1$^{35,41}$.0$^{9,13}$]tetrapentaconta-37,43(53),44,46(52)-tetraene-16,1'-cyclobutane]-2,5,8,14,17,20,24,27,30,33,54-undecone, PP3047: (1S,7S,IIR,13S,19S,22S,26S,29S,35S,37Z,47E)-7-[2-(3,4-dichlorophenyl)ethyl]-I1-ethoxy-19-(I-ethylpropyl)-3,18,21,25,31,34-hexamethyl-29-[(1S)-1-methylpropyl]-22-(pyrrolidine-1-carbonyl)spiro[3,6,9,15,18,21,25,28,31,34,41-undecazapentacyclo[24.15.11.2$^{43,46}$.1$^{35,41}$.0$^{9,13}$]pentapentaconta-37,43(54),44,46(53),47-pentaene-16,1'-cyclobutane]-2,5,8,14,17,20,24,27,30,33,55-undecone, PP3093: (1S,7S,11R,13S,19S,22S,26S,29S,35S,37Z)-19-cyclopentyl-11-ethoxy-7-[2-[3-methoxy-4-(trifluoromethyl)phenyl]ethyl]-3,3',3',18,21,25,31,34-octamethyl-29-[(1S)-1-methylpropyl]-22-(piperidine-1-carbonyl)spiro[3,6,9,15,18,21,25,28,31,34,41-undecazapentacyclo[24.15.9.2$^{43,46}$.1$^{35,41}$.0$^{9,13}$]tripentaconta-37,43(52),44,46(51)-tetraene-16,1'-cyclobutane]-2,5,8,14,17,20,24,27,30,33,53-undecone, PP3094: (1S,7S,11R,13S,19S,22S,26S,29S,35S,37Z)-19-cyclopentyl-7-[2-[3-methoxy-4-(trifluoromethyl)phenyl]ethyl]-3,3',3',18,21,25,31,34-octamethyl-29-[(1 S)-1-methylpropyl]-11-propoxy-22-(pyrrolidine-1-carbonyl)spiro[3,6,9,15,18,21,25,28,31,34,41-undecazapentacyclo[24.15.9.2$^{43,46}$.1$^{35,41}$.0$^{9,13}$]tripentaconta-37,43(52),44,46(51)-tetraene-16,1'-cyclobutane]-2,5,8,14,17,20,24,27,30,33,53-undecone, PP3095: (2S,8S,12R,14S,20S,23S,27S,30S,36S,38Z)-20-cyclopentyl-32-cyclopropyl-12-ethoxy-8-[2-[3-methoxy-4-(trifluoromethyl)phenyl]ethyl]-4,16,19,22,26,35-hexamethyl-30-[(1S)-1-methylpropyl]-23-(piperidine-1-carbonyl)-27-propyl-2-[[4-(trifluoromethyl)phenyl]methyl]spiro[1,4,7,10,16,19,22,26,29,32,35-undecazatricyclo[34.5.1.0$^{10,14}$]dotetracont-38-ene-17,1'-cyclobutane]-3,6,9,15,18,21,25,28,31,34,42-undecone, PP3096: (2S,8S,12R,14S,20S,23S,27S,30S,36S,38Z)-20-cyclopentyl-32-cyclopropyl-12-ethoxy-8-[2-[3-methoxy-4-(trifluoromethyl)phenyl]ethyl]-4,16,19,22,26,35-hexamethyl-30-[(1S)-1-methylpropyl]-23-(piperidine-1-carbonyl)-27-propyl-2-(p-tolylmethyl)spiro[[1,4,7,10,16,19,22,26,29,32,35-undecazatricyclo[34.5.1.0$^{10,14}$]dotetracont-38-ene-17,1-cyclobutane]-3,6,9,15,18,21,25,28,31,34,42-undecone, PP3097: (2S,8S,12R,14S,20S,23S,27S,30S,36S,38Z)-20-cyclopentyl-32-cyclopropyl-12-ethoxy-8-[2-[3-methoxy-4-(trifluoromethyl)phenyl]ethyl]-4,16,19,22,26,35-hexamethyl-30-[(1S)-1-methylpropyl]-27-propyl-23-(pyrrolidine-1-carbonyl)-2-[[4-(trifluoromethyl)phenyl]methyl]spiro[1,4,7,10,16,19,22,26,29,32,35-undecazatricyclo[34.5.1.0$^{10,14}$1dotetracont-38-ene-17,1'-cyclobutane]-3,6,9,15,18,21,25,28,31,34,42-undecone, PP3098: (2S,8S,12R,14S,20S,23S,27S,30S,36S,38Z)-20-cyclopentyl-32-cyclopropyl-12-ethoxy-8-[2-[3-methoxy-4-(trifluoromethyl)phenyl]ethyl]-4,16,19,22,26,35-hexamethyl-30-[(1S)-1-methylpropyl]-27-propyl-2-(p-tolylmethyl)-23-(pyrrolidine-1-carbonyl)spiro[1,4,7,10,16,19,22,26,29,32,35-undecazatricyclo[34.5.1.0$^{10,14}$]dotetracont-38-ene-17,1-cyclobutane]-3,6,9,15,18,21,25,28,31,34,42-undecone, PP3099: (1S,4S,10S,13S,17S,20S,26S,28R,32S,38S,42Z)-20-cyclopentyl-28-ethoxy-32-[2-[3-methoxy-4-(trifluoromethyl)phenyl]ethyl]-2,14,18,21,24,36-hexamethyl-10-[(1 S)-1-methylpropyl]-17-(piperidine-1-carbonyl)-13-propyl-38-[[4-(trifluoromethyl)phenyl]methyl]spiro[2,8,11,14,18,21,24,30,33,36,39-undecazatetracyclo

[37.5.1.0$^{4,8}$.0$^{26,30}$]pentatetracont-42-ene-23,1'-cyclobutane]-3,9,12,15,19,22,25,31,34,37,45-undecone, PP3100: (1S,4S,1OS,13S,17S,20S,26S,28R,32S,38S,42Z)-20-cyclopentyl-28-ethoxy-32-[2-[3-methoxy-4-(trifluoromethyl)phenyl]ethyl]-2,14,18,21,24,36-hexamethyl-10-[(1 S)-1-methylpropyl]-17-(piperidine-1-carbonyl)-13-propyl-38-(p-tolylmethyl)spiro[2,8,11,14,18,21,24,30,33,36,39-undecazatetracyclo[37.5.1.0$^{4,8}$.0$^{26,30}$]pentatetracont-42-ene-23,1'-cyclobutane]-3,9,12,15,19,22,25,31,34,37,45-undecone, PP3101: (1S,4S,1OS,13S,17S,20S,26S,28R,32S,38S,42Z)-20-cyclopentyl-28-ethoxy-32-[2-[3-methoxy-4-(trifluoromethyl)phenyl]ethyl]-2,14,18,21,24,36-hexamethyl-10-[(1 S)-1-methylpropyl]-13-propyl-17-(pyrrolidine-1-carbonyl)-38-[[4-(trifluoromethyl)phenyl]methyl]spiro[2,8,11,14,18,21,24,30,33,36,39-undecazatetracyclo[37.5.1.0$^{4,8}$.0$^{26,30}$]pentatetracont-42-ene-23,1'-cyclobutane]-3,9,12,15,19,22,25,31,34,37,45-undecone, PP3102: (1S,4S,1OS,13S,17S,20S,26S,28R,32S,38S,42Z)-20-cyclopentyl-28-ethoxy-32-[2-[3-methoxy-4-(trifluoromethyl)phenyl]ethyl]-2,14,18,21,24,36-hexamethyl-10-[(1 S)-1-methylpropyl]-13-propyl-38-(p-tolylmethyl)-17-(pyrrolidine-1-carbonyl)spiro[2,8,11,14,18,21,24,30,33,36,39-undecazatetracyclo[37.5.1.0$^{4,8}$.0$^{26,30}$]pentatetracont-42-ene-23,1'-cyclobutane]-3,9,12,15,19,22,25,31,34,37,45-undecone, PP3103: (2S,8S,12R,14S,20S,23S,27S,30S,36S,38Z)-20-cyclopentyl-12-ethoxy-8-[2-[3-methoxy-4-(trifluoromethyl)phenyl]ethyl]-4,16,19,22,26,32,35-heptamethyl-30-[(1 S)-1-methylpropyl]-23-(piperidine-1-carbonyl)-27-propyl-2-[[4-(trifluoromethyl)phenyl]methyl]spiro[1,4,7,10,16,19,22,26,29,32,35-undecazatricyclo[34.5.1.0$^{10,14}$]dotetracont-38-ene-17,1'-cyclobutane]-3,6,9,15,18,21,25,28,31,34,42-undecone, PP3104: (2S,8S,12R,14S,20S,23S,27S,30S,36S,38Z)-20-cyclopentyl-12-ethoxy-8-[2-[3-methoxy-4-(trifluoromethyl)phenyl]ethyl]-4,16,19,22,26,32,35-heptamethyl-30-[(1 S)-1-methylpropyl]-23-(piperidine-1-carbonyl)-27-propyl-2-(p-tolylmethyl)spiro[[1,4,7,10,16,19,22,26,29,32,35-undecazatricyclo[34.5.1.0$^{10,14}$]dotetracont-38-ene-17,1-cyclobutane]-3,6,9,15,18,21,25,28,31,34,42-undecone, PP3105: (2S,8S,12R,14S,20S,23S,27S,30S,36S,38Z)-20-cyclopentyl-12-ethoxy-8-[2-[3-methoxy-4-(trifluoromethyl)phenyl]ethyl]-4,16,19,22,26,32,35-heptamethyl-30-[(1 S)-1-methylpropyl]-27-propyl-23-(pyrrolidine-1-carbonyl)-2-[[4-(trifluoromethyl)phenyl]methyl]spiro[1,4,7,10,16,19,22,26,29,32,35-undecazatricyclo[34.5.1.0$^{10,14}$]dotetracont-38-ene-17,1'-cyclobutane]-3,6,9,15,18,21,25,28,31,34,42-undecone, PP3106: (2S,8S,12R,14S,20S,23S,27S,30S,36S,38Z)-20-cyclopentyl-12-ethoxy-8-[2-[3-methoxy-4-(trifluoromethyl)phenyl]ethyl]-4,16,19,22,26,32,35-heptamethyl-30-[(1 S)-1-methylpropyl]-27-propyl-2-(p-tolylmethyl)-23-(pyrrolidine-1-carbonyl)spiro[1,4,7,10,16,19,22,26,29,32,35-undecazatricyclo[34.5.1.0$^{10,14}$]dotetracont-38-ene-17,1-cyclobutane]-3,6,9,15,18,21,25,28,31,34,42-undecone, PP3110: (2S,8S,12R,14S,20S,23S,27S,30S,36S,38Z)-20-cyclopentyl-32-cyclopropyl-8-[2-[3,5-difluoro-4-(trifluoromethyl)phenyl]ethyl]-12-ethoxy-4,16,19,22,26,35-hexamethyl-30-[(1 S)-1-methylpropyl]-23-(piperidine-1-carbonyl)-27-propyl-2-[[4-(trifluoromethyl)phenyl]methyl]spiro[1,4,7,10,16,19,22,26,29,32,35-undecazatricyclo[34.5.1.0$^{10,14}$]dotetracont-38-ene-17,1'-cyclobutane]-3,6,9,15,18,21,25,28,31,34,42-undecone, PP3111: (2S,8S,12R,14S,20S,23S,27S,30S,36S,38Z)-20-cyclopentyl-32-cyclopropyl-8-[2-[3,5-difluoro-4-(trifluoromethyl)phenyl]ethyl]-12-ethoxy-4,16,19,22,26,35-hexamethyl-30-[(1 S)-1-methylpropyl]-23-(piperidine-1-carbonyl)-27-propyl-2-(p-tolylmethyl)spiro[[1,4,7,10,16,19,22,26,29,32,35-undecazatricyclo[34.5.1.0$^{10,14}$]dotetracont-38-ene-17,1-cyclobutane]-3,6,9,15,18,21,25,28,31,34,42-undecone, PP3112: (2S,8S,12R,14S,20S,23S,27S,30S,36S,38Z)-20-cyclopentyl-32-cyclopropyl-8-[2-[3,5-difluoro-4-(trifluoromethyl)phenyl]ethyl]-12-ethoxy-4,16,19,22,26,35-hexamethyl-30-[(1 S)-1-methylpropyl]-27-propyl-23-(pyrrolidine-1-carbonyl)-2-[[4-(trifluoromethyl)phenyl]methyl]spiro[1,4,7,10,16,19,22,26,29,32,35-undecazatricyclo[34.5.1.0$^{10,14}$]dotetracont-38-ene-17,1'-cyclobutane]-3,6,9,15,18,21,25,28,31,34,42-undecone, PP3113: (2S,8S,12R,14S,20S,23S,27S,30S,36S,38Z)-20-cyclopentyl-32-cyclopropyl-8-[2-[3,5-difluoro-4-(trifluoromethyl)phenyl]ethyl]-12-ethoxy-4,16,19,22,26,35-hexamethyl-30-[(1 S)-1-methylpropyl]-27-propyl-2-(p-tolylmethyl)-23-(pyrrolidine-l-carbonyl)spiro[1,4,7,10,16,19,22,26,29,32,35-undecazatricyclo[34.5.1.0$^{10,14}$]dotetracont-38-ene-17,1-cyclobutane]-3,6,9,15,18,21,25,28,31,34,42-undecone, PP3114: (1S,4S,1OS,13S,17S,20S,26S,28R,32S,38S,42Z)-20-cyclopentyl-32-[2-[3,5-difluoro-4-(trifluoromethyl)phenyl]ethyl]-28-ethoxy-2,14,18,21,24,36-hexamethyl-10-[(1 S)-1-methylpropyl]-17-(piperidine-1-carbonyl)-13-propyl-38-[[4-(trifluoromethyl)phenyl]methyl]spiro[2,8,11,14,18,21,24,30,33,36,39-undecazatetracyclo[37.5.1.0$^{4,8}$.0$^{26,30}$]pentatetracont-42-ene-23,1'-cyclobutane]-3,9,12,15,19,22,25,31,34,37,45-undecone, PP3115: (1S,4S,1OS,13S,17S,20S,26S,28R,32S,38S,42Z)-20-cyclopentyl-32-[2-[3,5-difluoro-4-(trifluoromethyl)phenyl]ethyl]-28-ethoxy-2,14,18,21,24,36-hexamethyl-10-[(1 S)-1-methylpropyl]-17-(piperidine-1-carbonyl)-13-propyl-38-(p-tolylmethyl)spiro[2,8,11,14,18,21,24,30,33,36,39-undecazatetracyclo[37.5.1.0$^{4,8}$.0$^{26,30}$]pentatetracont-42-ene-23,1'-cyclobutane]-3,9,12,15,19,22,25,31,34,37,45-undecone, PP3116: (1S,4S,1OS,13S,17S,20S,26S,28R,32S,38S,42Z)-20-cyclopentyl-32-[2-[3,5-difluoro-4-(trifluoromethyl)phenyl]ethyl]-28-ethoxy-2,14,18,21,24,36-hexamethyl-10-[(1 S)-1-methylpropyl]-13-propyl-17-(pyrrolidine-1-carbonyl)-38-[[4-(trifluoromethyl)phenyl]methyl]spiro[2,8,11,14,18,21,24,30,33,36,39-undecazatetracyclo[37.5.1.0$^{4,8}$.0$^{26,30}$]pentatetracont-42-ene-23,1'-cyclobutane]-3,9,12,15,19,22,25,31,34,37,45-undecone, PP3117: (1S,4S,1OS,13S,17S,20S,26S,28R,32S,38S,42Z)-20-cyclopentyl-32-[2-[3,5-difluoro-4-(trifluoromethyl)phenyl]ethyl]-28-ethoxy-2,14,18,21,24,36-hexamethyl-10-[(1 S)-1-methylpropyl]-13-propyl-38-(p-tolylmethyl)-17-(pyrrolidine-l-carbonyl)spiro[2,8,11,14,18,21,24,30,33,36,39-undecazatetracyclo[37.5.1.0$^{4,8}$.0$^{26,30}$]pentatetracont-42-ene-23,1'-cyclobutane]-3,9,12,15,19,22,25,31,34,37,45-undecone, PP3118: (2S,8S,12R,14S,20S,23S,27S,30S,36S,38Z)-20-cyclopentyl-8-[2-[3,5-difluoro-4-(trifluoromethyl)phenyl]ethyl]-12-ethoxy-4,16,19,22,26,32,35-heptamethyl-30-[(1 S)-1-methylpropyl]-23-(piperidine-1-carbonyl)-27-propyl-2-[[4-(trifluoromethyl)phenyl]methyl]spiro[1,4,7,10,16,19,22,26,29,32,35-undecazatricyclo[34.5.1.0$^{10,14}$]dotetracont-38-ene-17,1'-cyclobutane]-3,6,9,15,18,21,25,28,31,34,42-undecone, PP3119: (2S,8S,12R,14S,20S,23S,27S,30S,36S,38Z)-20-cyclopentyl-8-[2-[3,5-difluoro-4-(trifluoromethyl)phenyl]ethyl]-12-ethoxy-4,16,19,22,26,32,35-heptamethyl-30-[(1 S)-1-methylpropyl]-23-(piperidine-1-carbonyl)-27-propyl-2-(p-tolylmethyl)spiro[[1,4,7,10,16,19,22,26, 29,32,35-undecazatricyclo[34.5.1.0^{10,14}]dotetracont-38-ene-17,1-cyclobutane]-3,6,9,15,18,21,25,28,31,34,42-undecone, PP3120: (2S,8S,12R,14S,20S,23S,27S,30S,36S,38Z)-20-cyclopentyl-8-[2-[3,5-difluoro-4-(trifluoromethyl)phenyl]ethyl]-12-ethoxy-4,16,19,22,26,32,35-heptamethyl-30-[(1 S)-1-methylpropyl]-27-propyl-23-(pyrrolidine-1-carbonyl)-2-[[4-(trifluoromethyl)phenyl]methyl]spiro[1,4,7,10,16,19,22,26,29,32,35-undecazatricyclo[34.5.1.0^{10,14}]dotetracont-38-ene-17,1'-cyclobutane]-3,6,9,15,18,21,25,28,31,34,42-undecone, PP3121: (2S,8S,12R,14S,20S,23S,27S,30S,36S,38Z)-20-cyclopentyl-8-[2-[3,5-difluoro-4-(trifluoromethyl)phenyl]ethyl]-12-ethoxy-4,16,19,22,26,32,35-heptamethyl-30-[(1 S)-1-methylpropyl]-27-propyl-2-(p-tolylmethyl)-23-(pyrrolidine-1-carbonyl)spiro[1,4,7,10,16,19,22,26,29,32,35-undecazatric clo[34.5.1.0^{10,14}]dotetracont-38-ene-17,1'-cyclobutane]-3,6,9,15,18,21,25,28,31,34,42-undecone, (1S,7S,11R,13S,19S,22S,26S,29S,35S,37Z,47Z)-19-cyclopentyl-7-[2-[3,5-difluoro-4-(trifluoromethyl)phenyl]ethyl]-1I-ethoxy-N-ethyl-N,3,18,21,25,31,34-heptamethyl-29-[(1S)-l-methylpropyl]-2,5,8,14,17,20,24,27,30,33,55-undecaoxo-spiro[3,6,9,15,18,21,25,28,31,34,41-undecazapentacyclo[24.15.11.2^{43,46}.1^{35,41}.0^{9,13}]pentapentaconta-37,43(54),44,46(53),47-pentaene-16,1'-cyclobutane]-22-carboxamide, (1S,7S,11R,13S,19S,22S,26S,29S,35S,37Z,47Z)-19-cyclopentyl-11-ethoxy-N-ethyl-7-[2-[3-methoxy-4-(trifluoromethyl)phenyl]ethyl]-N,3,3',3',18,21,25,31,34-nonamethyl-29-[(1 S)-1-methylpropyl]-2,5,8,14,17,20,24,27,30,33,55-undecaoxo-spiro[3,6,9,15,18,21,25,28,31,34,41-undecazapentacyclo[24.15.11.2^{43,46}.1^{35,41}.0^{9,13}]pentapentaconta-37,43(54),44,46(53),47-pentaene-16,1'-cyclobutane]-22-carboxamide, (1 S,7S,11 R,13 S,19S,22S,26S,29S,35S,37Z,47Z)-19-cyclopentyl-7-[2-[3,5-difluoro-4-(trifluoromethyl)phenyl]ethyl]-11-ethoxy-3,3',3',18,21,25,31,34-octamethyl-29-[(1 S)-1-methylpropyl]-22-(pyrrolidine-1-carbonyl)spiro[3,6,9,15,18,21,25,28,31,34,41-undecazapentacyclo[24.15.10.2^{43,46}.1^{35,41}.0^{9,13}]tetrapentaconta-37,43(53),44,46(52),47-pentaene-16,1'-cyclobutane]-2,5,8,14,17,20,24,27,30,33,54-undecone, (1 S,7S,11R,13S,19S,22S,26S,29S,35S,37Z,47Z)-7-[2-[3,5-difluoro-4-(trifluoromethyl)phenyl]ethyl]-11-ethoxy-19-(1-ethylpropyl)-3,3',3',18,21,25,31,34-octamethyl-29-[(1 S)-1-methylpropyl]-22-(pyrrolidine-1-carbonyl)spiro[3,6,9,15,18,21,25,28,31,34,41-undecazapentacyclo[24.15.10.2^{43,46}.1^{35,41}.0^{9,13}]tetrapentaconta-37,43(53),44,46(52),47-pentaene-16,1'-cyclobutane]-2,5,8,14,17,20,24,27,30,33,54-undecone, (1 S,7S,11R,13 S,19S,22S,26S,29S,35 S,37Z,47Z)-19-cyclopentyl-31-cyclopropyl-7-[2-[3,5-difluoro-4-(trifluoromethyl)phenyl]ethyl]-11-ethoxy-3,3',3',18,21,25 ,34-heptamethyl-29-[(1 S)-1-methylpropyl]-22-(pyrrolidine-1-carbonyl)spiro[3,6,9,15,18,21,25,28,31,34,41-undecazapentacyclo[24.15.10.2^{43,46}.1^{35,41}.0^{9,13}]tetrapentaconta-37,43(53),44,46(52),47-pentaene-16,1'-cyclobutane]-2,5,8,14,17,20,24,27,30,33,54-undecone, (1S,7S,11R,13S,19S,22S,26S,29S,35S,37Z,47Z)-31-cyclopropyl-7-[2-[3,5-difluoro-4-(trifluoromethyl)phenyl]ethyl]-11-ethoxy-19-(1-ethylpropyl)-3,18,21,25,34-pentamethyl-29-[(1 S)-1-methylpropyl]-22-(pyrrolidine-1-carbonyl)spiro[3,6,9,15,18,21,25,28,31,34,41-undecazapentacyclo[24.15.10.2^{43,46}.1^{35,41}.0^{9,13}]tetrapentaconta-37,43(53),44,46(52),47-pentaene-16,1'-cyclobutane]-2,5,8,14,17,20,24,27,30,33,54-undecone, and (1S,7S,11R,13S,19S,22S,26S,29S,35S,37Z,47Z)-7-[2-(3,4-dichlorophenyl)ethyl]-11-ethoxy-19-(1-ethylpropyl)-3,18,21,25,31,34-hexamethyl-29-[(1 S)-1-methylpropyl]-22-(pyrrolidine-l-carbonyl)spiro[3,6,9,15,18,21,25,28,31,34,41-undecazapentacyclo[24.15.11.2^{43,46}.1^{35,41}.0^{9,13}]pentapentaconta-37,43(54),44,46(53),47-pentaene-16,1'-cyclobutane]-2,5,8,14,17,20,24,27,30,33,55-undecone or a salt thereof, or a solvate thereof. These compounds are included in the formula represented by the formula (1).

In an embodiment, the compound of the present invention is preferably a compound represented by formula (2):

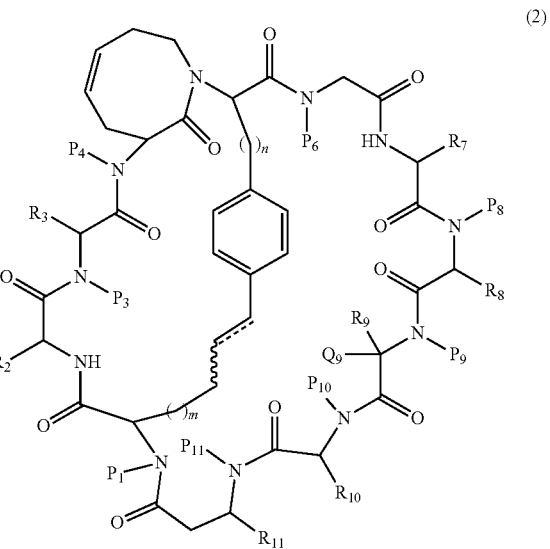

(2)

wherein

----, ~~~~ n, m, $P_1$, $R_2$, $R_3$, $P_3$, $P_4$, $P_6$, $R_7$, $R_8$, $P_8$, $R_9$, $P_9$, $Q_9$, $R_{10}$, $P_{10}$, $R_{11}$ and $P_{11}$ are the same as defined in formula (1).

For example, compounds PP1827, PP1830, PP2260, PP2574, PP2576, PP2583, PP2957, PP3033, PP3034, PP3036, PP3037, PP3047, PP3093 and PP3094 and the following compounds can be included in the formula (2).

(1 S,7S,11R,13S,19S,22S,26S,29S,35 S,37Z,47Z)-19-cyclopentyl-7-[2-[3,5-difluoro-4-(trifluoromethyl)phenyl]ethyl]-11-ethoxy-N-ethyl-N,3,18,21,25,31,34-heptamethyl-29-[(1 S)-1-methylpropyl]-2,5,8,14,17,20,24,27,30,33,55-undecaoxo-spiro[3,6,9,15,18,21,25,28,31,34,41-undecazapentacyclo[24.15.11.2^{43,46}.1^{35,41}.0^{9,13}]pentapentaconta-37,43(54),44,46(53),47-pentaene-16,1'-cyclobutane]-22-carboxamide, (1 S,7S,11R,13S,19S,22S,26S,29S,35S,37Z,47Z)-19-cyclopentyl-11-ethoxy-N-ethyl-7-[2-[3-methoxy-4-(trifluoromethyl)phenyl]ethyl]-N,3,3',3',18,21,25,31,34-nonamethyl-29-[(1 S)-1-methylpropyl]-2,5,8,14,17,20,24,27,30,33,55-undecaoxo-spiro[3,6,9,15,18,21,25,28,31,34,41-undecazapentacyclo[24.15.11.2^{43,46}.1^{35,41}.0^{9,13}]pentapentaconta-37,43(54),44,46(53),47-pentaene-16,1'-cyclobutane]-22-carboxamide, (1 S,7S,11R,13S,19S,22S,26S,29S,35S,37Z,47Z)-19-cyclopentyl-7-[2-[3,5-difluoro-4-(trifluoromethyl)phenyl]ethyl]-11-ethoxy-3,3',3',18,21,25,31,34-octamethyl-29-[(1 S)-1-methylpropyl]-22-(pyrrolidine-1-carbonyl)spiro[3,6,9,15,18,21,25,28,31,34,41-undecazapentacyclo

[24.15.10.2$^{43,46}$.1$^{35,41}$.0$^{9,13}$]tetrapentaconta-37,43(53), 44,46(52),47-pentaene-16,1'-cyclobutane]-2,5,8,14,17, 20,24,27,30,33,54-undecone, (1 S,7S,11R,13S,19S,22S,26S,29S,35S,37Z,47Z)-7-[2-[3,5-difluoro-4-(trifluoromethyl)phenyl]ethyl]-11-ethoxy-19-(1-ethylpropyl)-3,3',3',18,21,25,31,34-octamethyl-29-[(1 S)-1-methylpropyl]-22-(pyrrolidine-1-carbonyl)spiro[3,6,9,15,18,21,25,28,31,34,41-undecazapentacyclo [24.15.10.2$^{43,46}$.1$^{35,41}$.0$^{9,13}$]tetrapentaconta-37,43(53), 44,46(52),47-pentaene-16,1'-cyclobutane]-2,5,8,14,17, 20,24,27,30,33,54-undecone, (1 S,7S,11R,13S,19S,22S,26S,29S,35S,37Z,47Z)-19-cyclopentyl-31-cyclopropyl-7-[2-[3,5-difluoro-4-(trifluoromethyl)phenyl]ethyl]-11-ethoxy-3,3',3',18,21,25,34-heptamethyl-29-[(1 S)-1-methylpropyl]-22-(pyrrolidine-1-carbonyl)spiro[3,6,9,15,18,21,25,28,31,34,41-undecazapentacyclo[24.15.10.2$^{43,46}$.1$^{35,41}$.0$^{9,13}$] tetrapentaconta-37,43(53),44,46(52),47-pentaene-16,1'-cyclobutane]-2,5,8,14,17,20,24,27,30,33,54-undecone, (1S,7S,11R,13S,19S,22S,26S,29S,35S,37Z,47Z)-31-cyclopropyl-7-[2-[3,5-difluoro-4-(trifluoromethyl)phenyl] ethyl]-11-ethoxy-19-(1-ethylpropyl)-3,18, 21,25,34-pentamethyl-29-[(1 S)-1-methylpropyl]-22-(pyrrolidine-1-carbonyl)spiro[3,6,9,15,18,21,25,28,31,34,41-undecazapentacyclo[24.15.10.2$^{43,46}$.1$^{35,41}$.0$^{9,13}$] tetrapentaconta-37,43(53),44,46(52),47-pentaene-16,1'-cyclobutane]-2,5,8,14,17,20,24,27,30,33,54-undecone, and (1 S,7S,11R,13S,19S,22S,26S,29S,35S,37Z,47Z)-7-[2-(3,4-dichlorophenyl)ethyl]-11-ethoxy-19-(1-ethylpropyl)-3, 18,21,25,31,34-hexamethyl-29-[(1 S)-1-methylpropyl]-22-(pyrrolidine-1-carbonyl)spiro[3,6,9,15,18,21,25,28,31, 34,41-undecazapentacyclo [24.15.11.243.46.135.41.09.13] pentapentaconta-37,43 (54),44,46 (53),47-pentaene-16,1'-cyclobutane]-2,5,8,14, 17,20,24,27,30,33,55-undecone.

In an embodiment, the compound of the present invention is preferably a compound represented by formula (3):

(3)

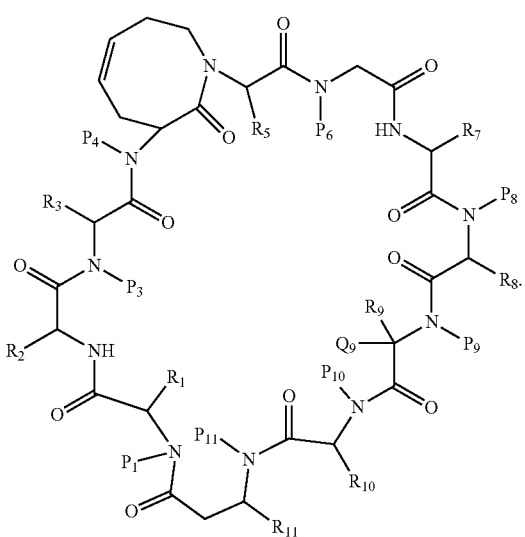

In formula (3), $R_1$ is a C1 to C7 alkyl;

$R_5$ is a benzyl optionally substituted with one or more groups selected from the group consisting of a $C_1$ to $C_6$ alkyl, a $C_1$ to $C_6$ haloalkyl and a $C_3$ to $C_8$ cycloalkyl;

═, ⁓, n, m, $P_1$, $R_2$, $R_3$, $P_3$, $P_4$, $P_6$, $R_7$, $R_8$, $P_9$, $R_9$, $P_9$, $Q_9$, $R_{10}$, $P_{10}$, $R_{11}$ and $P_{11}$ are the same as defined in formula (1).

For example, compounds PP1574, PP1650, PP2093, PP2316, PP2320, PP2328, PP2687, PP2691, PP3095, PP3096, PP3097, PP3098, PP3099, PP3100, PP3101, PP3102, PP3103, PP3104, PP3105, PP3106, PP3110, PP3111, PP3112, PP3113, PP3114, PP3115, PP3116, PP3117, PP3118, PP3119, PP3120, and PP3121 can be included in formula (3).

In an embodiment, the cyclic compound of the present invention has high selectivity for KRAS. In an embodiment, the cyclic compound of the present invention selectively inhibits KRAS. Without wishing to be bound by a particular theory, the divalent group that $R_4$ and $P_5$ together form interacts with His95 of KRAS, and thereby high selectivity for KRAS can be achieved. While it is known that there are three isotypes of RAS protein, i.e., HRAS, KRAS, and NRAS, His95 exists only in KRAS. Accordingly, a compound that specifically interacts with His95 of KRAS can inhibit KRAS with high selectivity over NRAS and/or HRAS.

In the present invention, the origin of NRAS, HRAS, and KRAS is not particularly limited, and may encompass those derived from a variety of animals such as human, mouse, rat, rabbit, dog, cat, cattle, horse, pig, goat, rhesus monkey, cynomolgus monkey, chimpanzee, and chicken, but human-derived HRAS, KRAS, and NRAS are preferable. The amino acid sequence of human-derived NRAS is shown in SEQ ID NO: 1, the amino acid sequence of human-derived HRAS is shown in SEQ ID NO: 2, and the amino acid sequence of human-derived KRAS is shown in SEQ ID NO: 3.

In an embodiment, the cyclic compound of the present invention has KRAS inhibitory activity that is 3 times or more higher than NRAS inhibitory activity and/or HRAS inhibitory activity. In an embodiment, the cyclic compound of the present invention has KRAS binding activity that is 3 times or more higher than NRAS binding activity and/or HRAS binding activity.

In an embodiment, the cyclic compound of the present invention has KRAS inhibitory activity that is 5 times, 7 times, 10 times, 15 times, or 20 times or more higher than NRAS inhibitory activity and/or HRAS inhibitory activity. In an embodiment, the cyclic compound of the present invention has KRAS binding activity that is 5 times, 7 times, 10 times, 15 times, or 20 times or more higher than NRAS binding activity and/or HRAS binding activity.

In the present invention, the KRAS inhibitory activity relative to the NRAS inhibitory activity and/or the HRAS inhibitory activity can be determined from the ratio of the KRAS inhibitory activity of the cyclic compound of the present invention to the NRAS inhibitory activity and/or the HRAS inhibitory activity of the cyclic compound of the present invention. For example, when this ratio is defined as [IC$_{50}$ value of cyclic compound of present invention with respect to NRAS and/or HRAS] divided by [IC$_{50}$ value of cyclic compound of present invention with respect to KRAS], a larger value of this ratio means that the KRAS inhibitory activity is higher than the NRAS inhibitory activity and/or the HRAS inhibitory activity, or in other words, the KRAS selective inhibitory activity of the cyclic compound of the present invention is high. On the other hand, a smaller value of this ratio means that the KRAS inhibitory activity is lower than the NRAS inhibitory activity and/or the HRAS inhibitory activity, or in other words, the KRAS selective inhibitory activity of the cyclic compound of the present invention is low.

In the present invention, the KRAS binding activity relative to the NRAS binding activity and/or the HRAS binding activity can be determined from the ratio of the KRAS binding activity of the cyclic compound of the present invention to the NRAS binding activity and/or the HRAS binding activity of the cyclic compound of the present invention. For example, when this ratio is defined as [KD value with respect to NRAS and HRAS] divided by [KD with respect to KRAS], a larger value means that the KRAS binding activity is higher than the NRAS binding activity and/or the HRAS binding activity, or in other words, the binding selectivity for KRAS over NRAS and/or HRAS is high. On the other hand, a smaller value means that the KRAS binding activity is lower than the NRAS binding activity and/or the HRAS binding activity, or in other words, the binding selectivity for KRAS over NRAS and/or HRAS is low.

In the present invention, the "interaction" means non-covalent interaction as exemplified by electrostatic interaction (including ionic bonding, hydrogen bonding, and dipole interaction), van der Waals interaction (including hydrophobic interaction), and the like. For example, it means CH-r interaction, NH-x interaction, S-a interaction, cation-x interaction, or halogen-x interaction. The interaction in the present invention may or may not be mediated by another molecule such as a water molecule, but is preferably not mediated by another molecule such as a water molecule.

In the present invention, whether the 95th amino acid residue histidine (denoted as His95 or H95) in the human KRAS wild-type protein interacts with the cyclic compound can be determined by the interatomic distance of their non-hydrogen atoms (in the case of bonding via another molecule such as a water molecule, the interatomic distance between their non-hydrogen atoms taking no account of such another molecule). When the interatomic distance is 5.1 angstroms (Å) or less, it can be determined that their non-hydrogen atoms interact with each other. In some embodiments, the interatomic distance between two interacting non-hydrogen atoms may be, for example, 5.1 Å or less, 4.8 Å or less, 4.5 Å or less, 4.3 Å or less, 4.2 Å or less, 4.1 Å or less, 4.0 Å or less, 3.9 Å or less, or 3.7 Å or less. Also, the interatomic distance may be 2.0 Å or more, 2.1 Å or more, or 2.5 Å or more.

In the present invention, the interatomic distance can be measured, for example, through an analysis of the three-dimensional structure of a complex of the human KRAS wild-type protein and the cyclic compound of the present invention. Specifically, a crystal of the complex of the human KRAS wild-type protein and the cyclic compound of the present invention is prepared. The crystal is subjected to X-ray diffractometry to obtain X-ray diffraction intensity data of space groups, unit cells, and the like. The obtained X-ray diffraction intensity data is applied to a program for initial structure or refined structure determination well known to those skilled in the art, such as Coot (Emsley, P. et al., 2010), Phenix (Adams, P. D. et al., 2010), Phaser (J. Appl. Cryst. 40:658-674 (2007)), Refmac5 (Acta Cryst. D67:355-467 (2011)), and ARP/wARP (Cohen, S. X. et al., 2008), and thereby the three-dimensional structure of the complex of the human KRAS wild-type protein and the cyclic compound of the present invention can be determined.

Once the three-dimensional structure of the complex of the human KRAS wild-type protein and the cyclic compound of the present invention is determined, the interatomic distance can be measured by a method well known to those skilled in the art. For example, the interatomic distance can be measured by allowing a software program for use in molecular modeling or molecular simulation, such as Discovery Studio 2020 Client, MOE (Molecular Operating Environment), or Maestro, to read the structural information of the complex of the cyclic compound of the present invention and the human KRAS wild-type protein, and using a function incorporated in the software program (such as the Distance Monitor function in the case of Discovery Studio 2020 Client). The details of conditions and criteria used by the software to determine the presence or absence of interactions can be viewed in a manual, specification, or the like appended to the software (e.g., in the case of Discovery Studio 2020 Client, the details of conditions and criteria for determining the presence or absence of interactions can be viewed by opening the web page of the specification from the Help button, selecting "Receptor-Ligand Interactions tools", then selecting "Theory-Receptor-Ligand Interactions", and further selecting "Non-bond Interactions").

The crystal of the complex of the human KRAS wild-type protein and the cyclic compound of the present invention can also be obtained by a method well known to those skilled in the art. For example, a solution containing the cyclic compound of the present invention is mixed with a solution containing the human KRAS wild-type protein to obtain the complex of the human KRAS wild-type protein and the cyclic compound of the present invention. By subjecting the resulting complex to a crystallization method well known to those skilled in the art such as a vapor diffusion method, a batch method (a bulk batch method or a microbatch method), a dialysis method, or a counter-diffusion method, the crystal of the complex of the human KRAS wild-type protein and the cyclic compound of the present invention can be prepared. Known vapor diffusion methods are a sitting drop method, a hanging drop method, and a sandwich drop method.

The human KRAS wild-type protein can also be obtained by a method known to those skilled in the art. For example, the human KRAS wild-type protein can be prepared by a recombinant polypeptide expressing method in which cells are used, but the method is not limited thereto. In one embodiment, a nucleic acid that encodes the human KRAS wild-type protein of the present invention is inserted into a suitable expression vector, the vector is introduced into a suitable cell, the transformed cell is cultured, and the expressed protein is isolated and purified. Such a protein can also be expressed as a fusion protein with another protein to facilitate purification. For example, it is possible to use a method of preparing a fusion protein with a maltose binding protein using *Escherichia coli* as a host (vector pMAL series sold by New England BioLabs, USA), a method of preparing a fusion protein with glutathione-S-transferase (GST) (vector pGEX series sold by Amersham Pharmacia Biotech), a method of preparing a protein to which a histidine tag is added (pET series of Novagen), and a method of preparing a protein to which an HAT tag is added. The host cell is not particularly limited as long as it is a cell suitable for expressing a recombinant protein, and, in addition to *E. coli* mentioned above, for example, yeast, various animal and plant cells, insect cells, and the like can be used. Various methods known to those skilled in the art can be used to introduce a vector into a host cell. For example, for introduction into *Escherichia coli*, introduction methods involving calcium ions (Mandel, M., Higa, A. (1970) Journal of Molecular Biology, 53, 158-162, and Hanahan, D. (1983)

Journal of Molecular Biology, 166, 557-580) can be used. The protein expressed in the host cell can be purified and recovered from the host cell or its cell culture or culture supernatant by a method known to those skilled in the art. When a protein is expressed as a fusion protein with the above maltose binding protein, HAT tag, or the like, affinity purification and gel filtration chromatography (size exclusion chromatography, SEC) purification can be easily performed. In affinity chromatography purification and SEC purification, AKTAxpress™ apparatus (GE Healthcare), NGC™ Chromatography System (Bio-Rad), BioLogic Duo-Flow™ Chromatography System (Bio-Rad), or the like can be used.

Interatomic energy can also be measured by a method well known to those skilled in the art. For example, interatomic energy can be easily calculated by allowing a molecular simulation program well known to those skilled in the art, such as Discovery Studio 2020 Client, MOE (Molecular Operating Environment), or Maestro, to read the three-dimensional structure of a substance to be measured, and, according to the instructions of the program, selecting a force field (such as Amber or CHARM) to be used in calculation and atoms for which energy calculation is performed. For example, in the case of Discovery Studio 2020 Client, interatomic energy can be calculated using the Calculate Interaction Energy function.

In one non-limiting embodiment, in a complex of the cyclic compound of the present invention and the human KRAS wild-type protein, the cyclic compound of the present invention interacts with His95 in the human KRAS wild-type protein.

Without wishing to be bound by a specific theory, it is considered that the formation of a complex by the cyclic compound of the present invention and the human KRAS wild-type protein in this manner is associated with contribution to the high binding activity of the cyclic compound of the present invention to the human KRAS wild-type protein and, moreover, with the binding selectivity over HRAS and NRAS.

The present invention also relates to a non-natural amino acid for use in the production of the cyclic compound of the present invention. In an embodiment, the non-natural amino acid of the present invention is an N-protected non-natural amino acid for use in the production of the peptide compound using a solid-phase synthesis method, and in another embodiment, the non-natural amino acid of the present invention is a non-natural amino acid having a free amino group obtained by removing the protecting group from the N-protected non-natural amino acid. Examples of the protecting group of the N-protected non-natural amino acid include an Fmoc group, a Boc group, a Cbz group, an Alloc group, a nosyl group, a dinitronosyl group, a t-Bu group, a trityl group, and a cumyl group. Of these, an Fmoc group, a Boc group, a Cbz group, and an Alloc group are preferable, and an Fmoc group is more preferable.

In an embodiment, examples of the N-protected non-natural amino acid having an Fmoc group as a protecting group in the present invention include the following amino acids listed in Table 4 or salts thereof, or solvates thereof.

aa004: (2S)-2-[9H-fluoren-9-ylmethoxycarbonyl(methyl) amino]octanoic acid, aa013: (2R)-2-[9H-fluoren-9-ylmethoxycarbonyl(methyl) amino]-3-methylsulfanyl-propanoic acid, aa019: (2S)-2-[9H-fluoren-9-ylmethoxycarbonyl(methyl) amino]-4,4-difluoro-butanoic acid, aa023: (2S)-2-[9H-fluoren-9-ylmethoxycarbonyl(methyl) amino]-3-(3-thienyl) propanoic acid, aa028: (2S)-3-(3,4-dichlorophenyl)-2-[9H-fluoren-9-ylmethoxycarbonyl(methyl)amino]propanoic acid, aa043: (2S)-5,5-dichloro-2-[9H-fluoren-9-ylmethoxycarbonyl(methyl)amino] pentanoic acid, aa056: (2R)-3-[9H-fluoren-9-ylmethoxycarbonyl(methyl) amino]-2-methyl-propanoic acid, aa098: (2S,3S)-1-(9H-fluoren-9-ylmethoxycarbonyl)-3-methyl-azetidine-2-carboxylic acid, aa099: (2S,3R)-1-(9H-fluoren-9-ylmethoxycarbonyl)-3-methyl-azetidine-2-carboxylic acid, aa 100: (2S)-1-(9H-fluoren-9-ylmethoxycarbonyl)-3,3-dimethyl-azetidine-2-carboxylic acid, aa111: (2R)-3-allyloxy-2-[9H-fluoren-9-ylmethoxycarbonyl (methyl)amino]propanoic acid, aa136: (2S)-2-[9H-fluoren-9-ylmethoxycarbonyl(propyl) amino]-3-[4-(trifluoromethyl)phenyl] propanoic acid, aa174: (2S)-2-[9H-fluoren-9-ylmethoxycarbonyl(propyl) amino]-3-(p-tolyl) propanoic acid, aa210: (2S)-2-cyclopentyl-2-[ethyl(9H-fluoren-9-ylmethoxycarbonyl)amino]acetic acid, aa220): (2S)-4-(4-chloro-3,5-difluoro-phenyl)-2-(9H-fluoren-9-ylmethoxycarbonylamino) butanoic acid, aa229: (2S)-4-(benzothiophen-5-yl)-2-(9H-fluoren-9-ylmethoxycarbonylamino) butanoic acid, aa233: (2S)-2-(9H-fluoren-9-ylmethoxycarbonylamino)-4-[3-methyl-4-(trifluoromethyl)phenyl]butanoic acid, aa235: (2S)-2-(9H-fluoren-9-ylmethoxycarbonylamino)-4-[3-methoxy-4-(trifluoromethyl)phenyl]butanoic acid, aa239: (2S,4S)-1-(9H-fluoren-9-ylmethoxycarbonyl)-4-methyl-pyrrolidine-2-carboxylic acid, aa244: (2S)-2-[9H-fluoren-9-ylmethoxycarbonyl(methyl) amino]-5,5-difluoro-pentanoic acid, aa246: (2S,4R)-1-(9H-fluoren-9-ylmethoxycarbonyl)-4-propoxy-pyrrolidine-2-carboxylic acid, aa250): (2R)-2-[9H-fluoren-9-ylmethoxycarbonyl(methyl) amino]-3-propoxy-propanoic acid, aa264: (2S,3R)-1-(9H-fluoren-9-ylmethoxycarbonyl)-3-tetrahydropyran-2-yloxy-pyrrolidine-2-carboxylic acid, aa265: (2S,3S)-1-(9H-fluoren-9-ylmethoxycarbonyl)-3-tetrahydropyran-2-yloxy-pyrrolidine-2-carboxylic acid, aa268: (1S,2S,5R)-3-(9H-fluoren-9-ylmethoxycarbonyl)-3-azabicyclo[3.1.0)] hexane-2-carboxylic acid, aa279: (2S,4R)-1-(9H-fluoren-9-ylmethoxycarbonyl)-4-tetrahydropyran-2-yloxy-pyrrolidine-2-carboxylic acid, aa281: (2S,4R)-1-(9H-fluoren-9-ylmethoxycarbonyl)-4-methoxy-pyrrolidine-2-carboxylic acid, aa331: (2S)-3-ethyl-2-[9H-fluoren-9-ylmethoxycarbonyl (methyl)amino] pentanoic acid, aa389: (2S)-2-[9H-fluoren-9-ylmethoxycarbonyl(propyl) amino]-4-methyl-pentanoic acid, aa391: (2S,3R)-2-(9H-fluoren-9-ylmethoxycarbonylamino)-3-propoxy-butanoic acid, aa397: (2S)-2-[9H-fluoren-9-ylmethoxycarbonyl(propyl) amino]-3-isopentyloxy-propanoic acid, aa398: (2S)-3-(cyclobutoxy)-2-[9H-fluoren-9-ylmethoxycarbonyl(propyl) amino]propanoic acid, aa399: (2S)-4-(7-chloro-1-methyl-indol-5-yl)-2-(9H-fluoren-9-ylmethoxycarbonylamino) butanoic acid, aa400: (2S)-2-(9H-fluoren-9-ylmethoxycarbonylamino)-4-(2-fluoro-3-methyl-benzothiophen-5-yl) butanoic acid, aa40) 1: (2S)-4-(7-chlorobenzothiophen-5-yl)-2-(9H-fluoren-9-ylmethoxycarbonylamino) butanoic acid, aa402: (2S)-2-(9H-fluoren-9-ylmethoxycarbonylamino)-4-(1-methyl indol-6-yl) butanoic acid, aa40) 3: (2S)-4-(1,3-dimethyl indol-6-yl)-2-(9H-fluoren-9-ylmethoxycarbonylamino) butanoic acid, aa404: (2S)-2-(9H-fluoren-9-ylmethoxycarbonylamino)-4-(1,2,3-trimethyl indol-6-yl) butanoic acid,
aa405: (2S)-4-(2,3-dimethyl benzothiophen-5-yl)-2-(9H-fluoren-9-ylmethoxycarbonylamino) butanoic acid,
aa406: (2S)-4-(3-chloro-4-ethyl-phenyl)-2-(9H-fluoren-9-ylmethoxycarbonylamino) butanoic acid,
aa407: (2S)-2-(9H-fluoren-9-ylmethoxycarbonylamino)-4-[4-(methoxymethyl)-3,5-dimethyl-phenyl]butanoic acid,
aa408: (2S)-4-(4-chloro-3-methoxy-phenyl)-2-(9H-fluoren-9-ylmethoxycarbonylamino) butanoic acid,
aa409: (2S)-4-[4-chloro-3-(trifluoromethyl)phenyl]-2-(9H-fluoren-9-ylmethoxycarbonylamino) butanoic acid,
aa410: (2S)-4-[4-(difluoromethyl)-3,5-difluoro-phenyl]-2-(9H-fluoren-9-ylmethoxycarbonylamino) butanoic acid,
aa411: (2S)-4-(4-chloro-3,5-dimethyl-phenyl)-2-(9H-fluoren-9-ylmethoxycarbonylamino) butanoic acid,
aa414: (2S,4R)-4-(cyclopentoxy)-1-(9H-fluoren-9-ylmethoxycarbonyl) pyrrolidin-2-carboxylic acid,
aa415: (2S,4R)-4-(cyclobutoxy)-1-(9H-fluoren-9-ylmethoxycarbonyl) pyrrolidin-2-carboxylic acid,
aa423: (3S)-3-cyclobutyl-3-[9H-fluoren-9-ylmethoxycarbonyl(methyl)amino]propanoic acid,
aa424: (3R)-3-[9H-fluoren-9-ylmethoxycarbonyl(methyl)amino] pentanoic acid,
aa425: (3S)-3-[9H-fluoren-9-ylmethoxycarbonyl(methyl)amino]-4-methyl-pentanoic acid,
aa426: (3S)-3-cyclohexyl-3-[9H-fluoren-9-ylmethoxycarbonyl(methyl)amino]propanoic acid, and
aa443: (2S)-2-[but-3-enyl(9H-fluoren-9-ylmethoxycarbonyl)amino]-3-(p-tolyl) propanoic acid.

(General Production Method)

General production methods for the cyclic compound of the present invention, and the oligopeptide compound and the non-natural amino acid for use in the production of these compounds will be described below. Herein, the cyclic compound may be referred to as "cyclic peptide compound". Herein, the "cyclic moiety" of a peptide compound means a cyclic portion formed by connection of two or more amino acid residues.

Chemical Synthesis Methods for Peptide Compounds

Examples of chemical synthesis methods for the peptide compounds or the cyclic compounds herein include a liquid-phase synthesis method, a solid-phase synthesis method using Fmoc synthesis, Boc synthesis, or the like, and a combination thereof. In Fmoc synthesis, a basic unit is an amino acid in which a main-chain amino group is protected with an Fmoc group, and a side-chain functional group is protected as necessary with a protecting group that is not cleaved by piperidine or such bases, such as a t-Bu group, a THP group, or a Trt group, and a main-chain carboxylic acid is not protected. The basic unit is not particularly limited as long as it is a combination having an Fmoc-protected amino group and a carboxyl group. For example, dipeptide or tripeptide may be a basic unit, and a cyclic structure may be formed between substituents on nitrogen atoms and/or side chains contained in the dipepetide or tripeptide. The basic unit disposed at the N terminus may be a unit other than the Fmoc amino acid. For example, it may be a Boc amino acid or a Tfa group or Ns group, or a carboxylic acid analog which does not have an amino group. The main-chain carboxyl group, or a side-chain carboxyl group of an amino acid that has a carboxyl group in a side chain and in which the main-chain carboxyl group is protected with a suitable protecting group, is supported on a solid phase by a chemical reaction with the functional group of a solid-phase carrier. Subsequently, the Fmoc group is deprotected by a base such as piperidine or DBU, and a newly produced amino group and a subsequently added, basic-unit protected amino acid having a carboxyl group are subjected to a condensation reaction to produce a peptide bond. In the condensation reaction, various combinations such as a combination of DIC and HOBt, a combination of DIC and HOAt, and a combination of HATU and DIPEA are possible as activating agents for the carboxyl group. The desired peptide sequence can be produced by repeating the Fmoc group deprotection and the subsequent peptide bond forming reaction. After the desired sequence is obtained, cleavage from the solid phase and deprotection of the optionally introduced protecting group of the side-chain functional group are conducted. Further, conformational conversion and cyclization of the peptide can be performed before cleaving from the solid phase. Cleaving from the solid phase and deprotection may be performed under the same conditions, e.g., in 90:10 TFA/H2O, or deprotection may be performed under different conditions as necessary. Cleaving from the solid phase may be achieved using a weak acid such as 1% TFA in some cases, and a protecting group that can be deprotected with a Pd-containing catalyst or the like may be used to utilize the orthogonality of both chemical reactions. During or at the end of these steps, a step such as cyclization can also be performed. For example, a side-chain carboxylic acid and an N-terminal main-chain amino group can be condensed, and a side-chain amino group and a C-terminal main-chain carboxylic acid can be condensed. In addition, an olefin can be introduced into two or more sites of the side chains and/or the substituents of nitrogen atoms, and cyclized by metathesis reaction. Moreover, a double bond produced by cyclization can be reduced to a single bond. Also, a double bond produced by cyclization can be converted to a cyclopropane ring under conditions involving diiodomethane-diethylzinc or the like. These steps of cyclization, reduction, conversion to a cyclopropane ring, and the like may be carried out during the course of synthesizing a basic unit such as dipeptide or tripeptide. In the meantime, reaction orthogonality is required between the carboxylic acid on the C-terminal side and the side-chain carboxylic acid to be cyclized, between the main-chain amino group or hydroxy group on the N-terminal side and the side-chain amino group to be cyclized, or between the olefins of side chains and/or substituents of nitrogen atoms and the olefins to be cyclized. As described above, the protecting group is selected in consideration of the orthogonality of the protecting group. In addition, by placing a chloroacetyl group at the N-terminus, cyclization can also be performed between the thiol groups of side chains of cysteine residues. The reaction product thus obtained can be purified by a reverse-phase column, a molecular sieve column, or the like. Details of these procedures are described in, for example, the Solid-Phase Synthesis Handbook published by Merck on May 1, 2002. Commercially available resins for solid phase synthesis are usable, and examples include CTC resin, Wang resin, and SASRIN resin.

A general method for synthesizing an amino acid-supported resin for use in peptide synthesis by a peptide synthesizer will be described below.

An Fmoc amino acid can be supported on a resin by the method described in WO2013/100132 or WO2018/225864. Specifically, for example, 2-chlorotrityl chloride resin and a solvent (e.g., dehydrated dichloromethane) are introduced into a filter-equipped reaction vessel to swell the resin. Next, the solvent and the resin are separated, and then a mixture of the resin, a C-terminal free Fmoc amino acid dissolved in a solvent (e.g., dehydrated dichloromethane), a solvent (e.g., dehydrated methanol), and a base (e.g., diisopropylethylamine) is added to the reaction vessel and mixed to support the Fmoc amino acid on the resin. After the resin and the reaction solution are separated, the resin is mixed with a mixture of one or more solvents and a base (e.g., a mixture of dehydrated dichloromethane, dehydrated methanol, and diisopropylethylamine) to wash the resin. After the resin is washed with a solvent (e.g., dichloromethane) multiple times as necessary, the resin and the reaction solution are separated. By drying the resulting resin under reduced pressure overnight, an Fmoc amino acid-supported resin can be obtained.

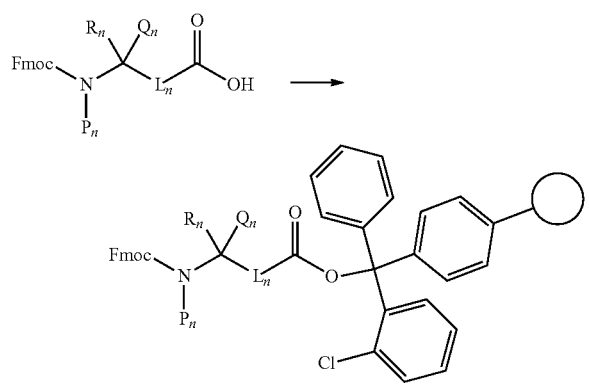

(wherein n represents an integer of 1 to 11; $P_1$ to $P_{11}$, $Q_1$ to $Q_{11}$, and $R_1$ to $R_{11}$ mean $P_1$ to $P_{11}$, $Q_1$ to $Q_{11}$, and $R_1$ to $R_{11}$ as defined herein, respectively; Li and Ln mean Li and Lu as described herein, respectively; $L_2$ to $L_{10}$ are single bonds; and: (circle) means a resin portion.) The above structure shows that in the Fmoc-amino acid, the 2-chlorotrityl group on the resin is bonded to the carboxylic acid of the Fmoc amino acid via an ester bond.

In the production of the compound described herein, when the defined group undergoes undesired chemical conversion under the conditions of the performed method, the compound can be produced by means of, for example, protection and deprotection of a functional group. Selection and introduction/removal procedures of a protecting group can be performed according to, for example, the methods described in Greene's "Protective Groups in Organic Synthesis" (5th Ed., John Wiley & Sons, 2014), which may be suitably used depending on the reaction conditions. Further, the order of reaction steps such as introduction of a substituent can be changed as necessary. For example, the protecting group for an amino group is an Fmoc, Boc, Cbz, or Alloc group. These carbamate groups can be introduced by reacting an amino group with a carbamating agent in the presence of a basic catalyst. Examples of the carbamating agent include BoczO, BocOPh, FmocOSu, FmocCl, CbzCl, and AllocCl. Examples of the basic catalyst include lithium carbonate, sodium carbonate, sodium hydrogen carbonate, potassium carbonate, potassium hydrogen carbonate, cesium carbonate, cesium hydrogen carbonate, lithium hydroxide, sodium hydroxide, potassium hydroxide, cesium hydroxide, sodium phosphate, potassium phosphate, N-methylmorpholine, triethylamine, diisopropylethylamine, and N,N-dimethylaminopyridine. A carbamate group which is a protecting group for an amino group can be removed under basic conditions, acidic conditions, hydrogenolysis reaction conditions, or the like.

(Synthesis Methods for Cyclic Compounds by Cyclization of Peptide Compounds)

A method for transforming a linear peptide compound into a cyclic peptide compound can be performed by carrying out a bond forming reaction within the molecule according to, for example, the method described in Comprehensive Organic Transformations, A Guide to Functional Group Preparations, 3rd Edition by R. C. Larock, or March's Advanced Organic Chemistry: Reactions, Mechanisms, and Structure, 7th Edition by M. B. March. After the bond forming reaction, further, a functional group transforming reaction can also be performed. Examples of the bond forming reaction include a C(O)—N bond formed from carboxylic acid and amine; a C—O—C bond, a C(O)—O bond, and a C(S)—O bond using an oxygen atom; a C(O)—S bond, a C(S)—S bond, a C—S—S—C bond, a C—S—C bond, a C—S(O)—C bond, and a C—S(O$_2$)—C bond using a sulfur atom; and a C—N—C bond, a C=N—C bond, an N—C(O)—N bond, an N—C(S) N bond, and a C(S)—N bond using a nitrogen atom. Furthermore, examples include C—C bond forming reactions catalyzed by a transition metal, such as Suzuki reaction, Heck reaction, Sonogashira reaction, and metathesis reaction. Examples of the functional group transforming reaction further performed after the bond forming reaction include an oxidation reaction and a reduction reaction. A specific example is a reaction for oxidizing a sulfur atom to transform it into a sulfoxide group or a sulfone group. Another example is a reduction reaction for reducing a triple bond or a double bond of carbon-carbon bonds to a double bond or a single bond. While a closed ring structure is formed by a peptide bond when two amino acids are bonded with the amino acid main chain, a covalent bond between two amino acids may be formed by bonding between side chains of two amino acids, bonding between a side chain and a main chain, or the like. A black circle or a black square below indicates an amino acid residue, and connected black circles or black squares represent a peptide chain connected by an amide bond. The number of amino acid residues constituting a peptide chain are not particularly limited, and the number of amino acid residues is not limited to the number of black circles or black squares exemplified below.

(General Preparation Method 1 for Cyclic Compounds)

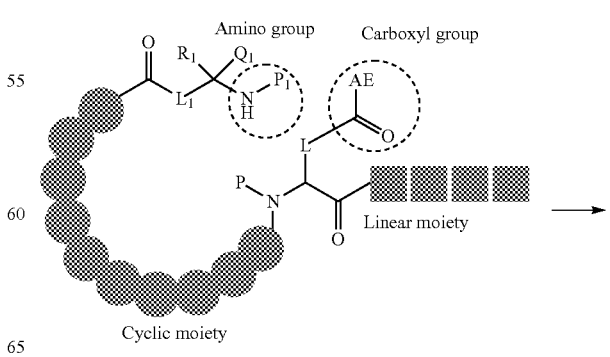

-continued

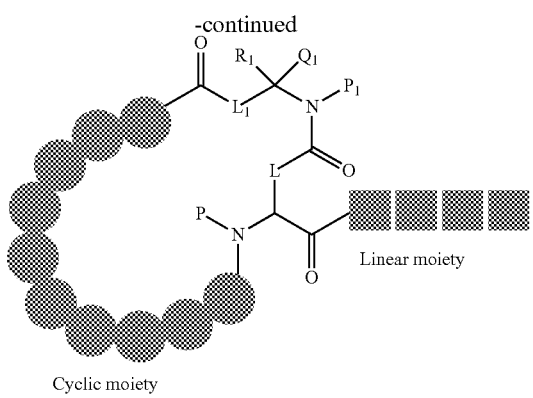

Cyclic moiety
R₁ and Q₁ represent a side chain of amino acid.
P₁ and P represent a hydrogen or an alkyl group.
L₁ and L represent a linker.
AE represents OH or active ester.

Cyclic moieties of cyclic compounds having linear moieties can be cyclized by activating the N-terminal amino group and the C-terminal side chain carboxyl group (e.g., L=—CH₂-in the case of aspartic acid or its derivative, and L=—CH₂CH₂-in the case of glutamic acid or its derivative) with an activating reagent or converting them to active esters, and then condensing them in the molecule to form a C(O)—N bond.
(General Preparation Method 2 for Cyclic Compounds)

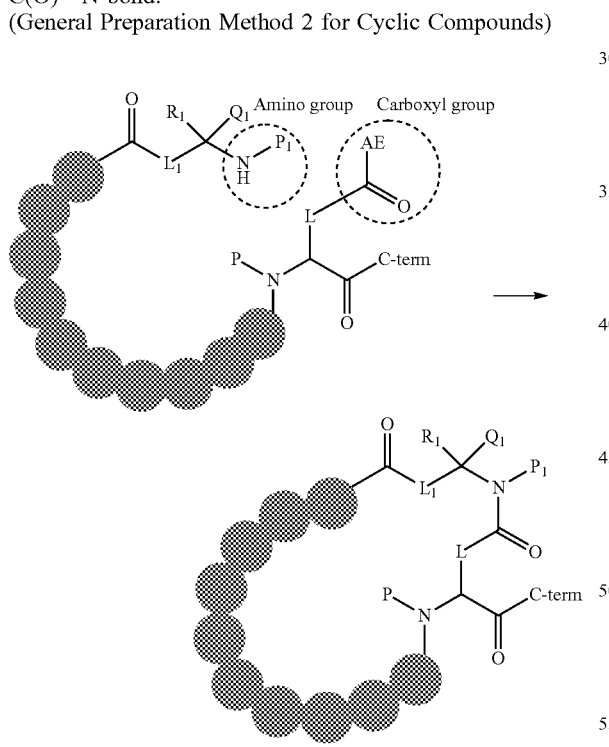

R₁ and Q₁ represent a side chain of amino acid.
P₁ and P represent a hydrogen or an alkyl group.
L₁ and L represent a linker.
AE represents OH or active ester.
C-Term represents OH, an alkoxy group, or an optionally substituted amino group.

Cyclic compounds described in "General preparation method 1 for cyclic compounds" in which the linear moiety is C-Term can be cyclized by activating the N-terminal amino group and the C-terminal side chain carboxyl group (e.g., L=—CH₂-in the case of aspartic acid or its derivative, and L=—CH₂CH₂-in the case of glutamic acid or its derivative) with an activating reagent or converting them to active esters, and then condensing them in the molecule to form a C(O)—N bond.
(General Preparation Method 3 for Cyclic Compounds)
(Method of Cyclizing with Haloalkyl and SH Groups)

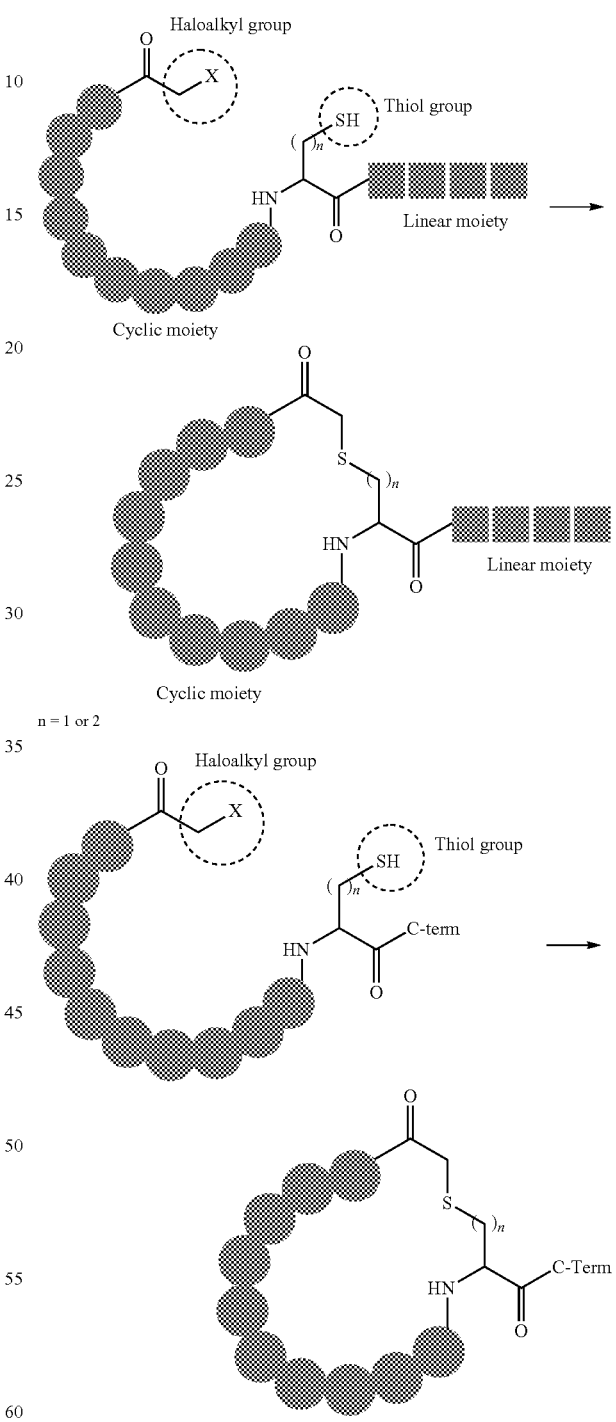

n = 1 or 2

C-Term represents OH, an alkoxy group, or an optionally substituted amino group.

Cyclic moieties of cyclic compounds having linear moieties can be cyclized by reacting the haloalkyl group of an amino acid residue with the thiol group of an amino acid residue in the molecule to form a C—S—C bond. Cyclic compounds described in "General preparation method 1 for cyclic compounds" in which the linear moiety is C-Term can also be similarly cyclized by reacting the haloalkyl group of an amino acid residue with the thiol group of an amino acid residue in the molecule to form a C—S—C bond. Further, a C—S(O)—C or C—S(O$_2$)—C bond can also be formed by oxidizing and converting a sulfur atom to a sulfoxide or sulfone.

(Method of cyclizing with vinyl and SH groups)

acid residue with the thiol group of an amino acid residue in the molecule to form a C—S—C bond. Cyclic compounds described in "General preparation method 1 for cyclic compounds" in which the linear moiety is C-Term can also be similarly cyclized by reacting the vinyl group of an amino acid residue with the thiol group of an amino acid residue in the molecule to form a C—S—C bond. Further, a C—S(O)—C or C—S(02)—C bond can also be formed by oxidizing and converting a sulfur atom to a sulfoxide or sulfone.

(Method of Cyclizing with Ethynyl and SH Groups)

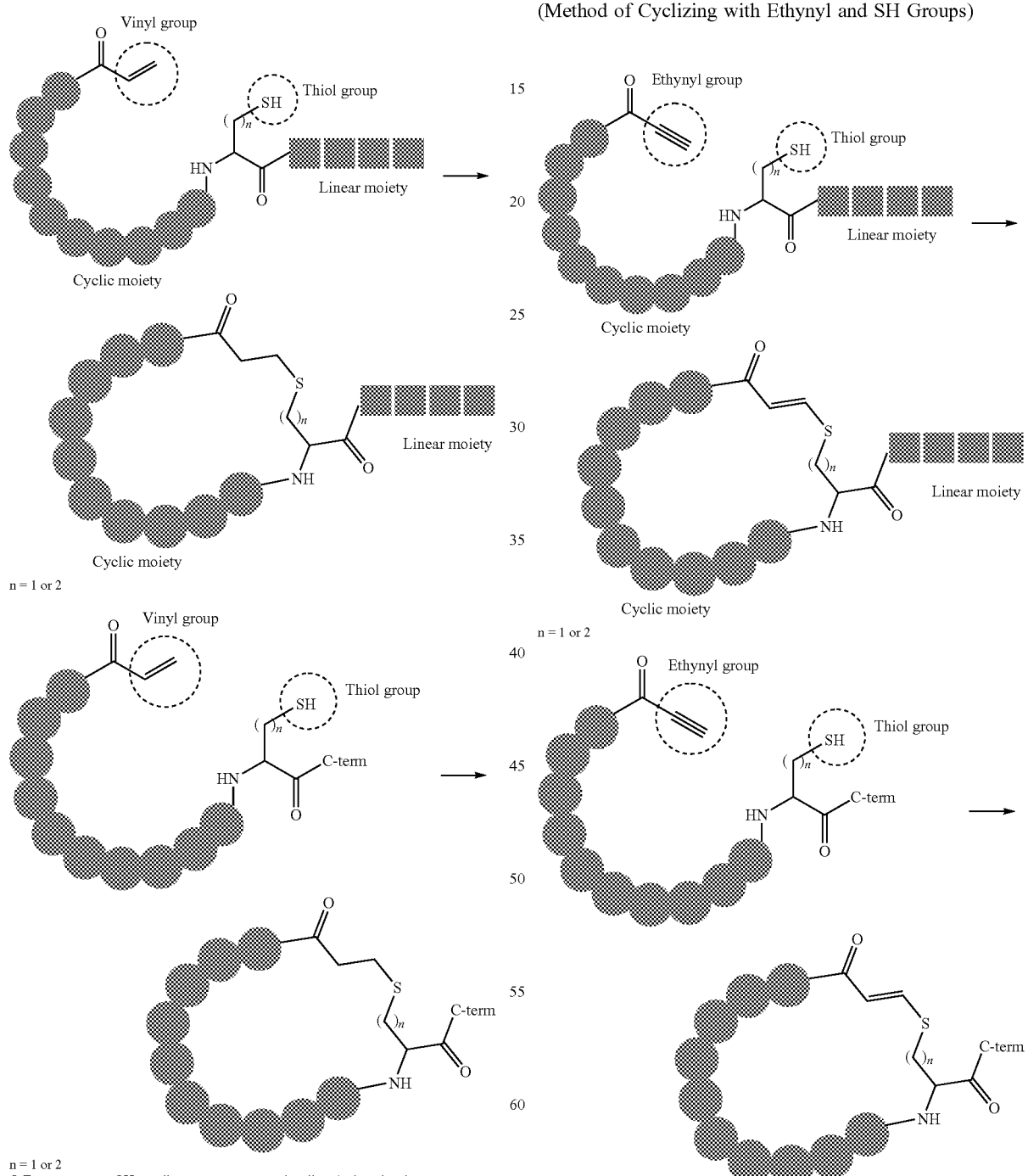

Cyclic moieties of cyclic compounds having linear moieties can be cyclized by reacting the vinyl group of an amino Cyclic moieties of cyclic compounds having linear moieties can be cyclized by reacting the ethynyl group of an amino acid residue with the thiol group of an amino acid residue in the molecule to form a C—S—C bond. Cyclic compounds described in "General preparation method 1 for cyclic compounds" in which the linear moiety is C-Term can also be similarly cyclized by reacting the ethynyl group of an amino acid residue with the thiol group of an amino acid residue in the molecule to form a C—S—C bond. Further, a C—S(O)—C or C—S($O_2$)—C bond can also be formed by oxidizing and converting a sulfur atom to a sulfoxide or sulfone. The double bond site can also be reduced and converted to a single bond.

(Method of Cyclizing with Vinyl and Vinyl Groups)

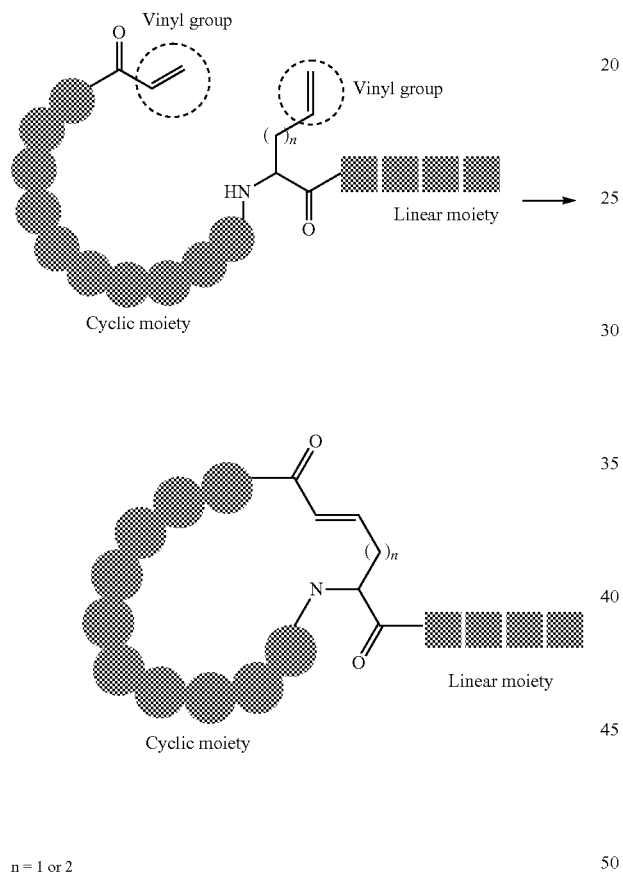

n = 1 or 2

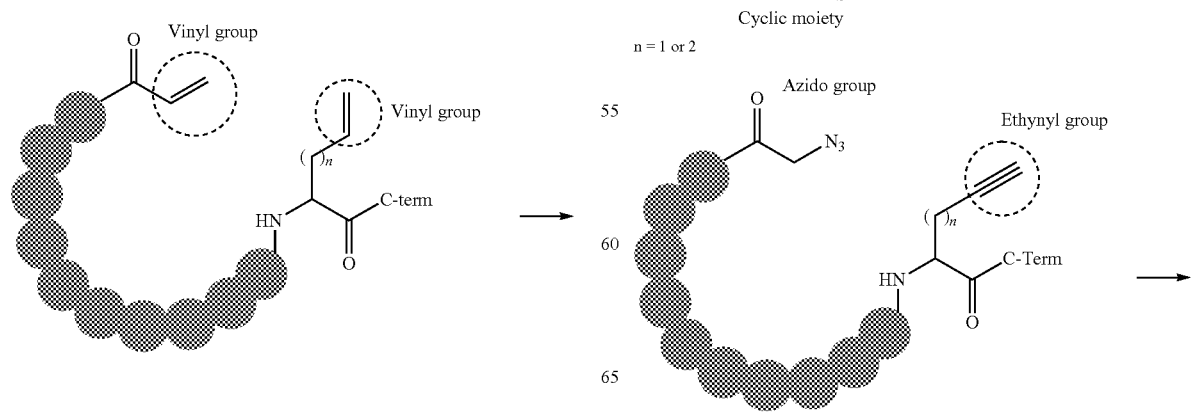

n = 1 or 2
C-Term represents OH, an alkoxy group, or an optionally substituted amino group.

Cyclic moieties of cyclic compounds having linear moieties can be cyclized by reacting different vinyl groups of amino acid residues with each other in the molecule to form a C—C bond. Cyclic compounds described in "General preparation method 1 for cyclic compounds" in which the linear moiety is C-Term can also be similarly cyclized by reacting different vinyl groups of amino acid residues with each other in the molecule to form a C—C bond.

(Method of Cyclizing by Forming a Triazole Ring with Azido and Ethynyl Groups)

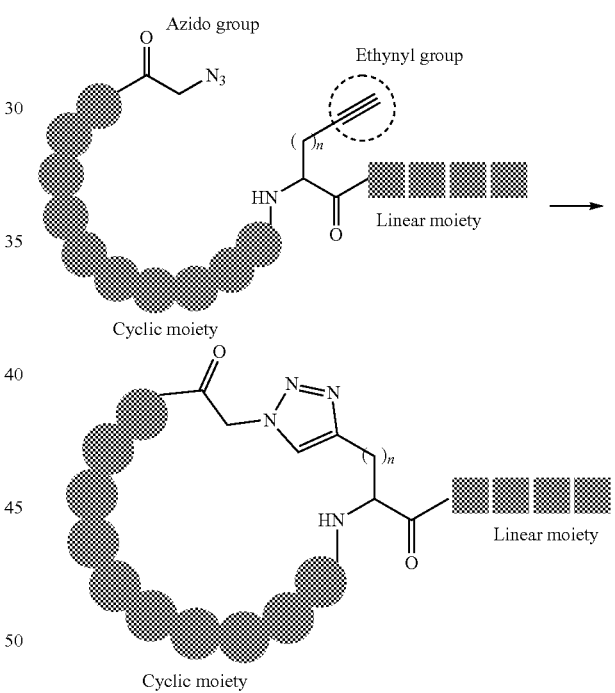

n = 1 or 2

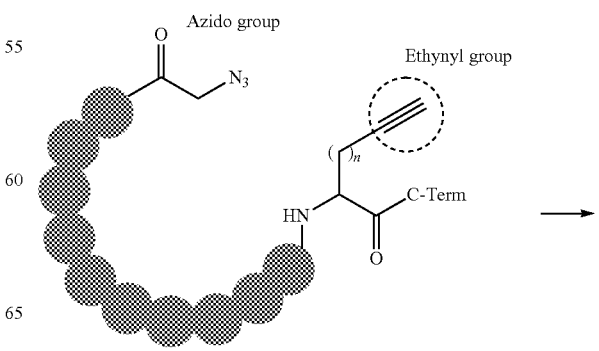

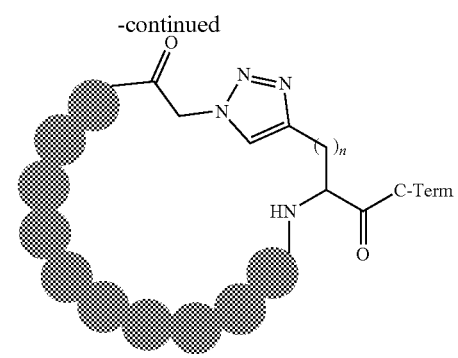

n = 1 or 2
C-Term represents OH, an alkoxy group, or an optionally substituted amino group.

Cyclic moieties of cyclic compounds having linear moieties can be cyclized by reacting the azido group of an amino acid residue with the ethynyl group of an amino acid residue in the molecule to form a triazole ring. Cyclic compounds described in "General preparation method 1 for cyclic compounds" in which the linear moiety is C-Term can also be similarly cyclized by reacting the azido group of an amino acid residue with the ethynyl group of an amino acid residue in the molecule to form a triazole ring.

General preparation methods for peptide compounds by peptide modification are shown below. In the following schemes, $P_n$ represents a substituent for a nitrogen atom, $R_n$ and $Q_n$ each represent an amino acid side chain, a black circle represents an amino acid residue, linked black circles represent a peptide chain linked by amide bonds, and m represents the number of amino acid residues and may be any integer of 1 or more.

(Method of Preparing Peptides Containing N-Alkylamino Acids)

Peptides containing N-alkylamino acids can be synthesized according to the general peptide synthesis method described in the present Examples using an Fmoc-protected N-alkylamino acid as a raw material, or alternatively can be prepared by alkylating the N-terminal nitrogen on a resin as illustrated below. Specifically, the target peptides having an N-alkylamino acid at the N-terminus can be prepared by reacting the nitrogen of the N-terminal Tfa amide (trifluoroacetamide) of a resin-loaded peptide with an alkyl halide under basic conditions, and then treating the peptide with a reducing agent by referring to Organic Letters, 2008, 10, 4815-4818 or the like. Further, cyclic compounds can be prepared by elongating, cleaving from the resin, cyclizing, deprotecting, and purifying the peptide according to the general peptide synthesis method described in the present Examples.

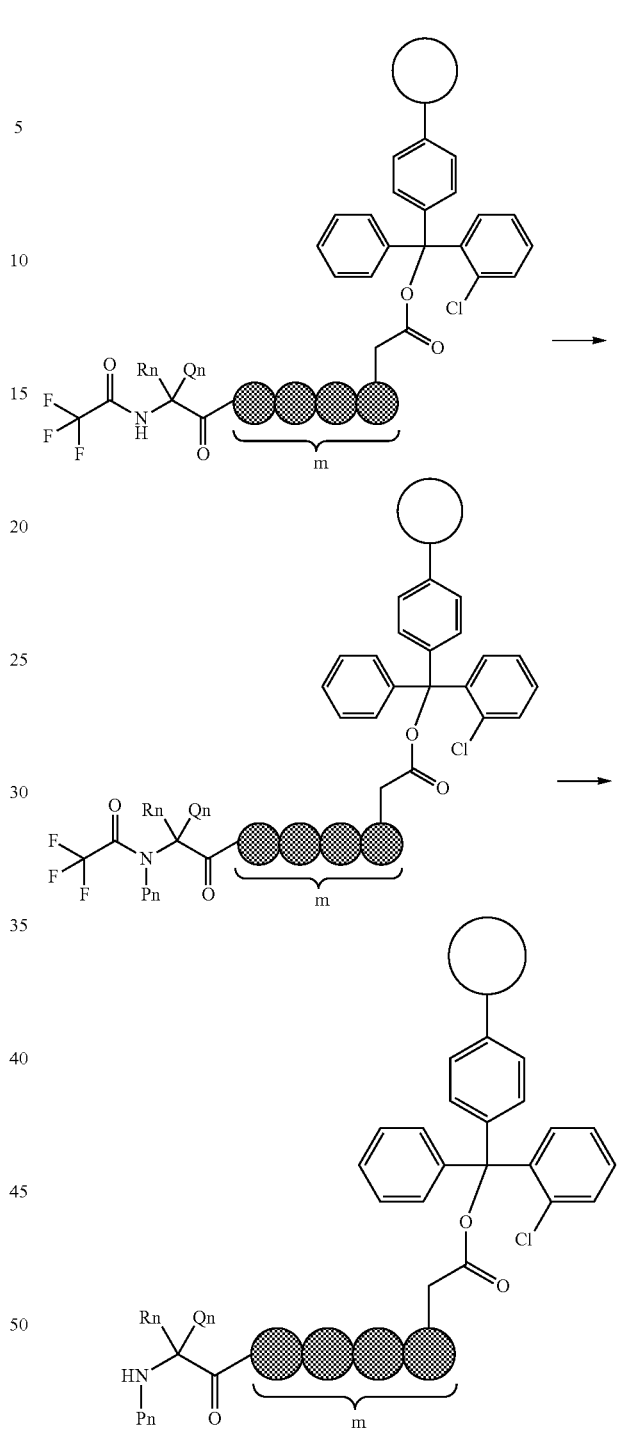

The method described in Nature Protocols, 2012, 7, 432-444 which is shown below can also be used as another method of introducing $P_n$ onto the N-terminal nitrogen. Specifically, the target peptides having $P_n$ at the N-terminus can be obtained by converting the N-terminal amine of a resin-loaded peptide to an Ns-substituted form, introducing $P_n$ by Mitsunobu reaction, and then deprotecting the Ns group. Further, cyclic compounds can be prepared by elongating, cleaving from the resin, cyclizing, deprotecting, and purifying the peptide according to the general peptide synthesis method described in the present Examples.

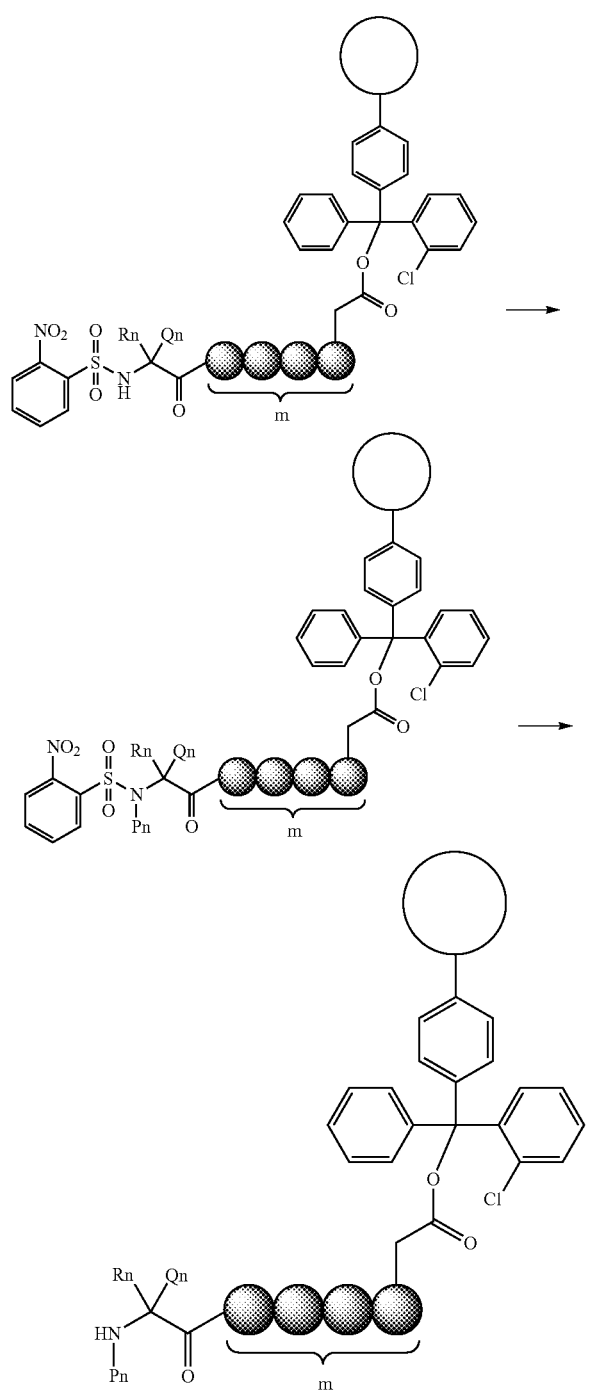

Peptides containing glycine with $P_n$ introduced onto the nitrogen atom can be synthesized according to the general peptide synthesis method described in the present Examples using glycine with $P_n$ introduced onto the Fmoc-protected nitrogen atom as a raw material, or alternatively can be prepared by substitution reaction between the N-terminal halogenated carbon and an amine as illustrated below. Specifically, the target peptides having N-terminal glycine with $P_n$ introduced onto the nitrogen atom can be obtained by reacting the N-terminal amine with iodoacetic acid and then reacting it with any primary amine by referring to Organic Letters, 2010, 12, 4928-4931 or the like. Further, cyclic compounds can be prepared by elongating, cleaving from the resin, cyclizing, deprotecting, and purifying the peptide according to the general peptide synthesis method described in the present Examples.

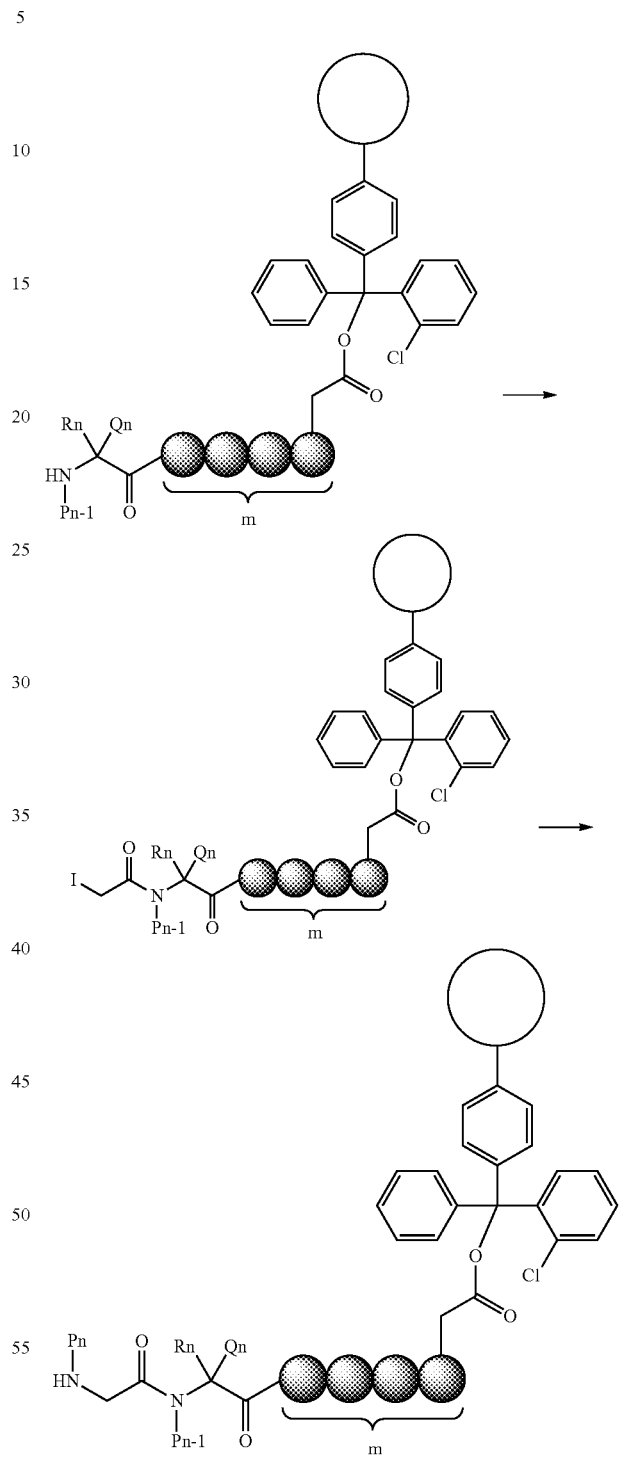

(Method of Preparing Peptides Containing an Aryloxy or Heteroaryloxy Group on the Side Chain)

Peptides containing an aryloxy or heteroaryloxy group on a side chain can be prepared according to the general peptide synthesis method described in the present Examples using an Fmoc amino acid having the target aryloxy or heteroaryloxy group on the side chain as a raw material, or alternatively can be prepared using a peptide having an alcohol on the side chain as a precursor by referring to Organic Letters, 2014, 16, 4944-4947, Tetrahedron Letters, 2003, 44, 3863-3865, or the like, as illustrated below. Specifically, peptides having an aryloxy or heteroaryloxy group on the side chain can be prepared by reacting a peptide having an alcohol on the side chain with triarylboroxane-pyridine complex in the presence of copper (II) acetate.

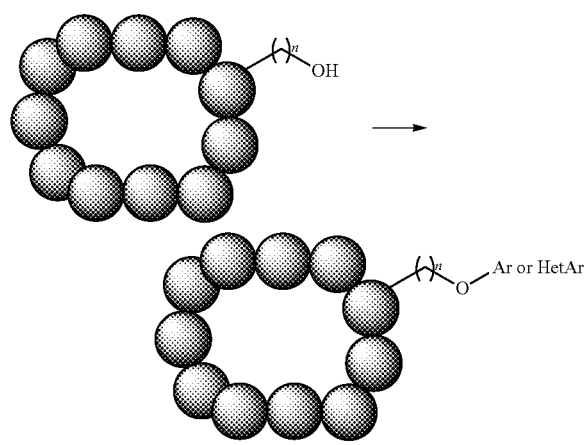

Peptides having an ether group excluding an aryloxy or heteroaryloxy group on a side chain can be prepared according to the general peptide synthesis method described in the present Examples using an Fmoc amino acid having the target ether group on the side chain as a raw material, or alternatively can be prepared using a peptide having an alcohol on the side chain as a precursor by referring to the method described in Journal of Medicinal Chemistry, 2011, 54, 4815-4830 or Journal of Medicinal Chemistry, 2014, 57, 159-170, as illustrated below. Specifically, the peptides having the target ether group on the side chain can be prepared by reacting a peptide having an alcohol with an alkyl halide in the presence of silver (I) oxide, or by reacting a peptide having an alcohol with an alkyl halide using an aqueous sodium hydroxide solution as a base in the presence of a phase transfer catalyst such as a tetraalkylammonium salt.

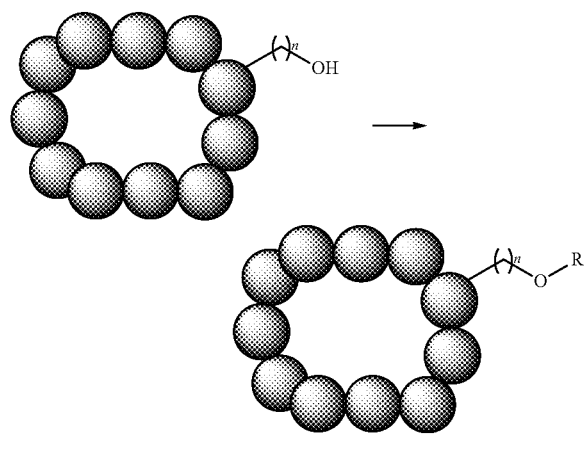

(Method of Preparing Peptides Containing an Aryl or Heteroaryl Group on the Side Chain)

Peptides having an aryl or heteroaryl group on a side chain can be prepared according to the general peptide synthesis method described in the present Examples using an Fmoc amino acid having the target aryl or heteroaryl group on the side chain as a raw material, or alternatively can be prepared using a peptide having a carboxylic acid on the side chain as a precursor by referring to the method described in J. Am. Chem. Soc., 2016, 138, 5016-5019 or the like, as illustrated below. Specifically, the peptides having the target aryl or heteroaryl group on the side chain can be prepared by activating a peptide having a carboxylic acid on the side chain with N-hydroxyphthalimide, and reacting it with any aryl halide or heteroaryl halide.

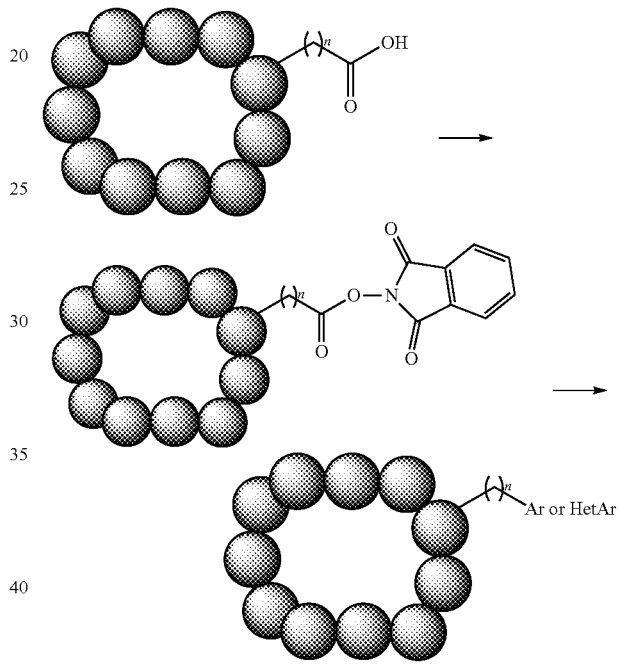

A peptide having carboxylic acid in a substituent of a nitrogen atom and/or in a side chain and having aryl halide or heteroaryl halide in a substituent of another nitrogen atom and/or in another side chain within the molecule can be used to produce a peptide compound in which the peptide main chain is crosslinked. Specifically, a crosslinked compound can be produced by activating a peptide having carboxylic acid with N-hydroxyphthalimide and crosslinking it by reaction with aryl halide or heteroaryl halide within the molecule.

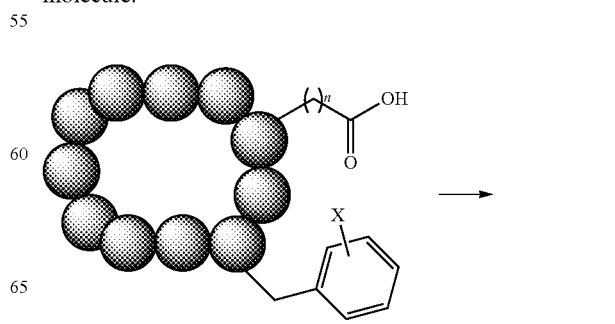

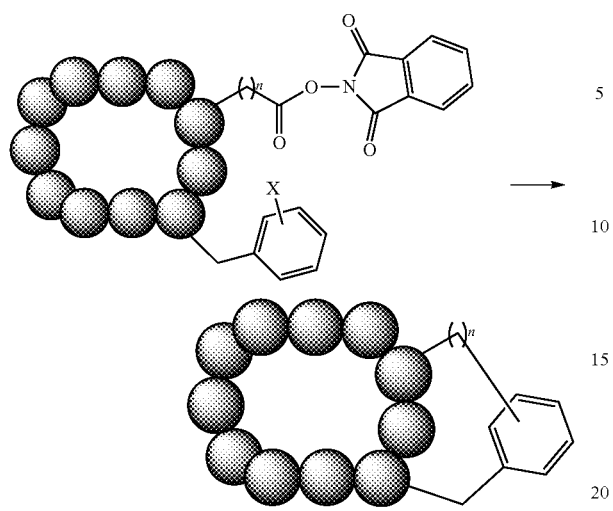

Alternatively, peptides having an aryl or heteroaryl group on a side chain can also be synthesized by Suzuki coupling using a peptide having a boronic acid on the side chain as a precursor, as illustrated below. Specifically, the target peptides having an aromatic ring on the side chain can be prepared by synthesizing a precursor peptide using an Fmoc amino acid having a boronic acid on the side chain as a raw material, and reacting it with any aryl halide in the presence of a palladium catalyst.

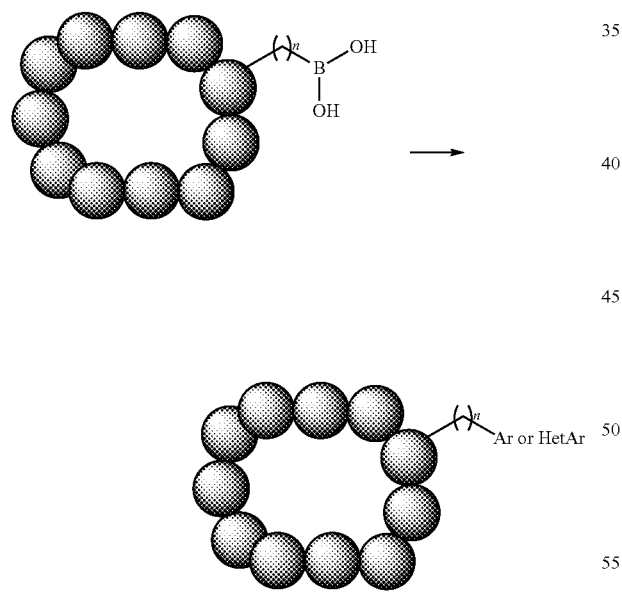

A peptide having boronic acid in a substituent of a nitrogen atom and/or in a side chain and having aryl halide in a substituent of another nitrogen atom and/or in another side chain within the molecule can be used to produce a peptide compound in which the peptide main chain is crosslinked. Specifically, a crosslinked compound can be produced by allowing a peptide having boronic acid to react and thereby crosslink with aryl halide within the molecule in the presence of a palladium catalyst.

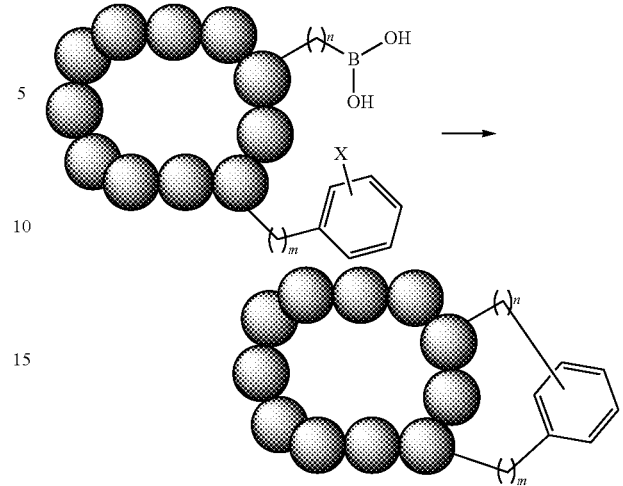

A peptide having olefin in the substituent of a nitrogen atom and/or in a side chain and having aryl halide in the substituent of another nitrogen atom and/or in another side chain within the molecule can be used to produce a peptide compound that is crosslinked by arylene-containing alkylene. Specifically, the crosslinked compound can be produced by conversion to a boron compound by a hydroboration reaction on olefin, and then causing the boron compound to be reacted, and thereby crosslinked, with the intramolecular aryl halide in the presence of a palladium catalyst.

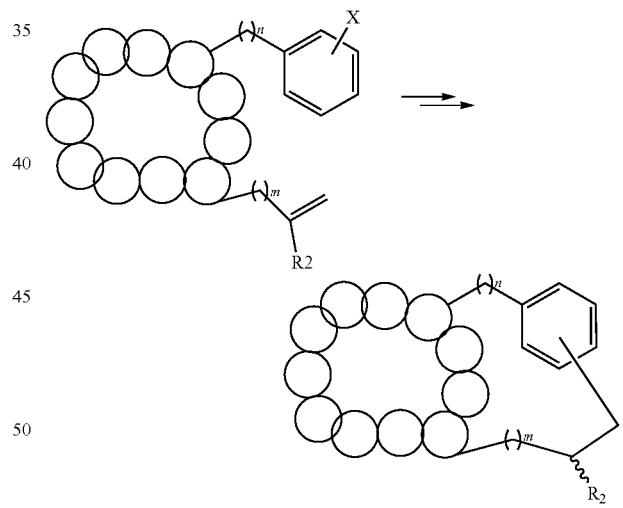

(Method of Preparing Peptides Containing an Amide Group on the Side Chain)

Peptides having an amide group on the side chain can be synthesized using an Fmoc amino acid having the target amide group on the side chain as a raw material, or alternatively can be synthesized by amidation of a peptide having a carboxylic acid on the side chain as a precursor, as illustrated below. Specifically, the target peptides having an amide group on the side chain can be obtained by deprotecting a peptide having a protected carboxylic acid on the side chain to synthesize a precursor peptide having a carboxylic acid on the side chain, and condensing it with any amine using a condensing agent such as HATU.

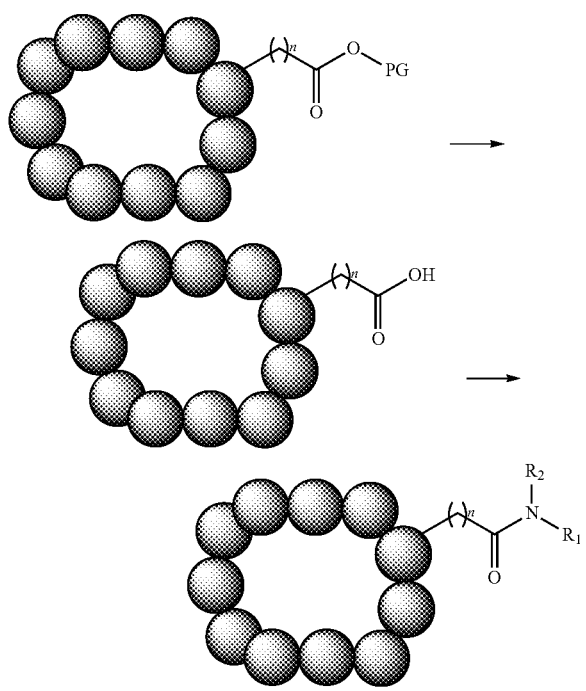

A peptide having carboxylic acid in a substituent of a nitrogen atom and/or in a side chain and having an amino group in a substituent of another nitrogen atom and/or in another side chain within the molecule can be used to produce a peptide compound in which the peptide main chain is crosslinked. Specifically, a crosslinked compound can be produced by synthesizing a precursor peptide having carboxylic acid and an amino group by deprotection, and condensing them using a condensing agent such as HATU for crosslinking by intramolecular amidation reaction.

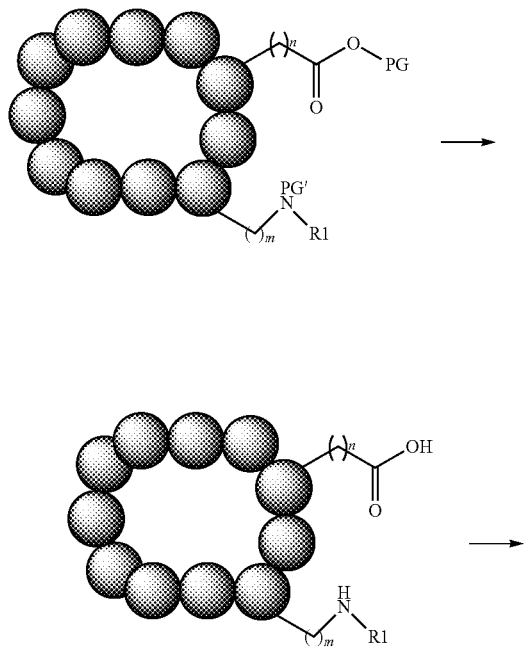

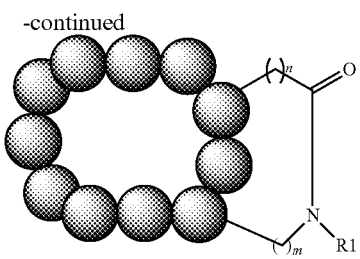

(Synthesis of Peptides Containing a Structure that is Highly Substituted and May Contain a Double Bond on the Side Chain)

Peptides having a structure that is highly substituted and may contain a double bond on the side chain can be synthesized using an Fmoc amino acid having the target double bond on the side chain as a raw material, or alternatively can be prepared by functionalization of a terminal olefin. Specifically, a peptide having a terminal olefin on the side chain can be synthesized according to the general peptide synthesis method described in the present Examples, and the side chain can be further converted to a side chain having a highly substituted olefin by coupling with a substrate having any terminal olefin by olefin metathesis reaction. Further, the side chain can be converted to a corresponding side chain by reducing the olefin by hydrogenation reaction.

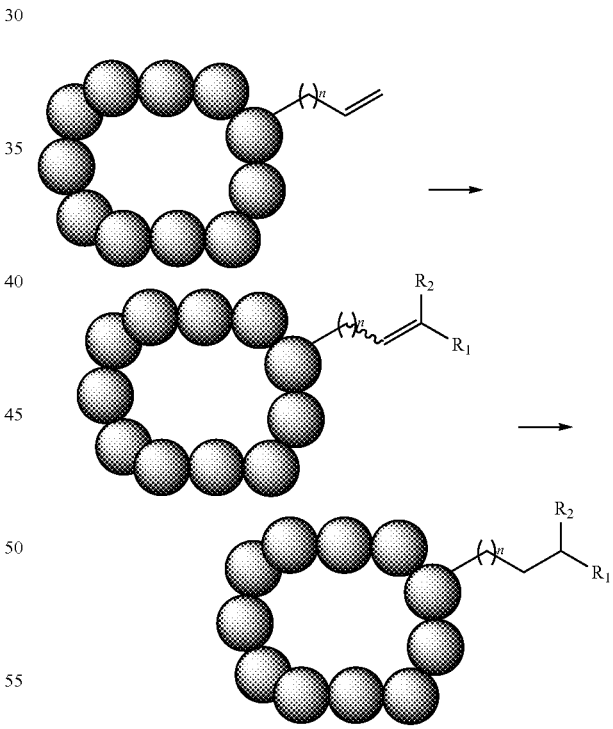

Peptide compounds with a peptide backbone crosslinked can also be prepared using a peptide having multiple double bonds in substituents of nitrogen atoms and/or in side chains. Specifically, crosslinked compounds can be prepared by synthesizing a peptide having an olefin at two sites of the substituents of nitrogen atoms and/or the side chains according to the general peptide synthesis method described in the present Examples, and further crosslinking the two olefins by olefin metathesis reaction by referring to Nature Protocols, 2011, 6, 761-771. Further, compounds crosslinked with saturated alkylenes can be prepared by reducing the olefins by hydrogenation reaction.

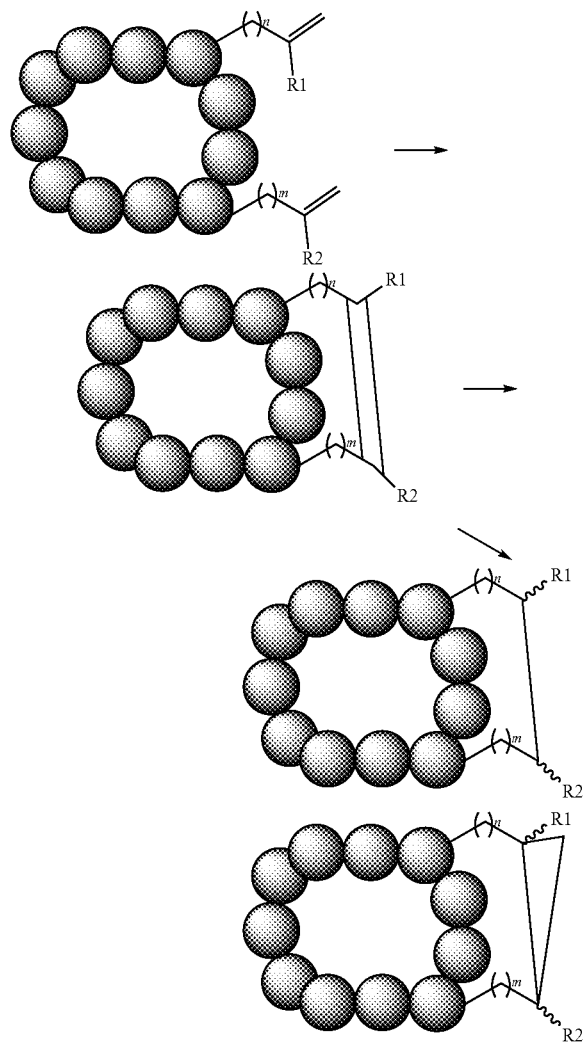

A peptide that contains aryl having an olefin-containing substituent in the substituent of a nitrogen atom and/or in a side chain can be used to produce, as the crosslinked compound, a peptide compound that is crosslinked by arylene and a divalent group containing a double bond. Specifically, the crosslinked compound can be produced by synthesizing a peptide having an aryl containing an olefin in the substituent of a nitrogen atom and/or in a side chain and having olefin in the substituent of another nitrogen atom and/or in another side chain within the molecule according to the general peptide synthesis method described in the Examples, and crosslinking the two olefins by an olefin metathesis reaction. Moreover, a compound crosslinked by arylene-containing alkylene can be produced by reducing olefin by a hydrogenation reaction.

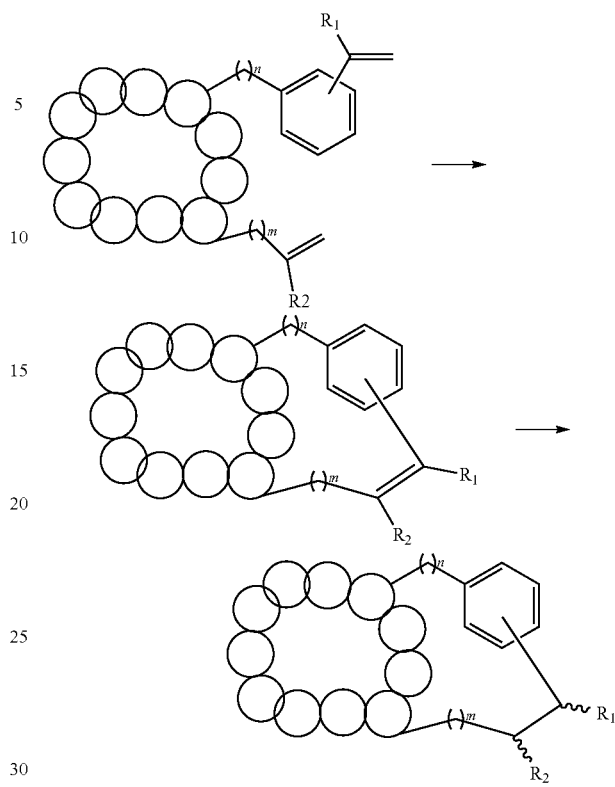

(Synthesis of Peptides Containing a Triazole on the Side Chain)

Peptides having a triazole on the side chain can be prepared by click reaction with an azido group. Specifically, peptide compounds having an azido group on the side chain can be prepared by synthesizing a peptide having an azido group on the side chain according to the general peptide synthesis method described in the present Examples, and coupling the peptide with any acetylene in the presence of copper (I) iodide by referring to Bioorganic & Medicinal Chemistry Letters, 2009, 19, 4130-4133 or the like.

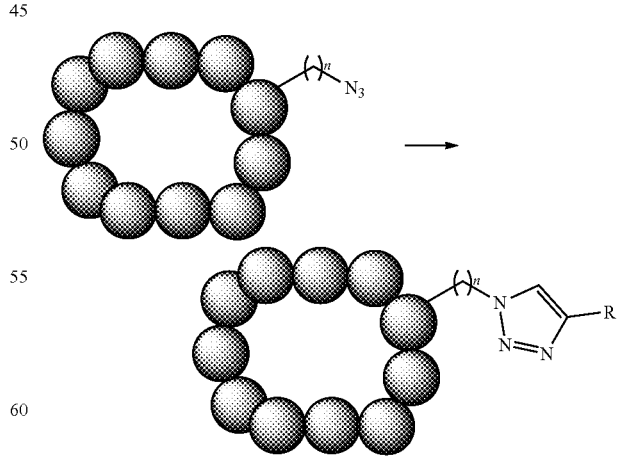

A peptide having an azide group in a substituent of a nitrogen atom and/or in a side chain and having acetylene in a substituent of another nitrogen atom and/or in another side chain within the molecule can be used to produce a peptide compound in which the peptide main chain is crosslinked. Specifically, a crosslinked compound can be produced by allowing a peptide having an azide group to react and thereby crosslink with acetylene within the molecule in the presence of a palladium catalyst.

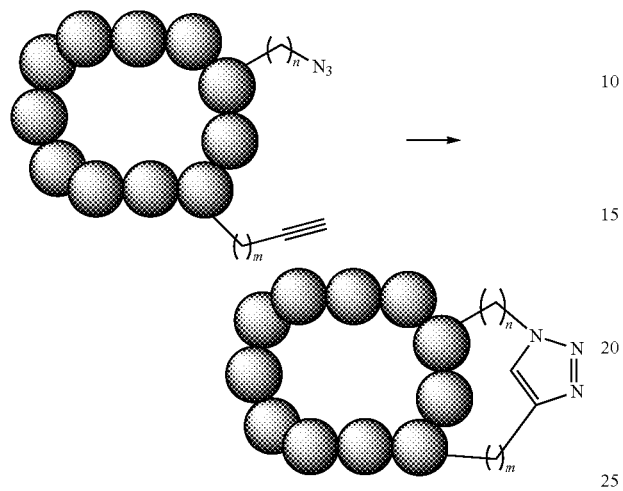

(Synthesis of Peptides Containing an Aryl Group Substituted with an Alkynyl Group on the Side Chain)

Peptides containing an aryl group substituted with an alkynyl group on the side chain can be synthesized by Sonogashira coupling reaction with an aryl halide group. Specifically, the conversion to peptide compounds having an aryl group substituted with an alkynyl group on the side chain can be conducted by synthesizing a peptide having an aryl iodide group on the side chain according to the general peptide synthesis method described in the present Examples, and coupling the peptide with any acetylene in the presence of copper (I) iodide.

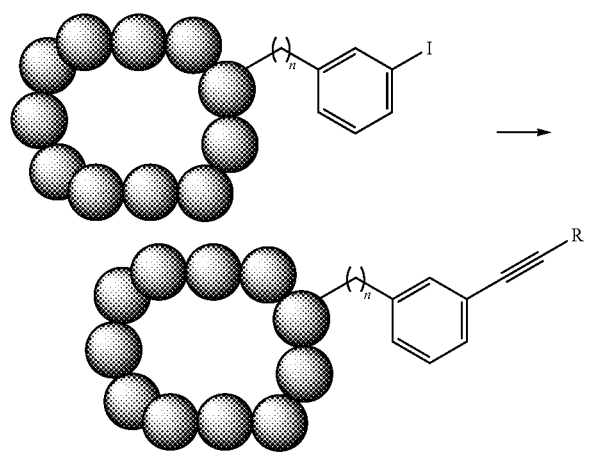

A peptide having an aryl halide in a substituent of a nitrogen atom and/or in a side chain and having acetylene in a substituent of another nitrogen atom and/or in another side chain within the molecule can be used to produce a peptide compound in which the peptide main chain is crosslinked. Specifically, a crosslinked compound can be produced by allowing a peptide having aryl iodide to be couple and thus crosslink with acetylene within the molecule in the presence of copper (I) iodide.

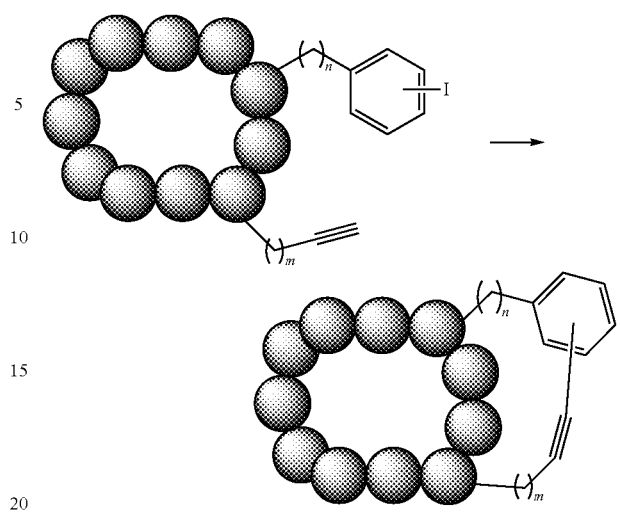

(General Method for Producing Oligopeptide Compounds)

Provided below is a general method for producing an oligopeptide having a cyclic structure formed between a substituent of a nitrogen atom and a side chain. In the following scheme, $PG_1$ and $PG_1'$ represent protecting groups of a nitrogen atom, $PG_2$ and $PG_2'$ represent protecting groups of an oxygen atom, $R_{n-1}$, $R_n$, $R_{n+1}$, and $Q_n$ represent side chains of an amino acid, $P_{n-1}$, $P_n$, and $P_{n+1}$ represent substituents of a nitrogen atom, and $Y_1$ and $Y_2$ each represent hydrogen, halogen, or alkyl. In the method for producing an amino acid provided below, groups other than the intended functional group may undergo chemical reaction. In such a case, introducing a protecting group to the unintended functional groups enables only the desired reaction to proceed. The reactions for attaching and detaching such a protecting group may be performed, for example, by the methods described in Greene's, "Protective Groups in Organic Synthesis" (5th edition, John Wiley & Sons 2014). As for the conversion reaction of functional groups of a compound, Comprehensive Organic Transformations: A Guide to Functional Group Preparations (5th edition) by Larock or March's Advanced Organic Chemistry: Reactions, Mechanisms, and Structure (8th edition) by Smith can be referred to.

An oligopeptide compound with a cyclic structure formed between a substituent of a nitrogen atom of an amino acid and a side chain of another amino acid can be synthesized using the following method. A protected amino acid can be reacted with an alkylating agent having an olefin in the presence of a base to introduce an alkyl group having an olefin. Then, the C-terminus can be elongated with an amino acid by condensation with a C-terminally protected amino acid. The condensation reaction can be carried out using various combinations of carboxyl-activating agents, such as the combination of DIC and HOBt, the combination of DIC and HOAt, and the combination of HATU and DIPEA. Subsequently, the protected nitrogen atom can be deprotected and then elongated with a protected amino acid having an olefin in the side chain. Then, the olefins within the molecule can be cyclized by metathesis reaction. Then, the C-terminal protecting group can be deprotected to produce an oligopeptide compound that has a free C-terminus and a double bond-containing cyclic structure formed between a substituent of a nitrogen atom and a side chain.

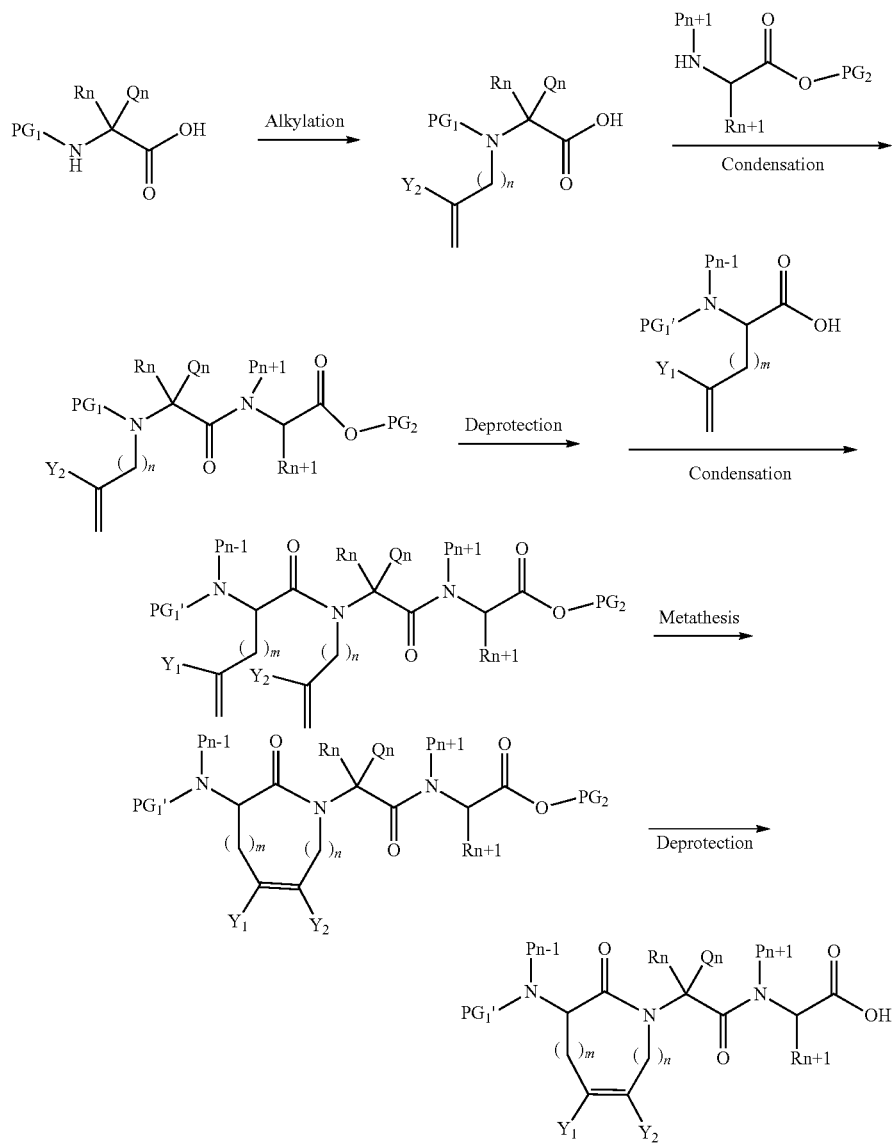

Also, an oligopeptide compound having a double bond-containing cyclic structure can be used to produce an oligopeptide compound having a cyclic structure in which the double bond is converted to a single bond. Specifically, a C-terminally protected compound having a double bond-containing cyclic structure is reduced by hydrogenation reaction and then the C-terminal protecting group is deprotected, whereby an oligopeptide compound having a free C-terminus and a cyclic structure formed with alkylene between a substituent of a nitrogen atom and a side chain can be produced.

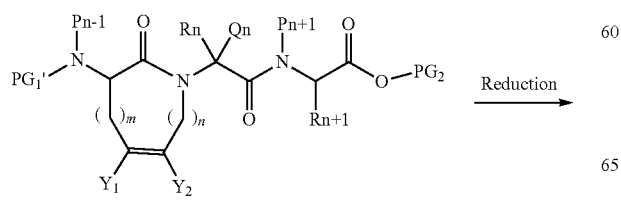

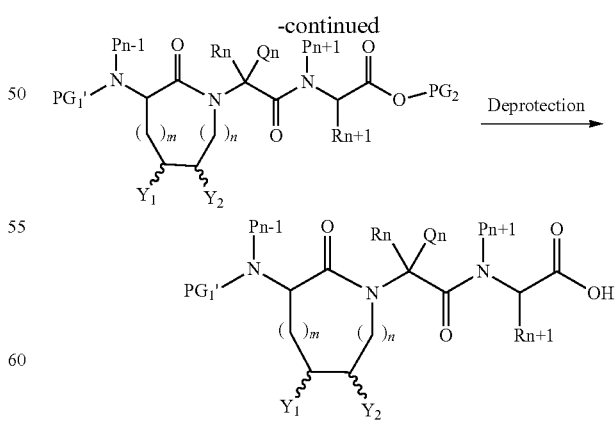

Moreover, an oligopeptide compound having a double bond-containing cyclic structure can be used to produce an oligopeptide compound having a crosslinked structure in which the double bond is converted to a cyclopropane ring. Specifically, a C-terminally protected compound having a double bond-containing cyclic structure can be subjected to conditions such as diiodomethane-diethylzinc to convert the double bond to a cyclopropane ring. Then, the C-terminal protecting group is deprotected, whereby an oligopeptide compound having a crosslinked structure in which the double bond is converted to a cyclopropane ring can be produced.

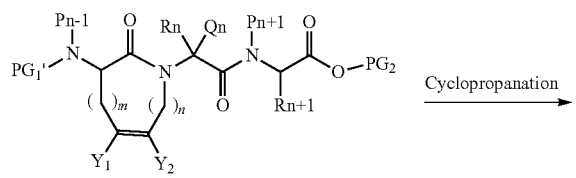

Cyclopropanation

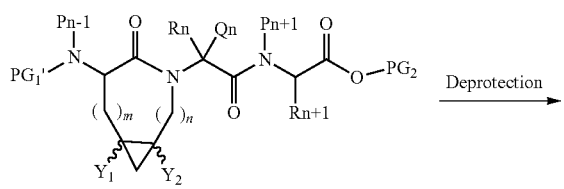

Deprotection

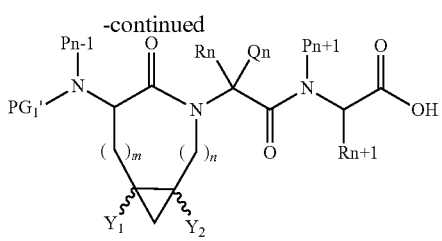

An oligopeptide compound having a cyclic structure formed between a substituent of a nitrogen atom of an amino acid and a side chain of another amino acid can also be synthesized by the following method. By allowing an aldehyde to act on a protected amino acid according to the method of Freidinger et al. (J. Org. Chem., 1983, 48 (1), 77-81), an oxazolidinone compound to which a cyclic protecting group is introduced can be obtained. Then, by carrying out a ring-opening reaction using a silicon compound having an olefin according to the method of Nguyen et al. (Synthesis, 2009, 12, 1991), an alkyl group having an olefin can be introduced to the nitrogen atom. The C-terminus can then be elongated with an amino acid by condensation with a C-terminally protected amino acid. Subsequently, the protected nitrogen atom can be deprotected and then elongated with a protected amino acid having an olefin in the side chain. Then, the olefins within the molecule can be cyclized by metathesis reaction. Then, the C-terminal protecting group is deprotected, whereby an oligopeptide compound having a free C-terminal and a cyclic structure containing a double bond between a substituent of a nitrogen atom and a side chain is formed can be produced.

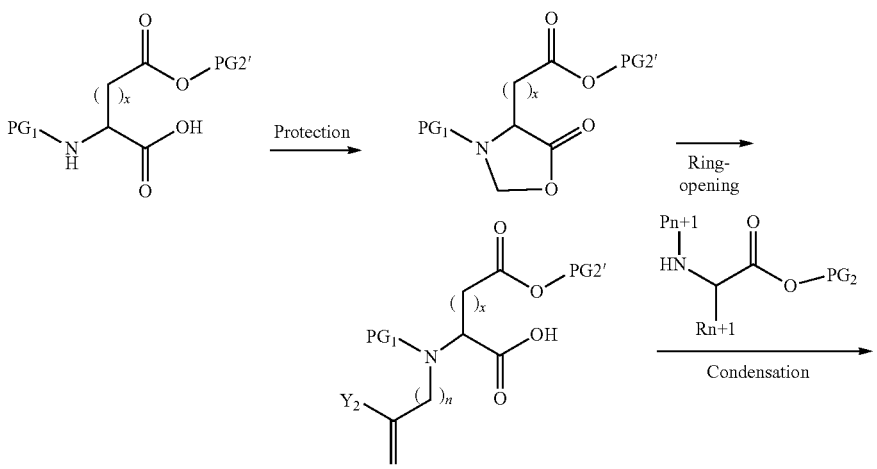

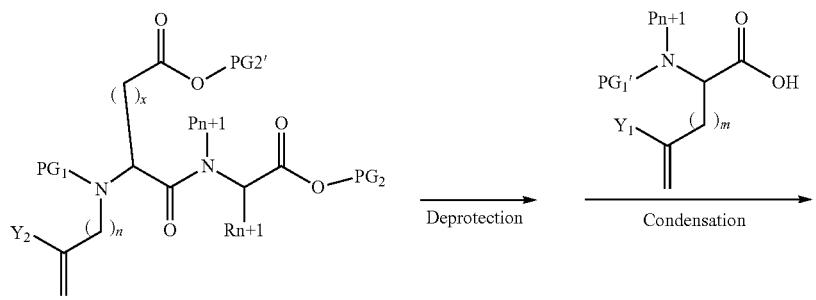

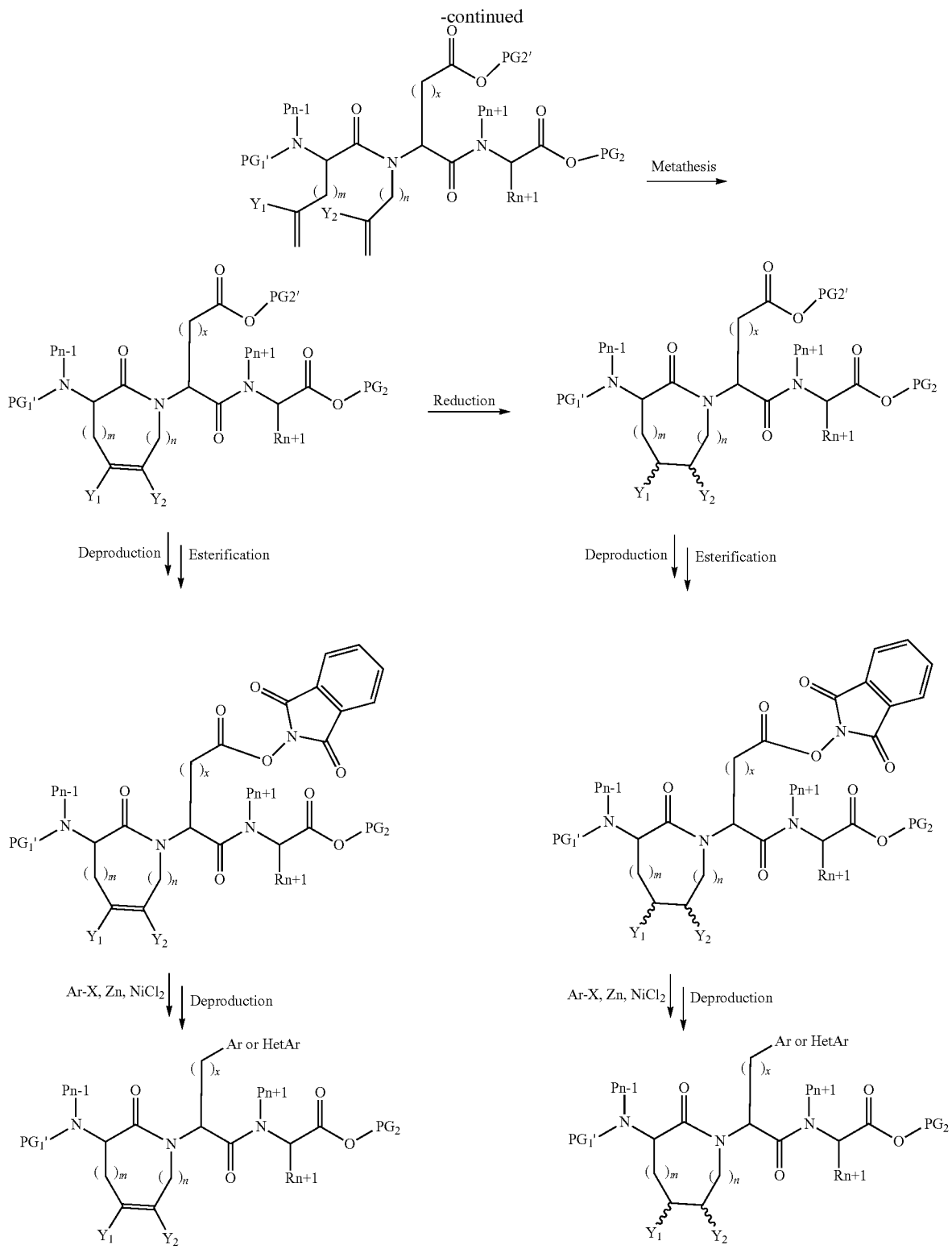

An oligopeptide containing an aryl group substituted with an alkenyl group (y=0 to 2) in a side chain can be produced by a Suzuki coupling reaction between an aryl halide group and a boron compound having an alkenyl group. Specifically, a peptide having an aryl iodide group in a side chain can be synthesized according to the general oligopeptide synthesis method described in the Examples, and then coupled with a boron compound having an alkenyl group in the presence of a palladium catalyst for conversion to an oligopeptide compound having an aryl group that is substituted with an alkenyl group (y=0 to 2) in a side chain.

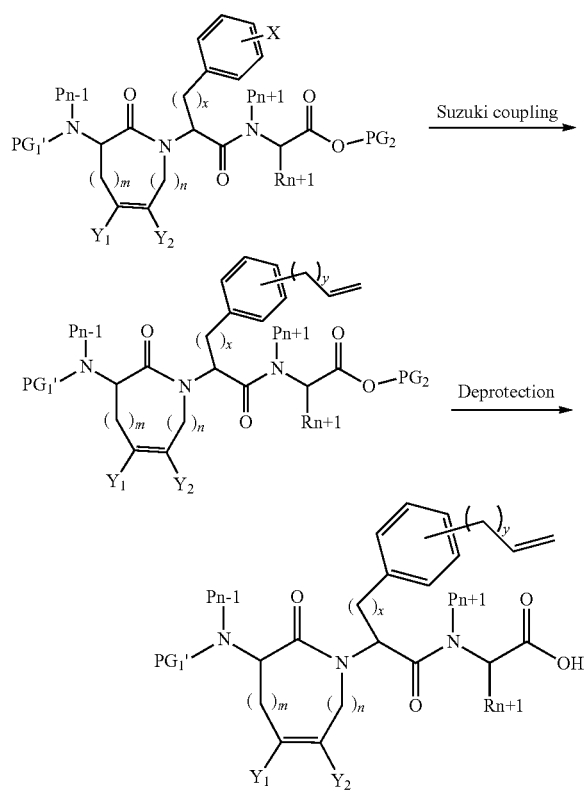

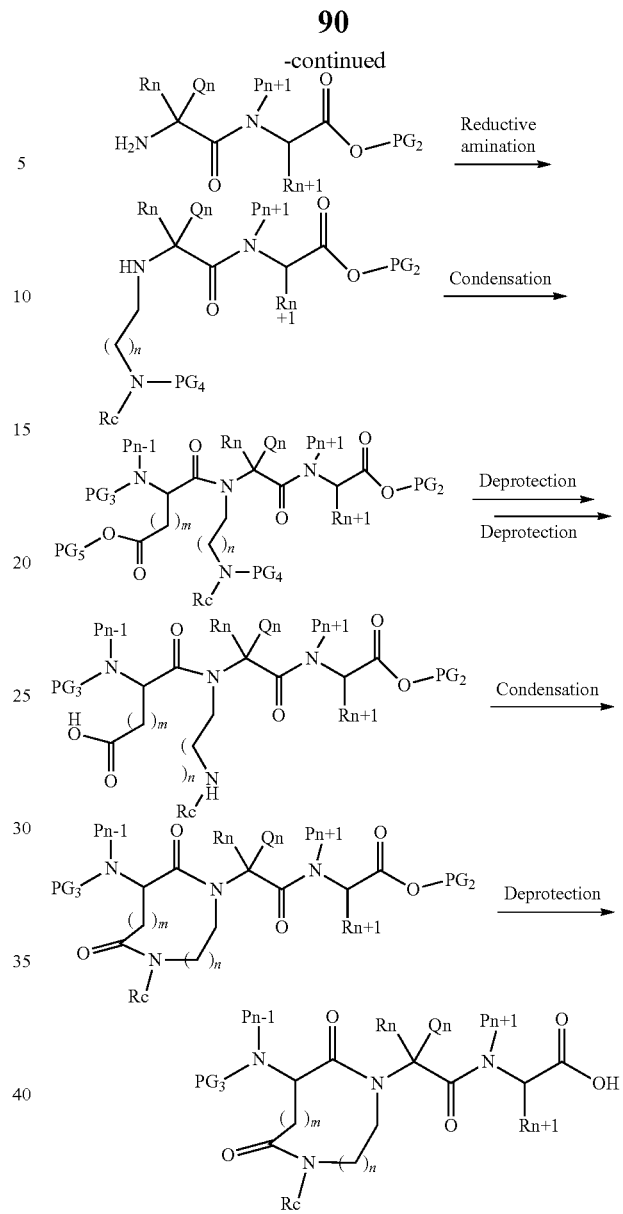

An oligopeptide compound in which a substituent for the nitrogen atom of an amino acid and the side chain of another amino acid form a cyclic structure by an amide bond can be synthesized using the following method. Specifically, a C-terminally protected peptide is synthesized according to the general synthesis method described in the Examples, then deprotected at the N-terminal, and subjected to a reductive amination reaction with an aldehyde compound containing an amino group having a protecting group to introduce an amino group having a protecting group in the N-substituent. This is then condensed with a protected amino acid that contains a carboxy group having a protecting group in a side chain. After the protecting groups for the carboxy group and the amino group are removed, the molecule is condensed intramolecularly and deprotected at the C-terminal, thereby achieving conversion to an oligopeptide compound in which a substituent for the nitrogen atom of an amino acid and the side chain of another amino acid form a cyclic structure by an amide bond.

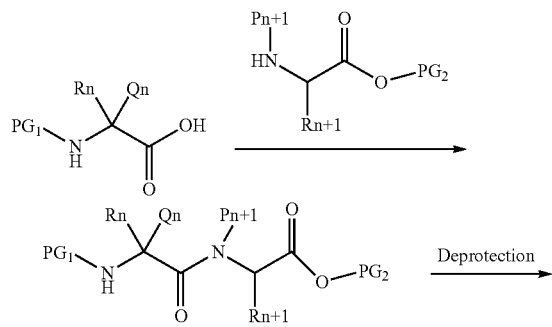

(Method for Cyclizing Peptide Compound on Resin)

Cyclic compounds and oligopeptide compounds having a cyclic structure can be cyclized by, in addition to cyclization according to the method described in the present Examples, metathesis reaction on a resin as shown in the following method. Specifically, as a resin-supported peptide, a peptide having an olefin in two sites of the substituents of nitrogen atoms and/or the side chains is synthesized according to the common peptide synthesis method described in the present Examples, then the two olefins can be cyclized by metathesis reaction to produce a compound having a cyclic structure. Moreover, peptide elongation, cleavage from resin, cyclization, deprotection, and purification can be performed according to the common peptide synthesis method described in the present Examples to produce a cyclic compound and an oligopeptide compound having a cyclic structure.

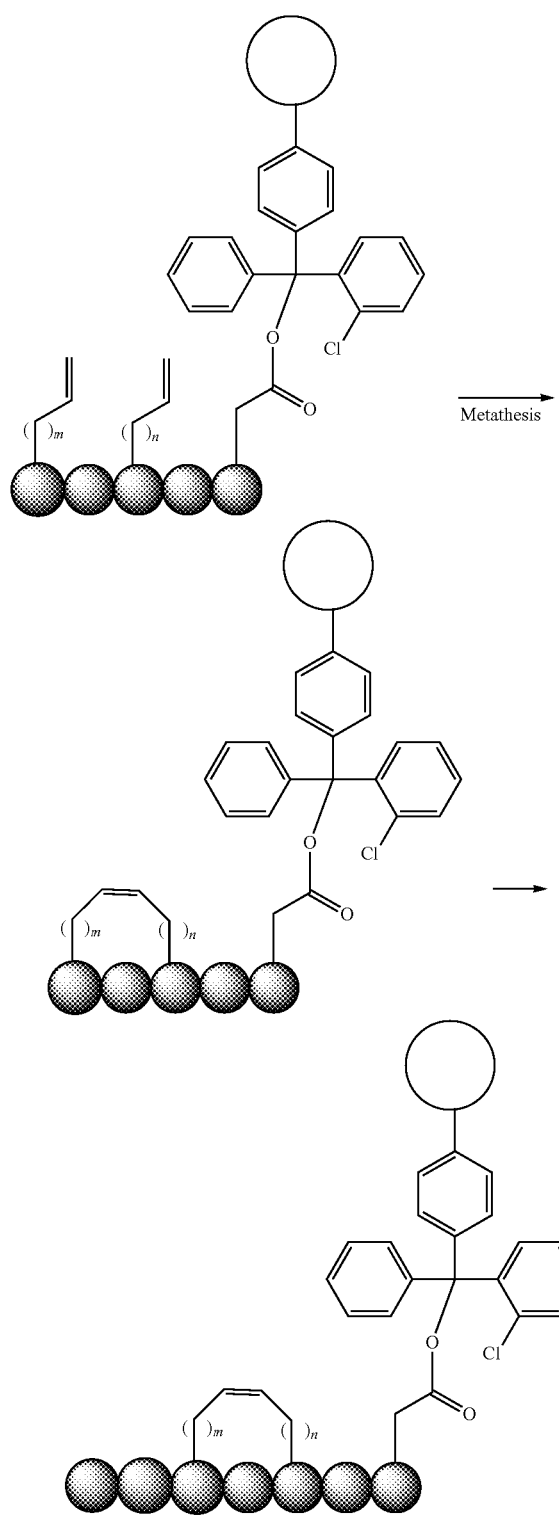

protecting group for an amino acid side chain, $R_n$ and $Q_n$ each represent an amino acid side chain, $P_n$ represents a substituent for a nitrogen atom, P' represents $C_1$-$C_5$ alkyl, and R, R', R", and R'" each represent a substituent for a hydrogen or amino group. In the methods of preparing amino acids shown below, a functional group other than the target functional group may cause chemical reaction. In such a case, only the desired reaction can be allowed to proceed by introducing a protecting group onto a non-target functional group. Examples of such protecting group introduction and removal reactions include methods described in Greene's "Protective Groups in Organic Synthesis" (5th ed., John Wiley & Sons 2014). For conversion reactions of compound functional groups, one can refer to Larock's "Comprehensive Organic Transformations: A Guide to Functional Group Preparations" (5th ed.) or Smith's "March's Advanced Organic Chemistry: Reactions, Mechanisms, and Structure" (8th ed.).

Non-natural amino acids having a protecting group ($PG_1$) introduced onto the amino acid nitrogen atom can be prepared using the following method. The target C-terminal-free non-natural amino acids can be prepared by introducing a protecting group onto an N-terminal-free amino acid available from a commercial supplier and deprotecting it as necessary according to conventional methods.

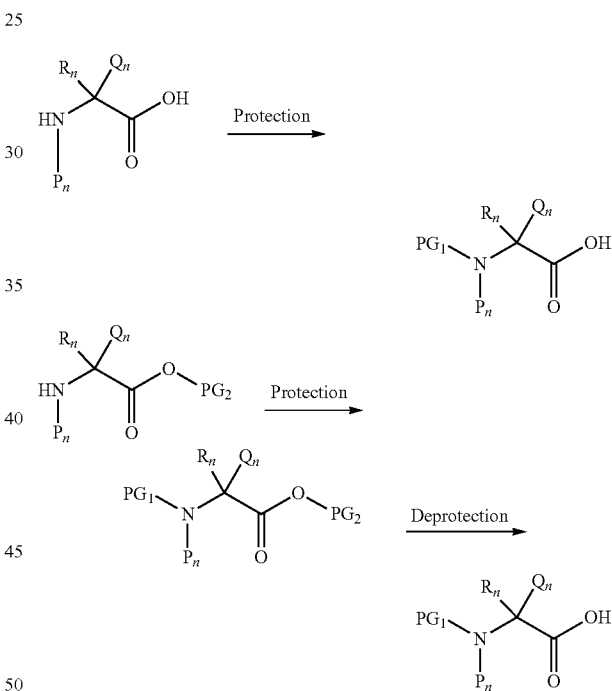

Non-natural amino acids having a protecting group ($PG_1'$) introduced onto the amino acid nitrogen atom can be prepared using the following method. The target C-terminal-free non-natural amino acids can be prepared by deprotecting an amino acid that has a protecting group ($PG_1$) introduced onto the N-terminus which is available from a commercial supplier, and introducing a protecting group, according to conventional methods.

(General Preparation Methods for Non-Natural Amino Acids)

General preparation methods for C-terminal-free non-natural amino acids where the nitrogen atoms of the amino acids are protected are shown below. In the following schemes, $PG_1$ and $PG_1'$ each represent a protecting group for a nitrogen atom, $PG_2$ and $PG_2'$ each represent a protecting group for an oxygen atom, $PG_3$ and $PG_4$ each represent a

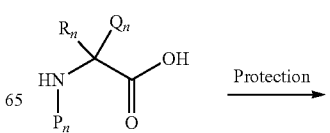

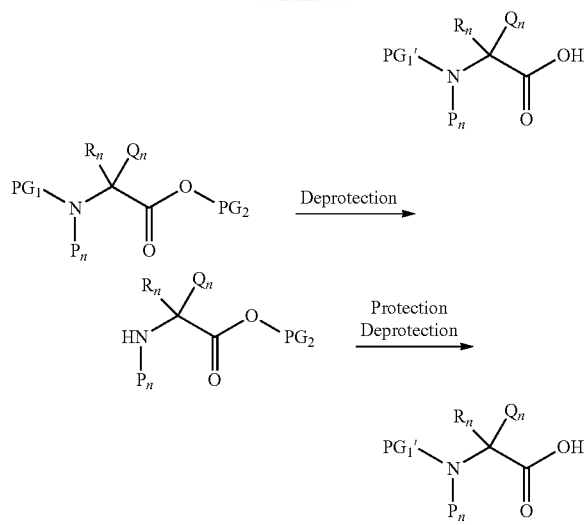

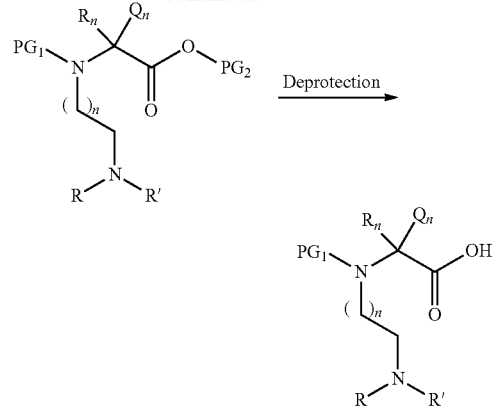

Non-natural amino acids having an aminoalkyl group introduced onto the substituent ($P_n$) of the amino acid nitrogen atom can be prepared using the following method. A bromoacetic acid ester derivative available from a commercial supplier is reacted with an amino alcohol according to the method of King et al. (Tetrahedron Letters, 2002, 43 (11), 1987-1990), and then a protecting group ($PG_1$) is introduced onto the nitrogen atom. Next, the hydroxyl group is oxidized according to the method of Dess et al. (J. Org. Chem., 1983, 48 (22), 4155-4156), and the aldehyde group is reductively aminated according to the method of Borch et al. (J. Org. Chem. 1972, 37 (10), 1673-1674) to introduce an amino group. Next, the target C-terminal-free non-natural amino acid can be prepared by deprotecting the protecting group for the oxygen atom.

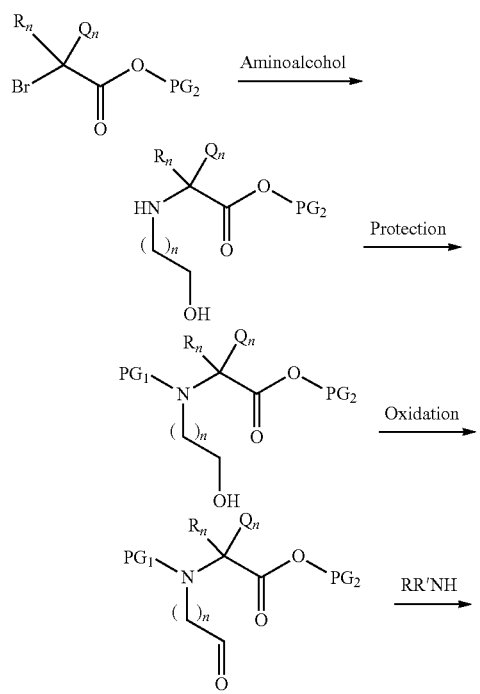

N-substituted amino acids can also be prepared by the following scheme of introducing a substituent ($P_n$) onto the amino acid nitrogen atom. A bromoacetic acid ester derivative available from a commercial supplier is reacted with an amine ($P_nNH_2$) in the presence of a base, and then a protecting group ($PG_1$) is introduced onto the nitrogen atom. Next, the target C-terminal-free non-natural amino acid can be prepared by deprotecting the protecting group for the oxygen atom.

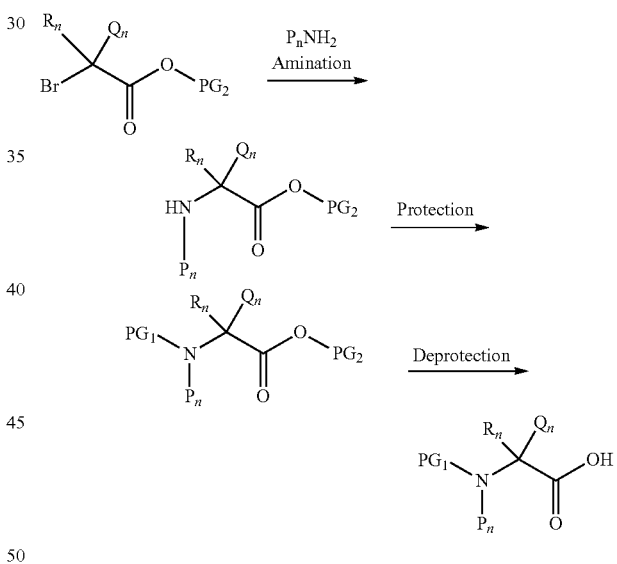

Non-natural amino acids having a-$CH_2$—P' group introduced onto the amino acid nitrogen atom can be prepared according to the following scheme. An oxazolidinone compound having an introduced cyclic protecting group can be obtained by allowing an aldehyde to act on a C-terminal-free amino acid available from a commercial supplier according to the method of Freidinger et al. (J. Org. Chem., 1983, 48 (1), 77-81). Next, the target C-terminal-free non-natural amino acid can be prepared by ring-opening reaction.

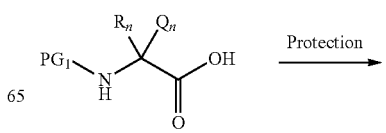

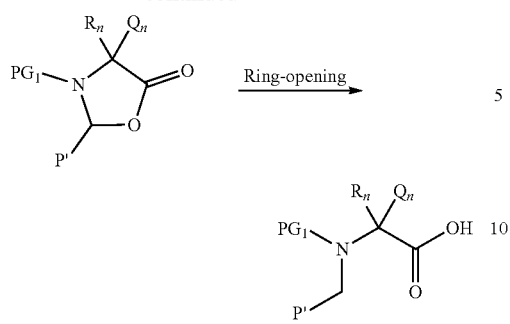

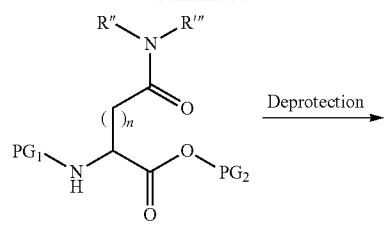

Non-natural amino acids having a $P_n$ group introduced onto the amino acid nitrogen atom can be produced according to the following scheme. The $P_n$ group can be introduced onto a commercially available C-terminal-free amino acid by allowing an alkylating agent ($P_n$—X) to act on it in the presence of a base. Then, a C-terminal-free non-natural amino acid can be produced by carrying out deprotection reaction and protecting group-introducing reaction by conventional methods.

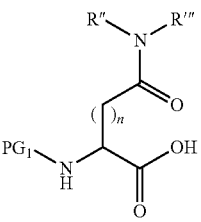

Non-natural amino acids having an amide group introduced onto the amino acid side chain and a-$CH_2$—P' group introduced onto the amino acid nitrogen atom can be prepared according to the following scheme. An oxazolidinone compound having an introduced cyclic protecting group can be obtained by allowing an aldehyde to act on a commercially available protected amino acid (n=1 or 2) according to the method of Freidinger et al. (J. Org. Chem., 1983, 48 (1), 77-81). Next, an amide compound can be obtained by deprotecting the side-chain protecting group and then allowing an amine (R"R"NH) to act on it. Next, the target C-terminal-free non-natural amino acid can be prepared by ring-opening reaction.

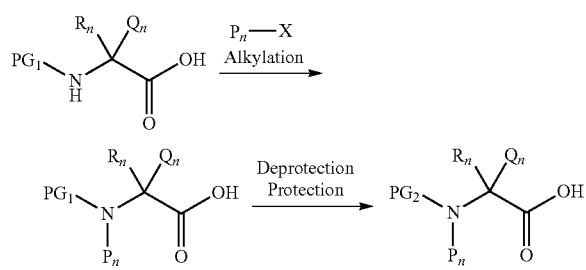

Non-natural amino acids having an amide group introduced onto the amino acid side chain can be prepared according to the following scheme. An amide group can be introduced onto the side chain by deprotecting a commercially available protected amino acid (n=1 or 2) and allowing an amine (R"R" "NH) to act on the resulting carboxylic acid. Next, a C-terminal-free non-natural amino acid can be prepared by deprotecting the C-terminal protecting group.

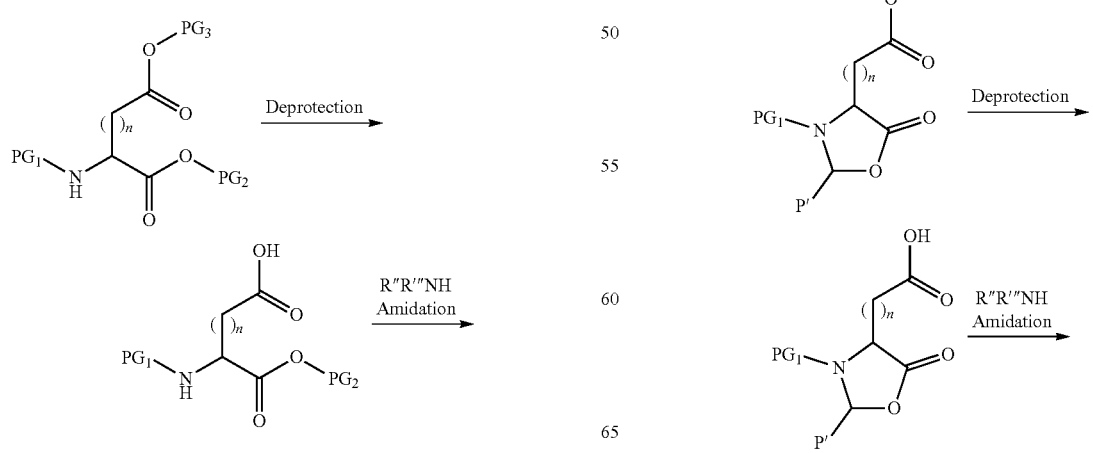

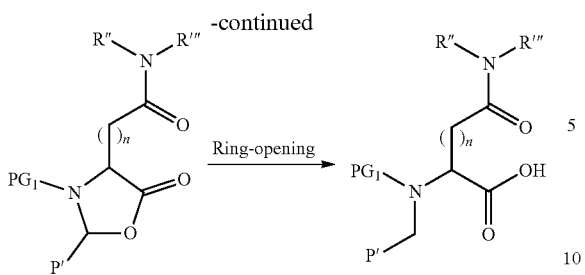

Non-natural amino acids having an amino group introduced onto the amino acid side chain can be prepared according to the following scheme. An amide group can be introduced onto the side chain by allowing an amine (R"R'"NH) to act on the carboxyl group of a commercially available protected amino acid (n=1 or 2). Next, a C-terminal-free non-natural amino acid can be prepared by conducting reduction reaction according to the method of Reeves et al. (Advanced Synthesis & Catalysis, 2013, 355 (1), 47-52) and then deprotecting the C-terminal protecting group.

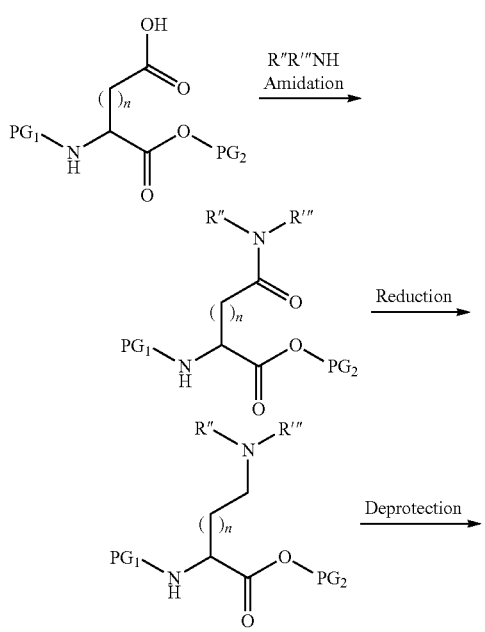

Non-natural amino acids having an amino group introduced onto the amino acid side chain and a-CH$_2$—P' group introduced onto the amino acid nitrogen atom can be prepared according to the following scheme. An amide group can be introduced onto the side chain by allowing an amine (R"R'"NH) to act on the carboxyl group of an amino acid protected by a cyclic protecting group (n=1 or 2). Next, the target C-terminal-free non-natural amino acid can be prepared by conducting reduction reaction according to the method of Reeves et al. (Advanced Synthesis & Catalysis, 2013, 355 (1), 47-52) and then performing ring-opening reaction.

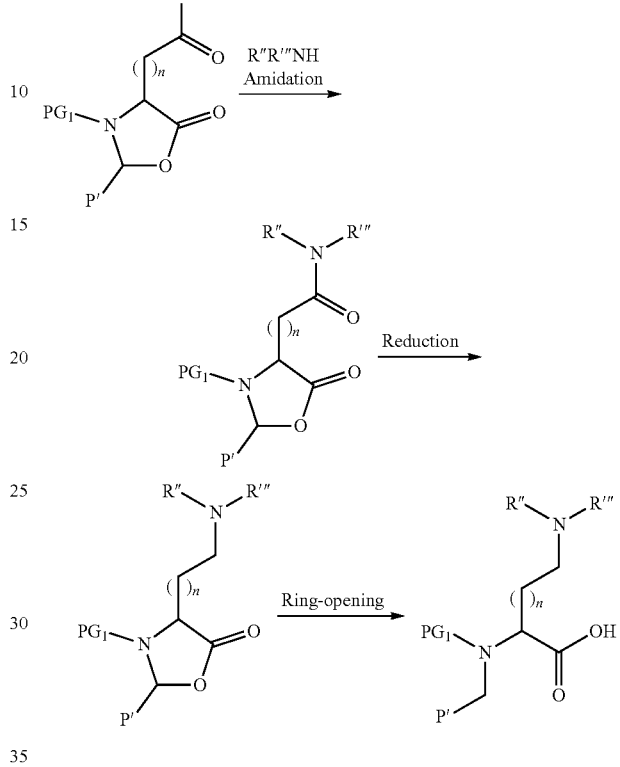

Non-natural amino acids having a fluoroalkyl group introduced onto the amino acid side chain can be prepared according to the following scheme. The carboxyl group of a commercially available protected amino acid (n=1 or 2) can be reduced and converted to an aldehyde group according to a conventional method, and the aldehyde group can be converted to a difluoromethyl group by introducing a fluorine atom according to a conventional method. Next, a C-terminal-free non-natural amino acid can be prepared by deprotecting the C-terminal protecting group.

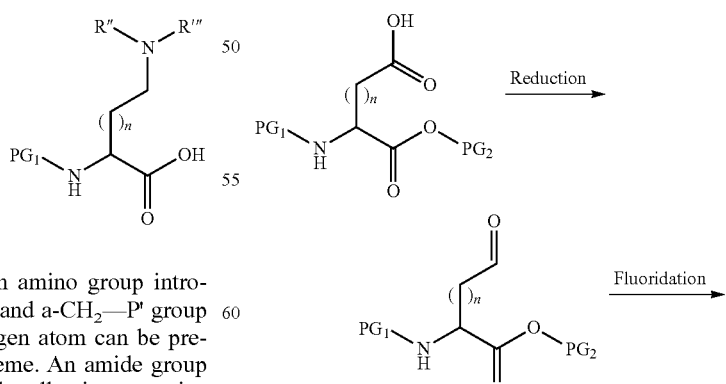

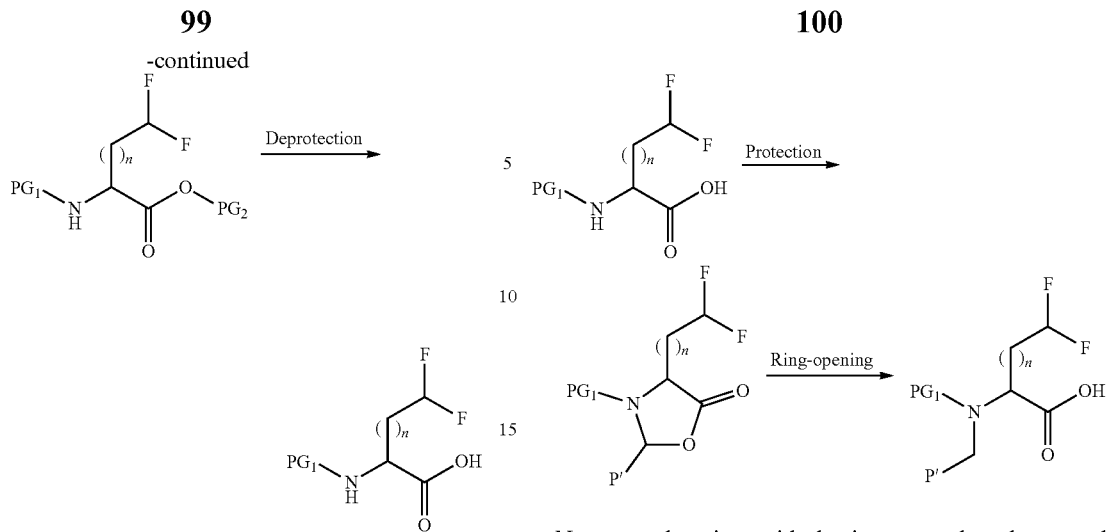

Non-natural amino acids having a halogenated alkyl group introduced onto the amino acid side chain and a-CH$_2$—P' group introduced onto the amino acid nitrogen atom can be prepared according to the following scheme. The carboxyl group of an amino acid protected by a cyclic protecting group (n=1 or 2) can be reduced and converted to an aldehyde group according to a conventional method, and the aldehyde group can be converted to a dihalogenated methyl group by introducing a halogen atom according to a conventional method. Next, a C-terminal-free non-natural amino acid can be prepared by ring-opening of the C-terminal cyclic protecting group.

Non-natural amino acids having an aryl or heteroaryl group (such groups are referred to as "Ar" in the scheme) introduced onto the amino acid side chain can be prepared according to the following scheme. An N-hydroxyphthalimide (NHPI) group can be introduced onto the side chain by allowing NHPI to act on the carboxyl group of a protected amino acid (n=1 or 2). A non-natural amino acid having an aryl or heteroaryl group introduced and possessing an aralkyl or heteroaralkyl group on the side chain can be prepared by allowing an aryl halide or heteroaryl halide to react according to the method of Huihui et al. (J. Am. Chem. Soc., 2016, 138 (15), 5016-5019). Next, a C-terminal-free non-natural amino acid can be prepared by deprotecting the C-terminal protecting group.

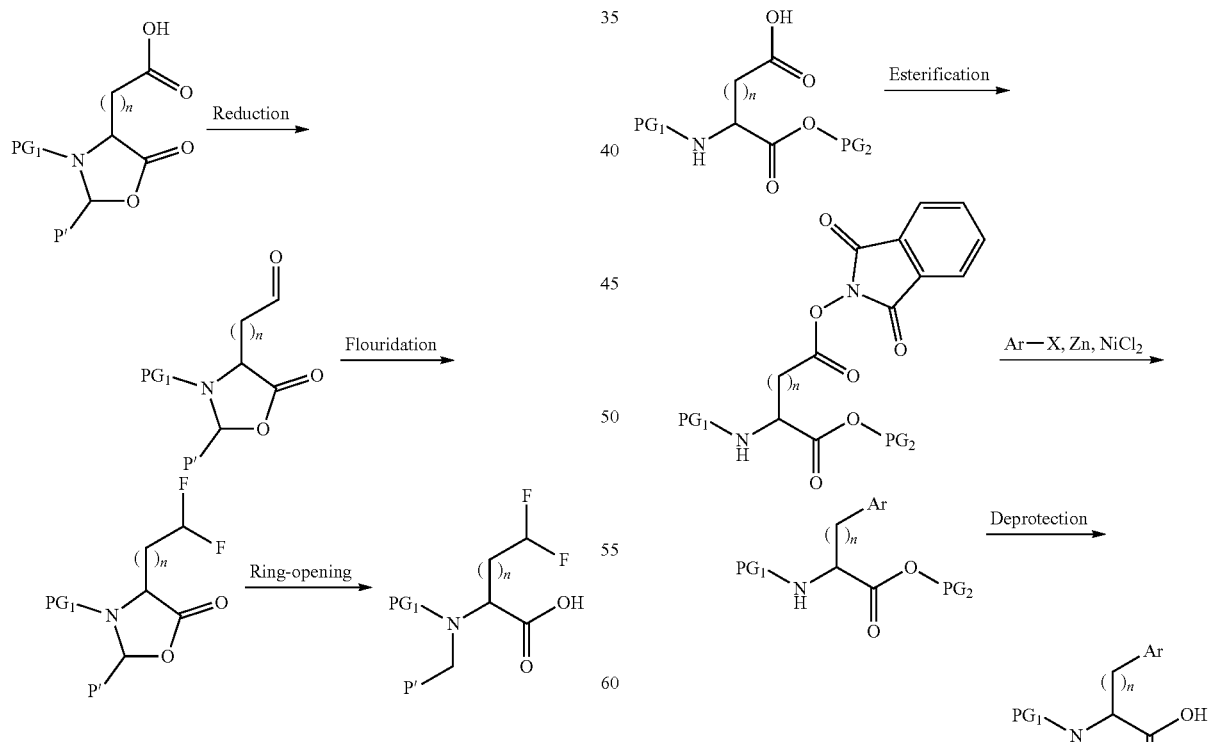

C-terminal-free non-natural amino acids having a halogenated alkyl group introduced onto the amino acid side chain and a-CH$_2$—P' group introduced onto the amino acid nitrogen atom can also be prepared by the method shown below.

Non-natural amino acids having an aryl or heteroaryl group (such groups are referred to as "Ar" in the scheme)

introduced onto the amino acid side chain and having a-CH₂—P' group introduced onto the amino acid nitrogen atom can be prepared according to the following scheme. An N-hydroxyphthalimide (NHPI) group can be introduced onto the side chain by allowing NHPI to act on the carboxyl group of an amino acid protected by a cyclic protecting group (n=1 or 2). A non-natural amino acid which has an aryl or heteroaryl group introduced, and has an aralkyl or heteroarylalkyl group on the side chain, and is protected by a cyclic protecting group, can be prepared by allowing an aryl halide or heteroaryl halide to react according to the method of Huihui et al. (J. Am. Chem. Soc., 2016, 138 (15), 5016-5019). Next, the target C-terminal-free non-natural amino acid can be prepared by ring-opening reaction.

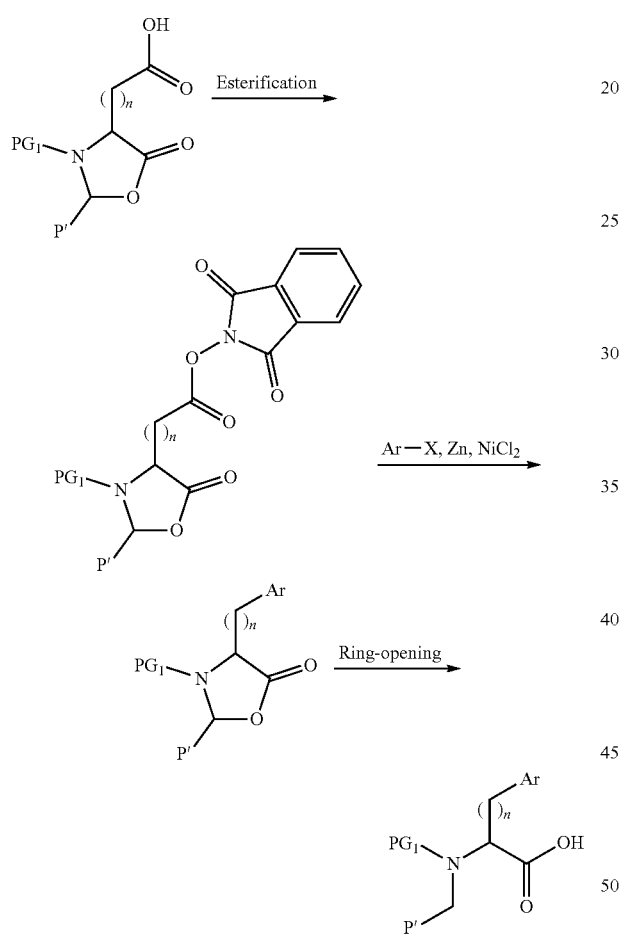

Non-natural amino acids having an aryl or heteroaryl group (such groups are referred to as "Ar" in the scheme) introduced onto the amino acid side chain can be prepared according to the following scheme. A non-natural amino acid having an aryl or heteroaryl group introduced and possessing an aralkyl or heteroaralkyl group on the side chain can be prepared by introducing a protecting group onto a commercially available protected amino group (n=0 or 1) and then allowing an aryl halide or heteroaryl halide to react according to the method of He et al. (Org. Lett. 2014, 16 (24), 6488-6491). Next, the target C-terminal-free non-natural amino acid can be prepared by deprotection reaction and protecting group introduction reaction.

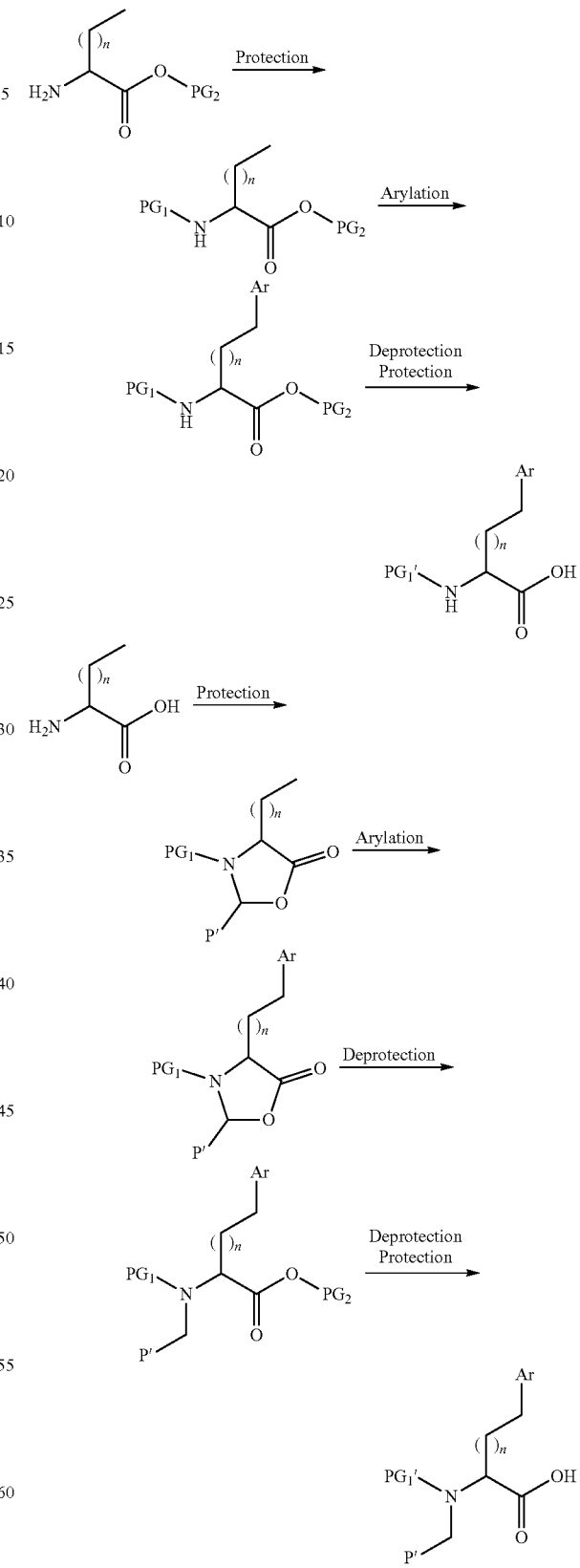

Non-natural amino acids having a halogen atom introduced onto the aralkyl group on the amino acid side chain can be prepared according to the following scheme. A boronic acid ester can be introduced onto the aralkyl group which may have a substituent (Ra) on the amino acid side chain according to the method of Ishiyama et al. (J. Am. Chem. Soc. 2002, 124 (3), 390-391). A halogen atom can be introduced onto the introduced boryl group using N-halosuccinimide according to the method of Lindner et al. (Chem. Eur. J., 2016, 22, 13218-13235). The target C-terminal-free non-natural amino acid can be prepared by appropriately introducing/removing a protecting group onto/from the obtained non-natural amino acid as necessary.

onto the introduced boryl group using N-halosuccinimide according to the method of Lindner et al. (Chem. Eur. J., 2016, 22, 13218-13235). The target C-terminal-free non-natural amino acid can be prepared by appropriately introducing/removing a protecting group onto/from the obtained non-natural amino acid as necessary.

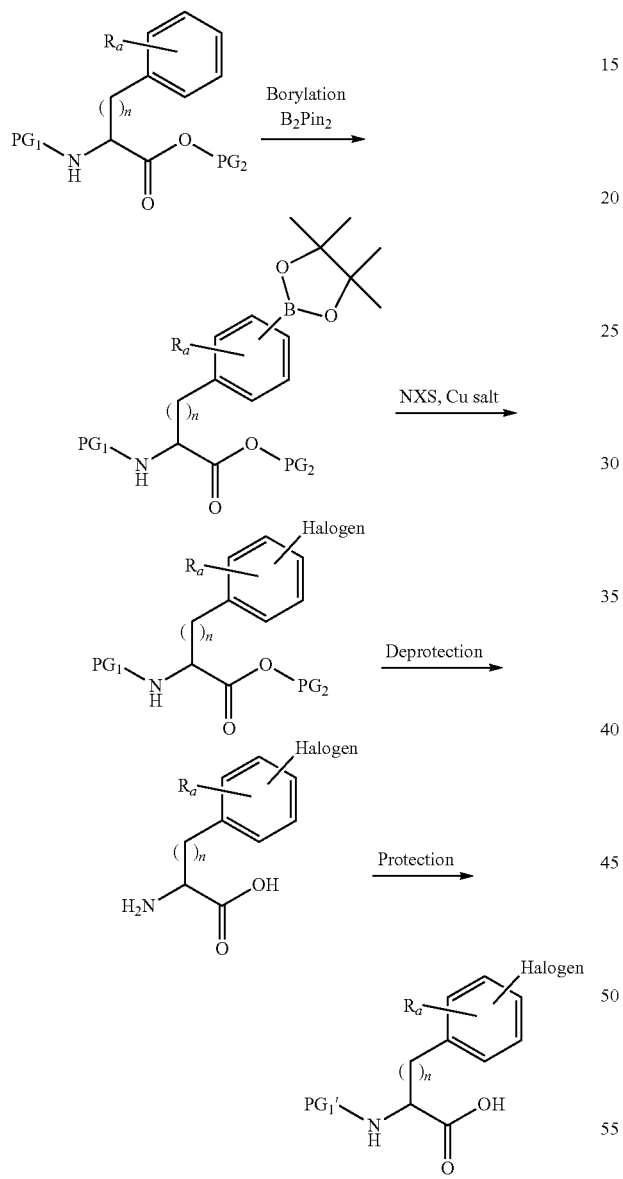

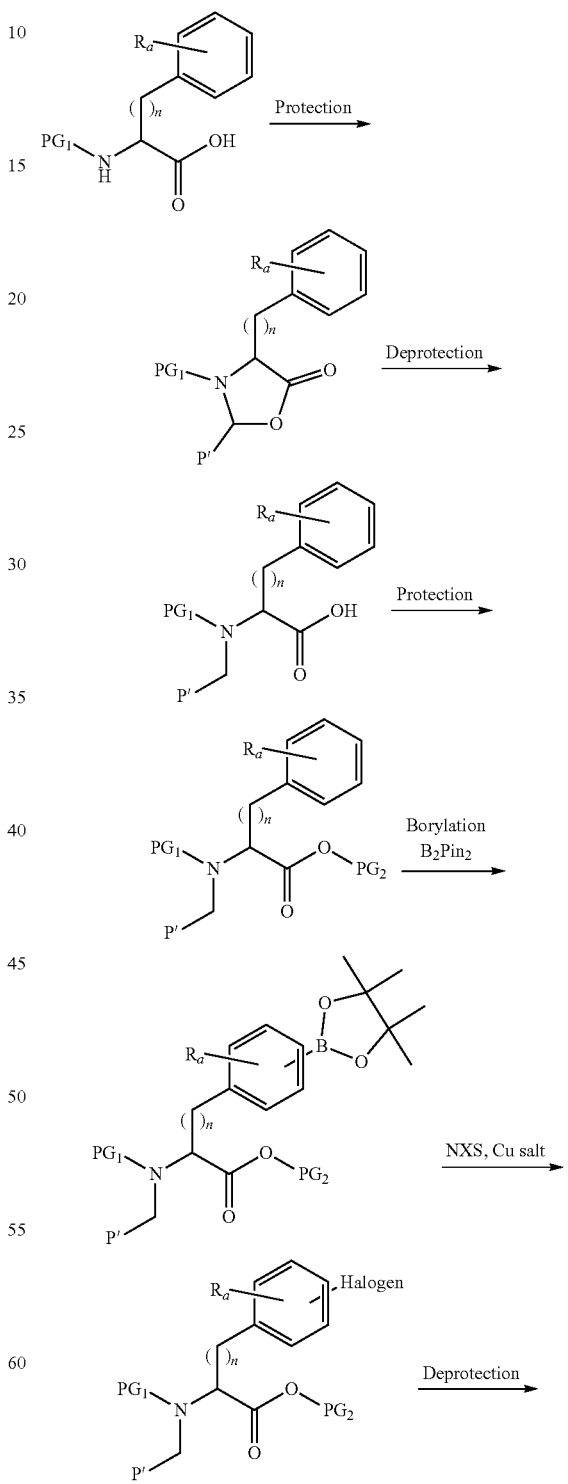

Non-natural amino acids having a halogen atom introduced onto the aralkyl group of the amino acid side chain and a-CH$_2$—P' group introduced onto the amino acid nitrogen atom can be prepared according to the following scheme. A boronic acid ester can be introduced onto the aryl group of the amino acid having an aralkyl group which may have a substituent (Ra) on the amino acid side chain according to the method of Ishiyama et al. (J. Am. Chem. Soc. 2002, 124 (3), 390-391). A halogen atom can be introduced

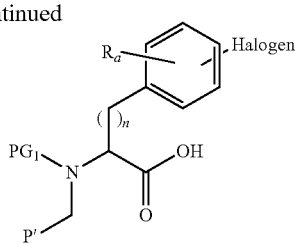

Non-natural amino acids having an optionally substituted alkoxy or aralkoxy (RbO) group on the amino acid side chain can be prepared according to the following scheme. A cyclized compound can be obtained according to the method of Mitsunobu et al. (Synthesis, 1981, 1, 1-28) after introducing a nosyl(Ns) group onto a commercially available serine derivative (n=1 or 2) according to a conventional method. A serine ether compound can be obtained by ring-opening of the cyclized compound with a suitable alcohol (RbOH) in the presence of a Lewis acid such as $BF_3 \cdot OEt_2$. The target C-terminal-free non-natural amino acid can be prepared by appropriately introducing/removing a protecting group onto/from the obtained non-natural amino acid as necessary.

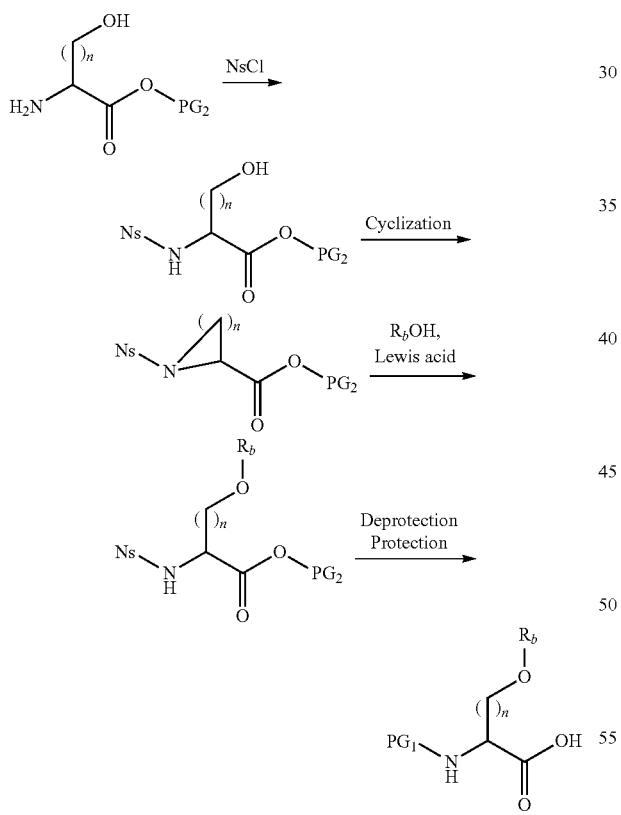

Non-natural amino acids having an optionally substituted alkoxy or aralkoxy (RbO) group on the amino acid side chain can be prepared according to the following scheme. A serine ether compound can be obtained by ring-opening of a commercially available cyclic compound (n=1 or 2) with a suitable alcohol (RbOH) in the presence of a Lewis acid such as $BF_3 \cdot OEt_2$ according to a conventional method. The target C-terminal-free non-natural amino acid can be prepared by appropriately introducing/removing a protecting group onto/from the obtained non-natural amino acid as necessary.

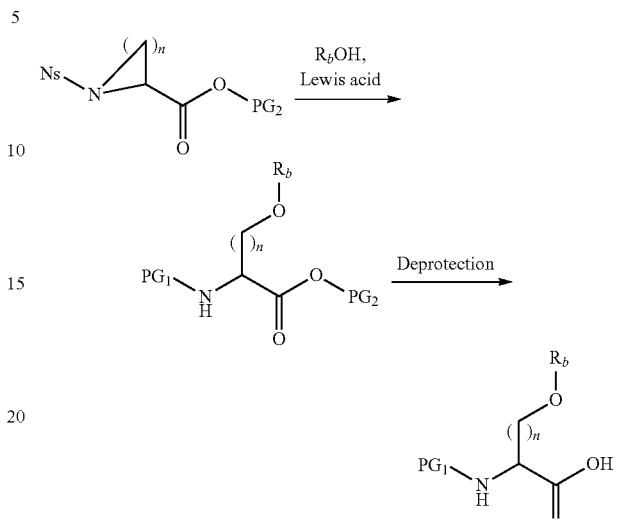

Non-natural amino acids having an optionally substituted alkoxy or aralkoxy (RbO) group on the amino acid side chain can be prepared according to the following scheme. A serine ether compound can be obtained by allowing an alkylating agent (Rb—X) to act on a commercially available serine derivative (n=1 or 2) in the presence of a suitable base according to the method of Williamson et al. (Liebigs Ann. Chem. 1851, 77, 37-49). When Rb has a further convertible functional group, Rb can be converted to a target functional group by additional functional group conversion. Examples of such additional functional group conversion include multiple bond reduction reaction. Next, the target C-terminal-free non-natural amino acid can be prepared by deprotecting the obtained non-natural amino acid.

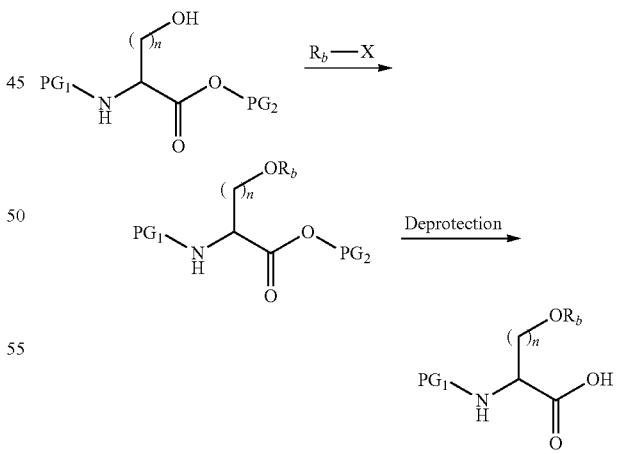

Non-natural amino acids having an optionally substituted alkoxy or aralkoxy (RbO) group on the amino acid side chain and having a-$CH_2$—P' group introduced onto the amino acid nitrogen atom can be prepared according to the following scheme. An oxazolidinone compound having a cyclic protecting group introduced can be obtained by allowing an aldehyde to act on a commercially available serine derivative or a serine derivative prepared by the above-described method (n=1 or 2) according to the method of Freidinger et al. (J. Org. Chem., 1983, 48 (1), 77-81). Next, the target C-terminal-free non-natural amino acid can be prepared by ring-opening reaction.

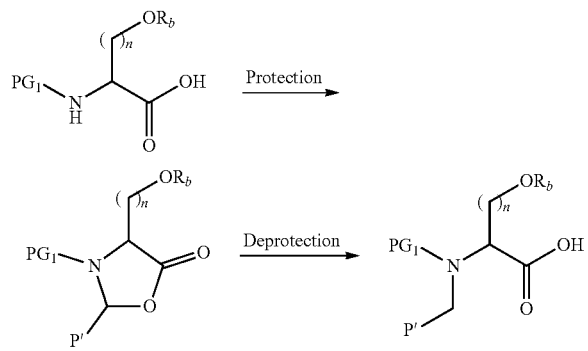

Non-natural amino acids having a protected hydroxy group on the amino acid side chain can be prepared according to the following scheme. The target C-terminal-free non-natural amino acid can be prepared by appropriately introducing/removing a protecting group onto/from a commercially available serine derivative or a serine derivative prepared by the above-described method (n=1 or 2).

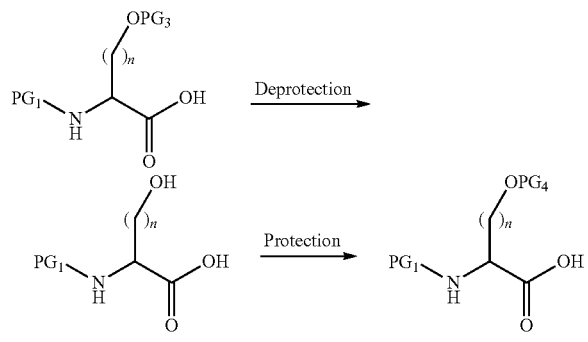

Non-natural amino acids having a protected hydroxy group on the amino acid side chain and a-CH$_2$—P' group introduced onto the amino acid nitrogen atom can be prepared according to the following scheme. An oxazolidinone compound having a cyclic protecting group introduced can be obtained by allowing an aldehyde to act on a commercially available serine derivative or a serine derivative prepared by the above-described method (n=1 or 2) according to the method of Freidinger et al. (J. Org. Chem., 1983, 48 (1), 77-81). Next, the target C-terminal-free non-natural amino acid can be prepared by ring-opening reaction and protecting group introduction reaction.

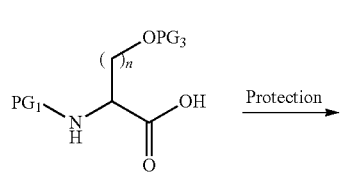

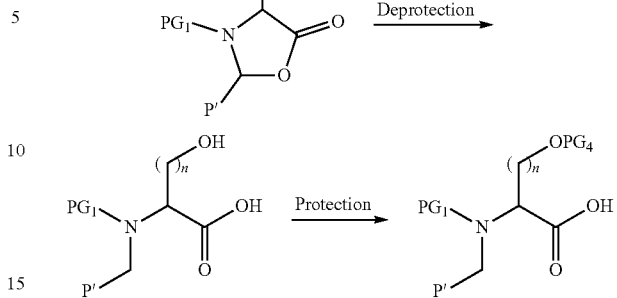

Cyclic non-natural amino acids having a substituent ($R_c$) introduced onto the hydroxyl group of the cyclic amino acid can be prepared according to the following scheme. The hydroxy group of a commercially available cyclic amino acid can be converted to the target —$OR_c$ group by appropriately introducing a functional group. As a reaction of converting the functional group, an ether bond can be produced by allowing an alkylating agent ($R_c$—X) to react in the presence of a suitable base according to the method of Williamson et al. (Liebigs Ann. Chem. 1851, 77, 37-49). When $R_c$ has a further convertible functional group, Re can be converted to a target functional group by additional functional group conversion. Next, the target C-terminal-free non-natural amino acid can be prepared by deprotection reaction.

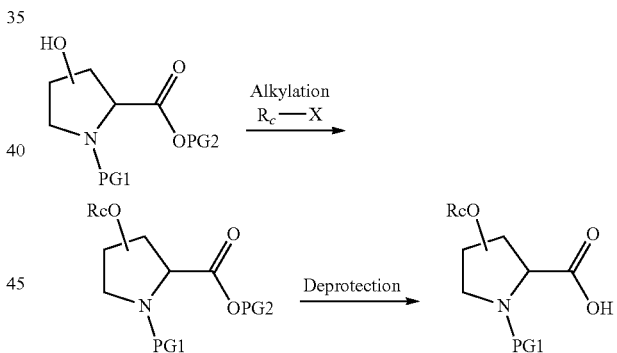

Cyclic non-natural amino acids having a protecting group ($PG_3$) introduced onto the hydroxyl group of the cyclic amino acid can be prepared according to the following scheme. The target C-terminal-free non-natural amino acid can be prepared by appropriately introducing/removing a protecting group onto/from a commercially available cyclic amino acid.

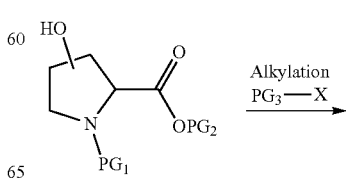

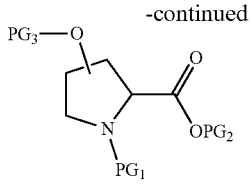

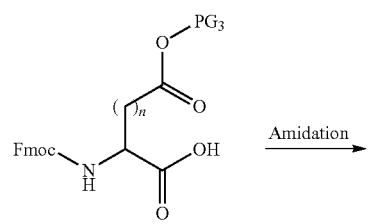

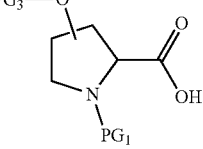

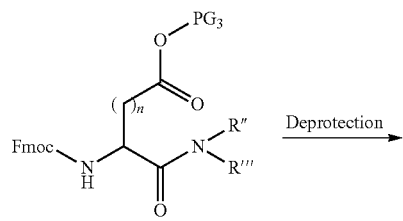

Non-natural amino acids having a boronic acid introduced onto the amino acid side chain can be prepared according to the following scheme. A non-natural amino acid having a boronic acid ester introduced can be obtained by allowing an aldehyde to act on a commercially available glycine derivative according to the method of Lee et al. (Bioorg. Med. Chem. Lett., 2009, 19 (17), 4887-5274). Next, the target C-terminal-free non-natural amino acid can be prepared by appropriately introducing or removing a protecting group.

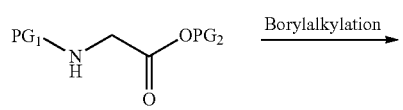

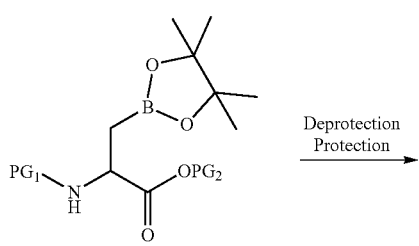

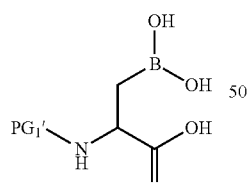

(Synthesis 2 of Fmoc Non-Natural Amino Acids Having a Carboxyl Group on the Side Chain)

Fmoc non-natural amino acids having a carboxyl group on the side chain and a-CH$_2$—P' group introduced onto the amino acid nitrogen atom can be prepared according to the following scheme. The main chain carboxyl group of a starting material which is available from a commercial supplier and has a side chain carboxyl group protected by PG$_3$ (n=1 or 2) can be converted to an amide group by condensing it with an amine (R"R"NH) in the presence of a condensing agent such as DIC. Next, the target Fmoc non-natural amino acid having a carboxyl group on the side chain can be prepared by deprotecting PG$_3$.

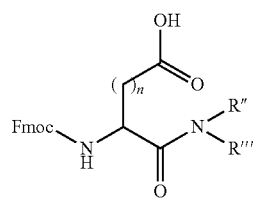

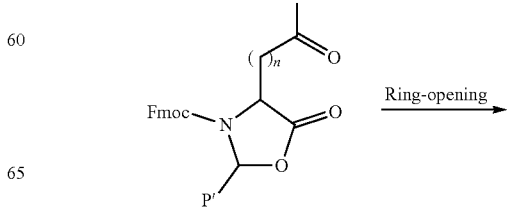

(Synthesis 1 of Fmoc non-natural amino acids having a carboxyl group on the side chain) Fmoc non-natural amino acids having a carboxyl group on the side chain can be prepared according to the following scheme. The main chain carboxyl group of a starting material which is available from a commercial supplier and has a side chain carboxyl group protected by PG$_3$ (n=1 or 2) can be converted to an amide group by condensing it with an amine (R"R"NH) in the presence of a condensing agent such as DIC. Next, the target Fmoc non-natural amino acid having a carboxyl group on the side chain can be prepared by deprotecting PG$_3$.

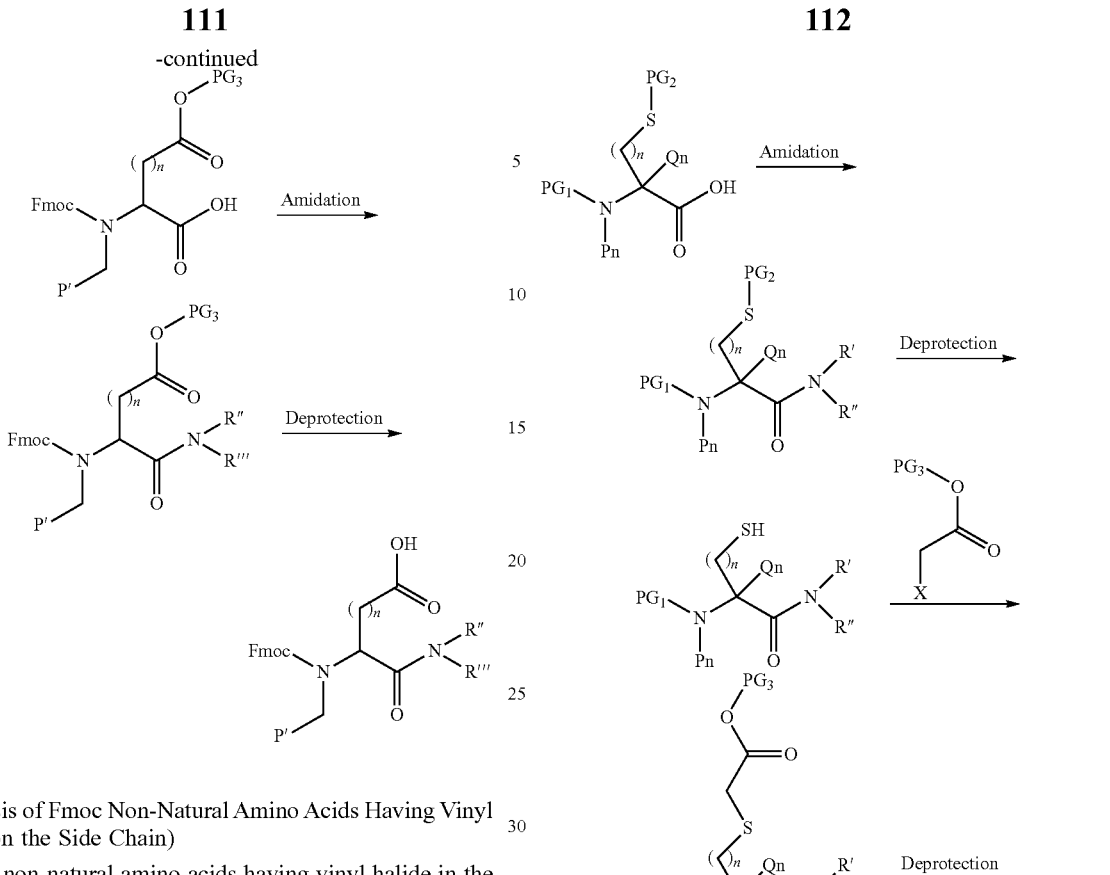

(Synthesis of Fmoc Non-Natural Amino Acids Having Vinyl Halide on the Side Chain)

Fmoc non-natural amino acids having vinyl halide in the side chain can be synthesized by the following scheme according to the method of Shendage et al. (Eur. J. Org. Chem., 2005, 719-727). Boc-2-t-butyl-3-methylimidazolidin-4-one available from a commercial supplier is reacted with an alkylating agent having vinyl halide in the side chain in the presence of a base, and the intended Fmoc non-natural amino acid having vinyl halide in the side chain can be produced by the method described in the literature.

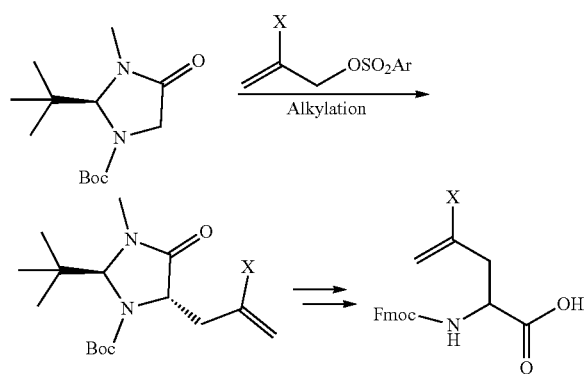

Non-natural amino acids containing a thioether group on the side chain (n=1 or 2) can be produced according to the following scheme. An amino acid having a protected side chain thiol group was subjected to carboxylic acid amidation, and following deprotection of the thiol group, halogenated acetic acid having a protected carboxylic acid was allowed to react to form a thioether bond. Next, the amino acid having a thioether group on the side chain can be produced by deprotecting the side chain carboxylic acid.

Peptides containing a thioether group on the peptide main chain can be produced by using as a raw material the aforementioned amino acid having a thioether group on the side chain, but alternatively, they can also be produced by the method of Roberts et al. in which an N-terminal bromoacetamide is reacted with a cysteine side chain (Tetrahedron Letters, 1998, 39, 8357-8360), or the method of Robey et al. in which an N-terminal chloroacetamide is reacted with a cysteine side chain (Journal of Peptide Research, 2000, 56, 115-120).

The compounds of the present invention and salts thereof, and solvates thereof include all stereoisomers (such as enantiomers and diastereomers (including cis and trans geometric isomers)) of the target compounds obtained through the above-described reaction steps, and racemates and other mixtures of such isomers. For example, the compounds of the present invention may have one or more asymmetric points, and the present invention encompasses racemic mixtures, diastereomeric mixtures, and enantiomers of such compounds.

When the compounds according to the present invention are obtained as free forms, they can be converted to salts that may be formed by such compounds, or hydrates or solvates thereof, according to conventional methods.

When the compounds according to the present invention are obtained as salts, hydrates, or solvates of such compounds, they can be converted to free forms of such compounds according to conventional methods.

<Pharmaceutical Compositions>

The present invention provides pharmaceutical compositions containing a cyclic compound of the present invention.

The pharmaceutical compositions of the present invention can be formulated by introducing a pharmaceutically acceptable carrier, in addition to a compound of the present invention, a salt thereof, or a solvate thereof by conventional methods. Commonly used excipients, binders, lubricants, colorants, correctives, and as necessary, stabilizers, emulsifiers, absorption promoters, surfactants, pH adjusters, preservatives, antioxidants, and the like can be used for formulation, and they are blended with ingredients generally used as raw materials of pharmaceutical formulations, and formulated by conventional methods.

For example, oral formulations are prepared by adding the compound of the present invention or a salt thereof, and an excipient, and as necessary, a binder, a disintegrant, a lubricant, a colorant, a corrective, and the like, and then formulating them into powder, fine granules, granules, tablets, coated tablets, capsules, and the like by a conventional method.

Examples of these ingredients include animal and vegetable oils such as soybean oil, beef tallow, and synthetic glyceride: hydrocarbons such as liquid paraffin, squalane, and solid paraffin; ester oils such as octyldodecyl myristate and isopropyl myristate: higher alcohols such as cetostearyl alcohol and behenyl alcohol; silicone resin; silicone oil; surfactants such as polyoxyethylene fatty acid ester, sorbitan fatty acid ester, glycerol fatty acid ester, polyoxyethylene sorbitan fatty acid ester, polyoxyethylene hydrogenated castor oil, and polyoxyethylene-polyoxypropylene block copolymer; water-soluble polymers such as hydroxyethylcellulose, polyacrylic acid, carboxyvinyl polymer, polyethylene glycol, polyvinylpyrrolidone, and methylcellulose; lower alcohols such as ethanol and isopropanol; polyhydric alcohols such as glycerol, propylene glycol, dipropylene glycol, and sorbitol; sugars such as glucose and sucrose; inorganic powders such as silicic anhydride, magnesium aluminum silicate, and aluminum silicate; and purified water.

Examples of the excipients include lactose, corn starch, white soft sugar, glucose, mannitol, sorbitol, microcrystalline cellulose, and silicon dioxide.

Examples of the binders include polyvinyl alcohol, polyvinyl ether, methylcellulose, ethylcellulose, acacia, tragacanth, gelatin, shellac, hydroxypropylmethylcellulose, hydroxypropylcellulose, polyvinylpyrrolidone, polypropylene glycol-polyoxyethylene block polymer, and meglumine.

Examples of the disintegrants include starch, agar, gelatin powder, microcrystalline cellulose, calcium carbonate, sodium bicarbonate, calcium citrate, dextrin, pectin, and carboxymethylcellulose calcium.

Examples of the lubricants include magnesium stearate, talc, polyethylene glycol, silica, and hydrogenated vegetable oil.

For colorants, those approved as additives to pharmaceuticals are used. For correctives, cocoa powder, peppermint camphor, empasm, mentha oil, borneol, powdered cinnamon bark, and the like are used.

Obviously, these tablets and granules may be sugar-coated or otherwise coated appropriately as necessary. When liquid formulations such as syrups and injectable formulations are prepared, they are formulated by adding pH adjusters, solubilizers, tonicity adjusting agents, and the like, and as necessary, solubilizing agents, stabilizers, and the like to the compounds according to the present invention or pharmacologically acceptable salts thereof using conventional methods.

For example, the pharmaceutical compositions can be parenterally used in the form of injectable sterile solutions or suspensions with water or other pharmaceutically acceptable liquids. For example, they would be formulated by appropriately combining with pharmacologically acceptable carriers or media, specifically, sterile water, saline, vegetable oils, emulsifiers, suspending agents, surfactants, stabilizers, flavoring agents, excipients, vehicles, preservatives, or binders, and blending in unit dosage forms required in generally approved formulation. Specifically, carriers may include light anhydrous silicic acid, lactose, microcrystalline cellulose, mannitol, starch, carmellose calcium, carmellose sodium, hydroxypropylcellulose, hydroxypropylmethylcellulose, polyvinyl acetal diethylaminoacetate, polyvinylpyrrolidone, gelatin, medium chain fatty acid triglyceride, polyoxyethylene hydrogenated castor oil 60, white soft sugar, carboxymethylcellulose, corn starch, and inorganic salts. The amount of the active ingredient in such a formulation is designed to provide a suitable dose within an indicated range.

Sterile compositions for injection can be formulated in a conventional formulation manner using a vehicle such as distilled water for injection.

Aqueous solutions for injection include, for example, isotonic solutions containing saline, glucose, and other adjuvants, such as D-sorbitol, D-mannose, D-mannitol, and sodium chloride, and may be used in combination with appropriate solubilizers, for example, alcohols, specifically, ethanol, polyalcohols, e.g., propylene glycol or polyethylene glycol, and nonionic surfactants, e.g., polysorbate 80 (registered trademark) or HCO-50.

Oily liquids include sesame oil and soybean oil, and may be used in combination with benzyl benzoate and benzyl alcohol as solubilizers. They may also be blended with buffering agents such as phosphate buffer and sodium acetate buffer; analgesics such as procaine hydrochloride; stabilizers such as benzyl alcohol and phenol; and antioxidants. Prepared injections are usually packed in suitable ampoules.

The administration method is preferably oral administration, but is not limited thereto. Specific examples of parenteral administration include dosage forms of injection, nasal administration, pulmonary administration, and transdermal administration. Examples of injection dosage forms include systemic or local administration by intravenous injection, intramuscular injection, intraperitoneal injection, subcutaneous injection, etc.

The administration method can also be selected according to the age and symptom of the patient. The dosage of the pharmaceutical composition containing the peptide compound prepared by the method of the present invention can be selected, for example, in the range of 0.0001 mg to 1000 mg per kg body weight per dose. Alternatively, the dosage can be selected, for example, in the range of 0.001 to 100000 mg/body per patient; however, it is not necessarily limited to such values. The dosage and the administration method vary according to the body weight, the age, the symptom, and the like of the patient, but can be appropriately selected by those skilled in the art.

In an embodiment, a cyclic compound of the present invention or a salt thereof, or a solvate thereof; or a pharmaceutical composition containing a cyclic compound of the present invention or a salt thereof, or a solvate thereof can bind or selectively bind to KRAS in a subject and can be used for selectively inhibiting KRAS.

In an embodiment, a cyclic compound of the present invention or a salt thereof, or a solvate thereof can bind or selectively bind to KRAS in a subject, and can be used for producing a medical drug for selectively inhibiting KRAS.

In an embodiment, the present invention relates to a method for binding or selectively binding a cyclic compound of the present invention or a salt thereof, or a solvate thereof to KRAS in a subject, or a method for selectively inhibiting KRAS in a subject, including a step of administering an effective amount of a cyclic compound of the present invention or a salt thereof, or a solvate thereof to a subject who needs it.

A cyclic compound of the present invention or a salt thereof, or a solvate thereof as mentioned above has high selectivity to KRAS in a subject. For example, a cyclic compound of the present invention has selectivity to KRAS (KRAS selectivity to NRAS and/or KRAS selectivity to HRAS) higher than PP1820: ((3S,9S,12S,17S,20S,23S,27S, 30S,36S)-3-[2-[3-chloro-4-(trifluoromethyl)phenyl]ethyl] 30)-cyclopentyl-23-isobutyl-9-(isopentyloxymethyl)-N,N, 7,17,18,24,28,31-octamethyl-20-[(1S)-1-methylpropyl]-2,5, 8,11,16,19,22,25,29,32,35-undecaoxo-10-propyl-spiro[1,4, 7,10,15,18,21,24,28,31,34-undecazatricyclo[34.3.0.012, 15] nonatriacontane-33,1'-cyclobutane]-27-carboxamide). In an embodiment, the pharmaceutical composition of the present invention has KRAS inhibitory activity that is 3 times or more higher than NRAS inhibitory activity and HRAS inhibitory activity.

In an embodiment, the pharmaceutical composition of the present invention has KRAS inhibitory activity that is 5 times, 7 times, 10 times, 15 times, or 20 times or more higher than NRAS inhibitory activity and HRAS inhibitory activity.

In an embodiment, the cyclic compound of the present invention, or a salt thereof, or a solvate thereof, or a pharmaceutical composition containing the cyclic compound of the present invention, or a salt thereof, or a solvate thereof, can be used to treat and/or prevent cancer in a subject.

In an embodiment, the cyclic compound of the present invention, or a salt thereof, or a solvate thereof, can be used in the manufacture of a medicament for treating and/or preventing cancer in a subject.

In an embodiment, the present invention relates to a method for treating and/or preventing cancer in a subject, comprising the step of administering an effective amount of the cyclic compound of the present invention, or a salt thereof, or a solvate thereof, to a subject in need thereof.

Specific examples of the cancer include lung cancer.

The term "subject" herein includes mammals, and mammals are preferably humans. All prior art documents cited in the present specification are incorporated herein by reference.

EXAMPLE

The scope of the present invention will now be further described by way of Examples and Reference Examples below, but the present invention is not limited thereto. When production methods are not described, starting materials and reagents were obtained from commercial suppliers or synthesized using known methods. The analytical conditions of LC/MS are provided in Table 1.

TABLE 1

| Analytical conditions | Apparatus | Column (I.D. × length)(mm) | Mobile phase |
|---|---|---|---|
| SQDFA05 | Acquity UPLC/SQD | Ascentis Express C18 (2.1 × 50) | A) 0.1% FA, $H_2O$ <br> B) 0.1% FA, MeCN |
| SQDFA50 | Acquity UPLC/SQD | Ascentis Express C18 (2.1 × 50) | A) 0.1% FA, $H_2O$ <br> B) 0.1% FA, MeCN |
| SQDFA50_2 | Acquity UPLC/SQD | Ascentis Express C18 (2.1 × 50) | A) 0.1% FA, $H_2O$ <br> B) 0.1% FA, MeCN |
| SQDFA40 | Acquity UPLC/SQD | Ascentis Express C18 (2.1 × 50) | A) 0.1% FA, $H_2O$ <br> B) 0.1% FA, MeCN |
| SQDFA05long | Acquity UPLC/SQD | Ascentis Express C18 (2.1 × 50) | A) 0.1% FA, $H_2O$ <br> B) 0.1% FA, MeCN |
| SQDFA50long | Acquity UPLC/SQD | Ascentis Express C18 (2.1 × 50) | A) 0.1% FA, $H_2O$ <br> B) 0.1% FA, MeCN |
| SQDAA05 | Acquity UPLC/SQD | Ascentis Express C18 (2.1 × 50) | A) 10 mM $AcONH_4$, $H_2O$ <br> B) MeOH |
| SQDAA50 | Acquity UPLC/SQD | Ascentis Express C18 (2.1 × 50) | A) 10 mM $AcONH_4$, $H_2O$ <br> B) MeOH |
| SQDAA50_2 | Acquity UPLC/SQD | Ascentis Express C18 (2.1 × 50) | A) 10 mM $AcONH_4$, $H_2O$ <br> B) MeOH |
| SMD method_02 | Shimazu LCMS-2020 | Shim-Pack XR-ODS (3.0 × 50) | A) 0.05% TFA, $H_2O$ <br> B) 0.05% TFA, MeCN |
| SMD method_03 | Nexera/2020 | Ascentis Express C18 (2.1 × 50) | A) 0.1% FA, $H_2O$ <br> B) 0.1% FA, MeCN |
| SMD method_04 | Nexera/2020 | Ascentis Express C18 (2.1 × 50) | A) 0.1% FA, $H_2O$ <br> B) 0.1% FA, MeCN |
| SMD method_05 | Nexera/2020 | Ascentis Express RP-Amide (2.1 × 50) | A) 0.1% FA, $H_2O$ <br> B) 0.1% FA, MeCN |
| SMD method_06 | Nexera/2020 | Ascentis Express C18 (2.1 × 50) | A) 0.1% FA, $H_2O$ <br> B) 0.1% FA, MeCN |
| SMD method_07 | Nexera/2020 | Ascentis Express RP-Amide (2.1 × 50) | A) 0.1% FA, $H_2O$ <br> B) 0.1% FA, MeCN |

TABLE 1-continued

| | | | |
|---|---|---|---|
| SMD method_08 | Nexera/2020 | Accucore C18 (2.1 × 50) | A) 10 mM NH4HCO3 in H2O<br>B) MeCN |
| SMD method_10 | Nexera/2020 | Kinetex EVO C18 (2.1 × 50) | A) 10 mM NH4HCO3 in H2O<br>B) MeCN |
| SMD method_11 | Shimazu LCMS-2020 | Shim-Pack XR-ODS-C18 (3.0 × 50) | A) 0.05% TFA, $H_2O$<br>B) 0.05% TFA, MeCN |
| SMD method_12 | Shimazu LCMS-2020 | Shim-Pack XR-ODS (3.0 × 50) | A) 0.05% TFA, $H_2O$<br>B) 0.05% TFA, MeCN |
| SMD method_13 | Shimazu LCMS-2020 | Shim-Pack XR-ODS (3.0 × 50) | A) 0.05% TFA, $H_2O$<br>B) 0.05% TFA, MeCN |
| SMD method_14 | Shimazu LCMS-2020 | Shim-Pack XR-ODS (3.0 × 50) | A) 0.05% TFA, $H_2O$<br>B) 0.05% TFA, MeCN |
| SMD method_15 | Shimazu LCMS-2020 | Shim-Pack XR-ODS-C18 (3.0 × 50) | A) 0.05% TFA, $H_2O$<br>B) 0.05% TFA, MeCN |
| SMD method_16 | Shimazu LCMS-2020 | Shim-Pack XR-ODS-C18 (3.0 × 50) | A) 0.05% TFA, $H_2O$<br>B) 0.05% TFA, MeCN |
| SMD method_17 | Shimadzu LCMS-2020 LC-20ADXR | kinetex XB-C18(3.0 × 50) | A) 0.1% FA, H2O<br>B) 0.1% FA, MeCN |
| SMD method_18 | Shimadzu LCMS-2020 LC-20AD | Shim-Pack XR-ODS (3.0 × 50) | A) 0.05% TFA, H2O<br>B) 0.05% TFA, MeCN |
| SMD method_19 | Shimadzu LCMS-2020 | ACQUITY BEH C18 (2.1 × 50) | A) 0.15% FA, $H_2O$<br>B) 0.15% FA, MeCN |
| SMD method_20 | Shimazu LCMS-2020 | Halo C18 (3.0 × 30) | A) 0.05% TFA, $H_2O$<br>B) 0.05% TFA, MeCN |
| SMD method_21 | Shimadzu LCMS-2020 LC-20AD | Ascentis Express C18 (4.6 × 100) | A) 0.1% FA, H2O<br>B) 0.1% FA, MeCN |
| SSC-AA-02/03 | Nexera UC/2020 | Ascentis Express C18 (2.1 × 50) | A) 10 mM $AcONH_4$, $H_2O$<br>B) MeOH |
| SSC-FA-02/03 | Nexera UC/2020 | Ascentis Express C18 (2.1 × 50) | A) 0.1% FA, H2O<br>B) 0.1% FA, MeCN |
| SMD method_22 | Shimazu LCMS-2020 | Halo C18 (3.0 × 30) | A) 0.05% TFA, $H_2O$<br>B) 0.05% TFA, MeCN |
| SMD method_23 | Shimazu LCMS-2020 | Halo C18 (3.0 × 30) | A) 0.05% TFA, $H_2O$<br>B) 0.05% TFA, MeCN |
| SMD method_24 | Shimazu LCMS-2020 | Halo C18 (3.0 × 30) | A) 0.05% TFA $H_2O$<br>B) 0.05% TFA, MeCN |
| SMD method_25 | Shimazu LCMS-2020 | Halo C18 (3.0 × 30) | A) 0.05% TFA, $H_2O$<br>B) 0.05% TFA, MeCN |
| SMD method_26 | Shimazu LCMS-2020 | Halo C18 (3.0 × 30) | A) 0.1% FA, $H_2O$<br>B) 0.1% FA, MeCN |
| SMD method_27 | Shimazu LCMS-2020 | Halo C18 (3.0 × 30) | A) 0.05% TFA, $H_2O$<br>B) 0.05% TFA, MeCN |
| SMD method_28 | Shimazu LCMS-2020 | Halo C18 (3.0 × 30) | A) 0.1% FA, $H_2O$<br>B) 0.1% FA, MeCN |
| SMD method_29 | Shimazu LCMS-2020 | Halo C18 (3.0 × 30) | A) 0.05% TFA, $H_2O$<br>B) 0.05% TFA, MeCN |
| SMD method_30 | Shimazu LCMS-2020 | Halo C18 (3.0 × 30) | A) 0.05% TFA, $H_2O$<br>B) 0.05% TFA, MeCN |
| SMD method_31 | Shimazu LCMS-2020 | Halo C18 (3.0 × 30) | A) 0.05% TFA, $H_2O$<br>B) 0.05% TFA, MeCN |
| SMD method_32 | Shimazu LCMS-2020 | Halo C18 (3.0 × 30) | A) 0.05% TFA, $H_2O$<br>B) 0.05% TFA, MeCN |
| SMD method_33 | Shimazu LCMS-2020 | Halo C18 (3.0 × 30) | A) 0 05% TFA, $H_2O$<br>B) 0.05% TFA, MeCN |
| SMD method_34 | Shimazu LCMS-2020 | Halo C18 (3 0 × 30) | A) 0.05% TFA, $H_2O$<br>B) 0.05% TFA, MeCN |
| SMD method_35 | Shimazu LCMS-2020 | Halo C18 (3 0 × 30) | A) 0.1% FA, $H_2O$<br>B) 0.1% FA, MeCN |
| SMD method_36 | Shimazu LCMS-2020 | Halo C18 (3 0 × 30) | A) 0.1% FA, $H_2O$<br>B) 0.1% FA, MeCN |
| SMD method_37 | Shimazu LCMS-2020 | Halo C18 (3.0 × 30) | A) 0.1% FA, $H_2O$<br>B) 0.1% FA, MeCN |
| SMD method_38 | Shimazu LCMS-2020 | Halo C18 (3.0 × 30) | A) 0.1% FA, $H_2O$<br>B) 0.1% FA, MeCN |
| SMD method_39 | Shimazu LCMS-2020 | Halo C18 (3 0 × 30) | A) 0.1% FA, $H_2O$<br>B) 0.1% FA, MeCN |
| SMD method_40 | Shimazu LCMS-2020 | Halo C18 (3.0 × 30) | A) 0.1% FA, $H_2O$<br>B) 0.1% FA, MeCN |
| SMD method_41 | Shimazu LCMS-2020 | Halo C18 (3 0 × 30) | A) 0.05% TFA, $H_2O$<br>B) 0.05% TFA, MeCN |

TABLE 1-continued

| Analytical conditions | Gradient (A/B) | Flow rate (mL/Min) | Column temperature (° C.) | Wave length |
|---|---|---|---|---|
| SQDFA05 | 95/5 => 0/100(1.0 Min) => 0/100(0.4 Min) | 1.0 | 35 | 210-400 nm PDA total |
| SQDFA50 | 50/50 => 0/100(0.7 Min) => 0/100(0.7 Min) | 1.0 | 35 | 210-400 nm PDA total |
| SQDFA50_2 | 50/50 => 0/100(1 Min) => 0/100(0.4 Min) | 1.0 | 35 | 210-400 nm PDA total |
| SQDFA40 | 60/40 => 0/100(1 Min) => 0/100(0.4 Min) | 1.0 | 35 | 210-400 nm PDA total |
| SQDFA05long | 95/5 => 0/100(4.5 Min) => 0/100(0.5 Min) | 1.0 | 35 | 210-400 nm PDA total |
| SQDFA50long | 50/50 => 0/100(4.5 Min) => 0/100(0.5 Min) | 1.0 | 35 | 210-400 nm PDA total |
| SQDAA05 | 95/5= > 0/100(1.0 Min) => 0/100(0.4 Min) | 1.0 | 35 | 210-400 nm PDA total |
| SQDAA50 | 50/50 => 0/100(0.7 Min) => 0/100(0.7 Min) | 1.0 | 35 | 210-400 nm PDA total |
| SQDAA50_2 | 50/50 => 0/100(0.7 Min) => 0/100(0.7 Min) | 0.9 | 35 | 210-400 nm PDA total |
| SMD method_02 | 60/40 => 5/95(3 Min) => 5/95(0.7 Min) | 1.2 | 40 | 190-400 PDA total |
| SMD method_03 | 95/5 => 0/100(4.5 Min) => 0/100(0.5 Min) | 1.0 | 35 | 210-400 nm PDA total |
| SMD method_04 | 95/5 => 0/100(1.5 Min) => 0/100(0.5 Min) | 1.0 | 35 | 210-400 nm PDA total |
| SMD method_05 | 95/5 =>0/100(1.5 Min) => 0/100(0.5 Min) | 1.0 | 35 | 210-400 nm PDA total |
| SMD method_06 | 50/50 =>0/100(1 Min) => 0/100(1 Min) | 1.0 | 35 | 210-400 nm PDA total |
| SMD method_07 | 50/50 =>0/100(1 Min) => 0/100(1 Min) | 1.0 | 35 | 210-400 nm PDA total |
| SMD method_08 | 95/5 =>5/95(1.5 Min) => 5/95(0.5 Min) | 1.0 | 35 | 210-400 nm PDA total |
| SMD method_10 | 95/5 =>5/95(1.5 Min) => 5/95(0.5 Min) | 1.0 | 35 | 210-400 nm PDA total |
| SMD method_11 | 95/5 => 5/95(2 Min) => 5/95(0.7 Min) | 1.2 | 40 | 190-400 nm PDA total |
| SMD method_12 | 95/5 => 0/100(1.2 Min) => 0/100(1 Min) | 1.0 | 40 | 190-800 nm PDA total |
| SMD method_13 | 95/5 => 0/100(2.2 Min) => 0/100(1 Min) | 1.0 | 40 | 190-800 nm PDA total |
| SMD method_14 | 95/5 => 0/100(1.1 Min) => 0/100(0.6 Min) | 1.2 | 40 | 190-400 nm PDA total |
| SMD method_15 | 70/30 => 5/95(3.8 Min) => 5/95(0.8 Min) | 1.2 | 40 | 190-400 nm PDA total |
| SMD method_16 | 95/5 => 5/95(3.0 Min) => 5/95(0.7 Min) | 1.2 | 40 | 190-400 nm PDA total |
| SMD method_17 | 90/10 => 0/100(1.2 Min) => 0/100(0.5 Min) => 90/10(0.1 Min) | 1.5 | 40 | 190-400 nm PDA total |
| SMD method_18 | 95/5 => 0/100(2.2 Min) => 0/100(1.0 Min) 95/5(0.1 Min) | 1.0 | 40 | 190-400 nm PDA total |
| SMD method_19 | 90/10 => 30/70(3.6 Min) => 30/70(1.0 Min) | 0.7 | 45 | 190-600 nm PDA total |
| SMD method_20 | 95/5 => 5/95(1.2 Min) => 5/95(0.6) => 95/5(0.02 Min) | 1.5 | 40 | 190-400 nm PDA total |
| SMD method_21 | 95/5 => 70/30(15.0 Min) => 70/30(3.0 Min) 5/95(2.0 Min) | 1.0 | 40 | 190-400 nm PDA total |
| SSC-AA-02/03 | 70/30 => 0/100(8.75 Min) => 0/100(1.25 Min) | 0.5 | 50 | 210-400 nm PDA total |
| SSC-FA-02/03 | 70/30 => 10/90(7.5 Min) => 0/100(0.01 Min) => 0/100(2.49 Min) | 0.5 | 50 | 210-400 nm PDA total |
| SMD method_22 | 95/5 => 5/95(0.7 Min) => 5/95(0.4 Min) | 1.5 | 40 | 190-400 nm PDA total |
| SMD method_23 | 60/40 => 0/100(2.0 Min) => 0/100(0.7 Min) | 1.2 | 40 | 190-400 nm PDA total |
| SMD method_24 | 95/5 => 0/100(1.1 Min) => 0/100(0.6 Min) | 1.5 | 40 | 190-400 nm PDA total |
| SMD method_25 | 95/5 => 0/100(1.1 Min) => 0/100(0.6 Min) | 1.2 | 40 | 190-400 nm PDA total |
| SMD method_26 | 95/5 => 5/95(1.1 Min) => 5/95(0.6 Min) | 1.5 | 40 | 190-400 nm PDA total |

TABLE 1-continued

| | | | | |
|---|---|---|---|---|
| SMD method_27 | 50/50 => 0/100(2.0 Min) => 0/100(0.7 Min) | 1.2 | 40 | 190-400 nm PDA total |
| SMD method_28 | 95/5 => 5/95(0.7 Min) => 5/95(0.4 Min) | 1.2 | 40 | 190-400 nm PDA total |
| SMD method_29 | 95/5 => 5/95(1.1 Min) => 5/95(0.6 Min) | 1.3 | 40 | 190-400 nm PDA total |
| SMD method_30 | 95/5 => 0/100(0.7 Min) => 0/100(0.4 Min) | 1.5 | 40 | 190-400 nm PDA total |
| SMD method_31 | 95/5 => 5/95(0.7 Min) => 5/95(0.4 Min) | 1.2 | 40 | 190-400 nm PDA total |
| SMD method_32 | 70/30 => 30/70(1.7 Min) => 0/100(0.6 Min) => 0/100(0.5 Min) | 1.2 | 40 | 190-400 nm PDA total |
| SMD method_33 | 95/5 => 0/100(0.7 Min) => 0/100(0.4 Min) | 1.3 | 40 | 190-400 nm PDA total |
| SMD method_34 | 60/40 => 0/100(2.0 Min) => 0/100(0.7 Min) | 1.3 | 40 | 190-400 nm PDA total |
| SMD method_35 | 95/5 => 0/100(0.7 Min) => 0/100(0.4 Min) | 1.0 | 40 | 190-400 nm PDA total |
| SMD method_36 | 95/5 => 5/95(0.7 Min) => 5/95(0.4 Min) | 1.0 | 40 | 190-400 nm PDA total |
| SMD method_37 | 60/40 => 5/95(2.3 Min) => 5/95(0.5 Min) | 1.2 | 40 | 190-400 nm PDA total |
| SMD method_38 | 95/5 => 5/95(1.1 Min) => 5/95(0.6 Min) | 1.2 | 40 | 190-400 nm PDA total |
| SMD method_39 | 95/5 => 5/95(0.7 Min) => 5/95(0.4 Min) | 1.5 | 40 | 190-400 nm PDA total |
| SMD method_40 | 95/5 => 0/100(0.7 Min) => 0/100(0.4 Min) | 1.2 | 40 | 190-400 nm PDA total |
| SMD method_41 | 95/5 => 5/95(1.1 Min) => 5/95(0.6 Min) | 1.5 | 40 | 190-400 nm PDA total |

Example 1 Solid-Phase Synthesis of Peptide Compound

Peptide elongation was performed through the following basic route (also called the basic peptide synthesis method) according to the peptide synthesis method by the Fmoc method described in WO2013/100132 or WO2018/225864. That is to say, it included the five steps of:

1) a peptide elongation reaction by the Fmoc method from the N-terminal of an amino acid in which the Asp side-chain carboxylic acid or the peptide main-chain carboxylic acid was supported on 2-chlorotrityl resin,
2) a process of cleaving a peptide from 2-chlorotrityl resin,
3) amide cyclization by condensation between the Asp side-chain carboxylic acid or the peptide main-chain carboxylic acid resulting from removal from 2-chlorotrityl resin by the cleaving process and the amino group at the peptide chain N-terminal (a triangular unit),
4) optional deprotection of the protecting group of a side-chain functional group contained in the peptide chain, and
5) purification of a compound by preparative HPLC. In the present Examples, peptide compounds were synthesized through this basic route unless specified otherwise.

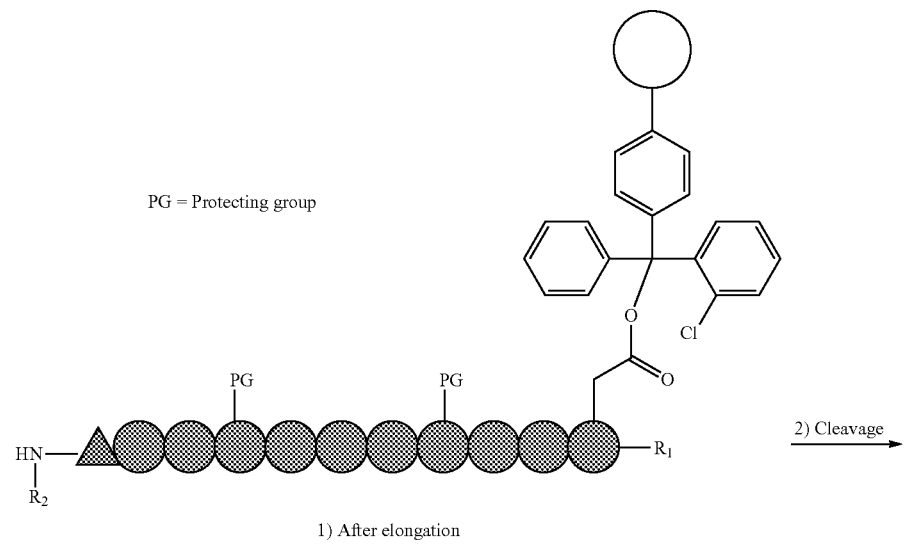

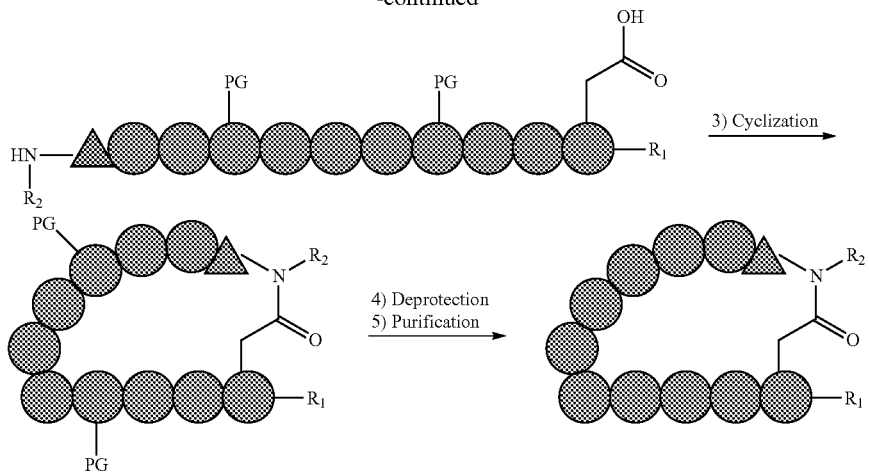

1-1. Fmoc-Amino Acid Used in Peptide Synthesis by Peptide Synthesizer

In the peptide synthesis described herein, the Fmoc-amino acids listed in Table 2 to Table 4 were used in synthesis by a peptide synthesizer.

The Fmoc-amino acids listed in Table 2 were synthesized according to the method described in WO2018/225851 or WO2018/225864.

The Fmoc-amino acids listed in Table 3 were purchased from commercial suppliers.

The Fmoc-amino acids listed in Table 4 were synthesized according to the scheme shown below.

TABLE 2

| Compound No. | Abbreviation | Structural Formula | Name |
|---|---|---|---|
| aa044 | Fmoc-MeSer(THP)-OH | | (2S)-2-[9H-fluoren-9-ylmethoxycarbonyl(methyl)amino]-3-tetrahydropyran-2-yloxy-propanoic acid |
| aa073 | Fmoc-Ser(THP)-OH | | (2S)-2-(9H-fluoren-9-ylmethoxycarbonylamino)-3-tetrahydropyran-2-yloxy-propanoic acid |
| aa270 | Fmoc-cisPro(4-pip-4-F2)-OH | | (2S,4S)-4-(4,4-difluoro-1-piperidyl)-1-(9H-fluoren-9-ylmethoxycarbonyl)pyrrolidine-2-carboxylic acid |

TABLE 2-continued

| Compound No. | Abbreviation | Structural Formula | Name |
|---|---|---|---|
| aa271 | Fmoc-Pro(4-pip-4-F2)-OH | | (2S,4R)-4-(4,4-difluoro-1-piperidyl)-1-(9H-fluoren-9-ylmethoxycarbonyl)pyrrolidine-2-carboxylic acid |

TABLE 3

| Compound No. | Abbreviation | Structural Formula | Name | CAS No. |
|---|---|---|---|---|
| aa001 | Fmoc-MeAla(cPr)-OH | | (2S)-3-cyclopropyl-2-[9H-fluoren-9-ylmethoxycarbonyl(methyl)amino]propanoic acid | 2304413-31-6 |
| aa002 | Fmoc-MeAbu-OH | | (2S)-2-[9H-fluoren-9-ylmethoxycarbonyl(methyl)amino]butanoic acid | 1310575-53-1 |
| aa003 | Fmoc-MeHnl-OH | | (2S)-2-[9H-fluoren-9-ylmethoxycarbonyl(methyl)amino]heptanoic acid | |
| aa007 | Fmoc-MeLeu-OH | | (2S)-2-[9H-fluoren-9-ylmethoxycarbonyl(methyl)amino]-4-methyl-pentanoic acid | 103478-62-2 |
| aa008 | Fmoc-MeAla(tBu)-OH | | (2S)-2-[9H-fluoren-9-ylmethoxycarbonyl(methyl)amino]-4,4-dimethyl-pentanoic acid | 1357308-53-2 |
| aa009 | Fmoc-MeAla-OH | | (2S)-2-[9H-fluoren-9-ylmethoxycarbonyl(methyl)amino]propanoic acid | 84000-07-7 |
| aa011 | Fmoc-MeAlgly-OH | | (2S)-2-[9H-fluoren-9-ylmethoxycarbony(methyl)amino]pent-4-enoic acid | 2606012-88-6 |

TABLE 3-continued

| Compound No. | Abbreviation | Structural Formula | Name | CAS No. |
|---|---|---|---|---|
| aa012 | Fmoc-MeNva-OH | | (2S)-2-[9H-fluoren-9-ylmethoxycarbonyl(methyl)amino] pentanoic acid | 252049-05-1 |
| aa014 | Fmoc-MeSer(Me)-OH | | (2S)-2-[9H-fluoren-9-ylmethoxycarbonyl(methyl)amino]-3-methoxy-propanoic acid | 1569103-64-5 |
| aa015 | Fmoc-MeCha-OH | | (2S)-3-cyclohexyl-2-[9H-fluoren-9-ylmethoxycarbonyl(methyl)amino] propanoic acid | 148983-03-3 |
| aa016 | Fmoc-MeSer(nPr)-OH | | (2S)-2-[9H-fluoren-9-ylmethoxycarbonyl(methyl)amino]-3-propoxy-propanoic acid | 2255321-10-7 |
| aa017 | Fmoc-MeNle-OH | | (2S)-2-[9H-fluoren-9-ylmethoxycarbonyl(methyl)amino] hexanoic acid | 112883-42-8 |
| aa024 | Fmoc-MeAla(2-Thie)-OH | | (2S)-2-[9H-fluoren-9-ylmethoxycarbonyl(methyl)amino]-3-(2-thienyl)propanoic acid | 1332600-71-1 |
| aa025 | Fmoc-MeAla(3-Pyr)-OH | | (2S)-2-[9H-fluoren-9-ylmethoxycarbonyl(methyl)amino]-3-(3-pyridyl)propanoic acid | 1979173-93-7 |
| aa026 | Fmoc-MePhe-OH | | (2S)-2-[9H-fluoren-9-ylmethoxycarbonyl(methyl)amino]-3-phenyl-propanoic acid | 77128-73-5 |
| aa027 | Fmoc-MeHse(Me)-OH | | (2S)-2-[9H-fluoren-9-ylmethoxycarbonyl(methyl)amino]-4-methoxy-butanoic acid | 1979169-11-3 |

TABLE 3-continued

| Compound No. | Abbreviation | Structural Formula | Name | CAS No. |
|---|---|---|---|---|
| aa032 | Fmoc-MePhe(3-Cl)-OH | | (2S)-3-(3-chlorophenyl)-2-[9H-fluoren-9-ylmethoxycarbonyl(methyl)amino]propanoic acid | 1446478-28-9 |
| aa033 | Fmoc-MePhe(3-F)-OH | | (2S)-2-[9H-fluoren-9-ylmethoxycarbonyl(methyl)amino]-3-(3-fluorophenyl)propanoic acid | 1820567-10-9 |
| aa034 | Fmoc-MeAbu(4-F3)-OH | | (2S)-2-[9H-fluoren-9-ylmethoxycarbonyl(methyl)amino]-4,4,4-trifluoro-butanoic acid | |
| aa035 | Fmoc-MeGln(Me2)-OH | | (2S)-5-(dimethylamino)-2-[9H-fluoren-9-ylmethoxycarbonyl(methyl)amino]-5-oxo-pentanoic acid | 2255321-26-5 |
| aa037 | Fmoc-MeVal-OH | | (2S)-2-[9H-fluoren-9-ylmethoxycarbonyl(methyl)amino]-3-methyl-butanoic acid | 84000-11-3 |
| aa038 | Fmoc-EtLeu-OH | | (2S)-2-[ethyl(9H-fluoren-9-ylmethoxycarbonyl)amino]-4-methyl-pentanoic acid | |
| aa039 | Fmoc-MeAocte(2)-OH | | (2S)-2-[9H-fluoren-9-ylmethoxycarbonyl(methyl)amino]oct-7-enoic acid | 1808268-11-2 |
| aa040 | Fmoc-MeAhpe(2)-OH | | (2S)-2-[9H-fluoren-9-ylmethoxycarbonyl(methyl)amino]hept-6-enoic acid | 856412-24-3 |

TABLE 3-continued

| Compound No. | Abbreviation | Structural Formula | Name | CAS No. |
|---|---|---|---|---|
| aa041 | Fmoc-MeAhxe(2)-OH | | (2S)-2-[9H-fluoren-9-ylmethoxycarbonyl(methyl)amino]hex-5-enoic acid | 856412-21-0 |
| aa042 | Fmoc-MeHph-OH | | (2S)-2-[9H-fluoren-9-ylmethoxycarbonyl(methyl)amino]-4-phenyl-butanoic acid | 1065076-30-3 |
| aa045 | Fmoc-MePhe(4-Me)-OH | | (2S)-2-[9H-fluoren-9-ylmethoxycarbonyl(methyl)amino]-3-(p-tolyl)propanoic acid | 227616-20-8 |
| aa046 | Fmoc-MePhe(3-Me)-OH | | (2S)-2-[9H-fluoren-9-ylmethoxycarbonyl(methyl)amino]-3-(m-tolyl)propanoic acid | |
| aa048 | Fmoc-MePhe(4-Cl)-OH | | (2S)-3-(4-chlorophenyl)-2-[9H-fluoren-9-ylmethoxycarbonyl(methyl)amino]propanoic acid | 1217716-50-1 |
| aa051 | Fmoc-MePhe(4-F)-OH | | (2S)-2-[9H-fluoren-9-ylmethoxycarbonyl(methyl)amino]-3-(4-fluorophenyl)propanoic acid | 1979176-87-8 |
| aa052 | Fmoc-MePhe(2-F)-OH | | (2S)-2-[9H-fluoren-9-ylmethoxycarbonyl(methyl)amino]-3-(2-fluorophenyl)propanoic acid | 2109724-64-1 |
| aa053 | Fmoc-MeSer(Al)-OH | | (2S)-3-allyloxy-2-[9H-fluoren-9-ylmethoxycarbonyl(methyl)amino]propanoic acid | |

TABLE 3-continued

| Compound No. | Abbreviation | Structural Formula | Name | CAS No. |
|---|---|---|---|---|
| aa054 | Fmoc-MeAla(4-Thz)-OH | | (2S)-2-[9H-fluoren-9-ylmethoxycarbonyl(methyl)amino]-3-thiazol-4-yl-propanoic acid | 1446478-22-3 |
| aa055 | Fmoc-MeAib-OH | | 2-[9H-fluoren-9-ylmethoxycarbonyl(methyl)amino]-2-methyl-propanoic acid | 400779-65-9 |
| aa057 | Fmoc-Azp(2)-OH | | (2S)-1-(9H-fluoren-9-ylmethoxycarbonyl)azepane-2-carboxylic acid | 2322925-11-9 |
| aa058 | Fmoc-D-MeLeu-OH | | (2R)-2-[9H-fluoren-9-ylmethoxycarbonyl(methyl)amino]-4-methyl-pentanoic acid | 103478-63-3 |
| aa059 | Fmoc-Leu-OH | | (2S)-2-(9H-fluoren-9-ylmethoxycarbonylamino)-4-methyl-pentanoic acid | 35661-60-0 |
| aa061 | Fmoc-Algly-OH | | (2S)-2-(9H-fluoren-9-ylmethoxycarbonylamino)pent-4-enoic acid | 146549-21-5 |
| aa062 | Fmoc-Ile-OH | | (2S,3S)-2-(9H-fluoren-9-ylmethoxycarbonylamino)-3-methyl-pentanoic acid | 71989-23-6 |
| aa063 | Fmoc-Val-OH | | (2S)-2-(9H-fluoren-9-ylmethoxycarbonylamino)-3-methyl-butanoic acid | 68858-20-8 |
| aa064 | Fmoc-Gly(cBu)-OH | | (2S)-2-cyclobutyl-2-(9H-fluoren-9-ylmethoxycarbonylamino)acetic acid | 1391630-31-1 |
| aa065 | Fmoc-Gly(cBu-3-F2)-OH | | (2S)-2-(3,3-difluorocyclobutyl)-2-(9H-fluoren-9-ylmethoxycarbonylamino)acetic acid | 2349734-08-1 |

TABLE 3-continued

| Compound No. | Abbreviation | Structural Formula | Name | CAS No. |
|---|---|---|---|---|
| aa066 | Fmoc-aIle-OH | | (2S,3R)-2-(9H-fluoren-9-ylmethoxycarbonylamino)-3-methyl-pentanoic acid | 251316-98-0 |
| aa067 | Fmoc-Nva(3-Et)-OH | | (2S)-3-ethyl-2-(9H-fluoren-9-ylmethoxycarbonylamino)pentanoic acid | 1310680-47-7 |
| aa068 | Fmoc-D-Ile-OH | | (2R,3R)-2-(9H-fluoren-9-ylmethoxycarbonylamino)-3-methyl-pentanoic acid | 143688-83-9 |
| aa069 | Fmoc-Gly(cPent)-OH | | (2S)-2-cyclopentyl-2-(9H-fluoren-9-ylmethoxycarbonylamino)acetic acid | 220497-61-0 |
| aa070 | Fmoc-Abu(4-F3)-OH | | (2S)-2-(9H-fluoren-9-ylmethoxycarbonylamino)-4,4,4-trifluoro-butanoic acid | 181128-48-3 |
| aa071 | Fmoc-Abu-OH | | (2S)-2-(9H-fluoren-9-ylmethoxycarbonylamino)butanoic acid | 135112-27-5 |
| aa074 | Fmoc-MeGly-OH | | 2-[9H-fluoren-9-ylmethoxycarbonyl(methyl)amino]acetic acid | 77128-70-2 |
| aa075 | Fmoc-Gly-OH | | 2-(9H-fluoren-9-ylmethoxycarbonylamino)acetic acid | 29022-11-5 |
| aa076 | Fmoc-Aze(2)-OH | | (2S)-1-(9H-fluoren-9-ylmethoxycarbonyl)azetidine-2-carboxylic acid | 136552-06-2 |
| aa077 | Fmoc-Aib-OH | | 2-(9H-fluoren-9-ylmethoxycarbonylamino)-2-methyl-propanoic acid | 94744-50-0 |
| aa078 | Fmoc-Ala-OH | | (2S)-2-(9H-fluoren-9-ylmethoxycarbonylamino)propanoic acid | 35661-39-3 |

TABLE 3-continued

| Compound No. | Abbreviation | Structural Formula | Name | CAS No. |
|---|---|---|---|---|
| aa079 | Fmoc-D-Aze(2)-OH | | (2R)-1-(9H-fluoren-9-ylmethoxycarbonyl)azetidine-2-carboxylic acid | 374791-02-3 |
| aa080 | Fmoc-(Me)Pro-OH | | (2S)-1-(9H-fluoren-9-ylmethoxycarbonyl)-2-methyl-pyrrolidine-2-carboxylic acid | 167275-47-0 |
| aa081 | Fmoc-D-(Me)Pro-OH | | (2R)-1-(9H-fluoren-9-ylmethoxycarbonyl)-2-methyl-pyrrolidine-2-carboxylic acid | 1286768-33-9 |
| aa082 | Fmoc-D-Pro-OH | | (2R)-1-(9H-fluoren-9-ylmethoxycarbonyl)pyrrolidine-2-carboxylic acid | 101555-62-8 |
| aa083 | Fmoc-Tmo(2)-OH | | (3R)-4-(9H-fluoren-9-ylmethoxycarbonyl)thiomorpholine-3-carboxylic acid | 959572-96-4 |
| aa084 | Fmoc-Mor(3)-OH | | (3S)-4-(9H-fluoren-9-ylmethoxycarbonyl)morpholine-3-carboxylic acid | 281655-37-6 |
| aa085 | Fmoc-Pic(2)-OH | | (2S)-1-(9H-fluoren-9-ylmethoxycarbonyl)piperidine-2-carboxylic acid | 86069-86-5 |
| aa086 | Fmoc-Hyp(Et)-OH | | (2S,4R)-4-ethoxy-1-(9H-fluoren-9-ylmethoxycarbonyl)pyrrolidine-2-carboxylic acid | 1446478-31-4 |
| aa087 | Fmoc-Pro-OH | | (2S)-1-(9H-fluoren-9-ylmethoxycarbonyl)pyrrolidine-2-carboxylic acid | 71989-31-6 |
| aa088 | Fmoc-EtAla-OH | | (2S)-2-[ethyl(9H-fluoren-9-ylmethoxycarbonyl)amino]propanoic acid | 84000-09-9 |

TABLE 3-continued

| Compound No. | Abbreviation | Structural Formula | Name | CAS No. |
|---|---|---|---|---|
| aa090 | Fmoc-nPrGly-OH | | 2-[9H-fluoren-9-ylmethoxycarbonyl(propyl)amino]acetic acid | 1310680-42-2 |
| aa091 | Fmoc-EtGly-OH | | 2-[ethyl(9H-fluoren-9-ylmethoxycarbonyl)amino]acetic acid | 162545-29-1 |
| aa092 | Fmoc-DfeGly-OH | | 2-[2,2-difluoroethyl(9H-fluoren-9-ylmethoxycarbonyl)amino]acetic acid | 2172536-70-6 |
| aa093 | Fmoc-MfeGly-OH | | 2-[9H-fluoren-9-ylmethoxycarbonyl(2-fluoroethyl)amino]acetic acid | |
| aa094 | Fmoc-PraGly-OH | | 2-[9H-fluoren-9-ylmethoxycarbonyl(prop-2-ynyl)amino]acetic acid | 1033622-38-6 |
| aa095 | Fmoc-AllylGly-OH | | 2-[allyl(9H-fluoren-9-ylmethoxycarbonyl)amino]acetic acid | 222725-35-1 |
| aa101 | Fmoc-1-ACPrC-OH | | 1-(9H-fluoren-9-ylmethoxycarbonylamino)cyclopropanecarboxylic acid | 126705-22-4 |
| aa102 | Fmoc-NCMeGly-OH | | 2-[cyanomethyl(9H-fluoren-9-ylmethoxycarbonyl)amino]acetic acid | 2172570-83-9 |
| aa103 | Fmoc-cPrGly-OH | | 2-[cyclopropyl(9H-fluoren-9-ylmethoxycarbonyl)amino]acetic acid | 1342767-08-1 |

TABLE 3-continued

| Compound No. | Abbreviation | Structural Formula | Name | CAS No. |
|---|---|---|---|---|
| aa104 | Fmoc-bMeAla-OH | | 3-[9H-fluoren-9-ylmethoxycarbonyl(methyl)amino] propanoic acid | 172965-84-3 |
| aa106 | Fmoc-MeMethagly-OH | | (2S)-2-[9H-fluoren-9-ylmethoxycarbonyl(methyl)amino]-4-methyl-pent-4-enoic acid | 145615-72-1 |
| aa113 | Fmoc-ButenylGly-OH | | 2-[but-3-enyl(9H-fluoren-9-ylmethoxycarbonyl)amino]acetic acid | 227006-55-5 |
| aa123 | Fmoc-nBuGly-OH | | 2-[butyl(9H-fluoren-9-ylmethoxycarbonyl)amino]acetic acid | 234442-58-1 |
| aa155 | Fmoc-AllylPhe-OH | | (2S)-2-[allyl(9H-fluoren-9-ylmethoxycarbonyl)amino]-3-phenyl-propanoic acid | 1054548-99-0 |
| aa208 | Fmoc-D-MePhe-OH | | (2R)-2-[9H-fluoren-9-ylmethoxycarbonyl(methyl)amino]-3-phenyl-propanoic acid | 138775-05-0 |
| aa212 | Fmoc-D-MeAla-OH | | (2R)-2-[9H-fluoren-9-ylmethoxycarbonyl(methyl)amino] propanoic acid | 138774-92-2 |
| aa221 | Fmoc-Hph(4-Me)-OH | | (2S)-2-(9H-fluoren-9-ylmethoxycarbonylamino)-4-(p-tolyl)butanoic acid | 1260587-57-2 |

TABLE 3-continued

| Compound No. | Abbreviation | Structural Formula | Name | CAS No. |
|---|---|---|---|---|
| aa231 | Fmoc-Hph(34-Cl2)-OH | | (2S)-4-(3,4-dichlorophenyl)-2-(9H-fluoren-9-ylmethoxycarbonylamino)butanoic acid | 1260616-12-3 |
| aa238 | Fmoc-Pro(4-F2)-OH | | (2S)-1-(9H-fluoren-9-ylmethoxycarbonyl)-4,4-difluoro-pyrrolidine-2-carboxylic acid | 203866-21-1 |
| aa240 | Fmoc-Pro(4R-CF3)-OH | | (2S,4R)-1-(9H-fluoren-9-ylmethoxycarbonyl)-4-(trifluoromethyl)pyrrolidine-2-carboxylic acid | 2549171-72-2 |
| aa241 | Fmoc-Pro(4R-F)-OH | | (2S,4R)-1-(9H-fluoren-9-ylmethoxycarbonyl)-4-fluoro-pyrrolidine-2-carboxylic acid | 203866-20-0 |
| aa245 | Fmoc-Hyp(iBu)-OH | | (2S,4R)-1-(9H-fluoren-9-ylmethoxycarbonyl)-4-isobutoxy-pyrrolidine-2-carboxylic acid | 865353-14-6 |
| aa249 | Fmoc-MeSer(iPen)-OH | | (2S)-2-[9H-fluoren-9-ylmethoxycarbonyl(methyl)amino]-3-isopentyloxy-propanoic acid | 2255321-12-9 |
| aa262 | Fmoc-Pro(4S-F)-OH | | (2S,4S)-1-(9H-fluoren-9-ylmethoxycarbonyl)-4-fluoro-pyrrolidine-2-carboxylic acid | 203866-19-7 |
| aa263 | Fmoc-cisHyp(Me)-OH | | (2S,4S)-1-(9H-fluoren-9-ylmethoxycarbonyl)-4-methoxy-pyrrolidine-2-carboxylic acid | 1190617-97-0 |

TABLE 3-continued

| Compound No. | Abbreviation | Structural Formula | Name | CAS No. |
| --- | --- | --- | --- | --- |
| aa274 | Fmoc-Pro(4-keto)-OH | | (2S)-1-(9H-fluoren-9-ylmethoxycarbonyl)-4-oxo-pyrrolidine-2-carboxylic acid | 223581-83-7 |
| aa275 | Fmoc-Pro(4-Me2)-OH | | (2S)-1-(9H-fluoren-9-ylmethoxycarbonyl)-4,4-dimethyl-pyrrolidine-2-carboxylic acid | 1380336-01-5 |
| aa277 | Fmoc-Pic(2)(4-F2)-OH | | (2S)-1-(9H-fluoren-9-ylmethoxycarbonyl)-4,4-difluoro-piperidine-2-carboxylic acid | 1221793-52-7 |
| aa278 | Fmoc-Pro(4-cPr)-OH | | (6S)-5-(9H-fluoren-9-ylmethoxycarbonyl)-5-azaspiro[2.4]heptane-6-carboxylic acid | 2170726-27-7 |
| aa280 | Fmoc-Nle-OH | | (2S)-2-(9H-fluoren-9-ylmethoxycarbonylamino)hexanoic acid | 77284-32-3 |
| aa301 | Fmoc-cVal-OH | | 1-(9H-fluoren-9-ylmethoxycarbonylamino)cyclobutanecarboxylic acid | 885951-77-9 |
| aa302 | Fmoc-cLeu-OH | | 1-(9H-fluoren-9-ylmethoxycarbonylamino)cyclopentanecarboxylic acid | 117322-30-2 |
| aa303 | Fmoc-cVal(3-Me2)-OH | | 1-(9H-fluoren-9-ylmethoxycarbonylamino)-3,3-dimethyl-cyclobutanecarboxylic acid | 1936161-54-4 |
| aa305 | Fmoc-Athpc-OH | | 4-(9H-fluoren-9-ylmethoxycarbonylamino)tetrahydropyran-4-carboxylic acid | 285996-72-7 |
| aa306 | Fmoc-cHex-OH | | 1-(9H-fluoren-9-ylmethoxycarbonylamino)cyclohexanecarboxylic acid | 162648-54-6 |

TABLE 3-continued

| Compound No. | Abbreviation | Structural Formula | Name | CAS No. |
|---|---|---|---|---|
| aa307 | Fmoc-cVal(3-F2)-OH | | 1-(9H-fluoren-9-ylmethoxycarbonylamino)-3,3-difluoro-cyclobutanecarboxylic acid | 1936532-04-5 |
| aa308 | Fmoc-bAla(2-Me2)-OH | | 3-(9H-fluoren-9-ylmethoxycarbonylamino)-2,2-dimethyl-propanoic acid | 1076197-00-6 |
| aa310 | Fmoc-cLeu(34-d)-OH | | 1-(9H-fluoren-9-ylmethoxycarbonylamino)cyclopent-3-ene-1-carboxylic acid | 2219369-66-9 |
| aa311 | Fmoc-D-Algly-OH | | (2R)-2-(9H-fluoren-9-ylmethoxycarbonylamino)pent-4-enoic acid | 170642-28-1 |
| aa312 | Fmoc-cHex(4-F2)-OH | | 1-(9H-fluoren-9-ylmethoxycarbonylamino)-4,4-difluoro-cyclohexanecarboxylic acid | 1986905-26-3 |
| aa314 | Fmoc-D-Ala-OH | | (2R)-2-(9H-fluoren-9-ylmethoxycarbonylamino)propanoic acid | 79990-15-1 |
| aa316 | Fmoc-(Me)Abu-OH | | (2S)-2-(9H-fluoren-9-ylmethoxycarbonylamino)-2-methyl-butanoic acid | 857478-30-9 |
| aa318 | Fmoc-AoxeC-OH | | 3-(9H-fluoren-9-ylmethoxycarbonylamino)oxetane-3-carboxylic acid | 1380327-56-9 |
| aa330 | Fmoc-MeGly(cPent)-OH | | (2S)-2-cyclopentyl-2-[9H-fluoren-9-ylmethoxycarbonyl(methyl)amino]acetic acid | 187475-29-2 |

TABLE 3-continued

| Compound No. | Abbreviation | Structural Formula | Name | CAS No. |
|---|---|---|---|---|
| aa336 | Fmoc-MeIle-OH | | (2S,3S)-2-[9H-fluoren-9-ylmethoxycarbonyl(methyl)amino]-3-methyl-pentanoic acid | 138775-22-1 |
| aa337 | Fmoc-MeChg-OH | | (2S)-2-cyclohexyl-2-[9H-fluoren-9-ylmethoxycarbonyl(methyl)amino]acetic acid | 925240-97-7 |
| aa338 | Fmoc-MeTle-OH | | (2S)-2-[9H-fluoren-9-ylmethoxycarbonyl(methyl)amino]-3,3-dimethyl-butanoic acid | 1172579-62-2 |
| aa340 | Fmoc-MeaIle-OH | | (2S,3R)-2-[9H-fluoren-9-ylmethoxycarbonyl(methyl)amino]-3-methyl-pentanoic acid | 1821797-58-3 |
| aa387 | Fmoc-MeGly(cPr)-OH | | (S)-2-((((9H-fluoren-9-yl)methoxy)carbonyl)(methyl)amino)-2-cyclopropyl-acetic acid | 2642726-08-5 |
| aa388 | Fmoc-MeAnone(2)-OH | | (2S)-2-[9H-fluoren-9-ylmethoxycarbonyl(methyl)amino] non-8-enoic acid | 1808268-51-0 |
| aa390 | Fmoc-Leu-OH | | (2S)-2-([(9H-fluoren-9-ylmethoxy)carbonyl]amino)-4-methyl-pentanoic acid | 35661-60-0 |
| aa392 | Fmoc-Thr(Et)-OH | | (2S,3R)-3-ethoxy-2-(9H-fluoren-9-ylmethoxycarbonyl amino)butanoic acid | 2108708-74-1 |
| aa393 | Fmoc-Gly(cPr)-OH | | (2S)-2-cyclopropyl-2-(9H-fluoren-9-ylmethoxycarbonyl amino)acetic acid | 1212257-18-5 |

TABLE 3-continued

| Compound No. | Abbreviation | Structural Formula | Name | CAS No. |
|---|---|---|---|---|
| aa394 | Fmoc-Gly(4-THP)-OH | | (2S)-2-(9H-fluoren-9-ylmethoxycarbonyl amino)-2-tetrahydropyran-4-yl-acetic acid | 368866-31-3 |
| aa395 | Fmoc-Thr(Me)-OH | | (2S,3R)-2-(9H-fluoren-9-ylmethoxycarbonyl amino)-3-methoxy-butanoic acid | 928063-81-4 |
| aa396 | Fmoc-(MeOEt)Gly-OH | | 2-[9H-fluoren-9-ylmethoxycarbonyl(2-methoxyethyl)amino]acetic acid | 1341969-00-3 |
| aa412 | Fmoc-Hph(4-Cl)-OH | | (2S)-4-(4-chlorophenyl)-2-(9H-fluoren-9-ylmethoxycarbonyl amino)butanoic acid | 1260608-62-5 |
| aa416 | Fmoc-Hyp(iPr)-OH | | (2S,4R)-1-(9H-fluoren-9-ylmethoxycarbonyl)-4-isopropoxy-pyrrolidine-2-carboxylic acid | |
| aa417 | Fmoc-Pro(4R-Me)-OH | | (2S,4R)-1-(9H-fluoren-9-ylmethoxycarbonyl)-4-methyl-pyrrolidine-2-carboxylic acid | 333777-34-7 |
| aa418 | Fmoc-Pro(4R-nPr)-OH | | (2S,4R)-1-(9H-fluoren-9-ylmethoxycarbonyl)-4-propyl-pyrrolidine-2-carboxylic acid | |
| aa419 | Fmoc-Pro(4R-Et)-OH | | (2S,4R)-4-ethyl-1-(9H-fluoren-9-ylmethoxycarbonyl)pyrrolidine-2-carboxylic acid | |

TABLE 3-continued

| Compound No. | Abbreviation | Structural Formula | Name | CAS No. |
|---|---|---|---|---|
| aa420 | Fmoc-MecVal(3-Me2)-OH | | 1-[9H-fluoren-9-ylmethoxycarbonyl(methyl)amino]-3,3-dimethyl-cyclobutane-carboxylic acid | 2025106-27-6 |
| aa421 | Fmoc-MecVal-OH | | 1-[9H-fluoren-9-ylmethoxycarbonyl(methyl)amino] cyclobutane-carboxylic acid | 1700368-07-5 |
| aa422 | Fmoc-MecLeu-OH | | 1-[9H-fluoren-9-ylmethoxycarbonyl(methyl)amino] cyclopentane-carboxylic acid | 1694050-88-8 |
| aa427 | Fmoc-Hyp-OH | | (2S,4R)-1-(9H-fluoren-9-ylmethoxycarbonyl)-4-hydroxy-pyrrolidine-2-carboxylic acid | 88050-17-3 |

TABLE 4

| Compound No. | Abbreviation | Structural Formula | Name |
|---|---|---|---|
| aa004 | Fmoc-MeAOC(2)-OH | | (2S)-2-[9H-fluoren-9-ylmethoxycarbonyl(methyl)amino]octanoic acid |
| aa006 | Fmoc-MeAla(cPent)-OH | | (2S)-3-cyclopentyl-2-[9H-fluoren-9-ylmethoxycarbonyl(methyl)amino]propanoic acid |
| aa010 | Fmoc-MeAla(cBu)-OH | | (2S)-3-cyclobutyl-2-[9H-fluoren-9-ylmethoxycarbonyl(methyl)amino]propanoic acid |
| aa013 | Fmoc-MeCys(Me)-OH | | (2R)-2-[9H-fluoren-9-ylmethoxycarbonyl(methyl)amino]-3-methylsulfanyl-propanoic acid |

TABLE 4-continued

| Compound No. | Abbreviation | Structural Formula | Name |
|---|---|---|---|
| aa018 | Fmoc-MePRA-OH | | (2S)-2-[9H-fluoren-9-ylmethoxycarbonyl(methyl)amino]pent-4-ynoic acid |
| aa019 | Fmoc-MeAbu(4-F2)-OH | | (2S)-2-[9H-fluoren-9-ylmethoxycarbonyl(methyl)amino]-4,4-difluoro-butanoic acid |
| aa020 | Fmoc-MeSer(cPr)-OH | | (2S)-3-(cyclopropoxy)-2-[9H-fluoren-9-ylmethoxycarbonyl(methyl)amino]propanoic acid |
| aa021 | Fmoc-MeSer(Tfe)-OH | | (2S)-2-[9H-fluoren-9-ylmethoxycarbonyl(methyl)amino]-3-(2,2,2-trifluoroethoxy)propanoic acid |
| aa022 | Fmoc-MeSer(Et)-OH | | (2S)-3-ethoxy-2-[9H-fluoren-9-ylmethoxycarbonyl(methyl)amino]propanoic acid |
| aa023 | Fmoc-MeAla(3-Thie)-OH | | (2S)-2-[9H-fluoren-9-ylmethoxycarbonyl(methyl)amino]-3-(3-thienyl)propanoic acid |
| aa028 | Fmoc-MePhe(34-Cl2)-OH | | (2S)-3-(3,4-dichlorophenyl)-2-[9H-fluoren-9-ylmethoxycarbonyl(methyl)amino]propanoic acid |
| aa029 | Fmoc-MePhe(4-CN)-OH | | (2S)-3-(4-cyanophenyl)-2-[9H-fluoren-9-ylmethoxycarbonyl(methyl)amino]propanoic acid |

TABLE 4-continued

| Compound No. | Abbreviation | Structural Formula | Name |
|---|---|---|---|
| aa030 | Fmoc-MePhe(3-CN)-OH | | (2S)-3-(3-cyanophenyl)-2-[9H-fluoren-9-ylmethoxycarbonyl(methyl)amino]propanoic acid |
| aa031 | Fmoc-MePhe(2-CN)-OH | | (2S)-3-(2-cyanophenyl)-2-[9H-fluoren-9-ylmethoxycarbonyl(methyl)amino]propanoic acid |
| aa244 | Fmoc-MeNva(5-F2)-OH | | (2S)-2-[9H-fluoren-9-ylmethoxycarbonyl(methyl)amino]-5,5-difluoro-pentanoic acid |
| aa043 | Fmoc-MeNva(5-Cl2)-OH | | (2S)-5,5-dichloro-2-[9H-fluoren-9-ylmethoxycarbonyl(methyl)amino]pentanoic acid |
| aa047 | Fmoc-MePhe(2-Me)-OH | | (2S)-2-[9H-fluoren-9-ylmethoxycarbonyl(methyl)amino]-3-(o-tolyl)propanoic acid |
| aa049 | Fmoc-MePhe(2-Cl)-OH | | (2S)-3-(2-chlorophenyl)-2-[9H-fluoren-9-ylmethoxycarbonyl(methyl)amino]propanoic acid |
| aa050 | Fmoc-MePhe(34-F2)-OH | | (2S)-3-(3,4-difluorophenyl)-2-[9H-fluoren-9-ylmethoxycarbonyl(methyl)amino]propanoic acid |

TABLE 4-continued

| Compound No. | Abbreviation | Structural Formula | Name |
|---|---|---|---|
| aa056 | Fmoc-R-MeAMPA-OH | | (2R)-3-[9H-fluoren-9-ylmethoxycarbonyl(methyl)amino]-2-methyl-propanoic acid |
| aa060 | Fmoc-MeGly(cBu)-OH | | (2S)-2-cyclobutyl-2-[9H-fluoren-9-ylmethoxycarbonyl(methyl)amino]acetic acid |
| aa098 | Fmoc-Aze(2)(3S-Me)-OH | | (2S,3S)-1-(9H-fluoren-9-ylmethoxycarbonyl)-3-methyl-azetidine-2-carboxylic acid |
| aa099 | Fmoc-Aze(2)(3R-Me)-OH | | (2S,3R)-1-(9H-fluoren-9-ylmethoxycarbonyl)-3-methyl-azetidine-2-carboxylic acid |
| aa100 | Fmoc-Aze(2)(3-Me2)-OH | | (2S)-1-(9H-fluoren-9-ylmethoxycarbonyl)-3,3-dimethyl-azetidine-2-carboxylic acid |
| aa111 | Fmoc-D-MeSer(Al)-OH | | (2R)-3-allyloxy-2-[9H-fluoren-9-ylmethoxycarbonyl(methyl)amino]propanoic acid |
| aa136 | Fmoc-nPrPhe(4-CF3)-OH | | (2S)-2-[9H-fluoren-9-ylmethoxycarbonyl(propyl)amino]-3-[4-(trifluoromethyl)phenyl]propanoic acid |
| aa164 | Fmoc-EtPhe(4-CF3)-OH | | (2S)-2-[ethyl(9H-fluoren-9-ylmethoxycarbonyl)amino]-3-[4-(trifluoromethyl)phenyl]propanoic acid |

TABLE 4-continued

| Compound No. | Abbreviation | Structural Formula | Name |
|---|---|---|---|
| aa174 | Fmoc-nPrPhe(4-Me)-OH | | (2S)-2-[9H-fluoren-9-ylmethoxycarbonyl(propyl)amino]-3-(p-tolyl)propanoic acid |
| aa199 | Fmoc-MePhe(4-CF3)-OH | | (2S)-2-[9H-fluoren-9-ylmethoxycarbonyl(methyl)amino]-3-[4-(trifluoromethyl)phenyl]propanoic acid |
| aa201 | Fmoc-EtPhe(4-Me)-OH | | (2S)-2-[ethyl(9H-fluoren-9-ylmethoxycarbonyl)amino]-3-(p-tolyl)propanoic acid |
| aa210 | Fmoc-EtGly(cPent)-OH | | (2S)-2-cyclopentyl-2-[ethyl(9H-fluoren-9-ylmethoxycarbonyl)amino]acetic acid |
| aa217 | Fmoc-Hph(4-CF3-35-F2)-OH | | (2S)-4-[3,5-difluoro-4-(trifluoromethyl)phenyl]-2-(9H-fluoren-9-ylmethoxycarbonylamino)butanoic acid |
| aa218 | Fmoc-Hph(4-CF3-3-Cl)-OH | | (2S)-4-[3-chloro-4-(trifluoromethyl)phenyl]-2-(9H-fluoren-9-ylmethoxycarbonylamino)butanoic acid |
| aa219 | Fmoc-Hph(4-CF3-3-F)-OH | | (2S)-2-(9H-fluoren-9-ylmethoxycarbonylamino)-4-[3-fluoro-4-(trifluoromethyl)phenyl]butanoic acid |

TABLE 4-continued

| Compound No. | Abbreviation | Structural Formula | Name |
|---|---|---|---|
| aa220 | Fmoc-Hph(4-Cl-35-F2)-OH | | (2S)-4-(4-chloro-3,5-difluoro-phenyl)-2-(9H-fluoren-9-ylmethoxycarbonylamino)butanoic acid |
| aa229 | Fmoc-Abu(5-Bzt)-OH | | (2S)-4-(benzothiophen-5-yl)-2-(9H-fluoren-9-ylmethoxycarbonylamino)butanoic acid |
| aa233 | Fmoc-Hph(4-CF3-3-Me)-OH | | (2S)-2-(9H-fluoren-9-ylmethoxycarbonylamino)-4-[3-methyl-4-(trifluoromethyl)phenyl]butanoic acid |
| aa235 | Fmoc-Hph(4-CF3-3-OMe)-OH | | (2S)-2-(9H-fluoren-9-ylmethoxycarbonylamino)-4-[3-methoxy-4-(trifluoromethyl)phenyl]butanoic acid |
| aa239 | Fmoc-Pro(4S-Me)-OH | | (2S,4S)-1-(9H-fluoren-9-ylmethoxycarbonyl)-4-methyl-pyrrolidine-2-carboxylic acid |
| aa246 | Fmoc-Hyp(nPr)-OH | | (2S,4R)-1-(9H-fluoren-9-ylmethoxycarbonyl)-4-propoxy-pyrrolidine-2-carboxylic acid |
| aa250 | Fmoc-D-MeSer(nPr)-OH | | (2R)-2-[9H-fluoren-9-ylmethoxycarbonyl(methyl)amino]-3-propoxy-propanoic acid |

TABLE 4-continued

| Compound No. | Abbreviation | Structural Formula | Name |
|---|---|---|---|
| aa264 | Fmoc-cisHyp(3)(THP)-OH | | (2S,3R)-1-(9H-fluoren-9-ylmethoxycarbonyl)-3-tetrahydropyran-2-yloxy-pyrrolidine-2-carboxylic acid |
| aa265 | Fmoc-Hyp(3)(THP)-OH | | (2S,3S)-1-(9H-fluoren-9-ylmethoxycarbonyl)-3-tetrahydropyran-2-yloxy-pyrrolidine-2-carboxylic acid |
| aa267 | Fmoc-cisHyp(THP)-OH | | (2S,4S)-1-(9H-fluoren-9-ylmethoxycarbonyl)-4-tetrahydropyran-2-yloxy-pyrrolidine-2-carboxylic acid |
| aa268 | Fmoc-Pro(3S4-Cl)-OH | | (1S,2S,5R)-3-(9H-fluoren-9-ylmethoxycarbonyl)-3-azabicyclo[3.1.0]hexane-2-carboxylic acid |
| aa279 | Fmoc-Hyp(THP)-OH | | (2S,4R)-1-(9H-fluoren-9-ylmethoxycarbonyl)-4-tetrahydropyran-2-yloxy-pyrrolidine-2-carboxylic acid |
| aa281 | Fmoc-Hyp(Me)-OH | | (2S,4R)-1-(9H-fluoren-9-ylmethoxycarbonyl)-4-methoxy-pyrrolidine-2-carboxylic acid |
| aa331 | Fmoc-MeNva(3-Et)-OH | | (2S)-3-ethyl-2-[9H-fluoren-9-ylmethoxycarbonyl(methyl)amino]pentanoic acid |
| aa389 | Fmoc-nPrLeu-OH | | (2S)-2-[9H-fluoren-9-ylmethoxycarbonyl(propyl)amino]-4-methyl-pentanoic acid |

TABLE 4-continued

| Compound No. | Abbreviation | Structural Formula | Name |
|---|---|---|---|
| aa391 | Fmoc-Thr(nPr)-OH | | (2S,3R)-2-(9H-fluoren-9-ylmethoxycarbonylamino)-3-propoxy-butanoic acid |
| aa397 | Fmoc-nPrSer(iPen)-OH | | (2S)-2-[9H-fluoren-9-ylmethoxycarbonyl(propyl)amino]-3-isopentyloxy-propanoic acid |
| aa398 | Fmoc-nPrSer(cBu)-OH | | (2S)-3-(cyclobutoxy)-2-[9H-fluoren-9-ylmethoxycarbonyl(propyl)amino]propanoic acid |
| aa399 | Fmoc-Abu(1-Me-7-Cl-5-Indo)-OH | | (2S)-4-(7-chloro-1-methyl-indol-5-yl)-2-(9H-fluoren-9-ylmethoxycarbonylamino)butanoic acid |
| aa400 | Fmoc-Abu(5-Bzt-2-F-3-Me)-OH | | (2S)-2-(9H-fluoren-9-ylmethoxycarbonylamino)-4-(2-fluoro-3-methyl-benzothiophen-5-yl)butanoic acid |
| aa401 | Fmoc-Abu(5-Bzt-7-Cl)-OH | | (2S)-4-(7-chlorobenzothiophen-5-yl)-2-(9H-fluoren-9-ylmethoxycarbonylamino)butanoic acid |
| aa402 | Fmoc-Abu(1-Me-6-Indo)-OH | | (2S)-2-(9H-fluoren-9-ylmethoxycarbonylamino)-4-(1-methylindol-6-yl)butanoic acid |
| aa403 | Fmoc-Abu(13-Me2-6-Indo)-OH | | (2S)-4-(1,3-dimethyl indol-6-yl)-2-(9H-fluoren-9-ylmethoxycarbonylamino)butanoic acid |

TABLE 4-continued

| Compound No. | Abbreviation | Structural Formula | Name |
|---|---|---|---|
| aa404 | Fmoc-Abu(123-Me3-6-Indo)-OH | | (2S)-2-(9H-fluoren-9-ylmethoxycarbonylamino)-4-(1,2,3-trimethyl indol-6-yl)butanoic acid |
| aa405 | Fmoc-Abu(5-Bzt-23-Me2)-OH | | (2S)-4-(2,3-dimethyl benzothiophen-5-yl)-2-(9H-fluoren-9-ylmethoxycarbonylamino) butanoic acid |
| aa406 | Fmoc-Hph(3-Cl-4-Et)-OH | | (2S)-4-(3-chloro-4-ethyl-phenyl)-2-(9H-fluoren-9-ylmethoxycarbonylamino)butanoic acid |
| aa407 | Fmoc-Hph(4-OMe-35-Me2)-OH | | (2S)-2-(9H-fluoren-9-ylmethoxycarbonylamino)-4-[4-(methoxymethyl)-3,5-dimethyl-phenyl] butanoic acid |
| aa408 | Fmoc-Hph(4-Cl-3-OMe)-OH | | (2S)-4-(4-chloro-3-methoxy-phenyl)-2-(9H-fluoren-9-ylmethoxycarbonylamino) butanoic acid |
| aa409 | Fmoc-Hph(4-Cl-3-CF3)-OH | | (2S)-4-[4-chloro-3-(trifluoromethyl)phenyl]-2-(9H-fluoren-9-ylmethoxycarbonylamino) butanoic acid |
| aa410 | Fmoc-Hph(4-CHF2-35-F2)-OH | | (2S)-4-[4-(difluoromethyl)-3,5-difluoro-phenyl]-2-(9H-fluoren-9-yl methoxycarbonylamino)butanoic acid |
| aa411 | Fmoc-Hph(4-Cl-35-Me2)-OH | | (2S)-4-(4-chloro-3,5-dimethyl-phenyl)-2-(9H-fluoren-9-ylmethoxycarbonylamino) butanoic acid |

TABLE 4-continued

| Compound No. | Abbreviation | Structural Formula | Name |
|---|---|---|---|
| aa414 | Fmoc-Hyp(cPent)-OH | | (2S,4R)-4-(cyclopentoxy)-1-(9H-fluoren-9-ylmethoxycarbonyl)pyrrolidin-2-carboxylic acid |
| aa415 | Fmoc-Hyp(cBu)-OH | | (2S,4R)-4-(cyclobutoxy)-1-(9H-fluoren-9-ylmethoxycarbonyl)pyrrolidin-2-carboxylic acid |
| aa443 | Fmoc-ButenylPhe(4-Me)-OH | | (2S)-2-[but-3-enyl(9H-fluoren-9-ylmethoxycarbonyl)amino]-3-(p-tolyl)propanoic acid |

Synthesis of Fmoc-Amino Acids
Synthesis of Compound aa004

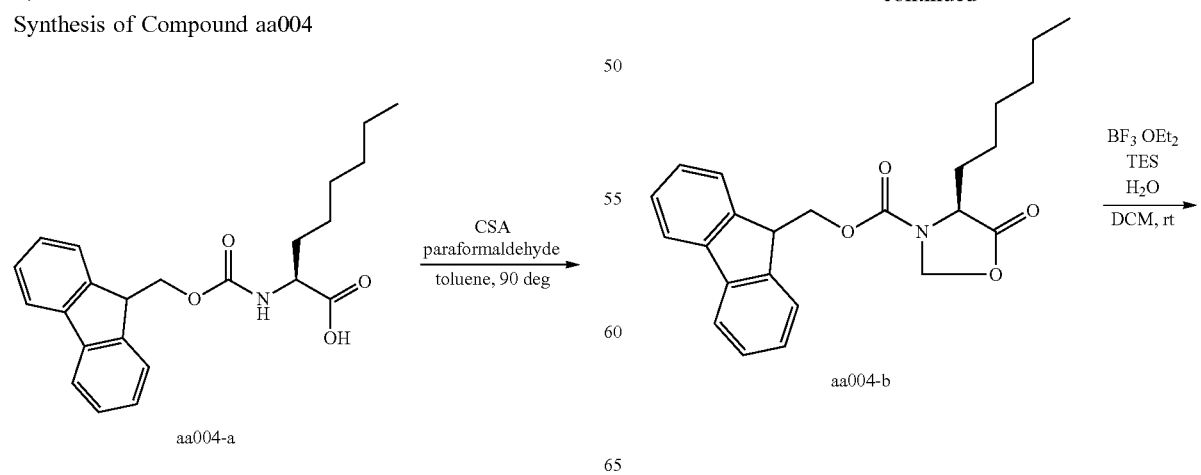

-continued

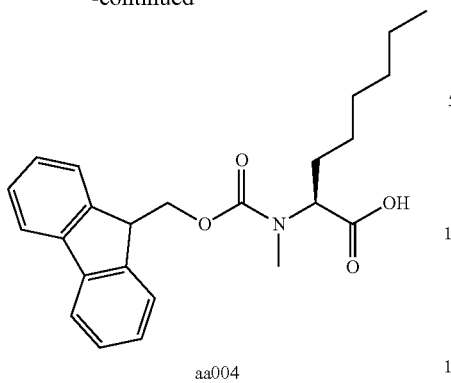

aa004

Compound aa004-a (3.00 g, 7.86 mmol) was dissolved in toluene (79 mL), paraformaldehyde (708 mg, 23.6 mmol) and CSA (91 mg, 0.393 mmol) were added, and the mixture was stirred at 90° C. for 5 hours. After cooling the mixture to room temperature, paraformaldehyde (236 mg, 7.86 mmol) and CSA (46 mg, 0.197 mmol) were added, and the mixture was further stirred at 90° C. for 30 minutes. After being cooled to room temperature, the mixture was filtered through Celite, and the residue was washed with ethyl acetate (50 mL). The filtrate was washed twice with a saturated aqueous sodium hydrogen carbonate solution (50 mL) and washed with 50% brine (50 mL). This was dried over sodium sulfate and filtered off, and the solvent was distilled off under reduced pressure to give Compound aa004-b as a crude product.

LCMS (ESI) m/z=394 (M+H)+

Retention time: 1.08 min (Analytical condition SQDFA05)

The crude product (7.86 mmol) of Compound aa004-b was dissolved in DCM (39 mL), then a boron trifluoride diethyl ether complex (BF3·OEt2)(2.96 mL, 23.6 mmol), TES (1.95 mL, 23.6 mmol), and water (0.142 mL, 7.86 mmol) were added, and the mixture was stirred at room temperature for 1 hour. The reaction solution was washed with a saturated ammonium chloride solution (40 mL), washed with 50% brine (40 mL), then dried over sodium sulfate, and filtered off, and the solvent was distilled off under reduced pressure. The resulting residue was dissolved in acetonitrile (40 mL) and washed twice with n-hexane (40 mL). The solvent was distilled off under reduced pressure to give Compound aa004 (3.04 g, 98%).

LCMS (ESI) m/z=396 (M+H)+

Retention time: 1.00 min (Analytical condition SQDFA05)

Synthesis of Compound aa028

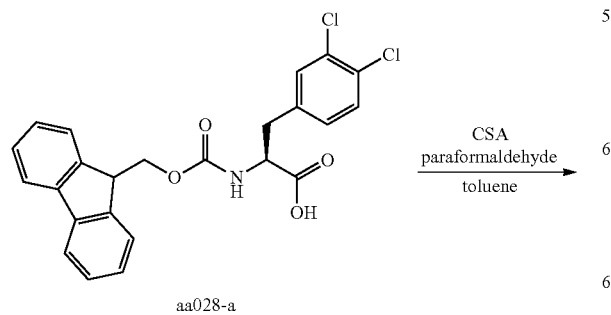

aa028-a

-continued

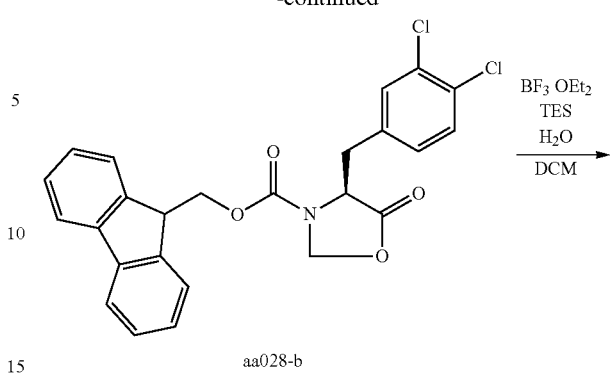

aa028-b

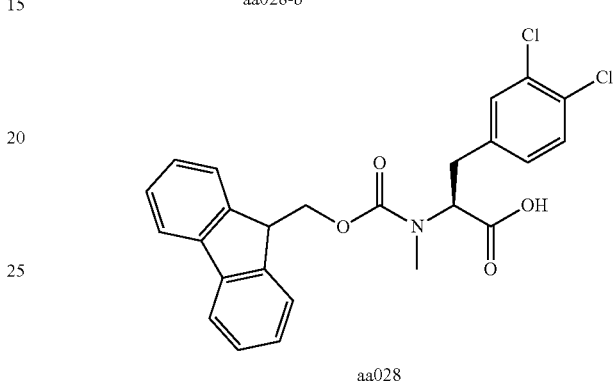

aa028

Using aa028-a as a starting material, aa028-b (9.61 g, 94%) was obtained as a crude product in the same manner as the synthesis of Compound aa004-b.

Using aa028-b as a starting material, aa028 (8.10 g, 84%) was obtained in the same manner as the synthesis of Compound aa004.

LCMS (ESI) m/z=470 (M+H)+

Retention time: 0.99 min (Analytical condition SQDFA05)

Synthesis of Compound aa018

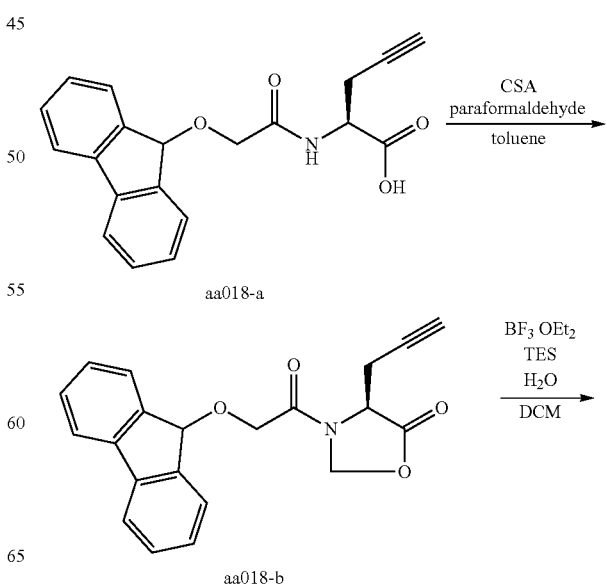

aa018-a aa018-b

-continued

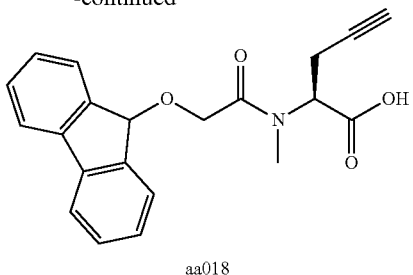

aa018

Using Compound aa018-a, ((2S)-2-[9H-fluoren-9-yl-methoxycarbonylamino] pent-4-ynoic acid, Fmoc-PRA-OH)(3 g, 8.95 mmol) as a starting material, Compound aa018-b (2.71 g, 87%) was obtained in the same manner as the synthesis of Compound aa004-b.

LCMS (ESI) m/z=348 (M+H)+

Retention time: 0.87 min (Analytical condition SQDFA05)

Using the resulting Compound aa018-b (989 mg, 2.85 mmol), Compound aa018 (986 mg, 99%) was obtained in the same manner as the synthesis of Compound aa004.

LCMS (ESI) m/z=350 (M+H)+

Retention time: 0.79 min (Analytical condition SQDFA05)

Synthesis of Compound aa049

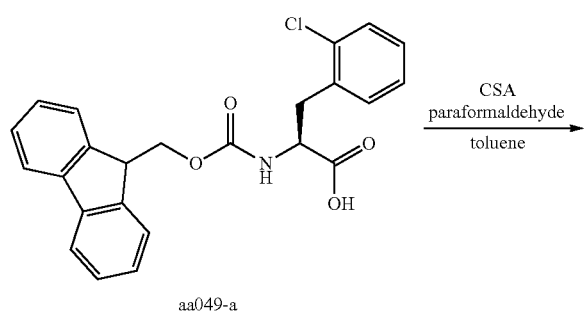

aa049-a

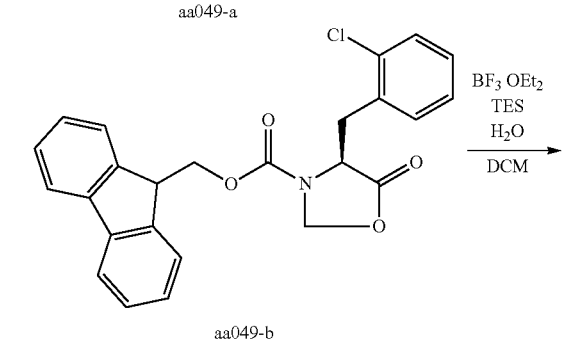

aa049-b

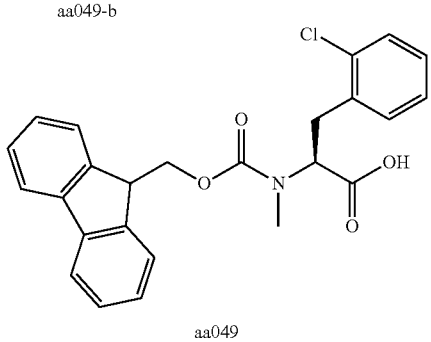

aa049

Using Compound aa049-a, ((2S)-3-(2-chlorophenyl)-2-[9H-fluoren-9-ylmethoxycarbonylamino]propanoic acid, Fmoc-Phe (2-Cl)—OH)(5 g, 11.85 mmol) as a starting material, Compound aa049-b (4.2 g, 82%) was obtained in the same manner as the synthesis of Compound aa004-b.

LCMS (ESI) m/z=434 (M+H)+

Retention time: 1.01 min (Analytical condition SQDFA05)

Using the resulting Compound aa049-b (4.2 g), Compound aa049 (3.32 g, 79%) was obtained in the same manner as the synthesis of Compound aa004.

LCMS (ESI) m/z=436 (M+H)+

Retention time: 0.94 min (Analytical condition SQDFA05)

Synthesis of Compound aa199

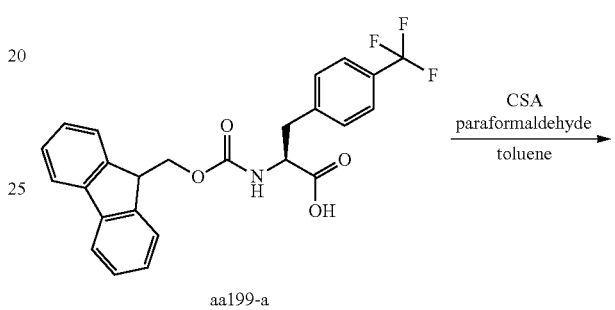

aa199-a

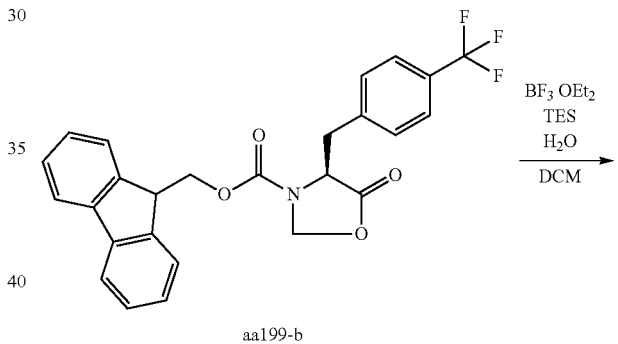

aa199-b

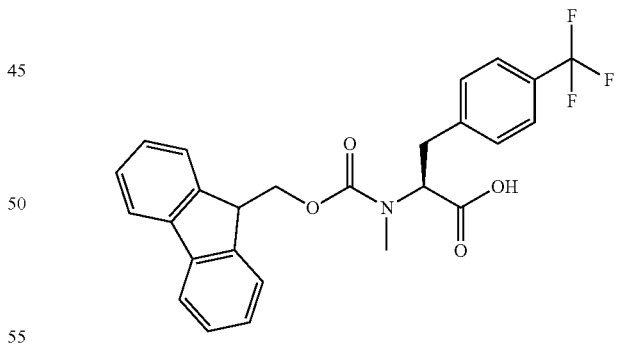

aa199

Using Compound aa199-a, ((2S)-2-[9H-fluoren-9-yl-methoxycarbonylamino]-3-[4-(trifluoromethyl)phenyl] propanoic acid, Fmoc-Phe (4—CF3)—OH)(200 g, 439 mmol) as a starting material, Compound aa199-b (206.8 g) was obtained as a crude product in the same manner as the synthesis of Compound aa004-b.

LCMS (ESI) m/z=469 (M+H)+

Retention time: 3.30 min (Analytical condition SMD method_03)

Using the resulting Compound aa 199-b (205 g), Compound aa199 (195 g, 2 steps, 95%) was obtained in the same manner as the synthesis of Compound aa004.

LCMS (ESI) m/z=470 (M+H)+

Retention time: 2.96 min (Analytical condition SMD Method_03)

Synthesis of Compound aa013

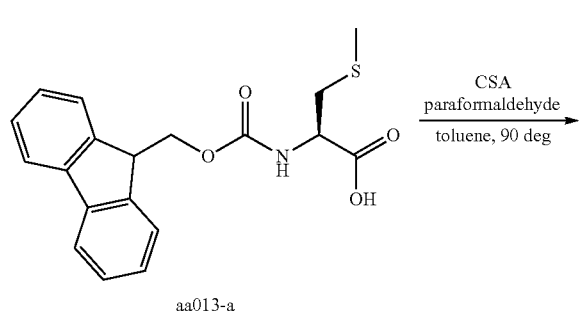

aa013-a

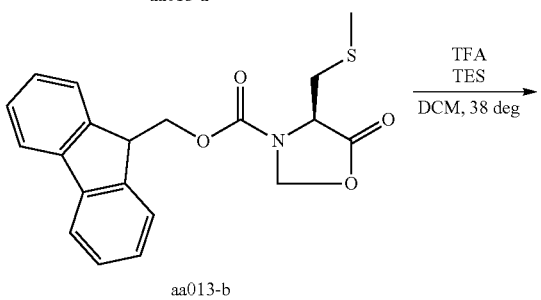

aa013-b

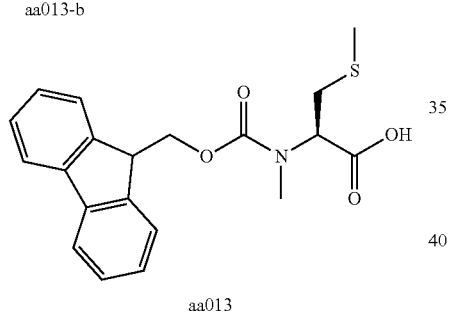

aa013

Using aa013-a as a starting material, aa013-b (5.29 g, 102%) was obtained as a crude product in the same manner as the synthesis of Compound aa004-b.

LCMS (ESI) m/z=370 (M+H)+

Retention time: 0.89 min (Analytical condition SQDFA05)

Compound aa013-b (5.29 g, 14.3 mmol) was dissolved in DCM (125 mL), TES (22.9 mL, 143 mmol) and TFA (36.4 mL, 473 mmol) were added, and the mixture was stirred at 38° C. for 8 hours. The solvent was distilled off under reduced pressure, and the residue was dissolved in TBME (100 mL) and washed with a 1 M aqueous dipotassium hydrogen phosphate solution (50 mL). The aqueous layer was extracted 3 times with TBME, the organic layers were combined, and the solvent was distilled off under reduced pressure. Acetonitrile/n-hexane=½ (100 mL) was added, and the mixture was extracted with a 5% aqueous potassium hydrogen carbonate solution (100 mL). The aqueous layer was acidified with 6 M hydrochloric acid, and extracted twice with TBME (30 mL). The organic layer was dried over sodium sulfate and filtered off, and the solvent was distilled off under reduced pressure. Acetonitrile (100 mL) was added, the mixture was washed with n-hexane (50) mL), and the solvent was distilled off under reduced pressure to give Compound aa013 (4.06 g, 76%).

LCMS (ESI) m/z=372 (M+H)+

Retention time: 0.83 min (Analytical condition SQDFA05)

Synthesis of Compound aa030

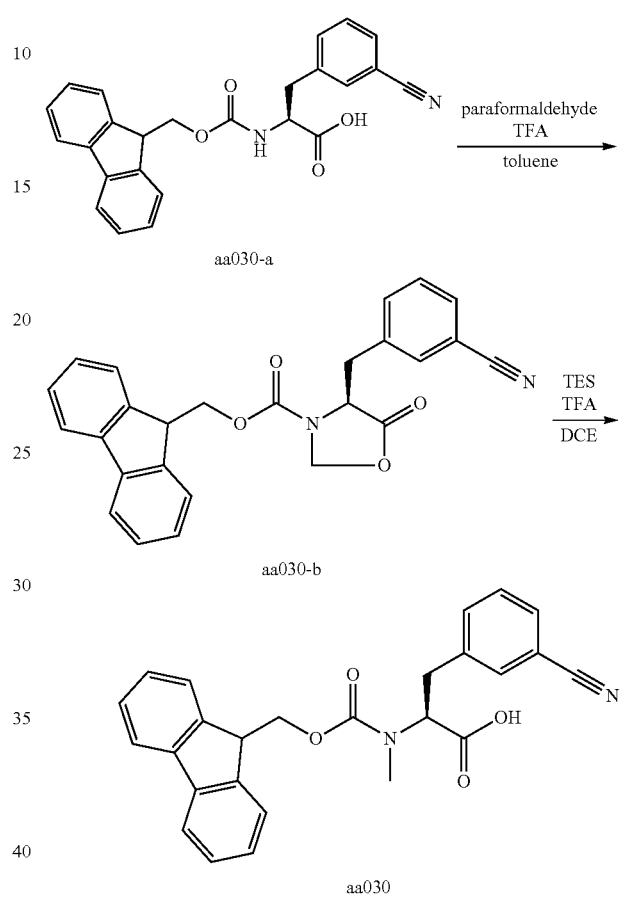

In a nitrogen atmosphere, paraformaldehyde (172 mg, 5.74 mmol) and TFA (1.326 mL, 17.22 mmol) were added to a toluene solution (5.7 mL) of(S)-2-((((9H-fluoren-9-yl) methoxy) carbonyl)amino)-3-(3-cyanophenyl) propanoic acid (aa030-a, Fmoc-Phe (3—CN)—OH) (789 mg, 1.913 mmol), and the mixture was stirred at room temperature for 5 hours and 30 minutes. The reaction solution was concentrated under reduced pressure, diluted with DCM, then washed with a saturated aqueous sodium hydrogen carbonate solution, dried over anhydrous magnesium sulfate, and filtered. The resulting solution was concentrated under reduced pressure to give Compound aa030-b (859 mg) as a crude product. The compound was used in the next reaction without further purification.

In a nitrogen atmosphere, TES (2.75 mL, 17.22 mmol) and TFA (3.98 mL, 51.7 mmol) were added to a DCE (10 mL) solution of Compound aa030-b (853 mg) at room temperature, and the mixture was stirred at 60° C. for 5 hours. The reaction solution was cooled to room temperature, the solvent was distilled off under reduced pressure, t-butyl methyl ether/n-hexane (1/1) was added to the resulting crude product, and the mixture was extracted 5 times with a saturated aqueous sodium hydrogen carbonate solution. The pH of the resulting aqueous layer was acidified with concentrated hydrochloric acid, and then the mixture was extracted with ethyl acetate 3 times. The organic layer was washed with saturated brine, dried over anhydrous magnesium sulfate, and filtered, and then the solvent was distilled off under reduced pressure to give Compound aa030 (811 mg, 2 steps, 99%). The resulting Compound aa060 was used in peptide synthesis without further purification.

LCMS (ESI) m/z=427 (M+H)+

Retention time: 0.83 min (Analytical condition SQDFA05)

Synthesis of Compound aa029

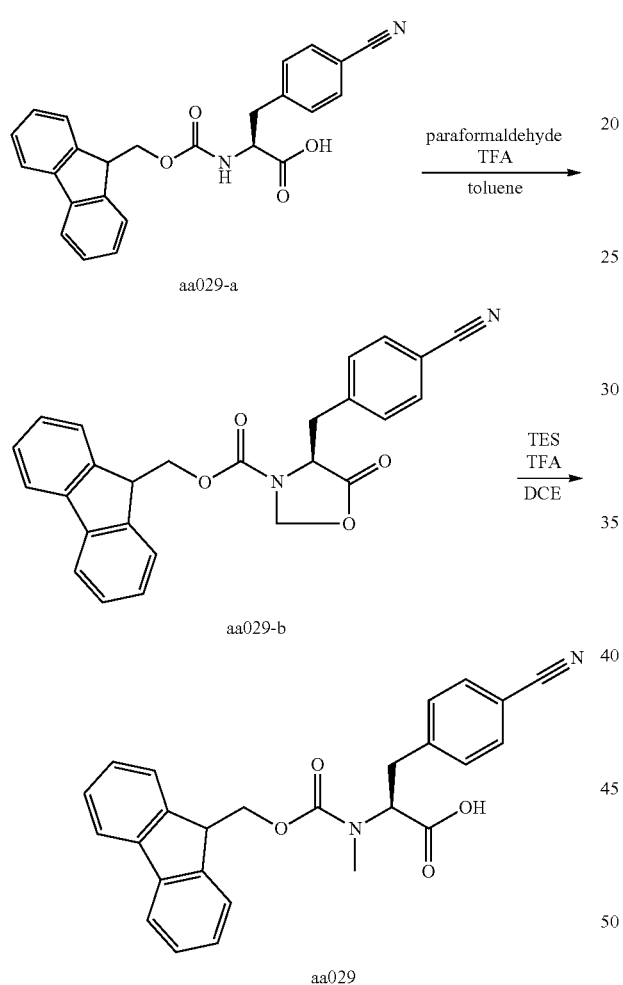

Synthesis of Compound aa031

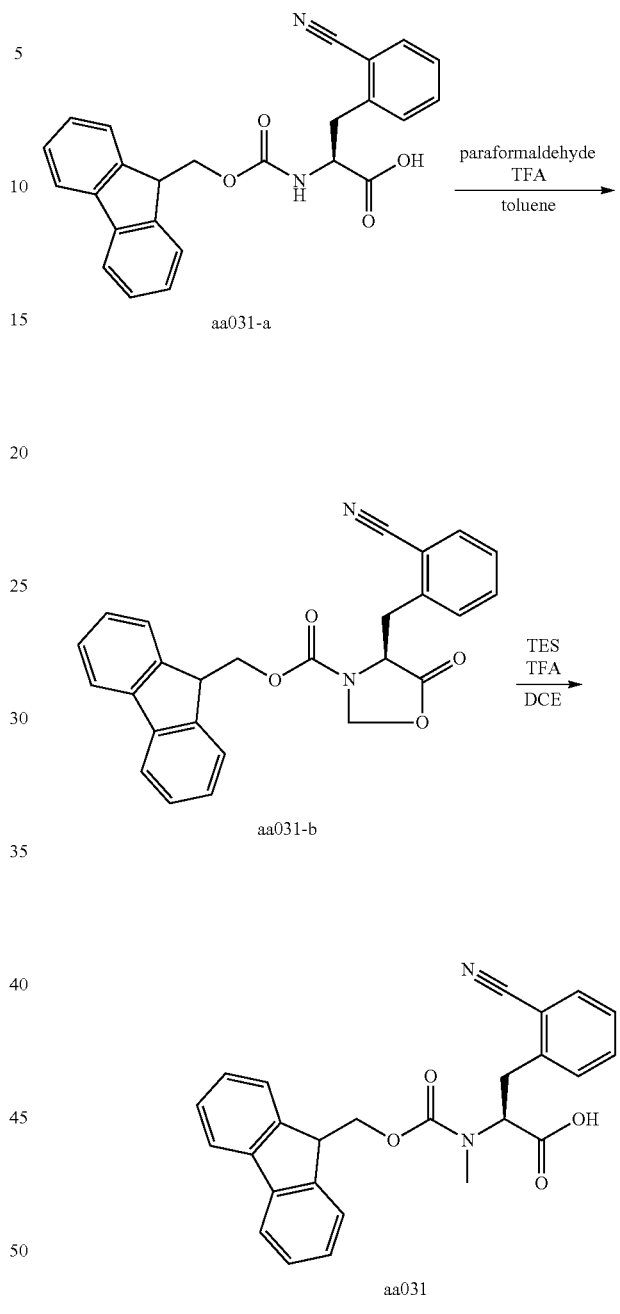

Using Compound aa029-a, ((2S)-3-(4-cyanophenyl)-2-(9H-fluoren-9-ylmethoxycarbonylamino) propanoic acid, Fmoc-Phe (4—CN)—OH)(1 g, 2.425 mmol) as a starting material, Compound aa029 (1.14 g, 2 steps, 108%) was obtained as a crude product in the same manner as the synthesis of Compound aa030. The resulting Compound aa029 was used in peptide synthesis without further purification.

LCMS (ESI) m/z=427 (M+H)+

Retention time: 0.82 min (Analytical condition SQDFA05)

Using Compound aa031-a, ((2S)-3-(2-cyanophenyl)-2-(9H-fluoren-9-ylmethoxycarbonylamino) propanoic acid, Fmoc-Phe (2—CN)—OH)(1 g, 2.425 mmol) as a starting material, Compound aa031-b was obtained as a crude product in the same manner as the synthesis of Compound aa030-b. Using the resulting Compound aa031-b, the crude product obtained in the same manner as the synthesis of Compound aa030 was purified by reverse phase column chromatography (0.1% aqueous formic acid solution/0.1% formic acid acetonitrile solution) to give Compound aa031 (529 mg, 2 steps, 51%).

LCMS (ESI) m/z=427 (M+H)+

Retention time: 0.85 min (Analytical condition SQDFA05)

Synthesis of Compound aa050

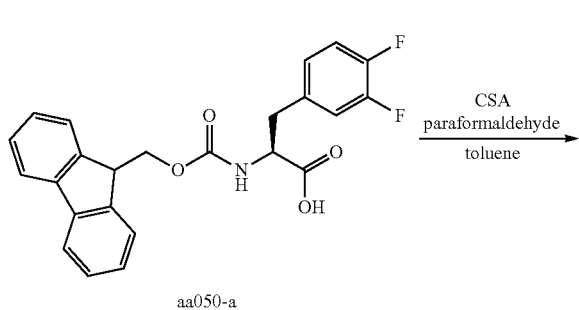

aa050-a

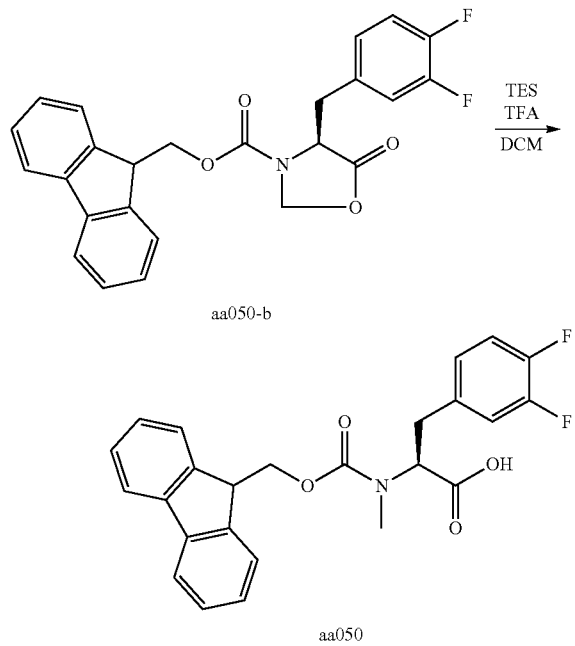

aa050

Using Compound aa050-a, ((2S)-3-(3,4-difluorophenyl)-2-[9H-fluoren-9-ylmethoxycarbonyl(methyl)amino]propanoic acid, Fmoc-Phe (34-F2)—OH)(105 mg, 0.247 mmol) as a starting material, Compound aa050-b was obtained as a crude product in the same manner as the synthesis of Compound aa004-b. Furthermore, using aa050-b, Compound aa050 (74.4 mg, 2 steps, 69%) was obtained in the same manner as the synthesis of Compound aa030. LCMS (ESI) m/z=438 (M+H)+

Retention time: 0.88 min (Analytical condition SQDFA05)

Synthesis of Compound aa019

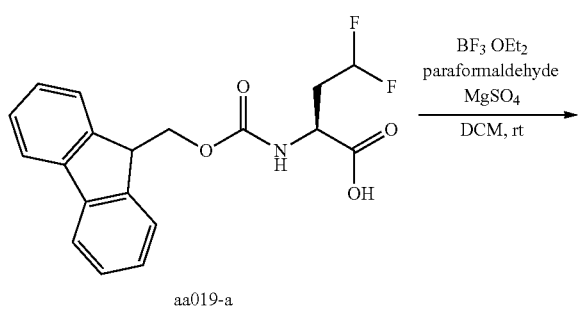

aa019-a

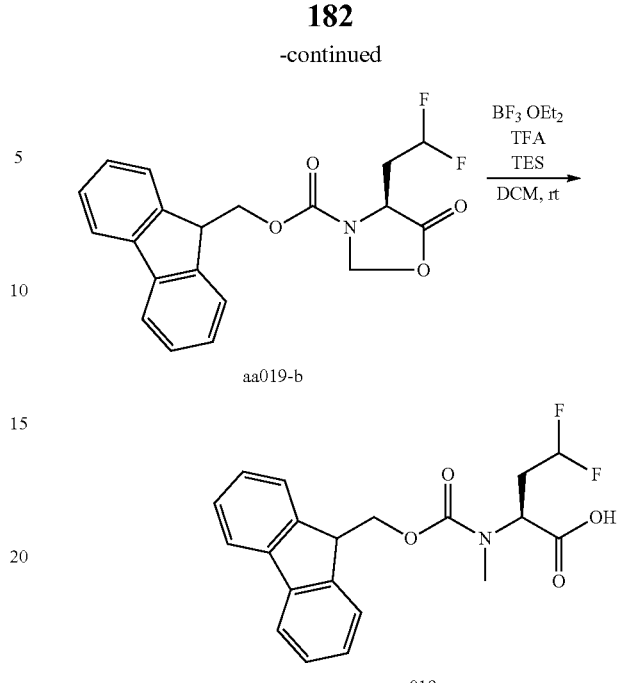

aa019

Compound aa019-a (5.00 g, 13.8 mmol) was suspended in DCM (46 mL), and paraformaldehyde (2.08 g, 69 mmol) and magnesium sulfate (4.16 g, 34.6 mmol) were added. A boron trifluoride diethyl ether complex (BF3·OEt2)(2.10 mL, 16.6 mmol) was added dropwise thereto, and the mixture was stirred at room temperature for 1 hour. Solids were filtered off, and TES (5.51 mL, 34.6 mmol) and water (0.249 mL, 13.8 mmol) were added. BF3·OEt2 (2.63 mL, 20.8 mmol) was added dropwise thereto at 0° C., and the mixture was stirred at room temperature for 1 hour. TES (1.10 mL, 6.92 mmol) was added, the mixture was stirred at room temperature for 40 minutes, BF3.OEt2 (0.877 mL, 6.92 mmol) was added, and the mixture was stirred at room temperature. The reaction solution was washed with a saturated aqueous sodium chloride solution (25 mL) and washed with saturated brine (50 mL). The organic layer was dried over sodium sulfate and filtered off, and the solvent was distilled off under reduced pressure. The resulting solids were pulverized and washed 3 times with n-hexane (50 mL) to give Compound aa019 (4.93 g, 95%).

LCMS (ESI) m/z=376 (M+H)+

Retention time: 0.80 min (Analytical condition SQDFA05)

Synthesis of Compound aa331

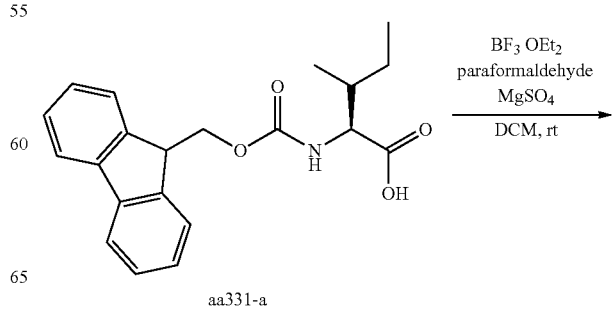

aa331-a

183

-continued

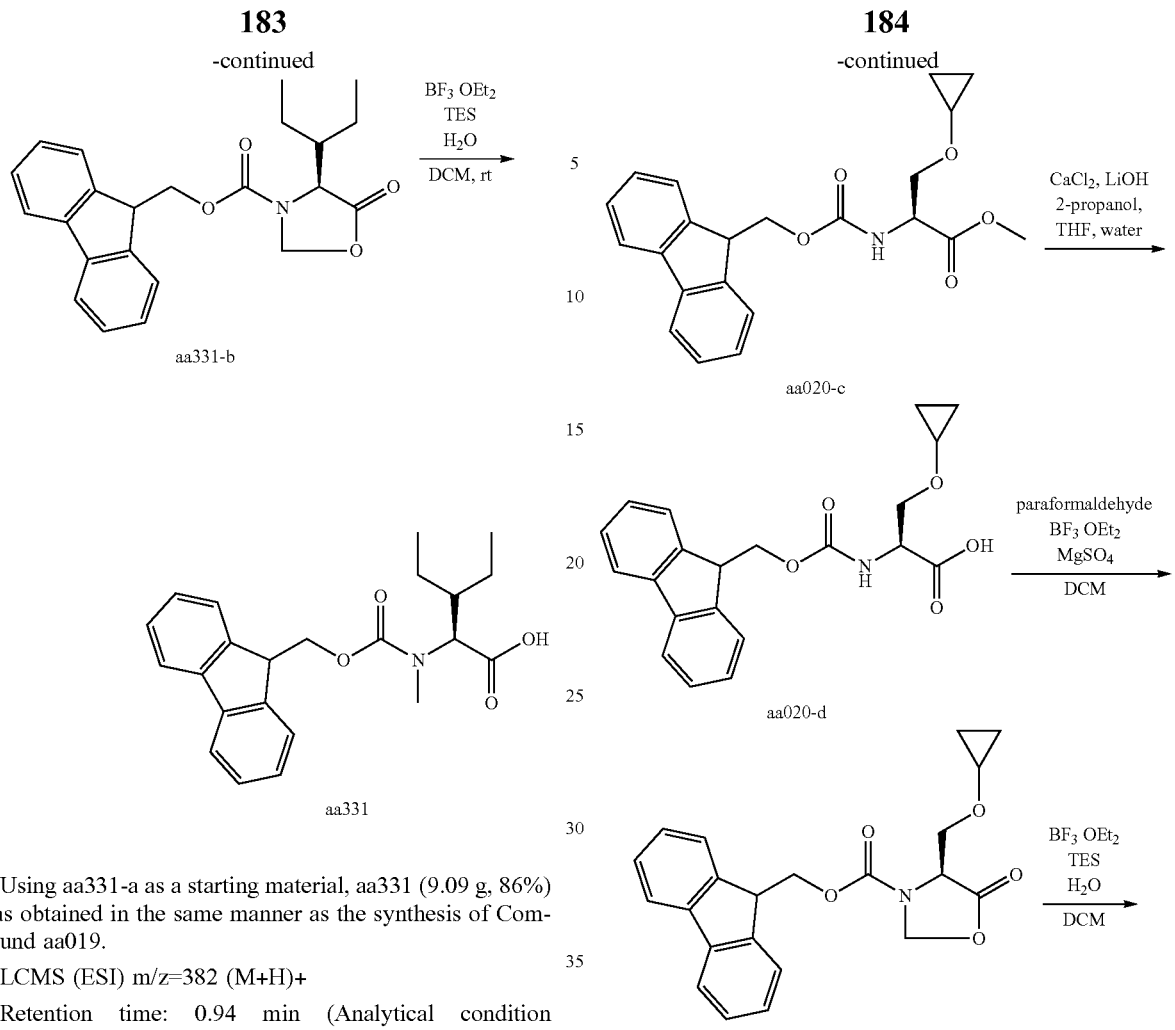

Using aa331-a as a starting material, aa331 (9.09 g, 86%) was obtained in the same manner as the synthesis of Compound aa019.

LCMS (ESI) m/z=382 (M+H)+

Retention time: 0.94 min (Analytical condition SQDFA05)

Synthesis of Compound aa020

184

-continued

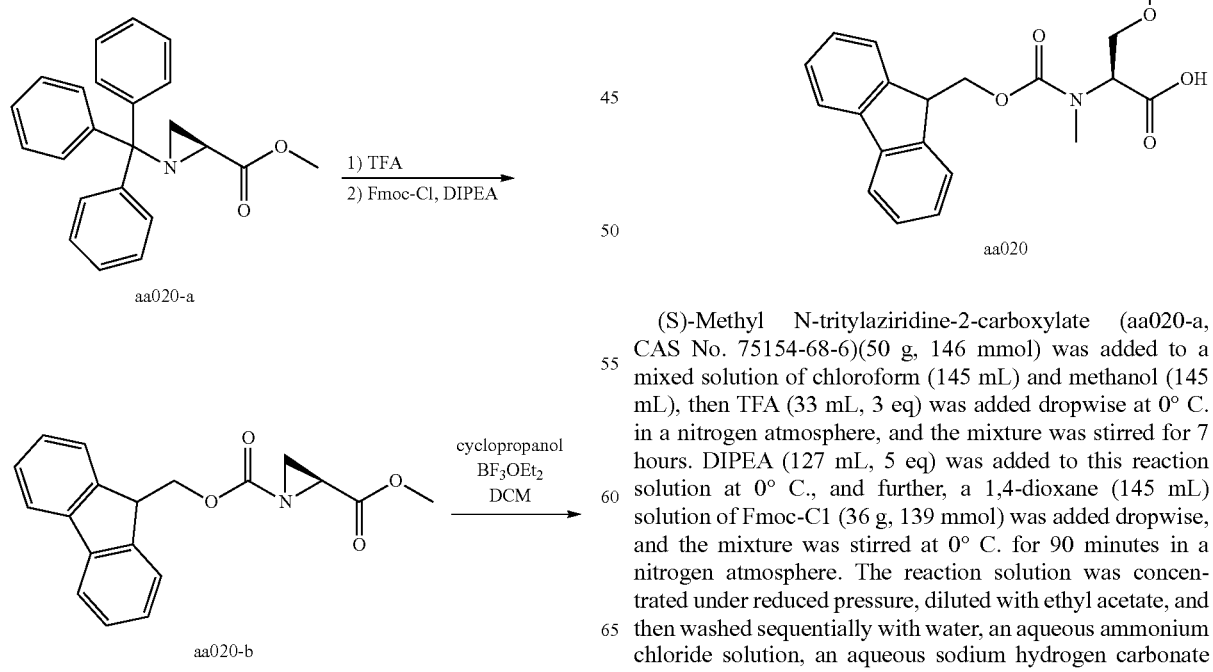

(S)-Methyl N-tritylaziridine-2-carboxylate (aa020-a, CAS No. 75154-68-6)(50 g, 146 mmol) was added to a mixed solution of chloroform (145 mL) and methanol (145 mL), then TFA (33 mL, 3 eq) was added dropwise at 0° C. in a nitrogen atmosphere, and the mixture was stirred for 7 hours. DIPEA (127 mL, 5 eq) was added to this reaction solution at 0° C., and further, a 1,4-dioxane (145 mL) solution of Fmoc-Cl (36 g, 139 mmol) was added dropwise, and the mixture was stirred at 0° C. for 90 minutes in a nitrogen atmosphere. The reaction solution was concentrated under reduced pressure, diluted with ethyl acetate, and then washed sequentially with water, an aqueous ammonium chloride solution, an aqueous sodium hydrogen carbonate solution, and saturated brine. After the resulting organic layer was dried with anhydrous sodium sulfate, the residue obtained by distilling off the solvent under reduced pressure was purified by silica gel column chromatography (ethyl acetate/petroleum ether, 0/100 to 10/90) to give Compound aa020-b (1-O-(9H-fluoren-9-ylmethyl)₂-O-methyl(2S)-aziridine-1,2-dicarboxylate)(40 g, 85%).

LCMS (ESI) m/z=324 (M+H)+

Retention time: 2.631 min (Analytical condition SMD method_10))

In a nitrogen atmosphere, Compound aa020-b, (1-O-(9H-fluoren-9-ylmethyl)₂-O-methyl(2S)-aziridine-1,2-dicarboxylate)(5 g, 15.46 mmol) was dissolved in DCM (30.9 mL), cyclopropanol (1.665 mL, 26.3 mmol) was added, and then a boron trifluoride diethyl ether complex (BF3·OEt2) (0).291 mL, 2.319 mmol) was added while the mixture was ice-cooled. After the mixture was reacted for 2 hours while being ice-cooled, water and a saturated aqueous sodium hydrogen carbonate solution were added to the reaction solution to quench the reaction, the aqueous layer was removed by a phase separator, and then the organic layer was concentrated under reduced pressure. The resulting residue was purified by silica gel column chromatography (n-hexane/ethyl acetate=4/1) to give Compound aa020-c (4.6 g, 78%).

LCMS (ESI) m/z=382 (M+H)+

Retention time: 0.89 min (Analytical condition SQDFA05)

Calcium chloride (20.08 g, 181 mmol) was dissolved in water (50.2 mL), lithium hydroxide monohydrate (2.024 g, 48.2 mmol) was added thereto, and the mixture was stirred at room temperature for 5 minutes to prepare Aqueous Solution A. Compound aa020-c (4.6 g, 12.06 mmol) was dissolved in isopropanol (201 mL) and THF (50.2 mL), Aqueous Solution A prepared in advance was added, and the mixture was stirred at room temperature for 5 hours. Then, 1 N hydrochloric acid (72 mL) was added to the reaction solution, and then isopropanol and THF were removed by concentration under reduced pressure. The resulting aqueous layer was diluted with water (50).2 mL), and extracted 3 times with ethyl acetate (total amount 100 mL). The organic layer was washed with water and saturated brine, dried over anhydrous sodium sulfate, and filtered, and the filtrate was concentrated under reduced pressure. The resulting residue was washed with ethyl acetate/n-hexane (1/2, 20 v/w) to give aa020-d, ((2S)-3-cyclopropyloxy-2-(9H-fluoren-9-ylmethoxycarbonylamino) propanoic acid, Fmoc-Ser (cPr)—OH) (3.5 g, 79%).

LCMS (ESI) m/z=368 (M+H)+

Retention time: 0.78 min (Analytical condition SQDFA05)

Paraformaldehyde (1.815 g, 60.5 mmol), magnesium sulfate (2.36 g, 19.63 mmol), and a boron trifluoride diethyl ether complex (BF3·OEt2)(1.184 mL, 9.42 mmol) were added in a nitrogen atmosphere to a DCM (87 mL) solution of Compound aa020-d, ((2S)-3-cyclopropyloxy-2-(9H-fluoren-9-ylmethoxycarbonylamino) propanoic acid, Fmoc-Ser (cPr)—OH) (2.89 g, 7.85 mmol), and the mixture was stirred at room temperature for 2 hours. A saturated aqueous sodium hydrogen carbonate solution was added to the reaction solution to separate the organic layer and the aqueous layer. The aqueous layer was extracted twice with DCM, the combined organic layer was washed with saturated brine and dried over sodium sulfate, and the solvent was distilled off under reduced pressure to give Compound aa020-e as a crude product (3.1 g, quant.).

LCMS (ESI) m/z=380)(M+H)+

Retention time: 0.93 min (Analytical condition SQDFA05)

Triethylsilane (3.13 mL, 19.64 mmol), water (0.141 mL, 7.85 mmol), and a boron trifluoride diethyl ether complex (BF3·OEt2)(2.49 mL, 19.6 mmol) were added to DCM (26.2 mL) solution of the resulting Compound aa020-e (2.98 g, 7.85 mmol) under an ice-cold condition in a nitrogen atmosphere, and the mixture was stirred for 2 hours. A saturated aqueous ammonium chloride solution was added to the reaction solution to separate the organic layer. The organic layer was washed with a saturated aqueous ammonium chloride solution, then washed with saturated brine, and concentrated under reduced pressure to give a crude product. The resulting crude product was dissolved in acetonitrile, washed with n-hexane, and the acetonitrile layer was concentrated under reduced pressure to give Compound aa020 (2.71 g, 90%).

LCMS (ESI) m/z=382 (M+H)+

Retention time: 0.83 min (Analytical condition SQDFA05)

Synthesis of Compound aa006

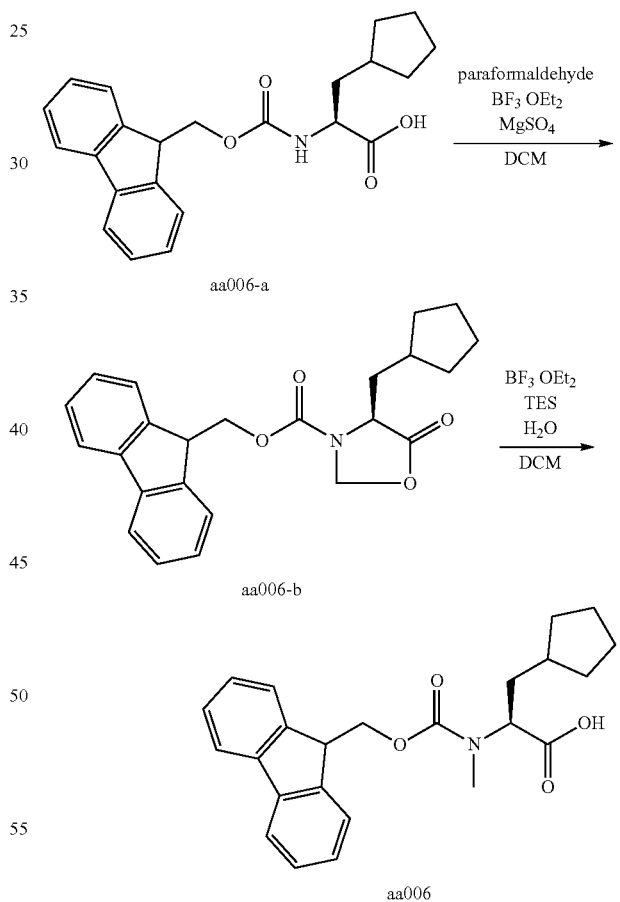

Using Compound aa006-a, ((2S)-3-cyclopentyl-2-[9H-fluoren-9-ylmethoxycarbonylamino]propanoic acid, Fmoc-Ala (cPent)-OH)(10 g, 26.4 mmol) as a starting material, Compound aa006-b (10.5 g) was obtained as a crude product in the same manner as the synthesis of Compound aa020-e.

LCMS (ESI) m/z=392 (M+H)+

Retention time: 1.05 min (Analytical condition SQDFA05)

The resulting Compound aa006-b (10.5 g) was reacted in the same manner as the synthesis of Compound aa020, and then the resulting crude product was purified by reverse phase column chromatography (0.1% aqueous formic acid solution/0.1% formic acid acetonitrile solution) to give Compound aa006 (10.11 g, 2 steps, 96%).

LCMS (ESI) m/z=394 (M+H)+

Retention time: 0.98 min (Analytical condition SQDFA05)

Synthesis of Compound aa010

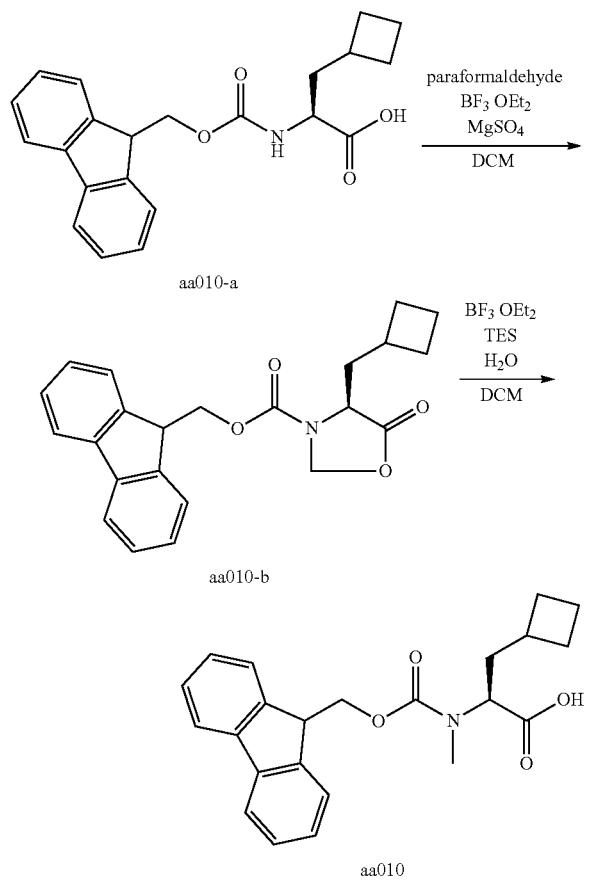

Using Compound aa010-a, ((2S)-3-cyclobutyl-2-[9H-fluoren-9-ylmethoxycarbonylamino]propanoic acid, Fmoc-Ala (cBu)-OH)(3.36 g, 9.19 mmol) as a starting material, Compound aa010-b (3.63 g) was obtained as a crude product in the same manner as the synthesis of Compound aa020-e.

LCMS (ESI) m/z=378 (M+H)+

Retention time: 1.01 min (Analytical condition SQDFA05)

The resulting Compound aa010-b (3.63 g) was reacted in the same manner as the synthesis of Compound aa020, and then the resulting crude product was purified by reverse phase column chromatography (0.1% formic acid-water/0.1% formic acid-acetonitrile) to give Compound aa010 (3.18 g, 2 steps, 91%).

LCMS (ESI) m/z=380 (M+H)+

Retention time: 0.94 min (Analytical condition SQDFA05)

Synthesis of Compound aa047

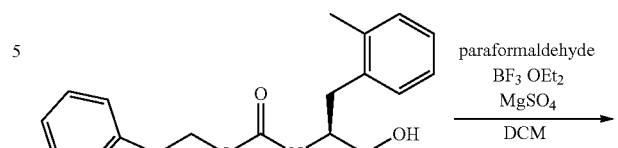

aa047-a

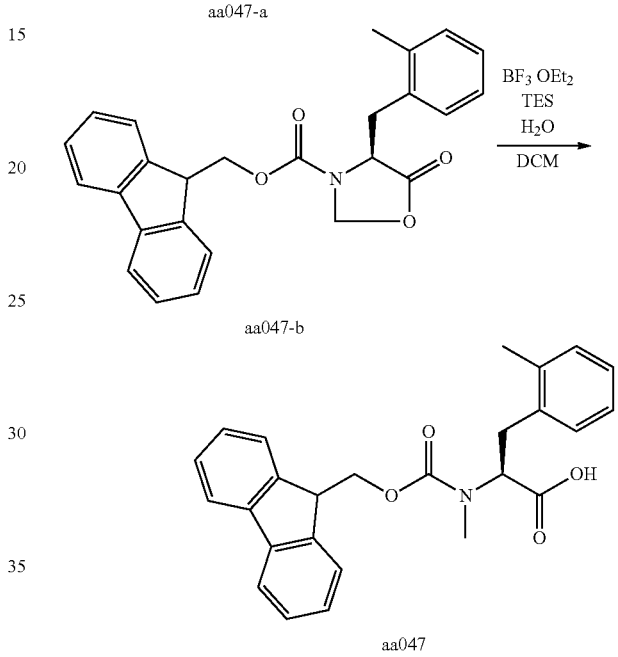

Using Compound aa047-a, ((2S)-2-[9H-fluoren-9-yl-methoxycarbonylamino]-3-(2-methylphenyl) propanoic acid, Fmoc-Phe (2-Me)-OH)(2 g, 4.98 mmol) as a starting material, a saturated aqueous sodium hydrogen carbonate solution was added to the reaction solution obtained in the same manner as the synthesis of Compound aa020-e, a silica gel column (2 v/w) was charged with the mixture, and this was eluted with DCM to give Compound aa047-b as a crude product (1.45 g). Using the resulting Compound aa047-b, Compound aa047 (1.21 g, 2 steps, 58%) was obtained in the same manner as the synthesis of Compound aa020.

LCMS (ESI) m/z=416 (M+H)+

Retention time: 0.94 min (Analytical condition SQDFA05)

Synthesis of Compound aa060

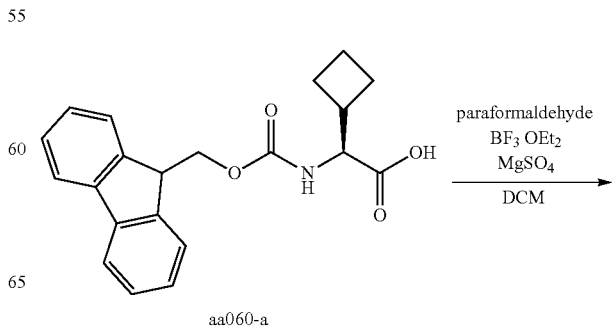

aa060-a

-continued

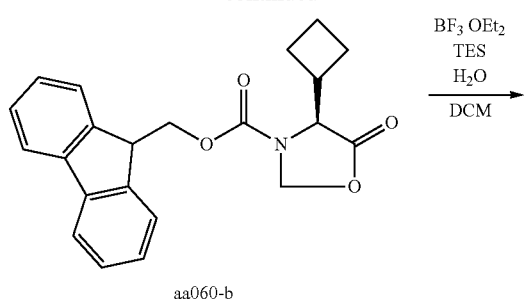

aa060-b

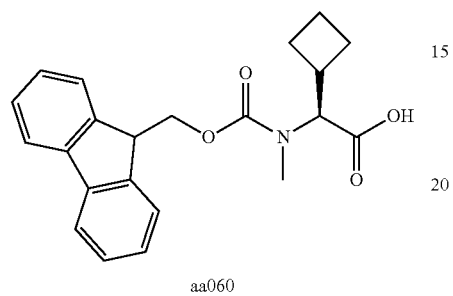

aa060

Using Compound aa060-a, ((2S)-2-cyclobutyl-2-[9H-fluoren-9-ylmethoxycarbonylamino]acetic acid, Fmoc-Gly(cBu)-OH)(2.5 g, 7.11 mmol) as a starting material, Compound aa075-b was obtained as a crude product in the same manner as the synthesis of Compound aa020-e.

LCMS (ESI) m/z=364 (M+H)+

Retention time: 0.97 min (Analytical condition SQDFA05)

The entire amount of Compound aa060-b obtained as mentioned above was reacted in the same manner as the synthesis of Compound aa020, and then the resulting crude product was purified by reverse phase column chromatography (0.1% aqueous formic acid solution/0.1% formic acid acetonitrile solution) to give Compound aa060 (2.32 g, 2 steps, 89%).

LCMS (ESI) m/z=366 (M+H)+

Retention time: 0.88 min (Analytical condition SQDFA05)

Synthesis of Compound aa021

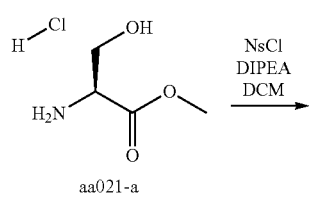

aa021-a

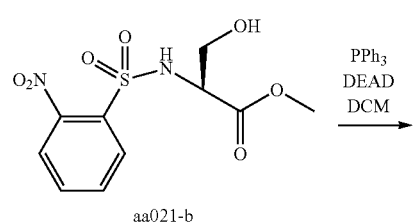

aa021-b

-continued

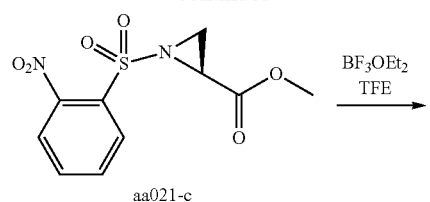

aa021-c

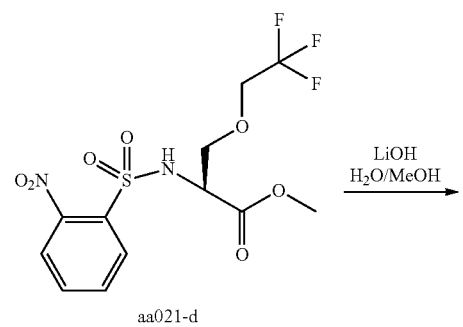

aa021-d

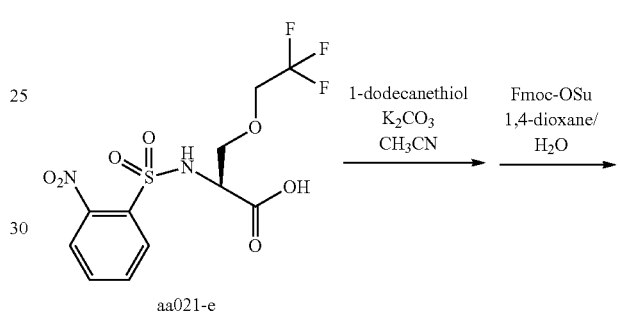

aa021-e

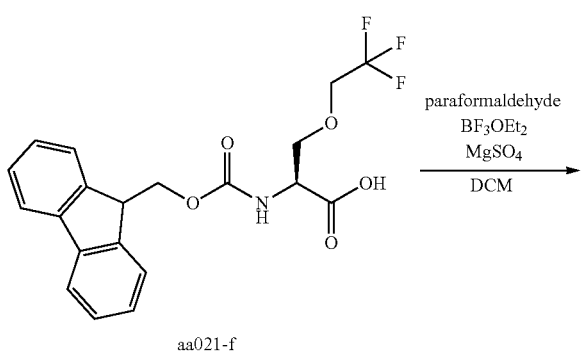

aa021-f

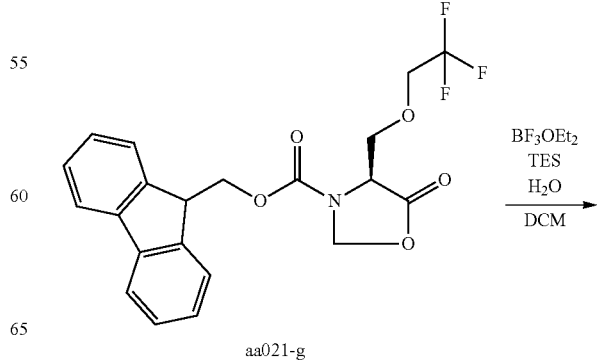

aa021-g

-continued

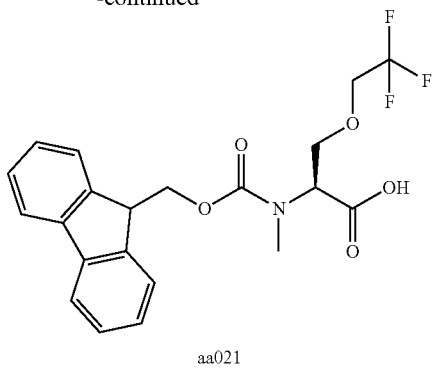

aa021

2-Nitrobenzenesulfonyl chloride (NsCl)(32.37 g, 146 mmol) and L-serine methyl ester hydrochloride (aa021-a, 25 g, 161 mmol, CAS No. 5680-80-8) were dissolved in DCM (874 mL), and DIPEA (51 mL, 292 mmol) was added at 5° C. The mixture was stirred at room temperature for 1 hour, then washed twice with water (440 mL), washed once with saturated brine/water (1/1, 440 mL), and then dried over magnesium sulfate. Magnesium sulfate was filtered off, and then the filtrate was concentrated under reduced pressure to give Compound aa021-b as a crude product (39.4 g, 89%).

LCMS (ESI) m/z=302.9 (M–H)–

Retention time: 0.729 min (Analytical condition SMD method_06)

Compound aa021-b (23 g, 75.6 mmol) was dissolved in DCM (598 mL), and triphenylphosphine (31.7 g, 121 mmol) was added at room temperature. After the mixture was cooled to –14° C., DEAD (55.0 mL, 121 mmol) was added over 10 minutes, and then the mixture was stirred at –5° C. for 50 minutes. n-Hexane (300 mL) was added, and the precipitate was filtered off. The filtrate was purified by silica gel column chromatography (n-hexane/DCM=50:50 to 0:100) to give Compound aa021-c (13.3 g, 62%).

LCMS (ESI) m/z=287 (M+H)+

Retention time: 0.872 min (Analytical condition SMD method_06)

Compound aa021-c (10.7 g, 37.3 mmol) was dissolved in TFE (75 mL), a boron trifluoride diethyl ether complex (BF3·OEt2)(0.469 mL, 3.73 mmol) was added, and then the mixture was stirred at 70° C. for 30 minutes. TFE was distilled off under reduced pressure, and the resulting crude product was purified by reverse phase column chromatography (0.1% formic acid-containing acetonitrile/0.1% formic acid-containing distilled water) to give Compound aa021-d (12.3 g, 85%).

LCMS (ESI) m/z=387 (M+H)+

Retention time: 0).72 min (Analytical condition SQDFA05)

Compound aa021-d (12 g, 31.1 mmol) was dissolved in methanol (47 mL), and an aqueous solution (31 mL) of lithium hydroxide monohydrate (5.21 g, 124 mmol) was added. The mixture was stirred at room temperature for 90 minutes, then formic acid (11.7 mL, 311 mmol) was added, and the mixture was diluted with water (30 mL) and then purified by reverse phase column chromatography (0.1% formic acid-containing acetonitrile/0.1% formic acid-containing distilled water) to give Compound aa021-e (7.90 g, 68%).

LCMS (ESI) m/z=373 (M+H)+

Retention time: 0.63 min (Analytical condition SQDFA05)

Compound aa021-e (7.72 g, 20.7 mmol) was dissolved in acetonitrile (104 mL), potassium carbonate (7.17 g, 51.8 mmol) and dodecanethiol (7.44 mL, 31.1 mmol) were added, and then the mixture was stirred at room temperature for 74 hours. This was diluted with water (1 ( )) mL), and washed twice with TBME (200 mL). A 1,4-dioxane (150) mL) solution of Fmoc-OSu (3.5 g) was added to the resulting aqueous solution, and the mixture was stirred for 25 minutes. Further, a 1,4-dioxane (10 mL) solution of Fmoc-OSu (700) mg) was added, and the mixture was stirred for 5 minutes. Furthermore, a 1,4-dioxane (5 mL) solution of Fmoc-OSu (350) mg) was added, and the mixture was stirred for 5 minutes. Further, a 1,4-dioxane (5 mL) solution of Fmoc-OSu (350 mg) was added, the mixture was stirred for 5 minutes, then formic acid (3.9 mL) was added, and the solvent was distilled off under reduced pressure. The resulting crude product was purified by reverse phase column chromatography (0).1% formic acid-containing acetonitrile/0).1% formic acid-containing distilled water) to give Compound aa ( ) 1-f, ((2S)-2-(9H-fluoren-9-ylmethoxycarbonylamino)-3-(2,2,2-trifluoroethoxy) propanoic acid, Fmoc-Ser (Tfe)-OH)(5.67 g, 67%).

LCMS (ESI) m/z=410)(M+H)+

Retention time: 2.35 min (Analytical condition SQDFA05 long)

Using Compound aa021-f (2.00 g, 4.89 mmol) as a starting material, Compound aa021-g was obtained as a crude product in the same manner as the synthesis of Compound aa020-e. Furthermore, Compound aa021 (1.80 g, 2 steps, 87%) was obtained in the same manner as the synthesis of Compound aa020.

LCMS (ESI) m/z=424 (M+H)+

Retention time: 0.84 min (Analytical condition SQDFA05)

Synthesis of Compound aa022

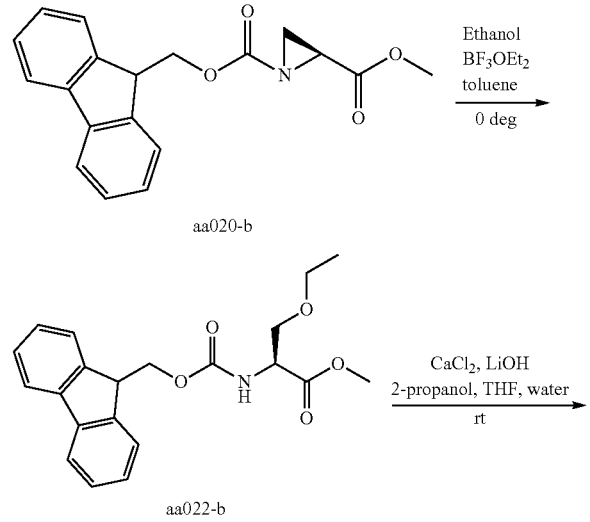

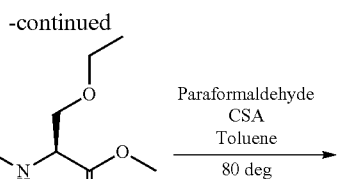

aa022-c

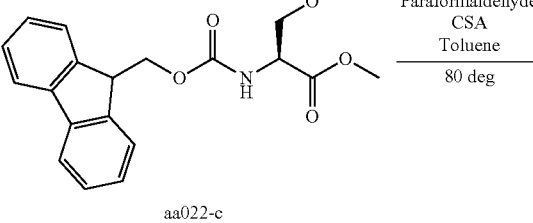

aa022-d

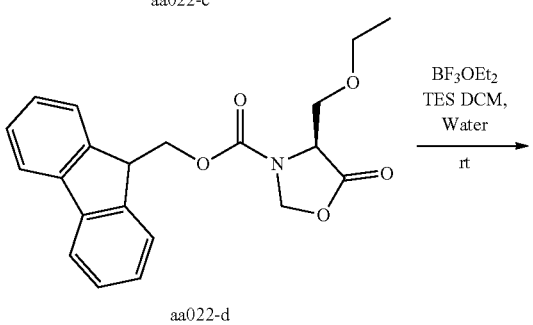

aa022

In a nitrogen atmosphere, Compound aa020-b (1 g, 3.09 mmol) was dissolved in toluene (6.2 mL), ethanol (0.542 mL, 9.28 mmol) was added, and then BF3.OEt2 (0.059 mL, 0.464 mmol) was added dropwise over 5 minutes while being ice-cooled. This was stirred for 2.5 hours while being brought back to room temperature. The reaction was quenched by adding a saturated aqueous NaHCO₃ solution, and the aqueous layer was removed by a phase separator. The organic layer was dried over anhydrous sodium sulfate, and the solvent was distilled off under reduced pressure. Ethyl acetate/hexane (3/1, 24 mL) was added to the resulting residue, and the solvent was distilled off under reduced pressure. Hexane/TBME (85/15, 24 mL) was added to the resulting solids, and the mixture was stirred for 30 minutes, and then the solvent was filtered off to give Compound aa022-b (787 mg, 69%).

LCMS (ESI) m/z=370 (M+H)+

Retention time: 0.86 min (Analytical condition SQDFA05)

Calcium chloride (2.25 g, 20.3 mmol) was dissolved in H₂O (5.7 mL), lithium hydroxide monohydrate (227 mg, 5.41 mmol) was added thereto, and the mixture was stirred at room temperature for 5 minutes to prepare Aqueous Solution A.

Compound aa022-b was dissolved in isopropanol (22.6 mL) and THF (57 mL), Aqueous Solution A prepared in advance was added, and the mixture was stirred at room temperature for 7 hours. Then, 1 N hydrochloric acid (8.1 mL) was added to the reaction solution, and then isopropanol and THF were removed by concentration under reduced pressure. The resulting aqueous layer was diluted with H₂O and extracted 3 times with ethyl acetate. The organic layer was washed with H₂O and saturated brine, dried over anhydrous sodium sulfate, filtered, and then concentrated under reduced pressure. The residue residue was triturated with ethyl acetate/n-hexane (1/5, 20 v/w) to give Compound aa022-c (3.5 g, 79%).

LCMS (ESI) m/z=356 (M+H)+

Retention time: 0.78 min (Analytical condition SQDFA05)

Using aa022-c as a starting material, aa022-d (871 mg, 84%) was obtained as a crude product in the same manner as the synthesis of Compound aa004-b.

LCMS (ESI) m/z=368 (M+H)+

Retention time: 0.84 min (Analytical condition SQDFA05)

Using aa022-d as a starting material, aa022 (254 mg, 90%) was obtained in the same manner as the synthesis of Compound aa004.

LCMS (ESI) m/z=370 (M+H)+

Retention time: 0.80 min (Analytical condition SQDFA05)

Synthesis of Compound aa210

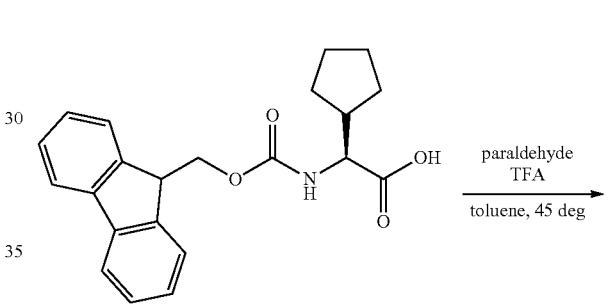

aa210-a

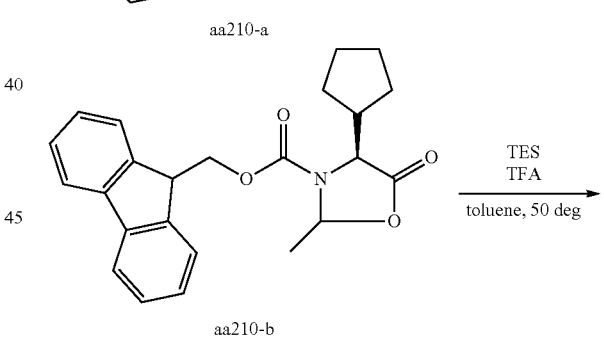

aa210-b

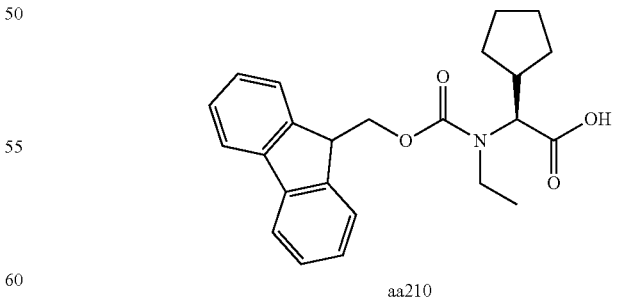

aa210

Compound aa210-a (5.00 g, 13.7 mmol) was dissolved in toluene (17 mL), TFA (9.49 mL, 123 mmol) and paraldehyde (5.42 mL, 41.0 mmol) were added, and the mixture was stirred at 45° C. for 24 hours. The mixture was cooled to 0° C., toluene (17 mL), TFA (19.0 mL, 246 mmol), and TES (19.6 mL, 123 mmol) were added, and the mixture was stirred at 50° C. overnight. The solvent was distilled off under reduced pressure, ethyl acetate was added, and the mixture was washed with a saturated aqueous sodium hydrogen carbonate solution and washed with saturated brine. The organic layer was dried over sodium sulfate and filtered off, and the solvent was distilled off under reduced pressure. Purification by reverse phase column chromatography (0.1% formic acid-containing acetonitrile/0.1% formic acid-containing distilled water) gave Compound aa210 (2.17 g, 40%).

LCMS (ESI) m/z=394 (M+H)+

Retention time: 0.94 min (Analytical condition SQDFA05)

Synthesis of Compound aa201

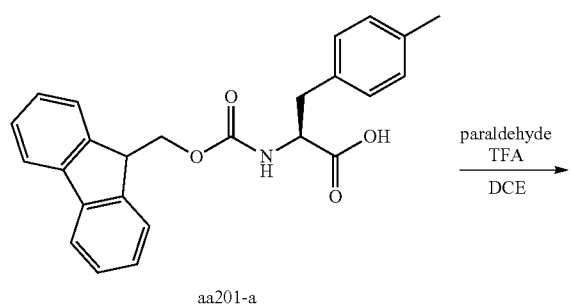

aa201-a

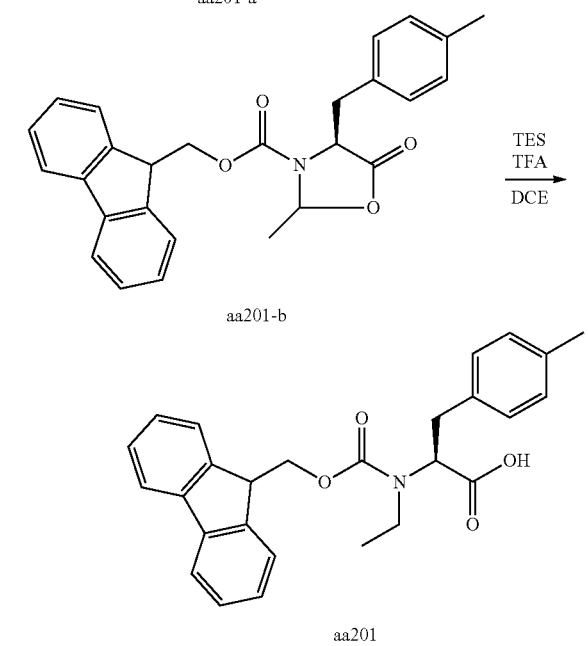

aa201-b aa201

In a nitrogen atmosphere, Compound aa201-a, ((2S)-2-(9H-fluoren-9-ylmethoxycarbonylamino)-3-(4-methylphenyl) propanoic acid, Fmoc-Phe (4-Me)-OH)(5.62 g, 14.0 mmol, CAS No. 199006-54-7) was suspended in DCE (17.5 mL), then paraldehyde (5.61 mL, 42.0 mmol) and TFA (9.65 mL, 126 mmol) were added, and the mixture was stirred at 60° C. for 6 hours. The resulting reaction solution containing Compound aa201-b was directly used in the next step.

LCMS (ESI) m/z=428 (M+H)+

Retention time: 1.03 min (Analytical condition SQDFA05)

DCE (17.5 mL), TFA (19.3 mL, 252 mmol), and TES (20.1 mL, 126 mmol) were added to the resulting reaction solution of Compound aa201-b, and the mixture was stirred at 60° C. for 17 hours. After the mixture was cooled to room temperature and concentrated under reduced pressure, the resulting residue was dissolved in ethyl acetate (40 mL). The organic layer was washed with a saturated aqueous sodium hydrogen carbonate solution (40 mL) and saturated brine (40 mL) and dried over anhydrous sodium sulfate, and then the solvent was distilled off under reduced pressure. The resulting residue was dissolved in acetonitrile (30 mL) and washed twice with hexane (15 mL), and the solvent was distilled off under reduced pressure. The resulting residue was purified by reverse phase column chromatography (0.1% formic acid-containing acetonitrile/0.1% formic acid-containing distilled water) to give Compounds aa201, ((2S)-2-[ethyl(9H-fluoren-9-ylmethoxycarbonyl)amino]-3-(4-methylphenyl) propanoic acid, Fmoc-EtPhe (4-Me)-OH) (4.4 g, 2 steps, 73%).

LCMS (ESI) m/z=430 (M+H)+

Retention time: 0.95 min (Analytical condition SQDFA05)

Synthesis of Compound aa164

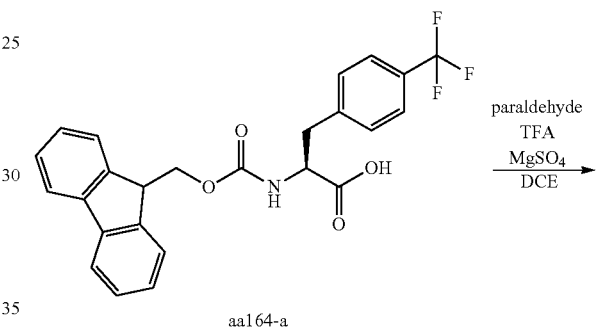

aa164-a

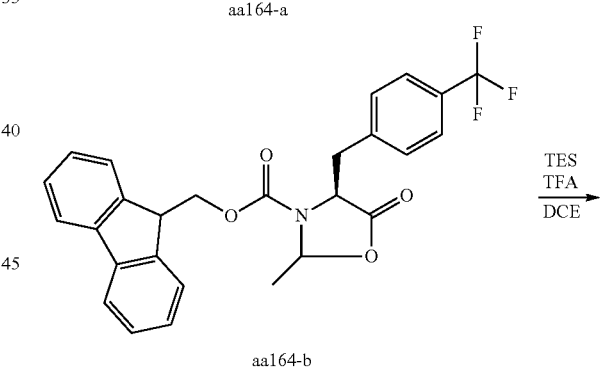

aa164-b

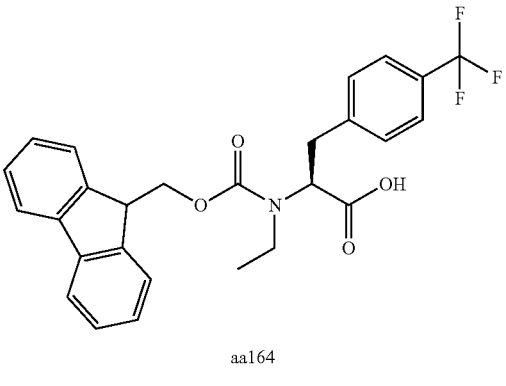

aa164

In a nitrogen atmosphere, Compound aa164-a, ((2S)-2-(9H-fluoren-9-ylmethoxycarbonylamino)-3-[4-(trifluoromethyl)phenyl] propanoic acid, Fmoc-Phe (4—CF3)—OH)

(4.04 g, 8.87 mmol, CAS No. 247113-86-6) was suspended in DCE (11.1 mL), then anhydrous magnesium sulfate (4.27 g, 35.4 mmol), paraldehyde (3.55 mL, 26.6 mmol), and TFA (6.11 mL, 80 mmol) were added, and the mixture was stirred at 60° C. for 3 hours. Furthermore, anhydrous magnesium sulfate (2.14 g, 17.7 mmol) was added, and the mixture was stirred at 60° C. for 1 hour. The resulting reaction solution containing Compound aa164-b was directly used in the next reaction.

LCMS (ESI) m/z=482 (M+H)+

Retention time: 1.04 min (Analytical condition SQDFA05)

DCE (11.1 mL), TFA (12.2 mL, 159 mmol), and triethylsilane (12.7 mL, 80 mmol) were added to the resulting reaction solution containing Compound aa164-b, and the mixture was stirred at 60° C. for 10 hours. The mixture was cooled to room temperature, magnesium sulfate was filtered off, and the mixture was concentrated under reduced pressure. Since the intended reaction was not complete, the resulting residue was dissolved in DCE (22.2 mL), then TFA (18.3 mL, 239 mmol) and triethylsilane (12.7 mL, 80 mmol) were added, and the mixture was stirred at 60° C. for 8 hours. After the mixture was cooled to room temperature and concentrated under reduced pressure, the resulting residue was dissolved in ethyl acetate (40 mL). The organic layer was washed with a saturated aqueous sodium hydrogen carbonate solution (40 mL) and saturated brine (40 mL) and dried over anhydrous sodium sulfate, and then the solvent was distilled off under reduced pressure. The resulting residue was dissolved in acetonitrile (30 mL) and washed twice with hexane (15 mL), and the solvent was distilled off under reduced pressure. The resulting residue was purified by reverse phase column chromatography (0.1% formic acid-containing water/acetonitrile) to give Compound aa164 (1.90 g, 2 steps, 44%).

LCMS (ESI) m/z=484 (M+H)+

Retention time: 0.97 min (Analytical condition SQDFA05)

Synthesis of Compound aa136

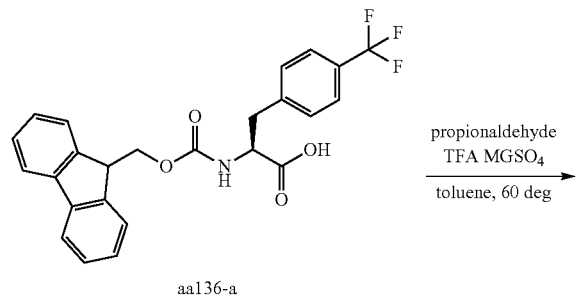

aa136-a propionaldehyde
TFA MGSO$_4$
toluene, 60 deg

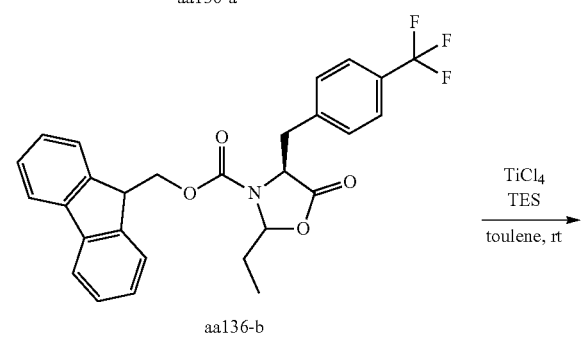

aa136-b

TiCl$_4$
TES
toulene, rt

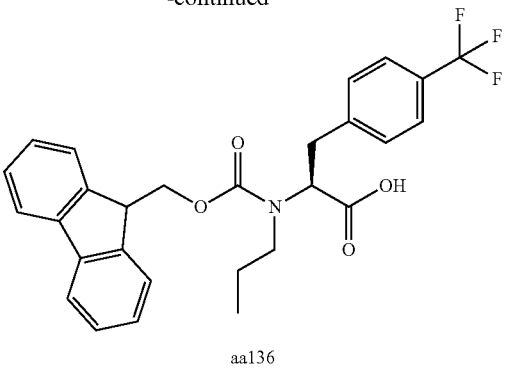

aa136

Compound aa136-a (10.1 g, 22.1 mmol) was dissolved in toluene (28 mL), then propionaldehyde (14.3 mL, 199 mmol), TFA (15.3 mL, 199 mmol), and magnesium sulfate (7.99 g, 66.4 mmol) were added, and the mixture was stirred at 60° C. for 3 hours. Solids were filtered off with a silica gel pad, and the filtrate was washed twice with water (100 mL). Acetonitrile (20) mL) was added thereto, and the mixture was washed with a 1 M aqueous dipotassium hydrogen phosphate solution (30 mL), washed 3 times with a 3.5% aqueous potassium hydrogen carbonate solution (40 mL), and washed with saturated brine (100 mL). The mixture was dried over anhydrous magnesium sulfate and filtered off, and the solvent was distilled off under reduced pressure to give Compound aa136-b as a crude product. The crude product of Compound aa136-b was dissolved in toluene (28 mL), and TES (7.07 mL, 44.3 mmol) was added. The mixture was cooled to 0° C., TiCl$_4$ (4.88 mL, 44.3 mmol) was added, and the mixture was stirred at room temperature for 15 minutes. Water (50 mL) was added dropwise, and the organic layer was washed with water (100 mL) and washed with a 1 M aqueous dipotassium hydrogen phosphate solution (50 mL). n-Hexane (90 mL) was added, and the mixture was extracted 3 times with a mixed solvent of acetonitrile (15 mL) and a 1% aqueous potassium hydrogen carbonate solution (30 mL). Furthermore, the mixture was extracted twice with a mixed solvent of acetonitrile (20 mL) and a 1% aqueous potassium hydrogen carbonate solution (30 mL). n-Hexane (90 mL) was added to the organic layer, and the mixture was extracted twice with a mixed solvent of acetonitrile (20 mL) and a 1% aqueous potassium hydrogen carbonate solution (30 mL). The aqueous layers were combined, n-hexane (80 mL) was added, phosphoric acid was added to adjust pH to 3, and then the mixture was extracted 3 times with TBME (150 mL). The organic layer was washed with saturated brine (50 mL), dried over anhydrous magnesium sulfate, and filtered off, and the solvent was distilled off under reduced pressure to give Compound aa136 (5.03 g, 46%).

LCMS (ESI) m/z=498 (M+H)+

Retention time: 1.02 min (Analytical condition SQDFA05)

Synthesis of Compound aa174

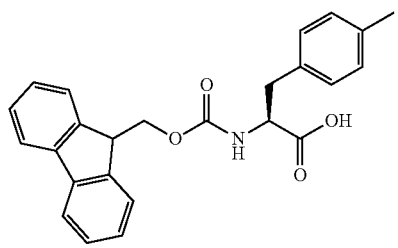

aa174-a

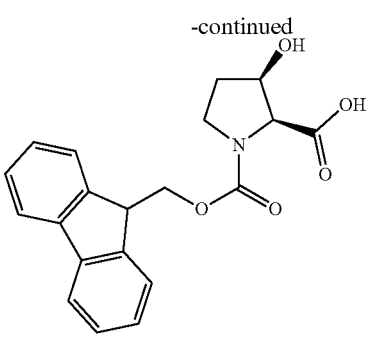

aa264-b

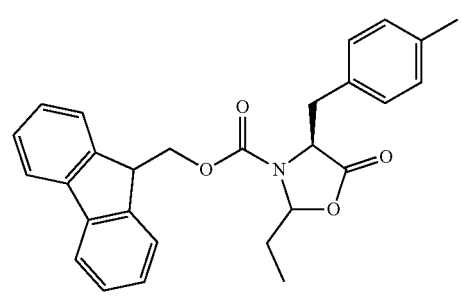

aa174-b

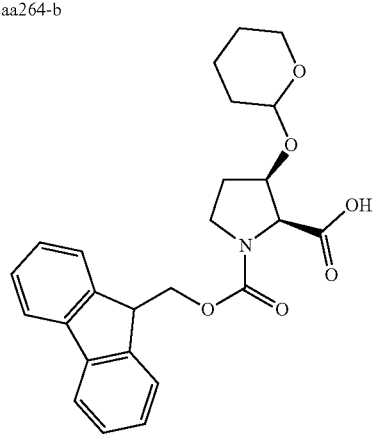

aa264-b

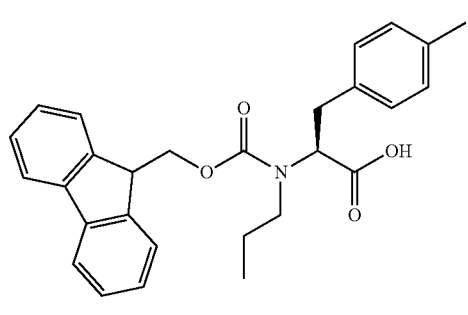

aa174

Using aa174-a as a starting material, aa174 (18.6 g, 84%) was obtained in the same manner as the synthesis of Compound aa136.

LCMS (ESI) m/z=460 (M+NH₄)+

Retention time: 1.41 min (Analytical condition SMD method_04)

Synthesis of Compound aa264

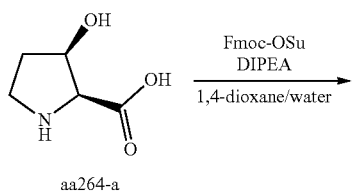

aa264-a

Compound aa264-a (H-cisHyp (3)—OH, 950 mg, 7.24 mmol) was dissolved in water (22 mL), and DIPEA (3.47 mL, 19.9 mmol) was added. A 1,4-dioxane solution (14.5 mL) of Fmoc-OSu (2.44 g, 7.24 mmol) was added thereto. The resulting solids were crushed with a spatula, and irradiated with ultrasonic waves for further pulverization. 1,4-Dioxane (15 mL) was added to and dissolve the solids, and the solution was stirred at room temperature for 40 minutes. Washing was performed twice with n-hexane/CPME (3/1, 10 mL), and potassium hydrogen sulfate (3.70 g, 27.2 mmol) was added. The mixture was extracted 3 times with isopropyl acetate (30 mL), the organic layer was washed with 50% brine (30 mL), dried over anhydrous sodium sulfate, filtered off, and the solvent was distilled off under reduced pressure to give Compound aa264-b (2.39 g, 93%).

LCMS (ESI) m/z=355 (M+H)+

Retention time: 0.64 min (Analytical condition SQDFA05)

Compound 264-b (2.39 g, 6.76 mmol) and PPTS (0.170 g, 0.676 mmol) were suspended in DCM (23 mL), then DHP (1.39 mL, 15.2 mmol) was added, and the mixture was stirred at room temperature for 19 hours. PPTS (0.085 g, 0.338 mmol) and DHP (0.741 mL, 8.11 mmol) were added, and the mixture was stirred at room temperature for 3 hours. This was washed with water, and washed with saturated brine. The mixture was dried over anhydrous sodium sulfate and filtered off, and the solvent was distilled off under reduced pressure. This was dissolved in THF (25 mL), a phosphate buffer (pH=8.2, 25 mL) was added, and the mixture was stirred at 50° C. for 11 hours. Ethyl acetate (25 mL) was added to remove the aqueous layer, and the aqueous layer was extracted twice with ethyl acetate. The organic layer was dried over anhydrous sodium sulfate and filtered off, and the solvent was distilled off under reduced pressure. This was dissolved in DCM (30 mL), and n-hexane (30 mL) was added. Only DCM was distilled off under reduced pressure, and further, n-hexane was distilled off under reduced pressure. n-Hexane was added to the resulting solids, and this was irradiated with ultrasonic waves, and n-hexane was removed by decantation, and this was dried under reduced pressure to give Compound aa264 as a sodium salt. This was dissolved in isopropyl acetate (50 mL), a 0.05 M aqueous phosphoric acid solution (pH=2, 90 mL) was added, the mixture was stirred at room temperature for 10 minutes, and then the aqueous layer was removed. The aqueous layer was extracted with isopropyl acetate, the organic layer was dried over anhydrous sodium sulfate and filtered off, and the solvent was distilled off under reduced pressure. The resulting crude product was purified by reverse phase chromatography (0.1% formic acid-containing acetonitrile/0.1% formic acid-containing distilled water) to give Compound aa264 (2.33 g, 79%).

LCMS (ESI) m/z=456 (M+NH$_3$)+

Retention time: 0.81 min (Analytical condition SQDFA05)

Synthesis of Compound aa265

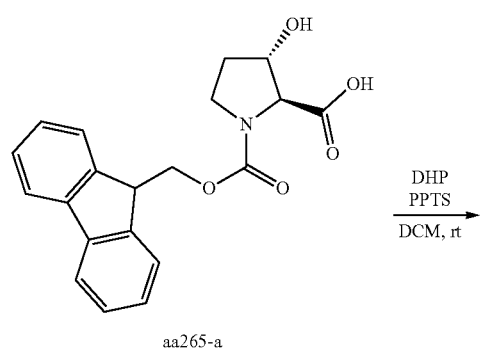

Using aa265-a as a starting material, aa265 (1.38 g, 78%) was obtained in the same manner as the synthesis of Compound aa264.

LCMS (ESI) m/z=439 (M+H)+

Retention time: 0.85 min (Analytical condition SQDFA05)

Synthesis of Compound aa267

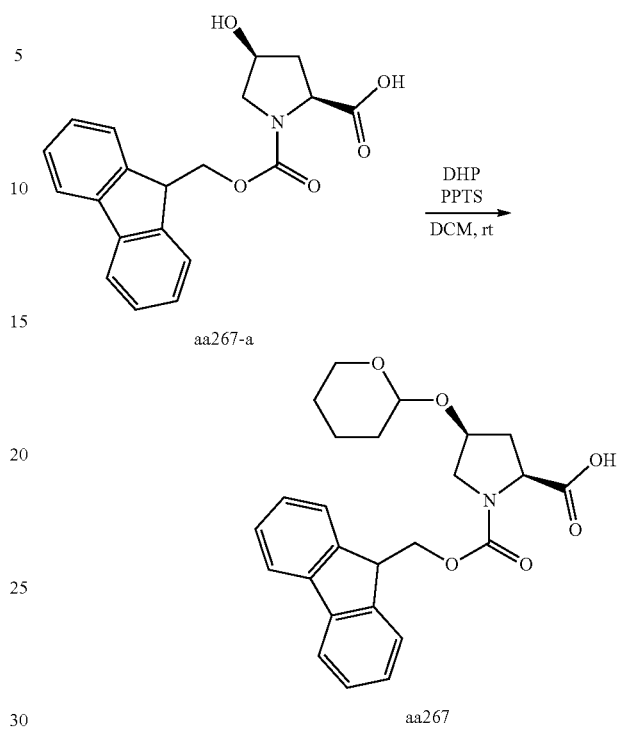

Using aa267-a as a starting material, aa267 (9.04 g, quant) was obtained in the same manner as the synthesis of Compound aa264.

LCMS (ESI) m/z=460 (M+Na)+

Retention time: 0.81 min (Analytical condition SQDFA05)

Synthesis of Compound aa279

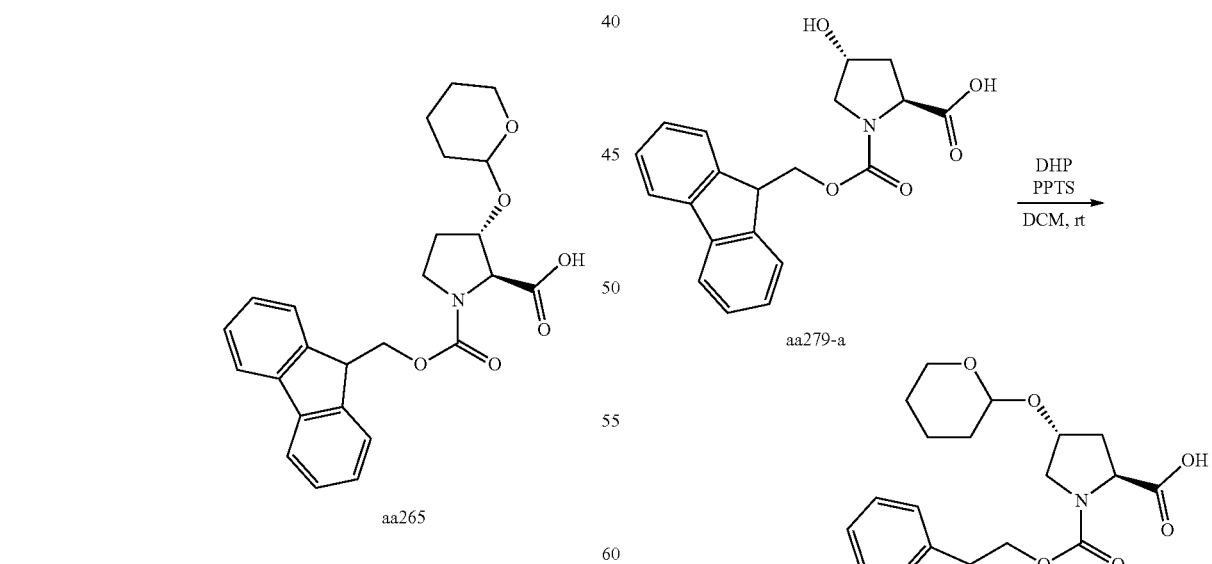

Using aa279-a as a starting material, aa279 (5.15 g, 83%) was obtained in the same manner as the synthesis of Compound aa264.

LCMS (ESI) m/z=460 (M+Na)+

Retention time: 0.85 min (Analytical condition SQDFA05)

Synthesis of Compound aa244

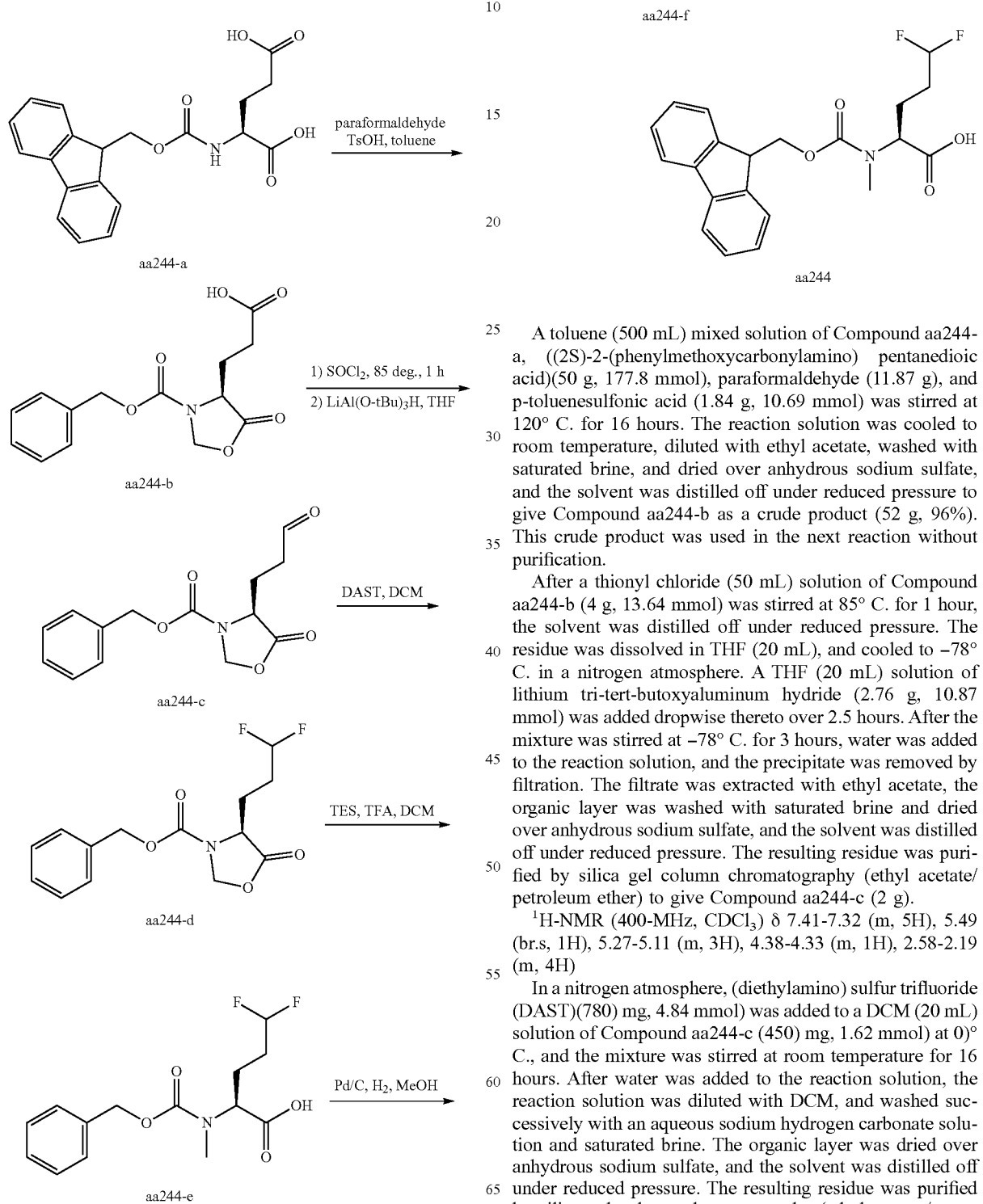

A toluene (500 mL) mixed solution of Compound aa244-a, ((2S)-2-(phenylmethoxycarbonylamino) pentanedioic acid)(50 g, 177.8 mmol), paraformaldehyde (11.87 g), and p-toluenesulfonic acid (1.84 g, 10.69 mmol) was stirred at 120° C. for 16 hours. The reaction solution was cooled to room temperature, diluted with ethyl acetate, washed with saturated brine, and dried over anhydrous sodium sulfate, and the solvent was distilled off under reduced pressure to give Compound aa244-b as a crude product (52 g, 96%). This crude product was used in the next reaction without purification.

After a thionyl chloride (50 mL) solution of Compound aa244-b (4 g, 13.64 mmol) was stirred at 85° C. for 1 hour, the solvent was distilled off under reduced pressure. The residue was dissolved in THF (20 mL), and cooled to −78° C. in a nitrogen atmosphere. A THF (20 mL) solution of lithium tri-tert-butoxyaluminum hydride (2.76 g, 10.87 mmol) was added dropwise thereto over 2.5 hours. After the mixture was stirred at −78° C. for 3 hours, water was added to the reaction solution, and the precipitate was removed by filtration. The filtrate was extracted with ethyl acetate, the organic layer was washed with saturated brine and dried over anhydrous sodium sulfate, and the solvent was distilled off under reduced pressure. The resulting residue was purified by silica gel column chromatography (ethyl acetate/ petroleum ether) to give Compound aa244-c (2 g).

$^1$H-NMR (400-MHz, CDCl$_3$) δ 7.41-7.32 (m, 5H), 5.49 (br.s, 1H), 5.27-5.11 (m, 3H), 4.38-4.33 (m, 1H), 2.58-2.19 (m, 4H)

In a nitrogen atmosphere, (diethylamino) sulfur trifluoride (DAST)(780) mg, 4.84 mmol) was added to a DCM (20 mL) solution of Compound aa244-c (450) mg, 1.62 mmol) at 0)° C., and the mixture was stirred at room temperature for 16 hours. After water was added to the reaction solution, the reaction solution was diluted with DCM, and washed successively with an aqueous sodium hydrogen carbonate solution and saturated brine. The organic layer was dried over anhydrous sodium sulfate, and the solvent was distilled off under reduced pressure. The resulting residue was purified by silica gel column chromatography (ethyl acetate/petroleum ether) to give Compound aa244-d (0).35 g, 72%). The compound was mixed with another similarly synthesized lot, and subjected to the next reaction.

$^1$H-NMR (400-MHz, CDCl$_3$) δ 7.42-7.35 (m, 5H), 5.97-5.58 (m, 2H), 5.25-5.16 (m, 3H), 4.50-4.35 (m, 1H), 2.14-1.68 (m, 4H)

$^{19}$F-NMR (400 MHZ, CDCl$_3$) δ-116.562

Compound aa244-d (1 g, 3.34 mmol) and TES (12.63 g, 109 mmol) were dissolved in TFA/DCM (10/10 mL), stirred at room temperature for 4 days, and then the solvent was distilled off under reduced pressure. The residue was diluted with an aqueous sodium hydrogen carbonate solution, washed with ether, and adjusted to pH 3 with 2 N hydrochloric acid. Extraction was performed with DCM, the organic layer was washed with saturated brine, dried over anhydrous sodium sulfate, and the solvent was distilled off under reduced pressure to give Compound aa244-e (0).6 g) as a crude product. This crude product was used in the next reaction without purification.

A methanol (10) mL) mixed solution of Compound aa244-e (0.6 g) and palladium carbon (10%, 60 mg) was stirred for 16 hours in a hydrogen atmosphere of about 3 atm. Palladium carbon was removed by filtration, and the solvent was distilled off from the filtrate under reduced pressure to give Compound aa244-f (0).23 g) as a crude product. This crude product was mixed with another similarly synthesized lot without purification, and subjected to the next reaction.

Fmoc-OSu (0).9 g, 1.5 eq) was added to a 1,4-dioxane/water (5/5 mL) mixed solution of Compound aa244-f (0).3 g, 1.79 mmol) and potassium carbonate (745 mg, 5.4 mmol), and the mixture was stirred for 2 hours. The reaction solution was diluted with water, washed with diethyl ether, and adjusted to pH 3 with 2 N hydrochloric acid. The reaction solution was extracted 3 times with ethyl acetate, the combined organic layer was washed with saturated brine and then dried over anhydrous sodium sulfate, and the solvent was distilled off under reduced pressure. The resulting residue was purified by reverse phase column chromatography (0.05% TFA-containing acetonitrile/0.05% TFA-containing distilled water) to give Compound aa244 (0.2 g, 29%). Another similarly synthesized lot was also used in the peptide synthesis in the present Examples.

Retention time: 3.153 min (Analytical condition SMD method_19)

$^1$H-NMR (300-MHz, DMSO-d$_6$) δ 12.94 (br.s, 1H), 7.92-7.88 (d, J=7.2 Hz, 2H), 7.66-7.61 (m, 2H), 7.44-7.31 (m, 4H), 6.35-5.75 (m, 1H), 4.49-4.26 (m, 4H), 2.72 (s, 3H), 1.78-1.65 (m, 4H)

$^{19}$F-NMR (300 MHz, DMSO-d$_6$) δ-115.730

Synthesis of Compound aa043

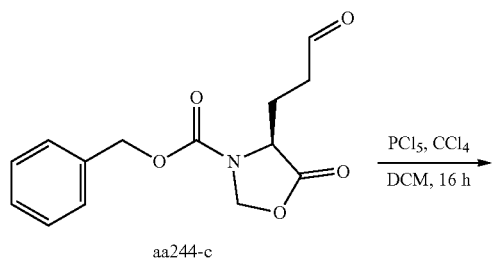

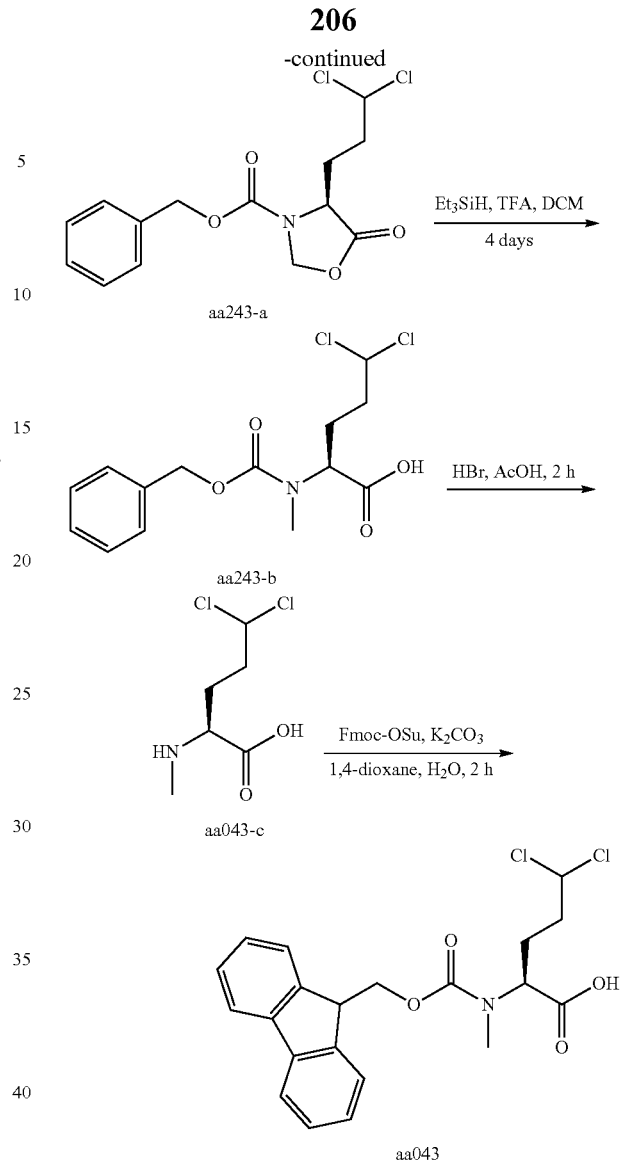

In a nitrogen atmosphere, aa244-c (18 g, 64.98 mmol) was dissolved in dichloromethane (50 mL), and a carbon tetrachloride (550 mL) solution of phosphorus pentachloride (27 g, 130 mmol) was slowly added dropwise at 0° C. The reaction solution was stirred at room temperature for 16 hours, and then dichloromethane was added for dilution. The resulting solution was washed with water, the aqueous phase was extracted twice with dichloromethane, and then the organic phases were combined and washed with an aqueous sodium hydrogen carbonate solution. The resulting solution was dried over anhydrous sodium sulfate, and then the solvent was distilled off under reduced pressure. The resulting crude product was purified by normal phase column chromatography (hexane/ethyl acetate) to give aa043-a (7.2 g, 33%).

aa043-a (7.2 g, 21.75 mmol) was dissolved in dichloromethane (150 mL), then triethylsilane (83.2 g, 718 mmol) and trifluoroacetic acid (24.8 g, 218 mmol) were added, and the mixture was stirred at room temperature for 4 days. The reaction solution was concentrated under reduced pressure, the resulting residue was dissolved in an aqueous sodium hydrogen carbonate solution, and the aqueous phase was washed with diethyl ether. Subsequently, the resulting solution was adjusted to pH 3 with 2 N hydrochloric acid. The mixed solution was extracted twice with dichloromethane, the organic phase was washed with saturated brine and dried over anhydrous sodium sulfate, and then the solvent was distilled off under reduced pressure. The resulting crude product aa043-b (5.5 g) was directly used in the next step.

A solution obtained by diluting an acetic acid solution (10 mL) of 33% hydrogen bromide with acetic acid (10 mL) was added to the crude product aa043-b (1.1 g), and the mixture was stirred at room temperature for 2 hours. The reaction mixture was concentrated under reduced pressure, and the residue was diluted with water. The resulting solution was washed with diethyl ether, and the solvent was distilled off under reduced pressure to give a crude product (1.0 g) of aa043-c. Crude product aa043-b was directly used in the next reaction. LCMS (ESI) m/z=200 (M+H)+

Retention time: 0.88 min (Analytical condition SMD method_12)

Crude product aa043-c (1.00 g) and potassium carbonate (1.48 g, 10.7 mmol) were dissolved in water (10 mL), and a 1,4-dioxane solution (10 mL) of Fmoc-OSu (1.8 g, 5.36 mmol) was added. After being stirred at room temperature for 2 hours, the reaction solution was diluted with water. The resulting solution was washed with diethyl ether (30 mL), and 2 N hydrochloric acid was added to adjust pH to 3. Subsequently, the mixed solution was extracted 3 times with ethyl acetate, the organic phase was washed with saturated brine and dried over anhydrous sodium sulfate, and the solvent was distilled off under reduced pressure. The resulting concentrate was purified by reverse phase column chromatography (water-acetonitrile) to give aa043 (0.5 g, 27%, 3 steps).

LCMS (ESI) m/z=422 (M+H)+

Retention time: 2.3 min (Analytical condition SMD method_13)

Synthesis of Compound aa056

In a nitrogen atmosphere, aa056-a (90 g, 443 mmol) and methyl iodide (314 g, 2.21 mol) were dissolved in tetrahydrofuran (3.15 µL). The mixed solution was cooled to 0° C., and sodium hydride (60%, 77.56 g, 2.21 mol) was added while stirring the mixed solution. The reaction solution was stirred at 25° C. for 3 hours, and then added to ice water. The resulting solution was washed 3 times with t-butyl methyl ether/n-hexane (1/3). Then, 1 N hydrochloric acid was added to the aqueous phase to adjust pH to 2-3, and the mixture was extracted 3 times with ethyl acetate. The resulting organic phase was washed with saturated brine, dried over anhydrous sodium sulfate, and concentrated under reduced pressure to give aa056-b (94 g) as a crude product. The resulting crude product was directly used in the next reaction. LCMS (ESI) m/z=240 (M+Na)+

Retention time: 1.1 min (Analytical condition SMD method_14)

The crude product (94 g) of aa056-b was dissolved in dichloromethane (600 mL). This solution was cooled to 0° C., and 4 N HCl/1,4-dioxane (660 mL) was added. The reaction solution was stirred at 25° C. for 3 hours and concentrated under reduced pressure to give a crude product (90 g) of aa056-c.

LCMS (ESI) m/z=118 (M+H)+

Retention time: 0.25 min (Analytical condition SMD method_14)

The crude product (90 g) of aa056-c was dissolved in water (560 mL), and potassium carbonate was added to adjust pH to 7. Subsequently, potassium carbonate (149 g, 1.08 mol), Fmoc-OSu (131 g, 389 mmol), and 1,4-dioxane (560 mL) were added to the reaction solution, and the mixture was stirred at 25° C. for 3 hours. Next, the reaction solution was washed with t-butyl methyl ether/n-hexane (1/3), then 1 N hydrochloric acid was added to adjust pH to 2 to 3, and solids were collected by filtration. The resulting solids were washed with water and dried under reduced pressure at 50° C. for 16 hours to give aa056 (130 g, 86% (3 steps)).

LCMS (ESI) m/z=362 (M+Na)+

Retention time: 2.0 min (Analytical condition SMD method_15)

Synthesis of Compound aa246

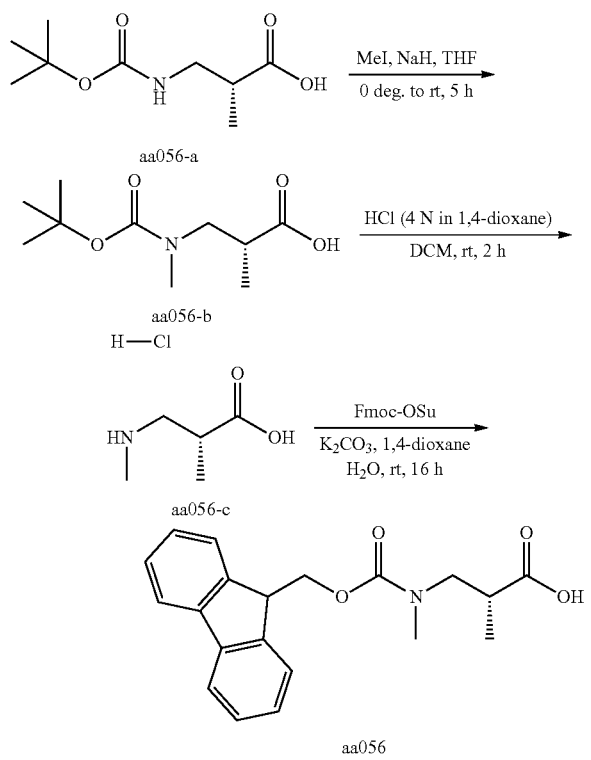

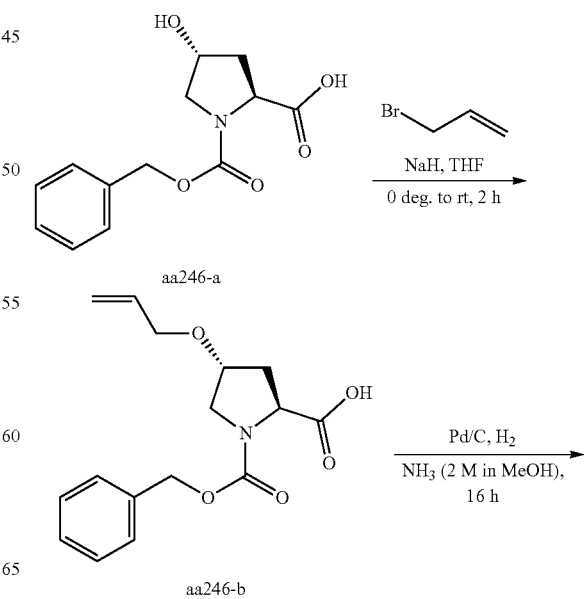

209
-continued

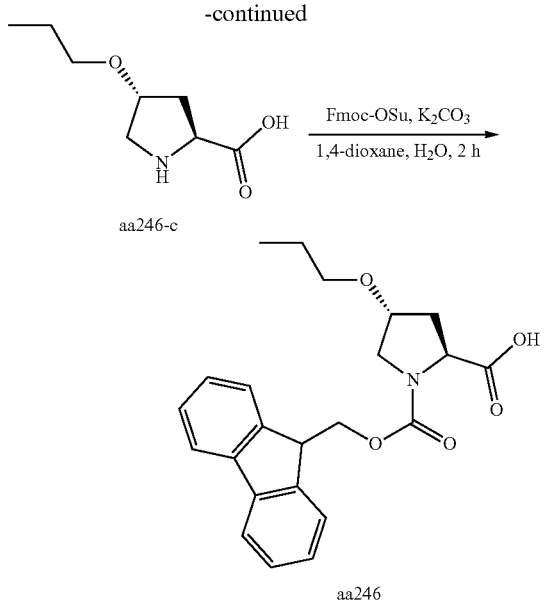

aa246-c aa246

In a nitrogen atmosphere, aa246-a (30 g, 113 mmol) was dissolved in tetrahydrofuran (300 mL), and sodium hydride (in oil, 60%, 5.97 g, 249 mmol) was added at 0° C. The reaction solution was stirred at room temperature for 4 hours and then cooled to 0° C., and 3-bromo-1-propene (15.73 g, 130 mmol) was added dropwise. Then, the reaction solution was stirred at room temperature for 2 hours, and ice water was added to quench the reaction. The pH of the resulting mixture was adjusted to 2 with concentrated hydrochloric acid, and then the mixture was extracted with ethyl acetate twice. The organic phase was washed with saturated brine, and dried over anhydrous sodium sulfate. The organic phase was concentrated under reduced pressure to give a crude product (27.3 g) of aa246-b.

LCMS (ESI) m/z=306 (M+H)+

Retention time: 2.0 min (Analytical condition SMD method_16)

The crude product (26 g) of aa246-b was dissolved in methanol (260 mL), and a 2 M ammonia-methanol solution (63.9 mL) and 10% palladium carbon (3.3 g) were added. The reaction solution was stirred at room temperature for 16 hours in a hydrogen atmosphere and then filtered. The resulting filtrate was concentrated under reduced pressure to give a crude product (14.2 g) of aa246-c.

LCMS (ESI) m/z=174 (M+H)+

Retention time: 0.84 min (Analytical condition SMD method_16)

The crude product (10 g) of aa246-c was dissolved in 1,4-dioxane (100 mL) and water (100 mL), and potassium carbonate (23.9 g, 172 mmol) was added. Fmoc-OSu (17.4 g, 51.7 mmol) was added to the reaction solution, and the mixture was stirred at room temperature for 16 hours and then filtered. The resulting filtrate was washed 5 times with t-butyl methyl ether/hexane (1/3), and the aqueous phase was adjusted to pH 2 with concentrated hydrochloric acid. The resulting solution was extracted twice with ethyl acetate. Subsequently, the organic phase was washed with saturated brine, dried over anhydrous sodium sulfate, and concentrated under reduced pressure to give aa246 (15.3 g, 58%, 3 steps).

LCMS (ESI) m/z=396 (M+H)+

210

Retention time: 2.0 min (Analytical condition SMD method_11)

Synthesis of Compound aa281

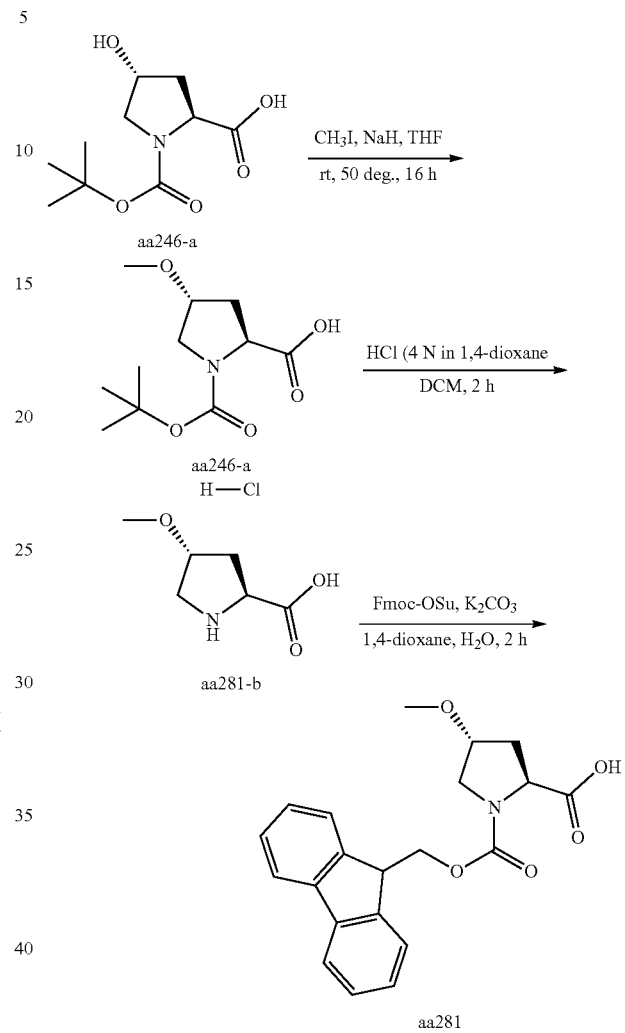

aa246-a aa246-a
H—Cl aa281-b aa281

In a nitrogen atmosphere, aa246-a (10 g, 43.2 mmol) was dissolved in tetrahydrofuran (150 mL) and cooled to −10° C., and then sodium hydride (60%, 3.8 g, 95.1 mmol) was added. The reaction solution was stirred at room temperature for 1 hour. Subsequently, methyl iodide (7.4 g, 51.9 mmol) was added dropwise at room temperature. The reaction solution was heated to 50° C., and stirred at 50° C. for 16 hours. Then, a saturated aqueous sodium hydrogen carbonate solution was added to the reaction solution. The aqueous phase was washed with diethyl ether (150 mL), and 1 N hydrochloric acid was added to adjust pH to 3. The resulting mixture was extracted twice with ethyl acetate (200 mL). The organic phase was washed with saturated brine and a 5% aqueous sodium thiosulfate solution, dried over anhydrous sodium sulfate, and then concentrated under reduced pressure to give a crude product (11.1 g) of aa281-a.

LCMS (ESI) m/z=268 (M+Na)+

Retention time: 0.75 min (Analytical condition SQDFA05)

The crude product (11.1 g) of aa281-a was dissolved in dichloromethane (110 mL), and 4 N HCl/1,4-dioxane (56.6 mL, 227 mL) was added. The reaction solution was stirred at room temperature for 2 hours, and then the solvent was distilled off under reduced pressure. The resulting residue was suspended in diethyl ether (110 mL), and solids were collected by filtration to give aa281-b (7.4 g, 94%, 2 steps).

LCMS (ESI) m/z=146 (M+H)+

Retention time: 0.14 min (Analytical condition SQDFA05)

aa281-b (7.4 g, 40.7 mmol) was dissolved in water (70 mL), and potassium carbonate was added to adjust pH to 7. Then, 1,4-dioxane (70 mL), potassium carbonate (11.3 g, 81.5 mmol), and Fmoc-OSu (12.4 g, 36.7 mmol) were added thereto at room temperature. After the reaction solution was stirred at room temperature for 2 hours, the aqueous phase was washed 3 times with t-butyl methyl ether-n-hexane (1/3, 70 mL). Subsequently, 1 N hydrochloric acid was added to the aqueous phase to adjust pH to 3, and the mixture was extracted with t-butyl methyl ether (140 mL). The organic phase was washed with saturated brine (70 mL), and dried over anhydrous sodium sulfate. The resulting organic phase was concentrated under reduced pressure to give aa281 (15 g, 98%).

LCMS (ESI) m/z=368 (M+H)+

Retention time: 1.79 min (Analytical condition SMD method_11)

Synthesis of Compound aa250

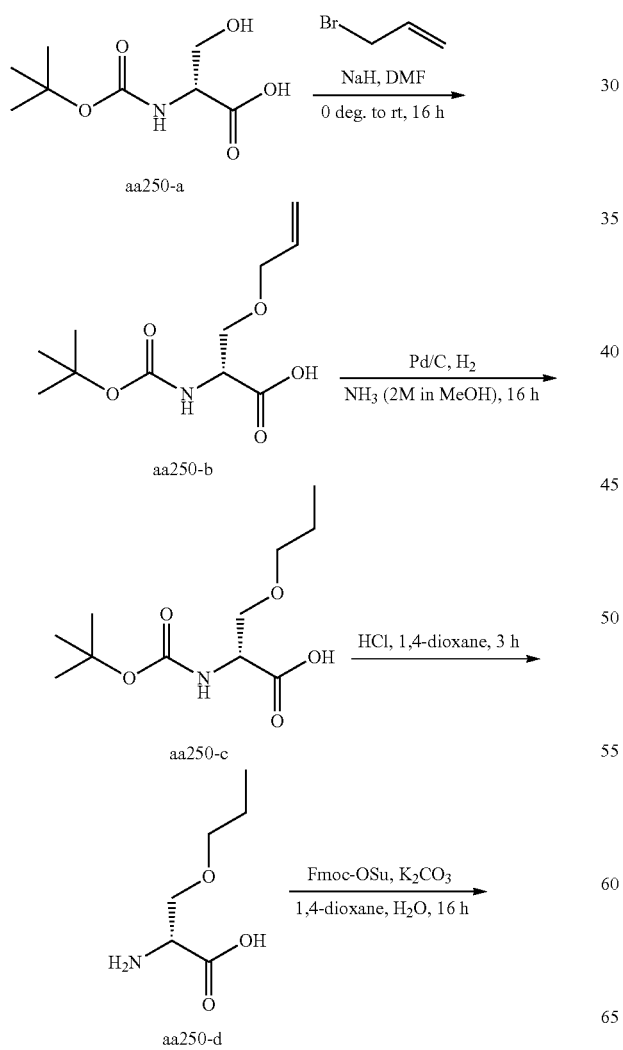

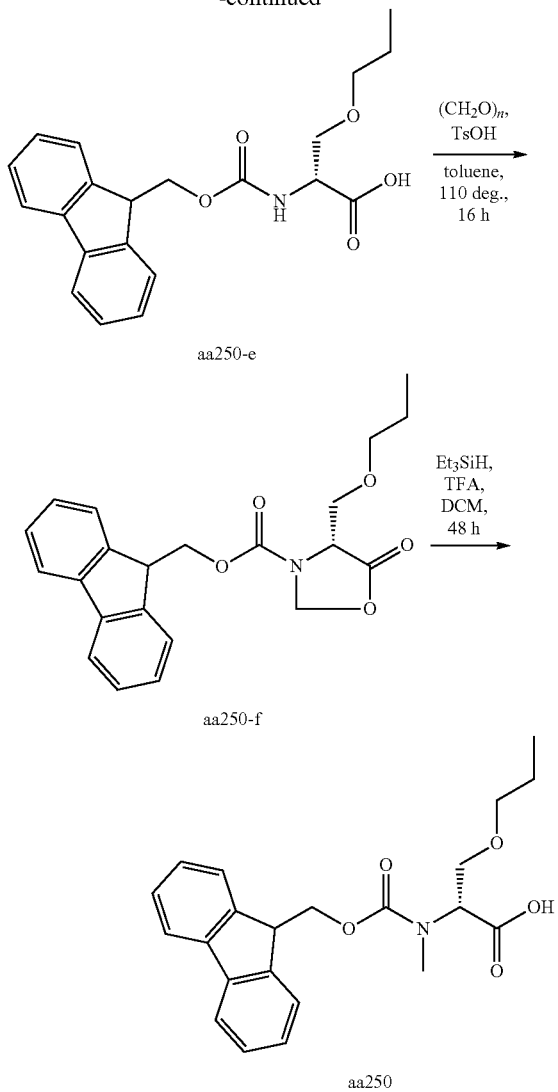

In a nitrogen atmosphere, aa250-a (233 g, 1.14 mol) was dissolved in DMF (1500 mL), and NaH (in oil, 60%, 100 g, 4.17 mol) was added while ice-cooling the mixture. The reaction solution was stirred at room temperature for 3 hours and cooled to 0° C., and a DMF (500 mL) solution of 3-bromo-1-propene (130 g, 1.07 mol) was added dropwise. Subsequently, the reaction solution was stirred at room temperature for 16 hours, and ice water was added to quench the reaction. The resulting solution was adjusted to pH 2 with concentrated hydrochloric acid. The mixed solution was extracted twice with ethyl acetate, the organic phase was washed with saturated brine, dried over anhydrous sodium sulfate, and concentrated under reduced pressure. The resulting residue was purified by silica gel column chromatography (ethyl acetate-n-hexane) to give aa250-b (200 g, 72%).

LCMS (ESI) m/z=246 (M+H)+

Retention time: 1.2 min (Analytical condition SMD method_14)

aa250-b (300 g, 1.22 mol) was dissolved in methanol (2 μL) and dissolved in a 2 M ammonia-methanol solution (918 mL) and methanol (2000 mL), and 10% palladium carbon (60 g) was added. The reaction solution was stirred at room temperature for 16 hours in a hydrogen atmosphere at 10 atm. The reaction solution was filtered and then concentrated under reduced pressure to give a crude product (290 g) of aa250-c.

LCMS (ESI) m/z=248 (M+H)+

Retention time: 1.2 min (Analytical condition SMD method_14)

The crude product (100 g) of aa250-c was dissolved in 1,4-dioxane (1500 mL), and 12 N hydrochloric acid (200 mL) was added. The reaction solution was stirred at room temperature for 4 hours, and then the volatile organic solvent was distilled off under reduced pressure to give an aqueous solution of aa250-d. The resulting aqueous solution was adjusted to pH 7 with potassium carbonate, and then 1,4-dioxane (500 mL), Fmoc-OSu (115 g, 0.34 mmol), and potassium carbonate (104.5 g, 0).76 mol) were added. The reaction solution was stirred at room temperature for 16 hours and then filtered. The filtrate was washed 5 times with t-butyl methyl ether/hexane (1/3), and then concentrated hydrochloric acid was added to adjust pH to 1. The resulting solution was extracted twice with ethyl acetate, the organic phase was dried over anhydrous sodium sulfate, and concentrated under reduced pressure to give aa250)-e (90 g, 58%, 3 steps).

LCMS (ESI) m/z=370)(M+H)+

Retention time: 1.3 min (Analytical condition SMD method_14)

aa250)-e (110) g, 298 mmol) was dissolved in toluene (1000 mL), and p-toluenesulfonic acid (3 g, 17.4 mmol) and paraformaldehyde (27 g, 893 mmol) were added. The reaction solution was stirred at 110° C. for 16 hours. The reaction solution was cooled, washed 4 times with an aqueous sodium hydrogen carbonate solution, and dried over anhydrous sodium sulfate. The resulting organic phase was concentrated under reduced pressure to give a crude product (90) g) of aa250-f.

LCMS (ESI) m/z=382 (M+H)+

Retention time: 2.9 min (Analytical condition SMD method_16)

The crude product (60 g) of aa250-f was dissolved in dichloromethane (700 mL), then triethylsilane (59 g, 507 mmol) and trifluoroacetic acid (700 mL, 1.41 mol) were added, and the mixture was stirred at room temperature for 48 hours. Then, the reaction solution was concentrated, and the resulting concentrate was dissolved in water (50 mL). The resulting aqueous solution was neutralized with a saturated aqueous potassium carbonate solution to adjust pH to 8. Subsequently, the mixture was washed 4 times with n-hexane, the resulting solution was adjusted to pH 2 with concentrated hydrochloric acid, and extracted twice with t-butyl methyl ether. The organic phase was dried over anhydrous sodium sulfate and concentrated under reduced pressure to give aa250)(50 g, 66%, 2 steps).

LCMS (ESI) m/z=384 (M+H)+

Retention time: 2.0 min (Analytical condition SMD method_11)

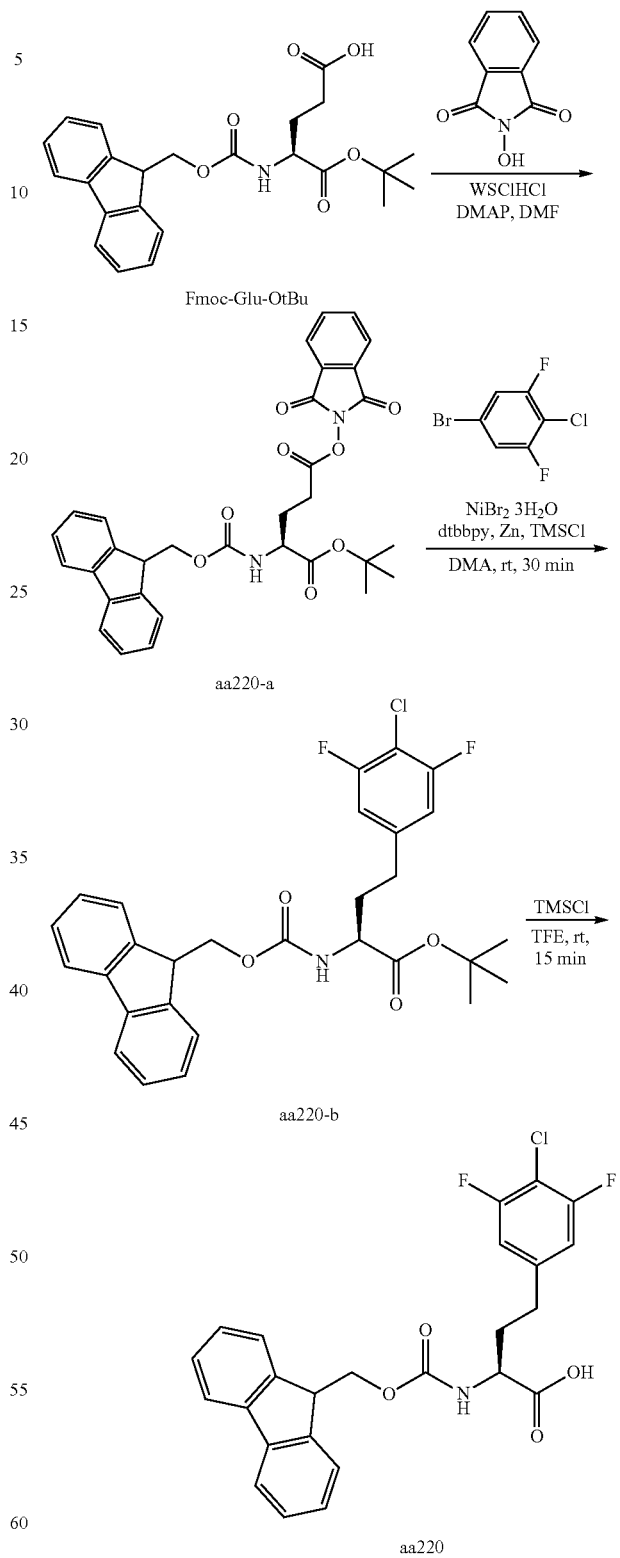

Synthesis of Compound aa220

Fmoc-Glu-OtBu ((4S)-4-(9H-fluoren-9-ylmethoxycarbonylamino)-5-[(2-methylpropan-2-yl)oxy]-5-oxopentanoic acid, CAS No. 84793-7-7)(175 g, 411 mmol), N-hydroxyphthalimide (67.1 g, 411 mmol), WSCI·HCl (78.85 g, 411 mmol), and DMAP (2.51 g, 20.6 mmol) were added to DMF (2 µL), and the mixture was stirred at room temperature for 16 hours. A 1 N hydrochloric acid solution was added to the reaction solution, and the reaction mixture was extracted with TBME. The organic layers were combined, sequentially washed with water, saturated aqueous sodium hydrogen carbonate solution/water (1/1), and saturated brine, and dried over anhydrous sodium sulfate, and then the solvent was distilled off under reduced pressure. The resulting residue was purified by silica gel column chromatography (ethyl acetate/petroleum ether, 0/100 to 30/70) to give Compound aa220-a (1-O-tert-butyl 5-O-(1,3-dioxoisoindol-2-yl)(2S)-2-(9H-fluoren-9-ylmethoxycarbonylamino) pentanedioate)(105 g, 45%).

LCMS (ESI) m/z=593.5 (M+Na)+

Retention time: 2.374 min (Analytical condition SMD method_09) $^1$H-NMR (300-MHz, DMSO-$d_6$) δ 8.00-7.91 (m, 4H), 7.85 (dd, J=23.0, 7.6 Hz, 3H), 7.75 (d, J=7.4 Hz, 2H), 7.75-7.32 (m, 4H), 4.60-4.31 (m, 2H), 4.30-4.02 (m, 2H), 3.01-2.74 (m, 2H), 2.26-1.86 (m, 2H), 1.41 (s, 9H)

In a nitrogen atmosphere, N,N-dimethylacetamide (35.1 mL) was added to nickel (II) bromide trihydrate (0.76 g, 2.8 mmol) and 4,4'-di-tert-butyl-2,2'-bipyridine (0.75 g, 2.8 mmol), and the mixture was stirred at room temperature for 10 minutes (sol A). Then, sol A and chlorotrimethylsilane (0.9 mL, 7.0 mmol) were added to an N,N-dimethylacetamide (35.1 mL) solution of aa220-a (8.0 g, 14.0 mmol), 5-bromo-2-chloro-1,3-difluorobenzene (4.5 mL, 35.1 mmol), and zinc (4.6 g, 70.1 mmol), and the mixture was stirred at room temperature for 30 minutes. tert-Butyl methyl ether (250 mL) was added, the mixture was passed through a filter obtained by coating Celite with sodium sulfate, and then a 5 wt % aqueous disodium ethylenediaminetetraacetate solution (250 mL) was added for extraction. The organic layer was washed twice with a 5 wt % aqueous sodium carbonate solution (150 mL), washed with a saturated aqueous ammonium chloride solution (150 mL), dried over anhydrous sodium sulfate, and then the solvent was distilled off under reduced pressure. The resulting concentrate was purified by reverse phase chromatography (0.1% formic acid-containing acetonitrile/0.1% formic acid-containing distilled water) to give aa220-b (4.75 g, 64%).

Retention time: 1.18 min (Analytical condition SQDFA05)

aa220-b (4.75 g, 9.0 mmol) was dissolved in 2,2,2-trifluoroethanol (90.0 mL), chlorotrimethylsilane (3.4 mL, 27.0 mmol) was added at room temperature, the mixture was stirred for 15 minutes, and then the solvent was distilled off under reduced pressure. A 20:1 mixed solution (100 mL) of n-hexane and tert-butyl methyl ether was added to the resulting concentrate, then the mixture was filtered under reduced pressure, and the resulting residue was washed twice with a 40:1 mixed solution (100 mL) of n-hexane and tert-butyl methyl ether and dried under reduced pressure to give aa220 (3.92 g, 92%).

LCMS (ESI) m/z=470 (M−H)−

Retention time: 0.99 min (Analytical condition SQDFA05)

Synthesis of Compound aa023

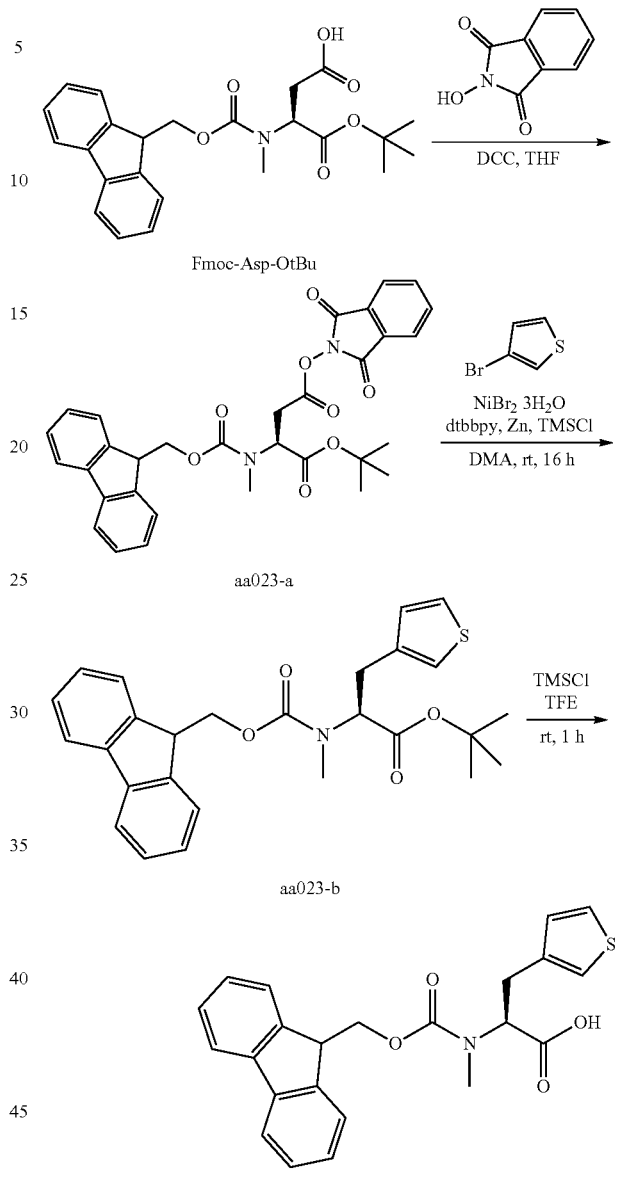

Fmoc-MeAsp-OtBu ((3S)-4-tert-butoxy-3-[9H-fluoren-9-ylmethoxycarbonyl(methyl)amino]-4-oxo-butanoic acid, CAS No. 2271413-88-6)(300 g, 729 mmol) and N-hydroxyphthalimide (130.8 g, 801.8 mmol) were added to THF (3 µL), and further, DCC(181.8 g, 1.1 mol) was added, and the mixture was stirred at room temperature for 3 hours. The solvent was distilled off from the reaction solution under reduced pressure, toluene was added to the residue, and solids were removed by filtration. The solvent was distilled off from the filtrate under reduced pressure, and the resulting residue was purified by silica gel column chromatography (hexane/ethyl acetate) to give Compound aa023-a (272 g, 67%).

LCMS (ESI) m/z=578.7 (M+Na)+

Retention time: 1.728 min (Analytical condition SMD method_08)

Using the resulting aa023-a, aa023-b (12.0 g, 51%) was obtained in the same manner as the synthesis of Compound aa220-b using 3-bromothiophene in place of 5-bromo-2-chloro-1,3-difluorobenzene.

LCMS (ESI) m/z=486 (M+Na)+

Retention time: 1.23 min (Analytical condition SMD method_20)

Using the resulting aa023-b, aa023 (8.8 g, 84%) was obtained under the same reaction conditions as the synthesis of Compound aa220.

LCMS (ESI) m/z=408 (M+H)+

Retention time: 0.86 min (Analytical condition SQDFA05)

Synthesis of Compound aa229

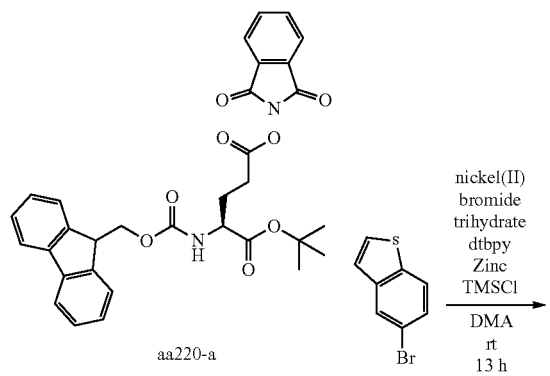

aa220-a

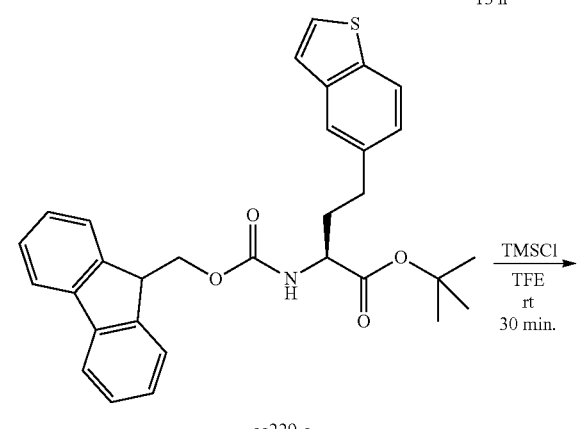

aa229-a

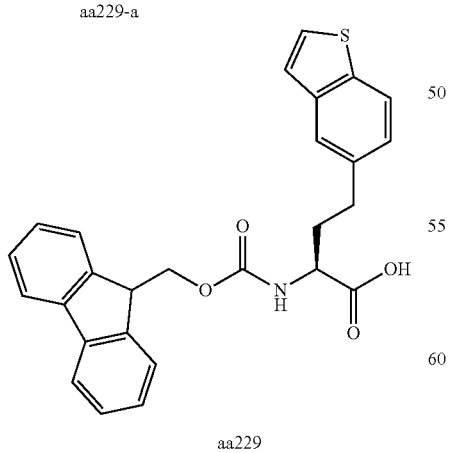

aa229

Compound aa220-b using 5-bromobenzothiophene in place of 5-bromo-2-chloro-1,3-difluorobenzene.

LCMS (ESI) m/z=515 (M+H)+

Retention time: 1.17 min (Analytical condition SQDFA05)

Using the resulting aa229-a, aa229 (3.05 g, 89%) was obtained under the same reaction conditions as the synthesis of Compound aa220.

LCMS (ESI) m/z=458 (M+H)+

Retention time: 0.96 min (Analytical condition SQDFA05)

Synthesis of Compound aa233

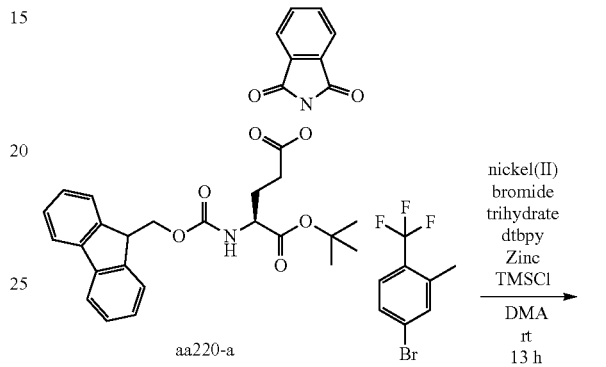

aa220-a

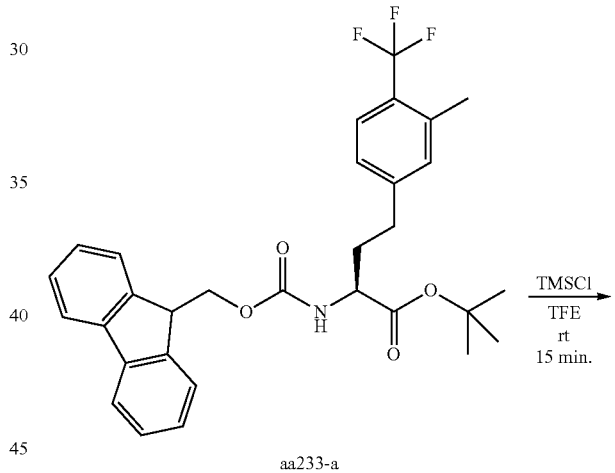

aa233-a

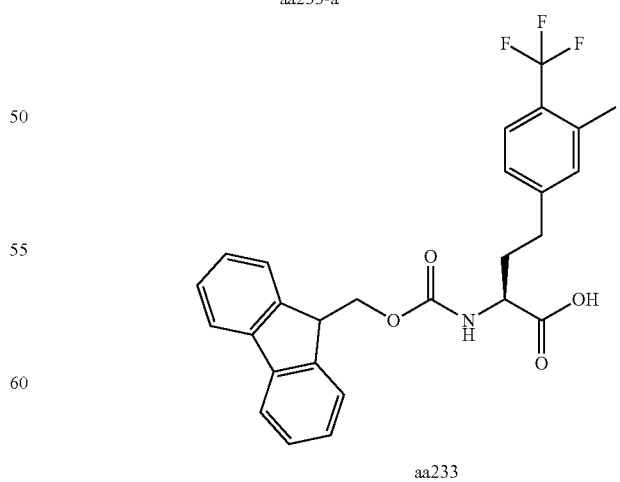

aa233

Using aa220-a as a starting material, aa229-a (3.83 g, 43%) was obtained in the same manner as the synthesis of Using aa220-a as a starting material, aa233-a (1.08 g, 67%) was obtained in the same manner as the synthesis of Compound aa220-b using 4-bromo-2-methyl-1-(trifluoromethyl)benzene in place of 5-bromo-2-chloro-1,3-difluorobenzene.

LCMS (ESI) m/z=541 (M+H)+

Retention time: 1.20 min (Analytical condition SQDFA05)

Using the resulting aa233-a, aa233 (0.65 g, 67%) was obtained under the same reaction conditions as the synthesis of Compound aa220.

LCMS (ESI) m/z=484 (M+H)+

Retention time: 1.01 min (Analytical condition SQDFA05)

Synthesis of Compound aa235

Using aa220-a as a starting material, aa235-a (4.73 g, 69%) was obtained in the same manner as the synthesis of Compound aa220-b using 4-bromo-2-methoxy-1-(trifluoromethyl)benzene in place of 5-bromo-2-chloro-1,3-difluorobenzene.

Retention time: 1.15 min (Analytical condition SQDFA05)

Using the resulting aa235-a, aa235 (3.91 g, 92%) was obtained under the same reaction conditions as the synthesis of Compound aa220.

LCMS (ESI) m/z=500 (M+H)+

Retention time: 0.96 min (Analytical condition SQDFA05)

Synthesis of Compound aa217

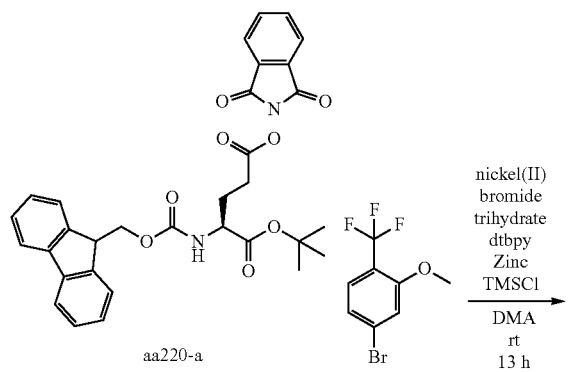

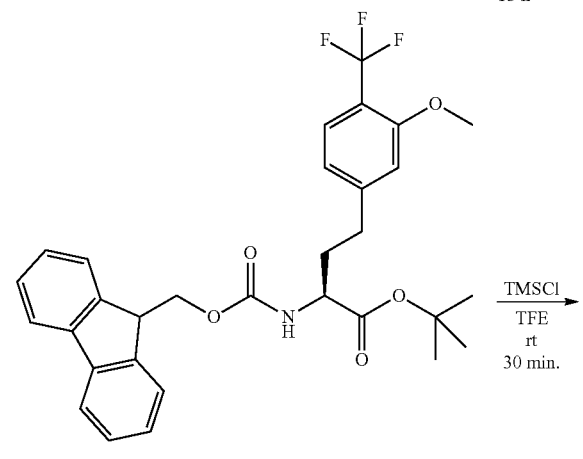

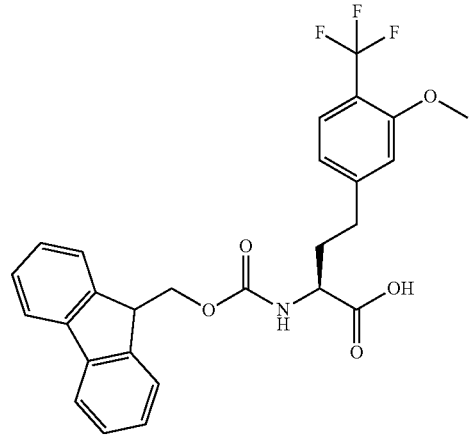

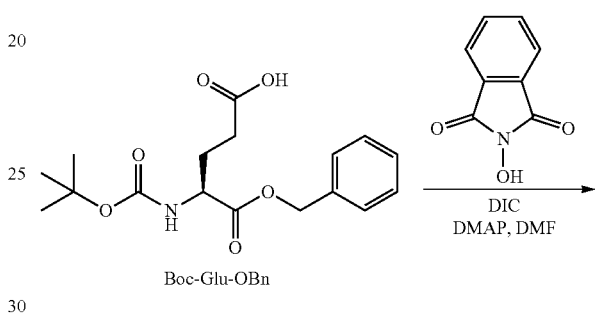

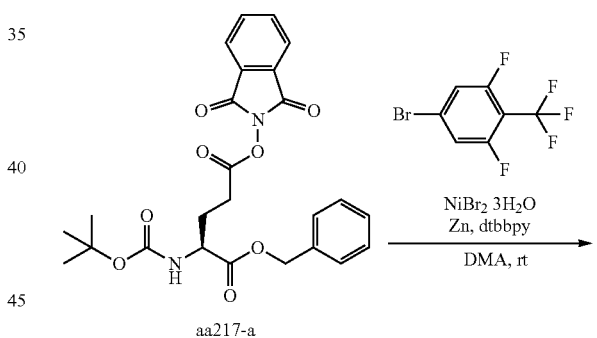

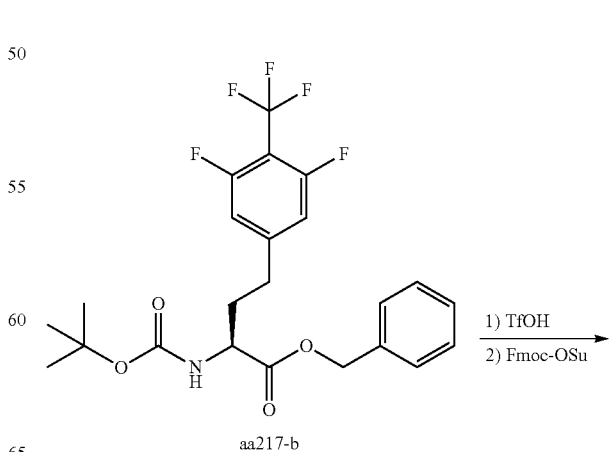

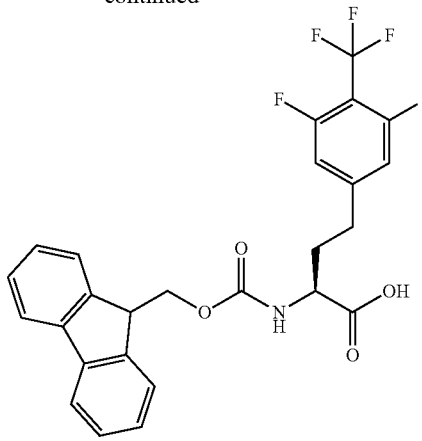

aa217

DIC(138 mL, 1.54 eq) was added dropwise at ( ) in a nitrogen atmosphere to a THF (2 μL) solution of (4S)-4-[(2-methylpropan-2-yl)oxycarbonylamino]-5-oxo-5-phenylmethoxypentanoic acid (Boc-Glu-OBn, CAS number 30924-93-7)(200 g, 592.82 mmol), N-hydroxyphthalimide (106 g, 649.78 mmol, 1.10 eq), and DMAP (3.6 g, 29.47 mmol, 0.05 eq). The reaction solution was stirred at 25° C. for 16 hours, solid matter was removed by filtration, and the solvent was distilled off from the filtrate under reduced pressure. The residue was diluted with toluene, the resulting solids were removed by filtration, and the solvent was distilled off from the filtrate under reduced pressure. The residue was purified by recrystallization (acetone/heptane) to give Compound aa217-a (1-O-benzyl 5-O-(1,3-dioxoisoindol-2-yl)(2S)-2-[(2-methylpropan-2-yl)oxycarbonylamino] pentanedioate)(230 g, 80%).

LCMS (ESI) m/z=505.2 (M+Na)+

Retention time: 0).992 min (Analytical condition SMD method_16) Nickel bromide trihydrate (NiBr₂: 3H₂O)(13.5 g, 49.7 mmol, 0).3 eq) and 4,4'-di-tert-butyl-2,2'-bipyridyl (dtbbpy, CAS No. 72914-19-3)(13.3 g, 49.7 mmol, 0.3 eq) were added to DMA (400 mL), and the mixture was stirred at 50° C. for 3 hours in a nitrogen atmosphere to prepare a Ni solution.

A DMA (400 mL) mixed solution of Compound aa217-a, (1-O-benzyl 5-O-(1,3-dioxoisoindol-2-yl)(2S)-2-[(2-methylpropan-2-yl)oxycarbonylamino] pentandioate)(80 g, 166 mmol), zinc powder (54.2 g, 829 mmol, 5 eq), and 4-bromo-1,3-difluoro-2-(trifluoromethyl)benzene (CAS No. 156243-64-0), 86.6 g, 332 mmol, 2 eq) was stirred at room temperature for 1 hour in a nitrogen atmosphere, the Ni solution prepared in advance was added, and the mixture was stirred at room temperature for 16 hours. An aqueous EDTA·2Na solution (800 mL, 10%) was added to the reaction solution, and solids were removed by filtration. The filtrate was extracted with ethyl acetate, the combined organic layer was washed with saturated brine and dried over anhydrous sodium sulfate, and the solvent was distilled off under reduced pressure. The resulting residue was purified by silica gel column chromatography (ethyl acetate/petroleum ether) to give Compound aa217-b (57.2 g, 69%).

LCMS (ESI) m/z=496 (M+Na)+

Retention time: 1.544 min (Analytical condition SMD method_15)

A toluene mixture (690) mL) of Compound aa217-b (57.2 g, 121 mmol) was cooled to 0° C., and trifluoromethanesulfonic acid (TfOH)(54.4 g, 362 mmol, 3 eq) was added dropwise. After 1 hour of stirring at room temperature, water (58 mL.) was added. The mixed solution was extracted with water, and the combined aqueous layer was extracted with ethyl acetate. The combined organic layer was washed with water and dried over anhydrous sodium sulfate, and the solvent was distilled off under reduced pressure to give 60 g of a residue. Acetonitrile/water (400/400 mL) was added to the residue, and pH was adjusted to 7 with an aqueous sodium hydroxide solution (48%). Fmoc-OSu (36.6 g, 108.6 mmol, 0.9 eq) was added to this solution, and pH was adjusted to 8.0 with an aqueous sodium hydroxide solution (48%), and then the mixture was stirred at room temperature for 16 hours. The reaction solution was filtered while being washed with acetonitrile/water (1/1) to remove solid components. The filtrate was diluted with acetonitrile and acidified with 6 N hydrochloric acid, and precipitated solids were collected by filtration to give Compound aa217 (52 g, 83%).

LCMS (ESI) m/z=528 (M+Na)+

Retention time: 3.538 min (Analytical condition SMD method_14)

¹H-NMR (300-MHz, DMSO-d₆) δ 12.69 (s, 1H), 7.90 (d, J=7.5 Hz, 2H), 7.78-7.54 (m, 3H), 7.48-7.20 (m, 6H), 4.33 (d, J=6.3 Hz, 2H), 4.24 (t, J=6.9 Hz, 1H), 3.97-3.84 (m, 1H), 2.79-2.65 (m, 2H), 2.15-2.00 (m, 1H), 2.00-1.83 (m, 1H)

Synthesis of Compound aa218

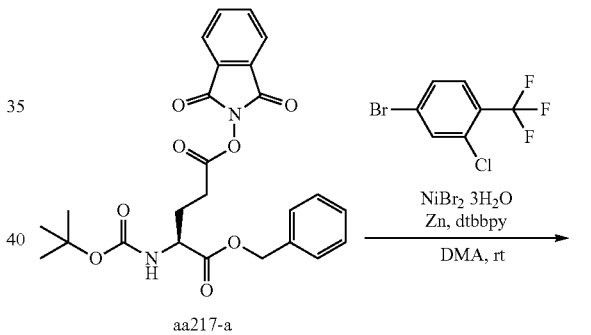

aa217-a

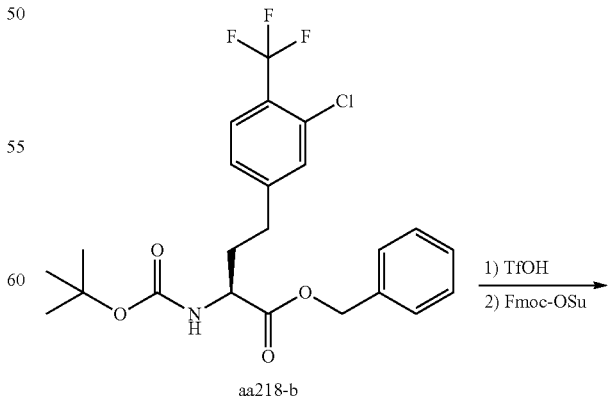

aa218-b

Synthesis of Compound aa219

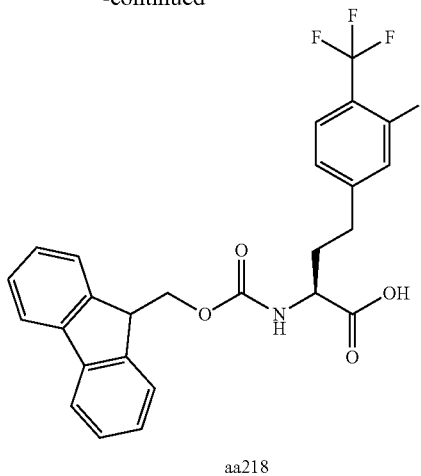

aa218

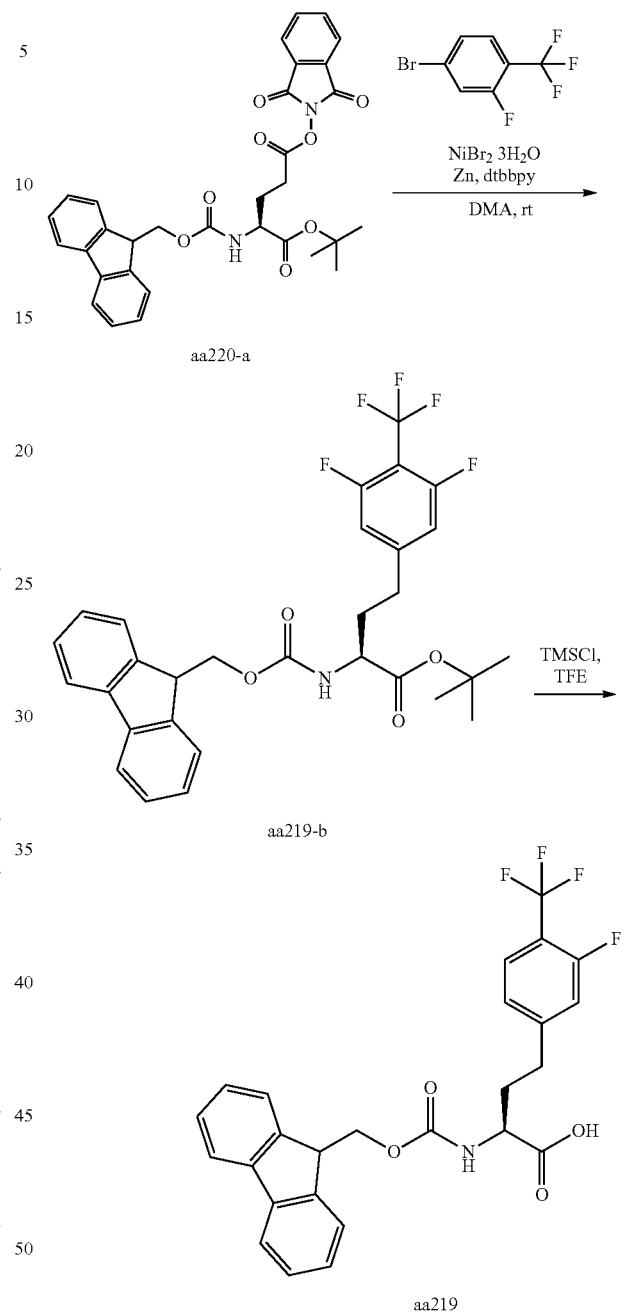

Nickel bromide trihydrate (NiBr$_2$: 3H$_2$O)(4 g, 0.07 eq) and 4,4'-di-tert-butyl-2,2'-bipyridyl(dtbbpy, CAS No. 72914-19-3)(3.9 g, 14.55 mmol, 0.07 eq) were added to DMA (500) mL), and the mixture was stirred at 50° C. for 2 hours in a nitrogen atmosphere to prepare a Ni solution.

The Ni solution prepared in advance was added to a DMA (500 mL) mixed solution of Compound aa217-a (100 g, 207.3 mmol), zinc powder (70 g, 5 eq), and 4-bromo-2-chloro-1-(trifluoromethyl)benzene (CAS No. 467435-07-0), 160 g, 617 mmol, 3 eq), and the mixture was stirred at 25° C. for 16 hours. An aqueous EDTA·2Na solution (10) %) was added to the reaction solution, and the mixture was extracted with ethyl acetate. The combined organic layer was washed with saturated brine and dried over anhydrous sodium sulfate, and the solvent was distilled off under reduced pressure. The resulting residue was purified by silica gel column chromatography (ethyl acetate/petroleum ether) to give Compound aa218-b (75 g, 77%).

LCMS (ESI) m/z=494 (M+Na)+

Retention time: 2.863 min (Analytical condition SMD method_17)

A toluene solution (900 mL) of Compound aa218-b (75 g, 158.93 mmol) was cooled to ( ), and trifluoromethanesulfonic acid (TfOH)(42 mL, 3.00) eq) was added dropwise. After 1 hour of stirring at room temperature, water (75 mL) was added. The mixed solution was extracted with water, and the combined aqueous layer was extracted with ethyl acetate. The combined organic layer was washed with water and dried over anhydrous sodium sulfate, and the solvent was distilled off under reduced pressure. Acetonitrile/water (900/900 mL) was added to the residue, and pH was adjusted to 7 with an aqueous sodium hydroxide solution (48%). Fmoc-OSu (51.2 g, 151.93 mmol, 0.95 eq) was added to this solution, and the mixture was stirred at room temperature for 16 hours while maintaining pH at 7.8 to 8.0. The reaction solution was filtered, and the filtrate was adjusted to pH 2 with 6 N hydrochloric acid. The precipitated solids were collected and dried at 50° C. to give Compound aa218 (70 g, 87%).

LCMS (ESI) m/z=526 (M+Na)+

Retention time: 2.180 min (Analytical condition SMD method_21)

$^1$H-NMR (300-MHz, DMSO-d$_6$) δ 12.70 (s, 1H), 7.91 (d, J=7.5 Hz, 2H), 7.79-7.59 (m, 5H), 7.45-7.28 (m, 5H), 4.40)-4.19 (m, 3H), 3.96-3.88 (m, 1H), 2.82-2.60)(m, 2H), 2.11-1.77 (m, 2H)

Nickel bromide trihydrate (NiBr$_2$: 3H$_2$O)(71.5 g, 263 mmol, 0.3 eq) and 4,4'-di-tert-butyl-2,2'-bipyridyl(dtbbpy, CAS Number 72914-19-3)(70.56 g, 263 mmol, 0.3 eq) were added to DMA (2 μL), and the mixture was stirred at 50° C. for 3 hours in a nitrogen atmosphere to prepare a Ni solution.

A DMA (2 μL) mixed solution of Compound aa220-a (1-O-tert-butyl 5-O-(1,3-dioxoisoindol-2-yl)(2S)-2-(9H-fluoren-9-ylmethoxycarbonylamino) pentanedioate)(500 g, 876 mmol), zinc powder (287 g, 4.38 mol, 5 eq), and 4-bromo-2-fluoro-1-(trifluoromethyl)benzene (CAS No. 142808-15-9, 425.87 g, 1.753 mol, 2 eq) was stirred at room temperature for 1 hour in a nitrogen atmosphere. The Ni solution prepared in advance was added to this mixed solution, and the mixture was stirred at room temperature for 16 hours. An aqueous EDTA·2Na solution (4 µL, 10%) was added to the reaction solution, and solids were removed by filtration while being washed with ethyl acetate. The filtrate was washed with saturated brine and then dried over anhydrous sodium sulfate, and the solvent was distilled off under reduced pressure. The resulting residue was purified by silica gel column chromatography (ethyl acetate/petroleum ether) to give Compound aa219-b (230 g, 43%).

LCMS (ESI) m/z=566 (M+Na)+

Retention time: 1.317 min (Analytical condition SMD method_18)

A trifluoroethanol (TFE)(2.3 µL) mixed solution of the resulting Compound aa219-b (230 g, 423 mmol) and chlorotrimethylsilane (TMSCI)(137.9 g, 1.269 mol) was stirred at room temperature for 1 hour, and the precipitated solids were collected by filtration. The operation of dissolving the resulting solids in TBME and distilling off the solvent under reduced pressure was repeated several times to give the intended Compound aa219 (190 g, 90%).

LCMS (ESI) m/z=510 (M+Na)+

Retention time: 1.585 min (Analytical condition SMD method_13)

$^1$H-NMR (300-MHz, DMSO-$d_6$) δ 12.69 (s, 1H), 7.90 (d, J=7.5 Hz, 2H), 7.81-7.66 (m, 4H), 7.47-7.37 (m, 3H), 7.37-7.29 (m, 2H), 7.25 (d, J=8.1 Hz, 1H), 4.44-4.14 (m, 3H), 3.97-3.84 (m, 1H), 2.80-2.63 (m, 2H), 2.12-1.81 (m, 2H)

Synthesis of Compound aa239

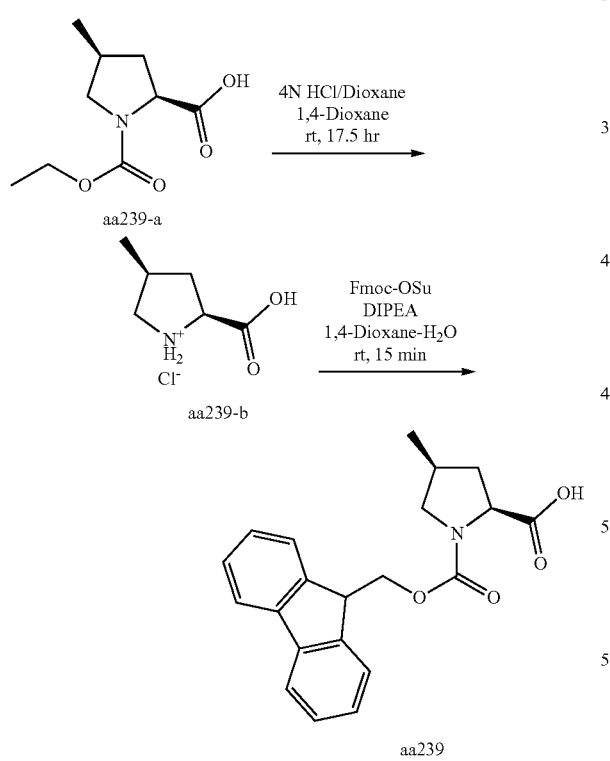

aa239-a (2 g, 8.72 mmol) was dissolved in 1,4-dioxane (2 mL) at room temperature, and 4 N HCl/dioxane (4.36 mL, 17.45 mmol) was added. The reaction mixture was stirred at room temperature for 17.5 hours, the solvent was distilled off under reduced pressure, and the resulting crude product was dissolved in water and freeze-dried to give aa239-a (1.49 g, quant.).

Water (22.5 mL) and DIPEA (5.89 mL, 33.7 mmol) were added to aa239-a (1.49 g, 9 mmol) at room temperature to dissolve it, 1,4-dioxane (15 mL) was added, then N-(9-fluorenylmethoxycarbonyloxy) succinimide (3.03 g, 9 mmol) was added, and the mixture was stirred at room temperature for 15 minutes. Hexane-CPME (3:1)(10 mL) was added to the reaction mixture, and the separated aqueous phase was washed twice with hexane-CPME (3:1) (10 mL). Potassium hydrogen sulfate (4.59 g, 33.7 mmol) and ethyl acetate were added to the aqueous phase, the separated organic phase (about 60 mL) was washed twice with brine (10 mL) and dried over anhydrous sodium sulfate, then the solvent was distilled off under reduced pressure, and the resulting crude product was purified by reverse phase chromatography (0.1% formic acid-containing acetonitrile/0.1% formic acid-containing distilled water) to give aa239 (2.89 g, 91%).

LCMS (ESI) m/z=352 (M+H)+

Retention time: 0.81 min (Analytical condition SQDFA05)

Synthesis of Compound aa098

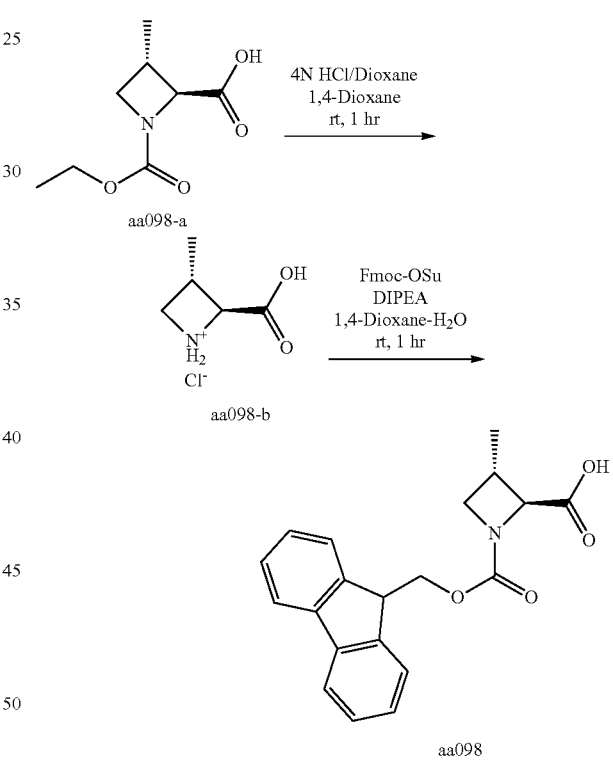

Using aa098-a as a starting material, aa098-b (2.30 g, quant.) was obtained in the same manner as the synthesis of Compound aa239-b.

LCMS (ESI) m/z=116 (M+H)+

Retention time: 0.16 min (Analytical condition SQDFA05)(retention time of MS peak is described)

Using the resulting aa098-b, aa098 (2.73 g, 87%) was obtained under the same reaction conditions as the synthesis of Compound aa239.

LCMS (ESI) m/z=338 (M+H)+

Retention time: 0.73 min (Analytical condition SQDFA05)

Synthesis of Compound aa111

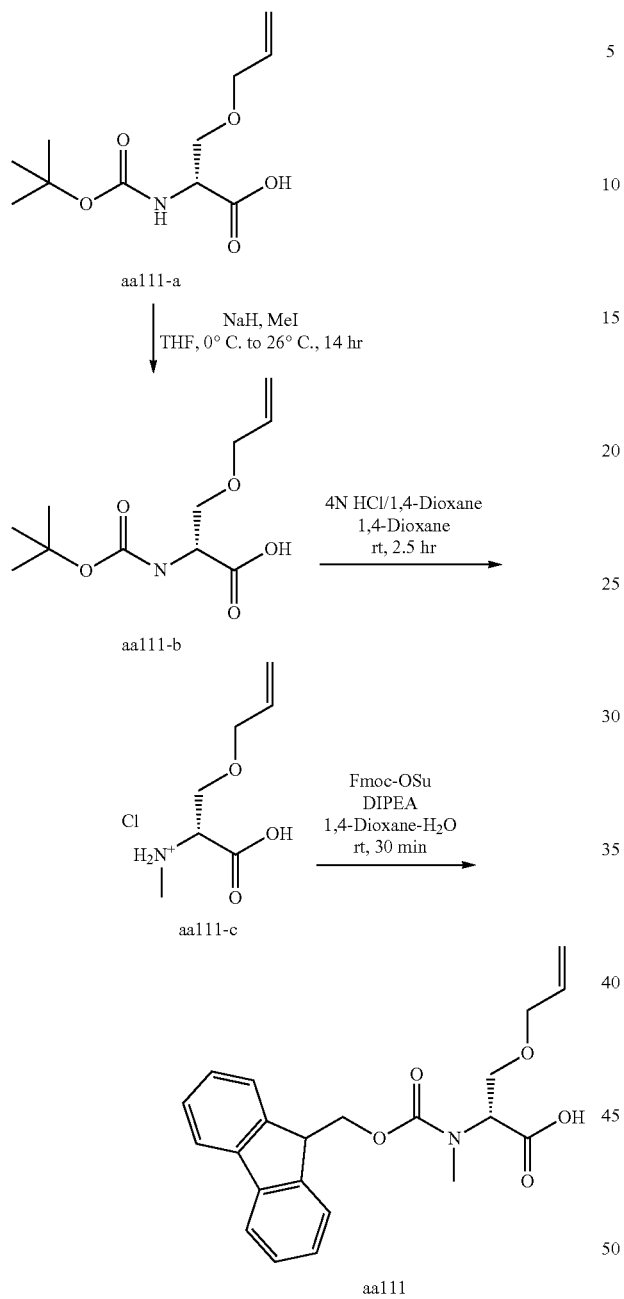

In a nitrogen atmosphere, dehydrated THF (40 mL) was added to sodium hydride (1.47 g, 36.7 mmol: calculated as having 60 wt %) cooled in an ice bath. A dehydrated THF (10 mL) solution of aa111-a (3 g, 12.23 mmol) and methyl iodide (4.59 mL, 73.4 mmol) was added dropwise to the resulting suspension. The reaction mixture was stirred for 14 hours from an ice-cooled temperature to 26° C., and then water (2 mL) was added while the mixture was ice-cooled. The resulting mixture was stirred at room temperature for 10 minutes, and then the solvent was distilled off under reduced pressure. Hexane-CPME (20:1)(20 mL) and water (20 mL) were added to the concentrated residue for extraction, and the aqueous phase (about 30 mL) was washed twice with hexane-CPME (20:1)(20 mL). Potassium hydrogen sulfate (4.1 g, 30.1 mmol) and ethyl acetate were added to the aqueous phase, the separated organic phase (about 50 mL) was washed twice with brine (20 mL) and dried over anhydrous sodium sulfate, and the solvent was distilled off under reduced pressure to give aa111-b (2.66 g, 84%).

LCMS (ESI) m/z=282 (M+H)+

Retention time: 0.62 min (Analytical condition SQDFA05)

Using aa111-b as a starting material, aa111-c (1.55 g, 77%) was obtained in the same manner as the synthesis of Compound aa239-b.

LCMS (ESI) m/z=160 (M+H)+

Retention time: 0.17 min (Analytical condition SQDFA05)(retention time of MS peak is described)

Using the resulting aa111-c, aa111 (0.837 g, 28%) was obtained under the same reaction conditions as the synthesis of Compound aa239.

LCMS (ESI) m/z=383 (M+H)+

Retention time: 0.82 min (Analytical condition SQDFA05)

Synthesis of Compound aa268

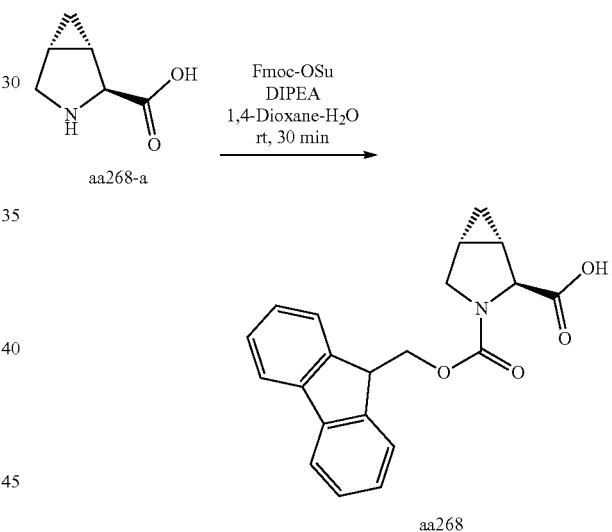

Water (10 mL) and DIPEA (4.81 mL, 27.5 mmol) were added to aa268-a (1 g, 7.87 mmol) at room temperature to dissolve it, 1,4-dioxane (15 mL) was added, then N-(9-fluorenylmethoxycarbonyloxy) succinimide (2.65 g, 7.87 mmol) was added, and the mixture was stirred at room temperature for 30 minutes. Water (15 ml) and hexane (10 mL) were added to the reaction mixture, and the separated aqueous phase was washed twice with hexane-CPME (3:1) (15 mL). Potassium hydrogen sulfate (3.75 g, 27.5 mmol) and ethyl acetate were added to the aqueous phase, the separated organic phase (about 60 mL) was washed twice with brine (15 mL) and dried over anhydrous sodium sulfate, and the solvent was distilled off under reduced pressure to give aa268 (2.85 g, quant).

LCMS (ESI) m/z=350 (M+H)+

Retention time: 0.78 min (Analytical condition SQDFA05)

Synthesis of Compound aa099

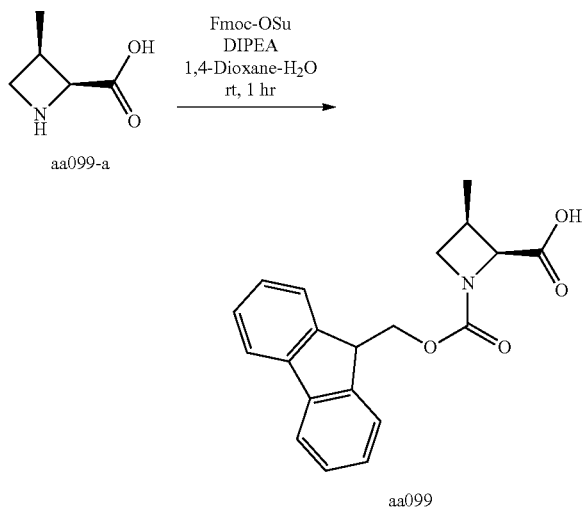

Using aa099-a, aa099 (9.91 g, 75%) was obtained under the same reaction conditions as the synthesis of Compound aa268.

LCMS (ESI) m/z=338 (M+H)+

Retention time: 0.72 min (Analytical condition SQDFA05)

Synthesis of Compound aa100

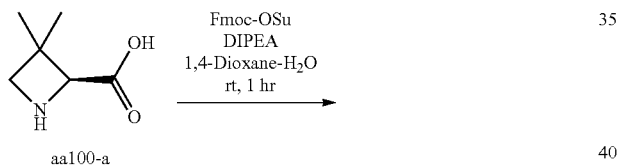

aa100-a

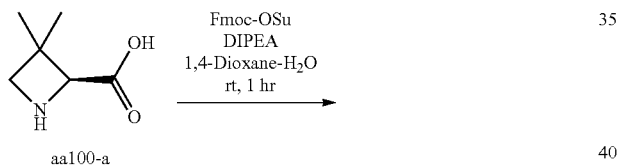

aa100

Using aa100-a, aa100 (2.15 g, 80%) was obtained under the same reaction conditions as the synthesis of Compound aa268.

LCMS (ESI) m/z=352 (M+H)+

Retention time: 0.76 min (Analytical condition SQDFA05)

Synthesis of Compound aa389

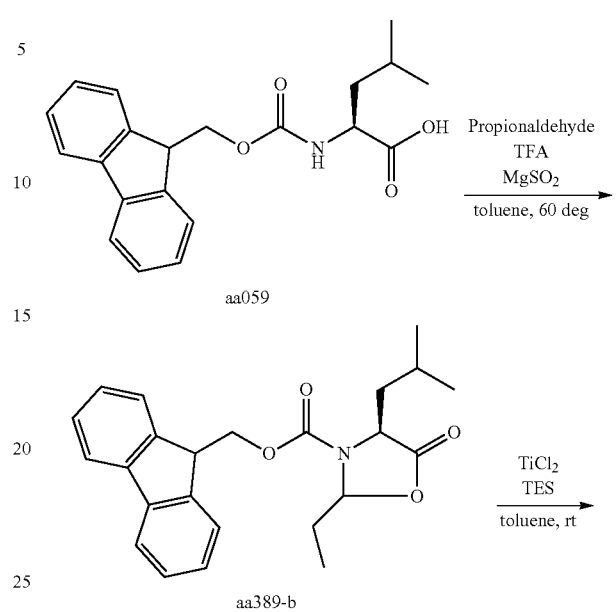

Using aa059 (Fmoc-Leu-OH) as a starting material, a crude product of aa389-b was obtained in the same manner as synthesis of Compound aa136-b.

Using the resulting aa389-b, aa389 (7.7 g, 69% in 2 steps) was obtained in the same manner as Compound aa136.

LCMS (ESI) m/z=396 (M+H)+

Retention time: 0.99 min (Analytical condition SQDFA05)

Synthesis of Compound aa397

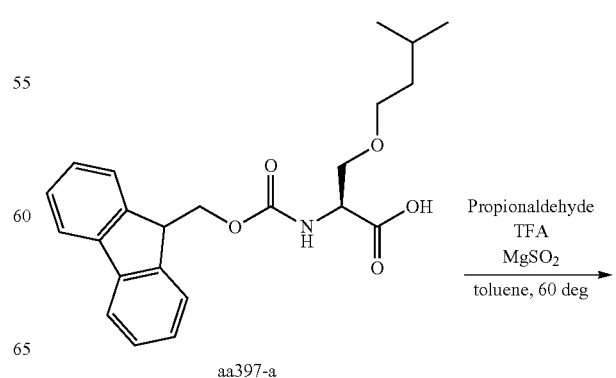

aa397-a

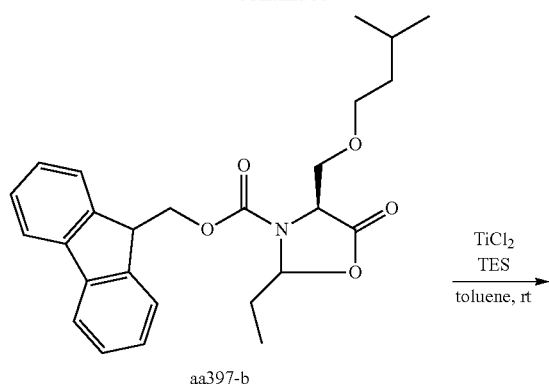

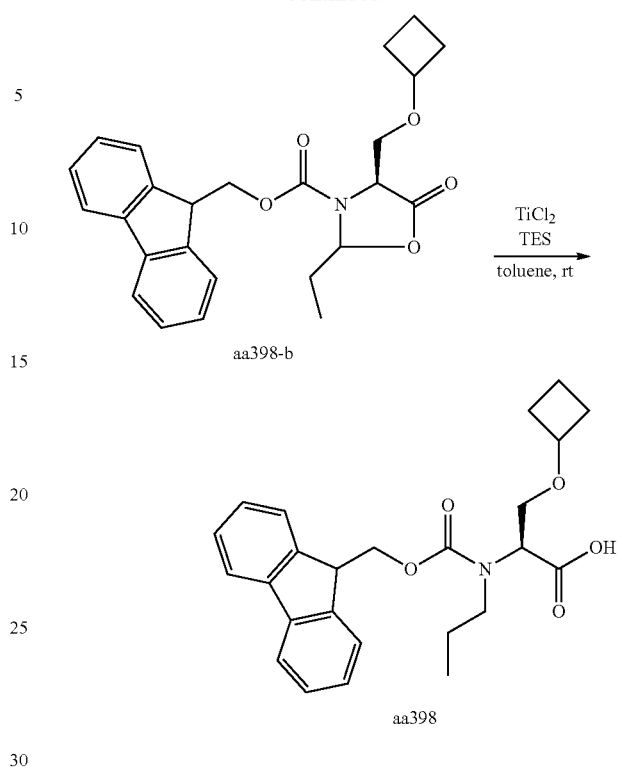

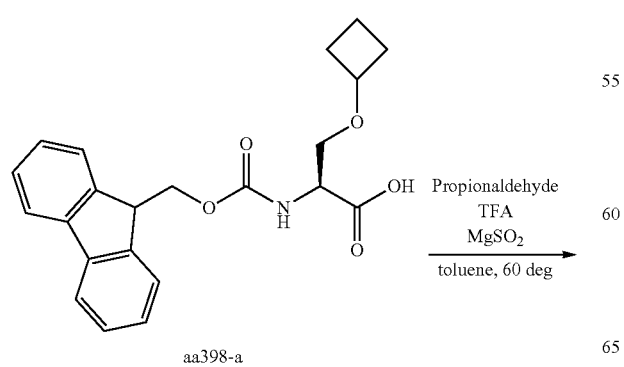

Using aa397-a (N-(((9H-fluoren-9-yl)methoxy) carbonyl)-O-isopentyl-L-serine, Fmoc-Ser (iPen)-OH, CAS No. 2255321-11-8) as a starting material, aa397-b was obtained in the same manner as synthesis of Compound aa136-b.

Using the resulting aa397-b, aa397 (8.1 g, 73% in 2 steps) was obtained in the same manner as synthesis of Compound aa136.

LCMS (ESI) m/z=440 (M+H)+

Retention time: 1.04 min (Analytical condition SQDFA05)

Synthesis of Compound aa398

Using aa398-a (N-(((9H-fluoren-9-yl)methoxy) carbonyl)-O-cyclobutyl-L-serine, Fmoc-Ser (cBu)-OH, CAS No. 2642331-49-3) as a starting material, aa398-b was obtained in the same manner as synthesis of Compound aa136-b. Using the resulting aa398-b, aa398 (5.3 g, 48% in 2 steps) was obtained in the same manner as synthesis of Compound aa136. LCMS (ESI) m/z=424 (M+H)+

Retention time: 0.95 min (Analytical condition SQDFA05)

Synthesis of Compound aa391

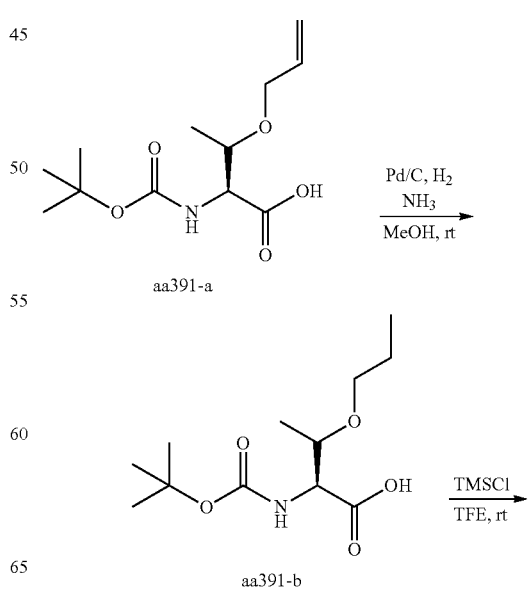

233

-continued

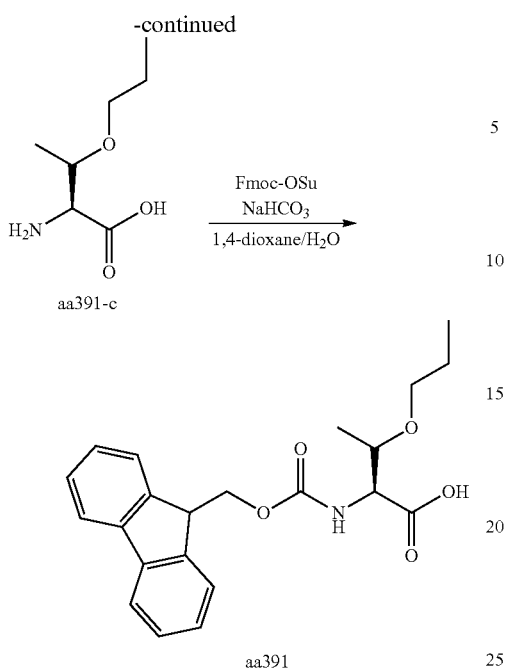

aa391-a (O-allyl-N-(tert-butoxycarbonyl)-L-threonine, CAS No. 300831-37-2)(5.00 g, 19.3 mmol) was dissolved in methanol (60 mL), and palladium on carbon (5%, 492 mg) and a 7 M ammonia methanol solution (4.13 mL) were added in a nitrogen atmosphere. The mixture was stirred at room temperature for 1.5 hours in a hydrogen atmosphere. Palladium on carbon was removed by filtration, and the solvent was distilled off from the filtrate under reduced pressure to give aa391-b as a crude product. The crude product was used in the next reaction without purification.

aa391-b was dissolved in TFE (89 mL), TMSCl (6.16 mL, 48.2 mmol) was added, and the mixture was stirred at room temperature for 30 minutes. The solvent was distilled off from the mixture under reduced pressure to give aa391-c as a crude product. The crude product was used in the next reaction without purification.

aa391-c was dissolved in water (54 mL), and sodium hydrogen carbonate (6.48 g, 77 mmol) and 1,4-dioxane (54 mL) were added. Fmoc-OSu (6.18 g, 18.3 mmol) was added to the mixture, and the mixture was stirred at room temperature for 4.5 hours. The reaction solution was washed with TBME (100 mL), and 2 N HCl (108 mL) was added to the aqueous layer, followed by extraction with DCM (40 mL) 3 times. The organic layer was dried over anhydrous sodium sulfate, the solvent was distilled off under reduced pressure, and the resulting residue was purified by reverse phase chromatography (0.1% formic acid-containing acetonitrile/0.1% formic acid-containing distilled water). The resulting crude product was dissolved in TBME (100 mL), extracted with a 3.5% aqueous sodium hydrogen carbonate solution (100 mL), and further extracted with a 3.5% aqueous sodium hydrogen carbonate solution (50 mL). After 2 M phosphoric acid was added to the aqueous layer to adjust the pH to 2, the mixture was extracted with ethyl acetate. The mixture was dried over anhydrous sodium sulfate, and then the solvent was distilled off under reduced pressure to give 391 (4.07 g, 55% in 3 steps).

LCMS (ESI) m/z=384 (M+H)+

Retention time: 0.84 min (Analytical condition SQDFA05)

234

Synthesis of Compound aa399

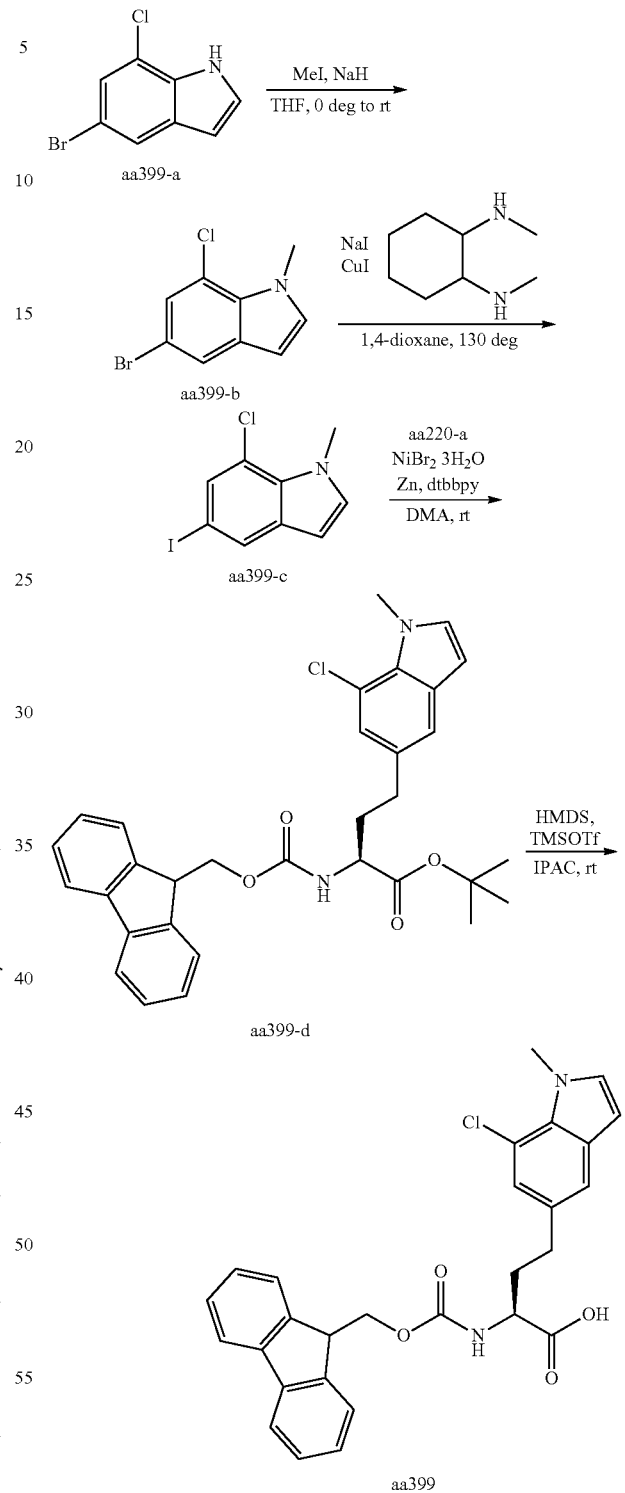

399-a (5-bromo-7-chloro-1H-indole, CAS No. 180623-89-6, 15.0 g, 65.1 mmol) was added to a THF solution (150 mL) of NaH (2.86 g, 71.6 mmol, 60%) under ice cooling, and the mixture was stirred at room temperature for 30 minutes. Iodomethane (10.2 g, 71.6 mmol) was added dropwise thereto under ice cooling, and the mixture was stirred at room temperature for 16 hours. Water was added thereto, followed by extraction with ethyl acetate 3 times. The solvent was distilled off from the organic layer under reduced pressure to give aa399-b as a crude product (17.2 g).

1,4-Dioxane solution (70 mL) of the crude product of aa399-b (6.10 g, 24.9 mmol), sodium iodide (18.7 g, 125 mmol), copper (I) iodide (0.48 g, 2.50 mmol), and trans-$N_1,N_2$-dimethylcyclohexane-1,2-diamine (0.71 g, 4.99 mmol) was stirred at 130° C. for 16 hours in a nitrogen atmosphere. After being cooled to room temperature, the mixture was diluted with water and extracted twice with ethyl acetate. The organic layer was washed twice with brine, dried over anhydrous sodium sulfate, and filtered off, and the solvent was distilled off under reduced pressure to give aa399-c as a crude product (6.1 g).

Using aa220-a (17.7 g, 31.0 mmol), aa399-d (10.5 g, 31%) was obtained in the same manner as Compound aa219-b except that aa399-c was used in place of 4-bromo-2-fluoro-1-(trifluoromethyl)benzene.

LCMS (ESI) m/z=567 (M+Na)+

Retention time: 0.95 min (Analytical condition SMD method_22)

TMSOTf (8.56 g, 38.5 mmol) was added to an IPAC solution (110 mL) of aa399-d (10.5 g, 19.3 mmol) and HMDS (6.22 g, 38.5 mmol) in a nitrogen atmosphere. The mixture was stirred at room temperature for 16 hours. After a 5% aqueous disodium hydrogen phosphate solution was added, the mixture was extracted 3 times with ethyl acetate. The organic layer was washed with a 2% aqueous phosphoric acid solution and washed with 15% brine. The organic layer was dried over sodium sulfate and filtered off, and the solvent was distilled off under reduced pressure. The resultant was purified by reverse phase chromatography (acetonitrile-water) and then washed with hexane/TBME (5/1) to give aa399 (7 g, 74%).

LCMS (ESI) m/z=489 (M+H)+

Retention time: 1.36 min (Analytical condition SMD method_23)

Synthesis of Compound aa400

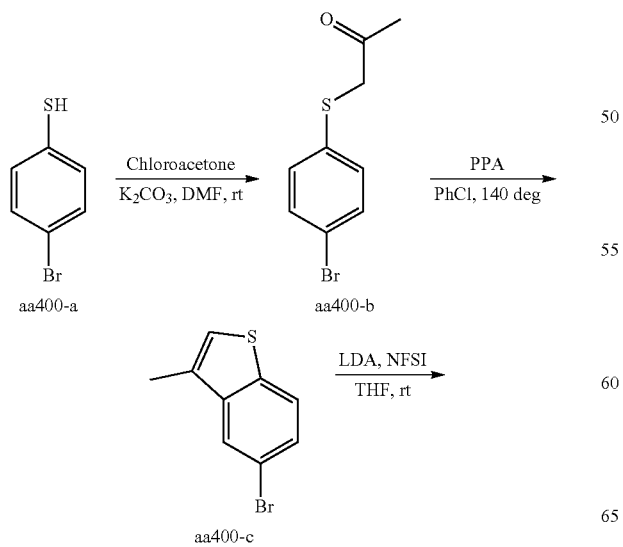

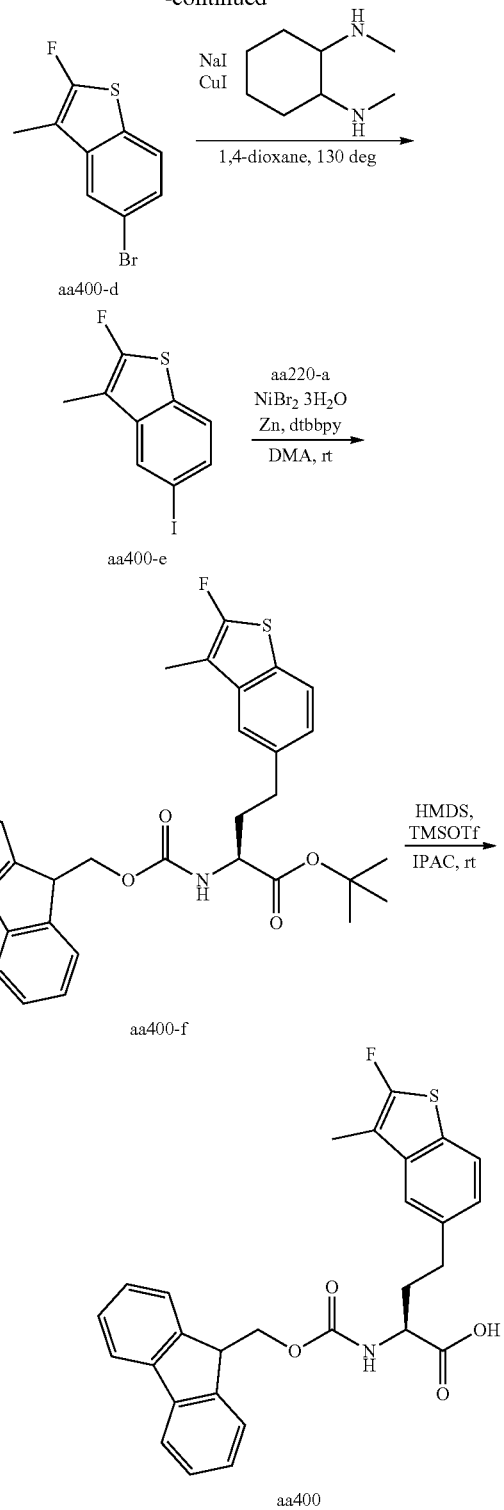

A DMF solution (500 mL) of aa400-a (4-bromobenzenethiol, CAS No. 106-53-6, 50 g, 264 mmol), potassium carbonate (73.1 g, 529 mmol), and chloroacetone (26.9 g, 291 mmol) was stirred at room temperature for 16 hours in a nitrogen atmosphere. Water was added, solids were filtered off, and the solvent was distilled off from the filtrate under reduced pressure to give aa400-b as a crude product (61.0 g).

A chlorobenzene solution (700 mL) of the crude product of aa400-b (84 g, 342 mmol) and PPA (250 g, 2.17 mmol) was stirred at 140° C. for 16 hours in a nitrogen atmosphere. After this solution was cooled to room temperature, the upper layer was added to ethyl acetate to be diluted, and washed with water, and then the solvent was distilled off under reduced pressure. The resulting residue was purified by silica gel column chromatography (ethyl acetate/petroleum ether) to give aa400-c (42.5 g, 54%).

Retention time: 1.13 min (Analytical condition SMD method_24)

A THF solution (300 mL) of aa400-c (40 g, 176 mmol) was cooled to −78° C., and LDA (2 M THF solution, 96 mL, 194 mmol) was added dropwise in a nitrogen atmosphere. The mixture was stirred at −78° C. for 30 minutes, and N-fluorobenzenesulfonimide (NFSI, 100 g, 317 mmol) was added dropwise at −78° C. After stirring this mixture at room temperature for 16 hours, an aqueous ammonium chloride solution was added, followed by extraction with ethyl acetate twice. The organic layer was washed twice with water, dried over anhydrous sodium sulfate, and filtered off, and the solvent was distilled off under reduced pressure. The resulting residue was purified by silica gel column chromatography (ethyl acetate/petroleum ether) to give aa400-d (20 g, 43%).

Retention time: 1.31 min (Analytical condition SMD method_26)

aa400-e was obtained as a crude product (25.0 g) in the same manner as Compound 399-c except that aa400-d (19 g, 77.5 mmol) was used in place of aa399-b.

Using aa220-a (19.0 g, 33.3 mmol), aa400-f (13.8 g, 73%) was obtained in the same manner as Compound aa219-b except that aa400-e was used in place of 4-bromo-2-fluoro-1-(trifluoromethyl)benzene.

LCMS (ESI) m/z=568 (M+Na)+

Retention time: 1.31 min (Analytical condition SMD method_26)

aa400 (8 g, 81%) was obtained in the same manner as Compound 399 except that aa400-f (3.0 g, 5.50 mmol) was used in place of aa399-d, and ethyl acetate was used as a solvent in place of IPAC.

LCMS (ESI) m/z=490 (M+H)+

Retention time: 1.31 min (Analytical condition SMD method_27)

Synthesis of Compound aa401

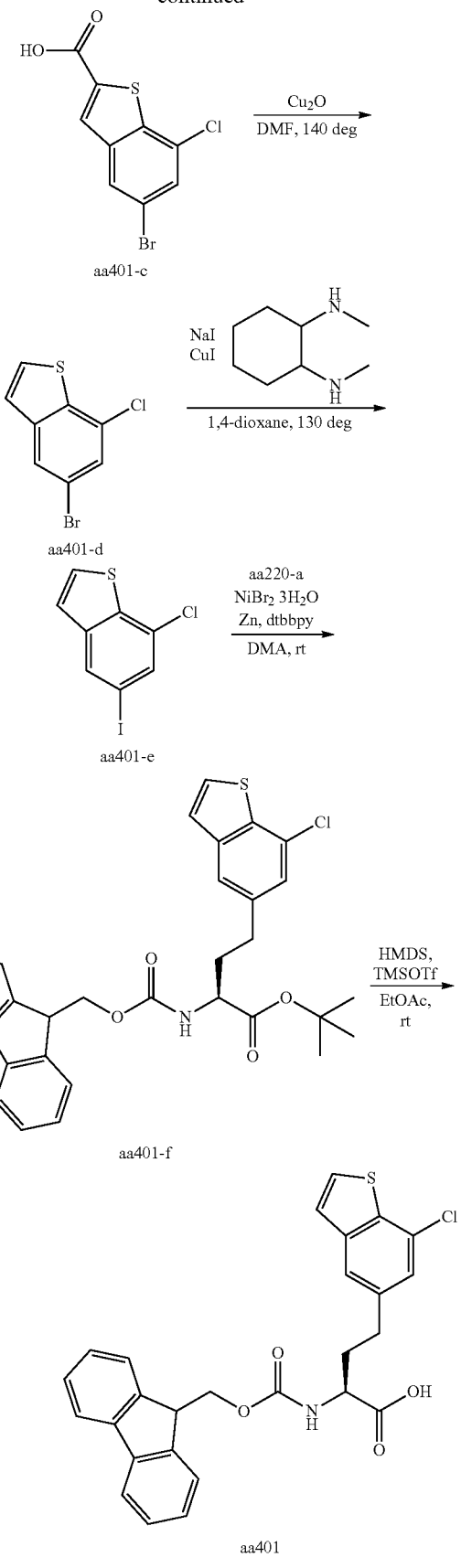

Methyl thioglycolate (10.2 g, 96.0 mmol) and potassium carbonate (22.1 g, 160 mmol) were added to an acetone solution (300 mL) of aa401-a (5-bromo-3-chloro-2-fluorobenzaldehyde, CAS No. 1280786-80-2, 19 g, 80 mmol) at room temperature, and the mixture was stirred at 60° C. for 2 hours in a nitrogen atmosphere. After the mixture was cooled to room temperature, solids were filtered off, and the solvent was distilled off under reduced pressure. The resulting residue was dissolved in ethyl acetate, dried over anhydrous sodium sulfate, and filtered off, and the solvent was distilled off under reduced pressure. The resulting residue was purified by silica gel column chromatography (ethyl acetate/petroleum ether) to give aa401-b (16.4 g, 67%).

Retention time: 0.89 min (Analytical condition SMD method_22)

Lithium hydroxide monohydrate (6.43 g, 268 mmol) was added to a THF (102 mL)/methanol (34 mL)/water (34 mL) solution of aa401-b (16.4 g, 53.7 mmol) at room temperature. After stirring this mixture at room temperature for 1 hour, the solvent was distilled off under reduced pressure. The resulting residue was dissolved in water, and 2 M hydrochloric acid was added to adjust the pH to 3, followed by extraction with ethyl acetate 3 times. The organic layer was washed with water, dried over anhydrous sodium sulfate, and filtered off, and the solvent was distilled off under reduced pressure to give aa401-c as a crude product (15.9 g).

Copper (I) oxide (31.2 g, 218 mmol) was added to a DMF solution (160 mL) of the crude product of 401-c (15.9 g, 54.5 mmol), and the mixture was stirred at 140° C. for 16 hours. After solids were filtered off, the filtrate was washed with water, dried over anhydrous sodium sulfate, and filtered off, and the solvent was distilled off under reduced pressure. The resulting residue was purified by silica gel column chromatography (ethyl acetate/petroleum ether) to give aa401-d (11.7 g, 87%).

Retention time: 0.99 min (Analytical condition SMD method_28)

aa401-e was obtained as a crude product (12.5 g) in the same manner as Compound 399-c except that aa401-d (11.7 g, 47.3 mmol) was used in place of aa399-b.

Using aa220-a (12.1 g, 21.2 mmol), aa401-f (8.6 g, 74%) was obtained in the same manner as Compound aa219-b except that aa401-e was used in place of 4-bromo-2-fluoro-1-(trifluoromethyl)benzene.

LCMS (ESI) m/z=570 (M+Na)+

Retention time: 0.96 min (Analytical condition SMD method_22)

aa401 (4.4 g, 57%) was obtained in the same manner as Compound 399 except that aa401-f (8.6 g) was used in place of aa399-d, and ethyl acetate was used as a solvent in place of IPAC.

LCMS (ESI) m/z=492 (M+H)+

Retention time: 1.33 min (Analytical condition SMD method_29)

Synthesis of Compound aa402

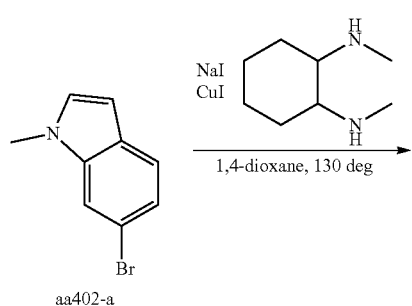

aa402-a

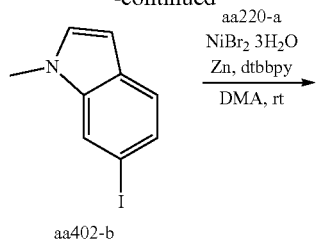

aa402-b

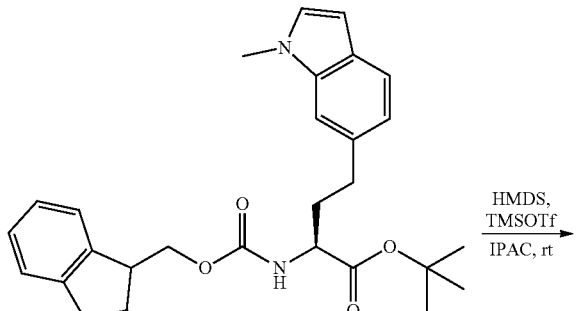

aa402-c

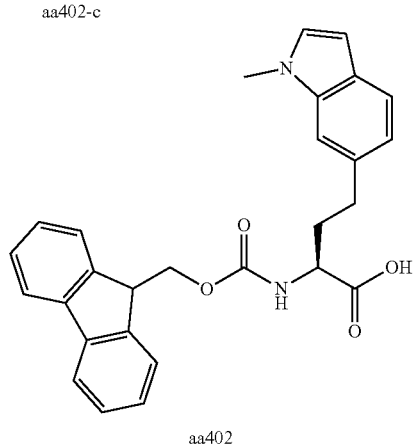

aa402 aa402-b was obtained as a crude product (23 g) in the same manner as Compound 399-c except that aa402-a (6-bromo-1-methyl-1H-indole, CAS No. 125872-95-9, 20 g, 95.2 mmol) was used in place of aa399-b.

Using aa220-a (9.00 g, 15.8 mmol), aa402-c (3.6 g, 44%) was obtained in the same manner as Compound aa219-b except that aa402-b was used in place of 4-bromo-2-fluoro-1-(trifluoromethyl)benzene.

LCMS (ESI) m/z=511 (M+H)+

Retention time: 0.92 min (Analytical condition SMD method_30)

aa402 (5 g, 70%) was obtained in the same manner as Compound 399 except that aa402-c (8.00 g, 15.7 mmol) was used in place of aa399-d.

LCMS (ESI) m/z=455 (M+H)+

Retention time: 1.04 min (Analytical condition SMD method_24)

Synthesis of Compound aa403

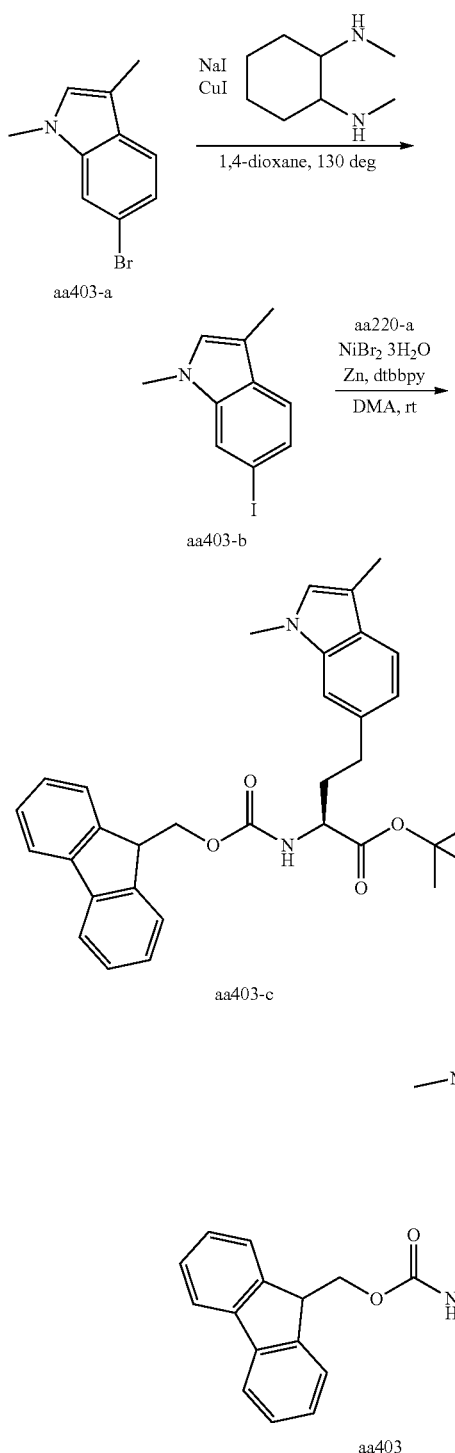

aa403-b was obtained as a crude product (18.1 g) in the same manner as Compound 399-c except that aa403-a (6-bromo-1,3-dimethyl-1H-indole, CAS No. 1616099-24-1, 15.3 g, 68.3 mmol) was used in place of aa399-b.

Using aa220-a (19.1 g, 33.4 mmol), aa403-c (9.5 g, 54%) was obtained in the same manner as Compound aa219-b except that aa403-b was used in place of 4-bromo-2-fluoro-1-(trifluoromethyl)benzene.

LCMS (ESI) m/z=525 (M+H)+

Retention time: 0.97 min (Analytical condition SMD method_31)

A crude product of aa403 was obtained in the same manner as Compound 219 except that aa403-c (9.5 g, 18.1 mmol) was used in place of aa219-b. The crude product was purified by reverse phase chromatography (acetonitrile-water) to give aa403 (4.5 g, 53%).

LCMS (ESI) m/z=469 (M+H)+

Retention time: 1.82 min (Analytical condition SMD method_32)

Synthesis of Compound aa404

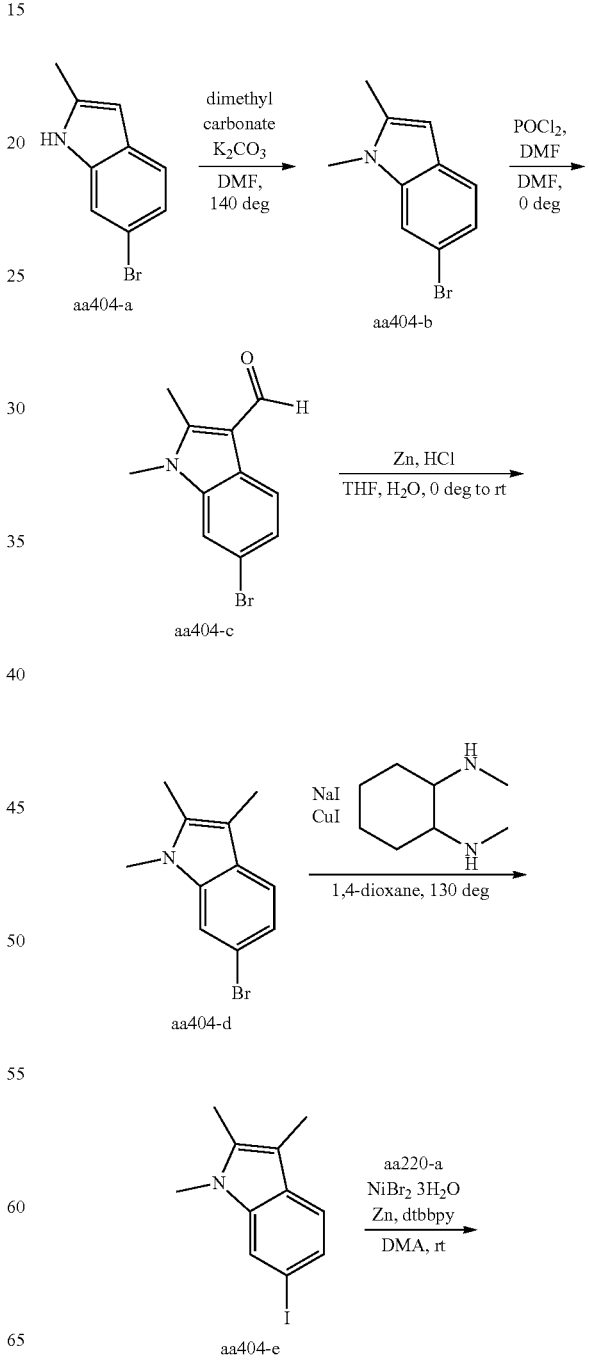

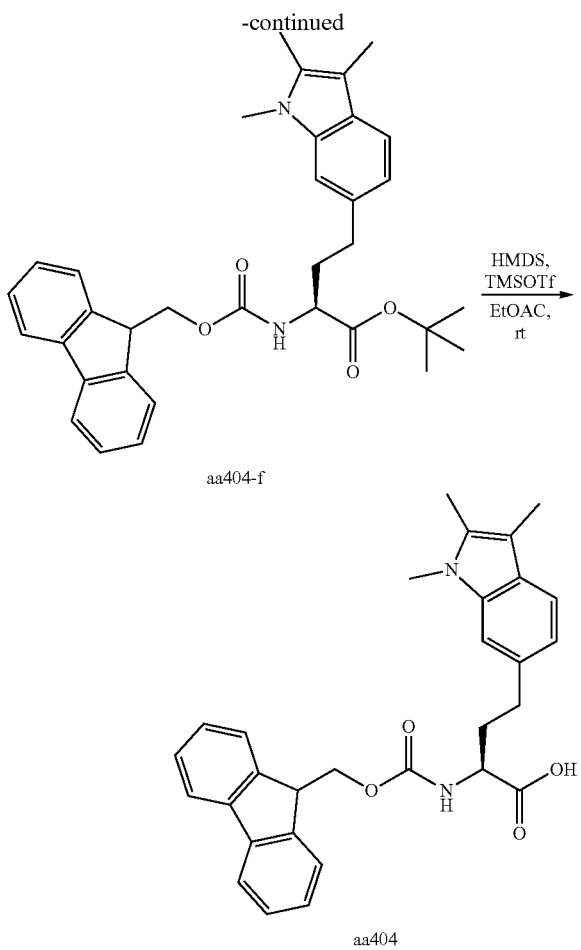

aa404-f aa404

A DMF solution (100 mL) of aa404-a (6-bromo-2-methyl-1H-indole, CAS No. 6127-19-1, 19 g, 90.4 mmol), potassium carbonate (18.9 g, 137 mmol), and dimethyl carbonate (24.4 g, 271 mmol) was stirred at 140° C. for 16 hours in a nitrogen atmosphere. After being cooled to room temperature, the solution was diluted with 1 M hydrochloric acid and extracted twice with ethyl acetate. The organic layer was washed with brine, dried over sodium sulfate, and filtered off, and the solvent was distilled off under reduced pressure. The resulting residue was purified by silica gel column chromatography (ethyl acetate/petroleum ether) to give aa404-b (25 g, quant.).

LCMS (ESI) m/z=224 (M+H)+

Retention time: 0.98 min (Analytical condition SMD method_33)

Phosphorus oxychloride (16.6 mL, 179 mmol) was added dropwise to DMF (200 mL) under ice cooling in a nitrogen atmosphere. The mixture was stirred for 10 minutes under ice cooling, and a DMF solution (50 mL) of aa404-b (20 g, 89.2 mmol) was added dropwise over 10 minutes under ice cooling. The mixture was stirred at room temperature for 40 minutes, and treated with an aqueous sodium hydrogen carbonate solution. The mixture was stirred for 10 minutes and then extracted twice with ethyl acetate, the organic layer was washed with brine, dried over sodium sulfate, and filtered off, and the solvent was distilled off under reduced pressure to give aa404-c as a crude product (19 g).

Hydrochloric acid (12 M, 21.5 mL, 377 mmol) was added dropwise to a THF solution (500 mL) of the crude product of aa404-c (19 g, 75.4 mmol) and zinc powder (14.8 g, 226 mmol) under ice cooling in a nitrogen atmosphere. The mixture was stirred at room temperature for 16 hours and then diluted with water. The mixture was extracted twice with ethyl acetate, the organic layer was washed with brine, dried over sodium sulfate, and filtered off, and the solvent was distilled off under reduced pressure to give aa404-d as a crude product (13 g).

aa404-e was obtained as a crude product (16 g) in the same manner as Compound 399-c except that aa404-d (13 g, 54.6 mmol) was used in place of aa399-b.

Using aa220-a (16.5 g, 28.9 mmol), Compound aa404-f (7.9 g, 45%) was obtained in the same manner as Compound aa219-b except that aa404-e was used in place of 4-bromo-2-fluoro-1-(trifluoromethyl)benzene.

LCMS (ESI) m/z=539 (M+H)+

Retention time: 1.08 min (Analytical condition SMD method_33)

aa404 (4.5 g, 62%) was obtained in the same manner as Compound 399 except that aa404-f (7.9 g, 14.7 mmol) was used in place of aa399-d, and ethyl acetate was used as a solvent in place of IPAC.

LCMS (ESI) m/z=483 (M+H)+

Retention time: 1.35 min (Analytical condition SMD method_34)

Synthesis of Compound aa405

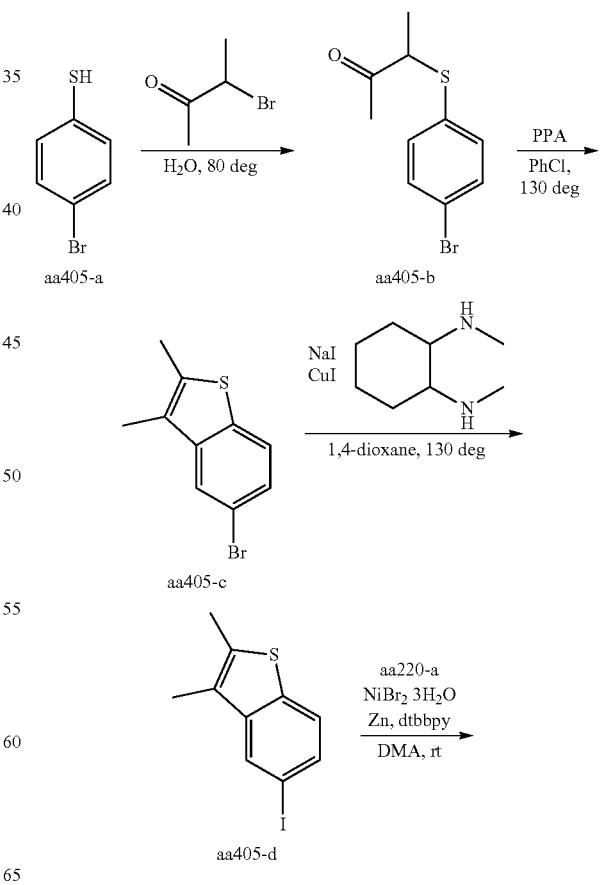

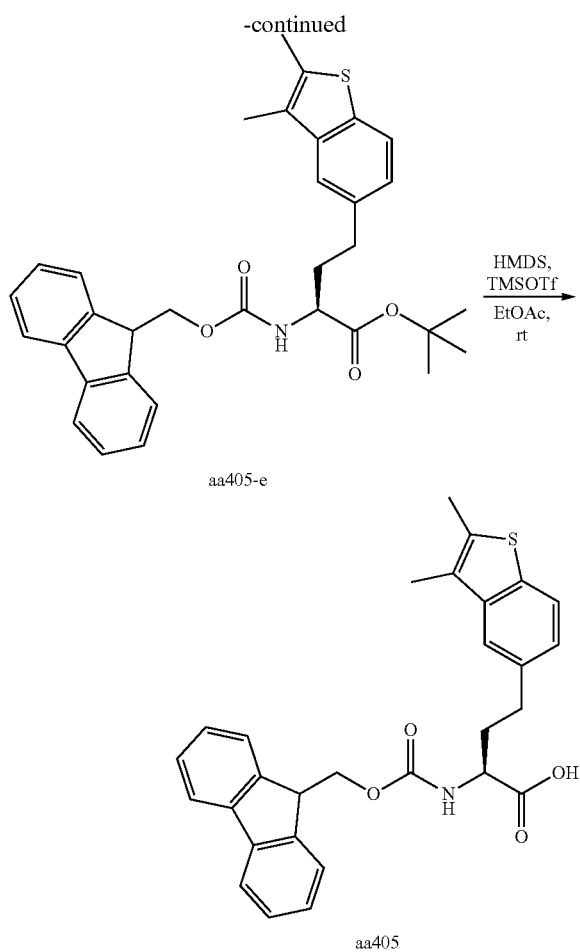

aa405-e aa405

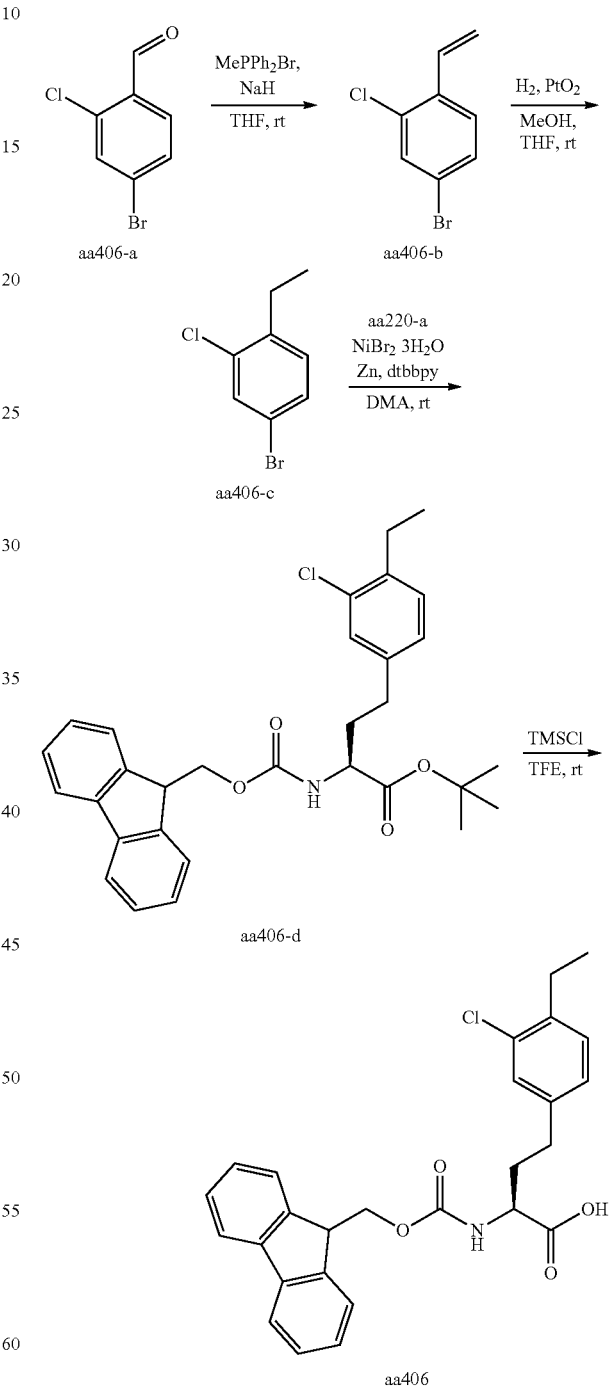

aa405 (5.03 g, 61%) was obtained in the same manner as Compound 399 except that aa405-e (9.06 g, 16.7 mmol) was used in place of aa399-d, and ethyl acetate was used as a solvent in place of IPAC.

LCMS (ESI) m/z=486 (M+H)+

Retention time: 1.47 min (Analytical condition SMD method_37)

Synthesis of Compound aa406

3-Bromo-2-butanone (28.8 g, 190 mmol) was added to an aqueous solution (300 mL) of aa405-a (4-bromobenzenethiol, CAS No. 106-53-6, 30 g, 159 mmol), and the mixture was stirred at 80° C. for 1 hour. The mixture was extracted 3 times with ethyl acetate, the organic layer was dried over anhydrous sodium sulfate and filtered off, and the solvent was distilled off under reduced pressure. The resulting residue was purified by silica gel column chromatography (ethyl acetate/petroleum ether) to give aa405-b (40 g, 85%).

LCMS (ESI) m/z=259 (M+H)+

Retention time: 0.71 min (Analytical condition SMD method_35)

aa405-c (13.7 g, 70%) was obtained in the same manner as Compound aa400-c except that aa405-b (20 g, 77.1 mmol) was used in place of aa400-b.

Retention time: 0.88 min (Analytical condition SMD method_36)

aa405-d was obtained as a crude product (15.4 g) in the same manner as Compound 399-c except that aa405-c (13.7 g, 56.8 mmol) was used in place of aa399-b.

Using aa220-a (15.3 g, 26.7 mmol), aa405-e (9.06 g, 61%) was obtained in the same manner as Compound aa219-b except that aa405-d was used in place of 4-bromo-2-fluoro-1-(trifluoromethyl)benzene.

LCMS (ESI) m/z=564 (M+Na)+

Retention time: 0.99 min (Analytical condition SMD method_36)

NaH (5.03 g, 210 mmol) was added in small divided portions to a THF solution (100 mL) of (bromomethyl)triphenylphosphonium bromide (49.9 g, 140 mmol) at 55° C. in a nitrogen atmosphere. The mixture was stirred at 55°

C. for 30 minutes and then cooled to room temperature, and a THF solution (50 mL) of aa406-a (2-chloro-4-bromobenzaldehyde, CAS No. 158435-41-7, 15.3 g, 70 mmol) was added dropwise. After stirring this mixture at room temperature for 16 hours, water was added. The mixture was extracted 3 times with ethyl acetate, the organic layer was washed with water, dried over sodium sulfate, and filtered off, and the solvent was distilled off under reduced pressure to give aa406-b as a crude product (43 g).

A methanol (10 mL)/THF (10 mL) solution of aa406-b (2.5 g, 11.5 mmol) and platinum (IV) oxide (0.25 g, 1.10 mmol) was stirred at room temperature for 2 hours in a hydrogen atmosphere. Solids were filtered off, and the solvent was distilled off from the filtrate under reduced pressure. The resulting residue was purified by silica gel column chromatography (ethyl acetate/petroleum ether) to give aa406-c (1.2 g, 42%).

Retention time: 1.41 min (Analytical condition SMD method_38)

Using aa220-a (17 g, 30.0 mmol), Compound aa406-d (4.8 g, 31%) was obtained in the same manner as Compound aa219-b except that aa406-c was used in place of 4-bromo-2-fluoro-1-(trifluoromethyl)benzene.

LCMS (ESI) m/z=542 (M+Na)+

Retention time: 1.53 min (Analytical condition SMD method_38)

aa406 (4.3 g, 95%) was obtained in the same manner as Compound 219 except that aa406-d (5 g, 9.61 mmol) was used in place of aa219-b.

LCMS (ESI) m/z=486 (M+Na)+

Retention time: 1.32 min (Analytical condition SMD method_38)

Synthesis of Compound aa407

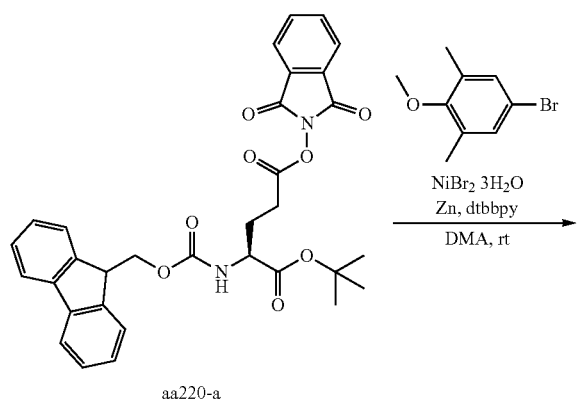

aa220-a

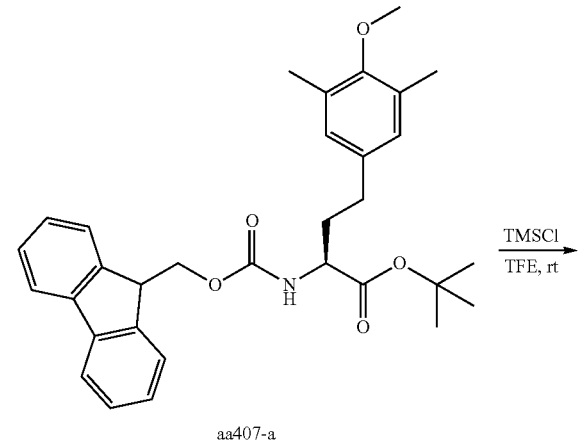

aa407-a

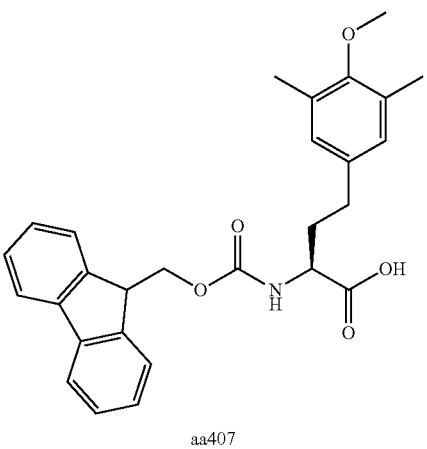

aa407

Using aa220-a (21 g, 36.8 mmol), aa407-a (9.84 g, 52%) was obtained in the same manner as Compound aa219-b except that 4-bromo-2,6-dimethylanisole (CAS No. 14804-38-7) was used in place of 4-bromo-2-fluoro-1-(trifluoromethyl)benzene.

LCMS (ESI) m/z=538 (M+Na)+

Retention time: 1.44 min (Analytical condition SMD method_38)

aa407 (4.3 g, 95%) was obtained in the same manner as Compound 219 except that aa407-a (9.84 g, 19.1 mmol) was used in place of aa219-b.

LCMS (ESI) m/z=460 (M+H)+

Retention time: 1.23 min (Analytical condition SMD method_38)

Synthesis of Compound aa408

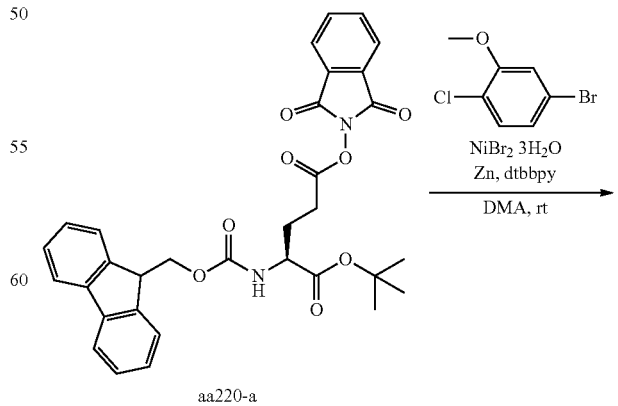

aa220-a

249

-continued

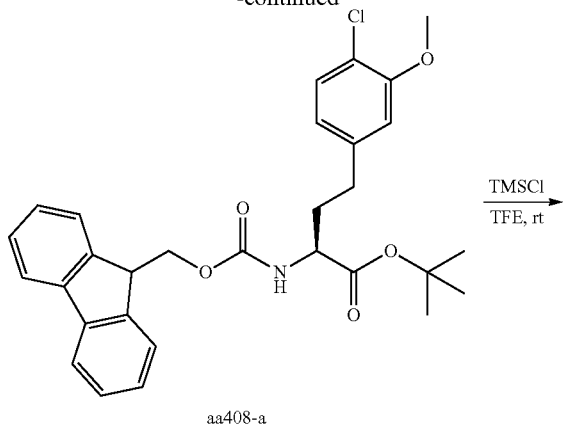

aa408-a

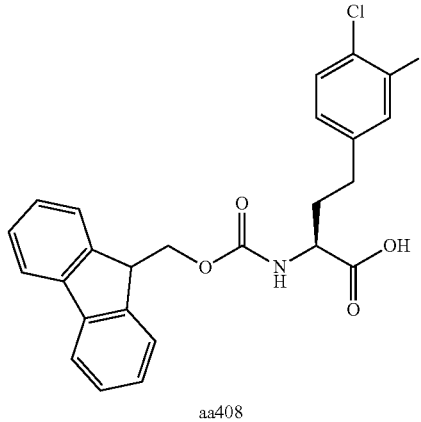

aa408

250

Synthesis of Compound aa409

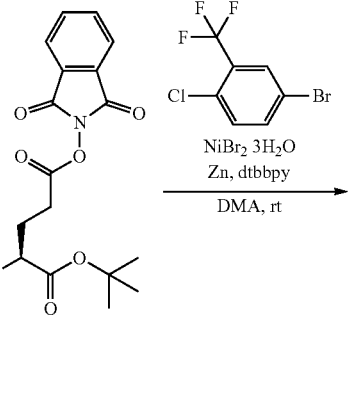

aa220-a

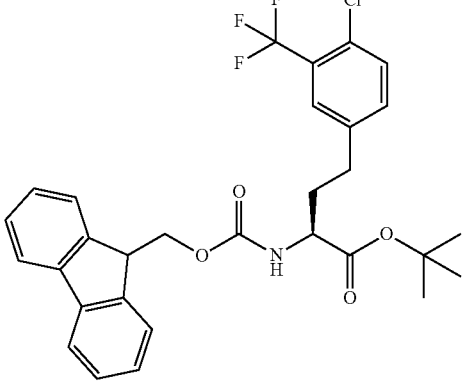

aa409-a

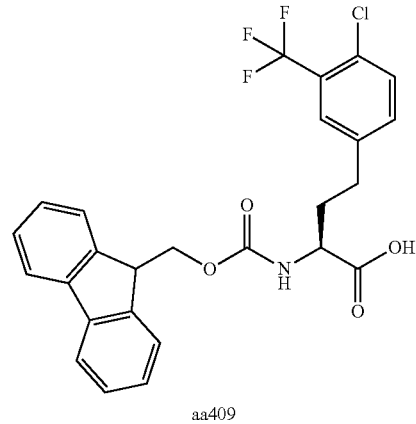

aa409

Using aa220-a (15 g, 26.3 mmol), aa408-a (6.4 g, 46%) was obtained in the same manner as Compound aa219-b except that 5-bromo-2-chloroanisole (CAS No. 16817-43-9) was used in place of 4-bromo-2-fluoro-1-(trifluoromethyl)benzene.

LCMS (ESI) m/z=544 (M+Na)+

Retention time: 0.89 min (Analytical condition SMD method_39)

aa408 (3.5 g, 62%) was obtained in the same manner as Compound 219 except that aa408-a (6.4 g, 12.3 mmol) was used in place of aa219-b.

LCMS (ESI) m/z=488 (M+Na)+

Retention time: 1.00 min (Analytical condition SMD method_26)

Using aa220-a (5 g, 8.76 mmol), aa409-a (3.8 g, 77%) was obtained in the same manner as Compound aa219-b except that 5-bromo-2-chlorobenzotrifluoride (CAS No. 445-01-2) was used in place of 4-bromo-2-fluoro-1-(trifluoromethyl)benzene.

LCMS (ESI) m/z=582 (M+Na)+

Retention time: 0.93 min (Analytical condition SMD method_40)

aa409 (3 g, 88%) was obtained in the same manner as Compound 219 except that aa409-a (3.8 g, 6.79 mmol) was used in place of aa219-b.

LCMS (ESI) m/z=526 (M+Na)+

Retention time: 1.08 min (Analytical condition SMD method_26)

Synthesis of Compound aa410

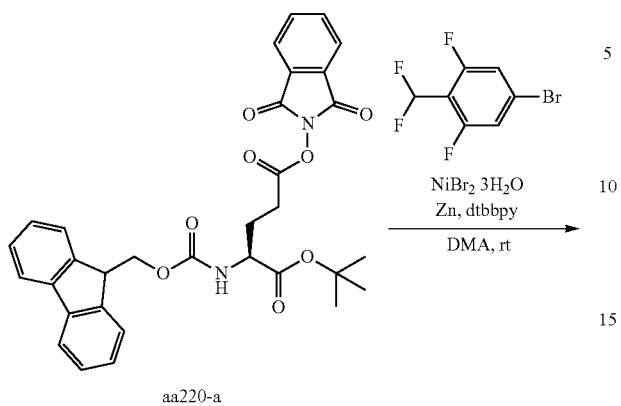

aa220-a

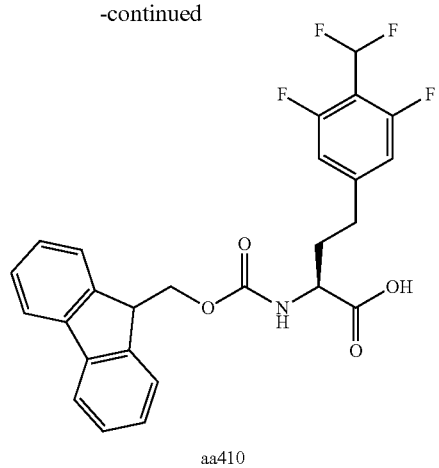

aa410

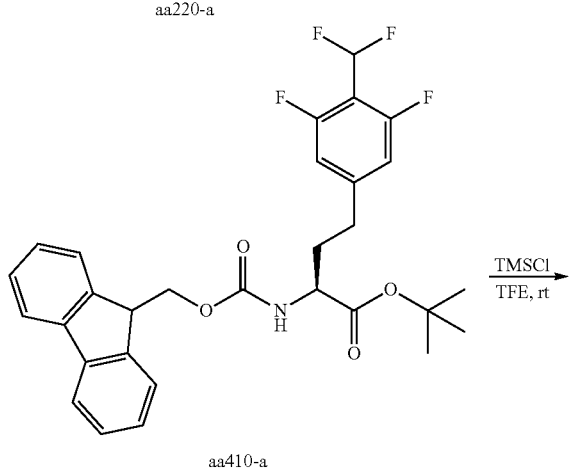

aa410-a

Using aa220-a (5 g, 8.76 mmol), aa410-a (3.5 g, 73%) was obtained in the same manner as Compound aa219-b except that 5-bromo-2-(difluoromethyl)-1,3-difluorobenzene
(CAS No. 1221272-77-0) was used in place of 4-bromo-2-fluoro-1-(trifluoromethyl)benzene. LCMS (ESI) m/z=566 (M+Na)+
Retention time: 1.21 min (Analytical condition SMD method_24)
aa410 (1.9 g, 60%) was obtained in the same manner as Compound 219 except that aa410-a (3.5 g, 6.44 mmol) was used in place of aa219-b.
LCMS (ESI) m/z=488 (M+H)+
Retention time: 0.99 min (Analytical condition SMD method_41)

Synthesis of Compound aa411

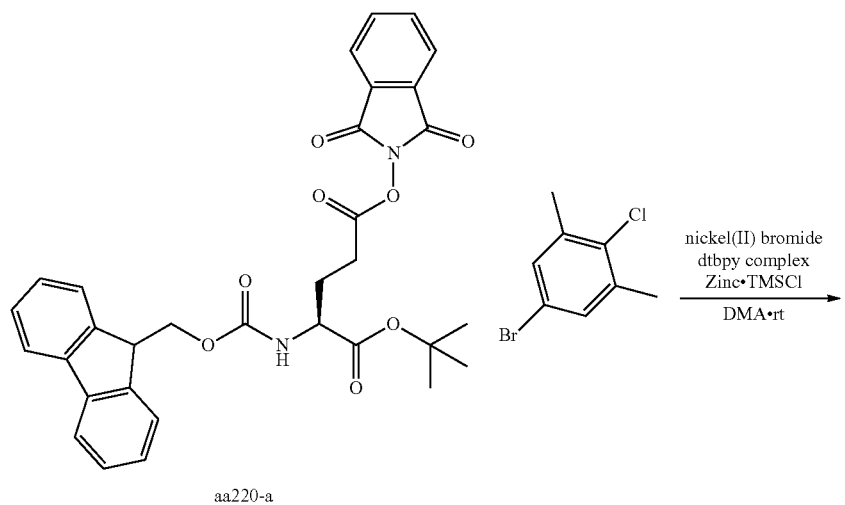

aa220-a

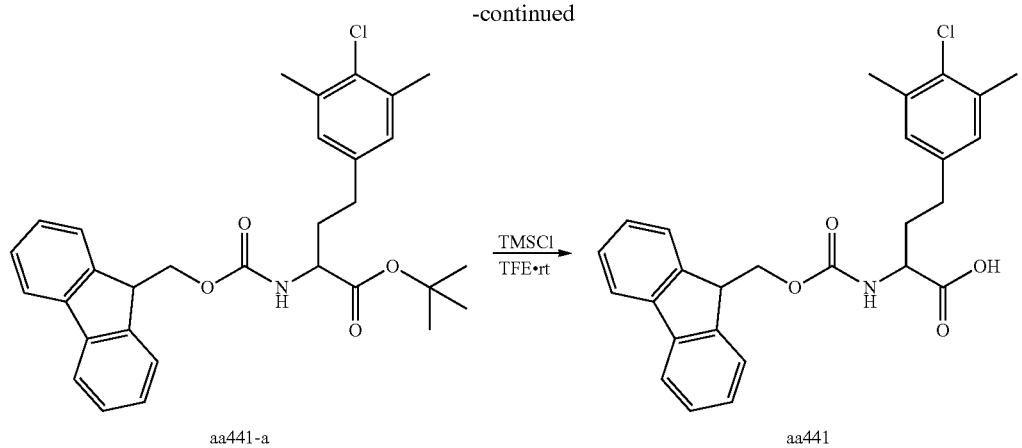

An N,N-dimethylacetamide (2.92 mL) solution of a nickel (II) bromide 4,4'-di-tert-butyl-2,2'-bipyridine complex (85 mg, 0.175 mmol) and chlorotrimethylsilane (0.111 mL, 0.876 mmol) were added to an N,N-dimethylacetamide (5.84 mL) solution of aa220-a (1.00 g, 1.75 mmol), 5-bromo-2-chloro-1,3-dimethylbenzene (577 mg, 2.63 mmol), and zinc (573 mg, 8.76 mmol), and the mixture was stirred at room temperature for 23 hours in a nitrogen atmosphere. tert-Butyl methyl ether (10 mL) was added, the mixture was passed through a Celite filter covered with sodium sulfate, and then a 5 wt % aqueous disodium ethylenediaminetetraacetate solution (40 mL) was added for extraction. The organic layer was washed with a 5 wt % aqueous sodium carbonate solution (20 mL), washed with a saturated aqueous ammonium chloride solution (20 mL), washed with brine (20 mL), and dried over anhydrous sodium sulfate, and then the solvent was distilled off under reduced pressure to give aa441-a as a crude product.

The crude product of aa441-a was dissolved in TFE (8.76 mL), TMSCl (0.667 mL, 5.26 mmol) was added, and the mixture was stirred at room temperature for 30 minutes. The solvent was distilled off from the mixture under reduced pressure, the resulting crude product was purified by reverse phase column chromatography (0.1% aqueous formic acid solution/0.1% formic acid acetonitrile solution) to give aa441 (364 mg, 45% in 2 steps).

LCMS (ESI) m/z=462 (M−H)−

Retention time: 1.01 min (Analytical condition SQDFA05)

Synthesis of Compound aa414

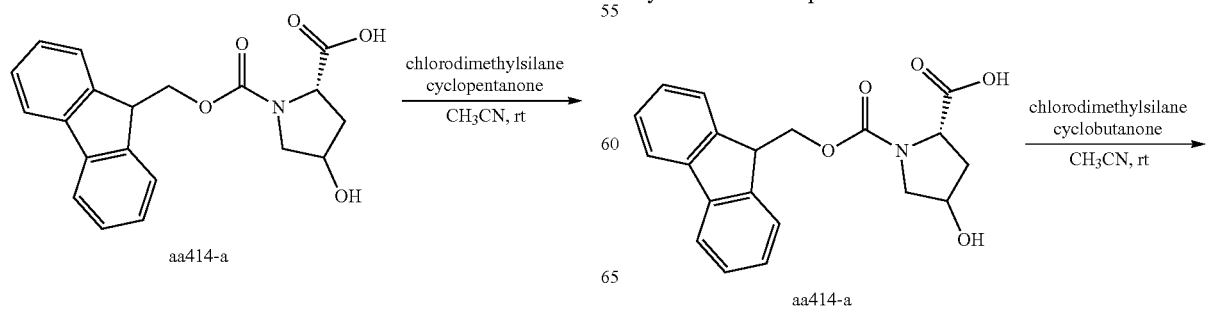

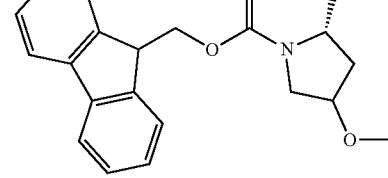

Chlorodimethylsilane (18.5 mL, 170 mmol) was added to an acetonitrile (51.5 mL) solution of aa414-a ((2S,4R)-1-(((9H-fluoren-9-yl)methoxy) carbonyl)-4-hydroxypyrrolidine-2-carboxylic acid, Fmoc-Hyp-OH, CAS No. 88050-17-3)(10.0 g, 28.3 mmol) and cyclopentanone (15.0 mL, 170 mmol), and the mixture was stirred at room temperature for 28 hours. A 2 N aqueous sodium hydroxide solution (85 mL) was slowly added dropwise thereto under ice cooling so as not to exceed 30° C. A 2 N aqueous sodium hydroxide solution (14 mL) was further added to adjust the pH to 11. Phosphoric acid was added thereto to adjust the pH to 7 to 8, and the mixture was washed with TBME/hexane (1/3, 150 mL). Phosphoric acid was added to the aqueous layer to adjust the pH to 3, followed by extraction with TBME (150 mL) and further extraction with TBME (100 mL). After the resulting organic layer was washed with brine and dried over anhydrous sodium sulfate, the solvent was distilled off under reduced pressure to give aa414 (11.7 g, 98%).

LCMS (ESI) m/z=422 (M+H)+

Retention time: 0.91 min (Analytical condition SQDFA05)

Synthesis of Compound aa415

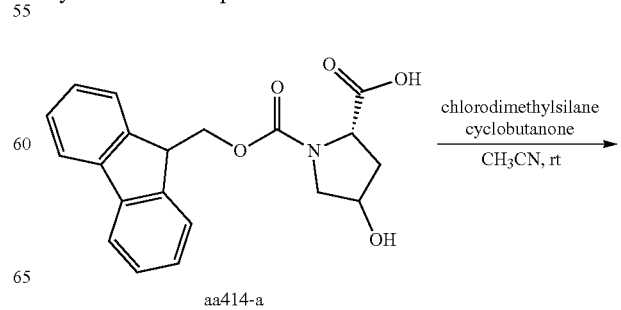

255
-continued

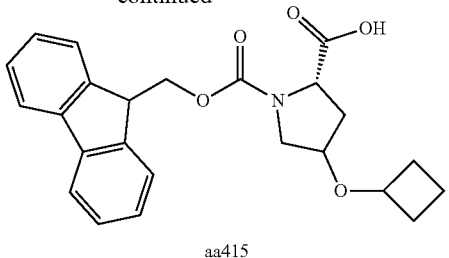

aa415 aa415 (10.8 g, 94%) was obtained in the same manner as Compound 414 except that cyclopentanone was used in place of cyclobutanone.
LCMS (ESI) m/z=408 (M+H)+
Retention time: 0.86 min (Analytical condition SQDFA05)
Synthesis of Compound aa443

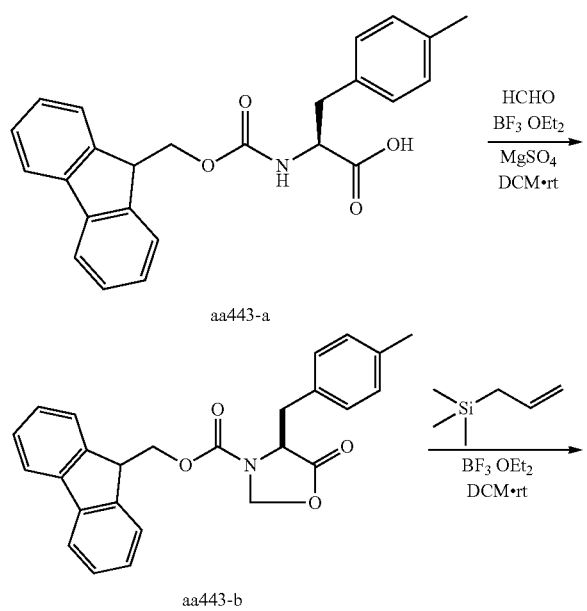

aa443-a aa443-b

256
-continued

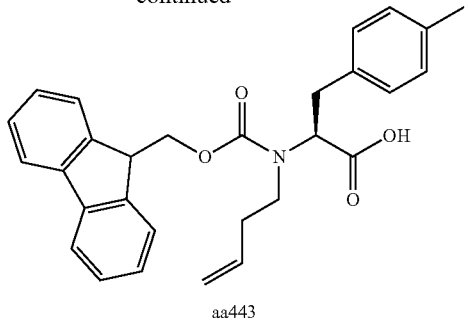

aa443

Using Compound aa443-a (N-([(9H-fluoren-9-yl) methoxy]carbonyl)-4-(methyl)-L-phenylalanine) as a starting material, a crude product of aa443-b (2.39 g, 93%) was obtained in the same manner as synthesis of Compound tp006-b.
LCMS (ESI) m/z=414.5 (M+H)+
Retention time: 1.01 min (Analytical condition SQDFA05)
Using the resulting crude product of Compound aa443-b, Compound aa443 (2.23 g, 85%) was obtained in the same manner as synthesis of Compound tp006-c.
LCMS (ESI) m/z=454 (M−H)+
Retention time: 0.99 min (Analytical condition SQDFA05)

1-2. Synthesis of Amino Acid-Supporting Resin Used in Solid-Phase Peptide Synthesis by Peptide Synthesizer Amino acids listed in Table 5 were synthesized by the method shown below, supported on a resin, and used in peptide synthesis by a peptide synthesizer. Resins on which Compound aa427 to Compound aa438 were supported were synthesized by the following method using resins on which the amino acids shown in Table 5 were supported as raw materials, and used in peptide synthesis with a peptide synthesizer. Amino acids listed in Table 6 were purchased from commercial suppliers, supported on a resin, and used in peptide synthesis by a peptide synthesizer. The reaction for causing Fmoc amino acid to be supported on a resin was carried out according to the method described in WO2013/100132 or WO2018/225864. 2-Chlorotrityl chloride resin (100 to 200 mesh, 1% DVB) was purchased from Watanabe Chemical Industries Ltd., and Chem-Impex.

TABLE 5

| Compound No. | Abbreviation | Structural Formula | Name |
|---|---|---|---|
| aa358 | Fmoc-MeAsp-mor |  | (3S)-3-[9H-fluoren-9-ylmethoxycarbonyl(methyl)amino]-4-morpholin-4-yl-4-oxobutanoic acid |

TABLE 5-continued

| Compound No. | Abbreviation | Structural Formula | Name |
|---|---|---|---|
| aa359 | Fmoc-MeAsp-NMe2 | | (3S)-4-(dimethylamino)-3-[9H-fluoren-9-ylmethoxycarbonyl(methyl)amino]-4-oxobutanoic acid |
| aa360 | Fmoc-MeAsp-pyrro | | (3S)-3-[9H-fluoren-9-ylmethoxycarbonyl(methyl)amino]-4-oxo-4-pyrrolidin-1-ylbutanoic acid |
| aa361 | Fmoc-MeAsp-aze | | (3S)-4-(azetidin-1-yl)-3-[9H-fluoren-9-ylmethoxycarbonyl(methyl)amino]-4-oxobutanoic acid |
| aa362 | Fmoc-MeAsp-pip | | (3S)-3-[9H-fluoren-9-ylmethoxycarbonyl(methyl)amino]-4-oxo-4-piperidin-1-ylbutanoic acid |
| aa363 | Fmoc-MeAsp-mor(26-bicyc) | | (3S)-3-[9H-fluoren-9-ylmethoxycarbonyl(methyl)amino]-4-(3-oxa-8-azabicyclo[3.2.1]octan-8-yl)-4-oxobutanoic acid |

TABLE 5-continued

| Compound No. | Abbreviation | Structural Formula | Name |
|---|---|---|---|
| aa364 | Fmoc-MeAsp-pyrro(3-Me2) | | (3S)-4-(3,3-dimethylpyrrolidin-1-yl)-3-[9H-fluoren-9-ylmethoxycarbonyl(methyl)amino]-4-oxobutanoic acid |
| aa365 | Fmoc-MeAsp-pip(4-Me) | | (3S)-3-[9H-fluoren-9-ylmethoxycarbonyl(methyl)amino]-4-(4-methylpiperidin-1-yl)-4-oxobutanoic acid |
| aa366 | Fmoc-MeAsp-piz(oxe) | | (3S)-3-[9H-fluoren-9-ylmethoxycarbonyl(methyl)amino]-4-[4-(oxetan-3-yl)piperazin-1-yl]-4-oxobutanoic acid |
| aa367 | Fmoc-MeAsp-oxz | | (3S)-3-[9H-fluoren-9-ylmethoxycarbonyl(methyl)amino]-4-(1,3-oxazolidin-3-yl)-4-oxobutanoic acid |
| aa368 | Fmoc-Asp-NMe2 | | (3S)-4-(dimethylamino)-3-(9H-fluoren-9-ylmethoxycarbonyl-amino)-4-oxobutanoic acid |

TABLE 5-continued

| Compound No. | Abbreviation | Structural Formula | Name |
|---|---|---|---|
| aa369 | Fmoc-Asp-mor | | (3S)-3-(9H-fluoren-9-ylmethoxy-carbonylamino)-4-morpholin-4-yl-4-oxobutanoic acid |
| aa373 | Fmoc-D-MeAsp-NMe2 | | (R)-3-((((9H-fluoren-9-yl)methoxy)carbonyl)(methyl)amino)-4-(dimethylamino)-4-oxobutanoic acid |
| aa374 | Fmoc-MeGly(cPent)-MeAsp-NMe2 | | (S)-3-((S)-2-((((9H-fluoren-9-yl)methoxy)carbonyl)(methyl)amino)-2-cyclopentyl-N-methylacetamido)-4-(dimethylamino)-4-oxobutanoic acid |
| aa375 | Fmoc-MeGly(cPent)-MeAsp-mor | | (S)-3-((S)-2-((((9H-fluoren-9-yl)methoxy)carbonyl)(methyl)amino)-2-cyclopentyl-N-methylacetamido)-4-morpholino-4-oxobutanoic acid |
| aa376 | Fmoc-MeGly(cPent)-EtAsp-NMe2 | | (3S)-3-[[(2S)-2-cyclopentyl-2-[9H-fluoren-9-ylmethoxycarbonyl(methyl)amino]acetyl]-ethyl-amino]-4-(dimethylamino)-4-oxo-butanoic acid |

TABLE 5-continued

| Compound No. | Abbreviation | Structural Formula | Name |
| --- | --- | --- | --- |
| aa377 | Fmoc-MeGly(cPent)-nPrAsp-NMe2 | | (3S)-3-[[(2S)-2-cyclopentyl-2-[9H-fluoren-9-ylmethoxycarbonyl(methyl)amino]acetyl]-propyl-amino]-4-(dimethylamino)-4-oxo-butanoic acid |
| aa378 | Fmoc-MeGly(cPent)-cBuEtAsp-NMe2 | | (3S)-3-[2-cyclobutylethyl-[(2S)-2-cyclopentyl-2-[9H-fluoren-9-ylmethoxycarbonyl(methyl)amino]acetyl]amino]-4-(dimethylamino)-4-oxo-butanoic acid |
| aa379 | Fmoc-MeGly(cPent)-cPentEtAsp-NMe2 | | (3S)-3-[2-cyclopentylethyl-[(2S)-2-cyclopentyl-2-[9H-fluoren-9-ylmethoxycarbonyl(methyl)amino]acetyl]amino]-4-(dimethylamino)-4-oxo-butanoic acid |
| aa380 | Fmoc-MeGly(cPent)-PhenethylAsp-NMe2 | | (3S)-3-[[(2S)-2-cyclopentyl-2-[9H-fluoren-9-ylmethoxycarbonyl(methyl)amino]acetyl]-(2-phenylethyl)amino]-4-(dimethylamino)-4-oxo-butanoic acid |
| aa381 | Fmoc-MeGly(cPent)-EtAsp-mor | | (3S)-3-[[(2S)-2-cyclopentyl-2-[9H-fluoren-9-ylmethoxycarbonyl(methyl)amino]acetyl]-ethyl-amino]-4-morpholino-4-oxo-butanoic acid |

TABLE 5-continued

| Compound No. | Abbreviation | Structural Formula | Name |
|---|---|---|---|
| aa382 | Fmoc-MeGly(cPent)-nPrAsp-mor | | (3S)-3-[[(2S)-2-cyclopentyl-2-[9H-fluoren-9-ylmethoxycarbonyl(methyl)amino]acetyl]-propyl-amino]-4-morpholino-4-oxo-butanoic acid |
| aa383 | Fmoc-MeGly(cPent)-cBuEtAsp-mor | | (3S)-3-[2-cyclobutylethyl-[(2S)-2-cyclopentyl-2-[9H-fluoren-9-ylmethoxycarbonyl(methyl)amino]acetyl]amino]-4-morpholino-4-oxo-butanoic acid |
| aa384 | Fmoc-MeGly(cPent)-cPentEtAsp-mor | | (3S)-3-[2-cyclopentylethyl-[(2S)-2-cyclopentyl-2-[9H-fluoren-9-ylmethoxycarbonyl(methyl)amino]acetyl]amino]-4-morpholino-4-oxo-butanoic acid |
| aa385 | Fmoc-MeGly(cPent)-PhenethylAsp-mor | | (3S)-3-[[(2S)-2-cyclopentyl-2-[9H-fluoren-9-ylmethoxycarbonyl(methyl)amino]acetyl]-(2-phenylethyl)amino]-4-morpholino-4-oxo-butanoic acid |
| aa386 | Fmoc-MeAsp(OPis) | | (3S)-3-[9H-fluoren-9-ylmethoxycarbonyl(methyl)amino]-4-(1-methyl-1-phenyl-ethoxy)-4-oxo-butanoic acid |

TABLE 5-continued

| Compound No. | Abbreviation | Structural Formula | Name |
| --- | --- | --- | --- |
| aa427 | Fmoc-Hyp(Et)-MecVal-MeGly(cPent)-MeAsp-NMe2 | | (3S)-3-[[(2S)-2-cyclopentyl-2-[[1-[[(2S,4R)-4-ethoxy-1-(9H-fluoren-9-ylmethoxycarbonyl) pyrrolidin-2-carbonyl]-methyl-amino]cyclobutan carbonyl]-methyl-amino]acetyl]-methyl-amino]-4-(dimethyl amino)-4-oxo-butanoic acid |
| aa428 | Fmoc-Pro(4S-Me)-MecVal-MeGly(cPent)-MeAsp-NMe2 | | (3S)-3-[[(2S)-2-cyclopentyl-2-[1-[[(2S,4S)-1-(9H-fluoren-9-ylmethoxycarbonyl)-4-methyl-pyrrolidin-2-carbonyl]-methyl-amino]cyclobutan carbonyl]-methyl-amino]acetyl]-methyl-amino]-4-(dimethyl amino)-4-oxo-butanoic acid |
| aa429 | Fmoc-Hyp(Et)-MecVal(3-Me2)-MeGly(cPent)-MeAsp-NMe2 | | (3S)-3-[[(2S)-2-cyclopentyl-2-[1-[[(2S,4R)-4-ethoxy-1-(9H-fluoren-9-ylmethoxycarbonyl) pyrrolidin-2-carbonyl]-methyl-amino]-3,3-dimethyl-cyclobutan carbonyl]-methyl-amino]acetyl]-methyl-amino]-4-(dimethyl amino)-4-oxo-butanoic acid |
| aa430 | Fmoc-Hyp(Et)-MecVal-MeNva(3-Et)-MeAsp-NMe2 | | (3S)-4-(dimethyl amino)-3-[[(2S)-2-[1-[[(2S,4R)-4-ethoxy-1-(9H-fluoren-9-ylmethoxycarbonyl) pyrrolidin-2-carbonyl]-methyl-amino]cyclobutan carbonyl]-methyl-amino]-3-ethyl-pentanoyl]-methyl-amino]-4-oxo-butanoic acid |
| aa431 | Fmoc-Hyp(Et)-MecVal(3-Me2)-MeNva(3-Et)-MeAsp-NMe2 | | (3S)-4-(dimethyl amino)-3-[[ (2S)-2-[1-[[(2S,4R)-4-ethoxy-1-(9H-fluoren-9-ylmethoxycarbonyl) pyrrolidin-2-carbonyl]-methyl-amino]-3,3-dimethyl-cyclobutan carbonyl]-methyl-amino]-3-ethyl-pentanoyl]-methyl-amino]-4-oxo-butanoic acid |

TABLE 5-continued

| Compound No. | Abbreviation | Structural Formula | Name |
|---|---|---|---|
| aa432 | Fmoc-Hyp(nPr)-MecVal(3-Me2)-MeNva(3-Et)-MeAsp-NMe2 | | (3S)-4-(dimethyl amino)-3-[(2S)-3-ethyl-2-[1-[[(2S,4R)-1-(9H-fluoren-9-ylmethoxycarbonyl)-4-propoxy-pyrrolidin-2-carbonyl]-methyl-amino]-3,3-dimethyl-cyclobutan carbonyl]-methyl-amino]pentanoyl]-methyl-amino]-4-oxo-butanoic acic |
| aa433 | Fmoc-Hyp(iPr)-MecVal(3-Me2)-MeNva(3-Et)-MeAsp-NMe2 | | (3S)-4-(dimethyl amino)-3-[(2S)-3-ethyl-2-[1-[[(2S,4R)-1-(9H-fluoren-9-ylmethoxycarbonyl)-4-isopropoxy-pyrrolidin-2-carbonyl]-methyl-amino]-3,3-dimethyl-cyclobutan carbonyl]-methyl-amino]pentanoyl]-methyl-amino]-4-oxo-butanoic acic |
| aa434 | Fmoc-Hyp(cBu)-MecVal(3-Me2)-MeNva(3-Et)-MeAsp-NMe2 | | (3S)-3-[[(2S)-2-[[1-[[(2S,4R)-4-(cyclobutoxy)-1-(9H-fluoren-9-ylmethoxycarbonyl)pyrrolidin-2-carbonyl]-methyl-amino]-3,3-dimethyl-cyclobutan carbonyl]-methyl-amino]-3-ethyl-pentanoyl]-methyl-amino]-4-(dimethyl amino)-4-oxo-butanoic acid |
| aa435 | Fmoc-Hyp(cPent)-MecVal(3-Me2)-MeNva(3-Et)-MeAsp-NMe2 | | (3S)-3-[[(2S)-2-[1-[(2S,4R)-4-(cyclopentoxy)-1-(9H-fluoren-9-ylmethoxycarbonyl)pyrrolidin-2-carbonyl]-methyl-amino]-3,3-dimethyl-cyclobutan carbonyl]-methyl-amino]-3-ethyl-pentanoyl]-methyl-amino]-4-(dimethyl amino)-4-oxo-butanoic acid |
| aa436 | Fmoc-Pro(4-cPr)-MecVal(3-Me2)-MeNva(3-Et)-MeAsp-NMe2 | | (3S)-4-(dimethyl amino)-3-[(2S)-3-ethyl-2-[[1-[(6S)-5-(9H-fluoren-9-ylmethoxycarbonyl)-5-azaspiro[2.4]heptan-6-carbonyl]-methyl-amino]-3,3-dimethyl-cyclobutan carbonyl]-methyl-amino]pentanoyl]-methyl-amino]-4-oxo-butanoic acid |

TABLE 5-continued

| Compound No. | Abbreviation | Structural Formula | Name |
|---|---|---|---|
| aa437 | Fmoc-Hyp(Et)-MecVal-MeGly(cPent)-MeAsp-pip | | (3S)-3-[[(2S)-2-cyclopentyl-2-[[1-[[(2S,4R)-4-ethoxy-1-(9H-fluoren-9-ylmethoxycarbonyl)pyrrolidin-2-carbonyl]-methyl-amino]cyclobutan carbonyl]-methyl-amino]acetyl]-methyl-amino]-4-oxo-4-(1-piperidyl)butanoic acid |
| aa438 | Fmoc-Hyp(Et)-MecVal-MeGly(cPent)-MeAsp-pyrro | | (3S)-3-[[(2S)-2-cyclopentyl-2-[1-[[(2S,4R)-4-ethoxy-1-(9H-fluoren-9-ylmethoxycarbonyl)pyrrolidin-2-carbonyl]-methyl-amino]cyclobutan carbonyl]-methyl-amino]acetyl]-methyl-amino]-4-oxo-4-pyrrolidin-1-yl-butanoic acid |
| aa439 | Fmoc-MeCys(AcOH)-NMe2 | | 2-[[(2R)-3-(dimethyl amino)-2-[9H-fluoren-9-ylmethoxycarbonyl(methyl)amino]-3-oxo-propyl]sulfanyl-acetic acid |
| aa440 | Fmoc-MeGly(cPent)-MeAsp-MeNEt | | (3S)-3-[[(2S)-2-cyclopentyl-2-[9H-fluoren-9-ylmethoxycarbonyl(methyl)amino]acetyl]-methyl-amino]-4-[ethyl(methyl)amino]-4-oxo-butanoic acid |
| aa441 | Fmoc-MeGly(cPent)-MeAsp-NEt2 | | (3S)-3-[[(2S)-2-cyclopentyl-2-[9H-fluoren-9-ylmethoxycarbonyl(methyl)amino]acetyl]-methyl-amino]-4-(diethyl amino)-4-oxo-butanoic acid |
| aa442 | Fmoc-MeGly(cPent)-MeAsp-MeNnPr | | (3S)-3-[(2S)-2-cyclopentyl-2-[9H-fluoren-9-ylmethoxycarbonyl(methyl)amino]acetyl]-methyl-amino]-4-[methyl(propyl)amino]-4-oxo-butanoic acid |

TABLE 6

| Compound No. | Abbreviation | Structural Formula | Name |
| --- | --- | --- | --- |
| aa370 | Fmoc-D-3-Abu-OH | | (3R)-3-(9H-fluoren-9-ylmethoxycarbonylamino)butanoic acid |
| aa371 | Fmoc-D-3-MeAbu-OH | | (3R)-3-[9H-fluoren-9-ylmethoxycarbonyl(methyl)amino]butanoic acid |
| aa372 | Fmoc-D-Pro-(C#CH2)-OH | | 2-[(2R)-1-(9H-fluoren-9-ylmethoxycarbonyl)pyrrolidin-2-yl]acetic acid |
| aa423 | Fmoc-MebAla(3S-cBu)-OH | | (3S)-3-cyclobutyl-3-[9H-fluoren-9-ylmethoxycarbonyl(methyl)amino] propanoic acid |
| aa424 | Fmoc-MebAla(3R-Et)-OH | | (3R)-3-[9H-fluoren-9-ylmethoxycarbonyl(methyl)amino] pentanoic acid |
| aa425 | Fmoc-D-MeVal-(C#CH2)-OH | | (3S)-3-[9H-fluoren-9-ylmethoxycarbonyl)methyl)amino]-4-methyl-pentanoic acid |

TABLE 6-continued

| Compound No. | Abbreviation | Structural Formula | Name |
|---|---|---|---|
| aa426 | Fmoc-MebAla(3S-cHex)-OH | 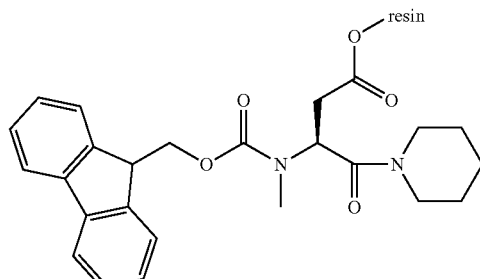 | (3S)-3-cyclohexyl-3-[9H-fluoren-9-ylmethoxycarbonyl(methyl)amino]propanoic acid |

Synthesis of Resin

Synthesis of Compound aa362-Resin

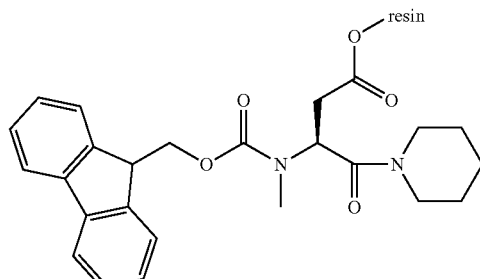

aa362-resin

Compound aa362-resin was synthesized by the method described in WO2018/225864.

Herein, when a resin and a compound are bonded, the resin moiety may be indicated as "O" (circle) or "resin". The 2-chlorotrityl group may be omitted. Further, to clarify the reaction point of the resin moiety, the chemical structure of the reaction moiety may be indicated in connection with "O" (circle) or "resin". In the above structure of Compound aa362-resin, the 2-chlorotrityl group on the resin is bonded to the side-chain carboxylic acid of MeAsp via an ester bond.

Synthesis of Compound aa358-Resin

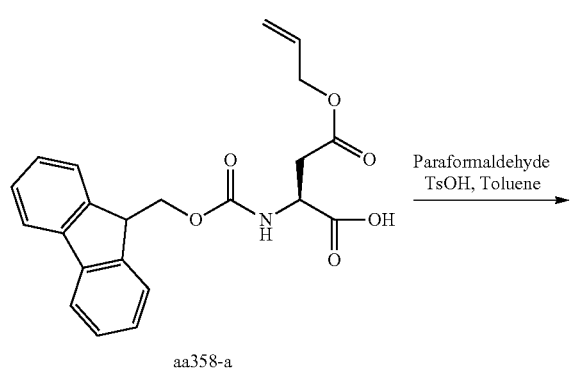

aa358-a

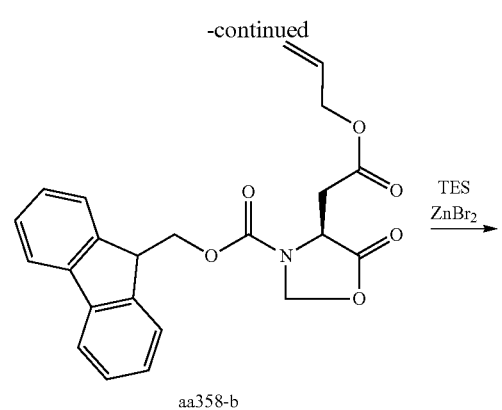

aa358-b

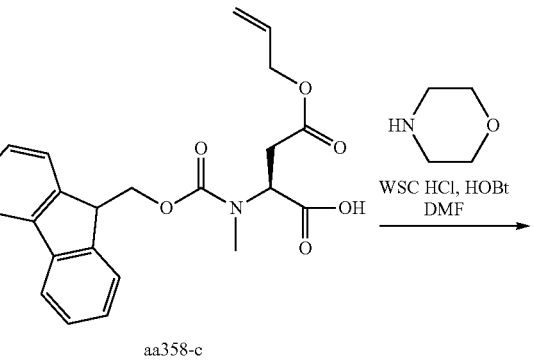

aa358-c

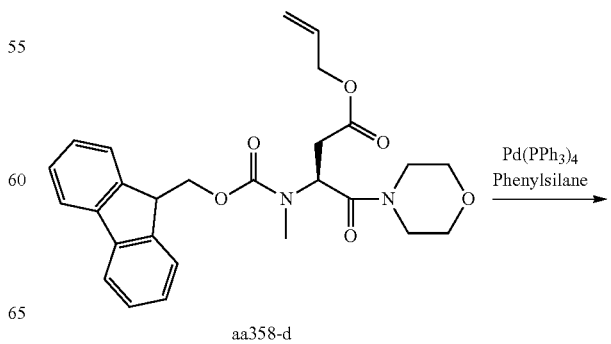

aa358-d

-continued

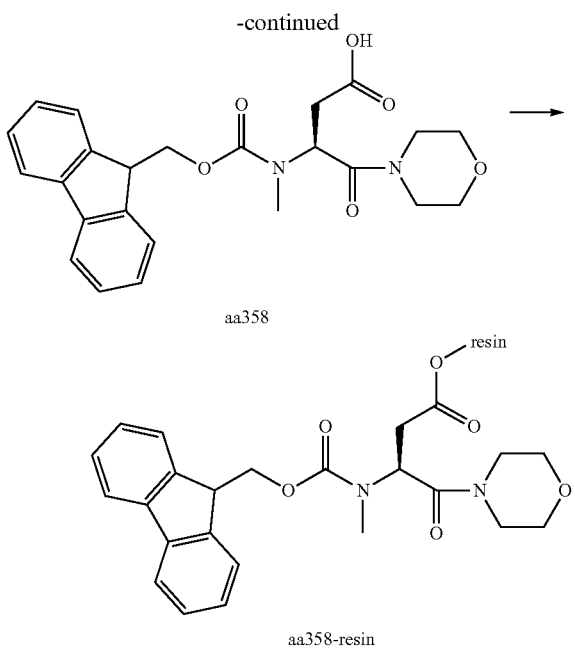

aa358 aa358-resin

Fmoc-Asp (OAl)—OH (Compound aa358-a, (2S)-2-(9H-fluoren-9-ylmethoxycarbonylamino)-4-oxo-4-prop-2-enoxybutanoic acid, CAS No. 146982-24-3)(200 g, 506 mmol), p-toluenesulfonic acid (5.7 g, 0.05 eq), and paraformaldehyde (45.6 g, 3 eq) were mixed with toluene (2000 mL), and the mixture was stirred at 110° C. for 16 hours. The solvent was distilled off from the reaction solution under reduced pressure, the residue was dissolved in ethyl acetate, and the mixture was washed twice with an aqueous sodium hydrogen carbonate solution. The organic layer was dried over sodium sulfate, and the solvent was distilled off under reduced pressure. The residue was purified by silica gel column chromatography (ethyl acetate/petroleum ether, 0/100 to 30/70) to give Compound aa358-b (9H-fluoren-9-ylmethyl(4S)-5-oxo-4-(2-oxo-2-prop-2-enoxyethyl)-1,3-oxazolidine-3-carboxylate)(175 g, 85%). The compound was mixed with another similarly synthesized batch, and used in the following reaction.

LCMS (ESI) m/z=408 (M+H)+

Retention time: 1.407 min (Analytical condition SMD method_20)

A DCM (1 µL) mixed solution of Compound aa358-b (100 g, 245 mmol), zinc bromide (ZnBr$_2$)(110 g, 496 mmol), and TES (56 g, 481.6 mmol) was stirred at room temperature for 48 hours in a nitrogen atmosphere. Four batches of the same scale of the reaction solution were mixed, and the solvent was distilled off under reduced pressure. The residue was dissolved in TBME and extracted 10 times with 0.5 M phosphate buffer (pH=about 7.5). The aqueous layers were combined, adjusted to pH 2 with 5 N hydrochloric acid, and extracted twice with isopropyl acetate (IPAC). The organic layers were combined, dried over anhydrous sodium sulfate, and the solvent was distilled off under reduced pressure. To remove IPAC, the procedure of adding TBME to the resulting residue and distilling off solvent under reduced pressure was repeated 6 times, and thus Compounds aa358-c ((2S)-2-[9H-fluoren-9-ylmethoxycarbonyl(methyl)amino]-4-oxo-4-prop-2-enoxybutanoic acid) was obtained (270 g, 54%).

LCMS (ESI) m/z=410 (M+H)+

Retention time: 1.956 min (Analytical condition SMD method_05)

WSCI·HCl (0.506 g, 2.64 mmol) was dissolved in DMF (4.4 mL), then HOBt (0.356 g, 2.64 mmol), Compound aa358-c ((2S)-2-[9H-fluoren-9-ylmethoxycarbonyl(methyl)amino]-4-oxo-4-prop-2-enoxybutanoic acid), Fmoc-MeAsp (OAl)—OH)(0).9 g, 2.2 mmol) were added, and the mixture was stirred at (° C.) for 10 minutes. Morpholine (0).23 mL, 2.64 mmol) was added dropwise to the reaction solution, and the mixture was stirred at 0° C. for 1 hour. Ethyl acetate (9 mL) was added to the reaction solution, the mixture was washed with 0).5 N hydrochloric acid, water, a saturated aqueous sodium hydrogen carbonate solution/water (1/1), and saturated brine/water (1/1), and dried over anhydrous sodium sulfate, and the solvent was distilled off under reduced pressure to give Compound aa358-d as a crude product (522 mg, 50%).

LCMS (ESI) m/z=479 (M+H)+

Retention time: 0.87 min (Analytical condition SQDFA05)

Tetrakis(triphenylphosphine) palladium (0))(10.8 mg, 0.0093 mmol) was added to a DCM (1.86 mL) solution of Compound aa358-d (446 mg, 0.932 mmol), and further, phenylsilane (0.081 mL, 0).653 mmol) was added dropwise, and the mixture was stirred at room temperature for 30 minutes. The reaction solution was diluted with TBME, and a 5% aqueous sodium hydrogen carbonate solution was added. The organic layer was removed, phosphoric acid (548 mg) was added to the aqueous layer, and the mixture was extracted with TBME. The organic layer was washed with saturated brine, dried over anhydrous sodium sulfate, and the solvent was distilled off under reduced pressure to give Compound aa358 (321 mg, 79%).

LCMS (ESI) m/z=439 (M+H)+

Retention time: 0).69 min (Analytical condition SQDFA05)

The reaction for causing the Fmoc amino acid to be supported on a resin was performed according to the method described in WO2013/100132 or WO2018/225864. 2-Chlorotrityl chloride resin (1.60 mmol/g, 100-200 mesh, 1% DVB, 1 g, 1.6 mmol) and dehydrated dichloromethane (13.3 mL) were placed in a filter-equipped reaction vessel, and shaken at room temperature for 10 minutes. After dichloromethane was removed by applying nitrogen pressure, a mixed solution obtained by adding dehydrated methanol (0.259 mL, 6.4 mmol) and DIPEA (0.671 mL, 3.84 mmol) to a dehydrated dichloromethane (13.3 mL) solution of Compound aa358 (317 mg, 0.723 mmol) was added to the reaction vessel, and the reaction vessel was shaken for 30 minutes. After the reaction solution was removed by applying nitrogen pressure, a mixed solution obtained by adding dehydrated methanol (1.99 mL) and DIPEA (0.671 mL) to dehydrated dichloromethane (13.3 mL) were added to the reaction vessel, and the reaction vessel was shaken for 1 hour and 30 minutes. After the reaction solution was removed by applying nitrogen pressure, dichloromethane was added to the reaction vessel, the reaction vessel was shaken for 5 minutes, and then the reaction solution was removed by applying nitrogen pressure. This resin washing operation with dichloromethane was repeated 2 more times, and the resulting resin was dried under reduced pressure overnight to give Compound aa358-resin (1.22 g, 0.37 mmol/g).

The amount of amino acid supported on the resin was calculated as follows. The resulting Compound aa358-resin (10.4 mg) was placed in the reaction vessel, DMF (2 mL) was added, and the reaction vessel was shaken at room temperature for 1 hour. Then, DBU (40 µL) was added, and the reaction vessel was shaken at 30° C. for 30 minutes.

Then, DMF (8 mL) was added to the reaction mixture, and 1 mL of the solution was diluted with DMF (11.5 mL). The absorbance (294 nm) of the resulting diluted solution was measured (measured with Shimadzu UV-1600PC(cell length 1.0 cm)), and thus the calculated amount of supported Compound aa358-resin was 0.370 mmol/g.

Another similarly synthesized lot having a different supported amount was also used in the peptide synthesis.
Synthesis of Compound aa359-Resin

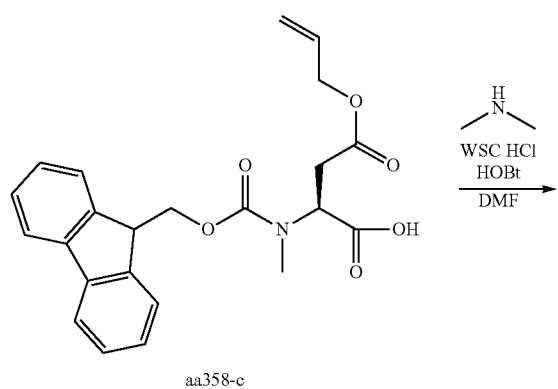

aa358-c

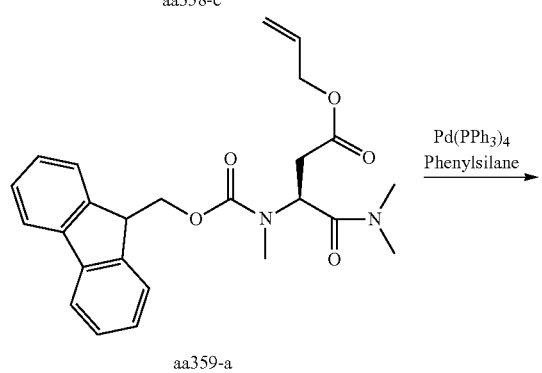

aa359-a

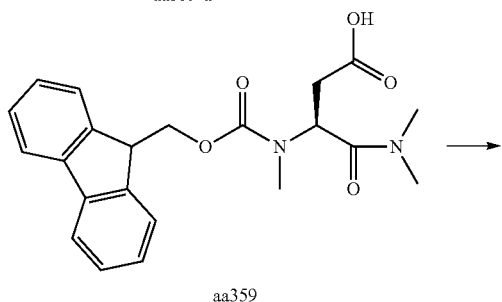

aa359

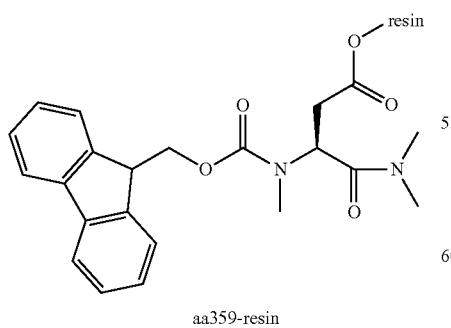

aa359-resin

Using Compound aa358-c ((2S)-2-[9H-fluoren-9-yl-methoxycarbonyl(methyl)amino]-4-oxo-4-prop-2-enoxybutanoic acid)(1.5 g, 3.66 mmol) as a starting material, Compound aa359-a (1.47 g, 92%) was obtained in the same manner as the synthesis of Compound aa358-d using a THF solution (2 mol/L) of dimethylamine in place of morpholine.

LCMS (ESI) m/z=437 (M+H)+

Retention time: 0.88 min (Analytical condition SQDFA05)

Using the resulting Compound aa359-a (1.4 g, 3.21 mmol), Compound aa359 (1.30 g, quant.) was obtained in the same manner as the synthesis of Compound aa358.

LCMS (ESI) m/z=397 (M+H)+

Retention time: 0.70 min (Analytical condition SQDFA05)

Using the resulting Compound aa359 (1.21 g, 3.05 mmol), Compound aa359-Resin (4.45 g, supported amount 0.318 mmol/g) was obtained in the same manner as the synthesis of Compound aa358-resin.

Another similarly synthesized lot having a different supported amount was also used in the peptide synthesis in the present Example.
Synthesis of Compound aa360-Resin

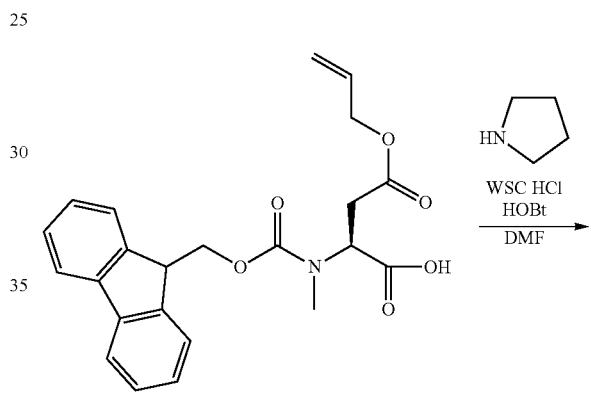

aa358-c

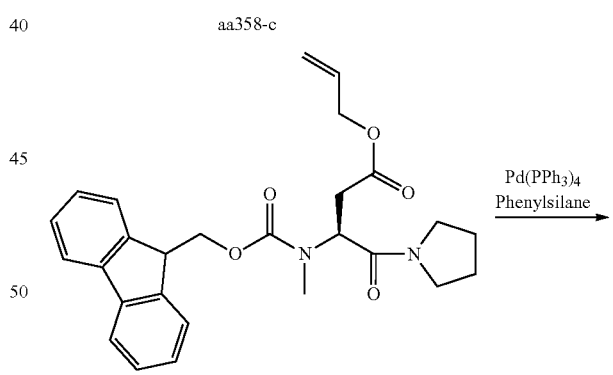

aa360-a

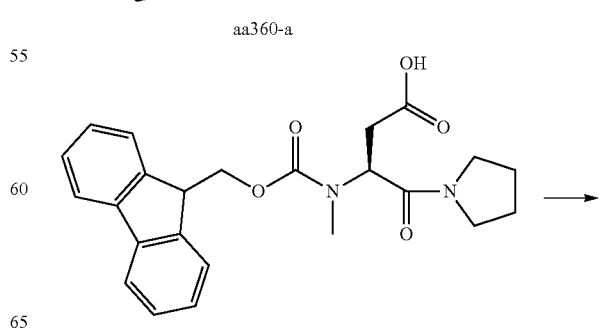

aa360

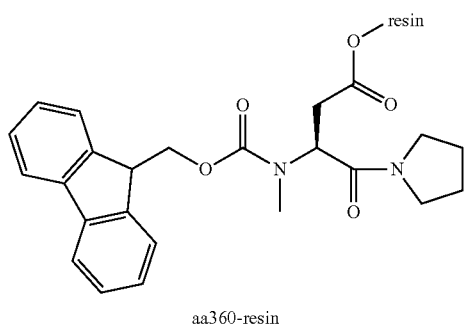

aa360-resin

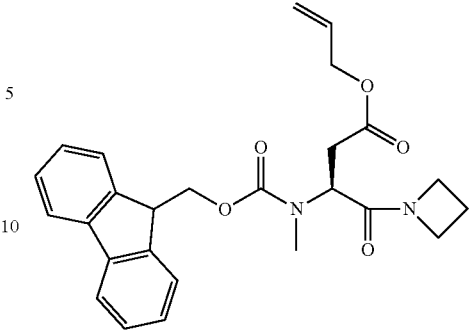

aa361-a

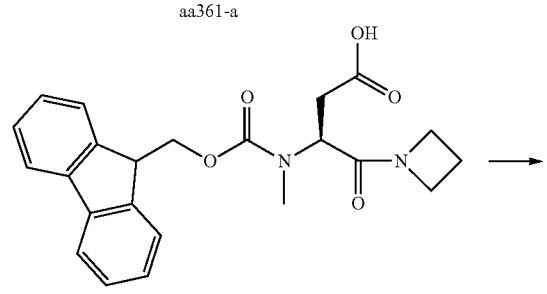

aa361

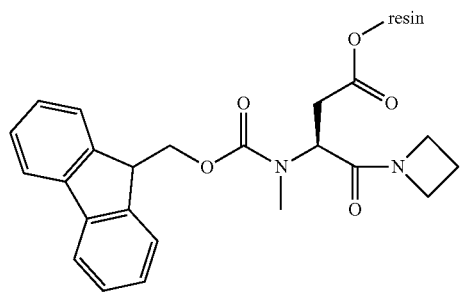

aa361-resin

Using Compound aa358-c ((2S)-2-[9H-fluoren-9-yl-methoxycarbonyl(methyl)amino]-4-oxo-4-prop-2-enoxybutanoic acid)(30 g, 73.3 mmol) as a starting material, Compound aa360-a (30.7 g, 91%) was obtained in the same manner as the synthesis of Compound aa358-d using pyrrolidine in place of morpholine.

LCMS (ESI) m/z=463 (M+H)+

Retention time: 0.88 min (Analytical condition SQDFA05)

Using the resulting Compound aa360-a (30.7 g, 66.4 mmol), Compound aa360 (26.2 g, 93%) was obtained in the same manner as the synthesis of Compound aa358.

LCMS (ESI) m/z=423 (M+H)+

Retention time: 0.71 min (Analytical condition SQDFA05)

Using the resulting Compound aa360 (24.6 g, 58.2 mmol), Compound aa360-resin was obtained in the same manner as the synthesis of Compound aa358-resin (84.1 g, supported amount 0.5216 mmol/g).

Another similarly synthesized lot having a different supported amount was also used in the peptide synthesis in the present Example.

Synthesis of Compound aa361-Resin

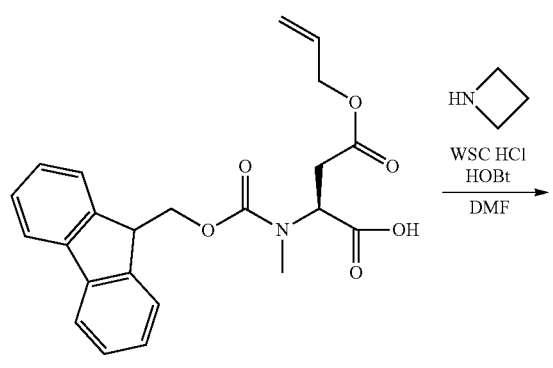

aa358-c

Using Compound aa358-c ((2S)-2-[9H-fluoren-9-yl-methoxycarbonyl(methyl)amino]-4-oxo-4-prop-2-enoxybutanoic acid)(1.5 g, 3.66 mmol) as a starting material, Compound aa361-a (1.41 g, 86%) was obtained in the same manner as the synthesis of Compound aa358-a using azetidine in place of morpholine.

LCMS (ESI) m/z=449 (M+H)+

Retention time: 0.86 min (Analytical condition SQDFA05)

Using the resulting Compound aa361-a (1.4 g, 3.12 mmol), Compound aa361 (1.14 g, 89%.) was obtained in the same manner as the synthesis of Compound aa358.

LCMS (ESI) m/z=409 (M+H)+

Retention time: 0.69 min (Analytical condition SQDFA05)

Using the resulting Compound aa361 (1.05 g, 2.57 mmol), Compound aa361-Resin (3.64 g, supported amount 0.2984 mmol/g) was obtained in the same manner as the synthesis of Compound aa358-resin.

Another similarly synthesized lot having a different supported amount was also used in the peptide synthesis in the present Example.

Synthesis of Compound aa363-Resin

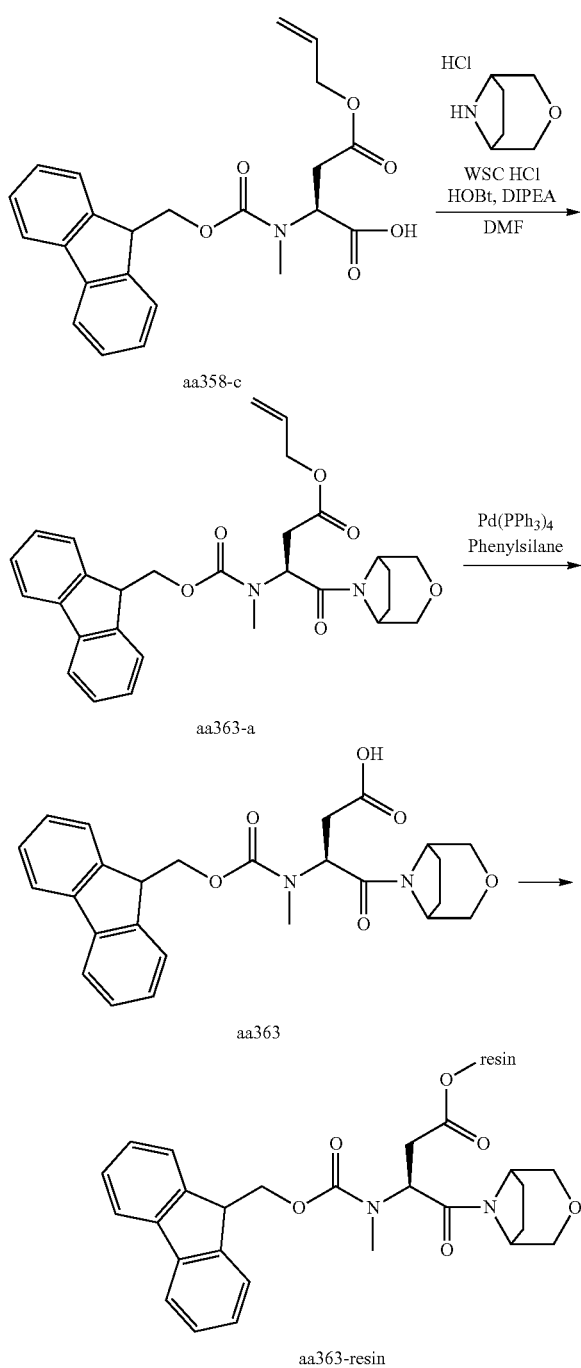

aa358-c aa363-a aa363 aa363-resin

Using Compound aa358-c ((2S)-2-[9H-fluoren-9-yl-methoxycarbonyl(methyl)amino]-4-oxo-4-prop-2-enoxybutanoic acid)(5 g, 12.21 mmol) as a starting material, Compound aa363-a (5.8 g, 94%) was obtained in the same manner as the synthesis of Compound aa358-d using (1R,5S)-3-oxa-8-azabicyclo[3.2.1]octane hydrochloride and 1 eq of DIPEA based on amine, in place of morpholine.

LCMS (ESI) m/z=505 (M+H)+

Retention time: 0.87 min (Analytical condition SQDFA05)

Using the resulting Compound aa363-a (5.8 g, 11.49 mmol), Compound aa363 (5.1 g, 96%) was obtained in the same manner as the synthesis of Compound aa358.

LCMS (ESI) m/z=465 (M+H)+

Retention time: 0.69 min (Analytical condition SQDFA05)

Using the resulting Compound aa363 (5.1 g, 10.98 mmol), Compound aa363-Resin (18.3 g, supported amount 0.419 mmol/g) was obtained in the same manner as the synthesis of Compound aa358-resin.

Another similarly synthesized lot having a different supported amount was also used in the peptide synthesis in the present Example.

Synthesis of Compound aa364-Resin

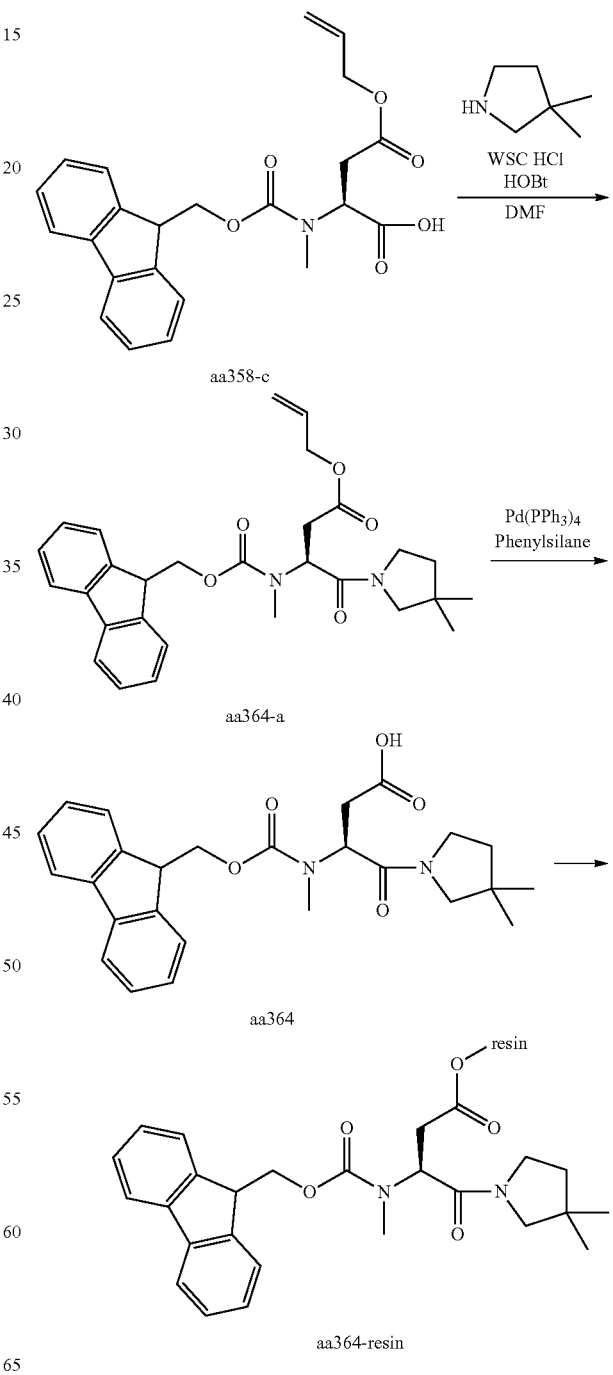

aa358-c aa364-a aa364 aa364-resin

Using Compound aa358-c ((2S)-2-[9H-fluoren-9-yl-methoxycarbonyl(methyl)amino]-4-oxo-4-prop-2-enoxybutanoic acid)(0.5 g, 1.221 mmol) as a starting material, Compound aa364-a (359.6 mg, 60%) was obtained in the same manner as the synthesis of Compound aa358-d using 3,3-dimethylpyrrolidine in place of morpholine.

LCMS (ESI) m/z=491 (M+H)+

Retention time: 0.98 min (Analytical condition SQDFA05)

Using the resulting Compound aa364-a (338 mg, 0.689 mmol), Compound aa364 (226.2 mg, 73%) was obtained in the same manner as the synthesis of Compound aa358. LCMS (ESI) m/z=451 (M+H)+

Retention time: 0.84 min (Analytical condition SQDFA05)

Using the resulting Compound aa364 (226 mg, 0.502 mmol), Compound aa364-Resin (731 mg, supported amount 0.455 mmol/g) was obtained in the same manner as the synthesis of Compound aa358-resin.

Synthesis of Compound aa365-Resin

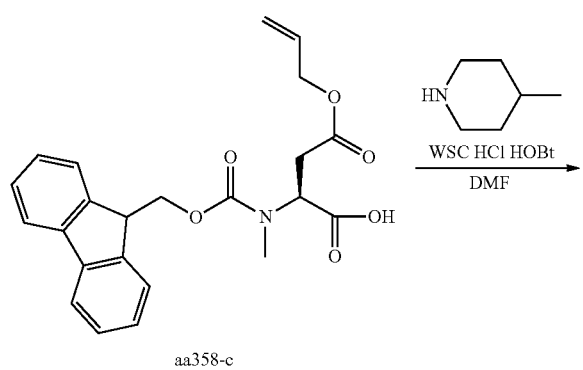

aa358-c

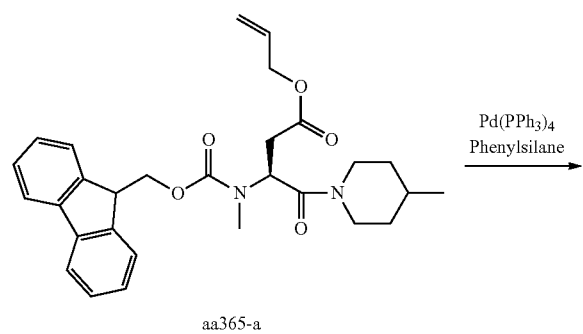

aa365-a

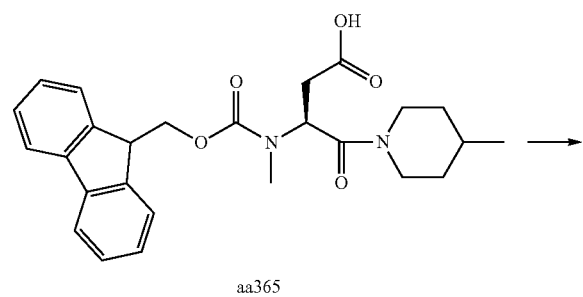

aa365

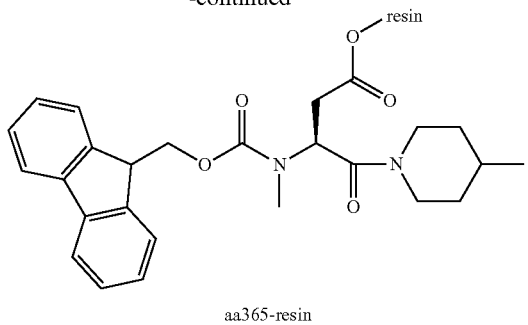

aa365-resin

Using Compound aa358-c ((2S)-2-[9H-fluoren-9-yl-methoxycarbonyl(methyl)amino]-4-oxo-4-prop-2-enoxybu-tanoic acid)(0.9 g, 2.198 mmol) as a starting material, a crude material of Compound aa365-a was obtained in the same manner as the synthesis of Compound aa358-d using 4-methylpiperidine in place of morpholine. The resulting crude product was purified by reverse phase column chromatography (0.1% formic acid-containing water-acetonitrile), and further, dissolved in 20% ethyl acetate-hexane, then washed twice with a saturated aqueous sodium hydrogen carbonate solution and once with a saturated aqueous sodium chloride solution, and dried over anhydrous sodium sulfate, and the solvent was distilled off under reduced pressure to give Compound aa365-a (0.587 g, 54%).

LCMS (ESI) m/z=491 (M+H)+

Retention time: 1.02 min (Analytical condition SQDFA05)

Using the resulting Compound aa365-a (535 mg, 1.09 mmol), Compound aa365 (376.6 mg, 77%) was obtained in the same manner as the synthesis of Compound aa358.

LCMS (ESI) m/z=451 (M+H)+

Retention time: 0.85 min (Analytical condition SQDFA05) Using the resulting Compound aa365 (364 mg, 0.808 mmol), Compound aa365-Resin (1.2 g, supported amount 0.403 mmol/g) was obtained in the same manner as the synthesis of Compound aa358-resin.

Synthesis of Compound aa366-Resin

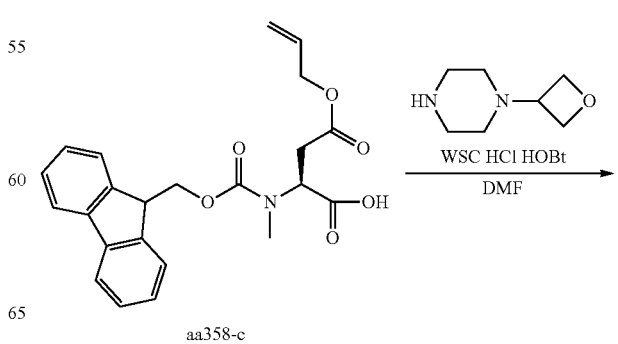

aa358-c

287

-continued

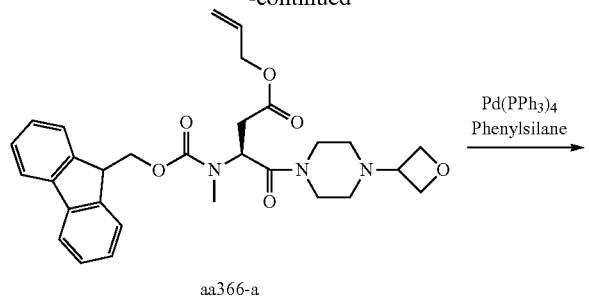

aa366-a

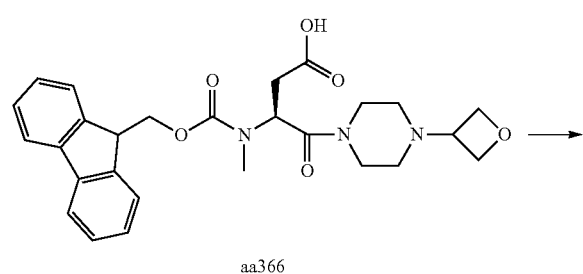

aa366

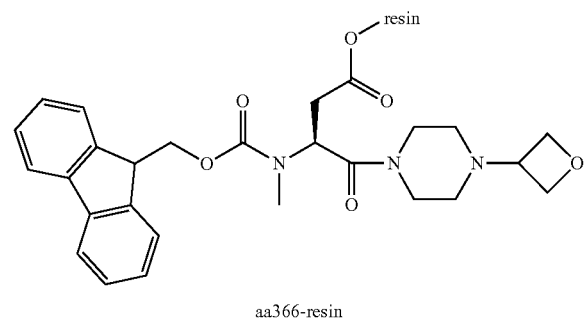

aa366-resin

Using Compound aa358-c ((2S)-2-[9H-fluoren-9-yl-methoxycarbonyl(methyl)amino]-4-oxo-4-prop-2-enoxybutanoic acid)(0.4 g, 0.977 mmol) as a starting material, Compound aa366-a (466 mg, 89%) was obtained in the same manner as the synthesis of Compound aa358-d using 1-(oxetan-3-yl) piperazine in place of morpholine.

LCMS (ESI) m/z=534 (M+H)+

Retention time: 0.64 min (Analytical condition SQDFA05)

A crude product obtained in the same manner as the synthesis of Compound aa358 using the resulting Compound aa366-a (466 mg, 0.873 mmol), was purified by reverse phase column chromatography (0.1% formic acid-containing acetonitrile/0.1% formic acid-containing distilled water) to give Compound aa366 (385 mg, 89%).

LCMS (ESI) m/z=494 (M+H)+

Retention time: 0.50 min (Analytical condition SQDFA05)

Using the resulting Compound aa366 (385 mg, 0.78 mmol), Compound aa366-Resin (1.49 g, supported amount 0.266 mmol/g) was obtained in the same manner as the synthesis of Compound aa358-resin.

288

Synthesis of Compound aa367-Resin

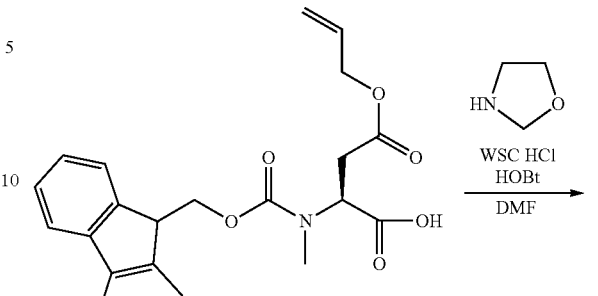

aa358-c

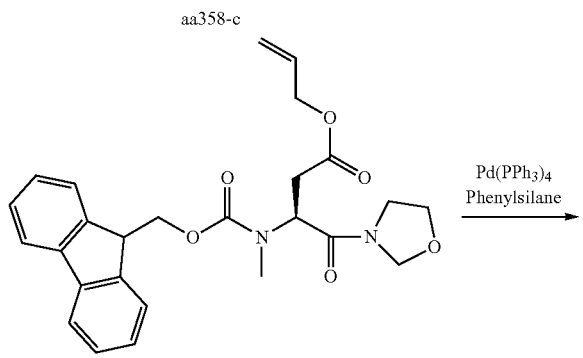

aa367-a

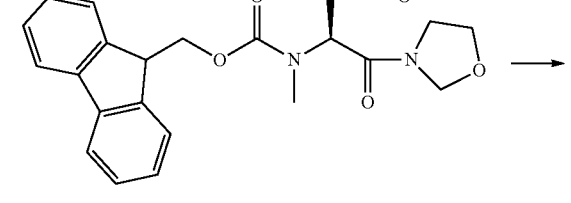

aa367

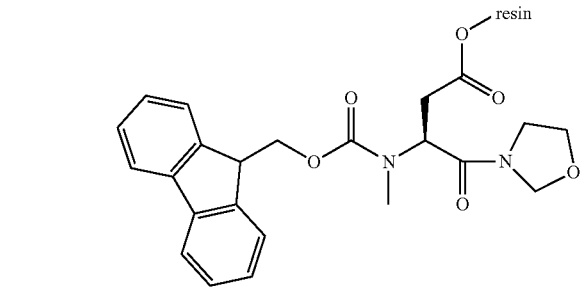

aa367-resin

Using Compound aa358-c ((2S)-2-[9H-fluoren-9-yl-methoxycarbonyl(methyl)amino]-4-oxo-4-prop-2-enoxybutanoic acid)(725 mg, 1.77 mmol) as a starting material, Compound aa367-a (164 mg, 20%) was obtained in the same manner as the synthesis of Compound aa358-d. LCMS (ESI) m/z=465 (M+H)+

Retention time: 0.86 min (Analytical condition SQDFA05)

Using the resulting Compound aa367-a (146.4 mg, 0.315 mmol), Compound aa367 (111 mg, 83%) was obtained in the same manner as the synthesis of Compound aa358. Another similarly synthesized lot was also added, and the following reaction was carried out. LCMS (ESI) m/z=425 (M+H)+

Retention time: 0.69 min (Analytical condition SQDFA05)

Using the resulting Compound aa367 (0.25 g, 0.589 mmol), Compound aa367-Resin (1.06 g, supported amount 0.283 mmol/g) was obtained in the same manner as the synthesis of Compound aa358-resin.

Synthesis of Compound aa368-Resin

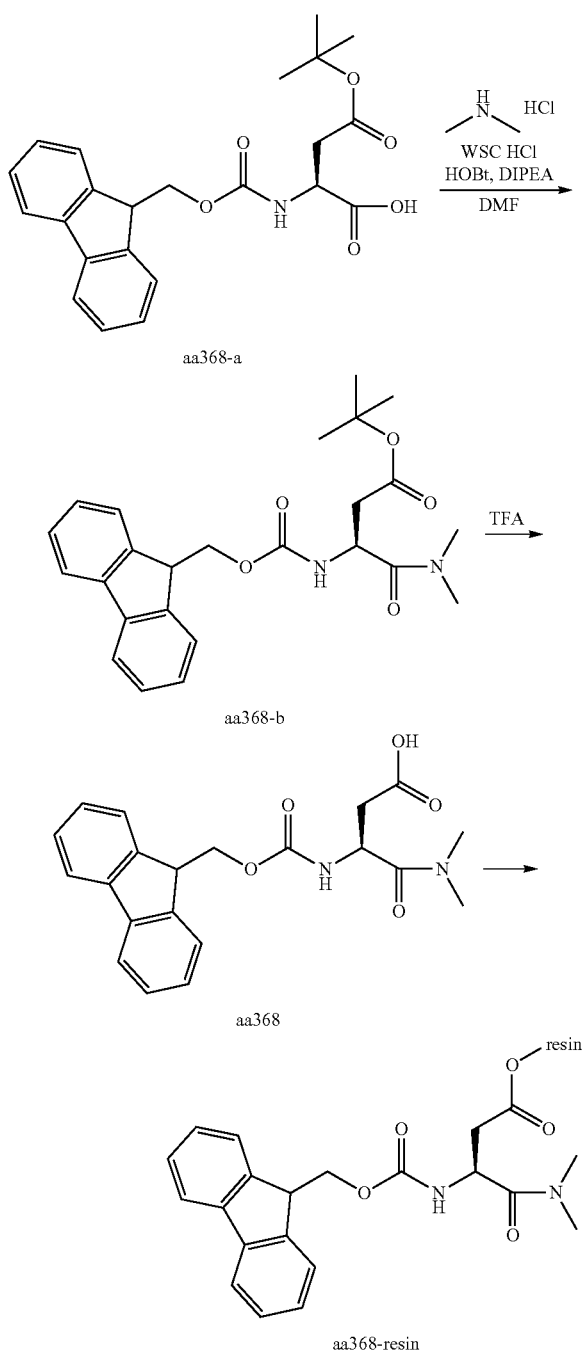

In a nitrogen atmosphere, dimethylamine hydrochloride (0.991 g, 12.15 mmol), WSCI·HCl (2.8 g, 14.58 mmol), and DIPEA (2.117 mL, 12.15 mmol) were successively added at 0° C. to a DMF (24.3 mL) solution of Fmoc-Asp (OtBu)-OH (Compound aa368-a), 4-tert-butyl N-[(9H-fluoren-9-yl-methoxy) carbonyl]-L-aspartate, CAS No. 71989-14-5)(5 g, 12.15 mmol), and HOBt monohydrate (2.047 g, 13.37 mmol), and the mixture was stirred at 0° C. for 50 minutes. Ethyl acetate/hexane (1/1, 100 mL) and saturated brine/water (1/1, 50 mL) were added to the reaction solution, and the organic layer was separated. The resulting organic layer was successively washed with a saturated aqueous ammonium chloride solution, water, and saturated brine, and dried over anhydrous sodium sulfate, and then the solvent was distilled off under reduced pressure. The resulting residue was purified by silica gel column chromatography (hexane/ethyl acetate) to give Compound aa368-b (5.02 g, 94%).

LCMS (ESI) m/z=439 (M+H)+

Retention time: 1.03 min (Analytical condition SQDAA05)

The operation of adding toluene (150 mL) to Compound aa368-b (5 g, 11.4 mmol) and distilling off the solvent under reduced pressure was performed three times. The residue was dissolved in DCM (5.06 mL), TFA (10.13 mL, 137 mmol) was added dropwise at 0° C. in a nitrogen atmosphere, and the mixture was stirred at room temperature for 1 hour. The reaction solution was cooled to 0° C., diethyl ether (10.1 mL) was added, and an 8 N aqueous sodium hydroxide solution (17.1 mL) was added dropwise. Furthermore, a saturated aqueous sodium dihydrogen phosphate solution (7.6 mL) and water (5 mL) were added. This solution was extracted with ethyl acetate, the resulting organic layer was washed with a saturated aqueous sodium dihydrogen phosphate solution/water (1/1), dried over anhydrous sodium sulfate, and then the solvent was distilled off under reduced pressure to give Compound aa368 (2.63 g, 60%). The compound was used in the next reaction without further purification.

LCMS (ESI) m/z=383 (M+H)+

Retention time: 0.80 min (Analytical condition SQDAA05)

Using the resulting Compound aa368 (2.367 g, 6.19 mmol), Compound aa368-Resin (9.07 g, supported amount 0.399 mmol/g) was obtained in the same manner as the synthesis of Compound aa358-resin.

Another similarly synthesized lot having a different supported amount was also used in the peptide synthesis in the present Example.

Synthesis of Compound aa369-Resin

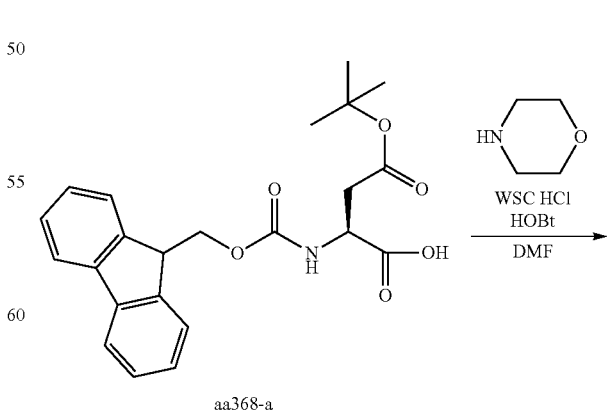

292
Synthesis of Compound aa370-Resin

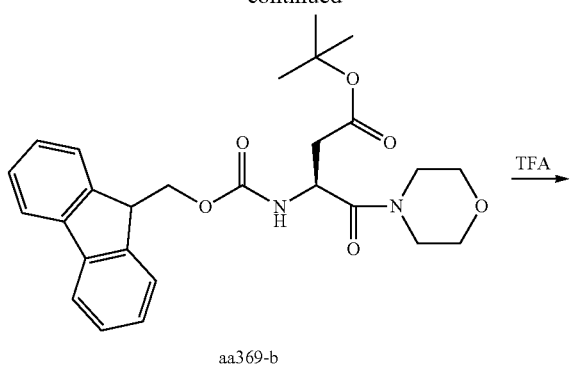

aa369-b

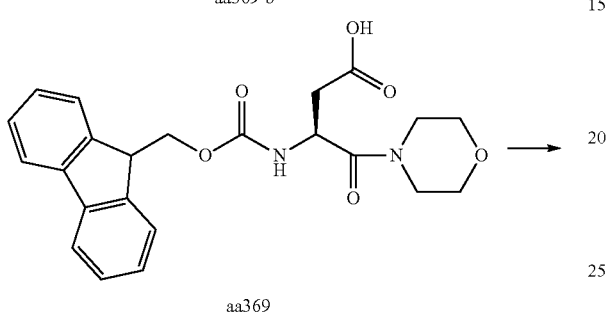

aa369

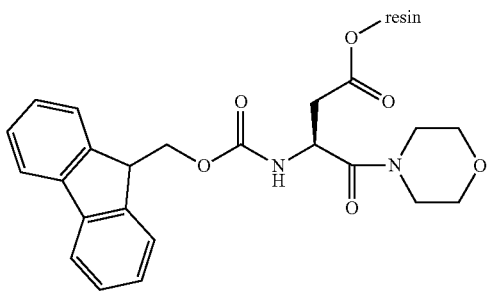

aa369-resin

Using Compound aa368-a (1 g, 2.43 mmol) as a starting material, Compound aa369-b (713 mg, 61%) was obtained in the same manner as the synthesis of Compound aa368-b using morpholine in place of dimethylamine hydrochloride and DIPEA.

LCMS (ESI) m/z=481 (M+H)+

Retention time: 0.88 min (Analytical condition SQDFA05)

Using the resulting Compound aa369-b (400 mg, 0.832 mmol), Compound aa369 (353.4 mg, 100%) was obtained in the same manner as the synthesis of Compound aa368, provided that triethylamine was used in place of an 8 N aqueous sodium hydroxide solution for work-up.

LCMS (ESI) m/z=425 (M+H)+

Retention time: 0.66 min (Analytical condition SQDFA05)

Using the resulting Compound aa369 (326 mg, 0.768 mmol), Compound aa369-Resin (1.21 g, supported amount 0.415 mmol/g) was obtained in the same manner as the synthesis of Compound aa358-resin.

Another similarly synthesized lot having a different supported amount was also used in the peptide synthesis in the present Example.

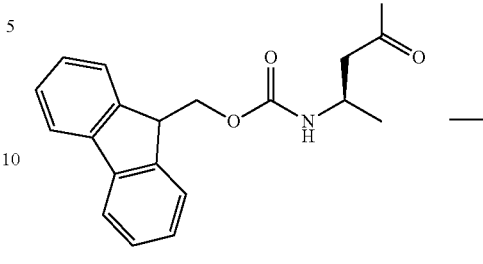

aa370

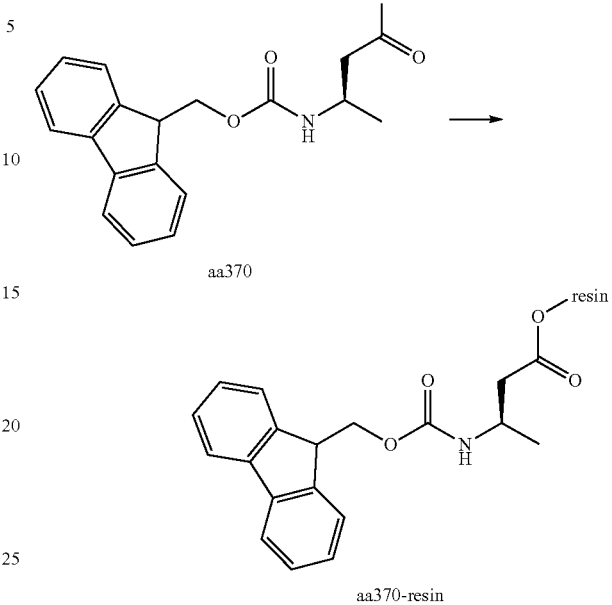

aa370-resin

Using Compound aa370 (7.1 g, 21.82 mmol) and 2-chlorotrityl chloride resin (1.6 mmol/g, 100-200 mesh, 1% DVB, 27.25 g, 43.6 mmol) purchased from a commercial supplier, Compound aa370-resin (33.44 g, supported amount 0.598 mmol/g) was obtained in the same manner as the synthesis of Compound aa358-resin.

Another similarly synthesized lot having a different supported amount was also used in the peptide synthesis in the present Example.

Synthesis of Compound aa371-Resin

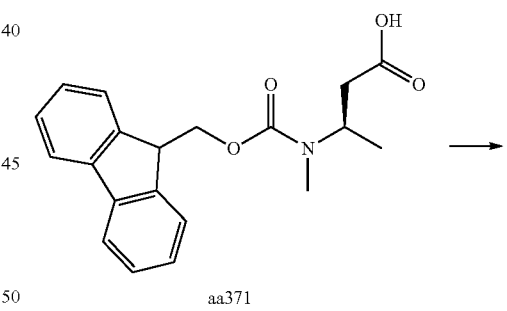

aa371

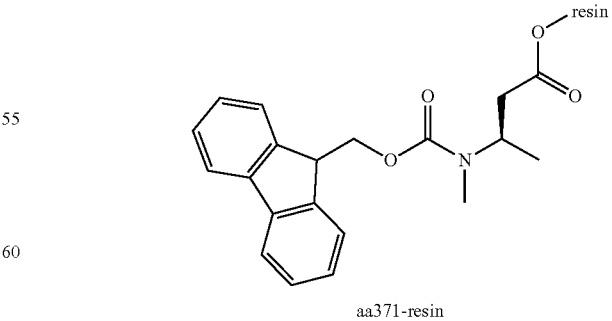

aa371-resin

Using Compound aa371 (11.5 g, 33.9 mmol) and 2-chlorotrityl chloride resin (1.69 mmol/g, 100-200 mesh, 1% DVB, 50 g, 84.5 mmol) purchased from a commercial supplier, Compound aa371-resin (58.95 g, supported amount 0.536 mmol/g) was obtained in the same manner as the synthesis of Compound aa358-resin.

Another similarly synthesized lot having a different supported amount was also used in the peptide synthesis in the present Example.

Synthesis of Compound aa372-Resin

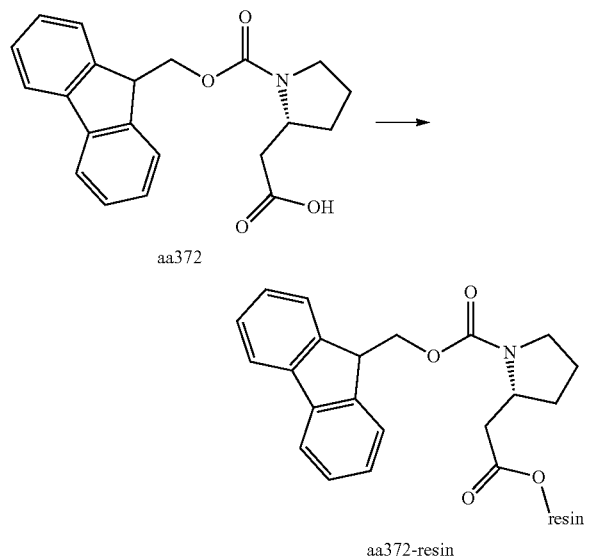

aa372 aa372-resin

Using Compound aa372 (1 g, 2.85 mmol) and 2-chlorotrityl chloride resin (1.6 mmol/g, 100-200 mesh, 1% DVB, 7 g, 21.39 mmol) purchased from a commercial supplier, Compound aa372-resin (7.19 g, supported amount 0.377 mmol/g) was obtained in the same manner as the synthesis of Compound aa358-resin.

Synthesis of Compound aa386

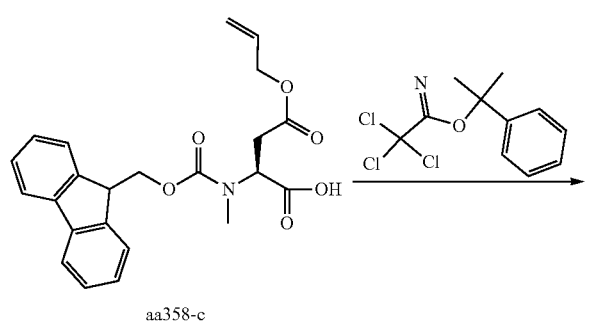

aa358-c

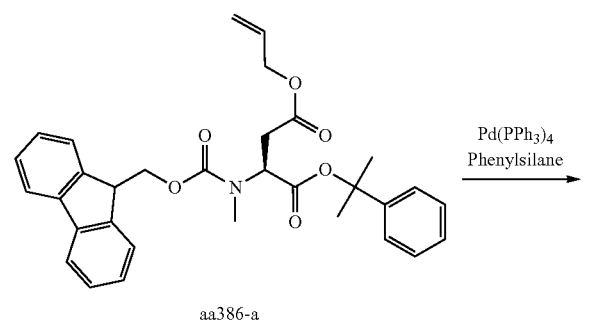

aa386-a

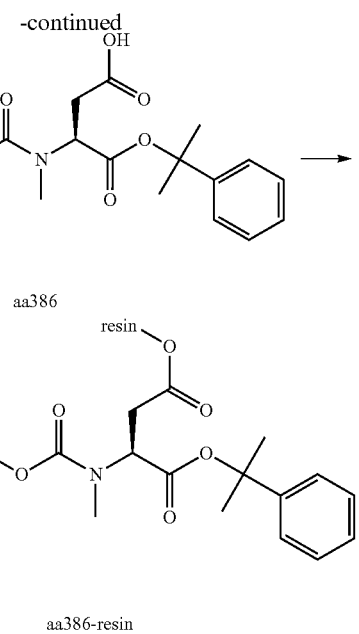

aa386 aa386-resin

A DCM solution of 2-phenylpropan-2-yl 2,2,2-trichloroacetoimidate (2.74 g, 9.77 mmol) was added to a DCM (15 mL) solution of Compound aa358-c (2 g, 4.88 mmol), and the mixture was stirred at room temperature for 2 hours. The solvent was distilled off from the reaction solution under reduced pressure, and the resulting residue was purified by reverse phase column chromatography to give Compound aa386-a (2.10 g, 81%).

LCMS (ESI) m/z=550.3 (M+Na)+

Retention time: 0.76 min (Analytical condition SQDAA50)

In a nitrogen atmosphere, tetrakis(triphenylphosphine)palladium (0)(0.046 g, 0.04 mmol) and phenylsilane (0.343 mL, 2.79 mmol) were added to a DCM (15 mL) solution of Compound aa386-a (2.1 g, 3.98 mmol) at room temperature, and the mixture was stirred for 1 hour. The reaction solution was diluted with TBME and a 5% aqueous sodium hydrogen carbonate solution, the solvent was distilled off under reduced pressure, and the resulting residue was purified by reverse phase column chromatography to give Compound aa386 (1.67 g, 86%). LCMS (ESI) m/z=510 (M+Na)+

Retention time: 0.94 min (Analytical condition SQDFA05)

Using the resulting Compound aa386 (1.17 g, 2.4 mmol), Compound aa386-resin (3.6 g, 0.377 mmol/g) was obtained in the same manner as the synthesis of Compound aa358-resin.

Synthesis of Compound aa373-Resin aa373-a

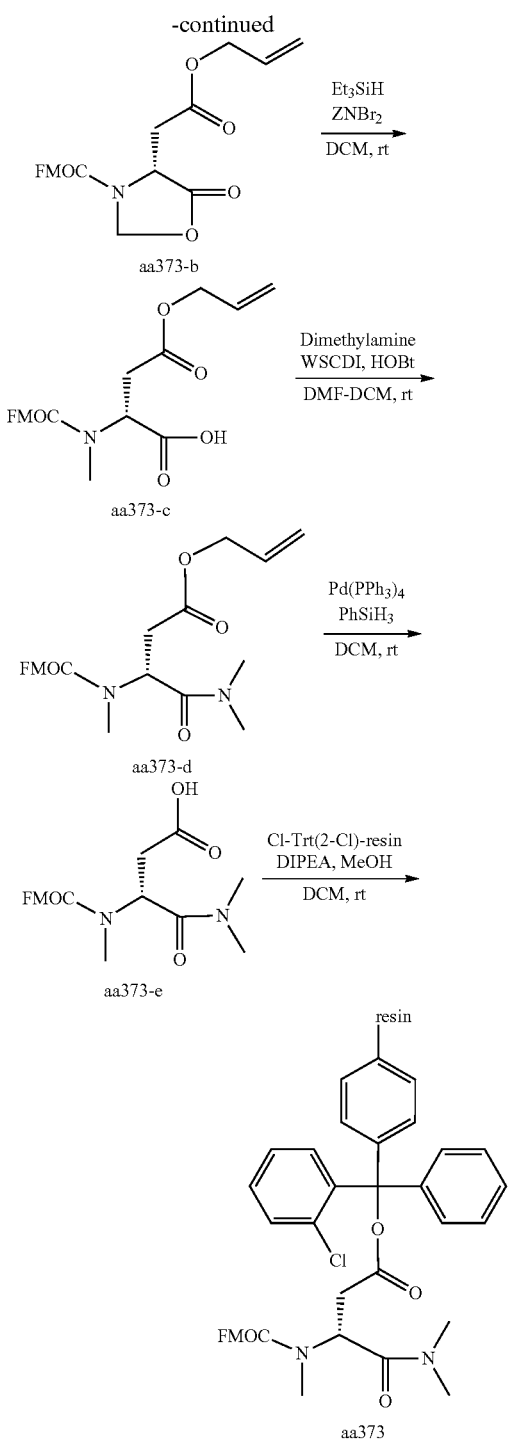

In a nitrogen atmosphere, a toluene (500 mL) suspension of aa373-a (20 g, 50.58 mmol), paraformaldehyde (4.56 g, 151.74 mmol), and p-toluenesulfonic acid (0.09 g, 0.5 mmol) was stirred at 105° C. for 16 hours. After the reaction mixture was cooled to room temperature, the solvent was distilled off under reduced pressure. The resulting residue was dissolved in tert-butyl methyl ether, washed with an aqueous sodium carbonate solution, and the organic phase was dried over sodium sulfate. The solvent was distilled off under reduced pressure to give aa373-b (20 g, 90%).

LCMS (ESI) m/z=408 (M+H)+

Retention time: 1.05 min (Analytical condition SMD method_02)

In a nitrogen atmosphere, zinc bromide (11.06 g, 49.09 mmol) was added to a DCM (200 mL) solution of aa373-b (20 g, 49.09 mmol) and triethylsilane (11.42 g, 98.18 mmol). The reaction mixture was stirred at room temperature for 48 hours, and the solvent was distilled off under reduced pressure. The resulting residue was dissolved in an aqueous potassium carbonate solution and washed twice with hexane. The aqueous phase was adjusted to pH 2 with hydrochloric acid, and then extracted with ethyl acetate 3 times. After the organic phase was dried over sodium sulfate, the solvent was distilled off under reduced pressure to give aa373-c (15 g, 93%).

LCMS (ESI) m/z=410 (M+H)+

Retention time: 0.98 min (Analytical condition SMD method_02)

HOBt (5.7 g, 42.18 mmol) was added to a DMF (110 mL)-DCM (32 mL) solution of aa373-c (15.7 g, 38.35 mmol), and then WSCDI (8.82 g, 46.01 mmol) was added. The reaction mixture was stirred at room temperature for 15 minutes, and then cooled in an ice bath. Dimethylamine (1,90) g, 42.18 mmol) was added dropwise over 5 minutes. The reaction mixture was stirred while being ice-cooled until the reaction was complete, and then ethyl acetate was added. The resulting mixture was washed with 1 N hydrochloric acid, water, an aqueous sodium hydrogen carbonate solution, and brine. After the organic phase was dried over sodium sulfate, the solvent was distilled off under reduced pressure to give aa373-d (13 g, 78%).

LCMS (ESI) m/z=437 (M+H)+

Retention time: 1.86 min (Analytical condition SMD method_02)

In a nitrogen atmosphere, phenylsilane (0).343 mL, 2.72 mmol) was added dropwise to a DCM (7.8 mL) solution of aa373-d (1.70 g, 3.88 mmol) and tetrakis(triphenylphosphine) palladium (( )(0).045 g, 0.039 mmol). The reaction mixture was stirred at room temperature for 30 minutes, and then diluted with tert-butyl methyl ether (17 mL). An aqueous sodium hydrogen carbonate solution (17 mL) was added to the resulting mixture to quench the reaction. The separated organic phase was extracted with water (8.5 mL), and DCM (17 mL) was added to the combined aqueous phase. Phosphoric acid (1.36 mL, 23.31 mmol) was added dropwise to the resulting mixture. After the organic phase was separated, the aqueous phase was extracted with DCM (17 mL), and the combined organic phase was washed with brine (17 mL). After the organic phase was dried over sodium sulfate, the solvent was distilled off under reduced pressure to give aa373 (1.31 g, 85%).

LCMS (ESI) m/z=397 (M+H)+

Retention time: 0.71 min (Analytical condition SQDFA05)

2-Chlorotrityl chloride resin (1.25 mmol/g, 5.3 g, 6.62 mmol) and DCM (37 mL) were placed in a filter-equipped reaction vessel (60 mL), and left to stand still at room temperature for 45 minutes. After DCM was removed by applying nitrogen pressure, a DCM (37 mL) solution of Compound aa373 (1.31 g, 3.31 mmol), DIPEA (2.77 mL, 15.9 mmol), and methanol (1.07 mL, 26.5 mmol) was added to the reaction vessel, and the reaction vessel was shaken at room temperature for 60 minutes. After the reaction solution was removed by applying nitrogen pressure, a DCM (37 mL) solution of DIPEA (2.77 mL, 15.9 mmol) and methanol (7.5 mL, 185 mmol) was added to the reaction vessel, and the reaction vessel was shaken at room temperature for 90 minutes. After the reaction solution was removed by applying nitrogen pressure, DCM (37 mL) was added, mixed, and then discharged by applying nitrogen pressure. This resin washing operation using DCM was repeated 5 times in total, and the resulting resin was dried under reduced pressure overnight to give aa373-resin (6.07 g).

The amount of supported amino acid on the resin was calculated as follows.

The resulting Compound aa373-resin (10) mg) was placed in a reaction vessel, DMF (4 mL) was added, and the reaction vessel was shaken at room temperature for 30 minutes. Then, DBU (40 μL) was added, and the reaction vessel was shaken at 30° C. for 15 minutes. Then, DMF was added to the reaction mixture to 10 mL, and 80 μL of this solution was diluted with DMF so as to have a liquid volume of 1 mL. The resulting diluted solution was analyzed by LC/MS (injection volume: 5 μL), and the amount of supported aa373 was calculated to be 0.404 mmol/g from the UV area value of dibenzofulvene (294 nm: 4211.62; 304 nm: 3791.08). Using a calibration curve created based on the UV area values of dibenzofulvene at wavelengths of 294 nm and 304 nm on each measurement day utilizing, as a standard substance, a mixed solution of Fmoc-Gly-OH (purchased from a commercial supplier) having a known concentration and DBU, the average value of the supported amounts calculated for each wavelength was regarded as the amount of supported resin.

Synthesis of Compound aa375-Resin

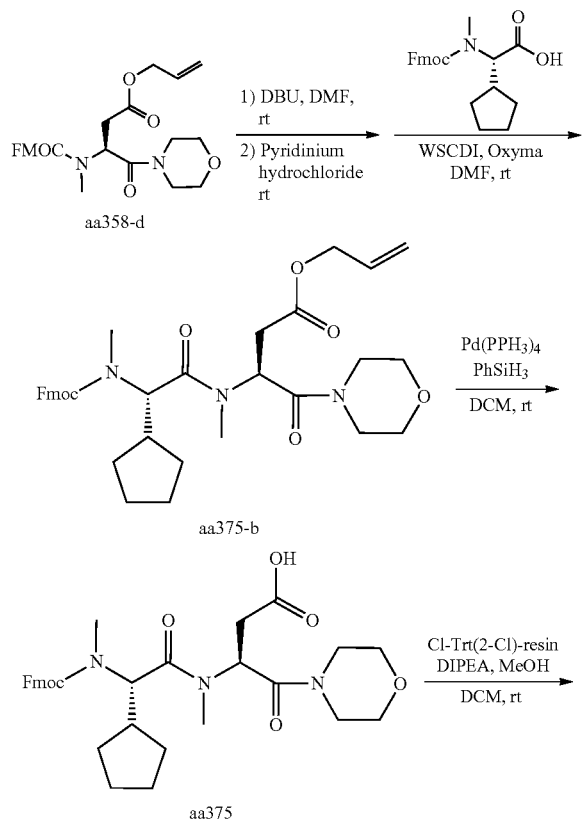

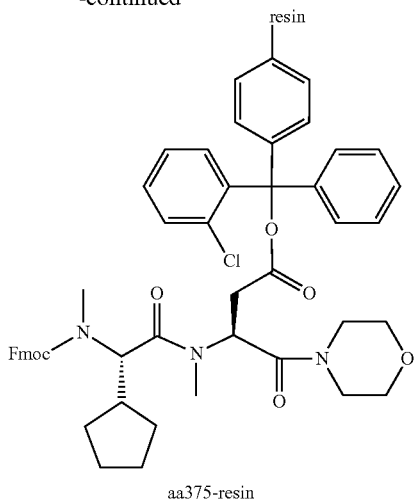

aa375-resin

In a nitrogen atmosphere, DBU (3.15 mL, 20.90 mmol) was added dropwise to a dehydrated DMF (50 mL) solution of aa358-d (10 g, 20.90 mmol) at room temperature, and the mixture was stirred for 10 minutes. Pyridine hydrochloride (2.66 g, 22.99 mmol) was added to the reaction mixture at room temperature, and the mixture was stirred for 10 minutes. A separately prepared active ester solution (as described below) was added to the reaction mixture at room temperature, and then DIPEA (4.01 mL, 22.99 mmol) was added dropwise. After the resulting reaction mixture was stirred at room temperature for 4 hours and 15 minutes, ethyl acetate (100 mL), hexane (20 mL), and 1 N hydrochloric acid (100 mL) were added. The resulting mixture was extracted with ethyl acetate-hexane (5:1)(total amount of organic phase of about 300 mL), the organic phase was washed with 1 N hydrochloric acid (100 mL), water (100 mL), an aqueous sodium hydrogen carbonate solution (100 mL×2), and brine (100 mL), dried over sodium sulfate, and the solvent was distilled off under reduced pressure. The resulting crude product was purified by normal phase silica gel chromatography (hexane/ethyl acetate). This was dissolved in TBME (100 mL) and washed with an aqueous potassium carbonate solution (1 w/v %, 50 mL). The organic phase was washed with saturated brine/water (1/1, 50 mL) and dried over sodium sulfate, and the solvent was distilled off under reduced pressure to give aa375-b (9.98 g, 81%).

The active ester solution was prepared as follows.

In a nitrogen atmosphere, dehydrated DMF (55 mL) was added to a mixture of (αS)-α-[(9H-fluoren-9-ylmethoxy) carbonyl]methylamino]cyclopentaneacetic acid (7.53 g, 19.85 mmol), WSCI·HCl (5.21 g, 27.2 mmol), and Oxyma (3.56 g, 25.08 mmol) at room temperature and stirred for 40 minutes, and the resulting reaction mixture was used as an active ester solution.

LCMS (ESI) m/z=618 (M+H)+

Retention time: 0).96 min (Analytical condition SQDFA05)

In a nitrogen atmosphere, dehydrated DCM (15 mL.) was added to a mixture of aa375-b (9.90 g, 16.03 mmol) and tetrakis(triphenylphosphine) palladium (( )(0.185 g, 0.16 mmol), and the mixture was stirred at room temperature. Phenylsilane (1.38 mL, 11.22 mmol) was added dropwise to the resulting solution. The resulting reaction mixture was stirred for 30 minutes, TBME (100 mL) was added, and then an aqueous sodium hydrogen carbonate solution (obtained by diluting a saturated aqueous solution by 2-fold)(100 mL) was slowly added dropwise to quench the reaction. The resulting mixture was extracted twice with water (total amount of aqueous phase of about 150 mL), and then DCM (100 mL) and phosphoric acid (5.6 mL) were added to the aqueous phase. The resulting mixture was extracted twice with DCM (total amount of organic phase of about 200 mL), the organic phase was washed with brine (80 mL×2) and dried over sodium sulfate, the solvent was distilled off under reduced pressure, and the resulting aa375 (9.57 g, quant.) was used in the next reaction.

LCMS (ESI) m/z=578 (M+H)+

Retention time: 0).79 min (Analytical condition SQDFA05)

2-Chlorotrityl chloride resin (1.36 mmol/g, 20.5 g, 15.07 mmol) and DCM (140 mL) were placed in a filter-equipped reaction vessel, and left to stand still at room temperature for 1 hour. After DCM was removed by applying nitrogen pressure, a DCM (140 mL) solution of Compound aa375 (9.50 g, 16.45 mmol), methanol (5.32 mL., 132 mmol), and DIPEA (13.8 mL, 79 mmol) was added to the reaction vessel, and the reaction vessel was shaken at 25° C. at 60 rpm for 60) minutes. After the reaction solution was removed by applying nitrogen pressure, a DCM (140) mL) solution of methanol (20 mL, 493 mmol) and DIPEA (13.8 mL, 79 mmol) was added to the reaction vessel, and the reaction vessel was shaken at 25° C. at 60 rpm for 60 minutes. After the reaction solution was removed by applying nitrogen pressure, DCM (140 mL) was added, mixed, and then discharged by applying nitrogen pressure. This resin washing operation with DCM was repeated 5 times in total, and the resulting resin was dried under reduced pressure for 1 day to give aa375-resin (26.89 g).

The amount of supported amino acid on the resin was calculated as follows.

The resulting compound aa375-resin (10 mg) was placed in a reaction vessel, DMF (2 mL) was added, and the mixture was left to stand still at room temperature for 1 hour. Then, DBU (40 μL) was added, and the reaction vessel was shaken at 25° C. for 30 minutes. Then, DMF (8 mL) was added to the reaction mixture, and 1 mL of this solution was diluted with DMF (11.5 mL). The absorbance (294 nm) of the resulting diluted solution was measured (measured with Shimadzu UV-1600PC(cell length 1.0 cm)), and thus the amount of supported Compound aa375 was calculated to be 0.415 mmol/g.

Synthesis of Compound aa374-Resin

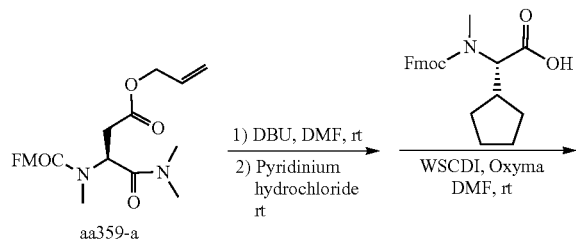

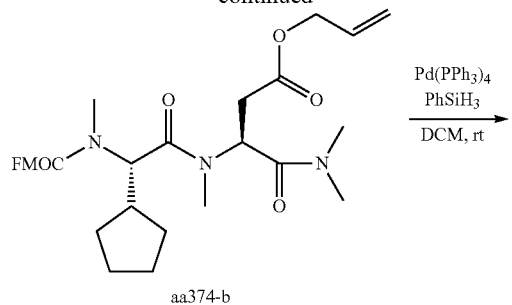

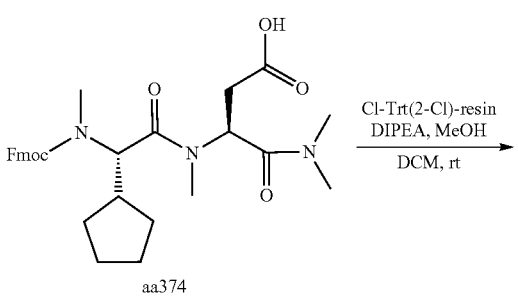

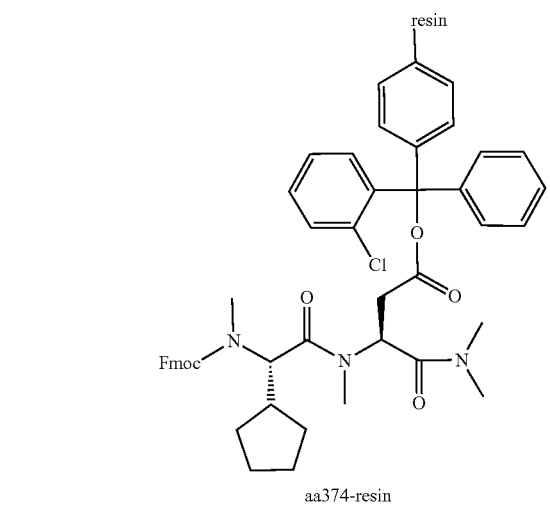

Using aa359-a as a starting material, aa074-b (5.0 g, 43%) was obtained in the same manner as the synthesis of Compound aa0375-b.

LCMS (ESI) m/z=576.5 (M+H)+

Retention time: 1.02 min (Analytical condition SQDFA05)

Using the resulting aa374-b, aa074 (0.786 g, 92%) was obtained under the same reaction conditions as the synthesis of Compound aa375.

LCMS (ESI) m/z=536 (M+H)+

Retention time: 0.85 min (Analytical condition SQDFA05) Using the resulting aa374, aa374-resin (2.72 g) was obtained under the same reaction conditions as the synthesis of Compound aa375-resin. The supported amount calculated in the same manner as aa375-resin was 0.345 mmol/g.

301
Synthesis of Compound aa376-Resin

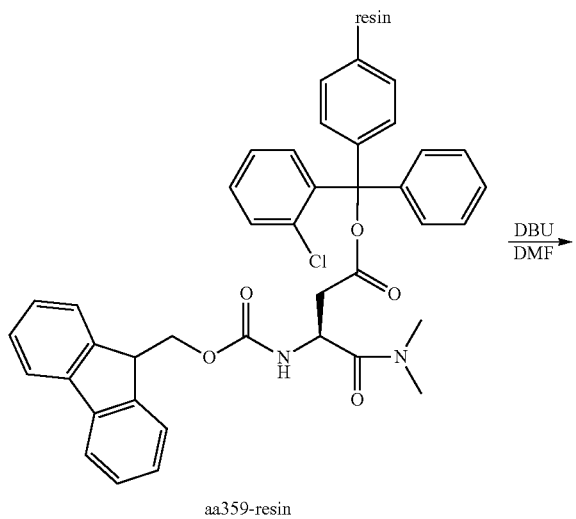

aa359-resin

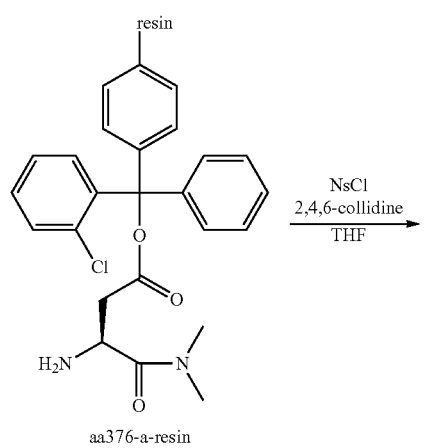

aa376-a-resin

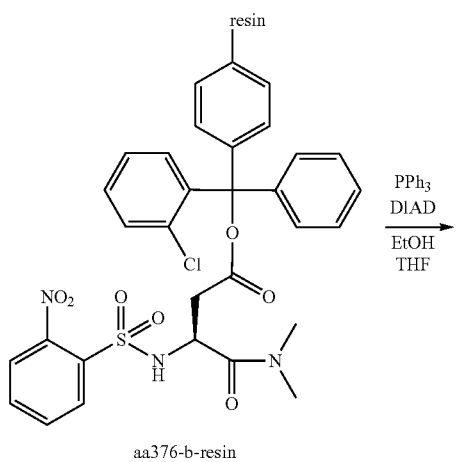

aa376-b-resin

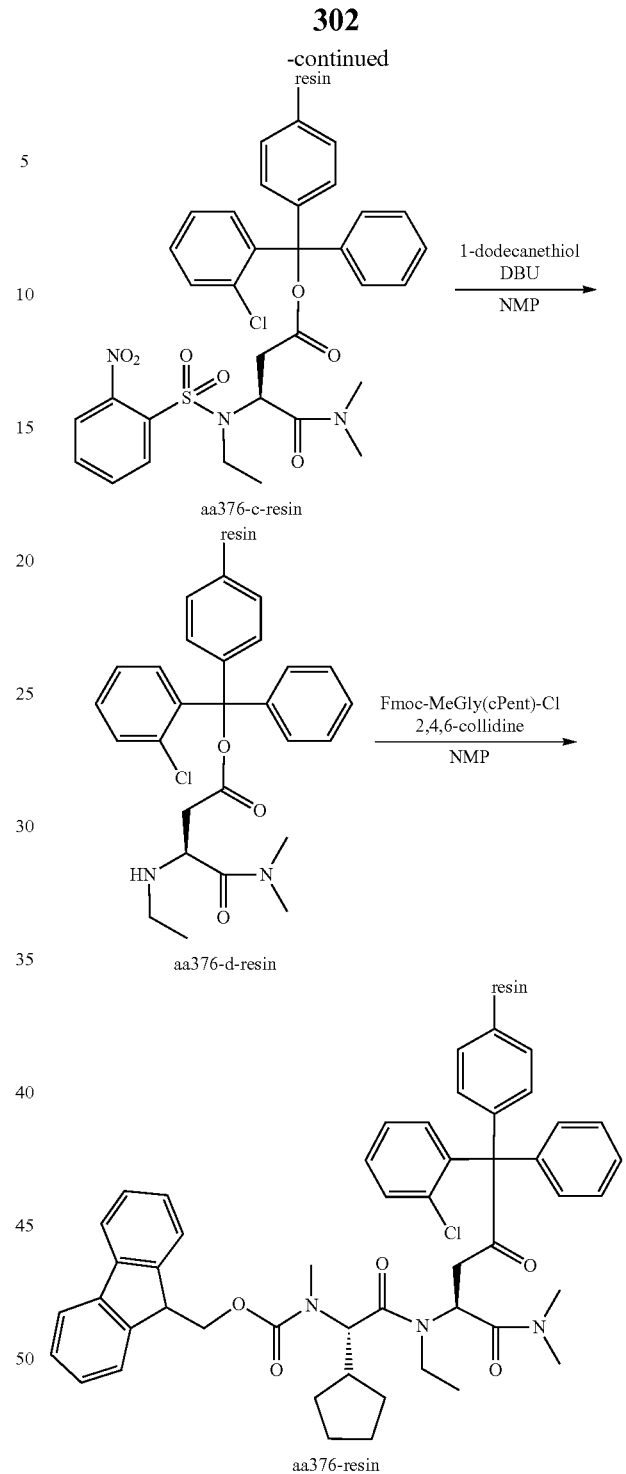

aa376-c-resin aa376-d-resin aa376-resin

Compound aa359-resin (10 g, 0.362 mmol/g, 3.62 mmol) and DCM (100 mL) were added to a filter-equipped reaction vessel to swell the resin. After DCM was removed, the resin was washed 4 times with DMF (100 mL). A DMF solution of DBU (2% v/v, 60 mL) was added, the mixture was shaken for 5 minutes at room temperature, and then the reaction solution was removed. The resin was washed 4 times with NMP (100 mL), and washed with a DCM solution (100 mL) of triethylamine hydrochloride (1.57 g, 11.4 mmol). The resin was washed 4 times with DCM (100 mL) and 4 times with THF (100 mL) to give the resin-supported Compound aa376-a.

A THE solution (100 mL) of nosyl chloride (3.66 g, 16.5 mmol) and 2,4,6-cholidine (6.60 mL, 49.6 mmol) were added thereto, and the mixture was shaken at room temperature for 3 hours. Then, the reaction solution was removed, and the resin was washed 4 times with THE (100 mL) and washed 4 times with DCM (100 mL) to give the resin-supported Compound aa376-b. The amino acid was cleaved from the resin by TFE/DCM (1/1) using a small amount of the resin-supported Compound aa376-b, and the structure was verified by LC/MS. LCMS (ESI) m/z=347 (M+H)+

Retention time: 0.45 min (Analytical condition SQDFA05)

Then, 6 g of this Compound 376-b-resin was weighed out, and swelled by adding DCM (60 mL). After DCM was removed, the resin was washed 3 times with THF (42 mL). A THF solution (20 mL) of DIAD (2.11 mL, 10.9 mmol) was added to a THE solution (20 mL) of triphenylphosphine (2.85 g, 10.9 mmol), and the mixture was shaken for 15 minutes. Ethanol (1.27 mL, 21.7 mmol) was added thereto, and the mixture was left to stand still for 5 minutes. This was added to the resin, the mixture was shaken at room temperature for 1 hour, and then the reaction solution was removed. The resin was washed 4 times with THF (42 mL) and washed 4 times with DCM (42 mL) to give the resin-supported Compound aa376-c. The amino acid was cleaved from the resin by TFE/DCM (1/1) using a small amount of the resin-supported Compound aa376-c, and the structure was verified by LC/MS.

LCMS (ESI) m/z=375 (M+H)+

Retention time: 0.56 min (Analytical condition SQDFA05)

DCM (60 mL) was added to swell this Compound aa376-c-resin. After DCM was removed, the resin was washed 3 times with NMP (42 mL). An NMP solution of DBU (1.64 mL, 10.9 mmol) and an NMP solution (20 mL) of 1-dodecanethiol (4.93 mL, 21.7 mmol) were added, and the mixture was shaken at 40° C. for 1 hour. Then, the reaction solution was removed, and the resin was washed 4 times with NMP (42 mL) and washed 4 times with DCM (42 mL). This was washed 8 times with DMF (42 mL) and washed 4 times with DCM (42 mL) to give the resin-supported Compound aa376-d. The amino acid was cleaved from the resin by TFE/DCM (1/1) using a small amount of the resin-supported Compound aa376-d, and the structure was verified by LC/MS.

LCMS (ESI) m/z=189 (M+H)+

Retention time: 0.14 min (Analytical condition SQDFA05)

Then, 5 g of this Compound 376-d-resin was weighed out, and swelled by adding DCM (50 mL). After DCM was removed, the resin was washed 4 times with NMP (50 mL). Compound aa330 (Fmoc-MeGly (cPent)-OH, 2.75 g, 7.24 mmol) was dissolved in DCM (72 mL), thionyl chloride (1.32 mL, 18.1 mmol) and DMF (0.056 mL, 0.724 mmol) were added thereto, and the mixture was stirred at room temperature for 2 hours. After the solvent was distilled off from this under reduced pressure, NMP (70 mL) and 2,4,6-cholidine (2.4 mL, 18.1 mmol) were added. This was added to the resin, and the mixture was shaken at 40° C. for 1.5 hours. Then, the reaction solution was removed, and the resin was washed 4 times with NMP (50 mL) and washed 4 times with DCM (50 mL) to give the resin-supported Compound aa376. The amino acid was cleaved from the resin by TFE/DCM (1/1) using a small amount of the resin-supported Compound aa376, and the structure was verified by LC/MS.

LCMS (ESI) m/z=551 (M+H)+

Retention time: 0.86 min (Analytical condition SQDFA05)

Synthesis of Compounds aa377-resin, aa378-resin, aa379-resin, and aa380-Resin

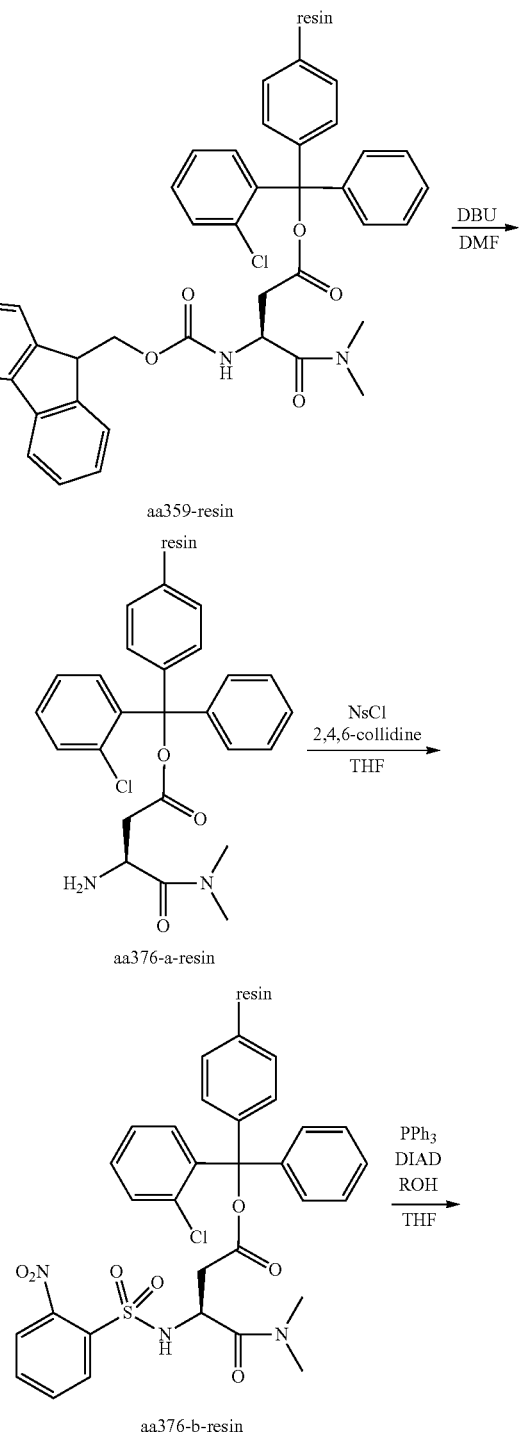

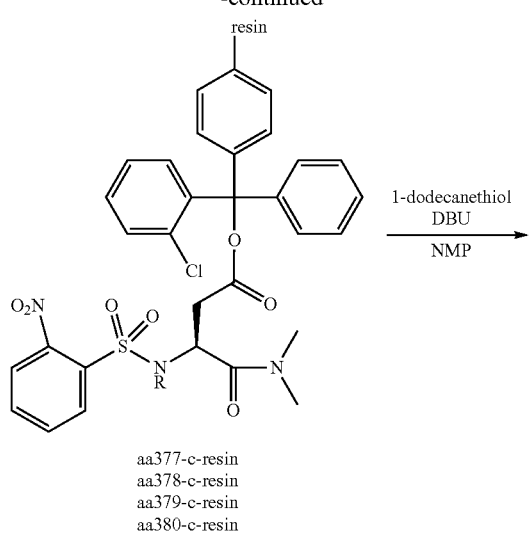

aa377-c-resin
aa378-c-resin
aa379-c-resin
aa380-c-resin

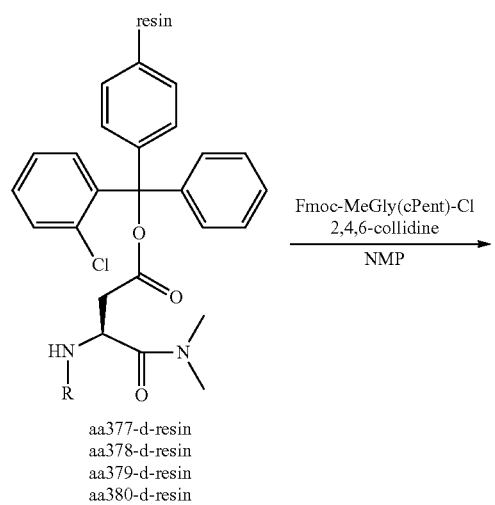

aa377-d-resin
aa378-d-resin
aa379-d-resin
aa380-d-resin

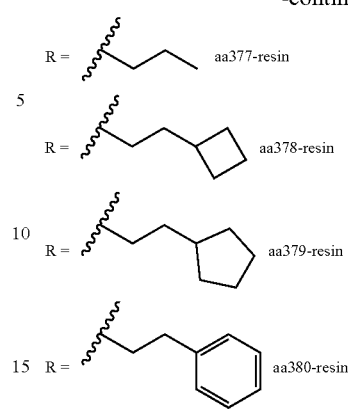

In place of ethanol, the alcohols shown in Table 7 below were reacted with aa376-b-resin in the same manner as aa376-c-resin, and thus resin-supported aa377-c to aa380-c were obtained. Using them, resin-supported aa377-d to aa380-d were obtained in the same manner as aa376-d-resin. Using them, resin-supported aa377 to aa380 were synthesized in the same manner as aa376-resin. The amino acid was cleaved from the resin by TFE/DCM (1/1) using a small amount of the resin-supported Compounds aa377 to aa380, and the structure was verified by LC/MS.

TABLE 7

| Intended product | Alcohol | LCMS (ESI) m/z (M + H)+ | Retention time (Analytical condition SQDFA05) |
|---|---|---|---|
| Compound aa377-resin | 1-propanol | 565 | 0.92 Min |
| Compound aa378-resin | 2-Cyclobutylethanol | 605 | 1.03 Min |
| Compound aa379-resin | 2-Cyclopentylethanol | 619 | 1.07 Min |
| Compound aa380-resin | 2-Phenylethanol | 627 | 1.01 Min |

Synthesis of Compounds aa381-resin, aa382-resin, aa383-resin, aa384-resin, and aa385-Resin

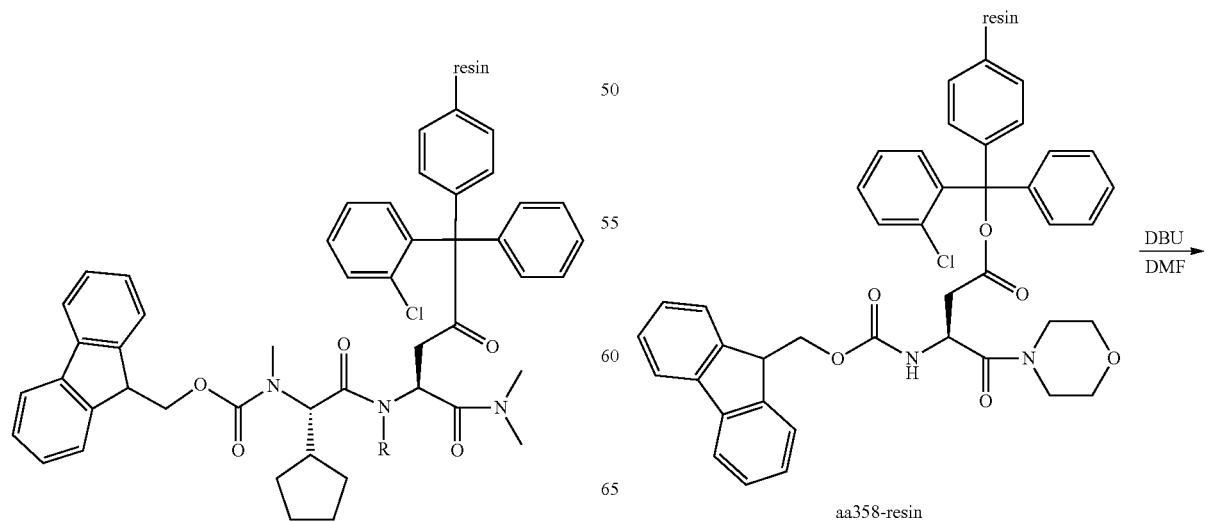

aa358-resin

307
-continued
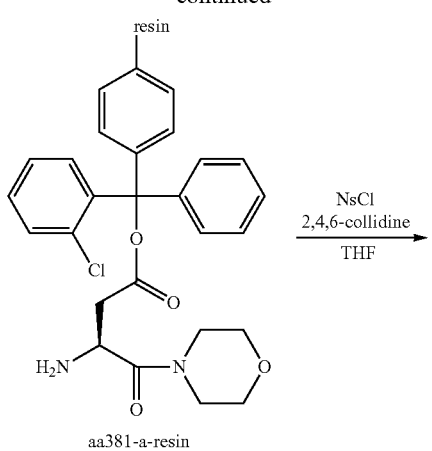
aa381-a-resin
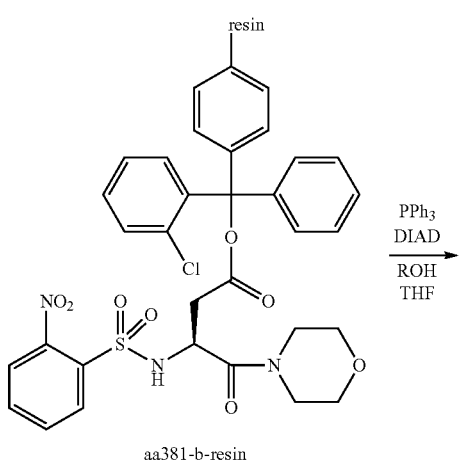
aa381-b-resin
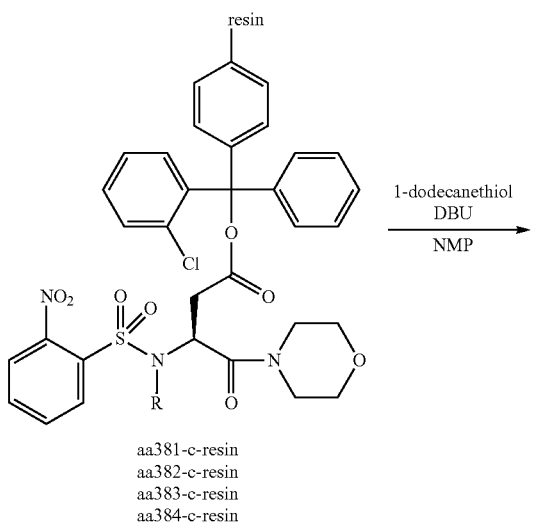
aa381-c-resin
aa382-c-resin
aa383-c-resin
aa384-c-resin
aa385-c-resin
308
-continued
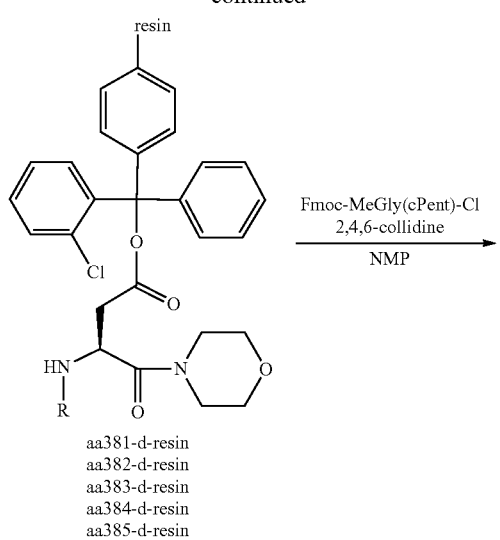
aa381-d-resin
aa382-d-resin
aa383-d-resin
aa384-d-resin
aa385-d-resin
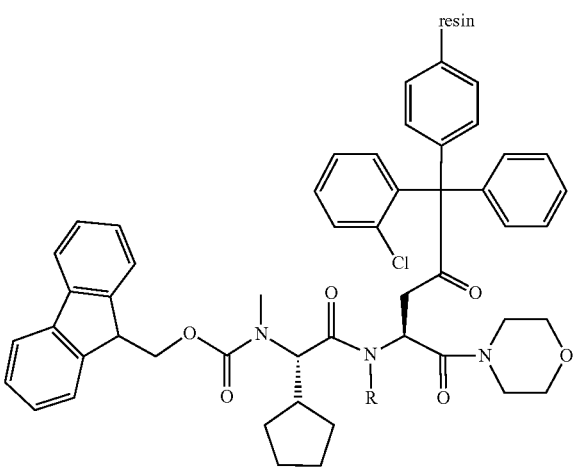

Using aa358-resin in place of aa359-resin, resin-supported aa381-a was obtained in the same manner as aa376-a-resin. Using this compound, resin-supported aa381-b was obtained in the same manner as aa376-b-resin. Using this compound, resin-supported aa381-c to aa385-c were obtained in the same manner as aa376-c-resin or using alcohols shown in Table 8 below to react with the compound in place of ethanol. Using these compounds, resin-supported aa381-d to aa385-d were obtained in the same manner as aa376-d-resin. Using these compounds, resin-supported aa381 to aa385 were synthesized in the same manner as aa376-resin. The amino acid was cleaved from the resin by TFE/DCM (1/1) using a small amount of resin-supported Compounds aa381 to aa385, and the structure was verified by LC/MS.

TABLE 8

| Intended product | Alcohol | LCMS (ESI) m/z (M + H)+ | Retention time (Analytical condition SQDFA05) |
|---|---|---|---|
| Compound aa381-resin | ethanol | 593 | 0.85 |
| Compound aa382-resin | 1-propanol | 607 | 0.91 |
| Compound aa383-resin | 2-Cyclobutylethanol | 647 | 1.02 |
| Compound aa384-resin | 2-Cyclopentylethanol | 661 | 1.06 |
| Compound aa385-resin | 2-Phynylethanol | 669 | 1.00 |

Synthesis of Compound aa427-Resin

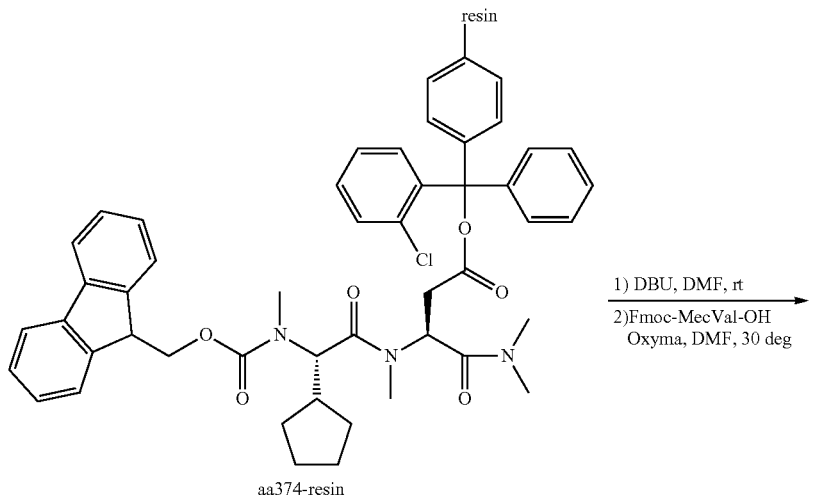

aa374-resin

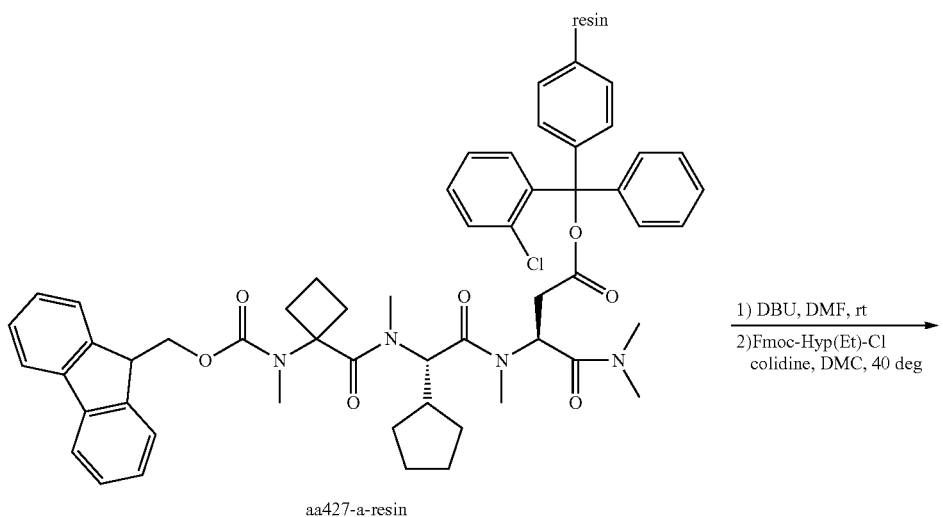

aa427-a-resin

-continued

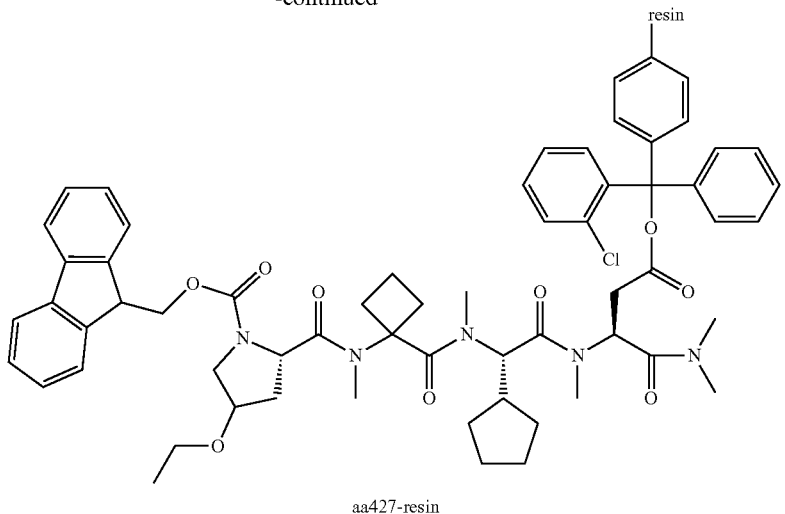

aa427-resin aa374-resin (0.420 mmol/g, 10 g) was placed in a filter-equipped reaction vessel, dichloromethane (100 mL) was added, and the mixture was shaken at room temperature for 5 minutes to swell the resin. After dichloromethane was removed with a filter, the resin was washed 4 times with DMF (100 mL). Subsequently, a 2% DBU/DMF solution (de-Fmoc solution: 60 mL) was added to the resin, and the mixture was shaken at room temperature for 10 minutes to carry out an Fmoc-removal reaction. After the de-Fmoc solution was removed, the resin was washed 6 times with DMF (100 mL). An Fmoc-MecVal-OH (Compound aa421) elongation reaction was carried out on the resulting resin. The elongation reaction was carried out by adding a solution obtained by mixing DIC(2.63 mL, 16.8 mmol) with a DMF solution (40 mL) of Fmoc-MecVal-OH (Compound aa421, 2.95 g, 8.40 mmol) and oxyma (597 mg, 4.20 mmol) to the resin, and shaking the mixture at 30° C. for 86 hours. After the liquid phase of the elongation reaction was removed with a filter, the resin was washed 6 times with DMF (100 mL) and 6 times with dichloromethane (100 mL) and dried to give aa427-a-resin.

Dichloromethane (100 mL) was added to the resulting aa427-a-resin, and the mixture was shaken at room temperature for 5 minutes to swell the resin. After dichloromethane was removed with a filter, the resin was washed 4 times with DMF (100 mL). Subsequently, a 2% DBU/DMF solution (de-Fmoc solution: 60 mL) was added to the resin, and the mixture was shaken at room temperature for 10 minutes to carry out an Fmoc-removal reaction. After the de-Fmoc solution was removed, the resin was washed 6 times with DMF (100 mL) and 6 times with dichloromethane (100 mL). An Fmoc-Hyp (Et)-OH (Compound aa086) elongation reaction was carried out on the resulting resin. The elongation reaction was carried out by, first, adding thionyl chloride (3.07 mL, 42.0 mmol) and DMF (0.131 mL, 1.68 mmol) to a DCM solution (84 mL) of Fmoc-Hyp (Et)-OH (Compound aa086, 6.41 g, 16.8 mmol), and stirring the mixture at room temperature for 4 hours in a nitrogen atmosphere. The solvent and thionyl chloride were distilled off under reduced pressure to give an acid chloride of Fmoc-Hyp (Et)-OH. This acid chloride was dissolved in DCM (100 mL) and mixed with collidine (5.59 mL, 42.0 mmol), the resulting solution was added to the resin, and the mixture was shaken at 40° C. for 13 hours. After the liquid phase of the elongation reaction was removed with a filter, the resin was washed 6 times with DMF (100 mL) and 6 times with dichloromethane (100 mL) and dried to give aa427-resin. Amino acid was cleaved from the resin by TFE/DCM (1/1) using a small amount of resin-supported Compound aa427, and the structure was verified by LC/MS.

LCMS (ESI) m/z=789 (M+H)+

Retention time: 0.84 min (Analytical condition SQDFA05)

Synthesis of Compound aa428-Resin

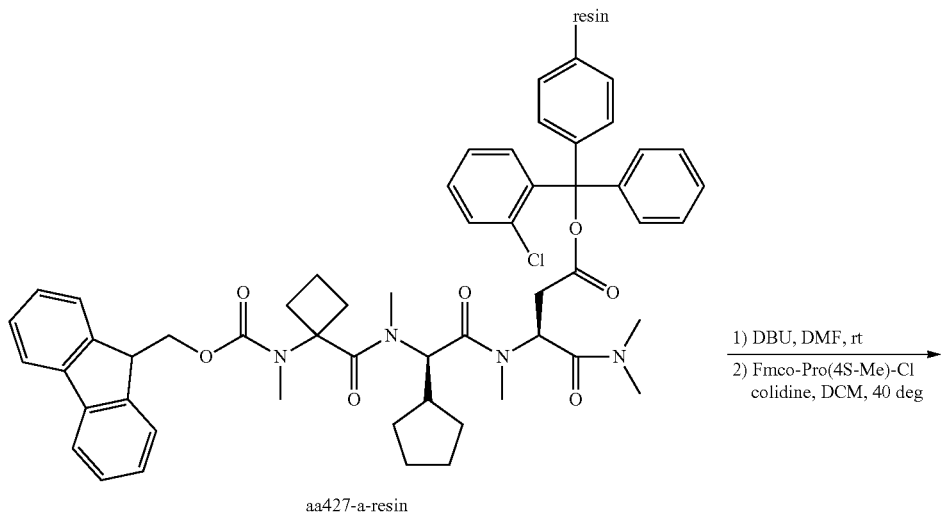

aa427-a-resin

1) DBU, DMF, rt
2) Fmco-Pro(4S-Me)-Cl colidine, DCM, 40 deg

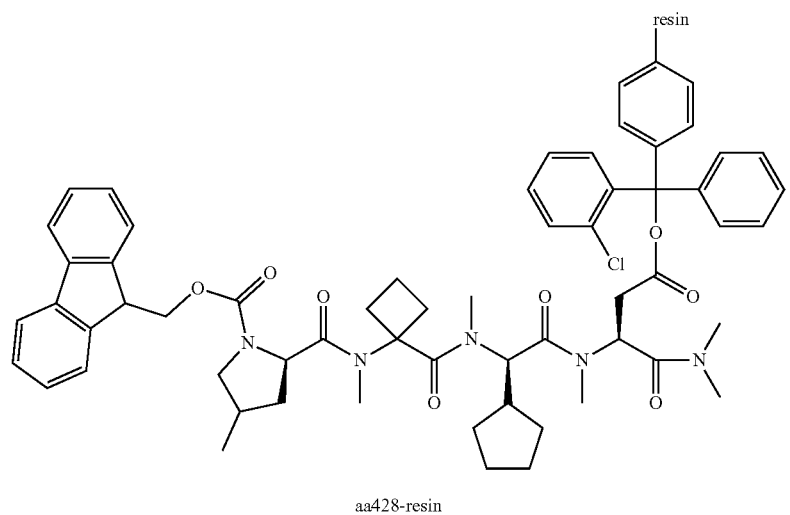

aa428-resin

Using aa427-a-resin, aa428-resin was obtained in the same manner as Compound aa427-resin except that Fmoc-Pro (4S-Me)-OH (Compound aa239) was used in place of Fmoc-Hyp (Et)-OH. Amino acid was cleaved from the resin by TFE/DCM (1/1) using a small amount of resin-supported Compound aa428, and the structure was verified by LC/MS.

LCMS (ESI) m/z=759 (M+H)+

Retention time: 0.85 min (Analytical condition SQDFA05)

Synthesis of Compound aa429-Resin

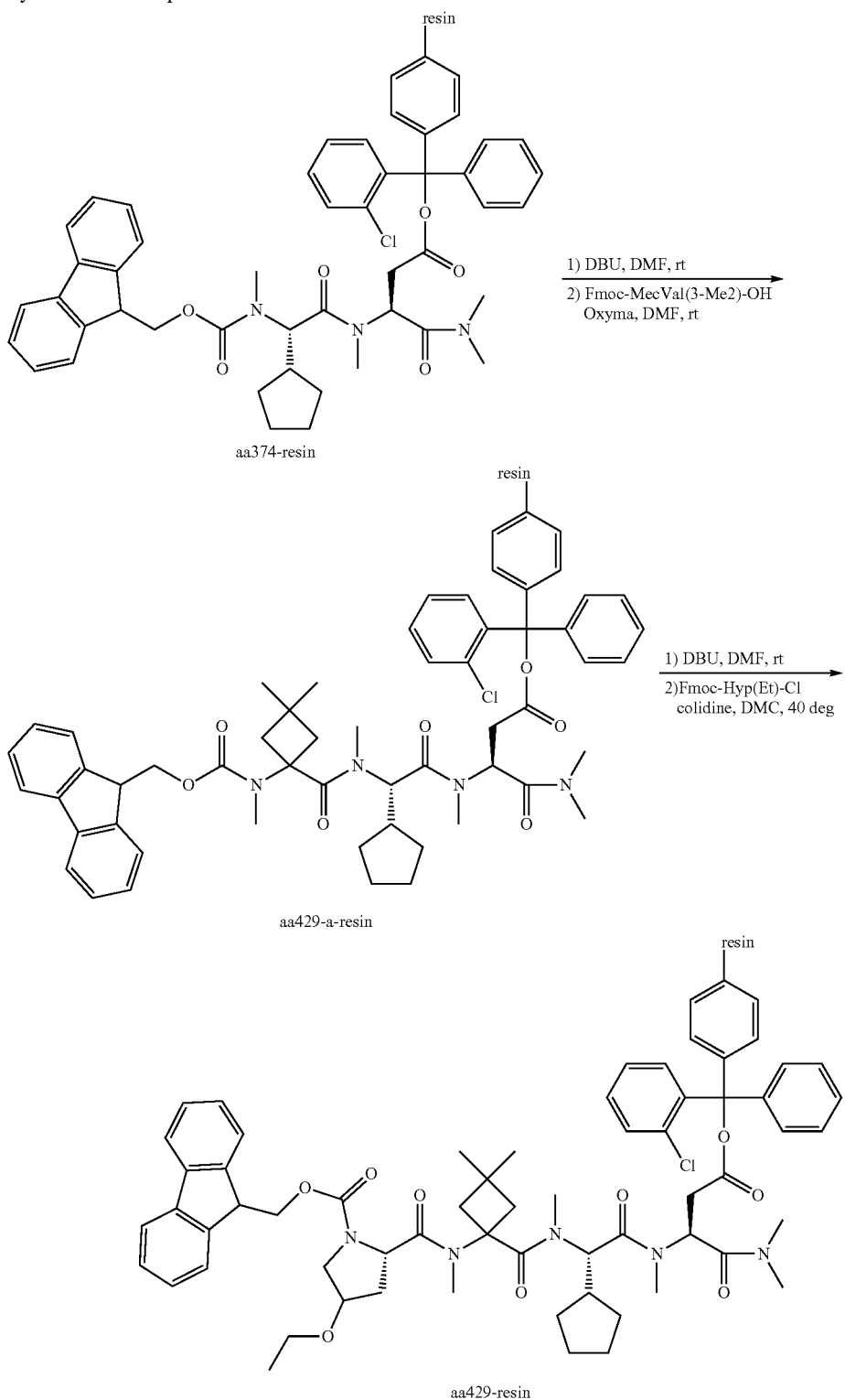

Using aa374-resin, aa429-a-resin was obtained in the same manner as Compound aa427-a-resin except that Fmoc-MecVal (3-Me2)-OH (Compound aa420) was used in place of Fmoc-Mec Val-OH.

Using the resulting aa429-a-resin, aa429-resin was obtained in the same manner as Compound aa427-resin. Amino acid was cleaved from the resin by TFE/DCM (1/1) using a small amount of resin-supported Compound aa429, and the structure was verified by LC/MS. LCMS (ESI) m/z=817 (M+H)+

Retention time: 0.94 min (Analytical condition SQDFA05)

Synthesis of Compound aa430-Resin
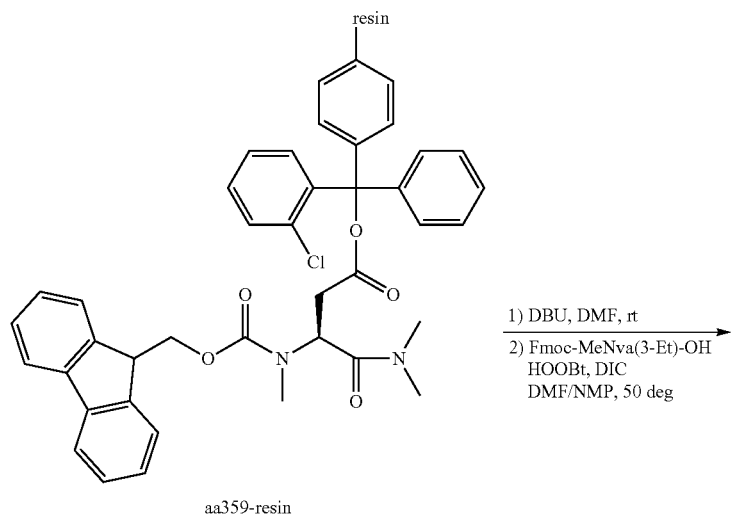
aa359-resin
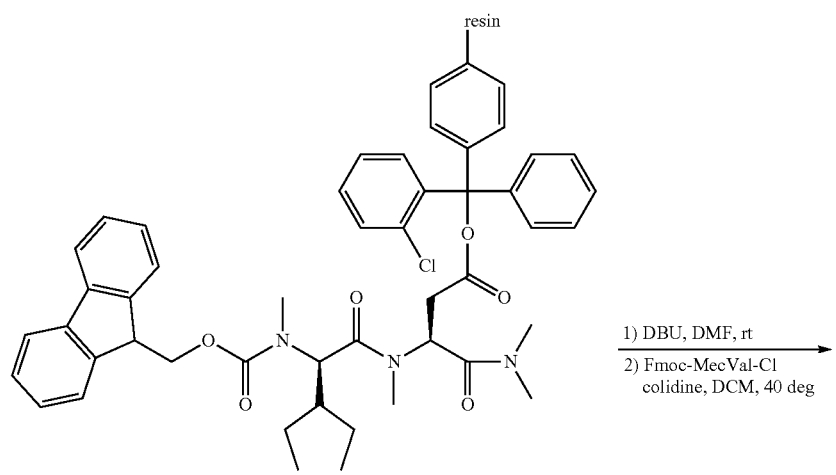
aa430-a-resin
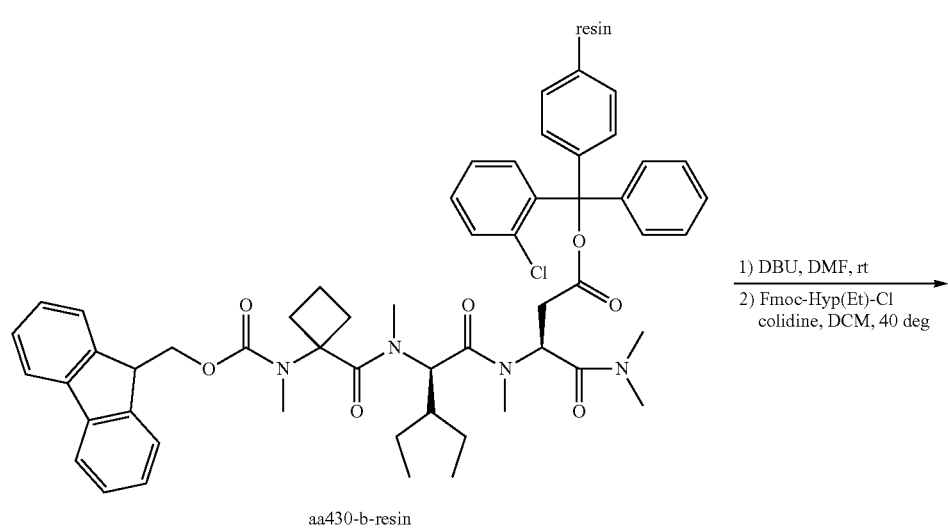
aa430-b-resin

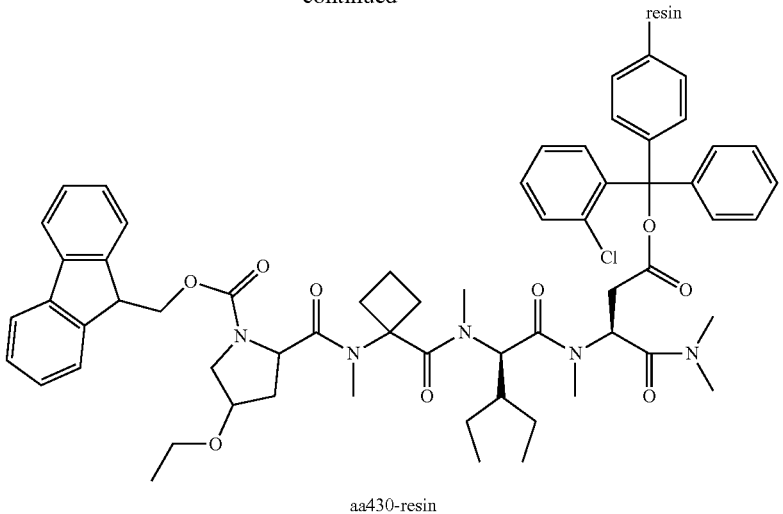

aa430-resin aa359-resin (0.320 mmol/g, 5 g) was placed in a filter-equipped reaction vessel, dichloromethane (50 mL) was added, and the mixture was shaken at room temperature for 5 minutes to swell the resin. After dichloromethane was removed with a filter, the resin was washed 4 times with DMF (50 mL). Subsequently, a 2% DBU/DMF solution (de-Fmoc solution: 30 mL) was added to the resin, and the mixture was shaken at room temperature for 10 minutes to carry out an Fmoc-removal reaction. After the de-Fmoc solution was removed, the resin was washed 6 times with DMF (50 mL). An Fmoc-MeNva (3-Et)-OH (Compound aa331) elongation reaction was carried out on the resulting resin. The elongation reaction was carried out by adding to the resin a solution obtained by mixing an NMP solution (15 mL) of Fmoc-MeNva (3-Et)-OH (Compound aa331, 2.44 g, 6.40 mmol) and HOOBt (653 mg, 4.00 mmol) with a DMF solution (15 mL) of DIC(1.50 mL, 9.60 mmol), shaking the mixture at 50° C. for 14 hours, removing the liquid phase of the elongation reaction with a filter, again adding to the resin a solution obtained by mixing an NMP solution (15 mL) of Fmoc-MeNva (3-Et)-OH (Compound aa331, 2.44 g, 6.40 mmol) and HOOBt (653 mg, 4.00 mmol) with a DMF solution (15 mL) of DIC(1.50 mL, 9.60 mmol), and shaking the mixture at 50° C. for 14 hours. After the liquid phase of the elongation reaction was removed with a filter, the resin was washed 4 times with DMF (100 mL) and 4 times with dichloromethane (100 mL) and dried to give aa430-a-resin.

Using the resulting aa430-a-resin, aa430-b-resin was obtained in the same manner as Compound aa427-resin except that Fmoc-Mec Val-OH was used in place of Fmoc-Hyp (Et)-OH.

Using the resulting aa430-b-resin, aa430-resin was obtained in the same manner as Compound aa427-resin. Amino acid was cleaved from the resin by TFE/DCM (1/1) using a small amount of resin-supported Compound aa430, and the structure was verified by LC/MS. LCMS (ESI) m/z=791 (M+H)+

Retention time: 0.88 min (Analytical condition SQDFA05)

Synthesis of Compound aa431-Resin

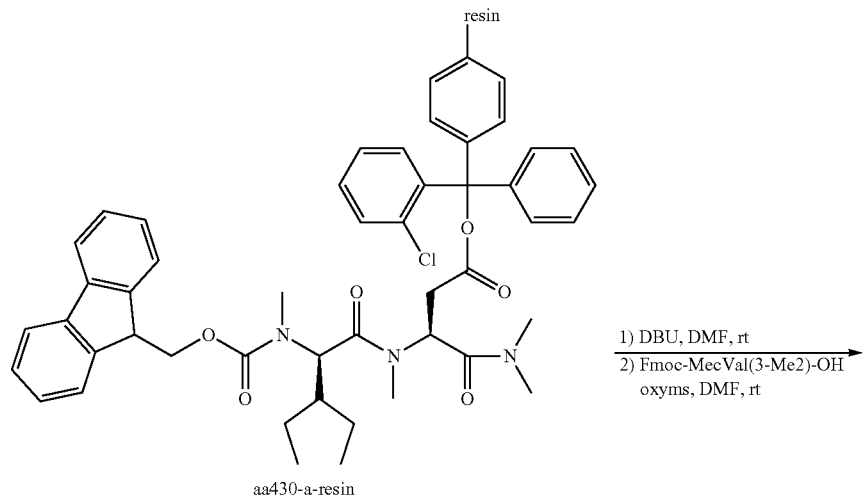

aa430-a-resin

1) DBU, DMF, rt
2) Fmoc-MecVal(3-Me2)-OH oxyms, DMF, rt

-continued

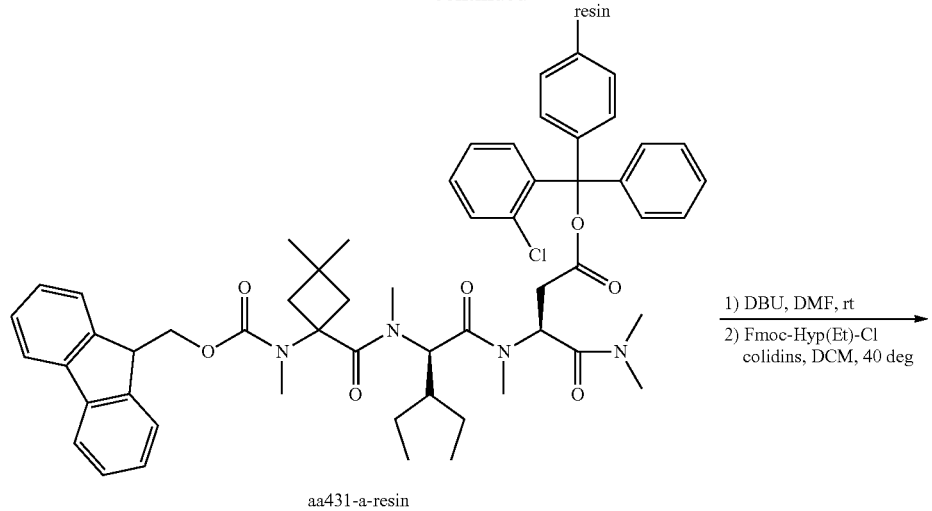

aa431-a-resin

1) DBU, DMF, rt
2) Fmoc-Hyp(Et)-Cl
   colidins, DCM, 40 deg

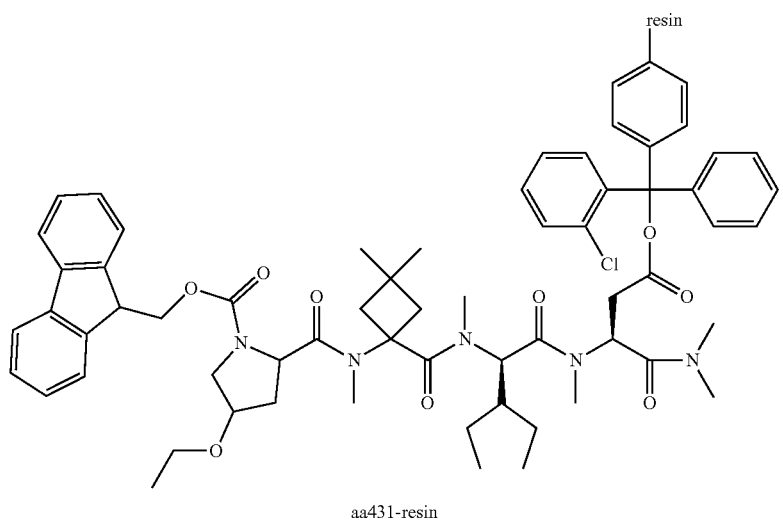

aa431-resin

Using aa430-a-resin, aa431-a-resin was obtained in the same manner as Compound aa427-a-resin except that Fmoc-MecVal (3-Me2)-OH (Compound aa420) was used in place of Fmoc-Mec Val-OH.

Using the resulting aa431-a-resin, aa431-resin was obtained in the same manner as Compound aa427-resin. Amino acid was cleaved from the resin by TFE/DCM (1/1) using a small amount of resin-supported Compound aa431, and the structure was verified by LC/MS. LCMS (ESI) m/z=819 (M+H)+

Retention time: 0.98 min (Analytical condition SQDFA05)

Synthesis of Compound aa432-Resin

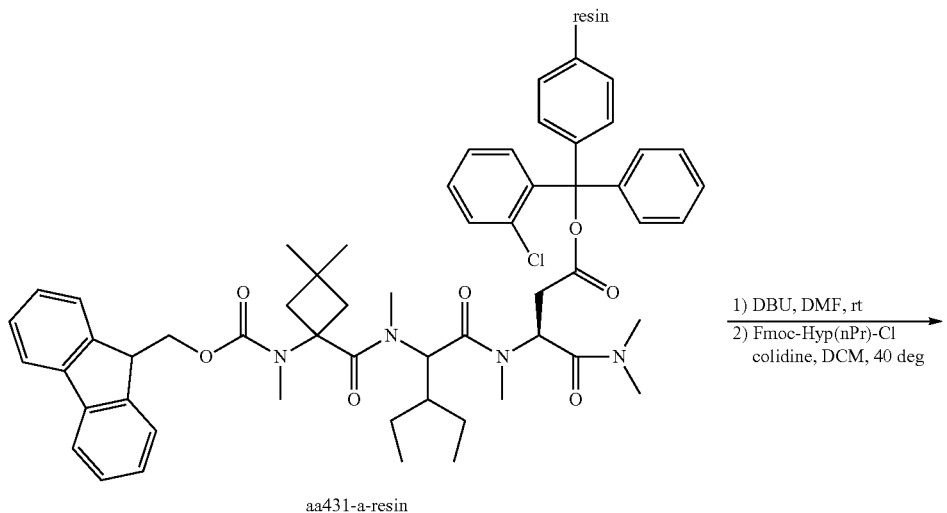

aa431-a-resin

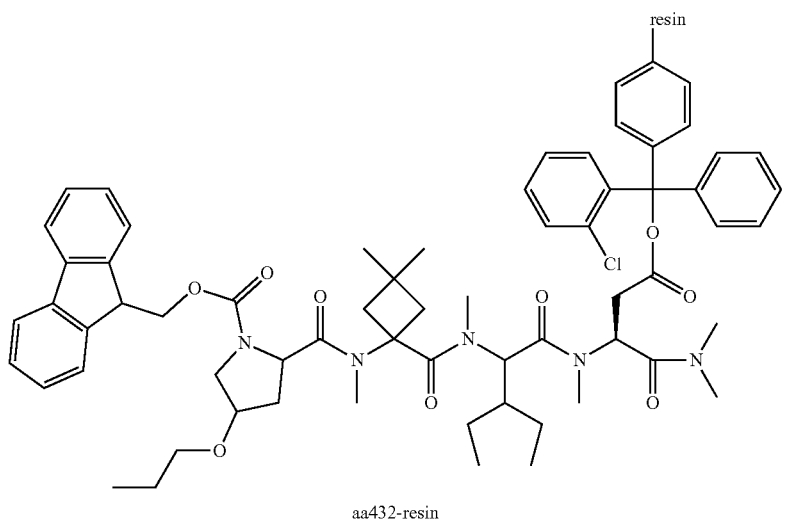

aa432-resin

Using aa431-a-resin, aa432-resin was obtained in the same manner as Compound aa427-resin except that Fmoc-Hyp (nPr)—OH (Compound aa246) was used in place of Fmoc-Hyp (Et)-OH. Amino acid was cleaved from the resin by TFE/DCM (1/1) using a small amount of resin-supported Compound aa432, and the structure was verified by LC/MS.

LCMS (ESI) m/z=833 (M+H)+

Retention time: 1.03 min (Analytical condition SQDFA05)

Synthesis of Compound aa433-Resin

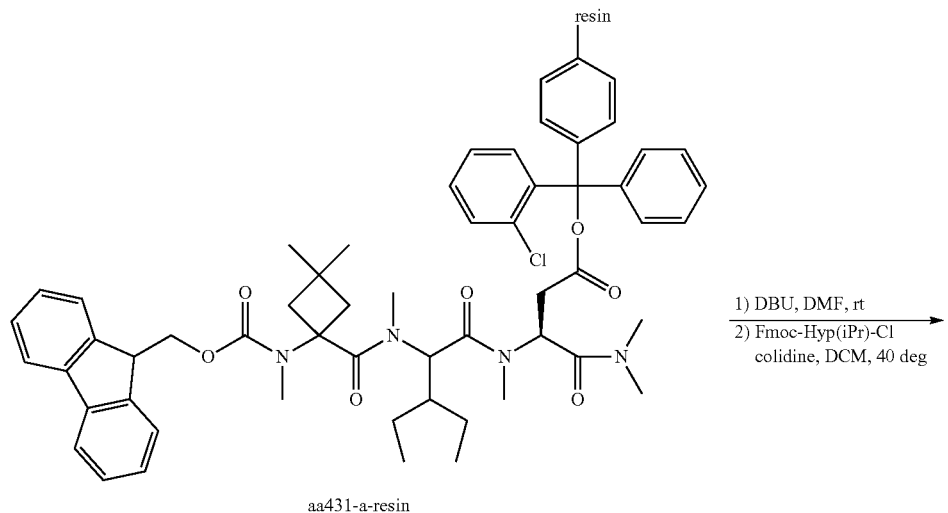

aa431-a-resin

1) DBU, DMF, rt
2) Fmoc-Hyp(iPr)-Cl
colidine, DCM, 40 deg

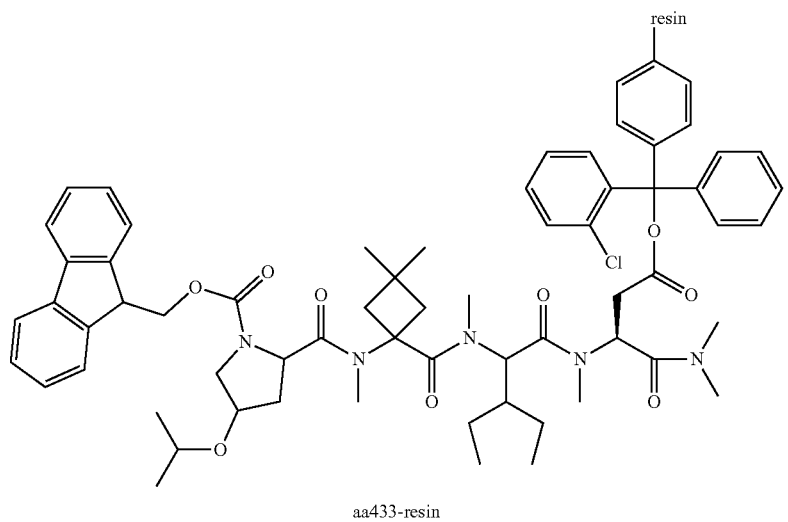

aa433-resin

Using aa431-a-resin, aa433-resin was obtained in the same manner as Compound aa427-resin except that Fmoc-Hyp (iPr)—OH (Compound aa416) was used in place of Fmoc-Hyp (Et)-OH. Amino acid was cleaved from the resin by TFE/DCM (1/1) using a small amount of resin-supported Compound aa433, and the structure was verified by LC/MS.

LCMS (ESI) m/z=833 (M+H)+

Retention time: 1.01 min (Analytical condition SQDFA05)

Synthesis of Compound aa434-Resin

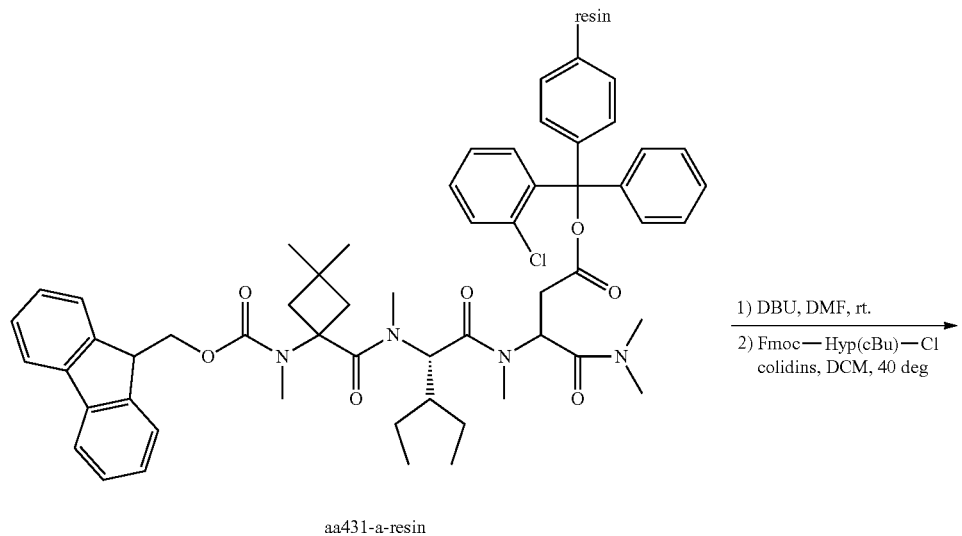

aa431-a-resin

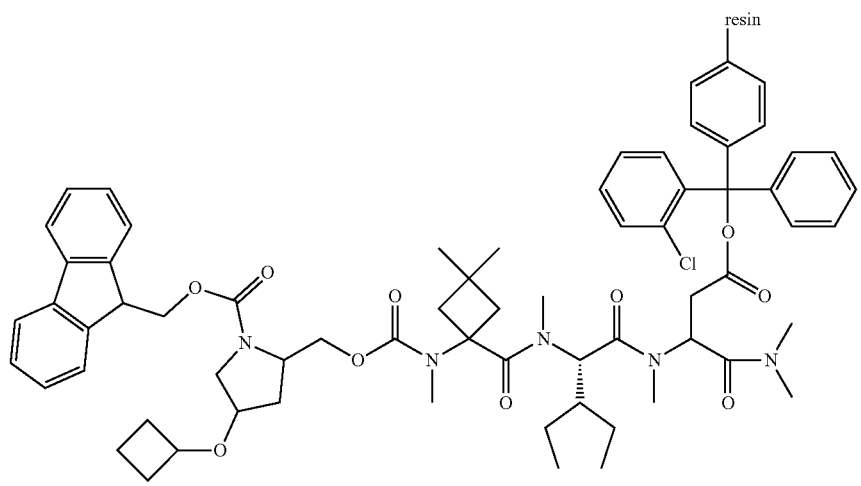

aa431-a-resin

Using aa431-a-resin, aa434-resin was obtained in the same manner as Compound aa427-resin except that Fmoc-Hyp (cBu)-OH (Compound aa415) was used in place of Fmoc-Hyp (Et)-OH. Amino acid was cleaved from the resin by TFE/DCM (1/1) using a small amount of resin-supported Compound aa434, and the structure was verified by LC/MS.

LCMS (ESI) m/z=845 (M+H)+

Retention time: 1.04 min (Analytical condition SQDFA05)

Synthesis of Compound aa435-Resin

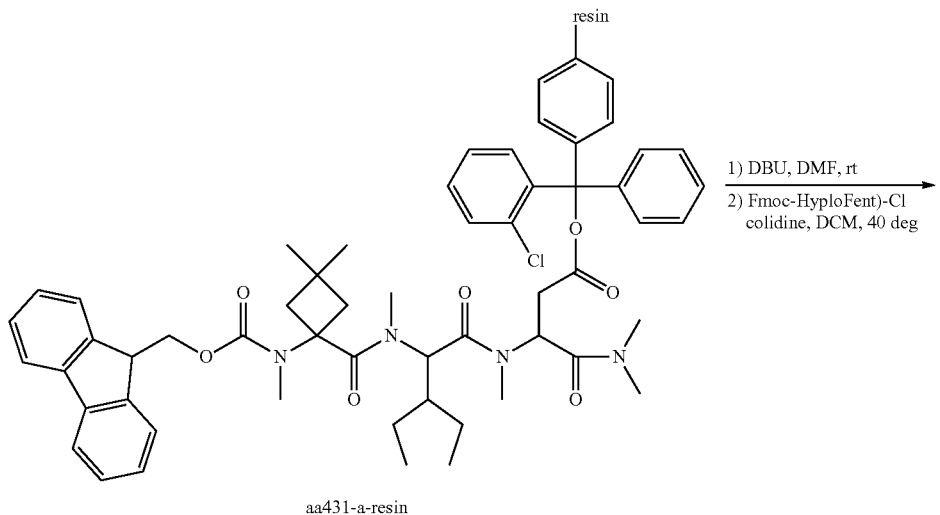

aa431-a-resin

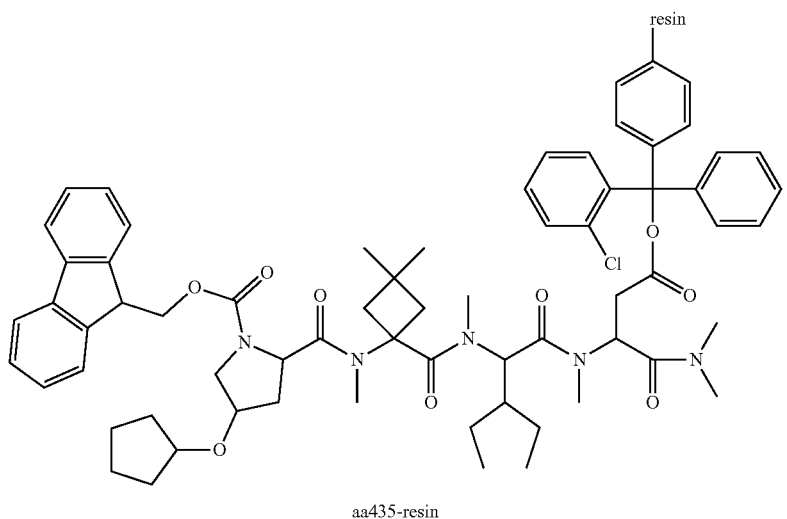

aa435-resin

Using aa431-a-resin, aa435-resin was obtained in the same manner as Compound aa427-resin except that Fmoc-Hyp (cPent)-OH (Compound aa414) was used in place of Fmoc-Hyp (Et)-OH. Amino acid was cleaved from the resin by TFE/DCM (1/1) using a small amount of resin-supported Compound aa435, and the structure was verified by LC/MS.

LCMS (ESI) m/z=859 (M+H)+

Retention time: 1.08 min (Analytical condition SQDFA05)

Synthesis of Compound aa436-Resin

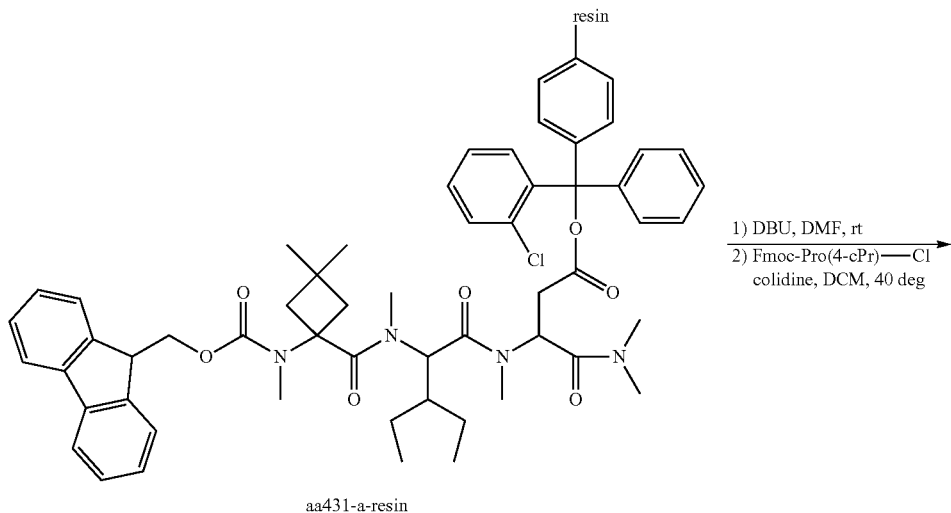

aa431-a-resin

1) DBU, DMF, rt
2) Fmoc-Pro(4-cPr)—Cl
   colidine, DCM, 40 deg

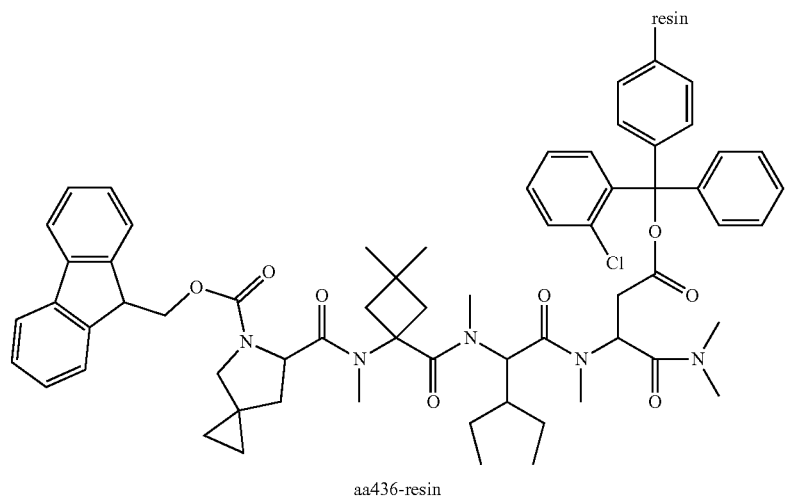

aa436-resin

Using aa431-a-resin, aa436-resin was obtained in the same manner as Compound aa427-resin except that Fmoc-Pro (4-cPr)—OH (Compound aa278) was used in place of Fmoc-Hyp (Et)-OH. Amino acid was cleaved from the resin by TFE/DCM (1/1) using a small amount of resin-supported Compound aa436, and the structure was verified by LC/MS.

LCMS (ESI) m/z=801 (M+H)+

Retention time: 0.99 min (Analytical condition SQDFA05)

Synthesis of Compound aa437-Resin
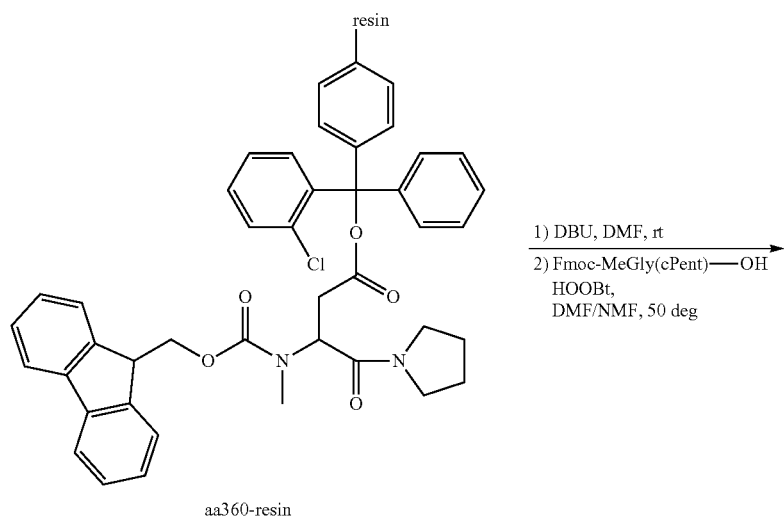
aa360-resin
1) DBU, DMF, rt
2) Fmoc-MeGly(cPent)—OH
   HOOBt,
   DMF/NMF, 50 deg
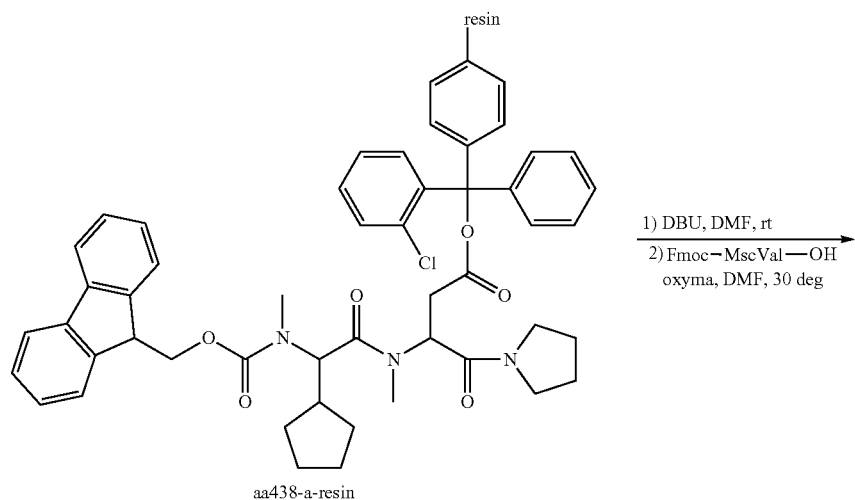
aa438-a-resin
1) DBU, DMF, rt
2) Fmoc—MscVal—OH
   oxyma, DMF, 30 deg
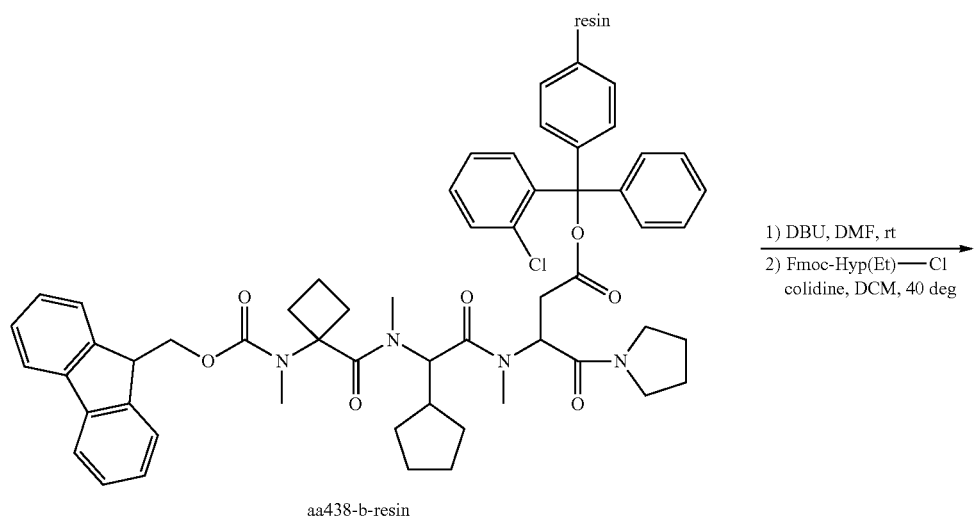
aa438-b-resin
1) DBU, DMF, rt
2) Fmoc-Hyp(Et)—Cl
   colidine, DCM, 40 deg -continued

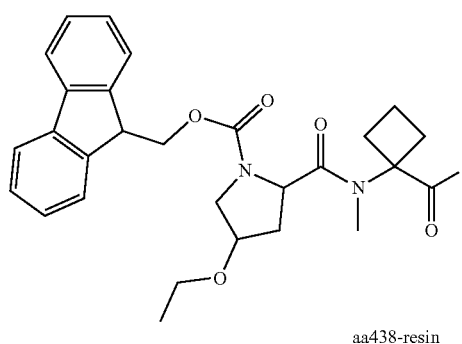
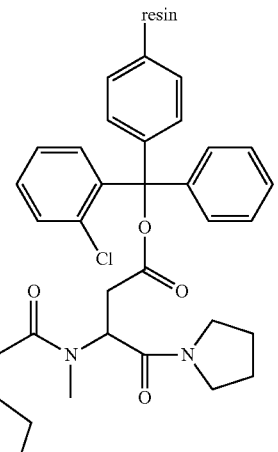

aa438-resin

Using aa362-resin as a starting material, aa437-a-resin was obtained in the same manner as Compound aa430-a-resin except that Fmoc-MeGly (cPent)-OH (Compound aa330) was used in place of Fmoc-MeNva (3-Et)-OH.

Using the resulting aa437-a-resin, aa437-b-resin was obtained in the same manner as Compound aa427-a-resin.

Using the resulting aa437-b-resin, aa437-resin was obtained in the same manner as Compound aa427-resin.

Amino acid was cleaved from the resin by TFE/DCM (1/1) using a small amount of resin-supported Compound aa437, and the structure was verified by LC/MS. LCMS (ESI) m/z=829 (M+H)+

Retention time: 0.93 min (Analytical condition SQDFA05)

Synthesis of Compound aa438-Resin

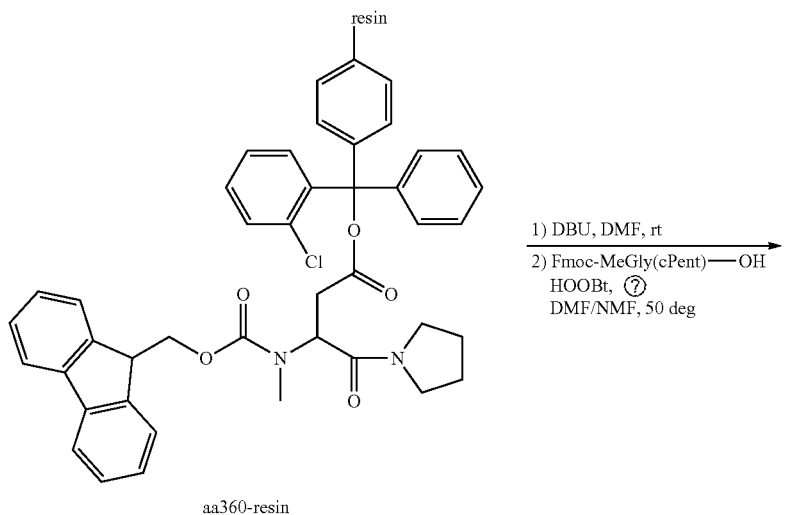

aa360-resin

1) DBU, DMF, rt
2) Fmoc-MeGly(cPent)—OH
   HOOBt, (?)
   DMF/NMF, 50 deg

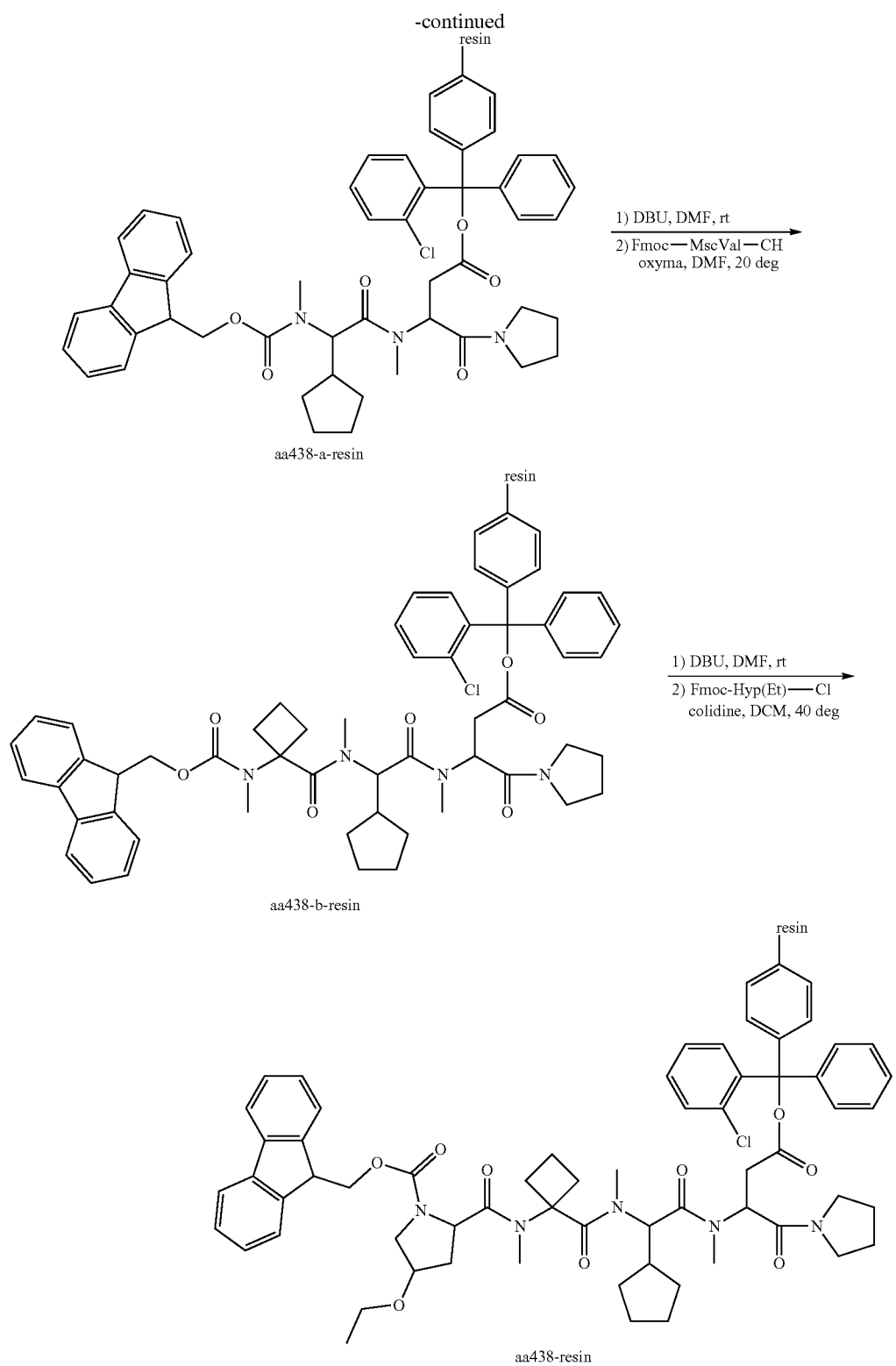

Using aa360-resin as a starting material, aa438-a-resin was obtained in the same manner as Compound aa430-a-resin except that Fmoc-MeGly (cPent)-OH (Compound aa330) was used in place of Fmoc-MeNva (3-Et)-OH.

Using the resulting aa438-a-resin, aa438-b-resin was obtained in the same manner as Compound aa427-a-resin.

Using the resulting aa438-b-resin, aa438-resin was obtained in the same manner as Compound aa427-resin. Amino acid was cleaved from the resin by TFE/DCM (1/1) using a small amount of resin-supported Compound aa438, and the structure was verified by LC/MS. LCMS (ESI) m/z=815 (M+H)+

Retention time: 0.87 min (Analytical condition SQDFA05)

Synthesis of Compound aa439-Resin

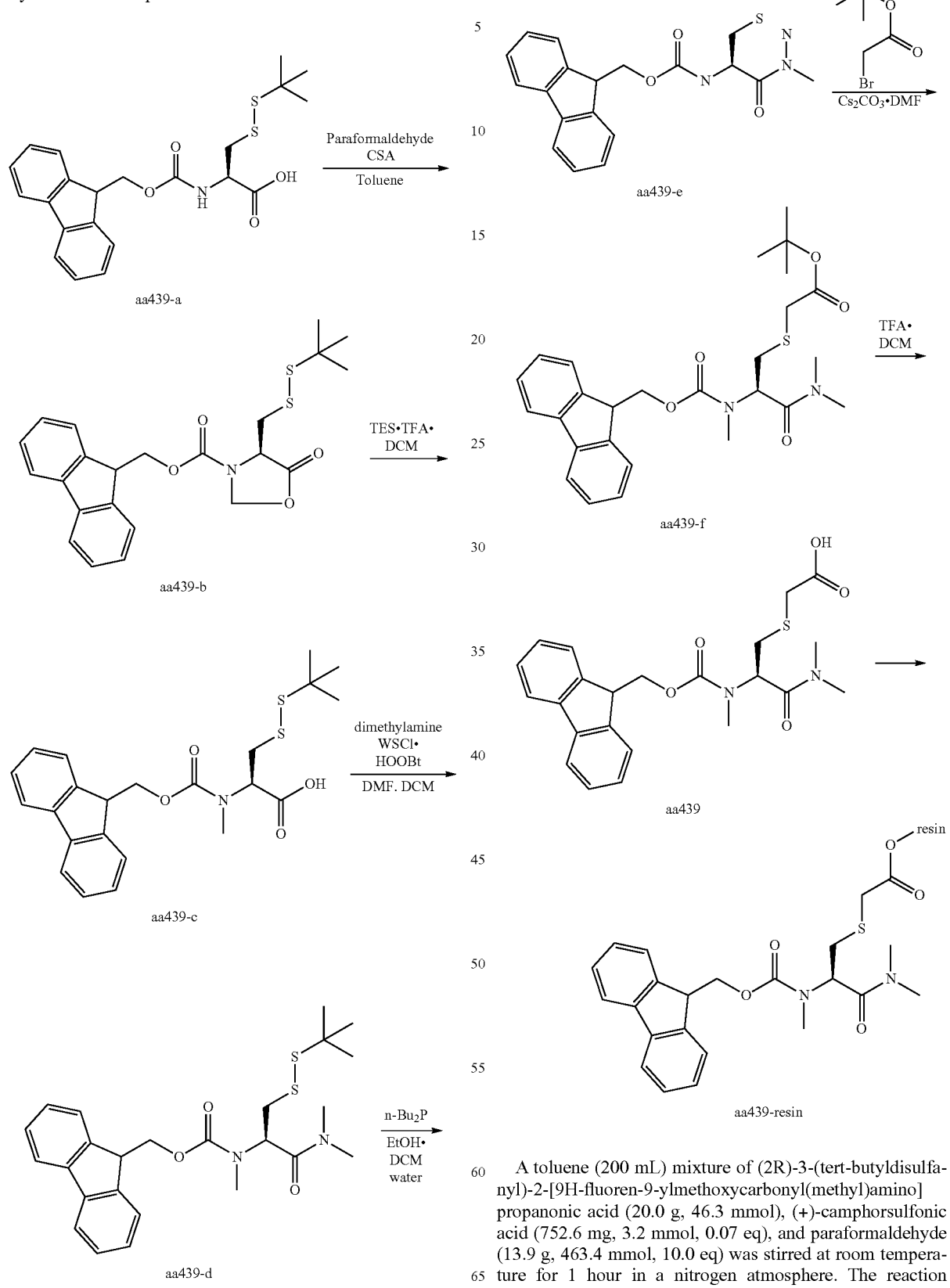

A toluene (200 mL) mixture of (2R)-3-(tert-butyldisulfanyl)-2-[9H-fluoren-9-ylmethoxycarbonyl(methyl)amino] propanonic acid (20.0 g, 46.3 mmol), (+)-camphorsulfonic acid (752.6 mg, 3.2 mmol, 0.07 eq), and paraformaldehyde (13.9 g, 463.4 mmol, 10.0 eq) was stirred at room temperature for 1 hour in a nitrogen atmosphere. The reaction solution was diluted with ethyl acetate, washed 3 times with an aqueous sodium hydrogen carbonate solution, and then washed with brine. The resulting organic layer was dried over anhydrous sodium sulfate, and the solvent was distilled off under reduced pressure to give Compound aa439-b (23 g) as a crude product.

LCMS (ESI) m/z=466.1 (M+Na)+

Retention time: 1.560 min (Analytical condition SMD method_20)

Trifluoroacetic acid (120 mL) was added to a mixed solution of Compound aa439-b (23 g) obtained above and triethylsilane (60.2 g, 518 mmol) in dichloromethane (120 mL) at room temperature in a nitrogen atmosphere, and the mixture was stirred for 40 hours. The solvent was distilled off from the reaction solution under reduced pressure, the resulting residue was purified by reverse phase column chromatography (C18, acetonitrile/water) to give Compound aa439-c (13 g, 63% in 2 steps).

LCMS (ESI) m/z=446.1 (M+H)+

Retention time: 0.852 min (Analytical condition SMD method_30))

Compound aa439-c (13.0) g, 29.2 mmol), WSCI·HCl (6.49 g, 33.84 mmol, 1.2 eq), and 3,4-dihydro-3-hydroxy-4-oxo-1,2,3-benzotriazine (HOOBt)(5.23 g, 32.09 mmol, 1.1 eq) were added to a mixed solution of DMF (26 mL) and DCM (90 mL) at room temperature in a nitrogen atmosphere, and the mixture was stirred for 5 minutes. The resulting reaction solution was cooled to 0° C.), dimethylamine (2 mol/L of THE solution, 15.60 mL, 31.2 mmol, 1.07 eq) was added dropwise, and the mixture was stirred at ( ) C for 1 hour. The reaction solution was diluted with ethyl acetate, washed twice with hydrochloric acid (1 mol/L, 130 mL), washed once with water (130 mL), washed twice with an aqueous sodium hydrogen carbonate solution (130 mL), and washed once with brine (130 mL). The resulting organic layer was dried over anhydrous sodium sulfate, and the solvent was distilled off under reduced pressure. The resulting residue was purified by normal phase chromatography (petroleum ether/ethyl acetate) to give Compound aa439-d (12.1 g, 88%).

LCMS (ESI) m/z=495.2 (M+Na)+

Retention time: 1.546 min (Analytical condition SMD method_20)

Tri-n-butylphosphine (6.0) g, 29.7 mmol, 1.2 eq) was added dropwise to a mixed solution of Compound aa439-d (11.7 g, 24.7 mmol), ethanol (100 mL), DCM (150 mL), and water (25 mL) at room temperature in a nitrogen atmosphere, and the mixture was stirred at room temperature for 3 hours. The reaction solution was extracted with dichloromethane (DCM), the resulting organic layer was washed with brine and dried over anhydrous sodium sulfate, and then the solvent was distilled off under reduced pressure. The resulting residue was purified by normal phase chromatography (petroleum ether/ethyl acetate), and the resulting mixture was purified by reverse phase column chromatography (C18, acetonitrile/water) to give Compound aa439-e (3.03 g, 32%).

LCMS (ESI) m/z=407.2 (M+Na)+

Retention time: 1.326 min (Analytical condition SMD method_20))

A mixed solution of Compound aa439-e (2.80 g, 7.29 mmol) and tert-butyl bromoacetate (2.10 g, 10.77 mmol, 1.5 eq) in DMF (40 mL) was stirred at room temperature for 5 minutes, cesium carbonate (2.80 g, 8.59 mmol, 1.2 eq) was added thereto, and the mixture was stirred for 1 hour. The reaction solution was diluted with ethyl acetate, and washed with water. The resulting organic layer was dried over anhydrous sodium sulfate, and the solvent was distilled off under reduced pressure to give Compound aa439-f (3.1 g) as a crude product. The resulting crude product was used in the next reaction without further purification.

LCMS (ESI) m/z=499.3 (M+H)+

Retention time: 1.467 min (Analytical condition SMD method_20)

Compound aa439-f (3.1 g) obtained above was dissolved in a mixed solution of trifluoroacetic acid (TFA)(30 mL) and dichloromethane (DCM)(30 mL), and stirred at room temperature for 2 hours in a nitrogen atmosphere. The solvent was distilled off from the reaction solution under reduced pressure, the resulting residue was purified by reverse phase column chromatography (C18, acetonitrile/water), and the resulting mixture was further purified by reverse phase high performance column chromatography (acetonitrile/water, containing TFA), and the resulting eluate was extracted with DCM. The resulting organic layer was washed successively with water and hydrochloric acid (1 mol/L), and the solvent was distilled off under reduced pressure to give Compound aa439 (1.79 g, 55% in 2 steps).

LCMS (ESI) m/z=443.2 (M+H)+

Retention time: 1.383 min (Analytical condition SMD method_31)

Using Compound aa439 (0.46 g, 1.04 mmol), Compound aa439-resin (1.54 g, supported amount 0.336 mmol/g) was obtained in the same manner as synthesis of Compound aa358-resin.

Synthesis of Compound aa440-Resin

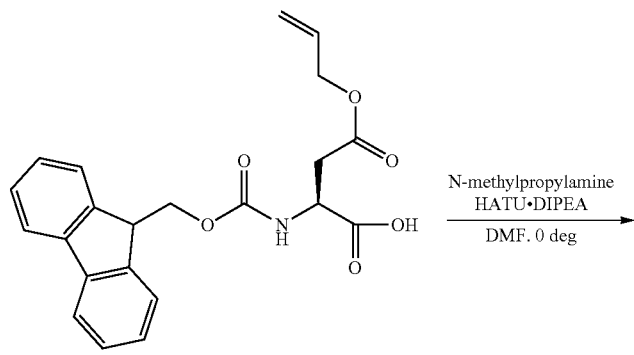

aa358-c

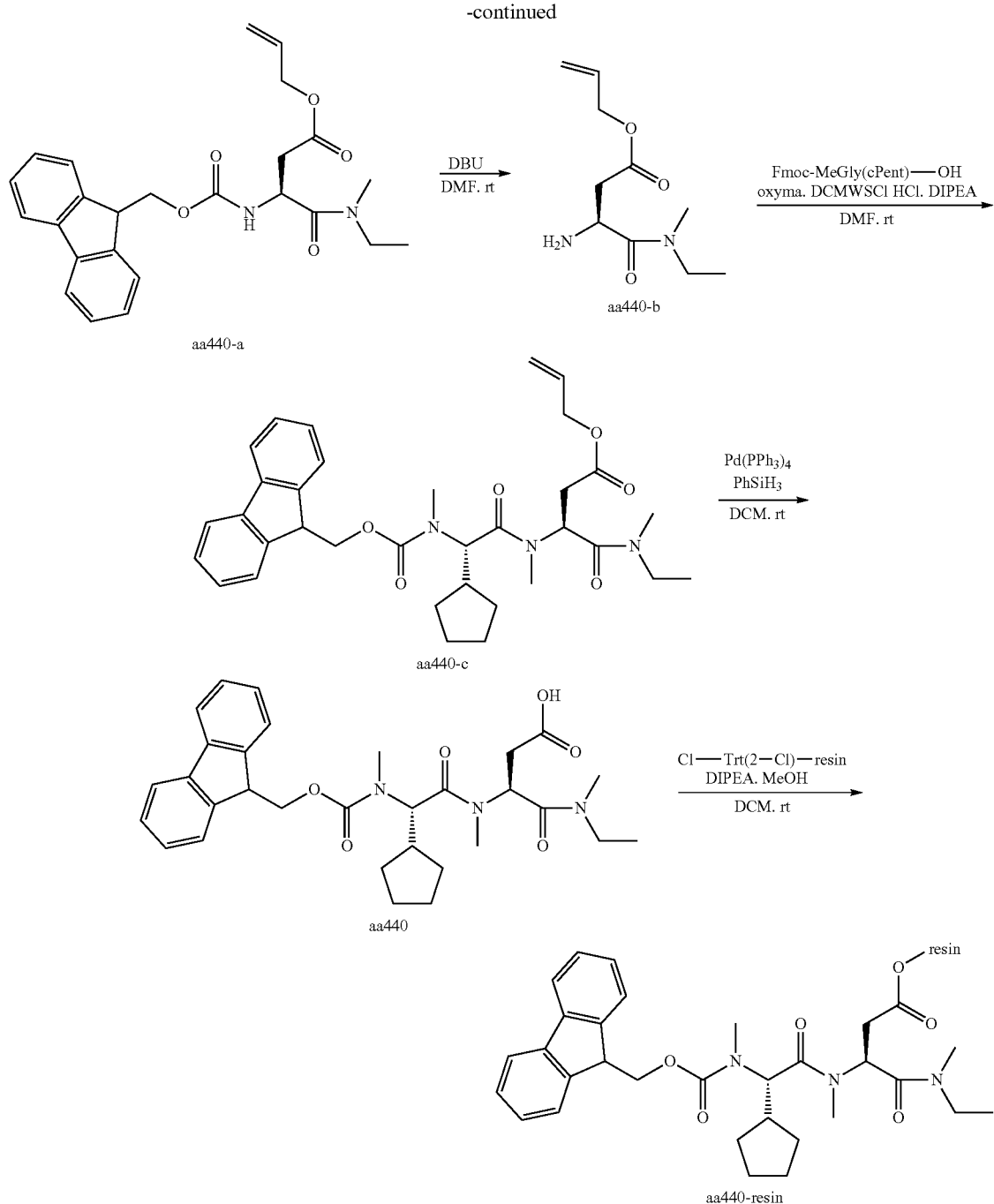

After DIPEA (26.3 mL, 148 mmol) was added to a DMF solution (211 mL) of aa358-c (30.3 g, 74.0 mmol) at 0° C., HATU (30.9 g, 81.0 mmol) and N-methylethaneamine (6.97 mL, 81.0 mmol) were added. After being stirred at 0° C. for 30 minutes, the mixture was diluted with toluene (300 mL), and 1 N hydrochloric acid (600 mL) was added. The organic layer was separated, washed with water (300 mL), washed with a 50% aqueous sodium hydrogen carbonate solution (300 mL), and washed with half brine (300 mL). The organic layer was dried over anhydrous sodium sulfate and filtered off, and the solvent was distilled off under reduced pressure to give Compound aa440-a as a crude product (36.6 g). The crude product was dissolved in toluene (211 mL), and DBU (11.0 mL, 74 mmol) was added at 0° C. After stirring at room temperature for 5 minutes, 1 N hydrochloric acid (333 mL) was added to separate the aqueous layer. After the aqueous layer was washed with toluene (333 mL), a 50% aqueous sodium hydroxide solution (7.5 mL) was added to adjust the pH to 8 to 9. The mixture was extracted 5 times with ethyl acetate (200 mL), and the organic layer was washed with half brine (333 mL). The organic layer was dried over anhydrous sodium sulfate and filtered off, and the solvent was distilled off under reduced pressure to give aa440-b as a crude product (12.6 g).

Oxyma (9.41 g, 66.2 mmol) was added to a DMF solution (158 mL) of Fmoc-MeGly (cPent)-OH (Compound aa330, 21 g, 55.2 mmol) at 0° C. WSCI·HCl (14.8 g, 77 mmol) was added thereto, and the mixture was stirred at room temperature for 30 minutes. A DMF solution (31 mL) of aa440-b (12.6 g, 55.2 mmol) and DIPEA (10.8 mL, 60.7 mmol) were added thereto, and the mixture was stirred at room temperature for 15 hours. Toluene (250 mL) and 0.5 N hydrochloric acid (250 mL) were added, and the organic layer was washed with a 50% aqueous sodium hydrogen carbonate solution (250 mL) and washed with half brine (250 mL). The organic layer was dried over anhydrous sodium sulfate and filtered off, the solvent was distilled off under reduced pressure, and the resulting residue was purified by silica gel chromatography (hexane-ethyl acetate) to give aa440-c (25.6 g, 59% in 3 steps).

LCMS (ESI) m/z=612 (M+Na)+

Retention time: 3.27 min (Analytical condition SMD method_03)

Phenylsilane (3.69 mL, 30.0 mmol) was added to a DCM solution (86 mL) of aa440-c (25.3 g, 42.9 mmol). Tetrakis(triphenylphosphine) palladium (0)(496 mg, 0.429 mmol) was added thereto, and the mixture was stirred at room temperature for 30 minutes. The mixture was diluted with TBME (250 mL), and extracted with a 50% aqueous sodium hydrogen carbonate solution (250 mL). The organic layer was further extracted with a 50% aqueous sodium hydrogen carbonate solution (125 mL), and phosphoric acid (17.9 mL, 323 mmol) was added to the combined aqueous layer to adjust the pH to 2 to 3. The mixture was extracted with DCM (250 mL), the organic layer was washed with half brine (250 mL), and the solvent was distilled off under reduced pressure to give aa440 as a crude product (23.6 g).

LCMS (ESI) m/z=572 (M+Na)+

Retention time: 2.64 min (Analytical condition SMD method_03)

Using the resulting aa440 (23.5 g, 42.8 mmol), aa440-resin (79.2 g) was obtained under the same reaction conditions as synthesis of Compound aa373-resin. The supported amount calculated in the same manner as aa373-resin was 0.333 mmol/g.

Synthesis of Compound aa441-Resin

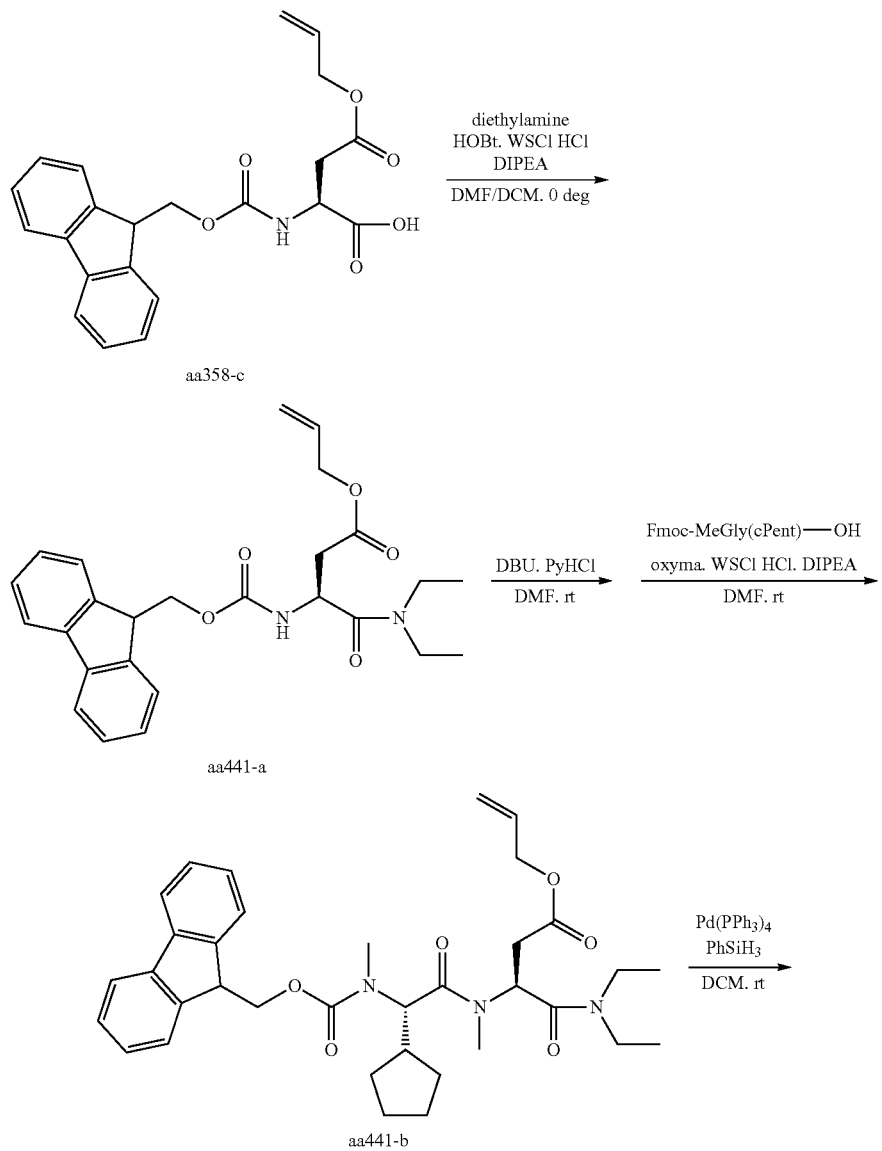

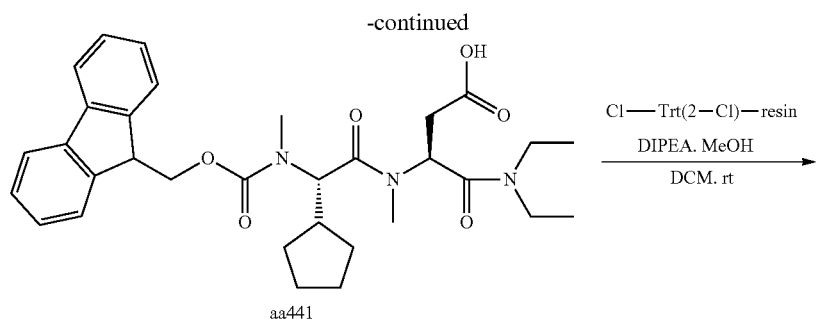

HOBt (7.30 g, 54.0 mmol) was added to a DMF solution (89 mL) of WSCI·HCl (11.3 g, 58.9 mmol) at 0° C. in a nitrogen atmosphere, and the mixture was stirred for 5 minutes. A DMF/DCM solution (1/1, 74 mL) of aa358-c (20.1 g, 49.1 mmol) was added thereto, and the mixture was stirred at 0° C. for 30 minutes. After diethylamine (5.60 mL, 54.0 mmol) was added thereto, the mixture was stirred at room temperature for 2 hours. The mixture was diluted with ethyl acetate (200 mL), washed with 1 N hydrochloric acid (160 mL), and washed with water (200 mL). The mixture was further washed twice with a 50% aqueous sodium hydrogen carbonate solution (200 mL) and washed with half brine (200 mL). The organic layer was dried over anhydrous sodium sulfate and filtered off, and the solvent was distilled off under reduced pressure to give aa441-a as a crude product (23.3 g).

DBU (6.61 mL, 44.2 mmol) was added dropwise to a DMF solution (147 mL) of aa441-a (20.5 g, 44.2 mmol) in a nitrogen atmosphere, and the mixture was stirred at room temperature for 5 minutes. Pyridine hydrochloride (5.62 g, 48.6 mmol) was added thereto, and the mixture was stirred at room temperature for 10 minutes. To this mixture was added a solution that is obtained by adding WSCI·HCl (11.9 g, 61.9 mmol) to a DMF solution (147 mL) of Fmoc-MeGly (cPent)-OH (Compound aa330, 15.9 g, 42.0 mmol) and oxyma (7.54 g, 53.0 mmol). The resulting mixture was stirred at room temperature for 30 minutes. Moreover, DIPEA (8.47 mL, 48.6 mL) was added, and then the mixture was stirred at room temperature for 17 hours. The mixture was diluted with ethyl acetate (200 mL), and washed twice with 1 N hydrochloric acid (200 mL). The aqueous layer was extracted with ethyl acetate (200 mL), and the combined organic layer was washed with water (200 ml), washed twice with a 50% aqueous sodium hydrogen carbonate solution (200 mL), and washed with half brine (200 mL). The organic layer was dried over magnesium sulfate and filtered off, the solvent was distilled off under reduced pressure, and the resulting residue was purified twice by silica gel chromatography (hexane-ethyl acetate) to give aa441-b (13.7 g, 52%).

LCMS (ESI) m/z=626 (M+Na)+

Retention time: 1.50 min (Analytical condition SMD method_04)

aa441 was obtained as a crude product (10.5 g) in the same manner as Compound aa440 except that aa441-b (13.7 g, 22.7 mmol) was used in place of aa440-c.

LCMS (ESI) m/z=586 (M+Na)+

Retention time: 1.17 min (Analytical condition SMD method_05)

Using the resulting Compound aa441 (10.5 g, 18.6 mmol), aa441-resin (36.3 g) was obtained under the same reaction conditions as synthesis of Compound aa373-resin. The supported amount calculated in the same manner as aa373-resin was 0.362 mmol/g.

Synthesis of Compound aa442-Resin
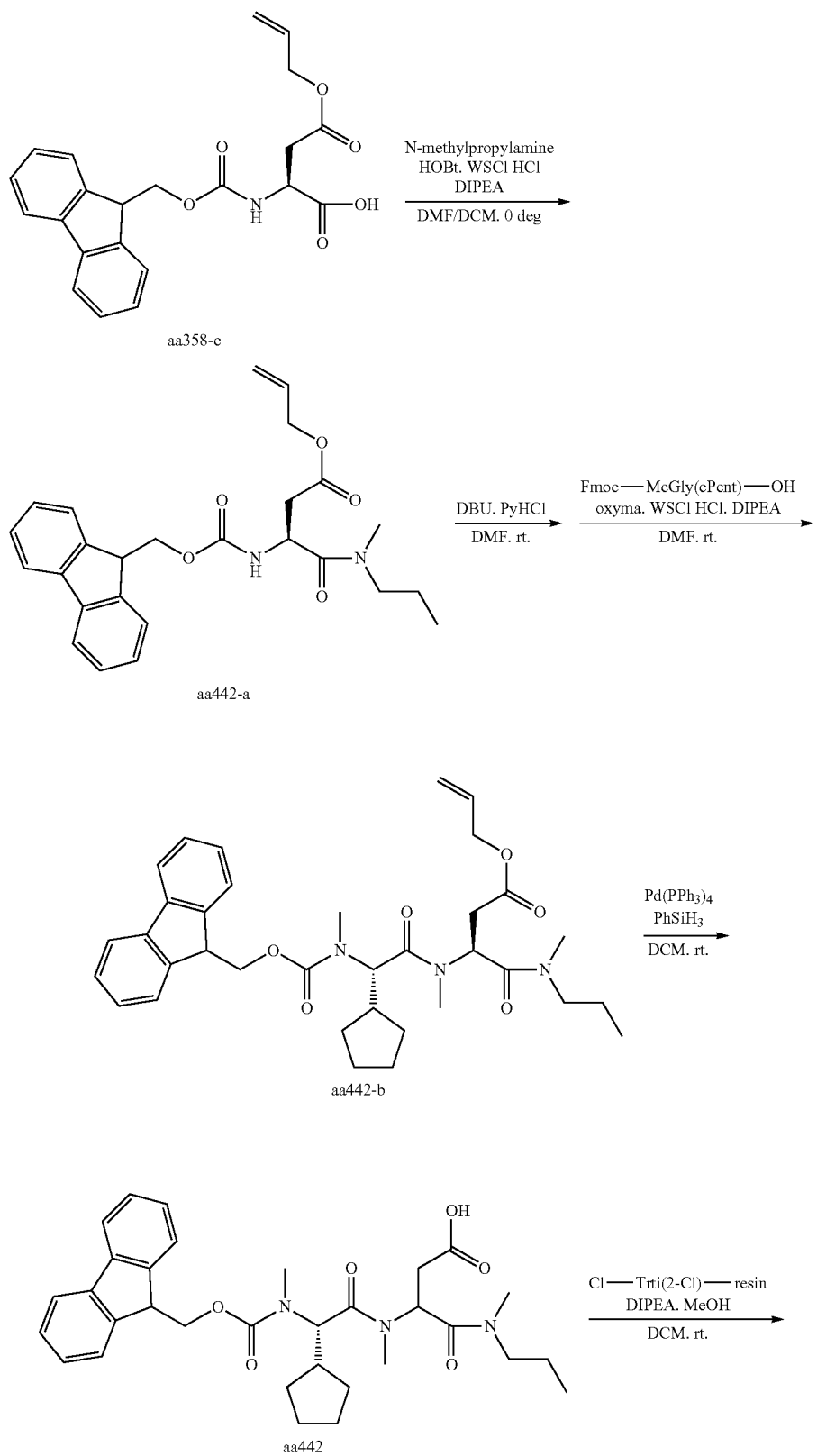

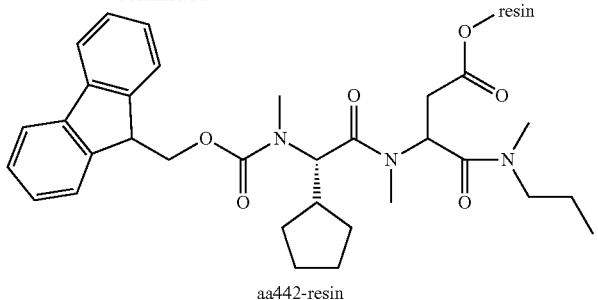

aa442-resin aa442-a was obtained as a crude product (23.6 g) in the same manner as Compound aa441-a except that N-methylpropylamine was used in place of diethylamine.

aa442-b (15.9 g, 53%) was obtained in the same manner as Compound aa441-b except that aa442-a (22.9 g, 49.4 mmol) was used in place of aa441-a.

LCMS (ESI) m/z=626 (M+Na)+

Retention time: 1.51 min (Analytical condition SMD method_04)

aa442 (13.7 g, 92%) was obtained in the same manner as Compound aa441 except that 442-b (15.9 g, 26.4 mmol) was used in place of aa441-b.

LCMS (ESI) m/z=564 (M+H)+

Retention time: 1.28 min (Analytical condition SMD method_04)

Using the resulting aa442 (13.6 g, 24.2 mmol), aa442-resin (47.1 g) was obtained under the same reaction conditions as synthesis of Compound aa373-resin. The supported amount calculated in the same manner as aa373-resin was 0.348 mmol/g.

1-3. Solid-Phase Peptide Synthesis by Peptide Synthesizer

Cyclic peptide compounds (Table 38) were synthesized by the method described in WO2013/100132 or WO2018/225864. Peptides were synthesized by the Fmoc method, which is described in more detail below, using a peptide synthesizer (Multipep RS and RSi; manufactured by Intavis). The detailed operational procedure was according to the manual appended to the synthesizer. The relationship between the formal name, structure, and abbreviation of each amino acid residues and oligo peptides constituting the cyclic peptides provided in Table 38 can be understood from Tables 2 to 6 above, and Table 9, Table 10, Table 9-1, Table 17-1, and Table 29-1 below.

A peptide synthesis method (a basic peptide synthesis method) by the Fmoc method is described in detail in 1-3-1 to 1-3-5 below.

1-3-1. Peptide Elongation Reaction by Fmoc Method from N-Terminal of Amino Acid

A peptide compound was synthesized by a solid-phase synthesis method involving an Fmoc-protected amino acid using a peptide synthesizer (Multipep RS or Multipep RSi) manufactured by Intavis. The detailed operational procedure was according to the manual appended to the synthesizer.

The Fmoc-protected amino acid (0).3 to 0.6 mol/L.) constituting the intended peptide, and HOAt, oxyma, or HOOBt (0.375 mol/L.) as a carboxyl group activator, were dissolved in NMP or NMP/DMF (1/1) to prepare Solution 1. When the Fmoc-protected amino acid was poorly soluble in the above solvents, DMSO was added so as to have a concentration of 20 to 30% (v/v) to prepare Solution 1. When, for example, Fmoc-Ser (THP)—OH or Fmoc-MeSer (THP)—OH was used as an Fmoc-protected amino acid having a THP-protecting group in a side chain, Solution 1 was prepared using oxyma as a carboxyl group activator, and Molecular Sieves 4A1/8 (Wako Pure Chemical Industries, Ltd.) or Molecular Sieves 4A1/16 (Wako Pure Chemical Industries, Ltd.) was added and then used in peptide synthesis. When the α,α-di-substituted Fmoc amino acid used was, for example, Fmoc-cVal-OH (Compound aa301), Fmoc-cLeu-OH (Compound aa302), Fmoc-cHex-OH (Compound aa306), Fmoc-cVal (3-Me2)-OH (Compound aa303), Fmoc-cVal (3-F2)—OH)(Compound aa307), Fmoc-AoxeC-OH (Compound aa318), Fmoc-Aib-OH (Compound aa315), or Fmoc-(Me) Abu-OH (Compound aa316), oxyma was used as a carboxyl group activator to prepare Solution 1. When the serin derivative used was, for example, Fmoc-MeSer (nPr)—OH (Compound aa016), Fmoc-MeSer (cPr)—OH (Compound aa020), Fmoc-MeSer (Tfe)-OH (Compound aa0)21), Fmoc-MeSer (Et)-OH (Compound aa0)22), Fmoc-MeSer (iPen)-OH (Compound aa249), Fmoc-D-MeSer (nPr)—OH (Compound aa250), or Fmoc-MeSer (Me)-OH (Compound aa252), HOAt or HOOBt was used as a carboxyl group activator to prepare Solution 1. When the azetidine or a derivative thereof used was, for example, Fmoc-Aze (2)—OH (Compound 076), Fmoc-D-Aze (2)—OH (Compound aa0) 79), Fmoc-Aze (2)(3S-Me)-OH (Compound aa098), Fmoc-Aze (2)(3R-Me)-OH (Compound aa0) 99), or Fmoc-Aze (2)(3-Me2)-OH (Compound aa100), HOOBt was used as a carboxyl group activator to prepare Solution 1. N,N'-diisopropylcarbodiimide (DIC) (10% v/v) and N,N-dimethylformamide (DMF) were mixed to prepare Solution 2.

2-Chlorotrityl resin (100) mg), which is bound to the side-chain carboxylic acid moiety of N-terminal Fmoc-protected aspartic acid or the main-chain carboxylic acid moiety of an N-terminal Fmoc-protected amino acid, was added to a solid-phase reaction vessel, and the reaction vessel was placed in a peptide synthesizer. Dichloromethane (DCM)(0.8 mL) was added to this resin (100 mg), and the mixture was left to stand still for 1 hour to swell the resin. The solution was then discharged from the frit. Solution 1 and Solution 2 were placed in the peptide synthesizer, and automatic synthesis by the peptide synthesizer was started.

A DMF solution (2% v/v, 0.7 ml.) of 1,8-diazabicyclo [5.4.0]-7-undecene (DBU) was added to a solid-phase reaction vessel containing the resin to deprotect the N-terminal Fmoc group at room temperature. Reaction was carried out for 4.5 minutes in the deprotection of the first residue, and for 10 minutes in the deprotection of the second and subsequent residues, and then the solution was discharged from the frit. DMF (0.7 ml.) was added thereto, and after being left to stand still for 5 minutes, the solution was discharged from the frit. By repeating this resin washing step 3 more times, an amino acid bonded to the resin, or the resin in which the Fmoc group at the N-terminal of the peptide was removed to yield an amino group, was obtained. The washing step may be carried out in such a manner that the resin is washed once with DMF (0.7 ml.), then washed once with a toluene solution (0.7 mL.) of DIPEA. HOAt (2 eq based on resin), and further washed 3 times with DMF (0).7 ml.).

Subsequently, Solution 1 (0.3 ml.) and Solution 2 (0.36 ml.) were mixed in the mixing vial of the synthesizer and then added to the resin that had undergone the above deprotection treatment, and the solid-phase reaction vessel was heated to 40° C. In the case of a poorly elongatable sequence, the temperature was increased to 60° C. as necessary. The condensation reaction of the amino group on the resin and the Fmoc-protected amino acid was carried out for 2.5 hours. In the case of a poorly elongatable sequence, the reaction was carried out for 20 hours as necessary. In the case of α,α-di-substituted Fmoc amino acid, the temperature was increased to 60° C. and the reaction was carried out for 16 hours, as necessary. In the case of Fmoc-protected amino acid of azetidine or a derivative thereof, the temperature was increased to 50° C. and the reaction was carried out for 10 hours, as necessary, then Solution 2 (0.36 ml.) was added again, and the reaction was further carried out at 50° C. for 10 hours. After reaction, the solution was discharged from the frit. When the elongation efficiency was poor, this condensation reaction of the Fmoc-protected amino acid was repeated one or two more times. For example, this corresponds to the condensation reaction of an N-alkylated Fmoc-protected amino acid on Compound aa358-resin (Fmoc-MeAsp (O-Trt (2-C1) resin)-mor) and Compound aa359-resin (Fmoc-MeAsp (O-Trt (2-C1) resin)-NMe2). In the case of Fmoc-protected amino acids of Mec Val and MecLeu, the mixture was heated to 60° C. and reacted for 6 hours if necessary, then Solution 2 (0.36 ml.) was added again, and the reaction was further carried out at 60° C. for 6 hours. This operation was repeated, so the reaction was carried out for a total of 24 hours. When elongating Fmoc protected proline or its derivative following MecVal and MecLeu, the operation of heating the mixture to 60° C. to be reacted for 6 hours, then adding again Solution 2 (0.36 ml.), further reacting the mixture at 60° C. for 6 hours, and discharging the solution from the frit was carried out 3 times. Then, the resin was washed 3 times with DMF (0.7 ml.). This Fmoc group deprotection reaction and the subsequent Fmoc amino acid condensation reaction were regarded as constituting one cycle, and a peptide was elongated on the resin surface by repeating this cycle. After completion of peptide elongation, a DMF solution (2% v/v, 0).7 mL) of DBU was added to the resin, and a reaction was carried out for 15 minutes to perform a deprotection reaction of the Fmoc group, and then the solution was discharged from the frit. The resulting resin was washed 4 times with DMF (0.7 mL.), and then washed 4 times with DCM (0.7 mL.).

1-3-2. Cleaving of Elongated Peptide from Resin

To the resin obtained by the method described in WO2013/100132 or WO2018/225864 or by the above method was added 2,2,2-trifluoroethanol (TFE)/DCM (1/1, v/v, 2 mL.) containing 0).75% (v/v) DIPEA, and the resin was reacted for 2 hours at room temperature to carry out the reaction of cleaving a peptide chain from the resin. After reaction, the solution in the tube was recovered from the frit. 2,2,2-Trifluoroethanol (TFE)/DCM (1/1, v/v, 1 mL) was added to the remaining resin, and the operation of recovering the solution from the frit was performed twice. The entirety of the resulting cleaved solutions was combined and mixed with DMF (4 mL) or 1,2-dichloroethane (4 mL.), and then the solvent was distilled off under reduced pressure using a high-throughput centrifugal evaporator (HT-12) manufactured by Genevac.

1-3-3. Method of Cyclizing Cleaved Peptide

The residue obtained by the above method was dissolved in a mixed solution of DMF (4 mL) and DCM (4 mL), a DMF solution (0.5 M, 1.5 eq) of (1-cyano-2-ethoxy-2-oxoethylideneaminooxy)dimethylamino-morpholino-carbenium hexafluorophosphate (COMU) or a DMF solution (0.5 M, 1.5 eq) of O-(7-aza-1 H-benzotriazol-1-yl)-N,N,N,N-tetramethyluronium hexafluorophosphate (HATU) and DIPEA (1.8 eq) were added, and the mixture was stirred at room temperature for 2 hours to carry out a condensation cyclization reaction of the N-terminal amino group and the C-terminal carboxyl group. The equivalent number was calculated based on the product of multiplying the amino acid supporting ratio (mmol/g) of the resin used as a raw material by the amount of the resin used (usually 100 mg). Production of the intended cyclic peptide was verified by LC/MS measurement (SQ Detector 2 manufactured by Waters), and then the solvent was distilled off from the reaction solution under reduced pressure by a high-throughput centrifugal evaporator (HT-12) manufactured by Genevac.

1-3-4. Deprotection of Protecting Group of Side-Chain Functional Group Contained in Cyclic Peptide In the sequences synthesized using Fmoc-protected amino acids having a THP-protected hydroxyl group in a side chain, such as Fmoc-Ser (THP)—OH (Compound aa0) 73), Fmoc-MeSer (THP)—OH (Compound aa044), Fmoc-Hyp (THP)—OH (Compound aa279), Fmoc-Hyp (3)(THP)—OH (Compound aa265), Fmoc-cisHyp (THP)—OH (Compound 267), and Fmoc-cisHyp (3)(THP)—OH (Compound aa264), and in the sequences synthesized using Fmoc-MeAsp (O-Trt (2-C1) resin)-OPis (Compound aa386-resin), 4 ml. of a 1,1,1,3,3,3-hexafluoroisopropyl alcohol (HFIP) solution (containing 2% (v/v) triisopropylsilane (TIPS) and 1% (v/v) 1,2-dichloroethane) of tetramethylammonium hydrogen sulfate (0.05 M) was added to the residue obtained above to dissolve the residue, and then the mixture was left to stand at room temperature for 4 hours to deprotect the THP protecting group or Pis protecting group. After completion of the reaction was confirmed with LC/MS (SQ Detector 2 manufactured by Waters), diisopropylethylamine (DIPEA)(70 μL) was added to the reaction solution, and the solvent was distilled off under reduced pressure with a high-throughput centrifugal evaporator (HT-12) manufactured by Genevac. In this deprotection reaction, another fluoroalcohol such as 2,2,2-trifluoroethanol (THE) can be used in place of HFIP.

1-3-5. Cyclic Peptide Purification Method

DMSO or DMF and acetonitrile were added to the residue obtained by the above method, insoluble matter was removed by filter filtration, and then the solution was purified by preparative-HPLC. The purification apparatus used was Waters Auto Purification System, the column used was YMC-Actus Triart C18 (inner diameter 20 mm, length 100 mm) or YMC-Actus Triart Phenyl(inner diameter 20 mm, length 100 mm), and the mobile phase used was an aqueous methanol-ammonium acetate solution (50 mmol/L.) or acetonitrile-water containing 0).1% formic acid. Fractions containing a compound as the main component were selected, the same amount of DMSO as the amount of the solution of each fraction was added, and the solvent was distilled off under reduced pressure with a high-throughput centrifugal evaporator (HT-12) manufactured by Genevac. The resulting residue was dissolved in DMSO, fractions were integrated as necessary, and again the solvent was distilled off under reduced pressure with a high-throughput centrifugal evaporator (HT-12) manufactured by Genevac to give the intended cyclic peptide.

Synthesis of Compound PP0247

Compound aa375-resin (0.448 mmol/g, 100 mg) was used as a raw material, and Fmoc-cLeu-OH, Fmoc-Pro-OH, Fmoc-Hph(4—CF3-3-Cl)—OH, Fmoc-MeGly-OH, Fmoc-nPrPhe (4—CF3)—OH, Fmoc-Ile-OH, and Fmoc-Azp(2)—OH were used as Fmoc-protected amino acids. The above-described peptide elongation reaction by the Fmoc method, cleaving of an elongated peptide from resin, cyclization of a cleaved peptide (using (1-cyano-2-ethoxy-2-oxoethylidencaminooxy)dimethylamino-morpholino-carbenium hexafluorophosphate (COMU) as a cyclization reagent), and purification of a cyclic peptide were performed to give the intended compound PP0247 (12.7 mg, 19%).

Compound PP0247

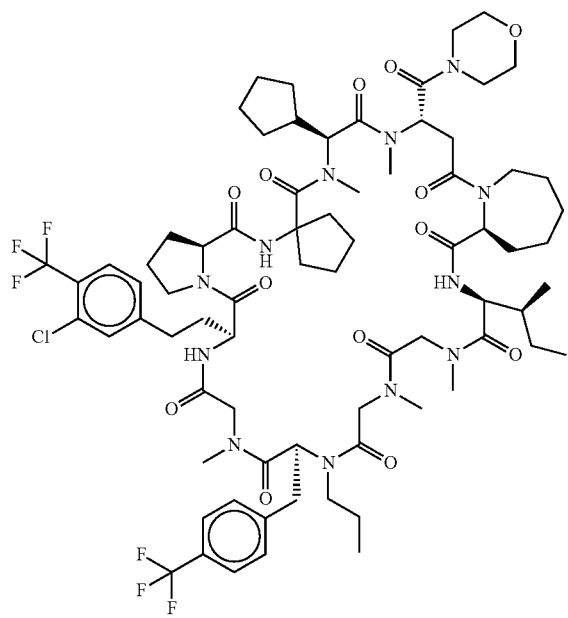

LCMS (ESI) m/z=1517.6 (M+H)+

Retention time: 7.775 min (Analytical condition SSC-AA-02/03)

Using the resins, on which amino acid shown in Table 5 and Table 6 was supported, as raw materials, the following compounds were produced according to the above-described Fmoc method in the same manner as the production method of Compound PP247. A deprotection reaction was added as necessary.

Compounds PP0001, PP0002, PP0003, PP0004, PP0006, PP0007, PP0011, PP0013, PP0014, PP0015, PP0016, PP0018, PP0019, PP0020, PP0021, PP0022, PP0023, PP0024, PP0025, PP0027, PP0028, PP0029, PP0030, PP0031, PP0032, PP0037, PP0039, PP0041, PP0042, PP0043, PP0044, PP0045, PP0047, PP0048, PP0049, PP0050, PP0051, PP0067, PP0068, PP0070, PP0071, PP0076, PP0077, PP0078, PP0138, PP0141, PP0144, PP0145, PP0146, PP0148, PP0149, PP0150, PP0151, PP0152, PP0153, PP0154, PP0155, PP0156, PP0158, PP0162, PP0165, PP0166, PP0168, PP0169, PP0170, PP0171, PP0172, PP0173, PP0174, PP0175, PP0176, PP0177, PP0178, PP0179, PP0180, PP0181, PP0182, PP0183, PP0184, PP0185, PP0186, PP0187, PP0188, PP0189, PP0190, PP0191, PP0192, PP0193, PP0194, PP0195, PP0196, PP0197, PP0198, PP0199, PP0200, PP0201, PP0202, PP0203, PP0204, PP0205, PP0206, PP0207, PP0208, PP0209, PP0212, PP0217, PP0220, PP0221, PP0222, PP0223, PP0224, PP0225, PP0226, PP0227, PP0228, PP0229, PP0230, PP0231, PP0232, PP0233, PP0234, PP0235, PP0236, PP0237, PP0238, PP0239, PP0240, PP0241, PP0247, PP0248, PP0249, PP0250, PP0251, PP0252, PP0253, PP0254, PP0256, PP0257, PP0258, PP0259, PP0260, PP0261, PP0262, PP0263, PP0264, PP0265, PP0266, PP0267, PP0268, PP0269, PP0270, PP0271, PP0272, PP0273, PP0274, PP0275, PP0276, PP0277, PP0278, PP0279, PP0281, PP0282, PP0283, PP0284, PP0285, PP0286, PP0287, PP0288, PP0289, PP0290, PP0291, PP0292, PP0293, PP29%, PP0295, PP0296, PP0297, PP0298, PP0299, PP0300, PP0301, PP0302, PP0303, PP0304, PP0305, PP0306, PP0307, PP0308, PP0309, PP0310, PP0311, PP0312, PP0313, PP0314, PP0315, PP0320, PP0321, PP0322, PP0323, PP0324, PP0325, PP0326, PP0327, PP0328, PP0329, PP0330, PP0331, PP0332, PP0333, PP0334, PP0335, PP0336, PP0337, PP0338, PP0339, PP0340, PP0341, PP0342, PP0343, PP0344, PP0345, PP0346, PP0347, PP0348, PP0349, PP0350, PP0351, PP0352, PP0353, PP0354, PP0355, PP0356, PP0357, PP0358, PP0359, PP0360, PP0361, PP0362, PP0363, PP0364, PP0365, PP0366, PP0367, PP0368, PP0369, PP0370, PP0371, PP0372, PP0373, PP0374, PP0375, PP0376, PP0377, PP0378, PP0379, PP0380, PP0381, PP0382, PP0383, PP0384, PP0385, PP0386, PP0387, PP0388, PP0389, PP0390, PP0392, PP0393, PP0394, PP0395, PP03%, PP0397, PP0398, PP0399, PP0400, PP0401, PP0402, PP0403, PP0404, PP0405, PP0406, PP0407, PP0408, PP0409, PP0410, PP0411, PP0412, PP0413, PP0414, PP0415, PP0416, PP0417, PP0418, PP0419, PP0420, PP0421, PP0422, PP0423, PP0424, PP0425, PP0426, PP0427, PP0428, PP0429, PP0430, PP0431, PP0432, PP0433, PP0434, PP0435, PP0436, PP0437, PP0438, PP0439, PP0440, PP0441, PP0442, PP0443, PP0444, PP0445, PP0446, PP0447, PP0448, PP0449, PP0450, PP0451, PP0452, PP0453, PP0454, PP0455, PP0456, PP0457, PP0745, PP0746, PP0747, PP0748, PP0749, PP0750, PP0751, PP0752, PP0753, PP0766, PP0767, PP0768, PP0769, PP0770, PP0783, PP0784, PP0785, PP0786, PP0787, PP0788, PP0789, PP0802, PP0803, PP0804, PP1815, PP1816, PP1817, PP1818, PP1819, PP1820, PP1914, PP1916, PP1918, PP1920, PP1922, PP1926, PP1928, PP1930, PP1946, PP1947, PP1948, PP1949, PP1950, PP1952, PP1953, PP1954, PP1955, PP1956, PP1957, PP1958, PP1959, PP1960, PP1961, PP1963, PP1964, PP1965, PP1967, PP1968, PP1969, PP1970, and PP1971.

1-4. Cyclic Peptide Synthesis Using Fmoc-Protected Tripeptide as Reagent Synthesis of Fmoc-Protected Tripeptides The tripeptides shown in Table 9 were synthesized by the following method and used in peptide synthesis by a peptide synthesizer.

TABLE 9

| Compound No. | Structural Formula | Name |
|---|---|---|
| tp001 | | N-((S)-2-((S)-3-((((9H-fluoren-9-yl)methoxy)carbonyl)(methyl)amino)-2-oxoazepan-1-yl)-3-(4-(trifluoromethyl)phenyl)propanoyl)-N-methylglycine |
| tp002 | | N-((S)-2-((S)-3-((((9H-fluoren-9-yl)methoxy)carbonyl)(methyl)amino)-2-oxoazocan-1-yl)-3-(4-(trifluoromethyl)phenyl)propanoyl)-N-methylglycine |
| tp003 | | N-((S)-2-((S)-3-((((9H-fluoren-9-yl)methoxy)carbonyl)(methyl)amino)-2-oxoazocan-1-yl)-3-(4-fluorophenyl)propanoyl)-N-methylglycine |
| tp004 | | N-((S)-2-((S)-3-((((9H-fluoren-9-yl)methoxy)carbonyl)(methyl)amino)-2-oxoazocan-1-yl)-4-(allyloxy)-4-oxobutanoyl)-N-methylglycine |

TABLE 9-continued

| Compound No. | Structural Formula | Name |
|---|---|---|
| tp005 | | N-((S)-2-((S)-3-((((9H-fluoren-9-yl)methoxy)carbonyl)(methyl)amino)-2-oxo-2,3,4,7-tetrahydro-1H-azepin-1-yl)-3-(4-(trifluoromethyl)phenyl)propanoyl)-N-methylglycine |
| tp006 | | N-((S)-2-((S,Z)-3-((((9H-fluoren-9-yl)methoxy)carbonyl)(methyl)amino)-2-oxo-3,4,7,8-tetrahydroazocin-1(2H)-yl)-3-(4-(trifluoromethyl)phenyl)propanoyl)-N-methylglycine |
| tp007 | | N-((S)-2-((S,Z)-3-((((9H-fluoren-9-yl)methoxy)carbonyl)(methyl)amino)-2-oxo-3,4,7,8-tetrahydroazocin-1(2H)-yl)-3-(p-tolyl)propanoyl)-N-methylglycine |
| tp008 | | N-((S)-2-((S,Z)-3-((((9H-fluoren-9-yl)methoxy)carbonyl)(methyl)amino)-2-oxo-3,4,7,8-tetrahydroazocin-1(2H)-yl)-3-(4-fluorophenyl)propanoyl)-N-methylglycine |
| tp009 | | N-((S)-2-((S,Z)-3-((((9H-fluoren-9-yl)methoxy)carbonyl)(methyl)amino)-2-oxo-3,4,7,8-tetrahydroazocin-1(2H)-yl)-3-(4fluoro-2-methylphenyl)propanoyl)-N-methylglycine |

TABLE 9-continued

| Compound No. | Structural Formula | Name |
|---|---|---|
| tp010 | | N-((S)-2-((S,Z)-3-((((9H-fluoren-9-yl)methoxy)carbonyl)(methyl)amino)-2-oxo-3,4,7,8-tetrahydroazocin-1(2H)-yl)-3-cyclohexylpropanoyl)-N-methylglycine |
| tp011 | | N-((S)-2-((S,Z)-3-((((9H-fluoren-9-yl)methoxy)carbonyl)(methyl)amino)-2-oxo-3,4,7,8-tetrahydroazocin-1(2H)-yl)-3-(4,4-difluorocyclohexyl)propanoyl)-N-methylglycine |
| tp012 | | N-((S)-2-((S,Z)-3-((((9H-fluoren-9-yl)methoxy)carbonyl)(methyl)amino)-2-oxo-3,4,7,8-tetrahydroazocin-1(2H)-yl)-3-(4-iodophenyl)propanoyl)-N-methylglycine |
| tp013 | | N-((S)-2-((S,Z)-3-((((9H-fluoren-9-yl)methoxy)carbonyl)(methyl)amino)-2-oxo-3,4,5,8-tetrahydroazocin-1(2H)-yl)-3-(4-(trifluoromethyl)phenyl)propanoyl)-N-methylglycine |
| tp014 | | N-((S)-2-((1R,5S,7R)-5-((((9H-fluoren-9-yl)methoxy)carbonyl)(methyl)amino)-4-oxo-3-azabicyclo[5.1.0]octan-3-yl)-3-(4-(trifluoromethyl)phenyl)propanoyl)-N-methylglycine |

TABLE 9-continued

| Compound No. | Structural Formula | Name |
| --- | --- | --- |
| tp015 | | N-((S)-2-((S)-3-((((9H-fluoren-9-yl)methoxy)carbonyl)(methyl)amino)-6-methyl-2-oxo-2,3,4,7-tetrahydro-1H-azepin-1-yl)-3-(4-(trifluoromethyl)phenyl)propanoyl)-N-methylglycine |
| tp016 | | N-((S)-2-((3S,6R)-3-((((9H-fluoren-9-yl)methoxy)carbonyl)(methyl)amino)-6-methyl-2-oxoazepan-1-yl)-3-(4-(trifluoromethyl)phenyl)propanoyl)-N-methylglycine |
| tp017 | | N-((S)-2-((3S,5R,6R)-3-((((9H-fluoren-9-yl)methoxy)carbonyl)(methyl)amino)-5,6-dimethyl-2-oxoazepan-1-yl)-3-(4-(trifluoromethyl)phenyl)propanoyl)-N-methylglycine |
| tp018 | | N-((S)-2-((3S,5S)-3-((((9H-fluoren-9-yl)methoxy)carbonyl)(methyl)amino)-5,6-dimethyl-2-oxoazepan-1-yl)-3-(4-(trifluoromethyl)phenyl)propanoyl)-N-methylglycine |

TABLE 9-continued

| Compound No. | Structural Formula | Name |
|---|---|---|
| tp019 | 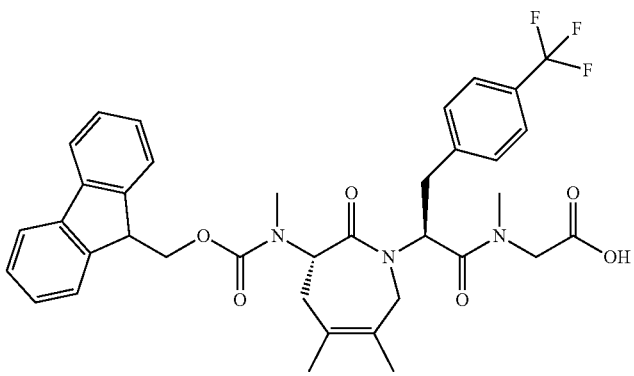 [SMILES: CC1=C(C)CN([C@@H](Cc2ccc(C(F)(F)F)cc2)C(=O)N(C)CC(=O)O)C(=O)[C@@H](N(C)C(=O)OCC2c3ccccc3-c3ccccc32)C1] | N-((S)-2-((S)-3-((((9H-fluoren-9-yl)methoxy)carbonyl)(methyl)amino)-5,6-dimethyl-2-oxo-2,3,4,7-tetrahydro-1H-azepin-1-yl)-3-(4-(trifluoromethyl)phenyl)propanoyl)-N-methylglycine |
| tp020 | 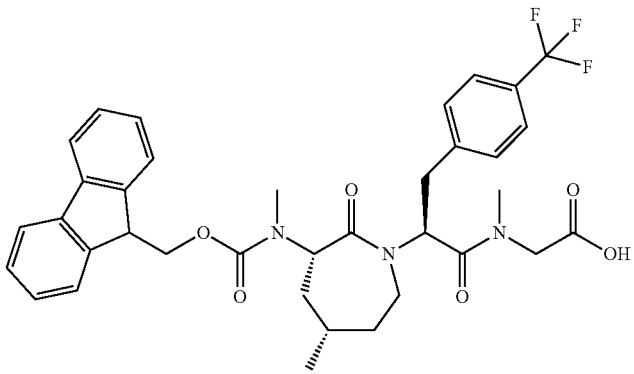 [SMILES: C[C@H]1CCN([C@@H](Cc2ccc(C(F)(F)F)cc2)C(=O)N(C)CC(=O)O)C(=O)[C@@H](N(C)C(=O)OCC2c3ccccc3-c3ccccc32)C1] | N-((S)-2-((3S,5S)-3-((((9H-fluoren-9-yl)methoxy)carbonyl)(methyl)amino)-5-methyl-2-oxoazepan-1-yl)-3-(4-(trifluoromethyl)phenyl)propanoyl)-N-methylglycine |
| tp021 | 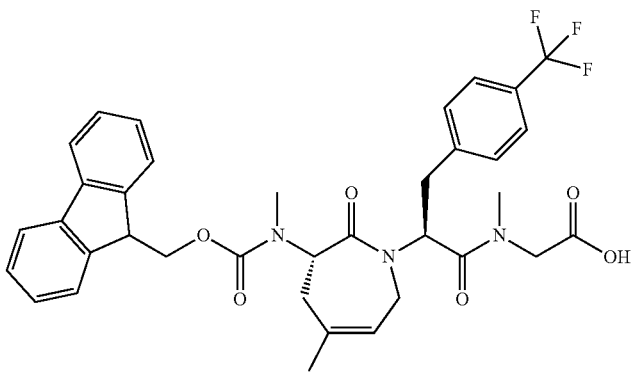 [SMILES: CC1=CCN([C@@H](Cc2ccc(C(F)(F)F)cc2)C(=O)N(C)CC(=O)O)C(=O)[C@@H](N(C)C(=O)OCC2c3ccccc3-c3ccccc32)C1] | N-((S)-2-((S)-3-((((9H-fluoren-9-yl)methoxy)carbonyl)(methyl)amino)-5-methyl-2-oxo-2,3,4,7-tetrahydro-1H-azepin-1-yl)-3-(4-(trifluoromethyl)phenyl)propanoyl)-N-methylglycine |
| tp022 | 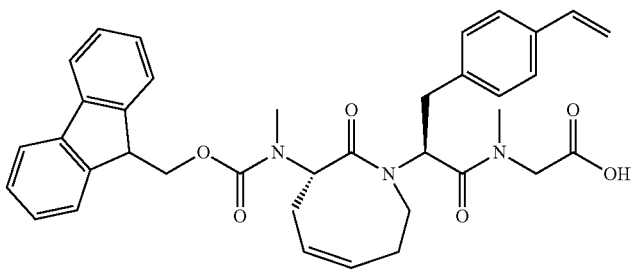 [SMILES: C=Cc1ccc(C[C@@H](C(=O)N(C)CC(=O)O)N2CC/C=C\C[C@H](N(C)C(=O)OCC3c4ccccc4-c4ccccc43)C2=O)cc1] | N-((S)-2-((S,Z)-3-((((9H-fluoren-9-yl)methoxy)carbonyl)(methyl)amino)-2-oxo-3,4,7,8-tetrahydroazocin-1(2H)-yl)-3-(4-vinyl phenyl)propanoyl)-N-methylglycine |

TABLE 9-continued
| Compound No. | Structural Formula | Name |
|---|---|---|
| tp023 | | N-((S)-2-((S)-7-((((9H-fluoren-9-yl)methoxy)carbonyl)(methyl)amino)-5,8-dioxo-1,4-diazocan-1-yl)-3-(4-(trifluoromethyl)phenyl)propanoyl)-N-methylglycine |
| tp024 | | N-((S)-2-((S,Z)-3-((((9H-fluoren-9-yl)methoxy)carbonyl)(methyl)amino)-2-oxo-3,4,7,8-tetrahydroazocin-1(2H)-yl)-3-(4-bromophenyl)propanoyl)-N-methylglycine |
Synthesis of Compound tp005
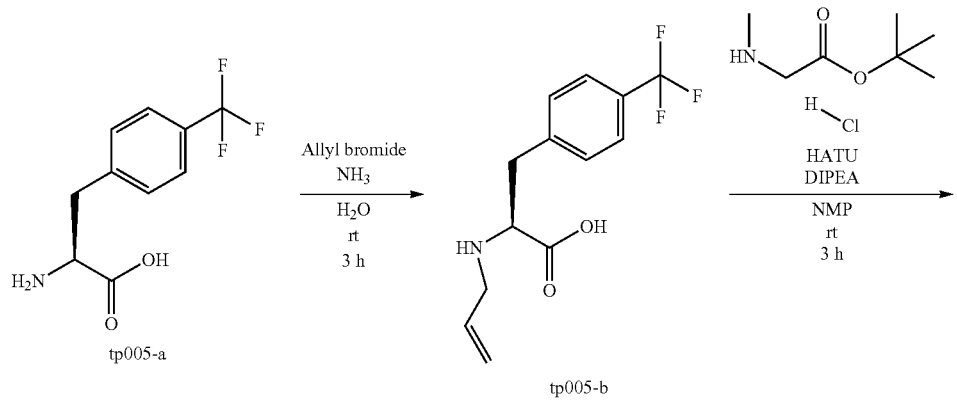

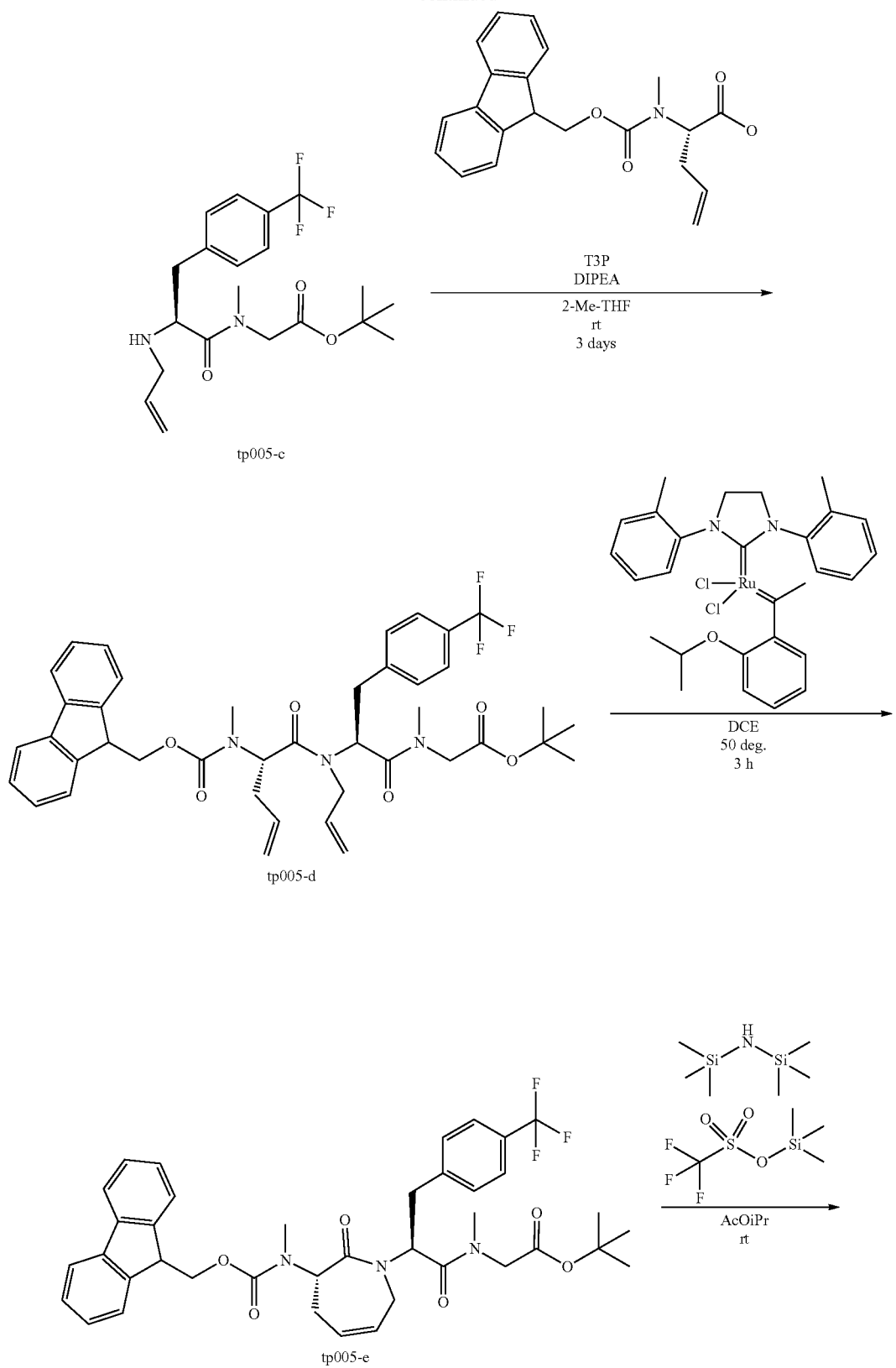

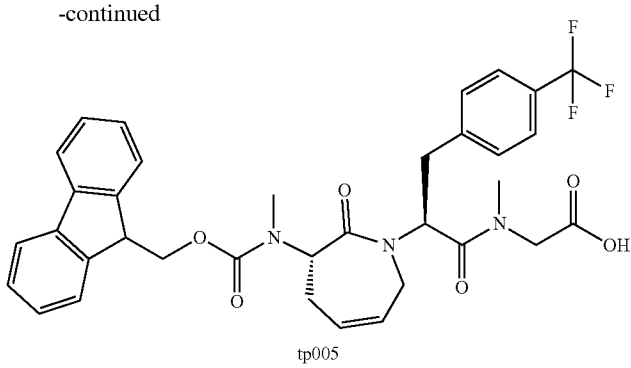

tp005

In a nitrogen atmosphere, water (257.0 mL) and a 28% aqueous ammonia solution (94.0 g, 1544.0 mmol) were added to tp005-a (30.0 g, 129.0 mmol), allyl bromide (65.3 mL, 772.0 mmol) was added dropwise, and the mixture was stirred at room temperature for 3 hours. Ethanol (290.0 mL) was added to the reaction solution, and the mixture was stirred at room temperature for 30 minutes. The mixture was filtered, and the resulting residue was washed with water (300 mL) and dried under reduced pressure to give tp005-b (30.4 g, 86%). LCMS (ESI) m/z=274 (M+H)+

Retention time: 0.64 min (Analytical condition SMD method_04)

In a nitrogen atmosphere, N-methyl-2-pyrrolidinone (209.0 mL) was added to a reaction vessel containing tp005-b (20.0 g, 73.2 mmol) and tert-butyl methyl glycinate hydrochloride (26.6 g, 146.0 mmol), N,N-diisopropylethylamine (51.1 mL, 293.0 mmol) was added dropwise, 1-[bis(dimethylamino)methylene]-1H-1,2,3-triazolo[4,5-b]pyridinium 3-oxidehexafluorophosphate (55.7 g, 146.0 mmol) was added in several times. After the mixture was stirred at room temperature for 3 hours, ethyl acetate (400 mL), water (200 mL), and a 5 wt % aqueous sodium carbonate solution (200 mL) were added for extraction. The organic layer was washed with a 5 wt % aqueous sodium carbonate solution (400 mL), washed twice with potassium hydrogen sulfate (400 mL), washed with 15 wt % brine (400 mL), and passed through a filter provided with anhydrous sodium sulfate, and the solvent was distilled off under reduced pressure to give tp005-c as a crude product (44.5 g).

LCMS (ESI) m/z=401 (M+H)+

Retention time: 0.77 min (Analytical condition SMD method_0) 4)

2-Methyltetrahydrofuran (293.0) ml was added to a reaction vessel containing tp005-c (29.3 g, 73.2 mmol) and (S)-2-((((9H-fluoren-9-yl)methoxy) carbonyl)(methyl)amino)pent-4-enoic acid (33.4 g, 95.0 mmol), N,N-diisopropylethylamine (63.7 mL, 366.0 mmol) was added, and a 50% propylphosphonic anhydride·ethyl acetate solution (93.0 g, 146.0 mmol) and a 50% propylphosphonic anhydride·toluene solution (23.3 g, 36.6 mmol) were added dropwise. After the mixture was stirred at room temperature for 3 days, ethyl acetate (300 mL) and a 5 wt % aqueous sodium carbonate solution (200 mL) were added for extraction. The organic layer was washed twice with 5 wt % potassium hydrogen sulfate (600 mL), washed twice with a 5 wt % aqueous sodium carbonate solution (600 ml), washed with 15 wt % brine (600 mL), and passed through a filter provided with anhydrous sodium sulfate, and the solvent was distilled off under reduced pressure. The resulting residue was purified by silica gel column chromatography (n-hexane/ethyl acetate) to give tp005-d (39.1 g, 73%). Moreover, ethyl acetate (37.0) ml was added to tp005-d (23.1 g, 31.5 mmol), the mixture was heated to 50° C. to be dissolved, and then returned to room temperature, and n-hexane (220.0 ml) was gradually added. The resulting precipitate was filtered, washed with a 95:5 mixed solution of n-hexane and ethyl acetate, and dried under reduced pressure to give tp005-d (19.8 g, 85%).

LCMS (ESI) m/z=734 (M+H)+

Retention time: 1.68 min (Analytical condition SMD method_0) 4)

In a nitrogen atmosphere, 1,2-Dichloroethane (467.0) ml was added to a reaction vessel containing tp005-d (10.3 g, 14.0 mmol) and dichloro [1,3-bis(2-methylphenyl)-2-imidazolidinilidene] (2-isopropoxyphenylmethylene) ruthenium (II)(0).4 g, 0).7 mmol), and the mixture was stirred at 50° C. for 3 hours. The reaction solution was concentrated under reduced pressure, and the resulting residue was purified by silica gel column chromatography (n-hexane/ethyl acetate) to give tp005-e (8.6 g, 87%).

LCMS (ESI) m/z=706 (M+H)+

Retention time: 0.70 min (Analytical condition SQDFA50)

In a nitrogen atmosphere, tp005-e (2.0 g, 2.8 mmol) was dissolved in isopropyl acetate (11.3 ml), then bis(trimethylsilyl)amine (1.5 ml, 7.1 mmol) and trimethylsilyltrifluoromethanesulfonic acid (1.0 ml, 5.7 mmol) were added dropwise at room temperature, and the mixture was stirred for 1 hour. A 1.0 M aqueous disodium hydrogen phosphate solution (15.0 ml) was added, and the mixture was extracted with ethyl acetate (15.0 ml). The organic layer was concentrated under reduced pressure, and the resulting residue was purified by reverse phase chromatography (0.1% formic acid-containing acetonitrile/0.1% formic acid-containing distilled water) to give tp005 (1.2 g, 64%).

LCMS (ESI) m/z=650 (M+H)+

Retention time: 0.48 min (Analytical condition SQDFA50)

Synthesis of Compound tp001

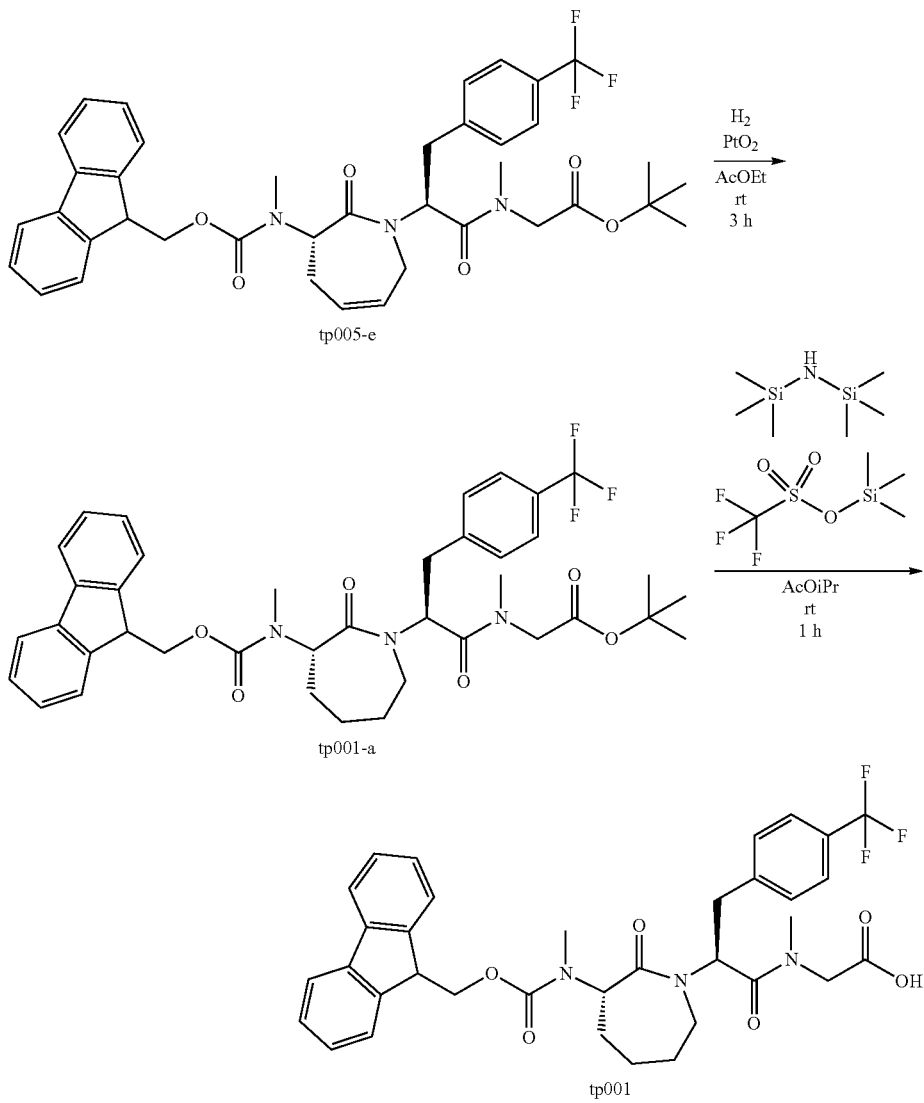

tp005-e (13.1 g, 18.6 mmol) was dissolved in ethyl acetate (124.0 ml), platinum (IV) oxide (844.0 mg, 3.7 mmol) was added, and the mixture was stirred at room temperature for 3 hours in a hydrogen atmosphere. After the solvent was distilled off under reduced pressure, the resulting residue was purified by silica gel column chromatography (n-hexane/ethyl acetate) to give tp001-a (11.4 g, 87%).

LCMS (ESI) m/z=708 (M+H)+

Retention time: 0.73 min (Analytical condition SQDFA50)

Using tp001-a as a starting material, tp001 (9.6 g, 91%) was obtained in the same manner as synthesis of Compound tp005.

LCMS (ESI) m/z=652 (M+H)+

Retention time: 0.46 min (Analytical condition SQDFA50)

Synthesis of Compound tp002
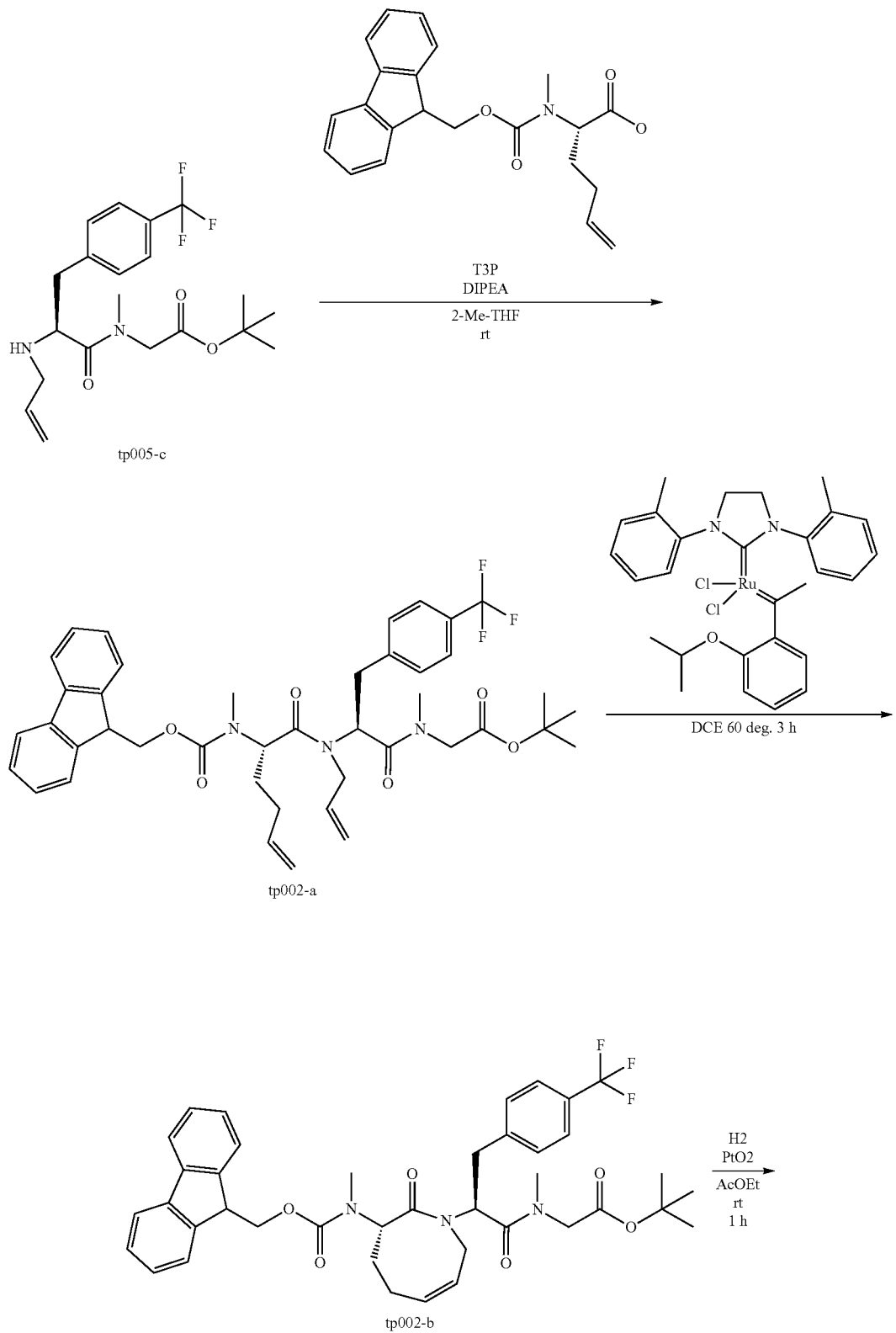

-continued

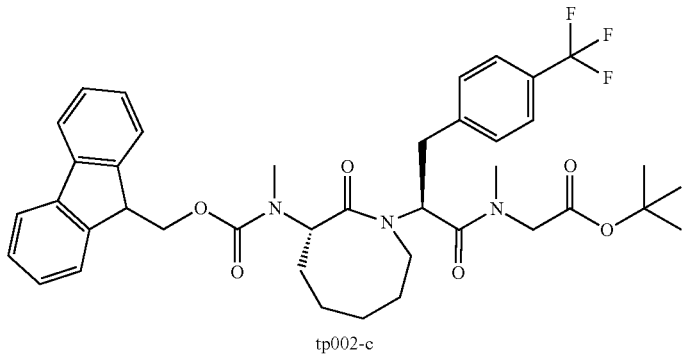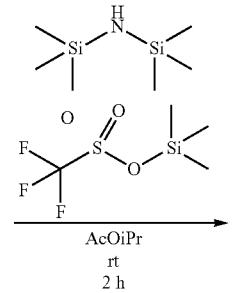

tp002-c

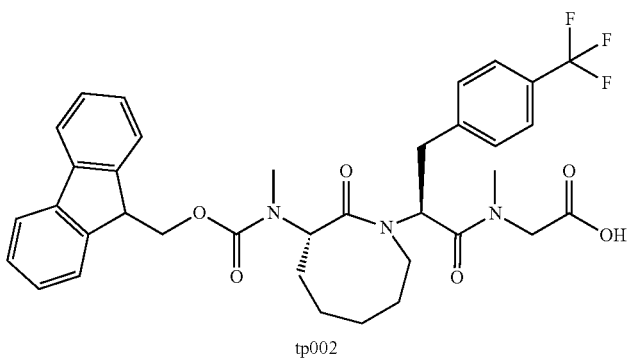

tp002

Using tp005-c as a starting material, tp002-a (26.3 g, 65%) was obtained in the same manner as synthesis of Compound tp005-d.

LCMS (ESI) m/z=748 (M+H)+

Retention time: 1.70 min (Analytical condition SMD method_04)

Using tp002-a as a starting material, tp002-b (2.9 g, 60%) was obtained in the same manner as synthesis of Compound tp005-e.

LCMS (ESI) m/z=720 (M+H)+

Retention time: 1.02 min (Analytical condition SMD method_06)

Using tp002-b as a starting material, tp002-c (9.1 g, 99%) was obtained in the same manner as synthesis of Compound tp001-a.

LCMS (ESI) m/z=722 (M+H)+

Retention time: 1.01 min (Analytical condition SMD method_06)

Using tp002-c as a starting material, tp002 (15.6 g, 90%) was obtained in the same manner as synthesis of Compound tp005.

LCMS (ESI) m/z=666 (M+H)+

Retention time: 1.30 min (Analytical condition SMD method_04)

Synthesis of Compound tp003

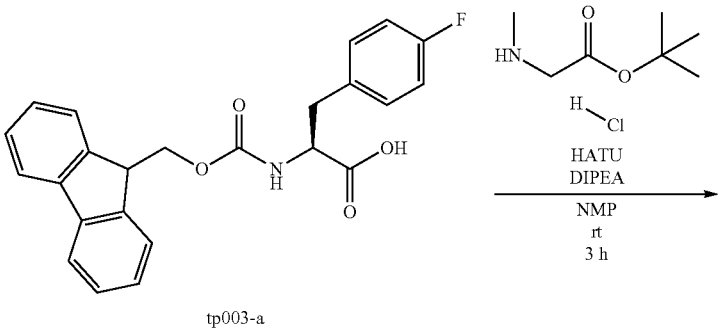

tp003-a

-continued
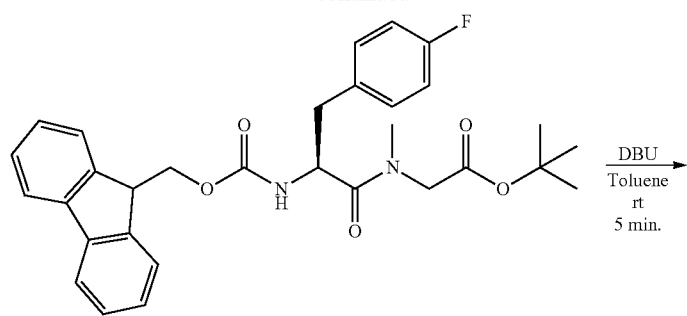
tp003-b
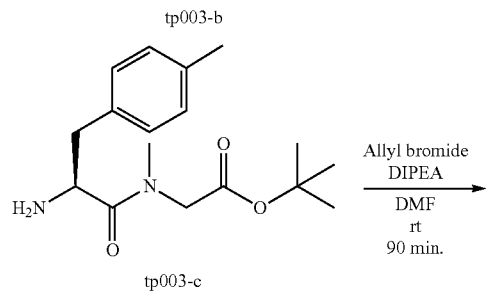
tp003-c
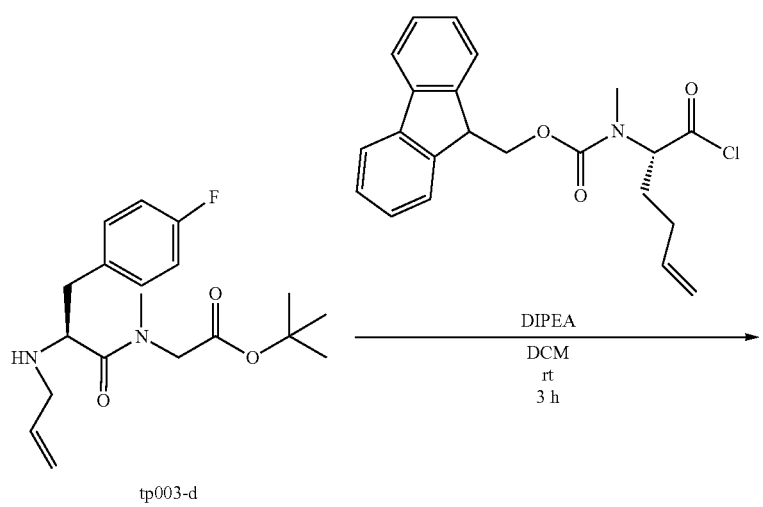
tp003-d
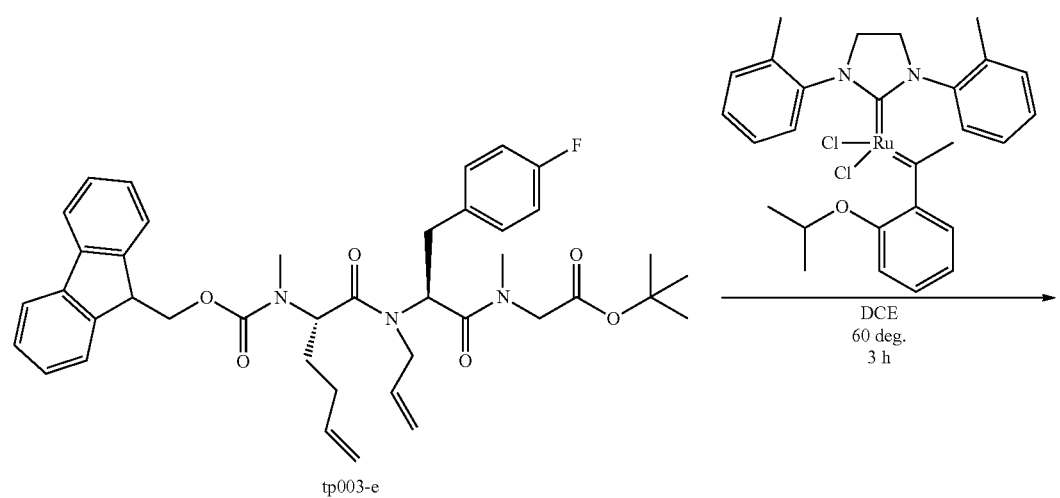
tp003-e

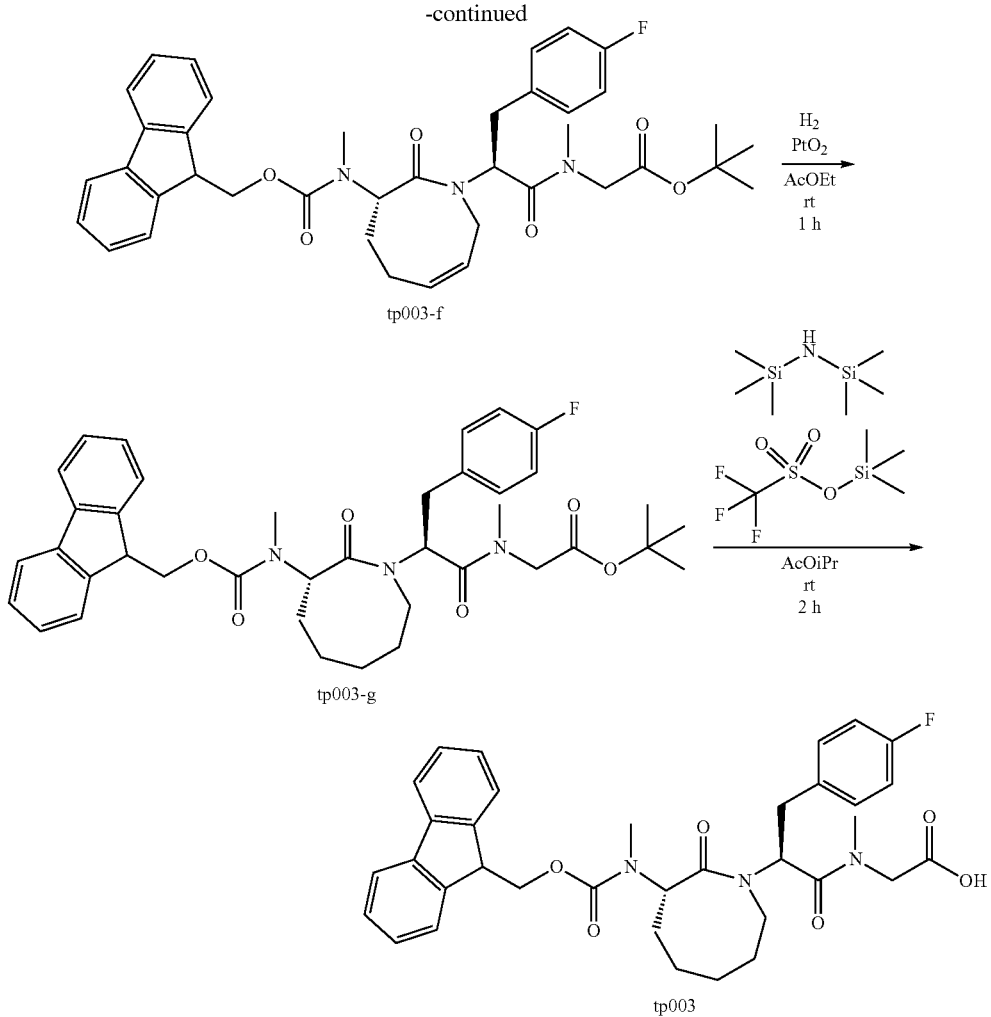

tp003-f tp003-g tp003

Using tp003-a as a starting material, tp003-b (24.6 g, 93%) was obtained in the same manner as synthesis of Compound tp005-c.

LCMS (ESI) m/z=533 (M+H)+

Retention time: 1.42 min (Analytical condition SMD method_04)

tp003-b (24.6 g, 46.2 mmol) and toluene (161.0 ml) were added to a reaction vessel, 1,8-diazabicyclo [5.4.0]-7-undecene (7.0 ml, 46.2 mmol) was added, and the mixture was stirred at room temperature for 5 minutes. Ethyl acetate (75 ml) was added, and the organic layer was washed with a 1.0 mmol/L aqueous potassium dihydrogen phosphate solution (150 ml). n-Hexane (225 ml) was added to the organic layer, and the mixture was extracted with a mixed solution of 2 N hydrochloric acid (35 ml) and water (300 ml). The resulting aqueous layer was adjusted to pH 8.01 with a 3.3 mmol/L aqueous potassium phosphate solution. The mixture was extracted with ethyl acetate (200 ml), and the organic layer was dried over magnesium sulfate. After filtration, the solvent was distilled off under reduced pressure to give tp003-c (9.7 g, 68%).

LCMS (ESI) m/z=311 (M+H)+

Retention time: 0.66 min (Analytical condition SMD method_0) 4)

tp003-c (9.7 g, 31.2 mmol), N,N-dimethylformamide (208.0 ml), and N,N-diisopropylethylamine (5.7 ml, 32.8 mmol) were added to the reaction vessel, allyl bromide (6.8 ml, 78.0 mmol) was added dropwise, and the mixture was stirred at room temperature for 90) minutes. Ethyl acetate (200) ml) was added, and the mixture was washed with water (200 ml) and then washed with a 1.0 mmol/L aqueous potassium dihydrogen phosphate solution (200 ml). n-Hexane (4 ( )) ml) was added to the organic layer, and the mixture was extracted with a mixed solution of 2 N hydrochloric acid (15.6 ml) and water (200 ml). The resulting aqueous layer was adjusted to pH 8.15 with a 3.3 mmol/L aqueous potassium phosphate solution. The mixture was extracted with ethyl acetate (200 ml), and the organic layer was dried over magnesium sulfate. After filtration, the solvent was distilled off under reduced pressure to give tp003-d (7.6 g, 69%).

LCMS (ESI) m/z=351 (M+H)+

Retention time: 0.68 min (Analytical condition SMD method_0) 4)

(S)-2-((((9H-Fluoren-9-yl)methoxy) carbonyl)(methyl) amino) hex-5-enoic acid (26.1 g, 71.3 mmol), dichloromethane (184.0 ml), and N,N-dimethylformamide (0).6 ml, 7.1 mmol) were added to the reaction vessel, thionyl chloride (13.0) ml, 178.0) mmol) was added, the mixture was stirred at room temperature for 1 hour, and the solvent was distilled off under reduced pressure. The resulting residue was dissolved in dichloromethane (81.0) ml), and this was added by cannulation to a reaction vessel containing tp003-d (22.7 g, 64.8 mmol), N,N-diisopropylethylamine (39.5 ml, 227.0) mmol), and dichloromethane (243.0 ml). After the mixture was stirred at room temperature for 3 hours, the solvent was distilled off under reduced pressure. The resulting residue was purified by silica gel column chromatography (n-hexane/ethyl acetate) to give tp003-e (38.3 g, 85%).

LCMS (ESI) m/z=698 (M+H)+

Retention time: 1.65 min (Analytical condition SMD method_0) 4)

Using tp003-e as a starting material, tp003-f (17.4 g, 58%) was obtained in the same manner as synthesis of Compound tp005-e.

LCMS (ESI) m/z=670 (M+H)+

Retention time: 0.93 min (Analytical condition SMD method_06)

Using tp003-f as a starting material, tp003-g (17.9 g, 100%) was obtained in the same manner as synthesis of Compound tp001-a.

LCMS (ESI) m/z=672 (M+H)+

Retention time: 0.91 min (Analytical condition SMD method_06)

Using tp003-g as a starting material, tp003 (16.7 g, 82%) was obtained in the same manner as synthesis of Compound tp005.

LCMS (ESI) m/z=616 (M+H)+

Retention time: 1.21 min (Analytical condition SMD method_04)

Synthesis of Compound tp004

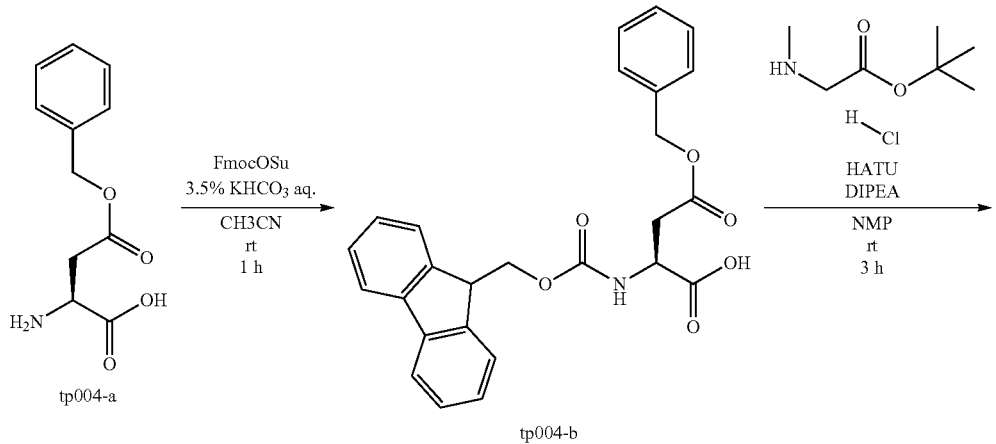

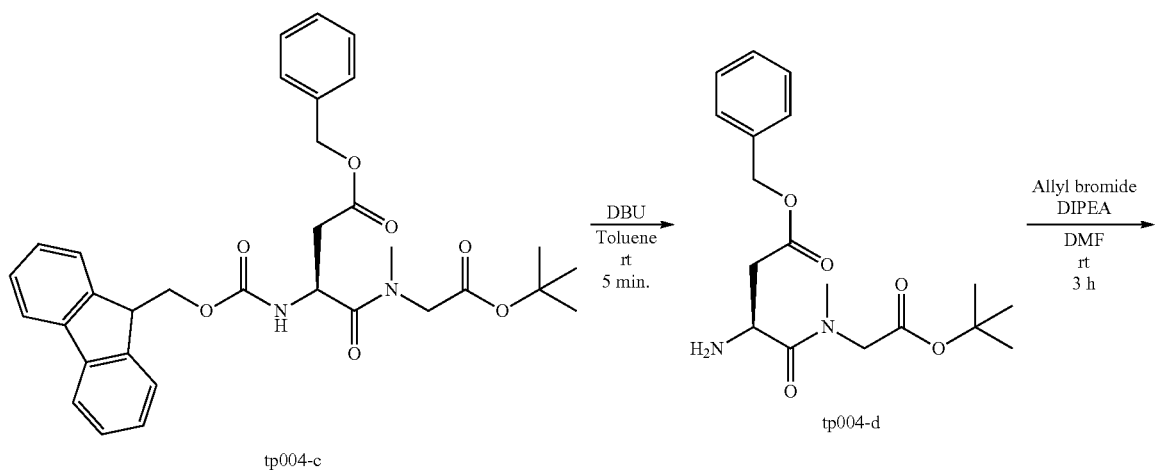

-continued
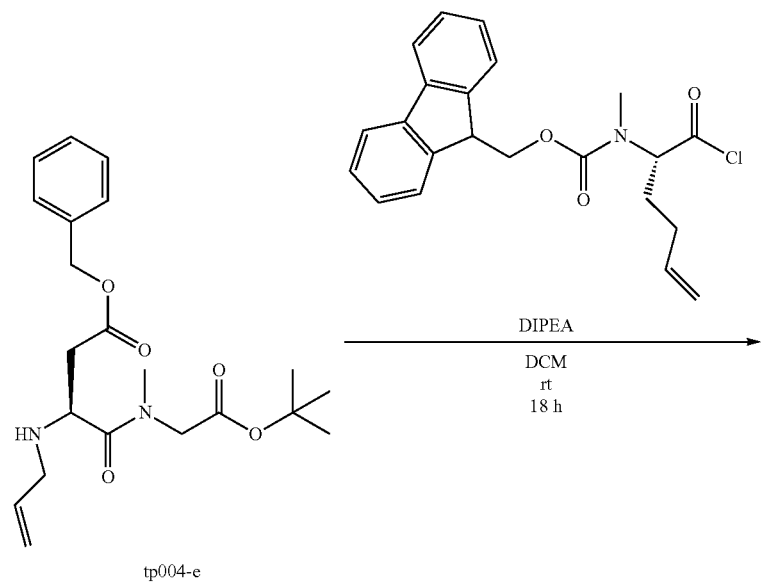
tp004-e
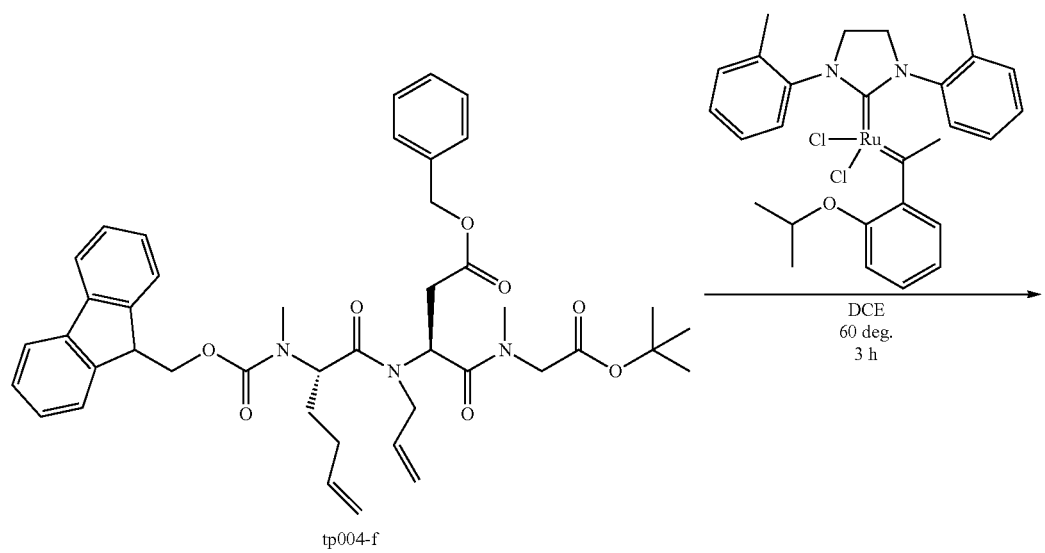
tp004-f
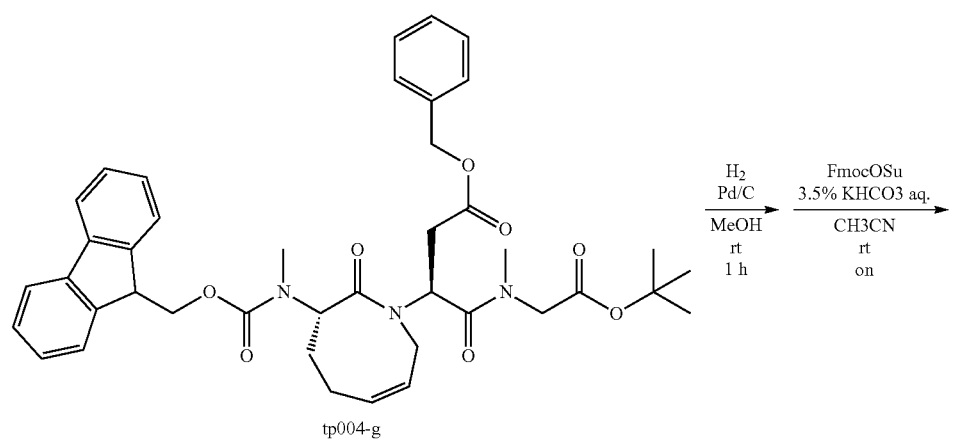
tp004-g

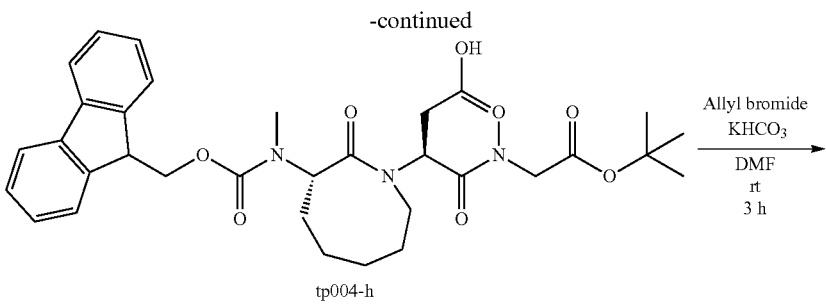

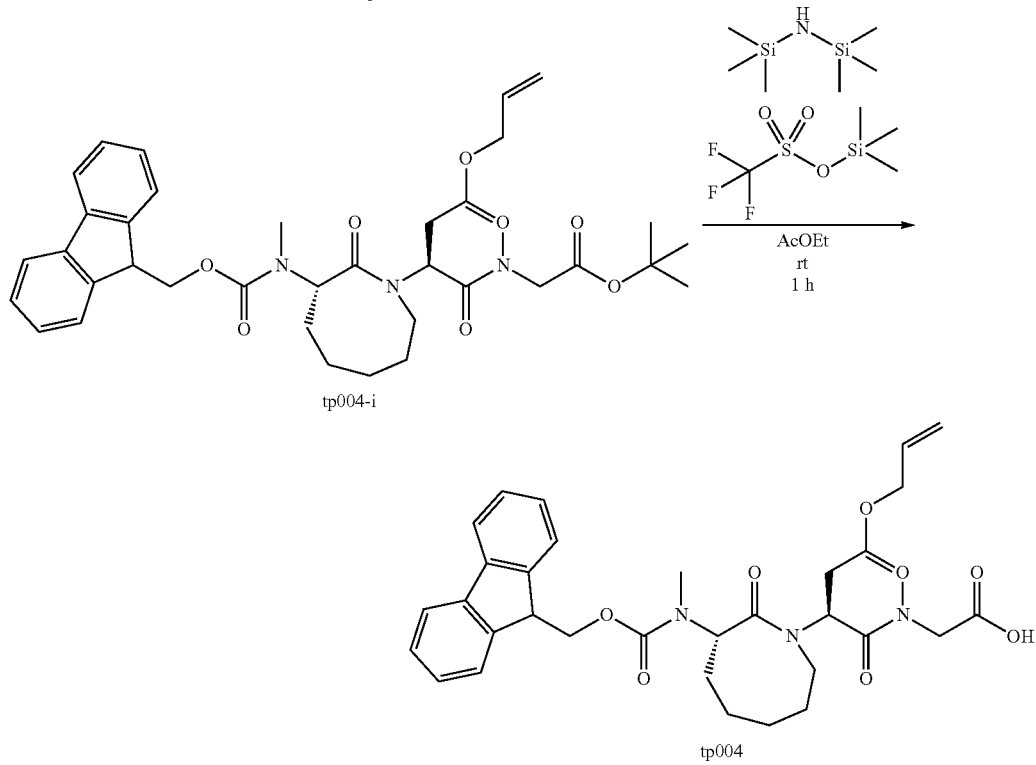

A 3.5 wt % aqueous potassium hydrogen carbonate solution (194 ml) and acetonitrile (194 ml) were added to tp004-a (13.0 g, 58.2 mmol), then (2.5-dioxopyrrolidin-1-yl)(9H-fluoren-9-yl)methyl carbonate (19.6 g, 58.2 mmol) was added, and then the mixture was vigorously stirred at room temperature for 1 hour. A 3.5 wt % aqueous potassium hydrogen carbonate solution (195 ml) was added, and the mixture was stirred at room temperature for 30 minutes. The reaction solution was washed with a 1:2 mixed solution (390 ml) of tert-butyl methyl ether and n-hexane, and then adjusted to pH 3 with phosphoric acid. The mixture was extracted with tert-butyl methyl ether (195 ml), and the organic layer was washed with a saturated aqueous sodium chloride solution (130 ml). The organic layer was dried over magnesium sulfate and filtered, and then the solvent was distilled off under reduced pressure to give tp004-b (25.9 g, 100%).

LCMS (ESI) m/z=446 (M+H)+

Retention time: 1.22 min (Analytical condition SMD method_04)

Using tp004-b as a starting material, tp004-c (32.1 g, 96%) was obtained in the same manner as synthesis of Compound tp005-c.

LCMS (ESI) m/z=573 (M+H)+

Retention time: 1.43 min (Analytical condition SMD method_04)

Using tp004-c as a starting material, tp004-d (17.7 g, 90%) was obtained in the same manner as synthesis of Compound tp003-c.

LCMS (ESI) m/z=351 (M+H)+

Retention time: 0.95 min (Analytical condition SMD method_08)

Using tp004-d as a starting material, tp004-e (13.6 g, 69%) was obtained in the same manner as synthesis of Compound tp003-d.

LCMS (ESI) m/z=391 (M+H)+

Retention time: 1.15 min (Analytical condition SMD method_08)

Using tp004-e as a starting material, tp004-f (1.4 g, 76%) was obtained in the same manner as synthesis of Compound tp003-e.

LCMS (ESI) m/z=760 (M+Na)+

Retention time: 1.65 min (Analytical condition SMD method_04)

Using tp004-f as a starting material, tp004-g (6.4 g, 59%) was obtained in the same manner as synthesis of Compound tp005-e.

LCMS (ESI) m/z=732 (M+Na)+

Retention time: 1.56 min (Analytical condition SMD method_04)

tp0) 04-g (6.4 g, 9.0) mmol) was dissolved in methanol (299 ml), 10% palladium carbon (636.0) mg) was added, and the mixture was stirred in a hydrogen atmosphere for 1 hour. After filtration, the solvent was distilled off under reduced pressure. Acetonitrile (128 ml) and a 3.5 wt % aqueous potassium hydrogen carbonate solution (128 ml) were added, then (2,5-dioxopyrrolidin-1-yl)(9H-fluoren-9-yl)methyl carbonate (5.4 g, 16.0) mmol) was added, and then the mixture was stirred at room temperature for 30 minutes. Moreover, (2,5-dioxopyrrolidin-1-yl)(9H-fluoren-9-yl)methyl carboxylate (5.4 g, 16.0 mmol) was added, and then the mixture was stirred overnight at room temperature. A 3.5 wt % aqueous potassium hydrogen carbonate solution (128 ml) and water (128 ml) were added, and the mixture was washed with a 1:2 mixed solution of ethyl acetate and n-hexane (384 ml) and adjusted to pH 3 with phosphoric acid. The mixture was extracted with ethyl acetate (128 ml), and the organic layer was washed with a saturated aqueous sodium chloride solution (64 ml). The organic layer was dried over magnesium sulfate and filtered, and then the solvent was distilled off under reduced pressure to give tp004-h (12.3 g, 100%).

LCMS (ESI) m/z=622 (M+H)+

Retention time: 1.28 min (Analytical condition SMD method_0) 4)

tp004-h (11.4 g, 18.3 mmol) was dissolved in N,N-dimethylformamide (183.0) ml), and after potassium hydrogen carbonate (4.6 g, 45.8 mmol) and then allyl bromide (10.6 ml, 122.0) mmol) were added, the mixture was vigorously stirred at room temperature for 3 hours. Ethyl acetate (200 ml) and n-hexane (200 ml) were added, the organic layer was washed with a 3.5 wt % aqueous potassium hydrogen carbonate solution (200 ml) and then water (200 ml), and the organic layer was dried over anhydrous magnesium sulfate. After filtration, the solvent was distilled off under reduced pressure, and the resulting residue was purified by silica gel column chromatography (n-hexane/ethyl acetate) to give tp00) 4-i (11.4 g, 92%).

LCMS (ESI) m/z=684 (M+Na)+

Retention time: 1.49 min (Analytical condition SMD method_0) 4)

Using tp004-i as a starting material, tp004 (5.3 g, 94%) was obtained in the same manner as synthesis of Compound tp005.

LCMS (ESI) m/z=628 (M+Na)+

Retention time: 1.16 min (Analytical condition SMD method_0) 4)

Synthesis of Compound tp013

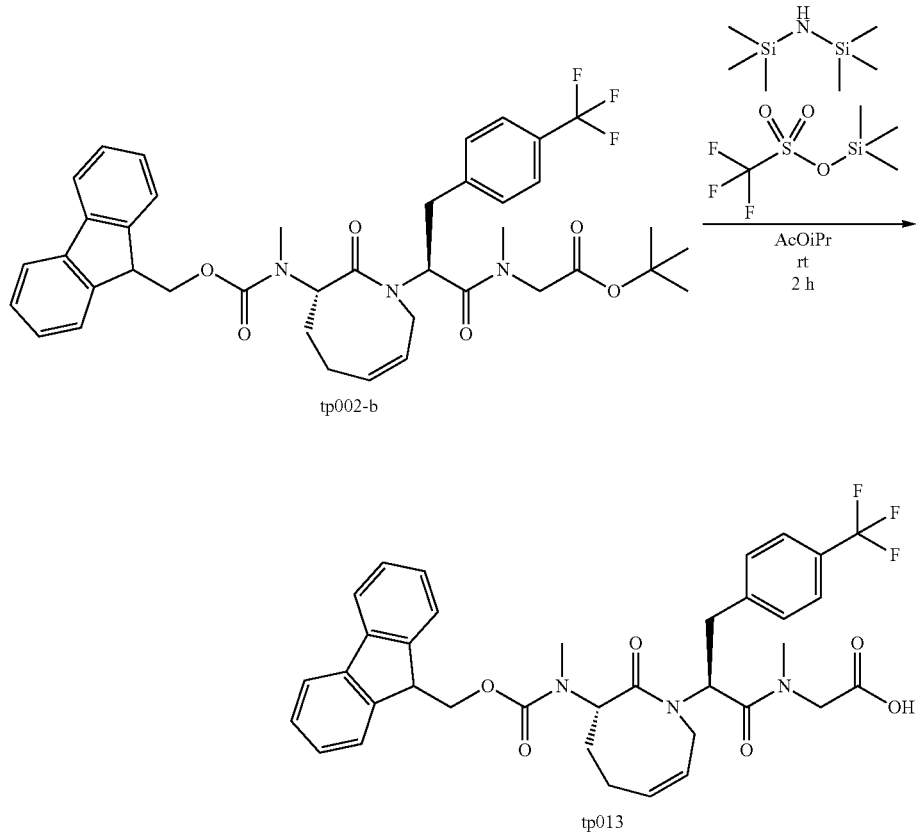

Using tp002-b as a starting material, tp013 (760.7 mg, 94%) was obtained in the same manner as synthesis of Compound tp005.

LCMS (ESI) m/z=664 (M+H)+

Retention time: 1.32 min (Analytical condition SMD method_04)

Synthesis of Compound tp006
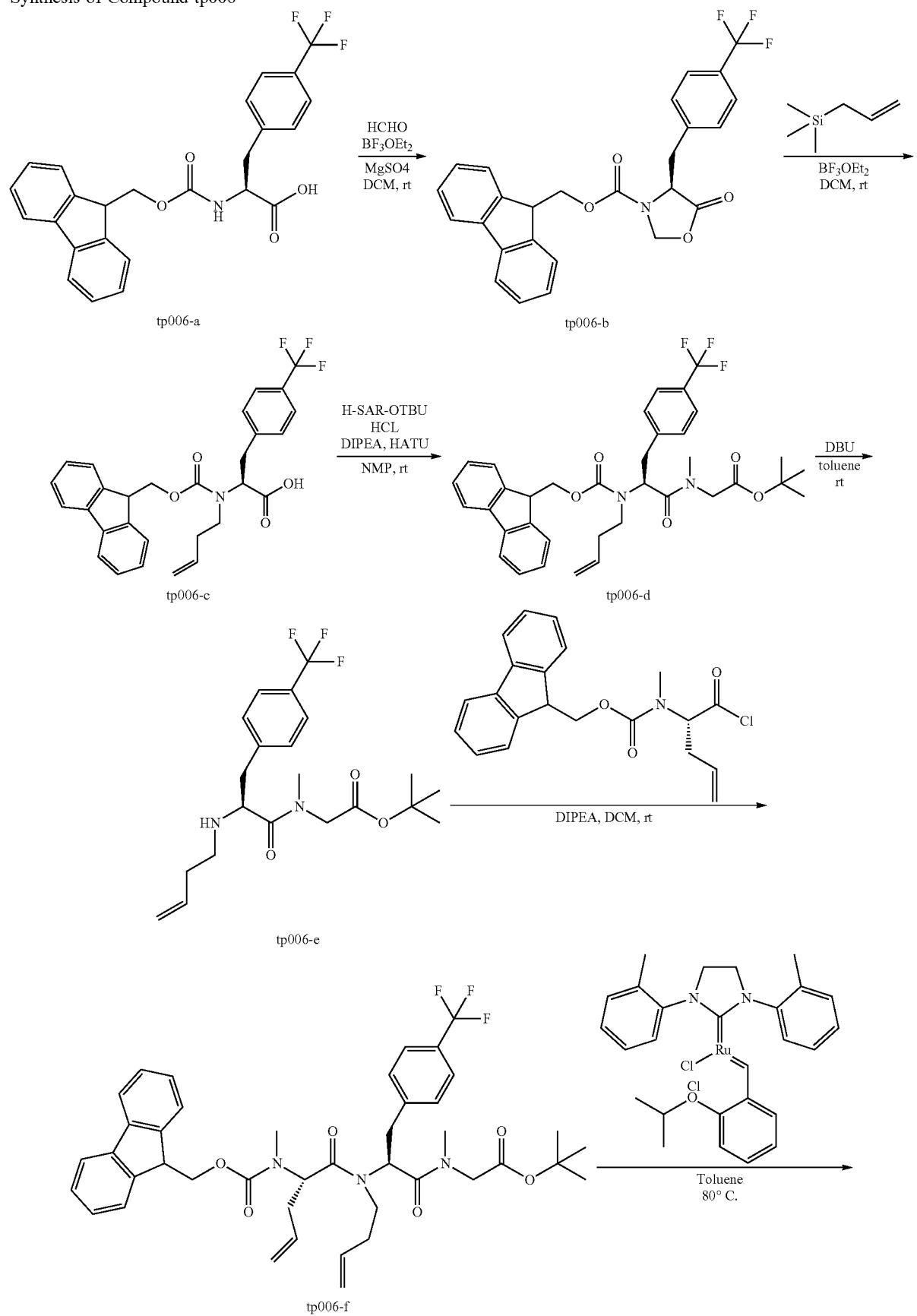

-continued

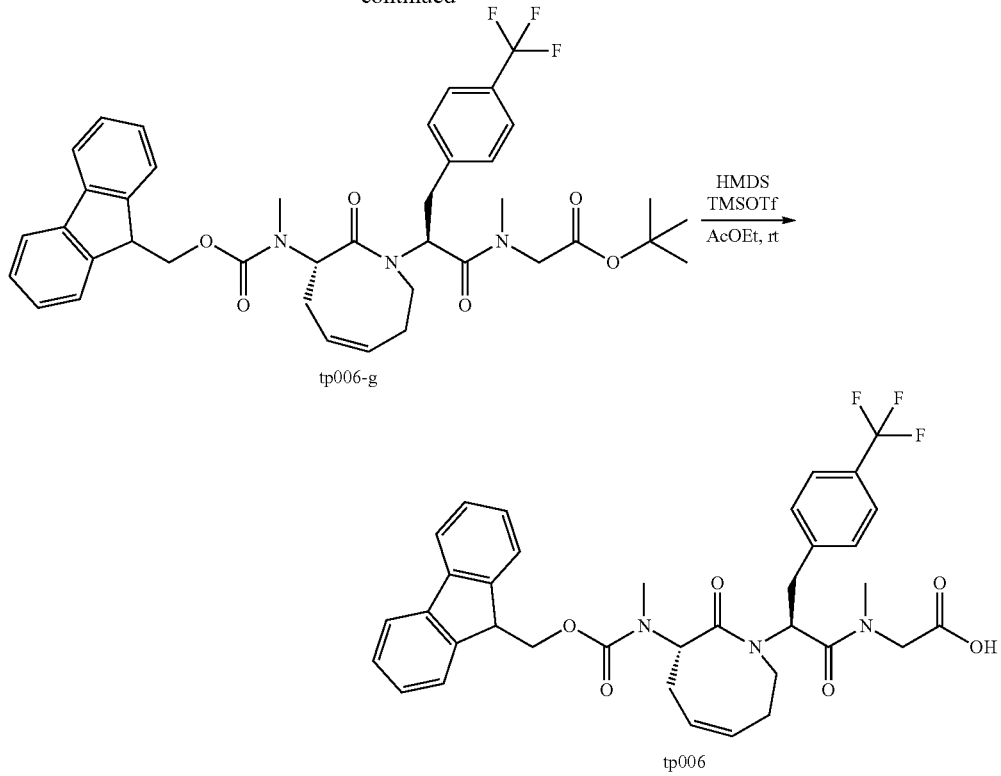

tp006-g tp006

Magnesium sulfate (6.61 g, 54.9 mmol) and paraformaldehyde (1.98 g, 65.9 mmol) were added at room temperature to a dichloromethane (200 mL) solution of Compound tp006-a (N-([(9H-fluoren-9-yl)methoxy]carbonyl)-4-(trifluoromethyl)-L-phenylalanine)(10.0 g, 22.0 mmol), and then a boron trifluoride diethyl ether complex (2.78 mL, 22.0 mmol) was added dropwise. After the reaction mixture was stirred at room temperature for 1 hour, the reaction solution was filtered through silica gel (24 g) and then concentrated under reduced pressure to give a crude product tp006-b (10.5 g, quant.).

LCMS (ESI) m/z=468 (M+H)+

Retention time: 1.45 min (Analytical condition SMD method_0) 4)

The resulting crude product tp006-b (10.3 g, 22.0 mmol) was dissolved in dichloromethane (200 mL), and allyltrimethylsilane (12.2 mL, 77.0 mmol) was added in a nitrogen atmosphere, and a boron trifluoride diethyl ether complex (7.0 mL, 54.9 mmol) was added dropwise. After the reaction mixture was stirred at room temperature for 6 hours, allyltrimethylsilane (12.2 mL, 77.0 mmol) and a boron trifluoride diethyl ether complex (7.0 mL, 54.9 mmol) were added, and the mixture was stirred for 3 days. Water (40) mL) was added to the reaction solution, the mixture was stirred at room temperature for 10 minutes, filtered through Celite, the filtrate was concentrated under reduced pressure, and the resulting residue was dissolved in toluene (24 mL). The organic layer was washed with water (48 mL), hexane (100 mL) was added, and the mixture was extracted with a mixed solution (2:1, 300 mL) of a 3.5% aqueous potassium hydrogen carbonate solution and acetonitrile. Phosphoric acid was added to the resulting aqueous layer until pH 3, and then the mixture was extracted with ethyl acetate (200 mL). The organic layer was washed with saturated brine (100 mL), dried over anhydrous magnesium sulfate, and then filtered. The resulting solution was concentrated under reduced pressure to give Compound tp006-c (10.3 g, 92%).

LCMS (ESI) m/z=510 (M+H)+

Retention time: 1.00 min (Analytical condition SMD method_08)

After HATU (60.4 g, 159 mmol) was added to an NMP (379 mL) solution of Compound tp006-c (67.5 g, 132 mmol) and sarcosine tert-butyl ester hydrochloride (25.3 g, 139 mmol), DIPEA (69.2 mL, 397 mmol) was added dropwise. After the reaction mixture was stirred at room temperature for 1.5 hours, toluene (1.0 µL, 15 v/w) was added, and the organic layer was washed with water (473 mL, 7 v/w), a 3.5% aqueous potassium hydrogen carbonate solution (473 mL, 7 v/w), and a 1 M aqueous potassium dihydrogen phosphate solution (473 mL, 7 v/w). The organic layer was dried by being passed through an anhydrous magnesium sulfate pad and washed with toluene (67.5 mL, 1 v/w), and the resulting filtrate and washing solution were combined to give Compound tp006-d, which was directly used in the next reaction as a solution.

LCMS (ESI) m/z=637 (M+H)+

Retention time: 1.66 min (Analytical condition SMD method_10))

DBU (1.97 mL., 13.2 mmol) was added to a toluene solution of the above Compound tp-006-d (132 mmol) at room temperature. The reaction mixture was stirred at room temperature for 17 hours and then washed with a 1 M aqueous potassium dihydrogen phosphate solution (420) mL., 5 v/w). The resulting organic layer was diluted with n-hexane (840 mL, 10) v/w), and then extracted twice with a mixed solution of 2 N hydrochloric acid (99 mL., 198 mmol), water (840 ml., 10 v/w), and acetonitrile (588 mL., 7 v/w). A 3.3 M aqueous potassium phosphate solution was added to the resulting aqueous layer to adjust the pH to 9.5, and the mixture was extracted with ethyl acetate (840 ml., 10 v/w). The organic layer was concentrated under reduced pressure, the resulting residue was dissolved in ethyl acetate (840 mL., 10 v/w), washed with brine (420 ml., 5 v/w), dried over anhydrous magnesium sulfate, and then filtered. The resulting solution was concentrated under reduced pressure to give Compound tp006-e (49.0 g, 90%).

LCMS (ESI) m/z=415 (M+H)+
Retention time: 1.31 min (Analytical condition SMD method_10)

DIPEA (72.3 mL., 414 mmol) was added to a dichloromethane (276 mL.) solution of Compound tp006-e (49.0 g, 118 mmol). The resulting mixture was added dropwise to a separately prepared dichloromethane (276 mL.) solution of (9H-fluoren-9-yl)methyl(S)-(1-chloro-1-oxopent-4-en-2-yl) (methyl) carbamate (described below) over 30 minutes. After the resulting reaction mixture was stirred at room temperature for 17 hours, the organic layer was washed with a 5% aqueous sodium dihydrogen phosphate solution (500 mL., 10 v/w), dried over anhydrous magnesium sulfate, and then filtered, and the solution was concentrated under reduced pressure. The resulting crude product was purified by normal phase silica gel chromatography (n-hexane/ethyl acetate) to give Compound tp006-f (45.0 g, 51%).

(9H-Fluoren-9-yl)methyl(S)-(1-chloro-1-oxopent-4-en-2-yl)(methyl) carbamate was prepared as follows. After thionyl chloride (21.6 mL., 296 mmol) was added to a dichloromethane (296 mL.) solution of(S)-2-((((9H-fluoren-9-yl) methoxy) carbonyl)(methyl)amino) pent-4-enoic acid (41.6 g, 118 mmol), DMF (0.92 mL, 11.8 mmol) was added dropwise. The resulting reaction mixture was stirred at room temperature for 15 minutes and then concentrated under reduced pressure. Toluene (20 mL., 5 v/w) was added to the resulting residue, and the mixture was concentrated under reduced pressure. The resulting crude product was dissolved in dichloromethane (276 mL.) and used in the above-described reaction.

LCMS (ESI) m/z=748 (M+H)+
Retention time: 1.71 min (Analytical condition SMD method_10)

A dichloroethane (891 mL) solution of Compound tp006-f (16.7 g, 22.3 mmol), benzoquinone (0.24 g, 2.23 mmol), and a Stewart-Grubbs catalyst (0.51 g, 0.89 mmol) was degassed 5 times, and stirred at 80° C. for 4 hours in a nitrogen atmosphere. The reaction mixture was cooled to room temperature, and then concentrated under reduced pressure, and the resulting crude product was purified by normal phase silica gel column chromatography (hexane/ethyl acetate) to give Compound tp006-g (33.9 g, 39%).

LCMS (ESI) m/z=720 (M+H)+
Retention time: 1.00 min (Analytical condition SMD method_07)

After hexamethyldisilazane (24.7 mL, 118 mmol) was added to an ethyl acetate (236 mL) solution of tp006-g (33.9 g, 47.1 mmol) in a nitrogen atmosphere, trimethylsilyl trifluoromethanesulfonate (17.0 mL, 94 mmol) was added dropwise while cooling the mixture in a water bath (25° C.). After the reaction mixture was stirred at room temperature for 1.5 hours, a 5% aqueous disodium hydrogen phosphate solution (340 mL, 10 v/w) was added while cooling the mixture in an ice bath to quench the reaction. Water (170 mL, 5 v/w) and phosphoric acid were added to the resulting mixture to adjust the pH to 3. The separated organic layer was washed with saturated brine (340 mL, 10 v/w), dried over anhydrous magnesium sulfate, and filtered, and the solution was concentrated under reduced pressure. The resulting crude product was purified by reverse phase column chromatography (0.1% formic acid-containing acetonitrile/0.1% formic acid-containing distilled water), and collected fractions were purified by reverse phase column chromatography (acetonitrile/distilled water) to give Compound tp006 (22.4 g, 72%).

LCMS (ESI) m/z=664 (M+H)+
Retention time: 0.63 min (Analytical condition SMD method_06)

Synthesis of Compound tp010

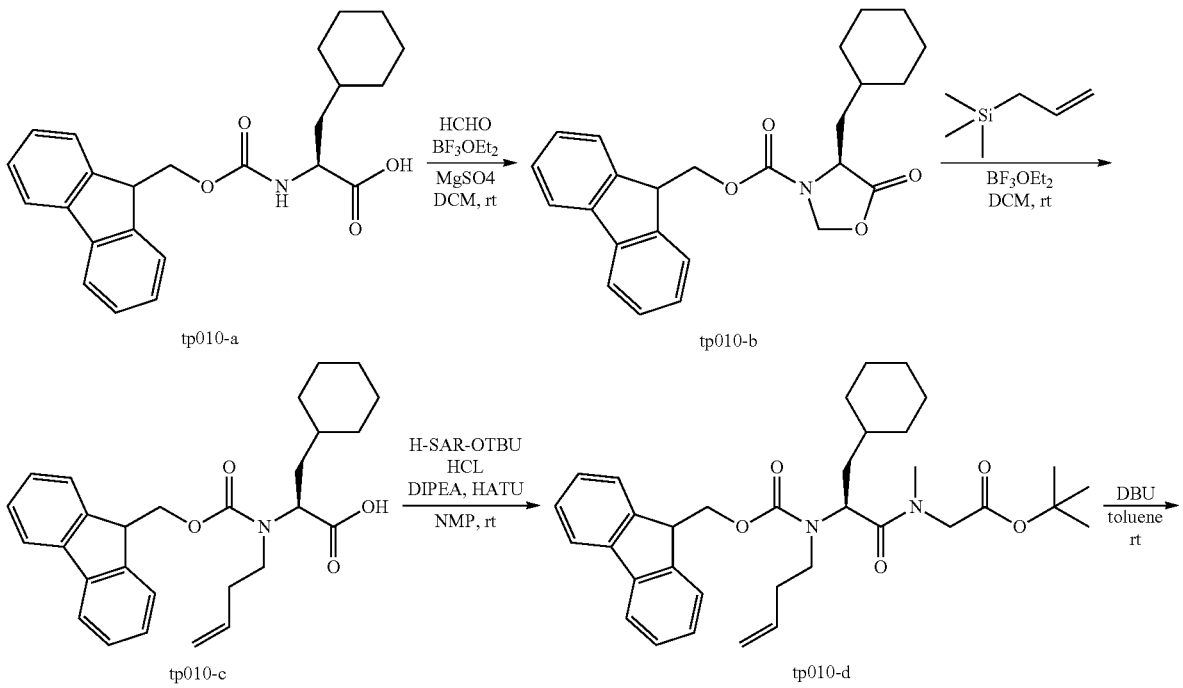

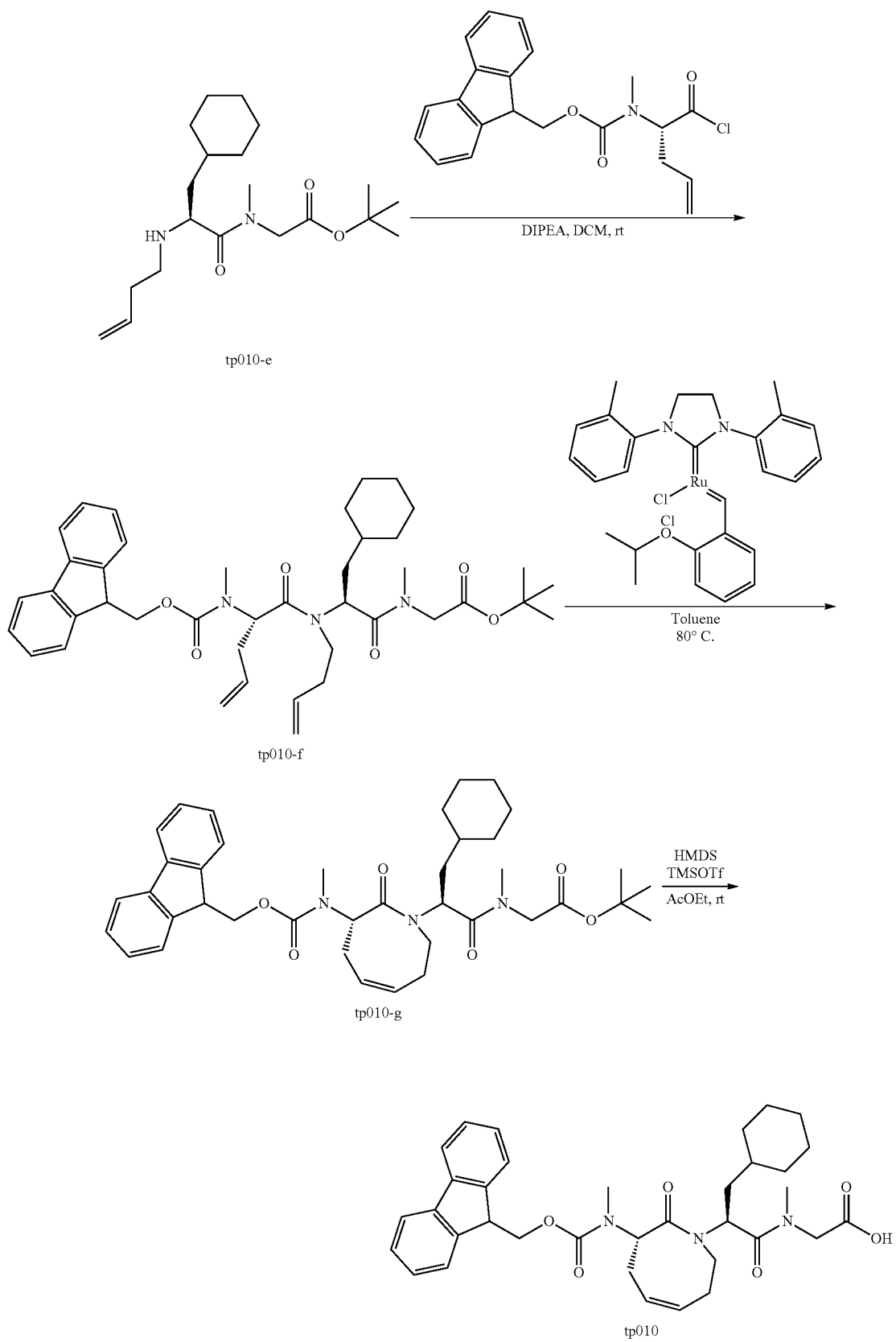

Using Compound tp010-a ((S)-2-((((9H-fluoren-9-yl)methoxy) carbonyl)amino)-3-cyclohexylpropanoic acid) (14.0 g, 35.6 mmol) as a starting material, a crude product tp010-b (14.4 g, quant.) was obtained in the same manner as synthesis of Compound tp006-b. LCMS (ESI) m/z=406 (M+H)+

Retention time: 0.78 min (Analytical condition SQDAA50_2)

Using the resulting crude product tp010-b (14.4 g, 35.6 mmol), Compound tp010-c (12.6 g, 79%) was obtained in the same manner as synthesis of Compound tp006-c. LCMS (ESI) m/z=448 (M+H)+

Retention time: 0.71 min (Analytical condition SQDAA50_2)

Using Compound tp010-c (12.6 g, 28.3 mmol), a toluene solution of Compound tp010-d was obtained in the same manner as synthesis of Compound tp006-d. The resulting solution of Compound tp010-d was directly used in the next reaction.

LCMS (ESI) m/z=575 (M+H)+

Retention time: 0.88 min (Analytical condition SQDAA50_2)

Using a toluene solution of the above Compound tp010-d (28.3 mmol), Compound tp010-e (9.0 g, 91%) was obtained in the same manner as synthesis of Compound tp006-e. LCMS (ESI) m/z=353 (M+H)+

Retention time: 0.66 min (Analytical condition SQDAA50_2)

Using Compound tp010-e (4.5 g, 12.8 mmol), Compound tp010-f (8.6 g, 98%) was obtained in the same manner as synthesis of Compound tp006-f.

LCMS (ESI) m/z=708 (M+Na)+

Retention time: 0.91 min (Analytical condition SQDAA50_2)

After nitrogen bubbling in a dichloroethane (469 mL) solution of Compound tp010-f (8.0 g, 11.7 mmol) and a Stewart-Grubbs catalyst (0.17 g, 0.29 mmol), the mixture was stirred at 80° C. for 16 hours in a nitrogen atmosphere. The reaction mixture was cooled to room temperature and then concentrated under reduced pressure, and the resulting crude product was purified by normal phase silica gel column chromatography (n-hexane/ethyl acetate) to give Compound tp010-g (5.7 g, 73%).

LCMS (ESI) m/z=680 (M+Na)+

Retention time: 0.84 min (Analytical condition SQDAA50_2)

Using Compound tp010-g (5.7 g, 8.6 mmol), Compound tp010 (3.8 g, 74%) was obtained in the same manner as synthesis of Compound tp006.

LCMS (ESI) m/z=624 (M+Na)+

Retention time: 0.69 min (Analytical condition SQDFA40)

Synthesis of Compound tp011

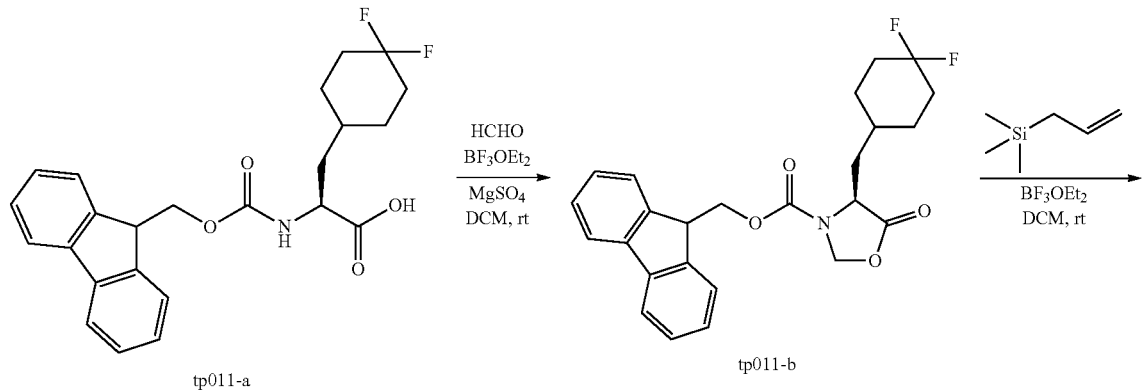

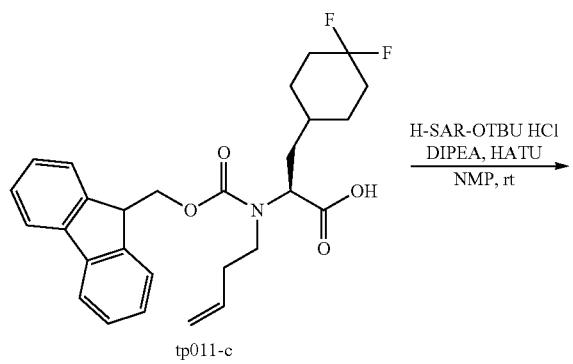

-continued
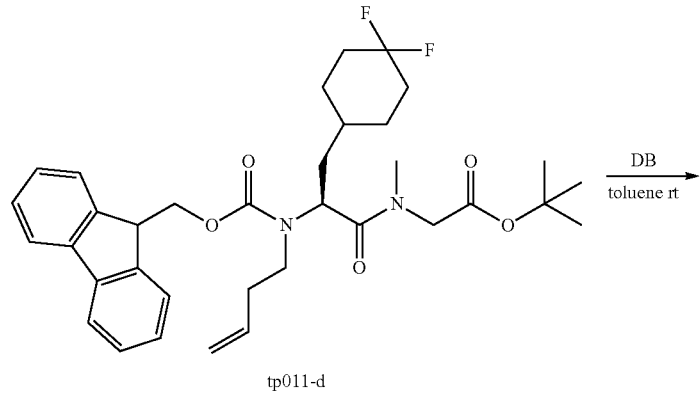
tp011-d
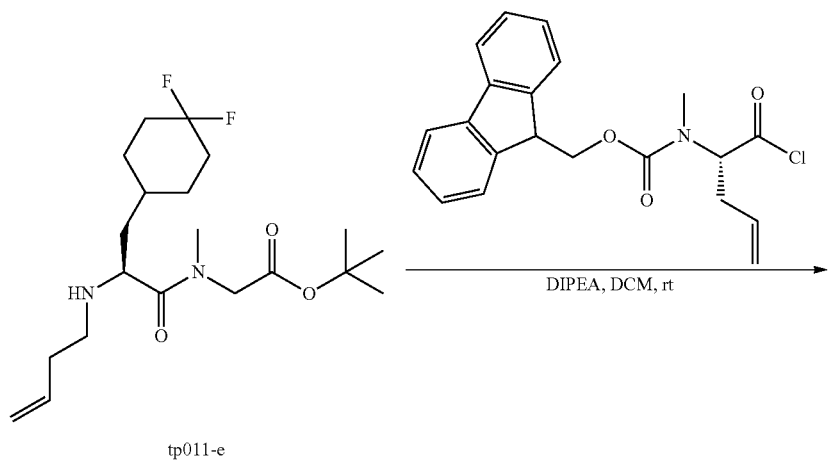
tp011-e
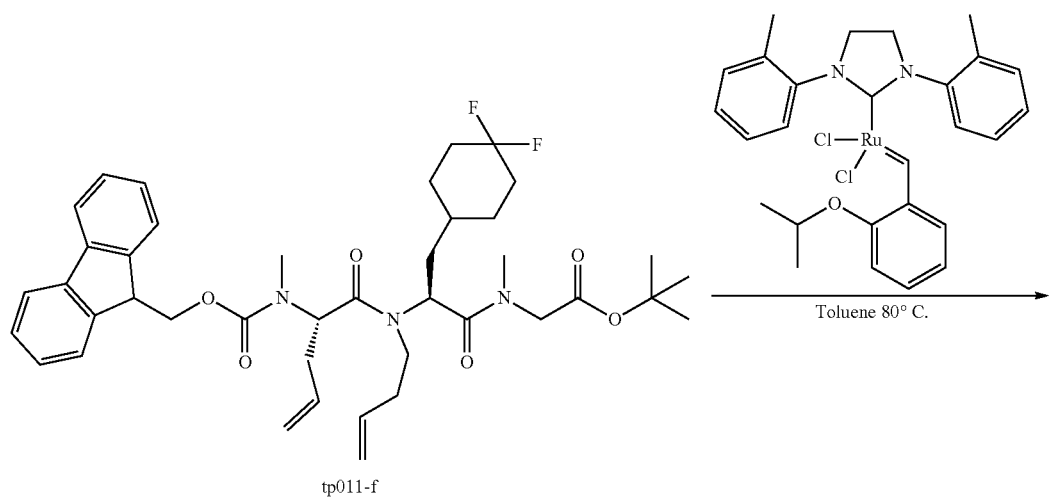
tp011-f
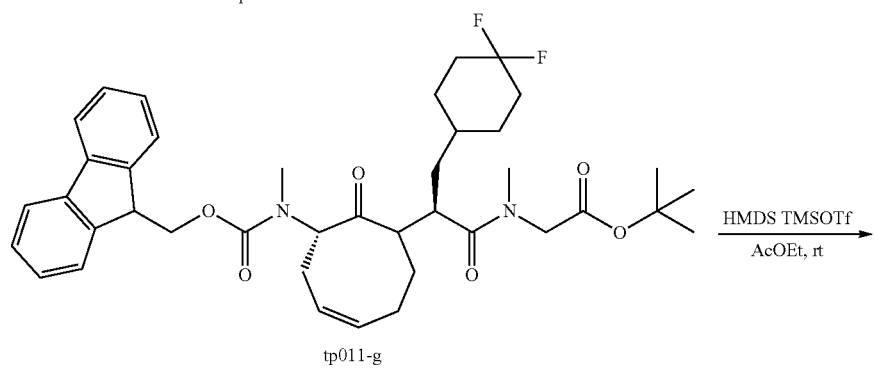
tp011-g

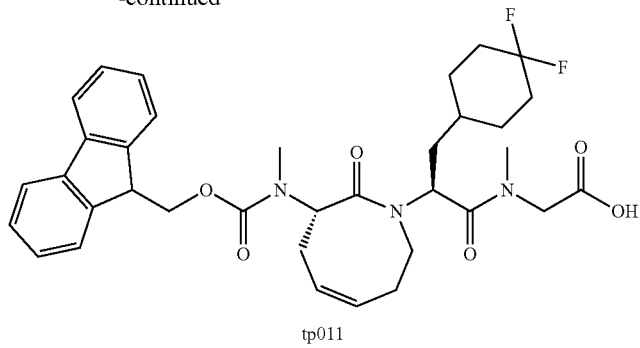

tp011

Using Compound tp011-a ((S)-2-((((9H-fluoren-9-yl) methoxy) carbonyl)amino)-3-(4,4-difluorocyclohexyl) propanoic acid)(14.0 g, 32.6 mmol) as a starting material, a crude product tp011-b (14.4 g, quant.) was obtained in the same manner as synthesis of Compound tp006-b.

LCMS (ESI) m/z=464 (M+Na)+
Retention time: 0.69 min (Analytical condition SQDAA50_2)

Using the resulting crude product tp011-b (14.4 g, 32.6 mmol), Compound tp011-c (11.6 g, 73%) was obtained in the same manner as synthesis of Compound tp006-c. LCMS (ESI) m/z=484 (M+H)+
Retention time: 0.65 min (Analytical condition SQDAA50_2)

Using Compound tp011-c (11.6 g, 23.9 mmol), a toluene solution of Compound tp011-d was obtained in the same manner as synthesis of Compound tp006-d. The resulting solution of Compound tp011-d was directly used in the next reaction.

LCMS (ESI) m/z=611 (M+H)+
Retention time: 0.82 min (Analytical condition SQDAA50_2)

Using a toluene solution of the above Compound tp011-d (23.9 mmol), Compound tp011-e (8.6 g, 92%) was obtained in the same manner as synthesis of Compound tp-006-e.

LCMS (ESI) m/z=389 (M+H)+
Retention time: 0.58 min (Analytical condition SQDAA50_2)

Using Compound tp011-e (4.3 g, 11.0 mmol), Compound tp011-f (6.9 g, 87%) was obtained in the same manner as synthesis of Compound tp006-f.

LCMS (ESI) m/z=744 (M+Na)+
Retention time: 0.86 min (Analytical condition SQDAA50_2)

Using Compound tp011-f (6.9 g, 9.6 mmol), Compound tp011-g (4.8 g, 72%) was obtained in the same manner as synthesis of Compound tp010-g.

LCMS (ESI) m/z=716 (M+Na)+
Retention time: 0.79 min (Analytical condition SQDAA50_2)

Using Compound tp011-g (4.8 g, 7.0 mmol), Compound tp011 (2.8 g, 64%) was obtained in the same manner as synthesis of Compound tp006.

LCMS (ESI) m/z=660 (M+Na)+
Retention time: 0.63 min (Analytical condition SQDFA40)

Synthesis of Compound tp007

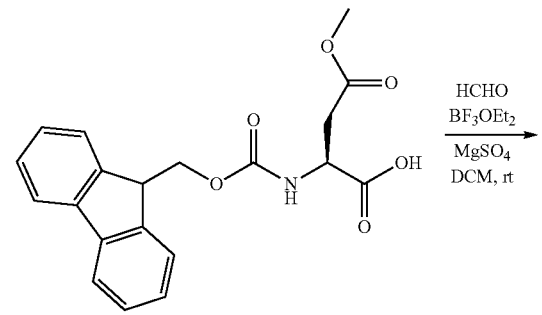

tp007-a

-continued
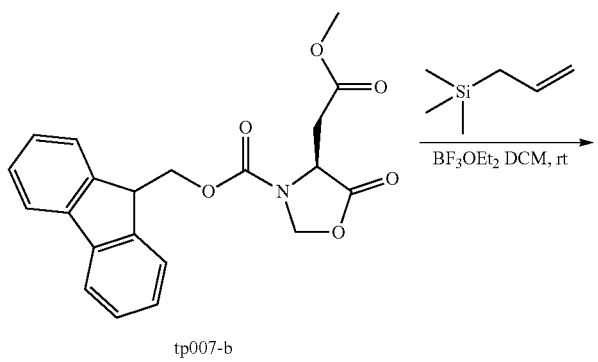
tp007-b
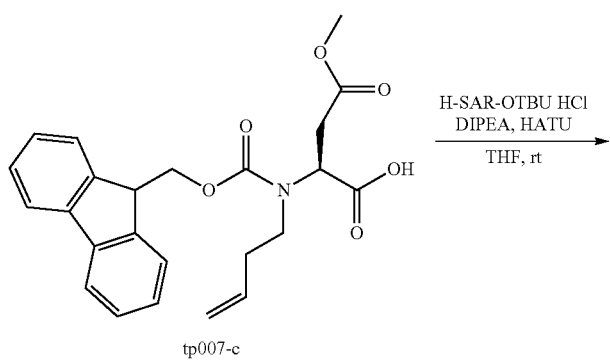
tp007-c
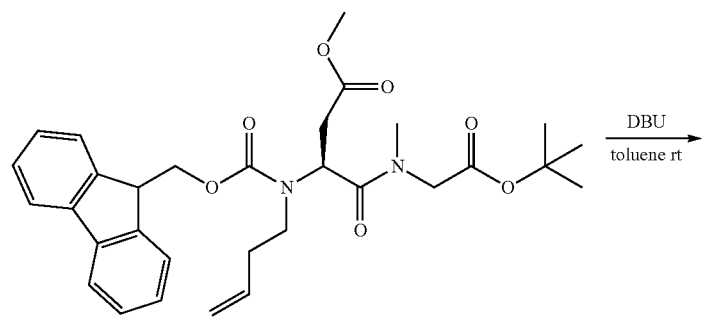
tp007-d
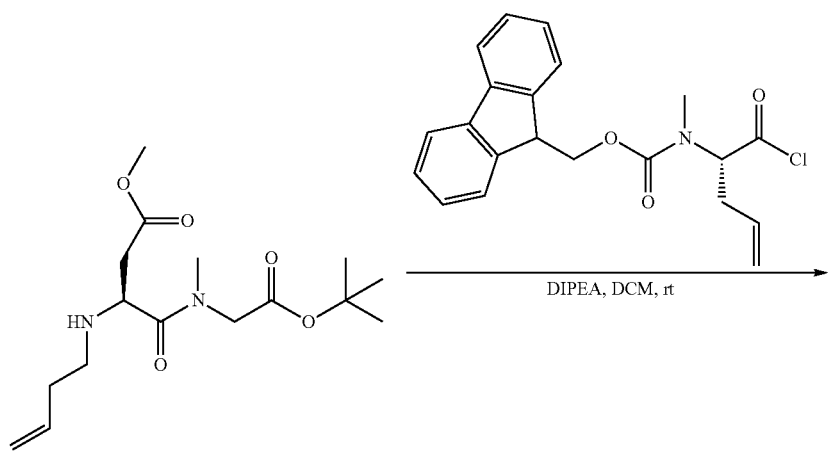
tp007-e -continued
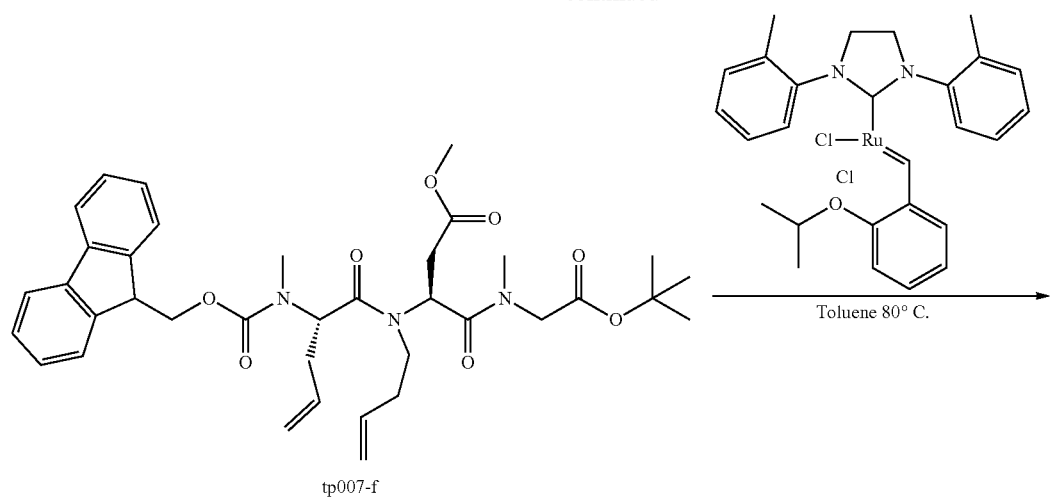
tp007-f
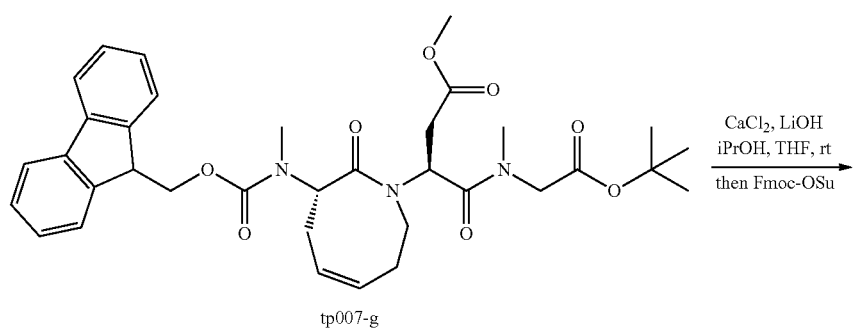
tp007-g
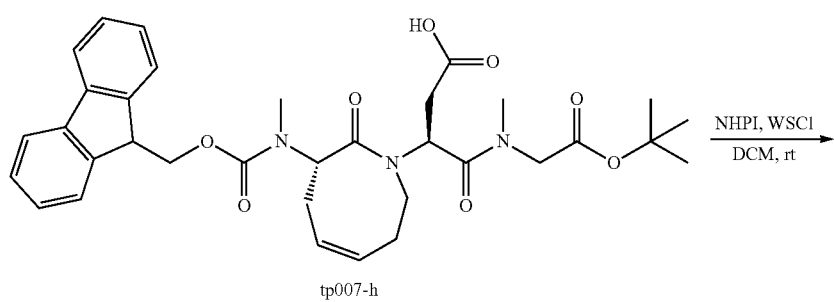
tp007-h
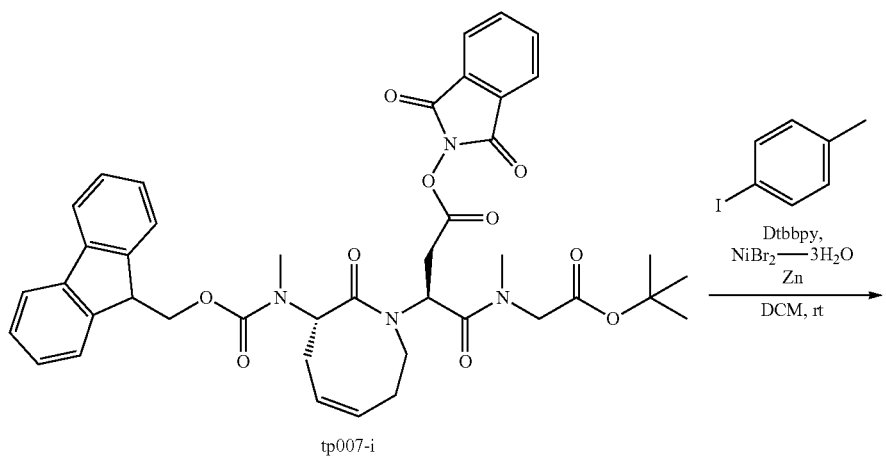
tp007-i -continued

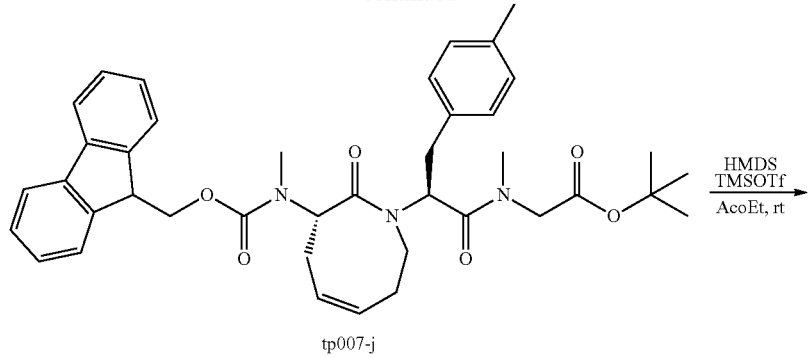

tp007-j

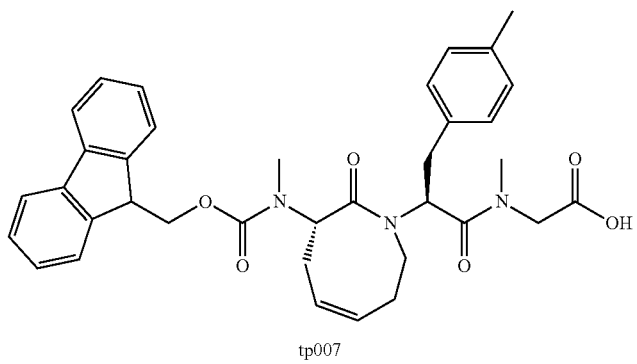

tp007

Compound tp007-a ((S)-2-((((9H-fluoren-9-yl)methoxy)carbonyl)amino)-4-methoxy-4-oxobutanoic acid)(30.0 g, 81.0 mmol) as a starting material was reacted in the same manner as synthesis of Compound tp006-b, and the filtrate obtained by Celite-filtering the reaction solution was regarded as Compound tp007-b and directly used in the next reaction.

LCMS (ESI) m/z=382 (M+H)+

Retention time: 1.22 min (Analytical condition SMD method_04)

Using a dichloromethane solution of the above Compound tp007-b (81.0 mmol), Compound tp007-c (35.9 g, quant.) was obtained in the same manner as synthesis of Compound tp006-c.

LCMS (ESI) m/z=424 (M+H)+

Retention time: 0.85 min (Analytical condition SMD method_10)

Compound tp007-c (34.3 g, 81.0) mmol) was dissolved in tetrahydrofuran (231 mL), reacted in the same manner as synthesis of tp006-d, and then purified by normal phase column chromatography (hexane/ethyl acetate) to give Compound tp007-d (44.4 g, 100%). LCMS (ESI) m/z=551 (M+H)+

Retention time: 1.45 min (Analytical condition SMD method_0) 4)

Using Compound tp007-d (44.4 g, 81.0 mmol), Compound tp007-e (23.3 g, 88%) was obtained in the same manner as synthesis of tp006-e.

LCMS (ESI) m/z=329 (M+H)+

Retention time: 0.58 min (Analytical condition SMD method_0) 4)

Using Compound tp007-e (23.3 g, 71.0 mmol), Compound tp007-f (43.5 g, 93%) was obtained in the same manner as synthesis of tp006-f.

LCMS (ESI) m/z=662 (M+H)+

Retention time: 1.54 min (Analytical condition SMD method_0) 4)

After a dichloroethane (996 mL) solution of a Stewart-Grubbs catalyst (0).47 g, 0.82 mmol) was degassed 4 times, a dichloroethane (100) mL) solution of Compound tp007-f (21.8 g, 32.9 mmol) was added dropwise over 1 hour while being stirred at 80° C. in a nitrogen atmosphere. The reaction mixture was stirred at 80° C. for 1 hour and then cooled to room temperature. The reaction mixture was concentrated under reduced pressure, and the resulting crude product was purified by reverse phase column chromatography (0).1% formic acid-containing acetonitrile/( ) 1% formic acid-containing distilled water) to give Compound tp007-g (20.8 g, 50%).

LCMS (ESI) m/z=634 (M+H)+

Retention time: 1.39 min (Analytical condition SMD method_0) 4)

After calcium chloride (61.1 g, 551 mmol) was dissolved in water (153 mL), lithium hydroxide monohydrate (6.16 g, 147 mmol) was added at room temperature. After the mixture was stirred for 5 minutes, isopropanol (612 mL) and a tetrahydrofuran solution (153 mL) of Compound tp007-g (23.3 g, 36.7 mmol) were added and stirred overnight at room temperature. Fmoc-OSu (12.4 g, 36.7 mmol) was added, the mixture was stirred for 2 hours, then water (460) mL, 20) v/w) was added, 2 N hydrochloric acid was added to adjust the pH to 2.5, and the mixture was extracted with ethyl acetate (460) mL, 20 v/w). The organic layer was washed with saturated brine (230) mL, 10) v/w) and concentrated under reduced pressure. Ethyl acetate (115 mL, 5 v/w), acetonitrile (115 mL, 5 v/w), and hexane (230) mL, 10) v/w) were added to and dissolve the resulting residue, and the mixture was extracted with a 3.5% aqueous potassium hydrogen carbonate solution (230) mL, 10) v/w). Phosphoric acid was added to the resulting aqueous layer to adjust the pH to 3, and then the mixture was extracted with ethyl acetate (115 mL, 5 v/w). The organic layer was washed with saturated brine (70) mL, 3 v/w) and concentrated under reduced pressure, and the resulting crude product was purified by reverse phase column chromatography (( ) 1%-formic acid containing acetonitrile/( ) 1% formic acid-containing distilled water) to give Compound tp007-h (12.6 g, 56%).

LCMS (ESI) m/z=620)(M+H)+

Retention time: 0.94 min (Analytical condition SMD method_10))

1-(3-Dimethylaminopropyl)-3-ethylcarbodiimide hydrochloride (5.87 g, 30.6 mmol) was added to a dichloromethane (93 ml) suspension of Compound tp007-h (12.6 g, 20.4 mmol) and N-hydroxyphthalimide (3.66 g, 22.4 mmol), and the mixture was stirred at room temperature for 2.5 hours. The reaction mixture was washed with water, then the organic layer was concentrated under reduced pressure, and the resulting crude product was purified by normal phase column chromatography (hexane/ethyl acetate) to give Compound tp007-i (15.1 g, 97%). LCMS (ESI) m/z=765 (M+H)+

Retention time: 1.35 min (Analytical condition SMD method_05)

Nickel (II) bromide trihydrate (2.47 g, 6.46 mmol) and 4,4'-di-tert-butyl-2,2'-bipyridine (1.73 g, 6.46 mmol) were dissolved in DMA (20 mL) to prepare a nickel solution. The nickel solution prepared in advance and chlorotrimethylsilane (0).41 mL, 3.23 mmol) were added to a DMA (110 mL) suspension of Compound tp007-i (4.94 g, 6.46 mmol), zinc powder (6.33 g, 97.0) mmol), and 1-iodo-4-methylbenzene (14.1 g, 64.6 mmol), and the mixture was stirred at room temperature for 2 hours. The resulting reaction mixture was purified by reverse phase column chromatography (( ) 1% formic acid-containing acetonitrile/0).1% formic acid-containing distilled water) to give Compound tp007-j (2.7 g, 63%).

LCMS (ESI) m/z=666 (M+H)+

Retention time: 1.57 min (Analytical condition SMD method_04)

Using Compound tp007-j (2.6 g, 3.90 mmol), Compound tp007 (1.78 g, 45%) was obtained in the same manner as synthesis of tp006.

LCMS (ESI) m/z=610 (M+H)+

Retention time: 1.26 min (Analytical condition SMD method_0) 4)

Synthesis of Compound tp008

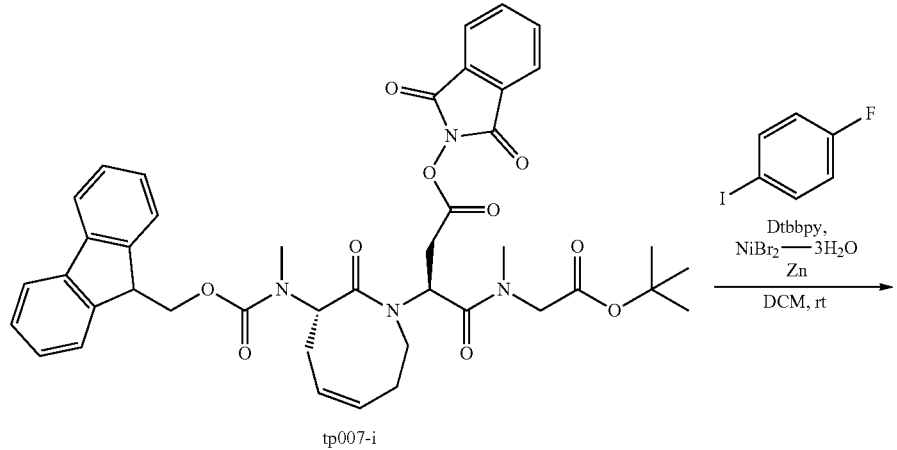

tp007-i

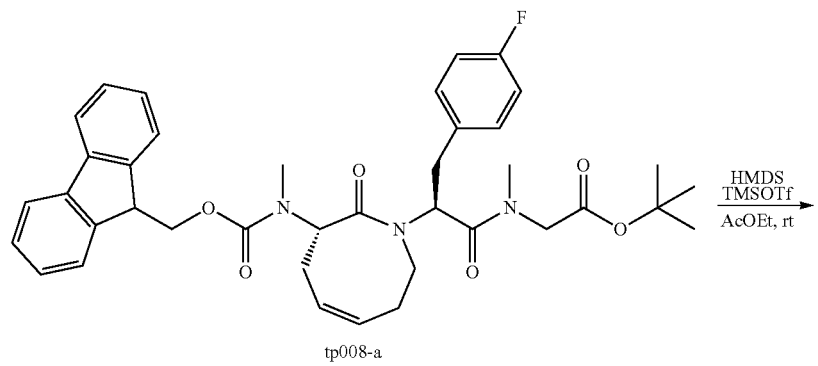

tp008-a

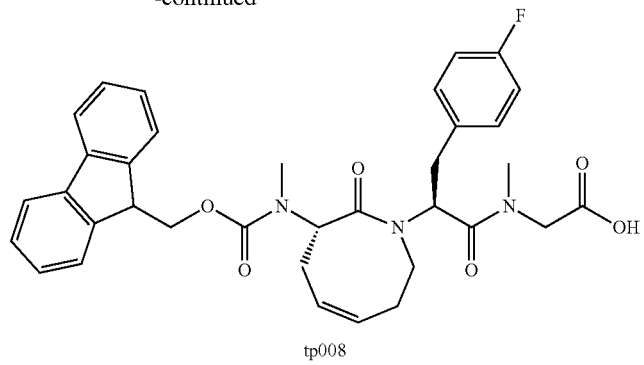

tp008

In a nitrogen atmosphere, nickel (II) bromide trihydrate (1.33 g, 4.89 mmol) and 4,4'-di-tert-butyl-2,2'-bipyridine (1.31 g, 4.89 mmol) were dissolved in DMA (48.9 mL), and the mixture was stirred at room temperature for 30 minutes to prepare a nickel solution. The nickel solution prepared in advance and chlorotrimethylsilane (0.31 mL, 2.45 mmol) were added to a DMA (48.9 mL) suspension of Compound tp007-i (3.74 g, 4.89 mmol), zinc powder (4.80 g, 73.3 mmol), and 1-fluoro-4-iodobenzene (10.2 mL, 88.0 mmol), and the mixture was stirred at room temperature for 1 hour. The resulting reaction mixture was filtered through Celite, and the filtrate was washed with an aqueous ammonium chloride solution (37 mL, 10 v/w). The organic layer was dried over anhydrous magnesium sulfate and then filtered, and the solution was concentrated under reduced pressure. The resulting crude product was purified by normal phase silica gel chromatography (hexane/ethyl acetate) to give Compound tp008-a (2.97 g, 72%). LCMS (ESI) m/z=670 (M+H)+

Retention time: 1.39 min (Analytical condition SMD method_05)

Using Compound tp008-a (2.97 g, 4.43 mmol), Compound tp008 (2.36 g, 87%) was obtained in the same manner as synthesis of tp006.

LCMS (ESI) m/z=614 (M+H)+

Retention time: 1.22 min (Analytical condition SMD method_04)

Synthesis of Compound tp009

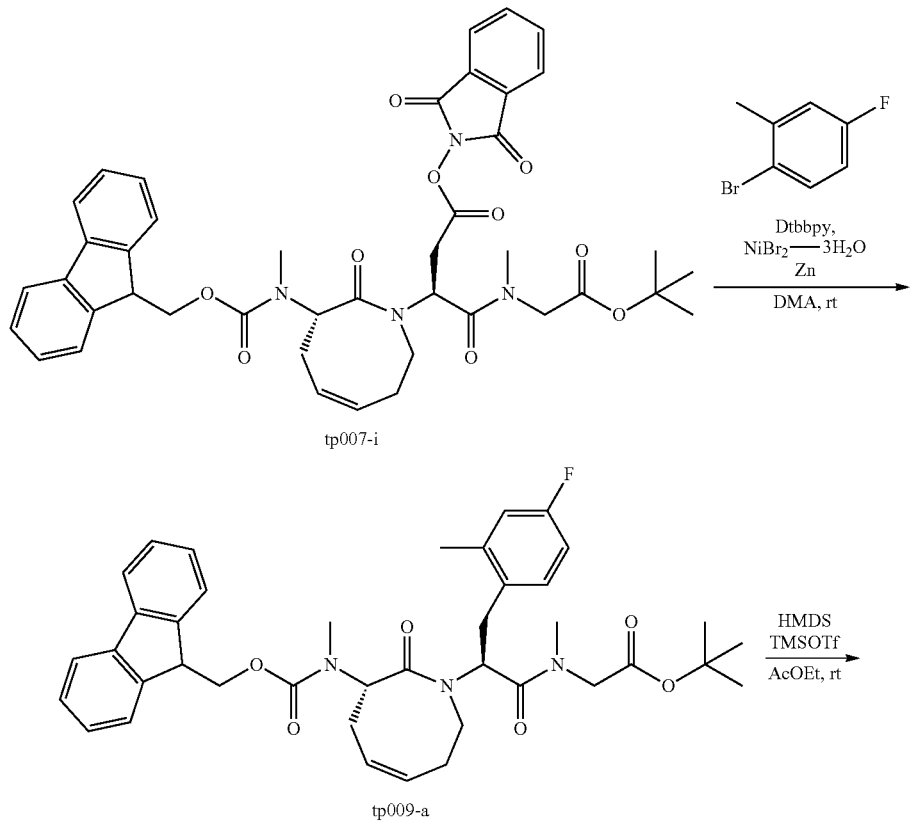

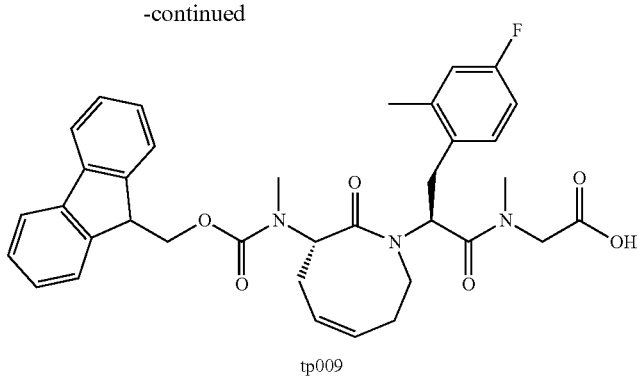

tp009

In a nitrogen atmosphere, nickel (II) bromide trihydrate (1.76 g, 6.41 mmol) and 4,4'-di-tert-butyl-2,2'-bipyridine (1.72 g, 6.41 mmol) were dissolved in DMA (64.1 mL) to prepare a nickel solution. The nickel solution prepared in advance and chlorotrimethylsilane (0.41 mL, 3.20 mmol) were added to a DMA (64.1 mL) suspension of Compound tp007-i (4.90 g, 6.41 mmol), zinc powder (6.28 g, 96.0 mmol), and 1-bromo-4-fluoro-2-methylbenzene (16.2 mL, 128 mmol), and the mixture was stirred at room temperature for 2 hours. The resulting reaction mixture was filtered through Celite, and a 15% aqueous ammonium chloride solution (150 mL, 30 v/w) was added to the filtrate to separate the organic layer. After the organic layer was washed with an 8% aqueous EDTA disodium solution (150 mL, 30 v/w) and 10% brine (150 mL, 30 v/w), the organic layer was dried over anhydrous magnesium sulfate and then filtered, and the solution was concentrated under reduced pressure. The resulting crude product was purified by normal phase silica gel chromatography (hexane/ethyl acetate) to give Compound tp009-a (2.43 g, 55%).

LCMS (ESI) m/z=684 (M+H)+

Retention time: 1.42 min (Analytical condition SMD method_05)

Using Compound tp009-a (2.42 g, 3.54 mmol), Compound tp009 (1.76 g, 79%) was obtained in the same manner as synthesis of tp006.

LCMS (ESI) m/z=628 (M+H)+

Retention time: 1.26 min (Analytical condition SMD method_04)

Synthesis of Compound tp012

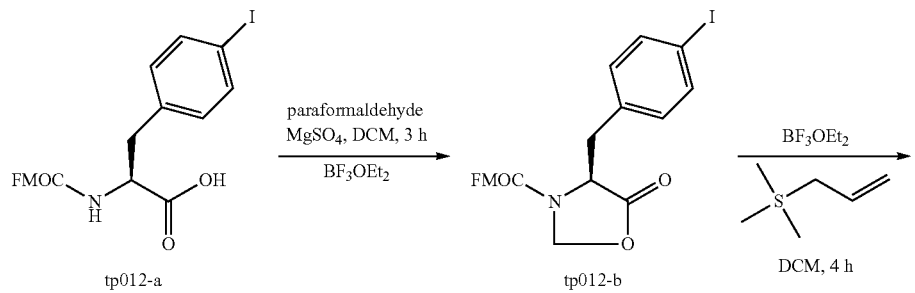

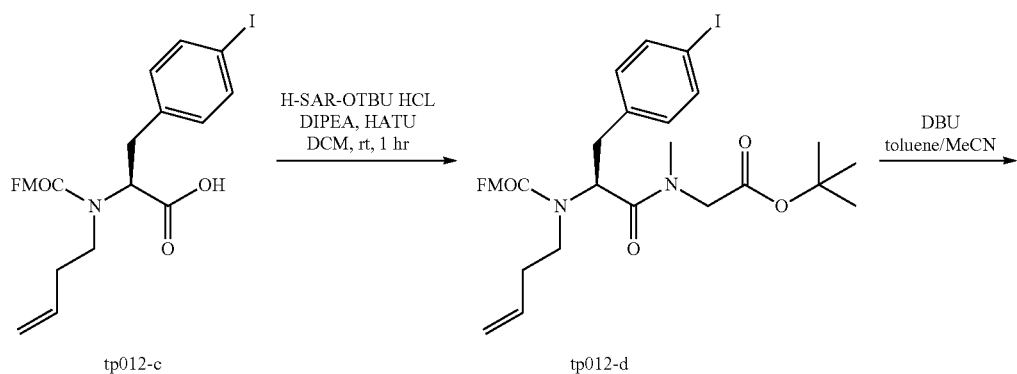

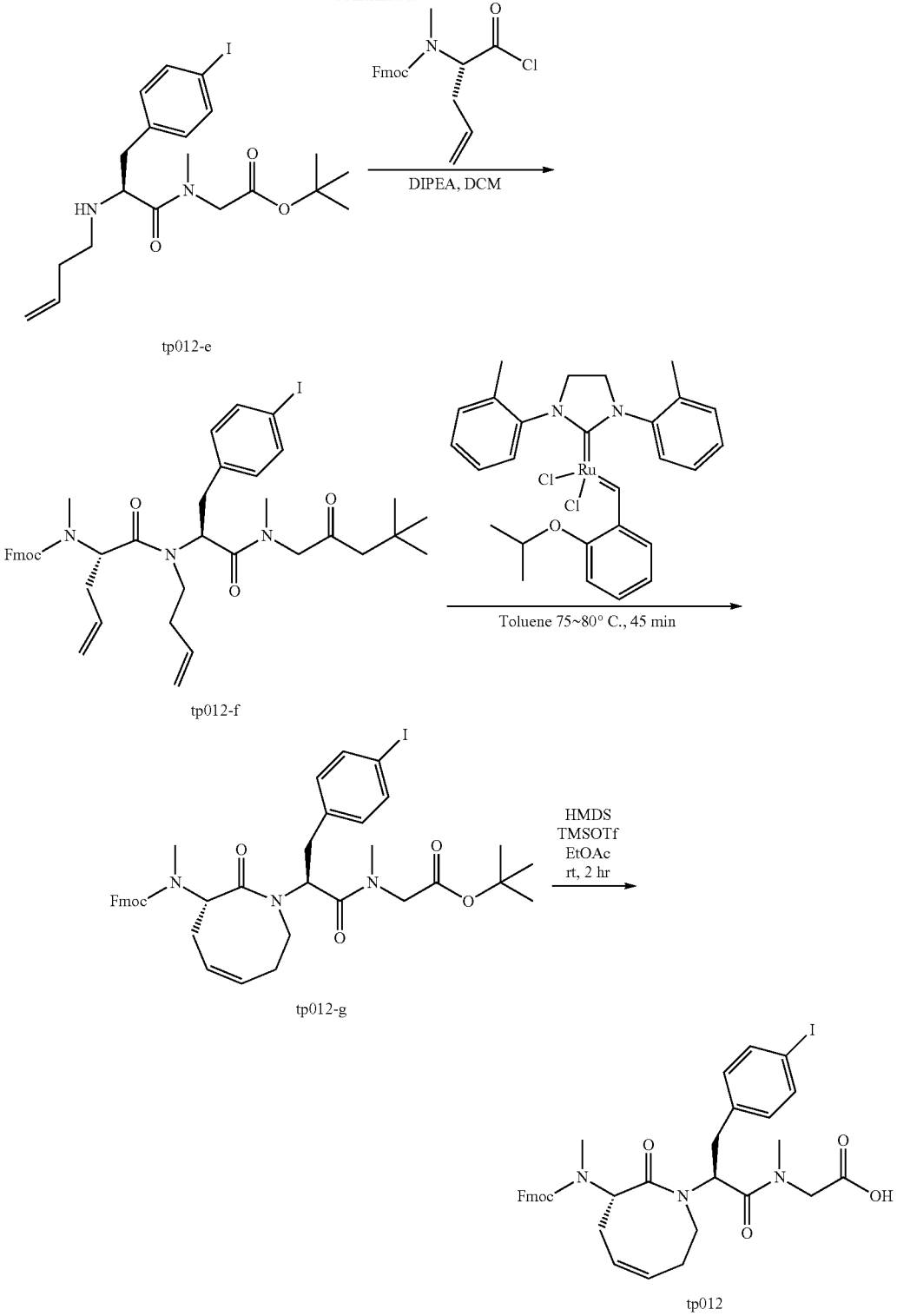

tp012-a (4.88 g, 9.51 mmol) was dissolved in dichloromethane (95 mL), then anhydrous magnesium sulfate (2.86 g, 23.8 mmol), paraformaldehyde (856 mg, 28.5 mmol), and a boron trifluoride diethyl ether complex (1.2 mL, 9.51 mmol) were added, and the mixture was stirred at room temperature for 3 hours. The reaction solution was filtered through silica gel, silica gel was washed with dichloromethane (100 mL), and the filtrate was concentrated under reduced pressure to give a crude product (4.50 g) of tp012-b.

LCMS (ESI) m/z=548 (M+Na)+

Retention time: 1.10 min (Analytical condition SQDAA05)

In a nitrogen atmosphere, the above tp012-b (9.51 mmol) was dissolved in dichloromethane (95 mL), then allyltrimethylsilane (10.6 mL, 66.6 mmol) and a boron trifluoride diethyl ether complex (6.0 mL, 47.6 mmol) were added, and the mixture was stirred at room temperature for 88 hours. The reaction solution was cooled to 0° C., and water (20 mL) was added. The mixed solution was filtered through Celite, and Celite was washed with dichloromethane (100 mL). The resulting filtrate was concentrated under reduced pressure, and the resulting residue was dissolved in toluene (50 mL) and washed with water (24 mL) and a 1 M aqueous dipotassium hydrogen phosphate solution (24 mL). Hexane (100 mL) was added to the organic phase, and the mixture was extracted 5 times with a 3.5% aqueous potassium hydrogen carbonate solution/acetonitrile (2/1, 42 mL). The aqueous phase was washed twice with hexane (40) mL), 2 N hydrochloric acid was added to adjust the pH to 2, and then the mixture was extracted 3 times with ethyl acetate (50 mL). The organic phase was washed with brine (24 mL) and concentrated under reduced pressure to give tp012-c (4.09 g, 76%). LCMS (ESI) m/z=568 (M+H)+

Retention time: 1.03 min (Analytical condition SQDFA05)

In a nitrogen atmosphere, tp012-c (3.09 g, 5.45 mmol) and sarcosine tert-butyl ester hydrochloride (989 mg, 5.45 mmol) were dissolved in dichloromethane (16 mL), then DIPEA (2.85 ml, 16.34 mmol) and HATU (2.49 g, 6.53 mmol) were added, and the mixture was stirred at room temperature for 1 hour. Subsequently, the reaction solution was successively washed with water (30 mL), a 3.5% aqueous potassium hydrogen carbonate solution (30 mL), and a 1 M aqueous dipotassium hydrogen phosphate solution (30 mL), and the organic phase was dried over anhydrous sodium sulfate. The resulting solution was concentrated under reduced pressure to give a crude product of tp012-d. The resulting tp012-d was directly used in the next step.

LCMS (ESI) m/z=695 (M+H)+

Retention time: 0.82 min (Analytical condition SQDFA50)

The crude product (5.45 mmol) of tp012-d was dissolved in toluene (32.7 mL) and acetonitrile (3.63 mL), DBU (0).81 mL) was added, and the mixture was stirred at room temperature for 20 minutes. A 1 M aqueous potassium dihydrogen phosphate solution (30 mL), n-hexane (60) mL), water (40) mL), acetonitrile (20 mL), and 2 N hydrochloric acid (4.2 mL) were added to the reaction solution and shaken, then the mixture separated into three layers. Water (40) mL), acetonitrile (20 mL), and toluene (20 mL) were further added, but the three-layer separation did not disappear, thus the upper-layer organic phase was discarded, and an aqueous 3 M potassium phosphate solution (4 mL) was added to the remaining lower two layers to adjust the pH to 8. The resulting mixed solution was extracted twice with ethyl acetate (30) mL), and the organic phase was washed with saturated brine (20 mL). The organic phase was dried over anhydrous sodium sulfate and concentrated under reduced pressure to give tp012-e (2.74 g, 85%, 2 steps).

LCMS (ESI) m/z=473.6 (M+H)+

Retention time: 0.57 min (Analytical condition SQDFA05)

In a nitrogen atmosphere, (S)-2-((((9H-fluoren-9-yl) methoxy) carbonyl)(methyl)amino) pent-4-enoic acid (2.80 g, 7.96 mmol) was dissolved in DCM (20 ml) at room temperature, DMF (0.062 ml, 0.796 mmol) was added, and then thionyl chloride (1.45 ml, 19.9 mmol) was added dropwise. The resulting reaction mixture was stirred for 20 minutes and then concentrated under reduced pressure. Toluene (7 ml) was added to the resulting residue, and the mixture was concentrated under reduced pressure. This operation was performed twice in total, and the resulting crude product was dissolved in DCM (16 mL.) and used in the subsequent reaction.

In a nitrogen atmosphere, a DCM (20 mL) solution of tp012-e (3.42 g, 7.24 mmol) and DIPEA (4.41 mL, 25.3 mmol) was added to the prepared DCM (16 ml) solution of (9H-fluoren-9-yl)methyl(S)-(1-chloro-1-oxopent-4-en-2-yl) (methyl) carbamate. The reaction solution was stirred at room temperature for 3 hours, and then washed with a 1 M aqueous potassium dihydrogen phosphate solution (35 mL). Subsequently, the organic phase was washed with a 3.5% aqueous potassium hydrogen carbonate solution (35 mL.) and concentrated under reduced pressure. The resulting crude product was purified by silica gel chromatography (n-hexane/ethyl acetate) to give tp012-f (4.45 g, 76%).

LCMS (ESI) m/z=806.5 (M+H)+

Retention time: 0.88 min (Analytical condition SQDAA50)

In a nitrogen atmosphere, tp012-f (2.79 g, 3.46 mmol) was dissolved in 1,2-dichloroethane (115 mL) in a three-neck flask, and a first-generation Grubbs catalyst (60 mg, 0.0715 mmol) was added. While warming to 80° C. and stirring the reaction solution, a 1,2-dichloroethane (15 mL) solution of a first-generation Grubbs catalyst (60 mg, 0.0715 mmol) was added dropwise over 2 hours with a syringe pump. Subsequently, the reaction solution was stirred at 80° C. for 1 hour, cooled to room temperature, and then concentrated under reduced pressure. To complete the reaction, the resulting crude product was again dissolved in 1,2-dichloroethane (115 mL) in a nitrogen atmosphere, a first-generation Grubbs catalyst (240 mg, ( )$_{286}$ mmol) was added, and the mixture was stirred at 80° C. for 90 minutes. The reaction solution was cooled to room temperature, and then concentrated under reduced pressure. The resulting crude product was purified by silica gel chromatography (n-hexane/ethyl acetate) to give tp012-g (1.57 g, 58%).

LCMS (ESI) m/z=778.5 (M+H)+

Retention time: 0.74 min (Analytical condition SQDFA50)

In a nitrogen atmosphere, tp012-g (1.57 g, 2.02 mmol) was dissolved in ethyl acetate (24 mL.), hexamethyldisilazane (1.481 mL, 7.07 mmol) was added, and then trimethylsilyl trifluoromethanesulfonate (1.02 mL., 5.65 mmol) was added dropwise. The resulting reaction mixture was stirred for 150) minutes, then the reaction solution was diluted with ethyl acetate (20) mL), and a 1 M aqueous disodium hydrogen phosphate solution (40 ml) was added to quench the reaction. The organic phase was separated, and the solvent was distilled off under reduced pressure. The resulting crude product was purified by reverse phase chromatography (0.1% formic acid-containing acetonitrile/0.1% formic acid-containing distilled water) to give tp012 (1.02 g, 70%).

LCMS (ESI) m/z=722 (M+H)+

Retention time: 0.47 min (Analytical condition SQDFA50)

Synthesis of Compound tp014

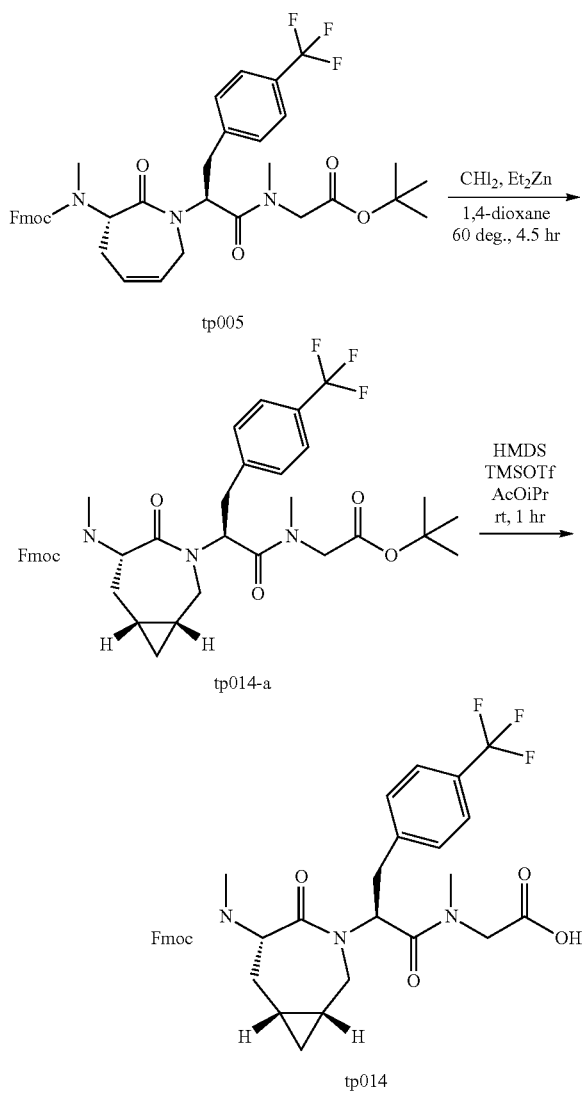

In a nitrogen atmosphere, tp005 (0.75 g, 1.06 mmol) was dissolved in 1,4-dioxane (5.3 mL), a 1 M diethylzinc toluene solution (5.31 mL, 5.31 mmol) was added, and then diiodomethane (0.856 mL, 10.63 mmol) was added dropwise. The reaction solution was heated to 60° C., stirred at 60° C. for 4 and a half hours and cooled to room temperature, and a saturated aqueous ammonium chloride solution was added to quench the reaction. The organic phase was separated, the aqueous phase was extracted with ethyl acetate, and the resulting organic phases were combined and concentrated under reduced pressure.

The same operation was repeated using tp005 (0.75 g, 1.06 mmol), and the resulting crude products were combined and purified by reverse phase chromatography (0.1% formic acid-containing acetonitrile/0.1% formic acid-containing distilled water) to give tp014-a (0.21 g, 14%). At this time, the raw-material tp005 (0.58 g, 39%) and a mixture of tp005 and tp014-a (3/2, 0.18 g, 12%) were also recovered.

LCMS (ESI) m/z=720.5 (M+H)+

Retention time: 0.74 min (Analytical condition SQDFA50)

In a nitrogen atmosphere, tp014-a (264 mg, 0.367 mmol) was dissolved in ethyl acetate (2.0 mL), hexamethyldisilazane (0.269 mL, 1.28 mmol) was added, and then trimethylsilyl trifluoromethanesulfonate (0.186 mL, 1.03 mmol) was added dropwise. The resulting reaction mixture was stirred for 1 hour, then the reaction solution was diluted with ethyl acetate (5 mL), and a 1 M aqueous disodium hydrogen phosphate solution (5 ml) was added to quench the reaction. The organic phase was separated, and the solvent was distilled off under reduced pressure. The resulting crude product was purified by reverse phase chromatography (0.1% formic acid-containing acetonitrile/0.1% formic acid-containing distilled water).

The same operation was repeated using tp014-a (142 mg, 0.197 mmol), hexamethyldisilazane (0.145 mL, 0.690 mmol), and trimethylsilyl trifluoromethanesulfonate (0.100 mL, 0.552 mmol), and, after reverse phase chromatography, the resulting products were combined to give tp014 (274 mg, 73%).

LCMS (ESI) m/z=664.5 (M+H)+

Retention time: 0.97 min (Analytical condition SQDFA50 long)

Synthesis of Compound tp015

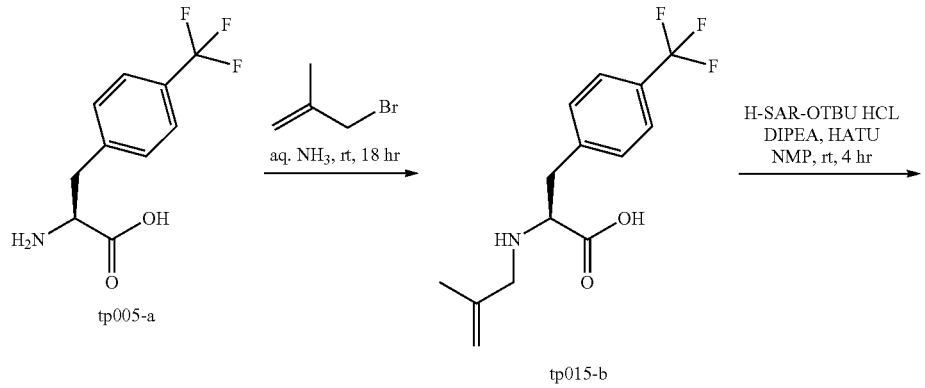

-continued
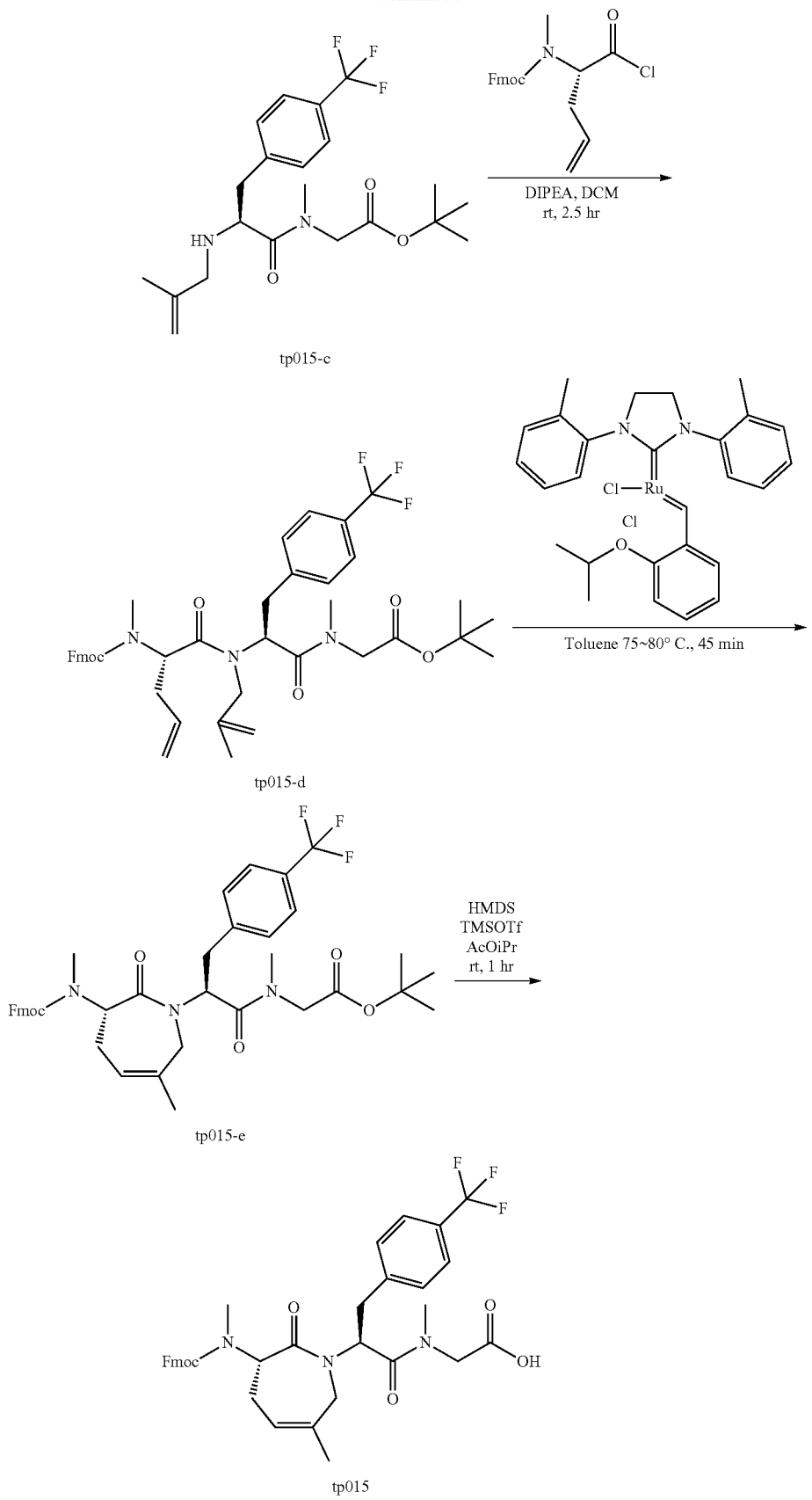
tp015-c
tp015-d
tp015-e
tp015

Aqueous ammonia (7.8 ml, 13.2 mmol) was added to a water (17.15 ml) suspension of tp005-a (2 g, 8.58 mmol) at room temperature to dissolve tp005-a, and then 3-bromo-2-methylpropene (5.19 ml, 51.5 mmol) was added dropwise. The reaction mixture was stirred at room temperature for 18 hours, ethanol (6 ml) was added, and the mixture was further stirred at room temperature for 2 hours. The resulting white solids were collected by filtration, washed with water, and the vacuum-dried to give tp015-b (2.61 g, quant.).

LCMS (ESI) m/z=289 (M+H)+

Retention time: 0.47 min (Analytical condition SQDFA05)

In a nitrogen atmosphere, dehydrated NMP (10 ml) was added to a mixture of tp015-b (1 g, 3.48 mmol) and sarcosine tert-butyl ester hydrochloride (1.26 g, 6.96 mmol). DIPEA (2.43 ml, 13.92 mmol) was added dropwise to the resulting suspension, the mixture was stirred for about 3 minutes, and then HATU (2.65 g, 6.96 mmol) was added. After the reaction mixture was stirred at room temperature for 4 hours, ethyl acetate (20 ml), water (10 ml), and a 5% aqueous sodium carbonate solution (10 ml) were added. The separated organic phase was washed with a 5% aqueous sodium carbonate solution (20 ml), a 5% aqueous potassium hydrogen sulfate solution (20 ml×2), and brine (20 ml), and dried over sodium sulfate. The crude product obtained by distilling off the solvent under reduced pressure was dissolved in TBME (5 ml), then hexane (5 ml) was added to precipitate the product, and the supernatant was removed. The operation of adding hexane (5 ml) and removing the supernatant was performed 2 more times, and vacuum drying was performed to give tp015-c (1.30 g, 90%).

LCMS (ESI) m/z=415 (M+H)+

Retention time: 0.55 min (Analytical condition SQDFA05)

In a nitrogen atmosphere, DIPEA (3.79 ml, 21.71 mmol) was added to a dehydrated DCM (20 ml) solution of tp015-c (3.0 g, 7.24 mmol). The resulting mixture was stirred while being cooled in a water bath (25° C.), and a separately prepared DCM (5 ml) solution of (9H-fluoren-9-yl)methyl (S)-(1-chloro-1-oxopent-4-en-2-yl)(methyl) carbamate (described below) was added dropwise over 5 minutes. The resulting reaction mixture was stirred at room temperature for 2.5 hours, and then the solvent was distilled off under reduced pressure. Ethyl acetate (30 ml) and water (12 ml) were added to the resulting residue. The separated organic phase was washed with brine (12 ml×2) and dried over sodium sulfate, and then the solvent was distilled off under reduced pressure. The resulting crude product was purified by normal phase silica gel chromatography (hexane/ethyl acetate) to give tp0) 15-d (4.56 g, 84%).

(9H-Fluoren-9-yl)methyl(S)-(1-chloro-1-oxopent-4-en-2-yl)(methyl) carbamate was prepared as follows.

In a nitrogen atmosphere, (S)-2-((((9H-fluoren-9-yl) methoxy) carbonyl)(methyl)amino) pent-4-enoic acid (2.8 g, 7.97 mmol) was dissolved in DCM (15 ml) at room temperature, DMF (0.031 ml, 0.398 mmol) was added, and then thionyl chloride (1.45 ml, 19.92 mmol) was added dropwise. The resulting reaction mixture was stirred for 20 minutes and then concentrated under reduced pressure. Toluene (5 ml) was added to the resulting residue, and the mixture was concentrated under reduced pressure. This operation was performed 3 times in total, and the resulting crude product was dissolved in DCM and used in the above-described reaction.

LCMS (ESI) m/z=749 (M+H)+

Retention time: 0.84 min (Analytical condition SQDFA05)

In a nitrogen atmosphere, tp015-d (1.1 g, 1.47 mmol) and a Stewart-Grubbs catalyst (0.042 g, 0.074 mmol) were dissolved in degassed dehydrated toluene (45 ml), and the mixture was stirred at 75° C. to 80° C. for 45 minutes. After cooling to room temperature, the solvent was distilled off under reduced pressure, and the resulting crude product was purified by normal phase silica gel chromatography (hexane/ethyl acetate) to give tp015-e (1.22 g, 94%). LCMS (ESI) m/z=721 (M+H)+

Retention time: 0.75 min (Analytical condition SQDFA05)

In a nitrogen atmosphere, tp015-e (1.0 g, 1.39 mmol) was dissolved in isopropyl acetate (5 ml), hexamethyldisilazane (0).728 ml, 3.47 mmol) was added, and then trimethylsilyl trifluoromethanesulfonate (0.5 ml, 2.78 mmol) was added dropwise. The resulting reaction mixture was stirred for 1 hour, and then 1 M dipotassium hydrogen phosphate (5 ml) was added to quench the reaction. The resulting mixture was extracted with ethyl acetate, the organic phase was washed with brine (10 ml×2) and dried over sodium sulfate, and then the solvent was distilled off under reduced pressure. The resulting crude product was purified by reverse phase chromatography (0.1% formic acid-containing acetonitrile/0).1% formic acid-containing distilled water) to give tp015 (1.0 g, 90%).

LCMS (ESI) m/z=665 (M+H)+

Retention time: 0.91 min (Analytical condition SQDFA05)

Synthesis of Compound tp016

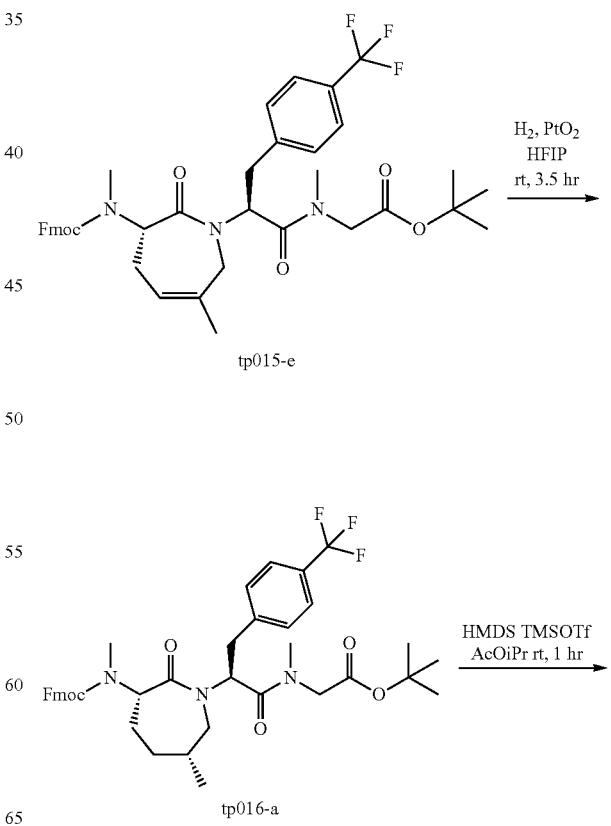

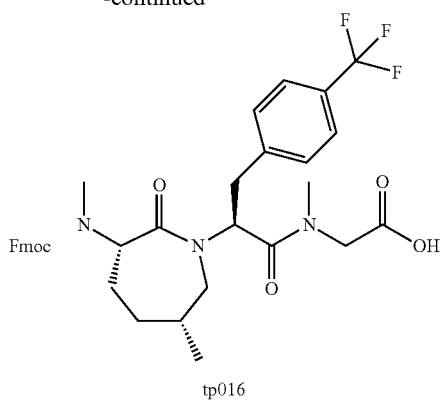

tp016

In a nitrogen atmosphere, 1,1,1,3,3,3-hexafluoropropan-2-ol (100 ml) was added to a mixture of tp015-e (4 g, 5.56 mmol) and platinum oxide (0.379 g, 1.67 mmol). The resulting mixture was depressurized while being stirred, and substituted with hydrogen. This hydrogen substitution operation was performed 3 times in total, and the mixture was stirred at room temperature for 3.5 hours in a hydrogen atmosphere. The reaction mixture was filtered through Celite and washed with ethyl acetate, and the solvent was distilled off under reduced pressure. The resulting crude product was purified by normal phase silica gel chromatography (hexane/ethyl acetate) to give tp016-a (3.05 g, 76%).

LCMS (ESI) m/z=723 (M+H)+

Retention time: 2.30 min (Analytical condition SQDFA50 long)

Using the resulting tp016-a, tp016 (2.61 g, 94%) was obtained under the same reaction conditions as synthesis of Compound tp015.

LCMS (ESI) m/z=666 (M+H)+

Retention time: 2.92 min (Analytical condition SQDFA05 long)

Synthesis of Compound tp019

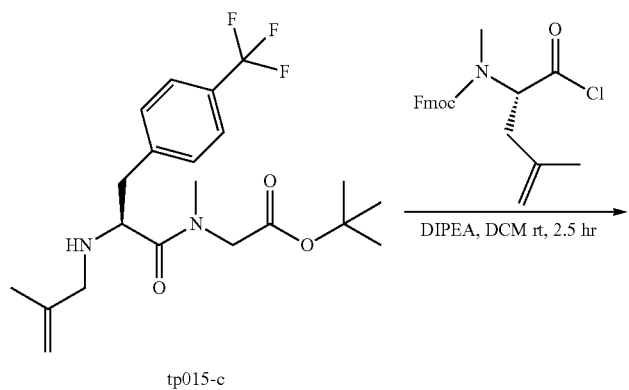

tp015-c

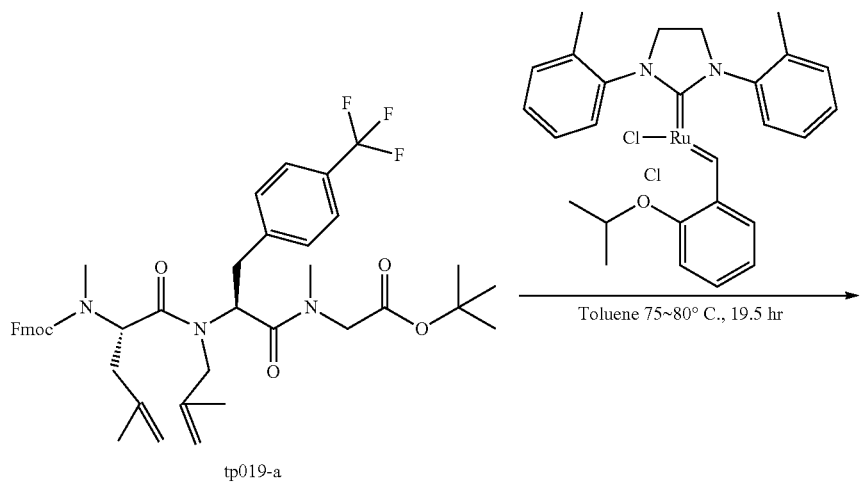

tp019-a

-continued

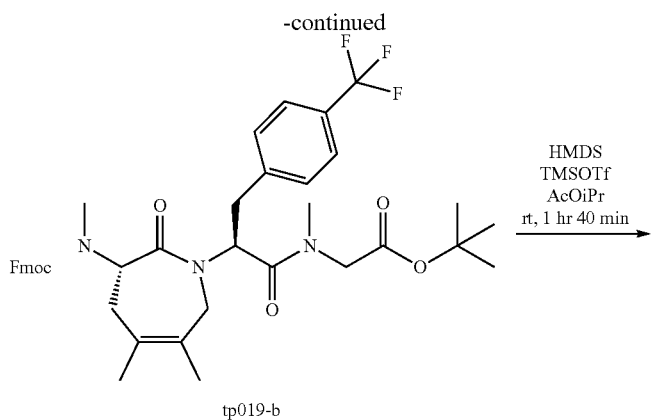
tp019-b

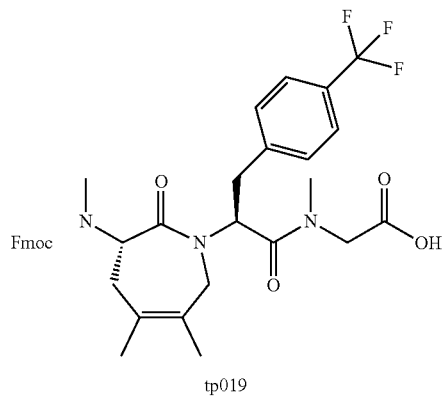
tp019

Using tp015-c as a starting material, tp0019-a (1.28 g, 70%) was obtained in the same manner as synthesis of Compound tp015-d.
LCMS (ESI) m/z=763 (M+H)+
Retention time: 3.13 min (Analytical condition SQDFA50 long)
Using the resulting tp019-a, tp019-b (0.667 g, 62%) was obtained under the same reaction conditions as synthesis of Compound tp015-e.
LCMS (ESI) m/z=735 (M+H)+

Retention time: 3.66 min (Analytical condition SQDFA05 long)
Using the resulting tp019-b, tp019 (0.54 g, 88%) was obtained under the same reaction conditions as synthesis of Compound tp015.
LCMS (ESI) m/z=679 (M+H)+
Retention time: 2.82 min (Analytical condition SQDFA05 long)

Synthesis of Compound tp021

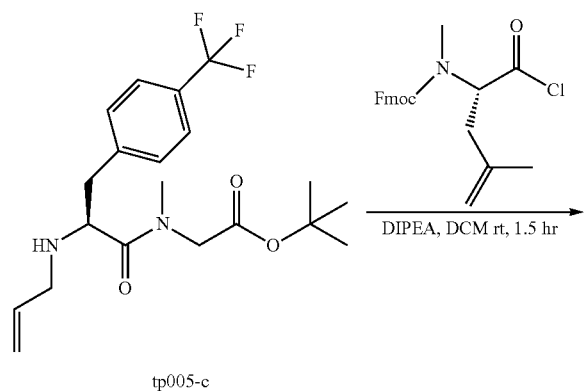
tp005-c

-continued

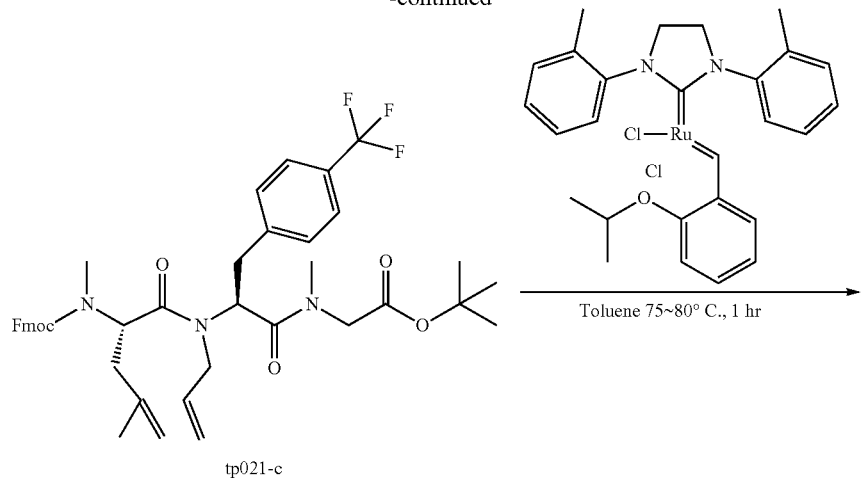
tp021-c

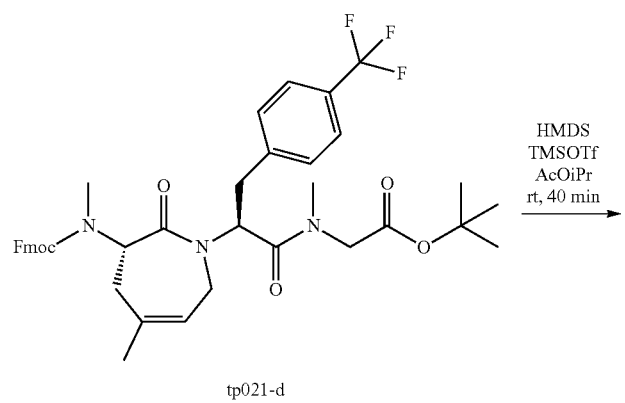
tp021-d

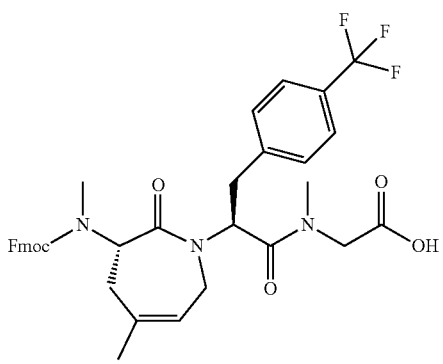
tp021

Using tp005-c, tp021-c (3.87 g, 72%) was obtained under the same reaction conditions as synthesis of Compound tp015-d.

LCMS (ESI) m/z=749 (M+H)+

Retention time: 2.88 min (Analytical condition SQDFA50 long)

Using the resulting tp021-c, tp021-d (3.35 g, 90%) was obtained under the same reaction conditions as synthesis of Compound tp015-e.

LCMS (ESI) m/z=720 (M+H)+

Retention time: 2.19 min (Analytical condition SQDFA50 long)

Using the resulting tp021-d, tp021 was obtained under the same reaction conditions as synthesis of Compound tp015 (1.13 g, 82%).

LCMS (ESI) m/z=664 (M+H)+

Retention time: 2.80 min (Analytical condition SQDFA05 long)

Synthesis of Compound tp020

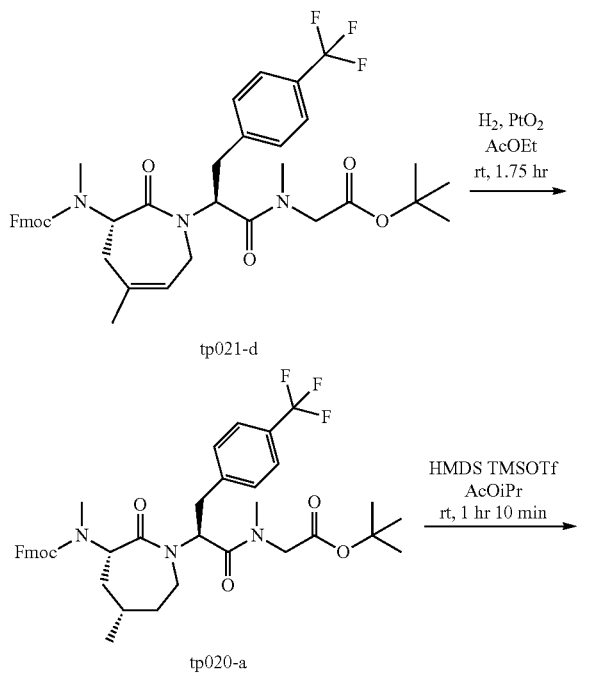

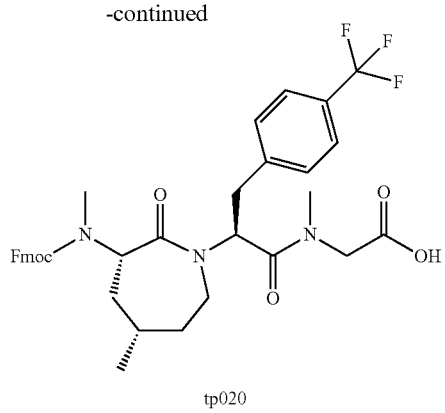

Using tp021-d as a starting material, tp0020-a (1.69 g, quant.) was obtained in the same manner as synthesis of Compound tp016-a.

LCMS (ESI) m/z=723 (M+H)+

Retention time: 2.35 min (Analytical condition SQDFA50 long)

Using the resulting tp020-a, tp020 (1.25 g, 77%) was obtained under the same reaction conditions as synthesis of Compound tp016.

LCMS (ESI) m/z=666 (M+H)+

Retention time: 2.91 min (Analytical condition SQDFA05 long)

Synthesis of Compounds tp017 and tp018

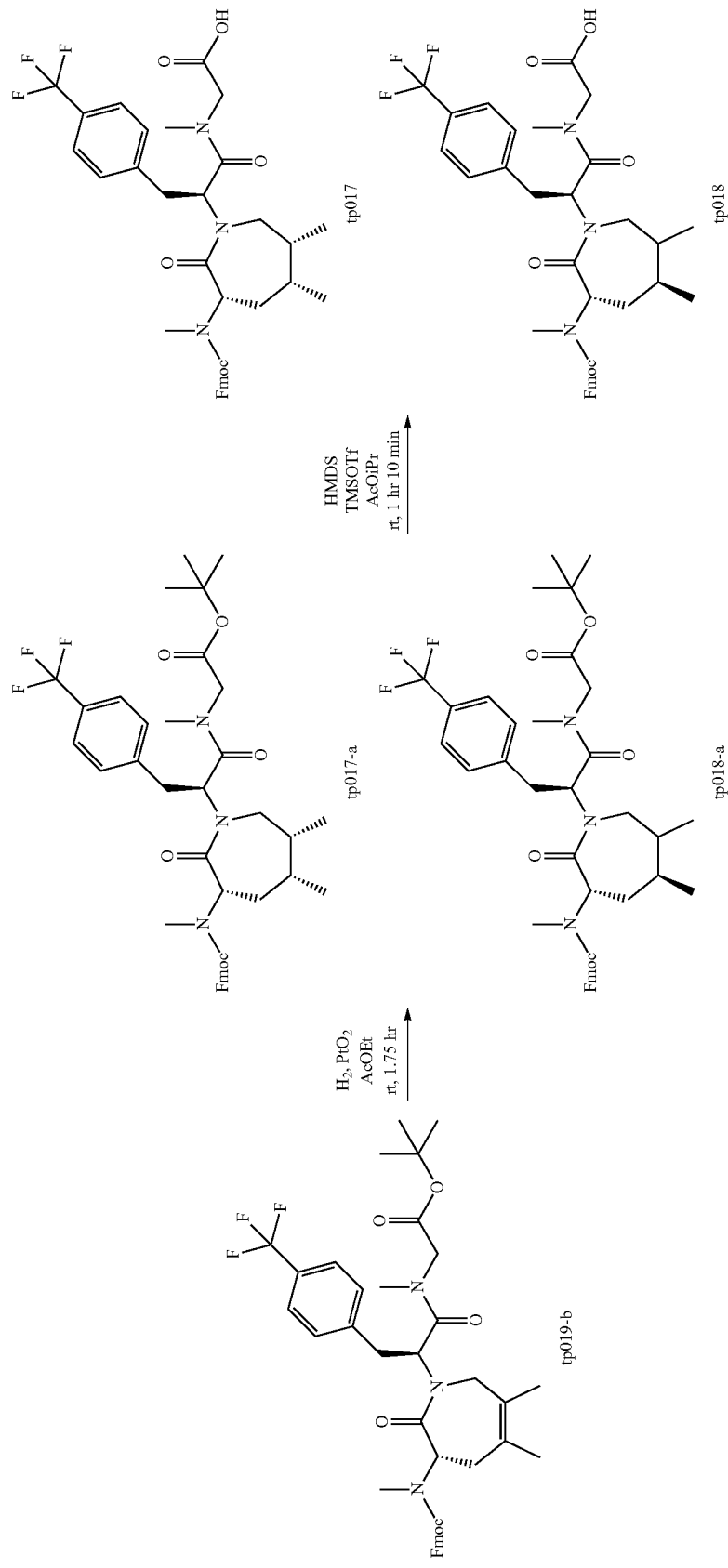

Using tp019-b as a starting material, a mixture of tp0017-a and tp018-a (2.3:1) was obtained (1.56 g, 58%) in the same manner as synthesis of Compound tp016-a.

LCMS (ESI) m/z=737 (M+H)+

Retention time: 2.51 min, 2.59 min (Analytical condition SQDFA50 long)

Using the resulting mixture of tp0017-a and tp018-a (2.3:1), a mixture of tp017 and tp018 (1.31 g, 91%) was obtained under the same reaction conditions as synthesis of Compound tp016.

LCMS (ESI) m/z=680 (M+H)+

Retention time: 3.04 min (Analytical condition SQDFA05 long)

tp017 and tp018 were not separated.

Synthesis of Compound tp022

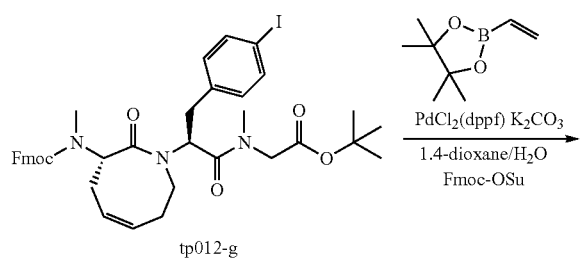

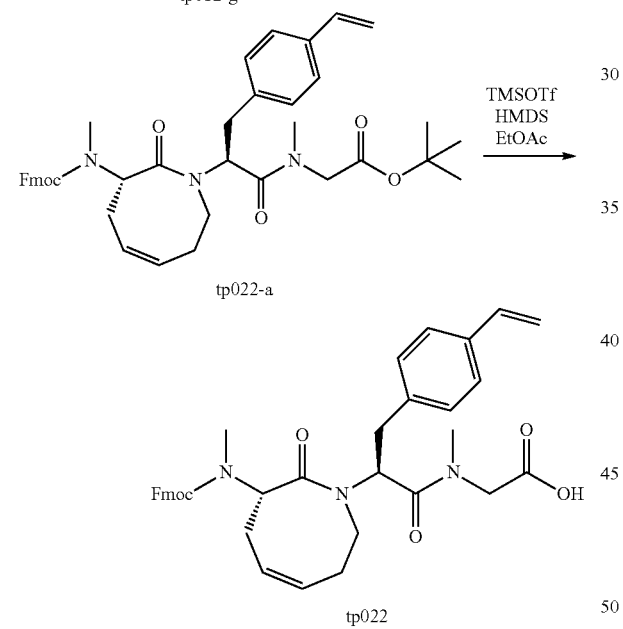

In a nitrogen atmosphere, tp012-g (20.1 g, 25.8 mmol) was dissolved in 1,4-dioxane (86 mL) and water (43 mL), and then potassium carbonate (10.7 g, 78.0 mmol), [1,1'-bis(diphenylphosphino) ferrocene] dichloropalladium (1.06 g, 1.29 mmol), and vinylboronic acid pinacol ester (5.97 g, 38.8 mmol) were added. The reaction solution was heated to 90° C. and stirred for 4 hours. The reaction solution was cooled to room temperature and left to stand still overnight, then Fmoc-OSu (4.36 g, 12.9 mmol) was added, and the mixture was stirred at room temperature for 1 hour. Ethyl acetate (200 mL) and half brine (200 mL) were added to the reaction solution and subjected to Celite filtration to isolate the organic phase. The organic phase was washed with half brine and dried over magnesium sulfate, and the resulting solution was concentrated under reduced pressure. The resulting crude product was purified by silica gel chromatography (n-hexane-ethyl acetate) to give a crude product of tp022-a (17.43 g). LCMS (ESI) m/z=678 (M+H)+

Retention time: 0.97 min (Analytical condition SMDFA50)

In a nitrogen atmosphere, the above tp022-a (17.43 g) was dissolved in ethyl acetate (129 mL), then hexamethyldisilazane (13.5 mL, 64.3 mmol) was added, and trimethylsilyl trifluoromethanesulfonate (9.29 mL, 51.4 mmol) was added dropwise over 3 minutes. After the resulting reaction mixture was stirred for 1 hour, a 5% aqueous disodium hydrogen phosphate solution (170 ml) was added to the reaction solution under ice cooling to quench the reaction. After the reaction solution was warmed to room temperature, water (85 mL) was added, and phosphoric acid was added to adjust the pH to 3. The organic phase was separated, and the solvent was distilled off under reduced pressure. The resulting crude product was purified by reverse phase chromatography (0.1% formic acid-containing acetonitrile/0.1% formic acid-containing distilled water) to give tp022 (7.60 g, 48%, 2 steps).

LCMS (ESI) m/z=622 (M+H)+

Retention time: 0.60 min (Analytical condition SMDFA50)

Synthesis of Compound tp023

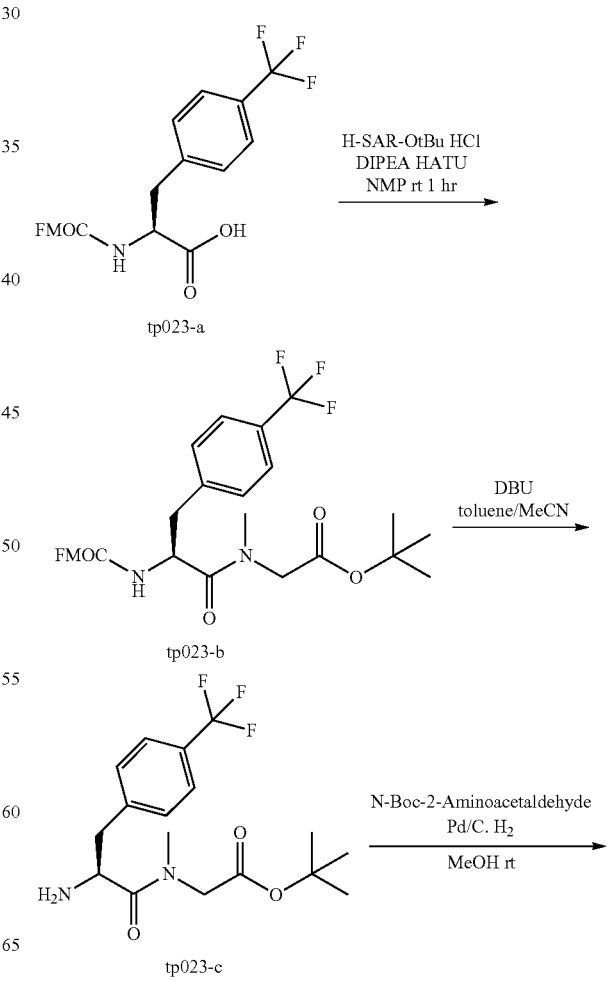

439
-continued

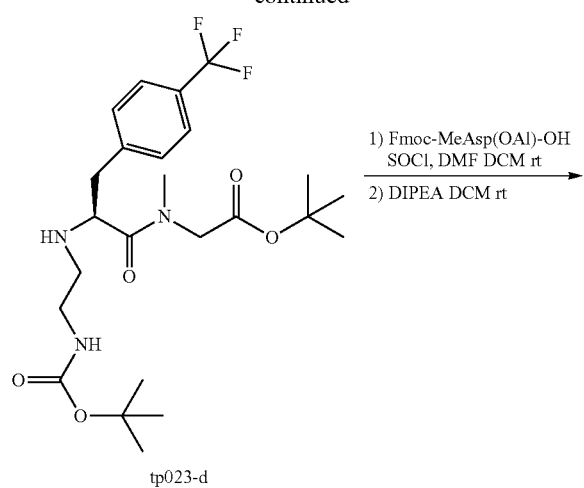

tp023-d

1) Fmoc-MeAsp(OAl)-OH
   SOCl, DMF DCM rt
2) DIPEA DCM rt

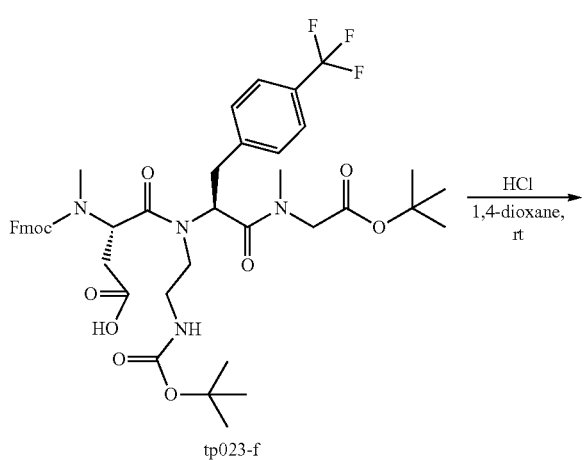

tp023-e

Pd(PPh₂)₂
PhSiH₃
DCM rt

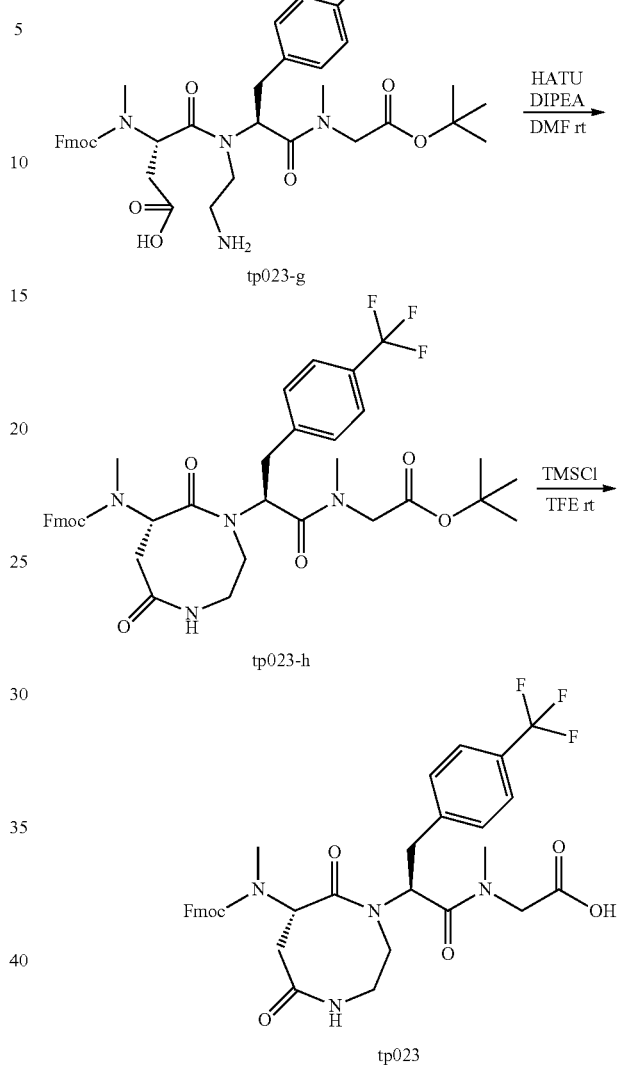

HCl
1,4-dioxane,
rt tp023-f

440
-continued tp023-g

HATU
DIPEA
DMF rt tp023-h

TMSCl
TFE rt tp023

In a nitrogen atmosphere, tp023-a (10.1 g, 22.2 mmol) and sarcosine tert-butyl ester hydrochloride (4.11 g, 22.6 mmol) were dissolved in NMP (55 mL), then DIPEA (11.6 ml, 66.5 mmol) and HATU (10.1 g, 26.6 mmol) were added, and the mixture was stirred at room temperature for 1.5 hours. Subsequently, the reaction solution was diluted with toluene (200 mL) and sequentially washed with water (100 mL), a 3.5% aqueous potassium hydrogen carbonate solution (100 mL), and a 1 M aqueous sodium dihydrogen phosphate solution (100 mL), and the organic phase was dried over anhydrous sodium sulfate. The resulting solution was concentrated under reduced pressure to give a crude product of tp023-b. The resulting tp0)₂₃-b was directly used in the next step.

LCMS (ESI) m/z=583 (M+H)+

Retention time: 1.03 min (Analytical condition SQDFA05)

The above crude product of tp023-b (22.2 mmol) was dissolved in toluene (130) mL), DBU (3.34 mL, 22.2 mmol) was added at 0° C. in a nitrogen atmosphere, and the mixture was stirred at ( ) C for 20 minutes. A 1 M aqueous sodium dihydrogen phosphate solution (100 mL) was added to the reaction solution, and the resulting precipitate was collected by filtration. The resulting precipitate was washed with toluene/n-hexane and water, and dried under reduced pressure to give the desired product. At this time, the organic phase was recovered from the filtrate and the washing solution, and extracted with ( )$_2$ N hydrochloric acid/acetonitrile (113 mL/50) mL) and water/acetonitrile (80) mL/40 mL). The aqueous phase was recovered, the pH was adjusted to 11 with a 3 N aqueous phosphoric acid solution, and this was extracted with ethyl acetate. The organic phase was dried over anhydrous sodium sulfate and concentrated under reduced pressure. The solids collected by filtration and the extract were combined to give tp023-c (7.56 g, 95%, 2 steps).

LCMS (ESI) m/z=361 (M+H)+

Retention time: 0.50 min (Analytical condition SQDFA05)

In a nitrogen atmosphere, N—BOC-2-aminoacetaldehyde (3.34 g, 21.0 mmol) was dissolved in methanol (210 mL) and ice-cooled to 0° C. 10% palladium carbon (1.67 g, 50 wt %) was added thereto, and then a methanol solution (6 mL) of tp023-c (7.56 g, 21.0 mmol) was added. The reaction solution was stirred at 0° C. for 2.5 hours at 1 atm of a hydrogen atmosphere, then heated to room temperature, and stirred for 1.5 hours. The reaction solution was subjected to Celite filtration, and the Celite was washed with ethyl acetate, followed by concentration under reduced pressure. The resulting crude product was purified by reverse phase chromatography (10) mM aqueous ammonium acetate solution-methanol) to give tp0)$_{23}$-d (7.03 g, 67%).

LCMS (ESI) m/z=505 (M+H)+

Retention time: 0.64 min (Analytical condition SQDFA05)

In a nitrogen atmosphere, Fmoc-MeAsp (OAl)—OH (Compound 358-c, 4.27 g, 10.4 mmol) was dissolved in DCM (26 ml) at room temperature, DMF (0).081 ml, 1.04 mmol) was added, and then thionyl chloride (2.08 ml, 28.7 mmol) was added dropwise. The resulting reaction mixture was stirred for 30 minutes, and then concentrated under reduced pressure. Toluene (30 ml) was added to the resulting residue, and the mixture was concentrated under reduced pressure. This operation was carried out twice in total, and the resulting crude product of Fmoc-MeAsp (OAl)—C1 was dissolved in DCM (10 mL) and used in the subsequent reaction.

In a nitrogen atmosphere, a DCM (30 mL) solution of tp023-d (3.07 g, 6.10 mmol) and DIPEA (6.05 mL, 34.7 mmol) was added to the prepared DCM (10 ml) solution of Fmoc-MeAsp (OAl)—C1. After the reaction solution was stirred at room temperature for 3 hours, a 3.5% aqueous potassium hydrogen carbonate solution (30) mL) was added. The organic phase was recovered and concentrated under reduced pressure. The resulting crude product was purified by reverse phase chromatography (0).1% formic acid-containing acetonitrile/0.1% formic acid-containing distilled water) to give tp023-e (4.72 g, 87%).

LCMS (ESI) m/z=896 (M+H)+

Retention time: 1.16 min (Analytical condition SQDFA50)

In a nitrogen atmosphere, tp023-e (4.72 g, 5.27 mmol) was dissolved in dichloromethane (53 mL), tetrakistriphenylphosphine palladium (183 mg, 0.158 mmol) was added, and then phenylsilane (0).454 mL., 3.69 mmol) was slowly added dropwise. The reaction solution was stirred at room temperature for 2.5 hours, and TBME (94 mL) was added. The organic phase was washed with 50% aqueous sodium hydrogen carbonate solution/acetonitrile (47 ml./9.4 mL.), and the organic phase was concentrated under reduced pressure. The resulting crude product was purified by reverse phase chromatography (0).1% formic acid-containing acetonitrile/0).1% formic acid-containing distilled water) to give tp023-f (3.99 g, 88%).

LCMS (ESI) m/z=856 (M+H)+

Retention time: 1.04 min (Analytical condition SQDFA05)

tp023-f (1.96 g, 2.29 mmol) was dissolved in 1,4-dioxane (40 mL), a 4 N hydrochloric acid/1,4-dioxane solution (20 mL) was added, and the mixture was stirred at room temperature for 4.5 hours. The reaction solution was concentrated under reduced pressure to give a crude product of tp023-g. The resulting crude product was directly used in the next step.

HATU (2.66 g, 7.00 mmol) was dissolved in DMF (75 mL), and a DMF solution (100 mL) of the above crude product of tp023-g and DIPEA (1.46 mL, 8.40) mmol) was added dropwise over 100 minutes. Thereafter, a saturated aqueous ammonium chloride solution (200 mL) was added to the reaction solution, and the resulting mixed solution was extracted twice with ethyl acetate (100 mL). The organic phases were combined and washed twice with water (100 mL) and once with brine (100 mL). The resulting organic phase was dried over anhydrous sodium sulfate and concentrated under reduced pressure. The resulting crude product was purified by reverse phase chromatography (0.1% formic acid-containing acetonitrile/0.1% formic acid-containing distilled water) to give tp023-h (0.56 g, 33%, 2 steps).

LCMS (ESI) m/z=738 (M+H)+

Retention time: 1.04 min (Analytical condition SQDFA50)

tp023-h (0.56 g, 0.760 mmol) was dissolved in 2,2,2-trifluoroethanol (10 mL), chlorotrimethylsilane (0.288 mL, 2.28 mmol) was added, and the mixture was stirred at room temperature for 1 hour. Chlorotrimethylsilane (0.15 mL, 1.19 mmol) was added to the reaction solution, then the mixture was stirred for 2.5 hours, chlorotrimethylsilane (0.05 mL, 0.396 mmol) was added, and the mixture was further stirred for 1.5 hours. The reaction solution was concentrated under reduced pressure, and the resulting crude product was purified by reverse phase chromatography (0.1% formic acid-containing acetonitrile/0.1% formic acid-containing distilled water) to give tp023 (0.28 g, 54%).

LCMS (ESI) m/z=682 (M+H)+

Retention time: 0.80 min (Analytical condition SQDFA50)

Synthesis of Compound tp024
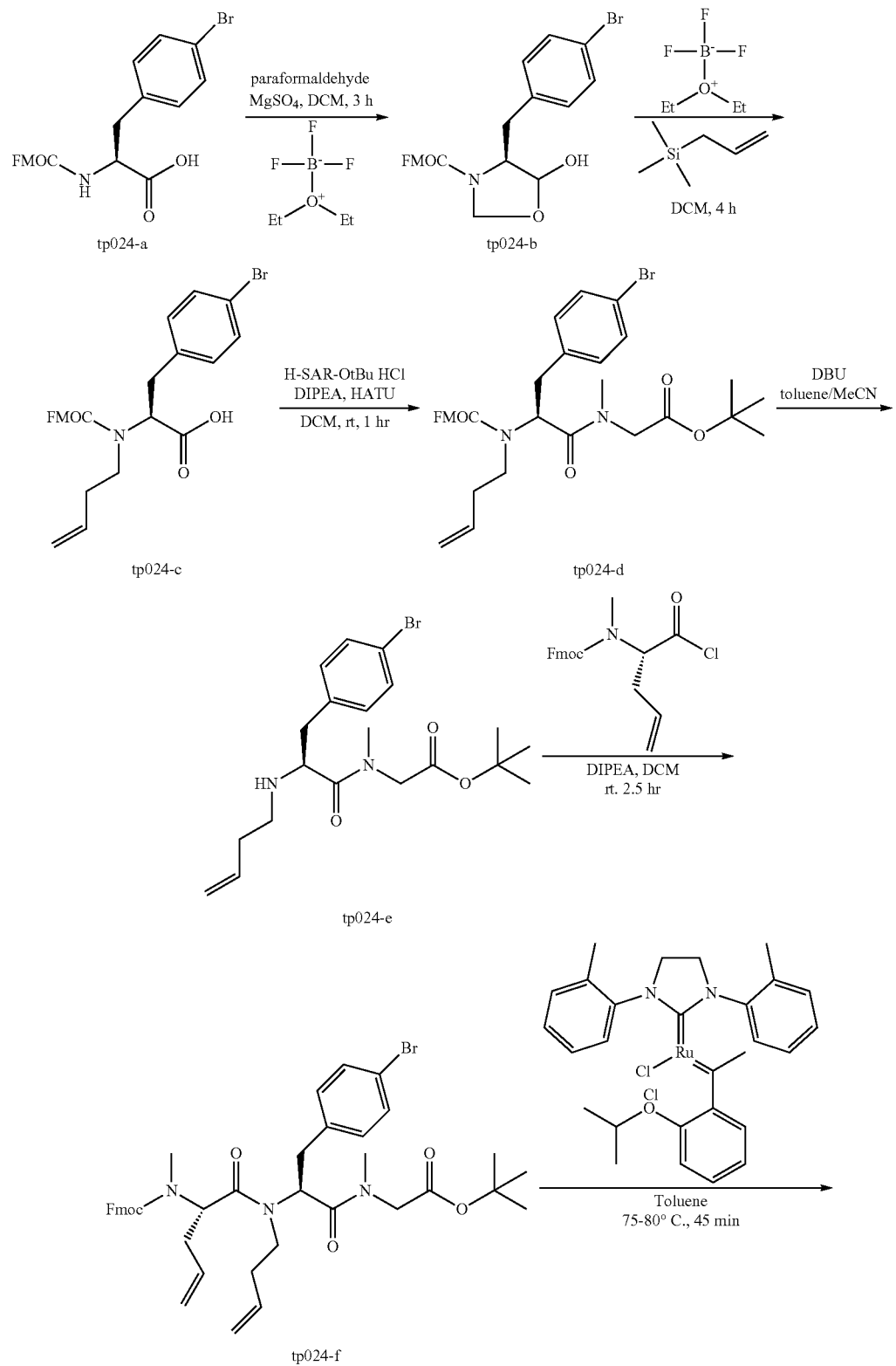

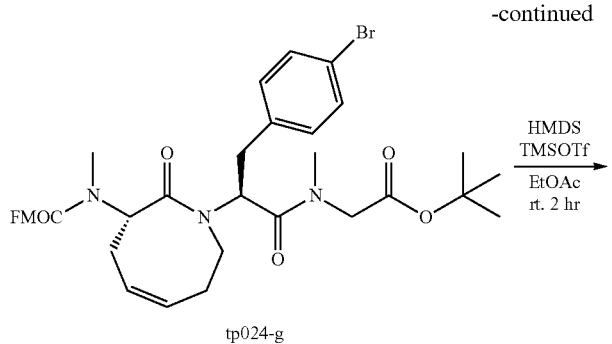

tp024-g

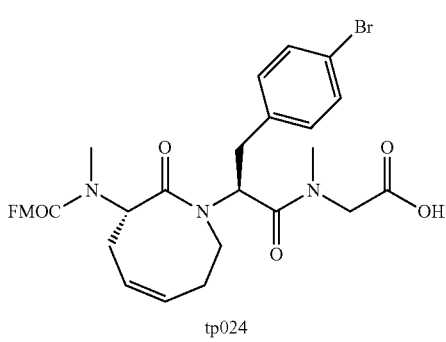

tp024 tp024-a (15.0 g, 32.2 mmol) was dissolved in dichloromethane (214 mL), then anhydrous magnesium sulfate (9.68 g, 80.0 mmol), paraformaldehyde (2.90 g, 96.0 mmol), and a boron trifluoride diethyl ether complex (4.08 mL, 32.2 mmol) were added, and the mixture was stirred at room temperature for 3 hours. The reaction solution was filtered through silica gel, the silica gel was washed with dichloromethane (200 mL), and the filtrate was concentrated under reduced pressure. The resulting crude product of tp024-b was directly used in the next reaction.

Retention time: 1.472 min (Analytical condition SMD method_04)

In a nitrogen atmosphere, the above crude product of tp0)$_{24}$-b (32.2 mmol) was dissolved in dichloromethane (322 mL.), then allyltrimethylsilane (35.8 ml., 225 mmol) and a boron trifluoride diethyl ether complex (20.2 mL., 161 mmol) were added, and the mixture was stirred at room temperature for 89 hours. The reaction solution was cooled to 0° C., and water (25 ml.) was added. The mixed solution was subjected to Celite filtration, and the Celite was washed with dichloromethane (100 mL). The resulting filtrate was washed with a 1 N aqueous dipotassium hydrogen phosphate solution (200 mL.) and half brine (100 ml.), dried over sodium sulfate, and concentrated under reduced pressure to give tp024-c (16.4 g, 98%, 2 steps). LCMS (ESI) m/z=520 (M+H)+

Retention time: 1.563 min (Analytical condition SMD method_0) 4)

In a nitrogen atmosphere, tp024-c (16.4 g, 31.5 mmol) and sarcosine tert-butyl ester hydrochloride (5.72 g, 31.5 mmol) were dissolved in dichloromethane (100 mL), then DIPEA (16.5 ml) and HATU (14.4 g, 37.8 mmol) were added, and the mixture was stirred at room temperature for 1 hour. Subsequently, the reaction solution was sequentially washed with water (100 mL.), a 3.5% aqueous potassium hydrogen carbonate solution (100 mL), and a 1 M aqueous dipotassium hydrogen phosphate solution (100 mL.), and the organic phase was dried over anhydrous sodium sulfate. The resulting solution was concentrated under reduced pressure to give a crude product of tp024-d. The resulting crude product was purified by silica gel chromatography (ethyl acetate-n-hexane) to give tp024-d (13.1 g, 64%).

LCMS (ESI) m/z=647 (M+Na)+

Retention time: 1.680) min (Analytical condition SMD method_0) 4) tp024-d (13.1 g, 20.2 mmol) was dissolved in toluene (135 mL), DBU (3.02 mL, 20.2 mmol) was added, and the mixture was stirred at room temperature for 20 minutes. The reaction solution was washed with a 1 M aqueous potassium dihydrogen phosphate solution (80) ml.), then n-hexane (140) ml.), water (140 ml.), acetonitrile (70 ml.), and 2 N hydrochloric acid (12 ml.) were added to the organic phase, and the mixture was shaken. The aqueous phase was recovered, and the organic phase was extracted with water/acetonitrile/2 N hydrochloric acid (30) ml./15 ml./3 ml.). The resulting aqueous phases were combined, and 3 N phosphoric acid (12 ml.) was added to adjust the pH to 8. The resulting mixed solution was extracted twice with ethyl acetate (100 mL, 50 mL.), and the organic phase was washed with brine (50 ml). The organic phase was dried over anhydrous sodium sulfate and concentrated under reduced pressure to give tp024-e (8.20 g, 95%).

LCMS (ESI) m/z=425 (M+H)+

Retention time: 0.849 min (Analytical condition SMD method_04)

In a nitrogen atmosphere, (S)-2-((((9H-fluoren-9-yl) methoxy) carbonyl)(methyl)amino) pent-4-enoic acid (7.45 g, 21.2 mmol) was dissolved in DCM (85 ml) at room temperature, DMF (0).164 ml, 2.12 mmol) was added, and then thionyl chloride (3.85 ml, 53.0 mmol) was added dropwise. The resulting reaction mixture was stirred for 20 minutes and then concentrated under reduced pressure. Toluene (20) ml) was added to the resulting residue, and the mixture was concentrated under reduced pressure. This operation was carried out twice in total, and the resulting crude product was dissolved in DCM (23 mL) and used in the subsequent reaction.

In a nitrogen atmosphere, a DCM (72 mL) solution of tp024-e (8.20 g, 19.3 mmol) and DIPEA (11.8 mL, 67.5 mmol) was added to the prepared DCM (23 ml) solution of(S)-(9H-fluoren-9-yl)methyl(1-chloro-1-oxopent-4-en-2-yl)(methyl) carbamate. The reaction solution was stirred at room temperature for 2 hours, and then washed with a 1 M aqueous potassium dihydrogen phosphate solution (82 mL). Subsequently, the organic phase was washed with a 3.5% aqueous potassium hydrogen carbonate solution (82 mL), and concentrated under reduced pressure. The resulting crude product was purified by silica gel chromatography (n-hexane-ethyl acetate) to give a crude product of tp024-f (14.0 g, 96%).

LCMS (ESI) m/z=758 (M+H)+

Retention time: 1.737 min (Analytical condition SMD method_0) 4)

In a nitrogen atmosphere, tp024-f (1.00 g, 1.32 mmol) and 1,4-benzoquinone were dissolved in 1,2-dichloroethane (40 mL) in a three-necked flask, and the reaction solution was heated to 80° C. A 1,2-dichloromethane solution (4 mL) of the first-generation Grubbs catalyst (55 mg, 0).066 mmol) was added dropwise over 1 hour to the reaction solution stirred at 80° C. Subsequently, the reaction solution was stirred at 80° C. for one more hour, cooled to room temperature, and then concentrated under reduced pressure. The resulting crude product was purified by silica gel chromatography (n-hexane-ethyl acetate) to give tp024-g (0.65 g, 68%). LCMS (ESI) m/z=730 (M+H)+

Retention time: 1.002 min (Analytical condition SMD method_06)

In a nitrogen atmosphere, tp024-g (1.80 g, 2.46 mmol) was dissolved in ethyl acetate (20) mL), hexamethyldisilazane (1.29 mL, 6.16 mmol) was added, and then trimethylsilyl trifluoromethanesulfonate (0.89 mL, 4.93 mmol) was added dropwise. After the resulting reaction mixture was stirred for 150 minutes, the reaction solution was diluted with n-hexane (50) mL), and extracted once with a 3.5% aqueous potassium hydrogen carbonate solution/acetonitrile (2/1, 40 mL). The pH of the aqueous phase was adjusted to 3 with phosphoric acid, and this was extracted with ethyl acetate (30 mL). The resulting organic phase was dried over sodium sulfate, and the solvent was distilled off under reduced pressure. The resulting crude product was purified by reverse phase chromatography (0.1% formic acid-containing acetonitrile/0.1% formic acid-containing distilled water) to give tp024 (0.92 g, 55%).

LCMS (ESI) m/z=674 (M+H)+

Retention time: 0.625 min (Analytical condition SMD method_06)

Synthesis of Compound PP0464

Using Compound aa375-resin (0.426 mmol/g, 100 mg) as a raw material, Fmoc-cVal-OH, Fmoc-Pro (4-F2)—OH, Fmoc-Hph(4—CF3-35-F2)—OH, Compound tp002, Fmoc-MeGly-OH, Fmoc-Ile-OH, and Fmoc-MeLeu-OH were used. Peptide elongation reaction by the basic Fmoc method described in the present Examples, cleaving of an elongated peptide from resin, cyclization of a cleaved peptide (using (1-cyano-2-ethoxy-2-oxoethylideneaminooxy)dimethyl-amino-morpholino-carbenium hexafluorophosphate (COMU) as a cyclization reagent), and purification of a cyclic peptide were performed to give the intended Compound PP0464 (17.2 mg, 26%).

Compound PP0464

LCMS (ESI) m/z=1568.2 (M–H)–

Retention time: 7.979 min (Analytical condition SSC-AA-02/03)

Using the resins, on which amino acid shown in Table 5 and Table 6 was supported, as raw materials, the following compounds were produced according to the above-described Fmoc method in the same manner as the production method of Compound PP0464. A deprotection reaction was added as necessary.

Compounds PP0464, PP0465, PP0466, PP0467, PP0468, PP0469, PP0470, PP0471, PP0472, PP0473, PP0474, PP0475, PP0476, PP0477, PP0478, PP0479, PP0480, PP0481, PP0483, PP0484, PP0485, PP0487, PP0488, PP0490, PP0491, PP0492, PP0493, PP0494, PP0495, PP0496, PP0497, PP0498, PP0499, PP0500, PP0501, PP0502, PP0503, PP0504, PP0505, PP0506, PP0507, PP0508, PP0509, PP0510, PP0511, PP0512, PP0513, PP0514, PP0515, PP0516, PP0520, PP0521, PP0522, PP0523, PP0538, PP0539, PP0540, PP0541, PP0542, PP0543, PP0544, PP0545, PP0546, PP0547, PP0548, PP0549, PP0550, PP0551, PP0552, PP0553, PP0554, PP0555, PP0556, PP0557, PP0558, PP0559, PP0560, PP0561, PP0562, PP0563, PP0564, PP0565, PP0566, PP0567, PP0568, PP0569, PP0570, PP0571, PP0572, PP0573, PP0574, PP0575, PP0576, PP0577, PP0578, PP0579, PP0580, PP0581, PP0582, PP0583, PP0584, PP0585, PP0586, PP0587, PP0588, PP0589, PP0590, PP0591, PP0594, PP0595, PP0596, PP0597, PP0598, PP0630, PP0631, PP0632, PP0633, PP0634, PP0635, PP0636, PP0637, PP0638, PP0639, PP0640, PP0641, PP0642, PP0643, PP0644, PP0645, PP0646, PP0647, PP0648, PP0649, PP0650, PP0651, PP0652, PP0653, PP0654, PP0655, PP0656, PP0657, PP0658, PP0659, PP0660, PP0661, PP0662, PP0663, PP0664, PP0665, PP0666, PP0667, PP0668, PP0669, PP0670, PP0671, PP0672, PP0673, PP0674, PP0675, PP0678, PP0679, PP0680, PP0681, PP0682, PP0683, PP0684, PP0685, PP0686, PP0687, PP0688, PP0689, PP0690, PP0693, PP0694, PP0695, PP0696, PP0697, PP0698, PP0699, PP0700, PP0701, PP0702, PP0703, PP0704, PP0705,

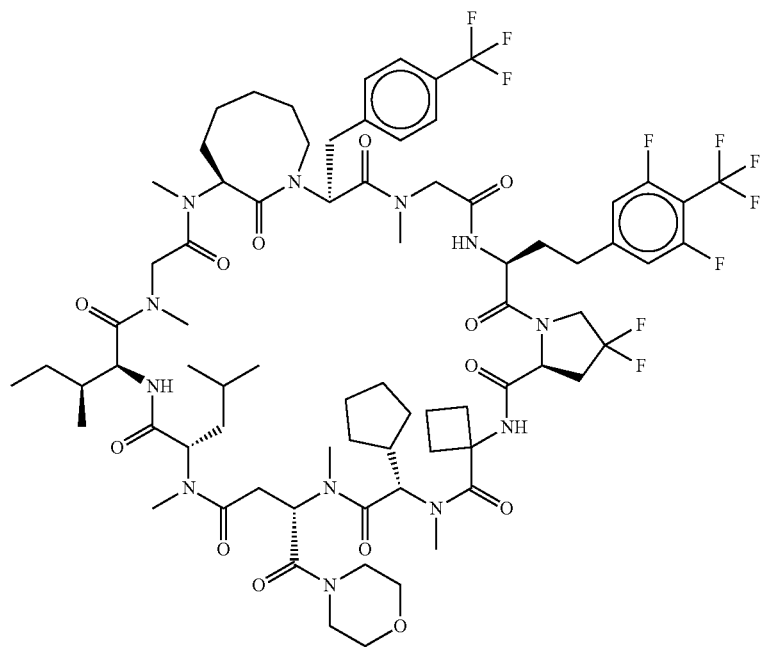

PP0706, PP0708, PP0709, PP0710, PP0711, PP0712, PP0713, PP0714, PP0715, PP0716, PP0717, PP0718, PP0719, PP0720, PP0721, PP0722, PP0723, PP0724, PP0725, PP0726, PP0727, PP0728, PP0729, PP0730, PP0731, PP0732, PP0733, PP0806, PP0807, PP0808, PP0809, PP0810, PP0811, PP0812, PP0813, PP0814, PP0815, PP0816, PP0817, PP0818, PP0819, PP0820, PP0821, PP0822, PP0823, PP0824, PP0825, PP0826, PP0827, PP0828, PP0829, PP0830, PP0831, PP0832, PP0833, PP0834, PP0835, PP0836, PP0837, PP0838, PP0839, PP0840, PP0841, PP0842, PP0843, PP0844, PP0845, PP0846, PP0847, PP0848, PP0849, PP0850, PP0951, PP0852, PP0853, PP0854, PP0855, PP0856, PP0857, PP0858, PP0859, PP0860, PP0861, PP0862, PP0863, PP0864, PP0865, PP0866, PP0867, PP0868, PP0869, PP0870, PP0871, PP0872, PP0873, PP0926, PP0927, PP0928, PP0929, PP0930, PP0931, PP0932, PP0933, PP0934, PP0935, PP0936, PP0937, PP0938, PP0939, PP0940, PP0941, PP0942, PP0943, PP0944, PP0945, PP0946, PP0947, PP0948, PP0949, PP0950, PP0951, PP0952, PP0953, PP0954, PP0955, PP0956, PP0958, PP0959, PP0960, PP0961, PP0962, PP0963, PP0964, PP0965, PP0966, PP0967, PP0968, PP0969, PP0970, PP0971, PP0972, PP0973, PP0975, PP0976, PP0977, PP0978, PP0979, PP0980, PP0981, PP0982, PP0983, PP0984, PP1017, PP1018, PP1019, PP1020, PP1021, PP1022, PP1024, PP1025, PP1026, PP1027, PP1028, PP1029, PP1030, PP1031, PP1032, PP1033, PP1034, PP1035, PP1036, PP1037, PP1038, PP1039, PP1040, PP1041, PP1042, PP1043, PP1044, PP1045, PP1046, PP1047, PP1048, PP1049, PP1050, PP1051, PP1052, PP1053, PP1054, PP1056, PP1057, PP1058, PP1059, PP1060, PP1063, PP1064, PP1065, PP1086, PP1087, PP1088, PP1089, PP1090, PP1091, PP1092, PP1093, PP1094, PP1095, PP1096, PP1097, PP1098, PP1099, PP1100, PP1101, PP1102, PP1103, PP1104, PP1105, PP1106, PP1107, PP1108, PP1109, PP1110, PP111, PP1112, PP1113, PP1114, PP1115, PP1116, PP1117, PP1118, PP1119, PP1120, PP1121, PP1122, PP1123, PP1124, PP1125, PP1126, PP1127, PP1128, PP1129, PP1130, PP1131, PP1132, PP1133, PP1134, PP1135, PP1136, PP1137, PP1138, PP1139, PP1140, PP1141, PP1142, PP1143, PP1144, PP1145, PP1146, PP1147, PP1148, PP1149, PP1150, PP1155, PP1156, PP1157, PP1158, PP1159, PP1160, PP1161, PP1162, PP1163, PP1164, PP1165, PP1166, PP1167, PP1168, PP1169, PP1170, PP1171, PP1172, PP1173, PP1174, PP1175, PP1176, PP1177, PP1178, PP1179, PP1180, PP1181, PP1182, PP1183, PP1184, PP1185, PP1186, PP1187, PP1188, PP1189, PP1190, PP1191, PP1192, PP1193, PP1194, PP1195, PP1196, PP1197, PP1198, PP1199, PP1200, PP1201, PP1202, PP1203, PP1204, PP1205, PP1206, PP1207, PP1208, PP1209, PP1210, PP1211, PP1212, PP1213, PP1214, PP1215, PP1216, PP1217, PP1218, PP1219, PP1220, PP1221, PP1222, PP1223, PP1224, PP1225, PP1226, PP1227, PP1228, PP1229, PP1230, PP1231, PP1232, PP1233, PP1234, PP1235, PP1242, PP1243, PP1244, PP1245, PP1246, PP1247, PP1248, PP1249, PP1250, PP1251, PP1252, PP1253, PP1254, PP1255, PP1256, PP1257, PP1258, PP1259, PP1260, PP1261, PP1262, PP1263, PP1264, PP1265, PP1266, PP1267, PP1268, PP1269, PP1270, PP1271, PP1272, PP1273, PP1274, PP1275, PP1276, PP1277, PP1278, PP1279, PP1280, PP1281, PP1282, PP1283, PP1284, PP1285, PP1286, PP1287, PP1288, PP1289, PP1290, PP1291, PP1292, PP1293, PP1294, PP1295, PP1296, PP1297, PP1298, PP1299, PP1336, PP1337, PP1338, PP1339, PP1340, PP1341, PP1342, PP1343, PP1344, PP1345, PP1346, PP1347, PP1348, PP1349, PP1350, PP1351, PP1352, PP1353, PP1354, PP1355, PP1356, PP1357, PP1358, PP1359, PP1360, PP1361, PP1362, PP1363, PP1364, PP1365, PP1366, PP1367, PP1368, PP1369, PP1370, PP1371, PP1372, PP1373, PP1374, PP1375, PP1376, PP1377, PP1378, PP1379, PP1380, PP1381, PP1382, PP1383, PP1384, PP1385, PP1386, PP1390, PP1391, PP1392, PP1393, PP1394, PP1395, PP1396, PP1397, PP1398, PP1399, PP1400, PP1401, PP1402, PP1403, PP1404, PP1405, PP1406, PP1407, PP1408, PP1409, PP1410, PP1411, PP1412, PP1413, PP1414, PP1415, PP1416, PP1417, PP1418, PP1419, PP1420, PP1421, PP1422, PP1423, PP1424, PP1425, PP1426, PP1427, PP1428, PP1429, PP1430, PP1431, PP1432, PP1433, PP1434, PP1435, PP1436, PP1437, PP1438, PP1439, PP1440, PP1441, PP1442, PP1443, PP1444, PP1445, PP1446, PP1447, PP1448, PP1449, PP1450, PP1451, PP1452, PP1453, PP1454, PP1455, PP1456, PP1457, PP1458, PP1459, PP1460, PP1461, PP1462, PP1463, PP1464, PP1465, PP1466, PP1467, PP1468, PP1469, PP1470, PP1471, PP1472, PP1473, PP1474, PP1475, PP1476, PP1477, PP1478, PP1479, PP1480, PP1481, PP1482, PP1483, PP1484, PP1485, PP1486, PP1487, PP1488, PP1489, PP1490, PP1491, PP1492, PP1493, PP1494, PP1495, PP1496, PP1497, PP1498, PP1499, PP1500, PP1501, PP1502, PP1503, PP1504, PP1505, PP1506, PP1507, PP1508, PP1509, PP1510, PP1511, PP1512, PP1513, PP1514, PP1515, PP1516, PP1517, PP1518, PP1519, PP1520, PP1521, PP1522, PP1523, PP1524, PP1525, PP1526, PP1527, PP1528, PP1529, PP1530, PP1531, PP1532, PP1558, PP1559, PP1560, PP1561, PP1562, PP1563, PP1564, PP1565, PP1566, PP1568, PP1569, PP1570, PP1571, PP1572, PP1573, PP1574, PP1575, PP1576, PP1577, PP1578, PP1579, PP1580, PP1582, PP1583, PP1584, PP1586, PP1587, PP1588, PP1589, PP1590, PP1591, PP1592, PP1593, PP1594, PP1595, PP1596, PP1598, PP1599, PP1600, PP1601, PP1603, PP1605, PP1606, PP1607, PP1608, PP1609, PP1610, PP1611, PP1612, PP1613, PP1614, PP1615, PP1616, PP1617, PP1620, PP1622, PP1623, PP1624, PP1625, PP1626, PP1627, PP1628, PP1629, PP1630, PP1631, PP1632, PP1633, PP1634, PP1635, PP1636, PP1637, PP1639, PP1640, PP1641, PP1643, PP1644, PP1645, PP1646, PP1648, PP1649, PP1650, PP1651, PP1653, PP1654, PP1655, PP1656, PP1657, PP1658, PP1660, PP1661, PP1662, PP1663, PP1665, PP1666, PP1667, PP1668, PP1670, PP1671, PP1672, PP1673, PP1674, PP1675, PP1676, PP1677, PP1678, PP1679, PP1682, PP1683, PP1684, PP1687, PP1688, PP1689, PP1691, PP1692, PP1693, PP1694, PP1696, PP1697, PP1698, PP1699, PP1700, PP1701, PP1702, PP1703, PP1704, PP1705, PP1706, PP1707, PP1709, PP1710, PP1711, PP1713, PP1714, PP1715, PP1716, PP1717, PP1718, PP1721, PP1722, PP1727, PP1728, PP1729, PP1731, PP1732, PP1733, PP1734, PP1735, PP1736, PP1737, PP1738, PP1739, PP1740, PP1741, PP1742, PP1743, PP1744, PP1746, PP1747, PP1748, PP1749, PP1750, PP1751, PP1752, PP1753, PP1754, PP1757, PP1758, PP1759, PP1760, PP1761, PP1762, PP1763, PP1764, PP1765, PP1767, PP1768, PP1769, PP1771, PP1772, PP1773, PP1776, PP1777, PP1779, PP1780, PP1781, PP1782, PP1783, PP1784, PP1785, PP1786, PP1787, PP1788, PP1789, PP1790, PP1791, PP1792, PP1793, PP1794, PP1795, PP1796, PP1797, PP1798, PP1799, PP1800, PP1801, PP1802, PP1803, PP1804, PP1805, PP1806,

PP1807, PP1808, PP1809, PP1810, PP1811, PP1812, PP1813, PP1814, PP1821, PP1822, PP1823, PP1825, PP1826, PP1836, PP1837, PP1838, PP1839, PP1840, PP1841, PP1842, PP1844, PP1846, PP1848, PP1849, PP1850, PP1851, PP1852, PP1853, PP1854, PP1855, PP1856, PP1857, PP1859, PP1860, PP1861, PP1862. PP1863, PP1864, PP1865, PP1866, PP1867, PP1868, PP1869, PP1870, PP1871, PP187Z PP1873, PP1874, PP1875, PP1876, PP1877, PP1878, PP1879, PP1880, PP1881, PP188Z PP1883, PP1884, PP1885, PP1886, PP1887, PP1888, PP1889, PP1890, PP1891, PP192, PP1893, PP1894, PP1895, PP1896, PP1897, PP1898, PP1899, PP1900, PP1901, PP1902, PP1903, PP1904, PP1905, PP1906, PP1907, PP1908, PP1909, PP1910, PP1911, PP1913, PP1915, PP1917, PP1919, PP1921, PP1923, PP1925, PP1927, PP1929, PP1931, PP1932, PP1934, PP1935, PP1936, PP1937, PP1938, PP1941, PP1942, PP1943, PP1944, PP1945, PP197Z PP1973, PP1974, PP1975, PP1976, PP1977, PP1979, PP1980, PP1981, PP1983, PP1984, PP1985, PP1987, PP1988, PP1989, PP1990, PP1991, PP1992, PP1993, PP1994, PP1995, PP1996, PP1997, PP1998, PP1999, PP2000, PP2001, PP2002, PP2003, PP2004, PP2005, PP2006, PP2007, PP2008, PP2009, PP2010, PP2011, PP2012, PP2013, PP2014, PP2015, PP2016, PP2017, PP2018, PP2019, PP2020, PP2021, PP22, PP2023, PP2024, PP2025, PP2026, PP2027, PP2028, PP2029, PP2030, PP2031, PP32, PP2033, PP2034, PP2036, PP2037, PP2038, PP2040, PP2041, PP2042, PP2043, PP2044, PP2045, PP2046, PP2047, PP2048, PP2049, PP2050, PP2051, PP2052, PP2053, PP2054, PP2055, PP2056, PP2057, PP2058, PP2059, PP2060, PP2061, PP2062, PP2063, PP2064, PP2065, PP2066, PP2067, PP2068, PP2069, PP2070, PP2071, PP2072, PP2073, PP2074, PP2075, PP2076, PP2077, PP2078, PP2079, PP2080, PP2081, PP202, PP2083, PP2087, PP2091, PP2093, PP2094, PP2095, PP2096, PP2097, PP2098, PP2099, PP2101, PP2102, PP2103, PP2105, PP2106, PP2107, PP2108, PP2109, P2119, PP2120, PP2121, P2122, PP2123, PP2124, PP2125, PP2126, PP2127, PP2128, PP2130, PP2131, 2132, PP2133, PP2135, PP2137, PP2138, PP2139, PP2140, PP2141, P2142, PP2143, PP2144, PP2145, PP2146, PP2147, PP2148, PP2149, PP2150, PP2151, P2152, PP2153, PP2154, PP2155, PP2156, PP2157, PP2158, PP2159, PP2160, PP2161, PP2163, PP2164, PP2165, PP2166, PP2167, PP2168, PP2169, PP2170, PP2171, PP217Z PP2173, PP2174, PP2175, PP2176, PP2178, PP2179, PP2180, PP2181, PP2182, PP2183, PP2184, PP2185, PP2186, PP2187, PP2188, PP2189, PP2190, PP2191, 2192, PP2193, PP2195, PP2196, PP2197, PP2198, PP2199, PP2200, PP2202, PP2203, PP2207, PP2208, PP2209, PP2210, PP2212, PP2214, PP2216, PP2218, PP2219, PP2220, PP2221, PP22Z PP2223, PP2224, PP2225, PP2226, PP2227, PP2229, PP2230, PP2231, PP2232, PP2233, PP2234, PP2235, PP2237, PP2238, PP2242, PP2257, PP2268, PP2269, PP2270, PP2271, PP2272, PP2273, PP2275, PP2385, PP2386, PP2387, PP2388, PP2389, PP2390, PP2391, PP2392, PP2393, PP2394, PP2395, PP2396, PP2397, PP2398, PP2399, PP2400, PP2401, PP2402, PP2403, PP2404, PP2405, PP2406, PP2407, PP2408, PP2409, PP2410, PP2411, PP2412, PP2413, PP2414, PP2415, PP2416, PP2417, PP2418, PP2419, PP2422, PP2423, PP2424, PP2425, PP2426, PP2427, PP2428, PP2429, PP2430, PP2431, PP2432, PP2433, PP2436, PP2437, PP2438, PP2439, PP2440, PP2441, PP2442 PP2443, PP2444, PP2445, PP2446, PP2447, PP2448, PP2449, PP2450, PP2451, PP2452, PP2453, PP2454, PP2455, PP2456, PP2457, PP2458, PP2460, PP2461, PP2462, PP2463, PP2464, PP2465, PP2466, PP2467, PP2468, PP2469, PP2470, PP2471, PP2472, PP2475, PP2477, PP2479, PP2480, PP2481, PP2482, PP2483, PP2484, PP2485, PP2488, PP2489, PP2490, PP2492, PP2494, PP2495, PP2496, PP2497, PP2498, PP2499, PP2500, PP2501, PP2502, PP2504, PP2505, PP2506, PP2507, PP2508, PP2509, PP2510, PP2511, PP2512, PP2513, PP2514, PP2515, PP2516, PP2517, PP2518, PP2519, PP2520, PP2521, PP2522, PP2523, PP2524, PP2525, PP2526, PP2527, PP2528, PP2529, PP2530, PP2531, PP2532, PP2533, PP2534, PP2535, PP2536, PP2537, PP2539, PP2540, PP2541, PP2542, PP2543, PP2545, PP2546, PP2547, PP2548, PP2549, PP2550, PP2551, PP2552, PP2553, PP2554, PP2555, PP2556, PP2557, PP2558, PP2559, PP2560, PP2561, PP2562, PP2563, PP2564, PP2565, PP2566, PP2567, PP2568, PP2569, PP2570, PP2571, PP2572, PP2606, PP2608, PP2610, PP2612, PP2614, PP2615, PP2616, PP2618, PP2619, PP2622, PP2624, PP2626, PP2627, PP2628, PP2630, PP2631, PP2633, PP2634, PP2635, PP2637, PP2638, PP2639, PP2640, PP2641, PP2642, PP2643, PP2644, PP2645, PP2646, PP2648, PP2649, PP2650, PP2651, PP2652, PP2654, PP2655, PP2656, PP2657, PP2659, PP2660, PP2661, PP2662, PP2663, PP2664, PP2665, PP2666, PP2667, PP2668, PP2669, PP2670, PP2671, PP2706, PP2708, PP2710, PP2712, PP2714, PP2716, PP2718, PP2720, PP2722, PP2724, PP2726, PP2728, PP2730, PP2732, PP2734, PP2736, PP2738, PP2740, PP2742, PP2744, PP2746, PP2748, PP2749, PP2750, PP2751, PP2752, PP2753, PP2754, PP2755, PP2756, PP2757, PP2760, PP2761, PP2762, PP2763, PP2764, PP2765, PP2766, PP2767, PP2768, PP2769, PP2770, PP2771, PP2772, PP2773, PP2776, PP2777, PP2778, PP2779, PP2780, PP2781, PP2782, PP2783, PP2784, PP2785, PP2786, PP2787, PP2788, PP2789, PP2790, PP2791, PP2796, PP2797, PP2798, PP2799, PP2800, PP2801, PP2802, PP2803, PP2804, PP2805, PP2806, PP2807, PP2808, PP2809, PP2811, PP2813, PP2815, PP2817, PP2819, PP2821, PP2822, PP2823, PP2824, PP2825, PP2826, PP2827, PP2828, PP2829, PP2830, PP2831, PP2832, PP2833, PP2834, PP2835, PP2836, PP2837, PP2838, PP2839, PP2840, PP2841, PP2842, PP2843, PP2844, PP2845, PP2846, PP2847, PP2848, PP2888, PP2889, PP2890, PP2891, PP2892, PP2893, PP2894, PP2895, PP2896, PP2897, PP2898, PP2899, PP2900, PP2901, PP2902, PP2904, PP2905, PP2906, PP2907, PP2908, PP2909, PP2910, PP2911, PP2912, PP2913, PP2914, PP2915, PP2916, PP2917, PP2918, PP2920, PP2921, PP2922, PP2923, PP2928, PP2929, PP2931, PP2932, PP2934, PP2935, PP2936, PP2937, PP2938, PP2941, PP2946, PP2947, PP2948, PP2949, PP2950, PP2951, PP2960, PP2961, PP2962, PP2963, PP2964, PP2965, PP2966, PP2967, PP2968, PP2969, PP2970, PP2971, PP2972, PP2973, PP2974, PP2975, PP2976, PP2977, PP2978, PP2979, PP2980, PP2961, PP2962, PP2983, PP2984, PP2985, PP2986, PP2987, PP2988, PP2989, PP2990, PP2991, PP2992. PP2993, PP2994, PP2995, PP2996, PP2997, PP2998, PP2999, PP3000, PP3001, PP3002, PP3003, PP3004, PP3005, PP3006, PP3007, PP3008, PP3009, PP3010, PP3011, PP3012, PP3013, PP3014, PP3015, PP3017, PP3018, PP3019, PP3021, PP3022, PP3026, PP3030, and PP3031.

The following compounds were produced according to the above-described Fmoc method in the same manner as the production method of Compound PP0464 using aa427-resin to aa438-resin as raw materials:

Compounds PP2312, PP2313, PP2314, PP2315, PP2316, PP2317, PP2318, PP2319, PP2320, PP2322, PP2323, PP2325, PP2326, PP2327, PP2328, PP2329, PP2330, PP2331, PP2332, PP2333, PP2334, PP2335, PP2336, PP2337, PP2338, PP2339, PP2340, PP2341, PP2342, PP2344, PP2345, PP2347, PP2348, PP2349, PP2350, PP2351, PP2352, PP2353, PP2354, PP2355, PP2356, PP2357, PP2358, PP2359, PP2360, PP2361, PP2362, PP2363, PP2364, PP2365, PP2366, PP2367, PP2368, PP2369, PP2370, PP2371, PP2372, PP2373, PP2374, PP2375, PP2376, PP2377, PP2378, PP2379, PP2380, PP2381, PP2382, PP2383, PP2810, PP2812, PP2814, PP2816, PP2818, PP2820, PP3095, PP3096, PP3097, PP3098, PP3099, PP3100, PP3101, PP3102, PP3103, PP3104, PP3105, PP3106, PP3110, PP3111, PP3112, PP3113, PP3114, PP3115, PP3116, PP3117, PP3118, PP3119, PP3120, and PP3121.

In a cyclic compound and an oligopeptide compound synthesized with a tripeptide, abbreviations and structures of amino acids contained as partial structures are provided below.

TABLE 9-1

| Compound No. | Abbreviation | Amino acid Structural Formula |
|---|---|---|
| bb001 | Phe(4-CF3) | 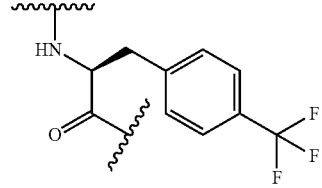 [SMILES: *N[C@@H](Cc1ccc(C(F)(F)F)cc1)C(*)=O] |
| bb002 | AllylPhe(4-CF3) | 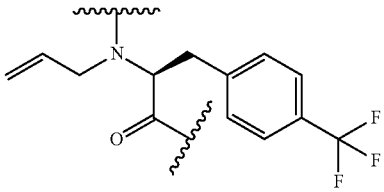 [SMILES: *C(=O)[C@H](Cc1ccc(C(F)(F)F)cc1)N(*)CC=C] |
| bb003 | Phe(4-F) | 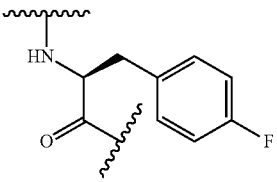 [SMILES: *N[C@@H](Cc1ccc(F)cc1)C(*)=O] |
| bb004 | AllylPhe(4-F) | 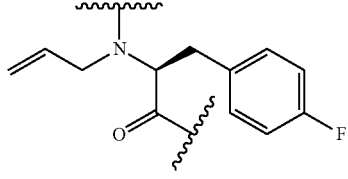 [SMILES: *C(=O)[C@H](Cc1ccc(F)cc1)N(*)CC=C] |
| bb005 | ButenylPhe(4-CF3) | 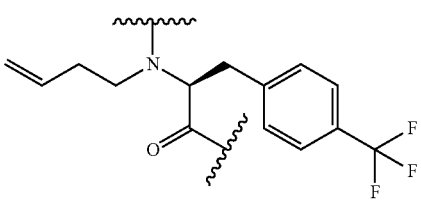 [SMILES: *C(=O)[C@H](Cc1ccc(C(F)(F)F)cc1)N(*)CCC=C] |
| bb006 | Cha | 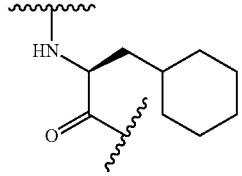 [SMILES: *N[C@@H](CC1CCCCC1)C(*)=O] |

TABLE 9-1-continued

| Compound No. | Abbreviation | Amino acid Structural Formula |
|---|---|---|
| bb007 | ButenylCha | |
| bb008 | Cha(4-F2) | |
| bb009 | ButenylCha(4-F2) | |
| bb010 | BuetnylAsp(OMe) | |
| bb011 | ButenylPhe(4-Me) | |
| bb012 | ButenylPhe(4-F | |
| bb013 | ButenylPhe(4-F-2-Me) | |
| bb014 | ButenylPhe(4-I) | |

TABLE 9-1-continued

| Compound No. | Abbreviation | Amino acid Structural Formula |
|---|---|---|
| bb015 | MethaPhe(4-CF3) | |

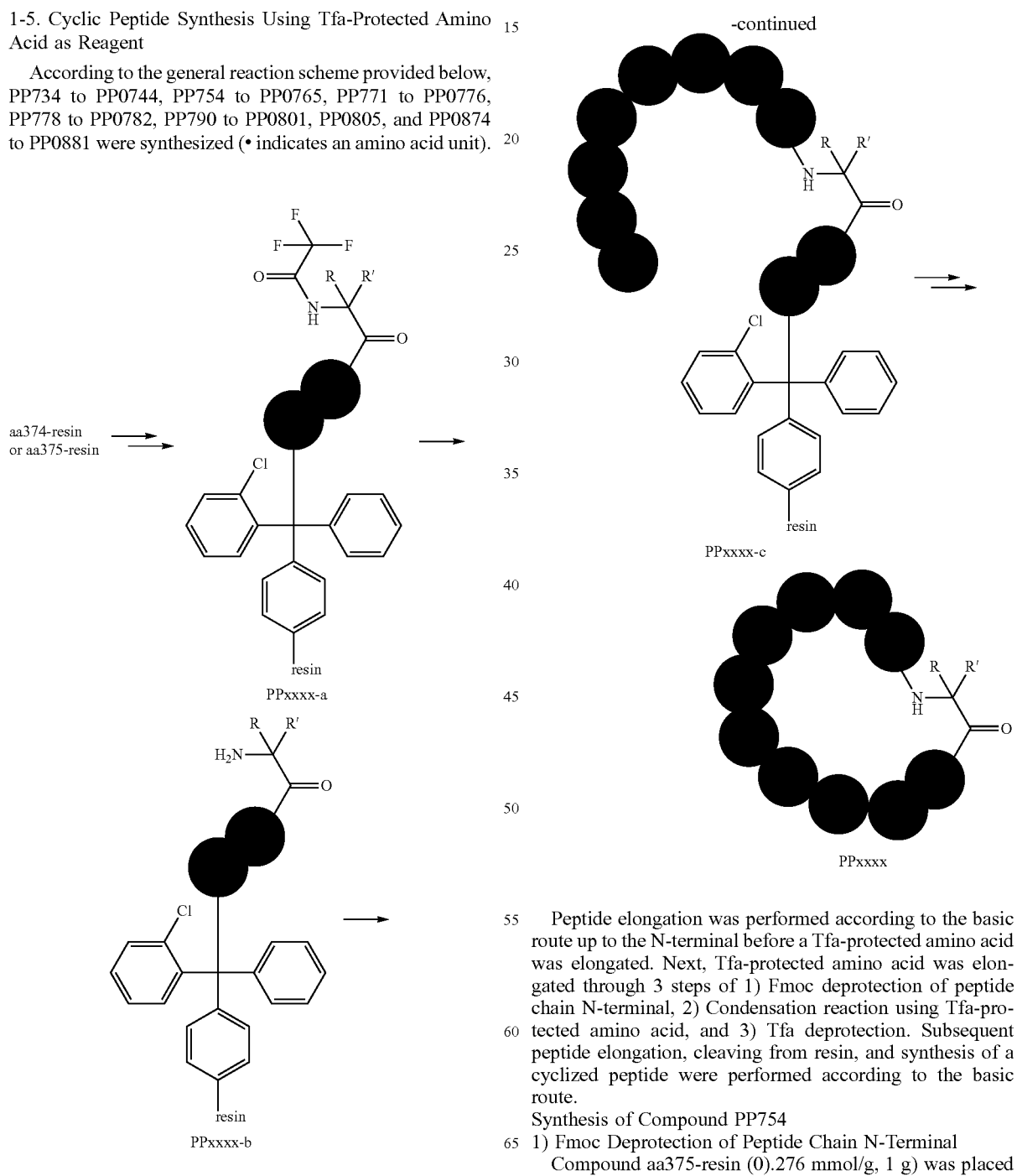

1-5. Cyclic Peptide Synthesis Using Tfa-Protected Amino Acid as Reagent

According to the general reaction scheme provided below, PP734 to PP0744, PP754 to PP0765, PP771 to PP0776, PP778 to PP0782, PP790 to PP0801, PP0805, and PP0874 to PP0881 were synthesized (• indicates an amino acid unit).

Peptide elongation was performed according to the basic route up to the N-terminal before a Tfa-protected amino acid was elongated. Next, Tfa-protected amino acid was elongated through 3 steps of 1) Fmoc deprotection of peptide chain N-terminal, 2) Condensation reaction using Tfa-protected amino acid, and 3) Tfa deprotection. Subsequent peptide elongation, cleaving from resin, and synthesis of a cyclized peptide were performed according to the basic route.

Synthesis of Compound PP754

1) Fmoc Deprotection of Peptide Chain N-Terminal
   Compound aa375-resin (0).276 mmol/g, 1 g) was placed in a filter-equipped reaction vessel, dichloromethane (10)

mL) was added, and the mixture was shaken at room temperature for 5 minutes to swell the resin. After dichloromethane was removed with the filter, the resin was washed twice with DMF (7 mL). Subsequently, a 2% DBU/DMF solution (de-Fmoc solution: 7 mL) was added to the resin, and the mixture was shaken at room temperature for 10 minutes to carry out a de-Fmoc reaction. After the de-Fmoc solution was removed, the resin was washed 4 times with DMF (7 mL).

2) Condensation Reaction Using Tfa-Protected Amino Acid

An elongation reaction of Tfa-(Me) Abu-OH (Compound aa317) was performed on the resulting resin. The elongation reaction was performed by adding a mixed solution of a 0.6 M Tfa-(Me) Abu-OH (Compound aa317)/DMF solution (3 mL) and a 10% DIC/DMF solution (3.6 mL) to the resin and shaking the mixture at 60° C. for 24 hours. After the liquid phase of the elongation reaction was removed with a filter, the resin was washed 4 times with DMF (7 mL) and 4 times with dichloromethane (7 mL) and dried to give Compound PP0754-a (Tfa-(Me) Abu-MeGly (cPent)-MeAsp (O-Trt) (2-C1)-resin)-mor).

3) Tfa Deprotection

NaBH4 (0).5 g, 13.2 mmol) was placed in a flask, pumped up, then dissolved in trigrim (6.6 mL) under nitrogen atmosphere to give Solution A. The resulting resin PP754-a (100 mg) was swollen with dichloromethane (1 mL) and then washed twice with tetrahydrofuran (0.7 mL). Tetrahydrofuran (0).5 mL), methanol (0.25 mL), and Solution A (0).25 mL) were added, and the mixture was left to stand still in an open system at room temperature for 2 hours. After the reaction solution was removed, tetrahydrofuran (0).5 mL), methanol (0).25 mL), and Solution A (0).25 mL) were added, and the mixture was left to stand still in an open system at room temperature for 30 minutes. After the reaction solution was removed, the operation of adding methanol (0).7 mL) and washing the mixture for 1 minute was repeated 4 times, and the mixture was further washed with dichloromethane (0).7 mL) 4 times. The amino acid was cleaved from the resin with TFE/DCM (1/1 (v/v)) containing DIPEA (0).045 mmol/L) using a small amount of resin-supported Compound PP754-b, and the structure was verified by LC/MS.

LCMS (ESI) m/z=455 (M+H)+

Retention time: 0.39 min (Analytical condition SQDFA05)

Subsequent peptide chain elongation, cleaving from resin, and synthesis of a cyclized peptide were performed according to the basic peptide synthesis method described in the present Examples. LC/MS data is provided in Table 36.

Using 0.374-resin and aa375-resin as raw materials, PP0734-a to PP0744-a, PP0754-a to PP0765-a, PP0771-a to PP0776-a, PP0778-a to PP0782-a, PP0790-a to PP0801-a, PP0805-a, and PP0874-a to PP0881-a were obtained in the same manner as synthesis of Compound PP0754-a using the Tfa-protected amino acids listed in Table 10 in place of Tfa-(Me)Abu-OH. Then, PP0734-b to PP0744-b, PP0754-b to PP0765-b, PP0771-b to PP0776-b, PP0778-b to PP0782-b, PP0790-b to PP0801-b, PP0805-b, and PP0874-b to PP0881-b were obtained in the same manner as synthesis of PP0754-b. Subsequent peptide chain elongation, cleaving from resin, and synthesis of a cyclized peptide were performed according to the basic peptide synthesis method described in the present Examples to give Compounds PP0734 to PP0744, PP0754 to PP0765, PP0771 to PP077, PP0778 to PP0782, PP0790 to PP0801, PP0605, and PP0874 to PP081. LC/MS data is provided in Table 36.

Synthesis of Tfa-Protected Amino Acids

The amino acids listed in Table 10 were synthesized by the following method and used in a peptide elongation reaction.

TABLE 10

| Compound No. | Abbreviation | Structural Formula | Name |
|---|---|---|---|
| aa309 | Tfa-D-(Me)Algly-OH | | (R)-2-methyl-2-(2,2,2-trifluoroacetamido)pent-4-enoic acid |
| aa317 | Tfa-(Me)Abu-OH | | (S)-2-methyl-2-(2,2,2-trifluoroacetamido)butanoic acid |
| aa319 | Tfa-AoxeC-OH | | 3-(2,2,2-trifluoroacetamido)oxetane-3-carboxylic acid |

TABLE 10-continued

| Compound No. | Abbreviation | Structural Formula | Name |
|---|---|---|---|
| aa320 | Tfa-(Me)Ser(tBu)-OH | | (S)-3-(tert-butoxy)-2-methyl-2-(2,2,2-trifluoroacetamido)propanoic acid |
| aa321 | Tfa-(Me)Ser(Al)-OH | | (S)-3-(allyloxy)-2-methyl-2-(2,2,2-trifluoroacetamido)propanoic acid |
| aa322 | Tfa-(Me)Ser(Me)-OH | | (S)-3-methoxy-2-methyl-2-(2,2,2-trifluoroacetamido)propanoic acid |
| aa323 | Tfa-(Me)Phe-OH | | (S)-2-methyl-3-phenyl-2-(2,2,2-trifluoroacetamido)propanoic acid |
| aa324 | Tfa-(Me)Cha-OH | | (S)-3-cyclohexyl-2-methyl-2-(2,2,2-trifluoroacetamido)propanoic acid |
| aa325 | Tfa-(Me)Leu-OH | | (S)-2,4-dimethyl-2-(2,2,2-trifluoroacetamido)pentanoic acid |
| aa326 | Tfa-(Me)Nva-OH | | (S)-2-methyl-2-(2,2,2-trifluoroacetamido)pentanoic acid |

TABLE 10-continued

| Compound No. | Abbreviation | Structural Formula | Name |
|---|---|---|---|
| aa327 | Tfa-(Me)Ile-OH | | (2S,3S)-2,3-dimethyl-2-(2,2,2-trifluoroacetamido)pentanoic acid |
| aa328 | Tfa-(Me)Val-OH | | (S)-2,3-dimethyl-2-(2,2,2-trifluoroacetamido)butanoic acid |
| aa329 | Tfa-(Me)Gly(cPr)-OH | | (S)-2-cyclopropyl-2-(2,2,2-trifluoroacetamido)propanoic acid |

Synthesis of Compound aa309

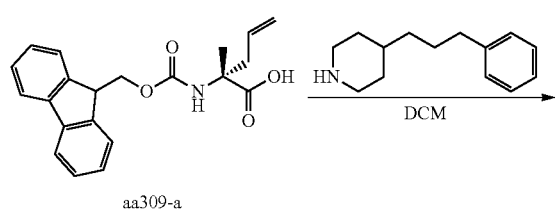

aa309-a

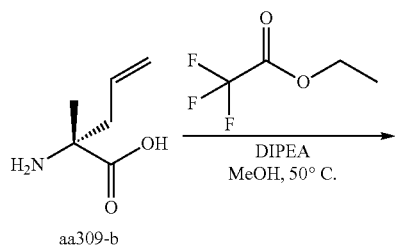

aa309-b

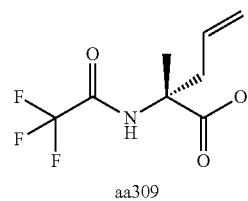

aa309

4-(3-Phenylpropyl) piperidine (9.0 mL, 42.7 mmol) was added to a dichloromethane (47.4 mL) solution of Compound aa309-a ((R)-2-((((9H-fluoren-9-yl)methoxy) carbonyl)amino)-2-methylpent-4-enoic acid, Fmoc-D-(Me) Algly-OH)(5.0 g, 14.2 mmol), and the mixture was stirred at room temperature for 36 hours in a nitrogen atmosphere. Water (10 mL) and 2 N hydrochloric acid (5 mL) were added to the reaction solution to extract the product, and the aqueous layer was purified by reverse phase column chromatography (0.1% formic acid-water/0.1% formic acid-acetonitrile) to give Compound aa309-b ((R)-2-amino-2-methylpent-4-enoic acid, H-D-(Me) Algly-OH)(1.9 g, quant.), which was used in the next reaction.

LCMS (ESI) m/z=130 (M+H)+

Retention time: 0.15 min (Analytical condition SQDFA05)(retention time of MS peak is provided)

After N,N-diisopropylethylamine (7.7 mL, 44.1 mmol) and ethyl 2,2,2-trifluoroacetate (5.3 mL, 44.1 mmol) were added to a methanol (24.5 mL) solution of Compound aa309-b ((R)-2-amino-2-methylpent-4-enoic acid, H-D-(Me) Algly-OH)(1.9 g, 14.7 mmol), and the mixture was stirred at 50° C. for 24 hours. The reaction solution was cooled to room temperature and then concentrated under reduced pressure, and the resulting residue was dissolved in TBME (60 mL) and then washed twice with 1 N hydrochloric acid (60 mL) and once with saturated brine (60 mL). The organic layer was dried over anhydrous sodium sulfate, filtered, and then concentrated under reduced pressure to give a crude product. The resulting crude product was purified by reverse phase column chromatography (0.1% formic acid-water/0.1% formic acid-acetonitrile) to give Compound aa309 (2.5 g, 75%).

LCMS (ESI) m/z=224 (M−H)−

Retention time: 0.52 min (Analytical condition SQDFA05)

Synthesis of Compound aa321

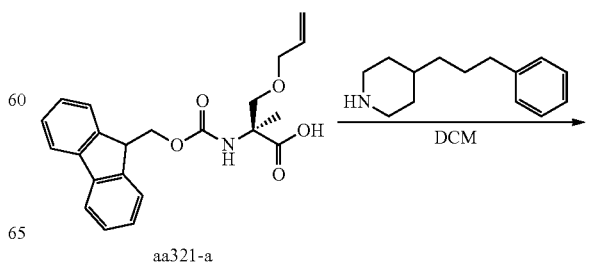

aa321-a

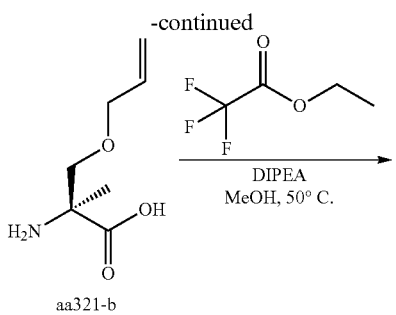

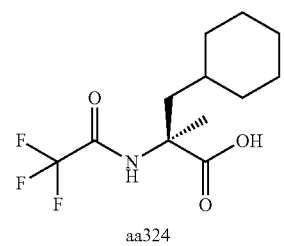

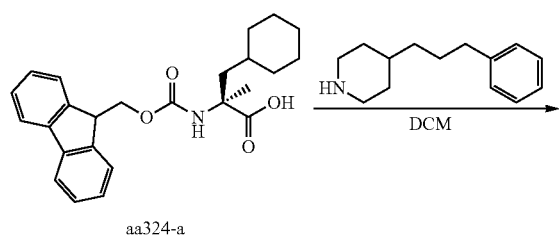

Using Compound aa321-a ((S)-2-((((9H-fluoren-9-yl)methoxy) carbonyl)amino)-3-(allyloxy)-2-methylpropanoic acid, Fmoc-(Me) Ser (Al))—OH)(2.0 g, 5.2 mmol) as a starting material, Compound aa321-b ((S)-3-(allyloxy)-2-amino-2-methylpropanoic acid, H—(Me) Ser (Al)—OH) (0.87 g, quant.) was obtained in the same manner as synthesis of Compound aa309-b, and was used in the next reaction.

LCMS (ESI) m/z=160 (M+H)+

Retention time: 0.16 min (Analytical condition SQDFA05)(retention time of MS peak is provided)

Using Compound aa321-b ((S)-3-(allyloxy)-2-amino-2-methylpropanoic acid, H—(Me) Ser (Al)—OH)(0.84 g, 5.3 mmol), Compound aa321 (1.0 g, 75%) was obtained in the same manner as synthesis of Compound aa309.

LCMS (ESI) m/z=256 (M+H)+

Retention time: 0.55 min (Analytical condition SQDFA05)

Synthesis of Compound aa324

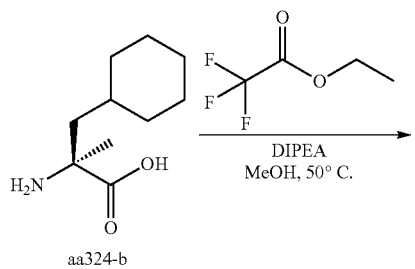

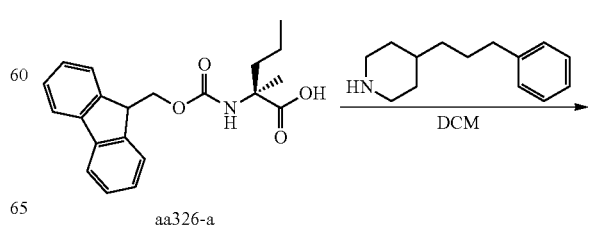

4-(3-Phenylpropyl) piperidine (4.7 mL, 22.1 mmol) was added to a dichloromethane (18.4 mL) solution of Compound aa324-a ((S)-2-(9H-fluoren-9-ylmethoxycarbonylamino)-3-cyclohexyl-2-methylpropanoic acid, Fmoc-(Me) Cha-OH)(3.0 g, 7.4 mmol), and the mixture was stirred in a nitrogen atmosphere at room temperature for 16 hours. Water (5 mL) and 2 N hydrochloric acid (5 mL) were added to the reaction solution to extract the product, and the aqueous layer was purified by reverse phase column chromatography (0.1% formic acid-water/0.1% formic acid-acetonitrile) to give Compound aa324-b ((S)-2-amino-3-cyclohexyl-2-methylpropanoic acid, H—(Me) Cha-OH)(1.1 g, 81%), which was used in the next reaction.

LCMS (ESI) m/z=186 (M+H)+

Retention time: 0.32 min (Analytical condition SQDFA05)

After N,N-diisopropylethylamine (3.1 mL, 18.0 mmol) and ethyl 2,2,2-trifluoroacetate (2.1 mL, 18.0 mmol) were added to a methanol (20.0 mL) solution of Compound aa324-b ((S)-2-amino-3-cyclohexyl-2-methylpropanoic acid, H—(Me) Cha-OH)(1.1 g, 6.0 mmol), and the mixture was stirred at 50° C. for 2 hours. Then, N,N-diisopropylethylamine (3.1 mL, 18.0 mmol) and ethyl 2,2,2-trifluoroacetate (2.1 mL, 18.0 mmol) were added, and the mixture was stirred at 50° C. for 20 hours. The reaction solution was cooled to room temperature and then concentrated under reduced pressure, and the resulting residue was dissolved in TBME (30 mL) and washed twice with 1 N hydrochloric acid (30 mL) and once with saturated brine (30 mL). The organic layer was dried over anhydrous sodium sulfate, filtered, and then concentrated under reduced pressure to give a crude product. The resulting crude product was purified by reverse phase column chromatography (0.1% formic acid-water/0.1% formic acid-acetonitrile) to give Compound aa324 (1.2 g, 72%).

LCMS (ESI) m/z=280 (M−H)−

Retention time: 0.75 min (Analytical condition SQDFA05)

Synthesis of Compound aa326

-continued

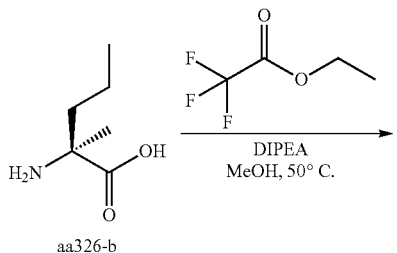

aa326-b

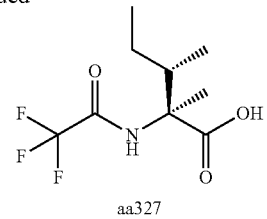

aa327

Using Compound aa327-a ((2S,3S)-2-((((9H-fluoren-9-yl)methoxy) carbonyl)amino)-2,3-dimethylpentanoic acid, Fmoc-(Me) Ile-OH)(3.0 g, 8.2 mmol) as a starting material, Compound aa327-b ((2S,3S)-2-amino-2,3-dimethylpentanoic acid, H—(Me) Ile-OH)(1.1 g, 96%) was obtained in the same manner as synthesis of Compound aa309-b, and used in the next reaction.

LCMS (ESI) m/z=146 (M+H)+

Retention time: 0.15 min (Analytical condition SQDFA05)

Using Compound aa327-b ((2S,3S)-2-amino-2,3-dimethylpentanoic acid, H—(Me) Ile-OH)(1.1 g, 7.9 mmol), Compound aa327 (1.4 g, 72%) was obtained in the same manner as synthesis of Compound aa309.

LCMS (ESI) m/z=240 (M−H)−

Retention time: 0.61 min (Analytical condition SQDFA05)

aa326

Using Compound aa326-a ((S)-2-((((9H-fluoren-9-yl)methoxy) carbonyl)amino)-2-methylpentanoic acid, Fmoc-(Me) Nva-OH)(3.0 g, 8.5 mmol) as a starting material, Compound aa326-b ((S)-2-amino-2-methylpentanoic acid, H—(Me) Nva-OH)(1.1 g, 96%) was obtained in the same manner as synthesis of Compound aa309-b, and used in the next reaction.

LCMS (ESI) m/z=132 (M+H)+

Retention time: 0.13 min (Analytical condition SQDFA05)

Using Compound aa326-b ((S)-2-amino-2-methylpentanoic acid, H—(Me) Nva-OH)(1.1 g, 8.2 mmol), Compound aa326 (1.2 g, 64%) was obtained in the same manner as synthesis of Compound aa309.

LCMS (ESI) m/z=226 (M−H)−

Retention time: 0.55 min (Analytical condition SQDFA05)

Synthesis of Compound aa327

Synthesis of Compound aa329

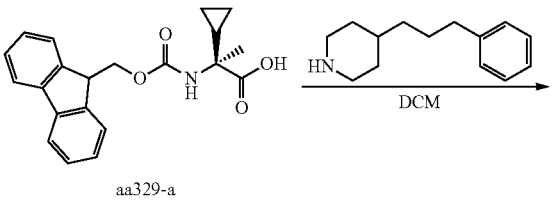

aa329-a

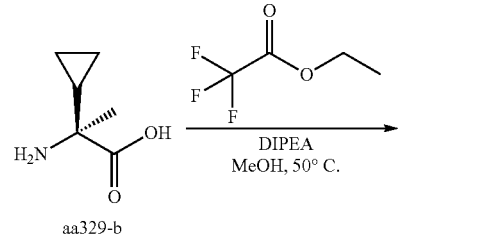

aa329-b

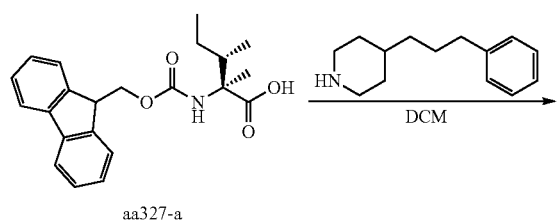

aa327-a

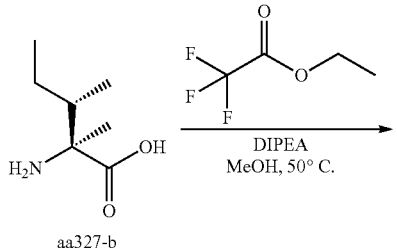

aa327-b aa329

Compound aa329-a ((S)-2-((((9H-fluoren-9-yl)methoxy) carbonyl)amino)-2-cyclopropylpropanoic acid, Fmoc-(Me) Gly (cPr)—OH)(3.0 g, 8.5 mmol) as a starting material, Compound aa329-b ((S)-2-amino-2-cyclopropylpropanoic acid, H—(Me)Gly (cPr)—OH)(1.1 g, 100%) was obtained in the same manner as synthesis of Compound aa309-b, and used in the next reaction.

LCMS (ESI) m/z=130 (M+H)+

Retention time: 0.13 min (Analytical condition SQDFA05)

Using Compound aa329-b ((S)-2-amino-2-cyclopropyl-propanoic acid, H—(Me)Gly (cPr)—OH)(1.1 g, 8.5 mmol), Compound aa329 (1.5 g, 76%) was obtained in the same manner as synthesis of Compound aa309.

LCMS (ESI) m/z=226 (M+H)+

Retention time: 0.46 min (Analytical condition SQDFA05)

Synthesis of Compound aa317

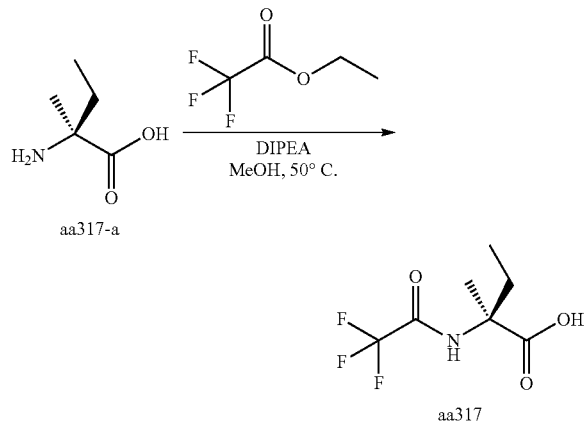

After N,N-diisopropylethylamine (82.7 g, 640 mmol) and ethyl 2,2,2-trifluoroacetate (54.6 g, 384 mmol) were added to a methanol (150 mL) solution of Compound aa317-a ((S)-2-amino-2-methylbutanoic acid, isovaline, H—(Me) Abu-OH)(15.0 g, 128 mmol), the mixture was stirred at 50° C. for 16 hours. The reaction solution was cooled to room temperature and then concentrated under reduced pressure, and the resulting residue was dissolved in TBME and then washed twice with 1 N hydrochloric acid. The organic layer was dried over anhydrous sodium sulfate, filtered, and then concentrated under reduced pressure to give a crude product. The resulting crude product was recrystallized from TBME/hexane (1:7) to give Compound aa317 (12 g, 44%).

LCMS (ESI) m/z=214 (M+H)+

Retention time: 0.32 min (Analytical condition SQDFA05)

Synthesis of Compound aa320

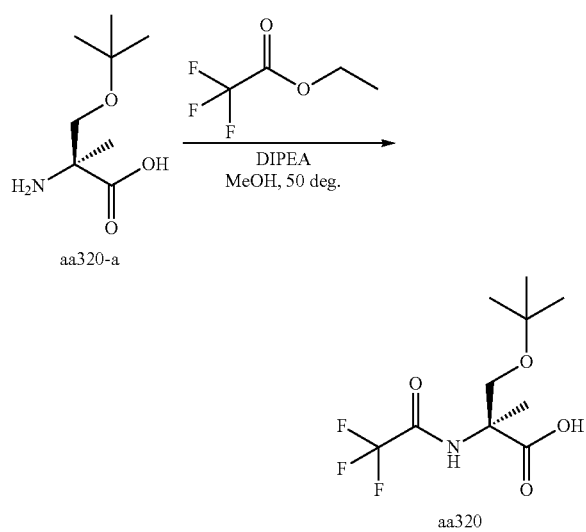

After N,N-diisopropylethylamine (5.4 mL, 30.8 mmol) and ethyl 2,2,2-trifluoroacetate (3.7 mL, 30.8 mmol) were added to a methanol (17.1 mL) solution of Compound aa320-a ((S)-2-amino-3-(tert-butoxy)-2-methylpropanoic acid, H—(Me) Ser (tBu)-OH)(1.8 g, 10.3 mmol), the mixture was stirred at 50° C. for 5 hours. Then, N,N-diisopropylethylamine (2.7 mL, 15.4 mmol) and ethyl 2,2,2-trifluoroacetate (1.8 mL, 15.4 mmol) were added, and the mixture was stirred at 50° C. for 16 hours. The reaction solution was cooled to room temperature and then concentrated under reduced pressure, and the resulting residue was dissolved in TBME (40 mL) and washed twice with 1 N hydrochloric acid (40 mL) and once with saturated brine (40 mL).

The organic layer was dried over anhydrous sodium sulfate, filtered, and then concentrated under reduced pressure to give a crude product. The resulting crude product was purified by reverse phase column chromatography (0.1% formic acid-water/0.1% formic acid-acetonitrile) to give Compound aa320 (2.3 g, 82%).

LCMS (ESI) m/z=270 (M-H)-

Retention time: 0.65 min (Analytical condition SQDFA05)

Synthesis of Compound aa322

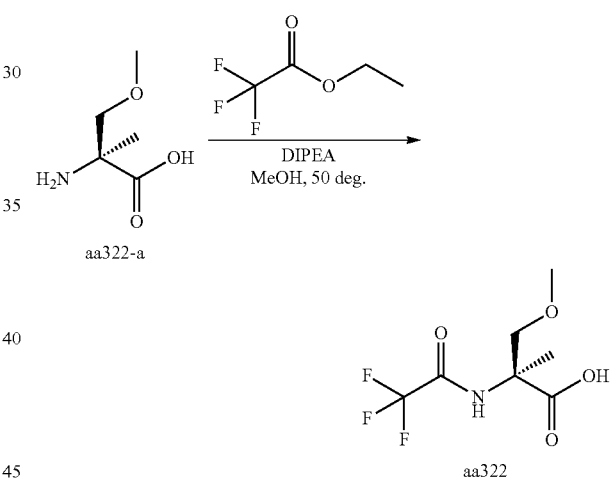

Diisopropylethylamine (5.9 mL, 33.8 mmol) and ethyl 2,2,2-trifluoroacetate (4.0 mL, 33.8 mmol) were added to a methanol (18.8 mL) solution of Compound aa322-a ((S)-2-amino-3-methoxy-2-methylpropanoic acid, H—(Me) Ser (Me)-OH)(1.5 g, 11.3 mmol), and the mixture was stirred at 50° C. for 21 hours. The reaction solution was cooled to room temperature and then concentrated under reduced pressure, and the resulting residue was dissolved in TBME (45 mL) and then washed twice with 1 N hydrochloric acid (45 mL) and once with saturated brine (45 mL). The organic layer was dried over anhydrous sodium sulfate, filtered, and then concentrated under reduced pressure to give a crude product. The resulting crude product was purified by reverse phase column chromatography (0.1% formic acid-water/0.1% formic acid-acetonitrile) to give Compound aa322 (2.1 g, 80%).

LCMS (ESI) m/z=230 (M+H)+

Retention time: 0.41 min (Analytical condition SQDFA05)

Synthesis of Compound aa323

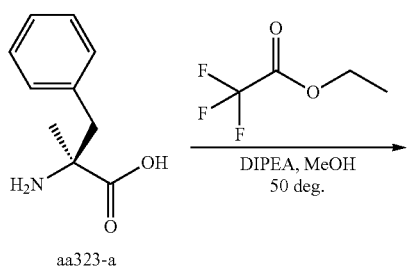

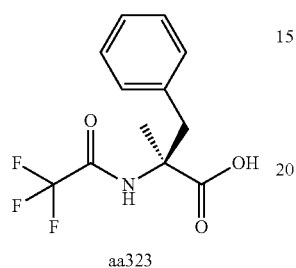

Using Compound aa323-a ((2S)-2-amino-2-methyl-3-phenylpropanoic acid, H—(Me) Phe-OH)(10.0 g, 55.8 mmol) as a starting material, Compound aa323 (8 g, 52%) was obtained in the same manner as synthesis of Compound aa317.

LCMS (ESI) m/z=276 (M+H)+

Retention time: 0.68 min (Analytical condition SQDFA05)

Synthesis of Compound aa325

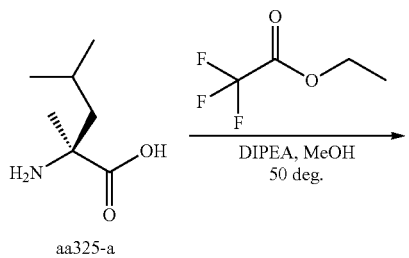

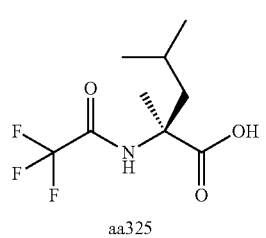

Using Compound aa325-a (2-methylleucine, (S)-2-amino-2,4-dimethylpentanoic acid, H—(Me) Leu-OH)(15.0 g, 103 mmol) as a starting material, Compound aa325 (10 g, 40%) was obtained in the same manner as synthesis of Compound aa317.

LCMS (ESI) m/z=242 (M+H)+

Retention time: 0.66 min (Analytical condition SQDFA05)

Synthesis of Compound aa328

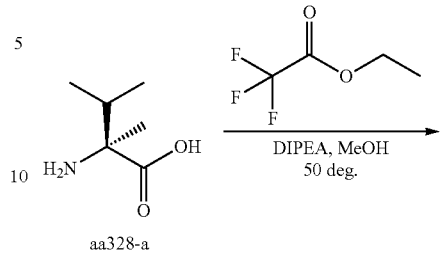

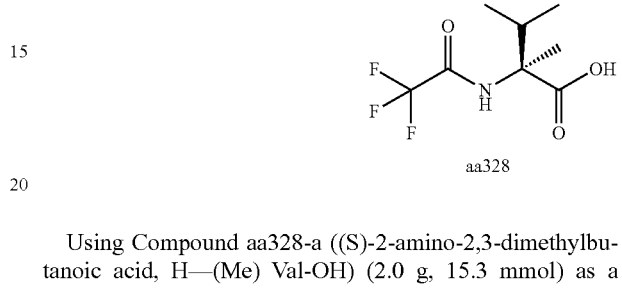

Using Compound aa328-a ((S)-2-amino-2,3-dimethylbutanoic acid, H—(Me) Val-OH) (2.0 g, 15.3 mmol) as a starting material, Compound aa328 (1.2 g, 34%) was obtained in the same manner as synthesis of Compound aa320.

LCMS (ESI) m/z=226 (M−H)−

Retention time: 0.54 min (Analytical condition SQDFA05)

Synthesis of Compound aa319

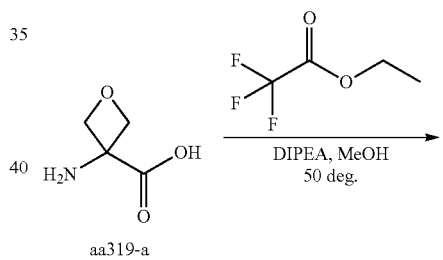

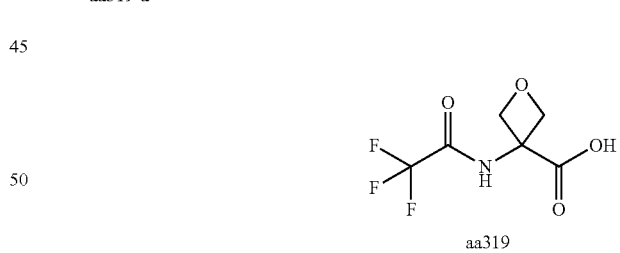

Using Compound aa319-a (3-aminooxetane-3-carboxylic acid, H-AoxeC-OH)(10.0 g, 85.4 mmol) as a starting material, Compound aa319 (9.8 g, 54%) was obtained in the same manner as synthesis of Compound aa317.

LCMS (ESI) m/z=214 (M+H)+

Retention time: 0.50 min (Analytical condition SQDFA05) 1-6. Cyclic peptide synthesis by peptide modification 1-6-1. Peptide modification by alkylation of OH Synthesis of Compound PP0242

Compound PP242 was synthesized according to the following scheme.

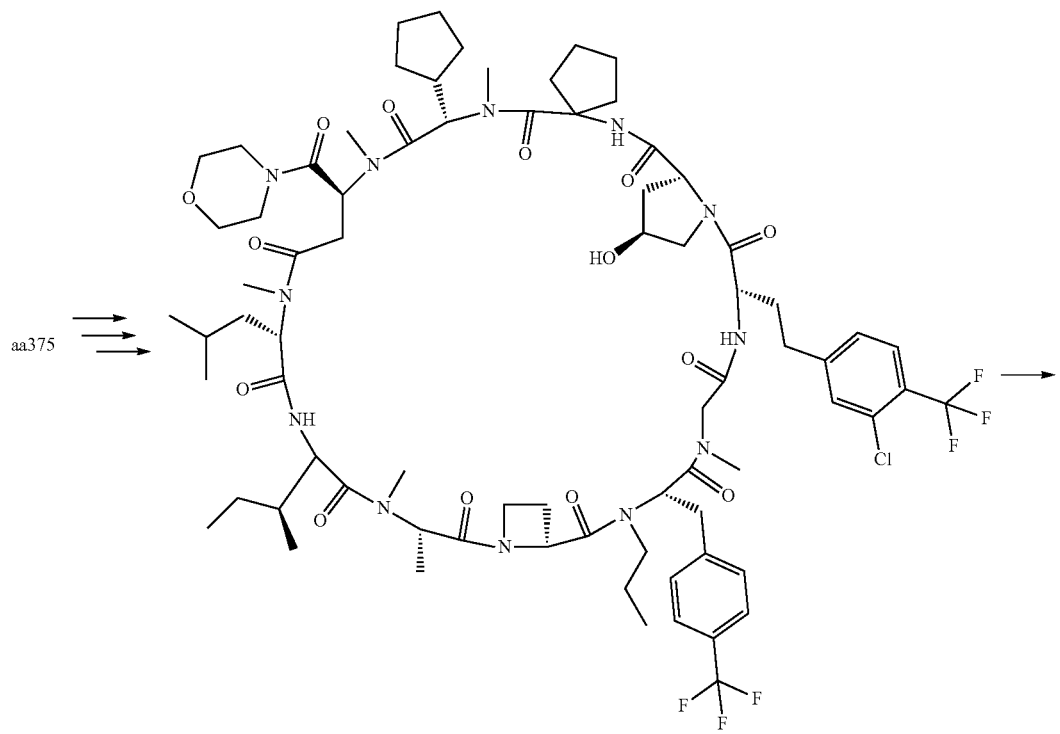

Compound PP0238

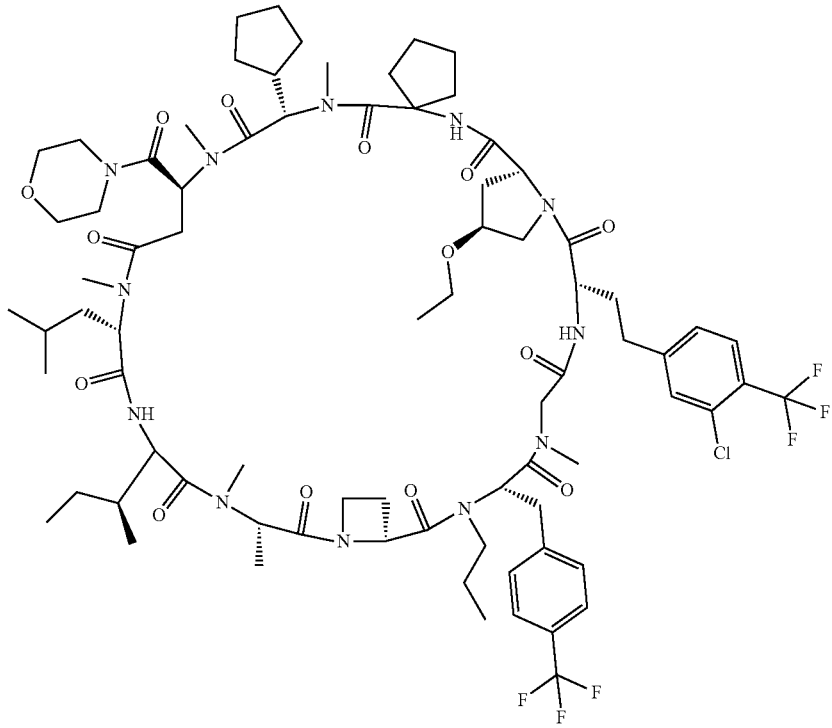

Compound PP0242

Using Compound aa375-resin as a raw material, peptide synthesis by the basic peptide synthesis method described in the present Examples was performed to give Compound PP0238 (120.3 mg, 0.077 mmol).

LCMS (ESI) m/z=1562 (M+H)+

Retention time: 0.99 min (Analytical condition SQDFA05)

Iodoethane (2.6 μL, 32.0 μmol), tetrabutylammonium bromide (3.1 mg, 9.6 μmol), and a 5 N aqueous sodium hydroxide solution (12.8 μL, 64.0 μmol) were added to a dichloromethane (80 μL) solution of Compound PP238 (5.0 mg, 3.20 µmol), and the mixture was stirred at room temperature for 7 days in a nitrogen atmosphere. The resulting reaction mixture was purified by reverse phase column chromatography (0.1% formic acid-containing acetonitrile/0.1% formic acid-containing distilled water) to give Compound PP0242 (2.3 mg, 45%). LC/MS data is provided in Table 36.

Synthesis of Compound PP0243

Compound PP243 was synthesized according to the following scheme.

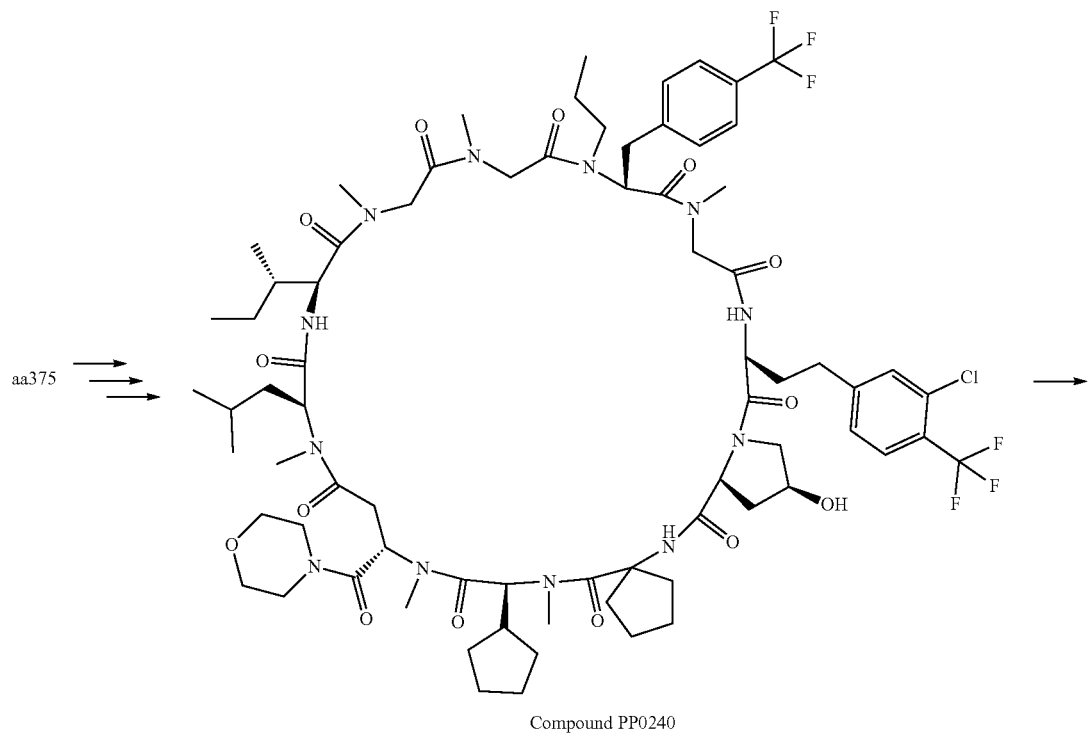

Compound PP0240

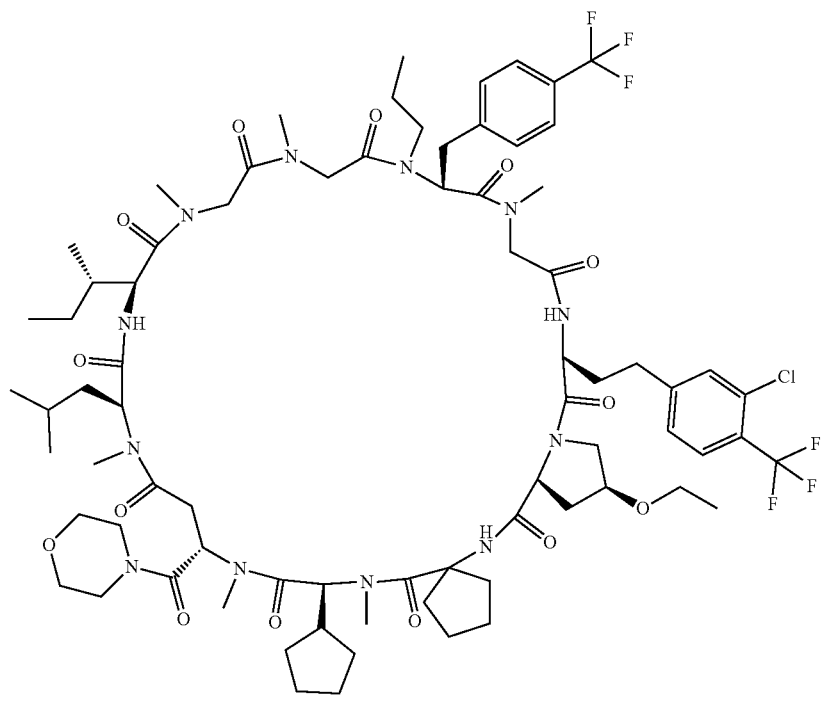

Compound PP0243

Using Compound aa375-resin as a raw material, peptide synthesis by the basic peptide synthesis method described in the present Examples was performed to give Compound PP0240 (119.2 mg, 0.078 mmol).

LCMS (ESI) m/z=1536 (M+H)+

Retention time: 0.97 min (Analytical condition SQDFA05)

Iodoethane (2.6 μL, 32.0 μmol), tetrabutylammonium bromide (3.1 mg, 9.6 μmol), and a 5 N aqueous sodium hydroxide solution (12.8 μL, 64.0 μmol) were added to a dichloromethane (80 μL) solution of Compound PP240 (4.9 mg, 3.20 μmol), and the mixture was stirred at room temperature for 7 days in a nitrogen atmosphere. The resulting reaction mixture was purified by reverse phase column chromatography (0.1% formic acid-containing acetonitrile/0.1% formic acid-containing distilled water) to give Compound PP0243 (2.6 mg, 52%). LC/MS data is provided in Table 36.

Synthesis of Compound PP0245

Compound PP245 was synthesized according to the following scheme.

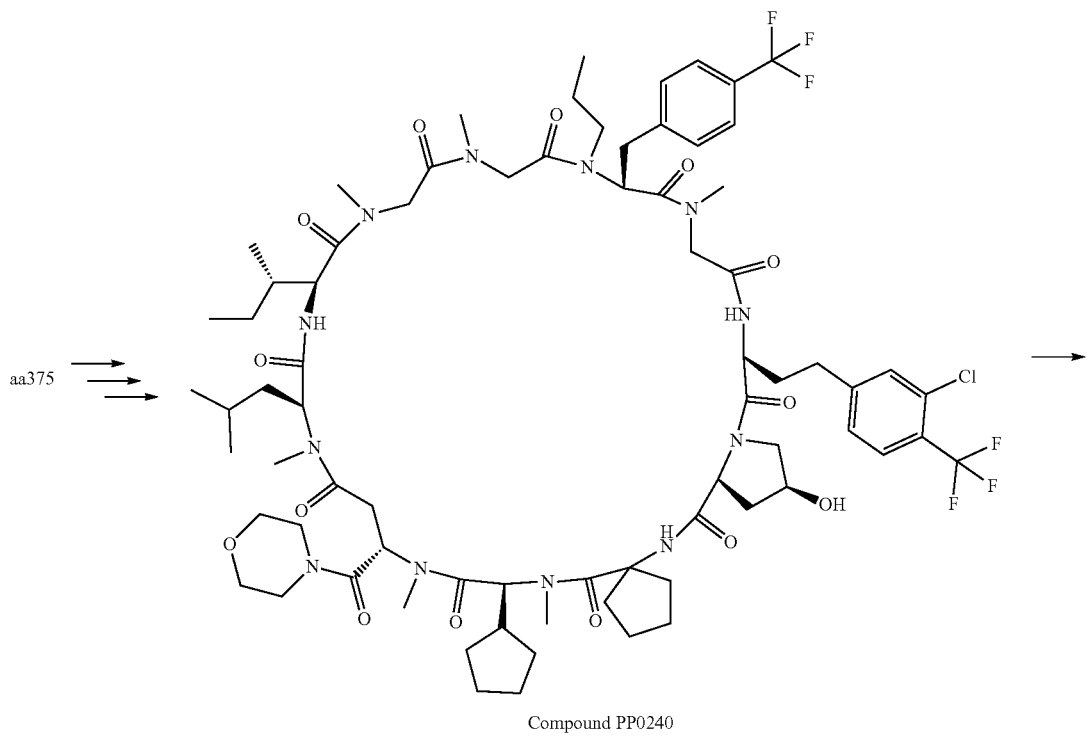

Compound PP0240

-continued

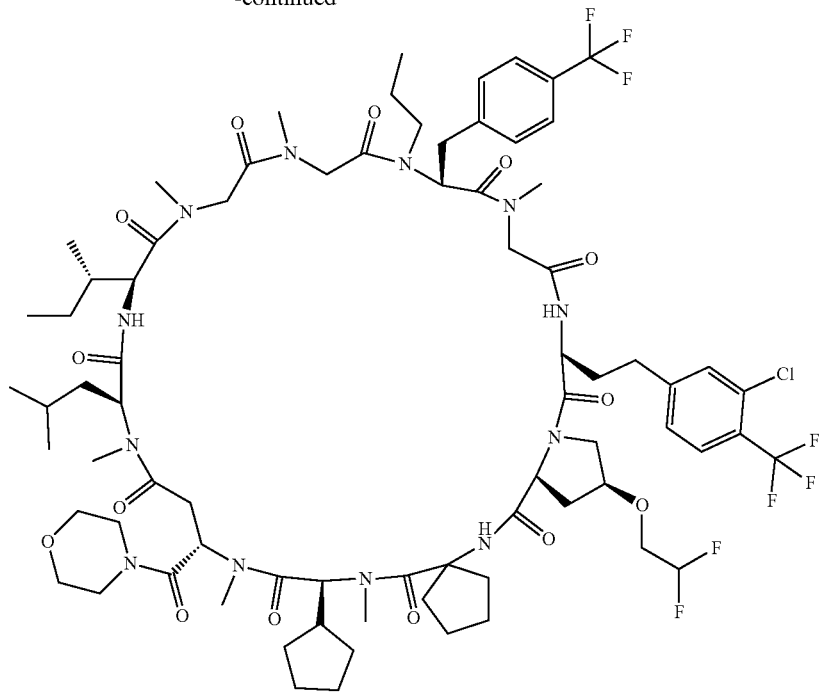

Compound PP0245

Using Compound aa375-resin as a raw material, peptide synthesis by the basic peptide synthesis method described in the present Examples was performed to give Compound PP0240 (119.2 mg, 0.078 mmol).

LCMS (ESI) m/z=1536 (M+H)+

Retention time: 0.97 min (Analytical condition SQDFA05)

2,2-Difluoroethyl trifluoromethanesulfonate (4.2 μL, 32.0 μmol), tetrabutylammonium bromide (3.1 mg, 9.6 μmol), and a 5 N aqueous sodium hydroxide solution (12.8 μL, 64.0 μmol) were added to a dichloromethane (80 μL) solution of Compound PP240 (4.9 mg, 3.20 μmol), and the mixture was stirred at room temperature for 48 hours in a nitrogen atmosphere. The resulting reaction mixture was purified by reverse phase column chromatography (0.1% formic acid-containing acetonitrile/0.1% formic acid-containing distilled water) to give Compound PP0245 (4.2 mg, 82%). LC/MS data is provided in Table 36.

Synthesis of Compound PP0246

Compound PP246 was synthesized according to the following scheme.

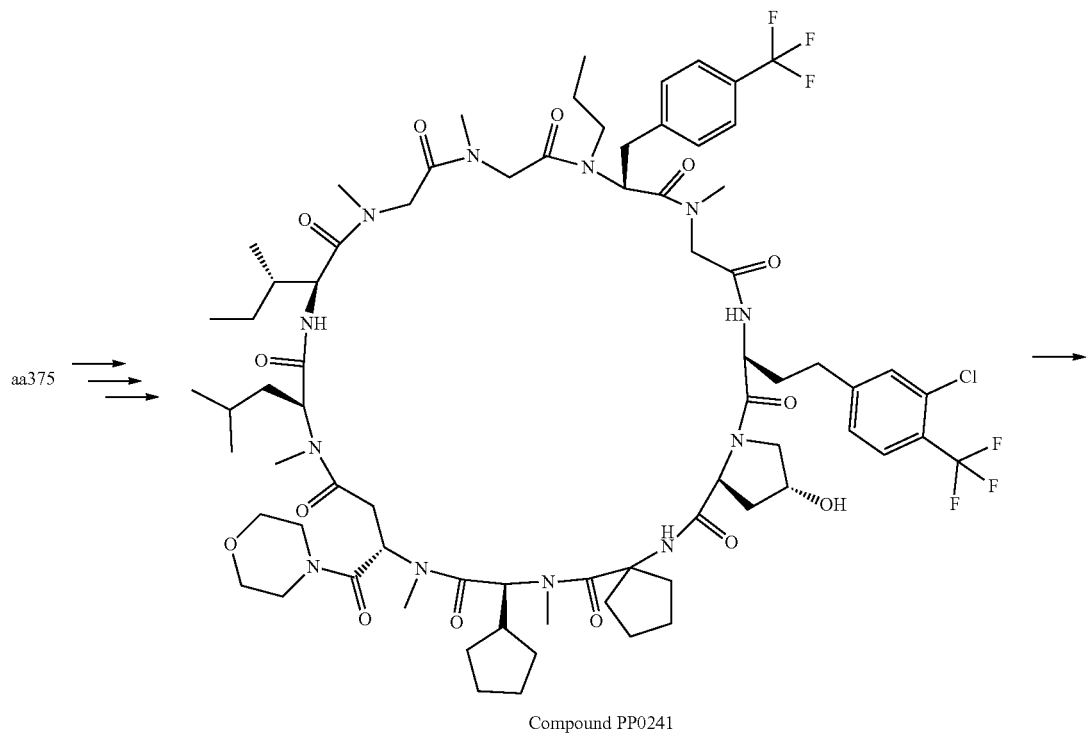

Compound PP0241

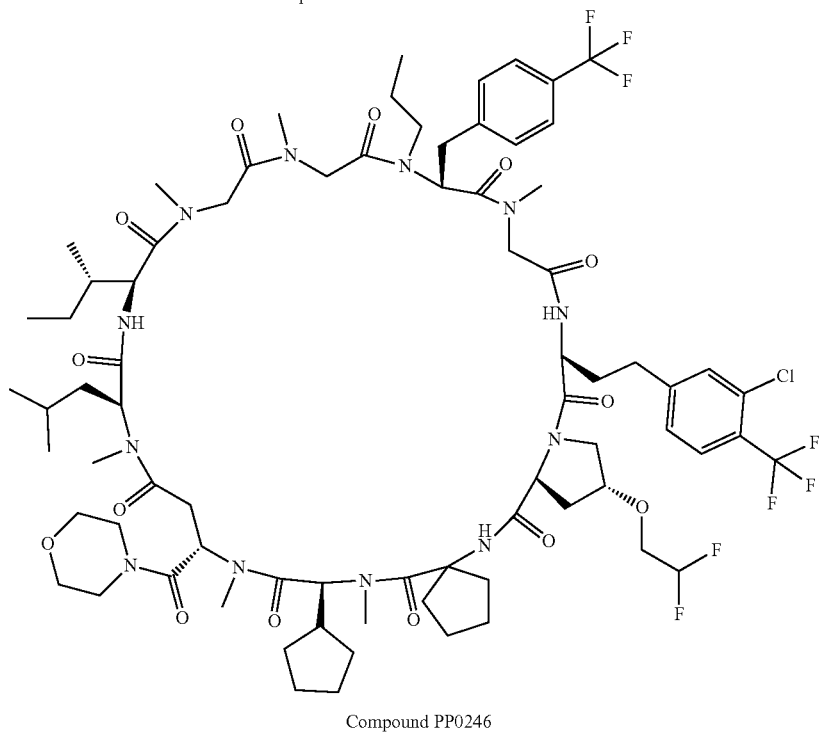

Compound PP0246

Using Compound aa375-resin as a raw material, peptide synthesis by the basic peptide synthesis method described in the present Examples was performed to give Compound PP0241 (109.6 mg, 0.071 mmol).

LCMS (ESI) m/z=1536 (M+H)+

Retention time: 0.95 min (Analytical condition SQDFA05)

2,2-Difluoroethyl trifluoromethanesulfonate (4.2 μL, 32.0 μmol), tetrabutylammonium bromide (3.1 mg, 9.6 μmol), and a 5 N aqueous sodium hydroxide solution (12.8 μL, 64.0 μmol) were added to a dichloromethane (80 μL) solution of Compound PP241 (4.9 mg, 3.20 μmol), and the mixture was stirred at room temperature for 48 hours in a nitrogen atmosphere. The resulting reaction mixture was purified by reverse phase column chromatography (0.1% formic acid-containing acetonitrile/0.1% formic acid-containing distilled water) to give Compound PP0246 (4.4 mg, 86%). LC/MS data is provided in Table 36.

Synthesis of Compound PP998
Compound PP998 was synthesized according to the following scheme.
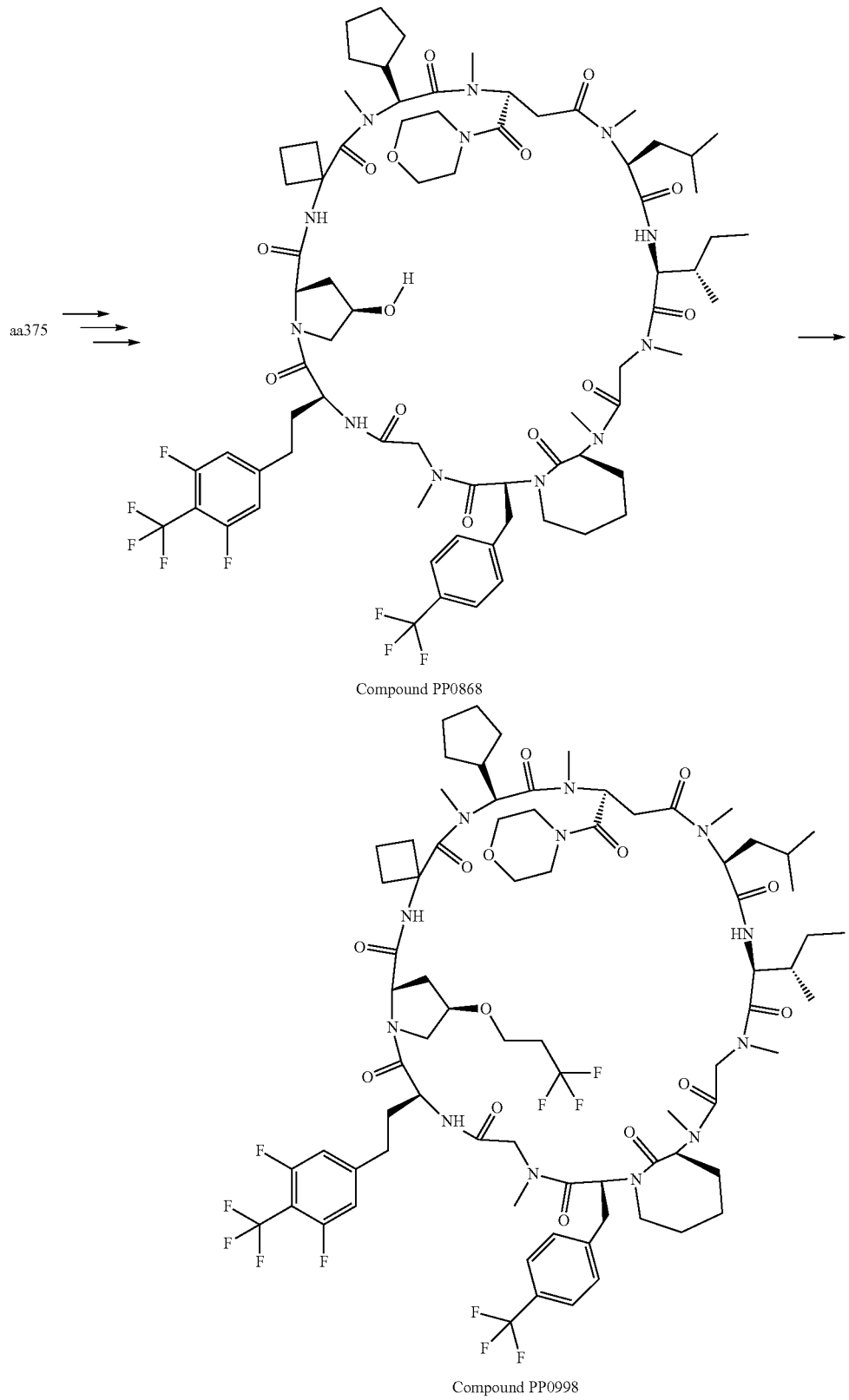
Compound PP0868
Compound PP0998

Using Compound aa375-resin as a raw material, peptide synthesis by the basic peptide synthesis method described in the present Examples was performed to give Compound PP0868 (76.8 mg, 0.0500 mmol).

LCMS (ESI) m/z=1536 (M+H)+

Retention time: 0.93 min (Analytical condition SQDFA50 long)

3,3,3-Trifluoropropyl trifluoromethanesulfonate (5.0 µL, 33.0 µmol), tetrabutylammonium bromide (3.2 mg, 9.77 µmol), and a 5 N aqueous sodium hydroxide solution (13.0 µL, 65.0 µmol) were added to a dichloromethane (65.1 µL) solution of Compound PP0868 (5.0 mg, 3.26 µmol), and the mixture was stirred at room temperature for 9 days in a nitrogen atmosphere. Dichloromethane (300 µL) and water (300 µL) were added to the resulting reaction mixture, the separated organic layer was concentrated under reduced pressure, and the resulting crude product was purified by reverse phase HPLC(methanol/50 mM aqueous ammonium acetate solution) to give Compound PP0998 (0.31 mg, 6%). LC/MS data is provided in Table 36.

Synthesis of Compounds PP999 to PP1003 and PP1013 to PP1015 Using Compound PP0868 as a raw material and the alkylating agents shown in Table 11, the following Compounds PP999 to PP1003 and PP1013 to PP1015 were obtained in the same manner as synthesis of PP998. LC/MS data is provided in Table 36.

TABLE 11

| Peptide | Alkylating agent | Raw material (mg) | Yield (mg) | Yield (%) |
| --- | --- | --- | --- | --- |
| PP0999 | 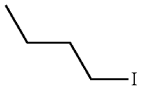 | 5.0 | 0.94 | 18 |
| PP1000 | | 5.0 | 1.56 | 30 |
| PP1001 | | 5.0 | 0.16 | 3 |
| PP1002 | | 5.0 | 4.07 | 78 |
| PP1003 | Me—I | 5.0 | 3.32 | 66 |
| PP1013 | — | — | 1.27 | 24 |
| PP1014 | — | — | 0.74 | 14 |
| PP1015 | — | — | 0.20 | 4 |

* PP1013 was obtained as a by-product of synthesis of PP0999.
* PP1014 was obtained as a by-product of synthesis of PP1000.
* PP1015 was obtained as a by-product of synthesis of PP1001.

Synthesis of Compound PP1004

Compound PP1004 was synthesized according to the following scheme.

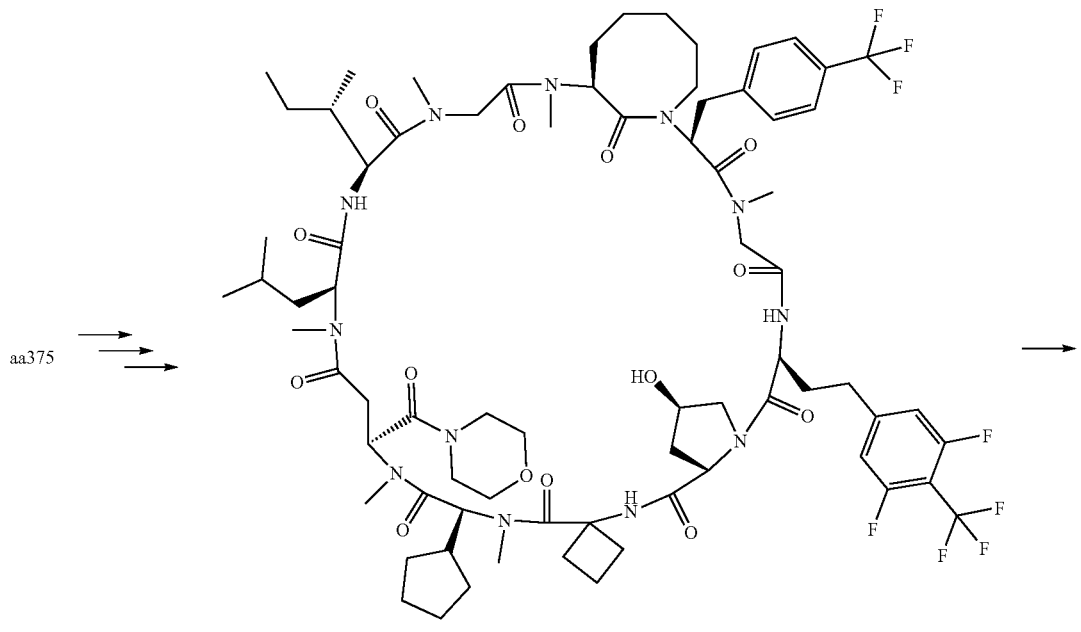

Compound PP0871

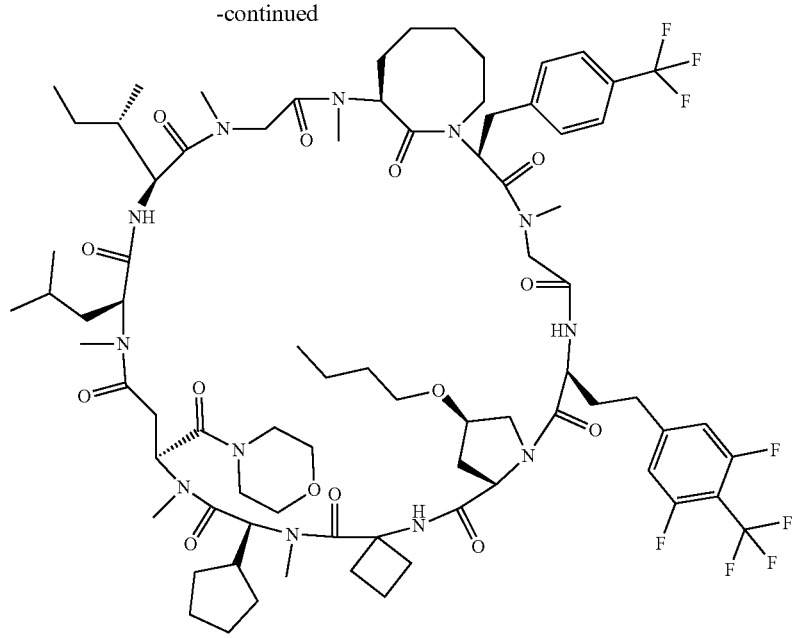

Compound PP1004

Using Compound aa375-resin as a raw material, peptide synthesis by the basic peptide synthesis method described in the present Examples was performed to give Compound PP0871 (57.5 mg, 0.0371 mmol).

LCMS (ESI) m/z=1550 (M+H)+

Retention time: 1.52 min (Analytical condition SQDFA50 long)

1-Iodobutane (3.7 µL, 32.0 µmol), tetrabutylammonium bromide (3.1 mg, 9.68 µmol), and a 5 N aqueous sodium hydroxide solution (12.9 µL, 65.0 µmol) were added to a dichloromethane (64.5 µL) solution of Compound PP0871 (5.0 mg, 3.23 µmol), and the mixture was stirred at room temperature for 7 days in a nitrogen atmosphere. Dichloromethane (300 µL) and water (300 µL) were added to the resulting reaction mixture, the separated organic layer was concentrated under reduced pressure, and the resulting crude product was purified by reverse phase HPLC(methanol/50 mM aqueous ammonium acetate solution) to give Compound PP1004 (0.76 mg, 15%). LC/MS data is provided in Table 36.

Synthesis of Compounds PP1005 to PP1006 and PP1016

Using Compound PP0871 as a raw material and the alkylating agents shown in Table 12, the following Compounds PP1005 to PP1006 and PP1016 were obtained in the same manner as synthesis of PP1004. LC/MS data is provided in Table 36.

TABLE 12

| Peptide | Alkylating agent | Raw material (mg) | Yield (mg) | Yield (%) |
|---|---|---|---|---|
| PP1005 | cyclopropylmethyl-I | 5.0 | 0.31 | 6 |
| PP1006 | CF₃SO₂-O-CH₂CHF₂ | 5.0 | 3.34 | 64 |
| PP1016 | Me—I | 5.0 | 1.14 | 22 |

Synthesis of Compound PP1008

Compound PP1008 was synthesized according to the following scheme.

aa375 →→→

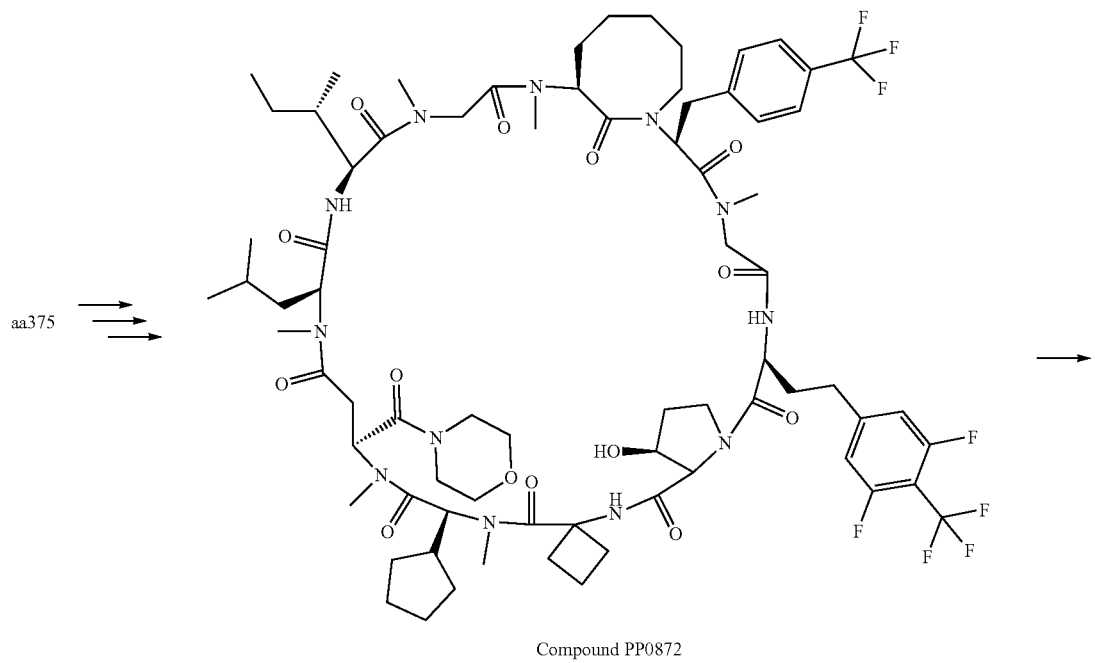

Compound PP0872

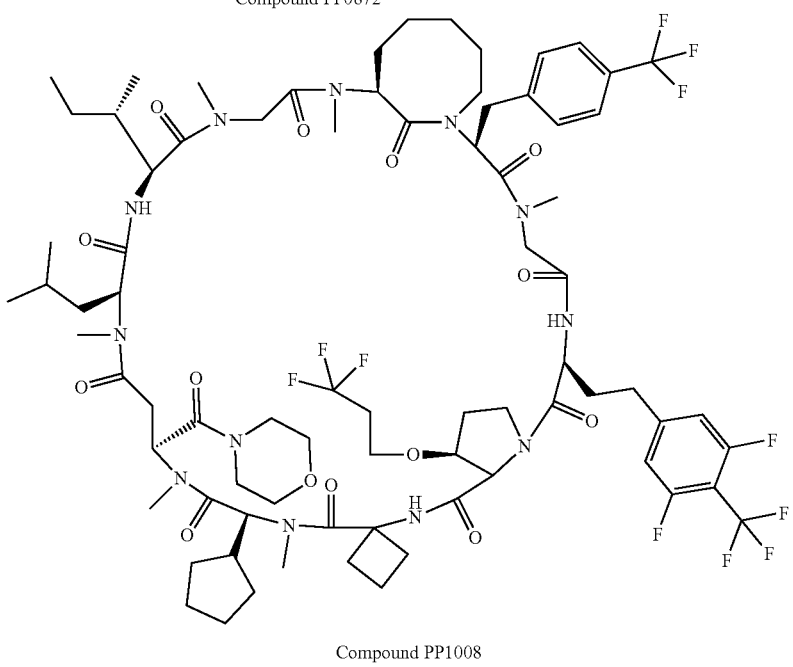

Compound PP1008

Using Compound aa375-resin as a raw material, peptide synthesis by the basic peptide synthesis method described in the present Examples was performed to give Compound PP0872 (71.7 mg, 0.0463 mmol).

LCMS (ESI) m/z=1550 (M+H)+

Retention time: 1.64 min (Analytical condition SQDFA50 long)

3,3,3-Trifluoropropyl trifluoromethanesulfonate (5.0 μL, 32.0 μmol), tetrabutylammonium bromide (3.1 mg, 9.68 μmol), and a 5 N aqueous sodium hydroxide solution (12.9 μL, 65.0 μmol) were added to a dichloromethane (64.5 μL) solution of Compound PP0872 (5.0 mg, 3.23 μmol), and the mixture was stirred at room temperature for 5 days in a nitrogen atmosphere. Dichloromethane (300 μL) and water (300 μL) were added to the resulting reaction mixture, the separated organic layer was concentrated under reduced pressure, and the resulting crude product was purified by reverse phase HPLC(methanol/50 mM aqueous ammonium acetate solution) to give Compound PP1008 (1.76 mg, 33%). LC/MS data is provided in Table 36.

Synthesis of Compounds PP1009 to PP1012 and PP1067 to PP1069

Using Compound PP0872 as a raw material and the alkylating agents shown in Table 13, the following Compounds PP1009 to PP1012 and PP1067 to PP1069 were obtained in the same manner as synthesis of PP1008. LC/MS data is provided in Table 36.

TABLE 13
| Peptide | Alkylating agent | Raw material (mg) | Yield (mg) | Yield (%) |
|---|---|---|---|---|
| PP1009 | CH2CH2CH2CH2-I | 5.0 | 1.52 | 29 |
| PP1010 | cyclopropyl-CH2-I | 5.0 | 1.64 | 32 |
| PP1011 | cyclopentyl-CH2-I | 5.0 | 0.42 | 8 |
| PP1012 | CF3-CF2-CH2-OSO2CF3 | 5.0 | 1.79 | 34 |
TABLE 13-continued
| Peptide | Alkylating agent | Raw material (mg) | Yield (mg) | Yield (%) |
|---|---|---|---|---|
| PP1067 | Me—I | 5.0 | 3.90 | 77 |
| PP1068 | CH3CH2-I | 5.0 | 1.66 | 33 |
| PP1069 | CH3CH2CH2-I | 5.0 | 2.12 | 41 |
Synthesis of Compound PP1070
Compound PP1070 was synthesized according to the following scheme.
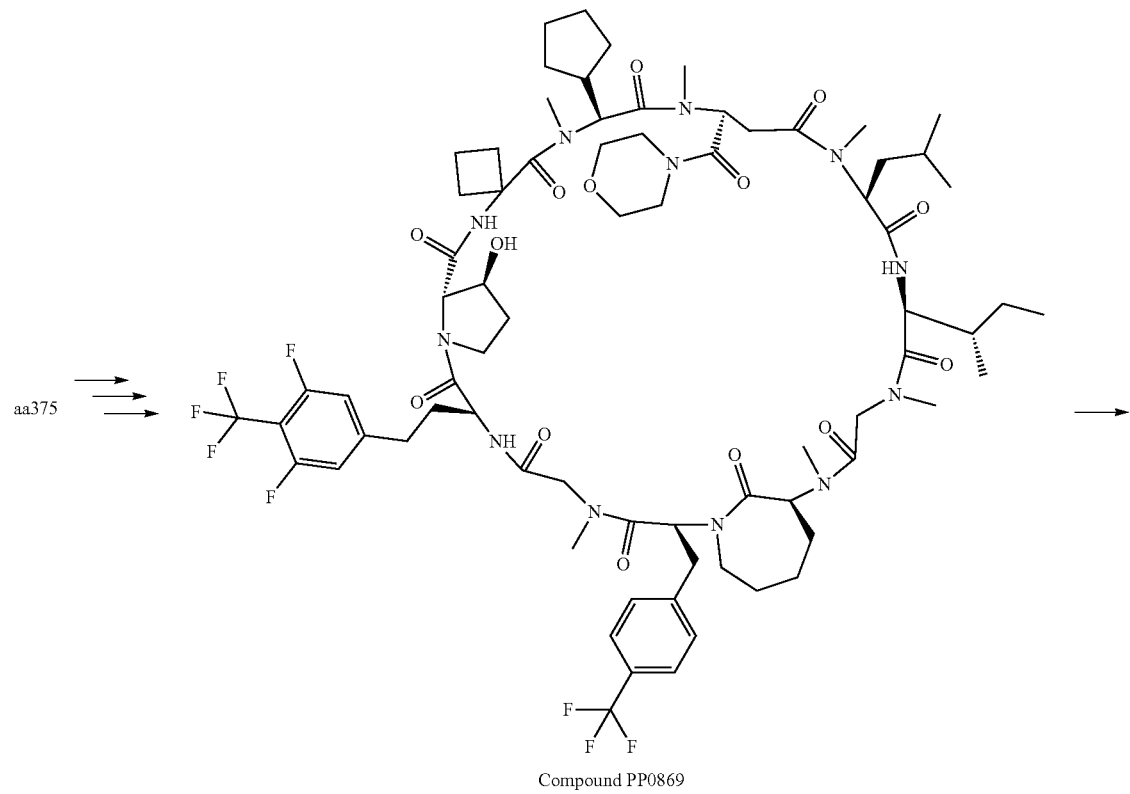
Compound PP0869

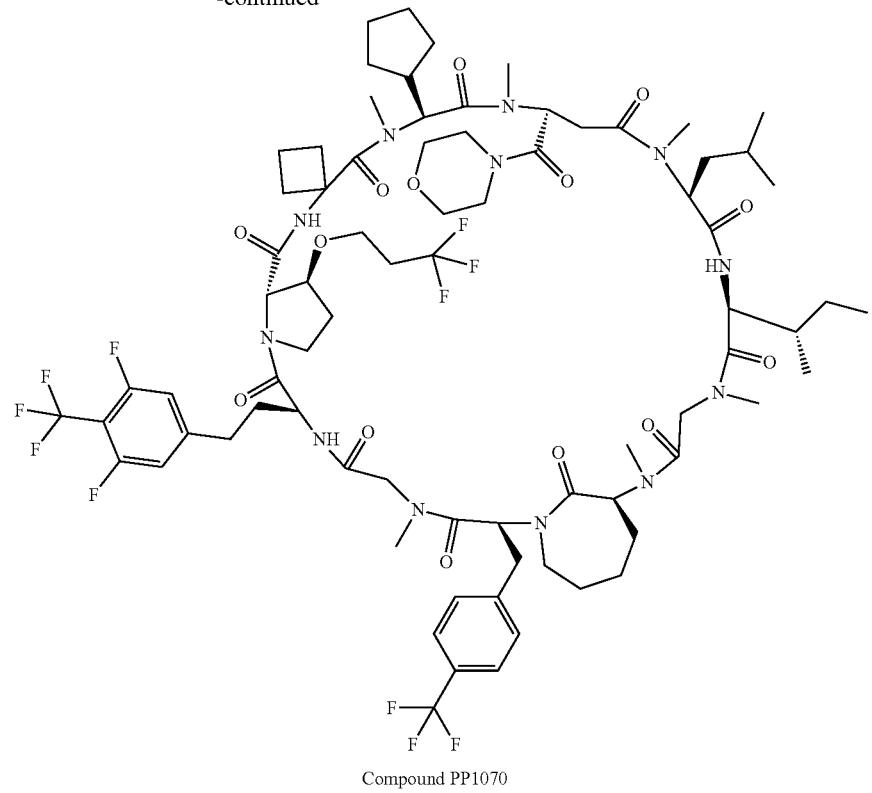

Compound PP1070

Using Compound aa375-resin as a raw material, peptide synthesis by the basic peptide synthesis method described in the present Examples was performed to give Compound PP0869 (78.0 mg, 0.0508 mmol).

LCMS (ESI) m/z=1536 (M+H)+

Retention time: 1.01 min (Analytical condition SQDFA50 long)

3,3,3-Trifluoropropyl trifluoromethanesulfonate (5.0 µL, 33.0 µmol), tetrabutylammonium bromide (3.2 mg, 9.77 µmol), and a 5 N aqueous sodium hydroxide solution (13.0 µL, 65.0 µmol) were added to a dichloromethane (65.1 µL) solution of Compound PP0869 (5.0 mg, 3.26 µmol), and the mixture was stirred at room temperature for 5 days in a nitrogen atmosphere. Dichloromethane (300 µL) and water (300 µL) were added to the resulting reaction mixture, the separated organic layer was concentrated under reduced pressure, and the resulting crude product was purified by reverse phase HPLC(methanol/50 mM aqueous ammonium acetate solution) to give Compound PP1070 (0.63 mg, 12%). LC/MS data is provided in Table 36.

Synthesis of Compounds PP1071 to PP1073 and PP1075 to PP1077

Using Compound PP0869 as a raw material and the alkylating agents shown in Table 14, the following Compounds PP1071 to PP1077 were obtained in the same manner as synthesis of PP1070. LC/MS data is provided in Table 36.

TABLE 14

| Peptide | Alkylating agent | Raw material (mg) | Yield (mg) | Yield (%) |
|---|---|---|---|---|
| PP1071 | (propyl iodide) | 5.0 | 2.45 | 47 |
| PP1072 | (cyclopropylmethyl iodide) | 5.0 | 2.37 | 46 |
| PP1073 | (cyclopentylmethyl iodide) | 5.0 | 0.47 | 9 |
| PP1075 | Me—I | 5.0 | 1.70 | 34 |
| PP1076 | | 5.0 | 3.33 | 65 |
| PP1077 | | 5.0 | 2.28 | 44 |

Synthesis of Compound PP1078

Compound PP1078 was synthesized according to the following scheme.

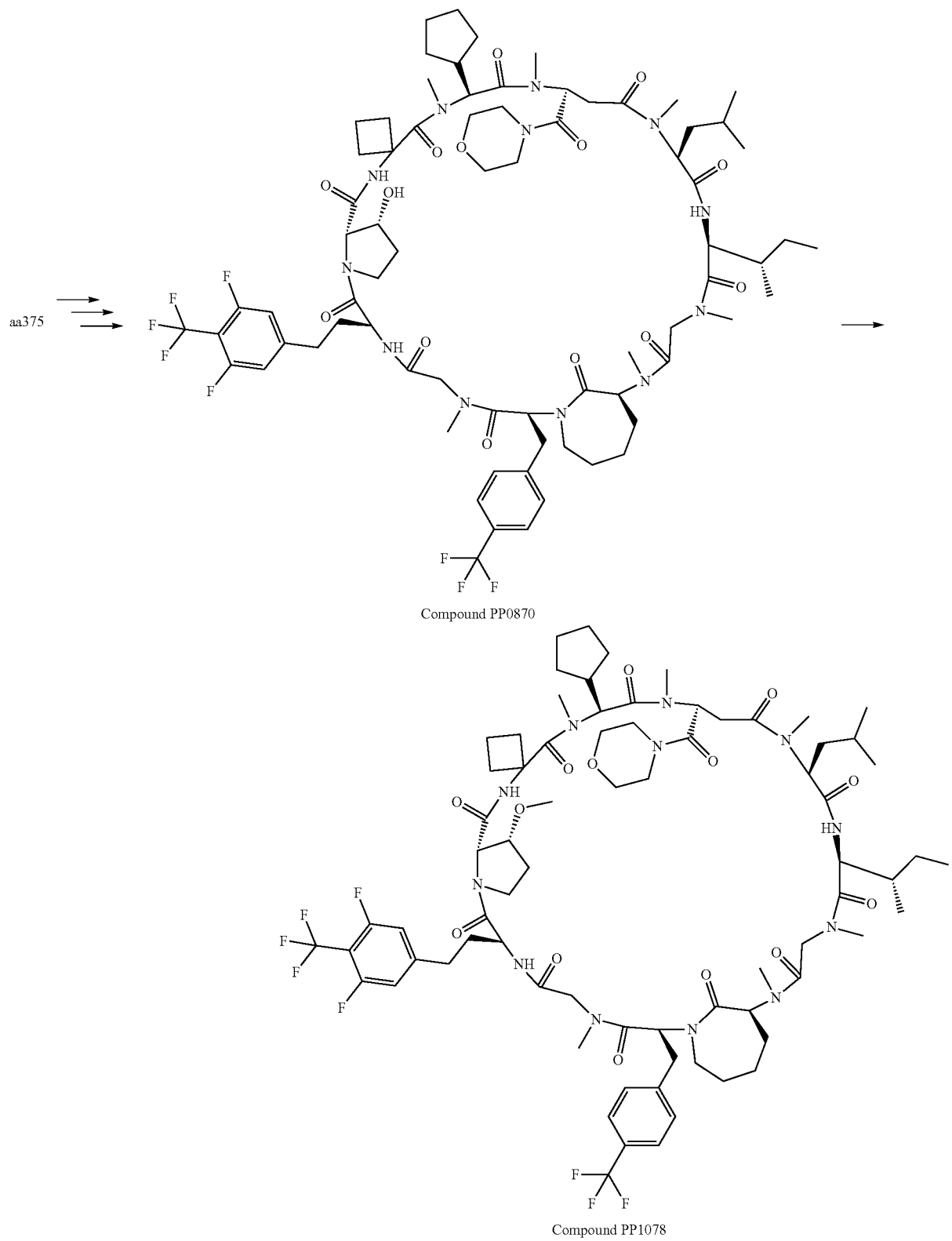
Compound PP0870
Compound PP1078
Using Compound aa375-resin as a raw material, peptide synthesis by the basic peptide synthesis method described in the present Examples was performed to give Compound PP0870 (53.6 mg, 0.0349 mmol).
LCMS (ESI) m/z=1536 (M+H)+
Retention time: 0.94 min (Analytical condition SQDFA50 long) Iodomethane (2.0 μL, 33.0 μmol), tetrabutylammonium bromide (3.2 mg, 9.77 μmol), and a 5 N aqueous sodium hydroxide solution (13.0 μL, 65.0 μmol) were added to a dichloromethane (65.1 μL) solution of Compound PP0870 (5.0 mg, 3.26 μmol), and the mixture was stirred at room temperature for 9 hours in a nitrogen atmosphere. Dichloromethane (300 μL) and water (300 μL) were added to the resulting reaction mixture, the separated organic layer was concentrated under reduced pressure, and the resulting crude product was purified by reverse phase HPLC(methanol/50 mM aqueous ammonium acetate solution) to give Compound PP1078 (0.37 mg, 7%). LC/MS data is provided in Table 36.

Synthesis of Compounds PP1079, PP1080, and PP1084

Using Compound PP0870 as a raw material and the alkylating agents shown in Table 15, the following Compounds PP1079, PP1080, and PP1084 were obtained in the same manner as synthesis of PP1078. LC/MS data is provided in Table 36.

TABLE 15

| Peptide | Alkylating agent | Raw material (mg) | Yield (mg) | Yield (%) |
|---|---|---|---|---|
| PP1079 |  | 5.0 | 2.35 | 46 |
| PP1080 |  | 5.0 | 2.17 | 42 |
| PP1084 | — | 5.0 | 0.92 | 17 |

* PP1084 was obtained as a by-product of synthesis of PP1078.

Synthesis of Compound PP1085

Compound PP1085 was synthesized according to the following scheme.

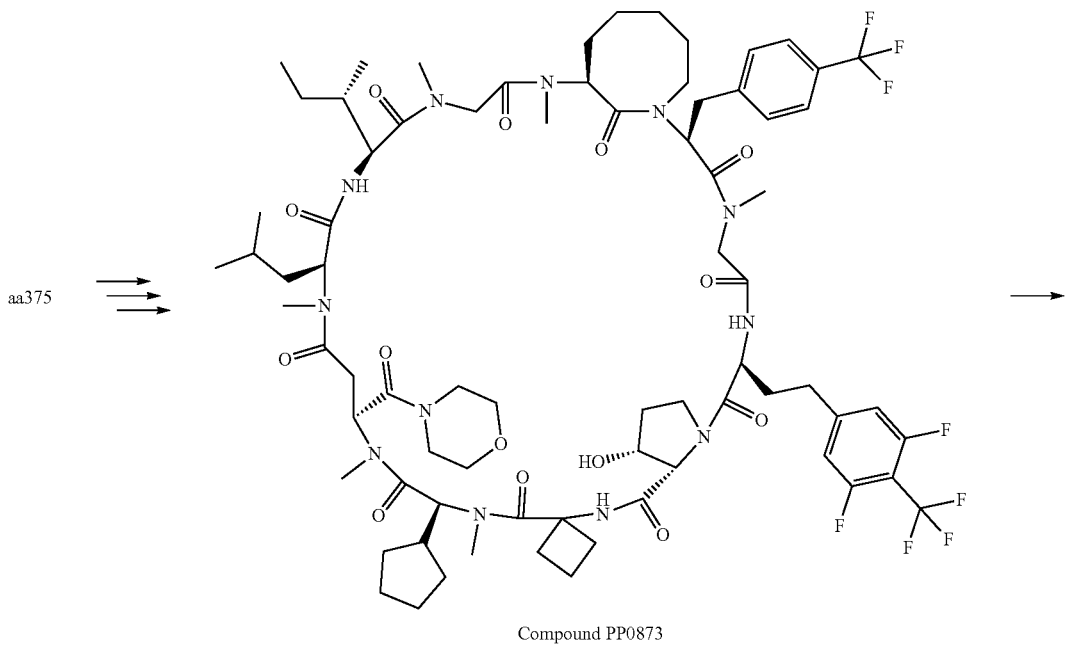

Compound PP0873

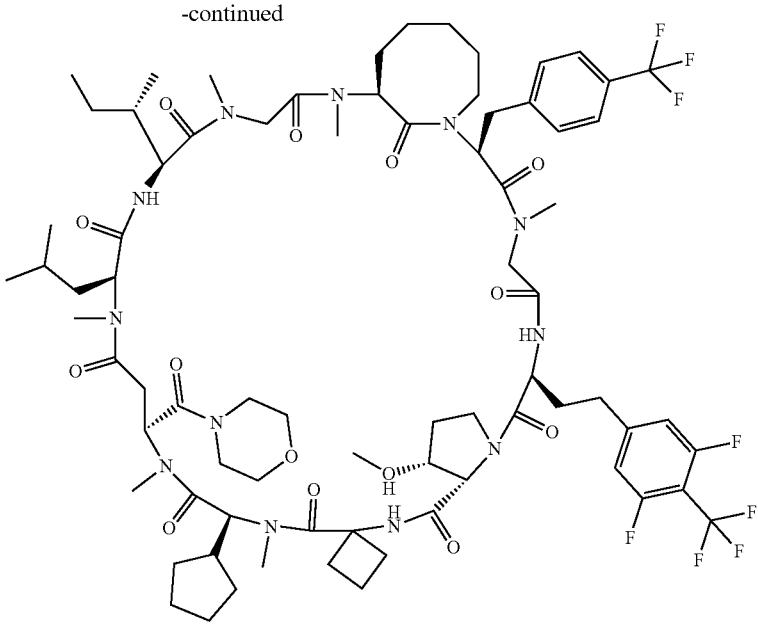

Compound PP1085

Using Compound aa375-resin as a raw material, peptide synthesis by the basic peptide synthesis method described in the present Examples was performed to give Compound PP0873 (37.3 mg, 0.0241 mmol).

LCMS (ESI) m/z=1550 (M+H)+

Retention time: 1.50 min (Analytical condition SQDFA50 long)

Iodomethane (2.0 µL, 32.0 µmol), tetrabutylammonium bromide (3.1 mg, 9.68 µmol), and a 5 N aqueous sodium hydroxide solution (12.9 µL, 65.0 µmol) were added to a dichloromethane (64.5 µL) solution of Compound PP0873 (5.0 mg, 3.23 µmol), and the mixture was stirred at room temperature for 9 hours in a nitrogen atmosphere. Dichloromethane (300 µL) and water (300 µL) were added to the resulting reaction mixture, the separated organic layer was concentrated under reduced pressure, and the resulting crude product was purified by reverse phase HPLC(methanol/50 mM aqueous ammonium acetate solution) to give Compound PP1085 (1.0 mg, 19%). LC/MS data is provided in Table 36.

Synthesis of Compounds PP1082 and PP1083

Using Compound PP0873 as a raw material and the alkylating agents shown in Table 17, the following Compounds PP1082 and PP1083 were obtained in the same manner as synthesis of PP1081. LC/MS data is provided in Table 36.

TABLE 17

| Peptide | Alkylating agent | Raw material (mg) | Yield (mg) | Yield (%) |
|---|---|---|---|---|
| PP1082 | ∖—I | 5.0 | 1.25 | 25 |
| PP1083 | ⌐∖—I | 5.0 | 0.93 | 18 |

Synthesis of Compound PP1533

Compound PP1533 was synthesized according to the following scheme.

aa374 →→→

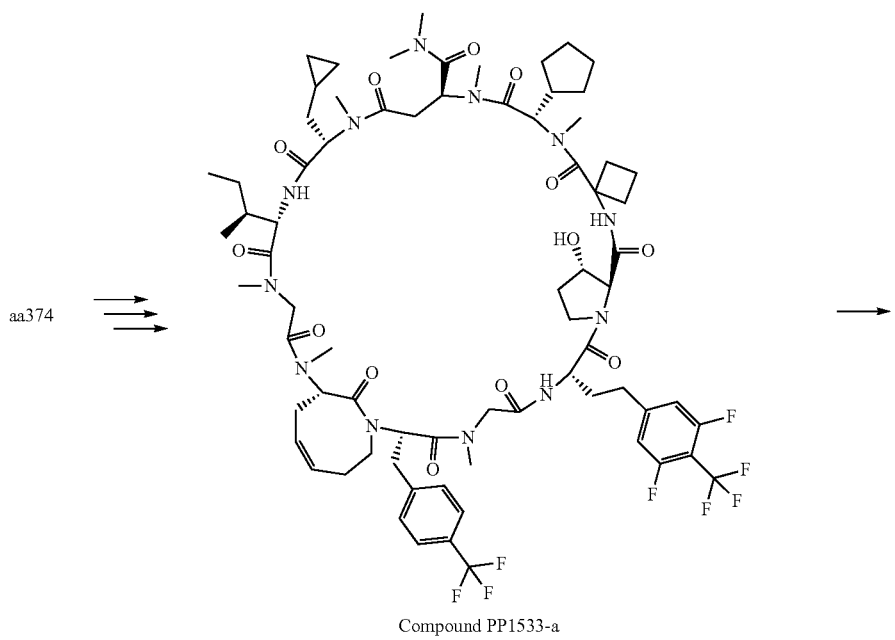

Compound PP1533-a

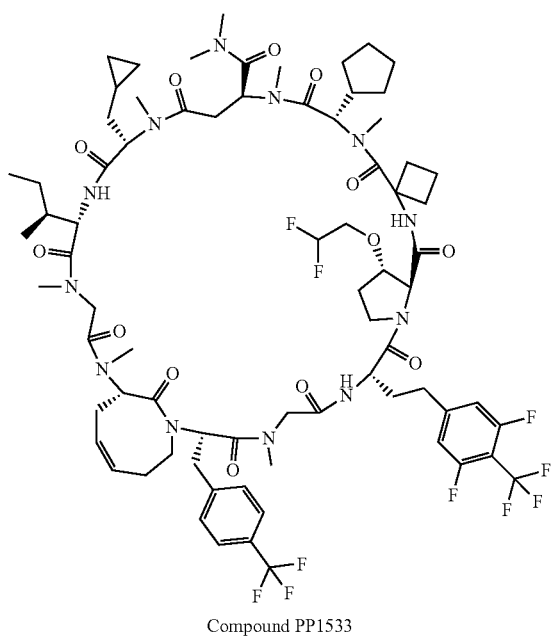

Compound PP1533

Using Compound aa374-resin as a raw material, peptide synthesis by the basic peptide synthesis method described in the present Examples was performed to give Compound PP1533-a (20.0 mg, 0.013 mmol).

LCMS (ESI) m/z=1504 (M+H)+

Retention time: 0.91 min (Analytical condition SQDFA05)

2,2-Difluoroethyl trifluoromethanesulfonic acid (18.2 μL, 0.14 mmol), tetrabutylammonium bromide (13.3 mg, 0.041 mol), and a 5 N aqueous sodium hydroxide solution (55.1 μL, 0.28 mmol) were added to a dichloromethane (275 μL) solution of Compound PP1533-a (20.7 mg, 0.014 mmol), and the mixture was stirred at room temperature for 3 days in a nitrogen atmosphere. Dichloromethane (300 μL) and water (300 μL) were added to the resulting reaction mixture, the separated organic layer was concentrated under reduced pressure, and the resulting crude product was purified by reverse phase HPLC(methanol/50 mM aqueous ammonium acetate solution) to give Compound PP1533 (11.5 mg, 54%). LC/MS data is provided in Table 36.

Synthesis of Compound PP1534

Compound PP1534 was synthesized according to the following scheme.

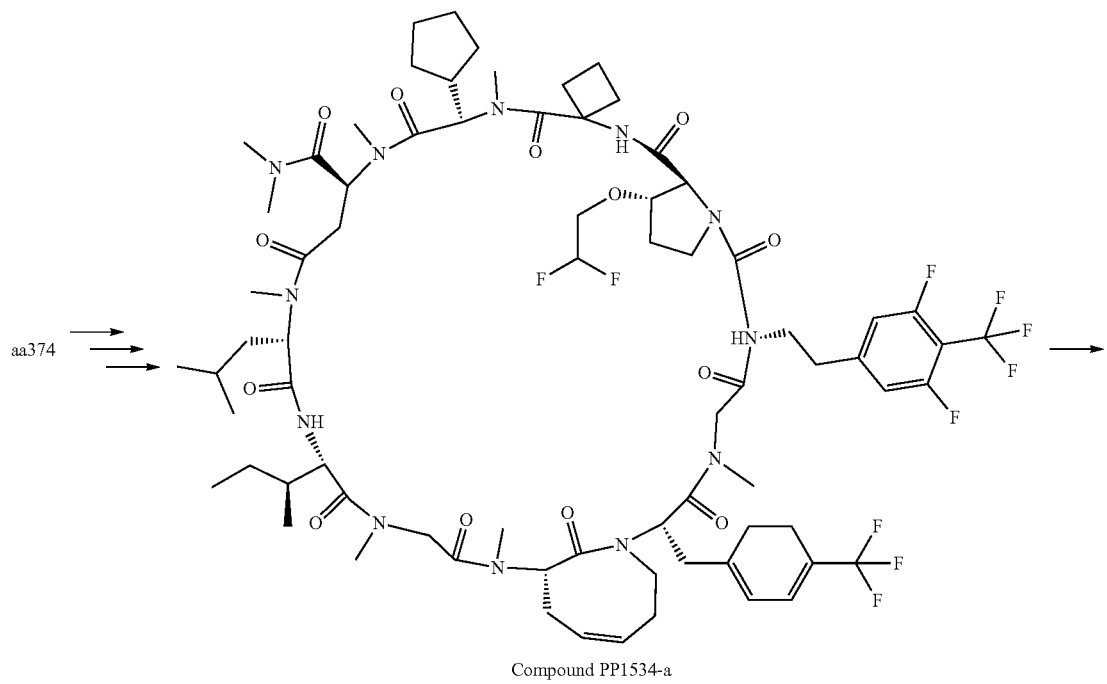

Compound PP1534-a

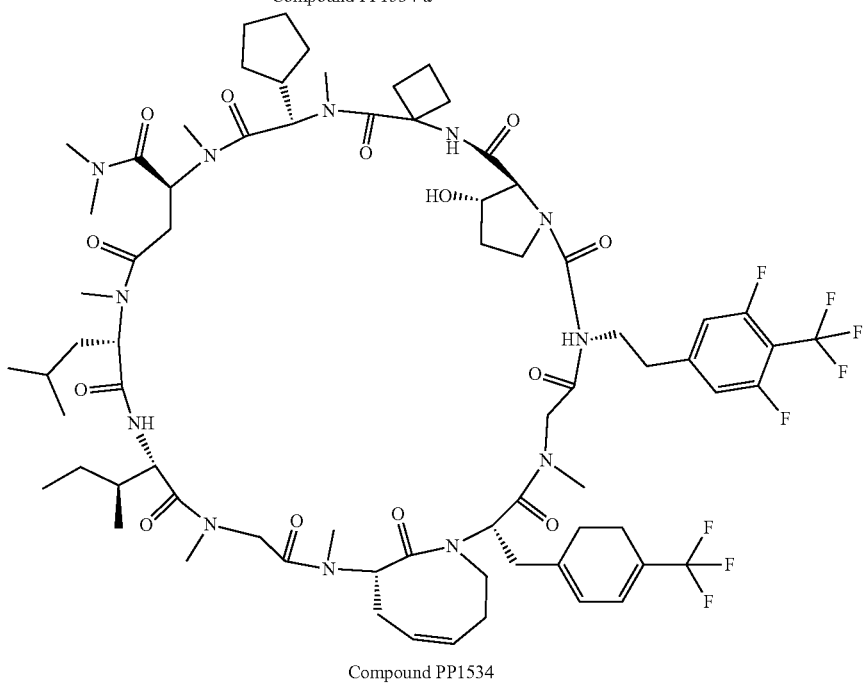

Compound PP1534

Using Compound aa374-resin as a raw material, PP1534-a (22.6 mg, 0.015 mmol) was obtained in the same manner as synthesis of PP1533-a.

LCMS (ESI) m/z=1506 (M+H)+

Retention time: 0.93 min (Analytical condition SQDFA05)

Using Compound PP1534-a (23.4 mg, 0.016 mmol) as a raw material, PP1534 (11.5 mg, 53%) was obtained in the same manner as synthesis of PP1533. LC/MS data is provided in Table 36.

Synthesis of Compound PP1535

Compound PP1535 was synthesized according to the following scheme.

aa374
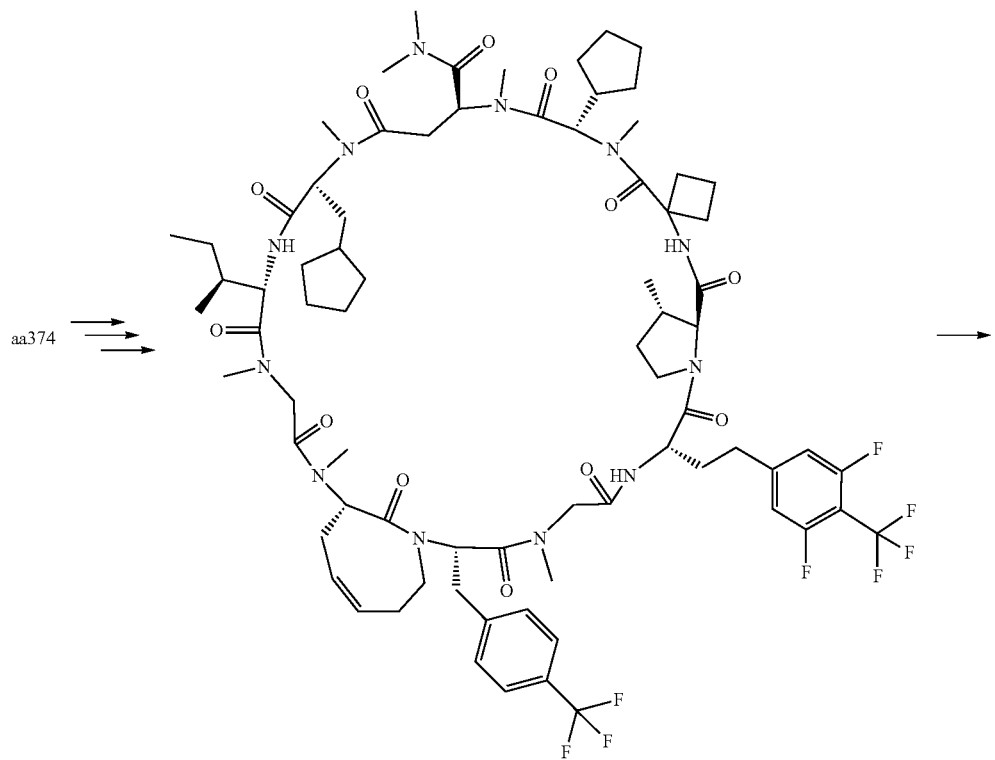
Compound PP1535-a
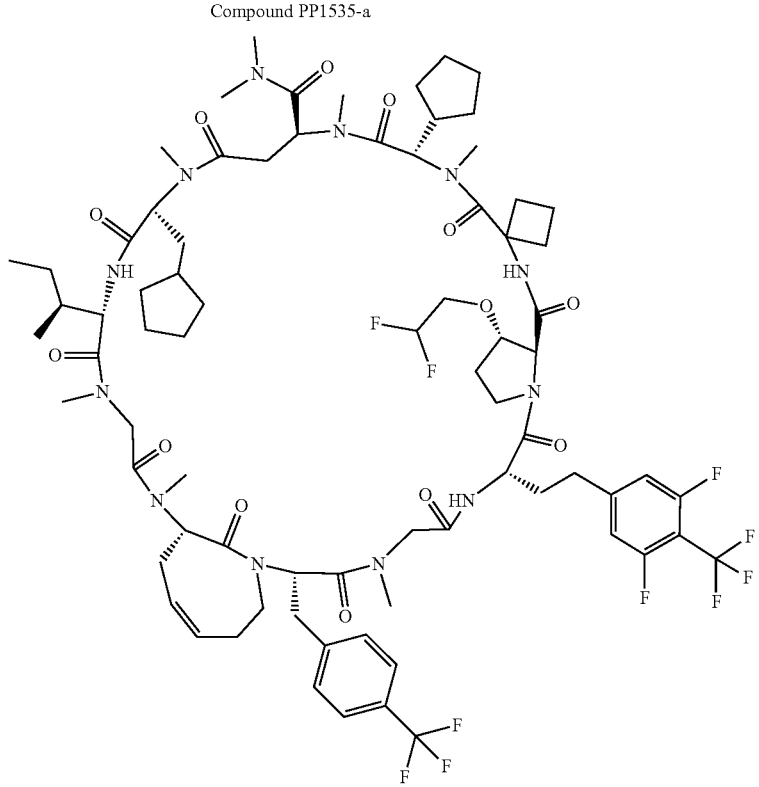
Compound PP1535

Using Compound aa374-resin as a raw material, PP1535-a (19.5 mg, 0.013 mmol) was obtained in the same manner as synthesis of PP1533-a.

LCMS (ESI) m/z=1532 (M+H)+

Retention time: 0.96 min (Analytical condition SQDFA05)

Using Compound PP1535-a (20.3 mg, 0.013 mmol) as a raw material, PP1535 (9.4 mg, 42%) was obtained in the same manner as synthesis of PP1533. LC/MS data is provided in Table 36.

Synthesis of Compound PP1536

Compound PP1536 was synthesized according to the following scheme.

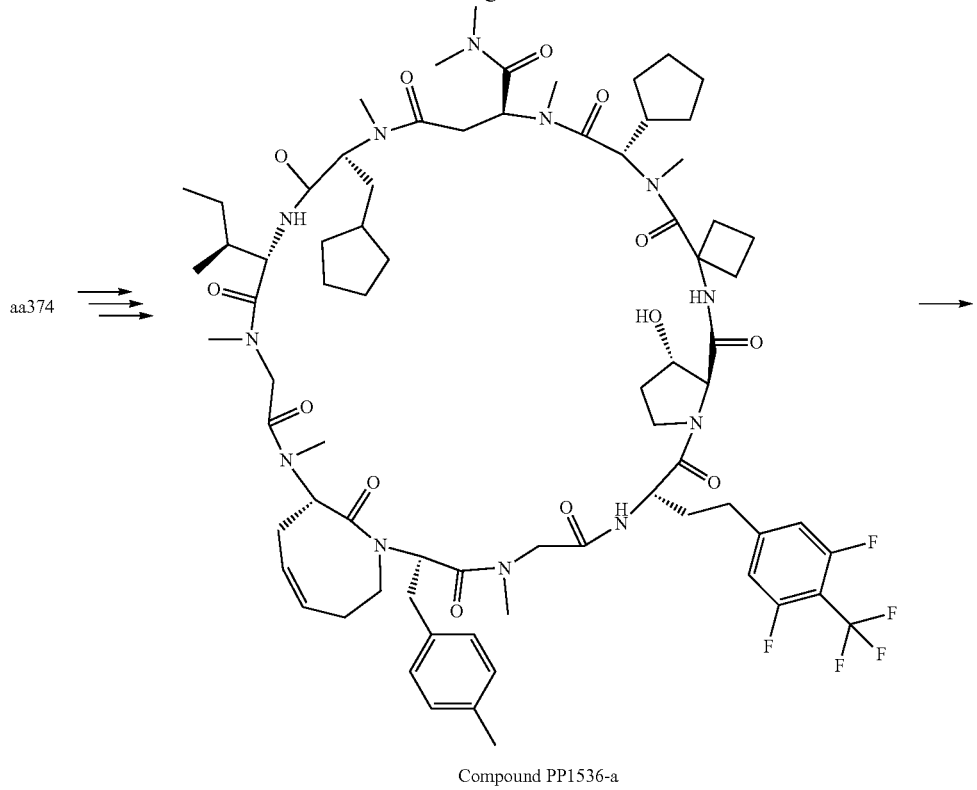

Compound PP1536-a

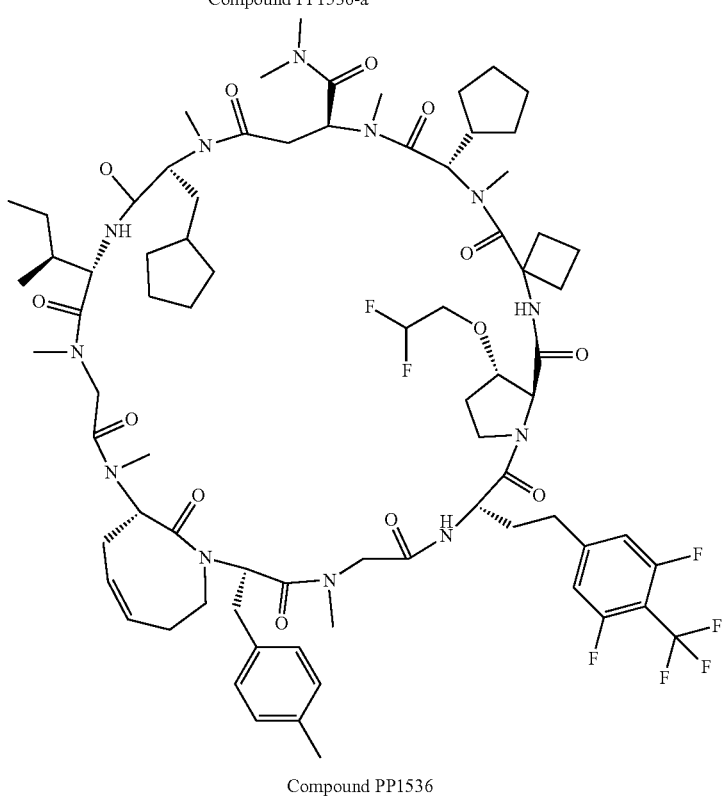

Compound PP1536

Using Compound aa374-resin as a raw material, PP1536-a (18.0 mg, 0.012 mmol) was obtained in the same manner as synthesis of PP1533-a.

LCMS (ESI) m/z=1478 (M+H)+

Retention time: 0.94 min (Analytical condition SQDFA05)

Using Compound PP1536-a (18.4 mg, 0.012 mmol) as a raw material, PP1536 (8.2 mg, 39%) was obtained in the same manner as synthesis of PP1533. LC/MS data is provided in Table 36.

In a cyclic compound and an oligopeptide compound synthesized by peptide modification by the alkylation of OH, abbreviations and structures of amino acids contained as partial structures are provided below.

[Table 17-1]

TABLE 17-1

| Compound No. | Abbreviation | Amino acid Structural Formula |
|---|---|---|
| bb016 | cisHyp | |
| bb017 | Hyp | |
| bb018 | cisHyp(3) | |
| bb019 | Hyp(3) | |
| bb020 | cisHyp(Et) | |
| bb021 | cisHyp(Et(2-F2)) | |

TABLE 17-1-continued

| Compound No. | Abbreviation | Amino acid Structural Formula |
|---|---|---|
| bb022 | Hyp(Et(2-F2)) | |
| bb023 | Hyp(Tfp) | |
| bb024 | Hyp(nBu) | |
| bb025 | Hyp(Me-cPr) | |
| bb026 | Hyp(Me-cPent) | |
| bb027 | Hyp(3)(nBu) | |

TABLE 17-1-continued
| Compound No. | Abbreviation | Amino acid Structural Formula |
|---|---|---|
| bb028 | Hyp(3)(Tfp) | 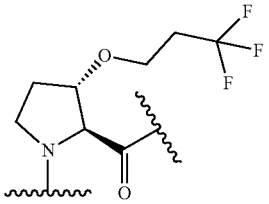 [SMILES: *C(=O)[C@@H]1[C@@H](OCCC(F)(F)F)CCN1*] |
| bb029 | Hyp(3)(Me-cPr) | |
| bb030 | Hyp(3)(Me-cPent) | |
| bb031 | Hyp(3)(Et(2-F2)) | |
| bb032 | Hyp(3)(Me) | |
TABLE 17-1-continued
| Compound No. | Abbreviation | Amino acid Structural Formula |
|---|---|---|
| bb033 | Hyp(3)(Et) | 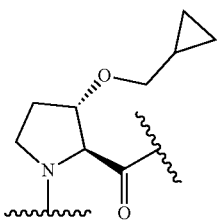 [SMILES: *C(=O)[C@@H]1[C@@H](OCC2CC2)CCN1*] |
| bb034 | Hyp(3)(nPr) | |
| bb035 | cisHyp(3)(Me) | |
| bb036 | cisHyp(3)(Et) | |
| bb037 | cisHyp(3)(nPr) | |

1-6-2. Peptide Modification by Reductive Coupling Reaction
Synthesis of Compound PP0244
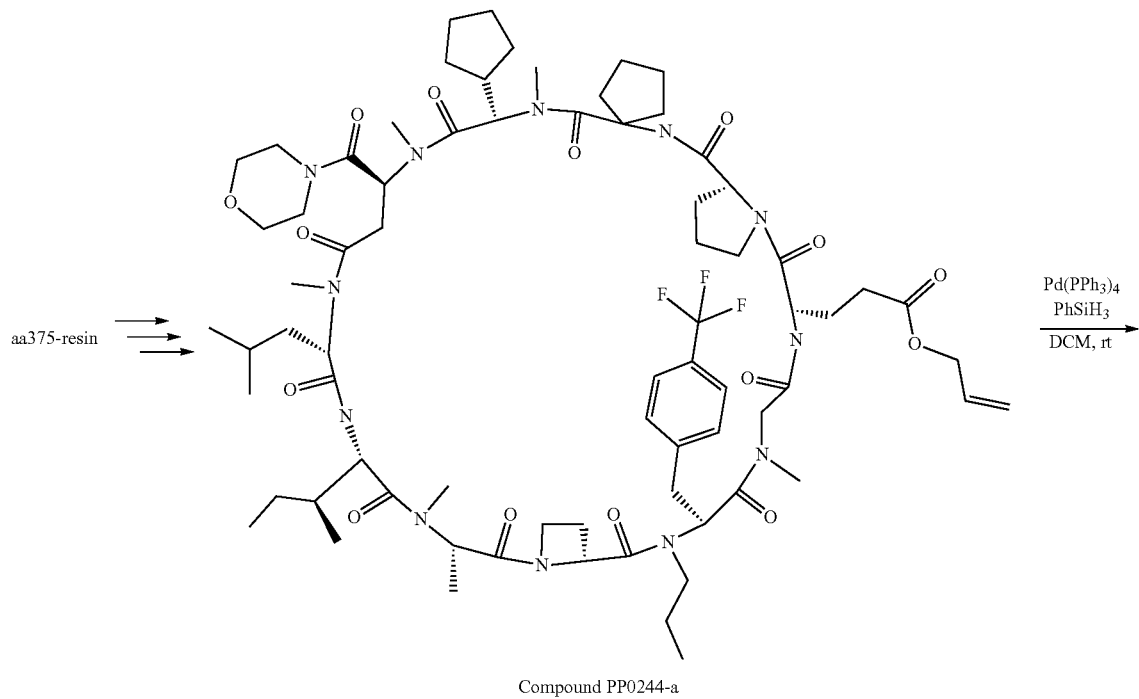
Compound PP0244-a
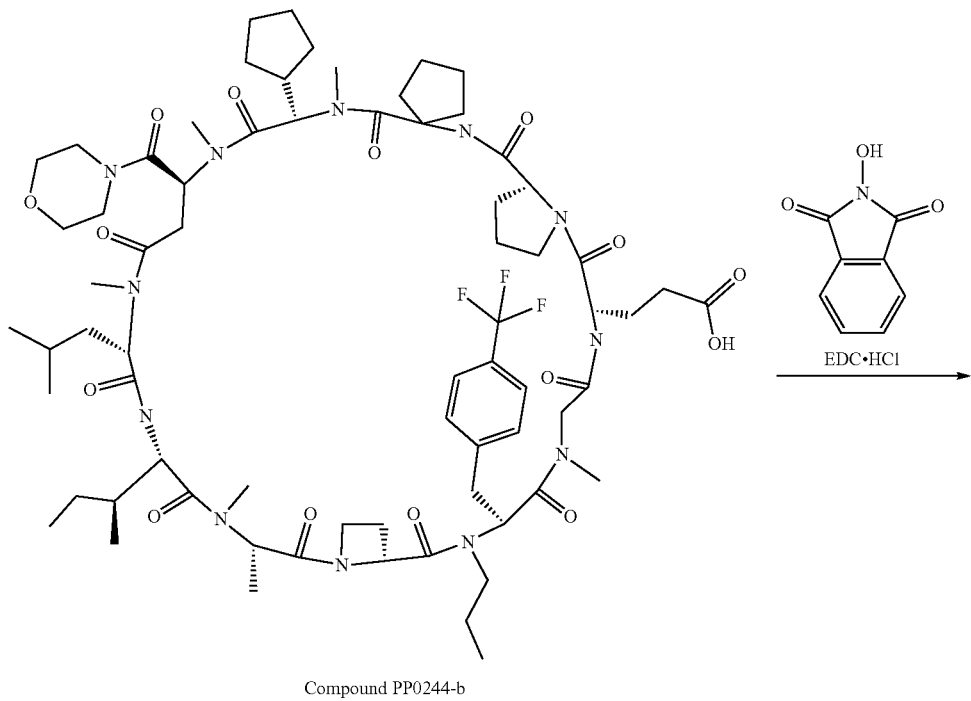
Compound PP0244-b

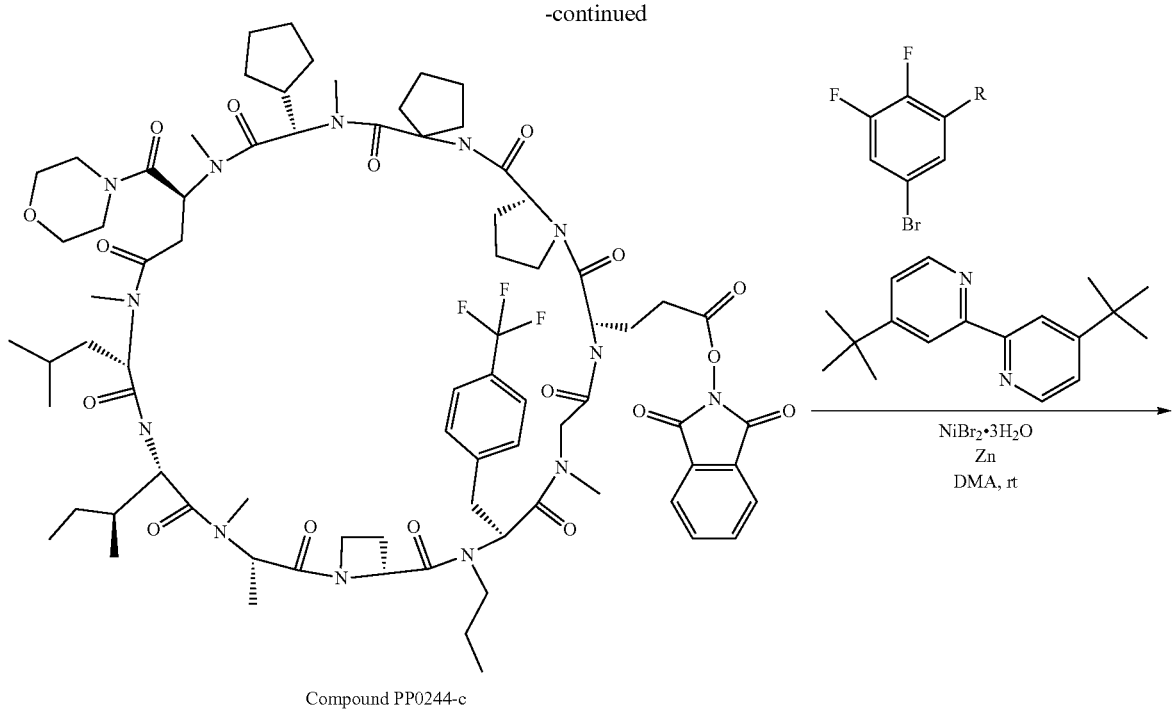

Compound PP0244-c

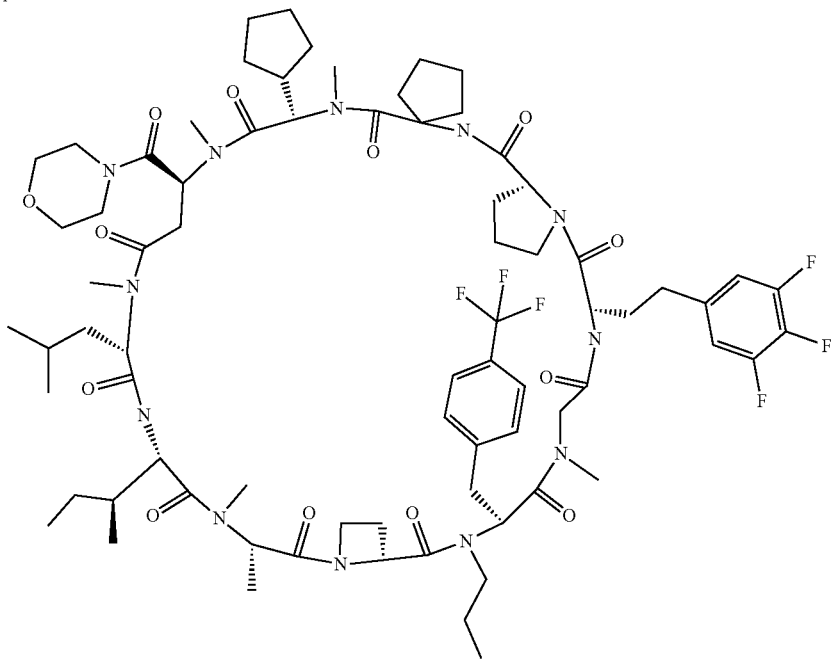

Compound PP0244

Using Compound aa375-resin as a raw material, peptide synthesis by the basic peptide synthesis method described in the present Examples was performed to give Compound PP0244-a (456.0 mg, 0.314 mmol).

LCMS (ESI) m/z=1452 (M+H)+

Retention time: 0.90 min (Analytical condition SQDFA05)

Compound PP244-a (456.0 mg, 0.314 mmol) and tetrakis (triphenylphosphine) palladium (0)(10.0 mg, 8.65 µmol) were dissolved in dichloromethane (3.0 mL), and phenylsilane (0.040 mL, 0.325 mmol) was added dropwise in a nitrogen atmosphere. The reaction solution was stirred at room temperature for 2 hours, and then purified by reverse phase chromatography (0.1% formic acid-containing acetonitrile/0.1% formic acid-containing distilled water) to give Compound PP0244-b (80.5 mg, 18%).

LCMS (ESI) m/z=1412 (M+H)+

Retention time: 0.78 min (Analytical condition SQDFA05)

Compound PP244-b (5.0 mg, 3.54 µmol) was placed in a reaction vessel, then a tetrahydrofuran (20 µL) solution of N-hydroxyphthalimide (0.867 mg, 5.31 µmol) and a dichloromethane (20 µL) solution of 1-(3-dimethylaminopropyl)-3-ethylcarbodiimide hydrochloride (0.55 mg, 3.54 µmol) were added, and the mixture was stirred overnight at room temperature. The solvent was distilled off under reduced pressure to give Compound PP0244-c as a crude product (5.51 mg, 100%).

LCMS (ESI) m/z=1557 (M+H)+

Retention time: 0.91 min (Analytical condition SQDFA05)

In a nitrogen atmosphere, nickel (II) bromide trihydrate (0.97 mg, 3.54 µmol) and 4,4'-di-tert-butyl-2,2'-bipyridine (0.95 mg, 3.54 µmol) were dissolved in N,N.-dimethylacetamide (91 µL), and this solution was added to an N,N-dimethylacetamide (80 µL) solution of Compound PP244-c (5.51 mg, 3.54 µmol), zinc (3.47 mg, 53.1 µmol), and 5-bromo-1,2,3-trifluorobenzene (4.2 µL, 35.4 µmol). After being stirred at room temperature for 19 hours, the mixture was purified by reverse phase chromatography (0.1% formic acid-containing acetonitrile/0.1% formic acid-containing distilled water) to give Compound PP0244 (3.3 mg, 62%).

LC/MS data is provided in Table 36.

Synthesis of Compound PP0882

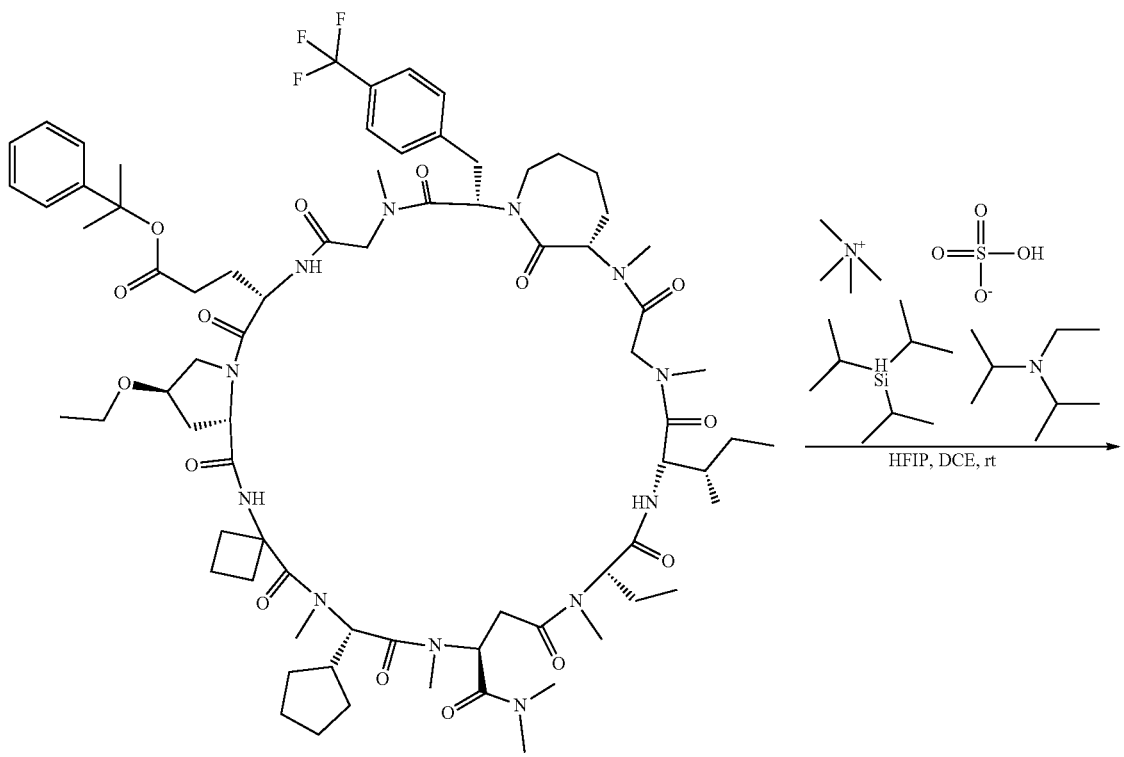

Compound PP0882-a

-continued
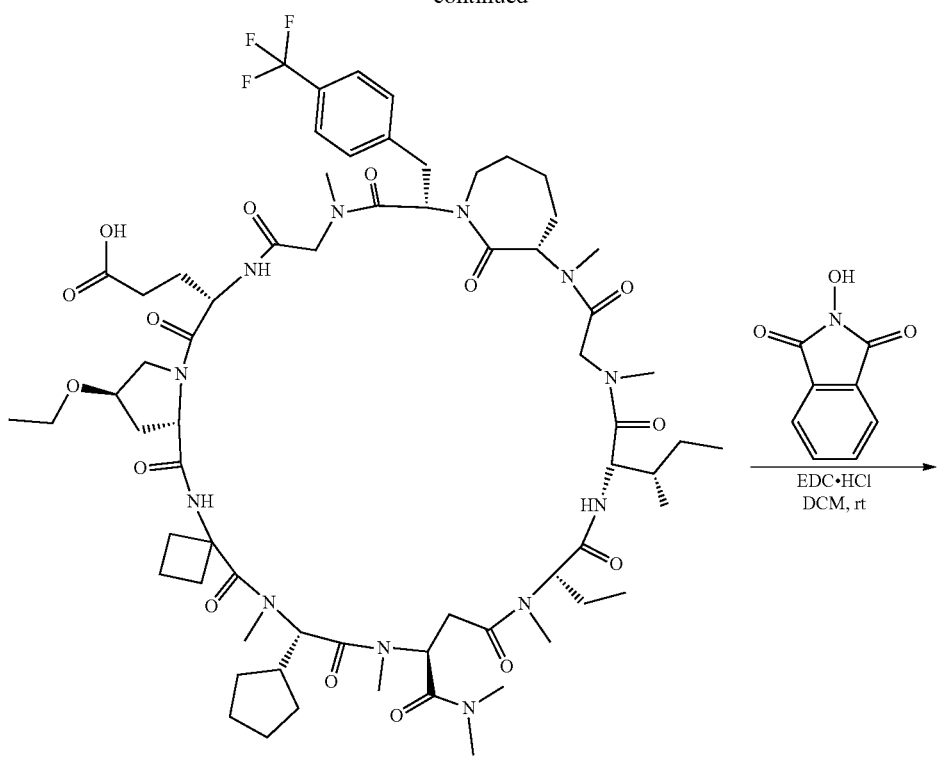
Compound PP0882-b
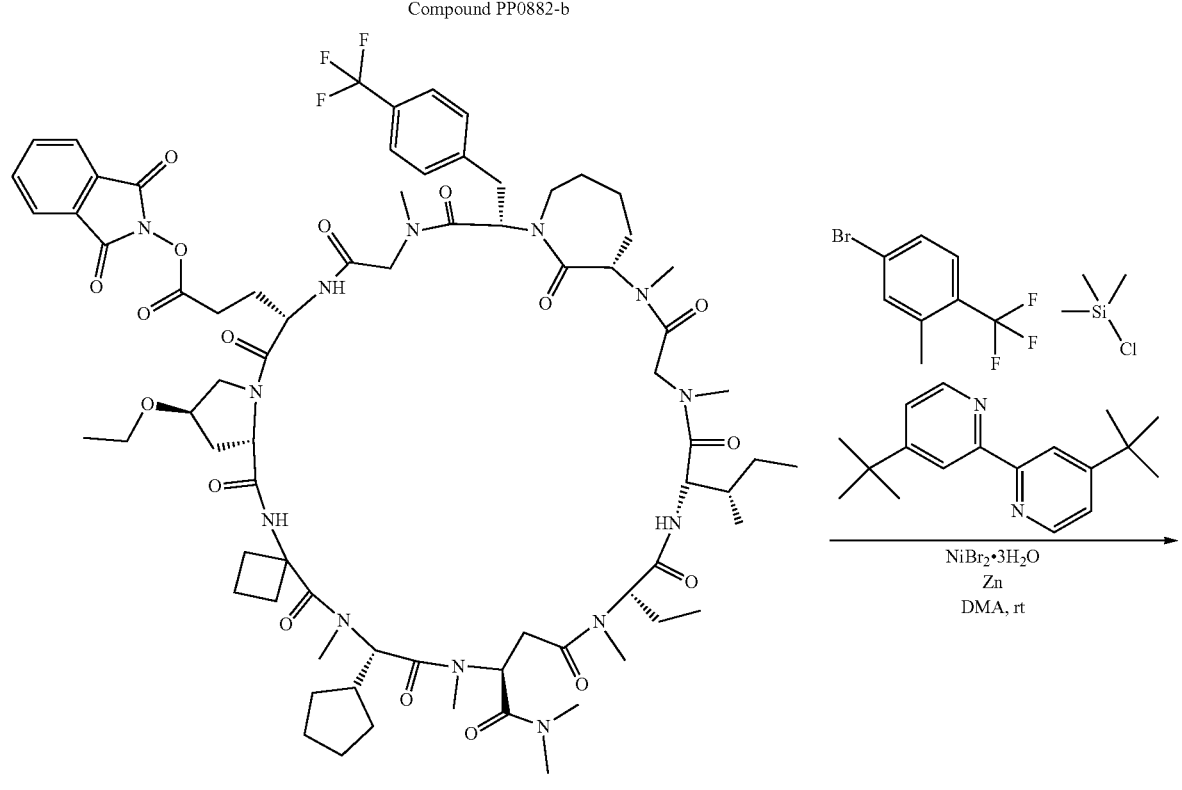
Compound PP0882 c

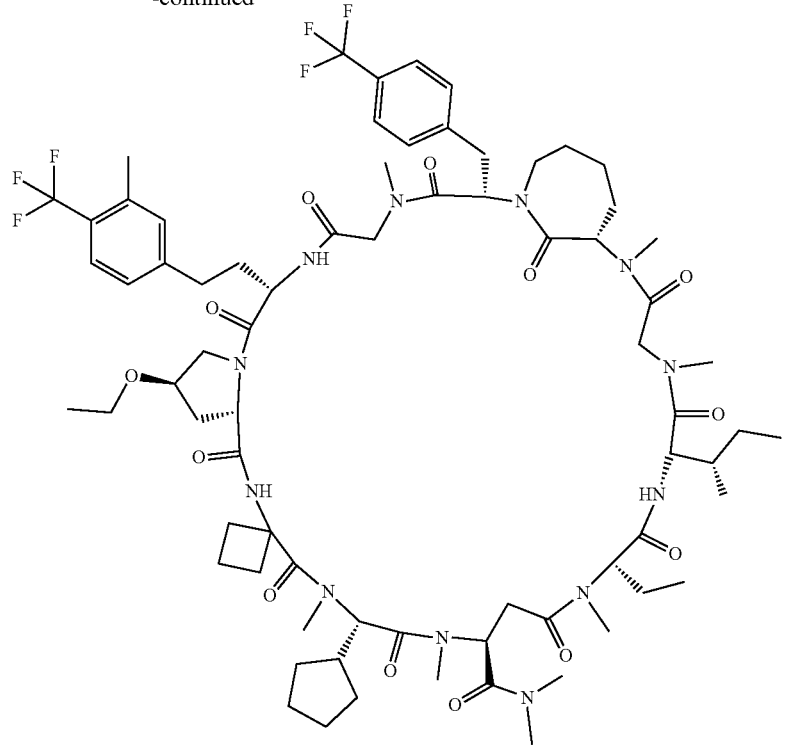

Compound PP0882

Using Compound aa374-resin as a raw material, peptide synthesis by the basic peptide synthesis method described in the present Examples was performed to give Compound PP0882-a (160.3 mg, 0.1086 mmol).

LCMS (ESI) m/z=1476 (M+H)+

Retention time: 0.93 min (Analytical condition SQDFA05)

1,1,1,3,3,3-Hexafluoro-2-propanol (11.66 mL), triisopropylsilane (0.24 mL), 1,2-dichloroethane (0.1 mL), and tetramethylammonium hydrogen sulfate (10.29 mg) were mixed, and the solution thereof (1.0 mL) was added to a reaction vessel containing Compound PP0882-a (5.0 mg, 3.39 μmol). After the mixture was stirred at room temperature for 1 hour, N,N-diisopropylethylamine (17.5 μL) was added. This was combined with a separately synthesized lot and purified by reverse phase chromatography (0.1% formic acid-containing acetonitrile/0.1% formic acid-containing distilled water) to give Compound PP0882-b (123 mg).

LCMS (ESI) m/z=1358 (M+H)+

Retention time: 0.74 min (Analytical condition SQDFA05)

Compound PP0882-b (10.0 mg, 7.37 μmol), N-hydroxyphthalimide (1.20 mg, 7.37 μmol), 1-(3-dimethylaminopropyl)-3-ethylcarbodiimide hydrochloride (2.12 mg, 0.011 mmol), and dichloromethane (73.7 μL) were placed in a reaction vessel, and the mixture was stirred at room temperature for 90 minutes. The reaction solution was diluted with dichloromethane (140 μL), and washed twice with water (200 μL). The organic layer was concentrated and dried under reduced pressure to give Compound PP0882-c as a crude product (11.1 mg, 100%).

LCMS (ESI) m/z=1503 (M+H)+

Retention time: 0.87 min (Analytical condition SQDFA05)

Nickel (II) bromide trihydrate (4.02 mg, 14.74 μmol) and 4,4'-di-tert-butyl-2,2'-bipyridine (3.96 mg, 14.74 μmol) were dissolved in N,N-dimethylacetamide (37 μL), and the mixture was stirred at room temperature for 30 minutes in a nitrogen atmosphere. After this solution was added to an N,N-dimethylacetamide (55 μL) solution of Compound PP0882-c (11.1 mg, 7.37 μmol), zinc (7.23 mg, 111.0 μmol), and 4-bromo-2-methyl-1-(trifluoromethyl)benzene (11.1 μL, 73.7 μmol), chlorotrimethylsilane (0.94 μL, 7.37 μmol) was added, and the mixture was stirred at room temperature for 14 hours. The reaction mixture was diluted with dimethyl sulfoxide (0.8 mL), filtered, and then purified by reverse phase HPLC(methanol/50 mM aqueous ammonium acetate solution) to give Compound PP0882 (4.8 mg, 44%). LC/MS data is provided in Table 36.

Synthesis of Compounds PP0884 to PP0888 and PP985 to PP0988

Using Compound PP0882-c (12.17 mg, 8.1 μmol) as a raw material, PP0884 to PP0888 and PP985 to PP0988 were obtained in the same manner as synthesis of Compound PP0882 using the bromides (10 eq) shown in Table 18. LC/MS data is provided in Table 36.

TABLE 18

| Intended product | Bromide | Yield (mg) | Yield (%) |
|---|---|---|---|
| PP0884 | ![structure] | 6.19 | 51 |

TABLE 18-continued

| Intended product | Bromide | Yield (mg) | Yield (%) |
|---|---|---|---|
| PP0885 | 2-bromo-1-fluoro-4-(trifluoromethyl)benzene | 3.94 | 33 |
| PP0886 | 1-bromo-2,3,5,6-tetrafluoro-4-(trifluoromethyl)benzene | 0.45 | 4 |
| PP0887 | 5-bromobenzo[b]thiophene | 2.72 | 23 |
| PP0888 | 6-bromobenzo[b]thiophene | 3.96 | 34 |

TABLE 18-continued

| Intended product | Bromide | Yield (mg) | Yield (%) |
|---|---|---|---|
| PP0985 | 4-bromo-2,6-dichloro-1-(trifluoromethyl)benzene | 4.18 | 34 |
| PP0986 | 4-bromo-1-(difluoromethoxy)-2-fluorobenzene | 3.78 | 32 |
| PP0987 | 4-bromo-1,2-dichlorobenzene | 0.44 | 4 |
| PP0988 | 5-bromo-1,2,3-trichlorobenzene | 4.01 | 33 |

Synthesis of Compound PP0833

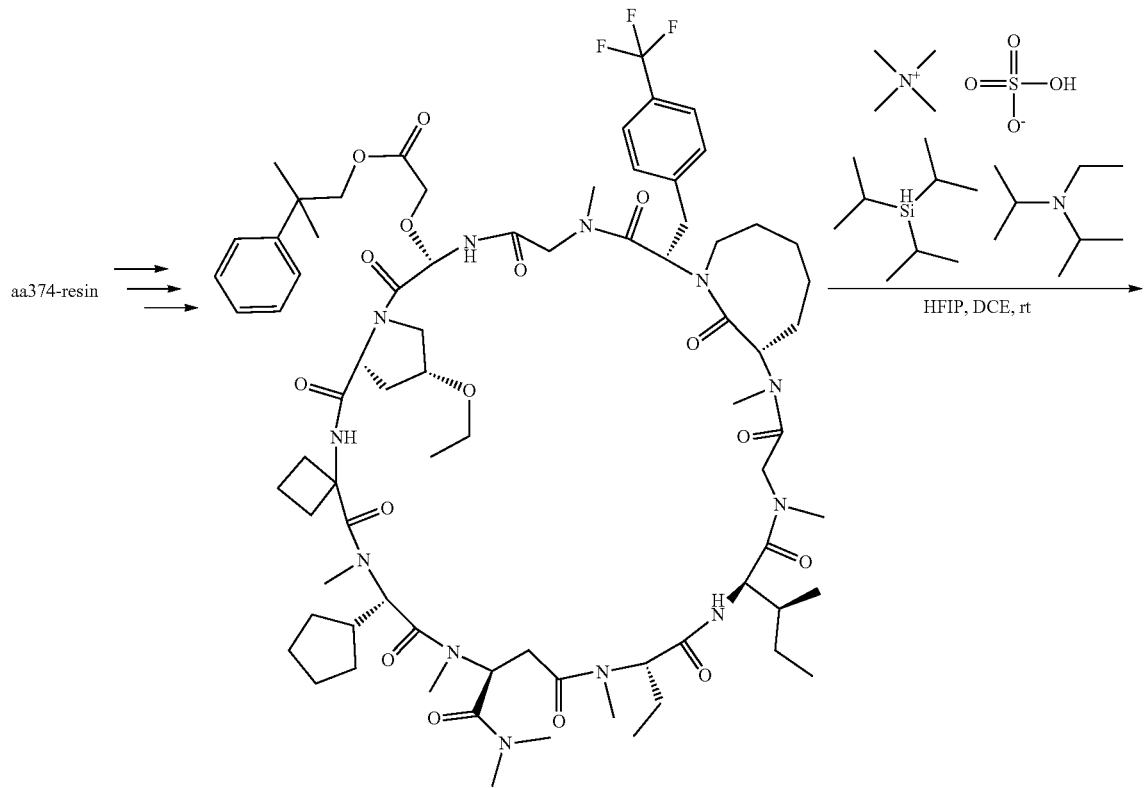

Compound PP0883-a

-continued
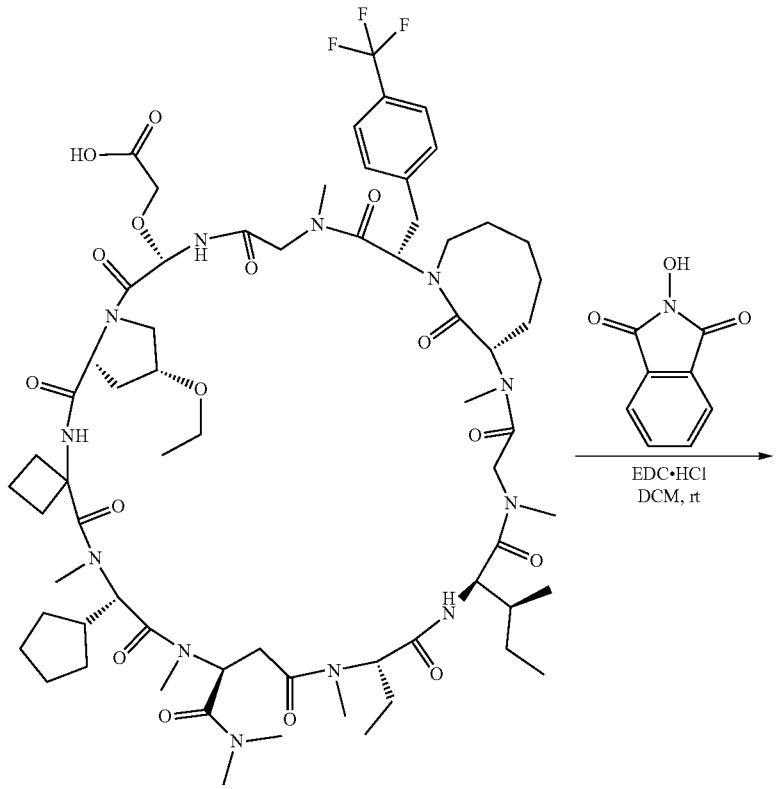
Compound PP0883-b
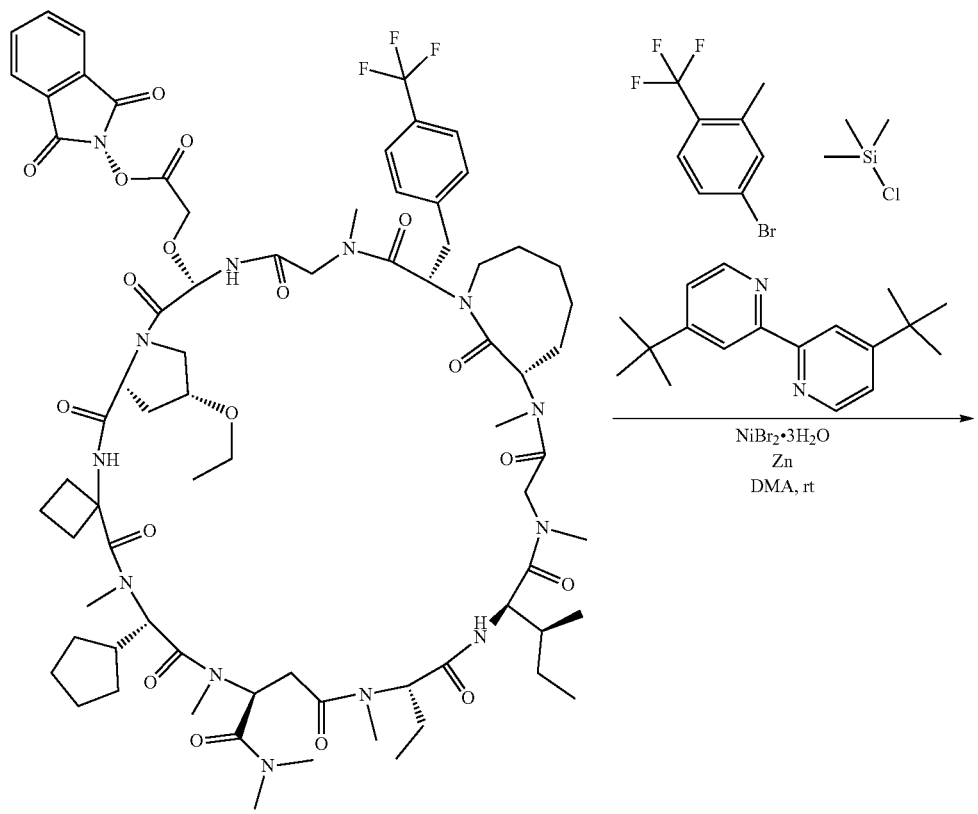
Compound PP0883-c

-continued

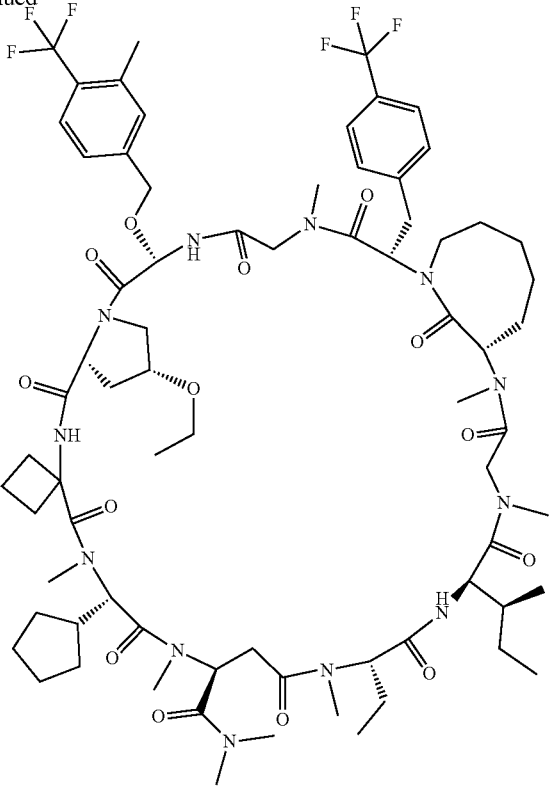

Compound PP0883

Using Compound aa374-resin as a raw material, peptide synthesis by the basic peptide synthesis method described in the present Examples was performed to give Compound PP0883-a (162.4 mg, 0.108 mmol).

LCMS (ESI) m/z=1490 (M+H)+

Retention time: 1.03 min (Analytical condition SQDFA05)

1,1,1,3,3,3-Hexafluoro-2-propanol (11.66 mL), triisopropylsilane (0).24 mL), 1,2-dichloroethane (0).1 mL), and tetramethylammonium hydrogen sulfate (10).29 mg) were mixed, and the solution thereof (1.0 mL) was added to a reaction vessel containing Compound PP0883-a (5.0) mg, 3.36 μmol). After the mixture was stirred at room temperature for 1 hour, N,N-diisopropylethylamine (17.5 μL) was added. This was combined with a separately synthesized lot and purified by reverse phase chromatography (0.1% formic acid-containing acetonitrile/0).1% formic acid-containing distilled water) to give Compound PP0883-b (91 mg).

LCMS (ESI) m/z=1372 (M+H)+

Retention time: 0.82 min (Analytical condition SQDFA05)

Compound PP0883-b (10.0 mg, 7.29 μmol), N-hydroxyphthalimide (1.189 mg, 7.29 μmol), 1-(3-dimethylaminopropyl)-3-ethylcarbodiimide hydrochloride (2.10 mg, 10.94 μmol), and dichloromethane (72.9 μL) were placed in a reaction vessel, and the mixture was stirred at room temperature for 90 minutes. The reaction solution was diluted with dichloromethane (140) μL), and washed twice with water (200 μL). The organic layer was concentrated and dried under reduced pressure to give Compound PP0883-c as a crude product (11.1 mg, 100%).

LCMS (ESI) m/z=1517 (M+H)+

Retention time: 0.95 min (Analytical condition SQDFA05)

Nickel (II) bromide trihydrate (3.97 mg, 14.58 μmol) and 4,4'-di-tert-butyl-2,2'-bipyridine (3.91 mg, 14.58 μmol) were dissolved in N,N-dimethylacetamide (37 μL), and the mixture was stirred at room temperature for 30 minutes in a nitrogen atmosphere. After this solution was added to an N,N-dimethylacetamide (55 μL) solution of Compound PP0883-c (11.1 mg, 7.29 μmol), zinc (7.15 mg, 109.0 μmol), and 4-bromo-2-methyl-1-(trifluoromethyl)benzene (11.0) μL, 72.9 μmol), chlorotrimethylsilane (0.93 μL, 7.29 μmol) was added, and the mixture was stirred at room temperature for 14 hours. The reaction mixture was diluted with dimethyl sulfoxide (0).8 mL), filtered, and then purified by reverse phase HPLC(methanol/50) mM aqueous ammonium acetate solution) to give Compound PP0883 (3.7 mg, 34%). LC/MS data is provided in Table 36.

Synthesis of Compounds PP0889 to PP0893 and PP989

Using Compound PP0883-c (12.59 mg, 8.3 μmol) as a raw material, PP0889 to PP0893 and PP989 were obtained in the same manner as synthesis of Compound PP0883 using the bromides (10 eq) shown in Table 19. LC/MS data is provided in Table 36.

TABLE 19

| Intended product | Bromide | Yield (mg) | Yield(%) |
|---|---|---|---|
| PP0889 | 6-bromobenzothiophene | 1.85 | 15 |
| PP0890 | 1-bromo-2-fluoro-4-(trifluoromethyl)benzene | 2.03 | 16 |
| PP0891 | 1-bromo-2,3,5,6-tetrafluoro-4-(trifluoromethyl)benzene (pentafluoro) | 0.26 | 2 |

TABLE 19-continued

| Intended product | Bromide | Yield (mg) | Yield(%) |
|---|---|---|---|
| PP0892 | 5-bromobenzothiophene | 0.27 | 2 |
| PP0893 | 6-bromobenzothiophene isomer | 0.74 | 6 |
| PP0989 | 4-bromo-2,6-dichloro-(trifluoromethyl)benzene | 2.2 | 17 |

Synthesis of Compound PP904

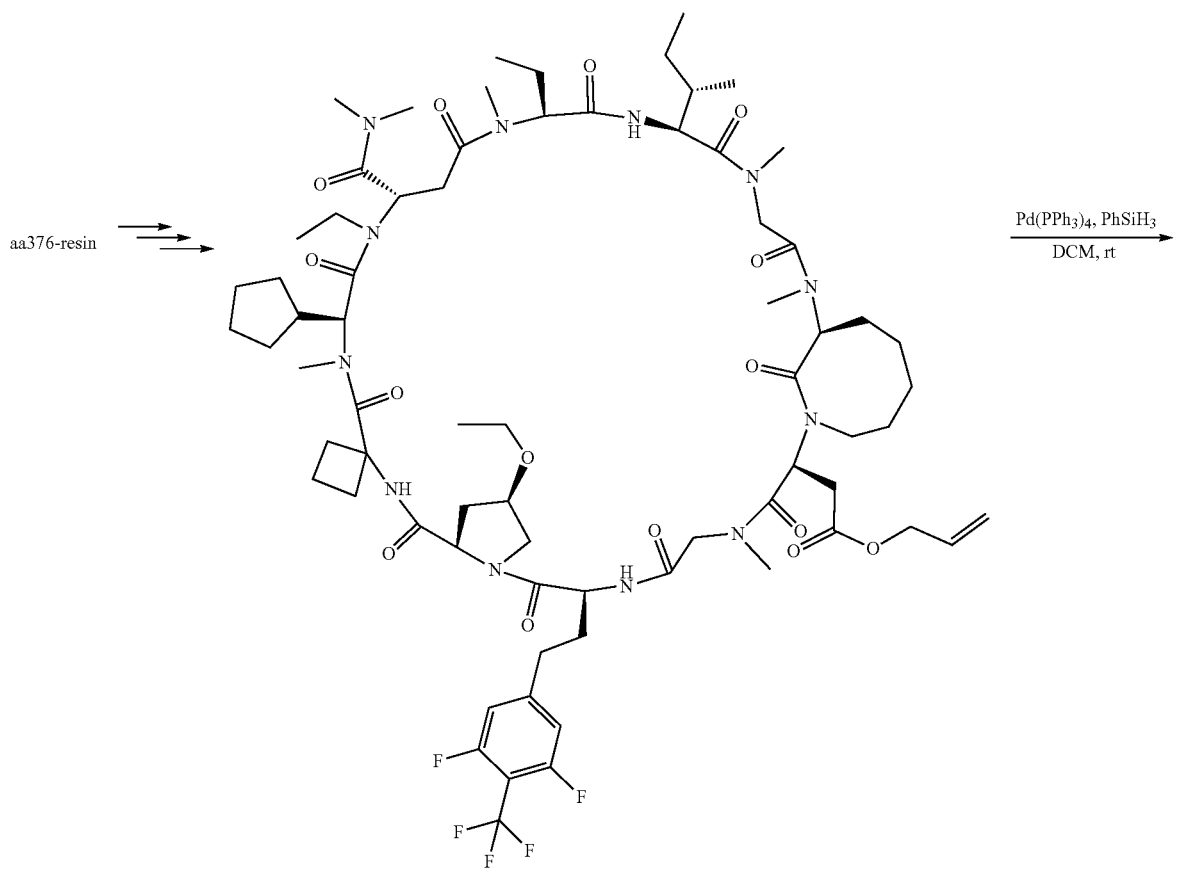

Compound PP0904-a

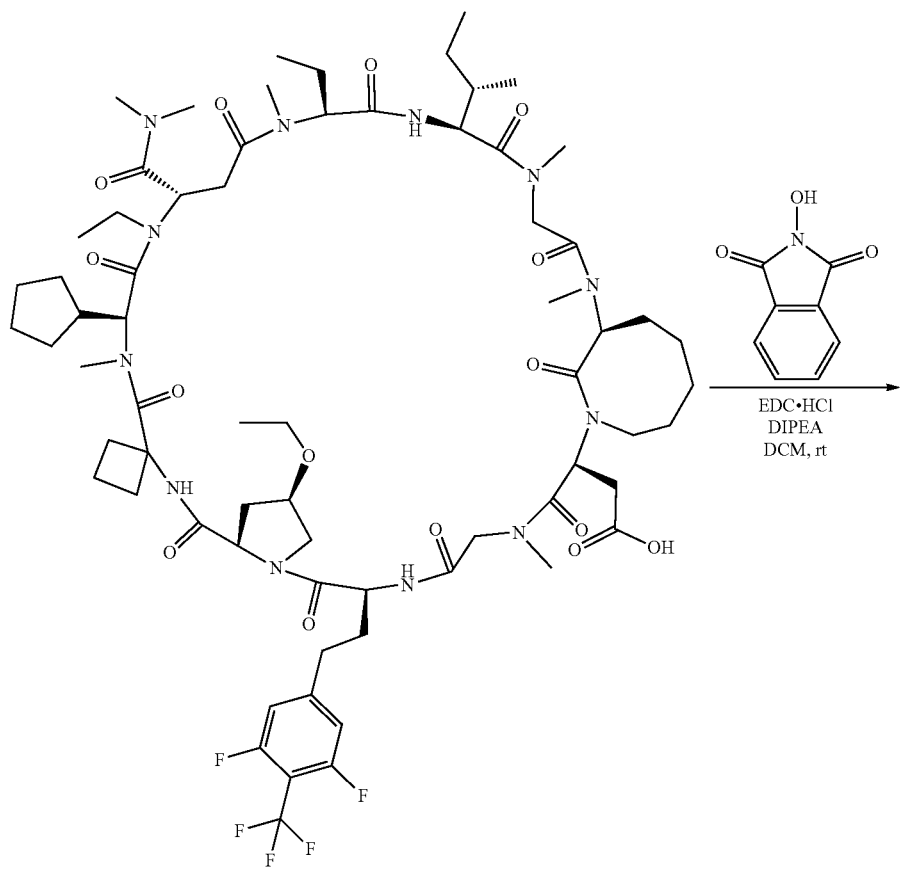
Compound PP0904-b

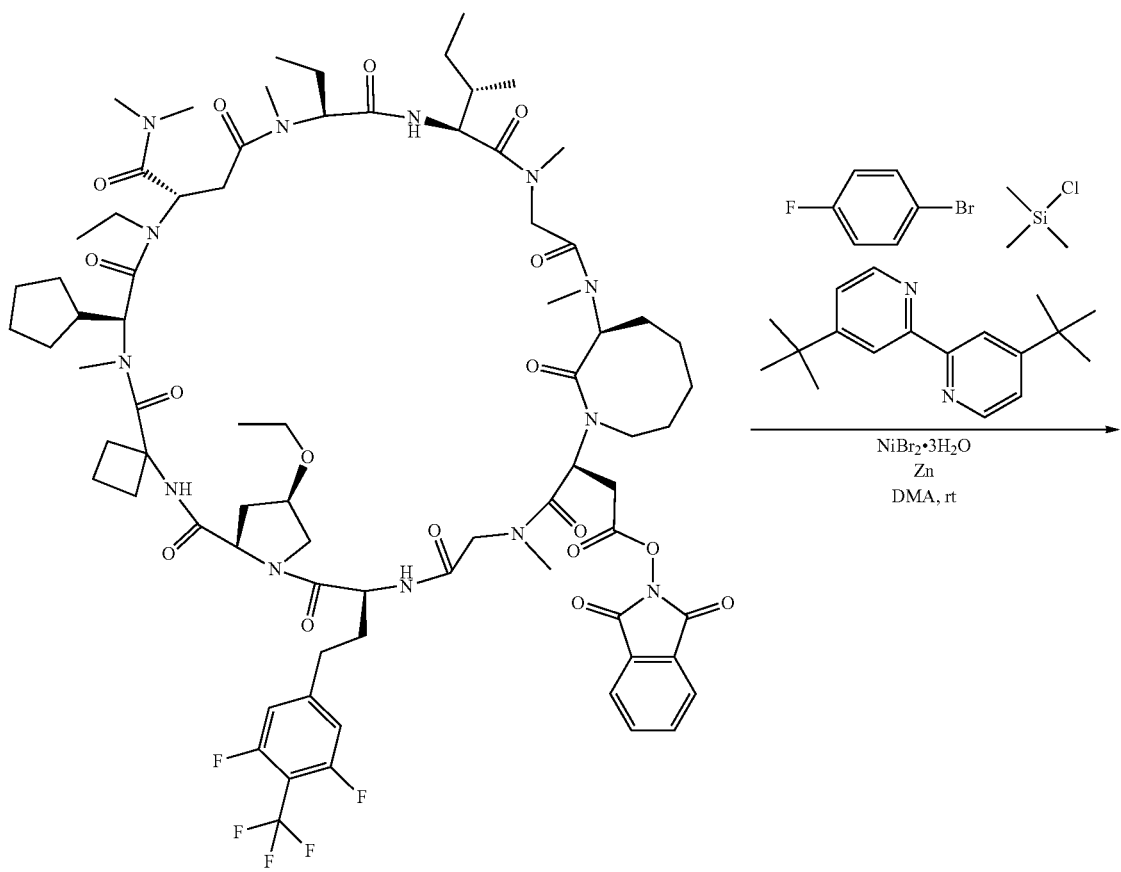
Compound PP0904-c

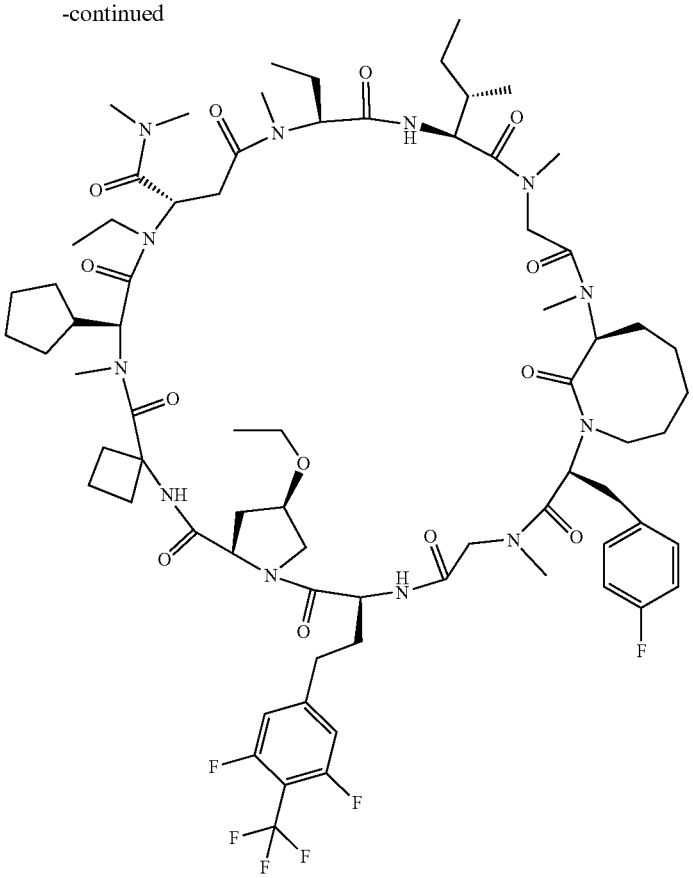

Compound PP0904

Using Compound aa376-resin as a raw material, peptide synthesis by the basic peptide synthesis method described in the present Examples was performed to give Compound PP0904-a.

LCMS (ESI) m/z=1462 (M+H)+

Retention time: 0.78 min (Analytical condition SQDAA50)

The resulting Compound PP904-a was dissolved in dichloromethane (1.0 mL), tetrakis(triphenylphosphine) palladium (0)(31.0 mg, 26.6 μmol) and phenylsilane (58.0 mg, 0.533 mmol) were added, and the mixture was stirred at room temperature for 30 minutes. After the solvent was distilled off under reduced pressure, the resulting crude product was purified by reverse phase HPLC(methanol/50 mM aqueous ammonium acetate solution) to give Compound PP0904-b (22.0 mg, 0.015 mmol, 11%).

LCMS (ESI) m/z=1422 (M+H)+

Retention time: 0.66 min (Analytical condition SQDAA50)

Dichloromethane (155 μL) was added to a reaction vessel containing Compound PP0904-b (22.0 mg, 0.015 mmol) and N-hydroxyphthalimide (2.5 mg, 0.015 mmol). After the mixture was stirred at room temperature for 1 hour, N,N-diisopropylethylamine (4.1 μL, 0.023 mmol) was added, and the mixture was stirred at room temperature for 1 hour. Then, 1-(3-dimethylaminopropyl)-3-ethylcarbodiimide hydrochloride (4.5 mg, 0.023 mmol) was added, and the mixture was stirred at room temperature for 1 hour. After dilution with dichloromethane, the organic layer was washed with a saturated aqueous ammonium chloride solution and then washed with water. After drying over anhydrous sodium sulfate and filtration, the solvent was distilled off under reduced pressure to give Compound PP0904-c (20.8 mg, 86%).

LCMS (ESI) m/z=1567 (M+H)+

Retention time: 0.88 min (Analytical condition SQDFA40)

Nickel (II) bromide trihydrate (1.74 mg, 6.39 μmol) and 4,4'-di-tert-butyl-2,2'-bipyridine (1.71 mg, 6.39 μmol) were dissolved in N,N-dimethylacetamide (75 μL), and this solution was added to an N,N-dimethylacetamide (80 μL) solution of Compound PP904-c (10.0 mg, 6.38 μmol), zinc (6.3 mg, 0.096 mmol), and 4-bromofluorobenzene (7.0 μL, 0.064 mmol). After the mixture was stirred at room temperature for 15 hours, chlorotrimethylsilane (0.82 μL, 6.39 μmol) was added, and the mixture was stirred for 3 hours. The reaction mixture was diluted with dimethyl sulfoxide, filtered, and then purified by reverse phase HPLC(methanol/50 mM aqueous ammonium acetate solution) to give Compound PP0904 (0.43 mg, 0.292 μmol). LC/MS data is provided in Table 36.

Synthesis of Compound PP905
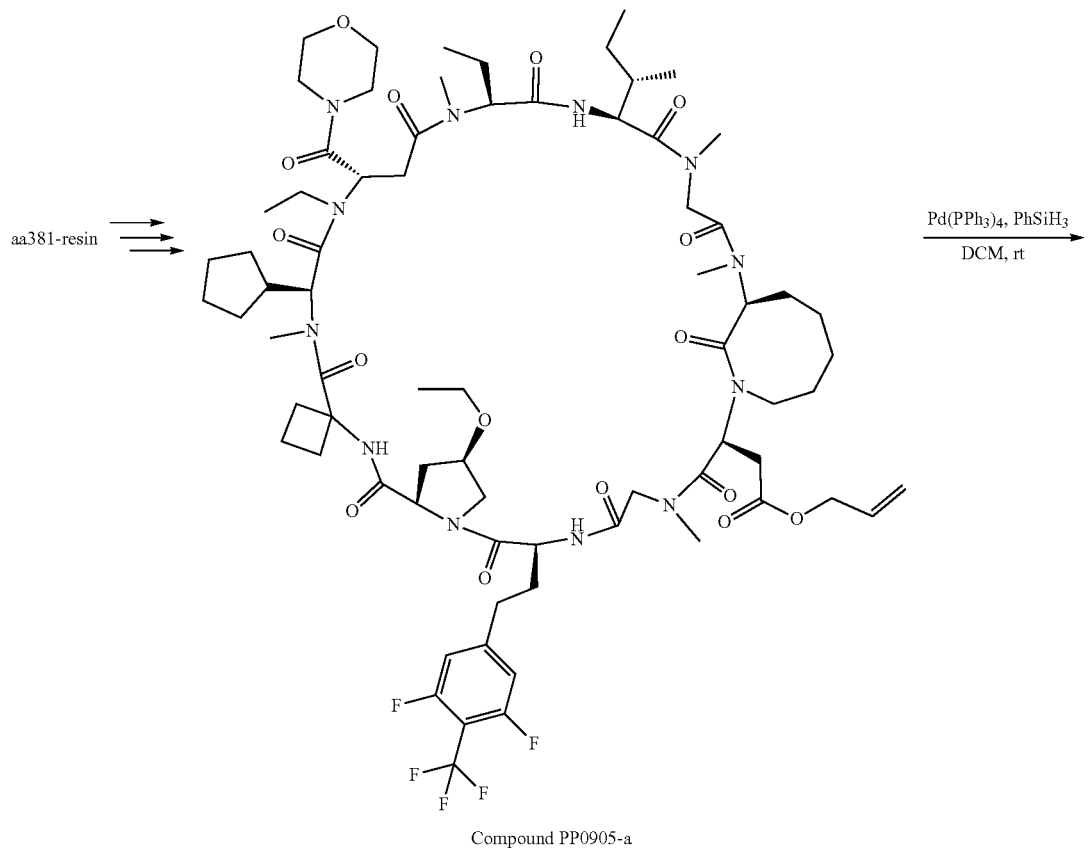
Compound PP0905-a
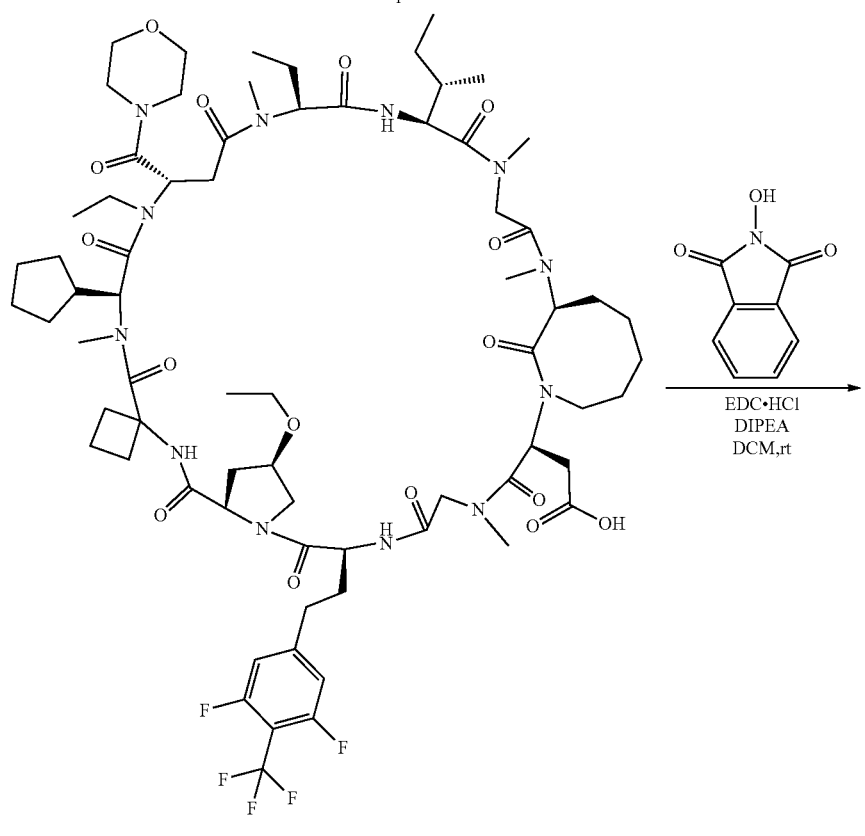
Compound PP0905-b 539 540
-continued
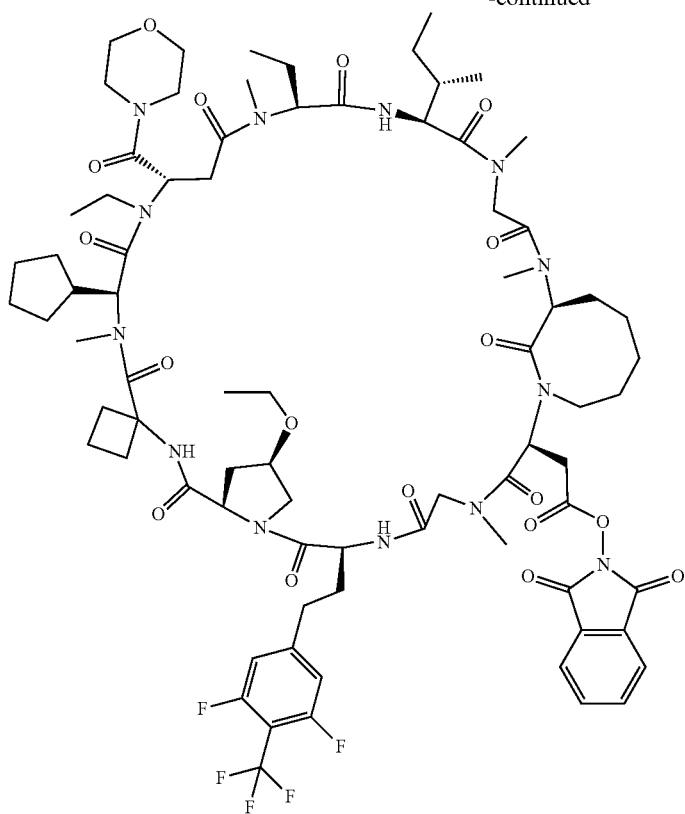
Compound PP0905-c
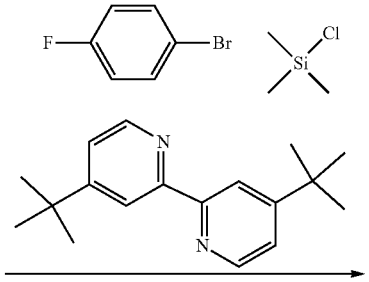
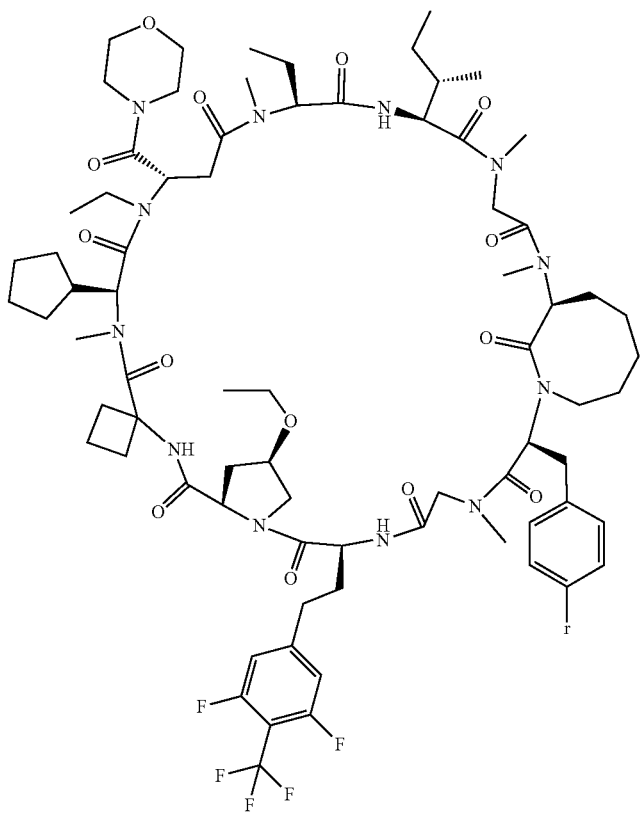
Compound PP0905

Using Compound aa381-resin as a raw material, peptide synthesis by the basic peptide synthesis method described in the present Examples was performed to give Compound PP0905-a. Using this as a starting material, PP905-b (27.0 mg, 0.018 mmol, 8%) was obtained in the same manner as synthesis of Compound PP904-b.

LCMS (ESI) m/z=1464 (M+H)+

Retention time: 0.66 min (Analytical condition SQDAA50)

Using PP905-b as a starting material, PP905-c (26.0 mg, 88%) was obtained in the same manner as synthesis of Compound PP904-c.

LCMS (ESI) m/z=1609 (M+H)+

Retention time: 0.88 min (Analytical condition SQDFA40)

Using PP905-c as a starting material, PP905 (1.57 mg, 1.037 μmol) was obtained in the same manner as synthesis of Compound PP904. LC/MS data is provided in Table 36.

Synthesis of Compound PP906

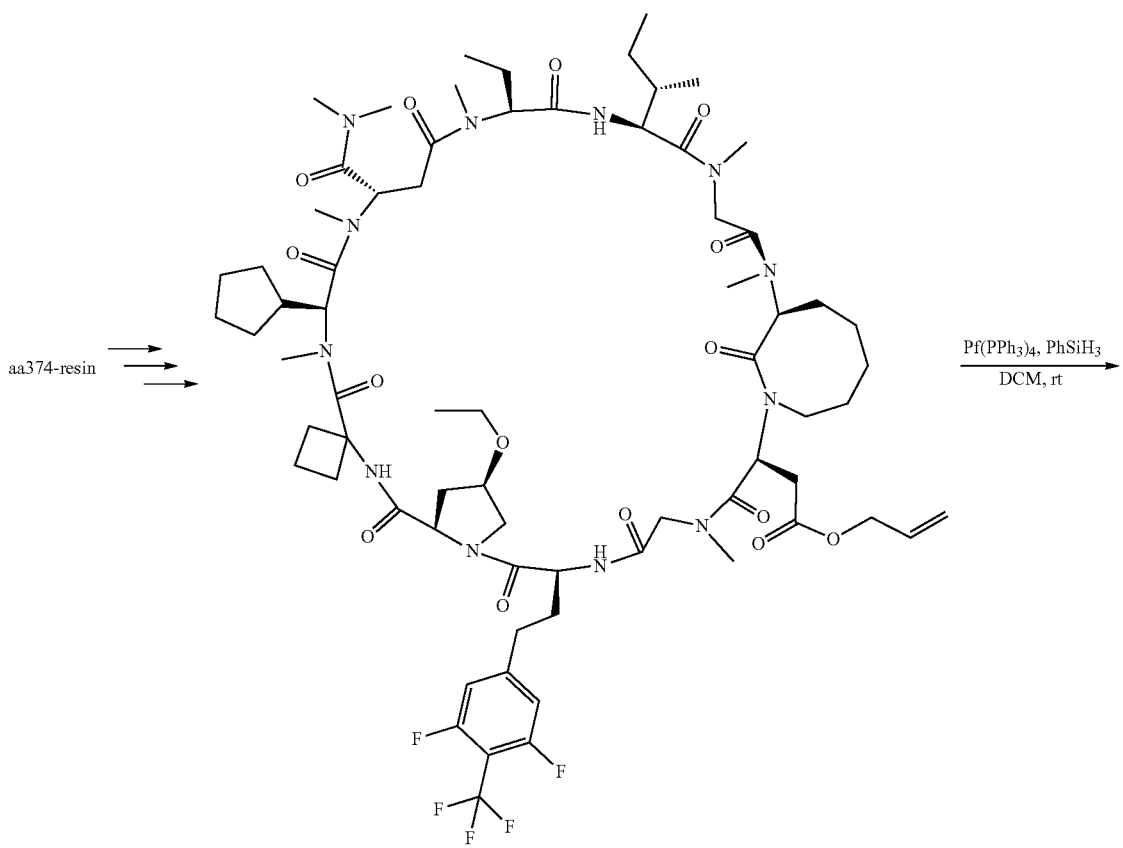

Compound PP0906-a

-continued
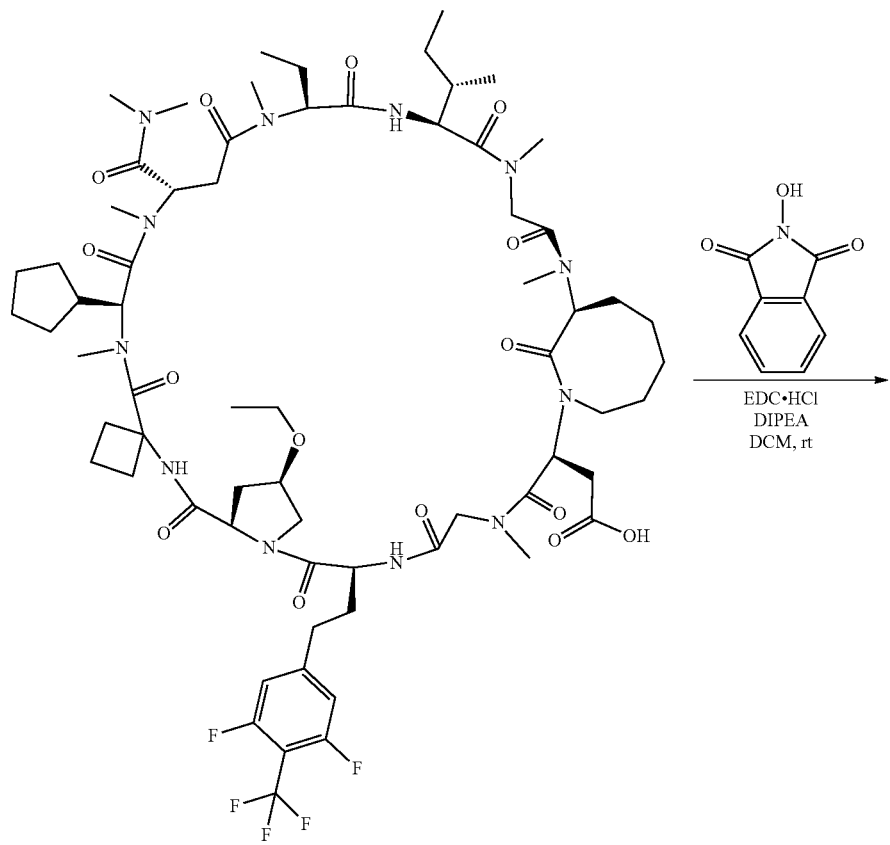
Compound PP0906-b

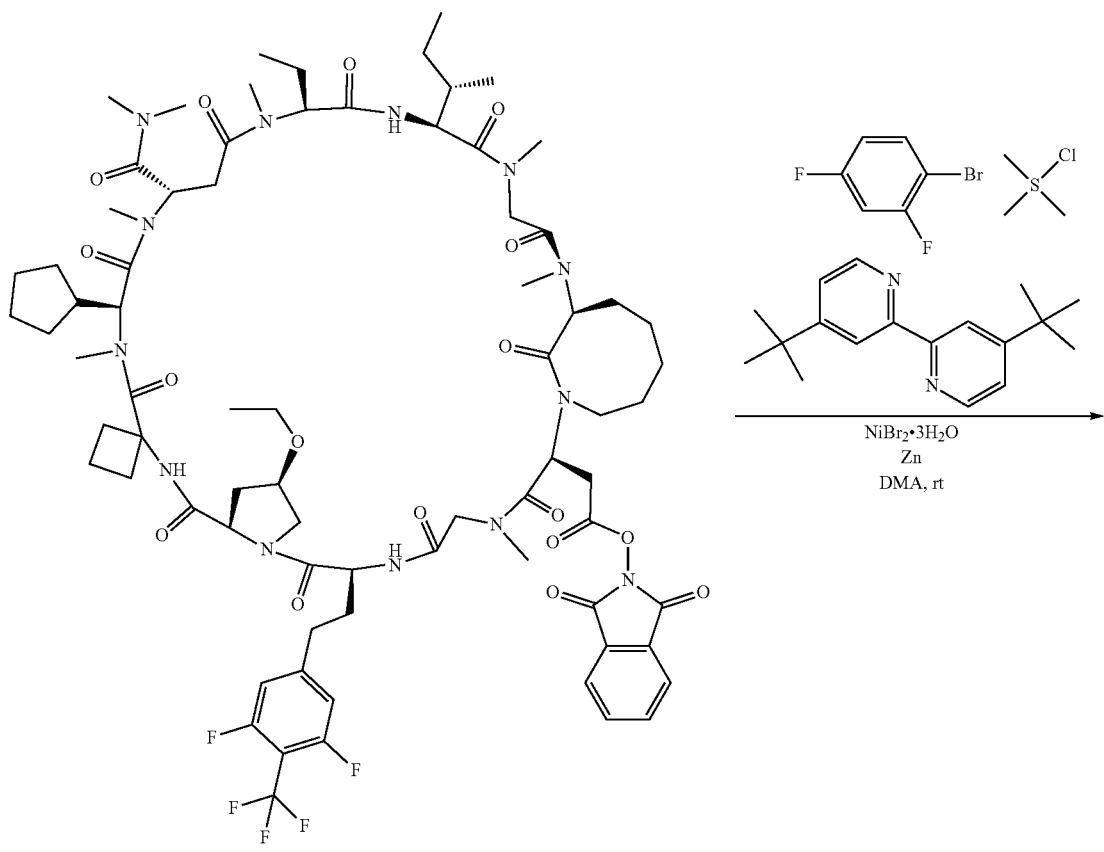
Compound PP0906-c

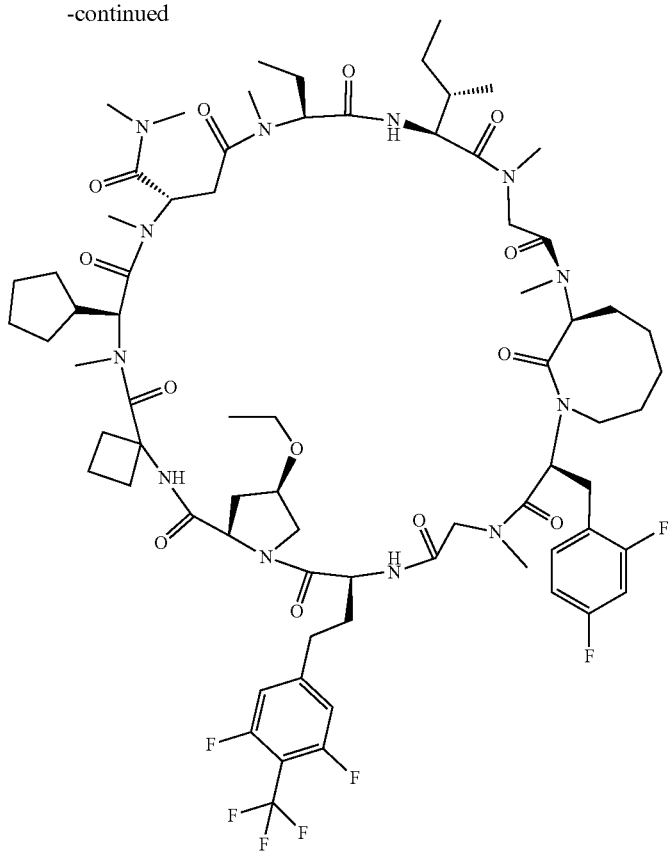

Compound PP0906

Using Compound aa374-resin as a raw material, peptide synthesis by the basic peptide synthesis method described in the present Examples was performed to give Compound PP0906-a. Using this as a starting material, PP906-b (138.0 mg, 18%) was obtained in the same manner as synthesis of Compound PP904-b.

LCMS (ESI) m/z=1408 (M+H)+

Retention time: 0.62 min (Analytical condition SQDAA50)

Using PP906-b as a starting material, PP906-c (130.3 mg, 100%) was obtained in the same manner as synthesis of Compound PP904-c.

LCMS (ESI) m/z=1553 (M+H)+

Retention time: 0.76 min (Analytical condition SQDAA50)

Using PP906-c as a starting material, PP906 (0.66 mg, 0.447 μmol) was obtained in the same manner as synthesis of Compound PP904 using 1-bromo-2,4-difluorobenzene in place of 4-bromofluorobenzene. LC/MS data is provided in Table 36.

Synthesis of Compounds PP907 to PP0915

Using Compound PP906-c (10 mg, 6.38 μmol) as a raw material, PP907 to PP0915 were obtained in the same manner as synthesis of Compound PP906 using the bromides (10 eq) shown in Table 20. LC/MS data is provided in Table 36.

TABLE 20

| Intended product | Bromide | Yield (mg) | Yield (%) |
|---|---|---|---|
| PP0907 | F—⌬—Br, F | 0.7 | 7 |
| PP0908 | F—⌬—Br, Cl | 0.61 | 6 |
| PP0909 | F—⌬—Br, Cl | 1.23 | 13 |
| PP0910 | Br—⌬(S) | 1.72 | 18 |

TABLE 20-continued
| Intended product | Bromide | Yield (mg) | Yield (%) |
|---|---|---|---|
| PP0911 | 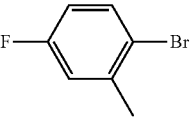 4-F, 2-methyl bromobenzene | 0.72 | 8 |
| PP0912 | 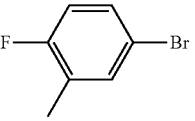 4-F, 3-methyl bromobenzene | 2.03 | 22 |
| PP0913 | 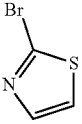 2-bromothiazole | 0.78 | 9 |
TABLE 20-continued
| Intended product | Bromide | Yield (mg) | Yield (%) |
|---|---|---|---|
| PP0914 | 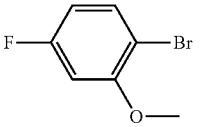 | 1.82 | 19 |
| PP0915 | 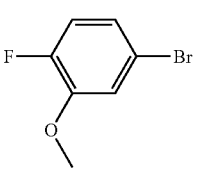 | 1.72 | 18 |
Synthesis of Compound PP916
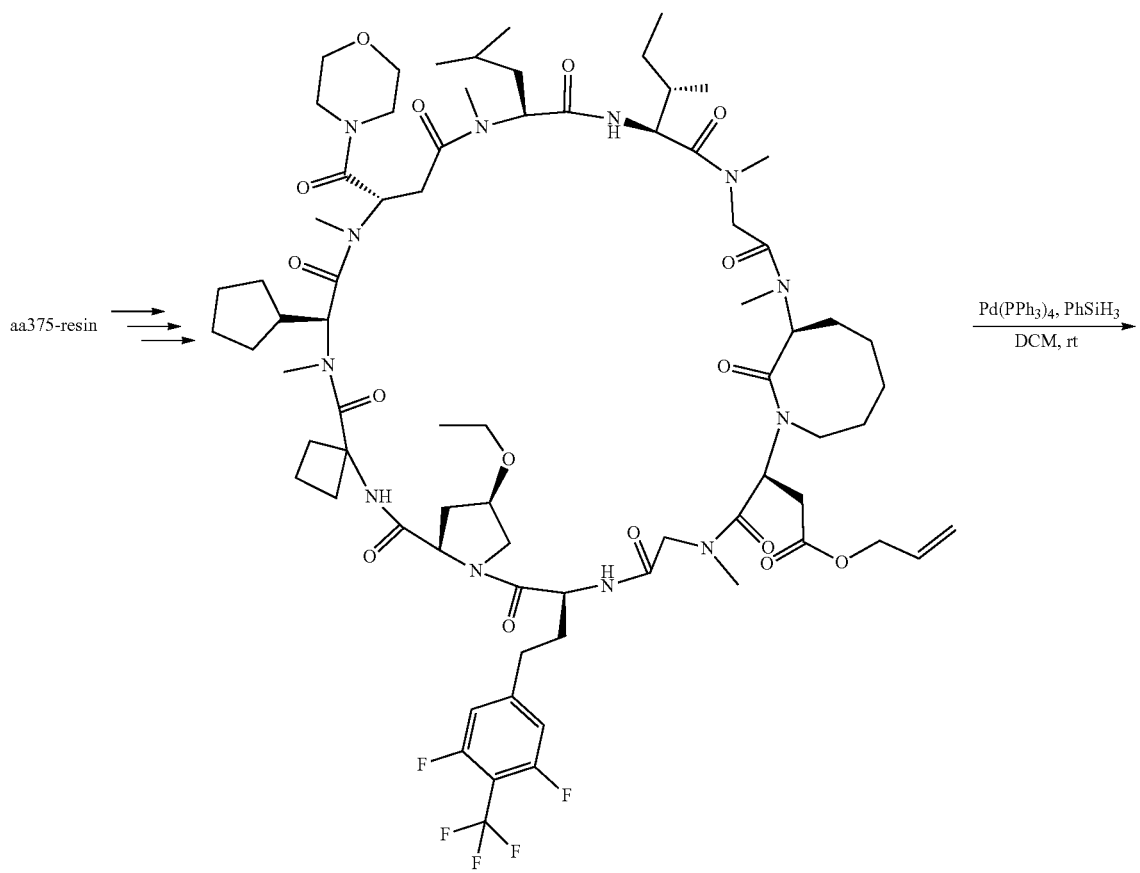
Compound PP0916-a

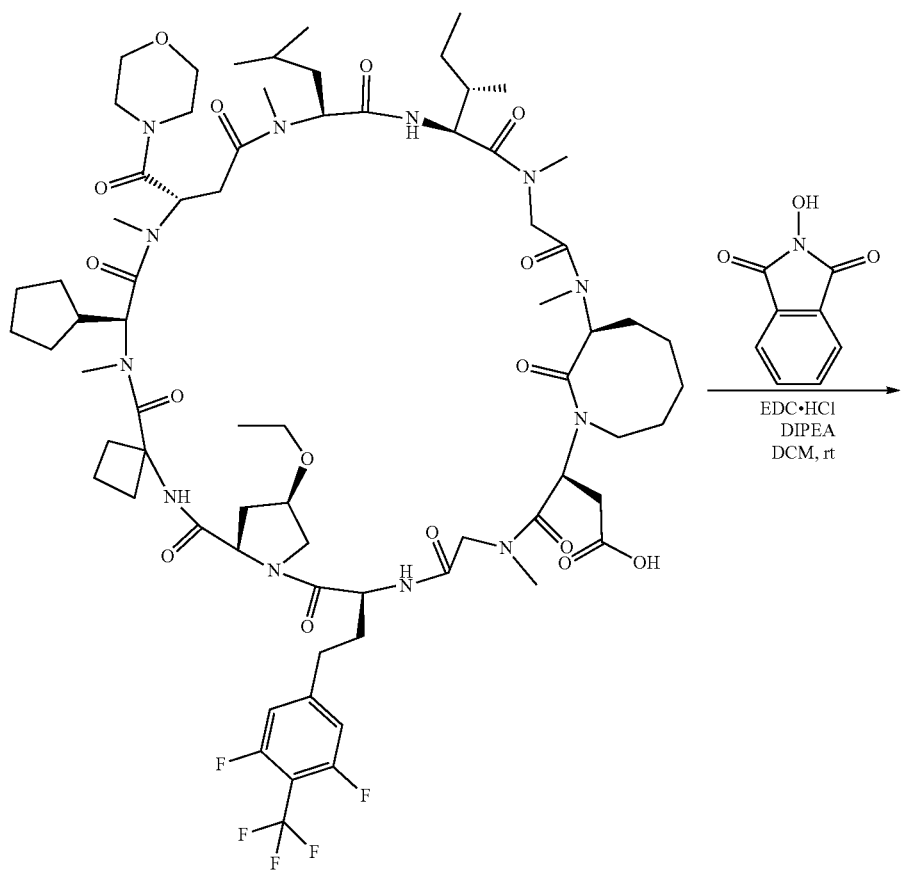
Compound PP0916-b

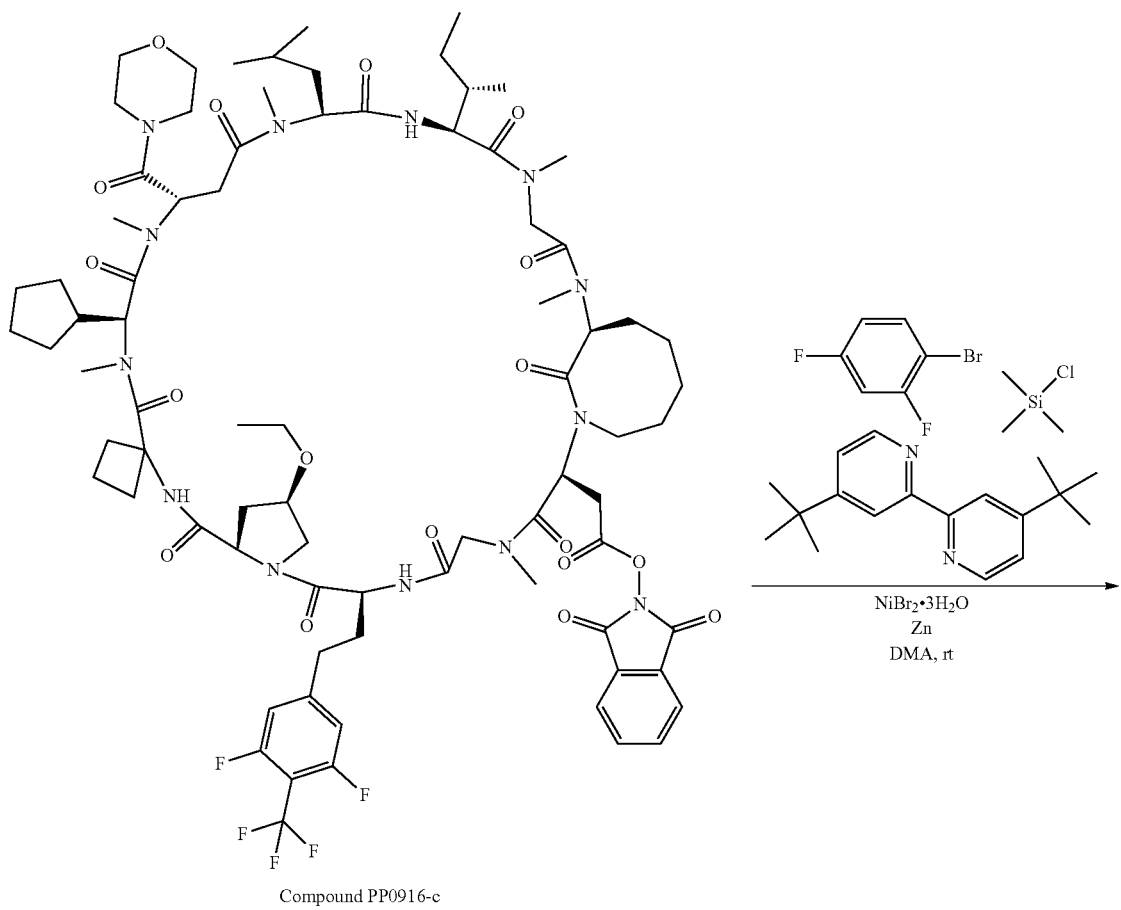
Compound PP0916-c

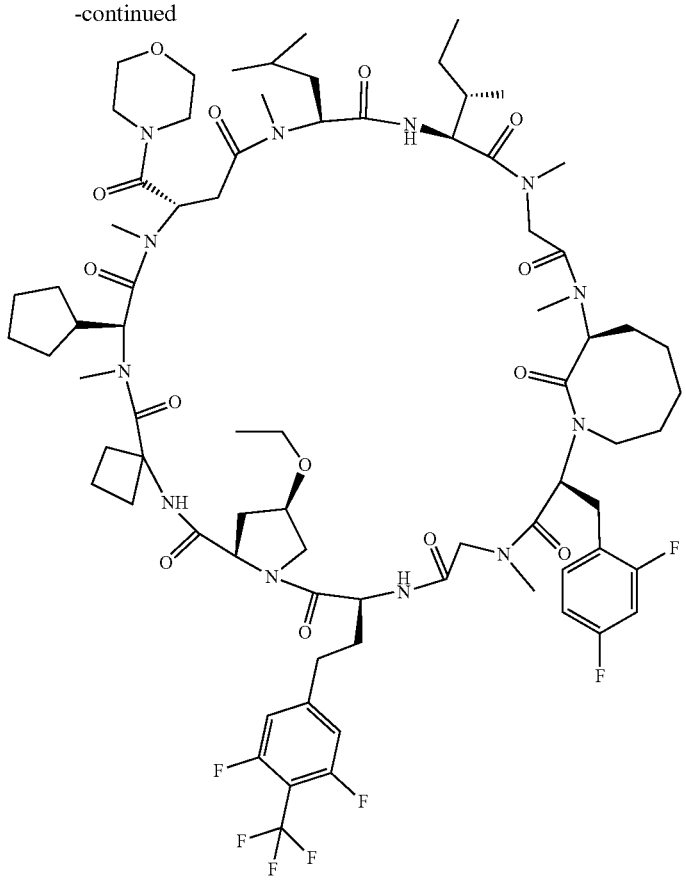

Compound PP0916

Using Compound aa375-resin as a raw material, peptide synthesis by the basic peptide synthesis method described in the present Examples was performed to give Compound PP0916-a. Using this as a starting material, PP916-b (109.0 mg, 14%) was obtained in the same manner as synthesis of Compound PP904-b.

LCMS (ESI) m/z=1478 (M+H)+

Retention time: 0.60 min (Analytical condition SQDAA50)

Using PP916-b as a starting material, PP916-c (95.3 mg, 92%) was obtained in the same manner as synthesis of Compound PP904-c.

LCMS (ESI) m/z=1623 (M+H)+

Retention time: 0.78 min (Analytical condition SQDAA50)

Using PP916-c as a starting material, PP916 (0.77 mg, 0.498 μmol) was obtained in the same manner as synthesis of Compound PP904 using 1-bromo-2,4-difluorobenzene in place of 4-bromofluorobenzene. LC/MS data is provided in Table 36.

Synthesis of Compounds PP917 to PP0924

Using Compound PP916-c (10 mg, 6.17 μmol) as a raw material, PP917 to PP0924 were obtained in the same manner as synthesis of Compound PP916 using the bromides (10 eq) shown in Table 21. LC/MS data is provided in Table 36.

TABLE 21

| Intended product | Bromide | Yield (mg) | Yield (%) |
|---|---|---|---|
| PP0917 | Br—⟨2,3-difluorophenyl⟩ | 0.38 | 4 |
| PP0918 | F—⟨3-chloro-4-bromophenyl⟩ | 0.29 | 3 |
| PP0919 | F—⟨3-chloro-4-bromophenyl⟩ | 1.02 | 10 |
| PP0920 | Br—⟨benzothiophene⟩ | 1.23 | 12 |

TABLE 21-continued
| Intended product | Bromide | Yield (mg) | Yield (%) |
|---|---|---|---|
| PP0921 | 6-bromobenzothiophene | 0.81 | 8 |
| PP0922 | 4-bromo-1-fluoro-2-methylbenzene | 1.02 | 10 |
TABLE 21-continued
| Intended product | Bromide | Yield (mg) | Yield (%) |
|---|---|---|---|
| PP0923 | 2-bromothiazole | 0.49 | 5 |
| PP0924 | 1-bromo-4-fluoro-2-methoxybenzene | 0.98 | 10 |
Synthesis of Compound PP02672
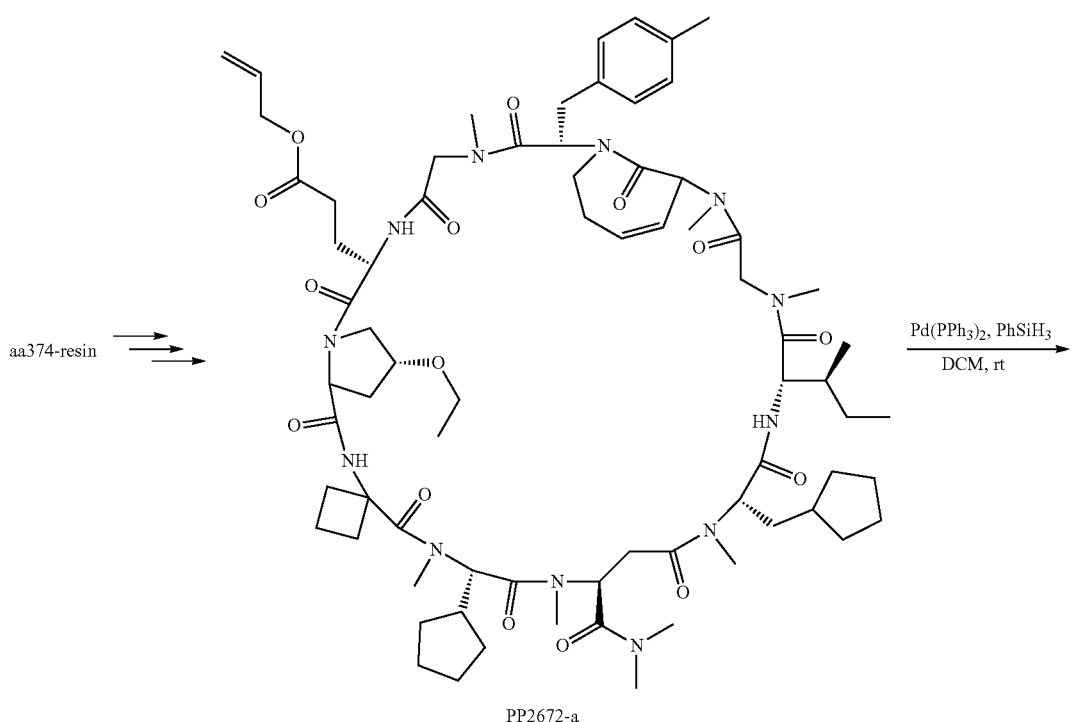
aa374-resin ⟶ ⟶ ⟶ [PP2672-a] $\xrightarrow{\text{Pd(PPh}_3)_2,\ \text{PhSiH}_3}{\text{DCM, rt}}$
PP2672-a

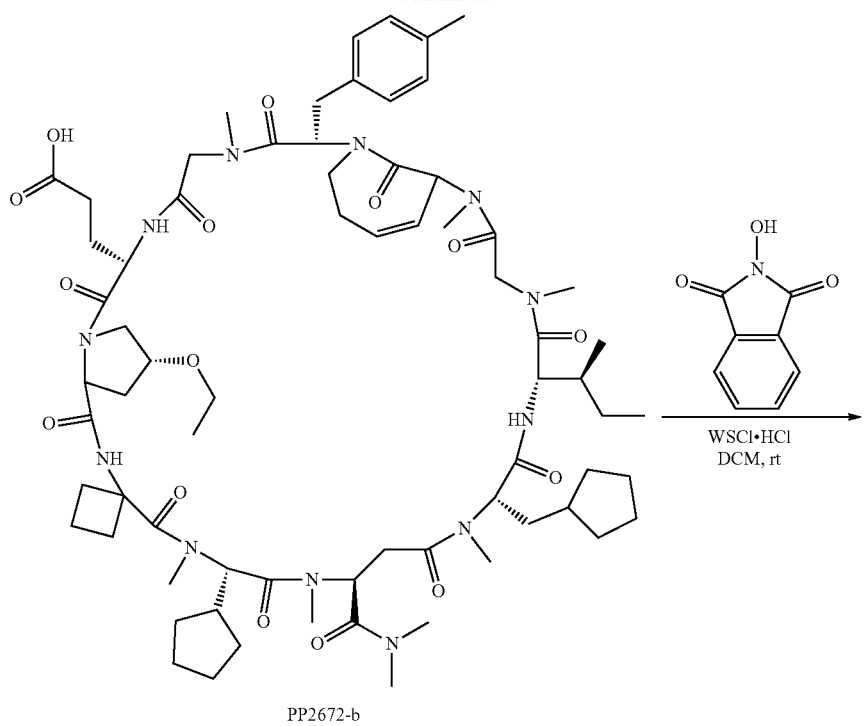
PP2672-b
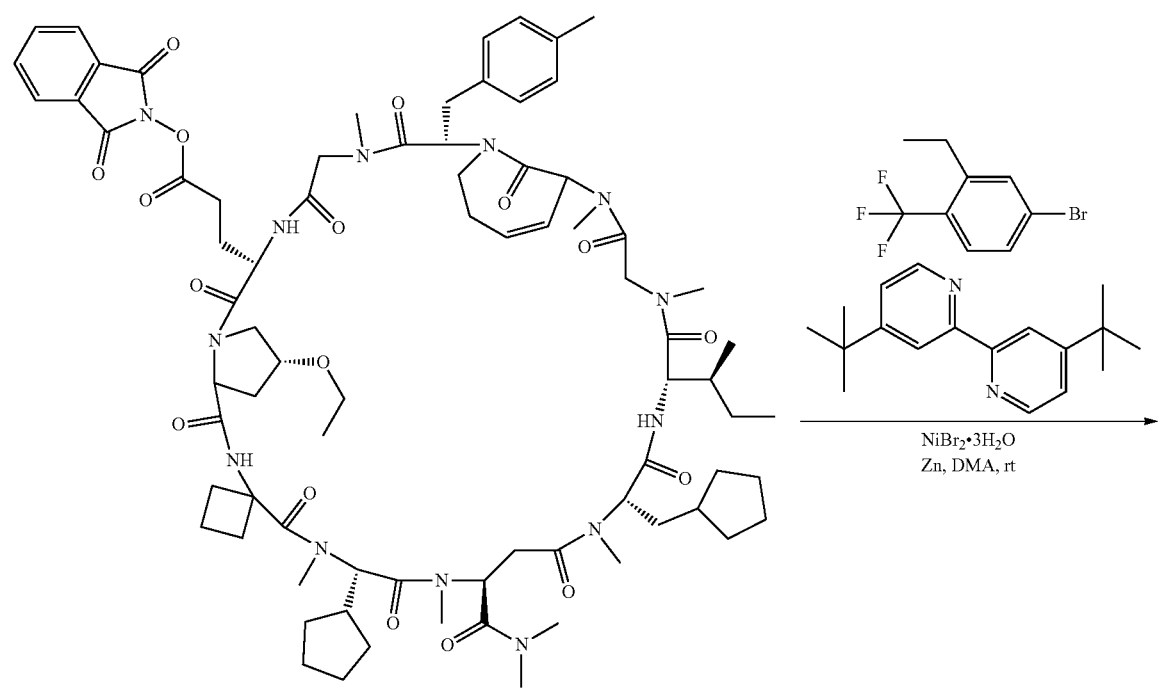
PP2672-c

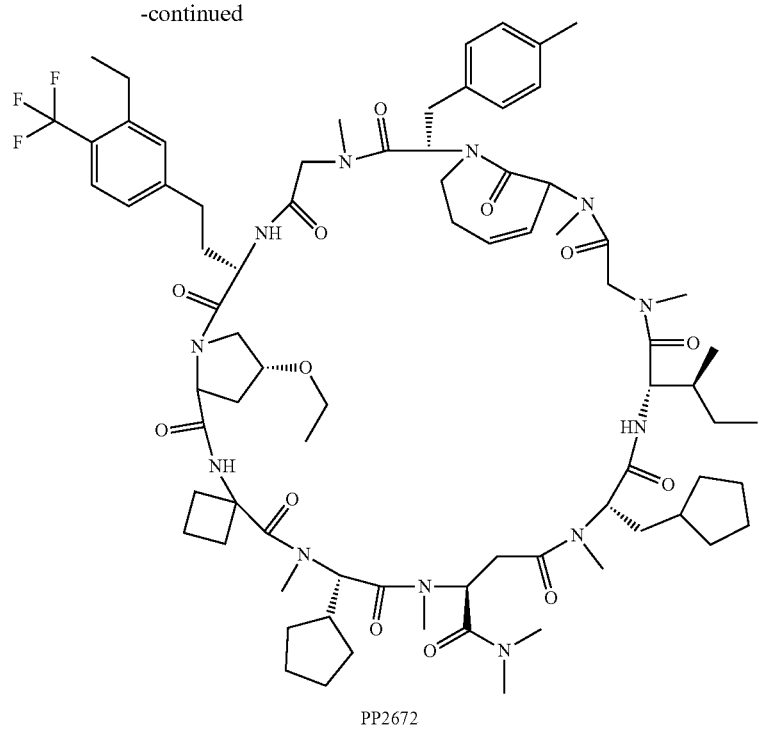

PP2672

Using Compound aa374-resin as a raw material, peptide synthesis was carried out by the basic peptide synthesis method described in the present Examples to give Compound PP2672-a. Using this as a starting material, PP2672-b (289 mg, 16%) was obtained in the same manner as the synthesis of Compound PP904-b.

LCMS (ESI) m/z=1370 (M+H)+

Retention time: 0.79 min (Analytical condition SQDFA05)

Using PP2672-b as a starting material, PP2672-c (329 mg, quant.) was obtained in the same manner as the synthesis of Compound PP904-c.

LCMS (ESI) m/z=1515 (M+H)+

Retention time: 0.92 min (Analytical condition SQDFA05)

Using PP2672-c as a starting material, PP2672 (6.2 mg, 41%) was obtained in the same manner as the synthesis of Compound PP904 except that 4-bromo-2-ethyl-1-(trifluoromethyl)benzene was used in place of 4-bromofluorobenzene. LC/MS data are provided in Table 36.

Synthesis of Compounds PP2673 to PP2686

Using Compound PP02672-c as a raw material, PP2673 to PP2686 were obtained in the same manner as the synthesis of Compound PP02672 using the bromides (10 eq) shown in Table 21-1. LC/MS data are provided in Table 36.

TABLE 21-1

| Intended product | Bromide | Yield (mg) | Yield (%) |
|---|---|---|---|
| PP2673 | Br-[3-F, 4-Cl, 5-OMe-phenyl] | 3.3 | 19 |

TABLE 21-1-continued

| Intended product | Bromide | Yield (mg) | Yield (%) |
|---|---|---|---|
| PP2674 | Br-[3-F, 4-Et, 5-OMe-phenyl] | 5.4 | 31 |
| PP2675 | Br-[3-Me, 4-CHF$_2$, 5-Me-phenyl] | 6.4 | 36 |
| PP2676 | Br-[3-F, 4-CHF$_2$, 5-Me-phenyl] | 7.6 | 43 |
| PP2677 | Br-[3-Me, 4-CHF$_2$, 5-Cl-phenyl] | 7.2 | 40 |

TABLE 21-1-continued
| Intended product | Bromide | Yield (mg) | Yield (%) |
|---|---|---|---|
| PP2678 | 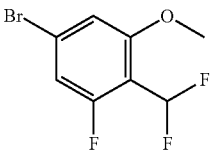 | 7.3 | 41 |
| PP2679 | 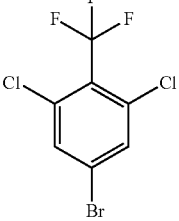 | 2.8 | 28 |
| PP2680 | 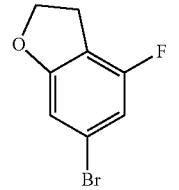 [SMILES: Fc1cc(Br)cc2c1CCO2] | 1.1 | 9.2 |
| PP2681 |  | 2.5 | 31 |
| PP2682 | 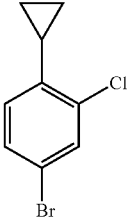 [SMILES: Clc1cc(Br)ccc1C1CC1] | 1.3 | 17 |
| PP2683 | 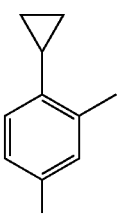 | 2.4 | 21 |
| PP2684 | 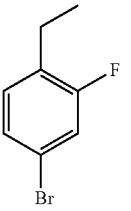 | 2.3 | 20 |
| PP2685 |  | 1.2 | 11 |
| PP2686 |  | 1.2 | 10 |

Synthesis of Compound PP02687
aa374-resin ⟶⟶
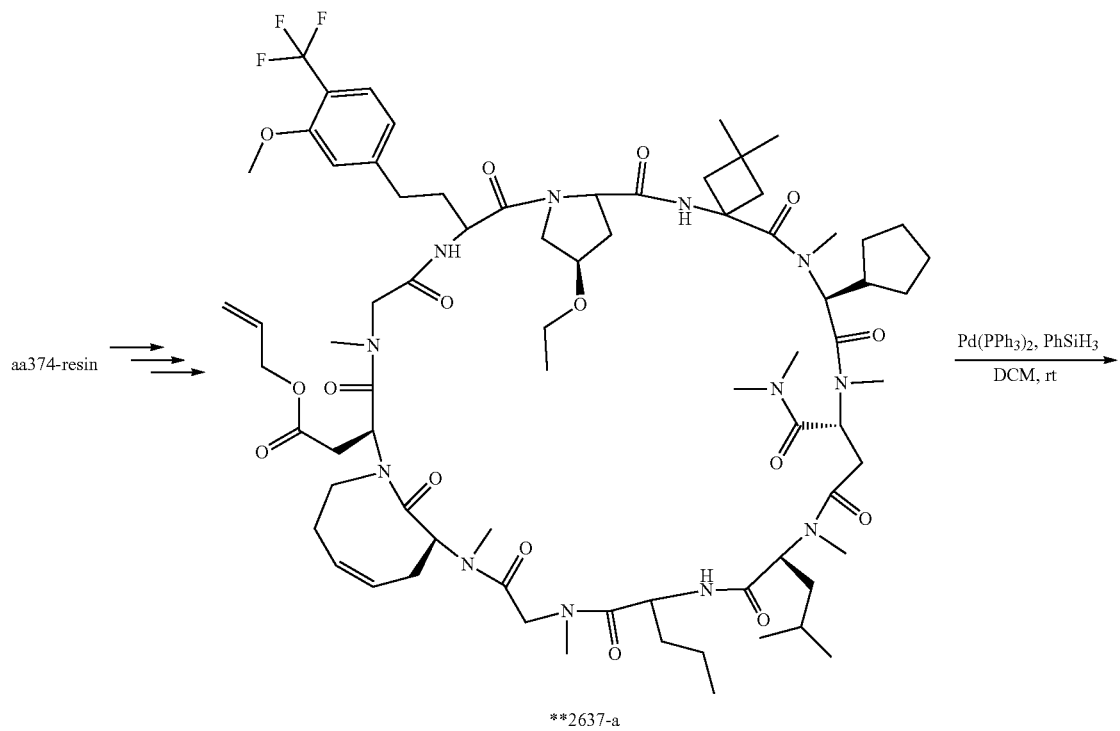
**2637-a
Pd(PPh₃)₂, PhSiH₃
DCM, rt
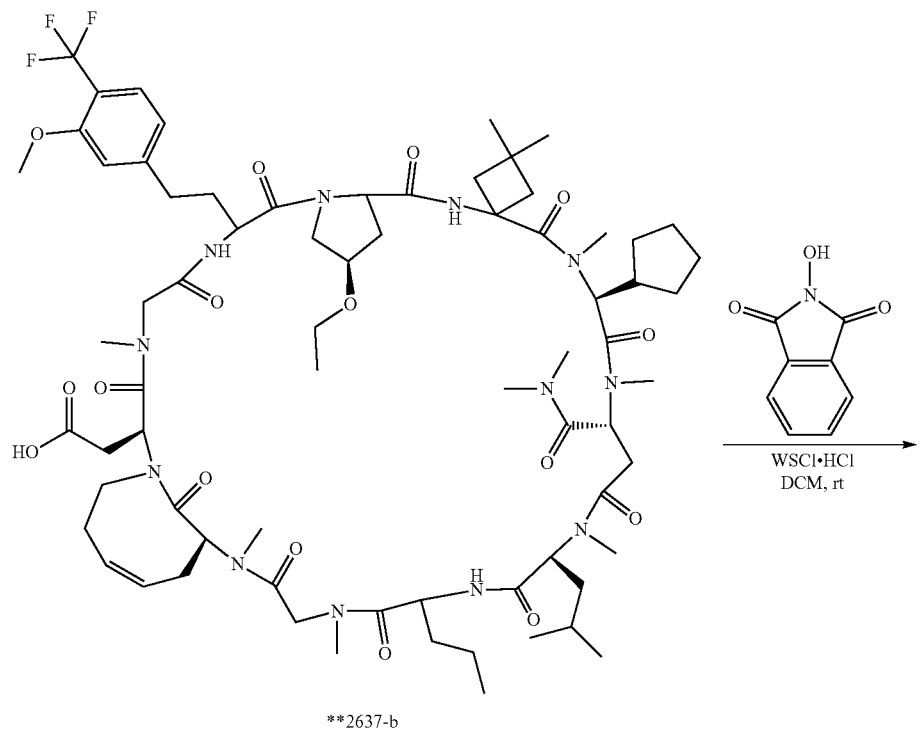
**2637-b
WSCl·HCl
DCM, rt -continued

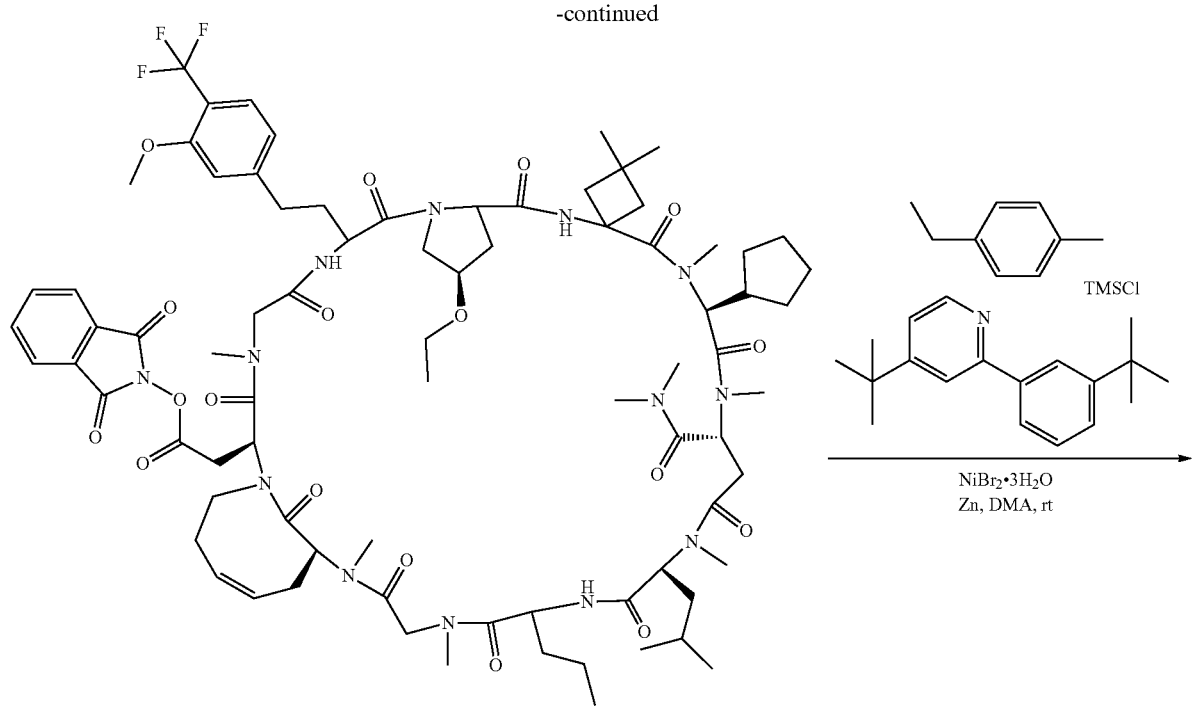

**2637-c

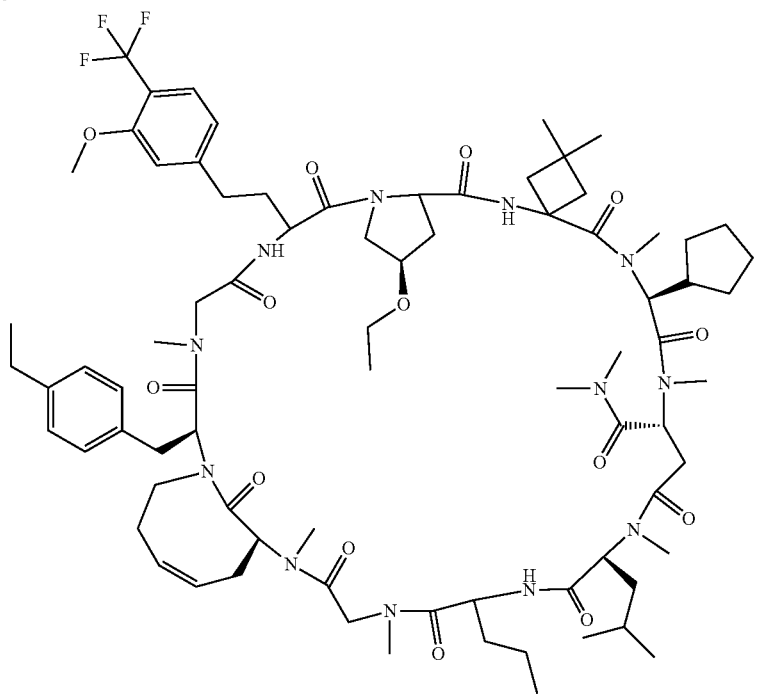

**2637

Using Compound aa374-resin as a raw material, peptide synthesis was carried out by the basic peptide synthesis method described in the present Examples to give Compound PP2687-a. Using this as a starting material, PP2687-b (97 mg, 16%) was obtained in the same manner as the synthesis of Compound PP904-b.

LCMS (ESI) m/z=1456 (M+H)+

Retention time: 0.91 min (Analytical condition SQDFA05)

Using PP2687-b as a starting material, PP2687-c (99 mg, 76%) was obtained in the same manner as the synthesis of Compound PP904-c.

LCMS (ESI) m/z=1601 (M+H)+

Retention time: 1.00 min (Analytical condition SQDFA05)

Using PP2687-c as a starting material, PP2687 (2.3 mg, 3.3%) was obtained in the same manner as the synthesis of Compound PP904 except that 1-ethyl-4-iodobenzene was used in place of 4-bromofluorobenzene. LC/MS data are provided in Table 36.

Synthesis of Compounds PP2688 to PP2695

Using Compound PP02687-c as a raw material, PP2688 to PP2695 were obtained in the same manner as the synthesis of Compound PP02687 using the halides (10 eq) shown in Table 21-2. LC/MS data are provided in Table 36.

TABLE 21-2

| Intended product | Bromide | Yield (mg) | Yield (%) |
|---|---|---|---|
| PP2688 | 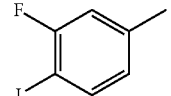 | 2.7 | 3.8 |
| PP2689 | 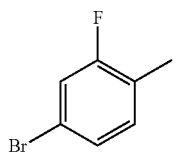 | 2.7 | 3.8 |
| PP2690 | 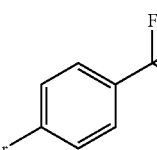 | 2.8 | 3.9 |
| PP2691 | 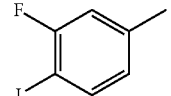 | 2.6 | 3.7 |
| PP2692 | 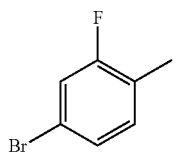 | 2.2 | 3.1 |
| PP2693 | 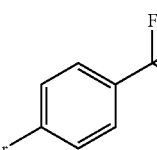 | 2.4 | 3.4 |
| PP2694 | 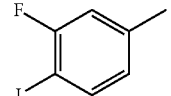 | 2.4 | 3.4 |
| PP2695 | 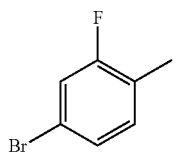 | 0.2 | 0.3 |

Synthesis of Compound PP02696

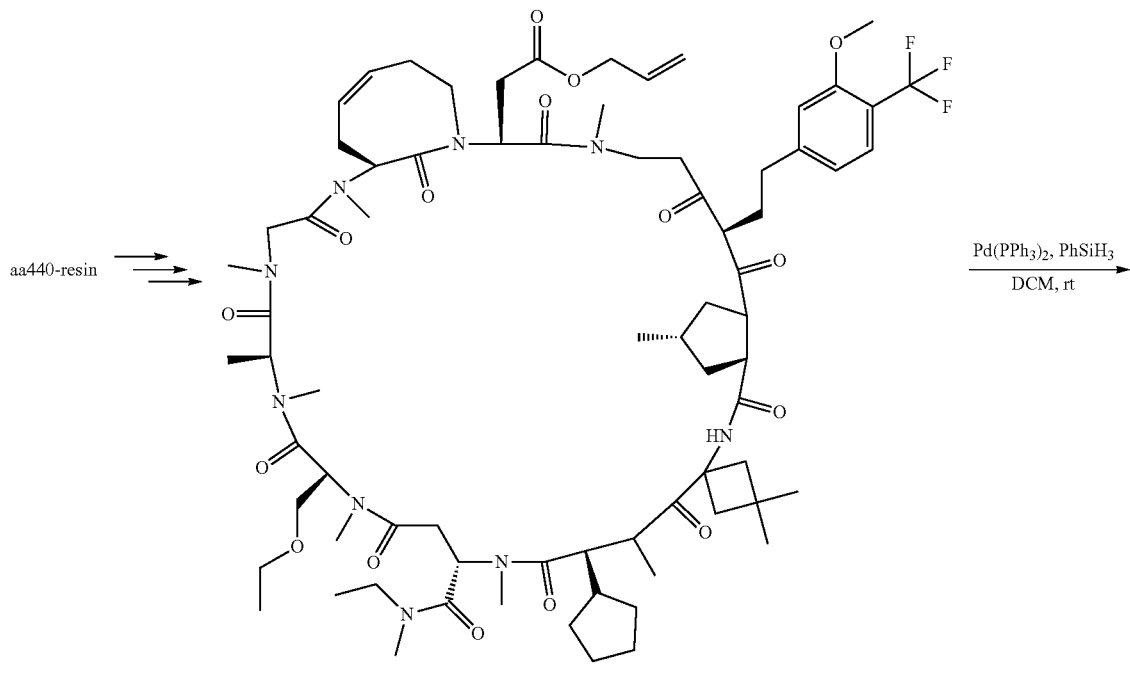

**2696-a

-continued
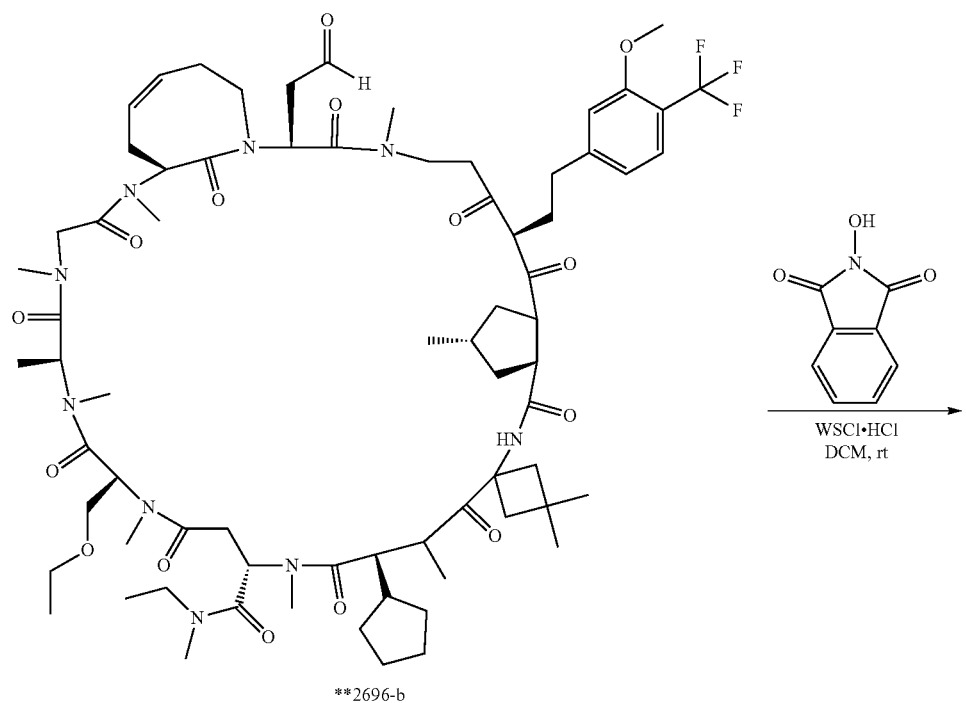
**2696-b
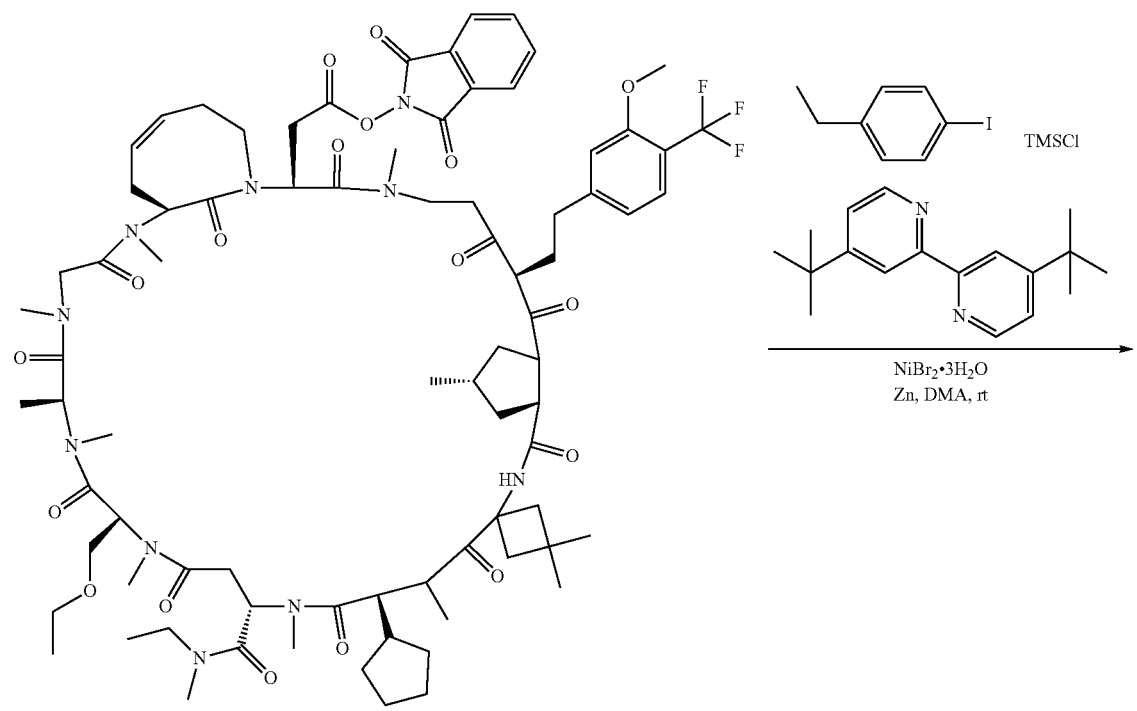
**2696-c

-continued

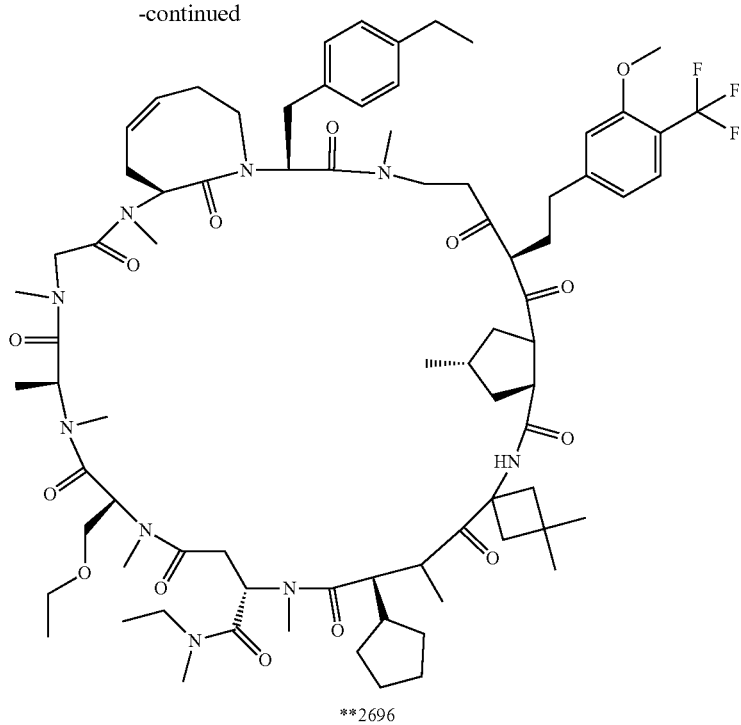

**2696

Using Compound aa440-resin as a raw material, peptide synthesis was carried out by the basic peptide synthesis method described in the present Examples to give Compound PP2696-a. Using this as a starting material, PP2696-b (117 mg, 27%) was obtained in the same manner as the synthesis of Compound PP904-b.

LCMS (ESI) m/z=1442 (M+H)+

Retention time: 0.92 min (Analytical condition SQDFA05)

Using PP2696-b as a starting material, PP2696-c (115 mg, 89%) was obtained in the same manner as the synthesis of Compound PP904-c.

LCMS (ESI) m/z=1586 (M−H)−

Retention time: 1.02 min (Analytical condition SQDFA05)

Using PP2696-c as a starting material, PP2696 (3.7 mg, 7.4%) was obtained in the same manner as the synthesis of Compound PP904 except that 1-ethyl-4-iodobenzene was used in place of 4-bromofluorobenzene. LC/MS data are provided in Table 36.

Synthesis of Compounds PP2697 to PP2704

Using Compound PP02696-c as a raw material, PP2697 to PP2704 were obtained in the same manner as the synthesis of Compound PP02696 using the halides (10 eq) shown in Table 21-3. LC/MS data are provided in Table 36.

TABLE 21-3

| Intended product | Bromide | Yield (mg) | Yield (%) |
|---|---|---|---|
| PP2697 |  | 3.8 | 7.6 |

TABLE 21-3-continued

| Intended product | Bromide | Yield (mg) | Yield (%) |
|---|---|---|---|
| PP2698 | 2-fluoro-4-bromotoluene | 4.1 | 8.2 |
| PP2699 | 1-bromo-4-(1,1-difluoroethyl)benzene | 4.1 | 8.0 |
| PP2700 | 1-cyclopropyl-4-iodobenzene | 3.8 | 7.5 |
| PP2701 | 1-iodo-4-isopropylbenzene | 3.5 | 7.0 |
| PP2702 | 1-iodo-4-methoxybenzene | 3.9 | 7.8 |

TABLE 21-3-continued
| Intended product | Bromide | Yield (mg) | Yield (%) |
|---|---|---|---|
| PP2703 | 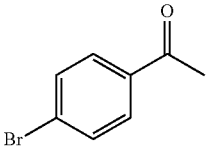 | 3.7 | 7.3 |
| PP2704 | 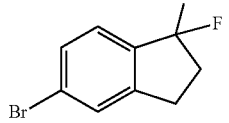 | 0.2 | 0.4 |
Synthesis of Compound PP02849
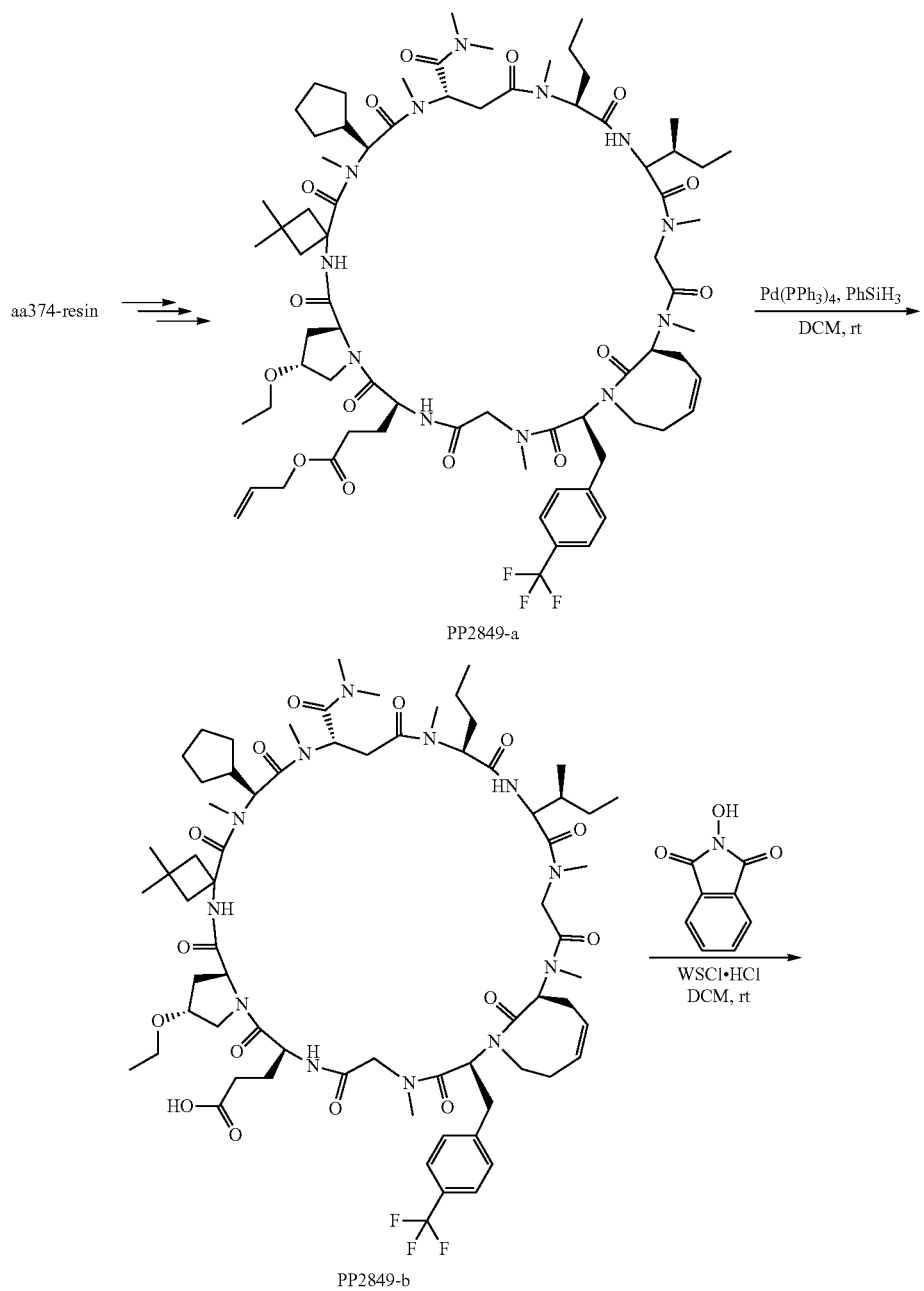

-continued

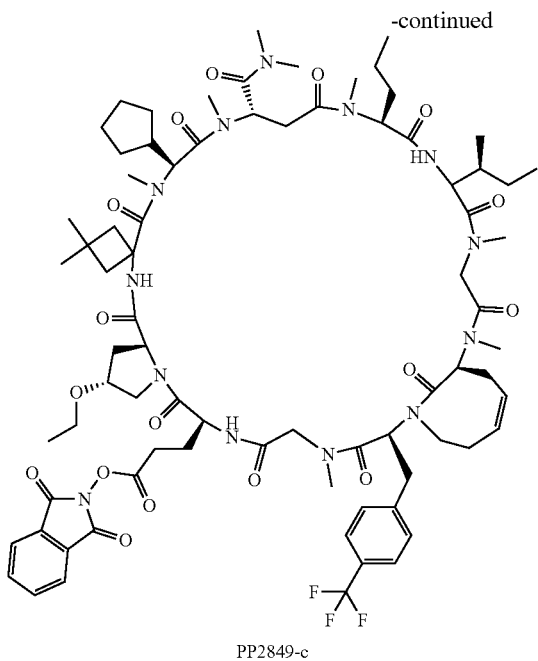
PP2849-c

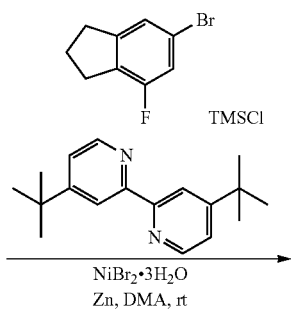

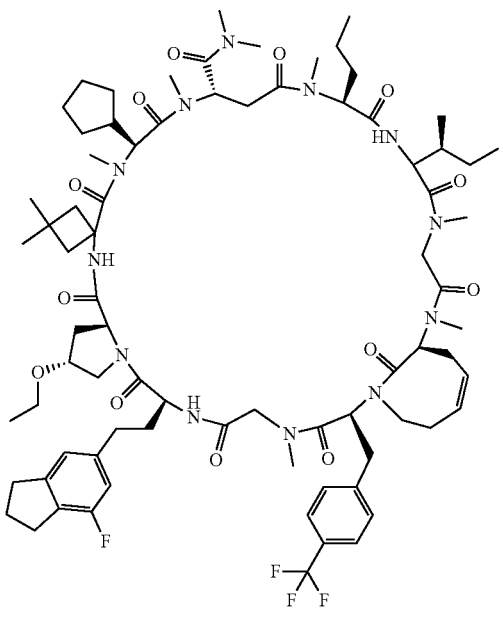
PP2849

Using Compound aa374-resin as a raw material, peptide synthesis was carried out by the basic peptide synthesis method described in the present Examples to give Compound PP2849-a. Using this as a starting material, PP2849-b (345 mg, 22%) was obtained in the same manner as the synthesis of Compound PP904-b.

LCMS (ESI) m/z=1412 (M+H)+

Retention time: 0.80 min (Analytical condition SQDFA05)

Using PP2849-b as a starting material, PP2849-c (395 mg, quant. %) was obtained in the same manner as the synthesis of Compound PP904-c.

LCMS (ESI) m/z=1557 (M+H)+

Retention time: 0.52 min (Analytical condition SQDFA50)

Using PP2849-c as a starting material, PP2849 (4.5 mg, 39%) was obtained in the same manner as the synthesis of Compound PP904 except that 6-bromo-4-fluoro-2,3-dihydro-1H-indene was used in place of 4-bromofluorobenzene. LC/MS data are provided in Table 36.

Synthesis of Compounds PP2850 to PP2869

Using Compound PP02849-c as a raw material, PP2850 to PP2869 were obtained in the same manner as the synthesis of Compound PP02849 using the bromides (10 eq) shown in Table 21-4. LC/MS data are provided in Table 36.

TABLE 21-4
| Intended product | Bromide | Yield (mg) | Yield (%) |
|---|---|---|---|
| PP2850 | 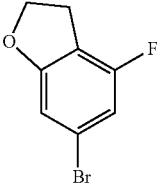 [SMILES: Fc1cc(Br)cc2c1CCO2] | 3.5 | 30 |
| PP2851 | 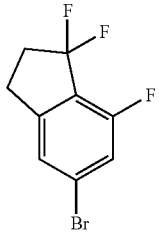 [SMILES: Fc1cc(Br)cc2c1C(F)(F)CC2] | 5.1 | 44 |
| PP2852 | 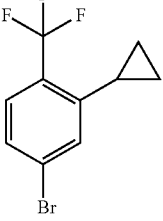 | 5.1 | 43 |
| PP2853 | 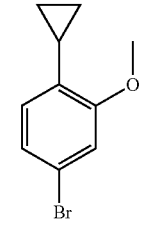 | 5.6 | 48 |
| PP2854 | 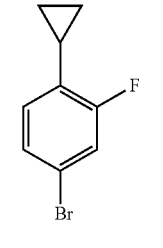 [SMILES: Fc1cc(Br)ccc1C1CC1] | 7.0 | 61 |
| PP2855 | 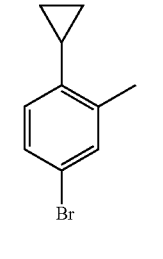 | 3.4 | 29 |
| PP2856 | 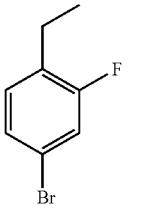 | 5.0 | 44 |
| PP2857 | 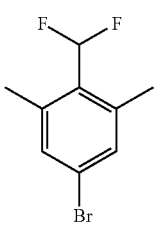 | 5.1 | 44 |
| PP2858 | 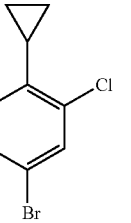 | 4.6 | 40 |
| PP2859 | 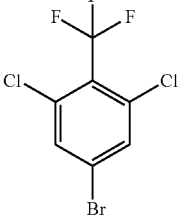 | 4.3 | 35 |
| PP2860 | 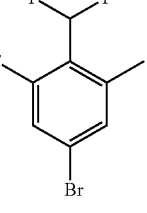 | 7.5 | 64 |
| PP2861 | 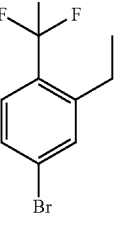 | 6.9 | 58 |

TABLE 21-4-continued

| Intended product | Bromide | Yield (mg) | Yield (%) |
|---|---|---|---|
| PP2862 | 2-ethyl-3-fluoro-6-methoxy-bromobenzene | 5.8 | 50 |
| PP2863 | 2,6-dimethyl-4-bromo-cyclopropylbenzene | 3.4 | 29 |
| PP2864 | 2-chloro-3-fluoro-6-methoxy-bromobenzene | 1.3 | 11 |
| PP2865 | 2,6-dichloro-4-bromo-(difluoromethyl)benzene | 7.8 | 65 |
| PP2866 | 2-chloro-6-methyl-4-bromo-(difluoromethyl)benzene | 7.6 | 64 |
| PP2867 | 2-fluoro-6-methoxy-4-bromo-(difluoromethyl)benzene | 7.2 | 60 |
| PP2868 | 2-methoxy-4-bromo-(difluoromethyl)benzene | 0.4 | 3.2 |
| PP2869 | 2-ethyl-6-methoxy-4-bromobenzene | 4.1 | 35 |

Synthesis of Compound PP02870

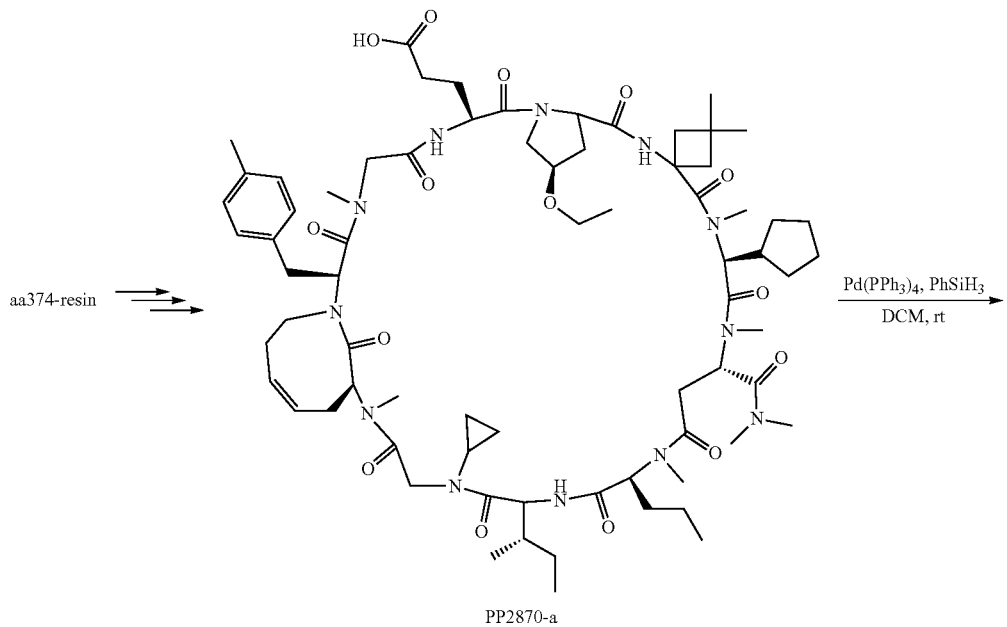

PP2870-a

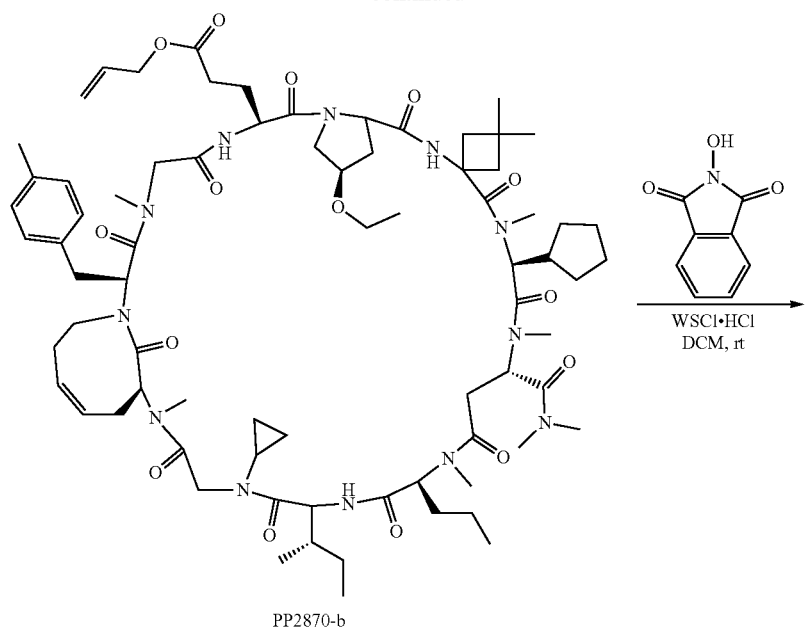
PP2870-b
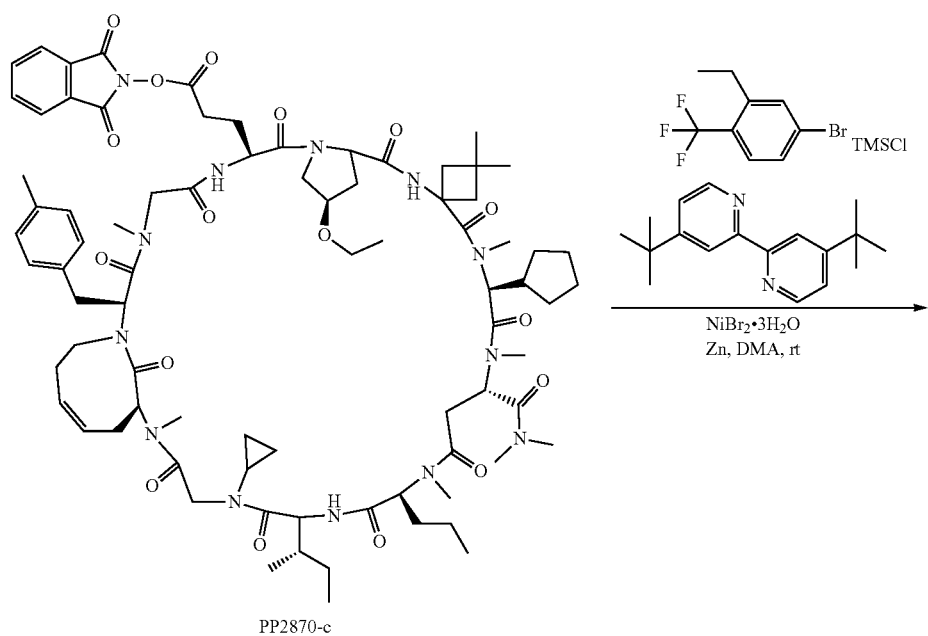
PP2870-c

-continued

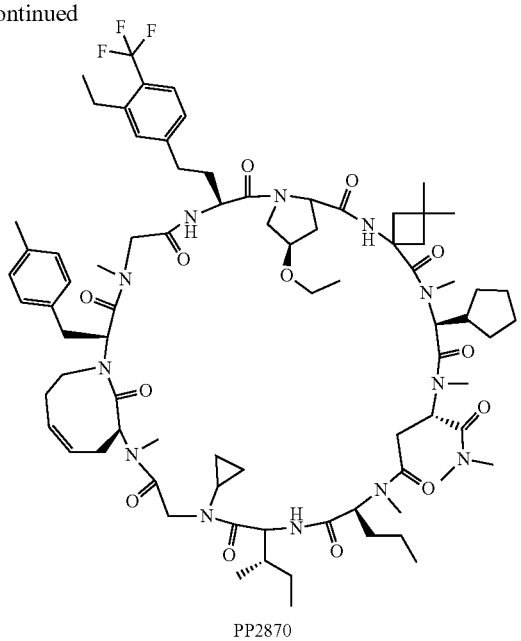

PP2870

Using Compound aa374-resin as a raw material, peptide synthesis was carried out by the basic peptide synthesis method described in the present Examples to give Compound PP2870-a. Using this as a starting material, PP2870-b (289 mg, 16%) was obtained in the same manner as the synthesis of Compound PP904-b.

LCMS (ESI) m/z=1370 (M+H)+

Retention time: 0.79 min (Analytical condition SQDFA05)

Using PP2870-b as a starting material, PP2870-c (329 mg, quant. %) was obtained in the same manner as the synthesis of Compound PP904-c.

LCMS (ESI) m/z=1515 (M+H)+

Retention time: 0.92 min (Analytical condition SQDFA05)

Using PP2870-c as a starting material, PP2870 (6.2 mg, 41%) was obtained in the same manner as the synthesis of Compound PP904 except that 4-bromo-2-ethyl-1-(trifluoromethyl)benzene was used in place of 4-bromofluorobenzene. LC/MS data are provided in Table 36.

Synthesis of Compounds PP2871 to PP2886

Using Compound PP02870-c as a raw material, PP2871 to PP2886 were obtained in the same manner as the synthesis of Compound PP02870 using the bromides (10 eq) shown in Table 21-5. LC/MS data are provided in Table 36.

TABLE 21-5

| Intended product | Bromide | Yield (mg) | Yield (%) |
|---|---|---|---|
| PP2871 | (structure) | 7.5 | 51 |

TABLE 21-5-continued

| Intended product | Bromide | Yield (mg) | Yield (%) |
|---|---|---|---|
| PP2872 | (structure) | 6.8 | 47 |
| PP2873 | (structure) | 7.4 | 51 |
| PP2874 | (structure) | 7.4 | 50 |
| PP2875 | (structure) | 8.6 | 58 |

TABLE 21-5-continued

| Intended product | Bromide | Yield (mg) | Yield (%) |
|---|---|---|---|
| PP2876 | 4-bromo-2-(difluoromethyl)-1-fluoro-3-methoxybenzene... (F, F difluoromethyl; F; OMe; Br) | 7.7 | 52 |
| PP2877 | 4-bromo-2,6-dichloro-1-(difluoromethyl)benzene (F,F difluoromethyl; Cl, Cl; Br) | 6.3 | 42 |
| PP2878 | 2-bromo-1-cyclopropyl-3,5-dimethylbenzene (cyclopropyl; Me, Me; Br) | 6.4 | 44 |
| PP2879 | 6-bromo-4-fluoro-2,3-dihydro-1H-indene | 6.7 | 46 |
| PP2880 | 6-bromo-4-fluoro-2,3-dihydrobenzofuran | 6.3 | 44 |
| PP2881 | 4-bromo-2-cyclopropyl-1-(trifluoromethyl)benzene | 6.9 | 46 |
| PP2882 | 5-bromo-1,1-difluoro-2,3-dihydro-1H-indene | 7.8 | 53 |
| PP2883 | 4-bromo-1-cyclopropyl-2-methoxybenzene | 8.5 | 59 |
| PP2884 | 4-bromo-1-cyclopropyl-2-fluorobenzene | 9.3 | 64 |
| PP2885 | 4-bromo-2-chloro-1-cyclopropylbenzene | 8.5 | 58 |
| PP2886 | 4-bromo-1-cyclopropyl-2-methylbenzene | 7.6 | 52 |

1-6-3. Peptide Modification by Amidation of Carboxylic Acid

Synthesis of Compound PP391 aa386-resin →
→→

-continued

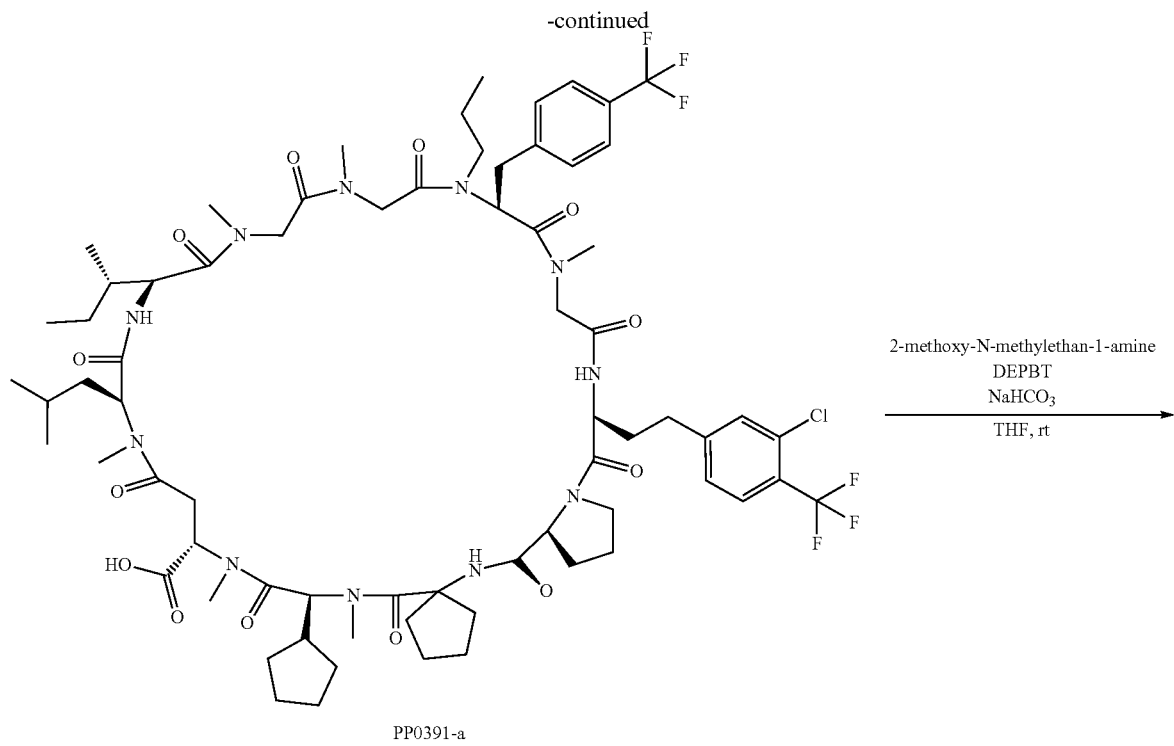

PP0391-a 2-methoxy-N-methylethan-1-amine
DEPBT
NaHCO₃
THF, rt

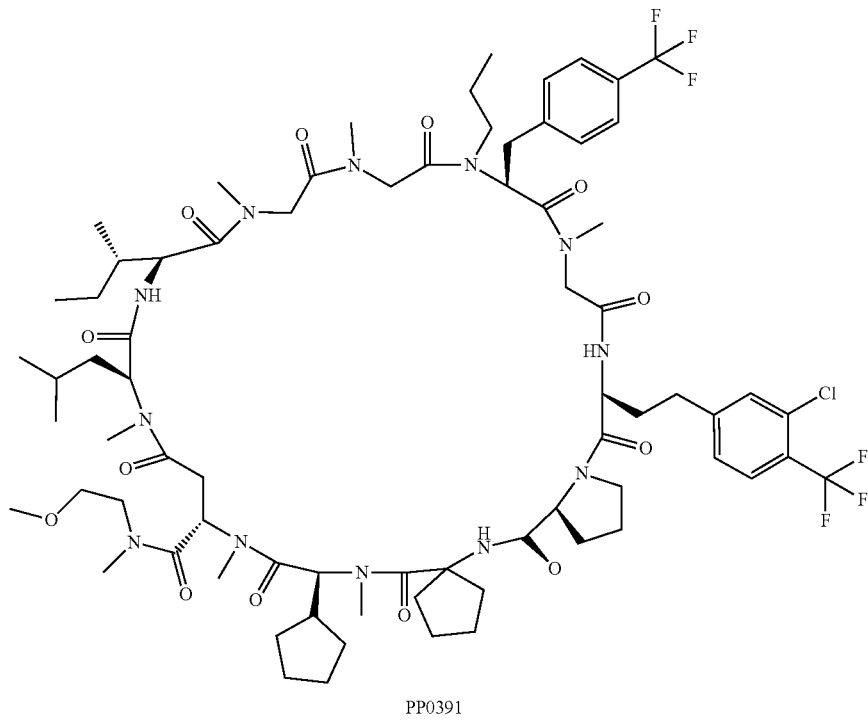

PP0391

Using Compound aa386-resin as a raw material, peptide synthesis by the basic peptide synthesis method described in the present Examples was performed to give Compound PP0391-a (5.6 mg, 0.00386 mmol).

LCMS (ESI) m/z=1451 (M+H)+

Retention time: 0.66 min (Analytical condition SQDFA50)

2-Methoxy-N-methylethan-1-amine (0.002 mL, 0.019 mmol) was added to a THF (0.039 mL) solution of Compound PP391-a (5.6 mg, 0.00386 mmol), sodium bicarbonate (1.62 mg, 0.019 mmol), and DEPBT (5.77 mg, 0.019 mmol), the mixture was stirred at room temperature for 1 hour, and then the solvent was distilled off under reduced pressure. The resulting crude product was purified by reverse phase chromatography (0.1% formic acid-containing acetonitrile/0.1% formic acid-containing distilled water) to give PP0391 (5.08 mg, 86%). LC/MS data is provided in Table 36.

Synthesis of Compounds PP1151 and PP1152

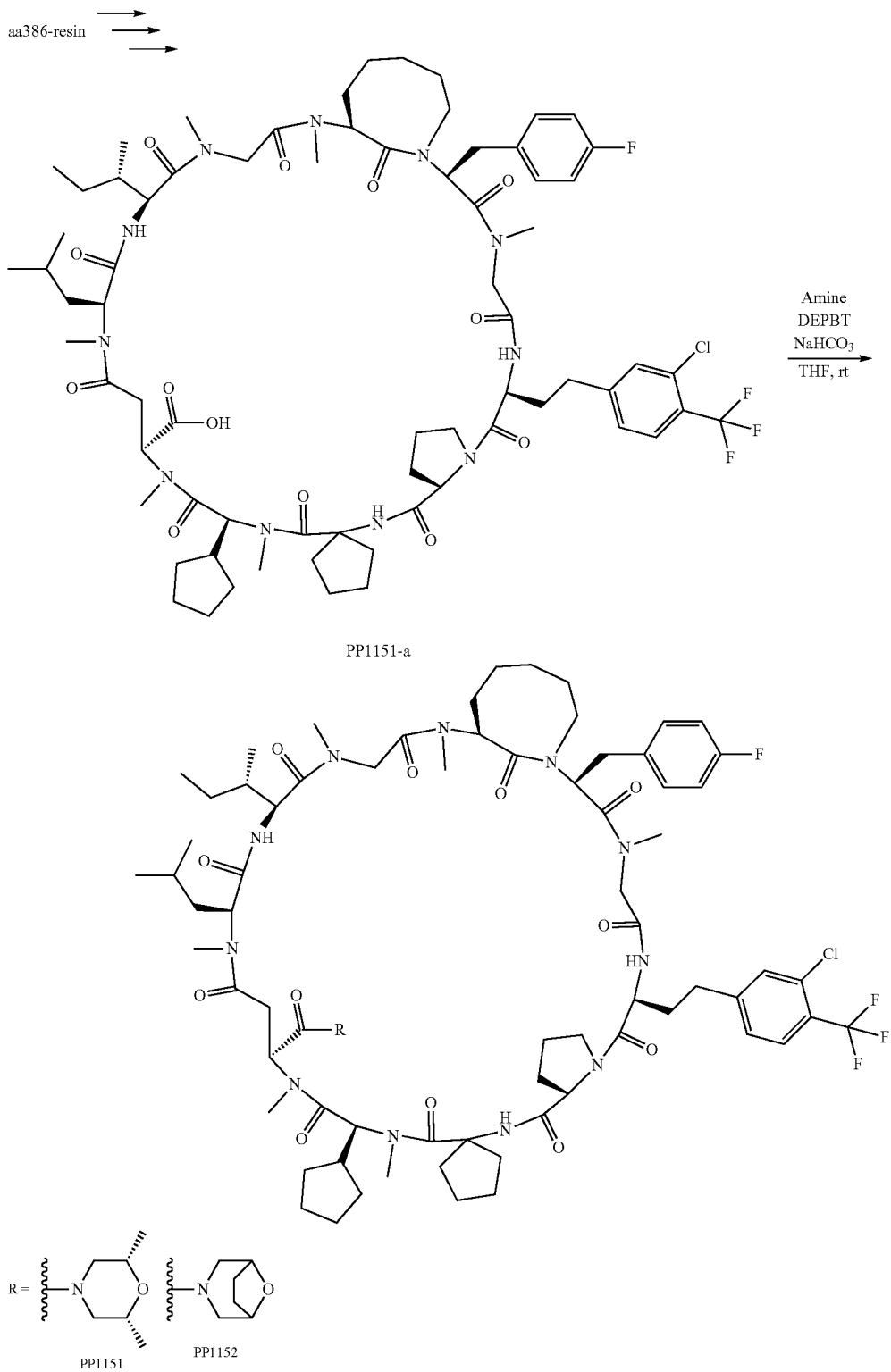

Using Compound aa386-resin as a raw material, peptide synthesis by the basic peptide synthesis method described in the present Examples was performed to give Compound PP1151-a. Using the resulting Compound PP1151-a (5.0 mg), the intended compounds were obtained in the same manner as synthesis of Compound PP391 using the amines shown in Table 22 in place of 2-methoxy-N-methylethan-1-amine. LC/MS data is provided in Table 36.

TABLE 22
| Intended product | Amine | Yield | Yield |
|---|---|---|---|
| PP1151 | | 3.2 mg | 60% |
TABLE 22-continued
| Intended product | Amine | Yield | Yield |
|---|---|---|---|
| PP1152 | | 2.8 mg | 53% |
Synthesis of Compounds PP1153 and PP1154
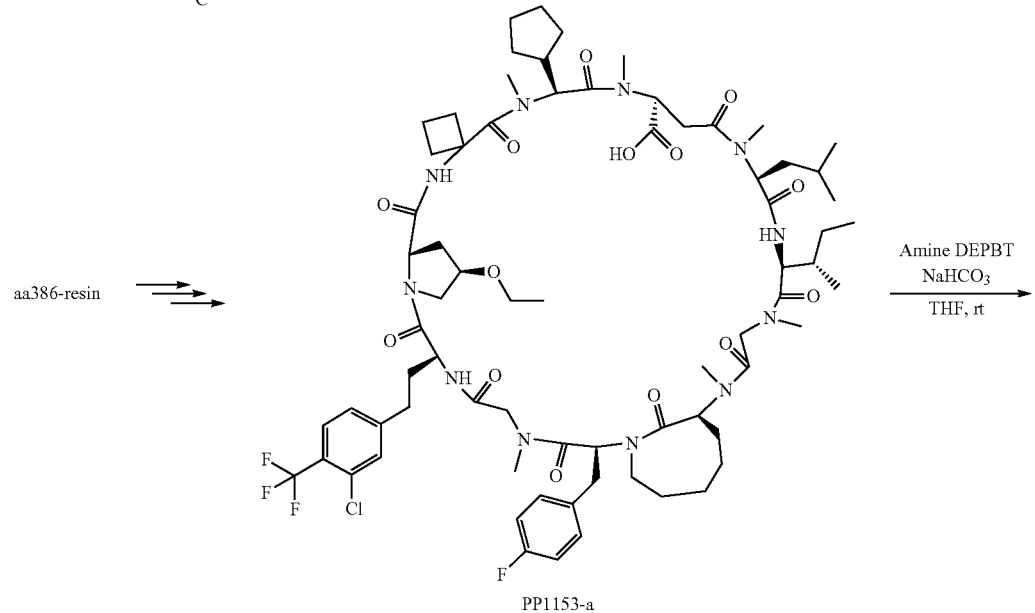
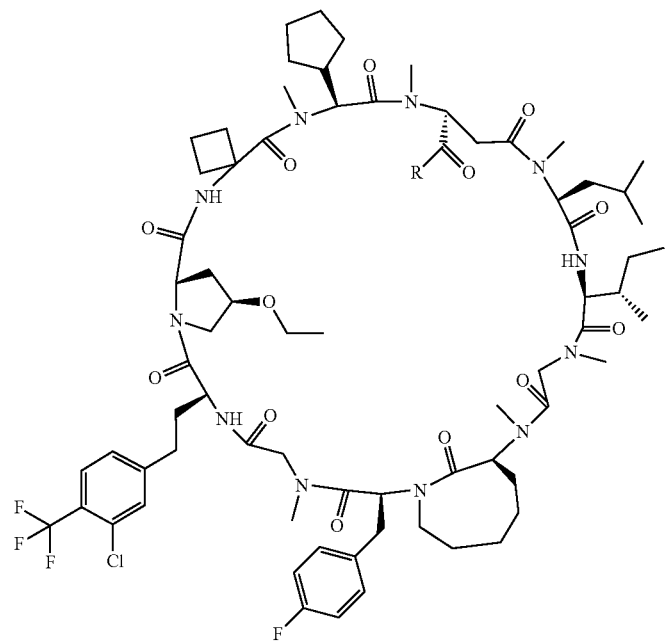

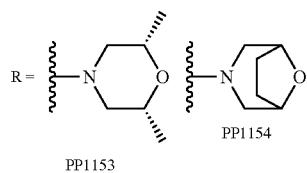

Using Compound aa386-resin as a raw material, peptide synthesis by the basic peptide synthesis method described in the present Examples was performed to give Compound PP1153-a. Using the resulting Compound PP1153-a (5.1 mg), the intended compounds were obtained in the same manner as synthesis of Compound PP391 using the amines shown in Table 23 in place of 2-methoxy-N-methylethan-1-amine. LC/MS data is provided in Table 36.

TABLE 23

| Intended product | Amine | Yield | Yield |
|---|---|---|---|
| PP1153 | | 2.4 mg | 44% |
| PP1154 | | 2.5 mg | 46% |

Synthesis of Compounds PP1300, PP1301, PP1302, PP1303, PP1304, PP1305, PP1306, PP1307. PP1308, PP1309, PP1310, PP1311, PP1312, PP1313, PP1314, PP1315, PP1316, PP1317, PP1318, PP1319, PP1320, PP1331, PP1387, PP1388, and PP1389

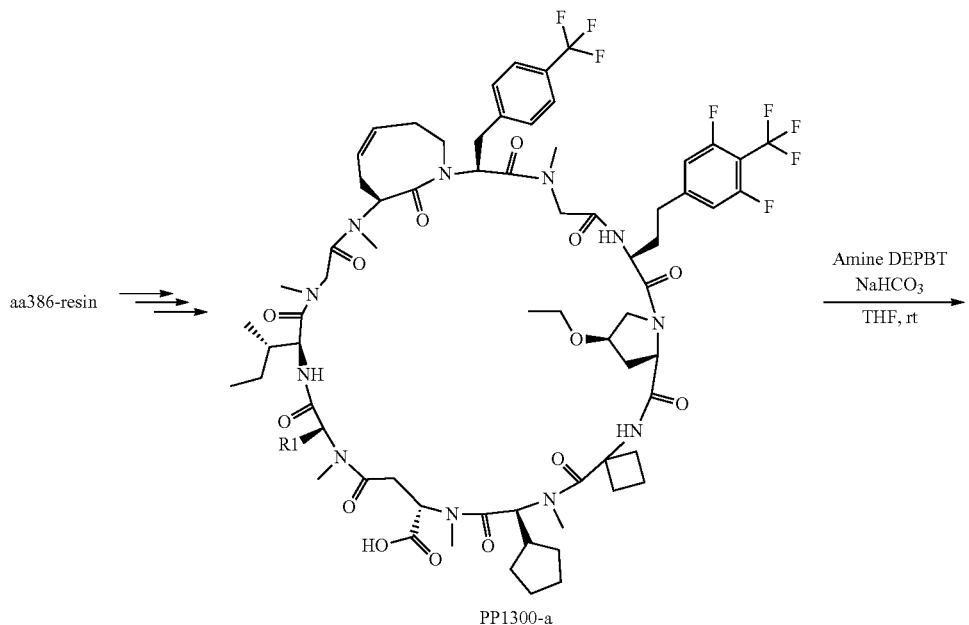

-continued

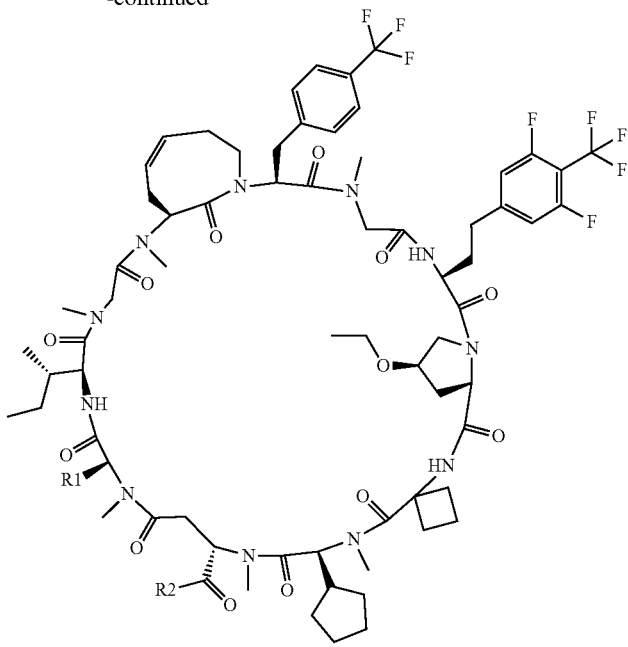

Using Compound aa386-resin as a raw material, peptide synthesis by the basic peptide synthesis method described in the present Examples was performed to give Compound PP1300-a. Using the resulting Compound PP1300-a (0.00574 mmol each), the intended compounds were obtained in the same manner as synthesis of Compound PP391 using the amines shown in Table 24 in place of 2-methoxy-N-methylethan-1-amine. LC/MS data is provided in Table 36.

TABLE 24

| Intended product | R1 | R2 | Amine | Yield | Yield |
|---|---|---|---|---|---|
| PP1300 | | | | 3.3 mg | 37% |
| PP1301 | | | | 3.1 mg | 35% |
| PP1302 | | | | 3.5 mg | 41% |
| PP1303 | | | | 2.0 mg | 23% |
| PP1304 | | | | 3.1 mg | 35% |

TABLE 24-continued

| Intended product | R1 | R2 | Amine | Yield | Yield |
|---|---|---|---|---|---|
| PP1305 | (isopropyl) | N(Et)(Et)- | Et-NH-Et | 2.8 mg | 31% |
| PP1306 | (isobutyl) | N(Et)(Et)- | Et-NH-Et | 2.8 mg | 32% |
| PP1307 | (cyclopropylmethyl) | N(Et)(Et)- | Et-NH-Et | 2.0 mg | 22% |
| PP1308 | (isopropylidene) | N(Et)(Et)- | Et-NH-Et | 3.4 mg | 39% |
| PP1309 | (2,2-difluoroethyl) | N(Et)(Et)- | Et-NH-Et | 2.4 mg | 27% |
| PP1310 | (n-butyl) | N(Et)(Et)- | Et-NH-Et | 2.8 mg | 32% |
| PP1311 | (isobutyl) | morpholinyl | morpholine | 2.6 mg | 28% |
| PP1312 | (cyclopropylmethyl) | morpholinyl | morpholine | 2.9 mg | 32% |
| PP1313 | (isopropylidene) | morpholinyl | morpholine | 4.3 mg | 48% |
| PP1314 | (isopropyl) | morpholinyl | morpholine | 4.3 mg | 48% |
| PP1315 | (n-butyl) | morpholinyl | morpholine | 3.3 mg | 36% |
| PP1316 | (n-propyl) | N(Et)(CH₂CH₂OMe)- | MeOCH₂CH₂-NH-Et | 3.5 mg | 39% |

TABLE 24-continued

| Intended product | R1 | R2 | Amine | Yield | Yield |
|---|---|---|---|---|---|
| PP1317 | isobutyl | N(CH2CH2OMe)(Et) | HN(Et)(CH2CH2OMe) | 3.0 mg | 33% |
| PP1318 | cyclopropylmethyl | N(CH2CH2OMe)(Et) | HN(Et)(CH2CH2OMe) | 3.1 mg | 34% |
| PP1319 | isopropyl | N(CH2CH2OMe)(Et) | HN(Et)(CH2CH2OMe) | 3.8 mg | 43% |
| PP1320 | 2,2-difluoroethyl | N(CH2CH2OMe)(Et) | HN(Et)(CH2CH2OMe) | 2.0 mg | 22% |
| PP1331 | n-butyl | N(CH2CH2OMe)(Et) | HN(Et)(CH2CH2OMe) | 3.4 mg | 38% |
| PP1387 | isobutyl | N(Me)(CH2CH2CH3) | HN(Me)(CH2CH2CH3) | 2.8 mg | 31% |
| PP1388 | cyclopropylmethyl | N(Me)(CH2CH2CH3) | HN(Me)(Et) | 2.0 mg | 22% |
| PP1389 | n-butyl | N(Me)(CH2CH2CH3) | HN(Me)(CH2CH2CH3) | 2.7 mg | 30% |

Synthesis of Compounds PP1321, PP1322, PP1323, PP1324, PP1325, PP1326, PP1327, PP1328, and PP1329
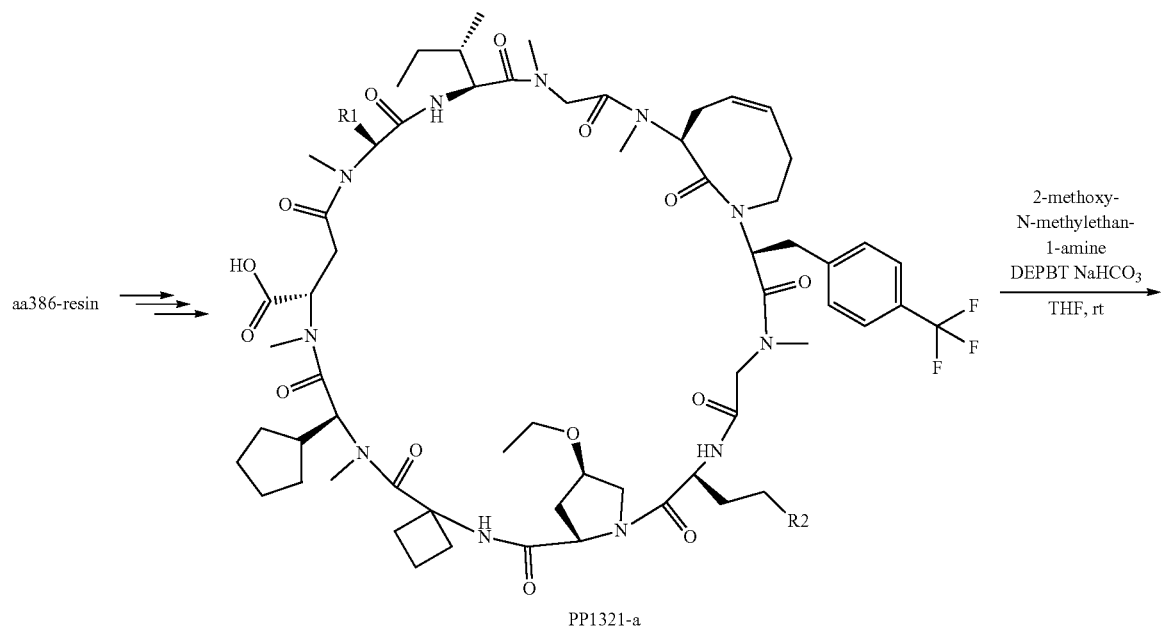
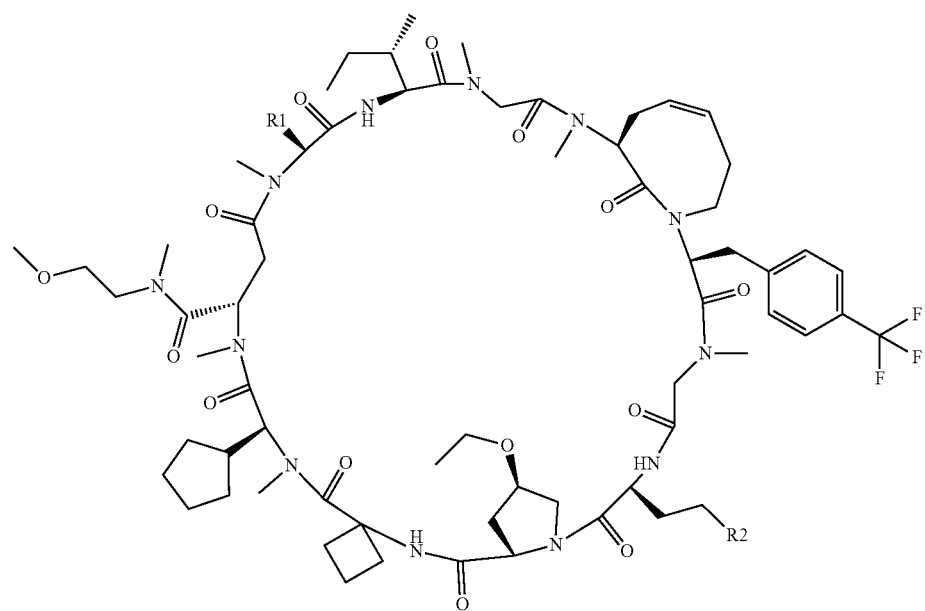

Using Compound aa386-resin as a raw material, peptide synthesis by the basic peptide synthesis method described in the present Examples was performed to give Compound PP1321-a. Using the resulting Compound PP1321-a (0.00574 mmol each), the intended compounds were obtained in the same manner as synthesis of Compound PP391. The intended products and yields are provided in Table 25. LC/MS data is provided in Table 36.

TABLE 25

| Intended product | R1 | R2 | Yield | Yield |
|---|---|---|---|---|
| PP1321 | propyl | 4-(difluoromethyl? OCF2)-3-methoxyphenyl | 4.2 mg | 47% |
| PP1322 | propyl | benzothiophen-5-yl | 3.6 mg | 42% |
| PP1323 | propyl | 3,4-dichlorophenyl | 3.2 mg | 37% |
| PP1324 | isobutyl | 4-(CF2)-3-methoxyphenyl | 3.0 mg | 33% |
| PP1325 | isobutyl | benzothiophen-5-yl | 2.6 mg | 29% |
| PP1326 | isobutyl | 3,4-dichlorophenyl | 3.8 mg | 43% |
| PP1327 | cyclopropylmethyl | 4-(CF2)-3-methoxyphenyl | 3.3 mg | 37% |
| PP1328 | cyclopropylmethyl | benzothiophen-5-yl | 2.8 mg | 32% |
| PP1329 | cyclopropylmethyl | 3,4-dichlorophenyl | 2.4 mg | 27% |

Synthesis of Compound PP1330

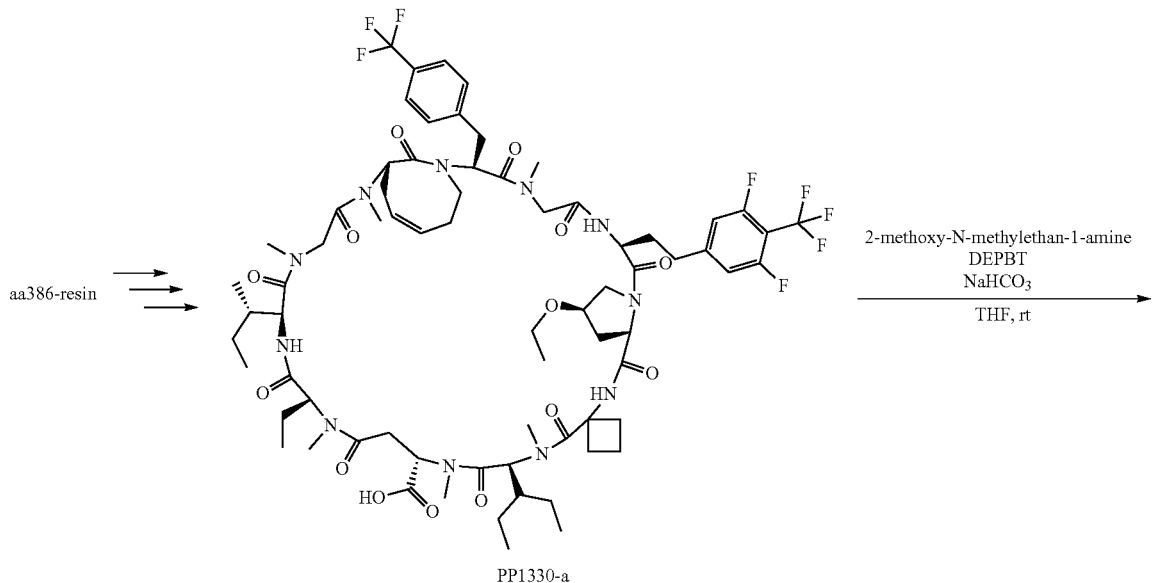

PP1330-a

-continued

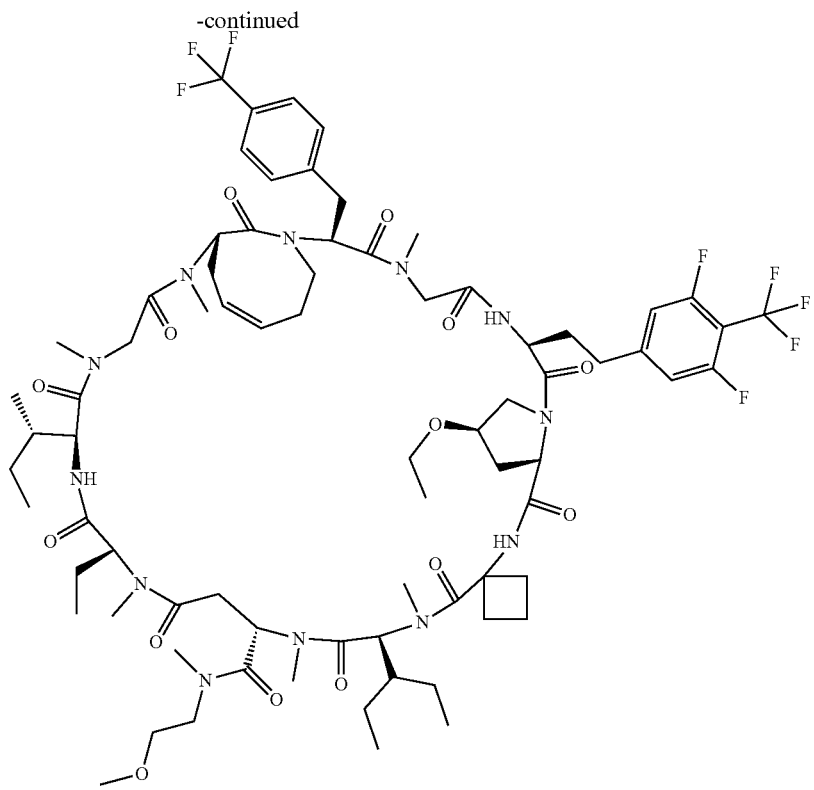

PP1330

Using Compound aa386-resin as a raw material, peptide synthesis by the basic peptide synthesis method described in the present Examples was performed to give Compound PP1330-a. Using the resulting Compound PP1330-a (0.00574 mmol), the intended compound (1.3 mg, 14%) was obtained in the same manner as synthesis of Compound PP391. LC/MS data is provided in Table 36.

Synthesis of Compounds PP1537 and PP1538

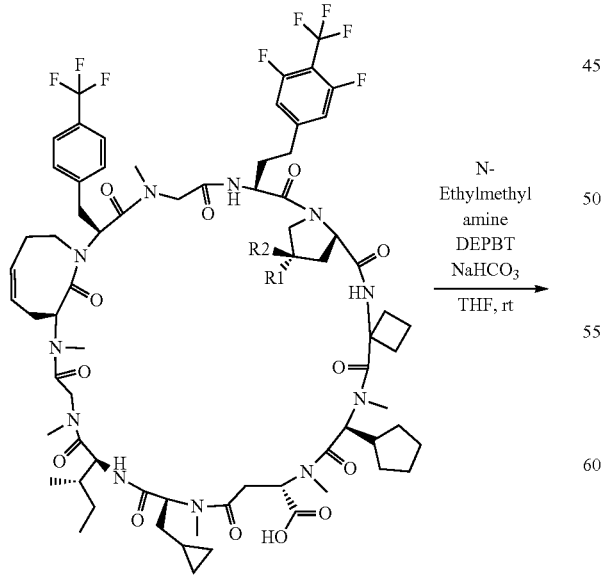

R1 = Me, R2 = H: PP1537-a
R1 = R2 = F: PP1538-a

N-Ethylmethylamine
DEPBT
NaHCO₃
THF, rt

-continued

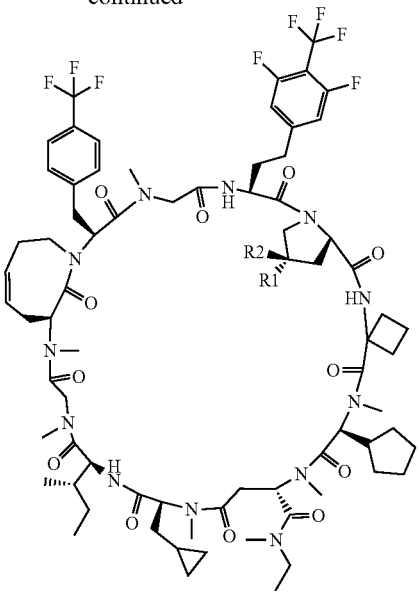

R1 = Me, R2 = H: PP1537
R1 = R2 = F: PP1538

Using Compound aa386-resin as a raw material, peptide synthesis by the basic peptide synthesis method described in the present Examples was performed to give Compounds PP1537-a and PP1538-a. Using the resulting Compounds PP1537-a and PP1538-a (8.8 mg each), Compounds PP1537 (3.2 mg, 35%) and PP1538 (3.9 mg, 42%) were obtained in the same manner as synthesis of Compound PP391 using N-ethylmethylamine in place of 2-methoxy-N-methylethan-1-amine. LC/MS data is provided in Table 36.

Synthesis of Compounds PP1552 and PP1553

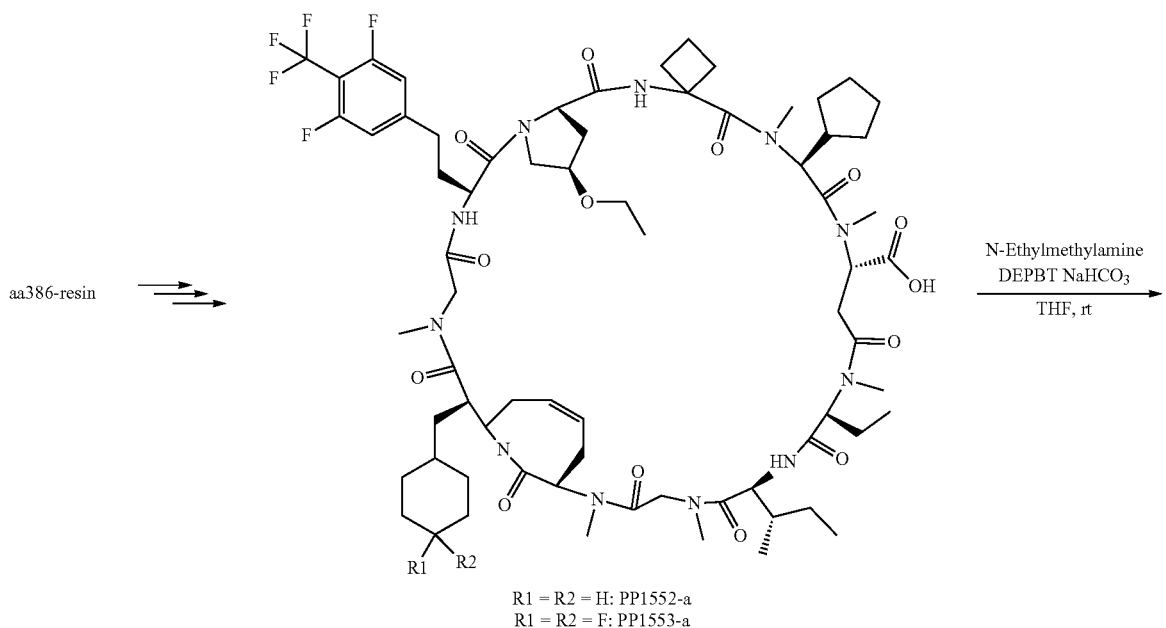

R1 = R2 = H: PP1552-a
R1 = R2 = F: PP1553-a

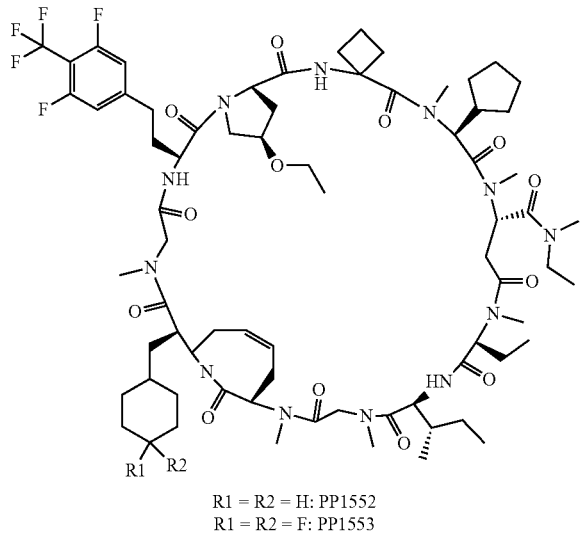

R1 = R2 = H: PP1552
R1 = R2 = F: PP1553

Using Compound aa386-resin as a raw material, peptide synthesis by the basic peptide synthesis method described in the present Examples was performed to give Compounds PP1552-a and PP1553-a. Using the resulting Compounds PP1552-a (3.8 mg) and PP1553-a (4.5 mg), Compounds PP1552 (1.7 mg, 44%) and PP1553 (1.9 mg, 41%) were obtained in the same manner as synthesis of Compound PP391 using N-ethylmethylamine in place of 2-methoxy-N-methylethan-1-amine. LC/MS data is provided in Table 36.

Synthesis of Compounds PP1554 and PP1557

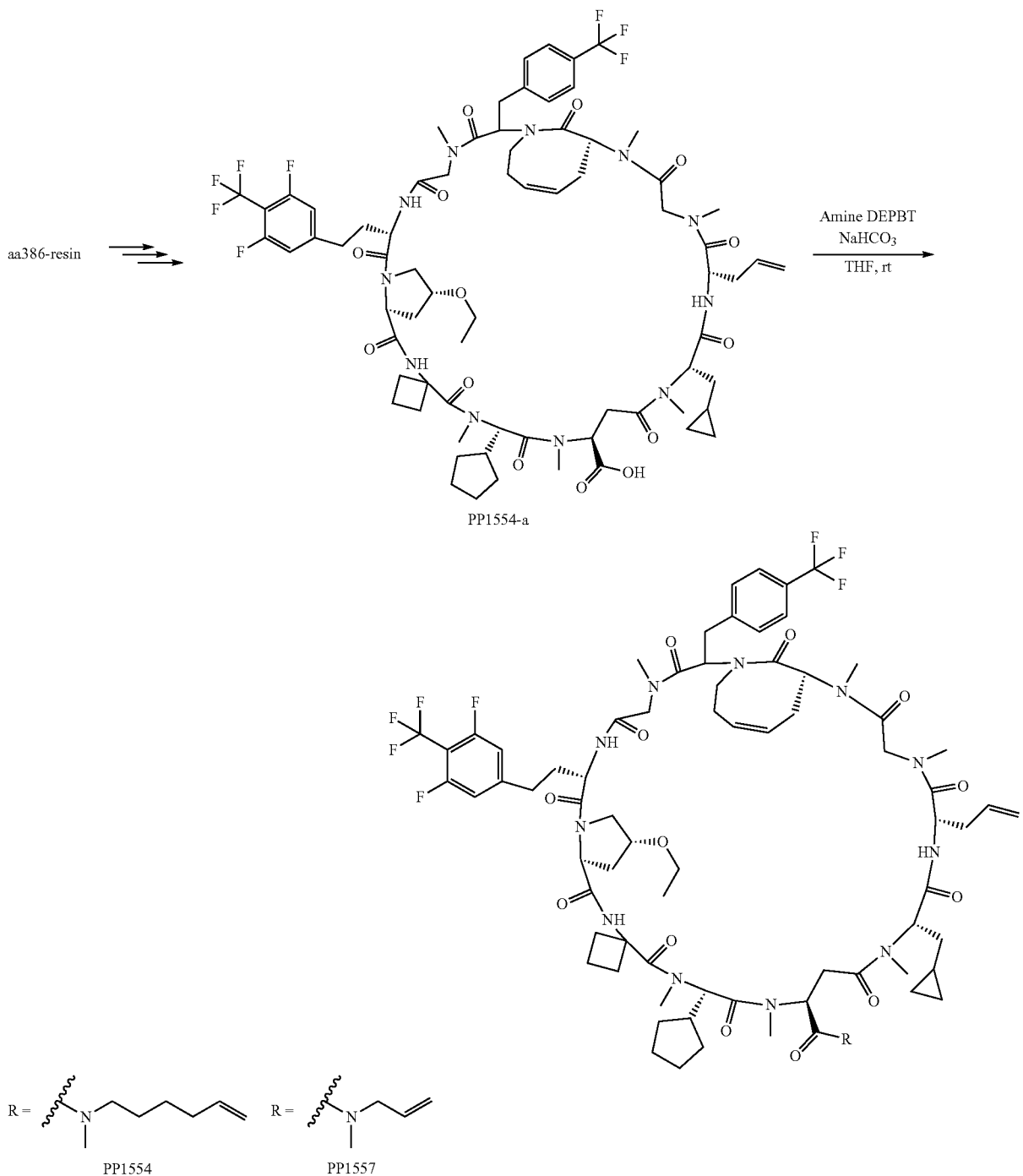

Using Compound aa386-resin as a raw material, peptide synthesis by the basic peptide synthesis method described in the present Examples was performed to give Compound PP1554-a. Using the resulting Compound PP1554-a (12.6 mg each), Compounds PP1554 (5.9 mg, 44%) and PP1557 (6.7 mg, 51%) were obtained in the same manner as synthesis of Compound PP391 using N-methylhex-5-ene-1-amine or N-methylprop-2-ene-1-amine in place of 2-methoxy-N-methylethan-1-amine. LC/MS data is provided in Table 36.

1-6-4. Peptide Synthesis Via N-Alkylation by Mitsunobu Reaction on Resin
Synthesis of Compound PP55
PP55 was synthesized according to the following scheme.
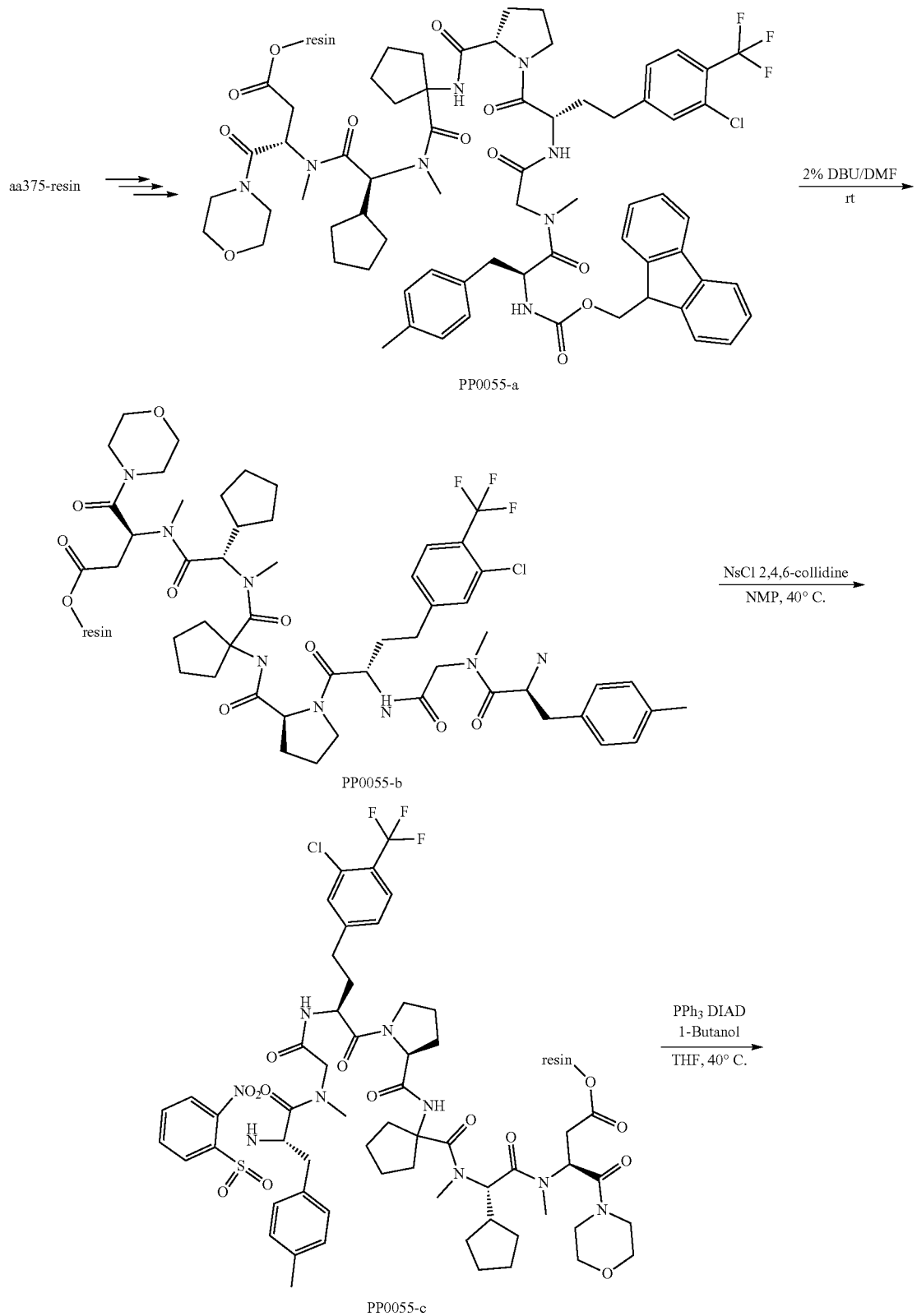

-continued
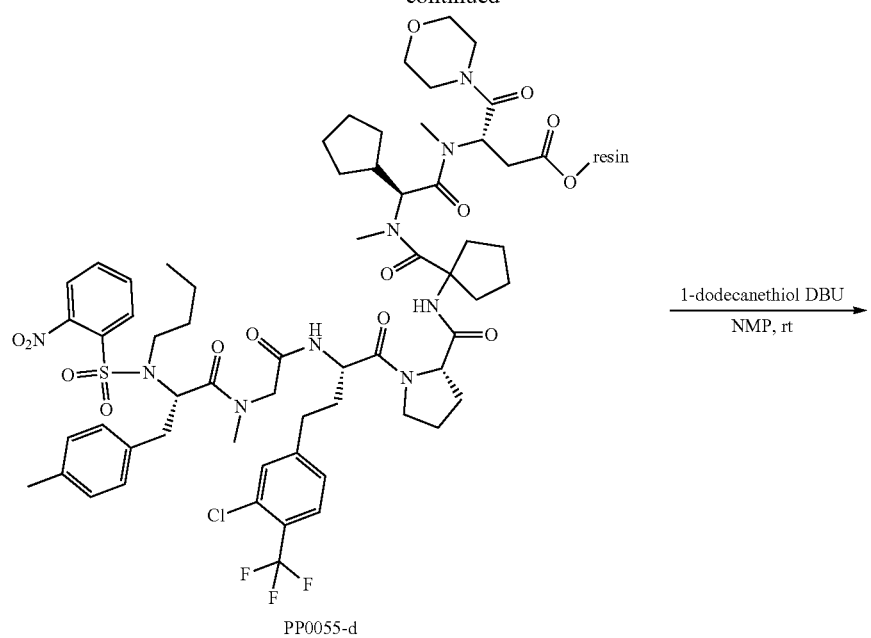
PP0055-d
1-dodecanethiol DBU
―――――――――→
NMP, rt
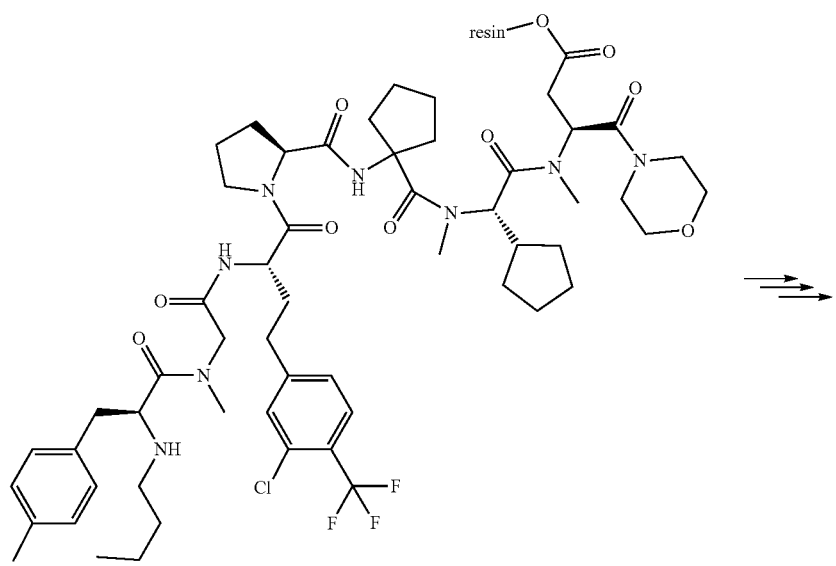
PP0055-e -continued

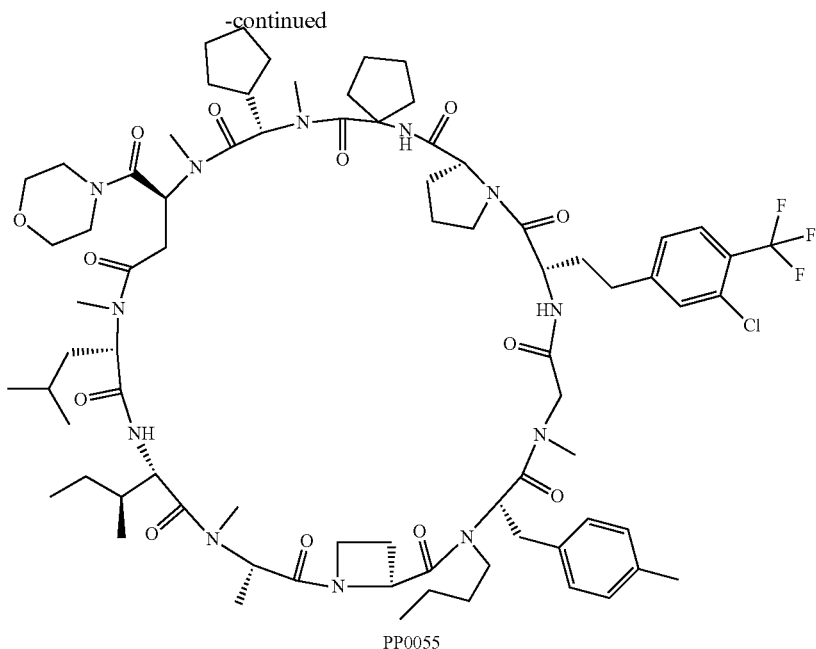

PP0055

Using Compound aa375-resin as a raw material, peptide synthesis by the basic peptide synthesis method described in the present Examples was performed to give resin-supported Compound PP55-a. Cleaving from the resin was performed with TFE/DCM (1/1) using a small amount of resin-supported Compound PP55-a, and the structure was verified by LC/MS.

LCMS (ESI) m/z=1282 (M+H)+
Retention time: 1.02 min (Analytical condition SQDFA05)

Compound PP55-a-resin (100 mg, 0.384 mmol/g, 0.0384 mmol) and DCM (1 mL) were added to a filter-equipped reaction vessel to swell the resin. After DCM was removed, the resin was washed 4 times with DMF (1 mL). A DMF solution (2% v/v, 0.600 mL) of DBU was added, the mixture was shaken for 15 minutes at room temperature, and then the reaction solution was removed. The resin was washed 6 times with NMP (1 mL) to give resin-supported Compound PP55-b. Cleaving from the resin was performed with TFE/DCM (1/1) using a small amount of resin-supported Compound PP55-b, and the structure was verified by LC/MS.

LCMS (ESI) m/z=1060 (M+H)+
Retention time: 0.62 min (Analytical condition SQDFA05)

An NMP solution (1 ml.) of nosyl chloride (34 mg, 0).154 mmol) and 2,4,6-cholidine (0.051 mL., 0).384 mmol) were added thereto, and the mixture was shaken at 40° C. for 1 hour. Then, the reaction solution was removed, and the resin was washed 4 times with NMP (1 ml.) and washed 4 times with DCM (1 mL) to give resin-supported Compound PP55-c. Cleaving from the resin was performed with THE/DCM (1/1) using a small amount of resin-supported Compound PP55-c, and the structure was verified by LC/MS.

LCMS (ESI) m/z=1245 (M+H)+
Retention time: 0.89 min (Analytical condition SQDFA05)

DCM (1 ml.) was added thereto for swelling. After DCM was removed, the resin was washed twice with DCM (1 mL.) and then 4 times with THE (1 ml.). A THE solution (1 ml.) obtained by dissolving triphenylphosphine (50) mg, 0.192 mmol), DIAD (0.038 mL, 0.192 mmol), and 1-butanol (0.035 ml., 0).384 mmol) was added, the mixture was shaken at 40° C. for 30 minutes, and then the reaction solution was removed. The resin was washed 4 times with THF (1 mL.) and washed 4 times with DCM (1 ml.) to give resin-supported Compound PP55-d. Cleaving from the resin was performed with THE/DCM (1/1) using a small amount of resin-supported Compound PP55-d, and the structure was verified by LC/MS.

LCMS (ESI) m/z=1301 (M+H)+
Retention time: 1.01 min (Analytical condition SQDFA05)

DCM (1 ml.) was added thereto for swelling. After DCM was removed, the resin was washed 4 times with NMP (1 mL.). An NMP solution (0.200 mL) of DBU (0.020 mL, 0.134 mmol) and an NMP solution (0).250 mL.) of 1-dodecanethiol (0.063 mL., 0.262 mmol) were added, and the mixture was shaken at room temperature for 1 hour. Then, the reaction solution was removed, and the resin was washed 4 times with NMP (1 mL.). An NMP solution (0.200 mL.) of DBU (0.020 mL., 0.134 mmol) and an NMP solution (0).250 mL) of 1-dodecanethiol (0).063 mL, 0).262 mmol) were added, and the mixture was shaken at room temperature for 13 hours. Then, the reaction solution was removed, and the resin was washed 4 times with NMP (1 mL.). An NMP solution (0.200 mL) of DBU (0.020 mL, 0.134 mmol) and an NMP solution (0).250 ml) of 1-dodecanethiol (0.063 ml., 0).262 mmol) were added, and the mixture was shaken at room temperature for 1 hour. Then, the reaction solution was removed, and the resin was washed 4 times with NMP (1 mL) and washed 4 times with DCM (1 mL) to give resin-supported Compound PP55-e. Cleaving from the resin was performed with TFE/DCM (1/1) using a small amount of resin-supported Compound PP55-e, and the structure was verified by LC/MS.

LCMS (ESI) m/z=1116 (M+H)+
Retention time: 0.66 min (Analytical condition SQDFA05)

Subsequent steps of peptide elongation, cleaving from resin, cyclization, and purification were performed according to the basic route to give Compound PP0055. LC/MS data is provided in Table 36.

Synthesis of Compound PP52, Compound PP56, Compound PP57, Compound PP59, Compound PP062, Compound PP063, Compound PP064, Compound PP065, Compound PP083, Compound PP084, Compound PP085, Compound PP086, Compound PP087, Compound PP088, Compound PP089, Compound PP90, Compound PP91, Compound PP92, Compound PP93, Compound PP94, Compound PP95, Compound PP96, Compound PP97, Compound PP98, Compound PP99, Compound PP100, Compound PP101, Compound PP102, Compound PP103, Compound PP104, Compound PP105, Compound PP134, Compound PP135, Compound PP139, and Compound PP140

Using resin-supported Compound PP55-c, the reaction was carried out in the same manner as synthesis of Compound PP55-d using the alcohols shown in Table 26 in place of 1-butanol. Moreover, the Ns group was deprotected in the same manner as synthesis of Compound PP55-e, and subsequent steps of peptide elongation, cleaving from resin, cyclization, and purification were carried out according to the basic route to give the intended compounds. LC/MS data is provided in Table 36.

TABLE 26

| Intended product | Alcohol |
| --- | --- |
| Compound PP0052 | 1-Propanol |
| Compound PP0056 | Isobutanol |
| Compound PP0057 | Cyclopropylmethanol |
| Compound PP0059 | 1-Propanol |

TABLE 26-continued

| Intended product | Alcohol |
| --- | --- |
| Compound PP0062 | 1-Butanol |
| Compound PP0063 | Isobutanol |
| Compound PP0064 | Cyclopropylmethanol |
| Compound PP0065 | 1-Propanol |
| Compound PP0083 | Cyclobutylmethanol |
| Compound PP0084 | Cyclopentylmethanol |
| Compound PP0085 | Cyclohexylmethanol |
| Compound PP0086 | 3-Methylbutan-1-ol |
| Compound PP0087 | 4-Methylpentan-1-ol |
| Compound PP0088 | 2-Propen-1-ol |
| Compound PP0089 | 3-Buten-1-ol |
| Compound PP0090 | 2-Propyn-1-ol |
| Compound PP0091 | 3,3,3-Trifluoro-1-propanol |
| Compound PP0092 | 2-Methoxyethanol |
| Compound PP0093 | 3-Methoxy-1-propanol |
| Compound PP0094 | 2-Propanol |
| Compound PP0095 | Cyclobutylmethanol |
| Compound PP0096 | Cyclopentylmethanol |
| Compound PP0097 | Cyclohexylmethanol |
| Compound PP0098 | 3-Methylbutan-1-ol |
| Compound PP0099 | 4-Methylpentan-1-ol |
| Compound PP0100 | 2-Propen-1-ol |
| Compound PP0101 | 3-Buten-1-ol |
| Compound PP0102 | 2-Propyn-1-ol |
| Compound PP0103 | 3,3,3-Trifluoro-1-propanol |
| Compound PP0104 | 2-Methoxyethanol |
| Compound PP0105 | 3-Methoxy-1-propanol |
| Compound PP0134 | 1-Propanol |
| Compound PP0135 | 1-Propanol |
| Compound PP0139 | 2-Propen-1-ol |
| Compound PP0140 | 3-Buten-1-ol |

Synthesis of Compound PP58, Compound PP066, and Compound PP069

Compound PP58, Compound PP066, and Compound PP069 were synthesized according to the following scheme.

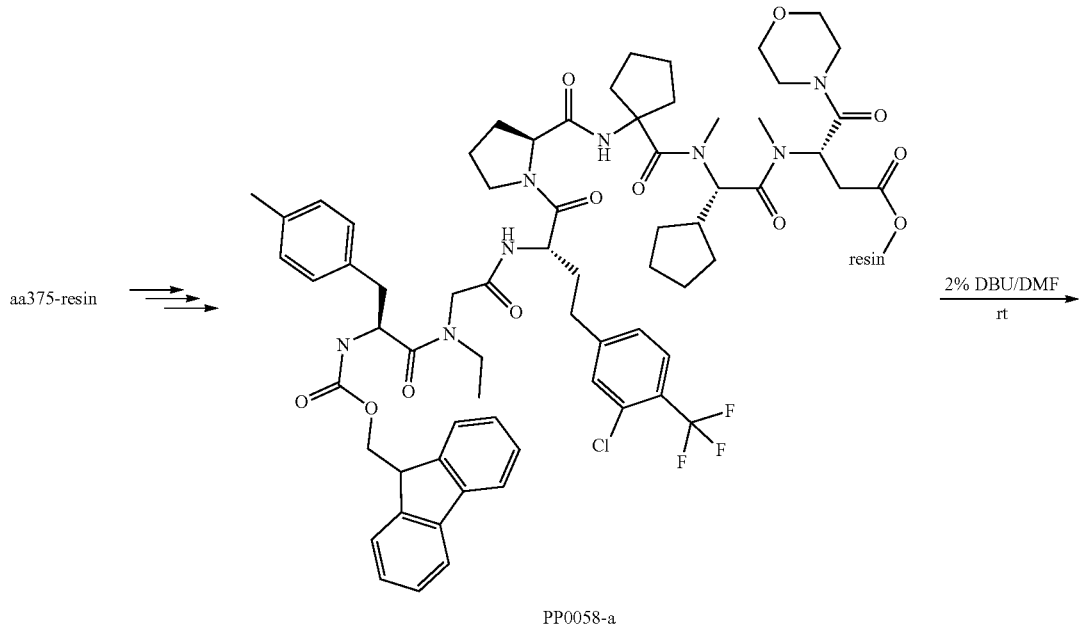

PP0058-a

-continued
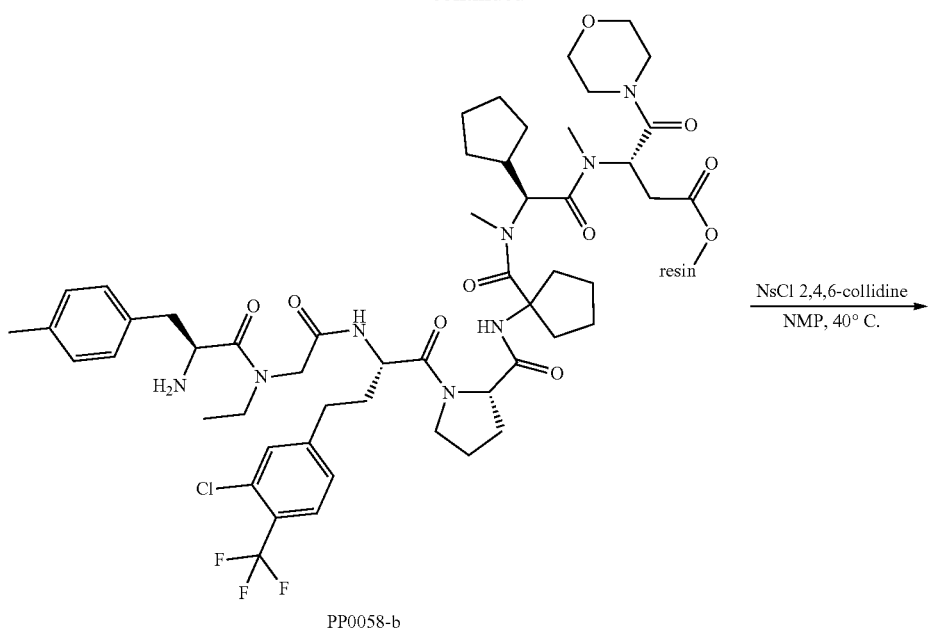
PP0058-b
NsCl 2,4,6-collidine
―――――→
NMP, 40° C.
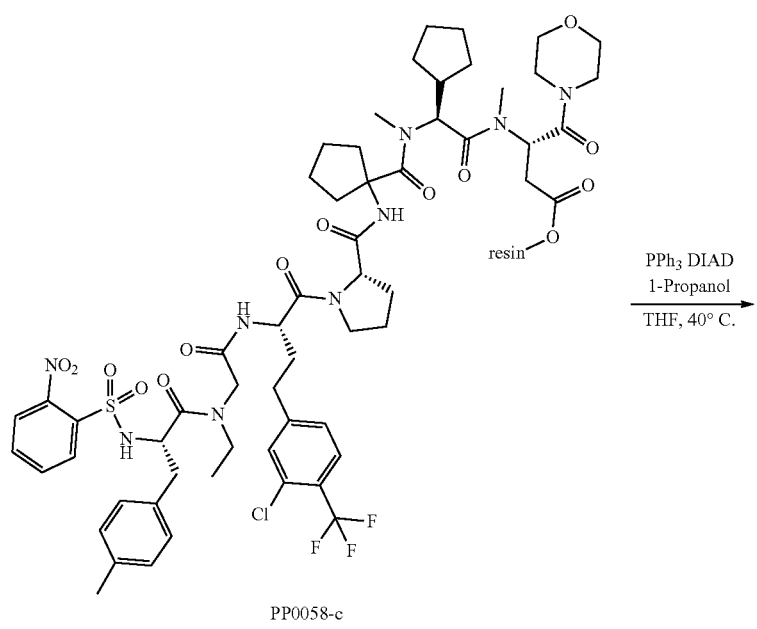
PP0058-c
PPh₃ DIAD
1-Propanol
―――――→
THF, 40° C.

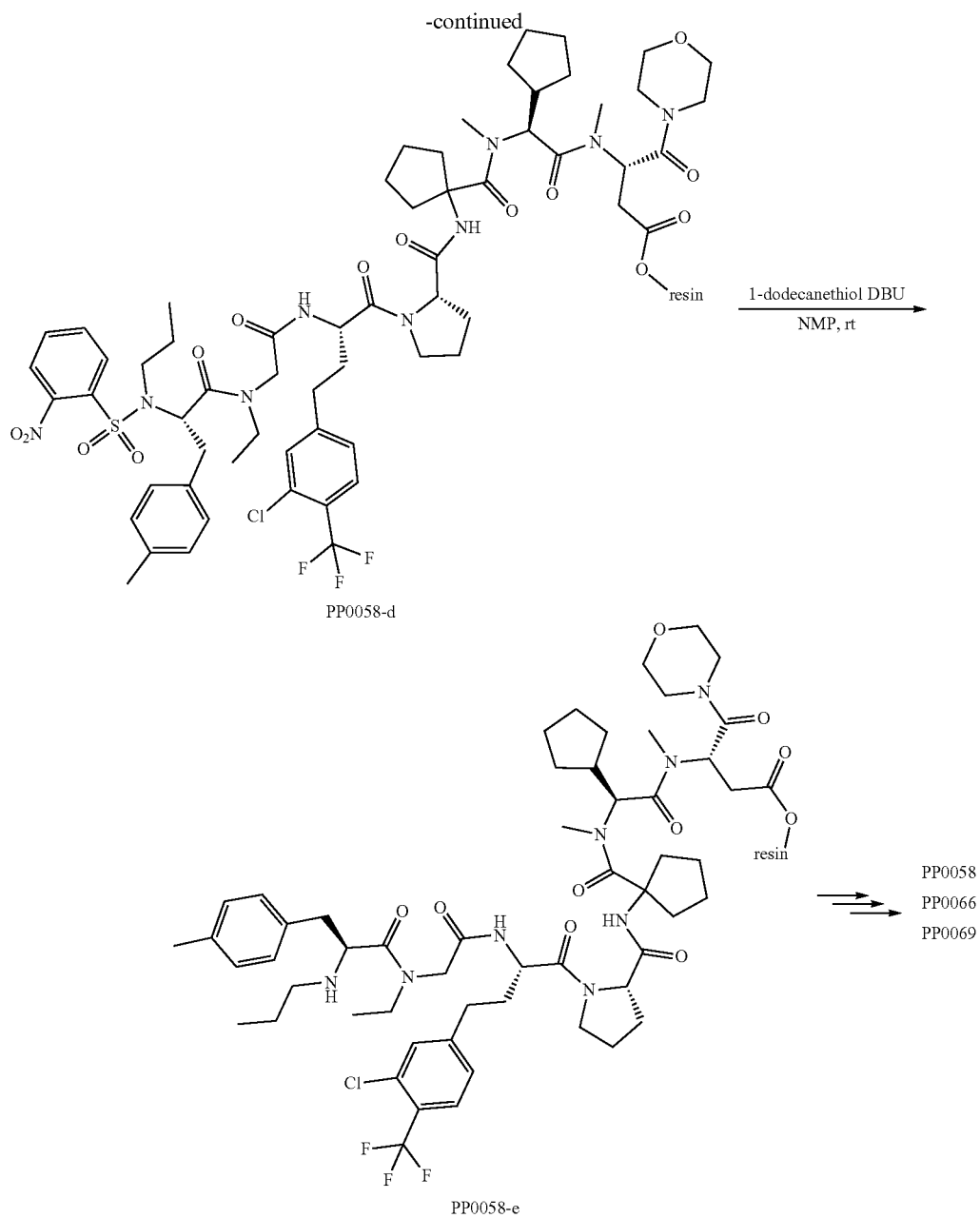

PP0058-d

PP0058-e

Using Compound aa375-resin as a raw material, peptide synthesis by the basic peptide synthesis method described in the present Examples was performed to give resin-supported Compound PP58-a. After resin-supported Compound PP58-b was obtained in the same manner as synthesis of Compound PP55-b, resin-supported Compound PP58-c was obtained in the same manner as synthesis of Compound PP55-c. After resin-supported Compound PP58-d was obtained in the same manner as synthesis of Compound PP55-d using 1-propanol in place of 1-butanol, resin-supported Compound PP58-e was obtained in the same manner as synthesis of Compound PP55-e. Subsequent steps of peptide elongation, cleaving from resin, cyclization, and purification were performed according to the basic route to give the intended compounds. LC/MS data is provided in Table 36.

Synthesis of Compound PP0053, Compound PP0060, Compound PP0106, Compound PP0107, Compound PP0108, Compound PP0109, Compound PP0110, Compound PP0112, Compound PP0113, Compound PP0114, Compound PP0115, Compound PP0116, Compound PP0117, Compound PP0118, Compound PP0119, Compound PP0120, Compound PP0121, Compound PP0122, Compound PP0123, Compound PP0124, Compound PP0126, Compound PP0127, Compound PP0128, Compound PP0129, Compound PP0130, Compound PP0131, Compound PP0132, and Compound PP0133

Compound PP0053, Compound PP0060, Compound PP0106, Compound PP0107, Compound PP0108, Compound PP0109, Compound PP0110, Compound PP0112, Compound PP0113, Compound PP0114, Compound PP0115, Compound PP0116, Compound PP0117, Compound PP0118, Compound PP0119, Compound PP0120, Compound PP0121, Compound PP0122, Compound PP0123, Compound PP0124, Compound PP0126, Compound PP0127, Compound PP0128, Compound PP0129, Compound PP0130, Compound PP0131, Compound PP0132, and Compound PP0133 were synthesized according to the following scheme.
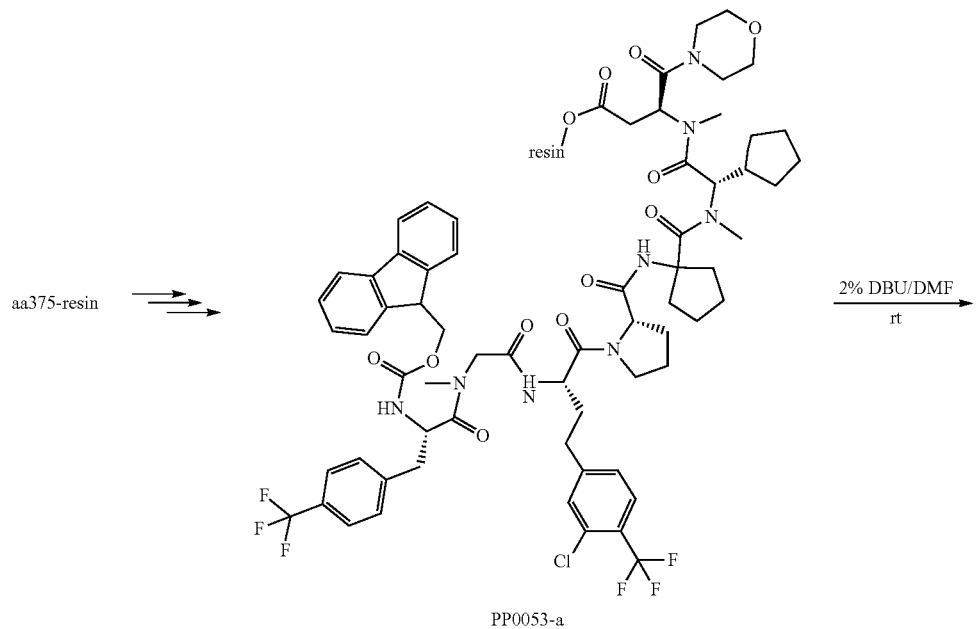
PP0053-a
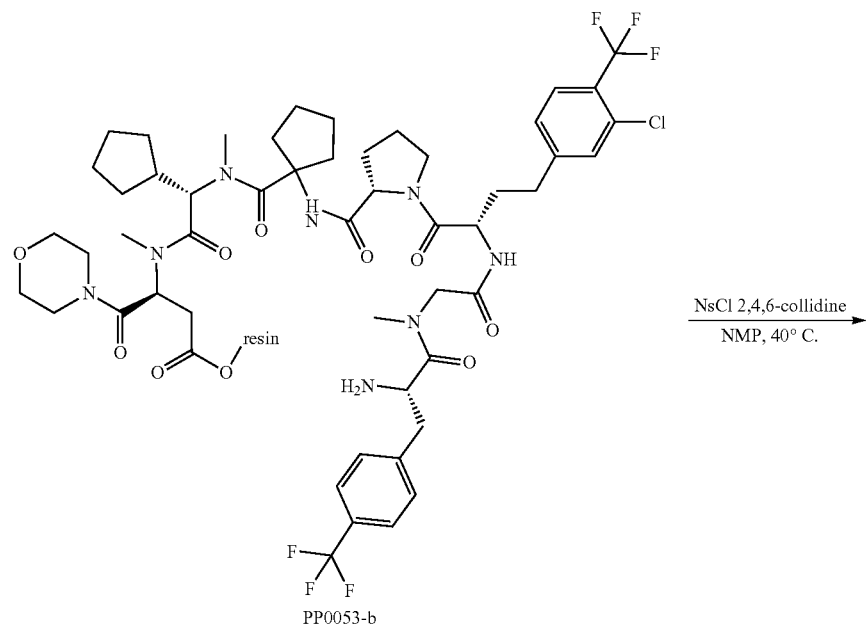
PP0053-b

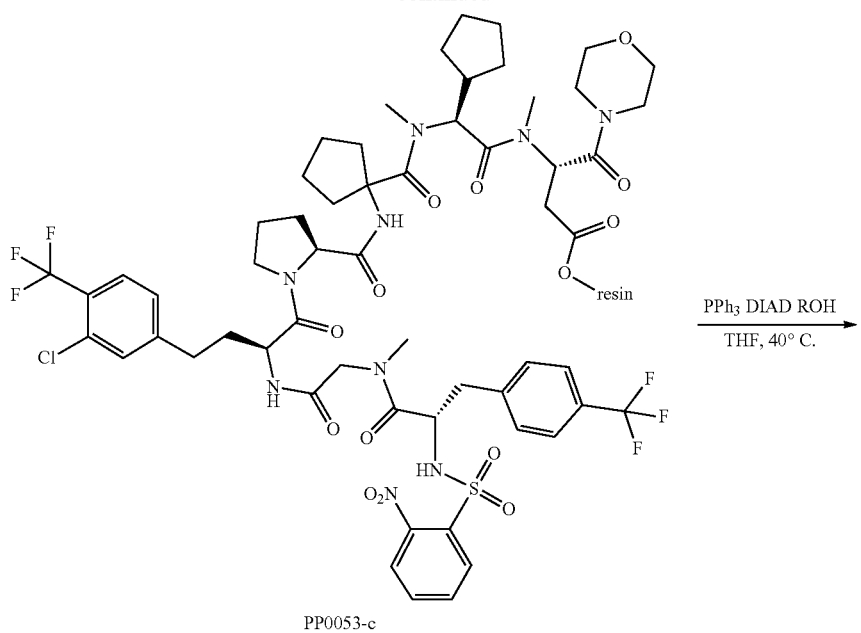
PP0053-c
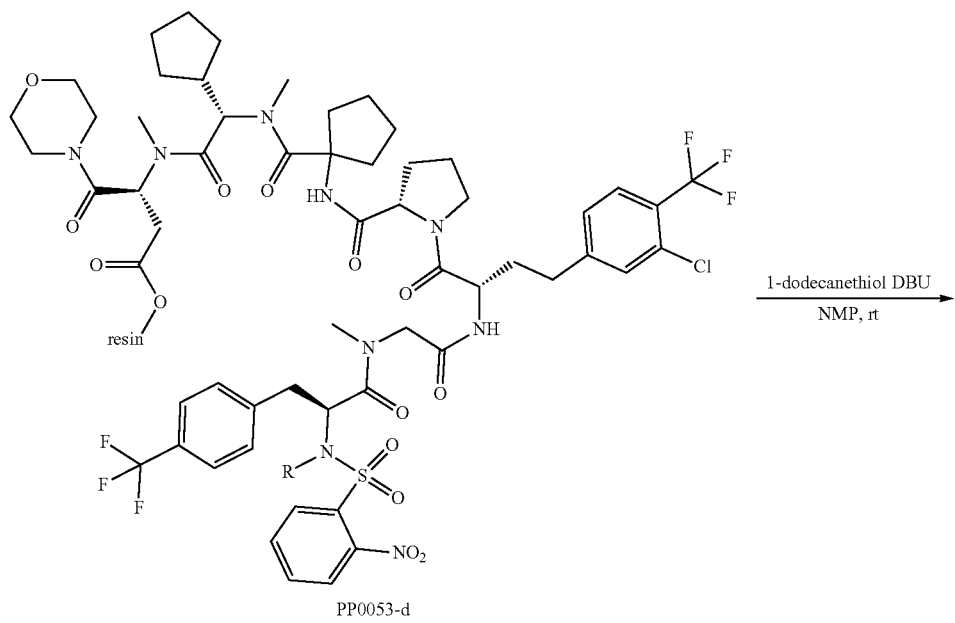
PP0053-d

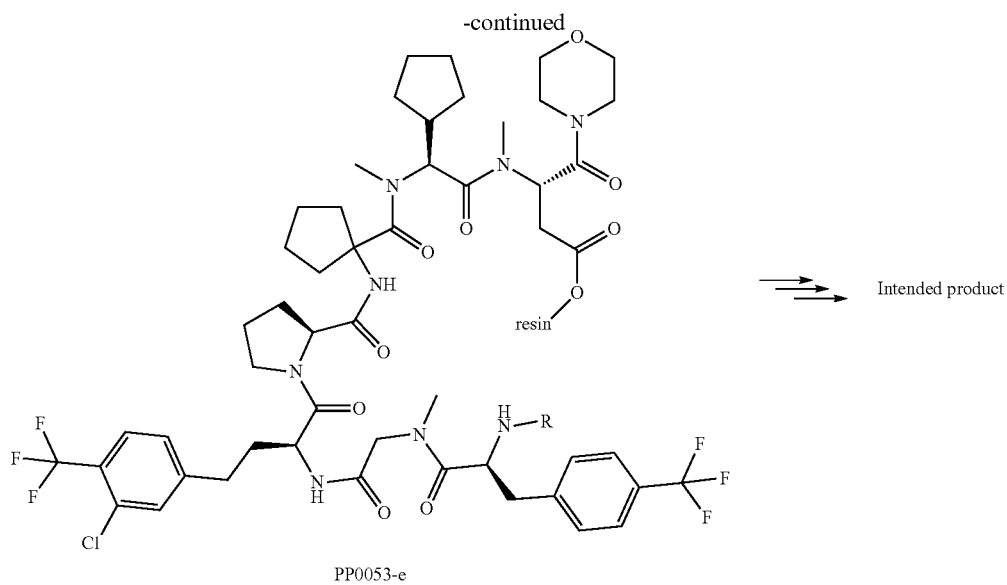

PP0053-e

→→ Intended product

Using Compound aa375-resin as a raw material, peptide synthesis by the basic peptide synthesis method described in the present Examples was performed to give resin-supported Compound PP53-a. After resin-supported Compound PP53-b was obtained in the same manner as synthesis of Compound PP55-b, resin-supported Compound PP53-c was obtained in the same manner as synthesis of Compound PP55-c. After resin-supported Compound PP53-d was obtained in the same manner as synthesis of Compound PP55-d using the alcohols shown in Table 27 in place of 1-butanol, resin-supported Compound PP53-e was obtained in the same manner as synthesis of Compound PP55-e. Subsequent steps of peptide elongation, cleaving from resin, cyclization, and purification were performed according to the basic route to give the intended compounds. LC/MS data is provided in Table 36.

TABLE 27

| Intended product | Alcohol |
| --- | --- |
| Compound PP0053 | 1-Propanol |
| Compound PP0060 | 1-Propanol |
| Compound PP0106 | 1-Butanol |
| Compound PP0107 | Isobutanol |
| Compound PP0108 | Cyclopropylmethanol |
| Compound PP0109 | Cyclobutylmethanol |
| Compound PP0110 | Cyclopentylmethanol |
| Compound PP0112 | 3-Methylbutan-1-ol |
| Compound PP0113 | 4-Methylpentan-1-ol |
| Compound PP0114 | 2-Propen-1-ol |

TABLE 27-continued

| Intended product | Alcohol |
| --- | --- |
| Compound PP0115 | 3-Buten-1-ol |
| Compound PP0116 | 2-Propyn-1-ol |
| Compound PP0117 | 3,3,3-Trifluoro-1-propanol |
| Compound PP0118 | 2-Methoxyethanol |
| Compound PP0119 | 3-Methoxy-1-propanol |
| Compound PP0120 | 1-Butanol |
| Compound PP0121 | Isobutanol |
| Compound PP0122 | Cyclopropylmethanol |
| Compound PP0123 | Cyclobutylmethanol |
| Compound PP0124 | Cyclopentylmethanol |
| Compound PP0126 | 3-Methylbutan-1-ol |
| Compound PP0127 | 4-Methylpentan-1-ol |
| Compound PP0128 | 2-Propen-1-ol |
| Compound PP0129 | 3-Buten-1-ol |
| Compound PP0130 | 2-Propyn-1-ol |
| Compound PP0131 | 3,3,3-Trifluoro-1-propanol |
| Compound PP0132 | 2-Methoxyethanol |
| Compound PP0133 | 3-Methoxy-1-propanol |

Synthesis of Compound PP54 and Compound PP061

Compound PP54 and Compound PP061 were synthesized according to the following scheme.

631
aa375-resin ⟶⟶ 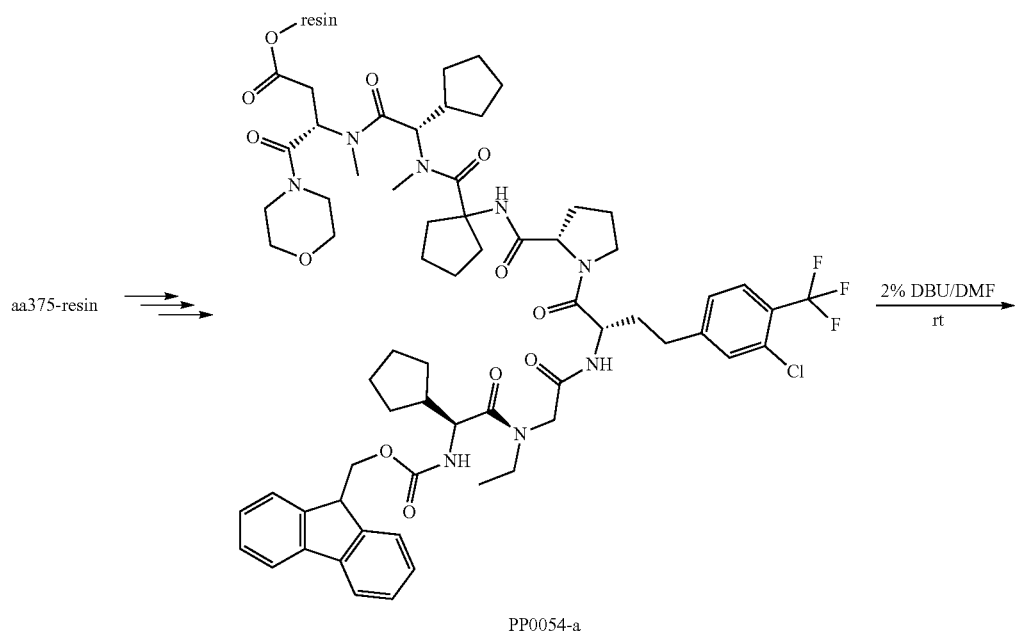
PP0054-a
2% DBU/DMF
rt
632
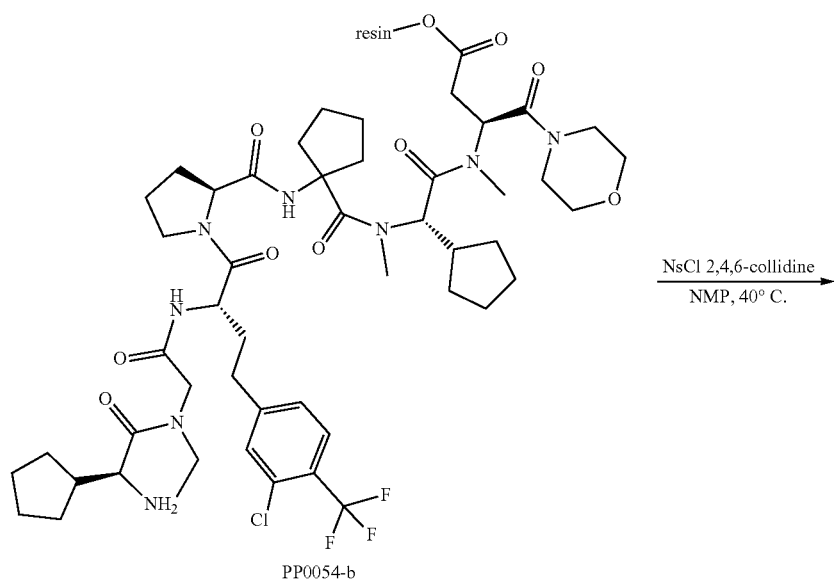
PP0054-b
NsCl 2,4,6-collidine
NMP, 40° C.

-continued
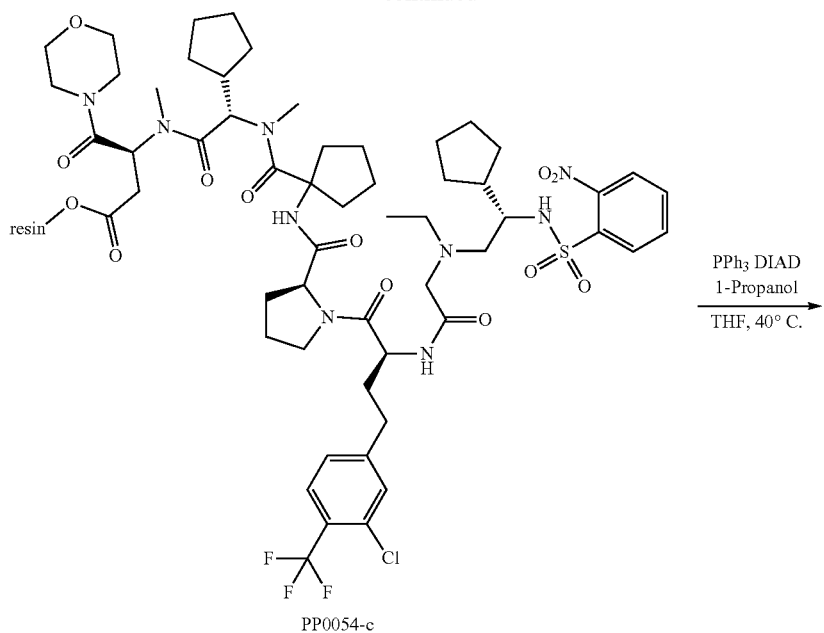
PP0054-c
PPh₃ DIAD
1-Propanol
―――――――→
THF, 40° C.
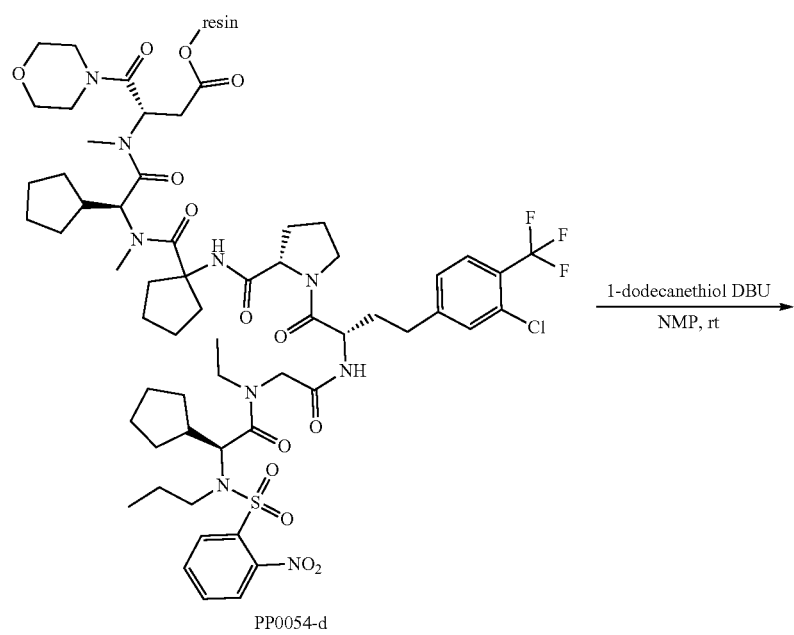
PP0054-d
1-dodecanethiol DBU
―――――――→
NMP, rt

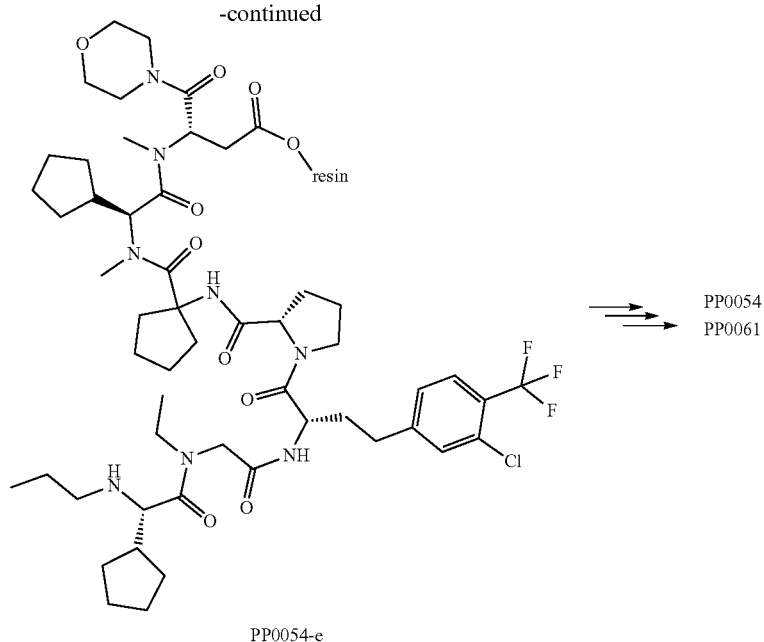

PP0054-e

→ PP0054
→→ PP0061

Using Compound aa375-resin as a raw material, peptide synthesis by the basic peptide synthesis method described in the present Examples was performed to give resin-supported Compound PP54-a. After resin-supported Compound PP54-b was obtained in the same manner as synthesis of Compound PP55-b, resin-supported Compound PP54-c was obtained in the same manner as synthesis of Compound PP55-c. After resin-supported Compound PP54-d was obtained in the same manner as synthesis of Compound PP55-d using 1-propanol in place of 1-butanol, resin-supported Compound PP54-e was obtained in the same manner as synthesis of Compound PP55-e. Subsequent steps of peptide elongation, cleaving from resin, cyclization, and purification were performed according to the basic route to give the intended compounds. LC/MS data is provided in Table 36.

Synthesis of Compound PP136 and Compound PP137

Compound PP136 and Compound PP137 were synthesized according to the following scheme.

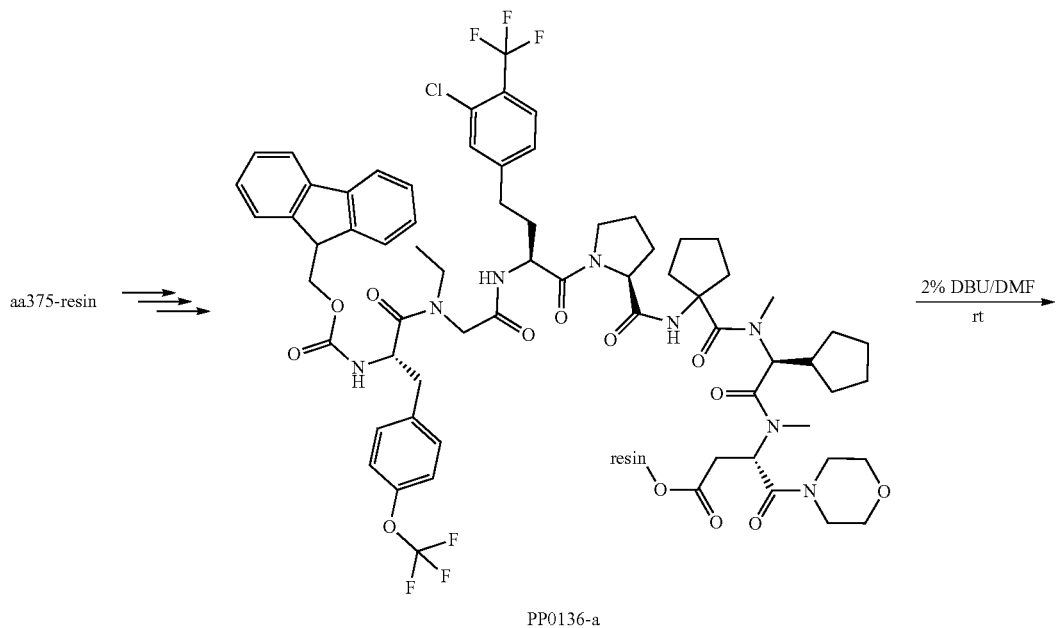

PP0136-a

-continued
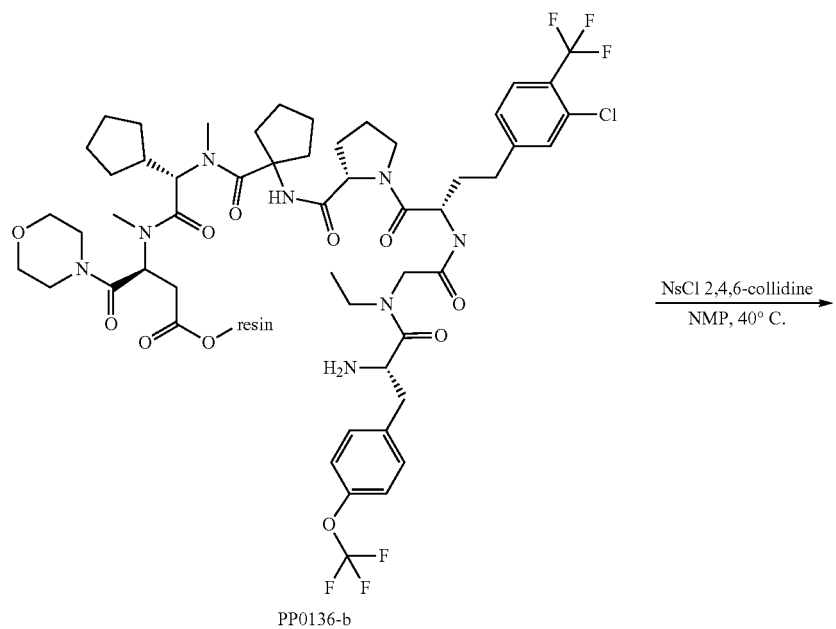
PP0136-b
NsCl 2,4,6-collidine
NMP, 40° C.
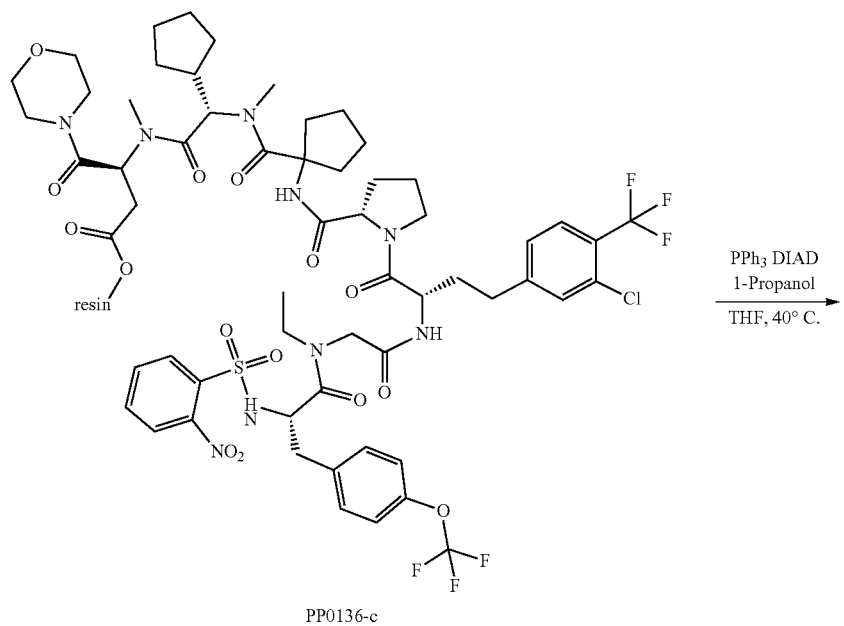
PP0136-c
PPh₃ DIAD
1-Propanol
THF, 40° C.

-continued

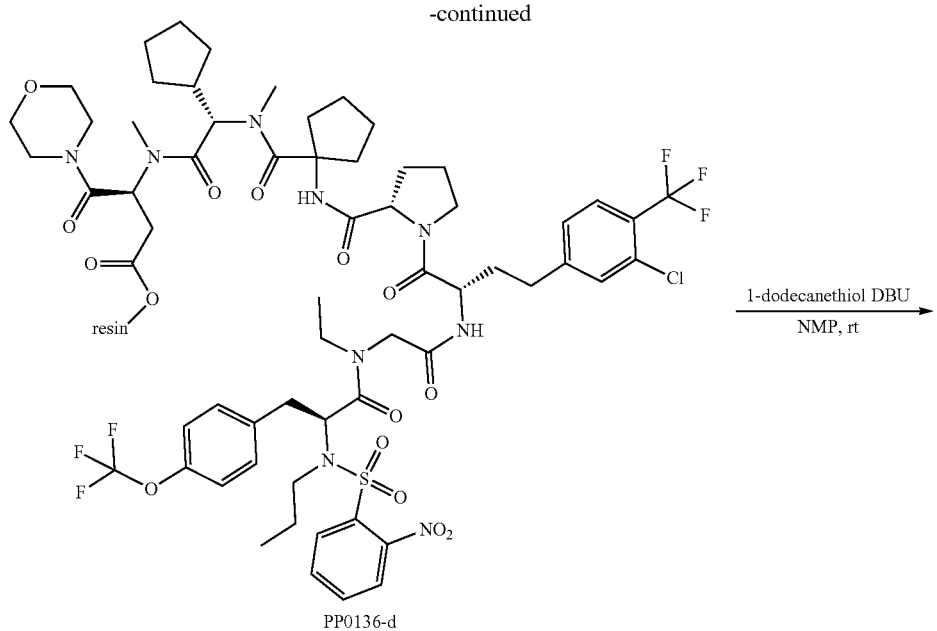

PP0136-d

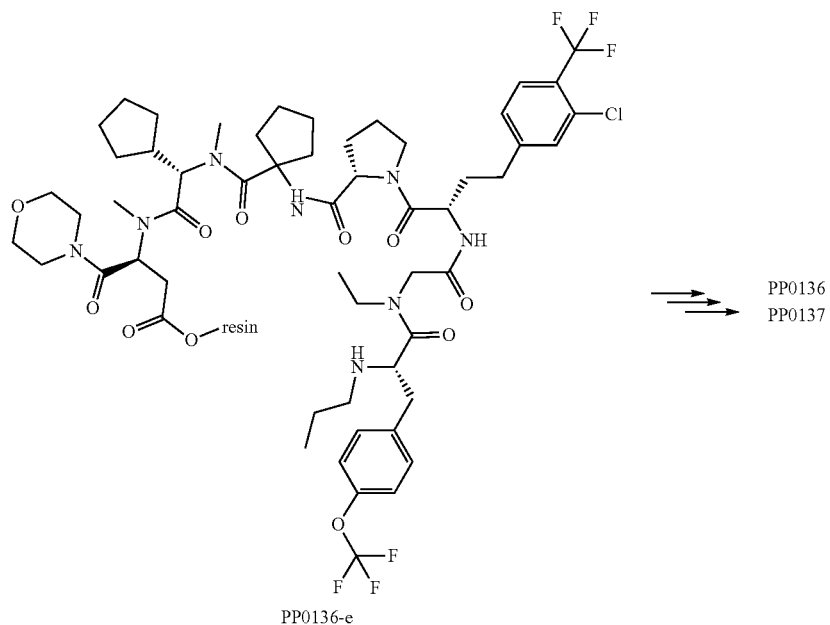

PP0136-e

Using Compound aa375-resin as a raw material, peptide synthesis by the basic peptide synthesis method described in the present Examples was performed to give resin-supported Compound PP136-a. After resin-supported Compound PP136-b was obtained in the same manner as synthesis of Compound PP55-b, resin-supported Compound PP136-c was obtained in the same manner as synthesis of Compound PP55-c. After resin-supported Compound PP136-d was obtained in the same manner as synthesis of Compound PP55-d using 1-propanol in place of 1-butanol, resin-supported Compound PP136-e was obtained in the same manner as synthesis of Compound PP55-e. Subsequent steps of peptide elongation, cleaving from resin, cyclization, and purification were performed according to the basic route to give the intended compounds. LC/MS data is provided in Table 36.

Synthesis of Compound PP0210, Compound PP0211, Compound PP0215, and Compound PP216

Compound PP0210, Compound PP0211, Compound PP0215, and Compound PP0216 were synthesized according to the following scheme.

aa375-resin 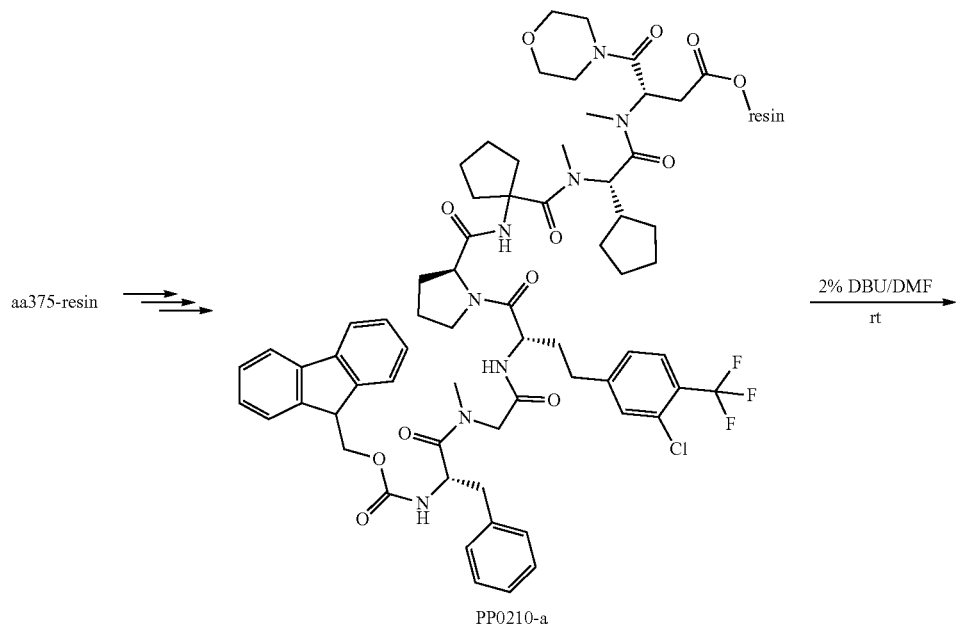 2% DBU/DMF
rt
PP0210-a
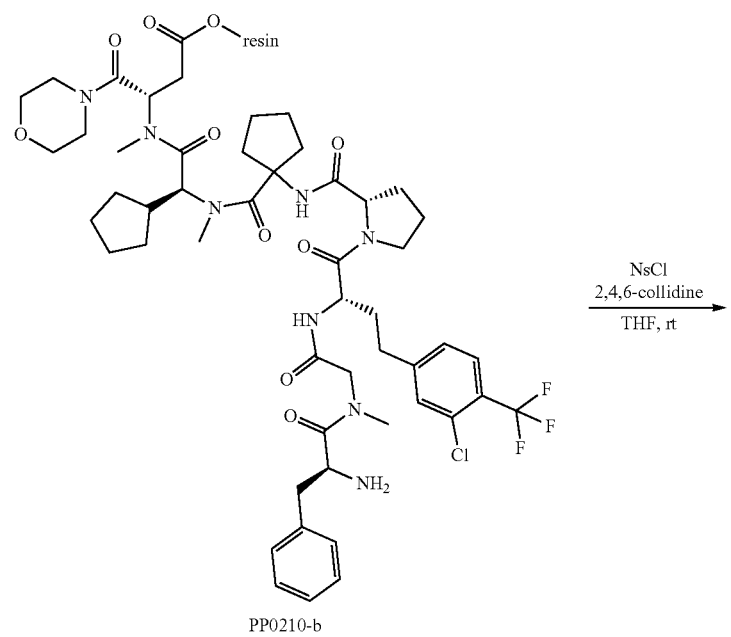
PP0210-b
NsCl
2,4,6-collidine
THF, rt -continued
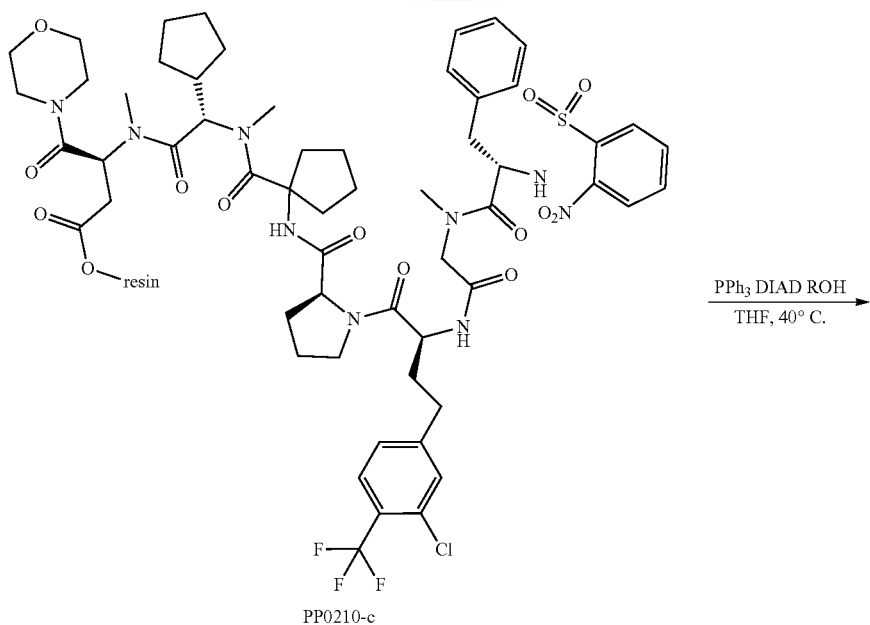
PP0210-c
$\xrightarrow{\text{PPh}_3 \text{ DIAD ROH}}{\text{THF, 40° C.}}$
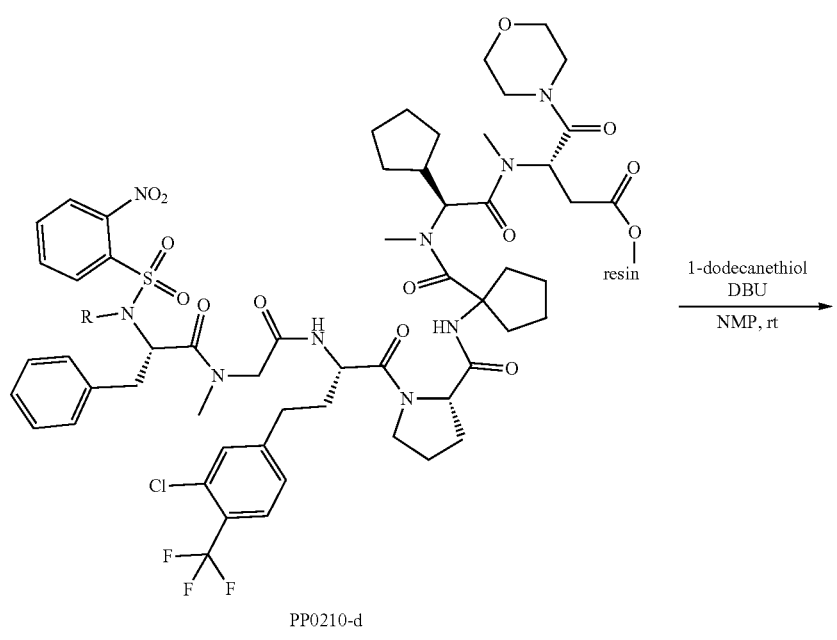
PP0210-d
$\xrightarrow[\text{NMP, rt}]{\substack{\text{1-dodecanethiol}\\\text{DBU}}}$ -continued

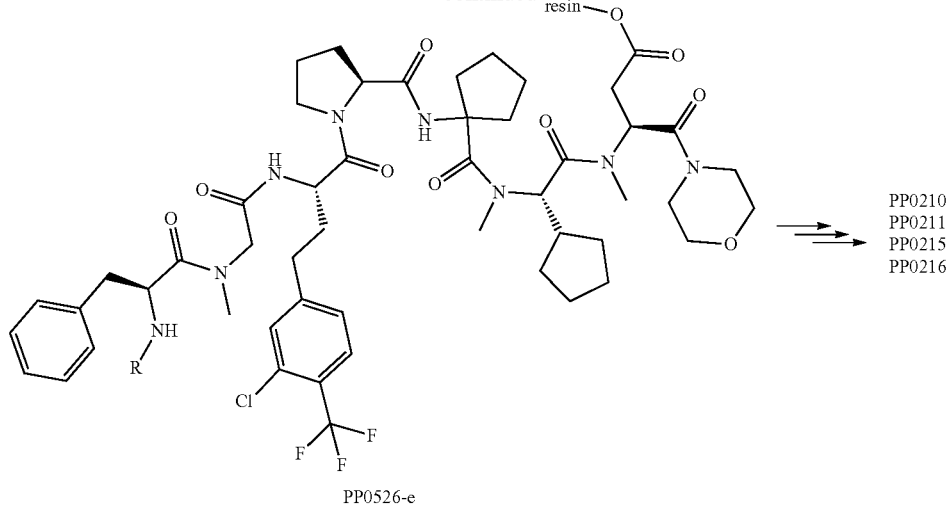

PP0526-e

→→ PP0210
PP0211
PP0215
PP0216

Using Compound aa375-resin as a raw material, peptide synthesis by the basic peptide synthesis method described in the present Examples was performed to give resin-supported Compound PP0210-a. After resin-supported Compound PP0210-b was obtained in the same manner as synthesis of Compound PP55-b, resin-supported Compound PP0210-c was obtained in the same manner as synthesis of Compound PP55-c using THF in place of NMP as a reaction solvent. After resin-supported Compound PP0210-d was obtained in the same manner as synthesis of Compound PP55-d using the alcohols shown in Table 28 in place of 1-butanol, resin-supported Compound PP0210-e was obtained in the same manner as synthesis of Compound PP55-e. Subsequent steps of peptide elongation, cleaving from resin, cyclization, and purification were performed according to the basic route to give the intended compounds. LC/MS data is provided in Table 36.

TABLE 28

| Intended product | Alcohol |
| --- | --- |
| Compound PP0210 | Ethanol |
| Compound PP0211 | 1-Propanol |
| Compound PP0215 | Ethanol |
| Compound PP0216 | 1-Propanol |

Synthesis of Compound PP0213, Compound PP0214, Compound PP0218, and Compound PP219

Compound PP0213, Compound PP0214, Compound PP0218, and Compound PP0219 were synthesized according to the following scheme.

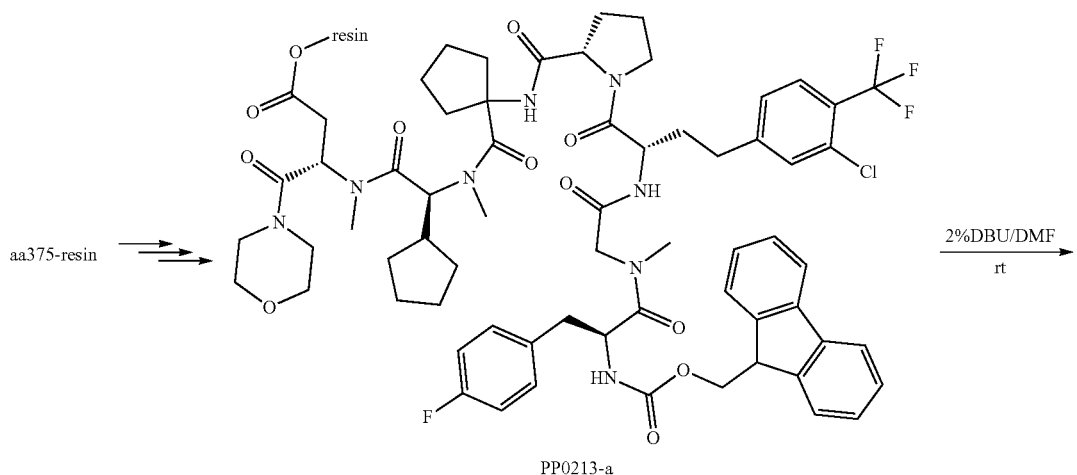

PP0213-a

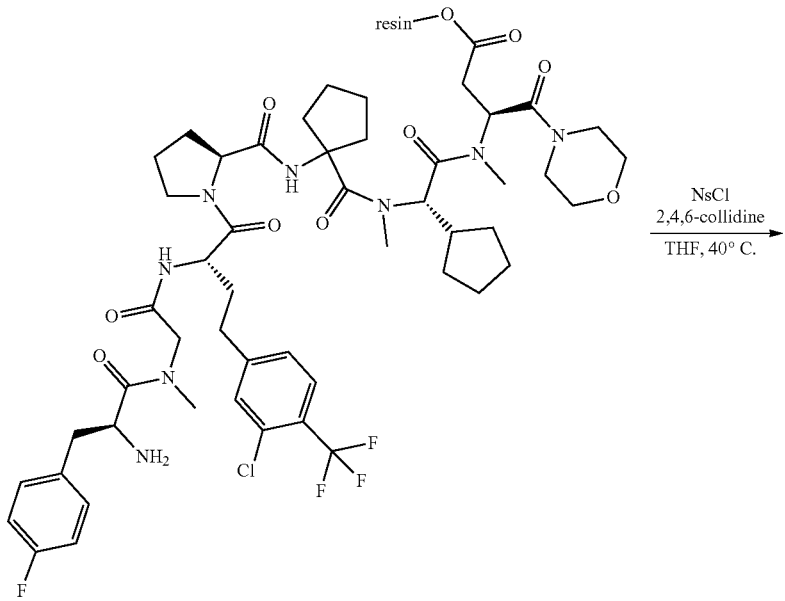
PP0213-b
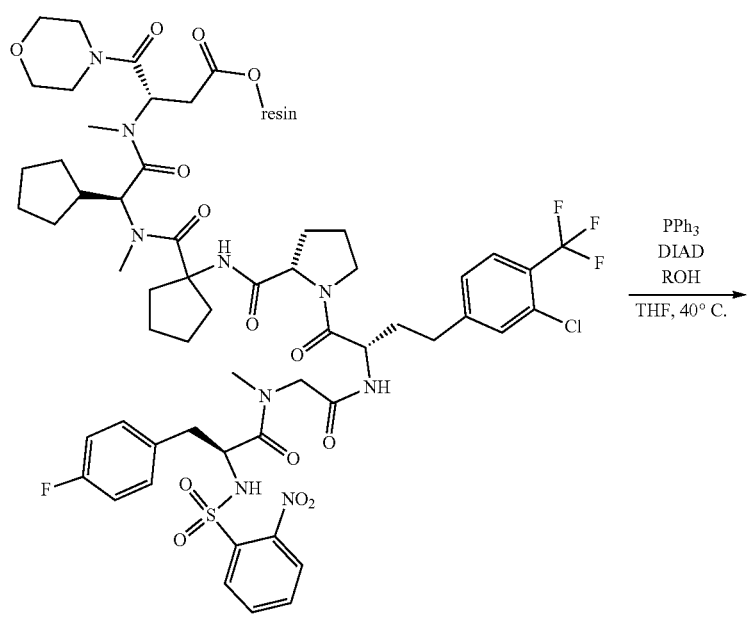
PP0213-c

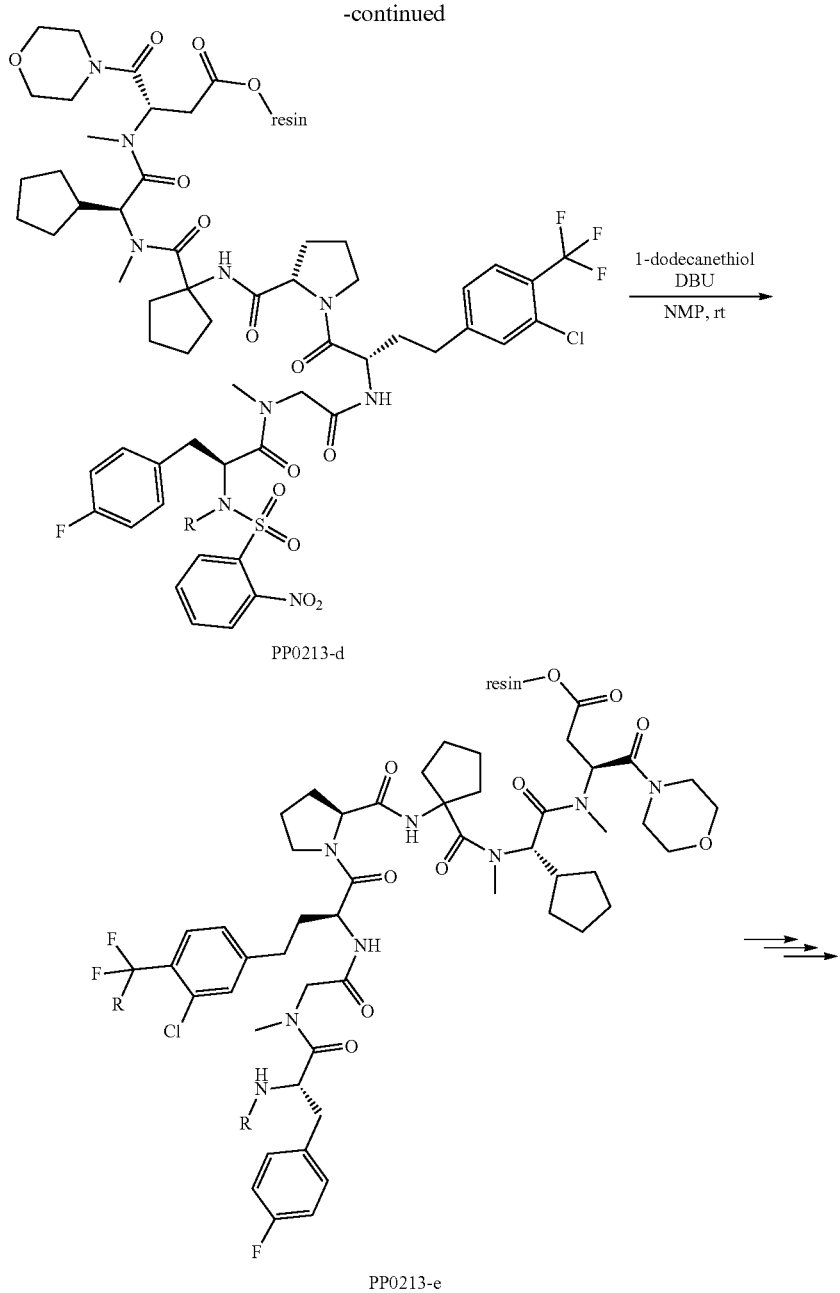

Using Compound aa375-resin as a raw material, peptide synthesis by the basic peptide synthesis method described in the present Examples was performed to give resin-supported Compound PP0213-a. After resin-supported Compound PP0213-b was obtained in the same manner as synthesis of Compound PP55-b, resin-supported Compound PP0213-c was obtained in the same manner as synthesis of Compound PP55-c using THF in place of NMP as a reaction solvent. After resin-supported Compound PP0213-d was obtained in the same manner as synthesis of Compound PP55-d using the alcohols shown in Table 29 in place of 1-butanol, resin-supported Compound PP0213-e was obtained in the same manner as synthesis of Compound PP55-e. Subsequent steps of peptide elongation, cleaving from resin, cyclization, and purification were performed according to the basic route to give the intended compounds. LC/MS data is provided in Table 36.

TABLE 29

| Intended product | Alcohol |
|---|---|
| Compound PP0213 | Ethanol |
| Compound PP0214 | 1-Propanol |
| Compound PP0218 | Ethanol |
| Compound PP0219 | 1-Propanol |

Synthesis of Compound PP524 and Compound PP525

Compound PP524 and Compound PP525 were synthesized according to the following scheme.

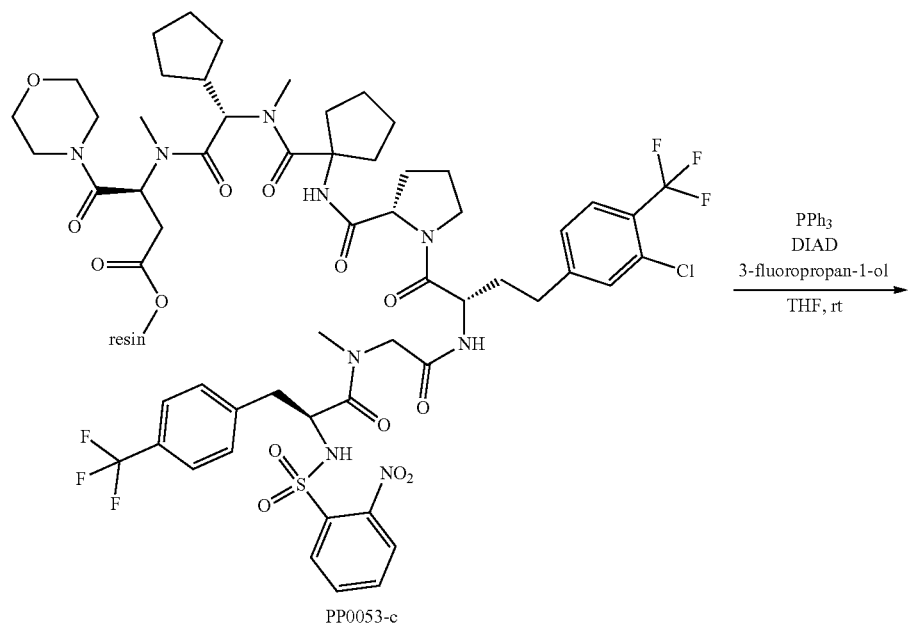
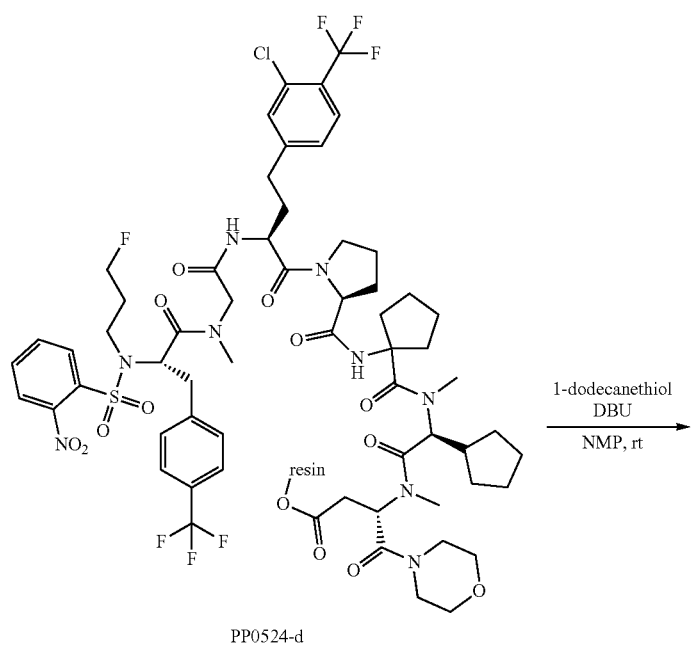

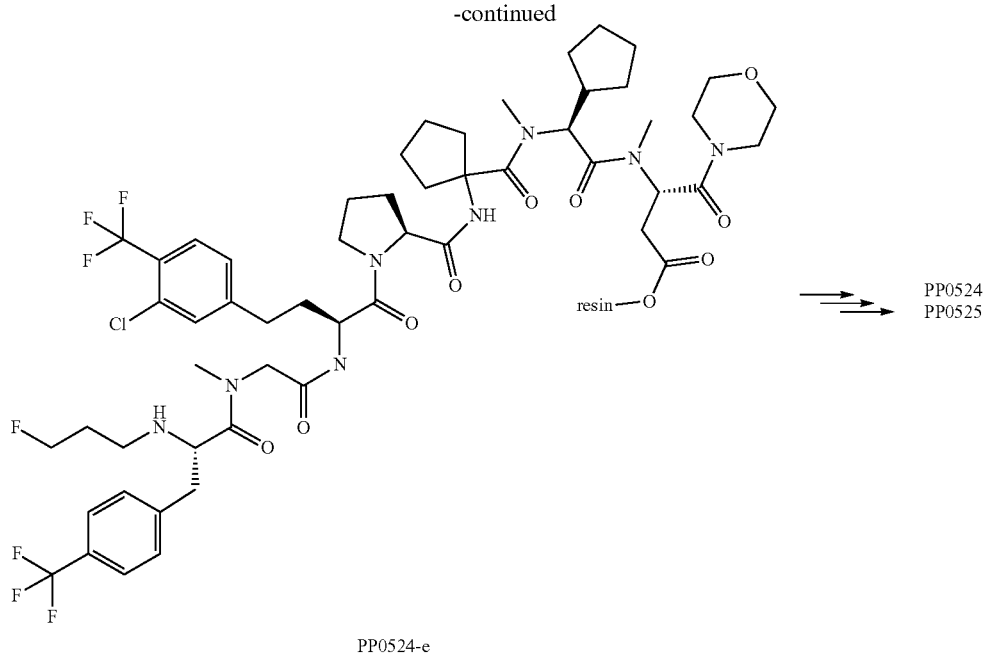

PP0524-e

DCM (1.5 mL) was added to swell resin-supported PP0053-c (210 mg). After DCM was removed, the resin was washed 4 times with THF. Triphenylphosphine (173 mg, 0.661 mmol) was dissolved in THF (0.600 mL), a mixed solution of DIAD (0.128 mL, 0.661 mmol) and THF (0.572 mL) was added thereto, and the mixture was stirred for 15 minutes. 3-Fluoropropan-1-ol (0.099 mL, 1.32 mmol) was added thereto, and the mixture was left to stand still for 5 minutes. This solution was added to the resin, the mixture was shaken at room temperature for 1 hour, and then the reaction solution was removed. The resin was washed 4 times with THF (1.5 mL) and washed 4 times with DCM (1.5 mL) to give resin-supported Compound PP524-d. Cleaving from the resin was performed with TFE/DCM (1/1) using a small amount of resin-supported Compound PP524-d, and the structure was verified by LC/MS.

LCMS (ESI) m/z=1359 (M+H)+

Retention time: 0.98 min (Analytical condition SQDFA05)

Using this, resin-supported Compound PP524-e was obtained in the same manner as synthesis of Compound PP55-e. Subsequent steps of peptide elongation, cleaving from resin, cyclization, and purification were performed according to the basic route to give the intended compounds. LC/MS data is provided in Table 36.

Synthesis of Compound PP526 and Compound PP527

Compound PP526 and Compound PP527 were synthesized according to the following scheme.

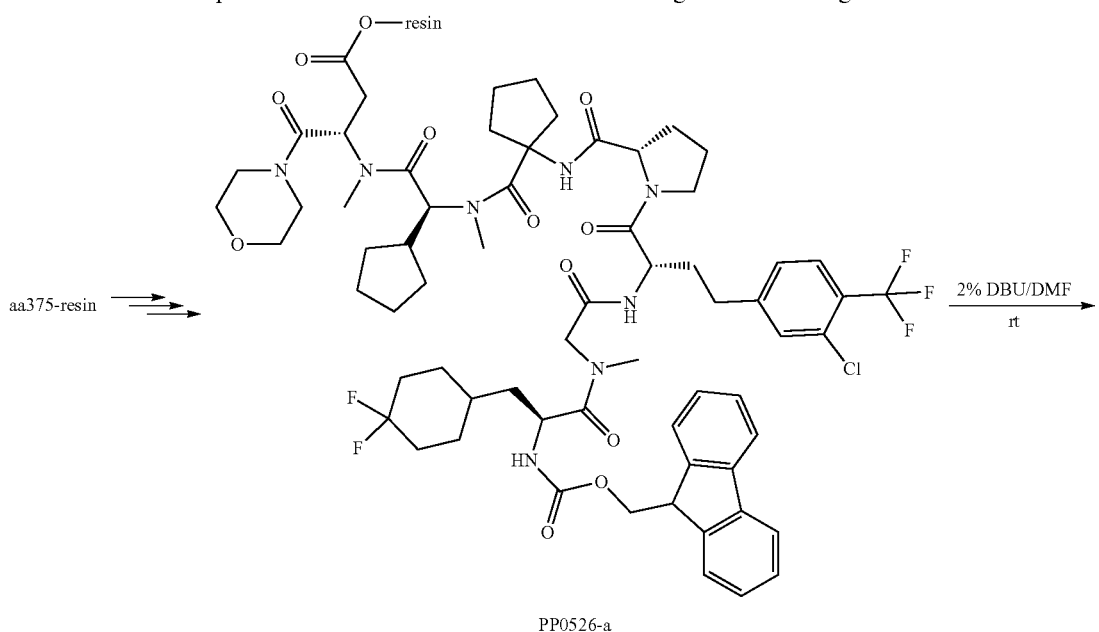

PP0526-a

-continued
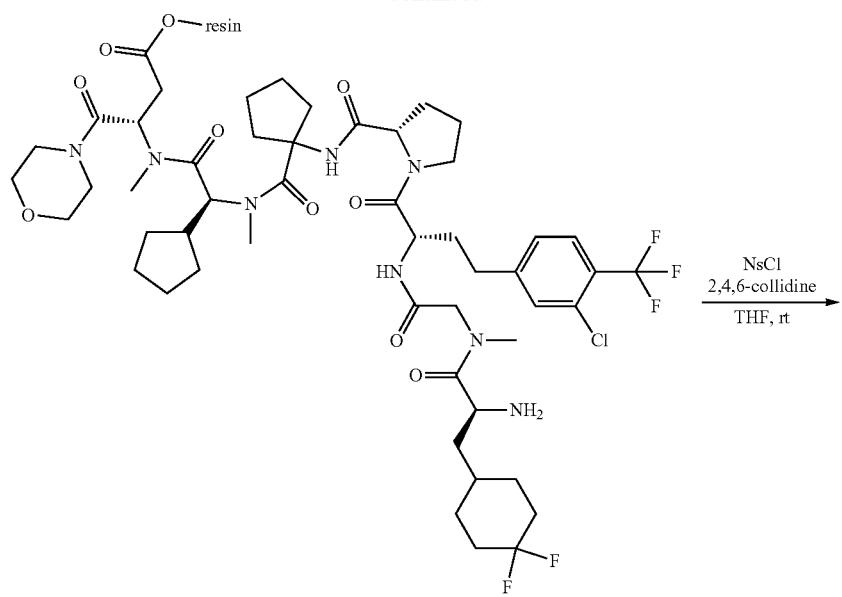
PP0526-b
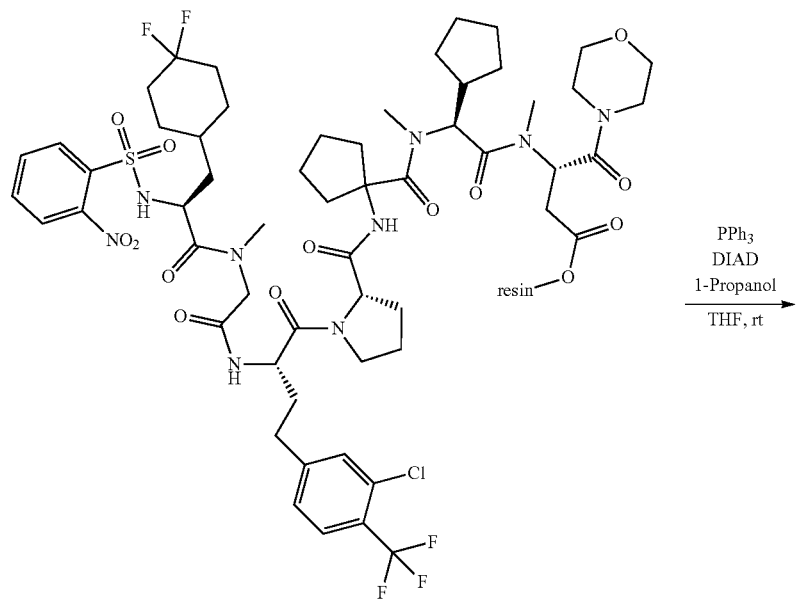
PP0526-c

-continued

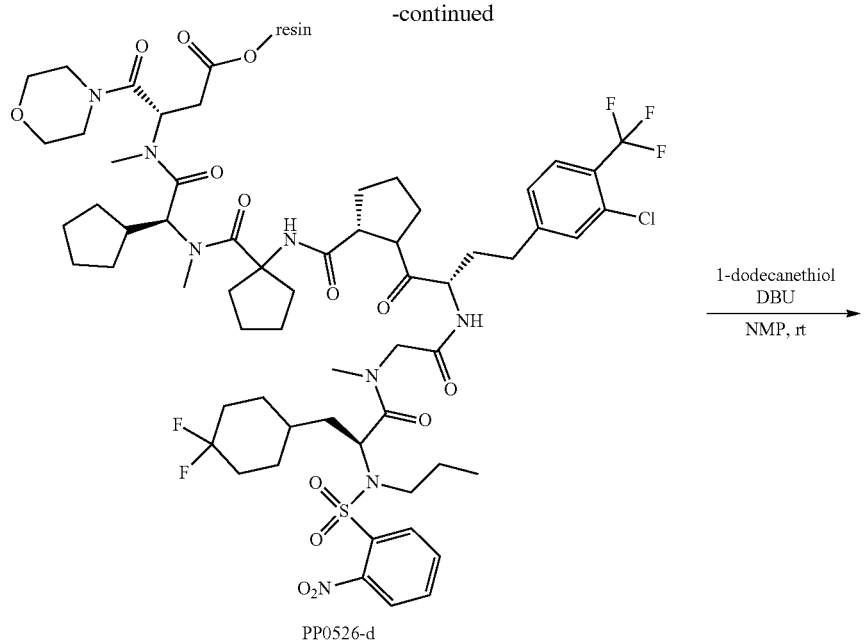

PP0526-d

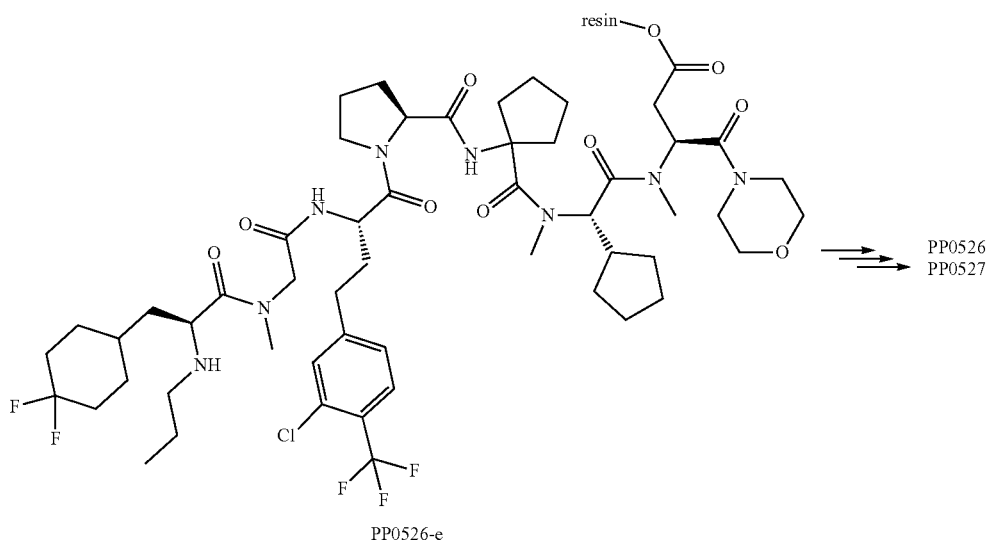

PP0526-e

Using Compound aa375-resin as a raw material, peptide synthesis by the basic peptide synthesis method described in the present Examples was performed to give resin-supported Compound PP526-a. After resin-supported Compound PP526-b was obtained in the same manner as synthesis of Compound PP55-b, resin-supported Compound PP526-c was obtained in the same manner as synthesis of Compound PP55-c using THF in place of NMP as a reaction solvent. After resin-supported Compound PP526-d was obtained in the same manner as synthesis of Compound PP524-d allowing 1-propanol to react in place of 3-fluoropropan-1-ol, resin-supported Compound PP526-e was obtained in the same manner as synthesis of Compound PP55-e. Subsequent steps of peptide elongation, cleaving from resin, cyclization, and purification were performed according to the basic route to give the intended compounds. LC/MS data is provided in Table 36.

Synthesis of Compound PP599

Compound PP599 was synthesized according to the following scheme.

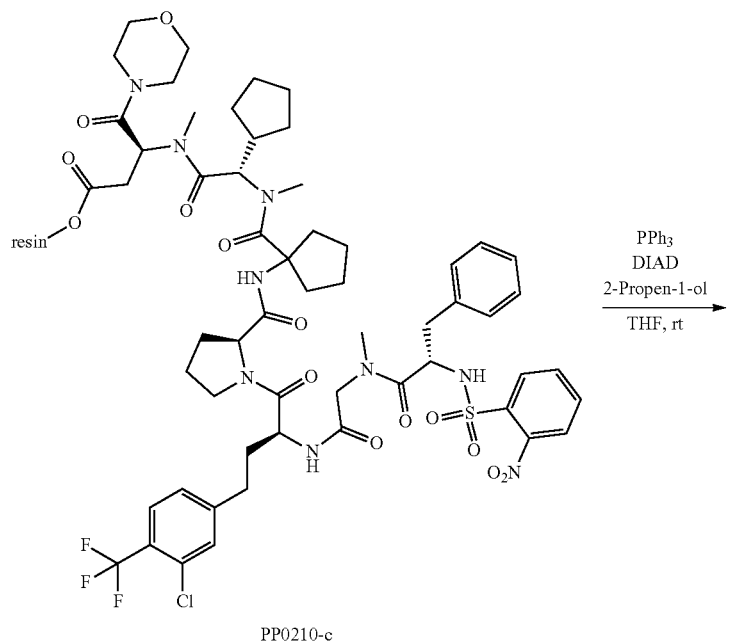
PP0210-c
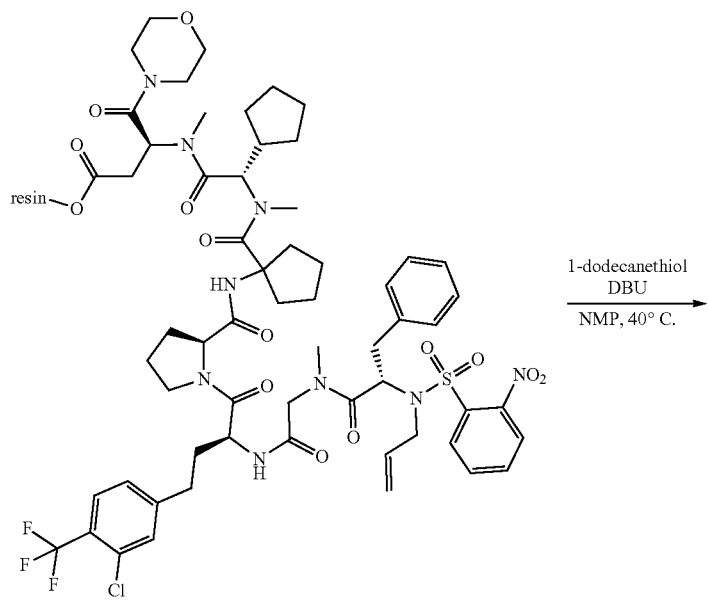
PP0599-d

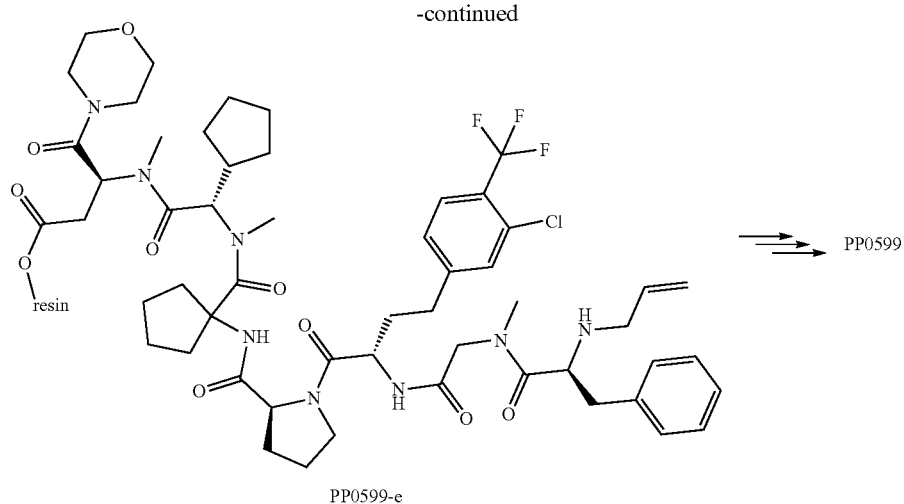

PP0599-e

Using resin-supported PP210-c, resin-supported Compound PP599-d was obtained in the same manner as synthesis of Compound PP524-d using 2-propen-1-ol in place of 3-fluoropropan-1-ol, and then resin-supported Compound PP599-e was obtained in the same manner as synthesis of Compound PP55-e. Subsequent steps of peptide elongation, cleaving from resin, cyclization, and purification were performed according to the basic route to give the intended compound. LC/MS data is provided in Table 36.

Synthesis of Compound PP0605

Compound PP0605 was synthesized according to the following scheme.

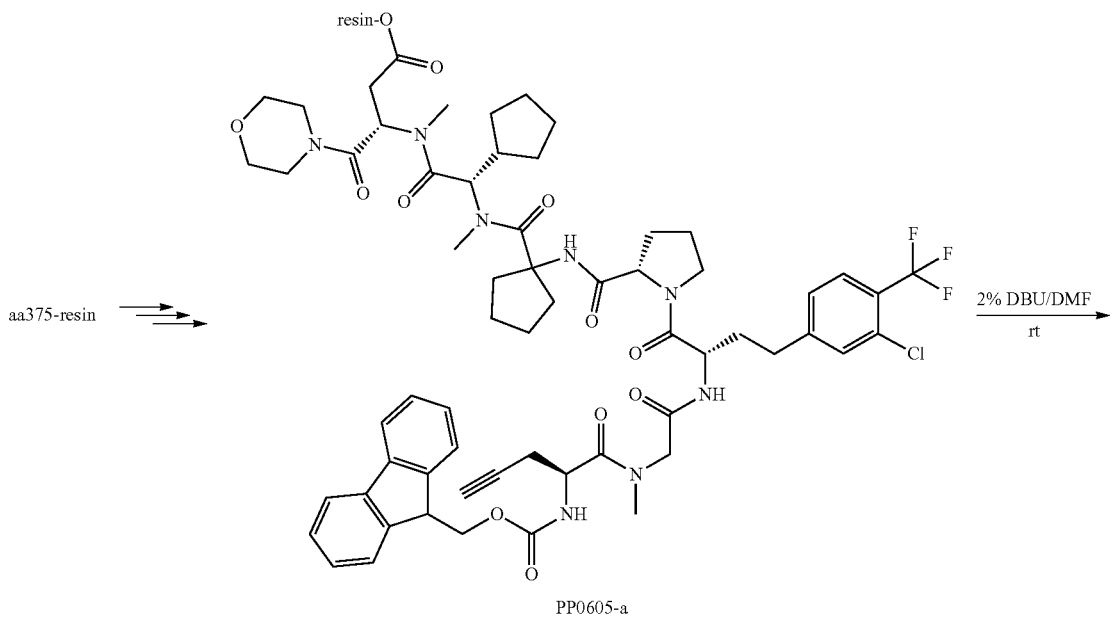

PP0605-a

-continued
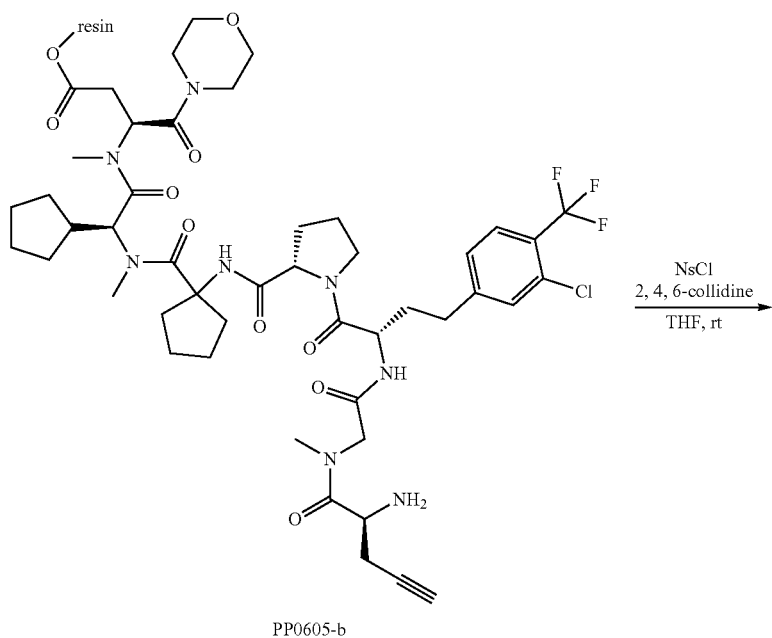
PP0605-b
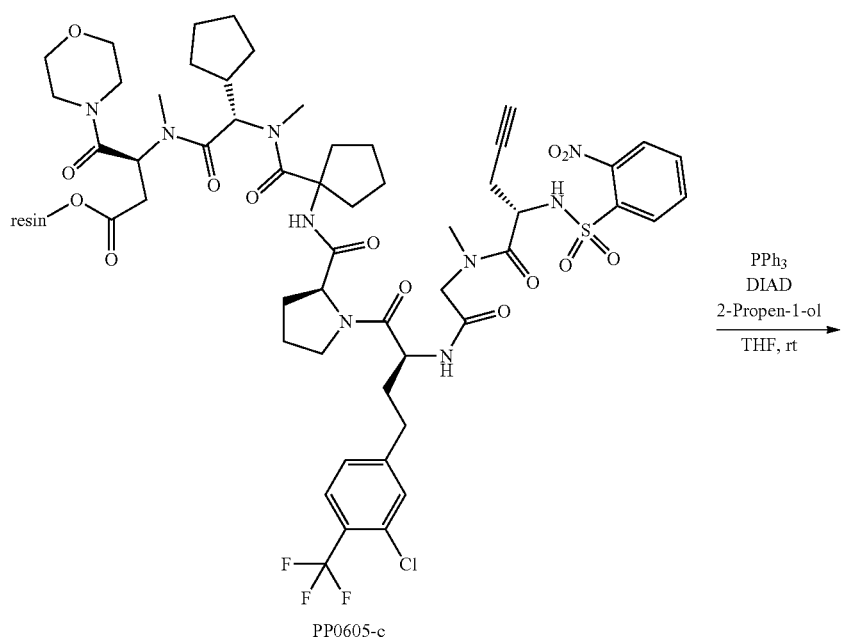
PP0605-c

-continued

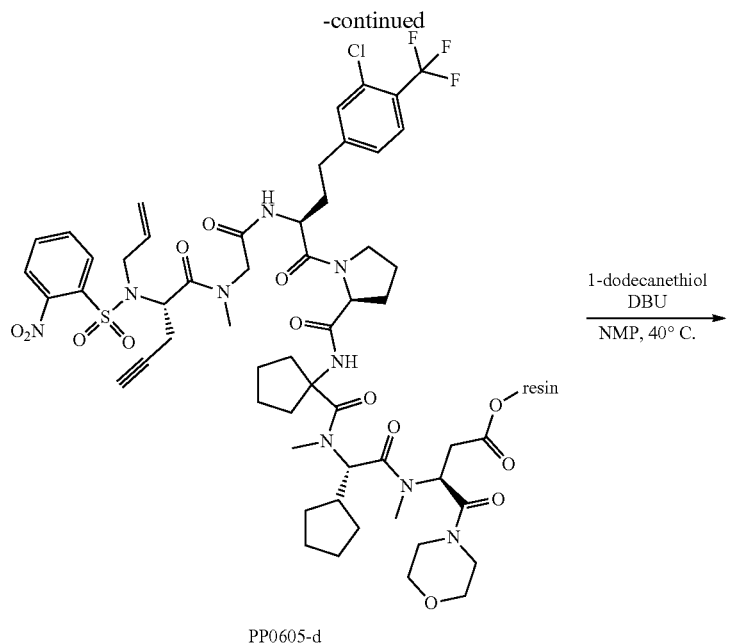

PP0605-d

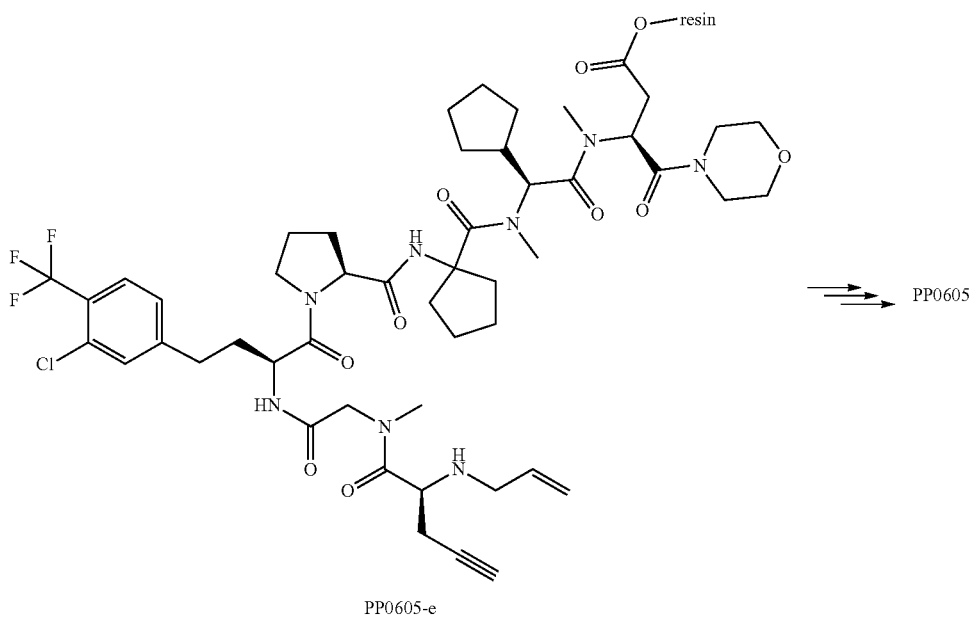

PP0605-e

Using Compound aa375-resin as a raw material, peptide synthesis by the basic peptide synthesis method described in the present Examples was performed to give resin-supported Compound PP0605-a. After resin-supported Compound PP0605-b was obtained in the same manner as synthesis of Compound PP55-b, resin-supported Compound PP0605-c was obtained in the same manner as synthesis of Compound PP55-c using THF in place of NMP as a reaction solvent. After resin-supported Compound PP0605-d was obtained in the same manner as synthesis of Compound PP524-d using 2-propen-1-ol in place of 3-fluoropropan-1-ol, resin-supported Compound PP0605-e was obtained in the same manner as synthesis of Compound PP55-e. Subsequent steps of peptide elongation, cleaving from resin, cyclization, and purification were performed according to the basic route to give the intended compound. LC/MS data is provided in Table 36.

Abbreviations and structures of amino acids contained as partial structures in a cyclic compound and an oligopeptide compound synthesized via N-alkylation by a Mitsunobu reaction on a resin are provided below.

TABLE 29-1
| Compound No. | Abbreviation | Amino acid Structural Formula |
|---|---|---|
| bb038 | Phe(4-Me) | 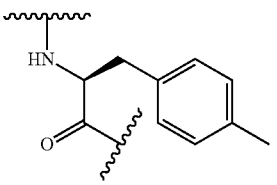 [SMILES: *N[C@@H](Cc1ccc(C)cc1)C(*)=O] |
| bb039 | nBuPhe(4-Me) | 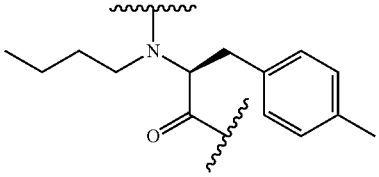 [SMILES: *C(=O)[C@H](Cc1ccc(C)cc1)N(*)CCCC] |
| bb040 | iBuPhe(4-Me) | 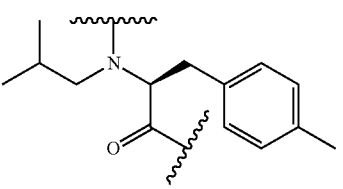 [SMILES: *C(=O)[C@H](Cc1ccc(C)cc1)N(*)CC(C)C] |
| bb041 | cPrMePhe(4-Me) | 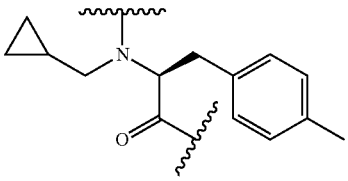 [SMILES: *C(=O)[C@H](Cc1ccc(C)cc1)N(*)CC1CC1] |
| bb042 | cBuMePhe(4-Me) | 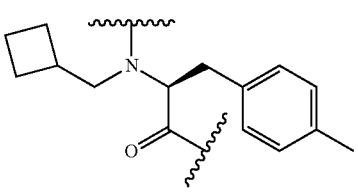 [SMILES: *C(=O)[C@H](Cc1ccc(C)cc1)N(*)CC1CCC1] |
| bb043 | cPentMePhe(4-Me) | 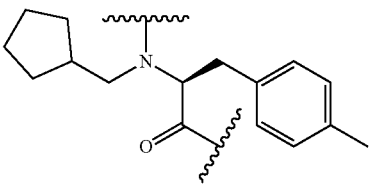 [SMILES: *C(=O)[C@H](Cc1ccc(C)cc1)N(*)CC1CCCC1] |
| bb044 | cHexMePhe(4-Me) | 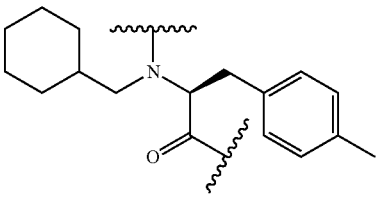 [SMILES: *C(=O)[C@H](Cc1ccc(C)cc1)N(*)CC1CCCCC1] |
| bb045 | iPenPhe(4-Me) | 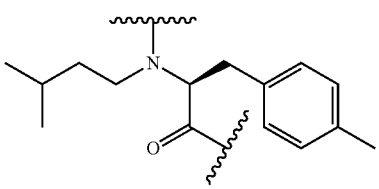 [SMILES: *C(=O)[C@H](Cc1ccc(C)cc1)N(*)CCC(C)C] |

TABLE 29-1-continued
| Compound No. | Abbreviation | Amino acid Structural Formula |
|---|---|---|
| bb046 | neoHexPhe(4-Me) | 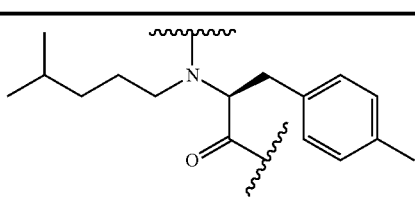 |
| bb047 | AllylPhe(4-Me) | 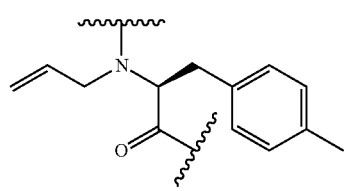 [SMILES: *C(=O)[C@H](Cc1ccc(C)cc1)N(*)CC=C] |
| bb048 | PraPhe(4-Me) | 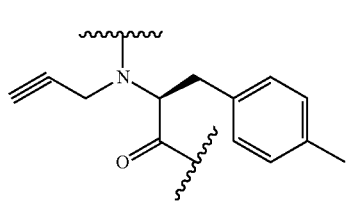 [SMILES: *C(=O)[C@H](Cc1ccc(C)cc1)N(*)CC#C] |
| bb049 | TfpPhe(4-Me) | 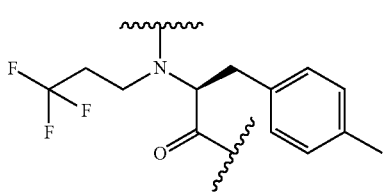 [SMILES: *C(=O)[C@H](Cc1ccc(C)cc1)N(*)CCC(F)(F)F] |
| bb050 | MeOEtPhe(4-Me) | 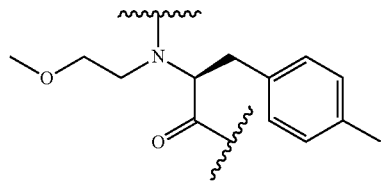 |
| bb051 | MeOnPrPhe(4-Me) | 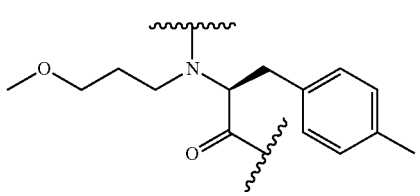 |
| bb052 | nBuPhe(4-CF3) | 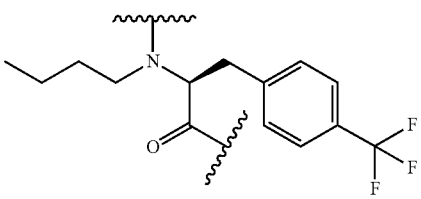 [SMILES: *C(=O)[C@H](Cc1ccc(C(F)(F)F)cc1)N(*)CCCC] |
| bb053 | iBuPhe(4-CF3) | 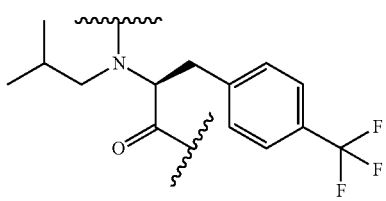 [SMILES: *C(=O)[C@H](Cc1ccc(C(F)(F)F)cc1)N(*)CC(C)C] |

TABLE 29-1-continued

| Compound No. | Abbreviation | Amino acid Structural Formula |
|---|---|---|
| bb054 | cPrMePhe(4-CF3) | |
| bb055 | cBuMePhe(4-CF3) | |
| bb056 | cPentMePhe(4-CF3) | |
| bb057 | cHexMePhe(4-CF3) | |
| bb058 | iPenPhe(4-CF3) | |
| bb059 | neoHexPhe(4-CF3) | |
| bb060 | PraPhe(4-CF3) | |

TABLE 29-1-continued

| Compound No. | Abbreviation | Amino acid Structural Formula |
|---|---|---|
| bb061 | TfpPhe(4-CF3) | |
| bb062 | MeOEtPhe(4-CF3) | |
| bb063 | MeOnPrPhe(4-CF3) | |
| bb064 | nPrGly(cPent) | |
| bb065 | Phe(4-OCF3) | |
| bb066 | nPrPhe(4-OCF3) | |
| bb067 | Phe | |
| bb068 | EtPhe | |

TABLE 29-1-continued

| Compound No. | Abbreviation | Amino acid Structural Formula |
|---|---|---|
| bb069 | nPrPhe | |
| bb070 | EtPhe(4-F) | |
| bb071 | nPrPhe(4-F) | |
| bb072 | MfpPhe(4-CF3) | |
| bb073 | nPrCha(4-F2) | |
| bb074 | AllylPRA | |
| bb075 | AllylPhe(4-Cl) | |

TABLE 29-1-continued
| Compound No. | Abbreviation | Amino acid Structural Formula |
|---|---|---|
| bb076 | AllylPhe(4-OMe) | |
| bb077 | AllylPhe(4-OCF3) | |
1-6-5. Peptide Modification by Olefin Metathesis Reaction
Synthesis of Compound PP0616
Compound PP0616 was synthesized according to the following scheme.
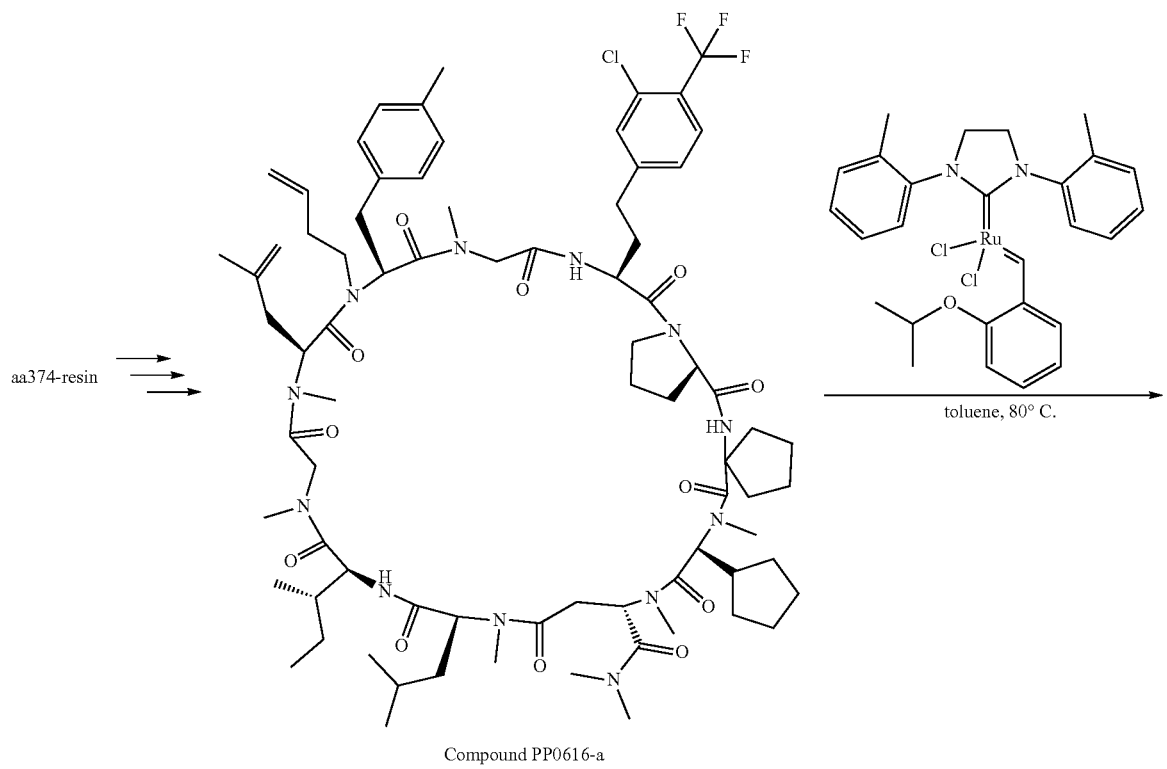
Compound PP0616-a -continued

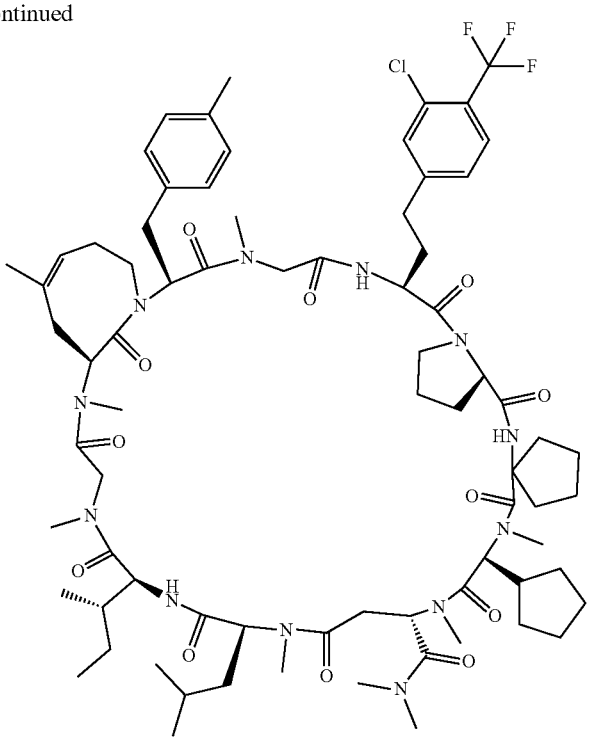

Compound PP0616

Using Compound aa374-resin as a raw material, peptide synthesis by the basic peptide synthesis method described in the present Examples was performed to give Compound PP0616-a (6.5 mg, 4.36 μmol).

LCMS (ESI) m/z=1491 (M+H)+

Retention time: 0.82 min (Analytical condition SQDFA50)

Compound PP0616-a (6.5 mg, 4.36 μmol) and a Stewart-Grubbs catalyst (2.5 mg, 4.36 μmol) were dissolved in toluene (1 mL), and the mixture was stirred at 80° C. for 24.5 hours in a nitrogen atmosphere. After cooling to room temperature, the solvent was distilled off under reduced pressure. The resulting crude product was purified by reverse phase HPLC(methanol/50 mM aqueous ammonium acetate solution) to give PP0616 (3.3 mg, 52%).

LC/MS data is provided in Table 36.

Synthesis of Compound PP0617

Compound PP0617 was synthesized according to the following scheme.

aa374-resin ⟶⟶

-continued

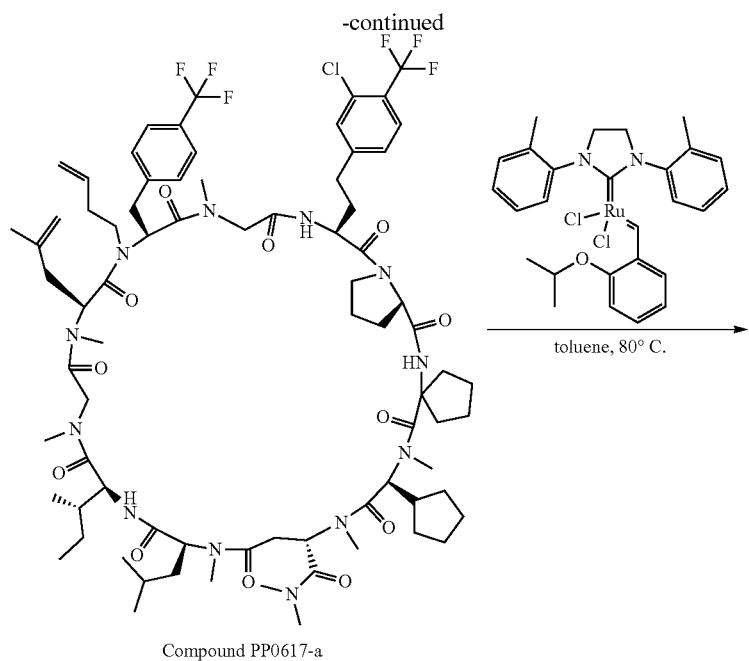

Compound PP0617-a

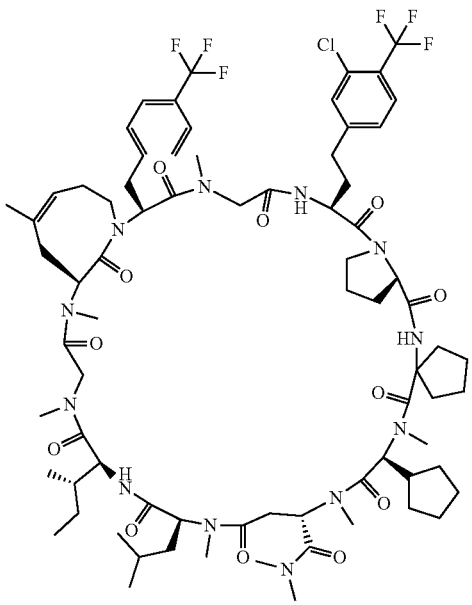

Compound PP0617

Using Compound aa374-resin as a raw material, peptide synthesis by the basic peptide synthesis method described in the present Examples was performed to give Compound PP0617-a (8.4 mg, 5.44 μmol). Using the resulting PP0617-a, PP0617 (1.7 mg, 22%) was obtained in the same manner as synthesis of Compound PP0616. LC/MS data is provided in Table 36.

Synthesis of Compound PP0618

Compound PP0618 was synthesized according to the following scheme.

aa374-resin →→

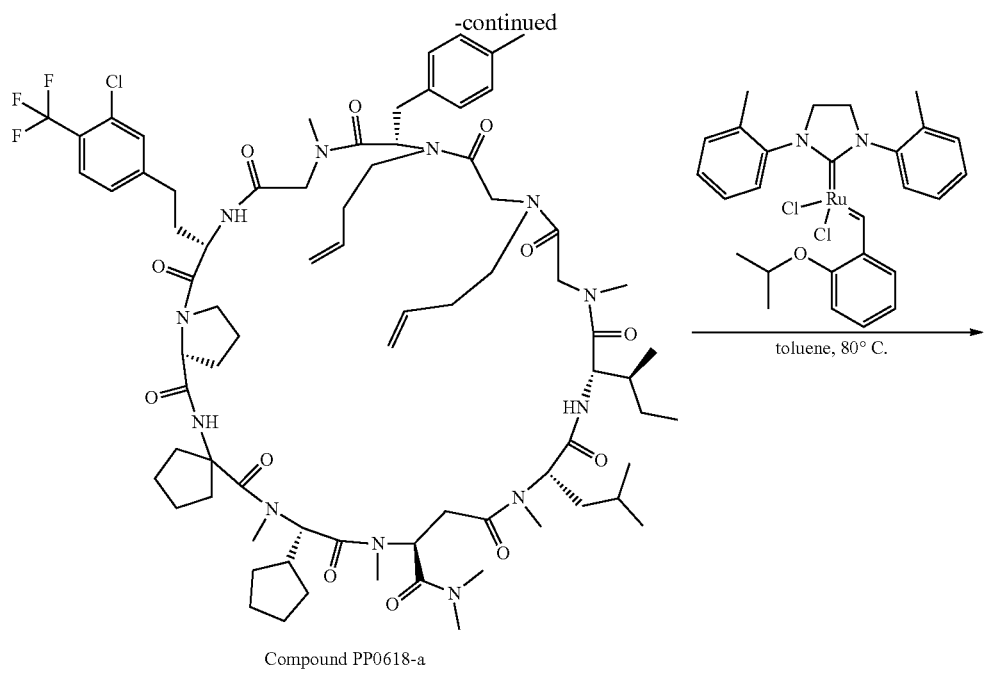

Compound PP0618-a

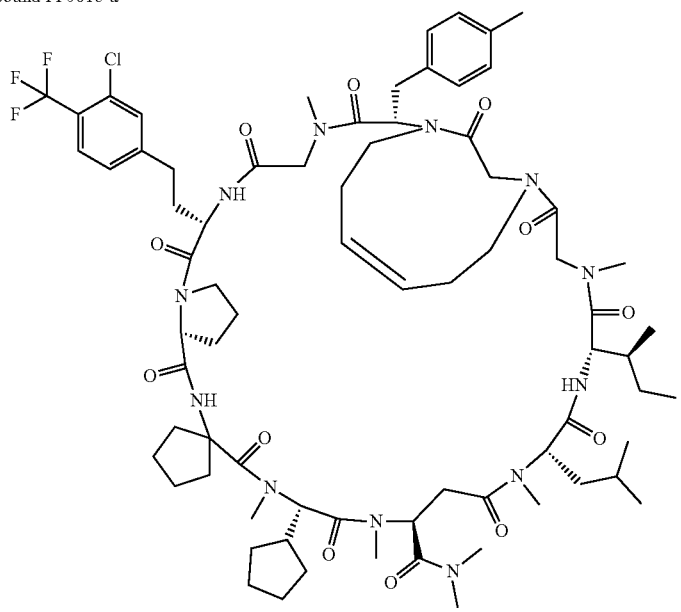

Compound PP0618

Using Compound aa374-resin as a raw material, peptide synthesis by the basic peptide synthesis method described in the present Examples was performed to give Compound PP0618-a (23.9 mg, 16.6 μmol). Using the resulting PP0618-a, PP0618 (2.4 mg, 11%) was obtained in the same manner as synthesis of Compound PP0616. LC/MS data is provided in Table 36.

Synthesis of Compound PP0619

Compound PP0619 was synthesized according to the following scheme.

aa374-resin →→

-continued

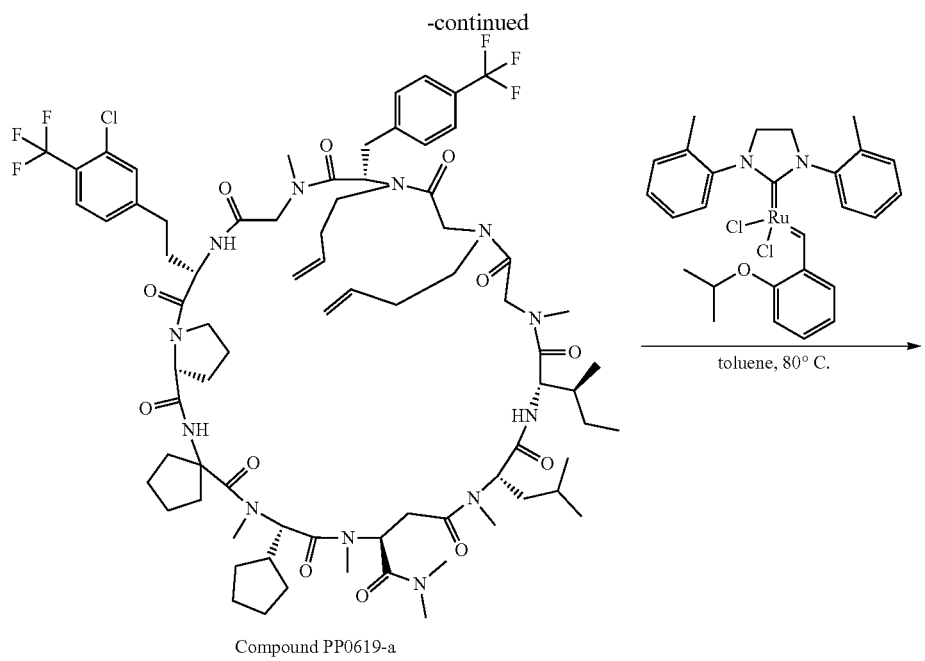

Compound PP0619-a

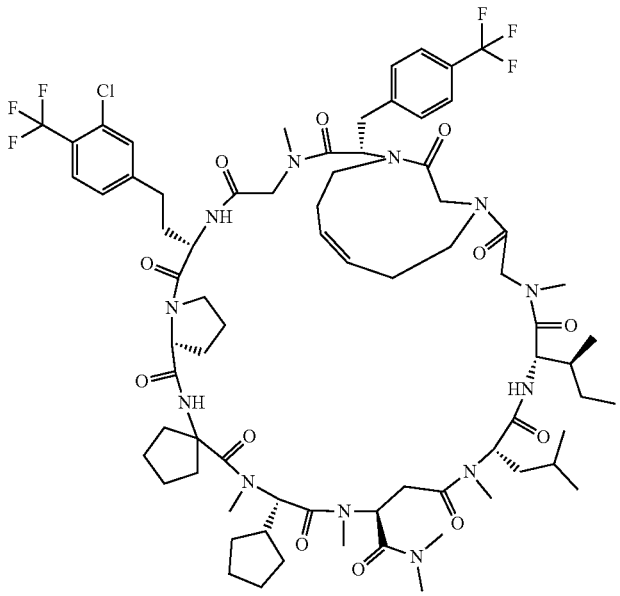

Compound PP0619

Using Compound aa374-resin as a raw material, peptide synthesis by the basic peptide synthesis method described in the present Examples was performed to give Compound PP0619-a (17.6 mg, 11.4 μmol). Using the resulting PP0619-a, PP0619 (0.57 mg, 3%) was obtained in the same manner as synthesis of Compound PP0616. LC/MS data is provided in Table 36.

Synthesis of Compound PP0620

Compound PP0620 was synthesized according to the following scheme.

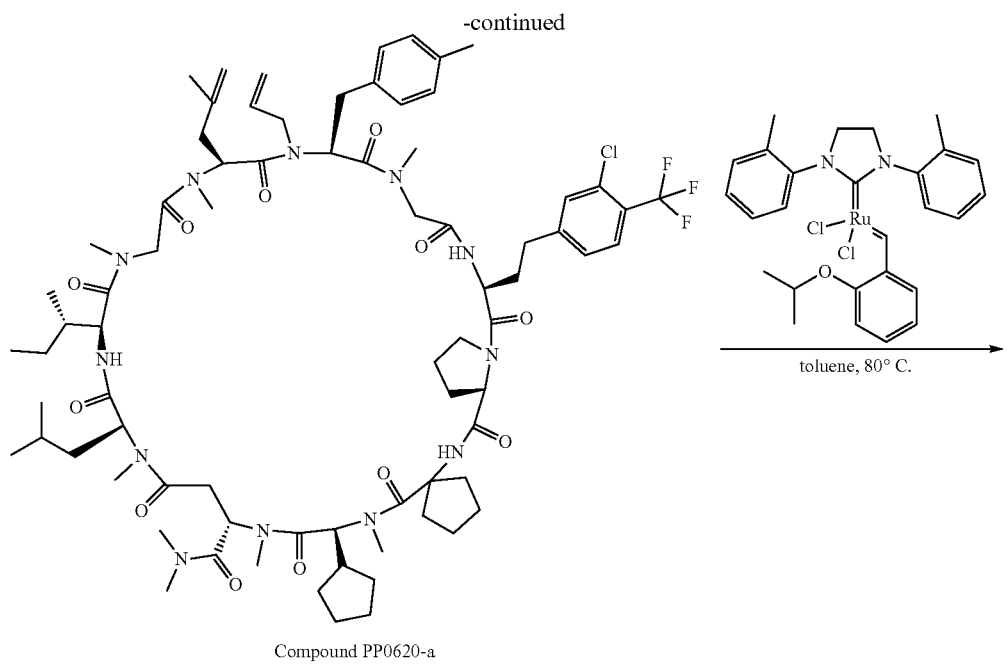

Compound PP0620-a

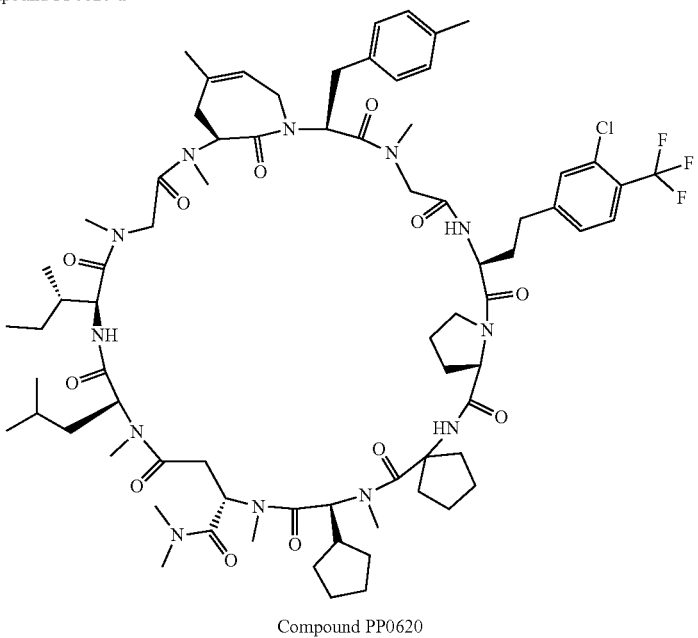

Compound PP0620

Using Compound aa374-resin as a raw material, peptide synthesis by the basic peptide synthesis method described in the present Examples was performed to give Compound PP0620-a (13.7 mg, 9.3 µmol). Using the resulting PP0620-a, PP0620 (6.7 mg, 53%) was obtained in the same manner as synthesis of Compound PP0616. LC/MS data is provided in Table 36.

Synthesis of Compound PP0621

Compound PP0621 was synthesized according to the following scheme.

aa374-resin →→

-continued

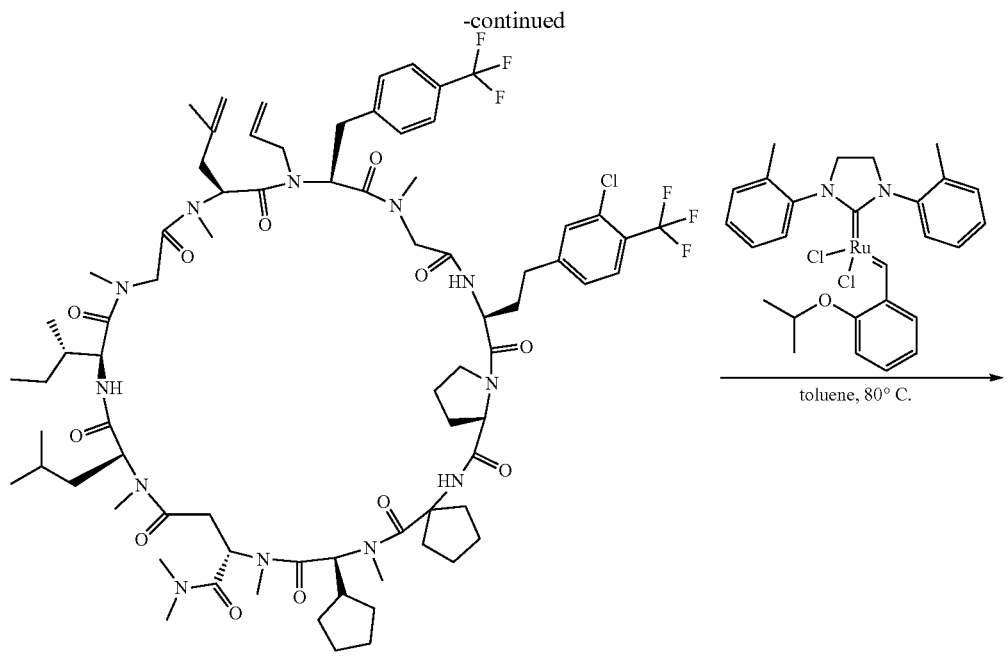
Compound PP0621-a

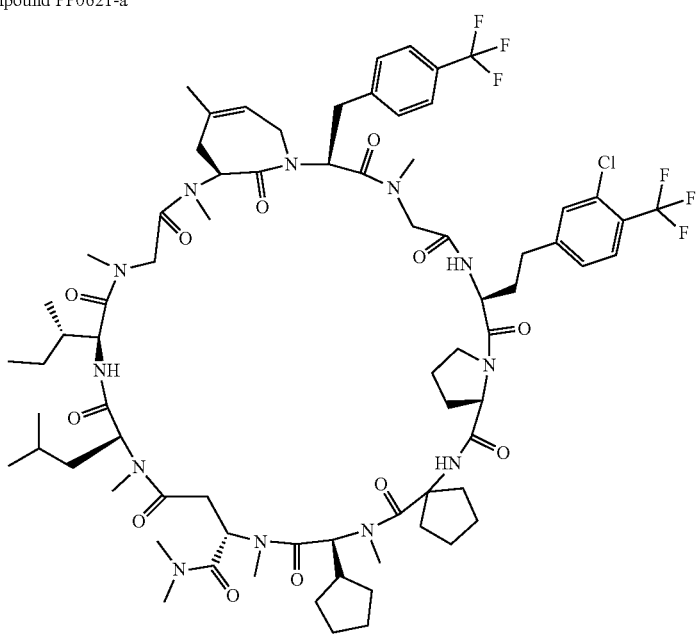
Compound PP0621

Using Compound aa374-resin as a raw material, peptide synthesis by the basic peptide synthesis method described in the present Examples was performed to give Compound PP0621-a (8.3 mg, 5.4 μmol). Using the resulting PP0621-a, PP0621 (3.9 mg, 44%) was obtained in the same manner as synthesis of Compound PP0616. LC/MS data is provided in Table 36.

Synthesis of Compound PP0622

Compound PP0622 was synthesized according to the following scheme.

aa374-resin →→

-continued

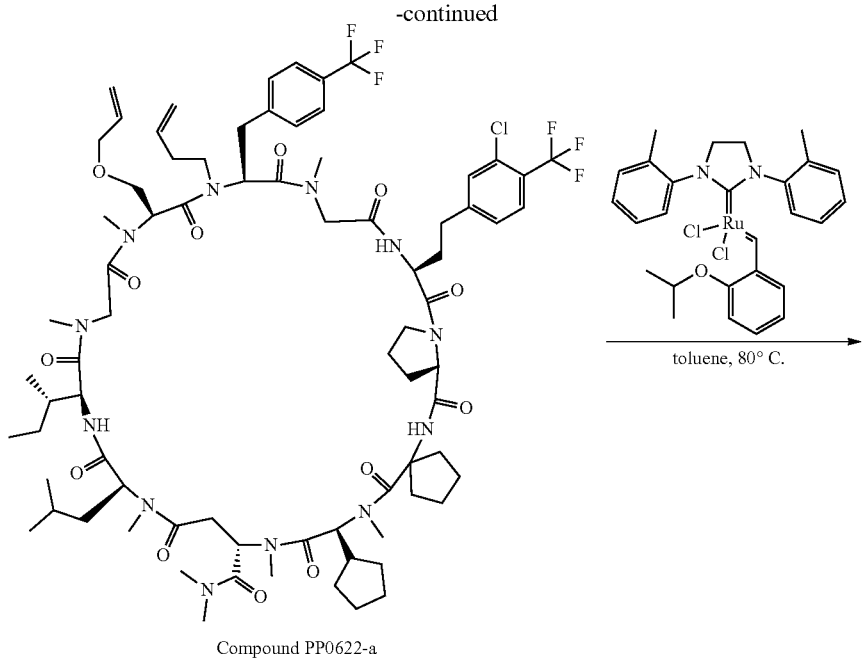

Compound PP0622-a

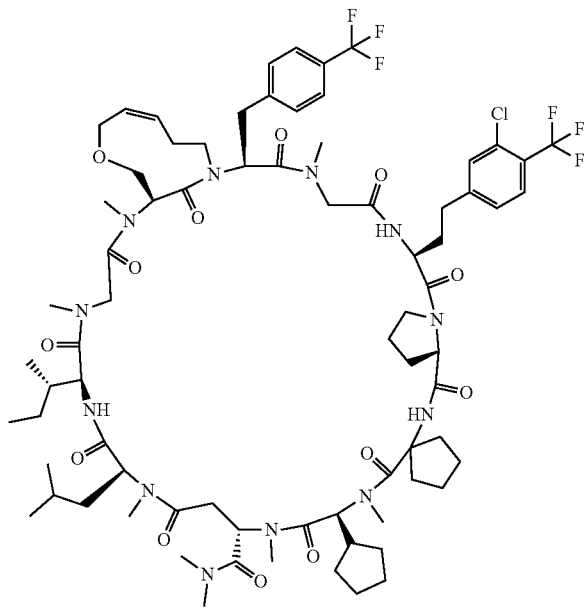

Compound PP0622

Using Compound aa374-resin as a raw material, peptide synthesis by the basic peptide synthesis method described in the present Examples was performed to give Compound PP0622-a (7.6 mg, 4.9 μmol). Using the resulting PP0622-a, PP0622 (0.25 mg, 4%) was obtained in the same manner as synthesis of Compound PP0616. LC/MS data is provided in Table 36.

Synthesis of Compound PP0623

Compound PP0623 was synthesized according to the following scheme.

aa374-resin ⟶

-continued

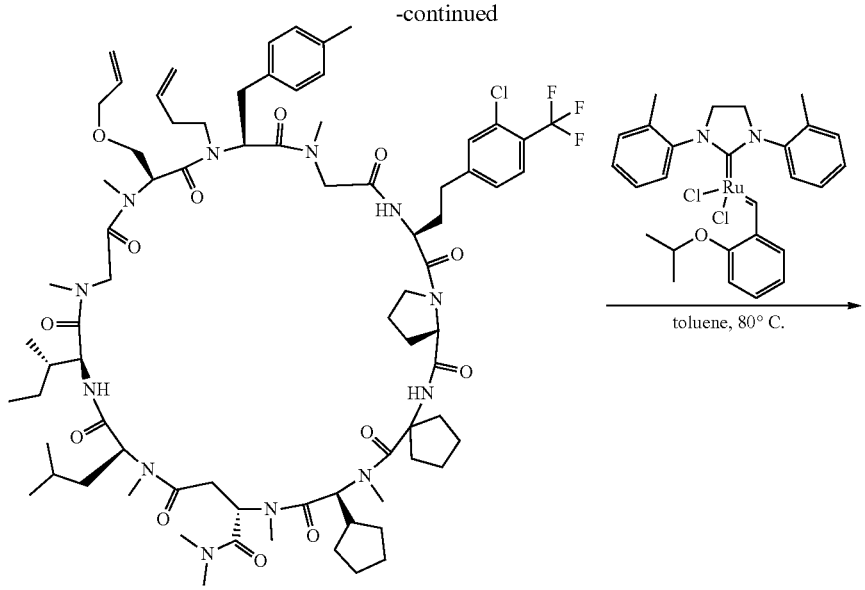

Compound PP0623-a

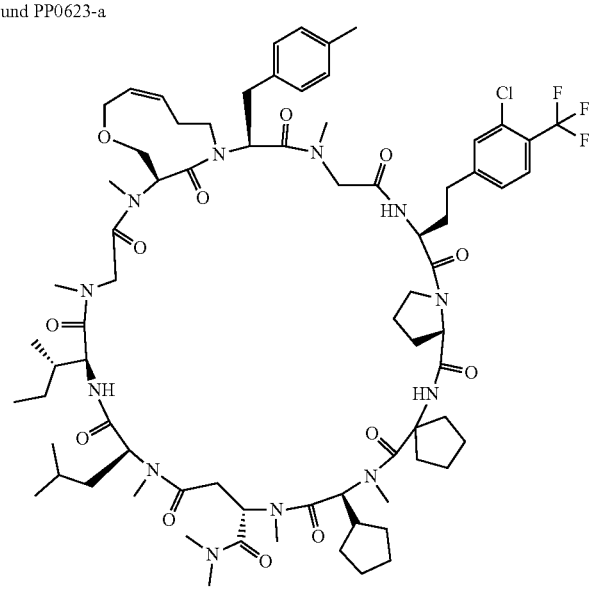

Compound PP0623

Using Compound aa374-resin as a raw material, peptide synthesis by the basic peptide synthesis method described in the present Examples was performed to give Compound PP0623-a (10.7 mg, 7.1 µmol). Using the resulting PP0623-a, PP0623 (0.4 mg, 4%) was obtained in the same manner as synthesis of Compound PP0616. LC/MS data is provided in Table 36.

Synthesis of Compound PP0624

Compound PP0624 was synthesized according to the following scheme.

aa374-resin →→→

-continued

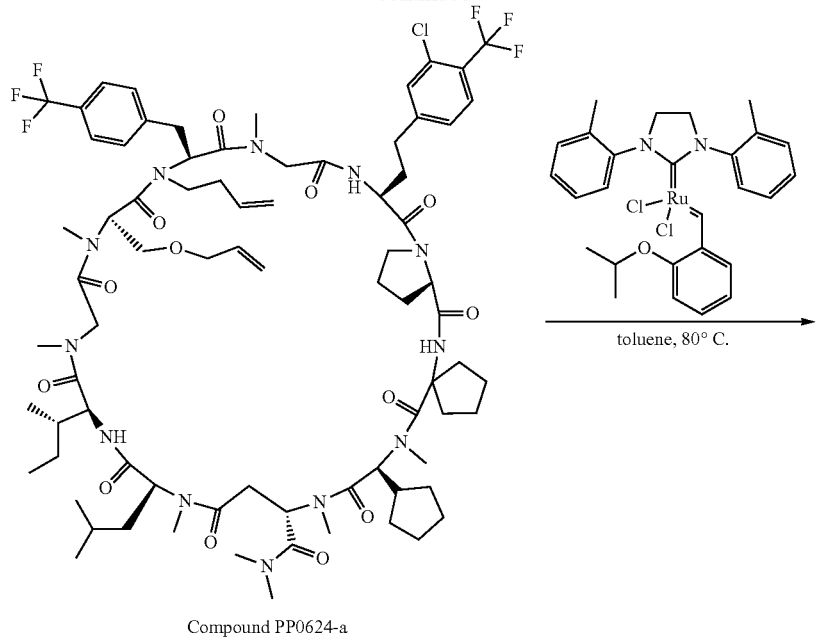

Compound PP0624-a

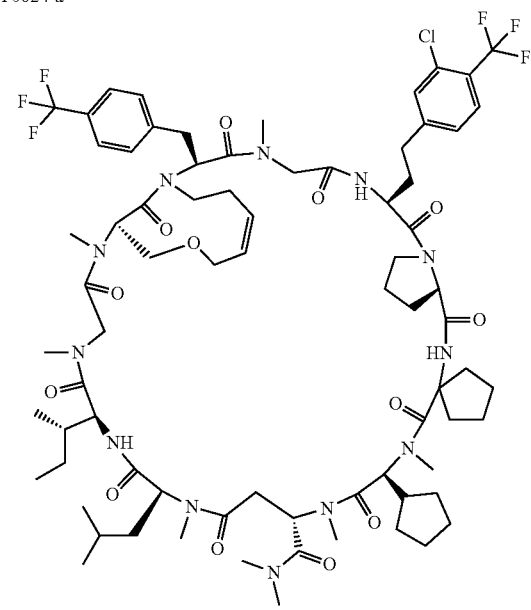

Compound PP0624

Using Compound aa374-resin as a raw material, peptide synthesis by the basic peptide synthesis method described in the present Examples was performed to give Compound PP0624-a (9.7 mg, 6.2 μmol). Using the resulting PP0624-a, PP0624 (0.3 mg, 3%) was obtained in the same manner as synthesis of Compound PP0616. LC/MS data is provided in Table 36.

Synthesis of Compound PP0625

Compound PP0625 was synthesized according to the following scheme.

aa374-resin →→

-continued

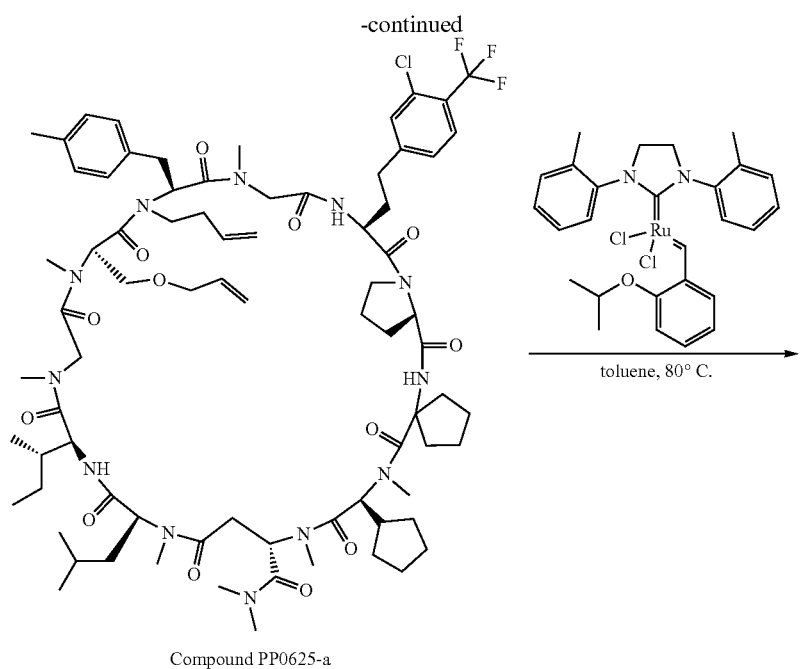

Compound PP0625-a

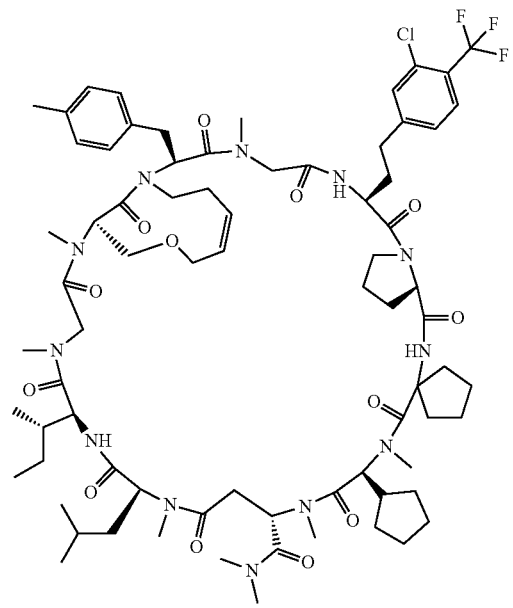

Compound PP0625

Using Compound aa374-resin as a raw material, peptide synthesis by the basic peptide synthesis method described in the present Examples was performed to give Compound PP0625-a (12.3 mg, 8.2 μmol). Using the resulting PP0625-a, PP0625 (0.3 mg, 3%) was obtained in the same manner as synthesis of Compound PP0616. LC/MS data is provided in Table 36.

Synthesis of Compound PP0626

Compound PP0626 was synthesized according to the following scheme.

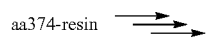

-continued

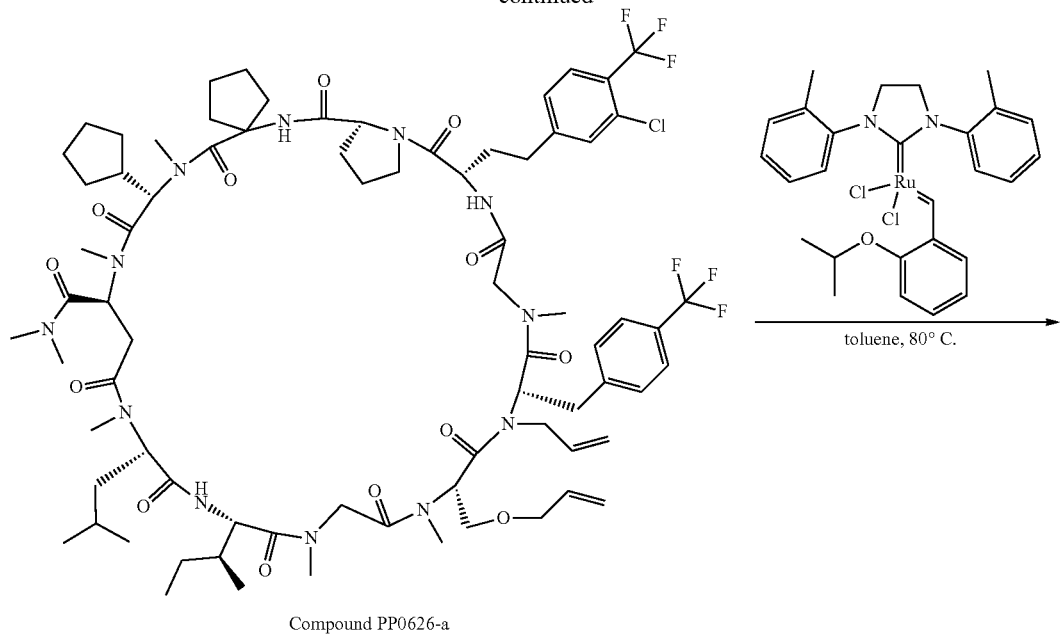

Compound PP0626-a

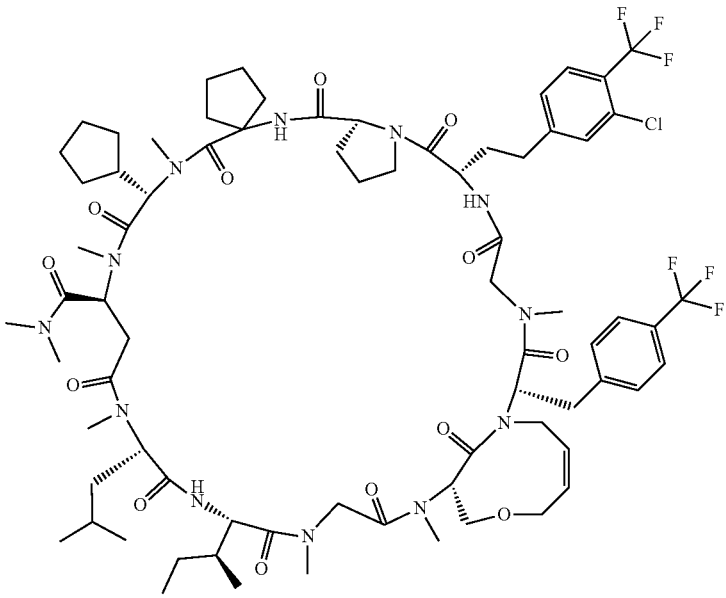

Compound PP0626

Using Compound aa374-resin as a raw material, peptide synthesis by the basic peptide synthesis method described in the present Examples was performed to give Compound PP0626-a (4.7 mg, 3.0 μmol). Using the resulting PP0626-a, PP0626 (1.6 mg, 40%) was obtained in the same manner as synthesis of Compound PP0616. LC/MS data is provided in Table 36.

Synthesis of Compound PP0627

Compound PP0627 was synthesized according to the following scheme.

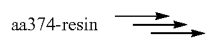

-continued

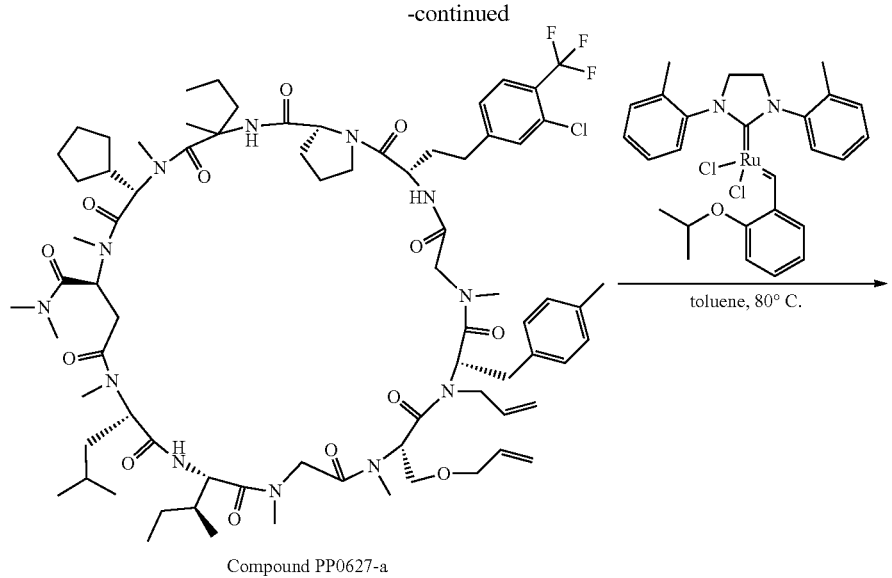

Compound PP0627-a

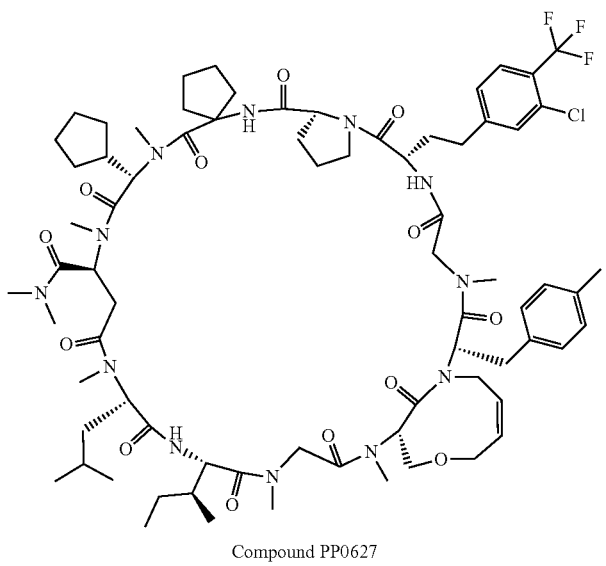

Compound PP0627

Using Compound aa374-resin as a raw material, peptide synthesis by the basic peptide synthesis method described in the present Examples was performed to give Compound PP0627-a (6.6 mg, 4.4 μmol). Using the resulting PP0627-a, PP0627 (1.2 mg, 20%) was obtained in the same manner as synthesis of Compound PP0616. LC/MS data is provided in Table 36.

Synthesis of Compound PP0628

Compound PP0628 was synthesized according to the following scheme.

aa374-resin →→

-continued

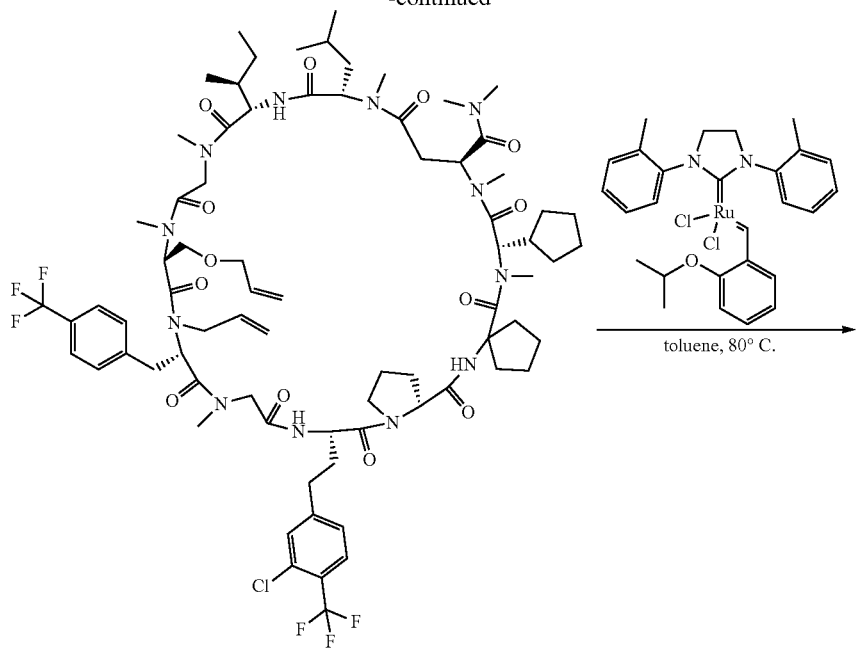

Compound PP0628-a

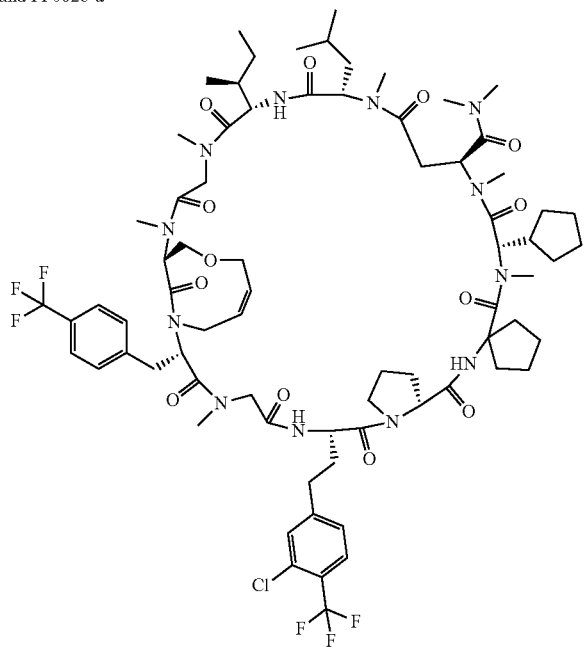

Compound PP0628

Using Compound aa374-resin as a raw material, peptide synthesis by the basic peptide synthesis method described in the present Examples was performed to give Compound PP0628-a (16.6 mg, 10.7 μmol). Using the resulting PP0628-a, PP0628 (0.5 mg, 3%) was obtained in the same manner as synthesis of Compound PP0616. LC/MS data is provided in Table 36.

Synthesis of Compound PP0629

Compound PP0629 was synthesized according to the following scheme.

aa374-resin ⟶ ⟶

-continued

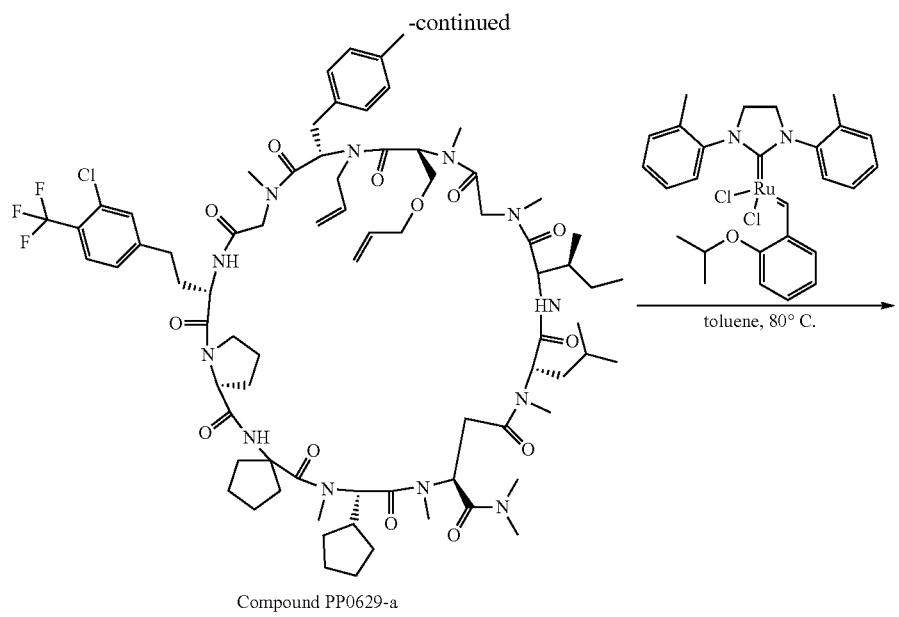

Compound PP0629-a toluene, 80° C.

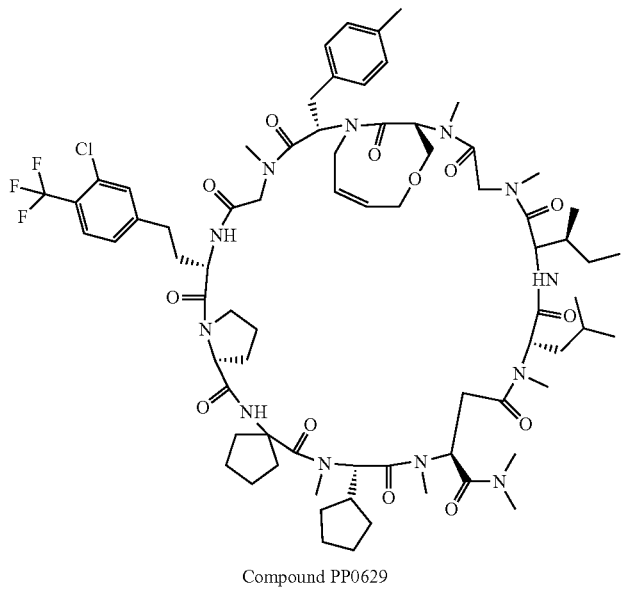

Compound PP0629

Using Compound aa374-resin as a raw material, peptide synthesis by the basic peptide synthesis method described in the present Examples was performed to give Compound PP0629-a (12.3 mg, 8.2 μmol). Using the resulting PP0629-a, PP0629 (0.7 mg, 6%) was obtained in the same manner as synthesis of Compound PP0616. LC/MS data is provided in Table 36.

Synthesis of Compound PP1332

Compound PP1332 was synthesized according to the following scheme.

aa374-resin →→

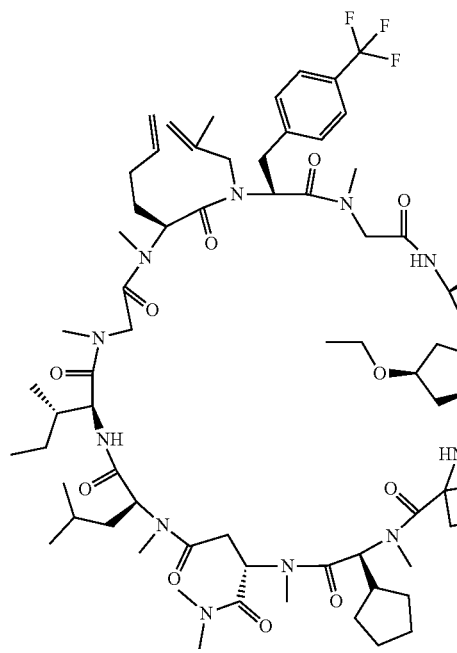

Compound PP1332-a

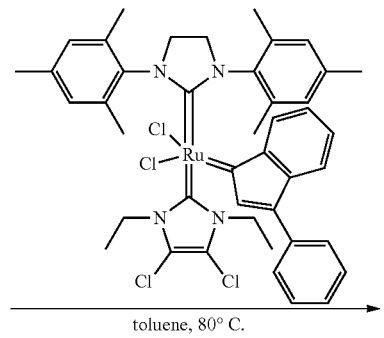

toluene, 80° C.

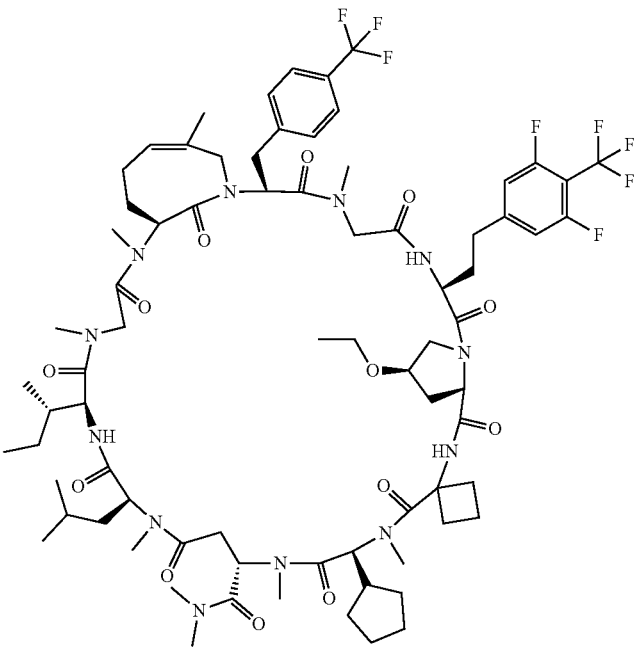

Compound PP1332

Using Compound aa374-resin as a raw material, peptide synthesis by the basic peptide synthesis method described in the present Examples was performed to give Compound PP1332-a (40.9 mg, 25.6 μmol). The resulting Compound PP1332-a (40 mg) and 1,3-bis(2,4,6-trimethylphenyl)-2-imidazolidinylidene)(3-phenyl-1H-inden-1-ylidene)(4,5-dichloro-1,3-diethyl-1,3-dihydro-2H-imidazol-2-ylidene) ruthenium (II) chloride (22 mg, 0.025 mmol) were dissolved in toluene (3 mL), and the mixture was stirred at 100° C. for 13.5 hours in a nitrogen atmosphere. After cooling to room temperature, the solvent was distilled off under reduced pressure. The resulting crude product was purified by reverse phase HPLC(methanol/50 mM aqueous ammonium acetate solution) to give PP1332 (11.5 mg, 17%). LC/MS data is provided in Table 36.

Synthesis of Compound PP1333

Compound PP1333 was synthesized according to the following scheme.

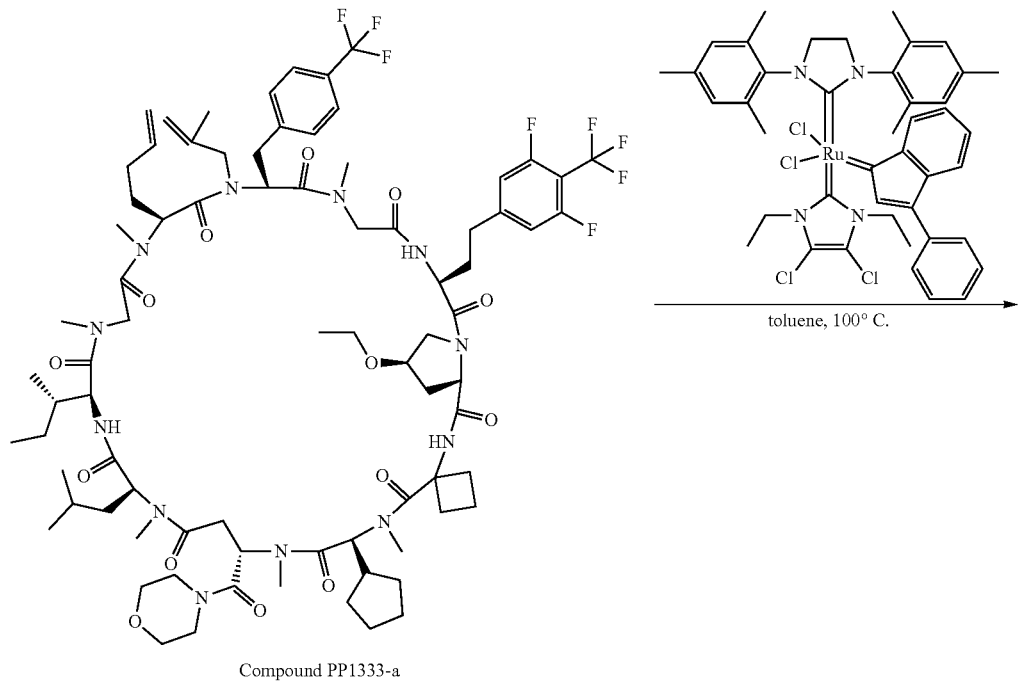

Compound PP1333-a

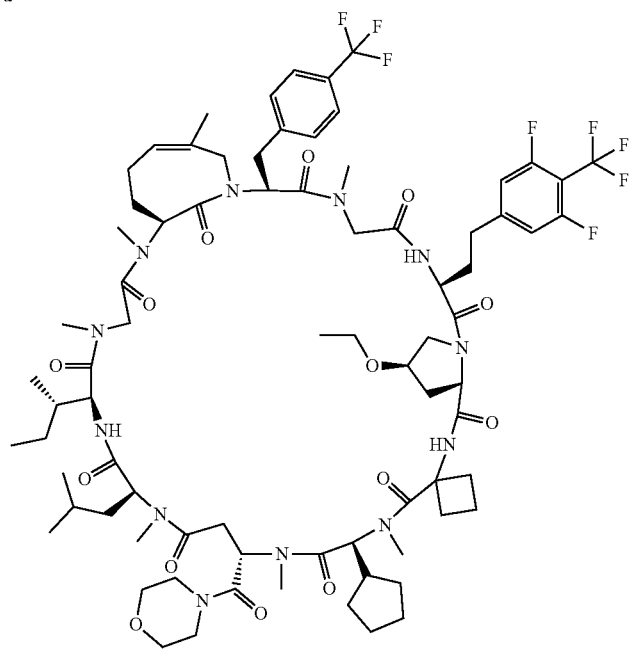

Compound PP1333

Using Compound aa375-resin as a raw material, peptide synthesis by the basic peptide synthesis method described in the present Examples was performed to give Compound PP1333-a (55.1 mg, 34.1 μmol). Using the resulting PP1333-a, PP1333 (8.2 mg, 15%) was obtained in the same manner as synthesis of Compound PP1332. LC/MS data is provided in Table 36.

Synthesis of Compound PP1334

Compound PP1334 was synthesized according to the following scheme.

711

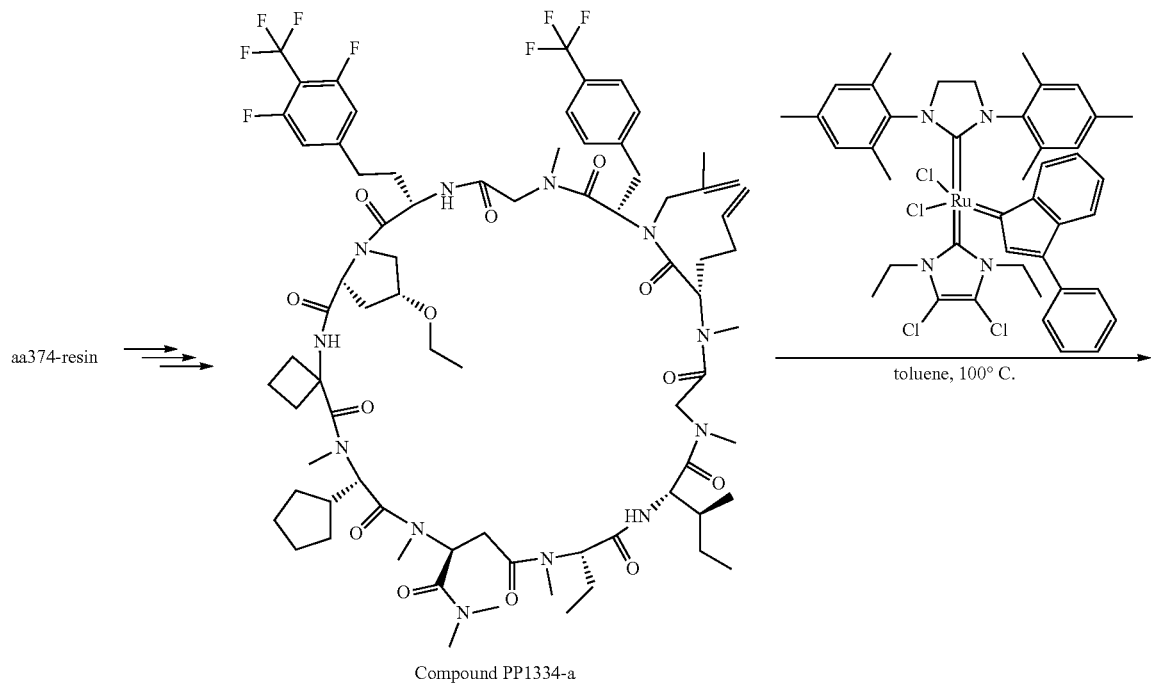

Compound PP1334-a

712

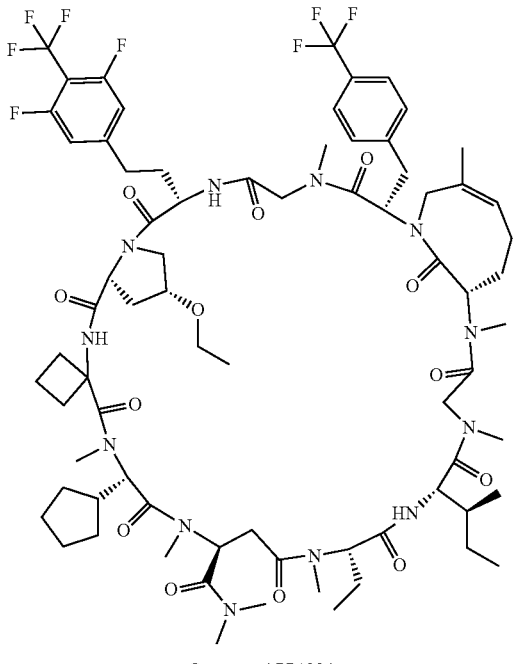

toluene, 100° C.

Compound PP1334

Using Compound aa374-resin as a raw material, peptide synthesis by the basic peptide synthesis method described in the present Examples was performed to give Compound PP1334-a (76.1 mg, 49.1 μmol). Using the resulting PP1334-a, PP1334 (2.8 mg, 4%) was obtained in the same manner as synthesis of Compound PP1332. LC/MS data is provided in Table 36.

Synthesis of Compound PP1335

Compound PP1335 was synthesized according to the following scheme.

713 aa375-resin ⟶⟶⟶

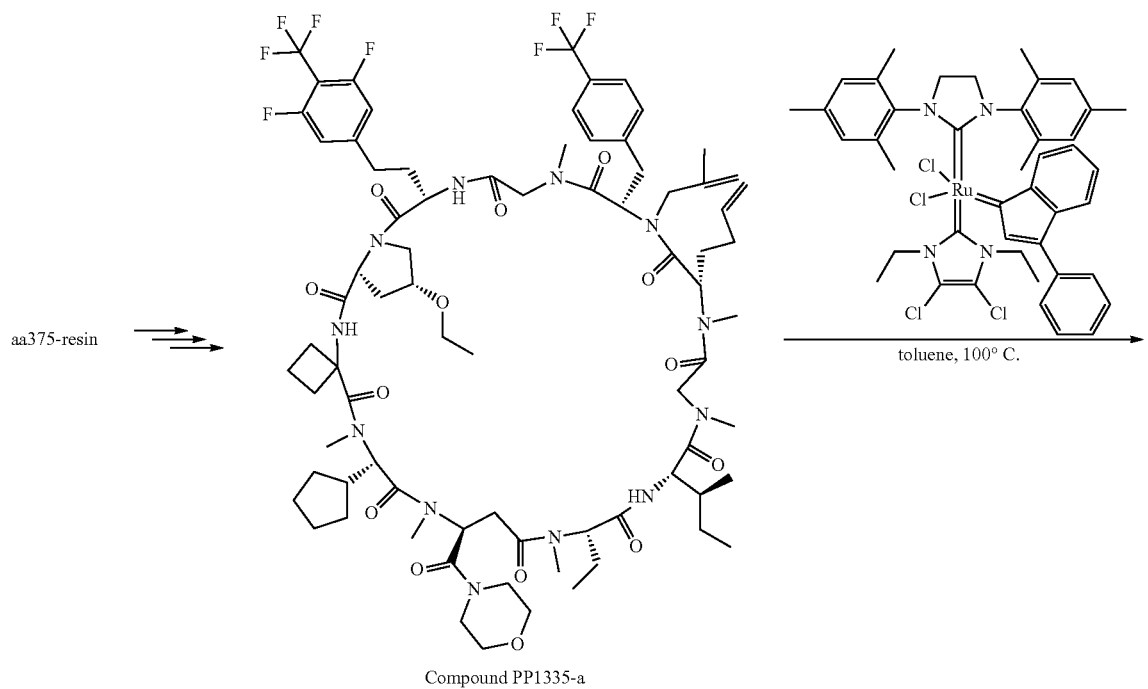

Compound PP1335-a

714

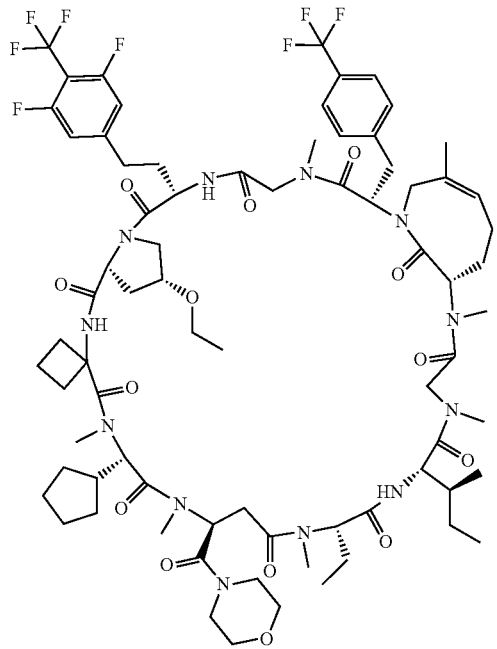

toluene, 100° C.
⟶

Compound PP1335

Using Compound aa375-resin as a raw material, peptide synthesis by the basic peptide synthesis method described in the present Examples was performed to give Compound PP1335-a (71.8 mg, 45.5 μmol). Using the resulting PP1335-a, PP1335 (2.5 mg, 4%) was obtained in the same manner as synthesis of Compound PP1332. LC/MS data is provided in Table 36.

Synthesis of Compound PP0894

Compound PP0894 was synthesized according to the following scheme.

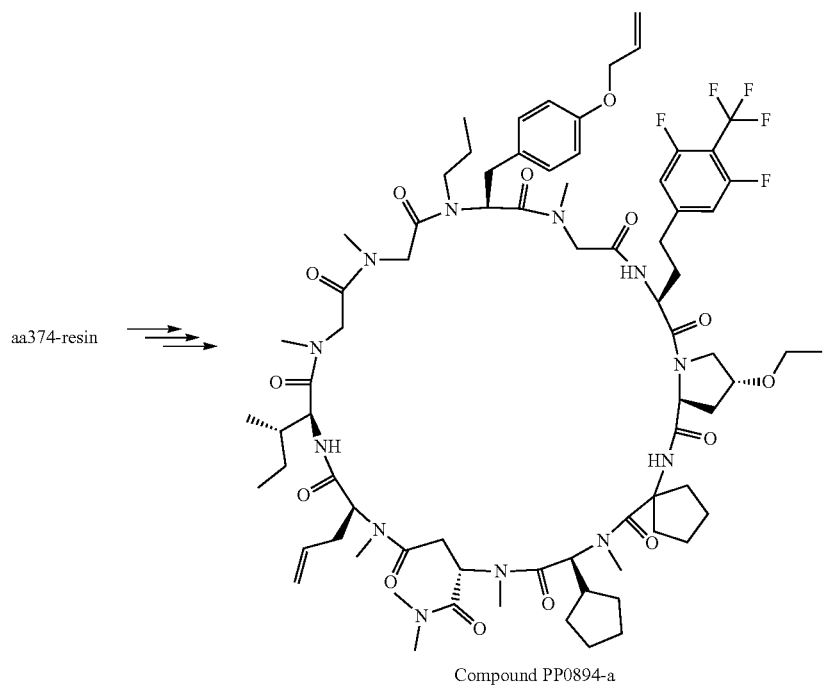
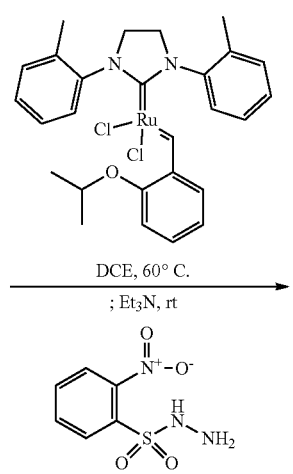

Compound PP0894-a

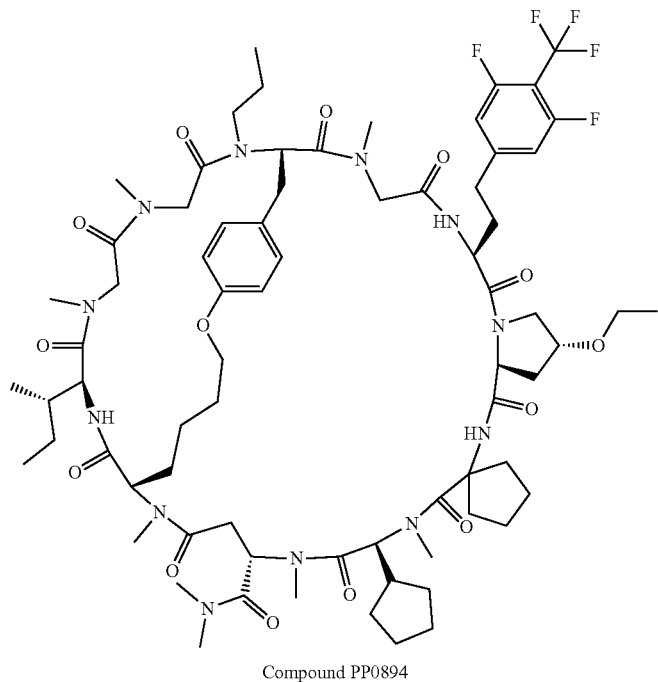

Compound PP0894

Using Compound aa374-resin as a raw material, peptide synthesis by the basic peptide synthesis method described in the present Examples was performed to give Compound PP0894-a (26.5 mg, 18 μmol).

LCMS (ESI) m/z=1496 (M+H)+

Retention time: 0.78 min (Analytical condition SQDAA50)

Compound PP0894-a (26.5 mg, 18 μmol) and a Stewart-Grubbs catalyst (5.0 mg, 8.76 μmol) were dissolved in 1,2-dichloroethane (0.58 mL), and the mixture was stirred at 60° C. for 20 hours in a nitrogen atmosphere. After cooling to room temperature, triethylamine (98 μL, 0.701 mmol) and 2-nitrobenzenesulfonohydrazide (152 mg, 0.701 mmol) were added, and the mixture was stirred at room temperature for 5 days. Then, the reaction solution was concentrated under reduced pressure. The resulting crude product was purified by reverse phase HPLC(methanol/50 mM aqueous ammonium acetate solution) to give PP0894 (4.5 mg, 17%). LC/MS data is provided in Table 36.

Synthesis of Compound PP0895 and Compound PP900

Compounds PP0895 and PP900 were synthesized according to the following scheme.

717
718
aa374-resin →→→ 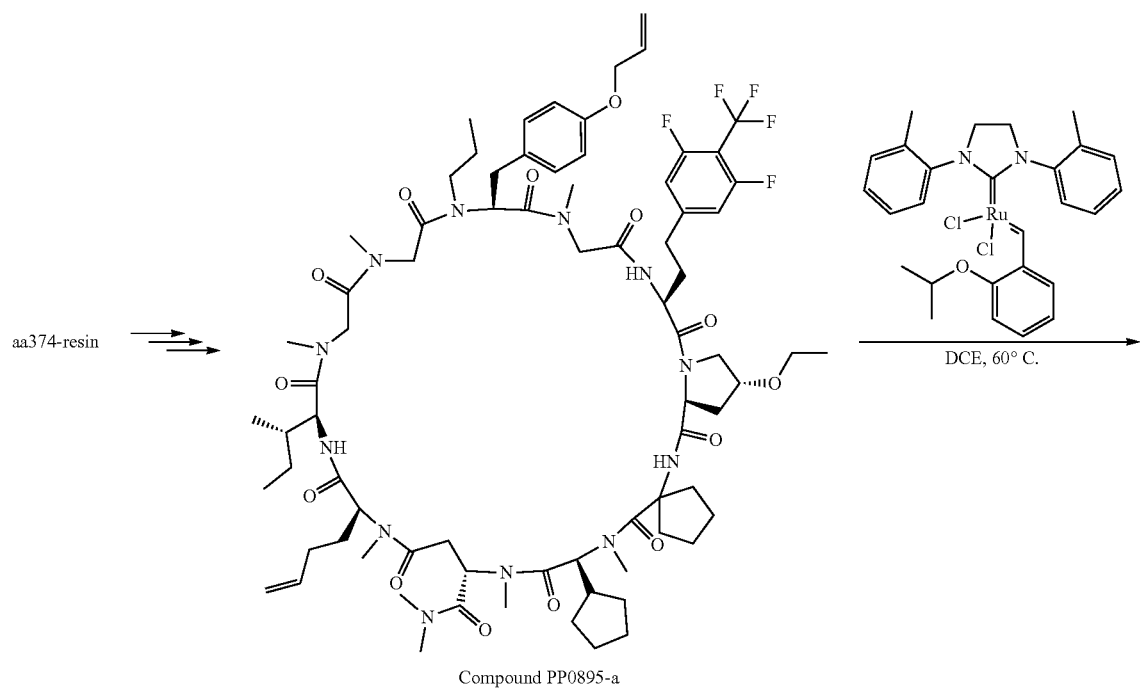
Compound PP0895-a
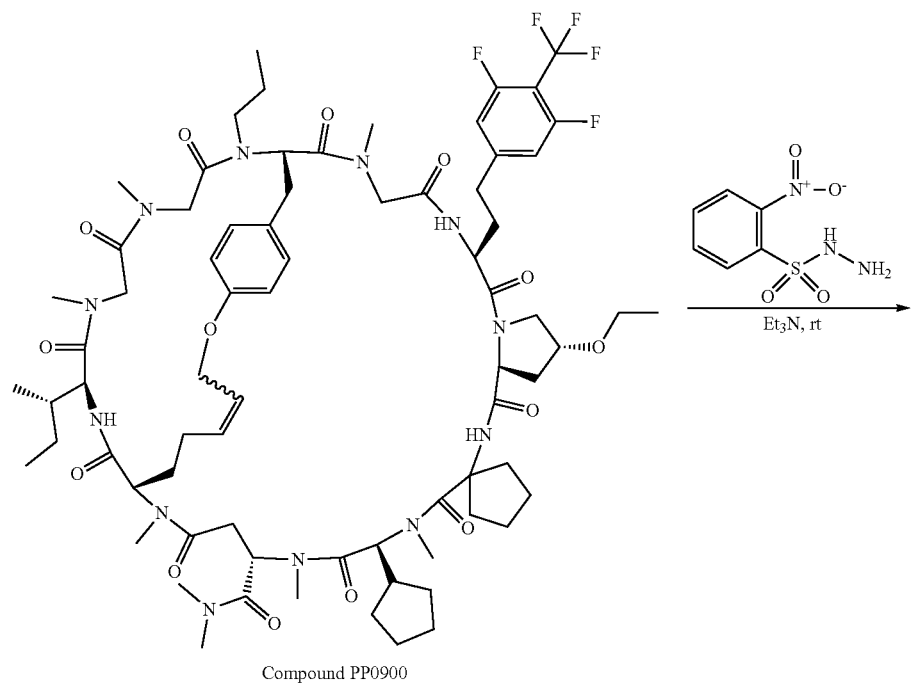
Compound PP0900

-continued

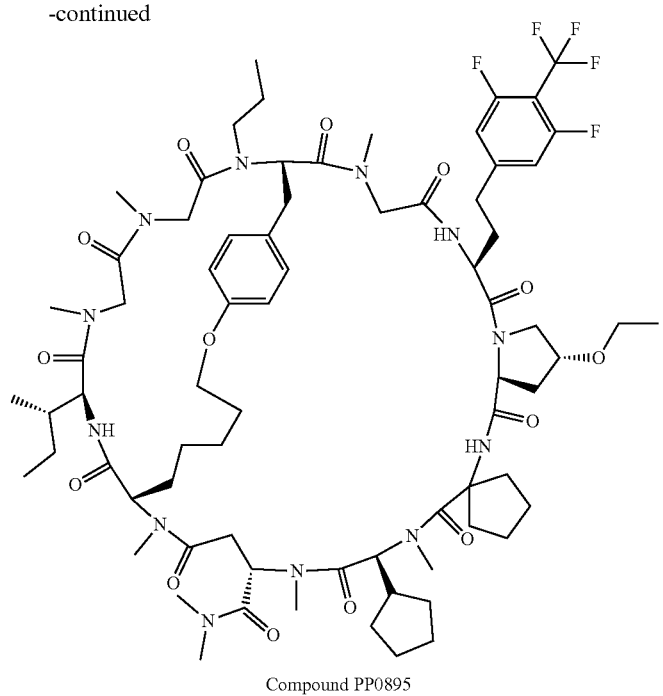

Compound PP0895

Using Compound aa374-resin as a raw material, peptide synthesis by the basic peptide synthesis method described in the present Examples was performed to give Compound PP0895-a. The resulting Compound PP0895-a (26.5 mg, 18 μmol) and a Stewart-Grubbs catalyst (5.0 mg, 8.76 μmol) were dissolved in 1,2-dichloroethane (0.58 mL), and the mixture was stirred at 60° C. for 20 hours in a nitrogen atmosphere. One-third of the reaction solution was recovered and concentrated under reduced pressure, and the resulting crude product was purified by reverse phase HPLC (methanol/50 mM aqueous ammonium acetate solution) to give PP0900 (2.1 mg, 8.1%). LC/MS data is provided in Table 36.

After the remaining reaction solution was cooled to room temperature, triethylamine (98 μL, 0.701 mmol) and 2-nitrobenzenesulfonohydrazide (152 mg, 0.701 mmol) were added, and the mixture was stirred at room temperature for 5 days. Then, the reaction solution was concentrated under reduced pressure. The resulting crude product was purified by reverse phase HPLC(methanol/50 mM aqueous ammonium acetate solution) to give PP0895 (4.4 mg, 17%). LC/MS data is provided in Table 36.

Synthesis of Compound PP0896

Compound PP0896 was synthesized according to the following scheme.

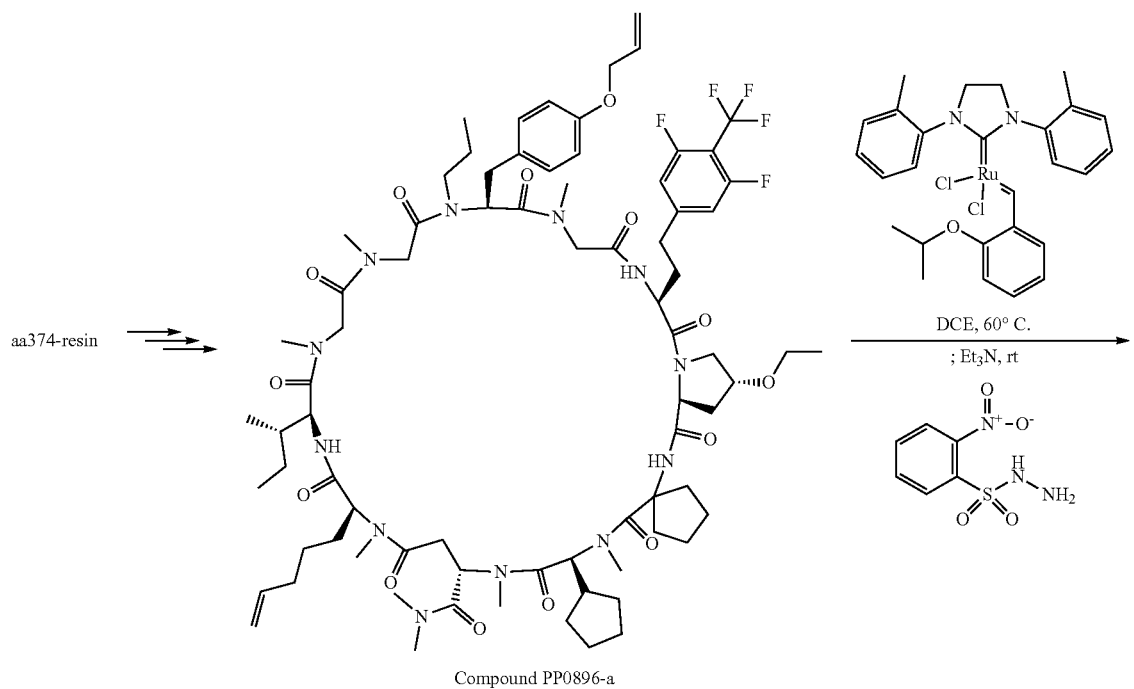

Compound PP0896-a

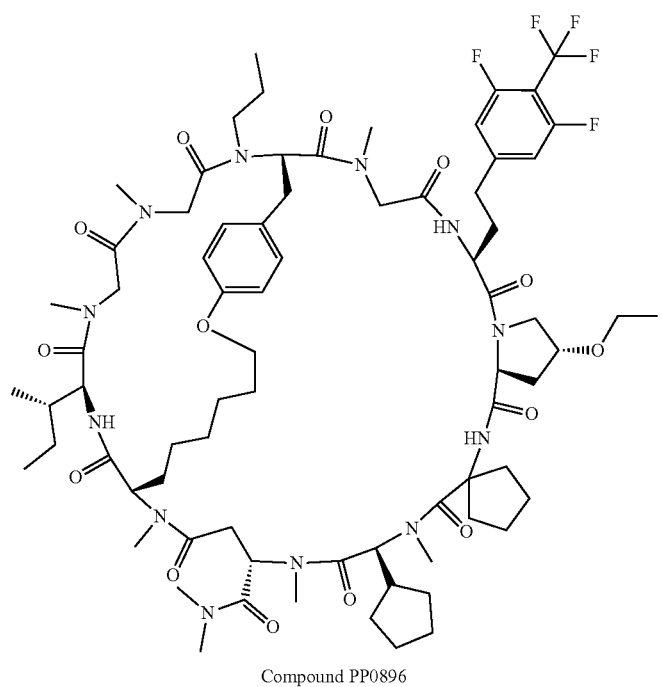

Compound PP0896

Using Compound aa374-resin as a raw material, peptide synthesis by the basic peptide synthesis method described in the present Examples was performed to give Compound PP0896-a. Using the resulting PP0896-a, PP0896 (4.5 mg, 17%) was obtained in the same manner as synthesis of Compound PP0894. LC/MS data is provided in Table 36.

Synthesis of Compound PP0898 and Compound PP902

Compounds PP0898 and PP902 were synthesized according to the following scheme.

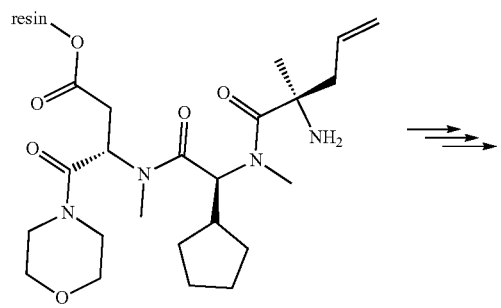
Compound PP0874-b
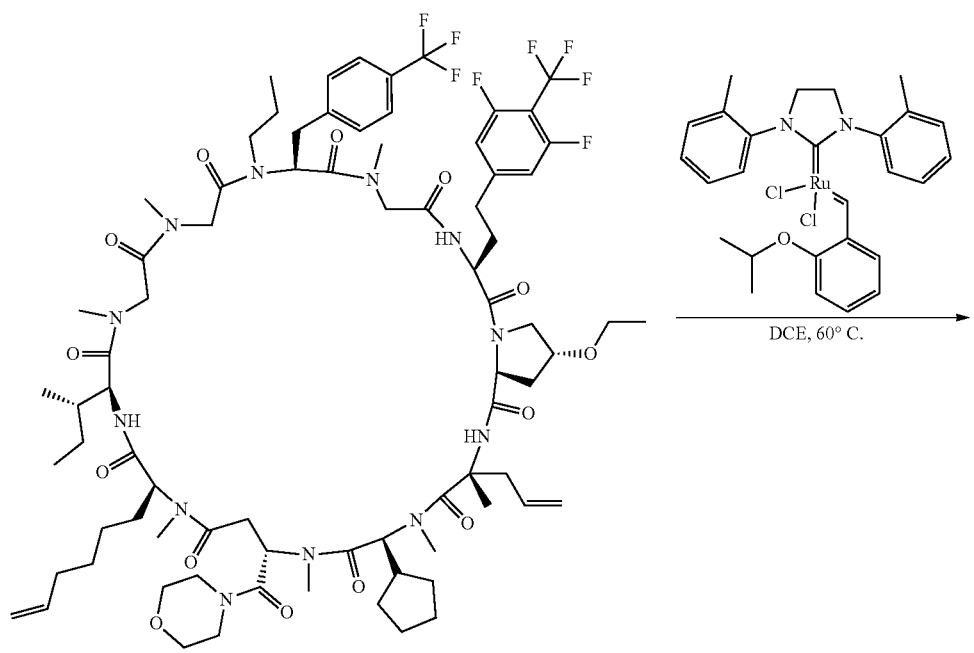
Compound PP0898-a
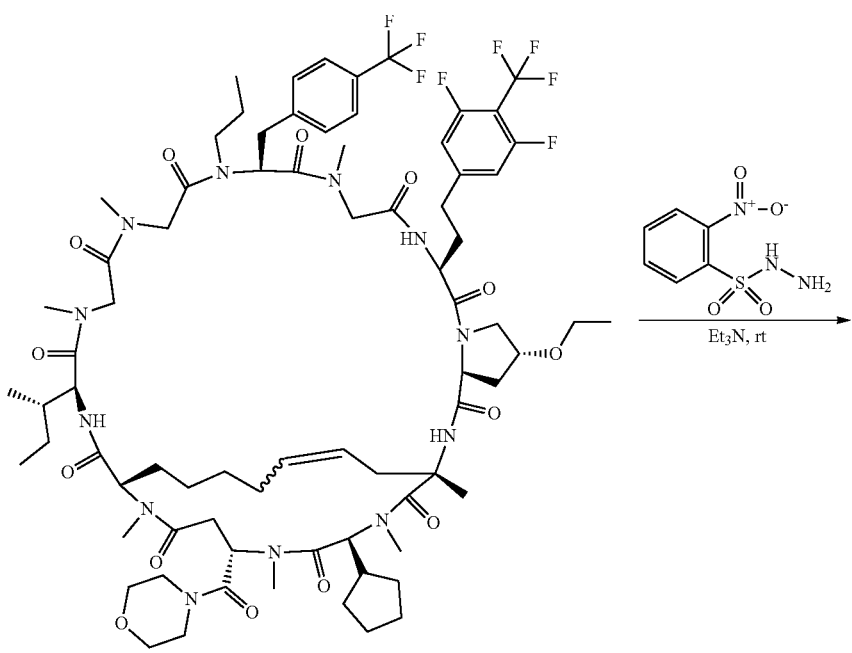
Compound PP0902

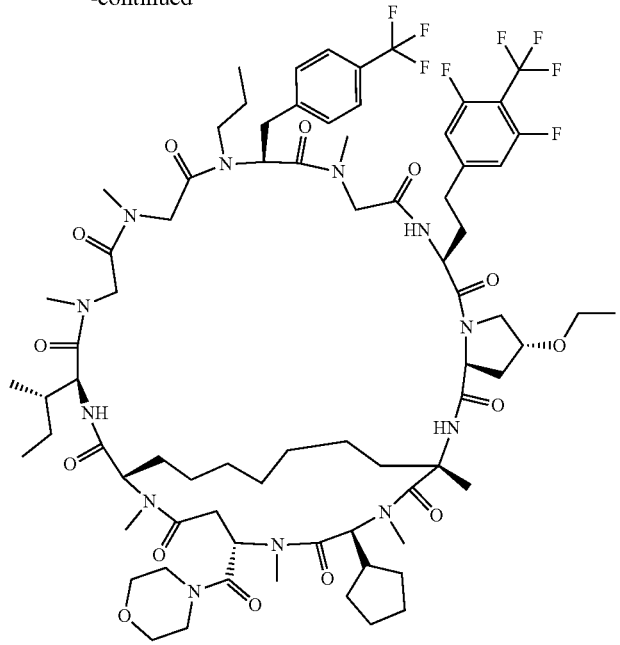

Compound PP0898

Using, as a raw material, resin-supported PP0874-b that was a synthesis intermediate of Compound PP0874 synthesized using Compound aa375-resin, peptide synthesis by the basic peptide synthesis method described in the present Examples was performed to give Compound PP0898-a. Using the resulting PP0898-a, PP902 (1.1 mg, 4.2%) was obtained in the same manner as synthesis of Compound PP900. Using Compound PP902, PP0898 (2.0 mg, 7.7%) was obtained in the same manner as synthesis of Compound PP0895. LC/MS data is provided in Table 36.

Synthesis of Compound PP0899 and Compound PP903

Compounds PP0899 and PP903 were synthesized according to the following scheme.

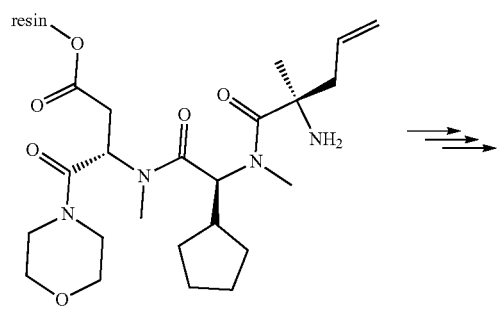

Compound PP0874-b

-continued
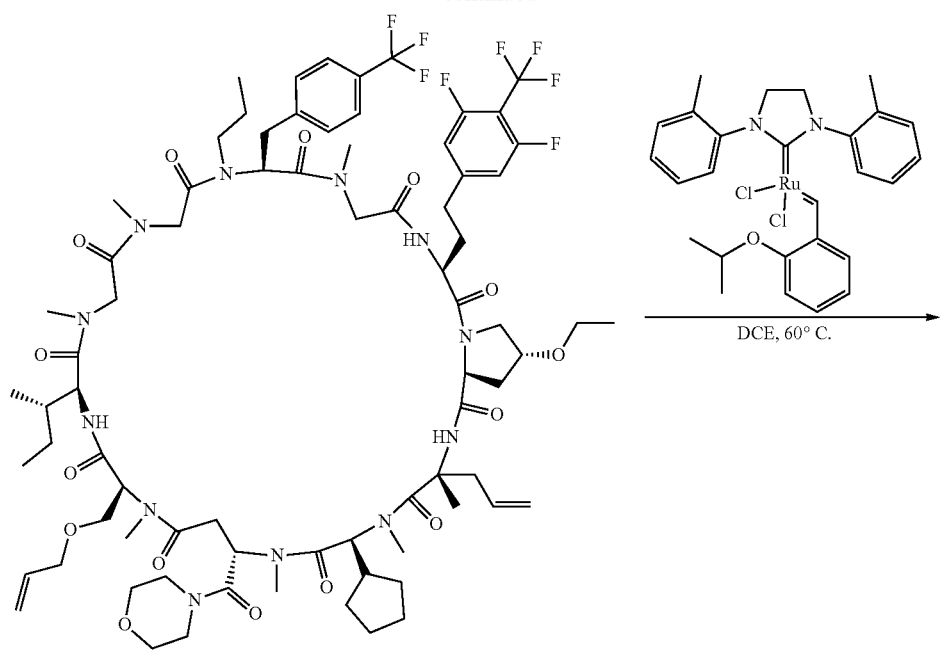
Compound PP0899-a
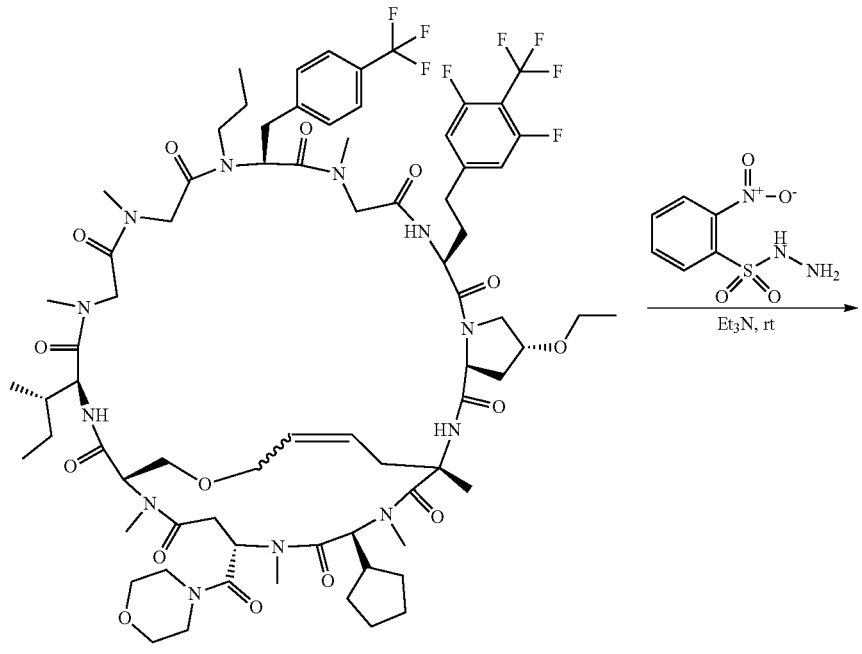
Compound PP0903

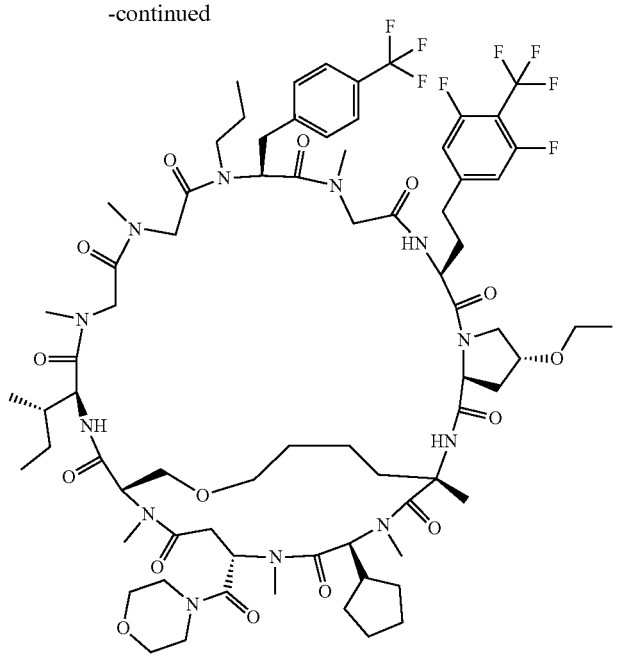

Compound PP0899

Using, as a raw material, resin-supported PP0874-b that was a synthesis intermediate of Compound PP0874 synthesized using Compound aa375-resin, peptide synthesis by the basic peptide synthesis method described in the present Examples was performed to give Compound PP0899-a. Using the resulting PP0899-a, PP903 (1.1 mg, 4%) was obtained in the same manner as synthesis of Compound PP900. Using Compound PP903, PP0899 (3.1 mg, 12%) was obtained in the same manner as synthesis of Compound PP0895. LC/MS data is provided in Table 36.

Synthesis of Compound PP901

Compound PP901 was synthesized according to the following scheme.

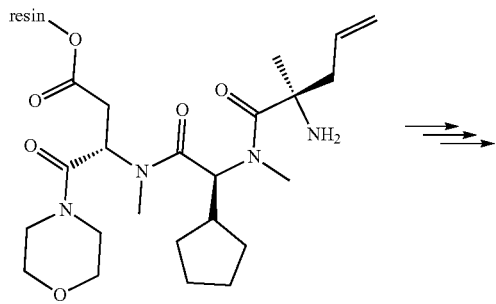

Compound PP0874-b

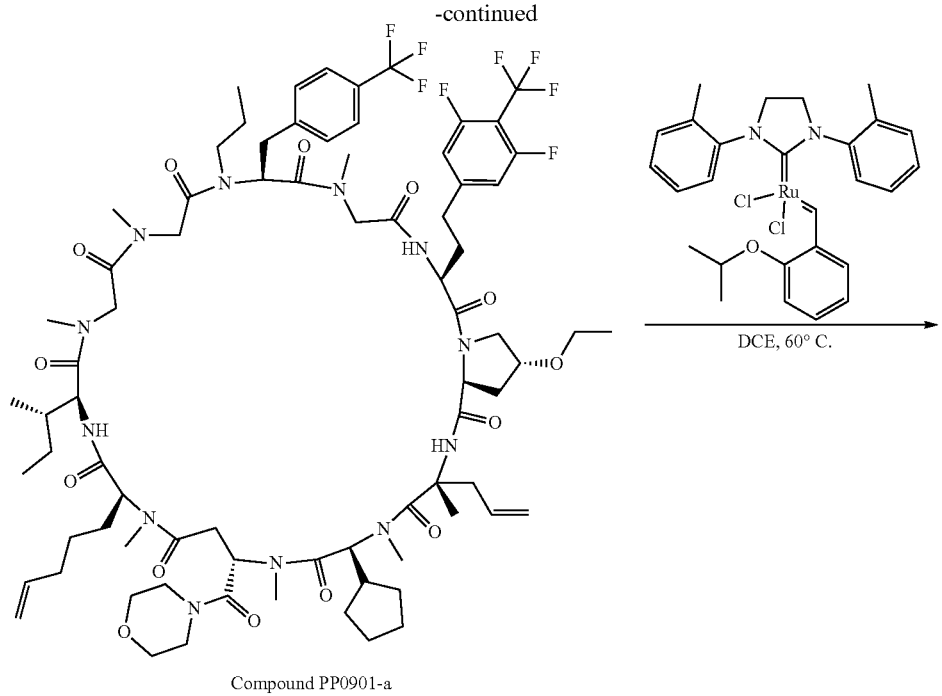

Compound PP0901-a

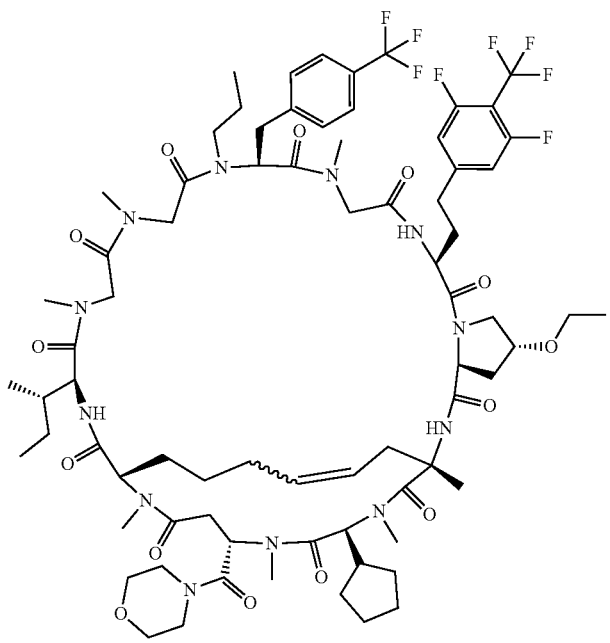

Compound PP0901

Using, as a raw material, resin-supported synthesis intermediate PP0874-b of Compound PP0874 synthesized using Compound aa375-resin, peptide synthesis by the basic peptide synthesis method described in the present Examples was performed to give Compound PP0901-a. The resulting Compound PP0901-a (26.5 mg, 18 μmol) and a Stewart-Grubbs catalyst (5.0 mg, 8.76 μmol) were dissolved in 1,2-dichloroethane (0.58 mL), and the mixture was stirred at 60° C. for 20 hours in a nitrogen atmosphere. After being cooled to room temperature, the reaction solution was concentrated under reduced pressure. The resulting crude product was purified by reverse phase HPLC(methanol/50 mM aqueous ammonium acetate solution) to give PP0901 (0.8 mg, 3%). LC/MS data is provided in Table 36.

Synthesis of Compound PP925

Compound PP925 was synthesized according to the following scheme.

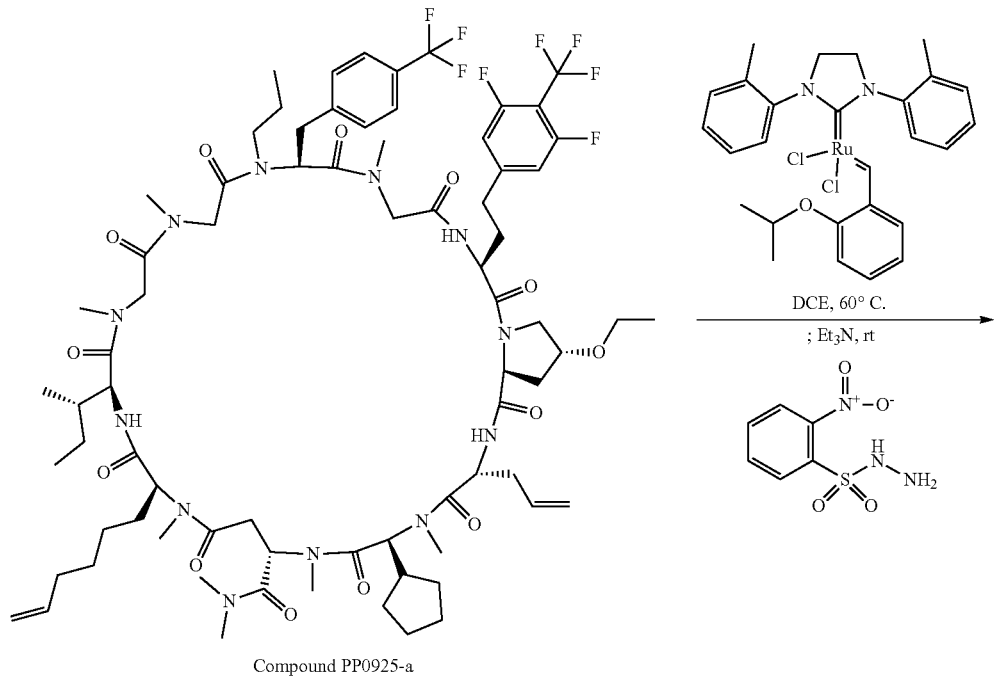

Compound PP0925-a

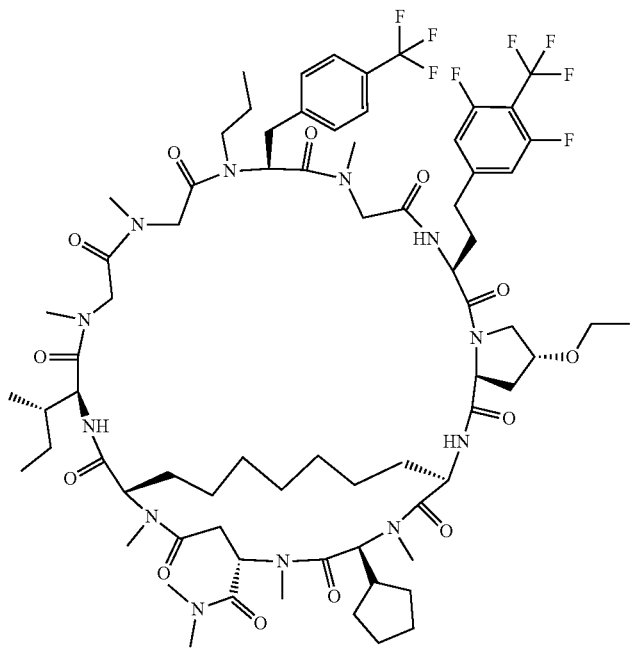

Compound PP0925

Using Compound aa374-resin as a raw material, peptide synthesis by the basic peptide synthesis method described in the present Examples was performed to give Compound PP0925-a. Using the resulting PP925-a, PP925 (1.1 mg, 4%) was obtained in the same manner as synthesis of Compound PP0894. LC/MS data is provided in Table 36.

Synthesis of Compound PP992

Compound PP992 was synthesized according to the following scheme.

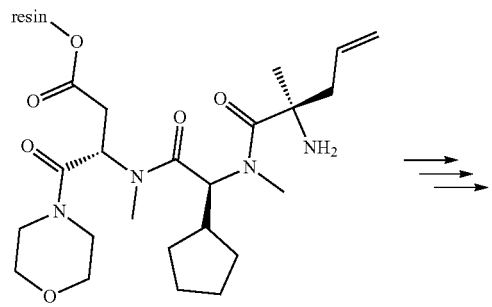
Compound PP0874-b
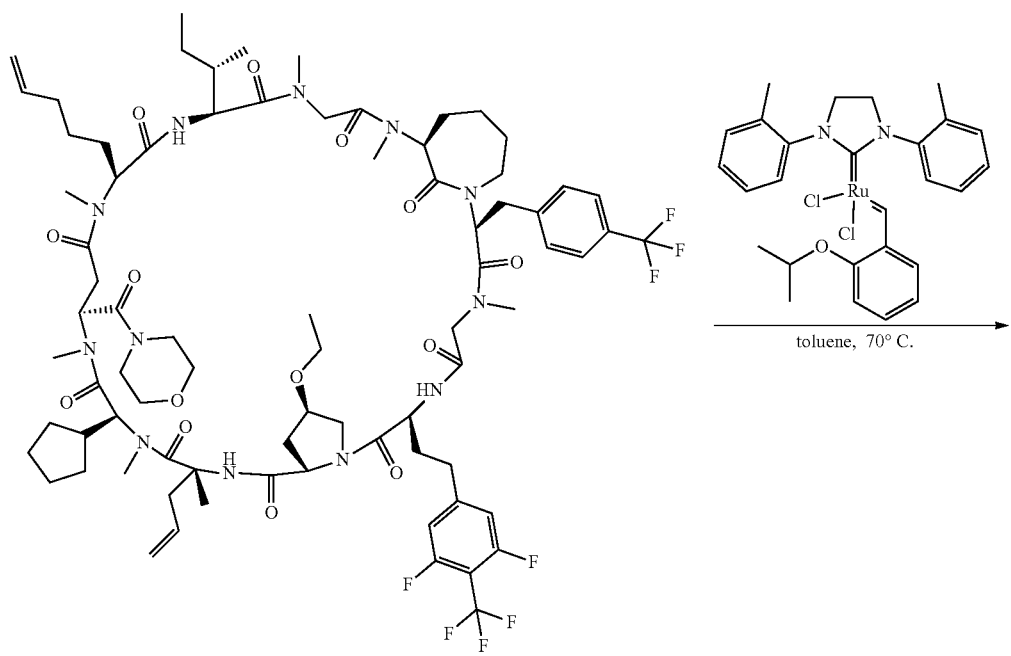
Compound PP0992-a
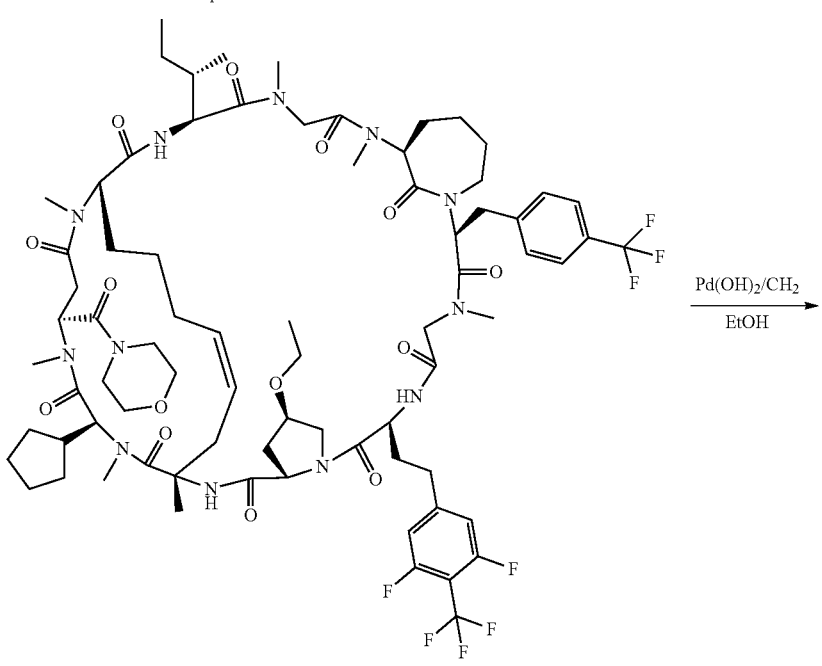
Compound PP0992-b -continued

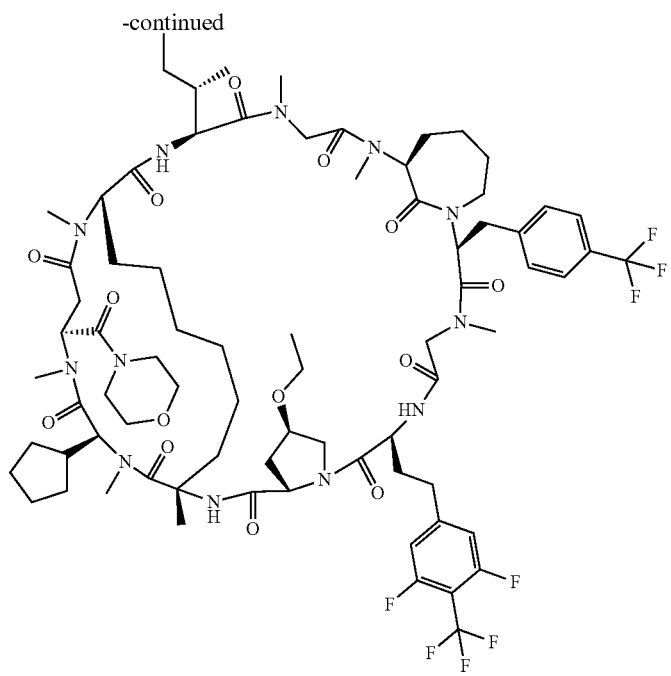

Compound PP0992

Using, as a raw material, resin-supported synthesis intermediate PP0874-b of Compound PP0874 synthesized using Compound aa375-resin, peptide synthesis by the basic peptide synthesis method described in the present Examples was performed to give Compound PP0992-a (10.07 mg, 6.33 µmol).

LCMS (ESI) m/z=1590 (M+H)+

Retention time: 1.85 min (Analytical condition SQDFA50 long)

Compound PP992-a (9.09 mg, 5.72 µmol) and a Stewart-Grubbs catalyst (1.8 mg, 3.1 µmol) were dissolved in toluene (0.41 mL), and the mixture was stirred at 70° C. for 5 hours in a nitrogen atmosphere. After cooling to room temperature, the solvent was distilled off under reduced pressure. The resulting crude product was purified by reverse phase HPLC (methanol/50 mM aqueous ammonium acetate solution) to give PP0992-b (3.5 mg, 36%).

LCMS (ESI) m/z=1562 (M+H)+

Retention time: 0.95 min (Analytical condition SQDFA05)

Compound PP992-b (3.5 mg, 2.24 µmol) was dissolved in ethanol (1.5 mL.), palladium hydroxide on carbon (20 wt %, 10 mg, 0.028 mmol) was added, and the mixture was stirred at room temperature for 2 hours in a hydrogen atmosphere. Subsequently, the reaction solution was filtered through Celite, Celite was washed with ethanol, and then the filtrate was concentrated under reduced pressure. The resulting crude product was purified by reverse phase HPLC(methanol/50 mM aqueous ammonium acetate solution) to give PP0992 (1.3 mg, 26%).

LCMS (ESI) m/z=1564 (M+H)+

Retention time: 1.22 min (Analytical condition SQDFA50 long)

Synthesis of Compound PP993

Compound PP993 was synthesized according to the following scheme.

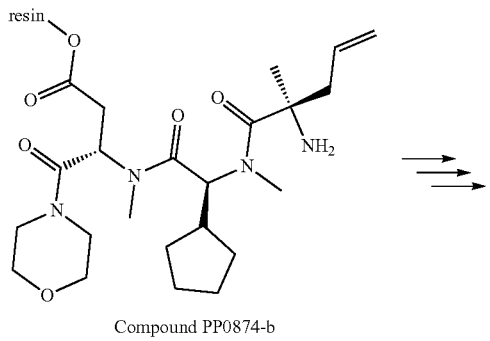

Compound PP0874-b

739
-continued
740
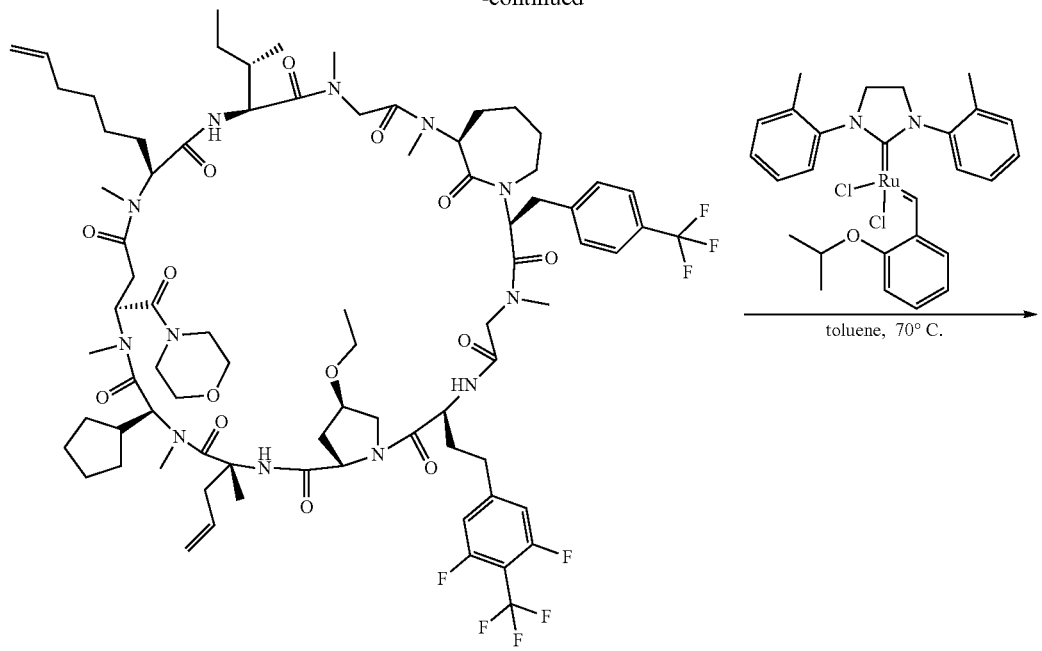
Compound PP0993-a
toluene, 70° C.
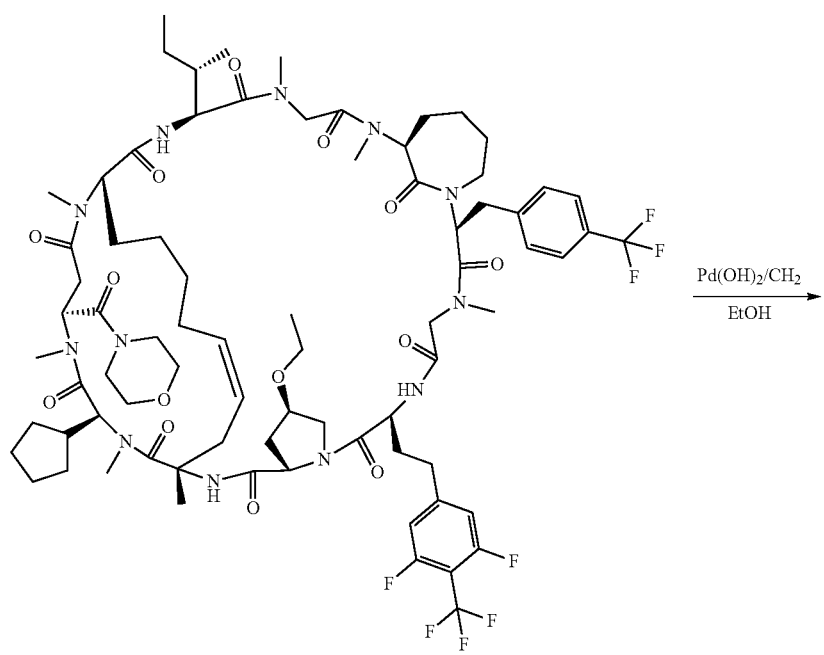
Compound PP0993-b
Pd(OH)$_2$/CH$_2$
EtOH -continued

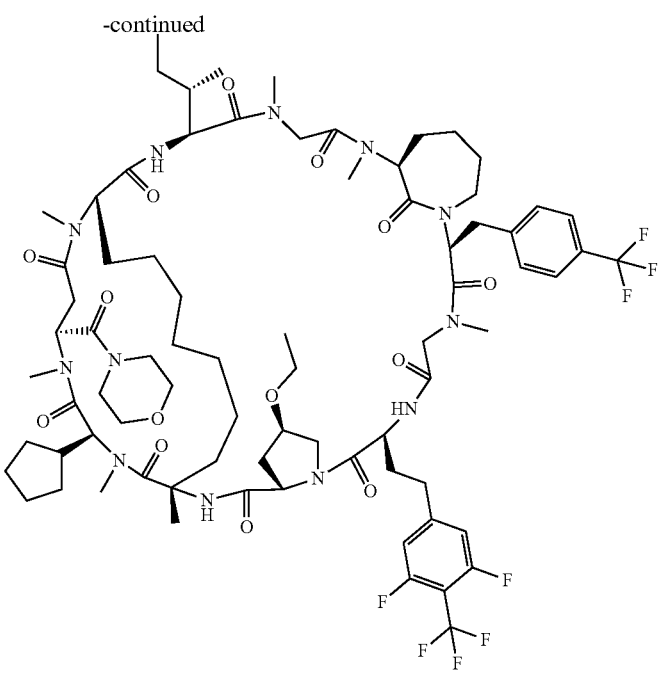

Compound PP0993

Using, as a raw material, resin-supported synthesis intermediate PP0874-b of Compound PP0874 synthesized using Compound aa375-resin, peptide synthesis by the basic peptide synthesis method described in the present Examples was performed to give Compound PP0993-a (10.6 mg). Using the resulting PP993-a, PP993-b was obtained in the same manner as synthesis of Compound PP992-b, and then PP993 (1.79 mg, 18%, 2 steps) was obtained in the same manner as synthesis of Compound PP992. LC/MS data is provided in Table 36.

Synthesis of Compound PP997

Compound PP997 was synthesized according to the following scheme.

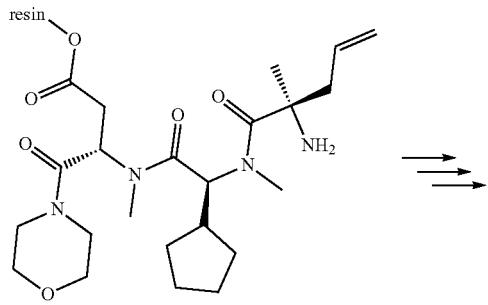

Compound PP0874-b

743
-continued
744
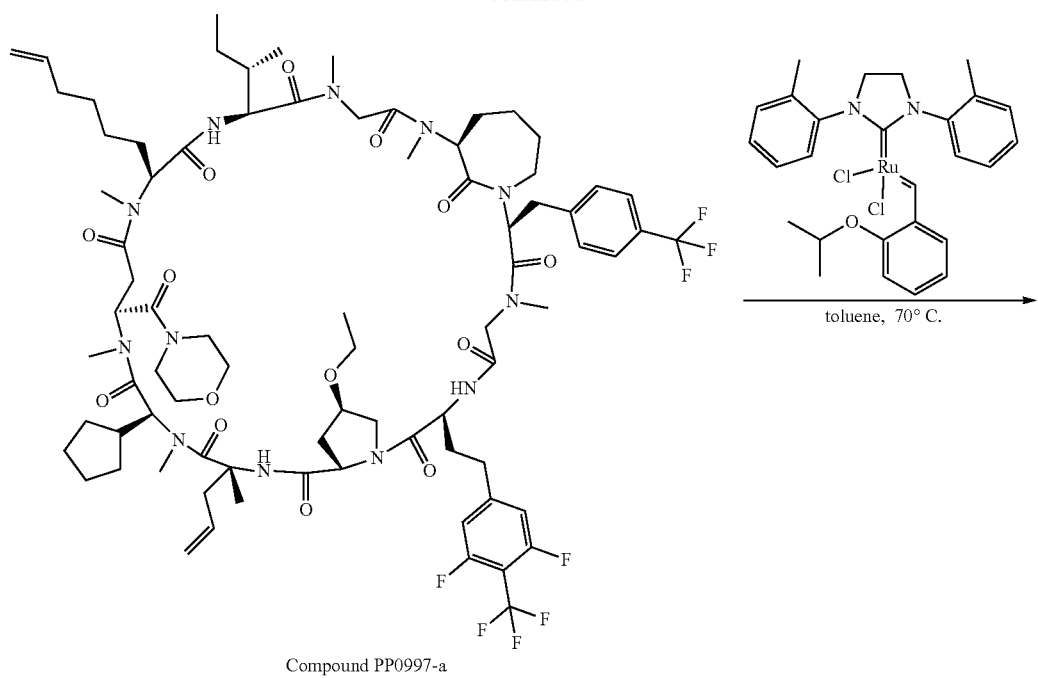
Compound PP0997-a
toluene, 70° C.
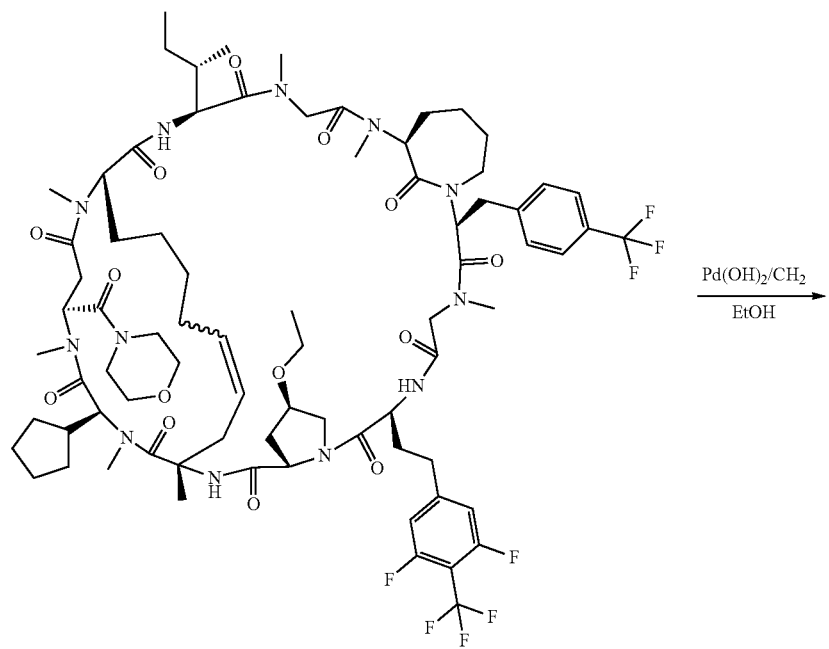
Compound PP0997-b
Pd(OH)$_2$/CH$_2$
EtOH

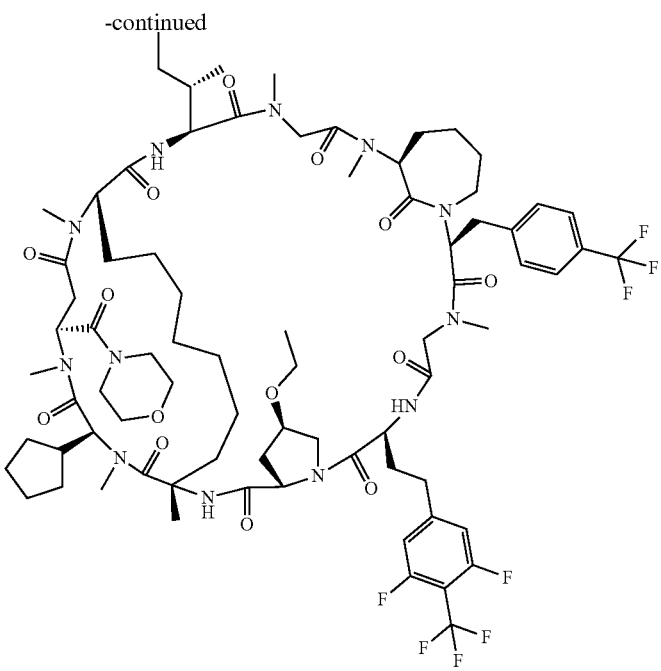

Compound PP0997

Using, as a raw material, resin-supported synthesis intermediate PP0874-b of Compound PP0874 synthesized using Compound aa375-resin, peptide synthesis by the basic peptide synthesis method described in the present Examples was performed to give Compound PP0997-a (9.5 mg). Using the resulting PP0997-a, PP997-b was obtained in the same manner as synthesis of Compound PP992-b. A half of this was reacted in the same manner as Compound PP992, the other half was reacted using 10% palladium on carbon in place of palladium hydroxide, and the resulting compounds were combined to give PP0997 (1.56 mg, 31%, 2 steps). LC/MS data is provided in Table 36.

Synthesis of Compound PP1828

Synthesis of PP1828 was carried out according to the following scheme.

aa440-resin →→

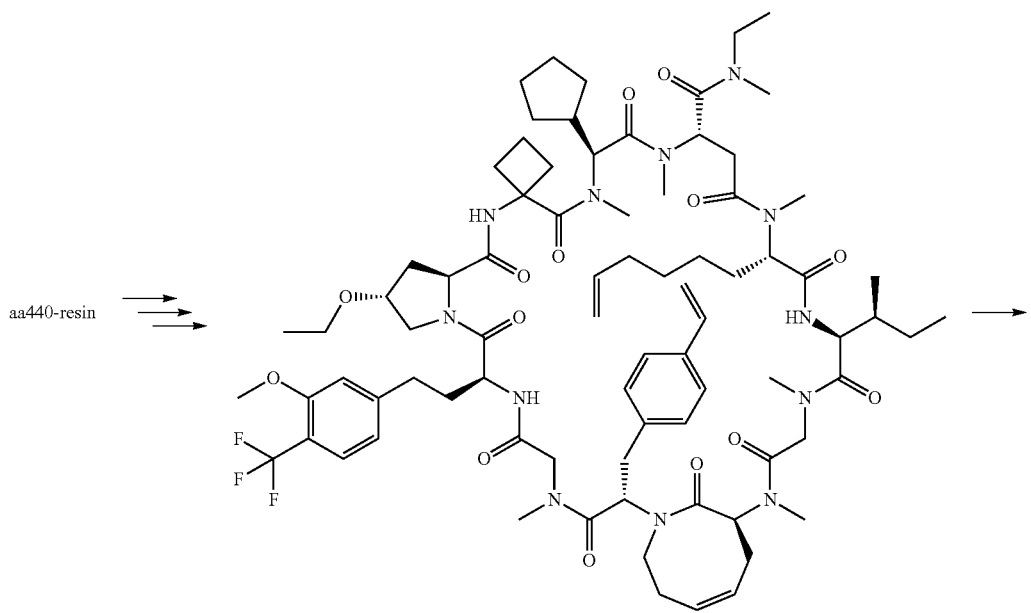

Compound PP 1828-a

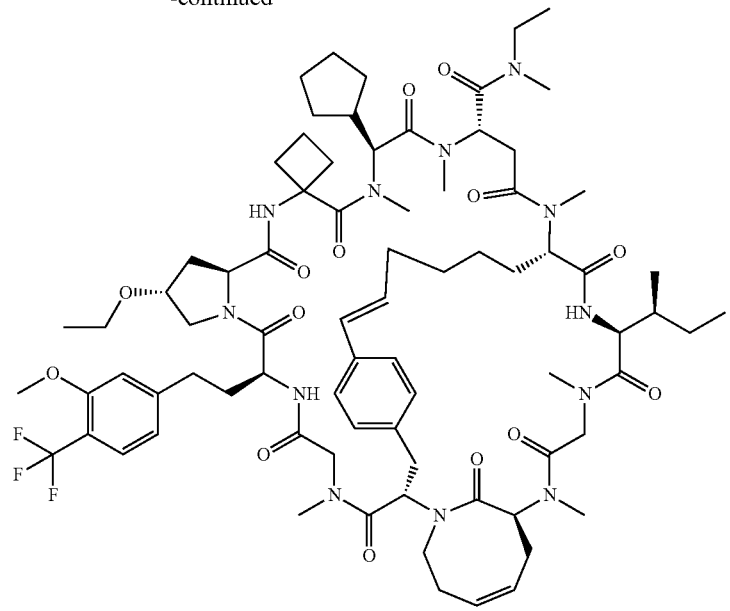

Compound PP 1828

Using Compound aa440-resin (Fmoc-MeGly (cPent)-MeAsp (O-Trt (2-Cl) resin)-MeNEt) as a raw material, peptide synthesis was carried out by the basic peptide synthesis method described in the present Examples to give Compound PP1828-a. Compound PP1828-a (10.9 mg, 7.28 µmol), 1,4-benzoquinone (3.6 mg, 33 µmol), and a Stewart-Grubbs catalyst (3.2 mg, 5.6 µmol) were dissolved in 1,4-dioxane (2.0 mL), and the mixture was stirred at 80° C. for 1.5 hours in a nitrogen atmosphere. After being cooled to room temperature, the reaction solution was purified by reverse phase HPLC(methanol/50 mM aqueous ammonium acetate solution) to give PP1828 (3.08 mg, 5.9%).

LCMS (ESI) m/z=1498 (M+H)+

Retention time: 3.09 min (Analytical condition SQDFA05 long)

Synthesis of Compound PP1827

Synthesis of PP1827 was carried out according to the following scheme.

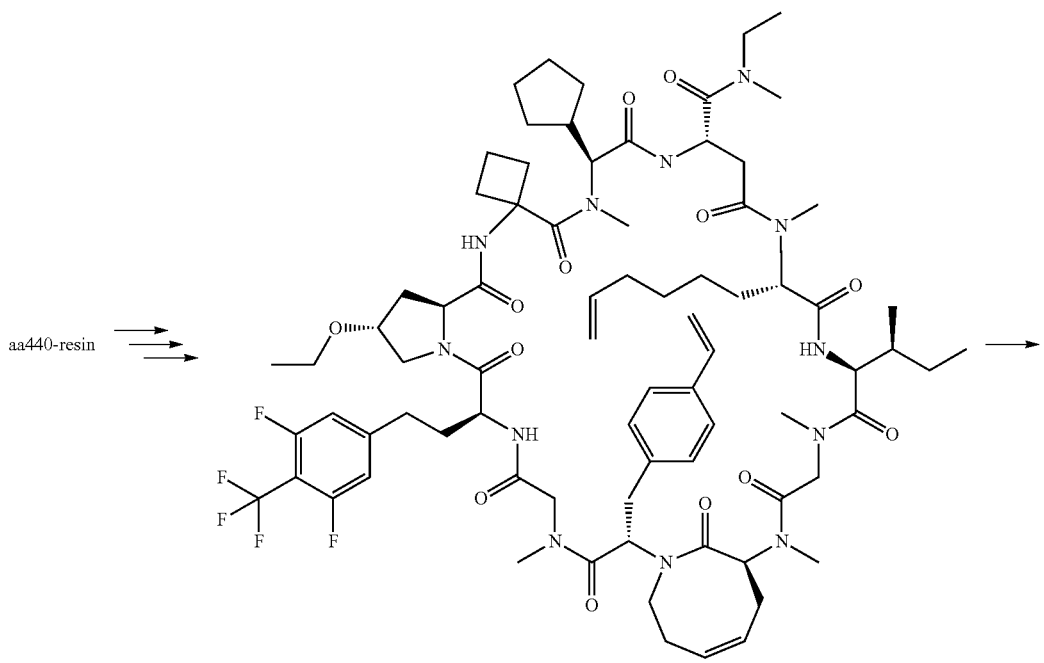

Compound PP 1827-a

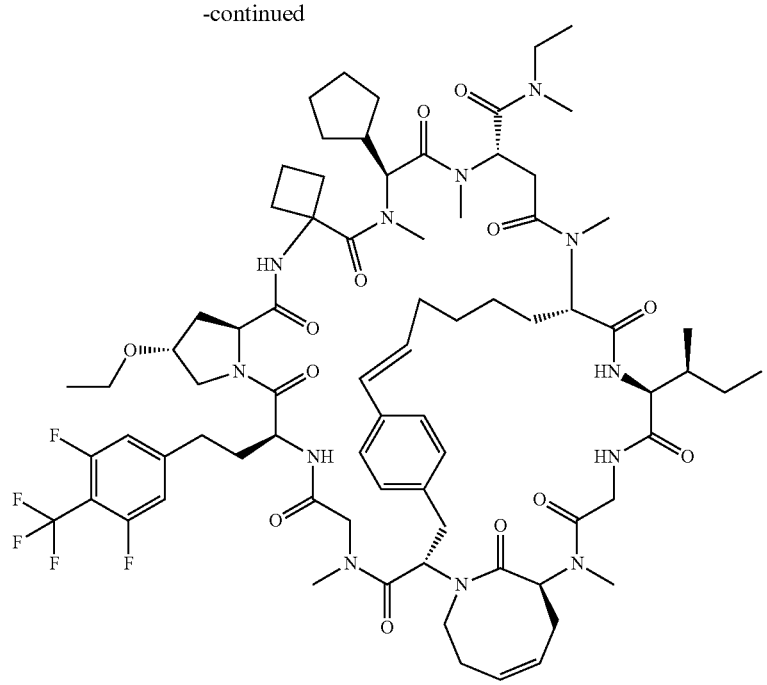

Compound PP 1827

Using Compound aa440-resin (Fmoc-MeGly (cPent)-MeAsp (O-Trt (2-Cl) resin)-MeNEt) as a raw material, peptide synthesis was carried out by the basic peptide synthesis method described in the present Examples to give Compound PP1827-a. The resulting compound was divided into 3 containers, and subjected to the following experiments. Compound PP1827-a (2.6 mg, 1.7 μmol), 1,4-benzoquinone (1.1 mg, 10.2 μmol), and a Stewart-Grubbs catalyst (1.0 mg, 1.7 μmol) were dissolved in 1,4-dioxane (0.66 mL), and the mixture was stirred at 80° C. for 2 hours in a nitrogen atmosphere and cooled to room temperature. Similarly, the entirety of a reaction solution obtained by stirring Compound PP1827-a (2.7 mg), the Stewart-Grubbs catalyst (1.0 mg, 1.7 μmol), and 1,4-dioxane (0.66 mL) which are other than 1,4-benzoquinone at 80° C. for 2 hours and the entirety of a reaction solution obtained by stirring PP1827-a (1.6 mg), a Hoveyda-Grubbs first-generation catalyst (1.0 mg, 1.7 μmol), and 1,4-dioxane (0.66 mL) at 80° C. for 2 hours were mixed, and concentrated under reduced pressure. The resulting crude product was purified by reverse phase HPLC(methanol/50 mM aqueous ammonium acetate solution) to give PP1827 (2.1 mg, 3.9%).

LCMS (ESI) m/z=1504 (M+H)+
Retention time: 3.17 min (Analytical condition SQDFA05 long)

Using any of Compounds aa359-resin, aa360-resin, aa362-resin, aa374-resin, aa429-resin, and aa440-resin as a raw material, peptide synthesis was carried out by the basic peptide synthesis method described in the present Examples to give a cyclic peptide as an intermediate. Using the resulting intermediate peptide, compounds shown in Table 29-2 were produced in the same manner as the synthesis of Compound PP1828 by reacting the side chain moiety of any of MeAlgly, MeAhxe (2), MeAhpe (2), MeAocte (2), and MeAnone (2) with the styrene moiety of ButenylPhe (4—CH═CH₂). Purification was carried out by reverse phase HPLC(methanol/50 mM aqueous ammonium acetate solution or 0.1% formic acid-containing acetonitrile/0.1% formic acid-containing distilled water). The yield (amount/percentage) is provided in Table 29-3. LC/MS data are provided in Table 36.

aa359-resin
aa360-resin
aa362-resin
aa374-resin
aa429-resin
aa440-resin

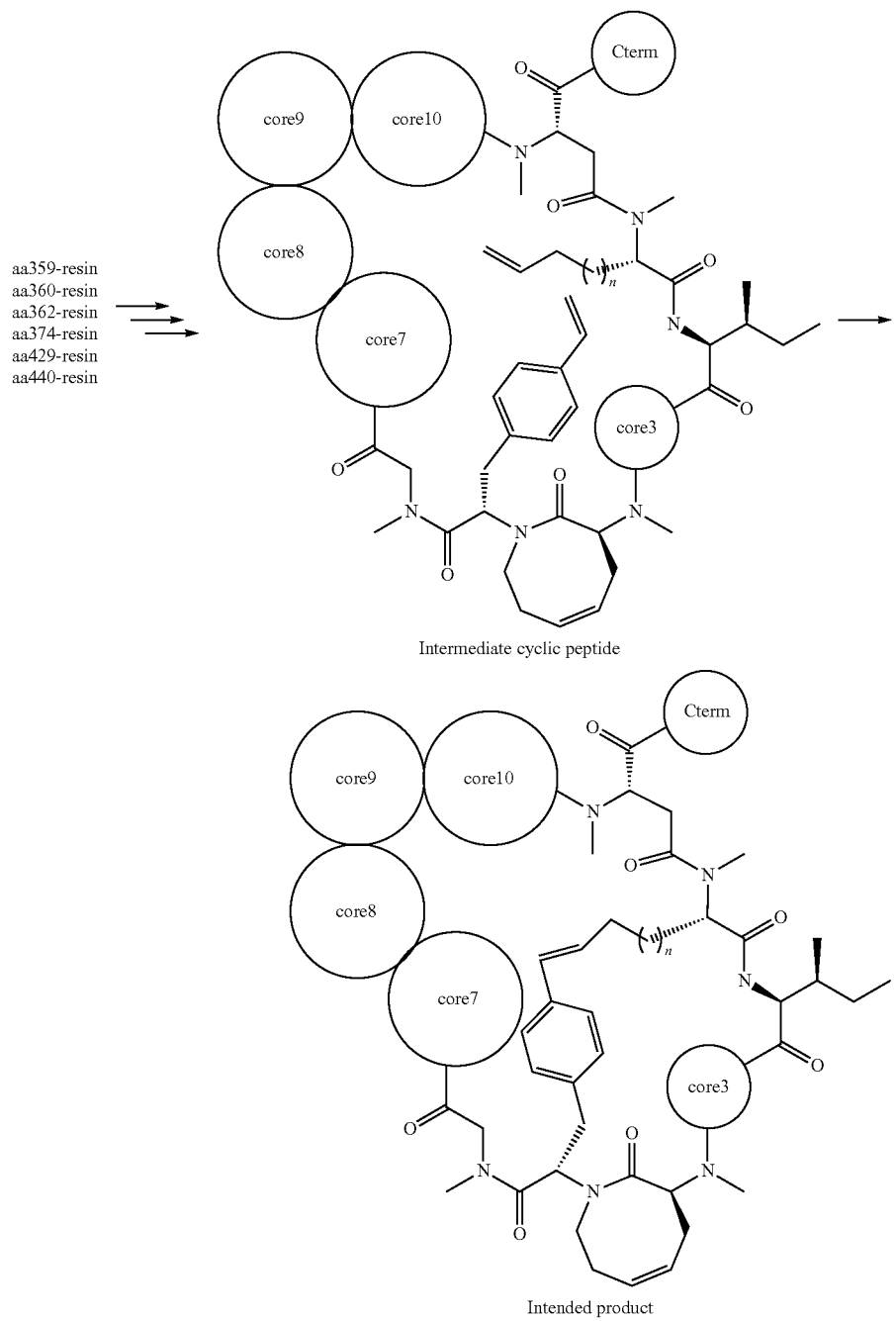

Intermediate cyclic peptide

Intended product

TABLE 29-2

| ID | core 1 | core 2 | core 3 | core 4 | core 5 | core 6 | core 7 |
|---|---|---|---|---|---|---|---|
| PP1829 | MeAocte(2) | Ile | MeGly | MeAlgly | ButenylPhe(4-CH=CH2) | MeGly | Hph(4-CF3-35-F2) |
| PP1830 | MeAocte(2) | Ile | MeGly | MeAlgly | ButenylPhe(4-CH=CH2) | MeGly | Hph(4-CF3-3-OMe) |
| PP1831 | MeAocte(2) | Ile | MeGly | MeAlgly | ButenylPhe(4-CH=CH2) | MeGly | Hph(4-CF3-35-F2) |
| PP1832 | MeAocte(2) | Ile | MeGly | MeAlgly | ButenylPhe(4-CH=CH2) | MeGly | Hph(4-CF3-3-OMe) |
| PP1833 | MeAhpe(2) | Ile | MeGly | MeAlgly | ButenylPhe(4-CH=CH2) | MeGly | Hph(4-CF3-35-F2) |
| PP1834 | MeAhpe(2) | Ile | MeGly | MeAlgly | ButenylPhe(4-CH=CH2) | MeGly | Hph(4-CF3-3-OMe) |
| PP1835 | MeAhpe(2) | Ile | MeGly | MeAlgly | ButenylPhe(4-CH=CH2) | MeGly | Hph(4-CF3-35-F2) |
| PP1827 | MeAocte(2) | Ile | MeGly | MeAlgly | ButenylPhe(4-CH=CH2) | MeGly | Hph(4-CF3-35-F2) |
| PP1828 | MeAocte(2) | Ile | MeGly | MeAlgly | ButenylPhe(4-CH=CH2) | MeGly | Hph(4-CF3-3-OMe) |
| PP2573 | MeAhpe(2) | Ile | MeGly | MeAlgly | ButenylPhe(4-CH=CH2) | MeGly | Hph(4-CF3-35-F2) |
| PP2574 | MeAhpe(2) | Ile | MeGly | MeAlgly | ButenylPhe(4-CH=CH2) | MeGly | Hph(4-CF3-35-F2) |

TABLE 29-2-continued

| | | | | | | | |
|---|---|---|---|---|---|---|---|
| PP2575 | MeAhpe(2) | Ile | MeGly | MeAlgly | ButenylPhe(4-CH=CH2) | MeGly | Hph(4-CF3-35-F2) |
| PP2576 | MeAhpe(2) | Ile | MeGly | MeAlgly | ButenylPhe(4-CH=CH2) | MeGly | Hph(4-CF3-35-F2) |
| PP2577 | MeAhpe(2) | Ile | MeGly | MeAlgly | ButenylPhe(4-CH=CH2) | MeGly | Hph(34-Cl2) |
| PP2578 | MeAhpe(2) | Ile | MeGly | MeAlgly | ButenylPhe(4-CH=CH2) | MeGly | Hph(34-Cl2) |
| PP2579 | MeAhpe(2) | Ile | MeGly | MeAlgly | ButenylPhe(4-CH=CH2) | MeGly | Hph(34-Cl2) |
| PP2580 | MeAhpe(2) | Ile | MeGly | MeAlgly | ButenylPhe(4-CH=CH2) | MeGly | Hph(34-Cl2) |
| PP2581 | MeAhpe(2) | Ile | MeGly | MeAlgly | ButenylPhe(4-CH=CH2) | MeGly | Hph(34-Cl2) |
| PP2583 | MeAhpe(2) | Ile | cPrGly | MeAlgly | ButenylPhe(4-CH=CH2) | MeGly | Hph(4-CF3-35-F2) |
| PP2585 | MeAhpe(2) | Ile | cPrGly | MeAlgly | ButenylPhe(4-CH=CH2) | MeGly | Hph(34-Cl2) |
| PP2586 | MeAhxe(2) | Ile | MeGly | MeAlgly | ButenylPhe(4-CH=CH2) | MeGly | Hph(4-CF3-35-F2) |
| PP2588 | MeAhxe(2) | Ile | MeGly | MeAlgly | ButenylPhe(4-CH=CH2) | MeGly | Hph(34-Cl2) |
| PP2589 | MeAhxe(2) | Ile | MeGly | MeAlgly | ButenylPhe(4-CH=CH2) | MeGly | Hph(34-Cl2) |
| PP2590 | MeAhxe(2) | Ile | MeGly | MeAlgly | ButenylPhe(4-CH=CH2) | MeGly | Hph(34-Cl2) |
| PP2591 | MeAhxe(2) | Ile | MeGly | MeAlgly | ButenylPhe(4-CH=CH2) | MeGly | Hph(34-Cl2) |
| PP2592 | MeAocte(2) | Ile | MeGly | MeAlgly | ButenylPhe(4-CH=CH2) | MeGly | Hph(34-Cl2) |
| PP2593 | MeAocte(2) | Ile | MeGly | MeAlgly | ButenylPhe(4-CH=CH2) | MeGly | Hph(34-Cl2) |
| PP2594 | MeAhpe(2) | Ile | MeGly | MeAlgly | ButenylPhe(4-CH=CH2) | MeGly | Hph(4-CF3-35-F2) |
| PP2595 | MeAhpe(2) | Ile | MeGly | MeAlgly | ButenylPhe(4-CH=CH2) | MeGly | Hph(34-Cl2) |
| PP2596 | MeAhpe(2) | Ile | MeGly | MeAlgly | ButenylPhe(4-CH=CH2) | MeGly | Hph(34-Cl2) |
| PP2597 | MeAhxe(2) | Ile | MeGly | MeAlgly | ButenylPhe(4-CH=CH2) | MeGly | Hph(34-Cl2) |
| PP2598 | MeAhxe(2) | Ile | cPrGly | MeAlgly | ButenylPhe(4-CH=CH2) | MeGly | Hph(34-Cl2) |
| PP2600 | MeAhpe(2) | Ile | MeGly | MeAlgly | ButenylPhe(4-CH=CH2) | MeGly | Hph(4-CF3-35-F2) |
| PP2601 | MeAhpe(2) | Ile | MeGly | MeAlgly | ButenylPhe(4-CH=CH2) | MeGly | Hph(34-Cl2) |
| PP2602 | MeAhpe(2) | Ile | MeGly | MeAlgly | ButenylPhe(4-CH=CH2) | MeGly | Hph(34-Cl2) |
| PP2603 | MeAhpe(2) | Ile | MeGly | MeAlgly | ButenylPhe(4-CH=CH2) | MeGly | Hph(34-Cl2) |
| PP2604 | MeAhpe(2) | Ile | MeGly | MeAlgly | ButenylPhe(4-CH=CH2) | MeGly | Hph(34-Cl2) |
| PP2605 | MeAocte(2) | Ile | cPrGly | MeAlgly | ButenylPhe(4-CH=CH2) | MeGly | Hph(34-Cl2) |
| PP2952 | MeAhpe(2) | Ile | MeGly | MeAlgly | ButenylPhe(4-CH=CH2) | MeGly | Hph(4-CF3-35-F2) |
| PP2953 | MeAhpe(2) | Ile | MeGly | MeAlgly | ButenylPhe(4-CH=CH2) | MeGly | Hph(34-Cl2) |
| PP2954 | MeAhpe(2) | Ile | cPrGly | MeAlgly | ButenylPhe(4-CH=CH2) | MeGly | Hph(4-CF3-35-F2) |
| PP2955 | MeAhpe(2) | Ile | cPrGly | MeAlgly | ButenylPhe(4-CH=CH2) | MeGly | Hph(4-CF3-35-F2) |
| PP2956 | MeAhpe(2) | Ile | cPrGly | MeAlgly | ButenylPhe(4-CH=CH2) | MeGly | Hph(4-CF3-35-F2) |
| PP2957 | MeAhpe(2) | Ile | cPrGly | MeAlgly | ButenylPhe(4-CH=CH2) | MeGly | Hph(4-CF3-35-F2) |
| PP2958 | MeAhpe(2) | Ile | cPrGly | MeAlgly | ButenylPhe(4-CH=CH2) | MeGly | Hph(34-Cl2) |
| PP2959 | MeAhpe(2) | Ile | cPrGly | MeAlgly | ButenylPhe(4-CH=CH2) | MeGly | Hph(34-Cl2) |
| PP3039 | MeAhpe(2) | Ile | cPrGly | MeAlgly | ButenylPhe(4-CH=CH2) | MeGly | Hph(34-Cl2) |
| PP3040 | MeAhpe(2) | Ile | cPrGly | MeAlgly | ButenylPhe(4-CH=CH2) | MeGly | Hph(34-Cl2) |
| PP3041 | MeAlgly | Ile | MeGly | MeAlgly | ButenylPhe(4-CH=CH2) | MeGly | Hph(34-Cl2) |
| PP3042 | MeAlgly | Ile | MeGly | MeAlgly | ButenylPhe(4-CH=CH2) | MeGly | Hph(34-Cl2) |
| PP3043 | MeAlgly | Ile | MeGly | MeAlgly | ButenylPhe(4-CH=CH2) | MeGly | Hph(34-Cl2) |
| PP3044 | MeAocte(2) | Ile | MeGly | MeAlgly | ButenylPhe(4-CH=CH2) | MeGly | Hph(4-CF3-35-F2) |
| PP3045 | MeAocte(2) | Ile | MeGly | MeAlgly | ButenylPhe(4-CH=CH2) | MeGly | Hph(34-Cl2) |
| PP3046 | MeAocte(2) | Ile | MeGly | MeAlgly | ButenylPhe(4-CH=CH2) | MeGly | Hph(34-Cl2) |
| PP3047 | MeAocte(2) | Ile | MeGly | MeAlgly | ButenylPhe(4-CH=CH2) | MeGly | Hph(34-Cl2) |
| PP3048 | MeAnone(2) | Ile | MeGly | MeAlgly | ButenylPhe(4-CH=CH2) | MeGly | Hph(4-CF3-35-F2) |
| PP3049 | MeAnone(2) | Ile | MeGly | MeAlgly | ButenylPhe(4-CH=CH2) | MeGly | Hph(34-Cl2) |
| PP3050 | MeAnone(2) | Ile | MeGly | MeAlgly | ButenylPhe(4-CH=CH2) | MeGly | Hph(34-Cl2) |
| PP3051 | MeAnone(2) | Ile | MeGly | MeAlgly | ButenylPhe(4-CH=CH2) | MeGly | Hph(34-Cl2) |
| PP3052 | MeAnone(2) | Ile | MeGly | MeAlgly | ButenylPhe(4-CH=CH2) | MeGly | Hph(34-Cl2) |
| PP3053 | MeAhpe(2) | Ile | MeGly | MeAlgly | ButenylPhe(4-CH=CH2) | MeGly | Hph(34-Cl2) |
| PP3054 | MeAhpe(2) | Ile | MeGly | MeAlgly | ButenylPhe(4-CH=CH2) | MeGly | Hph(34-Cl2) |
| PP3055 | MeAhpe(2) | Ile | MeGly | MeAlgly | ButenylPhe(4-CH=CH2) | MeGly | Hph(34-Cl2) |
| PP3056 | MeAlgly | Ile | MeGly | MeAlgly | ButenylPhe(4-CH=CH2) | MeGly | Hph(34-Cl2) |
| PP3057 | MeAnone(2) | Ile | MeGly | MeAlgly | ButenylPhe(4-CH=CH2) | MeGly | Hph(34-Cl2) |
| PP3058 | MeAhpe(2) | Ile | MeGly | MeAlgly | ButenylPhe(4-CH=CH2) | MeGly | Hph(34-Cl2) |
| PP3059 | MeAhpe(2) | Ile | MeGly | MeAlgly | ButenylPhe(4-CH=CH2) | MeGly | Hph(34-Cl2) |
| PP3060 | MeAhpe(2) | Ile | MeGly | MeAlgly | ButenylPhe(4-CH=CH2) | MeGly | Hph(4-CF3-35-F2) |
| PP3061 | MeAhpe(2) | Ile | cPrGly | MeAlgly | ButenylPhe(4-CH=CH2) | MeGly | Hph(34-Cl2) |
| PP3062 | MeAocte(2) | Ile | MeGly | MeAlgly | ButenylPhe(4-CH=CH2) | MeGly | Hph(34-Cl2) |

| ID | core 8 | core 9 | core 10 | core 11 | C term |
|---|---|---|---|---|---|
| PP1829 | Hyp(Et) | cVal(3-Me2) | MeGly(cPent) | MeAsp2 | MeNEt |
| PP1830 | Hyp(Et) | cVal(3-Me2) | MeGly(cPent) | MeAsp2 | MeNEt |
| PP1831 | Hyp(Et) | cVal(3-Me2) | MeGly(cPent) | MeAsp2 | NMe2 |
| PP1832 | Hyp(Et) | cVal(3-Me2) | MeGly(cPent) | MeAsp2 | NMe2 |
| PP1833 | Hyp(Et) | cVal | MeGly(cPent) | MeAsp2 | MeNEt |
| PP1834 | Hyp(Et) | cVal | MeGly(cPent) | MeAsp2 | MeNEt |
| PP1835 | Hyp(Et) | cVal(3-Me2) | MeGly(cPent) | MeAsp2 | MeNEt |
| PP1827 | Hyp(Et) | cVal | MeGly(cPent) | MeAsp2 | MeNEt |
| PP1828 | Hyp(Et) | cVal | MeGly(cPent) | MeAsp2 | MeNEt |
| PP2573 | Hyp(Et) | cVal(3-Me2) | MeGly(cPent) | MeAsp2 | pip |
| PP2574 | Hyp(Et) | cVal(3-Me2) | MeGly(cPent) | MeAsp2 | pyrro |
| PP2575 | Hyp(Et) | cVal(3-Me2) | MeNva(3-Et) | MeAsp2 | NMe2 |
| PP2576 | Hyp(Et) | cVal(3-Me2) | MeNva(3-Et) | MeAsp2 | pyrro |
| PP2577 | Hyp(Et) | cVal(3-Me2) | MeGly(cPent) | MeAsp2 | MeNEt |
| PP2578 | Hyp(Et) | cVal(3-Me2) | MeGly(cPent) | MeAsp2 | pip |
| PP2579 | Hyp(Et) | cVal(3-Me2) | MeGly(cPent) | MeAsp2 | pyrro |
| PP2580 | Hyp(Et) | cVal(3-Me2) | MeNva(3-Et) | MeAsp2 | NMe2 |
| PP2581 | Hyp(Et) | cVal(3-Me2) | MeNva(3-Et) | MeAsp2 | pyrro |

TABLE 29-2-continued

| | | | | | |
|---|---|---|---|---|---|
| PP2583 | Hyp(Et) | cVal(3-Me2) | MeGly(cPent) | MeAsp2 | pyrro |
| PP2585 | Hyp(Et) | cVal(3-Me2) | MeGly(cPent) | MeAsp2 | pyrro |
| PP2586 | Hyp(Et) | cVal(3-Me2) | MeNva(3-Et) | MeAsp2 | NMe2 |
| PP2588 | Hyp(Et) | cVal(3-Me2) | MeGly(cPent) | MeAsp2 | pyrro |
| PP2589 | Hyp(Et) | cVal(3-Me2) | MeNva(3-Et) | MeAsp2 | NMe2 |
| PP2590 | Hyp(Et) | cVal(3-Me2) | MeNva(3-Et) | MeAsp2 | pip |
| PP2591 | Hyp(Et) | cVal(3-Me2) | MeNva(3-Et) | MeAsp2 | pyrro |
| PP2592 | Hyp(Et) | cVal(3-Me2) | MeGly(cPent) | MeAsp2 | MeNEt |
| PP2593 | Hyp(Et) | cVal(3-Me2) | MeGly(cPent) | MeAsp2 | pyrro |
| PP2594 | Hyp(iPr) | cVal(3-Me2) | MeNva(3-Et) | MeAsp2 | NMe2 |
| PP2595 | Hyp(iPr) | cVal(3-Me2) | MeGly(cPent) | MeAsp2 | MeNEt |
| PP2596 | Hyp(iPr) | cVal(3-Me2) | MeGly(cPent) | MeAsp2 | pyrro |
| PP2597 | Hyp(Et) | cVal(3-Me2) | MeGly(cPent) | MeAsp2 | pip |
| PP2598 | Hyp(Et) | cVal(3-Me2) | MeGly(cPent) | MeAsp2 | MeNEt |
| PP2600 | Pro | cVal(3-Me2) | MeNva(3-Et) | MeAsp2 | NMe2 |
| PP2601 | Pro | cVal(3-Me2) | MeGly(cPent) | MeAsp2 | MeNEt |
| PP2602 | Pro | cVal(3-Me2) | MeGly(cPent) | MeAsp2 | pyrro |
| PP2603 | Pro | cVal(3-Me2) | MeNva(3-Et) | MeAsp2 | NMe2 |
| PP2604 | Pro | cVal(3-Me2) | MeNva(3-Et) | MeAsp2 | pyrro |
| PP2605 | Hyp(Et) | cVal | MeNva(3-Et) | MeAsp2 | NMe2 |
| PP2952 | Hyp(Et) | cVal(3-Me2) | MeNva(3-Et) | MeAsp2 | pip |
| PP2953 | Hyp(Et) | cVal(3-Me2) | MeNva(3-Et) | MeAsp2 | pip |
| PP2954 | Hyp(Et) | cVal | MeGly(cPent) | MeAsp2 | pip |
| PP2955 | Hyp(Et) | cVal(3-Me2) | MeNva(3-Et) | MeAsp2 | NMe2 |
| PP2956 | Hyp(Et) | cVal | MeNva(3-Et) | MeAsp2 | pip |
| PP2957 | Hyp(Et) | cVal | MeNva(3-Et) | MeAsp2 | pyrro |
| PP2958 | Hyp(Et) | cVal | MeGly(cPent) | MeAsp2 | pip |
| PP2959 | Hyp(Et) | cVal(3-Me2) | MeNva(3-Et) | MeAsp2 | NMe2 |
| PP3039 | Hyp(Et) | cVal | MeNva(3-Et) | MeAsp2 | pip |
| PP3040 | Hyp(Et) | cVal | MeNva(3-Et) | MeAsp2 | pyrro |
| PP3041 | Hyp(Et) | cVal(3-Me2) | MeGly(cPent) | MeAsp2 | pyrro |
| PP3042 | Hyp(Et) | cVal(3-Me2) | MeNva(3-Et) | MeAsp2 | pip |
| PP3043 | Hyp(Et) | cVal(3-Me2) | MeNva(3-Et) | MeAsp2 | pyrro |
| PP3044 | Hyp(Et) | cVal(3-Me2) | MeNva(3-Et) | MeAsp2 | NMe2 |
| PP3045 | Hyp(Et) | cVal(3-Me2) | MeNva(3-Et) | MeAsp2 | NMe2 |
| PP3046 | Hyp(Et) | cVal | MeNva(3-Et) | MeAsp2 | pip |
| PP3047 | Hyp(Et) | cVal | MeNva(3-Et) | MeAsp2 | pyrro |
| PP3048 | Hyp(Et) | cVal(3-Me2) | MeNva(3-Et) | MeAsp2 | NMe2 |
| PP3049 | Hyp(Et) | cVal | MeGly(cPent) | MeAsp2 | pyrro |
| PP3050 | Hyp(Et) | cVal(3-Me2) | MeNva(3-Et) | MeAsp2 | NMe2 |
| PP3051 | Hyp(Et) | cVal | MeNva(3-Et) | MeAsp2 | pip |
| PP3052 | Hyp(Et) | cVal | MeNva(3-Et) | MeAsp2 | pyrro |
| PP3053 | Hyp(cBu) | cVal(3-Me2) | MeGly(cPent) | MeAsp2 | pyrro |
| PP3054 | Hyp(cPent) | cVal(3-Me2) | MeGly(cPent) | MeAsp2 | pyrro |
| PP3055 | Pro | cVal(3-Me2) | MeNva(3-Et) | MeAsp2 | pip |
| PP3056 | Hyp(Et) | cVal(3-Me2) | MeGly(cPent) | MeAsp2 | MeNEt |
| PP3057 | Hyp(Et) | cVal(3-Me2) | MeGly(cPent) | MeAsp2 | NMe2 |
| PP3058 | Hyp(cBu) | cVal(3-Me2) | MeGly(cPent) | MeAsp2 | MeNEt |
| PP3059 | Hyp(Et) | MecVal(3-Me2) | MeGly(cPent) | MeAsp2 | NMe2 |
| PP3060 | Hyp(Et) | MecVal(3-Me2) | MeGly(cPent) | MeAsp2 | NMe2 |
| PP3061 | Hyp(Et) | MecVal(3-Me2) | MeGly(cPent) | MeAsp2 | NMe2 |
| PP3062 | Hyp(Et) | MecVal(3-Me2) | MeGly(cPent) | MeAsp2 | NMe2 |

TABLE 29-3

| ID | yield (mg) | yield (%) |
|---|---|---|
| PP1829 | 2.52 | 4.7 |
| PP1830 | 2.28 | 4.3 |
| PP1831 | 3.09 | 4.4 |
| PP1832 | 3.98 | 5.7 |
| PP1833 | 3.35 | 6.4 |
| PP1834 | 3.23 | 6.2 |
| PP1835 | 3.14 | 5.9 |
| PP1827 | 2.05 | 3.9 |
| PP1828 | 3.08 | 5.9 |
| PP2573 | 3.02 | 22.8 |
| PP2574 | 3.58 | 21.1 |
| PP2575 | 2.56 | 15.7 |
| PP2576 | 2.59 | 16.4 |
| PP2577 | 4.75 | 22.3 |
| PP2578 | 2.28 | 24.3 |
| PP2579 | 2.53 | 27.1 |
| PP2580 | 2.52 | 21.9 |
| PP2581 | 2.73 | 19.3 |
| PP2583 | 4.13 | 23.8 |
| PP2585 | 4.08 | 25.8 |
| PP2586 | 4.11 | 28.6 |
| PP2588 | 4.19 | 27.0 |
| PP2589 | 4.29 | 29.0 |
| PP2590 | 4.31 | 27.2 |
| PP2591 | 5.01 | 27.5 |
| PP2592 | 4.22 | 19.0 |
| PP2593 | 3.09 | 20.0 |
| PP2594 | 2.54 | 19.9 |
| PP2595 | 4.04 | 21.0 |
| PP2596 | 3.5 | 22.6 |
| PP2597 | 3.97 | 29.8 |
| PP2598 | 0.34 | 1.4 |
| PP2600 | 2.37 | 15.6 |
| PP2601 | 4.56 | 18.8 |
| PP2602 | 3.8 | 19.6 |
| PP2603 | 2.53 | 17.9 |
| PP2604 | 3.15 | 16.3 |
| PP2605 | 4.19 | 22.2 |
| PP2952 | 6.42 | 31.1 |
| PP2953 | 3.93 | 21.0 |

TABLE 29-3-continued

| ID | yield (mg) | yield (%) |
|---|---|---|
| PP2954 | 9.73 | 43.1 |
| PP2955 | 6.03 | 34.1 |
| PP2956 | 7.18 | 40.6 |
| PP2957 | 7.05 | 31.2 |
| PP2958 | 8.50 | 45.6 |
| PP2959 | 5.12 | 34.8 |
| PP3039 | 3.32 | 21.3 |
| PP3040 | 7.15 | 37.1 |
| PP3041 | 4.79 | 16.4 |
| PP3042 | 2.94 | 13.6 |
| PP3043 | 3.39 | 14.2 |
| PP3044 | 4.32 | 21.3 |
| PP3045 | 4.16 | 24.4 |
| PP3046 | 5.42 | 33.0 |
| PP3047 | 6.08 | 27.7 |
| PP3048 | 2.17 | 10.6 |
| PP3049 | 5.46 | 19.9 |
| PP3050 | 2.02 | 12.3 |
| PP3051 | 3.63 | 20.9 |
| PP3052 | 3.14 | 14.6 |
| PP3053 | 8.21 | 27.7 |
| PP3054 | 8.66 | 26.6 |
| PP3055 | 3.91 | 20.4 |
| PP3056 | 4.48 | 15.6 |
| PP3057 | 4.44 | 14.7 |
| PP3058 | 8.67 | 27.3 |
| PP3059 | 5.34 | 41.3 |
| PP3060 | 4.82 | 44.4 |
| PP3061 | 6.7 | 48.5 |
| PP3062 | 9.35 | 36.8 |

Concerning the double bonds contained in the crosslinked ring of $R_1$ to $R_5$ in PP1827, PP2583, PP2952, PP2954, PP2957, PP2958, PP3040, PP3046, PP3047, PP3049, PP3053, PP3054, PP3056, PP3057, PP3058, PP3059, PP3060, PP3061, and PP3062, the coupling constant between the protons bonded to the respective carbon atoms on the double bonds was observed at 15.0 to 16.4 Hz, and thus the double bonds were all identified as having an E structure. Further, concerning PP1828, PP1829, PP1830, PP1831, PP1832, PP1833, PP1834, PP1835, PP2573, PP2574, PP2575, PP2576, PP2577, PP2578, PP2579, PP2580, PP2581, PP2586, PP2588, PP2589, PP2590, PP2591, PP2592, PP2593, PP2594, PP2595, PP2596, PP2597, PP2598, PP2600, PP2601, PP2602, PP2603, PP2604, PP2605, PP2953, PP2955, PP2956, PP2959, PP3039, PP3044, PP3045, PP3048, PP3050, PP3051, PP3052, and PP3055, which have a similar ring structure, the double bonds are inferred as having an E structure.

1-6-6. Peptide Synthesis Via N-Alkylation by Mitsunobu Reaction on Resin and Olefin Metathesis Reaction on Resin Synthesis of Compounds PP528 and PP529

Compounds PP528 and PP529 were synthesized according to the following scheme.

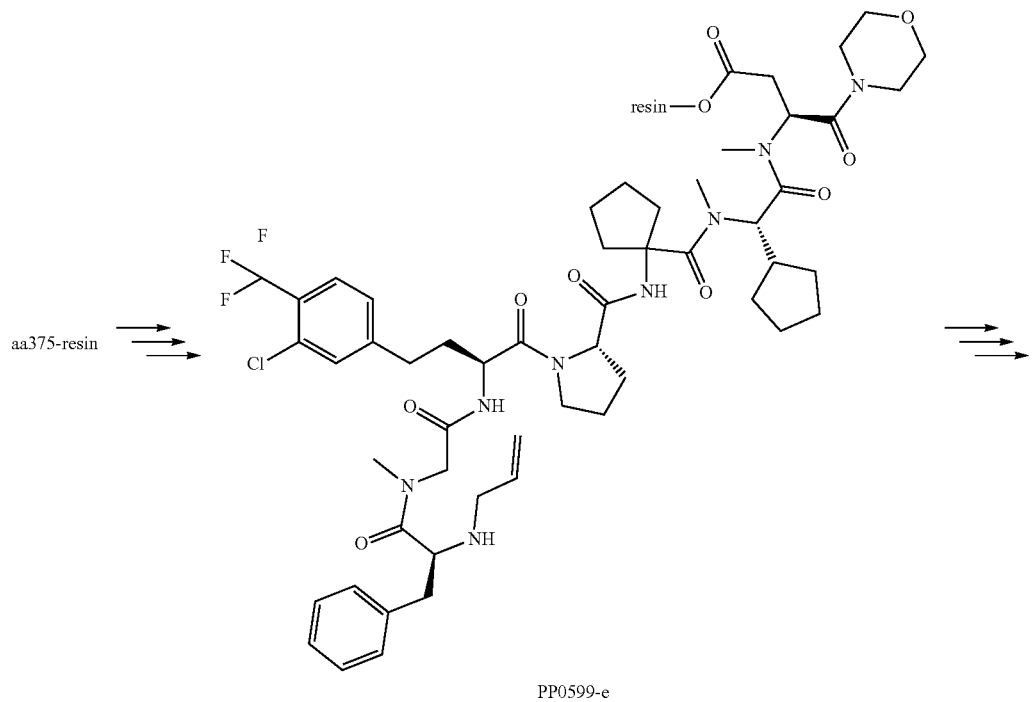

PP0599-e

759
760
-continued
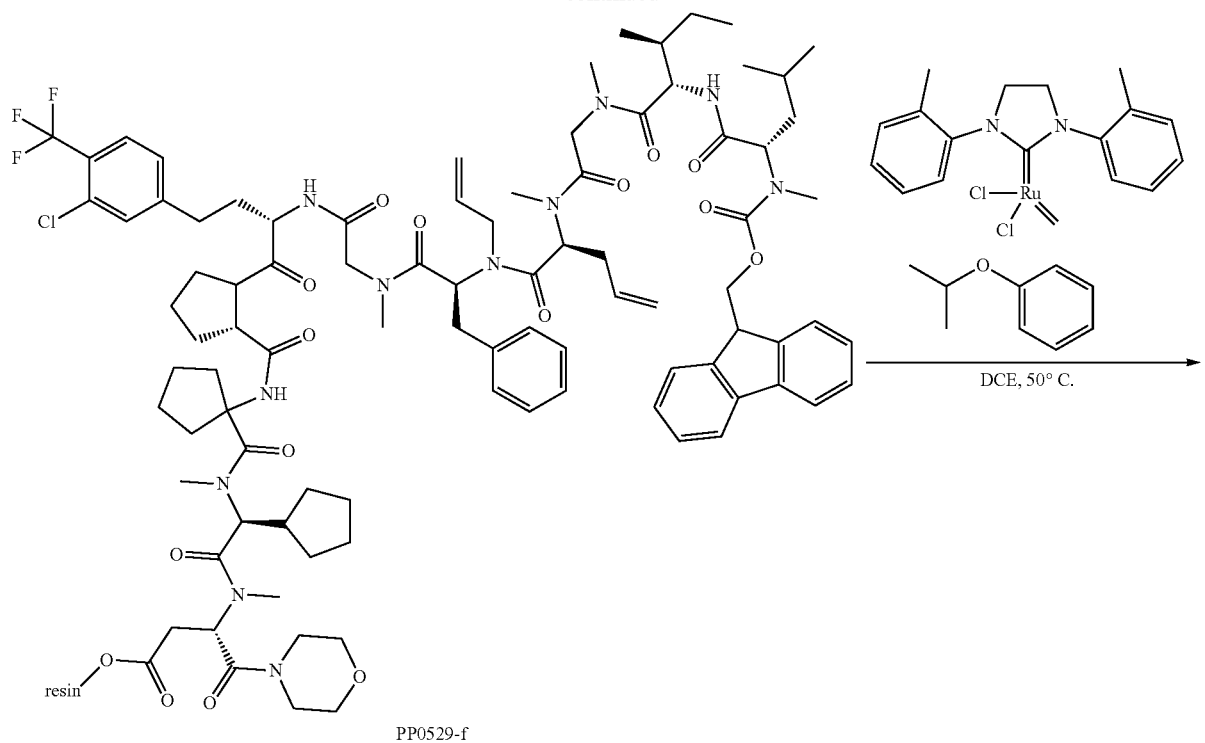
PP0529-f
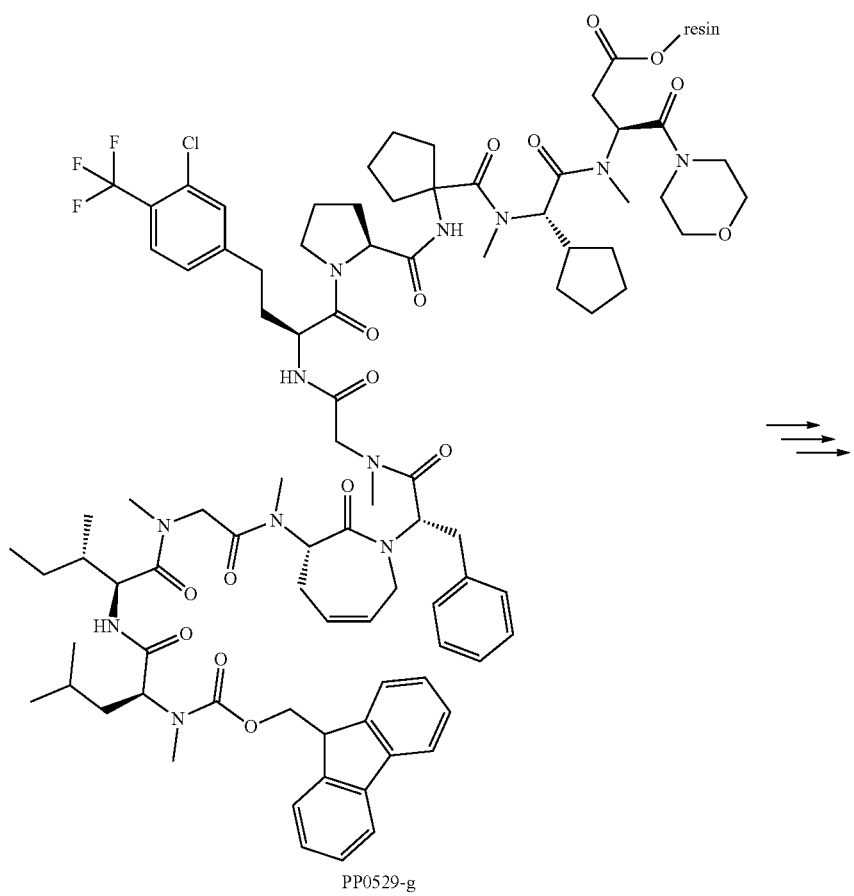
PP0529-g

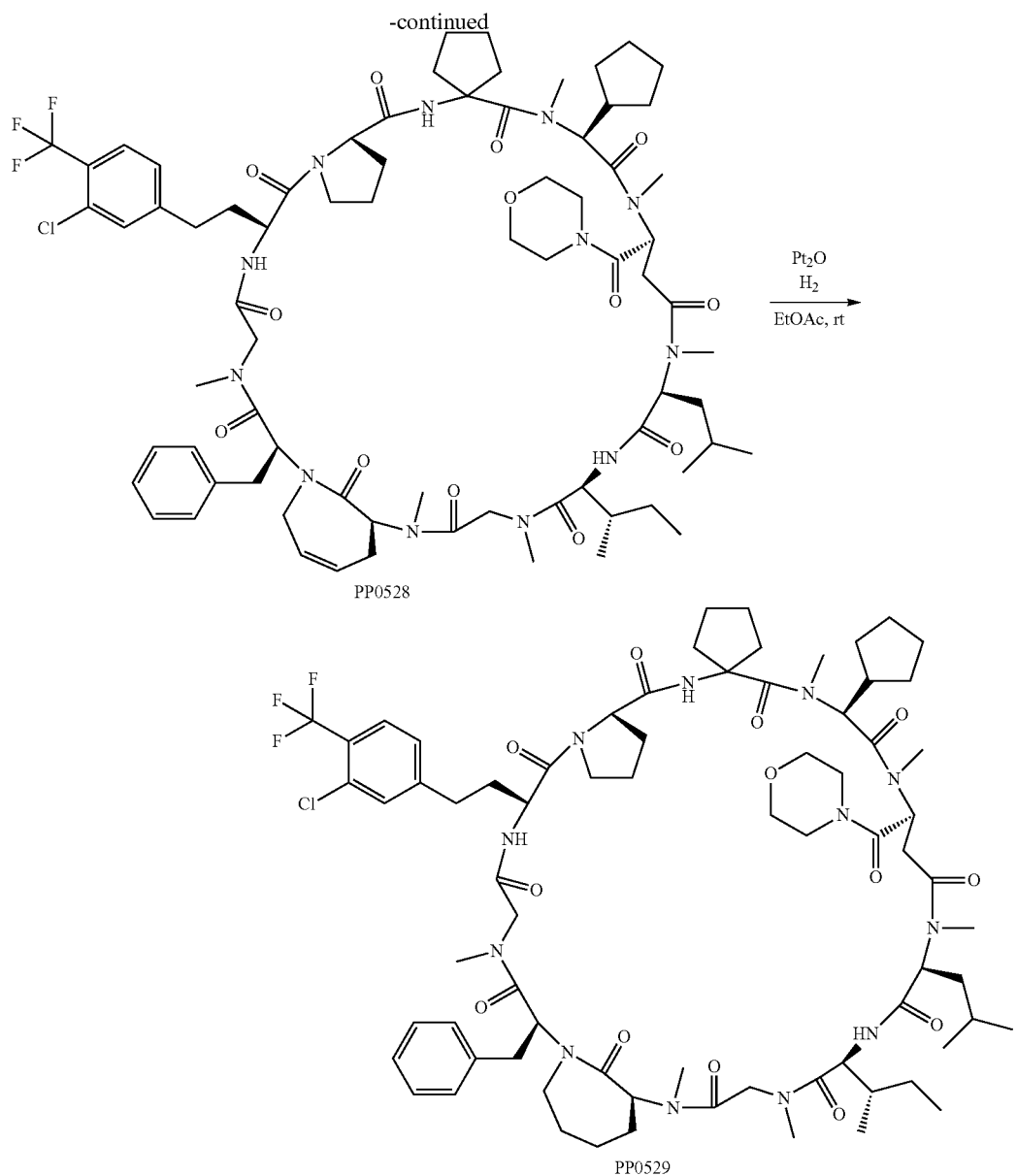

Using, as a raw material, synthesis intermediate PP599-e of Compound PP599 synthesized using Compound aa375-resin, peptide elongation was performed according to the basic route to give resin-supported PP0529-f.

Compound PP529-f-resin (100 mg, 0.45 mmol/g, 0.045 mmol) and DCM were added to a filter-equipped reaction vessel to swell the resin, DCM was removed, and then the resin was washed 4 times with DCE. A DCE (1.5 mL) solution of a Stewart-Grubbs catalyst (5.13 mg, 0.009 mmol) was added thereto, and the mixture was shaken at 50° C. for 21 hours. Then, the reaction solution was removed, and the resin was washed 4 times with DCE and then washed 4 times with DCM to give resin-supported Compound PP529-g. Cleaving from the resin was performed with TFE/DCM (1/1) using a small amount of resin-supported Compound PP529-g, and the structure was verified by LC/MS.

LCMS (ESI) m/z=1702 (M+H)+

Retention time: 3.74 min (Analytical condition SQDFA50_2)

Subsequent steps of cleaving from resin, cyclization, and purification were performed according to the basic route to give Compound PP0528 (6.9 mg). LC/MS data is provided in Table 36. Moreover, a separately synthesized Compound PP528 (132 mg, 0.09 mmol) at a crude product stage was dissolved in ethyl acetate (1 mL), platinum (IV) oxide (10.2 mg, 0.045 mmol) was added, and the mixture was stirred at room temperature for 15 hours in a hydrogen atmosphere. Platinum (IV) oxide (5.1 mg, 0.0225 mmol) was added, the mixture was stirred at room temperature in a hydrogen atmosphere for 5 more hours, then platinum (IV) oxide was filtered off, and the solvent was distilled off under reduced pressure. This was purified by reverse phase chromatography (methanol/10 mM aqueous ammonium acetate solution) to give PP0529 (9.8 mg). LC/MS data is provided in Table 36.

Synthesis of Compounds PP530 to PP0537

Compounds PP530 to PP0537 were synthesized according to the following scheme.

763
aa375-resin ⟶ ⟶ ⟶
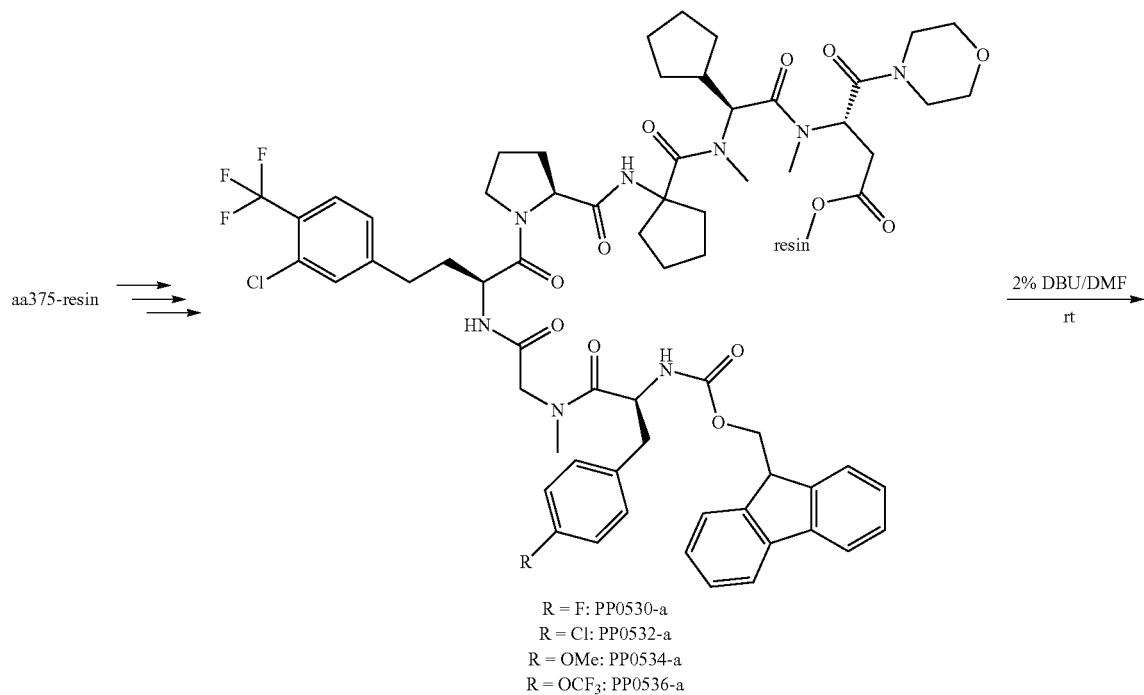
R = F: PP0530-a
R = Cl: PP0532-a
R = OMe: PP0534-a
R = OCF$_3$: PP0536-a
764
2% DBU/DMF
rt
⟶
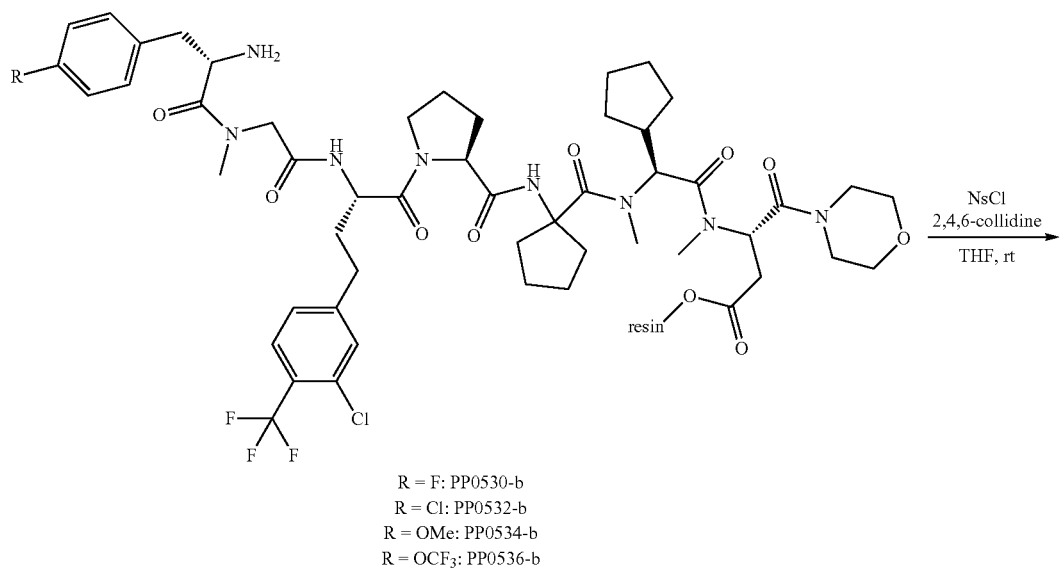
R = F: PP0530-b
R = Cl: PP0532-b
R = OMe: PP0534-b
R = OCF$_3$: PP0536-b
NsCl
2,4,6-collidine
⟶
THF, rt

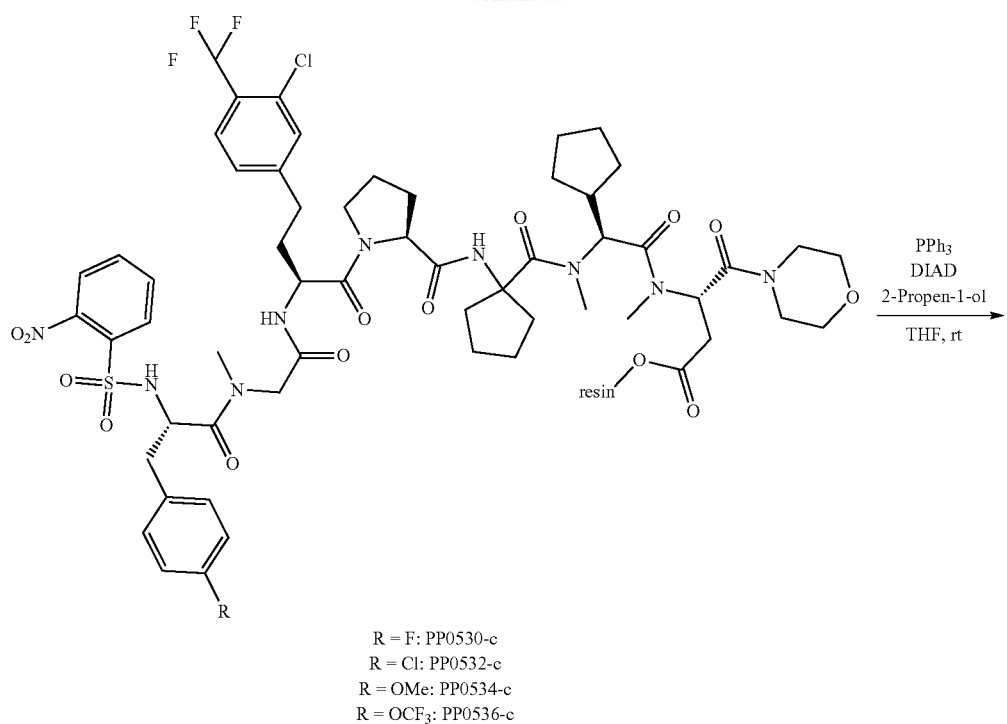
R = F: PP0530-c
R = Cl: PP0532-c
R = OMe: PP0534-c
R = OCF₃: PP0536-c
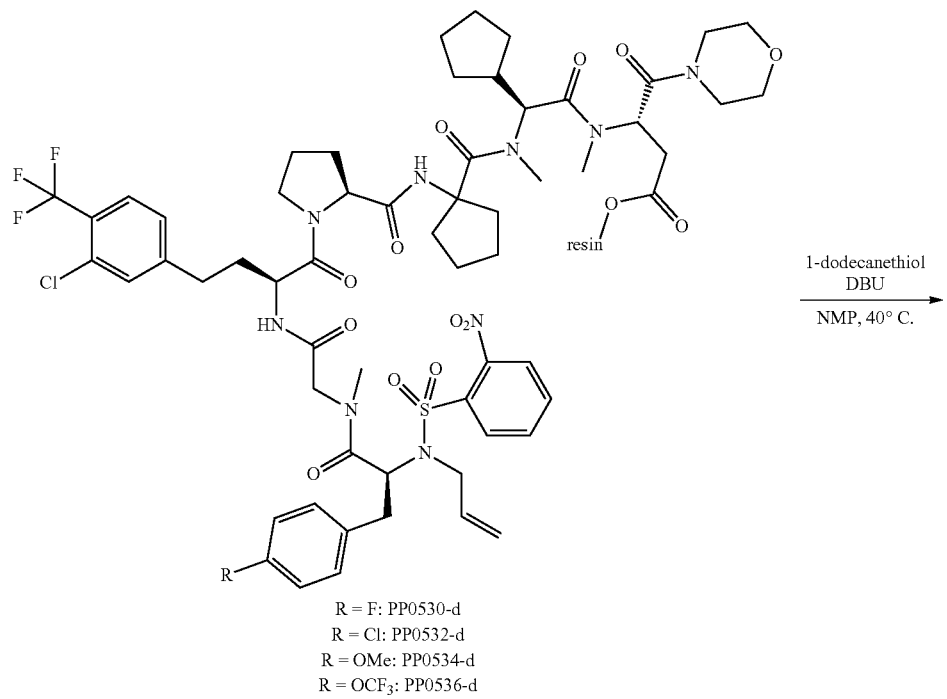
R = F: PP0530-d
R = Cl: PP0532-d
R = OMe: PP0534-d
R = OCF₃: PP0536-d -continued
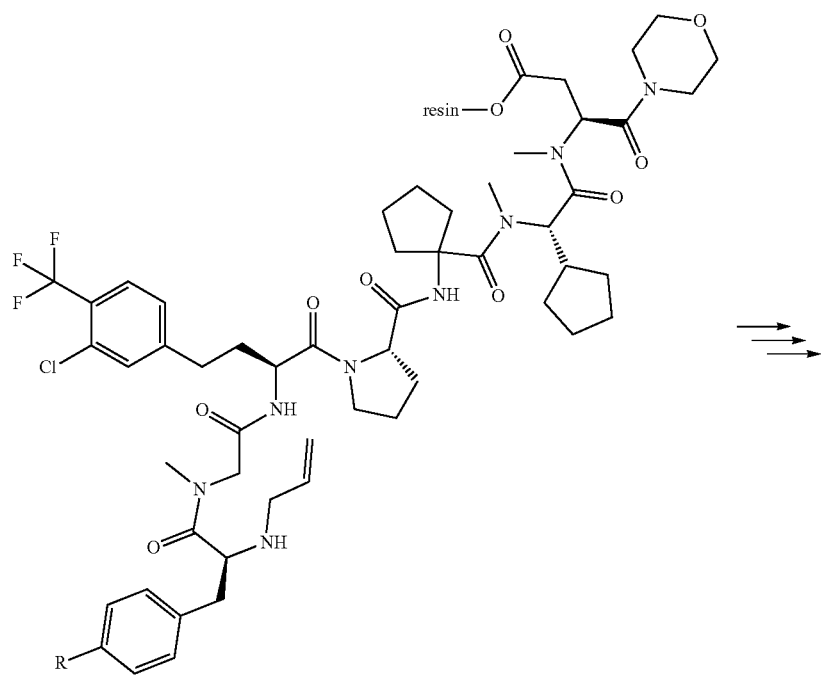
R = F: PP0530-e
R = Cl: PP0532-e
R = OMe: PP0534-e
R = OCF₃: PP0536-e
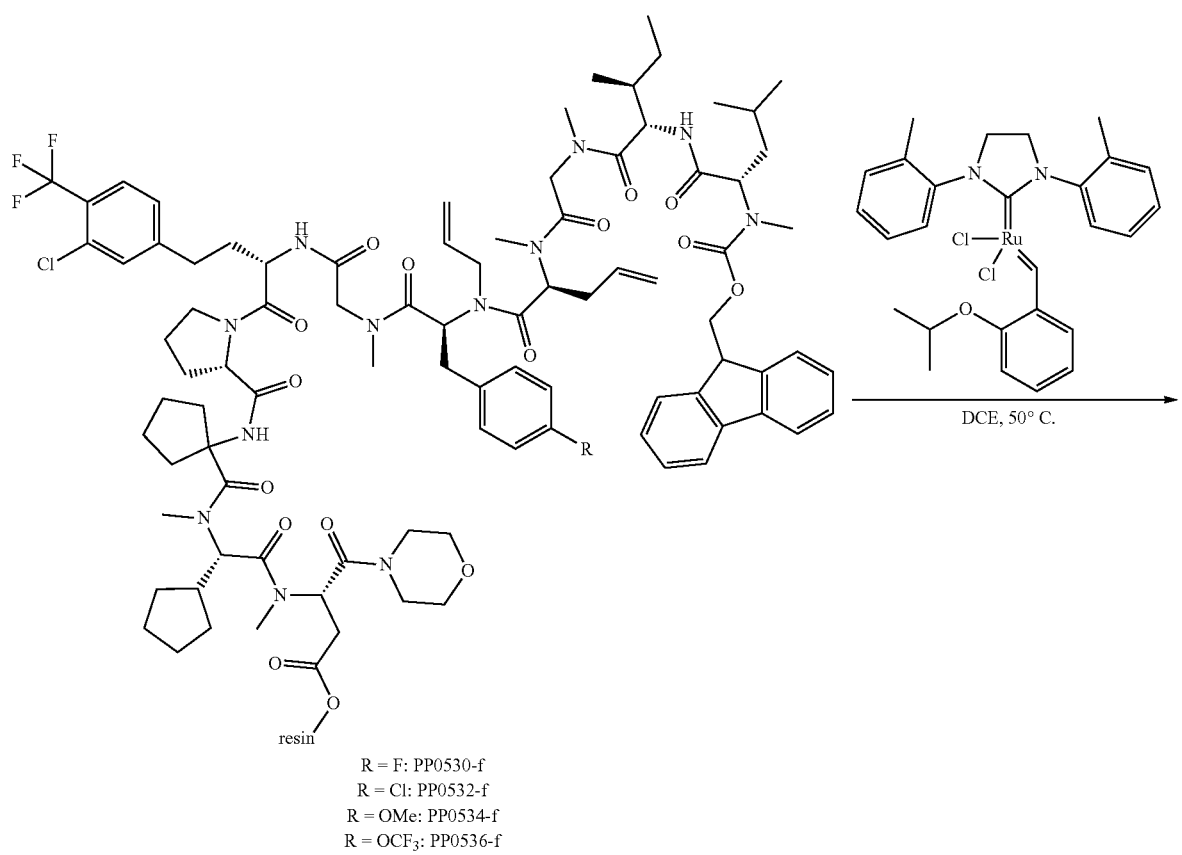
R = F: PP0530-f
R = Cl: PP0532-f
R = OMe: PP0534-f
R = OCF₃: PP0536-f -continued
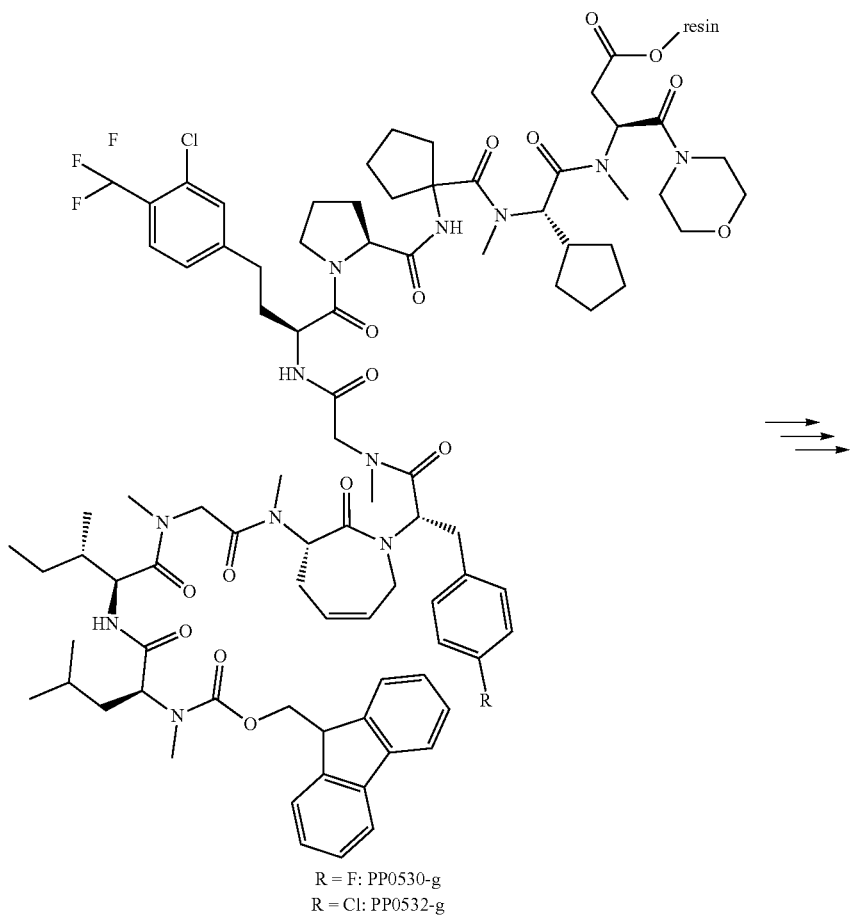
R = F: PP0530-g
R = Cl: PP0532-g
R = OMe: PP0534-g
R = OCF₃: PP0536-g
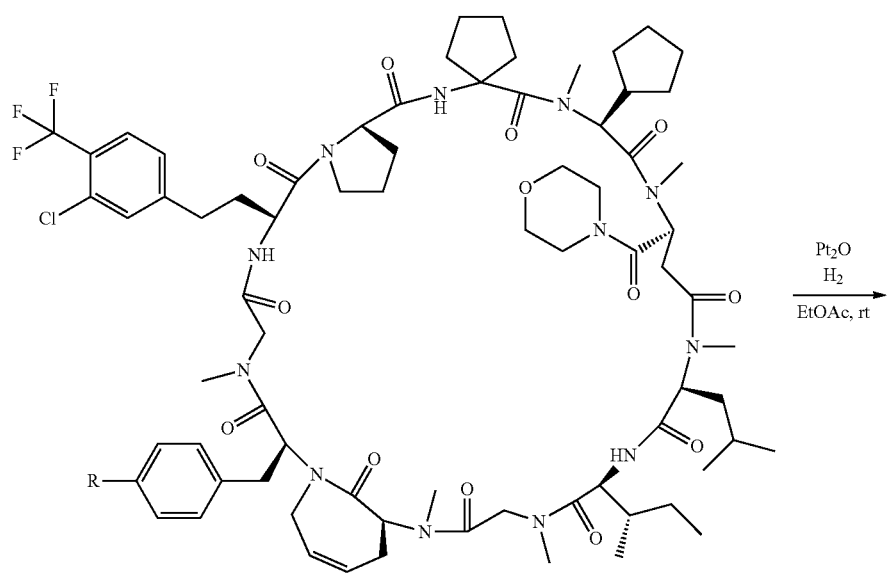
R = F: PP0531
R = Cl: PP0533
R = OMe: PP0535
R = OCF₃: PP0537

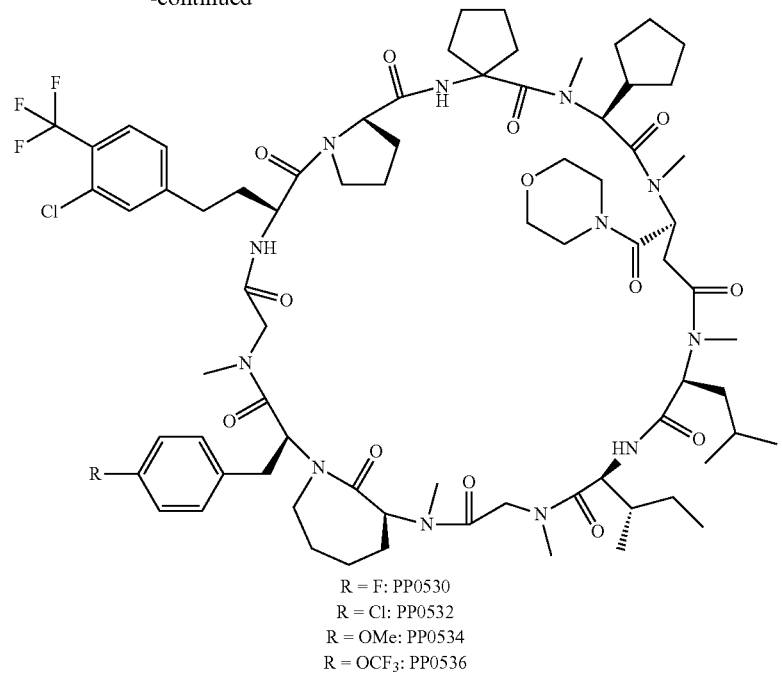

R = F: PP0530
R = Cl: PP0532
R = OMe: PP0534
R = OCF₃: PP0536

Using Compound aa375-resin as a raw material, peptide synthesis by the basic peptide synthesis method described in the present Examples was performed to give resin-supported Compound PP530-a, Compound PP532-a, Compound PP534-a, and Compound PP536-a.

After resin-supported Compound PP530-b, Compound PP532-b, Compound PP534-b, and Compound PP536-b were obtained in the same manner as synthesis of Compound PP55-b, resin-supported Compound PP530-c, Compound PP532-c, Compound PP534-c, and Compound PP536-c were obtained in the same manner as synthesis of Compound PP55-c using THE in place of NMP as a reaction solvent. After resin-supported Compound PP530-d, Compound PP532-d, Compound PP534-d, and Compound PP536-d were obtained in the same manner as Compound PP524-d by reacting 2-propen-1-ol in place of 3-fluoropropan-1-ol, resin-supported Compound PP530-e, Compound PP532-e, Compound PP534-e, and Compound PP536-e were obtained in the same manner as synthesis of Compound PP55-e. Subsequent peptide elongation was performed according to the basic route to give resin-supported Compound PP530-f, Compound PP532-f, Compound PP534-f, and Compound PP536-f. In the same manner as Compound PP529-g, resin-supported Compound PP530-g, Compound PP532-g, Compound PP534-g, and Compound PP536-g were obtained.

Subsequent steps of cleaving from resin, cyclization, and purification were performed according to the basic route to give Compound PP0531, Compound PP533, Compound PP535, and Compound PP537. LC/MS data is provided in Table 36. Moreover, using separately synthesized Compound PP531, Compound PP533, Compound PP535, and Compound PP537 that were at a crude product stage, Compound PP530, Compound PP532, Compound PP534, and Compound PP536 were obtained in the same manner as Compound PP529. LC/MS data is provided in Table 36.

1-6-7. Peptide Synthesis Via N-Alkylation by Mitsunobu Reaction on Resin and Olefin Metathesis Reaction Synthesis of Compounds PP0606 and PP0611

Compounds PP0606 and PP0611 were synthesized according to the following scheme.

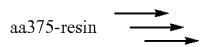

773 -continued
774
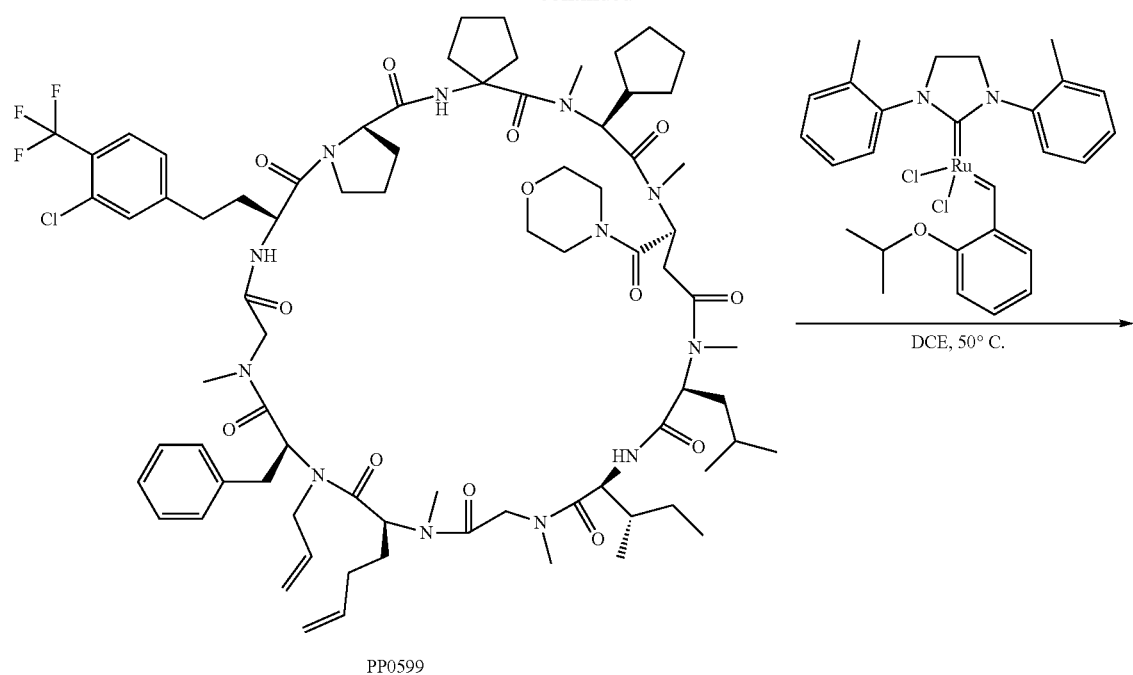
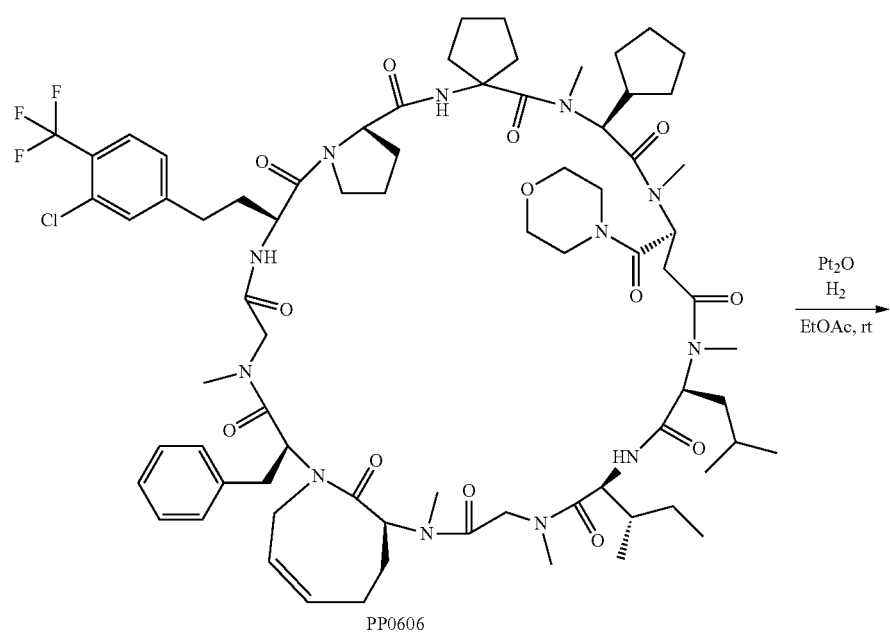

-continued

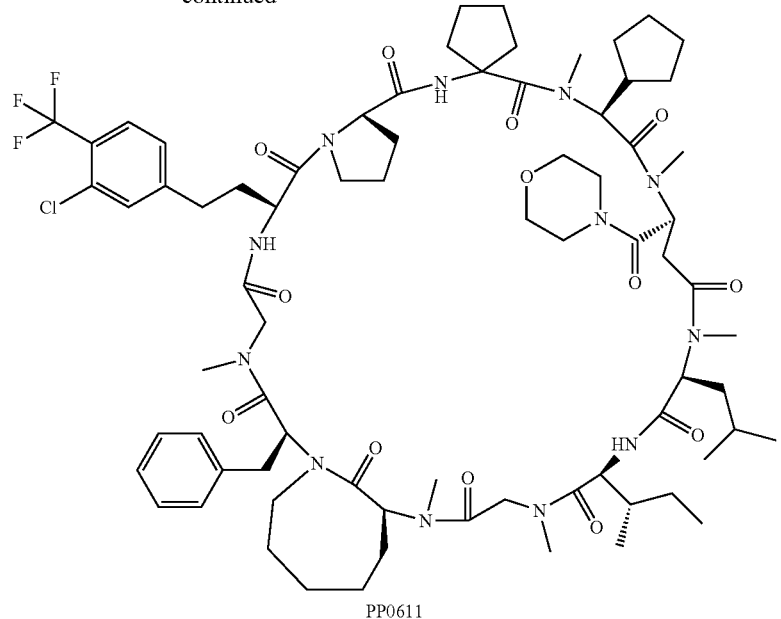
PP0611

PP599 (25 mg, 0.017 mmol) obtained using Compound aa375-resin as a raw material and a Stewart-Grubbs catalyst (2.4 mg, 0.0042 mmol) were dissolved in DCE (1.5 mL), and after a degassing operation, the mixture was stirred at 50° C. for 16 hours in a nitrogen atmosphere. A Stewart-Grubbs catalyst (2.4 mg, 0.0042 mmol) was added, and after a degassing operation, the mixture was stirred for 20 more hours at 50° C. in a nitrogen atmosphere, and then the solvent was distilled off under reduced pressure. This was purified by reverse phase chromatography (0.1% formic acid-containing acetonitrile/0.1% formic acid-containing distilled water) to give Compound PP0606 (4.1 mg, 17%). LC/MS data is provided in Table 36. Compound PP0606 (3.6 mg, 0.0024 mmol) was dissolved in ethyl acetate (1 mL), platinum (IV) oxide (0.28 mg, 0.0012 mmol) was added, and the mixture was stirred at room temperature for 5 hours in a hydrogen atmosphere. Platinum (IV) oxide was filtered off, and the solvent was distilled off under reduced pressure. The resulting crude product was purified by reverse phase chromatography (0.1% formic acid-containing acetonitrile/0.1% formic acid-containing distilled water) to give Compound PP0611 (1.9 mg, 53%). LC/MS data is provided in Table 36.

Synthesis of Compounds PP0607 to 0610 and PP0612 to 0615

Compounds PP0607 to 0610 and PP0612 to 0615 were synthesized according to the following scheme.

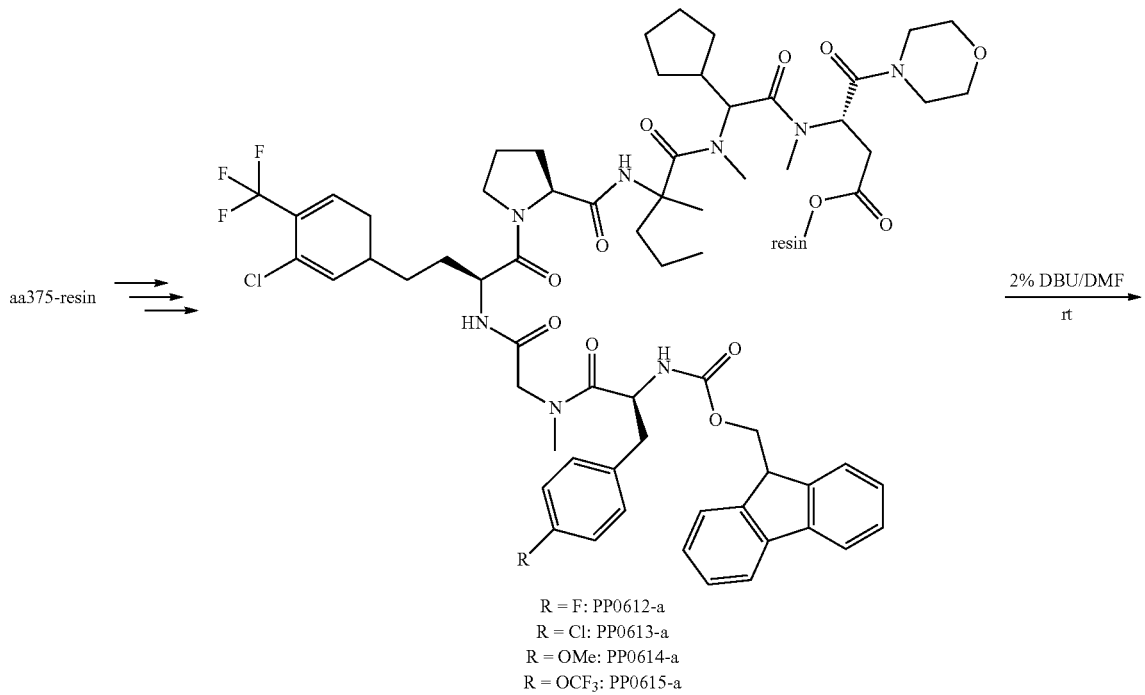

R = F: PP0612-a
R = Cl: PP0613-a
R = OMe: PP0614-a
R = OCF$_3$: PP0615-a

-continued
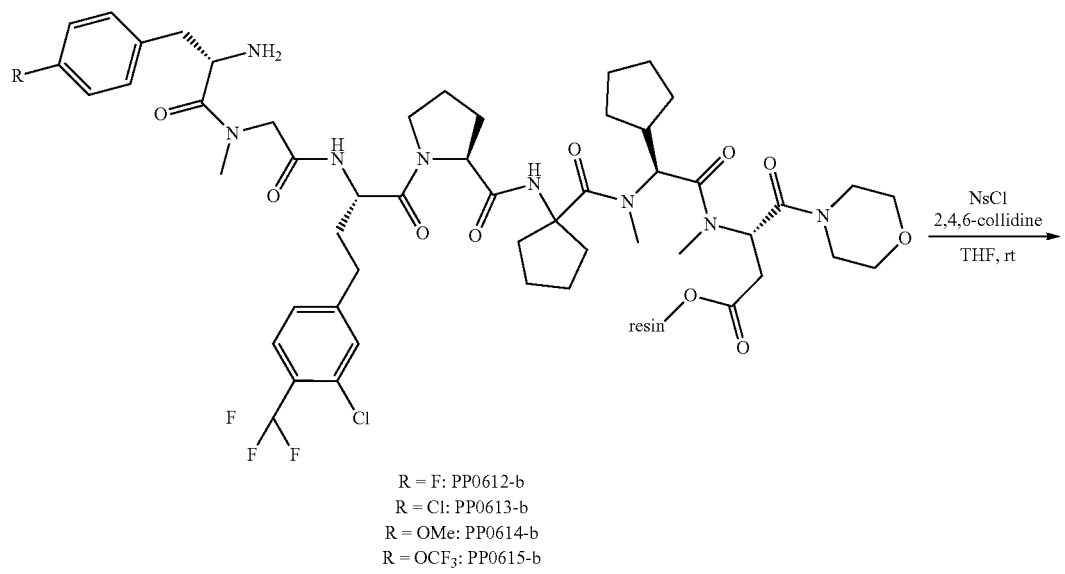
R = F: PP0612-b
R = Cl: PP0613-b
R = OMe: PP0614-b
R = OCF₃: PP0615-b
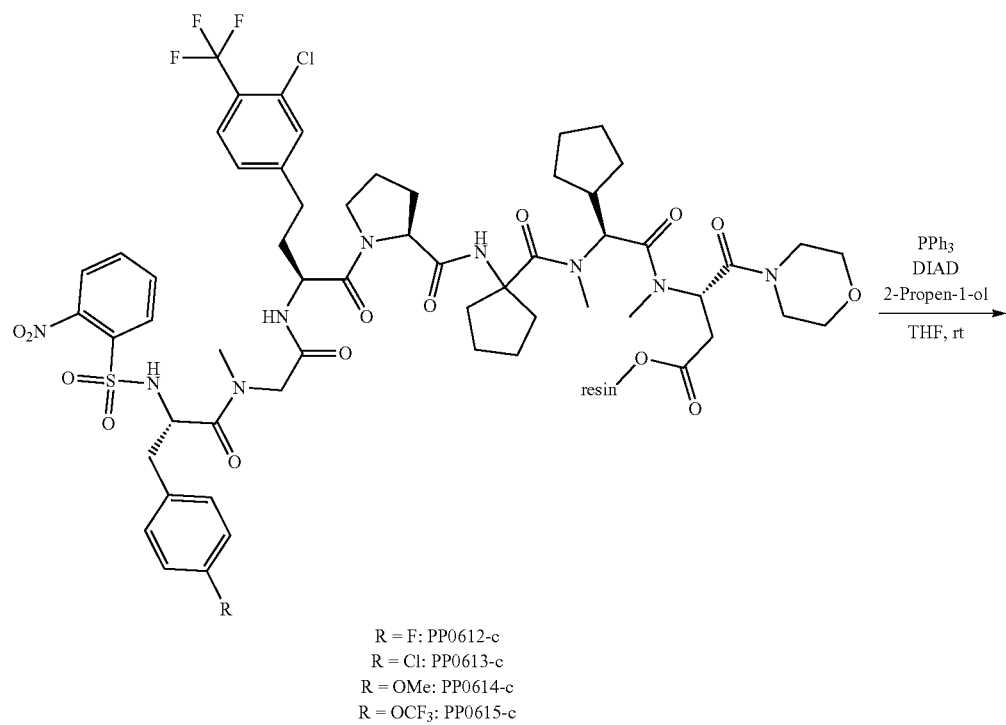
R = F: PP0612-c
R = Cl: PP0613-c
R = OMe: PP0614-c
R = OCF₃: PP0615-c

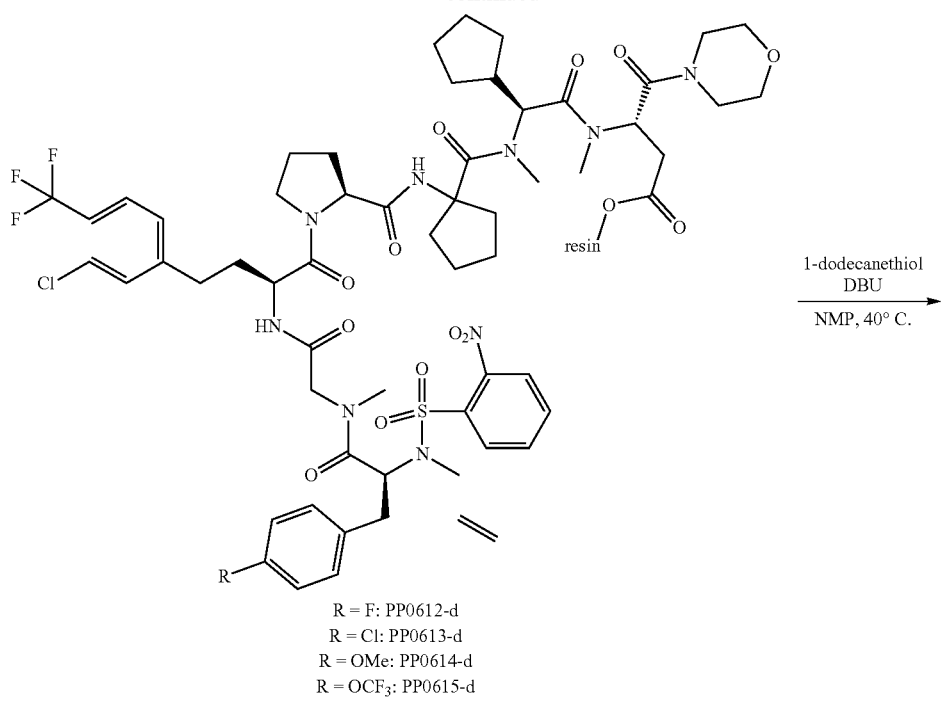
R = F: PP0612-d
R = Cl: PP0613-d
R = OMe: PP0614-d
R = OCF₃: PP0615-d
1-dodecanethiol
DBU
―――――――→
NMP, 40° C.
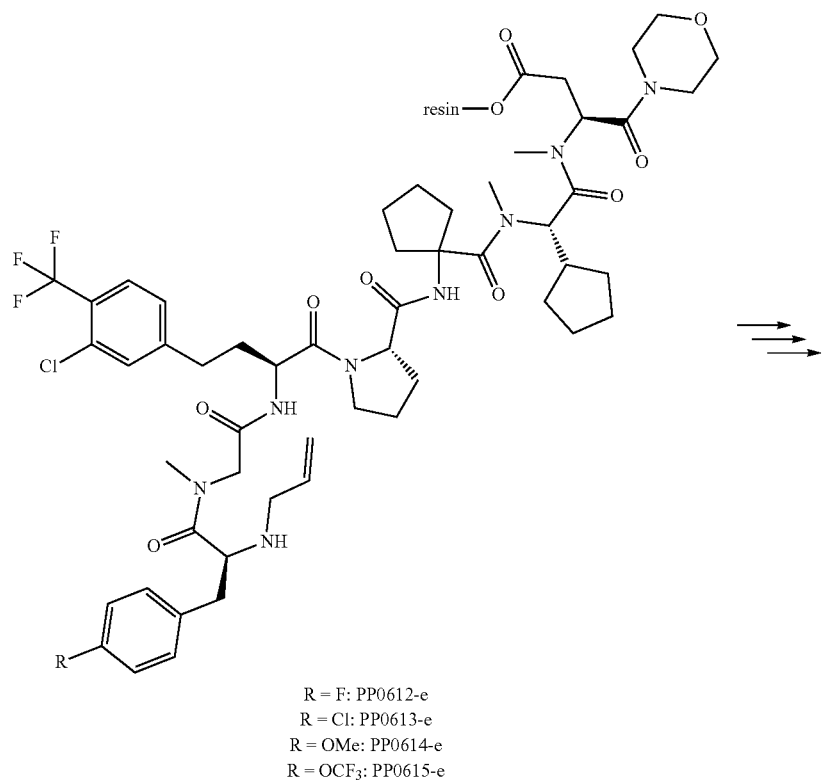
R = F: PP0612-e
R = Cl: PP0613-e
R = OMe: PP0614-e
R = OCF₃: PP0615-e

781 -continued 782
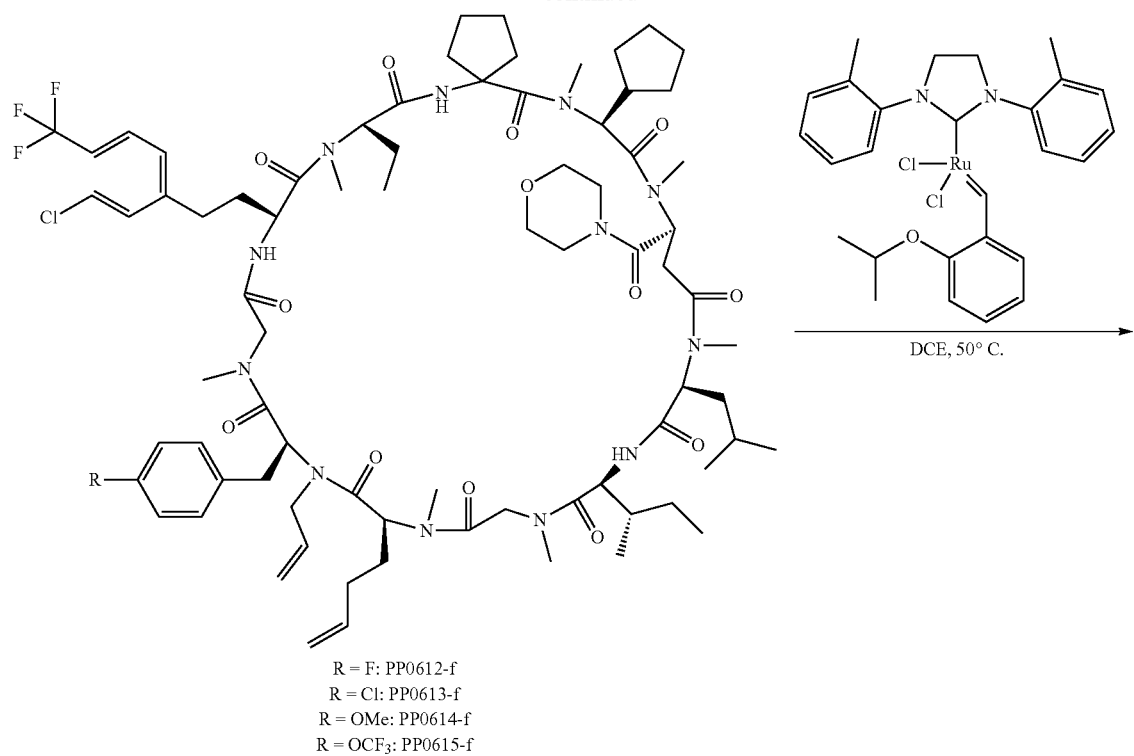
R = F: PP0612-f
R = Cl: PP0613-f
R = OMe: PP0614-f
R = OCF₃: PP0615-f
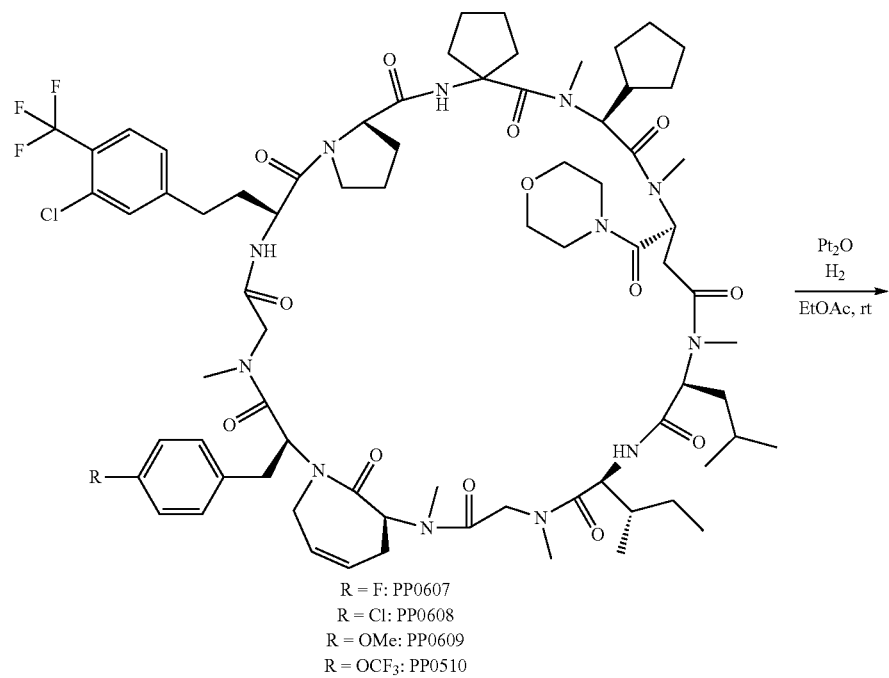
R = F: PP0607
R = Cl: PP0608
R = OMe: PP0609
R = OCF₃: PP0510

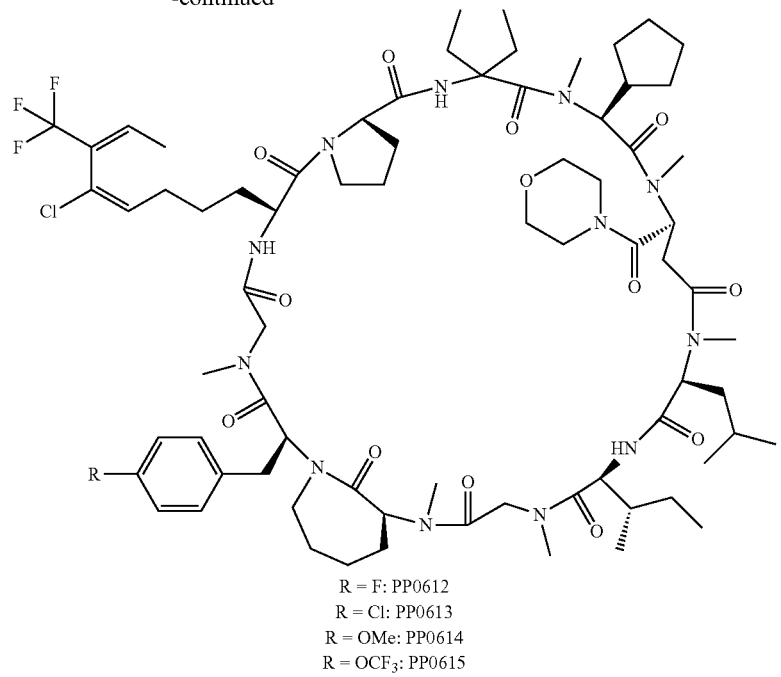

R = F: PP0612
R = Cl: PP0613
R = OMe: PP0614
R = OCF₃: PP0615

Using Compound aa375-resin as a raw material, peptide synthesis by the basic peptide synthesis method described in the present Examples was performed to give resin-supported Compound PP0612-a, Compound PP0613-a, Compound PP0614-a, and Compound PP0615-a.

After resin-supported Compound PP0612-b, Compound PP0613-b, Compound PP614-b, and Compound PP0615-b were obtained in the same manner as synthesis of Compound PP55-b, resin-supported Compound PP0612-c, Compound PP0613-c, Compound PP614-c, and Compound PP0615-c were obtained in the same manner as synthesis of Compound PP55-c using THF in place of NMP as a reaction solvent. After resin-supported Compound PP0612-d, Compound PP0613-d, Compound PP0614-d, and Compound PP0615-d were obtained in the same manner as synthesis of Compound PP524-d by reacting 2-propen-1-ol in place of 3-fluoropropan-1-ol, resin-supported Compound PP0612-e, Compound PP0613-e, Compound PP0614-e, and Compound PP0615-e were obtained in the same manner as synthesis of Compound PP55-e.

Subsequent steps of peptide elongation, cleaving from resin, cyclization, and purification were performed according to the basic route to give Compound PP0612-f, Compound PP0613-f, Compound PP0614-f, and Compound PP0615-f. Compound PP0607, Compound PP0608, Compound PP0609, and Compound PP0610 were obtained in the same manner as synthesis of Compound PP0606. Yields in amount and yields in percent are provided in Table 30. LC/MS data is provided in Table 36.

TABLE 30

| Raw material | Intended product | R | Yield | Yield |
| --- | --- | --- | --- | --- |
| Compound 0612-f | Compound 0607 | F | 6.9 mg | 28% |
| Compound 0613-f | Compound 0608 | Cl | 7.2 mg | 29% |
| Compound 0614-f | Compound 0609 | OMe | 6.9 mg | 28% |
| Compound 0615-f | Compound 0610 | OCF₃ | 5.3 mg | 20% |

Moreover, Compound PP0612, Compound PP0613, Compound PP0614, and Compound PP0615 were obtained in the same manner as synthesis of Compound PP0611. Yields in amount and yields in percent are provided in Table 31. LC/MS data is provided in Table 36.

TABLE 31

| Raw material | Intended product | R | Yield | Yield |
| --- | --- | --- | --- | --- |
| Compound 0607 | Compound 0612 | F | 6.4 mg | 100% |
| Compound 0608 | Compound 0613 | Cl | 6.6 mg | 98% |
| Compound 0609 | Compound 0614 | OMe | 5.8 mg | 91% |
| Compound 0610 | Compound 0615 | OCF₃ | 2.6 mg | 54% |

Synthesis of Compound PP316, Compound PP317, Compound PP0460, and Compound PP461

Compound PP316, Compound PP317, Compound PP0460, and Compound PP461 were synthesized according to the following scheme.

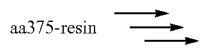

-continued
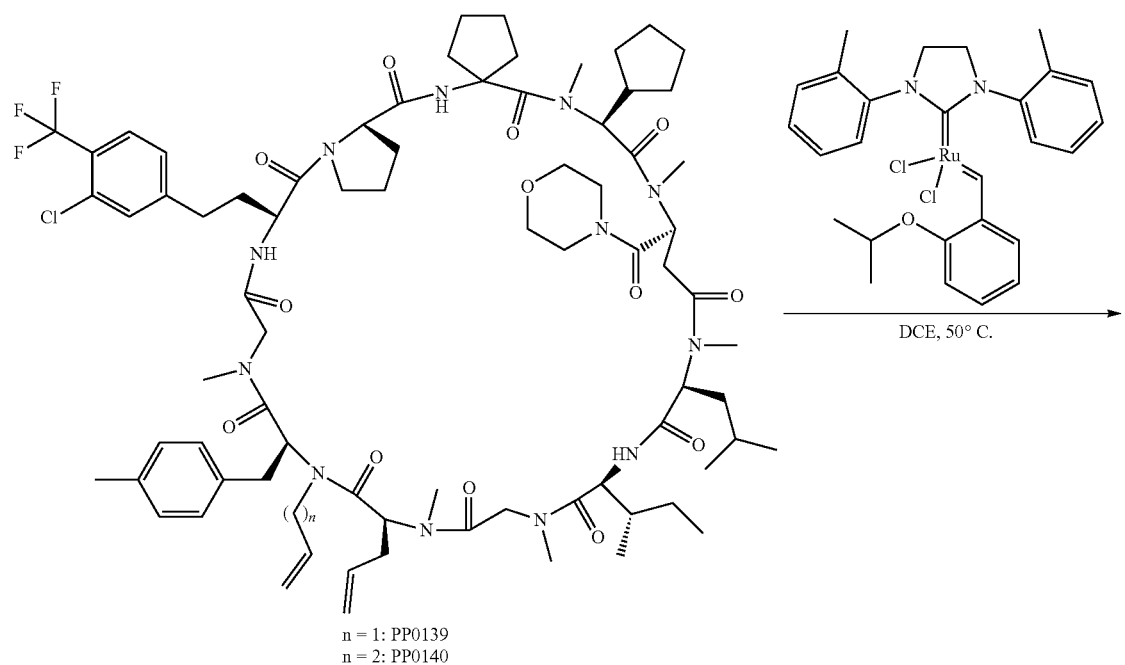
n = 1: PP0139
n = 2: PP0140
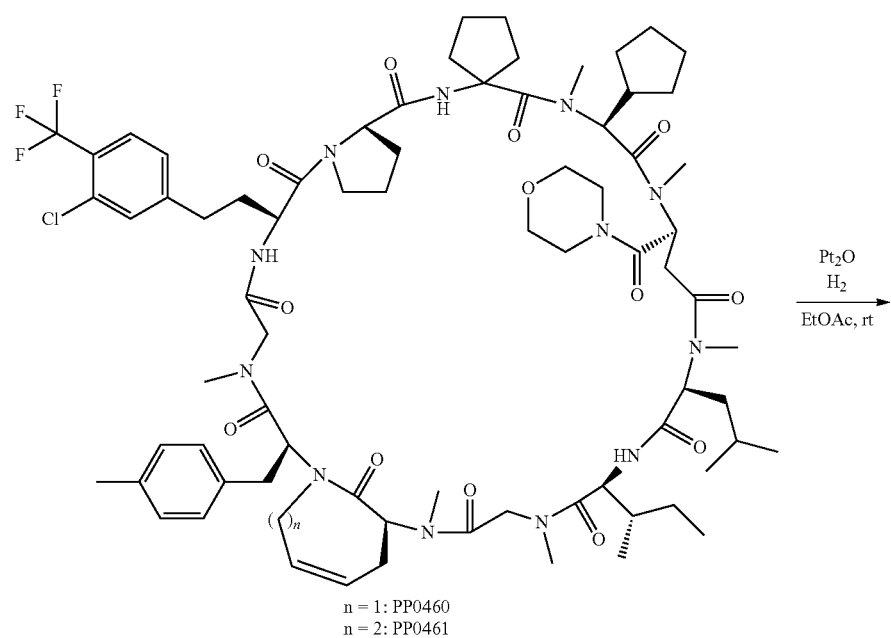
n = 1: PP0460
n = 2: PP0461

-continued

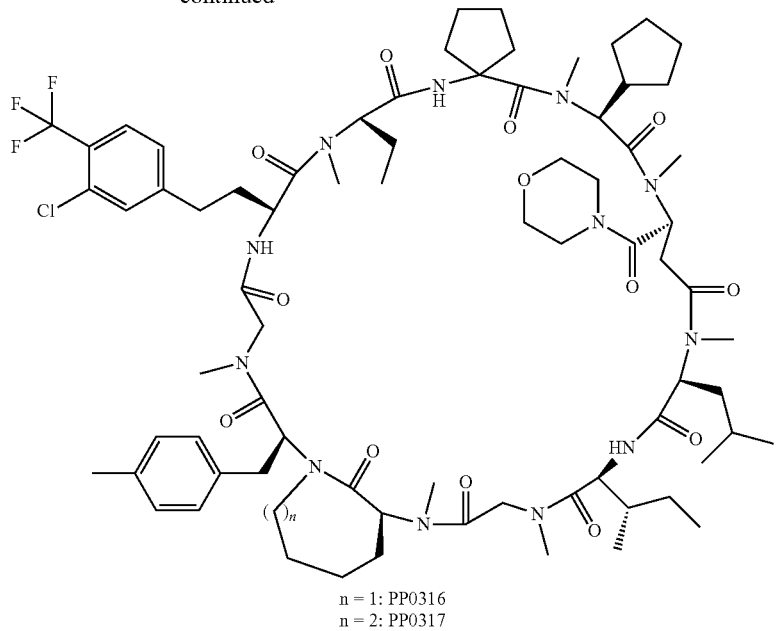

n = 1: PP0316
n = 2: PP0317

Using PP139 and PP140 obtained from Compound aa375-resin as a raw material, Compound PP0460 and Compound PP0461 were obtained in the same manner as synthesis of Compound PP0606. Yields in amount and yields in percent are provided in Table 32. LC/MS data is provided in Table 36.

TABLE 32

| Raw material | Intended product | n | Yield | Yield |
|---|---|---|---|---|
| Compound 0139 | Compound 0460 | 1 | 80 mg | 58% |
| Compound 0140 | Compound 0461 | 2 | 32 mg | 24% |

Moreover, Compound PP316 and Compound PP317 were obtained in the same manner as synthesis of Compound PP0611. Yields in amount and yields in percent are provided in Table 33. LC/MS data is provided in Table 36.

TABLE 33

| Raw material | Intended product | n | Yield | Yield |
|---|---|---|---|---|
| Compound 0460 | Compound 0316 | 1 | 60 mg | 80% |
| Compound 0461 | Compound 0317 | 2 | 18 mg | 64% |

Synthesis of Compound PP318, Compound PP319, Compound PP0462, and Compound PP463

Compound PP318, Compound PP319, Compound PP0462, and Compound PP0463 were synthesized according to the following scheme.

aa375-resin →→

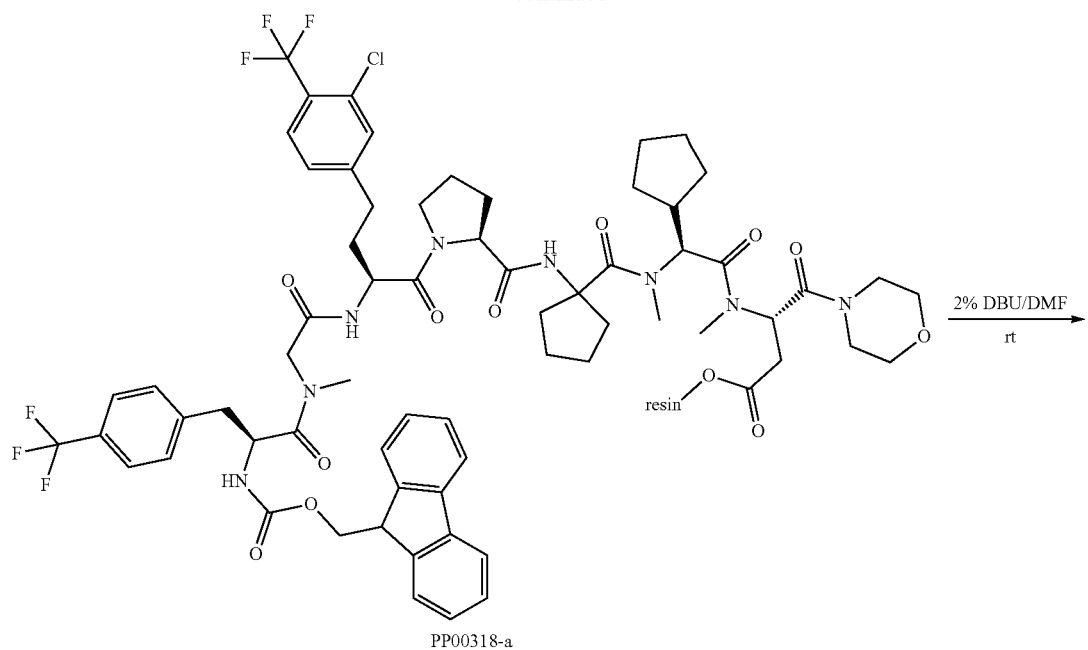
PP00318-a
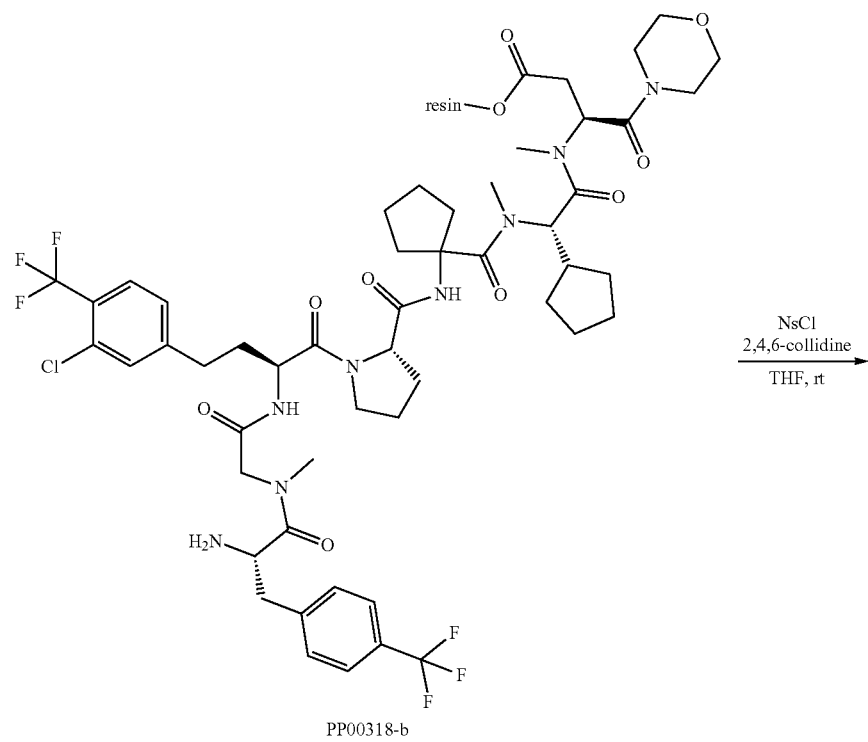
PP00318-b

-continued
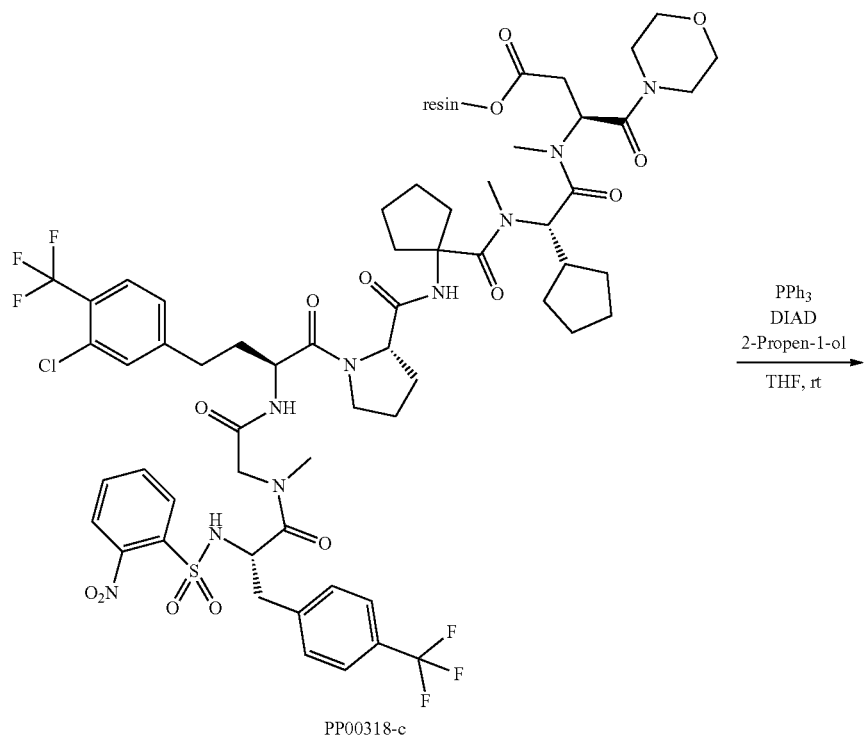
PP00318-c
PPh₃
DIAD
2-Propen-1-ol
THF, rt
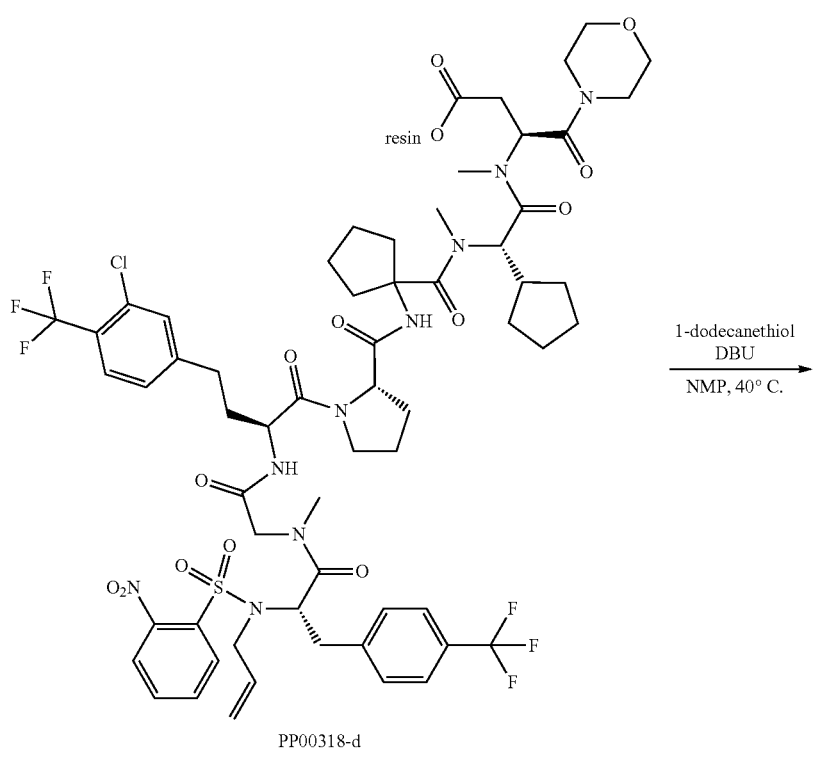
PP00318-d
1-dodecanethiol
DBU
NMP, 40° C.

-continued
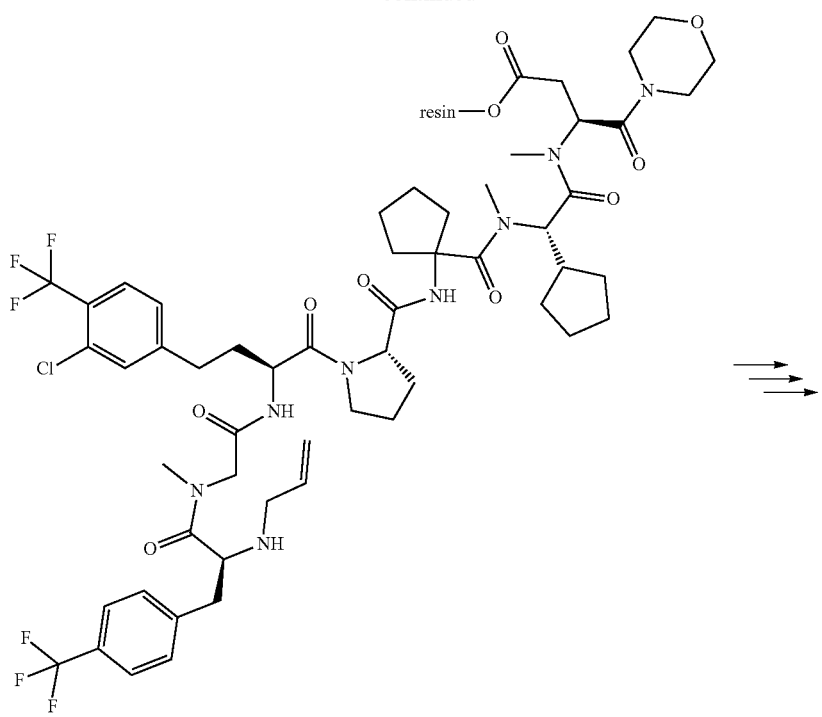
PP00318-e
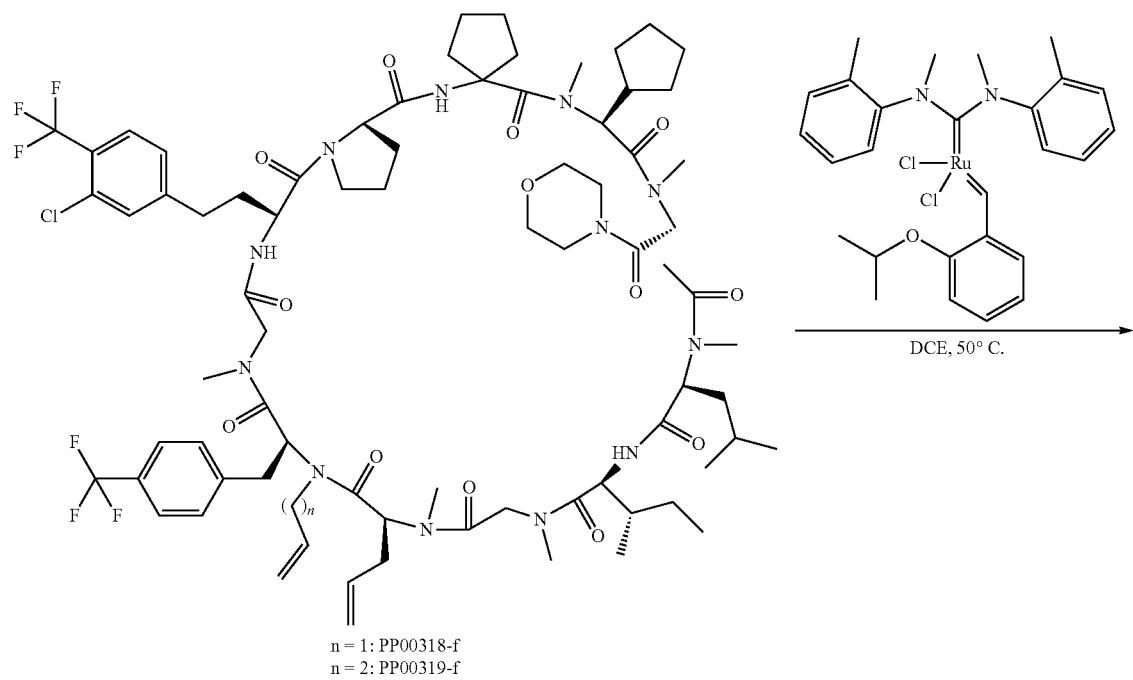
n = 1: PP00318-f
n = 2: PP00319-f

-continued

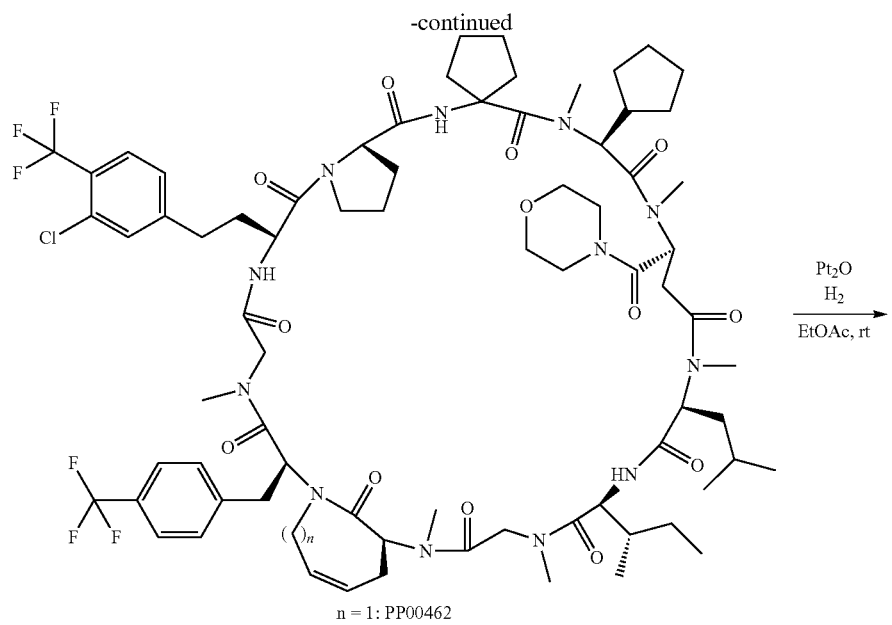

n = 1: PP00462
n = 2: PP00463

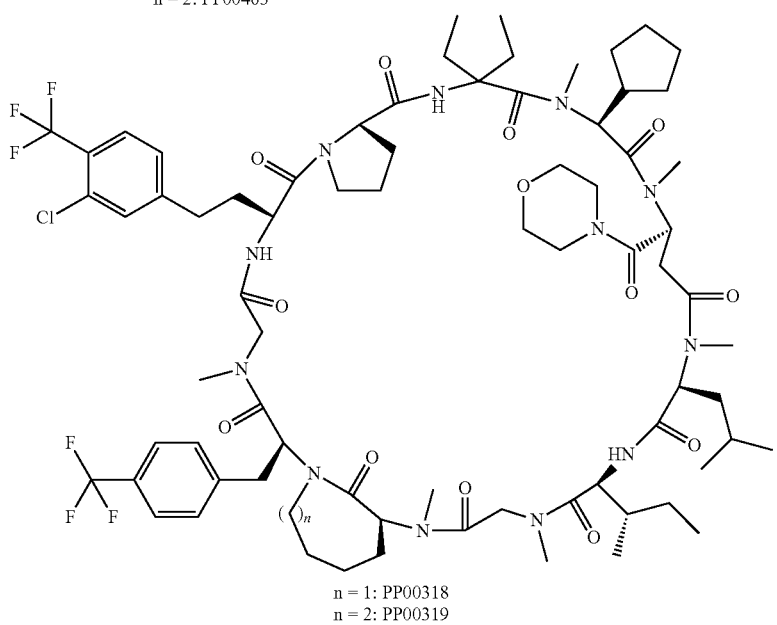

n = 1: PP00318
n = 2: PP00319

Using Compound aa375-resin as a raw material, peptide synthesis by the basic peptide synthesis method described in the present Examples was performed to give resin-supported Compound PP318-a.

After resin-supported Compound PP318-b was obtained in the same manner as synthesis of Compound PP55-b, resin-supported Compound PP318-c was obtained in the same manner as synthesis of Compound PP55-c using THE in place of NMP as a reaction solvent. After resin-supported Compound PP318-d was obtained in the same manner as synthesis of Compound PP524-d by reacting 2-propen-1-ol in place of 3-fluoropropan-1-ol, resin-supported Compound PP318-e was obtained in the same manner as synthesis of Compound PP55-e.

Subsequent steps of peptide elongation, cleaving from resin, cyclization, and purification were performed according to the basic route to give Compound PP0318-f and Compound PP319-f. Compound PP0462 and Compound PP0463 were obtained in the same manner as synthesis of Compound PP0606. Yields in amount and yields in percent are provided in Table 34. LC/MS data is provided in Table 36.

TABLE 34

| Raw material | Intended product | n | Yield | Yield |
| --- | --- | --- | --- | --- |
| Compound 0318-f | Compound 0462 | 1 | 59 mg | 76% |
| Compound 0319-f | Compound 0463 | 2 | 18 mg | 23% |

Moreover, Compound PP318 and Compound PP319 were obtained in the same manner as synthesis of Compound PP0611. Yields in amount and yields in percent are provided in Table 35. LC/MS data is provided in Table 36.

TABLE 35

| Raw material | Intended product | n | Yield | Yield |
|---|---|---|---|---|
| Compound 0462 | Compound 0318 | 1 | 46 mg | 81% |
| Compound 0463 | Compound 0319 | 2 | 10 mg | 65% |

1-6-8. Peptide Modification by Hydroboration Reaction and Suzuki Coupling
Synthesis of Compound PP02117

Using Compound aa440-resin (Fmoc-MeGly (cPent)-MeAsp (O-Trt (2-C1) resin)-MeNEt) as a raw material, peptide synthesis was carried out by the basic peptide synthesis method described in the present Examples to give Compound PP02117-a. A THF solution of 9-BBN (0.5 M, 240 μL, 120 μmol) was added to Compound PP02117-a (12.4 mg, 7.67 μmol), and the mixture was stirred for 1.5 hours in a nitrogen atmosphere. The resulting reaction solution was diluted with THF (500 μL), then water (4 μL,

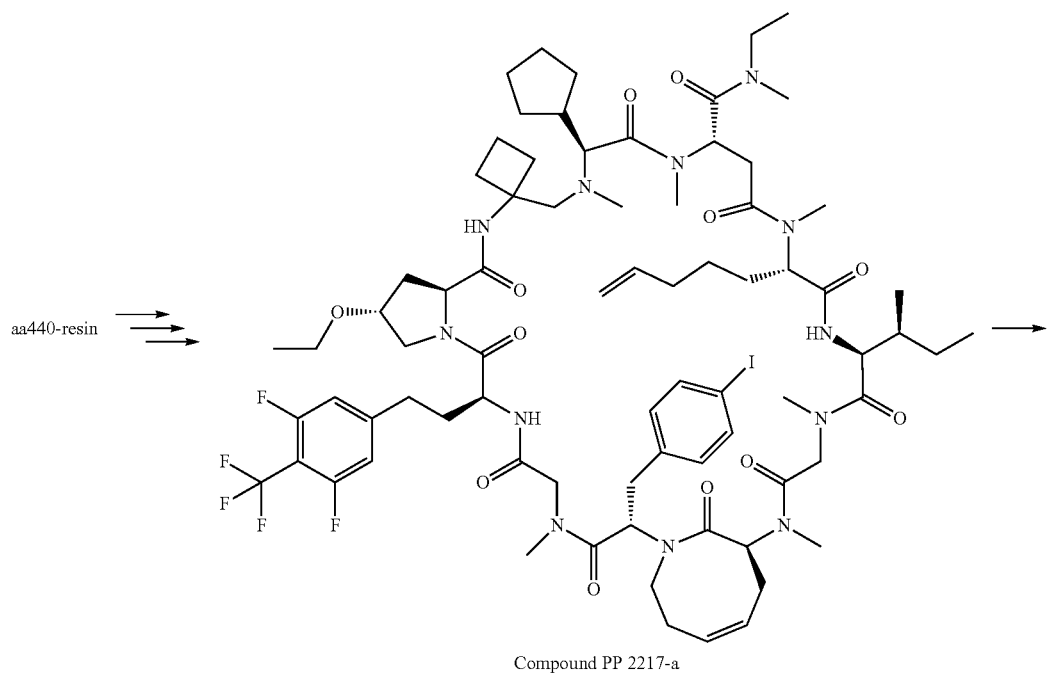

Compound PP 2217-a

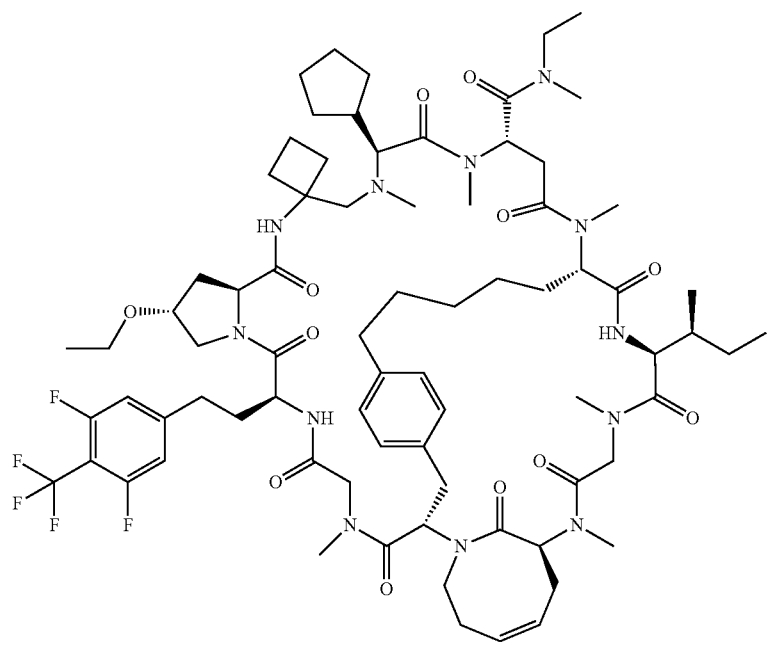

Compound PP 2217

222 µmol), cataCXium A Pd G4 (CAS No. 2230788-67-5, 2.7 mg, 3.64 µmol), and 2-tert-butyl-1,1,3,3-tetramethylguanidine (131 µL, 110 µmol) were added, and the mixture was stirred at 60° C. for 1 hour in a nitrogen atmosphere. After being cooled to room temperature, the reaction solution was halved, either a 2% aqueous N-acetylcysteine solution (100 µL) or a 10% aqueous dithiothreitol solution (100 µL) was added, the mixture was stirred for 1 hour, the reaction solution was purified twice by reverse phase HPLC(methanol/50 mM aqueous ammonium acetate solution, then 0.1% formic acid-containing acetonitrile/0.1% formic acid-containing distilled water), and the fractions were combined to give PP2117 (3.2 mg, 6.1%).

LCMS (ESI) m/z=1492 (M+H)+

Retention time: 0.56 min (Analytical condition SQDFA50)

Synthesis of Compound PP02118

Synthesis of PP2118 was carried out according to the following scheme.

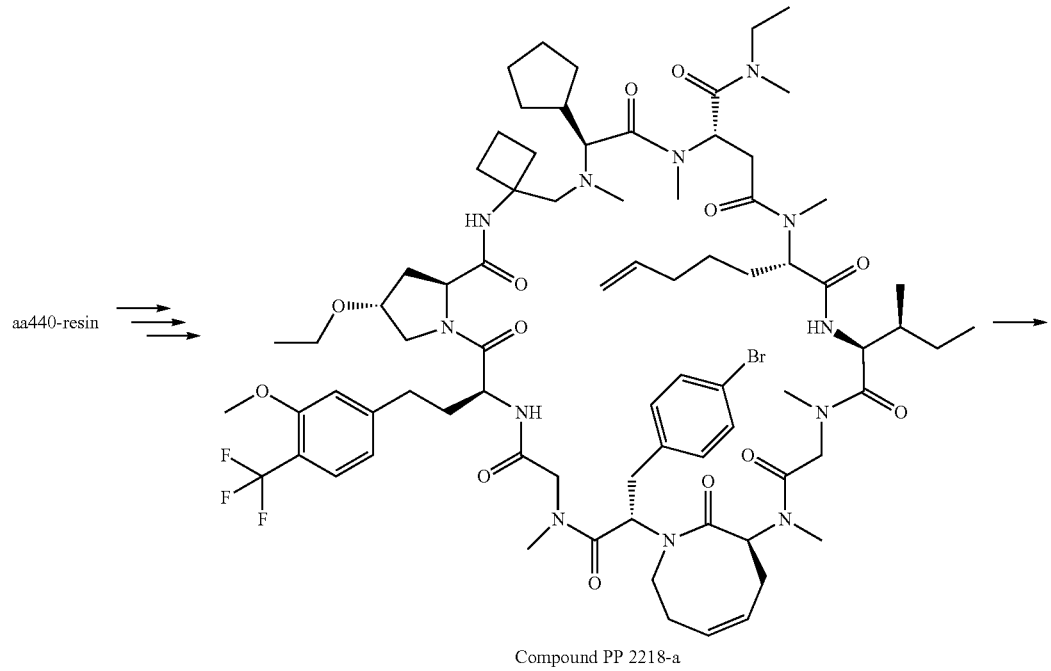

Compound PP 2218-a

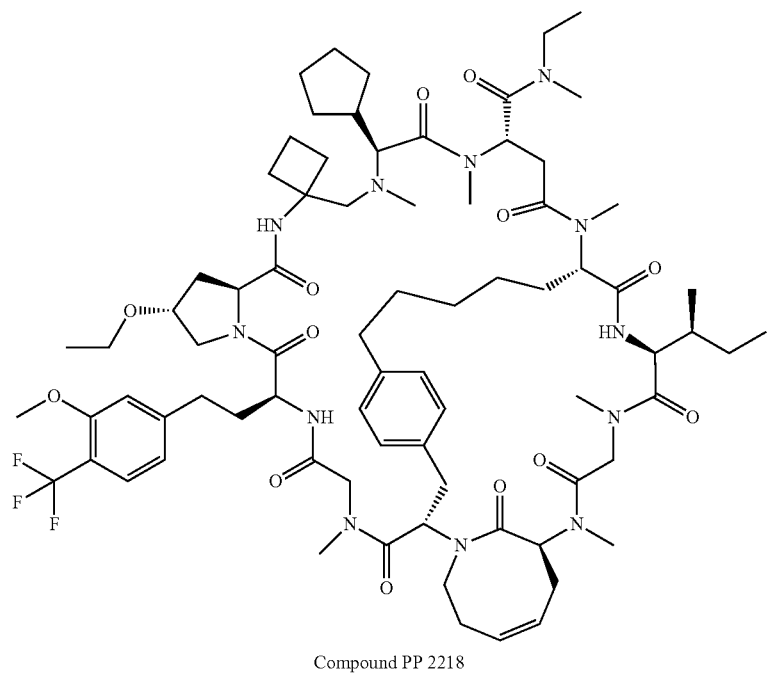

Compound PP 2218

Using Compound aa440-resin (Fmoc-MeGly (cPent)-MeAsp (O-Trt (2-Cl) resin)-MeNEt) as a raw material, peptide synthesis was carried out by the basic peptide synthesis method described in the present Examples to give Compound PP02118-a. A THF solution of 9-BBN (0.5 M, 240 μL, 120 μmol) was added to Compound PP02118-a (12.1 mg, 7.70 μmol), and the mixture was stirred for 1.5 hours in a nitrogen atmosphere. The resulting reaction solution was diluted with THF (500 μL), then water (4 μL, 222 μmol), cataCXium Pd G4 (CAS No. 2230788-67-5, 2.7 mg, 3.64 μmol), and 2-tert-butyl-1,1,3,3-tetramethylguanidine (131 μL, 110 μmol) were added, and the mixture was stirred at 60° C. for 1 hour in a nitrogen atmosphere. After being cooled to room temperature, the reaction solution was halved, either a 2% aqueous N-acetylcysteine solution (100 μL) or a 10% aqueous dithiothreitol solution (100 μL) was added, the mixture was stirred for 1 hour, the reaction solution was purified twice by reverse phase HPLC(methanol/50 mM aqueous ammonium acetate solution, then 0.1% formic acid-containing acetonitrile/0.1% formic acid-containing distilled water), and the fractions were combined to give PP2118 (3.2 mg, 6.1%).

LCMS (ESI) m/z=1486 (M+H)+

Retention time: 0.53 min (Analytical condition SQDFA50)

Synthesis of Compound PP02259 Synthesis of PP2259 was carried out according to the following scheme.

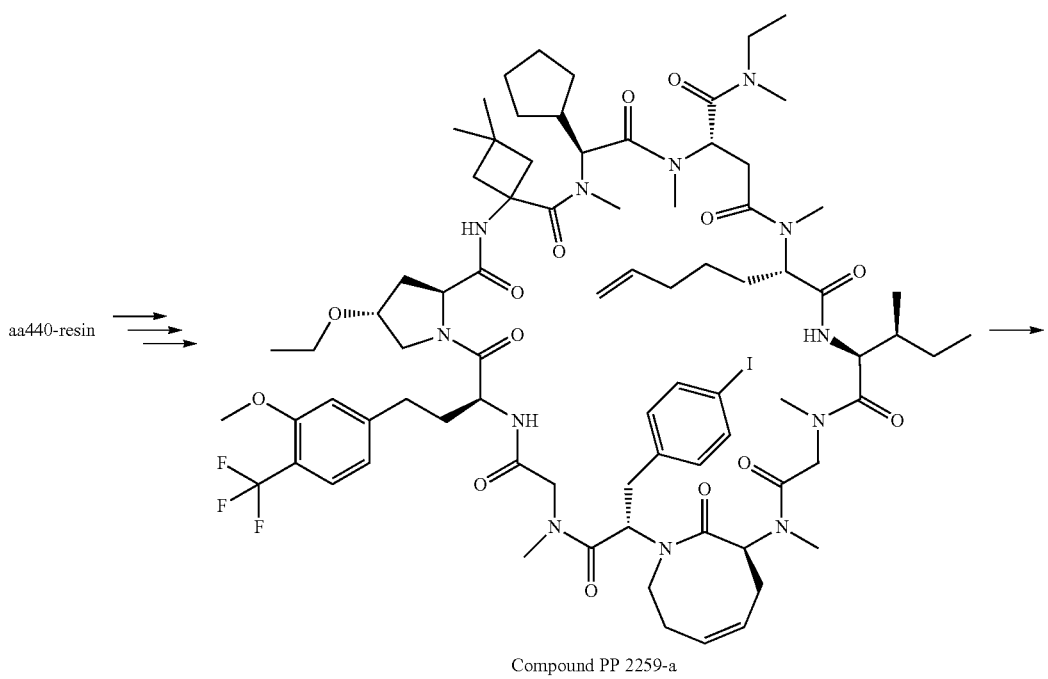

Compound PP 2259-a

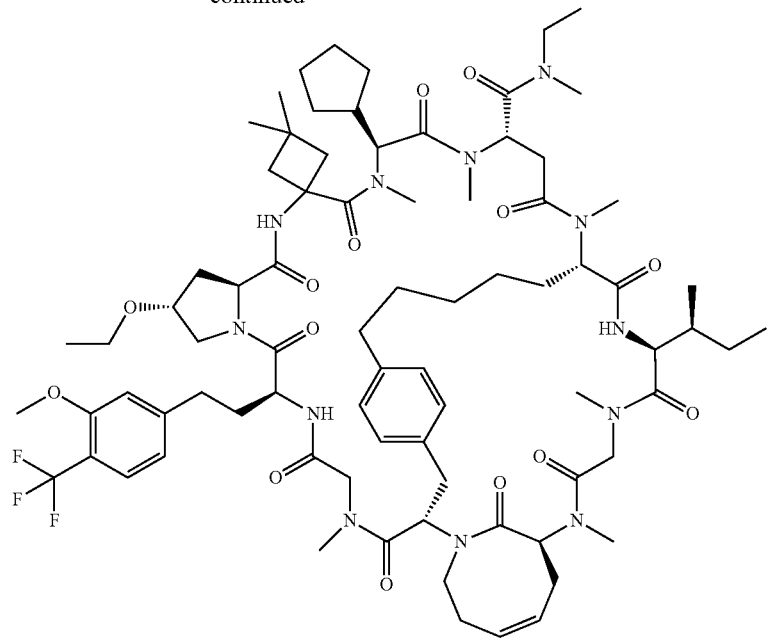

Compound PP 2259

Using Compound aa440-resin (Fmoc-MeGly (cPent)-MeAsp (O-Trt (2-C1) resin)-MeNEt) as a raw material, peptide synthesis was carried out by the basic peptide synthesis method described in the present Examples to give Compound PP02259-a. The resulting compound was azeotroped twice with toluene (1 mL). A THF solution of 9-BBN (0.1 M, 137 μL, 137 μmol, 2 eq) was added to Compound PP02259-a (11.2 mg, 6.83 μmol) azeotroped with toluene, and the mixture was stirred for 1 hour in a nitrogen atmosphere. The resulting reaction solution was diluted with THF (500 μL), then water (4 μL, 222 μmol, 30 eq), [1,1'-bis(di-tert-butylphosphino) ferrocene] dichloropalladium (2.3 mg, 3.5 μmol, 0.5 eq), and 2-tert-butyl-1,1,3,3-tetramethylguanidine (13 μL, 110 μmol, 15 eq) were added, and the mixture was stirred at 60° C. for 1 hour in a nitrogen atmosphere. After the mixture was cooled to room temperature, a 2% aqueous N-acetylcysteine solution (200 μL) was added, the mixture was stirred for 1 hour, then the reaction solution was purified by reverse phase HPLC(0.1% formic acid-containing acetonitrile/0.1% formic acid-containing distilled water) to give PP2259 (4.2 mg, 7.9%).

LCMS (ESI) m/z=1514 (M+H)+

Retention time: 0.62 min (Analytical condition SQDFA50)

Synthesis of Compound PP02260

Synthesis of PP2260 was carried out according to the following scheme.

aa440-resin →→→

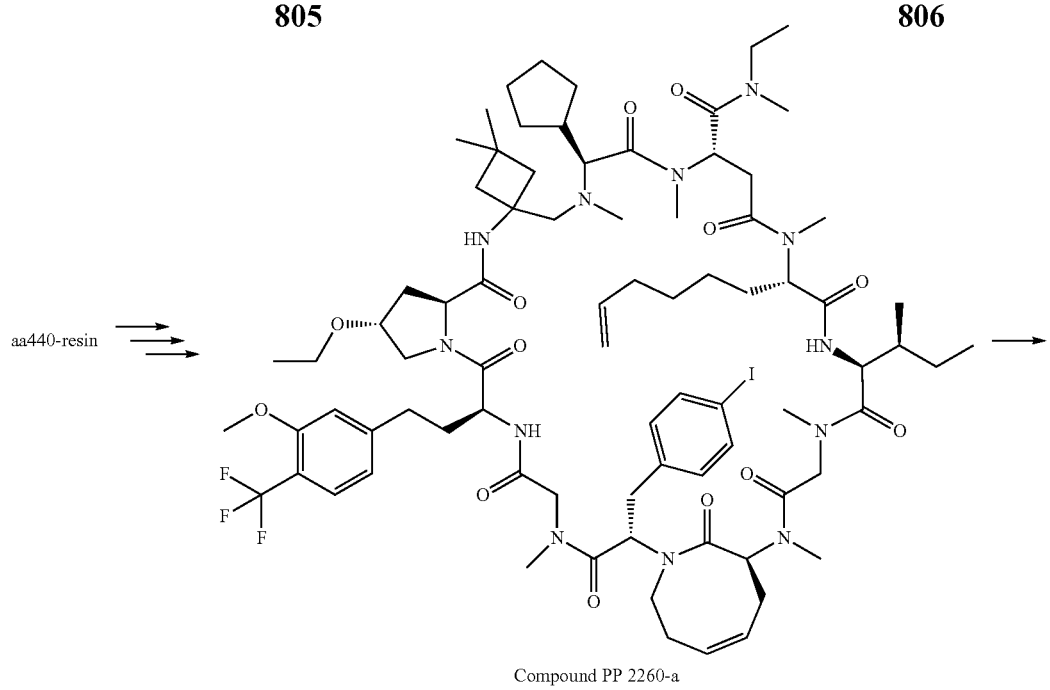

Compound PP 2260-a

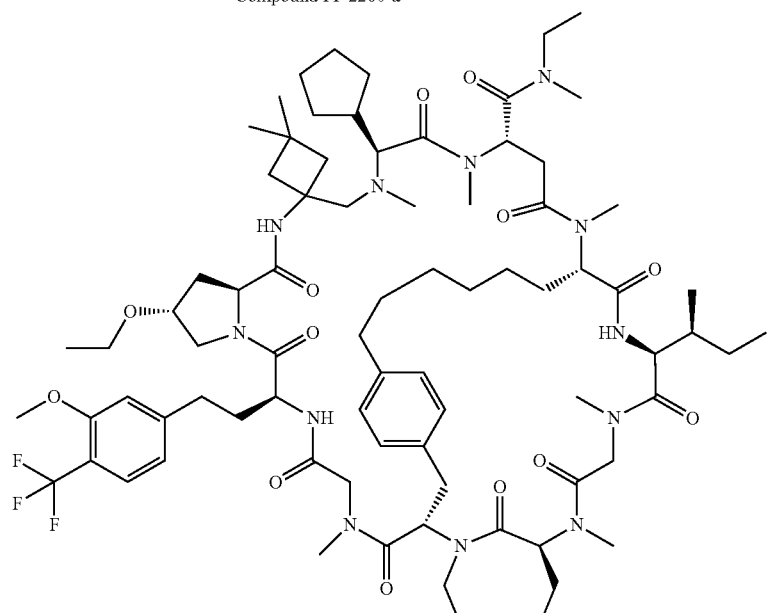

Compound PP 2260

Using Compound aa440-resin (Fmoc-MeGly (cPent)-MeAsp (O-Trt (2-C1) resin)-MeNEt) as a raw material, peptide synthesis was carried out by the basic peptide synthesis method described in the present Examples to give Compound PP02260-a. The resulting compound was azeotroped twice with toluene (1 mL). A THF solution of 9-BBN (0.1 M, 143 μL, 143 μmol, 2 eq) was added to Compound PP02260-a (11.8 mg, 7.14 μmol) azeotroped with toluene, and the mixture was stirred for 1 hour in a nitrogen atmosphere. The resulting reaction solution was diluted with THF (500 μL), then water (4 μL, 222 μmol, 30 eq), cataCXium Pd G4 (CAS No. 2230788-67-5, 2.7 mg, 3.6 μmol, 0.5 eq), and 2-tert-butyl-1,1,3,3-tetramethylguanidine (13 μL, 110 μmol, 15 eq) were added, and the mixture was stirred at 60° C. for 1 hour in a nitrogen atmosphere. After the mixture was cooled to room temperature, a 10% aqueous dithiothreitol solution (200 μL) was added, the mixture was stirred for 1 hour, the reaction solution was purified by reverse phase HPLC(0.1% formic acid-containing acetonitrile/0.1% formic acid-containing distilled water) to give PP2260 (4.1 mg, 7.6%).

LCMS (ESI) m/z=1528 (M+H)+

Retention time: 0.67 min (Analytical condition SQDFA50)

Using any of Compounds aa359-resin, aa360-resin, aa362-resin, aa374-resin, aa429-resin, and aa440-resin as a raw material, peptide synthesis was carried out by the basic peptide synthesis method described in the present Examples to give a cyclic peptide as an intermediate. Using the resulting intermediate peptide, compounds shown in Table 35-1 were produced in the same manner as the synthesis of Compound PP02259 by reacting the side chain moiety of any of MeAlgly, MeAhxe (2), MeAhpe (2), MeAocte (2), and MeAnone (2) with the iodide moiety of ButenylPhe (4-I). Purification was carried out by reverse phase HPLC purification (methanol/50 mM aqueous ammonium acetate solution or 0.1% formic acid-containing acetonitrile/0.1% formic acid-containing distilled water, or both if necessary). The intended product and the yield (amount/percentage) are provided in Table 35-2. LC/MS data are provided in Table 36.

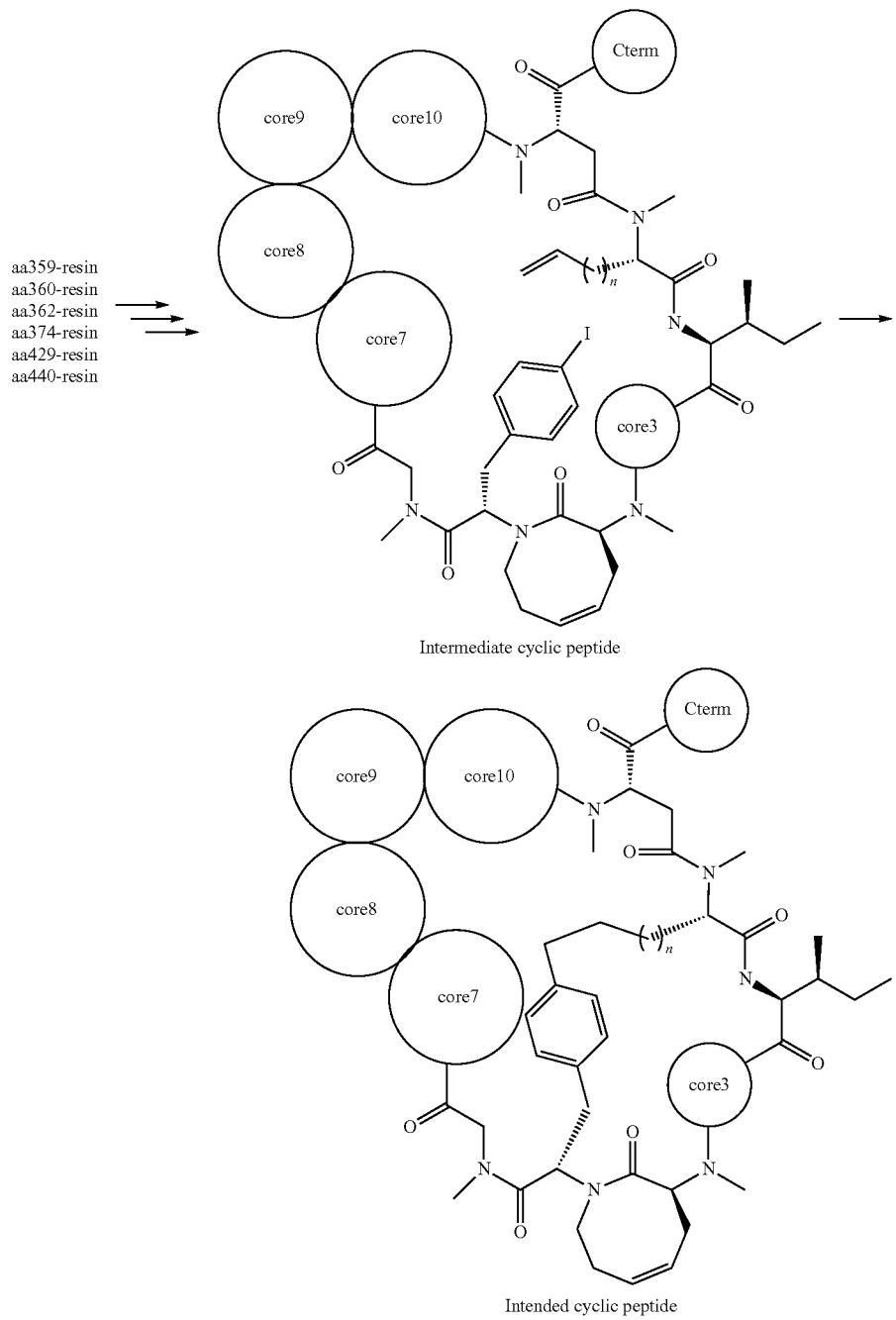

Intermediate cyclic peptide

Intended cyclic peptide

TABLE 35-1

| ID | 1 | 2 | 3 | 4 | 5 | 6 | 7 |
|---|---|---|---|---|---|---|---|
| PP2117 | MeAhpe(2) | Ile | MeGly | MeAlgly | ButenylPhe(4-CH=CH2) | MeGly | Hph(4-CF3-35-F2) |
| PP2118 | MeAhpe(2) | Ile | MeGly | MeAlgly | ButenylPhe(4-CH=CH2) | MeGly | Hph(4-CF3-3-OMe) |
| PP2259 | MeAhpe(2) | Ile | MeGly | MeAlgly | ButenylPhe(4-CH=CH2) | MeGly | Hph(4-CF3-3-OMe) |

TABLE 35-1-continued

| | | | | | | | |
|---|---|---|---|---|---|---|---|
| PP2260 | MeAocte(2) | Ile | MeGly | MeAlgly | ButenylPhe(4-CH=CH2) | MeGly | Hph(4-CF3-3-OMe) |
| PP2261 | MeAhpe(2) | Ile | MeGly | MeAlgly | ButenylPhe(4-CH=CH2) | MeGly | Hph(4-CF3-35-F2) |
| PP2262 | MeAhpe(2) | Ile | MeGly | MeAlgly | ButenylPhe(4-CH=CH2) | MeGly | Hph(4-CF3-3-OMe) |
| PP2263 | MeAocte(2) | Ile | MeGly | MeAlgly | ButenylPhe(4-CH=CH2) | MeGly | Hph(4-CF3-3-OMe) |
| PP2264 | MeAocte(2) | Ile | MeGly | MeAlgly | ButenylPhe(4-CH=CH2) | MeGly | Hph(4-CF3-3-OMe) |
| PP2265 | MeAnone(2) | Ile | MeGly | MeAlgly | ButenylPhe(4-CH=CH2) | MeGly | Hph(4-CF3-35-F2) |
| PP2266 | MeAnone(2) | Ile | MeGly | MeAlgly | ButenylPhe(4-CH=CH2) | MeGly | Hph(4-CF3-3-OMe) |
| PP2267 | MeAhpe(2) | Ile | MeGly | MeAlgly | ButenylPhe(4-CH=CH2) | MeGly | Hph(4-CF3-3-OMe) |
| PP3032 | MeAocte(2) | Ile | MeGly | MeAlgly | ButenylPhe(4-CH=CH2) | MeGly | Hph(4-CF3-3-OMe) |
| PP3033 | MeAocte(2) | Ile | MeGly | MeAlgly | ButenylPhe(4-CH=CH2) | MeGly | Hph(4-CF3-3-OMe) |
| PP3034 | MeAocte(2) | Ile | MeGly | MeAlgly | ButenylPhe(4-CH=CH2) | MeGly | Hph(4-CF3-3-OMe) |
| PP3035 | MeAhpe(2) | Ile | MeGly | MeAlgly | ButenylPhe(4-CH=CH2) | MeGly | Hph(4-CF3-3-OMe) |
| PP3036 | MeAhpe(2) | Ile | MeGly | MeAlgly | ButenylPhe(4-CH=CH2) | MeGly | Hph(4-CF3-3-OMe) |
| PP3037 | MeAhpe(2) | Ile | MeGly | MeAlgly | ButenylPhe(4-CH=CH2) | MeGly | Hph(4-CF3-3-OMe) |
| PP3038 | MeAhxe(2) | Ile | MeGly | MeAlgly | ButenylPhe(4-CH=CH2) | MeGly | Hph(4-CF3-3-OMe) |
| PP3063 | MeAlgly | Ile | MeGly | MeAlgly | ButenylPhe(4-CH=CH2) | MeGly | Hph(4-CF3-3-OMe) |
| PP3064 | MeAlgly | Ile | MeGly | MeAlgly | ButenylPhe(4-CH=CH2) | MeGly | Hph(4-CF3-3-OMe) |
| PP3065 | MeAlgly | Ile | MeGly | MeAlgly | ButenylPhe(4-CH=CH2) | MeGly | Hph(4-CF3-3-OMe) |
| PP3066 | MeAocte(2) | Ile | MeGly | MeAlgly | ButenylPhe(4-CH=CH2) | MeGly | Hph(4-CF3-3-OMe) |
| PP3067 | MeAocte(2) | Ile | MeGly | MeAlgly | ButenylPhe(4-CH=CH2) | MeGly | Hph(4-CF3-3-OMe) |
| PP3068 | MeAocte(2) | Ile | MeGly | MeAlgly | ButenylPhe(4-CH=CH2) | MeGly | Hph(4-CF3-3-OMe) |
| PP3069 | MeAocte(2) | Ile | MeGly | MeAlgly | ButenylPhe(4-CH=CH2) | MeGly | Hph(4-CF3-3-OMe) |
| PP3070 | MeAocte(2) | Ile | cPrGly | MeAlgly | ButenylPhe(4-CH=CH2) | MeGly | Hph(4-CF3-3-OMe) |
| PP3071 | MeAocte(2) | Ile | MeGly | MeAlgly | ButenylPhe(4-CH=CH2) | MeGly | Hph(34-Cl2) |
| PP3072 | MeAhpe(2) | Ile | MeGly | MeAlgly | ButenylPhe(4-CH=CH2) | MeGly | Hph(4-CF3-3-OMe) |
| PP3073 | MeAhpe(2) | Ile | MeGly | MeAlgly | ButenylPhe(4-CH=CH2) | MeGly | Hph(4-CF3-3-OMe) |
| PP3074 | MeAhpe(2) | Ile | MeGly | MeAlgly | ButenylPhe(4-CH=CH2) | MeGly | Hph(4-CF3-3-OMe) |
| PP3075 | MeAhpe(2) | Ile | cPrGly | MeAlgly | ButenylPhe(4-CH=CH2) | MeGly | Hph(4-CF3-3-OMe) |
| PP3076 | MeAhpe(2) | Ile | MeGly | MeAlgly | ButenylPhe(4-CH=CH2) | MeGly | Hph(34-Cl2) |
| PP3077 | MeAhxe(2) | Ile | MeGly | MeAlgly | ButenylPhe(4-CH=CH2) | MeGly | Hph(4-CF3-3-OMe) |
| PP3078 | MeAhxe(2) | Ile | MeGly | MeAlgly | ButenylPhe(4-CH=CH2) | MeGly | Hph(4-CF3-3-OMe) |
| PP3079 | MeAhxe(2) | Ile | MeGly | MeAlgly | ButenylPhe(4-CH=CH2) | MeGly | Hph(4-CF3-3-OMe) |
| PP3080 | MeAhxe(2) | Ile | MeGly | MeAlgly | ButenylPhe(4-CH=CH2) | MeGly | Hph(4-CF3-3-OMe) |
| PP3081 | MeAhxe(2) | Ile | MeGly | MeAlgly | ButenylPhe(4-CH=CH2) | MeGly | Hph(4-CF3-3-OMe) |
| PP3082 | MeAhxe(2) | Ile | cPrGly | MeAlgly | ButenylPhe(4-CH=CH2) | MeGly | Hph(4-CF3-3-OMe) |
| PP3083 | MeAlgly | Ile | MeGly | MeAlgly | ButenylPhe(4-CH=CH2) | MeGly | Hph(4-CF3-3-OMe) |
| PP3084 | MeAlgly | Ile | MeGly | MeAlgly | ButenylPhe(4-CH=CH2) | MeGly | Hph(4-CF3-3-OMe) |
| PP3085 | MeAlgly | Ile | MeGly | MeAlgly | ButenylPhe(4-CH=CH2) | MeGly | Hph(4-CF3-3-OMe) |
| PP3086 | MeAlgly | Ile | MeGly | MeAlgly | ButenylPhe(4-CH=CH2) | MeGly | Hph(4-CF3-3-OMe) |
| PP3087 | MeAlgly | Ile | MeGly | MeAlgly | ButenylPhe(4-CH=CH2) | MeGly | Hph(4-CF3-3-OMe) |
| PP3088 | MeAlgly | Ile | cPrGly | MeAlgly | ButenylPhe(4-CH=CH2) | MeGly | Hph(4-CF3-3-OMe) |
| PP3089 | MeAlgly | Ile | MeGly | MeAlgly | ButenylPhe(4-CH=CH2) | MeGly | Hph(34-Cl2) |
| PP3090 | MeAocte(2) | Ile | MeGly | MeAlgly | ButenylPhe(4-CH=CH2) | MeGly | Hph(4-CF3-3-OMe) |
| PP3091 | MeAhpe(2) | Ile | MeGly | MeAlgly | ButenylPhe(4-CH=CH2) | MeGly | Hph(4-CF3-3-OMe) |
| PP3092 | MeAhxe(2) | Ile | MeGly | MeAlgly | ButenylPhe(4-CH=CH2) | MeGly | Hph(34-Cl2) |
| PP3093 | MeAhxe(2) | Ile | MeGly | MeAlgly | ButenylPhe(4-CH=CH2) | MeGly | Hph(4-CF3-3-OMe) |
| PP3094 | MeAhxe(2) | Ile | MeGly | MeAlgly | ButenylPhe(4-CH=CH2) | MeGly | Hph(4-CF3-3-OMe) |

| ID | 8 | 9 | 10 | 11 | Cterm |
|---|---|---|---|---|---|
| PP2117 | Hyp(Et) | cVal | MeGly(cPent) | MeAsp2 | MeNEt |
| PP2118 | Hyp(Et) | cVal | MeGly(cPent) | MeAsp2 | MeNEt |
| PP2259 | Hyp(Et) | cVal(3-Me2) | MeGly(cPent) | MeAsp2 | MeNEt |
| PP2260 | Hyp(Et) | cVal(3-Me2) | MeGly(cPent) | MeAsp2 | MeNEt |
| PP2261 | Hyp(Et) | cVal | MeGly(cPent) | MeAsp2 | NMe2 |
| PP2262 | Hyp(Et) | cVal | MeGly(cPent) | MeAsp2 | NMe2 |
| PP2263 | Hyp(Et) | cVal | MeGly(cPent) | MeAsp2 | MeNEt |
| PP2264 | Hyp(Et) | cVal | MeGly(cPent) | MeAsp2 | NMe2 |
| PP2265 | Hyp(Et) | cVal | MeGly(cPent) | MeAsp2 | MeNEt |
| PP2266 | Hyp(Et) | cVal(3-Me2) | MeGly(cPent) | MeAsp2 | MeNEt |
| PP2267 | Hyp(Et) | cVal(3-Me2) | MeGly(cPent) | MeAsp2 | NMe2 |
| PP3032 | Hyp(Et) | cVal(3-Me2) | MeNva(3-Et) | MeAsp2 | NMe2 |
| PP3033 | Hyp(Et) | cVal | MeGly(cPent) | MeAsp2 | pip |
| PP3034 | Hyp(Et) | cVal(3-Me2) | MeGly(cPent) | MeAsp2 | pyrro |
| PP3035 | Hyp(Et) | cVal(3-Me2) | MeNva(3-Et) | MeAsp2 | NMe2 |
| PP3036 | Hyp(Et) | cVal(3-Me2) | MeGly(cPent) | MeAsp2 | pip |
| PP3037 | Hyp(Et) | cVal(3-Me2) | MeGly(cPent) | MeAsp2 | pyrro |
| PP3038 | Hyp(nPr) | cVal(3-Me2) | MeNva(3-Et) | MeAsp2 | NMe2 |
| PP3063 | Hyp(nPr) | cVal(3-Me2) | MeNva(3-Et) | MeAsp2 | NMe2 |
| PP3064 | Hyp(nPr) | cVal(3-Me2) | MeGly(cPent) | MeAsp2 | pip |
| PP3065 | Hyp(nPr) | cVal(3-Me2) | MeGly(cPent) | MeAsp2 | pyrro |
| PP3066 | Hyp(Et) | cVal(3-Me2) | MeGly(cPent) | MeAsp2 | NMe2 |
| PP3067 | Hyp(iPr) | cVal(3-Me2) | MeGly(cPent) | MeAsp2 | NMe2 |
| PP3068 | Hyp(cBu) | cVal(3-Me2) | MeGly(cPent) | MeAsp2 | NMe2 |
| PP3069 | Pro(4-cPr) | cVal(3-Me2) | MeGly(cPent) | MeAsp2 | NMe2 |
| PP3070 | Hyp(Et) | cVal(3-Me2) | MeGly(cPent) | MeAsp2 | NMe2 |
| PP3071 | Hyp(Et) | cVal(3-Me2) | MeGly(cPent) | MeAsp2 | NMe2 |
| PP3072 | Hyp(iPr) | cVal(3-Me2) | MeGly(cPent) | MeAsp2 | NMe2 |
| PP3073 | Hyp(cBu) | cVal(3-Me2) | MeGly(cPent) | MeAsp2 | NMe2 |
| PP3074 | Pro(4-cPr) | cVal(3-Me2) | MeGly(cPent) | MeAsp2 | NMe2 |

TABLE 35-1-continued

| | | | | | |
|---|---|---|---|---|---|
| PP3075 | Hyp(Et) | cVal(3-Me2) | MeGly(cPent) | MeAsp2 | NMe2 |
| PP3076 | Hyp(Et) | cVal(3-Me2) | MeGly(cPent) | MeAsp2 | NMe2 |
| PP3077 | Hyp(nPr) | cVal(3-Me2) | MeGly(cPent) | MeAsp2 | NMe2 |
| PP3078 | Hyp(iPr) | cVal(3-Me2) | MeGly(cPent) | MeAsp2 | MeNEt |
| PP3079 | Hyp(cBu) | cVal(3-Me2) | MeGly(cPent) | MeAsp2 | MeNEt |
| PP3080 | Hyp(cPent) | cVal(3-Me2) | MeGly(cPent) | MeAsp2 | NMe2 |
| PP3081 | Pro(4-cPr) | cVal(3-Me2) | MeGly(cPent) | MeAsp2 | MeNEt |
| PP3082 | Hyp(nPr) | cVal(3-Me2) | MeGly(cPent) | MeAsp2 | NMe2 |
| PP3083 | Hyp(nPr) | cVal(3-Me2) | MeGly(cPent) | MeAsp2 | MeNEt |
| PP3084 | Hyp(iPr) | cVal(3-Me2) | MeGly(cPent) | MeAsp2 | MeNEt |
| PP3085 | Hyp(cBu) | cVal(3-Me2) | MeGly(cPent) | MeAsp2 | MeNEt |
| PP3086 | Hyp(cPent) | cVal(3-Me2) | MeGly(cPent) | MeAsp2 | MeNEt |
| PP3087 | Pro(4-cPr) | cVal(3-Me2) | MeGly(cPent) | MeAsp2 | MeNEt |
| PP3088 | Hyp(nPr) | cVal(3-Me2) | MeGly(cPent) | MeAsp2 | MeNEt |
| PP3089 | Hyp(nPr) | cVal(3-Me2) | MeGly(cPent) | MeAsp2 | MeNEt |
| PP3090 | Hyp(Et) | MecVal(3-Me2) | MeGly(cPent) | MeAsp2 | NMe2 |
| PP3091 | Hyp(Et) | MecVal(3-Me2) | MeGly(cPent) | MeAsp2 | NMe2 |
| PP3092 | Hyp(nPr) | cVal(3-Me2) | MeGly(cPent) | MeAsp2 | NMe2 |
| PP3093 | Hyp(Et) | cVal(3-Me2) | MeGly(cPent) | MeAsp2 | pip |
| PP3094 | Hyp(nPr) | cVal(3-Me2) | MeGly(cPent) | MeAsp2 | pyrro |

TABLE 35-2

| ID | yield (mg) | yield (%) |
|---|---|---|
| PP2117 | 3.2 | 6.1 |
| PP2118 | 3.2 | 6.1 |
| PP2259 | 4.2 | 7.9 |
| PP2260 | 4.1 | 7.6 |
| PP2261 | 2.5 | 3.7 |
| PP2262 | 2.9 | 4.3 |
| PP2263 | 2.1 | 4.0 |
| PP2264 | 2.7 | 4.0 |
| PP2265 | 2.4 | 4.5 |
| PP2266 | 3.5 | 6.5 |
| PP2267 | 2.8 | 4.1 |
| PP3032 | 2.15 | 11.4 |
| PP3033 | 2.33 | 10.0 |
| PP3034 | 3.70 | 15.4 |
| PP3035 | 1.38 | 7.6 |
| PP3036 | 2.12 | 9.3 |
| PP3037 | 1.96 | 9.8 |
| PP3038 | 2.38 | 12.9 |
| PP3063 | 1.19 | 0.9 |
| PP3064 | 1.87 | 1.2 |
| PP3065 | 1.71 | 1.2 |
| PP3066 | 2.81 | 2.6 |
| PP3067 | 1.4 | 1.3 |
| PP3068 | 0.89 | 0.8 |
| PP3069 | 0.88 | 0.8 |
| PP3070 | 3.74 | 3.4 |
| PP3071 | 2.85 | 2.7 |
| PP3072 | 5.48 | 5.1 |
| PP3073 | 2.4 | 2.2 |
| PP3074 | 2.76 | 2.6 |
| PP3075 | 2.26 | 2.1 |
| PP3076 | 1.99 | 1.9 |
| PP3077 | 4.53 | 4.3 |
| PP3078 | 2.22 | 2.2 |
| PP3079 | 2.58 | 2.5 |
| PP3080 | 2.02 | 1.9 |
| PP3081 | 3.42 | 3.5 |
| PP3082 | 2.56 | 2.4 |
| PP3083 | 1.7 | 1.7 |
| PP3084 | 1.6 | 1.6 |
| PP3085 | 1.2 | 1.2 |
| PP3086 | 1.98 | 1.9 |
| PP3087 | 0.9 | 0.9 |
| PP3088 | 1.55 | 1.5 |
| PP3089 | 1.48 | 1.5 |
| PP3090 | 2.18 | 1.6 |
| PP3091 | 1.53 | 1.1 |
| PP3092 | 1.51 | 1.5 |
| PP3093 | 0.9 | 0.6 |
| PP3094 | 0.4 | 0.3 |

1-6-9. Synthesis of Cyclic Peptide Having Thioether Group in Main Chain Structure Synthesis of Compound PP3108 and Compound PP3109

In the synthesis of Compound PP3108 and Compound PP3109, Compound aa439-Resin (0.336 mmol/g, 100 mg) was used as a raw material, and Fmoc-MeGly (cPent)-OH, Fmoc-cLeu-OH, Fmoc-Pro-OH, Fmoc-Hph(4—CF3-35-F2)—OH, Fmoc-MeGly-OH, tp005, tp006, Fmoc-Ile-OH, and Fmoc-MeLeu-OH were used. A peptide elongation reaction by the basic Fmoc method described in the present Examples, cleaving of an elongated peptide from resin, cyclization of the cleaved peptide (using (1-cyano-2-ethoxy-2-oxoethylideneaminooxy)dimethylamino-morpholino-carbenium hexafluorophosphate (COMU) as a cyclization reagent), and purification of a cyclic peptide were carried out to give the intended Compound PP3108 (4.9 mg, 9.8%) and Compound PP3109 (5.6 mg, 11%).

Compound PP3108

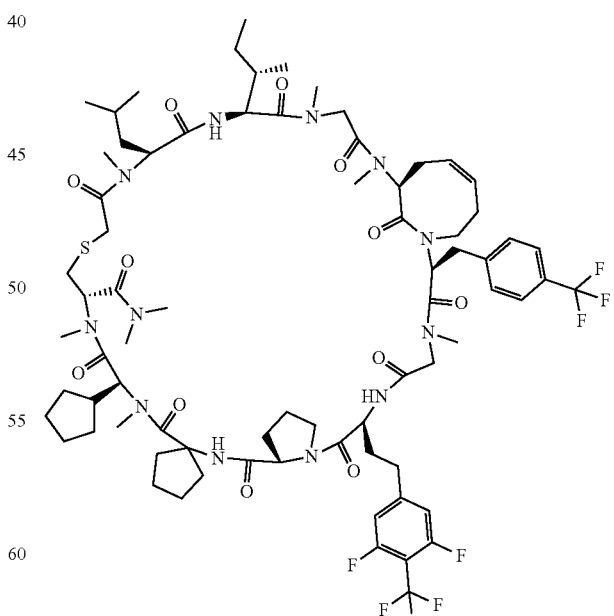

LCMS (ESI) m/z=1534.2 (M–HI)

Retention time: 5.989 min (Analytical condition SSC-FA-02)

Compound PP3109

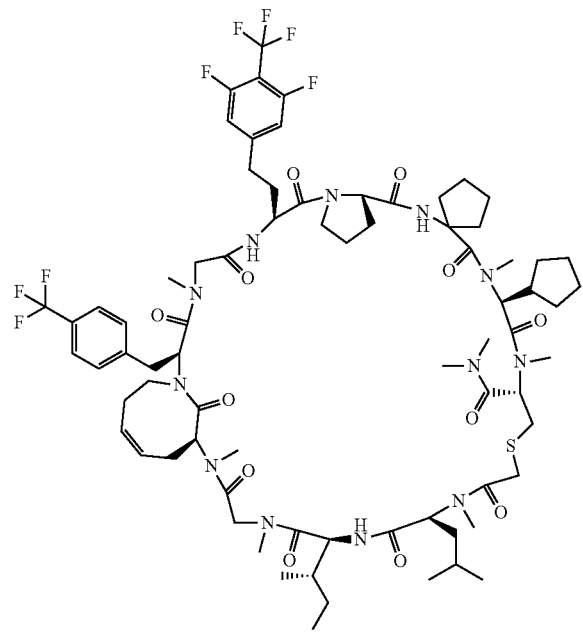 [SMILES: CC[C@H](C)[C@@H]1NC(=O)[C@H](CC(C)C)N(C)C(=O)CSC[C@H](C(=O)N(C)C)N(C)C(=O)[C@H](C2CCCC2)N(C)C(=O)C2(CCCC2)NC(=O)[C@@H]2CCCN2C(=O)[C@H](CCc2cc(F)c(C(F)(F)F)c(F)c2)NC(=O)CN(C)C(=O)[C@H](Cc2ccc(C(F)(F)F)cc2)N2CC/C=C\C[C@@H](C2=O)N(C)C(=O)CN(C)C1=O]

LCMS (ESI) m/z=1548.0 (M−H)−
Retention time: 6.083 min (Analytical condition SSC-FA-02)
In the measurement conditions in Table 36, FA denotes SSC-FA-02/03, and AA denotes SSC-AA-02/03.

TABLE 36

| Compound No. | Analytical condition | Retention time (min) | MS Found (m/z) | MS polarity |
|---|---|---|---|---|
| PP0001 | FA | 5.285 | 1462.1 | (M − H)− |
| PP0002 | FA | 5.776 | 1530.1 | (M − H)− |
| PP0003 | FA | 5.504 | 1441.6 | (M + H)+ |
| PP0004 | FA | 5.528 | 1476.2 | (M − H)− |
| PP0006 | AA | 7.936 | 1489.9 | (M − H)− |
| PP0007 | FA | 5.081 | 1435.6 | (M + H)+ |
| PP0011 | FA | 5.204 | 1449.6 | (M + H)+ |
| PP0013 | FA | 5.120 | 1491.9 | (M − H)− |
| PP0014 | AA | 7.951 | 1521.7 | (M + H)+ |
| PP0015 | FA | 5.405 | 1451.7 | (M + H)+ |
| PP0016 | FA | 5.643 | 1465.7 | (M + H)+ |
| PP0018 | FA | 5.321 | 1437.6 | (M + H)+ |
| PP0019 | FA | 5.552 | 1451.6 | (M + H)+ |
| PP0020 | AA | 7.809 | 1464.1 | (M − H)− |
| PP0021 | FA | 6.133 | 1478.0 | (M − H)− |
| PP0022 | FA | 5.495 | 1450.1 | (M − H). |
| PP0023 | FA | 5.713 | 1505.5 | (M + H)+ |
| PP0024 | FA | 5.419 | 1413.6 | (M − H)− |
| PP0025 | FA | 5.555 | 1450.0 | (M − H)− |
| PP0027 | FA | 5.724 | 1464.1 | (M − H)− |
| PP0028 | FA | 5.736 | 1464.1 | (M − H)− |
| PP0029 | AA | 7.771 | 1464.1 | (M − H)− |
| PP0030 | FA | 5.965 | 1477.8 | (M − H)− |
| PP0031 | FA | 4.945 | 1407.6 | (M − H)− |
| PP0032 | FA | 5.312 | 1477.5 | (M + H)+ |
| PP0037 | FA | 5.348 | 1467.6 | (M + H)+ |
| PP0039 | FA | 5.147 | 1423.6 | (M + H)+ |
| PP0041 | FA | 4.941 | 1484.8 | (M + NH4)+ |
| PP0042 | FA | 5.616 | 1493.8 | (M − H)− |
| PP0043 | FA | 5.561 | 1438.0 | (M − H)− |
| PP0044 | FA | 5.277 | 1425.6 | (M + H)+ |
| PP0045 | FA | 5.445 | 1438.1 | (M − H)− |
| PP0047 | FA | 6.448 | 1437.8 | (M − H)− |
| PP0048 | FA | 6.757 | 1452.1 | (M − H)− |

TABLE 36-continued

| Compound No. | Analytical condition | Retention time (min) | MS Found (m/z) | MS polarity |
|---|---|---|---|---|
| PP0049 | FA | 6.228 | 1413.7 | (M + H)+ |
| PP0050 | FA | 6.381 | 1444.8 | (M + NH4)+ |
| PP0051 | FA | 5.737 | 1475.8 | (M − H)− |
| PP0052 | FA | 5.991 | 1491.9 | (M + H)+ |
| PP0053 | FA | 6.075 | 1545.8 | (M + H)+ |
| PP0054 | FA | 6.159 | 1454.1 | (M − H)− |
| PP0055 | FA | 6.308 | 1505.7 | (M + H)+ |
| PP0056 | FA | 6.341 | 1504.2 | (M − H)− |
| PP0057 | FA | 6.084 | 1502.1 | (M − H)− |
| PP0058 | FA | 6.216 | 1504.2 | (M − H)− |
| PP0059 | FA | 5.764 | 1464.1 | (M − H)− |
| PP0060 | FA | 5.987 | 1518.0 | (M − H)− |
| PP0061 | FA | 5.720 | 1429.6 | (M + H)+ |
| PP0062 | AA | 7.943 | 1478.0 | (M − H)− |
| PP0063 | FA | 5.964 | 1478.0 | (M − H)− |
| PP0064 | AA | 7.836 | 1499.7 | (M + Na)+ |
| PP0065 | FA | 6.012 | 1477.8 | (M − H)− |
| PP0066 | AA | 7.939 | 1479.7 | (M + H)+ |
| PP0067 | FA | 6.075 | 1576.2 | (M − H)− |
| PP0068 | AA | 7.907 | 1550.1 | (M − H)− |
| PP0069 | FA | 6.248 | 1492.0 | (M − H)− |
| PP0070 | FA | 6.247 | 1515.8 | (M − H)− |
| PP0071 | AA | 7.843 | 1494.5 | (M + NH4)+ |
| PP0076 | FA | 5.551 | 1489.9 | (M − H)− |
| PP0077 | AA | 8.029 | 1569.8 | (M − H)− |
| PP0078 | FA | 5.900 | 1548.7 | (M + NH4)+ |
| PP0083 | AA | 8.248 | 1516.2 | (M − H)− |
| PP0084 | FA | 6.924 | 1529.8 | (M − H)− |
| PP0085 | FA | 7.169 | 1544.2 | (M − H)− |
| PP0086 | FA | 6.733 | 1518.0 | (M − H)− |
| PP0087 | FA | 6.975 | 1532.3 | (M − H)− |
| PP0088 | FA | 5.955 | 1489.7 | (M + H)+ |
| PP0089 | FA | 6.247 | 1502.1 | (M − H)− |
| PP0090 | FA | 5.647 | 1487.7 | (M + H)+ |
| PP0091 | FA | 6.411 | 1544.1 | (M − H)− |
| PP0092 | FA | 5.812 | 1506.1 | (M − H)− |
| PP0093 | FA | 5.817 | 1520.2 | (M − H)− |
| PP0094 | AA | 7.721 | 1488.0 | (M + Na)+ |
| PP0095 | FA | 6.296 | 1491.6 | (M + H)+ |
| PP0096 | FA | 6.504 | 1504.2 | (M − H)− |
| PP0097 | FA | 6.749 | 1518.2 | (M − H)− |
| PP0098 | FA | 6.475 | 1492.2 | (M − H)− |
| PP0099 | FA | 6.683 | 1506.0 | (M − H)− |
| PP0100 | FA | 5.744 | 1463.7 | (M + H)+ |
| PP0101 | FA | 6.005 | 1476.0 | (M − H)− |
| PP0102 | FA | 5.665 | 1459.7 | (M − H)− |
| PP0103 | FA | 6.069 | 1518.1 | (M − H)− |
| PP0104 | FA | 5.677 | 1480.2 | (M − H)− |
| PP0105 | FA | 5.668 | 1495.7 | (M + H)+ |
| PP0106 | FA | 6.533 | 1558.1 | (M − H)− |
| PP0107 | FA | 6.641 | 1559.6 | (M + H)+ |
| PP0108 | FA | 6.367 | 1556.1 | (M − H)− |
| PP0109 | FA | 6.769 | 1570.2 | (M − H)− |
| PP0110 | FA | 7.056 | 1583.7 | (M − H)− |
| PP0112 | FA | 6.804 | 1572.2 | (M − H)− |
| PP0113 | FA | 7.039 | 1586.1 | (M − H)− |
| PP0114 | AA | 7.827 | 1544.1 | (M + H)+ |
| PP0115 | FA | 6.373 | 1558.1 | (M + H)− |
| PP0116 | FA | 5.773 | 1540.2 | (M − H)− |
| PP0117 | FA | 6.544 | 1597.7 | (M − H)− |
| PP0118 | FA | 5.996 | 1562.1 | (M + H)+ |
| PP0119 | AA | 7.784 | 1575.8 | (M + H)+ |
| PP0120 | FA | 6.407 | 1531.8 | (M − H)− |
| PP0121 | FA | 6.313 | 1532.1 | (M + H)− |
| PP0122 | FA | 6.216 | 1532. | (M + H)− |
| PP0123 | FA | 6.496 | 1546.1 | (M + H)+ |
| PP0124 | FA | 6.692 | 1558.2 | (M − H)− |
| PP0126 | FA | 6.635 | 1547.7 | (M + H)− |
| PP0127 | FA | 6.82 | 1560.1 | (M − H)− |
| PP0128 | FA | 5.949 | 1534.7 | (M + NH4)+ |
| PP0129 | FA | 6.199 | 1529.9 | (M − H)− |
| PP0130 | FA | 5.883 | 1513.9 | (M − H)− |
| PP0131 | FA | 6.232 | 1573.6 | (M + H)− |
| PP0132 | FA | 5.921 | 1533.9 | (M − H)− |
| PP0133 | FA | 5.917 | 1547.7 | (M − H)− |
| PP0134 | FA | 5.900 | 1505.9 | (M − H)− |

TABLE 36-continued

| Compound No. | Analytical condition | Retention time (min) | MS Found (m/z) | MS polarity |
|---|---|---|---|---|
| PP0135 | FA | 5.693 | 1481.7 | (M + H)+ |
| PP0136 | AA | 8.043 | 1560.2 | (M − H)− |
| PP0137 | FA | 6.304 | 1534.2 | (M − H)− |
| PP0138 | FA | 6.353 | 1504.2 | (M − H)− |
| PP0139 | FA | 6.477 | 1502.2 | (M − H)− |
| PP0140 | FA | 6.779 | 1516.2 | (M − H)− |
| PP0141 | FA | 6.465 | 1557.8 | (M − H)− |
| PP0144 | FA | 6.033 | 1505.9 | (M − H)− |
| PP0145 | FA | 6.329 | 1532.1 | (M − H)− |
| PP0146 | FA | 6.016 | 1505.6 | (M + H)+ |
| PP0148 | FA | 6.403 | 1532.2 | (M − H)− |
| PP0149 | FA | 6.144 | 1545.7 | (M + H)+ |
| PP0150 | FA | 6.085 | 1477.7 | (M − H)− |
| PP0151 | AA | 8.072 | 1581.6 | (M + Na)+ |
| PP0152 | FA | 6.677 | 1558.0 | (M − H)− |
| PP0153 | FA | 6.077 | 1542.0 | (M + Na)+ |
| PP0154 | AA | 7.933 | 1530.1 | (M − H)− |
| PP0155 | FA | 5.944 | 1506.1 | (M + H)+ |
| PP0156 | FA | 5.841 | 1532.1 | (M + H)+ |
| PP0158 | FA | 6.103 | 1530.1 | (M − H)− |
| PP0162 | FA | 6.537 | 1558.0 | (M − H)− |
| PP0165 | FA | 6.257 | 1544.0 | (M − H)− |
| PP0166 | FA | 6.159 | 1555.7 | (M − H)− |
| PP0168 | FA | 6.028 | 1542.0 | (M − H)− |
| PP0169 | FA | 6.089 | 1475.9 | (M − H)− |
| PP0170 | FA | 6.245 | 1520.8 | (M + NH4)+ |
| PP0171 | FA | 6.748 | 1534.7 | (M + NH4)+ |
| PP0172 | FA | 6.028 | 1488.1 | (M − H)− |
| PP0173 | AA | 7.937 | 1543.7 | (M − H)− |
| PP0174 | FA | 5.992 | 1522.8 | (M + NH4)+ |
| PP0175 | FA | 5.095 | 1574.7 | (M + H)+ |
| PP0176 | FA | 7.011 | 1531.7 | (M + H)+ |
| PP0177 | FA | 6.711 | 1530.0 | (M − H)− |
| PP0178 | FA | 6.243 | 1502.0 | (M − H)− |
| PP0179 | FA | 6.432 | 1527.9 | (M − H)− |
| PP0180 | FA | 6.949 | 1542.0 | (M − H)− |
| PP0181 | FA | 6.175 | 1513.7 | (M + H)+ |
| PP0182 | FA | 6.381 | 1570.2 | (M − H)− |
| PP0183 | FA | 6.085 | 1530.1 | (M − H)− |
| PP0184 | AA | 7.676 | 1599.0 | (M − H)− |
| PP0185 | AA | 8.483 | 1557.7 | (M + H)+ |
| PP0186 | FA | 6.943 | 1556.0 | (M − H)− |
| PP0187 | FA | 5.819 | 1543.7 | (M − H)− |
| PP0188 | FA | 5.935 | 1515.9 | (M − H)− |
| PP0189 | FA | 5.872 | 1503.9 | (M − H)− |
| PP0190 | FA | 5.705 | 1491.6 | (M + H)+ |
| PP0191 | FA | 5.912 | 1570.1 | (M − H)− |
| PP0192 | FA | 6.140 | 1543.9 | (M + H)+ |
| PP0193 | FA | 5.992 | 1529.9 | (M − H)− |
| PP0194 | FA | 5.827 | 1516.1 | (M − H)− |
| PP0195 | FA | 6.177 | 1553.7 | (M − H)− |
| PP0196 | FA | 6.276 | 1581.6 | (M + H)+ |
| PP0197 | AA | 7.636 | 1527.8 | (M + Na)+ |
| PP0198 | FA | 6.024 | 1529.9 | (M − H)− |
| PP0199 | FA | 5.963 | 1581.8 | (M + H)+ |
| PP0200 | FA | 6.084 | 1551.9 | (M − H)− |
| PP0201 | FA | 6.023 | 1542.1 | (M + H)+ |
| PP0202 | FA | 5.849 | 1527.6 | (M − H)− |
| PP0203 | FA | 6.061 | 1606.1 | (M − H)− |
| PP0204 | FA | 6.271 | 1578.1 | (M − H)− |
| PP0205 | FA | 6.149 | 1567.6 | (M + H)+ |
| PP0206 | FA | 5.999 | 1553.6 | (M − H)− |
| PP0207 | FA | 6.007 | 1541.9 | (M − H)− |
| PP0208 | FA | 6.131 | 1566.0 | (M − H)− |
| PP0209 | FA | 7.039 | 1620.2 | (M − H)− |
| PP0210 | FA | 5.409 | 1435.6 | (M − H)− |
| PP0211 | FA | 5.681 | 1451.6 | (M + H)+ |
| PP0212 | FA | 5.231 | 1439.9 | (M − H)− |
| PP0213 | FA | 5.441 | 1454.0 | (M − H)− |
| PP0214 | FA | 5.708 | 1467.9 | (M − H)− |
| PP0215 | FA | 5.587 | 1463.6 | (M + H)+ |
| PP0216 | FA | 5.899 | 1477.6 | (M + H)+ |
| PP0217 | FA | 5.273 | 1466.1 | (M − H)− |
| PP0218 | FA | 5.584 | 1480.2 | (M − H)− |
| PP0219 | FA | 5.880 | 1493.7 | (M − H)− |
| PP0220 | FA | 5.635 | 1503.6 | (M + H)+ |
| PP0221 | FA | 5.637 | 1504.2 | (M − H)− |
| PP0222 | FA | 6.216 | 1545.7 | (M + H)+ |
| PP0223 | FA | 5.836 | 1497.6 | (M + H)+ |
| PP0224 | FA | 5.973 | 1515.7 | (M − H)− |
| PP0225 | FA | 5.960 | 1518.0 | (M − H)− |
| PP0226 | FA | 6.484 | 1559.8 | (M + H)+ |
| PP0227 | AA | 7.968 | 1534.0 | (M + Na)+ |
| PP0228 | FA | 6.308 | 1589.9 | (M + H)+ |
| PP0229 | FA | 5.677 | 1491.6 | (M + H)+ |
| PP0230 | FA | 5.788 | 1493.6 | (M + H)+ |
| PP0231 | FA | 6.372 | 1531.7 | (M − H)− |
| PP0232 | FA | 6.023 | 1484.0 | (M − H)− |
| PP0233 | FA | 6.161 | 1564.1 | (M + H)+ |
| PP0234 | FA | 5.388 | 1477.6 | (M + H)+ |
| PP0235 | FA | 5.511 | 1479.8 | (M + H)+ |
| PP0236 | FA | 6.101 | 1517.7 | (M − H)− |
| PP0237 | AA | 7.677 | 1493.7 | (M + Na)+ |
| PP0238 | FA | 5.729 | 1560.2 | (M − H)− |
| PP0239 | FA | 5.512 | 1562.1 | (M + H)+ |
| PP0240 | FA | 5.587 | 1533.7 | (M − H)− |
| PP0241 | FA | 5.384 | 1534.1 | (M − H)− |
| PP0242 | FA | 6.333 | 1588.2 | (M − H)− |
| PP0243 | AA | 8.097 | 1563.7 | (M + H)+ |
| PP0244 | AA | 7.768 | 1496.2 | (M − H)− |
| PP0245 | FA | 6.284 | 1599.7 | (M + H)+ |
| PP0246 | FA | 5.897 | 1598.2 | (M − H)− |
| PP0247 | AA | 7.775 | 1517.6 | (M + H)+ |
| PP0248 | FA | 5.639 | 1489.9 | (M − H)− |
| PP0249 | FA | 5.896 | 1545.6 | (M + H)+ |
| PP0250 | FA | 5.859 | 1517.6 | (M + H)+ |
| PP0251 | FA | 5.996 | 1529.7 | (M − H)− |
| PP0252 | FA | 6.333 | 1544.2 | (M − H)− |
| PP0253 | FA | 6.479 | 1547.9 | (M + H)+ |
| PP0254 | FA | 6.025 | 1543.0 | (M − H)− |
| PP0256 | FA | 6.420 | 1559.7 | (M + H)+ |
| PP0257 | FA | 6.197 | 1544.1 | (M − H)− |
| PP0258 | FA | 6.204 | 1545.6 | (M + H)+ |
| PP0259 | AA | 7.921 | 1545.9 | (M + H)+ |
| PP0260 | FA | 5.899 | 1505.6 | (M + H)+ |
| PP0261 | AA | 8.028 | 1546.1 | (M + H)+ |
| PP0262 | FA | 5.775 | 1547.7 | (M − H)− |
| PP0263 | FA | 6.343 | 1532.1 | (M − H)− |
| PP0264 | FA | 6.232 | 1569.6 | (M + H)+ |
| PP0265 | FA | 5.860 | 1533.7 | (M − H)− |
| PP0266 | FA | 5.788 | 1510.6 | (M + NH4)+ |
| PP0267 | FA | 6.143 | 1522.1 | (M + H)+ |
| PP0268 | FA | 5.909 | 1542.0 | (M − H)− |
| PP0269 | FA | 5.763 | 1516.1 | (M − H)− |
| PP0270 | FA | 5.991 | 1571.6 | (M + H)+ |
| PP0271 | FA | 5.983 | 1543.6 | (M + H)+ |
| PP0272 | FA | 6.127 | 1556.2 | (M − H)− |
| PP0273 | FA | 6.020 | 1556.0 | (M − H)− |
| PP0274 | FA | 6.303 | 1558.2 | (M − H)− |
| PP0275 | FA | 5.851 | 1556.6 | (M + H)+ |
| PP0276 | FA | 6.281 | 1541.9 | (M − H)− |
| PP0277 | FA | 6.431 | 1570.0 | (M − H)− |
| PP0278 | FA | 6.189 | 1555.9 | (M − H)− |
| PP0279 | FA | 6.105 | 1557.7 | (M + H)+ |
| PP0281 | FA | 6.055 | 1529.7 | (M − H)− |
| PP0282 | FA | 6.295 | 1570.0 | (M − H)− |
| PP0283 | FA | 5.912 | 1574.0 | (M − H)− |
| PP0284 | FA | 6.445 | 1559.6 | (M + H)+ |
| PP0285 | FA | 6.371 | 1617.4 | (M + Na)+ |
| PP0286 | FA | 6.084 | 1561.6 | (M + H)+ |
| PP0287 | FA | 6.023 | 1518.0 | (M − H)− |
| PP0288 | FA | 6.363 | 1546.0 | (M − H)− |
| PP0289 | FA | 6.003 | 1529.9 | (M − H)− |
| PP0290 | FA | 5.833 | 1522.7 | (M + NH4)+ |
| PP0291 | FA | 6.085 | 1557.9 | (M − H)− |
| PP0292 | FA | 6.072 | 1529.7 | (M − H)− |
| PP0293 | FA | 6.247 | 1543.7 | (M − H)− |
| PP0294 | FA | 6.168 | 1518.1 | (M − H)− |
| PP0295 | FA | 6.548 | 1558.2 | (M − H)− |
| PP0296 | FA | 6.023 | 1562.2 | (M − H)− |
| PP0297 | FA | 6.588 | 1545.8 | (M − H)− |
| PP0298 | FA | 6.540 | 1582.0 | (M − H)− |

TABLE 36-continued

| Compound No. | Analytical condition | Retention time (min) | MS Found (m/z) | MS polarity |
|---|---|---|---|---|
| PP0299 | FA | 6.165 | 1548.0 | (M − H)− |
| PP0300 | FA | 6.057 | 1506.1 | (M − H)− |
| PP0301 | FA | 6.372 | 1536.1 | (M + H)+ |
| PP0302 | FA | 5.845 | 1529.6 | (M + H)+ |
| PP0303 | FA | 5.631 | 1501.9 | (M − H)− |
| PP0304 | FA | 5.873 | 1557.6 | (M + H)+ |
| PP0305 | FA | 5.871 | 1528.1 | (M − H)− |
| PP0306 | FA | 6.072 | 1541.7 | (M − H)− |
| PP0307 | FA | 5.880 | 1515.7 | (M + H)+ |
| PP0308 | FA | 6.325 | 1557.6 | (M + H)+ |
| PP0309 | FA | 5.909 | 1561.6 | (M + H)+ |
| PP0310 | FA | 6.143 | 1573.8 | (M − H)− |
| PP0311 | FA | 6.369 | 1544.1 | (M − H)− |
| PP0312 | FA | 6.325 | 1582.1 | (M + H)+ |
| PP0313 | FA | 5.927 | 1545.7 | (M − H)− |
| PP0314 | FA | 5.848 | 1504.1 | (M − H)− |
| PP0315 | FA | 6.211 | 1533.6 | (M + H)+ |
| PP0316 | FA | 5.553 | 1477.7 | (M + H)+ |
| PP0317 | FA | 6.133 | 1491.7 | (M + H)+ |
| PP0318 | FA | 5.684 | 1530.2 | (M − H)− |
| PP0319 | FA | 6.311 | 1544.0 | (M − H)− |
| PP0320 | FA | 5.767 | 1491.6 | (M + H)+ |
| PP0321 | FA | 6.108 | 1539.7 | (M − H)− |
| PP0322 | FA | 5.963 | 1527.6 | (M + H)+ |
| PP0323 | FA | 5.955 | 1547.7 | (M − H)− |
| PP0324 | FA | 5.823 | 1533.7 | (M − H)− |
| PP0325 | FA | 5.807 | 1491.6 | (M + H)+ |
| PP0326 | FA | 5.679 | 1477.6 | (M + H)+ |
| PP0327 | AA | 7.799 | 1525.6 | (M − H)− |
| PP0328 | FA | 5.872 | 1513.6 | (M + H)+ |
| PP0329 | FA | 5.845 | 1534.2 | (M − H)− |
| PP0330 | FA | 5.759 | 1521.6 | (M + H)+ |
| PP0331 | FA | 6.181 | 1519.6 | (M + H)+ |
| PP0332 | FA | 6.035 | 1504.1 | (M − H)− |
| PP0333 | AA | 7.952 | 1555.6 | (M + H)+ |
| PP0334 | FA | 6.233 | 1541.6 | (M + H)+ |
| PP0335 | FA | 6.189 | 1563.7 | (M + H)+ |
| PP0336 | FA | 6.084 | 1547.9 | (M + H)+ |
| PP0337 | FA | 5.947 | 1517.6 | (M + H)+ |
| PP0338 | FA | 5.788 | 1503.6 | (M + H)+ |
| PP0339 | FA | 6.181 | 1553.6 | (M + H)+ |
| PP0340 | FA | 6.023 | 1539.6 | (M + H)+ |
| PP0341 | FA | 6.036 | 1559.9 | (M − H)− |
| PP0342 | FA | 5.881 | 1545.9 | (M − H)− |
| PP0343 | FA | 5.985 | 1529.9 | (M − H)− |
| PP0344 | FA | 5.895 | 1515.9 | (M − H)− |
| PP0345 | FA | 6.120 | 1565.6 | (M − H)− |
| PP0346 | FA | 6.015 | 1552.0 | (M − H)− |
| PP0347 | FA | 6.121 | 1575.9 | (M + H)+ |
| PP0348 | FA | 6.027 | 1560.0 | (M − H)− |
| PP0349 | FA | 5.729 | 1515.7 | (M + H)+ |
| PP0350 | FA | 5.572 | 1501.7 | (M − H)− |
| PP0351 | FA | 5.844 | 1553.6 | (M + H)+ |
| PP0352 | FA | 5.717 | 1539.6 | (M + H)+ |
| PP0353 | FA | 5.808 | 1561.7 | (M + H)+ |
| PP0354 | AA | 7.747 | 1546.0 | (M − H)− |
| PP0355 | FA | 5.937 | 1462.1 | (M − H)− |
| PP0356 | FA | 5.800 | 1449.6 | (M + H)+ |
| PP0357 | FA | 6.123 | 1499.6 | (M + H)+ |
| PP0358 | AA | 7.689 | 1485.6 | (M + H)+ |
| PP0359 | FA | 6.004 | 1506.1 | (M − H)− |
| PP0360 | FA | 5.879 | 1493.6 | (M + H)+ |
| PP0361 | FA | 5.819 | 1449.6 | (M + H)+ |
| PP0362 | FA | 5.713 | 1433.6 | (M − H)− |
| PP0363 | FA | 6.000 | 1485.6 | (M + H)+ |
| PP0364 | FA | 5.904 | 1469.5 | (M − H)− |
| PP0365 | FA | 5.869 | 1491.7 | (M + H)+ |
| PP0366 | FA | 5.791 | 1477.7 | (M − H)− |
| PP0367 | FA | 6.216 | 1477.6 | (M + H)+ |
| PP0368 | FA | 6.093 | 1463.6 | (M + H)+ |
| PP0369 | FA | 6.405 | 1513.6 | (M + H)+ |
| PP0370 | FA | 6.281 | 1497.9 | (M − H)− |
| PP0371 | FA | 6.247 | 1521.7 | (M + H)+ |
| PP0372 | FA | 6.155 | 1505.7 | (M − H)− |
| PP0373 | FA | 6.012 | 1475.6 | (M + H)+ |
| PP0374 | FA | 5.865 | 1461.6 | (M + H)+ |
| PP0375 | FA | 6.232 | 1509.9 | (M − H)− |
| PP0376 | FA | 6.075 | 1497.5 | (M − H)− |
| PP0377 | FA | 6.127 | 1517.7 | (M − H)− |
| PP0378 | FA | 5.972 | 1505.6 | (M + H)+ |
| PP0379 | FA | 6.072 | 1489.6 | (M + H)+ |
| PP0380 | FA | 5.999 | 1475.6 | (M + H)+ |
| PP0381 | FA | 6.213 | 1523.9 | (M − H)− |
| PP0382 | FA | 6.112 | 1511.6 | (M + H)+ |
| PP0383 | FA | 6.219 | 1532.0 | (M − H)− |
| PP0384 | FA | 6.128 | 1518.2 | (M − H)− |
| PP0385 | FA | 5.785 | 1475.6 | (M + H)+ |
| PP0386 | FA | 5.652 | 1461.6 | (M + H)+ |
| PP0387 | FA | 5.897 | 1511.5 | (M + H)+ |
| PP0388 | FA | 5.796 | 1497.5 | (M + H)+ |
| PP0389 | FA | 5.887 | 1518.1 | (M − H)− |
| PP0390 | FA | 5.784 | 1505.8 | (M + H)+ |
| PP0391 | FA | 6.095 | 1519.8 | (M − H)− |
| PP0392 | FA | 5.848 | 1549.6 | (M + H)+ |
| PP0393 | FA | 5.679 | 1491.6 | (M + H)+ |
| PP0394 | FA | 5.975 | 1539.7 | (M − H)− |
| PP0395 | FA | 5.813 | 1527.6 | (M + H)+ |
| PP0396 | FA | 5.923 | 1550.1 | (M + H)+ |
| PP0397 | FA | 5.773 | 1534.0 | (M − H)− |
| PP0398 | FA | 6.064 | 1536.9 | (M + NH4)+ |
| PP0399 | FA | 6.321 | 1568.0 | (M − H)− |
| PP0400 | FA | 6.177 | 1554.2 | (M − H)− |
| PP0401 | FA | 6.113 | 1562.2 | (M − H)− |
| PP0402 | FA | 5.827 | 1516.0 | (M − H)− |
| PP0403 | FA | 6.164 | 1565.7 | (M − H)− |
| PP0404 | FA | 6.005 | 1553.7 | (M + H)+ |
| PP0405 | FA | 5.977 | 1561.9 | (M + H)+ |
| PP0406 | FA | 6.013 | 1574.2 | (M − H)− |
| PP0407 | FA | 5.537 | 1534.7 | (M + NH4)+ |
| PP0408 | FA | 5.857 | 1565.7 | (M − H)− |
| PP0409 | FA | 5.667 | 1551.7 | (M − H)− |
| PP0410 | FA | 5.876 | 1575.7 | (M + H)+ |
| PP0411 | FA | 5.677 | 1560.2 | (M − H)− |
| PP0412 | FA | 5.824 | 1462.1 | (M − H)− |
| PP0413 | FA | 6.116 | 1511.9 | (M − H)− |
| PP0414 | FA | 5.952 | 1497.9 | (M − H)− |
| PP0415 | FA | 6.063 | 1520.2 | (M − H)− |
| PP0416 | FA | 5.915 | 1505.9 | (M − H)− |
| PP0417 | FA | 5.884 | 1461.6 | (M − H)− |
| PP0418 | FA | 5.733 | 1449.6 | (M + H)+ |
| PP0419 | FA | 6.029 | 1497.6 | (M − H)− |
| PP0420 | FA | 5.875 | 1483.6 | (M − H)− |
| PP0421 | FA | 5.967 | 1505.9 | (M + H)+ |
| PP0422 | FA | 5.833 | 1492.0 | (M − H)− |
| PP0423 | FA | 6.260 | 1508.6 | (M + NH4)+ |
| PP0424 | FA | 6.132 | 1476.1 | (M − H)− |
| PP0425 | FA | 6.372 | 1526.0 | (M − H)− |
| PP0426 | FA | 6.255 | 1512.0 | (M − H)− |
| PP0427 | FA | 6.320 | 1535.6 | (M + H)+ |
| PP0428 | AA | 7.909 | 1519.7 | (M − H)− |
| PP0429 | FA | 6.067 | 1487.9 | (M − H)− |
| PP0430 | FA | 5.929 | 1473.9 | (M − H)− |
| PP0431 | FA | 6.240 | 1524.1 | (M − H)− |
| PP0432 | FA | 6.104 | 1510.0 | (M − H)− |
| PP0433 | FA | 6.215 | 1532.0 | (M − H)− |
| PP0434 | FA | 6.076 | 1537.2 | (M + NH4)+ |
| PP0435 | FA | 6.024 | 1487.9 | (M − H)− |
| PP0436 | FA | 6.268 | 1537.9 | (M − H)− |
| PP0437 | FA | 6.144 | 1523.9 | (M − H)− |
| PP0438 | FA | 6.263 | 1546.2 | (M − H)− |
| PP0439 | FA | 6.137 | 1534.2 | (M + H)+ |
| PP0440 | FA | 5.816 | 1488.0 | (M − H)− |
| PP0441 | FA | 5.639 | 1473.9 | (M − H)− |
| PP0442 | AA | 7.711 | 1524.1 | (M − H)− |
| PP0443 | FA | 5.765 | 1509.6 | (M − H)− |
| PP0444 | FA | 5.948 | 1532.0 | (M − H)− |
| PP0445 | AA | 7.707 | 1519.6 | (M + H)+ |
| PP0446 | FA | 6.288 | 1547.7 | (M + H)+ |
| PP0447 | FA | 6.169 | 1534.1 | (M + H)+ |
| PP0448 | AA | 8.045 | 1531.7 | (M − H)− |
| PP0449 | FA | 6.089 | 1517.7 | (M − H)− |
| PP0450 | FA | 6.512 | 1561.7 | (M + H)+ |

TABLE 36-continued

| Compound No. | Analytical condition | Retention time (min) | MS Found (m/z) | MS polarity |
|---|---|---|---|---|
| PP0451 | FA | 6.408 | 1547.7 | (M + H)+ |
| PP0452 | FA | 6.423 | 1558.2 | (M − H)− |
| PP0453 | FA | 6.251 | 1543.7 | (M − H)− |
| PP0454 | FA | 6.301 | 1573.6 | (M + H)+ |
| PP0455 | FA | 6.227 | 1558.0 | (M − H)− |
| PP0456 | FA | 6.077 | 1558.1 | (M − H)− |
| PP0457 | FA | 6.007 | 1543.7 | (M − H)− |
| PP0460 | FA | 5.595 | 1473.7 | (M − H)− |
| PP0461 | FA | 5.591 | 1489.6 | (M + H)+ |
| PP0462 | FA | 5.761 | 1529.6 | (M + H)+ |
| PP0463 | FA | 5.769 | 1543.7 | (M + H)+ |
| PP0464 | AA | 7.979 | 1568.2 | (M − H)− |
| PP0465 | FA | 6.677 | 1540.2 | (M − H)− |
| PP0466 | FA | 6.488 | 1526.2 | (M − H)− |
| PP0467 | AA | 8.103 | 1577.9 | (M + H)+ |
| PP0468 | FA | 6.623 | 1549.7 | (M + H)+ |
| PP0469 | FA | 6.449 | 1536.3 | (M + H)+ |
| PP0470 | FA | 5.811 | 1448.1 | (M − H)− |
| PP0471 | FA | 5.992 | 1525.6 | (M − H)− |
| PP0472 | FA | 6.269 | 1498.0 | (M − H)− |
| PP0473 | FA | 6.093 | 1484.1 | (M − H)− |
| PP0474 | FA | 5.993 | 1535.6 | (M + H)+ |
| PP0475 | FA | 6.201 | 1506.2 | (M − H)− |
| PP0476 | FA | 6.076 | 1492.2 | (M − H)− |
| PP0477 | FA | 6.547 | 1561.7 | (M + H)+ |
| PP0478 | AA | 8.063 | 1533.6 | (M + H)+ |
| PP0479 | FA | 6.223 | 1532.2 | (M − H)− |
| PP0480 | FA | 6.377 | 1533.9 | (M + H)+ |
| PP0481 | FA | 6.199 | 1545.7 | (M − H)− |
| PP0483 | FA | 6.439 | 1561.7 | (M + H)+ |
| PP0484 | FA | 6.183 | 1559.7 | (M + H)+ |
| PP0485 | FA | 6.228 | 1571.8 | (M − H)− |
| PP0487 | FA | 5.892 | 1504.2 | (M − H)− |
| PP0488 | FA | 6.040 | 1518.2 | (M − H)− |
| PP0490 | AA | 8.129 | 1546.2 | (M − H)− |
| PP0491 | FA | 6.712 | 1582.3 | (M − H)− |
| PP0492 | FA | 6.520 | 1589.8 | (M + H)+ |
| PP0493 | FA | 6.228 | 1561.6 | (M − H)− |
| PP0494 | FA | 6.028 | 1563.7 | (M + H)+ |
| PP0495 | FA | 6.496 | 1576.3 | (M − H)− |
| PP0496 | FA | 6.079 | 1518.2 | (M − H)− |
| PP0497 | AA | 7.961 | 1531.7 | (M − H)− |
| PP0498 | FA | 6.605 | 1561.7 | (M + H)+ |
| PP0499 | FA | 6.375 | 1568.2 | (M − H)− |
| PP0500 | AA | 8.120 | 1533.8 | (M − H)− |
| PP0501 | FA | 5.909 | 1552.7 | (M + NH4)+ |
| PP0502 | AA | 7.992 | 1562.2 | (M − H)− |
| PP0503 | FA | 6.119 | 1521.7 | (M + H)+ |
| PP0504 | FA | 6.072 | 1532.2 | (M − H)− |
| PP0505 | FA | 6.565 | 1559.8 | (M − H)− |
| PP0506 | FA | 6.084 | 1560.2 | (M − H)− |
| PP0507 | AA | 8.101 | 1504.2 | (M − H)− |
| PP0508 | AA | 8.101 | 1516.2 | (M − H)− |
| PP0509 | AA | 8.252 | 1530.2 | (M − H)− |
| PP0510 | FA | 7.147 | 1543.8 | (M − H)− |
| PP0511 | FA | 6.587 | 1573.7 | (M + H)+ |
| PP0512 | FA | 6.255 | 1489.7 | (M − H)− |
| PP0513 | FA | 6.556 | 1561.7 | (M + H)+ |
| PP0514 | AA | 8.157 | 1518.2 | (M − H)− |
| PP0515 | FA | 6.679 | 1549.7 | (M + H)+ |
| PP0516 | FA | 6.165 | 1532.2 | (M − H)− |
| PP0520 | FA | 6.217 | 1572.2 | (M − H)− |
| PP0521 | AA | 8.087 | 1544.2 | (M − H)− |
| PP0522 | FA | 6.173 | 1544.2 | (M − H)− |
| PP0523 | FA | 6.575 | 1561.7 | (M + H)+ |
| PP0524 | FA | 5.801 | 1536.0 | (M − H)− |
| PP0525 | FA | 5.887 | 1563.7 | (M − H)− |
| PP0526 | FA | 5.900 | 1493.9 | (M + H)+ |
| PP0527 | FA | 5.988 | 1517.8 | (M − H)− |
| PP0528 | FA | 5.440 | 1460.1 | (M − H)− |
| PP0529 | FA | 5.444 | 1462.0 | (M − H)− |
| PP0530 | FA | 5.424 | 1479.7 | (M − H)− |
| PP0531 | FA | 5.407 | 1479.6 | (M + H)+ |
| PP0532 | FA | 5.639 | 1497.6 | (M + H)+ |
| PP0533 | FA | 5.695 | 1493.8 | (M − H)− |
| PP0534 | FA | 5.400 | 1493.7 | (M + H)+ |
| PP0535 | FA | 5.329 | 1490.1 | (M − H)− |
| PP0536 | FA | 6.032 | 1547.6 | (M + H)+ |
| PP0537 | FA | 6.037 | 1544.0 | (M − H)− |
| PP0538 | FA | 6.023 | 1546.2 | (M − H)− |
| PP0539 | FA | 5.872 | 1546.2 | (M − H)− |
| PP0540 | FA | 6.047 | 1518.2 | (M − H)− |
| PP0541 | FA | 5.669 | 1518.2 | (M − H)− |
| PP0542 | FA | 5.748 | 1518.1 | (M − H)− |
| PP0543 | FA | 5.829 | 1532.2 | (M − H)− |
| PP0544 | FA | 6.107 | 1546.2 | (M − H)− |
| PP0545 | AA | 7.820 | 1546.2 | (M − H)− |
| PP0546 | FA | 5.759 | 1563.2 | (M + NH4)+ |
| PP0547 | AA | 7.824 | 1557.8 | (M − H)− |
| PP0548 | FA | 6.387 | 1572.3 | (M − H)− |
| PP0549 | FA | 5.207 | 1490.2 | (M − H)− |
| PP0550 | FA | 5.363 | 1504.1 | (M − H)− |
| PP0551 | AA | 7.964 | 1561.7 | (M + H)+ |
| PP0552 | FA | 5.711 | 1532.2 | (M − H)− |
| PP0553 | FA | 5.872 | 1568.2 | (M − H)− |
| PP0554 | AA | 7.859 | 1575.8 | (M − H)− |
| PP0555 | FA | 5.569 | 1546.2 | (M − H)− |
| PP0556 | FA | 5.329 | 1549.6 | (M + H)+ |
| PP0557 | FA | 5.835 | 1562.2 | (M − H)− |
| PP0558 | FA | 5.372 | 1566.7 | (M + NH4)+ |
| PP0559 | FA | 5.304 | 1504.2 | (M − H)− |
| PP0560 | FA | 5.473 | 1518.2 | (M − H)− |
| PP0561 | AA | 7.955 | 1546.2 | (M − H)− |
| PP0562 | FA | 5.728 | 1554.2 | (M − H)− |
| PP0563 | FA | 5.175 | 1520.2 | (M − H)− |
| PP0564 | FA | 5.371 | 1549.6 | (M + H)+ |
| PP0565 | FA | 5.459 | 1506.2 | (M − H)− |
| PP0566 | FA | 5.483 | 1517.7 | (M − H)− |
| PP0567 | FA | 5.981 | 1545.7 | (M − H)− |
| PP0568 | FA | 5.647 | 1546.2 | (M − H)− |
| PP0569 | FA | 5.791 | 1490.1 | (M − H)− |
| PP0570 | FA | 5.705 | 1502.2 | (M − H)− |
| PP0571 | FA | 5.968 | 1517.7 | (M + H)+ |
| PP0572 | FA | 6.503 | 1530.2 | (M − H)− |
| PP0573 | AA | 7.929 | 1558.2 | (M − H)− |
| PP0574 | FA | 5.569 | 1476.2 | (M − H)− |
| PP0575 | FA | 5.659 | 1554.2 | (M − H)− |
| PP0576 | FA | 5.968 | 1526.2 | (M − H)− |
| PP0577 | FA | 5.755 | 1512.1 | (M − H)− |
| PP0578 | FA | 5.640 | 1562.3 | (M − H)− |
| PP0579 | FA | 5.931 | 1534.2 | (M − H)− |
| PP0580 | FA | 5.724 | 1520.2 | (M − H)− |
| PP0581 | FA | 5.087 | 1434.1 | (M − H)− |
| PP0582 | FA | 5.196 | 1512.1 | (M − H)− |
| PP0583 | FA | 5.503 | 1484.1 | (M − H)− |
| PP0584 | FA | 5.305 | 1469.6 | (M − H)− |
| PP0585 | FA | 5.171 | 1519.7 | (M − H)− |
| PP0586 | FA | 5.437 | 1492.1 | (M − H)− |
| PP0587 | FA | 5.249 | 1478.1 | (M − H)− |
| PP0588 | FA | 5.940 | 1547.7 | (M + H)+ |
| PP0589 | AA | 7.872 | 1533.7 | (M − H)− |
| PP0590 | AA | 7.776 | 1518.2 | (M − H)− |
| PP0591 | FA | 5.945 | 1532.2 | (M − H)− |
| PP0594 | FA | 5.489 | 1558.2 | (M − H)− |
| PP0595 | FA | 5.647 | 1548.6 | (M + NH4)+ |
| PP0596 | FA | 5.632 | 1530.2 | (M − H)− |
| PP0597 | FA | 5.939 | 1546.2 | (M − H)− |
| PP0598 | FA | 5.708 | 1520.2 | (M − H)− |
| PP0599 | FA | 6.553 | 1502.0 | (M − H)− |
| PP0605 | FA | 5.912 | 1450.1 | (M − H)− |
| PP0606 | AA | 7.968 | 1473.7 | (M − H)− |
| PP0607 | FA | 5.943 | 1492.0 | (M − H)− |
| PP0608 | FA | 6.260 | 1507.7 | (M − H)− |
| PP0609 | FA | 5.848 | 1504.1 | (M − H)− |
| PP0610 | FA | 6.572 | 1559.8 | (M + H)+ |
| PP0611 | FA | 6.048 | 1476.0 | (M − H)− |
| PP0612 | FA | 6.055 | 1494.0 | (M − H)− |
| PP0613 | FA | 6.373 | 1511.6 | (M + H)+ |
| PP0614 | FA | 5.959 | 1506.2 | (M − H)− |
| PP0615 | FA | 6.671 | 1562.1 | (M + H)+ |
| PP0616 | AA | 8.116 | 1459.9 | (M − H)− |
| PP0617 | AA | 8.148 | 1513.7 | (M − H)− |

TABLE 36-continued

| Compound No. | Analytical condition | Retention time (min) | MS Found (m/z) | MS polarity |
|---|---|---|---|---|
| PP0618 | AA | 7.713 | 1446.0 | (M − H)− |
| PP0619 | FA | 5.937 | 1501.7 | (M + H)+ |
| PP0620 | FA | 6.131 | 1446.1 | (M − H)− |
| PP0621 | FA | 6.251 | 1501.6 | (M + H)+ |
| PP0622 | FA | 6.568 | 1531.6 | (M + H)+ |
| PP0626 | AA | 7.993 | 1516.1 | (M − H)− |
| PP0627 | FA | 6.203 | 1462.0 | (M − H)− |
| PP0628 | FA | 6.401 | 1515.9 | (M − H)− |
| PP0629 | AA | 7.929 | 1461.9 | (M − H)− |
| PP0630 | AA | 8.139 | 1545.9 | (M + H)+ |
| PP0631 | FA | 6.224 | 1527.5 | (M + Na)+ |
| PP0632 | FA | 6.328 | 1575.7 | (M + H)+ |
| PP0633 | FA | 6.609 | 1521.6 | (M + H)+ |
| PP0634 | AA | 8.296 | 1535.7 | (M + H)+ |
| PP0635 | AA | 8.659 | 1573.9 | (M − H)− |
| PP0636 | AA | 8.760 | 1588.3 | (M − H)− |
| PP0637 | FA | 7.508 | 1597.7 | (M + H)+ |
| PP0638 | AA | 8.284 | 1592.3 | (M + H)+ |
| PP0639 | AA | 8.431 | 1604.3 | (M − H)− |
| PP0640 | FA | 7.527 | 1644.3 | (M − H)− |
| PP0641 | AA | 8.893 | 1682.3 | (M + Na)+ |
| PP0642 | FA | 7.443 | 1667.7 | (M + H)+ |
| PP0643 | AA | 7.596 | 1507.9 | (M + H)+ |
| PP0644 | FA | 6.017 | 1520.2 | (M − H)− |
| PP0645 | AA | 8.245 | 1560.2 | (M − H)− |
| PP0646 | FA | 7.035 | 1592.9 | (M + NH4)+ |
| PP0647 | AA | 8.219 | 1583.9 | (M + H)+ |
| PP0648 | AA | 7.820 | 1575.9 | (M − H)− |
| PP0649 | AA | 8.016 | 1591.9 | (M + H)+ |
| PP0650 | FA | 6.928 | 1632.3 | (M + H)+ |
| PP0651 | FA | 7.180 | 1646.0 | (M + H)+ |
| PP0652 | AA | 8.435 | 1671.3 | (M + NH4)+ |
| PP0653 | AA | 8.127 | 1582.7 | (M + H)+ |
| PP0654 | FA | 6.003 | 1447.7 | (M − H)− |
| PP0655 | FA | 6.387 | 1477.7 | (M + H)+ |
| PP0656 | FA | 4.625 | 1566.9 | (M − H)− |
| PP0657 | FA | 5.311 | 1435.7 | (M − H)− |
| PP0658 | AA | 7.512 | 1461.7 | (M − H)− |
| PP0659 | FA | 4.784 | 1581.2 | (M − H)− |
| PP0660 | FA | 5.501 | 1447.7 | (M − H)− |
| PP0661 | FA | 5.920 | 1476.2 | (M − H)− |
| PP0662 | FA | 6.243 | 1562.2 | (M − H)− |
| PP0663 | FA | 6.387 | 1507.7 | (M + H)+ |
| PP0664 | FA | 6.475 | 1521.6 | (M + H)+ |
| PP0665 | AA | 8.059 | 1519.7 | (M + H)+ |
| PP0666 | FA | 6.351 | 1517.6 | (M + H)+ |
| PP0667 | AA | 8.061 | 1532.2 | (M − H)− |
| PP0668 | FA | 6.653 | 1548.2 | (M + H)+ |
| PP0669 | FA | 6.699 | 1549.9 | (M + H)+ |
| PP0670 | FA | 6.783 | 1560.2 | (M − H)− |
| PP0671 | FA | 6.963 | 1574.3 | (M − H)− |
| PP0672 | FA | 6.635 | 1568.2 | (M − H)− |
| PP0673 | FA | 4.837 | 1571.2 | (M + H)+ |
| PP0674 | FA | 6.227 | 1523.6 | (M + H)+ |
| PP0675 | FA | 6.201 | 1536.1 | (M − H)− |
| PP0678 | FA | 6.327 | 1548.0 | (M − H)− |
| PP0679 | FA | 6.401 | 1561.9 | (M − H)− |
| PP0680 | AA | 8.087 | 1562.2 | (M + H)+ |
| PP0681 | FA | 6.251 | 1558.2 | (M − H)− |
| PP0682 | FA | 6.377 | 1592.9 | (M + NH4)+ |
| PP0683 | FA | 6.559 | 1589.7 | (M + H)+ |
| PP0684 | FA | 6.600 | 1591.7 | (M + H)+ |
| PP0685 | FA | 6.700 | 1604.2 | (M − H)− |
| PP0686 | FA | 6.872 | 1616.3 | (M − H)− |
| PP0687 | FA | 6.531 | 1611.7 | (M + H)+ |
| PP0688 | FA | 4.775 | 1612.7 | (M + H)+ |
| PP0689 | FA | 6.136 | 1564.2 | (M − H)− |
| PP0690 | FA | 6.104 | 1578.2 | (M − H)− |
| PP0693 | AA | 7.461 | 1493.7 | (M + H)+ |
| PP0694 | FA | 5.691 | 1506.2 | (M − H)− |
| PP0695 | AA | 7.520 | 1506.2 | (M + H)+ |
| PP0696 | AA | 7.404 | 1501.8 | (M − H)− |
| PP0697 | FA | 5.644 | 1517.8 | (M − H)− |
| PP0698 | FA | 5.889 | 1533.6 | (M + H)+ |
| PP0699 | FA | 6.079 | 1535.7 | (M + H)+ |
| PP0700 | FA | 6.083 | 1547.9 | (M + H)+ |
| PP0701 | FA | 6.292 | 1562.2 | (M + H)+ |
| PP0702 | FA | 5.835 | 1554.2 | (M − H)− |
| PP0703 | FA | 3.977 | 1555.2 | (M − H)− |
| PP0704 | FA | 5.360 | 1508.2 | (M − H)− |
| PP0705 | FA | 5.359 | 1523.6 | (M + H)+ |
| PP0706 | AA | 7.369 | 1493.6 | (M + H)+ |
| PP0708 | FA | 5.425 | 1535.6 | (M + H)+ |
| PP0709 | FA | 5.571 | 1549.7 | (M + H)+ |
| PP0710 | FA | 5.543 | 1548.2 | (M + H)+ |
| PP0711 | FA | 5.401 | 1544.1 | (M − H)− |
| PP0712 | FA | 5.567 | 1560.2 | (M − H)− |
| PP0713 | FA | 5.812 | 1575.7 | (M + H)+ |
| PP0714 | FA | 6.004 | 1577.8 | (M + H)+ |
| PP0715 | FA | 6.035 | 1590.0 | (M + H)+ |
| PP0716 | FA | 6.248 | 1603.8 | (M + H)+ |
| PP0717 | FA | 5.776 | 1597.7 | (M + H)+ |
| PP0718 | AA | 7.244 | 1597.2 | (M − H)− |
| PP0719 | FA | 5.303 | 1549.8 | (M − H)− |
| PP0720 | FA | 5.309 | 1565.7 | (M + H)+ |
| PP0721 | FA | 5.220 | 1535.7 | (M + H)+ |
| PP0722 | AA | 7.623 | 1552.8 | (M + NH4)+ |
| PP0723 | AA | 8.175 | 1521.8 | (M + H)+ |
| PP0724 | FA | 6.259 | 1522.7 | (M + NH4)+ |
| PP0725 | FA | 6.580 | 1557.7 | (M + H)+ |
| PP0726 | AA | 8.377 | 1604.3 | (M − H)− |
| PP0727 | FA | 6.560 | 1590.2 | (M + H)+ |
| PP0728 | FA | 6.849 | 1641.6 | (M + H)+ |
| PP0729 | FA | 6.168 | 1492.2 | (M − H)− |
| PP0730 | FA | 5.391 | 1479.5 | (M + H)+ |
| PP0731 | FA | 5.317 | 1581.2 | (M − H)− |
| PP0732 | AA | 7.544 | 1568.8 | (M + H)+ |
| PP0733 | FA | 4.717 | 1582.7 | (M + H)+ |
| PP0734 | FA | 6.195 | 1479.7 | (M + H)+ |
| PP0735 | FA | 6.653 | 1481.7 | (M + H)+ |
| PP0736 | FA | 6.919 | 1493.8 | (M − H)− |
| PP0737 | AA | 7.889 | 1480.2 | (M − H)− |
| PP0738 | FA | 6.653 | 1495.7 | (M + H)+ |
| PP0739 | FA | 7.215 | 1535.7 | (M + H)+ |
| PP0740 | AA | 8.051 | 1552.2 | (M + Na)+ |
| PP0741 | FA | 5.955 | 1481.7 | (M − H)− |
| PP0742 | FA | 6.300 | 1509.7 | (M + H)+ |
| PP0743 | FA | 6.732 | 1525.7 | (M + H)+ |
| PP0744 | FA | 5.749 | 1466.2 | (M − H)− |
| PP0745 | FA | 6.235 | 1500.1 | (M − H)− |
| PP0746 | FA | 6.107 | 1492.1 | (M − H)− |
| PP0747 | FA | 6.400 | 1492.2 | (M − H)− |
| PP0748 | FA | 6.081 | 1512.2 | (M − H)− |
| PP0749 | FA | 6.653 | 1544.2 | (M − H)− |
| PP0750 | FA | 6.459 | 1543.9 | (M + H)+ |
| PP0751 | FA | 6.447 | 1550.2 | (M − H)− |
| PP0752 | FA | 6.635 | 1587.1 | (M + NH4)+ |
| PP0753 | FA | 6.112 | 1520.2 | (M − H)− |
| PP0754 | FA | 6.075 | 1509.8 | (M + H)+ |
| PP0755 | FA | 6.152 | 1522.2 | (M + H)+ |
| PP0756 | FA | 6.615 | 1540.7 | (M + NH4)+ |
| PP0757 | AA | 8.203 | 1536.2 | (M − H)− |
| PP0758 | FA | 6.361 | 1523.7 | (M + H)+ |
| PP0759 | FA | 6.611 | 1555.3 | (M + NH4)+ |
| PP0760 | AA | 8.443 | 1576.2 | (M − H)− |
| PP0761 | FA | 6.501 | 1571.7 | (M + H)+ |
| PP0762 | FA | 5.869 | 1543.2 | (M + NH4)+ |
| PP0763 | FA | 6.224 | 1551.7 | (M + H)+ |
| PP0764 | FA | 6.683 | 1584.9 | (M + NH4)+ |
| PP0765 | FA | 5.636 | 1507.7 | (M − H)− |
| PP0766 | FA | 6.139 | 1542.1 | (M − H)− |
| PP0767 | AA | 7.645 | 1533.8 | (M − H)− |
| PP0768 | FA | 6.324 | 1535.7 | (M + H)+ |
| PP0769 | AA | 7.692 | 1555.6 | (M + H)+ |
| PP0770 | FA | 6.197 | 1533.6 | (M + H)+ |
| PP0771 | AA | 7.875 | 1521.7 | (M + H)+ |
| PP0772 | FA | 6.147 | 1532.2 | (M + H)+ |
| PP0773 | FA | 6.605 | 1535.8 | (M + H)+ |
| PP0774 | AA | 8.264 | 1548.0 | (M − H)− |
| PP0775 | AA | 8.021 | 1535.8 | (M + H)+ |
| PP0776 | AA | 8.173 | 1547.8 | (M − H)− |
| PP0778 | AA | 8.213 | 1582.2 | (M − H)− |

TABLE 36-continued

| Compound No. | Analytical condition | Retention time (min) | MS Found (m/z) | MS polarity |
|---|---|---|---|---|
| PP0779 | AA | 7.795 | 1537.7 | (M + H)+ |
| PP0780 | FA | 6.335 | 1563.7 | (M + H)+ |
| PP0781 | FA | 6.735 | 1580.3 | (M + H)+ |
| PP0782 | FA | 5.808 | 1519.8 | (M − H)− |
| PP0783 | FA | 6.280 | 1555.6 | (M + H)+ |
| PP0784 | FA | 6.172 | 1547.6 | (M + H)+ |
| PP0785 | FA | 6.397 | 1547.8 | (M + H)+ |
| PP0786 | AA | 7.799 | 1589.9 | (M + Na)+ |
| PP0787 | FA | 5.911 | 1567.6 | (M + H)+ |
| PP0788 | AA | 7.784 | 1501.6 | (M + Na)+ |
| PP0789 | FA | 5.840 | 1533.8 | (M + H)+ |
| PP0790 | FA | 5.888 | 1520.2 | (M − H)− |
| PP0791 | FA | 5.892 | 1533.7 | (M + H)+ |
| PP0792 | FA | 6.351 | 1535.8 | (M + H)+ |
| PP0793 | FA | 6.659 | 1548.2 | (M − H)− |
| PP0794 | AA | 7.957 | 1533.9 | (M − H)− |
| PP0795 | FA | 6.427 | 1549.7 | (M + H)+ |
| PP0796 | FA | 6.999 | 1589.7 | (M + H)+ |
| PP0797 | FA | 6.392 | 1583.7 | (M + H)+ |
| PP0798 | FA | 5.785 | 1537.8 | (M + H)+ |
| PP0799 | AA | 8.004 | 1563.8 | (M + H)+ |
| PP0800 | FA | 6.584 | 1579.8 | (M + H)+ |
| PP0801 | AA | 7.373 | 1521.6 | (M + H)+ |
| PP0802 | FA | 5.895 | 1555.6 | (M + H)+ |
| PP0803 | FA | 5.839 | 1546.2 | (M − H)− |
| PP0804 | FA | 6.088 | 1547.8 | (M + H)+ |
| PP0805 | FA | 6.051 | 1465.8 | (M − H)− |
| PP0806 | AA | 7.783 | 1561.9 | (M − H)− |
| PP0807 | FA | 5.681 | 1597.7 | (M + H)+ |
| PP0808 | FA | 5.832 | 1532.2 | (M − H)− |
| PP0809 | FA | 5.907 | 1587.7 | (M + H)+ |
| PP0810 | FA | 5.607 | 1530.2 | (M − H)− |
| PP0811 | AA | 7.841 | 1565.9 | (M + H)+ |
| PP0812 | FA | 5.688 | 1550.0 | (M − H)− |
| PP0813 | FA | 5.551 | 1557.7 | (M − H)− |
| PP0814 | AA | 7.716 | 1551.7 | (M + H)+ |
| PP0815 | FA | 6.467 | 1576.2 | (M − H)− |
| PP0816 | FA | 6.365 | 1610.0 | (M − H)− |
| PP0817 | FA | 6.440 | 1547.8 | (M + H)+ |
| PP0818 | FA | 6.677 | 1601.8 | (M + H)+ |
| PP0819 | FA | 6.377 | 1543.8 | (M − H)− |
| PP0820 | AA | 8.303 | 1579.7 | (M + H)+ |
| PP0821 | AA | 8.156 | 1563.9 | (M − H)− |
| PP0822 | FA | 6.043 | 1573.6 | (M + H)+ |
| PP0823 | FA | 6.313 | 1564.2 | (M − H)− |
| PP0824 | FA | 5.619 | 1505.7 | (M + H)+ |
| PP0825 | FA | 5.912 | 1574.2 | (M + H)+ |
| PP0826 | FA | 6.151 | 1575.7 | (M + H)+ |
| PP0827 | FA | 6.003 | 1505.6 | (M + H)+ |
| PP0828 | AA | 8.135 | 1609.9 | (M − H)− |
| PP0829 | FA | 6.285 | 1575.7 | (M + H)+ |
| PP0830 | AA | 8.035 | 1504.2 | (M − H)− |
| PP0831 | FA | 6.447 | 1611.6 | (M + H)+ |
| PP0832 | FA | 5.865 | 1560.2 | (M − H)− |
| PP0833 | FA | 5.912 | 1539.2 | (M + NH4)+ |
| PP0834 | FA | 6.159 | 1556.1 | (M − H)− |
| PP0835 | FA | 5.616 | 1536.1 | (M − H)− |
| PP0836 | FA | 5.961 | 1550.2 | (M − H)− |
| PP0837 | FA | 5.941 | 1550.2 | (M − H)− |
| PP0838 | FA | 6.355 | 1577.8 | (M − H)− |
| PP0839 | FA | 6.600 | 1592.2 | (M − H)− |
| PP0840 | AA | 7.792 | 1529.9 | (M + Na)+ |
| PP0841 | AA | 8.069 | 1579.7 | (M + H)+ |
| PP0842 | FA | 6.173 | 1576.2 | (M − H)− |
| PP0843 | FA | 6.319 | 1600.2 | (M − H)− |
| PP0844 | AA | 8.259 | 1592.2 | (M − H)− |
| PP0845 | FA | 6.047 | 1536.2 | (M − H)− |
| PP0846 | FA | 6.313 | 1570.1 | (M − H)− |
| PP0847 | FA | 5.747 | 1551.8 | (M + H)+ |
| PP0848 | AA | 7.863 | 1546.2 | (M − H)− |
| PP0849 | FA | 6.176 | 1562.2 | (M + H)+ |
| PP0850 | AA | 7.787 | 1473.9 | (M − H)− |
| PP0851 | FA | 6.221 | 1596.7 | (M + NH4)+ |
| PP0852 | FA | 6.313 | 1591.7 | (M + H)+ |
| PP0853 | FA | 6.447 | 1633.6 | (M + H)+ |
| PP0854 | FA | 6.255 | 1585.9 | (M + H)+ |
| PP0855 | AA | 7.997 | 1618.6 | (M + H)+ |
| PP0856 | FA | 6.527 | 1629.8 | (M + H)+ |
| PP0857 | AA | 8.320 | 1643.9 | (M − H)− |
| PP0858 | FA | 6.072 | 1549.7 | (M − H)− |
| PP0859 | FA | 6.156 | 1508.1 | (M − H)− |
| PP0860 | FA | 5.947 | 1524.7 | (M + NH4)+ |
| PP0861 | FA | 6.225 | 1543.7 | (M + H)+ |
| PP0862 | FA | 6.185 | 1583.1 | (M + NH4)+ |
| PP0863 | FA | 5.887 | 1577.6 | (M + H)+ |
| PP0864 | FA | 6.013 | 1535.8 | (M + H)+ |
| PP0865 | FA | 5.637 | 1532.1 | (M − H)− |
| PP0866 | FA | 5.788 | 1569.7 | (M + H)+ |
| PP0867 | FA | 6.007 | 1608.8 | (M + NH4)+ |
| PP0868 | FA | 5.119 | 1535.7 | (M + H)+ |
| PP0869 | FA | 5.223 | 1535.7 | (M + H)+ |
| PP0870 | FA | 5.128 | 1535.8 | (M + H)+ |
| PP0871 | FA | 5.860 | 1566.7 | (M + NH4)+ |
| PP0872 | FA | 6.025 | 1548.2 | (M − H)− |
| PP0873 | FA | 5.873 | 1549.7 | (M + H)+ |
| PP0874 | FA | 5.993 | 1561.7 | (M + H)+ |
| PP0875 | FA | 6.084 | 1575.7 | (M + H)+ |
| PP0876 | FA | 6.256 | 1589.7 | (M + H)+ |
| PP0877 | FA | 6.465 | 1603.7 | (M + H)+ |
| PP0878 | FA | 6.713 | 1574.2 | (M − H)− |
| PP0879 | FA | 6.731 | 1606.7 | (M + NH4)+ |
| PP0880 | AA | 8.416 | 1604.3 | (M + H)+ |
| PP0881 | FA | 7.051 | 1617.8 | (M + H)+ |
| PP0882 | FA | 5.689 | 1470.2 | (M − H)− |
| PP0883 | FA | 6.501 | 1484.2 | (M − H)− |
| PP0884 | FA | 5.379 | 1485.8 | (M − H)− |
| PP0885 | FA | 5.504 | 1474.1 | (M − H)− |
| PP0886 | FA | 5.732 | 1528.1 | (M − H)− |
| PP0887 | FA | 5.264 | 1445.6 | (M + H)+ |
| PP0888 | AA | 7.311 | 1444.2 | (M − H)− |
| PP0889 | FA | 6.176 | 1499.9 | (M − H)− |
| PP0890 | FA | 6.303 | 1506.8 | (M + NH4)+ |
| PP0891 | FA | 6.512 | 1544.1 | (M + H)+ |
| PP0892 | FA | 6.071 | 1476.8 | (M + NH4)+ |
| PP0893 | AA | 7.871 | 1457.8 | (M − H)− |
| PP0894 | FA | 5.287 | 1468.2 | (M − H)− |
| PP0895 | FA | 5.477 | 1481.9 | (M − H)− |
| PP0896 | FA | 5.767 | 1496.2 | (M − H)− |
| PP0898 | AA | 7.876 | 1565.7 | (M + H)+ |
| PP0899 | FA | 5.665 | 1553.7 | (M + H)+ |
| PP0900 | AA | 7.244 | 1480.2 | (M − H)− |
| PP0901 | AA | 7.671 | 1547.8 | (M − H)− |
| PP0902 | FA | 6.028 | 1563.7 | (M + H)+ |
| PP0903 | AA | 7.604 | 1549.8 | (M − H)− |
| PP0904 | AA | 7.955 | 1470.2 | (M − H)− |
| PP0905 | FA | 6.173 | 1513.9 | (M + H)+ |
| PP0906 | FA | 6.232 | 1474.2 | (M − H)− |
| PP0907 | FA | 6.139 | 1473.7 | (M − H)− |
| PP0908 | FA | 6.420 | 1489.7 | (M − H)− |
| PP0909 | FA | 6.411 | 1491.6 | (M + H)+ |
| PP0910 | FA | 6.383 | 1494.1 | (M − H)− |
| PP0911 | FA | 6.157 | 1470.2 | (M − H)− |
| PP0912 | AA | 8.052 | 1471.7 | (M + H)+ |
| PP0913 | FA | 5.441 | 1446.7 | (M + H)+ |
| PP0914 | AA | 7.984 | 1485.9 | (M − H)− |
| PP0915 | FA | 5.989 | 1487.9 | (M + H)+ |
| PP0916 | FA | 6.309 | 1545.7 | (M + H)+ |
| PP0917 | FA | 6.216 | 1543.8 | (M − H)− |
| PP0918 | FA | 6.515 | 1560.1 | (M − H)− |
| PP0919 | FA | 6.487 | 1560.2 | (M − H)− |
| PP0920 | FA | 6.473 | 1565.7 | (M + H)+ |
| PP0921 | FA | 6.487 | 1563.8 | (M − H)− |
| PP0922 | AA | 8.229 | 1540.3 | (M − H)− |
| PP0923 | AA | 7.612 | 1515.2 | (M − H)− |
| PP0924 | FA | 6.428 | 1557.7 | (M + H)+ |
| PP0925 | AA | 7.756 | 1509.9 | (M + H)+ |
| PP0926 | FA | 6.457 | 1629.7 | (M + H)+ |
| PP0927 | FA | 6.529 | 1646.8 | (M + NH4)+ |
| PP0928 | AA | 8.200 | 1647.7 | (M + H)+ |
| PP0929 | FA | 6.521 | 1645.7 | (M + H)+ |
| PP0930 | FA | 6.739 | 1646.2 | (M + H)+ |
| PP0931 | FA | 6.520 | 1626.0 | (M + H)+ |

TABLE 36-continued

| Compound No. | Analytical condition | Retention time (min) | MS Found (m/z) | MS polarity |
|---|---|---|---|---|
| PP0932 | FA | 6.656 | 1642.7 | (M + NH4)+ |
| PP0933 | FA | 6.693 | 1625.7 | (M + H)+ |
| PP0934 | FA | 6.569 | 1604.7 | (M + NH4)+ |
| PP0935 | FA | 6.603 | 1586.2 | (M − H)− |
| PP0936 | FA | 6.624 | 1586.2 | (M − H)− |
| PP0937 | AA | 8.172 | 1623.0 | (M + NH4)+ |
| PP0938 | FA | 6.639 | 1602.2 | (M − H)− |
| PP0939 | FA | 6.769 | 1604.1 | (M + H)+ |
| PP0940 | FA | 6.829 | 1603.7 | (M + H)+ |
| PP0941 | FA | 6.637 | 1582.2 | (M − H)− |
| PP0942 | FA | 6.760 | 1584.2 | (M + H)+ |
| PP0943 | AA | 8.311 | 1584.3 | (M + H)+ |
| PP0944 | FA | 6.528 | 1563.7 | (M + H)+ |
| PP0945 | FA | 6.029 | 1564.2 | (M − H)− |
| PP0946 | FA | 6.293 | 1579.7 | (M + H)+ |
| PP0947 | FA | 6.225 | 1594.3 | (M + H)+ |
| PP0948 | FA | 6.453 | 1630.7 | (M + NH4)+ |
| PP0949 | FA | 6.676 | 1662.7 | (M + NH4)+ |
| PP0950 | AA | 8.312 | 1626.0 | (M + H)+ |
| PP0951 | AA | 8.281 | 1644.0 | (M + H)+ |
| PP0952 | FA | 6.803 | 1676.7 | (M + NH4)+ |
| PP0953 | FA | 6.944 | 1638.3 | (M − H)− |
| PP0954 | FA | 6.603 | 1581.9 | (M − H)− |
| PP0955 | FA | 5.980 | 1564.2 | (M + H)+ |
| PP0956 | FA | 6.696 | 1604.2 | (M + H)+ |
| PP0958 | FA | 6.545 | 1578.3 | (M − H)− |
| PP0959 | FA | 5.652 | 1467.7 | (M + H)+ |
| PP0960 | FA | 5.573 | 1483.6 | (M + H)+ |
| PP0961 | AA | 7.997 | 1530.1 | (M + H)+ |
| PP0962 | FA | 6.109 | 1546.2 | (M − H)− |
| PP0963 | FA | 6.305 | 1563.6 | (M + H)+ |
| PP0964 | FA | 5.927 | 1497.7 | (M + H)+ |
| PP0965 | FA | 6.171 | 1537.9 | (M − H)− |
| PP0966 | FA | 6.251 | 1531.7 | (M + H)+ |
| PP0967 | FA | 5.807 | 1481.6 | (M + H)+ |
| PP0968 | FA | 5.993 | 1523.9 | (M − H)− |
| PP0969 | FA | 6.053 | 1516.2 | (M − H)− |
| PP0970 | FA | 6.203 | 1508.1 | (M − H)− |
| PP0971 | FA | 6.093 | 1452.2 | (M − H)− |
| PP0972 | FA | 6.095 | 1482.2 | (M − H)− |
| PP0973 | FA | 6.173 | 1474.2 | (M − H)− |
| PP0975 | FA | 7.624 | 1533.9 | (M − H)− |
| PP0976 | FA | 7.545 | 1564.3 | (M − H)− |
| PP0977 | FA | 7.576 | 1556.1 | (M − H)− |
| PP0978 | FA | 5.631 | 1502.1 | (M − H)− |
| PP0979 | AA | 7.675 | 1578.6 | (M + NH4)+ |
| PP0980 | FA | 5.704 | 1518.2 | (M − H)− |
| PP0981 | FA | 6.955 | 1629.8 | (M + H)+ |
| PP0982 | FA | 7.051 | 1586.3 | (M − H)− |
| PP0983 | FA | 5.533 | 1489.7 | (M − H)− |
| PP0984 | AA | 7.593 | 1516.1 | (M − H)− |
| PP0985 | AA | 7.892 | 1524.0 | (M − H)− |
| PP0986 | AA | 6.993 | 1471.7 | (M − H)− |
| PP0987 | FA | 5.475 | 1455.7 | (M − H)− |
| PP0988 | AA | 7.971 | 1489.7 | (M − H)− |
| PP0989 | FA | 6.839 | 1539.6 | (M + H)+ |
| PP0992 | FA | 5.424 | 1563.9 | (M + H)+ |
| PP0993 | FA | 5.696 | 1577.7 | (M + H)+ |
| PP0997 | FA | 6.353 | 1591.7 | (M + H)+ |
| PP0998 | FA | 6.000 | 1629.7 | (M − H)− |
| PP0999 | FA | 6.283 | 1590.3 | (M − H)− |
| PP1000 | AA | 7.893 | 1590.2 | (M + H)+ |
| PP1001 | FA | 6.631 | 1617.8 | (M + H)+ |
| PP1002 | FA | 5.665 | 1597.9 | (M − H)− |
| PP1003 | AA | 7.601 | 1548.2 | (M − H)− |
| PP1004 | FA | 6.909 | 1604.3 | (M − H)− |
| PP1005 | AA | 8.339 | 1626.3 | (M + Na)+ |
| PP1006 | FA | 6.405 | 1630.7 | (M + NH4)+ |
| PP1008 | AA | 8.244 | 1645.7 | (M + H)+ |
| PP1009 | FA | 6.955 | 1604.3 | (M − H)− |
| PP1010 | FA | 6.699 | 1621.0 | (M + NH4)+ |
| PP1011 | FA | 7.265 | 1631.8 | (M + H)+ |
| PP1012 | FA | 6.489 | 1631.0 | (M + NH4)+ |
| PP1013 | FA | 6.729 | 1608.8 | (M + NH4)+ |
| PP1014 | AA | 8.123 | 1611.9 | (M + Na)+ |
| PP1015 | FA | 7.051 | 1617.8 | (M + H)+ |
| PP1016 | FA | 6.219 | 1561.8 | (M − H)− |
| PP1017 | FA | 6.248 | 1547.8 | (M − H)− |
| PP1018 | FA | 6.057 | 1535.7 | (M + H)+ |
| PP1019 | AA | 7.920 | 1546.2 | (M − H)− |
| PP1020 | FA | 5.771 | 1507.7 | (M + H)+ |
| PP1021 | FA | 5.808 | 1518.2 | (M − H)− |
| PP1022 | FA | 5.924 | 1520.2 | (M − H)− |
| PP1024 | AA | 8.096 | 1590.3 | (M − H)− |
| PP1025 | FA | 5.959 | 1576.2 | (M − H)− |
| PP1026 | FA | 6.064 | 1606.7 | (M + NH4)+ |
| PP1027 | FA | 5.675 | 1547.7 | (M − H)− |
| PP1028 | FA | 5.691 | 1561.7 | (M + H)+ |
| PP1029 | AA | 7.875 | 1561.8 | (M − H)− |
| PP1030 | FA | 6.152 | 1608.7 | (M + NH4)+ |
| PP1031 | FA | 6.360 | 1546.2 | (M − H)− |
| PP1032 | AA | 8.017 | 1555.8 | (M + Na)+ |
| PP1033 | FA | 6.181 | 1545.6 | (M + H)+ |
| PP1034 | FA | 5.912 | 1505.8 | (M + H)+ |
| PP1035 | FA | 5.881 | 1517.6 | (M + H)+ |
| PP1036 | FA | 6.043 | 1520.2 | (M + H)+ |
| PP1037 | FA | 6.359 | 1547.6 | (M + H)+ |
| PP1038 | FA | 6.264 | 1588.3 | (M − H)− |
| PP1039 | FA | 6.065 | 1592.7 | (M + NH4)+ |
| PP1040 | FA | 6.065 | 1586.2 | (M − H)− |
| PP1041 | AA | 7.861 | 1546.2 | (M − H)− |
| PP1042 | FA | 5.777 | 1557.9 | (M − H)− |
| PP1043 | FA | 5.941 | 1560.2 | (M − H)− |
| PP1044 | FA | 6.265 | 1589.7 | (M + H)+ |
| PP1045 | FA | 6.608 | 1561.7 | (M + H)+ |
| PP1046 | FA | 6.440 | 1547.7 | (M + H)+ |
| PP1047 | FA | 6.531 | 1559.9 | (M + H)+ |
| PP1048 | FA | 6.189 | 1519.9 | (M + H)+ |
| PP1049 | FA | 6.319 | 1531.9 | (M + H)+ |
| PP1050 | FA | 6.288 | 1532.2 | (M − H)− |
| PP1051 | FA | 6.620 | 1560.2 | (M − H)− |
| PP1052 | FA | 5.807 | 1518.2 | (M − H)− |
| PP1053 | FA | 6.072 | 1532.2 | (M − H)− |
| PP1054 | FA | 5.976 | 1518.2 | (M − H)− |
| PP1056 | AA | 7.648 | 1530.2 | (M − H)− |
| PP1057 | FA | 5.992 | 1575.7 | (M + H)+ |
| PP1058 | FA | 6.261 | 1545.9 | (M + H)+ |
| PP1059 | FA | 5.929 | 1545.8 | (M − H)− |
| PP1060 | FA | 6.044 | 1563.6 | (M + H)+ |
| PP1063 | FA | 5.780 | 1544.2 | (M − H)− |
| PP1064 | AA | 7.671 | 1517.8 | (M + H)+ |
| PP1065 | FA | 5.823 | 1504.2 | (M − H)− |
| PP1066 | FA | 6.312 | 1563.6 | (M + H)+ |
| PP1067 | FA | 6.479 | 1577.7 | (M + H)+ |
| PP1068 | FA | 6.716 | 1591.8 | (M + H)+ |
| PP1069 | FA | 5.967 | 1631.9 | (M + H)+ |
| PP1070 | FA | 6.284 | 1590.3 | (M − H)− |
| PP1071 | AA | 7.909 | 1589.8 | (M + H)+ |
| PP1072 | FA | 6.641 | 1618.3 | (M + H)+ |
| PP1073 | FA | 5.537 | 1549.6 | (M + H)+ |
| PP1075 | FA | 5.732 | 1563.7 | (M + H)+ |
| PP1076 | FA | 6.011 | 1576.2 | (M − H)− |
| PP1077 | AA | 7.361 | 1548.2 | (M − H)− |
| PP1078 | AA | 7.759 | 1562.2 | (M − H)− |
| PP1079 | FA | 6.051 | 1577.8 | (M + H)+ |
| PP1080 | FA | 6.401 | 1577.7 | (M + H)+ |
| PP1082 | FA | 6.653 | 1609.3 | (M + NH4)+ |
| PP1083 | FA | 5.477 | 1549.8 | (M + H)+ |
| PP1084 | FA | 6.173 | 1563.7 | (M + H)+ |
| PP1085 | FA | 5.815 | 1519.7 | (M + H)+ |
| PP1086 | FA | 5.608 | 1491.7 | (M − H)− |
| PP1087 | FA | 5.253 | 1478.1 | (M − H)− |
| PP1088 | AA | 7.491 | 1492.2 | (M − H)− |
| PP1089 | FA | 5.711 | 1531.8 | (M + H)+ |
| PP1090 | FA | 5.492 | 1516.2 | (M − H)− |
| PP1091 | AA | 7.515 | 1546.2 | (M − H)− |
| PP1092 | FA | 5.676 | 1573.7 | (M + H)+ |
| PP1093 | FA | 5.495 | 1489.7 | (M − H)− |
| PP1094 | FA | 6.157 | 1448.7 | (M + H)+ |
| PP1095 | FA | 6.688 | 1490.8 | (M + H)+ |
| PP1096 | FA | 6.003 | 1459.2 | (M − H)− |
| PP1097 | FA | 5.993 | 1432.7 | (M − H)− |
| PP1098 | | | | |

TABLE 36-continued

| Compound No. | Analytical condition | Retention time (min) | MS Found (m/z) | MS polarity |
|---|---|---|---|---|
| PP1099 | FA | 6.355 | 1432.7 | (M + H)+ |
| PP1100 | FA | 6.528 | 1475.1 | (M − H)− |
| PP1101 | FA | 6.099 | 1416.7 | (M − H)− |
| PP1102 | FA | 6.528 | 1445.2 | (M − H)− |
| PP1103 | FA | 5.424 | 1481.7 | (M − H)− |
| PP1104 | FA | 5.535 | 1505.7 | (M + H)+ |
| PP1105 | FA | 6.016 | 1547.7 | (M + H)+ |
| PP1106 | AA | 7.469 | 1474.1 | (M − H)− |
| PP1107 | FA | 5.843 | 1533.7 | (M + H)+ |
| PP1108 | AA | 7.376 | 1489.7 | (M − H)− |
| PP1109 | FA | 5.671 | 1519.6 | (M + H)+ |
| PP1110 | AA | 7.577 | 1517.9 | (M − H)− |
| PP1111 | AA | 7.600 | 1529.8 | (M − H)− |
| PP1112 | FA | 6.104 | 1577.0 | (M + NH4)+ |
| PP1113 | FA | 5.385 | 1521.6 | (M + H)+ |
| PP1114 | FA | 5.647 | 1516.2 | (M − H)− |
| PP1115 | FA | 5.529 | 1515.7 | (M + H)+ |
| PP1116 | AA | 7.688 | 1565.9 | (M − H)− |
| PP1117 | FA | 6.079 | 1547.7 | (M + H)+ |
| PP1118 | FA | 5.919 | 1562.7 | (M + NH4)+ |
| PP1119 | FA | 5.551 | 1536.2 | (M − H)− |
| PP1120 | AA | 7.349 | 1539.7 | (M − H)− |
| PP1121 | FA | 5.601 | 1554.2 | (M − H)− |
| PP1122 | FA | 5.167 | 1577.0 | (M + H)+ |
| PP1123 | AA | 7.657 | 1571.8 | (M − H)− |
| PP1124 | AA | 7.379 | 1558.2 | (M − H)− |
| PP1125 | FA | 6.317 | 1573.8 | (M + H)+ |
| PP1126 | AA | 7.655 | 1584.2 | (M − H)− |
| PP1127 | AA | 7.815 | 1600.2 | (M − H)− |
| PP1128 | FA | 5.533 | 1489.7 | (M − H)− |
| PP1129 | FA | 5.568 | 1497.6 | (M + H)+ |
| PP1130 | FA | 5.319 | 1489.7 | (M − H)− |
| PP1131 | FA | 5.267 | 1478.1 | (M − H)− |
| PP1132 | FA | 5.405 | 1479.6 | (M + H)+ |
| PP1133 | AA | 7.509 | 1527.7 | (M − H)− |
| PP1134 | FA | 5.625 | 1475.7 | (M + H)+ |
| PP1135 | FA | 5.355 | 1461.8 | (M + H)+ |
| PP1136 | FA | 5.765 | 1474.2 | (M − H)− |
| PP1137 | FA | 5.643 | 1492.1 | (M − H)− |
| PP1138 | AA | 7.303 | 1476.2 | (M − H)− |
| PP1139 | FA | 5.311 | 1445.8 | (M − H)− |
| PP1140 | FA | 5.249 | 1433.6 | (M − H)− |
| PP1141 | FA | 5.629 | 1462.2 | (M − H)− |
| PP1142 | FA | 5.868 | 1476.1 | (M − H)− |
| PP1143 | FA | 5.436 | 1447.6 | (M − H)− |
| PP1144 | AA | 7.804 | 1505.9 | (M − H)− |
| PP1145 | AA | 7.487 | 1478.1 | (M − H)− |
| PP1146 | AA | 7.409 | 1447.7 | (M − H)− |
| PP1147 | FA | 6.083 | 1507.6 | (M + H)+ |
| PP1148 | FA | 6.739 | 1534.2 | (M − H)− |
| PP1149 | FA | 6.693 | 1530.3 | (M − H)− |
| PP1150 | AA | 7.776 | 1489.7 | (M − H)− |
| PP1151 | FA | 6.608 | 1523.7 | (M + H)+ |
| PP1152 | FA | 6.169 | 1521.6 | (M + H)+ |
| PP1153 | AA | 8.340 | 1552.3 | (M − H)− |
| PP1154 | FA | 6.147 | 1550.1 | (M − H)− |
| PP1155 | FA | 5.957 | 1544.7 | (M + H)+ |
| PP1156 | AA | 7.688 | 1544.7 | (M + H)+ |
| PP1157 | FA | 5.939 | 1544.7 | (M + H)+ |
| PP1158 | FA | 6.536 | 1587.6 | (M + H)+ |
| PP1159 | FA | 5.964 | 1577.7 | (M + H)+ |
| PP1160 | FA | 6.277 | 1591.7 | (M + H)+ |
| PP1161 | AA | 8.323 | 1592.3 | (M − H)− |
| PP1162 | FA | 6.900 | 1623.3 | (M + NH4)+ |
| PP1163 | AA | 8.179 | 1616.2 | (M − H)− |
| PP1164 | FA | 6.441 | 1617.7 | (M + H)+ |
| PP1165 | AA | 8.039 | 1637.3 | (M + H)+ |
| PP1166 | FA | 6.287 | 1637.3 | (M + H)+ |
| PP1167 | AA | 7.977 | 1637.2 | (M + H)+ |
| PP1168 | FA | 6.872 | 1680.1 | (M + H)+ |
| PP1169 | FA | 6.585 | 1575.6 | (M + H)+ |
| PP1170 | FA | 6.533 | 1574.2 | (M − H)− |
| PP1171 | FA | 6.425 | 1594.8 | (M + H)+ |
| PP1172 | FA | 6.393 | 1594.7 | (M + H)+ |
| PP1173 | FA | 6.416 | 1594.7 | (M + H)+ |
| PP1174 | FA | 6.972 | 1637.7 | (M + H)+ |
| PP1175 | FA | 5.511 | 1483.7 | (M − H)− |
| PP1176 | FA | 5.735 | 1498.2 | (M − H)− |
| PP1177 | AA | 7.697 | 1535.8 | (M + H)+ |
| PP1178 | FA | 5.811 | 1525.7 | (M + H)+ |
| PP1179 | FA | 5.547 | 1514.2 | (M − H)− |
| PP1180 | AA | 7.696 | 1528.2 | (M − H)− |
| PP1181 | FA | 5.991 | 1560.2 | (M − H)− |
| PP1182 | FA | 4.067 | 1563.3 | (M + H)+ |
| PP1183 | FA | 6.015 | 1565.9 | (M − H)− |
| PP1184 | AA | 7.915 | 1565.8 | (M − H)− |
| PP1185 | FA | 5.825 | 1603.8 | (M + NH4)+ |
| PP1186 | AA | 7.707 | 1587.2 | (M + H)+ |
| PP1187 | FA | 5.829 | 1586.8 | (M + H)+ |
| PP1188 | FA | 6.431 | 1629.7 | (M + H)+ |
| PP1189 | AA | 7.653 | 1441.7 | (M − H)− |
| PP1190 | AA | 7.765 | 1479.7 | (M + Na)+ |
| PP1191 | AA | 7.675 | 1491.7 | (M − H)− |
| PP1192 | AA | 7.845 | 1482.2 | (M − H)− |
| PP1193 | FA | 5.637 | 1472.2 | (M − H)− |
| PP1194 | FA | 5.600 | 1486.2 | (M − H)− |
| PP1195 | AA | 7.931 | 1518.2 | (M − H)− |
| PP1196 | FA | 4.143 | 1518.8 | (M − H)− |
| PP1197 | FA | 6.119 | 1524.2 | (M − H)− |
| PP1198 | FA | 6.065 | 1523.8 | (M − H)− |
| PP1199 | FA | 5.584 | 1493.7 | (M + H)+ |
| PP1200 | FA | 5.756 | 1524.8 | (M + NH4)+ |
| PP1201 | AA | 7.749 | 1535.7 | (M + H)+ |
| PP1202 | FA | 6.536 | 1563.9 | (M + H)+ |
| PP1203 | FA | 5.868 | 1532.2 | (M − H)− |
| PP1204 | FA | 6.251 | 1561.7 | (M + H)+ |
| PP1205 | AA | 7.549 | 1522.2 | (M − H)− |
| PP1206 | FA | 5.335 | 1487.7 | (M + H)+ |
| PP1207 | AA | 7.448 | 1499.8 | (M − H)− |
| PP1208 | FA | 5.652 | 1515.8 | (M + H)+ |
| PP1209 | AA | 7.608 | 1528.3 | (M − H)− |
| PP1210 | FA | 6.345 | 1558.3 | (M + H)+ |
| PP1211 | FA | 5.637 | 1544.8 | (M + NH4)+ |
| PP1212 | FA | 6.049 | 1555.7 | (M + H)+ |
| PP1213 | FA | 5.344 | 1516.2 | (M − H)− |
| PP1214 | FA | 5.631 | 1457.6 | (M + H)+ |
| PP1215 | FA | 5.824 | 1471.6 | (M + H)+ |
| PP1216 | AA | 7.828 | 1486.1 | (M + H)+ |
| PP1217 | FA | 6.039 | 1497.8 | (M − H)− |
| PP1218 | FA | 6.607 | 1527.7 | (M + H)+ |
| PP1219 | AA | 7.847 | 1496.0 | (M − H)− |
| PP1220 | AA | 8.073 | 1524.2 | (M − H)− |
| PP1221 | FA | 5.649 | 1486.0 | (M − H)− |
| PP1222 | FA | 5.239 | 1445.7 | (M + H)+ |
| PP1223 | AA | 7.503 | 1457.9 | (M − H)− |
| PP1224 | FA | 5.563 | 1472.2 | (M − H)− |
| PP1225 | FA | 5.691 | 1488.0 | (M + H)+ |
| PP1226 | AA | 8.040 | 1514.3 | (M − H)− |
| PP1227 | AA | 7.605 | 1484.2 | (M − H)− |
| PP1228 | AA | 7.867 | 1512.3 | (M − H)− |
| PP1229 | AA | 7.435 | 1474.2 | (M − H)− |
| PP1230 | FA | 5.683 | 1473.7 | (M + H)+ |
| PP1231 | FA | 5.797 | 1487.7 | (M + H)+ |
| PP1232 | AA | 7.791 | 1500.2 | (M − H)− |
| PP1233 | FA | 5.783 | 1498.2 | (M − H)− |
| PP1234 | AA | 7.499 | 1505.8 | (M + H)+ |
| PP1235 | AA | 7.947 | 1559.7 | (M + H)+ |
| PP1242 | FA | 6.381 | 1561.7 | (M + H)+ |
| PP1243 | FA | 5.303 | 1498.2 | (M − H)− |
| PP1244 | FA | 5.468 | 1512.2 | (M − H)− |
| PP1245 | FA | 5.629 | 1545.0 | (M + NH4)+ |
| PP1246 | AA | 7.908 | 1555.8 | (M + H)+ |
| PP1247 | FA | 5.460 | 1525.7 | (M + H)+ |
| PP1248 | FA | 5.913 | 1570.7 | (M + NH4)+ |
| PP1249 | FA | 5.547 | 1468.0 | (M − H)− |
| PP1250 | AA | 7.691 | 1482.1 | (M − H)− |
| PP1251 | FA | 5.847 | 1497.7 | (M + H)+ |
| PP1252 | FA | 6.417 | 1524.1 | (M − H)− |
| PP1253 | AA | 7.715 | 1496.0 | (M + H)+ |
| PP1254 | FA | 6.123 | 1523.6 | (M + H)+ |
| PP1255 | AA | 7.335 | 1456.2 | (M − H)− |
| PP1256 | FA | 5.347 | 1471.7 | (M + H)+ |

TABLE 36-continued

| Compound No. | Analytical condition | Retention time (min) | MS Found (m/z) | MS polarity |
|---|---|---|---|---|
| PP1257 | AA | 7.549 | 1484.2 | (M − H)− |
| PP1258 | FA | 5.872 | 1519.8 | (M − H)− |
| PP1259 | FA | 6.092 | 1513.7 | (M + H)+ |
| PP1260 | FA | 5.344 | 1482.2 | (M − H)− |
| PP1261 | FA | 5.805 | 1511.8 | (M + H)+ |
| PP1262 | FA | 5.427 | 1471.7 | (M + H)+ |
| PP1263 | FA | 5.732 | 1497.9 | (M − H)− |
| PP1264 | FA | 6.008 | 1524.2 | (M − H)− |
| PP1265 | AA | 7.596 | 1481.9 | (M − H)− |
| PP1266 | FA | 5.564 | 1533.7 | (M − H)− |
| PP1267 | FA | 5.824 | 1589.7 | (M + H)+ |
| PP1268 | FA | 5.659 | 1547.7 | (M + H)+ |
| PP1269 | FA | 5.432 | 1502.2 | (M − H)− |
| PP1270 | FA | 5.327 | 1490.2 | (M − H)− |
| PP1271 | FA | 5.203 | 1445.7 | (M − H)− |
| PP1272 | AA | 7.575 | 1487.8 | (M − H)− |
| PP1273 | FA | 5.551 | 1475.7 | (M + H)+ |
| PP1274 | AA | 7.539 | 1540.2 | (M − H)− |
| PP1275 | FA | 6.077 | 1532.2 | (M − H)− |
| PP1276 | FA | 5.689 | 1519.9 | (M + H)+ |
| PP1277 | FA | 5.968 | 1532.2 | (M − H)− |
| PP1278 | FA | 5.320 | 1505.8 | (M − H)− |
| PP1279 | FA | 5.421 | 1534.2 | (M − H)− |
| PP1280 | FA | 5.469 | 1492.2 | (M − H)− |
| PP1281 | FA | 5.535 | 1546.1 | (M + H)+ |
| PP1282 | FA | 5.740 | 1575.7 | (M + H)+ |
| PP1283 | FA | 5.593 | 1573.7 | (M + H)+ |
| PP1284 | AA | 7.412 | 1532.2 | (M − H)− |
| PP1285 | FA | 5.439 | 1583.6 | (M + H)+ |
| PP1286 | FA | 5.663 | 1549.7 | (M + H)+ |
| PP1287 | FA | 5.864 | 1575.8 | (M − H)− |
| PP1288 | AA | 7.624 | 1560.2 | (M − H)− |
| PP1289 | FA | 6.219 | 1545.7 | (M + H)+ |
| PP1290 | FA | 6.519 | 1574.0 | (M + H)+ |
| PP1291 | FA | 6.359 | 1571.7 | (M + H)+ |
| PP1292 | FA | 6.045 | 1530.2 | (M − H)− |
| PP1293 | FA | 6.211 | 1580.2 | (M − H)− |
| PP1294 | FA | 6.377 | 1558.2 | (M − H)− |
| PP1295 | FA | 6.000 | 1559.7 | (M + H)+ |
| PP1296 | FA | 5.868 | 1557.7 | (M + H)+ |
| PP1297 | AA | 7.569 | 1516.2 | (M − H)− |
| PP1298 | FA | 5.740 | 1565.8 | (M − H)− |
| PP1299 | FA | 5.865 | 1562.8 | (M + NH4)+ |
| PP1300 | FA | 6.151 | 1547.7 | (M + H)+ |
| PP1301 | FA | 5.992 | 1544.2 | (M − H)− |
| PP1302 | FA | 5.676 | 1504.1 | (M − H)− |
| PP1303 | FA | 5.844 | 1554.2 | (M − H)− |
| PP1304 | FA | 5.995 | 1532.2 | (M − H)− |
| PP1305 | FA | 6.144 | 1532.2 | (M − H)− |
| PP1306 | FA | 6.459 | 1561.7 | (M + H)+ |
| PP1307 | FA | 6.293 | 1559.9 | (M + H)+ |
| PP1308 | FA | 5.967 | 1519.7 | (M + H)+ |
| PP1309 | FA | 6.141 | 1569.6 | (M + H)+ |
| PP1310 | FA | 6.301 | 1546.2 | (M − H)− |
| PP1311 | FA | 5.915 | 1602.3 | (M + H)+ |
| PP1312 | FA | 5.753 | 1617.0 | (M + NH4)+ |
| PP1313 | FA | 5.436 | 1558.2 | (M − H)− |
| PP1314 | FA | 5.607 | 1590.8 | (M + NH4)+ |
| PP1315 | AA | 7.737 | 1585.9 | (M − H)− |
| PP1316 | FA | 5.688 | 1549.7 | (M + H)+ |
| PP1317 | FA | 5.995 | 1577.7 | (M + H)+ |
| PP1318 | FA | 5.843 | 1574.2 | (M + H)+ |
| PP1319 | AA | 7.475 | 1533.9 | (M + H)+ |
| PP1320 | FA | 5.704 | 1584.2 | (M − H)− |
| PP1321 | FA | 5.451 | 1543.7 | (M + H)+ |
| PP1322 | FA | 5.337 | 1499.8 | (M − H)− |
| PP1323 | FA | 5.713 | 1513.6 | (M − H)− |
| PP1324 | FA | 5.793 | 1570.3 | (M − H)− |
| PP1325 | FA | 5.675 | 1528.2 | (M − H)− |
| PP1326 | AA | 7.889 | 1542.1 | (M + H)+ |
| PP1327 | FA | 5.620 | 1568.3 | (M − H)− |
| PP1328 | FA | 5.512 | 1527.7 | (M + H)+ |
| PP1329 | FA | 5.864 | 1556.7 | (M + NH4)+ |
| PP1330 | FA | 5.904 | 1551.7 | (M + H)+ |
| PP1331 | FA | 5.848 | 1563.7 | (M + H)+ |
| PP1333 | FA | 6.700 | 1589.8 | (M + H)+ |
| PP1334 | FA | 6.580 | 1519.7 | (M + H)+ |
| PP1335 | AA | 8.217 | 1560.2 | (M − H)− |
| PP1336 | FA | 5.760 | 1474.1 | (M − H)− |
| PP1337 | FA | 5.693 | 1516.2 | (M − H)− |
| PP1338 | FA | 5.500 | 1502.1 | (M − H)− |
| PP1339 | FA | 6.060 | 1542.2 | (M − H)− |
| PP1340 | FA | 5.845 | 1483.8 | (M − H)− |
| PP1341 | AA | 7.875 | 1540.2 | (M − H)− |
| PP1342 | FA | 6.224 | 1513.9 | (M − H)− |
| PP1343 | FA | 5.909 | 1542.2 | (M − H)− |
| PP1344 | FA | 5.701 | 1528.2 | (M − H)− |
| PP1345 | FA | 6.132 | 1554.2 | (M − H)− |
| PP1346 | FA | 5.961 | 1500.2 | (M − H)− |
| PP1347 | FA | 6.155 | 1533.8 | (M − H)− |
| PP1348 | FA | 6.073 | 1595.0 | (M + NH4)+ |
| PP1349 | FA | 6.011 | 1490.2 | (M − H)− |
| PP1350 | FA | 5.919 | 1533.7 | (M + H)+ |
| PP1351 | FA | 5.971 | 1575.7 | (M + H)+ |
| PP1352 | FA | 6.032 | 1535.7 | (M + H)+ |
| PP1353 | FA | 5.951 | 1594.8 | (M + NH4)+ |
| PP1354 | FA | 5.827 | 1561.9 | (M − H)− |
| PP1355 | FA | 6.349 | 1603.8 | (M + H)+ |
| PP1356 | FA | 6.199 | 1561.8 | (M + H)+ |
| PP1357 | AA | 7.967 | 1574.2 | (M + H)+ |
| PP1358 | FA | 6.139 | 1532.1 | (M − H)− |
| PP1359 | FA | 6.060 | 1592.7 | (M + NH4)+ |
| PP1360 | FA | 5.929 | 1560.1 | (M − H)− |
| PP1361 | FA | 6.429 | 1601.7 | (M + H)+ |
| PP1362 | FA | 6.301 | 1558.1 | (M − H)− |
| PP1363 | FA | 5.805 | 1532.2 | (M + H)+ |
| PP1364 | FA | 5.861 | 1490.2 | (M − H)− |
| PP1365 | FA | 5.781 | 1531.8 | (M + H)+ |
| PP1366 | FA | 5.615 | 1519.6 | (M + H)+ |
| PP1367 | AA | 8.011 | 1557.9 | (M − H)− |
| PP1368 | AA | 7.852 | 1515.9 | (M − H)− |
| PP1369 | FA | 5.765 | 1560.2 | (M − H)− |
| PP1370 | FA | 5.812 | 1519.9 | (M − H)− |
| PP1371 | FA | 5.745 | 1563.7 | (M + H)+ |
| PP1372 | FA | 5.612 | 1547.9 | (M − H)− |
| PP1373 | FA | 6.120 | 1589.7 | (M + H)+ |
| PP1374 | FA | 5.983 | 1564.7 | (M + NH4)+ |
| PP1375 | FA | 5.852 | 1557.8 | (M − H)− |
| PP1376 | FA | 5.928 | 1517.8 | (M − H)− |
| PP1377 | AA | 7.845 | 1561.8 | (M + H)+ |
| PP1378 | AA | 7.735 | 1564.9 | (M + NH4)+ |
| PP1379 | FA | 6.200 | 1587.7 | (M + H)+ |
| PP1380 | FA | 6.089 | 1544.2 | (M − H)− |
| PP1381 | FA | 5.613 | 1517.7 | (M + H)+ |
| PP1382 | FA | 5.653 | 1476.1 | (M − H)− |
| PP1383 | FA | 5.583 | 1520.2 | (M + H)+ |
| PP1384 | FA | 5.400 | 1504.2 | (M − H)− |
| PP1385 | FA | 5.967 | 1545.7 | (M + H)+ |
| PP1386 | FA | 6.115 | 1535.1 | (M + NH4)+ |
| PP1387 | FA | 6.464 | 1561.9 | (M + H)+ |
| PP1388 | FA | 6.303 | 1559.6 | (M + H)+ |
| PP1389 | FA | 6.311 | 1547.7 | (M + H)+ |
| PP1390 | FA | 5.417 | 1461.7 | (M + H)+ |
| PP1391 | FA | 5.585 | 1487.7 | (M + H)+ |
| PP1392 | FA | 5.889 | 1532.2 | (M − H)− |
| PP1393 | AA | 7.932 | 1600.0 | (M − H)− |
| PP1394 | AA | 7.883 | 1546.3 | (M − H)− |
| PP1395 | AA | 7.717 | 1548.2 | (M − H)− |
| PP1396 | AA | 7.880 | 1559.7 | (M + H)+ |
| PP1397 | FA | 6.065 | 1545.9 | (M − H)− |
| PP1398 | AA | 8.033 | 1577.8 | (M + H)+ |
| PP1399 | FA | 6.152 | 1587.8 | (M − H)− |
| PP1400 | FA | 6.135 | 1522.3 | (M − H)− |
| PP1401 | FA | 6.012 | 1535.8 | (M + H)+ |
| PP1402 | FA | 6.027 | 1539.7 | (M + H)+ |
| PP1403 | FA | 6.073 | 1526.2 | (M + H)+ |
| PP1404 | FA | 6.577 | 1480.7 | (M + H)+ |
| PP1405 | FA | 6.612 | 1468.6 | (M + H)+ |
| PP1406 | AA | 7.607 | 1516.2 | (M − H)− |
| PP1407 | FA | 5.520 | 1477.7 | (M + H)+ |
| PP1408 | AA | 7.584 | 1536.7 | (M + NH4)+ |
| PP1409 | FA | 5.711 | 1502.2 | (M − H)− |

TABLE 36-continued

| Compound No. | Analytical condition | Retention time (min) | MS Found (m/z) | MS polarity |
|---|---|---|---|---|
| PP1410 | FA | 6.169 | 1418.9 | (M − H)− |
| PP1411 | FA | 5.968 | 1506.3 | (M + H)+ |
| PP1412 | AA | 7.989 | 1530.3 | (M − H)− |
| PP1413 | AA | 8.175 | 1448.7 | (M + H)+ |
| PP1414 | AA | 7.632 | 1477.9 | (M − H)− |
| PP1415 | AA | 7.667 | 1522.2 | (M + H)+ |
| PP1416 | FA | 5.856 | 1504.3 | (M − H)− |
| PP1417 | FA | 6.381 | 1420.8 | (M − H)− |
| PP1418 | FA | 6.243 | 1614.3 | (M − H)− |
| PP1419 | FA | 6.464 | 1598.3 | (M − H)− |
| PP1420 | FA | 6.109 | 1561.8 | (M + H)+ |
| PP1421 | FA | 6.329 | 1544.3 | (M − H)− |
| PP1422 | FA | 5.837 | 1585.9 | (M − H)− |
| PP1423 | FA | 6.085 | 1588.7 | (M + NH4)+ |
| PP1424 | AA | 7.751 | 1551.3 | (M + NH4)+ |
| PP1425 | FA | 5.940 | 1517.7 | (M + H)+ |
| PP1426 | FA | 4.965 | 1432.2 | (M − H)− |
| PP1427 | FA | 5.144 | 1434.2 | (M − H)− |
| PP1428 | AA | 8.004 | 1469.9 | (M − H)− |
| PP1429 | FA | 5.699 | 1506.3 | (M − H)− |
| PP1430 | FA | 6.507 | 1500.0 | (M + H)+ |
| PP1431 | FA | 6.131 | 1535.9 | (M + H)+ |
| PP1432 | FA | 6.237 | 1472.3 | (M − H)− |
| PP1433 | FA | 5.861 | 1508.3 | (M − H)− |
| PP1434 | AA | 7.965 | 1457.8 | (M + H)+ |
| PP1435 | FA | 6.085 | 1471.8 | (M + H)+ |
| PP1436 | FA | 5.544 | 1493.7 | (M + H)+ |
| PP1437 | FA | 5.663 | 1506.3 | (M − H)− |
| PP1438 | FA | 6.015 | 1487.8 | (M + H)+ |
| PP1439 | FA | 6.131 | 1500.3 | (M − H)− |
| PP1440 | FA | 5.564 | 1522.0 | (M − H)− |
| PP1441 | FA | 5.676 | 1535.9 | (M − H)− |
| PP1442 | FA | 5.488 | 1505.7 | (M + H)+ |
| PP1443 | FA | 5.885 | 1467.8 | (M − H)− |
| PP1444 | AA | 7.355 | 1491.8 | (M + H)+ |
| PP1445 | AA | 7.763 | 1455.8 | (M + H)+ |
| PP1446 | AA | 7.881 | 1469.7 | (M + H)+ |
| PP1447 | FA | 5.481 | 1505.8 | (M + H)+ |
| PP1448 | FA | 5.311 | 1470.1 | (M − H)− |
| PP1449 | FA | 5.375 | 1510.2 | (M − H)− |
| PP1450 | FA | 5.488 | 1491.7 | (M + H)+ |
| PP1451 | FA | 5.473 | 1501.7 | (M + H)+ |
| PP1452 | AA | 7.363 | 1478.2 | (M − H)− |
| PP1453 | FA | 5.677 | 1506.3 | (M − H)− |
| PP1454 | FA | 5.431 | 1491.8 | (M + H)+ |
| PP1455 | FA | 5.756 | 1518.3 | (M − H)− |
| PP1456 | FA | 5.275 | 1479.9 | (M + H)+ |
| PP1457 | AA | 7.371 | 1447.7 | (M − H)− |
| PP1458 | FA | 5.947 | 1533.8 | (M + H)+ |
| PP1459 | FA | 5.857 | 1521.7 | (M + H)+ |
| PP1460 | FA | 5.896 | 1521.7 | (M + H)+ |
| PP1461 | FA | 5.057 | 1433.7 | (M − H)− |
| PP1462 | FA | 5.712 | 1435.7 | (M + H)+ |
| PP1463 | AA | 7.776 | 1475.7 | (M + H)+ |
| PP1464 | FA | 5.871 | 1455.9 | (M − H)− |
| PP1465 | FA | 5.880 | 1465.8 | (M − H)− |
| PP1466 | FA | 5.697 | 1441.8 | (M − H)− |
| PP1467 | FA | 6.031 | 1471.7 | (M + H)+ |
| PP1468 | AA | 7.808 | 1454.2 | (M + H)+ |
| PP1469 | FA | 6.119 | 1482.3 | (M − H)− |
| PP1470 | FA | 5.681 | 1442.2 | (M − H)− |
| PP1471 | FA | 5.720 | 1411.8 | (M − H)− |
| PP1472 | FA | 6.307 | 1497.8 | (M + H)+ |
| PP1473 | AA | 8.117 | 1483.9 | (M − H)− |
| PP1474 | FA | 6.255 | 1485.8 | (M + H)+ |
| PP1475 | FA | 5.435 | 1397.8 | (M − H)− |
| PP1476 | FA | 5.559 | 1457.8 | (M − H)− |
| PP1477 | FA | 5.440 | 1460.2 | (M − H)− |
| PP1478 | FA | 5.333 | 1444.2 | (M − H)− |
| PP1479 | FA | 5.215 | 1445.7 | (M − H)− |
| PP1480 | AA | 7.805 | 1460.0 | (M + H)+ |
| PP1481 | FA | 5.632 | 1462.2 | (M − H)− |
| PP1482 | FA | 5.499 | 1447.7 | (M + H)+ |
| PP1483 | FA | 5.383 | 1448.2 | (M − H)− |
| PP1484 | FA | 5.401 | 1443.7 | (M + H)+ |
| PP1485 | FA | 5.524 | 1439.5 | (M − H)− |
| PP1486 | AA | 7.860 | 1470.2 | (M − H)− |
| PP1487 | FA | 5.971 | 1467.8 | (M − H)− |
| PP1488 | FA | 5.497 | 1483.7 | (M + H)+ |
| PP1489 | FA | 6.191 | 1436.9 | (M − H)− |
| PP1490 | FA | 5.980 | 1424.7 | (M + H)+ |
| PP1491 | AA | 8.220 | 1465.2 | (M − H)− |
| PP1492 | AA | 8.020 | 1452.7 | (M + H)+ |
| PP1493 | FA | 6.399 | 1440.7 | (M + H)+ |
| PP1494 | FA | 6.183 | 1425.1 | (M − H)− |
| PP1495 | AA | 7.635 | 1535.9 | (M − H)− |
| PP1496 | AA | 7.413 | 1522.2 | (M − H)− |
| PP1497 | FA | 5.436 | 1505.6 | (M + H)+ |
| PP1498 | FA | 5.876 | 1555.6 | (M + H)+ |
| PP1499 | FA | 5.815 | 1500.2 | (M − H)− |
| PP1500 | FA | 5.736 | 1522.1 | (M − H)− |
| PP1501 | FA | 5.937 | 1532.2 | (M − H)− |
| PP1502 | AA | 7.665 | 1531.8 | (M − H)− |
| PP1503 | FA | 5.743 | 1544.2 | (M − H)− |
| PP1504 | AA | 7.969 | 1582.2 | (M − H)− |
| PP1505 | FA | 6.292 | 1582.2 | (M − H)− |
| PP1506 | FA | 6.220 | 1595.7 | (M + H)+ |
| PP1507 | AA | 7.760 | 1531.8 | (M − H)− |
| PP1508 | FA | 5.968 | 1533.6 | (M + H)+ |
| PP1509 | FA | 5.904 | 1544.2 | (M − H)− |
| PP1510 | FA | 5.981 | 1525.9 | (M − H)− |
| PP1511 | AA | 7.813 | 1515.7 | (M + H)+ |
| PP1512 | FA | 5.919 | 1549.6 | (M + H)+ |
| PP1513 | FA | 5.925 | 1535.8 | (M − H)− |
| PP1514 | FA | 5.755 | 1497.7 | (M + H)+ |
| PP1515 | AA | 7.488 | 1481.8 | (M − H)− |
| PP1516 | AA | 7.971 | 1524.3 | (M − H)− |
| PP1517 | AA | 7.741 | 1511.7 | (M + H)+ |
| PP1518 | FA | 5.907 | 1498.2 | (M − H)− |
| PP1519 | AA | 7.551 | 1485.7 | (M + H)+ |
| PP1520 | FA | 6.412 | 1438.8 | (M − H)− |
| PP1521 | FA | 6.200 | 1424.7 | (M − H)− |
| PP1522 | FA | 6.879 | 1466.8 | (M − H)− |
| PP1523 | AA | 8.104 | 1454.7 | (M + H)+ |
| PP1524 | FA | 6.605 | 1440.9 | (M − H)− |
| PP1525 | AA | 7.932 | 1428.7 | (M + H)+ |
| PP1526 | FA | 5.655 | 1538.2 | (M − H)− |
| PP1527 | FA | 5.416 | 1524.2 | (M − H)− |
| PP1528 | AA | 7.601 | 1493.8 | (M − H)− |
| PP1529 | FA | 5.335 | 1499.2 | (M + NH4)+ |
| PP1530 | FA | 6.001 | 1541.0 | (M + NH4)+ |
| PP1531 | FA | 5.759 | 1507.9 | (M − H)− |
| PP1532 | FA | 5.747 | 1497.7 | (M + H)+ |
| PP1533 | AA | 7.528 | 1565.9 | (M − H)− |
| PP1534 | FA | 5.857 | 1569.7 | (M + H)+ |
| PP1535 | FA | 6.119 | 1595.7 | (M + H)+ |
| PP1536 | FA | 5.976 | 1541.7 | (M + H)+ |
| PP1537 | FA | 6.085 | 1514.2 | (M − H)− |
| PP1538 | FA | 6.028 | 1537.6 | (M + H)+ |
| PP1552 | AA | 7.925 | 1456.2 | (M − H)− |
| PP1553 | FA | 5.576 | 1492.2 | (M − H)− |
| PP1554 | AA | 8.196 | 1583.7 | (M + H)+ |
| PP1557 | AA | 7.747 | 1539.9 | (M − H)− |
| PP1558 | AA | 7.908 | 1565.3 | (M + NH$_4$)+ |
| PP1559 | AA | 7.691 | 1526.2 | (M − H)− |
| PP1560 | FA | 5.992 | 1540.2 | (M − H)− |
| PP1561 | FA | 6.204 | 1572.9 | (M + NH$_4$)+ |
| PP1562 | FA | 6.160 | 1573.0 | (M + NH$_4$)+ |
| PP1563 | FA | 5.988 | 1552.4 | (M − H)− |
| PP1564 | FA | 6.257 | 1585.3 | (M + NH$_4$)+ |
| PP1565 | FA | 6.461 | 1582.3 | (M + H)+ |
| PP1566 | AA | 7.821 | 1552.7 | (M + NH$_4$)+ |
| PP1568 | AA | 7.964 | 1582.2 | (M + Na)+ |
| PP1569 | AA | 7.920 | 1564.2 | (M + H)+ |
| PP1570 | FA | 6.217 | 1546.3 | (M − H)− |
| PP1571 | FA | 6.527 | 1560.0 | (M − H)− |
| PP1572 | FA | 6.585 | 1591.7 | (M + H)+ |
| PP1573 | FA | 6.211 | 1566.3 | (M − H)− |
| PP1574 | FA | 6.333 | 1561.9 | (M + H)+ |
| PP1575 | FA | 6.881 | 1606.3 | (M + H)+ |
| PP1576 | AA | 8.111 | 1561.8 | (M + H)+ |
| PP1577 | AA | 8.172 | 1537.8 | (M + H)+ |

TABLE 36-continued

| Compound No. | Analytical condition | Retention time (min) | MS Found (m/z) | MS polarity |
|---|---|---|---|---|
| PP1578 | AA | 8.343 | 1552.3 | (M + H)+ |
| PP1579 | AA | 8.029 | 1546.2 | (M − H)− |
| PP1580 | FA | 6.640 | 1579.2 | (M + NH$_4$)+ |
| PP1582 | AA | 8.784 | 1559.2 | (M − H)− |
| PP1583 | FA | 7.421 | 1533.0 | (M − H)− |
| PP1584 | AA | 8.520 | 1531.2 | (M − H)− |
| PP1586 | AA | 8.591 | 1568.7 | (M + H)+ |
| PP1587 | AA | 8.632 | 1506.7 | (M + H)+ |
| PP1588 | AA | 8.492 | 1522.2 | (M + NH$_4$)+ |
| PP1589 | AA | 8.289 | 1478.7 | (M + H)+ |
| PP1590 | AA | 8.180 | 1476.7 | (M + H)+ |
| PP1591 | AA | 8.352 | 1514.7 | (M + H)+ |
| PP1592 | AA | 8.265 | 1512.6 | (M + H)+ |
| PP1593 | AA | 8.721 | 1532.7 | (M + H)+ |
| PP1594 | AA | 8.617 | 1531.2 | (M + H)+ |
| PP1595 | AA | 8.395 | 1504.7 | (M + H)+ |
| PP1596 | AA | 8.313 | 1502.7 | (M + H)+ |
| PP1598 | AA | 8.400 | 1538.7 | (M + H)+ |
| PP1599 | AA | 8.156 | 1496.7 | (M + H)+ |
| PP1600 | AA | 8.020 | 1470.7 | (M + H)+ |
| PP1601 | AA | 8.405 | 1414.7 | (M + H)+ |
| PP1603 | AA | 8.695 | 1442.7 | (M + H)+ |
| PP1605 | AA | 8.229 | 1490.7 | (M + H)+ |
| PP1606 | AA | 8.119 | 1489.1 | (M + H)+ |
| PP1607 | AA | 7.893 | 1462.7 | (M + H)+ |
| PP1608 | FA | 6.600 | 1498.6 | (M + H)+ |
| PP1609 | AA | 7.920 | 1496.6 | (M + H)+ |
| PP1610 | AA | 8.288 | 1516.7 | (M + H)+ |
| PP1611 | AA | 8.208 | 1514.6 | (M + H)+ |
| PP1612 | AA | 7.989 | 1488.7 | (M + H)+ |
| PP1613 | AA | 7.927 | 1486.7 | (M + H)+ |
| PP1614 | AA | 8.115 | 1524.6 | (M + H)+ |
| PP1615 | AA | 8.041 | 1522.7 | (M + H)+ |
| PP1616 | AA | 7.749 | 1480.7 | (M + H)+ |
| PP1617 | AA | 7.637 | 1454.7 | (M + H)+ |
| PP1620 | AA | 8.259 | 1426.7 | (M + H)+ |
| PP1622 | AA | 8.452 | 1492.7 | (M + H)+ |
| PP1623 | AA | 8.305 | 1490.7 | (M + H)+ |
| PP1624 | AA | 8.091 | 1464.6 | (M + H)+ |
| PP1625 | AA | 7.991 | 1462.6 | (M + H)+ |
| PP1626 | FA | 6.973 | 1500.6 | (M + H)+ |
| PP1627 | AA | 8.080 | 1498.7 | (M + H)+ |
| PP1628 | AA | 8.536 | 1518.7 | (M + H)+ |
| PP1629 | FA | 7.181 | 1516.7 | (M + H)+ |
| PP1630 | AA | 8.204 | 1491.2 | (M + H)+ |
| PP1631 | AA | 8.123 | 1488.7 | (M + H)+ |
| PP1632 | AA | 8.295 | 1526.7 | (M + H)+ |
| PP1633 | AA | 8.229 | 1523.2 | (M − H)− |
| PP1634 | FA | 7.851 | 1545.2 | (M + H)+ |
| PP1635 | AA | 8.684 | 1542.7 | (M + H)+ |
| PP1636 | AA | 8.468 | 1516.7 | (M + H)+ |
| PP1637 | AA | 8.403 | 1514.7 | (M + H)+ |
| PP1639 | AA | 8.500 | 1549.2 | (M − H)− |
| PP1640 | FA | 5.499 | 1606.8 | (M + NH$_4$)+ |
| PP1641 | FA | 5.891 | 1517.7 | (M − H)− |
| PP1643 | AA | 7.899 | 1583.7 | (M + H)+ |
| PP1644 | FA | 6.128 | 1585.7 | (M − H)− |
| PP1645 | FA | 6.215 | 1546.4 | (M − H)− |
| PP1646 | FA | 6.489 | 1561.8 | (M + H)+ |
| PP1648 | FA | 6.481 | 1574.2 | (M + H)+ |
| PP1649 | FA | 6.412 | 1578.9 | (M + NH$_4$)+ |
| PP1650 | FA | 6.355 | 1560.0 | (M − H)− |
| PP1651 | FA | 6.459 | 1572.3 | (M + H)+ |
| PP1653 | AA | 7.856 | 1540.3 | (M − H)− |
| PP1654 | FA | 6.403 | 1572.9 | (M + NH$_4$)+ |
| PP1655 | FA | 6.093 | 1578.3 | (M + H)+ |
| PP1656 | FA | 6.216 | 1588.8 | (M + NH$_4$)+ |
| PP1657 | AA | 7.909 | 1571.8 | (M + H)+ |
| PP1658 | FA | 6.184 | 1539.7 | (M + H)+ |
| PP1660 | AA | 8.020 | 1547.2 | (M + NH$_4$)+ |
| PP1661 | FA | 6.581 | 1530.3 | (M − H)− |
| PP1662 | FA | 6.501 | 1530.2 | (M − H)− |
| PP1663 | FA | 6.189 | 1521.6 | (M + H)+ |
| PP1665 | FA | 6.529 | 1560.2 | (M − H)− |
| PP1666 | FA | 5.971 | 1519.6 | (M + H)+ |
| PP1667 | FA | 6.224 | 1558.2 | (M − H)− |
| PP1668 | AA | 8.079 | 1575.9 | (M − H)− |
| PP1670 | FA | 6.651 | 1561.9 | (M + H)+ |
| PP1671 | FA | 6.157 | 1563.7 | (M + H)+ |
| PP1672 | AA | 8.133 | 1578.2 | (M + H)+ |
| PP1673 | FA | 6.879 | 1606.3 | (M + H)+ |
| PP1674 | FA | 5.632 | 1512.4 | (M − H)− |
| PP1675 | FA | 5.928 | 1581.7 | (M + H)+ |
| PP1676 | FA | 6.260 | 1573.3 | (M + NH$_4$)+ |
| PP1677 | FA | 5.779 | 1554.8 | (M + NH$_4$)+ |
| PP1678 | AA | 7.967 | 1585.3 | (M + NH$_4$)+ |
| PP1679 | FA | 5.915 | 1558.3 | (M + H)+ |
| PP1682 | AA | 7.832 | 1558.2 | (M + H)+ |
| PP1683 | FA | 6.364 | 1517.8 | (M + H)+ |
| PP1684 | AA | 8.164 | 1542.1 | (M − H)− |
| PP1687 | FA | 6.327 | 1571.7 | (M + H)+ |
| PP1688 | AA | 7.523 | 1562.1 | (M + H)+ |
| PP1689 | AA | 7.737 | 1521.7 | (M + H)+ |
| PP1691 | AA | 7.749 | 1531.7 | (M + H)+ |
| PP1692 | AA | 7.945 | 1545.7 | (M + H)+ |
| PP1693 | AA | 7.861 | 1534.0 | (M − H)− |
| PP1694 | FA | 6.349 | 1549.7 | (M + H)+ |
| PP1696 | AA | 7.957 | 1551.7 | (M + H)+ |
| PP1697 | AA | 8.031 | 1587.9 | (M + Na)+ |
| PP1698 | AA | 8.215 | 1578.3 | (M − H)− |
| PP1699 | AA | 7.909 | 1532.0 | (M − H)− |
| PP1700 | AA | 7.791 | 1570.2 | (M + H)+ |
| PP1701 | AA | 7.597 | 1572.2 | (M − H)− |
| PP1702 | AA | 7.816 | 1588.2 | (M + H)+ |
| PP1703 | FA | 6.120 | 1542.2 | (M − H)− |
| PP1704 | AA | 8.124 | 1560.3 | (M − H)− |
| PP1705 | FA | 6.528 | 1573.8 | (M + H)+ |
| PP1706 | AA | 7.849 | 1567.2 | (M + NH$_4$)+ |
| PP1707 | FA | 5.896 | 1510.3 | (M − H)− |
| PP1709 | AA | 7.623 | 1560.2 | (M − H)− |
| PP1710 | FA | 6.144 | 1578.3 | (M − H)− |
| PP1711 | FA | 6.217 | 1540.2 | (M + H)+ |
| PP1713 | FA | 6.231 | 1551.8 | (M + H)+ |
| PP1714 | AA | 7.972 | 1554.2 | (M + H)+ |
| PP1715 | FA | 6.363 | 1553.8 | (M + H)+ |
| PP1716 | AA | 8.016 | 1566.2 | (M + H)+ |
| PP1717 | AA | 7.724 | 1541.7 | (M + H)+ |
| PP1718 | AA | 7.992 | 1569.7 | (M + H)+ |
| PP1721 | AA | 7.981 | 1554.2 | (M + H)+ |
| PP1722 | FA | 5.993 | 1543.8 | (M + H)+ |
| PP1727 | FA | 6.205 | 1516.2 | (M − H)− |
| PP1728 | FA | 6.307 | 1529.7 | (M + H)+ |
| PP1729 | FA | 6.356 | 1533.7 | (M + H)+ |
| PP1731 | FA | 6.260 | 1555.8 | (M + H)+ |
| PP1732 | AA | 7.944 | 1569.8 | (M + H)+ |
| PP1733 | FA | 6.392 | 1606.2 | (M + H)+ |
| PP1734 | FA | 6.473 | 1624.2 | (M + H)+ |
| PP1735 | FA | 6.259 | 1567.7 | (M − H)− |
| PP1736 | FA | 6.561 | 1583.7 | (M + H)+ |
| PP1737 | FA | 6.391 | 1580.2 | (M + H)+ |
| PP1738 | FA | 6.256 | 1581.7 | (M + H)+ |
| PP1739 | FA | 6.551 | 1595.7 | (M + H)+ |
| PP1740 | FA | 6.164 | 1569.7 | (M + H)+ |
| PP1741 | FA | 6.064 | 1570.3 | (M + H)+ |
| PP1742 | FA | 6.128 | 1598.7 | (M + NH$_4$)+ |
| PP1743 | FA | 6.196 | 1603.2 | (M + NH$_4$)+ |
| PP1744 | AA | 8.092 | 1614.3 | (M + H)+ |
| PP1746 | AA | 7.887 | 1549.1 | (M + NH$_4$)+ |
| PP1747 | AA | 7.759 | 1566.2 | (M − H)− |
| PP1748 | FA | 6.205 | 1544.3 | (M − H)− |
| PP1749 | FA | 6.196 | 1558.1 | (M + H)+ |
| PP1750 | FA | 6.392 | 1558.2 | (M − H)− |
| PP1751 | AA | 8.076 | 1560.1 | (M + H)+ |
| PP1752 | FA | 6.437 | 1572.1 | (M + H)+ |
| PP1753 | AA | 7.813 | 1569.3 | (M + Na)+ |
| PP1754 | FA | 6.291 | 1576.1 | (M + H)+ |
| PP1757 | AA | 8.087 | 1564.1 | (M + H)+ |
| PP1758 | FA | 6.044 | 1511.9 | (M − H)− |
| PP1759 | FA | 6.033 | 1526.1 | (M + H)+ |
| PP1760 | FA | 6.241 | 1527.7 | (M + H)+ |
| PP1761 | FA | 6.177 | 1526.2 | (M − H)− |
| PP1762 | AA | 8.099 | 1540.2 | (M + H)+ |

TABLE 36-continued

| Compound No. | Analytical condition | Retention time (min) | MS Found (m/z) | MS polarity |
|---|---|---|---|---|
| PP1763 | AA | 8.125 | 1544.2 | (M + H)+ |
| PP1764 | AA | 8.045 | 1561.2 | (M + NH4)+ |
| PP1765 | AA | 7.795 | 1548.3 | (M + H)+ |
| PP1767 | FA | 6.097 | 1548.1 | (M + H)+ |
| PP1768 | FA | 6.196 | 1546.3 | (M − H)− |
| PP1769 | FA | 6.077 | 1546.4 | (M − H)− |
| PP1771 | FA | 6.479 | 1561.7 | (M + H)+ |
| PP1772 | FA | 6.388 | 1561.9 | (M + H)+ |
| PP1773 | AA | 8.093 | 1560.9 | (M + H)+ |
| PP1776 | FA | 5.999 | 1490.2 | (M − H)− |
| PP1777 | AA | 7.727 | 1490.3 | (M − H)− |
| PP1779 | FA | 5.569 | 1520.1 | (M + H)+ |
| PP1780 | FA | 5.317 | 1474.1 | (M − H)− |
| PP1781 | AA | 7.419 | 1464.2 | (M − H)− |
| PP1782 | FA | 5.153 | 1420.3 | (M − H)− |
| PP1783 | FA | 5.467 | 1477.7 | (M + H)+ |
| PP1784 | FA | 5.213 | 1432.3 | (M − H)− |
| PP1785 | FA | 5.668 | 1490.3 | (M − H)− |
| PP1786 | FA | 5.432 | 1447.7 | (M + H)+ |
| PP1788 | AA | 7.464 | 1446.3 | (M − H)− |
| PP1789 | FA | 5.693 | 1461.9 | (M + H)+ |
| PP1790 | AA | 7.716 | 1492.0 | (M − H)− |
| PP1791 | AA | 7.531 | 1450.1 | (M + H)+ |
| PP1792 | AA | 7.692 | 1462.4 | (M − H)− |
| PP1793 | AA | 7.583 | 1478.4 | (M − H)− |
| PP1794 | FA | 5.392 | 1434.3 | (M − H)− |
| PP1795 | FA | 5.648 | 1489.7 | (M − H)− |
| PP1796 | AA | 7.409 | 1465.2 | (M + NH4)+ |
| PP1797 | FA | 5.919 | 1518.2 | (M + H)+ |
| PP1798 | FA | 5.683 | 1471.9 | (M − H)− |
| PP1799 | FA | 5.660 | 1449.7 | (M + H)+ |
| PP1800 | AA | 7.576 | 1460.3 | (M − H)− |
| PP1801 | FA | 5.945 | 1486.3 | (M − H)− |
| PP1802 | FA | 5.719 | 1461.8 | (M + H)+ |
| PP1803 | AA | 7.785 | 1474.4 | (M − H)− |
| PP1804 | FA | 5.693 | 1531.9 | (M − H)− |
| PP1805 | FA | 5.436 | 1488.2 | (M − H)− |
| PP1806 | AA | 7.547 | 1478.3 | (M − H)− |
| PP1807 | FA | 5.288 | 1435.7 | (M + H)+ |
| PP1808 | FA | 5.581 | 1490.1 | (M − H)− |
| PP1809 | AA | 7.423 | 1465.2 | (M + NH4)+ |
| PP1810 | FA | 5.740 | 1505.9 | (M + H)+ |
| PP1811 | FA | 5.504 | 1460.2 | (M − H)− |
| PP1812 | AA | 7.540 | 1448.2 | (M − H)− |
| PP1813 | FA | 5.588 | 1460.2 | (M − H)− |
| PP1814 | AA | 7.717 | 1474.2 | (M − H)− |
| PP1815 | FA | 6.153 | 1517.6 | (M − H)− |
| PP1816 | AA | 7.645 | 1429.6 | (M − H)− |
| PP1817 | FA | 6.024 | 1447.6 | (M + H)+ |
| PP1818 | AA | 7.941 | 1458.2 | (M − H)− |
| PP1819 | FA | 6.377 | 1473.4 | (M + H)+ |
| PP1820 | FA | 6.493 | 1432.2 | (M + H)+ |
| PP1821 | FA | 5.871 | 1461.6 | (M − H)− |
| PP1822 | FA | 5.683 | 1417.6 | (M − H)− |
| PP1823 | FA | 6.043 | 1475.7 | (M − H)− |
| PP1825 | FA | 6.259 | 1561.3 | (M + H)+ |
| PP1826 | FA | 6.137 | 1545.9 | (M − H)− |
| PP1827 | FA | 5.697 | 1503.8 | (M + H)+ |
| PP1828 | FA | 5.503 | 1497.8 | (M + H)+ |
| PP1829 | FA | 6.296 | 1531.8 | (M + H)+ |
| PP1830 | FA | 6.123 | 1542.5 | (M + NH4)+ |
| PP1831 | FA | 6.029 | 1517.8 | (M + H)+ |
| PP1832 | FA | 5.848 | 1529.0 | (M + NH4)+ |
| PP1833 | FA | 5.473 | 1506.4 | (M + NH4)+ |
| PP1834 | FA | 5.283 | 1501.3 | (M + NH4)+ |
| PP1835 | FA | 6.069 | 1516.0 | (M − H)− |
| PP1836 | AA | 7.579 | 1444.2 | (M + H)+ |
| PP1837 | FA | 6.201 | 1498.1 | (M + H)+ |
| PP1838 | FA | 5.519 | 1442.4 | (M + H)+ |
| PP1839 | AA | 7.921 | 1470.3 | (M − H)− |
| PP1840 | FA | 5.577 | 1444.3 | (M − H)− |
| PP1841 | FA | 6.097 | 1471.7 | (M + H)+ |
| PP1842 | FA | 5.516 | 1442.4 | (M − H)− |
| PP1844 | FA | 5.939 | 1446.2 | (M − H)− |
| PP1846 | FA | 5.844 | 1447.6 | (M + H)+ |
| PP1848 | AA | 7.795 | 1447.6 | (M + H)+ |
| PP1849 | FA | 6.016 | 1471.7 | (M + H)+ |
| PP1850 | FA | 5.839 | 1447.6 | (M + H)+ |
| PP1851 | AA | 7.664 | 1501.7 | (M + H)+ |
| PP1852 | FA | 5.765 | 1447.6 | (M + H)+ |
| PP1853 | FA | 5.360 | 1428.4 | (M − H)− |
| PP1854 | AA | 7.684 | 1469.4 | (M + Na)+ |
| PP1855 | AA | 7.369 | 1429.7 | (M + H)+ |
| PP1856 | FA | 5.852 | 1447.8 | (M − H)− |
| PP1857 | FA | 5.292 | 1447.3 | (M + NH4)+ |
| PP1859 | FA | 5.227 | 1430.2 | (M + H)+ |
| PP1860 | FA | 5.799 | 1449.7 | (M + H)+ |
| PP1861 | FA | 5.284 | 1440.4 | (M − H)− |
| PP1862 | AA | 7.695 | 1450.3 | (M + H)+ |
| PP1863 | FA | 5.225 | 1440.4 | (M − H)− |
| PP1864 | AA | 7.623 | 1467.3 | (M + NH4)+ |
| PP1865 | FA | 5.469 | 1442.3 | (M − H)− |
| PP1866 | FA | 5.619 | 1448.4 | (M − H)− |
| PP1867 | FA | 5.412 | 1442.4 | (M − H)− |
| PP1868 | FA | 5.879 | 1475.3 | (M + NH4)+ |
| PP1869 | AA | 7.411 | 1458.3 | (M − H)− |
| PP1870 | FA | 5.792 | 1456.4 | (M − H)− |
| PP1871 | FA | 5.211 | 1458.4 | (M − H)− |
| PP1872 | FA | 5.808 | 1486.4 | (M − H)− |
| PP1873 | AA | 7.563 | 1474.3 | (M + H)+ |
| PP1874 | FA | 6.220 | 1460.2 | (M − H)− |
| PP1875 | FA | 5.693 | 1478.4 | (M − H)− |
| PP1876 | FA | 6.124 | 1460.3 | (M − H)− |
| PP1877 | FA | 5.609 | 1480.3 | (M + H)+ |
| PP1878 | FA | 5.859 | 1495.1 | (M + NH4)+ |
| PP1879 | FA | 5.501 | 1484.3 | (M − H)− |
| PP1880 | FA | 6.141 | 1491.7 | (M + H)+ |
| PP1881 | AA | 7.921 | 1524.4 | (M + Na)+ |
| PP1882 | FA | 6.128 | 1462.4 | (M − H)− |
| PP1883 | FA | 6.449 | 1506.2 | (M + H)+ |
| PP1884 | AA | 7.880 | 1462.3 | (M − H)− |
| PP1885 | FA | 6.072 | 1470.5 | (M − H)− |
| PP1886 | FA | 6.052 | 1492.4 | (M − H)− |
| PP1887 | FA | 5.995 | 1502.4 | (M + H)+ |
| PP1888 | FA | 5.823 | 1457.7 | (M + H)+ |
| PP1889 | FA | 6.092 | 1471.7 | (M + H)+ |
| PP1890 | FA | 5.737 | 1456.4 | (M − H)− |
| PP1891 | AA | 7.837 | 1470.3 | (M − H)− |
| PP1892 | AA | 7.688 | 1486.0 | (M − H)− |
| PP1893 | FA | 6.419 | 1474.3 | (M − H)− |
| PP1894 | AA | 8.072 | 1476.1 | (M + H)+ |
| PP1895 | FA | 5.815 | 1476.3 | (M − H)− |
| PP1896 | FA | 6.023 | 1490.3 | (M − H)− |
| PP1897 | FA | 5.575 | 1454.3 | (M − H)− |
| PP1898 | FA | 5.821 | 1468.4 | (M − H)− |
| PP1899 | FA | 6.092 | 1482.4 | (M − H)− |
| PP1900 | FA | 5.520 | 1456.4 | (M + H)+ |
| PP1901 | AA | 7.687 | 1470.2 | (M + H)+ |
| PP1902 | AA | 7.857 | 1482.3 | (M − H)− |
| PP1903 | AA | 7.709 | 1500.4 | (M + H)+ |
| PP1904 | FA | 5.759 | 1456.4 | (M − H)− |
| PP1905 | FA | 6.000 | 1488.8 | (M + NH4)+ |
| PP1906 | FA | 6.280 | 1484.4 | (M − H)− |
| PP1907 | FA | 5.696 | 1456.3 | (M − H)− |
| PP1908 | AA | 7.796 | 1489.4 | (M + NH4)+ |
| PP1909 | FA | 6.209 | 1503.2 | (M + NH4)+ |
| PP1910 | AA | 7.641 | 1505.4 | (M + NH4)+ |
| PP1911 | FA | 6.275 | 1497.9 | (M + H)+ |
| PP1913 | AA | 7.848 | 1565.2 | (M + H)+ |
| PP1914 | FA | 5.860 | 1493.6 | (M + H)+ |
| PP1915 | AA | 8.093 | 1560.4 | (M + H)+ |
| PP1916 | FA | 5.925 | 1492.2 | (M − H)− |
| PP1917 | FA | 6.399 | 1590.4 | (M − H)− |
| PP1918 | FA | 6.004 | 1506.2 | (M − H)− |
| PP1919 | AA | 8.085 | 1590.0 | (M − H)− |
| PP1920 | FA | 6.113 | 1536.2 | (M − H)− |
| PP1921 | AA | 8.113 | 1590.4 | (M − H)− |
| PP1922 | FA | 7.480 | 1506.2 | (M − H)− |
| PP1923 | FA | 6.164 | 1616.4 | (M − H)− |
| PP1925 | FA | 6.241 | 1560.4 | (M + H)+ |
| PP1926 | FA | 6.055 | 1506.3 | (M − H)− |
| PP1927 | AA | 8.071 | 1570.3 | (M + Na)+ |

TABLE 36-continued

| Compound No. | Analytical condition | Retention time (min) | MS Found (m/z) | MS polarity |
|---|---|---|---|---|
| PP1928 | FA | 6.119 | 1537.2 | (M + NH4)+ |
| PP1929 | AA | 8.004 | 1542.4 | (M − H)− |
| PP1930 | FA | 6.532 | 1503.6 | (M + H)+ |
| PP1931 | FA | 6.131 | 1542.4 | (M − H)− |
| PP1932 | FA | 6.161 | 1509.9 | (M − H)− |
| PP1934 | FA | 6.071 | 1509.1 | (M + NH4)+ |
| PP1935 | FA | 6.017 | 1491.6 | (M + H)+ |
| PP1936 | FA | 6.197 | 1521.6 | (M + H)+ |
| PP1937 | FA | 6.011 | 1535.9 | (M + H)+ |
| PP1938 | FA | 6.128 | 1562.3 | (M − H)− |
| PP1941 | FA | 6.237 | 1533.8 | (M − H)− |
| PP1942 | FA | 6.345 | 1546.3 | (M − H)− |
| PP1943 | FA | 6.035 | 1558.3 | (M − H)− |
| PP1944 | AA | 7.965 | 1560.4 | (M + H)+ |
| PP1945 | FA | 6.639 | 1572.3 | (M − H)− |
| PP1946 | FA | 6.001 | 1518.2 | (M − H)− |
| PP1947 | FA | 6.237 | 1518.2 | (M − H)− |
| PP1948 | FA | 6.028 | 1520.1 | (M + H)+ |
| PP1949 | FA | 6.159 | 1519.6 | (M + H)+ |
| PP1950 | FA | 6.037 | 1517.8 | (M − H)− |
| PP1952 | FA | 6.071 | 1520.1 | (M + H)+ |
| PP1953 | FA | 5.936 | 1518.2 | (M − H)− |
| PP1954 | FA | 6.140 | 1518.2 | (M − H)− |
| PP1955 | FA | 5.913 | 1532.1 | (M + H)+ |
| PP1956 | FA | 6.005 | 1476.2 | (M − H)− |
| PP1957 | FA | 6.160 | 1502.2 | (M − H)− |
| PP1958 | FA | 6.016 | 1506.2 | (M − H)− |
| PP1959 | FA | 6.028 | 1520.1 | (M + H)+ |
| PP1960 | FA | 6.096 | 1464.2 | (M − H)− |
| PP1961 | FA | 6.301 | 1490.2 | (M − H)− |
| PP1963 | FA | 5.980 | 1536.1 | (M + H)+ |
| PP1964 | FA | 6.183 | 1548.3 | (M − H)− |
| PP1965 | FA | 6.484 | 1562.2 | (M − H)− |
| PP1967 | FA | 6.059 | 1518.2 | (M − H)− |
| PP1968 | FA | 6.108 | 1517.9 | (M − H)− |
| PP1969 | FA | 6.115 | 1517.9 | (M − H)− |
| PP1970 | FA | 6.055 | 1518.2 | (M − H)− |
| PP1971 | FA | 6.037 | 1518.3 | (M − H)− |
| PP1972 | FA | 6.279 | 1545.4 | (M − H)− |
| PP1973 | FA | 6.353 | 1584.0 | (M − H)− |
| PP1974 | FA | 6.568 | 1559.9 | (M − H)− |
| PP1975 | FA | 6.212 | 1586.3 | (M + H)+ |
| PP1976 | FA | 6.583 | 1529.8 | (M − H)− |
| PP1977 | FA | 6.235 | 1553.9 | (M − H)− |
| PP1979 | FA | 5.961 | 1540.1 | (M − H)− |
| PP1980 | FA | 6.395 | 1527.5 | (M − H)− |
| PP1981 | FA | 6.057 | 1552.1 | (M − H)− |
| PP1983 | FA | 6.357 | 1565.7 | (M − H)− |
| PP1984 | FA | 6.657 | 1541.3 | (M − H)− |
| PP1985 | FA | 6.323 | 1565.9 | (M − H)− |
| PP1987 | FA | 6.055 | 1551.9 | (M − H)− |
| PP1988 | FA | 6.156 | 1562.1 | (M − H)− |
| PP1989 | FA | 6.504 | 1559.9 | (M − H)− |
| PP1990 | FA | 5.951 | 1532.0 | (M − H)− |
| PP1991 | FA | 6.535 | 1554.1 | (M − H)− |
| PP1992 | FA | 6.265 | 1545.9 | (M − H)− |
| PP1993 | FA | 6.243 | 1539.9 | (M − H)− |
| PP1994 | FA | 6.103 | 1544.0 | (M − H)− |
| PP1995 | FA | 6.503 | 1553.7 | (M − H)− |
| PP1996 | FA | 6.043 | 1544.3 | (M − H)− |
| PP1997 | FA | 6.241 | 1539.7 | (M − H)− |
| PP1998 | FA | 6.347 | 1557.8 | (M − H)− |
| PP1999 | FA | 6.043 | 1539.4 | (M − H)− |
| PP2000 | FA | 6.235 | 1537.8 | (M − H)− |
| PP2001 | FA | 6.331 | 1553.5 | (M − H)− |
| PP2002 | FA | 6.263 | 1531.6 | (M − H)− |
| PP2003 | FA | 6.345 | 1523.9 | (M − H)− |
| PP2004 | FA | 5.963 | 1518.0 | (M − H)− |
| PP2005 | FA | 6.083 | 1509.4 | (M − H)− |
| PP2006 | AA | 7.963 | 1532.0 | (M − H)− |
| PP2007 | FA | 6.160 | 1521.9 | (M − H)− |
| PP2008 | FA | 6.516 | 1546.1 | (M − H)− |
| PP2009 | FA | 6.432 | 1535.4 | (M − H)− |
| PP2010 | AA | 7.924 | 1590.0 | (M − H)− |
| PP2011 | FA | 6.169 | 1521.9 | (M − H)− |
| PP2012 | FA | 6.400 | 1584.2 | (M − H)− |
| PP2013 | FA | 5.919 | 1561.4 | (M − H)− |
| PP2014 | FA | 6.096 | 1570.0 | (M − H)− |
| PP2015 | FA | 5.911 | 1555.4 | (M − H)− |
| PP2016 | FA | 5.856 | 1555.4 | (M − H)− |
| PP2017 | FA | 6.175 | 1569.8 | (M − H)− |
| PP2018 | FA | 5.735 | 1555.7 | (M − H)− |
| PP2019 | FA | 5.725 | 1525.9 | (M − H)− |
| PP2020 | AA | 7.812 | 1540.0 | (M − H)− |
| PP2021 | FA | 5.557 | 1524.1 | (M − H)− |
| PP2022 | FA | 5.809 | 1537.9 | (M − H)− |
| PP2023 | FA | 6.128 | 1552.1 | (M − H)− |
| PP2024 | FA | 6.025 | 1531.8 | (M − H)− |
| PP2025 | FA | 6.019 | 1525.9 | (M − H)− |
| PP2026 | FA | 5.721 | 1511.8 | (M − H)− |
| PP2027 | FA | 5.983 | 1526.1 | (M − H)− |
| PP2028 | FA | 6.287 | 1539.7 | (M − H)− |
| PP2029 | FA | 5.825 | 1525.8 | (M − H)− |
| PP2030 | AA | 8.088 | 1596.1 | (M − H)− |
| PP2031 | FA | 6.628 | 1589.9 | (M − H)− |
| PP2032 | FA | 6.325 | 1575.8 | (M − H)− |
| PP2033 | FA | 6.448 | 1590.4 | (M − H)− |
| PP2034 | AA | 8.095 | 1560.1 | (M − H)− |
| PP2036 | FA | 6.291 | 1557.8 | (M − H)− |
| PP2037 | FA | 6.587 | 1572.1 | (M − H)− |
| PP2038 | FA | 6.544 | 1574.0 | (M + H)+ |
| PP2040 | FA | 6.715 | 1566.0 | (M − H)− |
| PP2041 | AA | 8.279 | 1560.1 | (M − H)− |
| PP2042 | FA | 6.479 | 1546.0 | (M − H)− |
| PP2043 | FA | 6.725 | 1559.8 | (M − H)− |
| PP2044 | FA | 6.200 | 1506.3 | (M − H)− |
| PP2045 | FA | 6.480 | 1558.3 | (M − H)− |
| PP2046 | AA | 7.969 | 1556.3 | (M − H)− |
| PP2047 | FA | 5.607 | 1464.3 | (M − H)− |
| PP2048 | FA | 5.901 | 1516.2 | (M − H)− |
| PP2049 | FA | 5.717 | 1515.6 | (M + H)+ |
| PP2050 | AA | 8.169 | 1551.0 | (M + NH4)+ |
| PP2051 | AA | 7.737 | 1550.3 | (M − H)− |
| PP2052 | FA | 6.320 | 1530.3 | (M − H)− |
| PP2053 | AA | 7.919 | 1566.4 | (M + H)+ |
| PP2054 | FA | 6.223 | 1533.3 | (M + NH4)+ |
| PP2055 | FA | 6.137 | 1539.2 | (M + NH4)+ |
| PP2056 | AA | 7.997 | 1526.4 | (M − H)− |
| PP2057 | FA | 6.435 | 1552.7 | (M + NH4)+ |
| PP2058 | AA | 8.039 | 1526.4 | (M − H)− |
| PP2059 | FA | 5.801 | 1536.4 | (M − H)− |
| PP2060 | FA | 6.108 | 1524.3 | (M − H)− |
| PP2061 | FA | 5.639 | 1492.3 | (M − H)− |
| PP2062 | FA | 6.319 | 1533.9 | (M − H)− |
| PP2063 | AA | 7.685 | 1506.3 | (M − H)− |
| PP2064 | AA | 7.968 | 1494.4 | (M − H)− |
| PP2065 | FA | 5.737 | 1496.2 | (M − H)− |
| PP2066 | FA | 6.035 | 1530.3 | (M + H)+ |
| PP2067 | FA | 6.044 | 1510.4 | (M − H)− |
| PP2068 | FA | 5.948 | 1489.7 | (M + H)+ |
| PP2069 | FA | 5.559 | 1495.6 | (M + H)+ |
| PP2070 | FA | 5.851 | 1508.4 | (M − H)− |
| PP2071 | FA | 5.831 | 1508.4 | (M − H)− |
| PP2072 | FA | 6.136 | 1522.3 | (M − H)− |
| PP2073 | FA | 6.179 | 1558.2 | (M + H)+ |
| PP2074 | FA | 6.485 | 1572.4 | (M + H)+ |
| PP2075 | FA | 6.400 | 1527.7 | (M + H)+ |
| PP2076 | FA | 6.689 | 1540.3 | (M − H)− |
| PP2077 | AA | 7.863 | 1530.6 | (M + NH4)+ |
| PP2078 | FA | 5.973 | 1521.1 | (M + NH4)+ |
| PP2079 | FA | 6.275 | 1516.2 | (M − H)− |
| PP2080 | AA | 7.699 | 1500.3 | (M − H)− |
| PP2081 | FA | 6.093 | 1515.6 | (M + H)+ |
| PP2082 | FA | 6.048 | 1514.2 | (M − H)− |
| PP2083 | AA | 8.031 | 1528.2 | (M − H)− |
| PP2087 | AA | 7.925 | 1557.6 | (M + H)+ |
| PP2091 | FA | 6.004 | 1569.2 | (M + NH4)+ |
| PP2093 | FA | 6.337 | 1520.2 | (M + H)+ |
| PP2094 | FA | 6.387 | 1518.4 | (M − H)− |
| PP2095 | FA | 6.199 | 1516.3 | (M − H)− |
| PP2096 | AA | 7.893 | 1502.4 | (M + H)+ |
| PP2097 | FA | 6.113 | 1531.3 | (M + NH4)+ |

TABLE 36-continued

| Compound No. | Analytical condition | Retention time (min) | MS Found (m/z) | MS polarity |
|---|---|---|---|---|
| PP2098 | FA | 6.149 | 1512.3 | (M − H)− |
| PP2099 | FA | 5.964 | 1510.3 | (M − H)− |
| PP2101 | FA | 6.448 | 1574.4 | (M + H)+ |
| PP2102 | FA | 6.528 | 1572.4 | (M − H)− |
| PP2103 | FA | 6.379 | 1570.3 | (M − H)− |
| PP2105 | FA | 6.224 | 1568.2 | (M + H)+ |
| PP2106 | FA | 6.301 | 1566.4 | (M − H)− |
| PP2107 | FA | 6.129 | 1566.3 | (M + H)+ |
| PP2108 | AA | 8.140 | 1522.4 | (M + H)+ |
| PP2109 | FA | 6.515 | 1532.3 | (M − H)− |
| PP2117 | FA | 5.437 | 1492.0 | (M + H)+ |
| PP2118 | FA | 5.233 | 1484.0 | (M − H)− |
| PP2119 | FA | 6.471 | 1560.0 | (M − H)− |
| PP2120 | FA | 6.548 | 1484.1 | (M − H)− |
| PP2121 | FA | 6.183 | 1550.0 | (M − H)− |
| PP2122 | AA | 8.148 | 1457.8 | (M − H)− |
| PP2123 | FA | 6.328 | 1576.0 | (M − H)− |
| PP2124 | FA | 6.539 | 1558.0 | (M − H)− |
| PP2125 | FA | 6.475 | 1548.2 | (M − H)− |
| PP2126 | FA | 6.260 | 1548.0 | (M − H)− |
| PP2127 | FA | 6.515 | 1562.2 | (M − H)− |
| PP2128 | FA | 6.421 | 1573.8 | (M − H)− |
| PP2130 | FA | 6.559 | 1546.0 | (M − H)− |
| PP2131 | FA | 6.344 | 1546.2 | (M − H)− |
| PP2132 | FA | 6.617 | 1560.1 | (M − H)− |
| PP2133 | FA | 6.643 | 1575.6 | (M + H)+ |
| PP2135 | FA | 6.527 | 1548.2 | (M − H)− |
| PP2137 | FA | 6.264 | 1506.0 | (M − H)− |
| PP2138 | FA | 6.737 | 1572.1 | (M − H)− |
| PP2139 | FA | 6.128 | 1522.1 | (M − H)− |
| PP2140 | FA | 6.619 | 1546.1 | (M − H)− |
| PP2141 | AA | 8.064 | 1508.1 | (M − H)− |
| PP2142 | FA | 6.356 | 1506.4 | (M + H)+ |
| PP2143 | FA | 5.965 | 1467.6 | (M + H)+ |
| PP2144 | FA | 6.235 | 1520.1 | (M − H)− |
| PP2145 | FA | 6.123 | 1492.1 | (M − H)− |
| PP2146 | FA | 6.371 | 1492.3 | (M − H)− |
| PP2147 | FA | 6.179 | 1480.1 | (M − H)− |
| PP2148 | FA | 6.455 | 1506.0 | (M − H)− |
| PP2149 | FA | 6.333 | 1507.5 | (M + H)+ |
| PP2150 | FA | 6.052 | 1465.5 | (M + H)+ |
| PP2151 | FA | 6.477 | 1520.1 | (M − H)− |
| PP2152 | FA | 6.217 | 1492.3 | (M + H)+ |
| PP2153 | FA | 6.348 | 1494.3 | (M − H)− |
| PP2154 | FA | 6.268 | 1478.0 | (M − H)− |
| PP2155 | FA | 6.196 | 1554.2 | (M − H)− |
| PP2156 | FA | 6.569 | 1518.1 | (M − H)− |
| PP2157 | FA | 5.897 | 1544.2 | (M − H)− |
| PP2158 | FA | 6.436 | 1491.6 | (M − H)− |
| PP2159 | FA | 6.051 | 1570.1 | (M − H)− |
| PP2160 | FA | 6.208 | 1542.0 | (M − H)− |
| PP2161 | FA | 6.305 | 1556.3 | (M − H)− |
| PP2163 | FA | 6.059 | 1542.0 | (M + H)+ |
| PP2164 | FA | 6.420 | 1568.1 | (M − H)− |
| PP2165 | FA | 6.240 | 1541.6 | (M − H)− |
| PP2166 | FA | 6.016 | 1500.1 | (M − H)− |
| PP2167 | FA | 5.856 | 1516.1 | (M − H)− |
| PP2168 | FA | 6.141 | 1502.3 | (M − H)− |
| PP2169 | FA | 5.837 | 1486.3 | (M − H)− |
| PP2170 | FA | 5.887 | 1473.6 | (M − H)− |
| PP2171 | FA | 6.041 | 1500.2 | (M − H)− |
| PP2172 | FA | 6.257 | 1514.2 | (M − H)− |
| PP2173 | FA | 6.057 | 1488.3 | (M − H)− |
| PP2174 | AA | 8.243 | 1539.9 | (M − H)− |
| PP2175 | FA | 6.547 | 1513.9 | (M + H)+ |
| PP2176 | FA | 6.596 | 1525.8 | (M − H)− |
| PP2178 | FA | 6.428 | 1511.4 | (M + H)+ |
| PP2179 | FA | 6.492 | 1498.1 | (M − H)− |
| PP2180 | FA | 6.719 | 1538.1 | (M − H)− |
| PP2181 | AA | 8.216 | 1512.1 | (M − H)− |
| PP2182 | FA | 6.329 | 1469.8 | (M − H)− |
| PP2183 | FA | 6.216 | 1487.5 | (M + H)+ |
| PP2184 | FA | 6.344 | 1459.5 | (M + H)+ |
| PP2185 | FA | 6.421 | 1471.9 | (M − H)− |
| PP2186 | FA | 6.023 | 1429.8 | (M − H)− |
| PP2187 | FA | 6.201 | 1455.9 | (M − H)− |
| PP2188 | FA | 6.257 | 1443.8 | (M − H)− |
| PP2189 | FA | 5.912 | 1461.5 | (M − H)− |
| PP2190 | FA | 6.111 | 1489.7 | (M − H)− |
| PP2191 | FA | 6.179 | 1476.1 | (M − H)− |
| PP2192 | FA | 6.049 | 1516.2 | (M − H)− |
| PP2193 | AA | 8.176 | 1490.3 | (M − H)− |
| PP2195 | FA | 5.952 | 1490.0 | (M − H)− |
| PP2196 | FA | 6.337 | 1504.0 | (M − H)− |
| PP2197 | FA | 5.652 | 1486.1 | (M − H)− |
| PP2198 | FA | 6.151 | 1502.1 | (M − H)− |
| PP2199 | SQD | 1.050 | 1493.9 | (M + H)+ |
| PP2200 | FA | 6.428 | 1492.1 | (M − H)− |
| PP2202 | FA | 6.291 | 1491.8 | (M − H)− |
| PP2203 | FA | 6.717 | 1520.3 | (M − H)− |
| PP2207 | FA | 6.516 | 1505.8 | (M − H)− |
| PP2208 | FA | 6.365 | 1476.0 | (M − H)− |
| PP2209 | FA | 6.325 | 1504.1 | (M − H)− |
| PP2210 | FA | 6.120 | 1459.7 | (M − H)− |
| PP2212 | FA | 6.379 | 1474.0 | (M − H)− |
| PP2214 | FA | 6.671 | 1488.1 | (M − H)− |
| PP2216 | AA | 7.876 | 1462.2 | (M − H)− |
| PP2218 | FA | 6.152 | 1493.5 | (M + H)+ |
| PP2219 | FA | 6.275 | 1492.0 | (M − H)− |
| PP2220 | FA | 5.949 | 1462.2 | (M − H)− |
| PP2221 | FA | 6.096 | 1489.8 | (M − H)− |
| PP2222 | FA | 6.188 | 1480.0 | (M + H)+ |
| PP2223 | FA | 6.203 | 1476.2 | (M − H)− |
| PP2224 | FA | 6.073 | 1496.6 | (M + NH$_4$)+ |
| PP2225 | FA | 5.904 | 1478.0 | (M − H)− |
| PP2226 | AA | 7.797 | 1503.9 | (M − H)− |
| PP2227 | FA | 6.089 | 1462.0 | (M − H)− |
| PP2229 | FA | 6.440 | 1506.2 | (M − H)− |
| PP2230 | AA | 8.119 | 1491.6 | (M − H)− |
| PP2231 | FA | 6.232 | 1475.7 | (M − H)− |
| PP2232 | FA | 6.200 | 1492.0 | (M − H)− |
| PP2233 | FA | 5.851 | 1448.0 | (M − H)− |
| PP2234 | FA | 6.285 | 1490.0 | (M − H)− |
| PP2235 | FA | 6.537 | 1504.0 | (M − H)− |
| PP2237 | FA | 5.869 | 1445.6 | (M − H)− |
| PP2238 | FA | 6.157 | 1460.0 | (M − H)− |
| PP2242 | FA | 5.483 | 1458.2 | (M − H)− |
| PP2257 | FA | 6.225 | 1490.0 | (M − H)− |
| PP2259 | FA | 5.783 | 1511.9 | (M − H)− |
| PP2260 | AA | 7.825 | 1526.2 | (M − H)− |
| PP2261 | AA | 7.179 | 1476.2 | (M − H)− |
| PP2262 | FA | 4.957 | 1470.2 | (M − H)− |
| PP2263 | FA | 5.505 | 1497.5 | (M − H)− |
| PP2264 | FA | 5.225 | 1483.8 | (M − H)− |
| PP2268 | FA | 6.137 | 1515.9 | (M − H)− |
| PP2269 | FA | 5.912 | 1512.3 | (M − H)− |
| PP2270 | FA | 6.419 | 1513.8 | (M − H)− |
| PP2271 | FA | 6.111 | 1521.0 | (M + NH$_4$)+ |
| PP2272 | FA | 6.377 | 1515.6 | (M − H)− |
| PP2273 | FA | 6.372 | 1516.0 | (M − H)− |
| PP2275 | AA | 8.187 | 1543.8 | (M − H)− |
| PP2312 | FA | 5.669 | 1525.8 | (M − H)− |
| PP2313 | FA | 6.263 | 1554.1 | (M − H)− |
| PP2314 | FA | 5.736 | 1556.2 | (M − H)− |
| PP2315 | FA | 6.072 | 1570.3 | (M − H)− |
| PP2316 | FA | 6.085 | 1552.1 | (M − H)− |
| PP2317 | FA | 6.079 | 1554.1 | (M − H)− |
| PP2318 | FA | 6.163 | 1582.1 | (M − H)− |
| PP2319 | FA | 5.867 | 1569.7 | (M − H)− |
| PP2320 | FA | 5.915 | 1551.5 | (M − H)− |
| PP2322 | FA | 5.975 | 1582.2 | (M − H)− |
| PP2323 | FA | 5.815 | 1504.3 | (M − H)− |
| PP2325 | FA | 6.177 | 1500.1 | (M − H)− |
| PP2326 | FA | 5.604 | 1502.1 | (M − H)− |
| PP2327 | FA | 6.269 | 1530.2 | (M − H)− |
| PP2328 | FA | 5.995 | 1498.1 | (M − H)− |
| PP2329 | AA | 7.744 | 1500.1 | (M − H)− |
| PP2330 | FA | 6.083 | 1527.7 | (M − H)− |
| PP2331 | FA | 6.067 | 1529.9 | (M − H)− |
| PP2332 | FA | 5.804 | 1498.2 | (M − H)− |
| PP2333 | FA | 6.072 | 1465.7 | (M − H)− |
| PP2334 | FA | 5.879 | 1530.3 | (M + H)+ |

TABLE 36-continued

| Compound No. | Analytical condition | Retention time (min) | MS Found (m/z) | MS polarity |
|---|---|---|---|---|
| PP2335 | FA | 5.727 | 1468.1 | (M − H)− |
| PP2336 | FA | 5.760 | 1463.7 | (M − H)− |
| PP2337 | FA | 6.515 | 1492.3 | (M − H)− |
| PP2338 | FA | 5.619 | 1480.3 | (M − H)− |
| PP2339 | FA | 6.144 | 1494.3 | (M − H)− |
| PP2340 | FA | 6.223 | 1490.3 | (M − H)− |
| PP2341 | FA | 6.401 | 1492.3 | (M − H)− |
| PP2342 | FA | 6.079 | 1506.3 | (M − H)− |
| PP2344 | FA | 6.100 | 1490.1 | (M − H)− |
| PP2345 | FA | 5.720 | 1502.1 | (M − H)− |
| PP2347 | FA | 5.556 | 1518.1 | (M − H)− |
| PP2348 | AA | 7.396 | 1500.2 | (M − H)− |
| PP2349 | FA | 6.140 | 1528.3 | (M − H)− |
| PP2350 | FA | 5.516 | 1530.3 | (M − H)− |
| PP2351 | FA | 5.944 | 1544.1 | (M − H)− |
| PP2352 | FA | 5.843 | 1526.3 | (M − H)− |
| PP2353 | FA | 5.949 | 1528.3 | (M − H)− |
| PP2354 | FA | 5.933 | 1556.1 | (M − H)− |
| PP2355 | FA | 5.833 | 1544.3 | (M − H)− |
| PP2356 | FA | 5.648 | 1526.3 | (M − H)− |
| PP2357 | FA | 5.793 | 1556.3 | (M − H)− |
| PP2358 | FA | 5.732 | 1496.2 | (M − H)− |
| PP2359 | FA | 5.541 | 1511.6 | (M − H)− |
| PP2360 | FA | 6.183 | 1522.1 | (M − H)− |
| PP2361 | FA | 5.952 | 1538.0 | (M − H)− |
| PP2362 | FA | 5.984 | 1521.6 | (M − H)− |
| PP2363 | FA | 5.741 | 1538.0 | (M − H)− |
| PP2364 | FA | 5.613 | 1442.4 | (M − H)− |
| PP2365 | FA | 5.701 | 1472.2 | (M − H)− |
| PP2366 | FA | 6.071 | 1467.6 | (M − H)− |
| PP2367 | FA | 6.167 | 1498.1 | (M − H)− |
| PP2368 | FA | 5.865 | 1467.6 | (M − H)− |
| PP2369 | FA | 5.947 | 1498.1 | (M − H)− |
| PP2370 | FA | 5.848 | 1435.6 | (M + H)+ |
| PP2371 | FA | 5.727 | 1449.9 | (M − H)− |
| PP2372 | FA | 6.309 | 1461.6 | (M + H)+ |
| PP2373 | FA | 6.181 | 1476.3 | (M − H)− |
| PP2374 | FA | 6.204 | 1460.2 | (M − H)− |
| PP2375 | FA | 6.143 | 1476.1 | (M − H)− |
| PP2376 | FA | 5.533 | 1471.4 | (M + H)+ |
| PP2377 | FA | 5.659 | 1500.1 | (M − H)− |
| PP2378 | FA | 5.952 | 1495.6 | (M − H)− |
| PP2379 | FA | 6.071 | 1526.1 | (M − H)− |
| PP2380 | FA | 5.785 | 1496.2 | (M − H)− |
| PP2381 | FA | 5.957 | 1526.3 | (M − H)− |
| PP2382 | FA | 5.837 | 1527.6 | (M − H)− |
| PP2383 | FA | 5.655 | 1543.6 | (M − H)− |
| PP2385 | FA | 5.567 | 1458.2 | (M − H)− |
| PP2386 | FA | 6.048 | 1498.1 | (M − H)− |
| PP2387 | FA | 5.480 | 1459.5 | (M + H)+ |
| PP2388 | AA | 7.869 | 1512.3 | (M − H)− |
| PP2389 | FA | 5.765 | 1491.6 | (M − H)− |
| PP2390 | FA | 5.676 | 1514.3 | (M − H)− |
| PP2391 | FA | 5.680 | 1494.0 | (M − H)− |
| PP2392 | FA | 5.712 | 1502.2 | (M − H)− |
| PP2393 | FA | 5.713 | 1472.0 | (M − H)− |
| PP2394 | FA | 6.085 | 1476.1 | (M − H)− |
| PP2395 | FA | 5.945 | 1505.7 | (M − H)− |
| PP2396 | FA | 5.956 | 1508.2 | (M − H)− |
| PP2397 | FA | 5.856 | 1508.1 | (M − H)− |
| PP2398 | FA | 6.004 | 1516.3 | (M − H)− |
| PP2399 | FA | 6.469 | 1489.9 | (M − H)− |
| PP2400 | FA | 6.347 | 1520.1 | (M − H)− |
| PP2401 | FA | 6.233 | 1519.9 | (M − H)− |
| PP2402 | AA | 8.067 | 1520.1 | (M − H)− |
| PP2403 | FA | 6.264 | 1522.0 | (M − H)− |
| PP2404 | FA | 6.144 | 1522.3 | (M − H)− |
| PP2405 | FA | 6.316 | 1500.1 | (M − H)− |
| PP2406 | FA | 6.209 | 1530.3 | (M − H)− |
| PP2407 | FA | 6.561 | 1506.3 | (M − H)− |
| PP2408 | FA | 6.448 | 1536.3 | (M − H)− |
| PP2409 | FA | 6.293 | 1496.1 | (M − H)− |
| PP2410 | FA | 6.555 | 1510.1 | (M − H)− |
| PP2411 | FA | 6.768 | 1516.3 | (M − H)− |
| PP2412 | FA | 5.867 | 1486.3 | (M − H)− |
| PP2413 | AA | 7.915 | 1500.3 | (M − H)− |
| PP2414 | FA | 6.355 | 1506.3 | (M − H)− |
| PP2415 | FA | 6.167 | 1500.0 | (M − H)− |
| PP2416 | FA | 6.440 | 1514.1 | (M − H)− |
| PP2417 | FA | 6.657 | 1520.3 | (M − H)− |
| PP2418 | FA | 6.000 | 1512.0 | (M − H)− |
| PP2419 | FA | 6.255 | 1526.4 | (M − H)− |
| PP2422 | FA | 6.067 | 1508.3 | (M − H)− |
| PP2423 | FA | 6.105 | 1516.1 | (M − H)− |
| PP2424 | FA | 6.343 | 1522.2 | (M − H)− |
| PP2425 | FA | 6.133 | 1516.1 | (M − H)− |
| PP2426 | FA | 6.381 | 1521.7 | (M − H)− |
| PP2427 | FA | 6.175 | 1512.2 | (M − H)− |
| PP2428 | FA | 6.288 | 1548.1 | (M − H)− |
| PP2429 | FA | 6.461 | 1526.3 | (M − H)− |
| PP2430 | FA | 6.649 | 1532.1 | (M − H)− |
| PP2431 | FA | 6.228 | 1542.3 | (M − H)− |
| PP2432 | FA | 6.343 | 1578.1 | (M − H)− |
| PP2433 | FA | 5.944 | 1528.3 | (M − H)− |
| PP2436 | FA | 6.401 | 1578.1 | (M − H)− |
| PP2437 | FA | 6.081 | 1478.2 | (M − H)− |
| PP2438 | FA | 5.696 | 1518.3 | (M − H)− |
| PP2439 | FA | 5.992 | 1478.0 | (M − H)− |
| PP2440 | FA | 5.971 | 1524.0 | (M − H)− |
| PP2441 | FA | 6.119 | 1486.3 | (M − H)− |
| PP2442 | FA | 5.893 | 1488.0 | (M − H)− |
| PP2443 | AA | 7.855 | 1486.1 | (M − H)− |
| PP2444 | FA | 6.069 | 1522.0 | (M − H)− |
| PP2445 | FA | 5.901 | 1516.1 | (M − H)− |
| PP2446 | FA | 5.843 | 1532.3 | (M − H)− |
| PP2447 | FA | 6.027 | 1486.3 | (M − H)− |
| PP2448 | FA | 6.199 | 1494.0 | (M − H)− |
| PP2449 | FA | 5.901 | 1516.1 | (M − H)− |
| PP2450 | FA | 6.088 | 1537.7 | (M − H)− |
| PP2451 | FA | 6.357 | 1490.0 | (M − H)− |
| PP2452 | FA | 6.120 | 1482.3 | (M − H)− |
| PP2453 | FA | 6.344 | 1490.0 | (M − H)− |
| PP2454 | AA | 7.987 | 1515.6 | (M + Na)+ |
| PP2455 | FA | 6.375 | 1492.2 | (M − H)− |
| PP2456 | FA | 6.444 | 1488.2 | (M − H)− |
| PP2457 | FA | 6.268 | 1492.2 | (M − H)− |
| PP2458 | FA | 6.033 | 1521.1 | (M + NH$_4$)+ |
| PP2460 | FA | 6.188 | 1537.6 | (M + H)+ |
| PP2461 | FA | 6.292 | 1500.1 | (M − H)− |
| PP2462 | FA | 6.317 | 1508.0 | (M − H)− |
| PP2463 | FA | 6.180 | 1530.3 | (M − H)− |
| PP2464 | FA | 6.079 | 1546.1 | (M − H)− |
| PP2465 | FA | 6.641 | 1504.3 | (M − H)− |
| PP2466 | FA | 6.329 | 1452.1 | (M − H)− |
| PP2467 | FA | 6.623 | 1504.0 | (M − H)− |
| PP2468 | FA | 6.528 | 1486.1 | (M − H)− |
| PP2469 | FA | 6.496 | 1534.1 | (M − H)− |
| PP2470 | FA | 6.261 | 1496.3 | (M − H)− |
| PP2471 | FA | 6.527 | 1506.0 | (M − H)− |
| PP2472 | FA | 6.329 | 1553.5 | (M + H)+ |
| PP2475 | FA | 6.420 | 1506.1 | (M − H)− |
| PP2477 | FA | 6.051 | 1516.1 | (M − H)− |
| PP2479 | FA | 6.560 | 1502.2 | (M − H)− |
| PP2480 | FA | 6.015 | 1528.1 | (M − H)− |
| PP2481 | FA | 6.349 | 1522.3 | (M − H)− |
| PP2482 | FA | 6.031 | 1516.1 | (M − H)− |
| PP2483 | FA | 6.284 | 1516.1 | (M − H)− |
| PP2484 | FA | 6.419 | 1550.3 | (M − H)− |
| PP2485 | FA | 6.277 | 1534.3 | (M − H)− |
| PP2488 | FA | 6.636 | 1499.9 | (M − H)− |
| PP2489 | FA | 6.291 | 1522.3 | (M − H)− |
| PP2490 | FA | 6.557 | 1522.2 | (M − H)− |
| PP2492 | FA | 6.443 | 1520.1 | (M − H)− |
| PP2494 | FA | 6.144 | 1498.0 | (M − H)− |
| PP2495 | FA | 6.365 | 1532.1 | (M − H)− |
| PP2496 | FA | 6.445 | 1492.2 | (M − H)− |
| PP2497 | FA | 6.173 | 1486.2 | (M − H)− |
| PP2498 | FA | 6.389 | 1520.0 | (M − H)− |
| PP2499 | FA | 6.653 | 1538.7 | (M + NH$_4$)+ |
| PP2500 | FA | 6.413 | 1504.2 | (M − H)− |
| PP2501 | FA | 6.792 | 1516.0 | (M − H)− |
| PP2502 | FA | 5.905 | 1461.5 | (M − H)− |

TABLE 36-continued

| Compound No. | Analytical condition | Retention time (min) | MS Found (m/z) | MS polarity |
|---|---|---|---|---|
| PP2504 | FA | 5.835 | 1472.0 | (M − H)− |
| PP2505 | FA | 5.751 | 1472.3 | (M − H)− |
| PP2506 | FA | 6.181 | 1476.0 | (M − H)− |
| PP2507 | FA | 6.049 | 1505.8 | (M − H)− |
| PP2508 | FA | 6.423 | 1518.1 | (M − H)− |
| PP2509 | FA | 6.675 | 1501.4 | (M + H)+ |
| PP2510 | FA | 6.232 | 1512.3 | (M − H)− |
| PP2511 | FA | 6.667 | 1525.7 | (M − H)− |
| PP2512 | FA | 6.260 | 1535.2 | (M + NH4)+ |
| PP2513 | FA | 6.736 | 1490.1 | (M − H)− |
| PP2514 | FA | 6.031 | 1510.1 | (M − H)− |
| PP2515 | FA | 7.073 | 1528.3 | (M − H)− |
| PP2516 | FA | 6.308 | 1506.0 | (M − H)− |
| PP2517 | AA | 8.683 | 1493.5 | (M + H)+ |
| PP2518 | FA | 6.089 | 1500.3 | (M − H)− |
| PP2519 | FA | 6.536 | 1560.1 | (M − H)− |
| PP2520 | FA | 6.271 | 1536.0 | (M − H)− |
| PP2521 | FA | 6.595 | 1523.8 | (M − H)− |
| PP2522 | FA | 6.052 | 1530.3 | (M − H)− |
| PP2523 | FA | 6.567 | 1564.3 | (M − H)− |
| PP2524 | FA | 6.511 | 1516.0 | (M − H)− |
| PP2525 | AA | 8.288 | 1527.9 | (M − H)− |
| PP2526 | FA | 6.335 | 1514.1 | (M − H)− |
| PP2527 | FA | 6.607 | 1556.1 | (M − H)− |
| PP2528 | FA | 6.383 | 1504.0 | (M − H)− |
| PP2529 | FA | 6.775 | 1569.6 | (M − H)− |
| PP2530 | FA | 6.353 | 1535.6 | (M + H)+ |
| PP2531 | AA | 7.967 | 1494.2 | (M − H)− |
| PP2532 | FA | 5.975 | 1490.0 | (M − H)− |
| PP2533 | AA | 8.221 | 1551.4 | (M + Na)+ |
| PP2534 | FA | 5.771 | 1483.6 | (M − H)− |
| PP2535 | FA | 6.479 | 1507.9 | (M − H)− |
| PP2536 | FA | 5.785 | 1488.2 | (M − H)− |
| PP2537 | FA | 6.576 | 1473.5 | (M + H)+ |
| PP2539 | FA | 5.839 | 1478.0 | (M − H)− |
| PP2540 | FA | 5.611 | 1472.2 | (M − H)− |
| PP2541 | FA | 5.761 | 1508.0 | (M − H)− |
| PP2542 | FA | 5.539 | 1504.0 | (M + H)+ |
| PP2543 | FA | 6.053 | 1488.2 | (M − H)− |
| PP2545 | FA | 5.907 | 1476.0 | (M − H)− |
| PP2546 | FA | 5.848 | 1505.9 | (M − H)− |
| PP2547 | FA | 5.577 | 1522.4 | (M + H)+ |
| PP2548 | FA | 5.375 | 1515.5 | (M + H)+ |
| PP2549 | FA | 5.660 | 1517.8 | (M − H)− |
| PP2550 | FA | 5.645 | 1520.3 | (M − H)− |
| PP2551 | FA | 5.425 | 1514.1 | (M − H)− |
| PP2552 | FA | 5.731 | 1520.0 | (M + H)+ |
| PP2553 | FA | 6.060 | 1550.0 | (M + H)+ |
| PP2554 | FA | 5.857 | 1542.3 | (M − H)− |
| PP2555 | AA | 8.049 | 1545.9 | (M − H)− |
| PP2556 | FA | 6.125 | 1548.0 | (M − H)− |
| PP2557 | FA | 5.904 | 1542.4 | (M − H)− |
| PP2558 | FA | 6.207 | 1546.1 | (M − H)− |
| PP2559 | FA | 6.451 | 1483.5 | (M + H)+ |
| PP2560 | FA | 6.704 | 1521.7 | (M + H)+ |
| PP2561 | FA | 6.779 | 1503.3 | (M + NH4)+ |
| PP2562 | AA | 8.208 | 1512.2 | (M − H)− |
| PP2563 | FA | 6.537 | 1477.4 | (M + H)+ |
| PP2564 | FA | 6.908 | 1514.1 | (M − H)− |
| PP2565 | AA | 8.583 | 1477.9 | (M − H)− |
| PP2566 | FA | 6.360 | 1545.7 | (M − H)− |
| PP2567 | FA | 6.395 | 1528.9 | (M + NH4)+ |
| PP2568 | FA | 6.393 | 1550.3 | (M − H)− |
| PP2569 | FA | 6.500 | 1515.4 | (M + H)+ |
| PP2570 | FA | 6.608 | 1531.9 | (M − H)− |
| PP2571 | FA | 6.656 | 1497.4 | (M + H)+ |
| PP2572 | FA | 6.575 | 1536.3 | (M − H)− |
| PP2573 | FA | 6.411 | 1560.5 | (M + NH4)+ |
| PP2574 | FA | 5.873 | 1528.2 | (M − H)− |
| PP2575 | FA | 5.852 | 1504.0 | (M − H)− |
| PP2576 | FA | 5.976 | 1530.3 | (M − H)− |
| PP2577 | FA | 6.103 | 1481.4 | (M + H)+ |
| PP2578 | FA | 6.511 | 1507.4 | (M + H)+ |
| PP2579 | AA | 7.833 | 1510.8 | (M + NH4)+ |
| PP2580 | FA | 5.911 | 1486.5 | (M + NH4)+ |
| PP2581 | FA | 6.063 | 1493.8 | (M − H)− |
| PP2583 | FA | 6.408 | 1554.0 | (M − H)− |
| PP2586 | FA | 5.509 | 1490.2 | (M − H)− |
| PP2588 | FA | 5.575 | 1496.5 | (M + NH4)+ |
| PP2589 | FA | 5.575 | 1455.5 | (M + H)+ |
| PP2590 | FA | 6.331 | 1512.6 | (M + NH4)+ |
| PP2591 | AA | 7.741 | 1498.9 | (M + NH4)+ |
| PP2592 | FA | 6.320 | 1512.4 | (M + NH4)+ |
| PP2593 | FA | 6.159 | 1507.9 | (M + H)+ |
| PP2594 | FA | 6.072 | 1537.2 | (M + NH4)+ |
| PP2595 | FA | 6.320 | 1512.9 | (M + NH4)+ |
| PP2596 | AA | 7.975 | 1505.9 | (M − H)− |
| PP2597 | FA | 6.147 | 1493.5 | (M + H)+ |
| PP2598 | FA | 6.247 | 1492.2 | (M − H)− |
| PP2600 | FA | 5.611 | 1460.0 | (M − H)− |
| PP2601 | FA | 5.824 | 1436.1 | (M − H)− |
| PP2602 | FA | 5.676 | 1447.5 | (M − H)− |
| PP2603 | FA | 5.659 | 1425.4 | (M + H)+ |
| PP2604 | FA | 5.825 | 1449.8 | (M − H)− |
| PP2605 | FA | 6.024 | 1481.4 | (M + H)+ |
| PP2606 | FA | 6.780 | 1590.0 | (M − H)− |
| PP2608 | FA | 6.968 | 1604.3 | (M − H)− |
| PP2610 | FA | 6.911 | 1555.4 | (M + H)+ |
| PP2612 | FA | 7.109 | 1569.5 | (M + H)+ |
| PP2614 | FA | 6.735 | 1544.2 | (M − H)− |
| PP2615 | FA | 6.716 | 1576.3 | (M − H)− |
| PP2616 | AA | 8.399 | 1507.9 | (M − H)− |
| PP2618 | FA | 6.788 | 1538.1 | (M − H)− |
| PP2619 | FA | 6.907 | 1562.3 | (M − H)− |
| PP2622 | FA | 6.337 | 1576.0 | (M + H)+ |
| PP2624 | FA | 6.415 | 1539.3 | (M + H)+ |
| PP2626 | FA | 6.607 | 1560.0 | (M − H)− |
| PP2627 | FA | 6.901 | 1589.9 | (M − H)− |
| PP2628 | FA | 6.701 | 1525.4 | (M + H)+ |
| PP2630 | FA | 7.033 | 1552.1 | (M − H)− |
| PP2631 | FA | 6.556 | 1584.3 | (M − H)− |
| PP2633 | FA | 6.759 | 1598.3 | (M − H)− |
| PP2634 | AA | 8.184 | 1588.4 | (M − H)− |
| PP2635 | FA | 6.367 | 1539.9 | (M − H)− |
| PP2637 | FA | 6.407 | 1539.0 | (M + NH4)+ |
| PP2638 | AA | 8.244 | 1483.5 | (M − H)− |
| PP2639 | FA | 6.561 | 1554.1 | (M − H)− |
| PP2640 | FA | 6.580 | 1535.4 | (M + H)+ |
| PP2641 | AA | 8.371 | 1521.8 | (M + Na)+ |
| PP2642 | AA | 8.316 | 1539.8 | (M − H)− |
| PP2643 | FA | 6.620 | 1521.3 | (M + H)+ |
| PP2644 | AA | 8.369 | 1483.8 | (M − H)− |
| PP2645 | AA | 8.343 | 1566.0 | (M − H)− |
| PP2646 | AA | 8.264 | 1546.0 | (M − H)− |
| PP2648 | FA | 6.859 | 1555.4 | (M + H)+ |
| PP2649 | FA | 6.539 | 1537.5 | (M + H)+ |
| PP2650 | FA | 6.669 | 1501.7 | (M + H)+ |
| PP2651 | FA | 6.955 | 1581.8 | (M + H)+ |
| PP2652 | FA | 6.641 | 1561.9 | (M − H)− |
| PP2654 | FA | 6.395 | 1576.3 | (M − H)− |
| PP2655 | FA | 6.532 | 1588.3 | (M − H)− |
| PP2656 | FA | 6.759 | 1602.3 | (M − H)− |
| PP2657 | FA | 6.544 | 1588.2 | (M − H)− |
| PP2659 | FA | 5.972 | 1508.2 | (M − H)− |
| PP2660 | FA | 6.180 | 1523.6 | (M + H)+ |
| PP2661 | FA | 6.263 | 1526.2 | (M − H)− |
| PP2662 | AA | 8.237 | 1540.0 | (M − H)− |
| PP2663 | FA | 6.691 | 1602.3 | (M − H)− |
| PP2664 | FA | 6.813 | 1614.3 | (M − H)− |
| PP2665 | FA | 7.031 | 1628.3 | (M − H)− |
| PP2666 | FA | 6.851 | 1614.3 | (M − H)− |
| PP2667 | FA | 7.024 | 1628.4 | (M − H)− |
| PP2668 | FA | 6.327 | 1534.2 | (M − H)− |
| PP2669 | FA | 6.523 | 1548.2 | (M − H)− |
| PP2670 | FA | 6.591 | 1553.4 | (M + H)+ |
| PP2671 | FA | 6.792 | 1567.6 | (M + H)+ |
| PP2672 | FA | 6.280 | 1496.3 | (M − H)− |
| PP2673 | FA | 5.659 | 1482.4 | (M − H)− |
| PP2674 | FA | 6.103 | 1476.1 | (M − H)− |
| PP2675 | FA | 5.731 | 1478.1 | (M − H)− |
| PP2676 | FA | 5.663 | 1482.2 | (M − H)− |
| PP2677 | FA | 5.977 | 1497.8 | (M − H)− |

TABLE 36-continued

| Compound No. | Analytical condition | Retention time (min) | MS Found (m/z) | MS polarity |
|---|---|---|---|---|
| PP2678 | FA | 5.521 | 1498.1 | (M − H)− |
| PP2679 | FA | 6.307 | 1537.7 | (M + H)+ |
| PP2681 | FA | 6.192 | 1509.7 | (M + H)+ |
| PP2683 | FA | 5.773 | 1459.7 | (M + H)+ |
| PP2684 | FA | 6.069 | 1476.2 | (M + H)+ |
| PP2685 | FA | 6.003 | 1454.4 | (M − H)− |
| PP2686 | FA | 5.817 | 1447.7 | (M + H)+ |
| PP2687 | FA | 6.243 | 1514.3 | (M − H)− |
| PP2688 | FA | 6.092 | 1518.2 | (M − H)− |
| PP2689 | FA | 6.059 | 1518.2 | (M − H)− |
| PP2690 | FA | 6.076 | 1550.3 | (M − H)− |
| PP2691 | FA | 6.247 | 1526.1 | (M − H)− |
| PP2692 | FA | 6.492 | 1528.4 | (M − H)− |
| PP2693 | FA | 5.804 | 1518.2 | (M + H)+ |
| PP2694 | FA | 5.616 | 1528.4 | (M − H)− |
| PP2695 | FA | 6.063 | 1581.3 | (M + NH$_4$)+ |
| PP2696 | FA | 6.275 | 1500.3 | (M − H)− |
| PP2697 | FA | 6.117 | 1504.2 | (M − H)− |
| PP2698 | FA | 6.124 | 1503.7 | (M − H)− |
| PP2699 | FA | 6.099 | 1535.6 | (M − H)− |
| PP2700 | FA | 6.255 | 1512.3 | (M − H)− |
| PP2701 | AA | 8.196 | 1514.3 | (M − H)− |
| PP2702 | FA | 5.807 | 1502.1 | (M − H)− |
| PP2703 | FA | 5.624 | 1532.5 | (M + NH$_4$)+ |
| PP2704 | FA | 6.109 | 1548.4 | (M − H)− |
| PP2706 | FA | 6.205 | 1494.3 | (M − H)− |
| PP2708 | FA | 6.340 | 1524.1 | (M − H)− |
| PP2710 | FA | 5.971 | 1488.1 | (M − H)− |
| PP2712 | FA | 6.123 | 1518.1 | (M − H)− |
| PP2714 | FA | 6.240 | 1460.3 | (M + H)+ |
| PP2716 | FA | 6.389 | 1487.7 | (M − H)− |
| PP2718 | FA | 6.499 | 1520.1 | (M − H)− |
| PP2720 | FA | 6.384 | 1535.7 | (M − H)− |
| PP2722 | FA | 6.277 | 1514.1 | (M − H)− |
| PP2724 | FA | 6.161 | 1530.3 | (M − H)− |
| PP2726 | FA | 6.551 | 1485.5 | (M + H)+ |
| PP2728 | FA | 6.440 | 1500.2 | (M − H)− |
| PP2730 | FA | 6.377 | 1548.2 | (M − H)− |
| PP2732 | AA | 8.056 | 1564.3 | (M − H)− |
| PP2734 | FA | 6.159 | 1542.2 | (M − H)− |
| PP2736 | FA | 6.053 | 1558.3 | (M − H)− |
| PP2738 | AA | 8.199 | 1512.0 | (M − H)− |
| PP2740 | FA | 6.332 | 1527.5 | (M − H)− |
| PP2742 | FA | 6.635 | 1574.3 | (M − H)− |
| PP2744 | FA | 6.369 | 1576.2 | (M − H)− |
| PP2746 | FA | 6.421 | 1568.1 | (M − H)− |
| PP2748 | FA | 6.137 | 1569.6 | (M − H)− |
| PP2749 | FA | 6.697 | 1539.4 | (M + H)+ |
| PP2750 | AA | 8.179 | 1540.1 | (M − H)− |
| PP2751 | FA | 6.053 | 1491.6 | (M − H)− |
| PP2752 | FA | 6.201 | 1521.6 | (M − H)− |
| PP2753 | FA | 5.839 | 1486.1 | (M − H)− |
| PP2754 | FA | 5.980 | 1516.3 | (M − H)− |
| PP2755 | FA | 6.071 | 1456.1 | (M − H)− |
| PP2756 | FA | 6.223 | 1486.1 | (M − H)− |
| PP2757 | FA | 6.379 | 1518.2 | (M − H)− |
| PP2760 | FA | 6.049 | 1527.6 | (M − H)− |
| PP2761 | AA | 8.205 | 1481.8 | (M − H)− |
| PP2762 | AA | 8.177 | 1498.0 | (M − H)− |
| PP2763 | FA | 6.123 | 1562.0 | (M − H)− |
| PP2764 | FA | 6.024 | 1542.0 | (M + H)+ |
| PP2765 | FA | 5.907 | 1556.3 | (M − H)− |
| PP2766 | FA | 6.264 | 1528.5 | (M + NH$_4$)+ |
| PP2767 | FA | 6.167 | 1525.5 | (M − H)− |
| PP2768 | FA | 6.520 | 1572.3 | (M − H)− |
| PP2769 | FA | 6.240 | 1574.0 | (M − H)− |
| PP2770 | FA | 6.315 | 1566.3 | (M − H)− |
| PP2771 | FA | 6.020 | 1568.3 | (M − H)− |
| PP2772 | FA | 6.023 | 1469.7 | (M − H)− |
| PP2773 | FA | 6.115 | 1542.1 | (M − H)− |
| PP2776 | FA | 6.231 | 1546.2 | (M − H)− |
| PP2777 | FA | 6.813 | 1506.1 | (M − H)− |
| PP2778 | FA | 6.300 | 1450.0 | (M − H)− |
| PP2779 | FA | 6.611 | 1452.1 | (M − H)− |
| PP2780 | FA | 5.708 | 1527.6 | (M − H)− |
| PP2781 | FA | 5.960 | 1530.0 | (M − H)− |
| PP2782 | FA | 5.519 | 1474.3 | (M − H)− |
| PP2783 | FA | 5.760 | 1476.2 | (M − H)− |
| PP2784 | FA | 6.280 | 1544.2 | (M − H)− |
| PP2785 | FA | 6.588 | 1546.0 | (M − H)− |
| PP2786 | FA | 6.111 | 1489.7 | (M − H)− |
| PP2787 | FA | 6.389 | 1492.1 | (M − H)− |
| PP2788 | FA | 5.749 | 1505.7 | (M − H)− |
| PP2789 | FA | 6.021 | 1508.1 | (M − H)− |
| PP2790 | AA | 7.643 | 1452.1 | (M − H)− |
| PP2791 | FA | 5.812 | 1453.7 | (M − H)− |
| PP2796 | AA | 7.867 | 1491.6 | (M − H)− |
| PP2797 | FA | 5.783 | 1477.6 | (M − H)− |
| PP2798 | FA | 5.709 | 1478.2 | (M − H)− |
| PP2799 | FA | 5.761 | 1441.8 | (M − H)− |
| PP2800 | FA | 6.216 | 1505.6 | (M − H)− |
| PP2801 | FA | 6.115 | 1504.2 | (M − H)− |
| PP2802 | FA | 6.007 | 1492.3 | (M − H)− |
| PP2803 | FA | 5.932 | 1498.2 | (M − H)− |
| PP2804 | FA | 5.713 | 1478.0 | (M − H)− |
| PP2805 | AA | 8.045 | 1467.5 | (M − H)− |
| PP2806 | AA | 8.213 | 1574.1 | (M − H)− |
| PP2807 | FA | 5.979 | 1532.0 | (M − H)− |
| PP2808 | FA | 6.503 | 1520.3 | (M − H)− |
| PP2809 | FA | 5.776 | 1525.8 | (M − H)− |
| PP2810 | FA | 6.349 | 1473.8 | (M − H)− |
| PP2811 | AA | 7.927 | 1496.0 | (M − H)− |
| PP2812 | FA | 6.707 | 1489.4 | (M + H)+ |
| PP2813 | FA | 6.268 | 1558.1 | (M − H)− |
| PP2814 | FA | 6.611 | 1489.5 | (M + H)+ |
| PP2815 | AA | 7.840 | 1551.7 | (M − H)− |
| PP2816 | FA | 6.765 | 1502.3 | (M + H)+ |
| PP2817 | FA | 6.267 | 1540.8 | (M + NH$_4$)+ |
| PP2818 | FA | 7.097 | 1532.7 | (M + NH$_4$)+ |
| PP2819 | AA | 8.221 | 1535.9 | (M − H)− |
| PP2820 | FA | 6.523 | 1457.5 | (M + H)+ |
| PP2821 | AA | 8.080 | 1561.6 | (M + Na)+ |
| PP2822 | FA | 6.369 | 1528.9 | (M + NH$_4$)+ |
| PP2823 | FA | 6.396 | 1544.1 | (M − H)− |
| PP2824 | FA | 6.221 | 1521.6 | (M − H)− |
| PP2825 | FA | 5.976 | 1552.3 | (M − H)− |
| PP2826 | FA | 6.267 | 1556.1 | (M − H)− |
| PP2827 | FA | 6.435 | 1520.1 | (M − H)− |
| PP2828 | FA | 6.191 | 1550.3 | (M − H)− |
| PP2829 | FA | 6.472 | 1553.9 | (M − H)− |
| PP2830 | AA | 8.208 | 1540.1 | (M − H)− |
| PP2831 | FA | 6.457 | 1574.0 | (M − H)− |
| PP2832 | FA | 6.145 | 1551.8 | (M + H)+ |
| PP2833 | FA | 6.180 | 1585.8 | (M + H)+ |
| PP2834 | FA | 6.311 | 1541.5 | (M + H)+ |
| PP2835 | FA | 6.177 | 1527.4 | (M + H)+ |
| PP2836 | FA | 6.205 | 1559.8 | (M − H)− |
| PP2837 | FA | 6.029 | 1509.6 | (M − H)− |
| PP2838 | FA | 6.079 | 1544.0 | (M − H)− |
| PP2839 | FA | 6.181 | 1510.1 | (M − H)− |
| PP2840 | FA | 5.932 | 1540.0 | (M − H)− |
| PP2841 | AA | 7.976 | 1543.9 | (M − H)− |
| PP2842 | FA | 6.152 | 1556.0 | (M − H)− |
| PP2843 | AA | 8.048 | 1520.0 | (M − H)− |
| PP2844 | FA | 6.335 | 1554.0 | (M − H)− |
| PP2845 | AA | 7.976 | 1533.9 | (M + Na)+ |
| PP2846 | FA | 5.877 | 1540.2 | (M − H)− |
| PP2847 | FA | 6.183 | 1544.0 | (M − H)− |
| PP2848 | FA | 6.485 | 1504.0 | (M − H)− |
| PP2849 | FA | 6.236 | 1500.2 | (M − H)− |
| PP2850 | FA | 5.533 | 1501.7 | (M − H)− |
| PP2852 | FA | 6.504 | 1550.0 | (M − H)− |
| PP2853 | FA | 6.061 | 1512.3 | (M − H)− |
| PP2854 | FA | 6.109 | 1500.1 | (M − H)− |
| PP2855 | FA | 6.333 | 1495.6 | (M − H)− |
| PP2856 | FA | 6.161 | 1488.3 | (M − H)− |
| PP2857 | FA | 5.945 | 1519.8 | (M − H)− |
| PP2858 | FA | 6.411 | 1517.6 | (M + H)+ |
| PP2859 | AA | 8.267 | 1580.3 | (M + H)+ |
| PP2860 | FA | 5.881 | 1542.5 | (M + NH$_4$)+ |
| PP2861 | FA | 6.511 | 1540.2 | (M + H)+ |
| PP2862 | FA | 6.343 | 1518.3 | (M − H)− |

TABLE 36-continued

| Compound No. | Analytical condition | Retention time (min) | MS Found (m/z) | MS polarity |
|---|---|---|---|---|
| PP2863 | FA | 6.645 | 1510.3 | (M − H)− |
| PP2864 | FA | 5.904 | 1523.9 | (M − H)− |
| PP2865 | FA | 6.160 | 1559.8 | (M − H)− |
| PP2866 | FA | 6.205 | 1540.0 | (M − H)− |
| PP2867 | FA | 5.716 | 1540.0 | (M − H)− |
| PP2868 | FA | 5.692 | 1540.7 | (M + NH₄)+ |
| PP2869 | FA | 6.197 | 1500.3 | (M − H)− |
| PP2870 | FA | 6.725 | 1510.3 | (M − H)− |
| PP2871 | FA | 6.103 | 1496.1 | (M − H)− |
| PP2872 | FA | 6.544 | 1509.2 | (M + NH₄)+ |
| PP2873 | FA | 6.159 | 1492.4 | (M − H)− |
| PP2874 | FA | 6.095 | 1495.7 | (M − H)− |
| PP2875 | FA | 6.425 | 1511.6 | (M − H)− |
| PP2876 | FA | 5.951 | 1512.1 | (M − H)− |
| PP2877 | FA | 6.377 | 1533.4 | (M + H)+ |
| PP2879 | FA | 6.431 | 1472.2 | (M − H)− |
| PP2880 | FA | 5.748 | 1474.2 | (M − H)− |
| PP2881 | FA | 6.707 | 1522.1 | (M − H)− |
| PP2883 | FA | 6.267 | 1484.1 | (M − H)− |
| PP2884 | FA | 6.308 | 1472.1 | (M − H)− |
| PP2885 | AA | 8.295 | 1488.1 | (M − H)− |
| PP2886 | FA | 6.524 | 1468.1 | (M − H)− |
| PP2888 | AA | 8.199 | 1536.1 | (M + H)+ |
| PP2889 | FA | 6.476 | 1545.3 | (M + NH₄)+ |
| PP2890 | FA | 6.416 | 1481.8 | (M + H)+ |
| PP2891 | AA | 8.177 | 1472.3 | (M − H)− |
| PP2892 | FA | 6.859 | 1533.7 | (M + H)+ |
| PP2893 | FA | 6.203 | 1542.3 | (M + NH₄)+ |
| PP2894 | FA | 6.661 | 1480.4 | (M + H)+ |
| PP2895 | FA | 6.008 | 1487.8 | (M + NH₄)+ |
| PP2896 | FA | 6.300 | 1531.3 | (M − H)− |
| PP2897 | FA | 5.977 | 1528.4 | (M + NH₄)+ |
| PP2898 | FA | 6.095 | 1478.9 | (M + H)+ |
| PP2899 | FA | 5.781 | 1455.5 | (M − H)− |
| PP2900 | FA | 6.797 | 1528.3 | (M − H)− |
| PP2901 | FA | 5.625 | 1496.9 | (M + H)+ |
| PP2902 | AA | 8.317 | 1474.4 | (M − H)− |
| PP2904 | FA | 6.497 | 1525.5 | (M − H)− |
| PP2905 | FA | 5.593 | 1510.3 | (M + H)+ |
| PP2906 | FA | 6.292 | 1471.5 | (M − H)− |
| PP2907 | FA | 6.101 | 1518.3 | (M − H)− |
| PP2908 | FA | 6.263 | 1512.7 | (M + H)+ |
| PP2909 | FA | 5.573 | 1478.3 | (M − H)− |
| PP2910 | AA | 7.989 | 1457.5 | (M − H)− |
| PP2911 | FA | 5.092 | 1450.3 | (M − H)− |
| PP2912 | FA | 5.909 | 1515.8 | (M + NH₄)+ |
| PP2913 | FA | 6.317 | 1558.4 | (M − H)− |
| PP2914 | FA | 5.697 | 1443.4 | (M − H)− |
| PP2915 | FA | 5.887 | 1474.3 | (M − H)− |
| PP2916 | FA | 6.348 | 1521.6 | (M + H)+ |
| PP2917 | AA | 7.725 | 1522.3 | (M − H)− |
| PP2918 | FA | 6.041 | 1492.3 | (M − H)− |
| PP2920 | AA | 7.939 | 1484.1 | (M − H)− |
| PP2921 | FA | 6.265 | 1454.0 | (M − H)− |
| PP2922 | FA | 6.144 | 1466.4 | (M − H)− |
| PP2923 | AA | 7.680 | 1468.3 | (M − H)− |
| PP2928 | FA | 6.740 | 1516.3 | (M − H)− |
| PP2929 | FA | 6.316 | 1518.3 | (M − H)− |
| PP2931 | FA | 6.245 | 1464.2 | (M − H)− |
| PP2932 | FA | 5.867 | 1466.3 | (M − H)− |
| PP2934 | AA | 7.883 | 1514.4 | (M + H)+ |
| PP2935 | FA | 5.977 | 1514.3 | (M − H)− |
| PP2936 | FA | 5.960 | 1484.3 | (M − H)− |
| PP2937 | FA | 5.852 | 1460.4 | (M − H)− |
| PP2938 | FA | 5.505 | 1462.4 | (M − H)− |
| PP2941 | FA | 6.033 | 1487.6 | (M + H)+ |
| PP2946 | FA | 6.283 | 1532.3 | (M − H)− |
| PP2947 | FA | 6.099 | 1478.1 | (M − H)− |
| PP2948 | FA | 6.524 | 1530.3 | (M − H)− |
| PP2949 | FA | 6.351 | 1476.3 | (M − H)− |
| PP2950 | FA | 5.992 | 1531.1 | (M + H)+ |
| PP2951 | AA | 7.791 | 1475.3 | (M − H)− |
| PP2952 | FA | 6.541 | 1546.4 | (M + H)+ |
| PP2953 | FA | 6.660 | 1526.9 | (M + NH₄)+ |
| PP2954 | AA | 7.919 | 1540.3 | (M − H)− |
| PP2955 | FA | 6.400 | 1549.4 | (M + NH₄)+ |
| PP2956 | FA | 6.559 | 1543.7 | (M + H)+ |
| PP2957 | FA | 6.020 | 1530.4 | (M + H)+ |
| PP2958 | FA | 6.521 | 1523.1 | (M + NH₄)+ |
| PP2959 | FA | 6.475 | 1513.2 | (M + NH₄)+ |
| PP2960 | FA | 6.047 | 1480.3 | (M − H)− |
| PP2961 | FA | 6.456 | 1532.2 | (M − H)− |
| PP2962 | AA | 8.156 | 1441.9 | (M − H)− |
| PP2963 | FA | 6.228 | 1478.3 | (M − H)− |
| PP2964 | FA | 6.672 | 1530.1 | (M − H)− |
| PP2965 | FA | 6.563 | 1530.2 | (M − H)− |
| PP2966 | AA | 7.964 | 1478.1 | (M − H)− |
| PP2967 | FA | 6.339 | 1476.2 | (M − H)− |
| PP2968 | FA | 6.335 | 1526.4 | (M − H)− |
| PP2969 | FA | 6.480 | 1546.2 | (M − H)− |
| PP2970 | FA | 5.832 | 1474.3 | (M − H)− |
| PP2971 | FA | 6.519 | 1558.2 | (M − H)− |
| PP2972 | AA | 8.081 | 1498.1 | (M − H)− |
| PP2973 | AA | 8.073 | 1532.2 | (M − H)− |
| PP2974 | FA | 6.131 | 1445.8 | (M + H)+ |
| PP2975 | FA | 6.192 | 1558.1 | (M − H)− |
| PP2976 | FA | 6.215 | 1523.9 | (M − H)− |
| PP2977 | FA | 6.259 | 1532.2 | (M − H)− |
| PP2978 | FA | 5.941 | 1470.3 | (M − H)− |
| PP2979 | FA | 6.697 | 1528.2 | (M − H)− |
| PP2980 | FA | 6.337 | 1522.0 | (M − H)− |
| PP2981 | FA | 6.735 | 1540.2 | (M − H)− |
| PP2982 | FA | 6.055 | 1468.1 | (M − H)− |
| PP2983 | FA | 6.647 | 1514.1 | (M − H)− |
| PP2984 | FA | 6.287 | 1556.2 | (M − H)− |
| PP2985 | FA | 6.333 | 1540.1 | (M − H)− |
| PP2986 | FA | 6.467 | 1538.2 | (M − H)− |
| PP2987 | FA | 6.447 | 1514.1 | (M − H)− |
| PP2988 | FA | 6.025 | 1504.4 | (M − H)− |
| PP2989 | FA | 6.259 | 1506.3 | (M − H)− |
| PP2990 | FA | 6.219 | 1486.4 | (M − H)− |
| PP2991 | FA | 6.116 | 1480.3 | (M − H)− |
| PP2992 | FA | 5.808 | 1498.4 | (M − H)− |
| PP2993 | FA | 5.924 | 1506.2 | (M − H)− |
| PP2994 | FA | 6.016 | 1480.1 | (M − H)− |
| PP2995 | FA | 6.005 | 1480.3 | (M − H)− |
| PP2996 | AA | 8.119 | 1570.2 | (M − H)− |
| PP2997 | FA | 6.417 | 1476.2 | (M − H)− |
| PP2998 | FA | 6.335 | 1516.2 | (M − H)− |
| PP2999 | FA | 6.447 | 1488.3 | (M − H)− |
| PP3000 | FA | 5.547 | 1572.1 | (M − H)− |
| PP3001 | FA | 6.341 | 1462.2 | (M − H)− |
| PP3002 | FA | 5.379 | 1518.1 | (M − H)− |
| PP3003 | FA | 6.047 | 1488.0 | (M − H)− |
| PP3004 | FA | 6.167 | 1462.2 | (M − H)− |
| PP3005 | FA | 6.041 | 1500.3 | (M − H)− |
| PP3006 | FA | 5.853 | 1474.3 | (M − H)− |
| PP3007 | FA | 5.753 | 1500.0 | (M − H)− |
| PP3008 | FA | 5.793 | 1474.3 | (M − H)− |
| PP3009 | FA | 6.189 | 1470.3 | (M − H)− |
| PP3010 | FA | 6.220 | 1482.3 | (M − H)− |
| PP3011 | FA | 6.059 | 1456.2 | (M − H)− |
| PP3012 | FA | 5.869 | 1482.2 | (M − H)− |
| PP3013 | FA | 5.959 | 1456.3 | (M − H)− |
| PP3014 | FA | 6.759 | 1572.1 | (M − H)− |
| PP3015 | FA | 6.685 | 1558.1 | (M − H)− |
| PP3017 | FA | 6.524 | 1558.1 | (M − H)− |
| PP3018 | AA | 8.265 | 1518.2 | (M − H)− |
| PP3019 | FA | 6.489 | 1504.1 | (M − H)− |
| PP3021 | FA | 6.353 | 1505.4 | (M + H)+ |
| PP3022 | FA | 5.872 | 1574.1 | (M − H)− |
| PP3026 | FA | 5.624 | 1520.2 | (M − H)− |
| PP3030 | FA | 6.300 | 1534.4 | (M − H)− |
| PP3031 | FA | 6.657 | 1497.5 | (M + H)+ |
| PP3032 | FA | 5.919 | 1514.4 | (M − H)− |
| PP3033 | FA | 5.880 | 1524.4 | (M − H)− |
| PP3034 | FA | 5.919 | 1538.3 | (M − H)− |
| PP3035 | FA | 5.607 | 1500.4 | (M − H)− |
| PP3036 | FA | 6.156 | 1539.9 | (M + H)+ |
| PP3037 | FA | 5.600 | 1523.8 | (M − H)− |
| PP3038 | FA | 5.808 | 1500.4 | (M − H)− |
| PP3039 | FA | 6.689 | 1524.9 | (M + NH₄)+ |

TABLE 36-continued

| Compound No. | Analytical condition | Retention time (min) | MS Found (m/z) | MS polarity |
|---|---|---|---|---|
| PP3040 | FA | 6.124 | 1493.4 | (M + H)+ |
| PP3044 | FA | 6.105 | 1518.1 | (M − H)− |
| PP3045 | AA | 7.909 | 1482.0 | (M − H)− |
| PP3046 | FA | 6.276 | 1495.4 | (M + H)+ |
| PP3047 | FA | 5.712 | 1480.1 | (M − H)− |
| PP3048 | FA | 6.433 | 1532.4 | (M − H)− |
| PP3049 | AA | 7.837 | 1491.9 | (M − H)− |
| PP3050 | FA | 6.499 | 1497.4 | (M + H)+ |
| PP3051 | FA | 6.605 | 1507.6 | (M − H)− |
| PP3052 | FA | 6.025 | 1493.9 | (M − H)− |
| PP3053 | FA | 6.445 | 1517.8 | (M − H)− |
| PP3054 | FA | 6.717 | 1533.4 | (M + H)+ |
| PP3055 | FA | 6.424 | 1465.4 | (M + H)+ |
| PP3056 | FA | 5.672 | 1452.0 | (M − H)− |
| PP3057 | FA | 6.404 | 1493.9 | (M − H)− |
| PP3058 | FA | 6.616 | 1524.5 | (M + NH$_4$)+ |
| PP3059 | FA | 6.168 | 1498.5 | (M + NH$_4$)+ |
| PP3060 | FA | 6.128 | 1516.2 | (M − H)− |
| PP3061 | AA | 8.037 | 1524.9 | (M + NH$_4$)+ |
| PP3062 | AA | 7.981 | 1493.6 | (M − H)− |
| PP3063 | FA | 5.748 | 1486.0 | (M − H)− |
| PP3064 | FA | 6.260 | 1524.3 | (M − H)− |
| PP3065 | FA | 5.752 | 1510.0 | (M − H)− |
| PP3066 | FA | 5.829 | 1511.9 | (M − H)− |
| PP3067 | FA | 6.045 | 1526.1 | (M − H)− |
| PP3068 | FA | 6.267 | 1537.7 | (M − H)− |
| PP3069 | FA | 5.955 | 1495.5 | (M + H)+ |
| PP3070 | FA | 6.140 | 1538.2 | (M − H)− |
| PP3071 | FA | 6.035 | 1483.4 | (M + H)+ |
| PP3072 | FA | 5.720 | 1512.1 | (M − H)− |
| PP3073 | FA | 5.929 | 1524.2 | (M − H)− |
| PP3074 | FA | 5.615 | 1480.2 | (M − H)− |
| PP3075 | FA | 5.944 | 1523.5 | (M − H)− |
| PP3076 | FA | 5.733 | 1467.8 | (M − H)− |
| PP3077 | FA | 5.711 | 1498.3 | (M − H)− |
| PP3078 | FA | 5.872 | 1512.1 | (M − H)− |
| PP3079 | FA | 6.055 | 1543.4 | (M + NH$_4$)+ |
| PP3080 | FA | 6.057 | 1524.1 | (M − H)− |
| PP3081 | FA | 5.748 | 1480.3 | (M − H)− |
| PP3082 | FA | 6.144 | 1525.7 | (M + H)+ |
| PP3083 | FA | 5.876 | 1498.3 | (M − H)− |
| PP3084 | FA | 5.783 | 1498.2 | (M − H)− |
| PP3085 | FA | 5.949 | 1510.0 | (M − H)− |
| PP3086 | FA | 6.189 | 1524.4 | (M − H)− |
| PP3087 | FA | 5.604 | 1466.2 | (M − H)− |
| PP3088 | FA | 6.248 | 1524.1 | (M − H)− |
| PP3089 | AA | 7.901 | 1469.4 | (M + H)+ |
| PP3090 | FA | 6.193 | 1526.1 | (M − H)− |
| PP3091 | FA | 5.963 | 1512.3 | (M − H)− |
| PP3092 | FA | 5.997 | 1469.5 | (M + H)+ |
| PP3093 | FA | 6.052 | 1524.1 | (M − H)− |
| PP3094 | FA | 5.849 | 1524.1 | (M − H)− |
| PP3095 | FA | 6.699 | 1592.4 | (M − H)− |
| PP3096 | FA | 6.632 | 1540.4 | (M + H)+ |
| PP3097 | FA | 6.199 | 1580.4 | (M + H)+ |
| PP3098 | FA | 6.112 | 1524.4 | (M − H)− |
| PP3099 | FA | 6.524 | 1594.3 | (M + H)+ |
| PP3100 | FA | 6.423 | 1538.4 | (M − H)− |
| PP3101 | FA | 6.023 | 1578.4 | (M − H)− |
| PP3102 | FA | 5.915 | 1526.2 | (M + H)+ |
| PP3103 | FA | 6.276 | 1566.4 | (M − H)− |
| PP3104 | FA | 6.141 | 1512.4 | (M − H)− |
| PP3105 | FA | 5.753 | 1552.3 | (M − H)− |
| PP3106 | FA | 5.616 | 1498.3 | (M − H)− |
| PP3108 | FA | 5.989 | 1534.2 | (M − H)− |
| PP3109 | FA | 6.083 | 1548.0 | (M − H)− |
| PP3110 | FA | 6.917 | 1598.4 | (M − H)− |
| PP3111 | FA | 6.932 | 1546.3 | (M + H)+ |
| PP3112 | FA | 6.408 | 1584.1 | (M − H)− |
| PP3113 | FA | 6.312 | 1530.3 | (M − H)− |
| PP3114 | FA | 6.748 | 1598.4 | (M − H)− |
| PP3115 | FA | 6.651 | 1544.4 | (M − H)− |
| PP3116 | FA | 6.232 | 1584.3 | (M − H)− |
| PP3117 | FA | 6.125 | 1530.3 | (M − H)− |
| PP3118 | FA | 6.501 | 1572.3 | (M − H)− |
| PP3119 | FA | 6.367 | 1518.3 | (M − H)− |
| PP3120 | FA | 5.971 | 1558.2 | (M − H)− |
| PP3121 | FA | 5.831 | 1504.2 | (M − H)− |

Example 2 Pharmacological Test

Evaluation of Compound Binding to KRAS, NRAS, and HRAS by Surface Plasmon Resonance (SPR)

Surface plasmon resonance was used to analyze the binding affinity of compounds for KRAS, NRAS, and HRAS. The apparatus used was Biacore 8K, 8K+, or T200 (GE Healthcare), and the running buffer used was HBS (10 mM HEPES-NaOH, 150 mM NaCl, pH 7.4) containing 1 mM DTT, 10 mM MgCl$_2$, 0.01% Tween 20, 10 µM GDP, and 4% DMSO. The dilution series of each compound solution was prepared by, first, preparing a dilution series of a compound solution having a concentration 100-fold greater than the final concentration using DMSO as a solvent, and then diluting the solution 100-fold with a dilution buffer (1 mM DTT, 10 mM MgCl$_2$, 0.01% Tween 20, 10 µM GDP, 3.03% DMSO-containing HBS).

Biotinylated Avi-tag fusion KRAS, NRAS, and HRAS proteins were expressed in E. coli BL.21 (DE3) strains, and after cells were homogenized, they were purified using Streptavidin Mutein Matrix and Superdex 75. After purification, GDP-loaded KRAS, NRAS, and HRAS proteins were immobilized on the surface of Sensor Chip CAP (Cytiva) coated with Biotin CAPture Reagent in an immobilization amount of about 100 to 300 RU. Binding of each compound was evaluated by the Single Cycle Kinetics method, and a running buffer or a compound solution was added to the RAS protein non-immobilized surface and the immobilized surface to obtain a binding response. The flow rate was set to 100 µL/min, and in the compound-adding cycle, compound solutions having different concentrations were intermittently added for 75 seconds each, starting from a low concentration. The dissociation phase was observed for 3500 seconds. In the blank cycle, a running buffer was intermittently added and not the compound solution. The Biotin CAPture Reagent and RAS proteins were immobilized for each cycle, and at the end of each cycle, the sensor chip was regenerated by the regeneration solution appended to the Biotin CAPture Kit (Cytiva). Measurement was carried out at 30° C.

The resulting sensorgram was subjected to curve fitting based on a 1:1 binding model on Biacore Insight Evaluation Software or T200 Evaluation Software, and thereby the dissociation constant KD of each compound with respect to KRAS, NRAS, and HRAS was determined. Table 37 shows the KD value of each test compound with respect to GDP-bound KRAS wild-type protein, and the ratio of the KD value with respect to GDP-bound NRAS wild-type protein and HRAS wild-type protein to the KD value with respect to KRAS. A compound having a KD ratio of 0).1 or more and less than 3 is denoted as C, a compound having 3 or more and less than 10 is denoted as B, a compound having 10 or more and less than 20 is denoted as A, and a compound having 20 or more is denoted as AA. Blank indicates a compound from which the KD value with respect to NRAS or HRAS was not obtained.

Measurement of NCI-H441 Cell Proliferation Inhibitory Activity

A test compound was dispensed into a U-bottom 384-well plate as 40 nL serially diluted dimethyl sulfoxide solutions using a liquid handler Echo (LABCYTE). As for human lung cancer strain NCI-H441 (ATCC), a cell suspension was prepared so as to have 250 cells/40 µL in an RPMI-1640 medium (Sigma) supplemented with 10% fetal bovine serum (Sigma), a 2.5 g/L D-(+)-glucose solution, 10 mmol/L HEPES, and 1 mmol/L sodium pyruvate. This cell suspension was dispensed in an amount of 40 µL per well into a plate containing the test compound, and cultured at 37° C. in a 5% carbon dioxide gas incubator. Four days later, 20 µL of CellTiter-Glo (registered trademark)(Promega) was added to each well and fluorescence was measured. From the growth inhibition ratio attained when the test compound was added to that of the control to which the test compound was not added, the cell proliferation inhibitory activity of the test compound was calculated in terms of a 50% proliferation inhibitory concentration (an $IC_{50}$ value). The $IC_{50}$ value of each test compound is shown in Table 37.

TABLE 37

| Compound No. | KRAS KD (M) | NRAS/ KRAS | HRAS/ KRAS | NCI-H441 $IC_{50}$ (nM) |
|---|---|---|---|---|
| PP0001 | 1.4E−10 | C | C | 6.3 |
| PP0002 | 1.8E−10 | C | C | 2.1 |
| PP0003 | 2.0E−09 | C | C | 41.4 |
| PP0004 | 2.4E−09 | C | C | 52.9 |
| PP0006 | 1.5E−09 | C | C | 20.6 |
| PP0007 | 7.4E−11 | C | C | 4.8 |
| PP0011 | 3.0E−10 | C | C | 5.8 |
| PP0013 | 7.3E−11 | C | C | 9.8 |
| PP0014 | 9.0E−11 | C | C | 2.0 |
| PP0015 | 2.7E−09 | C | C | 24.5 |
| PP0016 | 1.6E−09 | C | C | 24.6 |
| PP0018 | 7.7E−11 | C | C | 7.0 |
| PP0019 | 3.4E−10 | C | C | 6.7 |
| PP0020 | 7.7E−10 | C | C | 9.9 |
| PP0021 | 6.5E−10 | C | C | 9.8 |
| PP0022 | 1.8E−10 | B | C | 14.4 |
| PP0023 | 1.4E−10 | B | C | 4.5 |
| PP0024 | 5.9E−09 | B | C | 101.6 |
| PP0025 | 2.4E−09 | C | C | 27.5 |
| PP0027 | 8.0E−10 | C | C | 17.1 |
| PP0028 | 2.4E−09 | C | C | 54.5 |
| PP0029 | 7.0E−09 | C | C | 26.4 |
| PP0030 | 7.7E−09 | C | C | 86.7 |
| PP0031 | 1.8E−10 | B | C | 11.4 |
| PP0032 | 3.7E−10 | C | C | 26.9 |
| PP0037 | 7.6E−09 | C | C | 429.7 |
| PP0039 | 1.7E−10 | C | C | 20.1 |
| PP0041 | 1.2E−10 | B | C | 62.7 |
| PP0042 | 1.2E−10 | C | C | 7.2 |
| PP0043 | 8.7E−10 | C | C | 20.4 |
| PP0044 | 3.6E−09 | C | C | 142.2 |
| PP0045 | 2.3E−09 | C | C | 292.3 |
| PP0047 | 1.8E−08 | C | C | 229.3 |
| PP0048 | 6.3E−08 | C | C | 464.1 |
| PP0049 | 6.3E−09 | C | C | 201.4 |
| PP0050 | 2.3E−08 | B | C | 499.0 |
| PP0051 | 9.1E−10 | C | C | 22.1 |
| PP0052 | 1.2E−10 | C | B | 1.7 |
| PP0053 | 1.2E−10 | C | C | 4.6 |
| PP0054 | 4.5E−09 | C | C | 82.0 |
| PP0055 | 2.7E−10 | C | C | 3.5 |
| PP0056 | 2.9E−09 | C | B | 49.6 |
| PP0057 | 2.1E−10 | C | B | 6.2 |
| PP0058 | 2.0E−09 | C | C | 25.8 |
| PP0059 | 1.5E−10 | B | C | 6.1 |
| PP0060 | 9.9E−11 | B | B | 1.5 |
| PP0061 | 3.8E−09 | B | C | 84.4 |
| PP0062 | 2.1E−10 | C | C | 3.8 |
| PP0063 | 2.9E−09 | C | C | 39.3 |

TABLE 37-continued

| Compound No. | KRAS KD (M) | NRAS/ KRAS | HRAS/ KRAS | NCI-H441 $IC_{50}$ (nM) |
|---|---|---|---|---|
| PP0064 | 4.2E−10 | C | C | 9.9 |
| PP0065 | 5.4E−10 | C | C | 4.3 |
| PP0066 | 1.4E−09 | B | C | 26.1 |
| PP0067 | 7.2E−11 | C | C | 2.7 |
| PP0068 | 1.4E−10 | C | C | 9.1 |
| PP0069 | 6.9E−09 | C | C | 39.7 |
| PP0070 | 1.6E−10 | C | B | 2.1 |
| PP0071 | 1.5E−10 | | | 3.8 |
| PP0076 | 6.4E−11 | C | C | 10.9 |
| PP0077 | 2.0E−10 | C | B | 5.3 |
| PP0078 | 1.9E−10 | C | B | 4.8 |
| PP0083 | 1.1E−09 | | | 11.3 |
| PP0084 | 2.7E−09 | C | B | 50.0 |
| PP0085 | 8.4E−09 | C | C | 108.5 |
| PP0086 | 2.6E−10 | C | B | 6.4 |
| PP0087 | 7.5E−10 | C | C | 24.0 |
| PP0088 | 1.2E−10 | | | 4.1 |
| PP0089 | 1.7E−10 | C | B | 5.5 |
| PP0090 | 8.3E−11 | | | 1.9 |
| PP0091 | 2.3E−10 | C | B | 4.1 |
| PP0092 | 1.5E−10 | C | C | 3.7 |
| PP0093 | 7.6E−11 | C | B | 2.2 |
| PP0094 | 9.4E−10 | C | C | 10.6 |
| PP0095 | 7.9E−10 | C | C | 18.2 |
| PP0096 | 2.8E−09 | C | C | 68.9 |
| PP0097 | 9.3E−09 | C | C | 240.1 |
| PP0098 | 2.3E−10 | | | 9.4 |
| PP0099 | 7.0E−10 | | | 18.7 |
| PP0100 | 1.9E−10 | B | C | 24.3 |
| PP0101 | 1.6E−10 | B | C | 10.4 |
| PP0102 | 2.0E−10 | C | C | 13.4 |
| PP0103 | 1.5E−10 | B | C | 8.2 |
| PP0104 | 2.5E−10 | B | C | 6.7 |
| PP0105 | 1.4E−10 | B | C | 8.3 |
| PP0106 | 1.9E−10 | C | B | 12.3 |
| PP0107 | 1.7E−09 | C | C | 32.2 |
| PP0108 | 2.0E−10 | C | C | 9.0 |
| PP0109 | 1.3E−09 | C | B | 21.7 |
| PP0110 | 4.0E−09 | C | B | 56.5 |
| PP0112 | 3.6E−10 | C | B | 6.1 |
| PP0113 | 7.5E−10 | C | B | 7.1 |
| PP0114 | 1.6E−10 | C | C | 6.1 |
| PP0115 | 2.1E−10 | C | C | 2.0 |
| PP0116 | 2.7E−10 | C | C | 6.8 |
| PP0117 | 1.9E−10 | B | B | 9.2 |
| PP0118 | 2.1E−10 | C | C | 6.0 |
| PP0119 | 1.0E−10 | C | C | 1.6 |
| PP0120 | 1.9E−10 | B | C | 5.6 |
| PP0121 | 2.1E−09 | C | C | 29.5 |
| PP0122 | 3.2E−10 | C | C | 12.0 |
| PP0123 | 8.3E−10 | B | C | 12.5 |
| PP0124 | 3.5E−09 | C | C | 48.8 |
| PP0126 | 4.3E−10 | C | C | 9.3 |
| PP0127 | 9.2E−10 | C | C | 25.3 |
| PP0128 | 2.5E−10 | C | C | 10.4 |
| PP0129 | 2.0E−10 | B | C | 8.8 |
| PP0130 | 2.5E−10 | C | C | 8.8 |
| PP0131 | 1.4E−10 | B | C | 11.1 |
| PP0132 | 2.0E−10 | C | C | 14.8 |
| PP0133 | 8.0E−11 | B | C | 6.4 |
| PP0134 | 6.6E−10 | C | B | 18.5 |
| PP0135 | 7.5E−10 | B | C | 26.1 |
| PP0136 | 1.3E−09 | | | 19.6 |
| PP0137 | 4.7E−10 | | | 13.4 |
| PP0138 | 7.7E−10 | C | C | 20.6 |
| PP0139 | 2.3E−07 | C | C | 1495.7 |
| PP0140 | 8.0E−07 | C | B | 712.5 |
| PP0141 | 5.5E−10 | C | B | 3.5 |
| PP0144 | 2.4E−10 | B | C | 18.3 |
| PP0145 | 5.0E−10 | B | B | 8.8 |
| PP0146 | 4.2E−10 | B | B | 23.9 |
| PP0148 | 3.4E−09 | B | B | 38.0 |
| PP0149 | 2.3E−08 | C | B | 317.4 |
| PP0150 | 1.7E−09 | B | C | 49.1 |
| PP0151 | 5.0E−10 | C | C | 5.3 |
| PP0152 | 2.8E−09 | C | B | 37.9 |
| PP0153 | 3.3E−10 | C | C | 11.6 |

TABLE 37-continued

| Compound No. | KRAS KD (M) | NRAS/ KRAS | HRAS/ KRAS | NCI-H441 IC$_{50}$ (nM) |
|---|---|---|---|---|
| PP0154 | 2.3E−10 | C | B | 9.9 |
| PP0155 | 1.8E−10 | B | C | 2.8 |
| PP0156 | 1.2E−10 | C | B | 8.1 |
| PP0158 | 8.5E−10 | A | B | 15.4 |
| PP0162 | 1.7E−08 | B | C | 165.8 |
| PP0165 | 2.9E−09 | B | B | 35.0 |
| PP0166 | 2.0E−09 | C | B | 24.9 |
| PP0168 | 6.7E−10 | C | B | 26.6 |
| PP0169 | 3.5E−11 | B | B | 2.3 |
| PP0170 | 1.2E−10 | B | B | 5.2 |
| PP0171 | 3.1E−10 | B | C | 6.9 |
| PP0172 | 1.3E−10 | B | C | 3.8 |
| PP0173 | 6.7E−10 | B | C | 11.6 |
| PP0174 | 1.5E−10 | B | B | 5.2 |
| PP0175 | 3.5E−10 | B | B | 6.6 |
| PP0176 | 5.5E−10 | B | C | 17.7 |
| PP0177 | 5.5E−10 | B | C | 34.4 |
| PP0178 | 7.3E−11 | C | B | 1.5 |
| PP0179 | 1.1E−10 | C | B | 4.5 |
| PP0180 | 7.2E−10 | C | C | 7.5 |
| PP0181 | 8.1E−11 | C | B | 1.5 |
| PP0182 | 8.8E−11 | C | B | 6.2 |
| PP0183 | 1.7E−10 | C | B | 1.6 |
| PP0184 | 3.2E−10 | C | B | 2.1 |
| PP0185 | 1.1E−09 | C | B | 32.2 |
| PP0186 | 1.7E−09 | C | B | 20.5 |
| PP0187 | 1.9E−10 | B | C | 3.0 |
| PP0188 | 2.5E−10 | B | C | 3.9 |
| PP0189 | 2.2E−10 | B | C | 3.0 |
| PP0190 | 1.3E−10 | B | B | 4.1 |
| PP0191 | 1.4E−10 | C | B | 3.9 |
| PP0192 | 1.9E−10 | C | B | 2.6 |
| PP0193 | 1.7E−10 | C | C | 1.4 |
| PP0194 | 9.0E−11 | C | B | 1.9 |
| PP0195 | 9.1E−11 | B | C | 2.7 |
| PP0196 | 1.5E−10 | C | C | 3.7 |
| PP0197 | 1.3E−10 | B | C | 3.6 |
| PP0198 | 1.9E−10 | C | B | 5.7 |
| PP0199 | 1.3E−10 | B | C | 3.5 |
| PP0200 | 2.2E−10 | C | C | 2.5 |
| PP0201 | 6.0E−11 | B | C | 3.4 |
| PP0202 | 7.6E−11 | B | C | 3.9 |
| PP0203 | 9.4E−11 | C | C | 2.8 |
| PP0204 | 2.1E−10 | C | C | 5.4 |
| PP0205 | 1.1E−10 | C | C | 4.6 |
| PP0206 | 7.1E−11 | C | B | 2.2 |
| PP0207 | 6.6E−11 | B | C | 1.9 |
| PP0208 | 2.6E−10 | C | C | 4.6 |
| PP0209 | 1.1E−07 | C | C | 568.8 |
| PP0210 | 5.2E−10 | C | C | 17.1 |
| PP0211 | 2.7E−10 | B | C | 10.8 |
| PP0212 | 9.8E−11 | C | C | 26.6 |
| PP0213 | 2.5E−10 | C | C | 10.3 |
| PP0214 | 1.3E−10 | B | C | 5.4 |
| PP0215 | 4.1E−10 | C | C | 4.8 |
| PP0216 | 2.8E−10 | C | B | 3.0 |
| PP0217 | 1.8E−10 | C | C | 18.1 |
| PP0218 | 2.0E−10 | C | C | 3.9 |
| PP0219 | 1.3E−10 | C | B | 2.2 |
| PP0220 | 3.5E−10 | C | C | 7.7 |
| PP0221 | 1.9E−10 | C | C | 2.9 |
| PP0222 | 5.7E−10 | C | C | 17.1 |
| PP0223 | 4.0E−10 | C | C | 5.0 |
| PP0224 | 2.2E−10 | C | B | 2.0 |
| PP0225 | 2.3E−10 | C | C | 2.4 |
| PP0226 | 4.7E−10 | C | B | 15.3 |
| PP0227 | 2.6E−10 | C | B | 4.1 |
| PP0228 | 3.7E−11 | C | B | 1.8 |
| PP0229 | 2.5E−10 | B | B | 24.7 |
| PP0230 | 3.9E−10 | B | C | 15.5 |
| PP0231 | 5.5E−10 | B | C | 13.1 |
| PP0232 | 2.8E−10 | B | B | 4.7 |
| PP0233 | 5.2E−11 | B | C | 1.6 |
| PP0234 | 4.9E−10 | B | C | 49.9 |
| PP0235 | 1.5E−10 | B | C | 4.5 |
| PP0236 | 5.4E−10 | B | C | 20.3 |
| PP0237 | 2.8E−10 | B | C | 4.0 |
| PP0238 | 4.1E−11 | C | C | 1.3 |
| PP0239 | 5.0E−11 | C | B | 6.2 |
| PP0240 | 3.5E−11 | B | C | 7.9 |
| PP0241 | 5.2E−11 | B | C | 4.9 |
| PP0242 | 2.0E−10 | C | C | 5.0 |
| PP0243 | 3.1E−10 | B | C | 23.2 |
| PP0244 | 3.5E−09 | C | B | 17.4 |
| PP0245 | 3.7E−10 | | | 22.9 |
| PP0246 | 5.4E−11 | B | C | 1.8 |
| PP0247 | 3.8E−10 | B | C | 41.3 |
| PP0248 | 1.1E−09 | B | B | 84.0 |
| PP0249 | 6.9E−10 | B | C | 25.5 |
| PP0250 | 1.2E−10 | B | C | 6.7 |
| PP0251 | 2.5E−10 | | | 8.4 |
| PP0252 | 3.4E−10 | B | B | 19.4 |
| PP0253 | 5.5E−10 | B | B | 15.1 |
| PP0254 | 1.6E−10 | B | C | 5.6 |
| PP0256 | 9.9E−10 | B | C | 26.6 |
| PP0257 | 1.4E−09 | B | B | 30.8 |
| PP0258 | 5.2E−10 | B | C | 11.3 |
| PP0259 | 4.2E−10 | C | B | 10.2 |
| PP0260 | 3.9E−10 | B | C | 16.8 |
| PP0261 | 1.4E−10 | B | C | 4.6 |
| PP0262 | 4.4E−11 | B | B | 1.9 |
| PP0263 | 4.7E−10 | B | C | 19.2 |
| PP0264 | 4.2E−10 | B | C | 16.4 |
| PP0265 | 2.8E−10 | B | C | 13.3 |
| PP0266 | 2.0E−10 | B | C | 15.2 |
| PP0267 | 8.7E−10 | B | B | 38.2 |
| PP0268 | 3.4E−10 | C | B | 15.4 |
| PP0269 | 1.4E−09 | C | B | 34.7 |
| PP0270 | 7.6E−10 | C | B | 8.5 |
| PP0271 | 2.2E−10 | C | B | 6.5 |
| PP0272 | 1.7E−10 | C | B | 3.7 |
| PP0273 | 5.6E−10 | C | B | 12.2 |
| PP0274 | 4.7E−10 | C | B | 9.1 |
| PP0275 | 3.0E−10 | C | C | 9.3 |
| PP0276 | 1.5E−07 | | | 752.2 |
| PP0277 | 5.3E−10 | C | C | 6.7 |
| PP0278 | 6.2E−10 | C | B | 12.4 |
| PP0279 | 3.6E−10 | | | 15.0 |
| PP0281 | 4.8E−10 | C | C | 7.8 |
| PP0282 | 1.1E−10 | C | C | 3.9 |
| PP0283 | 6.3E−11 | C | C | 1.9 |
| PP0284 | 6.7E−10 | C | B | 29.0 |
| PP0285 | 7.5E−10 | C | B | 18.9 |
| PP0286 | 5.2E−10 | C | B | 35.0 |
| PP0287 | 2.6E−10 | C | C | 14.5 |
| PP0288 | 4.2E−10 | C | B | 14.3 |
| PP0289 | 2.2E−09 | B | B | 76.4 |
| PP0290 | 4.8E−09 | B | C | 149.0 |
| PP0291 | 2.2E−09 | B | B | 31.0 |
| PP0292 | 5.4E−10 | B | C | 36.3 |
| PP0293 | 8.4E−10 | B | C | 37.6 |
| PP0294 | 1.7E−09 | B | C | 55.4 |
| PP0295 | 5.2E−10 | B | C | 33.2 |
| PP0296 | 1.5E−10 | B | C | 4.3 |
| PP0297 | 2.3E−09 | B | C | 74.3 |
| PP0298 | 3.0E−09 | B | C | 41.1 |
| PP0299 | 1.4E−09 | B | B | 20.2 |
| PP0300 | 1.4E−09 | B | C | 73.9 |
| PP0301 | 4.8E−09 | B | C | 88.2 |
| PP0302 | 1.6E−09 | B | C | 126.2 |
| PP0303 | 4.0E−09 | B | B | 349.2 |
| PP0304 | 1.9E−09 | B | B | 112.4 |
| PP0305 | 9.6E−10 | B | C | 49.6 |
| PP0306 | 1.2E−09 | B | B | 141.5 |
| PP0307 | 2.1E−09 | B | B | 204.8 |
| PP0308 | 1.1E−09 | B | B | 56.0 |
| PP0309 | 2.9E−10 | B | C | 11.7 |
| PP0310 | 4.5E−10 | B | C | 13.8 |
| PP0311 | 3.3E−09 | B | B | 146.6 |
| PP0312 | 3.4E−09 | B | B | 82.4 |
| PP0313 | 2.2E−09 | B | C | 56.6 |
| PP0314 | 1.6E−09 | B | C | 58.1 |
| PP0315 | 3.8E−09 | B | B | 148.0 |
| PP0316 | 5.4E−11 | C | B | 2.8 |

TABLE 37-continued

| Compound No. | KRAS KD (M) | NRAS/ KRAS | HRAS/ KRAS | NCI-H441 IC$_{50}$ (nM) |
|---|---|---|---|---|
| PP0317 | 8.6E−10 | B | B | 32.2 |
| PP0318 | 3.4E−11 | B | B | 2.3 |
| PP0319 | 1.8E−09 | B | B | 23.5 |
| PP0320 | 9.0E−10 | B | B | 92.3 |
| PP0321 | 1.0E−09 | B | B | 55.7 |
| PP0322 | 8.4E−10 | B | C | 74.2 |
| PP0323 | 2.5E−10 | B | B | 64.0 |
| PP0324 | 4.1E−10 | B | B | 38.5 |
| PP0325 | 1.1E−09 | B | B | 163.2 |
| PP0326 | 1.5E−09 | B | B | 172.5 |
| PP0327 | 1.9E−09 | B | B | 162.5 |
| PP0328 | 1.6E−09 | B | B | 242.6 |
| PP0329 | 7.4E−10 | B | C | 65.8 |
| PP0330 | 9.5E−10 | B | C | 98.2 |
| PP0331 | 2.8E−09 | B | B | 84.7 |
| PP0332 | 3.2E−09 | B | B | 167.1 |
| PP0333 | 2.4E−09 | B | C | 41.6 |
| PP0334 | 4.7E−09 | B | C | 129.7 |
| PP0335 | 1.3E−09 | B | C | 41.7 |
| PP0336 | 1.6E−09 | B | B | 73.2 |
| PP0337 | 2.5E−09 | B | B | 333.4 |
| PP0338 | 3.6E−09 | B | B | 295.9 |
| PP0339 | 5.0E−09 | B | B | 157.9 |
| PP0340 | 3.7E−09 | B | B | 177.3 |
| PP0341 | 1.4E−09 | B | B | 134.9 |
| PP0342 | 1.7E−09 | B | B | 141.0 |
| PP0343 | 1.3E−09 | C | B | 47.6 |
| PP0344 | 1.1E−09 | C | B | 82.9 |
| PP0345 | 1.3E−09 | C | B | 54.9 |
| PP0346 | 1.2E−09 | C | B | 69.5 |
| PP0347 | 3.6E−10 | C | B | 10.9 |
| PP0348 | 3.8E−10 | C | B | 15.1 |
| PP0349 | 7.3E−10 | C | B | 75.9 |
| PP0350 | 1.1E−09 | C | B | 69.8 |
| PP0351 | 1.1E−09 | C | B | 39.0 |
| PP0352 | 8.2E−10 | C | B | 72.4 |
| PP0353 | 4.7E−10 | C | B | 46.7 |
| PP0354 | 4.4E−10 | C | B | 24.7 |
| PP0355 | 3.3E−10 | B | B | 48.2 |
| PP0356 | 4.9E−10 | B | B | 99.4 |
| PP0357 | 4.0E−10 | B | B | 39.8 |
| PP0358 | 3.3E−10 | B | C | 34.8 |
| PP0359 | 1.4E−10 | B | B | 33.1 |
| PP0360 | 2.5E−10 | B | C | 18.0 |
| PP0361 | 7.2E−10 | B | C | 69.0 |
| PP0362 | 1.0E−09 | B | B | 148.6 |
| PP0363 | 1.0E−09 | B | C | 91.4 |
| PP0364 | 7.7E−10 | B | B | 103.0 |
| PP0365 | 2.9E−10 | B | B | 42.6 |
| PP0366 | 3.8E−10 | B | B | 80.2 |
| PP0367 | 1.3E−09 | B | B | 99.1 |
| PP0368 | 1.7E−09 | B | B | 114.8 |
| PP0369 | 1.9E−09 | B | C | 68.9 |
| PP0370 | 1.5E−09 | B | C | 63.2 |
| PP0371 | 4.8E−10 | B | C | 30.9 |
| PP0372 | 7.9E−10 | B | B | 34.2 |
| PP0373 | 1.2E−09 | B | B | 152.0 |
| PP0374 | 1.8E−09 | B | B | 141.9 |
| PP0375 | 2.3E−09 | B | B | 57.1 |
| PP0376 | 2.0E−09 | B | B | 114.2 |
| PP0377 | 7.0E−10 | B | C | 33.4 |
| PP0378 | 8.5E−10 | B | B | 109.6 |
| PP0379 | 3.8E−10 | C | B | 4.4 |
| PP0380 | 5.9E−10 | C | B | 16.4 |
| PP0381 | 4.9E−10 | C | B | 11.1 |
| PP0382 | 3.5E−10 | C | B | 12.1 |
| PP0383 | 2.4E−10 | C | B | 2.6 |
| PP0384 | 1.8E−10 | C | B | 7.0 |
| PP0385 | 3.7E−10 | | | 15.2 |
| PP0386 | 6.9E−10 | C | B | 29.6 |
| PP0387 | 5.4E−10 | C | B | 20.0 |
| PP0388 | 7.8E−10 | C | B | 11.6 |
| PP0389 | 1.6E−10 | C | B | 3.0 |
| PP0390 | 2.0E−10 | C | B | 7.6 |
| PP0391 | 9.2E−11 | B | B | 1.1 |
| PP0392 | 6.7E−11 | B | C | 0.9 |
| PP0393 | 1.1E−10 | B | B | 2.7 |
| PP0394 | 2.4E−10 | C | C | 2.6 |
| PP0395 | 6.8E−11 | B | C | 0.8 |
| PP0396 | 1.3E−10 | B | C | 0.9 |
| PP0397 | 1.2E−10 | C | C | 0.7 |
| PP0398 | 4.8E−10 | B | C | 3.6 |
| PP0399 | 3.3E−10 | B | C | 6.3 |
| PP0400 | 1.7E−10 | B | B | 7.8 |
| PP0401 | 1.5E−10 | B | B | 5.1 |
| PP0402 | 1.2E−09 | B | C | 58.1 |
| PP0403 | 8.3E−10 | B | B | 19.4 |
| PP0404 | 3.7E−10 | B | C | 21.7 |
| PP0405 | 3.1E−10 | B | C | 14.3 |
| PP0406 | 4.2E−11 | C | B | 2.5 |
| PP0407 | 1.1E−10 | C | B | 7.6 |
| PP0408 | 9.4E−11 | C | B | 5.7 |
| PP0409 | 5.6E−11 | C | C | 4.4 |
| PP0410 | 5.8E−11 | C | B | 1.4 |
| PP0411 | 4.6E−11 | C | C | 2.8 |
| PP0412 | 4.3E−11 | B | C | 1.8 |
| PP0413 | 4.9E−11 | C | C | 2.0 |
| PP0414 | 2.9E−11 | B | C | 1.9 |
| PP0415 | 1.8E−11 | B | B | 1.9 |
| PP0416 | 2.7E−11 | B | C | 1.1 |
| PP0417 | 7.4E−11 | B | C | 3.9 |
| PP0418 | 7.4E−11 | B | C | 4.6 |
| PP0419 | 6.7E−11 | B | C | 4.2 |
| PP0420 | 3.4E−11 | B | C | 1.2 |
| PP0421 | 3.3E−11 | B | C | 2.0 |
| PP0422 | 1.7E−11 | B | B | 1.6 |
| PP0423 | 1.8E−11 | B | C | 7.1 |
| PP0424 | 1.7E−10 | B | C | 9.5 |
| PP0425 | 9.9E−11 | B | C | 6.5 |
| PP0426 | 1.2E−10 | C | C | 4.8 |
| PP0427 | 1.1E−10 | B | C | 2.2 |
| PP0428 | 6.3E−11 | B | C | 4.6 |
| PP0429 | 3.9E−10 | B | C | 12.4 |
| PP0430 | 2.6E−10 | B | B | 27.9 |
| PP0431 | 3.5E−10 | B | C | 9.9 |
| PP0432 | 1.7E−10 | B | B | 10.7 |
| PP0433 | 1.5E−10 | B | B | 11.0 |
| PP0434 | 1.2E−10 | B | C | 9.7 |
| PP0435 | 4.7E−11 | C | C | 2.6 |
| PP0436 | 5.4E−11 | C | C | 1.0 |
| PP0437 | 3.6E−11 | C | B | 1.2 |
| PP0438 | 3.0E−11 | C | C | 1.0 |
| PP0439 | 2.1E−11 | | | 0.7 |
| PP0440 | 4.6E−11 | C | B | 4.4 |
| PP0441 | 7.2E−11 | C | C | 3.4 |
| PP0442 | 3.7E−11 | C | C | 0.8 |
| PP0443 | 2.7E−11 | C | C | 0.9 |
| PP0444 | 3.1E−11 | C | C | 1.4 |
| PP0445 | 2.5E−11 | C | C | 1.7 |
| PP0446 | 1.0E−10 | B | C | 1.6 |
| PP0447 | 1.8E−10 | B | C | 3.9 |
| PP0448 | 1.5E−10 | B | C | 2.0 |
| PP0449 | 3.5E−10 | C | C | 9.2 |
| PP0450 | 3.8E−10 | B | C | 8.4 |
| PP0451 | 7.5E−10 | | | 11.2 |
| PP0452 | 7.3E−10 | B | B | 34.1 |
| PP0453 | 1.2E−09 | B | C | 20.3 |
| PP0454 | 7.3E−11 | C | C | 2.9 |
| PP0455 | 1.8E−10 | | | 9.9 |
| PP0456 | 7.0E−11 | C | C | 7.0 |
| PP0457 | 8.3E−11 | C | B | 12.1 |
| PP0460 | 1.4E−10 | C | C | 5.4 |
| PP0461 | 4.9E−10 | A | A | 23.2 |
| PP0462 | 3.2E−10 | C | C | 15.1 |
| PP0463 | 5.4E−10 | A | A | 26.3 |
| PP0464 | 9.2E−10 | B | B | 17.6 |
| PP0465 | 5.1E−10 | B | B | 18.0 |
| PP0466 | 2.0E−10 | B | B | 22.6 |
| PP0467 | 5.9E−10 | B | B | 33.8 |
| PP0468 | 8.0E−10 | B | B | 37.2 |
| PP0469 | 7.6E−10 | B | B | 36.1 |
| PP0470 | 5.5E−10 | B | B | 51.9 |
| PP0471 | 9.3E−10 | B | B | 37.7 |
| PP0472 | 7.7E−10 | B | B | 24.4 |

TABLE 37-continued

| Compound No. | KRAS KD (M) | NRAS/KRAS | HRAS/KRAS | NCI-H441 IC$_{50}$ (nM) |
|---|---|---|---|---|
| PP0473 | 5.6E−10 | C | C | 14.8 |
| PP0474 | 6.3E−10 | B | B | 19.9 |
| PP0475 | 4.6E−10 | B | B | 18.7 |
| PP0476 | 2.0E−10 | B | B | 4.9 |
| PP0477 | 1.1E−08 | A | A | 138.6 |
| PP0478 | 4.0E−07 | | | 2751.8 |
| PP0479 | 2.9E−08 | B | B | 2435.2 |
| PP0480 | 3.1E−09 | A | B | 47.3 |
| PP0481 | 8.5E−07 | B | B | >1000 |
| PP0483 | 3.4E−08 | B | B | 524.9 |
| PP0484 | 3.2E−09 | A | B | 165.1 |
| PP0485 | 2.8E−08 | A | B | 1264.5 |
| PP0487 | 1.7E−09 | B | B | 260.4 |
| PP0488 | 2.8E−09 | A | B | 54.3 |
| PP0490 | 2.4E−09 | B | B | 50.5 |
| PP0491 | 1.1E−09 | B | B | 33.1 |
| PP0492 | 1.2E−09 | B | B | 31.9 |
| PP0493 | 2.0E−09 | B | B | 628.4 |
| PP0494 | 5.1E−10 | B | B | 135.9 |
| PP0495 | 5.1E−09 | A | B | 837.4 |
| PP0496 | 4.8E−09 | B | B | 398.7 |
| PP0497 | 8.5E−10 | B | B | 44.2 |
| PP0498 | 1.8E−08 | B | B | 147.2 |
| PP0499 | 1.1E−09 | B | B | 44.9 |
| PP0500 | 1.8E−08 | B | B | 962.8 |
| PP0501 | 3.2E−09 | B | B | 715.8 |
| PP0502 | 1.2E−08 | A | B | 1818.1 |
| PP0503 | 4.4E−09 | A | B | 282.9 |
| PP0504 | 1.4E−08 | B | B | 234.9 |
| PP0505 | 1.0E−08 | B | B | 209.6 |
| PP0506 | 2.5E−08 | B | B | 705.0 |
| PP0507 | 9.4E−10 | B | B | 62.1 |
| PP0508 | 2.9E−09 | B | B | 251.6 |
| PP0509 | 2.4E−09 | B | B | 108.6 |
| PP0510 | 1.2E−08 | B | B | 391.2 |
| PP0511 | 1.6E−08 | A | B | 413.5 |
| PP0512 | 3.7E−10 | B | B | 29.4 |
| PP0513 | 6.2E−09 | B | B | 238.3 |
| PP0514 | 1.1E−08 | B | B | 311.3 |
| PP0515 | 2.9E−08 | B | B | 632.8 |
| PP0516 | 1.0E−08 | B | B | 457.0 |
| PP0520 | 9.9E−10 | B | B | 17.1 |
| PP0521 | 7.2E−09 | B | B | 585.5 |
| PP0522 | 2.8E−09 | B | B | 83.0 |
| PP0523 | 1.2E−08 | A | B | 734.1 |
| PP0524 | 1.1E−10 | B | C | 4.8 |
| PP0525 | 1.4E−10 | C | B | 2.1 |
| PP0526 | 7.4E−11 | B | C | 6.6 |
| PP0527 | 2.1E−10 | C | C | 5.7 |
| PP0528 | 3.7E−10 | C | C | 21.8 |
| PP0529 | 9.5E−11 | C | B | 6.5 |
| PP0530 | 6.0E−11 | C | B | 7.0 |
| PP0531 | 1.4E−10 | C | B | 21.2 |
| PP0532 | 6.6E−11 | C | B | 6.9 |
| PP0533 | 1.7E−10 | C | C | 8.9 |
| PP0534 | 1.6E−10 | B | B | 16.7 |
| PP0535 | 5.0E−10 | C | B | 55.4 |
| PP0536 | 6.3E−10 | B | B | 21.8 |
| PP0537 | 5.8E−09 | C | C | 196.7 |
| PP0538 | 6.7E−10 | B | B | 78.0 |
| PP0539 | 1.7E−10 | B | B | 6.3 |
| PP0540 | 1.7E−08 | B | B | 765.9 |
| PP0541 | 4.7E−10 | B | B | 83.3 |
| PP0542 | 1.1E−10 | B | B | 3.4 |
| PP0543 | 1.0E−09 | B | B | 41.5 |
| PP0544 | 1.8E−08 | B | B | 646.9 |
| PP0545 | 2.4E−10 | B | B | 14.0 |
| PP0546 | 1.4E−10 | B | B | 5.9 |
| PP0547 | 3.6E−10 | B | B | 21.5 |
| PP0548 | 1.5E−08 | C | B | 500.8 |
| PP0549 | 6.2E−11 | C | B | 13.0 |
| PP0550 | 5.7E−11 | B | B | 4.9 |
| PP0551 | 3.8E−08 | C | B | 401.4 |
| PP0552 | 5.2E−11 | B | B | 2.8 |
| PP0553 | 4.9E−11 | B | B | 5.6 |
| PP0554 | 3.6E−11 | B | B | 1.6 |
| PP0555 | 6.6E−11 | B | B | 48.5 |
| PP0556 | 2.4E−11 | C | B | 21.0 |
| PP0557 | 1.1E−10 | B | B | 14.8 |
| PP0558 | 6.7E−11 | B | B | 31.4 |
| PP0559 | 1.6E−10 | B | B | 23.1 |
| PP0560 | 5.0E−11 | B | B | 5.2 |
| PP0561 | 3.1E−10 | B | B | 20.9 |
| PP0562 | 4.0E−11 | B | B | 4.4 |
| PP0563 | 1.0E−10 | B | B | 29.0 |
| PP0564 | 1.8E−10 | B | B | 18.4 |
| PP0565 | 1.6E−10 | C | B | 11.5 |
| PP0566 | 2.9E−10 | B | B | 18.4 |
| PP0567 | 2.1E−10 | B | B | 8.3 |
| PP0568 | 1.1E−09 | B | B | 79.5 |
| PP0569 | 3.4E−11 | C | B | 2.8 |
| PP0570 | 4.6E−11 | B | B | 7.5 |
| PP0571 | 5.0E−11 | B | B | 5.4 |
| PP0572 | 1.4E−10 | B | B | 9.0 |
| PP0573 | 3.4E−10 | B | B | 8.7 |
| PP0574 | 2.6E−11 | C | B | 3.1 |
| PP0575 | 2.3E−11 | B | B | 3.2 |
| PP0576 | 1.9E−11 | C | B | 2.4 |
| PP0577 | 1.9E−11 | C | C | 2.4 |
| PP0578 | 2.9E−11 | B | B | 2.2 |
| PP0579 | 1.7E−11 | C | B | 2.4 |
| PP0580 | 1.5E−11 | C | C | 1.8 |
| PP0581 | 2.0E−11 | C | B | 8.0 |
| PP0582 | 2.0E−11 | C | B | 9.6 |
| PP0583 | 1.9E−11 | C | C | 10.3 |
| PP0584 | 7.7E−12 | C | C | 7.0 |
| PP0585 | 2.2E−11 | B | B | 6.2 |
| PP0586 | 1.0E−11 | C | B | 5.3 |
| PP0587 | 1.4E−11 | C | C | 5.1 |
| PP0588 | 1.1E−10 | B | B | 16.7 |
| PP0589 | 3.6E−10 | B | B | 24.8 |
| PP0590 | 2.7E−10 | C | B | 20.9 |
| PP0591 | 8.7E−08 | B | B | 3887.5 |
| PP0594 | 7.3E−11 | C | B | 2.5 |
| PP0595 | 1.0E−09 | C | B | 80.0 |
| PP0596 | 1.0E−10 | B | B | 8.3 |
| PP0597 | 3.3E−10 | B | B | 18.2 |
| PP0598 | 2.9E−10 | B | B | 19.6 |
| PP0599 | 1.8E−07 | C | B | 2800.0 |
| PP0605 | 2.8E−07 | C | C | 888.7 |
| PP0606 | 1.8E−09 | C | B | 266.0 |
| PP0607 | 9.7E−10 | C | B | 119.0 |
| PP0608 | 1.7E−09 | C | B | 252.2 |
| PP0609 | 3.9E−09 | B | B | 468.3 |
| PP0610 | 4.9E−08 | B | B | 689.4 |
| PP0611 | 7.3E−10 | B | B | 88.9 |
| PP0612 | 3.9E−10 | B | B | 43.3 |
| PP0613 | 6.0E−10 | B | B | 42.4 |
| PP0614 | 1.1E−09 | B | B | 110.3 |
| PP0615 | 6.2E−09 | B | B | 216.3 |
| PP0616 | 4.9E−09 | B | B | 73.8 |
| PP0617 | 6.9E−09 | B | B | 159.1 |
| PP0618 | 6.2E−09 | C | C | 79.1 |
| PP0619 | 3.7E−09 | C | C | 70.7 |
| PP0620 | 6.9E−10 | C | C | 38.4 |
| PP0621 | 2.4E−09 | C | C | 83.6 |
| PP0622 | 1.1E−08 | B | B | 330.2 |
| PP0626 | 7.1E−09 | C | C | 158.0 |
| PP0627 | 3.3E−09 | C | C | 98.3 |
| PP0628 | 2.4E−09 | C | C | 46.3 |
| PP0629 | 2.4E−09 | B | C | 45.1 |
| PP0630 | 6.9E−09 | C | B | 388.8 |
| PP0631 | 5.9E−10 | C | B | 41.4 |
| PP0632 | 1.1E−09 | C | B | 56.7 |
| PP0633 | 2.3E−09 | B | B | 116.3 |
| PP0634 | 4.0E−09 | B | B | 273.8 |
| PP0635 | 2.7E−09 | B | B | 85.6 |
| PP0636 | 8.6E−09 | A | A | 728.8 |
| PP0637 | 2.3E−08 | B | B | 951.6 |
| PP0638 | 3.4E−09 | B | B | 340.7 |
| PP0639 | 8.5E−09 | B | B | 630.6 |
| PP0640 | 2.0E−08 | B | B | >600 |
| PP0641 | 2.6E−08 | A | A | >1300 |
| PP0642 | 1.1E−07 | B | B | 2650.9 |

TABLE 37-continued

| Compound No. | KRAS KD (M) | NRAS/KRAS | HRAS/KRAS | NCI-H441 IC$_{50}$ (nM) |
|---|---|---|---|---|
| PP0643 | 7.4E−11 | C | B | 6.5 |
| PP0644 | 1.5E−10 | C | B | 20.7 |
| PP0645 | 2.8E−11 | B | B | 12.0 |
| PP0646 | 1.4E−10 | C | B | 17.0 |
| PP0647 | 6.8E−10 | C | B | 45.0 |
| PP0648 | 2.1E−10 | B | B | 20.8 |
| PP0649 | 7.5E−10 | C | B | 30.2 |
| PP0650 | 6.2E−10 | C | B | 45.7 |
| PP0651 | 6.0E−10 | B | B | 136.3 |
| PP0652 | 2.5E−09 | B | B | 208.5 |
| PP0653 | 1.4E−09 | B | B | 165.7 |
| PP0654 | 2.0E−09 | B | B | 690.0 |
| PP0655 | 1.9E−09 | B | B | 124.7 |
| PP0656 | 3.9E−11 | C | C | 26.5 |
| PP0657 | 7.6E−11 | B | B | 32.9 |
| PP0658 | 3.4E−11 | C | B | 10.3 |
| PP0659 | 4.2E−10 | B | B | 184.2 |
| PP0660 | 2.9E−10 | B | B | 131.3 |
| PP0661 | 3.4E−10 | C | B | 56.6 |
| PP0662 | 3.1E−09 | B | B | 1569.0 |
| PP0663 | 2.8E−10 | B | B | 22.7 |
| PP0664 | 1.9E−10 | B | B | 15.3 |
| PP0665 | 2.4E−10 | B | B | 15.6 |
| PP0666 | 3.3E−10 | B | B | 19.1 |
| PP0667 | 2.7E−10 | B | B | 8.8 |
| PP0668 | 3.8E−10 | B | B | 22.7 |
| PP0669 | 5.2E−10 | B | B | 20.3 |
| PP0670 | 2.8E−10 | B | B | 11.3 |
| PP0671 | 6.7E−10 | B | B | 32.5 |
| PP0672 | 3.0E−10 | B | B | 19.7 |
| PP0673 | 1.2E−10 | B | B | 52.5 |
| PP0674 | 1.6E−10 | B | B | 13.9 |
| PP0675 | 2.2E−10 | B | B | 25.5 |
| PP0678 | 4.7E−10 | B | B | 35.6 |
| PP0679 | 5.8E−10 | B | B | 40.2 |
| PP0680 | 4.3E−10 | B | B | 21.2 |
| PP0681 | 4.4E−10 | B | B | 24.2 |
| PP0682 | 5.4E−10 | B | B | 22.6 |
| PP0683 | 6.1E−10 | B | B | 44.7 |
| PP0684 | 1.1E−09 | B | B | 45.0 |
| PP0685 | 8.0E−10 | B | B | 52.3 |
| PP0686 | 1.0E−09 | B | B | 65.7 |
| PP0687 | 6.4E−10 | B | B | 44.1 |
| PP0688 | 2.1E−10 | A | B | 187.4 |
| PP0689 | 3.0E−10 | B | B | 34.4 |
| PP0690 | 4.6E−10 | B | B | 60.7 |
| PP0693 | 1.6E−11 | C | C | 3.8 |
| PP0694 | 2.5E−11 | C | C | 3.5 |
| PP0695 | 1.5E−11 | C | C | 2.9 |
| PP0696 | 1.2E−11 | B | B | 3.3 |
| PP0697 | 2.1E−11 | C | C | 3.8 |
| PP0698 | 1.5E−11 | C | C | 4.1 |
| PP0699 | 3.6E−11 | C | C | 2.9 |
| PP0700 | 1.3E−11 | C | B | 2.9 |
| PP0701 | 1.7E−11 | C | B | 3.8 |
| PP0702 | 4.4E−11 | C | C | 3.3 |
| PP0703 | 1.3E−11 | C | B | 26.7 |
| PP0704 | 1.1E−11 | C | C | 11.4 |
| PP0705 | 2.7E−11 | C | B | 17.5 |
| PP0706 | 3.6E−09 | B | B | 5394.0 |
| PP0708 | 2.6E−11 | C | B | 5.5 |
| PP0709 | 3.0E−11 | C | B | 1.0 |
| PP0710 | 2.9E−11 | C | B | 4.9 |
| PP0711 | 2.5E−11 | C | B | 6.5 |
| PP0712 | 4.2E−11 | C | C | 7.1 |
| PP0713 | 3.3E−11 | C | B | 4.2 |
| PP0714 | 4.7E−11 | C | B | 5.1 |
| PP0715 | 3.5E−11 | C | B | 4.5 |
| PP0716 | 5.5E−11 | C | B | 6.3 |
| PP0717 | 3.2E−11 | B | B | 4.8 |
| PP0718 | 2.9E−11 | C | B | 42.3 |
| PP0719 | 2.0E−11 | C | B | 8.5 |
| PP0720 | 3.6E−11 | C | B | 13.7 |
| PP0721 | 1.1E−08 | B | B | 4701.7 |
| PP0722 | 2.5E−08 | C | B | 2599.5 |
| PP0723 | 4.7E−10 | B | B | 10.8 |
| PP0724 | 4.4E−10 | B | B | 127.3 |
| PP0725 | 5.0E−09 | B | B | 193.9 |
| PP0726 | 1.1E−09 | B | B | 32.7 |
| PP0727 | 1.3E−09 | B | B | 85.2 |
| PP0728 | 1.1E−08 | B | B | 252.0 |
| PP0729 | 2.7E−09 | B | B | 216.0 |
| PP0730 | 9.4E−11 | C | C | 29.6 |
| PP0731 | 1.6E−09 | B | B | 109.6 |
| PP0732 | 3.9E−11 | C | B | 39.6 |
| PP0733 | 7.7E−10 | B | B | 220.1 |
| PP0734 | 3.8E−10 | B | C | 28.8 |
| PP0735 | 2.7E−10 | B | C | 40.9 |
| PP0736 | 1.8E−09 | B | C | 129.9 |
| PP0737 | 5.5E−10 | B | C | 38.2 |
| PP0738 | 6.4E−10 | B | B | 99.2 |
| PP0739 | 3.7E−09 | B | C | 296.8 |
| PP0740 | 4.7E−10 | B | C | 51.2 |
| PP0741 | 2.8E−10 | B | B | 51.5 |
| PP0742 | 5.1E−10 | B | B | 73.3 |
| PP0743 | 6.8E−10 | B | C | 76.3 |
| PP0744 | 6.0E−11 | B | B | 57.0 |
| PP0745 | 2.9E−11 | B | C | 3.9 |
| PP0746 | 4.3E−10 | B | C | 35.4 |
| PP0747 | 3.6E−10 | B | C | 45.9 |
| PP0748 | 8.0E−11 | B | B | 10.7 |
| PP0749 | 5.9E−10 | B | C | 19.8 |
| PP0750 | 3.7E−10 | B | C | 11.1 |
| PP0751 | 5.2E−10 | B | C | 25.5 |
| PP0752 | 5.4E−10 | B | B | 25.8 |
| PP0753 | 1.4E−10 | B | C | 8.2 |
| PP0754 | 4.9E−10 | B | C | 40.4 |
| PP0755 | 5.6E−10 | B | B | 83.8 |
| PP0756 | 8.7E−10 | B | B | 69.5 |
| PP0757 | 4.0E−09 | B | C | 480.2 |
| PP0758 | 1.6E−09 | B | C | 153.1 |
| PP0759 | 2.7E−09 | B | B | 184.7 |
| PP0760 | 1.6E−08 | B | C | 309.6 |
| PP0761 | 1.6E−09 | B | C | 58.4 |
| PP0762 | 7.3E−10 | B | B | 30.1 |
| PP0763 | 9.8E−10 | B | B | 83.0 |
| PP0764 | 3.4E−09 | B | B | 215.3 |
| PP0765 | 3.1E−10 | B | C | 123.0 |
| PP0766 | 9.6E−11 | B | B | 8.7 |
| PP0767 | 1.9E−09 | B | C | 157.5 |
| PP0768 | 9.7E−10 | B | C | 36.1 |
| PP0769 | 2.1E−10 | B | C | 43.3 |
| PP0770 | 8.4E−10 | B | B | 62.2 |
| PP0771 | 3.3E−09 | B | B | 203.7 |
| PP0772 | 4.3E−09 | B | B | 434.5 |
| PP0773 | 4.0E−09 | B | B | 170.1 |
| PP0774 | 1.7E−08 | B | B | 478.1 |
| PP0775 | 9.2E−09 | B | B | 416.7 |
| PP0776 | 1.5E−08 | B | B | 591.2 |
| PP0778 | 1.0E−08 | B | B | 545.9 |
| PP0779 | 5.1E−09 | B | B | 364.5 |
| PP0780 | 7.8E−09 | B | B | 527.3 |
| PP0781 | 1.7E−08 | B | B | 651.2 |
| PP0782 | 2.3E−09 | B | B | 425.1 |
| PP0783 | 8.5E−10 | B | B | 122.1 |
| PP0784 | 1.7E−08 | B | B | 446.6 |
| PP0785 | 3.0E−09 | B | B | 324.4 |
| PP0786 | 6.0E−10 | B | B | 44.8 |
| PP0787 | 3.4E−10 | C | B | 38.3 |
| PP0788 | 5.4E−11 | B | C | 7.1 |
| PP0789 | 1.2E−10 | C | B | 12.5 |
| PP0790 | 5.6E−10 | C | B | 28.8 |
| PP0791 | 9.8E−10 | C | B | 86.0 |
| PP0792 | 9.0E−10 | C | B | 111.9 |
| PP0793 | 3.4E−09 | C | B | 689.7 |
| PP0794 | 1.5E−09 | C | B | 122.5 |
| PP0795 | 2.5E−09 | C | B | 355.8 |
| PP0796 | 7.5E−09 | C | B | 437.6 |
| PP0797 | 1.7E−09 | C | B | 80.6 |
| PP0798 | 1.9E−09 | C | B | 61.5 |
| PP0799 | 1.5E−09 | C | B | 36.3 |
| PP0800 | 2.7E−09 | C | B | 186.4 |
| PP0801 | 4.5E−10 | C | B | 28.7 |
| PP0802 | 8.2E−11 | C | B | 6.5 |

TABLE 37-continued

| Compound No. | KRAS KD (M) | NRAS/KRAS | HRAS/KRAS | NCI-H441 IC$_{50}$ (nM) |
|---|---|---|---|---|
| PP0803 | 1.7E−09 | C | B | 52.5 |
| PP0804 | 1.4E−09 | C | B | 40.9 |
| PP0805 | 1.6E−10 | B | C | 10.3 |
| PP0806 | 1.9E−10 | B | B | 16.9 |
| PP0807 | 5.9E−11 | B | B | 16.7 |
| PP0808 | 2.7E−11 | B | B | 16.7 |
| PP0809 | 2.7E−11 | B | B | 8.4 |
| PP0810 | 4.0E−11 | B | B | 12.8 |
| PP0811 | 8.3E−11 | B | B | 9.8 |
| PP0812 | 2.2E−10 | B | B | 17.9 |
| PP0813 | 4.0E−10 | C | B | 90.3 |
| PP0814 | 3.9E−11 | B | B | 19.4 |
| PP0815 | 3.9E−09 | B | B | 344.7 |
| PP0816 | 5.0E−10 | A | B | 92.5 |
| PP0817 | 3.6E−10 | A | B | 111.7 |
| PP0818 | 1.7E−09 | B | B | 43.7 |
| PP0819 | 5.6E−10 | A | B | 75.7 |
| PP0820 | 1.2E−09 | A | B | 60.1 |
| PP0821 | 2.0E−09 | A | B | 250.2 |
| PP0822 | 5.7E−09 | B | B | 1988.1 |
| PP0823 | 8.2E−10 | A | B | 130.5 |
| PP0824 | 5.5E−11 | A | A | 23.6 |
| PP0825 | 2.3E−10 | A | A | 26.5 |
| PP0826 | 1.3E−10 | C | B | 11.5 |
| PP0827 | 1.1E−10 | C | C | 15.7 |
| PP0828 | 1.7E−10 | C | C | 7.3 |
| PP0829 | 8.1E−11 | B | C | 4.4 |
| PP0830 | 5.8E−11 | C | C | 3.4 |
| PP0831 | 3.2E−10 | C | C | 3.7 |
| PP0832 | 2.1E−10 | C | C | 21.5 |
| PP0833 | 9.0E−10 | B | B | 41.3 |
| PP0834 | 1.9E−10 | A | B | 13.6 |
| PP0835 | 1.4E−10 | B | B | 122.1 |
| PP0836 | 6.3E−10 | B | B | 359.8 |
| PP0837 | 1.9E−10 | B | B | 63.4 |
| PP0838 | 5.3E−10 | B | B | 50.4 |
| PP0839 | 1.1E−09 | B | B | 122.5 |
| PP0840 | 5.0E−09 | B | B | 571.8 |
| PP0841 | 7.3E−10 | B | B | 112.5 |
| PP0842 | 6.0E−10 | B | B | 173.8 |
| PP0843 | 5.2E−10 | B | B | 38.6 |
| PP0844 | 1.2E−09 | B | B | 50.2 |
| PP0845 | 2.2E−10 | B | B | 134.9 |
| PP0846 | 9.9E−10 | B | B | 22.2 |
| PP0847 | 2.8E−10 | B | B | 135.6 |
| PP0848 | 5.7E−10 | B | B | 37.5 |
| PP0849 | 4.6E−10 | B | B | 35.7 |
| PP0850 | 1.2E−08 | B | B | 3085.5 |
| PP0851 | 5.2E−10 | B | B | 37.9 |
| PP0852 | 4.6E−10 | B | B | 35.3 |
| PP0853 | 6.7E−10 | B | B | 24.3 |
| PP0854 | 3.8E−10 | B | B | 21.7 |
| PP0855 | 8.4E−10 | B | B | 114.2 |
| PP0856 | 9.6E−10 | B | B | 66.7 |
| PP0857 | 1.4E−09 | B | B | 111.2 |
| PP0858 | 6.6E−10 | B | B | 52.5 |
| PP0859 | 3.1E−10 | B | B | 22.4 |
| PP0860 | 1.1E−09 | B | B | 142.8 |
| PP0861 | 6.6E−10 | B | B | 20.7 |
| PP0862 | 1.1E−09 | B | B | 81.1 |
| PP0863 | 6.0E−10 | B | B | 228.5 |
| PP0864 | 4.9E−10 | B | B | 185.2 |
| PP0865 | 1.1E−09 | B | B | 767.1 |
| PP0866 | 5.3E−10 | B | B | 197.4 |
| PP0867 | 1.2E−09 | B | B | 205.9 |
| PP0868 | 5.3E−11 | C | B | 70.8 |
| PP0869 | 5.6E−11 | B | B | 134.3 |
| PP0870 | 5.7E−11 | B | B | 79.7 |
| PP0871 | 4.0E−10 | B | B | 438.1 |
| PP0872 | 1.7E−09 | A | A | 2599.3 |
| PP0873 | 8.6E−10 | A | B | 896.1 |
| PP0874 | 1.0E−10 | C | B | 4.9 |
| PP0875 | 9.6E−11 | C | B | 4.8 |
| PP0876 | 4.0E−10 | C | C | 7.1 |
| PP0877 | 2.1E−10 | C | B | 18.8 |
| PP0878 | 3.2E−09 | B | B | 85.9 |
| PP0879 | 8.6E−09 | B | B | 194.9 |
| PP0880 | 4.5E−09 | B | B | 160.2 |
| PP0881 | 5.5E−09 | | | 374.1 |
| PP0882 | 2.0E−11 | C | B | 7.1 |
| PP0883 | 3.7E−10 | B | B | 59.3 |
| PP0884 | 2.2E−11 | C | C | 6.2 |
| PP0885 | 9.8E−11 | C | B | 11.5 |
| PP0886 | 8.6E−11 | C | B | 14.3 |
| PP0887 | 9.3E−11 | C | C | 19.0 |
| PP0888 | 1.7E−10 | C | B | 25.6 |
| PP0889 | 1.3E−10 | B | B | 26.7 |
| PP0890 | 1.2E−09 | B | B | 183.0 |
| PP0891 | 6.2E−10 | B | B | 154.0 |
| PP0892 | 3.3E−10 | B | B | 53.6 |
| PP0893 | 1.3E−09 | B | B | 226.5 |
| PP0894 | 8.8E−12 | C | C | 3.7 |
| PP0895 | 7.2E−12 | C | C | 2.2 |
| PP0896 | 1.8E−11 | C | C | 3.1 |
| PP0898 | 8.8E−10 | B | B | 119.8 |
| PP0899 | 9.9E−10 | A | B | 922.8 |
| PP0900 | 1.2E−11 | C | C | 4.9 |
| PP0901 | 3.0E−09 | B | B | 332.0 |
| PP0902 | 6.3E−10 | A | B | 72.6 |
| PP0903 | 3.6E−09 | B | C | 596.2 |
| PP0904 | 8.0E−10 | B | B | 58.7 |
| PP0905 | 7.9E−10 | B | B | 92.0 |
| PP0906 | 2.9E−10 | B | B | 36.9 |
| PP0907 | 1.6E−10 | B | B | 24.8 |
| PP0908 | 1.9E−10 | B | B | 38.5 |
| PP0909 | 4.8E−10 | B | B | 58.1 |
| PP0910 | 6.2E−10 | B | B | 66.2 |
| PP0911 | 6.0E−11 | B | B | 10.2 |
| PP0912 | 3.2E−10 | B | B | 40.5 |
| PP0913 | 1.1E−09 | B | B | 206.4 |
| PP0914 | 4.3E−10 | B | B | 40.2 |
| PP0915 | 1.4E−10 | B | B | 37.6 |
| PP0916 | 3.4E−10 | B | B | 35.9 |
| PP0917 | 1.6E−10 | B | B | 25.2 |
| PP0918 | 4.0E−10 | B | B | 27.7 |
| PP0919 | 8.1E−10 | B | B | 109.5 |
| PP0920 | 2.9E−10 | B | B | 75.5 |
| PP0921 | 2.6E−09 | B | B | 139.0 |
| PP0922 | 5.0E−10 | B | B | 98.2 |
| PP0923 | 1.6E−09 | B | B | 445.2 |
| PP0924 | 8.2E−10 | B | B | 92.0 |
| PP0925 | 1.1E−09 | A | B | 91.0 |
| PP0926 | 2.4E−09 | B | B | 113.4 |
| PP0927 | 1.0E−09 | B | B | 112.9 |
| PP0928 | 1.0E−09 | A | B | 182.3 |
| PP0929 | 2.7E−09 | A | B | 316.8 |
| PP0930 | 1.8E−09 | A | B | 141.9 |
| PP0931 | 1.9E−09 | A | B | 180.7 |
| PP0932 | 2.9E−09 | B | B | 158.3 |
| PP0933 | 1.6E−09 | A | B | 150.1 |
| PP0934 | 7.2E−10 | B | B | 51.8 |
| PP0935 | 4.3E−10 | B | B | 26.9 |
| PP0936 | 4.2E−10 | B | B | 42.4 |
| PP0937 | 1.0E−09 | B | B | 39.0 |
| PP0938 | 1.1E−09 | B | B | 175.1 |
| PP0939 | 9.1E−10 | B | B | 114.1 |
| PP0940 | 2.0E−09 | B | C | 110.1 |
| PP0941 | 1.2E−09 | B | B | 63.9 |
| PP0942 | 9.9E−10 | B | B | 66.1 |
| PP0943 | 1.1E−09 | B | B | 154.2 |
| PP0944 | 3.9E−09 | A | A | 344.2 |
| PP0945 | 3.7E−09 | B | A | 986.7 |
| PP0946 | 2.2E−09 | A | B | 377.8 |
| PP0947 | 3.4E−09 | A | A | 596.6 |
| PP0948 | 3.2E−09 | A | A | 234.5 |
| PP0949 | 6.7E−09 | A | A | 658.8 |
| PP0950 | 6.0E−09 | A | B | 958.4 |
| PP0951 | 6.3E−09 | A | A | 945.5 |
| PP0952 | 8.5E−09 | A | A | 1080.4 |
| PP0953 | 2.7E−08 | A | A | 1612.8 |
| PP0954 | 7.5E−09 | A | A | 438.5 |
| PP0955 | 1.9E−08 | A | A | 6475.4 |
| PP0956 | 7.2E−09 | A | A | 690.3 |
| PP0958 | 7.5E−09 | B | B | 1038.1 |

TABLE 37-continued

| Compound No. | KRAS KD (M) | NRAS/ KRAS | HRAS/ KRAS | NCI-H441 IC$_{50}$ (nM) |
|---|---|---|---|---|
| PP0959 | 3.9E−10 | B | B | 156.2 |
| PP0960 | 3.7E−10 | B | B | 101.4 |
| PP0961 | 6.2E−10 | B | B | 53.6 |
| PP0962 | 6.5E−10 | B | B | 83.9 |
| PP0963 | 7.8E−10 | B | B | 100.0 |
| PP0964 | 5.9E−10 | B | B | 56.6 |
| PP0965 | 5.7E−10 | B | B | 48.8 |
| PP0966 | 2.3E−10 | B | B | 34.6 |
| PP0967 | 3.3E−10 | B | B | 77.7 |
| PP0968 | 3.2E−10 | B | B | 38.8 |
| PP0969 | 1.2E−10 | B | B | 13.6 |
| PP0970 | 2.2E−09 | B | B | 340.5 |
| PP0971 | 3.4E−10 | B | B | 54.0 |
| PP0972 | 1.5E−10 | B | B | 15.8 |
| PP0973 | 8.5E−11 | B | B | 11.6 |
| PP0975 | 8.9E−09 | | | 1567.6 |
| PP0976 | 4.8E−09 | B | B | 1178.5 |
| PP0977 | 7.7E−09 | B | A | 1115.5 |
| PP0978 | 8.8E−11 | A | B | 22.7 |
| PP0979 | 1.7E−09 | AA | A | 281.1 |
| PP0980 | 8.8E−10 | A | B | 222.8 |
| PP0981 | 1.1E−08 | AA | A | 797.4 |
| PP0982 | 9.9E−10 | AA | A | 372.4 |
| PP0983 | 7.8E−11 | A | A | 19.5 |
| PP0984 | 2.8E−10 | A | A | 64.6 |
| PP0985 | 2.2E−11 | C | C | 12.2 |
| PP0986 | 2.7E−10 | C | C | 45.9 |
| PP0987 | 2.4E−11 | C | C | 6.8 |
| PP0988 | 4.6E−11 | C | B | 10.3 |
| PP0989 | 1.3E−09 | B | B | 134.8 |
| PP0992 | 4.6E−09 | B | B | 790.3 |
| PP0993 | 1.4E−09 | B | B | 331.8 |
| PP0997 | 5.6E−08 | A | A | 2627.1 |
| PP0998 | 1.2E−10 | B | B | 19.7 |
| PP0999 | 1.1E−10 | C | B | 7.6 |
| PP1000 | 3.9E−11 | B | B | 7.5 |
| PP1001 | 1.0E−10 | B | B | 28.1 |
| PP1002 | 2.5E−11 | B | B | 2.1 |
| PP1003 | 7.6E−11 | C | B | 29.1 |
| PP1004 | 3.7E−09 | B | B | 254.6 |
| PP1005 | 1.1E−09 | A | A | 274.7 |
| PP1006 | 3.2E−10 | B | B | 81.9 |
| PP1008 | 1.1E−09 | A | A | 101.6 |
| PP1009 | 2.0E−09 | B | B | 195.0 |
| PP1010 | 1.5E−09 | B | B | 179.1 |
| PP1011 | 3.7E−09 | A | B | 314.2 |
| PP1012 | 9.0E−10 | A | B | 41.6 |
| PP1013 | 3.4E−09 | C | C | 269.3 |
| PP1014 | 1.1E−09 | C | C | 114.4 |
| PP1015 | 5.0E−09 | C | C | 110.0 |
| PP1016 | 2.7E−10 | A | B | 61.2 |
| PP1017 | 4.8E−11 | C | B | 5.0 |
| PP1018 | 1.7E−11 | C | B | 6.8 |
| PP1019 | 5.5E−11 | C | B | 7.4 |
| PP1020 | 2.2E−11 | C | B | 18.0 |
| PP1021 | 5.7E−11 | C | B | 14.0 |
| PP1022 | 3.6E−11 | C | B | 17.5 |
| PP1024 | 8.8E−11 | B | B | 12.7 |
| PP1025 | 5.6E−11 | C | B | 10.7 |
| PP1026 | 1.2E−10 | B | B | 10.4 |
| PP1027 | 5.6E−11 | C | B | 7.2 |
| PP1028 | 9.9E−11 | B | B | 17.3 |
| PP1029 | 7.8E−11 | C | B | 24.3 |
| PP1030 | 2.6E−10 | B | B | 27.9 |
| PP1031 | 6.7E−10 | C | C | 86.2 |
| PP1032 | 3.8E−10 | C | C | 43.9 |
| PP1033 | 4.3E−10 | C | C | 67.2 |
| PP1034 | 4.3E−10 | C | C | 96.8 |
| PP1035 | 5.2E−10 | C | C | 127.6 |
| PP1036 | 7.5E−10 | C | C | 149.8 |
| PP1037 | 7.6E−10 | C | C | 296.0 |
| PP1038 | 3.0E−09 | C | C | 187.8 |
| PP1039 | 5.9E−10 | C | C | 98.4 |
| PP1040 | 1.2E−09 | C | C | 18.7 |
| PP1041 | 5.7E−10 | C | C | 223.4 |
| PP1042 | 1.3E−09 | C | C | 348.8 |
| PP1043 | 2.4E−09 | C | C | 386.8 |
| PP1044 | 1.8E−09 | C | C | 44.1 |
| PP1045 | 1.7E−09 | C | C | 206.7 |
| PP1046 | 3.8E−10 | C | C | 109.4 |
| PP1047 | 8.5E−10 | C | C | 117.2 |
| PP1048 | 4.9E−10 | C | C | 133.8 |
| PP1049 | 9.1E−10 | C | C | 358.6 |
| PP1050 | 9.4E−10 | C | C | 815.0 |
| PP1051 | 1.8E−09 | C | C | 285.7 |
| PP1052 | 2.5E−10 | A | A | 58.7 |
| PP1053 | 2.3E−10 | A | A | 67.8 |
| PP1054 | 3.9E−09 | A | B | 468.9 |
| PP1056 | 2.1E−10 | A | A | 75.0 |
| PP1057 | 3.1E−10 | A | B | 96.9 |
| PP1058 | 2.9E−09 | A | B | 599.1 |
| PP1059 | 9.1E−10 | A | B | 200.7 |
| PP1060 | 2.6E−09 | A | A | 306.8 |
| PP1063 | 1.2E−09 | A | A | 380.1 |
| PP1064 | 1.7E−08 | A | A | 1392.2 |
| PP1065 | 4.5E−10 | A | B | 96.7 |
| PP1067 | 2.9E−09 | B | B | 299.0 |
| PP1068 | 1.1E−09 | A | B | 120.9 |
| PP1069 | 2.5E−09 | A | B | 126.9 |
| PP1070 | 7.5E−11 | B | B | 11.9 |
| PP1071 | 1.0E−10 | B | B | 24.7 |
| PP1072 | 6.3E−11 | B | B | 13.0 |
| PP1073 | 3.6E−10 | B | B | 83.7 |
| PP1075 | 6.6E−11 | B | B | 21.8 |
| PP1076 | 6.8E−11 | B | B | 4.6 |
| PP1077 | 8.5E−11 | B | B | 14.9 |
| PP1078 | 4.7E−10 | B | B | 610.2 |
| PP1079 | 2.3E−10 | B | B | 27.2 |
| PP1080 | 2.4E−10 | B | B | 39.2 |
| PP1082 | 3.5E−09 | A | B | 299.6 |
| PP1083 | 3.4E−09 | B | B | 221.4 |
| PP1084 | 9.1E−11 | C | B | 83.9 |
| PP1085 | 9.5E−10 | A | A | 589.9 |
| PP1086 | 1.3E−10 | AA | A | 22.4 |
| PP1087 | 9.5E−11 | A | A | 40.4 |
| PP1088 | 5.5E−10 | A | A | 195.0 |
| PP1089 | 1.2E−10 | AA | A | 57.3 |
| PP1090 | 8.6E−11 | AA | A | 20.9 |
| PP1091 | 1.1E−10 | A | B | 17.9 |
| PP1092 | 1.5E−10 | A | A | 15.8 |
| PP1093 | 5.8E−10 | AA | A | 78.7 |
| PP1094 | 8.4E−10 | A | B | 778.0 |
| PP1095 | 1.8E−10 | B | B | 14.9 |
| PP1096 | 2.4E−10 | B | B | 38.1 |
| PP1097 | 1.2E−10 | B | B | 10.2 |
| PP1098 | 6.8E−10 | B | B | 100.9 |
| PP1099 | 5.8E−10 | B | A | 68.1 |
| PP1100 | 1.9E−10 | B | B | 17.6 |
| PP1101 | 4.6E−10 | B | B | 68.4 |
| PP1102 | 9.5E−10 | B | A | 83.1 |
| PP1103 | 3.6E−11 | A | B | 34.8 |
| PP1104 | 5.9E−11 | A | A | 44.6 |
| PP1105 | 7.0E−11 | A | A | 12.0 |
| PP1106 | 8.1E−10 | A | A | 154.6 |
| PP1107 | 3.8E−11 | A | A | 5.4 |
| PP1108 | 3.3E−11 | A | A | 28.3 |
| PP1109 | 1.2E−10 | A | B | 17.0 |
| PP1110 | 5.6E−11 | A | B | 11.2 |
| PP1111 | 4.5E−11 | A | A | 13.0 |
| PP1112 | 6.0E−11 | A | B | 10.4 |
| PP1113 | 3.1E−11 | A | A | 21.4 |
| PP1114 | 5.4E−11 | A | A | 12.2 |
| PP1115 | 5.4E−11 | A | A | 29.0 |
| PP1116 | 6.9E−11 | A | A | 19.8 |
| PP1117 | 7.0E−11 | A | A | 16.5 |
| PP1118 | 5.6E−11 | A | B | 6.5 |
| PP1119 | 3.7E−11 | A | A | 25.5 |
| PP1120 | 4.2E−11 | A | A | 20.6 |
| PP1121 | 4.9E−11 | A | A | 17.3 |
| PP1122 | 4.7E−11 | A | B | 274.9 |
| PP1123 | 7.2E−11 | A | B | 13.4 |
| PP1124 | 5.6E−11 | A | B | 12.4 |
| PP1125 | 7.0E−11 | A | A | 15.0 |
| PP1126 | 8.9E−11 | A | A | 7.1 |

TABLE 37-continued

| Compound No. | KRAS KD (M) | NRAS/KRAS | HRAS/KRAS | NCI-H441 IC$_{50}$ (nM) |
|---|---|---|---|---|
| PP1127 | 1.1E−10 | AA | A | 11.9 |
| PP1128 | 1.2E−10 | AA | A | 120.7 |
| PP1129 | 5.6E−11 | A | B | 10.2 |
| PP1130 | 3.5E−11 | A | B | 19.6 |
| PP1131 | 2.5E−10 | A | B | 32.0 |
| PP1132 | 6.6E−11 | A | B | 86.8 |
| PP1133 | 5.0E−11 | A | A | 16.5 |
| PP1134 | 6.0E−11 | A | B | 20.0 |
| PP1135 | 9.4E−11 | A | A | 43.9 |
| PP1136 | 1.4E−10 | A | A | 193.4 |
| PP1137 | 1.1E−10 | AA | A | 141.7 |
| PP1138 | 1.9E−10 | A | A | 244.5 |
| PP1139 | 4.3E−10 | A | A | 296.8 |
| PP1140 | 1.5E−10 | A | A | 1776.6 |
| PP1141 | 3.2E−10 | AA | A | 423.6 |
| PP1142 | 6.5E−10 | A | A | 321.5 |
| PP1143 | 1.7E−10 | A | A | 75.3 |
| PP1144 | 2.4E−10 | AA | A | 155.4 |
| PP1145 | 2.1E−10 | A | B | 140.0 |
| PP1146 | 3.2E−10 | A | B | 202.3 |
| PP1147 | 7.1E−10 | A | A | 888.4 |
| PP1148 | 1.2E−09 | A | A | 357.1 |
| PP1149 | 4.3E−10 | A | A | 173.0 |
| PP1150 | 1.7E−10 | AA | A | 42.7 |
| PP1151 | 6.4E−10 | B | B | 97.1 |
| PP1152 | 1.3E−09 | B | B | 299.8 |
| PP1153 | 2.8E−10 | B | B | 15.5 |
| PP1154 | 4.3E−10 | B | B | 69.6 |
| PP1155 | 1.5E−10 | B | B | 73.1 |
| PP1156 | 6.3E−11 | B | B | 33.7 |
| PP1157 | 6.1E−11 | B | B | 30.3 |
| PP1158 | 1.8E−10 | B | B | 57.5 |
| PP1159 | 3.6E−11 | C | B | 13.0 |
| PP1160 | 3.2E−11 | B | B | 18.4 |
| PP1161 | 6.0E−10 | B | B | 153.4 |
| PP1162 | 1.2E−09 | B | B | 198.5 |
| PP1163 | 5.9E−10 | B | B | 93.3 |
| PP1164 | 5.2E−10 | B | B | 95.9 |
| PP1165 | 1.5E−09 | A | B | 295.3 |
| PP1166 | 5.0E−10 | B | B | 124.5 |
| PP1167 | 5.0E−10 | B | B | 134.1 |
| PP1168 | 1.8E−09 | A | A | 337.7 |
| PP1169 | 3.2E−10 | B | B | 74.0 |
| PP1170 | 2.3E−10 | B | B | 64.7 |
| PP1171 | 6.9E−10 | B | B | 117.5 |
| PP1172 | 1.7E−10 | B | B | 48.3 |
| PP1173 | 1.8E−10 | B | B | 70.8 |
| PP1174 | 1.0E−09 | B | B | 85.2 |
| PP1175 | 1.6E−10 | B | B | 23.5 |
| PP1176 | 1.3E−10 | B | B | 50.0 |
| PP1177 | 8.1E−11 | B | B | 32.5 |
| PP1178 | 1.6E−10 | B | B | 26.3 |
| PP1179 | 9.1E−11 | B | B | 56.9 |
| PP1180 | 1.7E−10 | B | B | 46.9 |
| PP1181 | 1.9E−10 | B | B | 26.3 |
| PP1182 | 8.0E−11 | B | B | 134.5 |
| PP1183 | 2.6E−10 | B | B | 27.8 |
| PP1184 | 1.6E−10 | B | B | 91.9 |
| PP1185 | 5.0E−10 | B | B | 175.0 |
| PP1186 | 9.4E−11 | B | B | 54.4 |
| PP1187 | 1.2E−10 | B | B | 52.3 |
| PP1188 | 4.3E−10 | B | B | 33.5 |
| PP1189 | 6.6E−11 | B | B | 16.1 |
| PP1190 | 9.2E−11 | B | B | 15.5 |
| PP1191 | 5.6E−11 | A | B | 13.0 |
| PP1192 | 4.0E−11 | B | A | 10.5 |
| PP1193 | 7.0E−11 | B | B | 16.3 |
| PP1194 | 6.8E−11 | B | B | 25.3 |
| PP1195 | 7.4E−11 | B | B | 18.3 |
| PP1196 | 4.0E−11 | B | B | 50.8 |
| PP1197 | 9.6E−11 | B | B | 14.8 |
| PP1198 | 1.9E−10 | B | B | 35.2 |
| PP1199 | 1.7E−10 | A | A | 39.1 |
| PP1200 | 2.0E−10 | AA | A | 19.2 |
| PP1201 | 1.7E−10 | AA | A | 9.7 |
| PP1202 | 4.0E−10 |  |  | 24.1 |
| PP1203 | 2.3E−10 | A | A | 20.8 |
| PP1204 | 2.4E−10 | AA | A | 23.4 |
| PP1205 | 1.6E−10 | AA | A | 25.4 |
| PP1206 | 1.7E−10 | AA | A | 109.4 |
| PP1207 | 2.1E−10 | AA | A | 29.9 |
| PP1208 | 1.7E−10 | AA | A | 24.4 |
| PP1209 | 2.2E−10 | AA | A | 15.9 |
| PP1210 | 4.0E−10 | AA | A | 44.3 |
| PP1211 | 2.7E−10 | A | B | 26.8 |
| PP1212 | 2.8E−10 | AA | A | 35.6 |
| PP1213 | 1.8E−10 | AA | A | 40.4 |
| PP1214 | 3.4E−10 | AA | A | 93.4 |
| PP1215 | 4.2E−10 | AA | A | 33.4 |
| PP1216 | 3.9E−10 | AA | A | 19.8 |
| PP1217 | 4.8E−10 | AA | A | 17.8 |
| PP1218 | 8.8E−10 | AA | A | 67.9 |
| PP1219 | 3.5E−10 | AA | A | 21.4 |
| PP1220 | 5.7E−10 | AA | A | 22.2 |
| PP1221 | 4.0E−10 | AA | A | 40.6 |
| PP1222 | 1.2E−09 | A | A | 301.2 |
| PP1223 | 1.2E−09 | AA | A | 117.3 |
| PP1224 | 1.2E−09 | A | A | 122.4 |
| PP1225 | 1.1E−09 | AA | A | 92.5 |
| PP1226 | 2.4E−09 | AA | A | 105.8 |
| PP1227 | 1.6E−09 | A | A | 127.6 |
| PP1228 | 1.6E−09 | AA | A | 55.1 |
| PP1229 | 1.3E−09 | A | A | 144.5 |
| PP1230 | 7.7E−10 | A | A | 109.7 |
| PP1231 | 5.6E−10 | AA | A | 23.1 |
| PP1232 | 6.7E−10 | A | A | 59.7 |
| PP1233 | 6.6E−10 | AA | A | 34.7 |
| PP1234 | 3.8E−09 | B | C | 398.0 |
| PP1235 | 6.7E−09 | B | C | 386.0 |
| PP1242 | 7.6E−11 | A | A | 12.8 |
| PP1243 | 5.8E−11 | A | A | 13.2 |
| PP1244 | 6.1E−11 | A | B | 8.9 |
| PP1245 | 6.0E−11 | A | B | 3.7 |
| PP1246 | 8.1E−11 | A | A | 9.0 |
| PP1247 | 4.6E−11 | A | A | 6.4 |
| PP1248 | 6.9E−11 | A | A | 7.3 |
| PP1249 | 1.8E−10 | A | A | 55.4 |
| PP1250 | 1.9E−10 | AA | A | 18.7 |
| PP1251 | 1.8E−10 | AA | A | 10.2 |
| PP1252 | 3.0E−10 | AA | A | 51.2 |
| PP1253 | 2.0E−10 | A | A | 22.2 |
| PP1254 | 2.0E−10 | AA | A | 28.3 |
| PP1255 | 3.9E−10 | A | A | 156.0 |
| PP1256 | 3.6E−10 | A | A | 69.0 |
| PP1257 | 3.3E−10 | A | A | 54.3 |
| PP1258 | 1.9E−10 | AA | A | 21.3 |
| PP1259 | 4.9E−10 | A | A | 62.0 |
| PP1260 | 3.7E−10 | A | A | 60.4 |
| PP1261 | 4.4E−10 | A | A | 76.8 |
| PP1262 | 2.4E−10 | A | B | 56.7 |
| PP1263 | 2.3E−10 | A | A | 18.9 |
| PP1264 | 3.7E−10 | A | B | 15.9 |
| PP1265 | 1.7E−10 | A | B | 14.1 |
| PP1266 | 4.5E−11 | A | A | 12.2 |
| PP1267 | 4.6E−11 | A | A | 10.8 |
| PP1268 | 4.5E−11 | A | A | 12.1 |
| PP1269 | 9.1E−11 | A | B | 29.0 |
| PP1270 | 1.3E−10 | A | B | 53.5 |
| PP1271 | 5.4E−11 | AA | A | 90.7 |
| PP1272 | 1.1E−10 | A | A | 24.0 |
| PP1273 | 1.2E−10 | A | B | 16.5 |
| PP1274 | 3.2E−11 | A | A | 7.5 |
| PP1275 | 4.7E−11 | A | A | 4.9 |
| PP1276 | 6.6E−11 | A | B | 20.8 |
| PP1277 | 2.5E−10 | A | A | 79.8 |
| PP1278 | 1.4E−10 | A | B | 45.7 |
| PP1279 | 2.7E−10 | A | A | 72.6 |
| PP1280 | 1.5E−10 | A | A | 34.4 |
| PP1281 | 1.4E−10 | AA | A | 10.2 |
| PP1282 | 2.0E−10 | A | A | 12.3 |
| PP1283 | 2.0E−10 | AA | A | 42.6 |
| PP1284 | 1.2E−10 | AA | A | 54.8 |
| PP1285 | 1.5E−10 | AA | A | 24.6 |
| PP1286 | 6.5E−10 | AA | A | 58.8 |

TABLE 37-continued

| Compound No. | KRAS KD (M) | NRAS/KRAS | HRAS/KRAS | NCI-H441 IC$_{50}$ (nM) |
|---|---|---|---|---|
| PP1287 | 5.6E−10 | AA | A | 49.7 |
| PP1288 | 1.8E−10 | AA | A | 22.2 |
| PP1289 | 1.7E−10 | AA | A | 34.7 |
| PP1290 | 2.4E−10 | AA | A | 15.4 |
| PP1291 | 2.4E−10 | A | A | 16.7 |
| PP1292 | 1.6E−10 | A | A | 24.6 |
| PP1293 | 2.2E−10 | AA | A | 4.9 |
| PP1294 | 2.9E−10 | A | A | 10.0 |
| PP1295 | 1.2E−10 | AA | A | 6.2 |
| PP1296 | 1.2E−10 | AA | A | 14.7 |
| PP1297 | 8.7E−11 | AA | A | 23.1 |
| PP1298 | 1.3E−10 | AA | A | 11.4 |
| PP1299 | 1.4E−10 | A | A | 11.0 |
| PP1300 | 8.2E−11 | A | A | 9.5 |
| PP1301 | 8.3E−11 | A | A | 4.7 |
| PP1302 | 5.7E−11 | A | A | 9.2 |
| PP1303 | 6.8E−11 | AA | A | 4.2 |
| PP1304 | 7.0E−11 | A | A | 8.8 |
| PP1305 | 1.2E−10 | AA | A | 13.0 |
| PP1306 | 2.0E−10 | AA | A | 14.7 |
| PP1307 | 1.4E−10 | A | A | 7.0 |
| PP1308 | 1.0E−10 | A | A | 10.9 |
| PP1309 | 1.6E−10 | A | A | 5.3 |
| PP1310 | 1.3E−10 | AA | A | 4.5 |
| PP1311 | 3.9E−10 | AA | A | 40.3 |
| PP1312 | 4.2E−10 | AA | A | 72.8 |
| PP1313 | 2.7E−10 | AA | A | 66.3 |
| PP1314 | 4.0E−10 | A | A | 57.2 |
| PP1315 | 3.4E−10 | AA | A | 34.5 |
| PP1316 | 7.2E−11 | A | A | 13.2 |
| PP1317 | 9.4E−11 | A | B | 7.6 |
| PP1318 | 9.1E−11 | A | A | 11.5 |
| PP1319 | 6.9E−11 | A | B | 57.5 |
| PP1320 | 5.7E−11 | A | A | 7.7 |
| PP1321 | 8.0E−11 | A | B | 13.9 |
| PP1322 | 5.9E−10 | A | A | 56.2 |
| PP1323 | 2.6E−10 | AA | A | 41.8 |
| PP1324 | 9.3E−11 | A | A | 4.4 |
| PP1325 | 5.5E−10 | A | A | 42.7 |
| PP1326 | 2.7E−10 | AA | A | 23.1 |
| PP1327 | 1.1E−10 | A | A | 12.4 |
| PP1328 | 5.6E−10 | A | A | 134.3 |
| PP1329 | 2.4E−10 | AA | A | 34.5 |
| PP1330 | 4.2E−10 | AA | A | 79.6 |
| PP1331 | 8.0E−11 | A | A | 13.9 |
| PP1333 | 5.8E−08 | C | B | 979.5 |
| PP1334 | 1.1E−08 | B | B | 968.3 |
| PP1335 | 1.8E−08 | B | B | 736.5 |
| PP1336 | 7.4E−11 | B | B | 10.8 |
| PP1337 | 1.7E−10 | B | B | 29.8 |
| PP1338 | 1.4E−10 | B | B | 35.0 |
| PP1339 | 6.5E−10 | A | B | 42.1 |
| PP1340 | 8.1E−11 | B | B | 10.9 |
| PP1341 | 8.1E−10 | A | B | 46.3 |
| PP1342 | 9.1E−11 | B | B | 5.0 |
| PP1343 | 2.7E−10 | A | B | 19.3 |
| PP1344 | 1.4E−10 | B | B | 16.7 |
| PP1345 | 7.1E−10 | A | B | 34.8 |
| PP1346 | 8.4E−11 | B | B | 7.2 |
| PP1347 | 1.7E−10 | B | B | 3.6 |
| PP1348 | 7.6E−11 | B | B | 8.7 |
| PP1349 | 9.0E−11 | C | B | 14.7 |
| PP1350 | 1.8E−10 | B | B | 20.1 |
| PP1351 | 1.3E−10 | A | B | 12.8 |
| PP1352 | 2.4E−11 | A | B | 4.6 |
| PP1353 | 1.0E−10 | A | B | 3.7 |
| PP1354 | 5.6E−11 | A | B | 3.6 |
| PP1355 | 1.6E−10 | A | B | 10.2 |
| PP1356 | 4.7E−11 | B | B | 3.3 |
| PP1357 | 1.3E−10 | A | B | 5.4 |
| PP1358 | 3.0E−11 | A | B | 4.1 |
| PP1359 | 6.8E−11 | A | B | 3.2 |
| PP1360 | 5.5E−11 | A | B | 4.9 |
| PP1361 | 1.5E−10 | A | B | 6.2 |
| PP1362 | 3.7E−11 | A | B | 3.7 |
| PP1363 | 3.2E−10 | A | B | 34.7 |
| PP1364 | 5.0E−11 | A | B | 7.1 |
| PP1365 | 1.3E−10 | A | B | 4.2 |
| PP1366 | 1.1E−10 | A | B | 14.0 |
| PP1367 | 3.4E−10 | A | B | 29.3 |
| PP1368 | 6.1E−11 | A | B | 2.9 |
| PP1369 | 2.6E−10 | B | B | 13.4 |
| PP1370 | 5.7E−11 | C | C | 2.3 |
| PP1371 | 7.7E−11 | A | B | 5.1 |
| PP1372 | 7.8E−11 | B | B | 5.0 |
| PP1373 | 3.5E−10 | B | B | 12.2 |
| PP1374 | 3.3E−11 | B | B | 1.9 |
| PP1375 | 2.3E−10 | B | B | 11.5 |
| PP1376 | 3.7E−11 | B | B | 3.5 |
| PP1377 | 8.7E−11 | B | B | 5.8 |
| PP1378 | 8.1E−11 | B | C | 6.6 |
| PP1379 | 2.9E−10 | A | B | 10.3 |
| PP1380 | 4.5E−11 | B | B | 4.1 |
| PP1381 | 7.2E−10 | B | B | 80.4 |
| PP1382 | 6.8E−11 | B | B | 15.8 |
| PP1383 | 1.7E−10 | B | B | 11.2 |
| PP1384 | 1.1E−10 | A | B | 13.5 |
| PP1385 | 8.0E−10 | B | B | 19.6 |
| PP1386 | 8.2E−11 | B | B | 4.2 |
| PP1387 | 9.8E−11 | A | B | 15.3 |
| PP1388 | 7.6E−11 | A | B | 8.8 |
| PP1389 | 6.6E−11 | AA | A | 2.4 |
| PP1390 | 1.1E−09 | A | A | 305.4 |
| PP1391 | 1.6E−09 | A | A | 271.1 |
| PP1392 | 4.7E−11 | A | A | 1.4 |
| PP1393 | 1.9E−10 | A | A | 18.2 |
| PP1394 | 2.4E−10 | AA | A | 25.1 |
| PP1395 | 6.3E−11 | A | B | 3.8 |
| PP1396 | 1.4E−10 | AA | A | 19.4 |
| PP1397 | 7.3E−11 | A | A | 3.7 |
| PP1398 | 3.2E−11 | A | A | 2.3 |
| PP1399 | 1.9E−10 | A | A | 18.8 |
| PP1400 | 4.9E−11 | A | B | 5.1 |
| PP1401 | 2.6E−10 | A | A | 34.4 |
| PP1402 | 3.0E−10 | A | A | 82.0 |
| PP1403 | 6.0E−10 | AA | A | 110.6 |
| PP1404 | 4.8E−09 | A | A | 498.2 |
| PP1405 | 8.5E−09 | A | A | 466.1 |
| PP1406 | 7.2E−11 | A | B | 10.9 |
| PP1407 | 7.4E−11 | A | A | 18.7 |
| PP1408 | 2.2E−10 | A | A | 37.6 |
| PP1409 | 2.1E−10 | A | A | 43.5 |
| PP1410 | 3.2E−10 | B | B | 51.0 |
| PP1411 | 8.0E−11 | A | B | 6.0 |
| PP1412 | 1.9E−10 | A | A | 23.0 |
| PP1413 | 4.2E−10 | B | B | 62.5 |
| PP1414 | 7.4E−11 | A | B | 4.4 |
| PP1415 | 2.5E−10 | A | A | 9.5 |
| PP1416 | 1.7E−10 | A | A | 3.8 |
| PP1417 | 2.6E−10 | B | B | 18.4 |
| PP1418 | 2.4E−10 | AA | A | 29.9 |
| PP1419 | 2.6E−10 | AA | A | 40.4 |
| PP1420 | 3.5E−10 | A | A | 31.4 |
| PP1421 | 3.0E−10 | A | A | 27.9 |
| PP1422 | 2.2E−10 | AA | A | 14.1 |
| PP1423 | 1.4E−10 | AA | A | 4.4 |
| PP1424 | 2.3E−10 | A | A | 26.3 |
| PP1425 | 2.4E−10 | A | B | 20.2 |
| PP1426 | 1.0E−09 | A | B | 474.8 |
| PP1427 | 9.9E−10 | A | B | 465.1 |
| PP1428 | 8.7E−10 | AA | A | 38.8 |
| PP1429 | 5.2E−10 | AA | A | 38.7 |
| PP1430 | 8.5E−10 | A | A | 70.4 |
| PP1431 | 5.7E−10 | AA | A | 41.2 |
| PP1432 | 6.1E−10 | AA | A | 51.3 |
| PP1433 | 4.6E−10 | AA | A | 44.4 |
| PP1434 | 6.9E−10 | A | A | 111.8 |
| PP1435 | 1.1E−09 | A | A | 178.0 |
| PP1436 | 2.9E−10 | AA | A | 47.4 |
| PP1437 | 6.1E−10 | A | A | 219.8 |
| PP1438 | 5.5E−10 | AA | A | 89.4 |
| PP1439 | 1.2E−09 | AA | A | 87.3 |
| PP1440 | 3.5E−10 | AA | A | 69.7 |
| PP1441 | 7.0E−10 | A | A | 87.6 |

TABLE 37-continued

| Compound No. | KRAS KD (M) | NRAS/ KRAS | HRAS/ KRAS | NCI-H441 IC$_{50}$ (nM) |
|---|---|---|---|---|
| PP1442 | 1.3E−10 | A | A | 48.3 |
| PP1443 | 1.5E−10 | AA | A | 34.8 |
| PP1444 | 1.9E−10 | A | A | 102.6 |
| PP1445 | 2.7E−10 | A | A | 92.8 |
| PP1446 | 2.0E−10 | A | A | 32.0 |
| PP1447 | 1.2E−10 | A | A | 28.9 |
| PP1448 | 5.9E−11 | A | A | 8.3 |
| PP1449 | 9.8E−11 | A | A | 30.6 |
| PP1450 | 1.4E−10 | A | A | 50.1 |
| PP1451 | 1.4E−10 | A | A | 61.1 |
| PP1452 | 1.3E−10 | A | A | 30.5 |
| PP1453 | 1.2E−10 | A | A | 13.6 |
| PP1454 | 9.6E−11 | A | A | 15.2 |
| PP1455 | 1.1E−10 | A | A | 13.4 |
| PP1456 | 1.2E−10 | A | A | 90.0 |
| PP1457 | 1.5E−10 | A | A | 30.4 |
| PP1458 | 1.5E−10 | A | A | 18.2 |
| PP1459 | 2.0E−10 | A | A | 38.6 |
| PP1460 | 2.3E−10 | A | A | 32.9 |
| PP1461 | 2.7E−10 | A | A | 120.7 |
| PP1462 | 1.2E−10 | A | A | 27.5 |
| PP1463 | 1.3E−10 | A | A | 44.5 |
| PP1464 | 1.5E−10 | A | A | 32.3 |
| PP1465 | 3.6E−10 | A | A | 34.1 |
| PP1466 | 1.4E−10 | A | A | 33.2 |
| PP1467 | 1.2E−10 | A | A | 11.2 |
| PP1468 | 1.2E−10 | A | A | 9.5 |
| PP1469 | 1.8E−10 | A | A | 22.2 |
| PP1470 | 2.2E−10 | A | A | 110.7 |
| PP1471 | 2.5E−10 | A | A | 48.2 |
| PP1472 | 1.4E−10 | A | A | 37.1 |
| PP1473 | 1.9E−10 | A | A | 36.6 |
| PP1474 | 2.3E−10 | A | A | 48.2 |
| PP1475 | 5.5E−10 | A | A | 48.9 |
| PP1476 | 1.0E−09 | A | B | 215.5 |
| PP1477 | 1.4E−09 | A | B | 308.8 |
| PP1478 | 3.4E−10 | A | A | 101.8 |
| PP1479 | 4.9E−10 | A | B | 139.8 |
| PP1480 | 9.2E−10 | A | B | 85.8 |
| PP1481 | 1.2E−09 | A | B | 14.8 |
| PP1482 | 4.5E−10 | A | B | 76.4 |
| PP1483 | 5.1E−10 | A | B | 90.3 |
| PP1484 | 4.5E−10 | A | A | 59.3 |
| PP1485 | 2.8E−10 | A | A | 30.5 |
| PP1486 | 4.6E−10 | A | A | 15.0 |
| PP1487 | 3.4E−10 | A | A | 46.6 |
| PP1488 | 8.1E−11 | A | B | 23.2 |
| PP1489 | 2.6E−09 | B | B | 118.1 |
| PP1490 | 6.0E−10 | B | B | 48.9 |
| PP1491 | 3.7E−09 | B | A | 197.9 |
| PP1492 | 9.4E−10 | B | B | 129.2 |
| PP1493 | 2.3E−09 | B | B | 135.1 |
| PP1494 | 5.8E−10 | B | B | 142.5 |
| PP1495 | 5.5E−10 | A | B | 98.7 |
| PP1496 | 2.6E−10 | A | B | 36.7 |
| PP1497 | 2.2E−11 | A | A | 10.7 |
| PP1498 | 6.9E−11 | A | A | 10.3 |
| PP1499 | 5.4E−11 | A | B | 5.5 |
| PP1500 | 3.9E−11 | A | A | 6.9 |
| PP1501 | 2.4E−11 | A | A | 1.5 |
| PP1502 | 3.8E−11 | A | A | 2.0 |
| PP1503 | 1.1E−10 | A | A | 3.8 |
| PP1504 | 3.2E−10 | A | A | 38.0 |
| PP1505 | 9.2E−11 | A | A | 4.0 |
| PP1506 | 3.4E−10 | AA | A | 73.4 |
| PP1507 | 1.7E−10 | A | A | 16.2 |
| PP1508 | 1.5E−10 | A | A | 28.1 |
| PP1509 | 4.0E−10 | A | A | 67.9 |
| PP1510 | 1.1E−10 | AA | A | 34.5 |
| PP1511 | 9.9E−11 | AA | A | 13.7 |
| PP1512 | 8.4E−11 | AA | A | 16.9 |
| PP1513 | 7.1E−11 | A | A | 8.3 |
| PP1514 | 6.5E−10 | A | A | 72.7 |
| PP1515 | 4.2E−10 | A | A | 91.9 |
| PP1516 | 9.8E−10 | A | B | 45.7 |
| PP1517 | 4.3E−10 | A | A | 33.6 |
| PP1518 | 5.8E−10 | A | B | 49.4 |
| PP1519 | 4.1E−10 | A | A | 78.2 |
| PP1520 | 6.6E−09 | A | A | 575.0 |
| PP1521 | 2.6E−09 | A | B | 173.2 |
| PP1522 | 8.8E−09 | A | A | 566.7 |
| PP1523 | 4.1E−09 | | | 320.2 |
| PP1524 | 5.7E−09 | B | B | 438.6 |
| PP1525 | 1.7E−09 | A | A | 131.6 |
| PP1526 | 1.3E−09 | A | A | 118.0 |
| PP1527 | 9.5E−10 | A | A | 142.9 |
| PP1528 | 2.0E−10 | A | B | 45.6 |
| PP1529 | 8.1E−11 | A | B | 30.2 |
| PP1530 | 2.1E−10 | A | B | 17.2 |
| PP1531 | 1.2E−10 | A | B | 13.9 |
| PP1532 | 1.9E−10 | A | B | 13.4 |
| PP1533 | 1.3E−10 | AA | A | 23.8 |
| PP1534 | 1.3E−10 | AA | A | 24.7 |
| PP1535 | 1.8E−10 | A | A | 18.9 |
| PP1536 | 2.0E−10 | A | B | 24.8 |
| PP1537 | 6.7E−11 | AA | A | 7.9 |
| PP1538 | 8.6E−11 | A | B | 7.5 |
| PP1552 | 1.9E−10 | A | A | 15.9 |
| PP1553 | 1.3E−10 | A | A | 12.1 |
| PP1554 | 2.7E−09 | A | A | 120.8 |
| PP1557 | 1.2E−09 | A | A | 86.3 |
| PP1558 | 1.1E−10 | A | B | 3.4 |
| PP1559 | 4.7E−11 | A | A | 1.8 |
| PP1560 | 6.9E−11 | A | B | 1.8 |
| PP1561 | 6.4E−11 | A | B | 2.7 |
| PP1562 | 4.6E−11 | A | A | 1.7 |
| PP1563 | 4.8E−11 | A | A | 2.6 |
| PP1564 | 7.3E−11 | A | A | 3.0 |
| PP1565 | 1.1E−10 | A | B | 6.5 |
| PP1566 | 2.6E−11 | A | A | 2.3 |
| PP1568 | 3.1E−11 | A | A | 2.2 |
| PP1569 | 1.1E−10 | A | B | 2.8 |
| PP1570 | 5.1E−11 | AA | A | 2.6 |
| PP1571 | 1.5E−10 | A | A | 6.8 |
| PP1572 | 7.8E−11 | A | A | 3.6 |
| PP1573 | 1.2E−10 | A | A | 5.2 |
| PP1574 | 1.5E−10 | A | A | 6.5 |
| PP1575 | 5.5E−10 | B | B | 11.1 |
| PP1576 | 1.4E−10 | AA | A | 7.6 |
| PP1577 | 1.7E−10 | B | B | 6.7 |
| PP1578 | 2.0E−10 | A | A | 12.6 |
| PP1579 | 8.7E−11 | A | B | 4.1 |
| PP1580 | 1.7E−10 | A | A | 9.7 |
| PP1582 | 5.7E−10 | A | A | 27.4 |
| PP1583 | 7.8E−10 | B | B | 45.7 |
| PP1584 | 5.6E−10 | B | B | 66.4 |
| PP1586 | 7.6E−10 | A | A | 85.5 |
| PP1587 | 3.6E−09 | A | A | 106.4 |
| PP1588 | 6.0E−10 | B | B | 24.2 |
| PP1589 | 1.8E−09 | A | A | 86.6 |
| PP1590 | 2.9E−10 | A | B | 8.0 |
| PP1591 | 4.6E−09 | A | A | 85.4 |
| PP1592 | 7.1E−10 | A | B | 17.2 |
| PP1593 | 4.3E−09 | A | A | 143.9 |
| PP1594 | 7.1E−10 | A | A | 48.8 |
| PP1595 | 2.3E−09 | A | A | 64.6 |
| PP1596 | 5.6E−10 | A | B | 18.1 |
| PP1598 | 7.6E−10 | A | A | 36.6 |
| PP1599 | 3.7E−10 | A | A | 10.2 |
| PP1600 | 3.2E−10 | A | B | 13.8 |
| PP1601 | 2.1E−09 | B | A | 78.6 |
| PP1603 | 5.3E−09 | B | B | 132.0 |
| PP1605 | 7.9E−10 | A | A | 31.6 |
| PP1606 | 3.7E−10 | B | B | 12.6 |
| PP1607 | 5.7E−10 | | A | 39.3 |
| PP1608 | 6.7E−10 | A | A | 70.1 |
| PP1609 | 2.0E−10 | A | A | 37.0 |
| PP1610 | 1.4E−09 | A | A | 86.8 |
| PP1611 | 1.3E−09 | B | B | 28.0 |
| PP1612 | 1.2E−09 | B | B | 61.9 |
| PP1613 | 1.5E−10 | B | B | 14.7 |
| PP1614 | 1.1E−09 | A | A | 54.2 |
| PP1615 | 4.5E−10 | B | B | 20.9 |
| PP1616 | 2.9E−10 | B | B | 33.5 |

TABLE 37-continued

| Compound No. | KRAS KD (M) | NRAS/ KRAS | HRAS/ KRAS | NCI-H441 IC$_{50}$ (nM) |
|---|---|---|---|---|
| PP1617 | 2.6E−10 | B | B | 41.9 |
| PP1620 | 6.4E−09 | B | B | 170.3 |
| PP1622 | 1.3E−09 | A | A | 28.1 |
| PP1623 | 1.9E−10 | A | A | 4.5 |
| PP1624 | 1.1E−09 | A | A | 55.8 |
| PP1625 | 2.9E−10 | B | B | 20.2 |
| PP1626 | 3.0E−09 | A | A | 108.1 |
| PP1627 | 2.5E−10 | A | A | 22.9 |
| PP1628 | 2.5E−09 | A | A | 149.9 |
| PP1629 | 3.6E−10 | B | B | 20.7 |
| PP1630 | 1.8E−09 | A | A | 144.5 |
| PP1631 | 3.3E−10 | A | B | 17.6 |
| PP1632 | 3.7E−09 | A | A | 115.6 |
| PP1633 | 6.0E−10 | A | B | 15.1 |
| PP1634 | 5.1E−09 | A | A | 144.5 |
| PP1635 | 6.4E−10 | B | A | 36.3 |
| PP1636 | 2.8E−09 | A | A | 95.2 |
| PP1637 | 3.2E−10 | A | A | 32.5 |
| PP1639 | 6.8E−10 | A | A | 44.8 |
| PP1640 | 1.4E−10 | B | B | 28.3 |
| PP1641 | 9.8E−11 | A | A | 4.6 |
| PP1643 | 5.5E−11 | A | A | 1.6 |
| PP1644 | 3.8E−11 | A | A | 2.7 |
| PP1645 | 4.0E−11 | A | A | 1.8 |
| PP1646 | 1.2E−10 | A | A | 2.8 |
| PP1648 | 1.1E−10 | A | A | 2.1 |
| PP1649 | 6.4E−11 | A | B | 2.2 |
| PP1650 | 5.7E−11 | A | A | 1.2 |
| PP1651 | 7.9E−11 | A | B | 2.3 |
| PP1653 | 9.7E−11 | A | A | 1.6 |
| PP1654 | 9.7E−11 | A | A | 2.5 |
| PP1655 | 8.3E−11 | A | A | 1.6 |
| PP1656 | 6.5E−11 | AA | A | 1.5 |
| PP1657 | 6.0E−11 | A | B | 2.0 |
| PP1658 | 1.2E−10 | A | A | 3.8 |
| PP1660 | 1.1E−10 | A | A | 4.3 |
| PP1661 | 1.9E−10 | A | A | 5.7 |
| PP1662 | 1.4E−10 | A | B | 6.4 |
| PP1663 | 3.8E−11 | AA | A | 3.6 |
| PP1665 | 6.6E−11 | AA | A | 3.1 |
| PP1666 | 7.6E−11 | A | A | 8.1 |
| PP1667 | 8.1E−11 | A | A | 2.0 |
| PP1668 | 1.3E−10 | A | A | 5.3 |
| PP1670 | 1.0E−10 | A | A | 6.7 |
| PP1671 | 7.7E−11 | A | A | 3.0 |
| PP1672 | 8.7E−11 | A | A | 6.0 |
| PP1673 | 1.6E−10 | A | A | 6.0 |
| PP1674 | 3.6E−11 | A | A | 5.1 |
| PP1675 | 7.1E−11 | A | B | 3.0 |
| PP1676 | 1.2E−10 | A | A | 5.0 |
| PP1677 | 4.2E−11 | A | A | 3.4 |
| PP1678 | 1.7E−10 | A | B | 5.6 |
| PP1679 | 6.5E−11 | A | A | 3.1 |
| PP1682 | 8.2E−11 | AA | A | 2.6 |
| PP1683 | 9.7E−11 | A | A | 2.5 |
| PP1684 | 1.5E−10 | A | A | 7.7 |
| PP1687 | 7.5E−11 | A | A | 2.7 |
| PP1688 | 2.5E−11 | A | A | 1.5 |
| PP1689 | 2.3E−11 | A | B | 1.4 |
| PP1691 | 6.0E−11 | A | A | 3.1 |
| PP1692 | 1.1E−10 | AA | A | 4.3 |
| PP1693 | 2.7E−11 | AA | A | 1.1 |
| PP1694 | 5.1E−11 | A | A | 4.1 |
| PP1696 | 4.1E−11 | AA | A | 2.9 |
| PP1697 | 4.7E−11 | A | A | 3.6 |
| PP1698 | 7.5E−11 | A | A | 5.1 |
| PP1699 | 9.5E−11 | A | A | 2.5 |
| PP1700 | 1.1E−10 | A | A | 3.6 |
| PP1701 | 8.0E−11 | A | A | 3.7 |
| PP1702 | 8.5E−11 | A | A | 4.9 |
| PP1703 | 1.3E−10 | A | A | 7.2 |
| PP1704 | 1.4E−10 | A | A | 10.3 |
| PP1705 | 1.4E−10 | AA | A | 8.0 |
| PP1706 | 7.5E−11 | A | A | 6.7 |
| PP1707 | 3.7E−11 | AA | A | 7.4 |
| PP1709 | 5.8E−11 | A | A | 3.8 |
| PP1710 | 1.0E−10 | A | B | 4.1 |
| PP1711 | 9.3E−11 | A | B | 5.0 |
| PP1713 | 9.6E−11 | A | A | 7.9 |
| PP1714 | 1.0E−10 | A | A | 4.3 |
| PP1715 | 6.1E−11 | AA | A | 2.7 |
| PP1716 | 9.9E−11 | AA | A | 3.8 |
| PP1717 | 5.1E−11 | A | A | 2.4 |
| PP1718 | 6.7E−11 | AA | A | 2.5 |
| PP1721 | 3.0E−10 | A | A | 10.0 |
| PP1722 | 6.0E−11 | AA | A | 1.8 |
| PP1727 | 1.3E−10 | A | A | 4.0 |
| PP1728 | 1.6E−10 | A | A | 18.3 |
| PP1729 | 2.0E−10 | AA | A | 20.6 |
| PP1731 | 7.0E−11 | A | A | 7.4 |
| PP1732 | 9.9E−11 | AA | A | 6.4 |
| PP1733 | 1.1E−10 | A | A | 3.8 |
| PP1734 | 1.7E−10 | A | A | 4.4 |
| PP1735 | 8.1E−11 | AA | A | 2.2 |
| PP1736 | 1.3E−10 | A | A | 3.6 |
| PP1737 | 1.1E−10 | A | A | 2.7 |
| PP1738 | 7.1E−11 | AA | A | 5.1 |
| PP1739 | 5.4E−11 | AA | AA | 5.5 |
| PP1740 | 5.3E−11 | A | A | 3.6 |
| PP1741 | 3.9E−11 | A | B | 2.3 |
| PP1742 | 5.1E−11 | A | A | 1.6 |
| PP1743 | 7.6E−11 | AA | A | 5.1 |
| PP1744 | 1.3E−10 | A | A | 5.3 |
| PP1746 | 5.4E−11 | A | A | 1.9 |
| PP1747 | 5.8E−11 | A | A | 2.3 |
| PP1748 | 6.2E−11 | A | B | 3.1 |
| PP1749 | 3.9E−11 | A | A | 3.3 |
| PP1750 | 6.9E−11 | A | B | 3.4 |
| PP1751 | 4.7E−11 | A | A | 2.2 |
| PP1752 | 8.5E−11 | A | A | 5.8 |
| PP1753 | 3.8E−11 | A | A | 5.9 |
| PP1754 | 6.4E−11 | A | A | 3.0 |
| PP1757 | 3.1E−10 | AA | A | 7.1 |
| PP1758 | 1.9E−10 | AA | A | 6.0 |
| PP1759 | 1.5E−10 | A | A | 6.2 |
| PP1760 | 1.7E−10 | A | A | 6.2 |
| PP1761 | 1.7E−10 | A | A | 5.2 |
| PP1762 | 2.6E−10 | A | A | 8.4 |
| PP1763 | 2.3E−10 | A | A | 13.3 |
| PP1764 | 1.1E−10 | AA | A | 11.1 |
| PP1765 | 8.4E−11 | A | A | 16.8 |
| PP1767 | 3.4E−10 | A | B | 17.9 |
| PP1768 | 3.2E−10 | A | A | 4.9 |
| PP1769 | 7.8E−10 | A | A | 12.9 |
| PP1771 | 9.7E−11 | A | A | 6.6 |
| PP1772 | 2.3E−10 | B | B | 13.4 |
| PP1773 | 5.3E−10 | A | A | 39.9 |
| PP1776 | 5.4E−10 | A | A | 98.7 |
| PP1777 | 3.6E−10 | A | B | 79.3 |
| PP1779 | 3.4E−11 | A | B | 5.4 |
| PP1780 | 6.5E−11 | A | A | 8.2 |
| PP1781 | 2.4E−11 | A | B | 2.1 |
| PP1782 | 4.4E−11 | A | B | 6.7 |
| PP1783 | 2.8E−11 | A | B | 3.5 |
| PP1784 | 8.3E−11 | A | B | 7.8 |
| PP1785 | 5.1E−11 | A | A | 6.9 |
| PP1786 | 1.4E−10 | A | B | 11.4 |
| PP1787 | 7.1E−11 | A | B | 9.0 |
| PP1788 | 6.3E−11 | B | B | 6.2 |
| PP1789 | 1.3E−10 | A | A | 9.5 |
| PP1790 | 3.0E−11 | A | B | 1.7 |
| PP1791 | 4.2E−11 | A | A | 3.7 |
| PP1792 | 8.0E−11 | A | B | 9.6 |
| PP1793 | 2.3E−11 | A | B | 2.4 |
| PP1794 | 6.0E−11 | A | B | 8.7 |
| PP1795 | 3.1E−11 | A | B | 3.0 |
| PP1796 | 5.7E−11 | A | B | 5.3 |
| PP1797 | 1.0E−10 | A | A | 5.1 |
| PP1798 | 1.5E−10 | A | A | 7.8 |
| PP1799 | 6.8E−11 | B | B | 7.6 |
| PP1800 | 5.1E−11 | A | A | 6.5 |
| PP1801 | 2.1E−10 | A | B | 13.0 |
| PP1802 | 8.2E−11 | A | B | 5.8 |
| PP1803 | 1.0E−10 | A | B | 7.6 |

TABLE 37-continued

| Compound No. | KRAS KD (M) | NRAS/KRAS | HRAS/KRAS | NCI-H441 IC$_{50}$ (nM) |
|---|---|---|---|---|
| PP1804 | 5.6E−11 | A | A | 3.5 |
| PP1805 | 7.1E−11 | A | A | 7.0 |
| PP1806 | 6.0E−11 | A | B | 4.0 |
| PP1807 | 6.2E−11 | A | B | 5.0 |
| PP1808 | 8.4E−11 | A | B | 8.8 |
| PP1809 | 1.2E−10 | A | B | 22.4 |
| PP1810 | 1.6E−10 | A | B | 4.6 |
| PP1811 | 2.3E−10 | A | B | 14.3 |
| PP1812 | 5.9E−11 | A | A | 7.8 |
| PP1813 | 1.2E−10 | A | B | 22.6 |
| PP1814 | 2.7E−10 | A | A | 26.2 |
| PP1815 | 3.4E−10 | B | B | 83.0 |
| PP1816 | 1.2E−09 | B | C | 63.8 |
| PP1817 | 4.7E−10 | C | C | 20.4 |
| PP1818 | 9.0E−10 | C | B | 74.8 |
| PP1819 | 1.0E−09 | C | C | 148.7 |
| PP1820 | 6.0E−10 | C | C | 40.7 |
| PP1821 | 6.3E−10 | A | A | 104.7 |
| PP1822 | 1.1E−09 | A | B | 107.0 |
| PP1823 | 1.0E−09 | A | A | 55.9 |
| PP1825 | 1.4E−10 | A | A | 8.0 |
| PP1826 | 3.2E−10 | A | A | 17.6 |
| PP1827 | 2.9E−11 | A | A | 2.4 |
| PP1828 | 3.9E−11 | A | B | 1.9 |
| PP1829 | 3.3E−11 | A | B | 2.3 |
| PP1830 | 5.4E−11 | A | B | 4.7 |
| PP1831 | 2.5E−11 | A | A | 3.0 |
| PP1832 | 4.0E−11 | B | B | 2.5 |
| PP1833 | 4.4E−11 | A | A | 2.7 |
| PP1834 | 6.5E−11 | A | B | 2.1 |
| PP1835 | 5.1E−11 | A | B | 4.9 |
| PP1836 | 1.0E−10 | A | B | 10.7 |
| PP1837 | 2.0E−10 | A | A | 15.6 |
| PP1838 | 1.0E−10 | A | A | 20.0 |
| PP1839 | 3.1E−10 | A | B | 24.3 |
| PP1840 | 1.2E−10 | A | B | 26.8 |
| PP1841 | 3.8E−10 | AA | A | 24.3 |
| PP1842 | 1.9E−10 | A | B | 26.9 |
| PP1844 | 7.0E−11 | A | B | 12.3 |
| PP1846 | 1.0E−10 | A | A | 9.8 |
| PP1848 | 1.1E−10 | A | A | 22.5 |
| PP1849 | 3.8E−10 | A | A | 37.1 |
| PP1850 | 1.6E−10 | A | B | 49.1 |
| PP1851 | 1.8E−09 | A | A | 165.4 |
| PP1852 | 7.1E−11 | A | B | 6.0 |
| PP1853 |  |  |  | 30.4 |
| PP1854 | 9.6E−11 | A | A | 5.2 |
| PP1855 | 1.9E−10 | AA | A | 17.7 |
| PP1856 | 1.1E−10 | A | A | 1.4 |
| PP1857 | 9.1E−11 | A | B | 5.0 |
| PP1859 | 1.4E−10 | A | A | 28.8 |
| PP1860 | 1.1E−10 | A | A | 10.3 |
| PP1861 | 9.1E−11 | A | B | 25.7 |
| PP1862 | 1.2E−10 | A | A | 22.2 |
| PP1863 | 1.3E−10 | A | A | 88.8 |
| PP1864 | 6.4E−11 | A | B | 10.2 |
| PP1865 | 8.3E−11 | A | B | 36.0 |
| PP1866 | 9.3E−11 | A | B | 11.1 |
| PP1867 | 1.7E−10 | A | B | 47.8 |
| PP1868 | 8.7E−11 | A | B | 10.7 |
| PP1869 | 1.3E−10 | A | A | 36.4 |
| PP1870 | 1.9E−10 | A | A | 12.4 |
| PP1871 | 9.9E−11 | A | A | 13.1 |
| PP1872 | 1.2E−10 | A | A | 12.4 |
| PP1873 | 7.5E−11 | A | B | 8.5 |
| PP1874 | 1.3E−10 | A | A | 9.9 |
| PP1875 | 8.3E−11 | A | B | 7.7 |
| PP1876 | 2.0E−10 | A | A | 23.0 |
| PP1877 | 1.6E−10 | A | A | 18.4 |
| PP1878 | 6.3E−11 | A | A | 8.8 |
| PP1879 | 1.8E−10 | A | B | 16.9 |
| PP1880 | 1.5E−10 | A | B | 15.6 |
| PP1881 | 2.9E−10 | A | A | 16.7 |
| PP1882 | 1.2E−10 | A | B | 20.2 |
| PP1883 | 2.8E−10 | A | A | 24.0 |
| PP1884 | 1.6E−10 | A | A | 17.3 |
| PP1885 | 2.3E−10 | AA | A | 18.3 |
| PP1886 | 1.2E−10 | A | B | 1.9 |
| PP1887 | 3.0E−10 | A | B | 19.2 |
| PP1888 | 7.4E−11 | A | B | 3.5 |
| PP1889 | 2.1E−10 | A | B | 12.5 |
| PP1890 | 1.5E−10 | A | B | 3.6 |
| PP1891 | 2.9E−10 | A | A | 2.6 |
| PP1892 | 7.4E−11 | A | B | 4.8 |
| PP1893 | 1.7E−10 | A | B | 18.5 |
| PP1894 | 2.0E−10 | A | A | 15.9 |
| PP1895 | 1.3E−10 | A | B | 15.6 |
| PP1896 | 6.0E−11 | A | B | 5.3 |
| PP1897 | 1.6E−10 | B | B | 22.6 |
| PP1898 | 1.3E−10 | B | B | 6.3 |
| PP1899 | 1.2E−10 | A | B | 15.1 |
| PP1900 | 1.7E−10 | A | A | 24.7 |
| PP1901 | 9.8E−11 | A | B | 7.6 |
| PP1902 | 2.0E−10 | A | A | 12.5 |
| PP1903 | 6.3E−11 | A | B | 5.5 |
| PP1904 | 1.2E−10 | A | B | 18.3 |
| PP1905 | 7.5E−11 | A | A | 6.7 |
| PP1906 | 1.5E−10 | A | A | 10.8 |
| PP1907 | 1.7E−10 | AA | A | 23.6 |
| PP1908 | 1.1E−10 | A | B | 10.1 |
| PP1909 | 3.4E−10 | A | B | 15.3 |
| PP1910 | 1.4E−10 | A | B | 9.7 |
| PP1911 | 2.1E−10 | A | A | 11.7 |
| PP1913 | 3.7E−10 | A | A | 44.0 |
| PP1914 |  |  |  | 39.7 |
| PP1915 | 3.1E−10 | A | A | 18.5 |
| PP1916 | 4.9E−10 | B | C | 16.8 |
| PP1917 | 2.9E−10 | A | A | 22.5 |
| PP1918 | 1.9E−10 | B | C | 32.8 |
| PP1919 | 2.3E−10 | A | A | 6.3 |
| PP1920 | 3.1E−10 | B | C | 32.4 |
| PP1921 | 5.5E−11 | A | A | 7.8 |
| PP1922 | 2.3E−10 | B | C | 44.1 |
| PP1923 | 3.4E−09 | A | A | 68.0 |
| PP1925 | 2.3E−10 | A | A | 9.7 |
| PP1926 | 3.6E−10 | B | B | 17.4 |
| PP1927 | 8.5E−10 | A | A | 23.5 |
| PP1928 | 2.5E−10 | B | B | 18.4 |
| PP1929 | 6.6E−10 | A | A | 41.7 |
| PP1930 | 2.3E−10 | B | C | 7.0 |
| PP1931 | 1.2E−10 | A | B | 9.5 |
| PP1932 | 1.5E−10 | A | A | 13.1 |
| PP1934 | 7.2E−10 | A | A | 68.5 |
| PP1935 | 4.6E−10 | A | A | 13.1 |
| PP1936 | 4.0E−10 | AA | A | 12.3 |
| PP1937 | 3.1E−10 | A | A | 6.8 |
| PP1938 | 3.4E−10 | AA | A | 34.6 |
| PP1941 | 1.7E−10 | A | A | 9.2 |
| PP1942 | 1.5E−10 | AA | A | 25.7 |
| PP1943 | 1.1E−10 | A | B | 9.2 |
| PP1944 | 1.9E−10 | A | A | 14.8 |
| PP1945 | 3.1E−10 | AA | A | 33.8 |
| PP1946 | 1.6E−10 | B | C | 15.2 |
| PP1947 | 3.7E−10 | B | B | 22.0 |
| PP1948 | 4.1E−10 | C | C | 16.2 |
| PP1949 | 9.2E−10 | C | C | 9.3 |
| PP1950 | 1.9E−09 | B | C | 32.5 |
| PP1952 | 1.3E−10 | B | B | 14.0 |
| PP1953 | 4.2E−10 | B | B | 8.7 |
| PP1954 | 7.7E−10 | B | B | 8.1 |
| PP1955 | 8.2E−10 | C | C | 4.4 |
| PP1956 | 2.8E−10 | B | B | 2.2 |
| PP1957 | 3.6E−10 | C | B | 8.6 |
| PP1958 | 5.3E−10 | B | B | 57.8 |
| PP1959 | 5.5E−10 | C | C | 14.7 |
| PP1960 | 1.7E−10 | B | C | 6.0 |
| PP1961 | 2.2E−10 | C | C | 8.0 |
| PP1963 | 1.8E−10 | B | C | 9.1 |
| PP1964 | 1.9E−10 | B | B | 10.3 |
| PP1965 | 3.0E−10 | B | B | 17.4 |
| PP1967 | 3.6E−10 | B | B | 10.9 |
| PP1968 | 7.6E−10 | C | C | 13.5 |
| PP1969 | 2.1E−09 | B | C | 74.0 |
| PP1970 | 6.2E−10 | B | B | 16.8 |

TABLE 37-continued

| Compound No. | KRAS KD (M) | NRAS/ KRAS | HRAS/ KRAS | NCI-H441 IC$_{50}$ (nM) |
|---|---|---|---|---|
| PP1971 | 5.0E−09 | B | B | 38.0 |
| PP1972 | 1.5E−10 | A | A | 13.2 |
| PP1973 | 9.9E−11 | A | B | 8.7 |
| PP1974 | 1.8E−10 | A | A | 50.0 |
| PP1975 | 1.1E−10 | A | A | 13.4 |
| PP1976 | 3.7E−10 | AA | A | 92.0 |
| PP1977 | 1.5E−10 | AA | A | 20.2 |
| PP1979 | 8.7E−11 | AA | A | 12.5 |
| PP1980 | 3.6E−10 | A | B | 30.1 |
| PP1981 | 1.0E−10 | A | A | 20.7 |
| PP1983 | 1.4E−10 | AA | A | 20.2 |
| PP1984 | 3.0E−10 | A | A | 50.8 |
| PP1985 | 2.3E−10 |  | B | 17.7 |
| PP1987 | 5.3E−11 | A | A | 6.6 |
| PP1988 | 6.0E−11 | A | A | 11.0 |
| PP1989 | 1.9E−10 | A | A | 11.1 |
| PP1990 | 1.4E−10 | A | A | 6.6 |
| PP1991 | 1.5E−10 | A | A | 10.8 |
| PP1992 | 2.1E−10 | AA | B | 17.7 |
| PP1993 | 1.2E−10 | A | A | 13.3 |
| PP1994 | 1.0E−10 | AA | A | 22.4 |
| PP1995 | 2.1E−10 | A | B | 17.8 |
| PP1996 | 1.2E−10 | A | B | 15.5 |
| PP1997 | 9.8E−11 | A | B | 14.2 |
| PP1998 | 1.7E−10 | A | B | 16.1 |
| PP1999 | 1.3E−10 | A | B | 26.6 |
| PP2000 | 1.8E−10 | A | B | 17.7 |
| PP2001 | 1.1E−10 | A | A | 18.1 |
| PP2002 |  |  |  | 15.7 |
| PP2003 | 3.4E−10 | A | B | 11.3 |
| PP2004 | 6.2E−11 | A | A | 5.1 |
| PP2005 | 1.3E−10 | A | A | 10.7 |
| PP2006 | 1.1E−10 | A | A | 7.8 |
| PP2007 | 1.4E−10 | AA | B | 14.9 |
| PP2008 | 1.3E−10 | A | A | 15.2 |
| PP2009 | 1.9E−10 | A | A | 19.7 |
| PP2010 | 1.4E−10 | A | B | 6.6 |
| PP2011 | 1.1E−10 | A | A | 10.3 |
| PP2012 | 9.7E−11 | AA | A | 11.6 |
| PP2013 | 1.3E−10 | A | B | 7.7 |
| PP2014 | 9.3E−11 | A | A | 6.9 |
| PP2015 | 1.1E−10 | A | B | 5.6 |
| PP2016 | 1.1E−10 | A | A | 8.2 |
| PP2017 | 9.3E−11 | A | A | 2.5 |
| PP2018 | 1.0E−10 | A | B | 5.3 |
| PP2019 | 1.6E−10 | A | A | 4.5 |
| PP2020 | 1.9E−10 | A | A | 8.3 |
| PP2021 | 1.2E−10 | A | B | 4.9 |
| PP2022 | 1.1E−10 | A | A | 2.7 |
| PP2023 | 1.1E−10 | A | B | 10.5 |
| PP2024 | 8.2E−11 | A | B | 10.1 |
| PP2025 | 6.1E−11 | A | B | 13.4 |
| PP2026 | 8.9E−11 | A | A | 22.6 |
| PP2027 | 1.1E−10 | A | B | 14.0 |
| PP2028 | 1.1E−10 | A | B | 17.5 |
| PP2029 | 6.9E−11 | A | B | 18.9 |
| PP2030 | 1.2E−10 | A | A | 4.5 |
| PP2031 | 1.4E−10 | B | B | 5.5 |
| PP2032 | 6.1E−11 | A | B | 8.1 |
| PP2033 |  |  |  | 11.8 |
| PP2034 | 1.9E−10 | A | A | 8.8 |
| PP2036 | 8.9E−11 | A | A | 9.1 |
| PP2037 | 1.2E−10 | A | A | 16.0 |
| PP2038 | 1.6E−10 | A | A | 5.5 |
| PP2040 | 3.1E−10 | A | A | 10.5 |
| PP2041 | 1.9E−10 | A | A | 7.7 |
| PP2042 | 1.4E−10 | A | A | 5.9 |
| PP2043 | 2.1E−10 | A | A | 28.0 |
| PP2044 | 1.4E−10 | A | A | 5.0 |
| PP2045 | 1.7E−10 | A | B | 5.1 |
| PP2046 | 6.3E−11 | A | A | 2.2 |
| PP2047 | 1.3E−10 | A | B | 5.5 |
| PP2048 | 7.1E−11 | A | B | 3.6 |
| PP2049 | 4.0E−11 | A | B | 6.1 |
| PP2050 | 1.9E−10 | A | A | 7.5 |
| PP2051 | 1.2E−10 | A | A | 6.9 |
| PP2052 | 1.6E−10 | A | A | 4.1 |
| PP2053 | 1.3E−10 | A | A | 9.3 |
| PP2054 | 4.1E−10 | A | A | 8.5 |
| PP2055 | 1.8E−10 | A | B | 16.1 |
| PP2056 | 3.3E−10 | A | A | 7.3 |
| PP2057 | 2.6E−10 | A | A | 12.3 |
| PP2058 | 2.1E−10 | A | A | 3.7 |
| PP2059 | 9.3E−11 | A | A | 4.9 |
| PP2060 | 1.6E−10 | A | A | 7.4 |
| PP2061 | 7.5E−11 | AA | A | 6.1 |
| PP2062 | 1.9E−10 | AA | A | 13.7 |
| PP2063 | 9.0E−11 | AA | A | 13.6 |
| PP2064 | 2.6E−10 | A | A | 13.6 |
| PP2065 | 2.2E−10 | A | B | 17.0 |
| PP2066 | 2.5E−10 | A | B | 3.2 |
| PP2067 | 2.4E−10 | AA | A | 17.7 |
| PP2068 | 3.6E−10 | A | B | 11.1 |
| PP2069 | 8.2E−11 | AA | A | 27.4 |
| PP2070 | 1.1E−10 | A | A | 11.3 |
| PP2071 | 1.0E−10 | A | A | 6.2 |
| PP2072 | 1.2E−10 | A | A | 8.5 |
| PP2073 | 7.8E−11 | A | A | 3.5 |
| PP2074 | 1.1E−10 | A | A | 5.9 |
| PP2075 | 2.2E−10 | A | A | 11.8 |
| PP2076 | 3.9E−10 | A | A | 15.6 |
| PP2077 | 1.2E−10 | A | A | 10.9 |
| PP2078 | 1.7E−10 | AA | A | 10.3 |
| PP2079 | 2.9E−10 | A | A | 16.0 |
| PP2080 | 9.3E−11 | A | A | 17.8 |
| PP2081 | 1.2E−10 | A | A | 11.2 |
| PP2082 | 1.1E−10 | AA | A | 7.8 |
| PP2083 | 2.2E−10 | A | B | 10.3 |
| PP2087 | 1.5E−10 | A | A | 4.8 |
| PP2091 | 1.8E−10 | A | B | 4.6 |
| PP2093 | 3.3E−10 | A | A | 7.4 |
| PP2094 | 2.9E−10 | A | A | 5.4 |
| PP2095 | 1.5E−10 | A | A | 5.7 |
| PP2096 | 4.2E−10 | A | A | 10.7 |
| PP2097 | 3.0E−10 | A | A | 8.0 |
| PP2098 | 2.0E−10 | A | A | 8.4 |
| PP2099 | 1.4E−10 | A | A | 9.1 |
| PP2101 | 3.2E−10 | A | B | 16.6 |
| PP2102 | 1.6E−10 | A | A | 7.0 |
| PP2103 | 2.5E−10 | A | A | 4.3 |
| PP2105 | 1.8E−10 | A | A | 10.4 |
| PP2106 | 2.0E−10 | A | A | 6.1 |
| PP2107 | 1.5E−10 | A | A | 7.8 |
| PP2108 | 3.4E−10 | A | A | 17.6 |
| PP2109 | 2.9E−10 | A | A | 5.7 |
| PP2117 | 1.7E−10 | A | A | 28.9 |
| PP2118 | 1.5E−10 | A | B | 8.1 |
| PP2119 | 5.0E−09 | A | B | 8.9 |
| PP2120 | 9.1E−10 | AA | A | 75.5 |
| PP2121 | 1.5E−09 | AA | A | 11.4 |
| PP2122 | 1.4E−09 | AA | A | 106.8 |
| PP2123 | 2.5E−10 | A | A | 24.3 |
| PP2124 | 2.6E−10 | AA | A | 18.7 |
| PP2125 | 2.2E−10 | AA | A | 4.0 |
| PP2126 | 2.3E−10 | A | B | 13.4 |
| PP2127 | 1.8E−10 | AA | A | 12.5 |
| PP2128 | 4.0E−10 | AA | A | 14.8 |
| PP2130 | 6.2E−10 | AA | A | 7.5 |
| PP2131 | 4.3E−10 | A | A | 22.3 |
| PP2132 | 2.7E−10 | AA | A | 18.4 |
| PP2133 | 1.9E−10 | AA | A | 16.2 |
| PP2135 | 4.9E−10 | AA | A | 15.7 |
| PP2137 | 3.7E−10 | A | A | 16.8 |
| PP2138 | 4.4E−10 | A | A | 15.7 |
| PP2139 | 3.8E−10 | AA | A | 38.0 |
| PP2140 | 7.0E−10 | AA | A | 24.7 |
| PP2141 | 1.7E−10 | A | A | 9.4 |
| PP2142 | 3.0E−10 | AA | A | 10.3 |
| PP2143 | 3.1E−10 | A | A | 6.6 |
| PP2144 | 4.8E−10 | AA | A | 29.0 |
| PP2145 | 3.9E−10 | A | A | 17.2 |
| PP2146 | 3.3E−10 | A | A | 8.2 |
| PP2147 | 3.3E−10 | A | B | 9.7 |
| PP2148 | 3.4E−10 | A | A | 41.5 |

TABLE 37-continued

| Compound No. | KRAS KD (M) | NRAS/KRAS | HRAS/KRAS | NCI-H441 IC$_{50}$ (nM) |
|---|---|---|---|---|
| PP2149 | 5.8E−10 | A | A | 17.7 |
| PP2150 | 3.8E−09 | AA | A | 58.0 |
| PP2151 | 2.9E−10 | A | A | 23.3 |
| PP2152 | 6.7E−10 | AA | A | 29.4 |
| PP2153 | 4.9E−10 | A | A | 20.0 |
| PP2154 | 3.6E−10 | A | A | 17.7 |
| PP2155 | 3.7E−10 | A | B | 10.7 |
| PP2156 | 4.1E−10 | AA | A | 20.6 |
| PP2157 | 1.9E−10 | A | A | 5.9 |
| PP2158 | 7.9E−10 | AA | A | 25.4 |
| PP2159 | 3.3E−10 | AA | A | 19.5 |
| PP2160 | 2.2E−10 | A | A | 5.4 |
| PP2161 | 2.0E−10 | AA | A | 12.4 |
| PP2163 | 4.1E−10 | A | A | 18.2 |
| PP2164 | 2.9E−10 | A | A | 14.2 |
| PP2165 | 5.1E−10 | A | A | 17.5 |
| PP2166 | 2.9E−10 | A | A | 23.7 |
| PP2167 | 7.1E−10 | AA | A | 39.1 |
| PP2168 | 3.3E−10 | A | A | 16.9 |
| PP2169 | 6.3E−10 | AA | A | 62.1 |
| PP2170 | 3.3E−10 | A | A | 8.5 |
| PP2171 | 7.5E−10 | A | A | 19.6 |
| PP2172 | 5.1E−10 | A | B | 5.8 |
| PP2173 | 5.5E−10 | A | A | 19.9 |
| PP2174 | 4.0E−10 | AA | A | 24.0 |
| PP2175 | 4.5E−10 | AA | A | 25.7 |
| PP2176 | 4.7E−10 | AA | A | 52.9 |
| PP2178 | 4.9E−10 | AA | A | 35.9 |
| PP2179 | 1.5E−09 | AA | A | 13.5 |
| PP2180 | 6.6E−10 | AA | A | 27.8 |
| PP2181 | 1.4E−09 | AA | A | 40.3 |
| PP2182 | 7.2E−10 | AA | A | 19.5 |
| PP2183 | 6.8E−10 | A | A | 34.7 |
| PP2184 | 7.0E−10 | AA | A | 29.2 |
| PP2185 | 7.1E−10 | AA | A | 36.1 |
| PP2186 | 2.3E−09 | AA | A | 33.7 |
| PP2187 | 6.9E−10 | AA | A | 31.4 |
| PP2188 | 7.1E−10 | AA | A | 26.7 |
| PP2189 | 1.7E−10 | A | A | 10.5 |
| PP2190 | 9.1E−10 | A | A | 84.5 |
| PP2191 | 2.3E−10 | A | B | 91.6 |
| PP2192 | 3.3E−09 | A | A | 91.9 |
| PP2193 | 4.1E−10 | A | A | 33.1 |
| PP2195 | 9.6E−11 | A | A | 7.8 |
| PP2196 | 2.4E−10 | A | B | 6.6 |
| PP2197 | 1.5E−10 | A | B | 4.6 |
| PP2198 | 2.1E−10 | A | A | 13.8 |
| PP2199 | 1.6E−10 | A | B | 10.3 |
| PP2200 | 3.0E−09 | A | A | 49.9 |
| PP2202 | 4.9E−09 | A | A | 94.7 |
| PP2203 | 3.4E−10 | A | A | 20.5 |
| PP2207 | 7.9E−10 | A | A | 25.8 |
| PP2208 | 2.0E−10 | A | A | 17.8 |
| PP2209 | 8.1E−10 | A | A | 37.0 |
| PP2210 | 1.3E−10 | A | B | 6.2 |
| PP2212 | 3.4E−10 | A | B | 23.5 |
| PP2214 | 3.0E−10 | A | A | 29.6 |
| PP2216 | 2.3E−10 | A | A | 50.8 |
| PP2218 | 2.9E−10 | A | A | 24.0 |
| PP2219 | 1.6E−09 | A | A | 50.9 |
| PP2220 | 1.4E−10 | A | A | 32.1 |
| PP2221 | 1.7E−09 | A | A | 40.5 |
| PP2222 | 1.8E−10 | AA | A | 6.8 |
| PP2223 | 1.0E−10 | A | A | 5.3 |
| PP2224 | 3.8E−10 | A | A | 15.4 |
| PP2225 | 2.0E−10 | A | A | 41.4 |
| PP2226 | 8.2E−10 | A | A | 14.7 |
| PP2227 | 2.7E−10 | A | A | 50.3 |
| PP2229 | 3.8E−10 | A | A | 39.8 |
| PP2230 | 8.2E−11 | A | A | 7.0 |
| PP2231 | 1.8E−10 | A | B | 16.2 |
| PP2232 | 2.2E−10 | A | A | 18.7 |
| PP2233 | 1.8E−10 | A | A | 27.6 |
| PP2234 | 1.9E−10 | A | A | 11.1 |
| PP2235 | 2.8E−10 | A | A | 22.1 |
| PP2237 | 1.4E−10 | A | A | 64.7 |
| PP2238 | 2.0E−10 | A | A | 39.3 |
| PP2242 | 1.8E−09 | A | A | 178.4 |
| PP2257 | 6.3E−10 | AA | A | 48.6 |
| PP2259 | 1.2E−10 | A | B | 6.5 |
| PP2260 | 1.2E−10 | A | A | 1.9 |
| PP2261 | 1.8E−10 | A | A | 16.6 |
| PP2262 | 2.4E−10 | A | B | 3.8 |
| PP2263 | 9.8E−10 | A | A | 19.5 |
| PP2264 | 1.1E−10 | AA | A | 13.1 |
| PP2268 | 1.2E−10 | A | A | 9.8 |
| PP2269 | 3.8E−10 | A | A | 20.0 |
| PP2270 | 2.4E−10 | B | B | 10.4 |
| PP2271 | 2.9E−10 | A | A | 60.6 |
| PP2272 | 4.9E−10 | AA | A | 105.9 |
| PP2273 | 1.9E−10 | AA | A | 16.0 |
| PP2275 | 3.6E−10 | A | A | 12.2 |
| PP2312 | 3.0E−11 | A | B | 1.6 |
| PP2313 | 4.9E−10 | AA | A | 7.4 |
| PP2314 | 2.3E−11 | A | A | 1.8 |
| PP2315 | 3.3E−10 | A | A | 9.0 |
| PP2316 | 1.2E−10 | A | A | 1.6 |
| PP2317 | 4.0E−10 | A | A | 12.5 |
| PP2318 | 1.2E−10 | A | A | 3.3 |
| PP2319 | 3.5E−10 | AA | A | 9.6 |
| PP2320 | 1.1E−10 | A | A | 0.6 |
| PP2322 | 1.8E−10 | A | B | 5.8 |
| PP2323 | 1.4E−10 | A | A | 3.7 |
| PP2325 | 4.0E−10 | A | A | 8.2 |
| PP2326 | 3.1E−11 | A | B | 1.6 |
| PP2327 | 5.0E−10 | A | A | 9.9 |
| PP2328 | 7.9E−11 | A | A | 2.2 |
| PP2329 | 4.2E−10 | A | A | 6.5 |
| PP2330 | 1.1E−10 | A | A | 5.5 |
| PP2331 | 3.6E−10 | AA | A | 11.8 |
| PP2332 | 1.0E−10 | A | B | 3.8 |
| PP2333 | 1.9E−09 | A | A | 44.7 |
| PP2334 | 1.3E−10 | A | B | 5.7 |
| PP2335 | 1.4E−09 | A | A | 64.2 |
| PP2336 | 4.1E−10 | A | A | 16.3 |
| PP2337 | 3.2E−09 | A | A | 33.9 |
| PP2338 | 5.1E−10 | A | B | 34.1 |
| PP2339 | 2.6E−09 | A | A | 59.3 |
| PP2340 | 1.1E−09 | B | B | 44.9 |
| PP2341 | 3.6E−09 | A | A | 133.0 |
| PP2342 | 5.5E−10 | A | A | 70.3 |
| PP2344 | 9.5E−10 | A | A | 44.9 |
| PP2345 | 1.7E−09 | A | A | 77.2 |
| PP2347 | 1.6E−09 | A | A | 142.9 |
| PP2348 | 3.4E−10 | A | A | 52.7 |
| PP2349 | 3.8E−09 | A | A | 73.2 |
| PP2350 | 3.5E−10 | A | A | 60.3 |
| PP2351 | 3.2E−09 | A | A | 177.4 |
| PP2352 | 7.6E−10 | A | A | 15.6 |
| PP2353 | 4.1E−09 | A | A | 68.8 |
| PP2354 | 7.9E−10 | A | A | 9.3 |
| PP2355 | 3.9E−09 | AA | A | 103.0 |
| PP2356 | 9.4E−10 | A | A | 14.7 |
| PP2357 | 1.2E−09 | A | B | 59.7 |
| PP2358 | 2.0E−11 | A | B | 2.5 |
| PP2359 | 2.0E−11 | A | B | 7.6 |
| PP2360 | 1.6E−10 | A | B | 2.9 |
| PP2361 | 6.4E−11 | A | A | 4.4 |
| PP2362 | 7.6E−11 | A | A | 4.8 |
| PP2363 | 6.2E−11 | A | B | 7.5 |
| PP2364 | 1.6E−11 | A | B | 4.6 |
| PP2365 | 2.0E−11 | A | B | 3.3 |
| PP2366 | 4.8E−11 | A | A | 4.5 |
| PP2367 | 7.5E−11 | A | B | 2.1 |
| PP2368 | 4.5E−11 | A | A | 4.1 |
| PP2369 | 6.2E−11 | A | B | 4.5 |
| PP2370 | 5.4E−10 | B | B | 25.7 |
| PP2371 | 6.4E−10 | A | B | 41.9 |
| PP2372 | 7.9E−10 | A | B | 3.3 |
| PP2373 | 6.6E−10 | A | A | 6.5 |
| PP2374 | 8.5E−10 | A | A | 67.2 |
| PP2375 | 1.1E−09 | A | B | 171.7 |
| PP2376 | 2.8E−10 | A | A | 4.8 |
| PP2377 | 3.2E−10 | A | A | 5.7 |

TABLE 37-continued

| Compound No. | KRAS KD (M) | NRAS/ KRAS | HRAS/ KRAS | NCI-H441 IC$_{50}$ (nM) |
|---|---|---|---|---|
| PP2378 | 8.8E−10 | B | A | 48.3 |
| PP2379 | 7.6E−10 | A | A | 2.2 |
| PP2380 | 8.5E−10 | A | A | 2.1 |
| PP2381 | 9.3E−10 | A | A | 3.2 |
| PP2382 | 1.2E−10 | A | A | 4.6 |
| PP2383 | 1.2E−10 | A | A | 5.2 |
| PP2385 | 1.2E−10 | A | B | 7.8 |
| PP2386 | 1.2E−09 | A | B | 28.1 |
| PP2387 | 1.1E−10 | A | A | 16.5 |
| PP2388 | 3.3E−10 | A | B | 22.9 |
| PP2389 | 7.9E−11 | A | B | 21.3 |
| PP2390 | 2.8E−10 | A | B | 96.7 |
| PP2391 | 4.3E−11 | A | A | 8.9 |
| PP2392 | 1.1E−10 | A | A | 25.4 |
| PP2393 | 1.2E−10 | A | A | 28.2 |
| PP2394 | 1.2E−10 | A | B | 8.3 |
| PP2395 | 7.2E−11 | A | B | 6.3 |
| PP2396 | 6.9E−11 | A | A | 4.1 |
| PP2397 | 5.1E−11 | A | A | 4.7 |
| PP2398 | 2.3E−10 | A | A | 11.4 |
| PP2399 | 3.1E−10 | AA | A | 7.7 |
| PP2400 | 2.0E−10 | A | A | 5.8 |
| PP2401 | 1.2E−10 | A | A | 5.3 |
| PP2402 | 9.2E−11 | A | A | 10.6 |
| PP2403 | 2.2E−10 | A | A | 7.2 |
| PP2404 | 9.0E−11 | A | A | 4.1 |
| PP2405 | 3.1E−10 | A | A | 8.6 |
| PP2406 | 2.9E−10 | A | A | 21.3 |
| PP2407 | 5.0E−10 | A | A | 60.1 |
| PP2408 | 2.3E−10 | A | A | 21.3 |
| PP2409 | 4.8E−10 | A | B | 31.9 |
| PP2410 | 1.1E−09 | A | A | 107.9 |
| PP2411 | 1.0E−09 | A | A | 91.4 |
| PP2412 | 1.5E−10 | A | B | 21.0 |
| PP2413 | 2.5E−10 | A | A | 115.4 |
| PP2414 | 3.3E−10 | A | A | 9.8 |
| PP2415 | 9.3E−11 | AA | A | 10.3 |
| PP2416 | 2.9E−10 | A | B | 33.1 |
| PP2417 | 3.0E−10 | A | A | 15.9 |
| PP2418 | 9.7E−10 | A | B | 132.1 |
| PP2419 | 2.0E−09 | A | A | 125.1 |
| PP2422 | 4.6E−10 | A | A | 117.4 |
| PP2423 | 3.8E−10 | A | A | 71.9 |
| PP2424 | 3.7E−10 | A | A | 50.9 |
| PP2425 | 2.3E−10 | AA | A | 51.7 |
| PP2426 | 3.1E−10 | AA | A | 48.0 |
| PP2427 | 7.0E−10 | AA | A | 36.6 |
| PP2428 | 6.2E−10 | A | A | 4.8 |
| PP2429 | 4.5E−09 | A | B | 8.3 |
| PP2430 | 1.4E−09 | AA | A | 33.2 |
| PP2431 | 2.3E−10 | A | A | 79.5 |
| PP2432 | 1.4E−09 | A | A | 138.1 |
| PP2433 | 2.1E−09 | AA | | 120.0 |
| PP2436 | 1.6E−09 | A | A | 126.4 |
| PP2437 | 1.2E−10 | A | A | 18.8 |
| PP2438 | 6.4E−10 | A | A | 41.4 |
| PP2439 | 1.2E−10 | A | A | 6.6 |
| PP2440 | 4.4E−10 | A | A | 20.1 |
| PP2441 | 2.9E−10 | AA | A | 22.9 |
| PP2442 | 9.7E−10 | A | A | 79.7 |
| PP2443 | 1.3E−10 | A | A | 9.1 |
| PP2444 | 5.9E−10 | A | A | 32.3 |
| PP2445 | 1.4E−10 | A | B | 11.7 |
| PP2446 | 8.1E−10 | A | A | 124.4 |
| PP2447 | 1.1E−10 | A | B | 8.6 |
| PP2448 | 1.4E−09 | A | A | 26.9 |
| PP2449 | 6.1E−11 | A | A | 7.8 |
| PP2450 | 5.5E−10 | A | A | 29.2 |
| PP2451 | 1.7E−10 | A | A | 8.6 |
| PP2452 | 1.5E−09 | A | A | 43.4 |
| PP2453 | 9.0E−11 | A | A | 9.2 |
| PP2454 | 1.2E−09 | AA | A | 80.2 |
| PP2455 | 3.2E−10 | AA | A | 23.4 |
| PP2456 | 1.1E−09 | A | A | 18.8 |
| PP2457 | 1.7E−10 | A | A | 13.3 |
| PP2458 | 1.3E−09 | A | A | 80.7 |
| PP2460 | 7.1E−10 | A | A | 18.7 |
| PP2461 | 1.5E−10 | A | A | 10.6 |
| PP2462 | 1.6E−09 | A | A | 87.2 |
| PP2463 | 1.1E−10 | A | A | 6.5 |
| PP2464 | 9.8E−10 | A | A | 66.0 |
| PP2465 | 5.1E−10 | AA | A | 39.4 |
| PP2466 | 3.9E−09 | A | A | 170.3 |
| PP2467 | 2.6E−10 | A | B | 21.8 |
| PP2468 | 1.3E−09 | AA | A | 72.2 |
| PP2469 | 1.9E−10 | A | B | 15.7 |
| PP2470 | 1.8E−09 | A | A | 117.8 |
| PP2471 | 1.6E−10 | A | A | 15.3 |
| PP2472 | 5.8E−10 | A | A | 42.3 |
| PP2475 | 1.5E−09 | AA | A | 175.6 |
| PP2477 | 1.8E−09 | A | A | 126.6 |
| PP2479 | 1.4E−09 | AA | A | 26.0 |
| PP2480 | 8.4E−10 | A | A | 30.5 |
| PP2481 | 1.6E−09 | A | A | 33.6 |
| PP2482 | 9.3E−10 | A | A | 23.8 |
| PP2483 | 1.6E−09 | A | A | 195.4 |
| PP2484 | 1.0E−09 | A | A | 74.3 |
| PP2485 | 7.8E−10 | A | A | 55.5 |
| PP2488 | 1.6E−09 | A | A | 170.9 |
| PP2489 | 5.5E−10 | A | A | 30.5 |
| PP2490 | 1.7E−09 | AA | A | 161.9 |
| PP2492 | 2.4E−09 | AA | A | 76.7 |
| PP2494 | 1.8E−09 | A | A | 39.6 |
| PP2495 | 8.4E−10 | A | A | 17.4 |
| PP2496 | 6.2E−09 | A | A | 97.3 |
| PP2497 | 1.5E−09 | A | A | 84.8 |
| PP2498 | 6.7E−10 | A | A | 21.9 |
| PP2499 | 2.1E−09 | AA | A | 115.2 |
| PP2500 | 1.7E−09 | A | A | 125.4 |
| PP2501 | 1.8E−09 | AA | A | 180.0 |
| PP2502 | 6.5E−11 | A | A | 7.9 |
| PP2504 | 1.6E−10 | A | B | 12.9 |
| PP2505 | 1.3E−10 | A | B | 17.2 |
| PP2506 | 1.3E−10 | A | A | 10.6 |
| PP2507 | 6.1E−11 | AA | A | 8.9 |
| PP2508 | 3.4E−09 | A | B | 123.8 |
| PP2509 | 2.6E−09 | AA | A | 91.3 |
| PP2510 | 3.9E−09 | A | B | 180.5 |
| PP2511 | 9.5E−10 | A | A | 107.3 |
| PP2512 | 2.0E−09 | A | A | 108.7 |
| PP2513 | 2.6E−09 | A | A | 303.1 |
| PP2514 | 2.4E−09 | A | B | 86.8 |
| PP2515 | 5.1E−09 | A | A | 383.7 |
| PP2516 | 2.9E−09 | A | B | 124.4 |
| PP2517 | 9.3E−09 | | A | 561.6 |
| PP2518 | 3.3E−09 | A | A | 81.2 |
| PP2519 | 8.2E−10 | A | A | 27.0 |
| PP2520 | 3.3E−09 | A | A | 209.7 |
| PP2521 | 2.8E−09 | A | A | 129.0 |
| PP2522 | 3.2E−09 | B | B | 113.4 |
| PP2523 | 1.7E−09 | A | A | 91.9 |
| PP2524 | 3.6E−09 | A | B | 185.3 |
| PP2525 | 3.8E−09 | AA | A | 142.4 |
| PP2526 | 4.0E−09 | A | B | 54.5 |
| PP2527 | 6.5E−10 | AA | A | 31.0 |
| PP2528 | 4.6E−09 | A | B | 206.8 |
| PP2529 | 7.7E−10 | AA | A | 64.0 |
| PP2530 | 3.6E−09 | A | B | 131.3 |
| PP2531 | 5.1E−10 | AA | A | 16.3 |
| PP2532 | 4.1E−09 | A | B | 143.6 |
| PP2533 | 4.9E−10 | AA | A | 20.0 |
| PP2534 | 4.1E−09 | A | B | 195.4 |
| PP2535 | 5.4E−10 | AA | A | 26.8 |
| PP2536 | 2.4E−09 | A | B | 152.3 |
| PP2537 | 7.4E−10 | AA | A | 75.1 |
| PP2539 | 4.3E−09 | A | B | 330.4 |
| PP2540 | 4.6E−09 | A | B | 562.4 |
| PP2541 | 4.9E−09 | A | B | 373.6 |
| PP2542 | 4.6E−09 | B | B | 393.8 |
| PP2543 | 4.2E−09 | | B | 179.1 |
| PP2545 | 4.3E−09 | A | A | 279.0 |
| PP2546 | 4.7E−09 | B | B | 295.0 |
| PP2547 | 4.4E−09 | A | B | 1063.5 |
| PP2548 | 7.8E−09 | A | B | 1046.6 |

TABLE 37-continued

| Compound No. | KRAS KD (M) | NRAS/ KRAS | HRAS/ KRAS | NCI-H441 IC$_{50}$ (nM) |
|---|---|---|---|---|
| PP2549 | 6.0E−09 | A | B | 506.3 |
| PP2550 | 2.9E−10 | A | B | 38.5 |
| PP2551 | 4.0E−10 | A | B | 36.4 |
| PP2552 | 2.8E−10 | A | B | 30.5 |
| PP2553 | 3.4E−09 | A | B | 120.7 |
| PP2554 | 5.6E−09 | A | B | 271.4 |
| PP2555 | 4.1E−09 | A | B | 211.9 |
| PP2556 | 2.1E−10 | A | B | 9.4 |
| PP2557 | 3.0E−10 | A | B | 14.2 |
| PP2558 | 3.2E−10 | A | B | 14.1 |
| PP2559 | 9.1E−10 | A | A | 103.2 |
| PP2560 | 1.0E−09 | AA | A | 46.3 |
| PP2561 | 1.9E−09 | AA | A | 96.4 |
| PP2562 | 9.1E−10 | B | B | 46.5 |
| PP2563 | 2.3E−09 | A | A | 107.5 |
| PP2564 | 7.6E−09 | A | A | 222.3 |
| PP2565 | 8.2E−09 | A | A | 206.5 |
| PP2566 | 5.7E−10 | A | B | 17.6 |
| PP2567 | 1.9E−09 | A | A | 101.6 |
| PP2568 | 1.2E−09 | A | B | 23.4 |
| PP2569 | 2.8E−09 | AA | A | 184.9 |
| PP2570 | 3.9E−10 | A | A | 8.9 |
| PP2571 | 1.0E−09 | A | A | 76.1 |
| PP2572 | 1.2E−09 | A | A | 82.7 |
| PP2573 | 1.0E−10 | A | A | 10.1 |
| PP2574 | 5.1E−11 | A | A | 4.2 |
| PP2575 | 8.6E−11 | A | A | 4.1 |
| PP2576 | 1.4E−10 | A | A | 5.7 |
| PP2577 | 1.2E−10 | A | A | 4.1 |
| PP2578 | 2.7E−10 | AA | A | 17.7 |
| PP2579 | 1.7E−10 | A | A | 14.5 |
| PP2580 | 2.0E−10 | AA | A | 7.9 |
| PP2581 | 2.1E−10 | AA | A | 32.1 |
| PP2583 | 1.1E−10 | A | A | 4.1 |
| PP2586 | 1.7E−10 | A | B | 14.4 |
| PP2588 | 2.6E−10 | A | A | 13.2 |
| PP2589 | 4.5E−10 | AA | A | 74.1 |
| PP2590 | 1.3E−09 | AA | A | 27.1 |
| PP2591 | 5.6E−10 | AA | A | 9.1 |
| PP2592 | 1.3E−10 | A | A | 7.9 |
| PP2593 | 1.5E−10 | A | A | 11.5 |
| PP2594 | 1.0E−10 | A | A | 6.0 |
| PP2595 | 1.7E−10 | A | B | 12.7 |
| PP2596 | 1.6E−10 | A | A | 13.7 |
| PP2597 | 5.1E−10 | A | A | 20.1 |
| PP2598 | 1.9E−09 | A | A | 23.0 |
| PP2600 | 1.7E−10 | A | A | 2.9 |
| PP2601 | 2.0E−10 | A | A | 8.9 |
| PP2602 | 2.5E−10 | A | A | 12.8 |
| PP2603 | 4.4E−10 | AA | A | 25.7 |
| PP2604 | 4.0E−10 | AA | A | 20.8 |
| PP2605 | 3.4E−10 | AA | A | 8.7 |
| PP2606 | 8.1E−10 | AA | AA | 68.7 |
| PP2608 | 1.4E−09 | AA | A | 53.0 |
| PP2610 | 1.3E−09 | AA | A | 125.5 |
| PP2612 | 2.4E−09 | AA | A | 199.3 |
| PP2614 | 2.7E−10 | A | A | 12.1 |
| PP2615 | 2.0E−09 | A | A | 88.7 |
| PP2616 | 8.0E−10 | A | A | 66.4 |
| PP2618 | 1.4E−09 | A | A | 69.5 |
| PP2619 | 1.2E−09 | AA | A | 131.5 |
| PP2622 | 5.3E−10 | A | B | 43.8 |
| PP2624 | 1.3E−09 | A | A | 174.0 |
| PP2626 | 4.1E−10 | A | A | 33.4 |
| PP2627 | 2.6E−09 | A | A | 95.2 |
| PP2628 | 9.0E−10 | A | A | 67.9 |
| PP2630 | 3.0E−09 | A | B | 190.3 |
| PP2631 | 5.0E−10 | AA | A | 56.9 |
| PP2633 | 6.4E−10 | AA | A | 29.0 |
| PP2634 | 6.8E−10 | A | A | 45.4 |
| PP2635 | 9.7E−10 | AA | A | 50.2 |
| PP2637 | 1.0E−09 | AA | A | 61.4 |
| PP2638 | 2.5E−09 | AA | A | 97.0 |
| PP2639 | 1.1E−09 | AA | A | 81.6 |
| PP2640 | 1.4E−09 | AA | A | 84.1 |
| PP2641 | 2.0E−09 | AA | A | 98.6 |
| PP2642 | 4.4E−10 | AA | A | 36.6 |
| PP2643 | 4.9E−10 | AA | A | 32.7 |
| PP2644 | 8.1E−10 | AA | A | 75.0 |
| PP2645 | 1.1E−09 | AA | A | 86.7 |
| PP2646 | 1.6E−09 | AA | A | 92.6 |
| PP2648 | 8.5E−10 | A | A | 68.5 |
| PP2649 | 4.0E−10 | AA | A | 61.0 |
| PP2650 | 9.8E−10 | AA | A | 42.2 |
| PP2651 | 1.9E−09 | AA | A | 147.1 |
| PP2652 | 1.5E−09 | AA | A | 82.7 |
| PP2654 | 1.2E−10 | A | A | 12.4 |
| PP2655 | 1.0E−10 | AA | A | 17.0 |
| PP2656 | 3.1E−10 | A | B | 22.5 |
| PP2657 | 4.4E−10 | A | A | 29.2 |
| PP2659 | 1.9E−10 | A | A | 20.6 |
| PP2660 | 1.8E−10 | A | A | 14.3 |
| PP2661 | 2.7E−10 | AA | A | 13.4 |
| PP2662 | 2.9E−10 | AA | A | 13.1 |
| PP2663 | 2.4E−10 |  | A | 11.2 |
| PP2664 | 3.7E−10 | A | B | 19.8 |
| PP2665 | 5.6E−10 | A | A | 23.4 |
| PP2666 | 7.2E−10 | AA | AA | 28.6 |
| PP2667 | 1.8E−09 | A | A | 30.6 |
| PP2668 | 1.8E−10 | A | A | 10.3 |
| PP2669 | 2.9E−10 | A | A | 18.7 |
| PP2670 | 4.8E−10 | AA | A | 25.2 |
| PP2671 | 6.7E−10 | A | A | 26.3 |
| PP2672 | 1.9E−10 | B | B | 9.5 |
| PP2673 | 6.9E−10 | A | A | 50.8 |
| PP2674 | 5.0E−10 | A | A | 48.6 |
| PP2675 | 4.5E−09 | A | A | 138.4 |
| PP2676 | 8.7E−10 | A | A | 60.8 |
| PP2677 | 1.3E−09 | A | A | 70.6 |
| PP2678 | 5.5E−10 | A | B | 45.5 |
| PP2679 | 9.9E−11 | A | A | 17.7 |
| PP2681 | 3.7E−10 | A | A | 29.1 |
| PP2683 | 8.7E−10 | A | A | 63.3 |
| PP2684 | 4.3E−10 | A | A | 57.9 |
| PP2685 | 2.1E−09 | A | A | 133.4 |
| PP2686 | 3.3E−09 | A | A | 162.1 |
| PP2687 | 7.7E−11 | A | A | 2.9 |
| PP2688 | 1.3E−10 | A | B | 6.9 |
| PP2689 | 1.8E−10 | A | B | 6.2 |
| PP2690 | 3.9E−11 | AA | A | 3.0 |
| PP2691 | 5.6E−11 | AA | A | 3.5 |
| PP2692 | 1.4E−10 | A | A | 7.7 |
| PP2693 | 1.8E−10 | A | B | 10.4 |
| PP2694 | 1.9E−10 | A | B | 12.0 |
| PP2695 | 5.4E−11 | A | B | 3.8 |
| PP2696 | 1.9E−10 | A | B | 20.5 |
| PP2697 | 4.8E−10 | A | A | 42.8 |
| PP2698 | 3.8E−10 | A | A | 30.4 |
| PP2699 | 1.3E−10 | A | B | 14.2 |
| PP2700 | 2.0E−10 | A | B | 23.1 |
| PP2701 | 2.4E−10 | A | A | 21.7 |
| PP2702 | 1.8E−10 | A | B | 21.4 |
| PP2703 | 2.6E−10 | AA | A | 80.5 |
| PP2704 | 1.5E−10 | B | B | 10.7 |
| PP2706 | 7.6E−11 | A | B | 2.3 |
| PP2708 | 7.2E−11 | A | A | 5.1 |
| PP2710 | 1.0E−10 | B | B | 5.3 |
| PP2712 | 1.1E−10 | A | B | 6.3 |
| PP2714 | 2.5E−10 | A | A | 13.2 |
| PP2716 | 3.4E−10 | A | A | 13.8 |
| PP2718 | 3.3E−10 | A | A | 7.6 |
| PP2720 | 3.5E−10 | A | A | 7.7 |
| PP2722 | 4.0E−10 | B | B | 13.9 |
| PP2724 | 4.3E−10 | A | B | 20.0 |
| PP2726 | 1.1E−09 | AA | A | 51.0 |
| PP2728 | 1.1E−09 | AA | A | 54.3 |
| PP2730 | 6.5E−11 | A | A | 5.8 |
| PP2732 | 6.7E−11 | A | A | 5.3 |
| PP2734 | 1.0E−10 | A | B | 3.1 |
| PP2736 | 6.1E−11 | A | A | 7.5 |
| PP2738 | 1.7E−10 | AA | A | 8.5 |
| PP2740 | 1.7E−10 | AA | A | 24.2 |
| PP2742 | 2.6E−10 | AA | A | 14.9 |
| PP2744 | 2.3E−10 | A | A | 10.7 |

TABLE 37-continued

| Compound No. | KRAS KD (M) | NRAS/ KRAS | HRAS/ KRAS | NCI-H441 IC$_{50}$ (nM) |
|---|---|---|---|---|
| PP2746 | 2.8E−10 | A | A | 10.2 |
| PP2748 | 2.0E−10 | A | A | 7.1 |
| PP2749 | 8.7E−10 | AA | A | 22.1 |
| PP2750 | 5.4E−10 | AA | A | 19.0 |
| PP2751 | 8.5E−10 | A | A | 39.3 |
| PP2752 | 1.2E−09 | A | A | 70.3 |
| PP2753 | 9.7E−10 | A | B | 52.0 |
| PP2754 | 1.2E−09 | A | A | 57.1 |
| PP2755 | 5.6E−10 | A | A | 35.7 |
| PP2756 | 6.2E−10 | A | A | 93.6 |
| PP2757 | 4.3E−09 | A | A | 91.1 |
| PP2760 | 4.8E−09 | A | B | 144.4 |
| PP2761 | 2.8E−09 | A | A | 68.4 |
| PP2762 | 2.9E−09 | A | A | 122.3 |
| PP2763 | 8.6E−10 | A | A | 71.9 |
| PP2764 | 8.5E−10 | A | A | 55.8 |
| PP2765 | 7.0E−10 | A | A | 180.4 |
| PP2766 | 5.2E−10 | A | A | 26.0 |
| PP2767 | 4.9E−10 | A | A | 62.6 |
| PP2768 | 5.5E−09 | A | A | 119.6 |
| PP2769 | 2.5E−09 | AA | A | 133.2 |
| PP2770 | 5.0E−10 | A | A | 137.2 |
| PP2771 | 2.2E−09 | AA | A | 148.4 |
| PP2772 | 4.3E−10 | B | B | 28.1 |
| PP2773 | 5.2E−10 | B | B | 8.6 |
| PP2776 | 8.6E−10 | A | A | 60.1 |
| PP2777 | 2.4E−09 | AA | A | 110.9 |
| PP2778 | 6.2E−10 | A | A | 22.3 |
| PP2779 | 3.4E−09 | A | A | 111.7 |
| PP2780 | 3.0E−10 | A | A | 17.8 |
| PP2781 | 1.5E−09 | AA | A | 64.1 |
| PP2782 | 4.9E−10 | A | A | 59.1 |
| PP2783 | 1.7E−09 | A | A | 33.9 |
| PP2784 | 1.3E−10 | A | A | 7.2 |
| PP2785 | 2.6E−10 | AA | A | 10.5 |
| PP2786 | 1.4E−10 | A | A | 9.8 |
| PP2787 | 3.6E−10 | AA | A | 22.1 |
| PP2788 | 4.5E−10 | A | A | 24.4 |
| PP2789 | 1.0E−09 | AA | A | 47.3 |
| PP2790 | 5.4E−10 | A | A | 59.4 |
| PP2791 | 1.9E−09 |  | A | 89.8 |
| PP2796 | 1.2E−10 | A | A | 9.6 |
| PP2797 | 6.0E−10 | A | A | 52.8 |
| PP2798 | 7.5E−11 | A | A | 8.5 |
| PP2799 | 1.2E−09 | A | A | 136.3 |
| PP2800 | 5.6E−11 | A | A | 7.9 |
| PP2801 | 2.2E−09 | A | A | 109.7 |
| PP2802 | 3.4E−11 | AA | A | 5.5 |
| PP2803 | 5.9E−09 | A | A | 119.7 |
| PP2804 | 3.3E−11 | A | A | 2.2 |
| PP2805 | 3.7E−09 | A | A | 83.0 |
| PP2806 | 1.2E−10 | A | A | 11.3 |
| PP2807 | 3.4E−10 | AA | A | 28.0 |
| PP2808 | 4.3E−10 | B | B | 13.1 |
| PP2809 | 9.0E−10 | A | A | 76.6 |
| PP2810 | 4.6E−10 | AA | A | 38.1 |
| PP2811 | 8.2E−10 | A | A | 100.2 |
| PP2812 | 5.6E−10 | AA | A | 41.0 |
| PP2813 | 1.7E−09 | AA | A | 86.0 |
| PP2814 | 3.7E−10 | AA | A | 44.4 |
| PP2815 | 3.6E−09 | A | A | 187.6 |
| PP2816 | 3.9E−10 | AA | A | 22.8 |
| PP2817 | 2.4E−09 | A | A | 55.2 |
| PP2818 | 8.8E−10 | A | A | 77.1 |
| PP2819 | 2.2E−09 | A | A | 101.5 |
| PP2820 | 9.4E−10 | AA | A | 62.4 |
| PP2821 | 1.8E−09 | A | A | 90.4 |
| PP2822 | 2.6E−10 | A | A | 14.1 |
| PP2823 | 1.3E−10 | A | A | 7.6 |
| PP2824 | 4.4E−10 | A | A | 23.4 |
| PP2825 | 1.2E−10 | A | B | 7.6 |
| PP2826 | 1.4E−10 | A | A | 8.6 |
| PP2827 | 3.8E−10 | A | B | 21.0 |
| PP2828 | 1.1E−10 | A | A | 5.0 |
| PP2829 | 9.5E−11 | A | A | 7.9 |
| PP2830 | 3.7E−10 | A | A | 28.8 |
| PP2831 | 1.1E−10 | A | A | 14.1 |
| PP2832 | 1.8E−10 | A | A | 4.8 |
| PP2833 | 5.2E−11 | A | A | 3.8 |
| PP2834 | 2.2E−10 | A | A | 24.6 |
| PP2835 | 1.9E−10 | A | A | 13.0 |
| PP2836 | 6.5E−11 | A | A | 5.1 |
| PP2837 | 2.1E−10 | AA | A | 12.8 |
| PP2838 | 6.6E−11 | AA | A | 7.9 |
| PP2839 | 2.5E−10 | A | A | 27.0 |
| PP2840 | 1.0E−10 | A | A | 8.3 |
| PP2841 | 8.6E−11 | A | A | 8.3 |
| PP2842 | 8.0E−11 | A | B | 7.2 |
| PP2843 | 2.6E−10 | A | A | 17.7 |
| PP2844 | 1.2E−10 | A | A | 7.6 |
| PP2845 | 3.0E−10 | AA | A | 22.7 |
| PP2846 | 9.1E−11 | AA | A | 5.1 |
| PP2847 | 8.3E−11 | A | A | 7.3 |
| PP2848 | 4.7E−10 | A | A | 28.9 |
| PP2849 | 5.8E−10 | A | A | 28.2 |
| PP2850 | 1.8E−09 | A | A | 98.9 |
| PP2852 | 3.0E−10 | B | B | 8.7 |
| PP2853 | 7.4E−10 | A | A | 40.2 |
| PP2854 | 4.1E−10 | A | A | 12.4 |
| PP2855 | 1.4E−09 | A | A | 37.9 |
| PP2856 | 1.1E−09 | A | A | 33.5 |
| PP2857 | 2.3E−09 | A | A | 61.6 |
| PP2858 | 3.3E−10 | A | B | 11.8 |
| PP2859 | 1.2E−10 | A | A | 6.8 |
| PP2860 | 3.4E−10 | A | A | 12.9 |
| PP2861 | 1.1E−10 | A | B | 6.3 |
| PP2862 | 5.4E−10 | A | B | 36.3 |
| PP2863 | 1.6E−09 | A | A | 127.6 |
| PP2864 | 2.0E−09 | A | A | 124.3 |
| PP2865 | 5.8E−10 | A | A | 37.7 |
| PP2866 | 7.3E−10 | A | A | 39.6 |
| PP2867 | 2.2E−10 | A | A | 17.1 |
| PP2868 | 4.2E−10 | A | A | 41.4 |
| PP2869 | 9.0E−10 | A | A | 37.6 |
| PP2870 | 5.8E−10 | A | A | 11.5 |
| PP2871 | 1.5E−09 | A | A | 28.4 |
| PP2872 | 2.3E−09 | A | A | 88.3 |
| PP2873 | 2.5E−08 | A | A | 128.1 |
| PP2874 | 2.7E−09 | A | A | 44.0 |
| PP2875 | 4.7E−09 | A | A | 120.7 |
| PP2876 | 1.7E−09 | A | A | 79.9 |
| PP2877 | 2.7E−09 | A | A | 96.0 |
| PP2879 | 3.9E−09 | A | A | 121.7 |
| PP2880 | 1.2E−08 | A | A | 126.7 |
| PP2881 | 1.0E−09 | A | A | 28.2 |
| PP2883 | 5.1E−09 | A | A | 76.2 |
| PP2884 | 2.7E−09 | A | A | 35.9 |
| PP2885 | 2.1E−09 | A | A | 80.6 |
| PP2886 | 7.2E−09 | A | A | 111.8 |
| PP2888 | 3.9E−10 | AA | A | 14.2 |
| PP2889 | 2.9E−10 | A | A | 20.9 |
| PP2890 | 4.2E−10 | AA | A | 10.3 |
| PP2891 | 3.3E−10 | A | B | 17.2 |
| PP2892 | 2.8E−10 | A | A | 8.0 |
| PP2893 | 2.0E−09 | A | A | 72.0 |
| PP2894 | 3.1E−10 | AA | A | 9.6 |
| PP2895 | 3.2E−09 | A | A | 59.0 |
| PP2896 | 2.8E−09 | A | A | 79.3 |
| PP2897 | 5.6E−10 | A | B | 10.5 |
| PP2898 | 4.8E−09 | A | A | 98.1 |
| PP2899 | 8.5E−10 | A | B | 18.8 |
| PP2900 | 4.4E−10 | AA | A | 14.5 |
| PP2901 | 3.1E−09 | A | A | 86.5 |
| PP2902 | 7.1E−10 | AA | A | 56.3 |
| PP2904 | 3.8E−09 | AA | A | 82.4 |
| PP2905 | 2.4E−10 | AA | A | 35.2 |
| PP2906 | 5.5E−09 | A | A | 99.3 |
| PP2907 | 2.3E−10 | AA | A | 46.3 |
| PP2908 | 1.5E−09 | AA | A | 20.2 |
| PP2909 | 1.0E−09 | B | B | 61.3 |
| PP2910 | 3.0E−09 | AA | A | 39.8 |
| PP2911 | 5.2E−10 | A | B | 64.8 |
| PP2912 | 8.7E−09 | AA | A | 86.0 |
| PP2913 | 1.7E−10 | A | A | 10.3 |

TABLE 37-continued

| Compound No. | KRAS KD (M) | NRAS/ KRAS | HRAS/ KRAS | NCI-H441 IC$_{50}$ (nM) |
|---|---|---|---|---|
| PP2914 | 1.4E−08 | AA | A | 310.6 |
| PP2915 | 1.2E−09 | A | A | 128.8 |
| PP2916 | 1.3E−09 | A | A | 106.1 |
| PP2917 | 1.4E−09 | AA | A | 130.2 |
| PP2918 | 1.8E−09 | AA | A | 126.2 |
| PP2920 | 4.0E−09 | AA | A | 118.3 |
| PP2921 | 6.9E−09 | AA | A | 160.1 |
| PP2922 | 1.1E−09 | AA | A | 55.4 |
| PP2923 | 1.5E−09 | A | A | 58.6 |
| PP2928 | 4.8E−09 | AA | A | 167.9 |
| PP2929 | 2.3E−09 | AA | A | 90.3 |
| PP2931 | 1.9E−09 | A | A | 65.5 |
| PP2932 | 1.6E−09 | A | A | 120.9 |
| PP2934 | 2.0E−09 | AA | A | 107.8 |
| PP2935 | 1.5E−09 | A | A | 50.5 |
| PP2936 | 2.7E−09 | AA | A | 187.3 |
| PP2937 | 1.1E−09 | A | A | 137.0 |
| PP2938 | 1.1E−09 | AA | A | 104.0 |
| PP2941 | 2.5E−09 | AA | A | 104.1 |
| PP2946 | 5.2E−11 | A | | 5.3 |
| PP2947 | 1.2E−10 | B | B | 3.5 |
| PP2948 | 5.5E−11 | A | A | 3.3 |
| PP2949 | 5.9E−11 | A | | 3.5 |
| PP2950 | 7.6E−10 | A | A | 24.2 |
| PP2951 | 1.0E−09 | A | A | 37.0 |
| PP2952 | 7.9E−10 | AA | | 45.0 |
| PP2953 | 6.2E−10 | AA | A | 33.4 |
| PP2954 | 3.7E−10 | A | A | 16.5 |
| PP2955 | 1.4E−10 | A | A | 7.7 |
| PP2956 | 1.1E−09 | AA | | 27.8 |
| PP2957 | 2.3E−10 | AA | | 4.6 |
| PP2958 | 3.8E−10 | AA | A | 19.5 |
| PP2959 | 2.7E−10 | AA | A | 14.6 |
| PP2960 | 3.2E−10 | A | A | 8.9 |
| PP2961 | 3.6E−10 | AA | A | 13.9 |
| PP2962 | 1.2E−09 | AA | A | 39.2 |
| PP2963 | 3.9E−10 | AA | | 13.4 |
| PP2964 | 8.5E−10 | AA | A | 50.1 |
| PP2965 | 4.7E−10 | AA | A | 27.1 |
| PP2966 | 5.7E−10 | A | A | 29.3 |
| PP2967 | 4.1E−10 | AA | A | 17.0 |
| PP2968 | 5.5E−10 | AA | | 29.5 |
| PP2969 | 7.3E−11 | AA | A | 2.7 |
| PP2970 | 4.6E−10 | A | | 23.0 |
| PP2971 | 1.9E−10 | A | 4 | 5.1 |
| PP2972 | 1.4E−09 | AA | A | 81.6 |
| PP2973 | 1.8E−10 | A | A | 7.9 |
| PP2974 | 1.3E−09 | A | A | 38.6 |
| PP2975 | 9.6E−10 | A | A | 16.7 |
| PP2976 | 1.8E−10 | A | B | 8.7 |
| PP2977 | 3.0E−10 | A | A | 8.1 |
| PP2978 | 1.1E−10 | A | A | 5.9 |
| PP2979 | 2.8E−10 | A | B | 5.0 |
| PP2980 | 2.3E−10 | A | B | 11.7 |
| PP2981 | 3.1E−10 | AA | A | 20.3 |
| PP2982 | 1.6E−10 | A | A | 11.9 |
| PP2983 | 5.0E−10 | AA | A | 18.7 |
| PP2984 | 2.0E−10 | A | B | 9.6 |
| PP2985 | 1.4E−09 | AA | A | 46.5 |
| PP2986 | 3.4E−10 | AA | A | 25.1 |
| PP2987 | 6.6E−10 | AA | A | 31.7 |
| PP2988 | 2.9E−10 | B | B | 8.1 |
| PP2989 | 8.7E−11 | AA | A | 6.5 |
| PP2990 | 2.6E−10 | A | A | 8.9 |
| PP2991 | 1.5E−10 | A | A | 4.1 |
| PP2992 | 1.9E−10 | AA | A | 7.5 |
| PP2993 | 4.3E−10 | A | A | 14.1 |
| PP2994 | 2.1E−10 | AA | A | 15.8 |
| PP2995 | 3.2E−10 | A | A | 12.9 |
| PP2996 | 3.6E−10 | AA | A | 13.7 |
| PP2997 | 1.2E−10 | A | B | 4.1 |
| PP2998 | 4.3E−10 | A | AA | 8.3 |
| PP2999 | 1.3E−10 | AA | A | 11.4 |
| PP3000 | 1.3E−09 | AA | A | 63.0 |
| PP3001 | 4.3E−10 | A | B | 14.2 |
| PP3002 | 2.1E−09 | A | A | 127.7 |
| PP3003 | 7.2E−10 | AA | A | 31.2 |
| PP3004 | 4.1E−10 | A | A | 19.2 |
| PP3005 | 1.5E−10 | A | B | 8.8 |
| PP3006 | 4.1E−10 | A | A | 14.1 |
| PP3007 | 1.3E−09 | A | A | 63.4 |
| PP3008 | 3.8E−10 | A | A | 16.0 |
| PP3009 | 7.3E−11 | A | A | 7.7 |
| PP3010 | 4.1E−10 | B | B | 18.2 |
| PP3011 | 5.8E−10 | A | B | 31.1 |
| PP3012 | 1.9E−09 | A | A | 74.8 |
| PP3013 | 5.3E−10 | AA | B | 29.7 |
| PP3014 | 3.7E−10 | AA | A | 20.6 |
| PP3015 | 2.2E−09 | AA | A | 102.6 |
| PP3017 | 1.5E−09 | AA | A | 46.3 |
| PP3018 | 3.2E−10 | A | B | 19.1 |
| PP3019 | 2.0E−09 | AA | A | 42.6 |
| PP3021 | 1.1E−09 | AA | A | 76.7 |
| PP3022 | 5.9E−10 | AA | A | 51.4 |
| PP3026 | 6.6E−10 | A | A | 53.6 |
| PP3030 | 3.1E−10 | AA | A | 22.4 |
| PP3031 | 1.9E−09 | AA | A | 94.2 |
| PP3032 | 1.0E−10 | AA | A | 2.1 |
| PP3033 | 1.8E−10 | A | B | 4.7 |
| PP3034 | 1.1E−10 | A | B | 5.3 |
| PP3035 | 9.2E−11 | AA | A | 4.2 |
| PP3036 | 1.7E−10 | A | B | 8.0 |
| PP3037 | 1.1E−10 | A | B | 3.4 |
| PP3038 | 1.5E−10 | A | A | 3.1 |
| PP3039 | 1.3E−09 | AA | A | 18.0 |
| PP3040 | 2.9E−10 | AA | A | 10.0 |
| PP3044 | 5.2E−11 | AA | A | 7.1 |
| PP3045 | 1.3E−10 | AA | A | 15.9 |
| PP3046 | 3.9E−10 | AA | A | 16.7 |
| PP3047 | 1.8E−10 | AA | A | 6.1 |
| PP3048 | 1.1E−10 | A | A | 11.1 |
| PP3049 | 2.0E−10 | AA | A | 12.6 |
| PP3050 | 2.9E−10 | AA | A | 19.3 |
| PP3051 | 7.5E−10 | AA | A | 42.1 |
| PP3052 | 2.6E−10 | AA | A | 27.6 |
| PP3053 | 1.6E−10 | A | A | 27.0 |
| PP3054 | 2.7E−10 | A | A | 38.4 |
| PP3055 | 1.0E−09 | AA | A | 69.2 |
| PP3056 | 1.4E−09 | A | A | 150.8 |
| PP3057 | 1.7E−10 | A | B | 8.5 |
| PP3058 | 2.1E−10 | A | A | 21.2 |
| PP3059 | 5.5E−11 | A | A | 2.1 |
| PP3060 | 4.2E−11 | B | B | 2.7 |
| PP3061 | 1.3E−10 | A | A | 4.4 |
| PP3062 | 6.6E−11 | A | A | 6.3 |
| PP3063 | 5.6E−10 | B | B | 32.2 |
| PP3064 | 3.7E−10 | B | B | 26.9 |
| PP3065 | 2.3E−10 | A | B | 27.3 |
| PP3066 | 4.2E−11 | A | B | 2.2 |
| PP3067 | 5.3E−11 | A | B | 1.1 |
| PP3068 | 5.0E−11 | A | B | 4.5 |
| PP3069 | 3.4E−11 | A | B | 2.1 |
| PP3070 | 1.7E−10 | | B | 1.4 |
| PP3071 | 1.2E−10 | A | B | 6.6 |
| PP3072 | 4.8E−11 | A | B | 2.6 |
| PP3073 | 2.5E−11 | A | A | 1.9 |
| PP3074 | 2.5E−11 | A | A | 2.4 |
| PP3075 | 7.6E−11 | A | A | 1.1 |
| PP3076 | 5.9E−11 | AA | A | 4.1 |
| PP3077 | 4.0E−11 | A | B | 0.8 |
| PP3078 | 4.8E−11 | A | B | 2.3 |
| PP3079 | 5.0E−11 | A | B | 1.8 |
| PP3080 | 3.7E−11 | A | B | 4.3 |
| PP3081 | 6.8E−11 | A | B | 1.9 |
| PP3082 | 5.1E−10 | B | B | 1.7 |
| PP3083 | 7.7E−11 | A | A | 2.5 |
| PP3084 | 1.2E−10 | A | B | 3.7 |
| PP3085 | 1.1E−10 | A | B | 6.3 |
| PP3086 | 2.0E−10 | B | B | 7.9 |
| PP3087 | 2.2E−10 | B | B | 6.9 |
| PP3088 | 3.4E−10 | B | B | 15.1 |
| PP3089 | 3.3E−10 | B | B | 27.0 |
| PP3090 | 3.3E−11 | A | B | 1.3 |
| PP3091 | 3.1E−11 | A | B | 1.2 |

TABLE 37-continued

| Compound No. | KRAS KD (M) | NRAS/ KRAS | HRAS/ KRAS | NCI-H441 IC$_{50}$ (nM) |
|---|---|---|---|---|
| PP3092 | 9.0E−11 | A | A | 7.4 |
| PP3093 | 9.7E−11 | A | A | 3.2 |
| PP3094 | 8.1E−11 | A | B | 2.2 |
| PP3095 | 6.7E−10 | A | A | 33.7 |
| PP3096 | 5.4E−10 | A | A | 35.8 |
| PP3097 | 3.8E−10 | A | A | 5.4 |
| PP3098 | 2.4E−10 | A | A | 4.7 |
| PP3099 | 6.1E−10 | A | A | 13.3 |
| PP3100 | 2.9E−10 | A | B | 15.0 |
| PP3101 | 2.7E−10 | A | A | 4.9 |
| PP3102 | 1.8E−10 | A | A | 6.7 |
| PP3103 | 2.1E−10 |   | A | 21.5 |
| PP3104 | 9.7E−11 | A | A | 3.8 |
| PP3105 | 6.0E−11 | AA | A | 2.5 |
| PP3106 | 4.8E−11 | A | A | 2.9 |
| PP3108 | 8.7E−07 | C | B | 9253.9 |
| PP3109 | 3.0E−06 |   |   | 3415.3 |
| PP3110 | 4.3E−09 | A | A | 69.9 |
| PP3111 | 4.8E−09 | A | A | 17.8 |
| PP3112 | 3.1E−09 | A | B | 32.4 |
| PP3113 | 1.7E−10 | A | A | 6.1 |
| PP3114 | 4.5E−09 | AA | A | 14.7 |
| PP3115 | 2.6E−09 | A | B | 5.7 |
| PP3116 | 2.7E−10 | A | A | 7.8 |
| PP3117 | 1.5E−10 | A | A | 2.6 |
| PP3118 | 1.2E−10 | A | B | 6.7 |
| PP3119 | 9.0E−11 | A | A | 3.5 |
| PP3120 | 5.2E−11 | AA | A | 1.9 |
| PP3121 | 4.3E−11 | A | A | 1.5 |

List of Structures of Cyclic Compounds

TABLE 38

| Compound No. | Structural Formula |
|---|---|
| PP0001 | 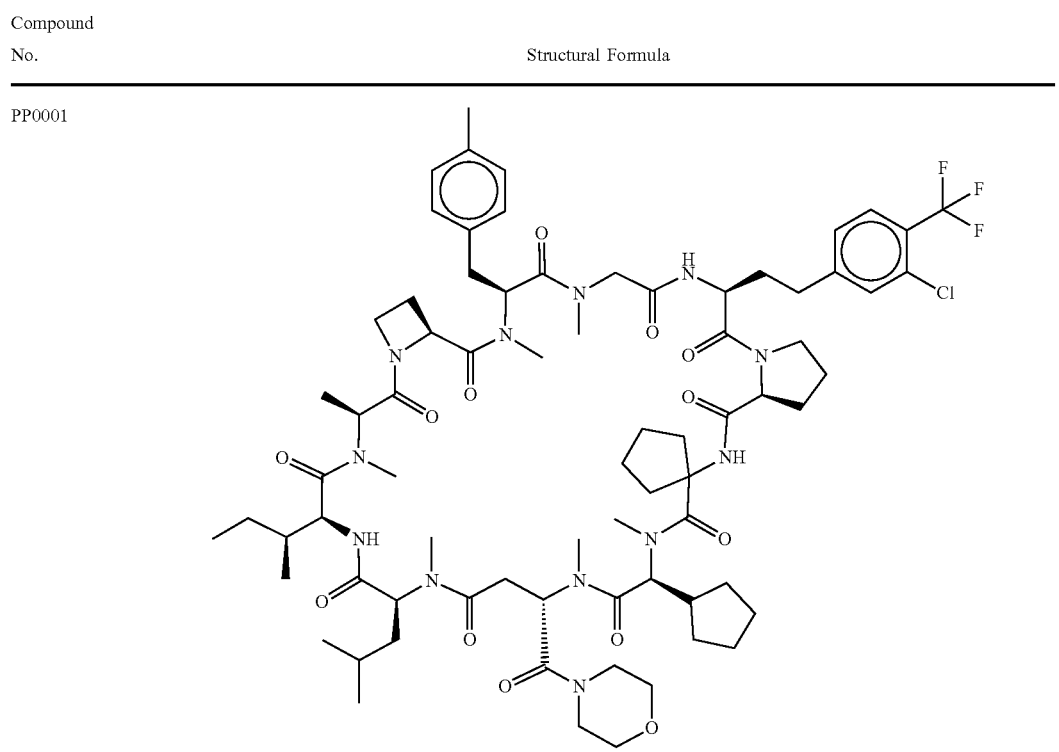 |

TABLE 38-continued
| Compound No. | Structural Formula |
| --- | --- |
| PP0002 | 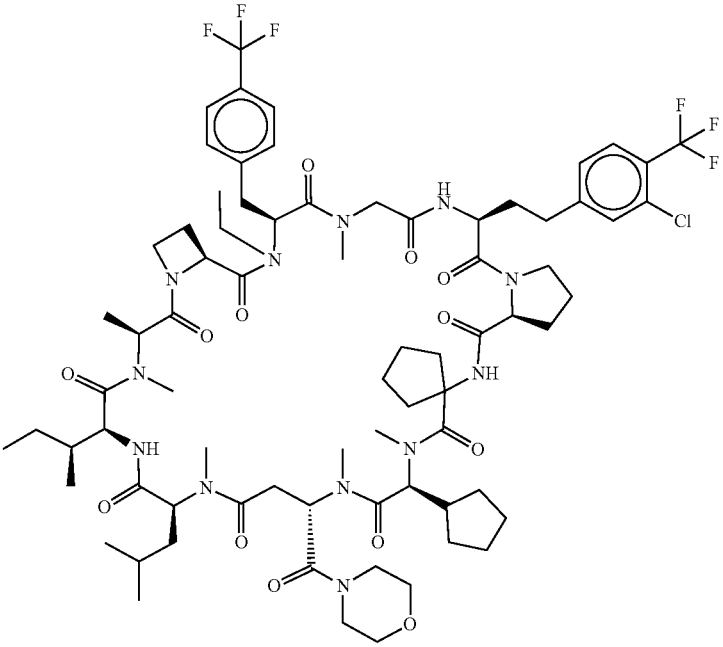 |
| PP0003 | 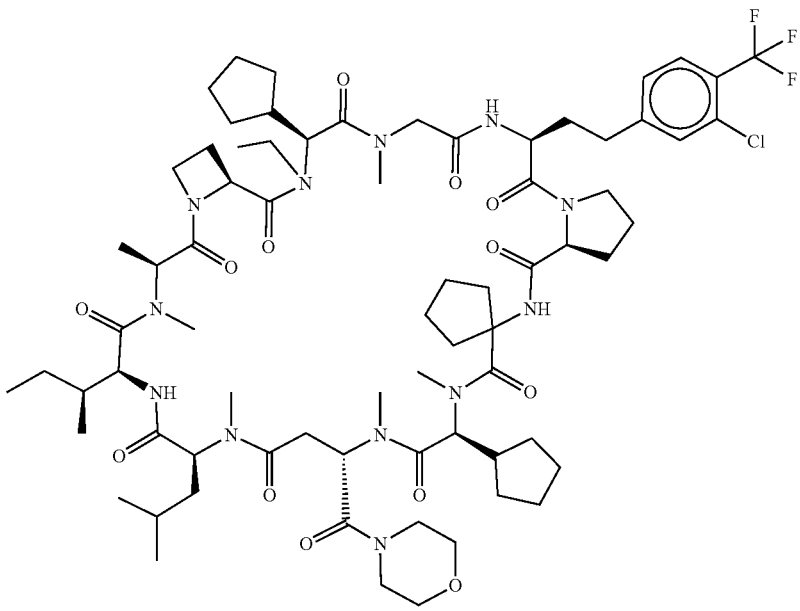 |

TABLE 38-continued
| Compound No. | Structural Formula |
|---|---|
| PP0004 | 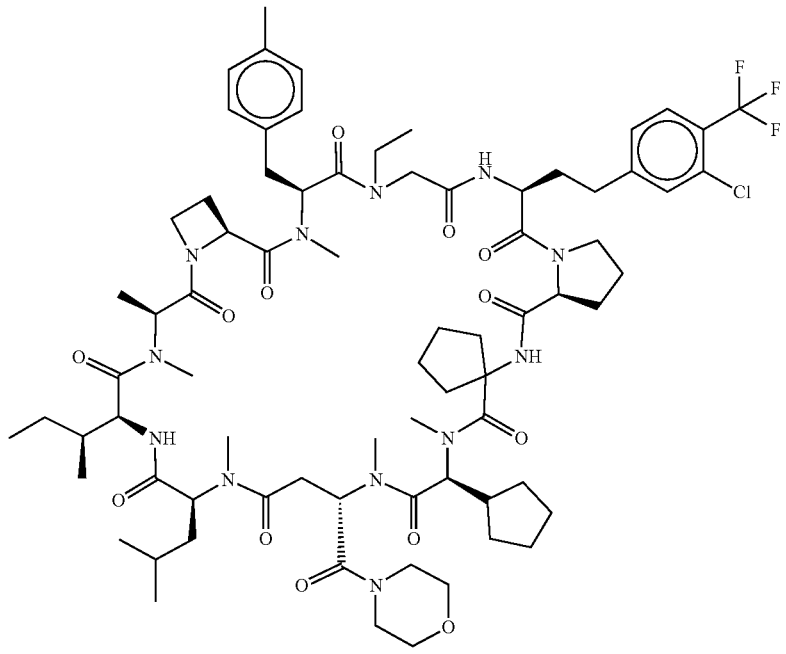 |
| PP0006 | 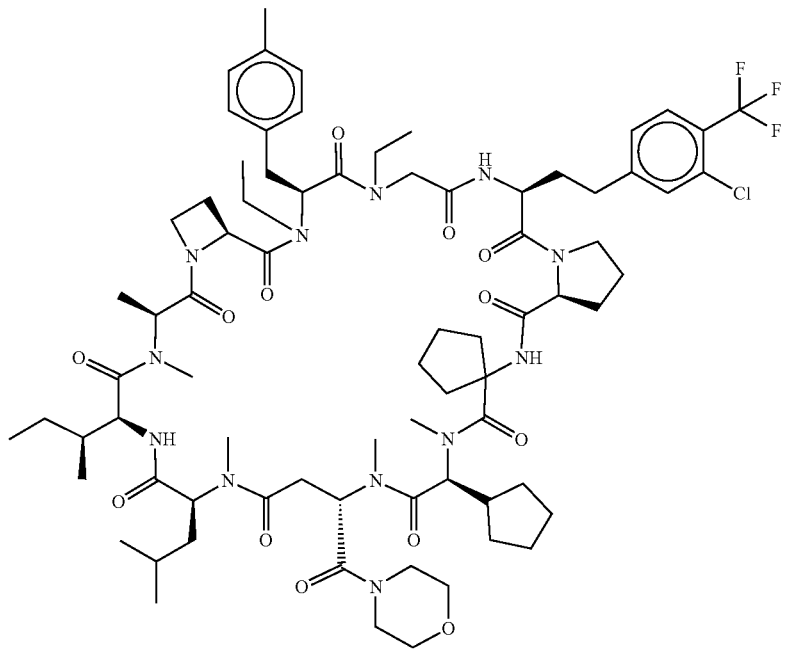 |

TABLE 38-continued
| Compound No. | Structural Formula |
|---|---|
| PP0007 | 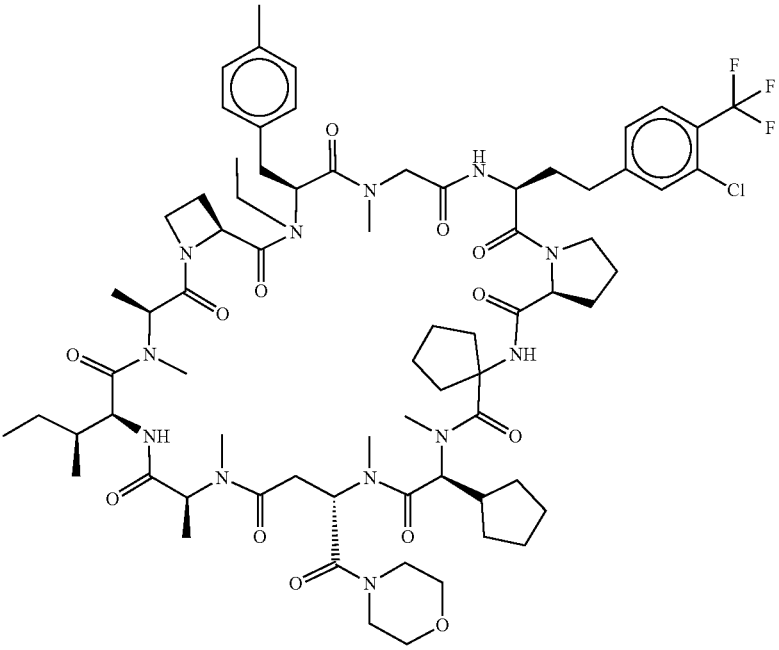 |
| PP0011 | 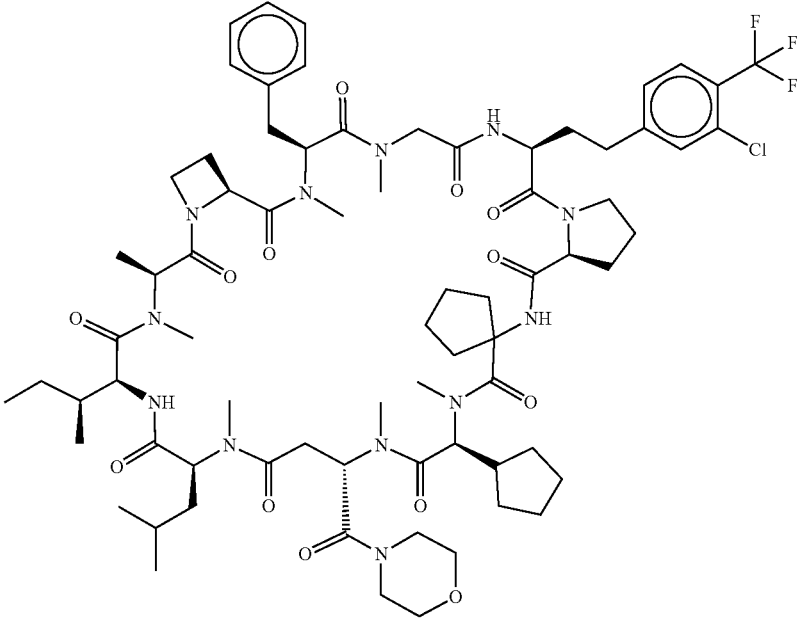 |

TABLE 38-continued
| Compound No. | Structural Formula |
|---|---|
| PP0013 | 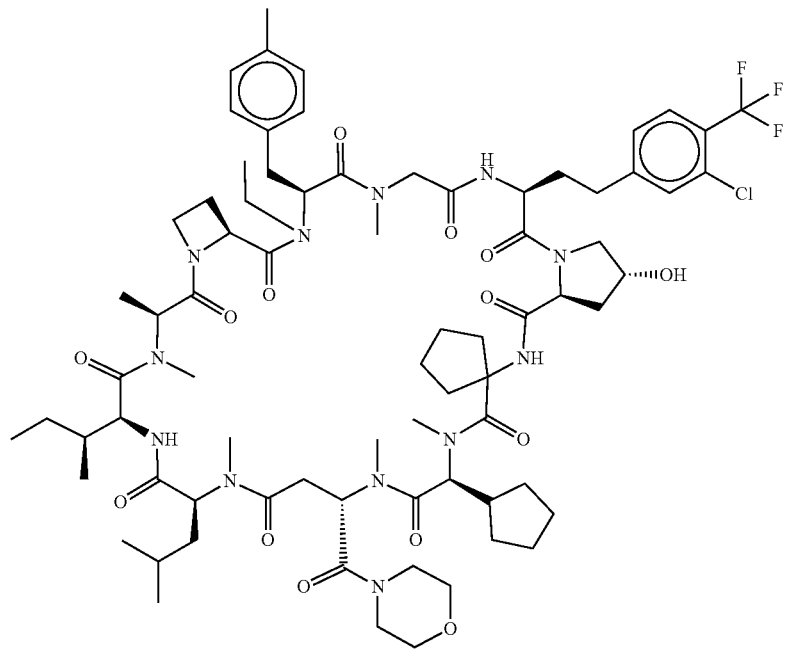 |
| PP0014 | 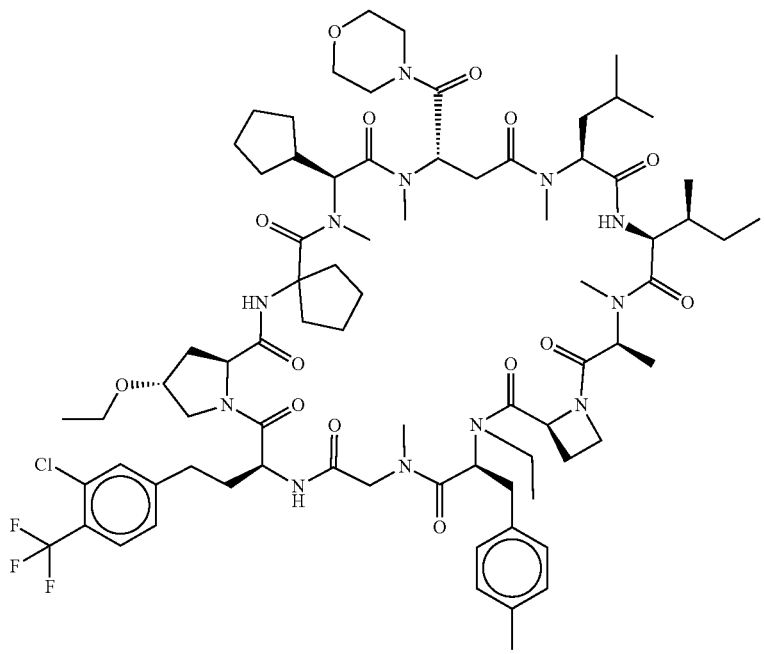 |

TABLE 38-continued
| Compound No. | Structural Formula |
|---|---|
| PP0015 | 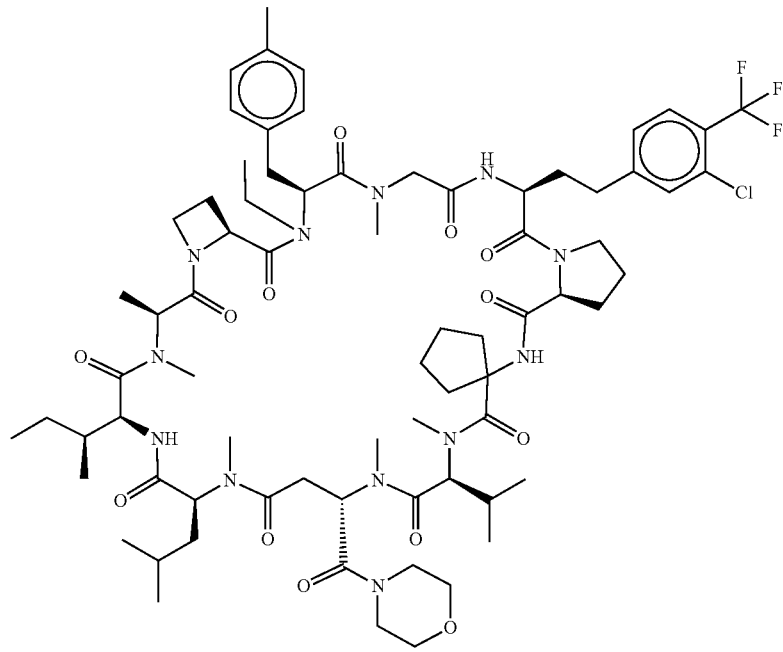 |
| PP0016 | 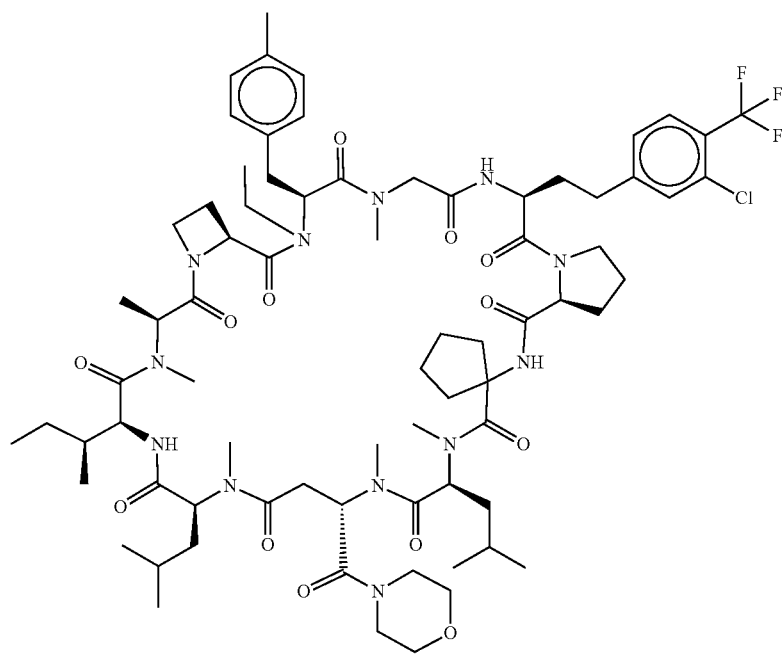 |

TABLE 38-continued

| Compound No. | Structural Formula |
|---|---|
| PP0018 | |
| PP0019 | |

TABLE 38-continued
| Compound No. | Structural Formula |
|---|---|
| PP0020 | 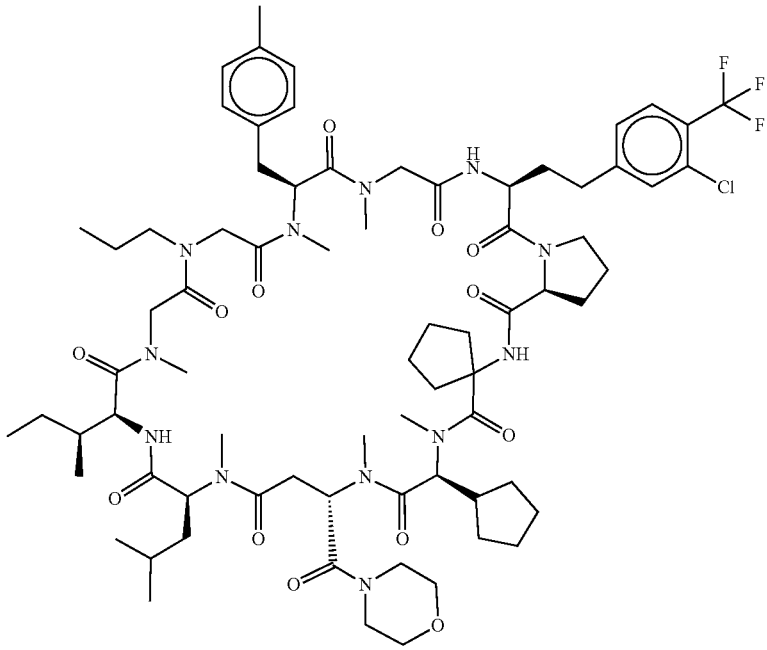 |
| PP0021 | 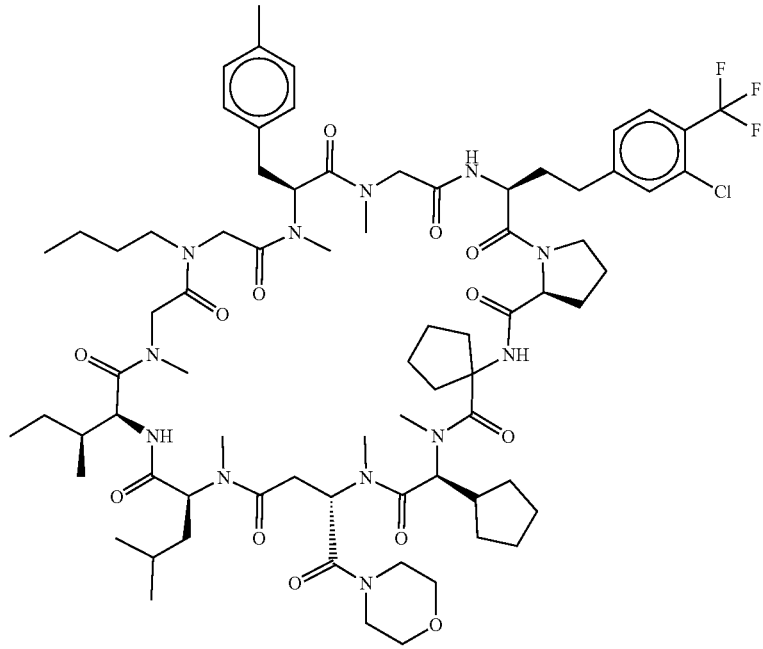 |

TABLE 38-continued

| Compound No. | Structural Formula |
|---|---|
| PP0022 | |
| PP0023 | |

TABLE 38-continued
| Compound No. | Structural Formula |
|---|---|
| PP0024 | 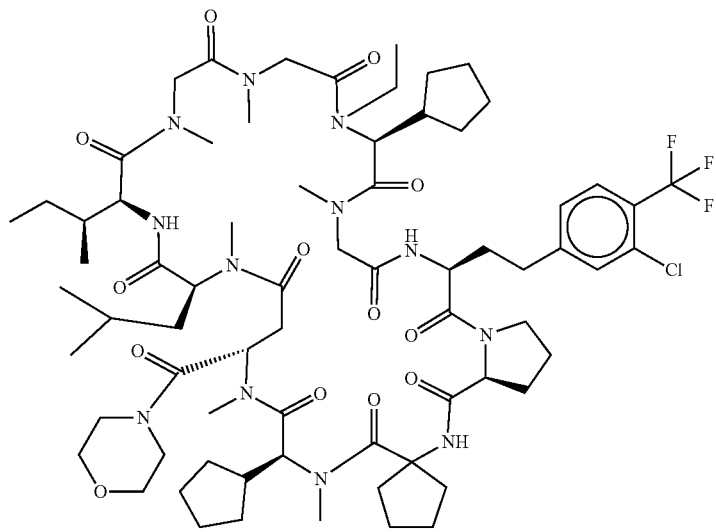 |
| PP0025 | 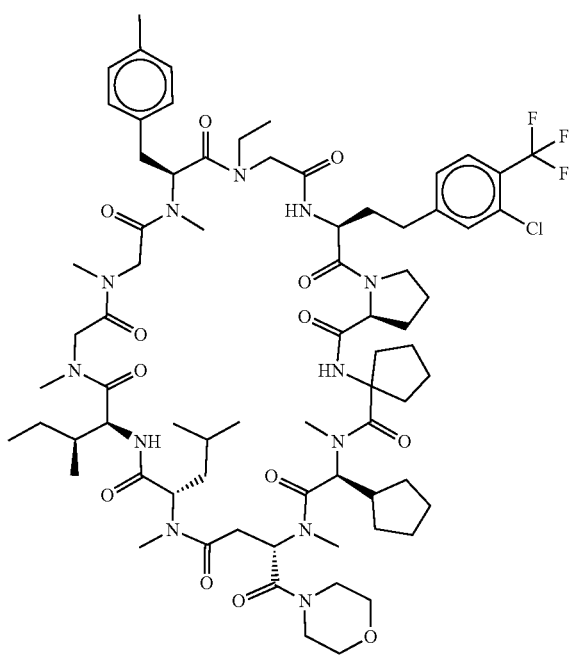 |

TABLE 38-continued
| Compound No. | Structural Formula |
| --- | --- |
| PP0027 | 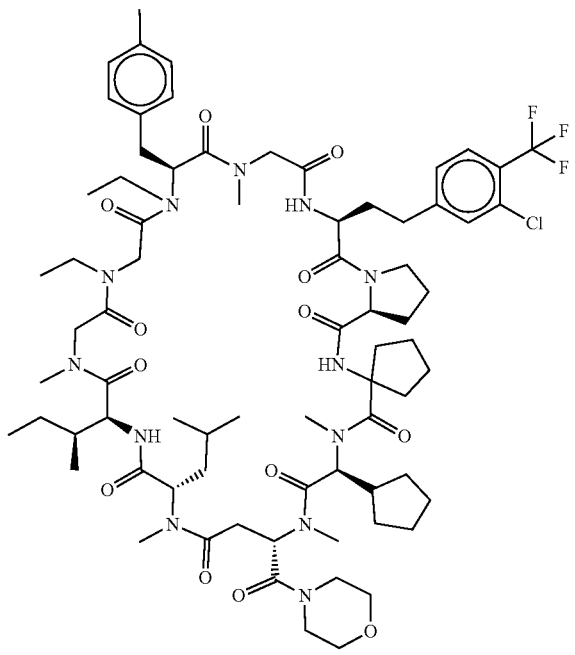 |
| PP0028 | 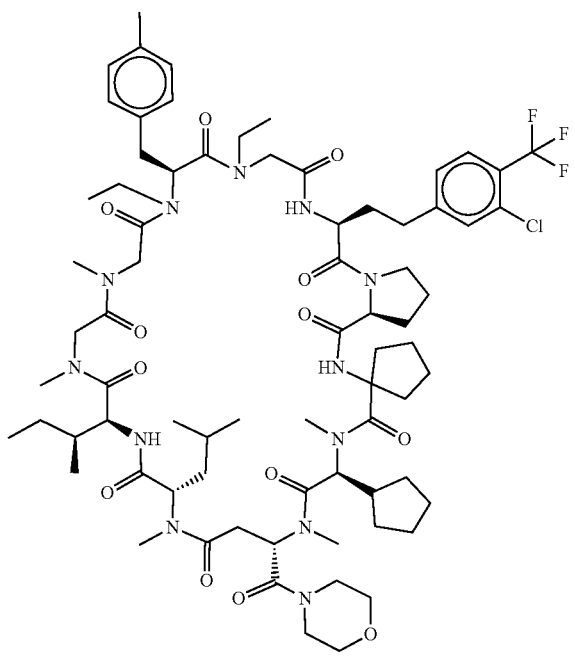 |

TABLE 38-continued
| Compound No. | Structural Formula |
|---|---|
| PP0029 | 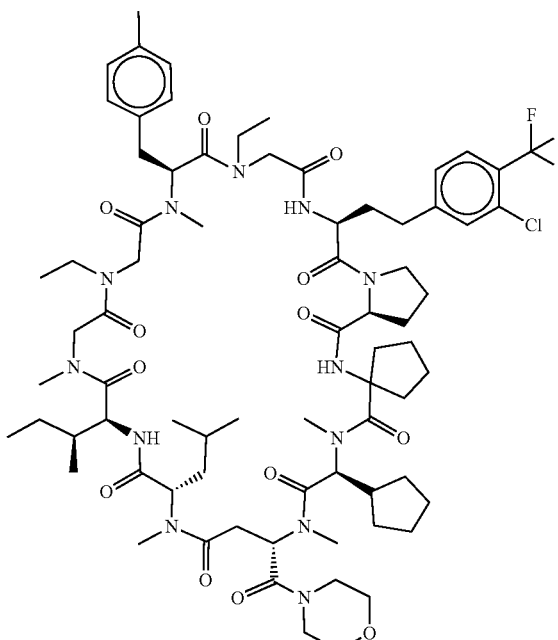 |
| PP0030 | 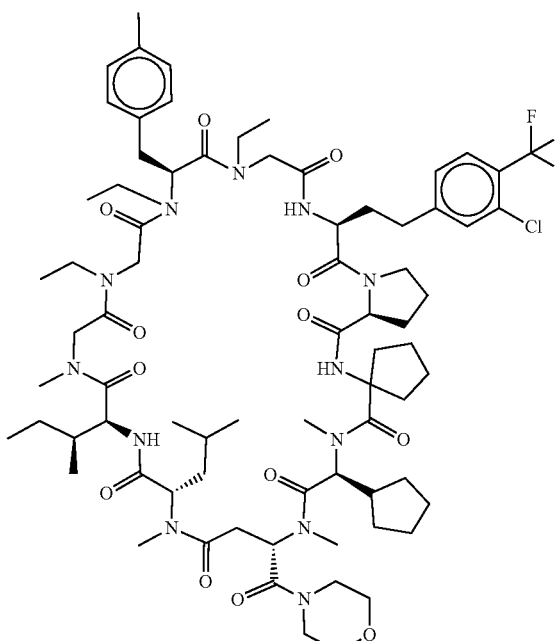 |

TABLE 38-continued
| Compound No. | Structural Formula |
|---|---|
| PP0031 | 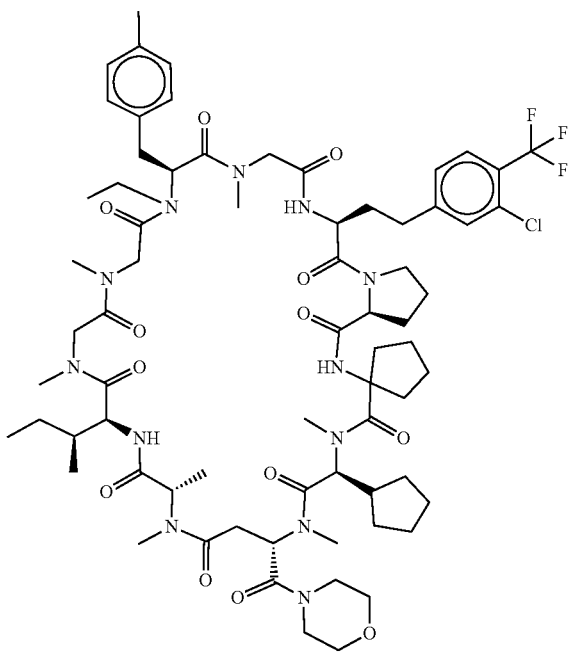 |
| PP0032 | 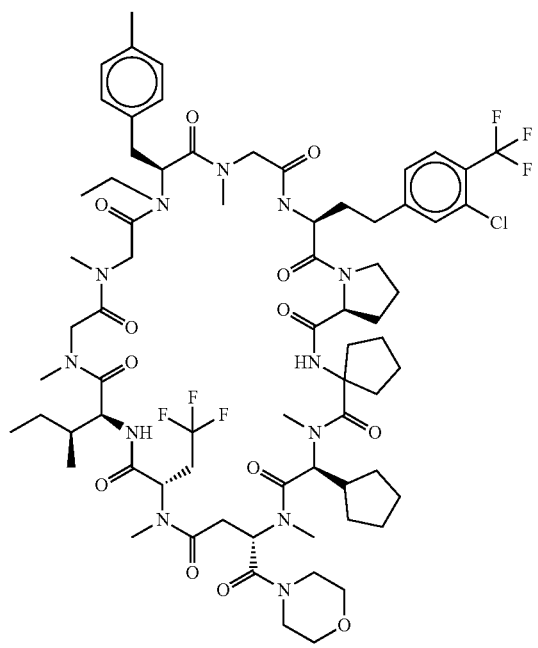 |

TABLE 38-continued
| Compound No. | Structural Formula |
|---|---|
| PP0037 | 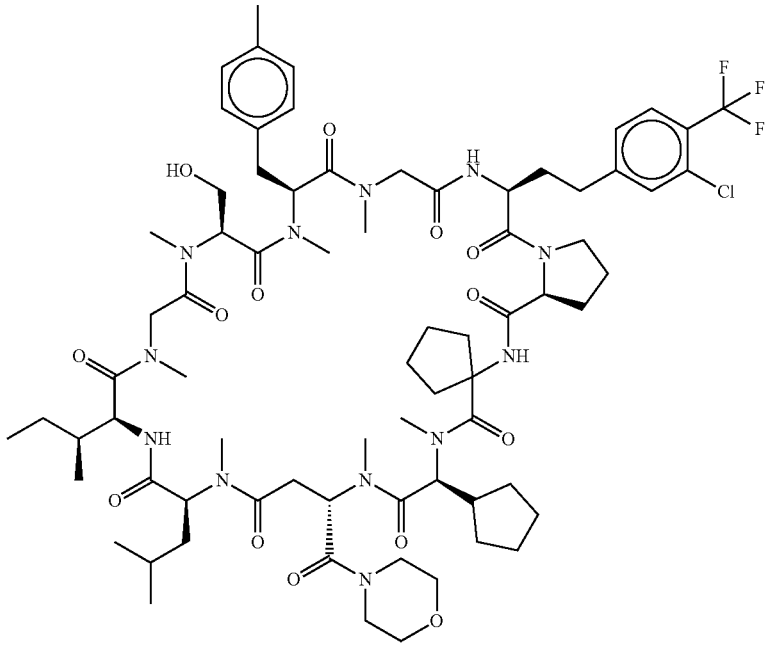 |
| PP0039 | 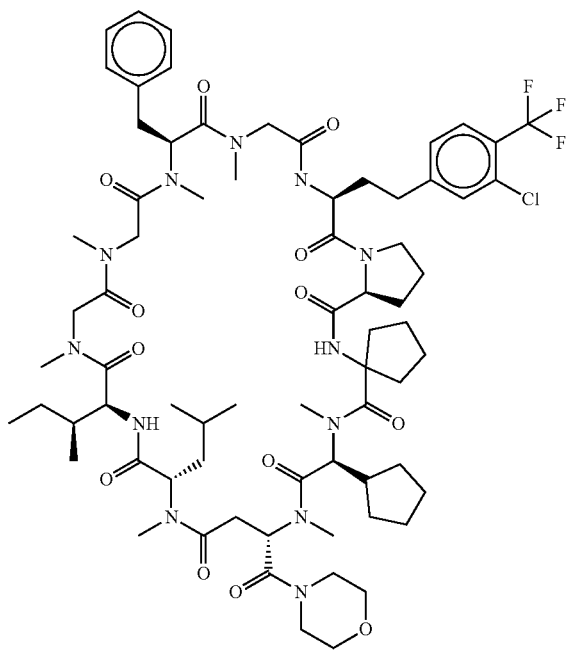 |

TABLE 38-continued
| Compound No. | Structural Formula |
|---|---|
| PP0041 | 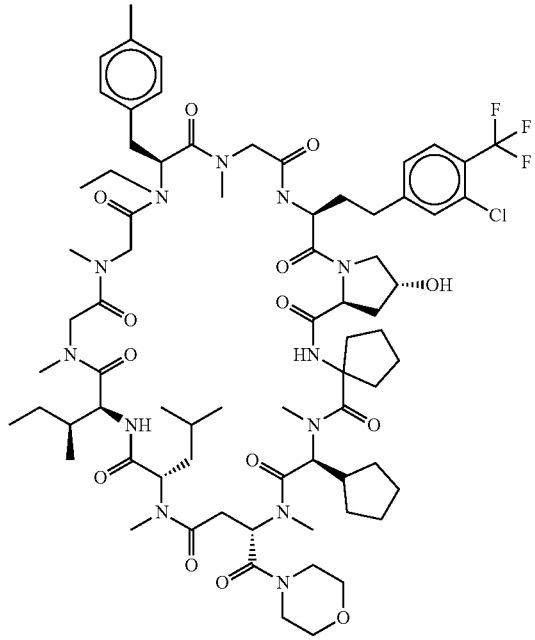 |
| PP0042 | 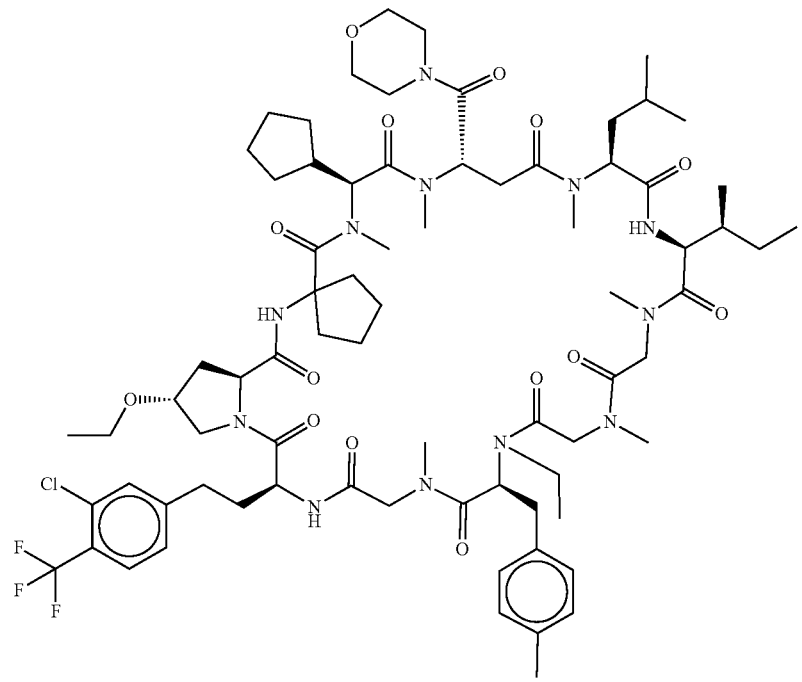 |

TABLE 38-continued

| Compound No. | Structural Formula |
| --- | --- |
| PP0043 | |
| PP0044 | |

TABLE 38-continued

| Compound No. | Structural Formula |
| --- | --- |
| PP0045 | |
| PP0047 | |

TABLE 38-continued
| Compound No. | Structural Formula |
|---|---|
| PP0048 | 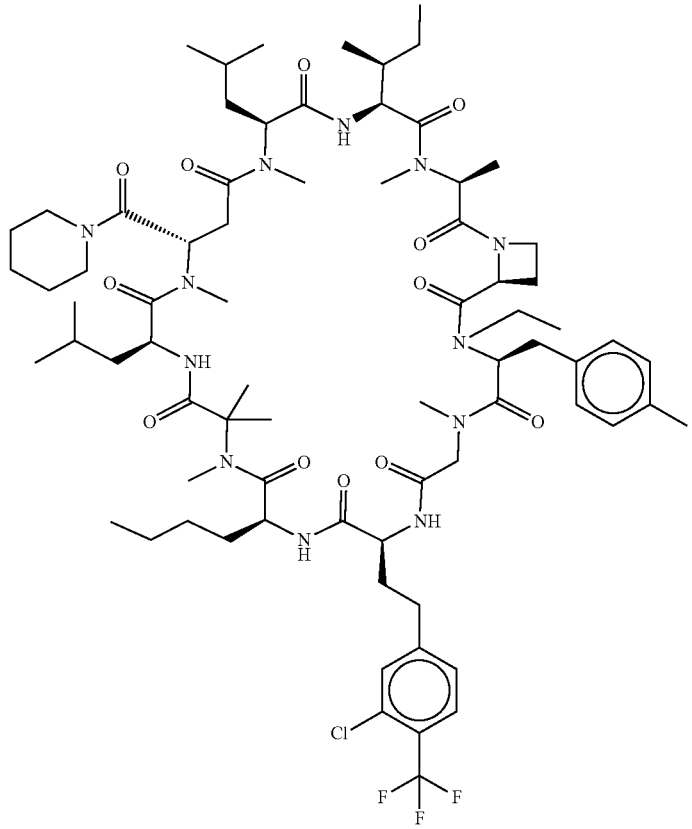 |
| PP0049 | 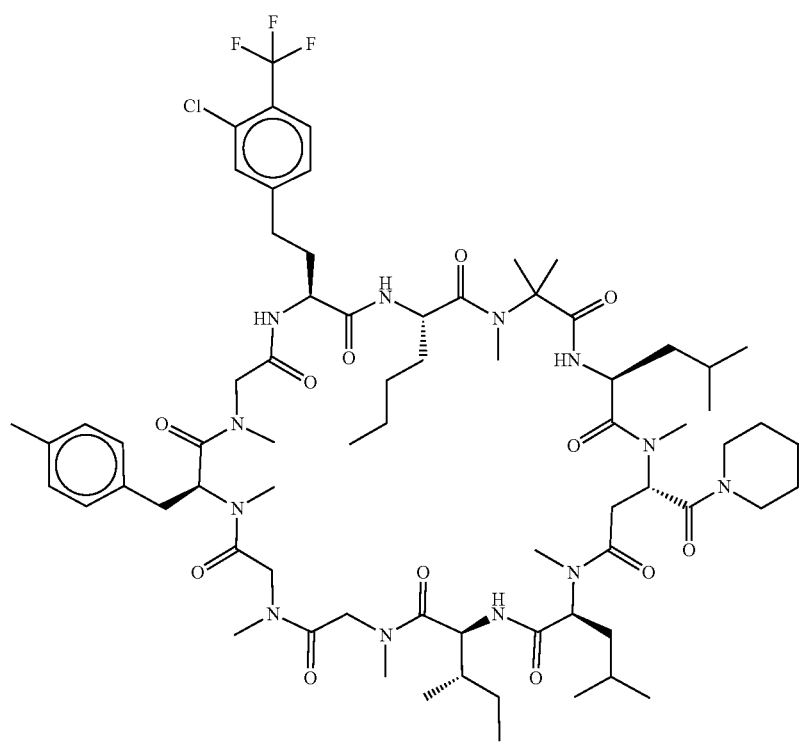 |

TABLE 38-continued
| Compound No. | Structural Formula |
|---|---|
| PP0050 | 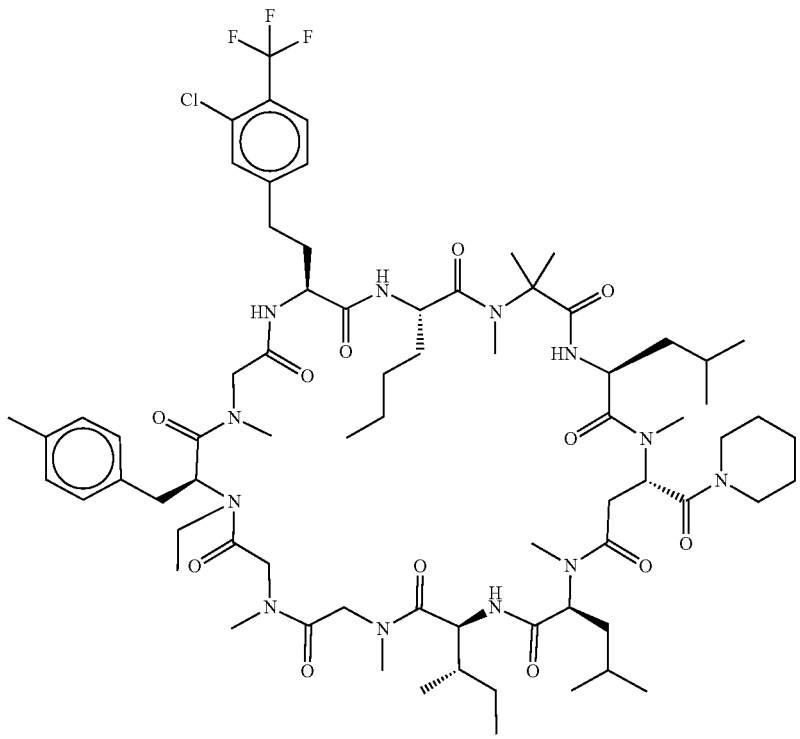 |
| PP0051 | 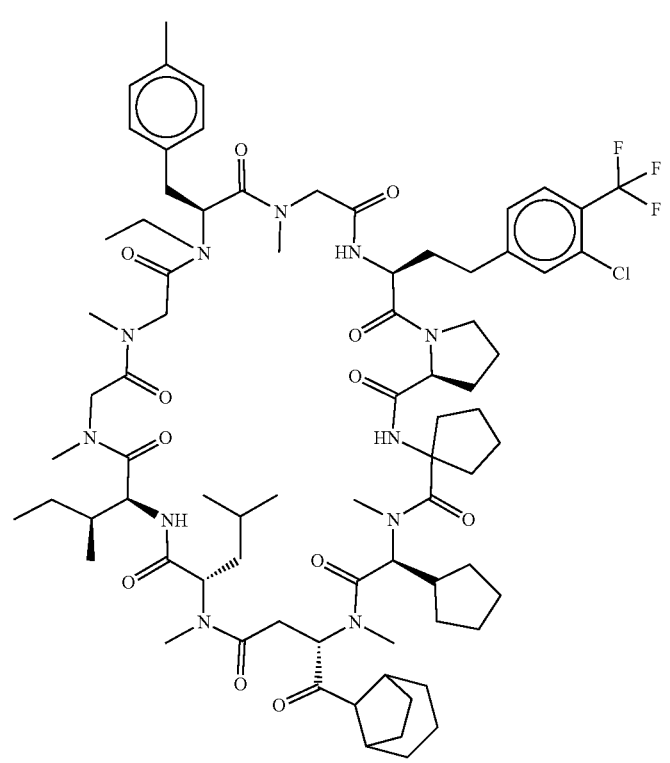 |

TABLE 38-continued

| Compound No. | Structural Formula |
|---|---|
| PP0052 | |
| PP0053 | |

TABLE 38-continued
| Compound No. | Structural Formula |
|---|---|
| PP0054 | 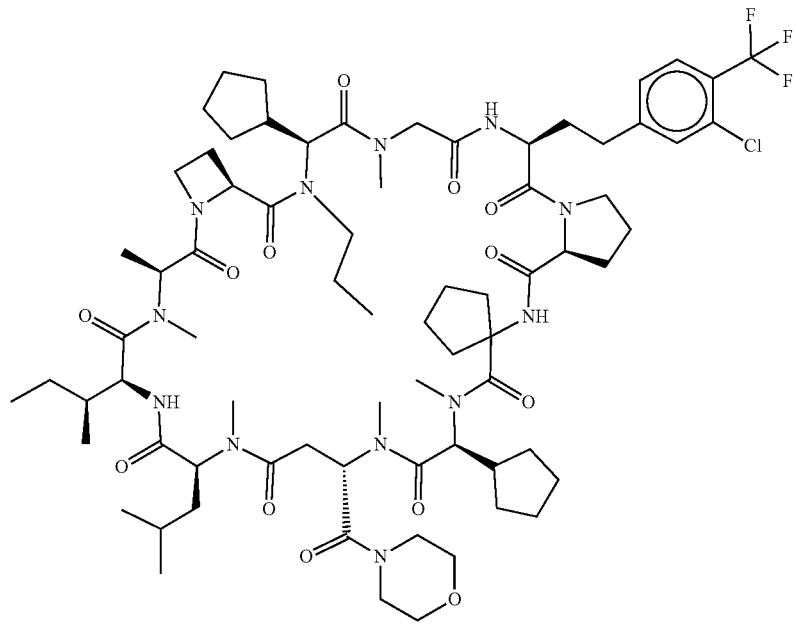 |
| PP0055 | 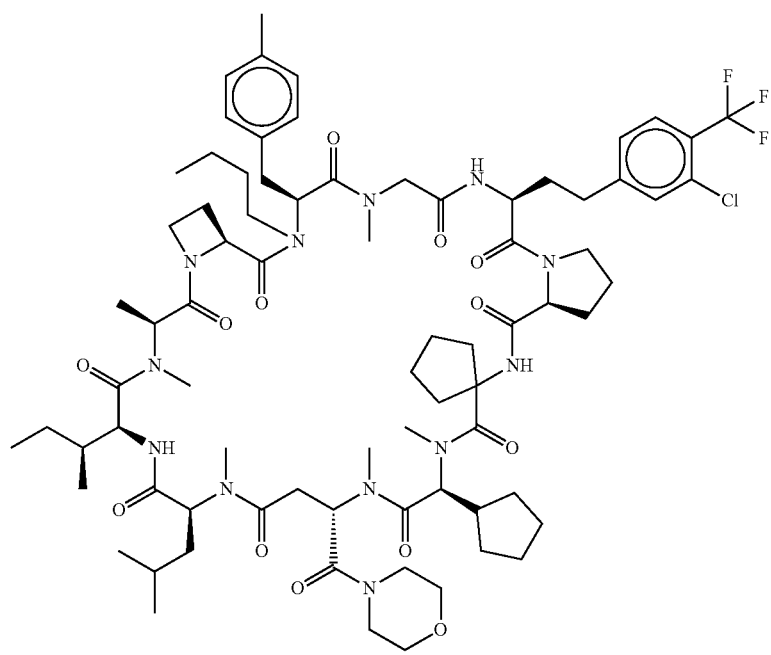 |

TABLE 38-continued
| Compound No. | Structural Formula |
|---|---|
| PP0056 | 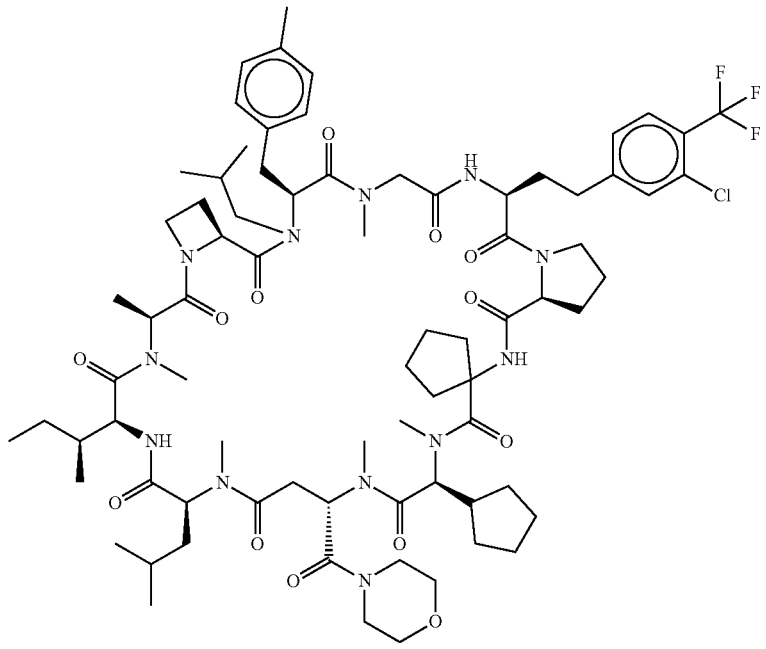 |
| PP0057 | 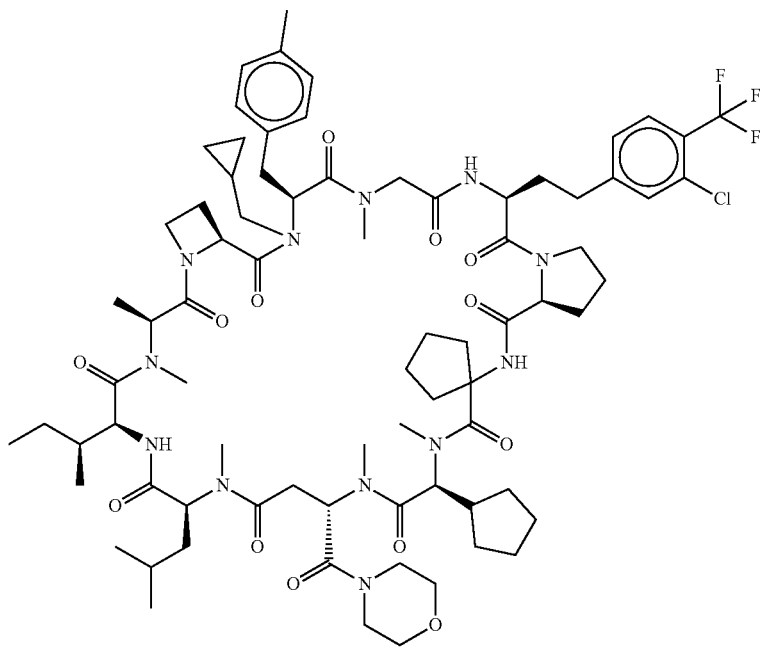 |

TABLE 38-continued
| Compound No. | Structural Formula |
|---|---|
| PP0058 | 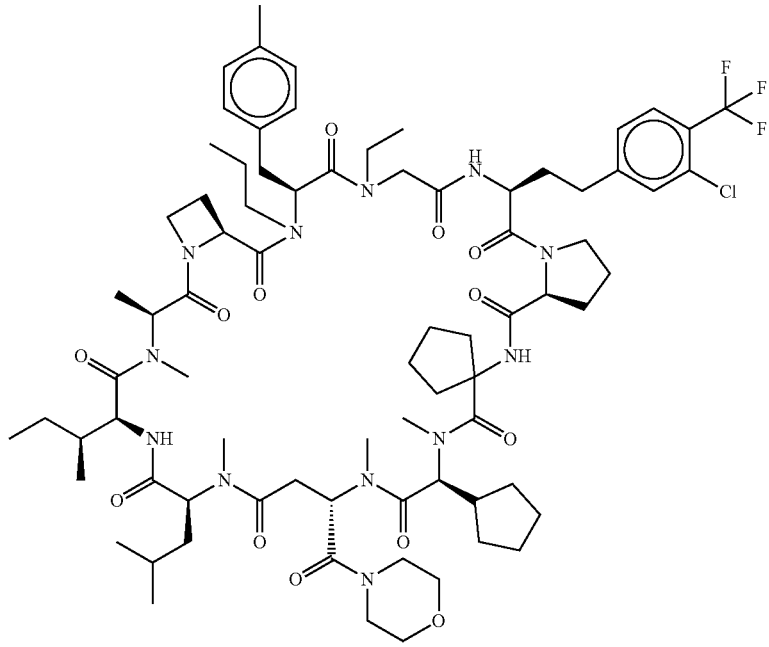 |
| PP0059 | 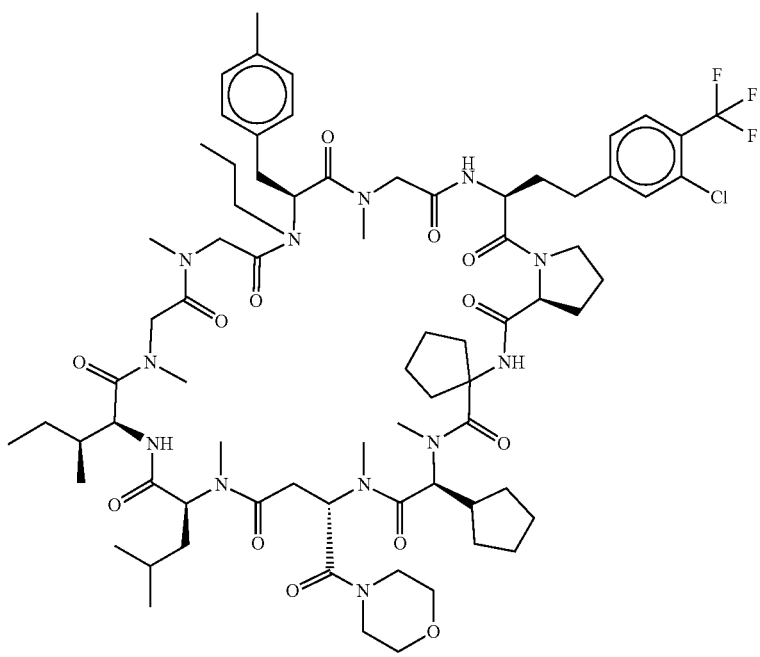 |

TABLE 38-continued
| Compound No. | Structural Formula |
|---|---|
| PP0060 | 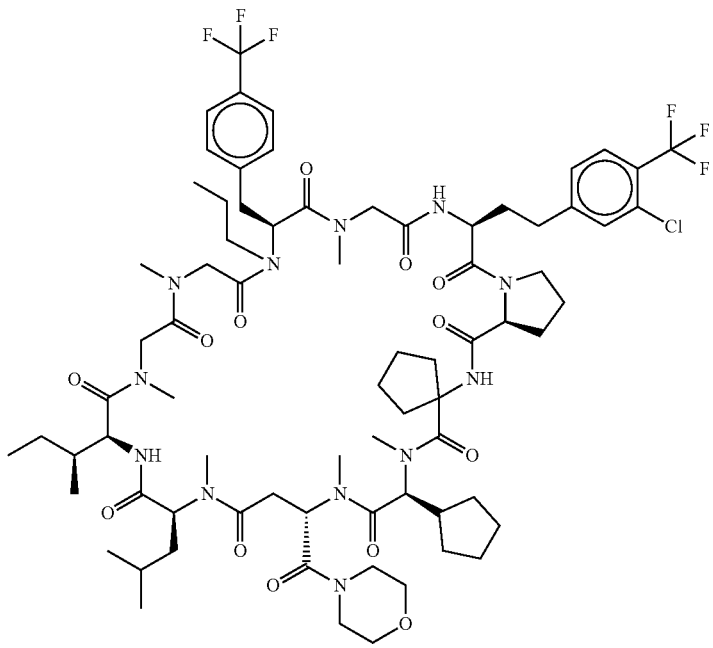 |
| PP0061 | 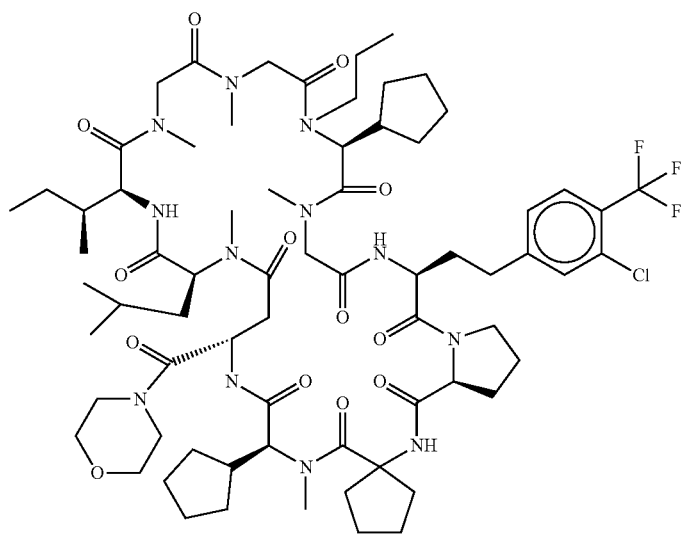 |

TABLE 38-continued

| Compound No. | Structural Formula |
| --- | --- |
| PP0062 | |
| PP0063 | |

TABLE 38-continued
| Compound No. | Structural Formula |
|---|---|
| PP0064 | 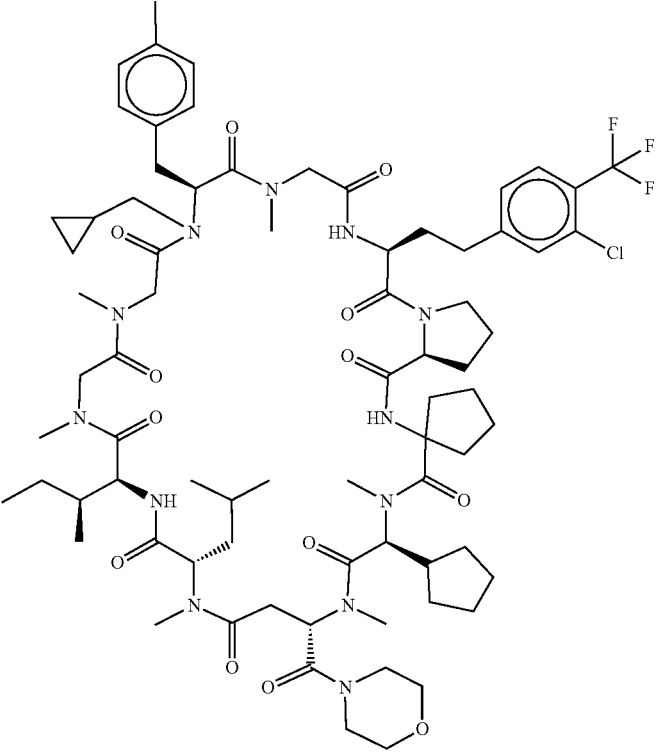 |
| PP0065 | 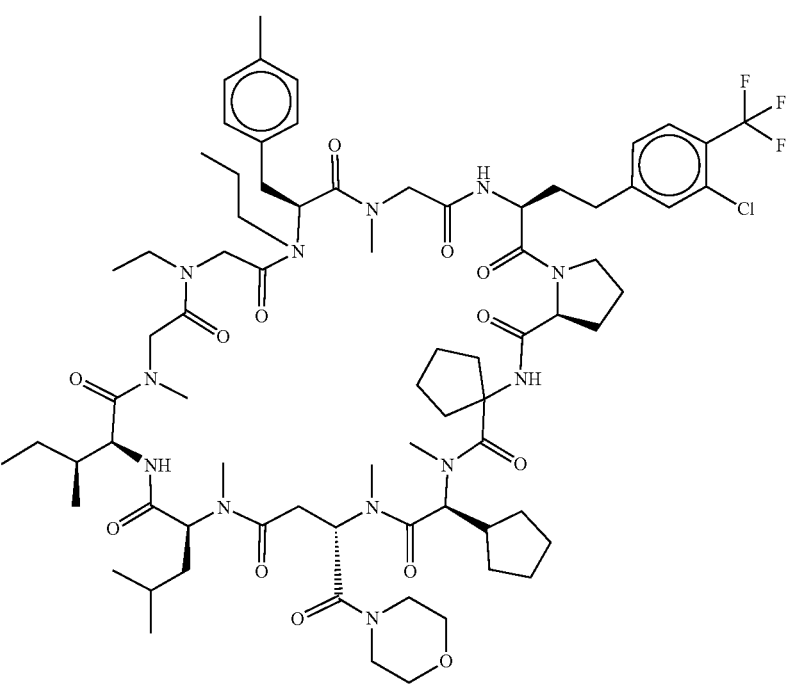 |

TABLE 38-continued
| Compound No. | Structural Formula |
|---|---|
| PP0066 | 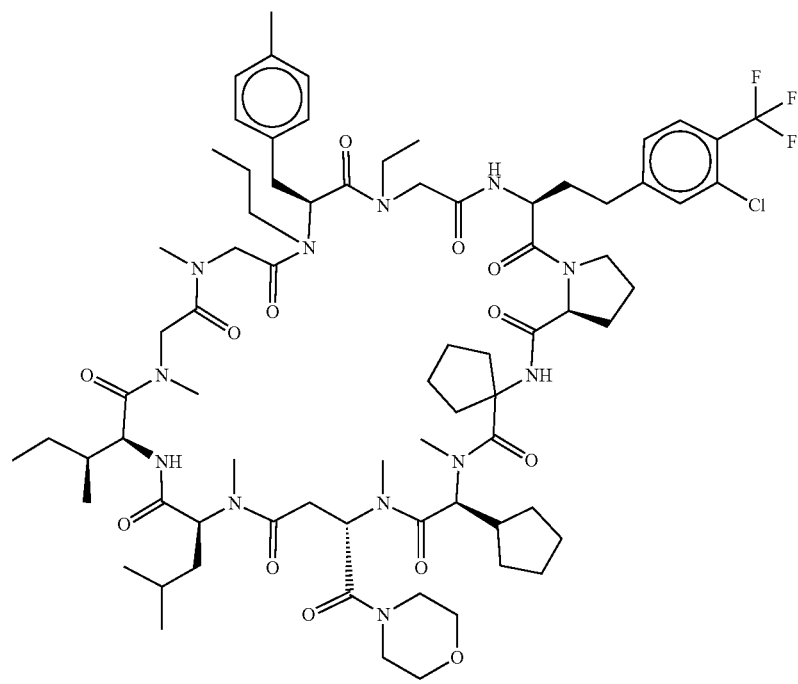 |
| PP0067 | 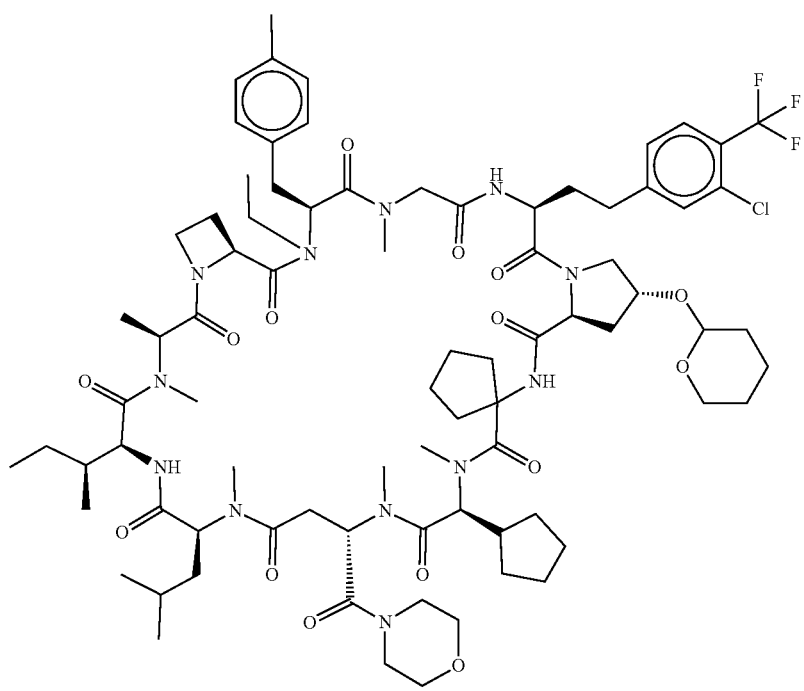 |

TABLE 38-continued
| Compound No. | Structural Formula |
|---|---|
| PP0068 | 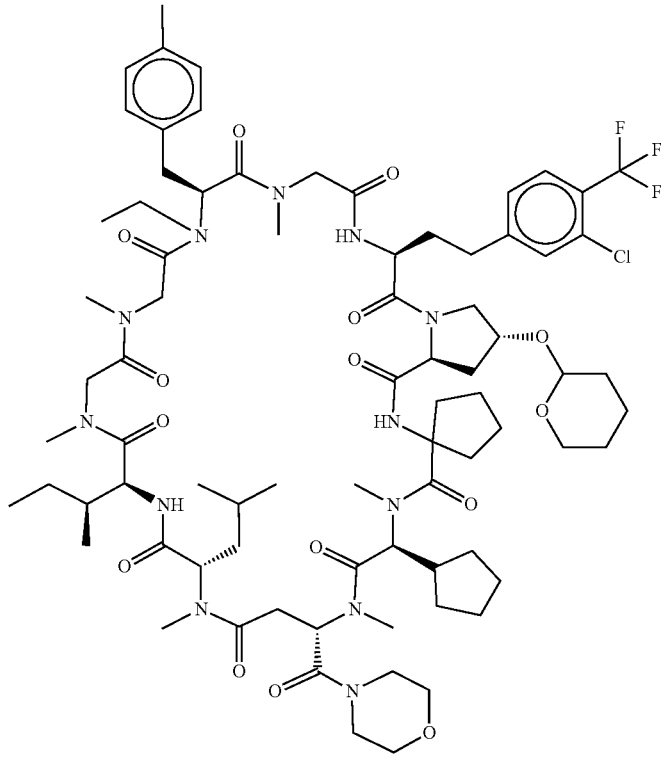 |
| PP0069 | 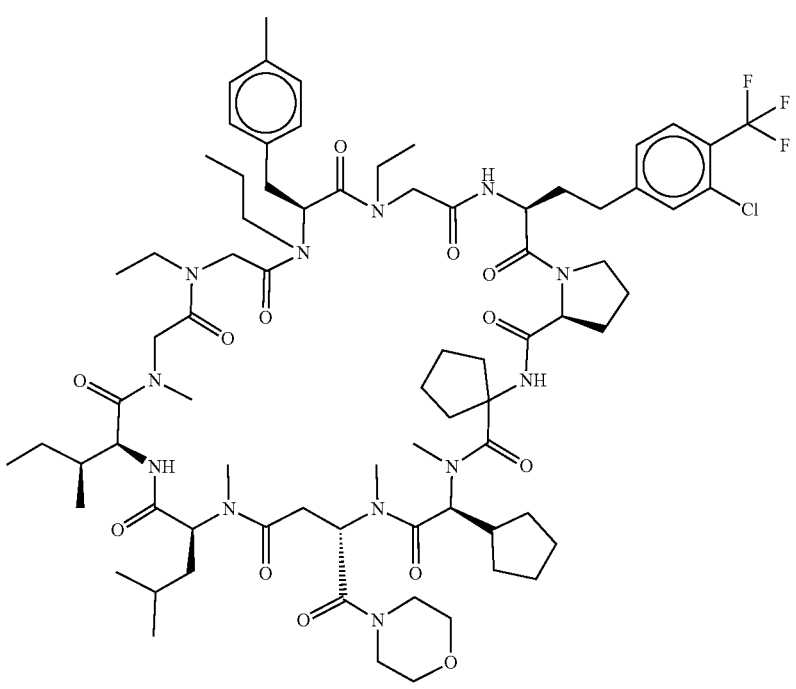 |

TABLE 38-continued
| Compound No. | Structural Formula |
|---|---|
| PP0070 | 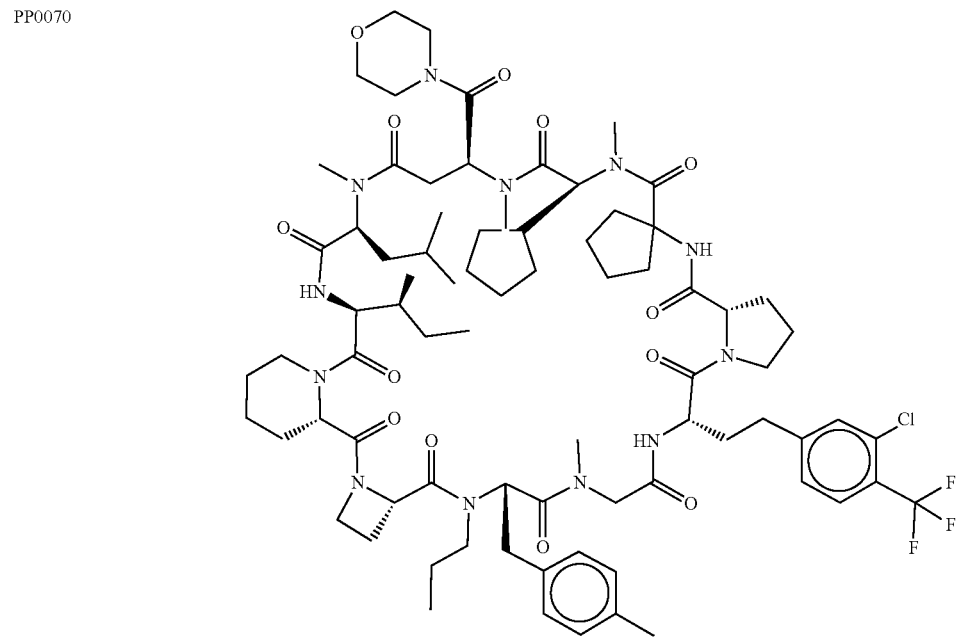 |
| PP0071 | 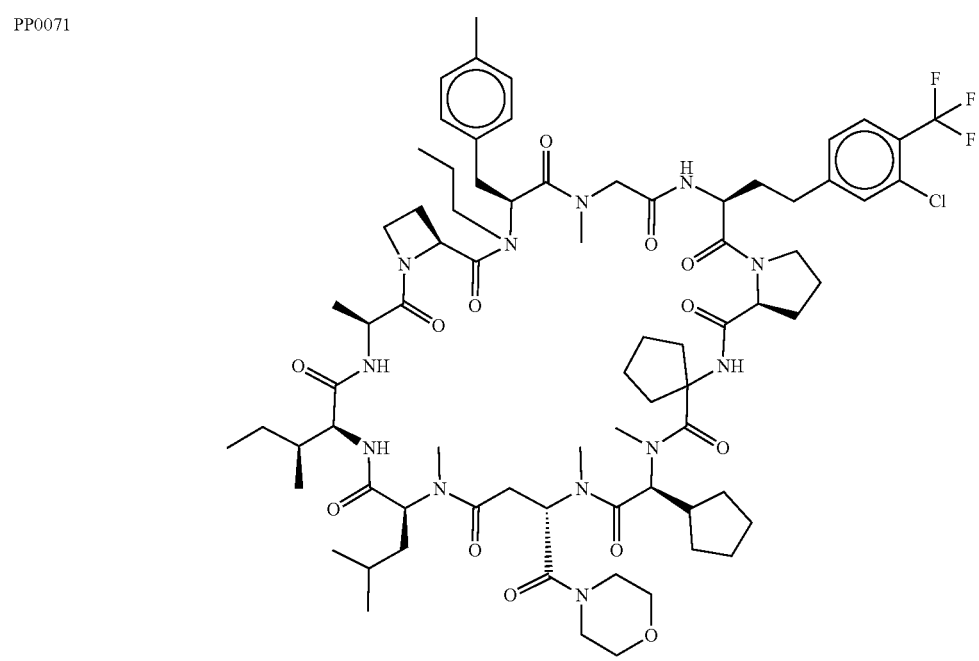 |

TABLE 38-continued
| Compound No. | Structural Formula |
|---|---|
| PP0076 | 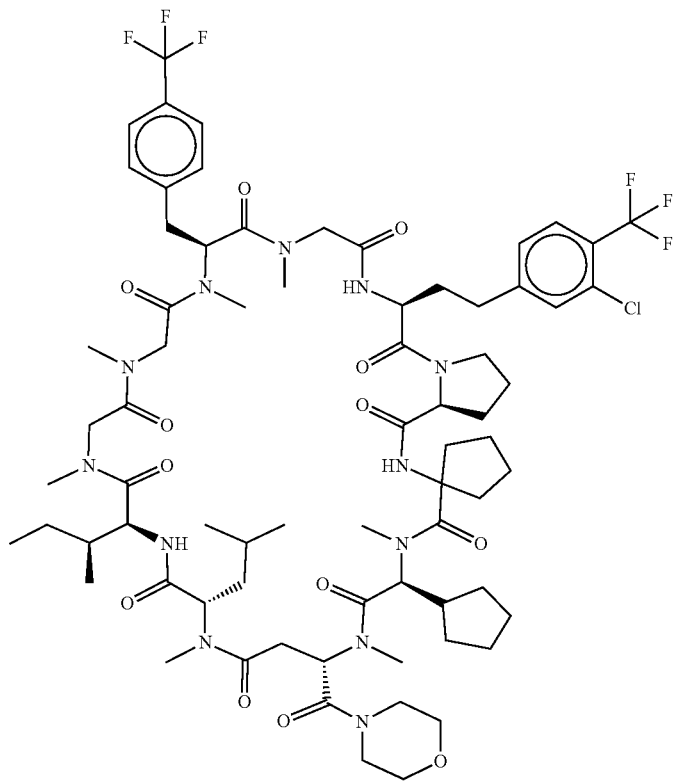 |
| PP0077 | 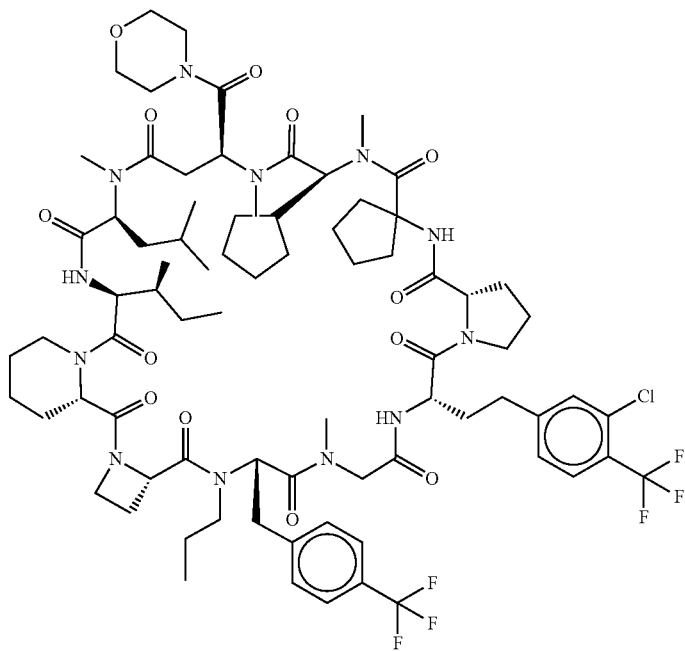 |

TABLE 38-continued
| Compound No. | Structural Formula |
|---|---|
| PP0078 | 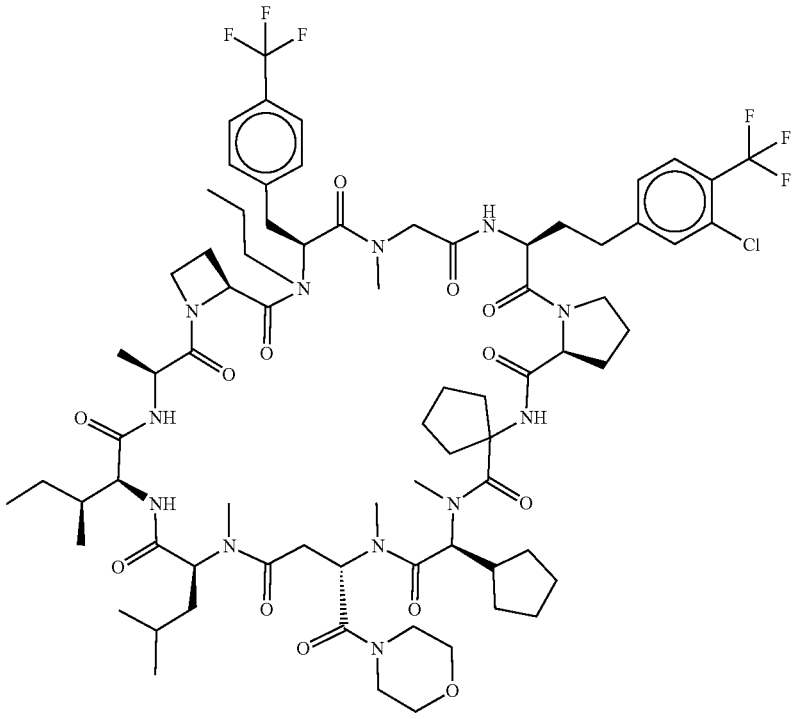 |
| PP0083 | 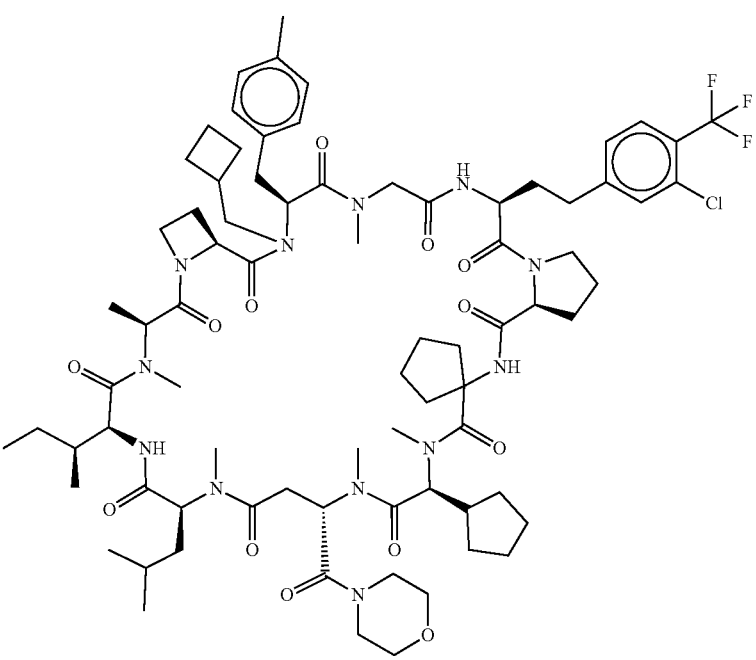 |

TABLE 38-continued
| Compound No. | Structural Formula |
|---|---|
| PP0084 | 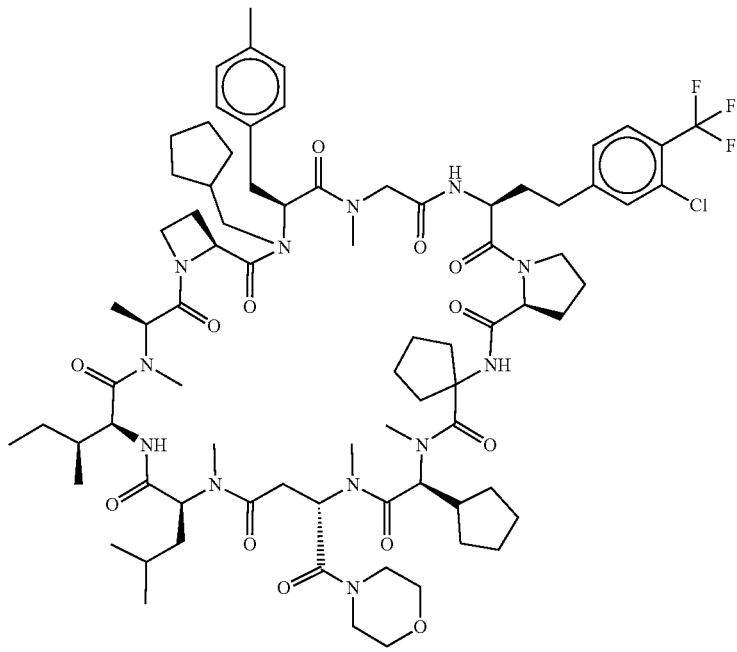 |
| PP0085 | 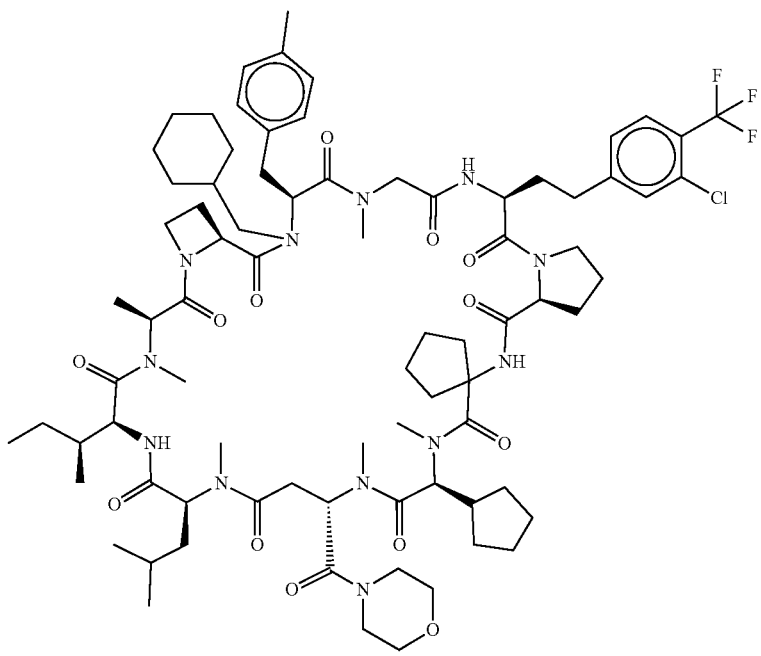 |

TABLE 38-continued
| Compound No. | Structural Formula |
| --- | --- |
| PP0086 | 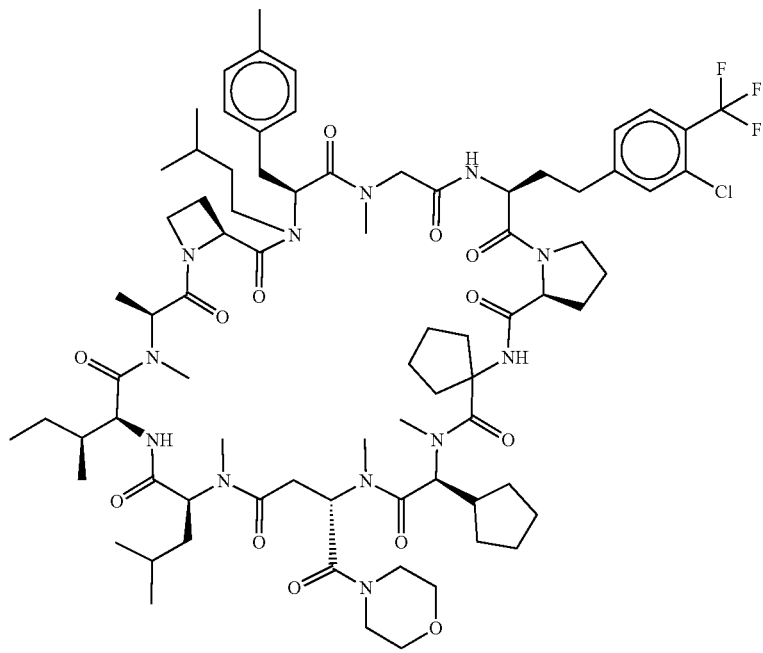 |
| PP0087 | 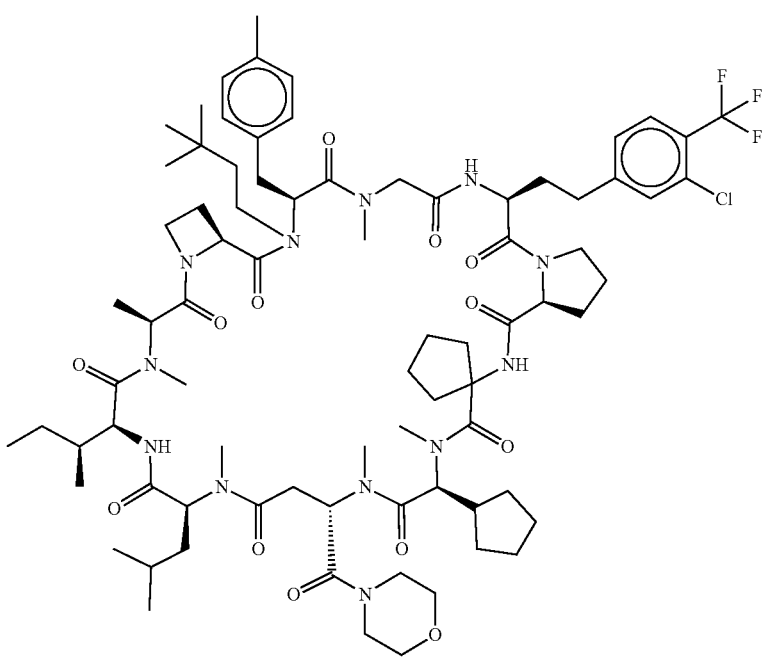 |

TABLE 38-continued
| Compound No. | Structural Formula |
|---|---|
| PP0088 | 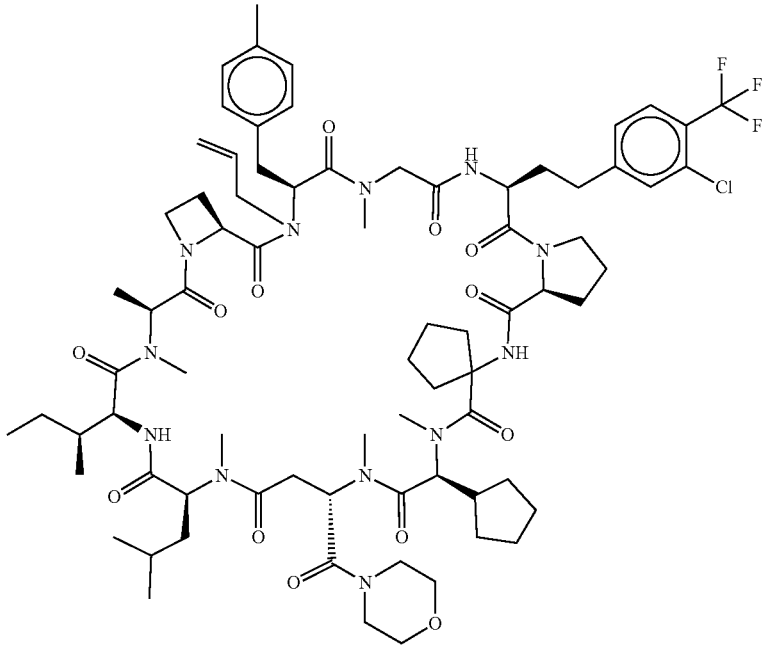 |
| PP0089 | 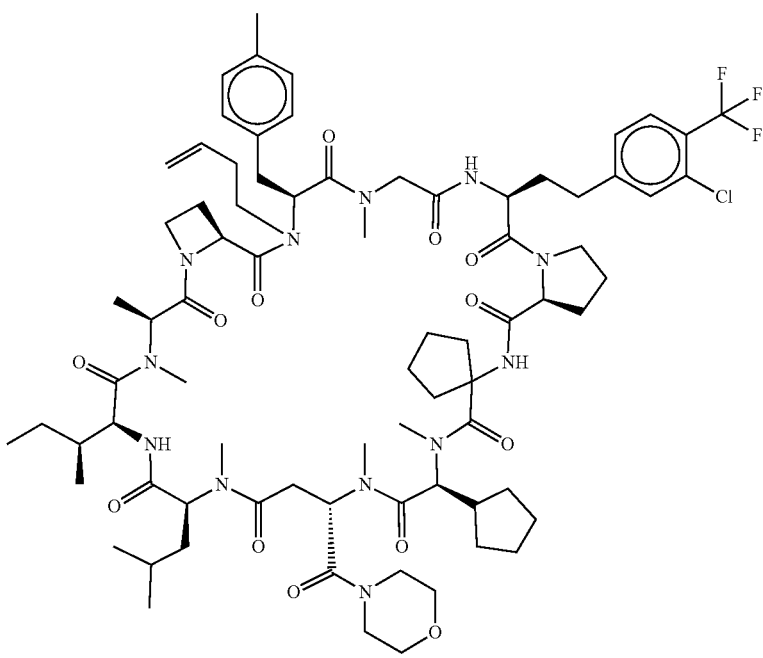 |

TABLE 38-continued
| Compound No. | Structural Formula |
|---|---|
| PP0090 | 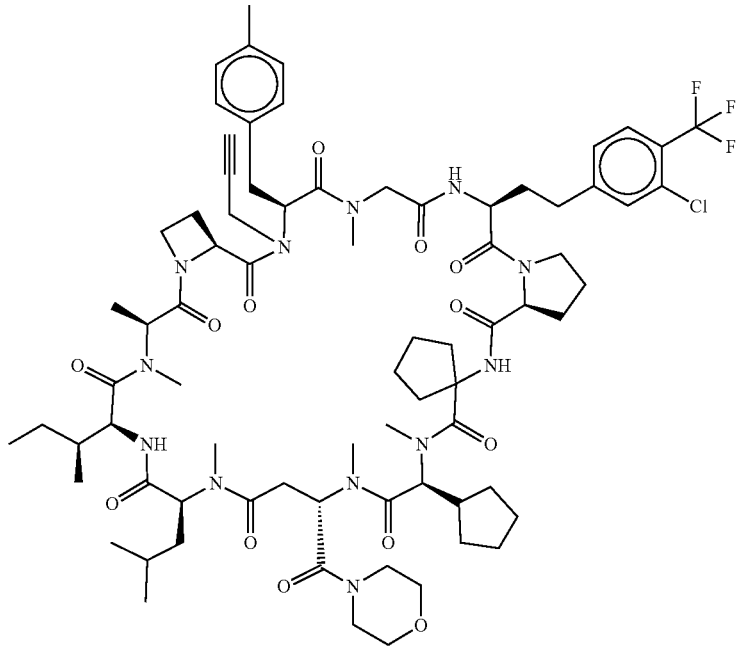 |
| PP0091 | 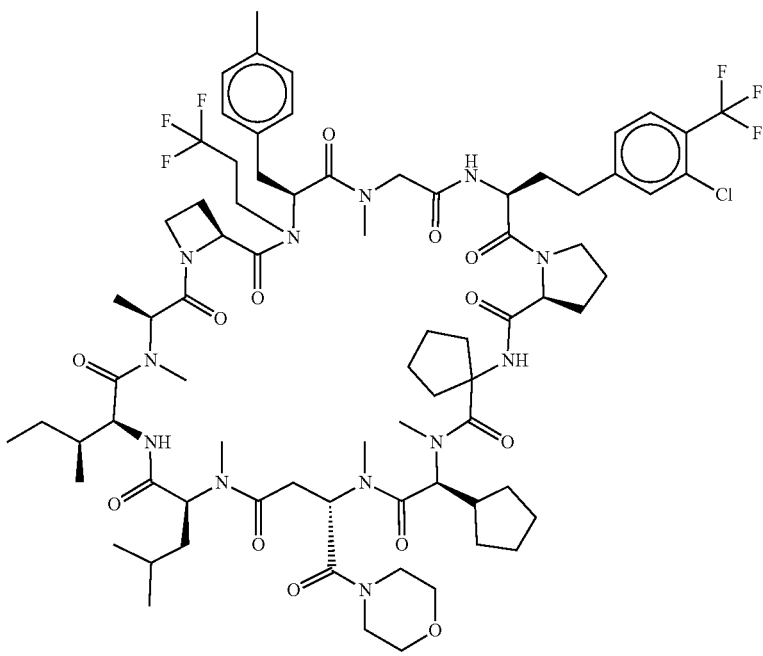 |

TABLE 38-continued
| Compound No. | Structural Formula |
|---|---|
| PP0092 | 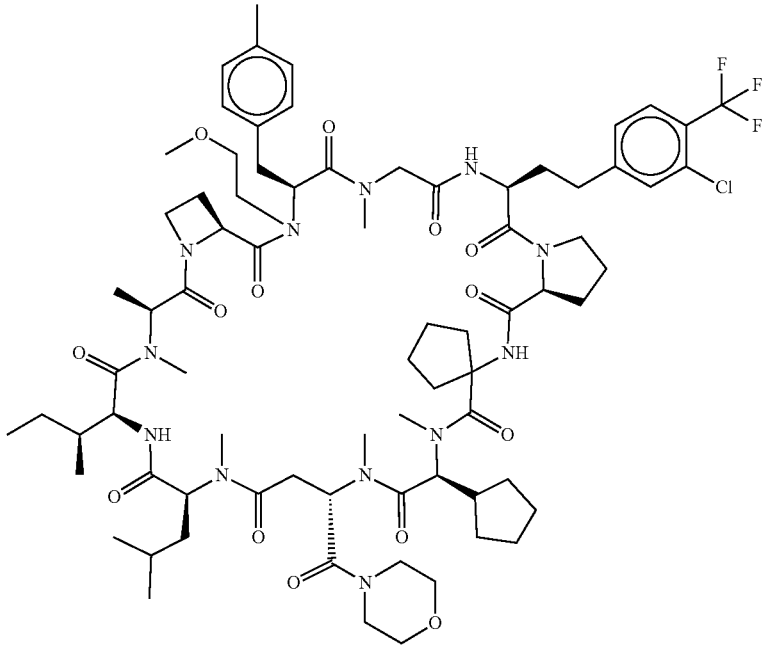 |
| PP0093 | 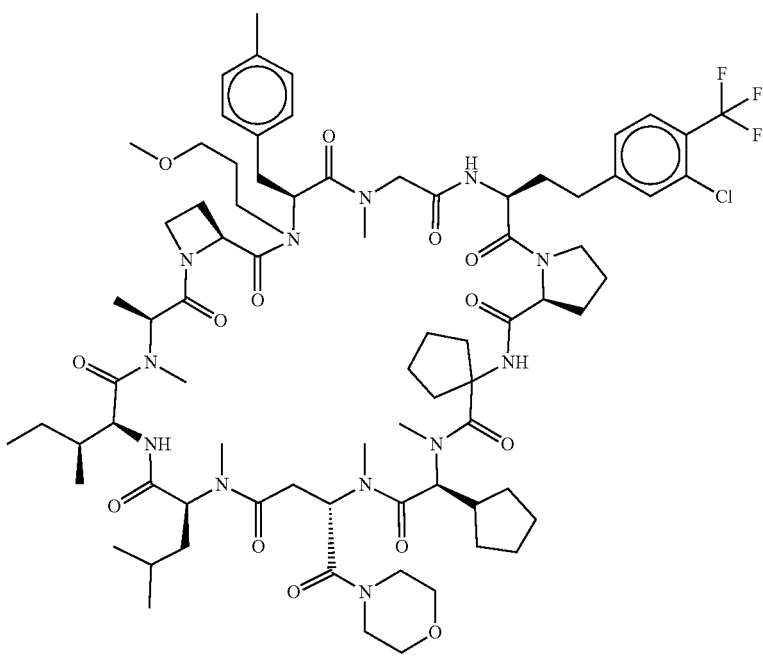 |

| Compound No. | Structural Formula |
|---|---|
| PP0094 | |
| PP0095 | |

TABLE 38-continued
| Compound No. | Structural Formula |
|---|---|
| PP0096 | 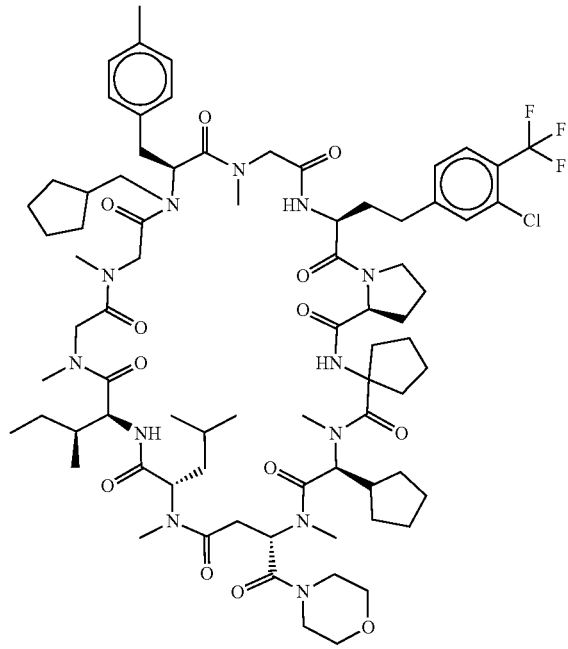 |
| PP0097 | 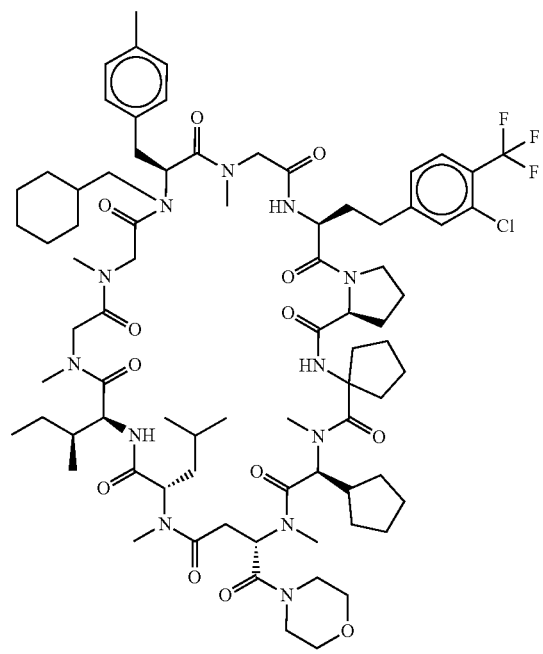 |

TABLE 38-continued
| Compound No. | Structural Formula |
| --- | --- |
| PP0098 | 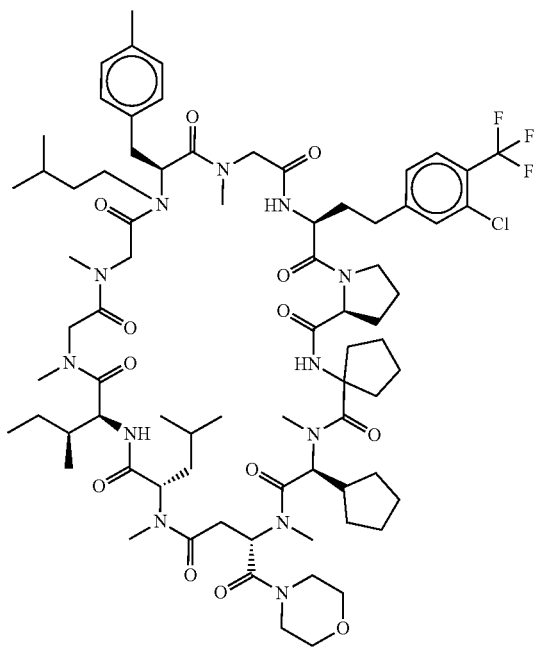 |
| PP0099 | 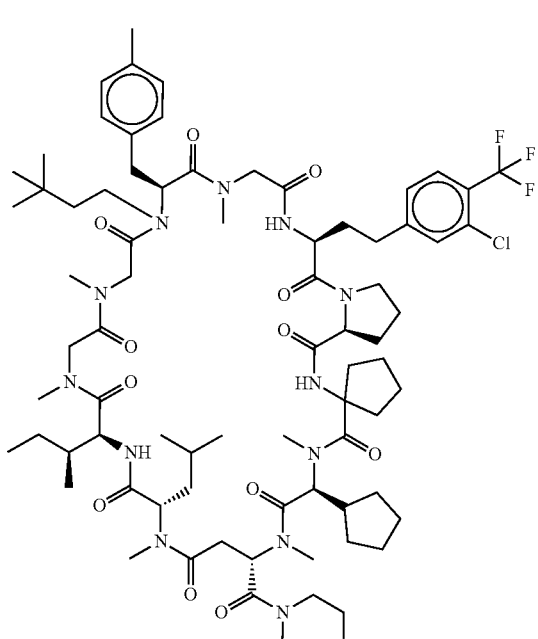 |

TABLE 38-continued

| Compound No. | Structural Formula |
|---|---|
| PP0100 | |
| PP0101 | |

TABLE 38-continued
| Compound No. | Structural Formula |
|---|---|
| PP0102 | 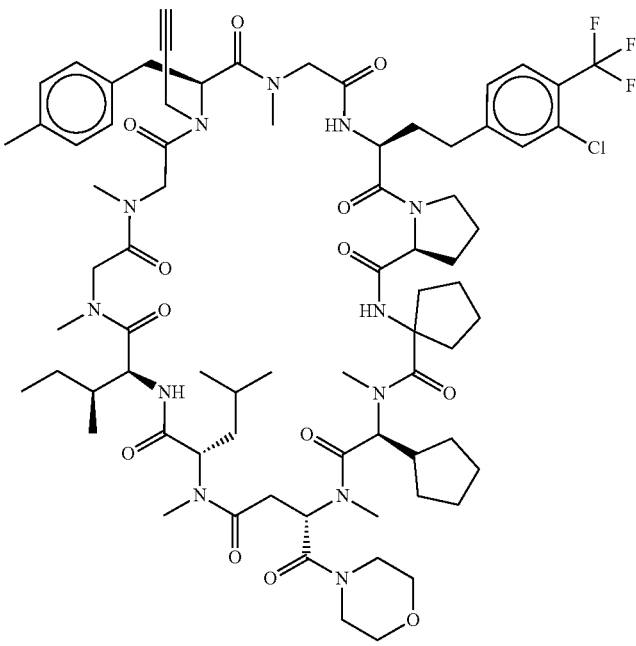 |
| PP0103 | 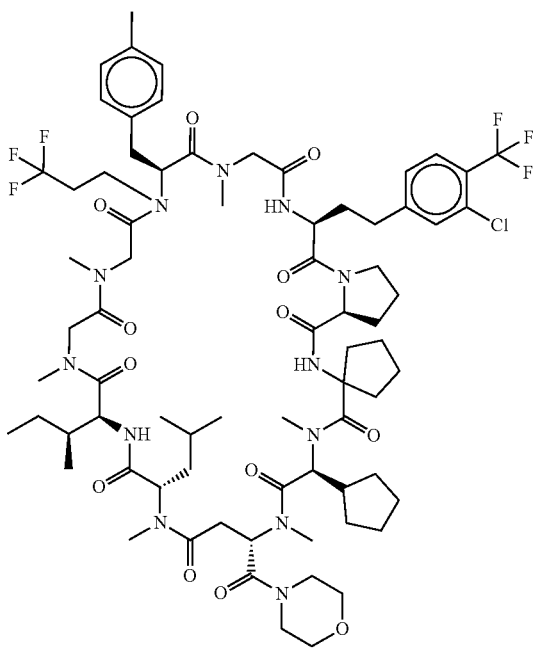 |

…
TABLE 38-continued
| Compound No. | Structural Formula |
|---|---|
| PP0104 | 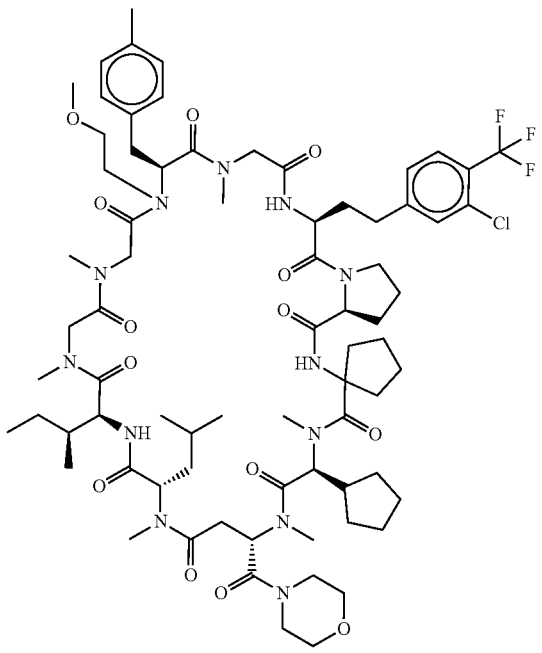 |
| PP0105 | 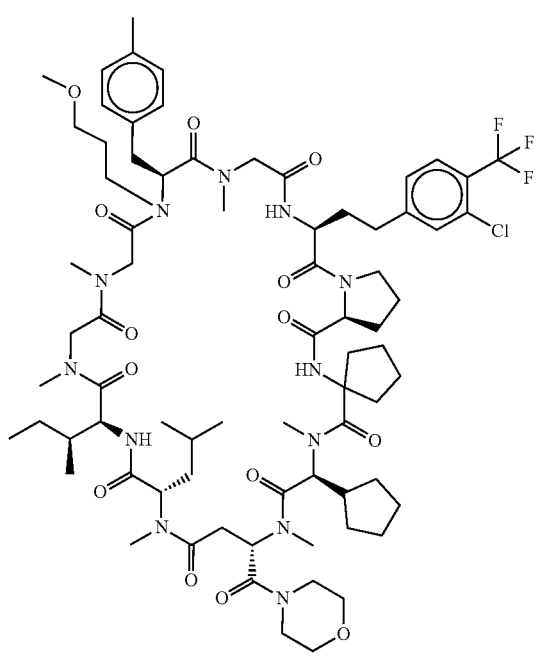 |

TABLE 38-continued
| Compound No. | Structural Formula |
|---|---|
| PP0106 | 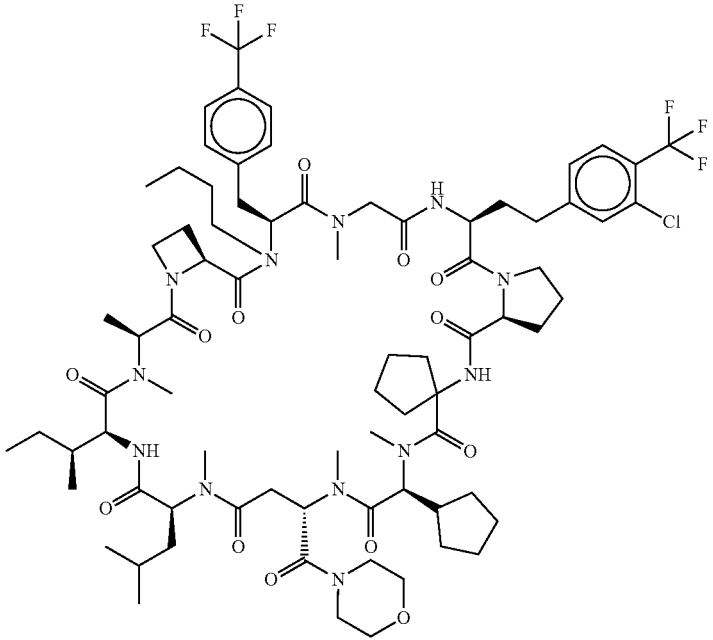 |
| PP0107 | 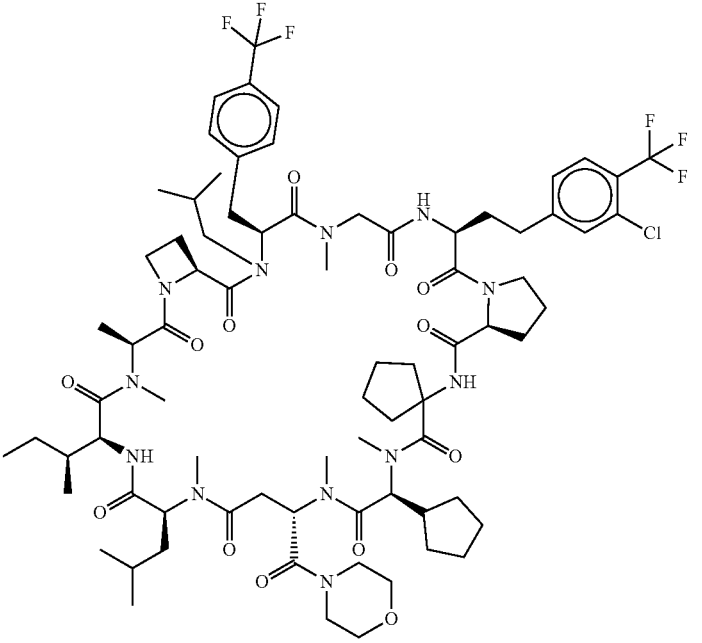 |

TABLE 38-continued
| Compound No. | Structural Formula |
|---|---|
| PP0108 | 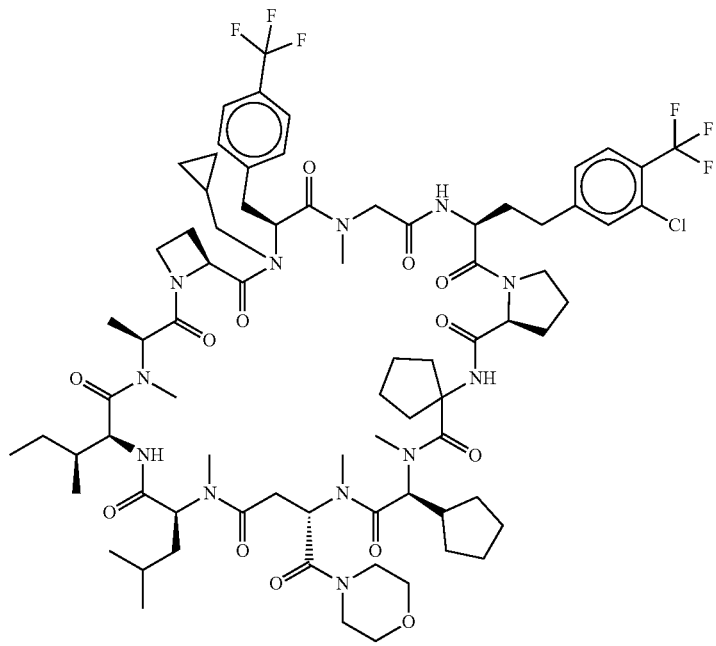 |
| PP0109 | 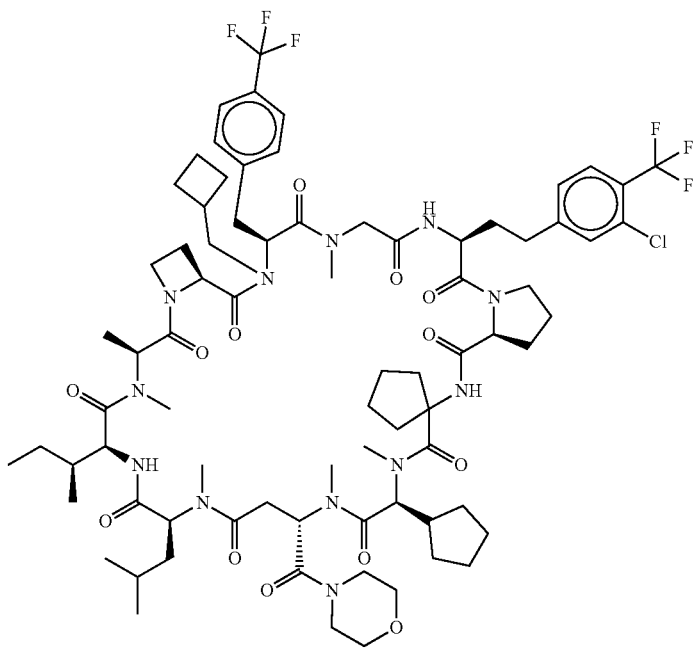 |

TABLE 38-continued
| Compound No. | Structural Formula |
| --- | --- |
| PP0110 | 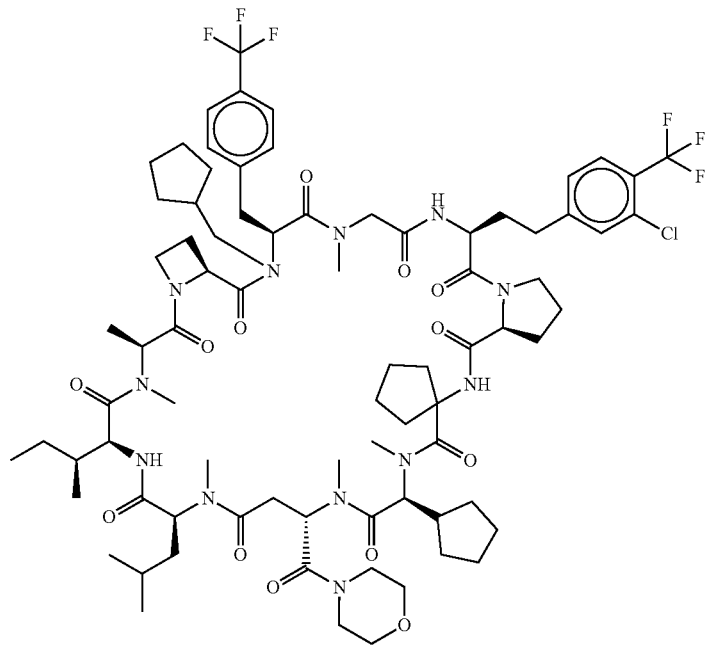 |
| PP0112 | 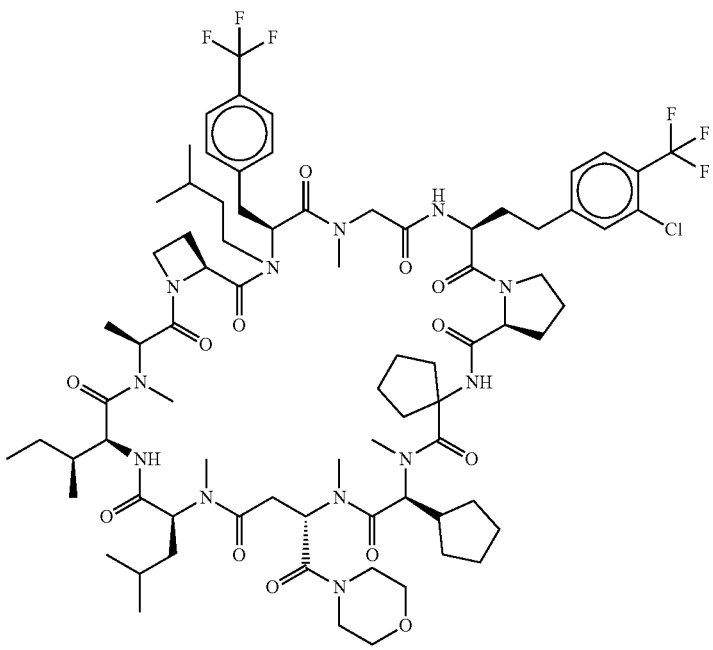 |

TABLE 38-continued

| Compound No. | Structural Formula |
|---|---|
| PP0113 | |
| PP0114 | |

TABLE 38-continued
| Compound No. | Structural Formula |
|---|---|
| PP0115 | 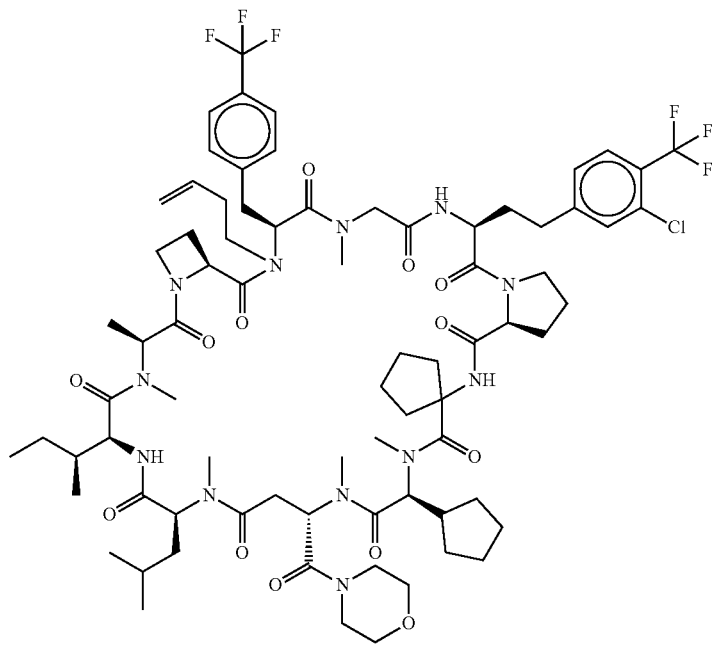 |
| PP0116 | 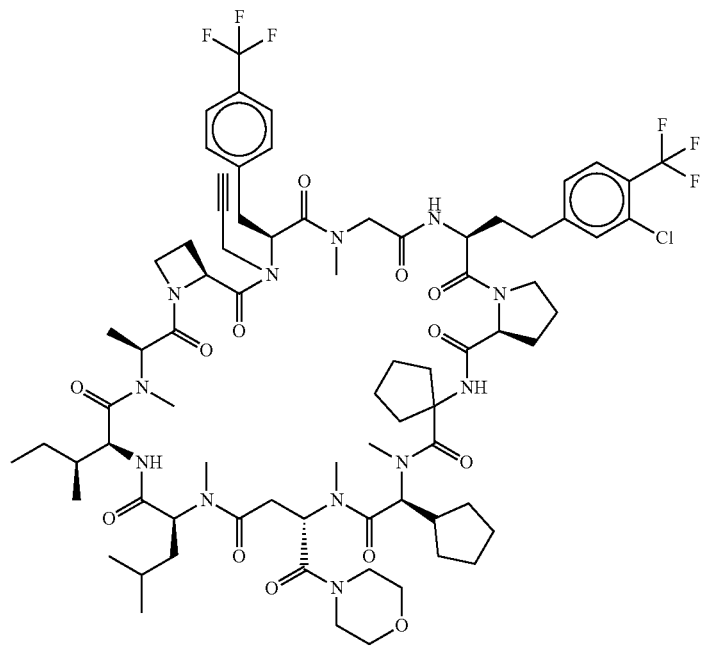 |

TABLE 38-continued
| Compound No. | Structural Formula |
|---|---|
| PP0117 | 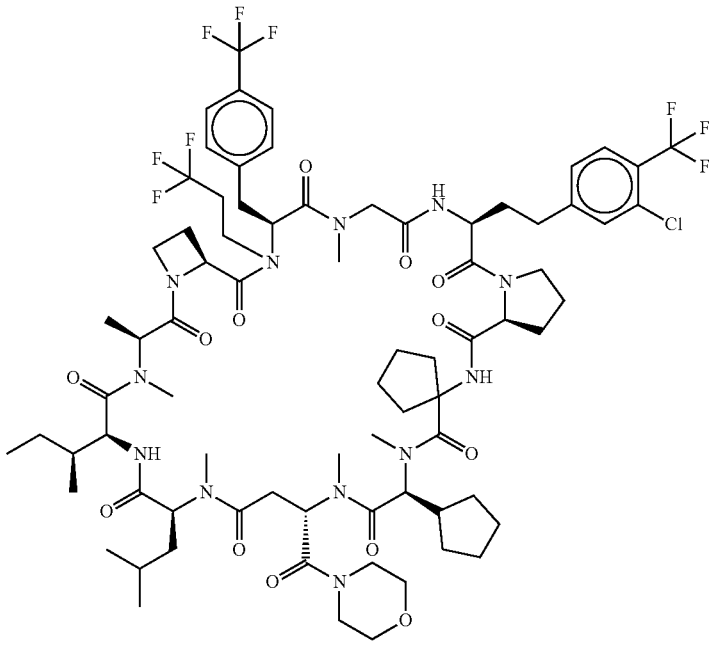 |
| PP0118 | 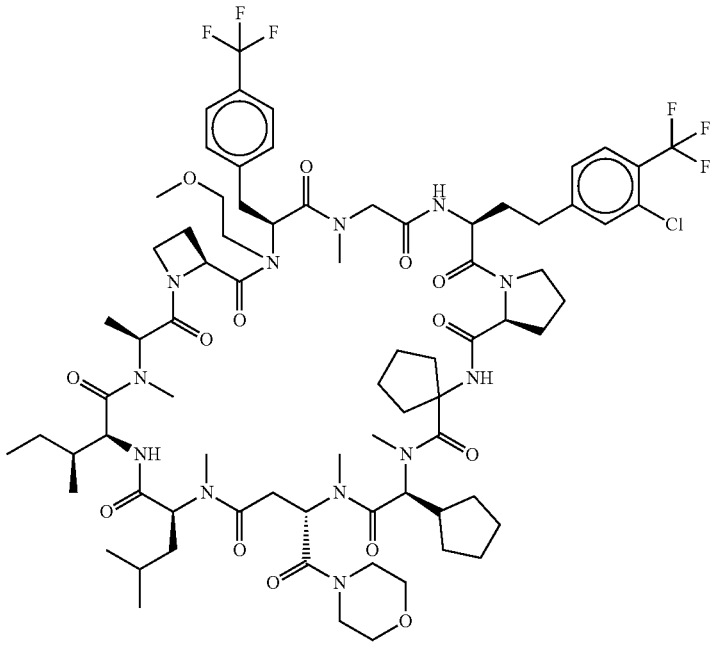 |

TABLE 38-continued
| Compound No. | Structural Formula |
|---|---|
| PP0119 | 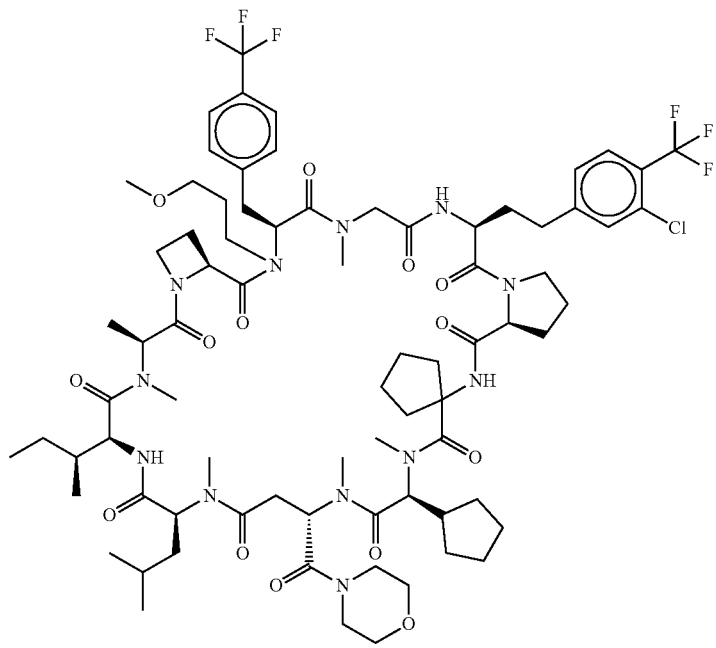 |
| PP0120 | 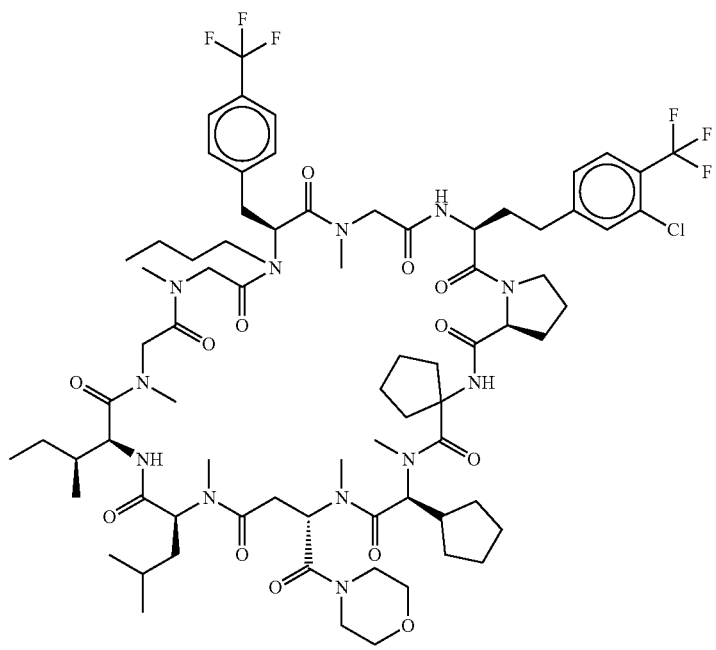 |

TABLE 38-continued
| Compound No. | Structural Formula |
|---|---|
| PP0121 | 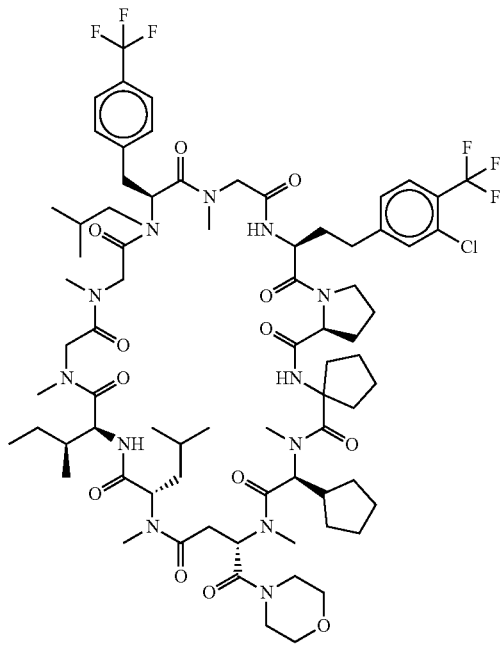 |
| PP0122 | 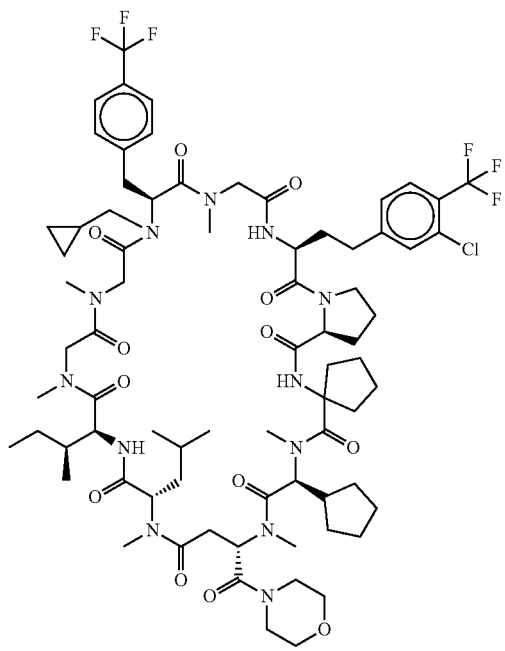 |

TABLE 38-continued
| Compound No. | Structural Formula |
|---|---|
| PP0123 | 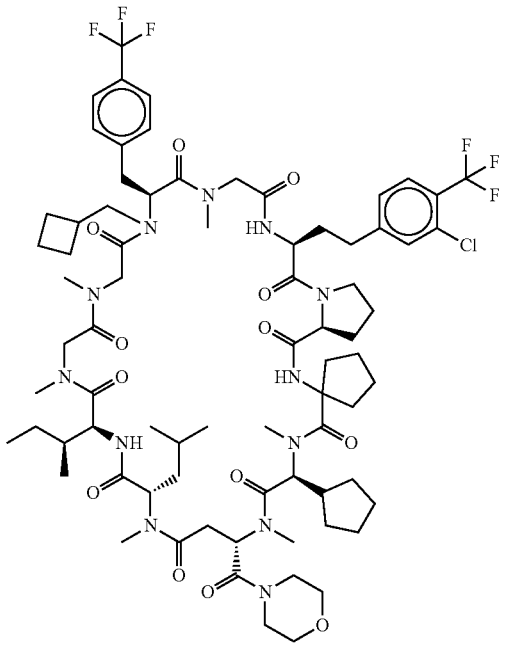 |
| PP0124 | 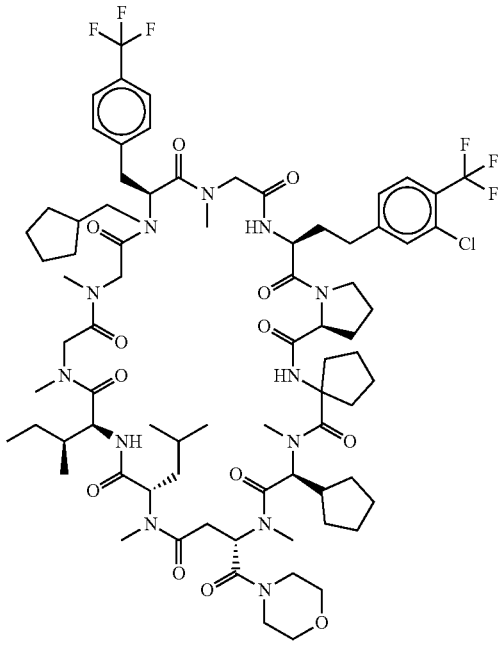 |

| Compound No. | Structural Formula |
|---|---|
| PP0126 | 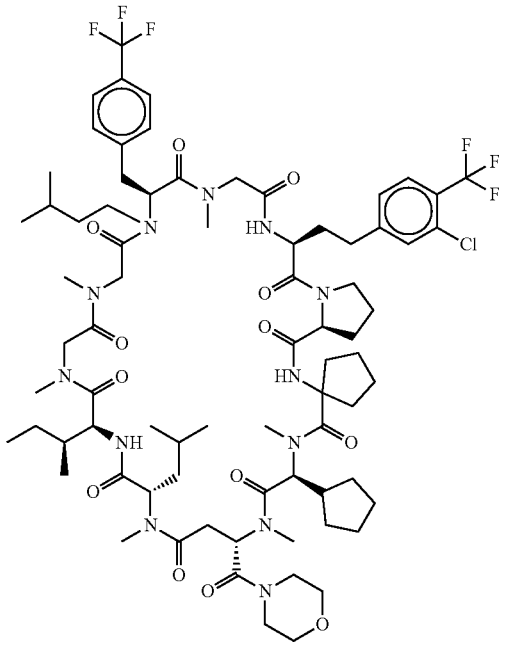 |
| PP0127 | 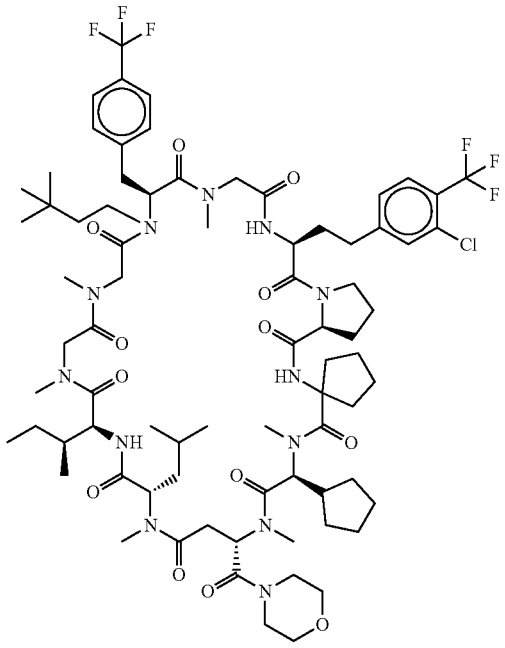 |

TABLE 38-continued
| Compound No. | Structural Formula |
|---|---|
| PP0128 | 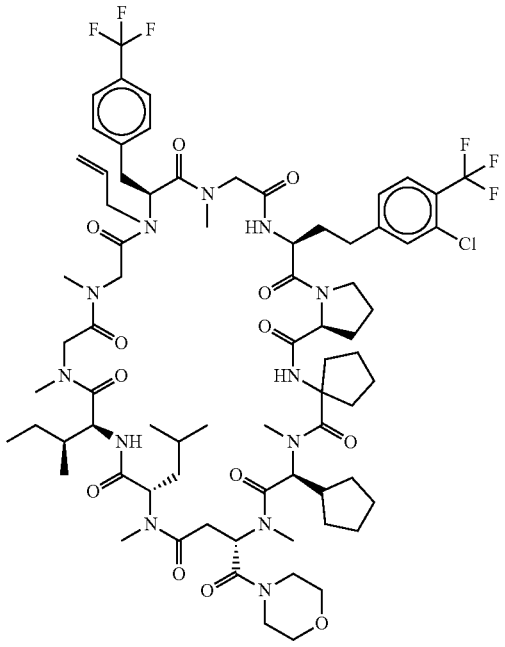 |
| PP0129 | 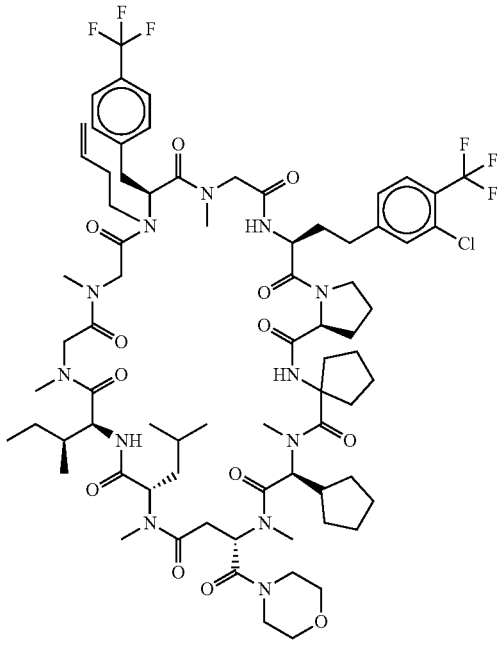 |

TABLE 38-continued

| Compound No. | Structural Formula |
|---|---|
| PP0130 | |
| PP0131 | |

TABLE 38-continued
| Compound No. | Structural Formula |
|---|---|
| PP0132 | 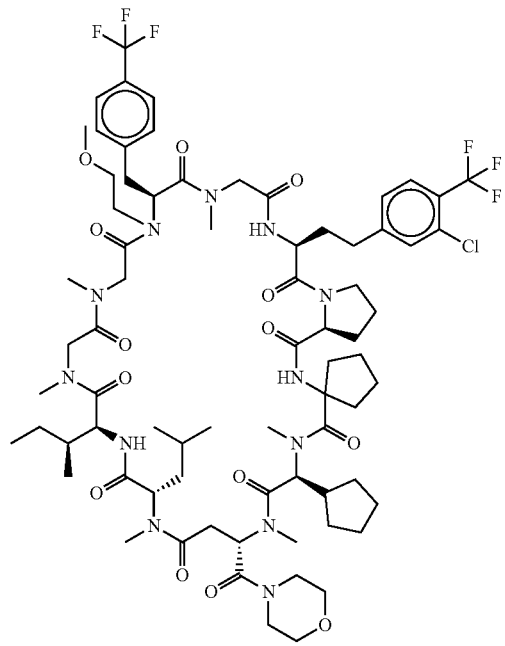 |
| PP0133 | 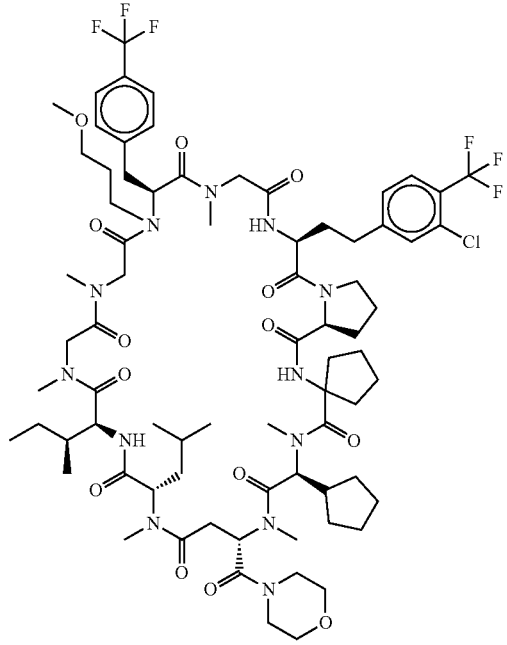 |

TABLE 38-continued
| Compound No. | Structural Formula |
|---|---|
| PP0134 | 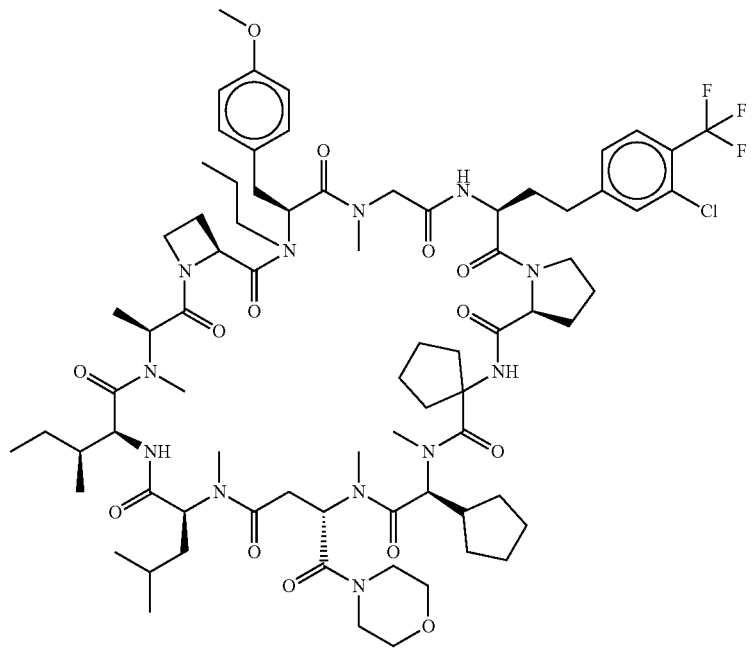 |
| PP0135 | 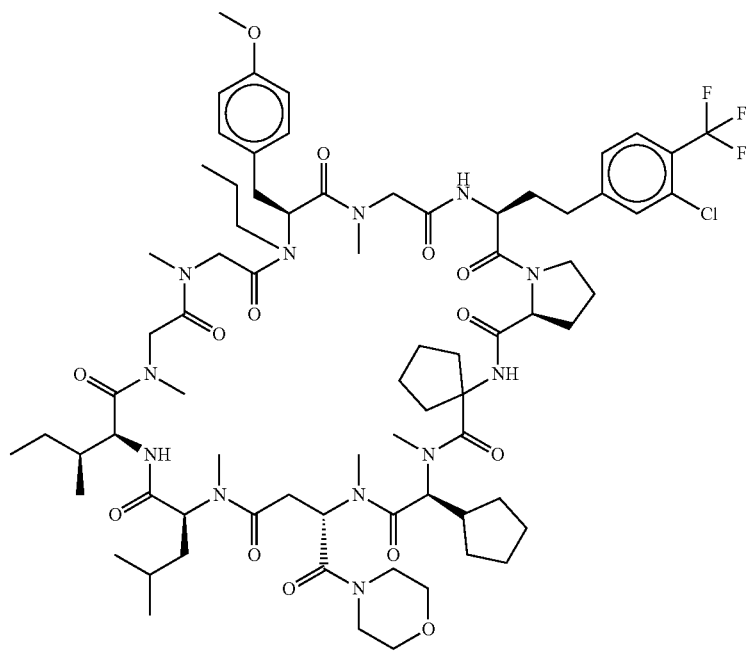 |

TABLE 38-continued
| Compound No. | Structural Formula |
|---|---|
| PP0136 | 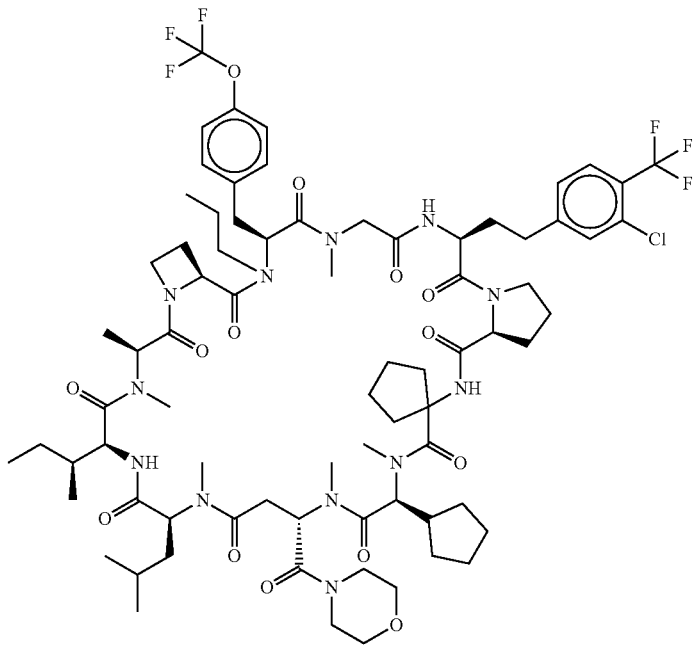 |
| PP0137 | 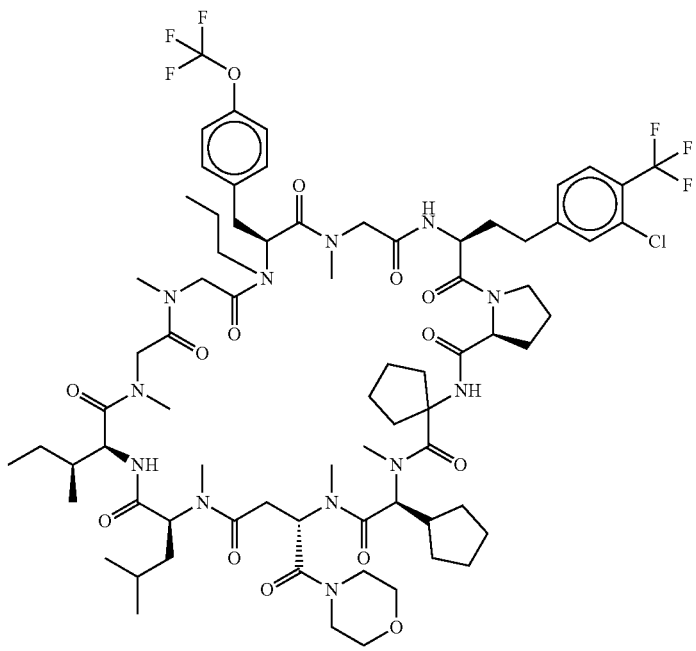 |

TABLE 38-continued
| Compound No. | Structural Formula |
|---|---|
| PP0138 | 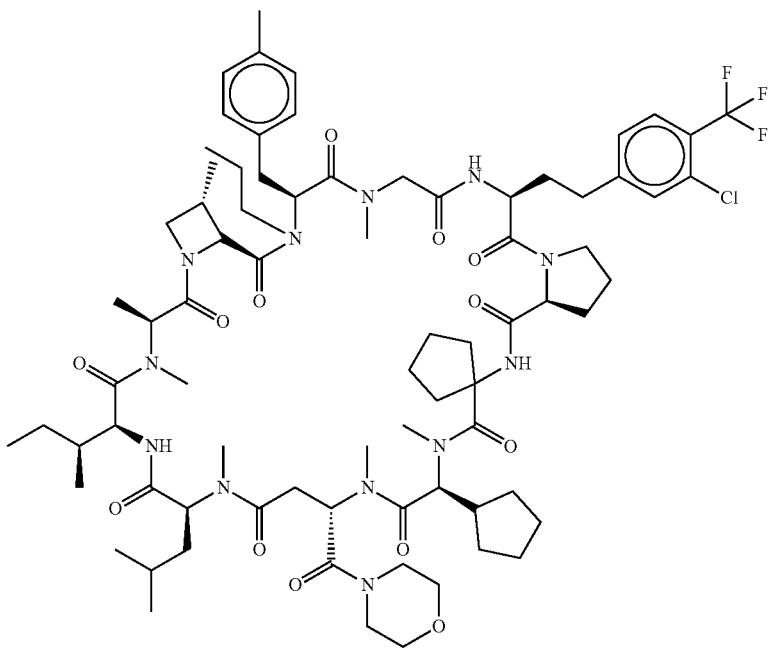 |
| PP0139 | 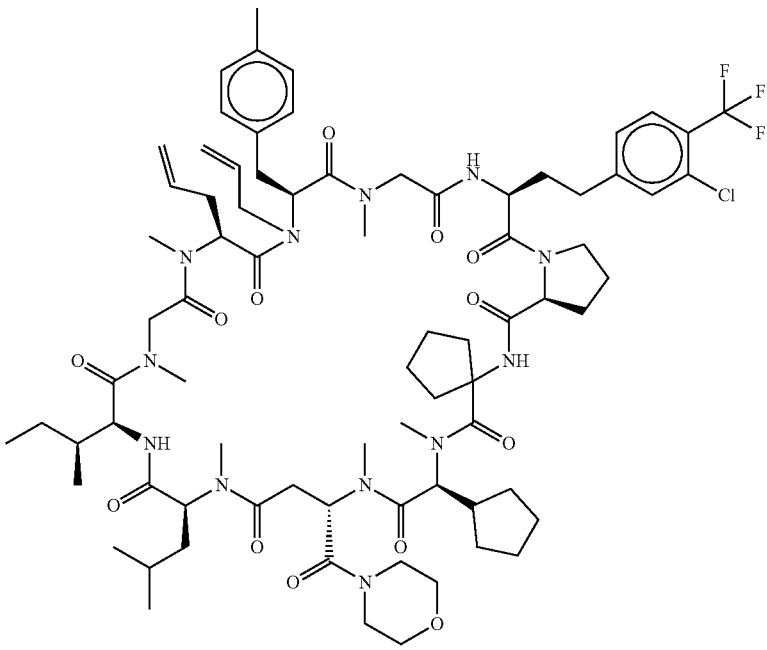 |

TABLE 38-continued

| Compound No. | Structural Formula |
|---|---|
| PP0140 | |
| PP0141 | |

TABLE 38-continued
| Compound No. | Structural Formula |
|---|---|
| PP0144 | 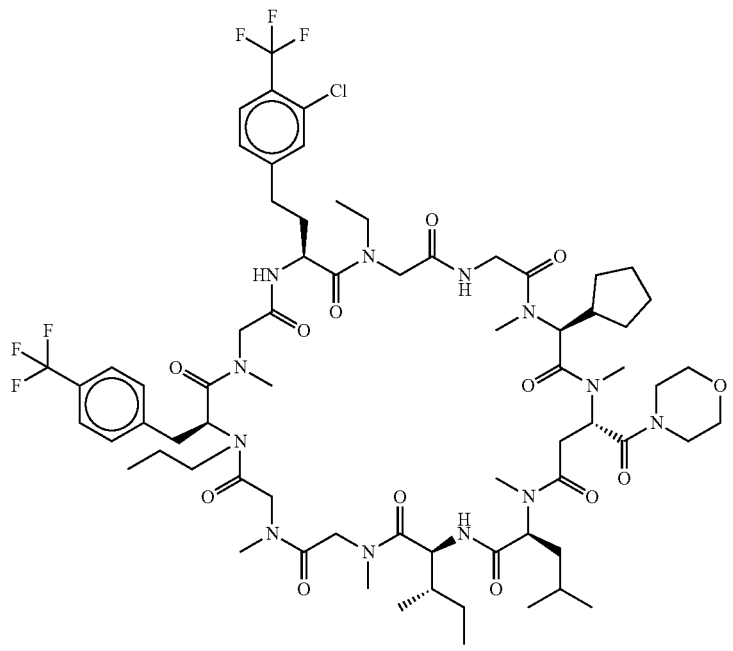 |
| PP0145 | 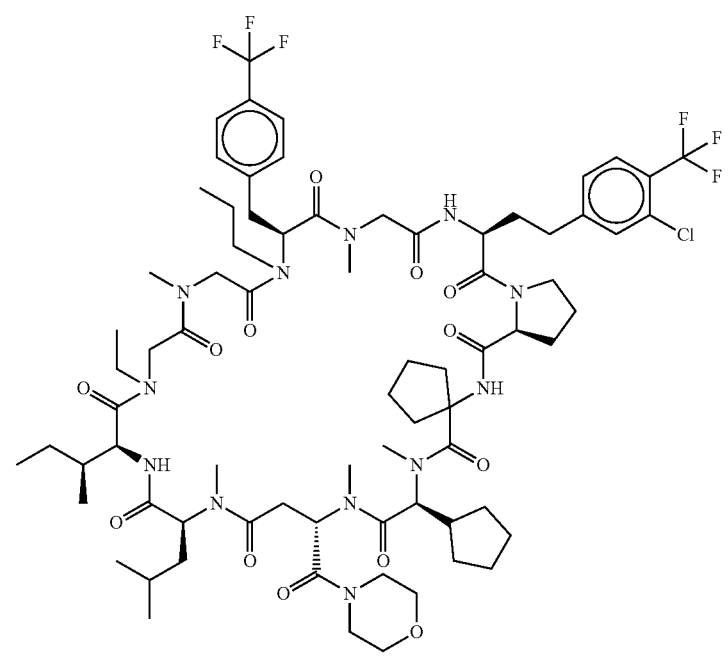 |

TABLE 38-continued
| Compound No. | Structural Formula |
|---|---|
| PP0146 | 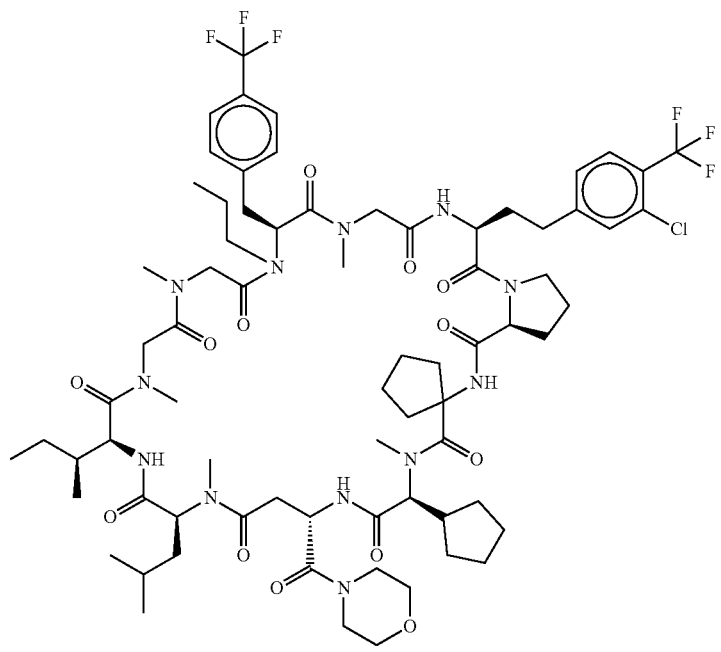 |
| PP0148 | 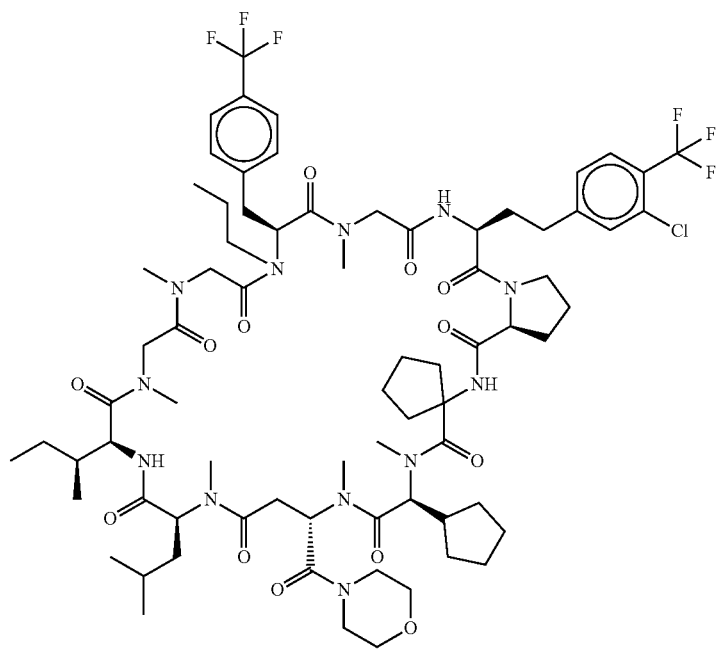 |

TABLE 38-continued
| Compound No. | Structural Formula |
|---|---|
| PP0149 | 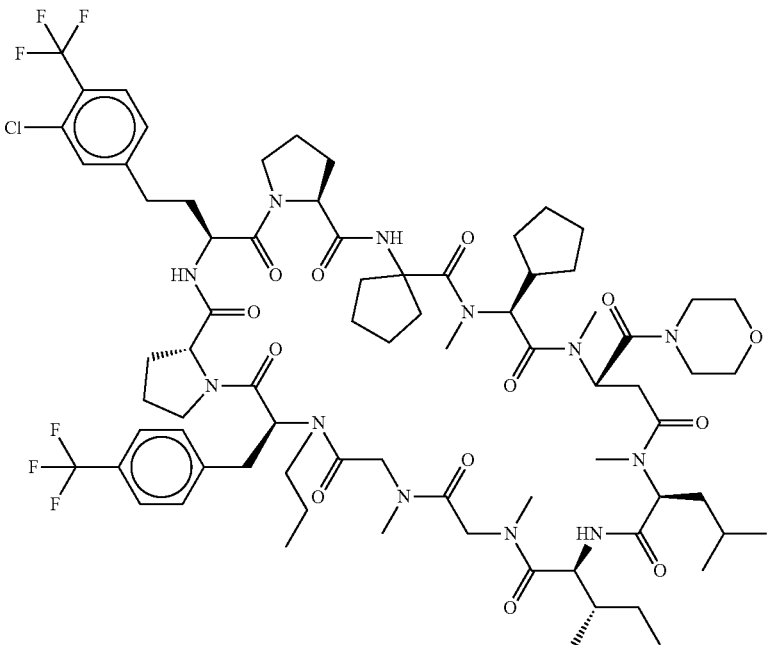 |
| PP0150 | 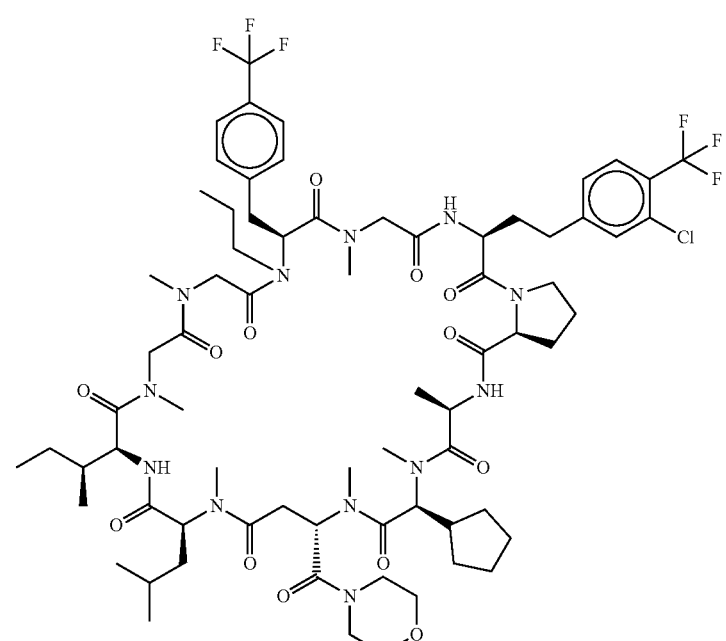 |

TABLE 38-continued

| Compound No. | Structural Formula |
|---|---|
| PP0151 | |
| PP0152 | |

TABLE 38-continued
| Compound No. | Structural Formula |
|---|---|
| PP0153 | 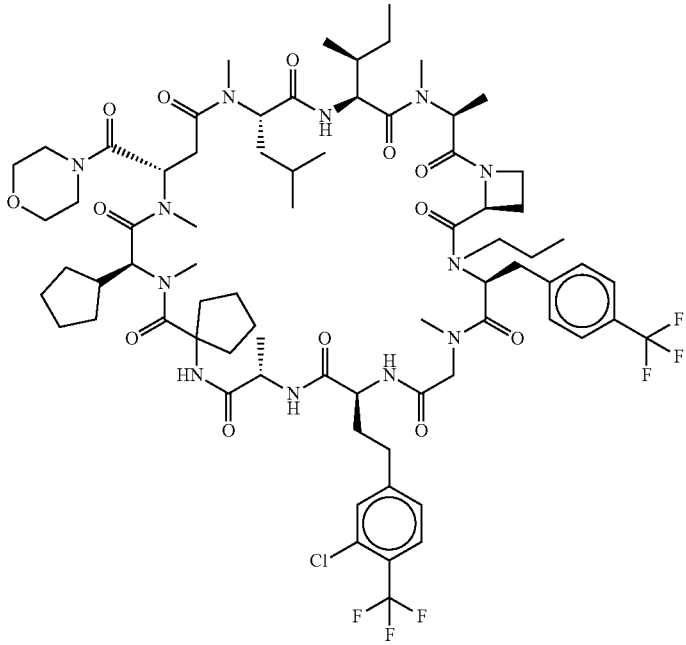 |
| PP0154 | 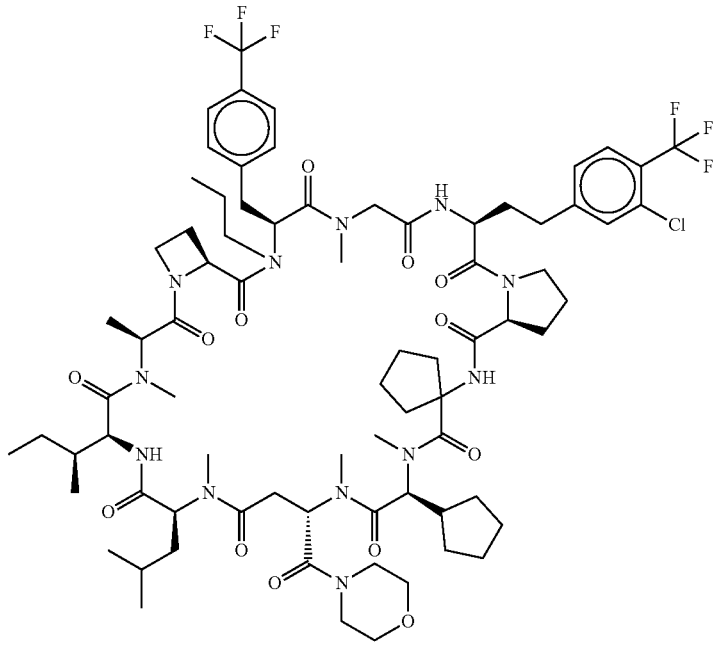 |

TABLE 38-continued
| Compound No. | Structural Formula |
|---|---|
| PP0155 | 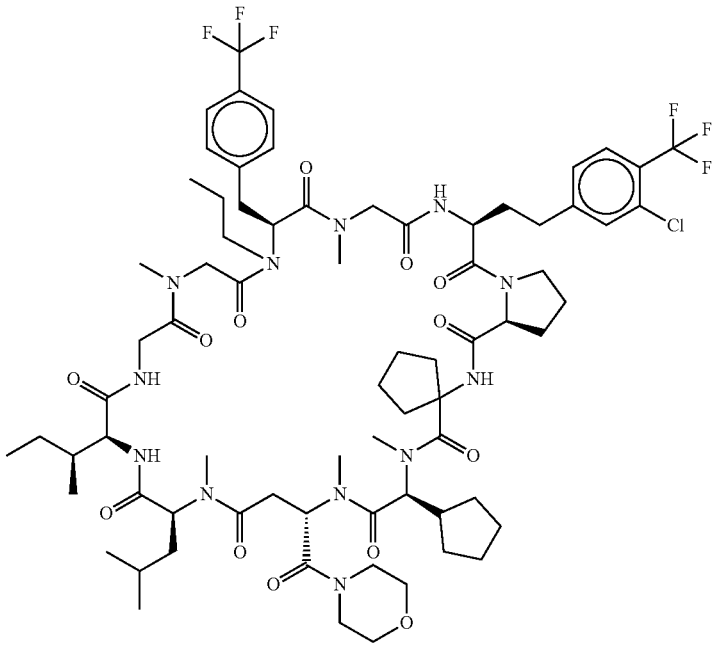 |
| PP0156 | 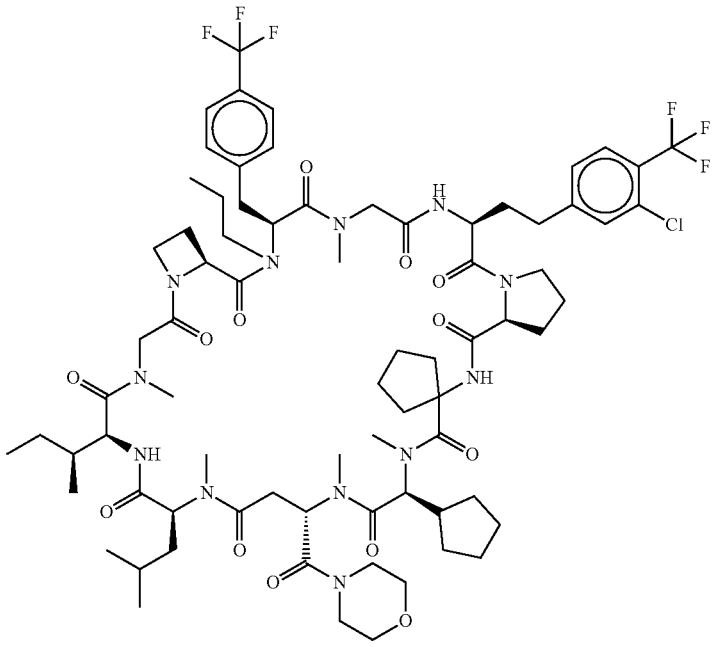 |

TABLE 38-continued
| Compound No. | Structural Formula |
|---|---|
| PP0158 | 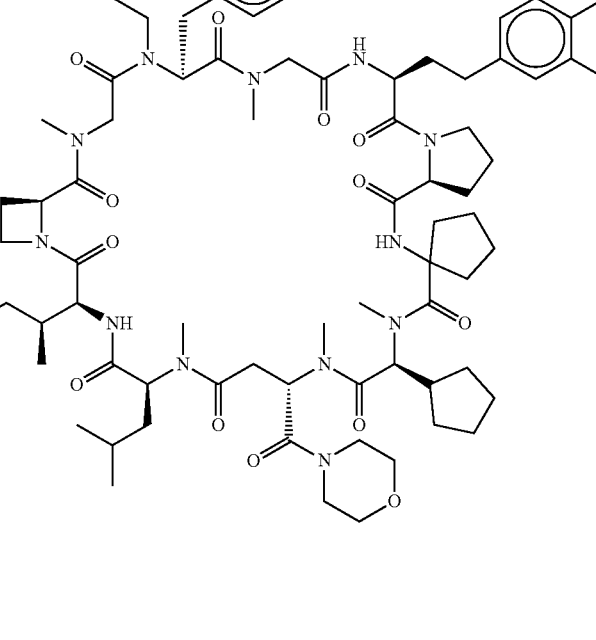 |
| PP0162 | 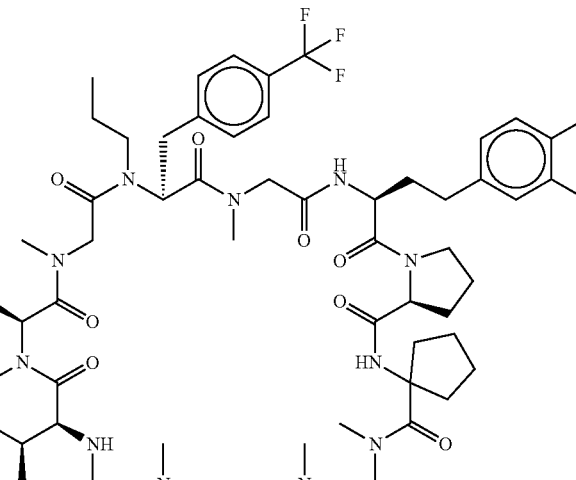 |

TABLE 38-continued

| Compound No. | Structural Formula |
|---|---|
| PP0165 | |
| PP0166 | |

TABLE 38-continued
| Compound No. | Structural Formula |
|---|---|
| PP0168 | 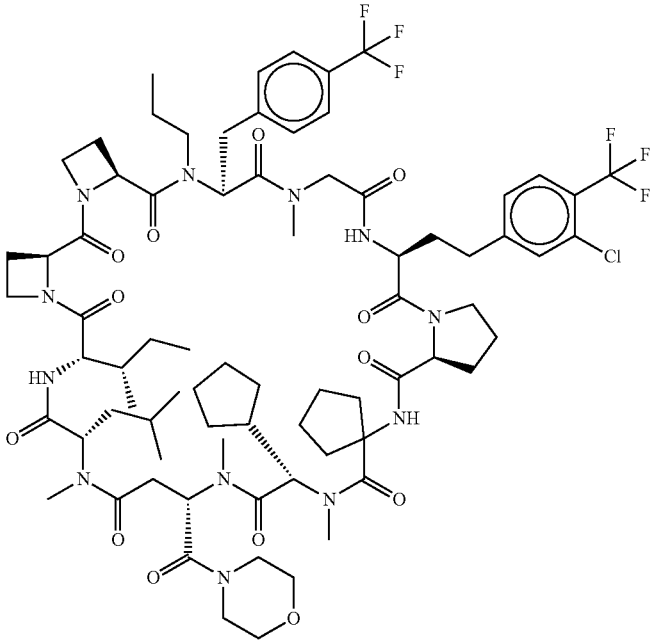 |
| PP0169 | 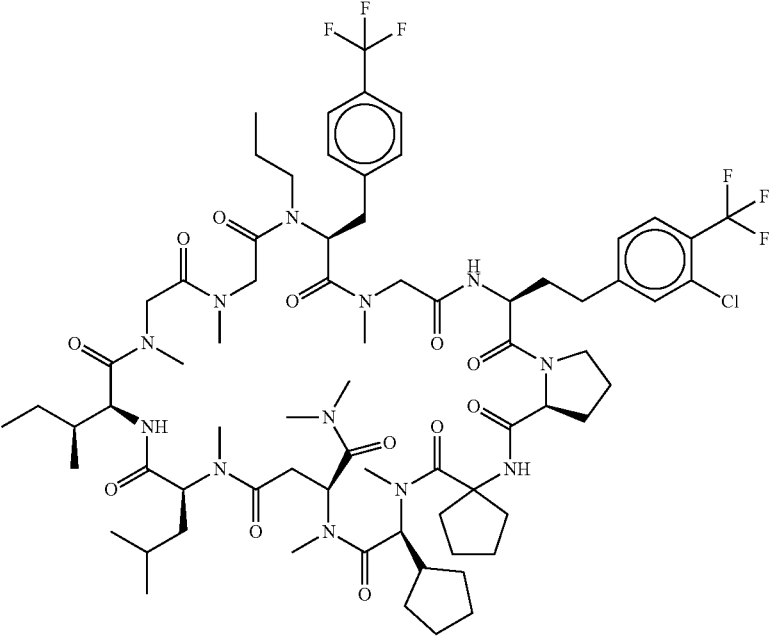 |

TABLE 38-continued
| Compound No. | Structural Formula |
|---|---|
| PP0170 | 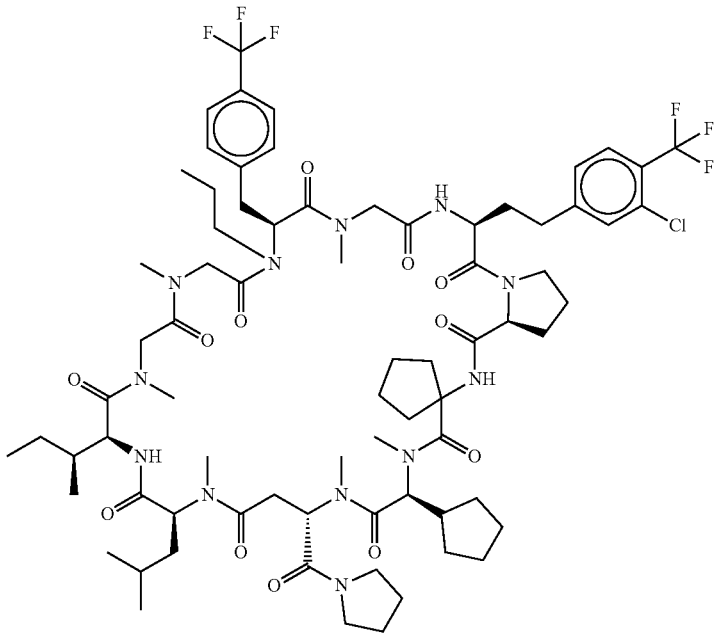 |
| PP0171 | 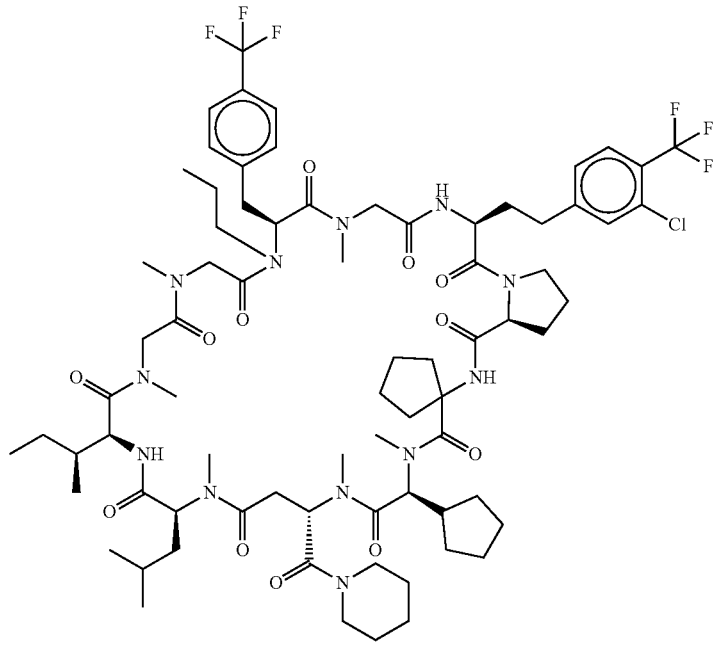 |

TABLE 38-continued
| Compound No. | Structural Formula |
|---|---|
| PP0172 | 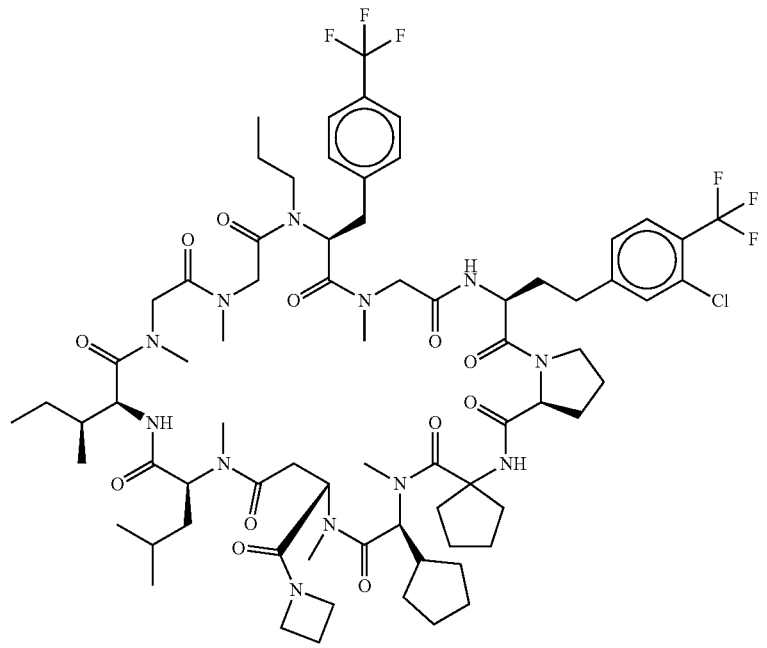 |
| PP0173 | 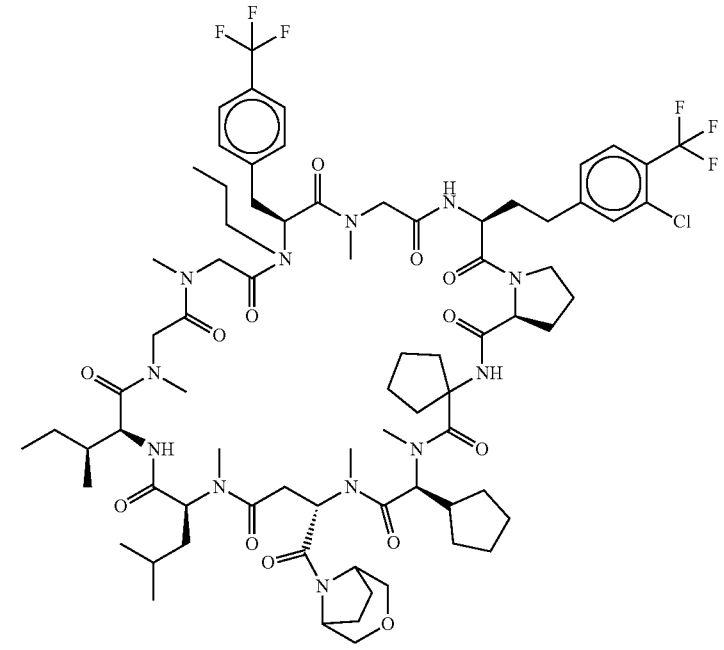 |

TABLE 38-continued
| Compound No. | Structural Formula |
|---|---|
| PP0174 | 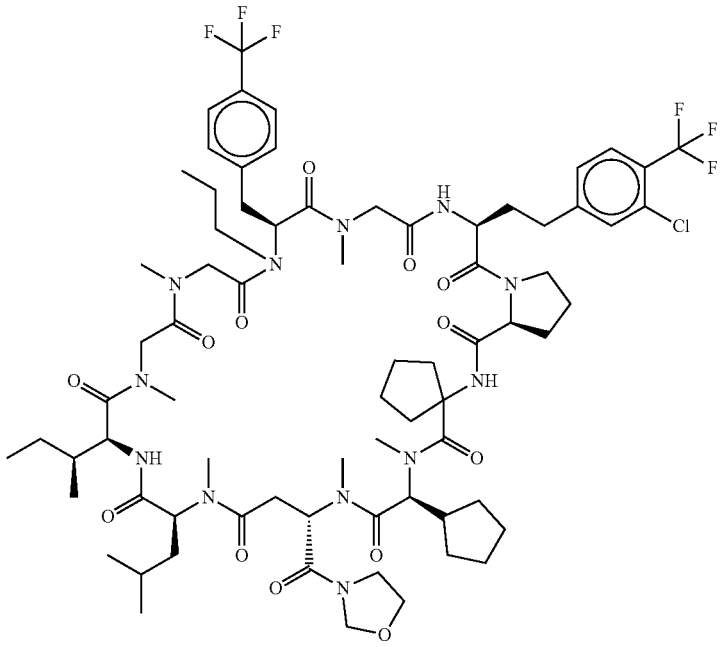 |
| PP0175 | 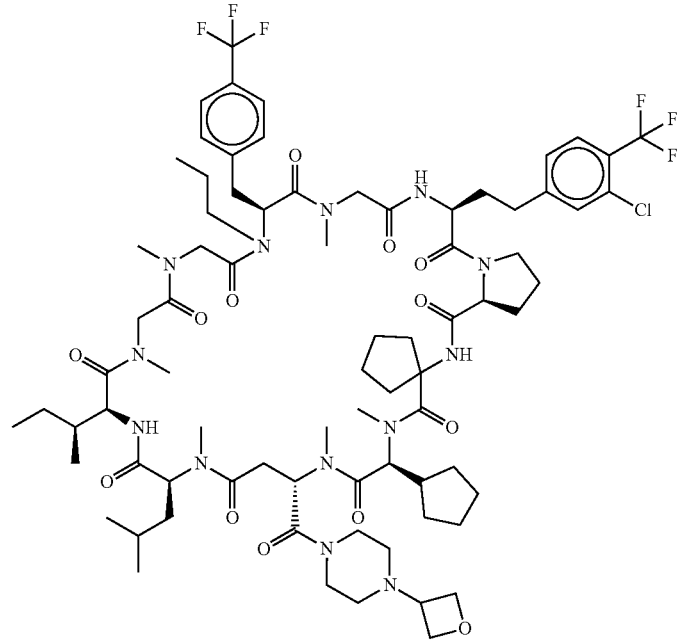 |

TABLE 38-continued
| Compound No. | Structural Formula |
|---|---|
| PP0176 | 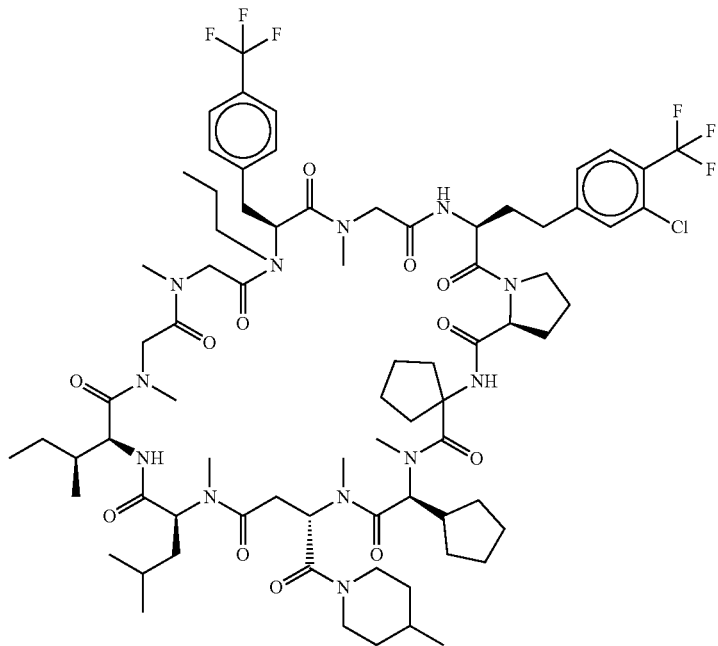 |
| PP0177 | 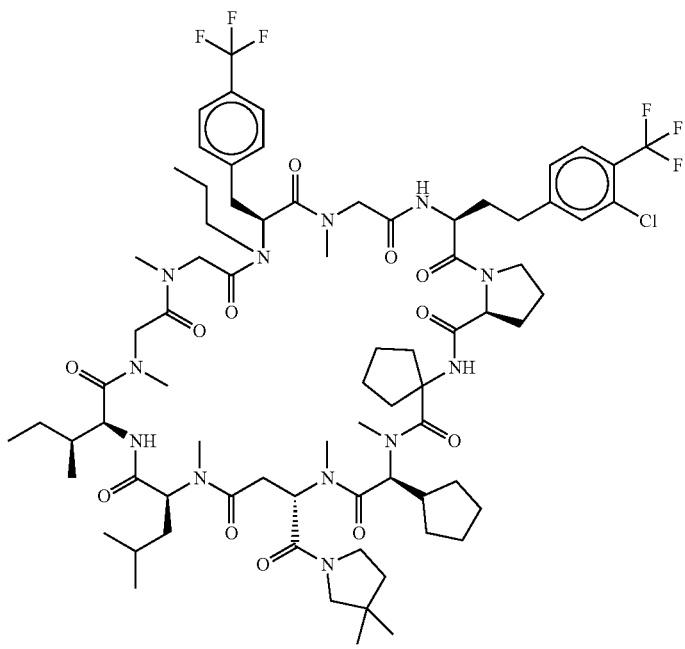 |

TABLE 38-continued

| Compound No. | Structural Formula |
|---|---|
| PP0178 | |
| PP0179 | |

TABLE 38-continued
| Compound No. | Structural Formula |
|---|---|
| PP0180 | 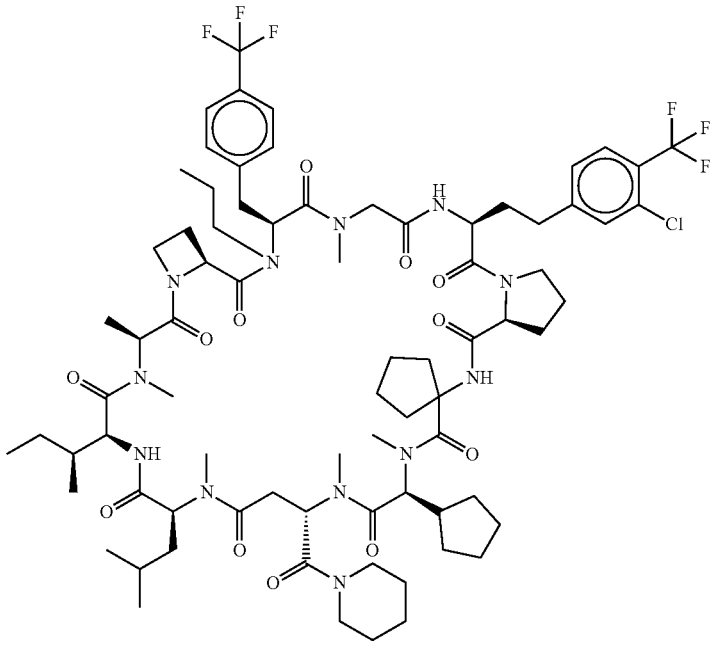 |
| PP0181 | 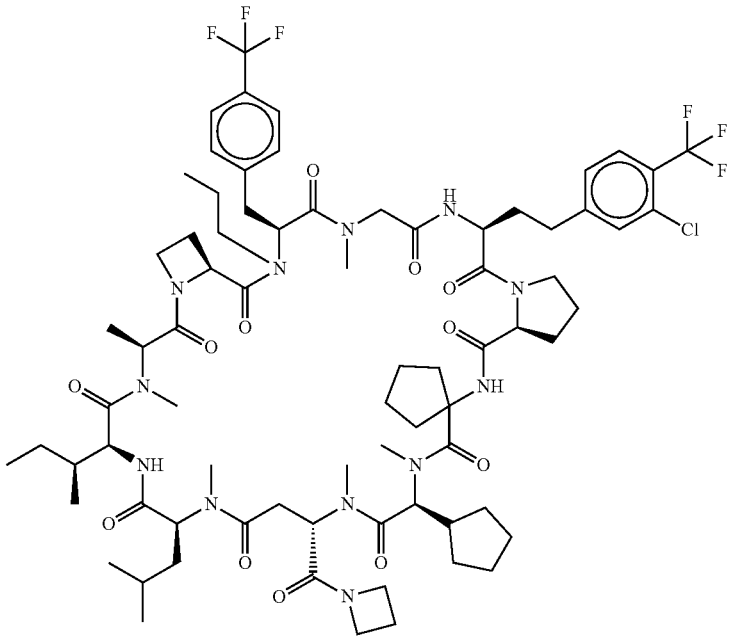 |

TABLE 38-continued
| Compound No. | Structural Formula |
|---|---|
| PP0182 | 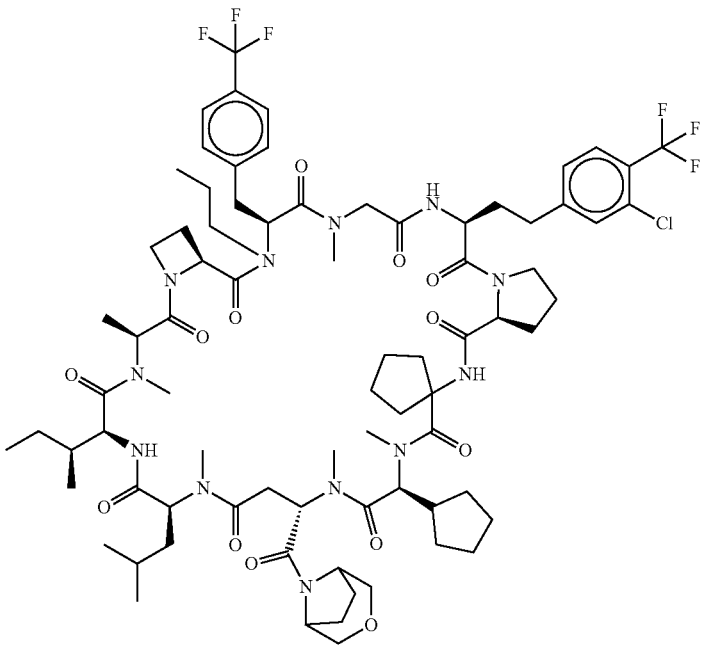 |
| PP0183 | 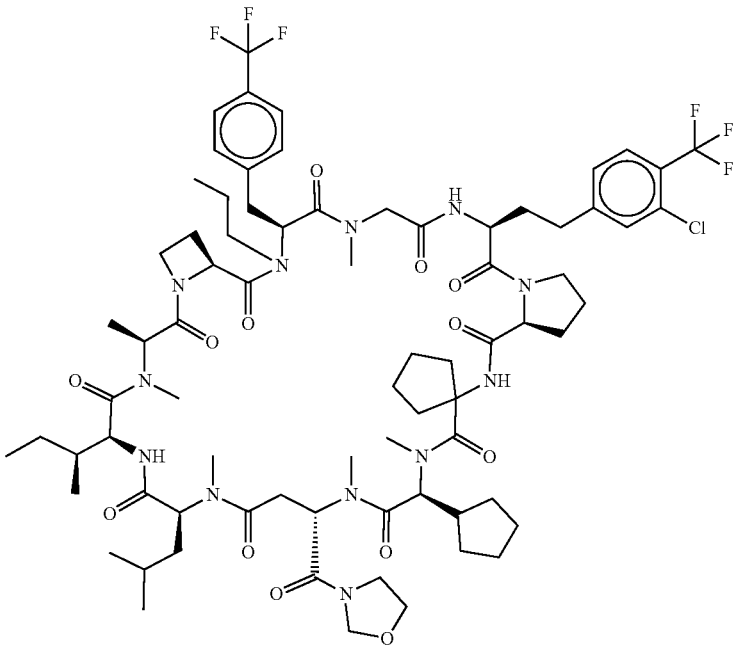 |

TABLE 38-continued
| Compound No. | Structural Formula |
|---|---|
| PP0184 | 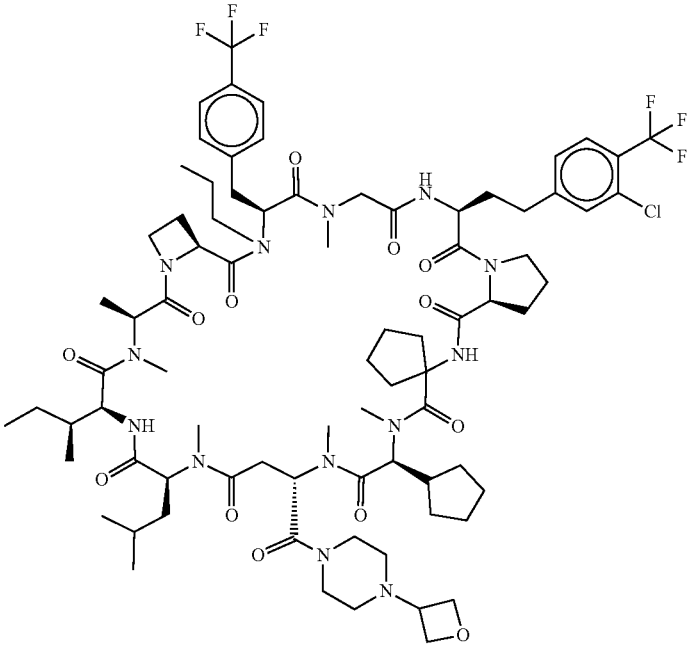 |
| PP0185 | 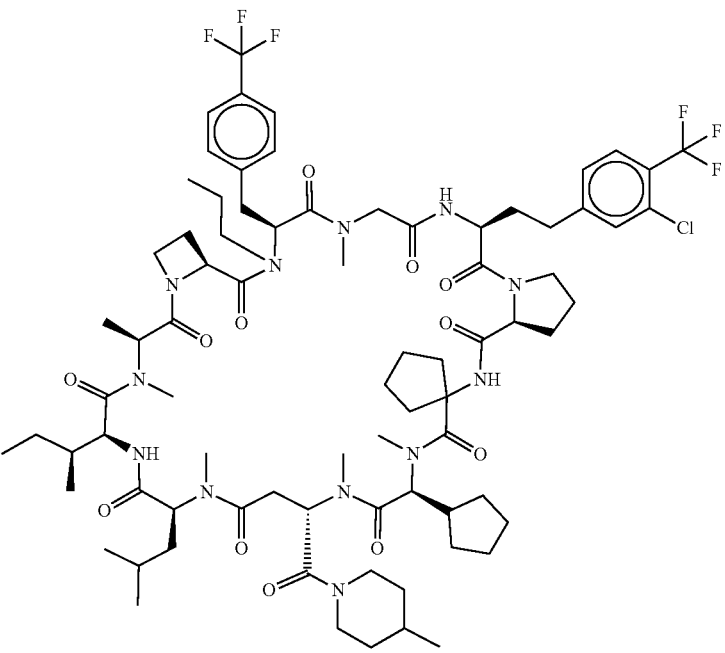 |

TABLE 38-continued
| Compound No. | Structural Formula |
|---|---|
| PP0186 | 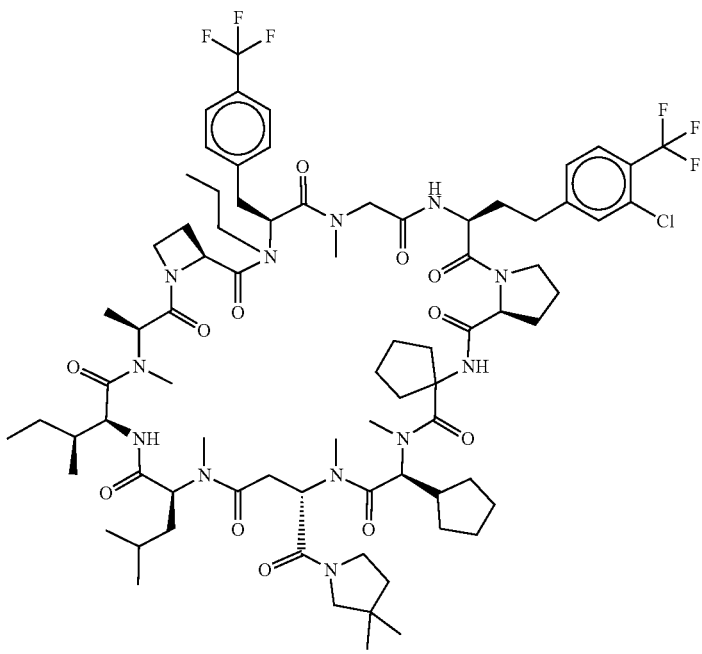 |
| PP0187 | 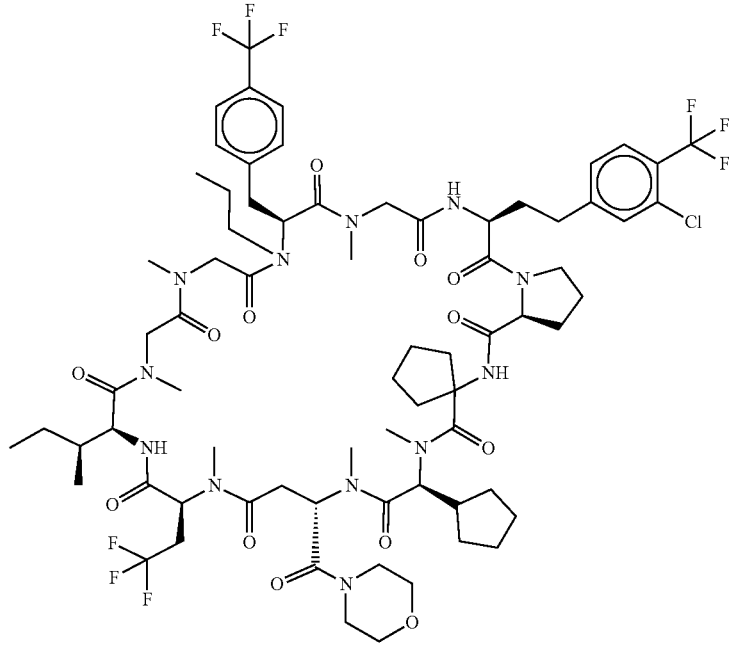 |

TABLE 38-continued
| Compound No. | Structural Formula |
| --- | --- |
| PP0188 | 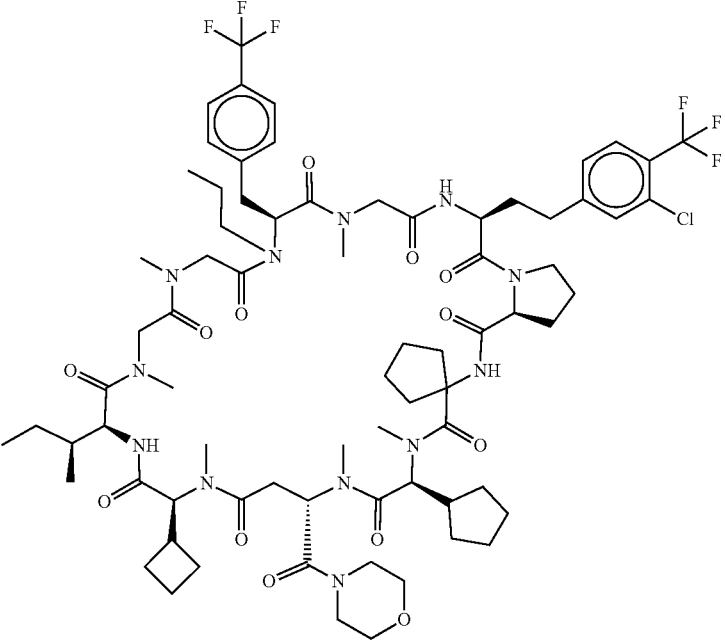 |
| PP0189 | 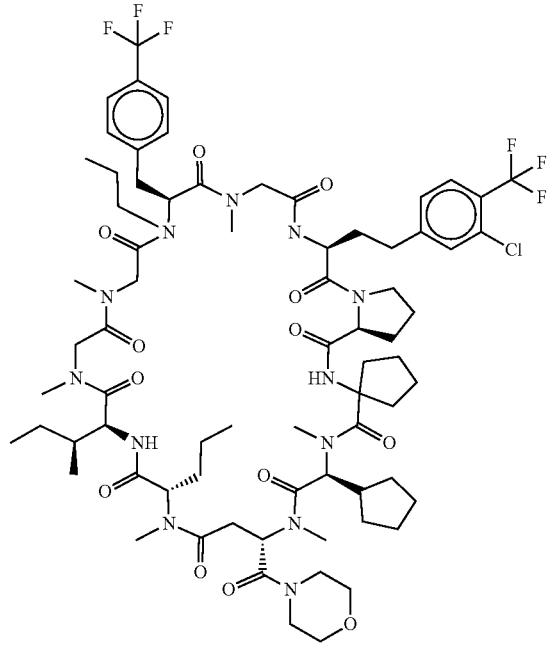 |

… TABLE 38-continued
| Compound No. | Structural Formula |
|---|---|
| PP0190 | 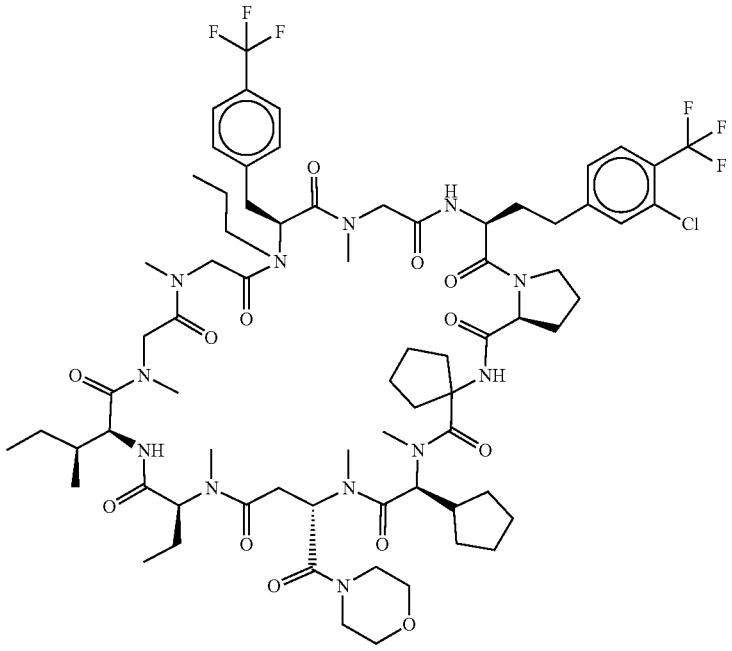 |
| PP0191 | 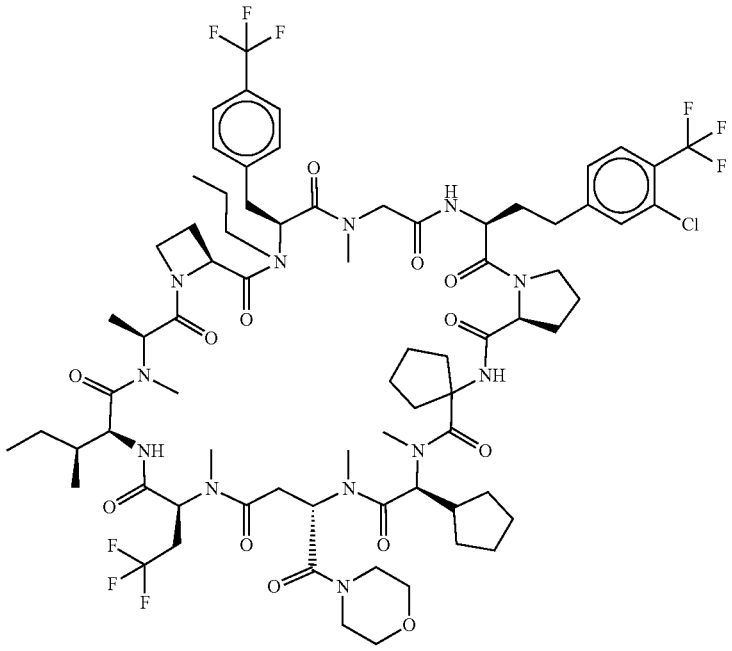 |

TABLE 38-continued
| Compound No. | Structural Formula |
|---|---|
| PP0192 | 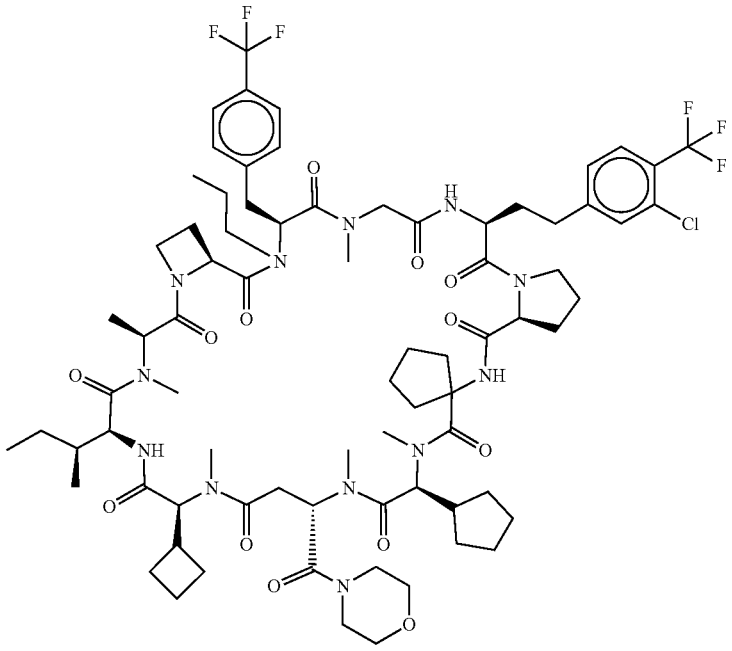 |
| PP0193 | 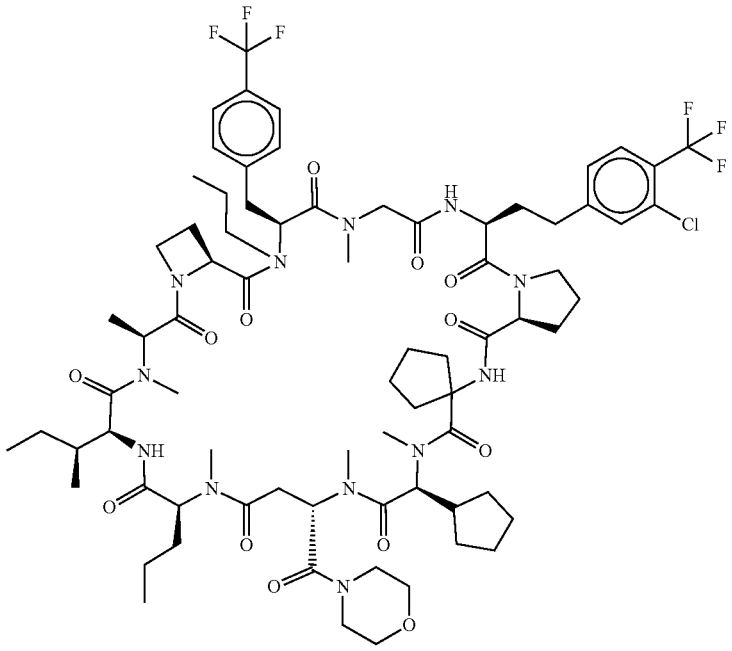 |

TABLE 38-continued
| Compound No. | Structural Formula |
|---|---|
| PP0194 | 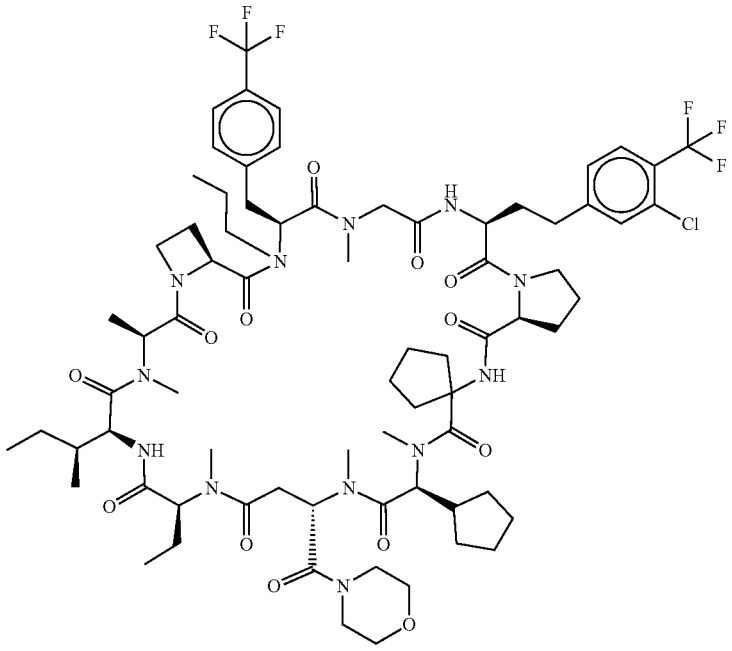 |
| PP0195 | 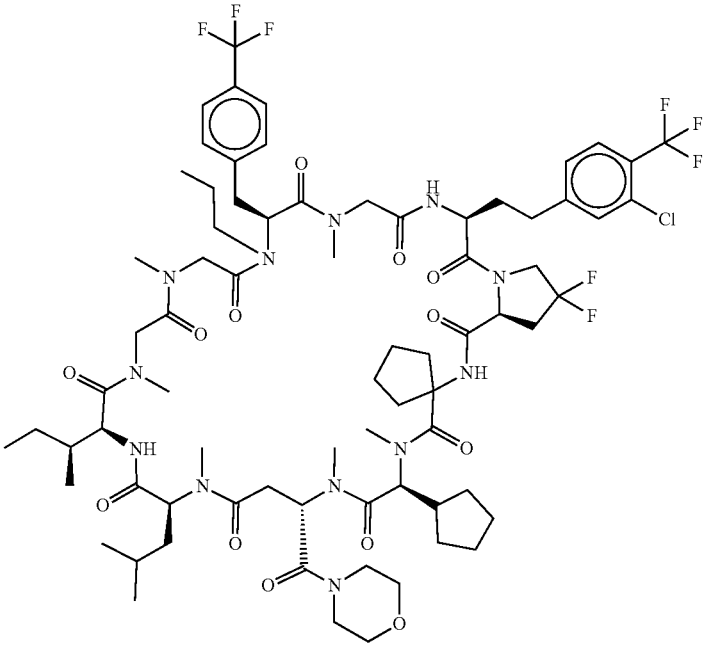 |

TABLE 38-continued
| Compound No. | Structural Formula |
|---|---|
| PP0196 | 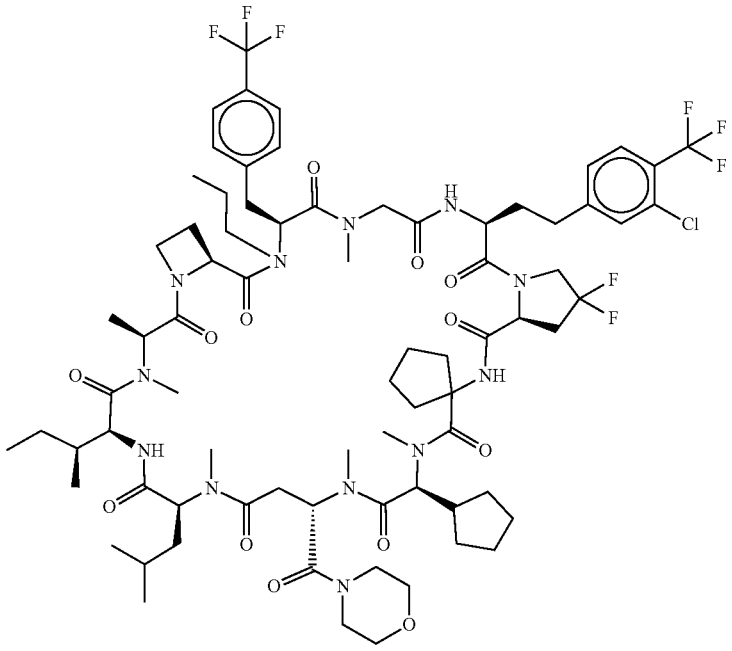 |
| PP0197 | 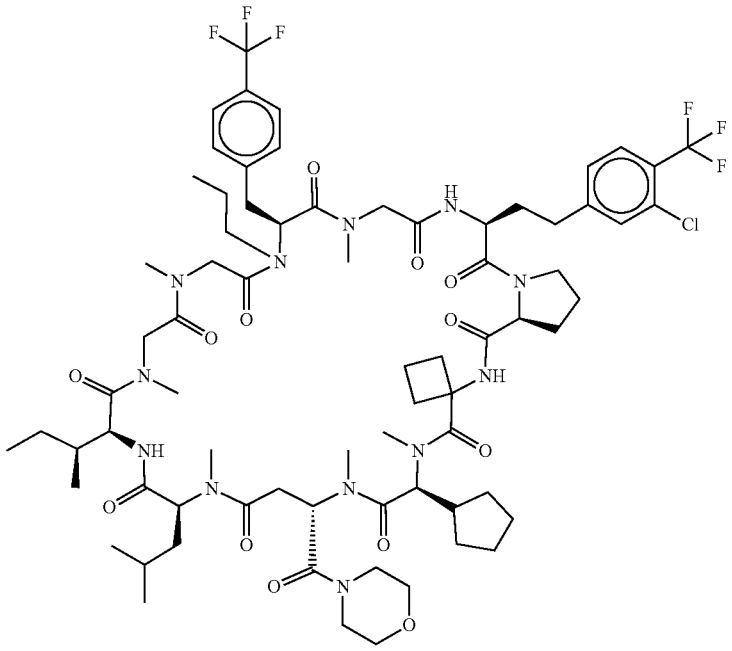 |

TABLE 38-continued
| Compound No. | Structural Formula |
|---|---|
| PP0198 | 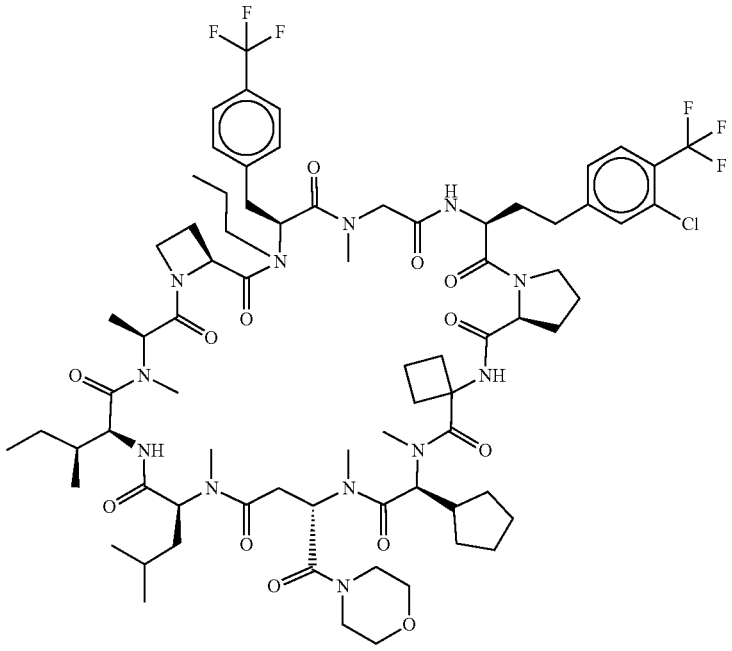 |
| PP0199 | 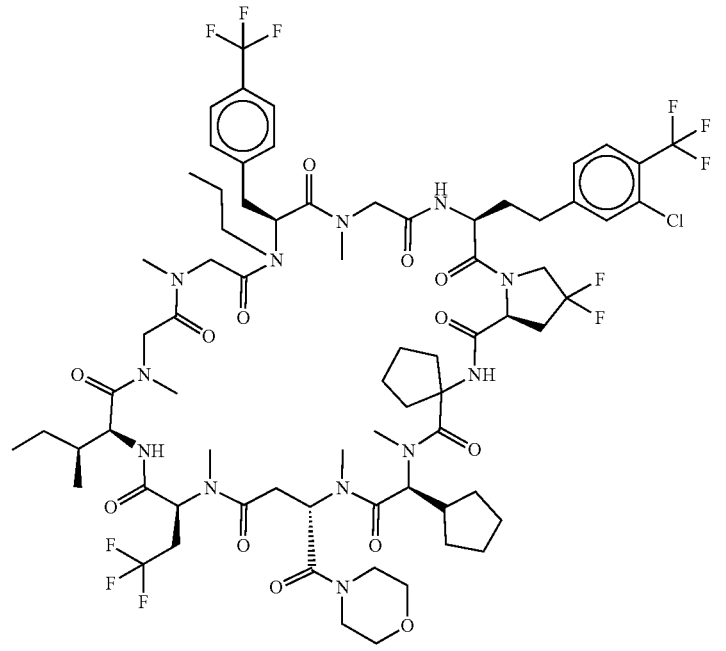 |

TABLE 38-continued
| Compound No. | Structural Formula |
|---|---|
| PP0200 | 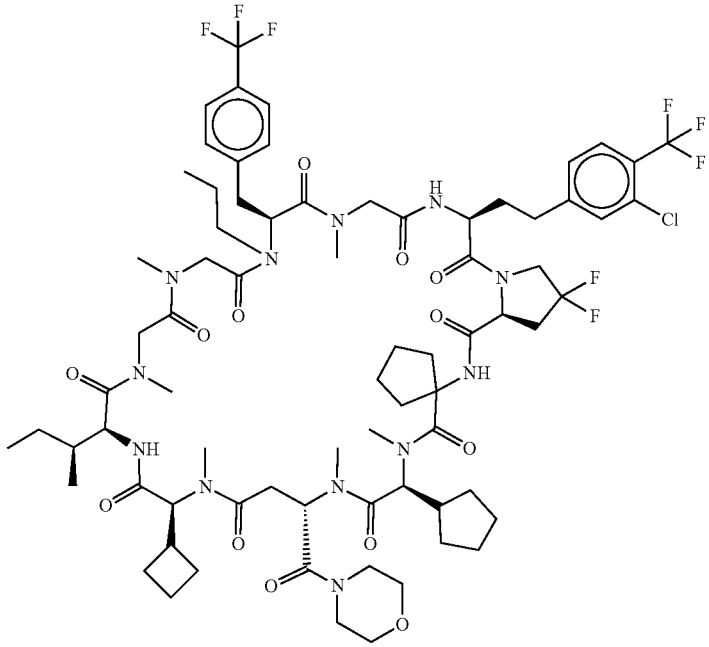 |
| PP0201 | 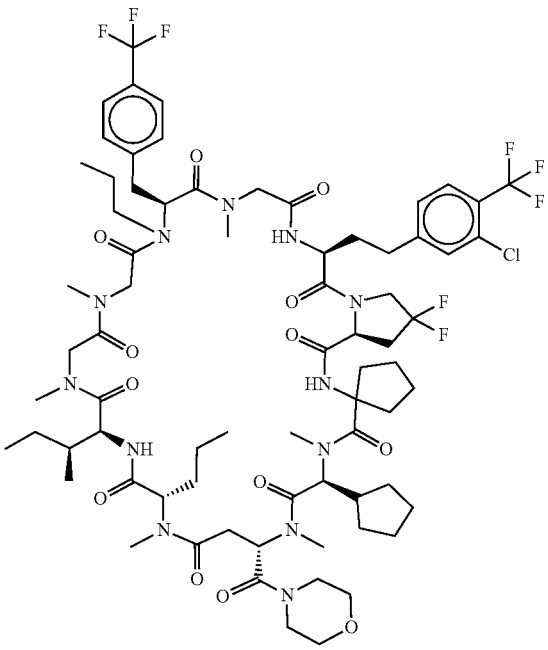 |

TABLE 38-continued

| Compound No. | Structural Formula |
|---|---|
| PP0202 | |
| PP0203 | |

| Compound No. | Structural Formula |
|---|---|
| PP0204 | |
| PP0205 | |

TABLE 38-continued
| Compound No. | Structural Formula |
| --- | --- |
| PP0206 | 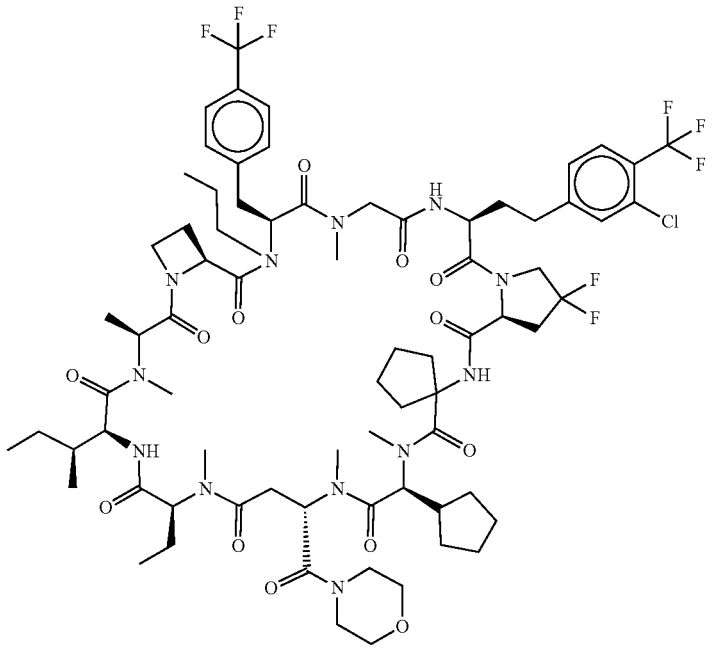 |
| PP0207 | 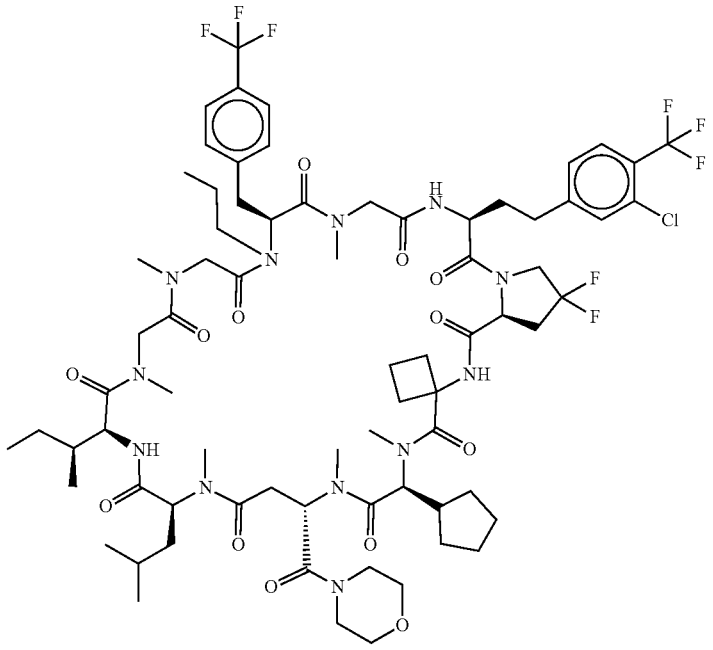 |

TABLE 38-continued
| Compound No. | Structural Formula |
|---|---|
| PP0208 | 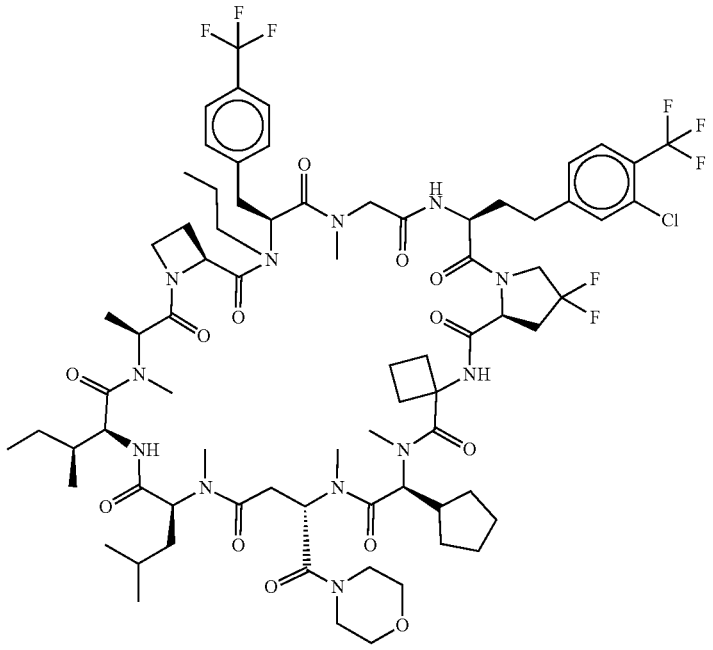 |
| PP0209 | 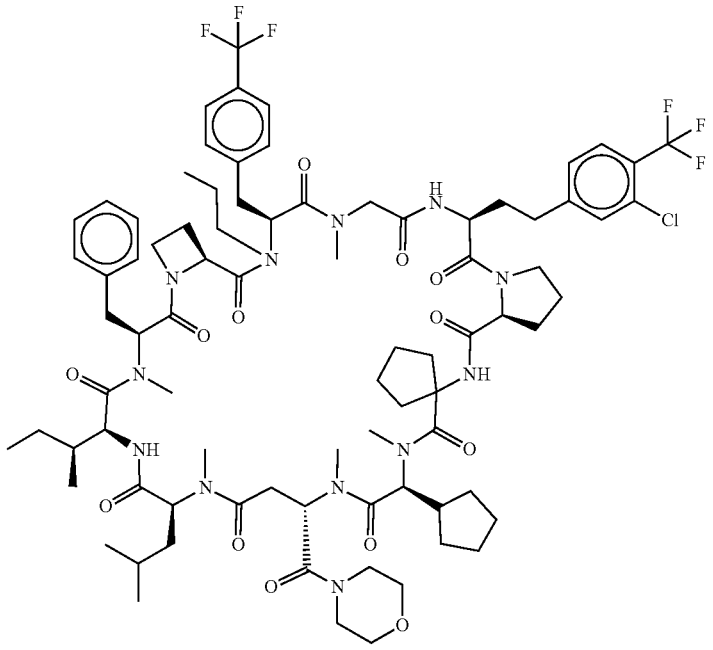 |

TABLE 38-continued
| Compound No. | Structural Formula |
|---|---|
| PP0210 | 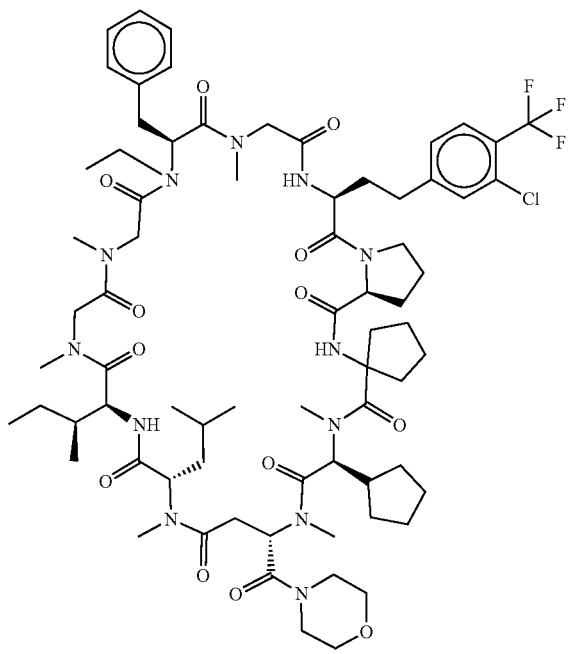 |
| PP0211 | 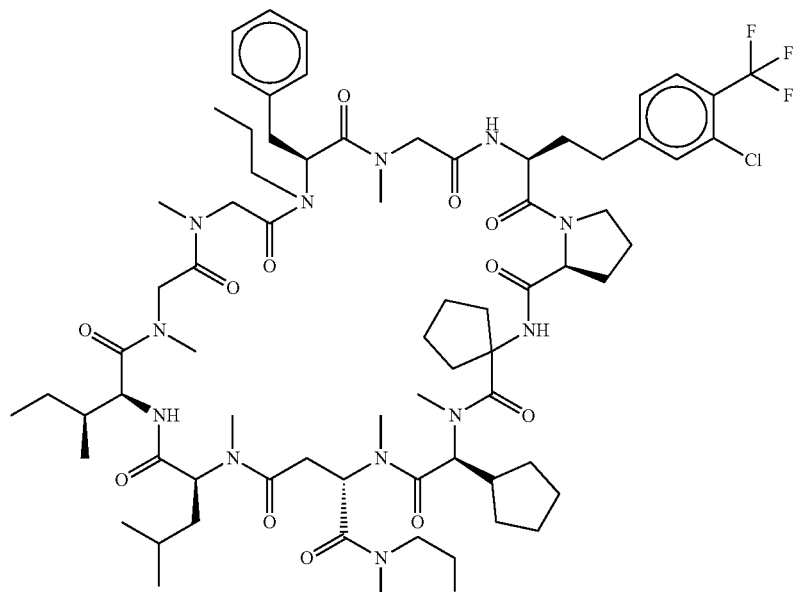 |

US 12,410,212 B2
1065                                    1066
TABLE 38-continued
| Compound No. | Structural Formula |
|---|---|
| PP0212 | 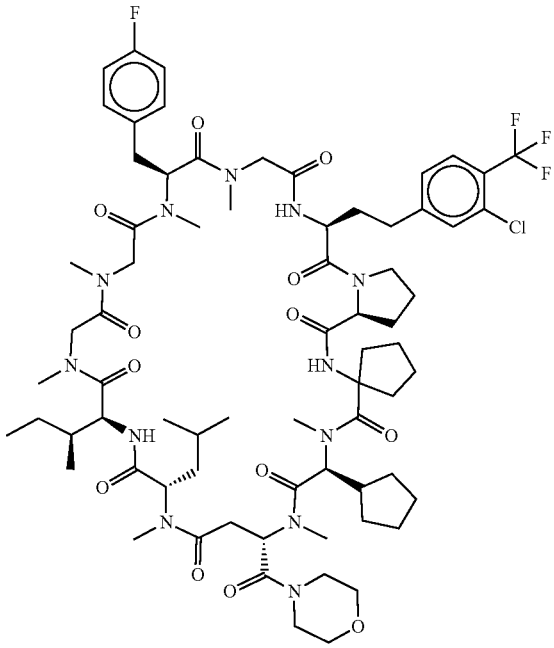 |
| PP0213 | 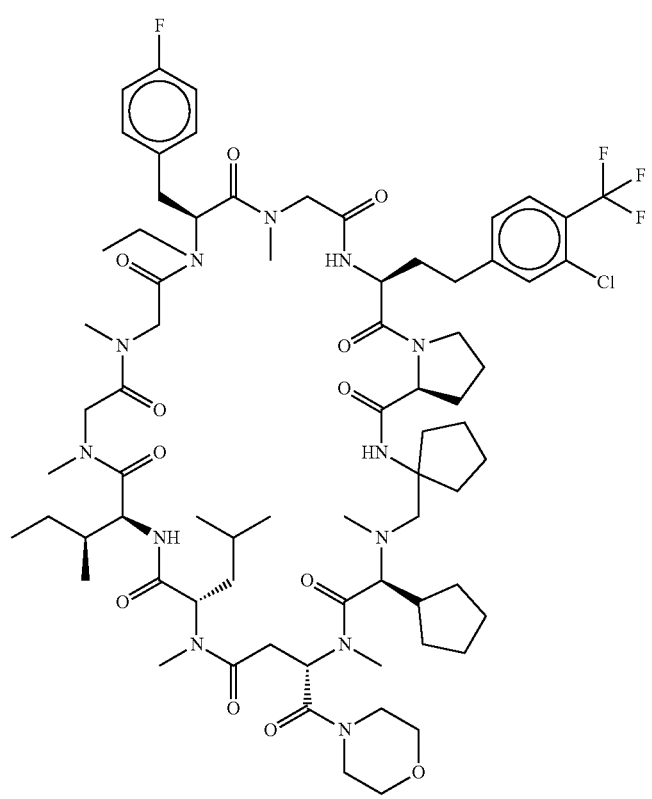 |

TABLE 38-continued

| Compound No. | Structural Formula |
| --- | --- |
| PP0214 | |
| PP0215 | |

TABLE 38-continued

| Compound No. | Structural Formula |
|---|---|
| PP0216 | |
| PP0217 | |

TABLE 38-continued
| Compound No. | Structural Formula |
|---|---|
| PP0218 | 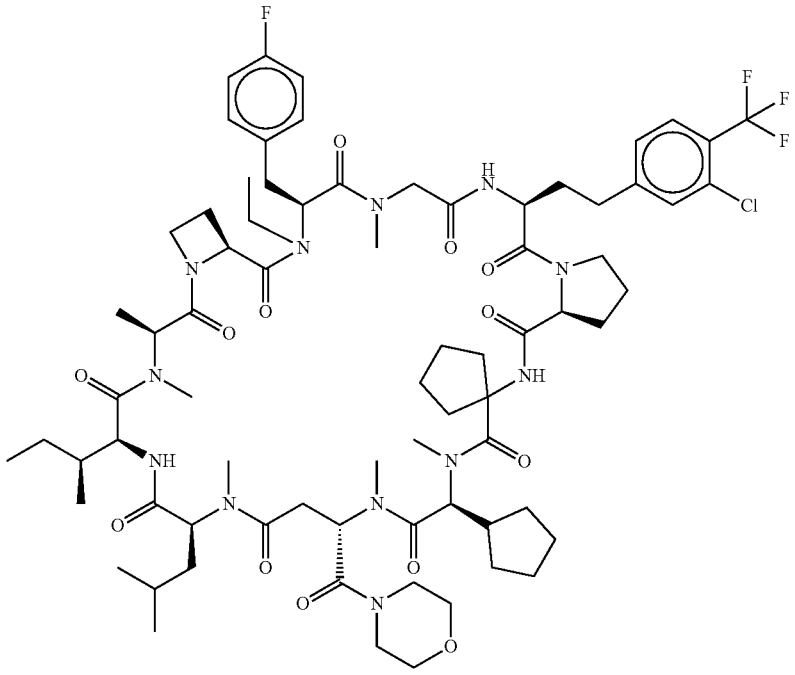 |
| PP0219 | 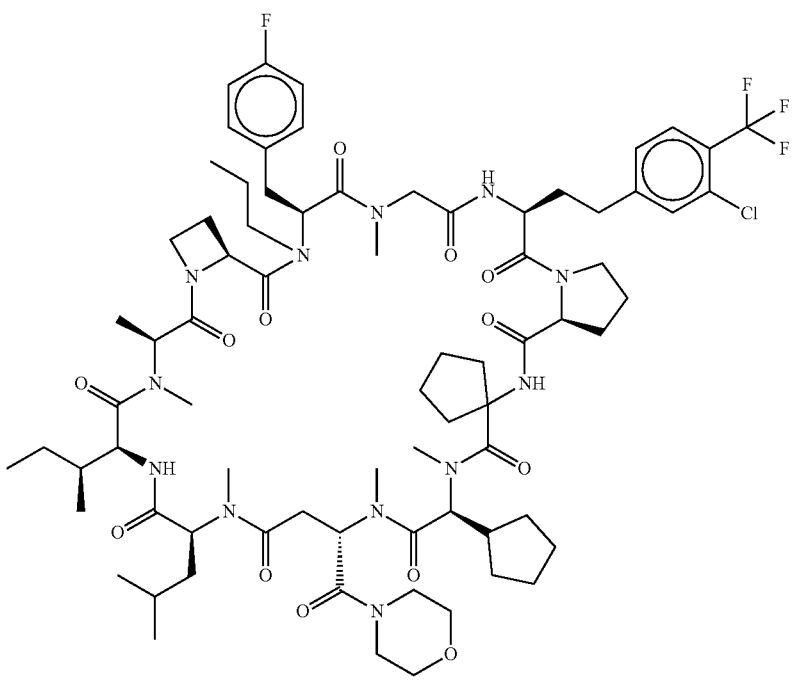 |

TABLE 38-continued
| Compound No. | Structural Formula |
|---|---|
| PP0220 | 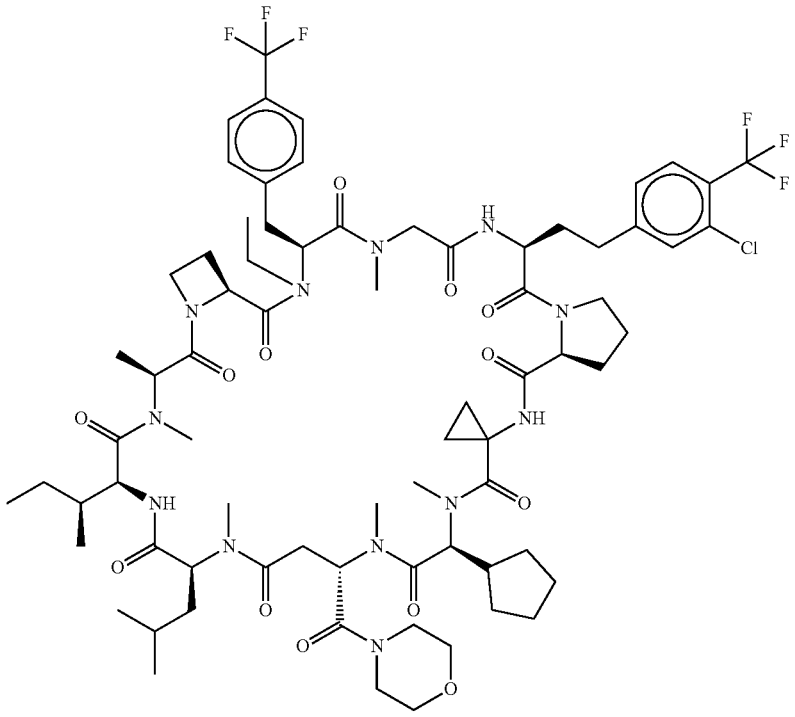 |
| PP0221 | 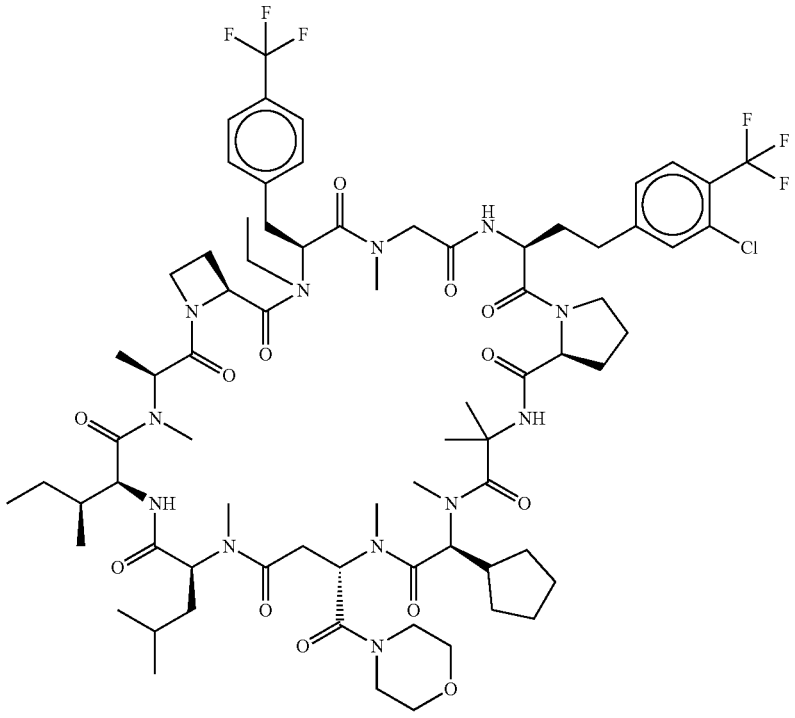 |

TABLE 38-continued
| Compound No. | Structural Formula |
|---|---|
| PP0222 | 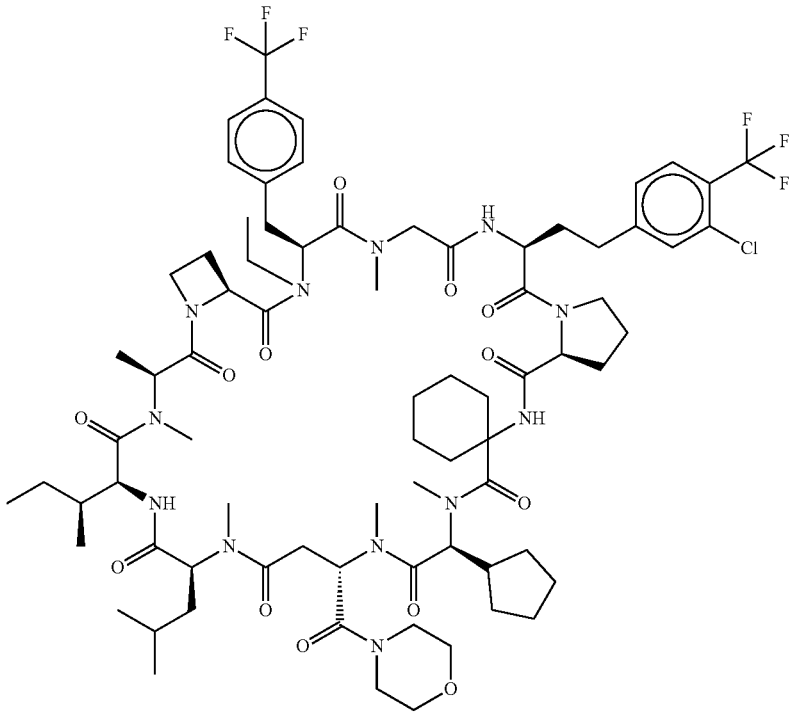 |
| PP0223 | 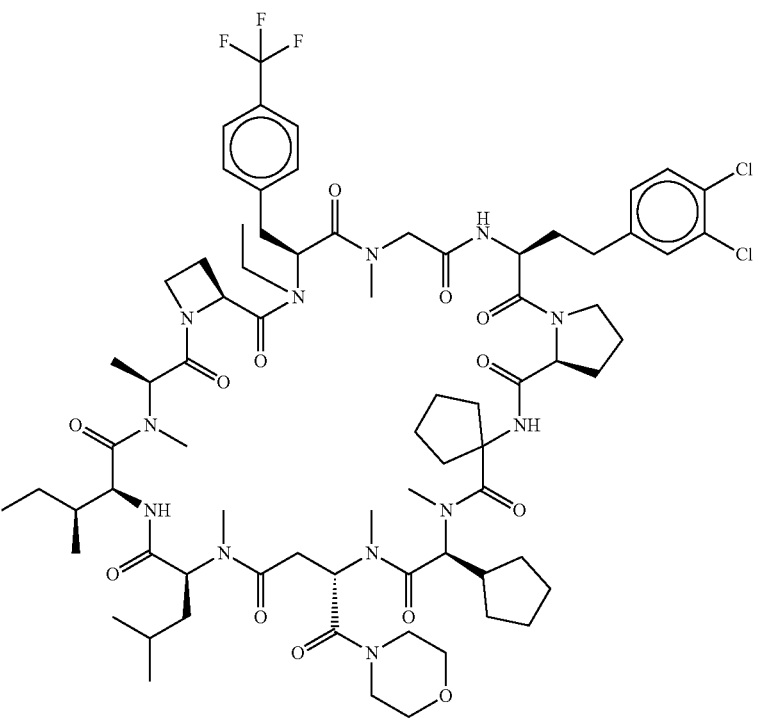 |

TABLE 38-continued

| Compound No. | Structural Formula |
| --- | --- |
| PP0224 | |
| PP0225 | |

TABLE 38-continued
| Compound No. | Structural Formula |
|---|---|
| PP0226 | 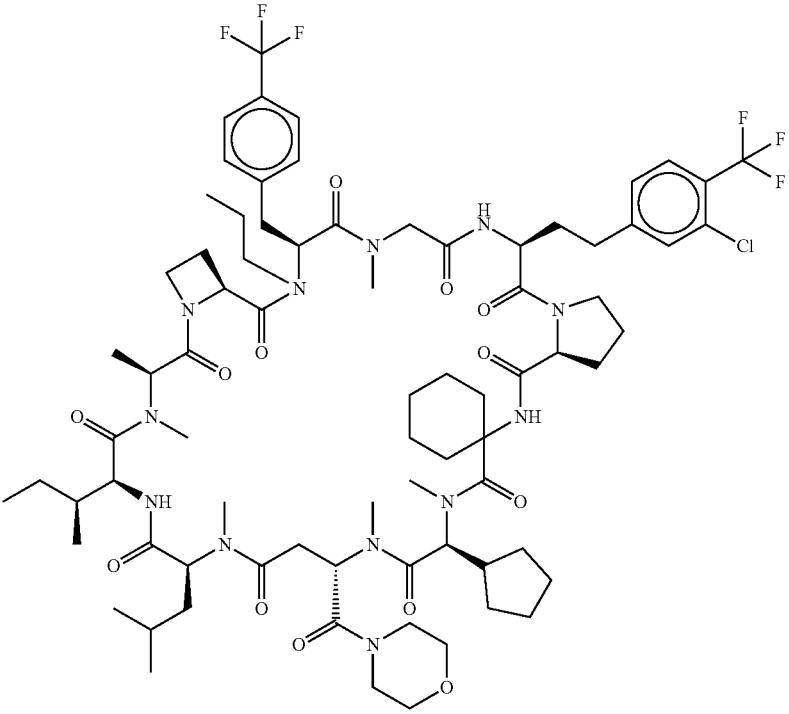 |
| PP0227 | 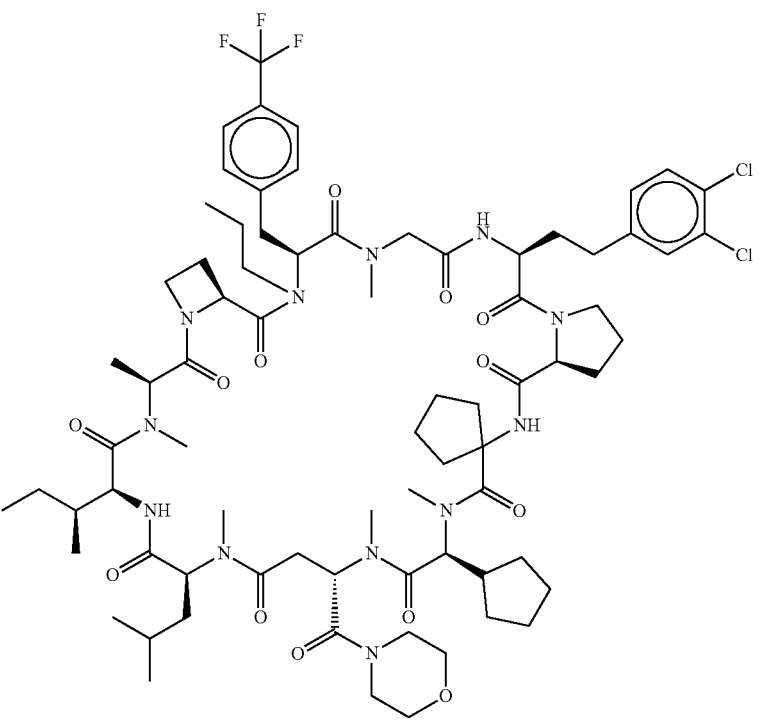 |

TABLE 38-continued
| Compound No. | Structural Formula |
|---|---|
| PP0228 | 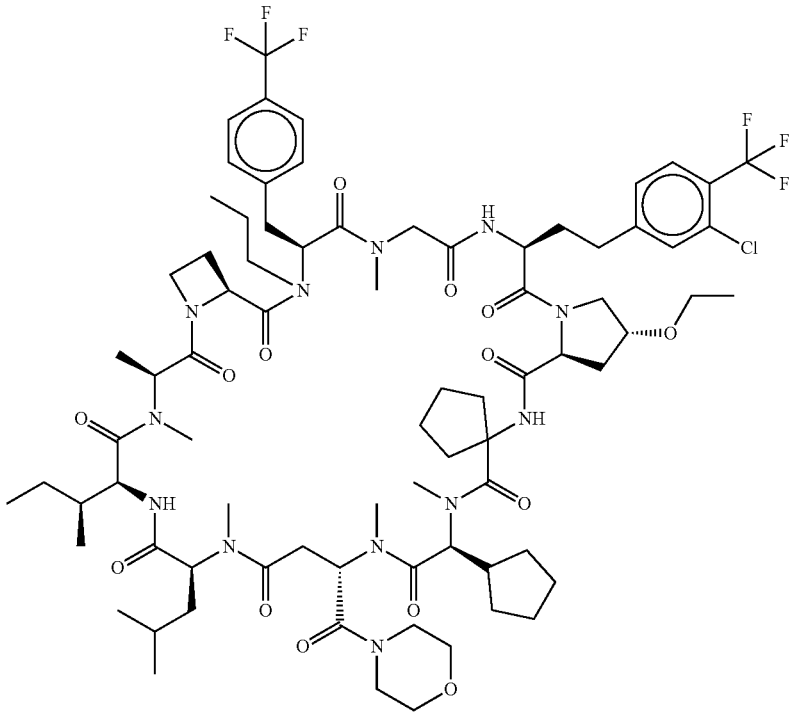 |
| PP0229 | 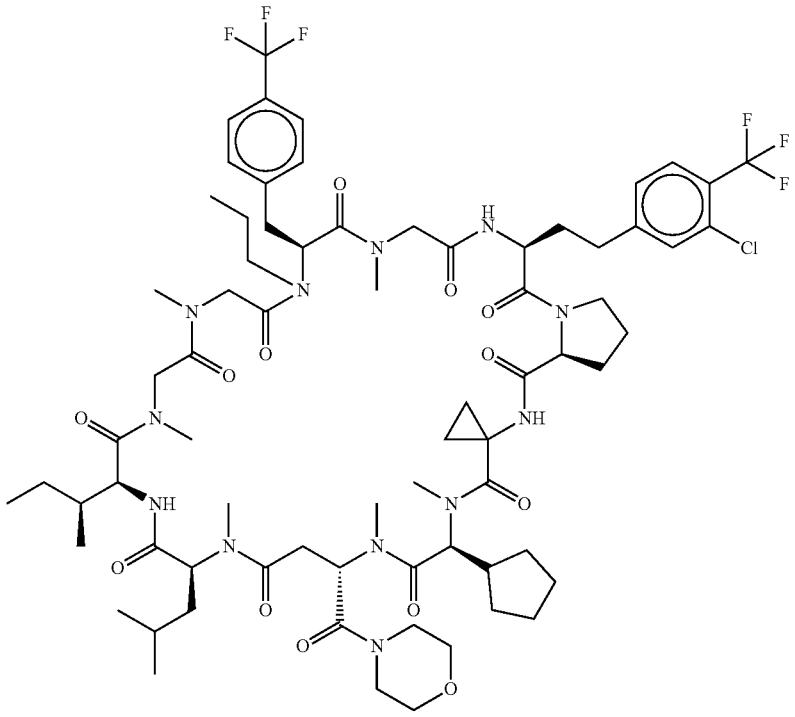 |

TABLE 38-continued
| Compound No. | Structural Formula |
|---|---|
| PP0230 | 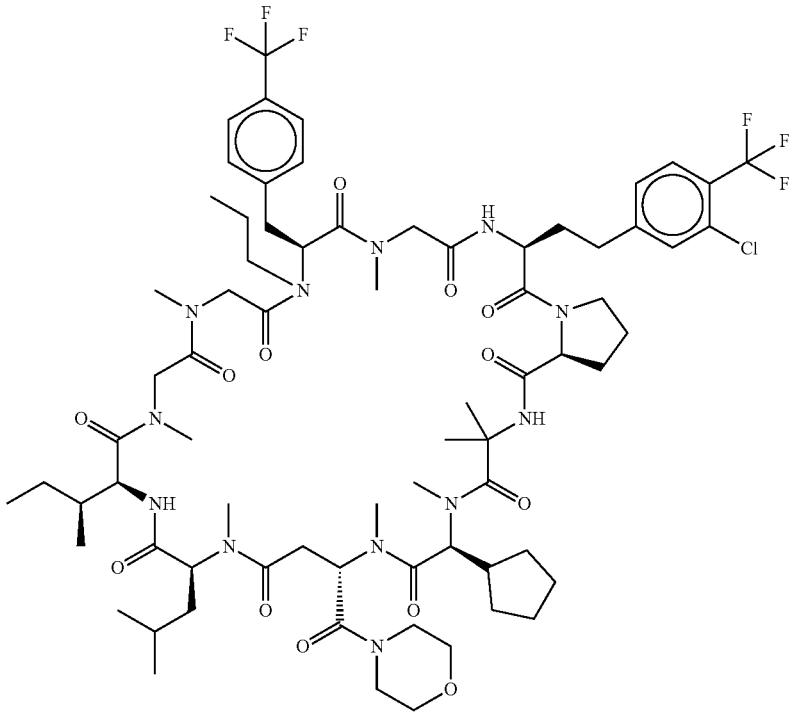 |
| PP0231 | 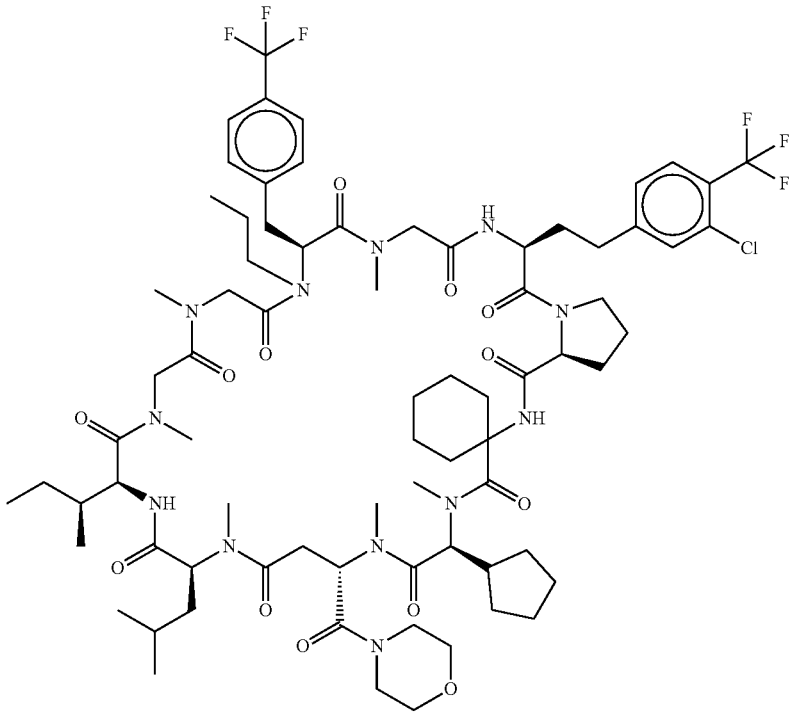 |

TABLE 38-continued
| Compound No. | Structural Formula |
|---|---|
| PP0232 | 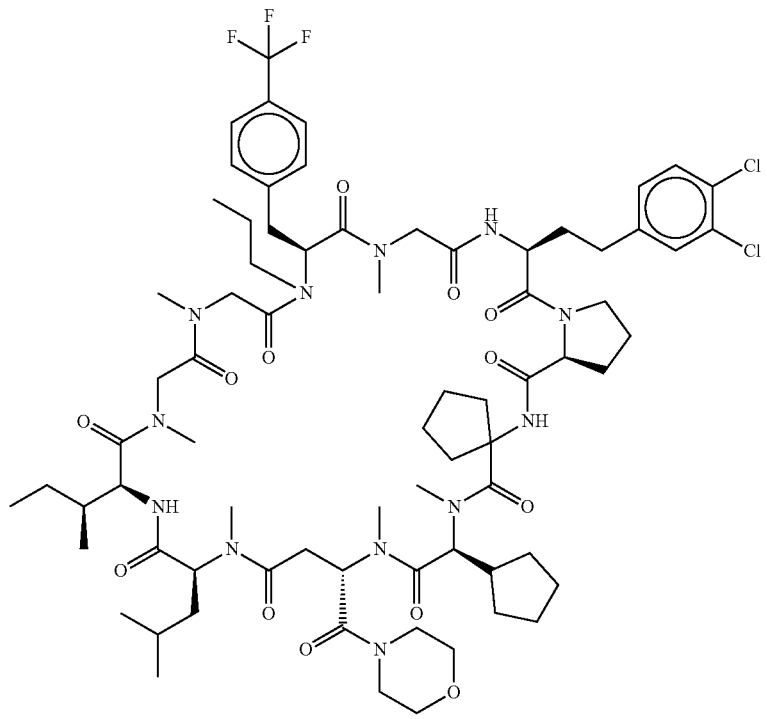 |
| PP0233 | 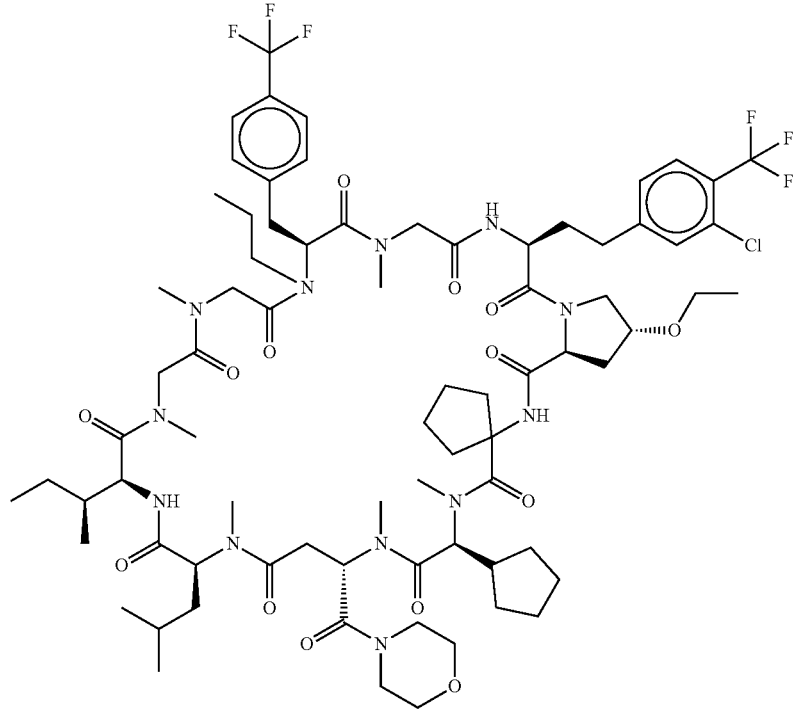 |

TABLE 38-continued
| Compound No. | Structural Formula |
|---|---|
| PP0234 | 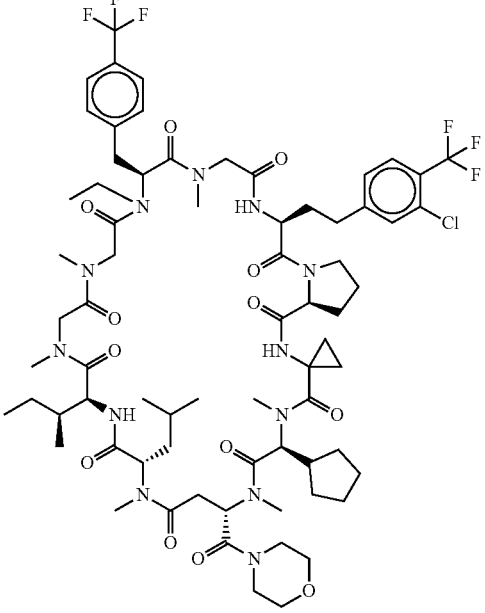 |
| PP0235 | 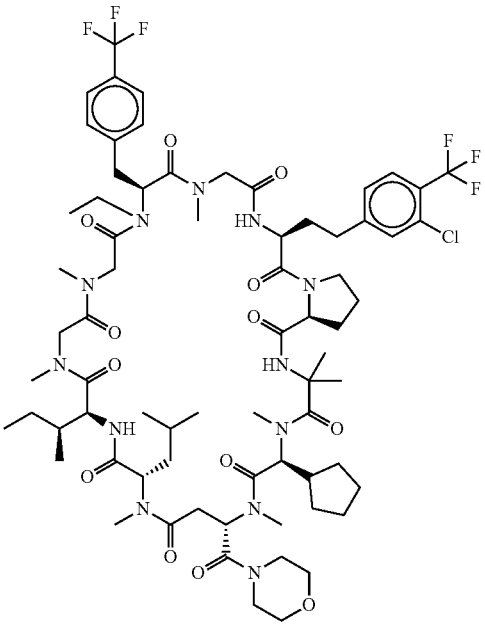 |

TABLE 38-continued

| Compound No. | Structural Formula |
|---|---|
| PP0236 | |
| PP0237 | |

TABLE 38-continued

| Compound No. | Structural Formula |
|---|---|
| PP0238 | |
| PP0239 | |

TABLE 38-continued
| Compound No. | Structural Formula |
|---|---|
| PP0240 | 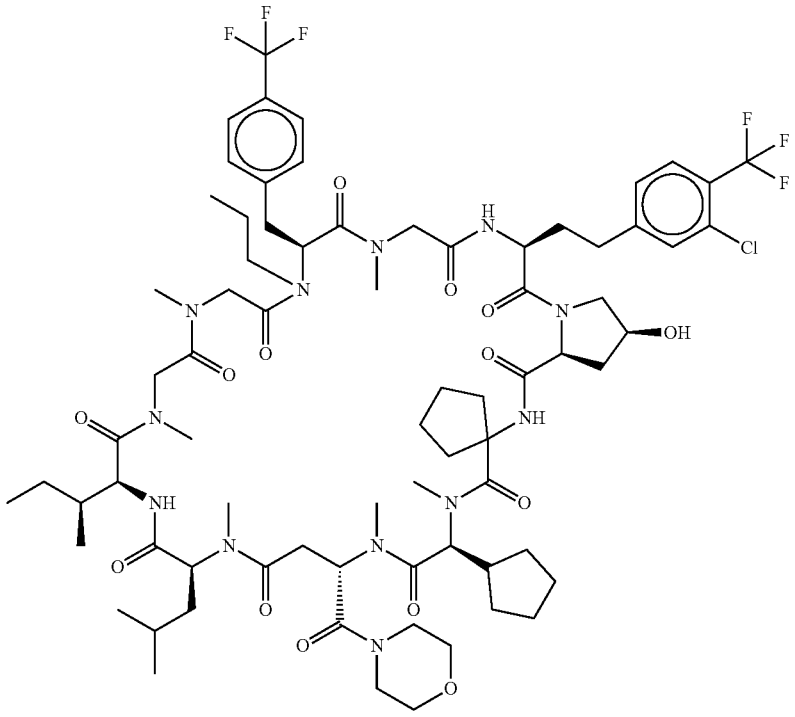 |
| PP0241 | 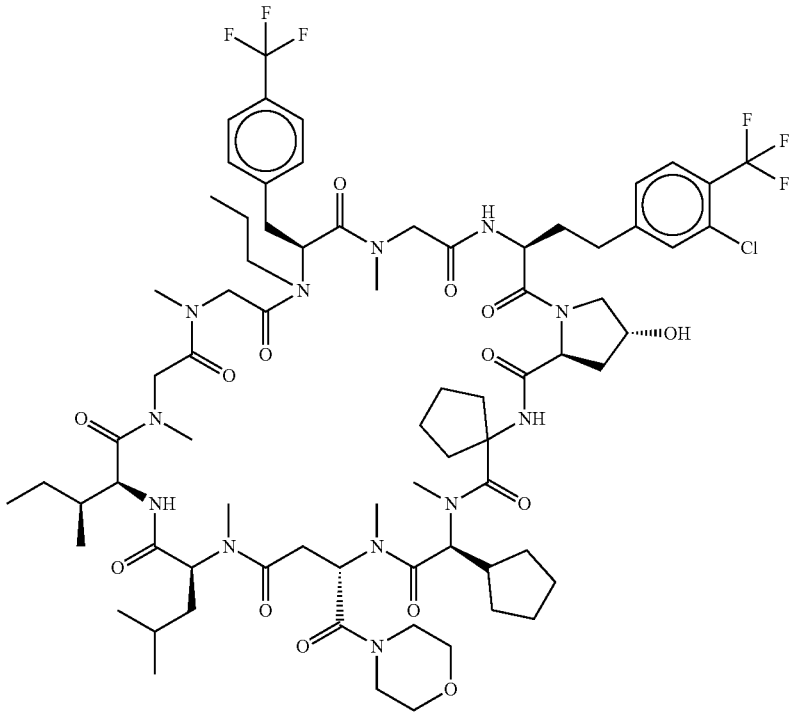 |

TABLE 38-continued

| Compound No. | Structural Formula |
|---|---|
| PP0242 | |
| PP0243 | |

TABLE 38-continued
| Compound No. | Structural Formula |
|---|---|
| PP0244 | 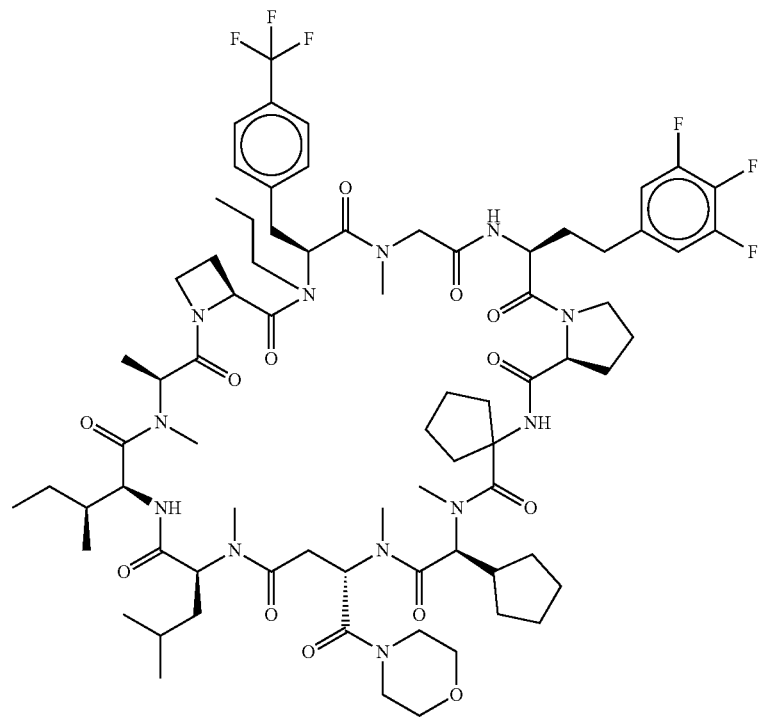 |
| PP0245 | 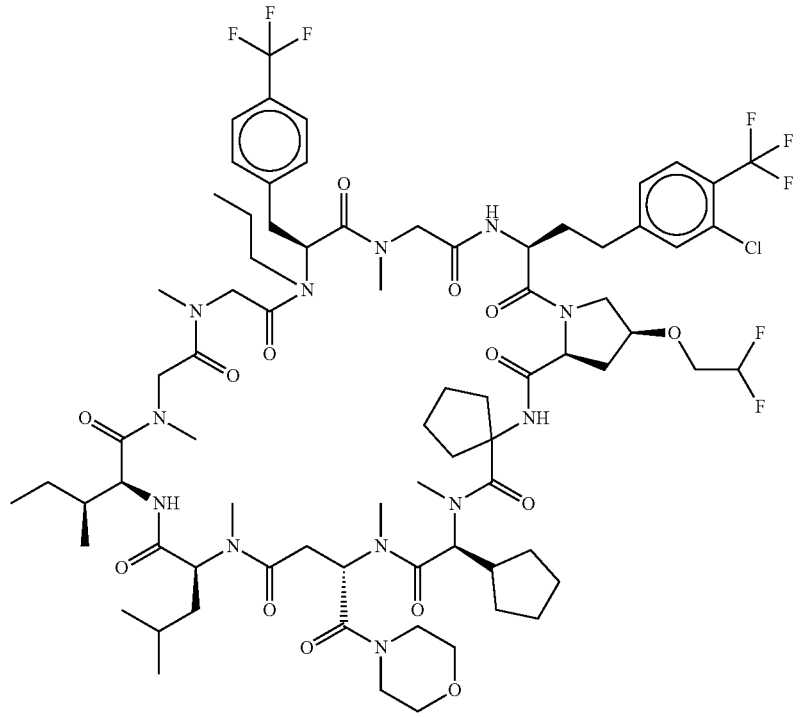 |

TABLE 38-continued
| Compound No. | Structural Formula |
|---|---|
| PP0246 | 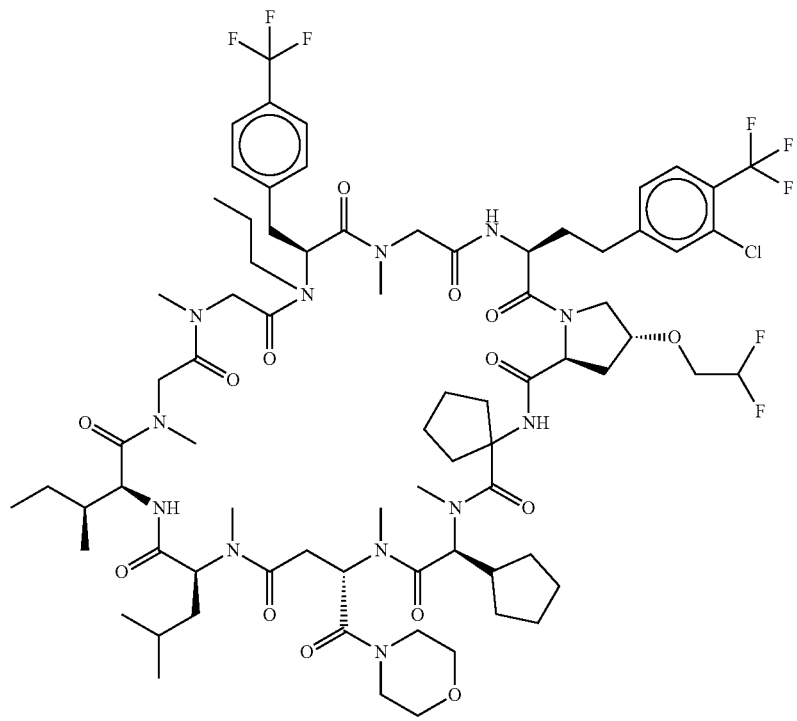 |
| PP0247 | 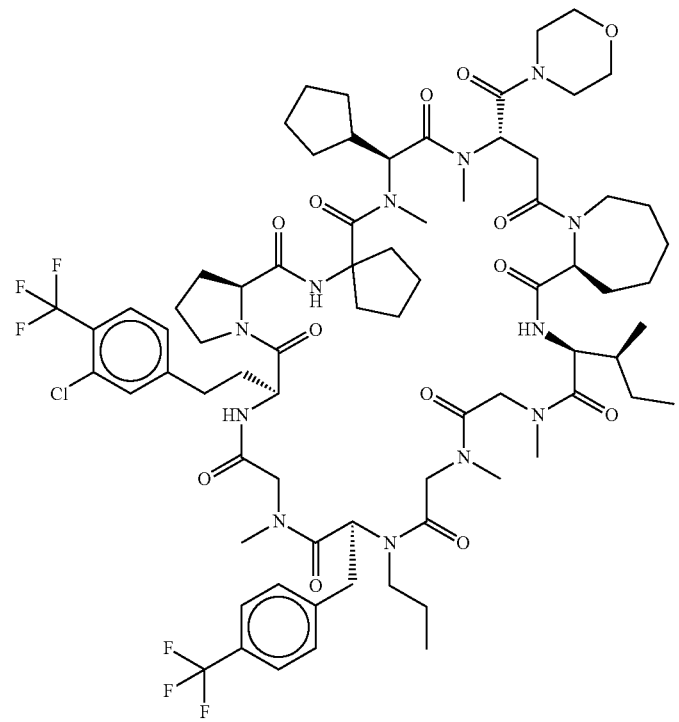 |

TABLE 38-continued
| Compound No. | Structural Formula |
| --- | --- |
| PP0248 | 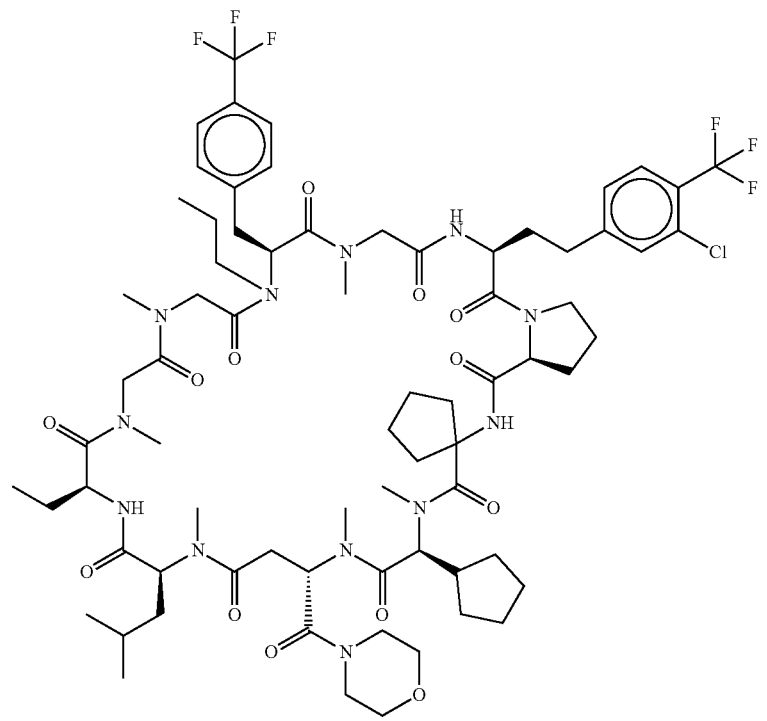 |
| PP0249 | 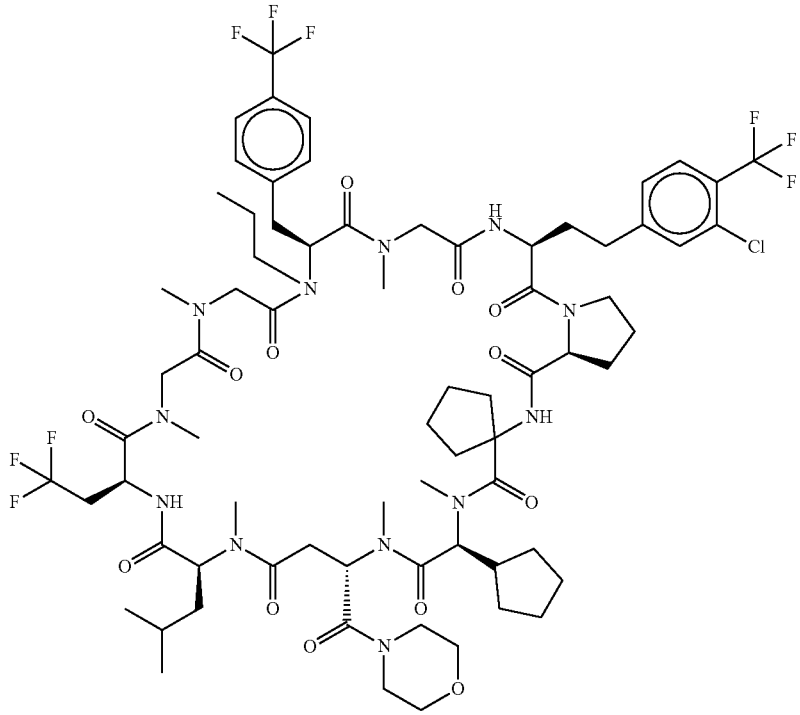 |

TABLE 38-continued
| Compound No. | Structural Formula |
|---|---|
| PP0250 | 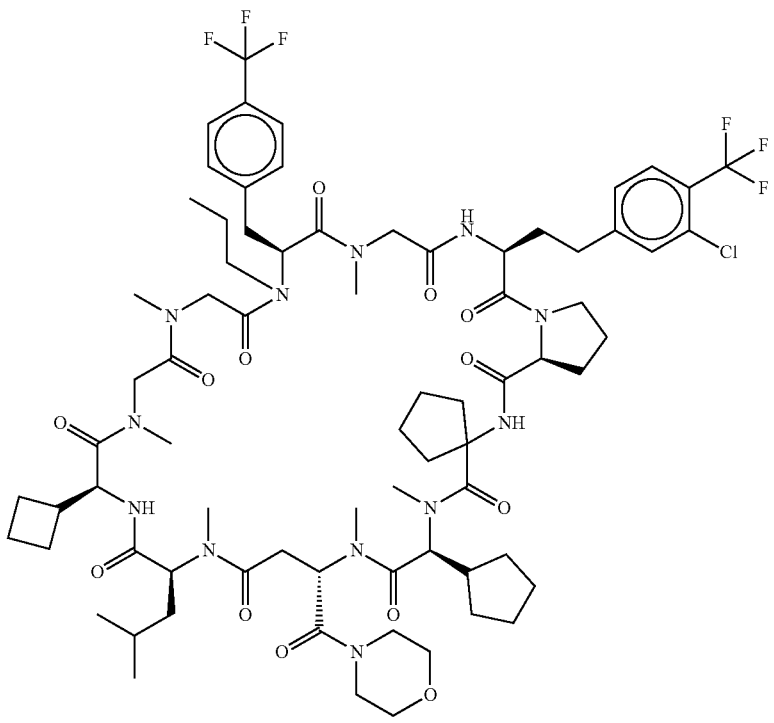 |
| PP0251 | 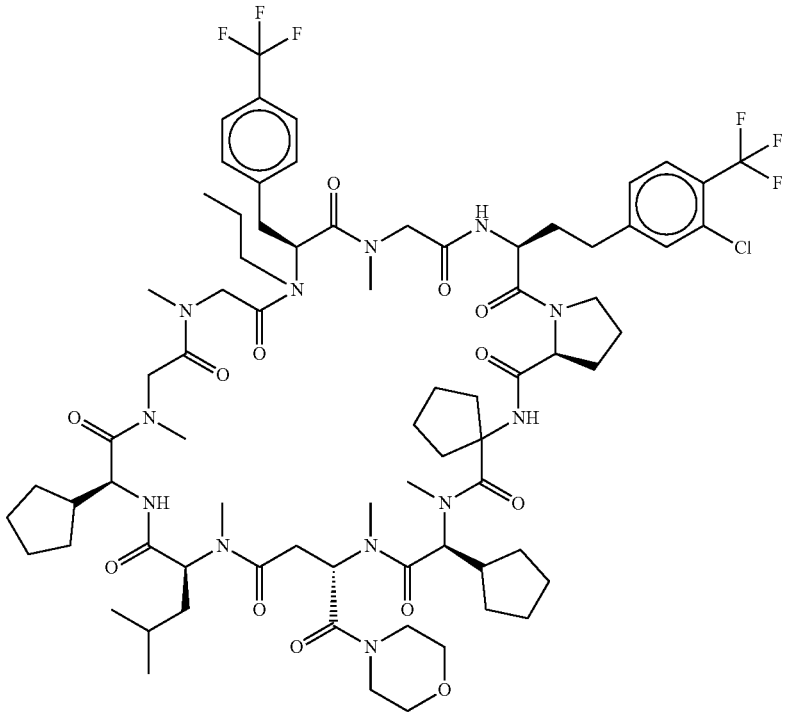 |

TABLE 38-continued
| Compound No. | Structural Formula |
|---|---|
| PP0252 | 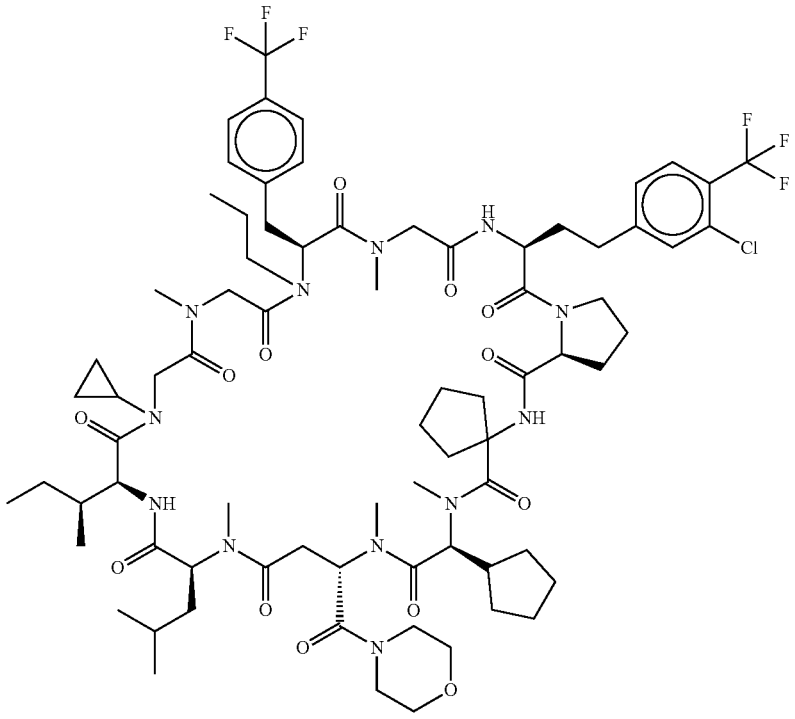 |
| PP0253 | 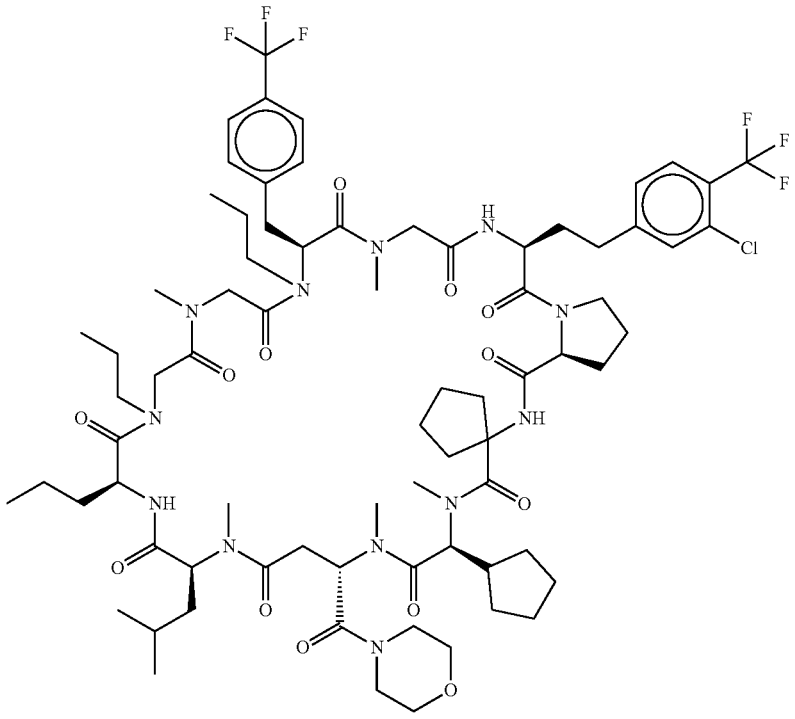 |

TABLE 38-continued
| Compound No. | Structural Formula |
|---|---|
| PP0254 | 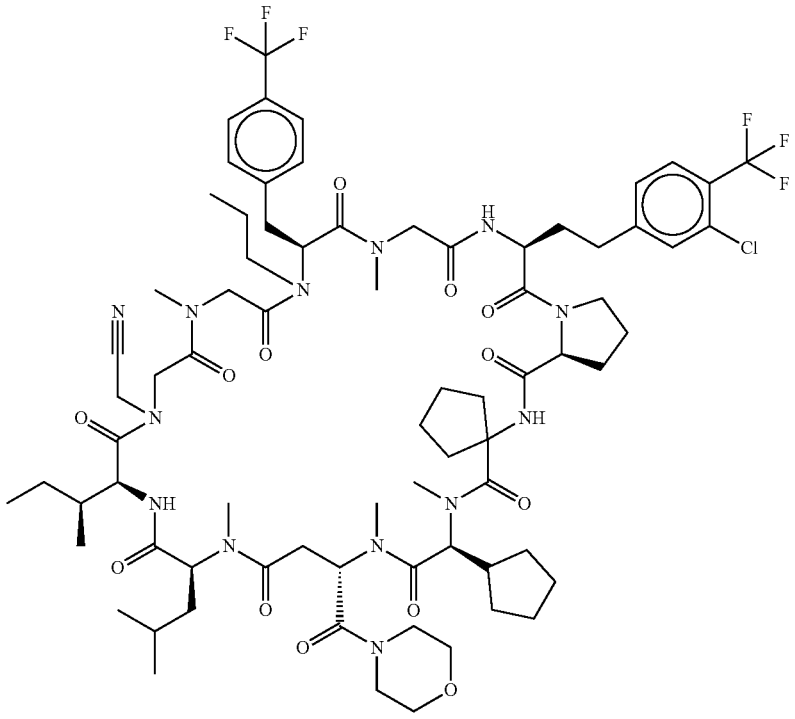 |
| PP0256 | 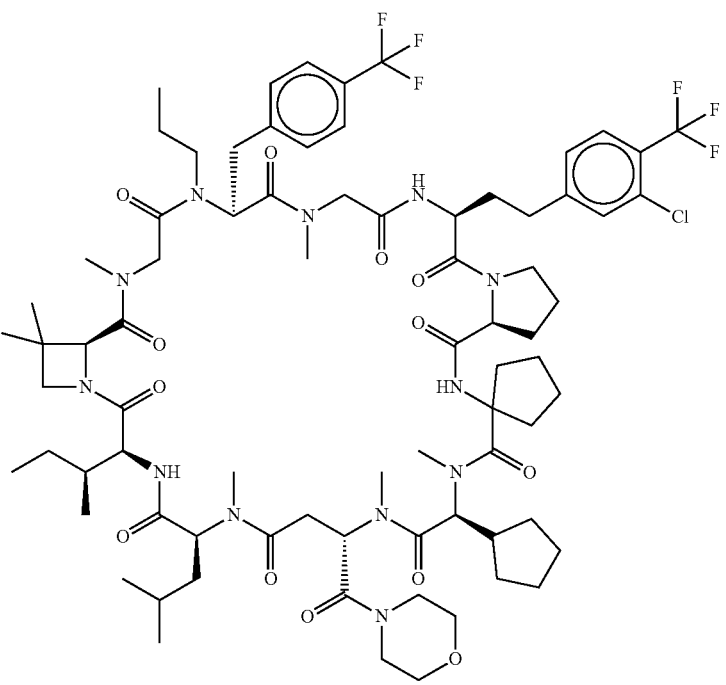 |

TABLE 38-continued

| Compound No. | Structural Formula |
|---|---|
| PP0257 | |
| PP0258 | |

TABLE 38-continued
| Compound No. | Structural Formula |
|---|---|
| PP0259 | 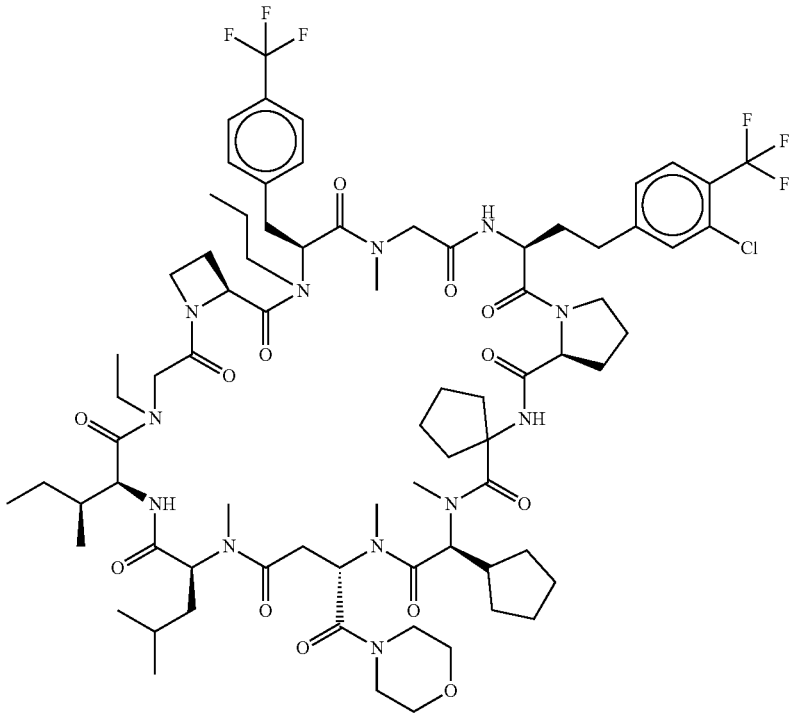 |
| PP0260 | 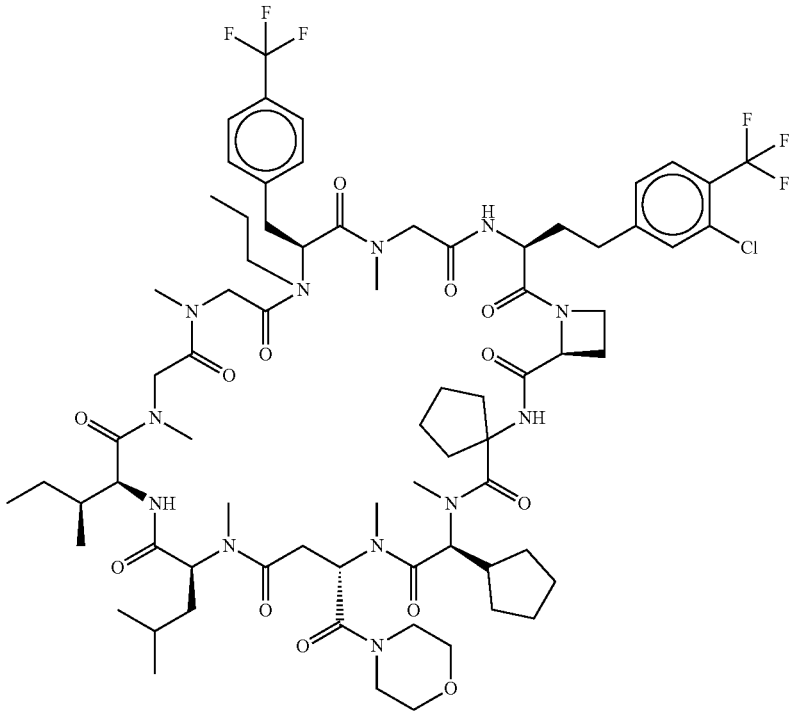 |

TABLE 38-continued
| Compound No. | Structural Formula |
|---|---|
| PP0261 | 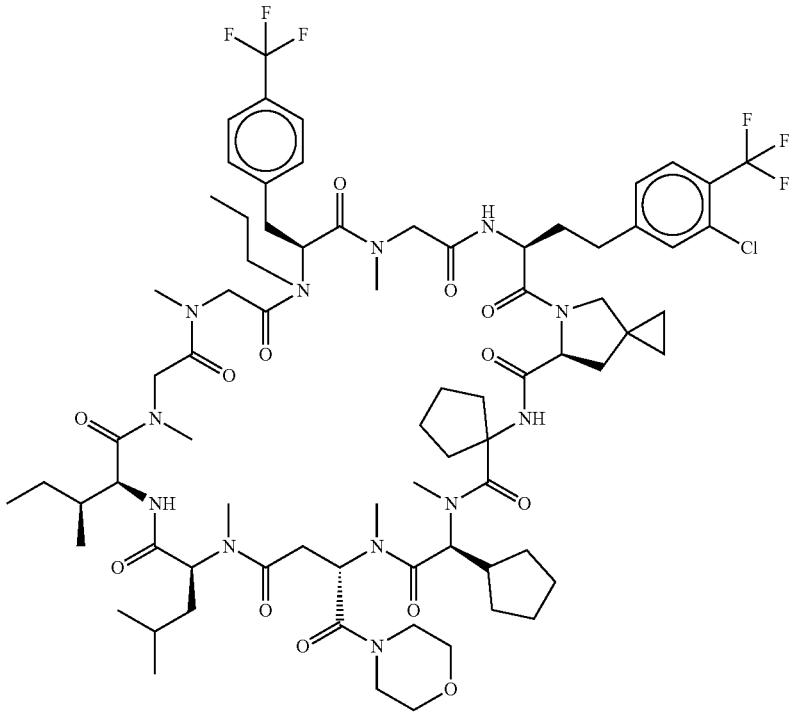 |
| PP0262 | 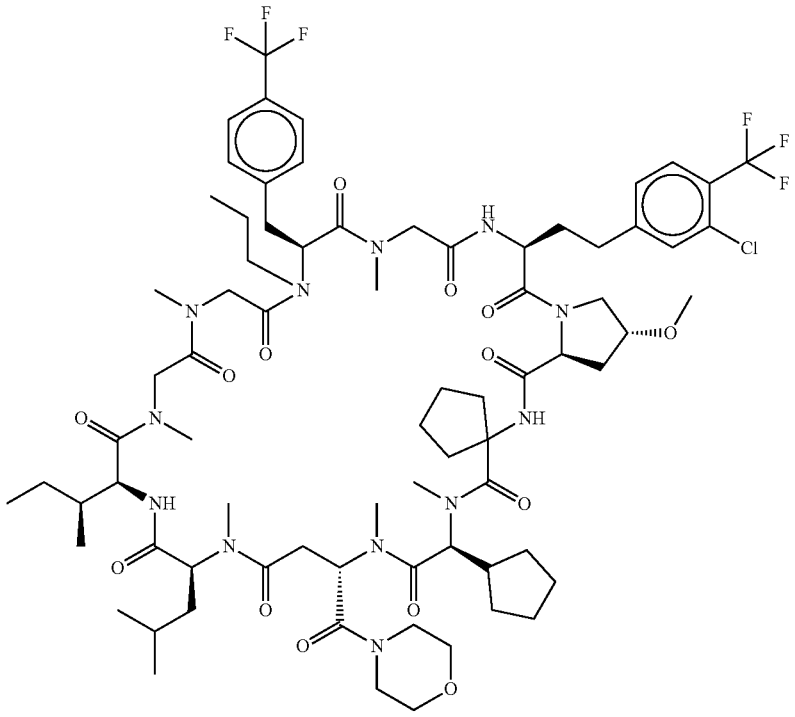 |

TABLE 38-continued
| Compound No. | Structural Formula |
|---|---|
| PP0263 | 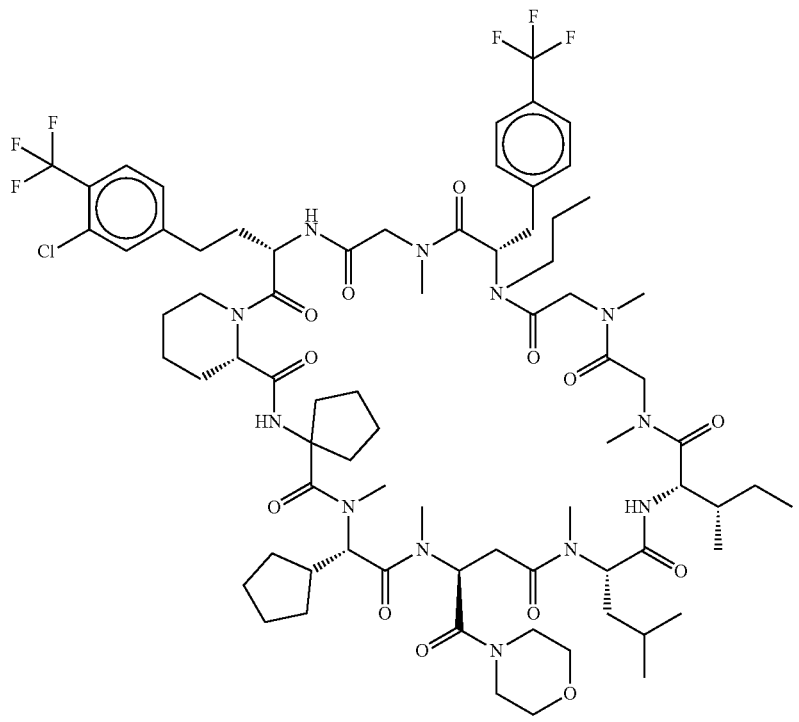 |
| PP0264 | 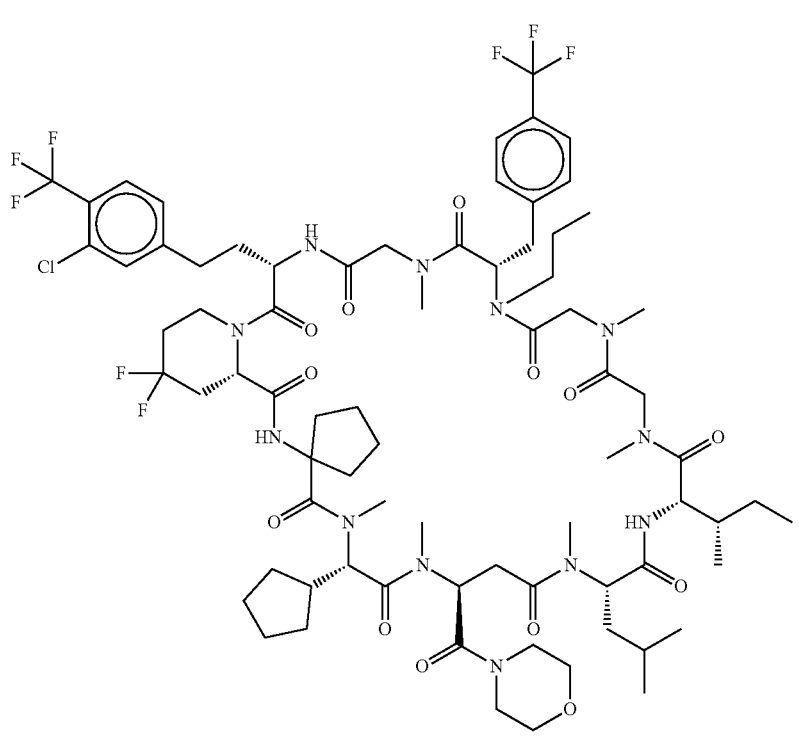 |

TABLE 38-continued

| Compound No. | Structural Formula |
|---|---|
| PP0265 | |
| PP0266 | |

TABLE 38-continued
| Compound No. | Structural Formula |
|---|---|
| PP0267 | 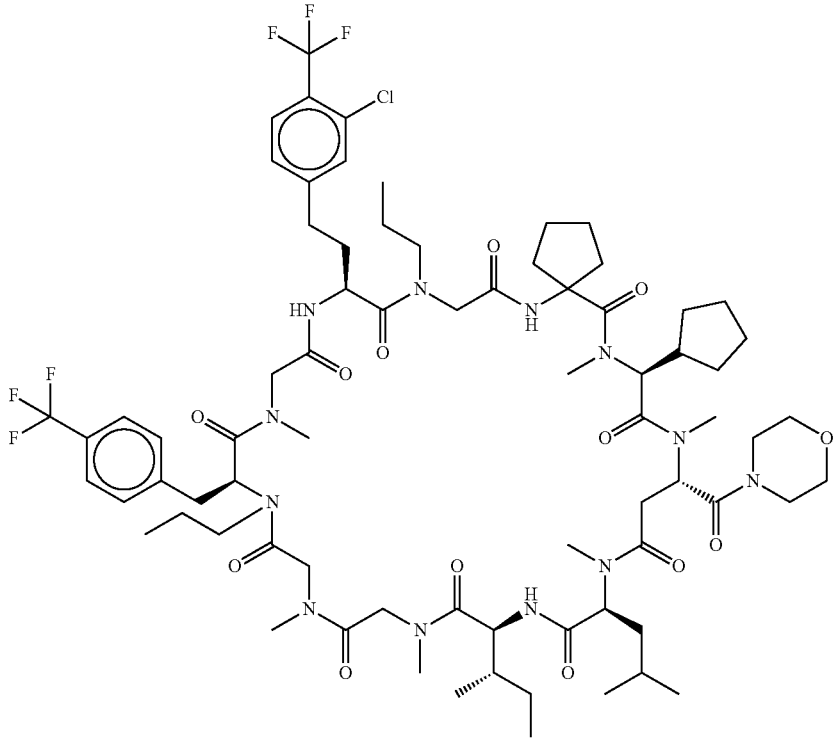 |
| PP0268 | 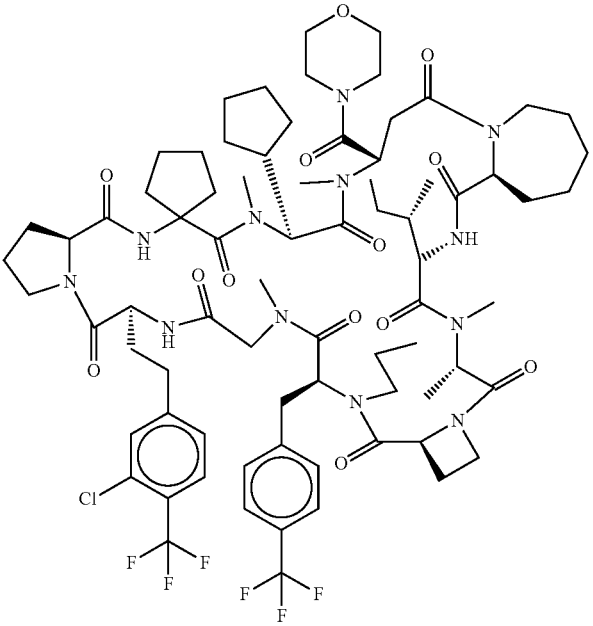 |

TABLE 38-continued
| Compound No. | Structural Formula |
| --- | --- |
| PP0269 | 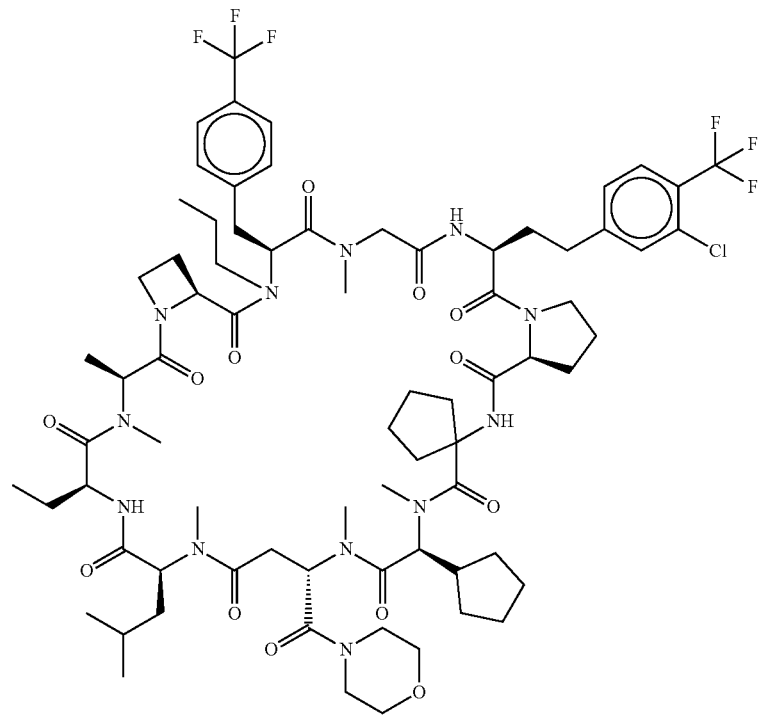 |
| PP0270 | 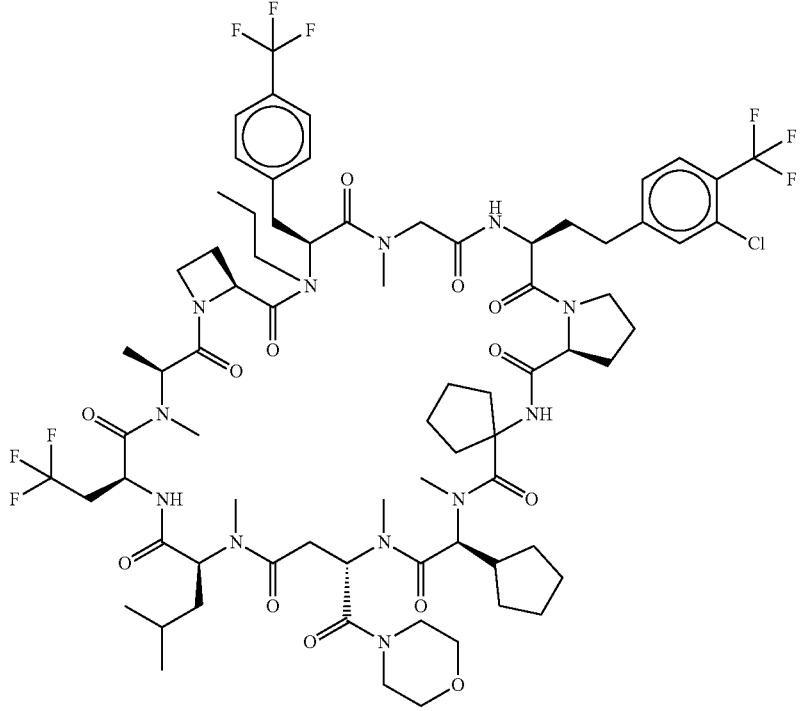 |

TABLE 38-continued
| Compound No. | Structural Formula |
|---|---|
| PP0271 | 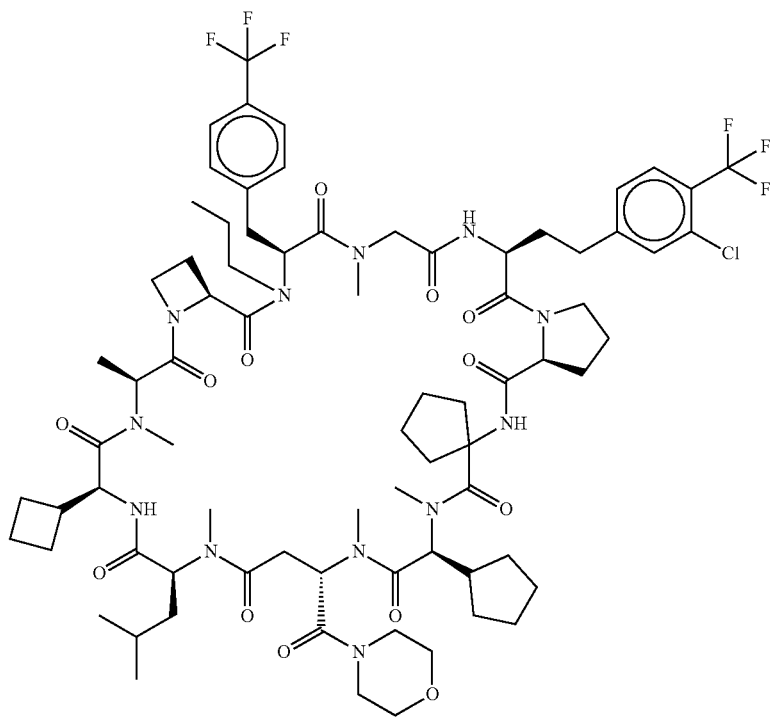 |
| PP0272 | 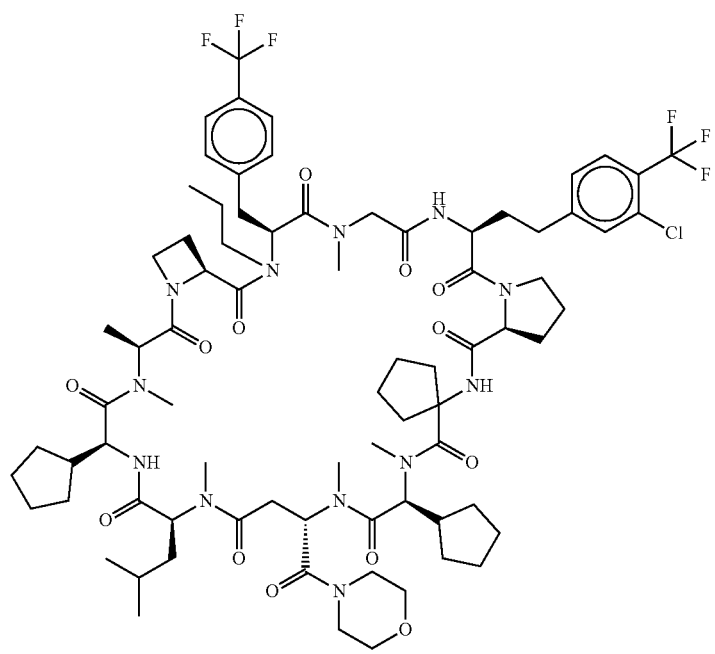 |

TABLE 38-continued
| Compound No. | Structural Formula |
|---|---|
| PP0273 | 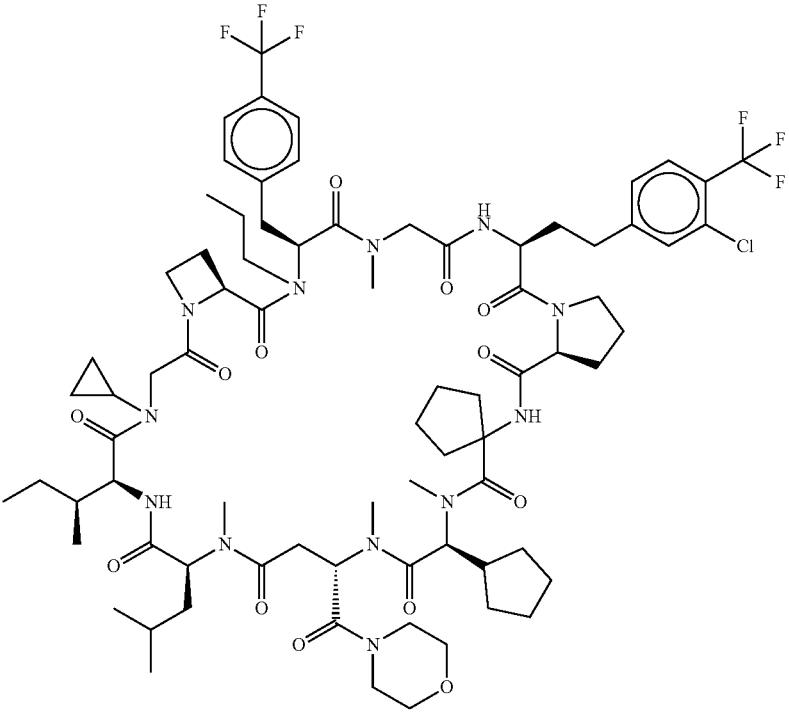 |
| PP0274 | 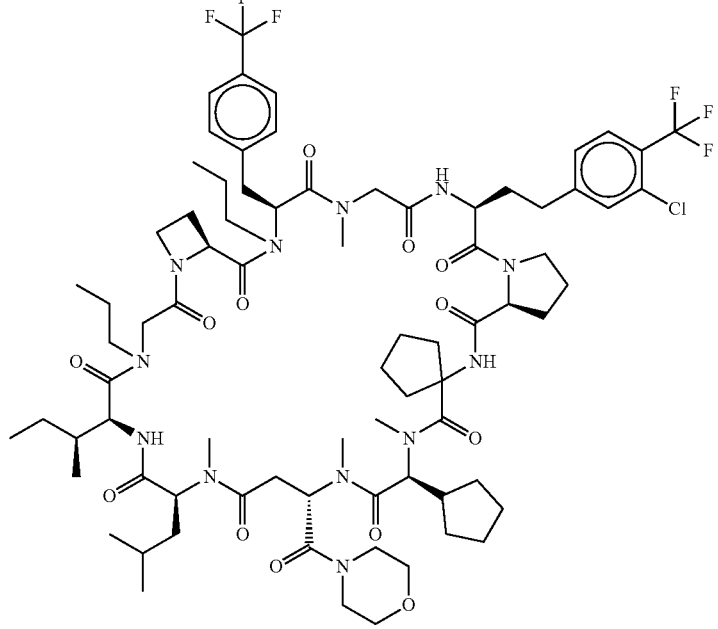 |

TABLE 38-continued
| Compound No. | Structural Formula |
|---|---|
| PP0275 | 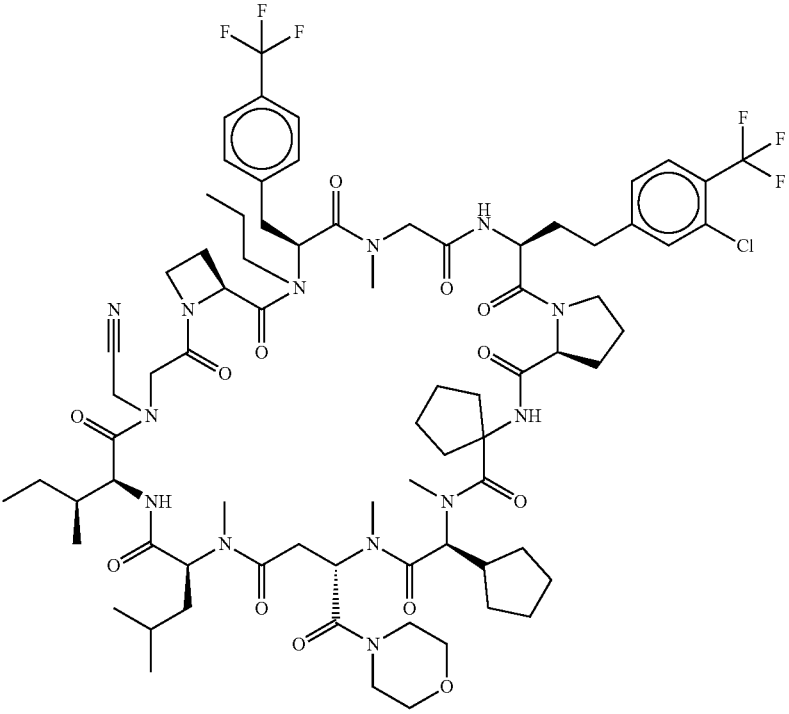 |
| PP0276 | 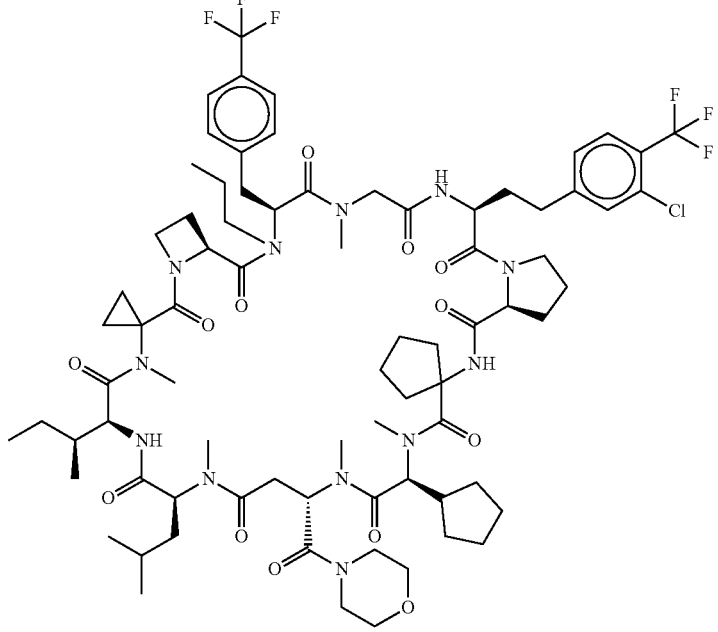 |

TABLE 38-continued

| Compound No. | Structural Formula |
| --- | --- |
| PP0277 | |
| PP0278 | |

TABLE 38-continued
| Compound No. | Structural Formula |
|---|---|
| PP0279 | 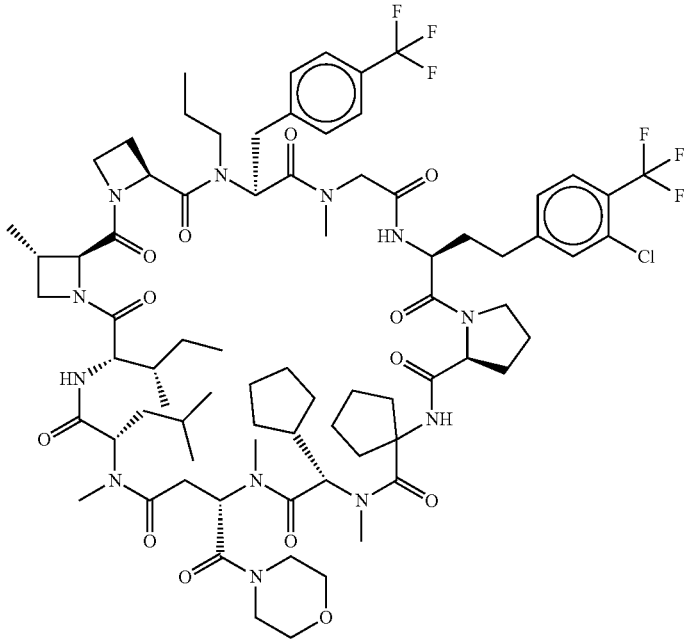 |
| PP0281 | 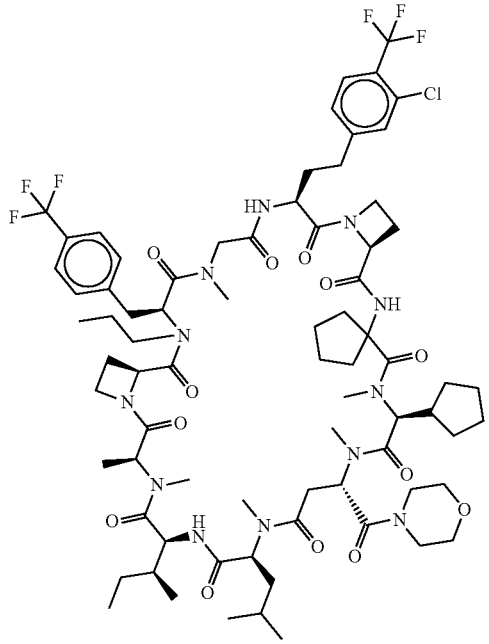 |

TABLE 38-continued
| Compound No. | Structural Formula |
|---|---|
| PP0282 | 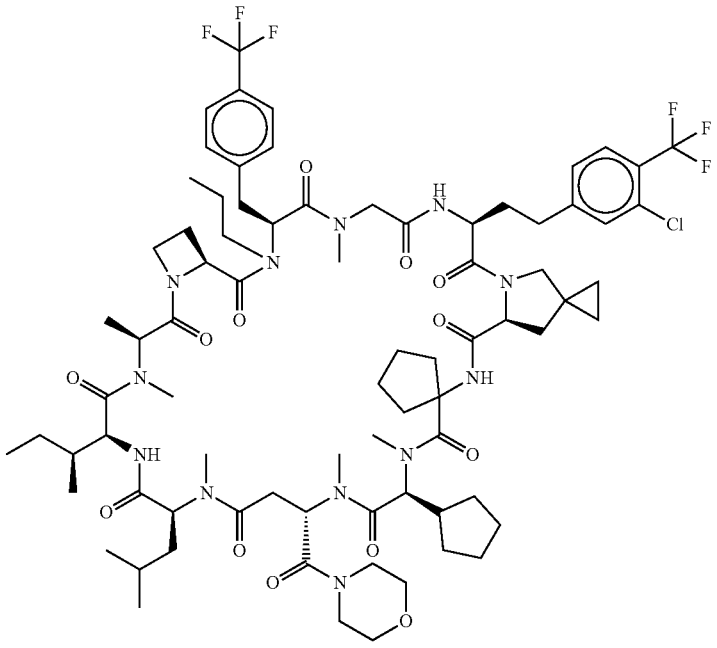 |
| PP0283 | 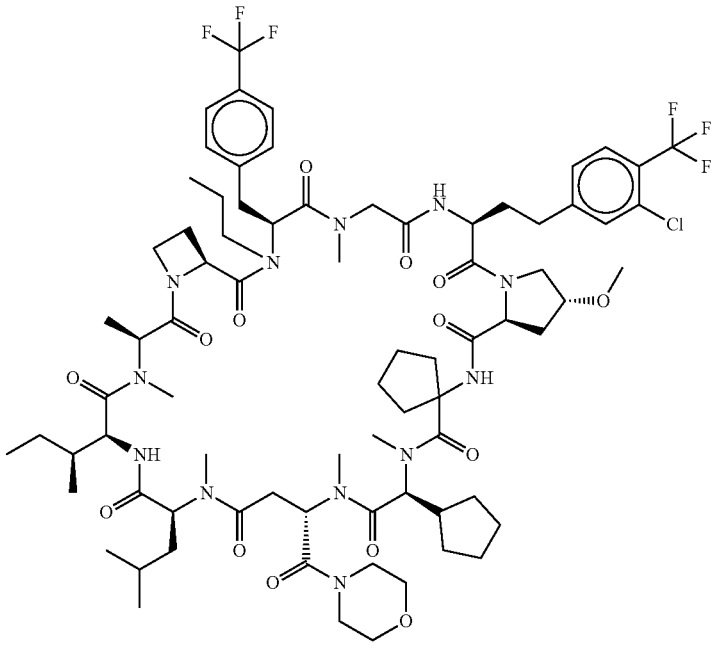 |

TABLE 38-continued

| Compound No. | Structural Formula |
| --- | --- |
| PP0284 | |
| PP0285 | |

TABLE 38-continued

| Compound No. | Structural Formula |
|---|---|
| PP0286 | |
| PP0287 | |

TABLE 38-continued
| Compound No. | Structural Formula |
|---|---|
| PP0288 | 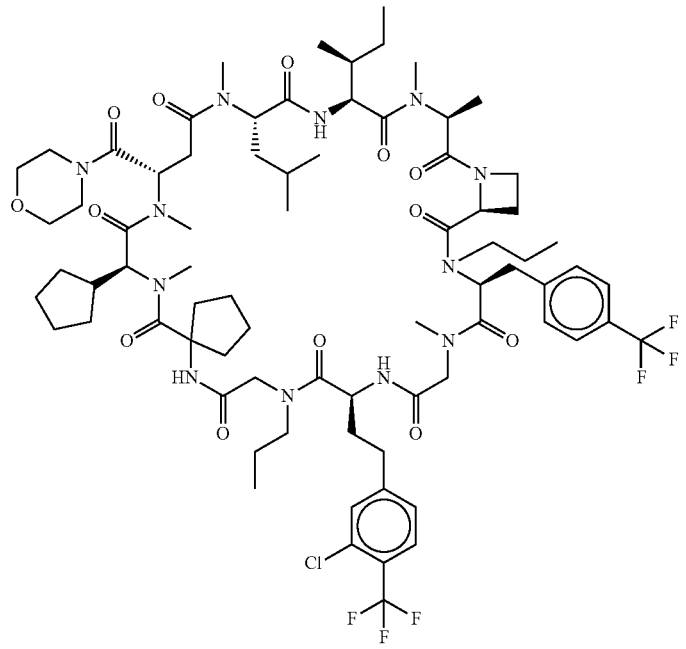 |
| PP0289 | 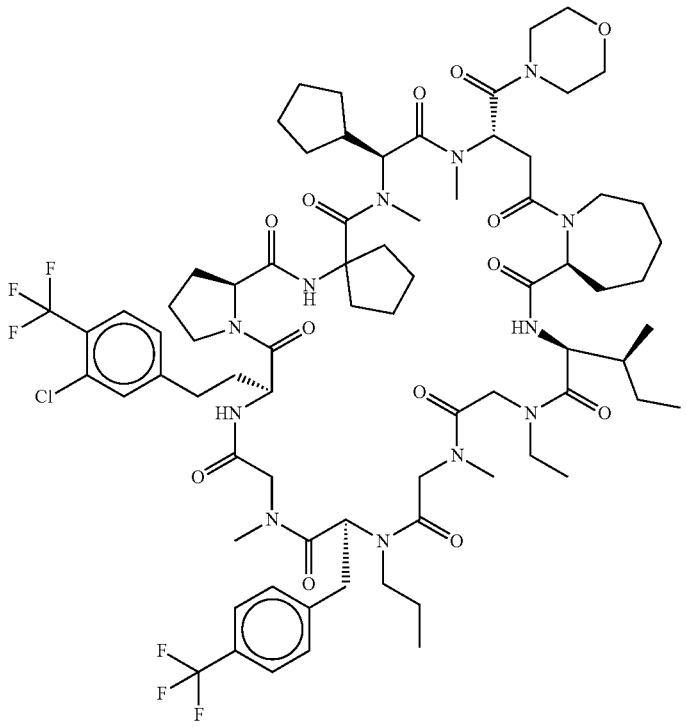 |

TABLE 38-continued

| Compound No. | Structural Formula |
| --- | --- |
| PP0290 | |
| PP0291 | |

| Compound No. | Structural Formula |
|---|---|
| PP0292 | |
| PP0293 | |

TABLE 38-continued
| Compound No. | Structural Formula |
|---|---|
| PP0294 | 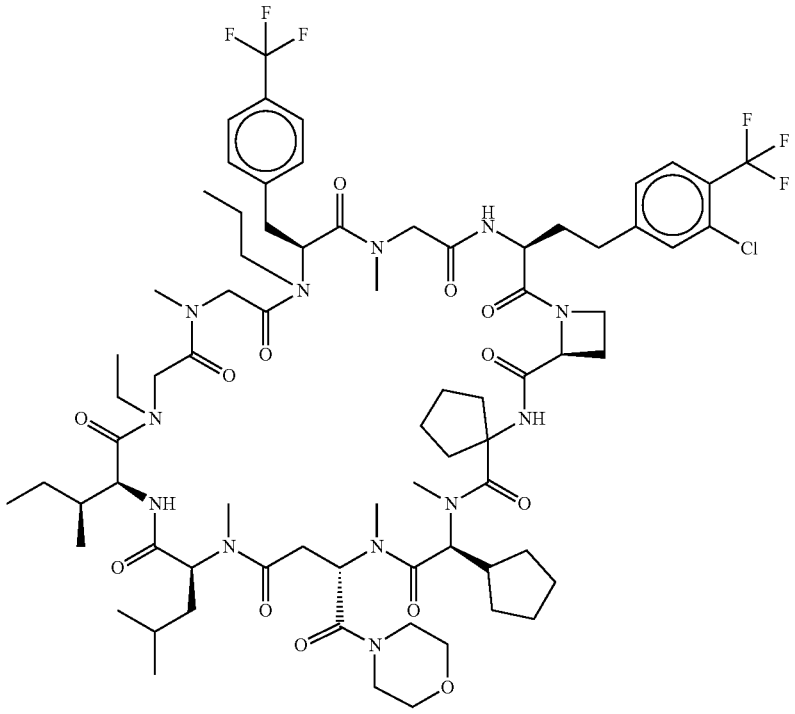 |
| PP0295 | 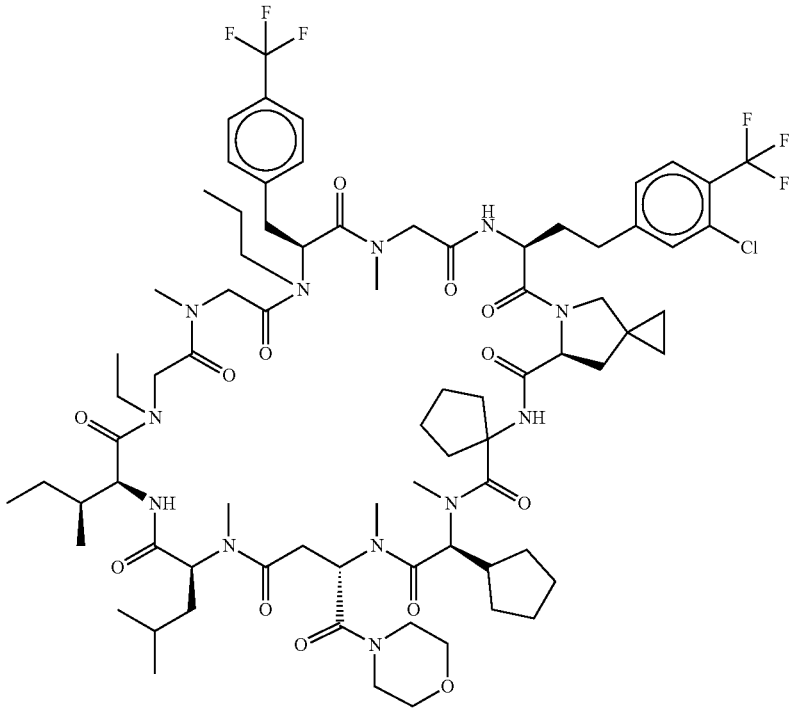 |

TABLE 38-continued
| Compound No. | Structural Formula |
|---|---|
| PP0296 | 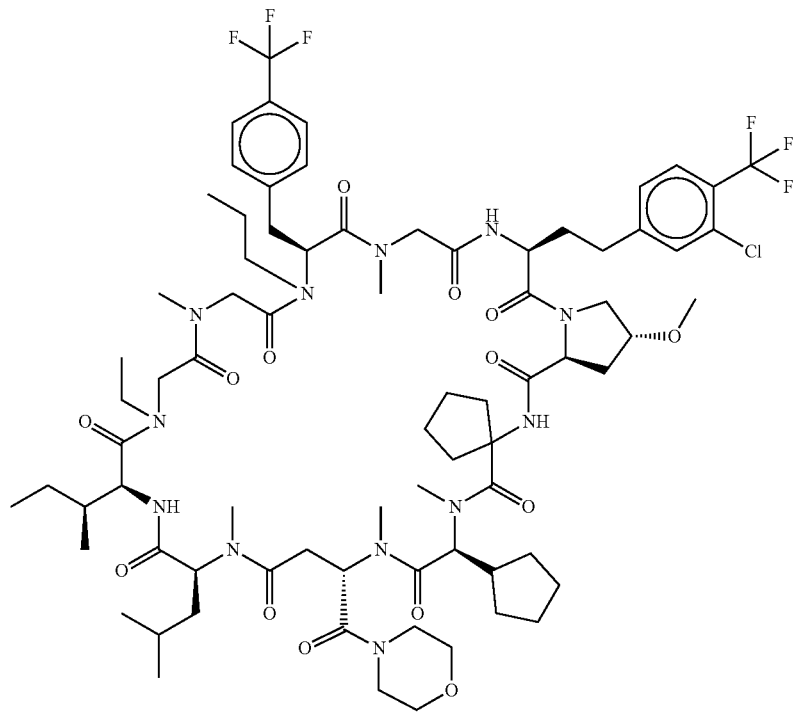 |
| PP0297 | 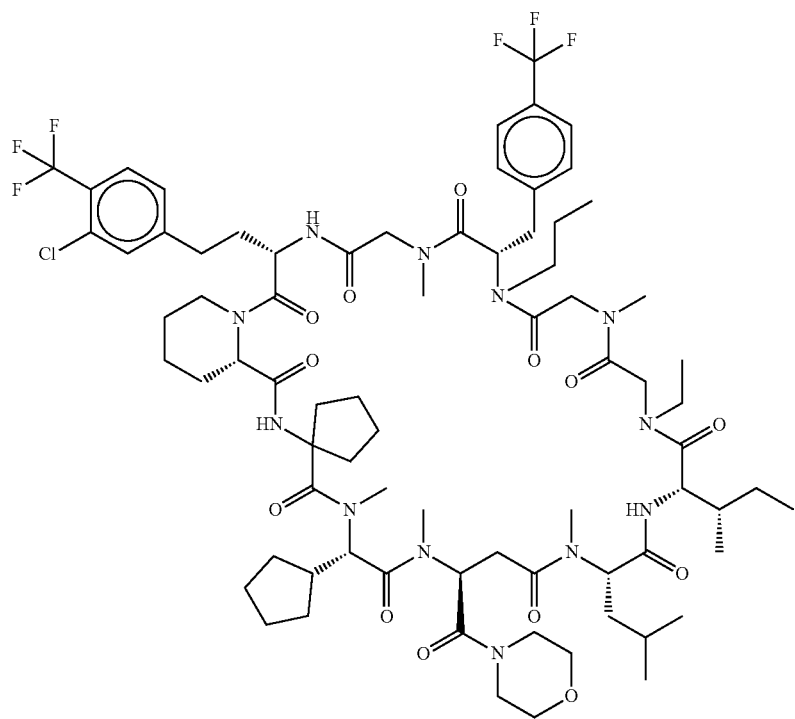 |

TABLE 38-continued
| Compound No. | Structural Formula |
|---|---|
| PP0298 | 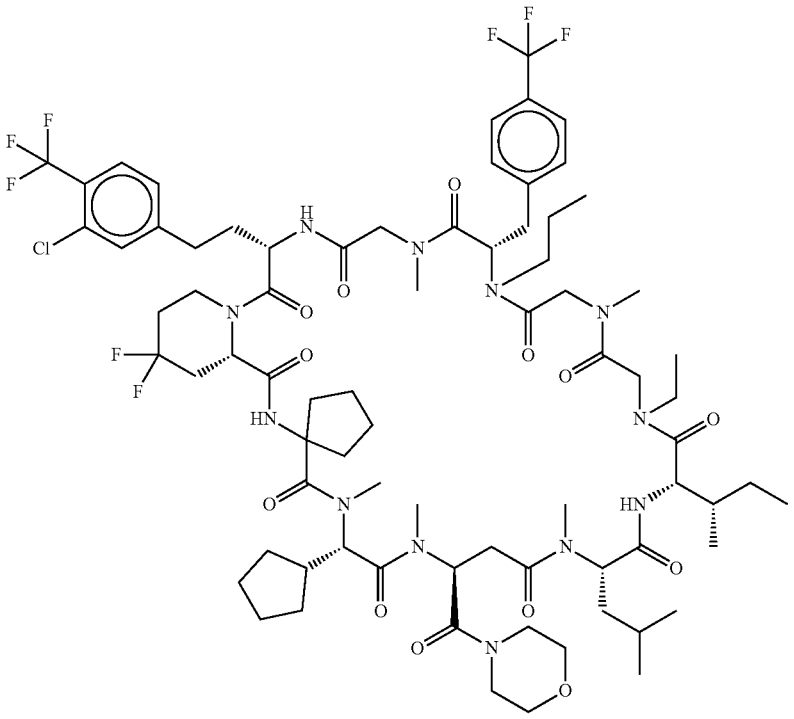 |
| PP0299 | 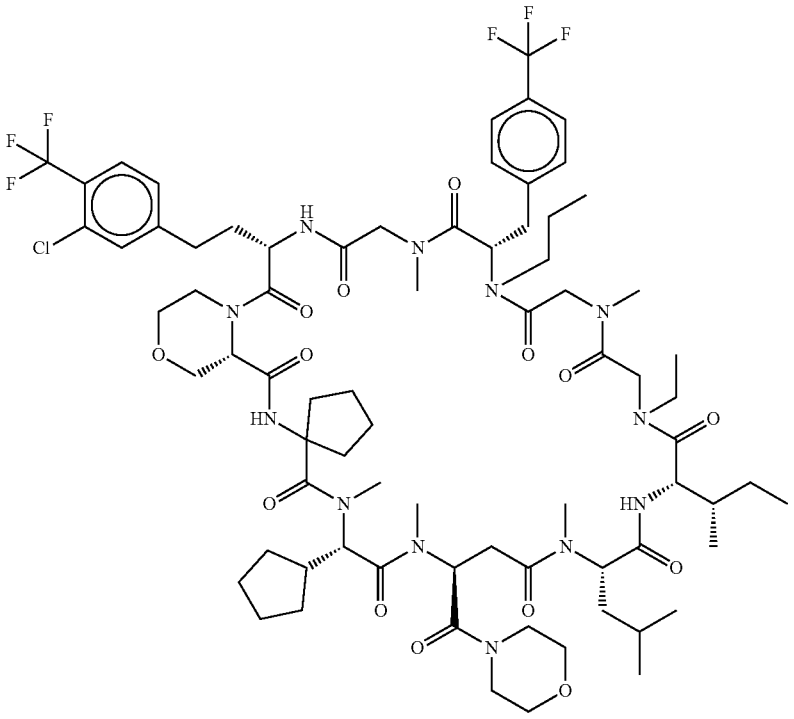 |

TABLE 38-continued
| Compound No. | Structural Formula |
|---|---|
| PP0300 | 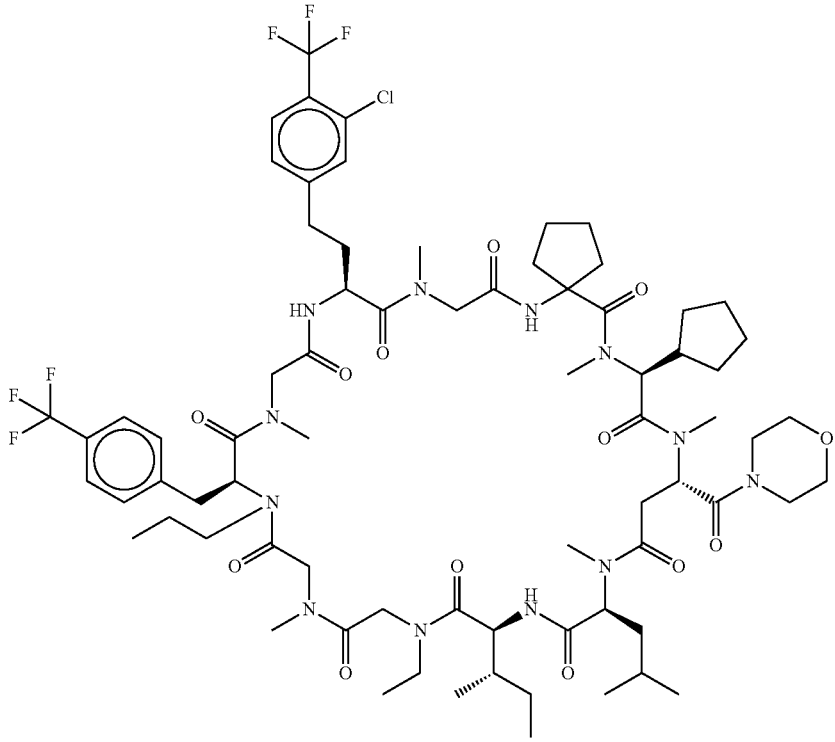 |
| PP0301 | 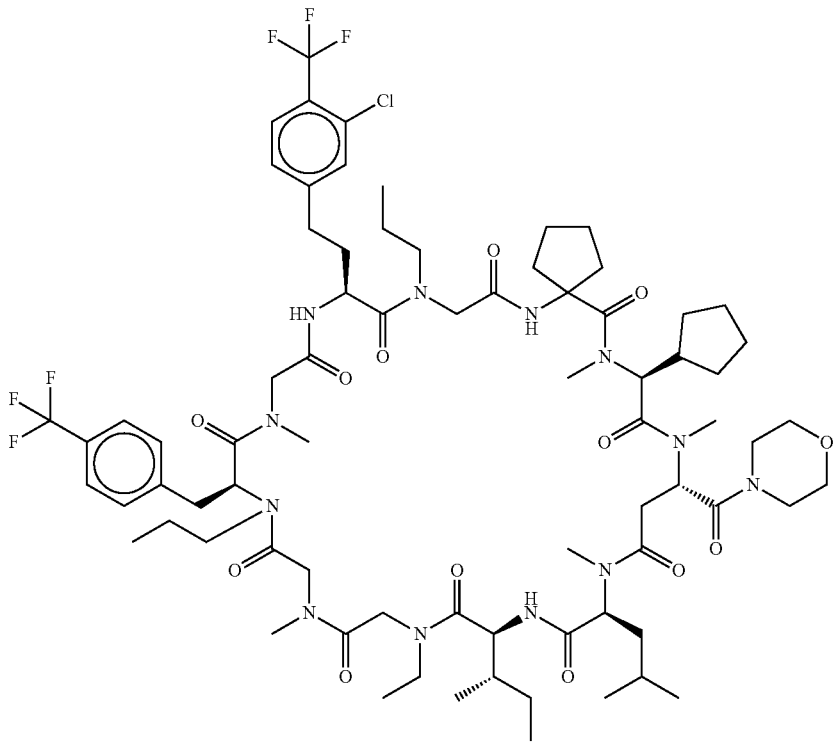 |

TABLE 38-continued
| Compound No. | Structural Formula |
|---|---|
| PP0302 | 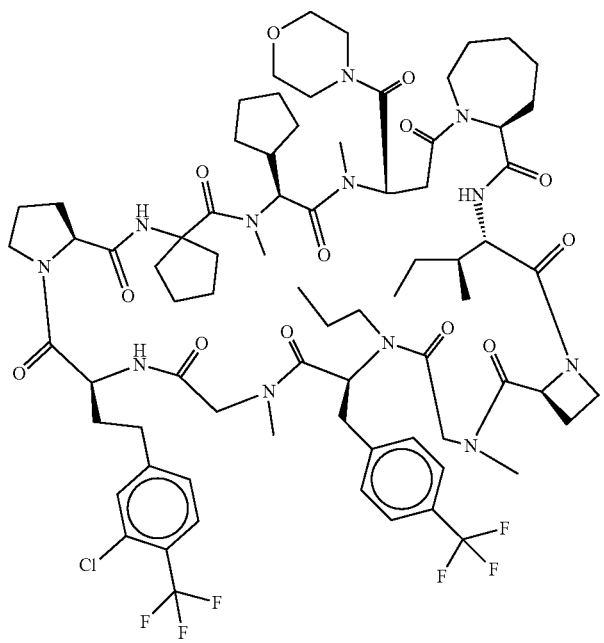 |
| PP0303 | 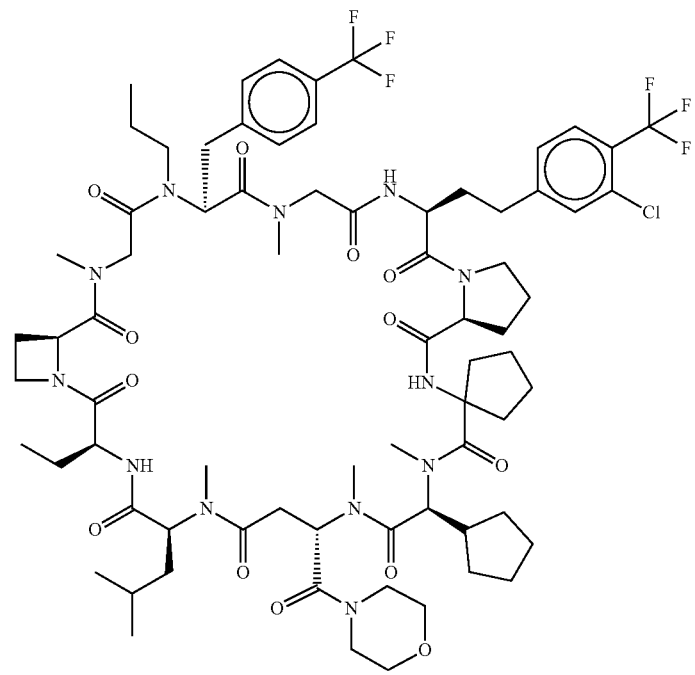 |

TABLE 38-continued
| Compound No. | Structural Formula |
|---|---|
| PP0304 | 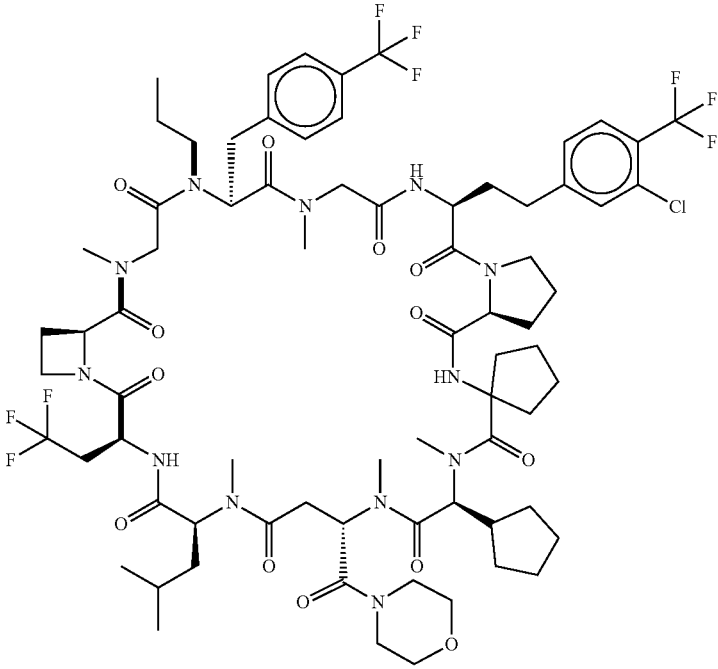 |
| PP0305 | 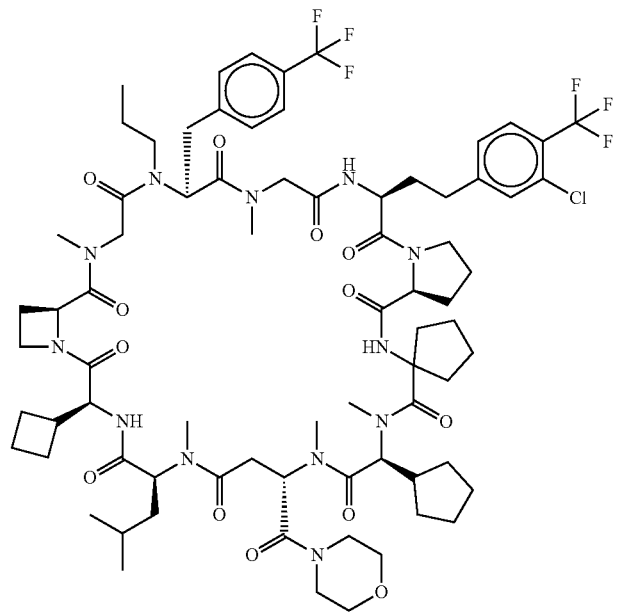 |

| Compound No. | Structural Formula |
|---|---|
| PP0306 | 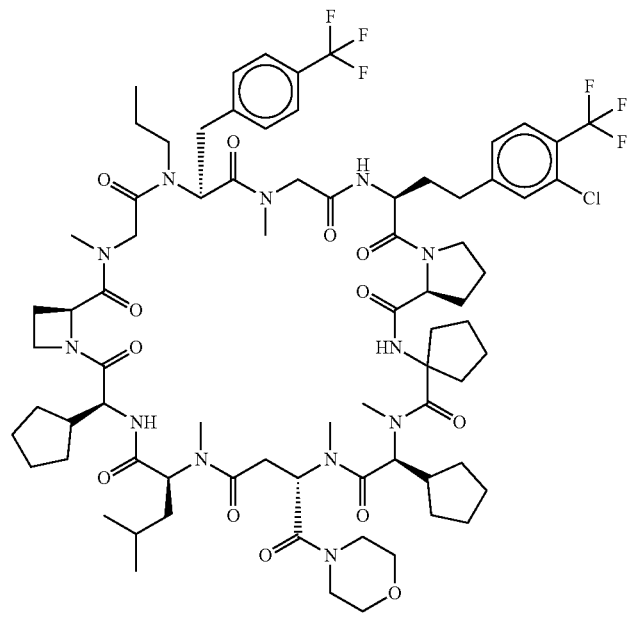 |
| PP0307 | 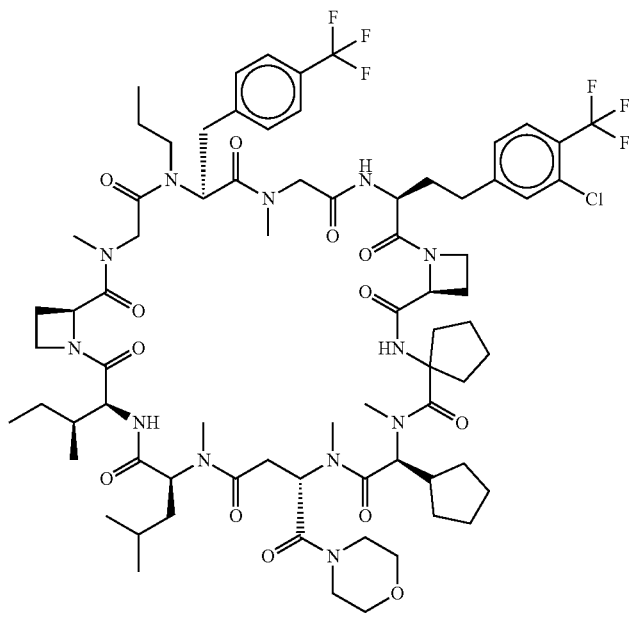 |

TABLE 38-continued
| Compound No. | Structural Formula |
|---|---|
| PP0308 | 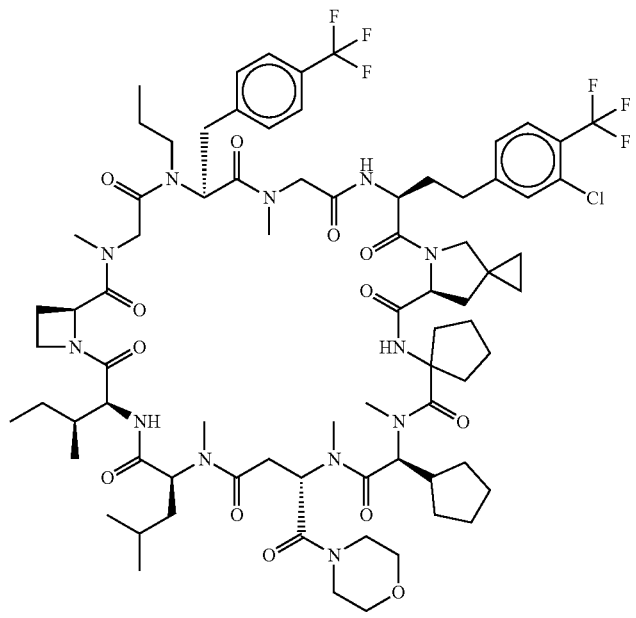 |
| PP0309 | 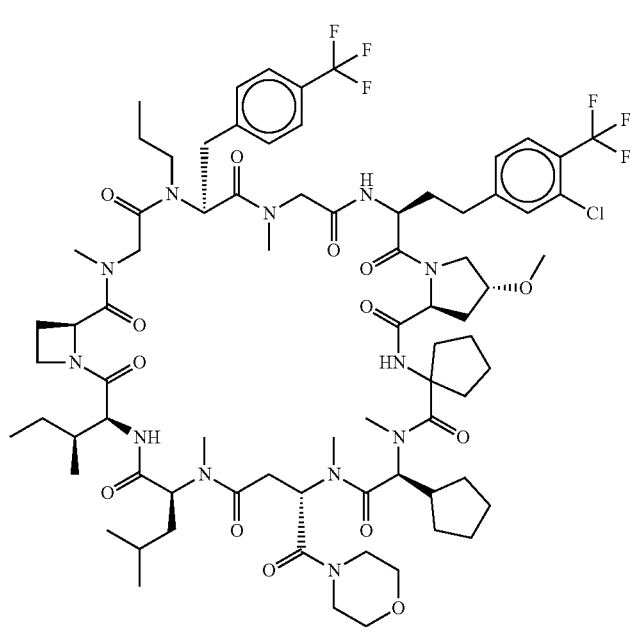 |

TABLE 38-continued
| Compound No. | Structural Formula |
|---|---|
| PP0310 | 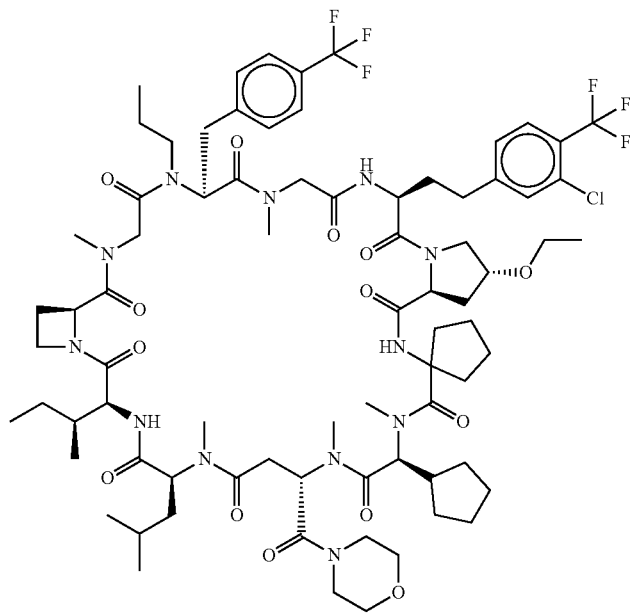 |
| PP0311 | 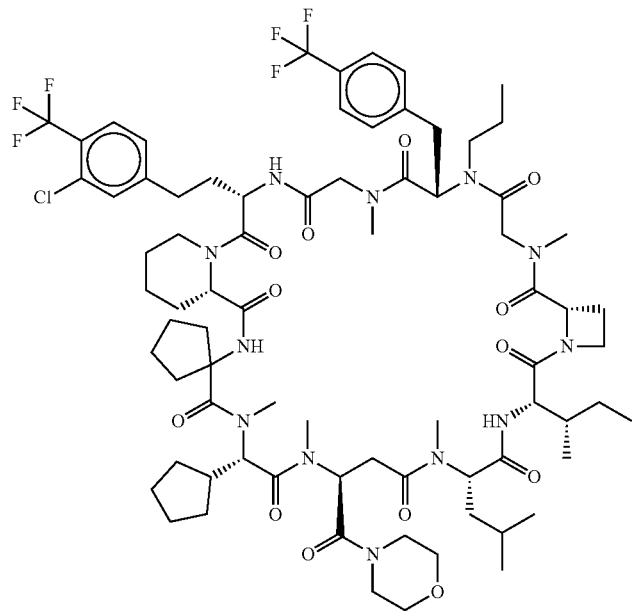 |

TABLE 38-continued

| Compound No. | Structural Formula |
|---|---|
| PP0312 | |
| PP0313 | |

TABLE 38-continued
| Compound No. | Structural Formula |
|---|---|
| PP0314 | 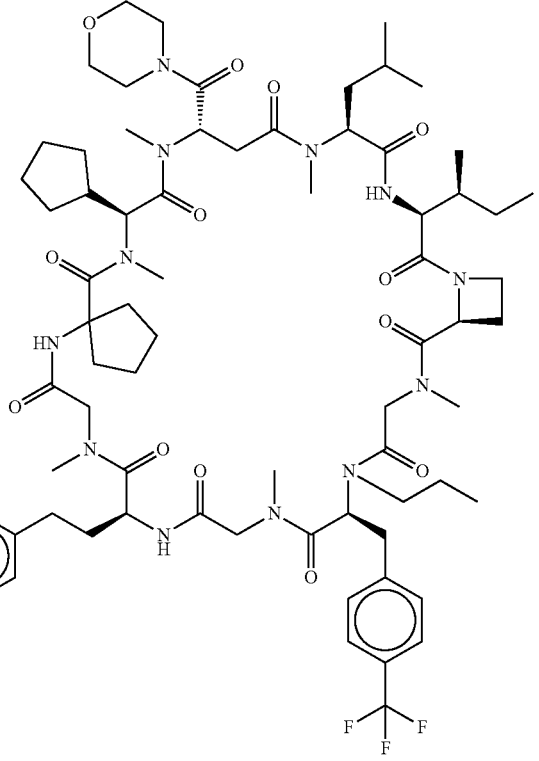 |
| PP0315 | 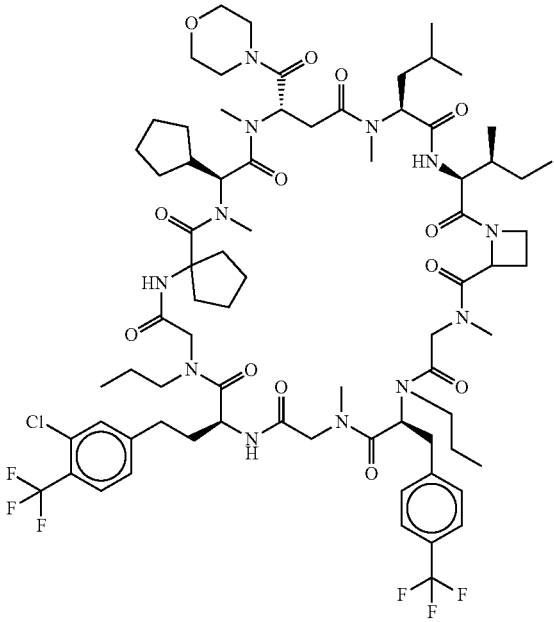 |

TABLE 38-continued
| Compound No. | Structural Formula |
|---|---|
| PP0316 | 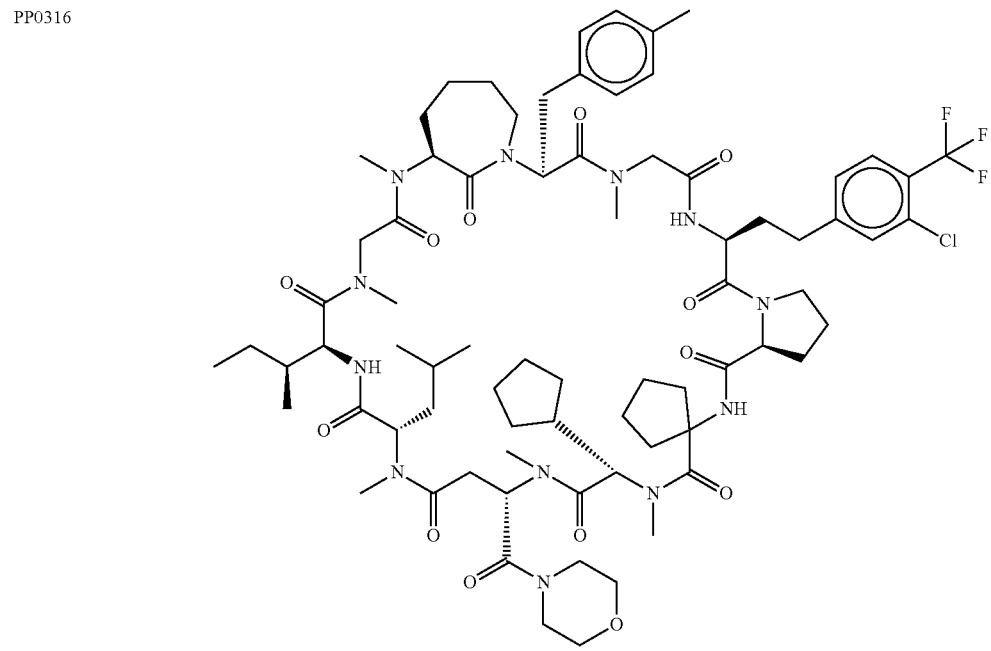 |
| PP0317 | 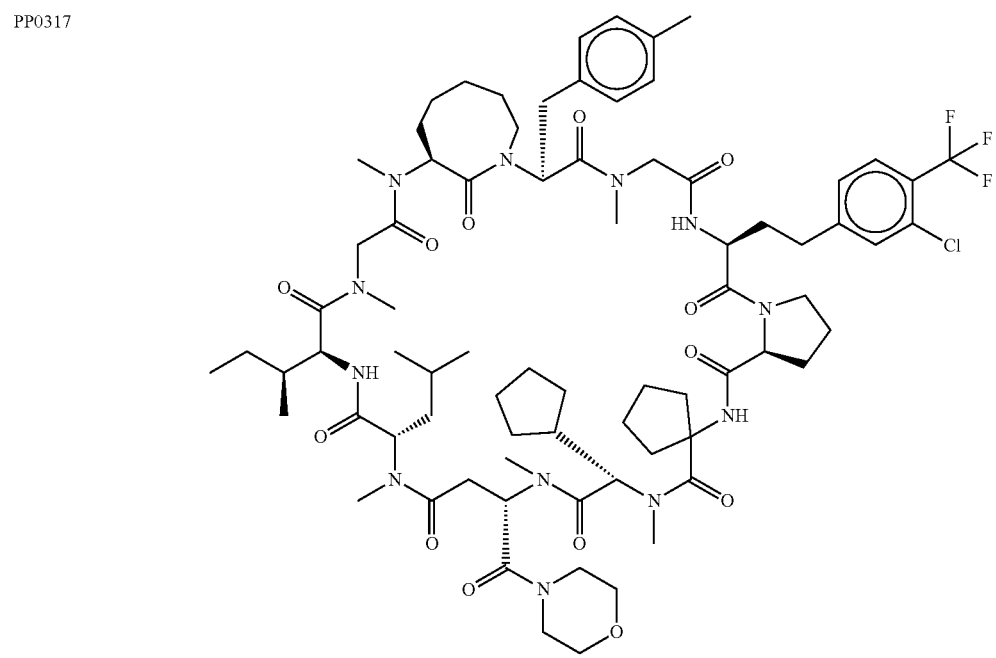 |

TABLE 38-continued
| Compound No. | Structural Formula |
|---|---|
| PP0318 | 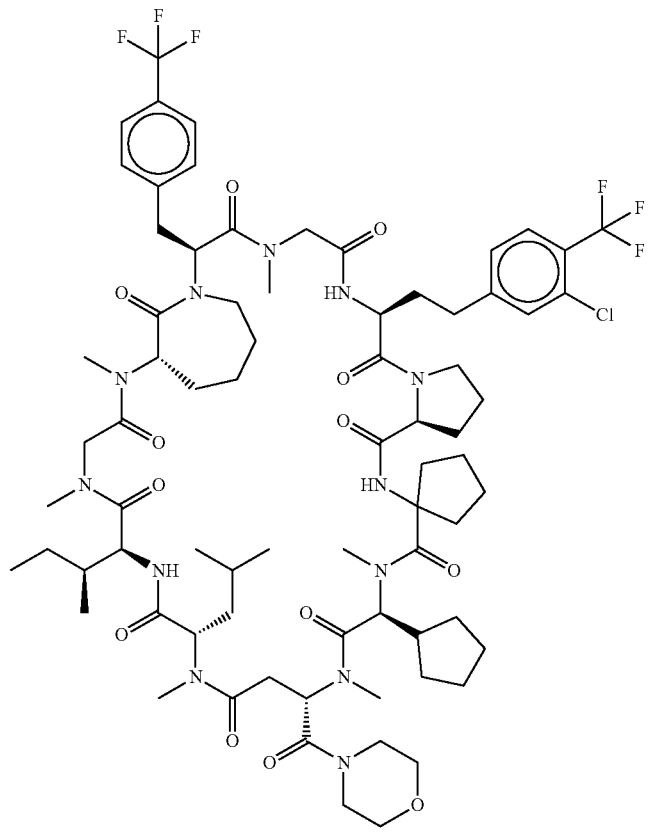 |

TABLE 38-continued
| Compound No. | Structural Formula |
|---|---|
| PP0319 | 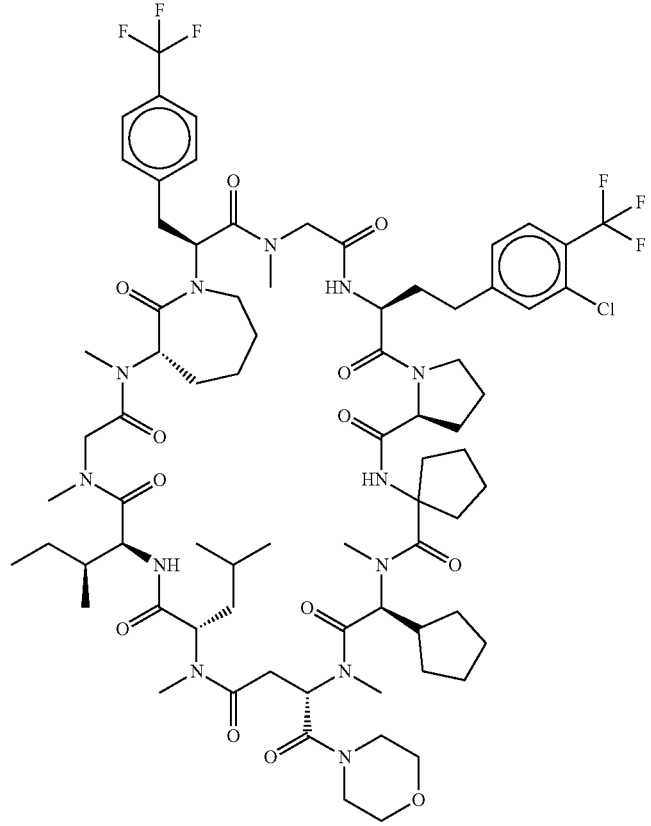 |
| PP0320 | 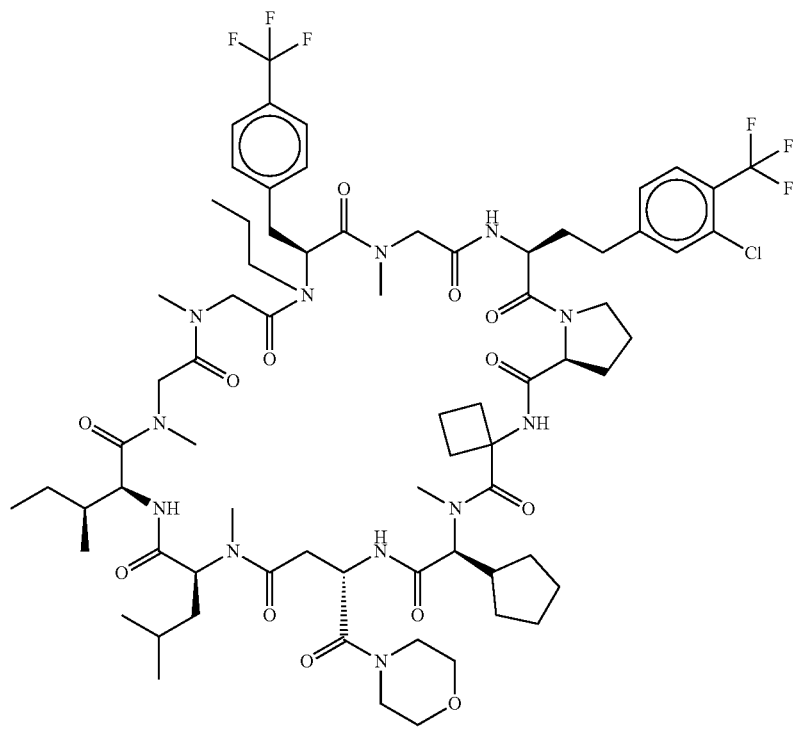 |

TABLE 38-continued
| Compound No. | Structural Formula |
|---|---|
| PP0321 | 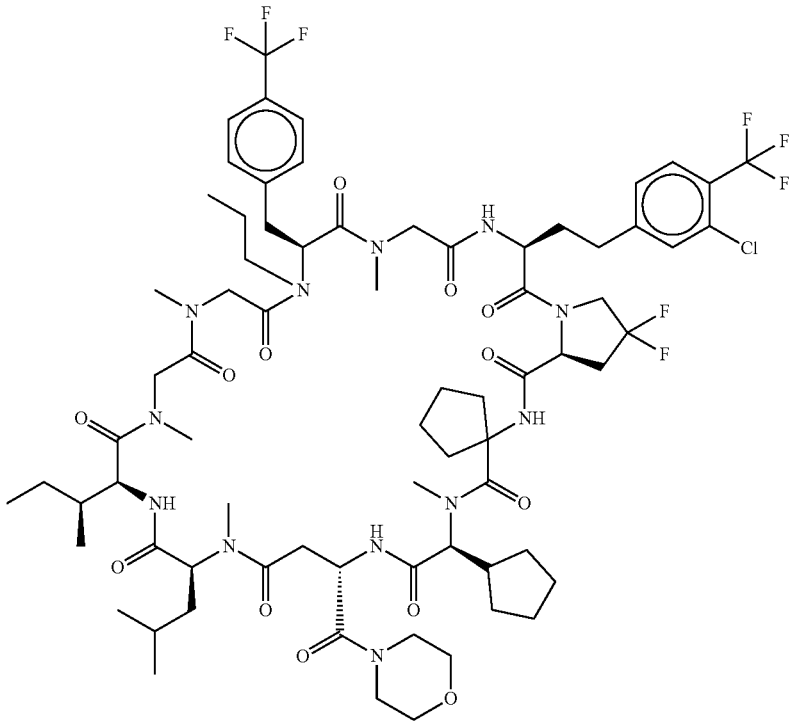 |
| PP0322 | 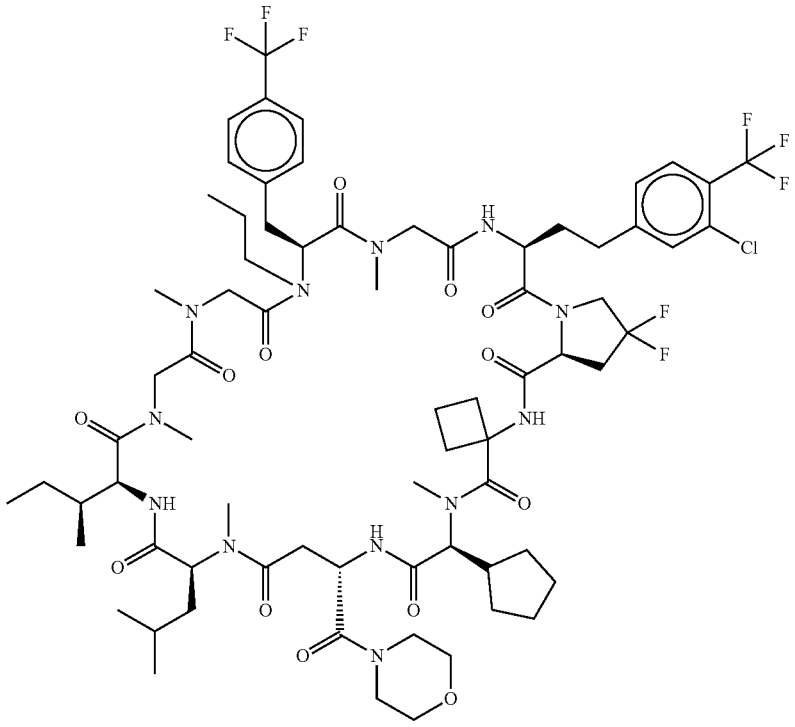 |

TABLE 38-continued
| Compound No. | Structural Formula |
|---|---|
| PP0323 | 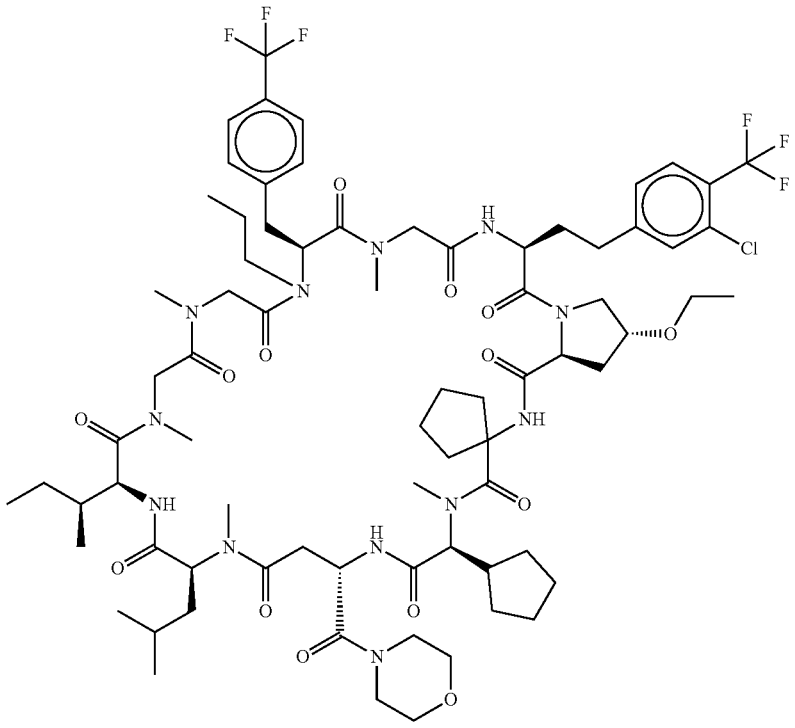 |
| PP0324 | 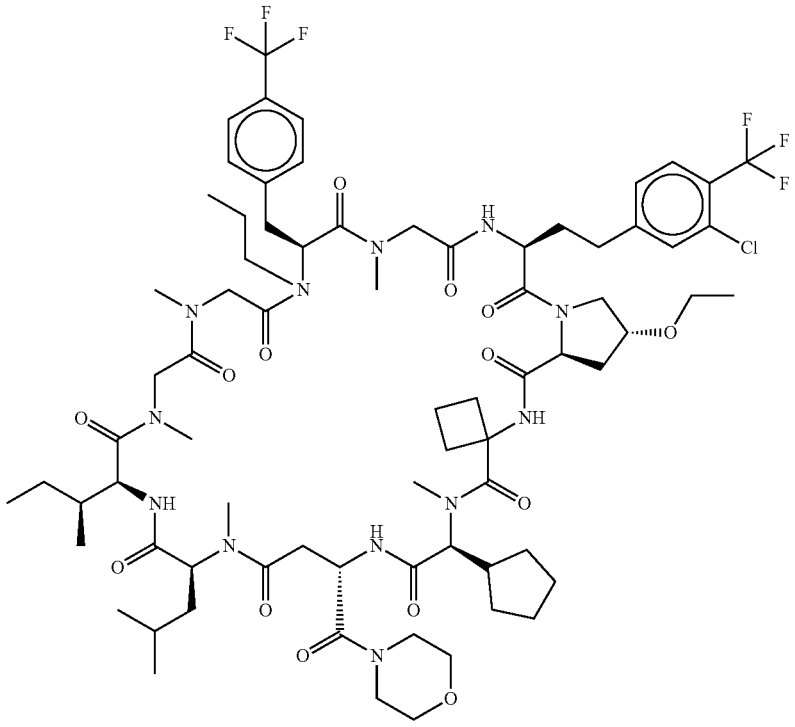 |

TABLE 38-continued
| Compound No. | Structural Formula |
|---|---|
| PP0325 | 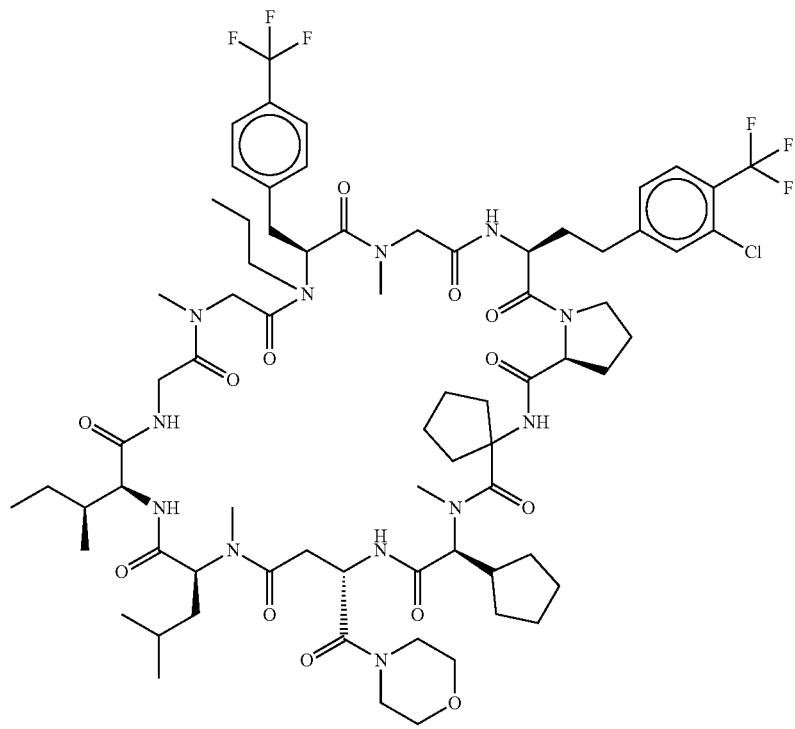 |
| PP0326 | 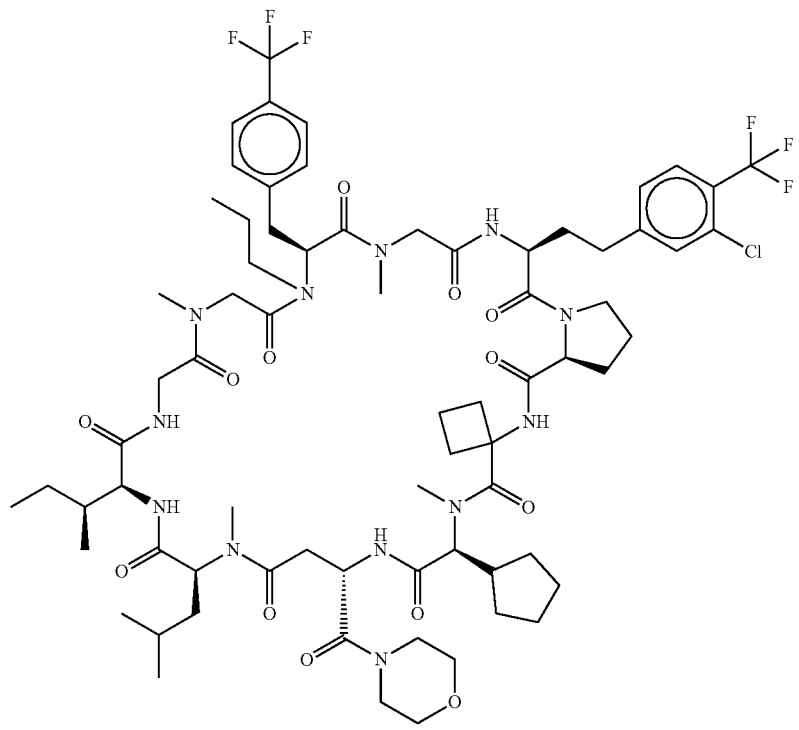 |

TABLE 38-continued
| Compound No. | Structural Formula |
| --- | --- |
| PP0327 | 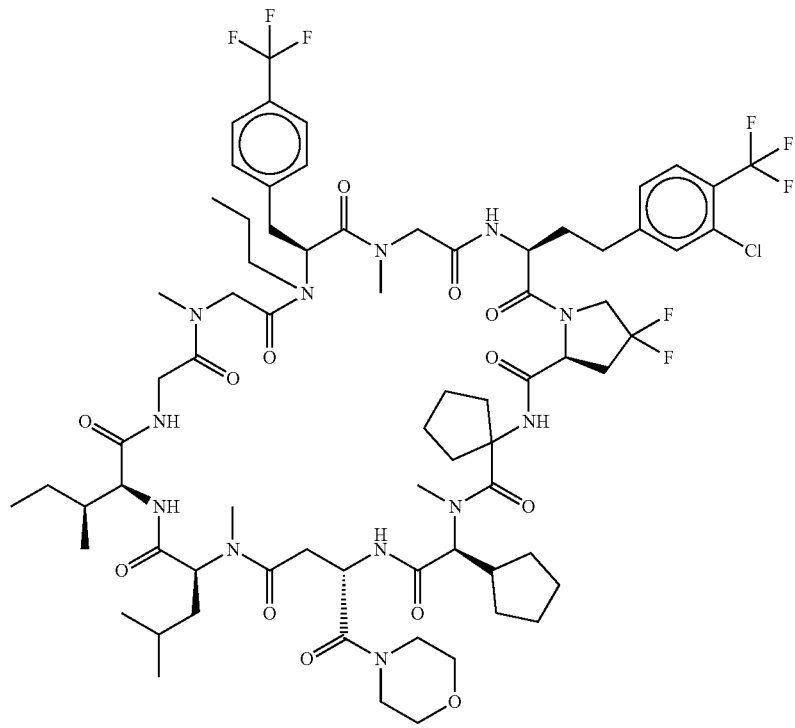 |
| PP0328 | 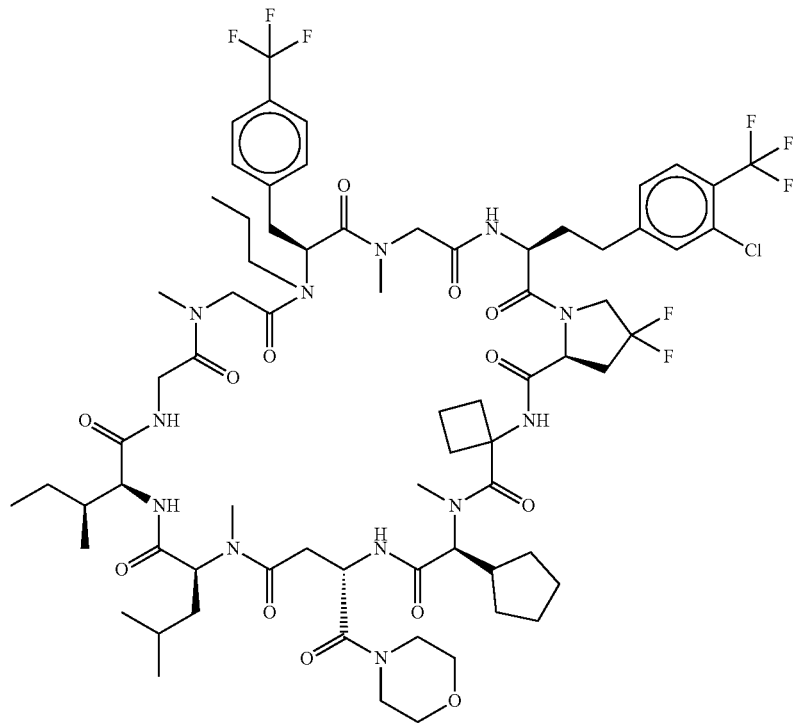 |

TABLE 38-continued

| Compound No. | Structural Formula |
|---|---|
| PP0329 | |
| PP0330 | |

TABLE 38-continued
| Compound No. | Structural Formula |
|---|---|
| PP0331 | 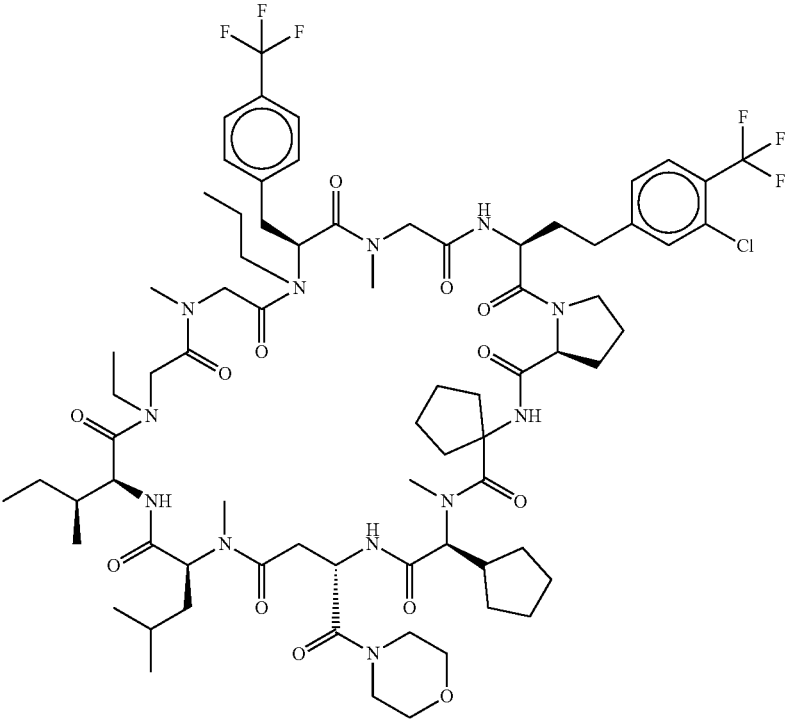 |
| PP0332 | 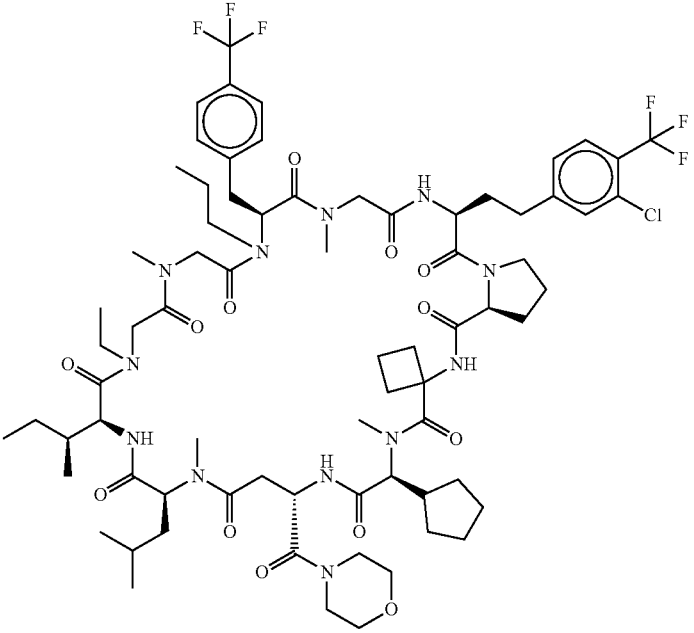 |

TABLE 38-continued
| Compound No. | Structural Formula |
|---|---|
| PP0333 | 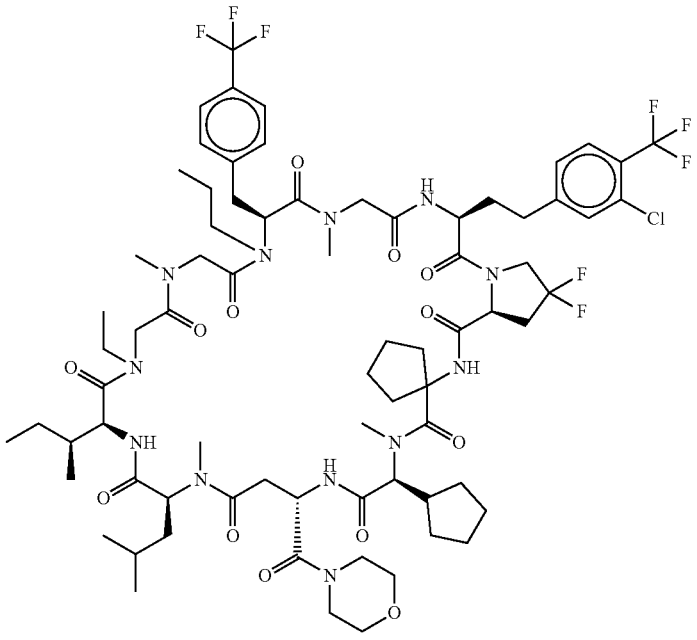 |
| PP0334 | 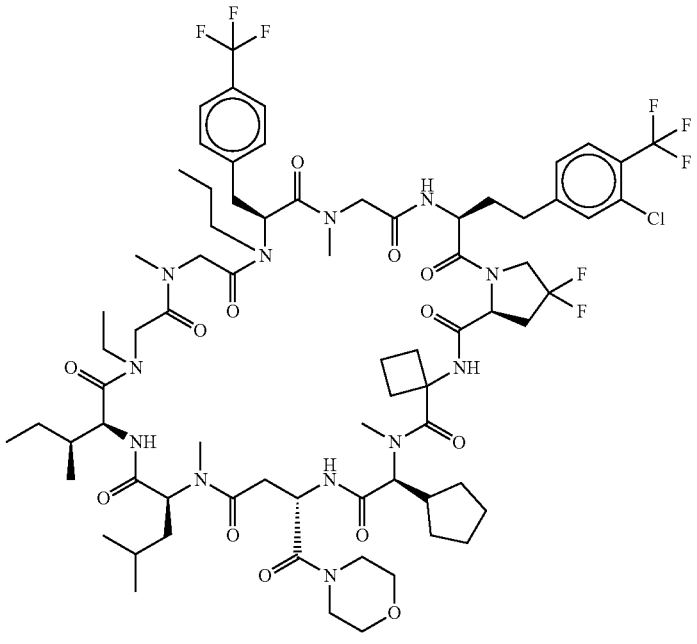 |

| Compound No. | Structural Formula |
|---|---|
| PP0335 | 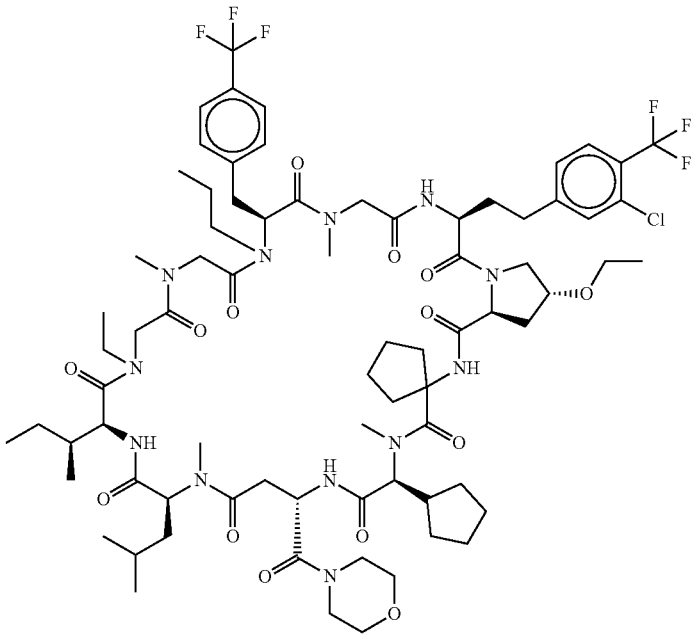 |
| PP0336 | 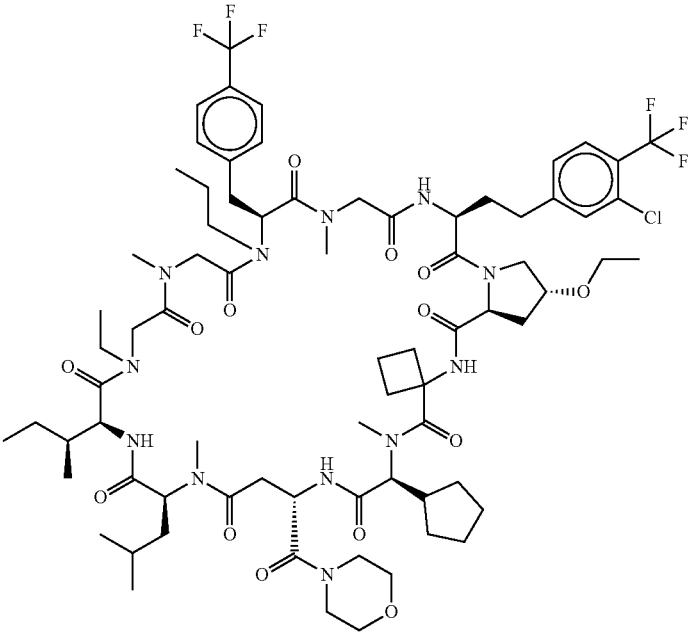 |

TABLE 38-continued
| Compound No. | Structural Formula |
| --- | --- |
| PP0337 | 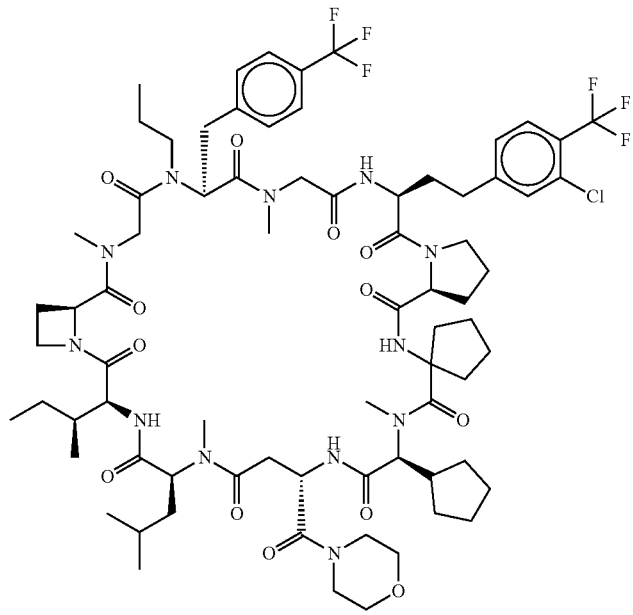 |
| PP0338 | 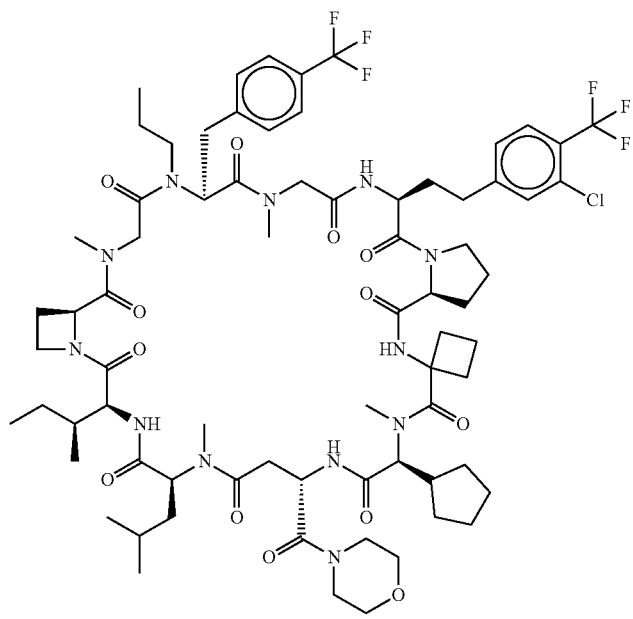 |

TABLE 38-continued
| Compound No. | Structural Formula |
|---|---|
| PP0339 | 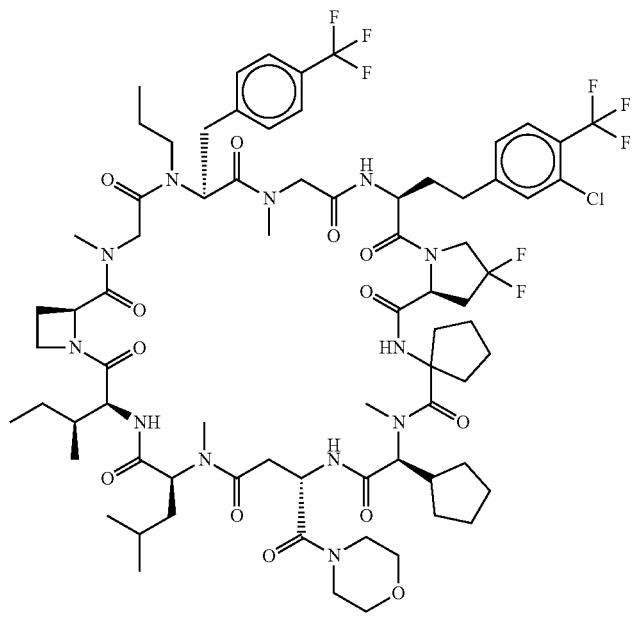 |
| PP0340 | 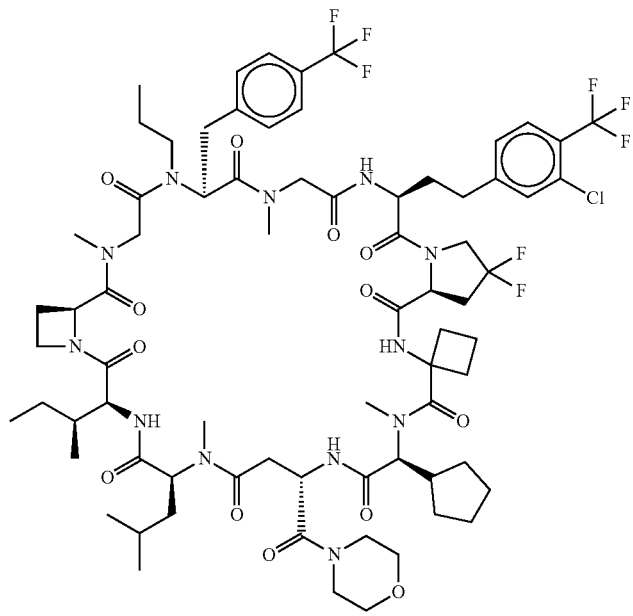 |

TABLE 38-continued
| Compound No. | Structural Formula |
|---|---|
| PP0341 | 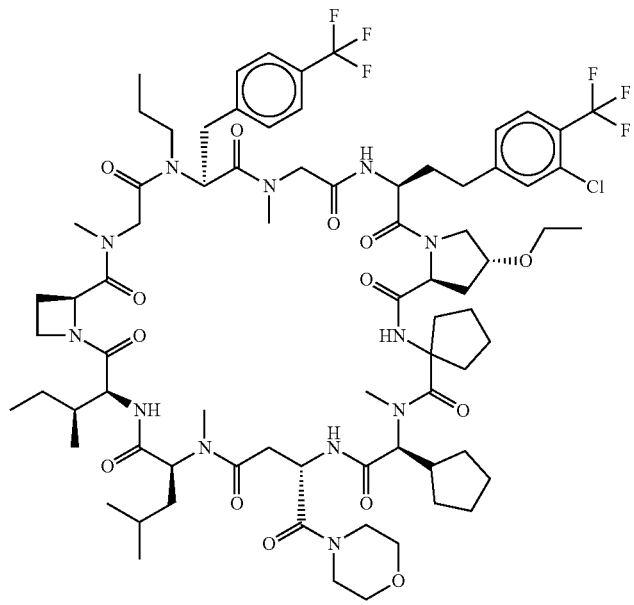 |
| PP0342 | 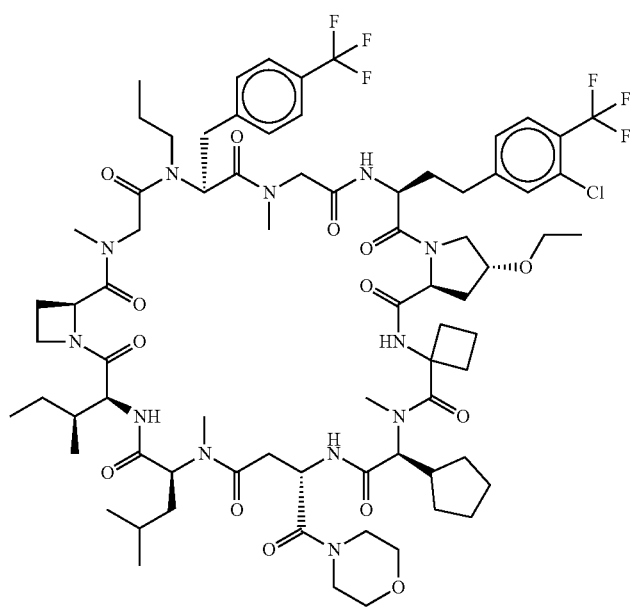 |

TABLE 38-continued

| Compound No. | Structural Formula |
|---|---|
| PP0343 | |
| PP0344 | |

TABLE 38-continued

| Compound No. | Structural Formula |
|---|---|
| PP0345 | |
| PP0346 | |

TABLE 38-continued
| Compound No. | Structural Formula |
|---|---|
| PP0347 | 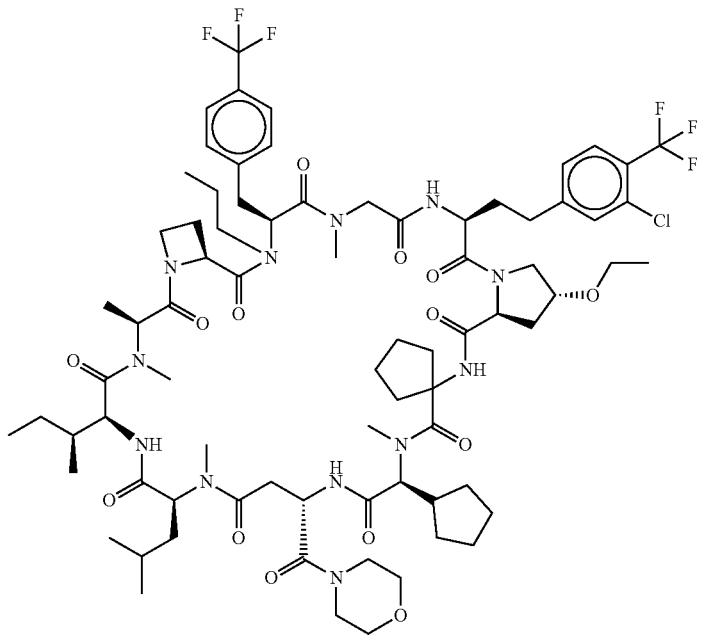 |
| PP0348 | 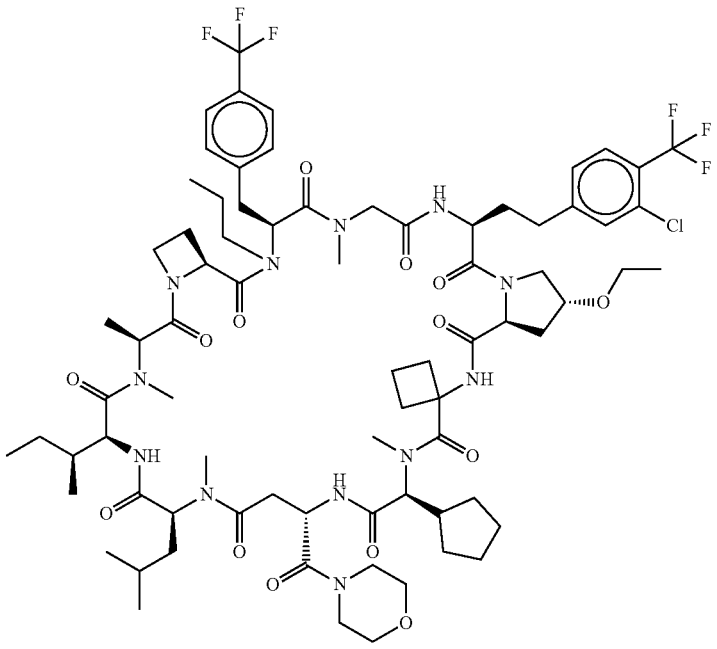 |

TABLE 38-continued
| Compound No. | Structural Formula |
|---|---|
| PP0349 | 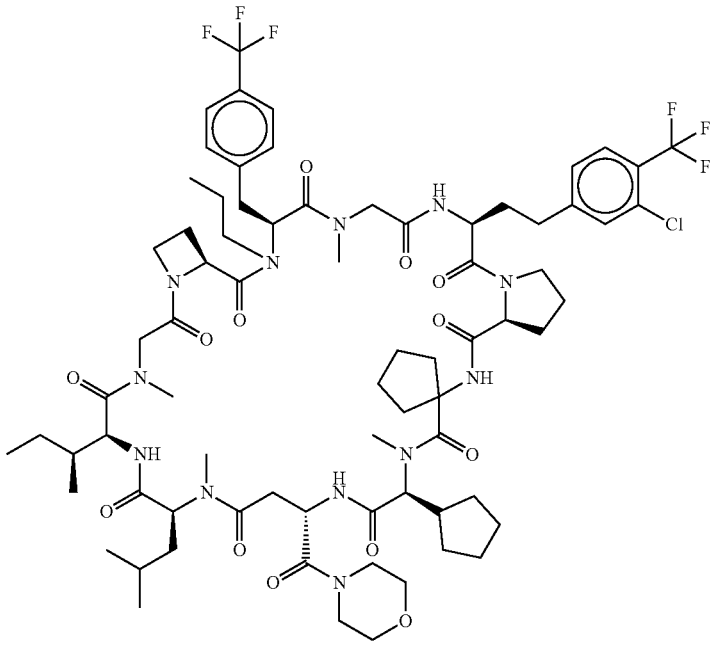 |
| PP0350 | 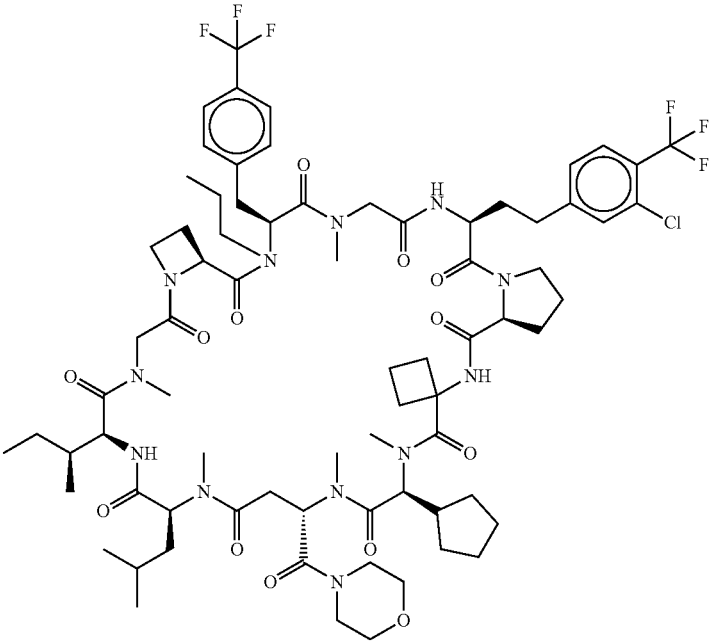 |

| Compound No. | Structural Formula |
|---|---|
| PP0351 | |
| PP0352 | |

TABLE 38-continued

| Compound No. | Structural Formula |
|---|---|
| PP0353 | (structure) |
| PP0354 | (structure) |

TABLE 38-continued
| Compound No. | Structural Formula |
|---|---|
| PP0355 | 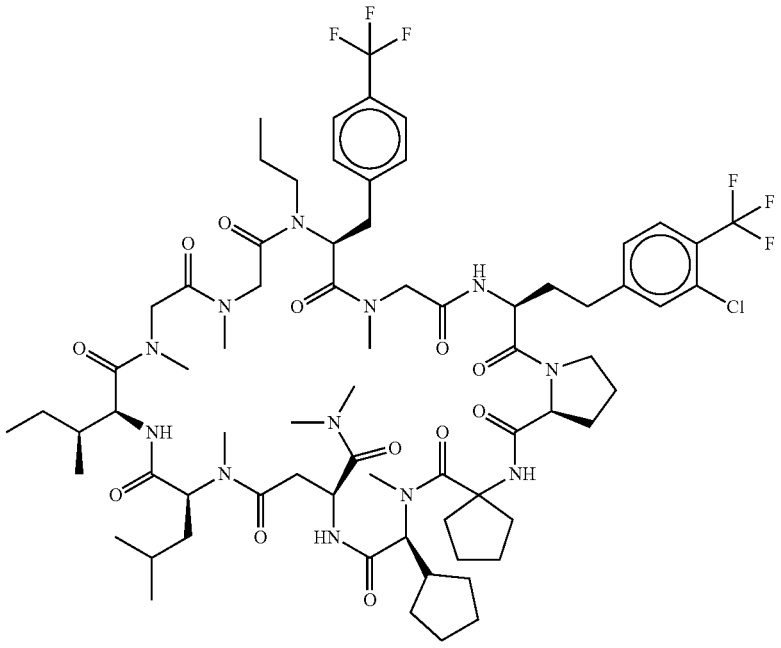 |
| PP0356 | 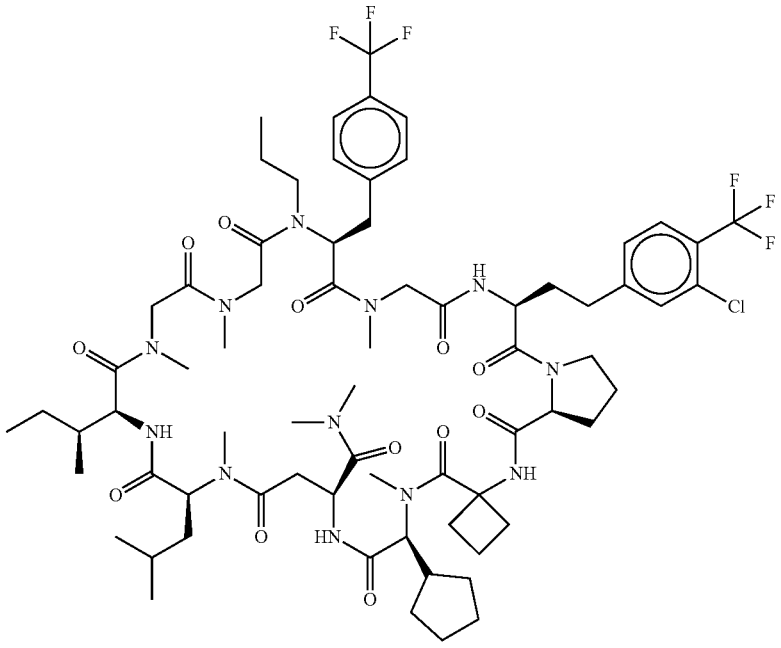 |

TABLE 38-continued

| Compound No. | Structural Formula |
|---|---|
| PP0357 | |
| PP0358 | |

TABLE 38-continued
| Compound No. | Structural Formula |
|---|---|
| PP0359 | 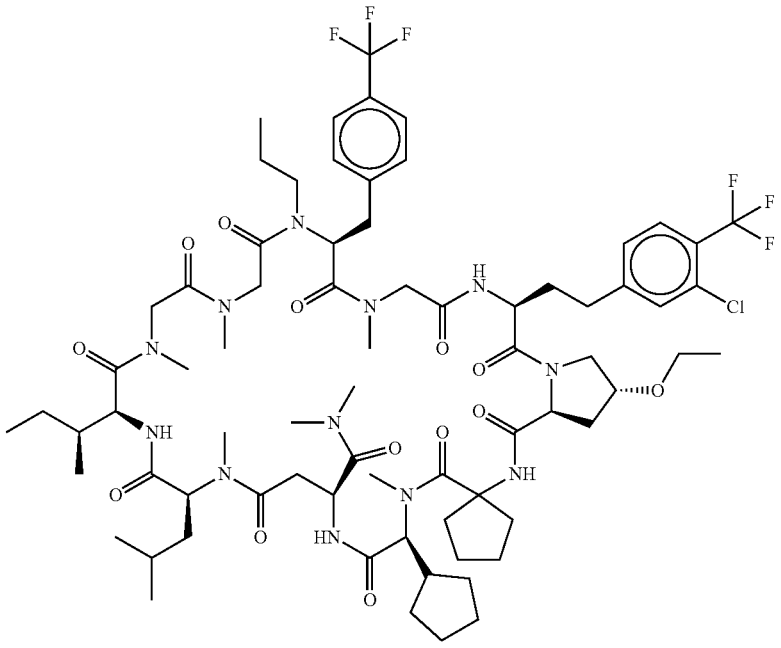 |
| PP0360 | 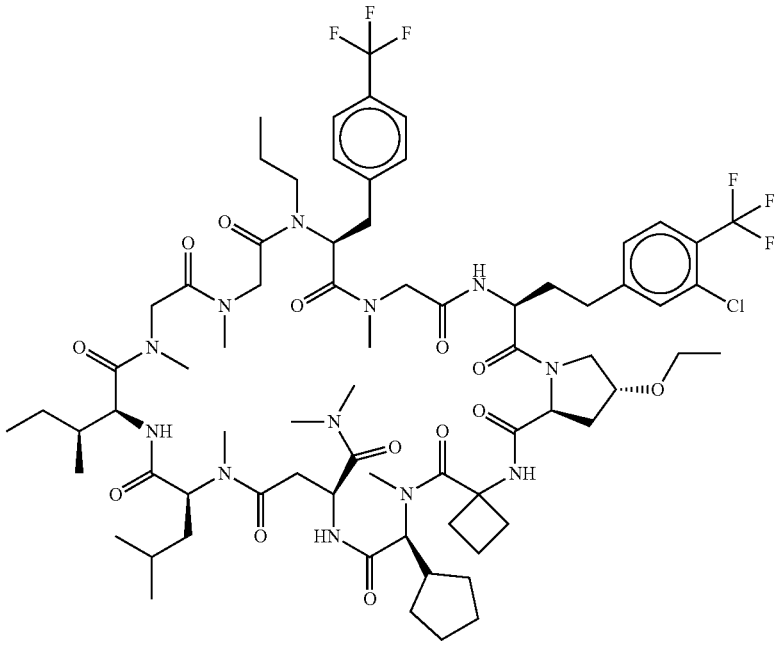 |

TABLE 38-continued
| Compound No. | Structural Formula |
|---|---|
| PP0361 | 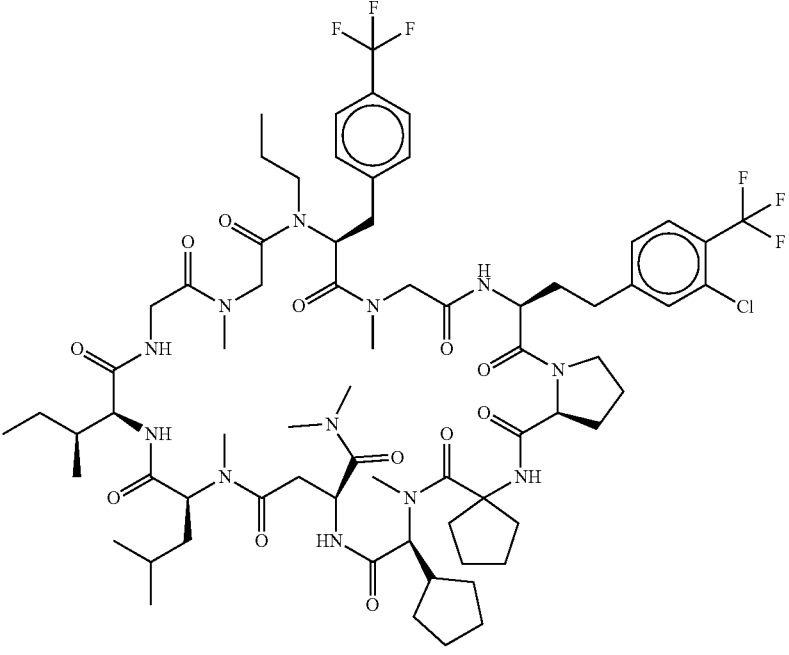 |
| PP0362 | 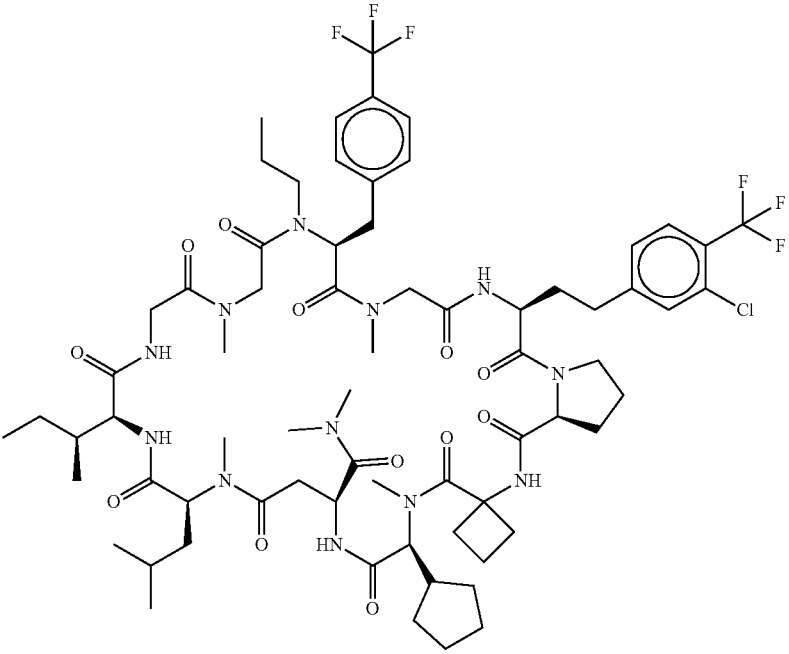 |

TABLE 38-continued
| Compound No. | Structural Formula |
|---|---|
| PP0363 | 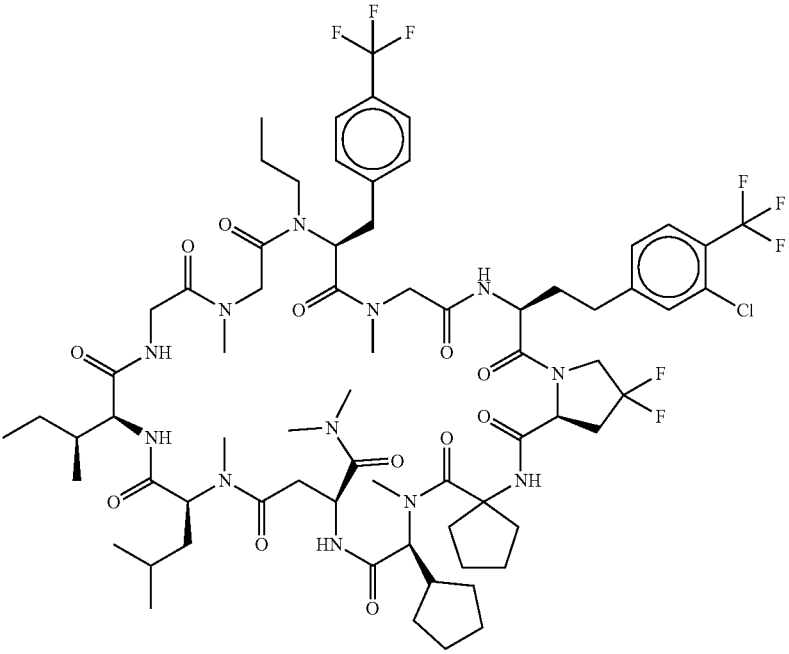 |
| PP0364 | 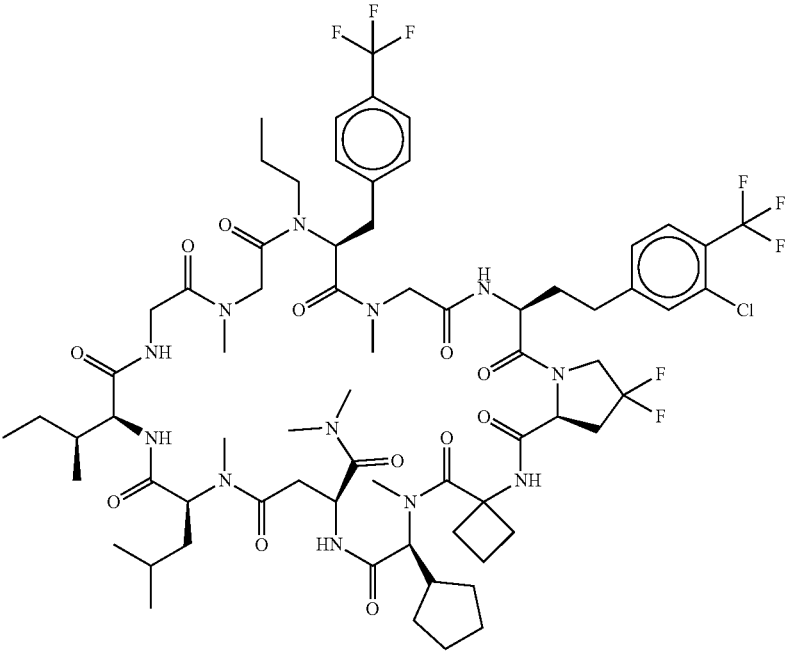 |

TABLE 38-continued
| Compound No. | Structural Formula |
|---|---|
| PP0365 | 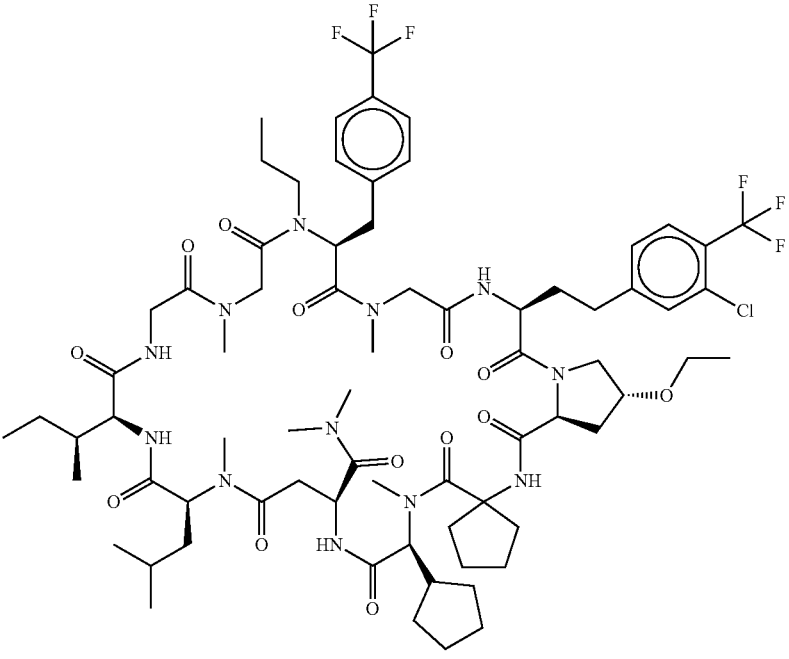 |
| PP0366 | 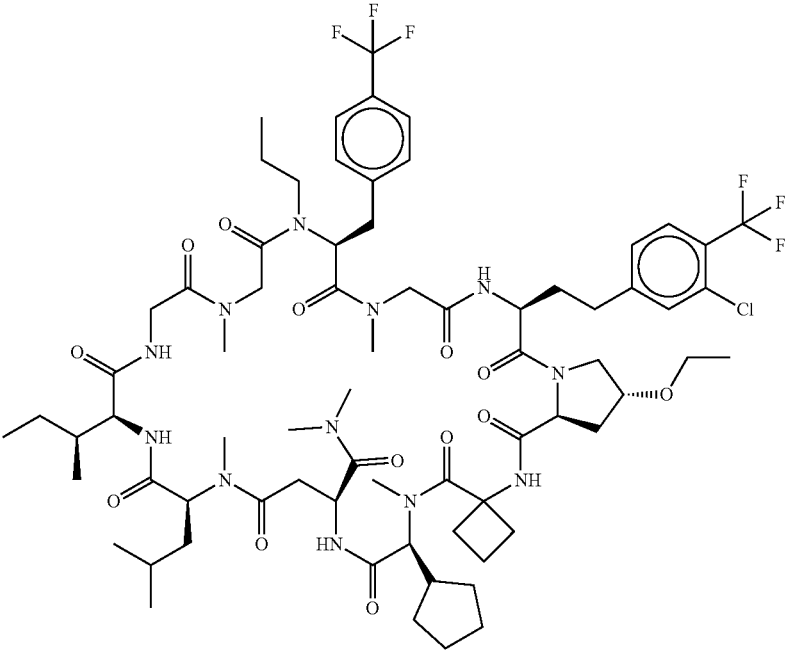 |

TABLE 38-continued
| Compound No. | Structural Formula |
|---|---|
| PP0367 | 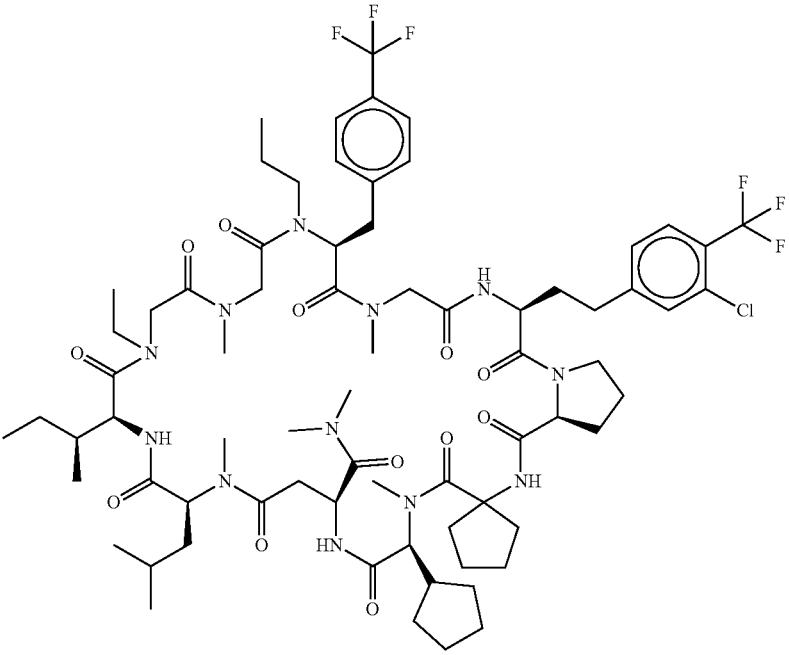 |
| PP0368 | 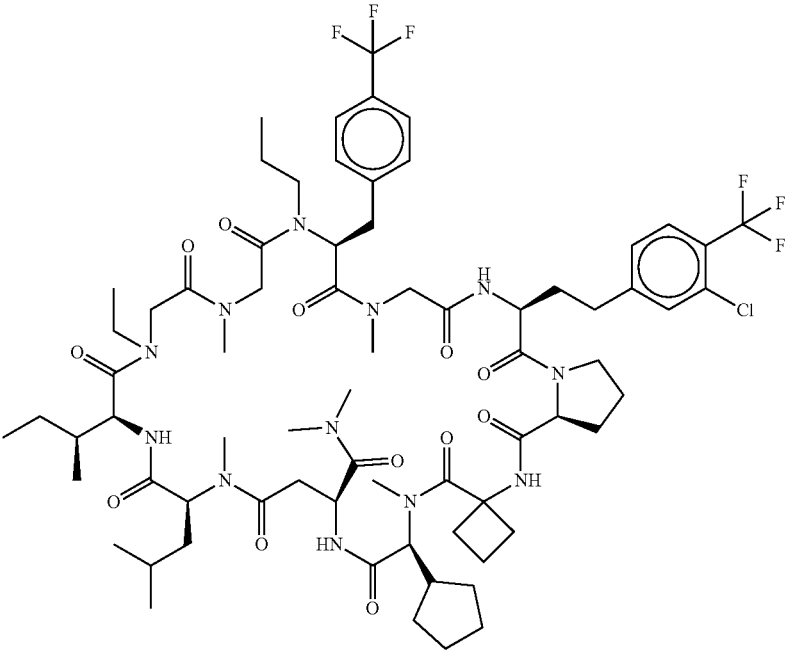 |

TABLE 38-continued
| Compound No. | Structural Formula |
|---|---|
| PP0369 | 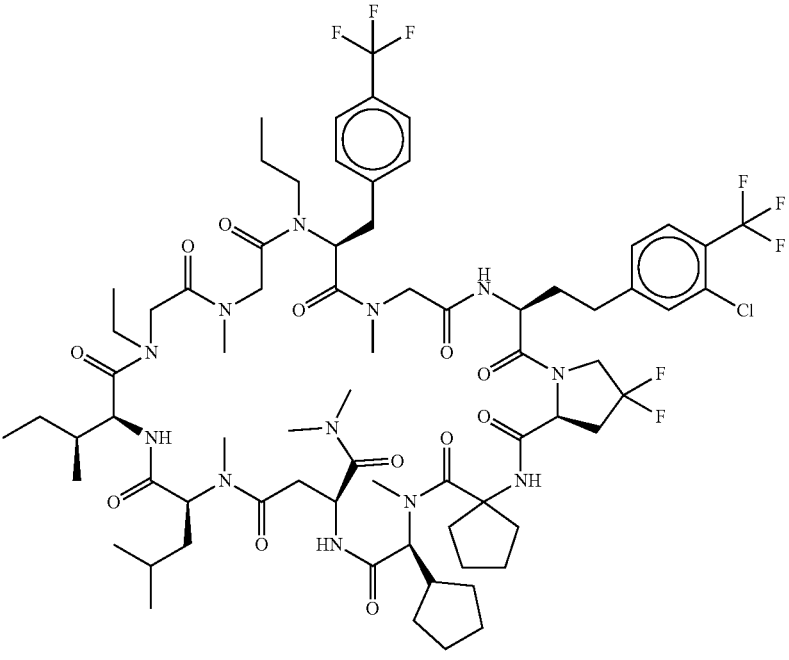 |
| PP0370 | 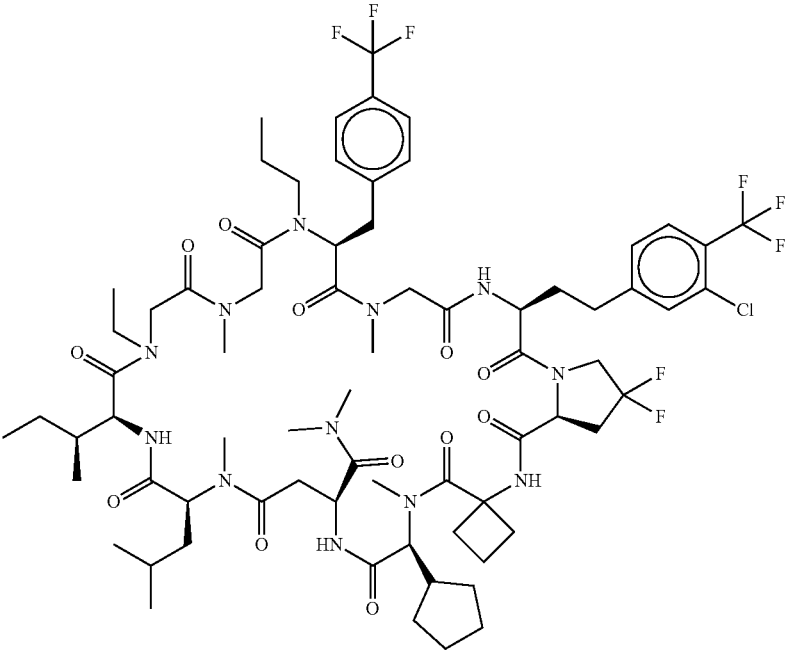 |

TABLE 38-continued
| Compound No. | Structural Formula |
| --- | --- |
| PP0371 | 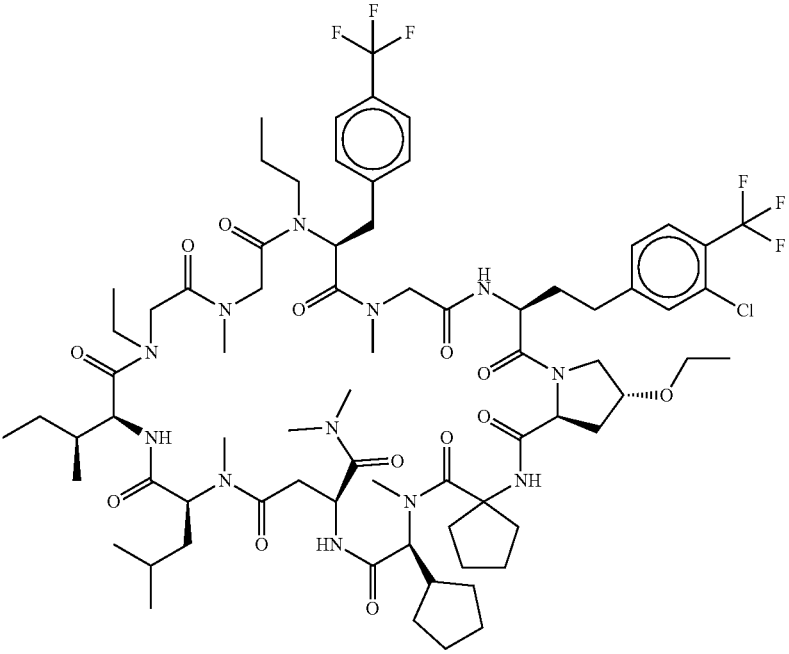 |
| PP0372 | 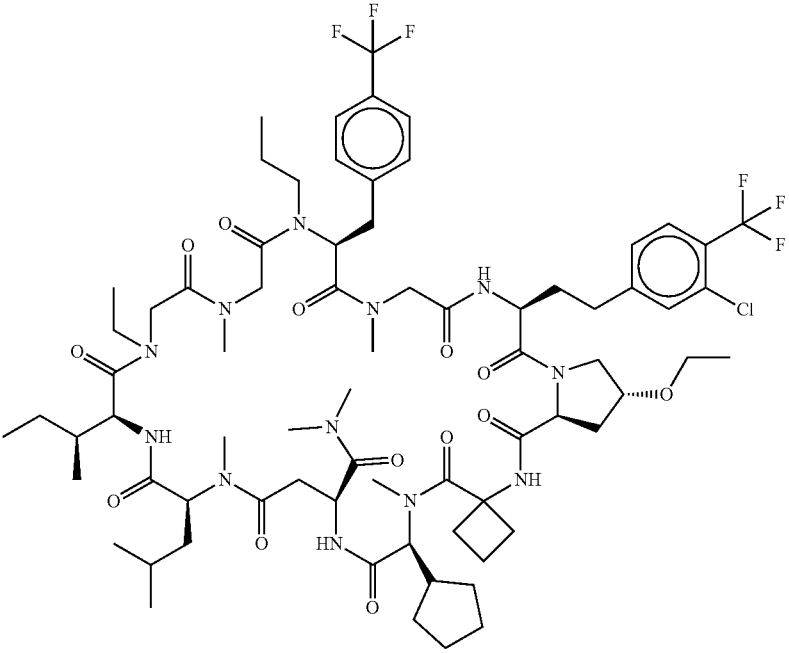 |

TABLE 38-continued

| Compound No. | Structural Formula |
|---|---|
| PP0373 | |
| PP0374 | |

TABLE 38-continued
| Compound No. | Structural Formula |
|---|---|
| PP0375 | 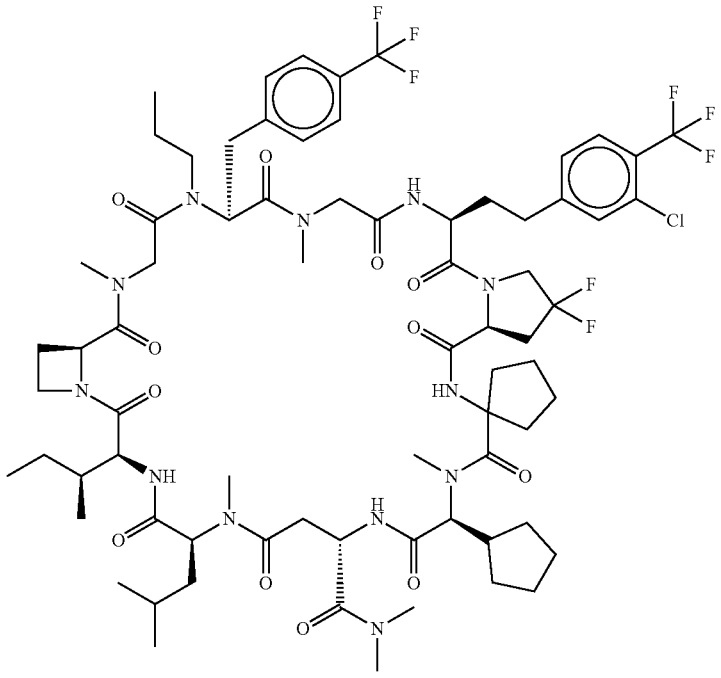 |
| PP0376 | 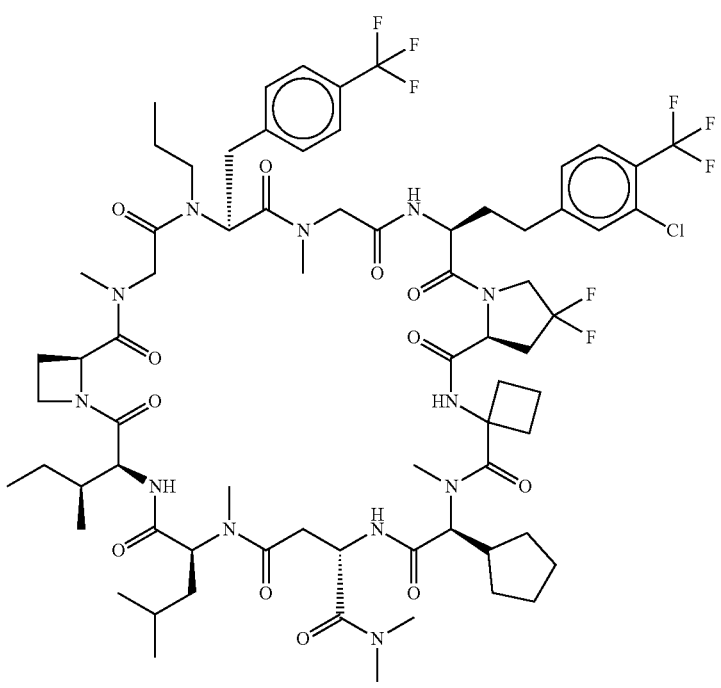 |

TABLE 38-continued
| Compound No. | Structural Formula |
|---|---|
| PP0377 | 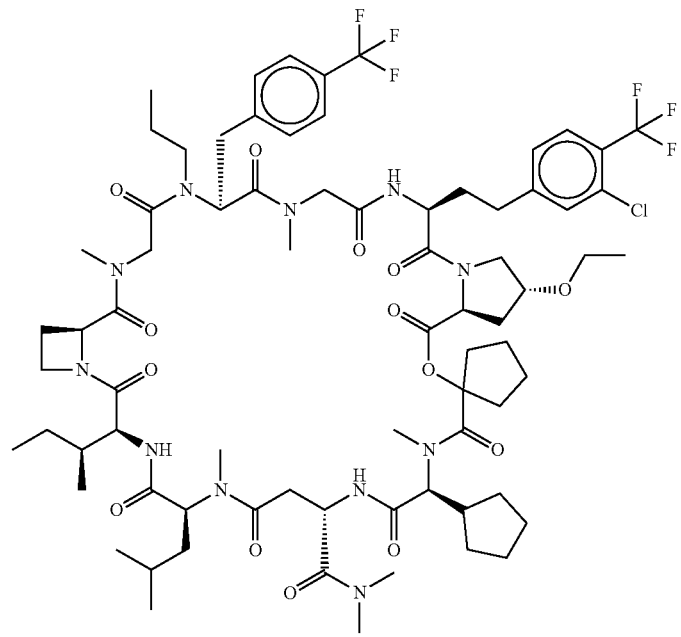 |
| PP0378 | 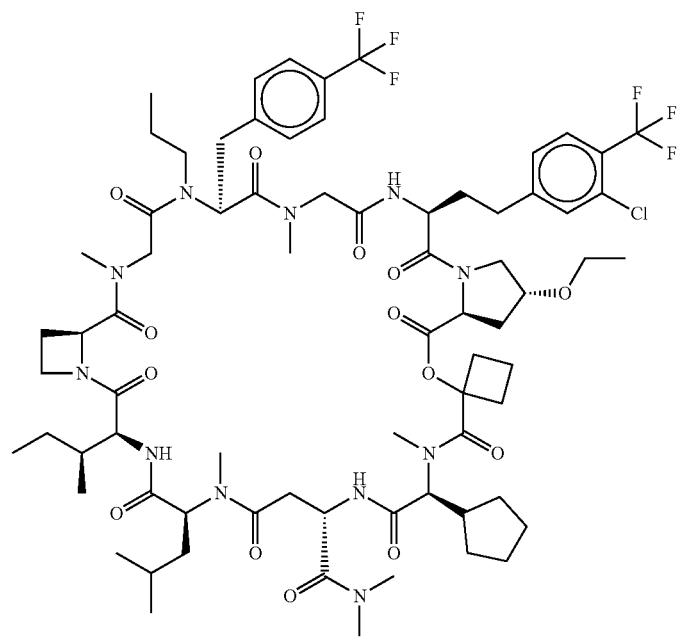 |

TABLE 38-continued

| Compound No. | Structural Formula |
|---|---|
| PP0379 | |
| PP0380 | |

TABLE 38-continued

| Compound No. | Structural Formula |
| --- | --- |
| PP0381 | |
| PP0382 | |

TABLE 38-continued
| Compound No. | Structural Formula |
|---|---|
| PP0383 | 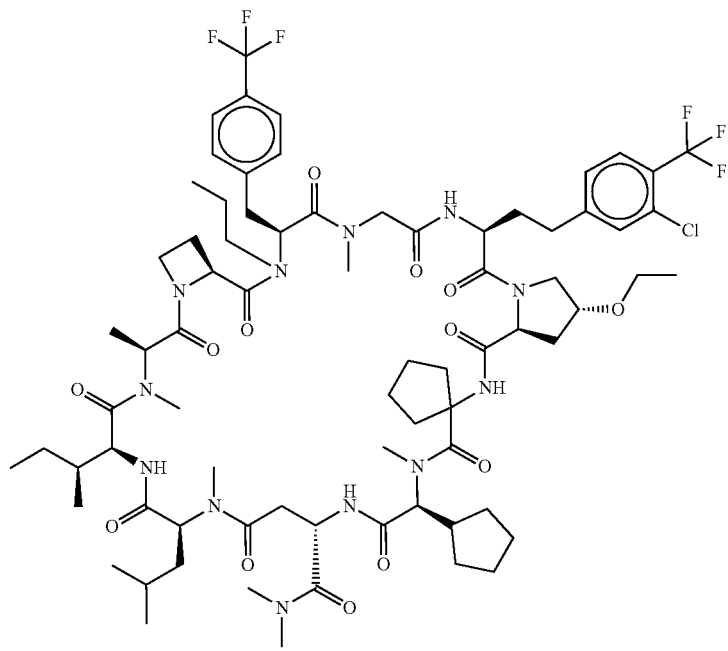 |
| PP0384 | 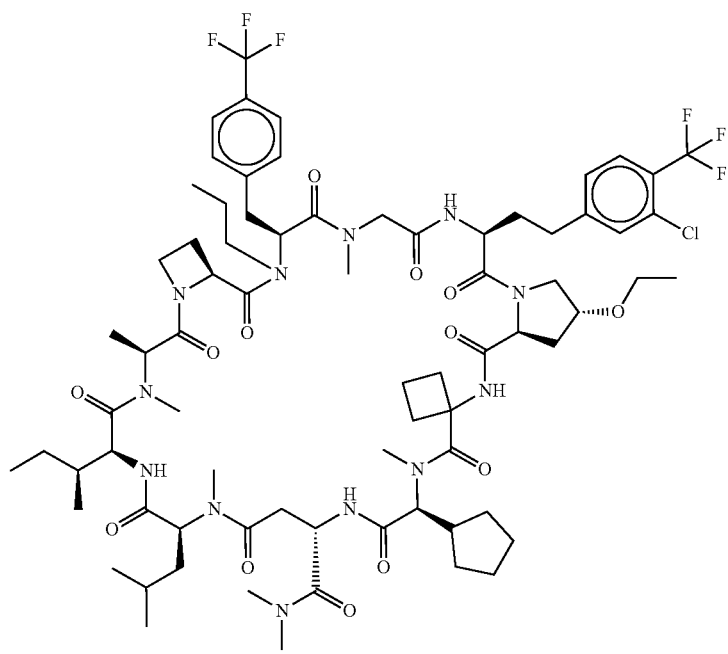 |

TABLE 38-continued

| Compound No. | Structural Formula |
|---|---|
| PP0385 | |
| PP0386 | |

TABLE 38-continued
| Compound No. | Structural Formula |
|---|---|
| PP0387 | 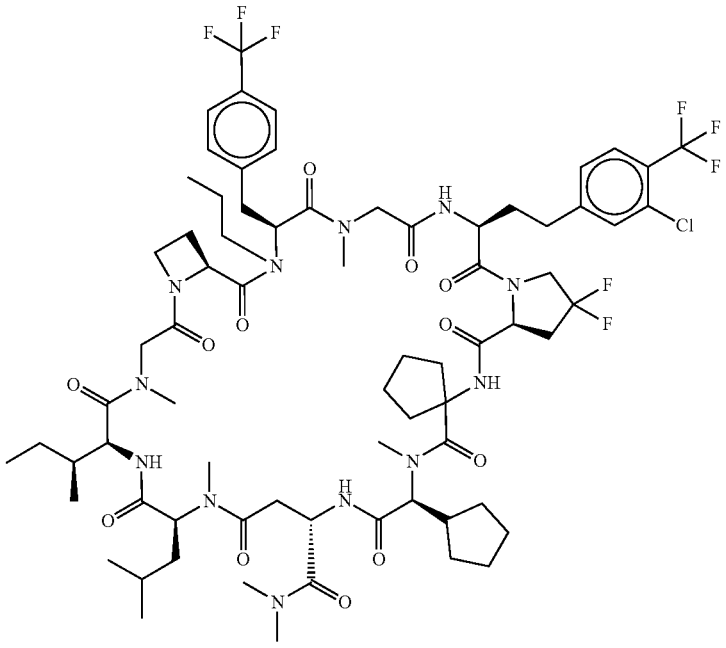 |
| PP0388 | 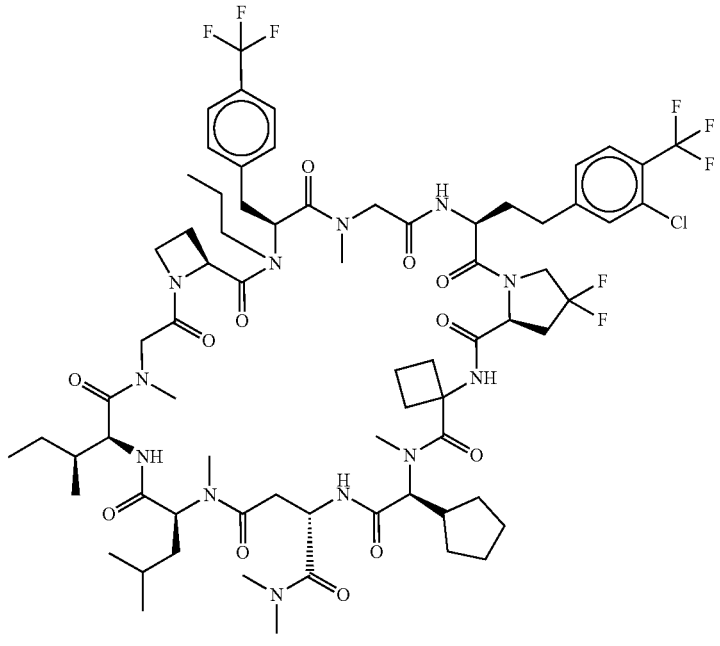 |

TABLE 38-continued

| Compound No. | Structural Formula |
|---|---|
| PP0389 | |
| PP0390 | |

TABLE 38-continued
| Compound No. | Structural Formula |
|---|---|
| PP0391 | 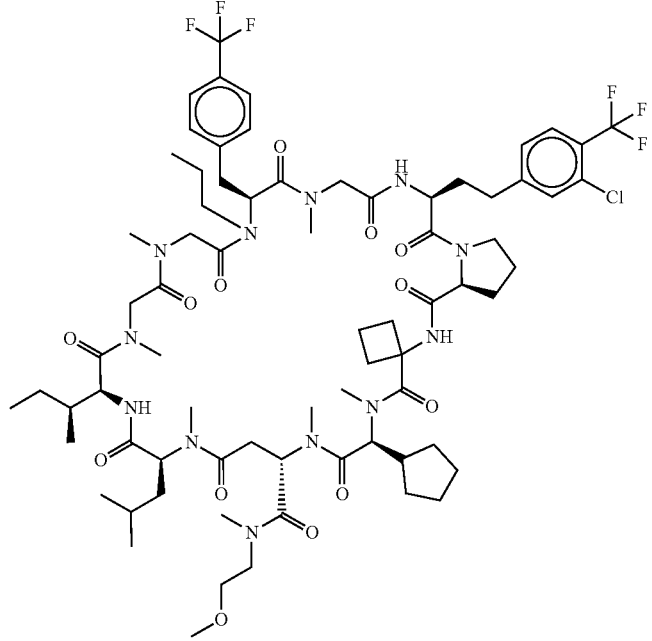 |
| PP0392 | 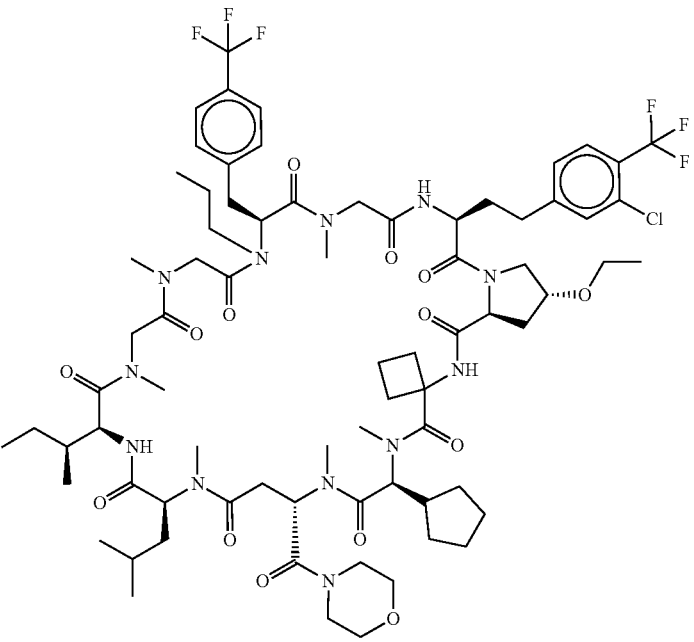 |

TABLE 38-continued
| Compound No. | Structural Formula |
|---|---|
| PP0393 | 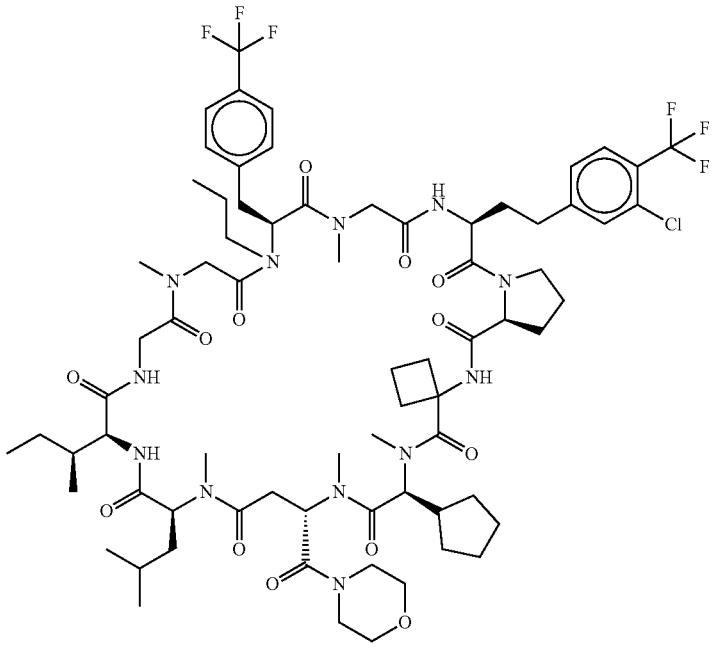 |
| PP0394 | 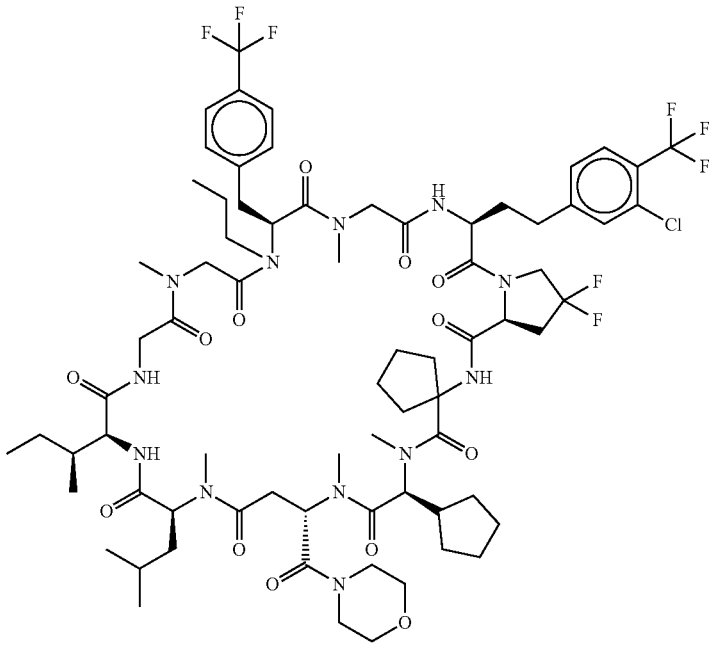 |

TABLE 38-continued

| Compound No. | Structural Formula |
| --- | --- |
| PP0395 | |
| PP0396 | |

TABLE 38-continued
| Compound No. | Structural Formula |
|---|---|
| PP0397 | 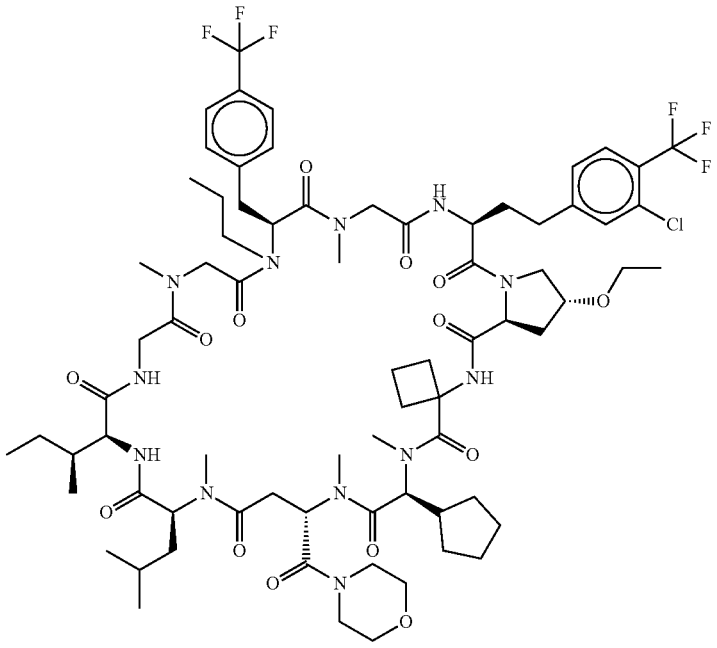 |
| PP0398 | 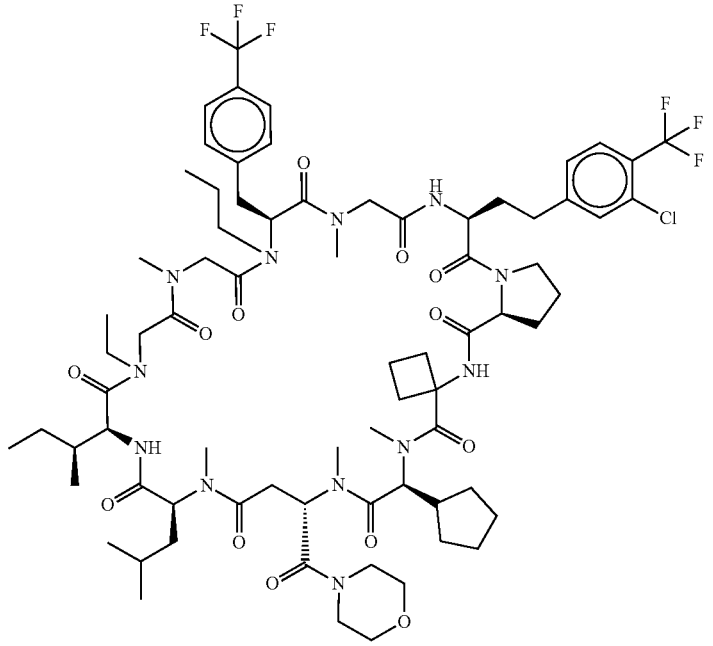 |

TABLE 38-continued

| Compound No. | Structural Formula |
|---|---|
| PP0399 | |
| PP0400 | |

TABLE 38-continued
| Compound No. | Structural Formula |
|---|---|
| PP0401 | 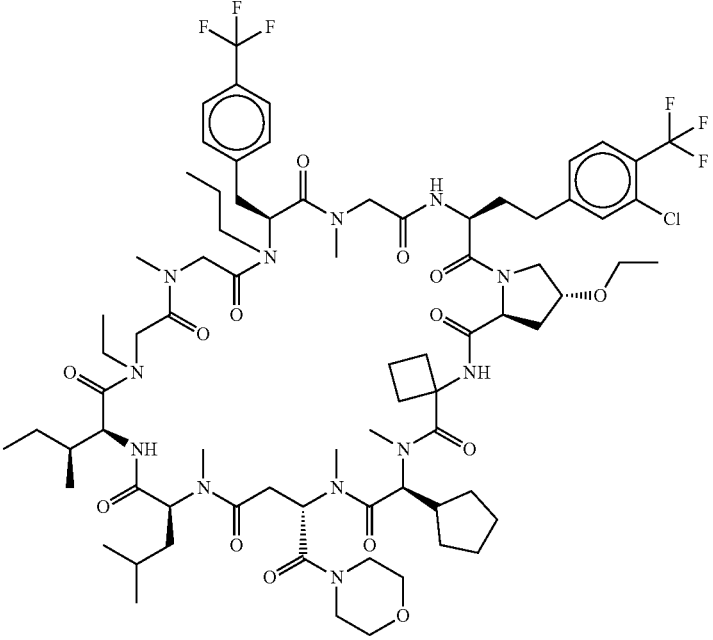 |
| PP0402 | 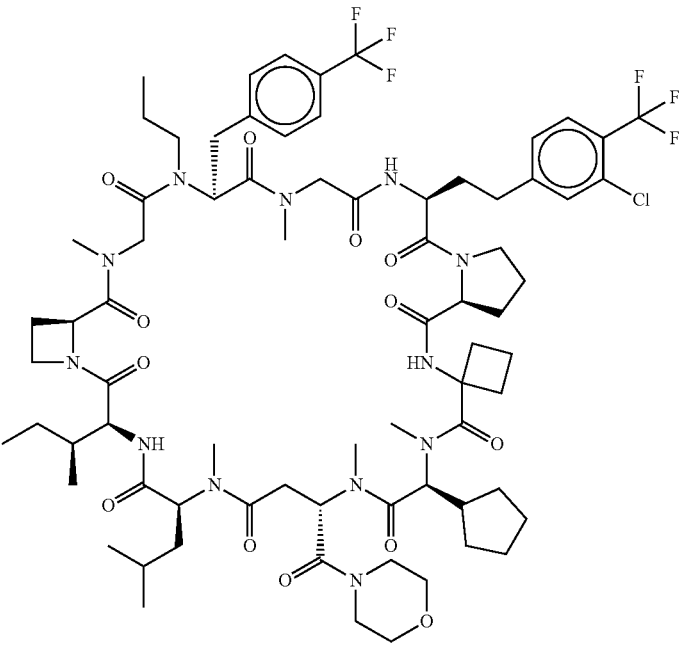 |

TABLE 38-continued
| Compound No. | Structural Formula |
|---|---|
| PP0403 | 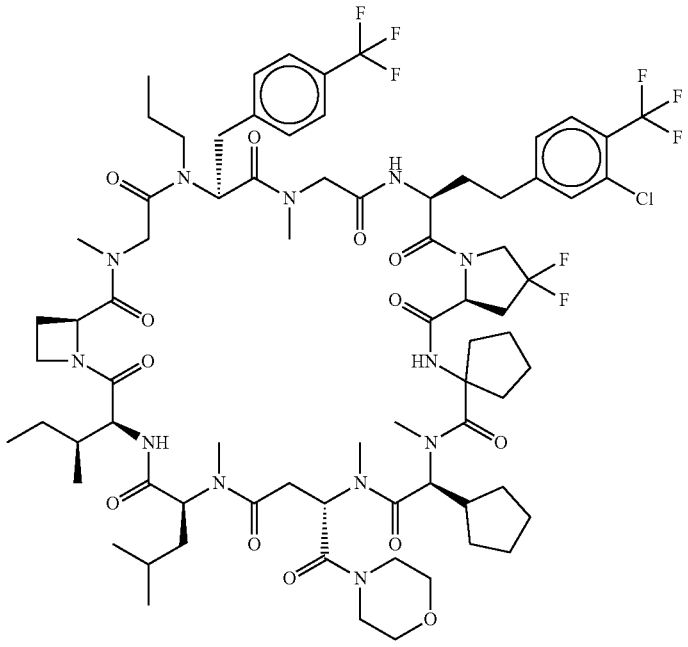 |
| PP0404 | 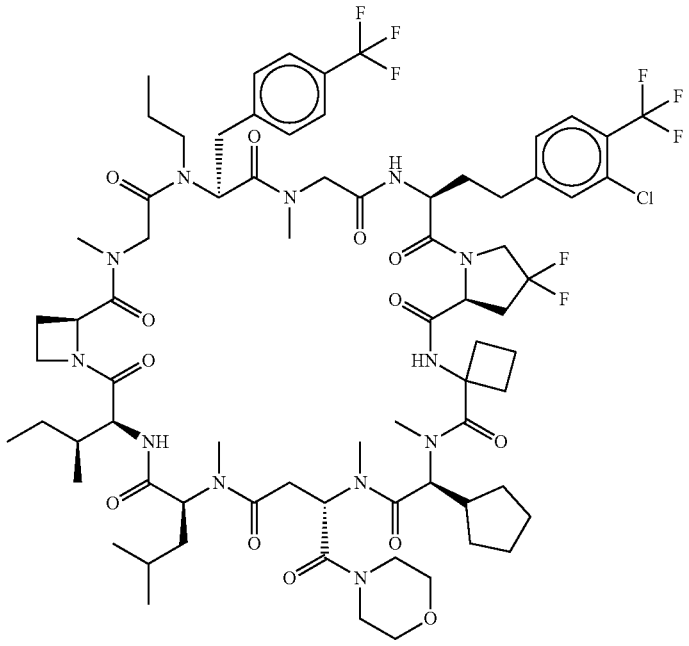 |

TABLE 38-continued

| Compound No. | Structural Formula |
|---|---|
| PP0405 | |
| PP0406 | |

TABLE 38-continued

| Compound No. | Structural Formula |
|---|---|
| PP0407 | |
| PP0408 | |

TABLE 38-continued

| Compound No. | Structural Formula |
|---|---|
| PP0409 | |
| PP0410 | |

TABLE 38-continued
| Compound No. | Structural Formula |
|---|---|
| PP0411 | 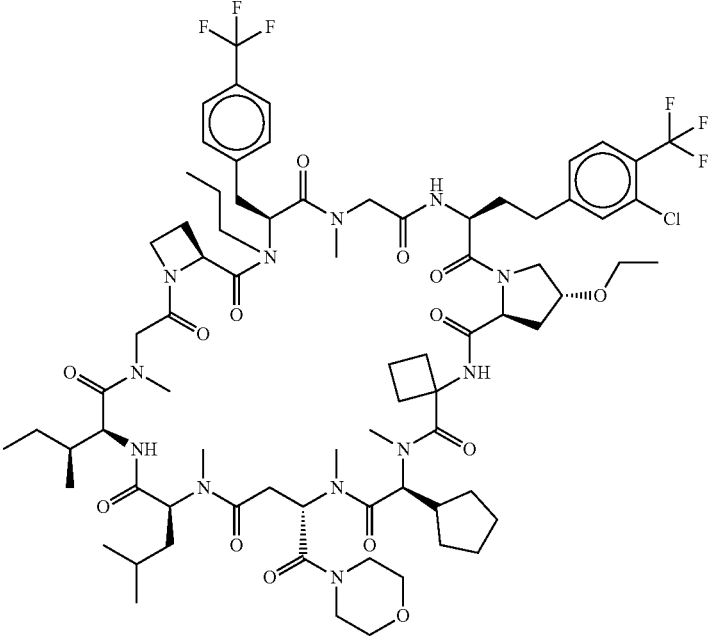 |
| PP0412 | 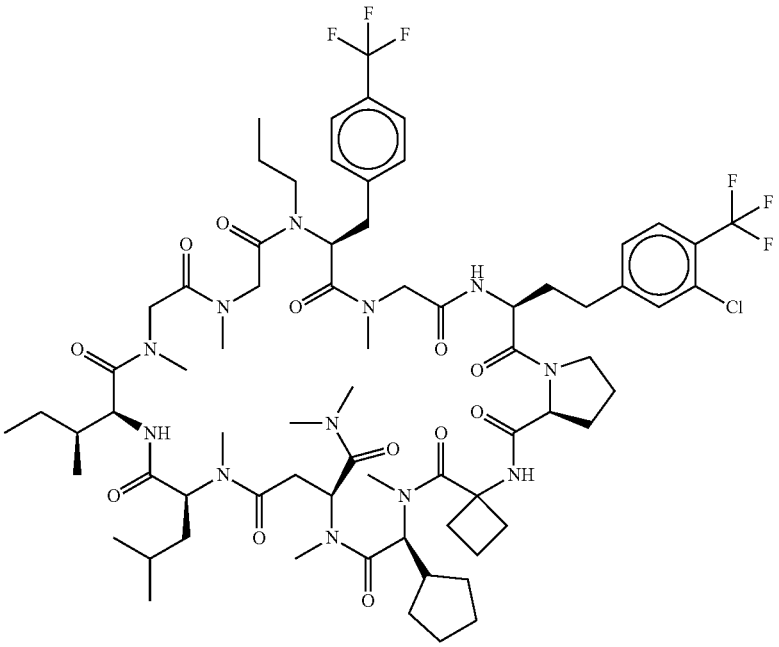 |

TABLE 38-continued

| Compound No. | Structural Formula |
| --- | --- |
| PP0413 | |
| PP0414 | |

TABLE 38-continued
| Compound No. | Structural Formula |
|---|---|
| PP0415 | 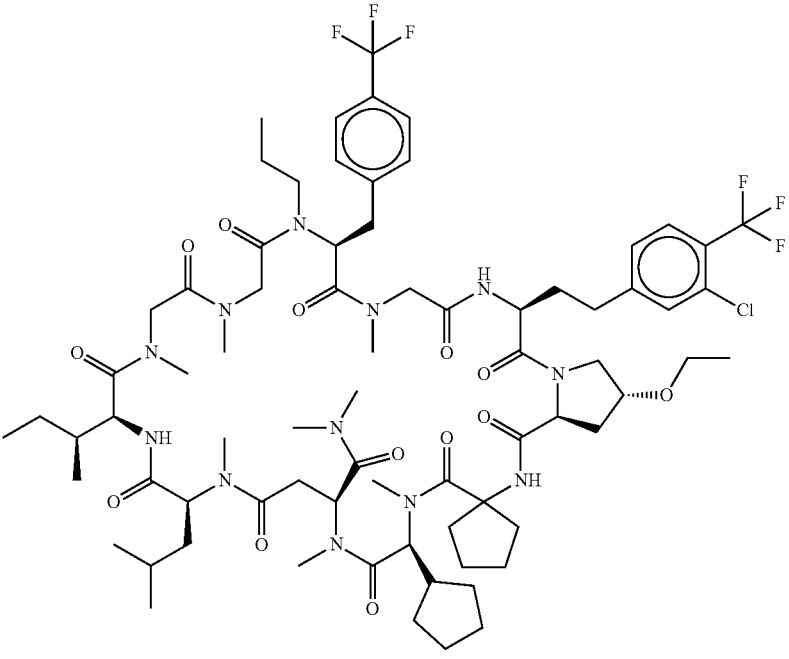 |
| PP0416 | 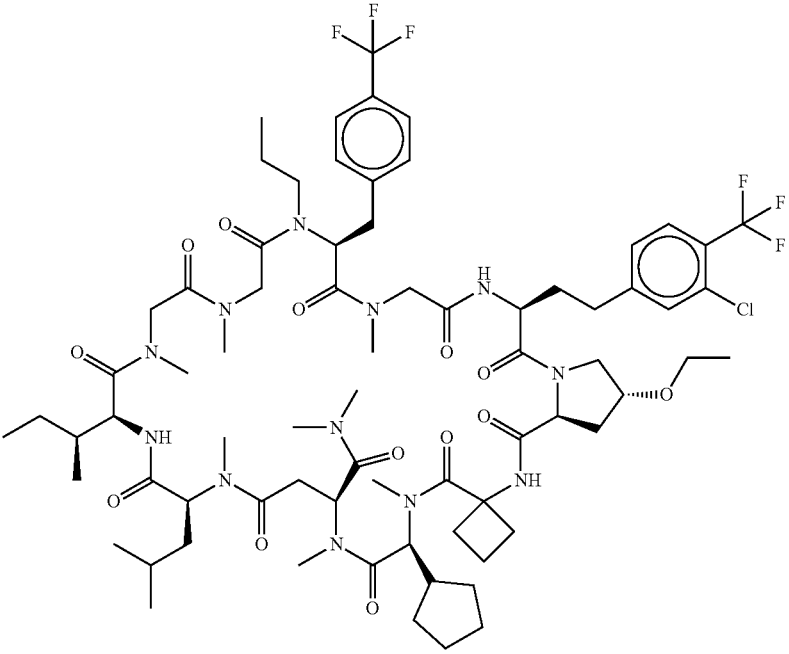 |

TABLE 38-continued
| Compound No. | Structural Formula |
|---|---|
| PP0417 | 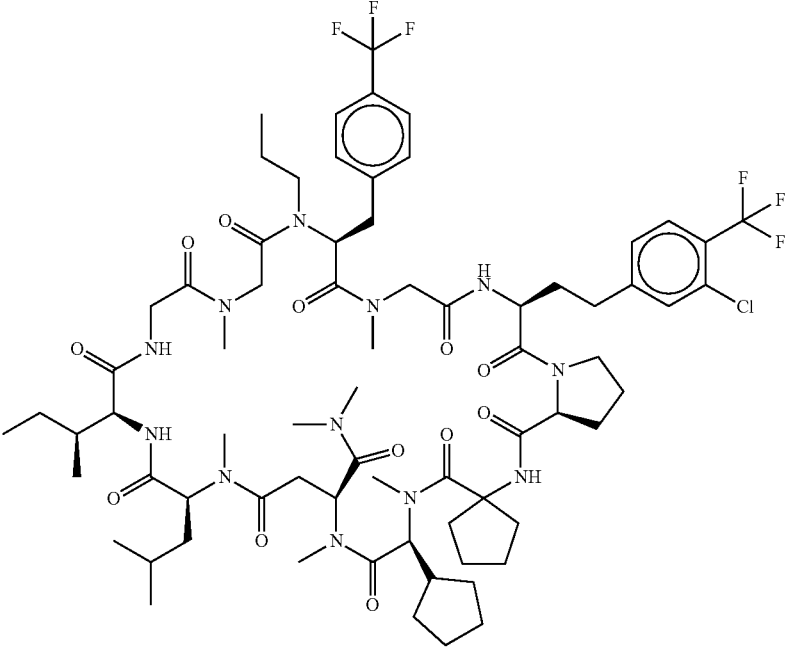 |
| PP0418 | 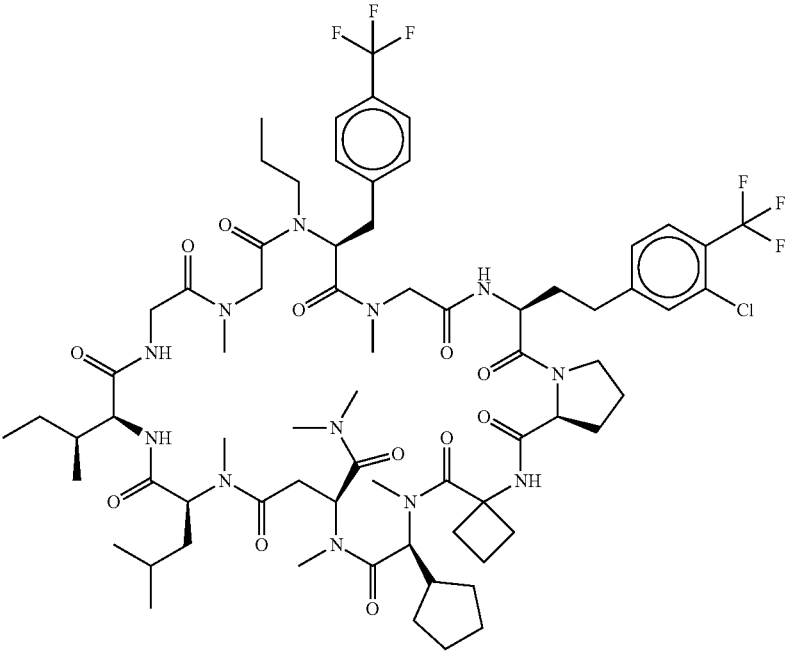 |

TABLE 38-continued

| Compound No. | Structural Formula |
|---|---|
| PP0419 | |
| PP0420 | |

TABLE 38-continued
| Compound No. | Structural Formula |
|---|---|
| PP0421 | 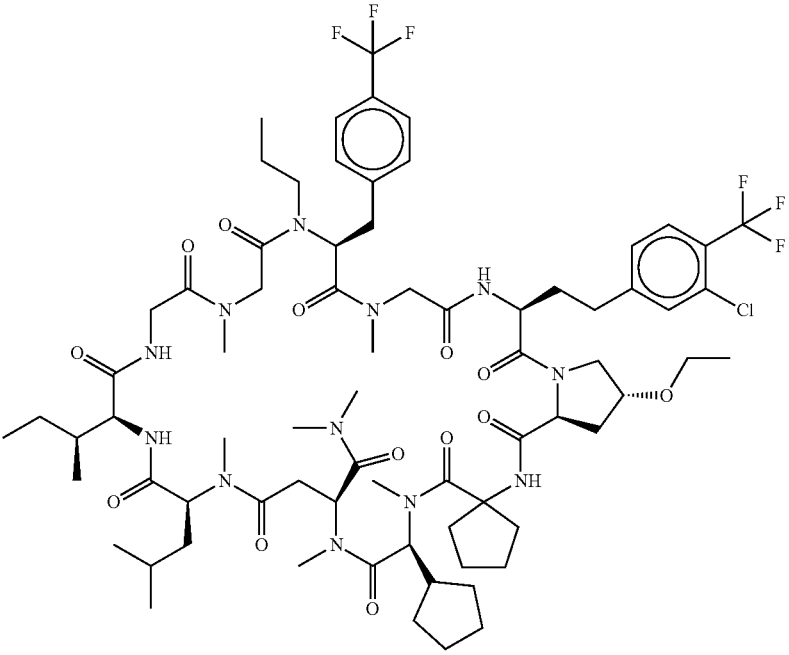 |
| PP0422 | 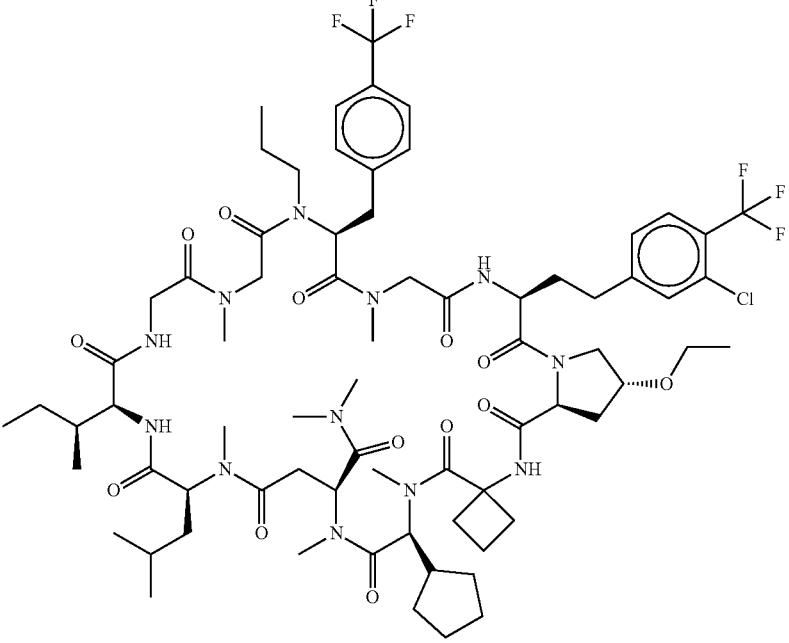 |

TABLE 38-continued
| Compound No. | Structural Formula |
|---|---|
| PP0423 | 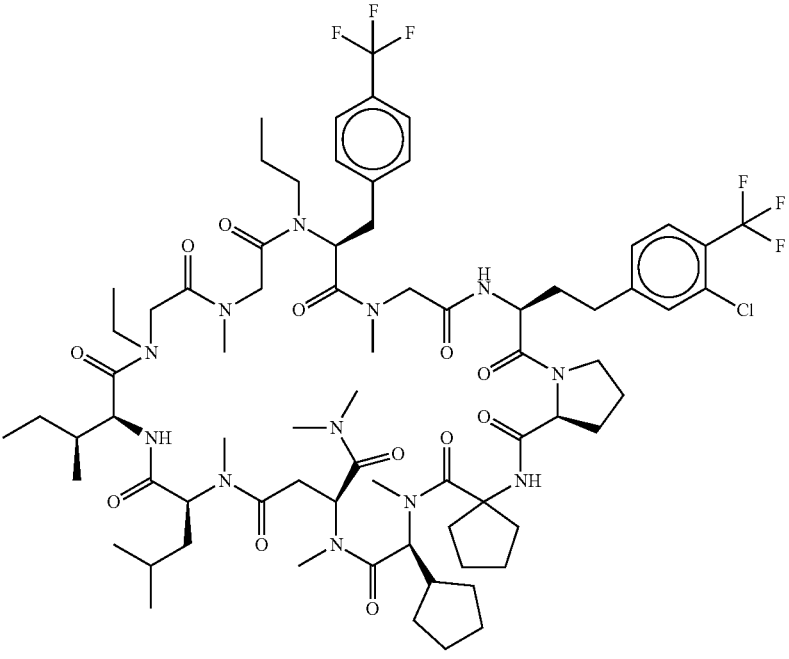 |
| PP0424 | 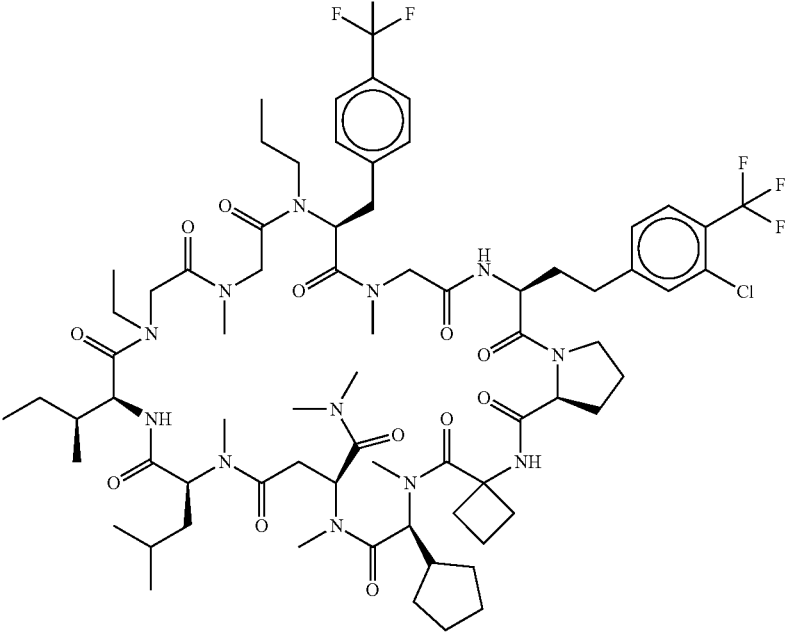 |

TABLE 38-continued
| Compound No. | Structural Formula |
|---|---|
| PP0425 | 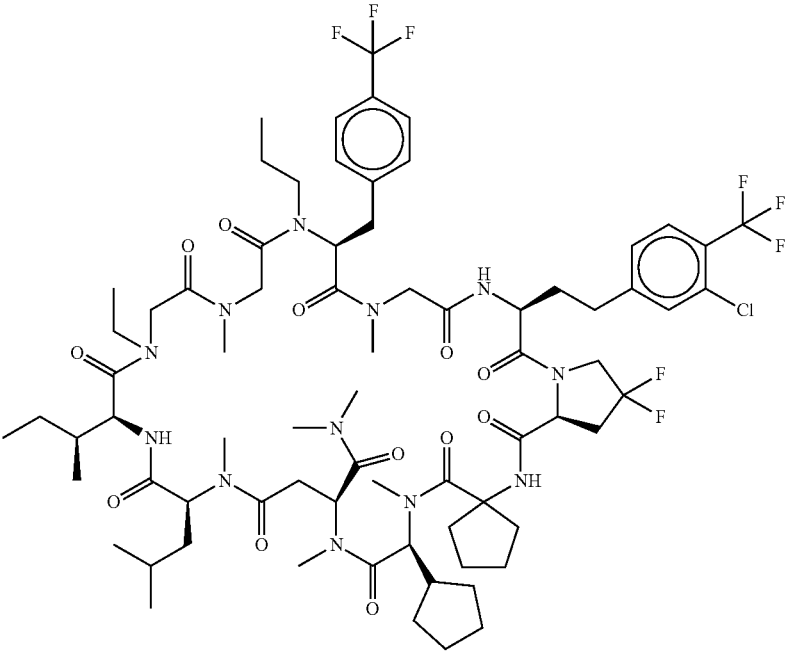 |
| PP0426 | 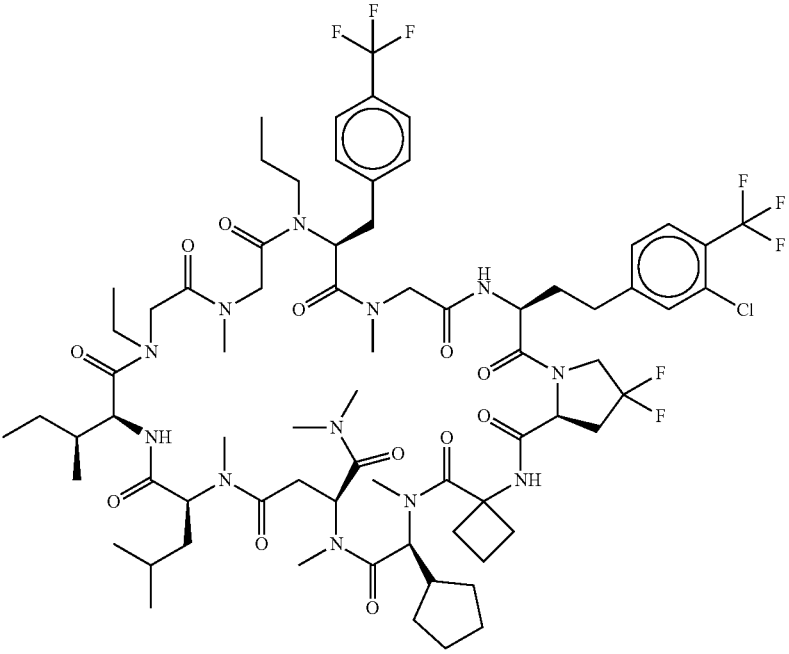 |

TABLE 38-continued

| Compound No. | Structural Formula |
|---|---|
| PP0427 | |
| PP0428 | |

TABLE 38-continued

| Compound No. | Structural Formula |
|---|---|
| PP0429 | |
| PP0430 | |

TABLE 38-continued

| Compound No. | Structural Formula |
|---|---|
| PP0431 | |
| PP0432 | |

TABLE 38-continued

| Compound No. | Structural Formula |
|---|---|
| PP0433 | |
| PP0434 | |

TABLE 38-continued

| Compound No. | Structural Formula |
|---|---|
| PP0435 | |
| PP0436 | |

TABLE 38-continued
| Compound No. | Structural Formula |
|---|---|
| PP0437 | 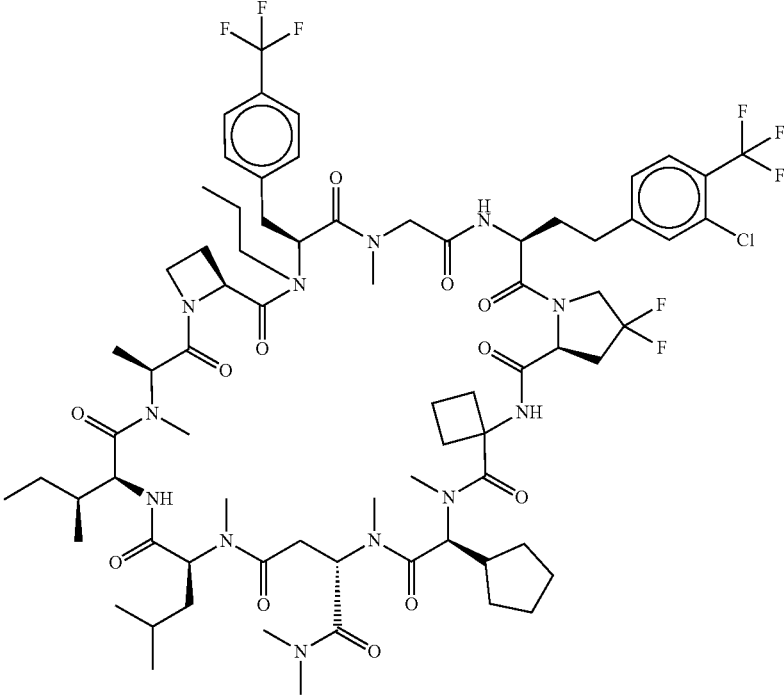 |
| PP0438 | 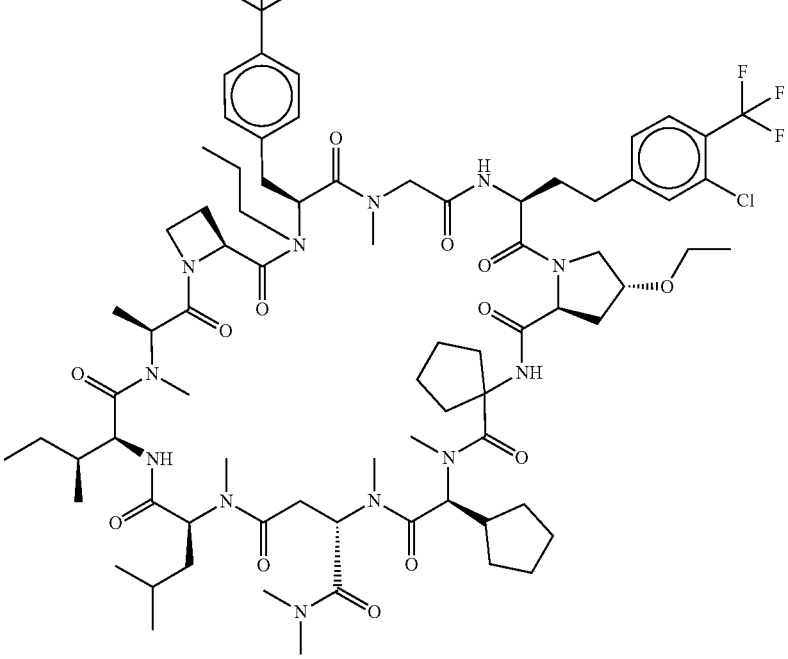 |

TABLE 38-continued

| Compound No. | Structural Formula |
|---|---|
| PP0439 | |
| PP0440 | |

TABLE 38-continued

| Compound No. | Structural Formula |
|---|---|
| PP0441 | |
| PP0442 | |

TABLE 38-continued

| Compound No. | Structural Formula |
| --- | --- |
| PP0443 | |
| PP0444 | |

TABLE 38-continued

| Compound No. | Structural Formula |
|---|---|
| PP0445 | |
| PP0446 | |

TABLE 38-continued
| Compound No. | Structural Formula |
|---|---|
| PP0447 | 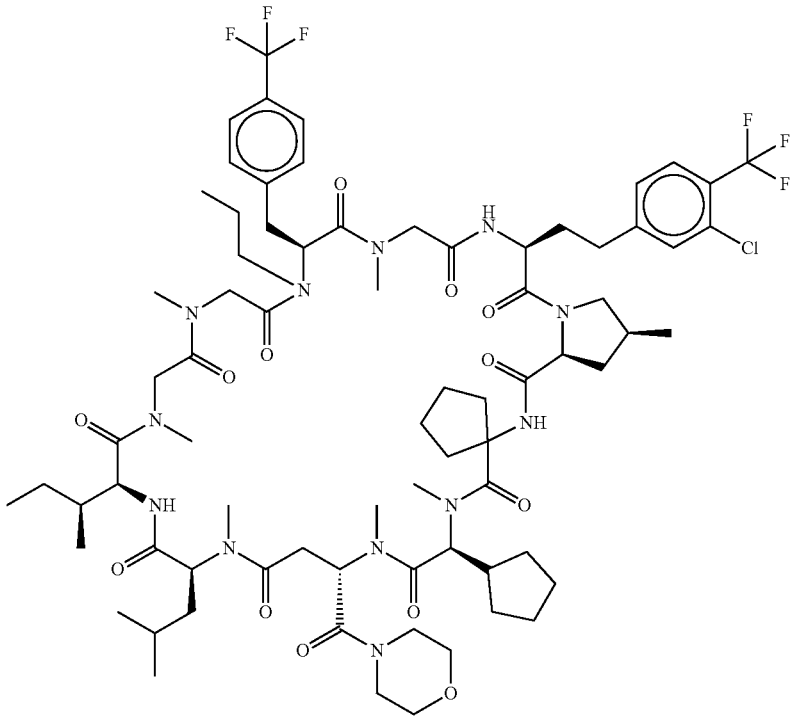 |
| PP0448 | 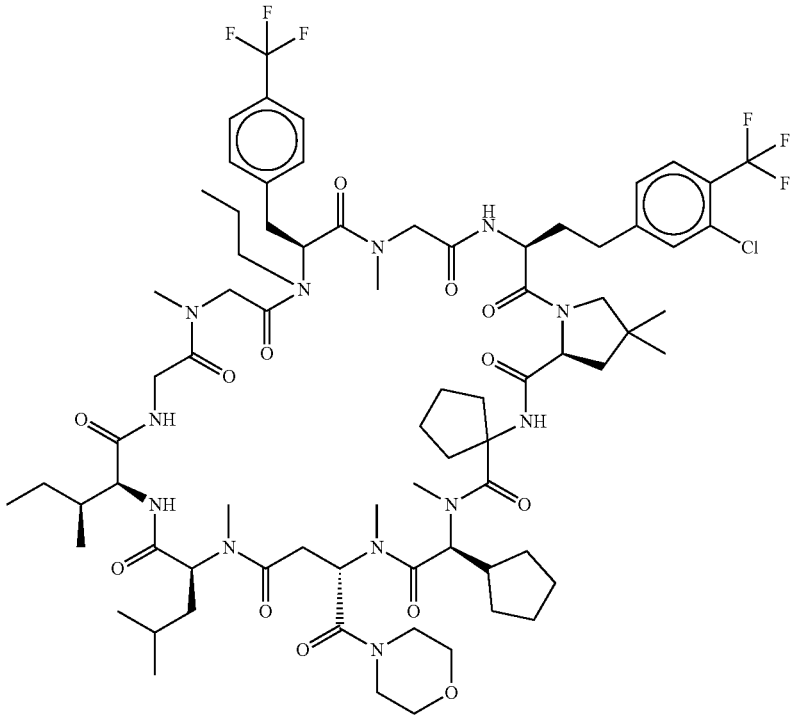 |

TABLE 38-continued

| Compound No. | Structural Formula |
|---|---|
| PP0449 | |
| PP0450 | |

TABLE 38-continued
| Compound No. | Structural Formula |
|---|---|
| PP0451 | 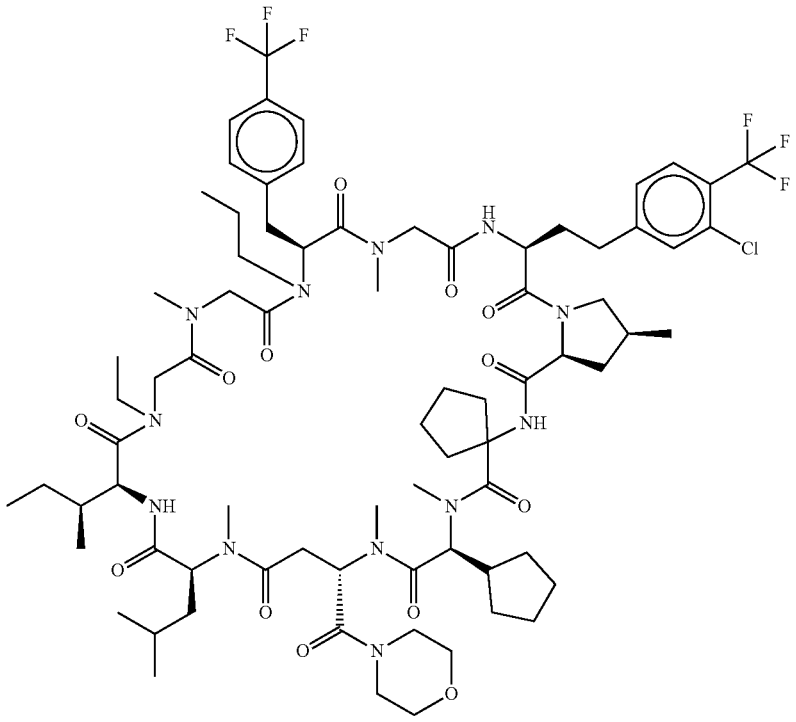 |
| PP0452 | 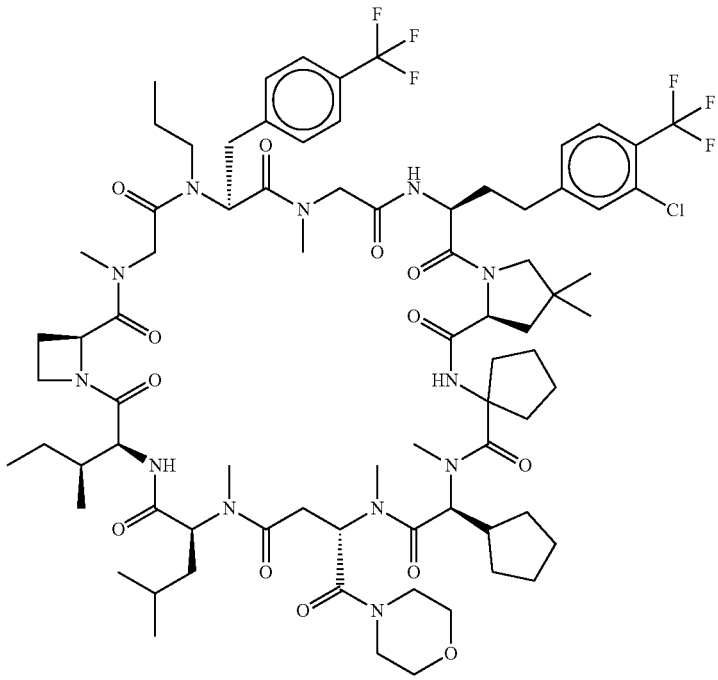 |

TABLE 38-continued

| Compound No. | Structural Formula |
|---|---|
| PP0453 | |
| PP0454 | |

TABLE 38-continued

| Compound No. | Structural Formula |
|---|---|
| PP0455 | |
| PP0456 | |

TABLE 38-continued
| Compound No. | Structural Formula |
|---|---|
| PP0457 | 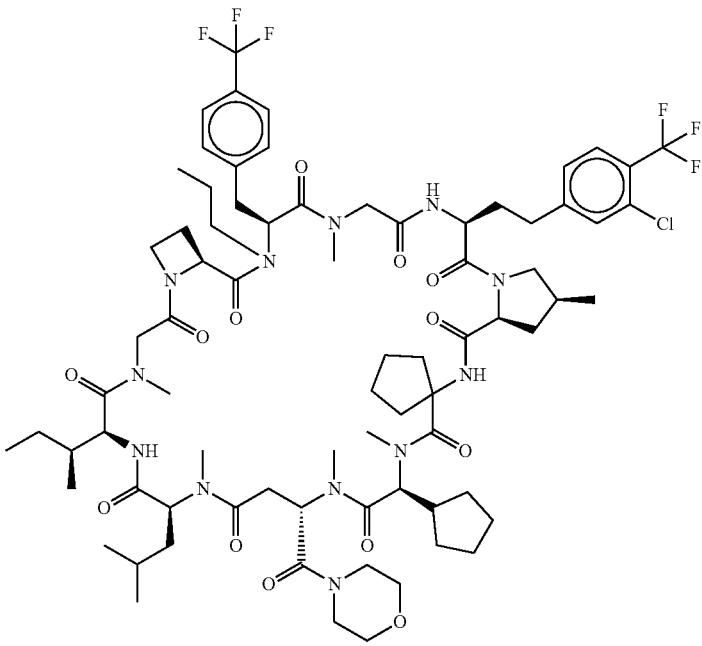 |
| PP0460 | 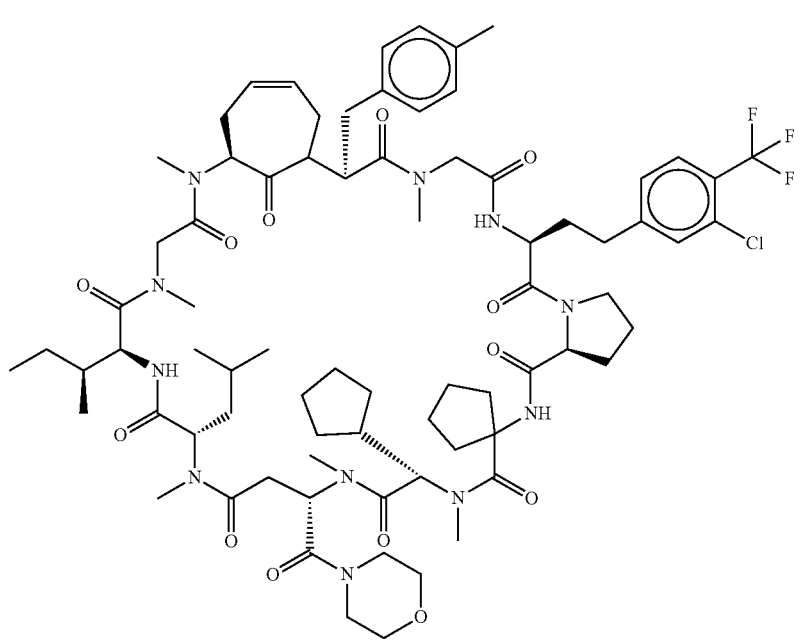 |

TABLE 38-continued

| Compound No. | Structural Formula |
|---|---|
| PP0461 | |
| PP0462 | |

TABLE 38-continued

| Compound No. | Structural Formula |
| --- | --- |
| PP0463 | |
| PP0464 | |

TABLE 38-continued

| Compound No. | Structural Formula |
|---|---|
| PP0465 | |
| PP0466 | |

TABLE 38-continued
| Compound No. | Structural Formula |
|---|---|
| PP0467 | 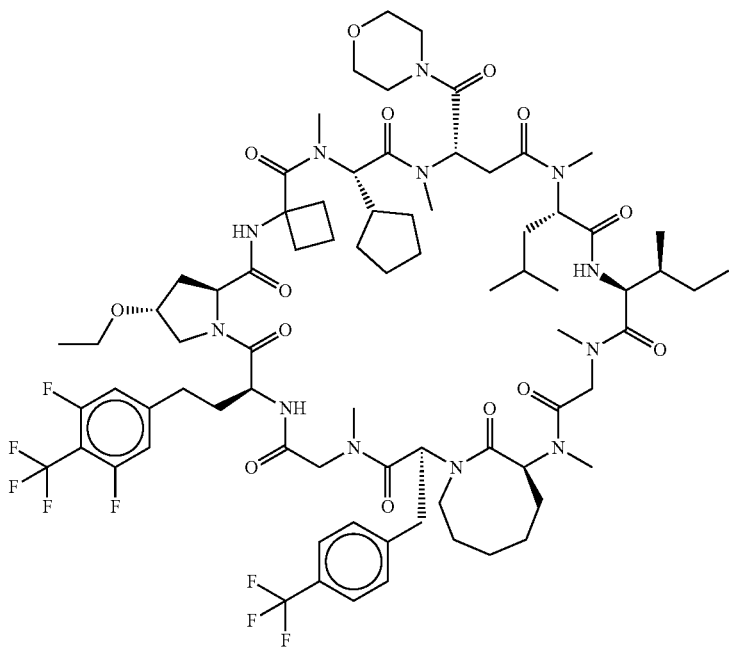 |
| PP0468 | 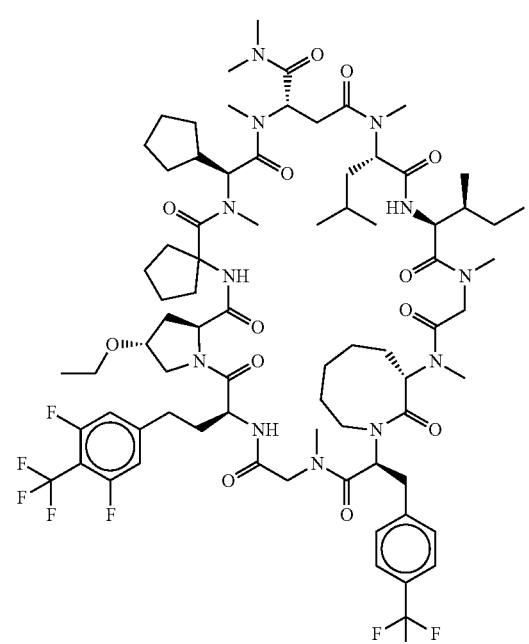 |

TABLE 38-continued
| Compound No. | Structural Formula |
|---|---|
| PP0469 | 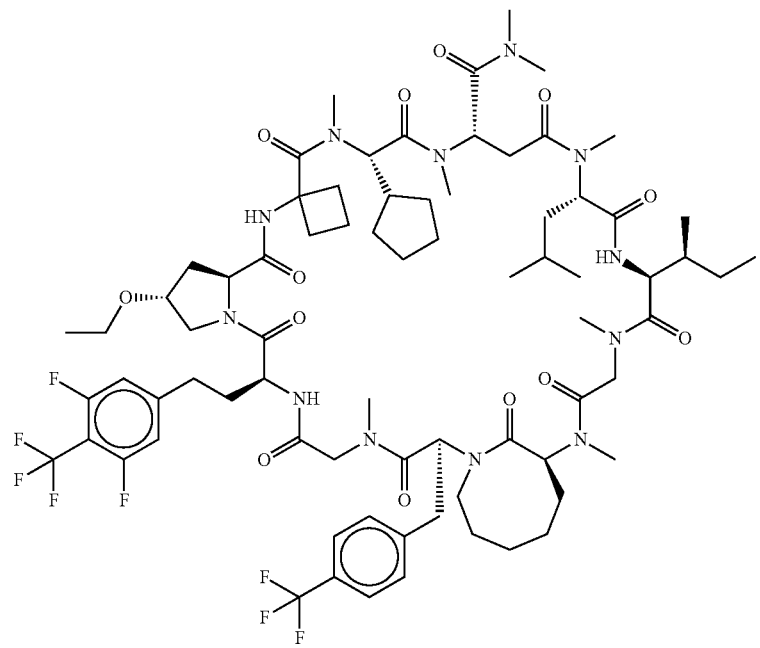 |
| PP0470 | 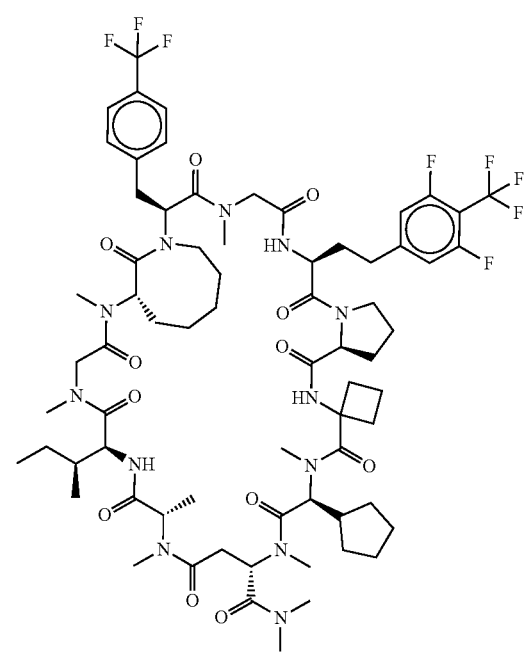 |

TABLE 38-continued

| Compound No. | Structural Formula |
|---|---|
| PP0471 | |
| PP0472 | |

TABLE 38-continued

| Compound No. | Structural Formula |
|---|---|
| PP0473 | |
| PP0474 | |

TABLE 38-continued
| Compound No. | Structural Formula |
|---|---|
| PP0475 | 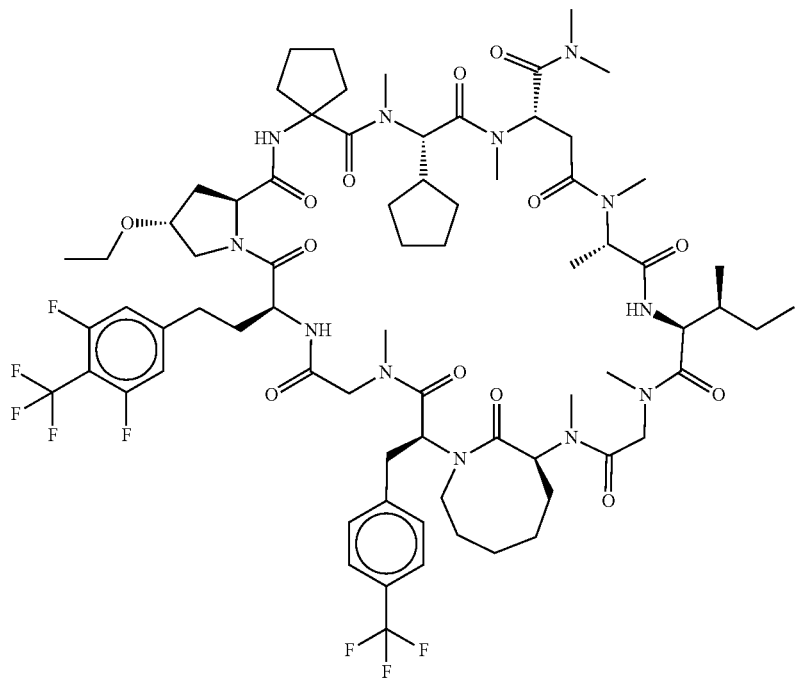 |
| PP0476 | 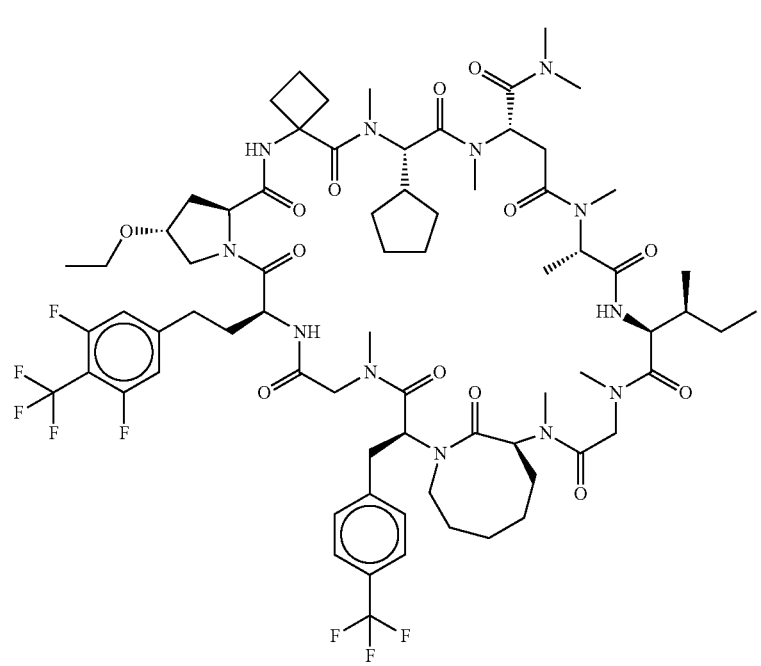 |

TABLE 38-continued
| Compound No. | Structural Formula |
|---|---|
| PP0477 | 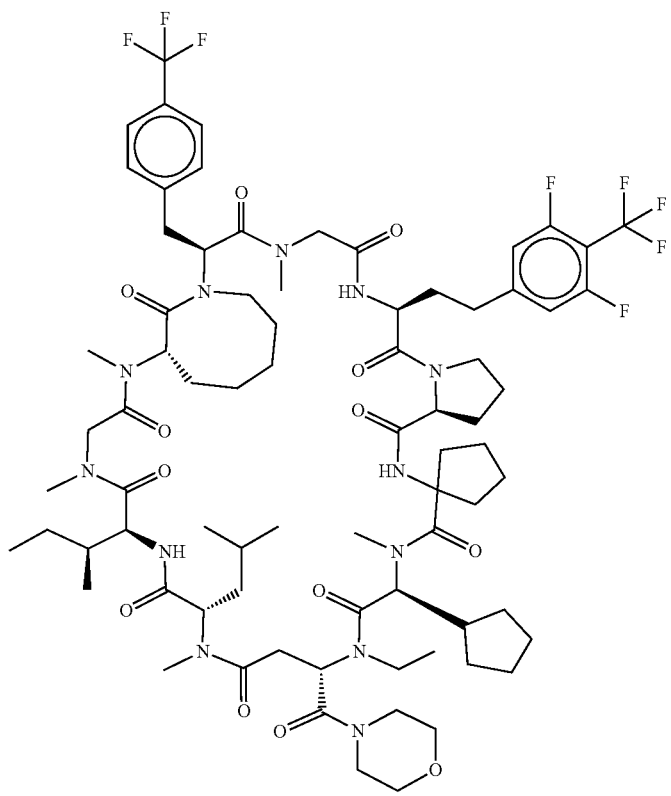 |
| PP0478 | 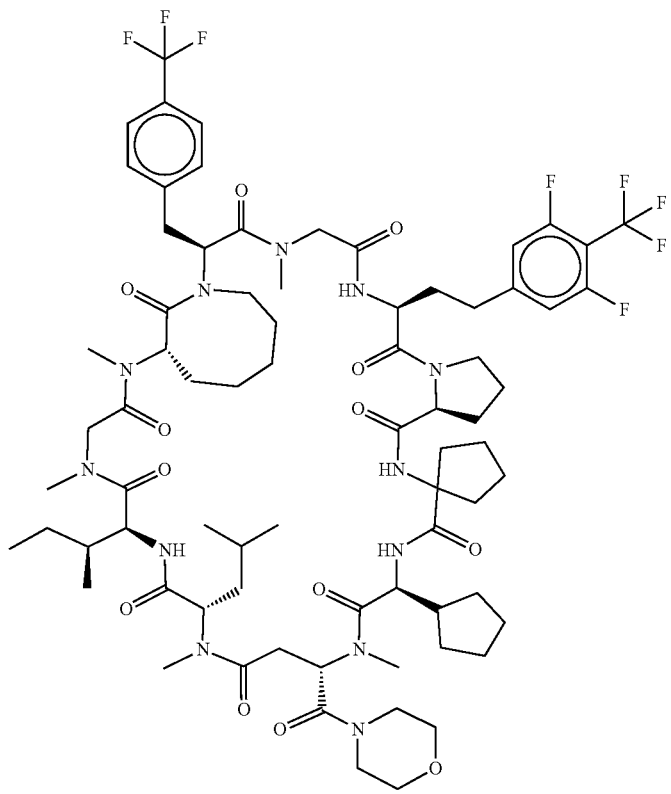 |

TABLE 38-continued
| Compound No. | Structural Formula |
|---|---|
| PP0479 | 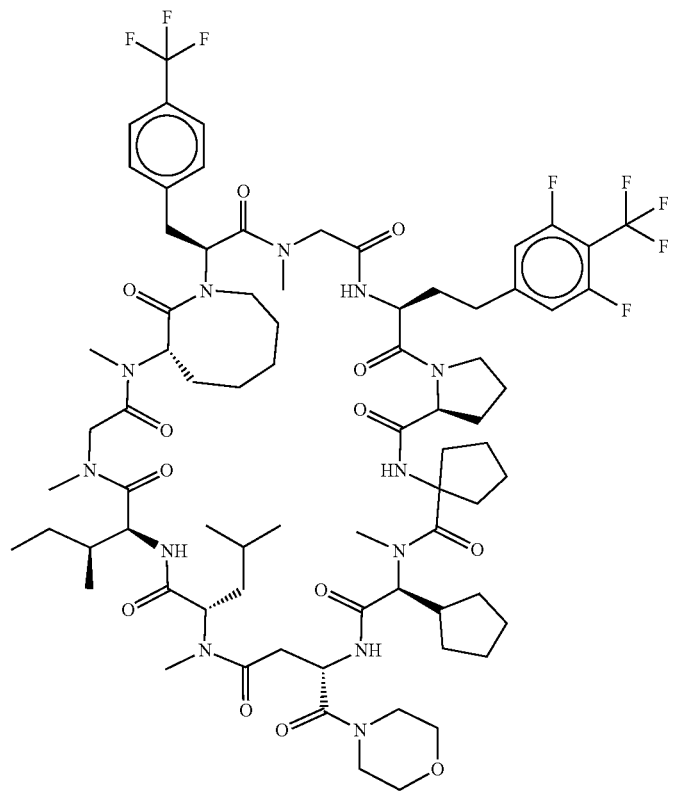 |
| PP0480 | 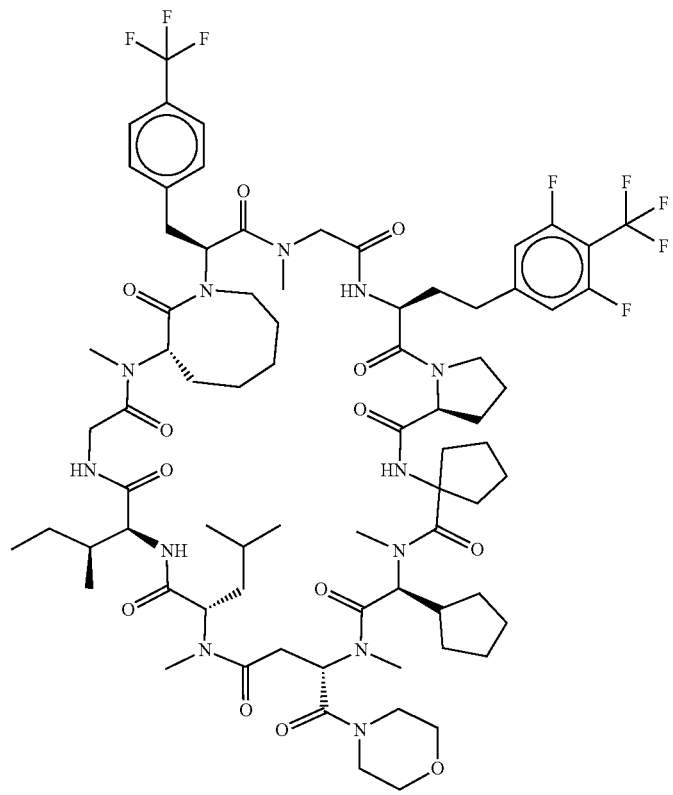 |

TABLE 38-continued
| Compound No. | Structural Formula |
|---|---|
| PP0481 | 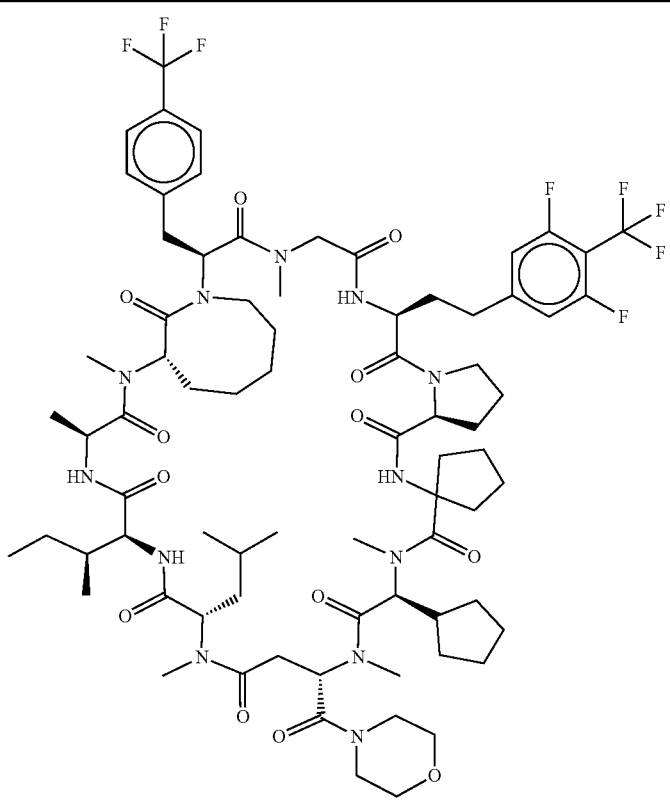 |
| PP0483 | 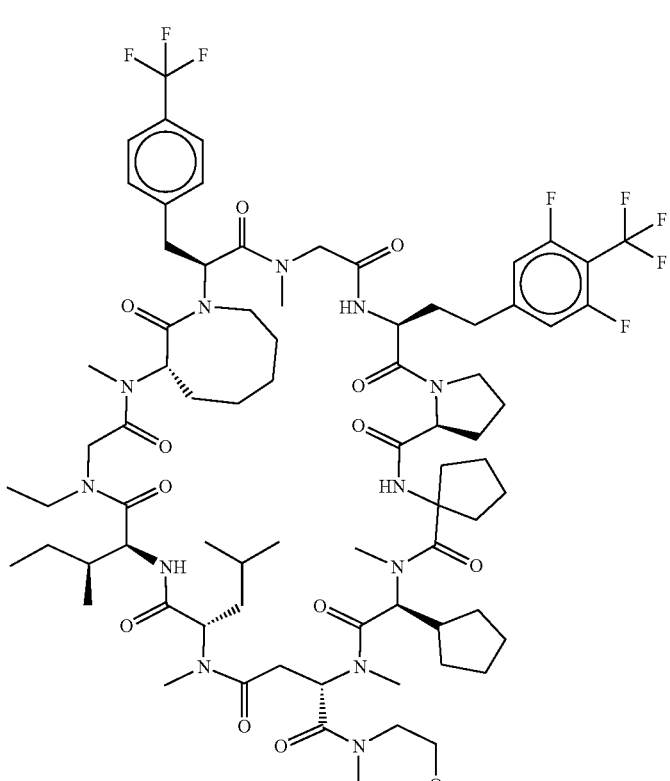 |

TABLE 38-continued
| Compound No. | Structural Formula |
|---|---|
| PP0484 | 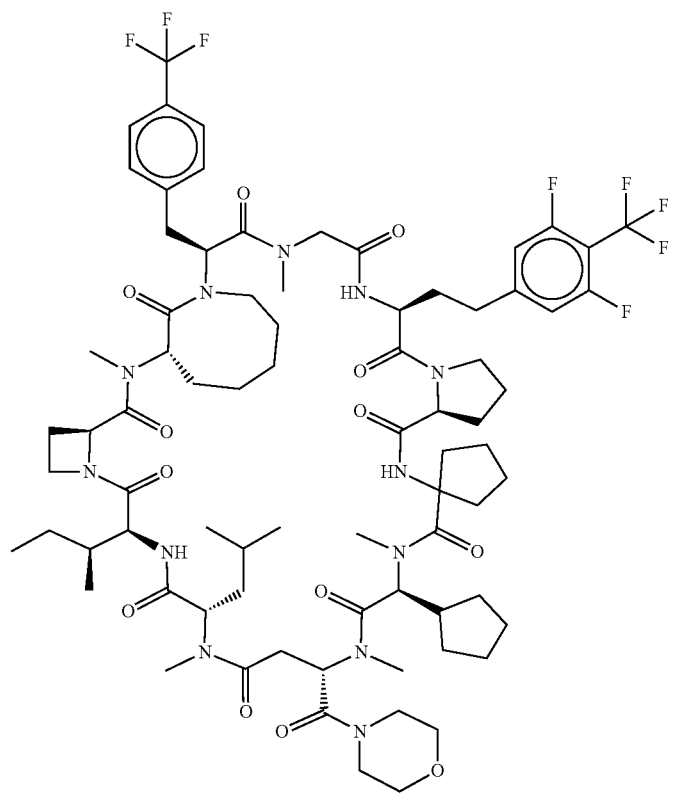 |
| PP0485 | 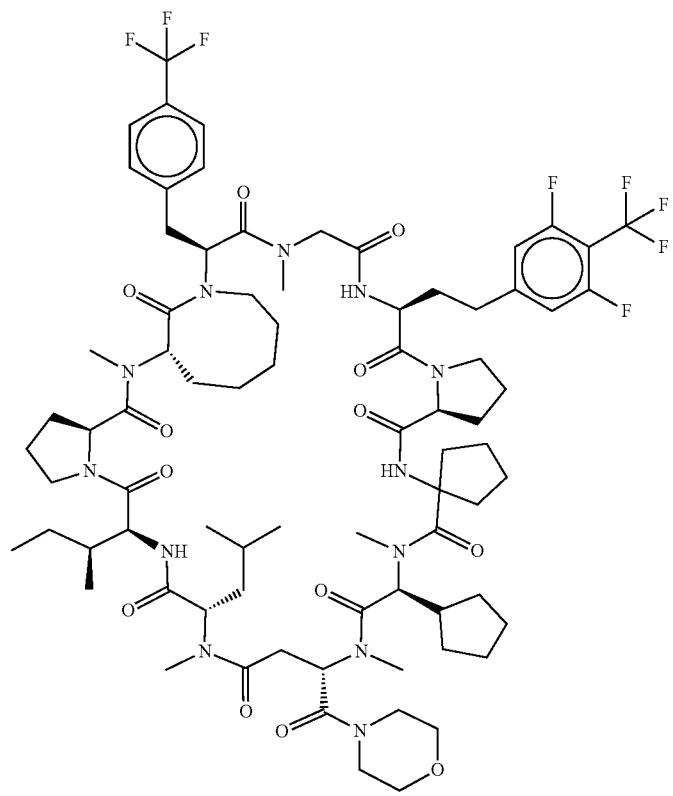 |

TABLE 38-continued
| Compound No. | Structural Formula |
|---|---|
| PP0487 | 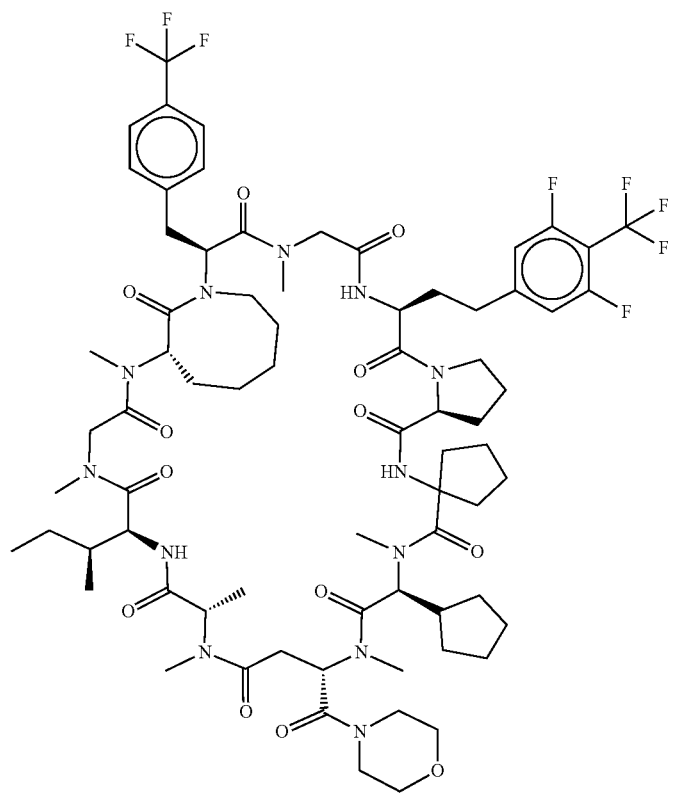 |
| PP0488 | 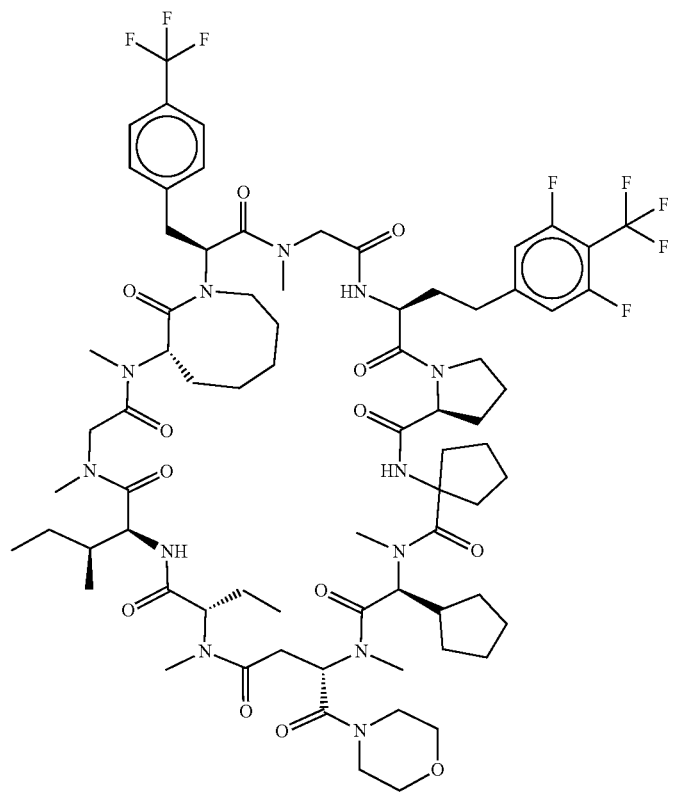 |

TABLE 38-continued
| Compound No. | Structural Formula |
|---|---|
| PP0490 | 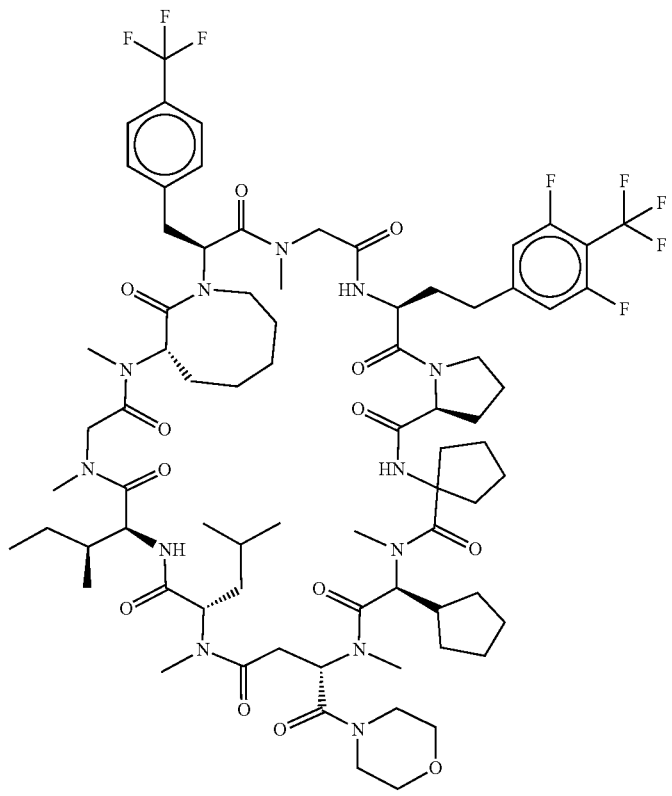 |
| PP0491 | 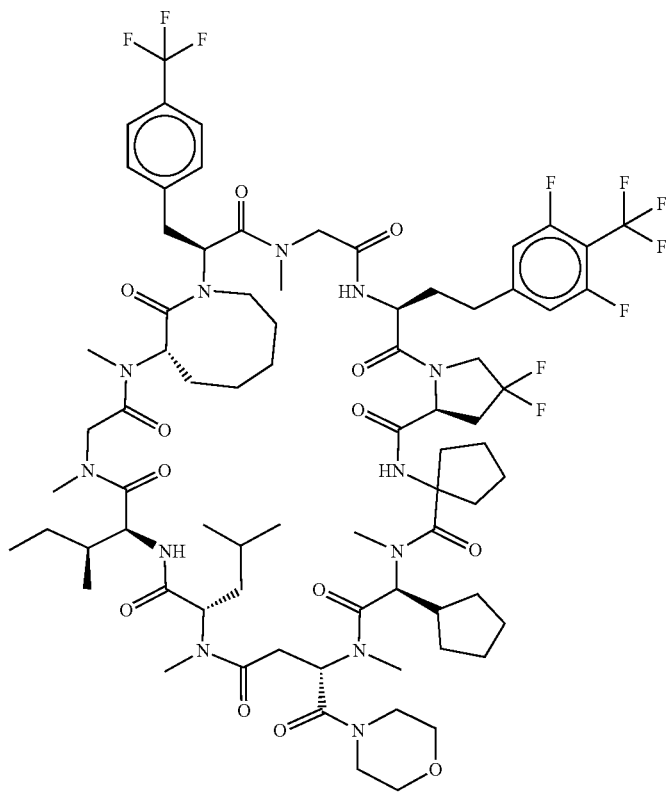 |

TABLE 38-continued
| Compound No. | Structural Formula |
|---|---|
| PP0492 | 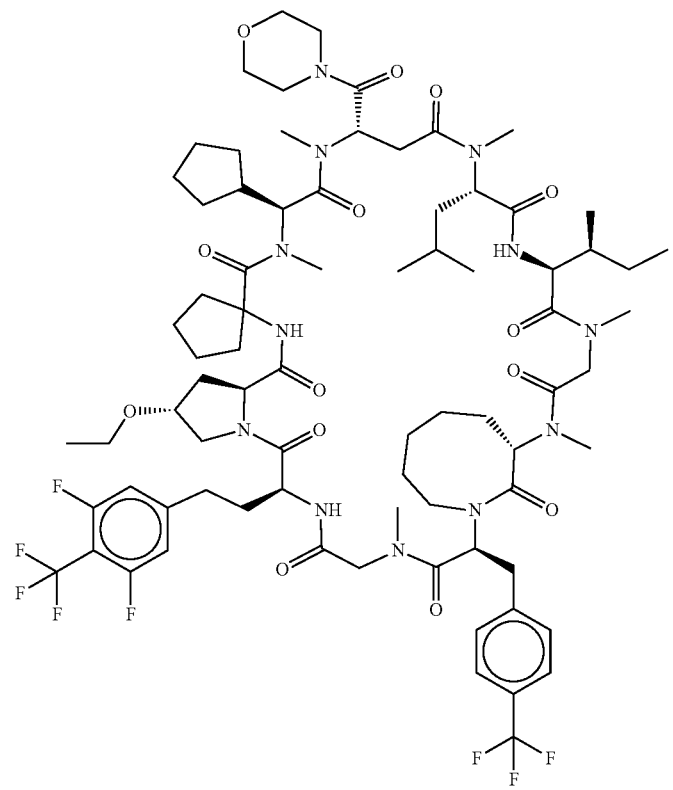 |
| PP0493 | 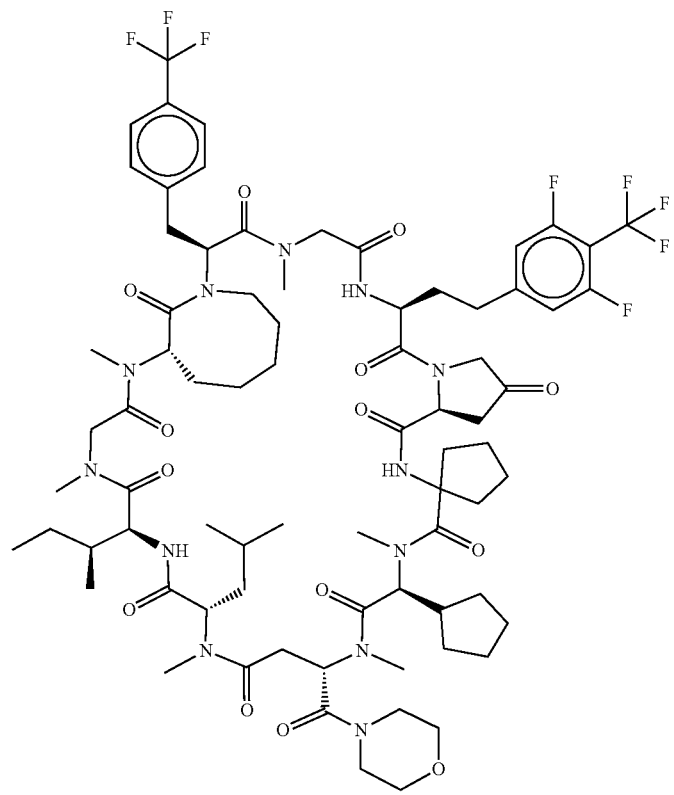 |

TABLE 38-continued

| Compound No. | Structural Formula |
| --- | --- |
| PP0494 | |
| PP0495 | |

| Compound No. | Structural Formula |
|---|---|
| PP0496 | |
| PP0497 | |

TABLE 38-continued
| Compound No. | Structural Formula |
|---|---|
| PP0498 | 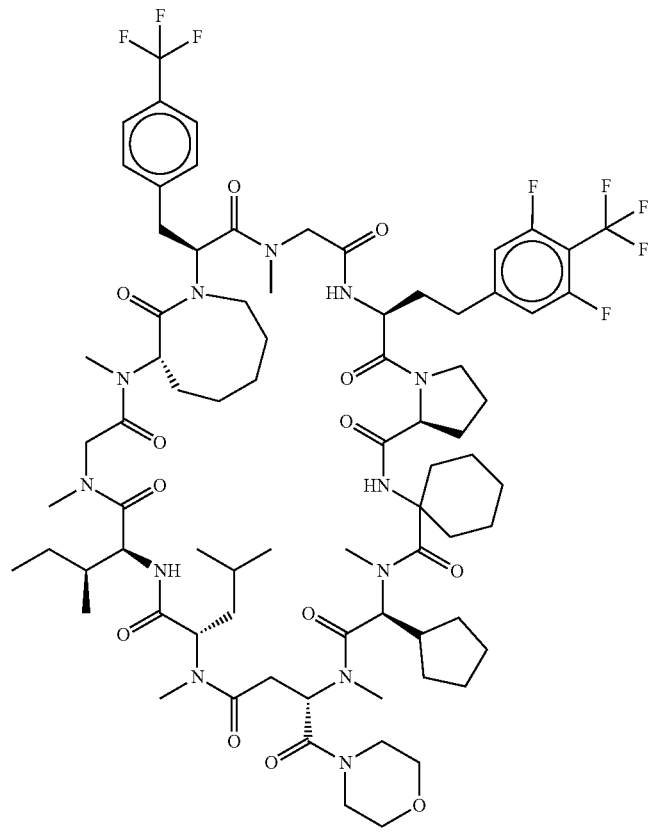 |

TABLE 38-continued
| Compound No. | Structural Formula |
|---|---|
| PP0499 | 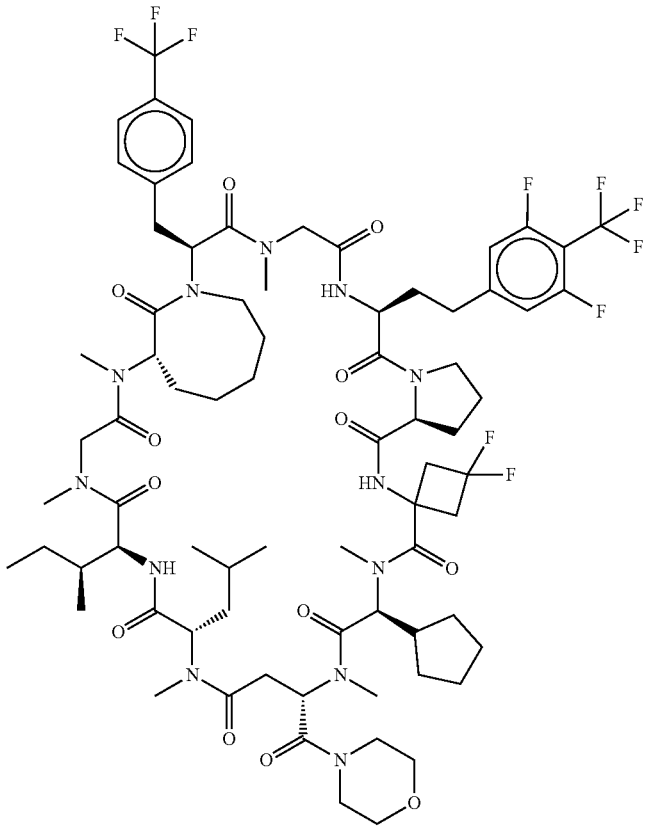 |
| PP0500 | 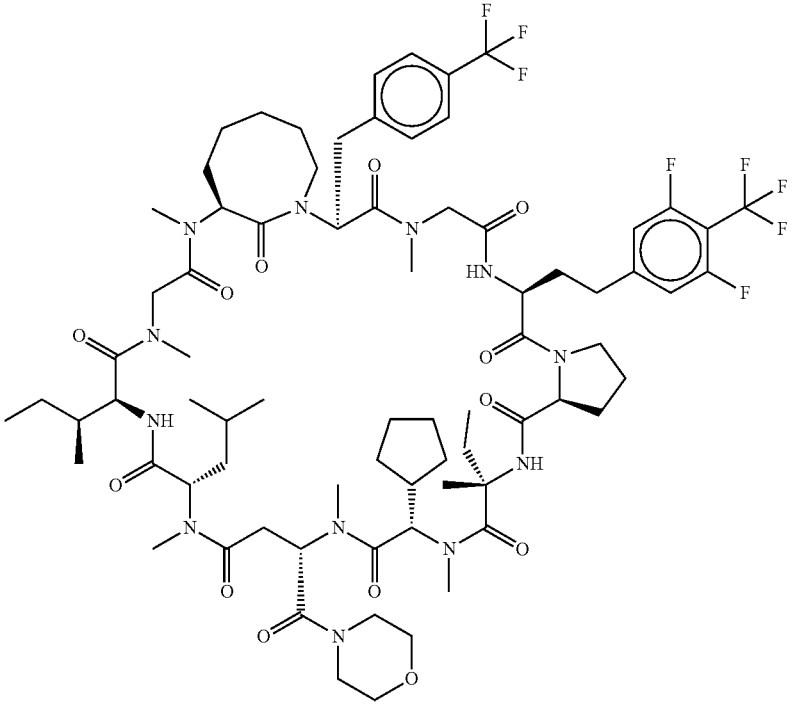 |

TABLE 38-continued
| Compound No. | Structural Formula |
|---|---|
| PP0501 | 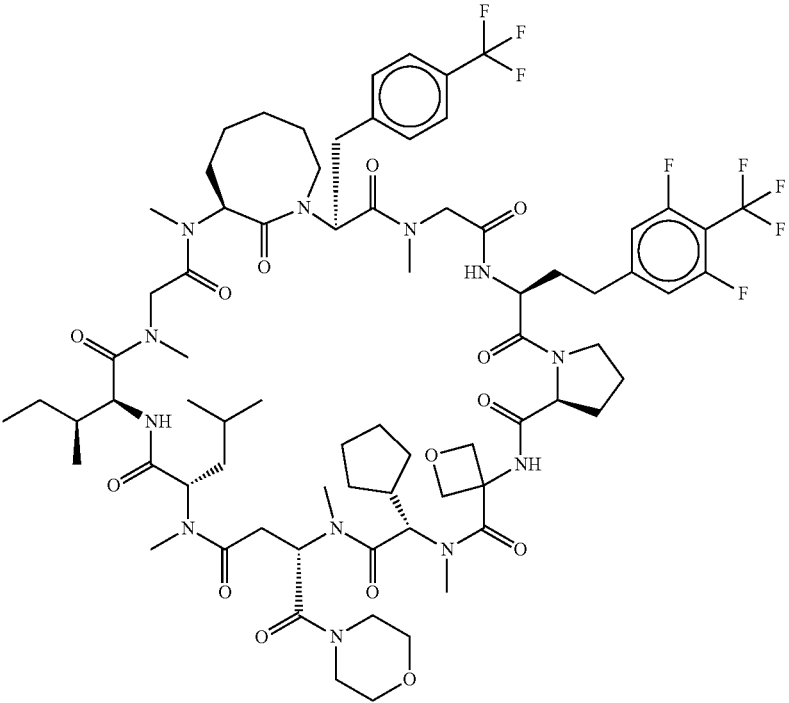 |
| PP0502 | 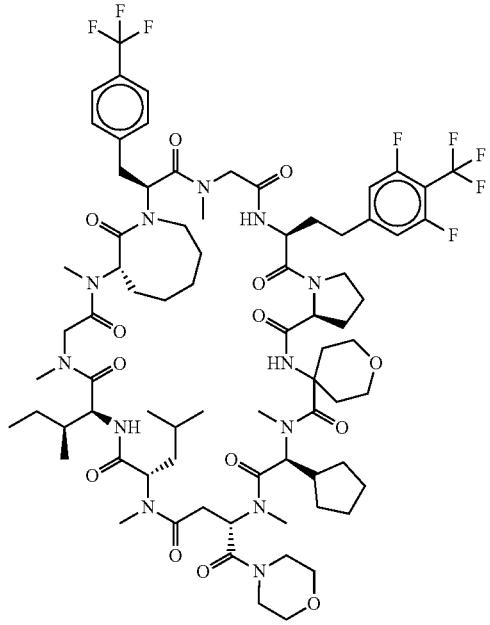 |

TABLE 38-continued

| Compound No. | Structural Formula |
|---|---|
| PP0503 | |
| PP0504 | |

TABLE 38-continued
| Compound No. | Structural Formula |
|---|---|
| PP0505 | 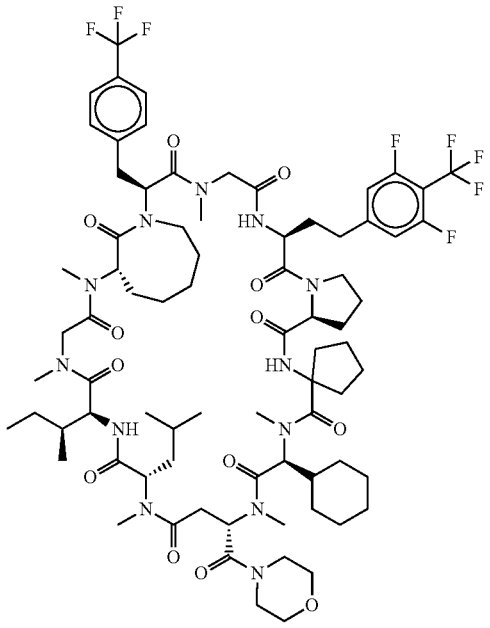 |
| PP0506 | 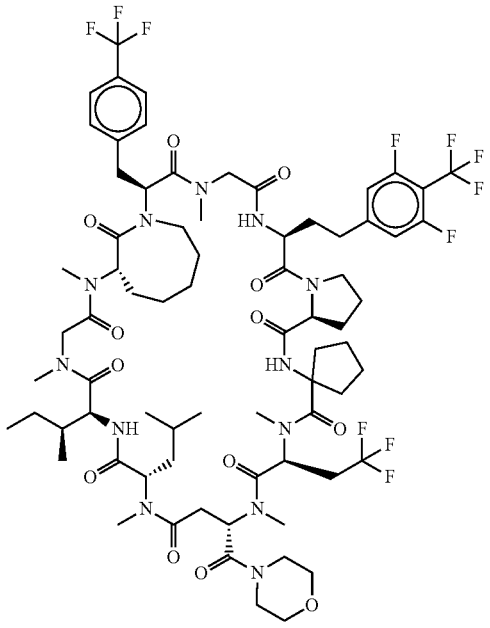 |

TABLE 38-continued
| Compound No. | Structural Formula |
|---|---|
| PP0507 | 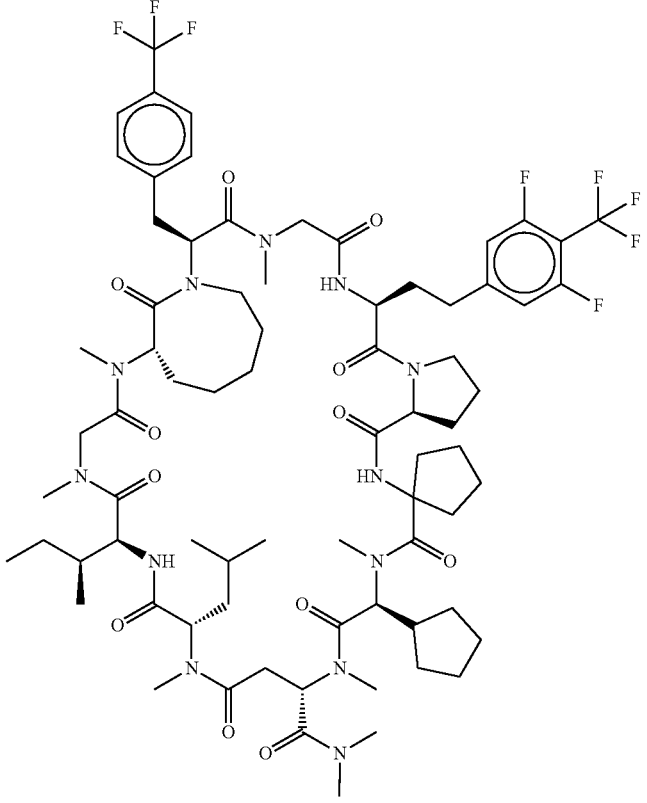 |
| PP0508 | 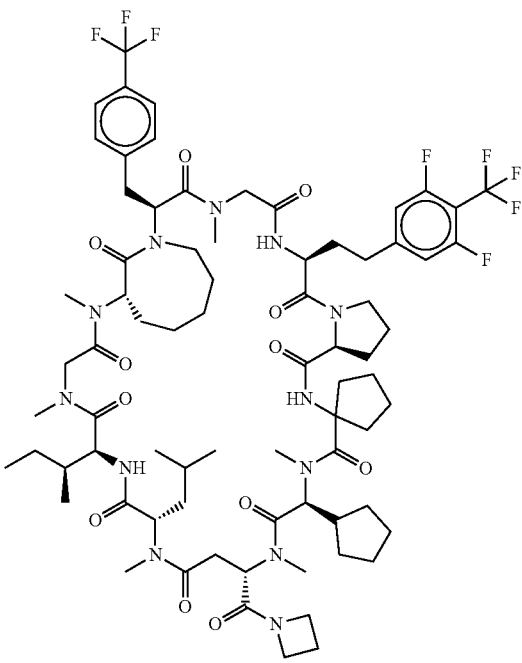 |

TABLE 38-continued

| Compound No. | Structural Formula |
|---|---|
| PP0509 | |
| PP0510 | |

TABLE 38-continued

| Compound No. | Structural Formula |
|---|---|
| PP0511 | |
| PP0512 | |

TABLE 38-continued

| Compound No. | Structural Formula |
|---|---|
| PP0513 | |
| PP0514 | |

TABLE 38-continued
| Compound No. | Structural Formula |
|---|---|
| PP0515 | 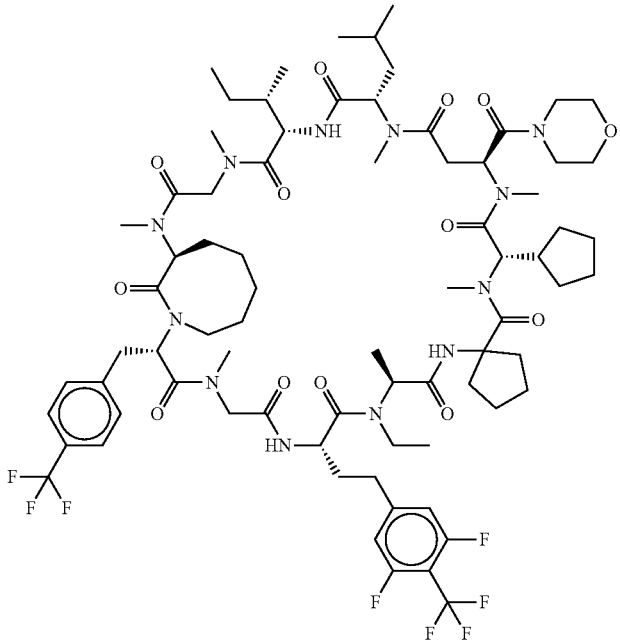 |
| PP0516 | 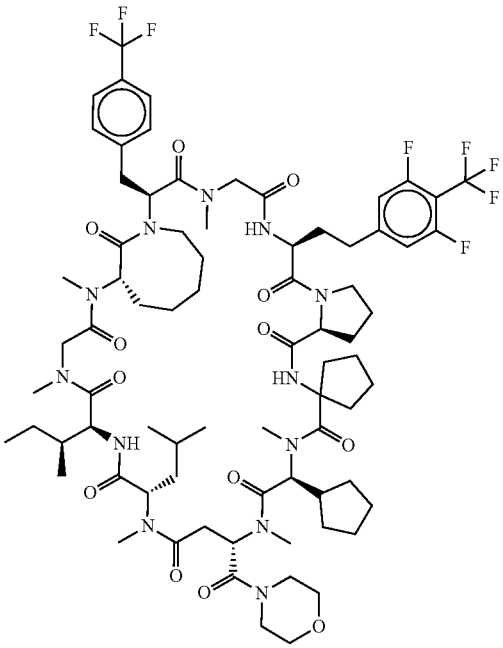 |

TABLE 38-continued
| Compound No. | Structural Formula |
|---|---|
| PP0520 | 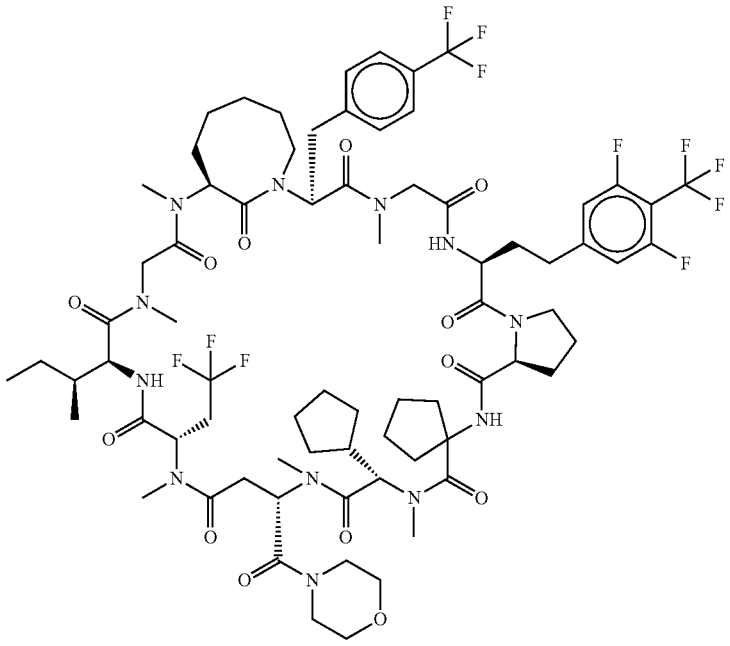 |
| PP0521 | 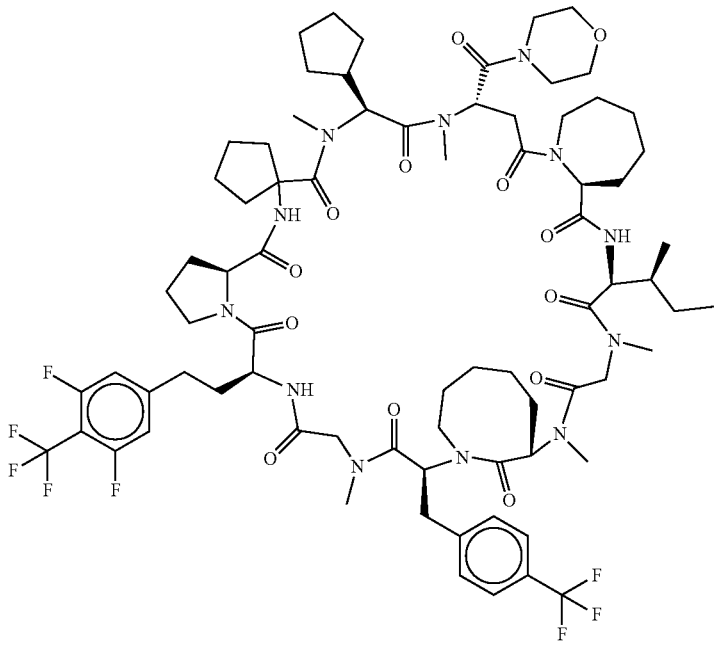 |

TABLE 38-continued

| Compound No. | Structural Formula |
| --- | --- |
| PP0522 | |
| PP0523 | |

TABLE 38-continued
| Compound No. | Structural Formula |
|---|---|
| PP0524 | 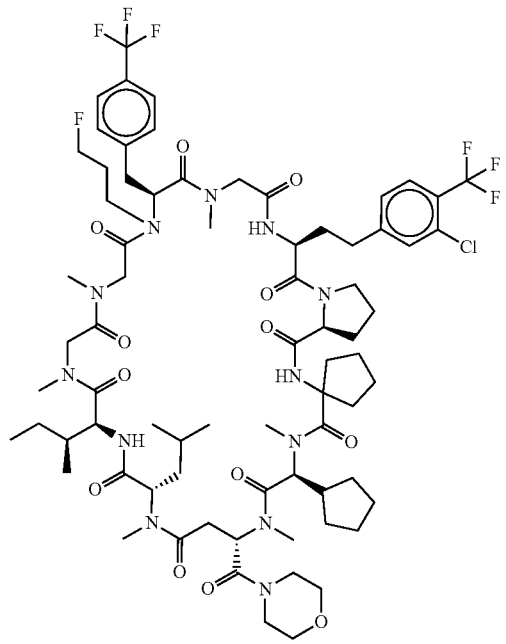 |
| PP0525 | 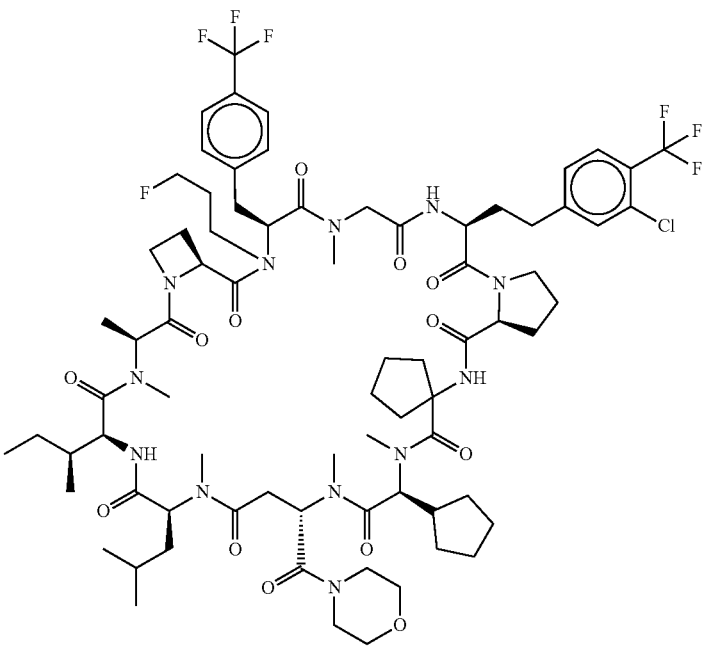 |

TABLE 38-continued

| Compound No. | Structural Formula |
|---|---|
| PP0526 | |
| PP0527 | |

TABLE 38-continued

| Compound No. | Structural Formula |
|---|---|
| PP0528 | |
| PP0529 | |

TABLE 38-continued
| Compound No. | Structural Formula |
|---|---|
| PP0530 | 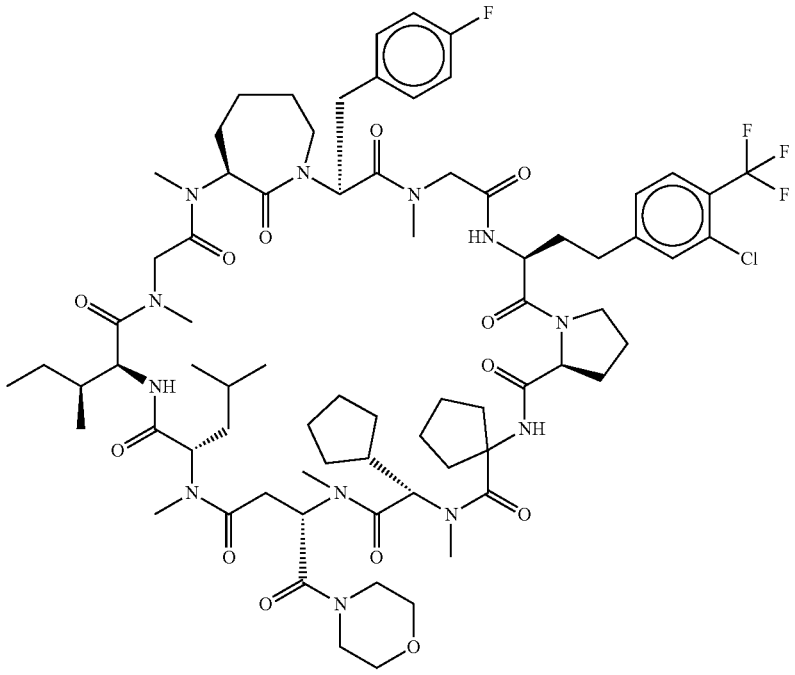 |
| PP0531 | 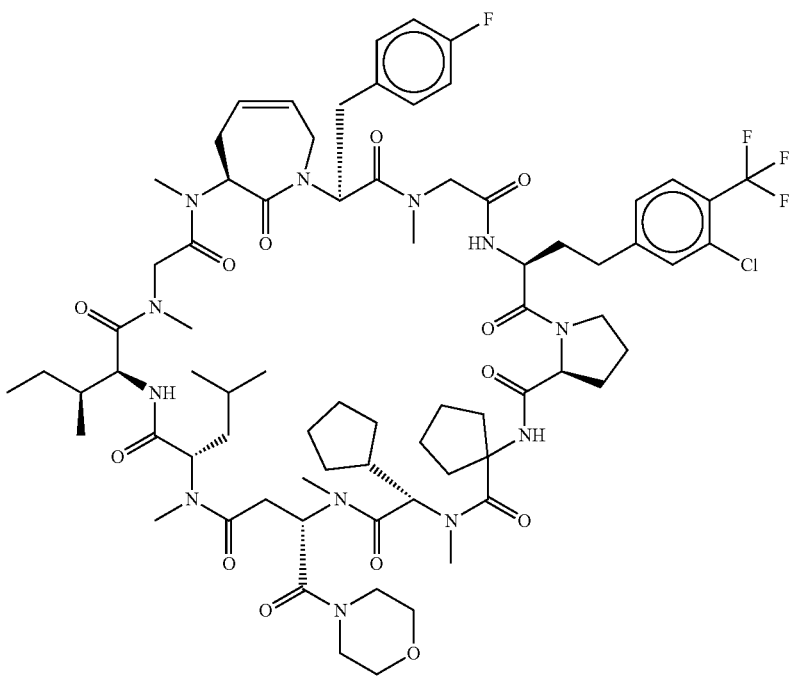 |

TABLE 38-continued
| Compound No. | Structural Formula |
|---|---|
| PP0532 | 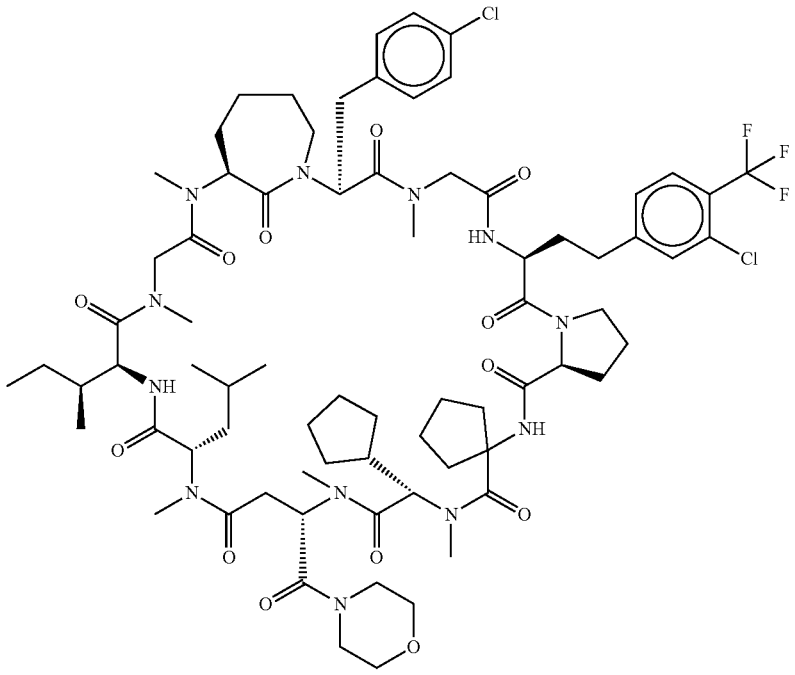 |
| PP0533 | 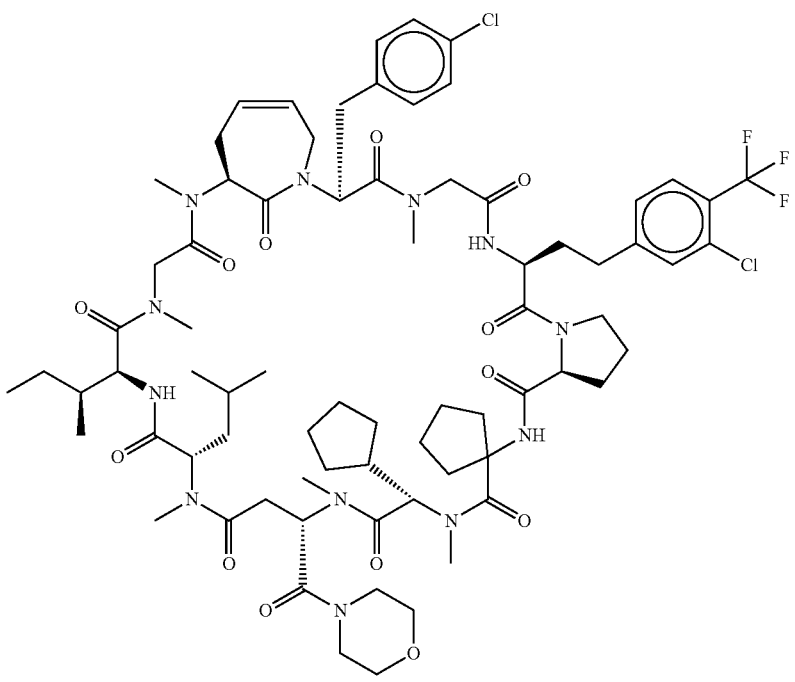 |

TABLE 38-continued
| Compound No. | Structural Formula |
|---|---|
| PP0534 | 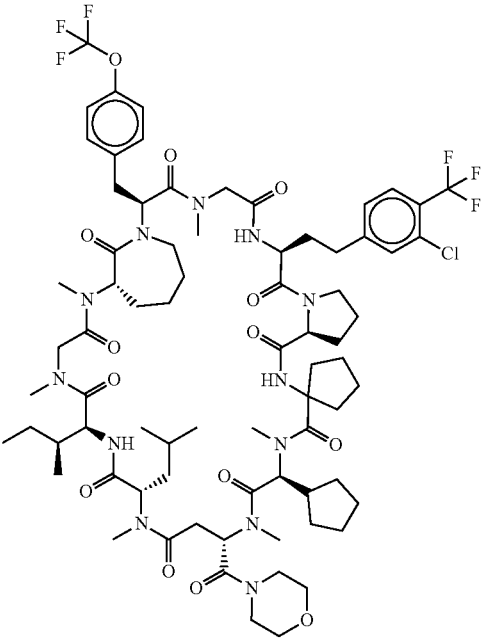 |
| PP0535 | 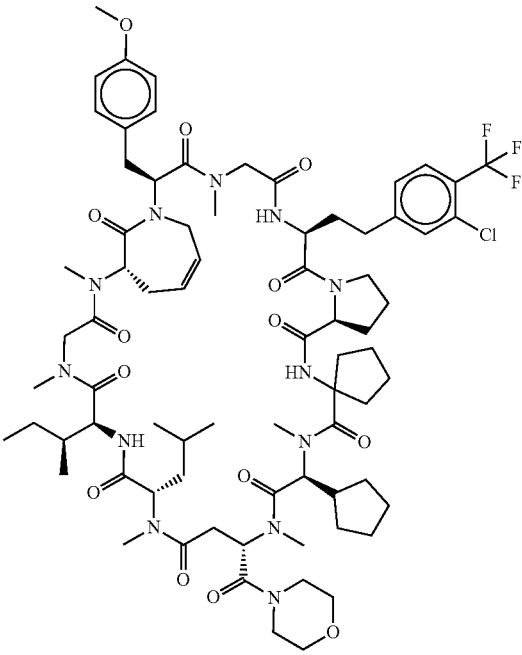 |

| Compound No. | Structural Formula |
|---|---|
| PP0536 | |
| PP0537 | |

TABLE 38-continued

| Compound No. | Structural Formula |
|---|---|
| PP0538 | |
| PP0539 | |

TABLE 38-continued
| Compound No. | Structural Formula |
|---|---|
| PP0540 | 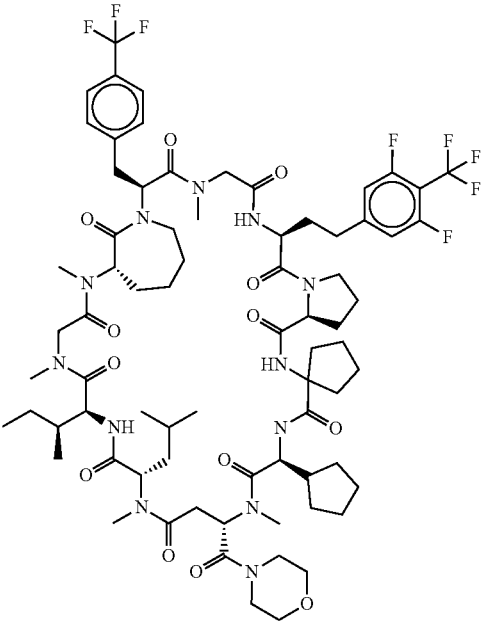 |
| PP0541 | 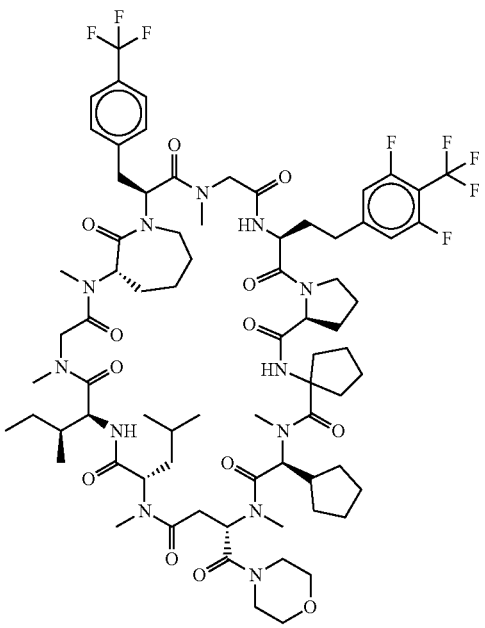 |

TABLE 38-continued

| Compound No. | Structural Formula |
|---|---|
| PP0542 | |
| PP0543 | |

TABLE 38-continued

| Compound No. | Structural Formula |
|---|---|
| PP0544 | |
| PP0545 | |

TABLE 38-continued
| Compound No. | Structural Formula |
|---|---|
| PP0546 | 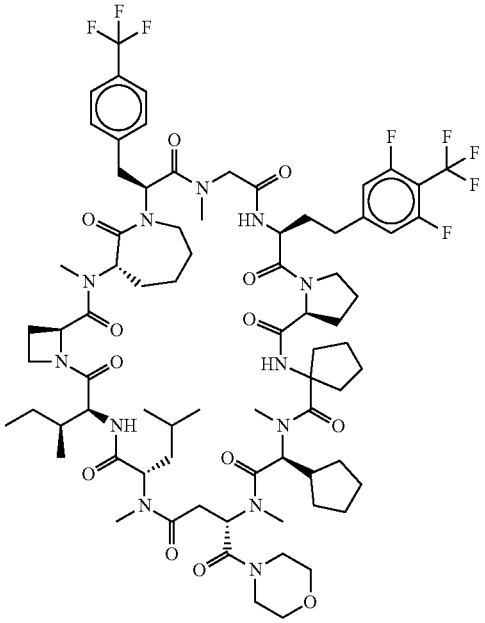 |
| PP0547 | 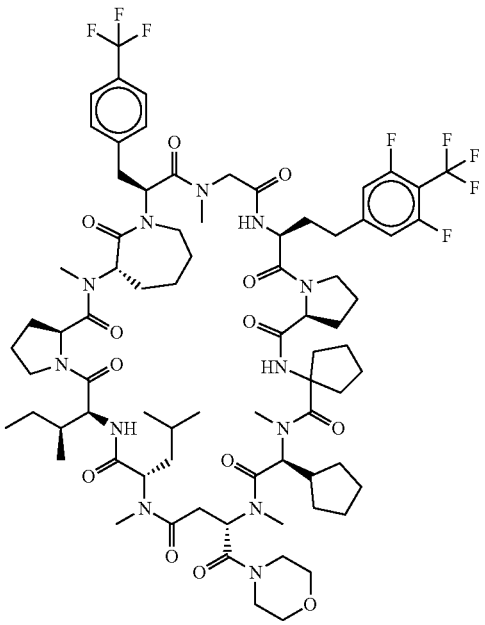 |

TABLE 38-continued
| Compound No. | Structural Formula |
| --- | --- |
| PP0548 | 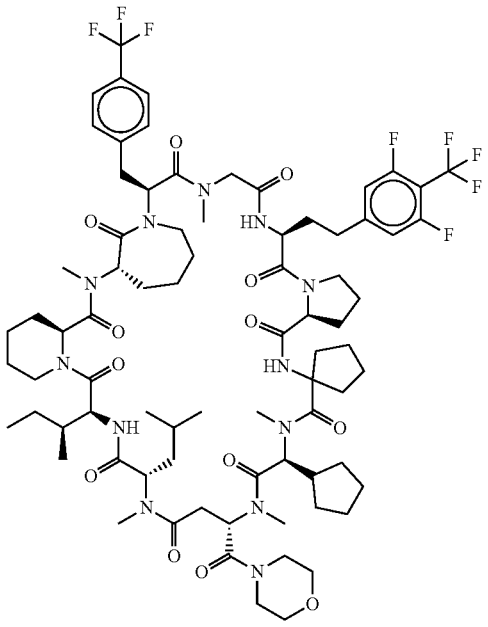 |
| PP0549 | 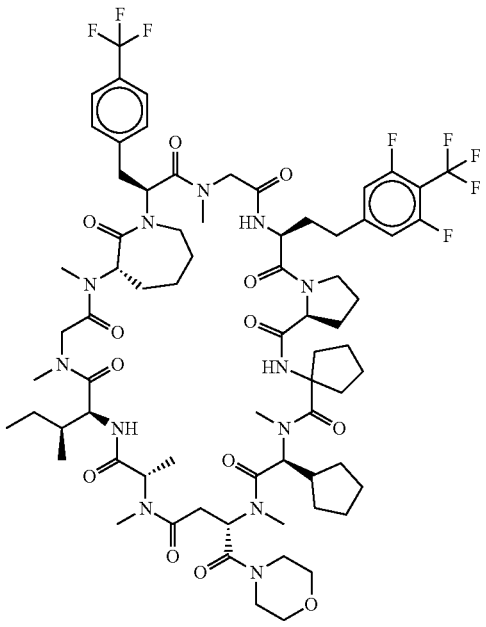 |

TABLE 38-continued

| Compound No. | Structural Formula |
|---|---|
| PP0550 | |
| PP0551 | |

TABLE 38-continued

| Compound No. | Structural Formula |
|---|---|
| PP0552 | |
| PP0553 | |

TABLE 38-continued

| Compound No. | Structural Formula |
|---|---|
| PP0554 | |
| PP0555 | |

TABLE 38-continued
| Compound No. | Structural Formula |
|---|---|
| PP0556 | 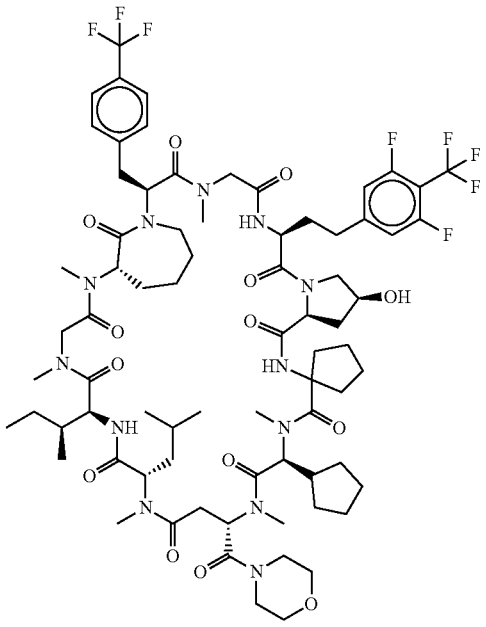 |
| PP0557 | 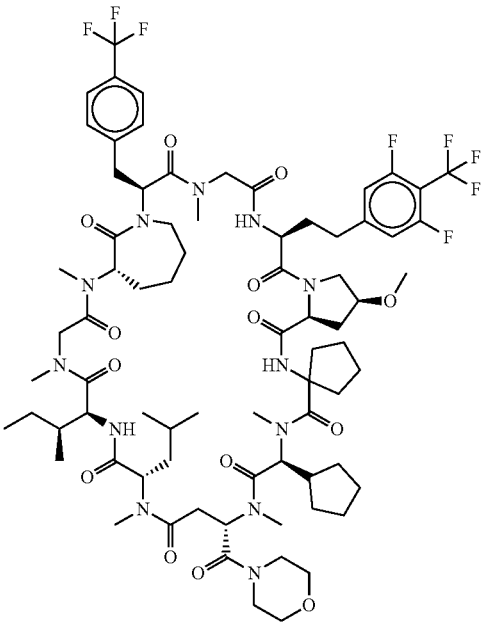 |

TABLE 38-continued
| Compound No. | Structural Formula |
|---|---|
| PP0558 | 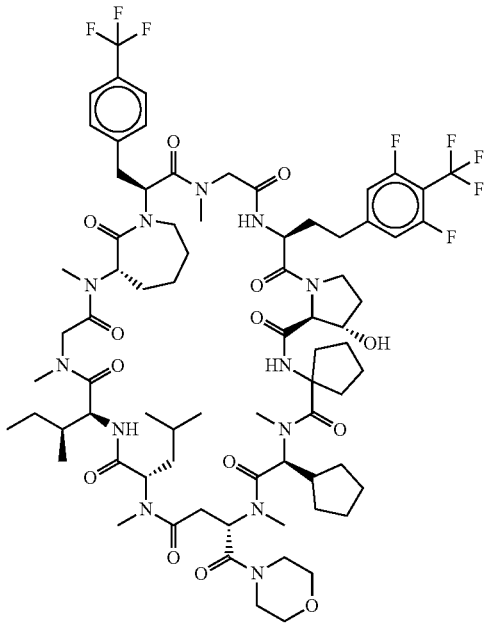 |
| PP0559 | 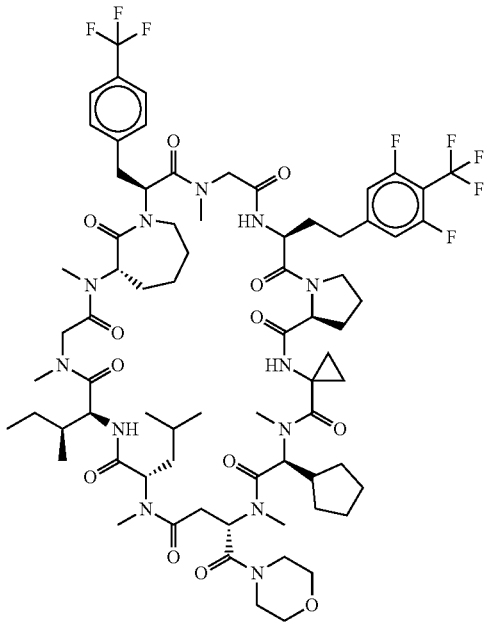 |

TABLE 38-continued

| Compound No. | Structural Formula |
|---|---|
| PP0560 | |
| PP0561 | |

TABLE 38-continued

| Compound No. | Structural Formula |
|---|---|
| PP0562 | |
| PP0563 | |

TABLE 38-continued

| Compound No. | Structural Formula |
|---|---|
| PP0564 | |
| PP0565 | |

TABLE 38-continued

| Compound No. | Structural Formula |
|---|---|
| PP0566 | |
| PP0567 | |

TABLE 38-continued

| Compound No. | Structural Formula |
| --- | --- |
| PP0568 | |
| PP0569 | |

TABLE 38-continued
| Compound No. | Structural Formula |
|---|---|
| PP0570 | 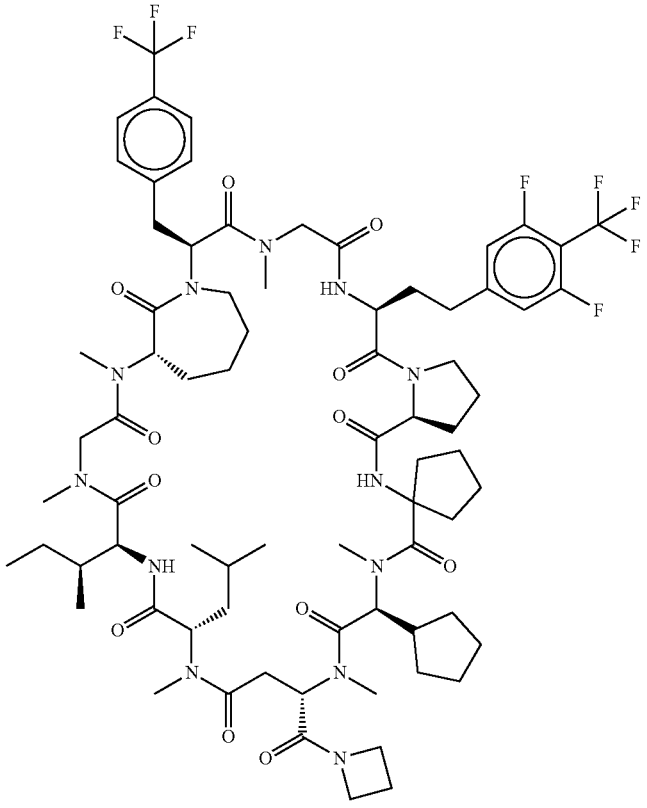 |
| PP0571 | 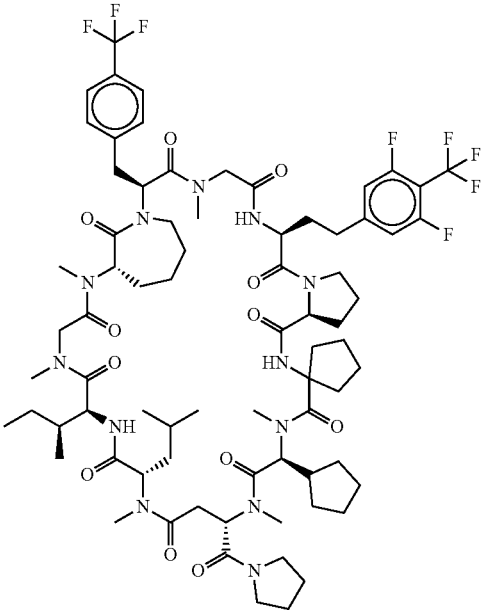 |

TABLE 38-continued
| Compound No. | Structural Formula |
|---|---|
| PP0572 | 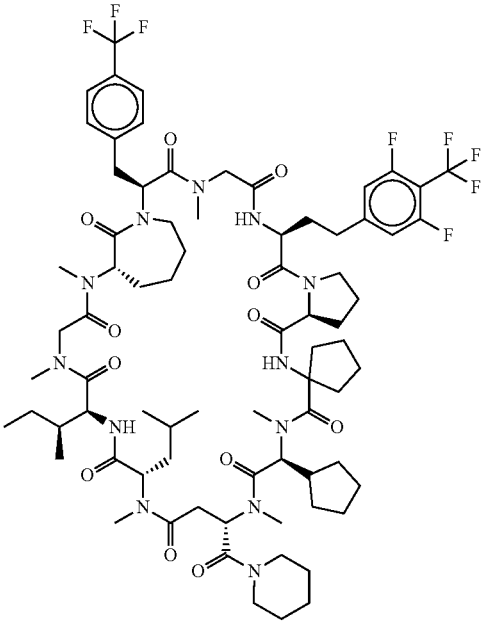 |
| PP0573 | 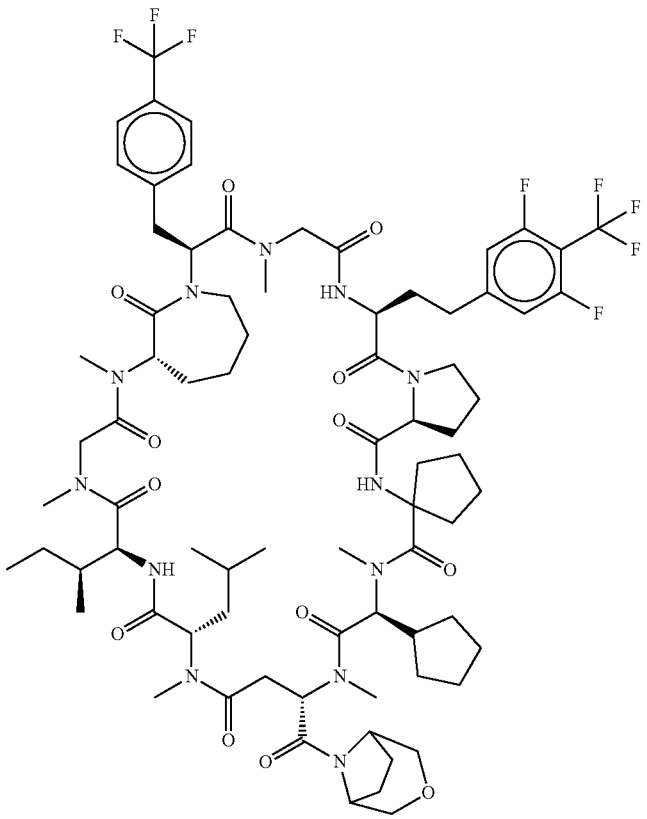 |

TABLE 38-continued
| Compound No. | Structural Formula |
|---|---|
| PP0574 | 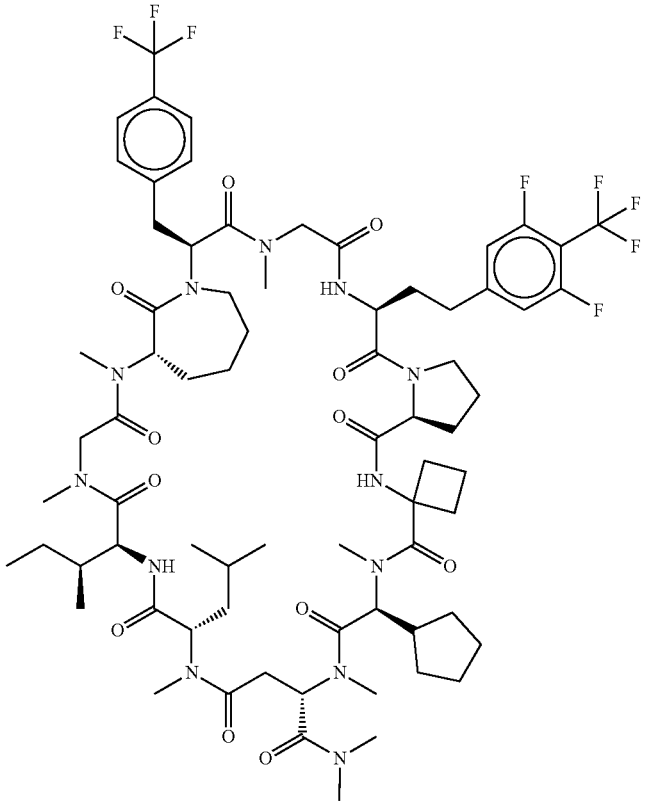 |
| PP0575 | 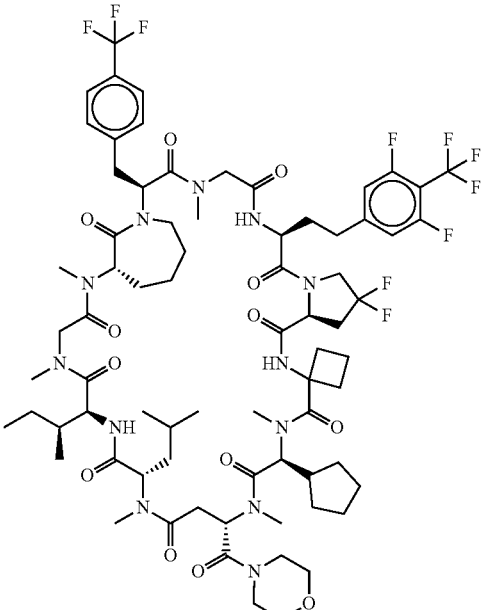 |

TABLE 38-continued
| Compound No. | Structural Formula |
|---|---|
| PP0576 | 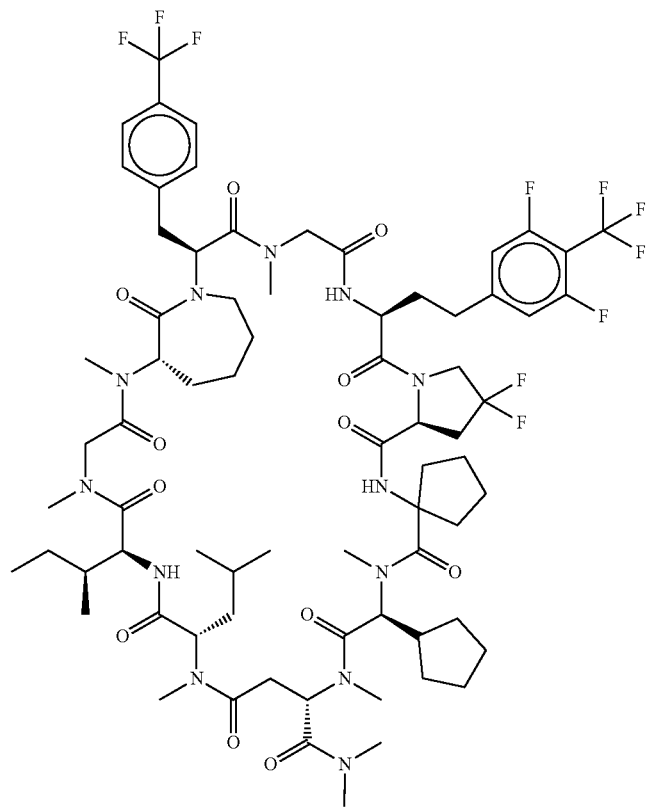 |
| PP0577 | 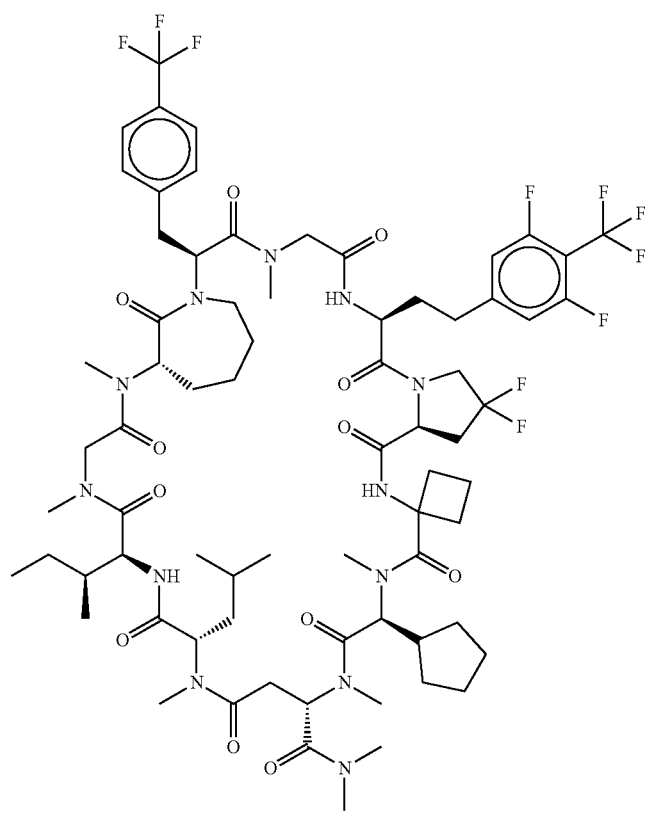 |

TABLE 38-continued
| Compound No. | Structural Formula |
|---|---|
| PP0578 | 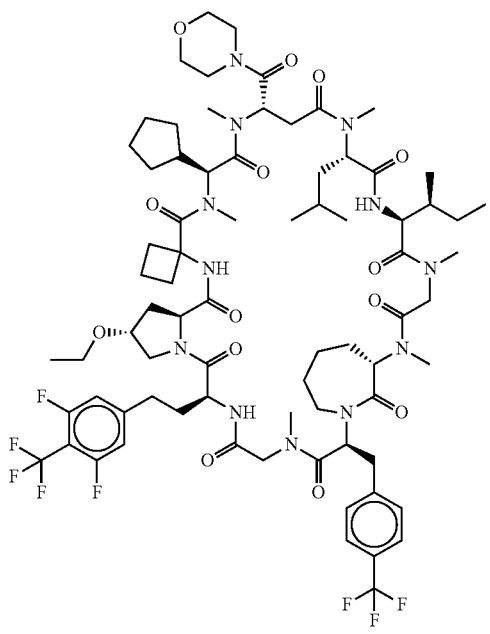 |
| PP0579 | 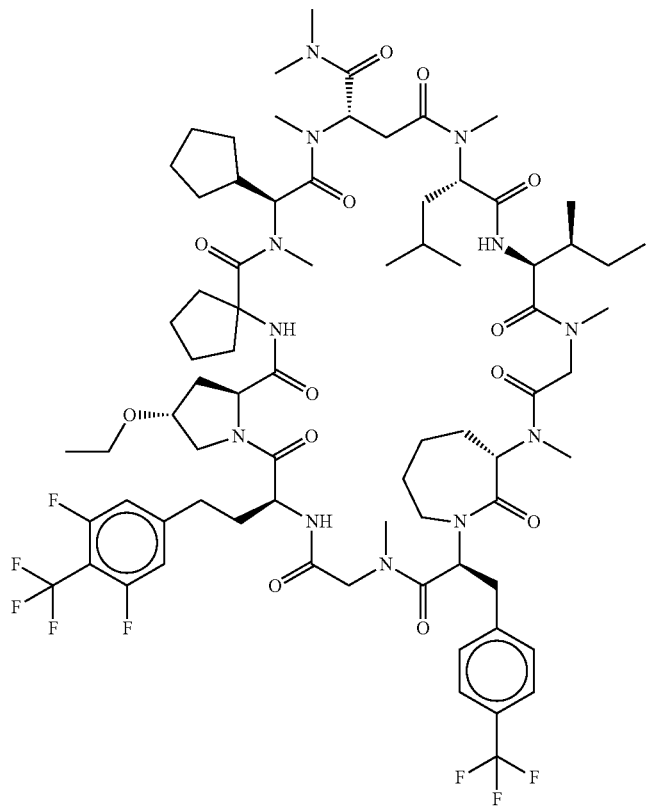 |

TABLE 38-continued
| Compound No. | Structural Formula |
|---|---|
| PP0580 | 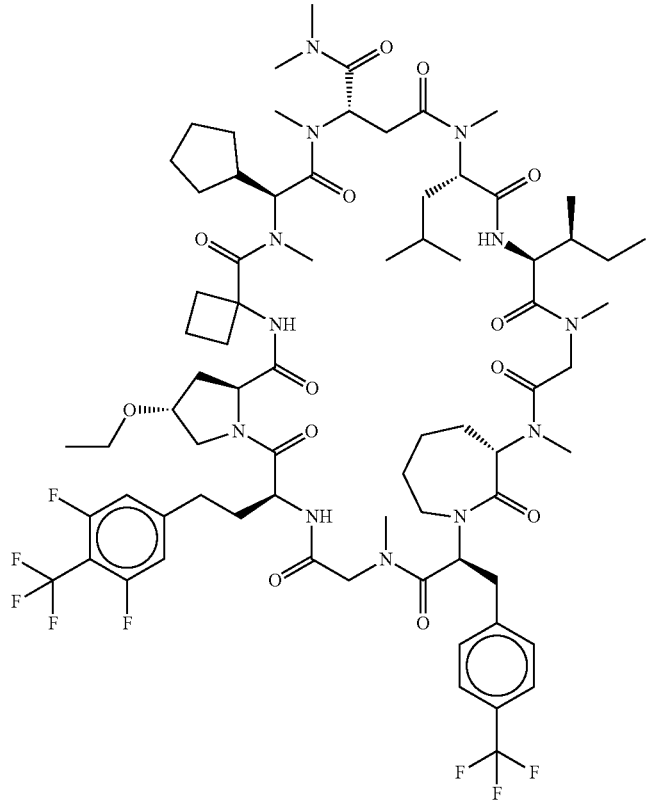 |
| PP0581 | 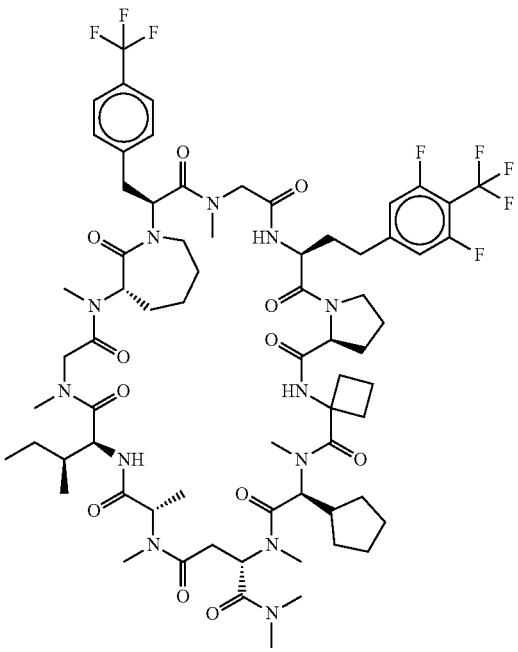 |

1427                                                                                                    1428
TABLE 38-continued
| Compound No. | Structural Formula |
|---|---|
| PP0582 | 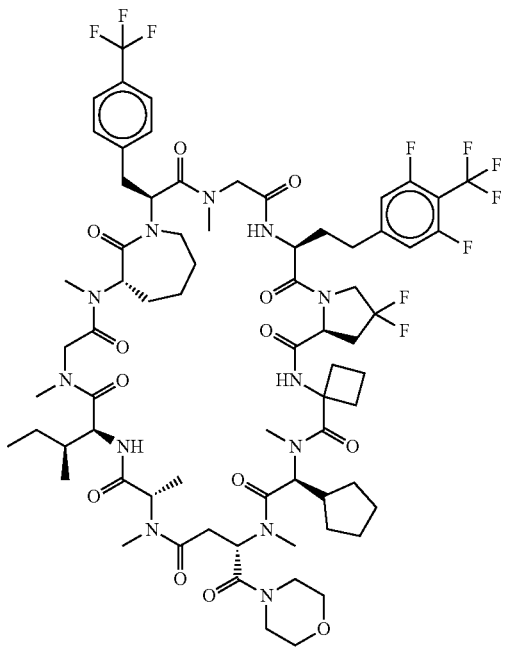 |
| PP0583 | 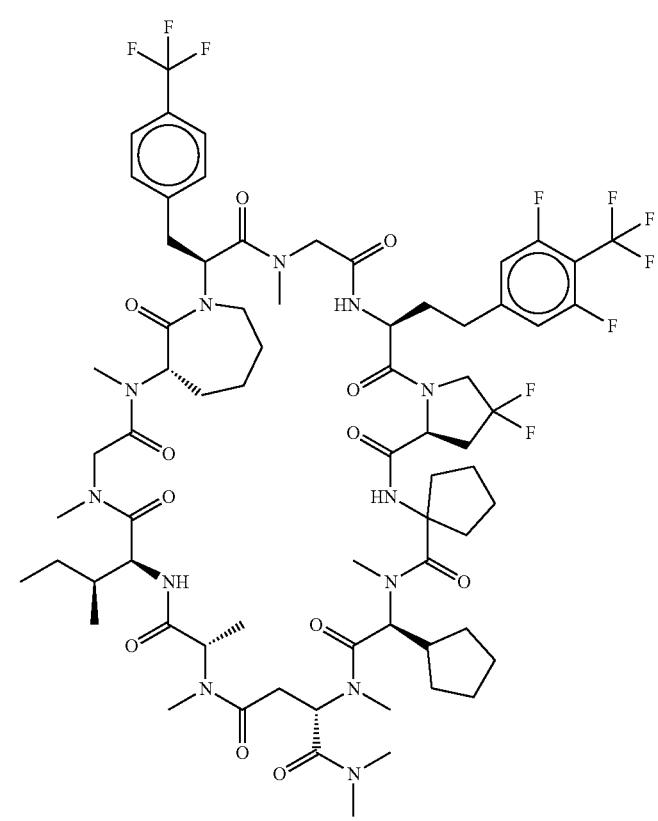 |

TABLE 38-continued
| Compound No. | Structural Formula |
| --- | --- |
| PP0584 | 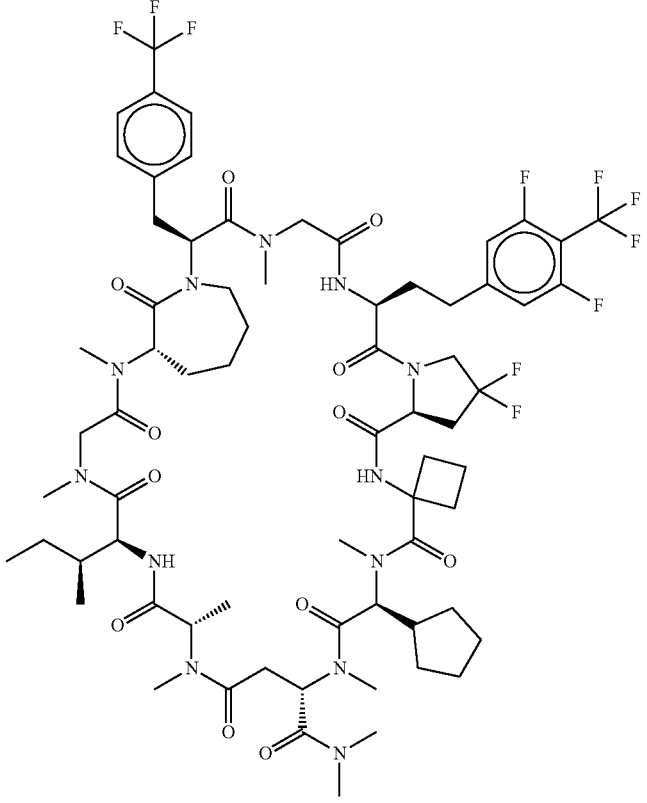 |
| PP0585 | 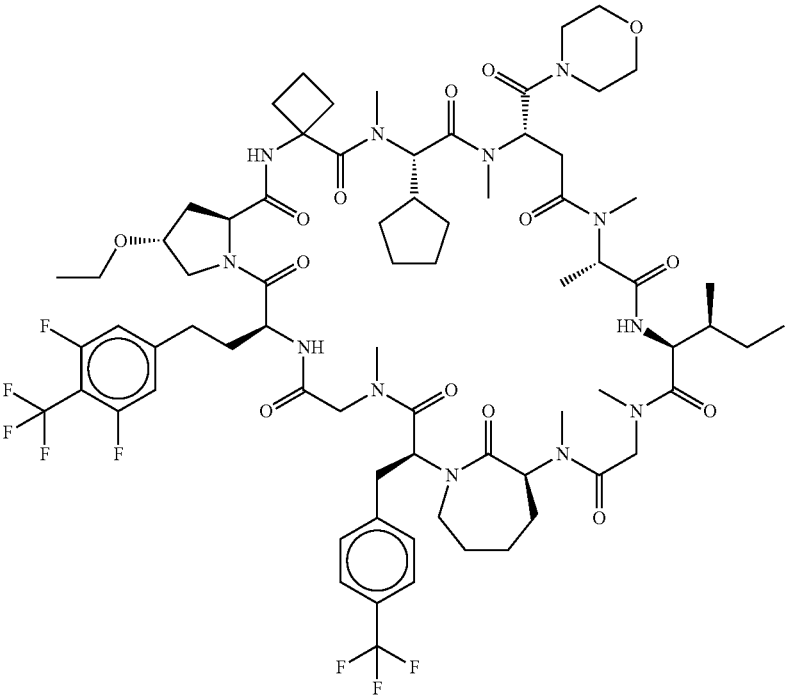 |

TABLE 38-continued
| Compound No. | Structural Formula |
|---|---|
| PP0586 | 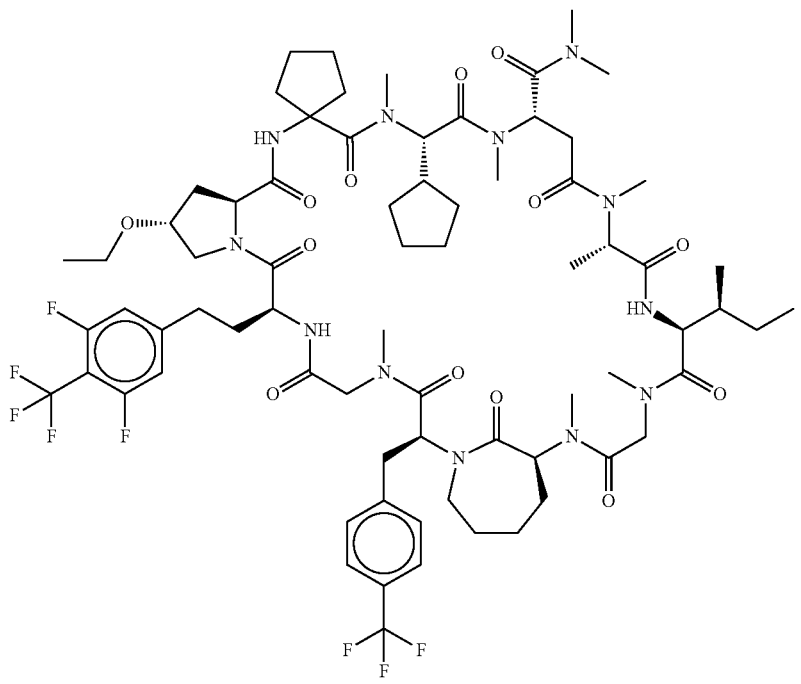 |
| PP0587 | 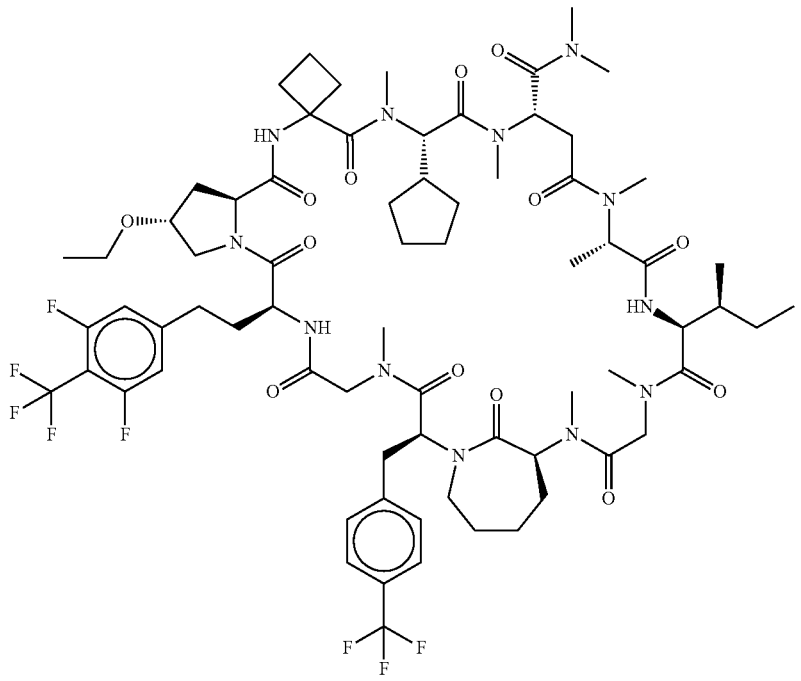 |

TABLE 38-continued
| Compound No. | Structural Formula |
|---|---|
| PP0588 | 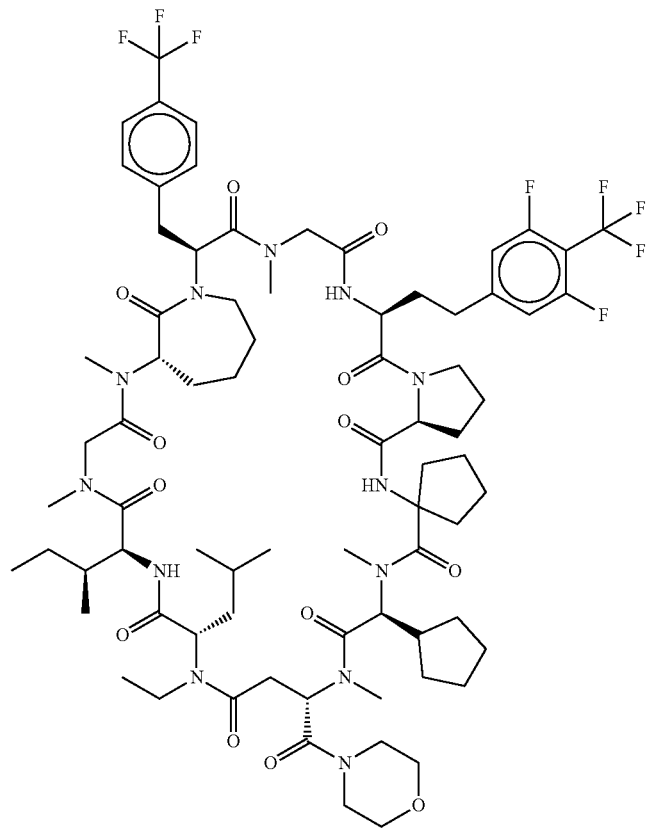 |
| PP0589 | 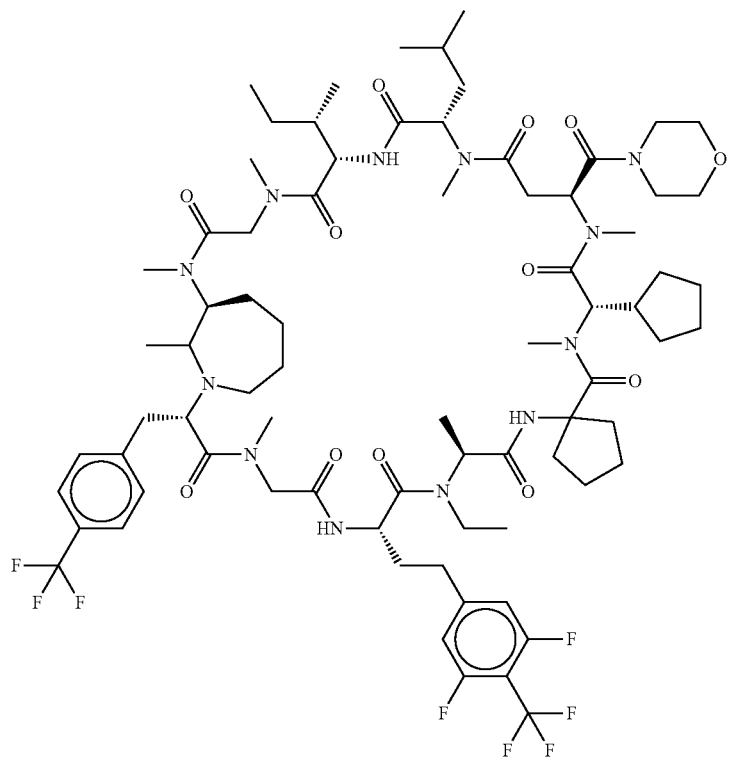 |

TABLE 38-continued
| Compound No. | Structural Formula |
| --- | --- |
| PP0590 | 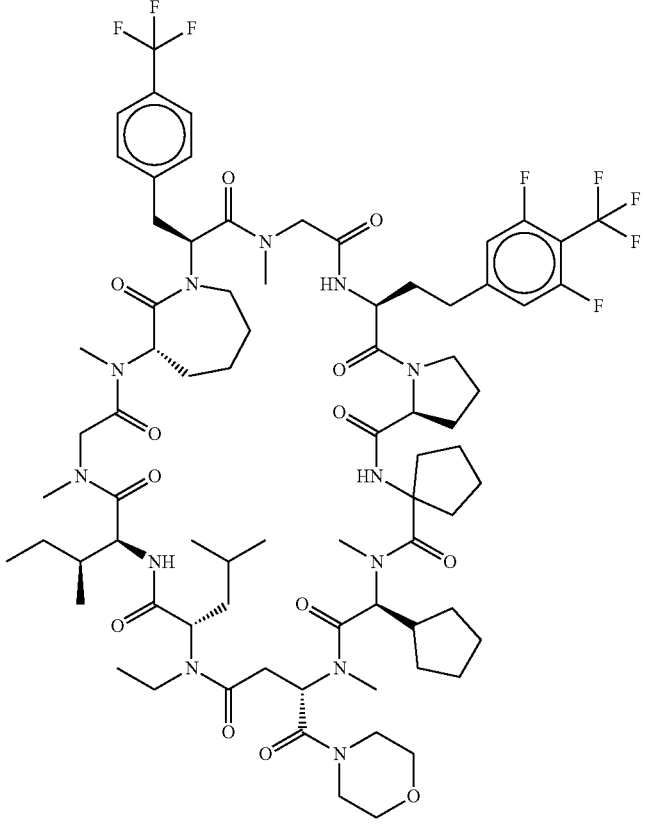 |
| PP0591 | 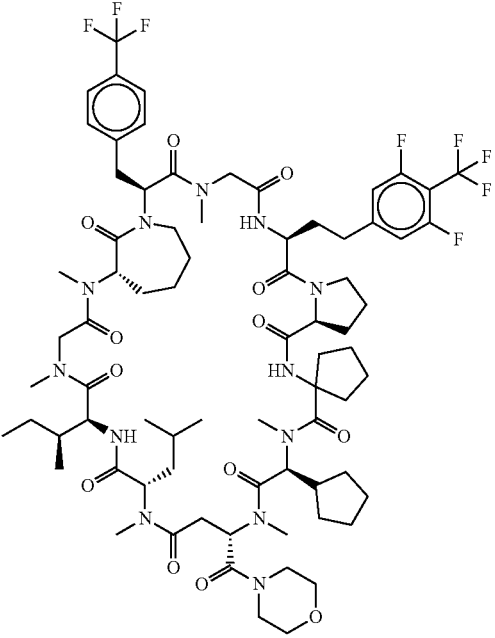 |

TABLE 38-continued
| Compound No. | Structural Formula |
|---|---|
| PP0594 | 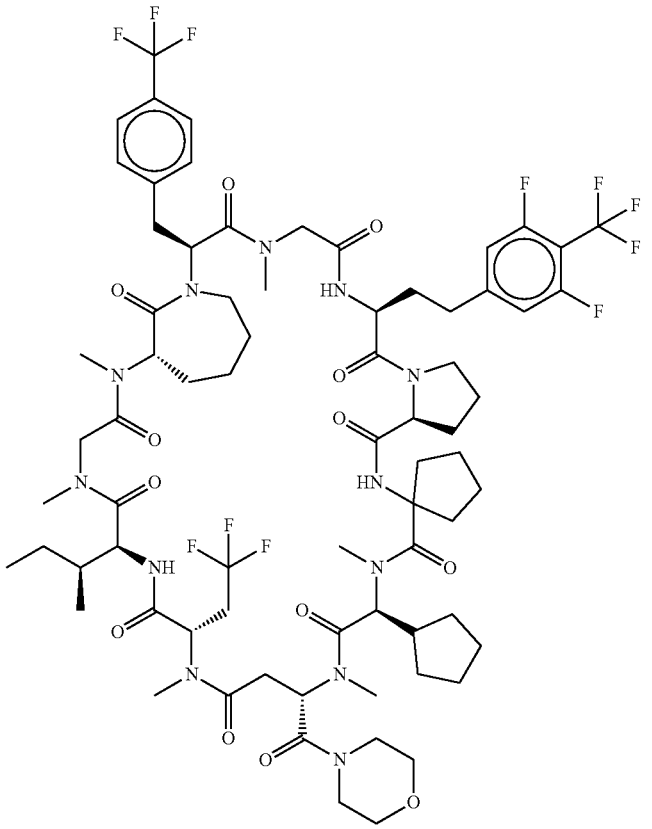 |
| PP0595 | 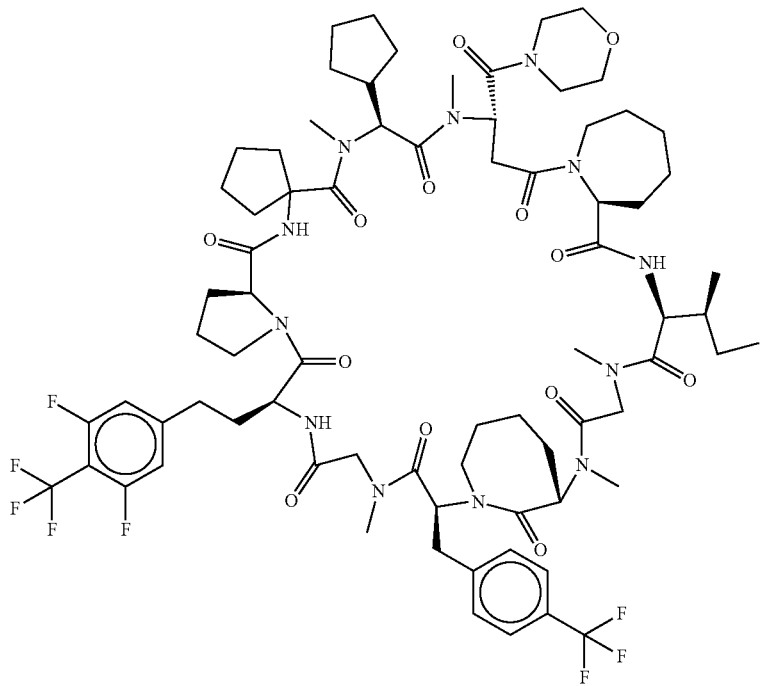 |

TABLE 38-continued

| Compound No. | Structural Formula |
|---|---|
| PP0596 | |
| PP0597 | |

TABLE 38-continued
| Compound No. | Structural Formula |
|---|---|
| PP0598 | 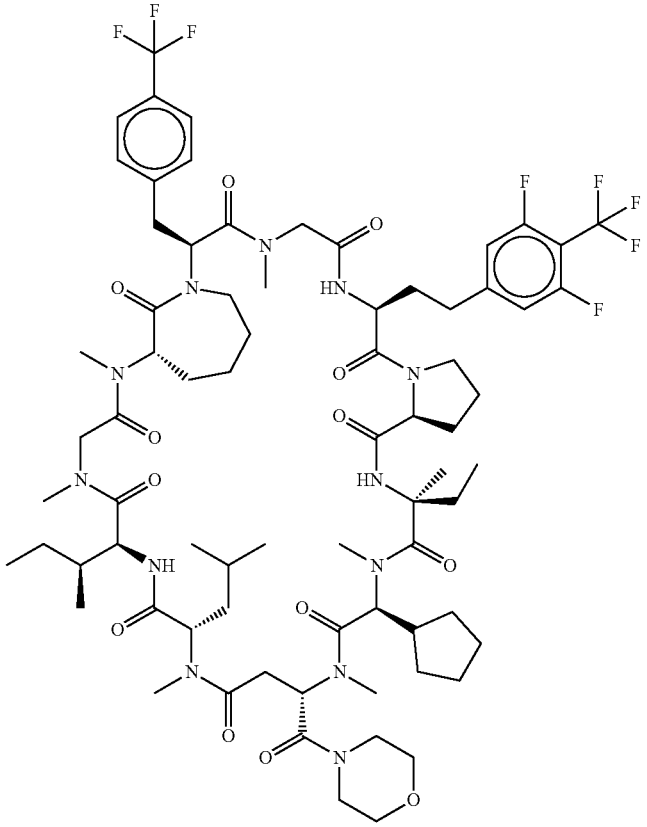 |
| PP0599 | 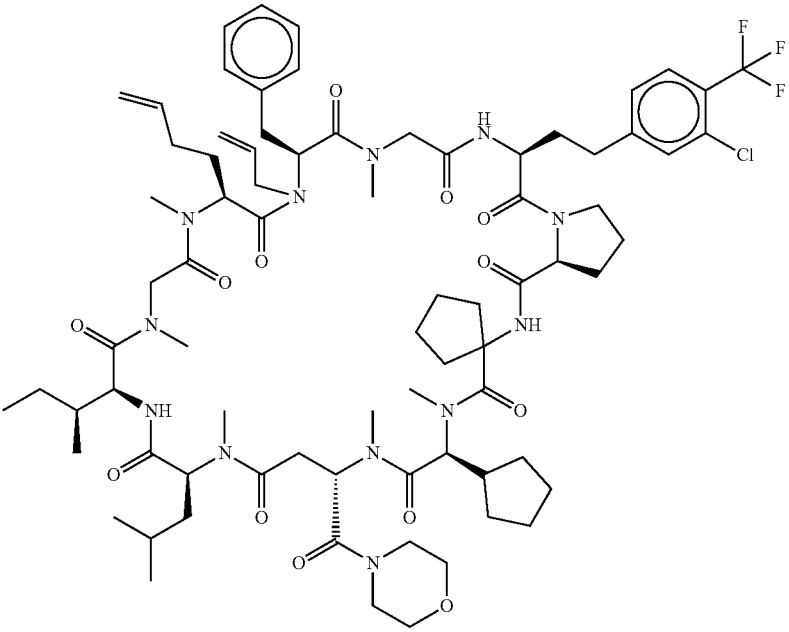 |

TABLE 38-continued

| Compound No. | Structural Formula |
| --- | --- |
| PP0605 | |
| PP0606 | |

TABLE 38-continued

| Compound No. | Structural Formula |
|---|---|
| PP0607 | |
| PP0608 | |

TABLE 38-continued

| Compound No. | Structural Formula |
|---|---|
| PP0609 | |
| PP0610 | |

TABLE 38-continued

| Compound No. | Structural Formula |
|---|---|
| PP0611 | |
| PP0612 | |

TABLE 38-continued
| Compound No. | Structural Formula |
|---|---|
| PP0613 | 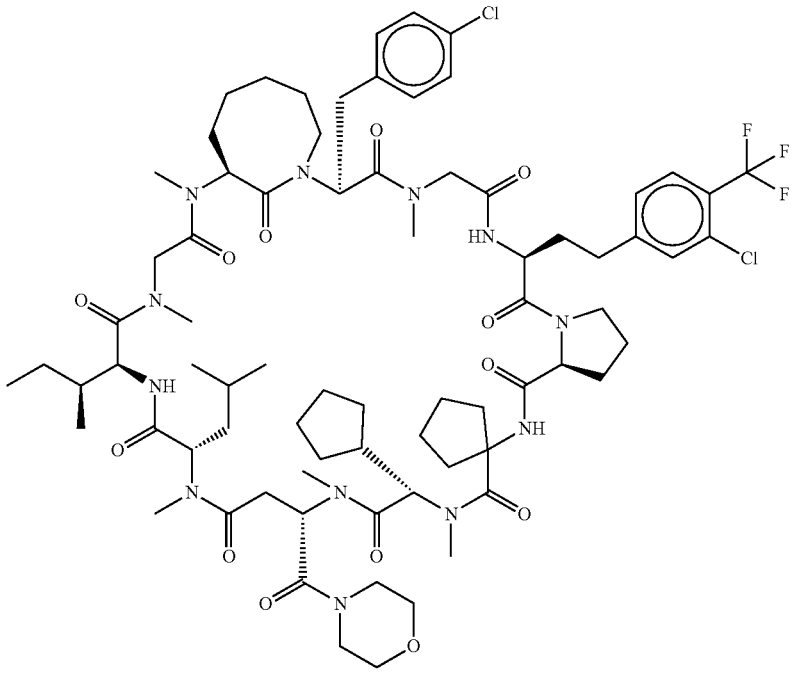 |
| PP0614 | 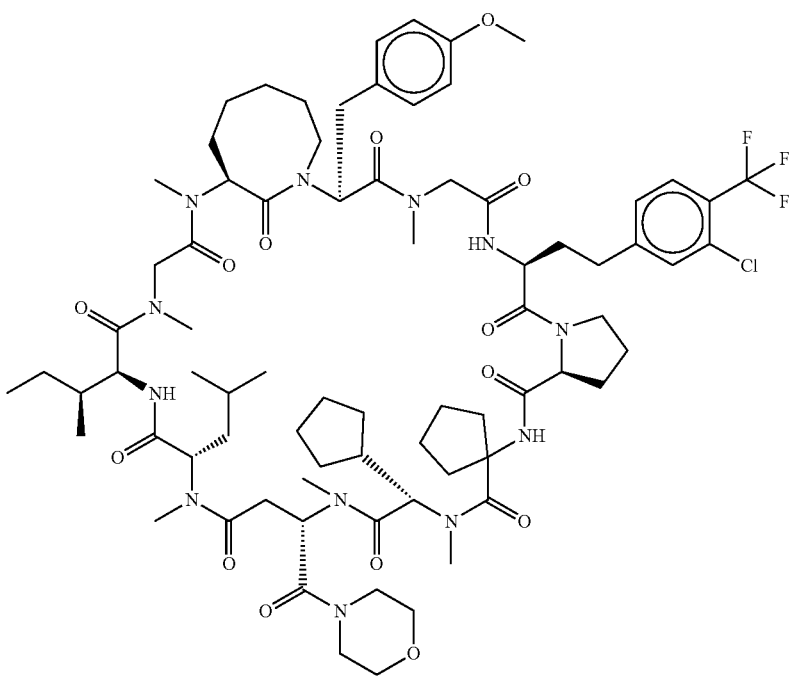 |

TABLE 38-continued

| Compound No. | Structural Formula |
|---|---|
| PP0615 | |
| PP0616 | |

TABLE 38-continued
| Compound No. | Structural Formula |
|---|---|
| PP0617 | 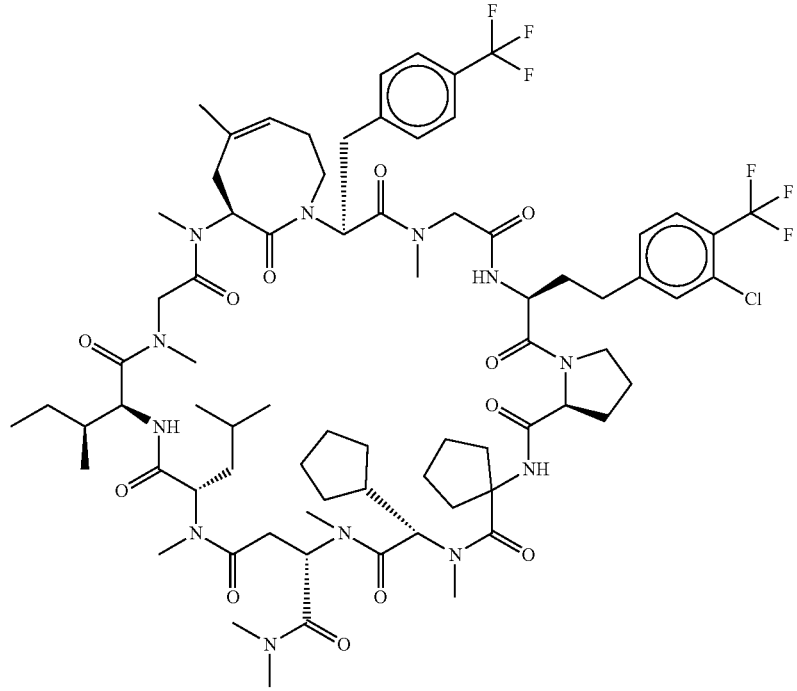 |
| PP0618 | 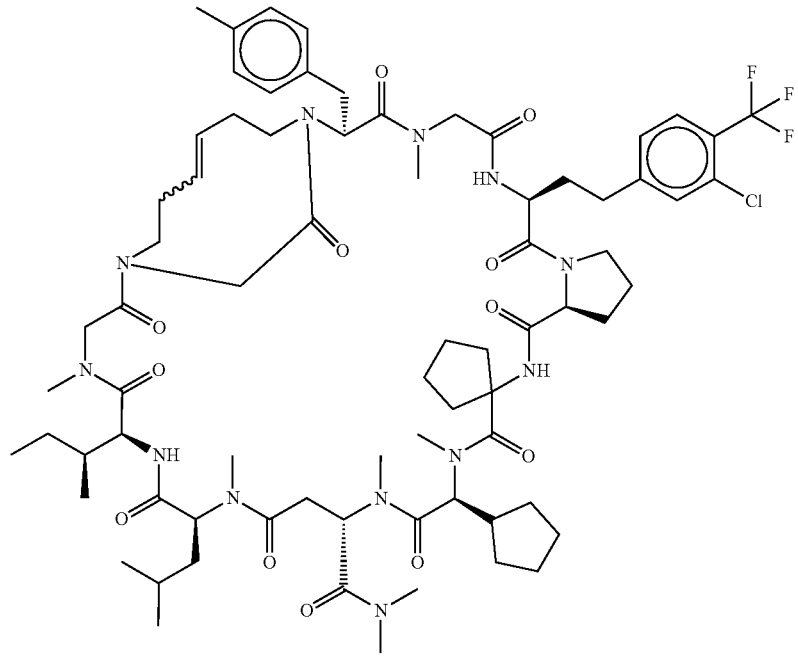 |

TABLE 38-continued
| Compound No. | Structural Formula |
|---|---|
| PP0619 | 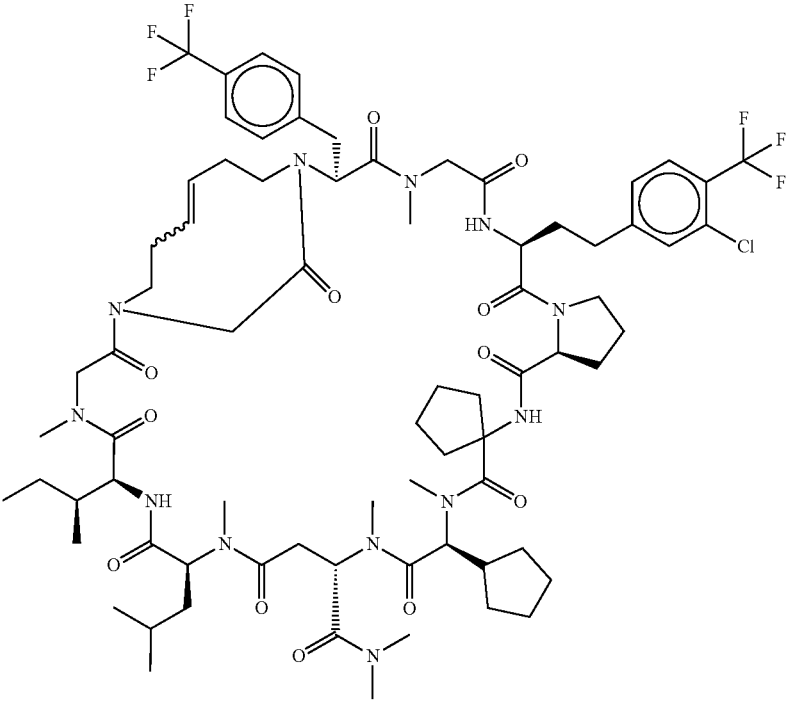 |
| PP0620 | 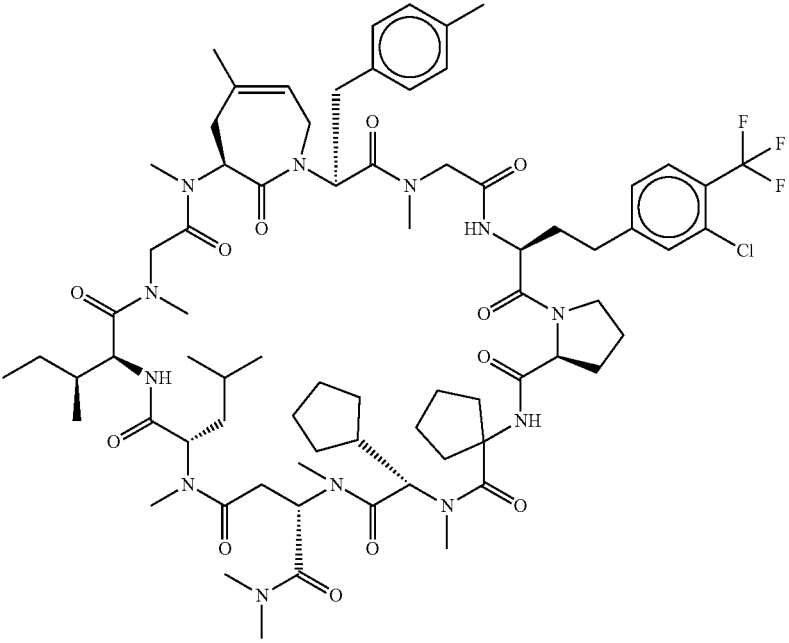 |

TABLE 38-continued
| Compound No. | Structural Formula |
|---|---|
| PP0621 | 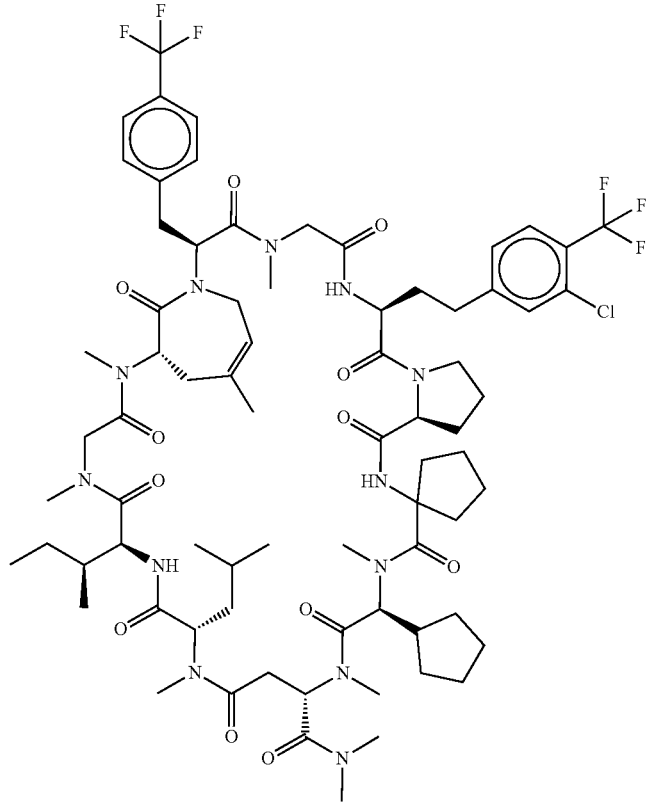 |
| PP0622 | 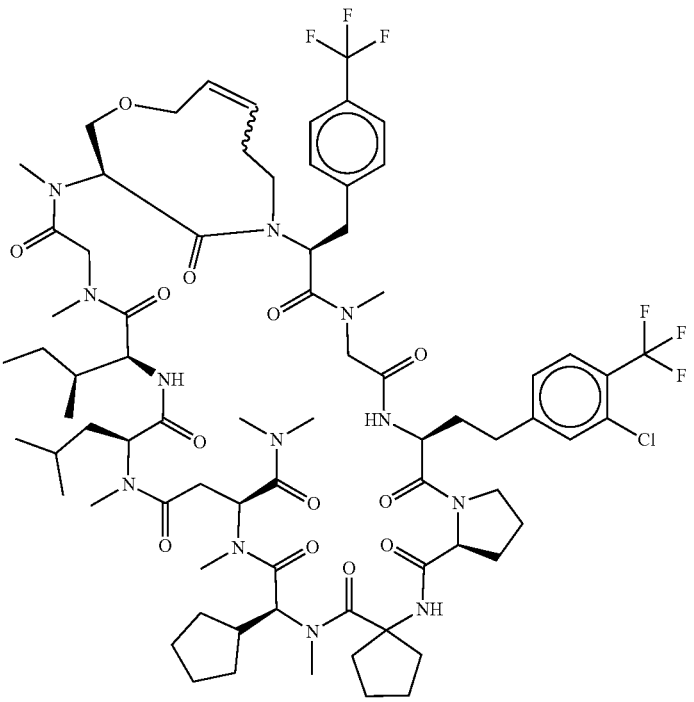 |

TABLE 38-continued
| Compound No. | Structural Formula |
|---|---|
| PP0626 | 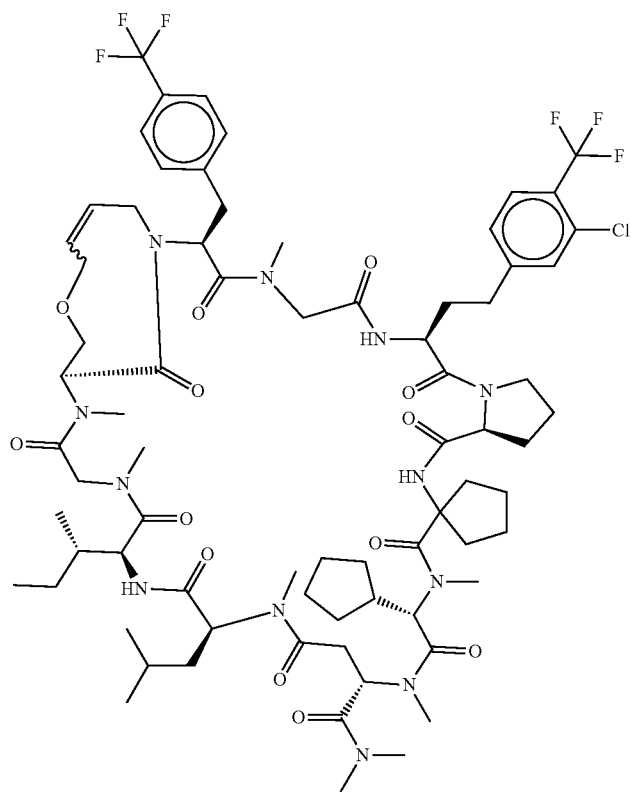 |
| PP0627 | 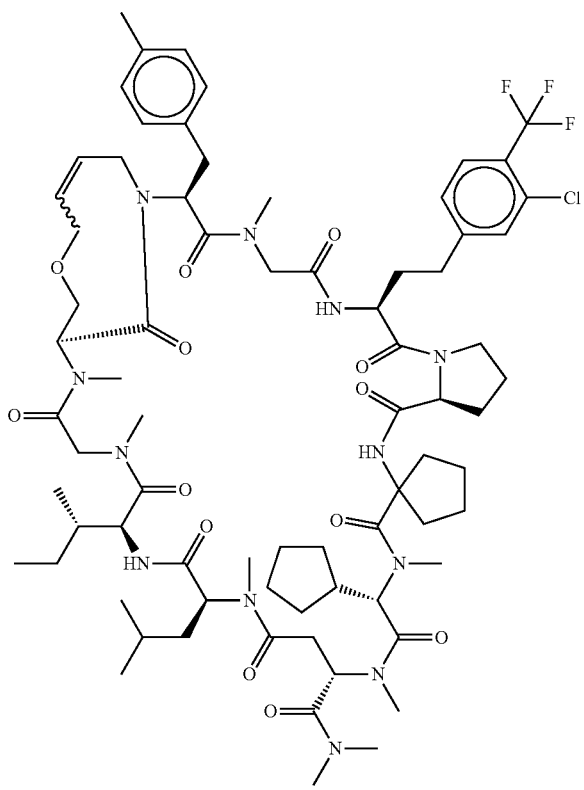 |

TABLE 38-continued
| Compound No. | Structural Formula |
|---|---|
| PP0628 | 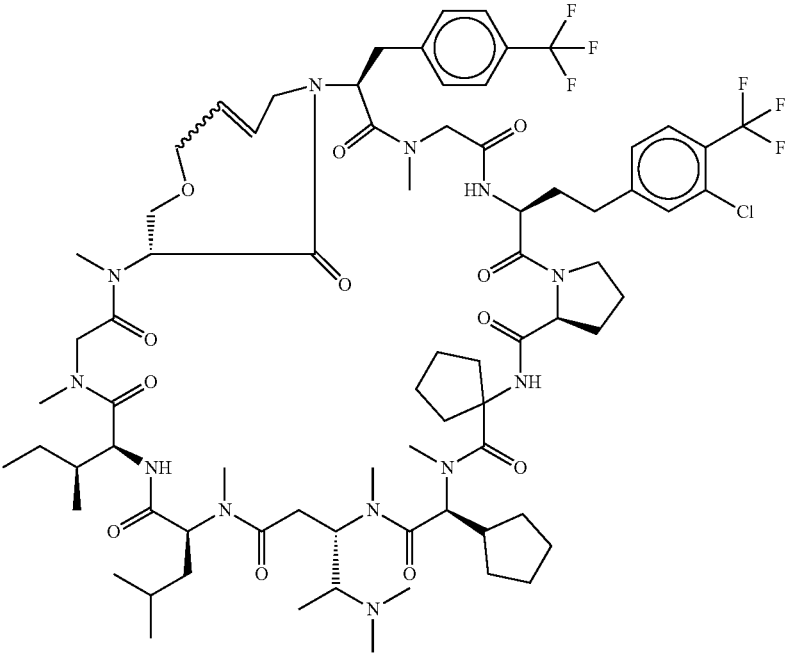 |
| PP0629 | 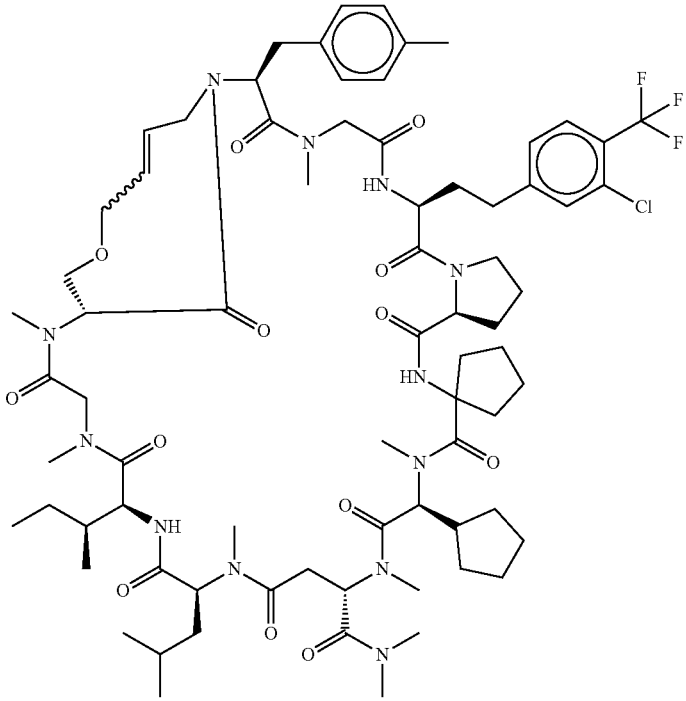 |

TABLE 38-continued

| Compound No. | Structural Formula |
|---|---|
| PP0630 | |
| PP0631 | |

TABLE 38-continued
| Compound No. | Structural Formula |
|---|---|
| PP0632 | 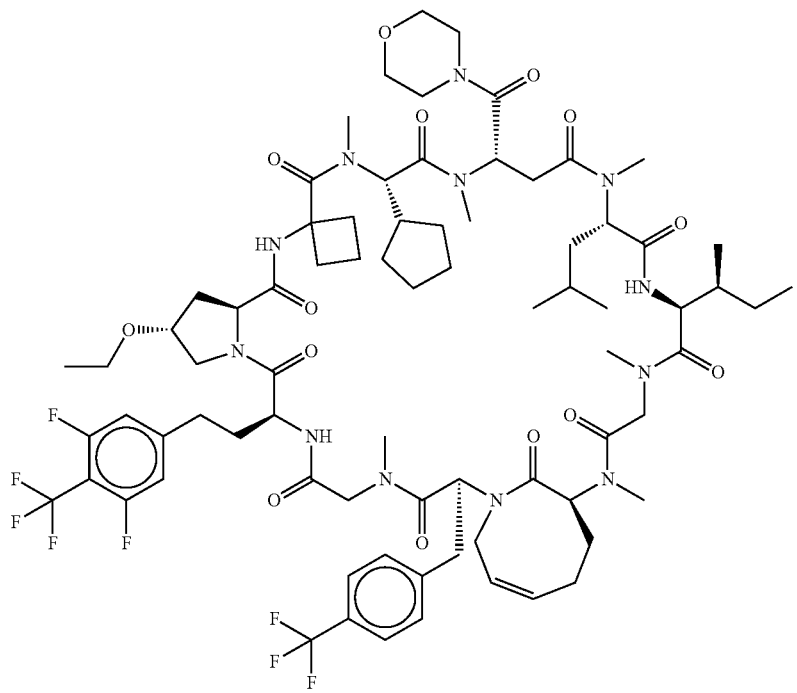 |
| PP0633 | 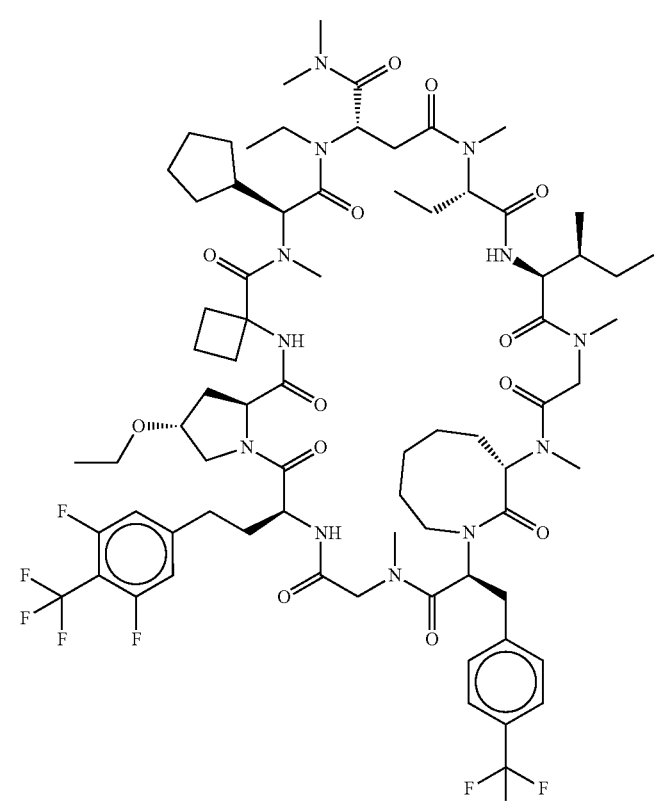 |

TABLE 38-continued
| Compound No. | Structural Formula |
|---|---|
| PP0634 | 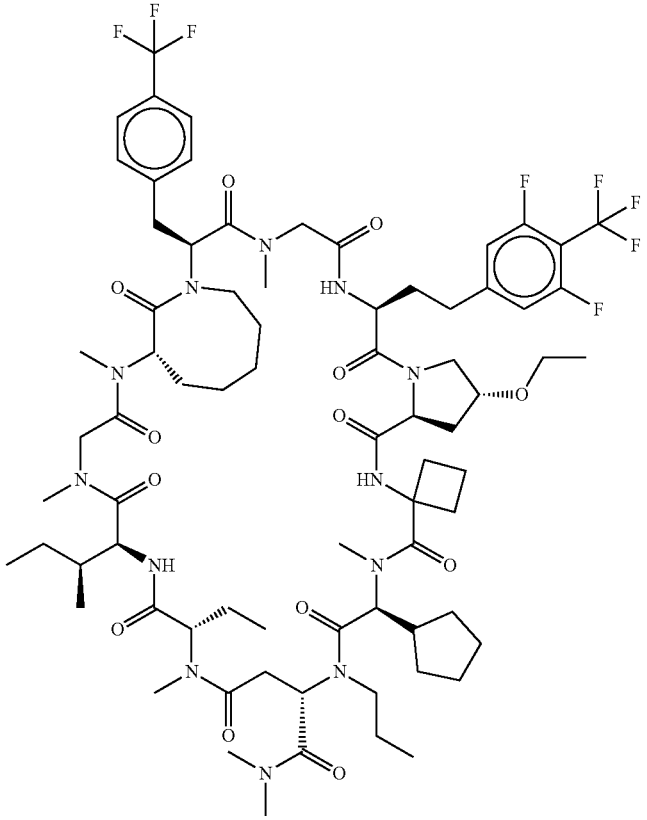 |
| PP0635 | 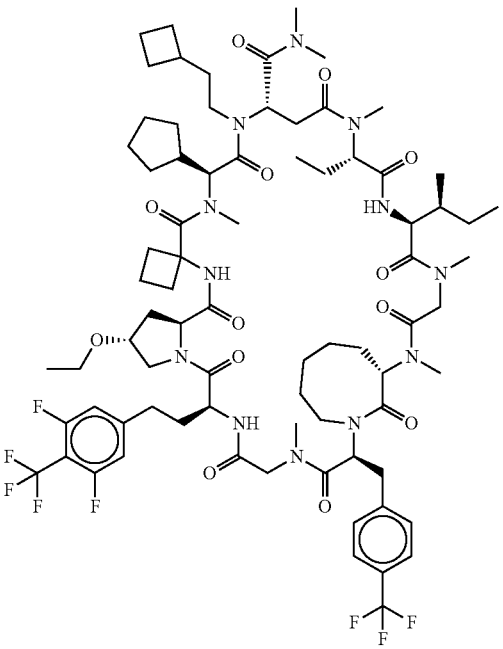 |

TABLE 38-continued
| Compound No. | Structural Formula |
|---|---|
| PP0636 | 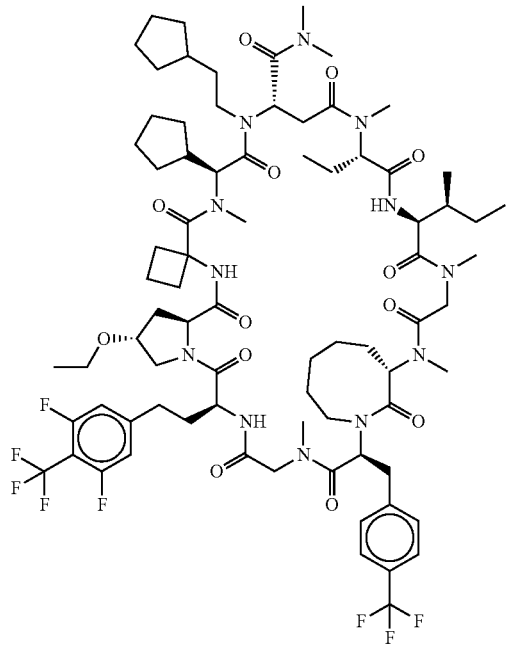 |
| PP0637 | 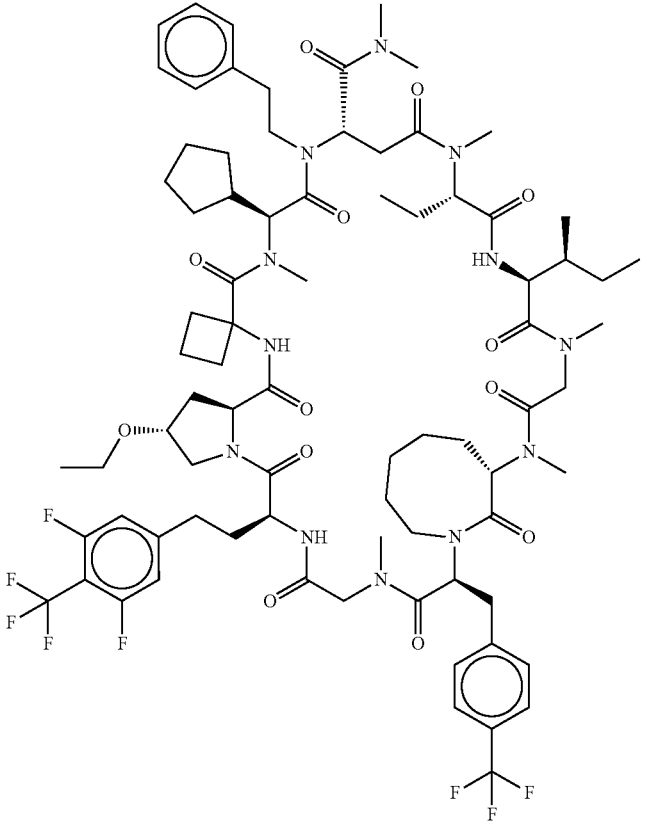 |

TABLE 38-continued

| Compound No. | Structural Formula |
|---|---|
| PP0638 | |
| PP0639 | |

TABLE 38-continued
| Compound No. | Structural Formula |
| --- | --- |
| PP0640 | 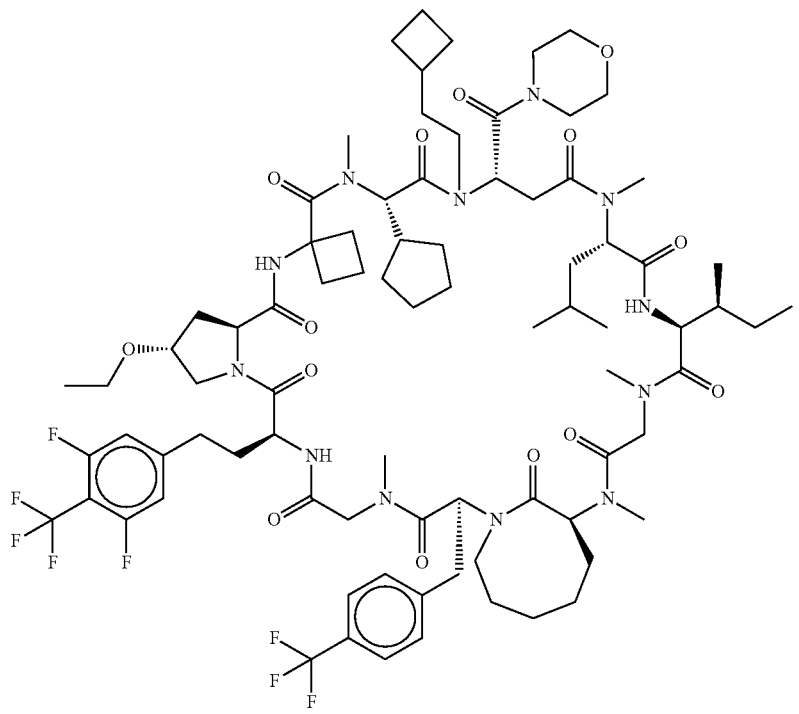 |
| PP0641 | 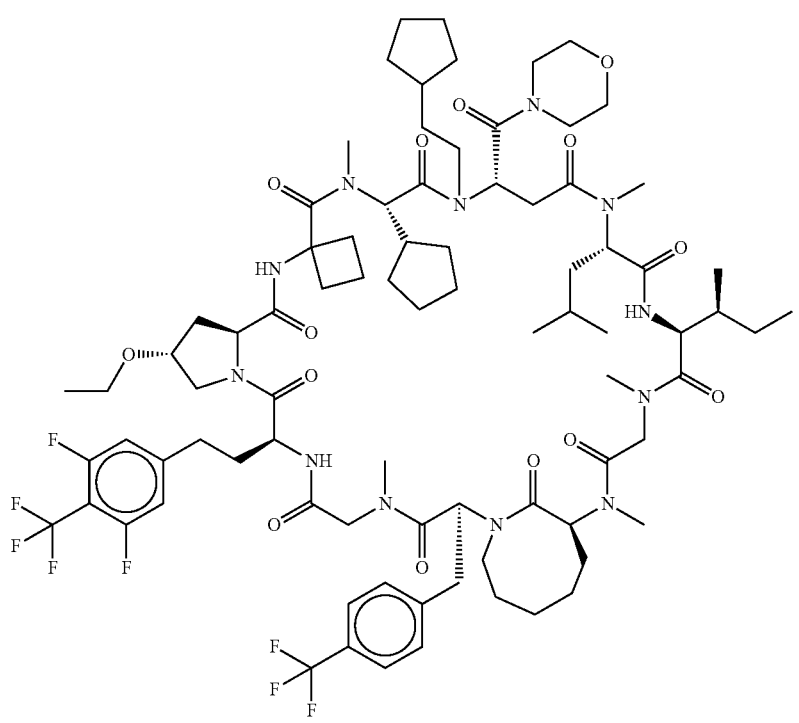 |

TABLE 38-continued
| Compound No. | Structural Formula |
|---|---|
| PP0642 | 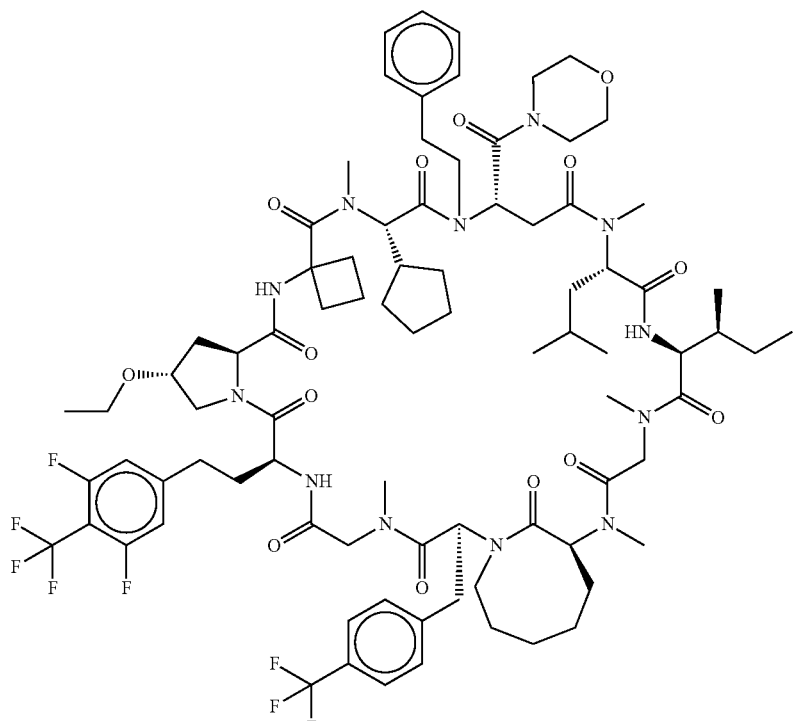 |
| PP0643 | 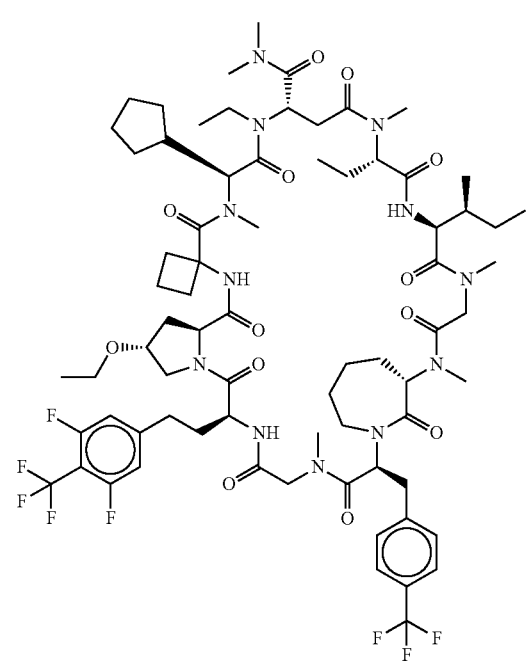 |

TABLE 38-continued
| Compound No. | Structural Formula |
|---|---|
| PP0644 | 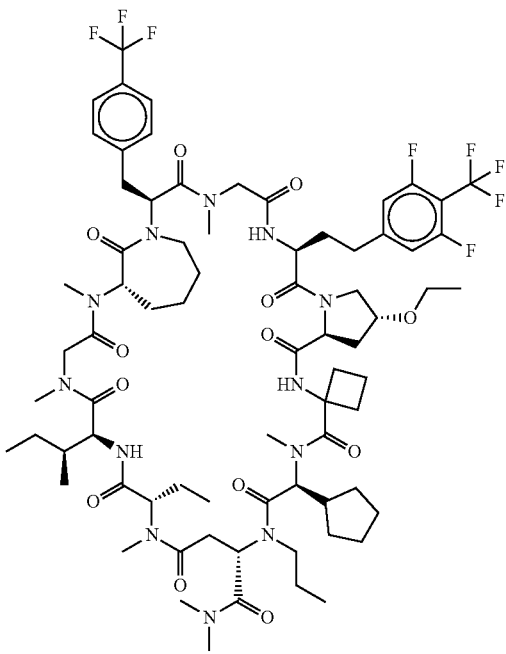 |
| PP0645 | 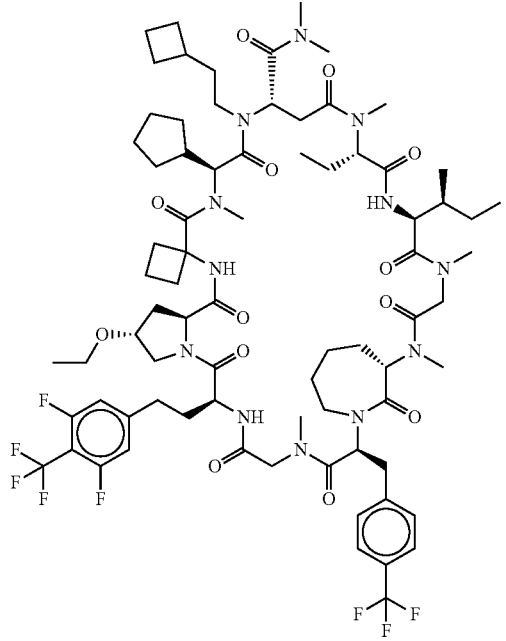 |

TABLE 38-continued
| Compound No. | Structural Formula |
|---|---|
| PP0646 | 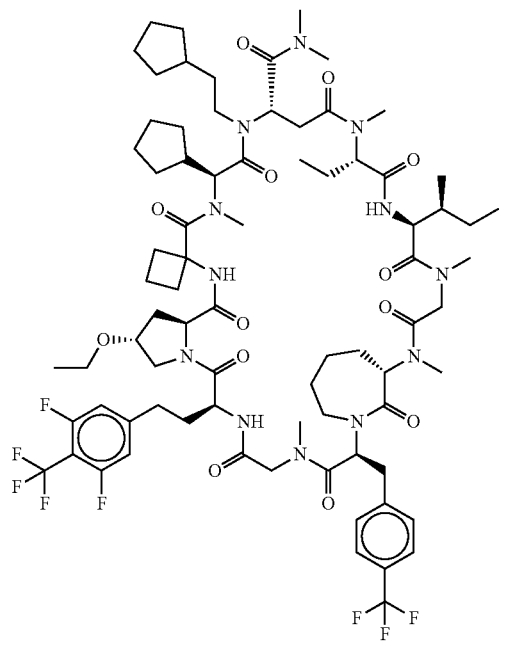 |
| PP0647 | 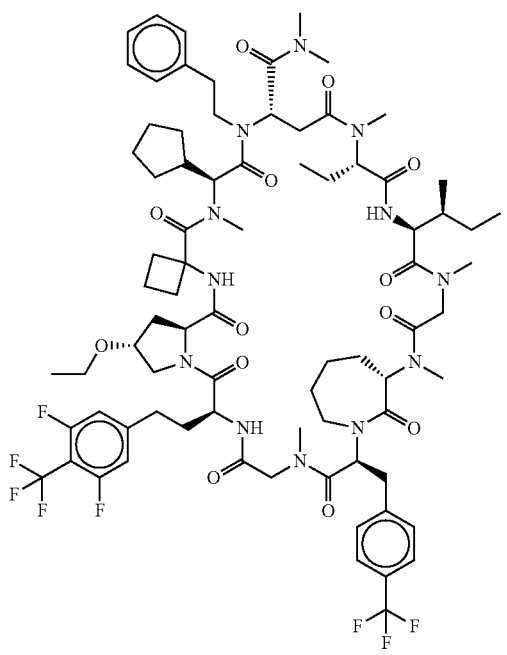 |

TABLE 38-continued
| Compound No. | Structural Formula |
|---|---|
| PP0648 | 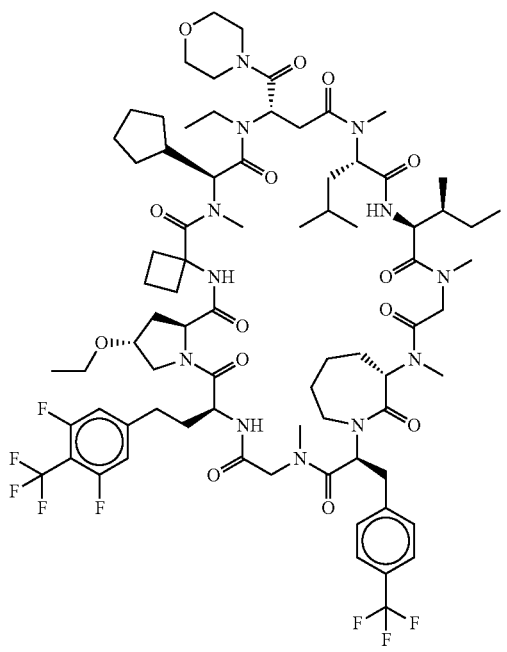 |
| PP0649 | 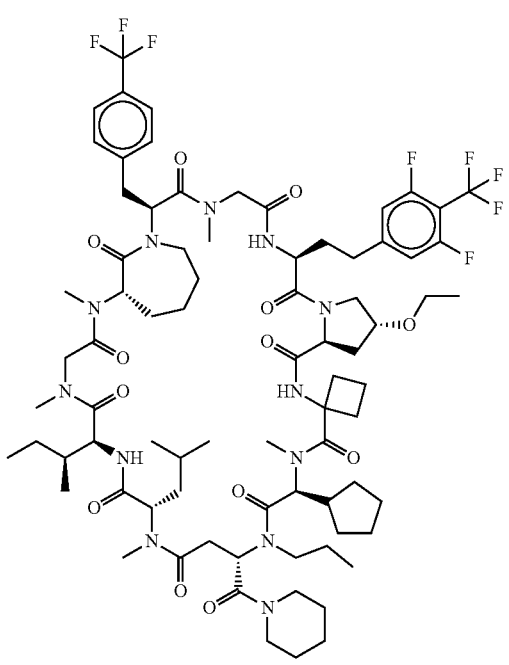 |

TABLE 38-continued

| Compound No. | Structural Formula |
|---|---|
| PP0650 | |
| PP0651 | |

TABLE 38-continued

| Compound No. | Structural Formula |
|---|---|
| PP0652 | |
| PP0653 | |

TABLE 38-continued
| Compound No. | Structural Formula |
|---|---|
| PP0654 | 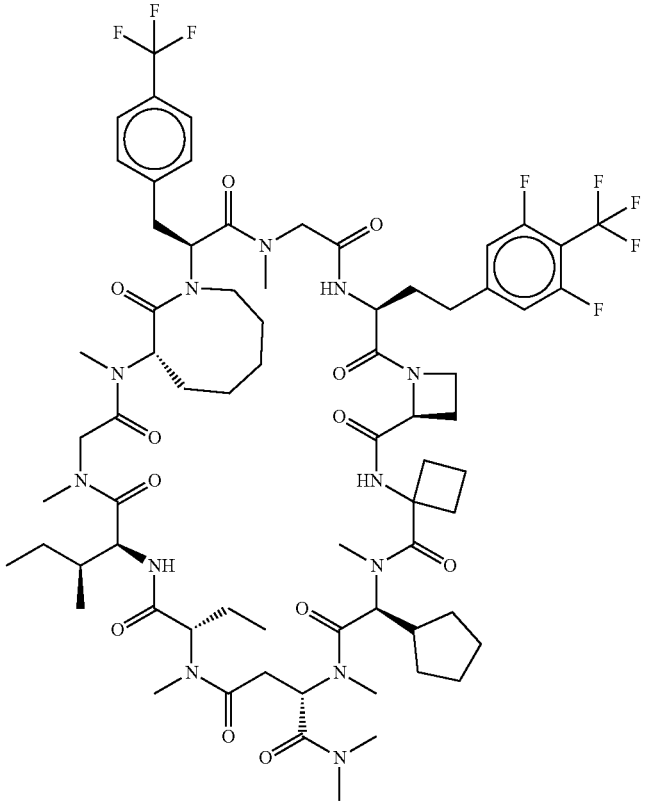 |
| PP0655 | 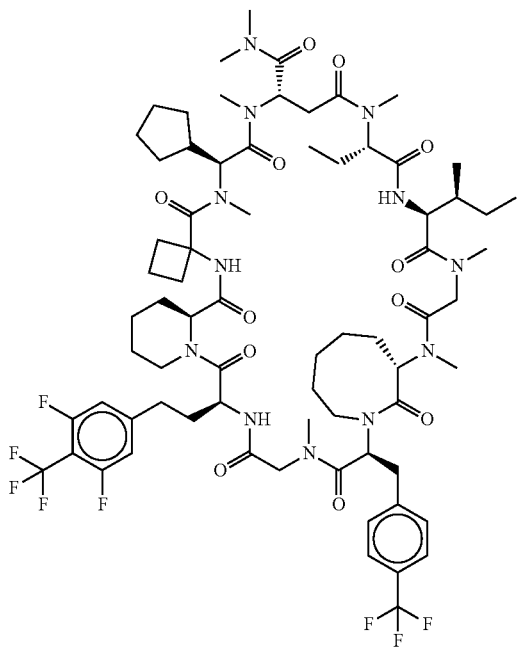 |

| Compound No. | Structural Formula |
|---|---|
| PP0656 | 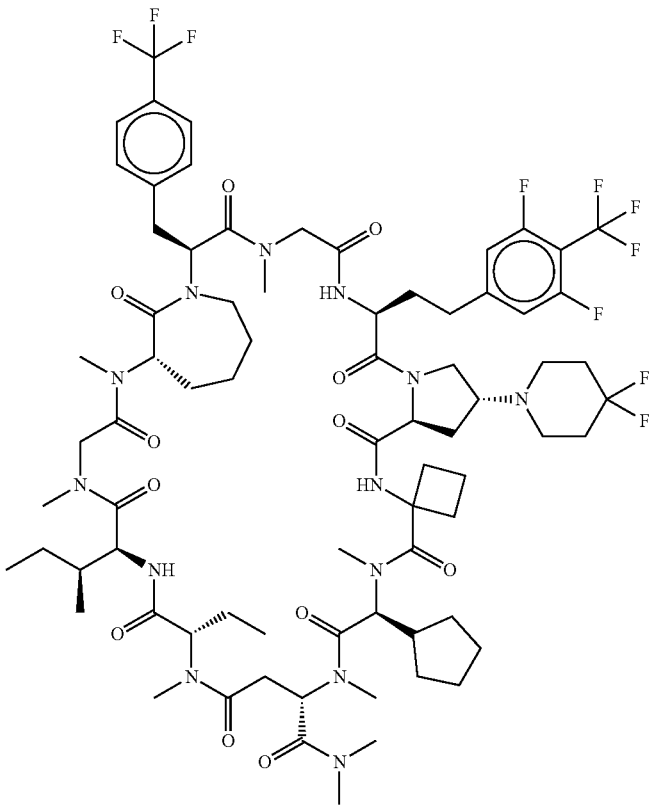 |
| PP0657 | 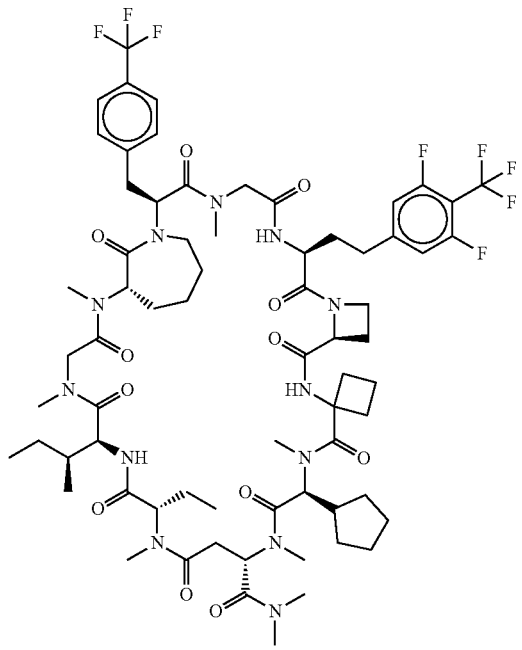 |

TABLE 38-continued

| Compound No. | Structural Formula |
|---|---|
| PP0658 | |
| PP0659 | |

TABLE 38-continued
| Compound No. | Structural Formula |
|---|---|
| PP0660 | 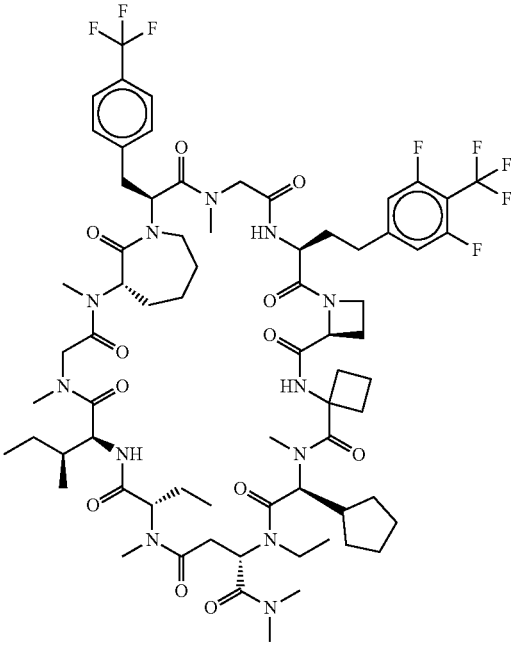 |
| PP0661 | 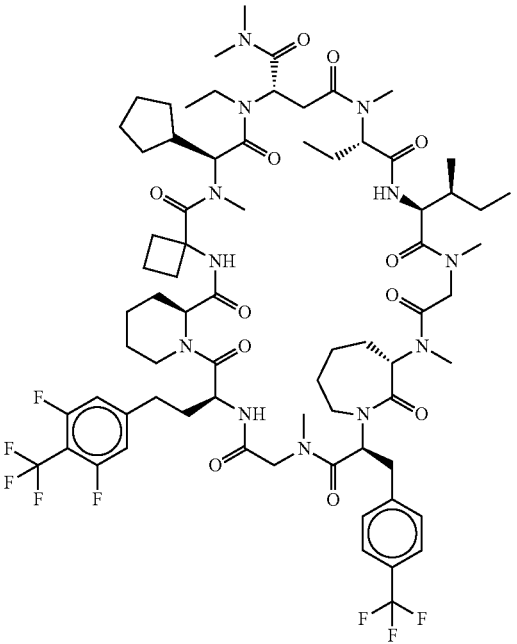 |

TABLE 38-continued
| Compound No. | Structural Formula |
|---|---|
| PP0662 | 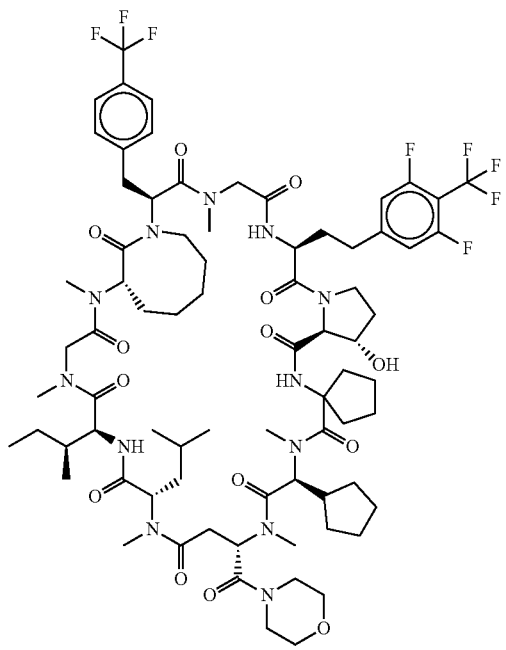 |
| PP0663 | 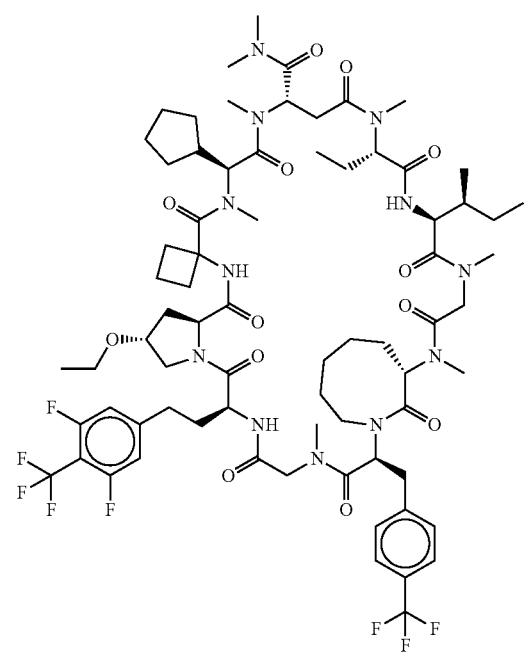 |

| Compound No. | Structural Formula |
|---|---|
| PP0664 | 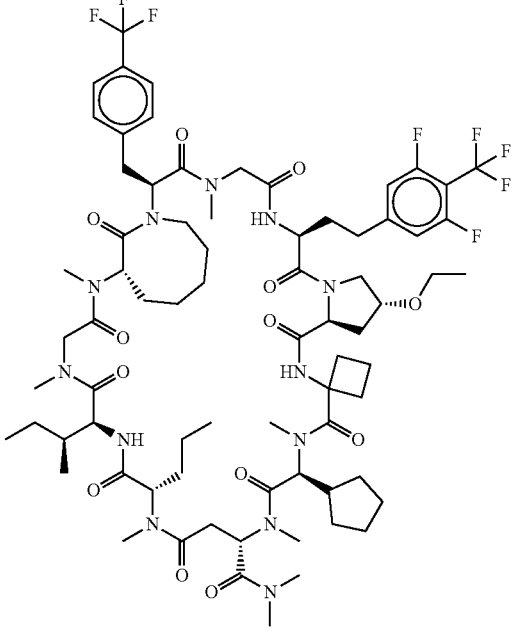 |
| PP0665 | 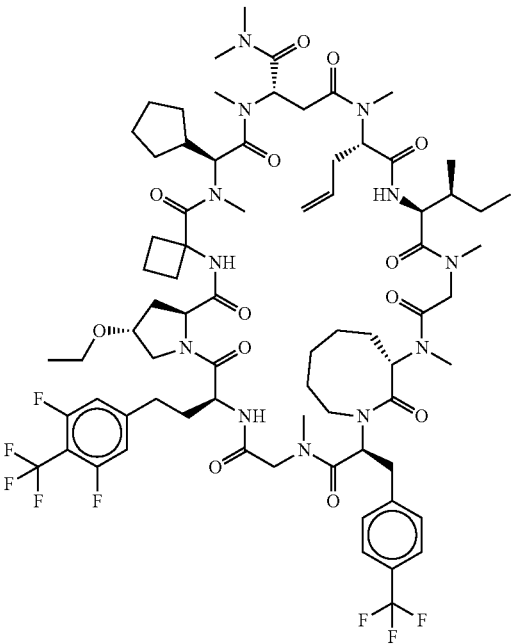 |

ёа
| Compound No. | Structural Formula |
|---|---|
| PP0666 | 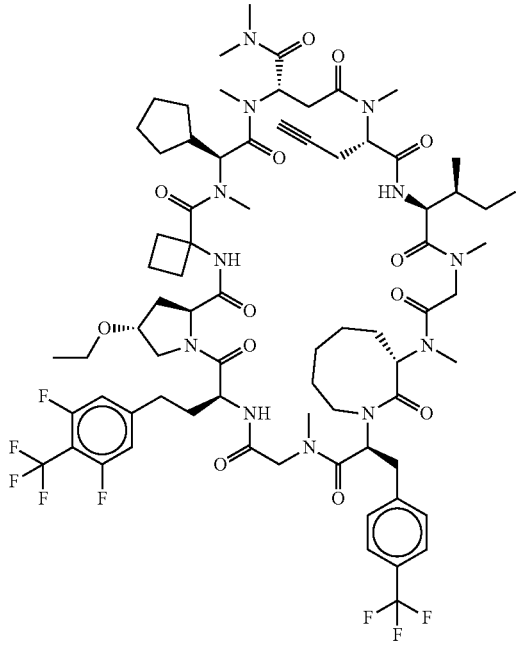 |
| PP0667 | 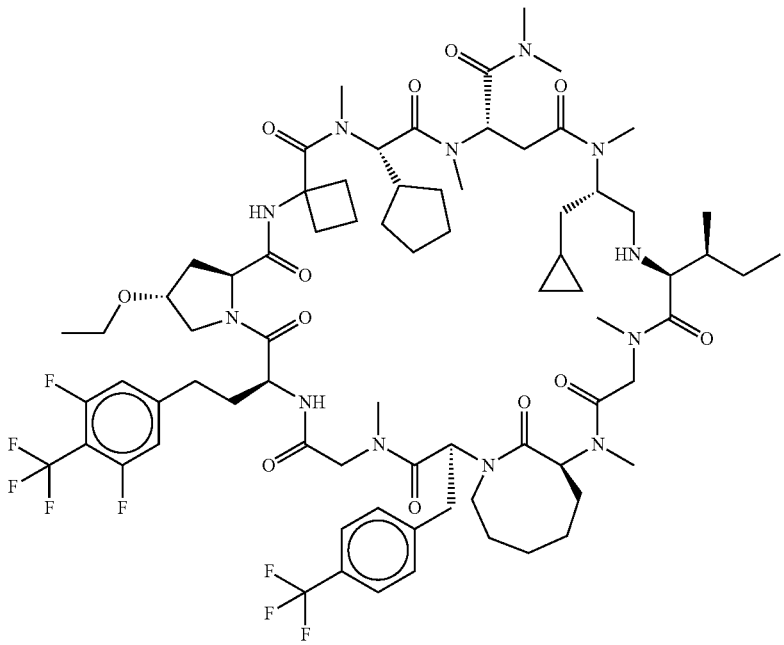 |

TABLE 38-continued
| Compound No. | Structural Formula |
|---|---|
| PP0668 | 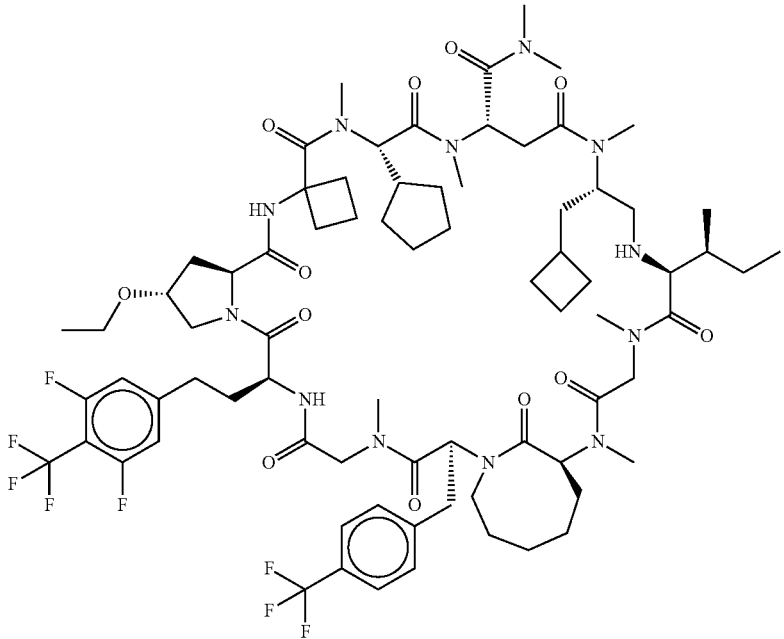 |
| PP0669 | 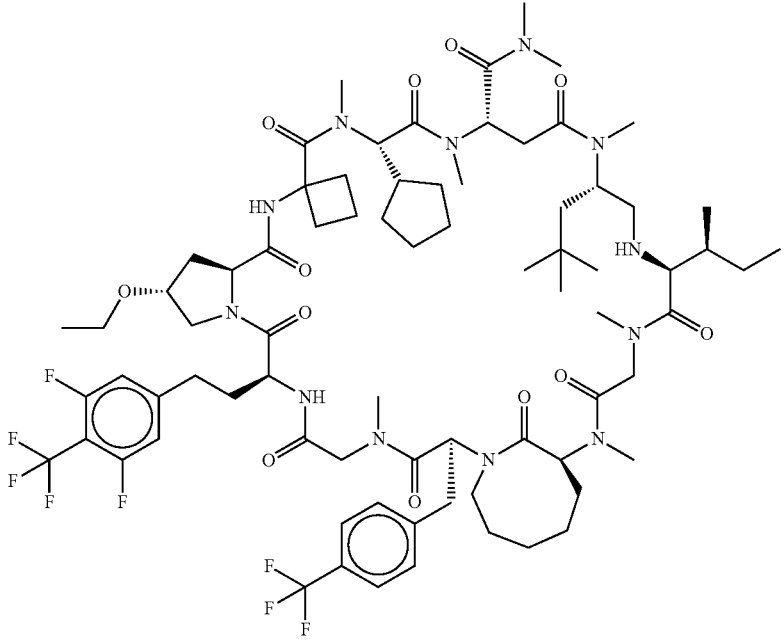 |

татBLE 38-continued
| Compound No. | Structural Formula |
|---|---|
| PP0670 | 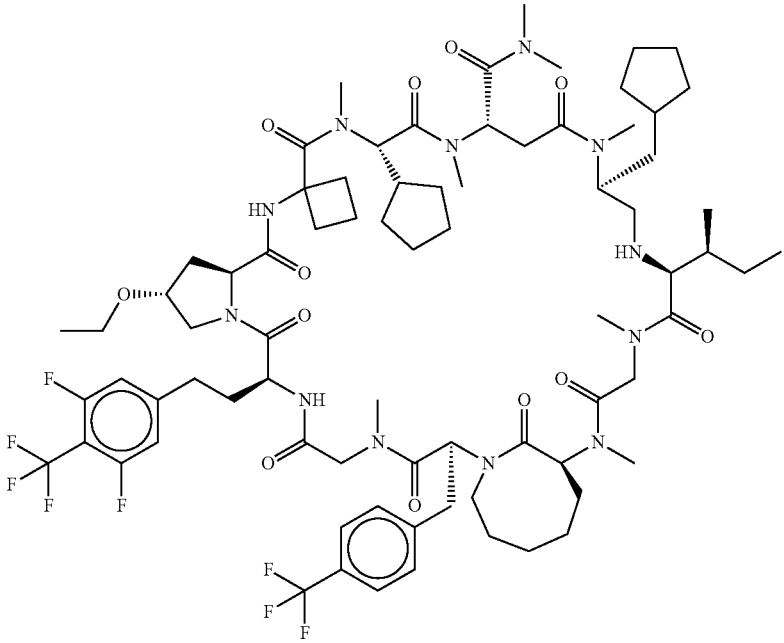 |
| PP0671 | 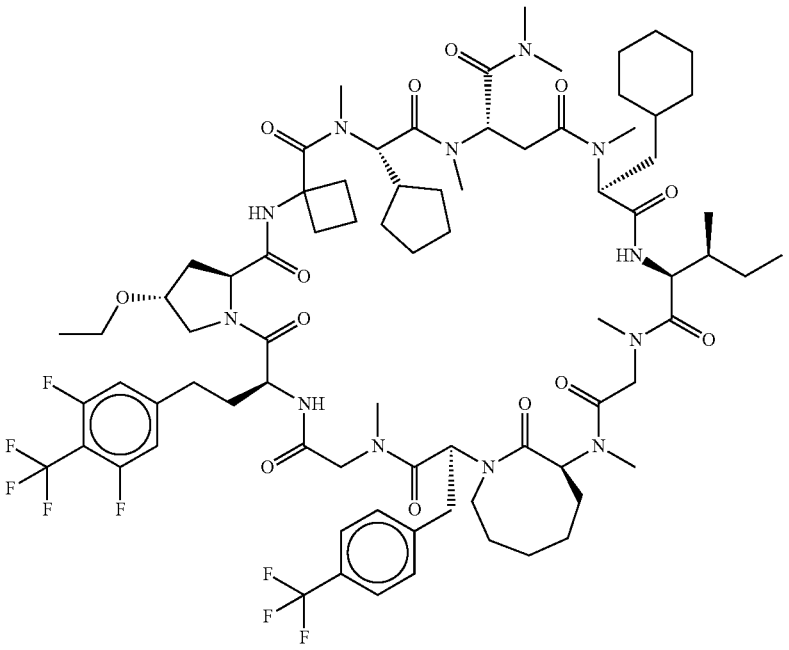 |

TABLE 38-continued
| Compound No. | Structural Formula |
|---|---|
| PP0672 | 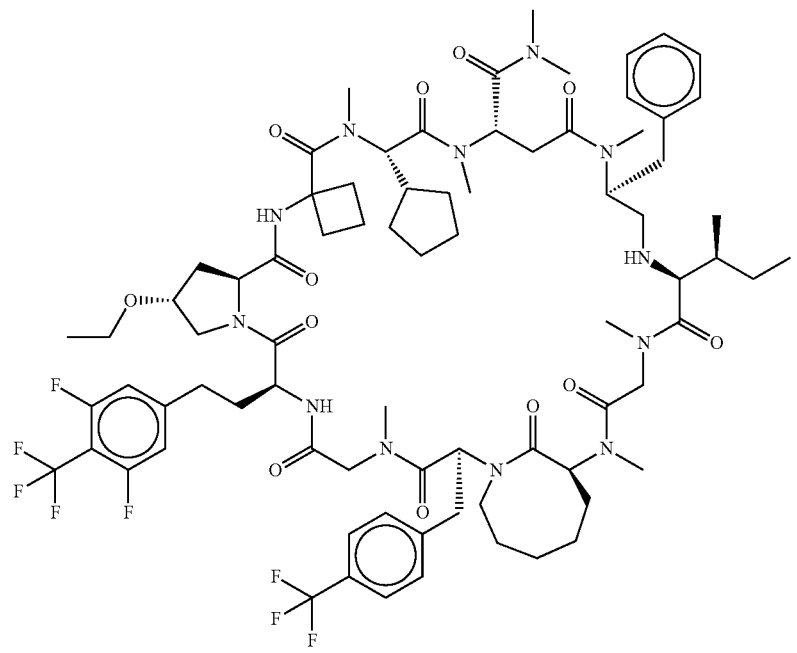 |
| PP0673 | 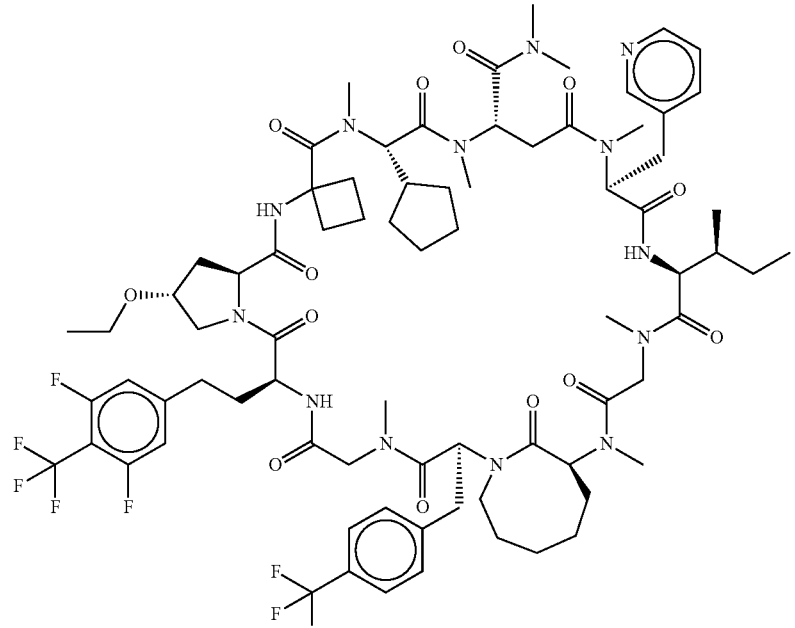 |

TABLE 38-continued
| Compound No. | Structural Formula |
|---|---|
| PP0674 | 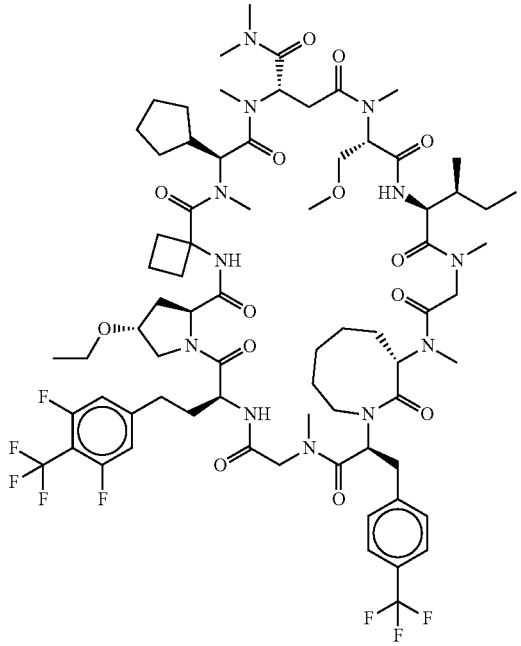 |
| PP0675 | 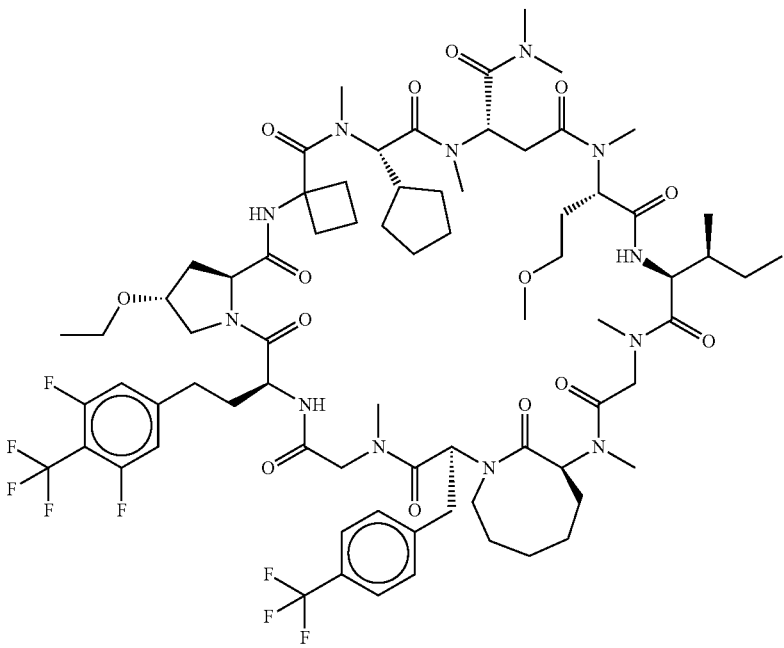 |

TABLE 38-continued
| Compound No. | Structural Formula |
|---|---|
| PP0678 | 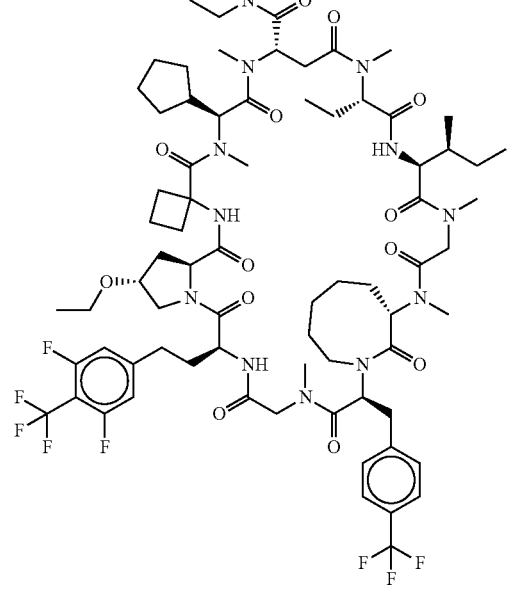 |
| PP0679 | 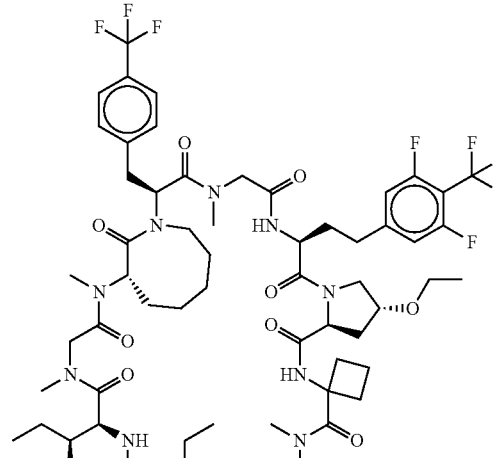 |

TABLE 38-continued
| Compound No. | Structural Formula |
| --- | --- |
| PP0680 | 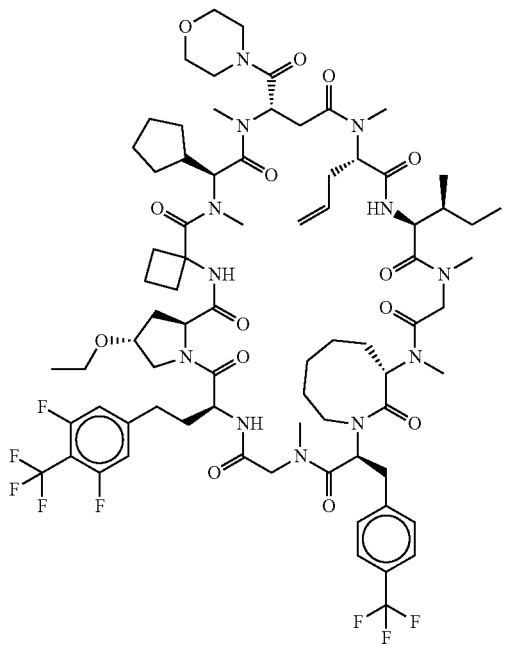 |
| PP0681 | 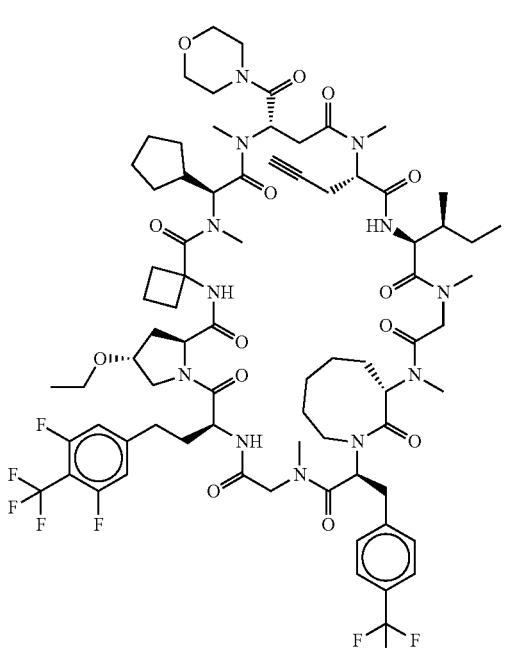 |

TABLE 38-continued
| Compound No. | Structural Formula |
|---|---|
| PP0682 | 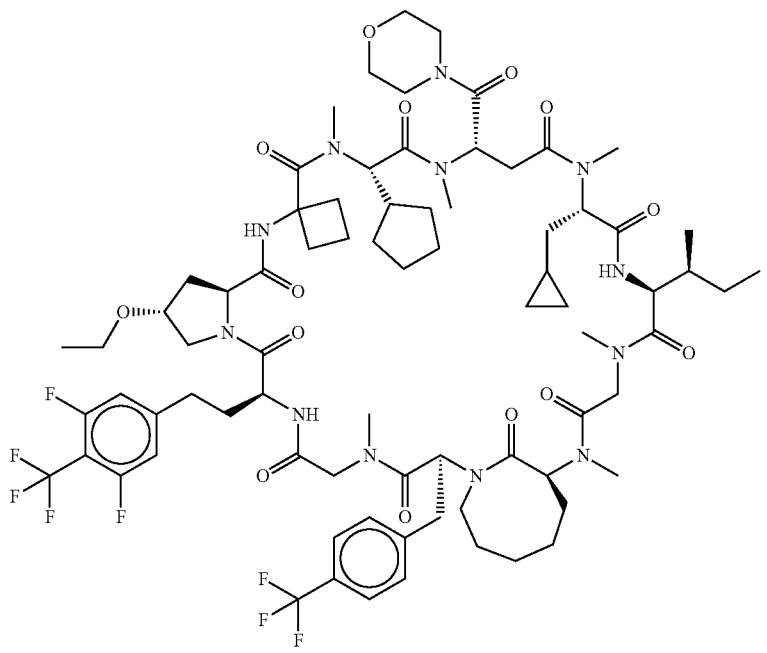 |
| PP0683 | 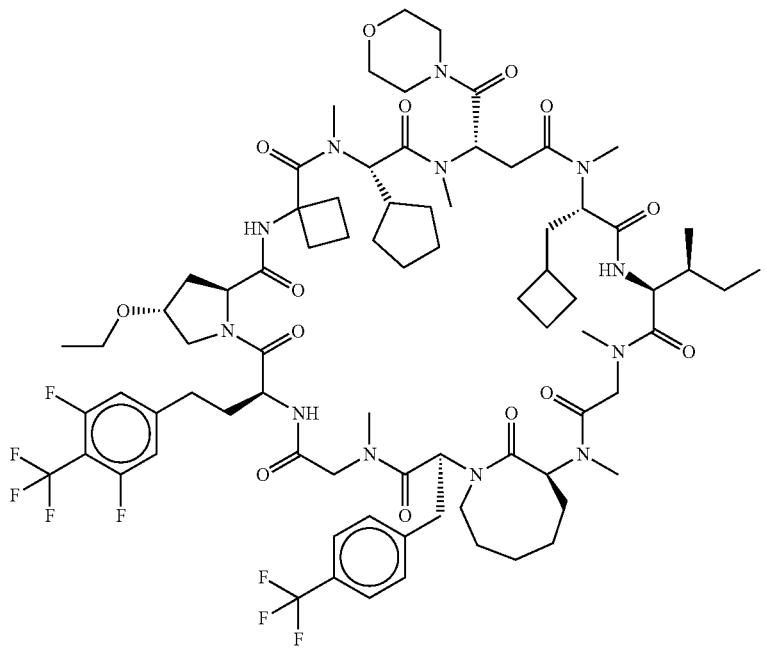 |

TABLE 38-continued
| Compound No. | Structural Formula |
|---|---|
| PP0684 | 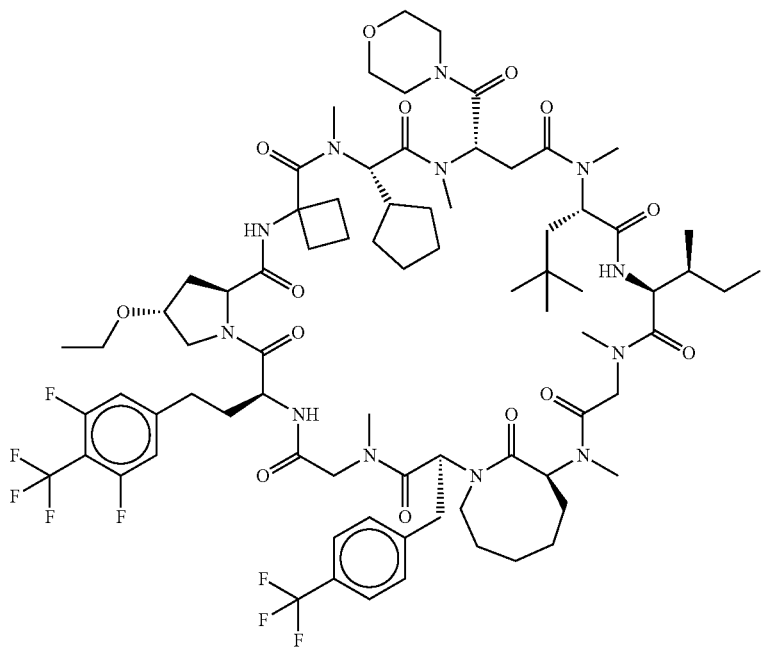 |
| PP0685 | 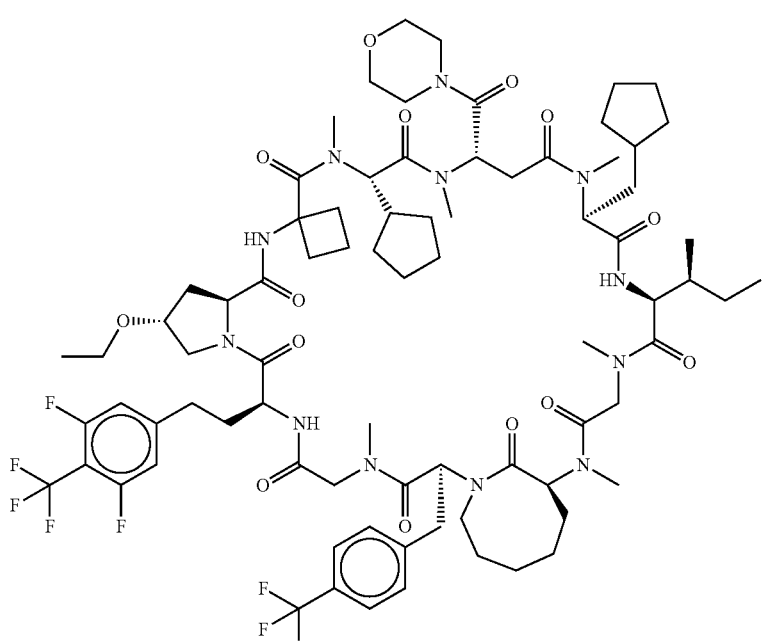 |

TABLE 38-continued
| Compound No. | Structural Formula |
| --- | --- |
| PP0686 | 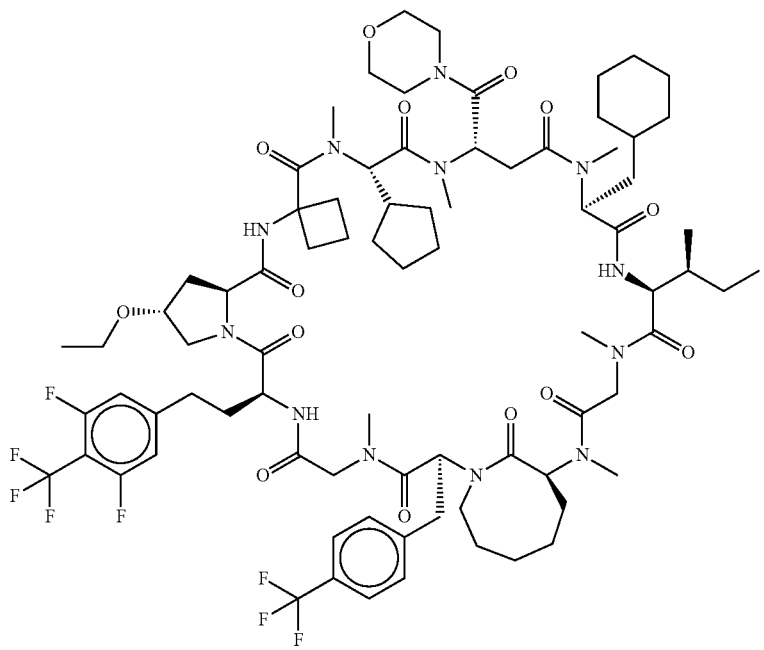 |
| PP0687 | 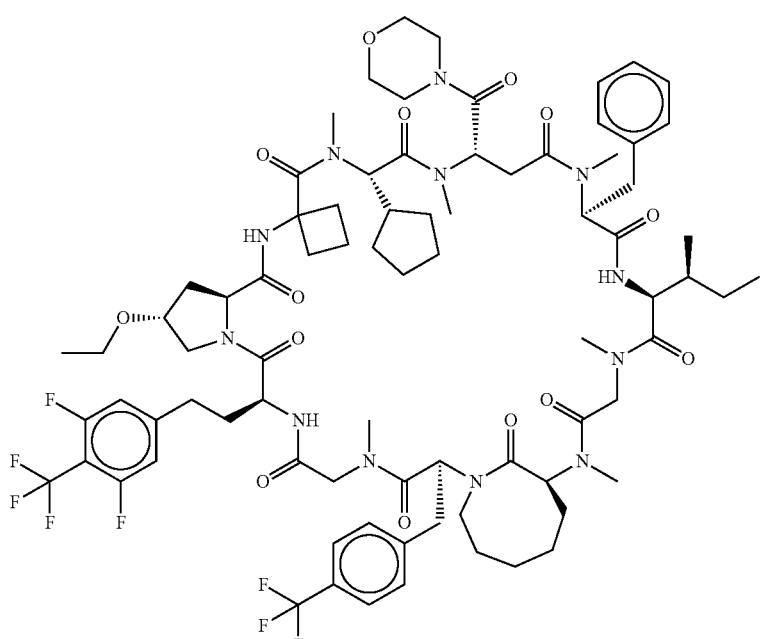 |

TABLE 38-continued
| Compound No. | Structural Formula |
|---|---|
| PP0688 | 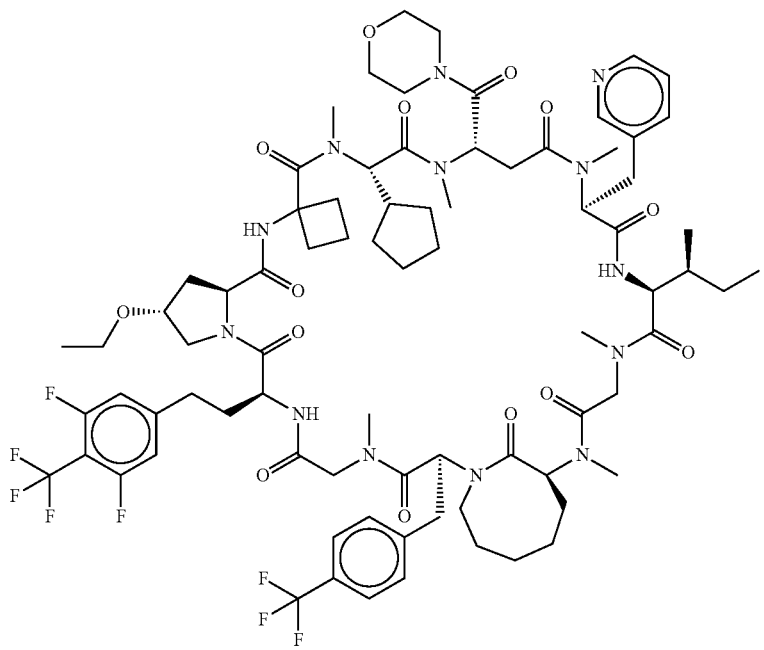 |
| PP0689 | 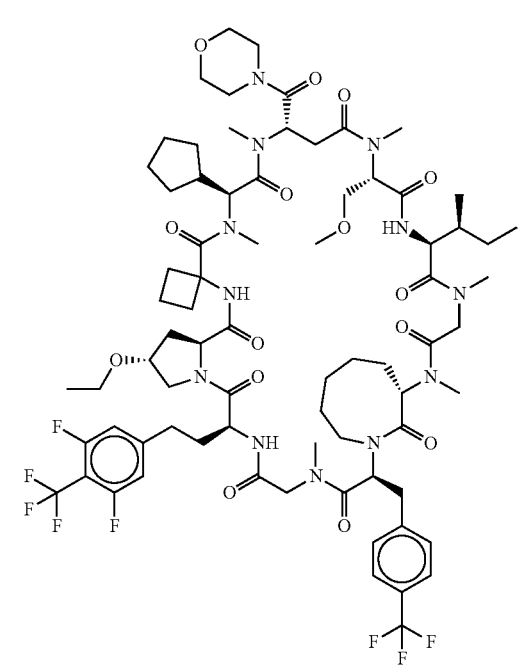 |

TABLE 38-continued
| Compound No. | Structural Formula |
|---|---|
| PP0690 | 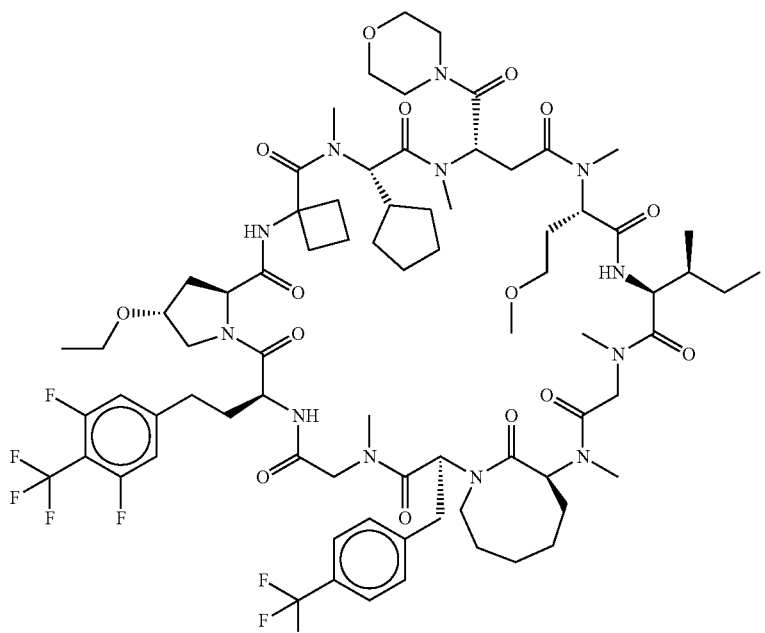 |
| PP0693 | 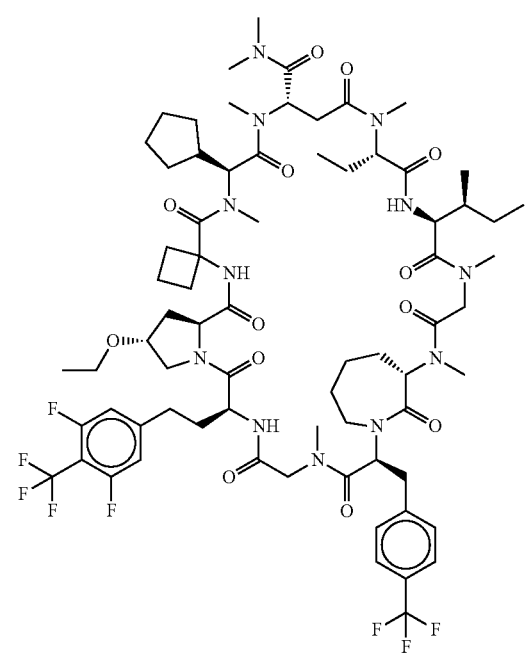 |

TABLE 38-continued

| Compound No. | Structural Formula |
|---|---|
| PP0694 | |
| PP0695 | |

//
TABLE 38-continued
| Compound No. | Structural Formula |
|---|---|
| PP0696 | 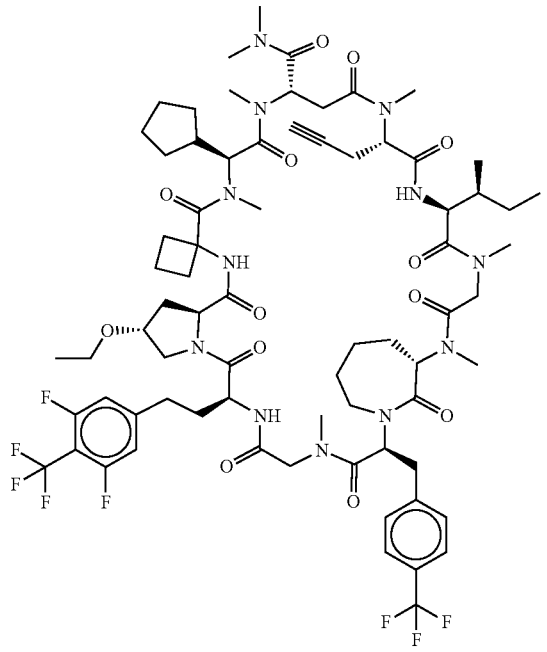 |
| PP0697 | 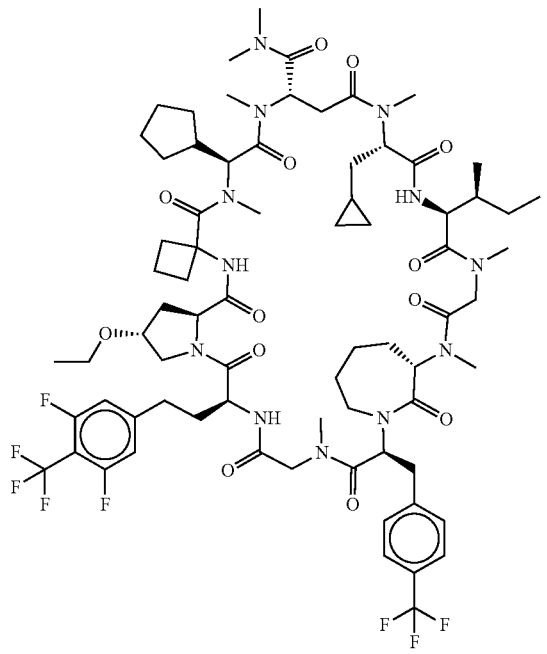 |

TABLE 38-continued
| Compound No. | Structural Formula |
|---|---|
| PP0698 | 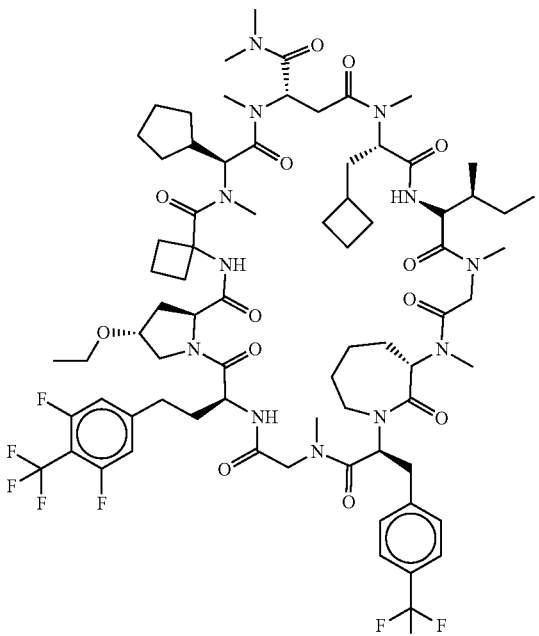 |
| PP0699 | 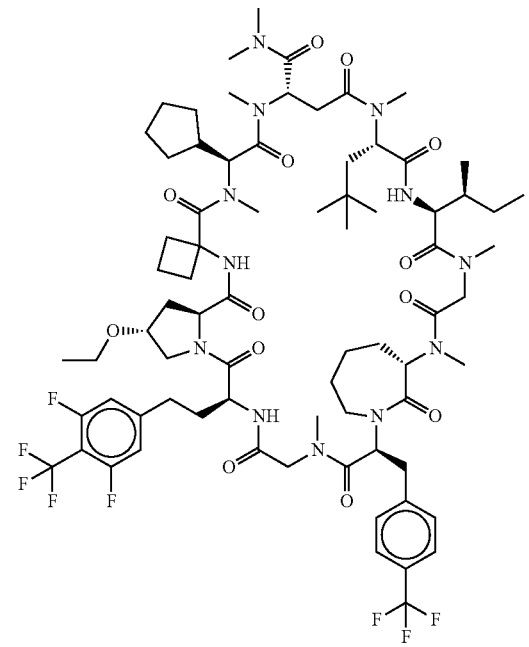 |

TABLE 38-continued

| Compound No. | Structural Formula |
|---|---|
| PP0700 | |
| PP0701 | |

TABLE 38-continued
| Compound No. | Structural Formula |
|---|---|
| PP0702 | 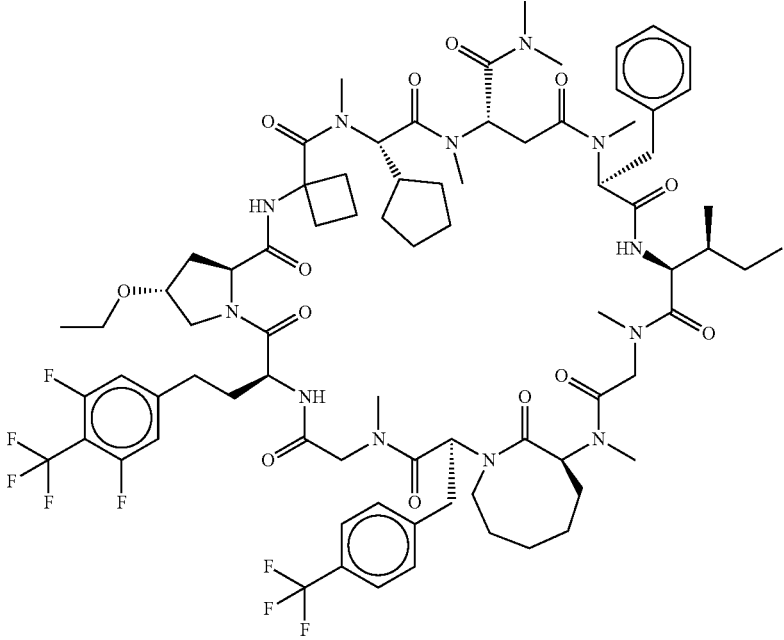 |
| PP0703 | 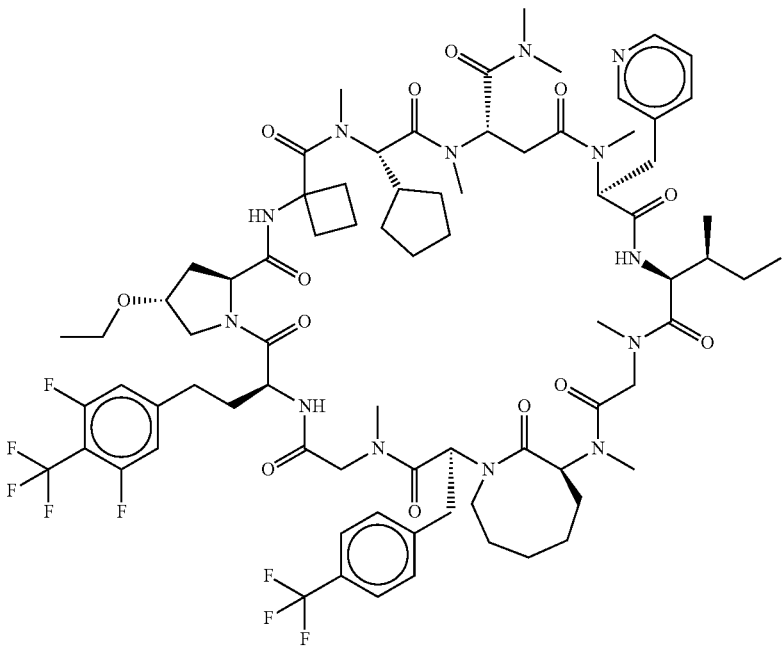 |

TABLE 38-continued

| Compound No. | Structural Formula |
|---|---|
| PP0704 | |
| PP0705 | |

TABLE 38-continued

| Compound No. | Structural Formula |
|---|---|
| PP0706 | |
| PP0708 | |

TABLE 38-continued
| Compound No. | Structural Formula |
|---|---|
| PP0709 | 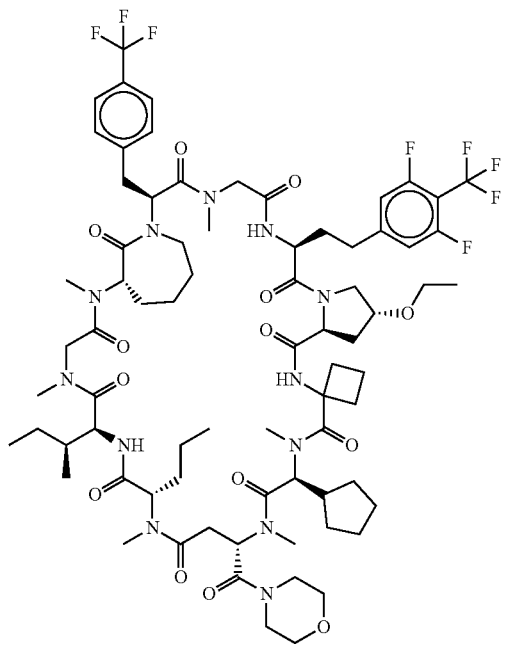 |
| PP0710 | 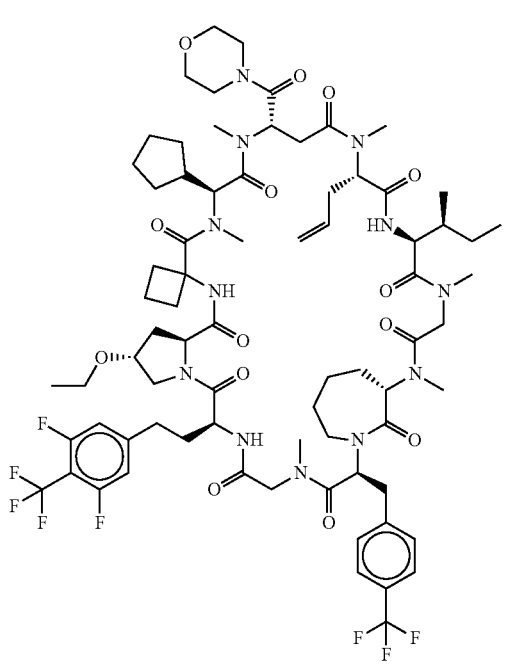 |

| Compound No. | Structural Formula |
|---|---|
| PP0711 | |
| PP0712 | |

TABLE 38-continued

| Compound No. | Structural Formula |
|---|---|
| PP0713 | |
| PP0714 | |

TABLE 38-continued
| Compound No. | Structural Formula |
|---|---|
| PP0715 | 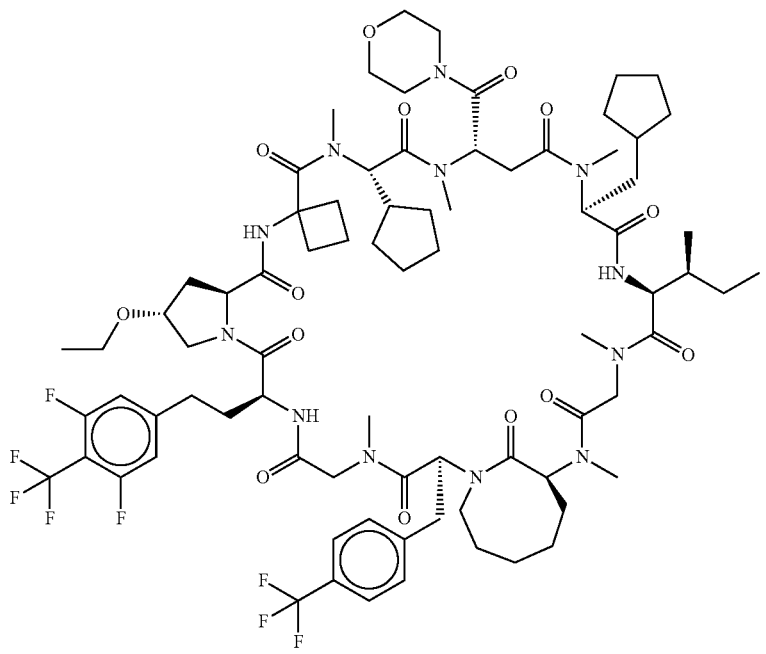 |
| PP0716 | 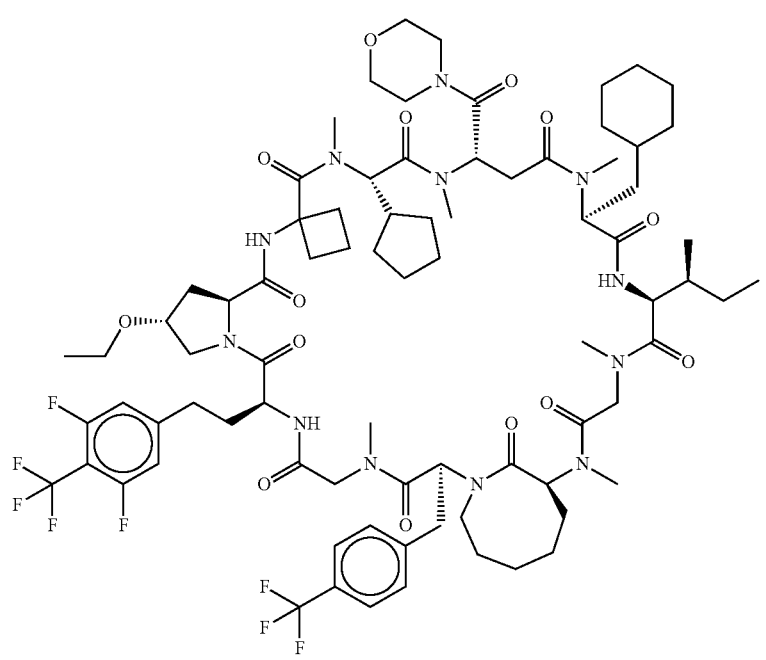 |

TABLE 38-continued

| Compound No. | Structural Formula |
| --- | --- |
| PP0717 | |
| PP0718 | |

TABLE 38-continued
| Compound No. | Structural Formula |
|---|---|
| PP0719 | 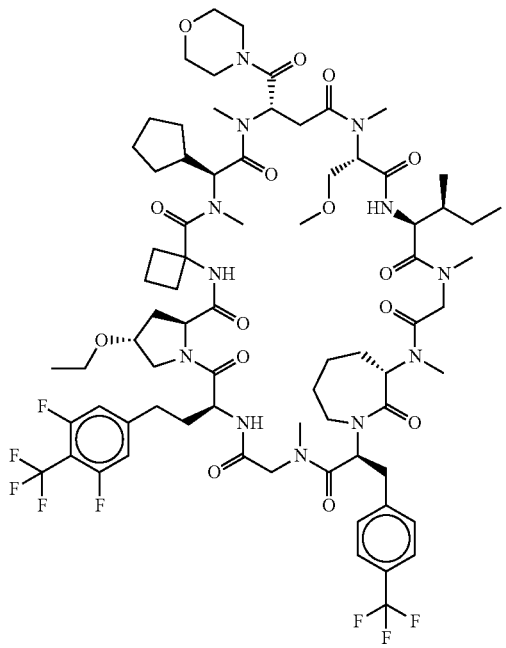 |
| PP0720 | 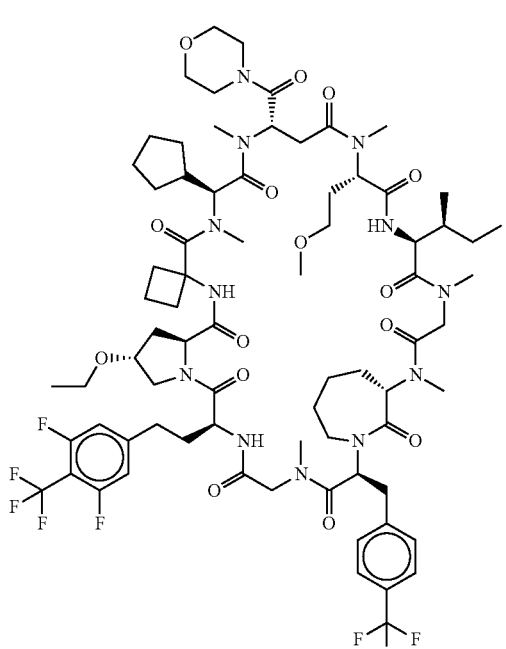 |

TABLE 38-continued

| Compound No. | Structural Formula |
|---|---|
| PP0721 | |
| PP0722 | |

TABLE 38-continued
| Compound No. | Structural Formula |
|---|---|
| PP0723 | 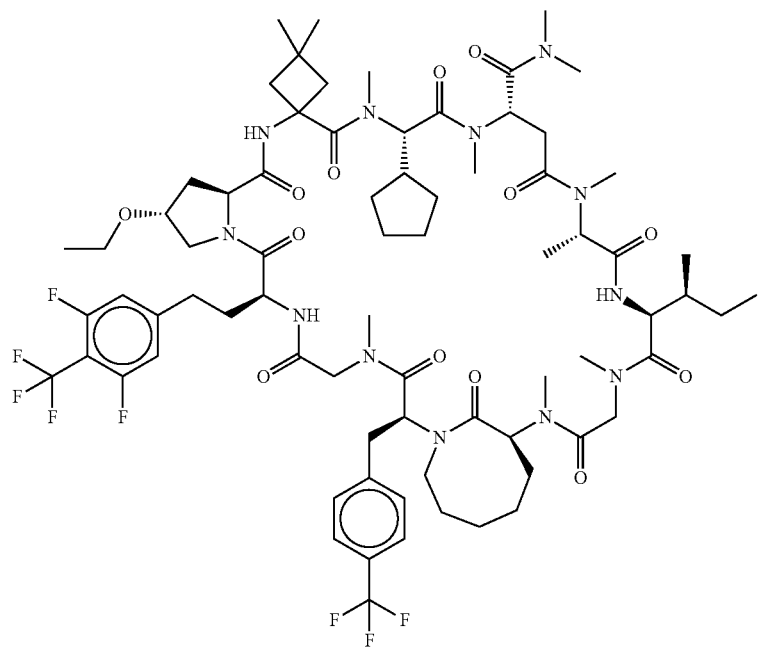 |
| PP0724 | 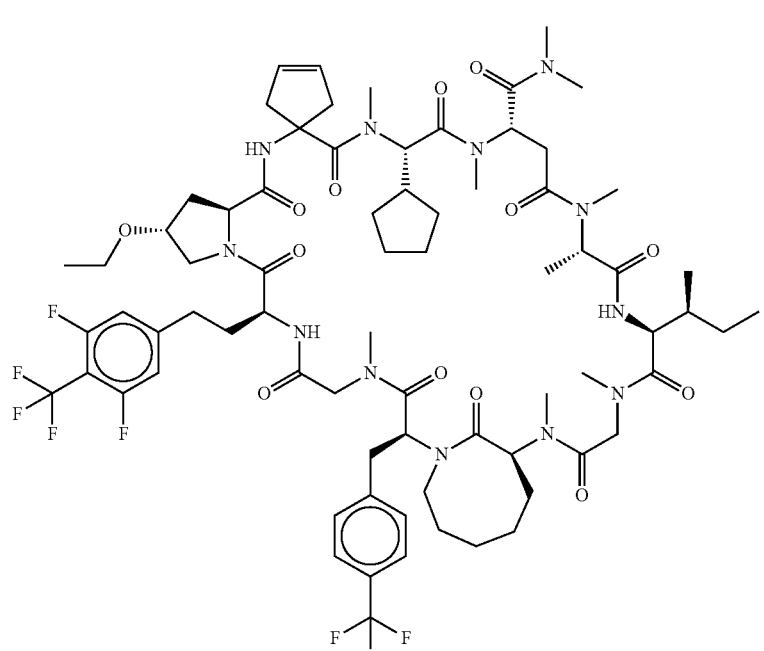 |

TABLE 38-continued

| Compound No. | Structural Formula |
|---|---|
| PP0725 | |
| PP0726 | |

TABLE 38-continued
| Compound No. | Structural Formula |
|---|---|
| PP0727 | 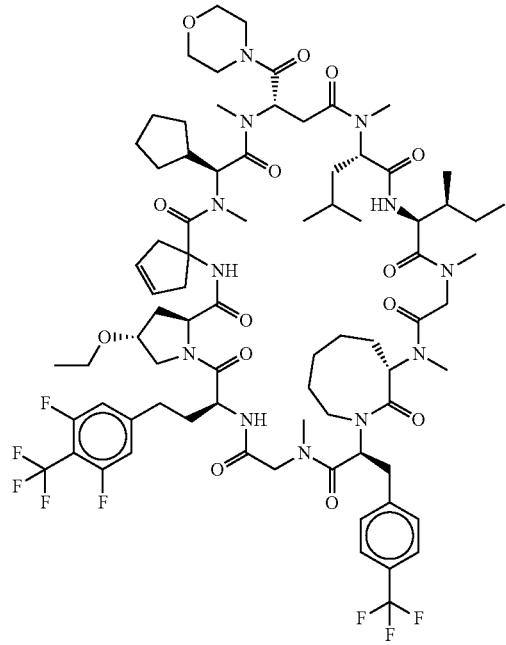 |
| PP0728 | 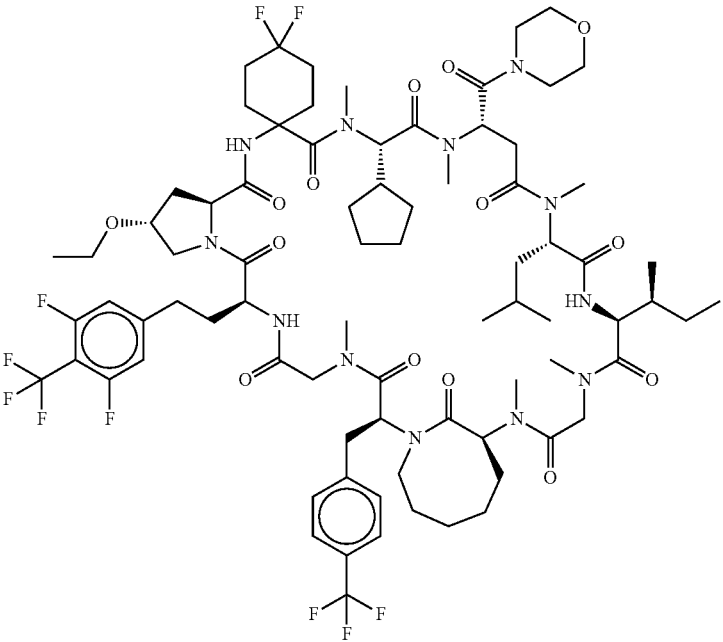 |

TABLE 38-continued
| Compound No. | Structural Formula |
|---|---|
| PP0729 | 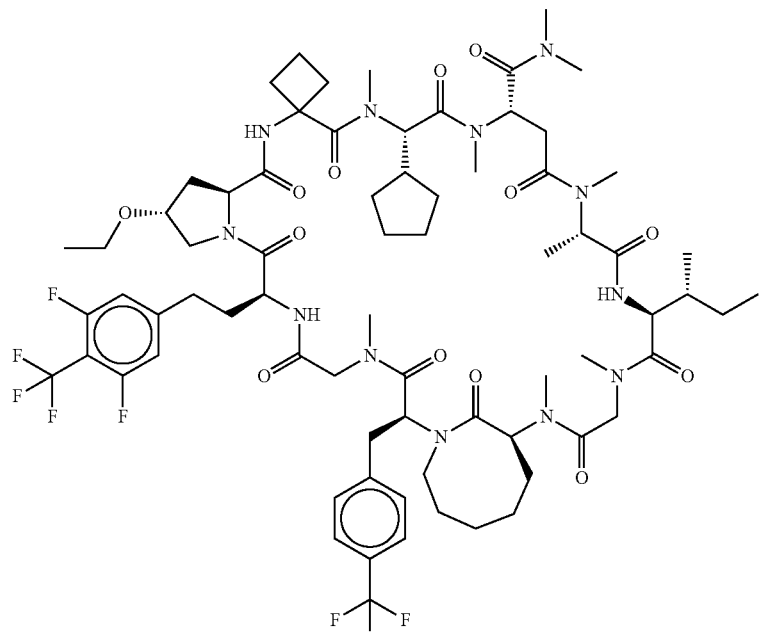 |
| PP0730 | 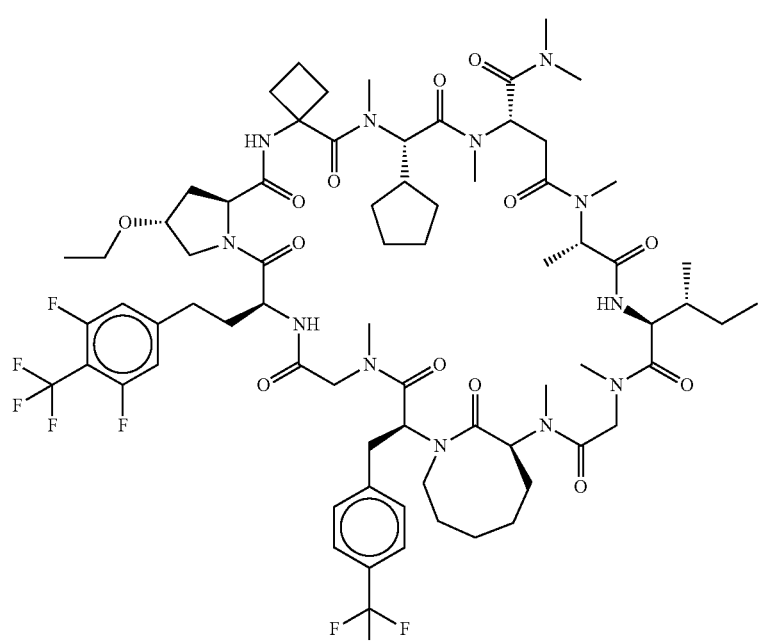 |

TABLE 38-continued
| Compound No. | Structural Formula |
|---|---|
| PP0731 | 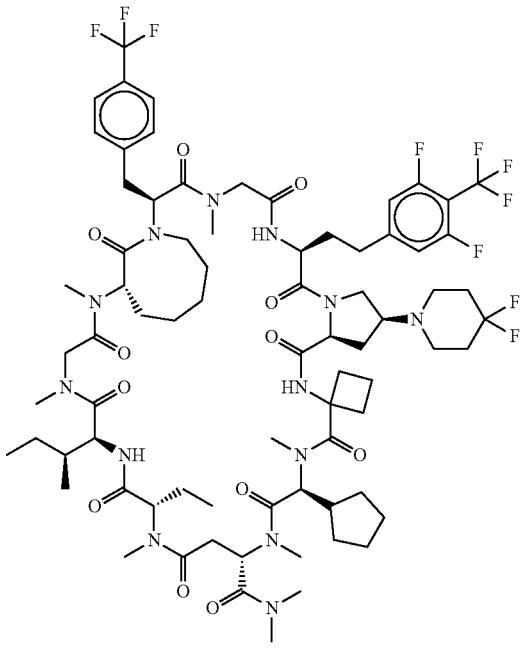 |
| PP0732 | 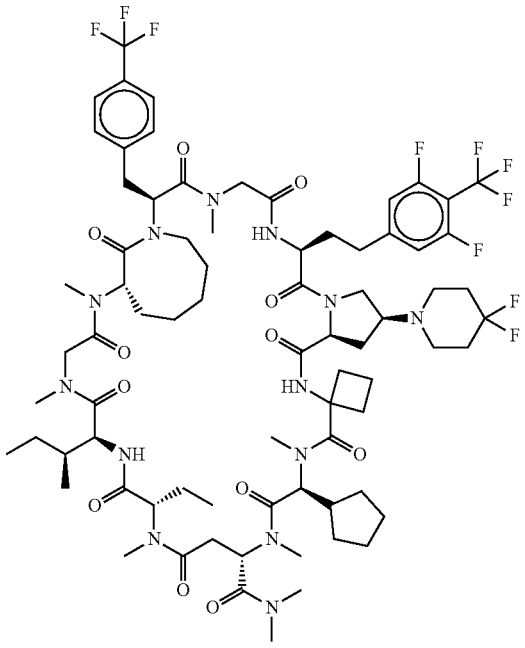 |

TABLE 38-continued
| Compound No. | Structural Formula |
|---|---|
| PP0733 | 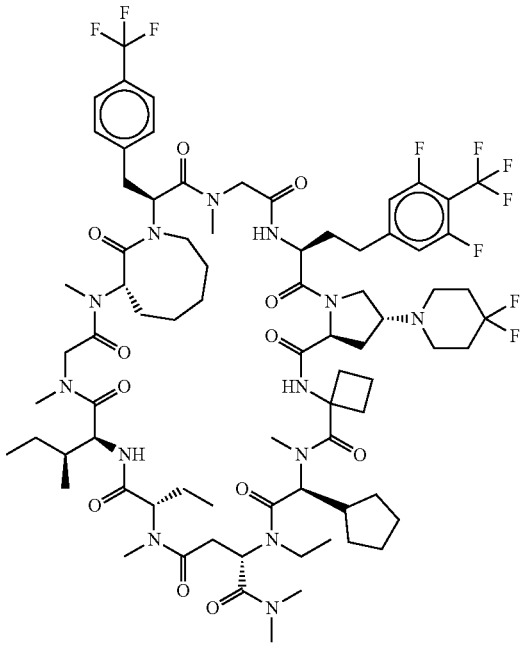 |
| PP0734 | 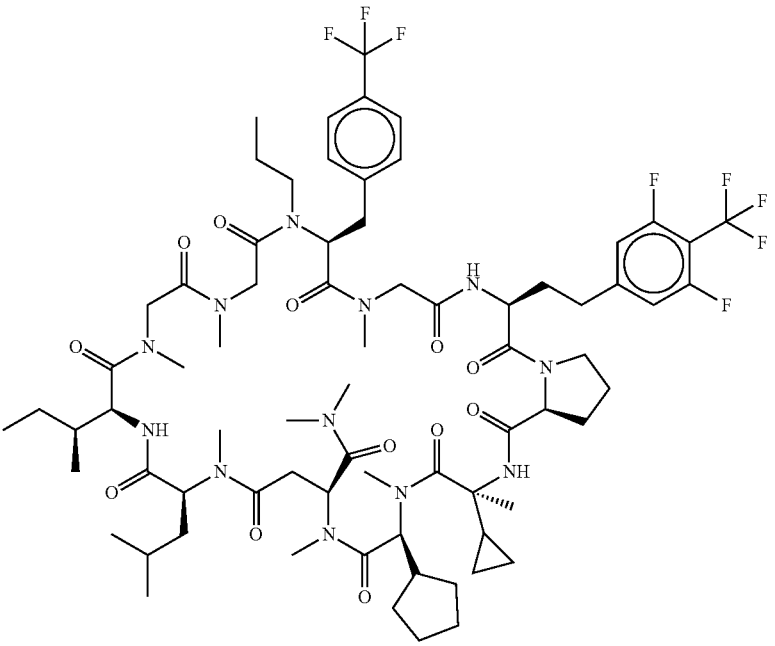 |

TABLE 38-continued
| Compound No. | Structural Formula |
|---|---|
| PP0735 | 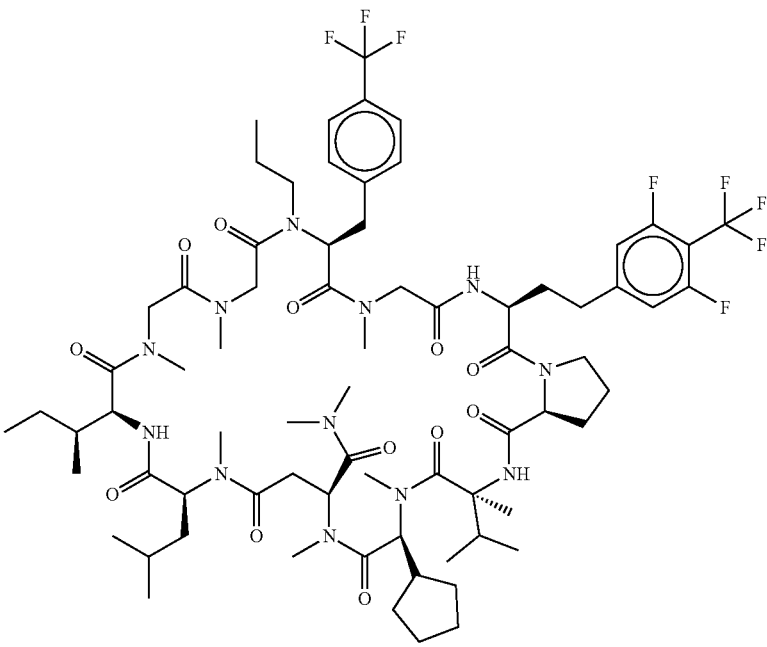 |
| PP0736 | 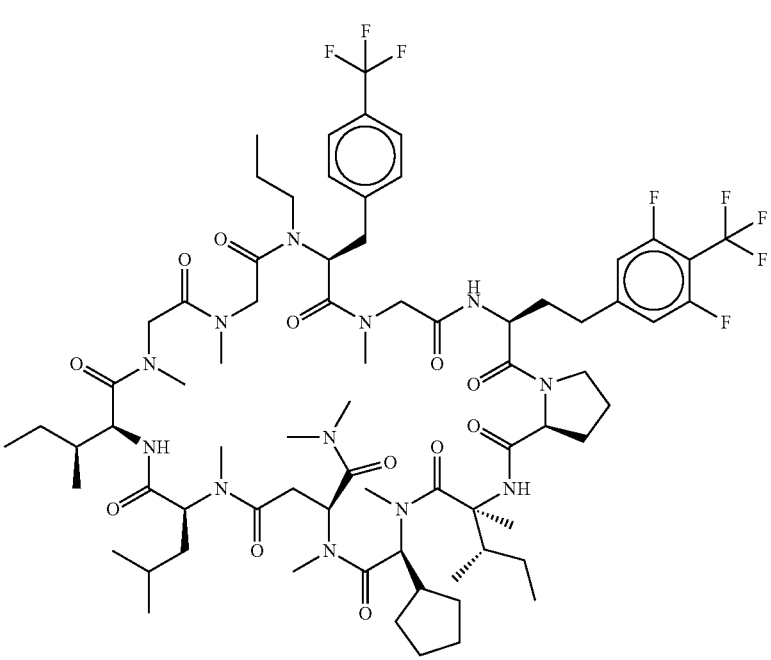 |

TABLE 38-continued
| Compound No. | Structural Formula |
|---|---|
| PP0737 | 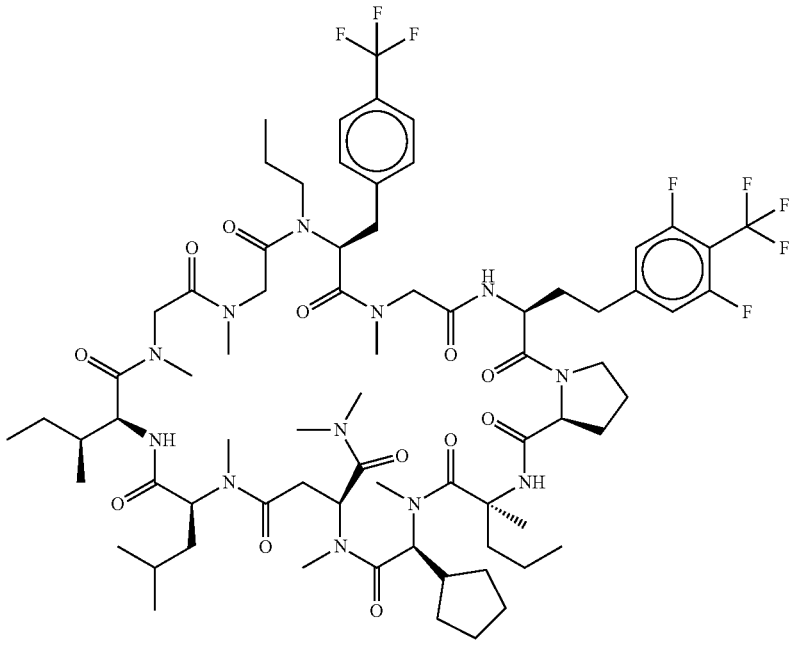 |
| PP0738 | 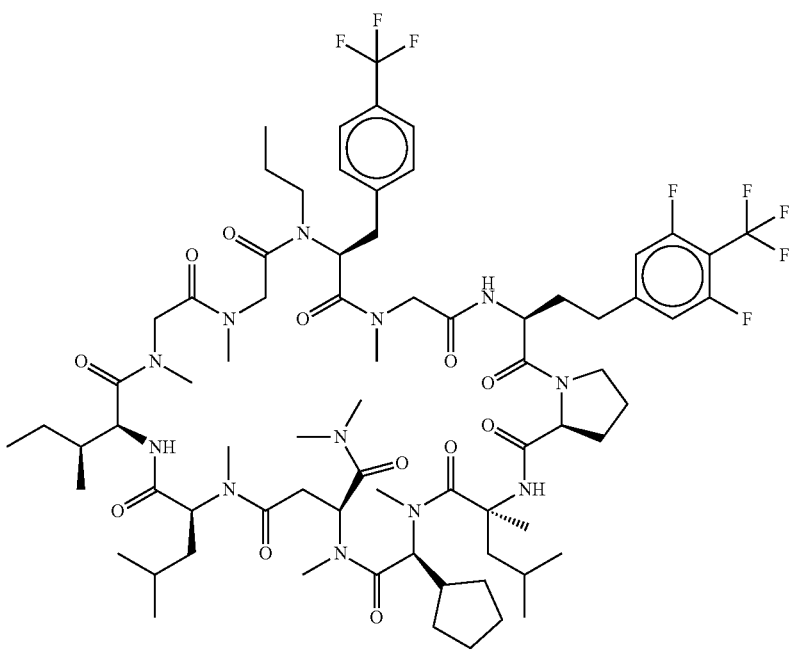 |

TABLE 38-continued
| Compound No. | Structural Formula |
|---|---|
| PP0739 | 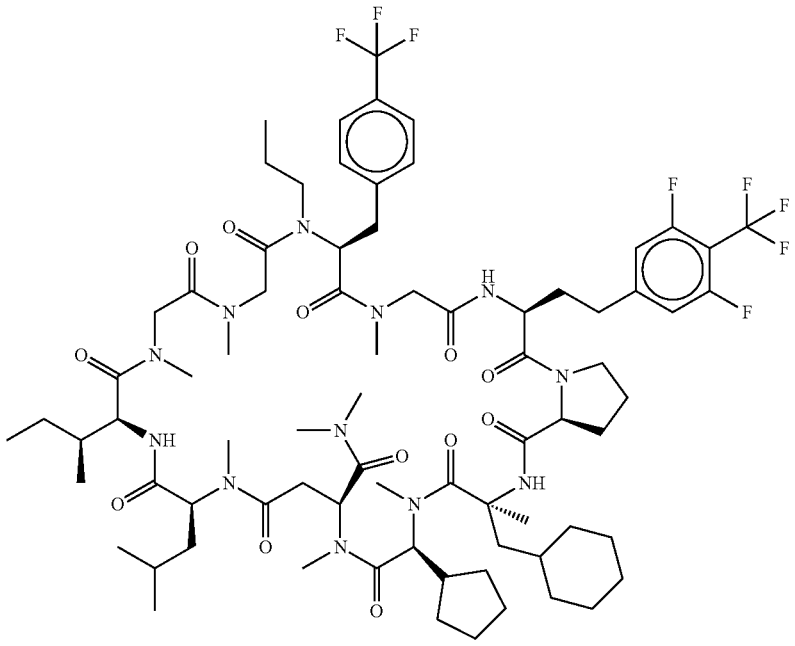 |
| PP0740 | 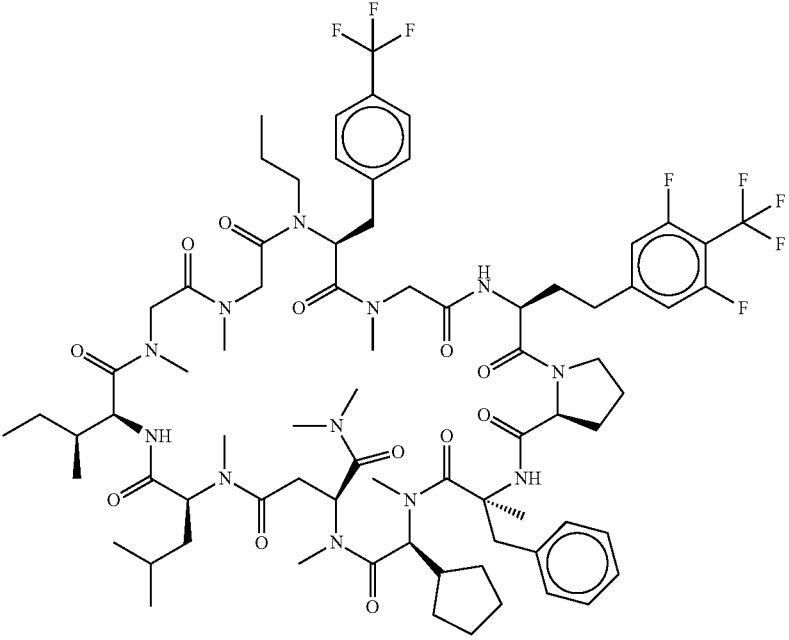 |

TABLE 38-continued
| Compound No. | Structural Formula |
|---|---|
| PP0741 | 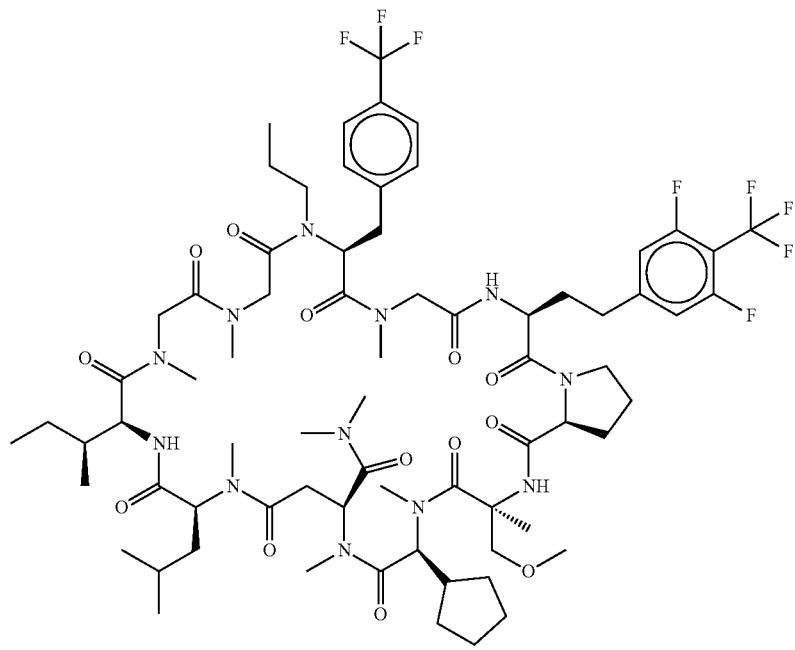 |
| PP0742 | 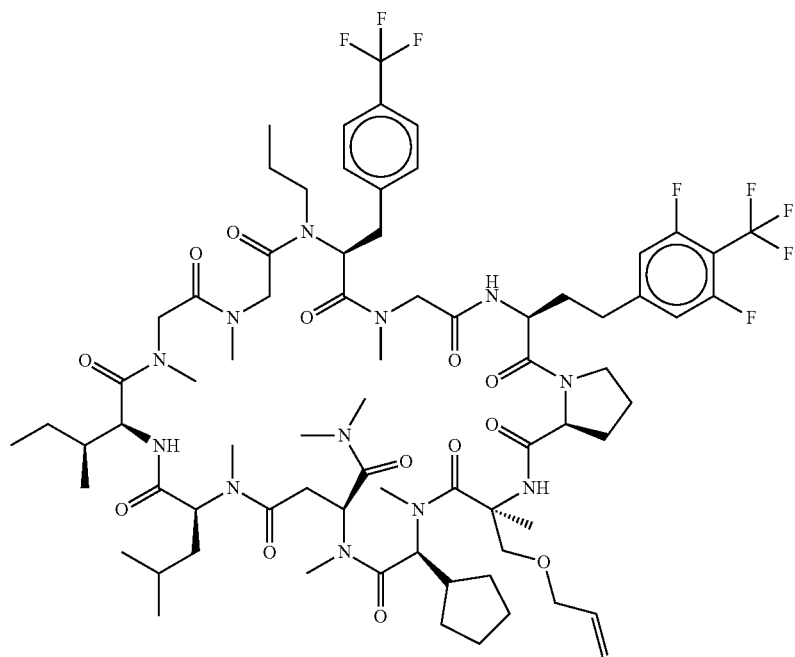 |

TABLE 38-continued
| Compound No. | Structural Formula |
|---|---|
| PP0743 | 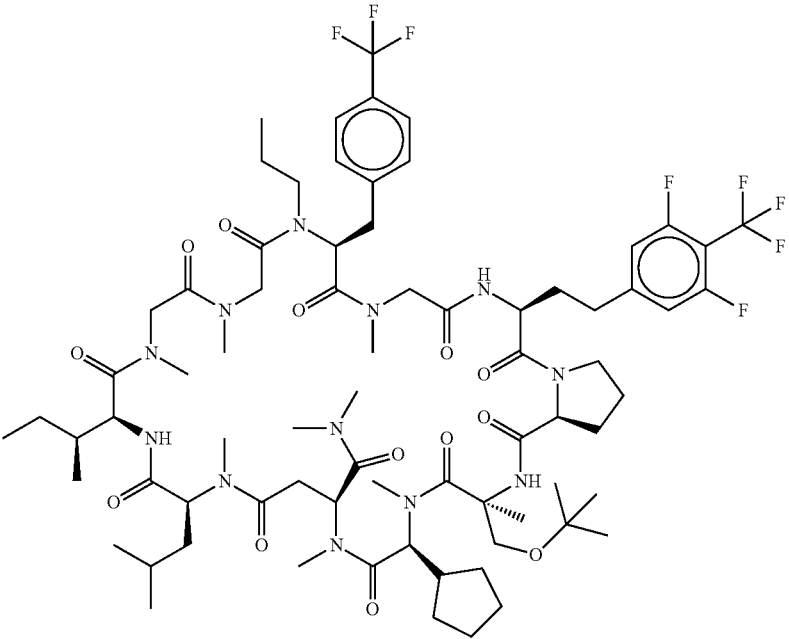 |
| PP0744 | 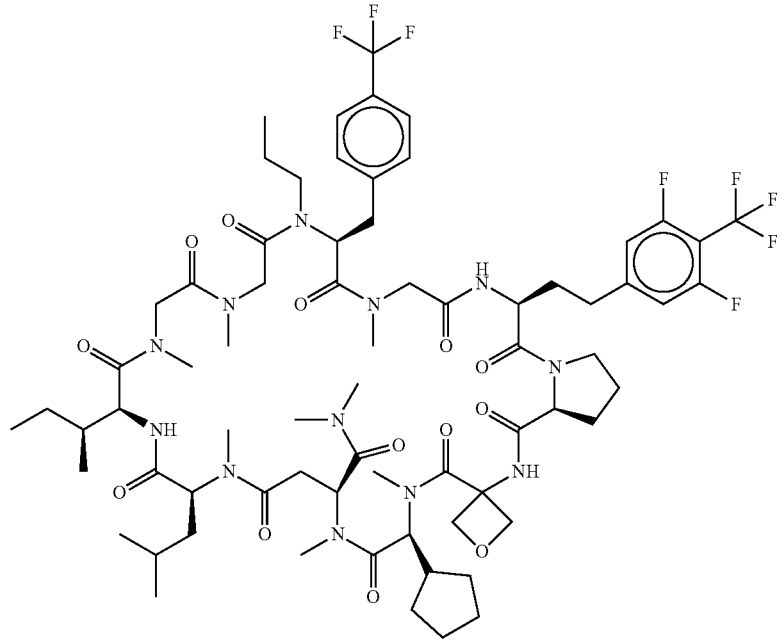 |

TABLE 38-continued
| Compound No. | Structural Formula |
|---|---|
| PP0745 | 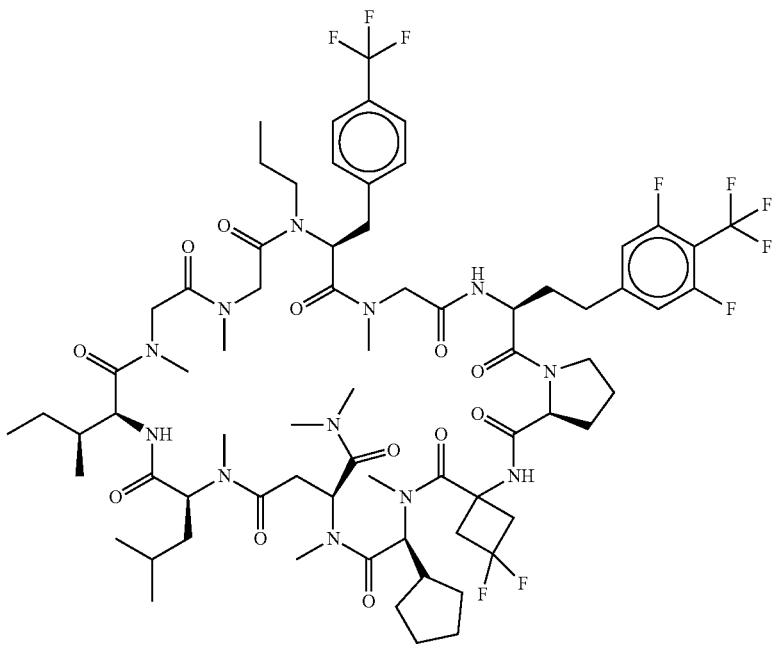 |
| PP0746 | 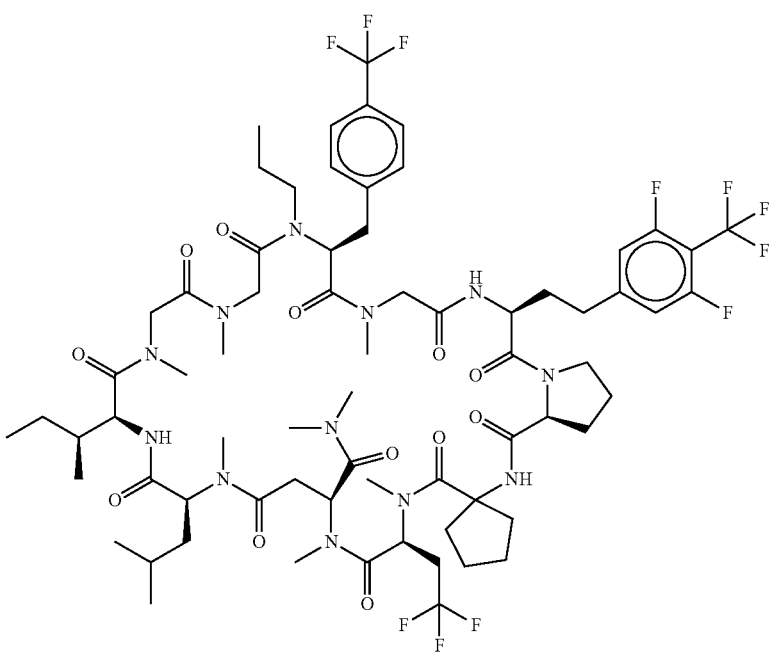 |

TABLE 38-continued
| Compound No. | Structural Formula |
|---|---|
| PP0747 | 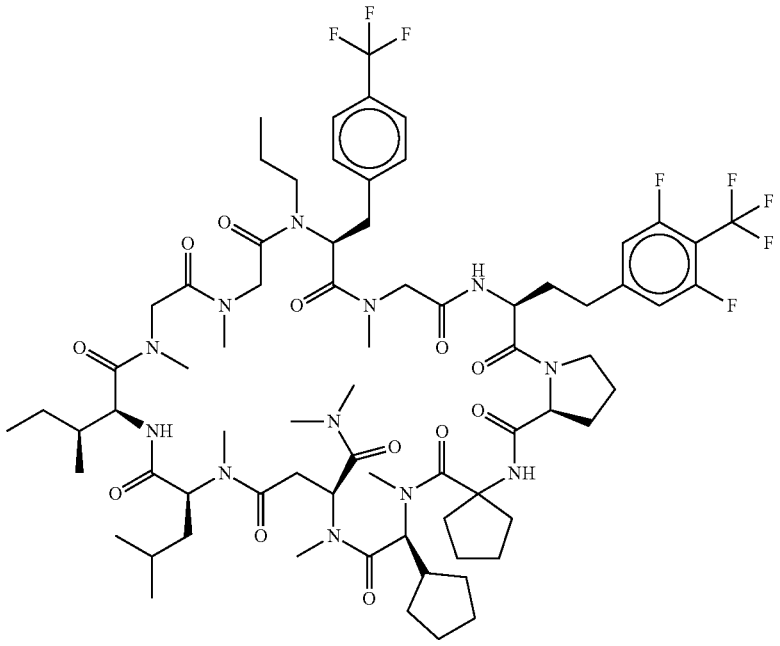 |
| PP0748 | 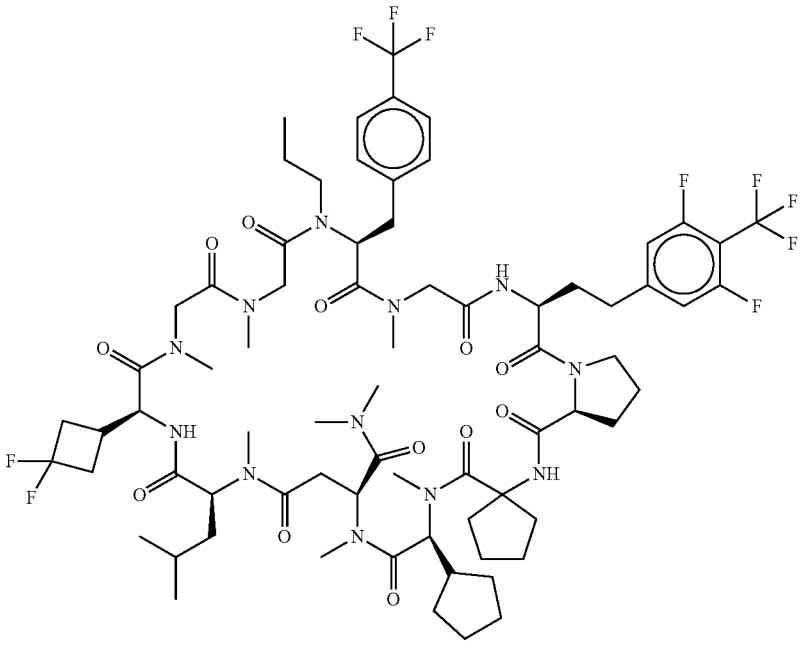 |

TABLE 38-continued

| Compound No. | Structural Formula |
|---|---|
| PP0749 | |
| PP0750 | |

TABLE 38-continued
| Compound No. | Structural Formula |
|---|---|
| PP0751 | 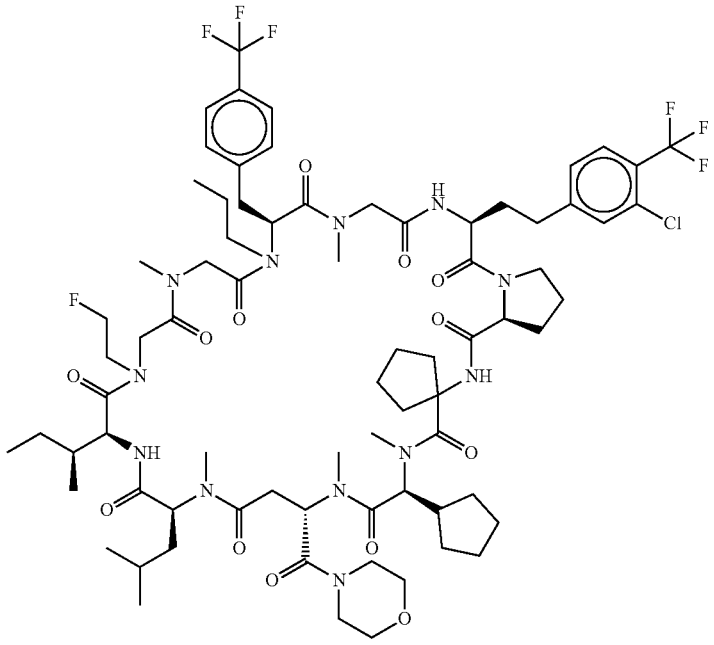 |
| PP0752 | 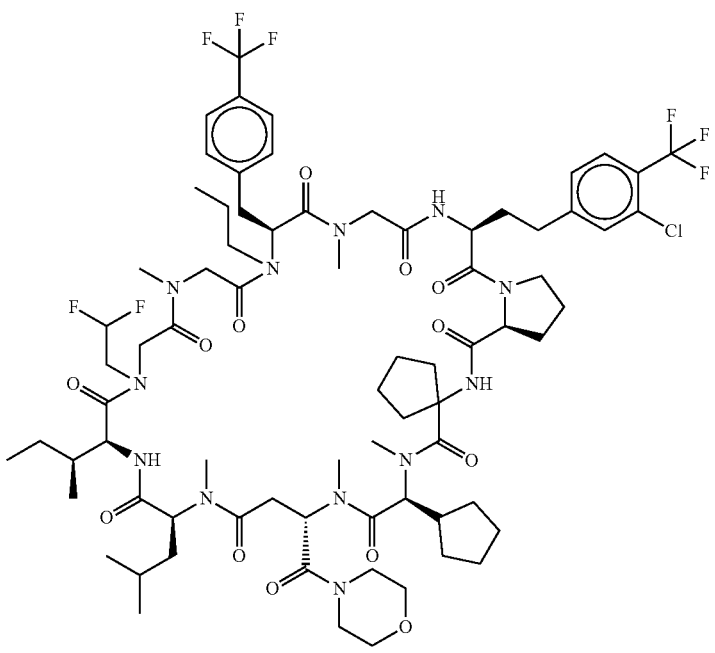 |

TABLE 38-continued

| Compound No. | Structural Formula |
|---|---|
| PP0753 | |
| PP0754 | |

TABLE 38-continued
| Compound No. | Structural Formula |
|---|---|
| PP0755 | 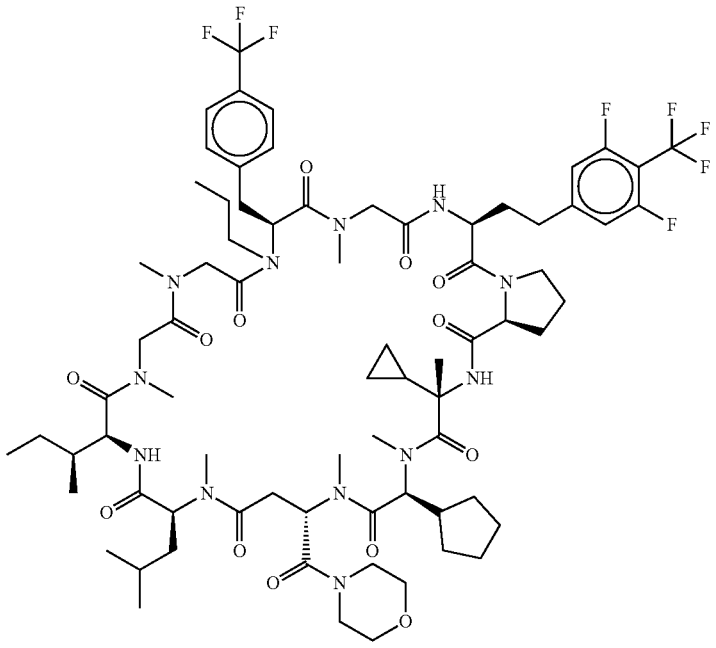 |
| PP0756 | 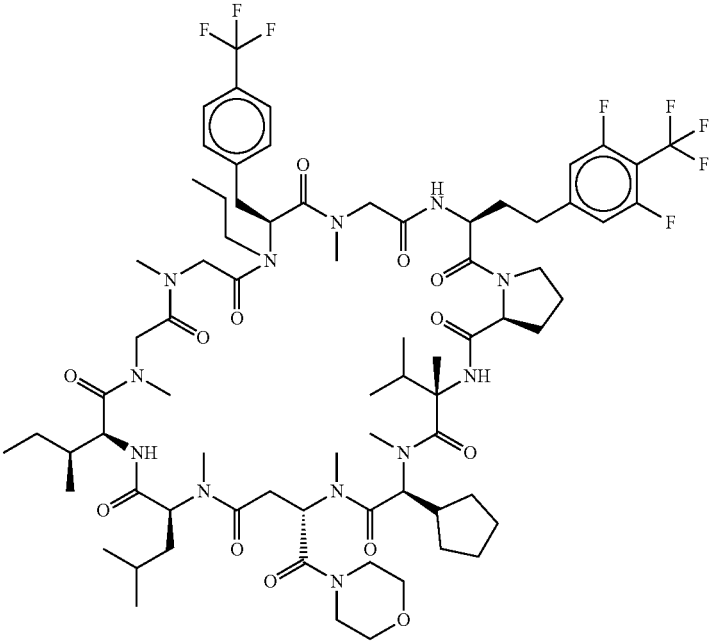 |

TABLE 38-continued
| Compound No. | Structural Formula |
|---|---|
| PP0757 | 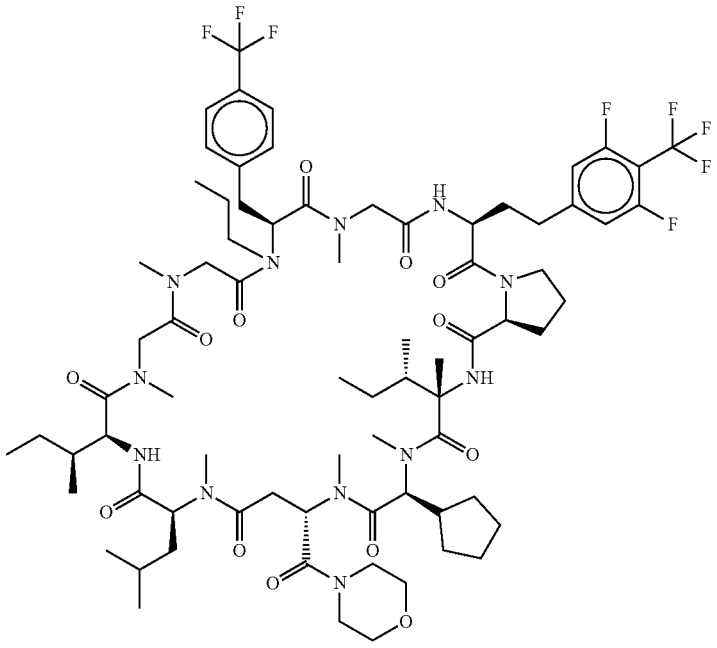 |
| PP0758 | 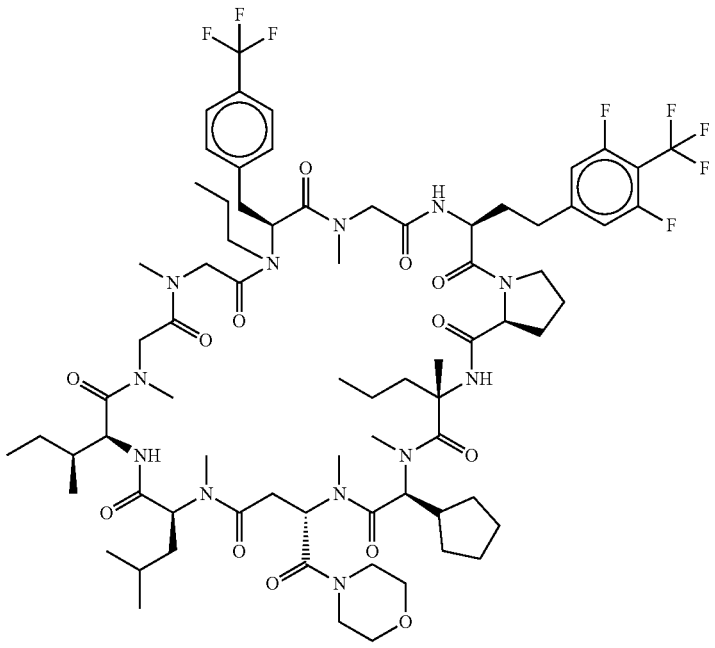 |

TABLE 38-continued
| Compound No. | Structural Formula |
|---|---|
| PP0759 | 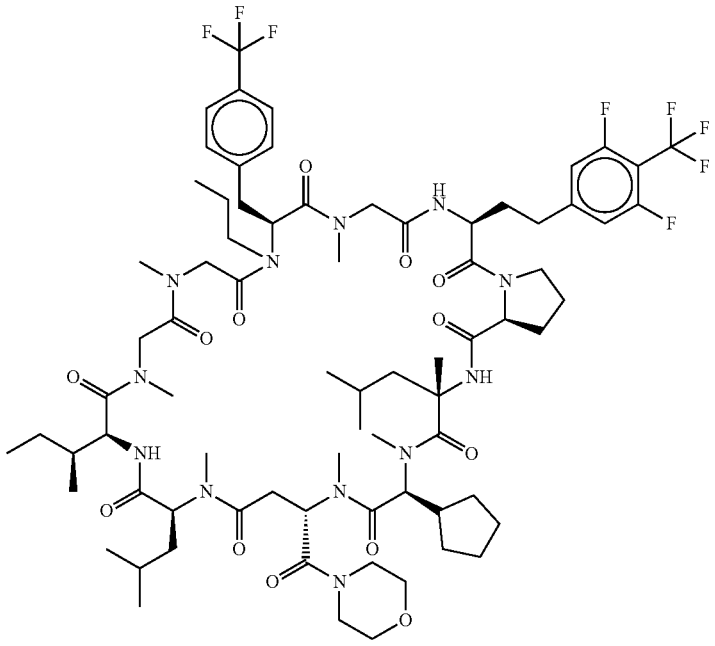 |
| PP0760 | 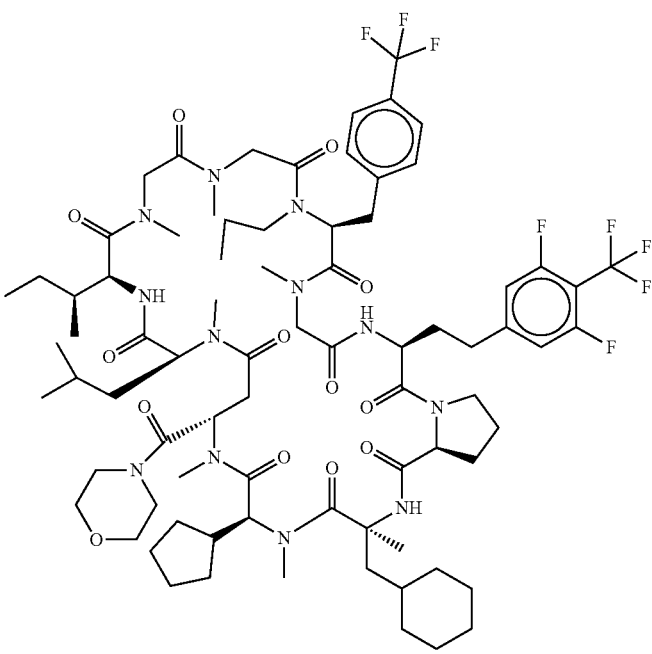 |

TABLE 38-continued
| Compound No. | Structural Formula |
|---|---|
| PP0761 | 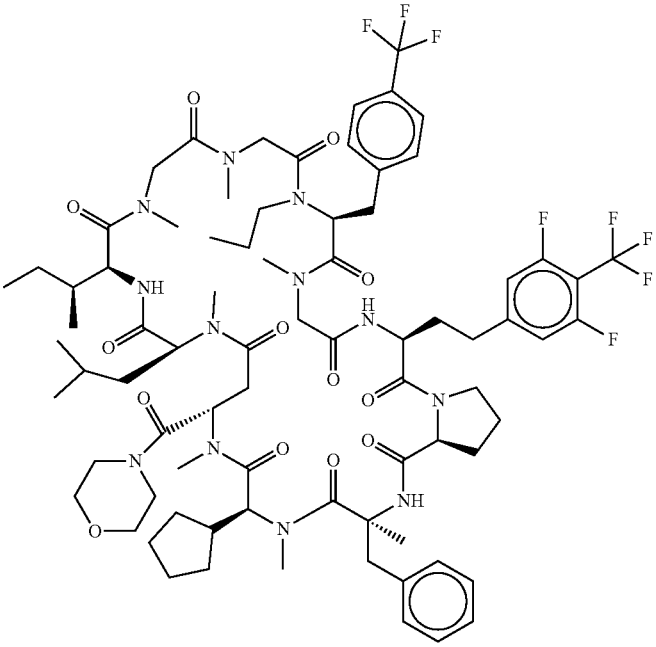 |
| PP0762 | 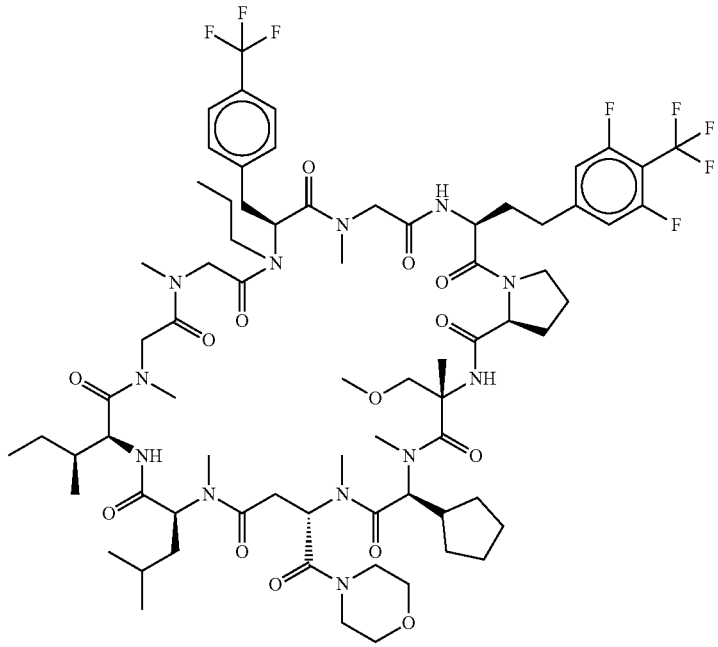 |

TABLE 38-continued
| Compound No. | Structural Formula |
|---|---|
| PP0763 | 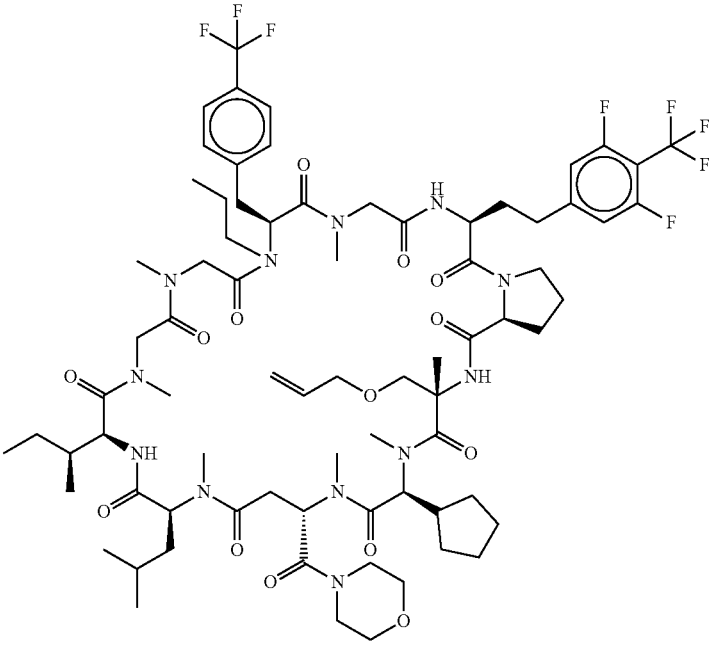 |
| PP0764 | 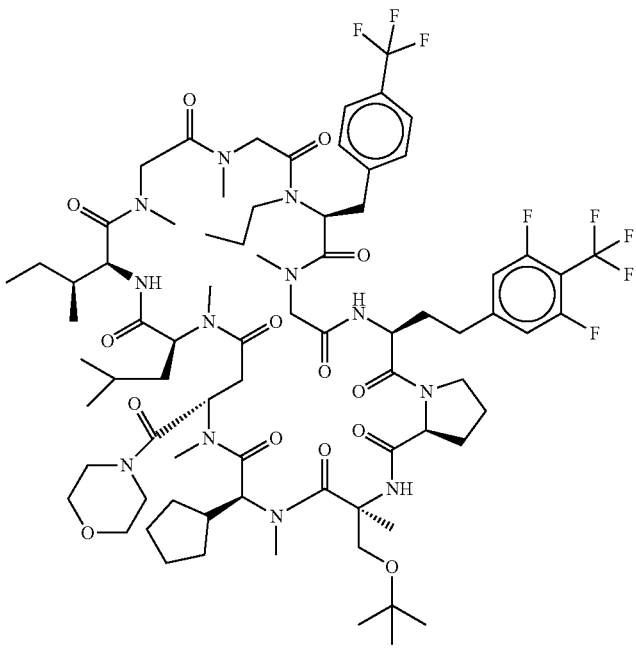 |

TABLE 38-continued

| Compound No. | Structural Formula |
|---|---|
| PP0765 | |
| PP0766 | |

TABLE 38-continued

| Compound No. | Structural Formula |
| --- | --- |
| PP0767 | |
| PP0768 | |

TABLE 38-continued
| Compound No. | Structural Formula |
|---|---|
| PP0769 | 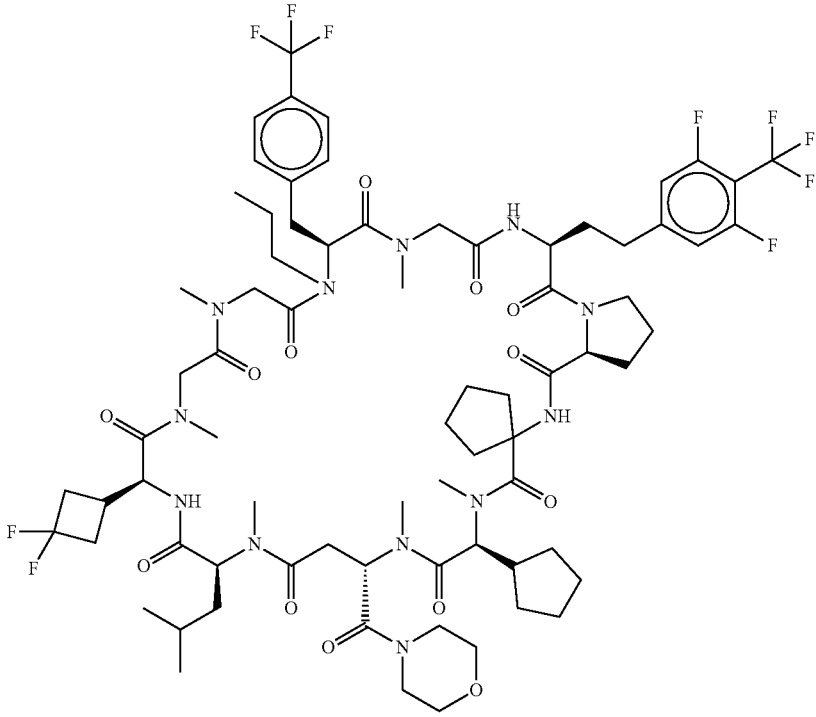 |
| PP0770 | 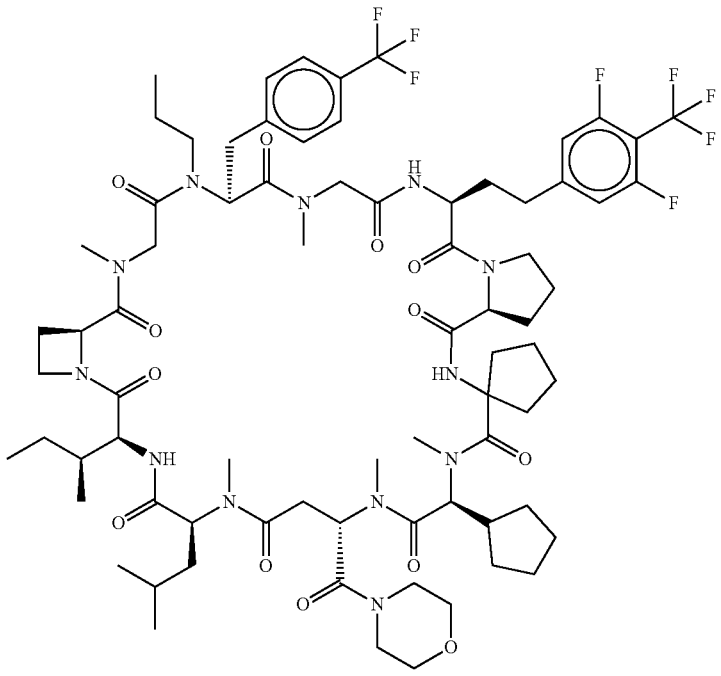 |

TABLE 38-continued
| Compound No. | Structural Formula |
| --- | --- |
| PP0771 | 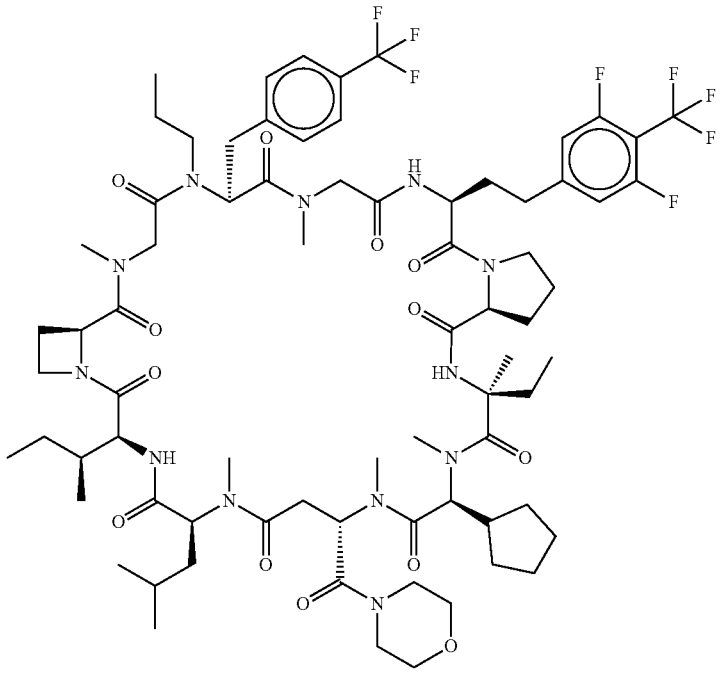 |
| PP0772 | 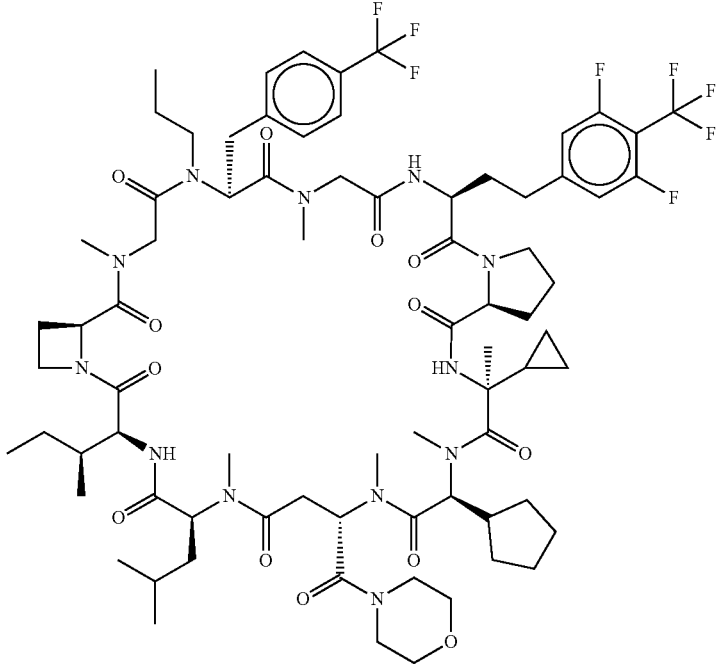 |

TABLE 38-continued
| Compound No. | Structural Formula |
|---|---|
| PP0773 | 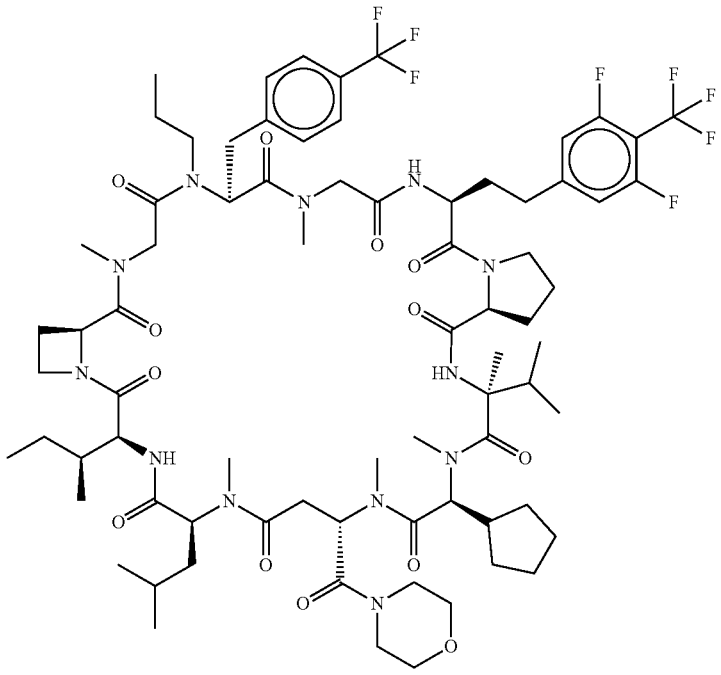 |
| PP0774 | 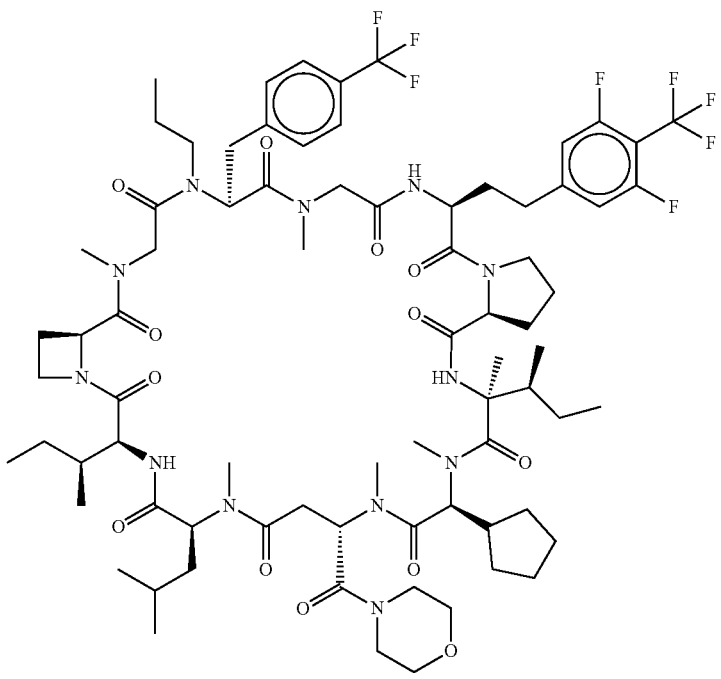 |

TABLE 38-continued

| Compound No. | Structural Formula |
|---|---|
| PP0775 | |
| PP0776 | |

| Compound No. | Structural Formula |
|---|---|
| PP0778 | 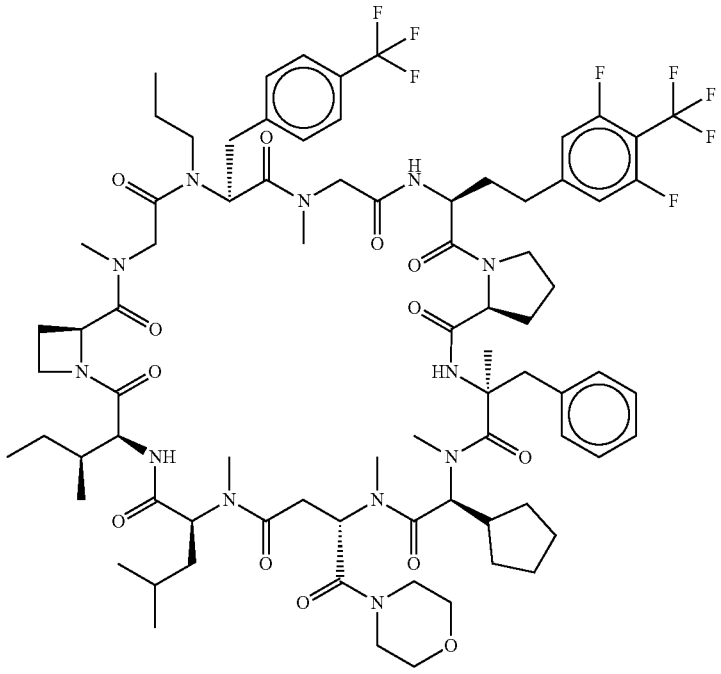 |
| PP0779 | 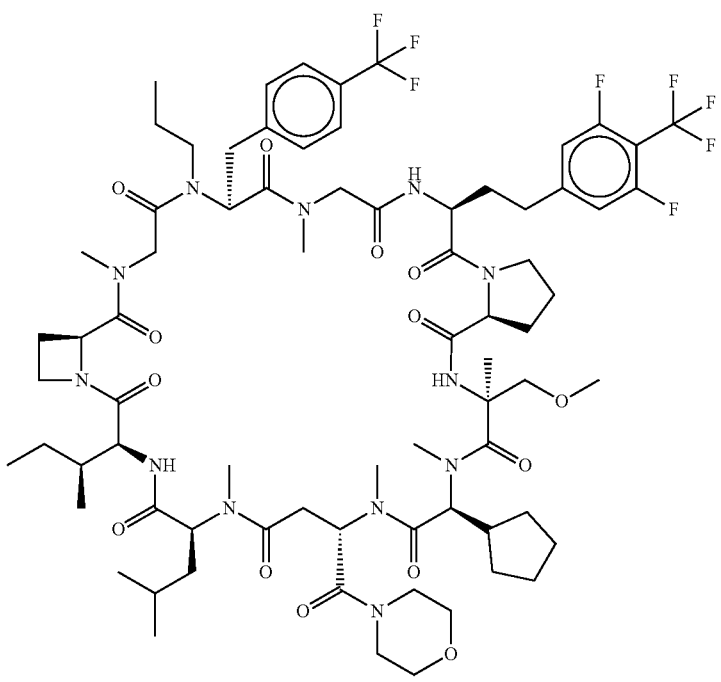 |

| Compound No. | Structural Formula |
|---|---|
| PP0780 | 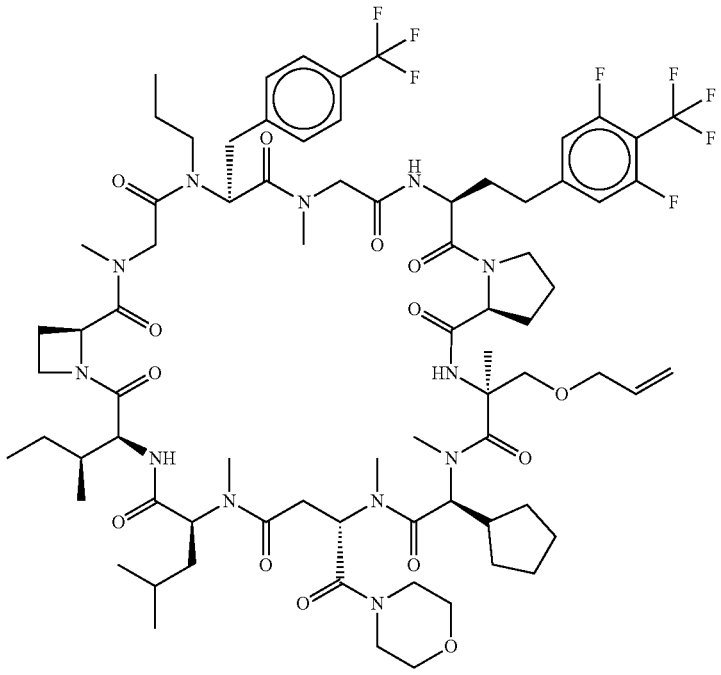 |
| PP0781 | 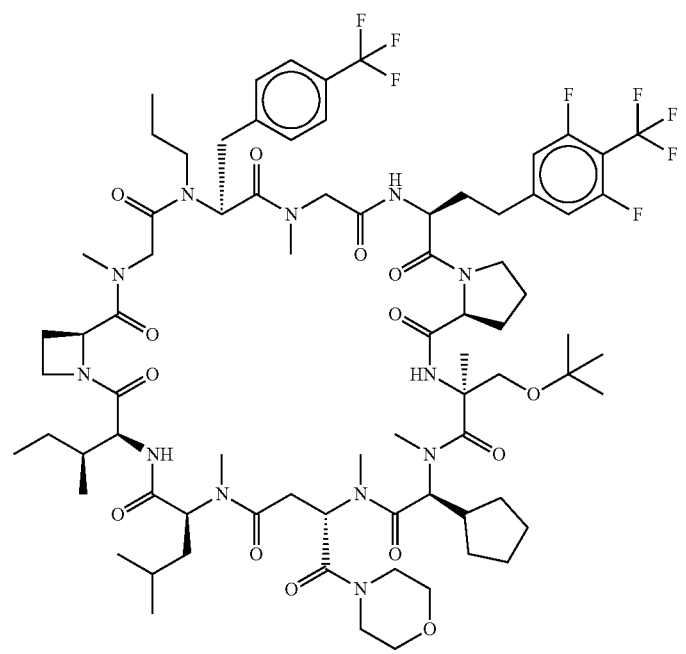 |

TABLE 38-continued
| Compound No. | Structural Formula |
| --- | --- |
| PP0782 | 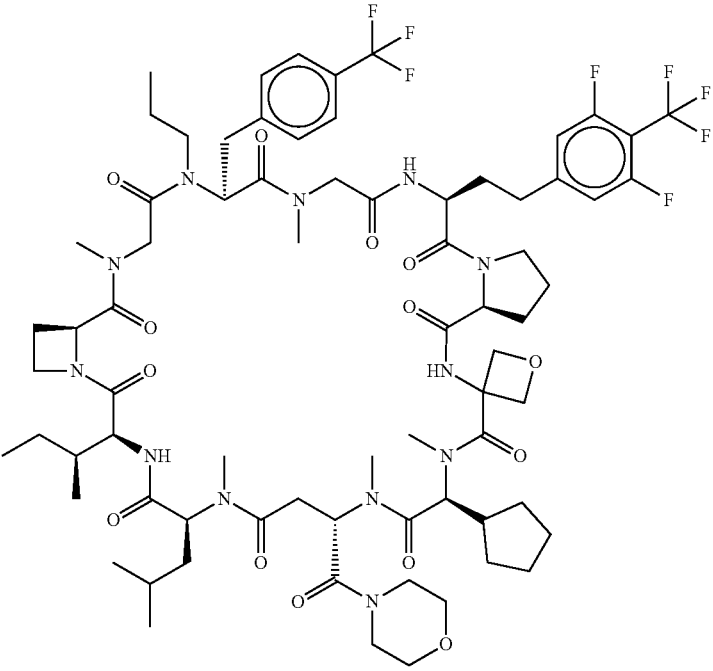 |
| PP0783 | 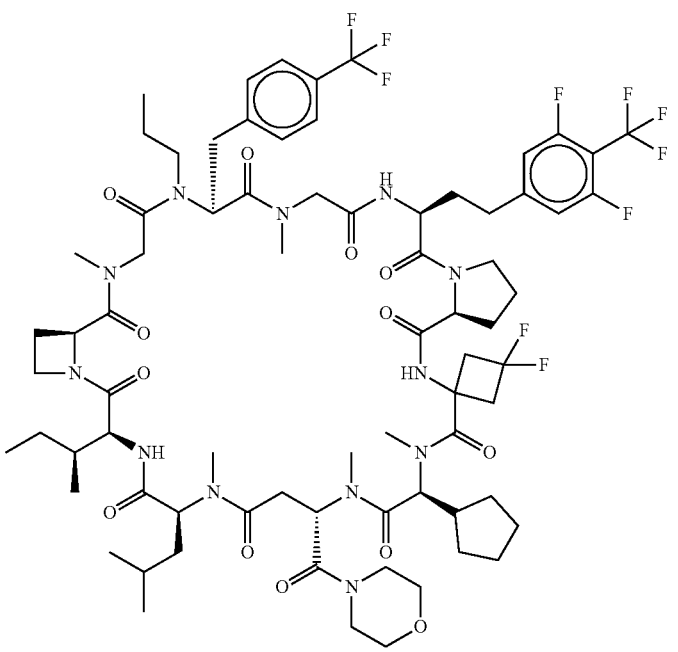 |

TABLE 38-continued

| Compound No. | Structural Formula |
|---|---|
| PP0784 | |
| PP0785 | |

TABLE 38-continued
| Compound No. | Structural Formula |
|---|---|
| PP0786 | 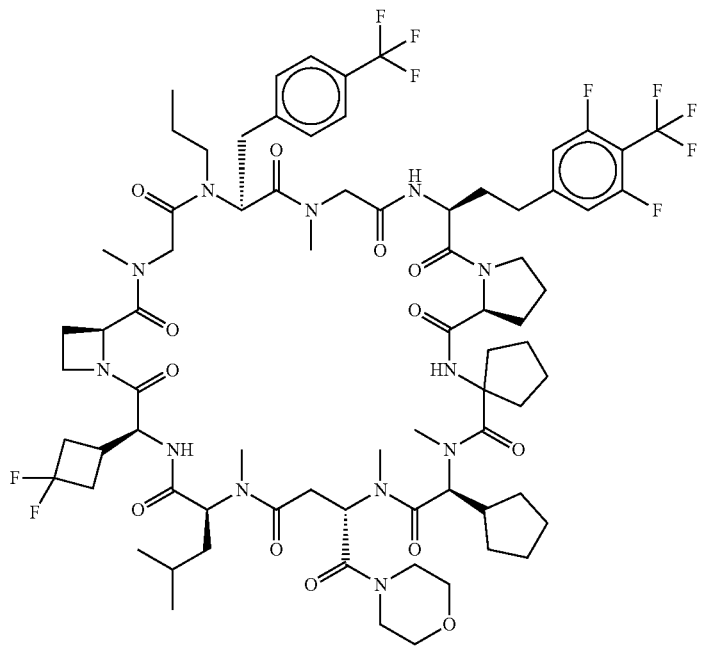 |
| PP0787 | 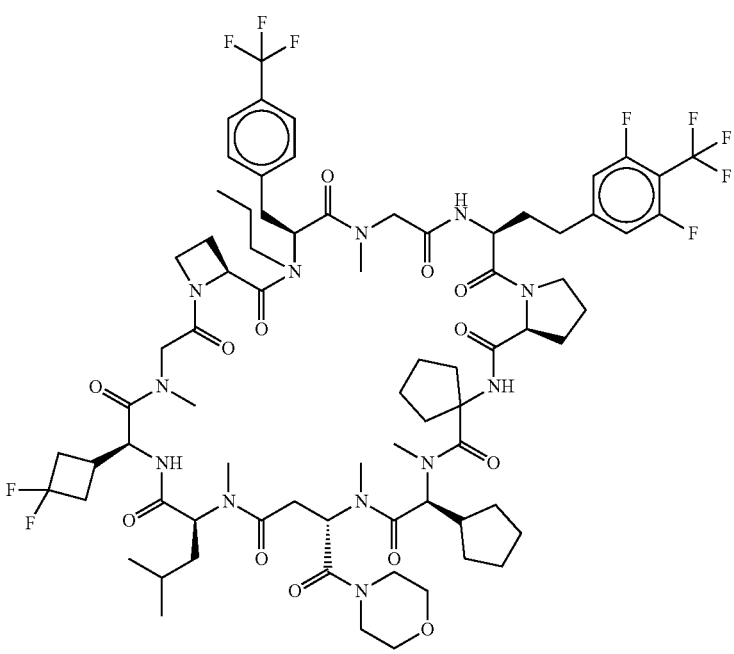 |

TABLE 38-continued
| Compound No. | Structural Formula |
|---|---|
| PP0788 | 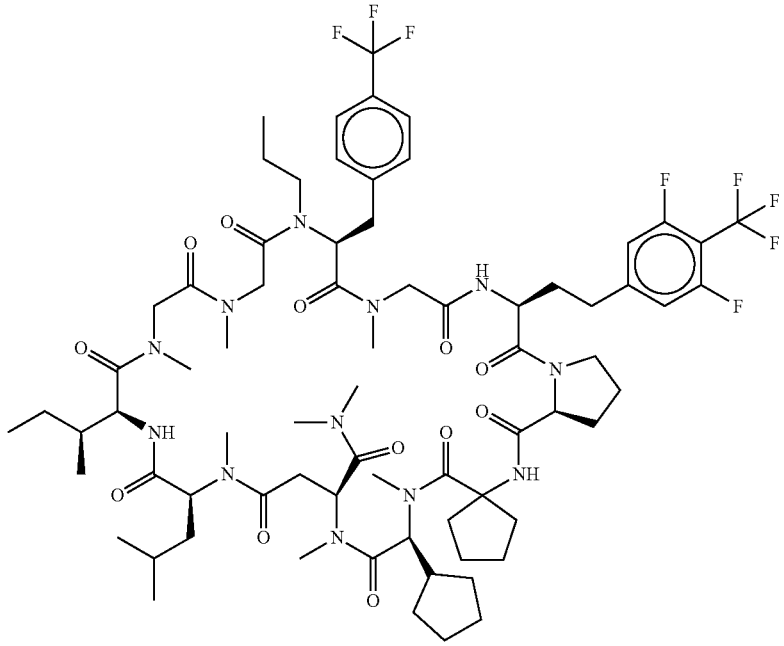 |
| PP0789 | 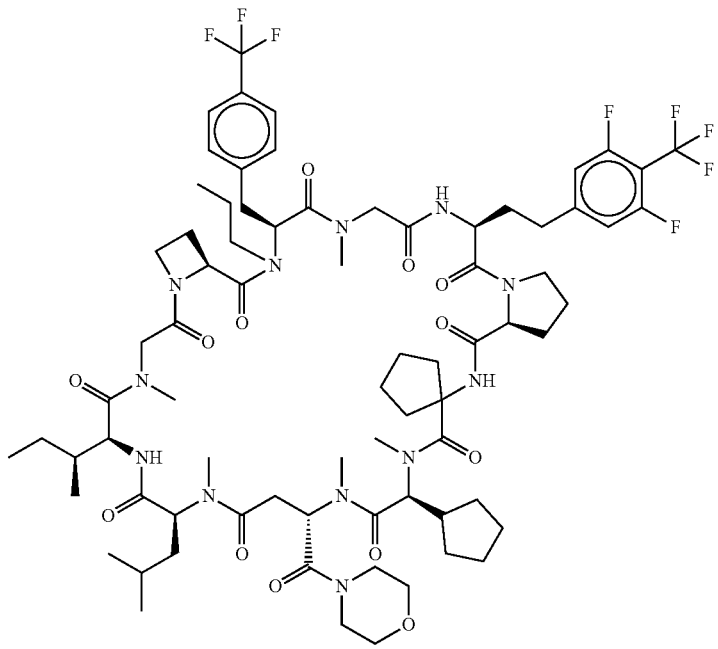 |

TABLE 38-continued

| Compound No. | Structural Formula |
|---|---|
| PP0790 | |
| PP0791 | |

TABLE 38-continued

| Compound No. | Structural Formula |
|---|---|
| PP0792 | |
| PP0793 | |

TABLE 38-continued

| Compound No. | Structural Formula |
| --- | --- |
| PP0794 | |
| PP0795 | |

TABLE 38-continued

| Compound No. | Structural Formula |
|---|---|
| PP0796 | |
| PP0797 | |

TABLE 38-continued

| Compound No. | Structural Formula |
| --- | --- |
| PP0798 | |
| PP0799 | |

TABLE 38-continued
| Compound No. | Structural Formula |
|---|---|
| PP0800 | 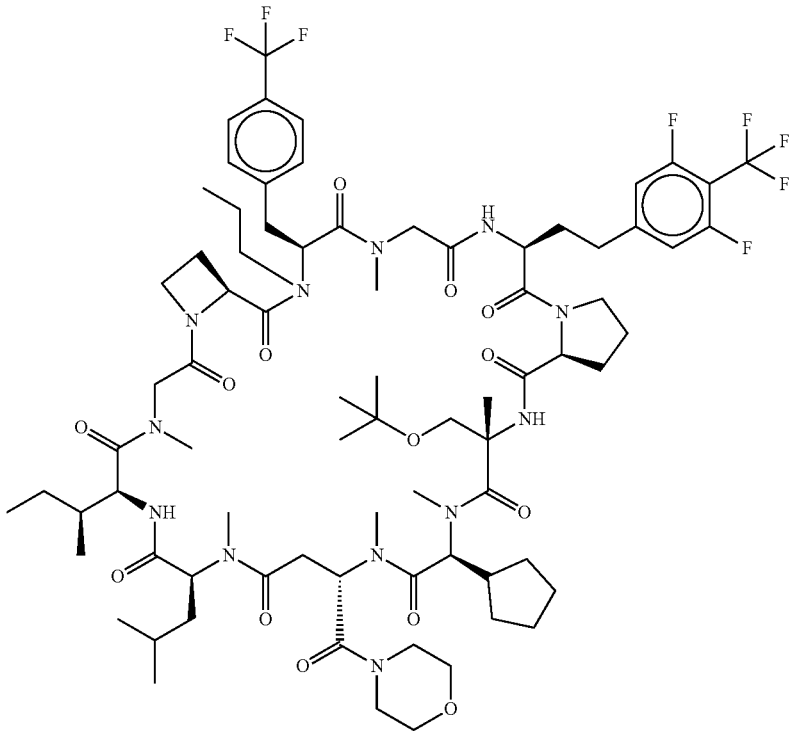 |
| PP0801 | 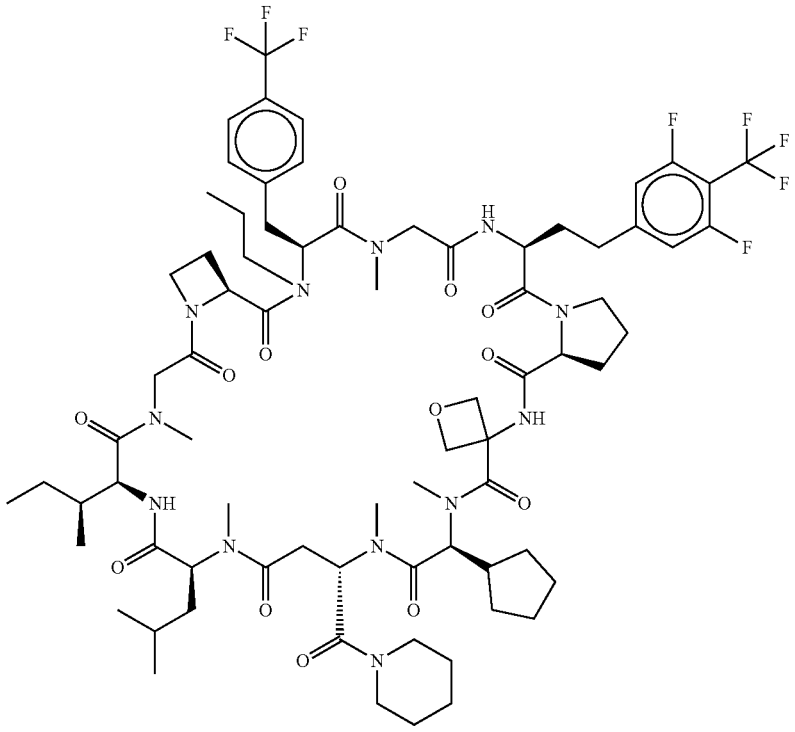 |

TABLE 38-continued

| Compound No. | Structural Formula |
|---|---|
| PP0802 | |
| PP0803 | |

TABLE 38-continued
| Compound No. | Structural Formula |
|---|---|
| PP0804 | 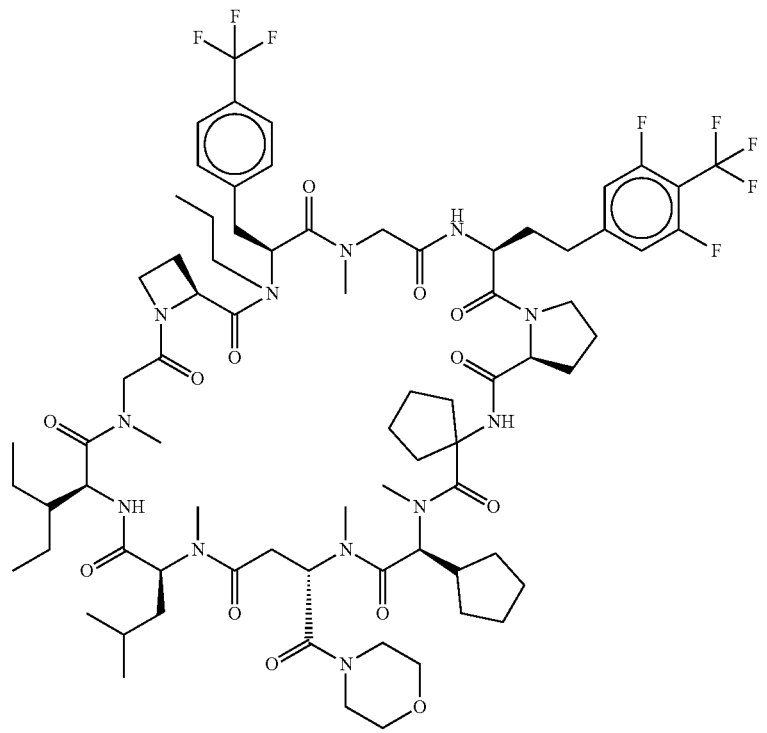 |
| PP0805 | 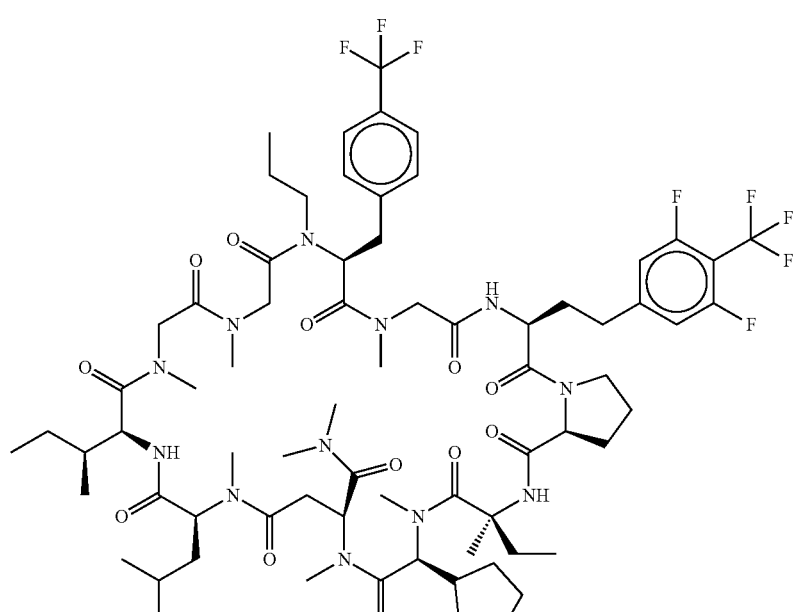 |

| Compound No. | Structural Formula |
|---|---|
| PP0806 | 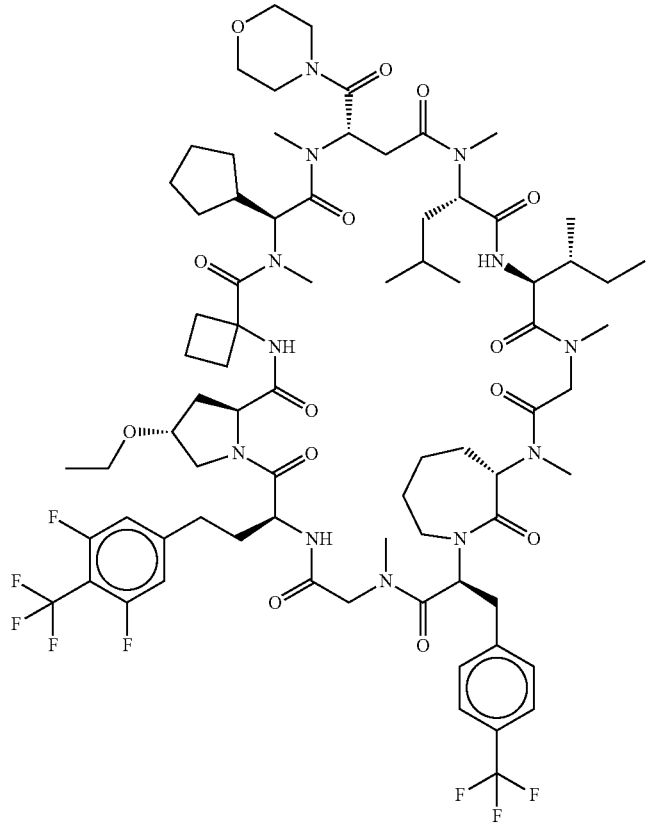 |
| PP0807 | 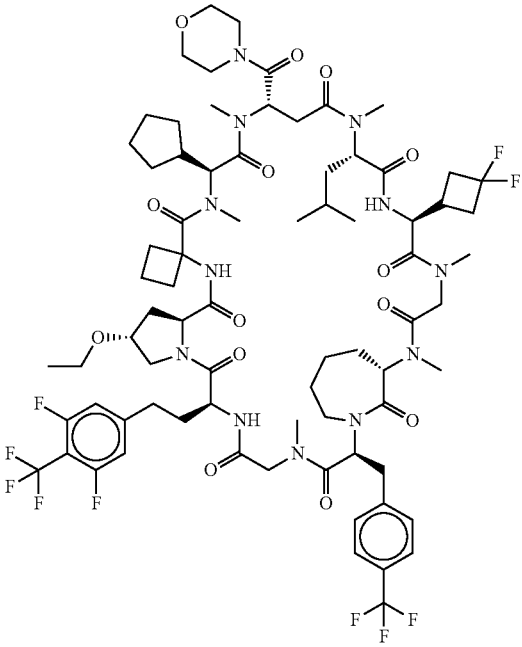 |

TABLE 38-continued

| Compound No. | Structural Formula |
|---|---|
| PP0808 | |
| PP0809 | |

TABLE 38-continued

| Compound No. | Structural Formula |
|---|---|
| PP0810 | |
| PP0811 | |

TABLE 38-continued
| Compound No. | Structural Formula |
|---|---|
| PP0812 | 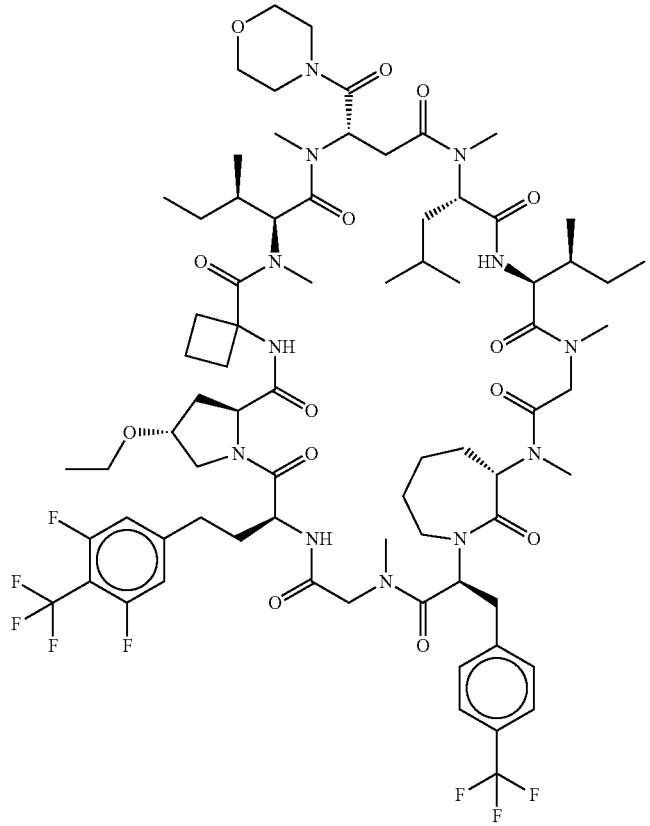 |
| PP0813 | 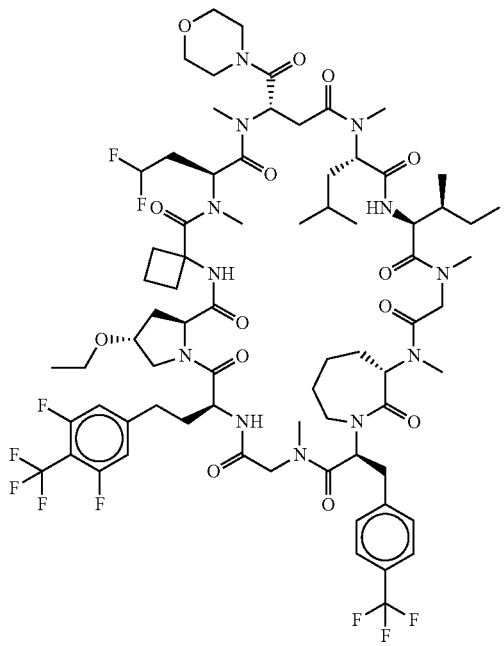 |

TABLE 38-continued
| Compound No. | Structural Formula |
|---|---|
| PP0814 | 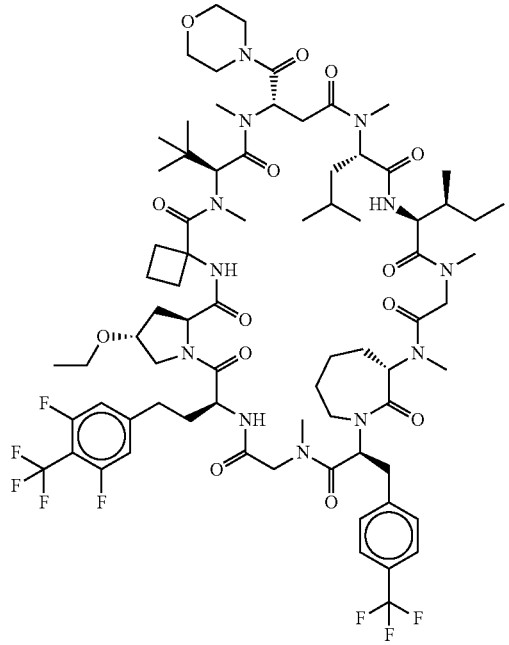 |
| PP0815 | 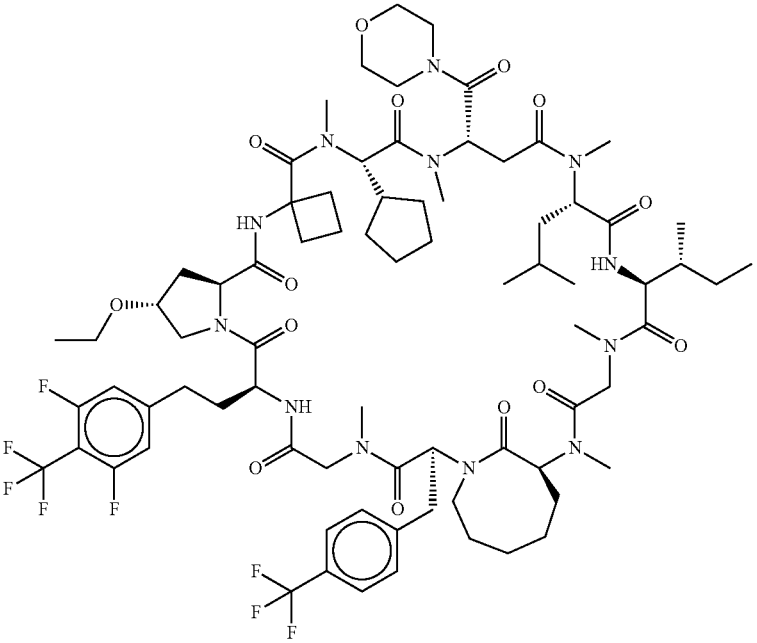 |

TABLE 38-continued
| Compound No. | Structural Formula |
|---|---|
| PP0816 | 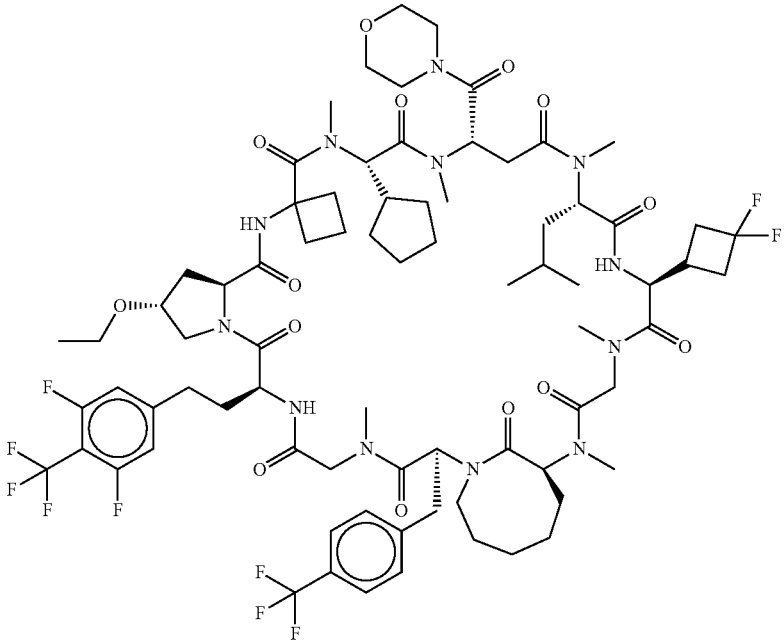 |
| PP0817 | 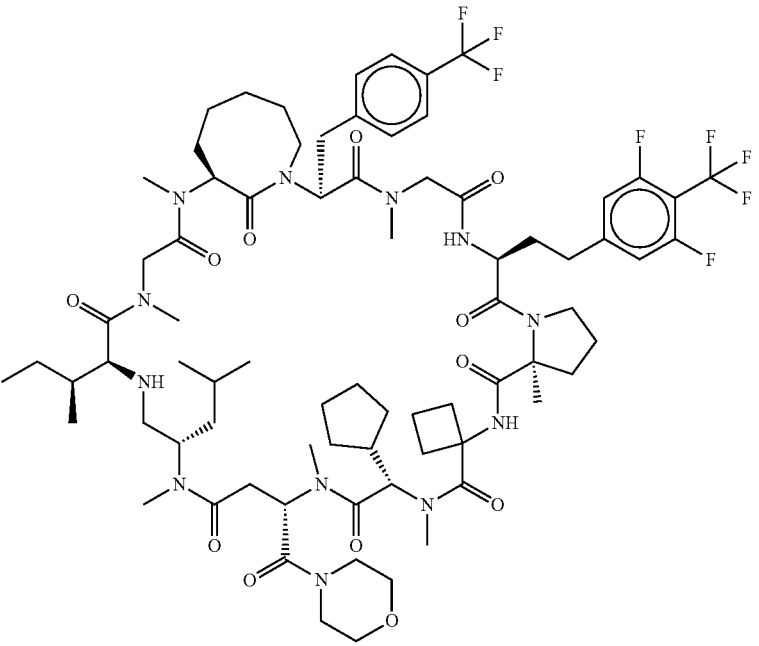 |

TABLE 38-continued
| Compound No. | Structural Formula |
|---|---|
| PP0818 | 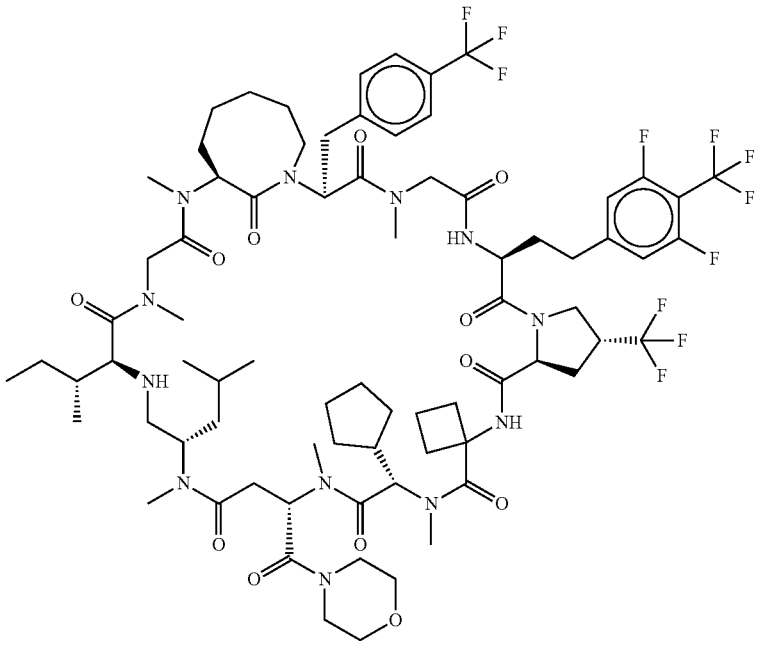 |
| PP0819 | 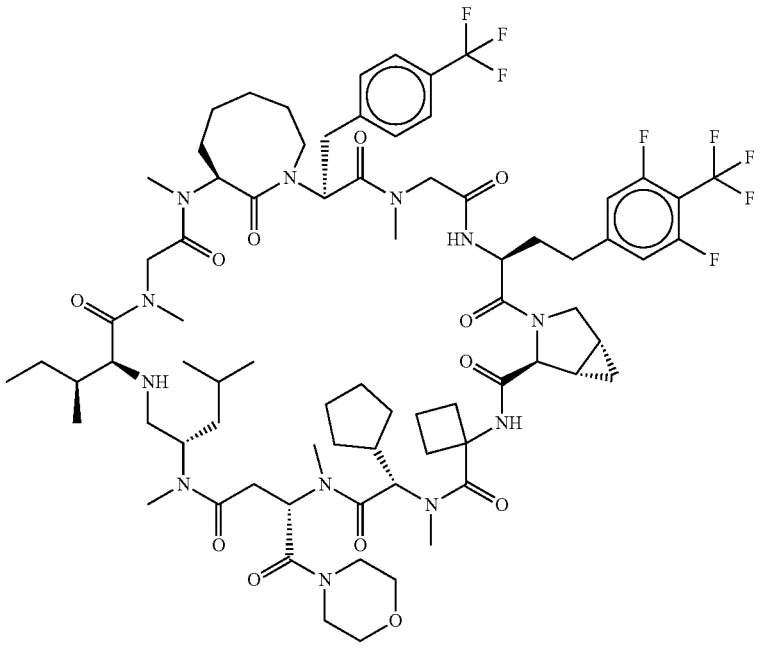 |

TABLE 38-continued
| Compound No. | Structural Formula |
|---|---|
| PP0820 | 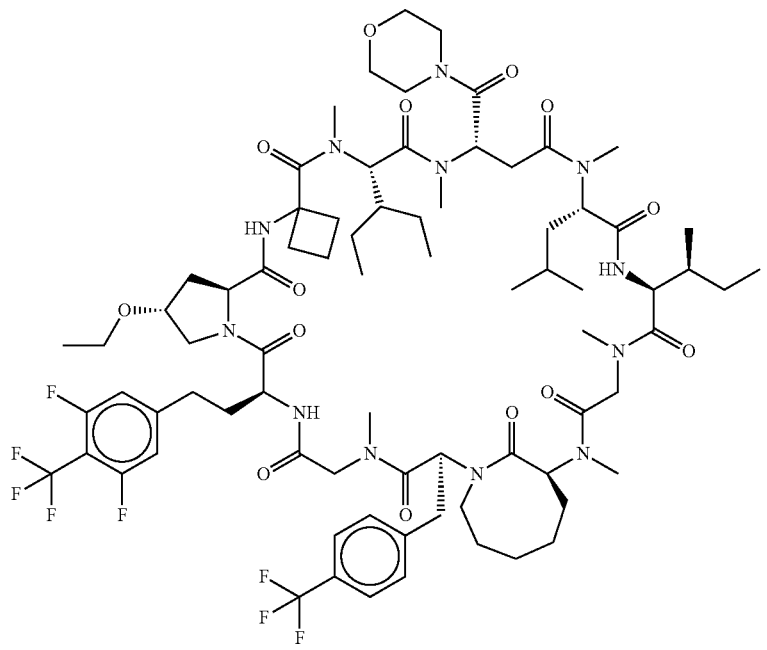 |
| PP0821 | 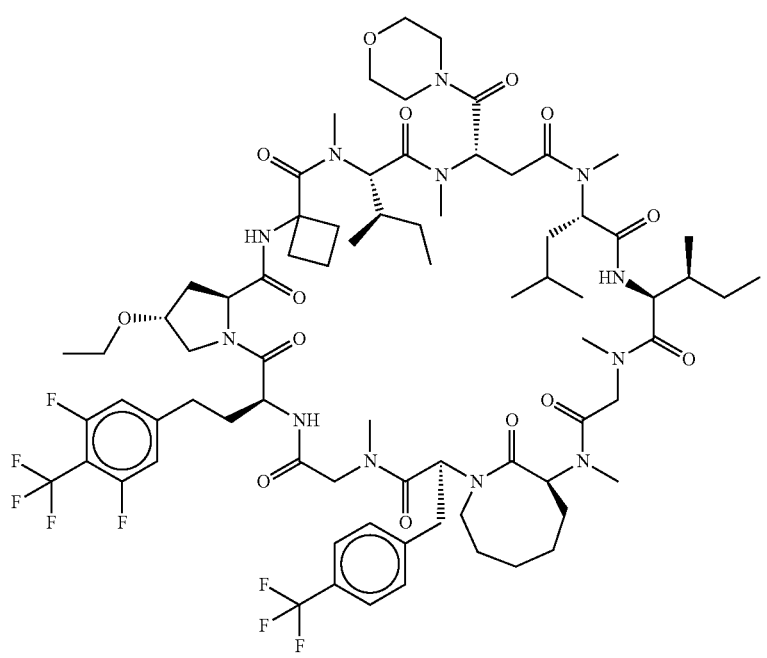 |

TABLE 38-continued
| Compound No. | Structural Formula |
| --- | --- |
| PP0822 | 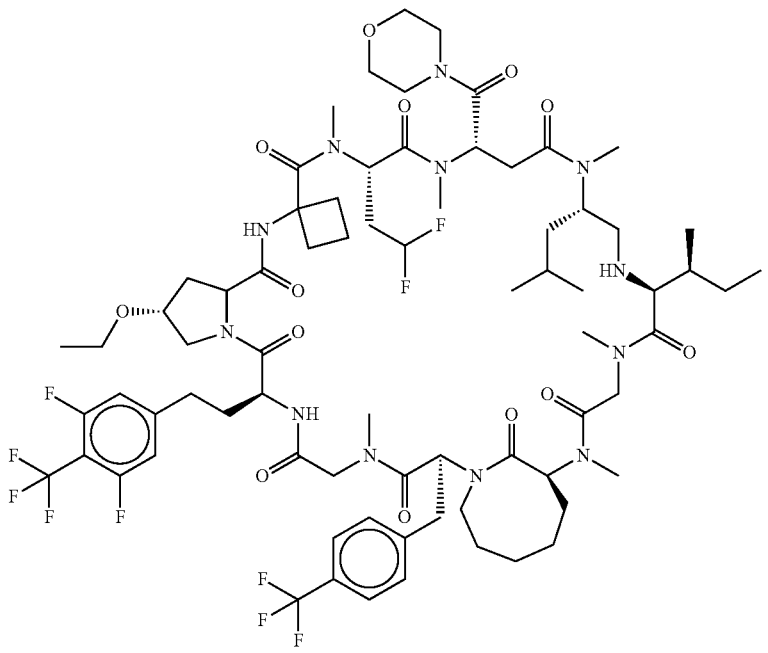 |
| PP0823 | 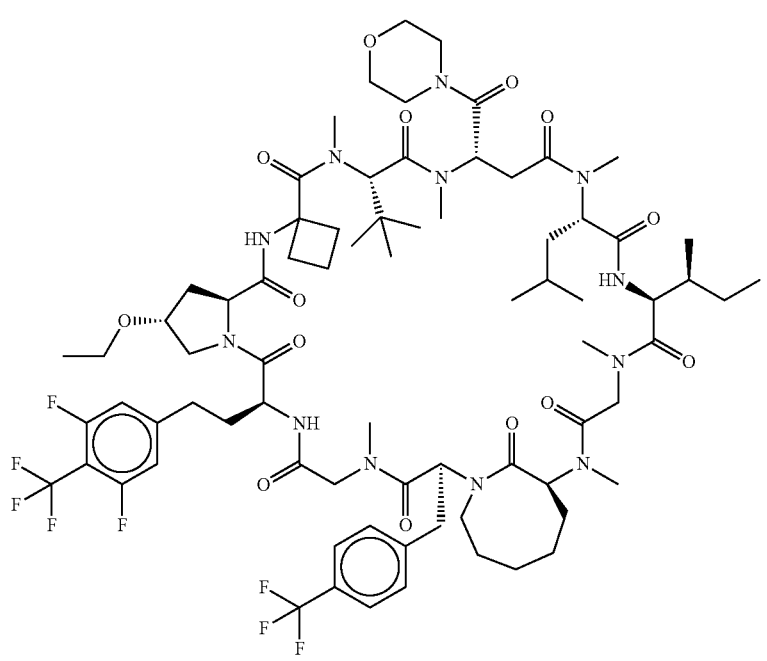 |

TABLE 38-continued
| Compound No. | Structural Formula |
|---|---|
| PP0824 | 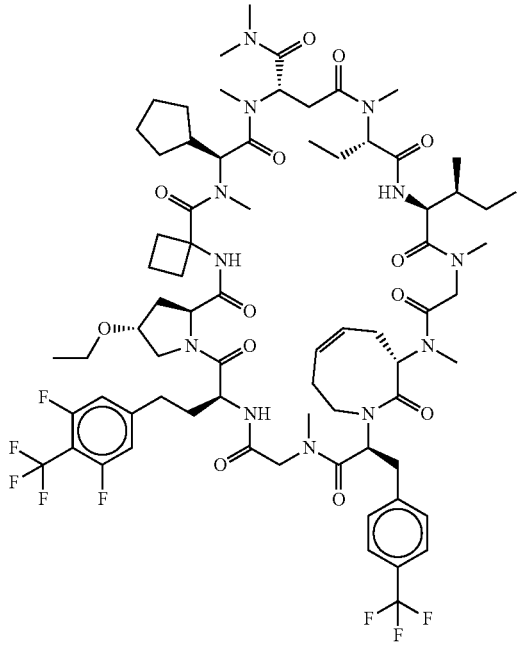 |
| PP0825 | 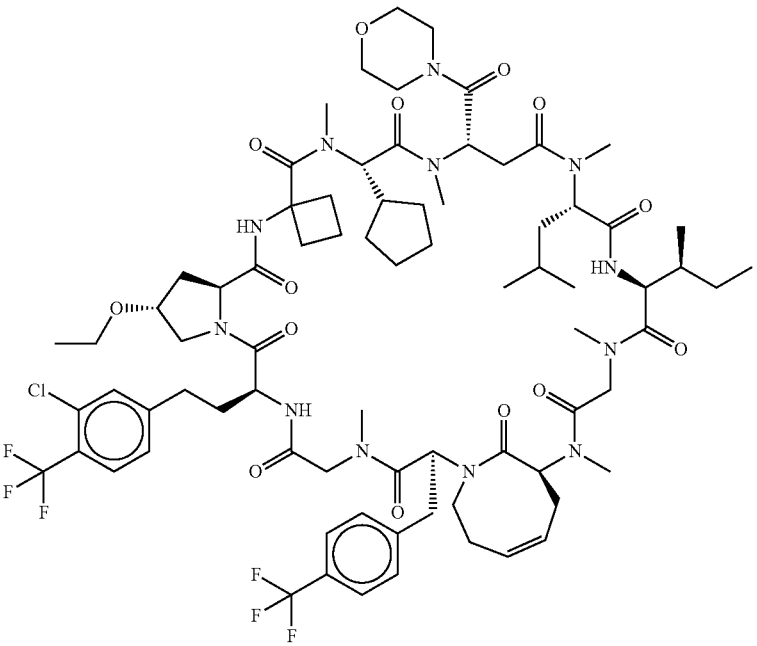 |

TABLE 38-continued
| Compound No. | Structural Formula |
|---|---|
| PP0826 | 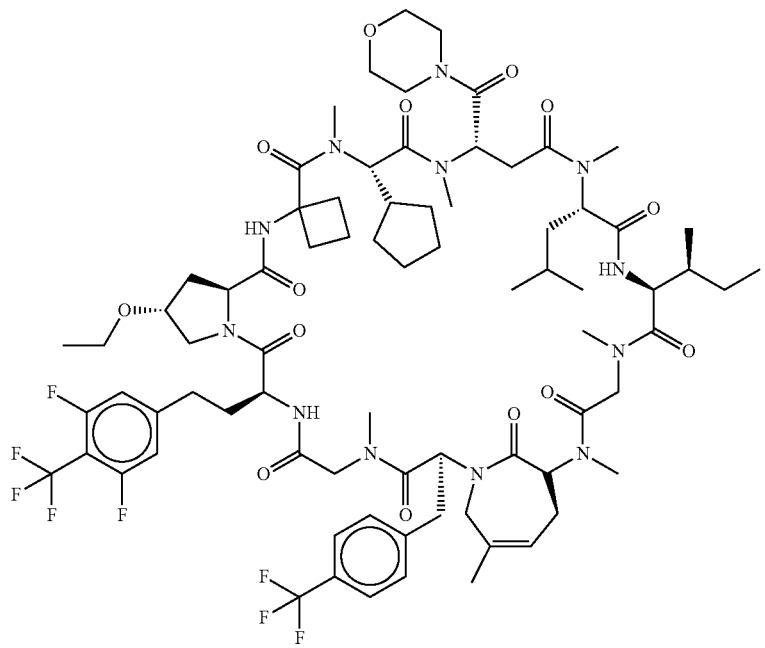 |
| PP0827 | 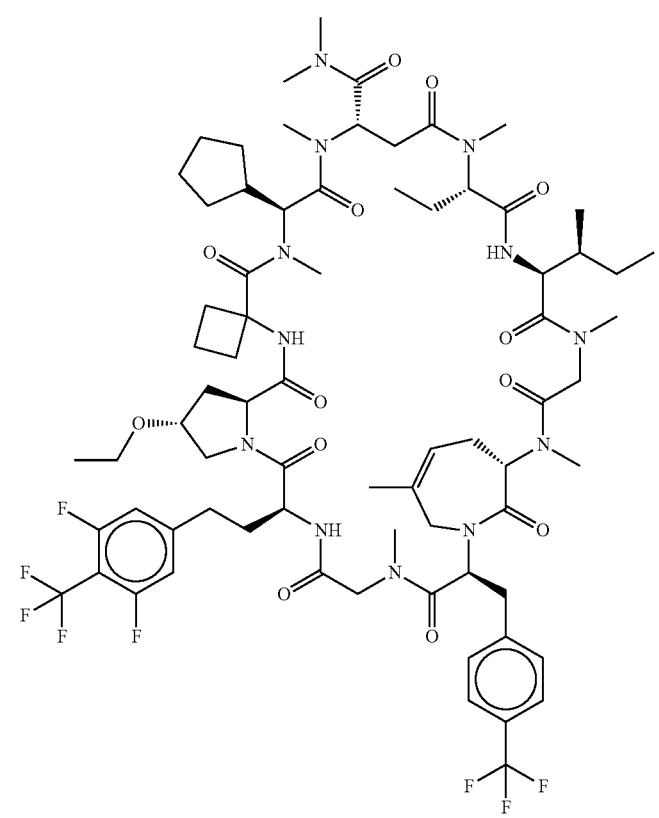 |

TABLE 38-continued
| Compound No. | Structural Formula |
|---|---|
| PP0828 | 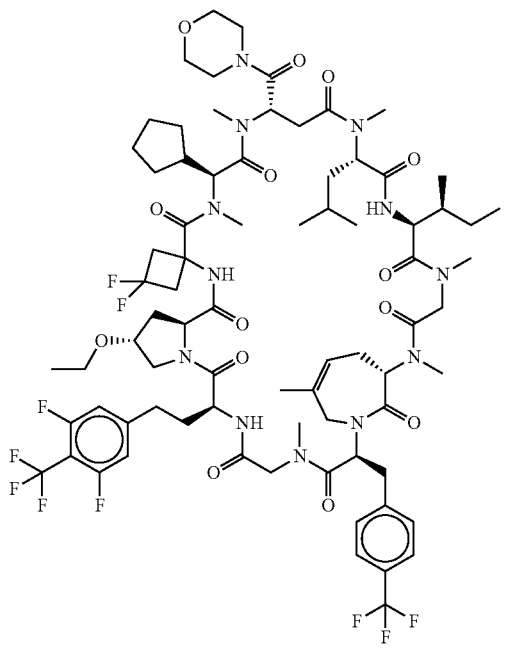 |
| PP0829 | 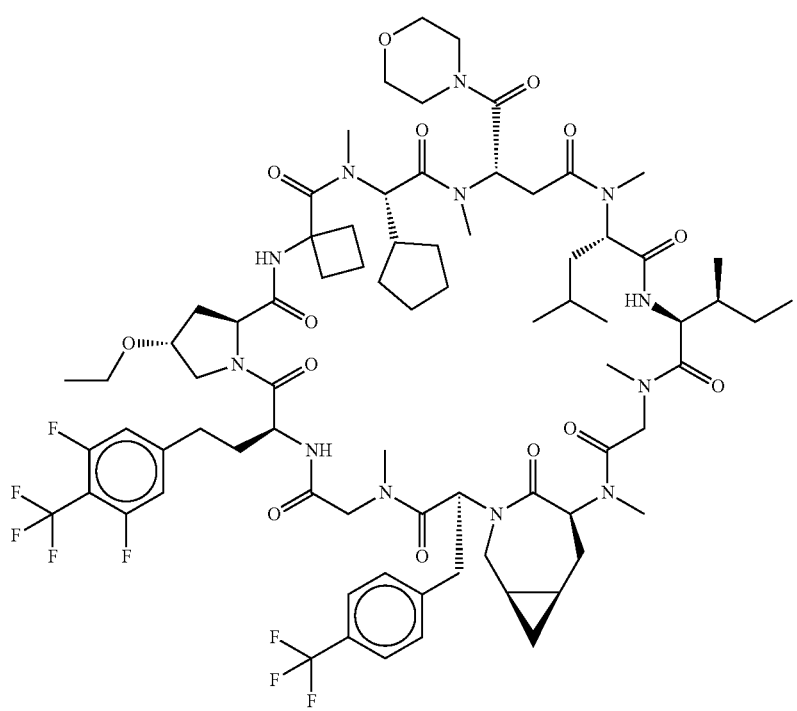 |

TABLE 38-continued
| Compound No. | Structural Formula |
|---|---|
| PP0830 | 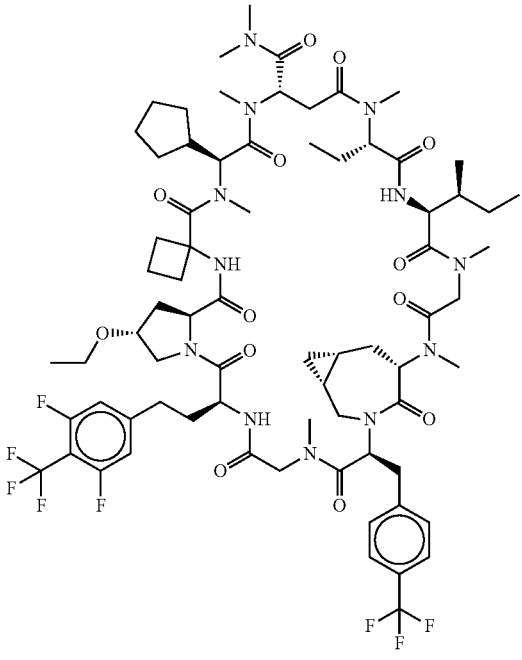 |
| PP0831 | 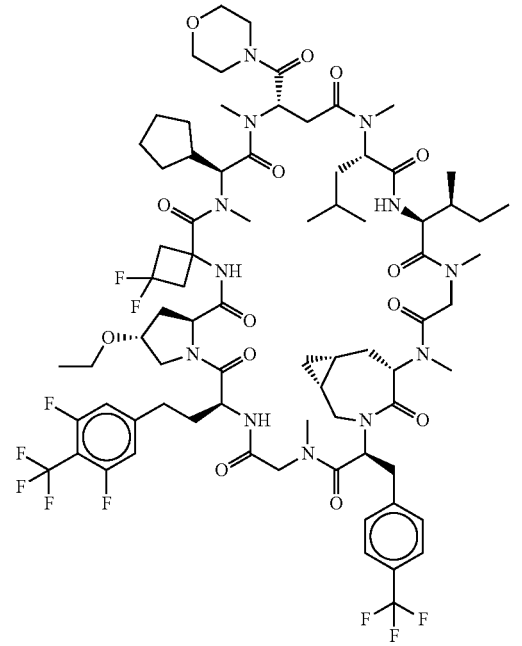 |

TABLE 38-continued
| Compound No. | Structural Formula |
|---|---|
| PP0832 | 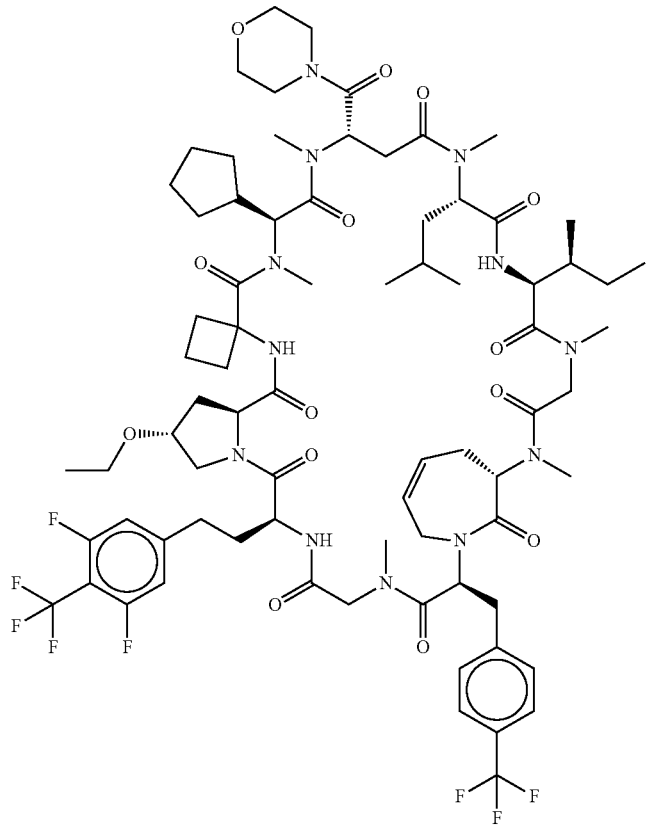 |
| PP0833 | 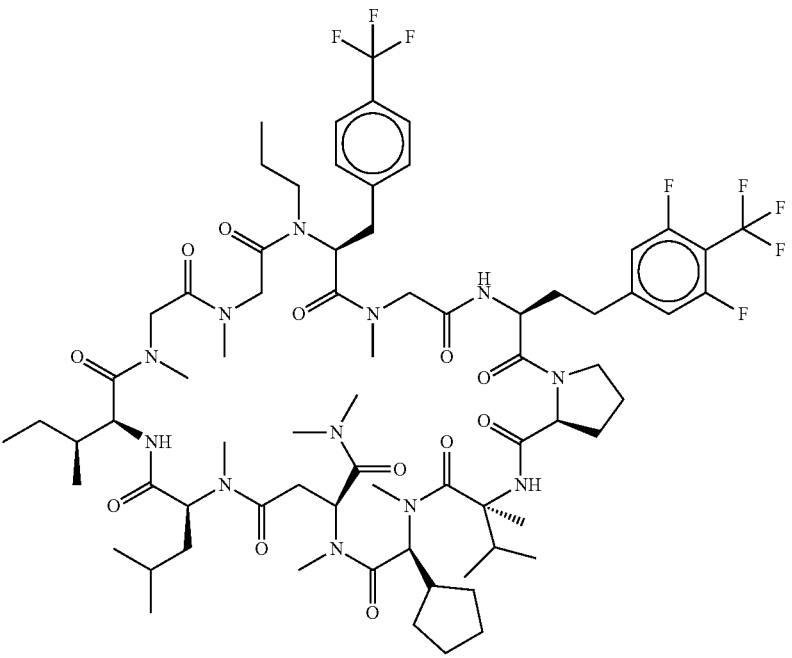 |

TABLE 38-continued
| Compound No. | Structural Formula |
|---|---|
| PP0834 | 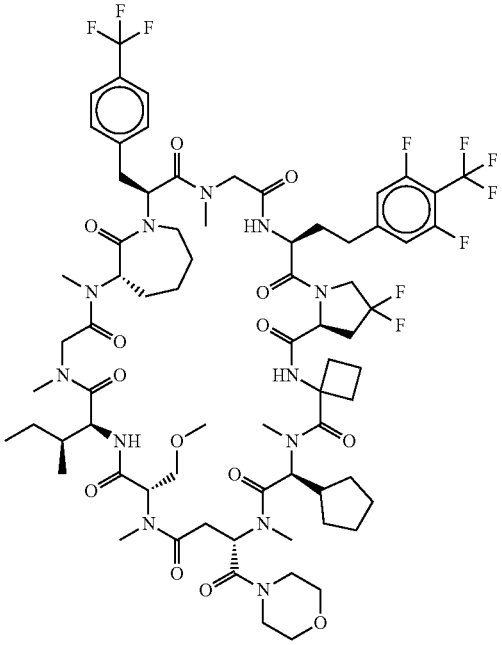 |
| PP0835 | 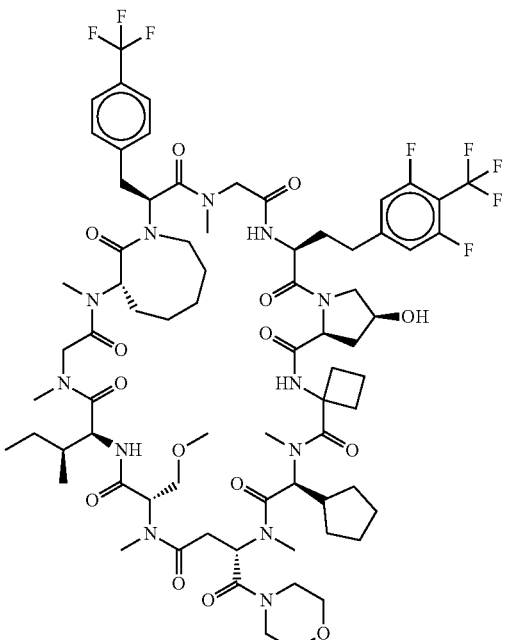 |

TABLE 38-continued

| Compound No. | Structural Formula |
|---|---|
| PP0836 | |
| PP0837 | |

TABLE 38-continued
| Compound No. | Structural Formula |
|---|---|
| PP0838 | 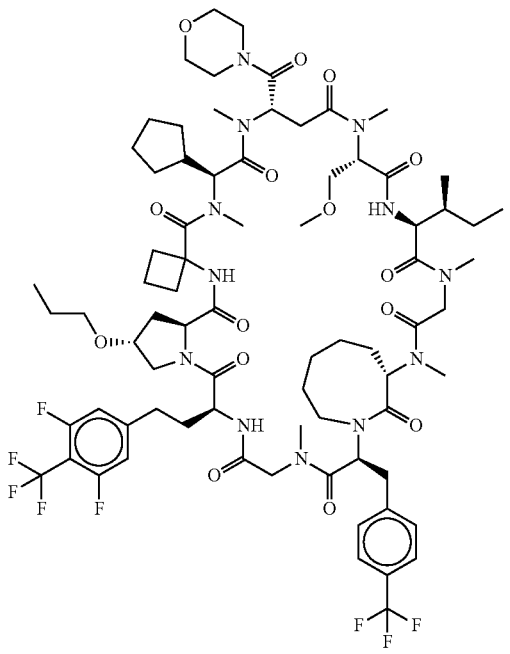 |
| PP0839 | 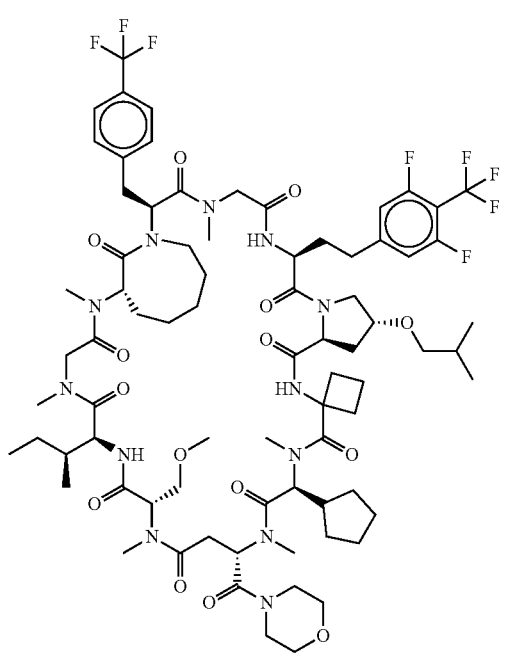 |

TABLE 38-continued

| Compound No. | Structural Formula |
|---|---|
| PP0840 | |
| PP0841 | |

TABLE 38-continued
| Compound No. | Structural Formula |
|---|---|
| PP0842 | 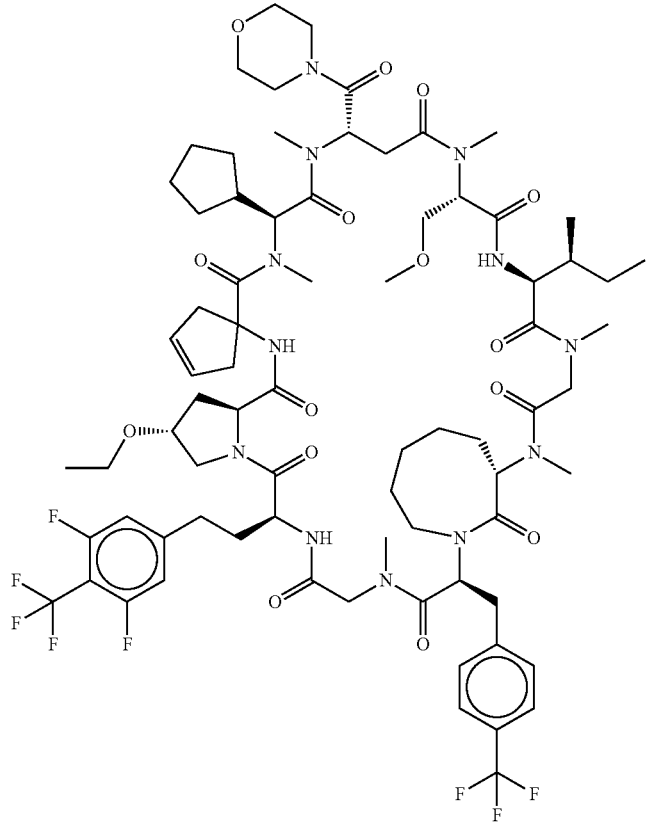 |
| PP0843 | 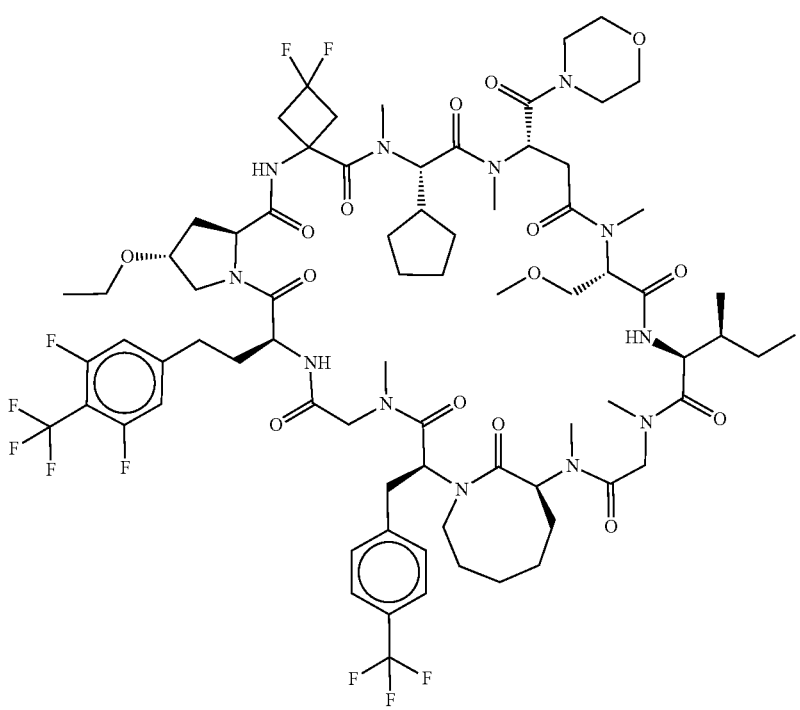 |

TABLE 38-continued
| Compound No. | Structural Formula |
|---|---|
| PP0844 | 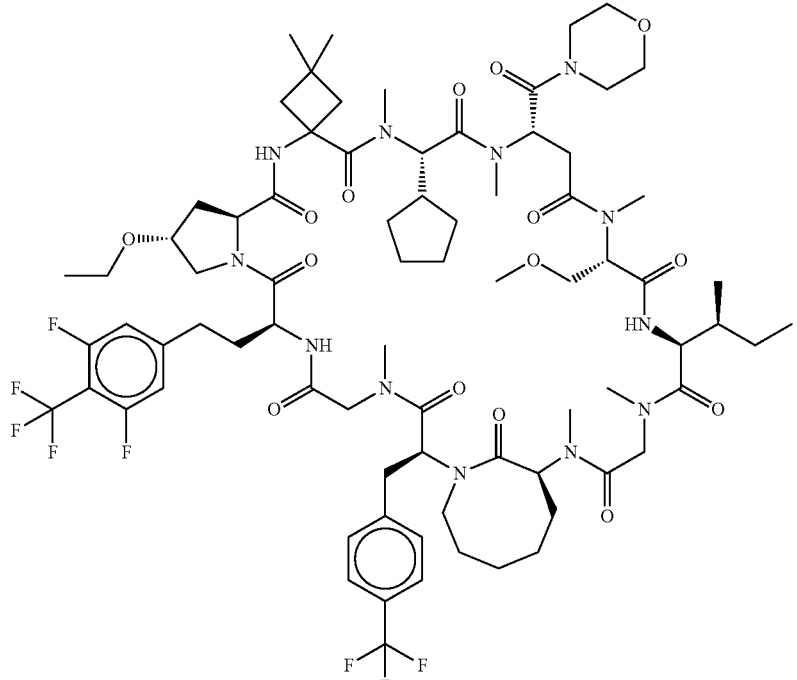 |
| PP0845 | 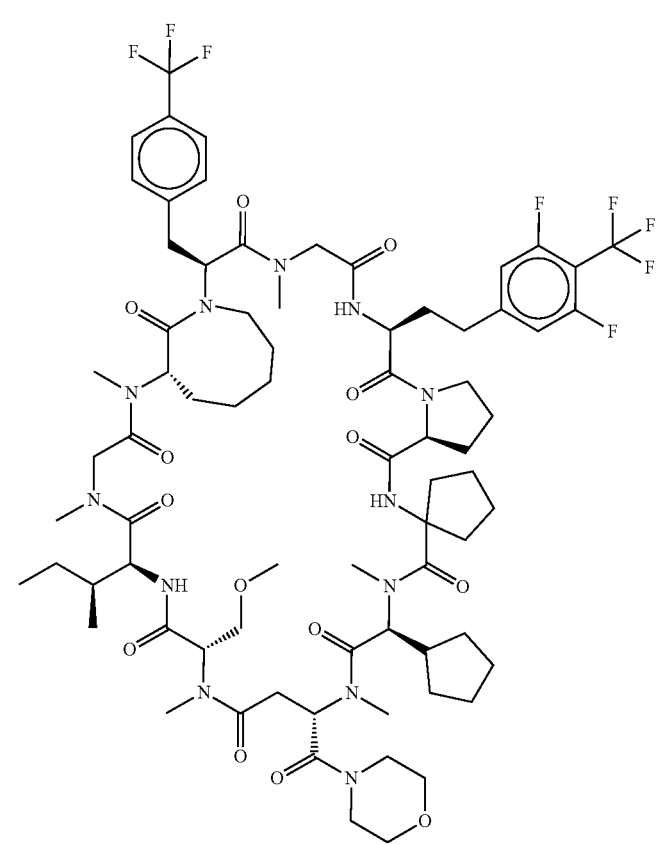 |

TABLE 38-continued

| Compound No. | Structural Formula |
|---|---|
| PP0846 | |
| PP0847 | |

TABLE 38-continued
| Compound No. | Structural Formula |
|---|---|
| PP0848 | 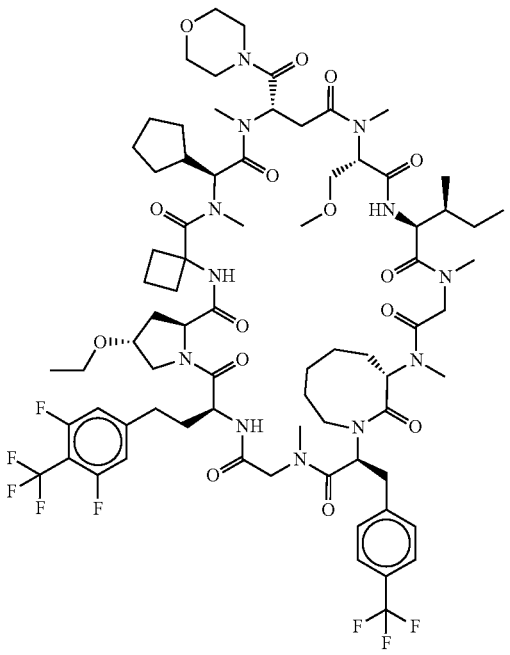 |
| PP0849 | 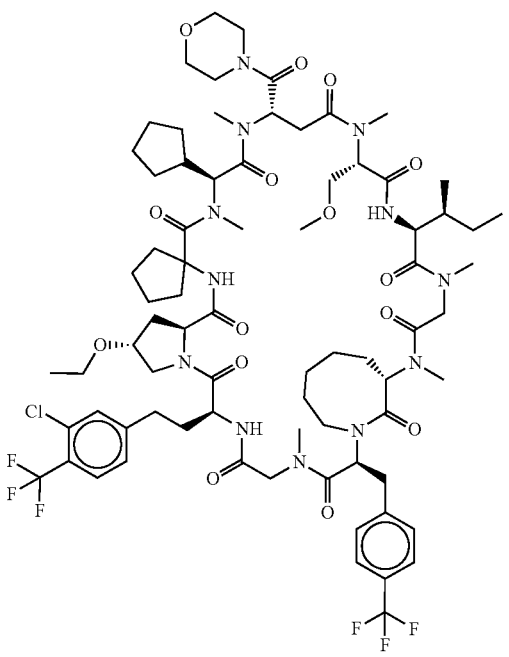 |

TABLE 38-continued
| Compound No. | Structural Formula |
| --- | --- |
| PP0850 | 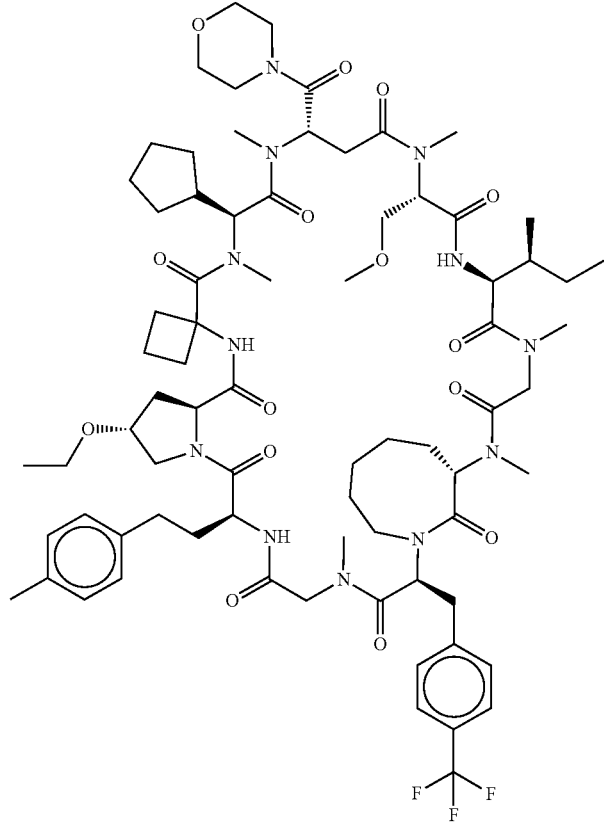 |
| PP0851 | 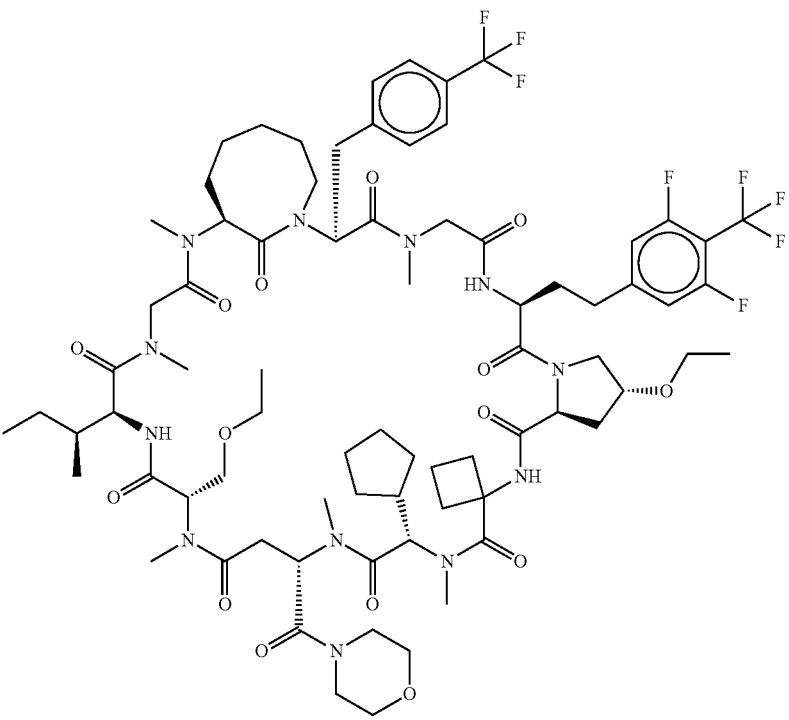 |

TABLE 38-continued
| Compound No. | Structural Formula |
|---|---|
| PP0852 | 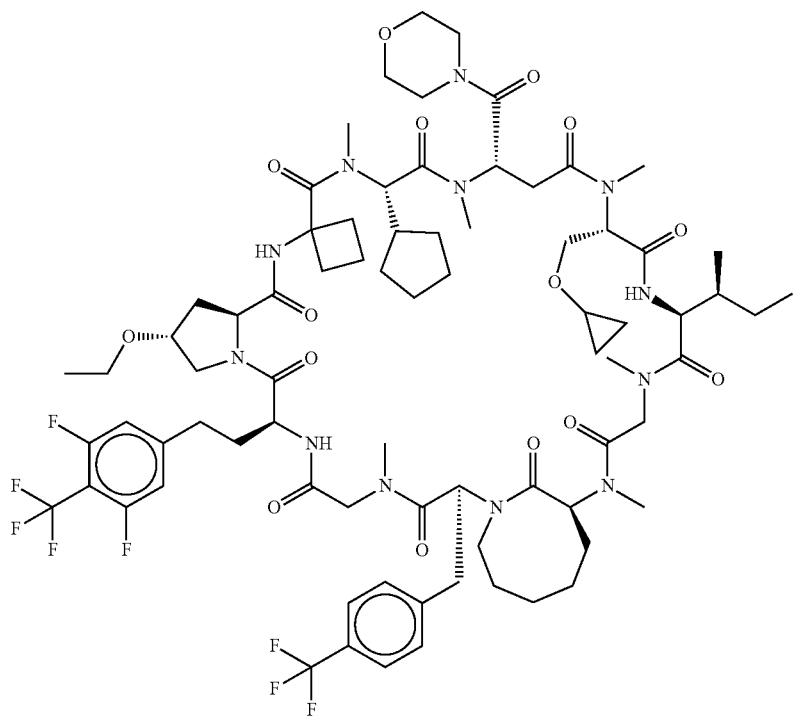 |
| PP0853 | 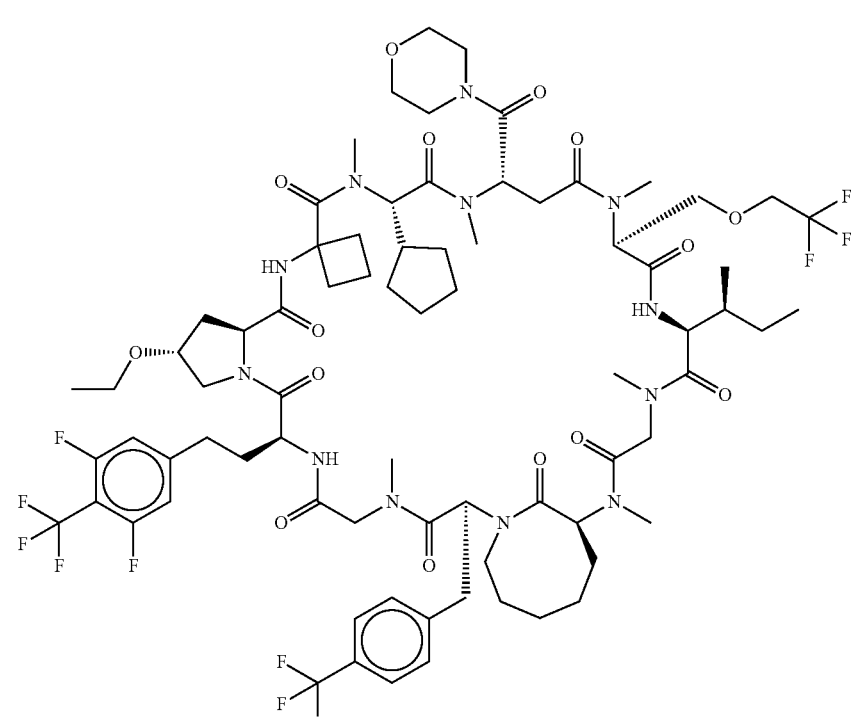 |

TABLE 38-continued
| Compound No. | Structural Formula |
|---|---|
| PP0854 | 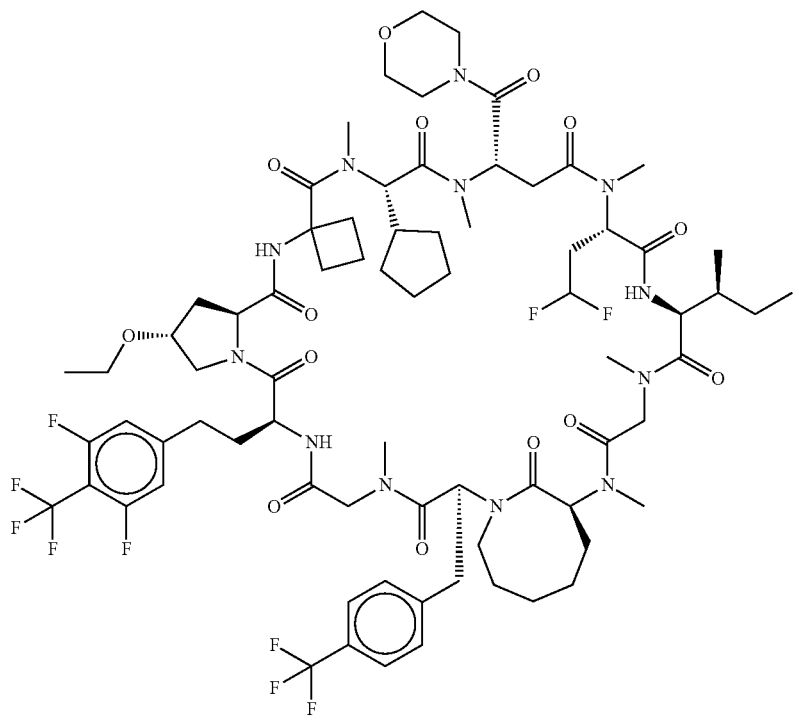 |
| PP0855 | 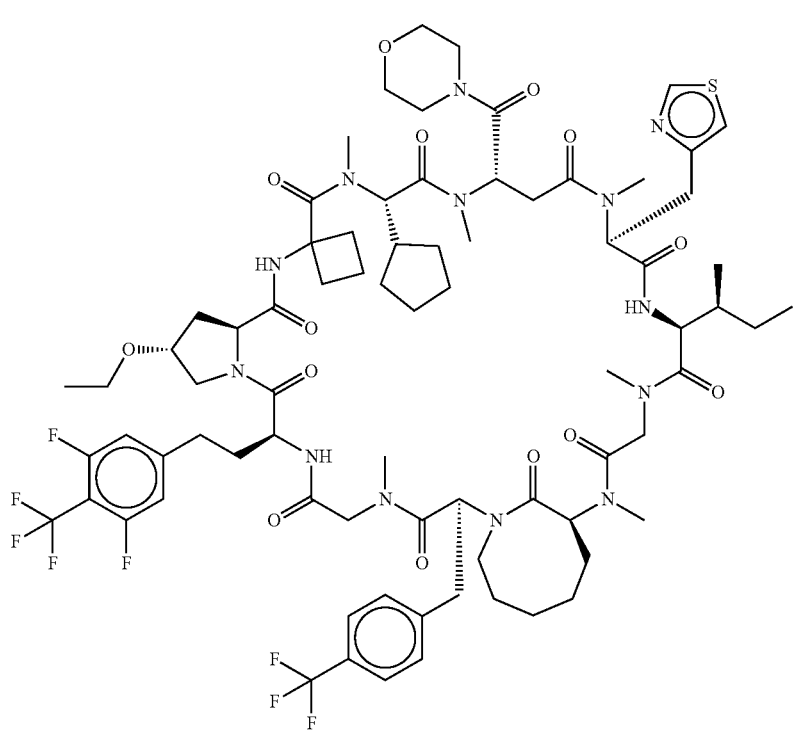 |

TABLE 38-continued
| Compound No. | Structural Formula |
|---|---|
| PP0856 | 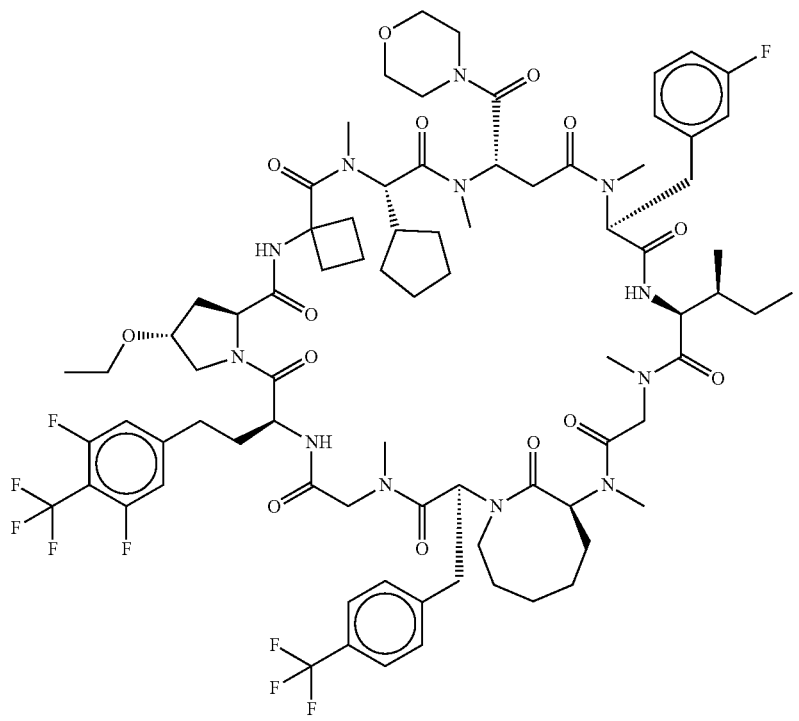 |
| PP0857 | 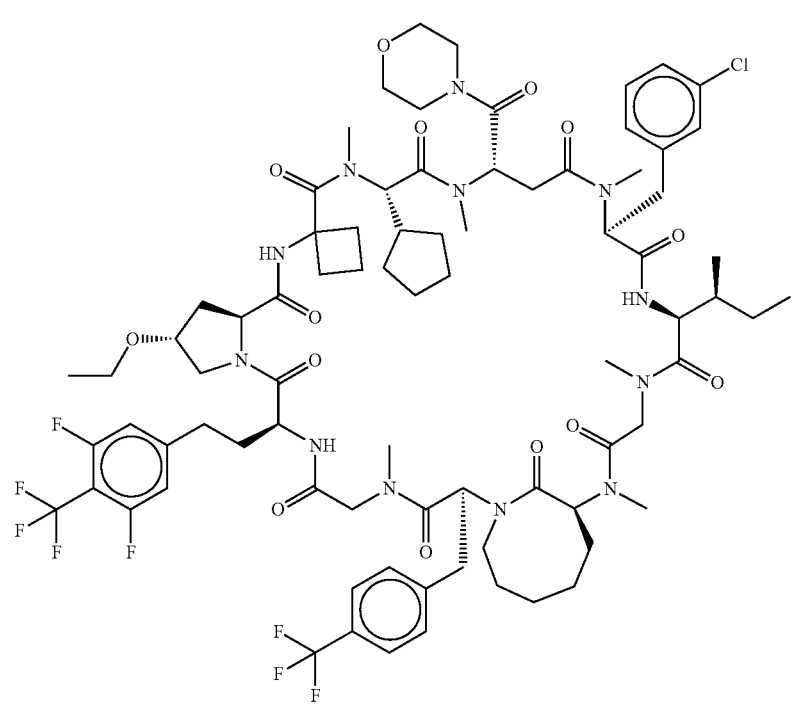 |

TABLE 38-continued
| Compound No. | Structural Formula |
|---|---|
| PP0858 | 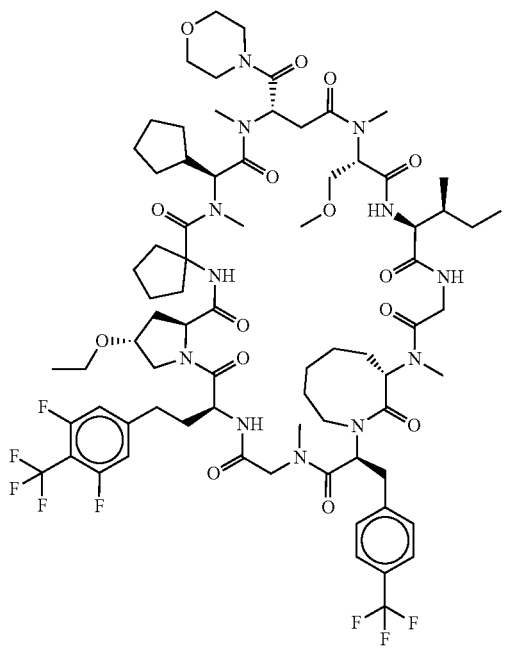 |
| PP0859 | 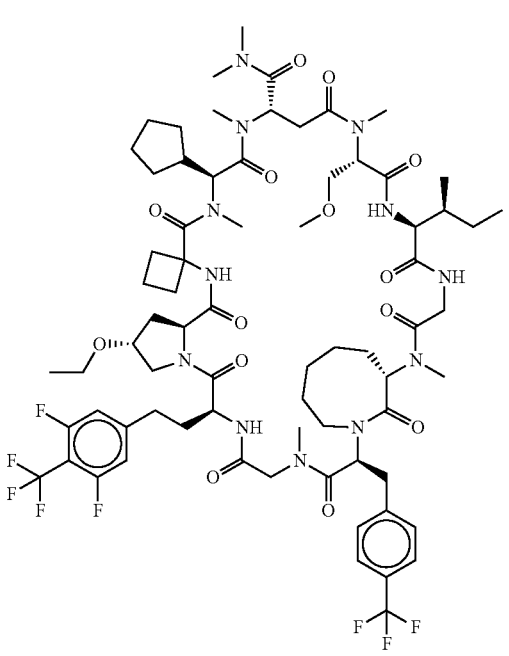 |

TABLE 38-continued
| Compound No. | Structural Formula |
|---|---|
| PP0860 | 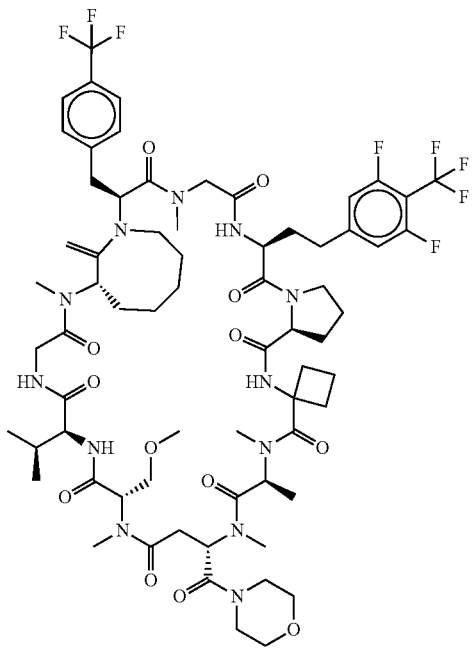 |
| PP0861 | 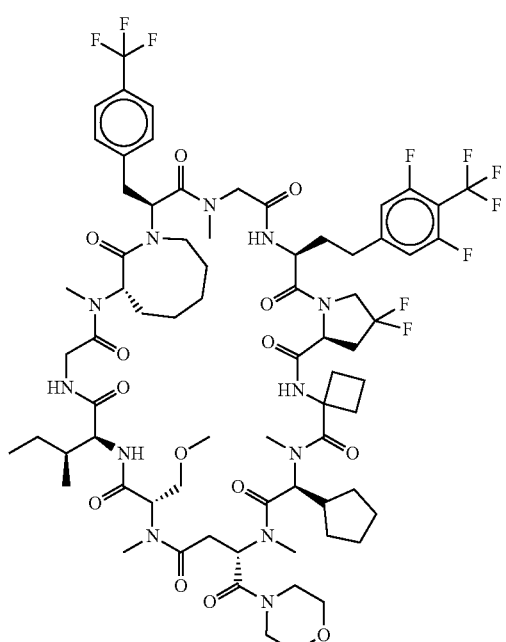 |

TABLE 38-continued
| Compound No. | Structural Formula |
|---|---|
| PP0862 | 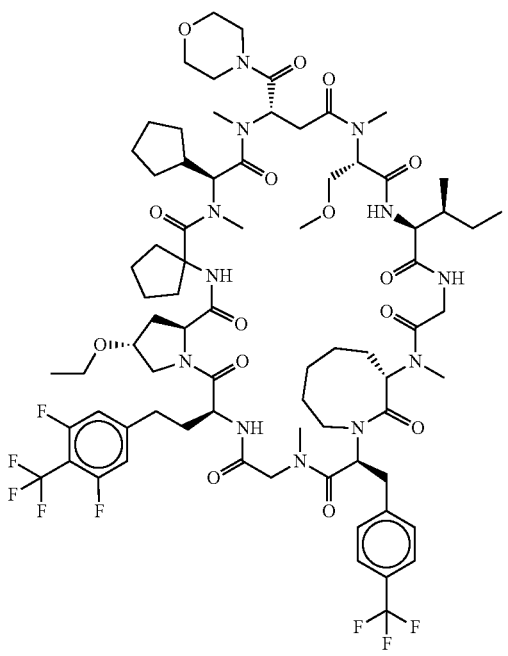 |
| PP0863 | 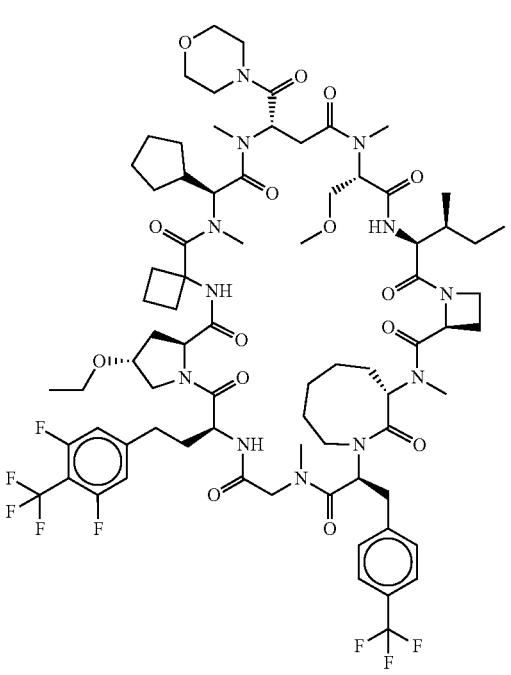 |

TABLE 38-continued
| Compound No. | Structural Formula |
|---|---|
| PP0864 | 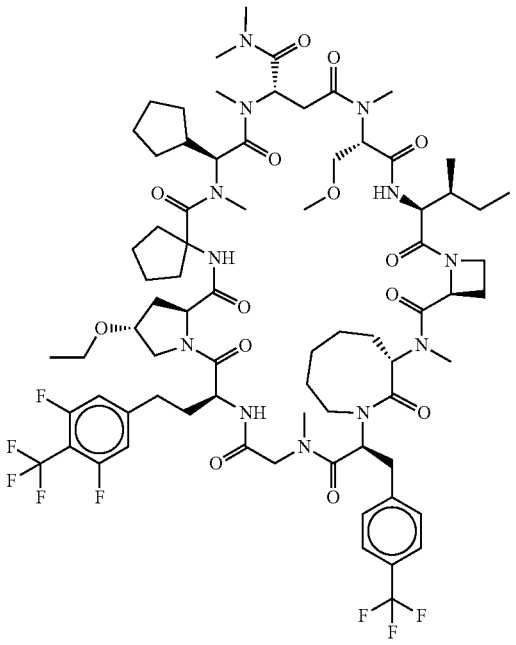 |
| PP0865 | 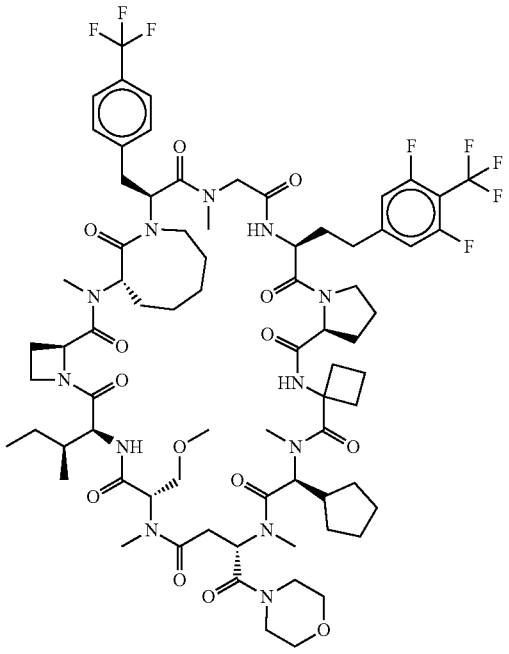 |

TABLE 38-continued

| Compound No. | Structural Formula |
|---|---|
| PP0866 | |
| PP0867 | |

TABLE 38-continued

| Compound No. | Structural Formula |
|---|---|
| PP0868 | |
| PP0869 | |

TABLE 38-continued
| Compound No. | Structural Formula |
|---|---|
| PP0870 | 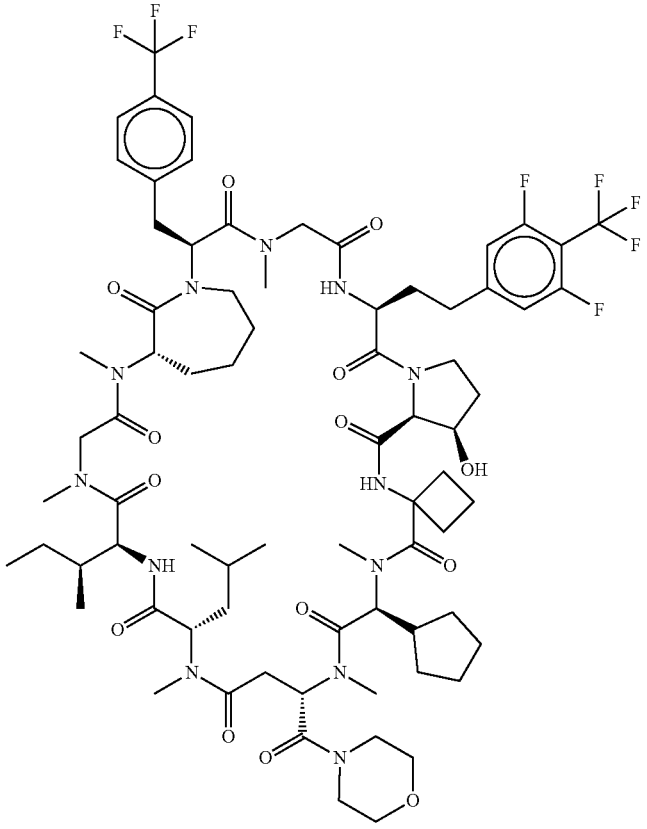 |
| PP0871 | 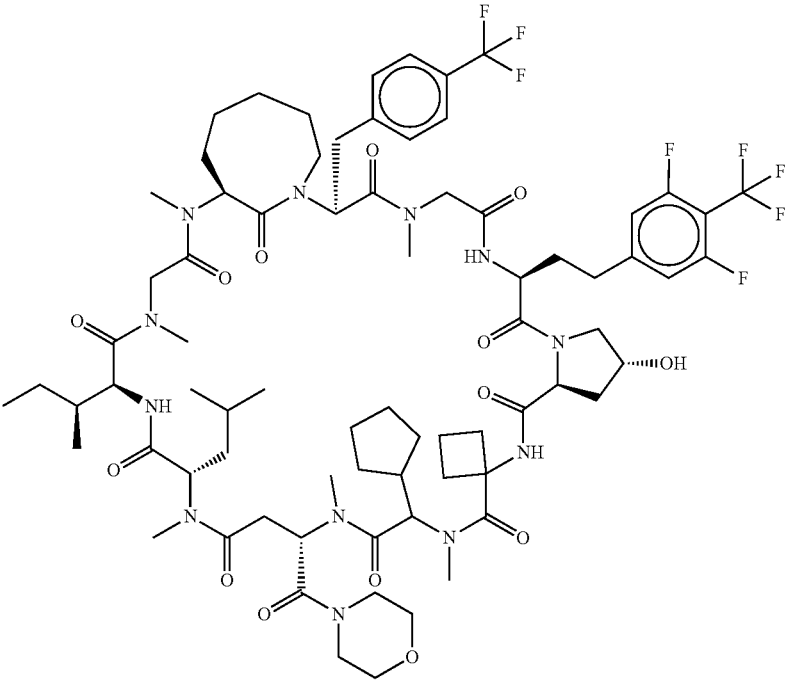 |

| Compound No. | Structural Formula |
|---|---|
| PP0872 | 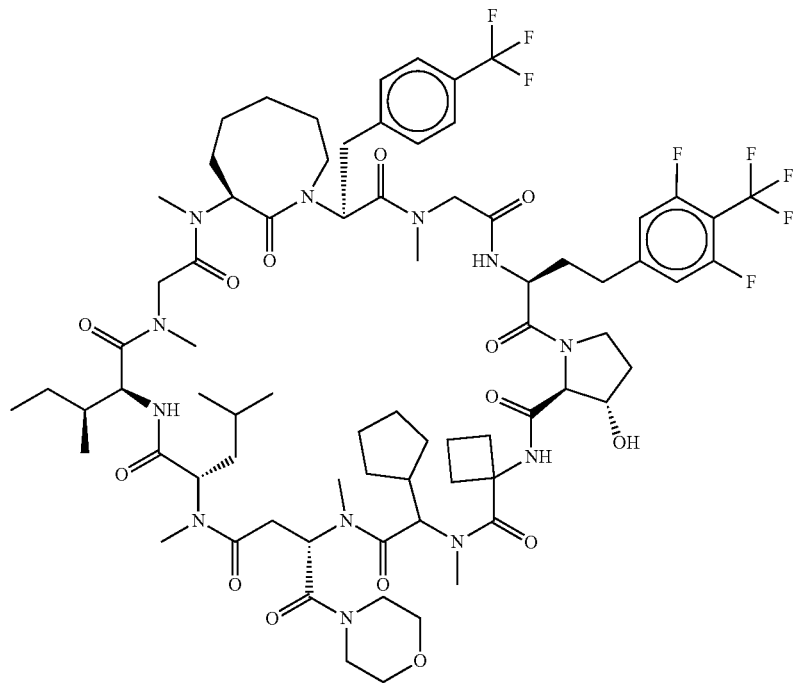 |
| PP0873 | 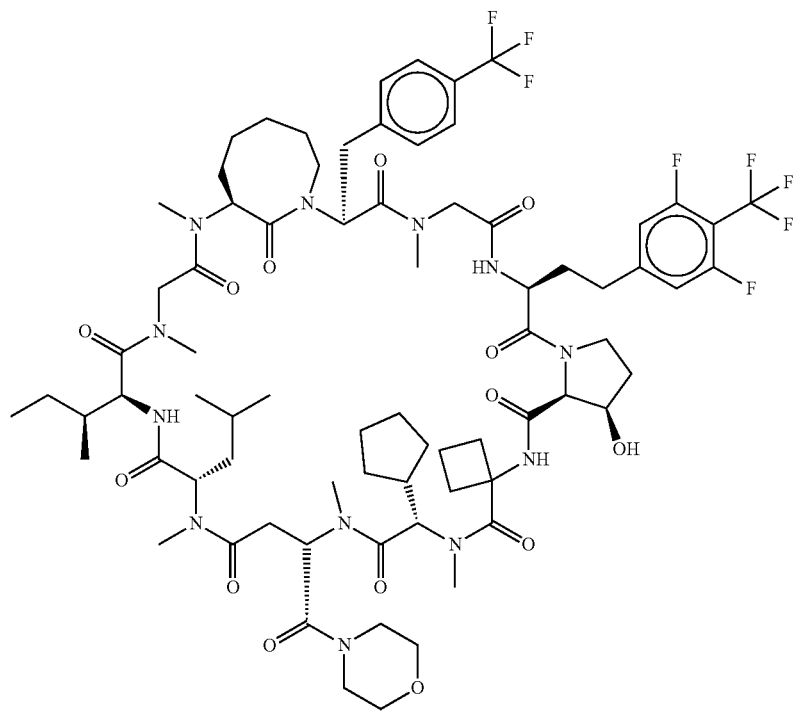 |

TABLE 38-continued

| Compound No. | Structural Formula |
|---|---|
| PP0874 | |
| PP0875 | |

TABLE 38-continued
| Compound No. | Structural Formula |
|---|---|
| PP0876 | 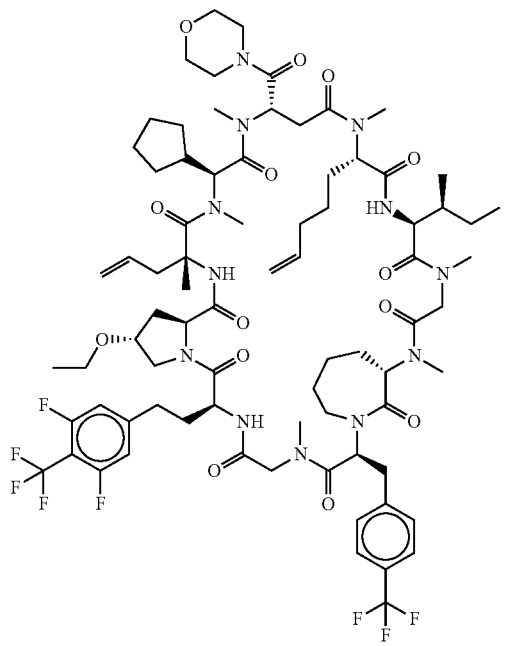 |
| PP0877 | 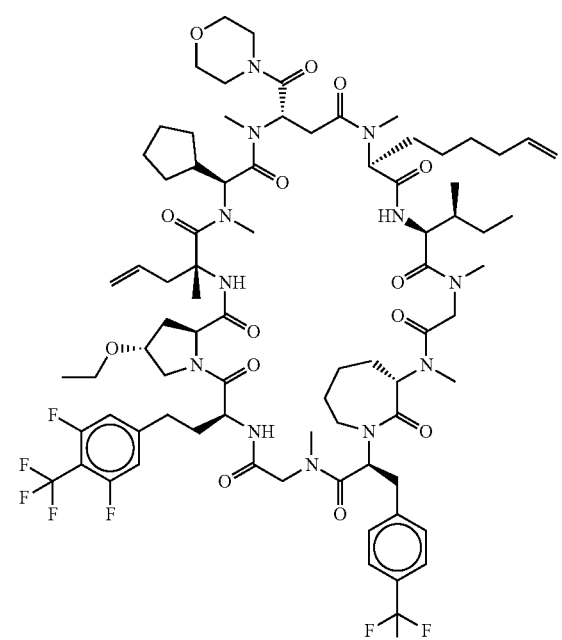 |

TABLE 38-continued
| Compound No. | Structural Formula |
|---|---|
| PP0878 | 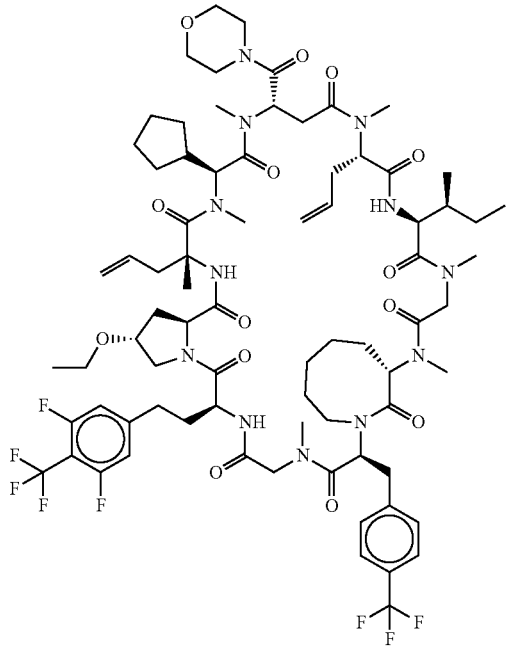 |
| PP0879 | 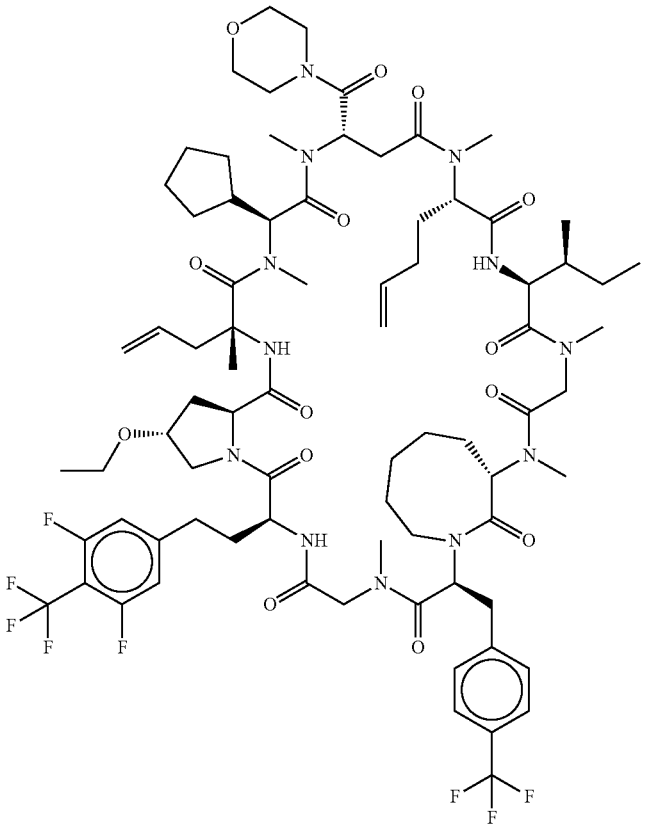 |

TABLE 38-continued
| Compound No. | Structural Formula |
|---|---|
| PP0880 | 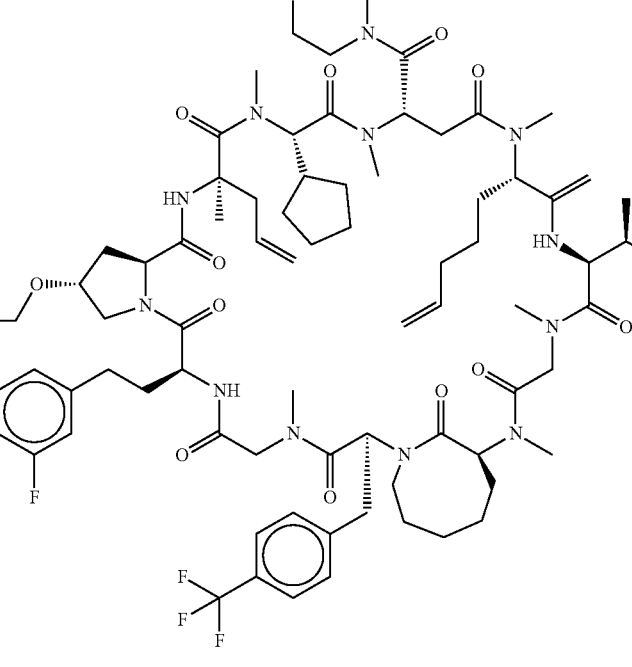 |
| PP0881 | 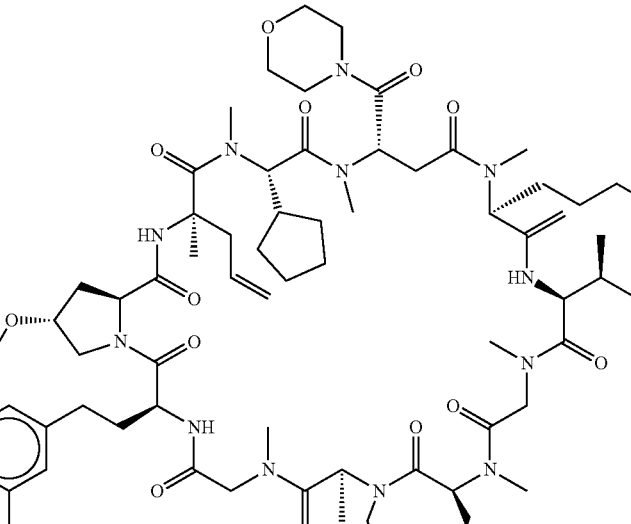 |

TABLE 38-continued
| Compound No. | Structural Formula |
|---|---|
| PP0882 | 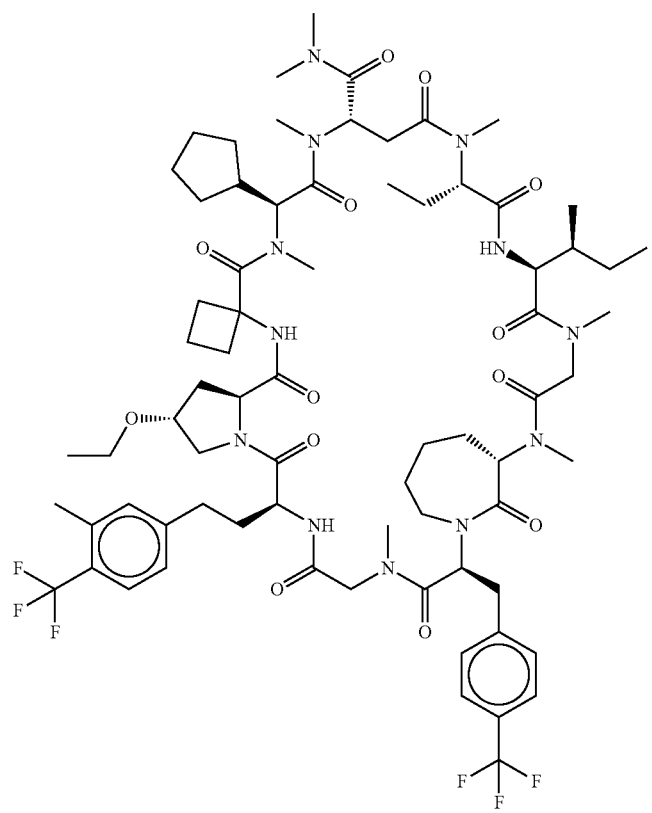 |
| PP0883 | 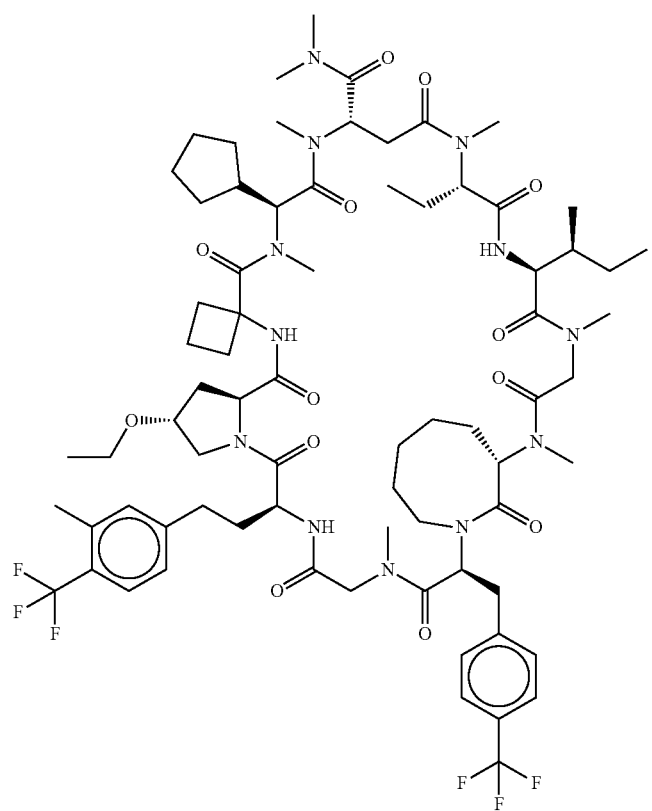 |

TABLE 38-continued
| Compound No. | Structural Formula |
|---|---|
| PP0884 | 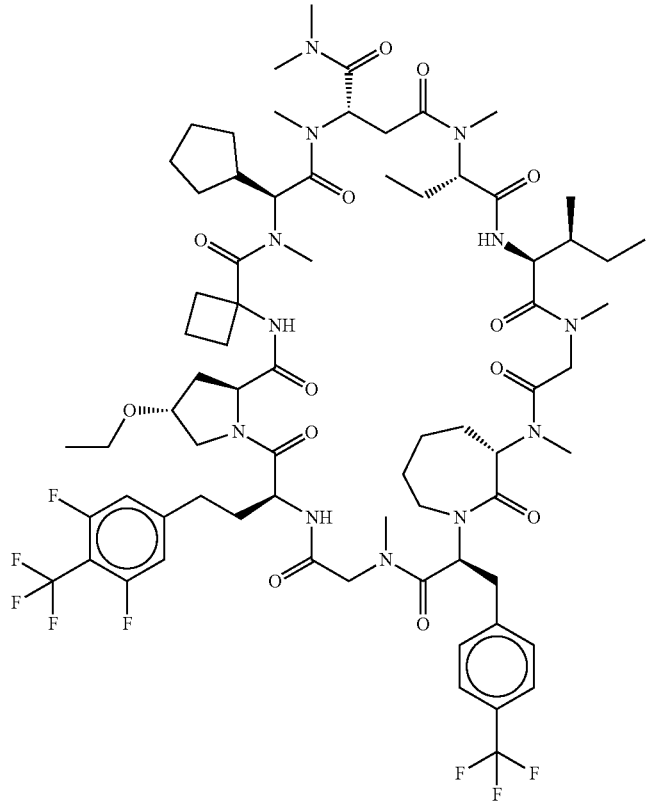 |
| PP0885 | 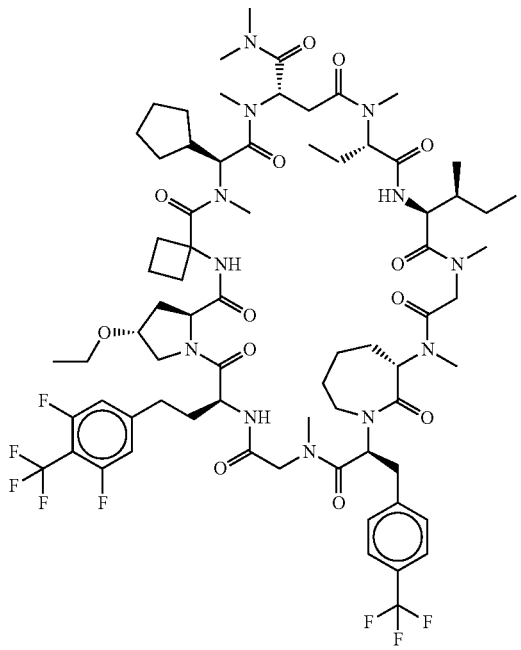 |

TABLE 38-continued
| Compound No. | Structural Formula |
|---|---|
| PP0886 | 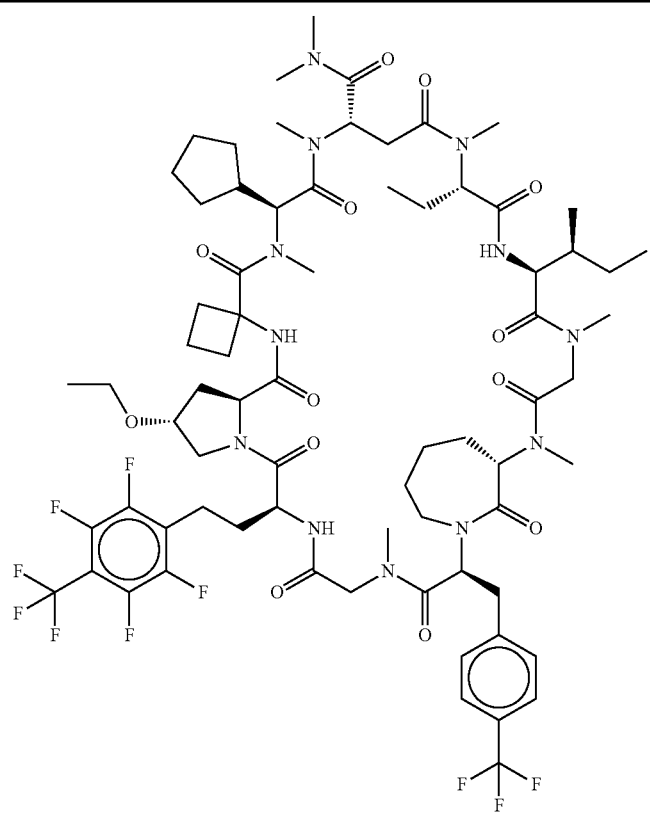 |
| PP0887 | 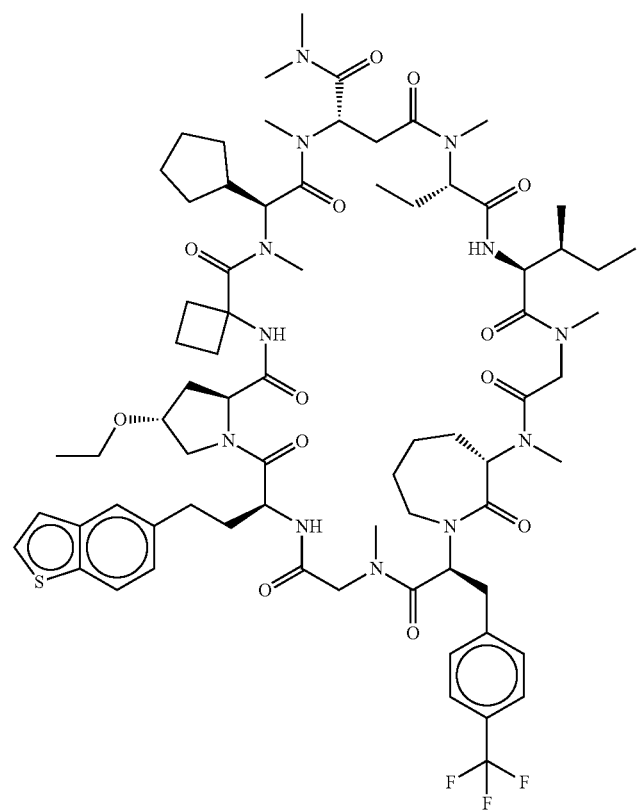 |

TABLE 38-continued
| Compound No. | Structural Formula |
|---|---|
| PP0888 | 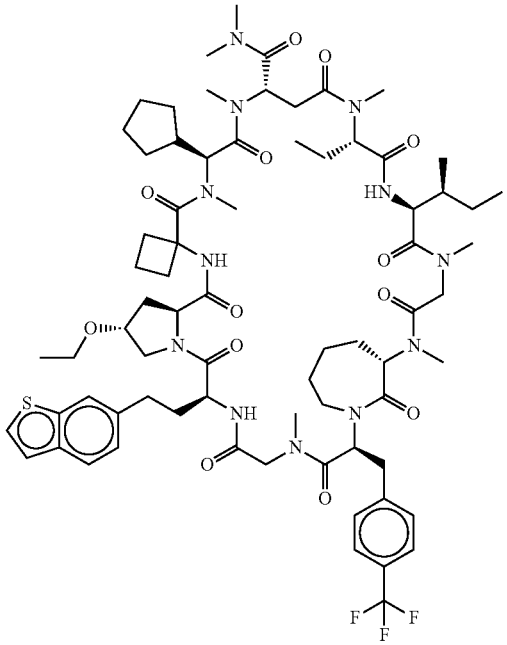 |
| PP0889 | 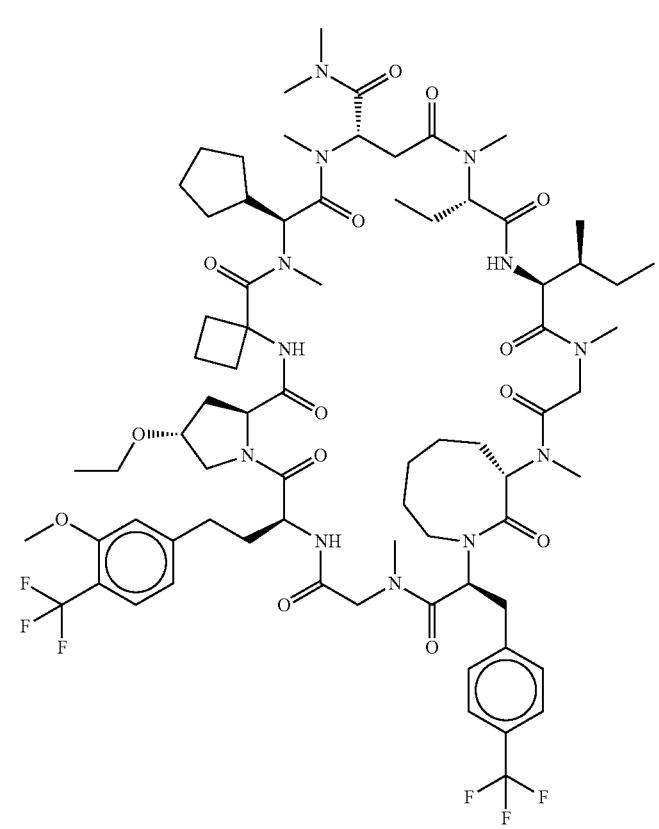 |

TABLE 38-continued
| Compound No. | Structural Formula |
| --- | --- |
| PP0890 | 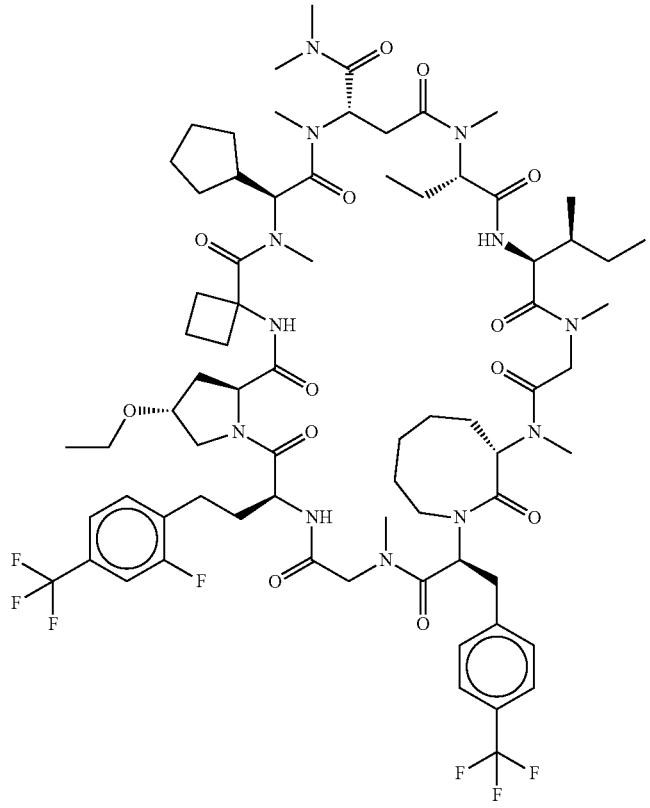 |
| PP0891 | 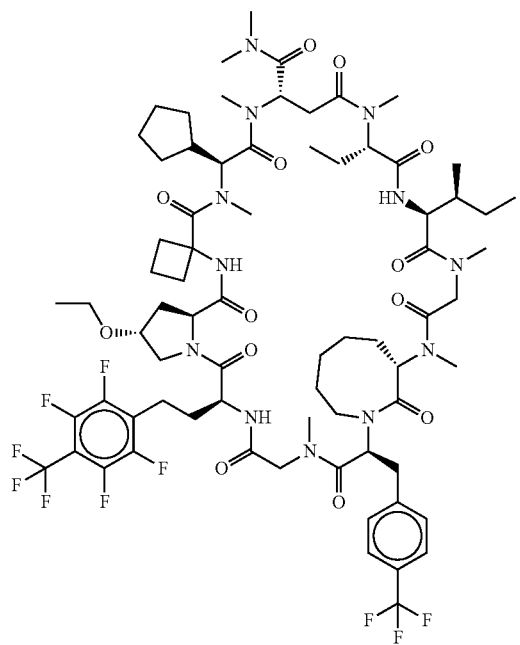 |

TABLE 38-continued
| Compound No. | Structural Formula |
|---|---|
| PP0892 | 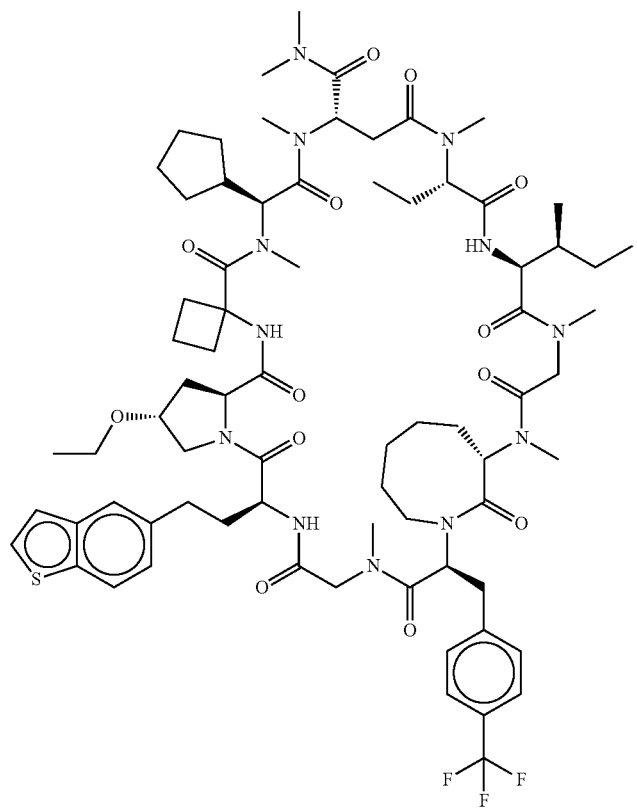 |
| PP0893 | 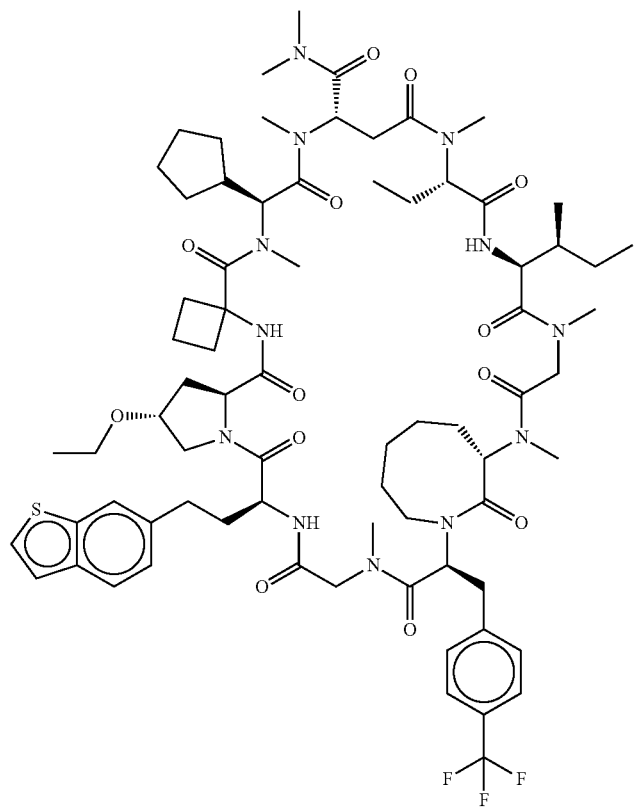 |

TABLE 38-continued

| Compound No. | Structural Formula |
|---|---|
| PP0894 | |
| PP0895 | |

TABLE 38-continued
| Compound No. | Structural Formula |
|---|---|
| PP0896 | 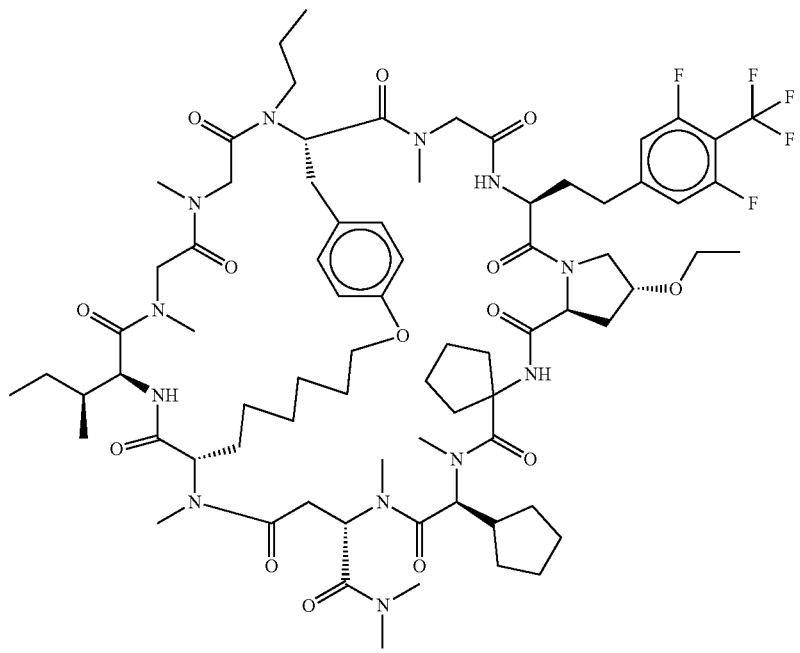 |
| PP0898 | 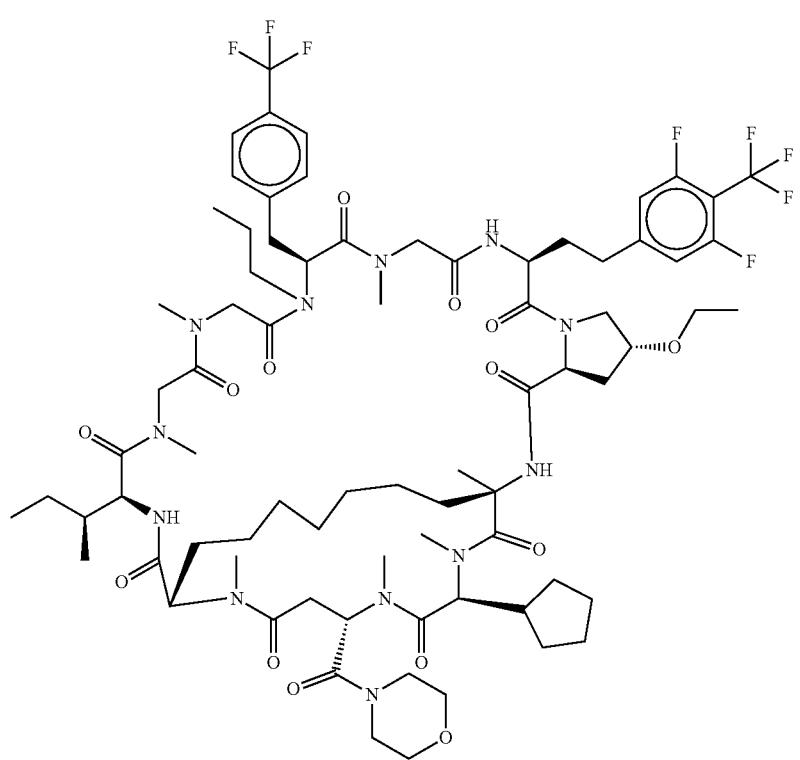 |

TABLE 38-continued
| Compound No. | Structural Formula |
|---|---|
| PP0899 | 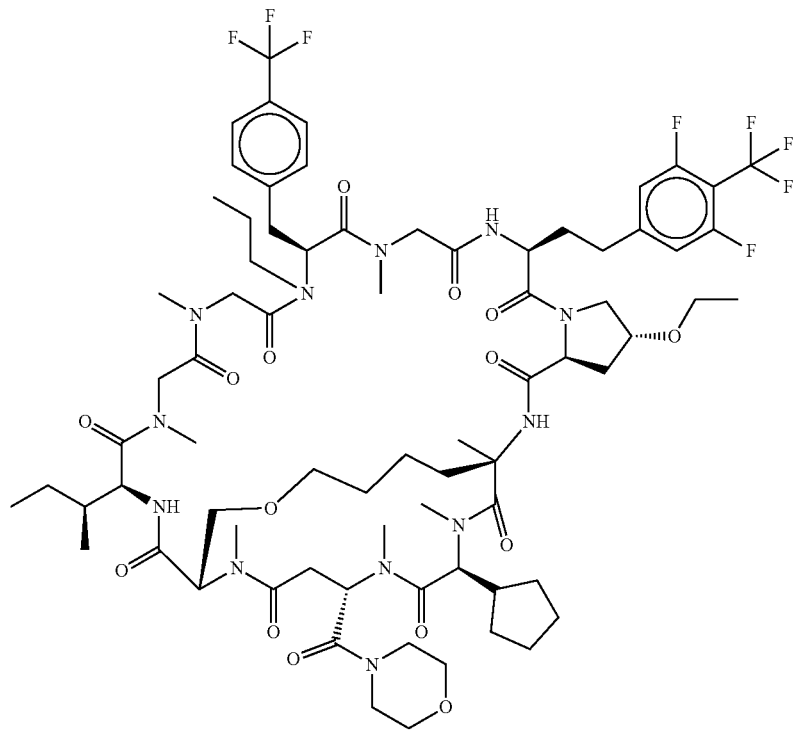 |
| PP0900 | 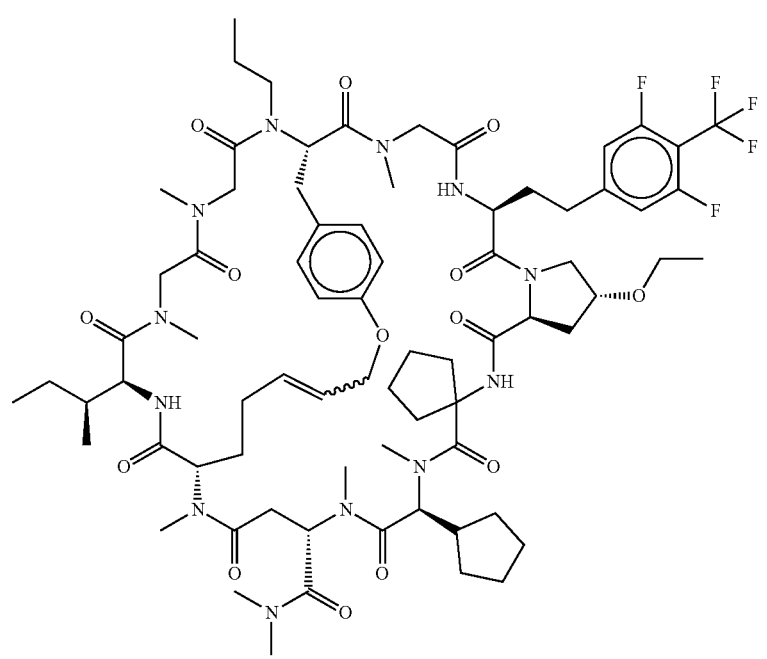 |

TABLE 38-continued
| Compound No. | Structural Formula |
|---|---|
| PP0901 | 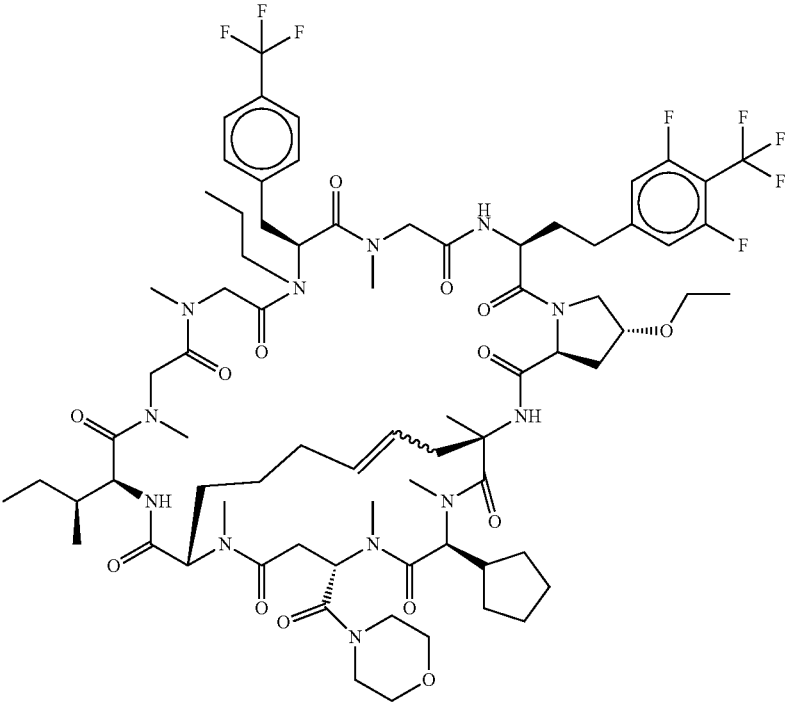 |
| PP0902 | 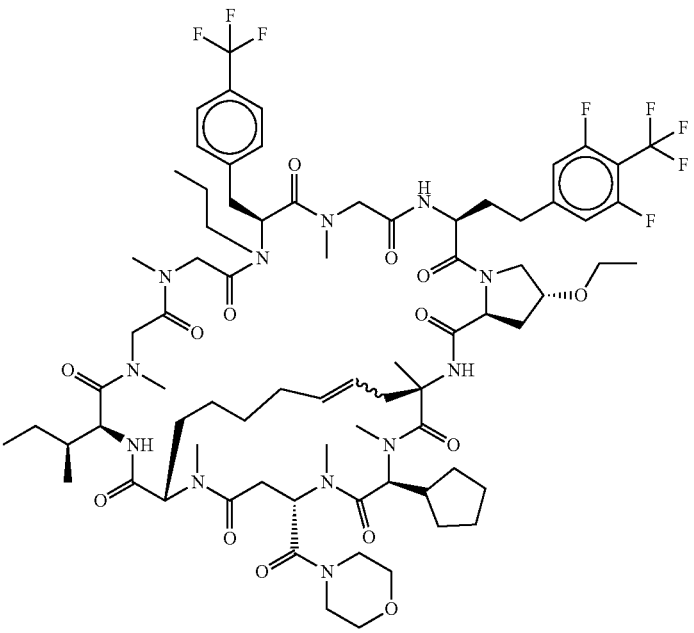 |

TABLE 38-continued
| Compound No. | Structural Formula |
|---|---|
| PP0903 | 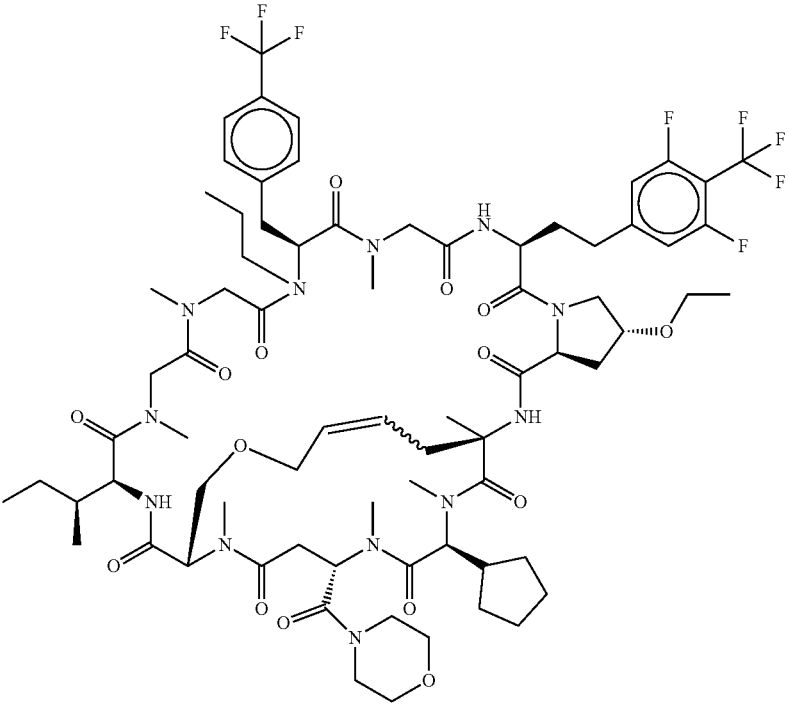 |
| PP0904 | 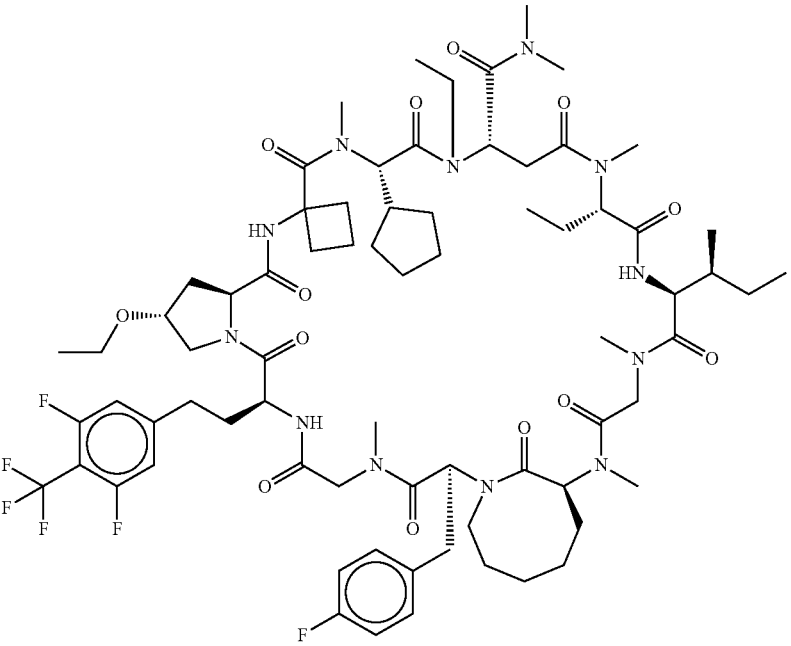 |

TABLE 38-continued
| Compound No. | Structural Formula |
| --- | --- |
| PP0905 | 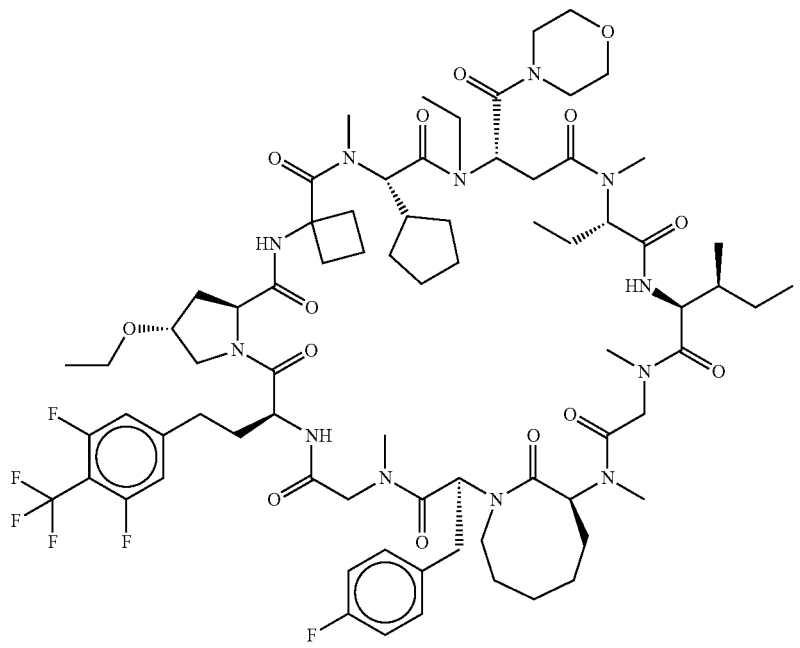 |
| PP0906 | 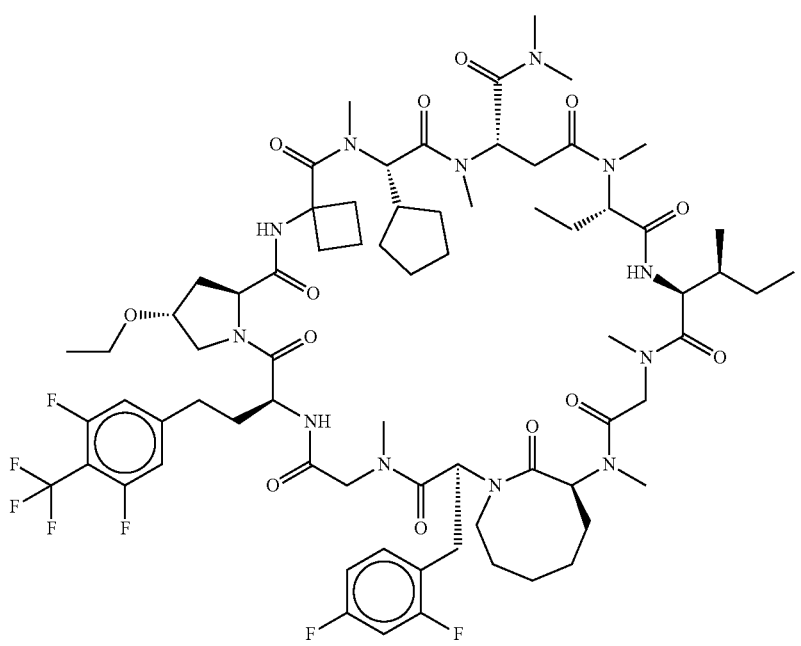 |

TABLE 38-continued
| Compound No. | Structural Formula |
|---|---|
| PP0907 | 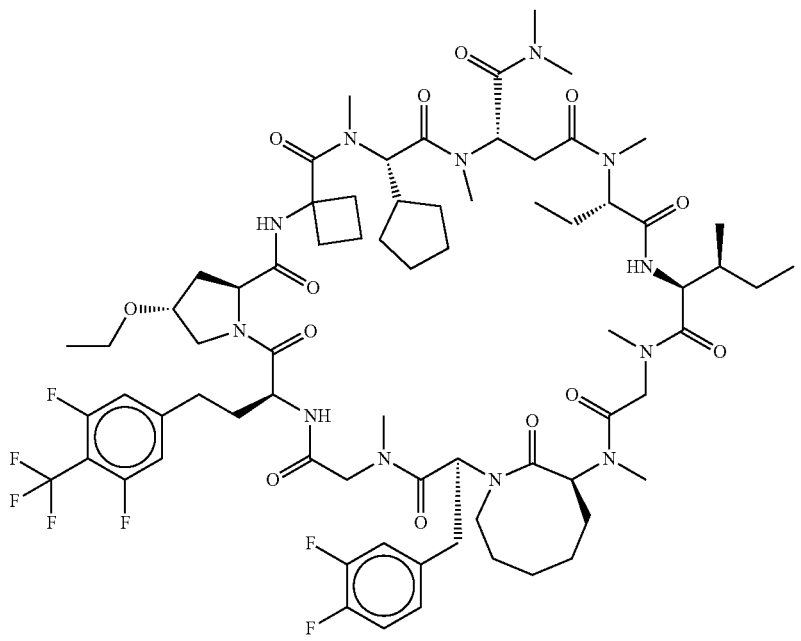 |
| PP0908 | 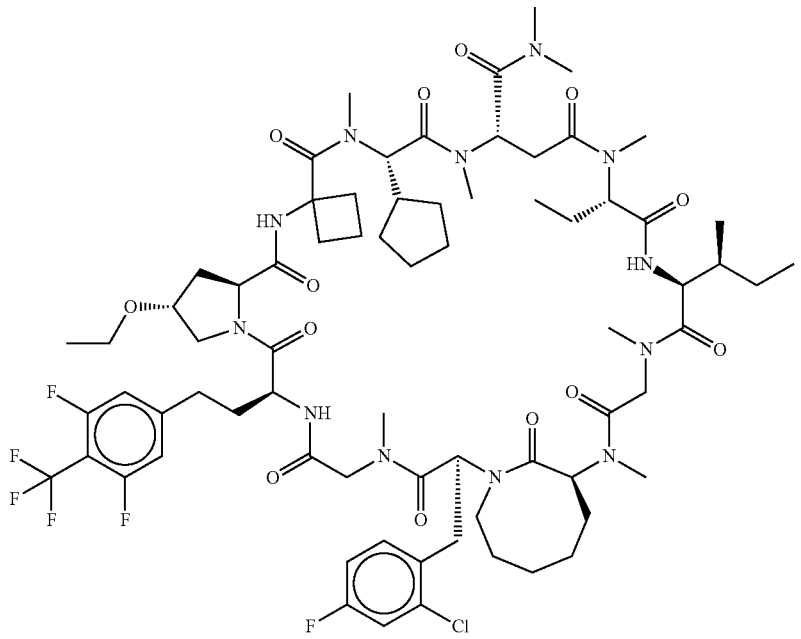 |

TABLE 38-continued
| Compound No. | Structural Formula |
| --- | --- |
| PP0909 | 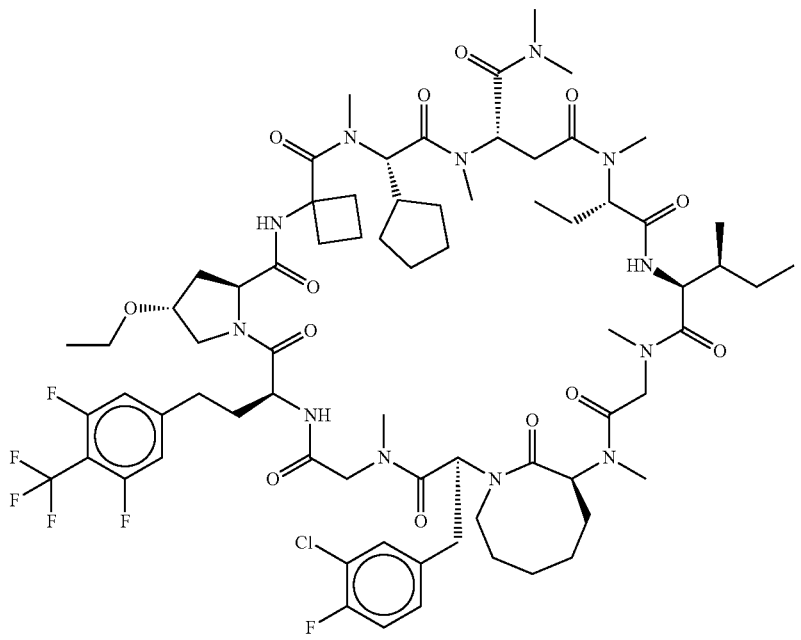 |
| PP0910 | 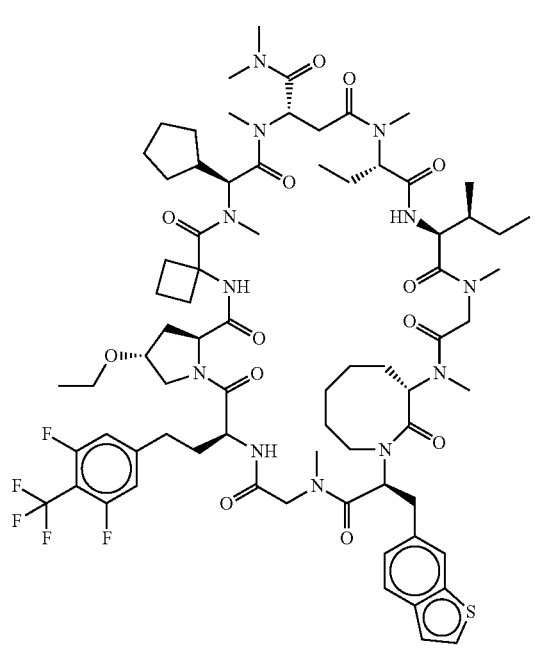 |

TABLE 38-continued
| Compound No. | Structural Formula |
| --- | --- |
| PP0911 | 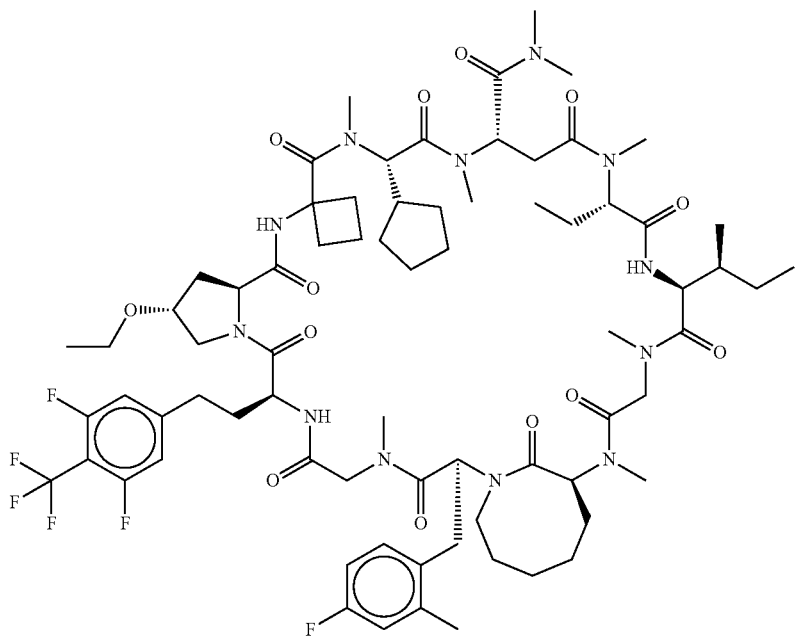 |
| PP0912 | 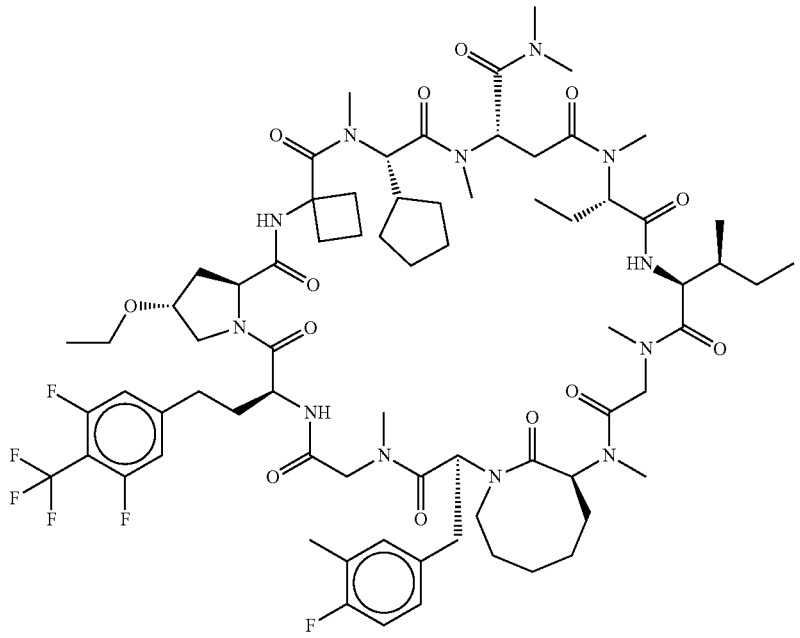 |

| Compound No. | Structural Formula |
|---|---|
| PP0913 | 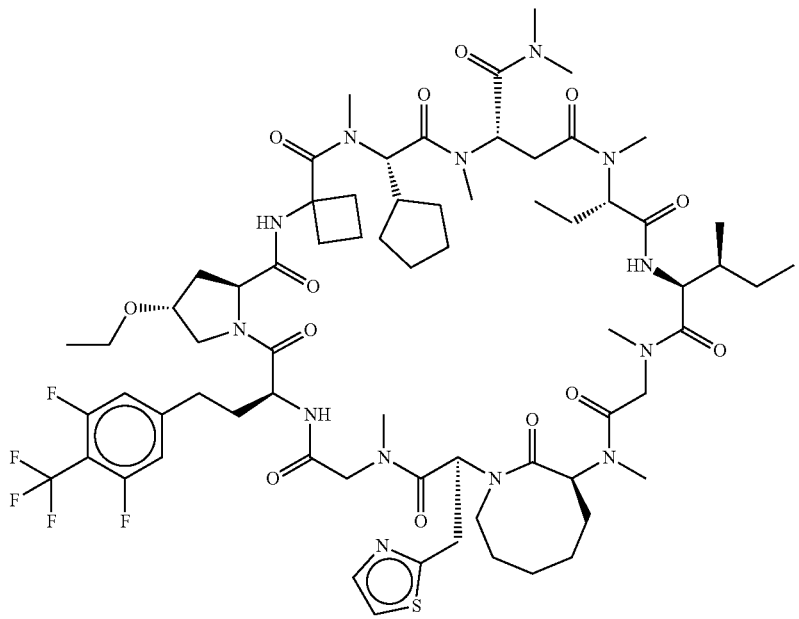 |
| PP0914 | 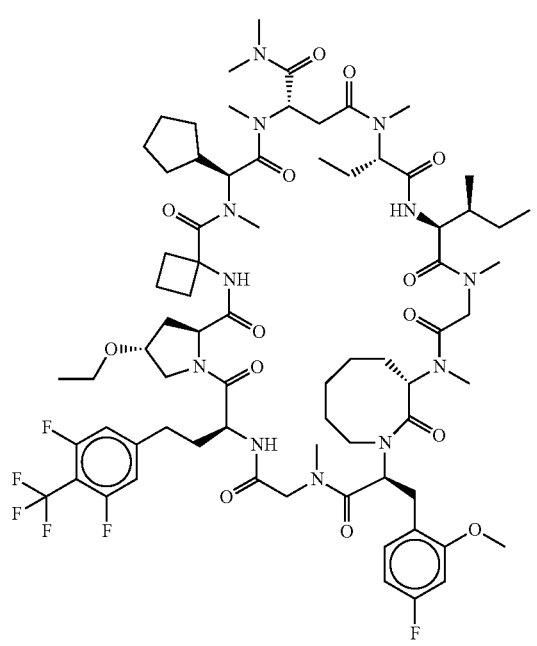 |

TABLE 38-continued

| Compound No. | Structural Formula |
|---|---|
| PP0915 | |
| PP0916 | |

TABLE 38-continued
| Compound No. | Structural Formula |
|---|---|
| PP0917 | 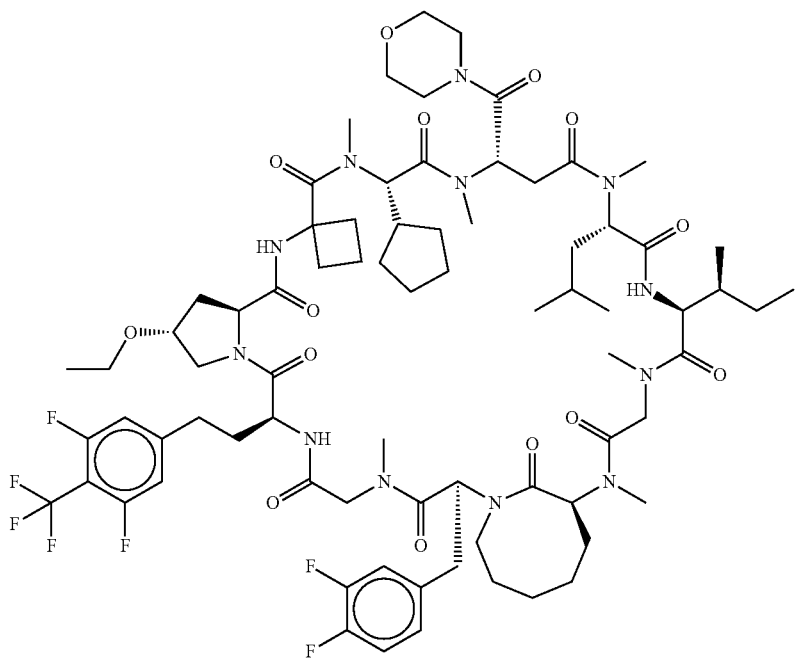 |
| PP0918 | 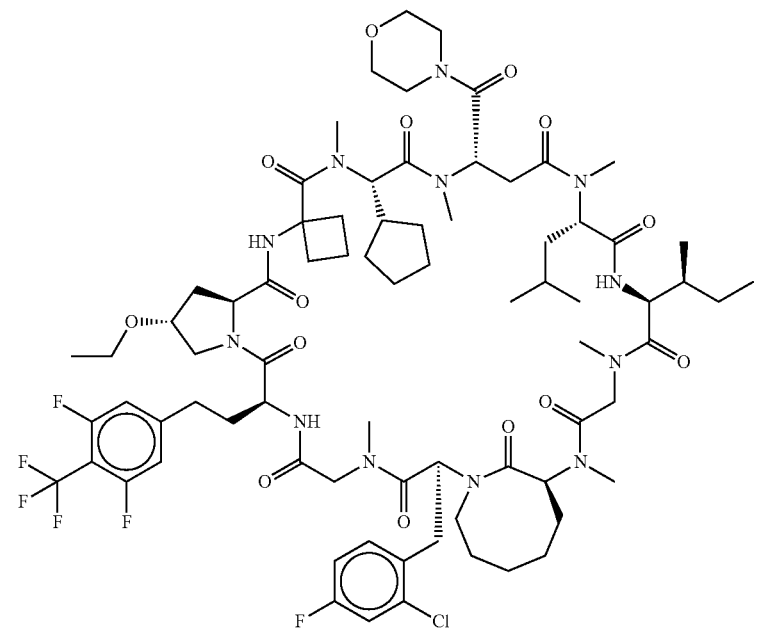 |

TABLE 38-continued
| Compound No. | Structural Formula |
|---|---|
| PP0919 | 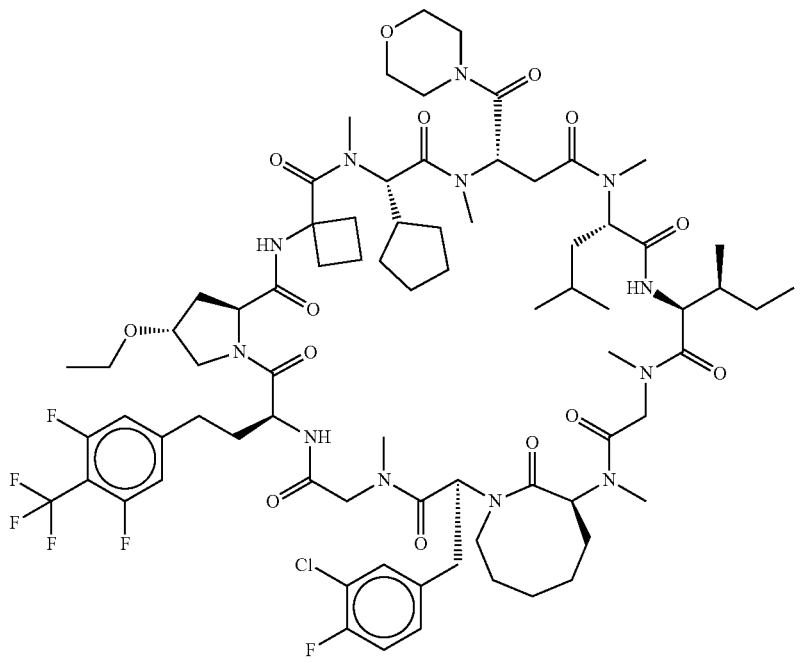 |
| PP0920 | 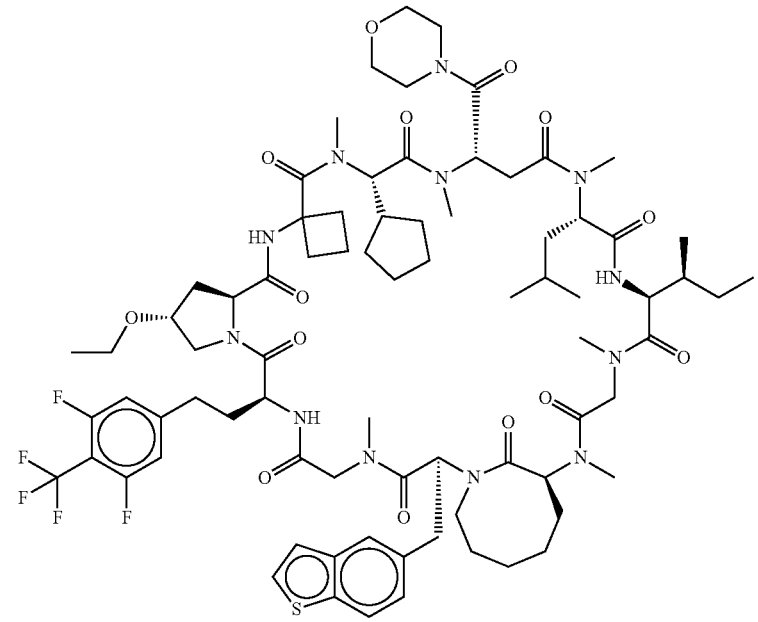 |

TABLE 38-continued
| Compound No. | Structural Formula |
|---|---|
| PP0921 | 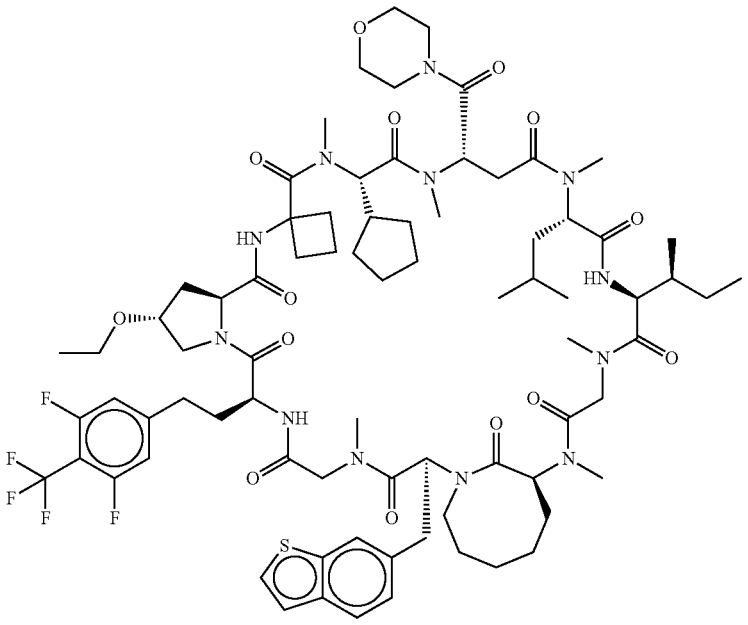 |
| PP0922 | 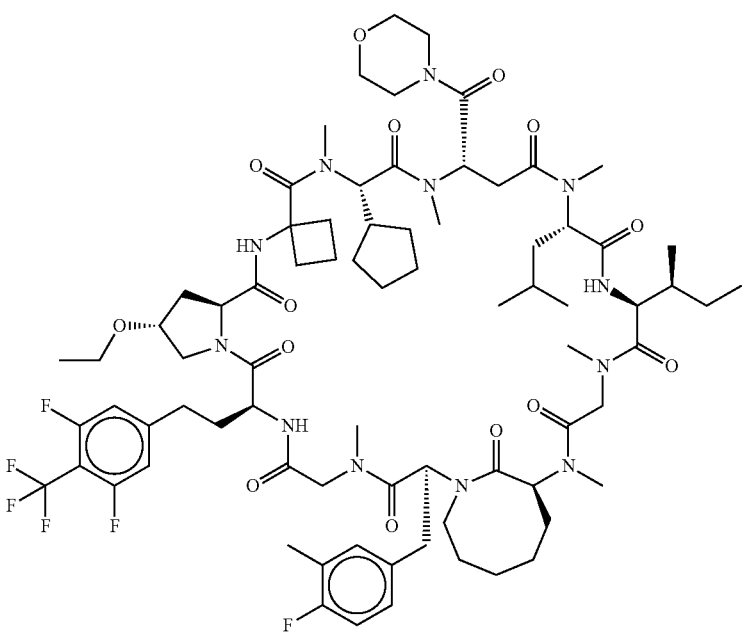 |

TABLE 38-continued
| Compound No. | Structural Formula |
|---|---|
| PP0923 | 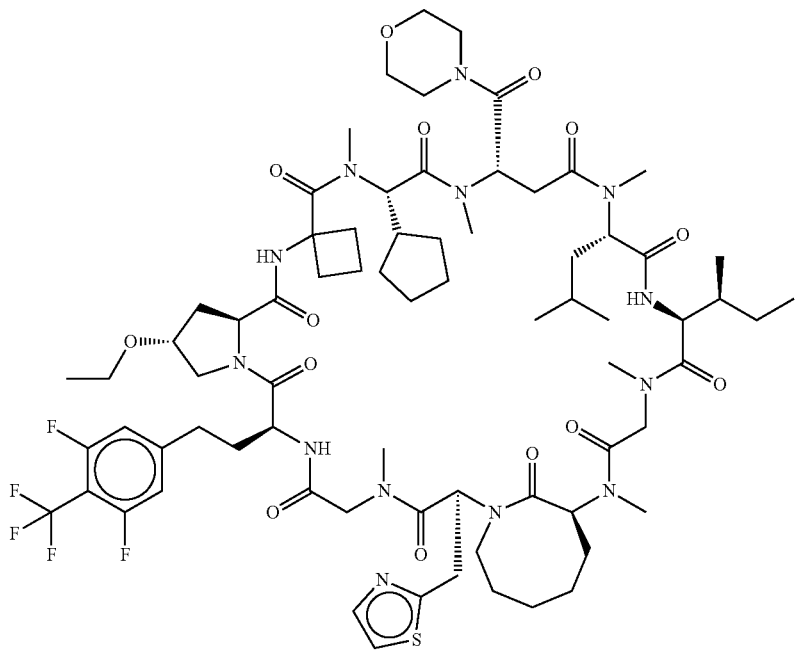 |
| PP0924 | 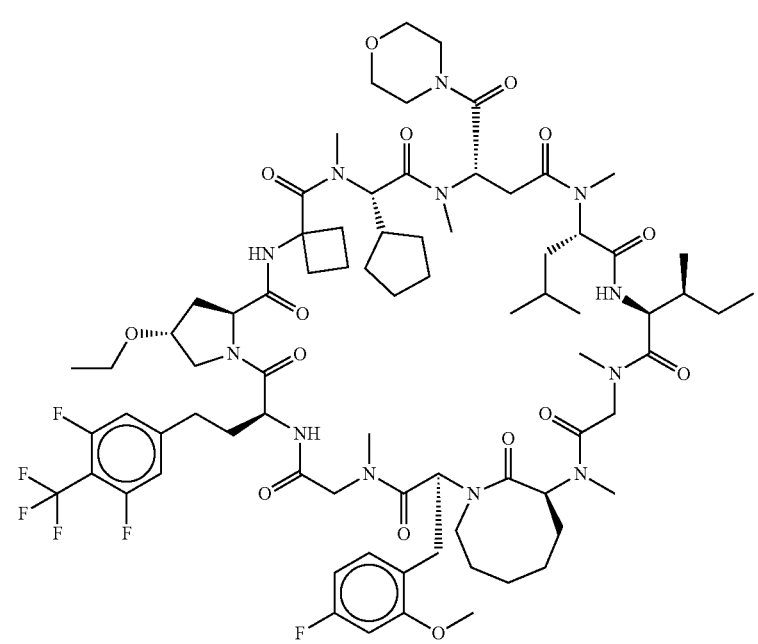 |

TABLE 38-continued
| Compound No. | Structural Formula |
|---|---|
| PP0925 | 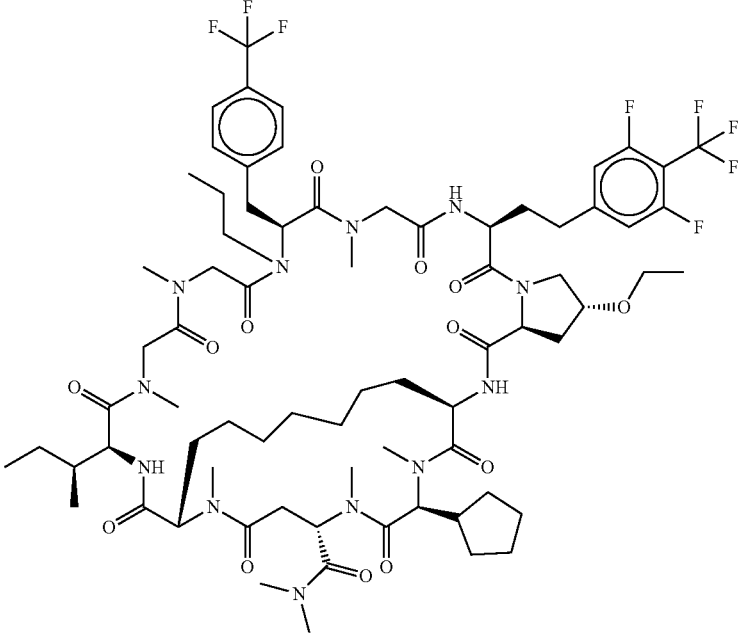 |
| PP0926 | 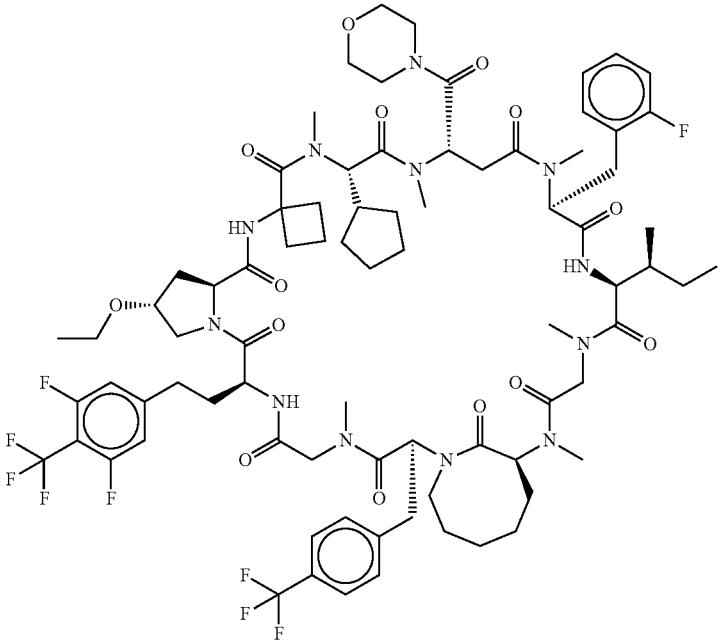 |

1755                         1756
TABLE 38-continued
| Compound No. | Structural Formula |
| --- | --- |
| PP0927 | 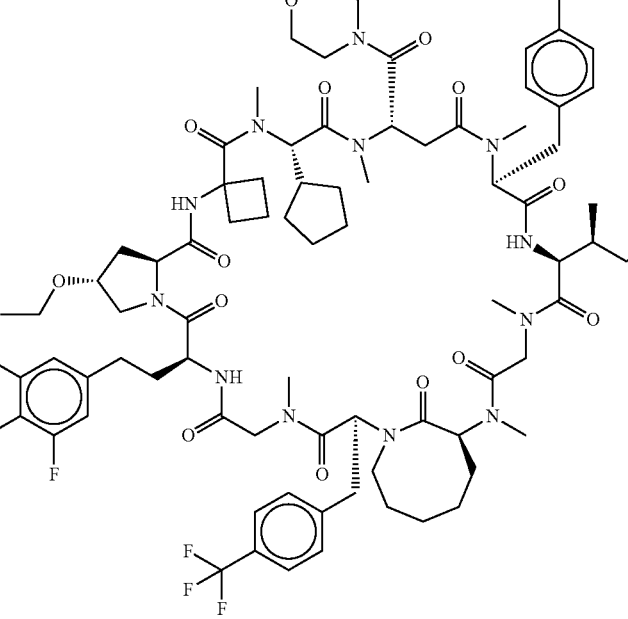 |
| PP0928 | 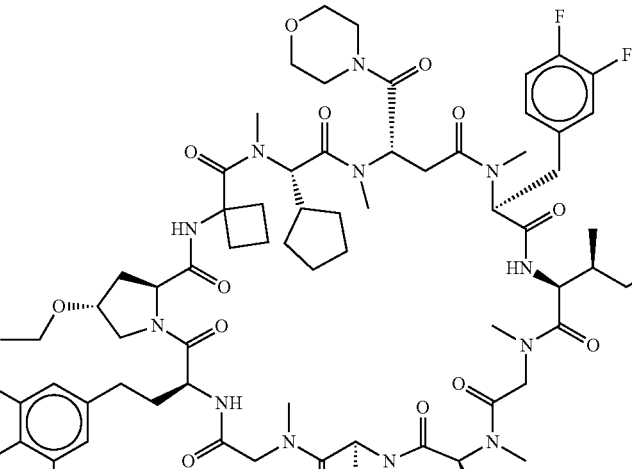 |

TABLE 38-continued
| Compound No. | Structural Formula |
| --- | --- |
| PP0929 | 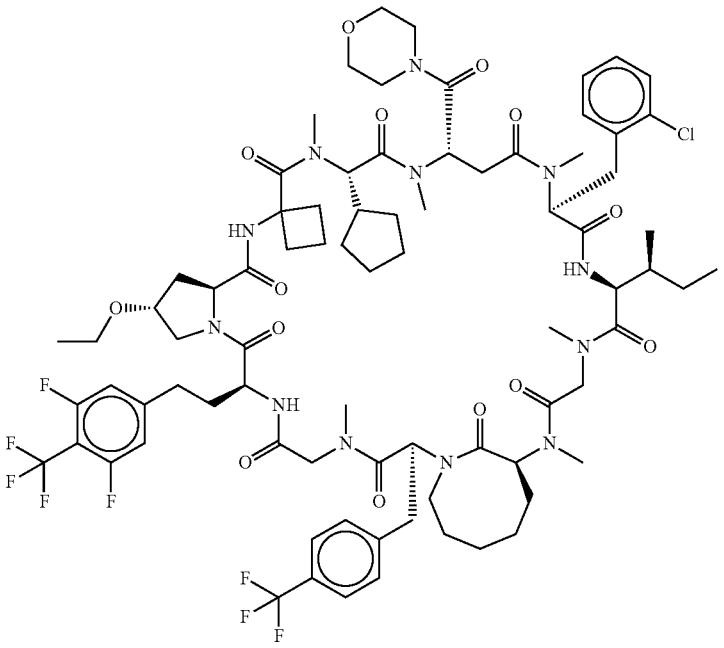 |
| PP0930 | 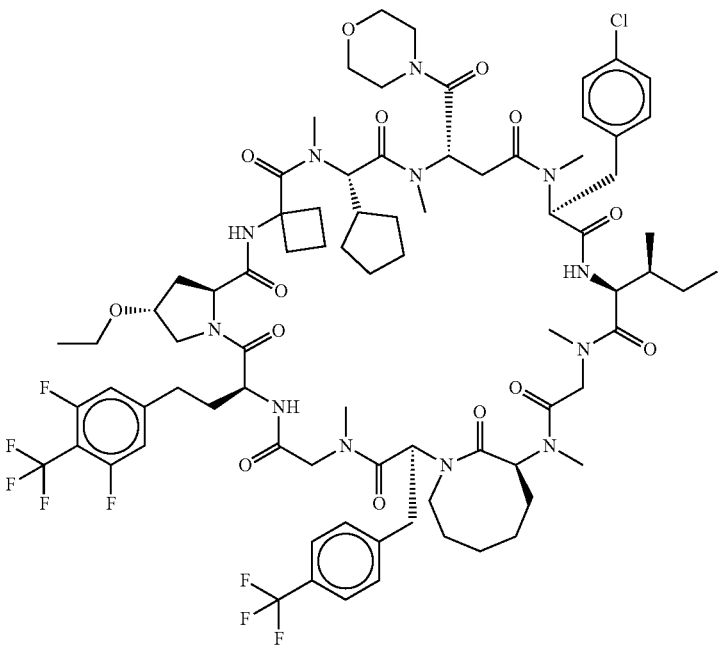 |

TABLE 38-continued
| Compound No. | Structural Formula |
| --- | --- |
| PP0931 | 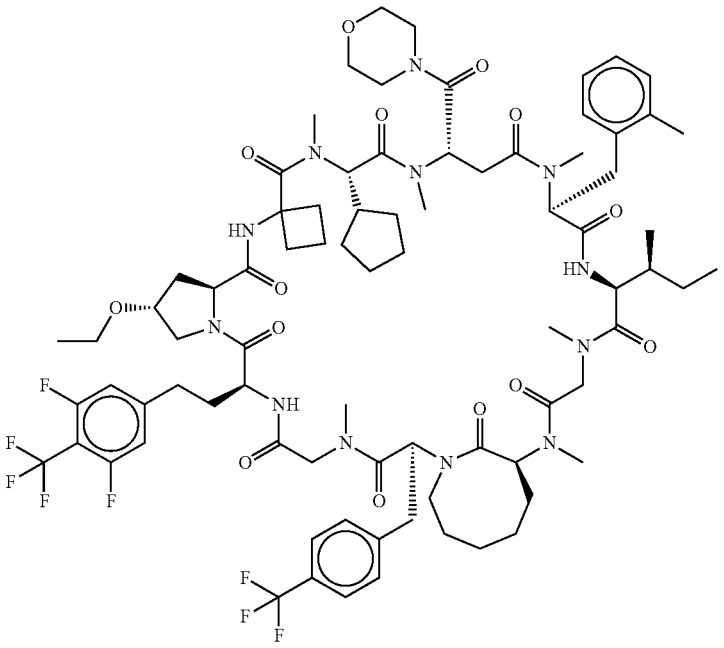 |
| PP0932 | 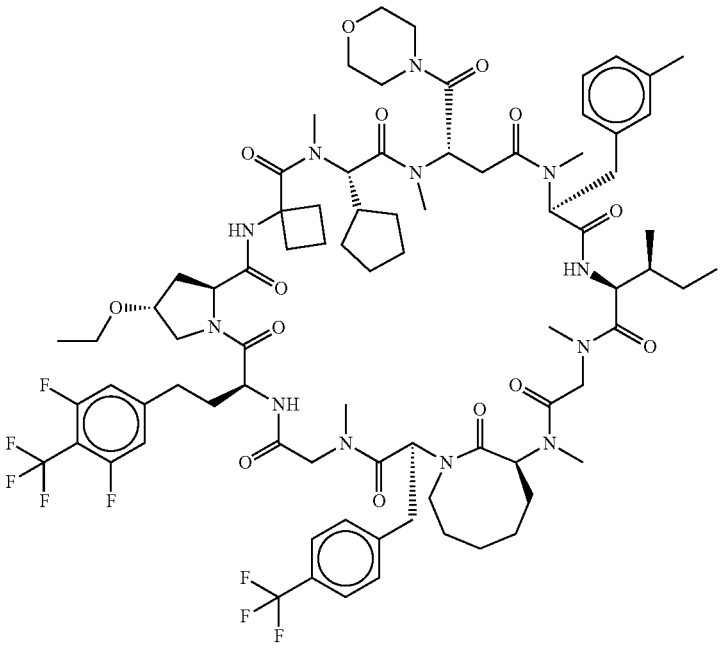 |

| Compound No. | Structural Formula |
|---|---|
| PP0933 | 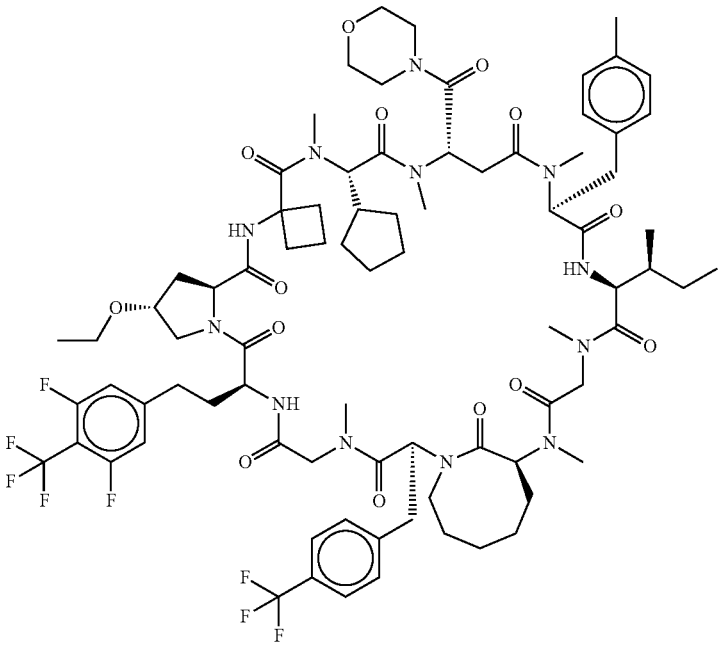 |
| PP0934 | 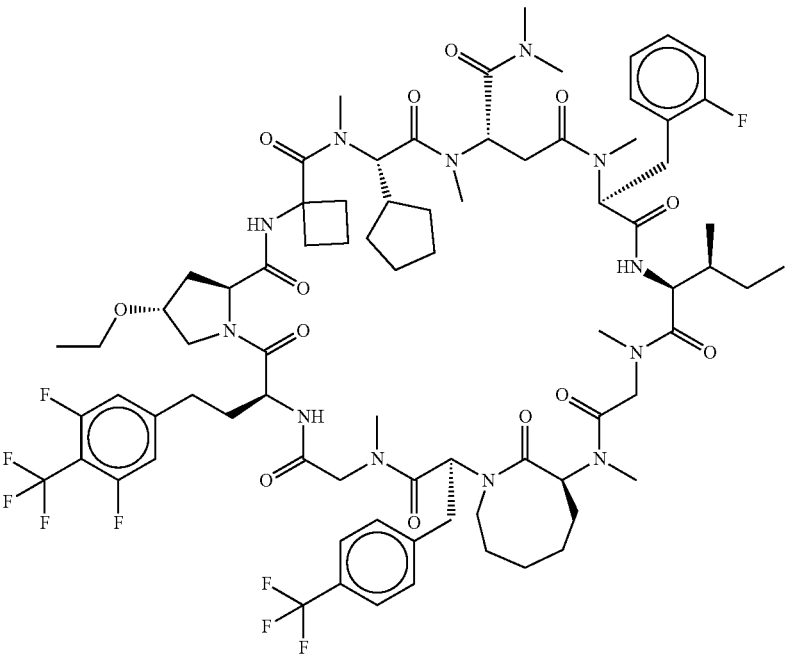 |

TABLE 38-continued
| Compound No. | Structural Formula |
|---|---|
| PP0935 | 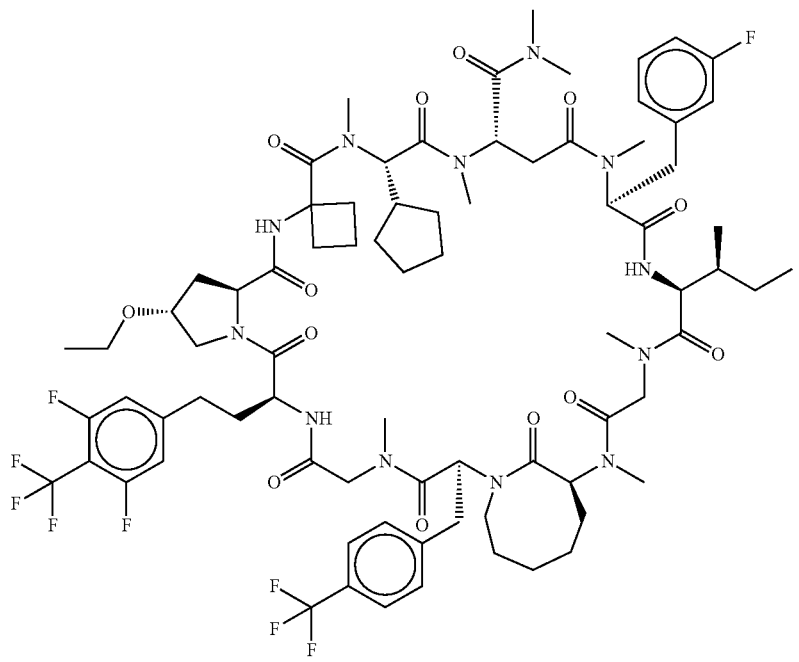 |
| PP0936 | 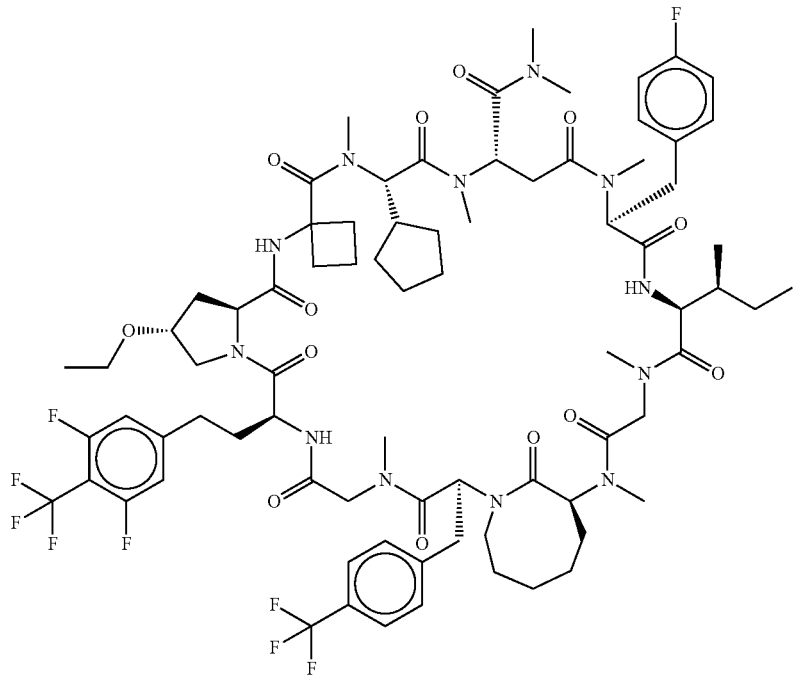 |

TABLE 38-continued
| Compound No. | Structural Formula |
|---|---|
| PP0937 | 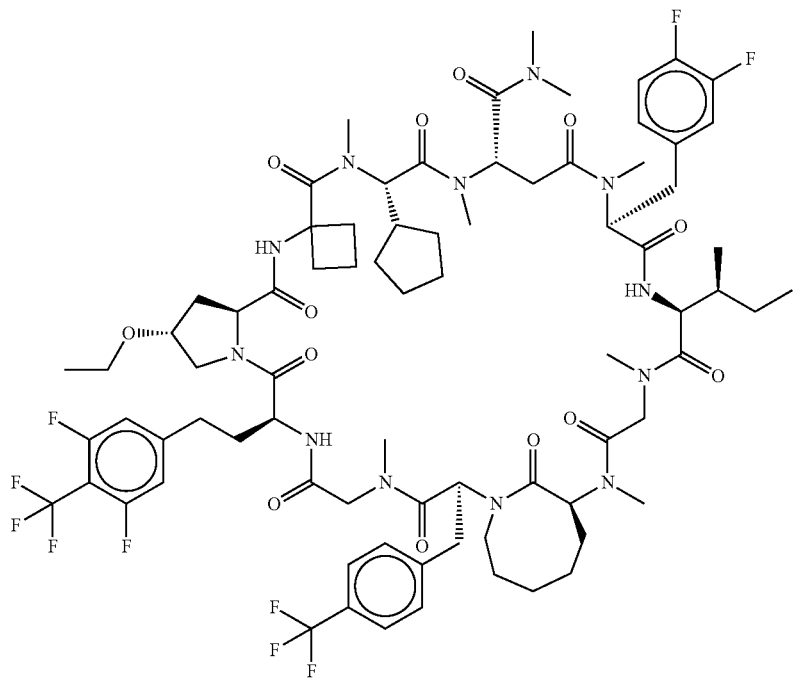 |
| PP0938 | 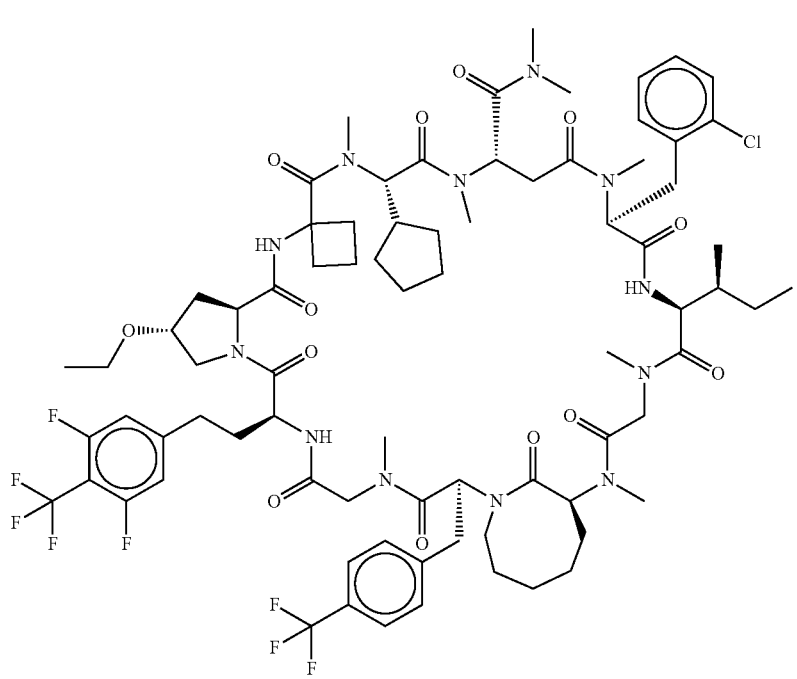 |

TABLE 38-continued
| Compound No. | Structural Formula |
|---|---|
| PP0939 | 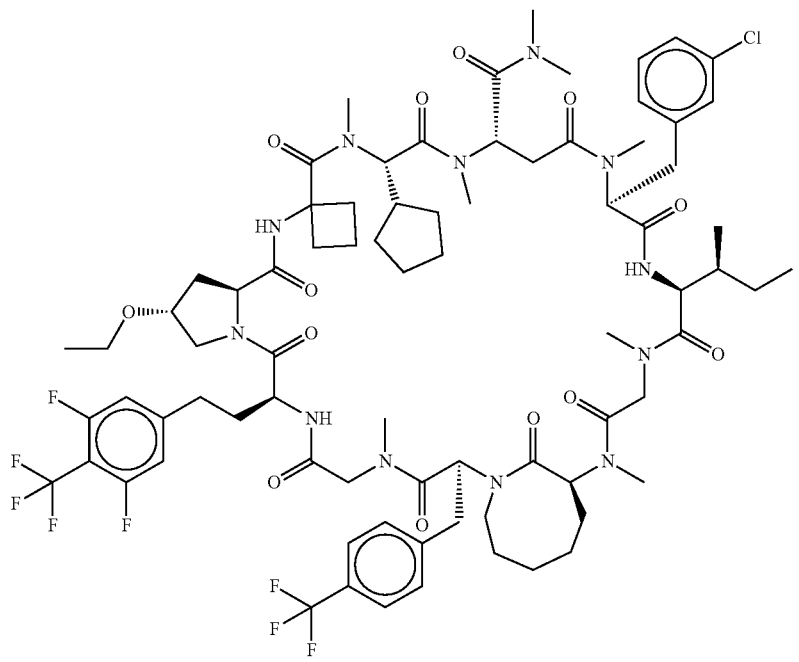 |
| PP0940 | 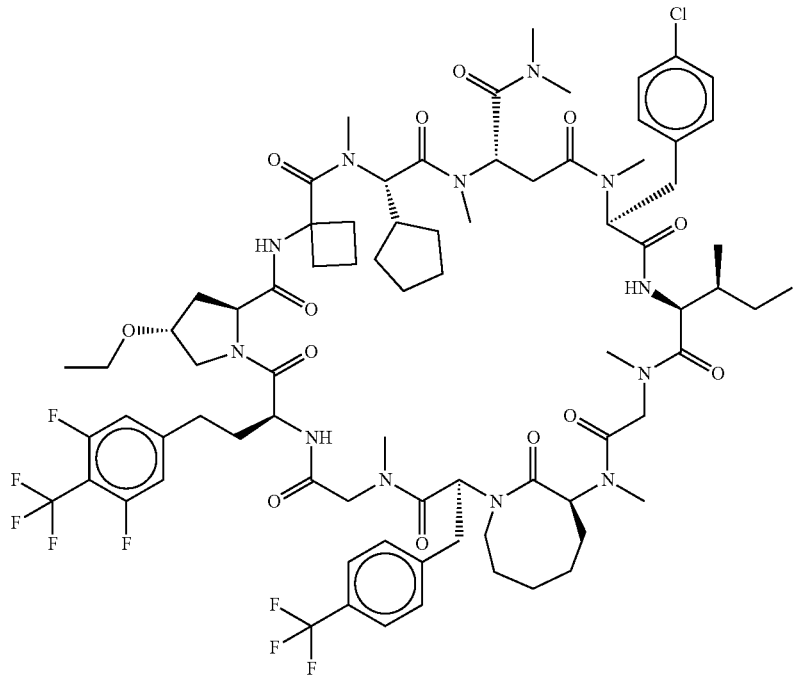 |

TABLE 38-continued
| Compound No. | Structural Formula |
|---|---|
| PP0941 | 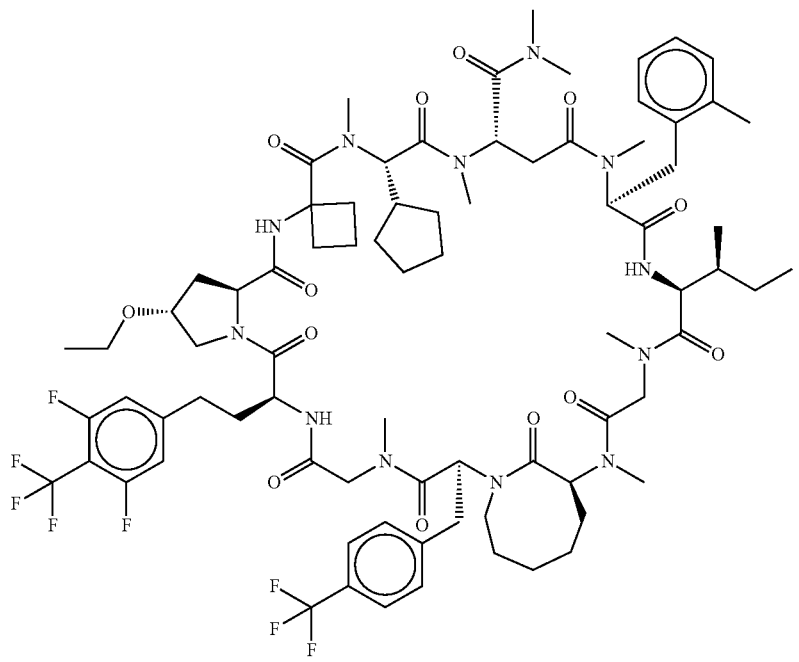 |
| PP0942 | 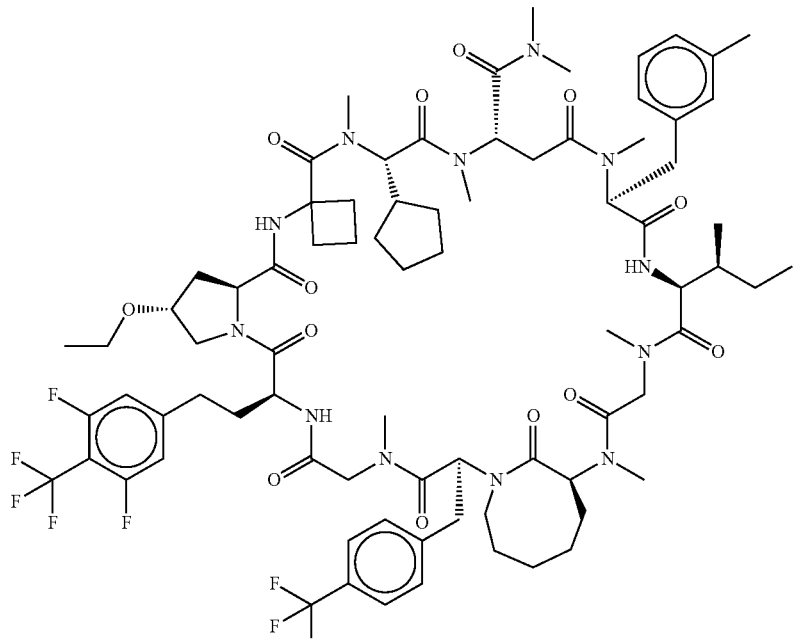 |

TABLE 38-continued
| Compound No. | Structural Formula |
|---|---|
| PP0943 | 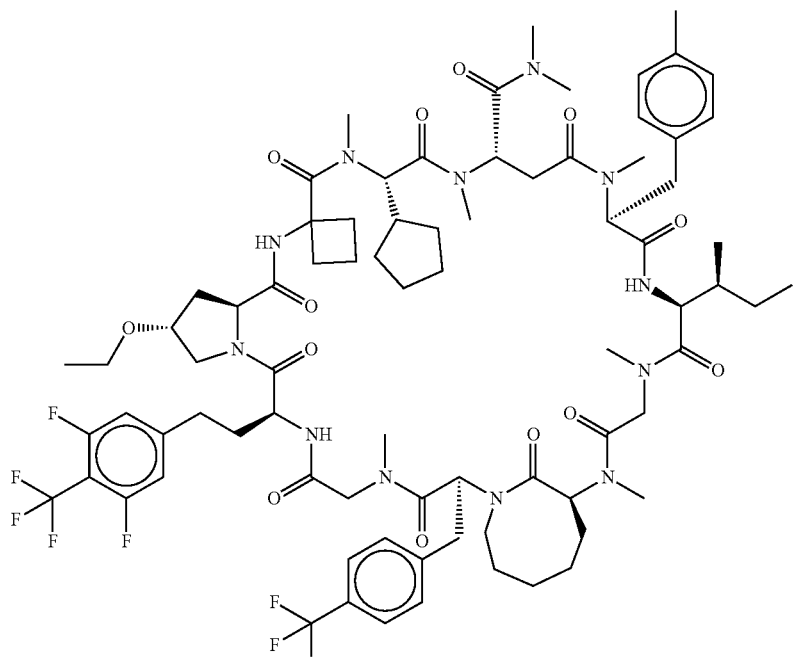 |
| PP0944 | 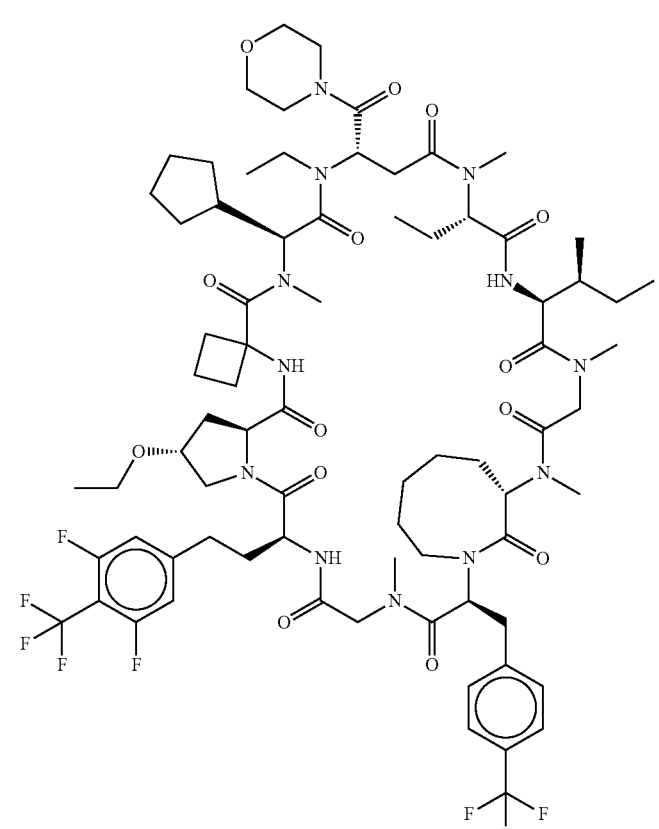 |

TABLE 38-continued

| Compound No. | Structural Formula |
|---|---|
| PP0945 | |
| PP0946 | |

TABLE 38-continued
| Compound No. | Structural Formula |
|---|---|
| PP0947 | 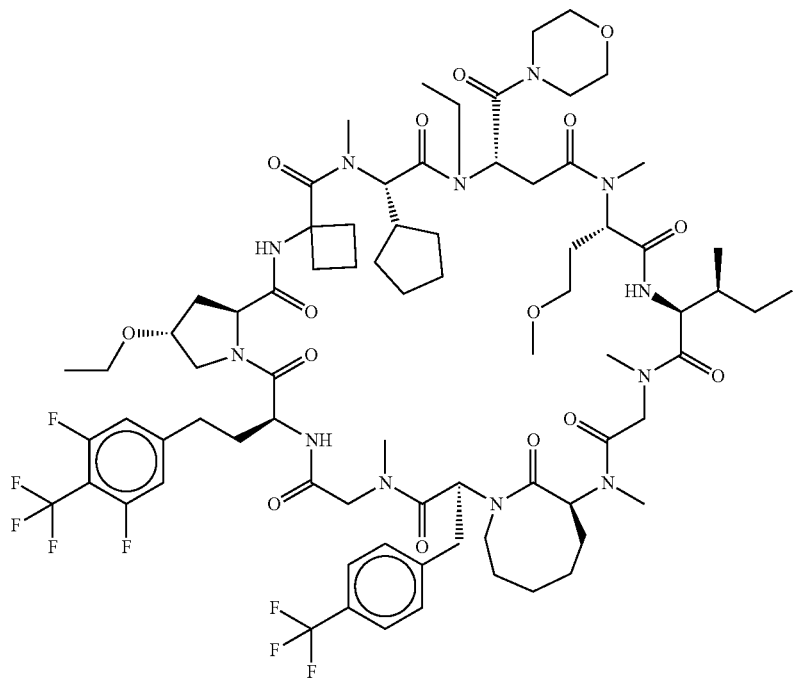 |
| PP0948 | 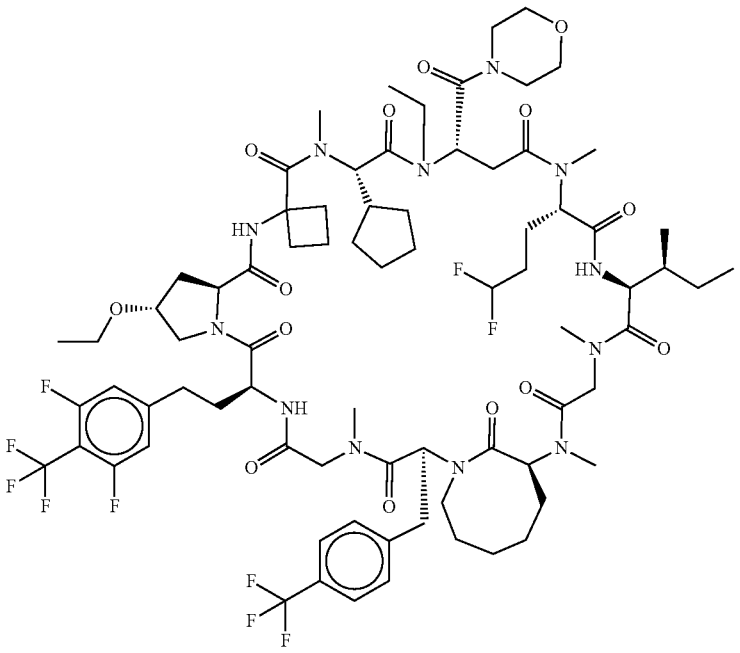 |

| Compound No. | Structural Formula |
|---|---|
| PP0949 | |
| PP0950 | |

TABLE 38-continued
| Compound No. | Structural Formula |
|---|---|
| PP0951 | 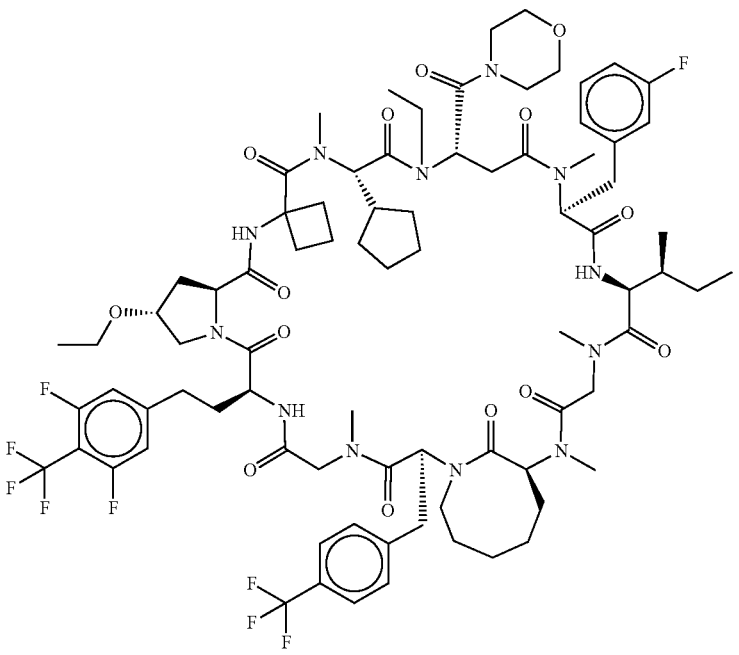 |
| PP0952 | 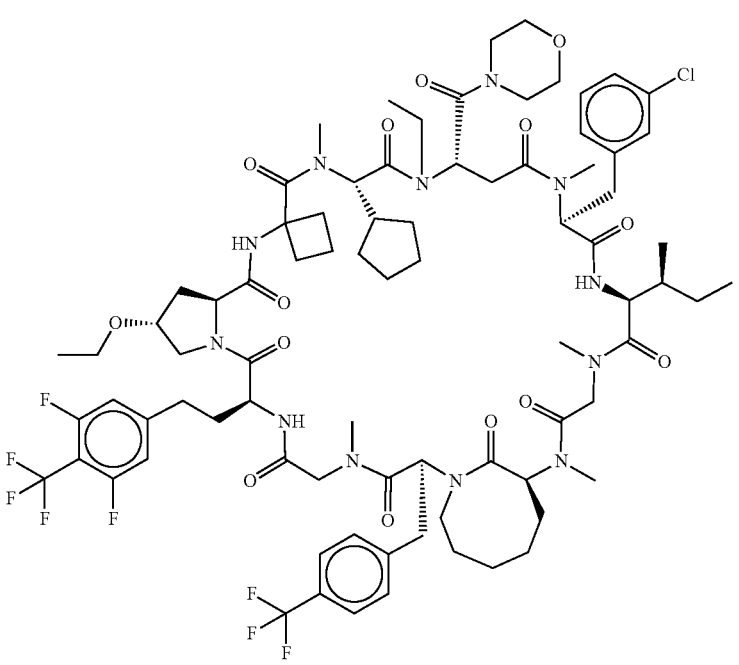 |

TABLE 38-continued

| Compound No. | Structural Formula |
|---|---|
| PP0953 | |
| PP0954 | |

TABLE 38-continued
| Compound No. | Structural Formula |
|---|---|
| PP0955 | 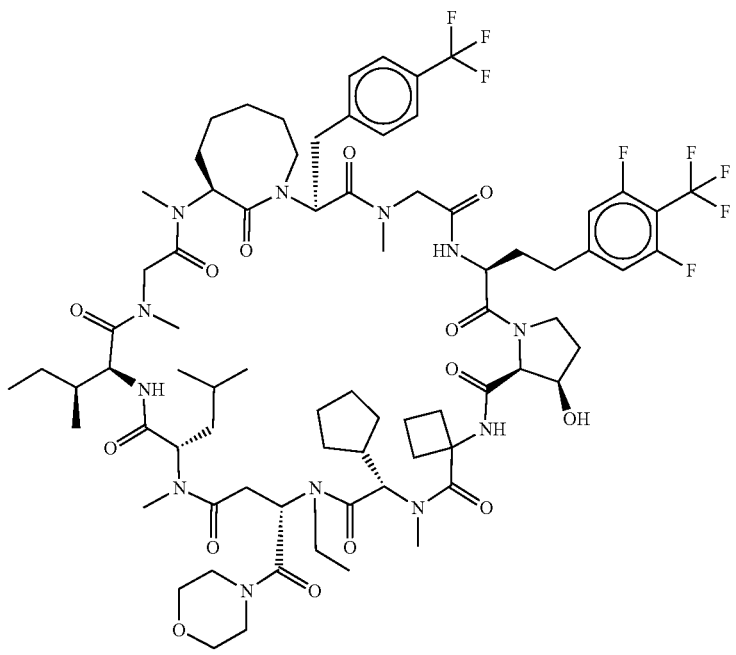 |
| PP0956 | 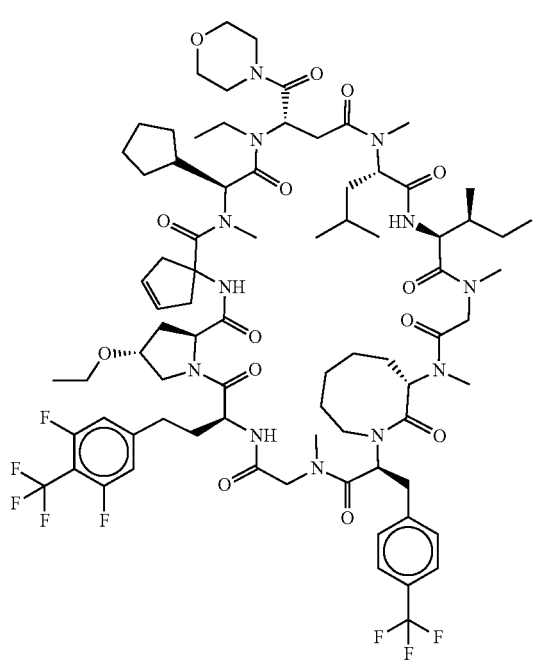 |

TABLE 38-continued

| Compound No. | Structural Formula |
|---|---|
| PP0958 | |
| PP0959 | |

TABLE 38-continued

| Compound No. | Structural Formula |
|---|---|
| PP0960 | |
| PP0961 | |

TABLE 38-continued
| Compound No. | Structural Formula |
|---|---|
| PP0962 | 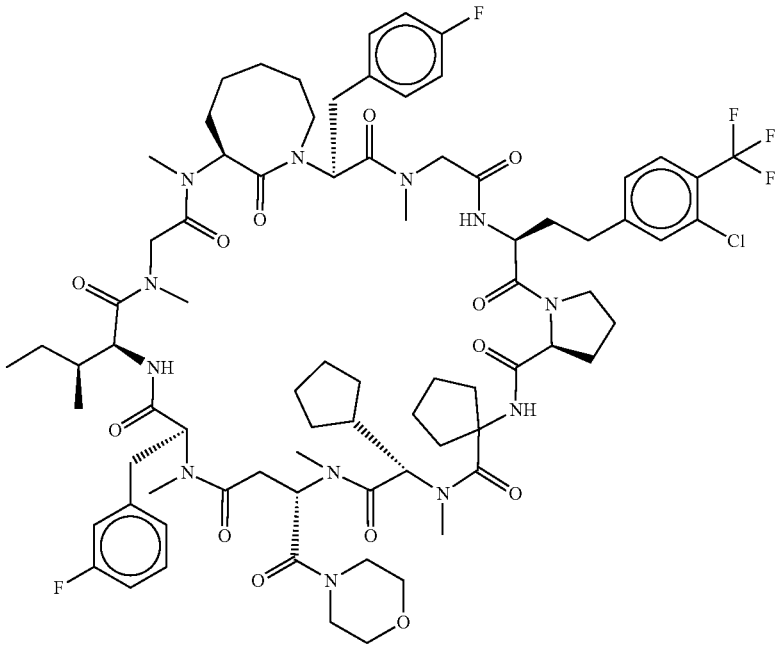 |
| PP0963 | 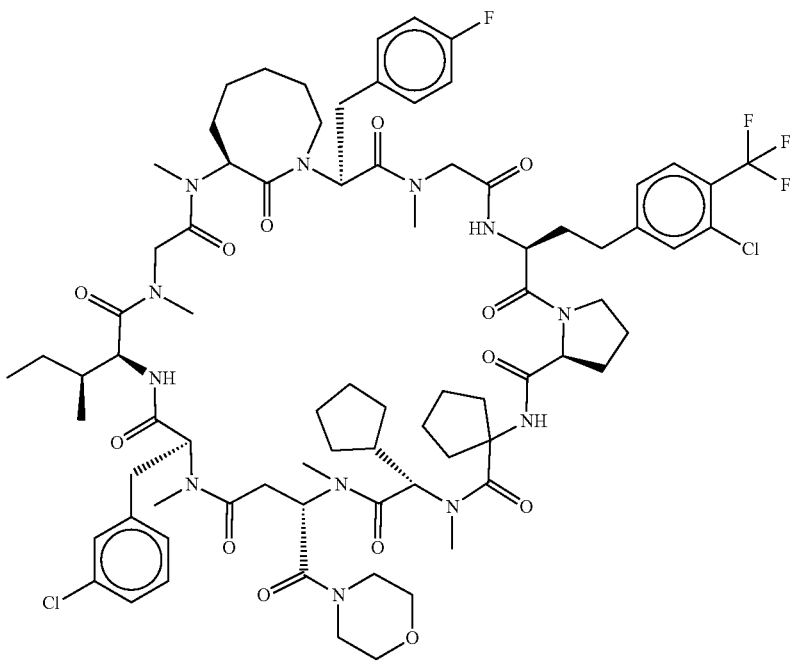 |

TABLE 38-continued

| Compound No. | Structural Formula |
|---|---|
| PP0964 | |
| PP0965 | |

TABLE 38-continued
| Compound No. | Structural Formula |
|---|---|
| PP0966 | 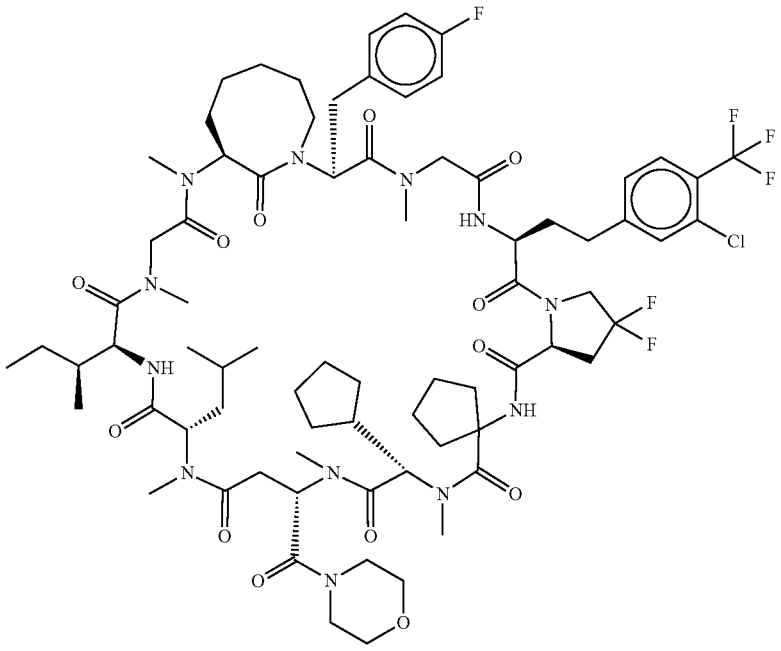 |
| PP0967 | 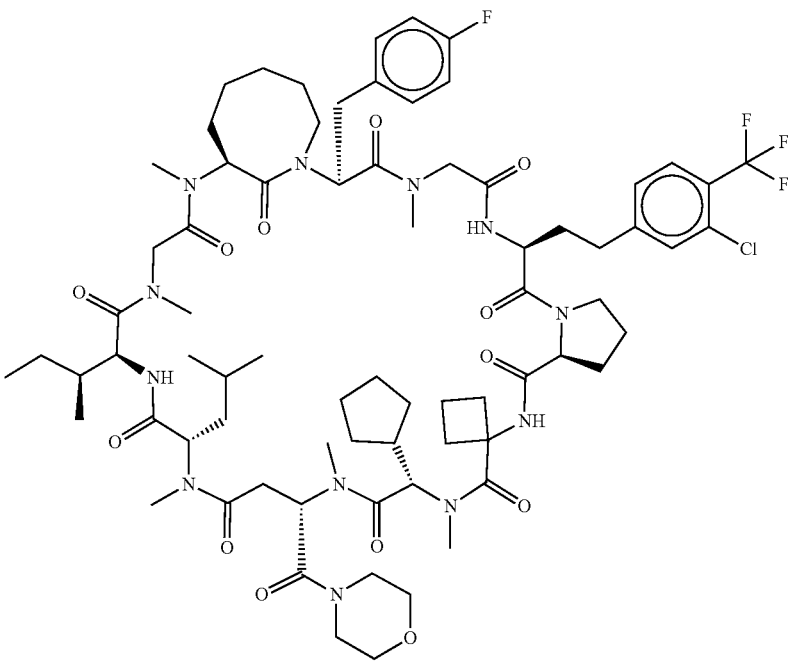 |

TABLE 38-continued
| Compound No. | Structural Formula |
|---|---|
| PP0968 | 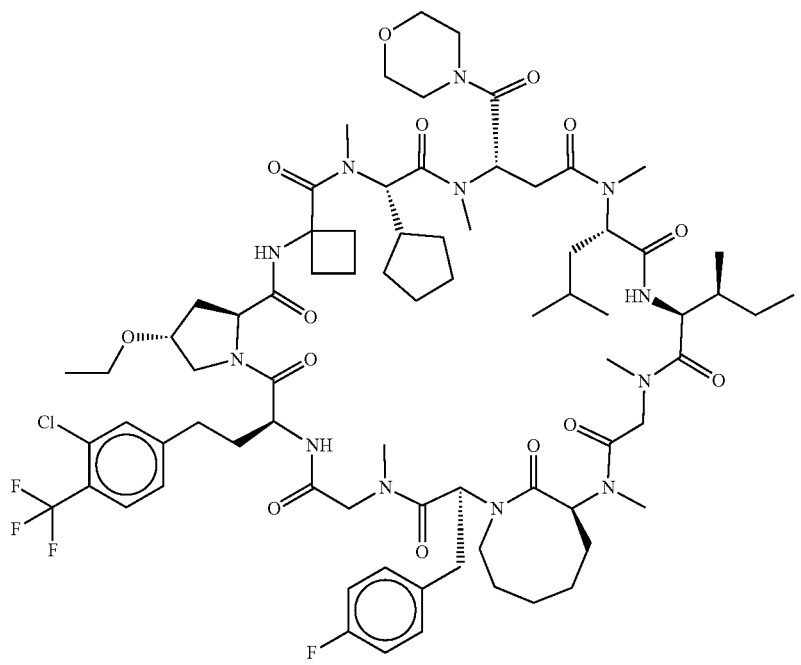 |
| PP0969 | 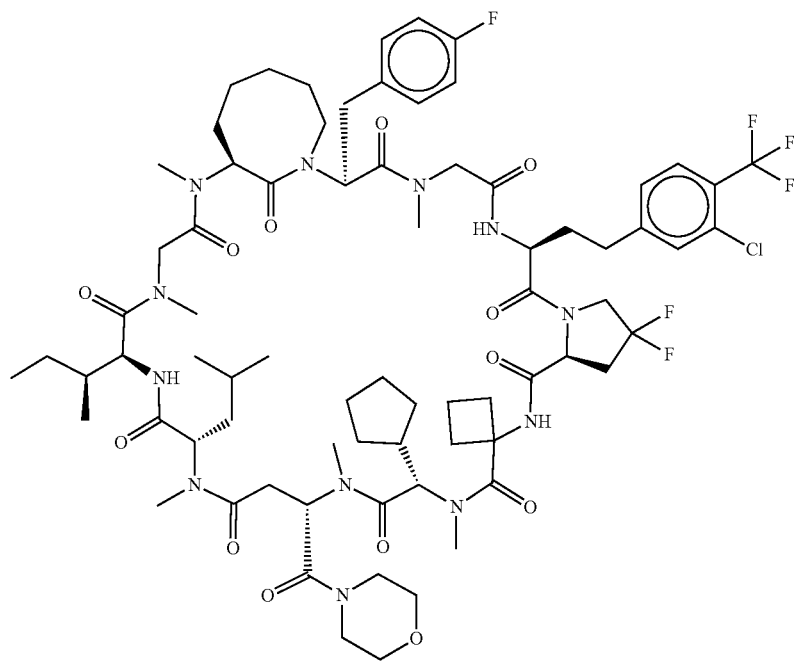 |

TABLE 38-continued

| Compound No. | Structural Formula |
|---|---|
| PP0970 | |
| PP0971 | |

TABLE 38-continued
| Compound No. | Structural Formula |
|---|---|
| PP0972 | 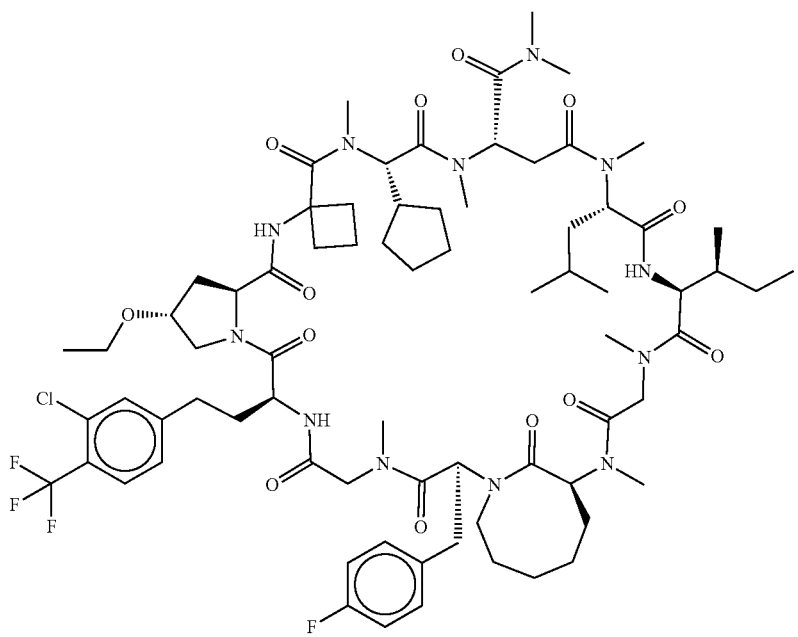 |
| PP0973 | 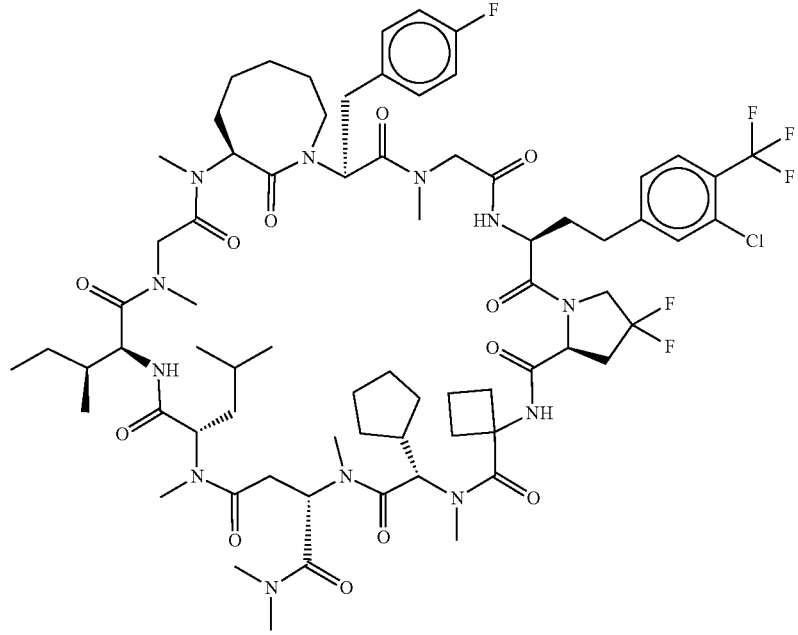 |

| Compound No. | Structural Formula |
|---|---|
| PP0975 | 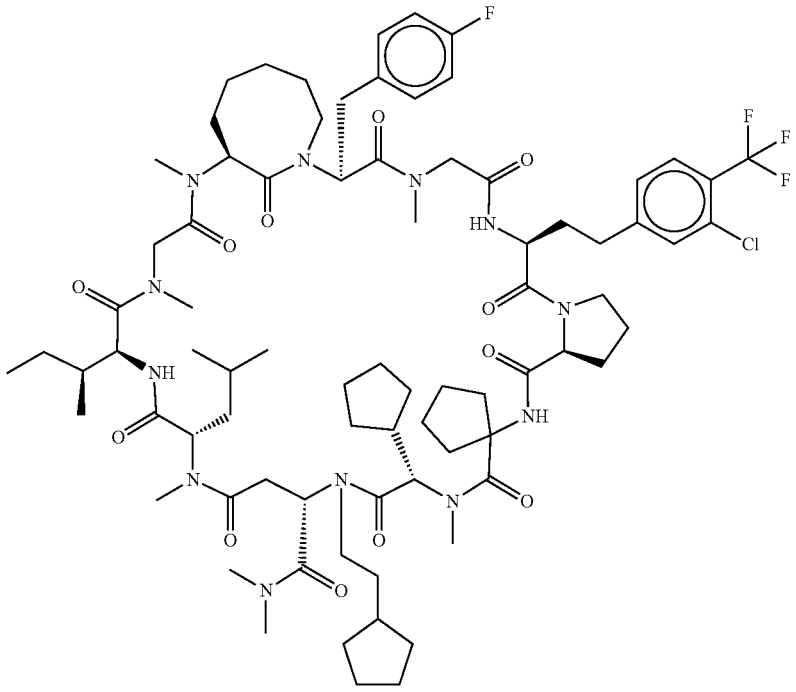 |
| PP0976 | 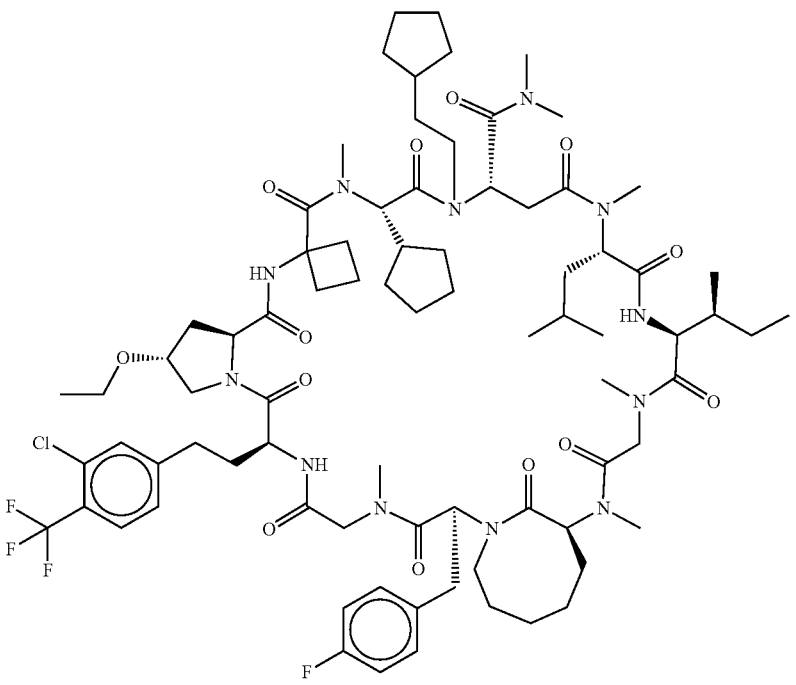 |

TABLE 38-continued

| Compound No. | Structural Formula |
|---|---|
| PP0977 | (structural formula) |
| PP0978 | (structural formula) |

TABLE 38-continued
| Compound No. | Structural Formula |
|---|---|
| PP0979 | 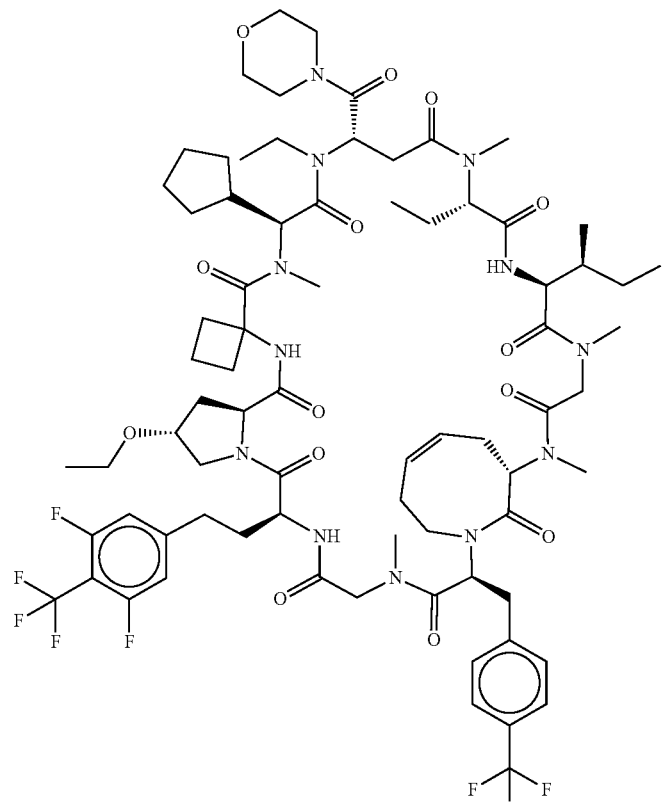 |
| PP0980 | 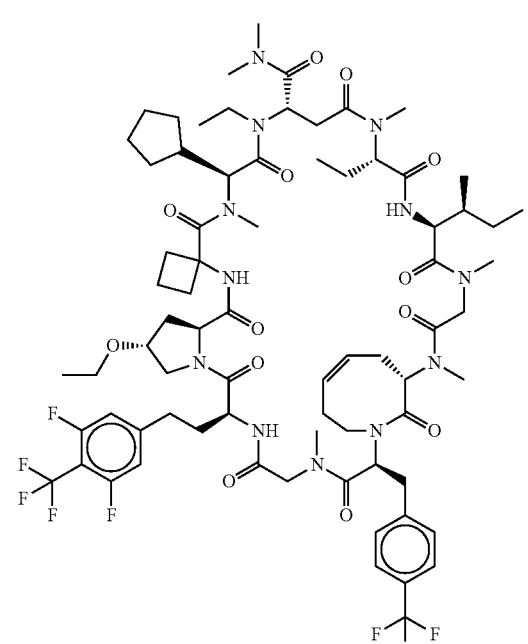 |

TABLE 38-continued
| Compound No. | Structural Formula |
|---|---|
| PP0981 | 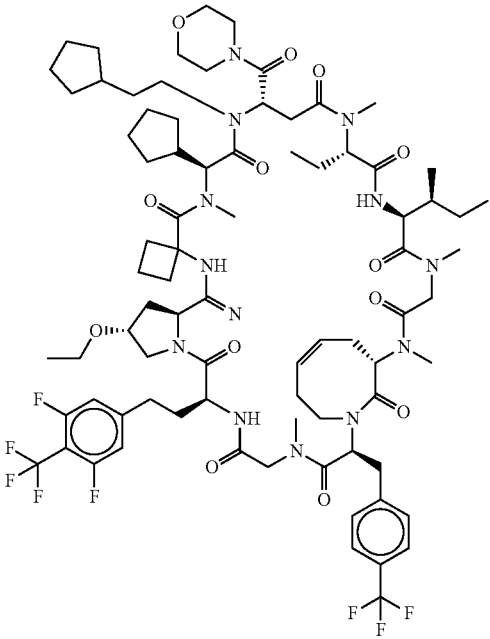 |
| PP0982 | 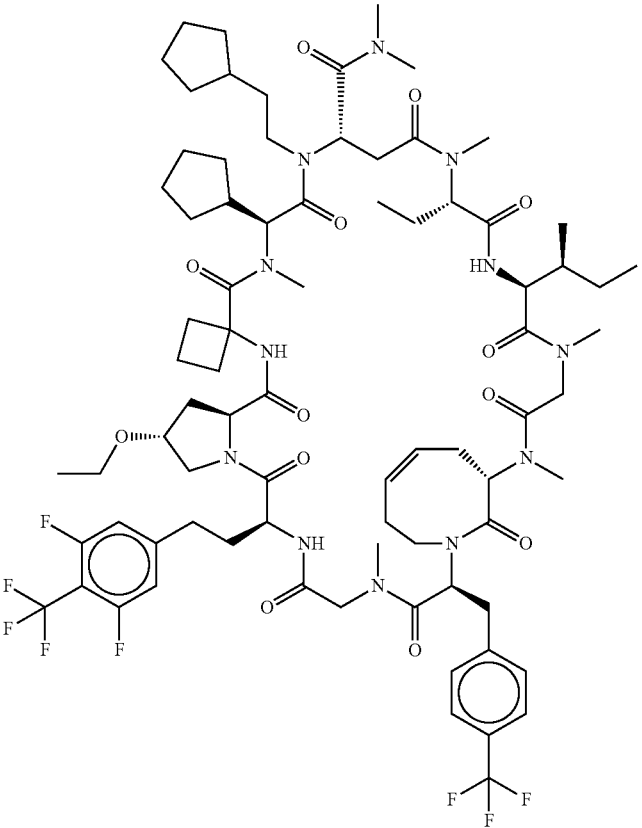 |

TABLE 38-continued
| Compound No. | Structural Formula |
|---|---|
| PP0983 | 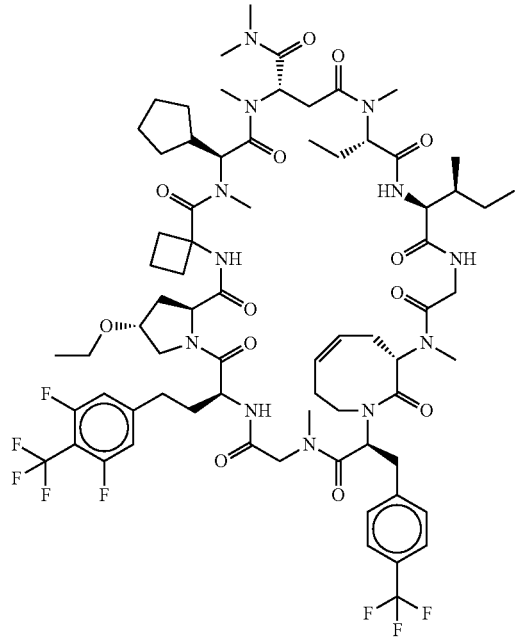 |
| PP0984 | 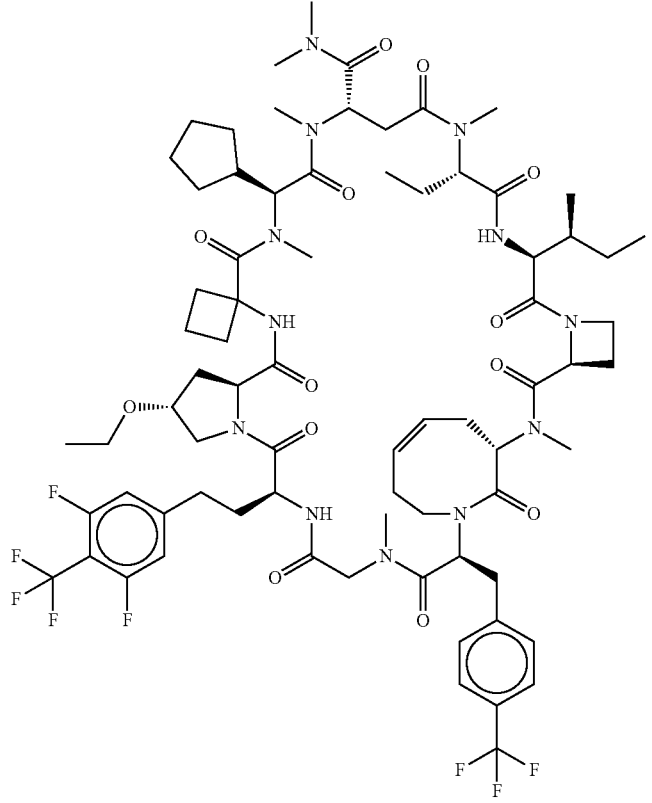 |

TABLE 38-continued

| Compound No. | Structural Formula |
| --- | --- |
| PP0985 | |
| PP0986 | |

TABLE 38-continued
| Compound No. | Structural Formula |
|---|---|
| PP0987 | 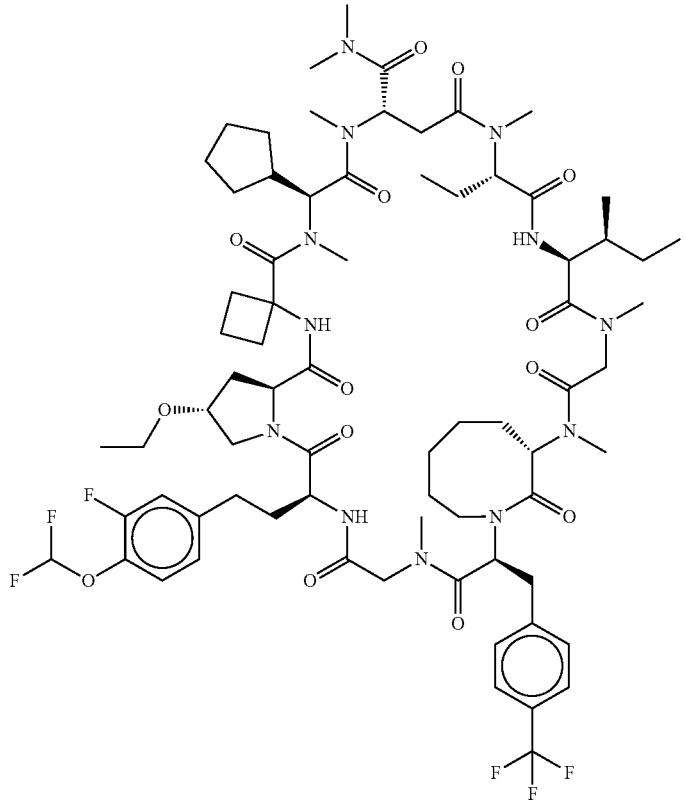 |
| PP0988 | 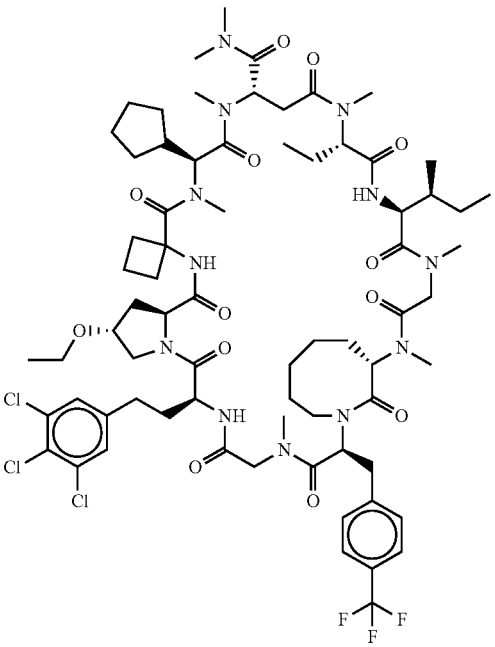 |

TABLE 38-continued
| Compound No. | Structural Formula |
|---|---|
| PP0989 | 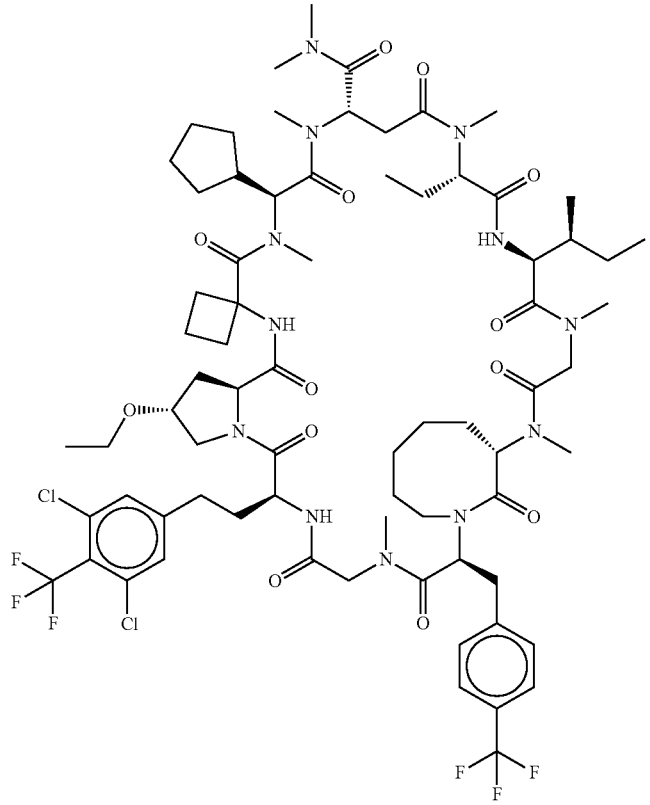 |
| PP0992 | 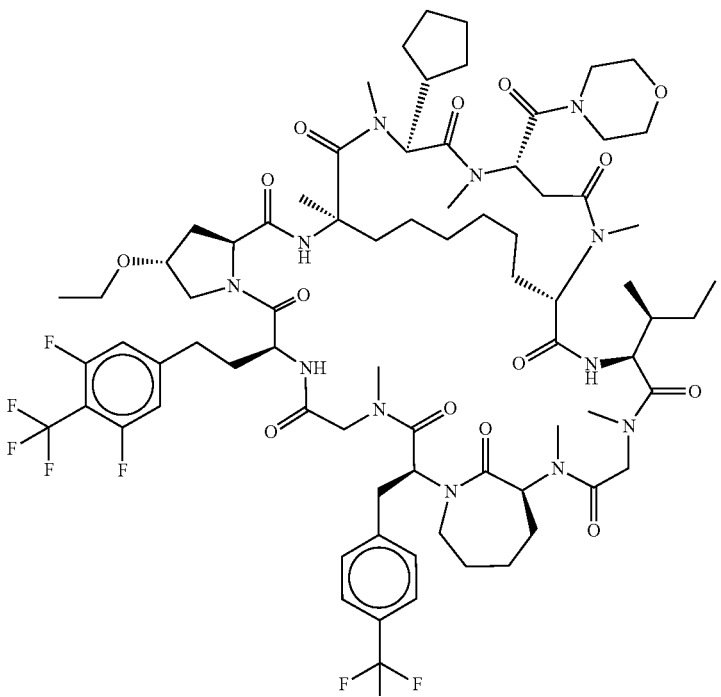 |

TABLE 38-continued

| Compound No. | Structural Formula |
|---|---|
| PP0993 | |
| PP0997 | |

TABLE 38-continued

| Compound No. | Structural Formula |
|---|---|
| PP0998 | |
| PP0999 | |

TABLE 38-continued
| Compound No. | Structural Formula |
|---|---|
| PP1000 | 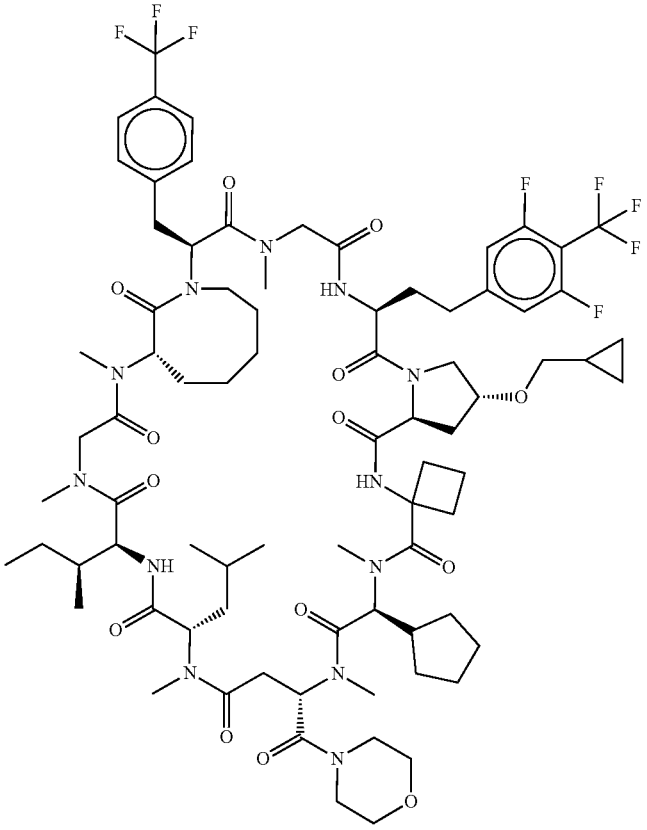 |
| PP1001 | 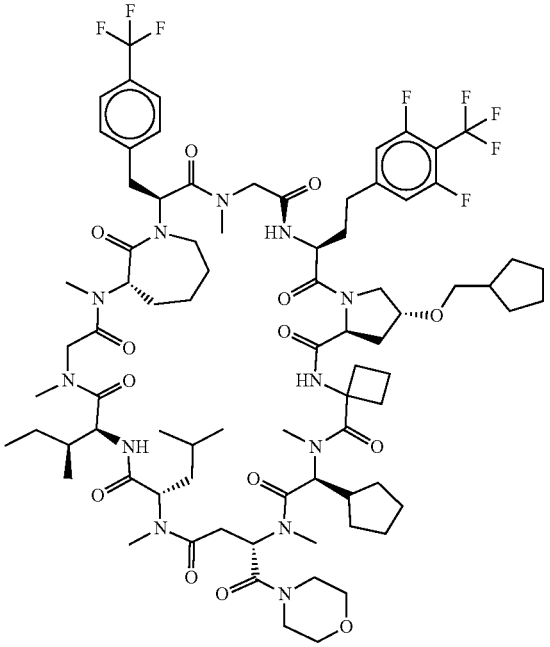 |

TABLE 38-continued

| Compound No. | Structural Formula |
|---|---|
| PP1002 | |
| PP1003 | |

TABLE 38-continued
| Compound No. | Structural Formula |
|---|---|
| PP1004 | 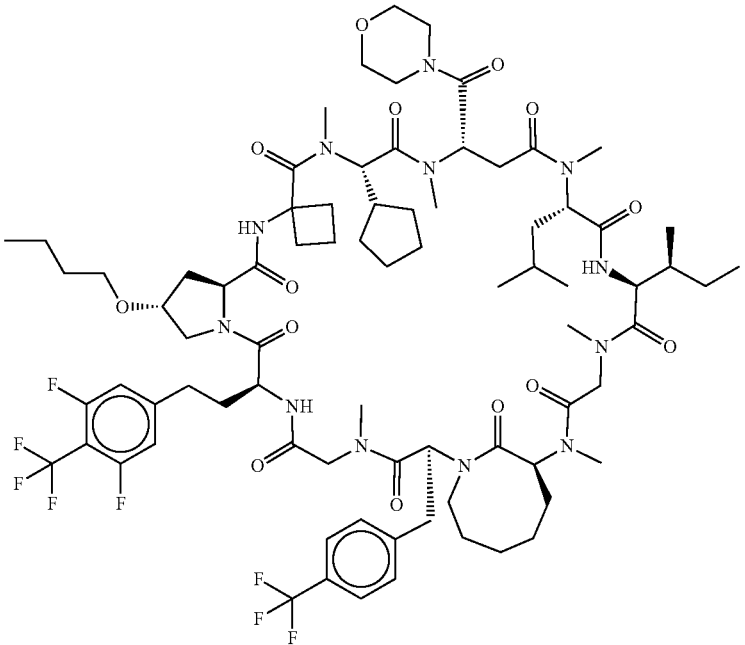 |
| PP1005 | 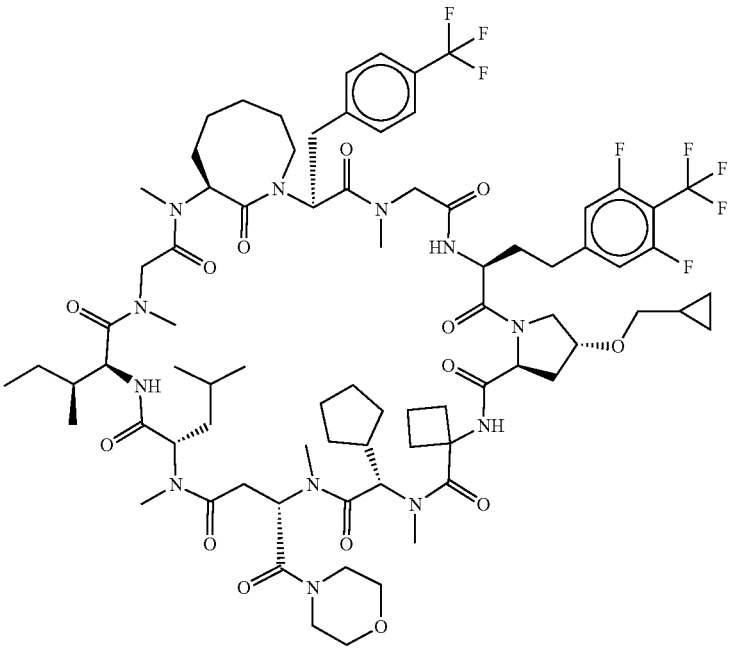 |

TABLE 38-continued

| Compound No. | Structural Formula |
|---|---|
| PP1006 | |
| PP1008 | |

TABLE 38-continued

| Compound No. | Structural Formula |
|---|---|
| PP1009 | |
| PP1010 | |

TABLE 38-continued

| Compound No. | Structural Formula |
|---|---|
| PP1011 | |
| PP1012 | |

TABLE 38-continued

| Compound No. | Structural Formula |
|---|---|
| PP1013 | |
| PP1014 | |

TABLE 38-continued
| Compound No. | Structural Formula |
|---|---|
| PP1015 | 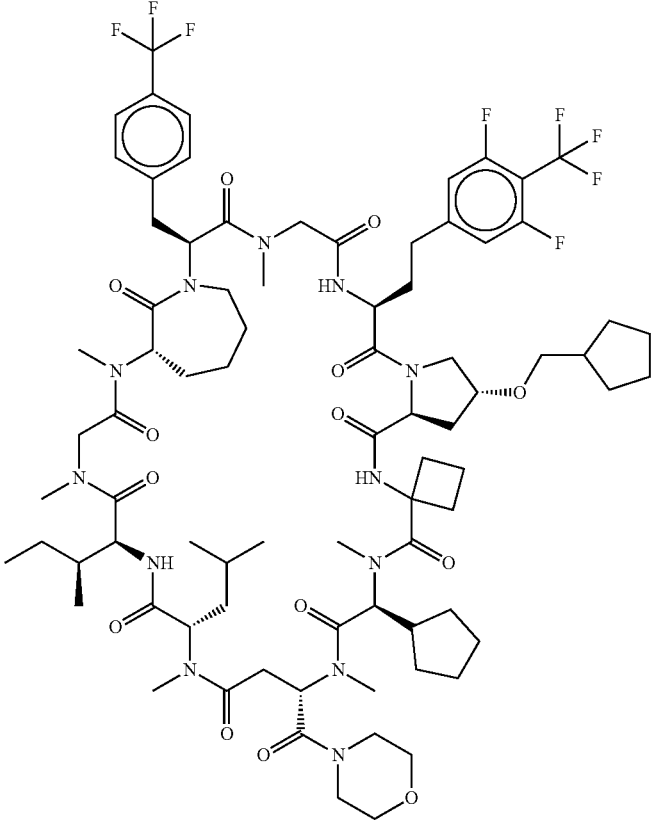 |
| PP1016 | 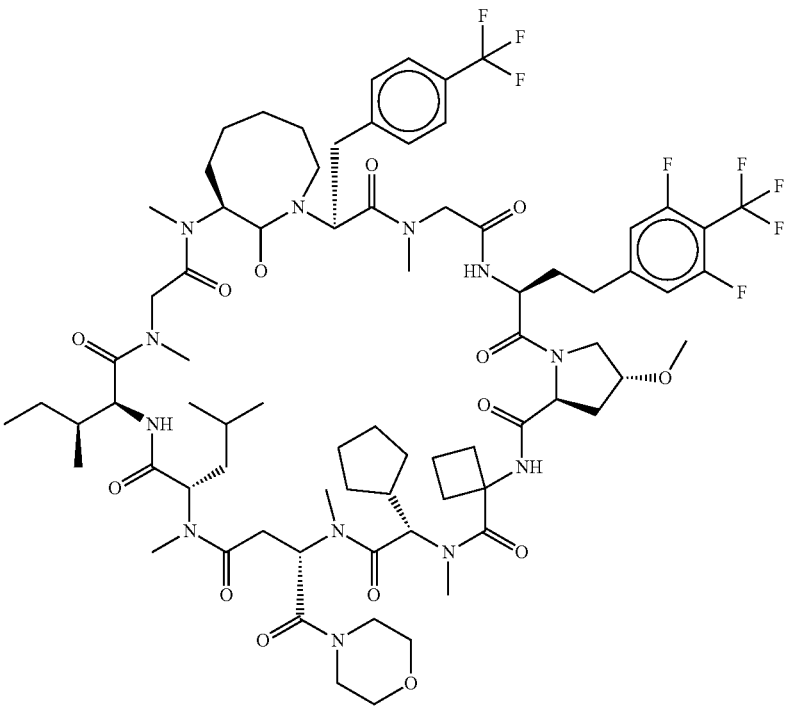 |

TABLE 38-continued
| Compound No. | Structural Formula |
| --- | --- |
| PP1017 | 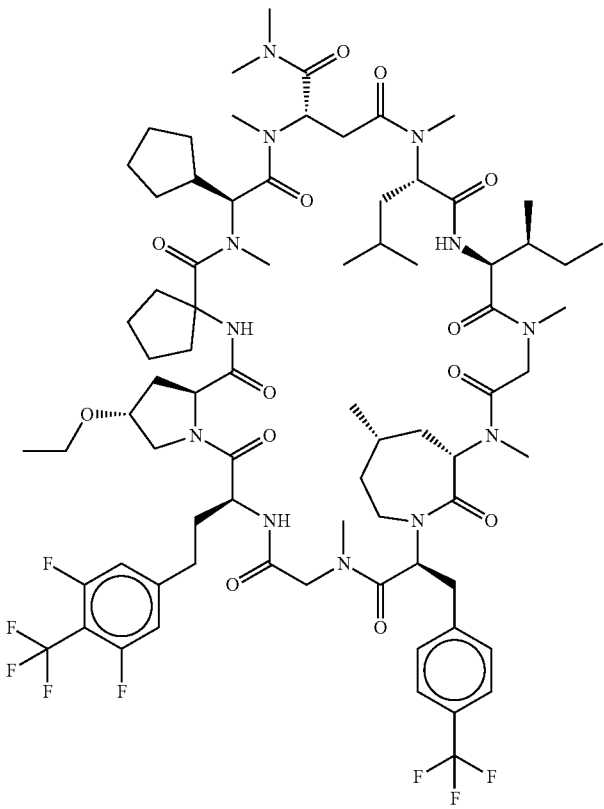 |
| PP1018 | 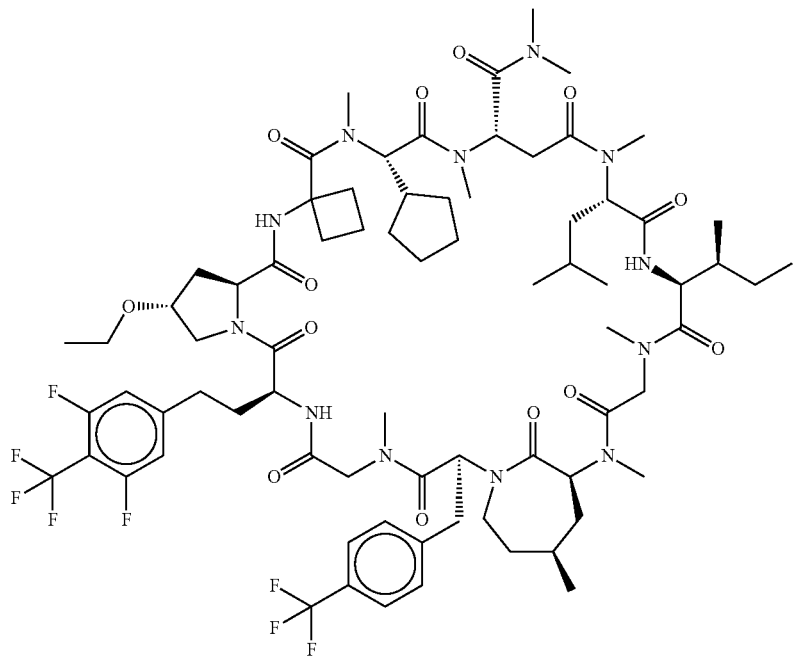 |

TABLE 38-continued
| Compound No. | Structural Formula |
| --- | --- |
| PP1019 | 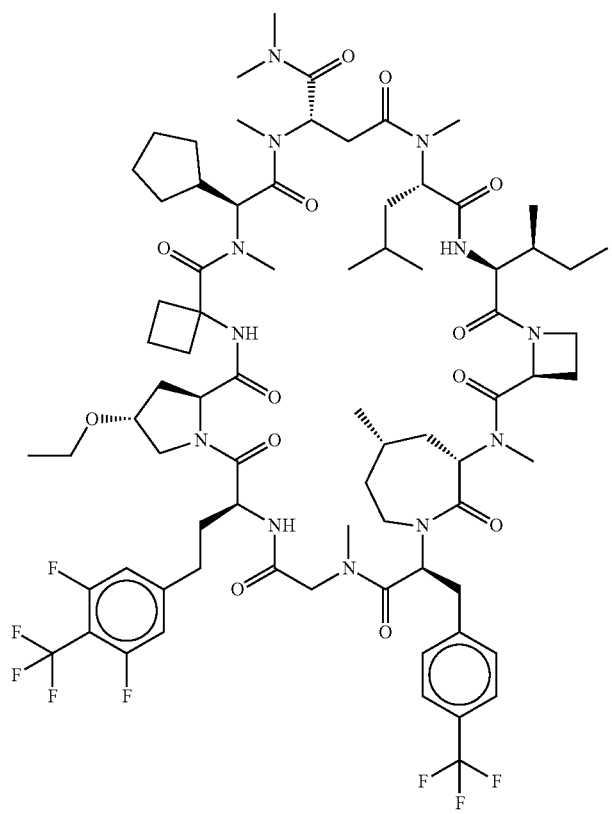 |
| PP1020 | 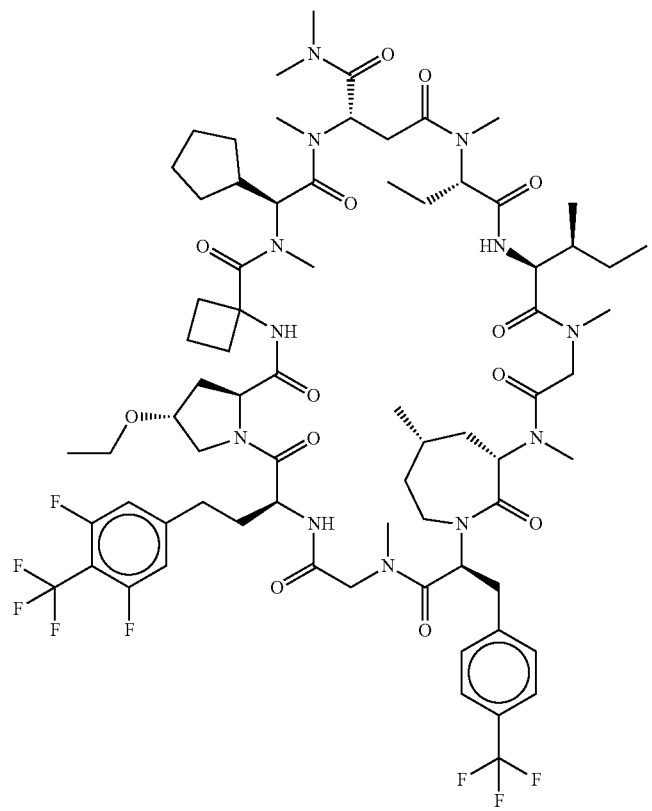 |

TABLE 38-continued

| Compound No. | Structural Formula |
|---|---|
| PP1021 | |
| PP1022 | |

TABLE 38-continued
| Compound No. | Structural Formula |
|---|---|
| PP1024 | 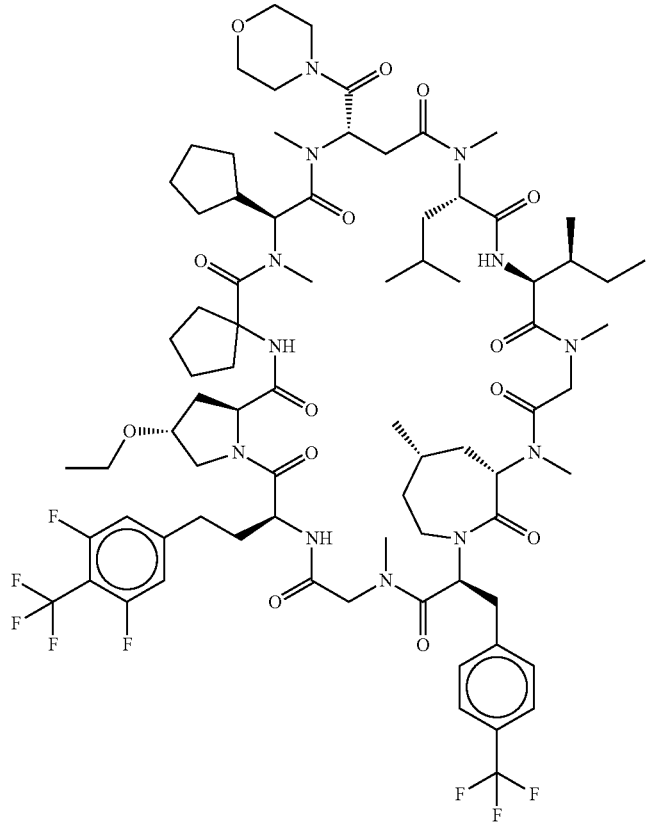 |
| PP1025 | 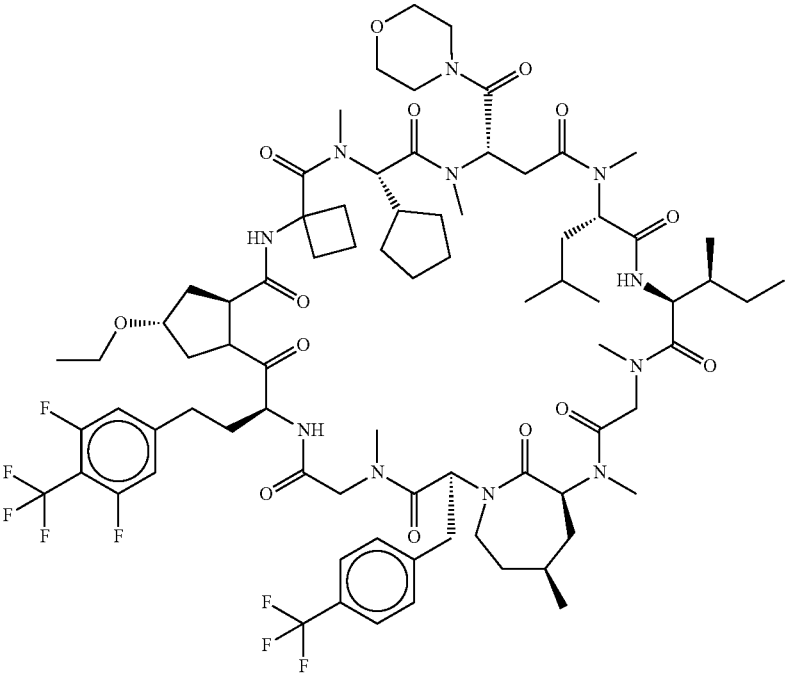 |

TABLE 38-continued

| Compound No. | Structural Formula |
|---|---|
| PP1026 | |
| PP1027 | |

TABLE 38-continued
| Compound No. | Structural Formula |
|---|---|
| PP1028 | 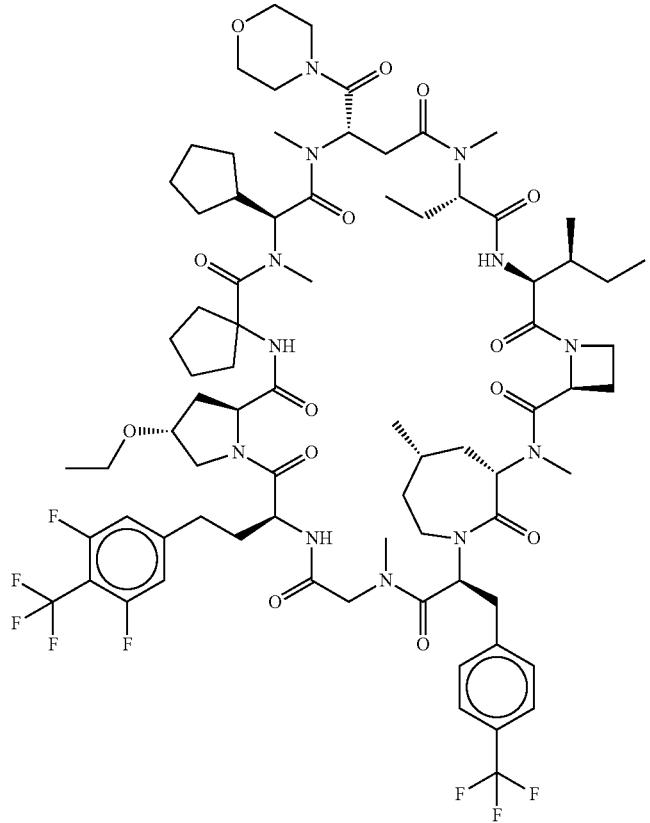 |
| PP1029 | 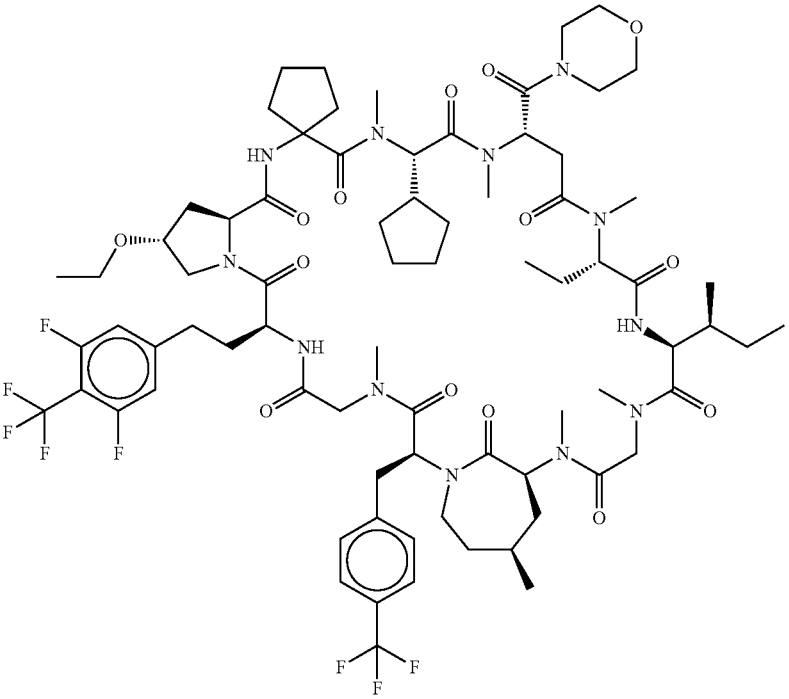 |

TABLE 38-continued
| Compound No. | Structural Formula |
|---|---|
| PP1030 | 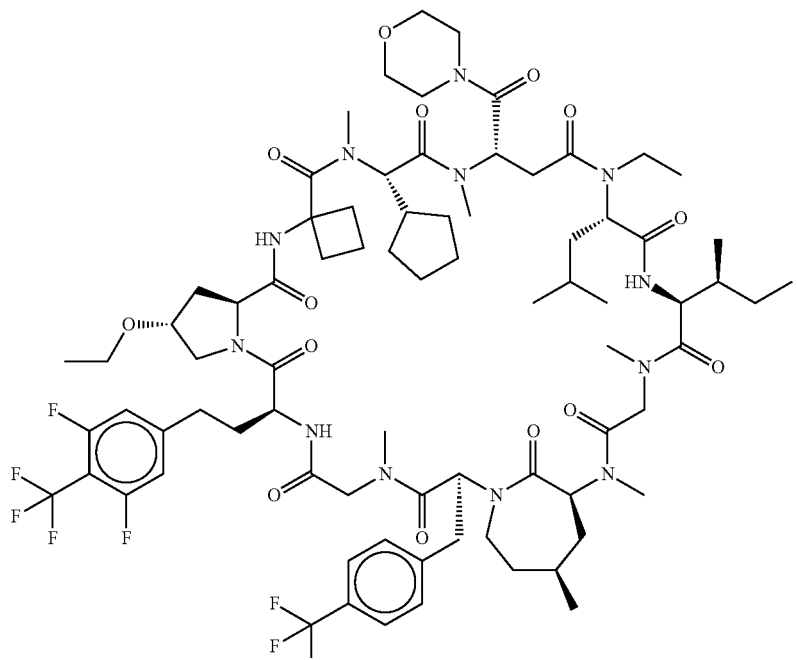 |
| PP1031 | 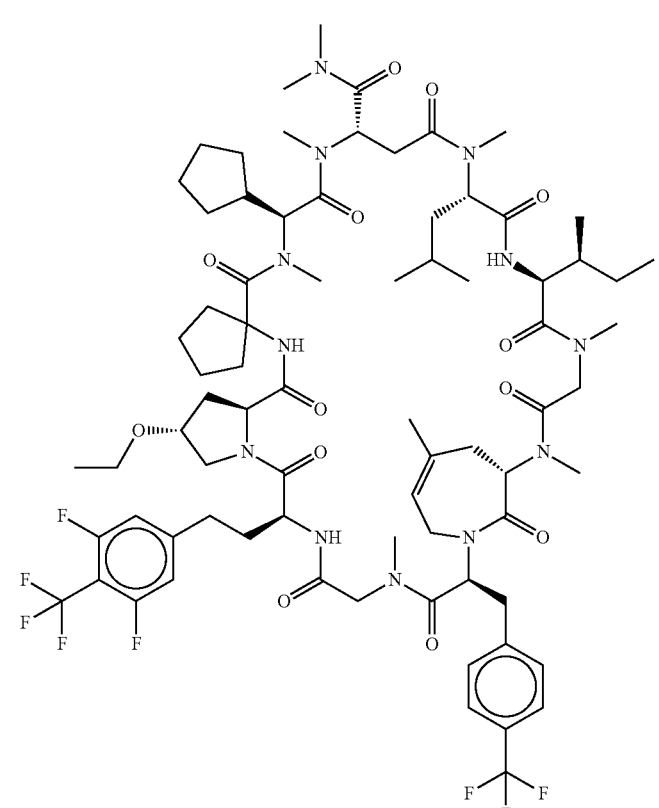 |

TABLE 38-continued
| Compound No. | Structural Formula |
| --- | --- |
| PP1032 | 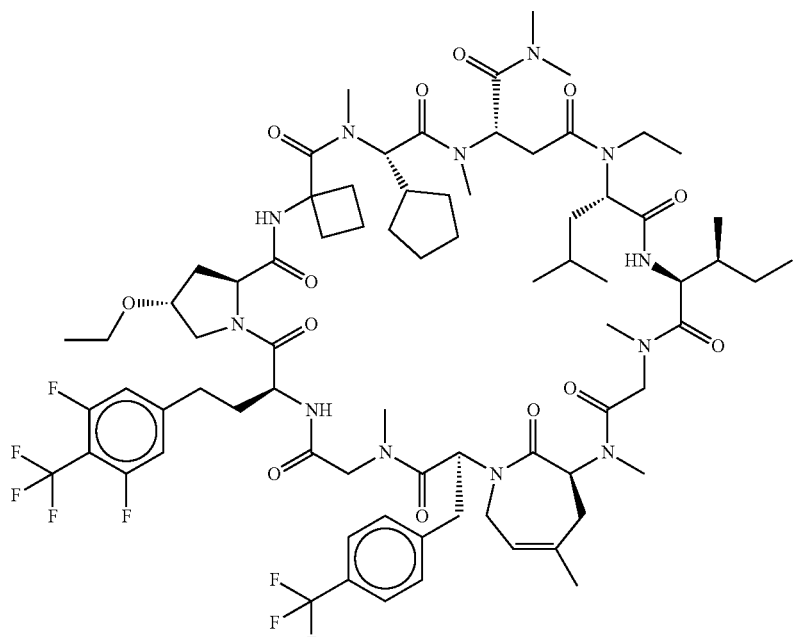 |
| PP1033 | 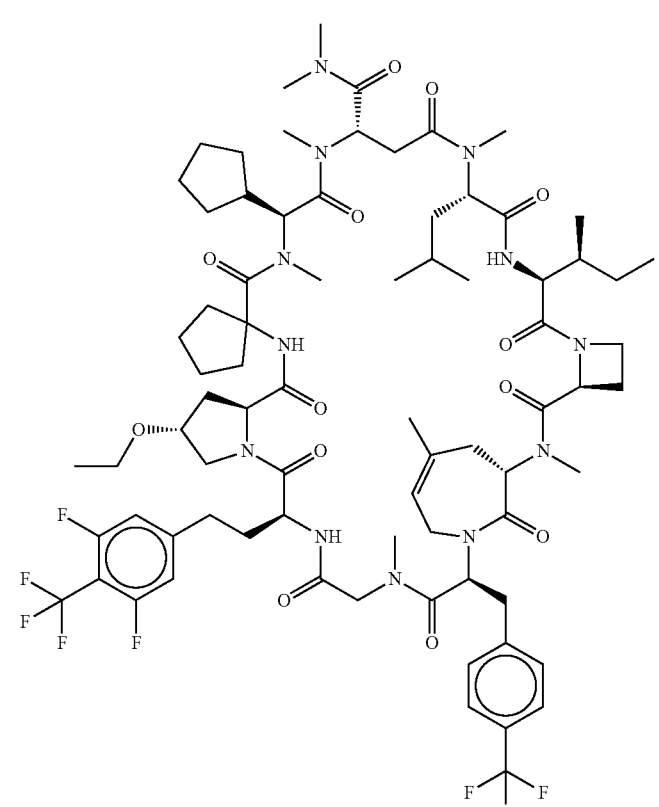 |

| Compound No. | Structural Formula |
|---|---|
| PP1034 | 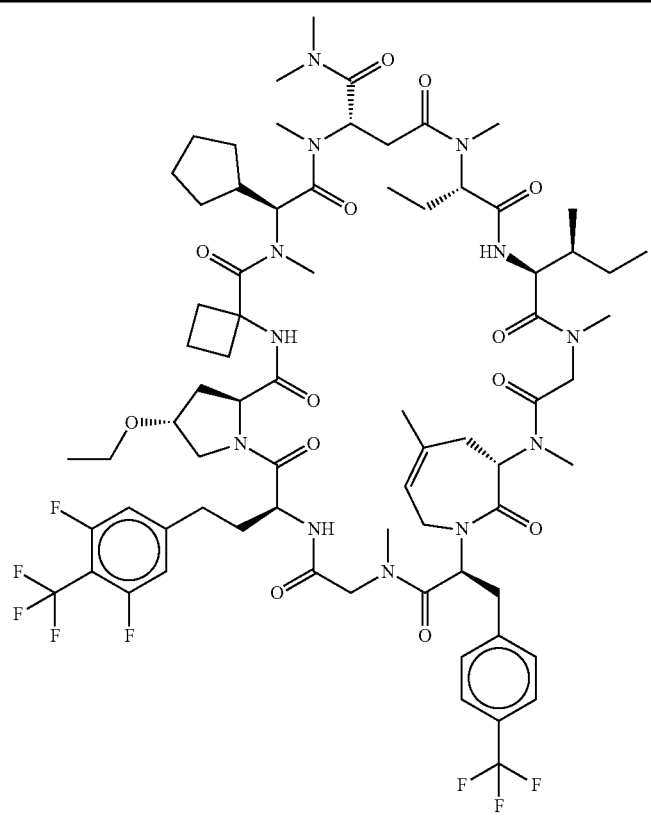 |
| PP1035 | 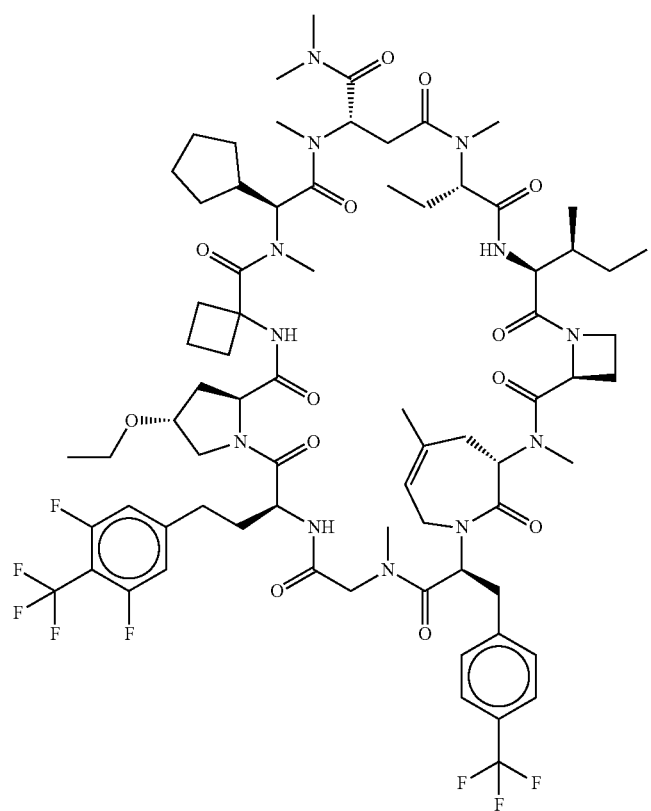 |

TABLE 38-continued

| Compound No. | Structural Formula |
|---|---|
| PP1036 | |
| PP1037 | |

TABLE 38-continued
| Compound No. | Structural Formula |
|---|---|
| PP1038 | 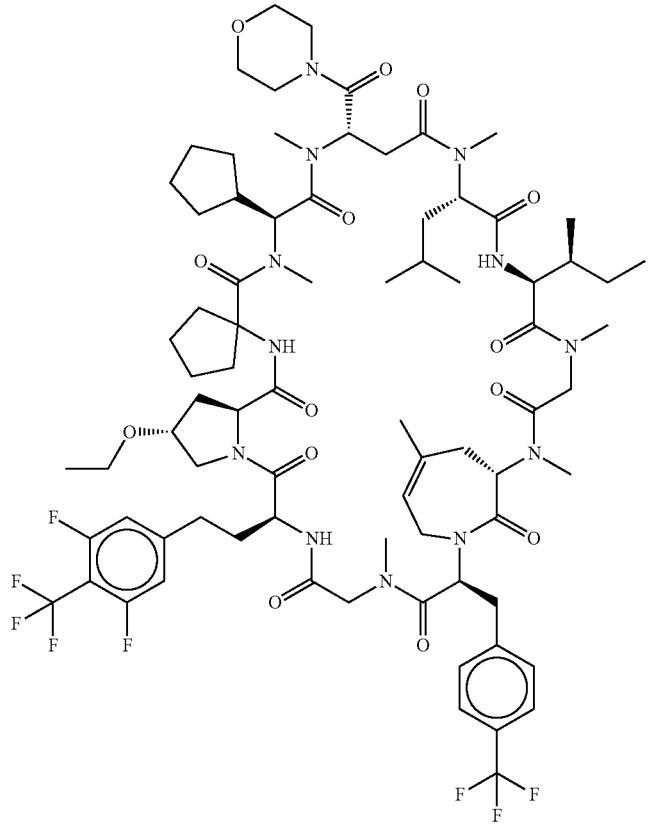 |
| PP1039 | 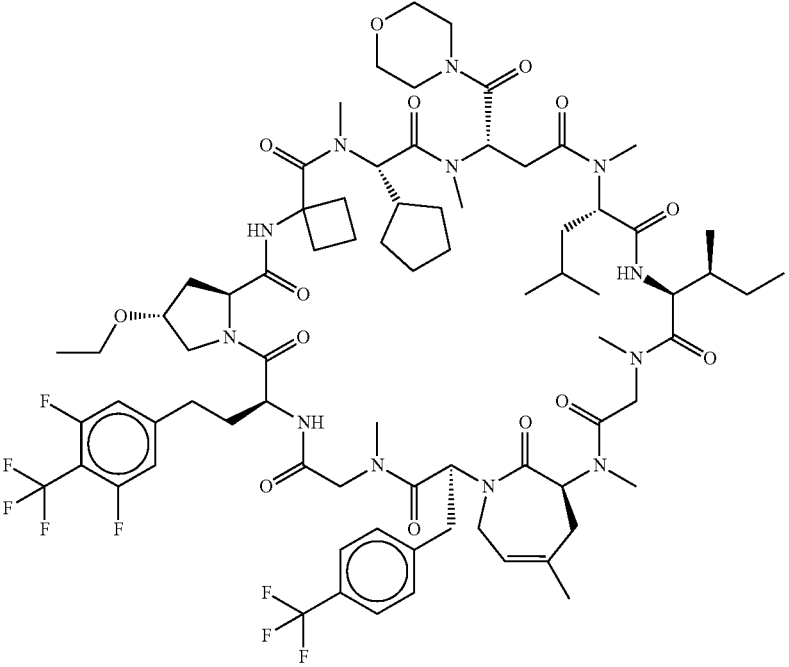 |

TABLE 38-continued
| Compound No. | Structural Formula |
|---|---|
| PP1040 | 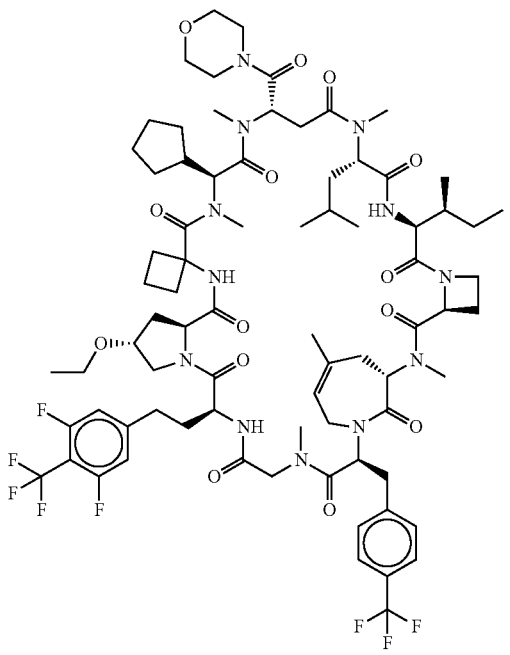 |
| PP1041 | 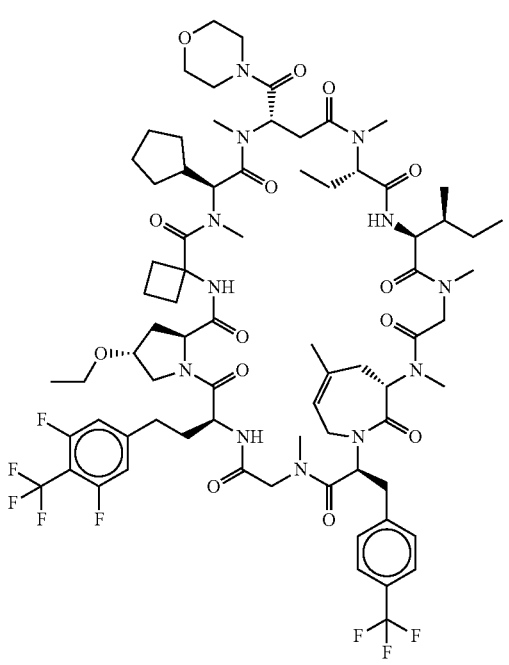 |

TABLE 38-continued
| Compound No. | Structural Formula |
|---|---|
| PP1042 | 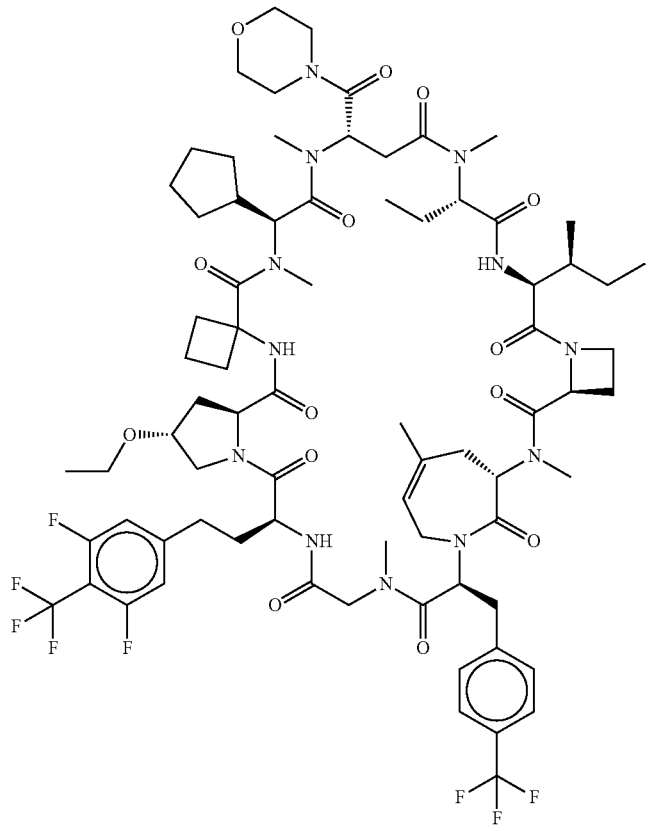 |
| PP1043 | 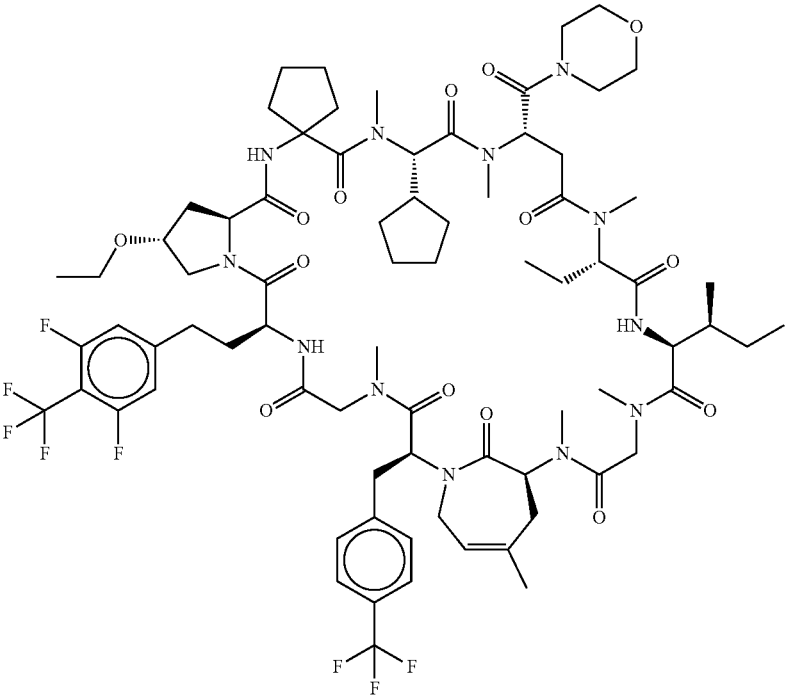 |

TABLE 38-continued

| Compound No. | Structural Formula |
|---|---|
| PP1044 | |
| PP1045 | |

TABLE 38-continued
| Compound No. | Structural Formula |
|---|---|
| PP1046 | 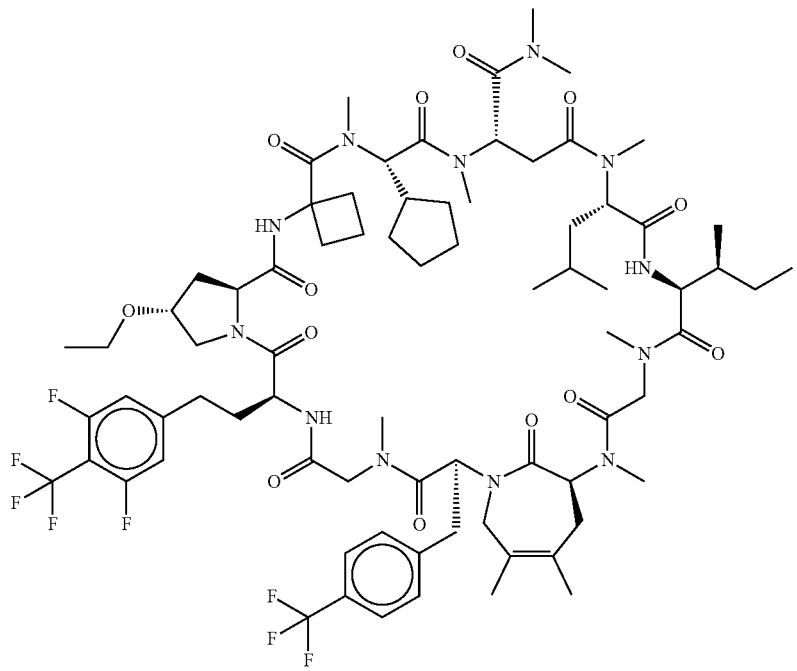 |
| PP1047 | 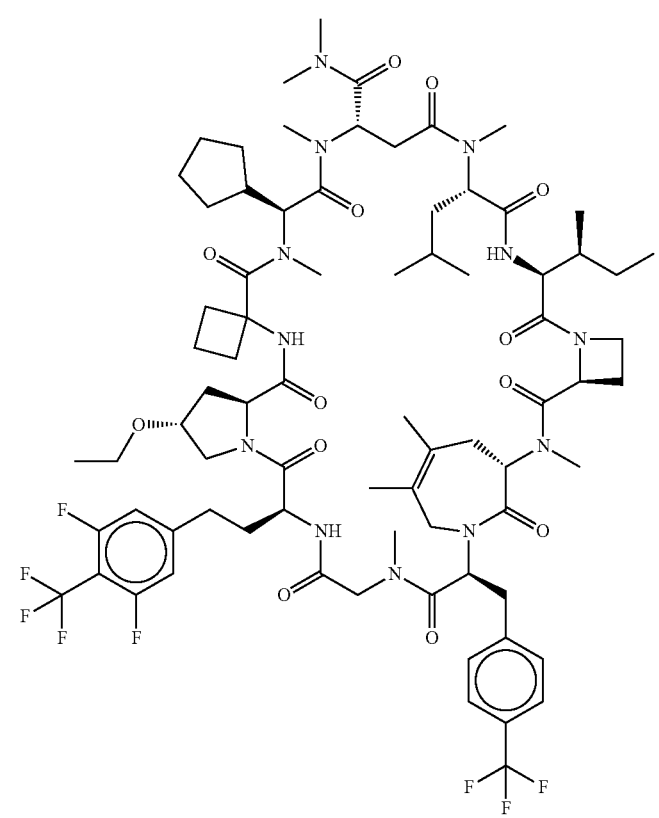 |

TABLE 38-continued
| Compound No. | Structural Formula |
|---|---|
| PP1048 | 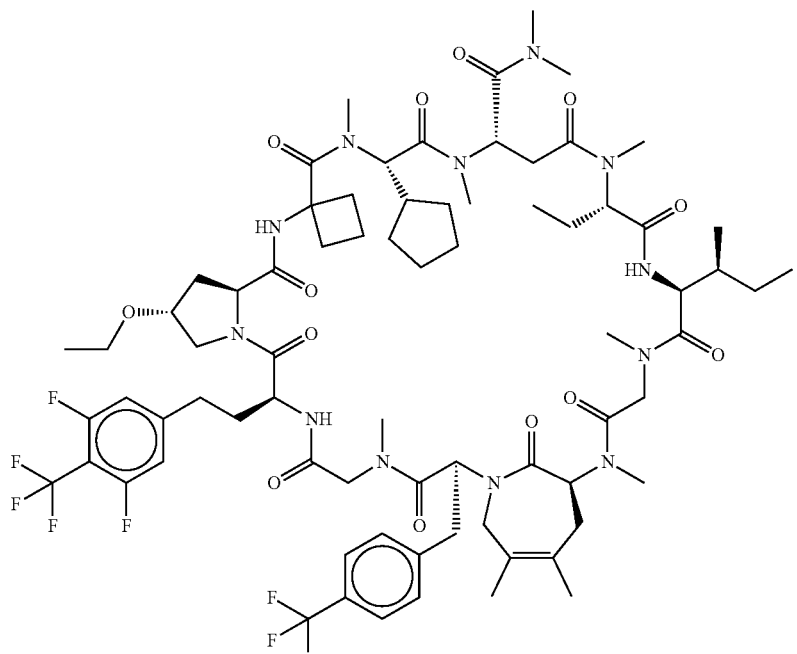 |
| PP1049 | 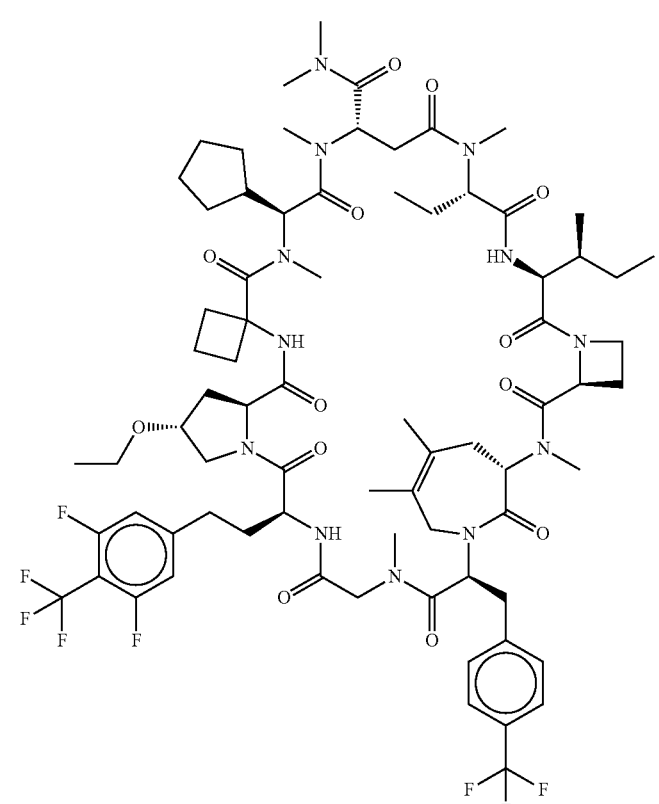 |

TABLE 38-continued

| Compound No. | Structural Formula |
|---|---|
| PP1050 | |
| PP1051 | |

TABLE 38-continued
| Compound No. | Structural Formula |
| --- | --- |
| PP1052 | 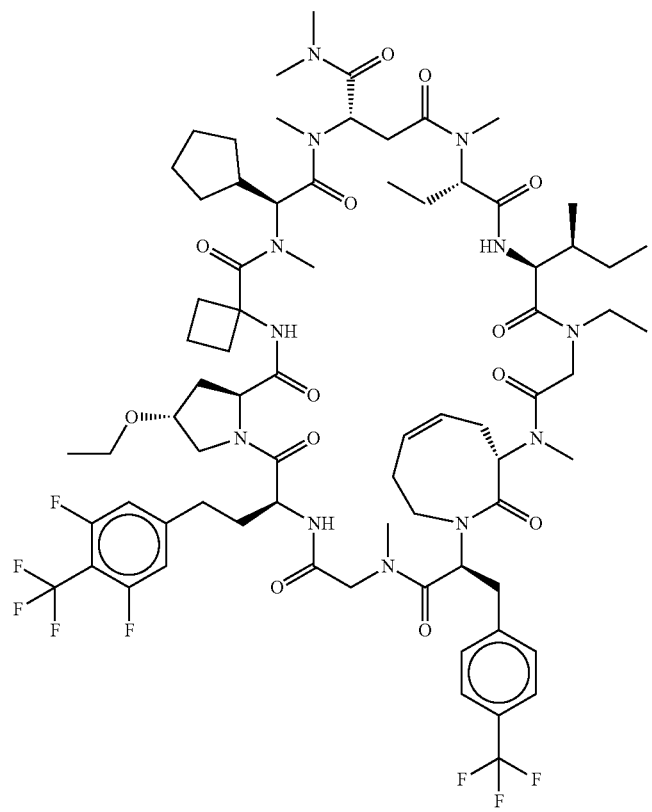 |
| PP1053 | 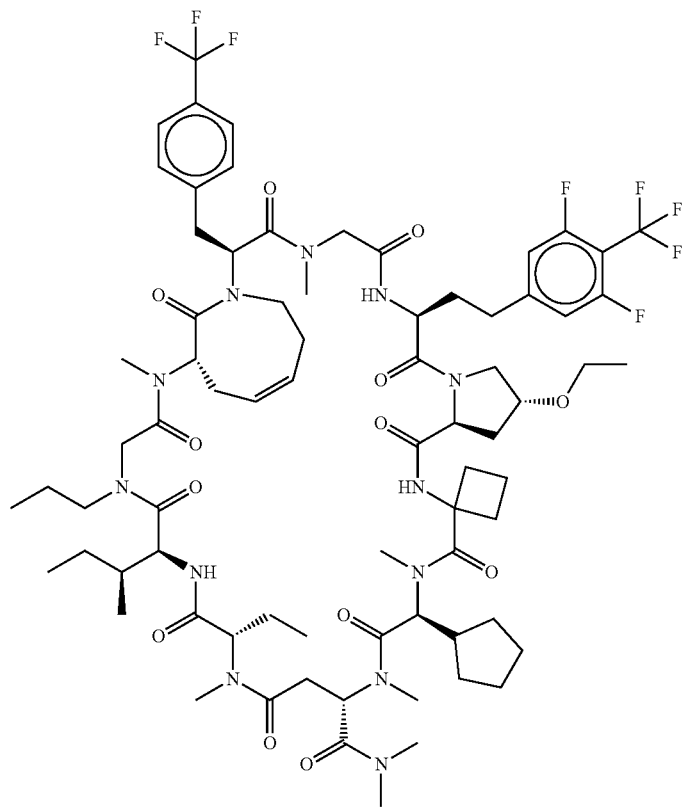 |

//
TABLE 38-continued
| Compound No. | Structural Formula |
|---|---|
| PP1054 | 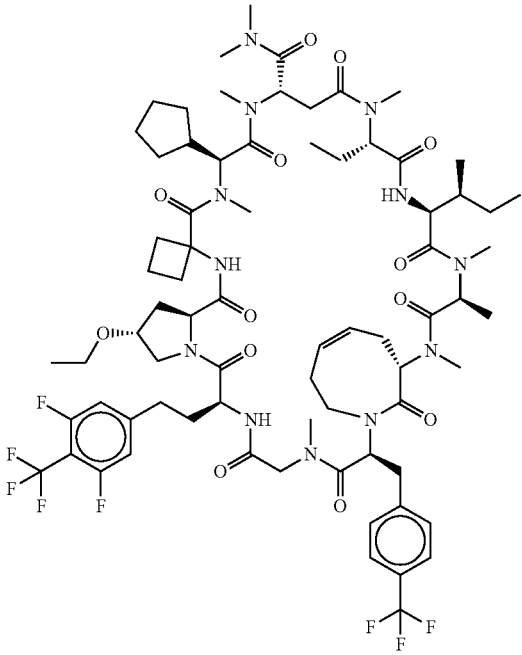 |
| PP1056 | 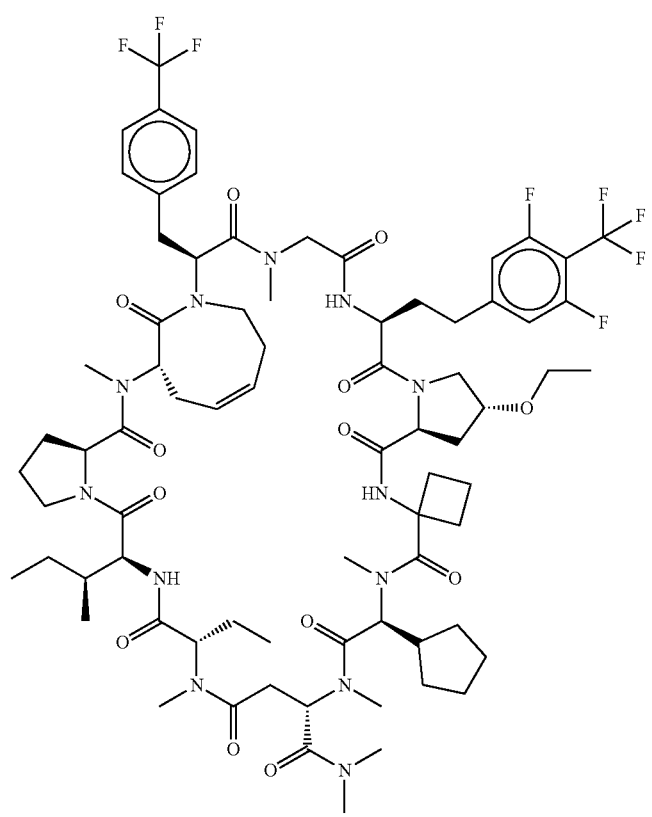 |

TABLE 38-continued
| Compound No. | Structural Formula |
|---|---|
| PP1057 | 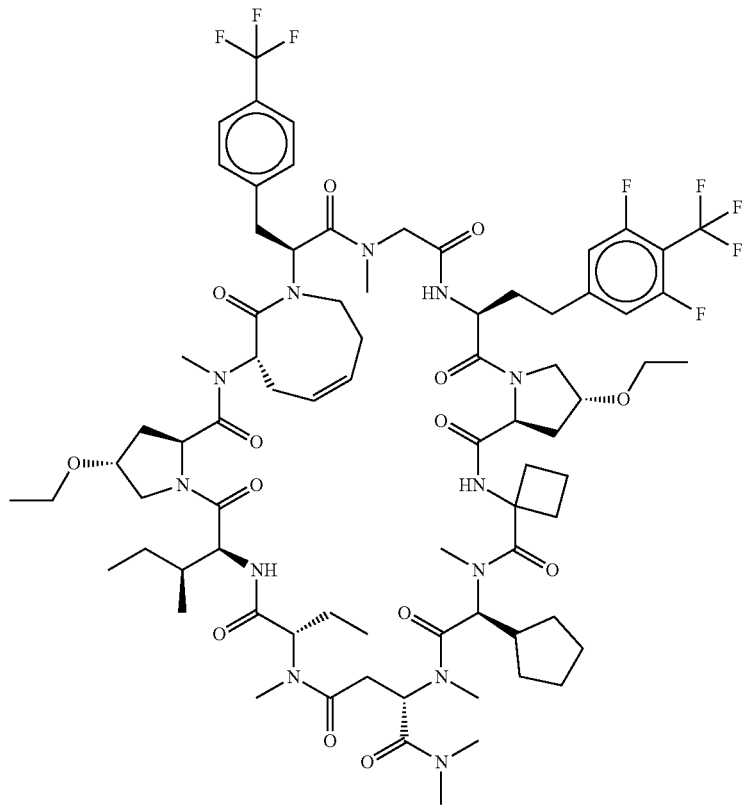 |
| PP1058 | 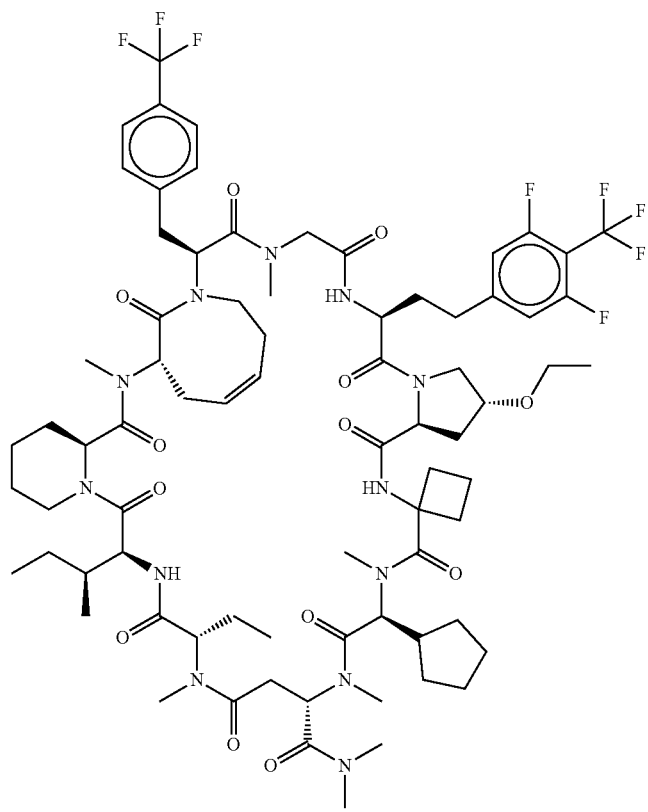 |

TABLE 38-continued
| Compound No. | Structural Formula |
|---|---|
| PP1059 | 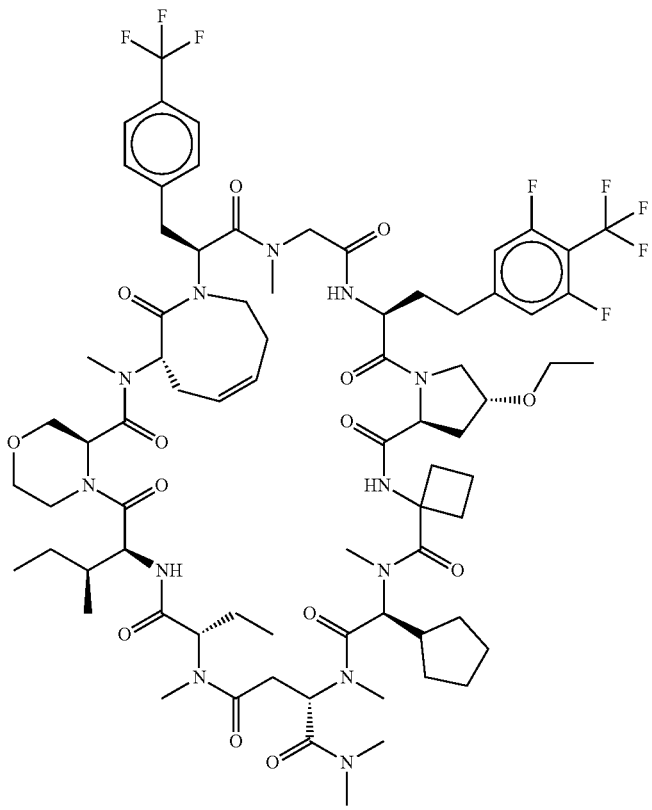 |

TABLE 38-continued
| Compound No. | Structural Formula |
| --- | --- |
| PP1060 | 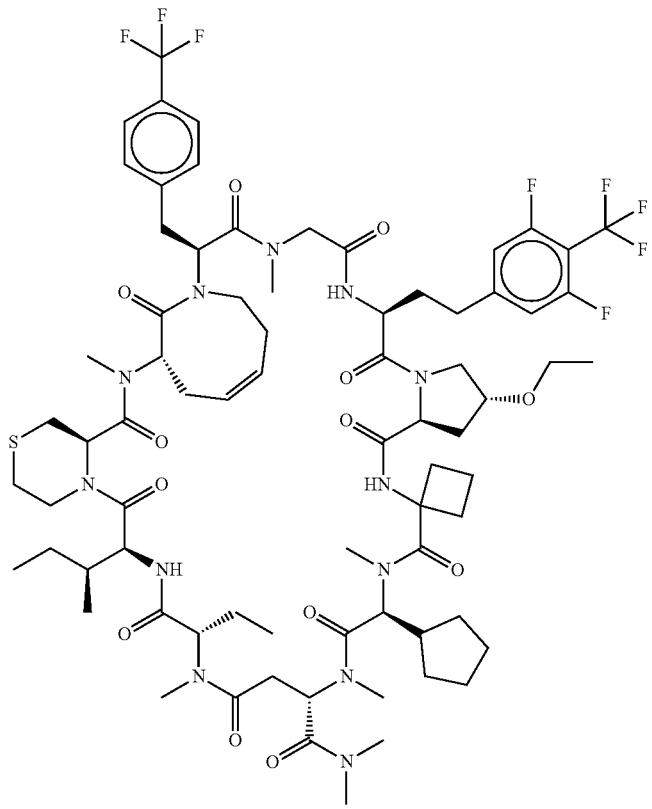 |
| PP1063 | 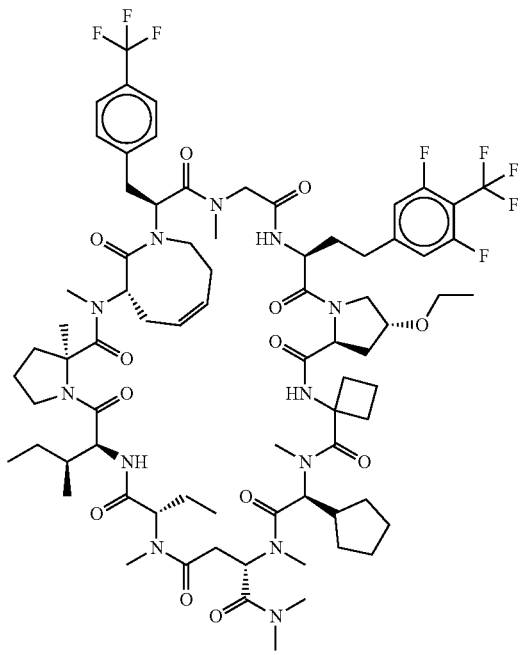 |

TABLE 38-continued
| Compound No. | Structural Formula |
|---|---|
| PP1064 | 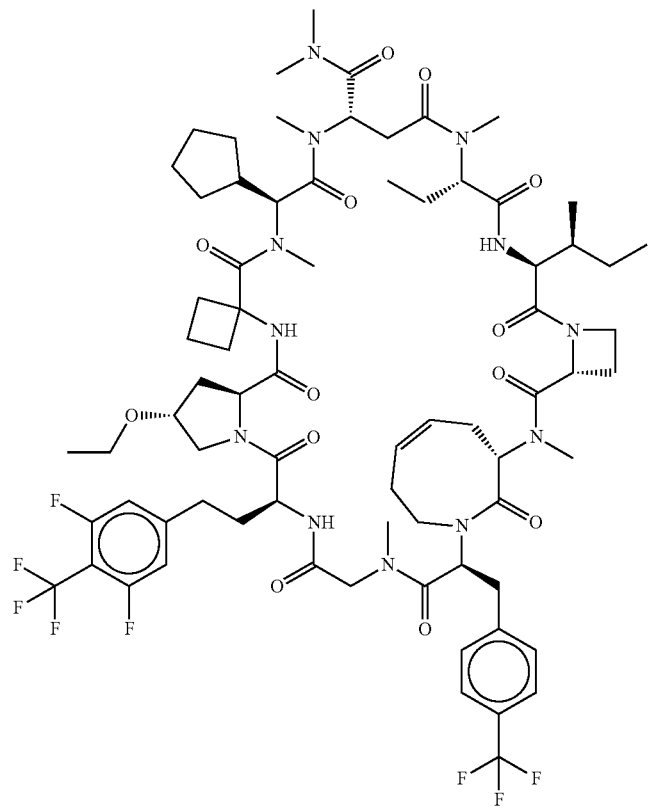 |
| PP1065 | 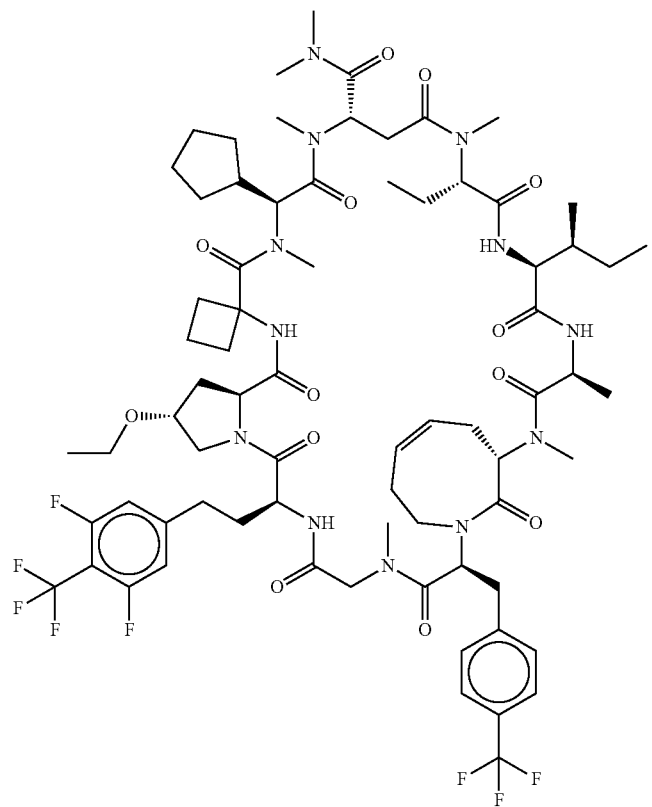 |

TABLE 38-continued
| Compound No. | Structural Formula |
|---|---|
| PP1067 | 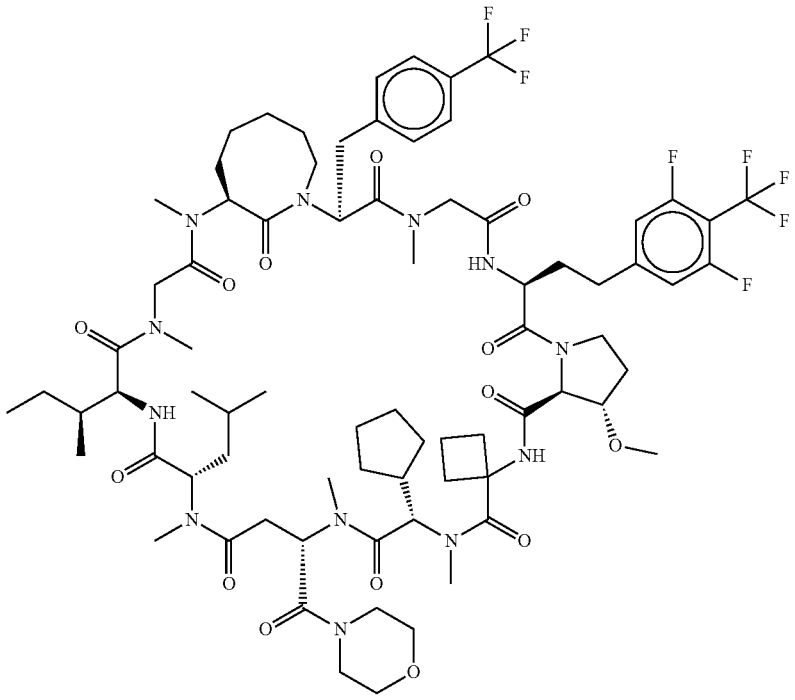 |
| PP1068 | 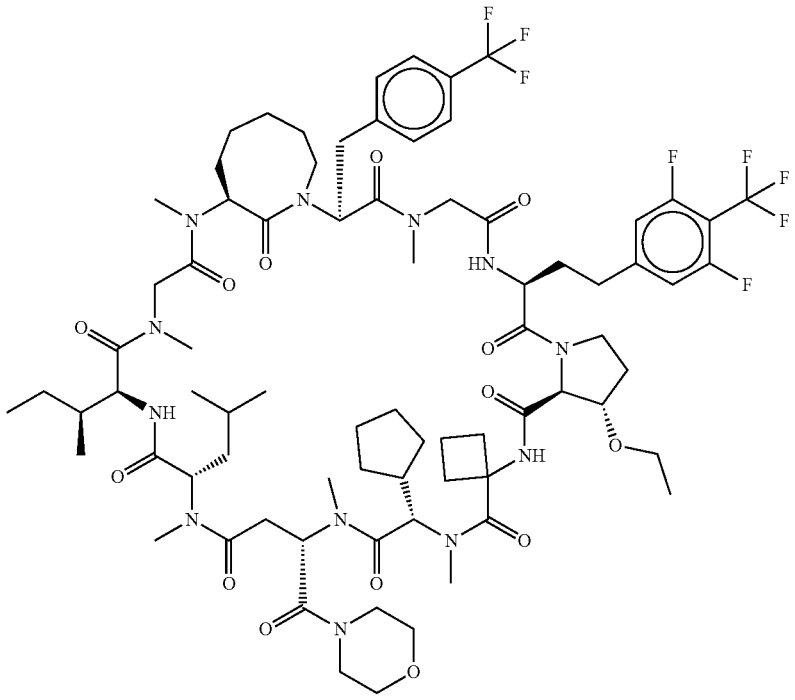 |

TABLE 38-continued
| Compound No. | Structural Formula |
|---|---|
| PP1069 | 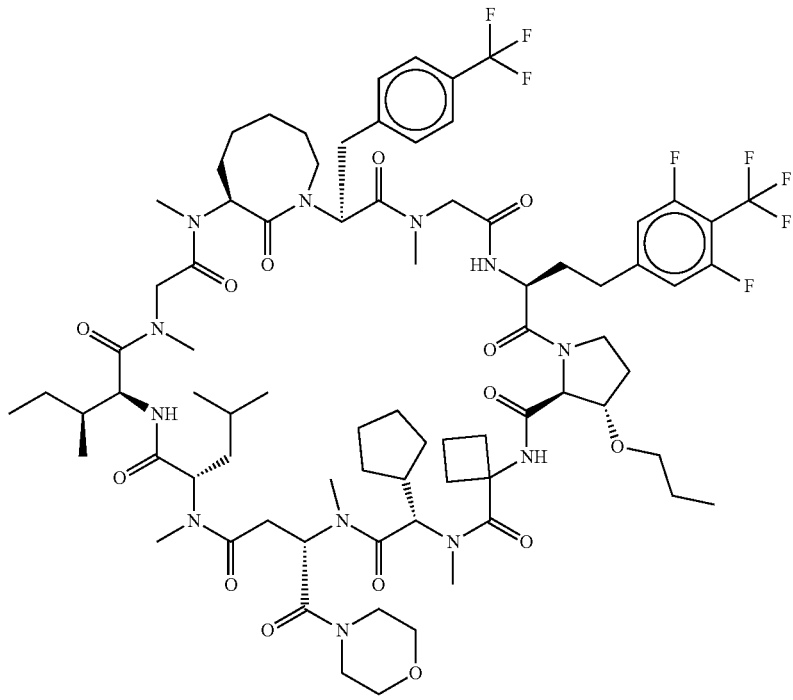 |
| PP1070 | 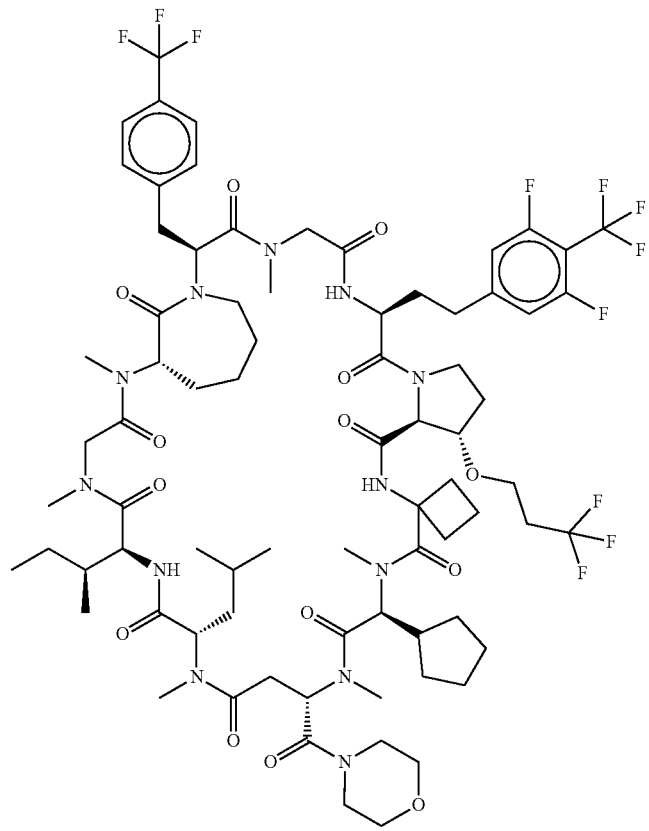 |

TABLE 38-continued
| Compound No. | Structural Formula |
|---|---|
| PP1071 | 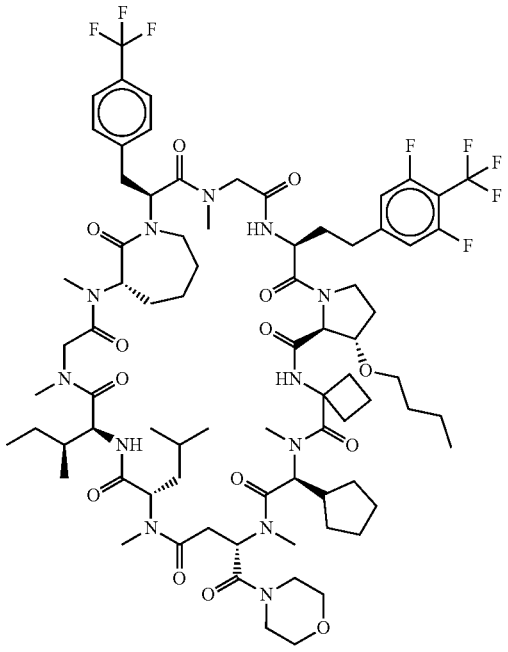 |
| PP1072 | 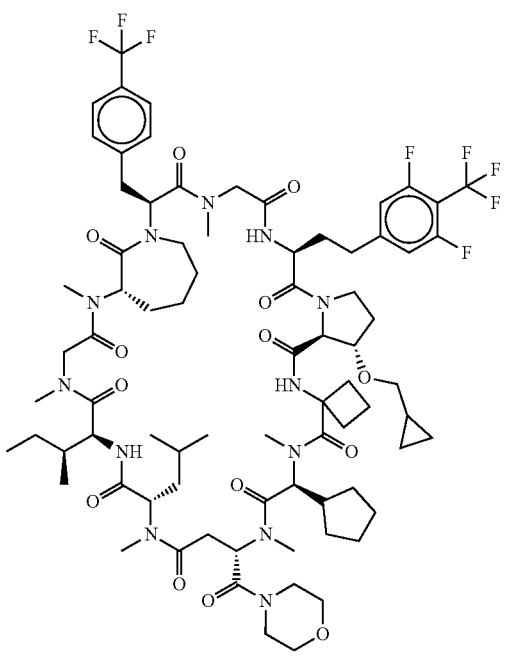 |

TABLE 38-continued

| Compound No. | Structural Formula |
| --- | --- |
| PP1073 | |
| PP1075 | |

TABLE 38-continued

| Compound No. | Structural Formula |
|---|---|
| PP1076 | |
| PP1077 | |

TABLE 38-continued
| Compound No. | Structural Formula |
| --- | --- |
| PP1078 | 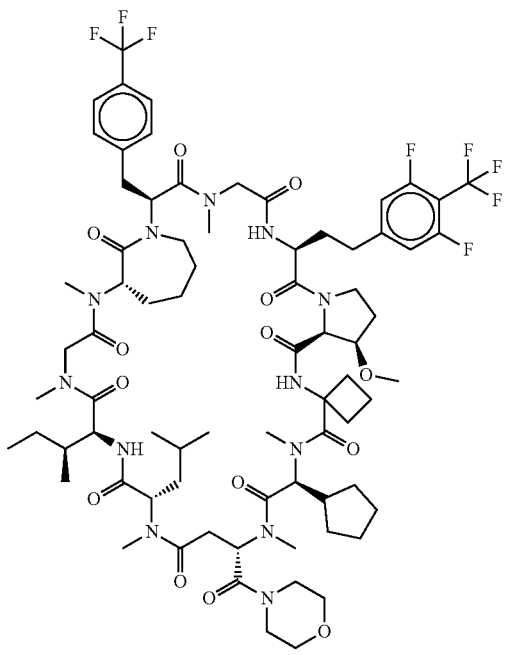 |
| PP1079 | 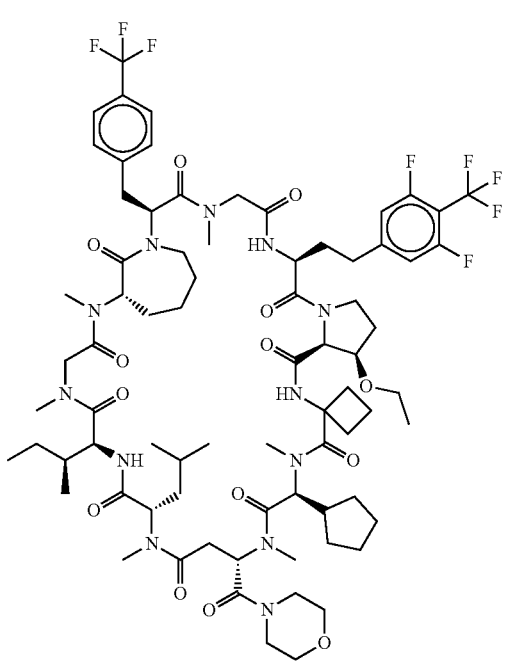 |

TABLE 38-continued
| Compound No. | Structural Formula |
|---|---|
| PP1080 | 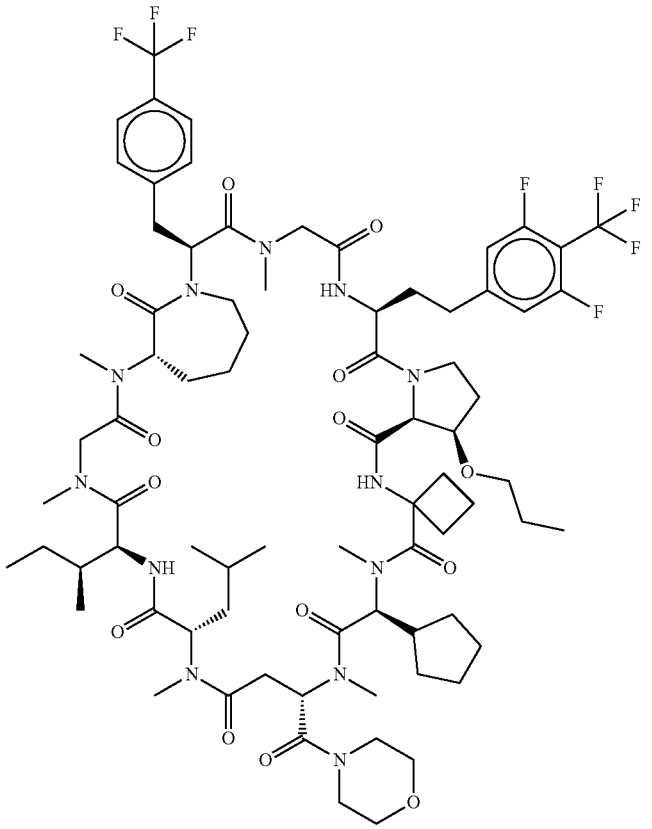 |
| PP1082 | 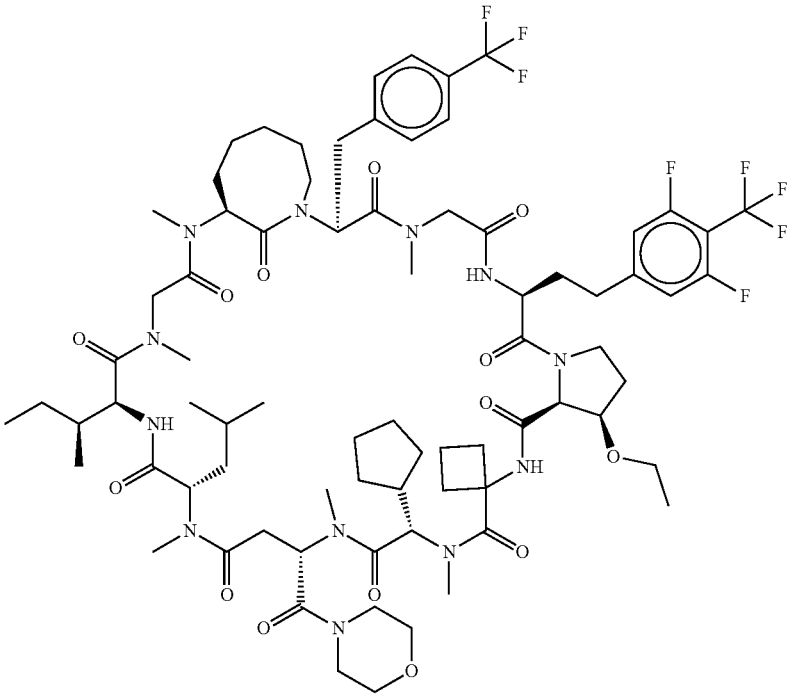 |

TABLE 38-continued

| Compound No. | Structural Formula |
|---|---|
| PP1083 | |
| PP1084 | |

TABLE 38-continued
| Compound No. | Structural Formula |
|---|---|
| PP1085 | 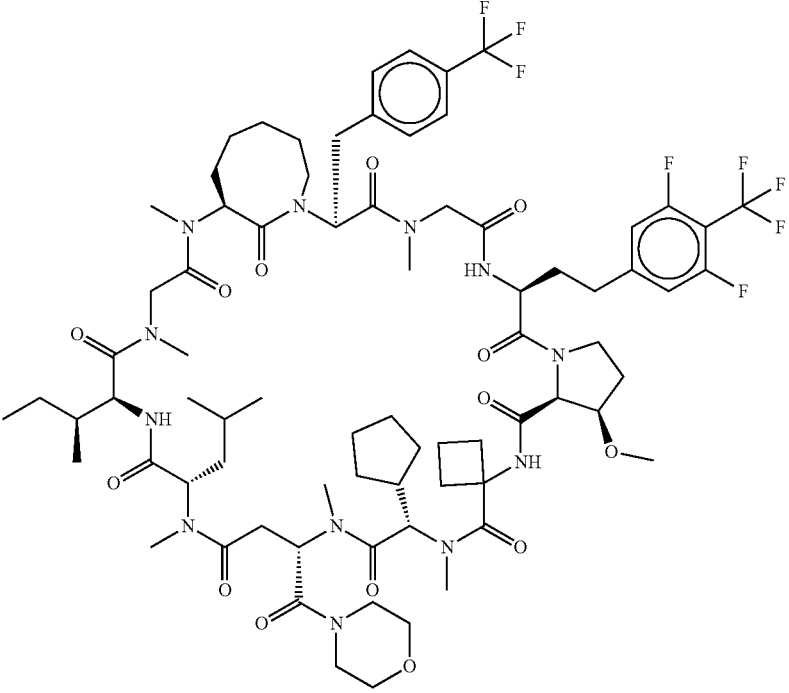 |
| PP1086 | 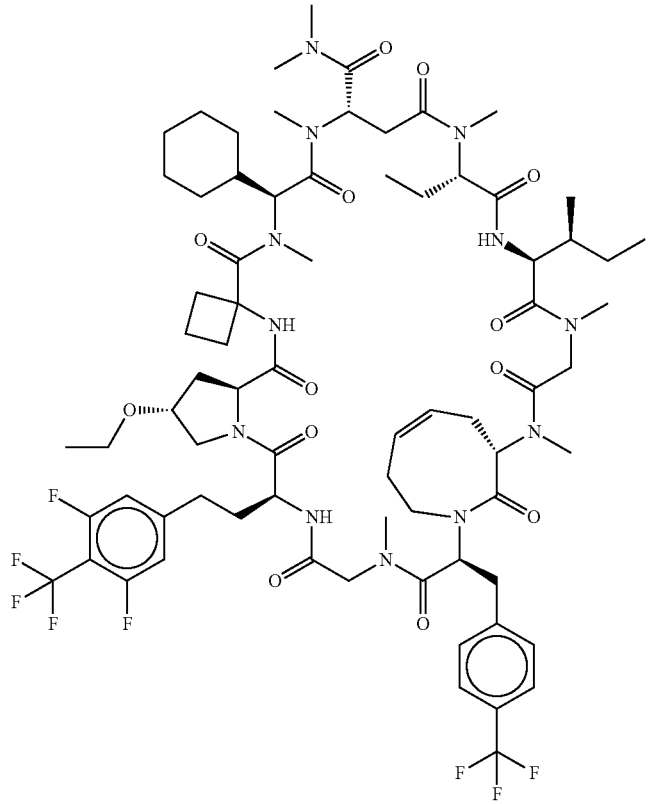 |

TABLE 38-continued
| Compound No. | Structural Formula |
|---|---|
| PP1087 | 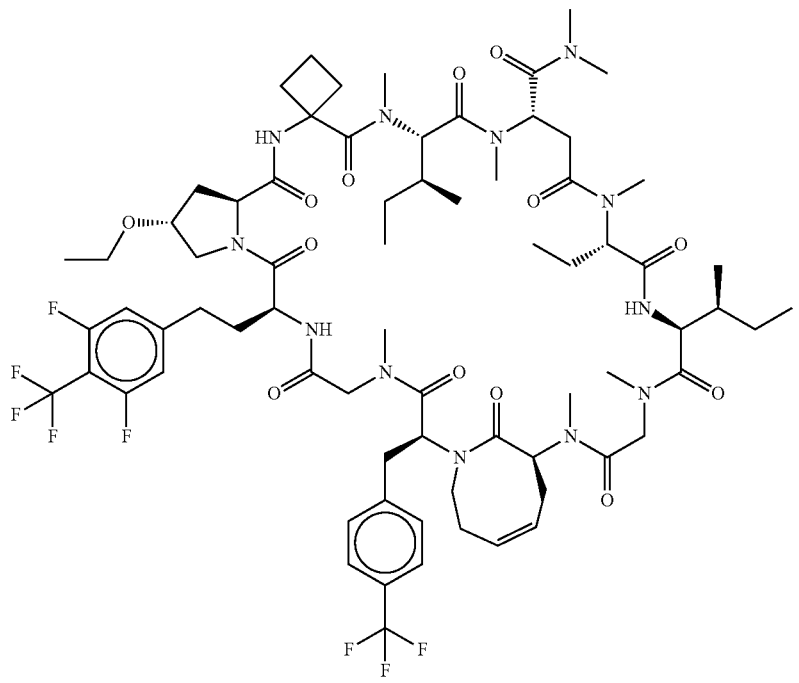 |
| PP1088 | 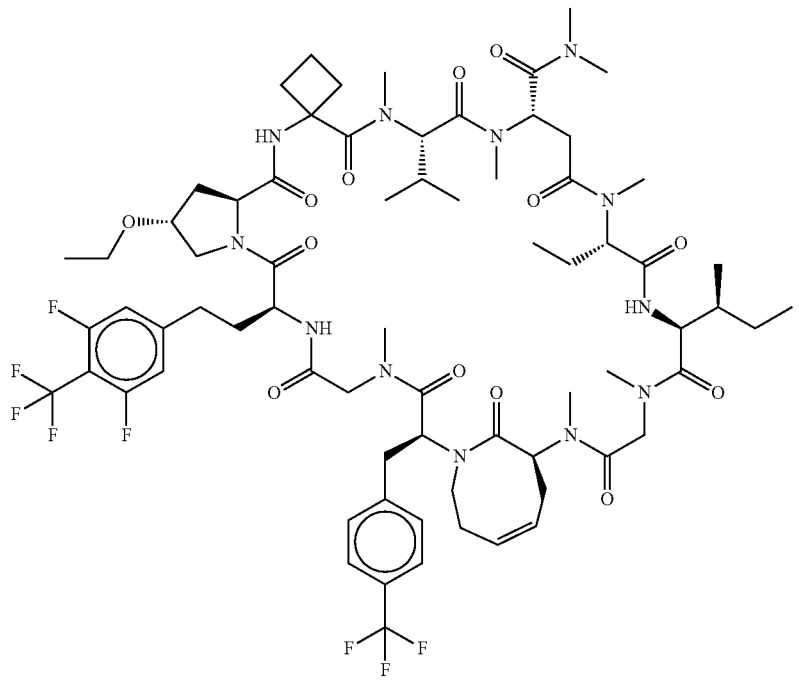 |

TABLE 38-continued
| Compound No. | Structural Formula |
|---|---|
| PP1089 | 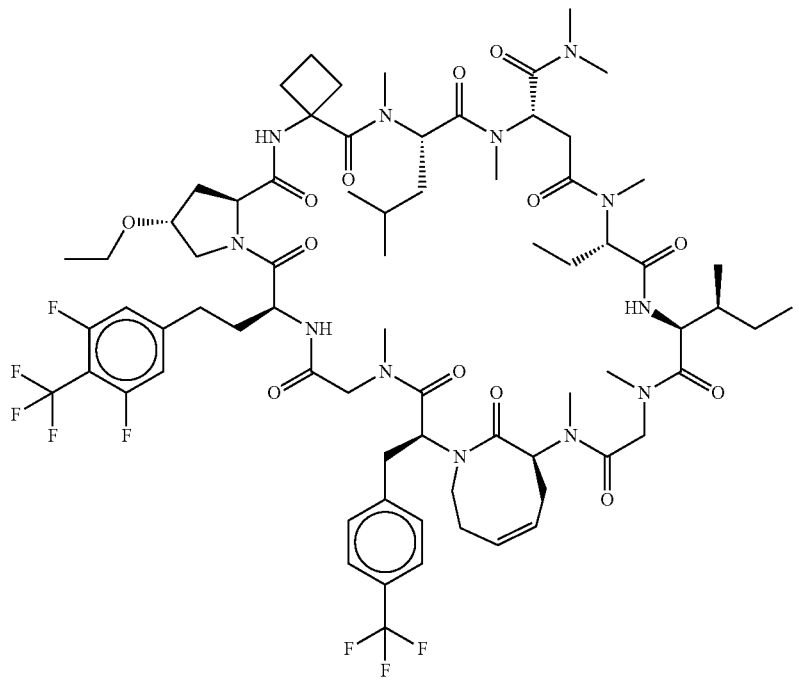 |
| PP1090 | 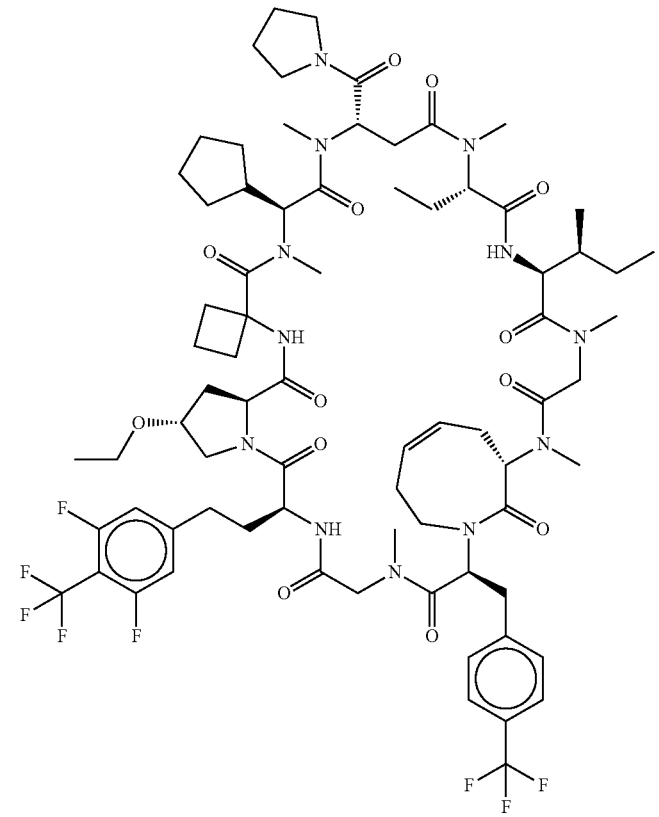 |

TABLE 38-continued

| Compound No. | Structural Formula |
|---|---|
| PP1091 | |
| PP1092 | |

TABLE 38-continued
| Compound No. | Structural Formula |
|---|---|
| PP1093 | 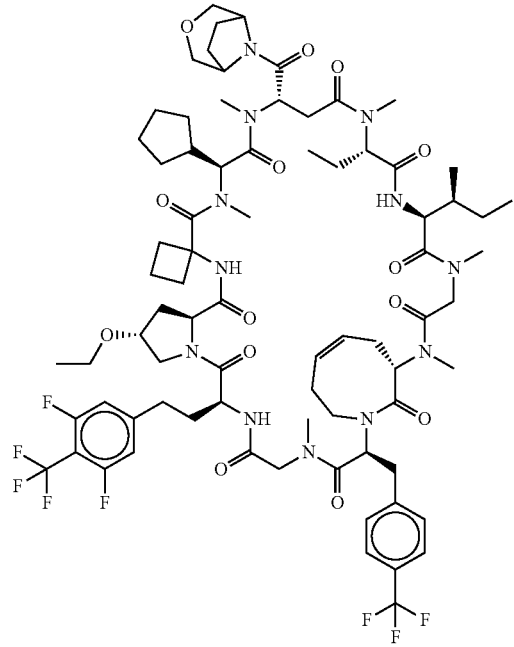 |
| PP1094 | 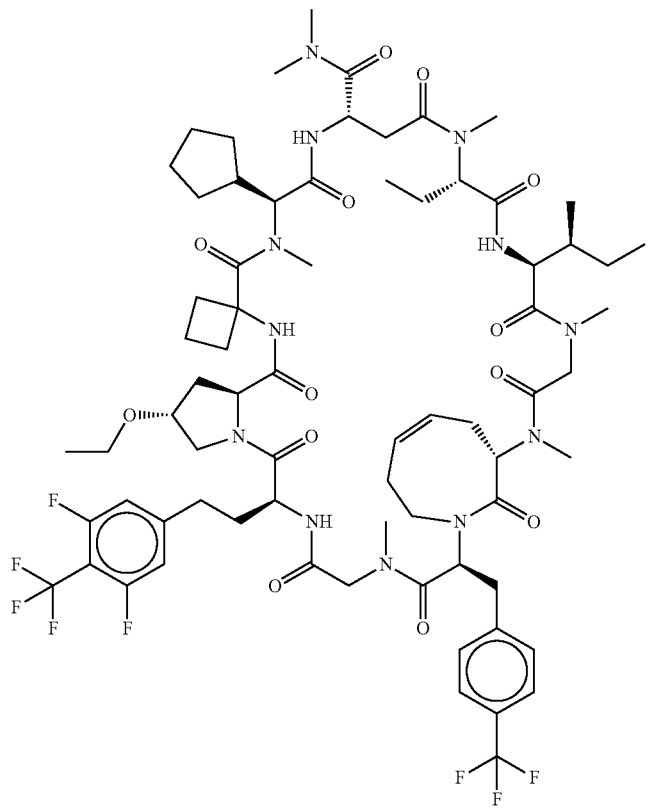 |

1909 TABLE 38-continued 1910
| Compound No. | Structural Formula |
|---|---|
| PP1095 | 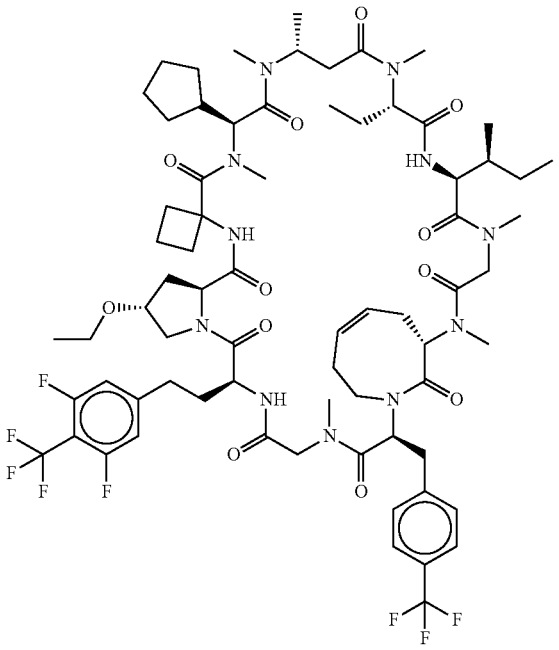 |
| PP1096 | 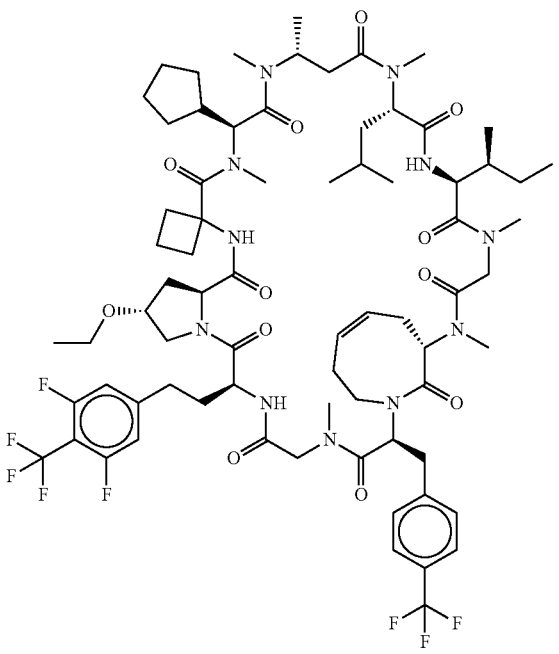 |

TABLE 38-continued

| Compound No. | Structural Formula |
|---|---|
| PP1097 | |
| PP1098 | |

TABLE 38-continued
| Compound No. | Structural Formula |
|---|---|
| PP1099 | 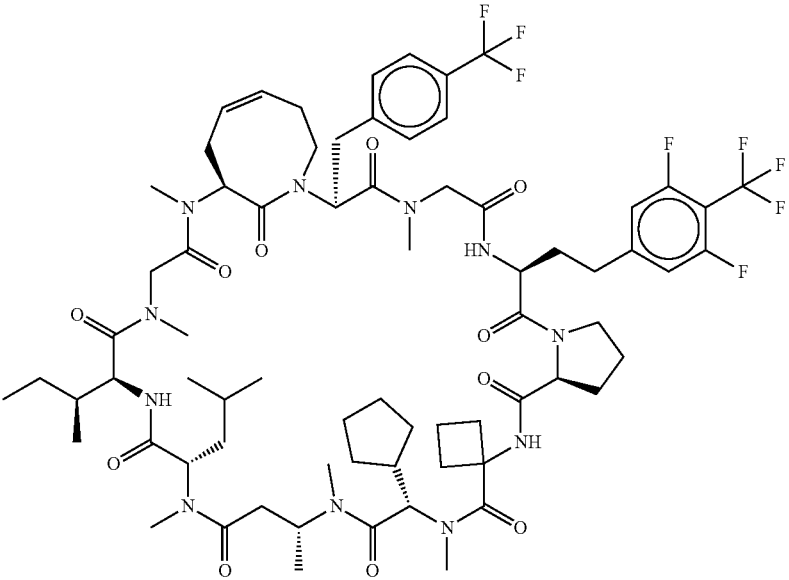 |
| PP1100 | 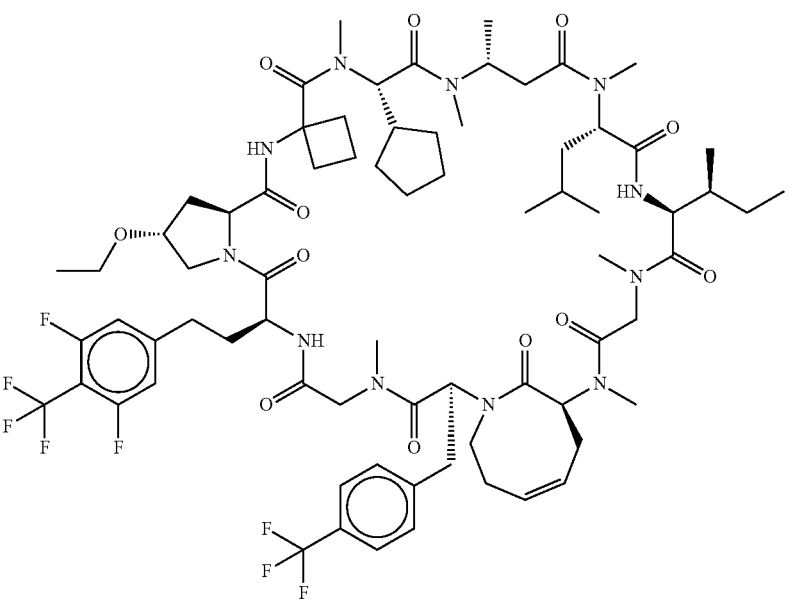 |

TABLE 38-continued

| Compound No. | Structural Formula |
|---|---|
| PP1101 | |
| PP1102 | |

TABLE 38-continued
| Compound No. | Structural Formula |
|---|---|
| PP1103 | 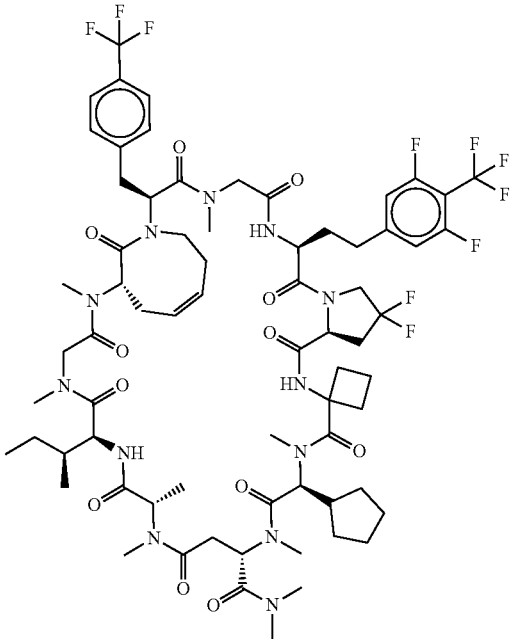 |
| PP1104 | 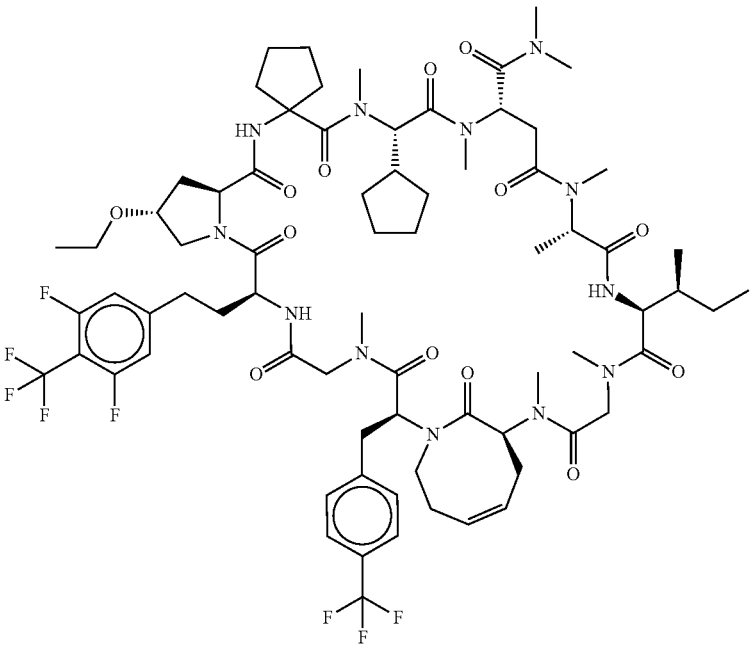 |

TABLE 38-continued

| Compound No. | Structural Formula |
| --- | --- |
| PP1105 | |
| PP1106 | |

TABLE 38-continued
| Compound No. | Structural Formula |
|---|---|
| PP1107 | 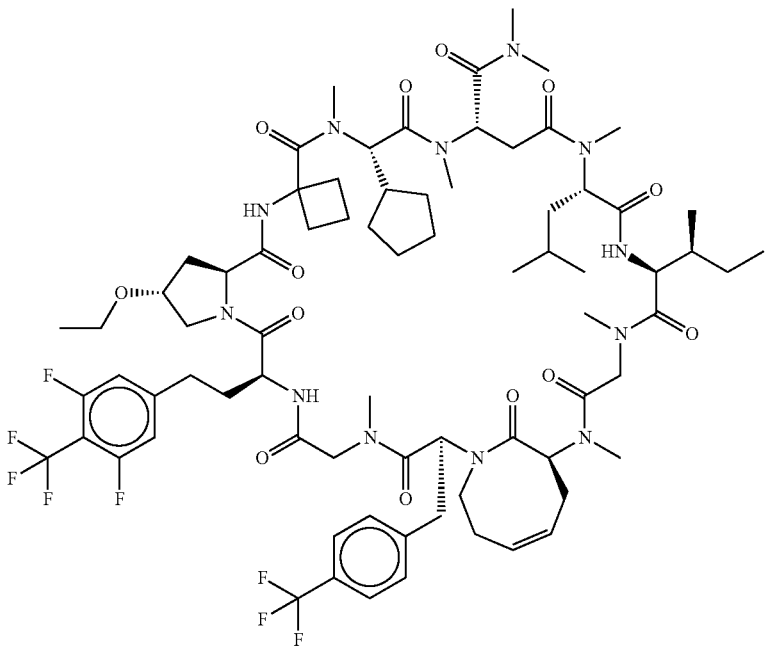 |
| PP1108 | 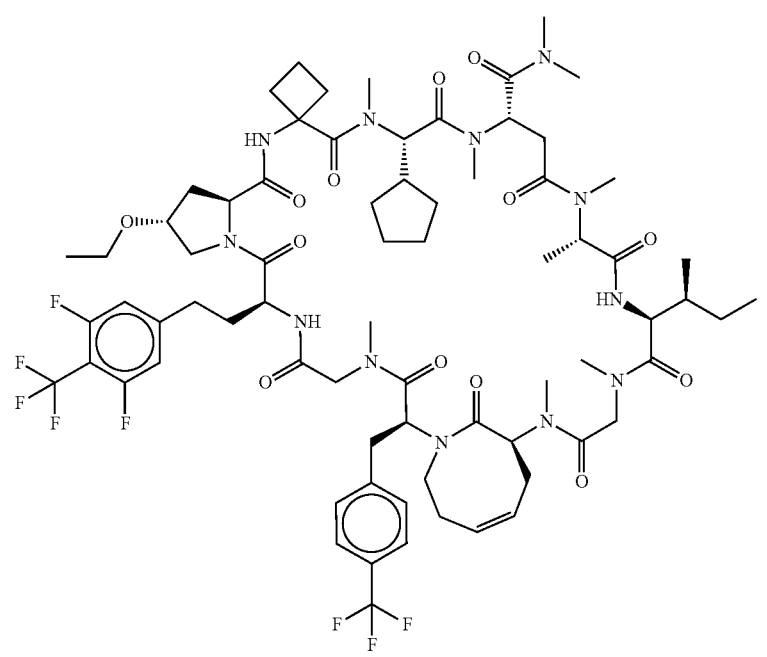 |

TABLE 38-continued
| Compound No. | Structural Formula |
|---|---|
| PP1109 | 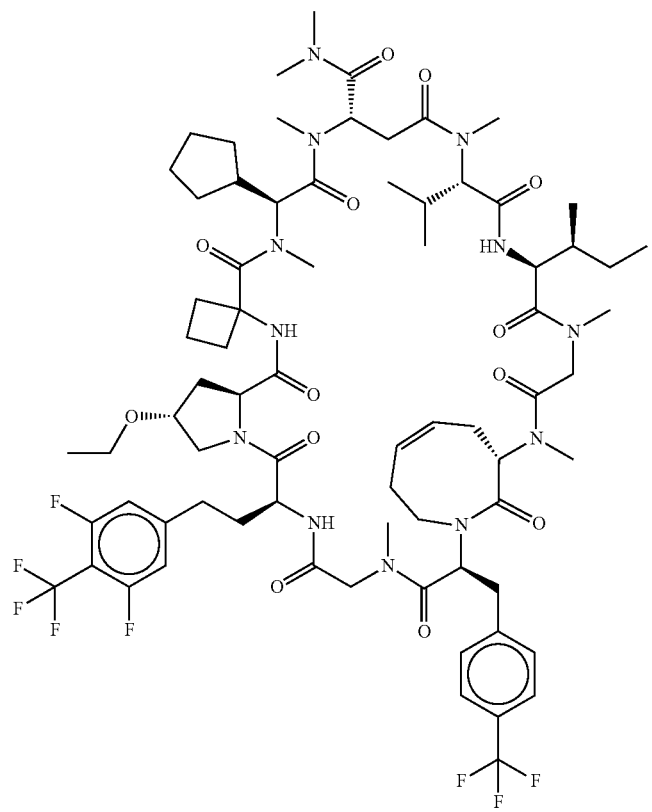 |
| PP1110 | 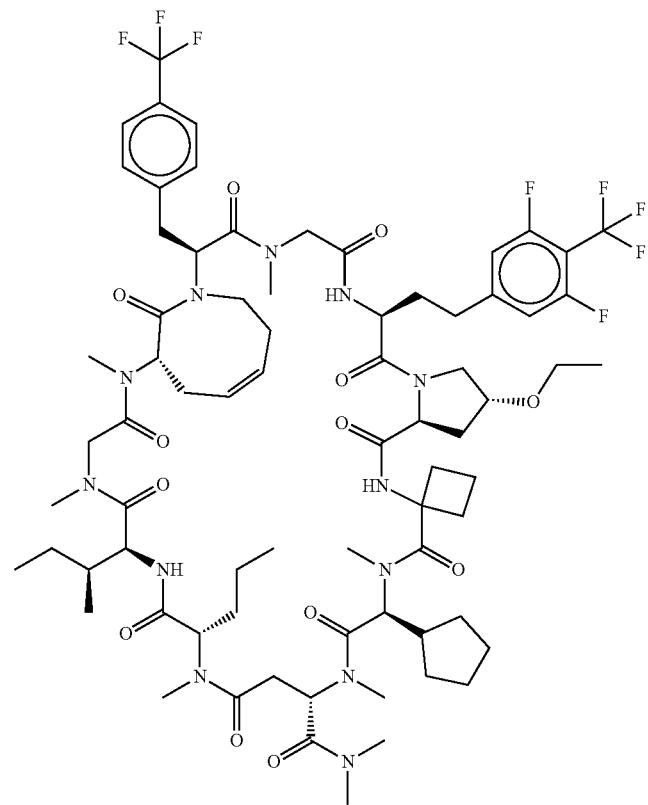 |

TABLE 38-continued
| Compound No. | Structural Formula |
|---|---|
| PP1111 | 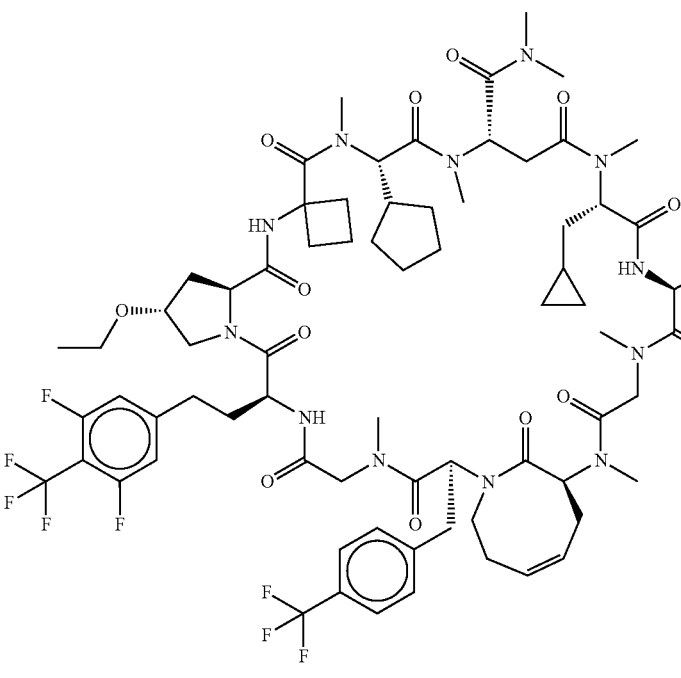 |
| PP1112 | 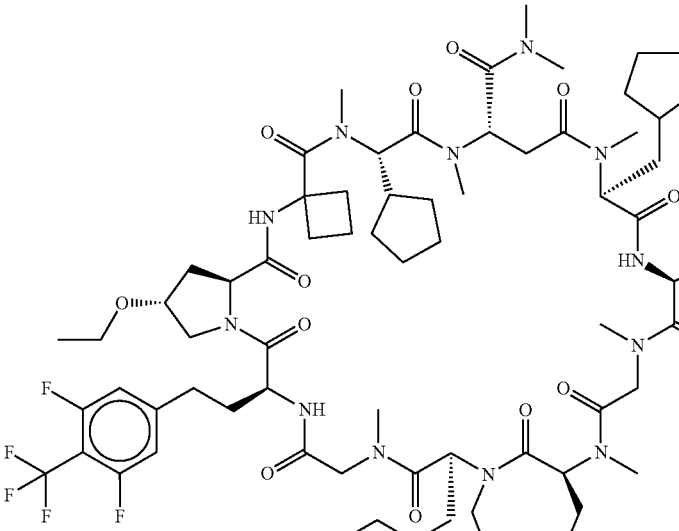 |

TABLE 38-continued
| Compound No. | Structural Formula |
|---|---|
| PP1113 | 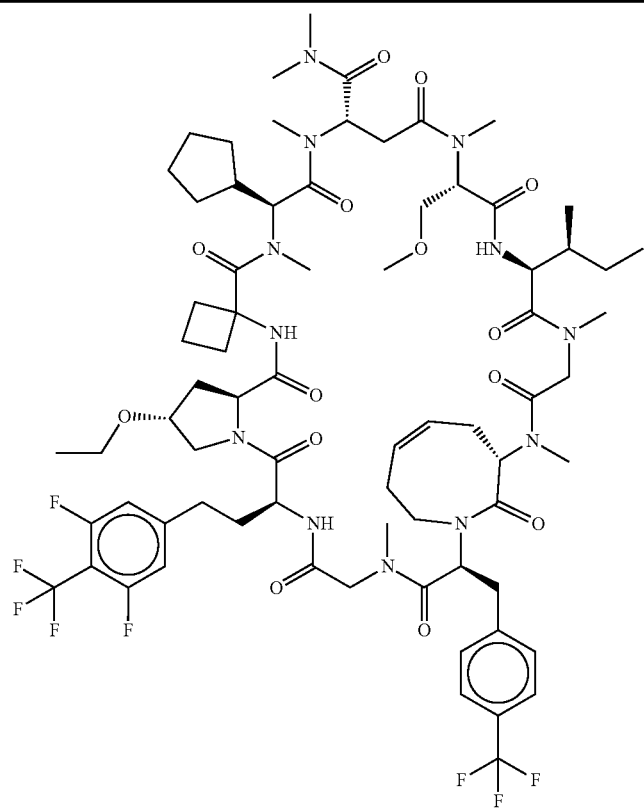 |
| PP1114 | 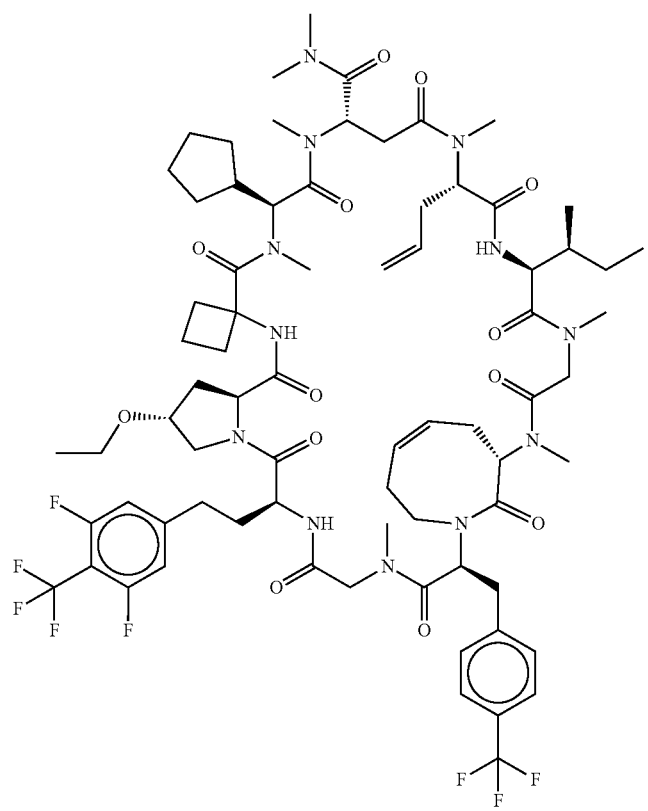 |

TABLE 38-continued
| Compound No. | Structural Formula |
|---|---|
| PP1115 | 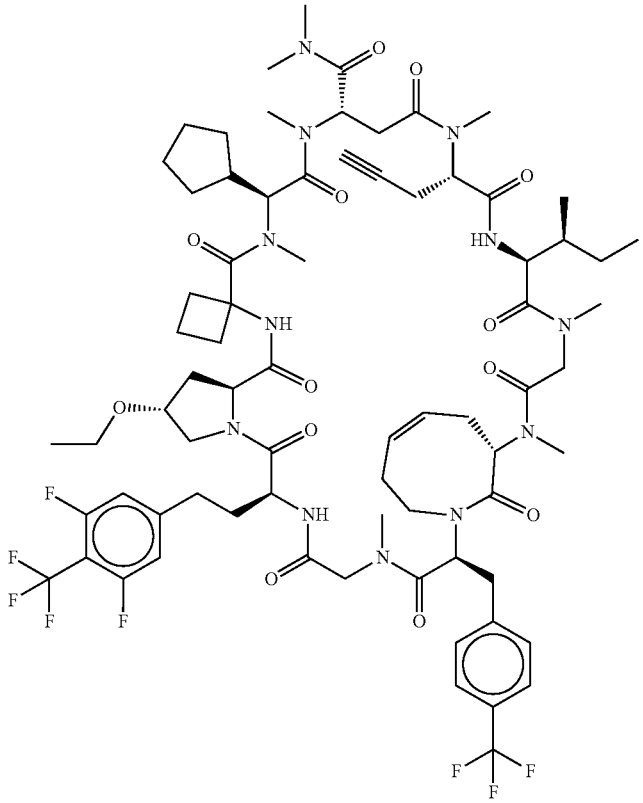 |
| PP1116 | 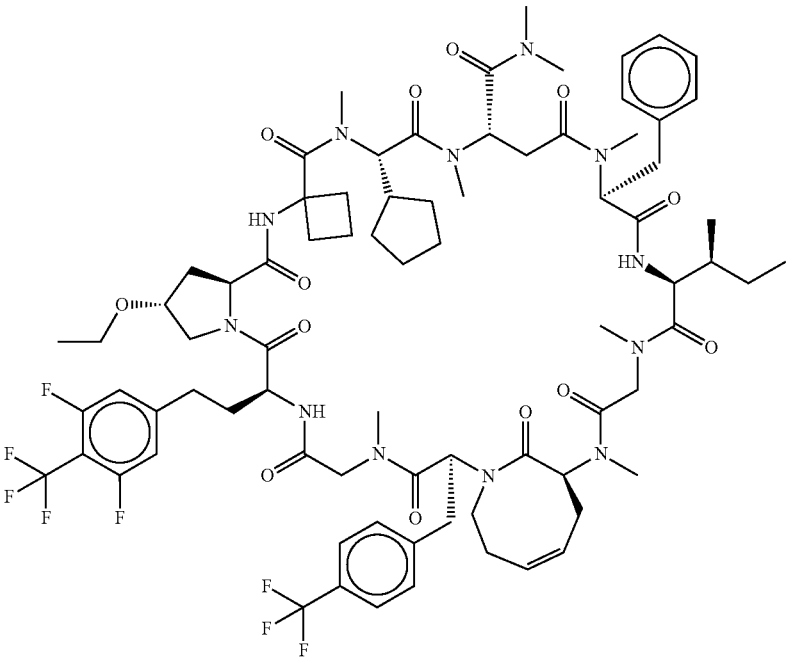 |

TABLE 38-continued
| Compound No. | Structural Formula |
|---|---|
| PP1117 | 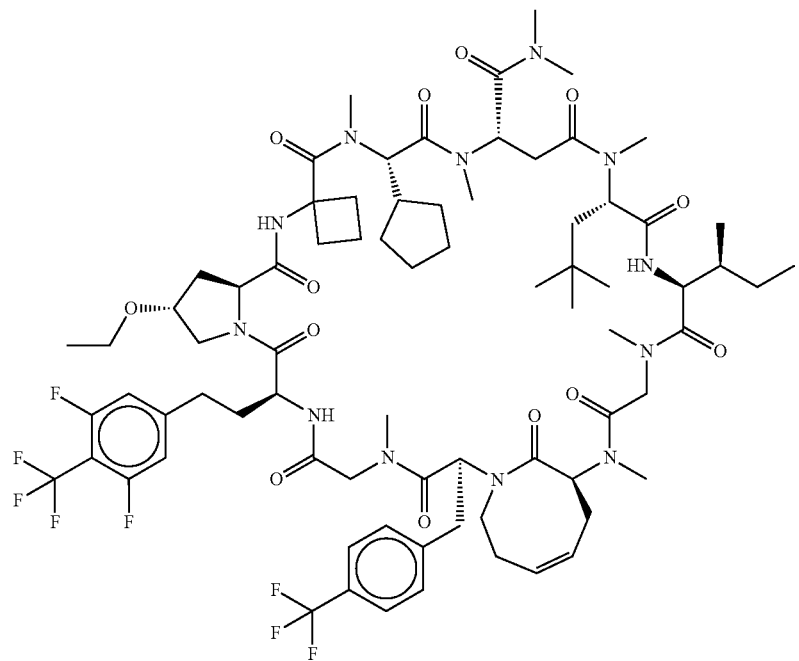 |
| PP1118 | 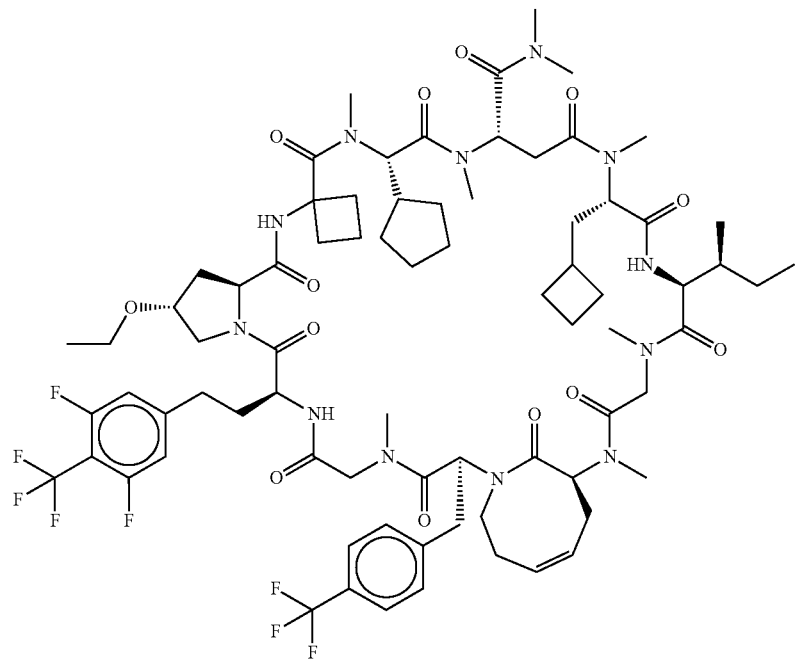 |

TABLE 38-continued
| Compound No. | Structural Formula |
|---|---|
| PP1119 | 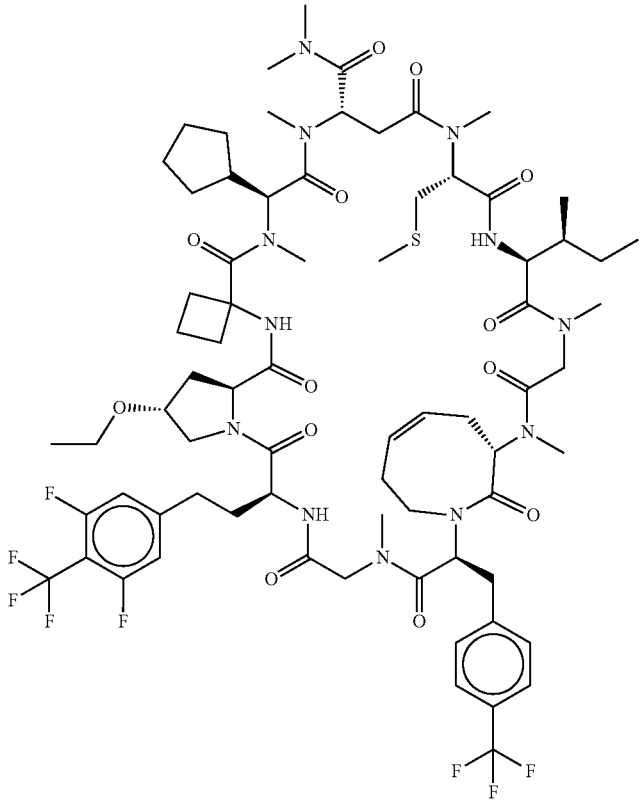 |
| PP1120 | 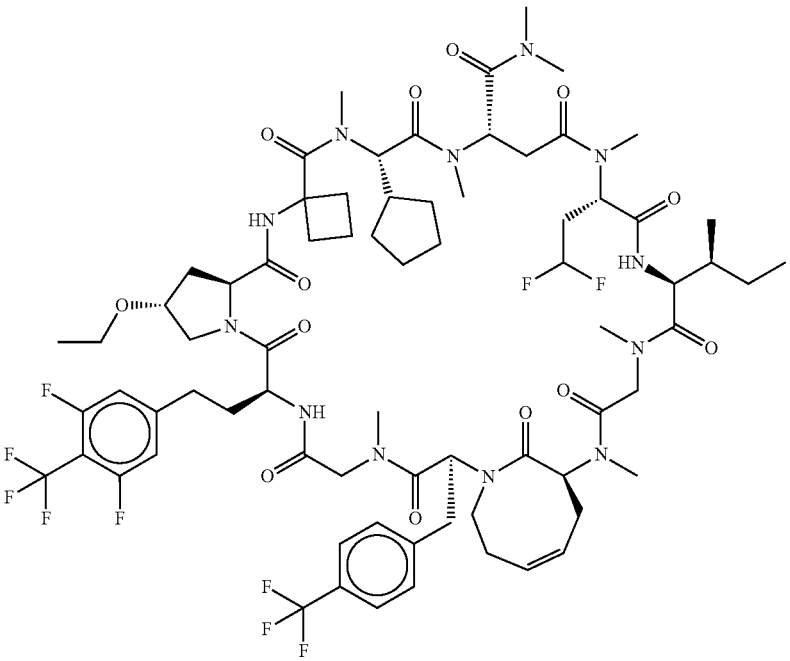 |

TABLE 38-continued
| Compound No. | Structural Formula |
|---|---|
| PP1121 | 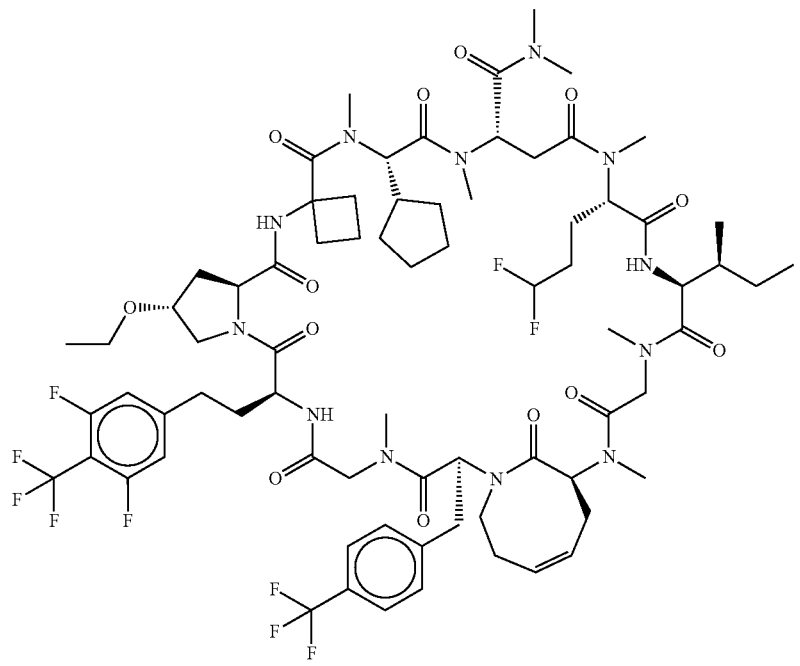 |
| PP1122 | 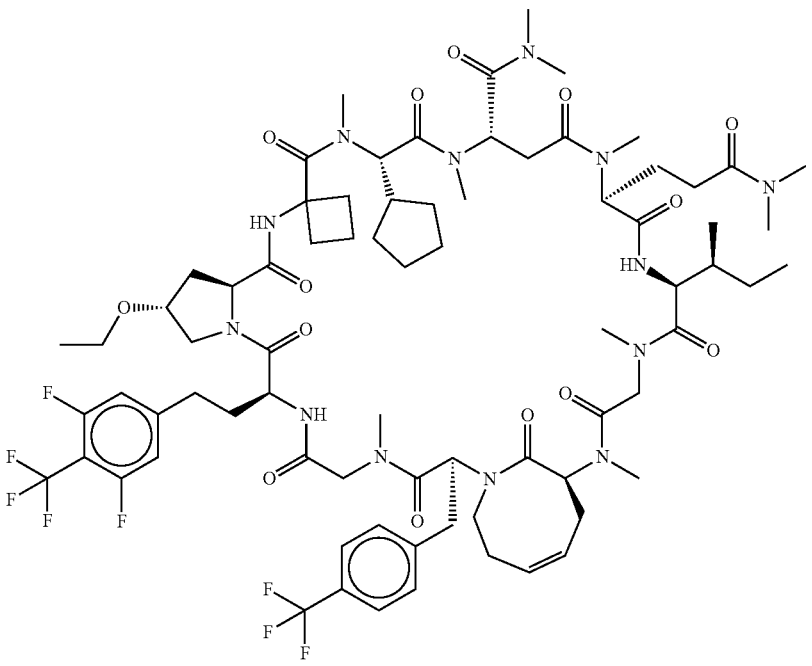 |

TABLE 38-continued
| Compound No. | Structural Formula |
|---|---|
| PP1123 | 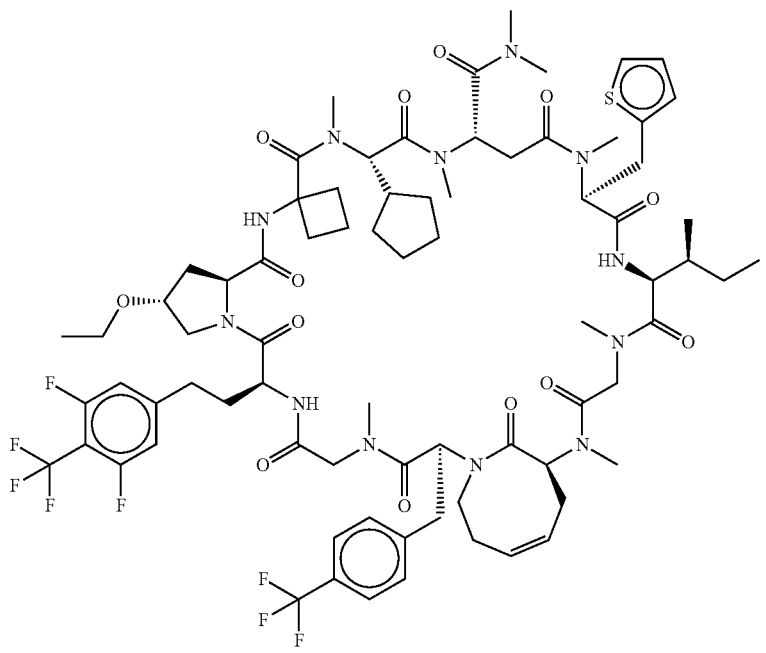 |
| PP1124 | 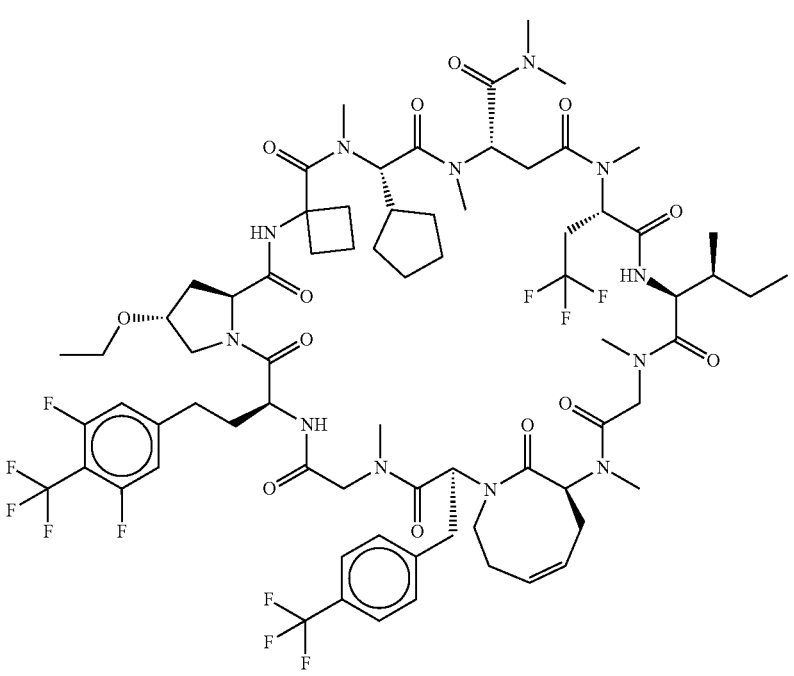 |

TABLE 38-continued
| Compound No. | Structural Formula |
|---|---|
| PP1125 | 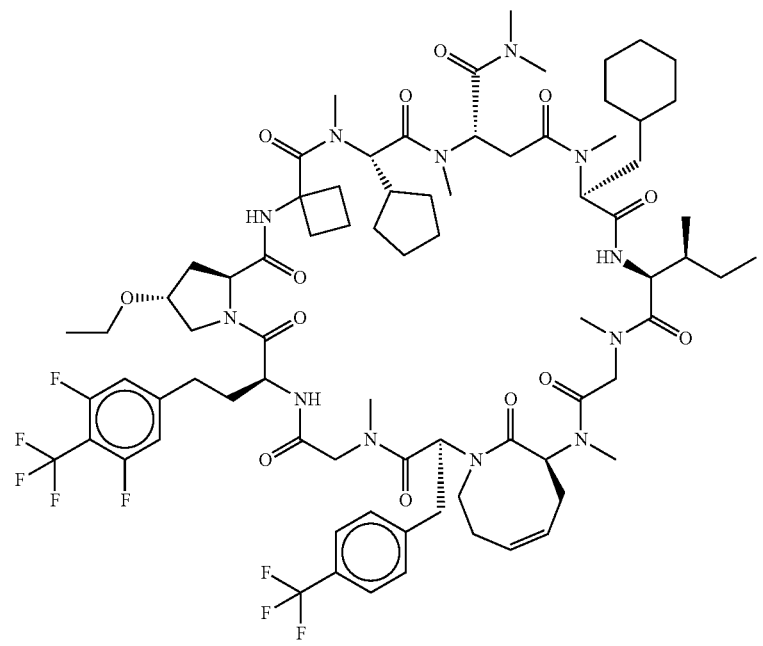 |
| PP1126 | 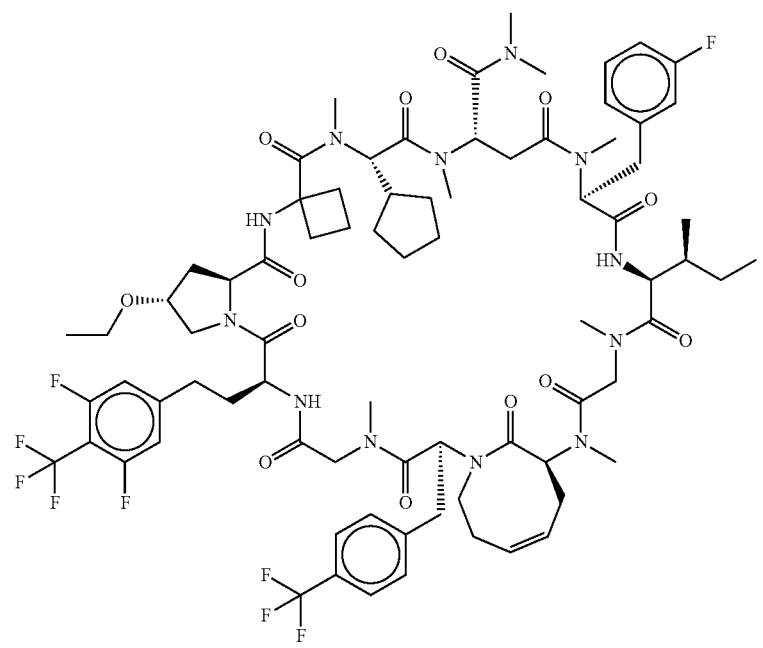 |

TABLE 38-continued
| Compound No. | Structural Formula |
|---|---|
| PP1127 | 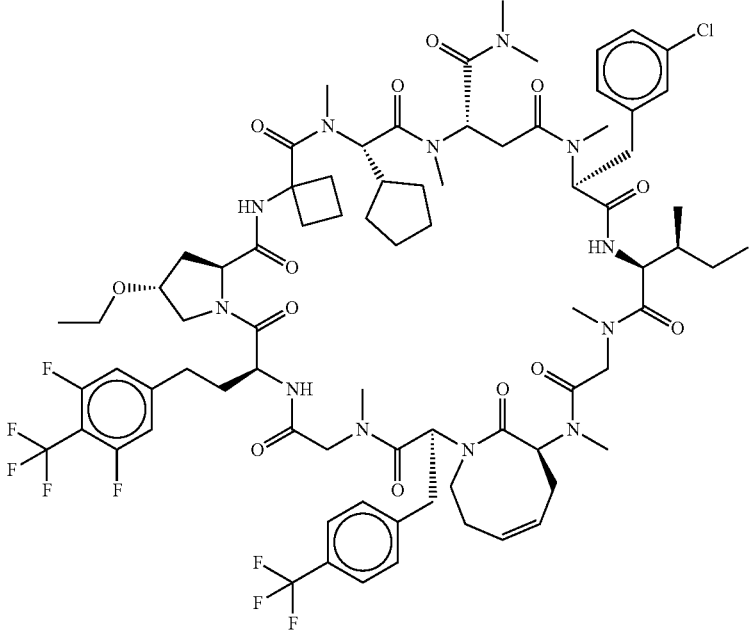 |
| PP1128 | 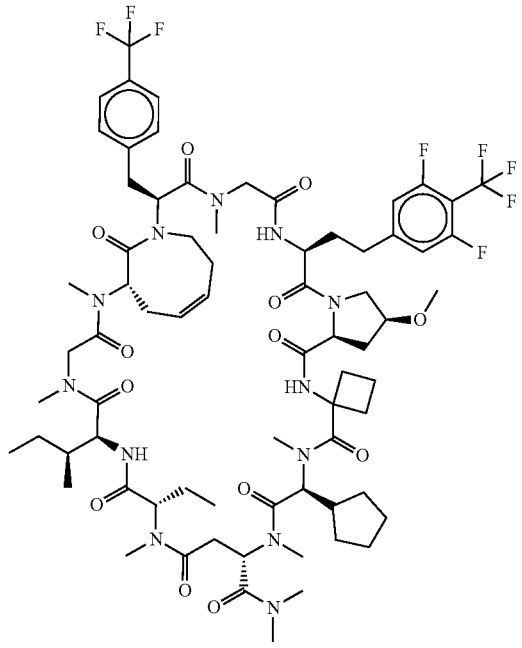 |

TABLE 38-continued
| Compound No. | Structural Formula |
|---|---|
| PP1129 | 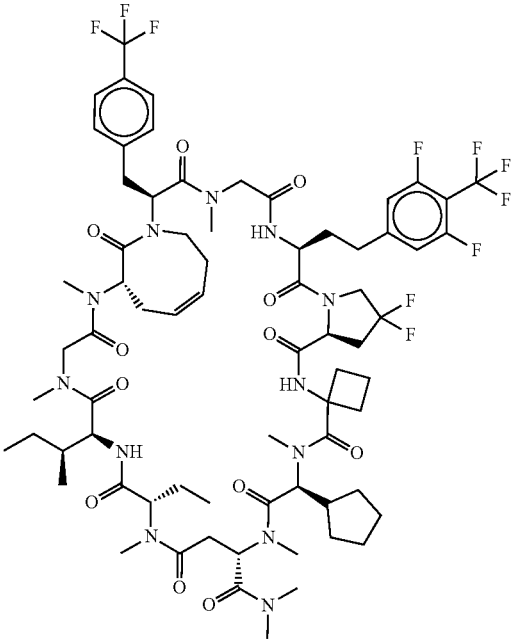 |
| PP1130 | 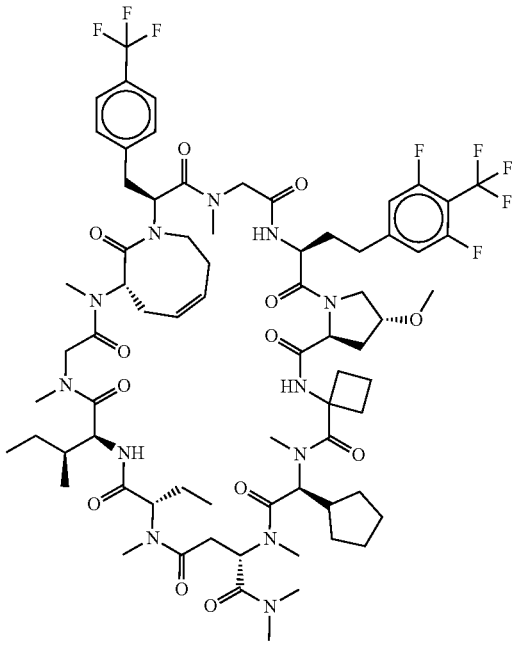 |

TABLE 38-continued

| Compound No. | Structural Formula |
|---|---|
| PP1131 | |
| PP1132 | |

TABLE 38-continued

| Compound No. | Structural Formula |
|---|---|
| PP1133 | |
| PP1134 | |

TABLE 38-continued

| Compound No. | Structural Formula |
|---|---|
| PP1135 | |
| PP1136 | |

TABLE 38-continued

| Compound No. | Structural Formula |
| --- | --- |
| PP1137 | |
| PP1138 | |

TABLE 38-continued
| Compound No. | Structural Formula |
|---|---|
| PP1139 | 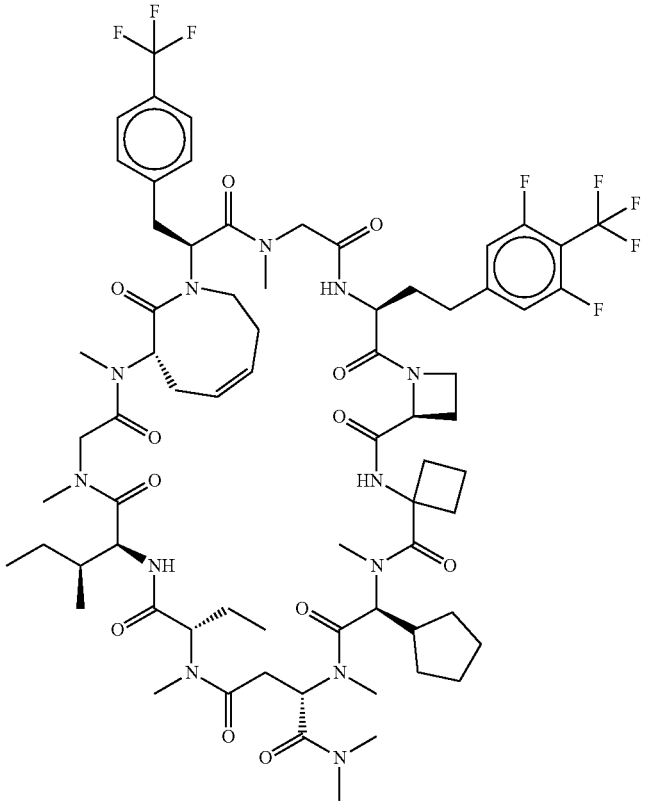 |
| PP1140 | 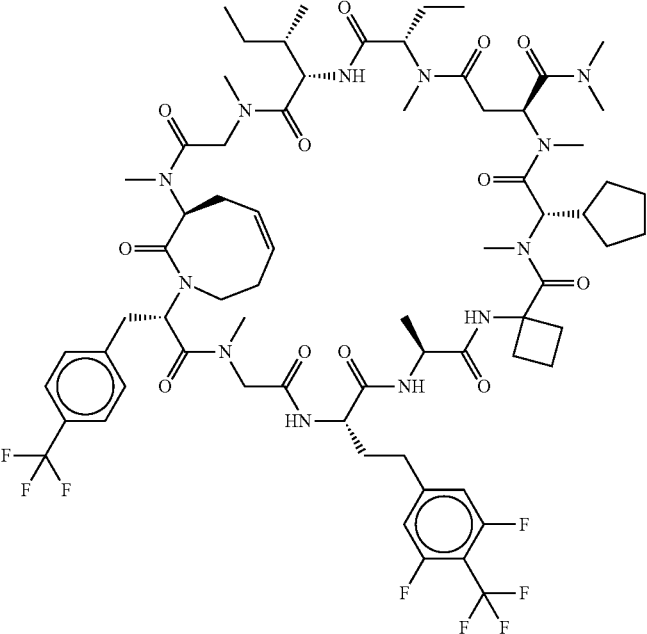 |

TABLE 38-continued
| Compound No. | Structural Formula |
|---|---|
| PP1141 | 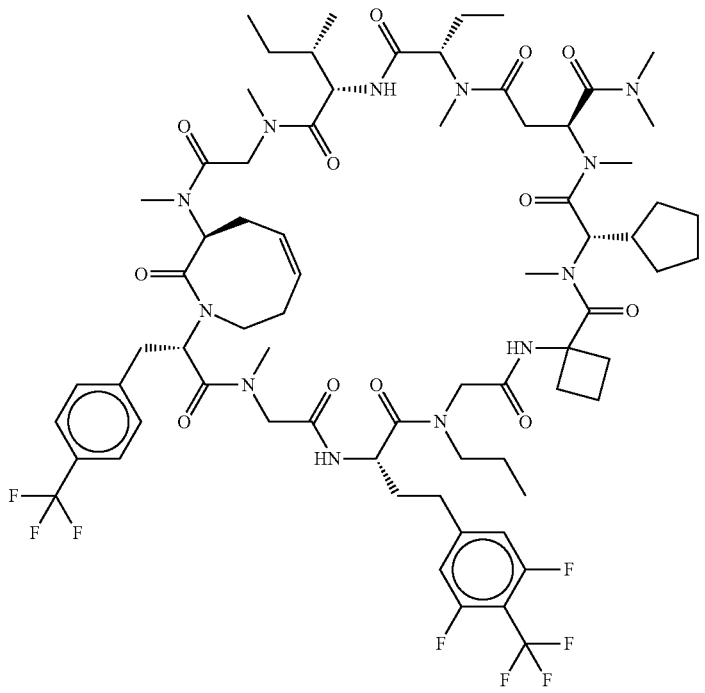 |
| PP1142 | 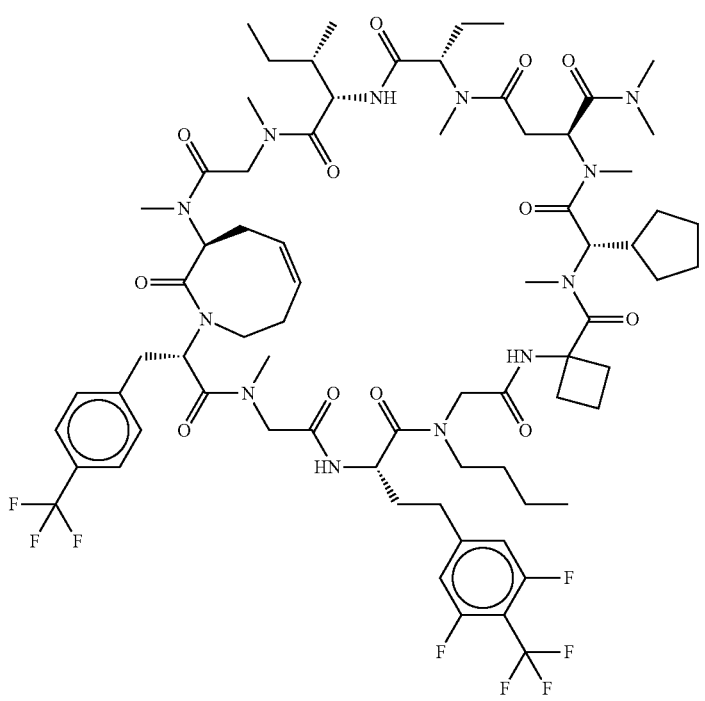 |

TABLE 38-continued
| Compound No. | Structural Formula |
| --- | --- |
| PP1143 | 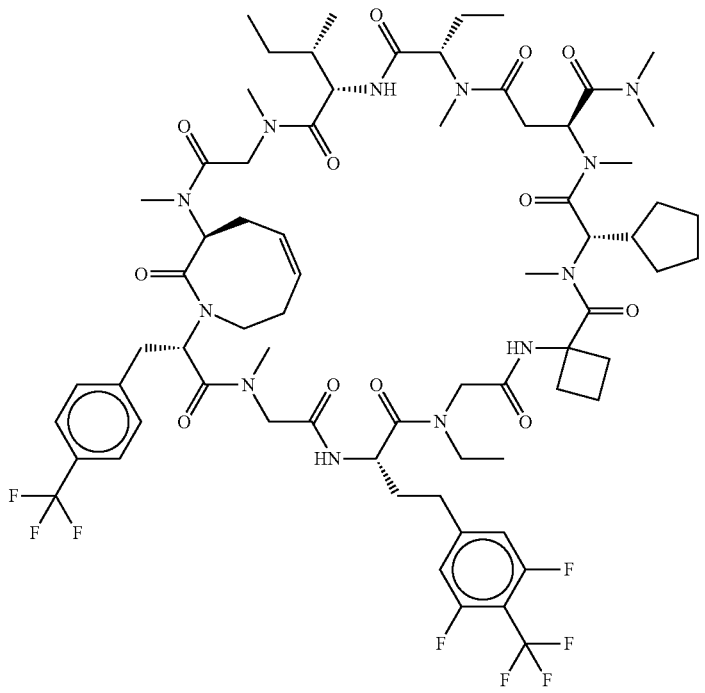 |
| PP1144 | 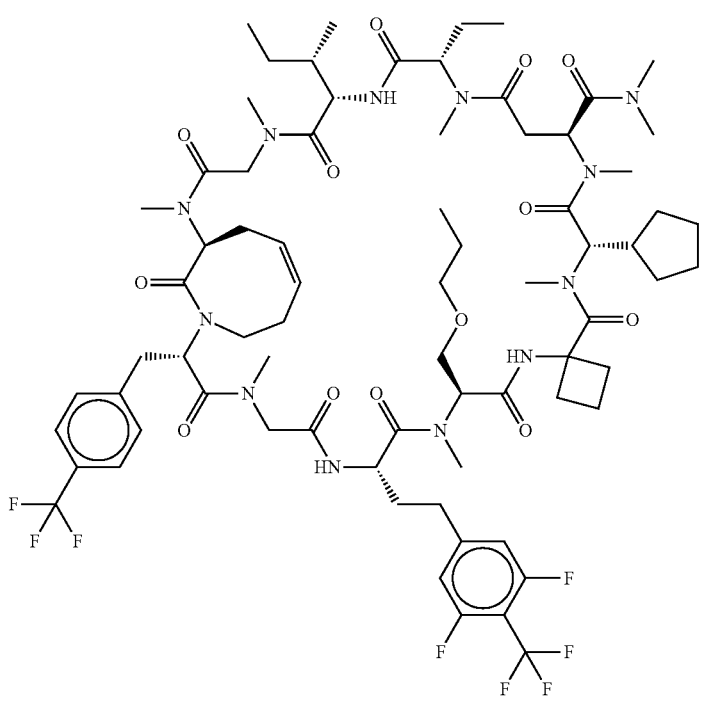 |

TABLE 38-continued
| Compound No. | Structural Formula |
|---|---|
| PP1145 | 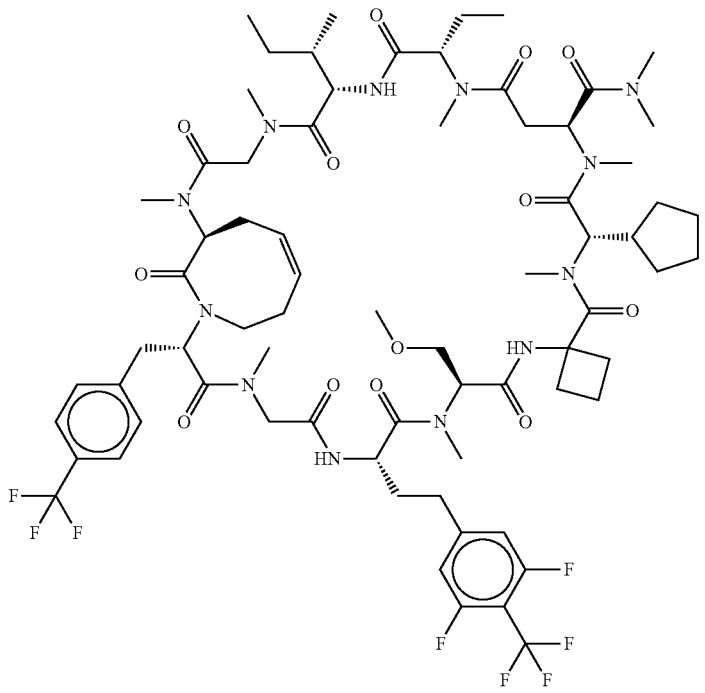 |
| PP1146 | 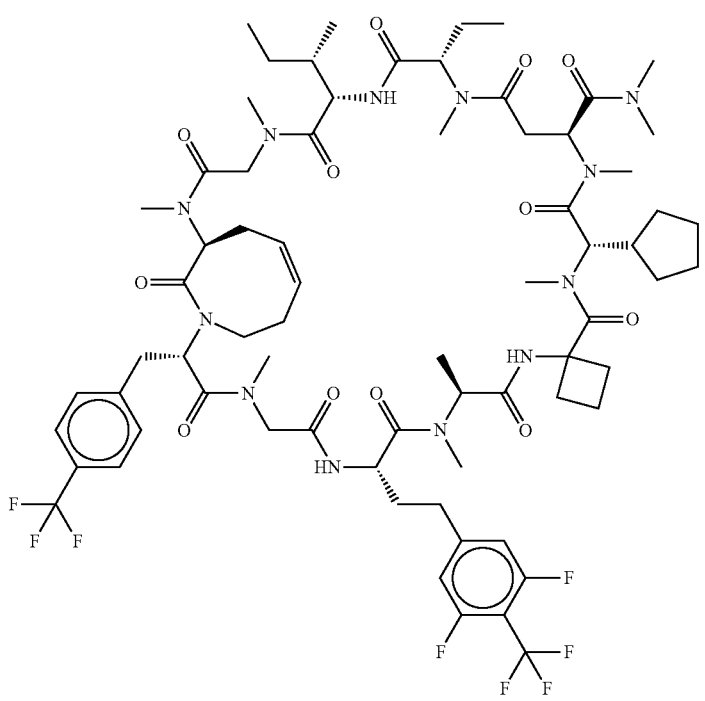 |

TABLE 38-continued
| Compound No. | Structural Formula |
|---|---|
| PP1147 | 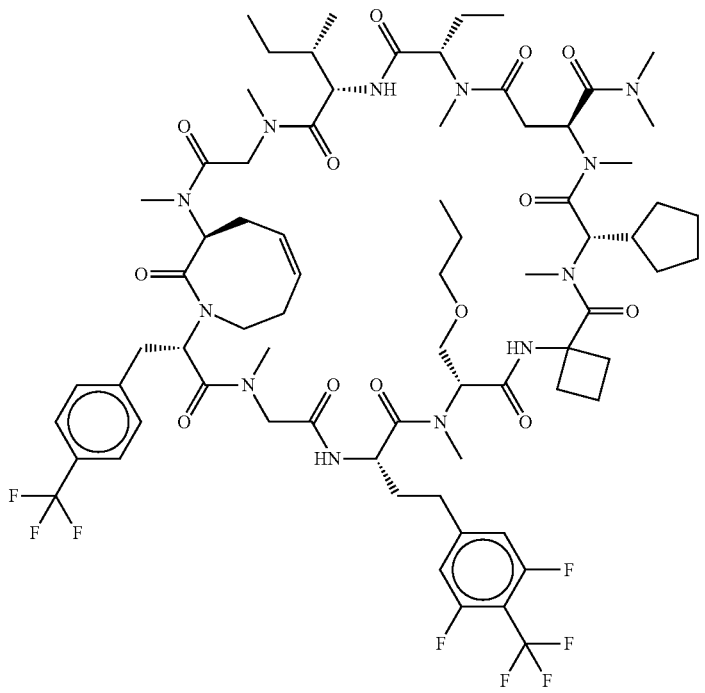 |
| PP1148 | 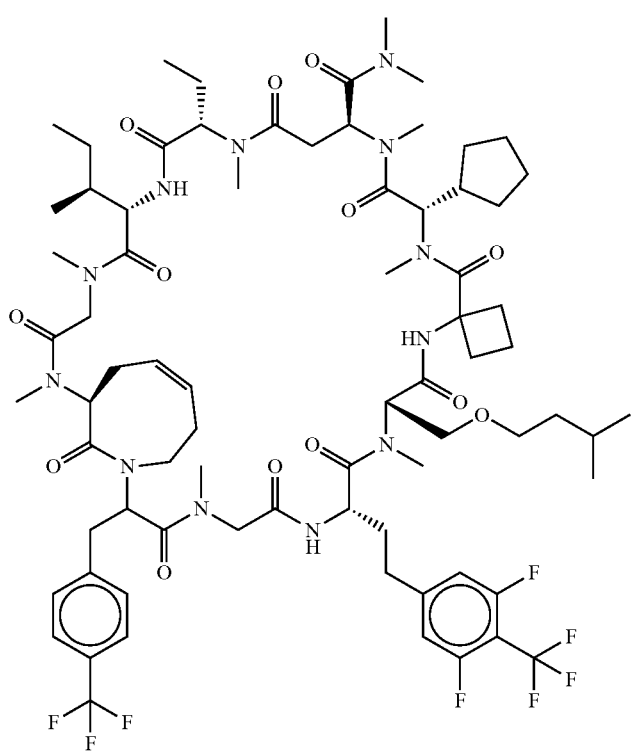 |

TABLE 38-continued
| Compound No. | Structural Formula |
|---|---|
| PP1149 | 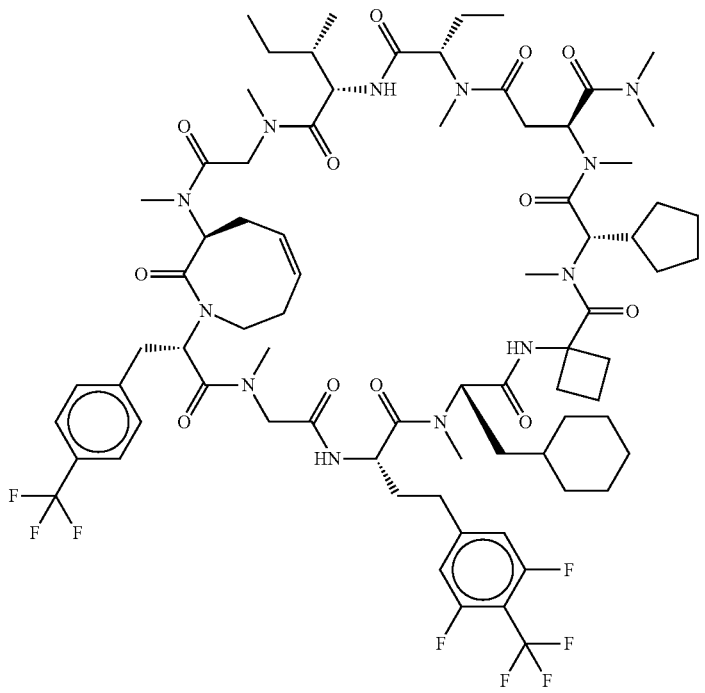 |
| PP1150 | 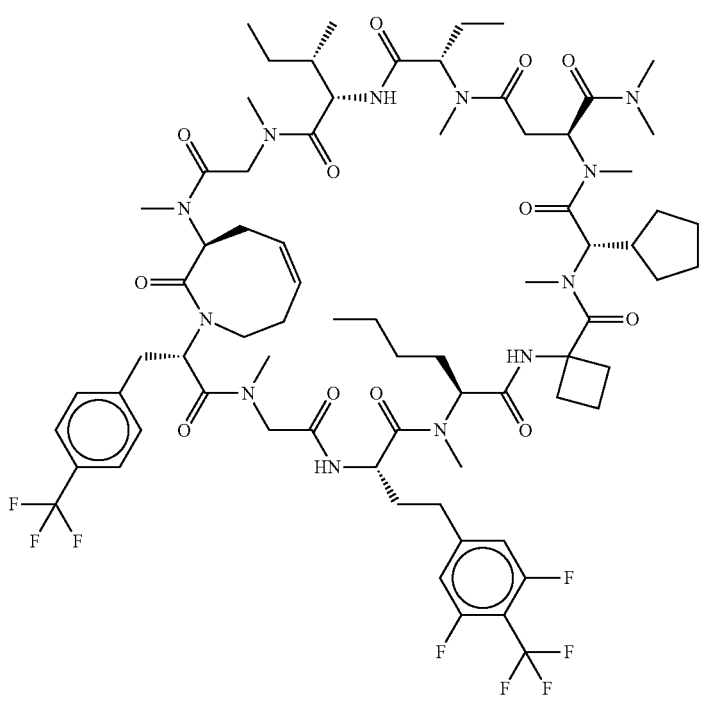 |

TABLE 38-continued

| Compound No. | Structural Formula |
|---|---|
| PP1151 | |
| PP1152 | |

TABLE 38-continued
| Compound No. | Structural Formula |
|---|---|
| PP1153 | 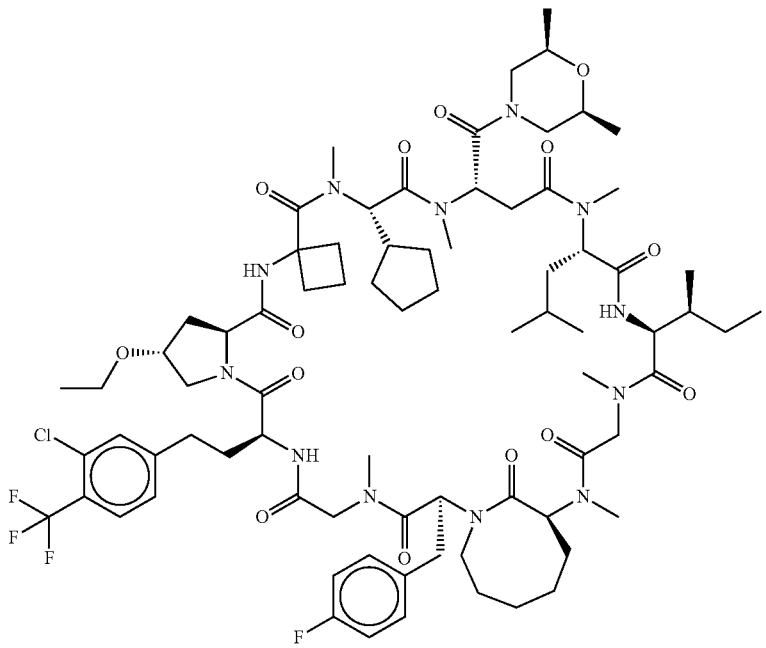 |
| PP1154 | 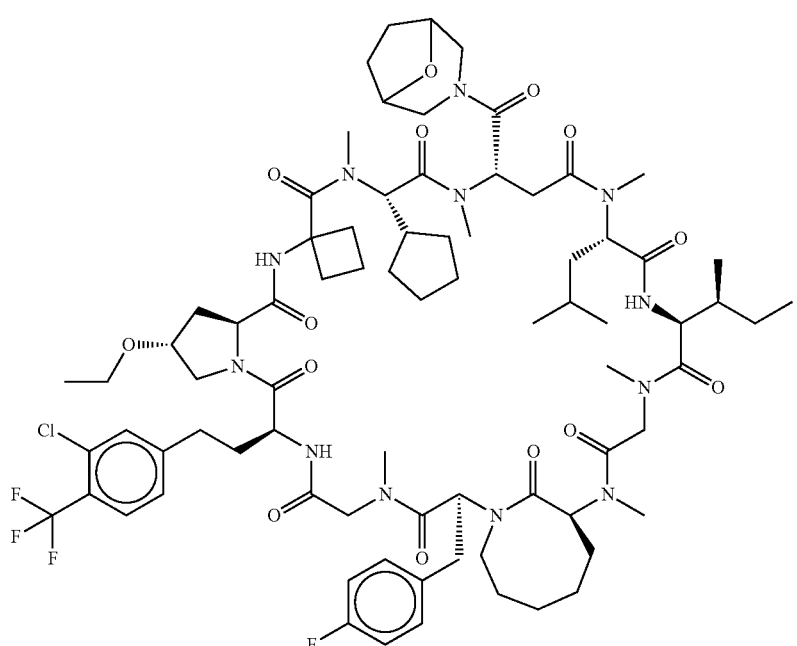 |

TABLE 38-continued

| Compound No. | Structural Formula |
| --- | --- |
| PP1155 | |
| PP1156 | |

TABLE 38-continued
| Compound No. | Structural Formula |
|---|---|
| PP1157 | 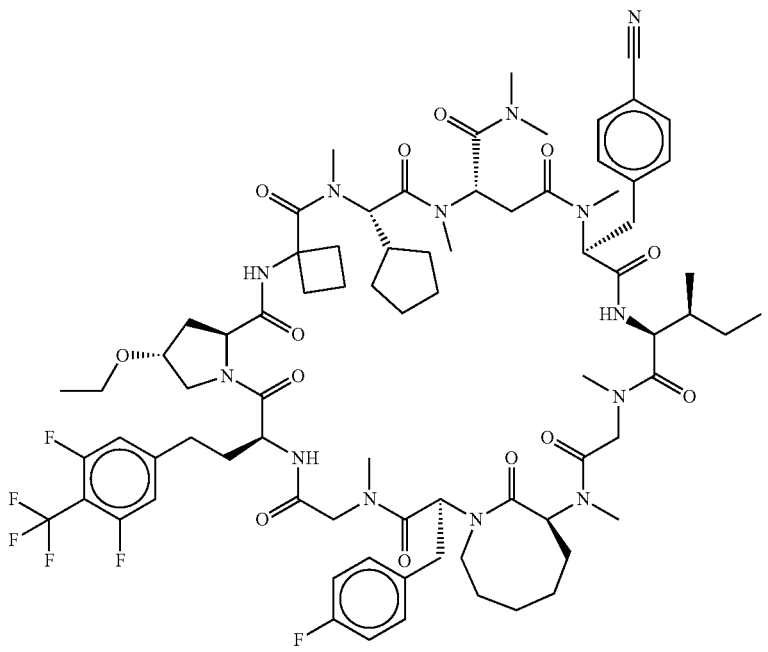 |
| PP1158 | 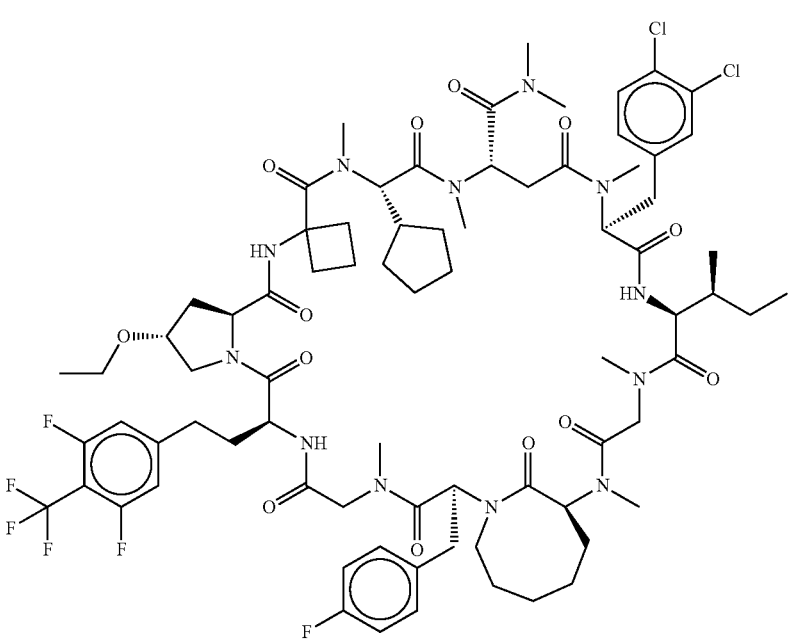 |

1973
TABLE 38-continued
| Compound No. | Structural Formula |
|---|---|
| PP1159 | 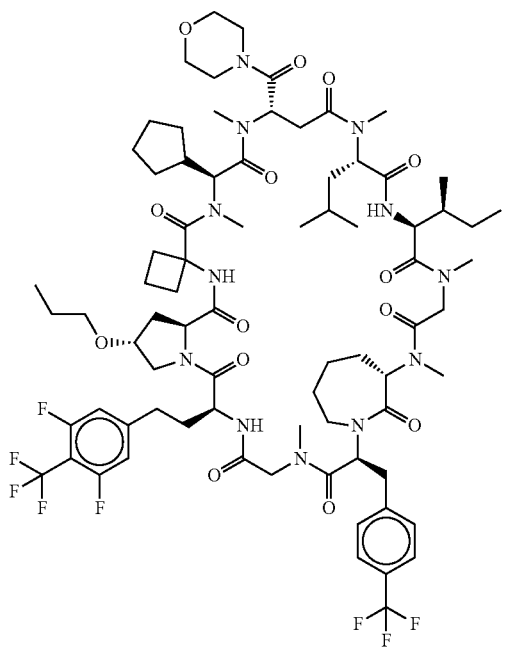 |
| PP1160 | 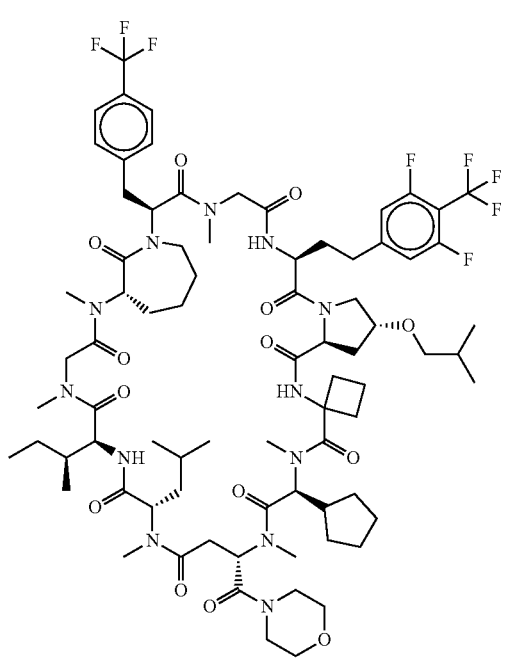 |

TABLE 38-continued
| Compound No. | Structural Formula |
|---|---|
| PP1161 | 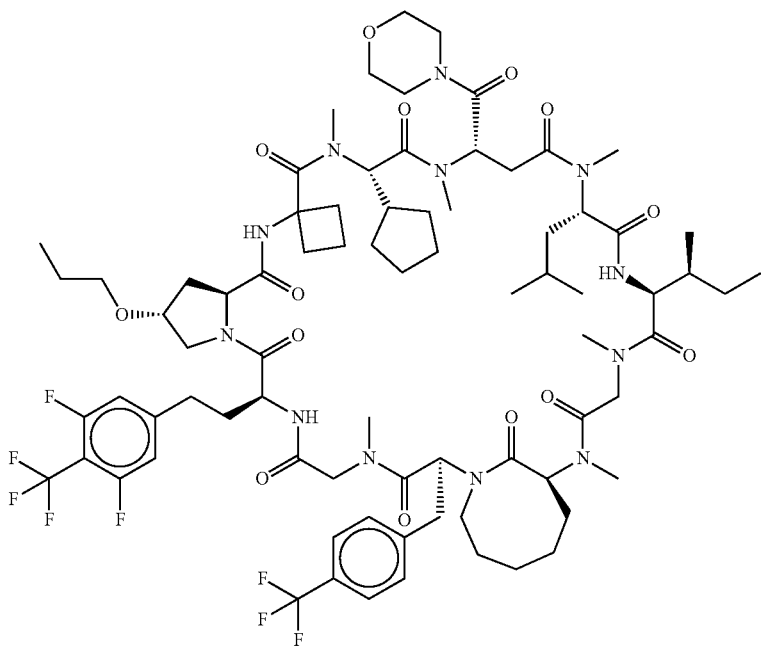 |
| PP1162 | 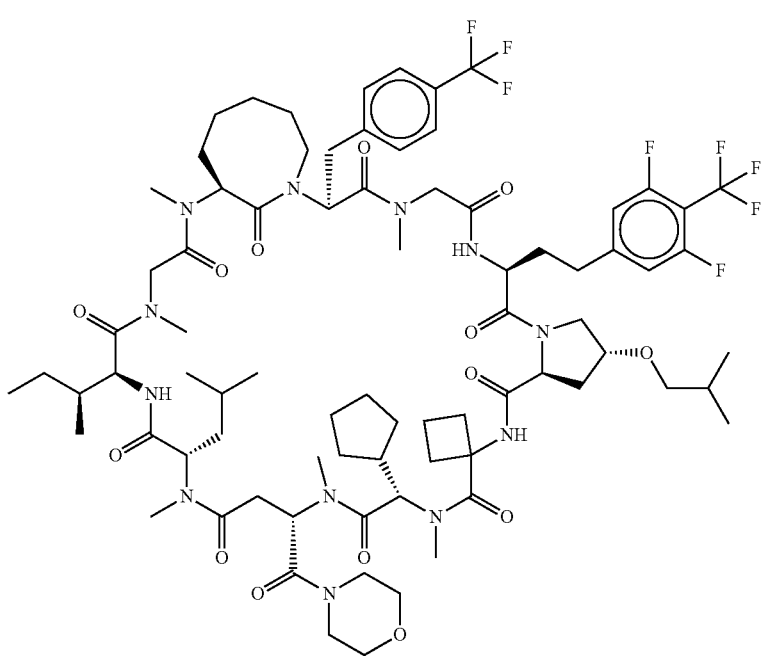 |

TABLE 38-continued

| Compound No. | Structural Formula |
|---|---|
| PP1163 | |
| PP1164 | |

TABLE 38-continued

| Compound No. | Structural Formula |
|---|---|
| PP1165 | |
| PP1166 | |

1981
TABLE 38-continued
| Compound No. | Structural Formula |
| --- | --- |
| PP1167 | 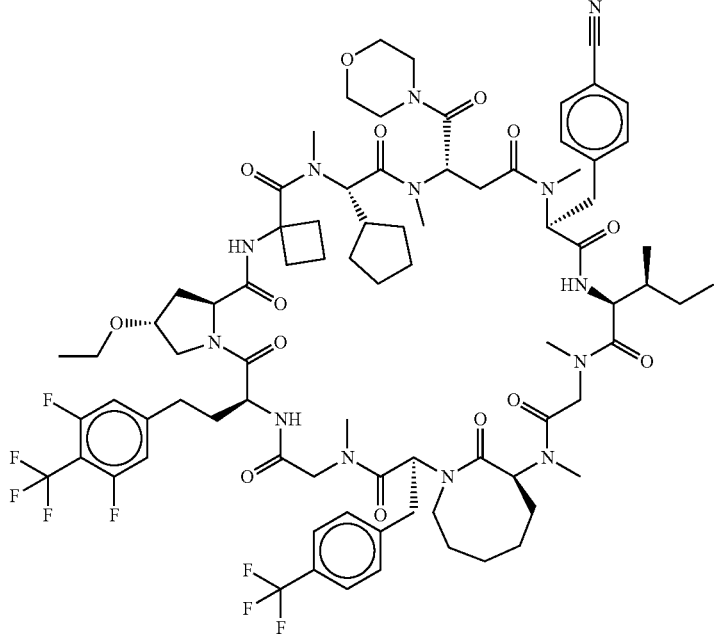 |
| PP1168 | 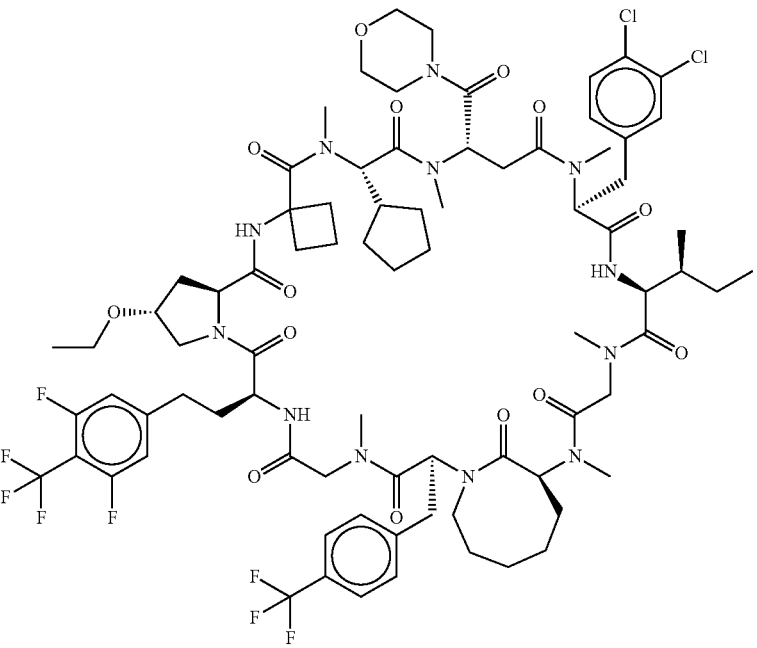 |

TABLE 38-continued
| Compound No. | Structural Formula |
|---|---|
| PP1169 | 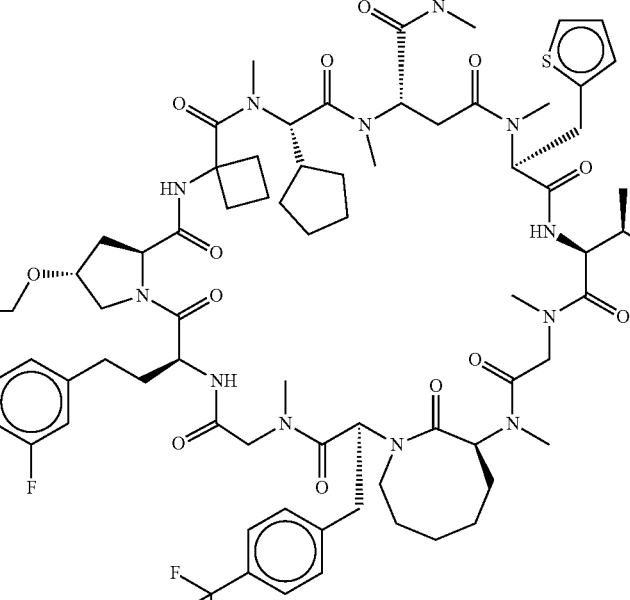 |
| PP1170 | 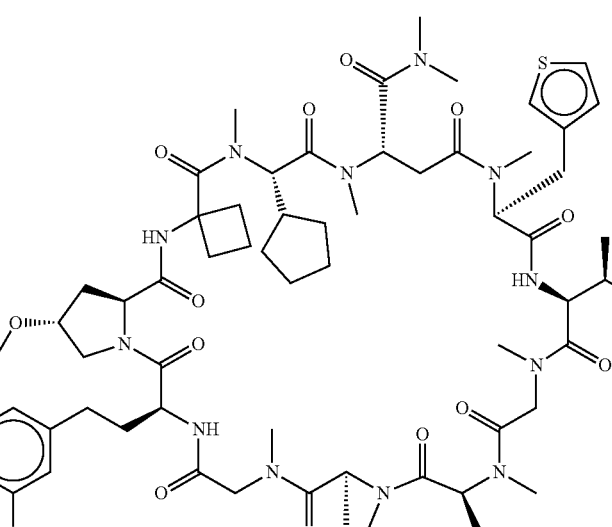 |

TABLE 38-continued
| Compound No. | Structural Formula |
|---|---|
| PP1171 | 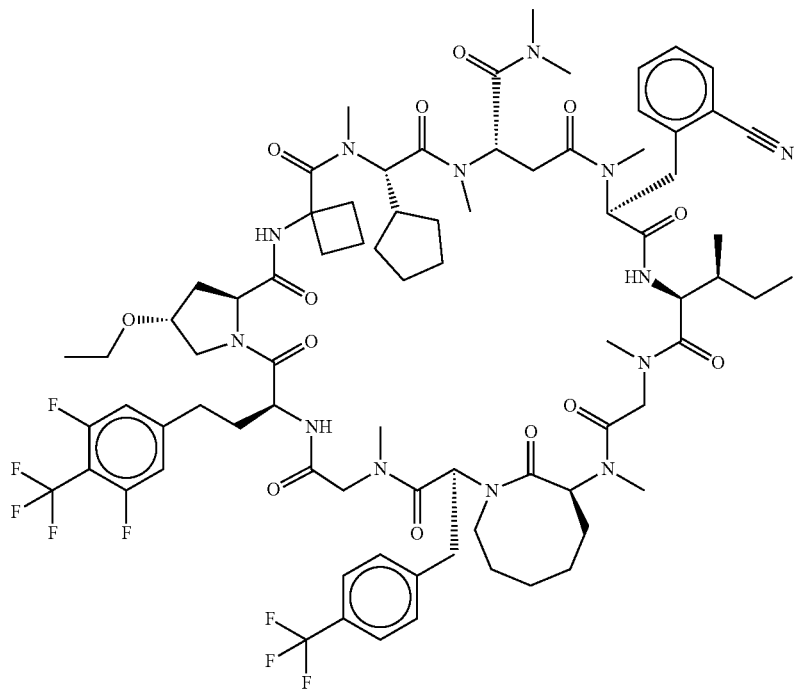 |
| PP1172 | 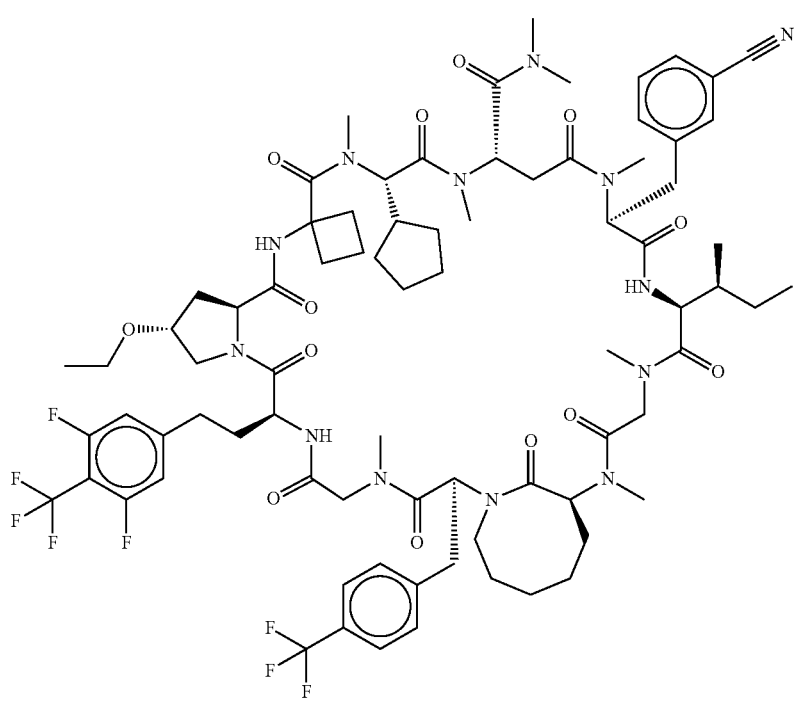 |

TABLE 38-continued
| Compound No. | Structural Formula |
|---|---|
| PP1173 | 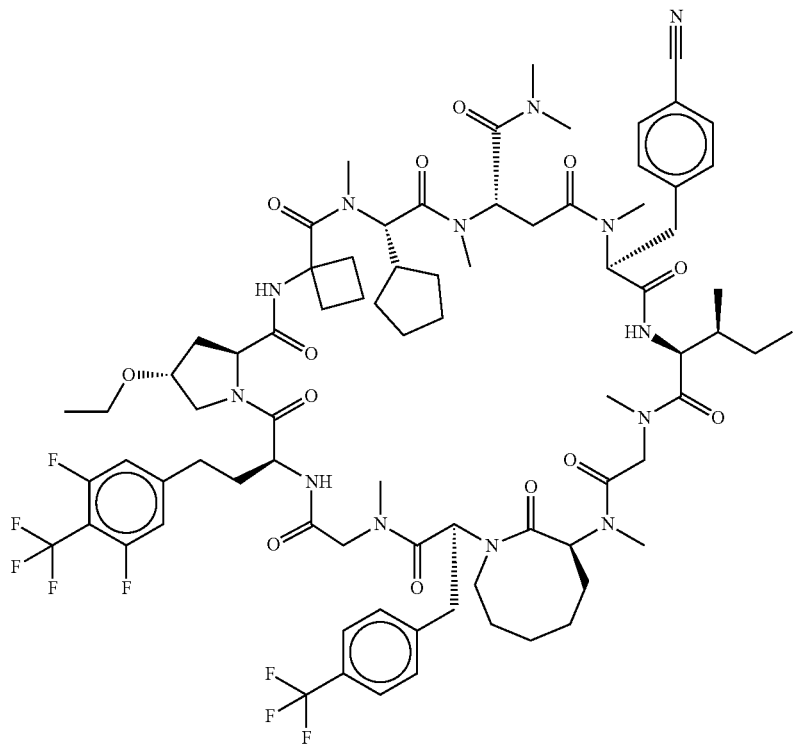 |
| PP1174 | 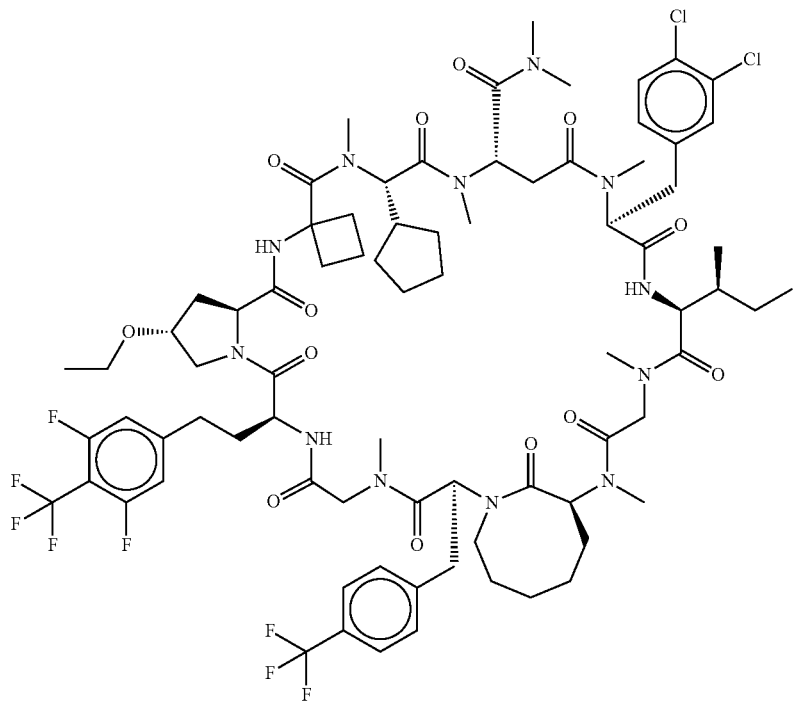 |

TABLE 38-continued
| Compound No. | Structural Formula |
|---|---|
| PP1175 | 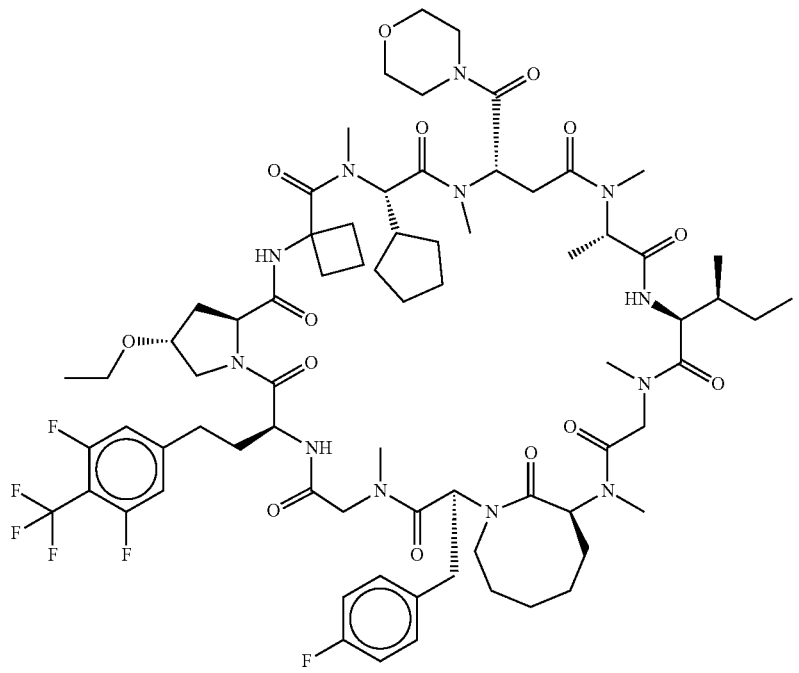 |
| PP1176 | 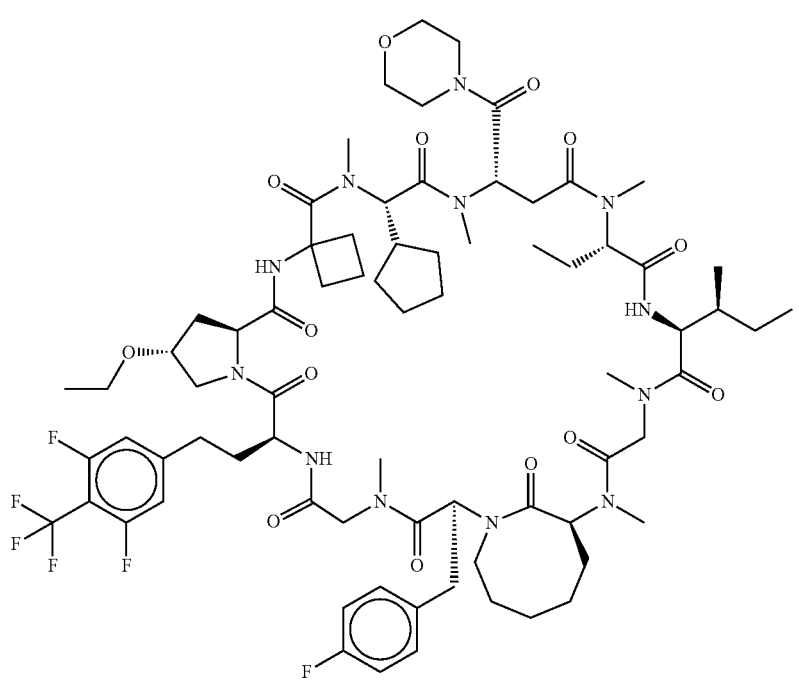 |

TABLE 38-continued
| Compound No. | Structural Formula |
|---|---|
| PP1177 | 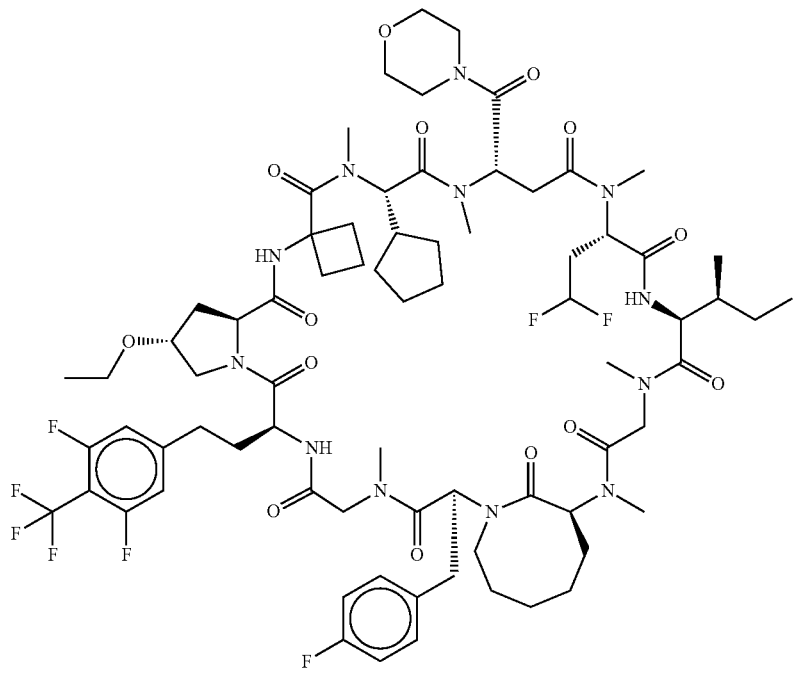 |
| PP1178 | 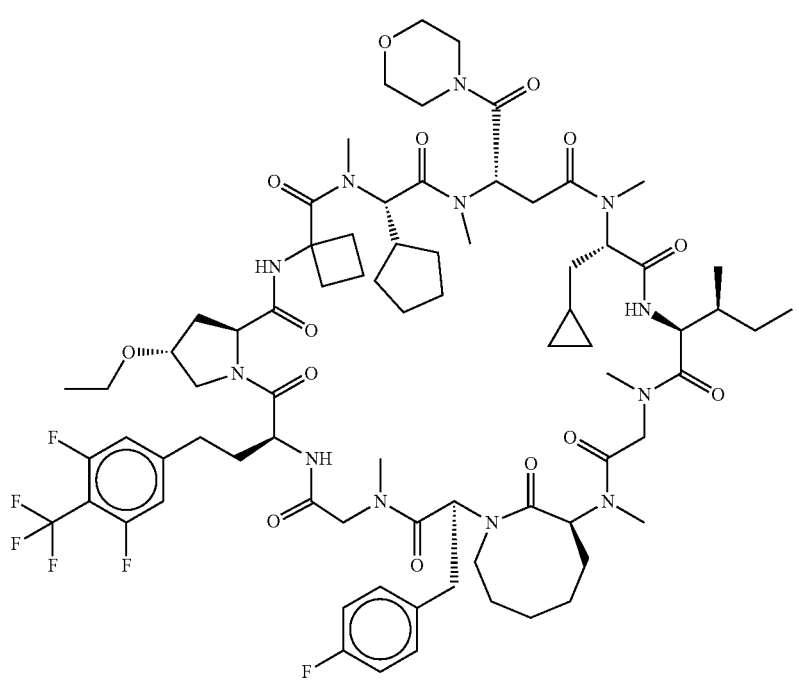 |

TABLE 38-continued
| Compound No. | Structural Formula |
|---|---|
| PP1179 | 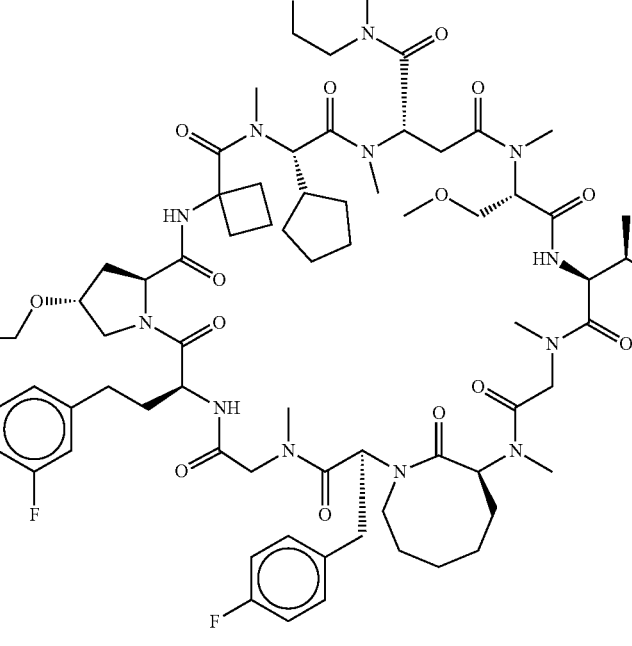 |
| PP1180 | 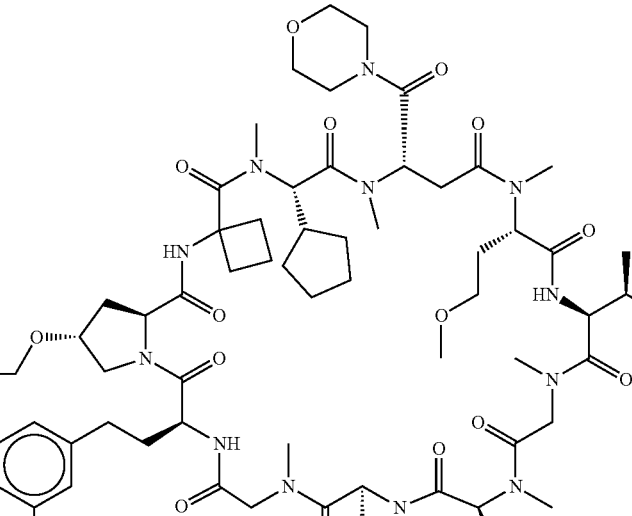 |

TABLE 38-continued
| Compound No. | Structural Formula |
|---|---|
| PP1181 | 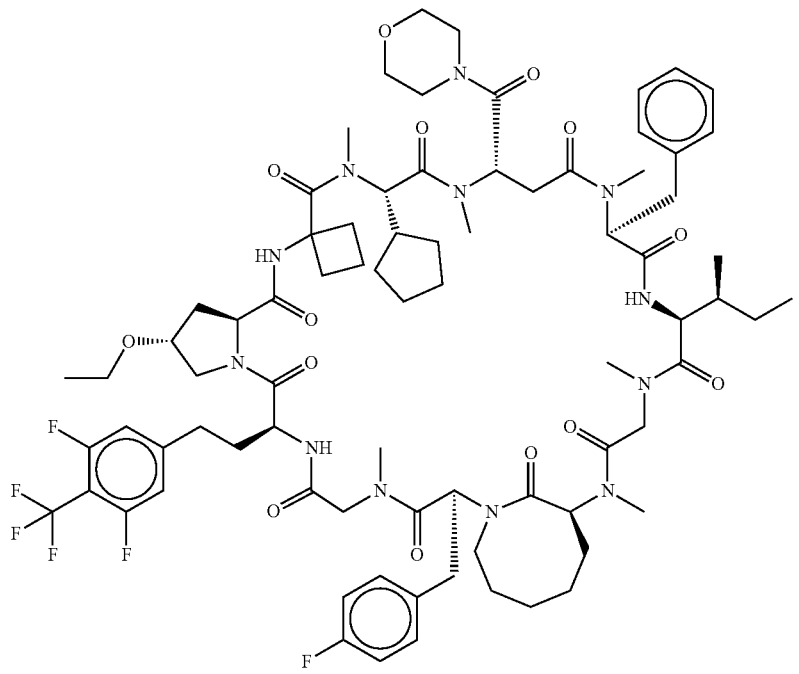 |
| PP1182 | 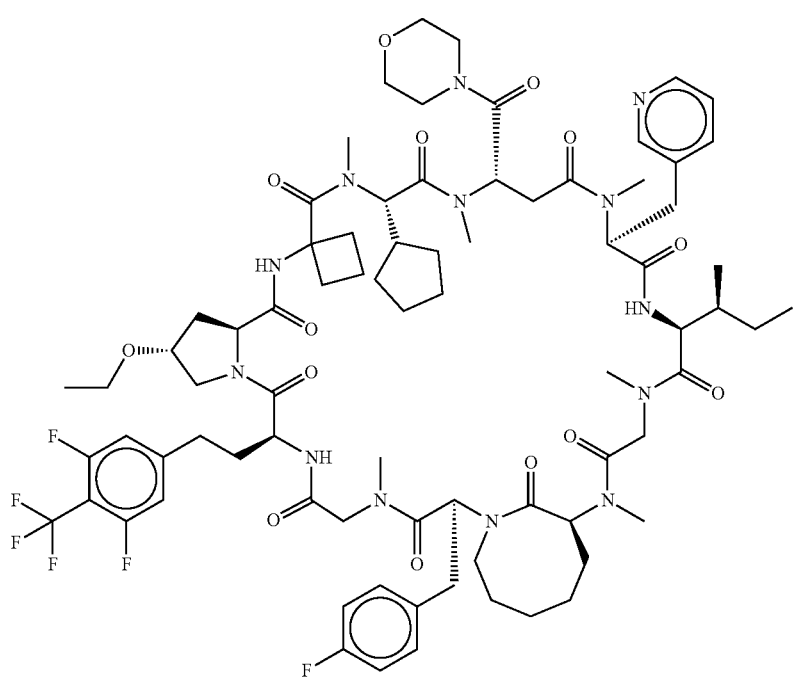 |

TABLE 38-continued
| Compound No. | Structural Formula |
|---|---|
| PP1183 | 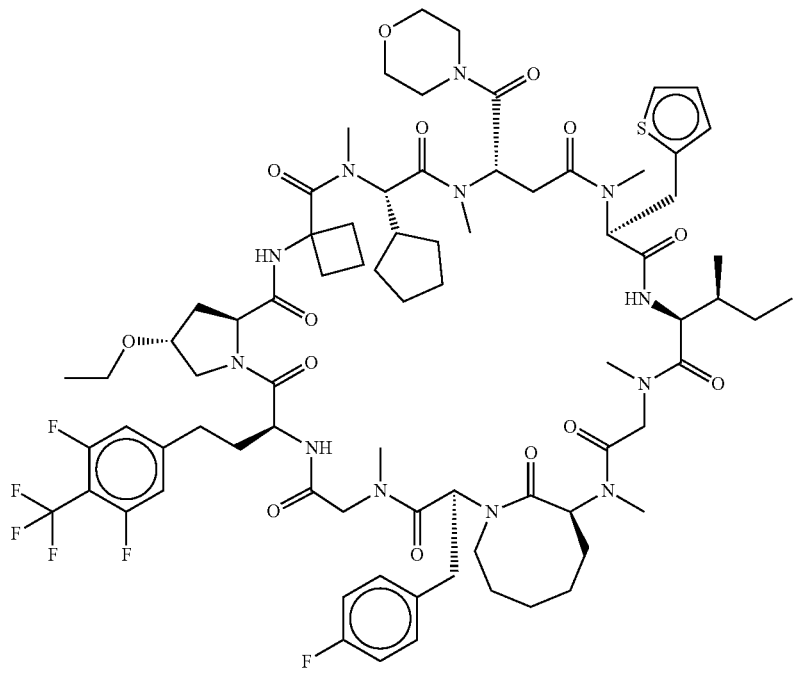 |
| PP1184 | 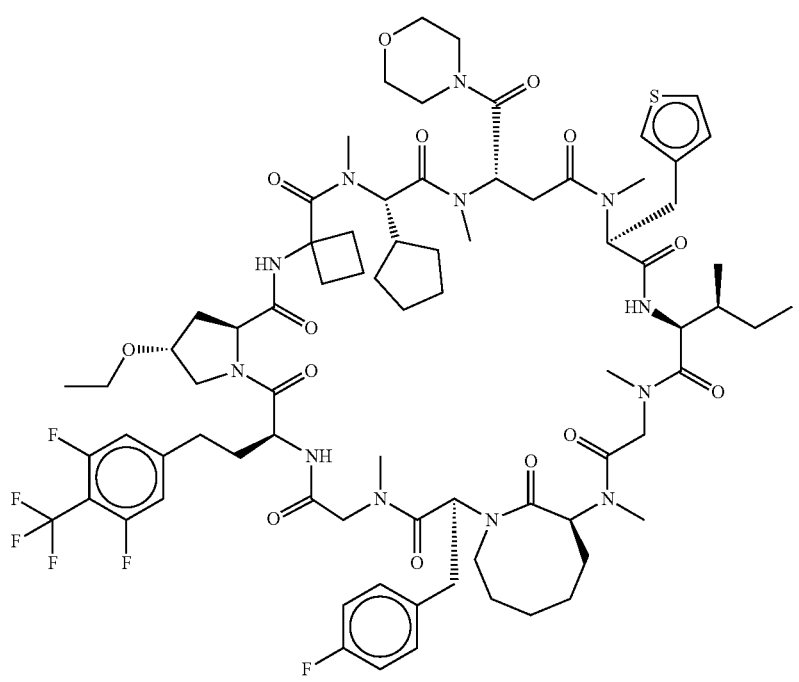 |

TABLE 38-continued
| Compound No. | Structural Formula |
|---|---|
| PP1185 | 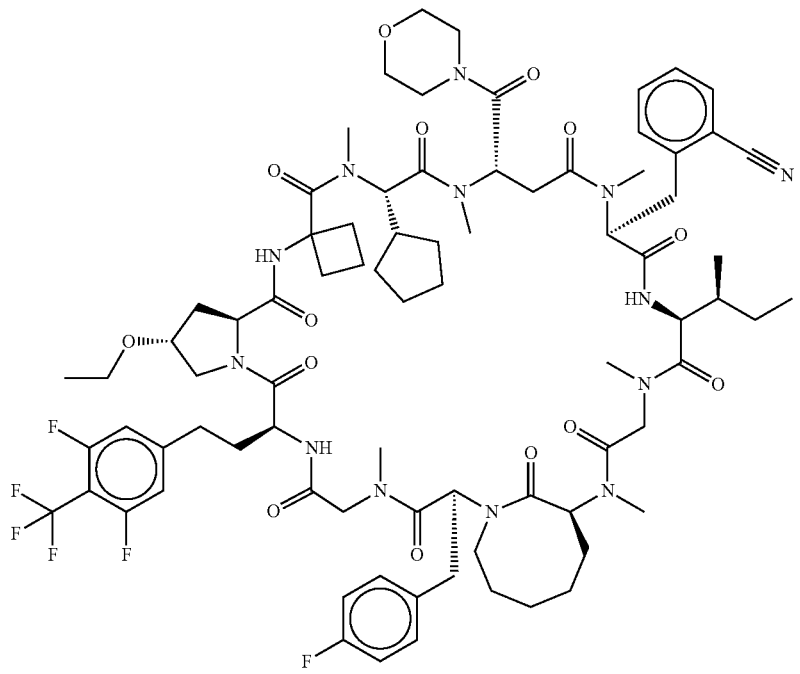 |
| PP1186 | 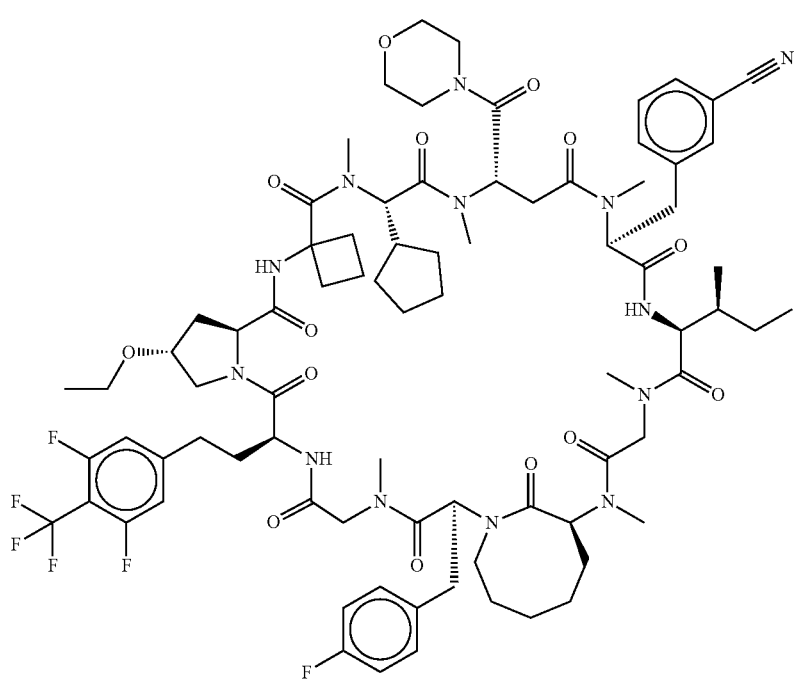 |

TABLE 38-continued

| Compound No. | Structural Formula |
|---|---|
| PP1187 | |
| PP1188 | |

TABLE 38-continued
| Compound No. | Structural Formula |
|---|---|
| PP1189 | 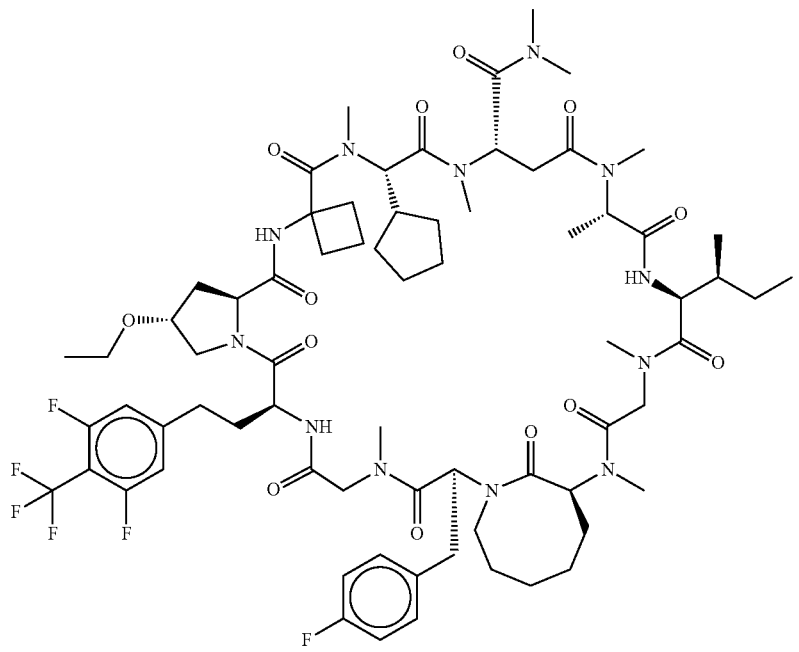 |
| PP1190 | 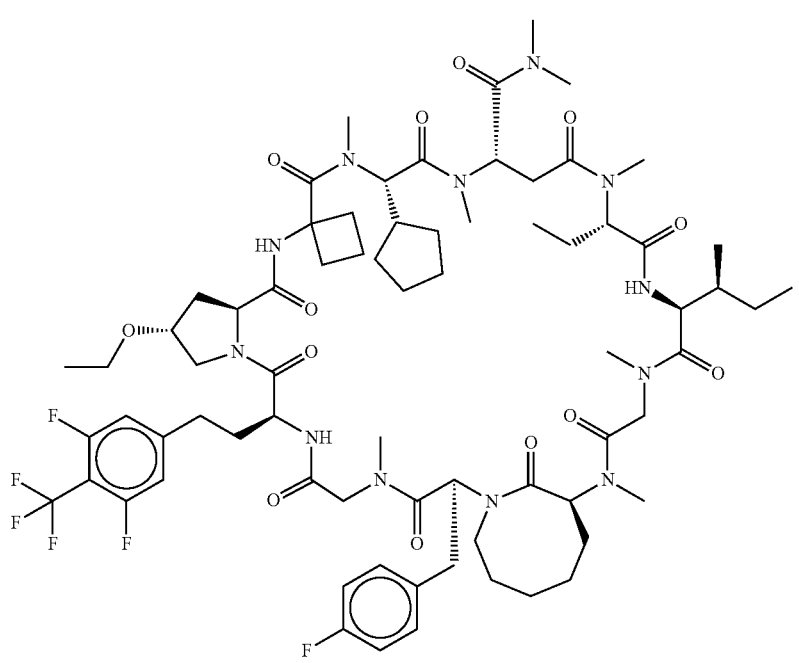 |

TABLE 38-continued
| Compound No. | Structural Formula |
|---|---|
| PP1191 | 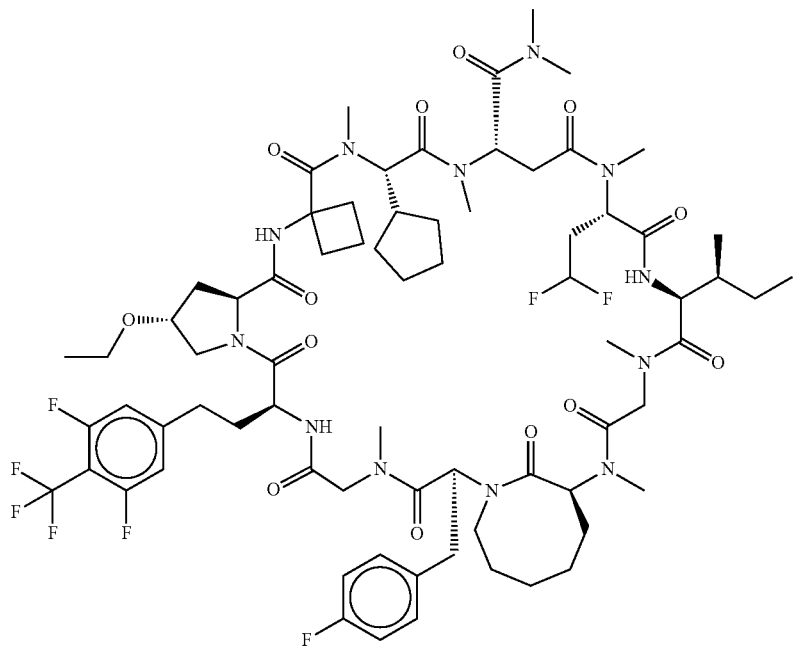 |
| PP1192 | 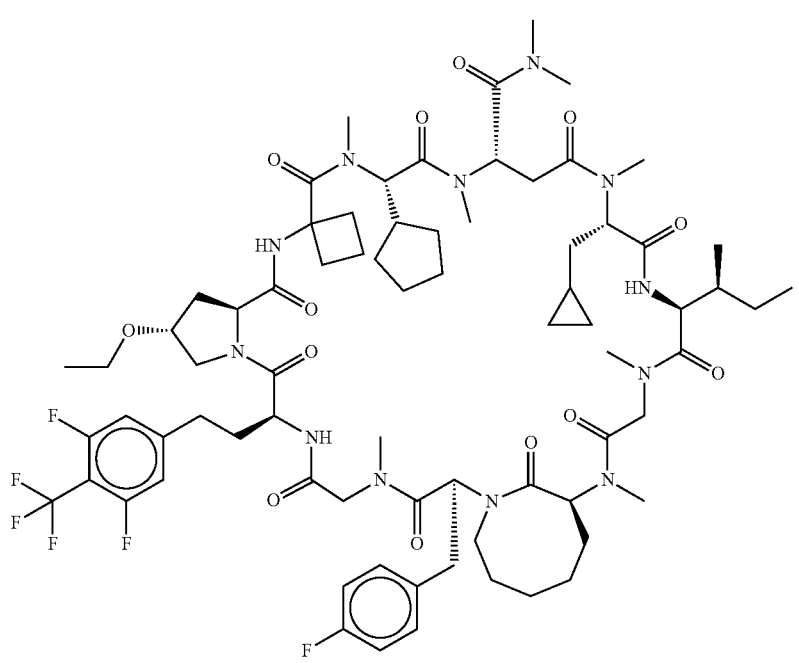 |

TABLE 38-continued
| Compound No. | Structural Formula |
|---|---|
| PP1193 | 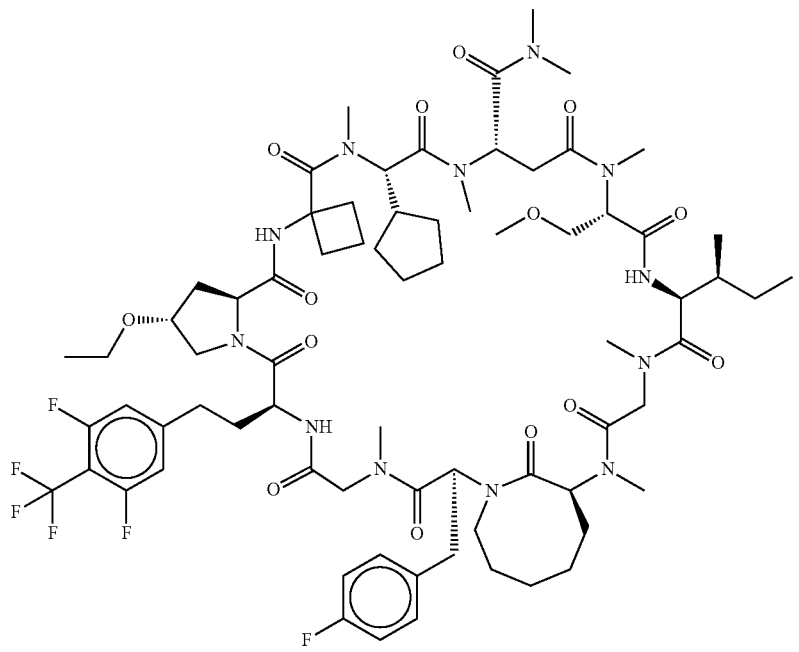 |
| PP1194 | 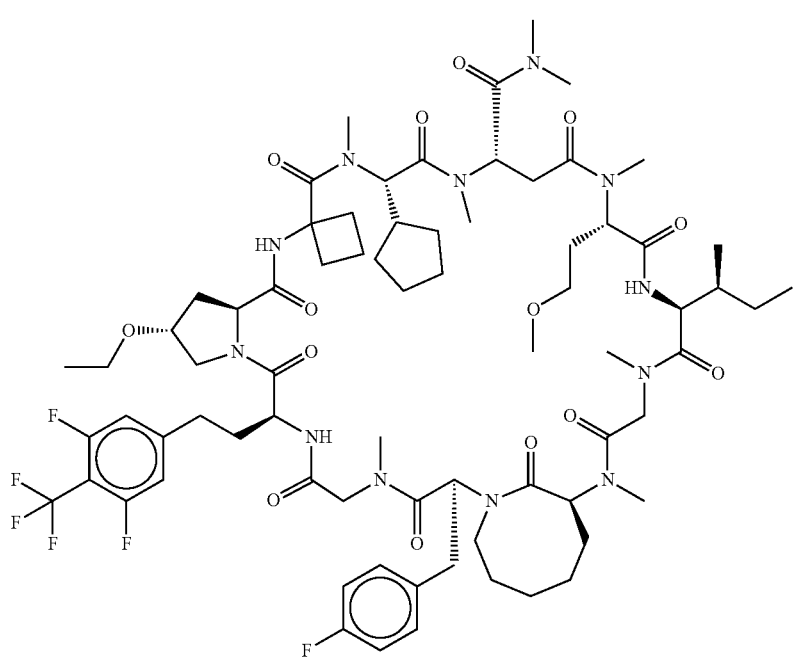 |

TABLE 38-continued
| Compound No. | Structural Formula |
|---|---|
| PP1195 | 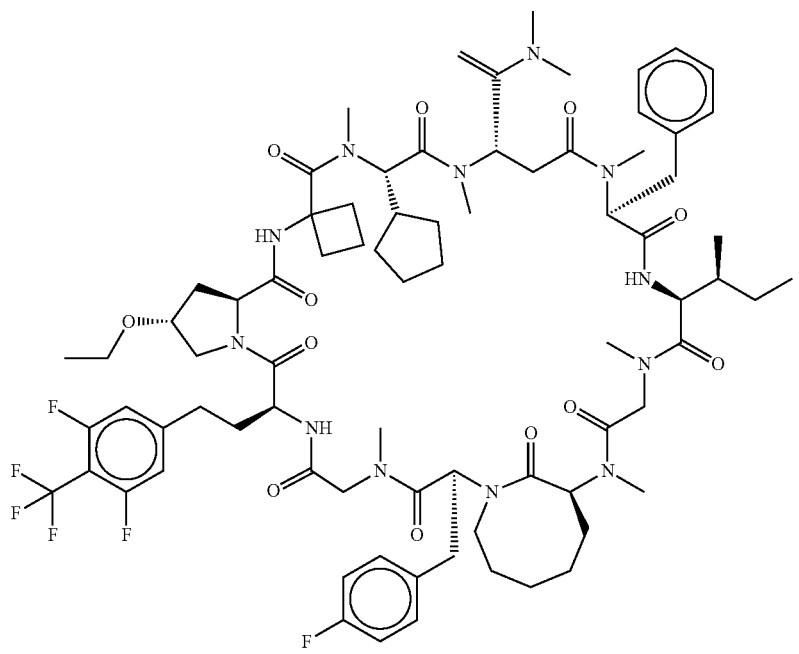 |
| PP1196 | 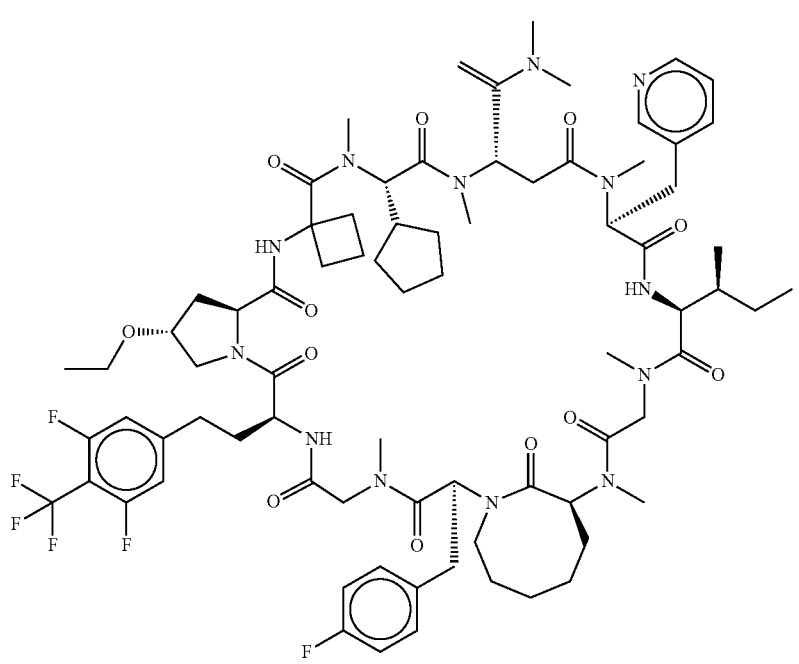 |

TABLE 38-continued
| Compound No. | Structural Formula |
|---|---|
| PP1197 | 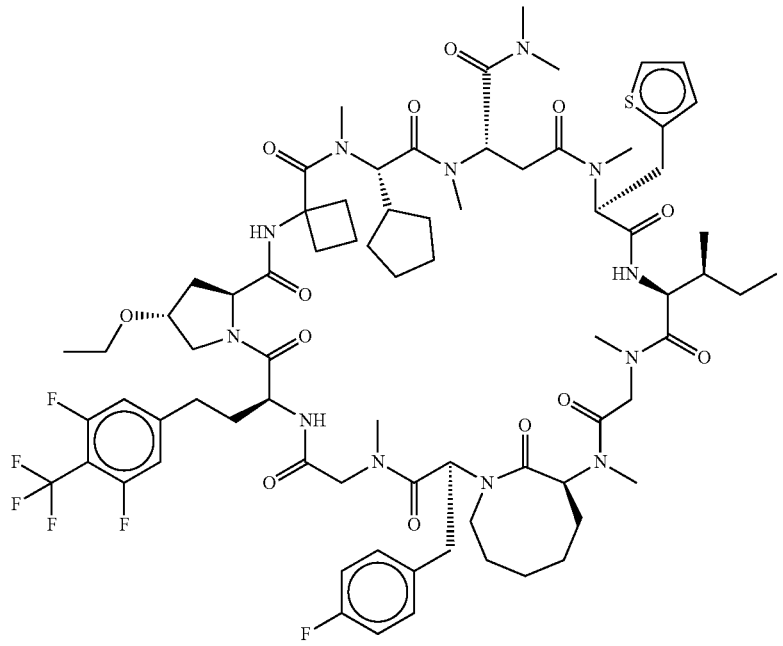 |
| PP1198 | 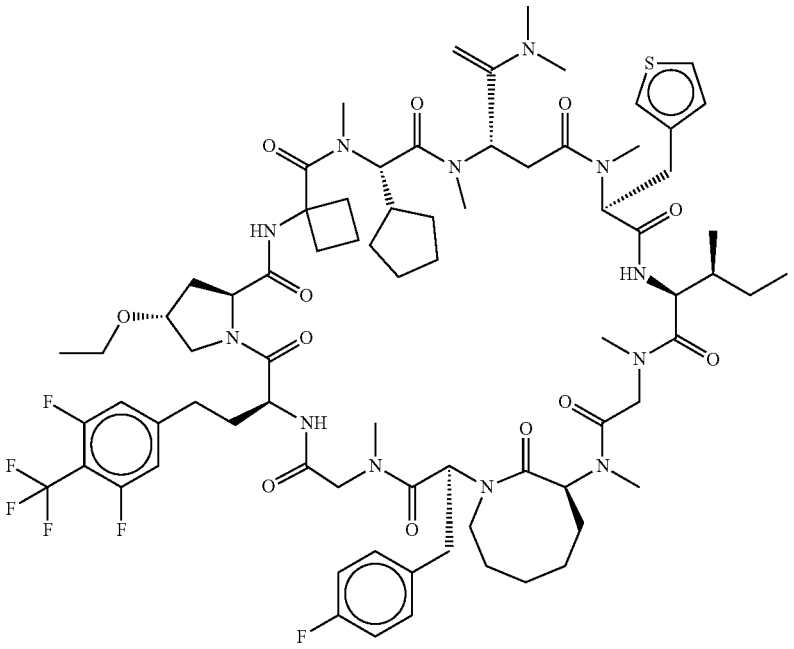 |

TABLE 38-continued

| Compound No. | Structural Formula |
| --- | --- |
| PP1199 | |
| PP1200 | |

TABLE 38-continued
| Compound No. | Structural Formula |
| --- | --- |
| PP1201 | 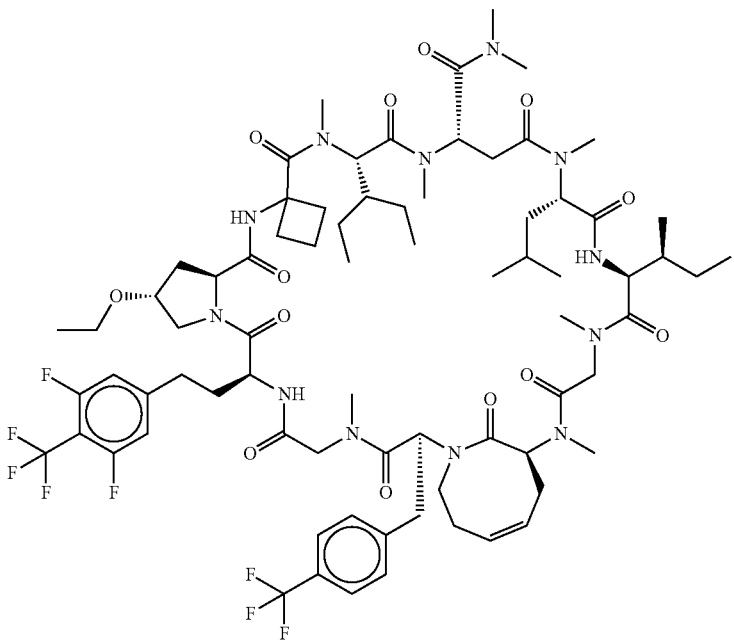 |
| PP1202 | 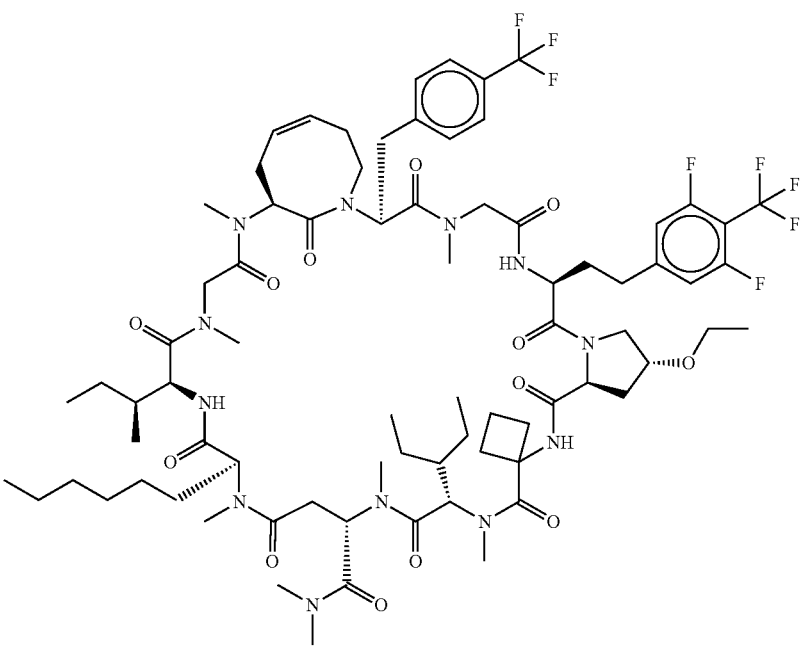 |

TABLE 38-continued

| Compound No. | Structural Formula |
|---|---|
| PP1203 | |
| PP1204 | |

TABLE 38-continued

| Compound No. | Structural Formula |
|---|---|
| PP1205 | |
| PP1206 | |

TABLE 38-continued
| Compound No. | Structural Formula |
|---|---|
| PP1207 | 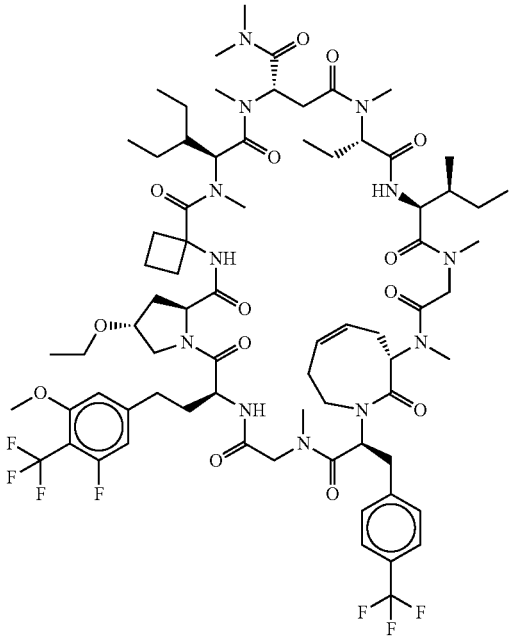 |
| PP1208 | 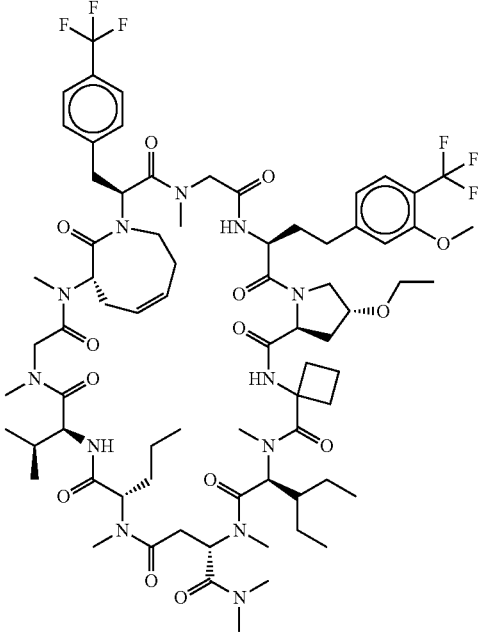 |

TABLE 38-continued
| Compound No. | Structural Formula |
|---|---|
| PP1209 | 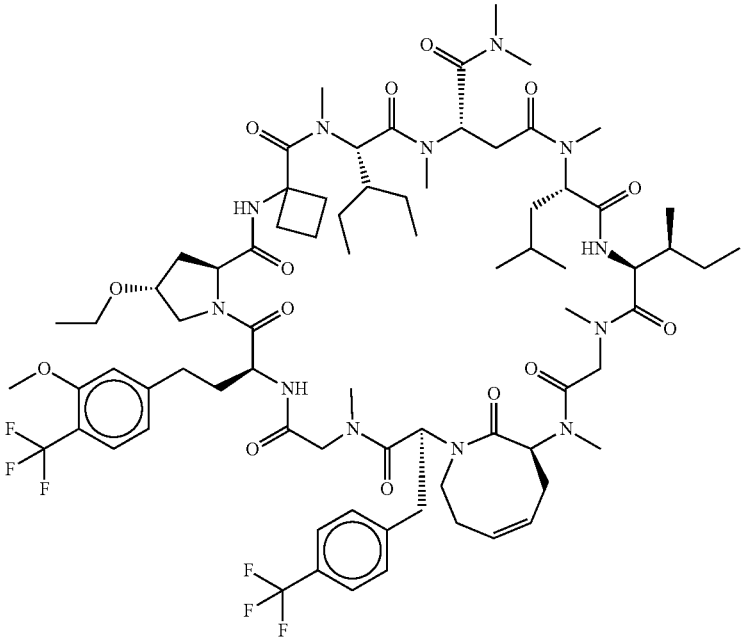 |
| PP1210 | 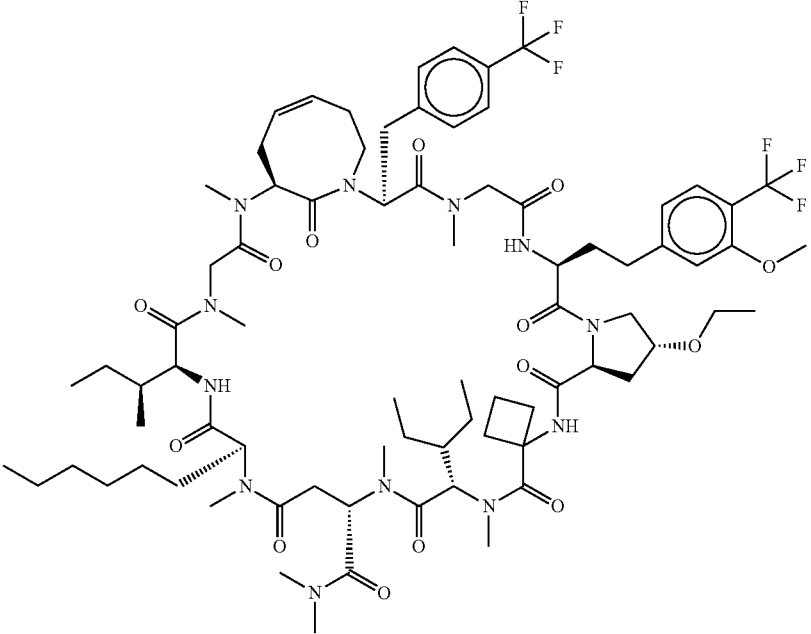 |

TABLE 38-continued
| Compound No. | Structural Formula |
|---|---|
| PP1211 | 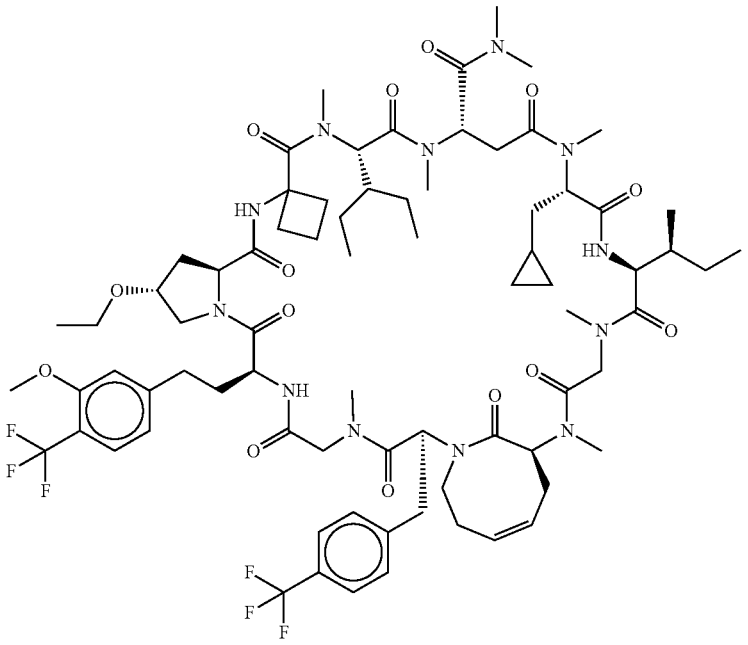 |
| PP1212 | 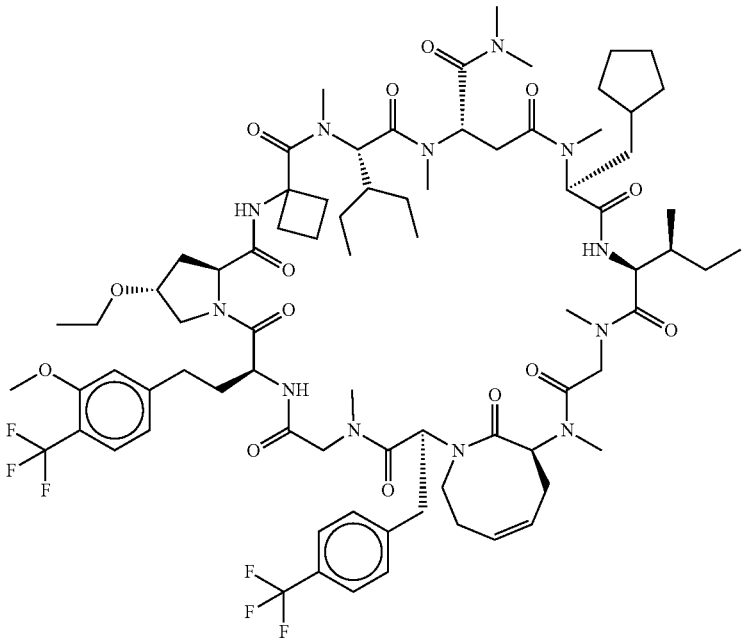 |

TABLE 38-continued
| Compound No. | Structural Formula |
|---|---|
| PP1213 | 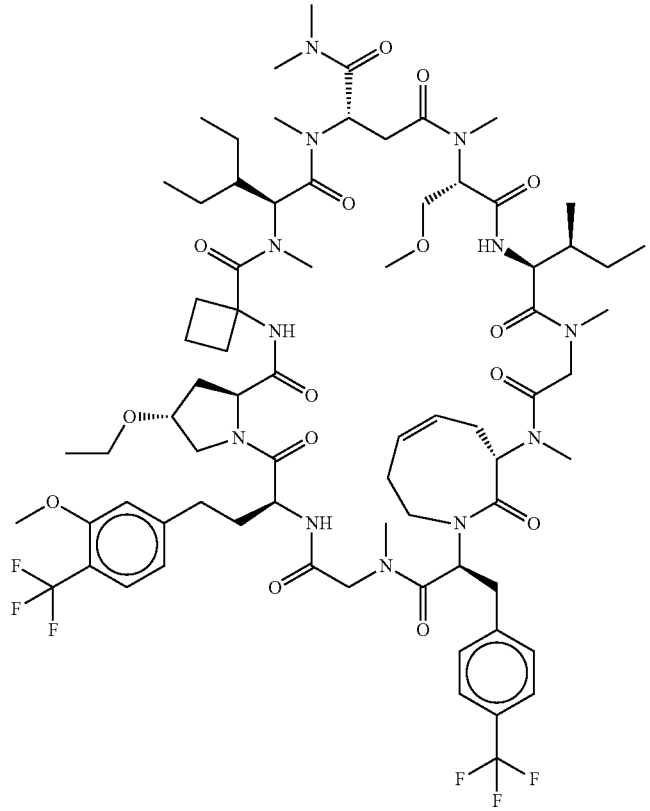 |
| PP1214 | 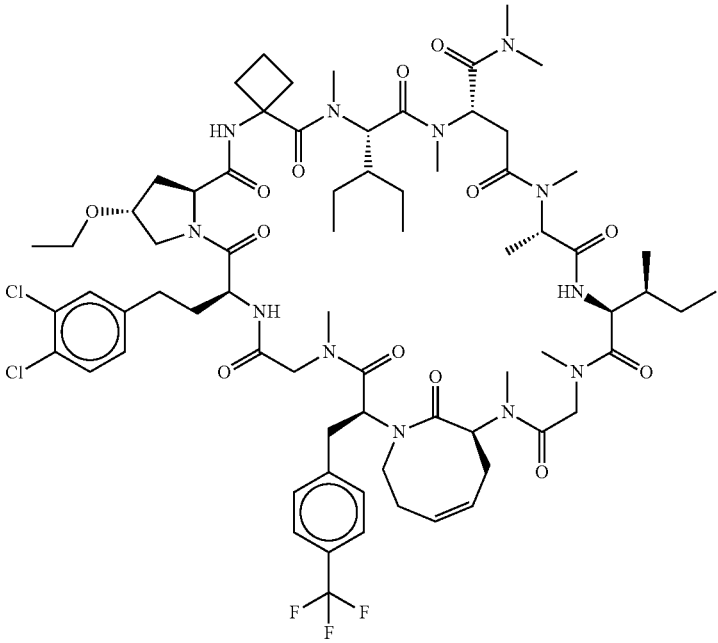 |

TABLE 38-continued
| Compound No. | Structural Formula |
|---|---|
| PP1215 | 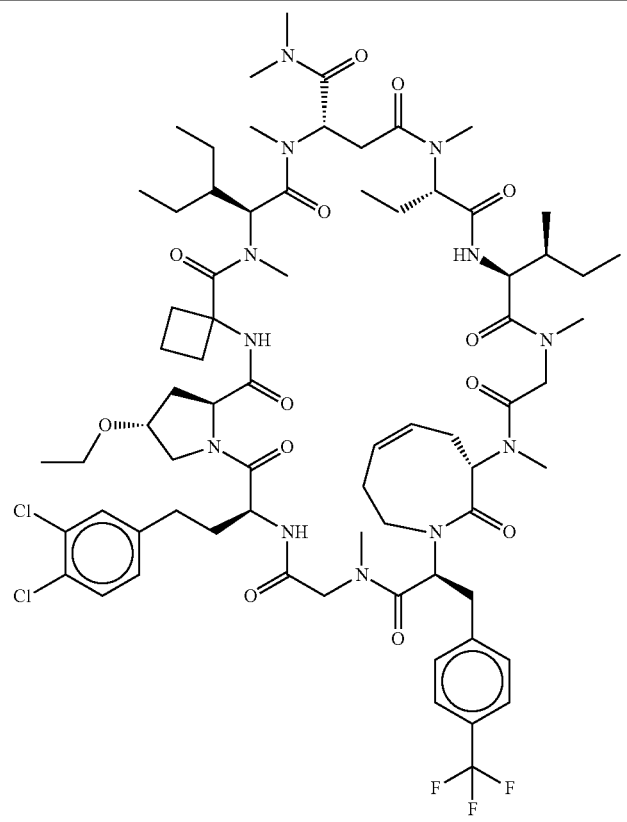 |
| PP1216 | 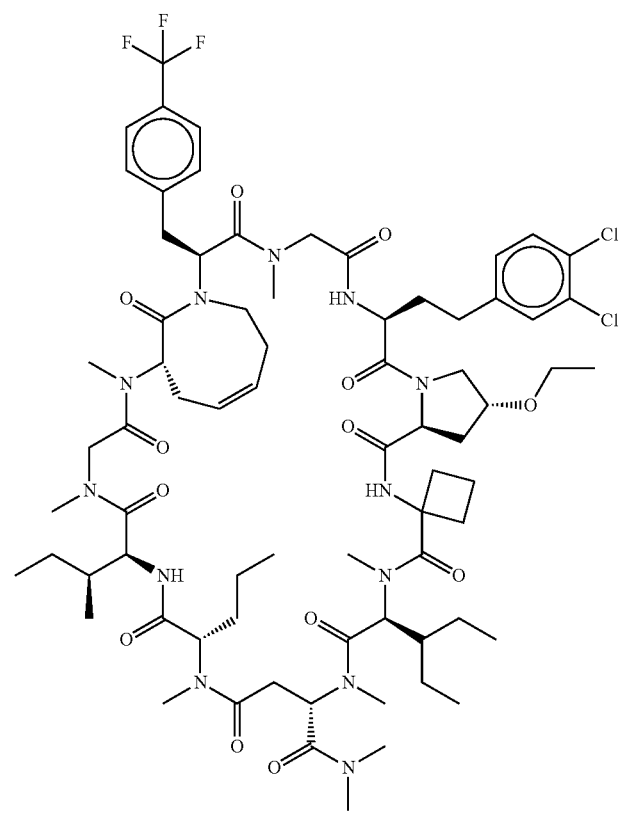 |

TABLE 38-continued
| Compound No. | Structural Formula |
|---|---|
| PP1217 | 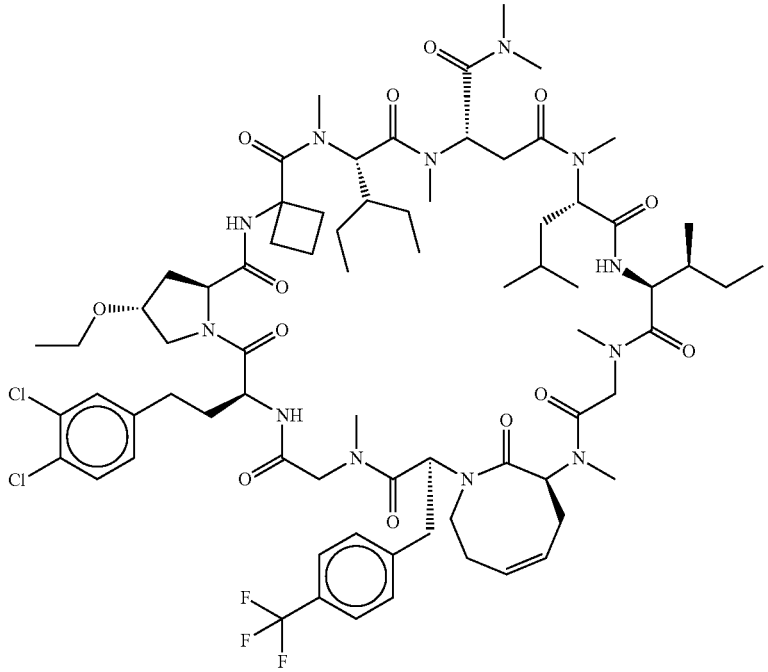 |
| PP1218 | 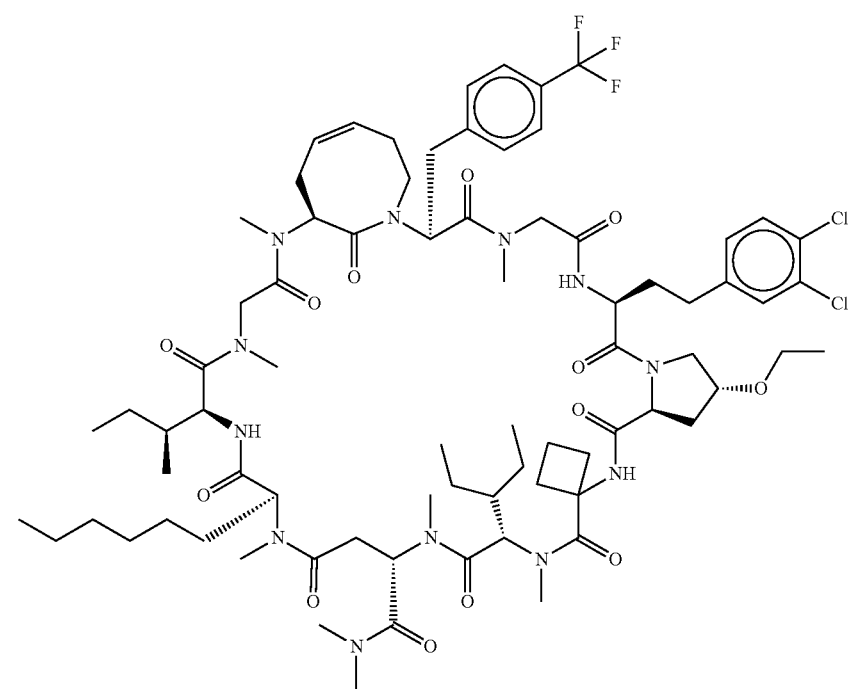 |

TABLE 38-continued
| Compound No. | Structural Formula |
|---|---|
| PP1219 | 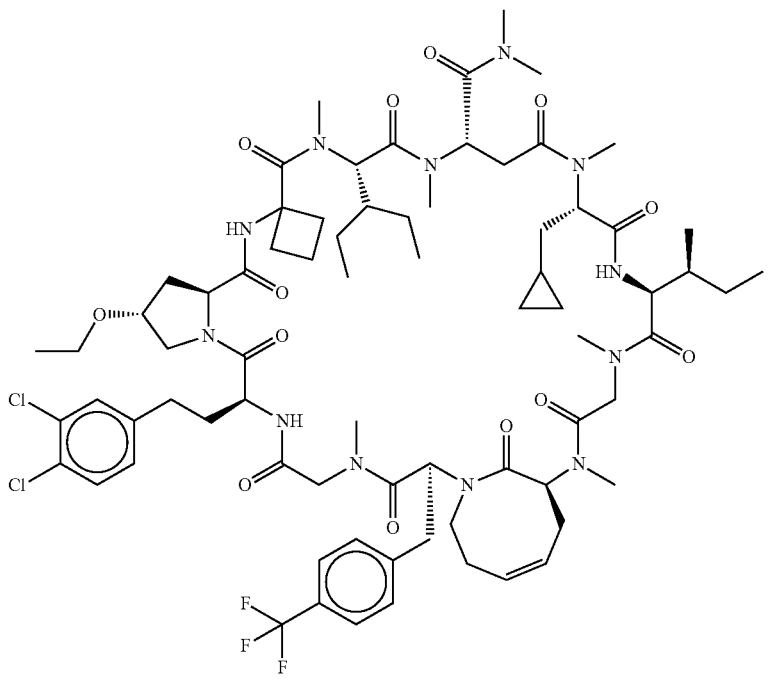 |
| PP1220 | 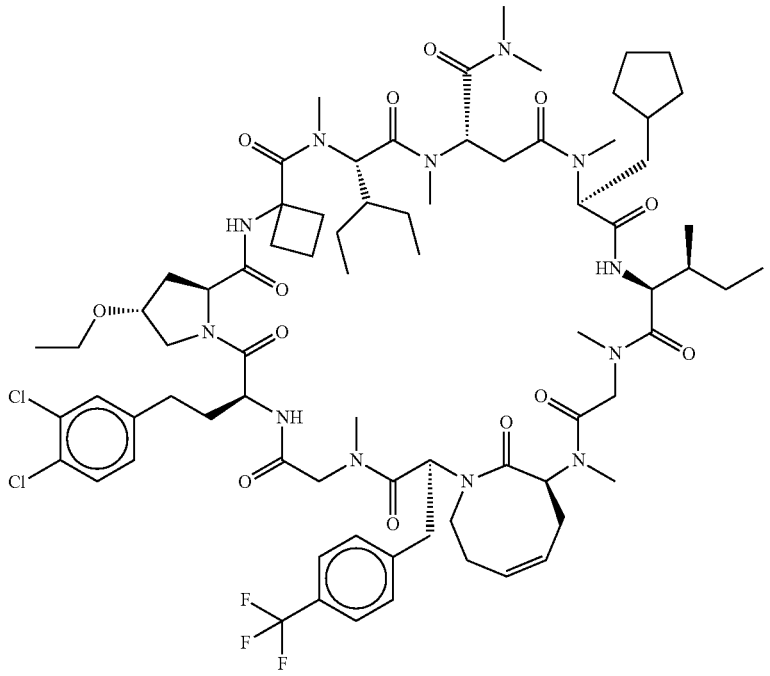 |

TABLE 38-continued
| Compound No. | Structural Formula |
|---|---|
| PP1221 | 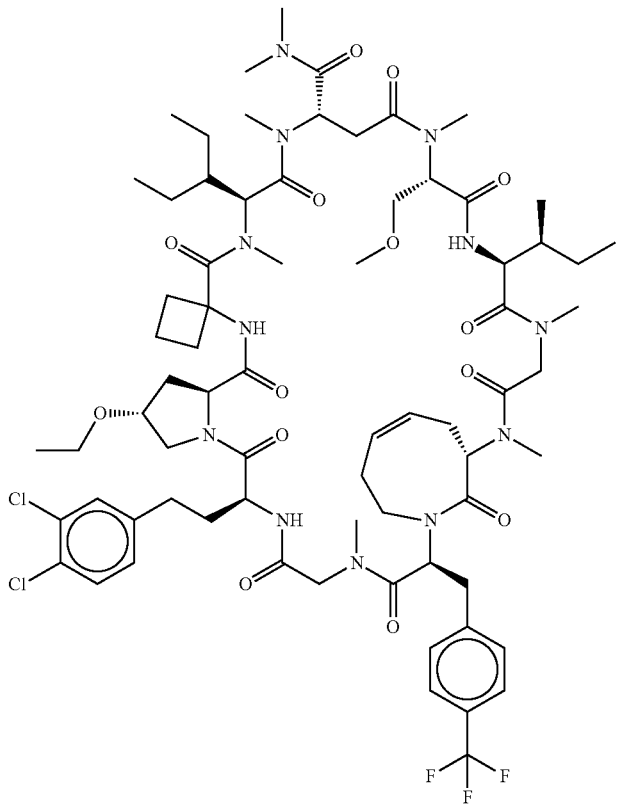 |
| PP1222 | 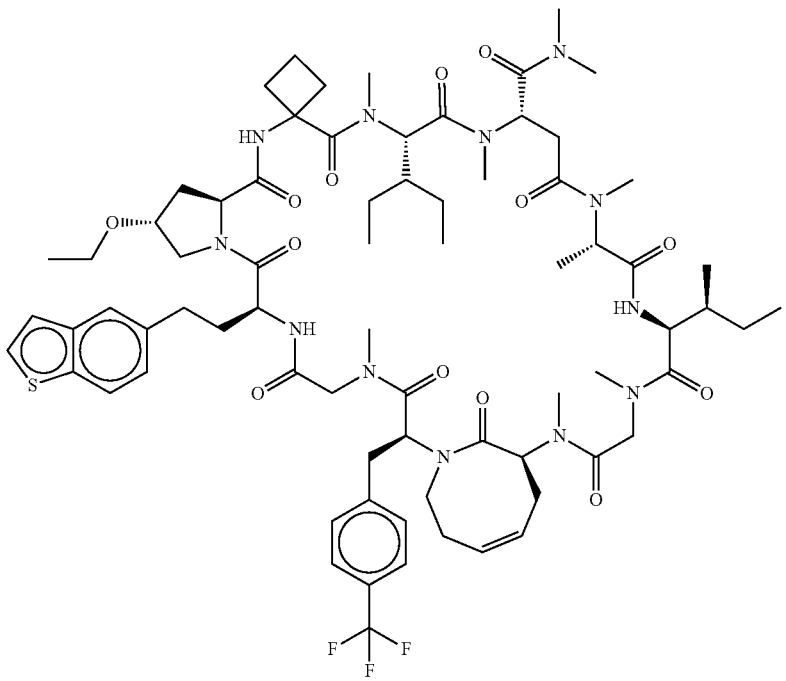 |

TABLE 38-continued
| Compound No. | Structural Formula |
|---|---|
| PP1223 | 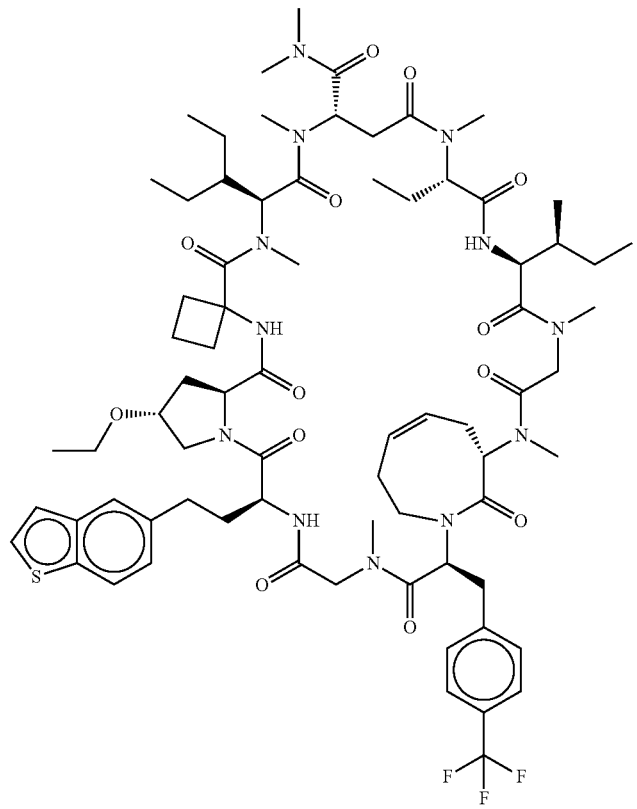 |
| PP1224 | 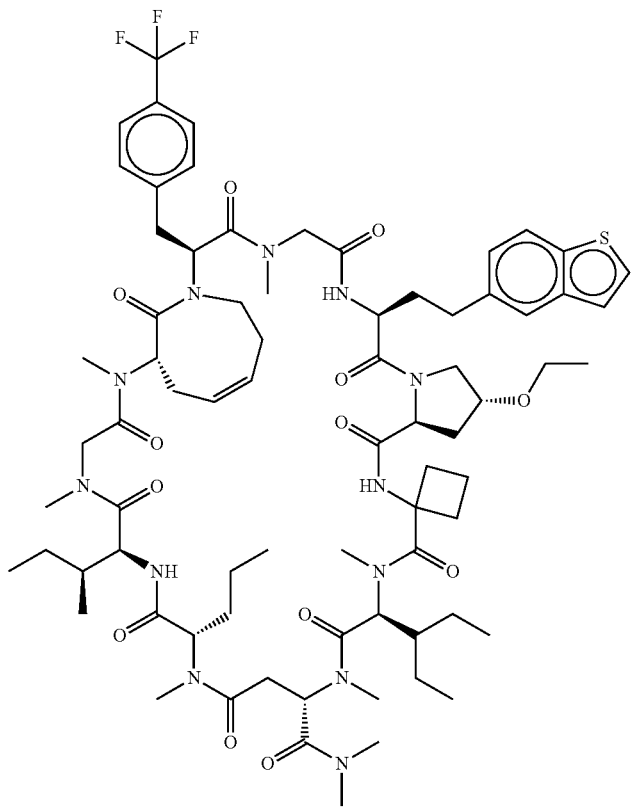 |

TABLE 38-continued
| Compound No. | Structural Formula |
|---|---|
| PP1225 | 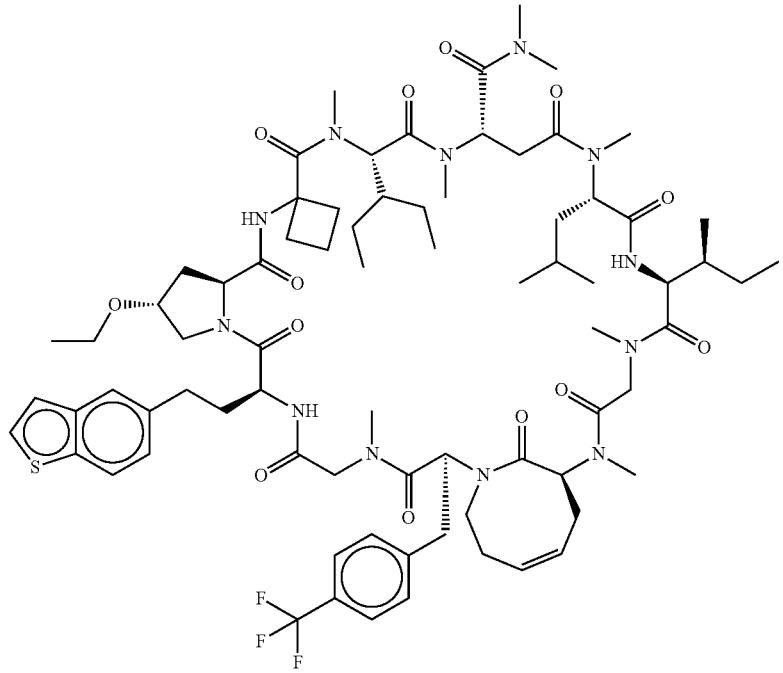 |
| PP1226 | 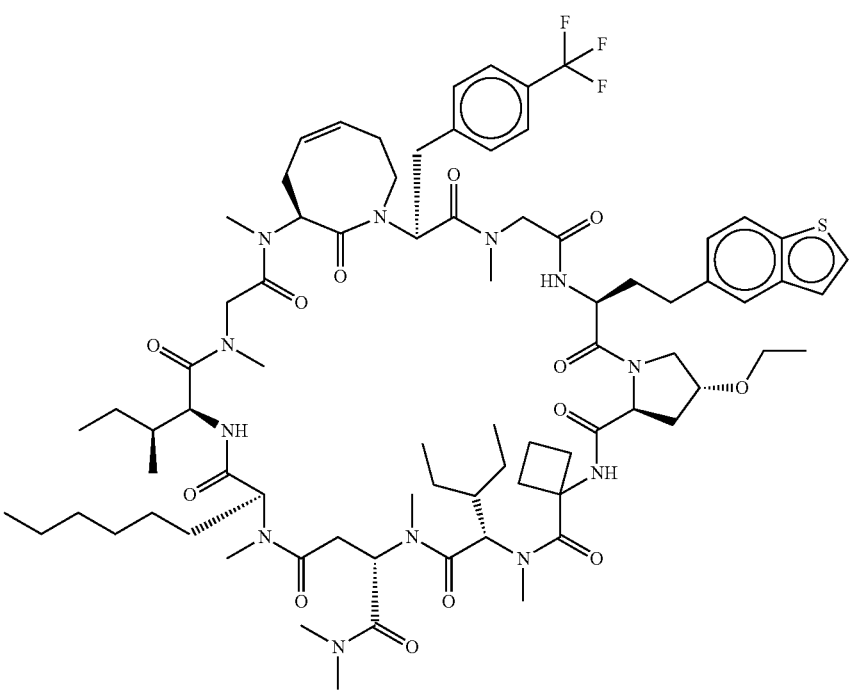 |

TABLE 38-continued
| Compound No. | Structural Formula |
|---|---|
| PP1227 | 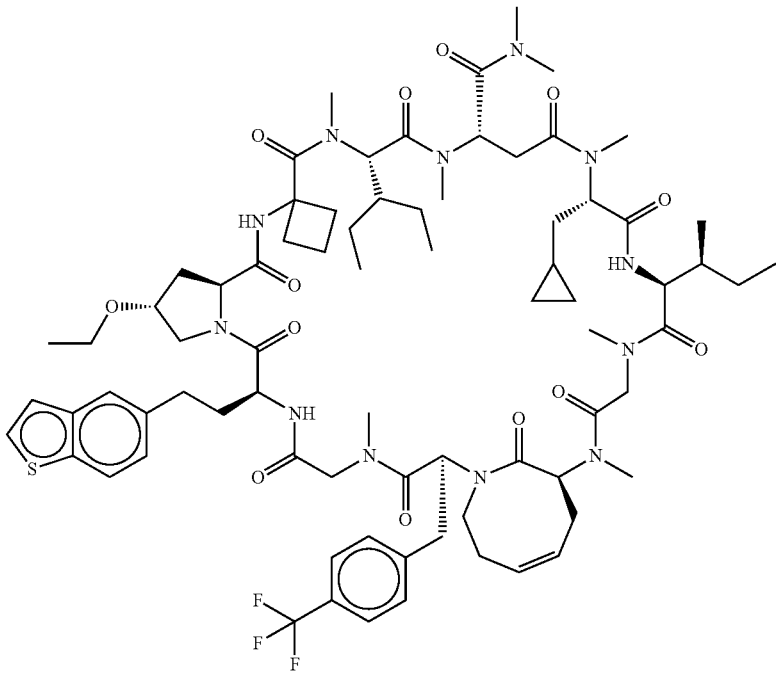 |
| PP1228 | 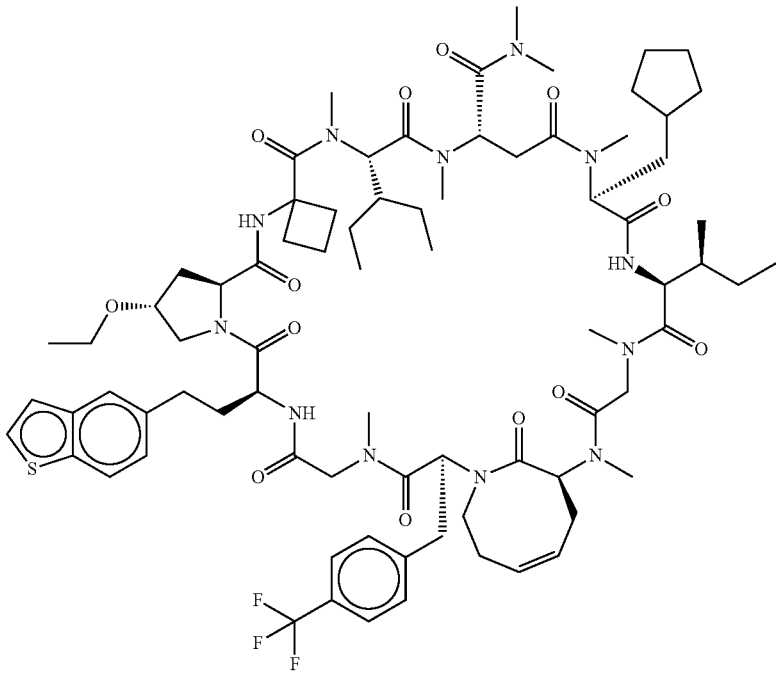 |

TABLE 38-continued
| Compound No. | Structural Formula |
|---|---|
| PP1229 | 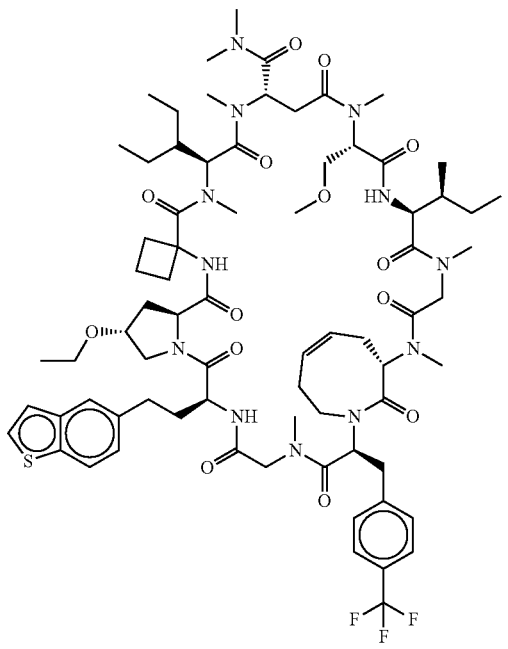 |
| PP1230 | 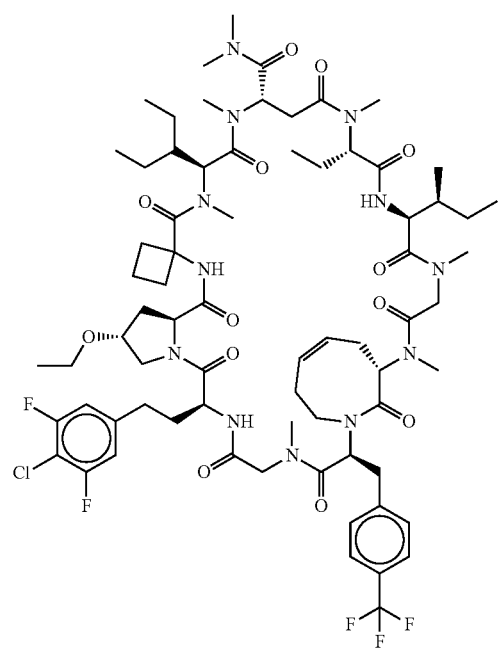 |

TABLE 38-continued

| Compound No. | Structural Formula |
|---|---|
| PP1231 | |
| PP1232 | |

TABLE 38-continued
| Compound No. | Structural Formula |
|---|---|
| PP1233 | 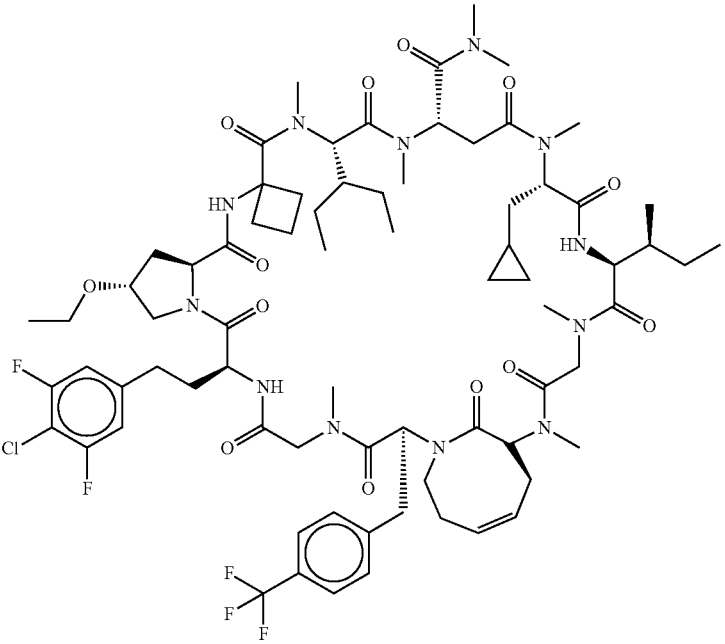 |
| PP1234 | 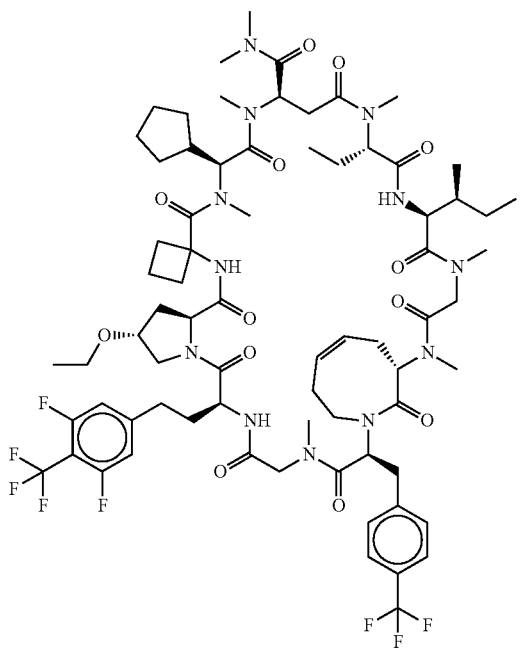 |

TABLE 38-continued
| Compound No. | Structural Formula |
|---|---|
| PP1235 | 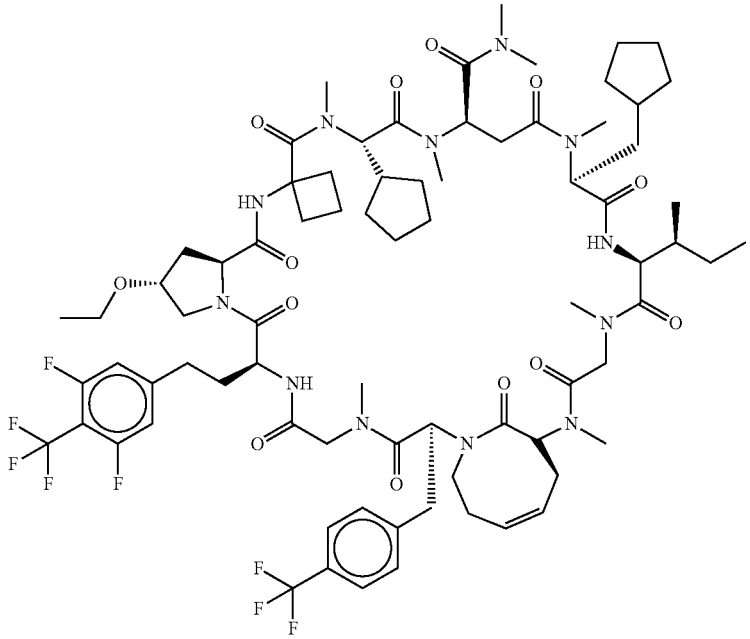 |
| PP1242 | 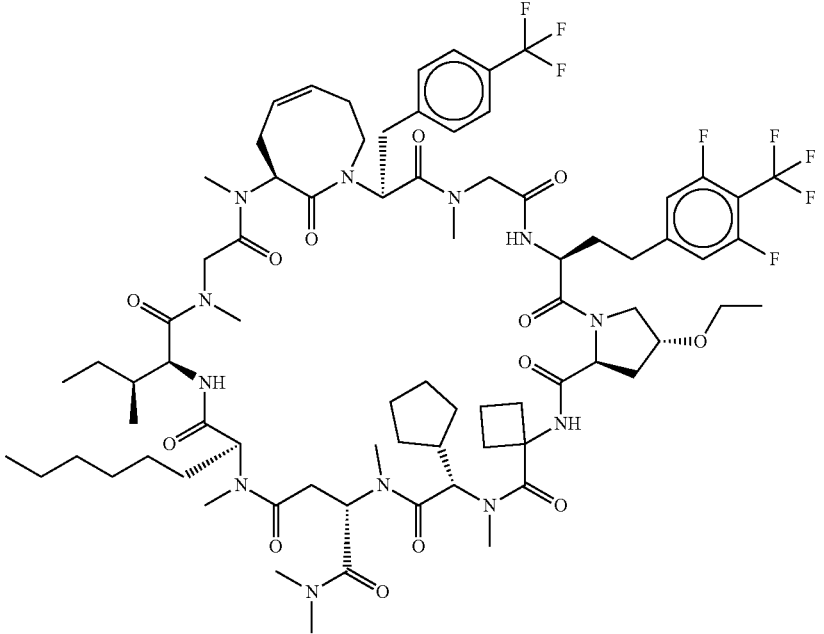 |

TABLE 38-continued
| Compound No. | Structural Formula |
|---|---|
| PP1243 | 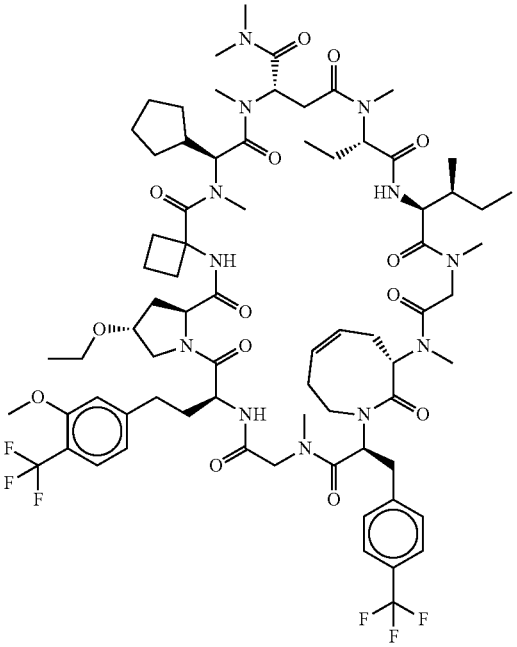 |
| PP1244 | 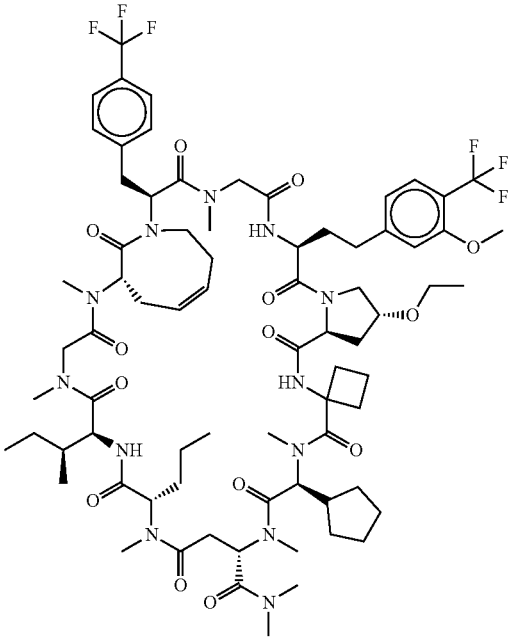 |

TABLE 38-continued
| Compound No. | Structural Formula |
|---|---|
| PP1245 | 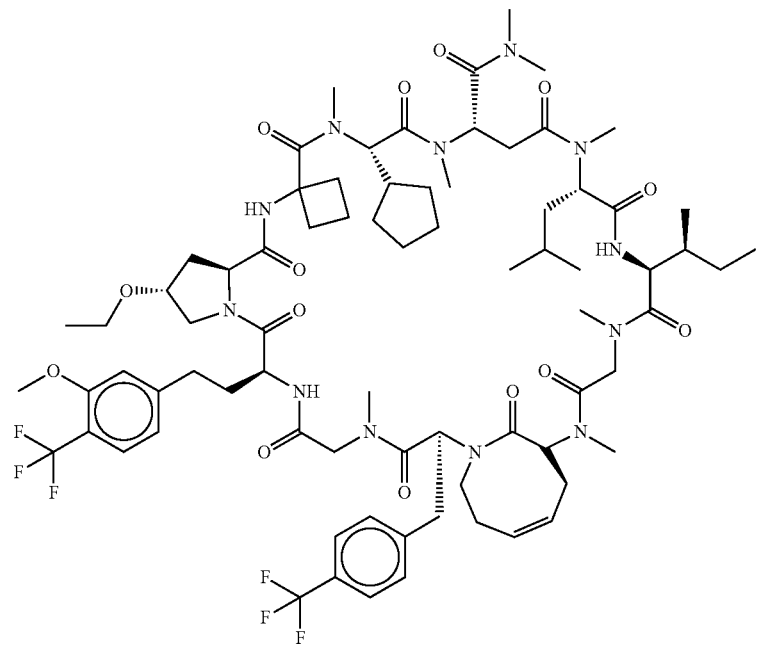 |
| PP1246 | 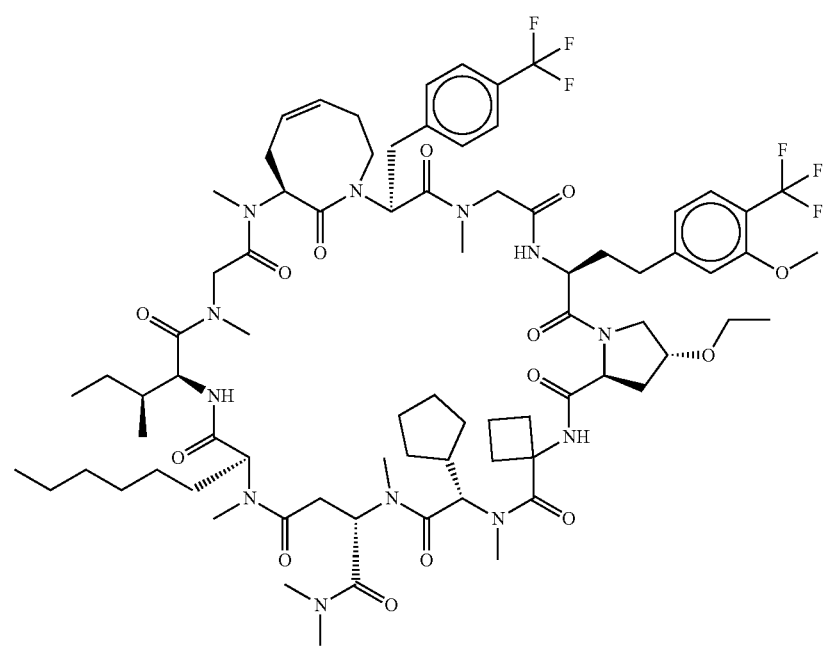 |

TABLE 38-continued
| Compound No. | Structural Formula |
|---|---|
| PP1247 | 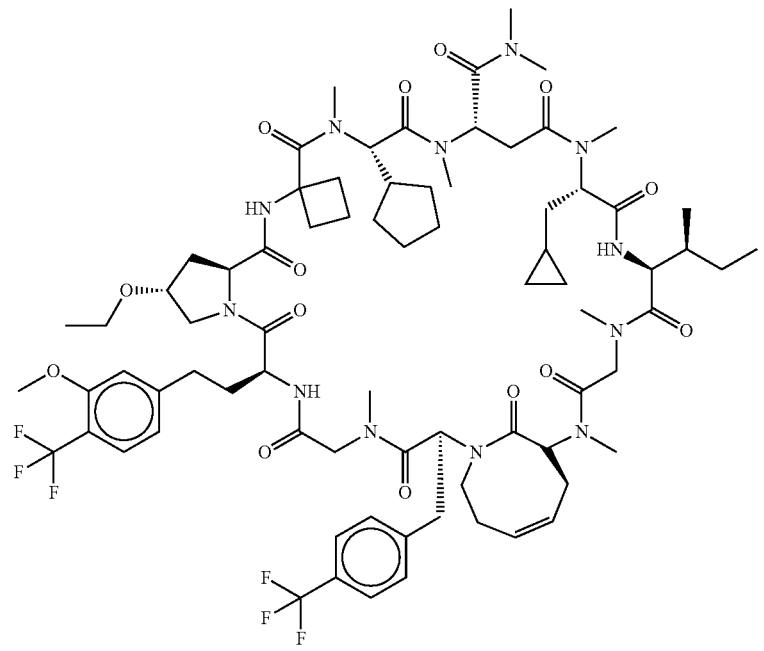 |
| PP1248 | 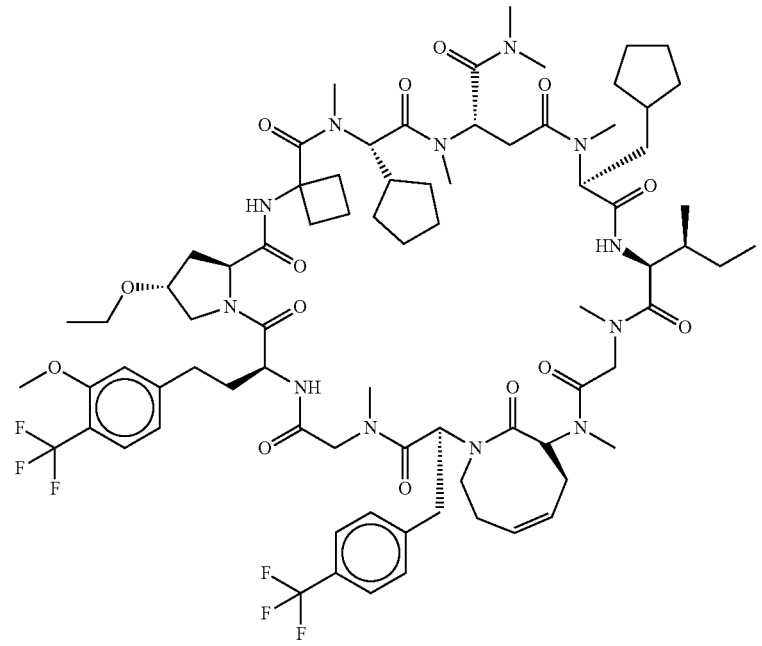 |

TABLE 38-continued
| Compound No. | Structural Formula |
|---|---|
| PP1249 | 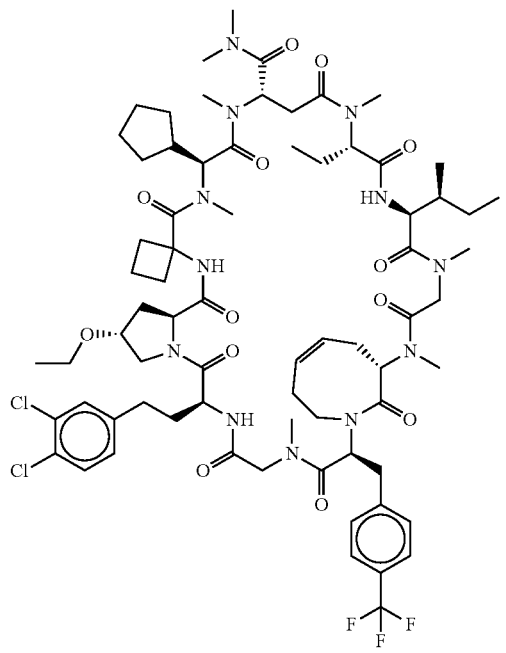 |
| PP1250 | 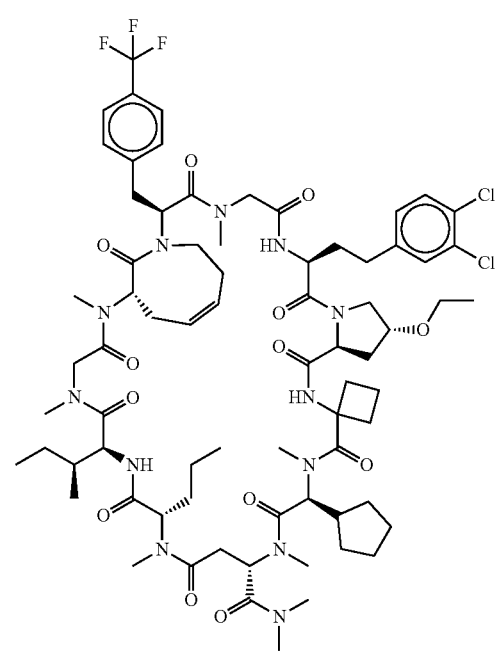 |

TABLE 38-continued
| Compound No. | Structural Formula |
| --- | --- |
| PP1251 | 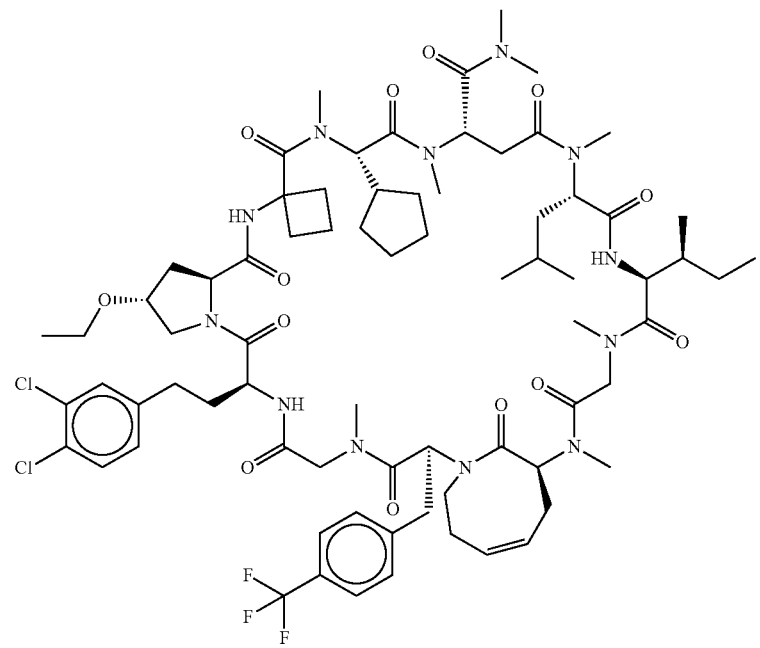 |
| PP1252 | 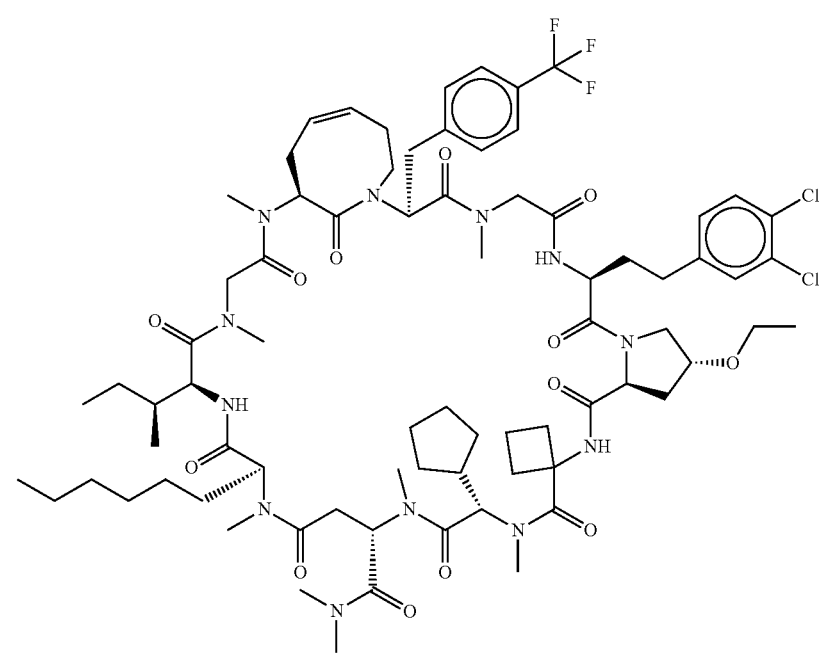 |

TABLE 38-continued
| Compound No. | Structural Formula |
|---|---|
| PP1253 | 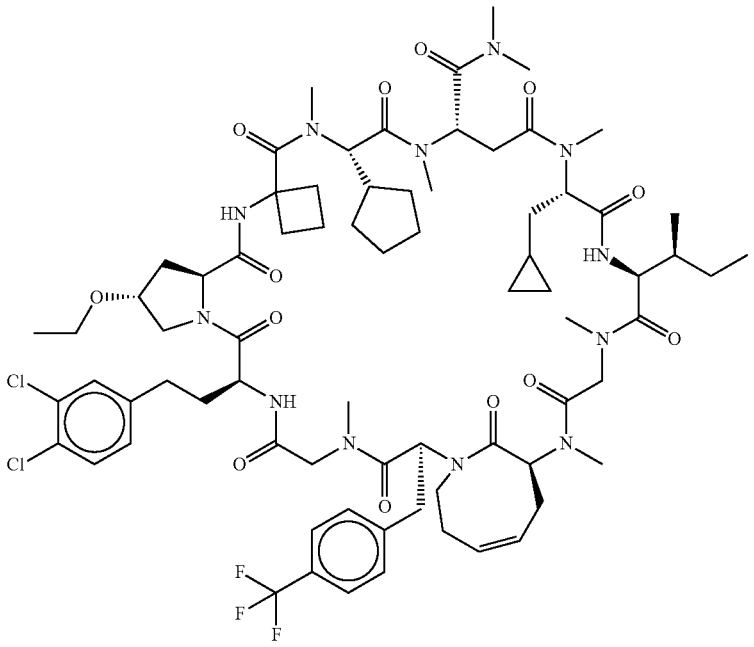 |
| PP1254 | 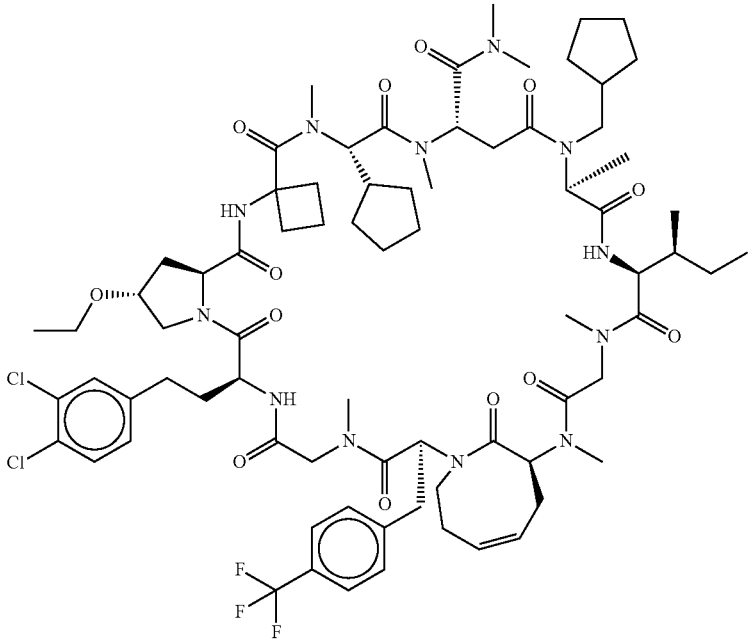 |

TABLE 38-continued

| Compound No. | Structural Formula |
|---|---|
| PP1255 | |
| PP1256 | |

TABLE 38-continued

| Compound No. | Structural Formula |
|---|---|
| PP1257 | |
| PP1258 | |

TABLE 38-continued
| Compound No. | Structural Formula |
|---|---|
| PP1259 | 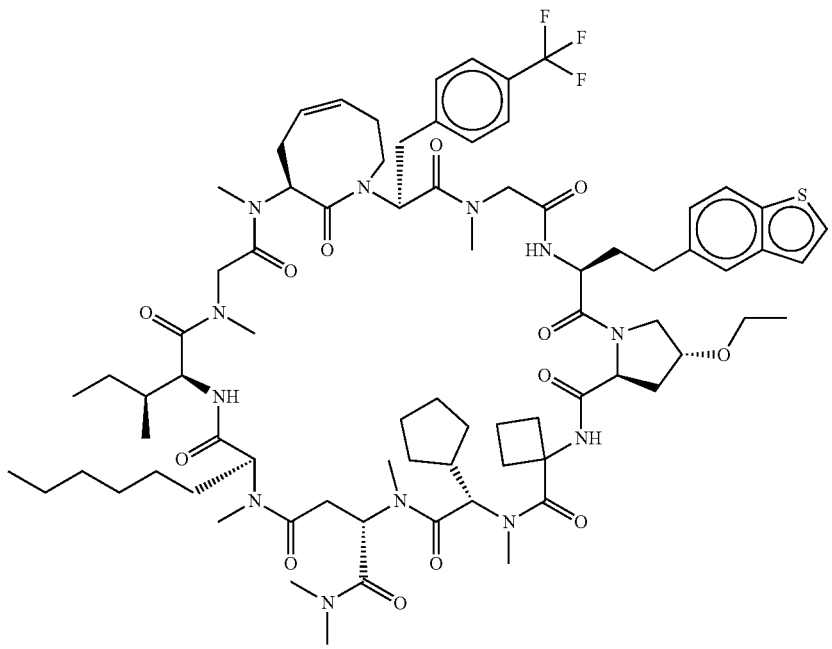 |
| PP1260 | 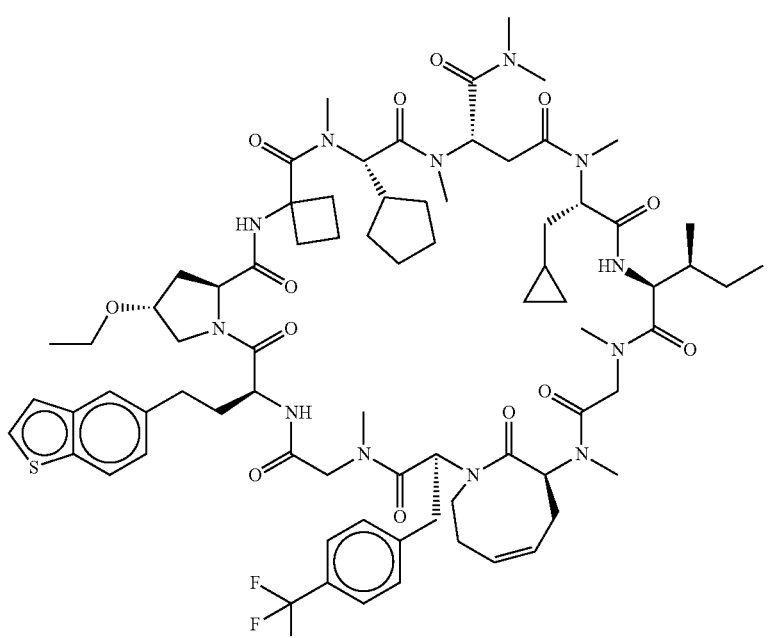 |

TABLE 38-continued
| Compound No. | Structural Formula |
|---|---|
| PP1261 | 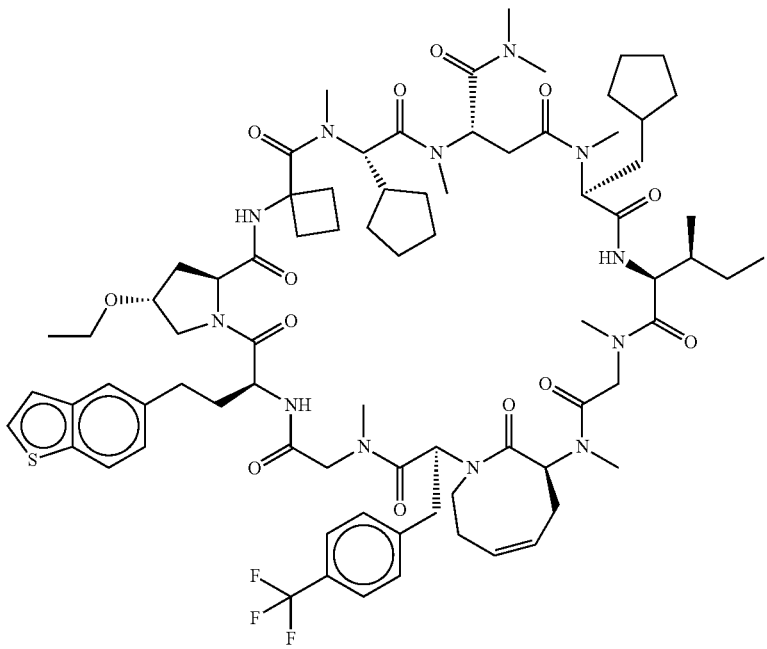 |
| PP1262 | 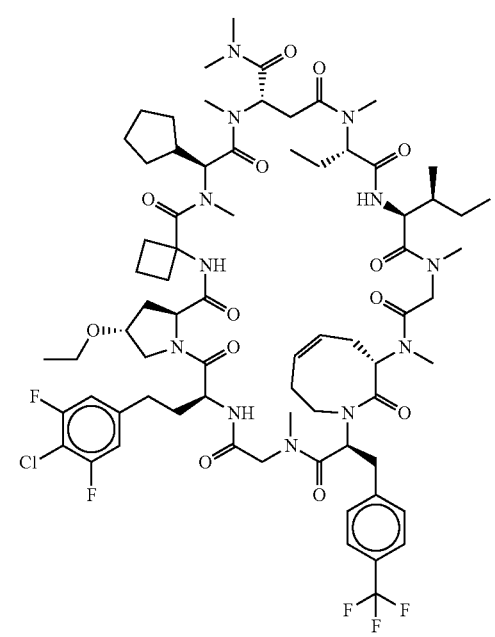 |

TABLE 38-continued
| Compound No. | Structural Formula |
|---|---|
| PP1263 | 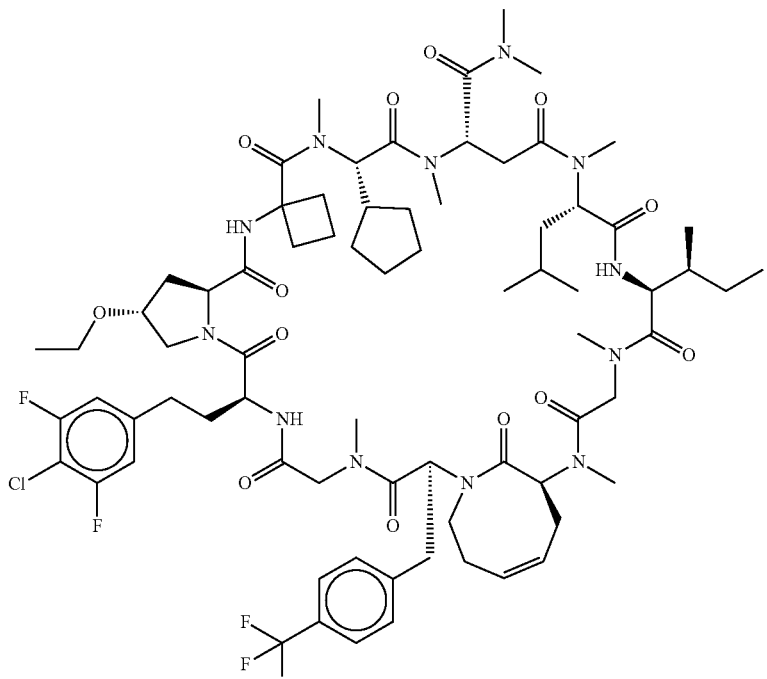 |
| PP1264 | 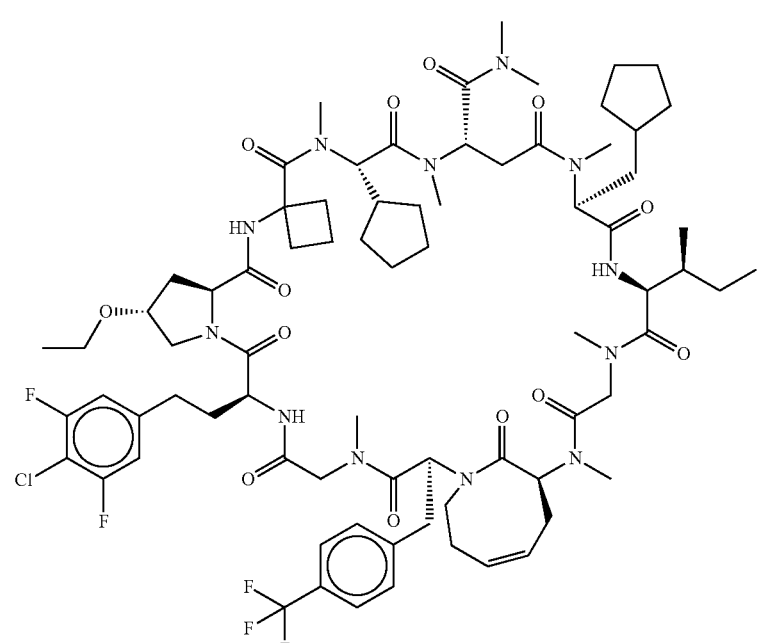 |

TABLE 38-continued

| Compound No. | Structural Formula |
|---|---|
| PP1265 | |
| PP1266 | |

TABLE 38-continued
| Compound No. | Structural Formula |
|---|---|
| PP1267 | 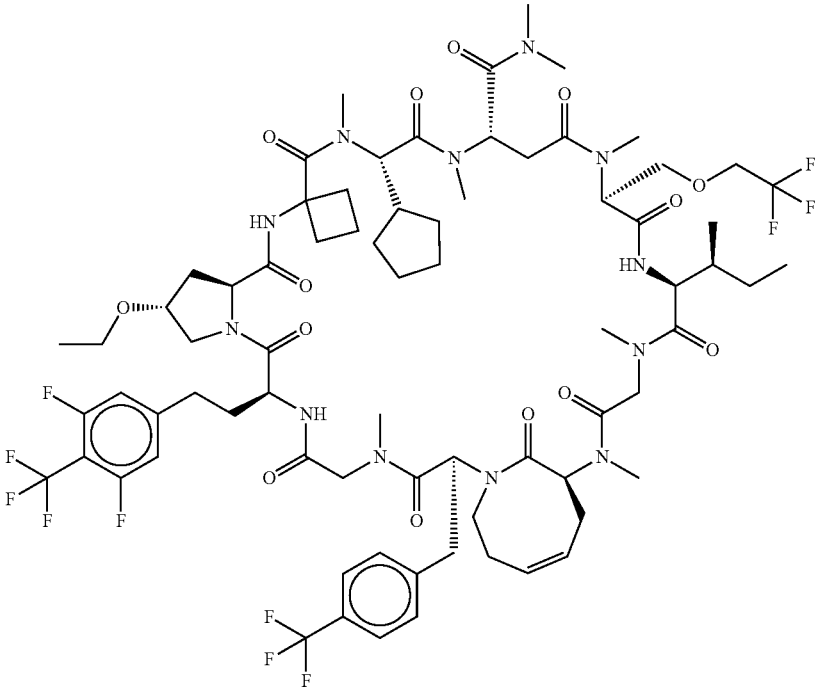 |
| PP1268 | 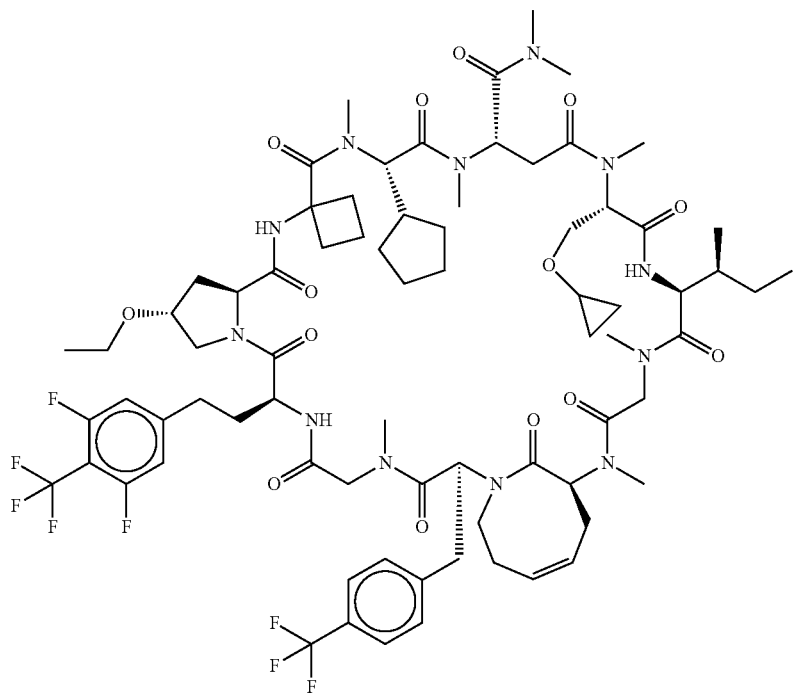 |

TABLE 38-continued
| Compound No. | Structural Formula |
|---|---|
| PP1269 | 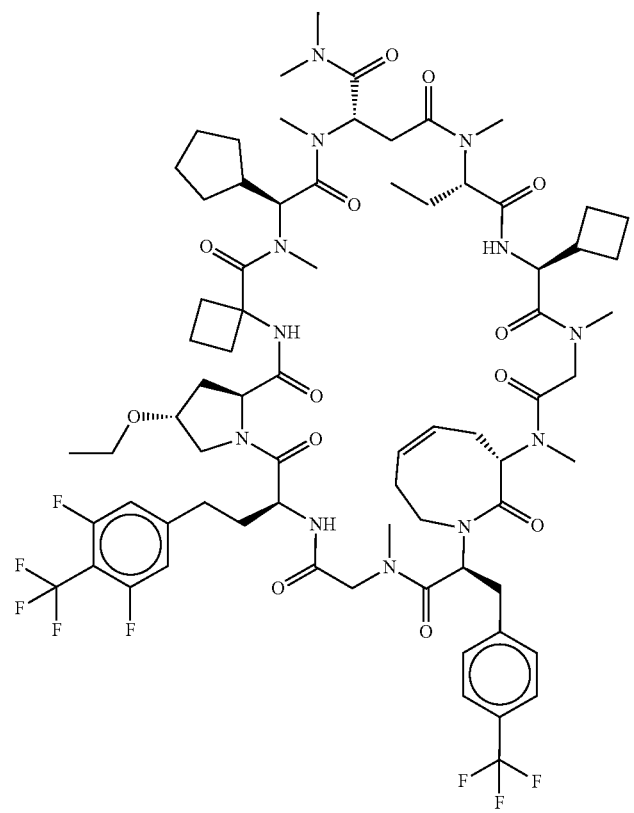 |
| PP1270 | 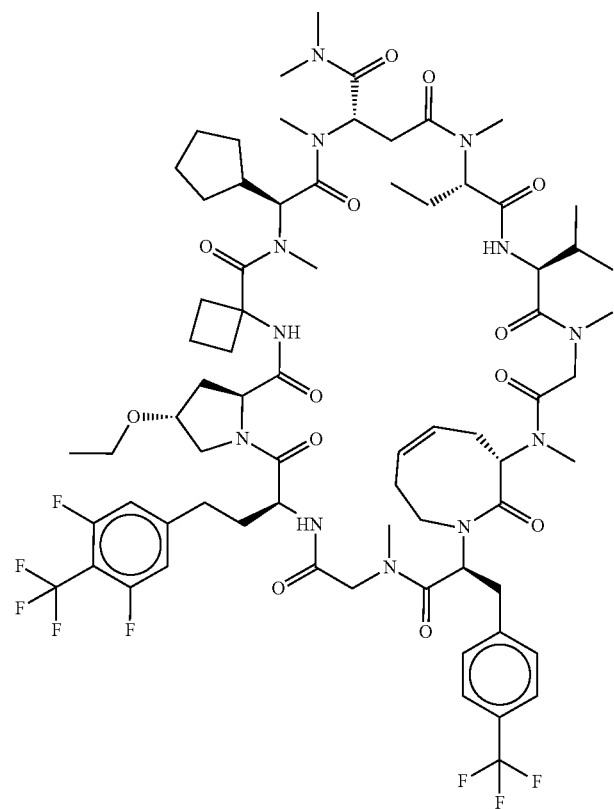 |

TABLE 38-continued
| Compound No. | Structural Formula |
|---|---|
| PP1271 | 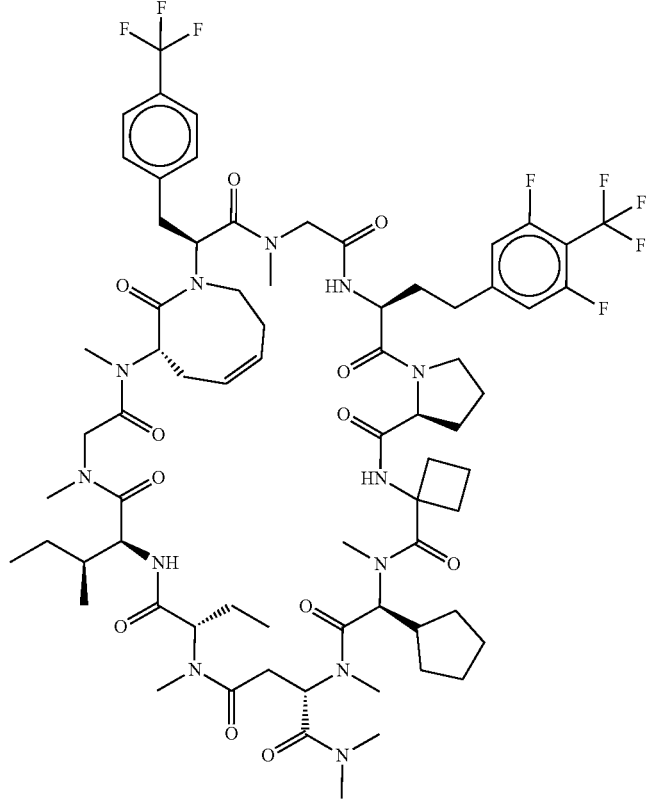 |
| PP1272 | 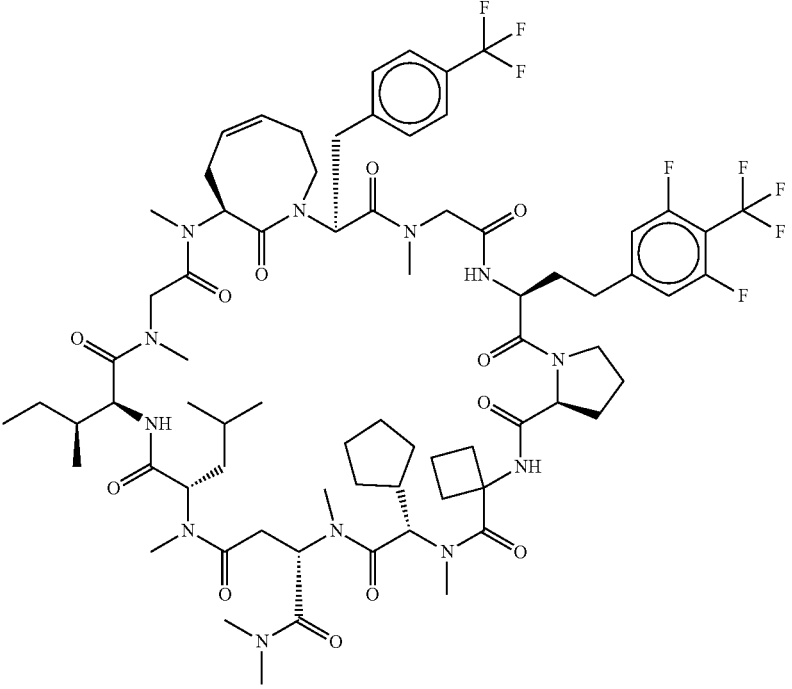 |

TABLE 38-continued
| Compound No. | Structural Formula |
|---|---|
| PP1273 | 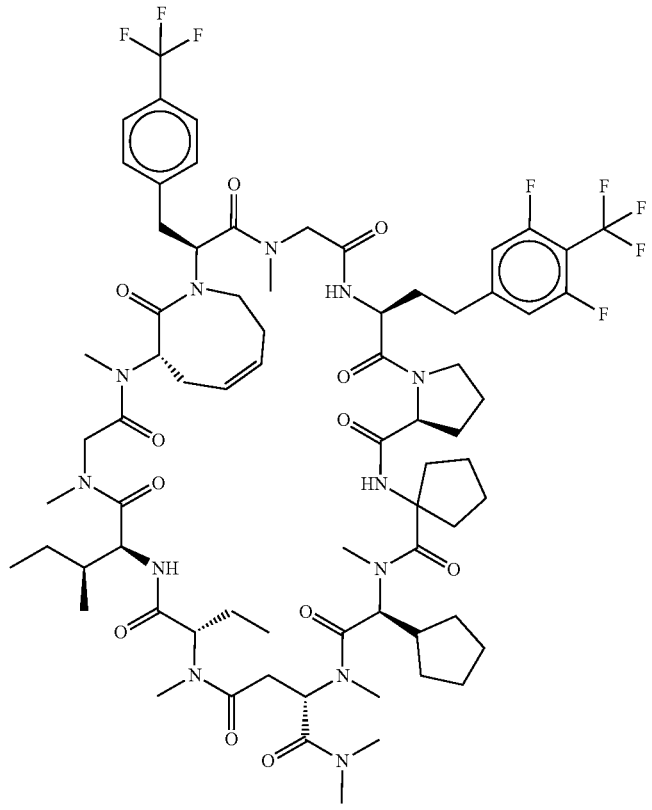 |
| PP1274 | 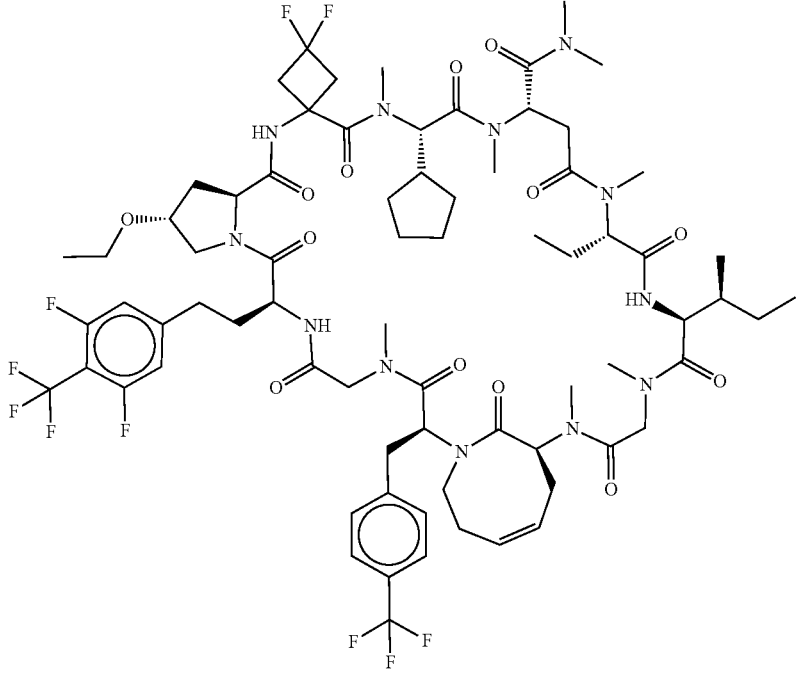 |

TABLE 38-continued

| Compound No. | Structural Formula |
|---|---|
| PP1275 | |
| PP1276 | |

TABLE 38-continued
| Compound No. | Structural Formula |
|---|---|
| PP1277 | 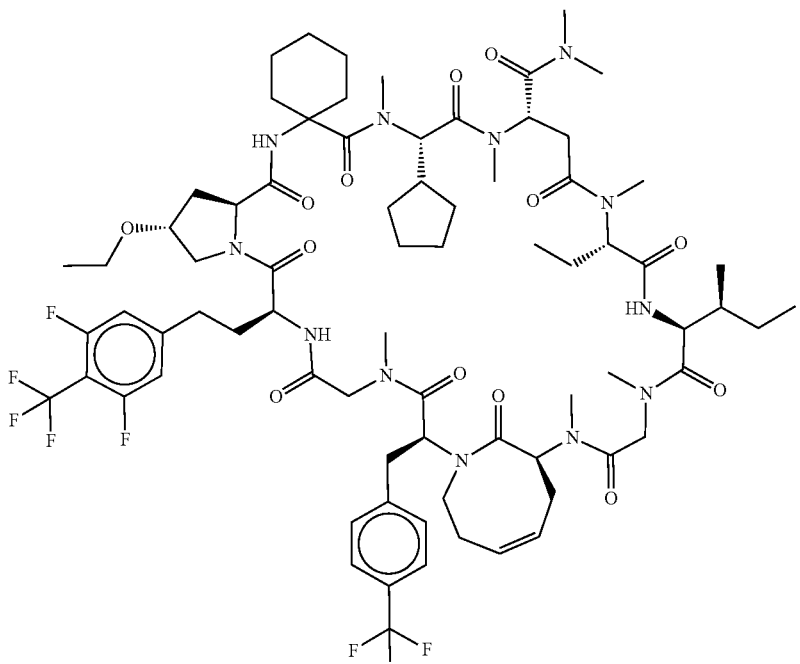 |
| PP1278 | 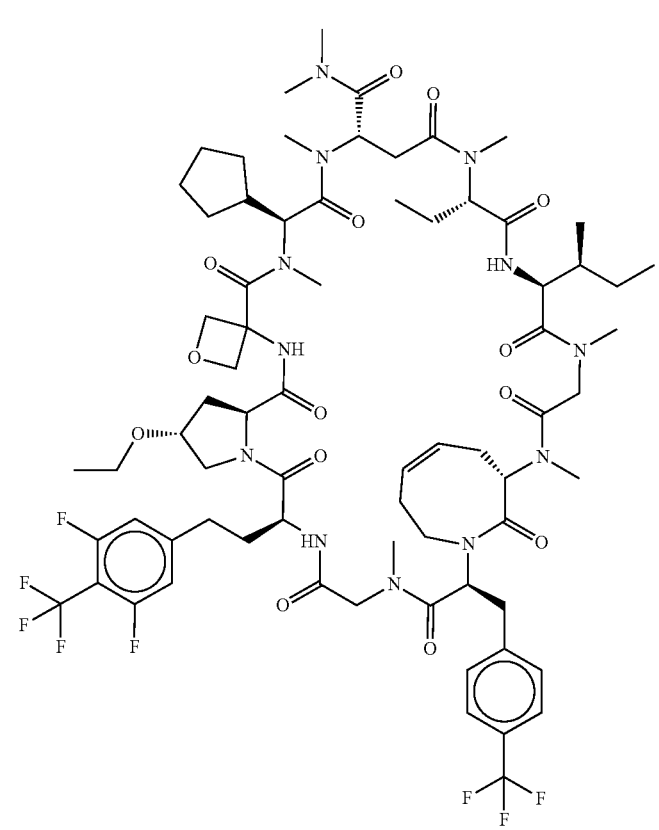 |

TABLE 38-continued
| Compound No. | Structural Formula |
|---|---|
| PP1279 | 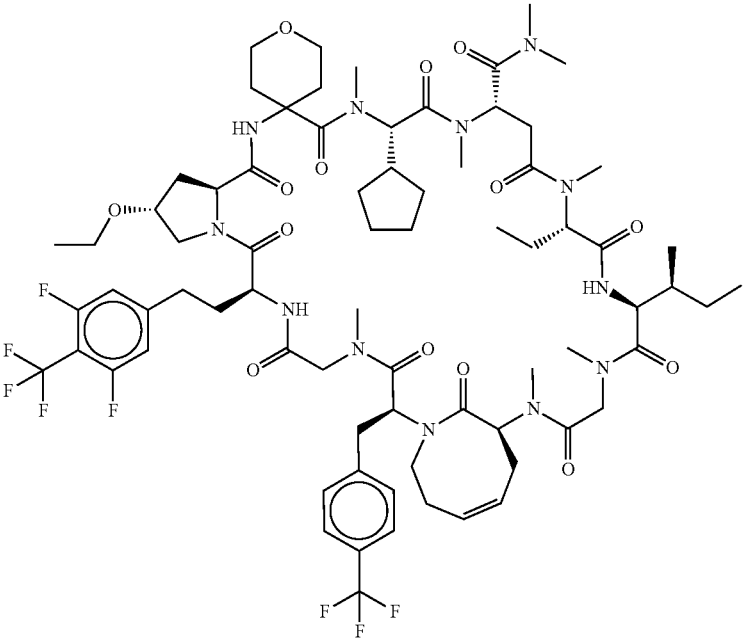 |
| PP1280 | 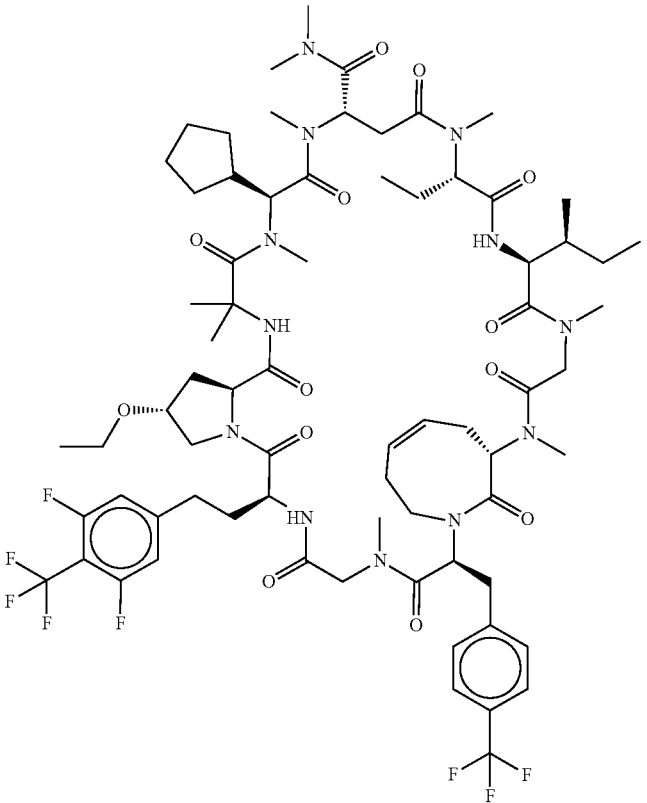 |

TABLE 38-continued
| Compound No. | Structural Formula |
|---|---|
| PP1281 | 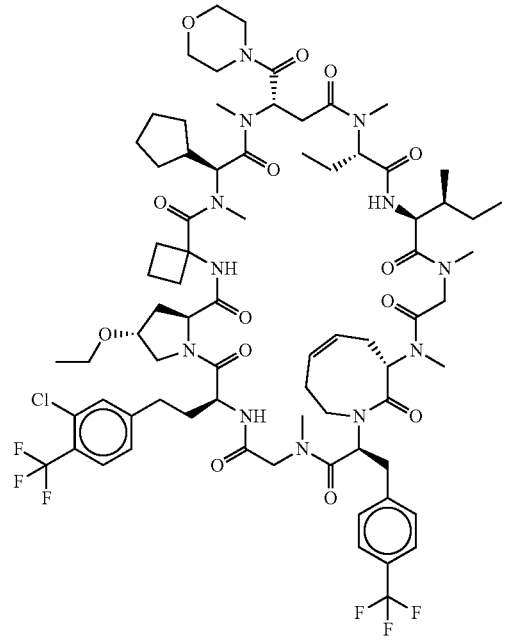 |
| PP1282 | 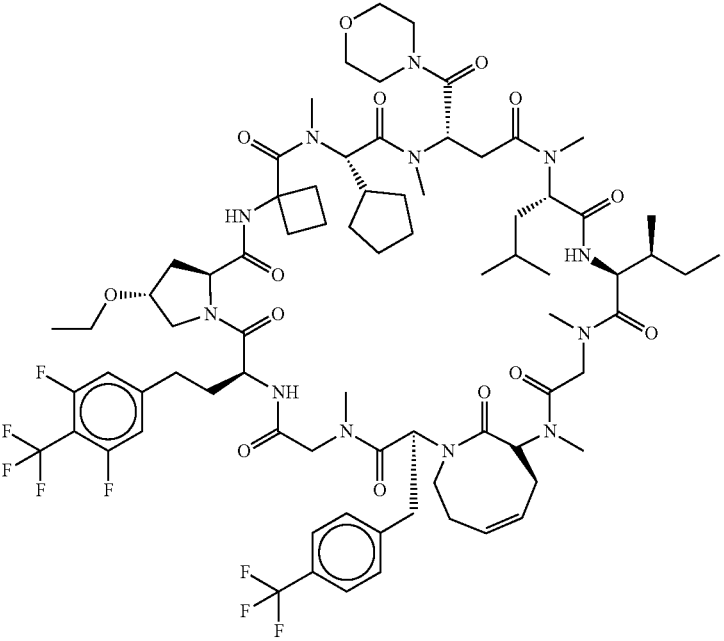 |

TABLE 38-continued
| Compound No. | Structural Formula |
|---|---|
| PP1283 | 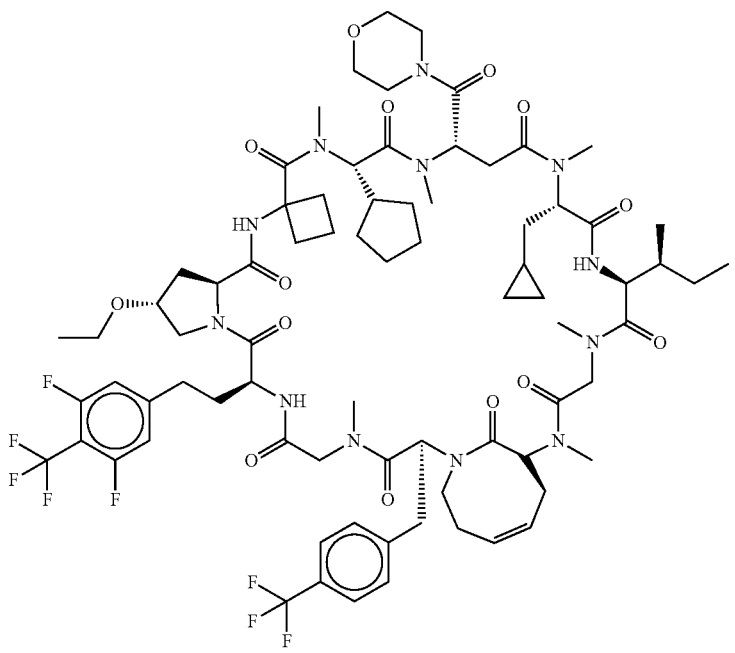 |
| PP1284 | 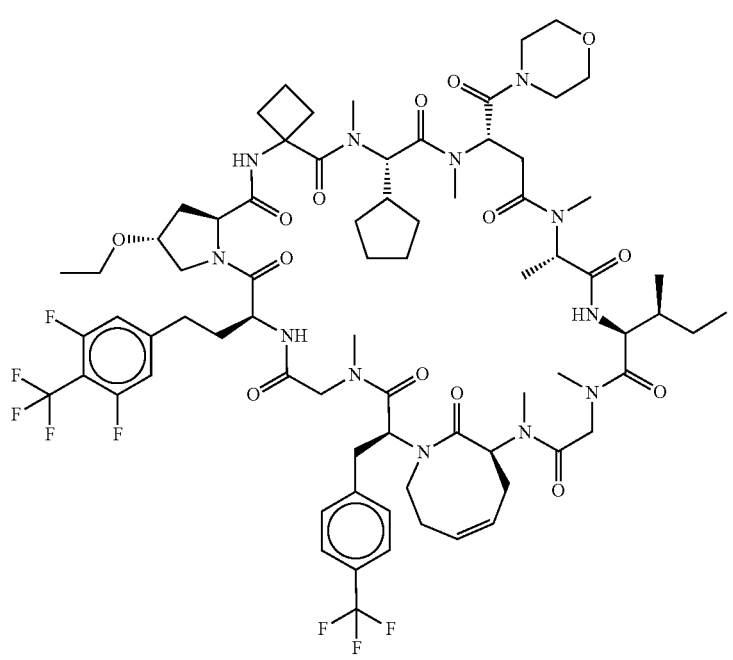 |

TABLE 38-continued
| Compound No. | Structural Formula |
|---|---|
| PP1285 | 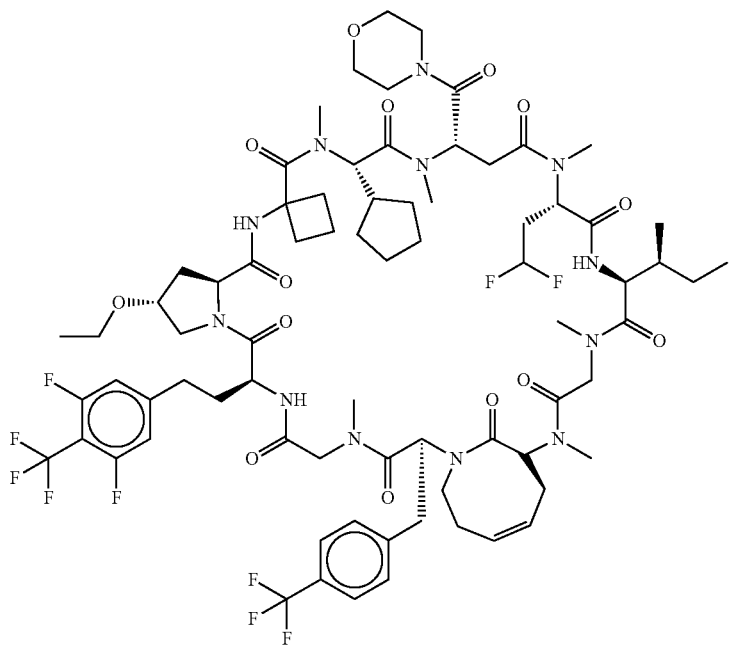 |
| PP1286 | 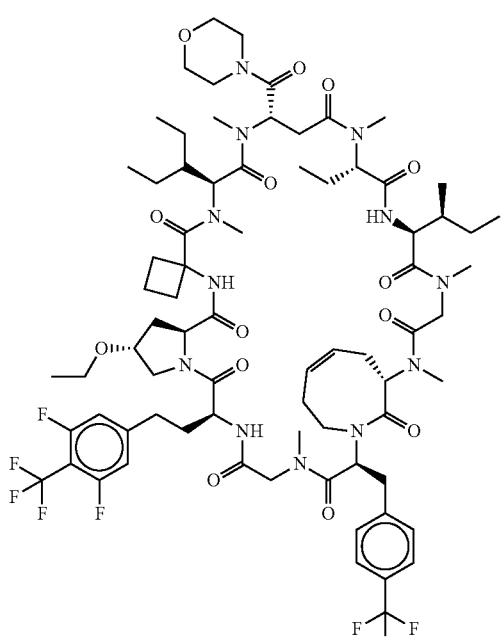 |

TABLE 38-continued

| Compound No. | Structural Formula |
|---|---|
| PP1287 | |
| PP1288 | |

TABLE 38-continued

| Compound No. | Structural Formula |
|---|---|
| PP1289 | |
| PP1290 | | mula
| Compound No. | Structural Formula |
|---|---|
| PP1291 | 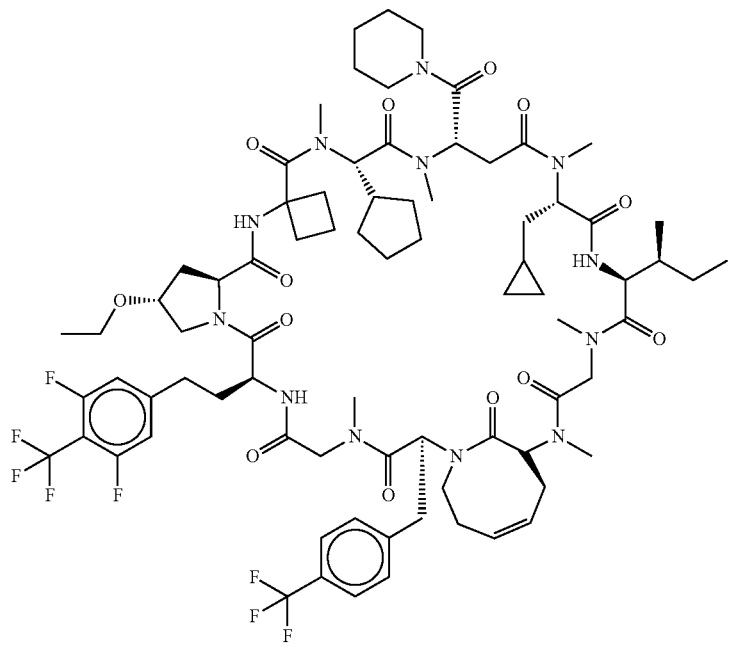 |
| PP1292 | 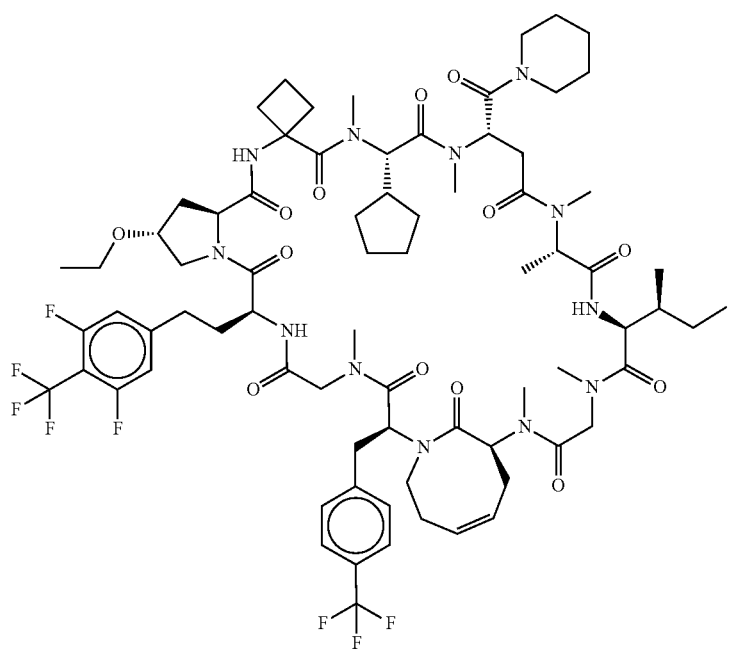 |

2101
TABLE 38-continued
| Compound No. | Structural Formula |
|---|---|
| PP1293 | 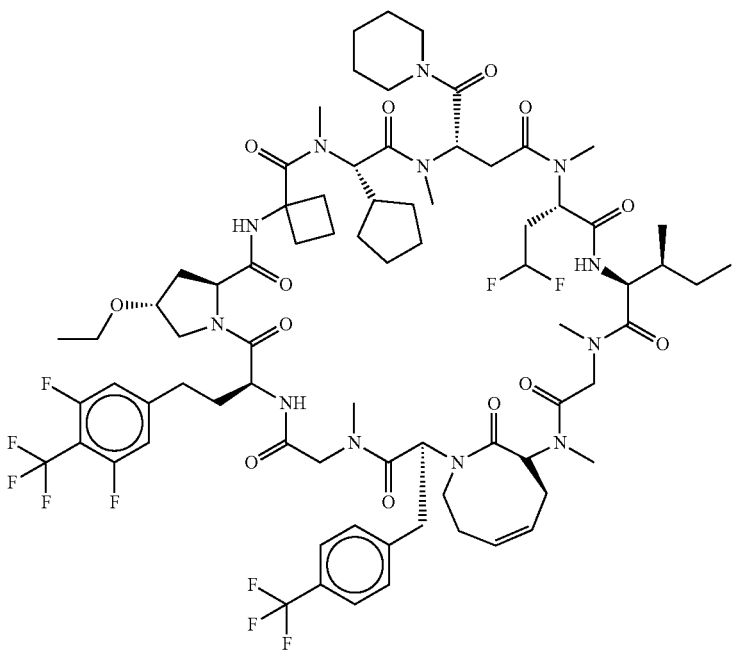 |
| PP1294 | 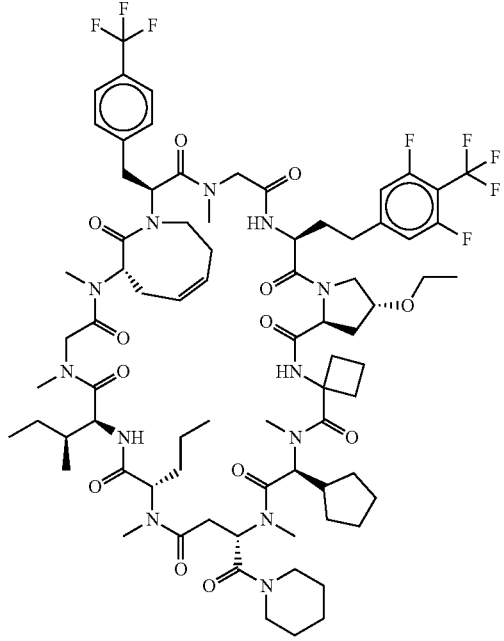 |

TABLE 38-continued
| Compound No. | Structural Formula |
| --- | --- |
| PP1295 | 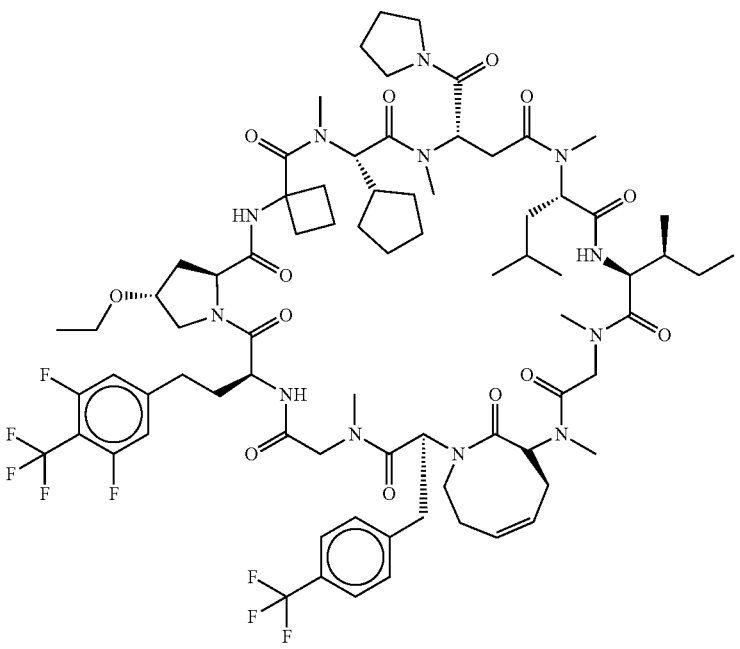 |
| PP1296 | 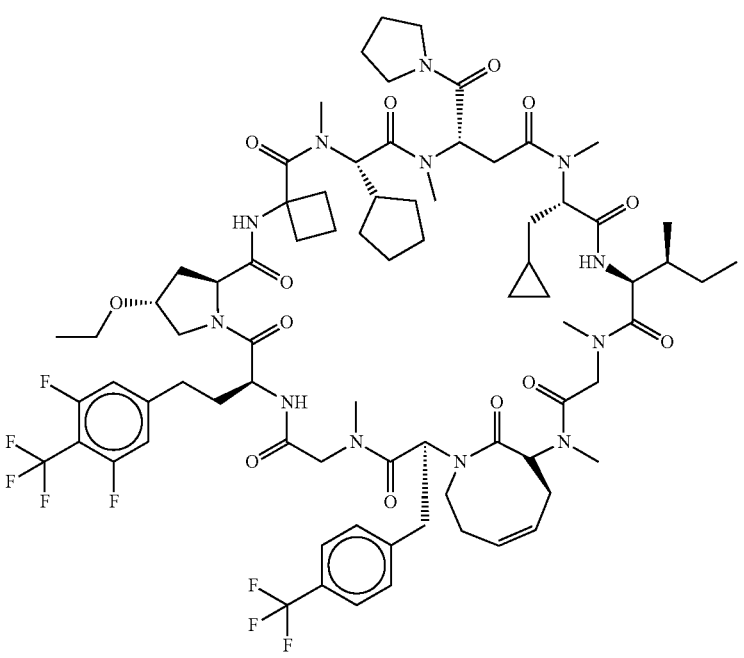 |

TABLE 38-continued
| Compound No. | Structural Formula |
|---|---|
| PP1297 | 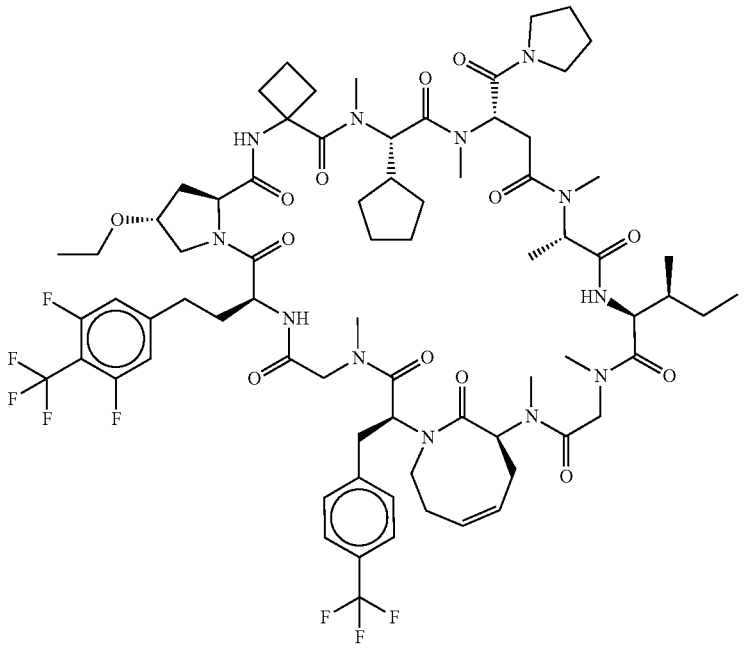 |
| PP1298 | 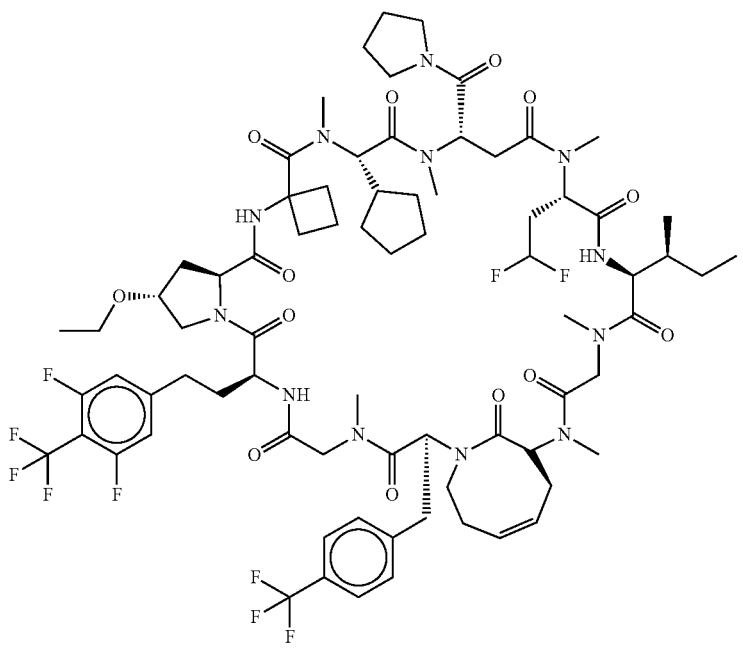 |

TABLE 38-continued
| Compound No. | Structural Formula |
|---|---|
| PP1299 | 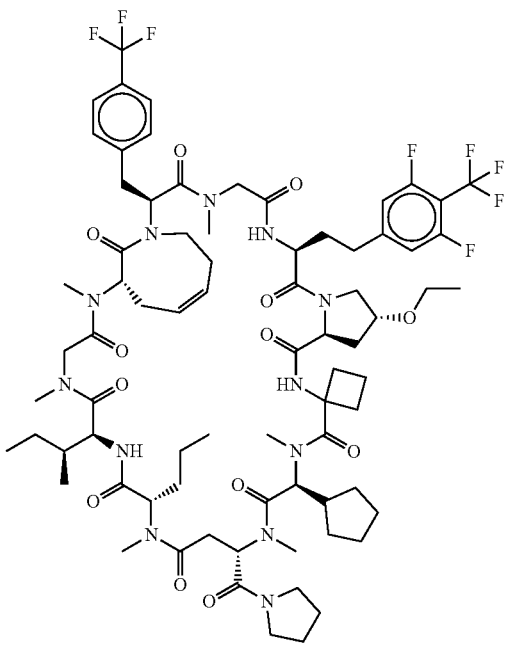 |
| PP1300 | 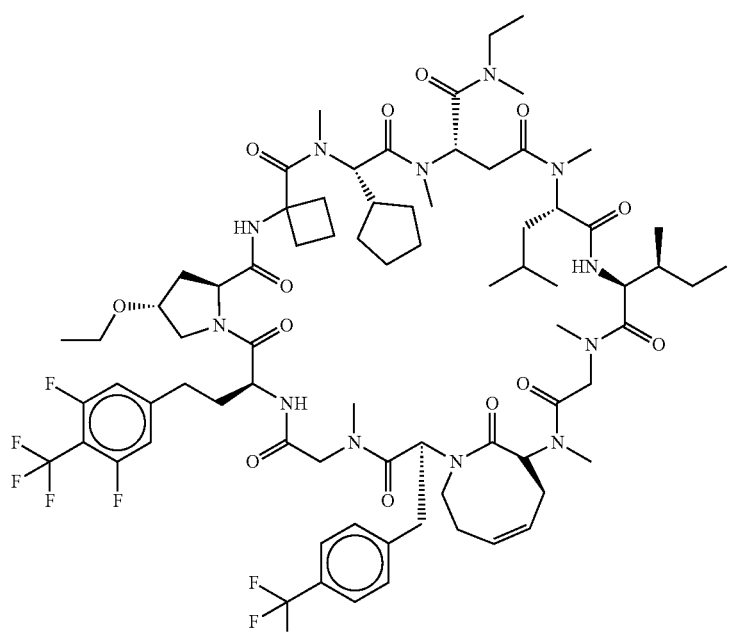 |

TABLE 38-continued
| Compound No. | Structural Formula |
|---|---|
| PP1301 | 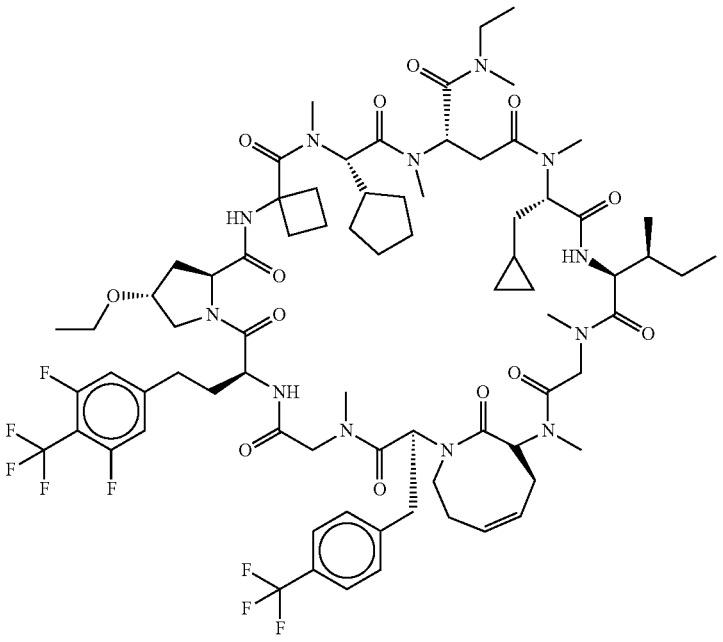 |
| PP1302 | 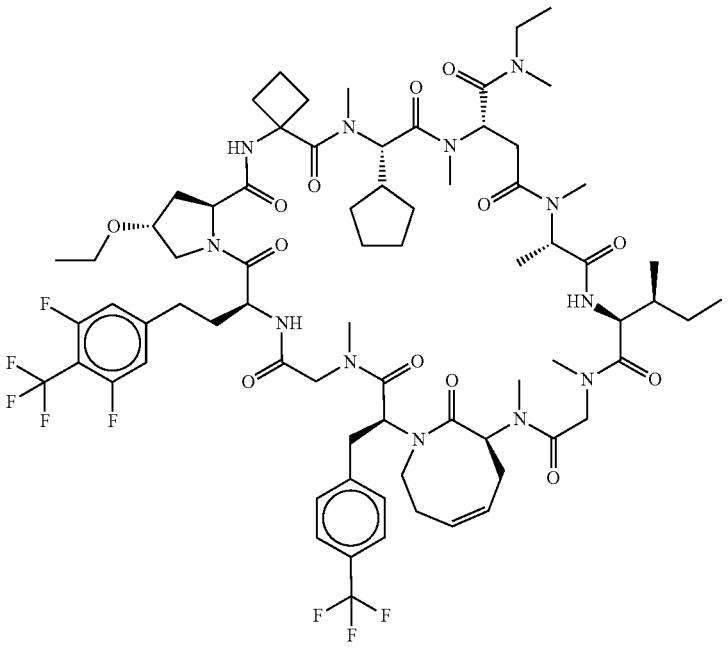 |

TABLE 38-continued
| Compound No. | Structural Formula |
|---|---|
| PP1303 | 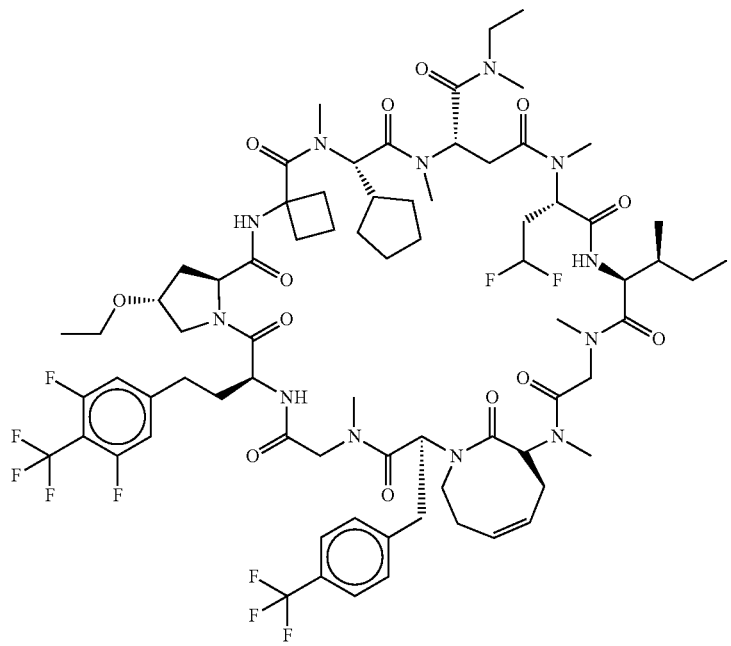 |
| PP1304 | 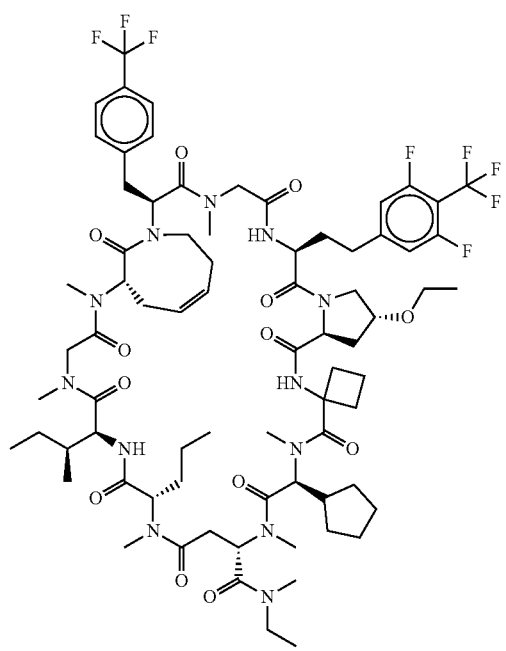 |

TABLE 38-continued

| Compound No. | Structural Formula |
| --- | --- |
| PP1305 | |
| PP1306 | |

TABLE 38-continued
| Compound No. | Structural Formula |
|---|---|
| PP1307 | 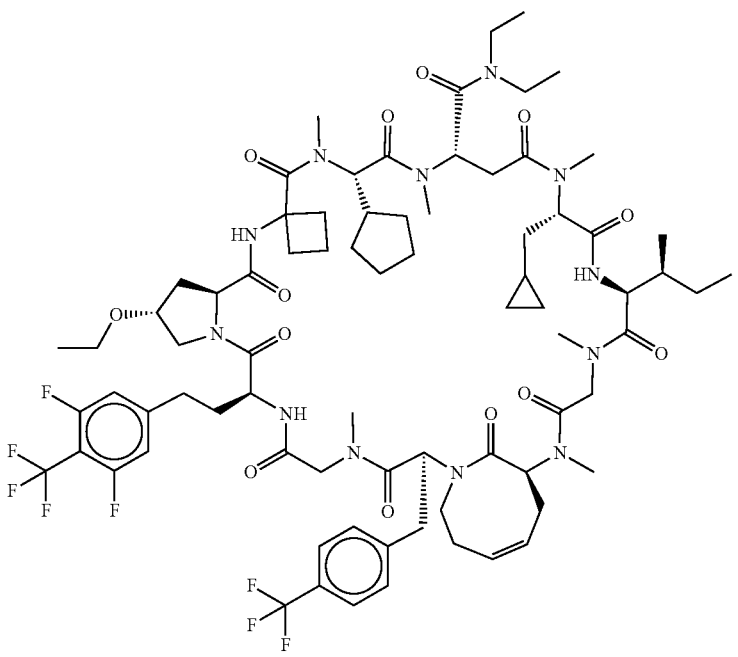 |
| PP1308 | 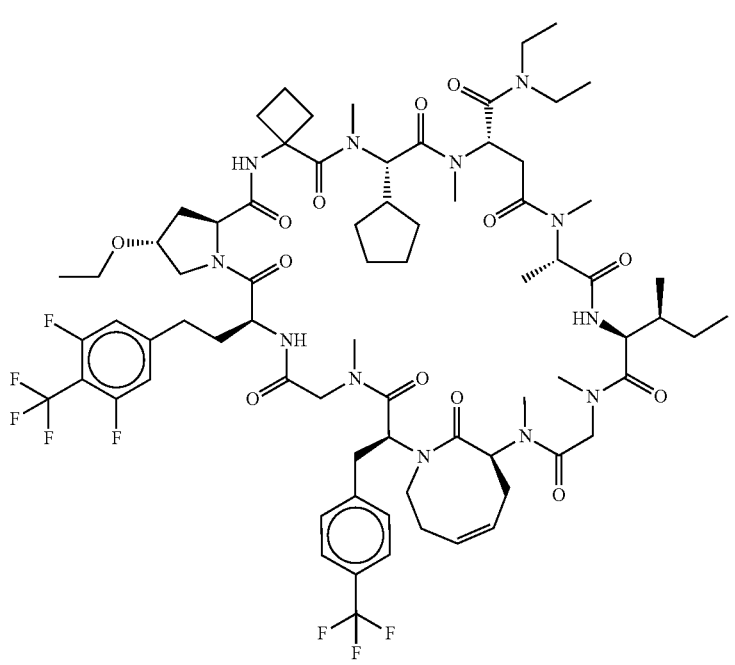 |

TABLE 38-continued

| Compound No. | Structural Formula |
|---|---|
| PP1309 | |
| PP1310 | |

TABLE 38-continued
| Compound No. | Structural Formula |
|---|---|
| PP1311 | 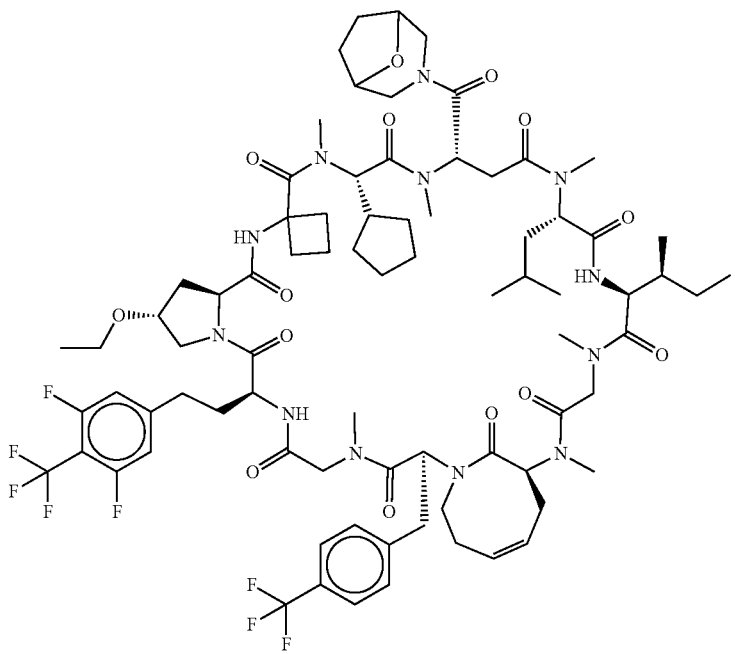 |
| PP1312 | 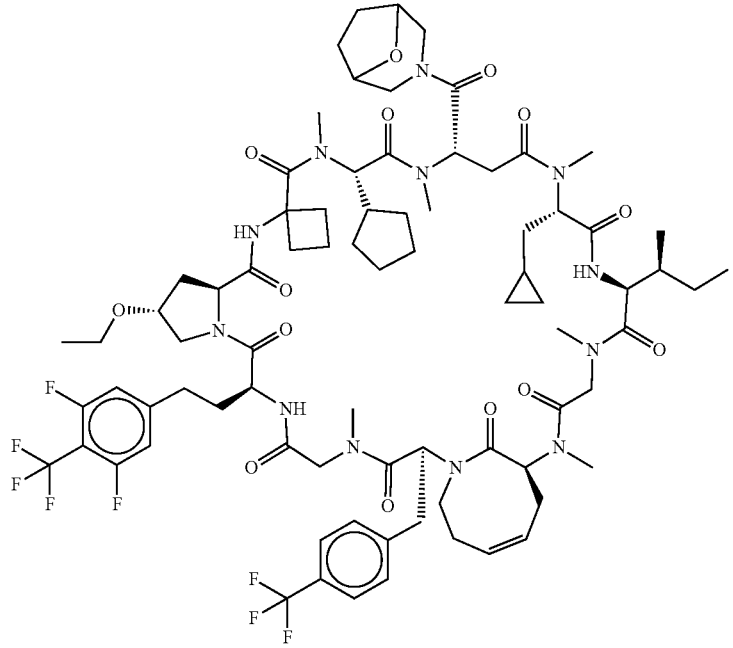 |

TABLE 38-continued
| Compound No. | Structural Formula |
|---|---|
| PP1313 | 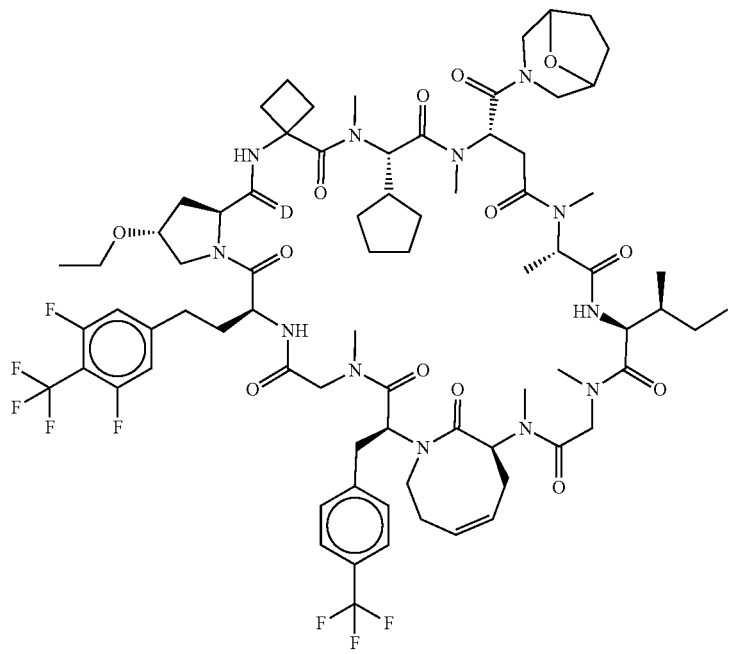 |
| PP1314 | 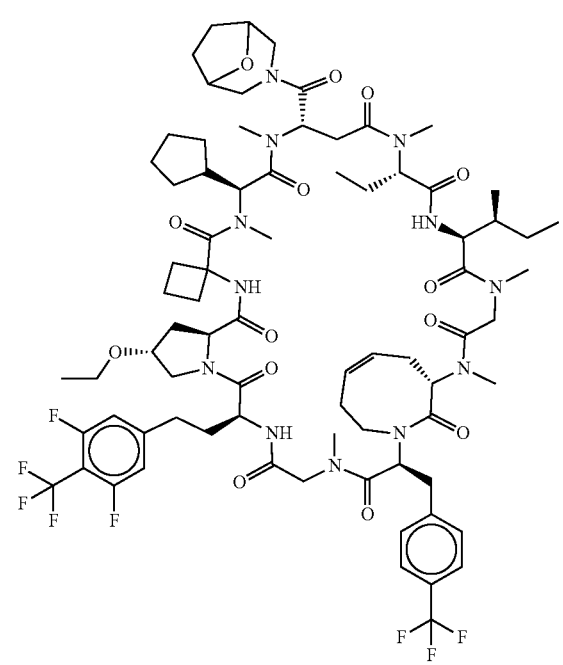 |

TABLE 38-continued
| Compound No. | Structural Formula |
|---|---|
| PP1315 | 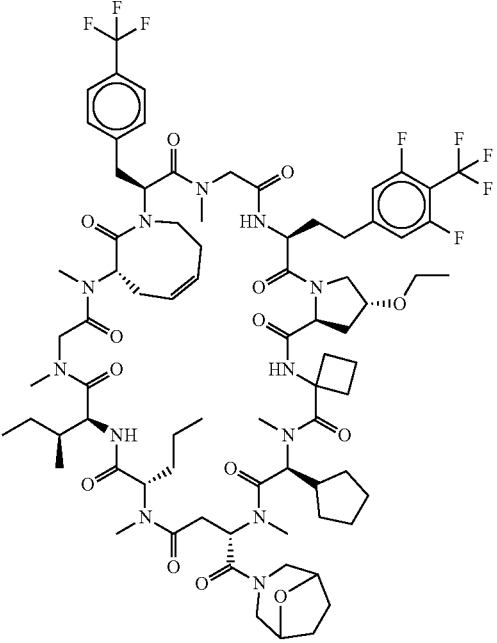 |
| PP1316 | 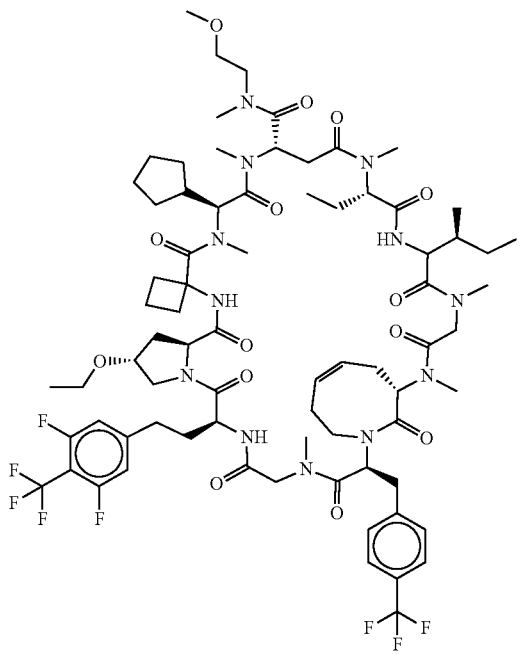 |

TABLE 38-continued

| Compound No. | Structural Formula |
|---|---|
| PP1317 | |
| PP1318 | |

TABLE 38-continued

| Compound No. | Structural Formula |
|---|---|
| PP1319 | |
| PP1320 | |

TABLE 38-continued
| Compound No. | Structural Formula |
|---|---|
| PP1321 | 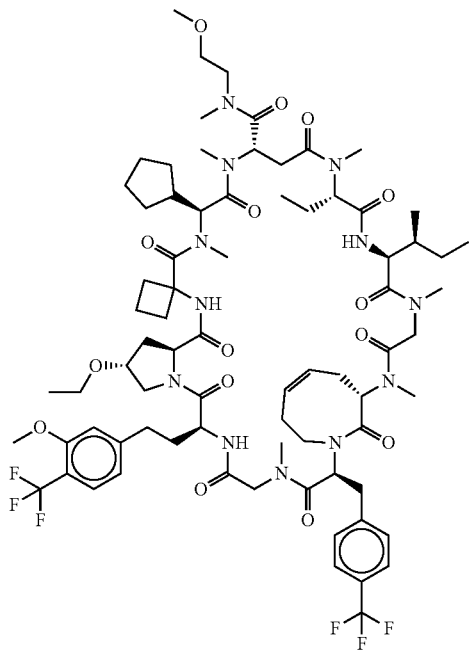 |
| PP1322 | 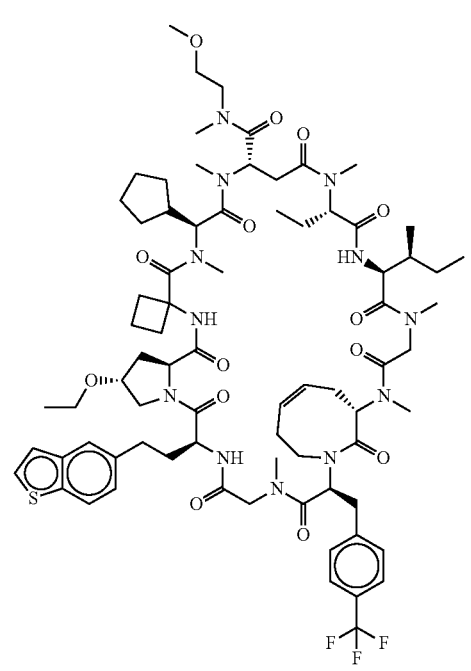 |

TABLE 38-continued

| Compound No. | Structural Formula |
|---|---|
| PP1323 | |
| PP1324 | |

US 12,410,212 B2
TABLE 38-continued
| Compound No. | Structural Formula |
|---|---|
| PP1325 | 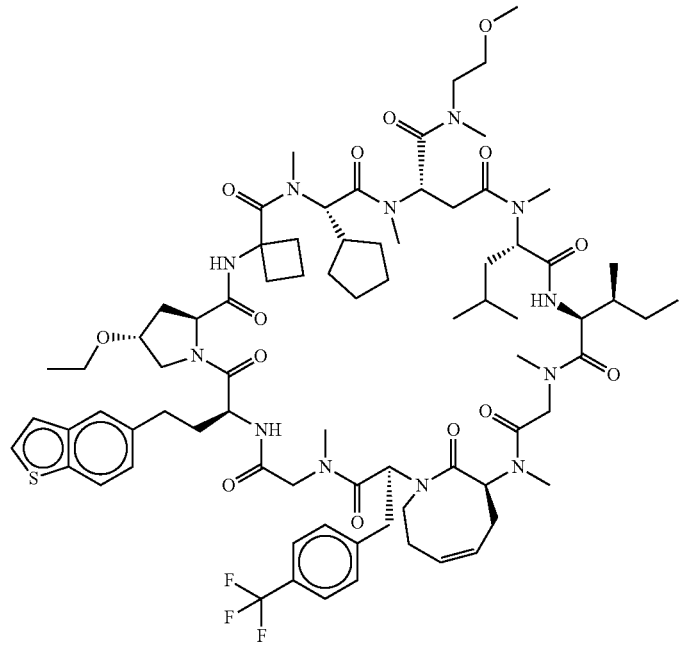 |
| PP1326 | 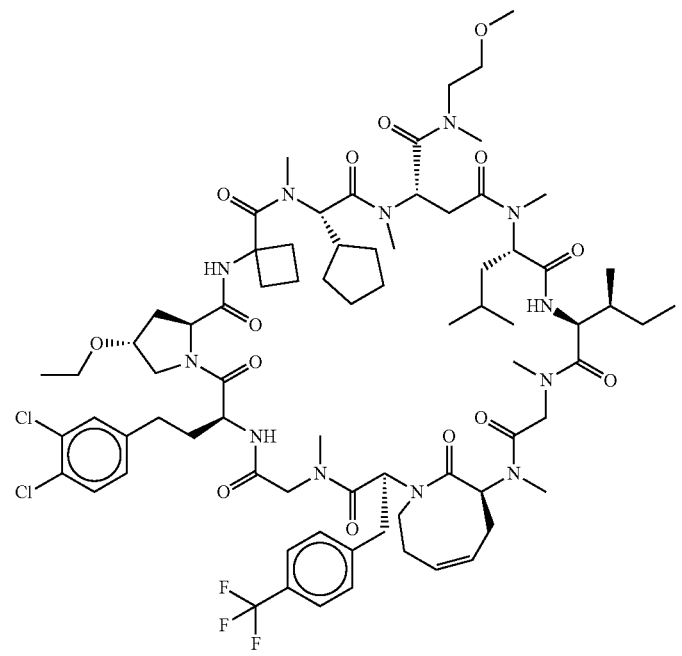 |

TABLE 38-continued
| Compound No. | Structural Formula |
|---|---|
| PP1327 | 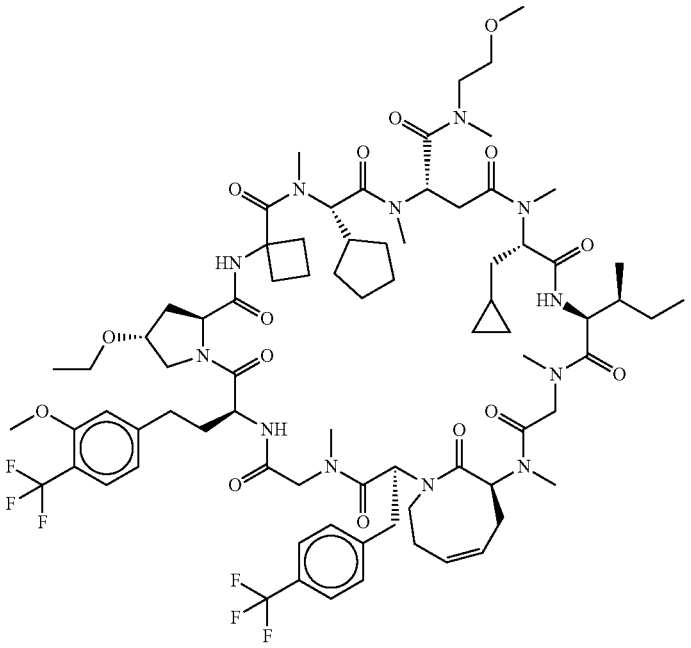 |
| PP1328 | 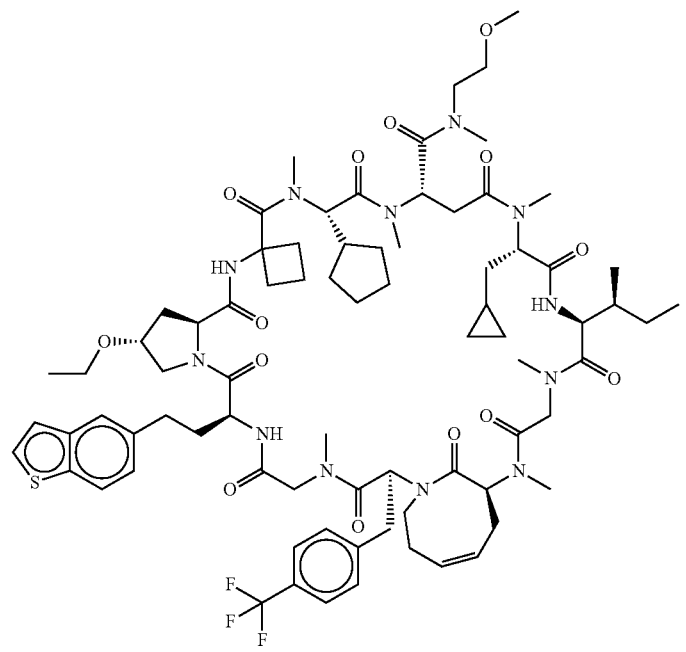 |

TABLE 38-continued
| Compound No. | Structural Formula |
|---|---|
| PP1329 | 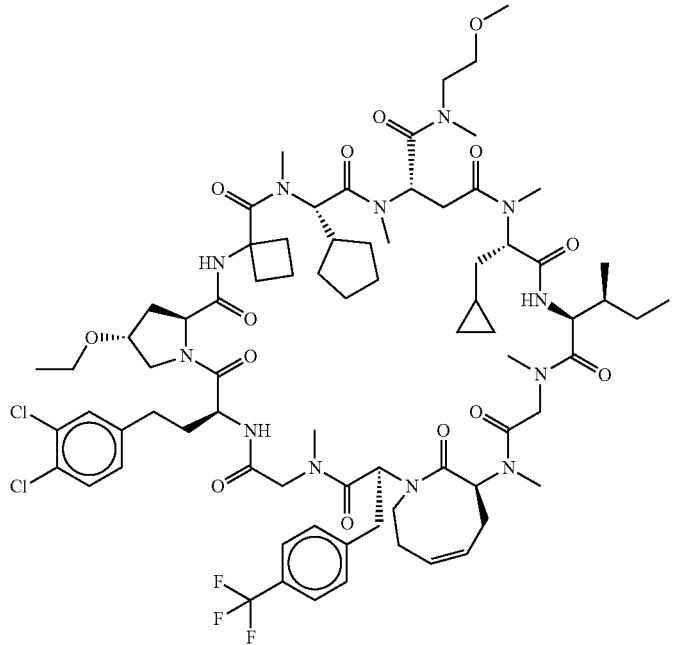 |
| PP1330 | 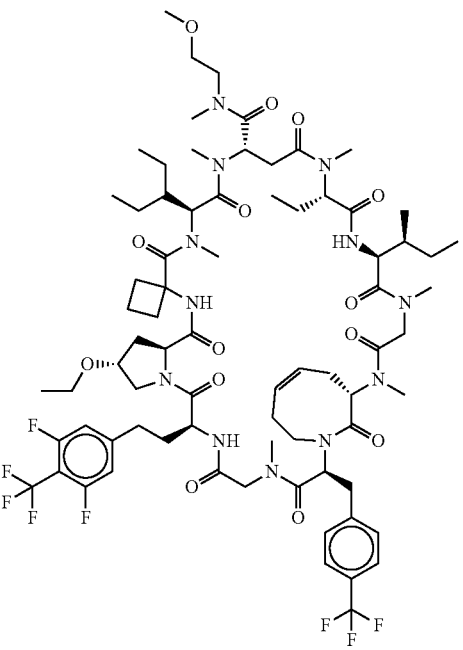 |

TABLE 38-continued

| Compound No. | Structural Formula |
| --- | --- |
| PP1331 | |
| PP1333 | |

TABLE 38-continued
| Compound No. | Structural Formula |
| --- | --- |
| PP1334 | 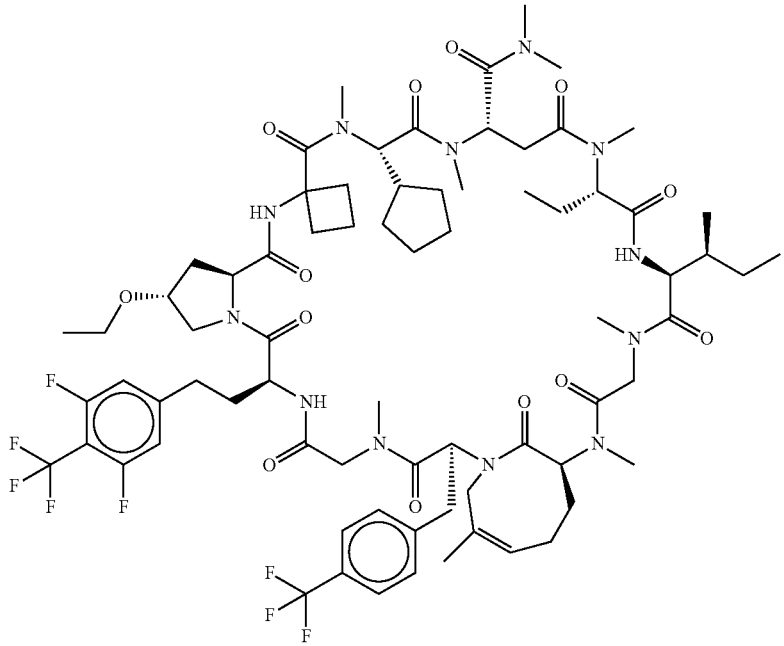 |
| PP1335 | 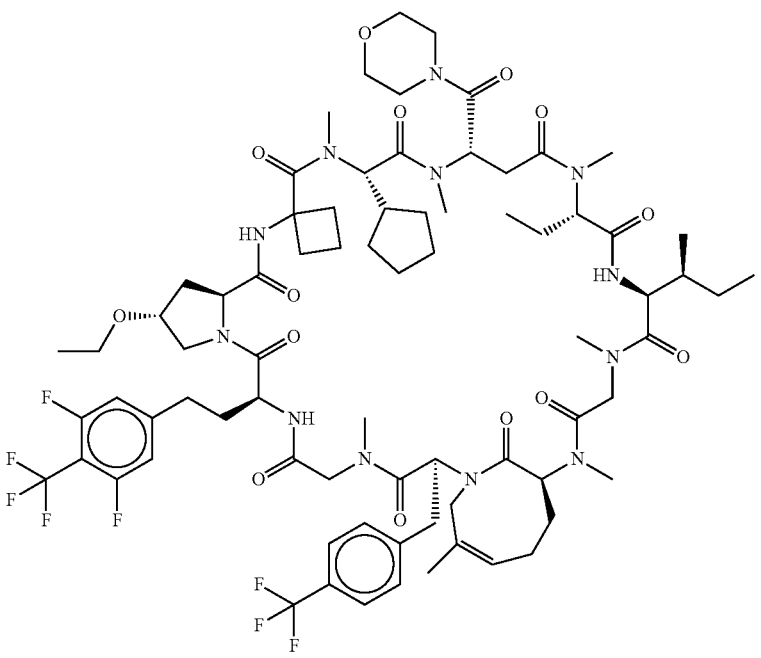 |

TABLE 38-continued

| Compound No. | Structural Formula |
|---|---|
| PP1336 | |
| PP1337 | |

TABLE 38-continued
| Compound No. | Structural Formula |
|---|---|
| PP1338 | 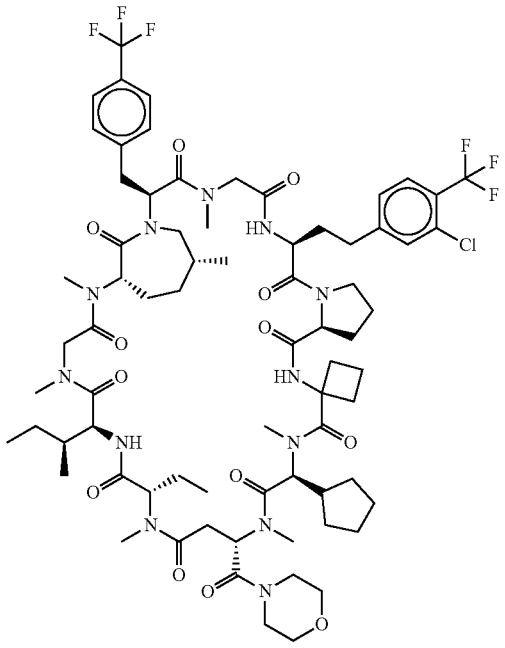 |
| PP1339 | 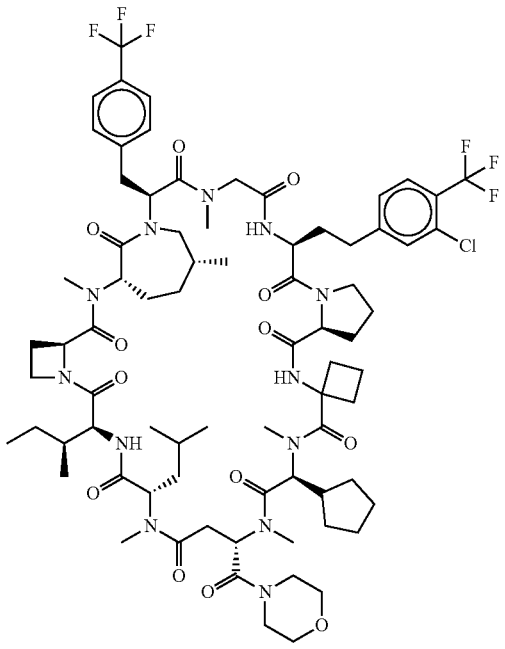 |

TABLE 38-continued

| Compound No. | Structural Formula |
|---|---|
| PP1340 | |
| PP1341 | |

TABLE 38-continued
| Compound No. | Structural Formula |
| --- | --- |
| PP1342 | 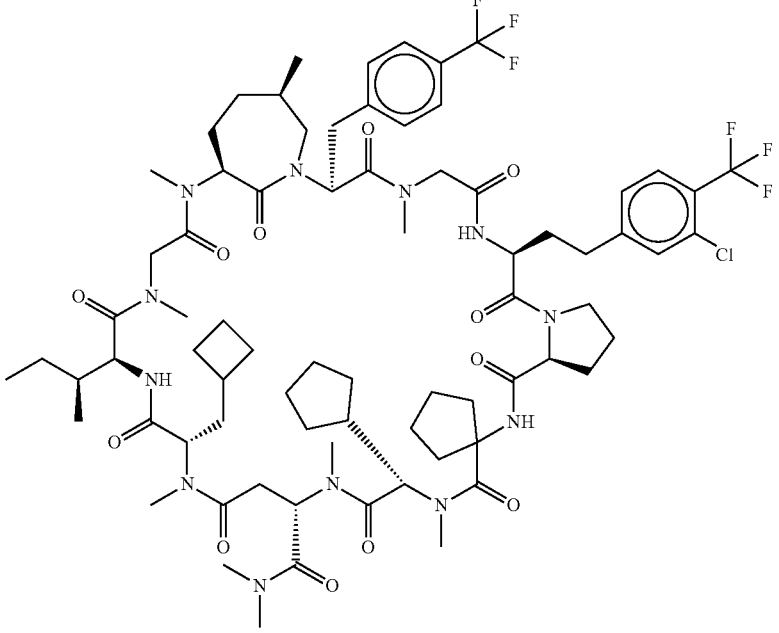 |
| PP1343 | 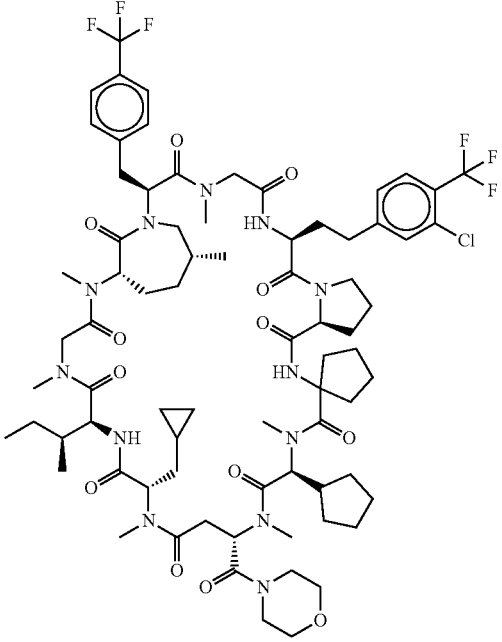 |

TABLE 38-continued
| Compound No. | Structural Formula |
|---|---|
| PP1344 | 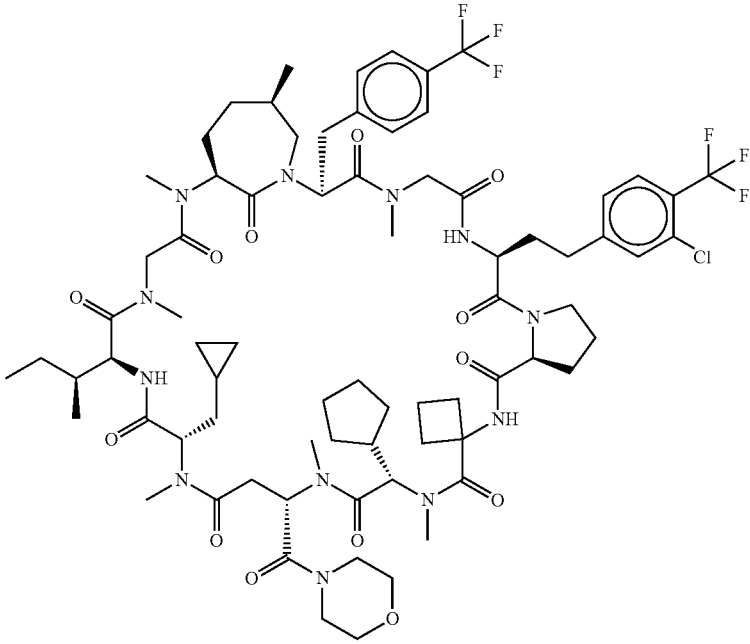 |
| PP1345 | 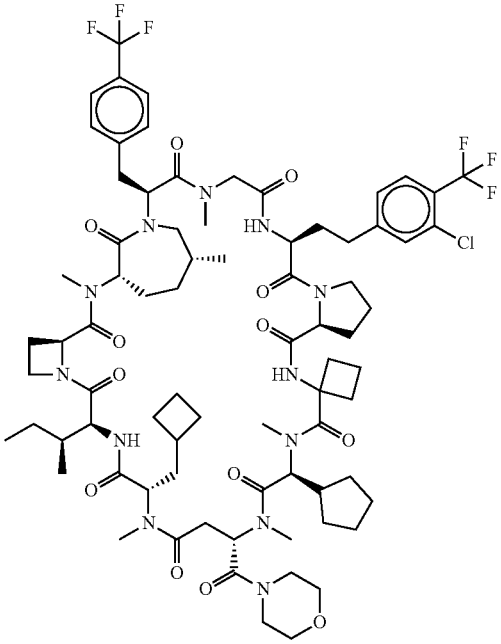 |

TABLE 38-continued

| Compound No. | Structural Formula |
| --- | --- |
| PP1346 | |
| PP1347 | |

| Compound No. | Structural Formula |
|---|---|
| PP1348 | |
| PP1349 | |

TABLE 38-continued

| Compound No. | Structural Formula |
|---|---|
| PP1350 | |
| PP1351 | |

| Compound No. | Structural Formula |
|---|---|
| PP1352 | 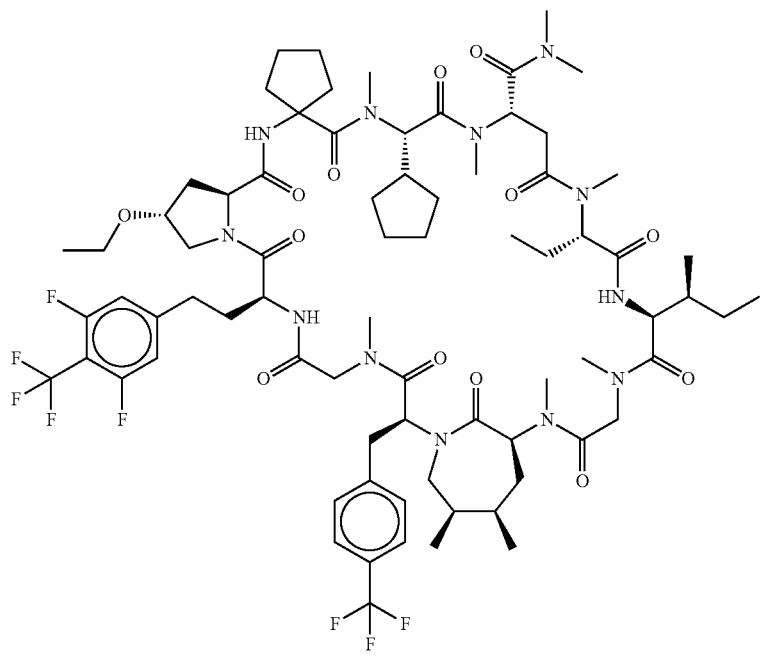 |
| PP1353 | 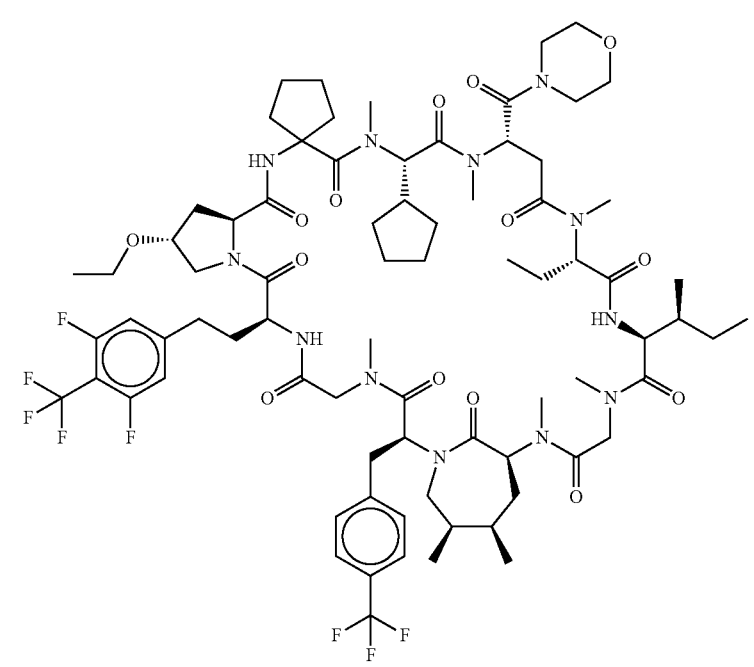 |

TABLE 38-continued
| Compound No. | Structural Formula |
|---|---|
| PP1354 | 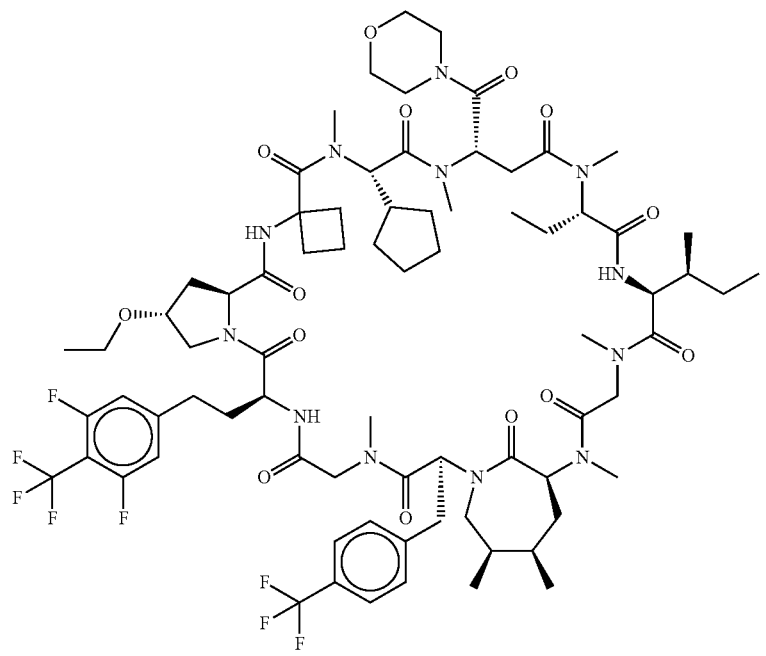 |
| PP1355 | 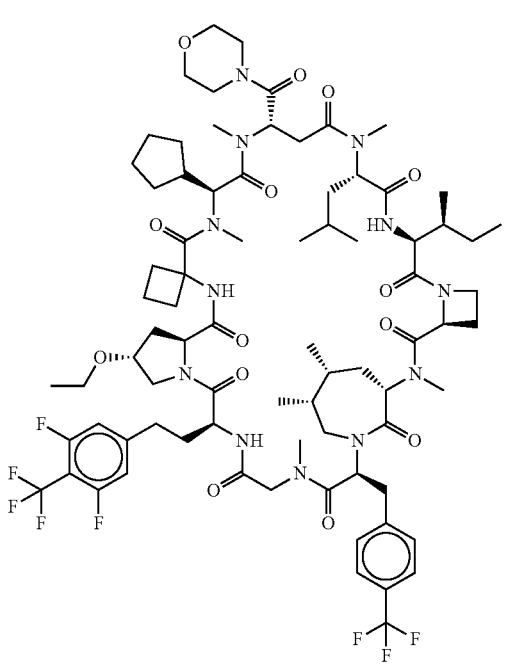 |

TABLE 38-continued
| Compound No. | Structural Formula |
|---|---|
| PP1356 | 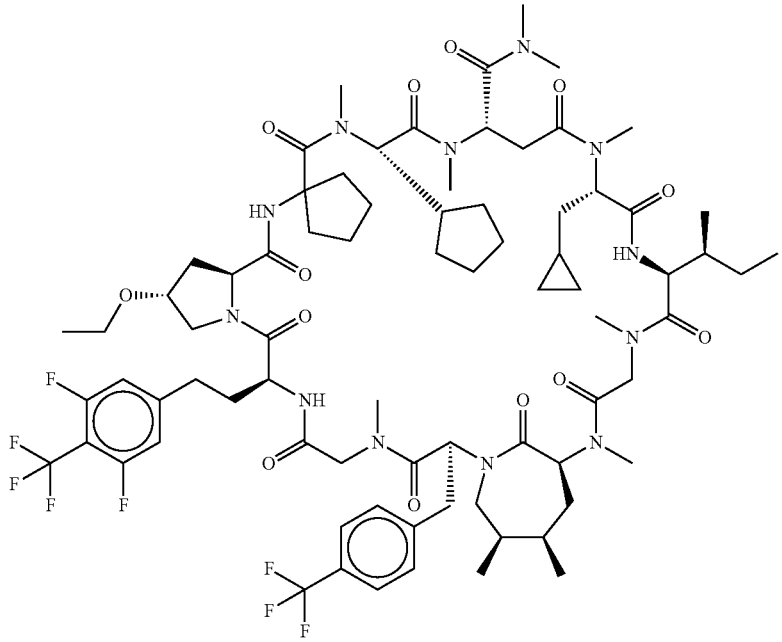 |
| PP1357 | 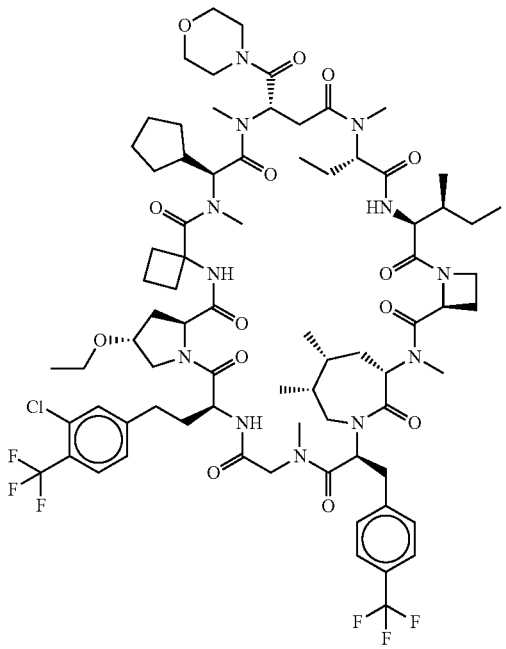 |

TABLE 38-continued
| Compound No. | Structural Formula |
|---|---|
| PP1358 | 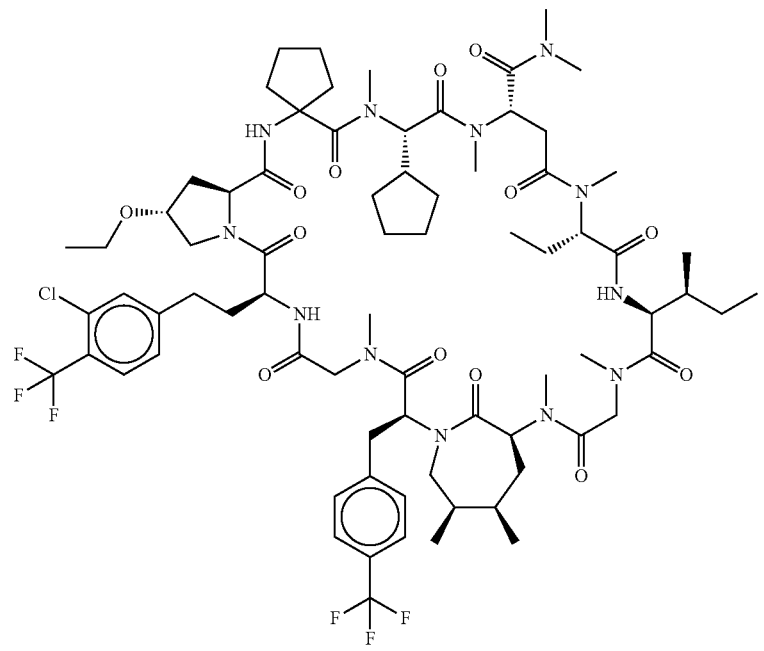 |
| PP1359 | 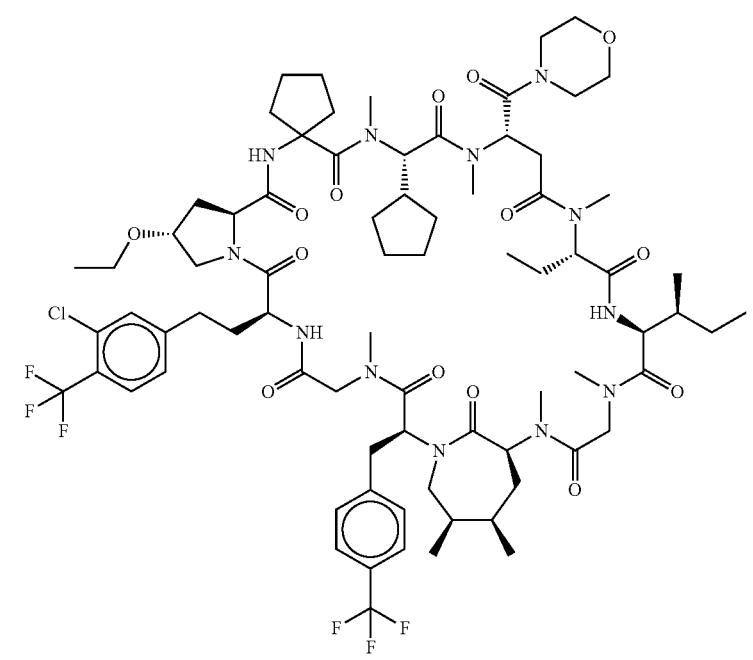 |

TABLE 38-continued
| Compound No. | Structural Formula |
|---|---|
| PP1360 | 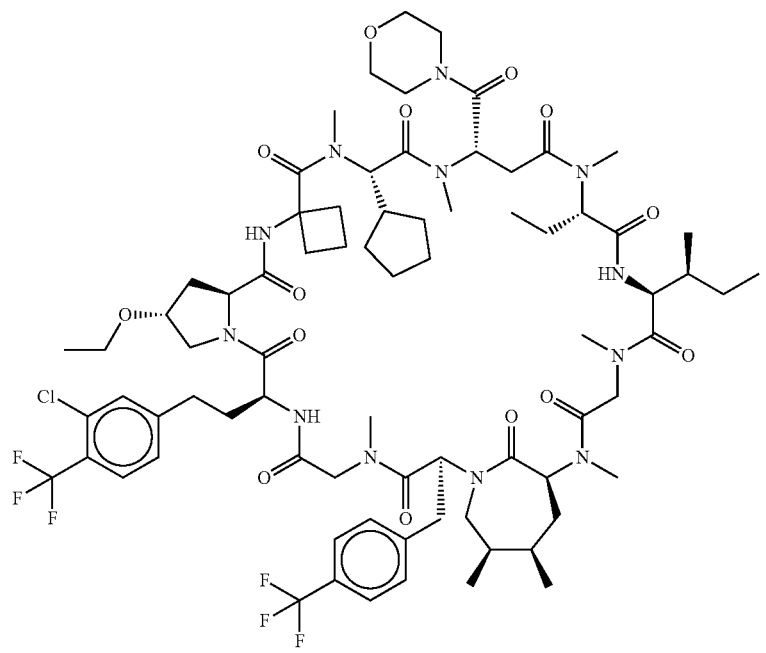 |
| PP1361 | 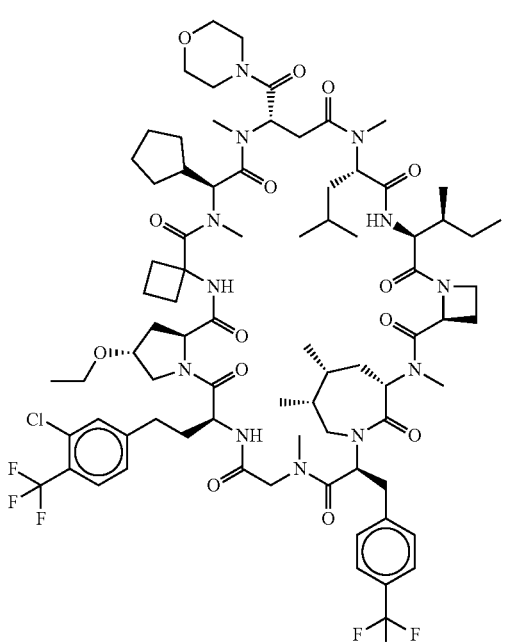 |

TABLE 38-continued

| Compound No. | Structural Formula |
|---|---|
| PP1362 | |
| PP1363 | |

TABLE 38-continued

| Compound No. | Structural Formula |
|---|---|
| PP1364 | |
| PP1365 | |

TABLE 38-continued

| Compound No. | Structural Formula |
|---|---|
| PP1366 | |
| PP1367 | |

TABLE 38-continued
| Compound No. | Structural Formula |
|---|---|
| PP1368 | 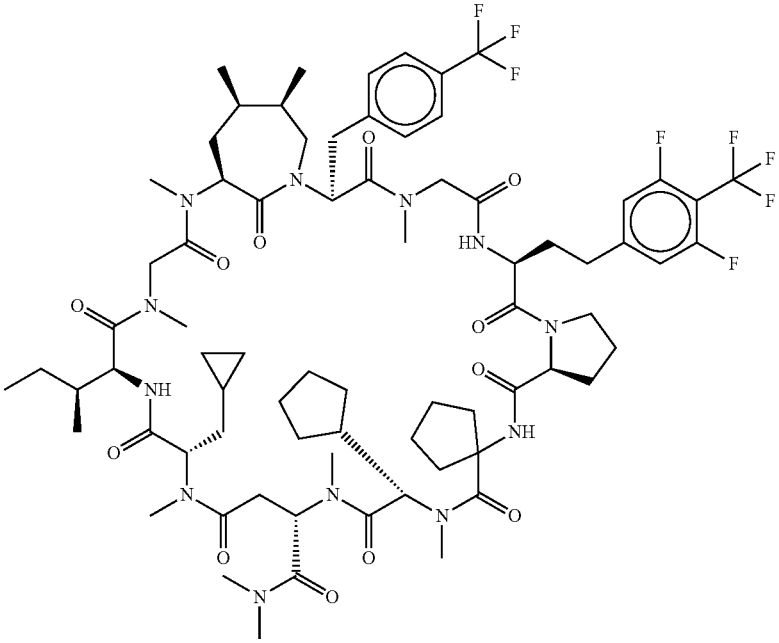 |
| PP1369 | 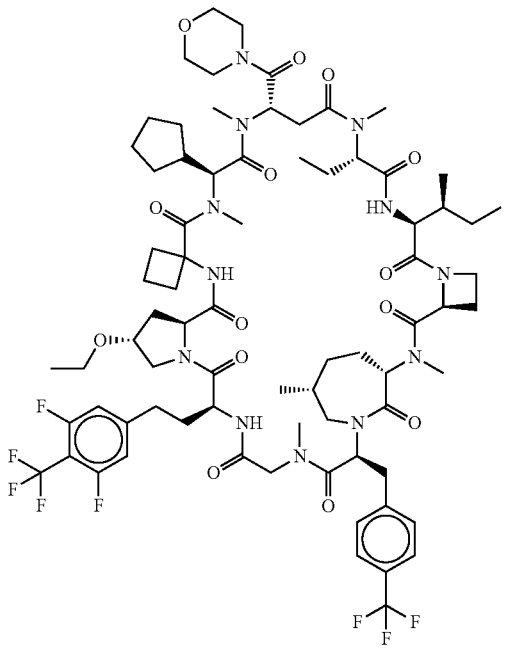 |

TABLE 38-continued
| Compound No. | Structural Formula |
|---|---|
| PP1370 | 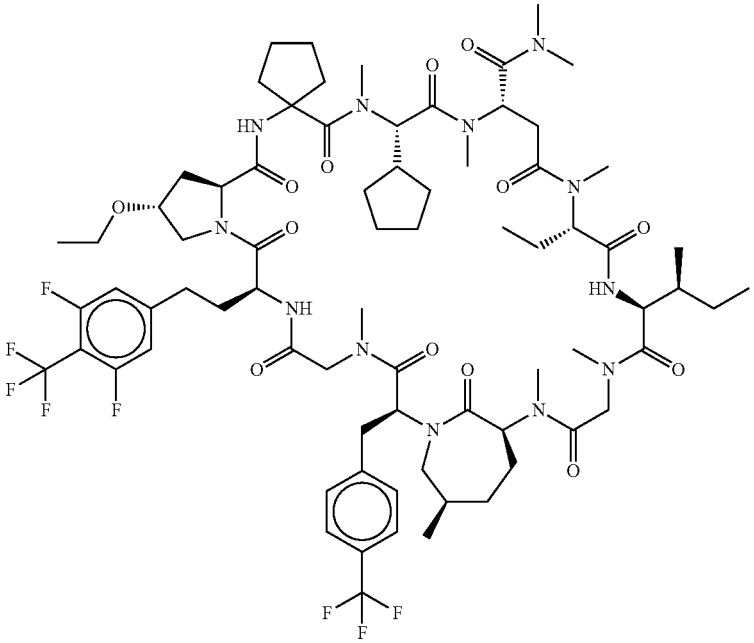 |
| PP1371 | 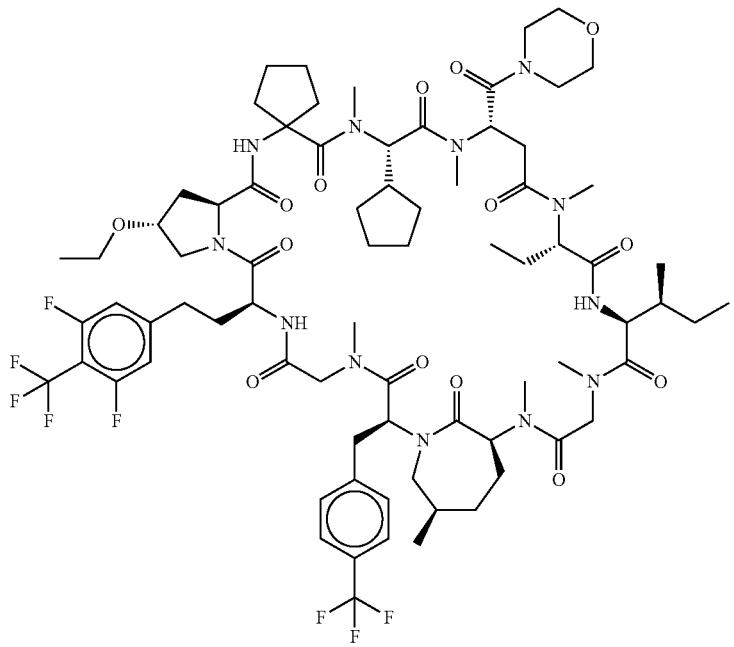 |

TABLE 38-continued
| Compound No. | Structural Formula |
|---|---|
| PP1372 | 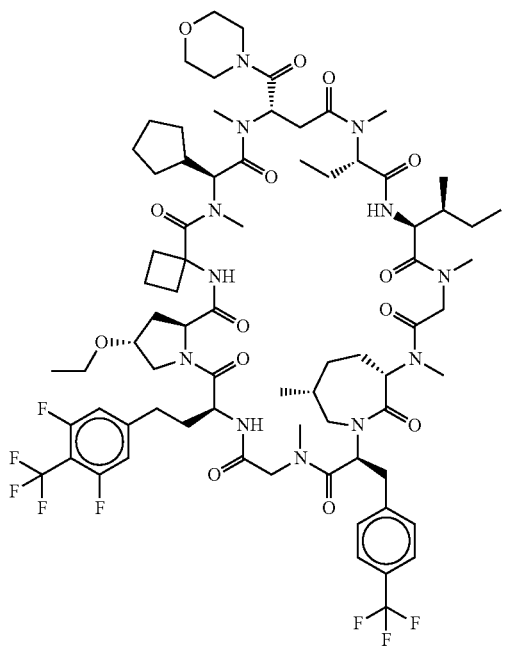 |
| PP1373 | 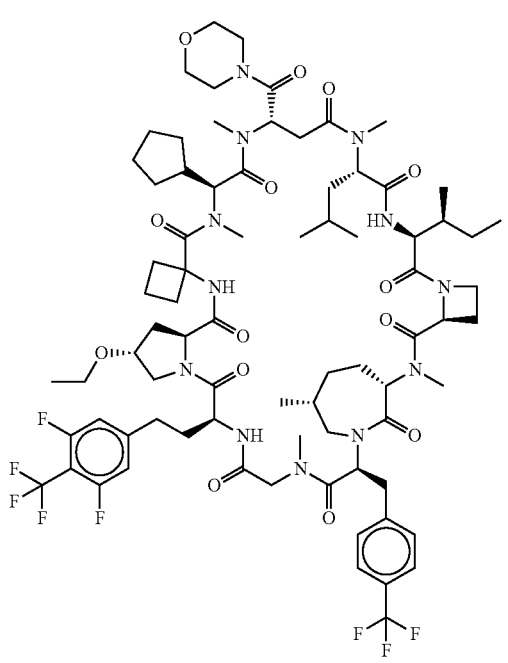 |

TABLE 38-continued

| Compound No. | Structural Formula |
| --- | --- |
| PP1374 | |
| PP1375 | |

TABLE 38-continued
| Compound No. | Structural Formula |
|---|---|
| PP1376 | 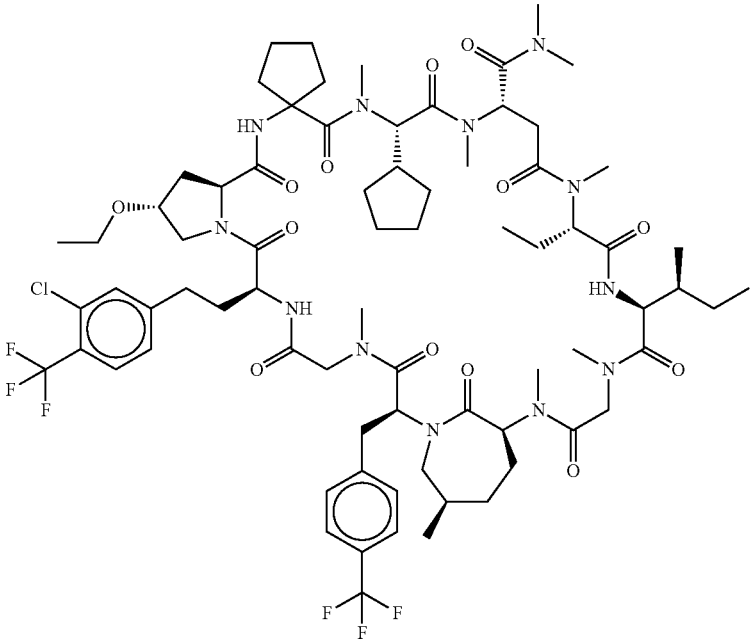 |
| PP1377 | 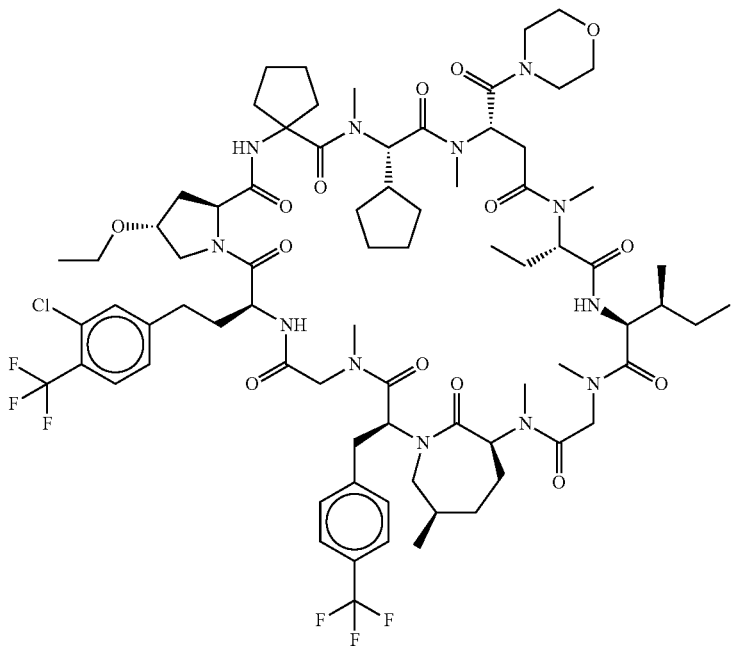 |

TABLE 38-continued
| Compound No. | Structural Formula |
|---|---|
| PP1378 | 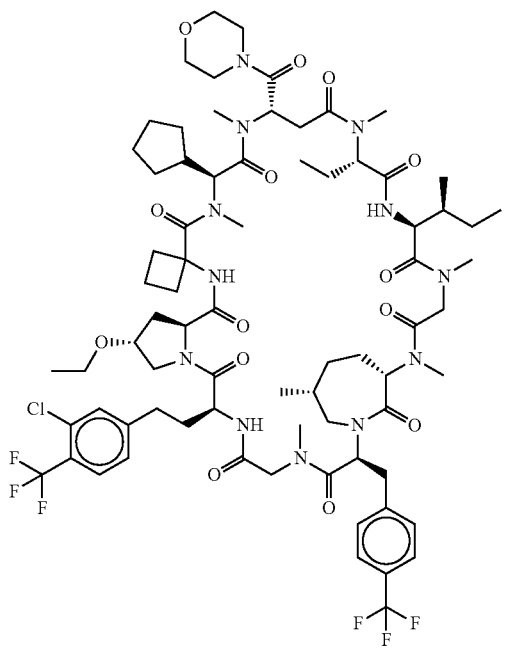 |
| PP1379 | 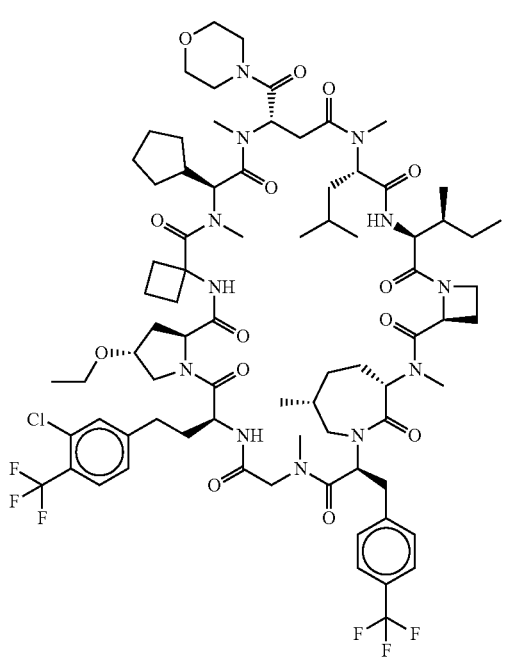 |

TABLE 38-continued

| Compound No. | Structural Formula |
|---|---|
| PP1380 | |
| PP1381 | |

TABLE 38-continued

| Compound No. | Structural Formula |
|---|---|
| PP1382 | |
| PP1383 | |

TABLE 38-continued
| Compound No. | Structural Formula |
|---|---|
| PP1384 | 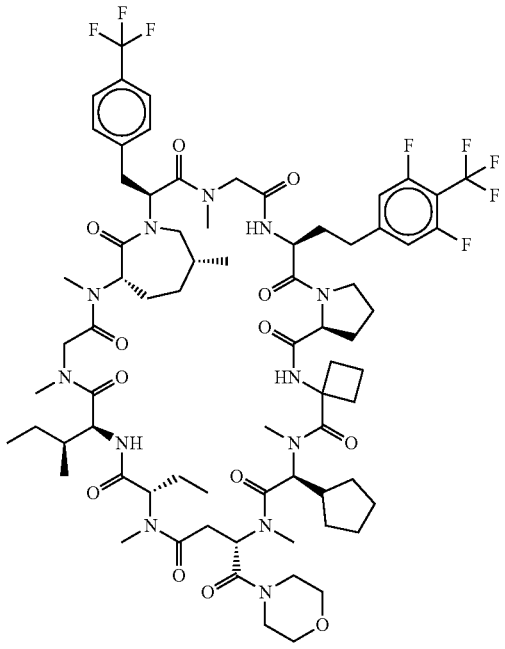 |
| PP1385 | 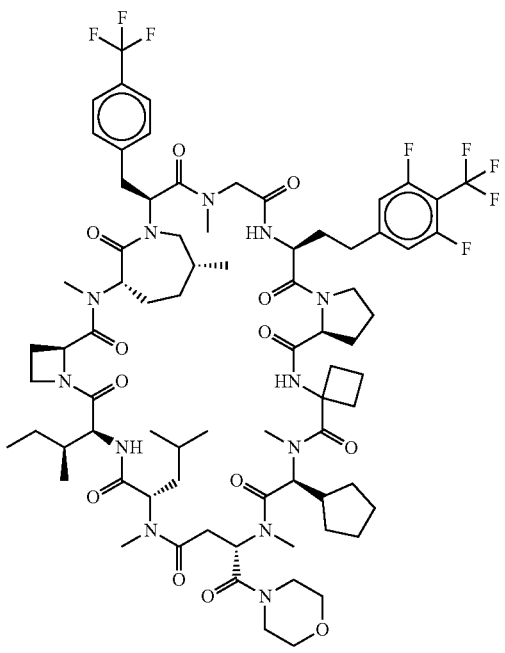 |

TABLE 38-continued

| Compound No. | Structural Formula |
|---|---|
| PP1386 | |
| PP1387 | |

TABLE 38-continued

| Compound No. | Structural Formula |
|---|---|
| PP1388 | |
| PP1389 | |

TABLE 38-continued

| Compound No. | Structural Formula |
| --- | --- |
| PP1390 | |
| PP1391 | |

TABLE 38-continued

| Compound No. | Structural Formula |
|---|---|
| PP1392 | |
| PP1393 | |

TABLE 38-continued
| Compound No. | Structural Formula |
| --- | --- |
| PP1394 | 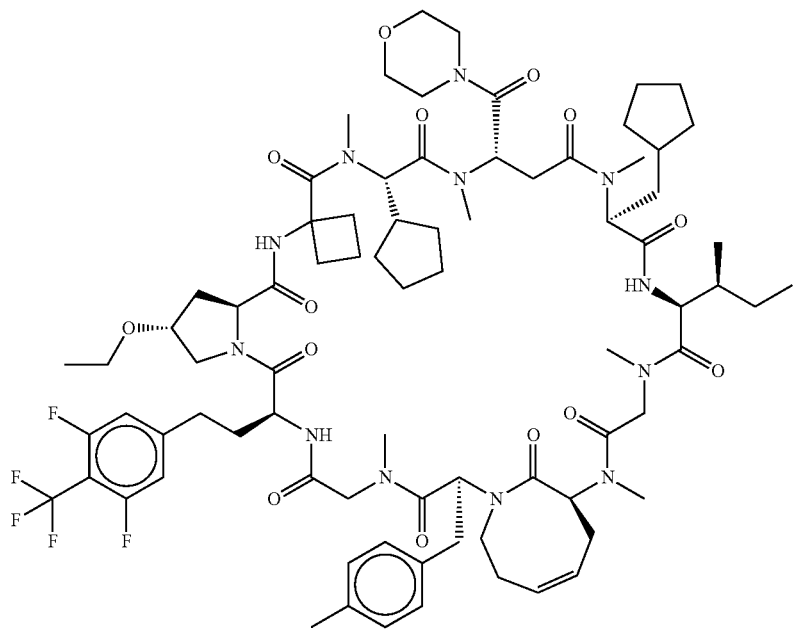 |
| PP1395 | 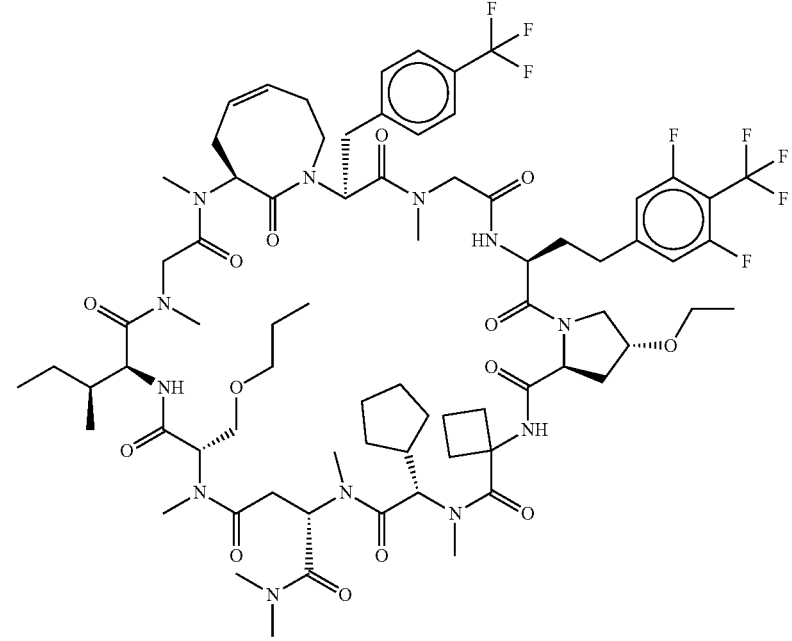 |

TABLE 38-continued

| Compound No. | Structural Formula |
|---|---|
| PP1396 | |
| PP1397 | |

TABLE 38-continued

| Compound No. | Structural Formula |
|---|---|
| PP1398 | |
| PP1399 | |

TABLE 38-continued

| Compound No. | Structural Formula |
|---|---|
| PP1400 | |
| PP1401 | |

TABLE 38-continued

| Compound No. | Structural Formula |
|---|---|
| PP1402 | |
| PP1403 | |

TABLE 38-continued
| Compound No. | Structural Formula |
|---|---|
| PP1404 | 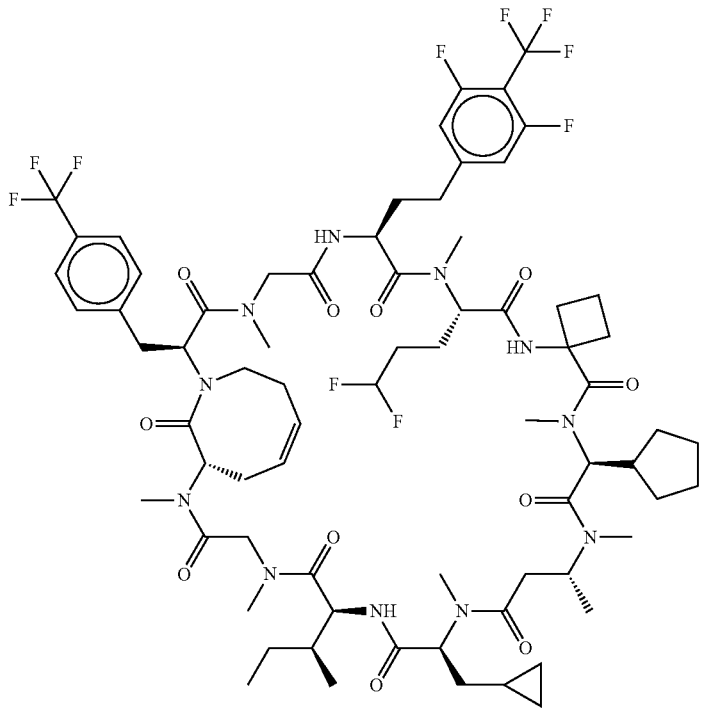 |
| PP1405 | 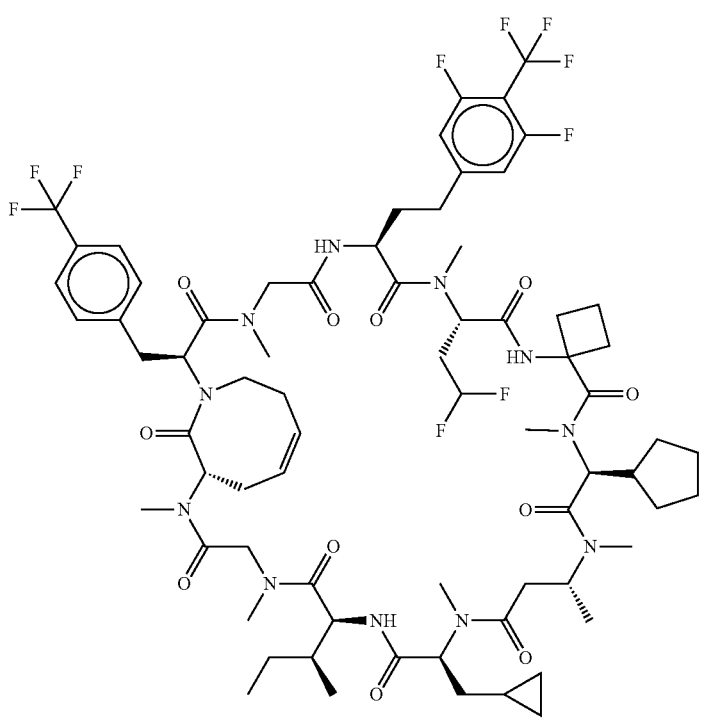 |

TABLE 38-continued
| Compound No. | Structural Formula |
|---|---|
| PP1406 | 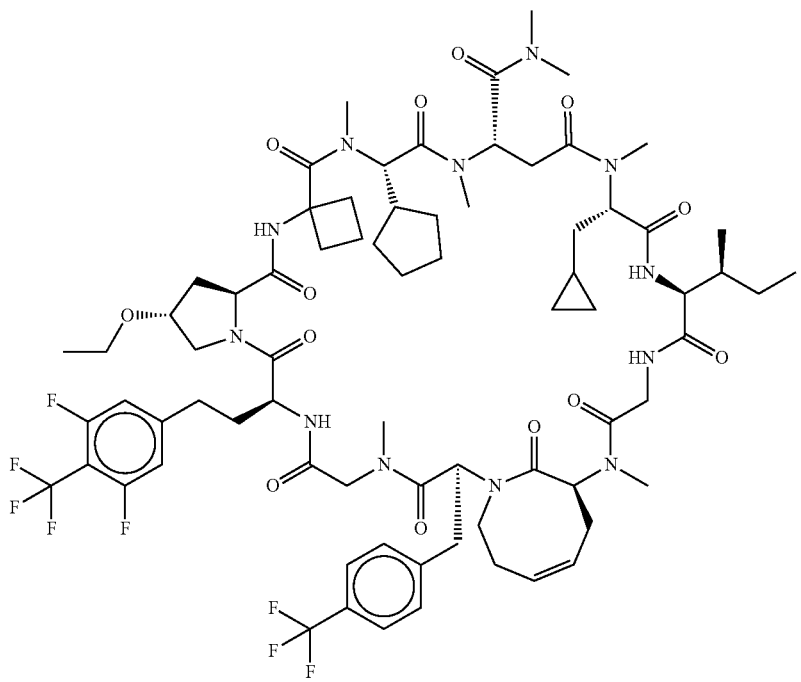 |
| PP1407 | 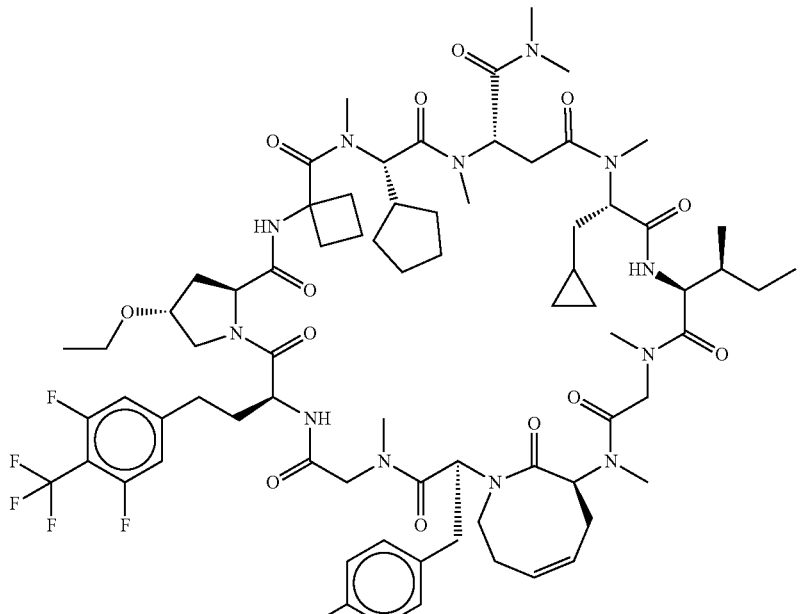 |

TABLE 38-continued

| Compound No. | Structural Formula |
|---|---|
| PP1408 | |
| PP1409 | |

TABLE 38-continued
| Compound No. | Structural Formula |
|---|---|
| PP1410 | 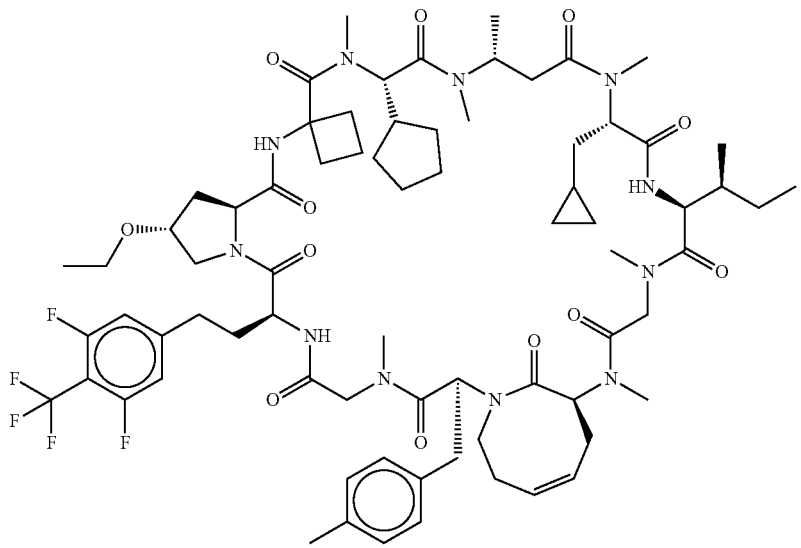 |
| PP1411 | 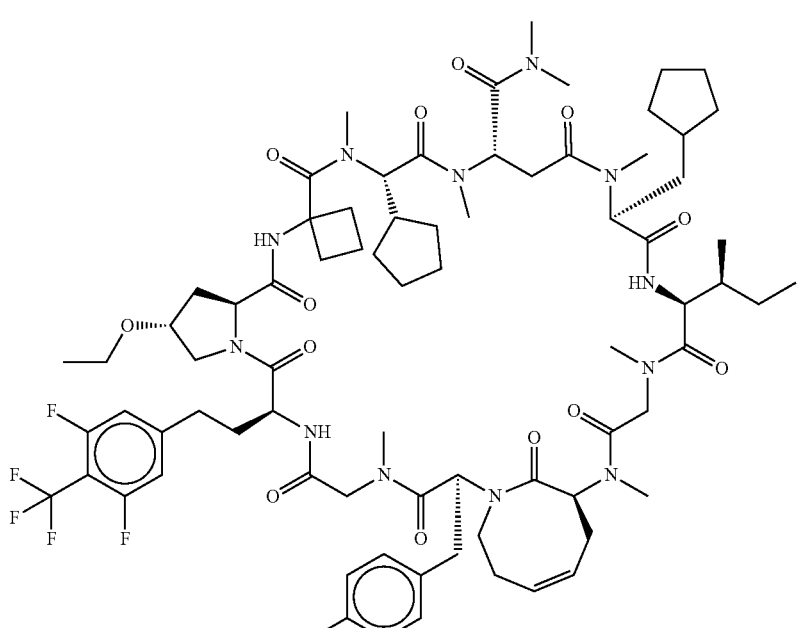 |

TABLE 38-continued
| Compound No. | Structural Formula |
|---|---|
| PP1412 | 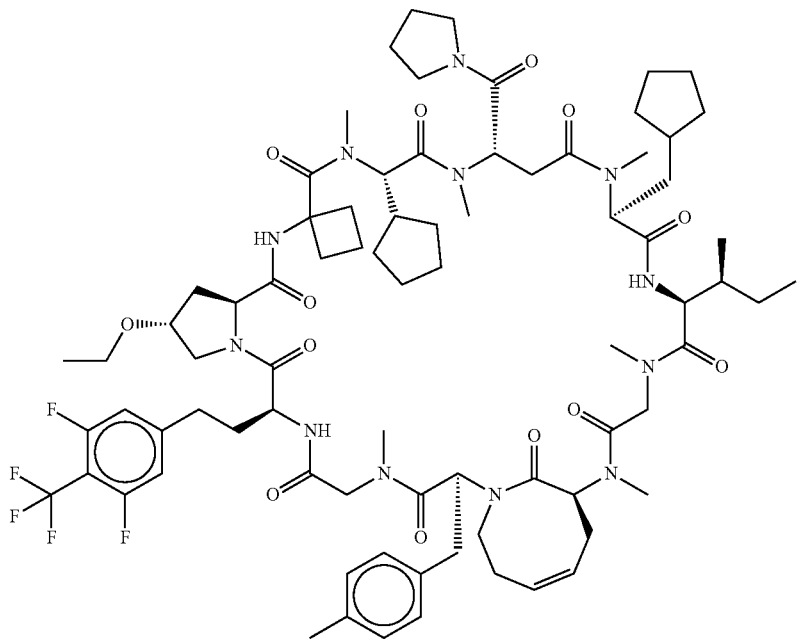 |
| PP1413 | 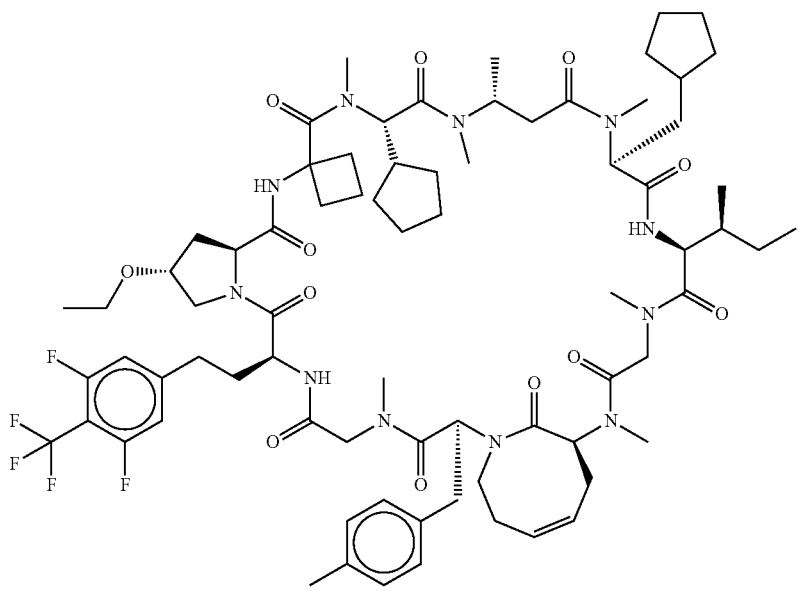 |

TABLE 38-continued
| Compound No. | Structural Formula |
|---|---|
| PP1414 | 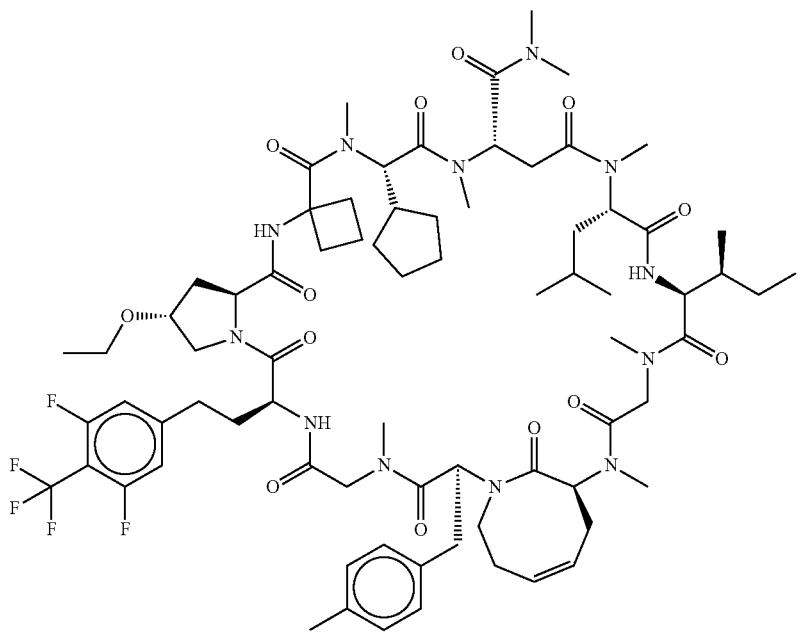 |
| PP1415 | 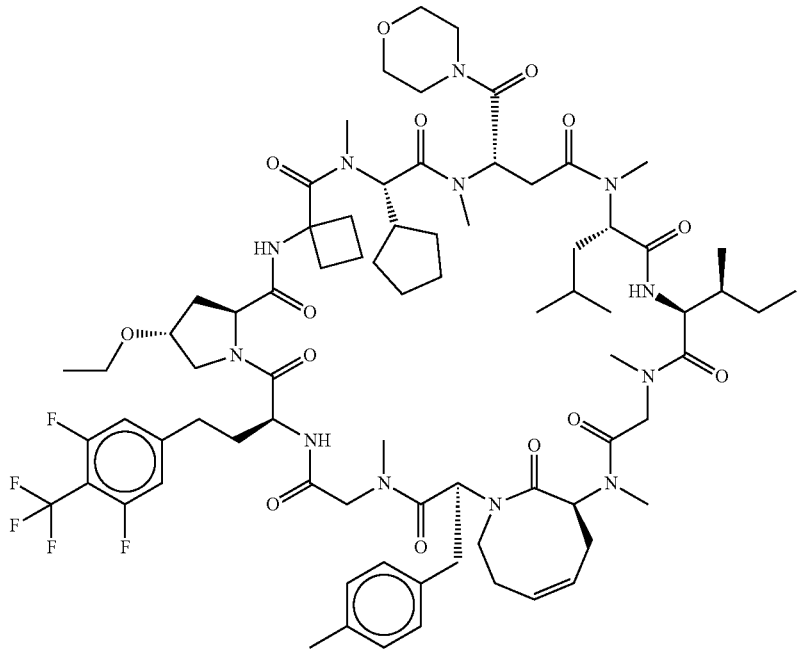 |

TABLE 38-continued
| Compound No. | Structural Formula |
|---|---|
| PP1416 | 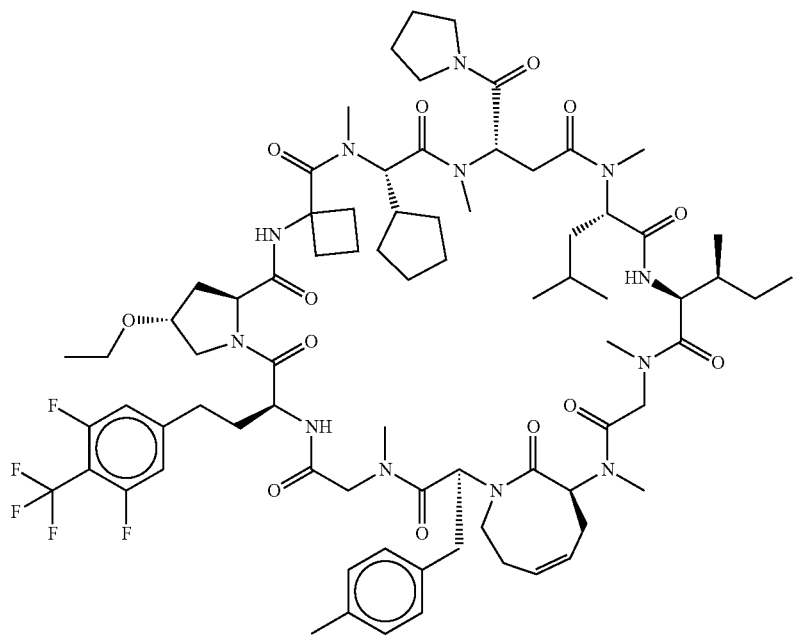 |
| PP1417 | 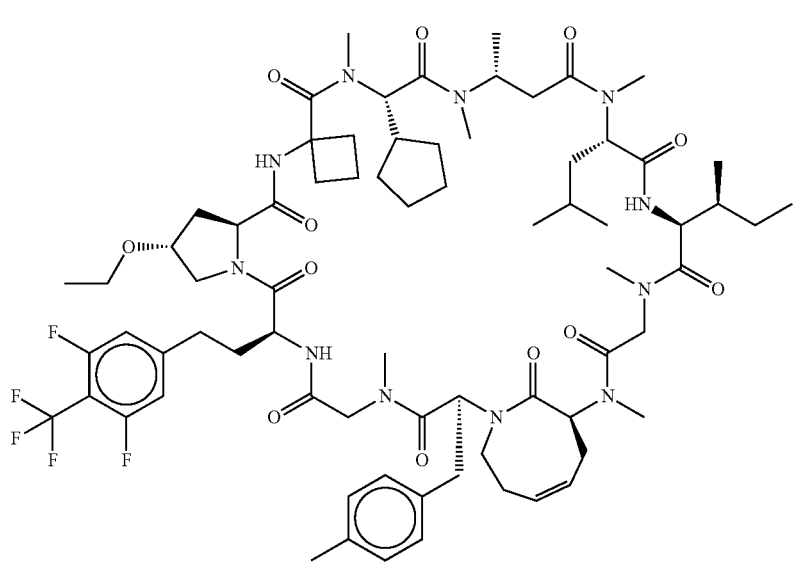 |

TABLE 38-continued
| Compound No. | Structural Formula |
|---|---|
| PP1418 | 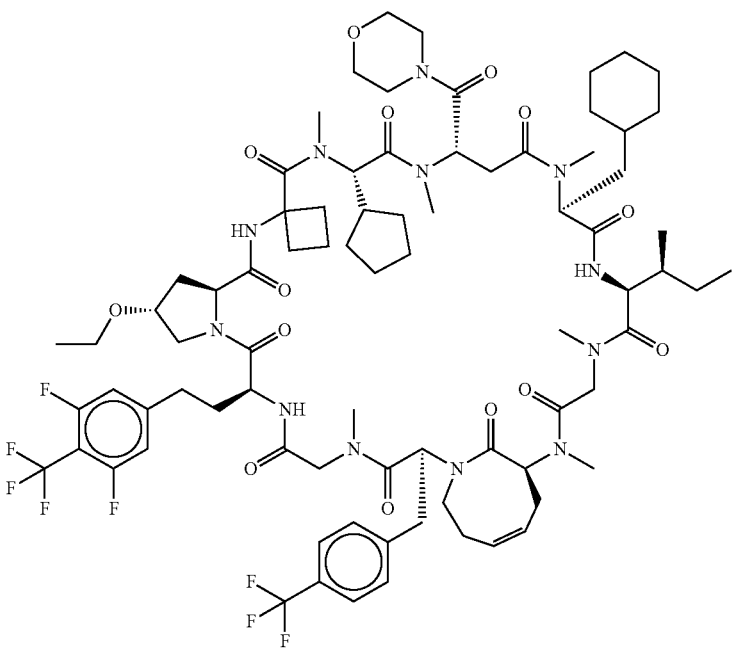 |
| PP1419 | 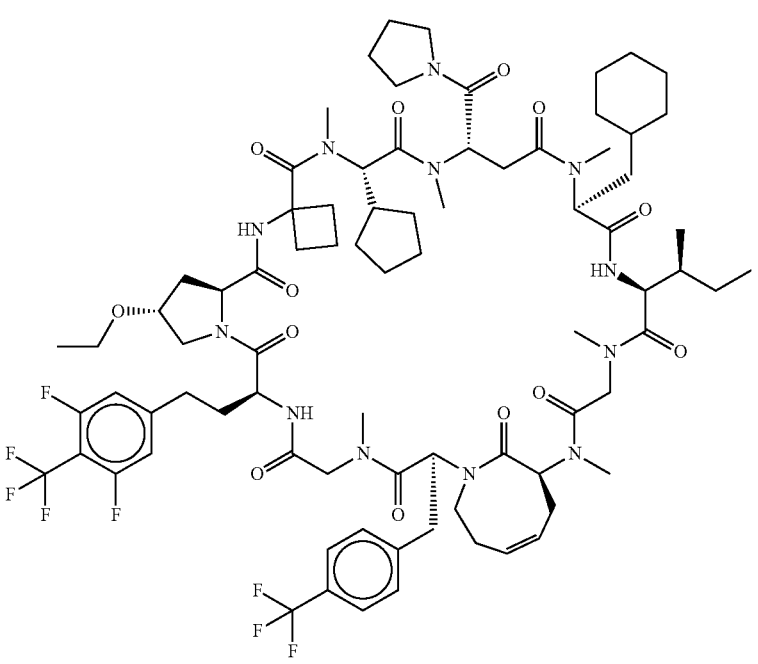 |

| Compound No. | Structural Formula |
|---|---|
| PP1420 | |
| PP1421 | |

TABLE 38-continued
| Compound No. | Structural Formula |
|---|---|
| PP1422 | 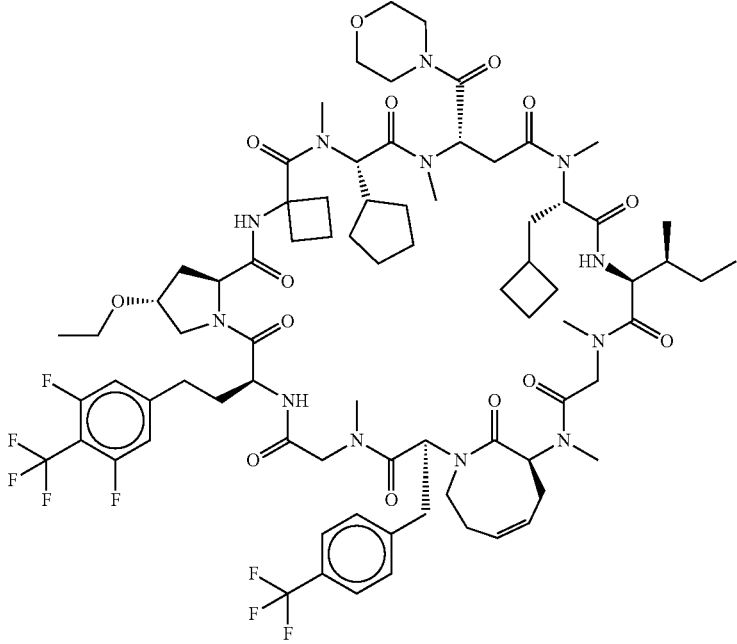 |
| PP1423 | 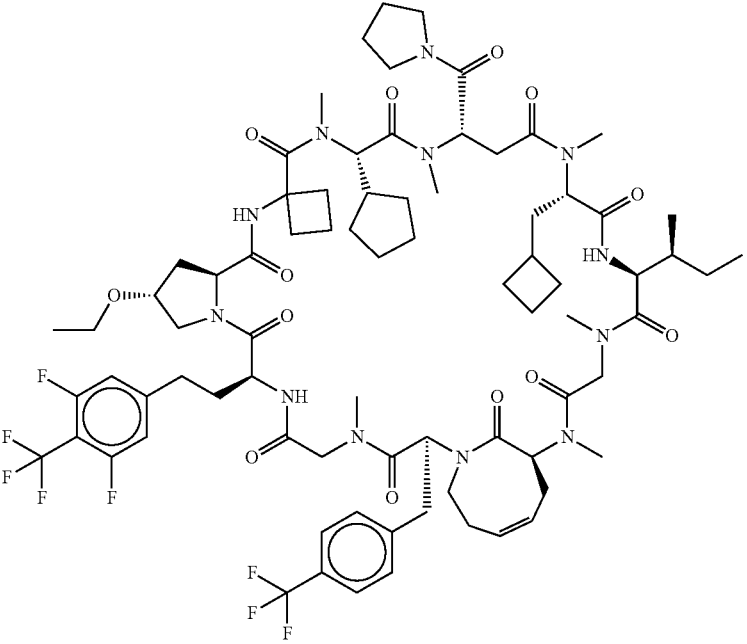 |

TABLE 38-continued
| Compound No. | Structural Formula |
|---|---|
| PP1424 | 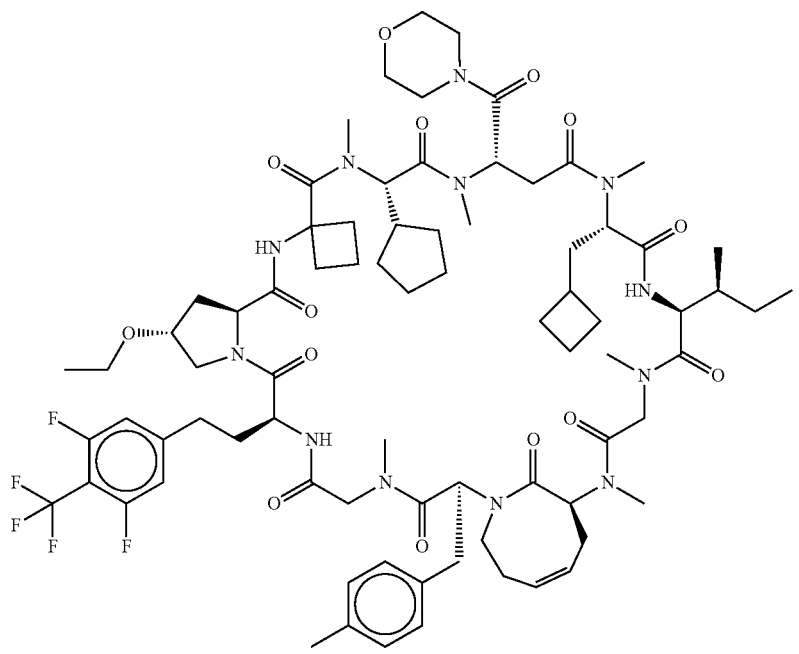 |
| PP1425 | 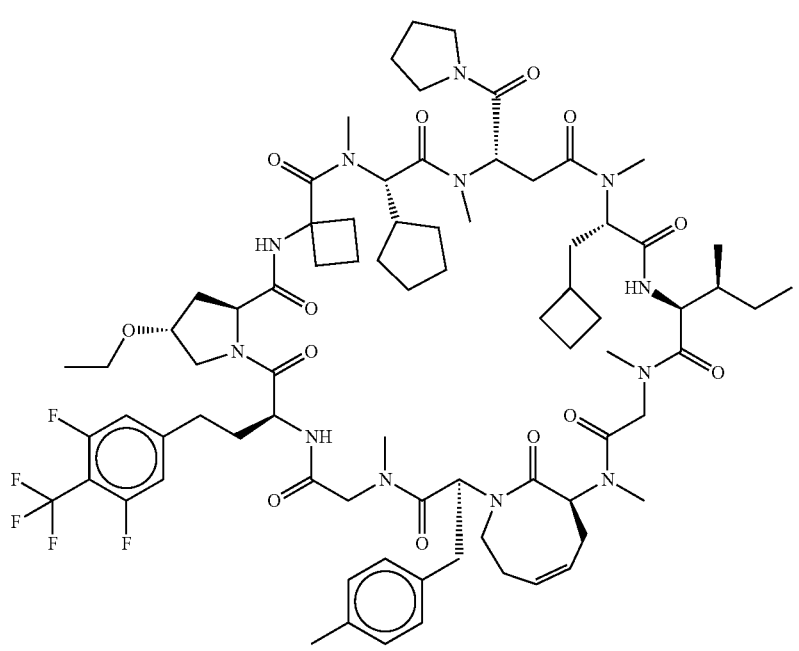 |

TABLE 38-continued

| Compound No. | Structural Formula |
|---|---|
| PP1426 | |
| PP1427 | |

TABLE 38-continued
| Compound No. | Structural Formula |
|---|---|
| PP1428 | 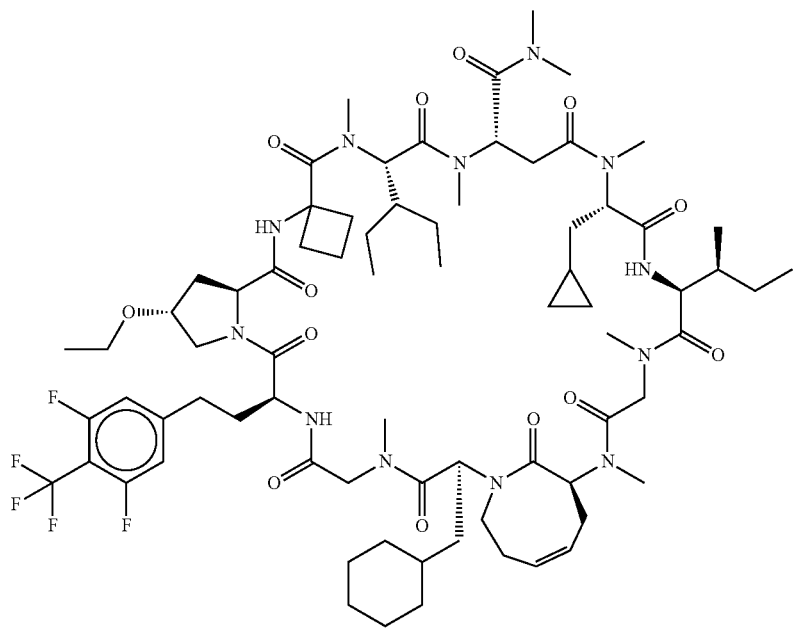 |
| PP1429 | 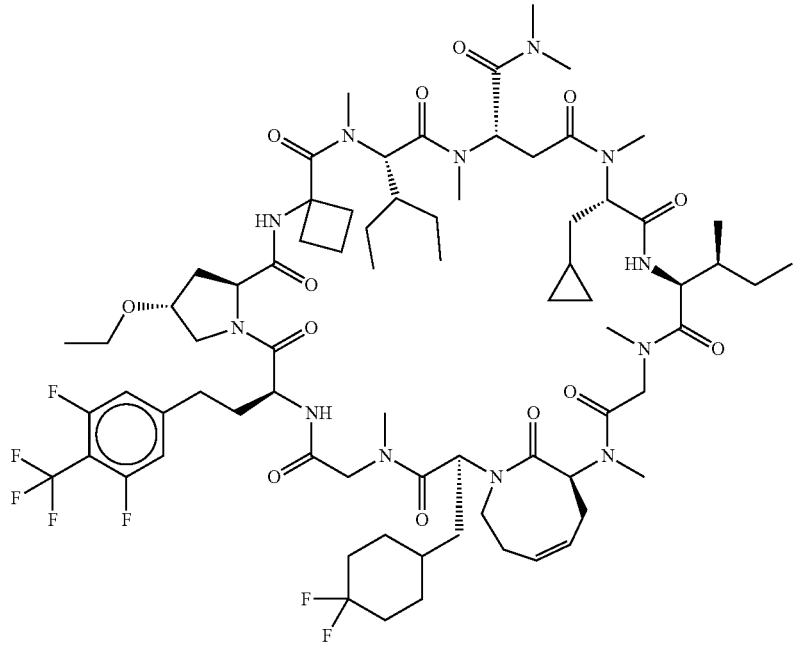 |

TABLE 38-continued
| Compound No. | Structural Formula |
|---|---|
| PP1430 | 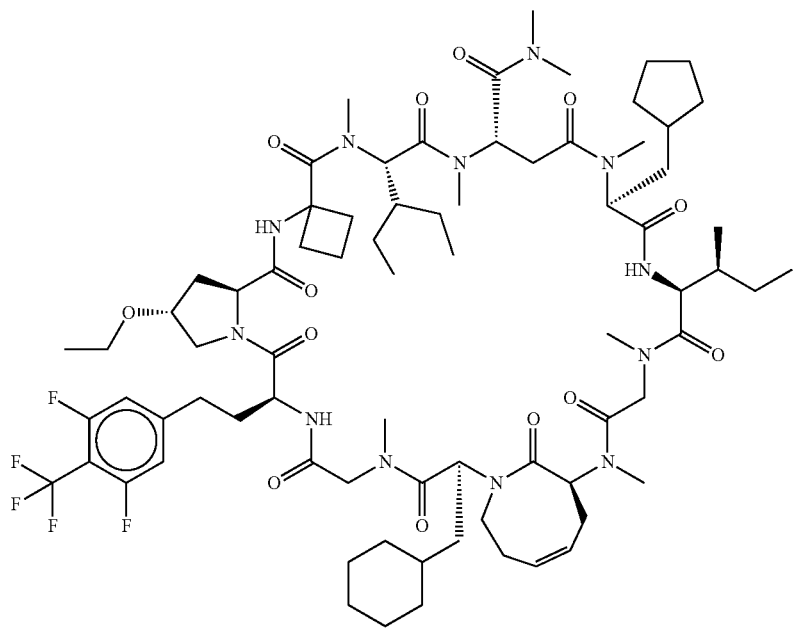 |
| PP1431 | 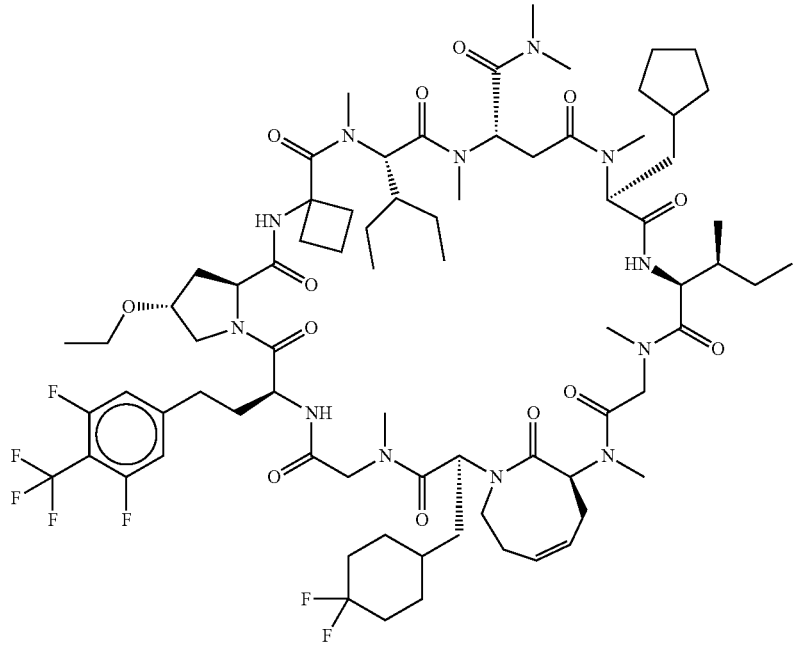 |

TABLE 38-continued
| Compound No. | Structural Formula |
|---|---|
| PP1432 | 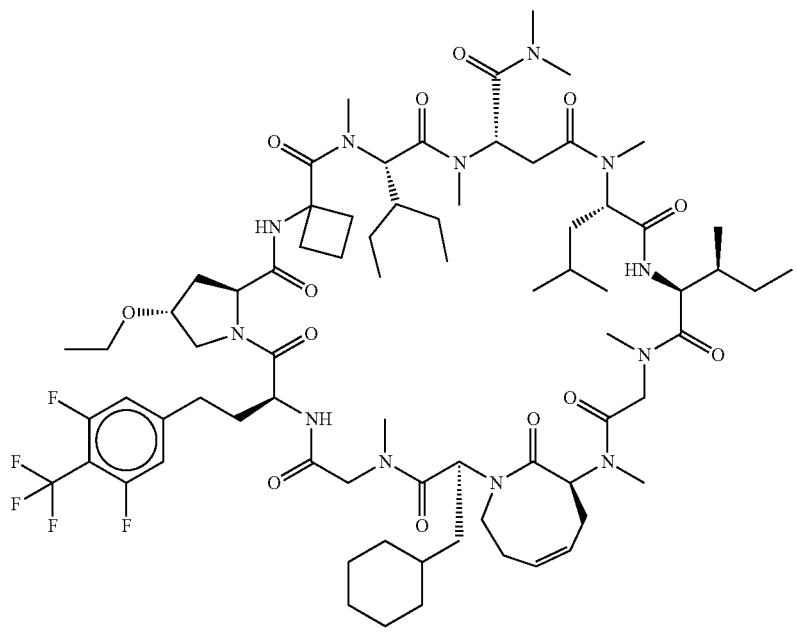 |
| PP1433 | 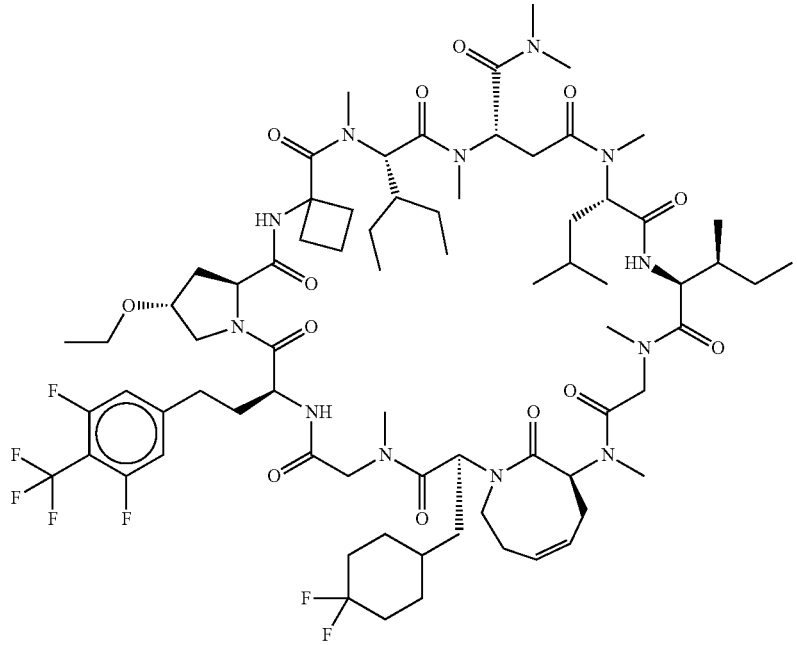 |

TABLE 38-continued
| Compound No. | Structural Formula |
|---|---|
| PP1434 | 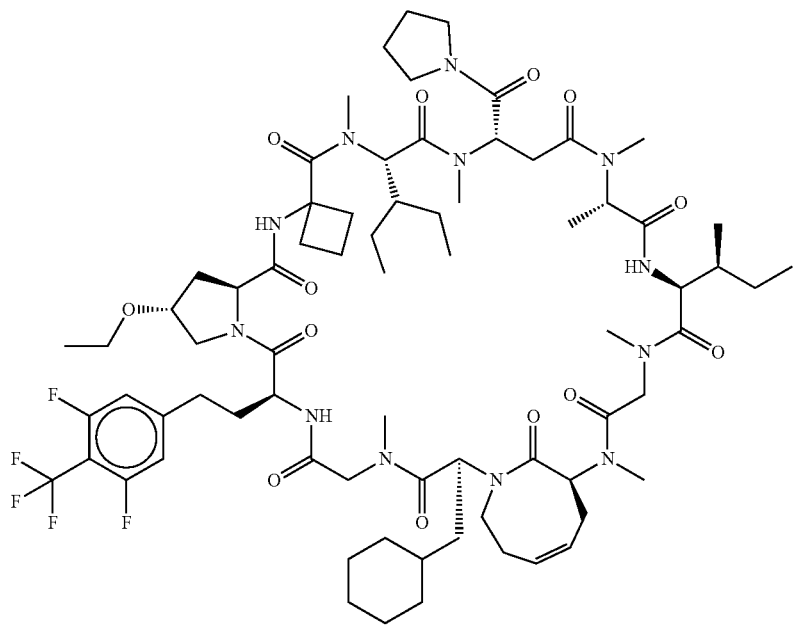 |
| PP1435 | 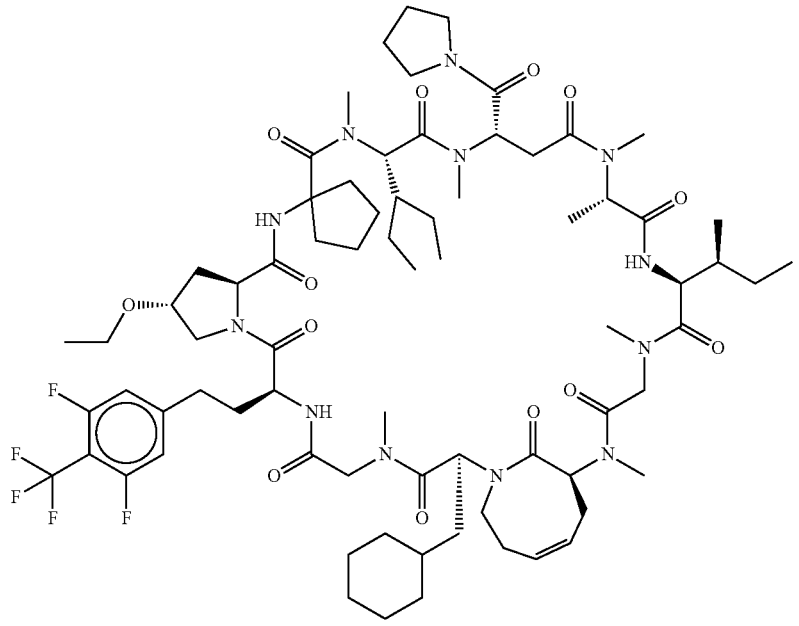 |

TABLE 38-continued

| Compound No. | Structural Formula |
|---|---|
| PP1436 | |
| PP1437 | |

TABLE 38-continued
| Compound No. | Structural Formula |
|---|---|
| PP1438 | 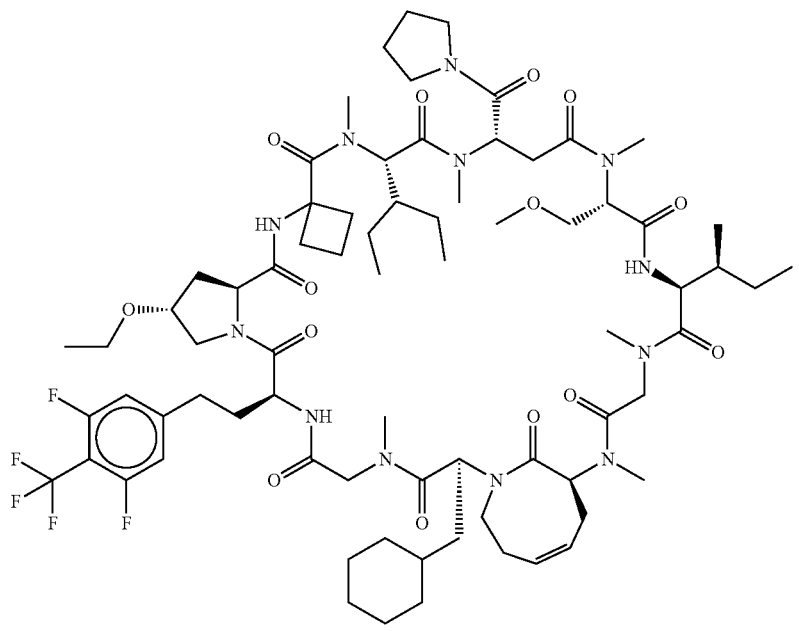 |
| PP1439 | 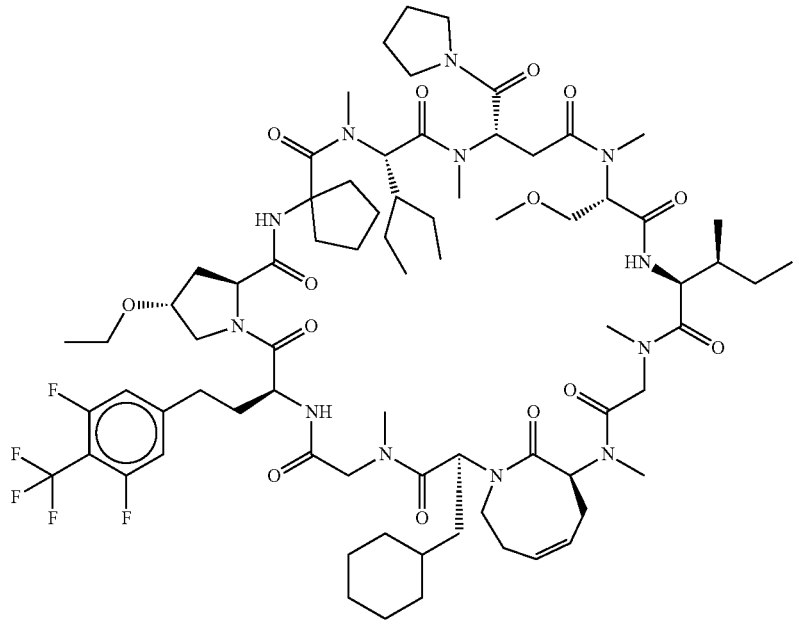 |

TABLE 38-continued
| Compound No. | Structural Formula |
|---|---|
| PP1440 | 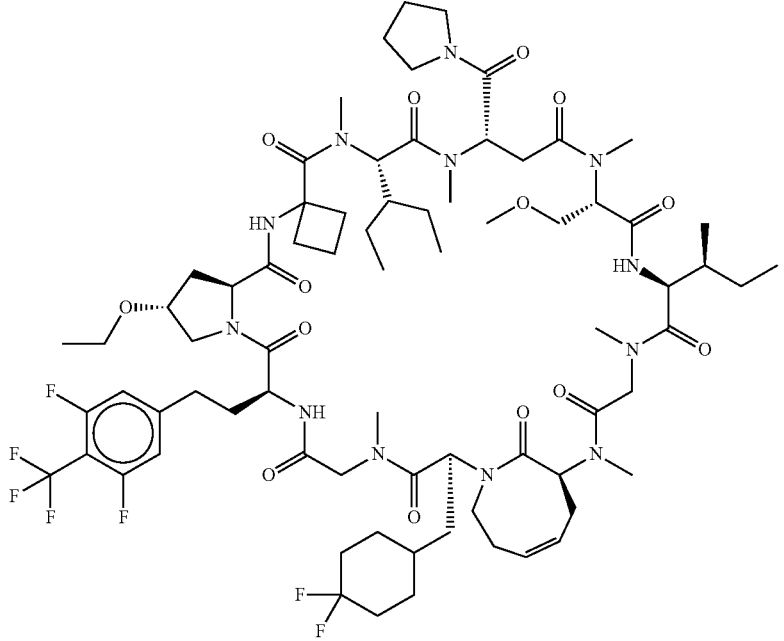 |
| PP1441 | 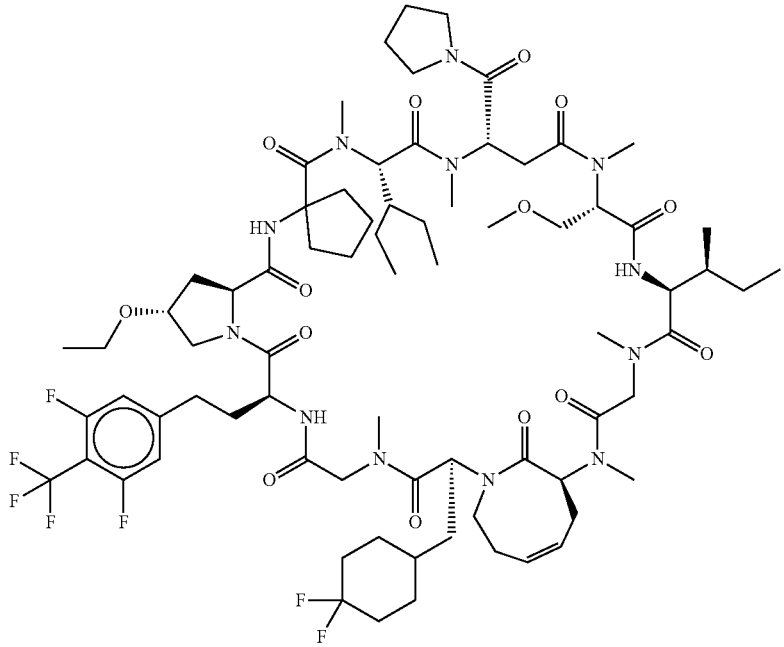 |

TABLE 38-continued
| Compound No. | Structural Formula |
|---|---|
| PP1442 | 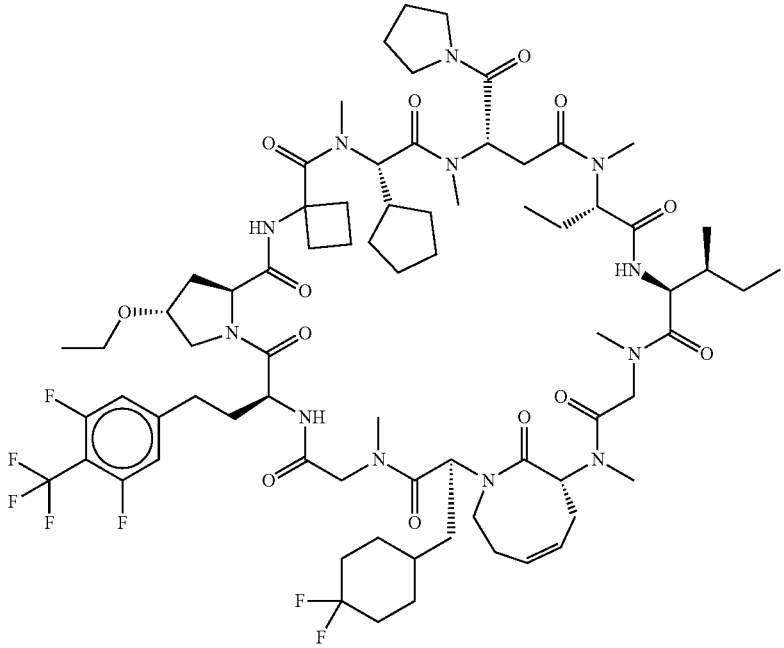 |
| PP1443 | 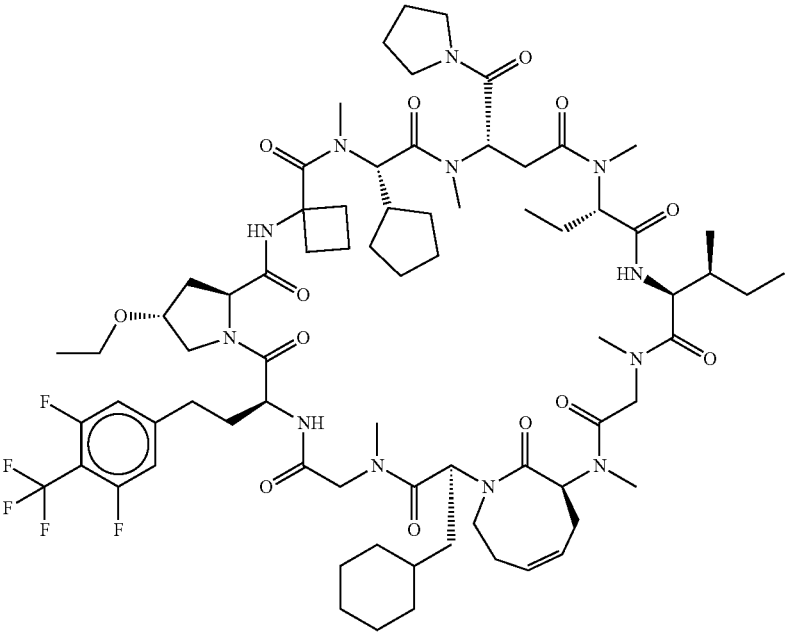 |

US 12,410,212 B2
TABLE 38-continued
| Compound No. | Structural Formula |
|---|---|
| PP1444 | 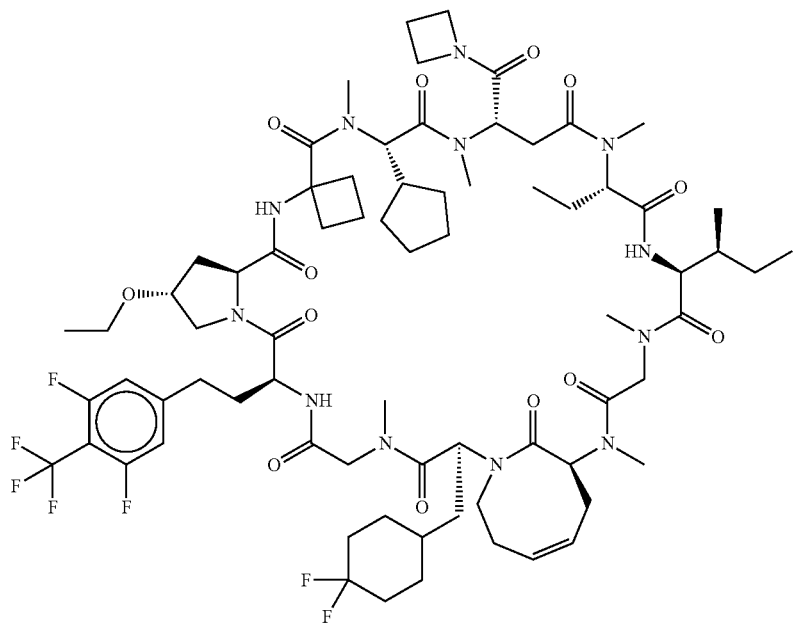 |
| PP1445 | 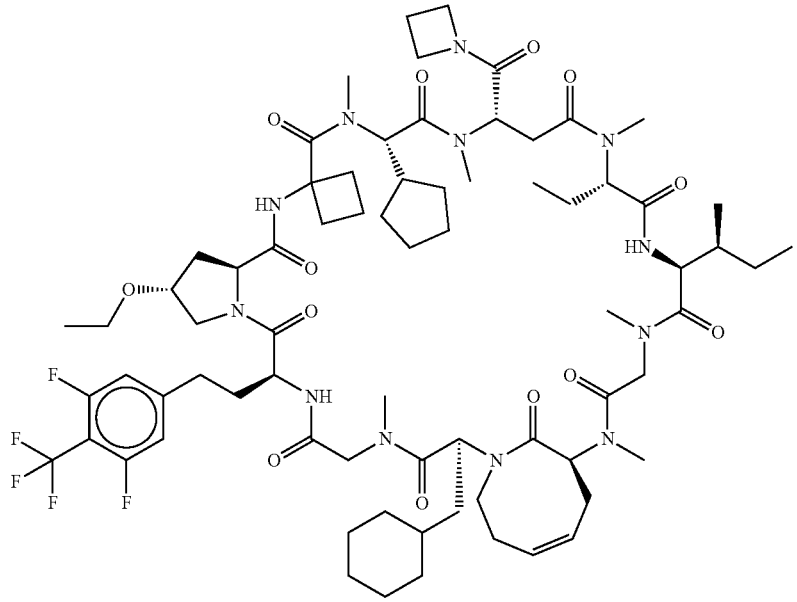 |

TABLE 38-continued
| Compound No. | Structural Formula |
|---|---|
| PP1446 | 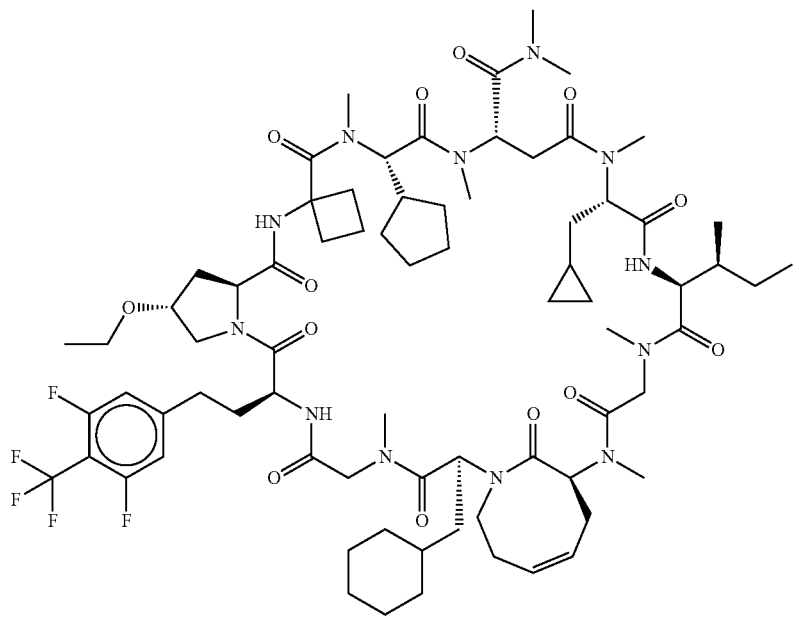 |
| PP1447 | 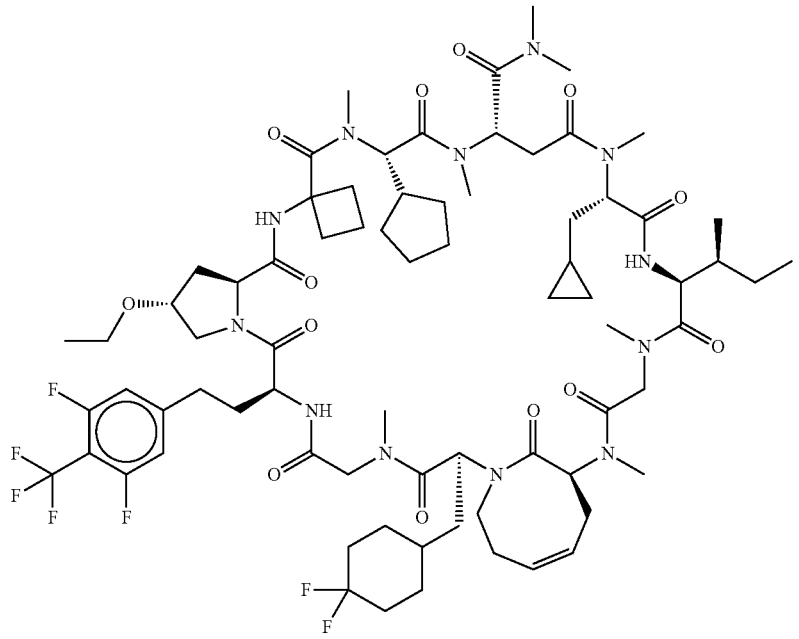 |

TABLE 38-continued

| Compound No. | Structural Formula |
|---|---|
| PP1448 | |
| PP1449 | |

TABLE 38-continued
| Compound No. | Structural Formula |
|---|---|
| PP1450 | 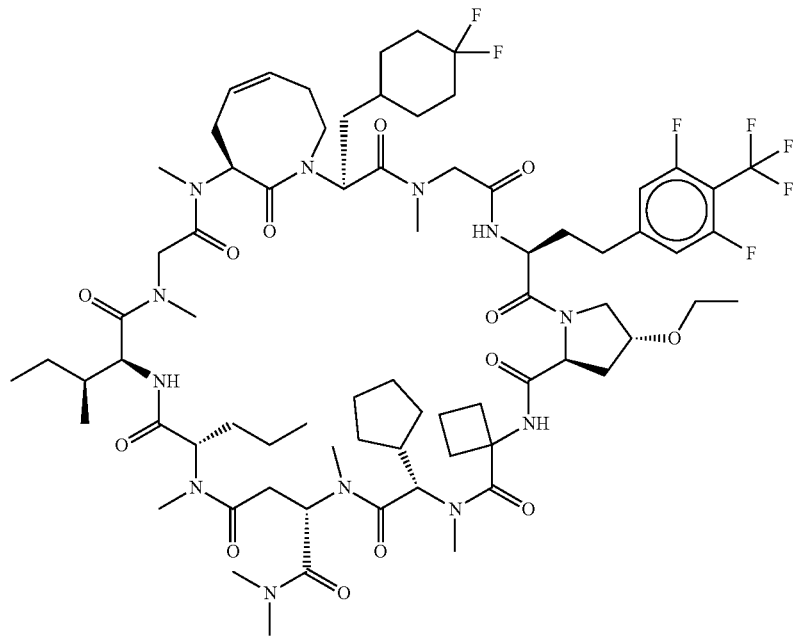 |
| PP1451 | 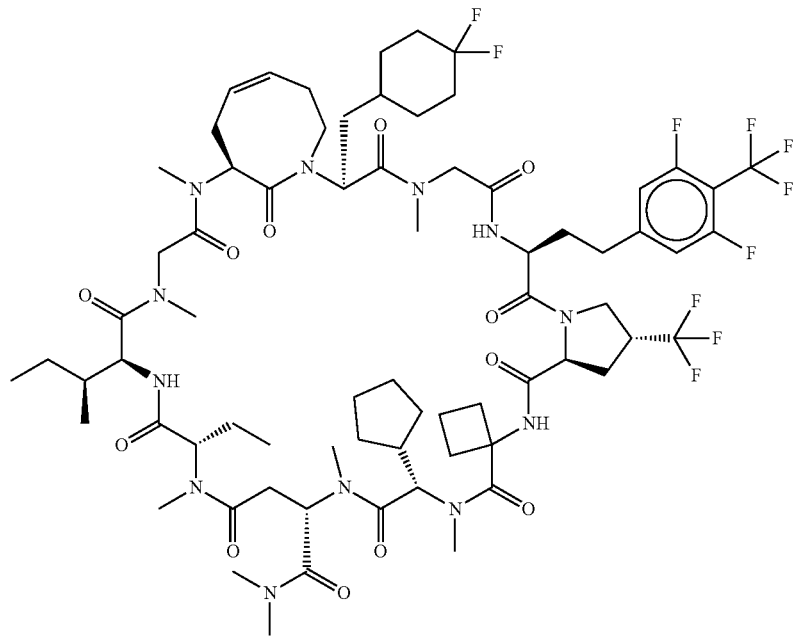 |

TABLE 38-continued
| Compound No. | Structural Formula |
|---|---|
| PP1452 | 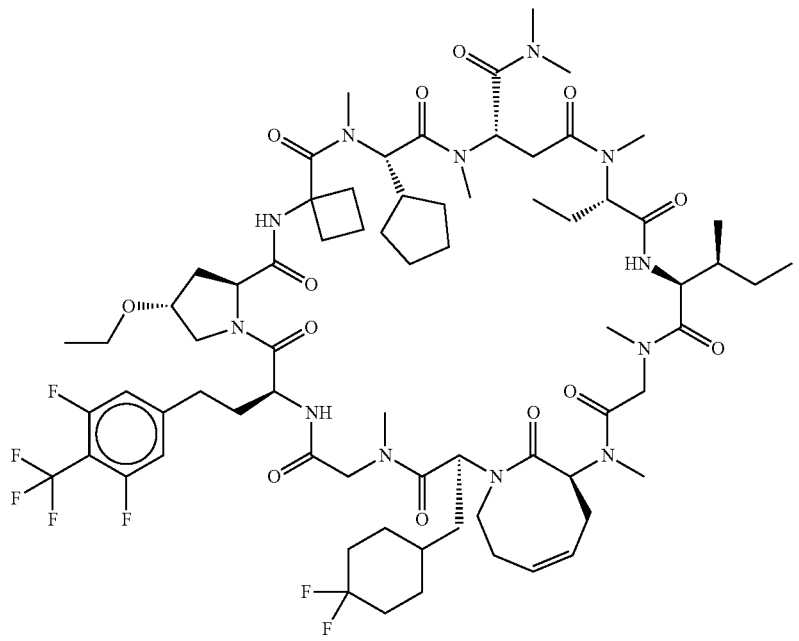 |
| PP1453 | 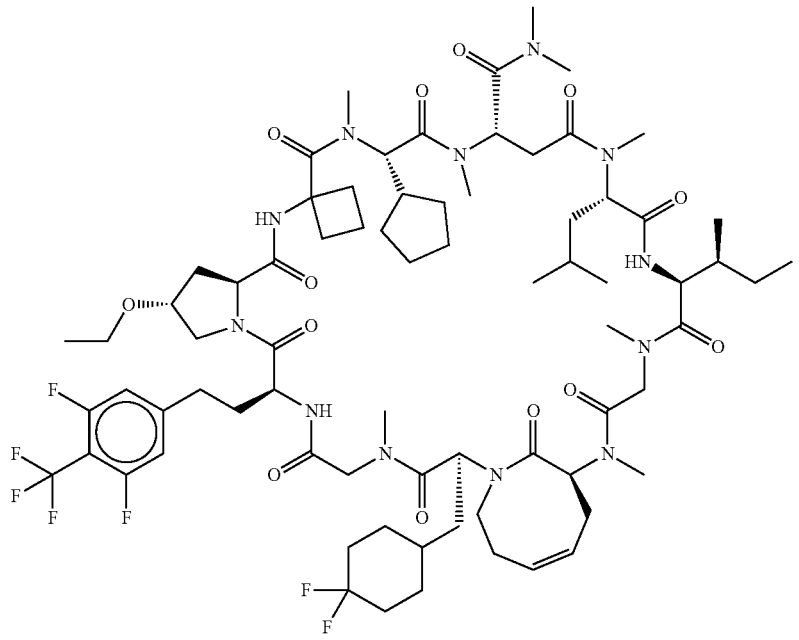 |

TABLE 38-continued

| Compound No. | Structural Formula |
|---|---|
| PP1454 | |
| PP1455 | |

TABLE 38-continued

| Compound No. | Structural Formula |
|---|---|
| PP1456 | |
| PP1457 | |

TABLE 38-continued
| Compound No. | Structural Formula |
|---|---|
| PP1458 | 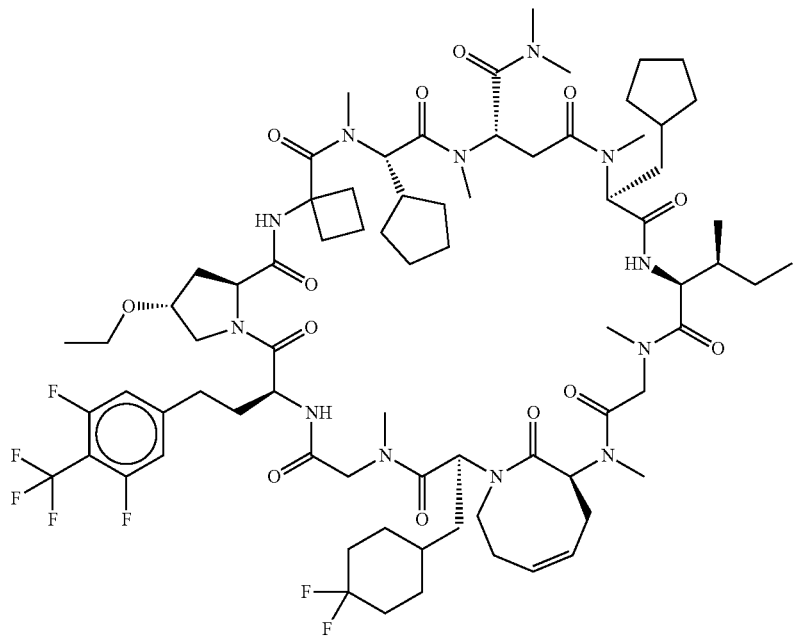 |
| PP1459 | 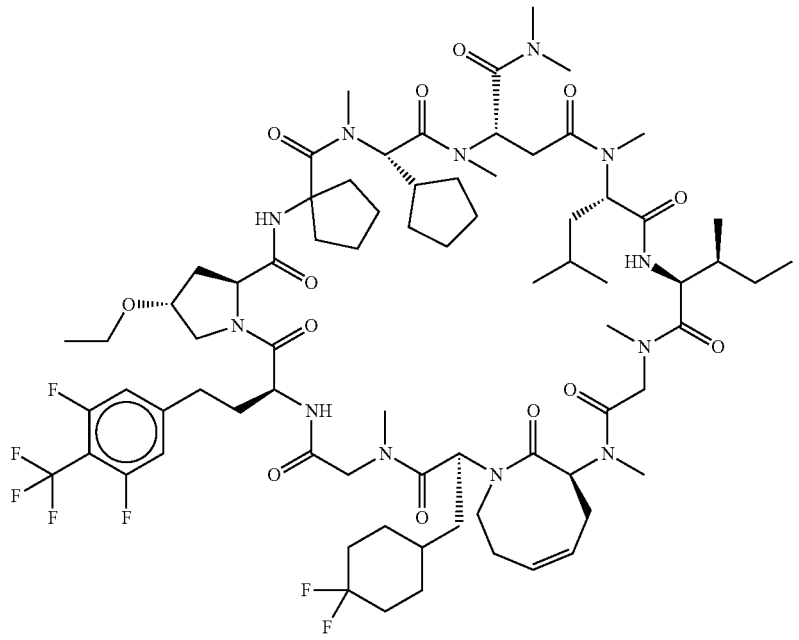 |

TABLE 38-continued
| Compound No. | Structural Formula |
|---|---|
| PP1460 | 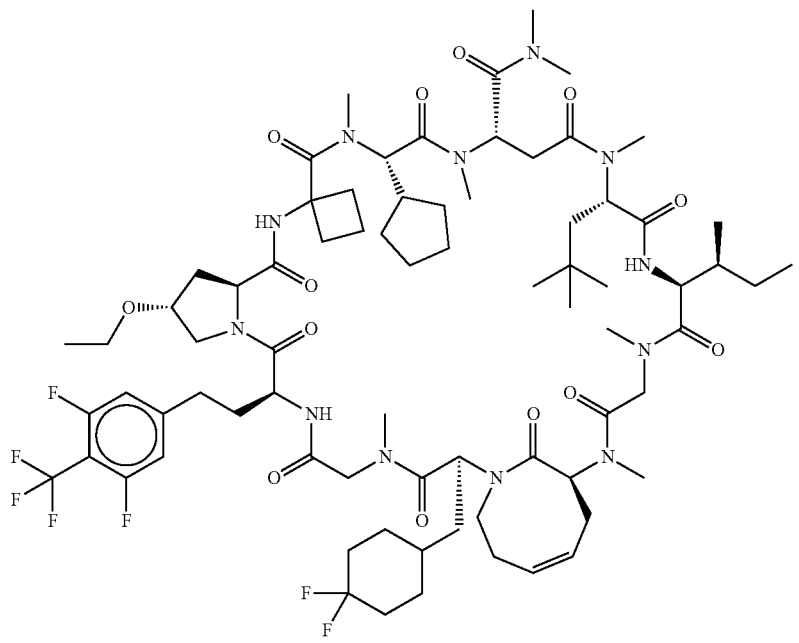 |
| PP1461 | 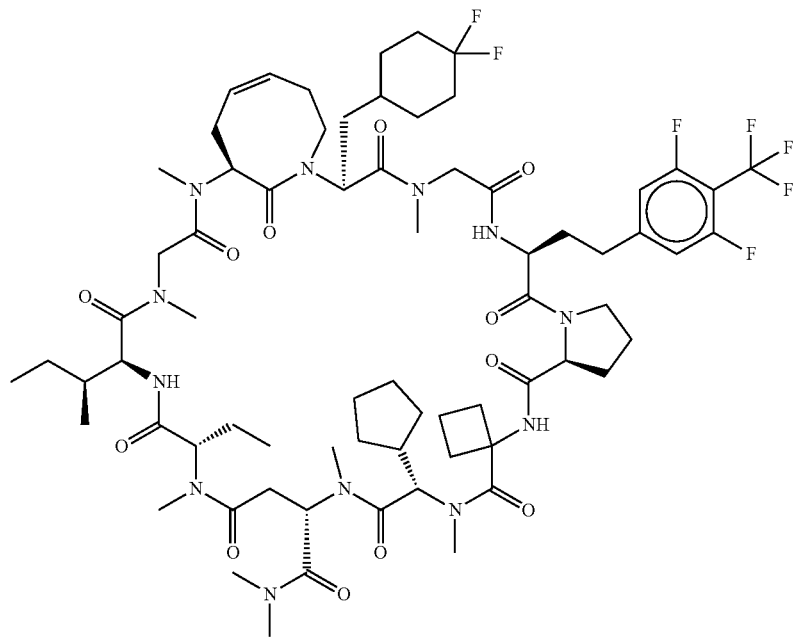 |

TABLE 38-continued
| Compound No. | Structural Formula |
|---|---|
| PP1462 | 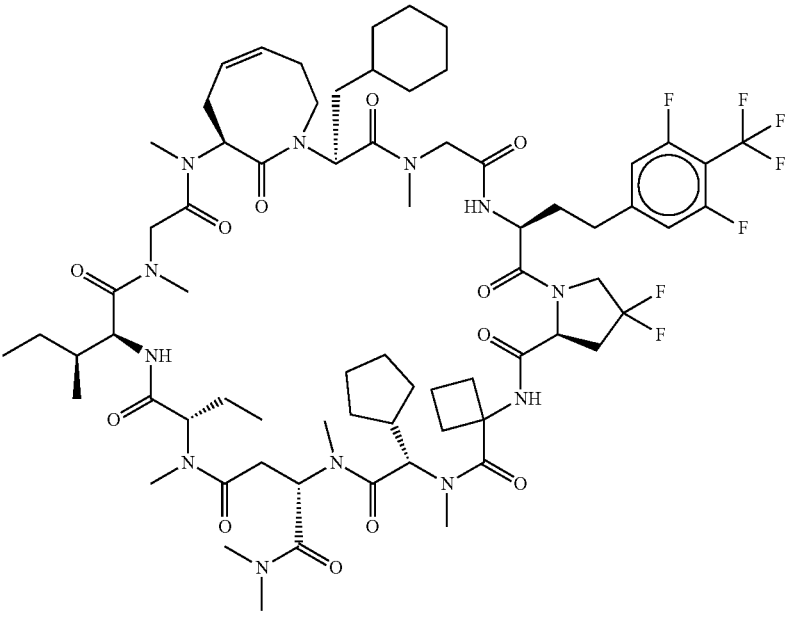 |
| PP1463 | 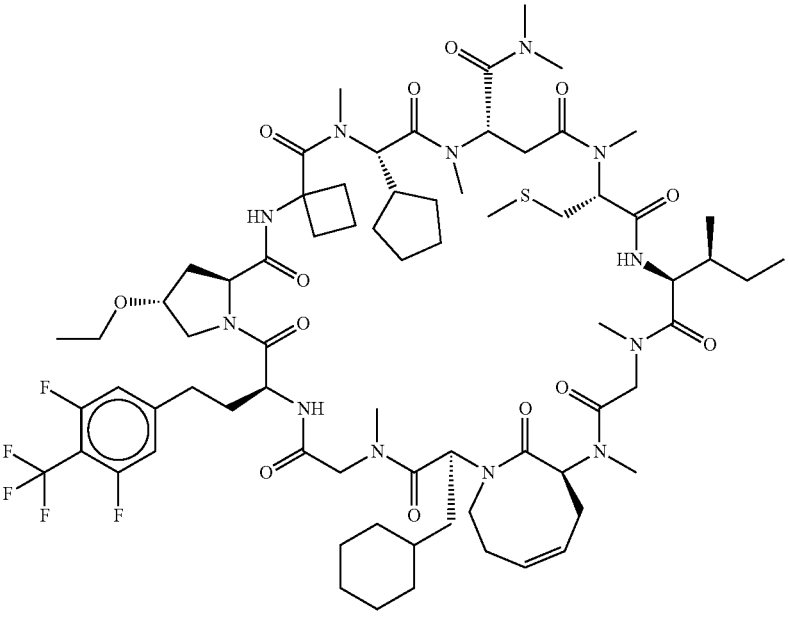 |

TABLE 38-continued
| Compound No. | Structural Formula |
|---|---|
| PP1464 | 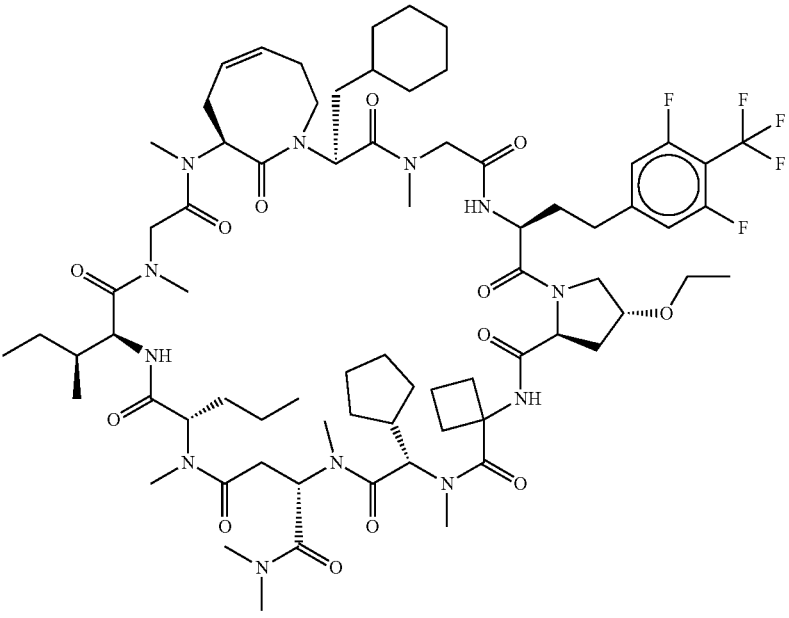 |
| PP1465 | 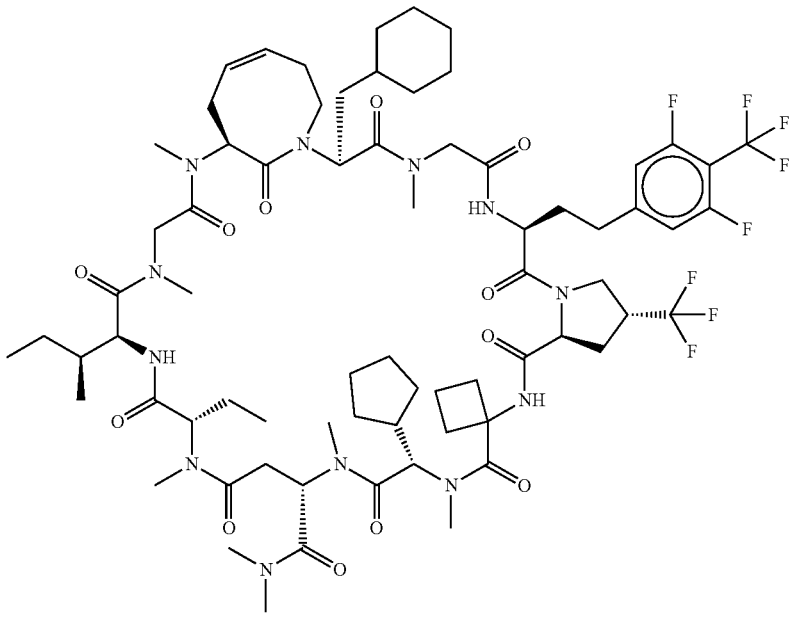 |

TABLE 38-continued
| Compound No. | Structural Formula |
|---|---|
| PP1466 | 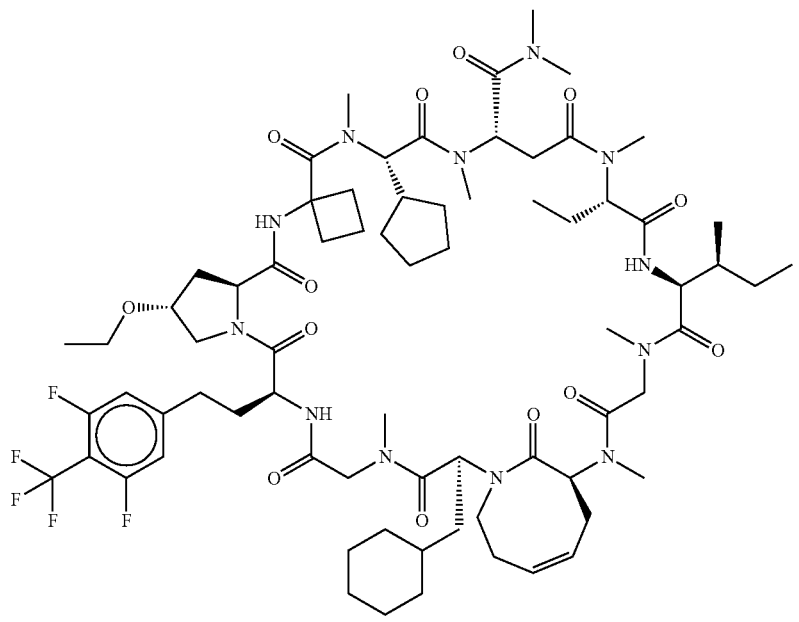 |
| PP1467 | 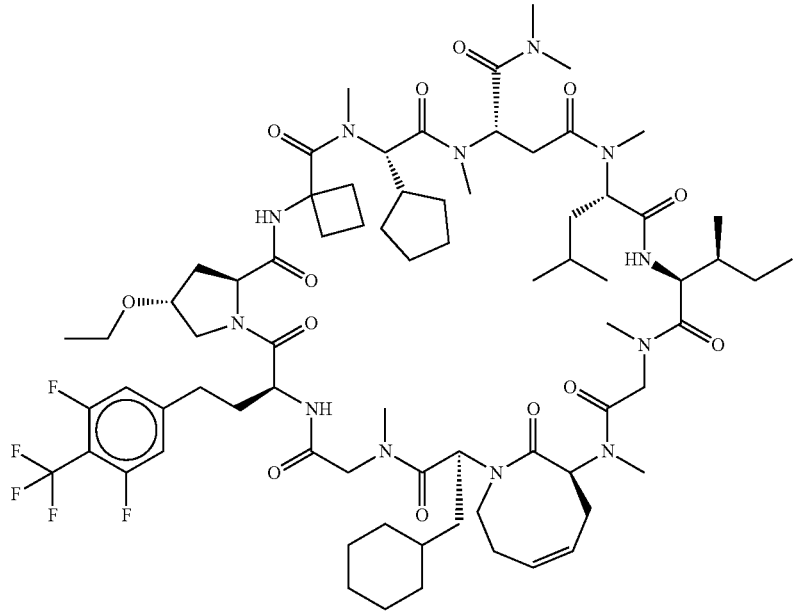 |

TABLE 38-continued

| Compound No. | Structural Formula |
|---|---|
| PP1468 | |
| PP1469 | |

TABLE 38-continued
| Compound No. | Structural Formula |
|---|---|
| PP1470 | 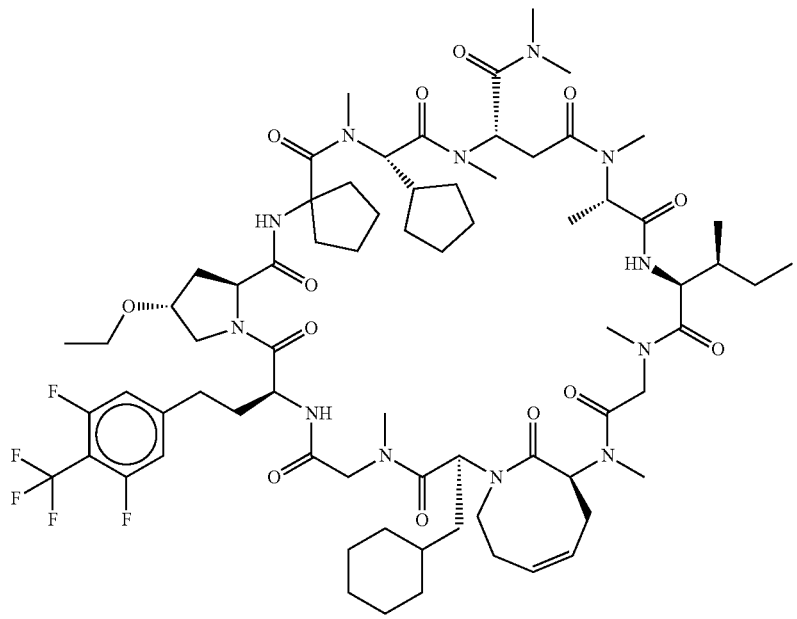 |
| PP1471 | 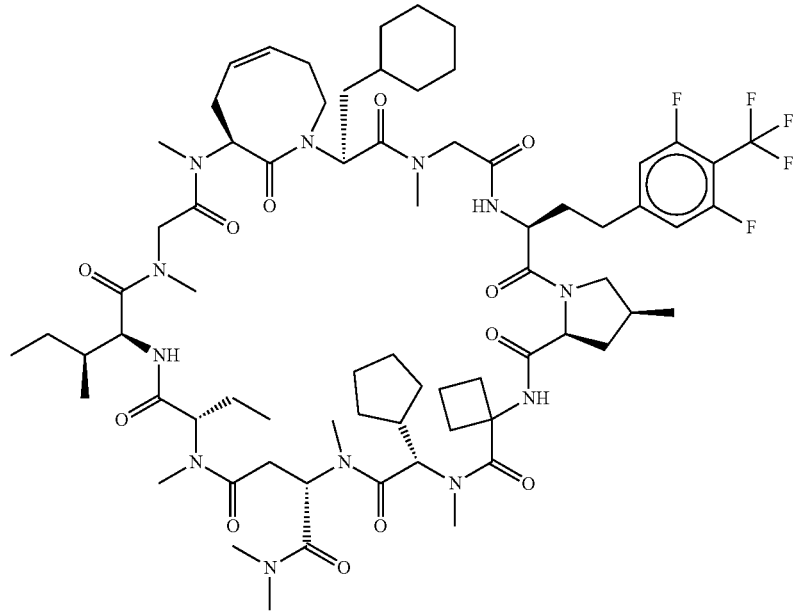 |

TABLE 38-continued
| Compound No. | Structural Formula |
|---|---|
| PP1472 | 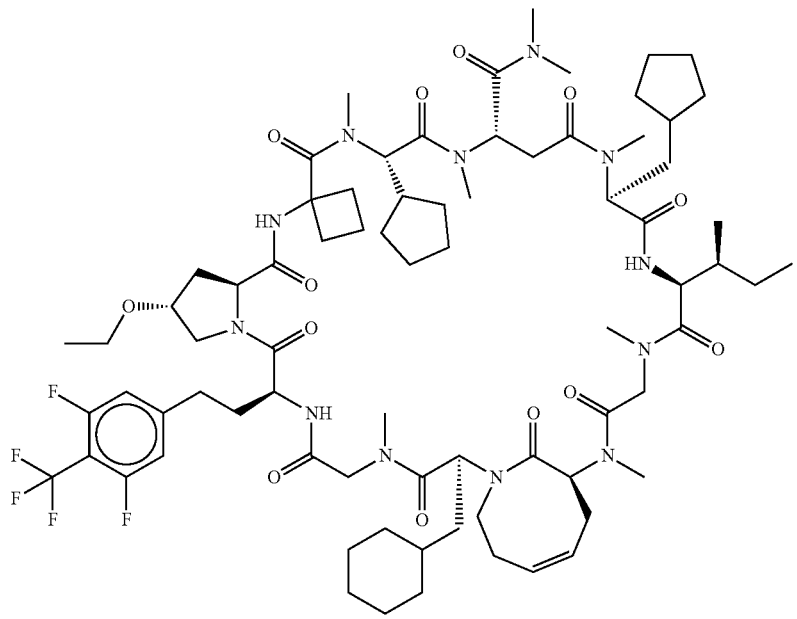 |
| PP1473 | 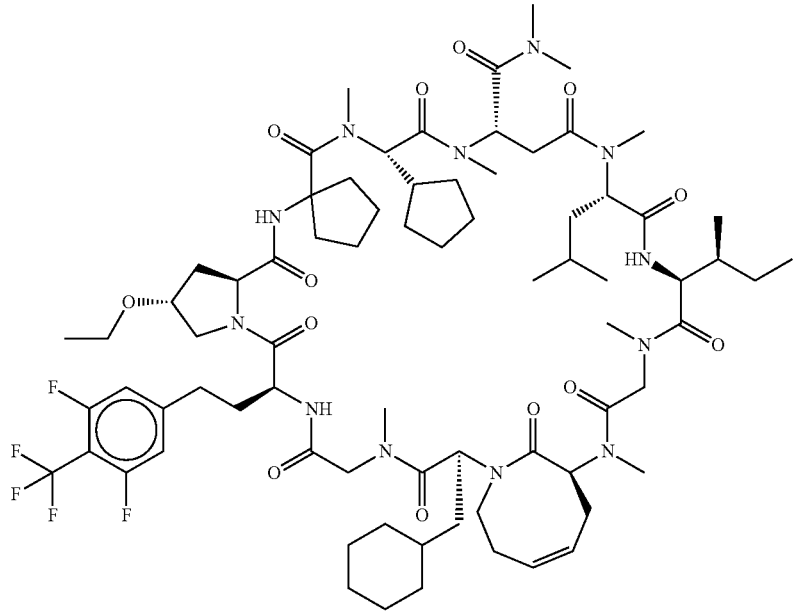 |

TABLE 38-continued
| Compound No. | Structural Formula |
| --- | --- |
| PP1474 | 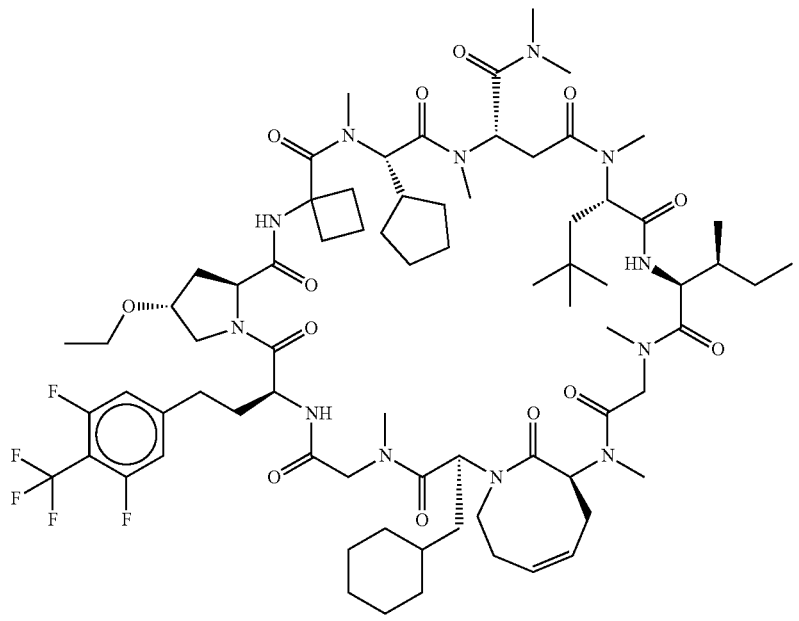 |
| PP1475 | 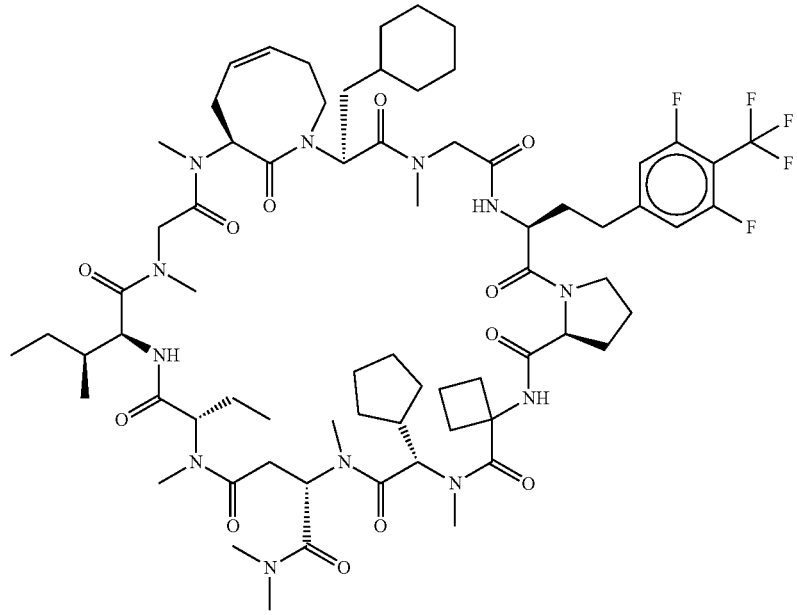 |

TABLE 38-continued

| Compound No. | Structural Formula |
| --- | --- |
| PP1476 | |
| PP1477 | |

TABLE 38-continued

| Compound No. | Structural Formula |
| --- | --- |
| PP1478 | |
| PP1479 | |

TABLE 38-continued

| Compound No. | Structural Formula |
| --- | --- |
| PP1480 | |
| PP1481 | |

TABLE 38-continued

| Compound No. | Structural Formula |
|---|---|
| PP1482 | |
| PP1483 | |

TABLE 38-continued
| Compound No. | Structural Formula |
|---|---|
| PP1484 | 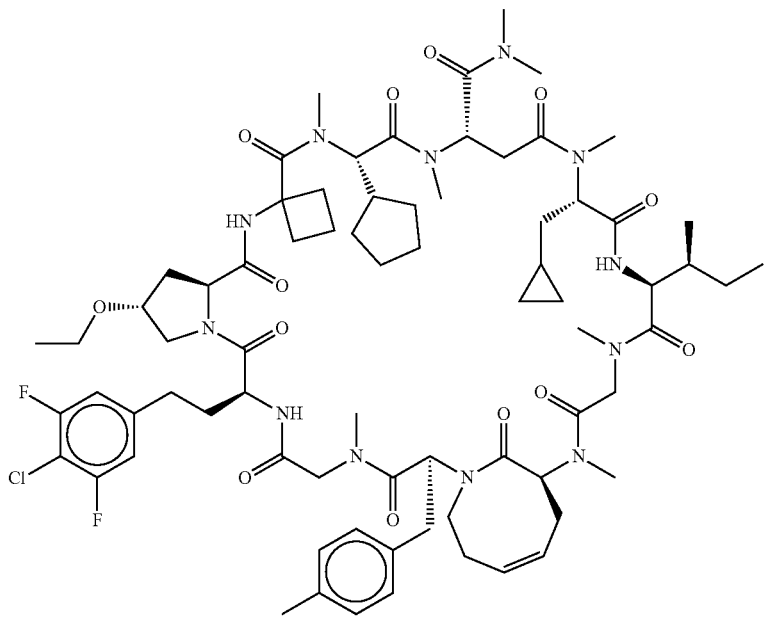 |
| PP1485 | 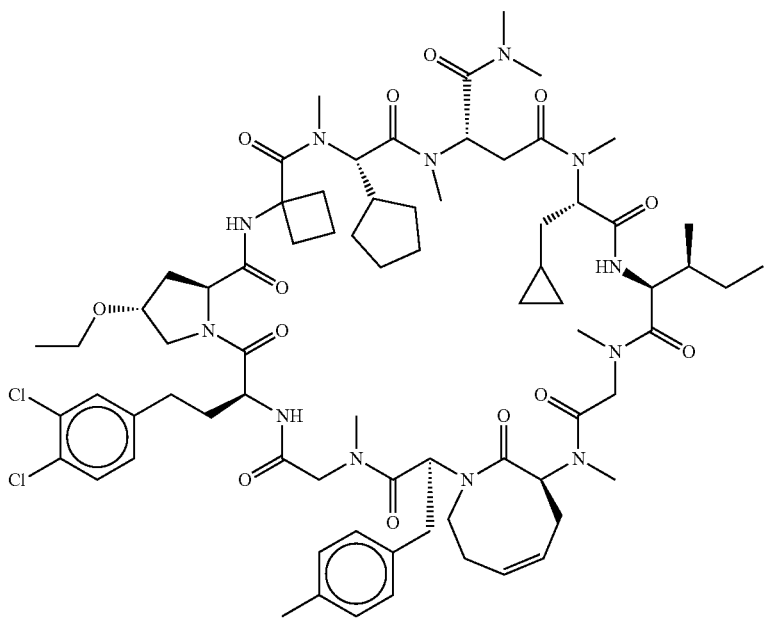 |

TABLE 38-continued
| Compound No. | Structural Formula |
|---|---|
| PP1486 | 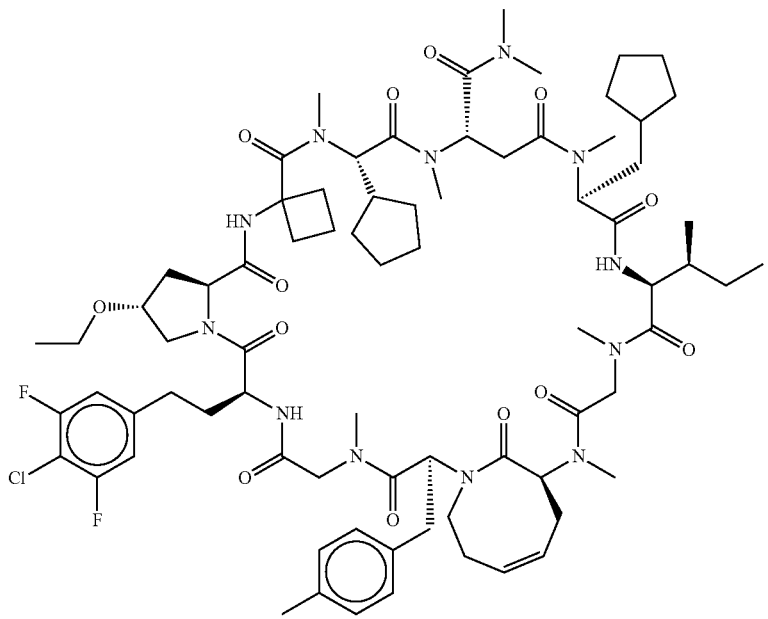 |
| PP1487 | 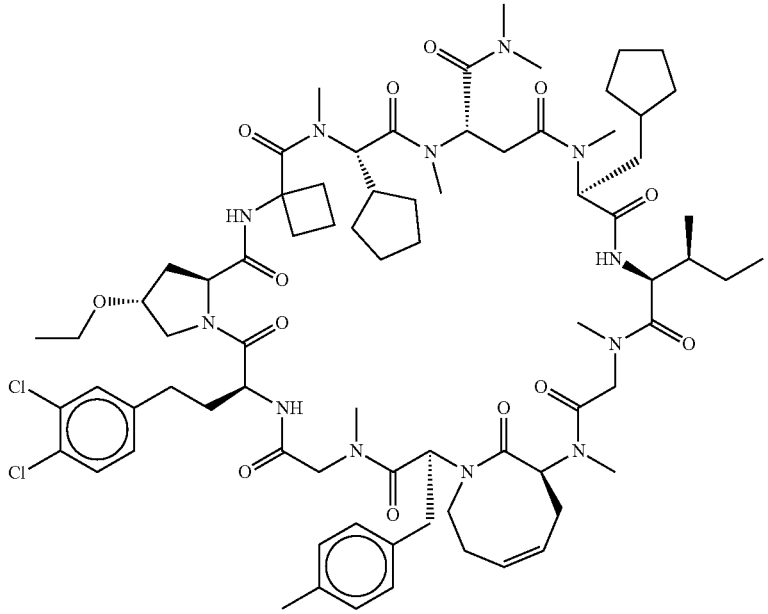 |

TABLE 38-continued
| Compound No. | Structural Formula |
|---|---|
| PP1488 | 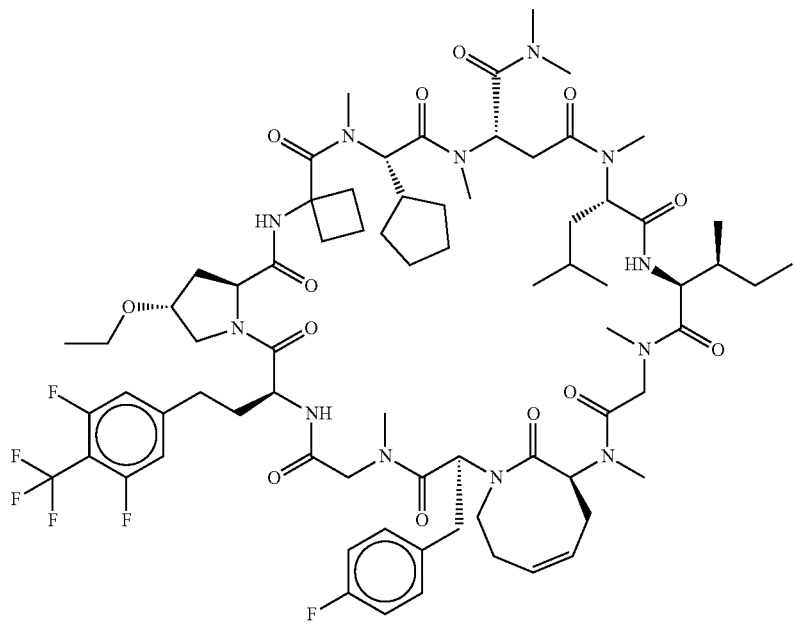 |
| PP1489 | 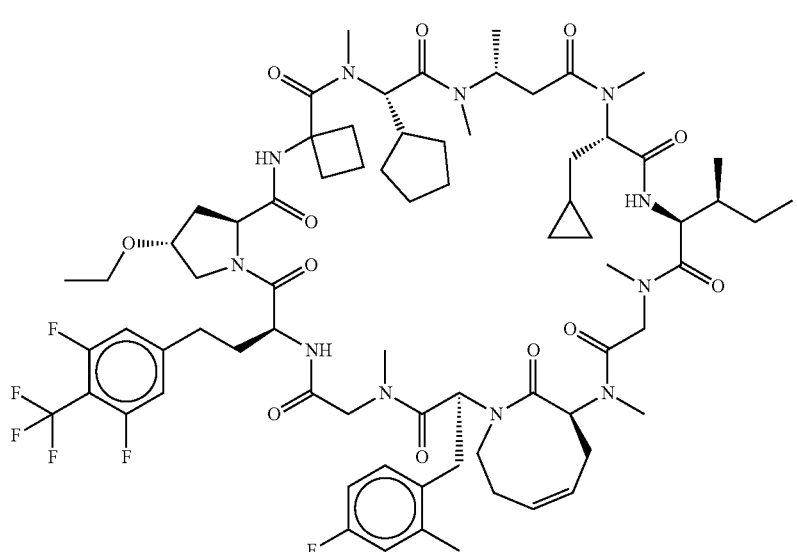 |

TABLE 38-continued

| Compound No. | Structural Formula |
|---|---|
| PP1490 | |
| PP1491 | |

TABLE 38-continued
| Compound No. | Structural Formula |
|---|---|
| PP1492 | 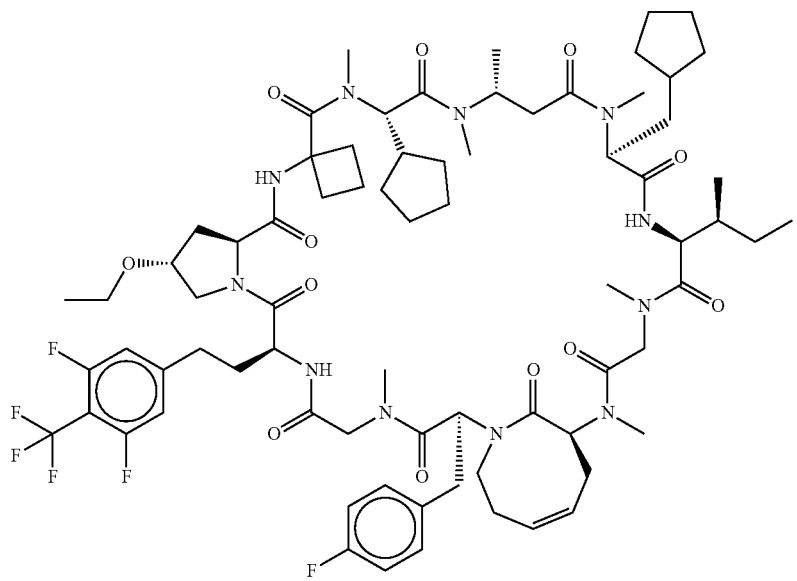 |
| PP1493 | 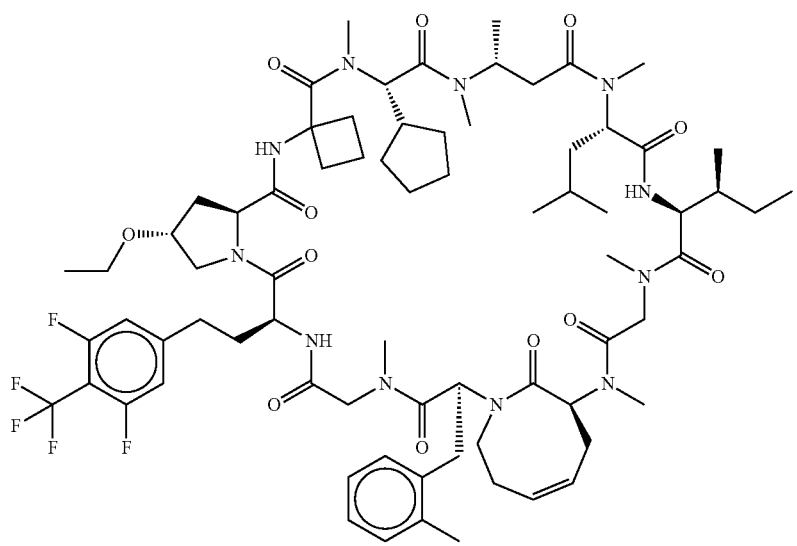 |

TABLE 38-continued

| Compound No. | Structural Formula |
|---|---|
| PP1494 | |
| PP1495 | |

TABLE 38-continued

| Compound No. | Structural Formula |
|---|---|
| PP1496 | |
| PP1497 | |

2305 2306
TABLE 38-continued
| Compound No. | Structural Formula |
|---|---|
| PP1498 | 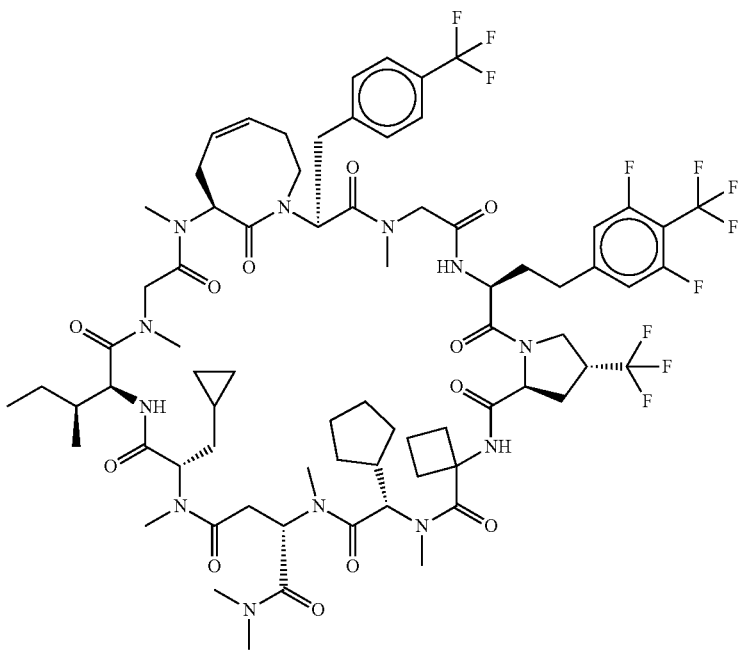 |
| PP1499 | 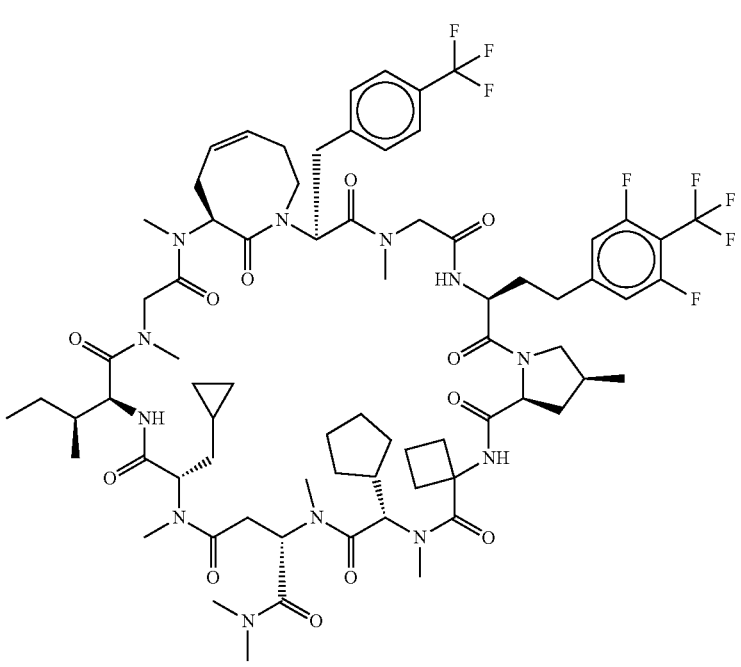 |

TABLE 38-continued

| Compound No. | Structural Formula |
| --- | --- |
| PP1500 | |
| PP1501 | |

TABLE 38-continued

| Compound No. | Structural Formula |
| --- | --- |
| PP1502 | |
| PP1503 | |

TABLE 38-continued
| Compound No. | Structural Formula |
|---|---|
| PP1504 | 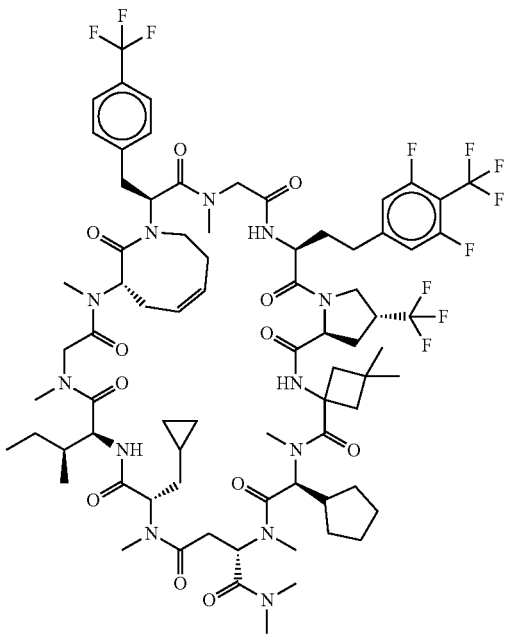 |
| PP1505 | 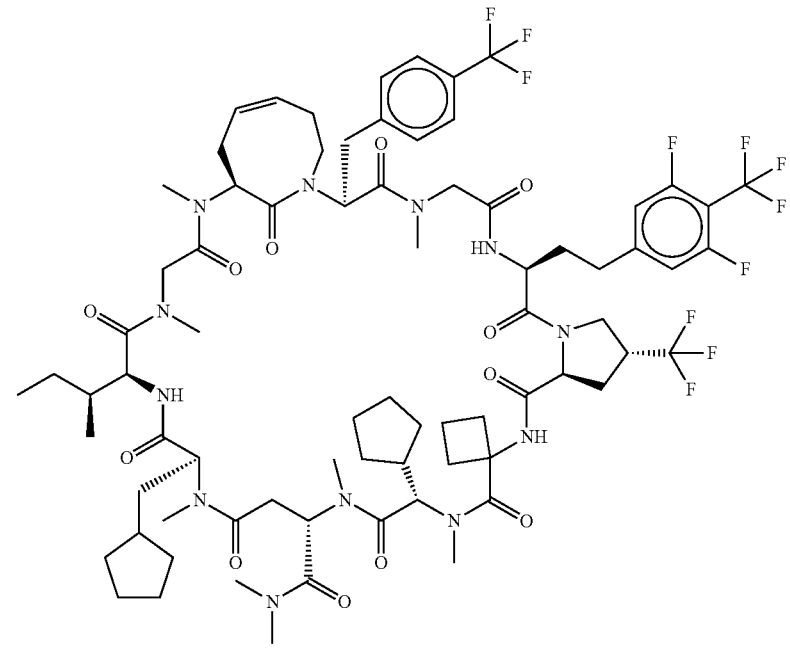 |

TABLE 38-continued

| Compound No. | Structural Formula |
|---|---|
| PP1506 | |
| PP1507 | |

TABLE 38-continued
| Compound No. | Structural Formula |
|---|---|
| PP1508 | 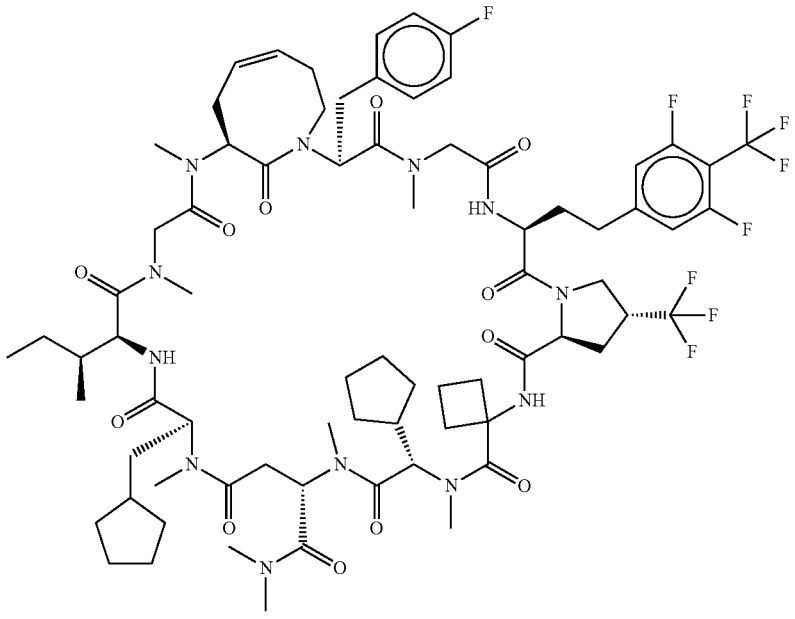 |
| PP1509 | 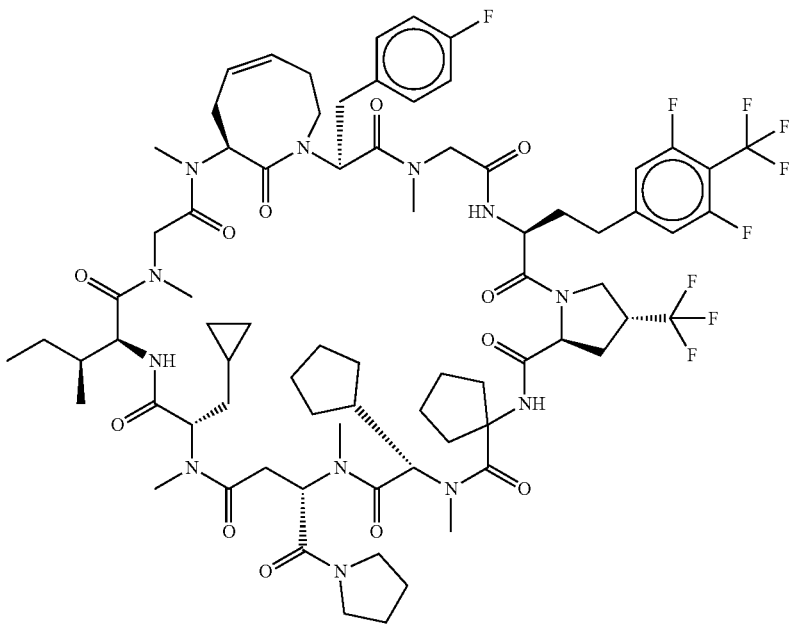 |

TABLE 38-continued

| Compound No. | Structural Formula |
|---|---|
| PP1510 | |
| PP1511 | |

TABLE 38-continued

| Compound No. | Structural Formula |
|---|---|
| PP1512 | |
| PP1513 | |

TABLE 38-continued
| Compound No. | Structural Formula |
|---|---|
| PP1514 | 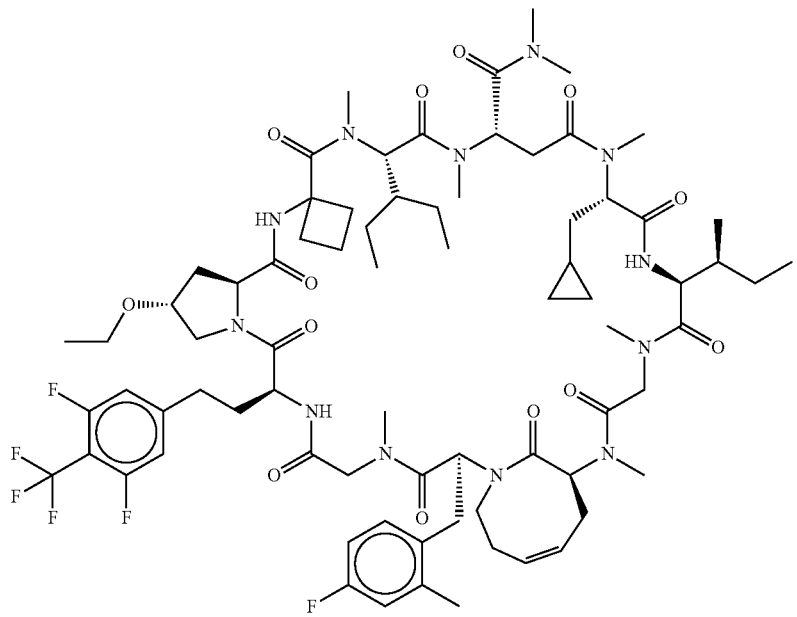 |
| PP1515 | 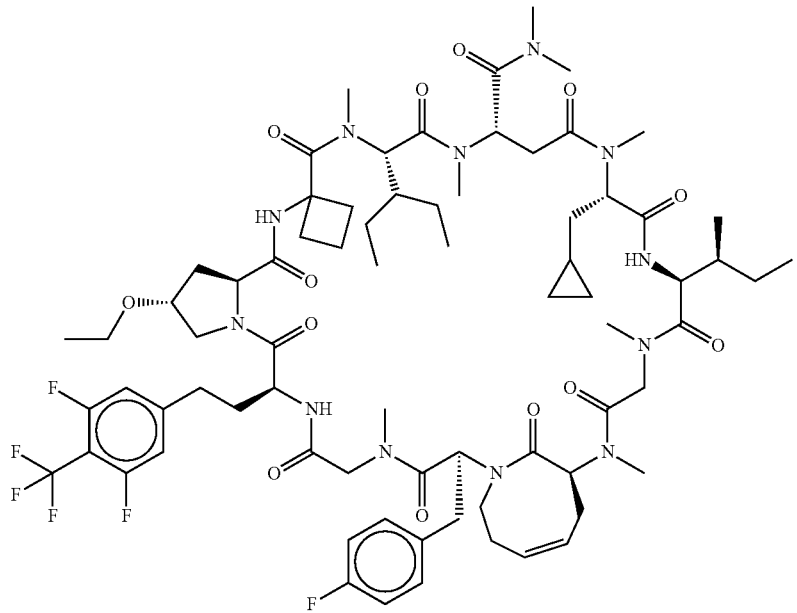 |

TABLE 38-continued
| Compound No. | Structural Formula |
|---|---|
| PP1516 | 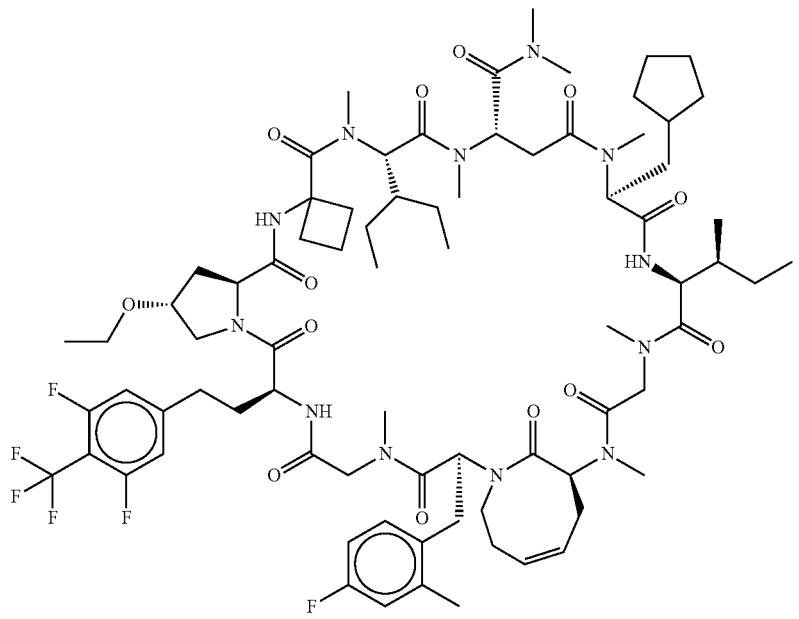 |
| PP1517 | 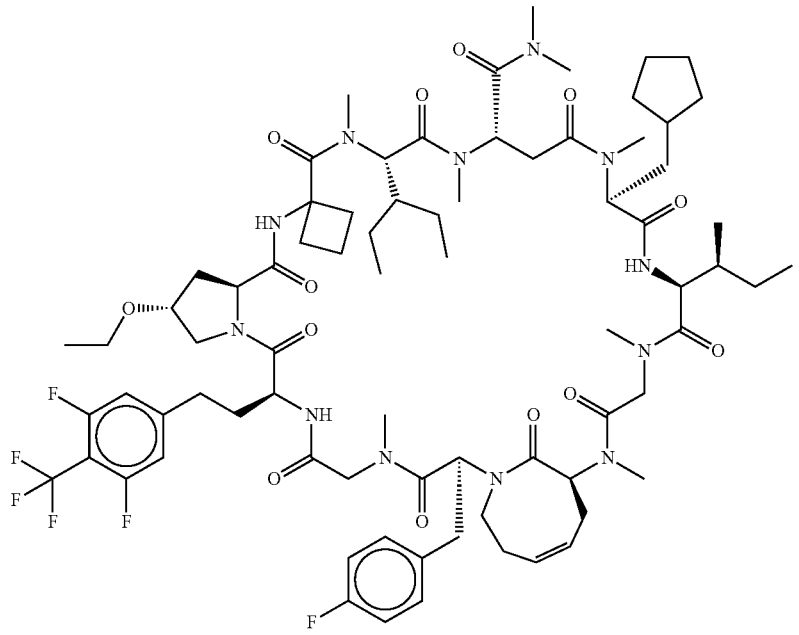 |

TABLE 38-continued
| Compound No. | Structural Formula |
|---|---|
| PP1518 | 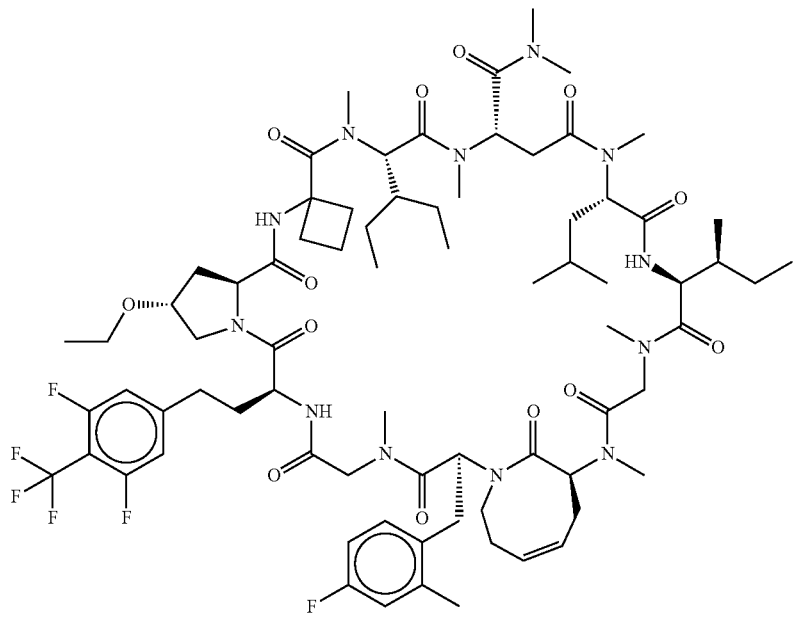 |
| PP1519 | 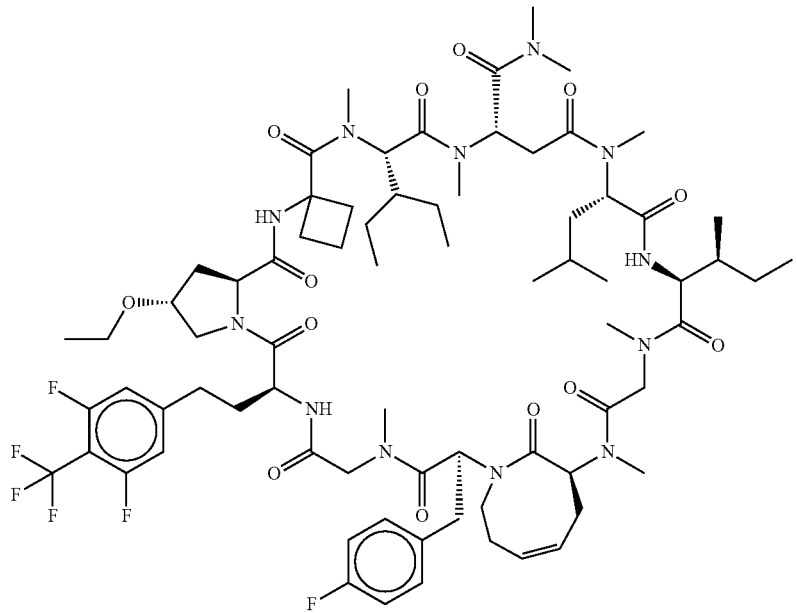 |

TABLE 38-continued
| Compound No. | Structural Formula |
|---|---|
| PP1520 | 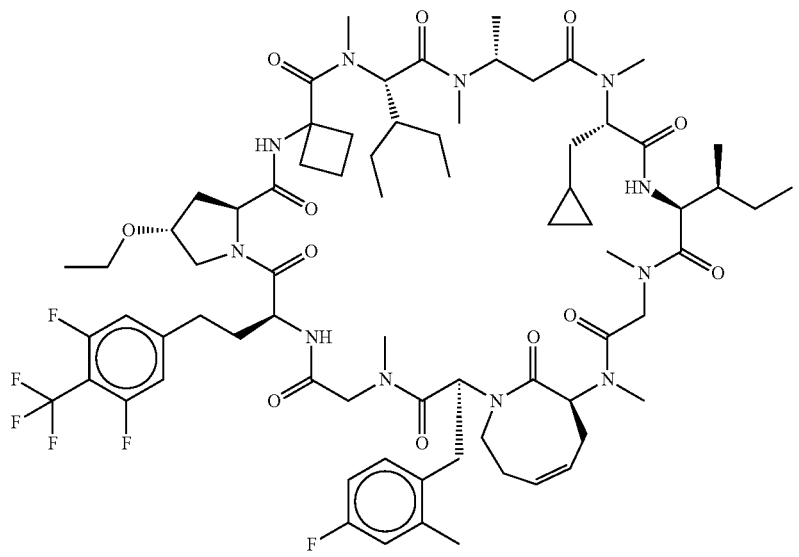 |
| PP1521 | 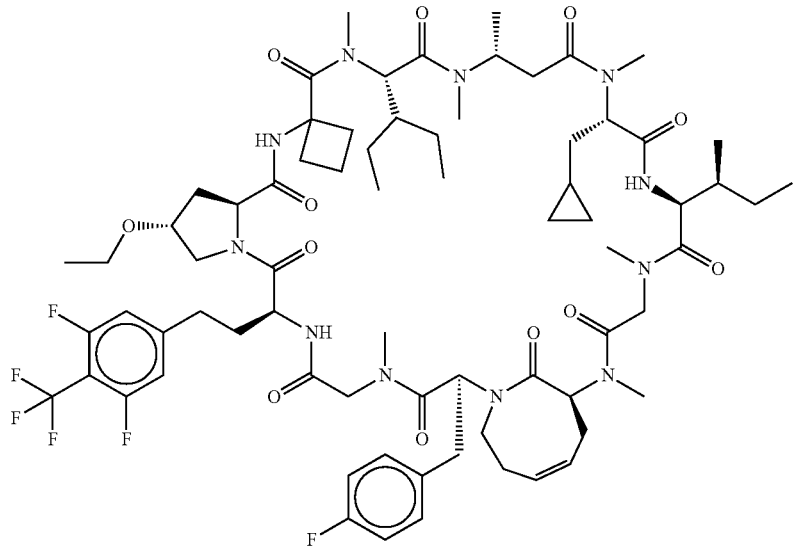 |

TABLE 38-continued
| Compound No. | Structural Formula |
|---|---|
| PP1522 | 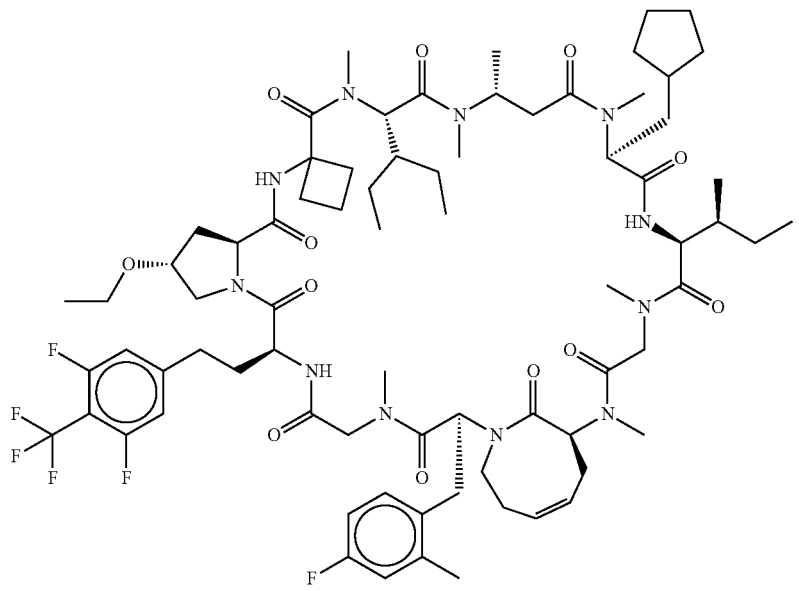 |
| PP1523 | 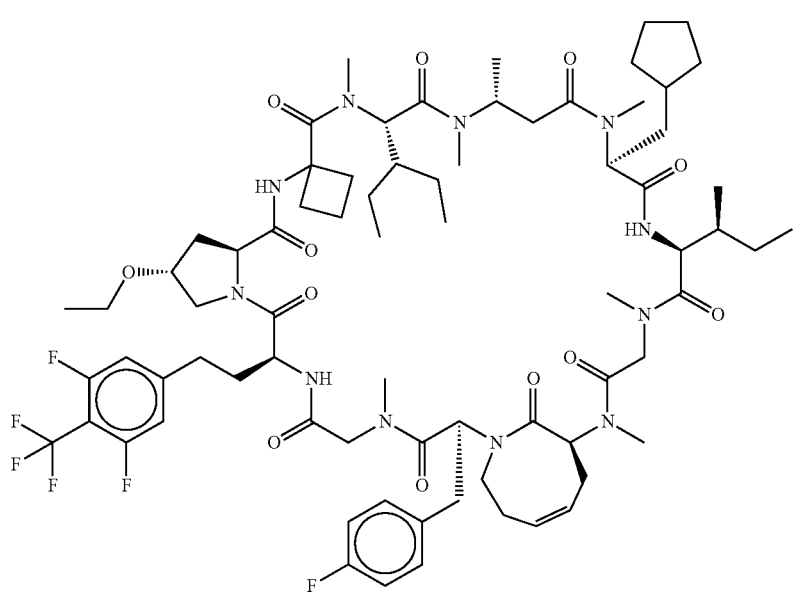 |

TABLE 38-continued
| Compound No. | Structural Formula |
| --- | --- |
| PP1524 | 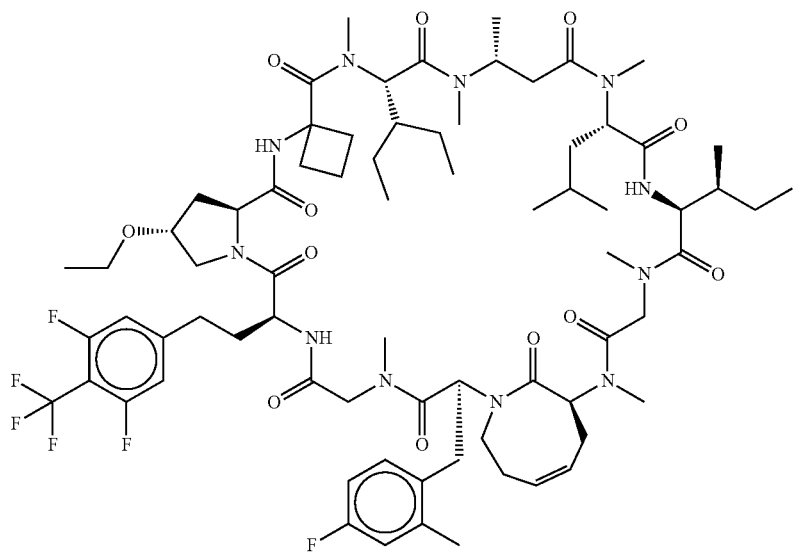 |
| PP1525 | 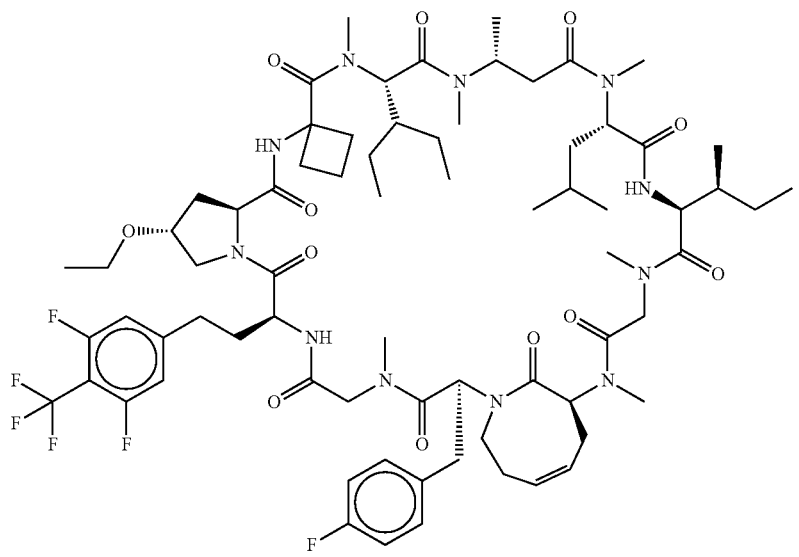 |

TABLE 38-continued
| Compound No. | Structural Formula |
|---|---|
| PP1526 | 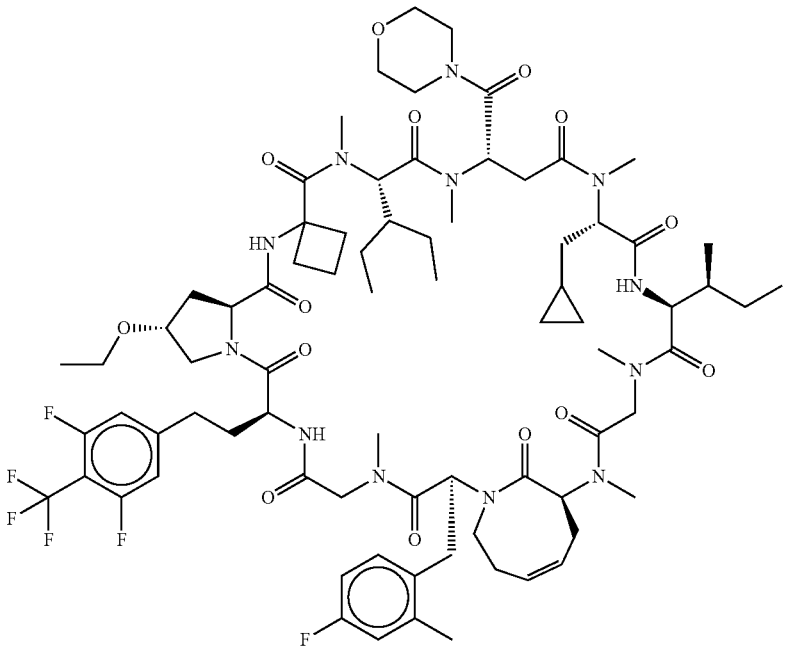 |
| PP1527 | 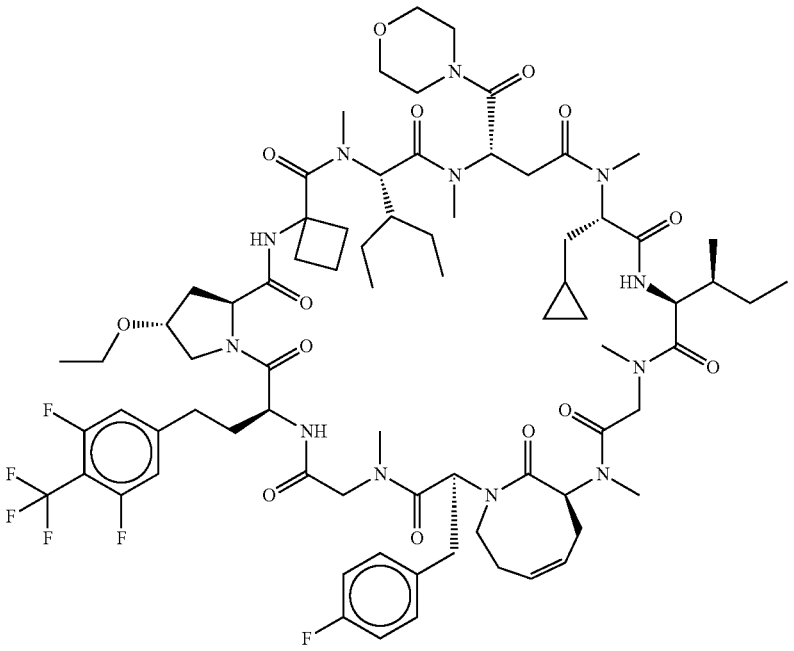 |

TABLE 38-continued

| Compound No. | Structural Formula |
|---|---|
| PP1528 | |
| PP1529 | |

TABLE 38-continued

| Compound No. | Structural Formula |
|---|---|
| PP1530 | |
| PP1531 | |

TABLE 38-continued
| Compound No. | Structural Formula |
|---|---|
| PP1532 | 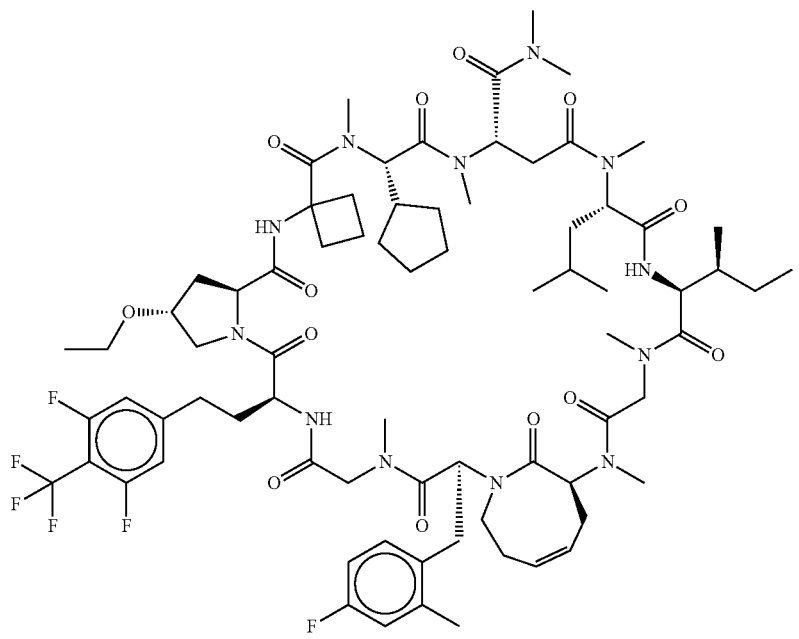 |
| PP1533 | 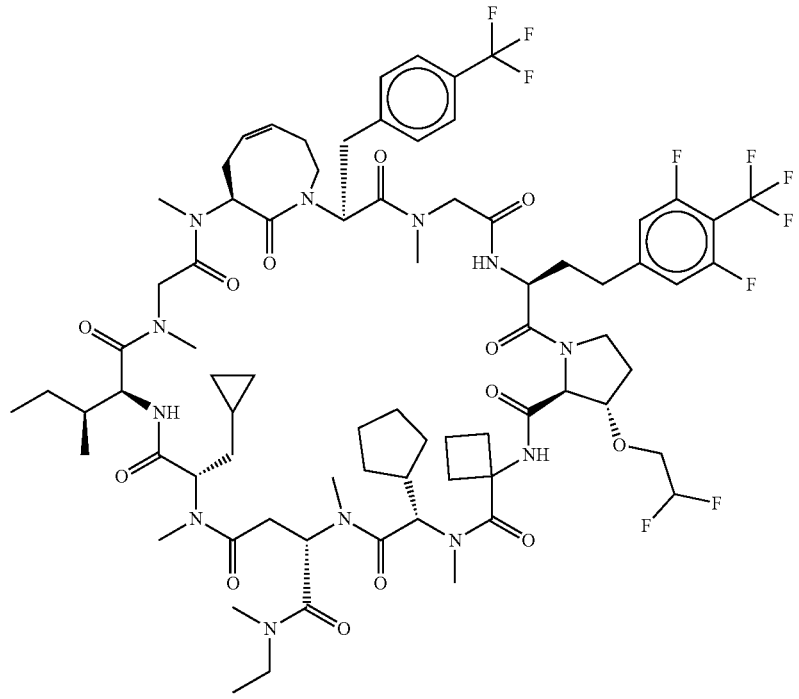 |

TABLE 38-continued
| Compound No. | Structural Formula |
| --- | --- |
| PP1534 | 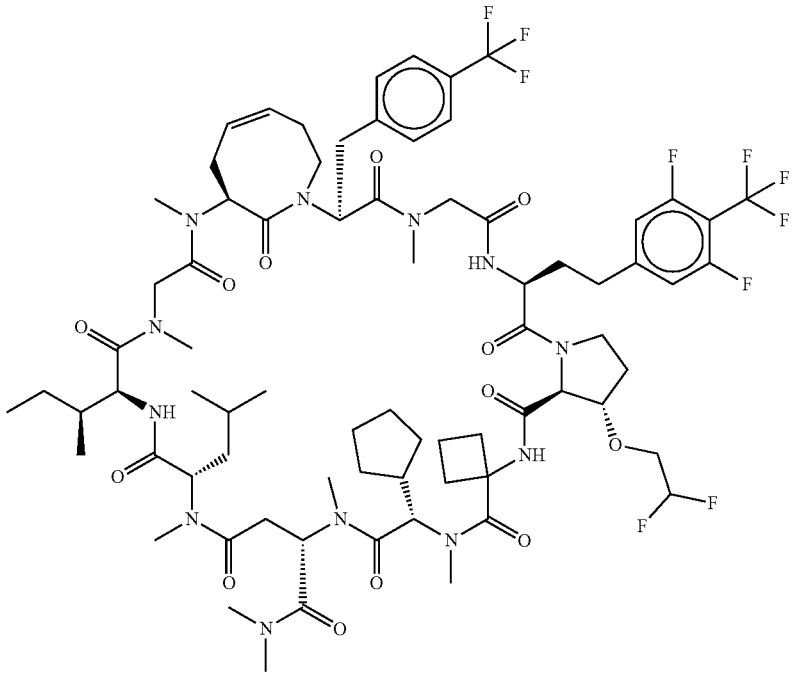 |
| PP1535 | 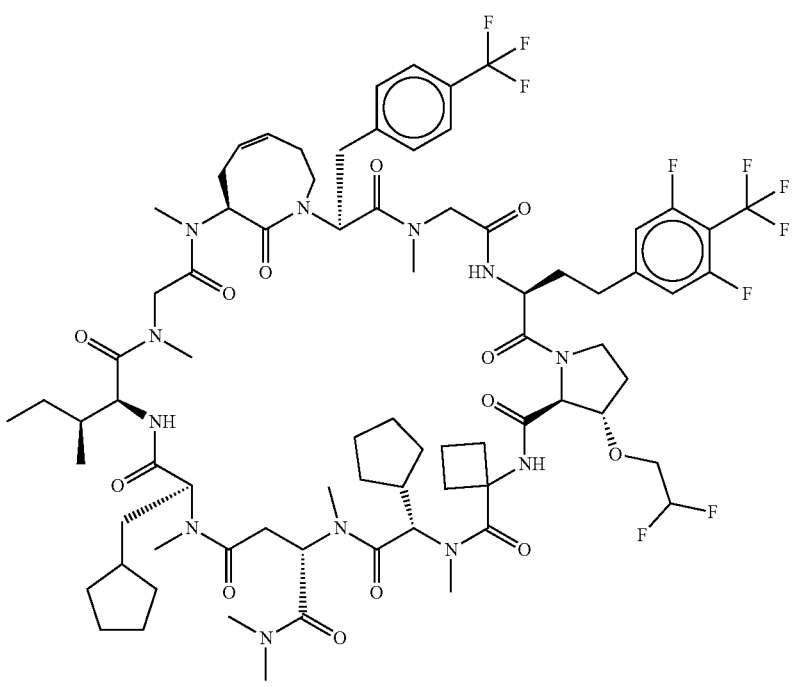 |

TABLE 38-continued

| Compound No. | Structural Formula |
| --- | --- |
| PP1536 | |
| PP1537 | |

TABLE 38-continued

| Compound No. | Structural Formula |
|---|---|
| PP1538 | |
| PP1552 | |

TABLE 38-continued

| Compound No. | Structural Formula |
|---|---|
| PP1553 | |
| PP1554 | |

TABLE 38-continued
| Compound No. | Structural Formula |
|---|---|
| PP1557 | 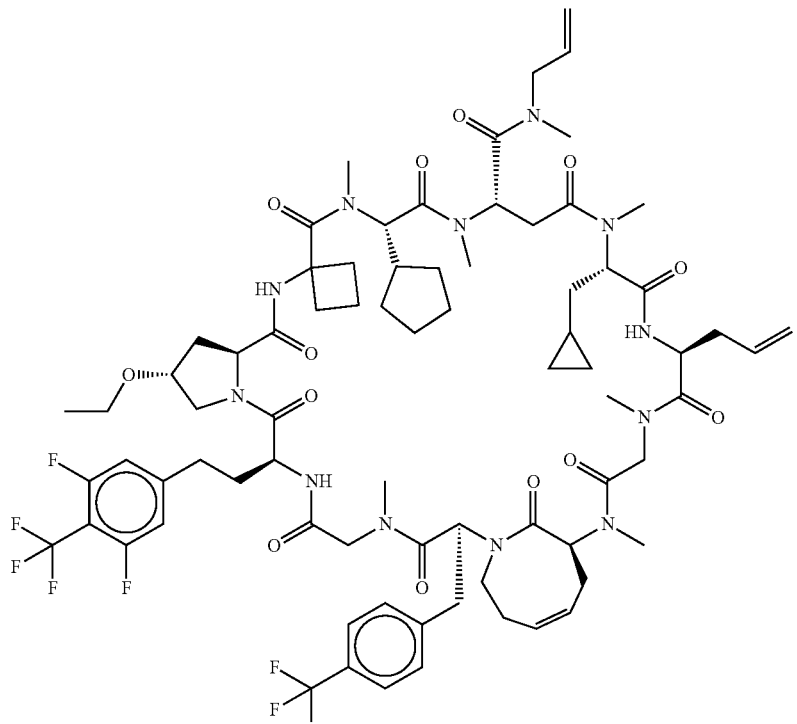 |
| PP1558 | 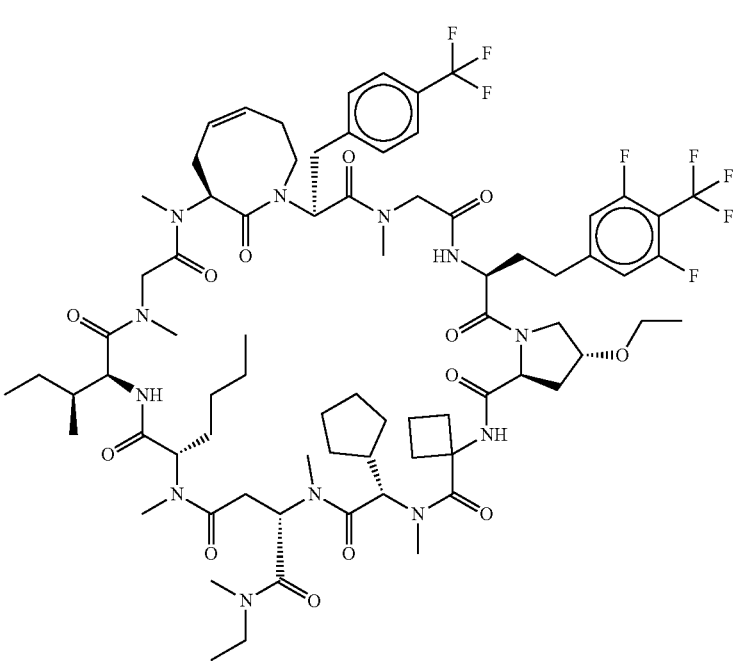 |

TABLE 38-continued

| Compound No. | Structural Formula |
|---|---|
| PP1559 | |
| PP1560 | |

TABLE 38-continued
| Compound No. | Structural Formula |
|---|---|
| PP1561 | 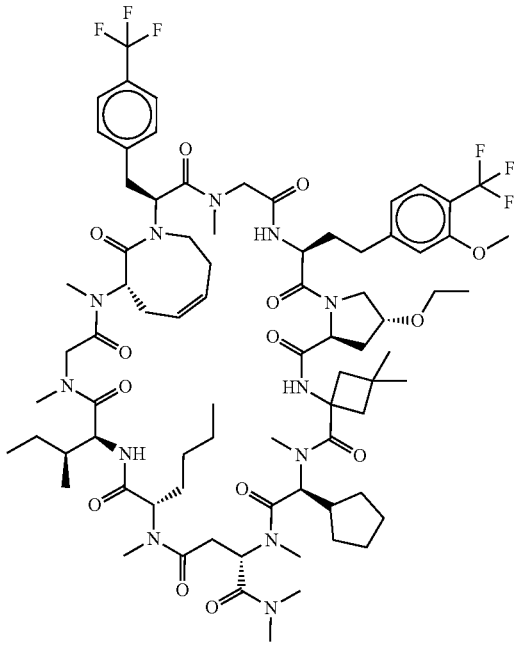 |
| PP1562 | 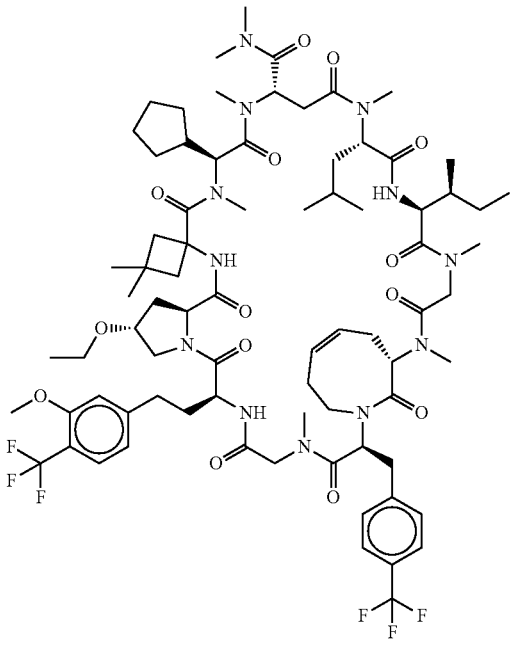 |

TABLE 38-continued

| Compound No. | Structural Formula |
|---|---|
| PP1563 | |
| PP1564 | |

TABLE 38-continued
| Compound No. | Structural Formula |
| --- | --- |
| PP1565 | 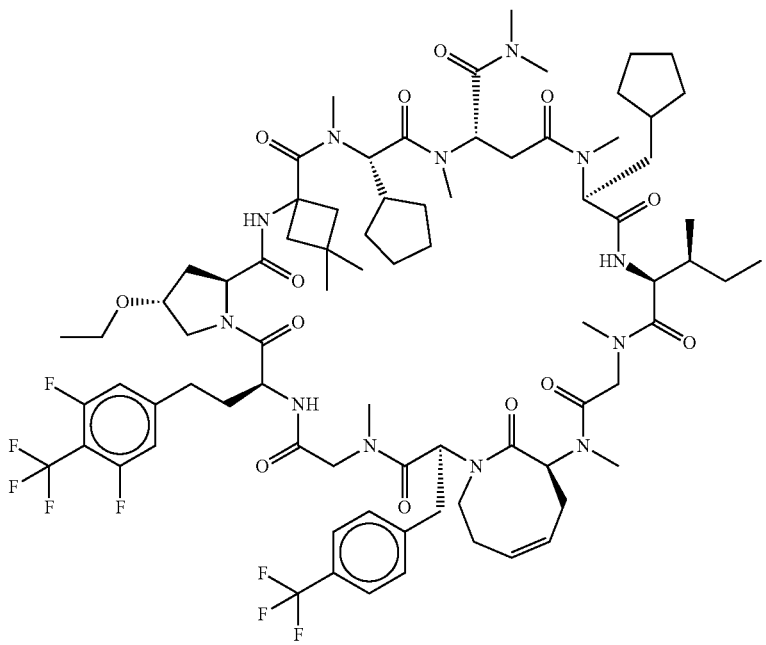 |
| PP1566 | 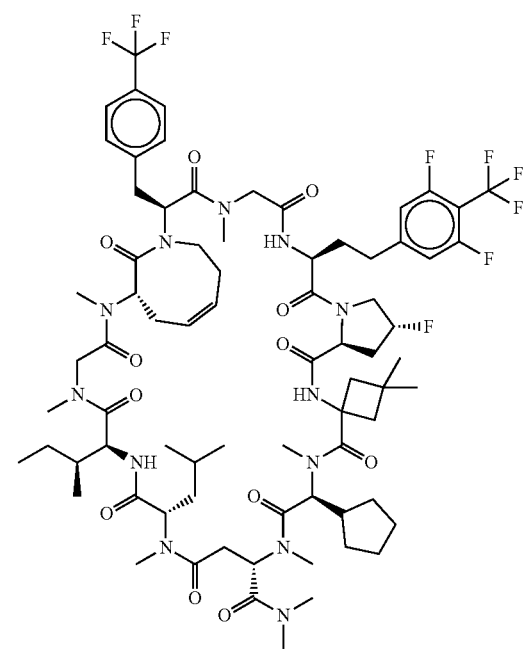 |

TABLE 38-continued

| Compound No. | Structural Formula |
|---|---|
| PP1568 | |
| PP1569 | |

TABLE 38-continued

| Compound No. | Structural Formula |
| --- | --- |
| PP1570 | |
| PP1571 | |

TABLE 38-continued

| Compound No. | Structural Formula |
|---|---|
| PP1572 | |
| PP1573 | |

US 12,410,212 B2
2365                                                                                                    2366
TABLE 38-continued
| Compound No. | Structural Formula |
|---|---|
| PP1574 | 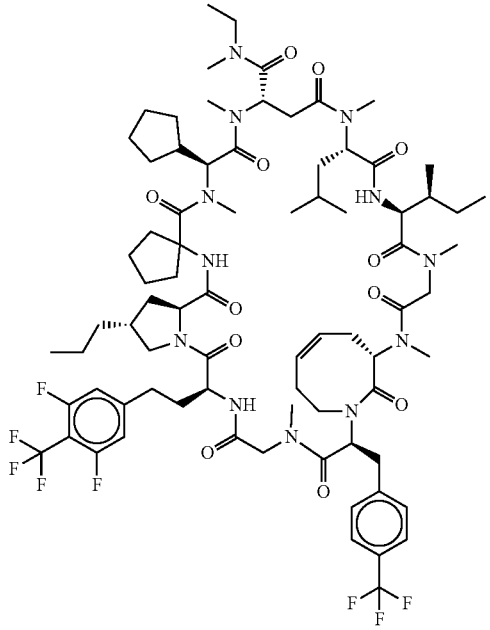 |
| PP1575 | 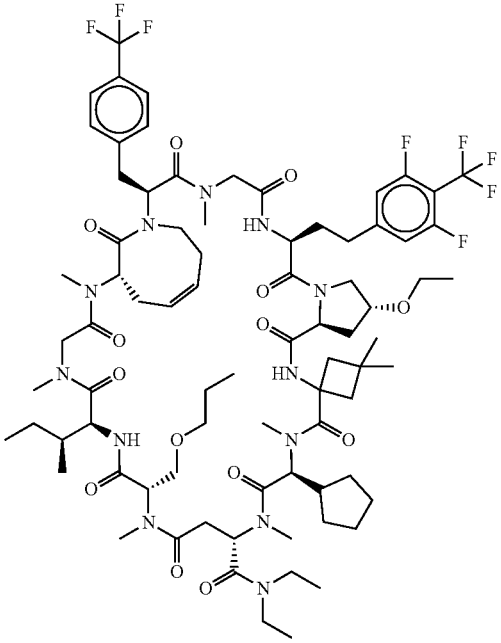 |

TABLE 38-continued
| Compound No. | Structural Formula |
|---|---|
| PP1576 | 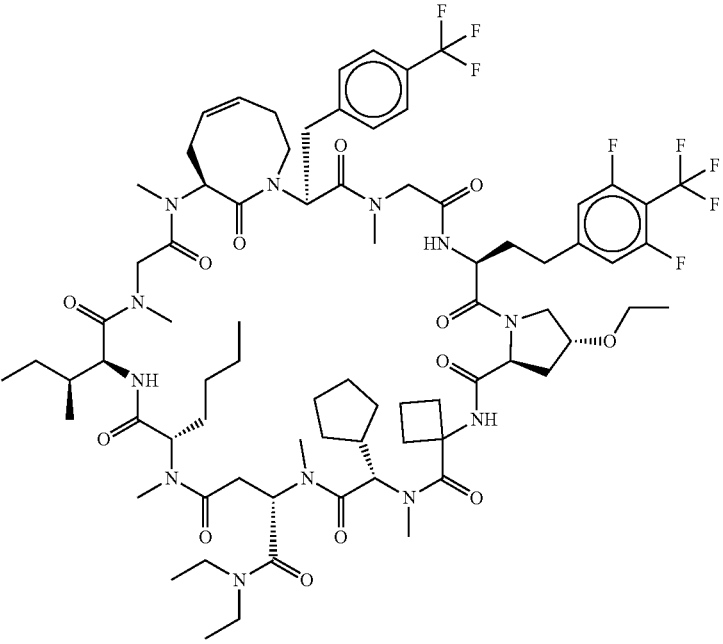 |
| PP1577 | 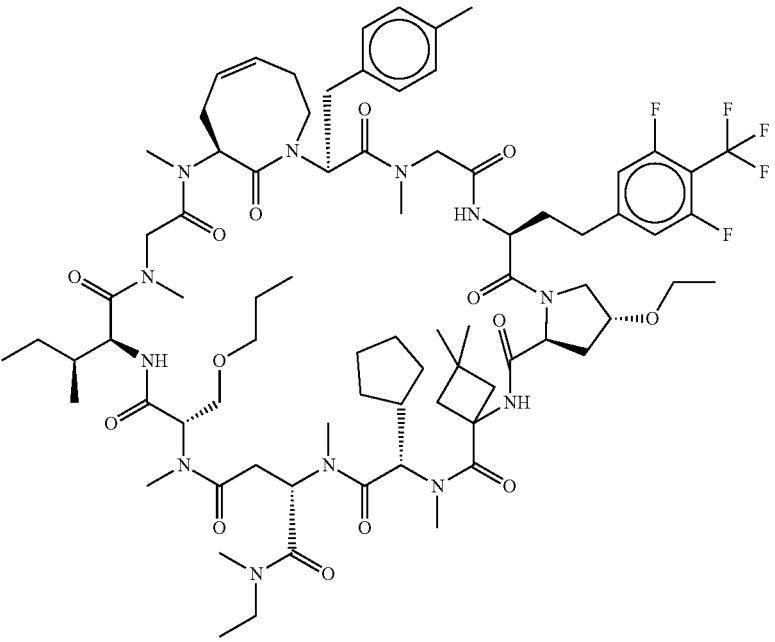 |

TABLE 38-continued

| Compound No. | Structural Formula |
|---|---|
| PP1578 | |
| PP1579 | |

TABLE 38-continued

| Compound No. | Structural Formula |
|---|---|
| PP1580 | |
| PP1581 | |

TABLE 38-continued

| Compound No. | Structural Formula |
|---|---|
| PP1582 | |
| PP1583 | |

TABLE 38-continued
| Compound No. | Structural Formula |
|---|---|
| PP1584 | 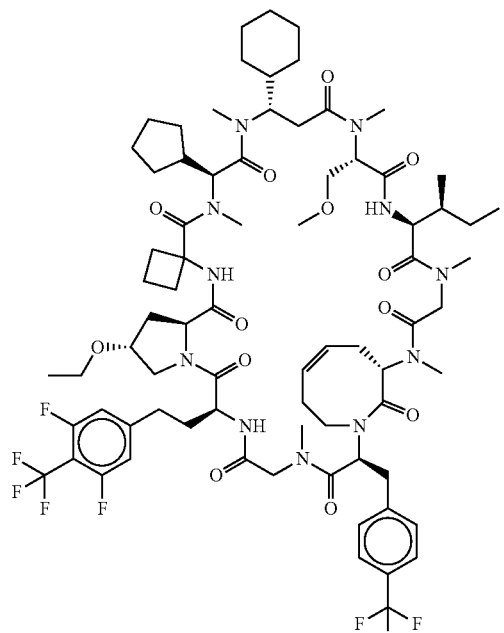 |
| PP1585 | 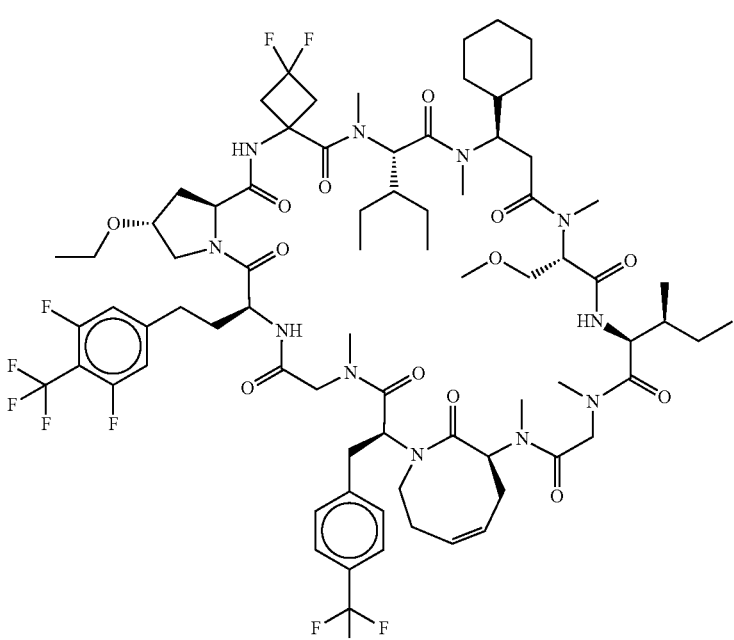 |

| Compound No. | Structural Formula |
|---|---|
| PP1586 | 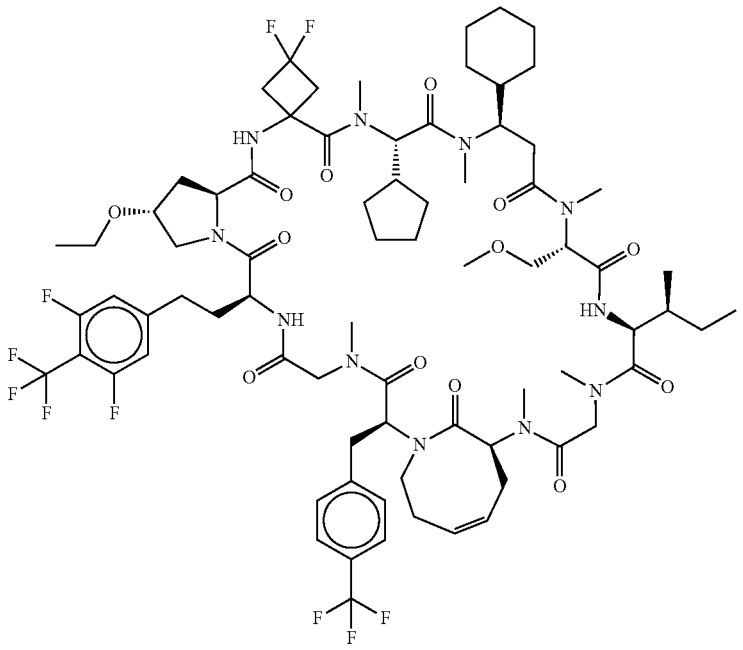 |
| PP1587 | 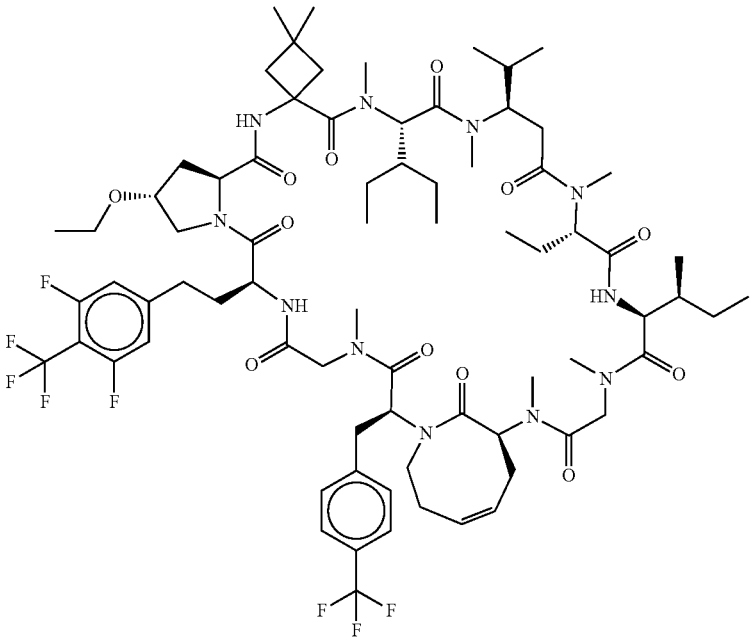 |

TABLE 38-continued

| Compound No. | Structural Formula |
|---|---|
| PP1588 | |
| PP1589 | |

//
| Compound No. | Structural Formula |
|---|---|
| PP1590 | 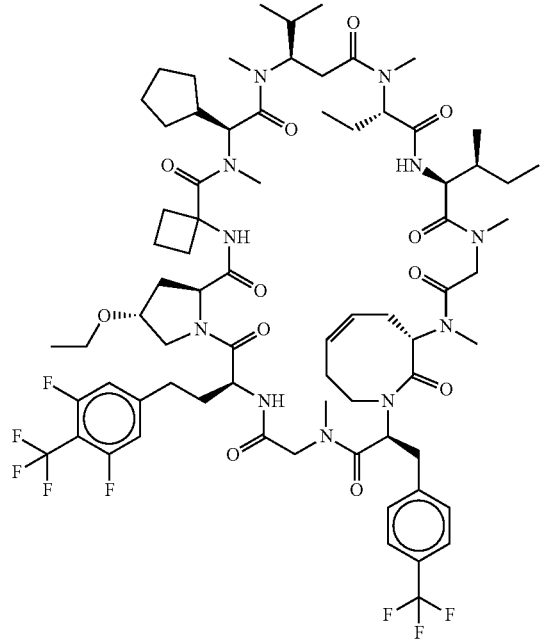 |
| PP1591 | 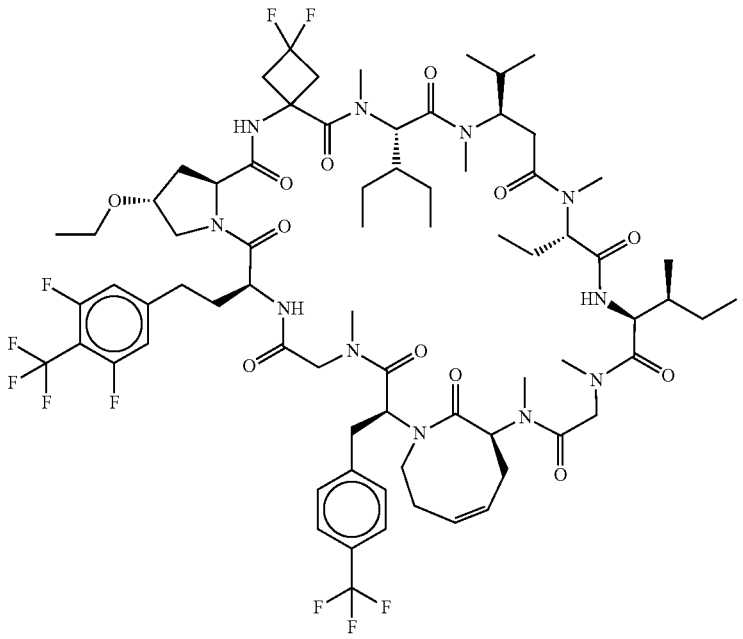 |

TABLE 38-continued
| Compound No. | Structural Formula |
|---|---|
| PP1592 | 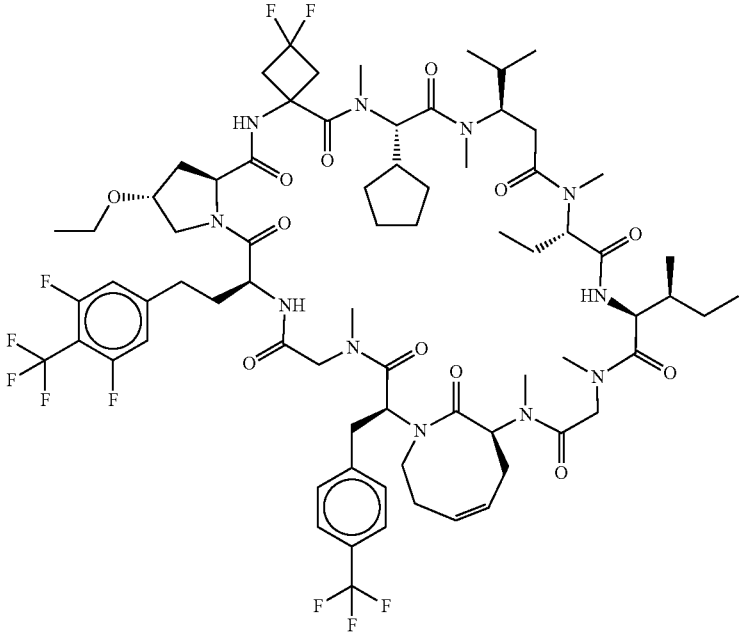 |
| PP1593 | 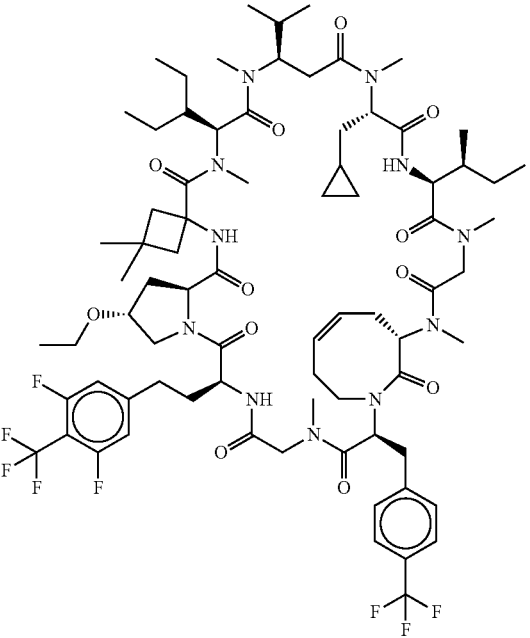 |

TABLE 38-continued
| Compound No. | Structural Formula |
|---|---|
| PP1594 | 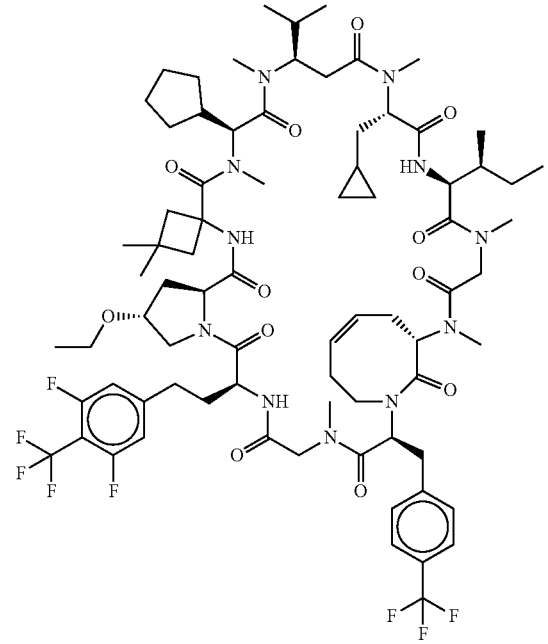 |
| PP1595 | 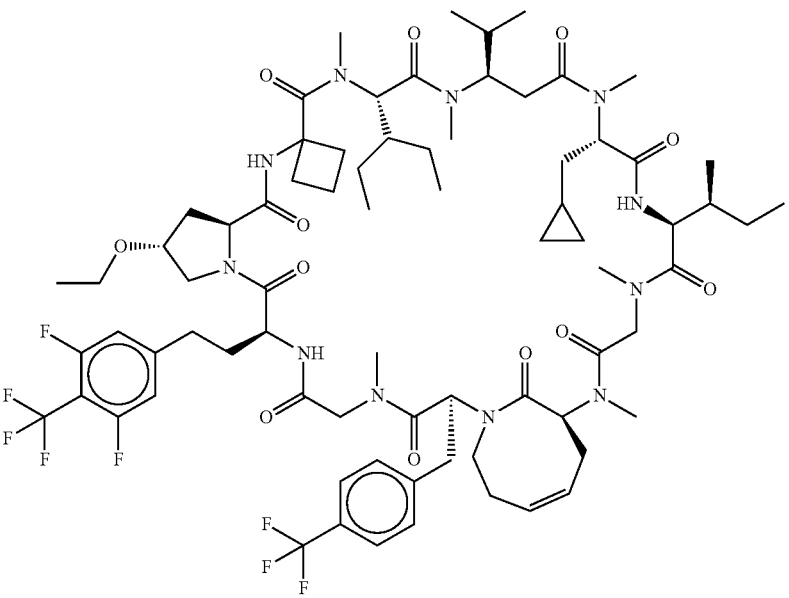 |

TABLE 38-continued

| Compound No. | Structural Formula |
|---|---|
| PP1596 | |
| PP1597 | |

TABLE 38-continued
| Compound No. | Structural Formula |
|---|---|
| PP1598 | 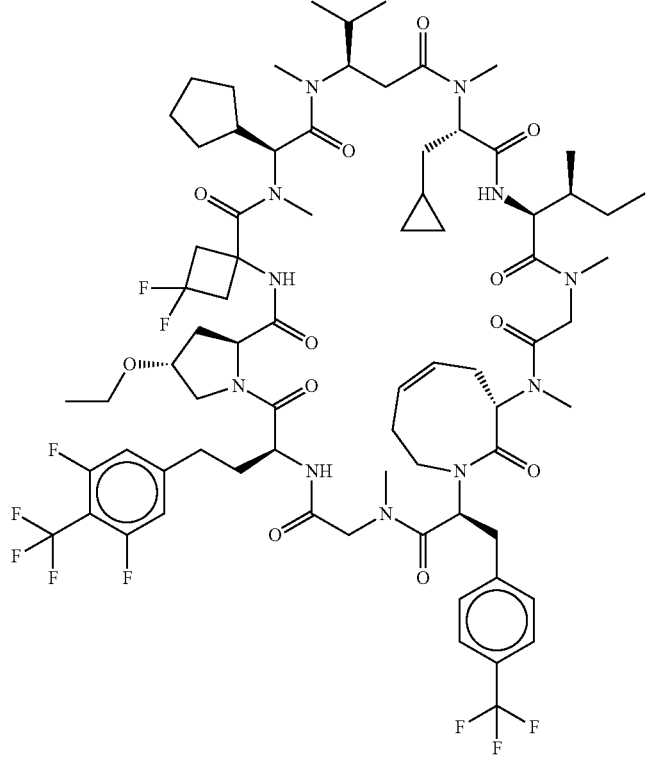 |
| PP1599 | 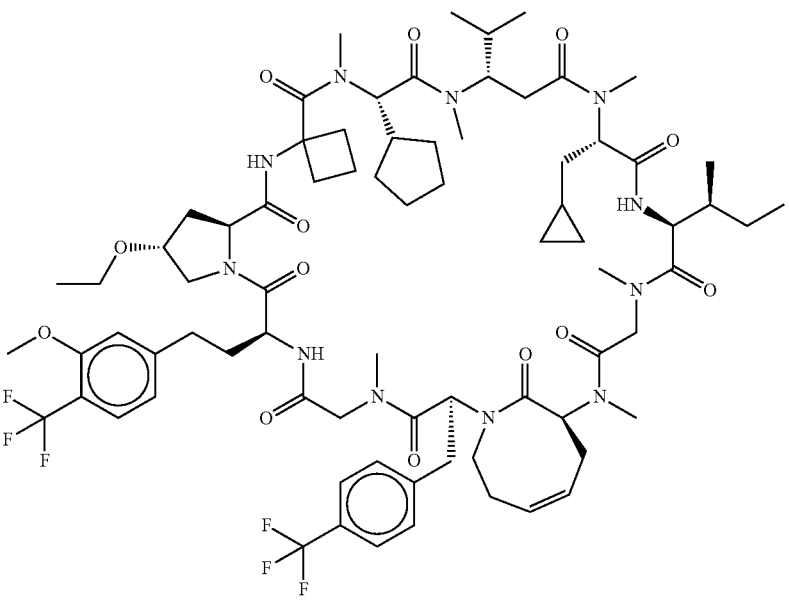 |

TABLE 38-continued
| Compound No. | Structural Formula |
| --- | --- |
| PP1600 | 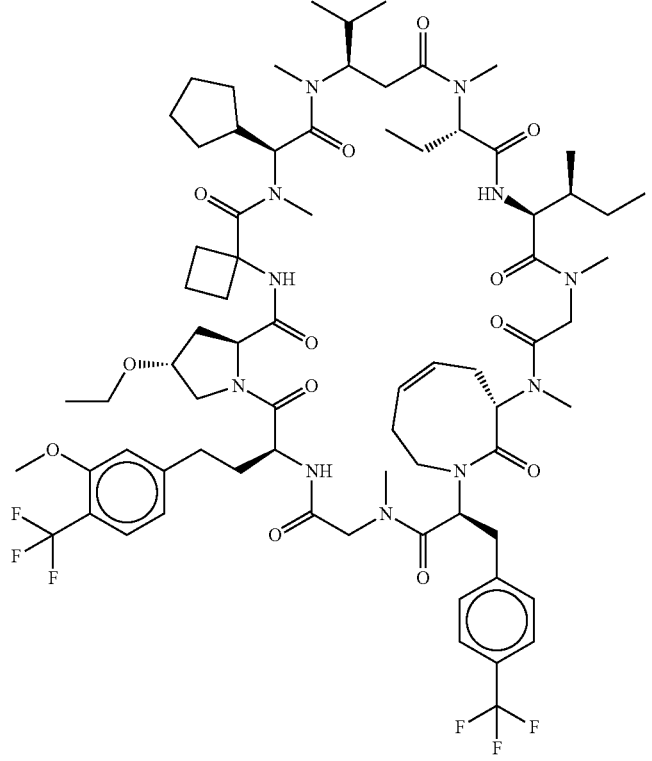 |
| PP1601 | 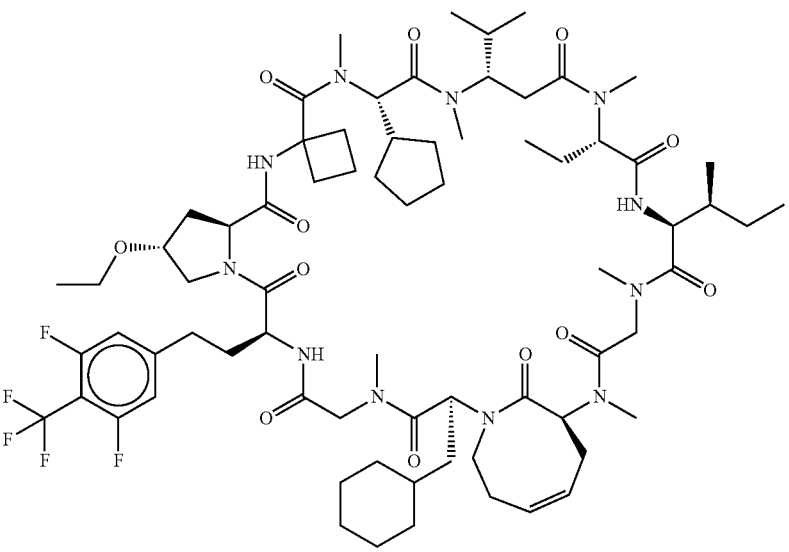 |

TABLE 38-continued
| Compound No. | Structural Formula |
|---|---|
| PP1602 | 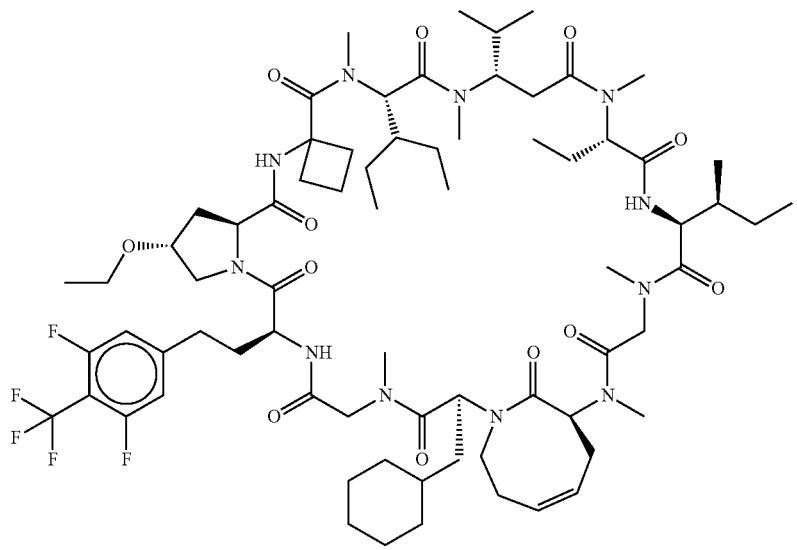 |
| PP1603 | 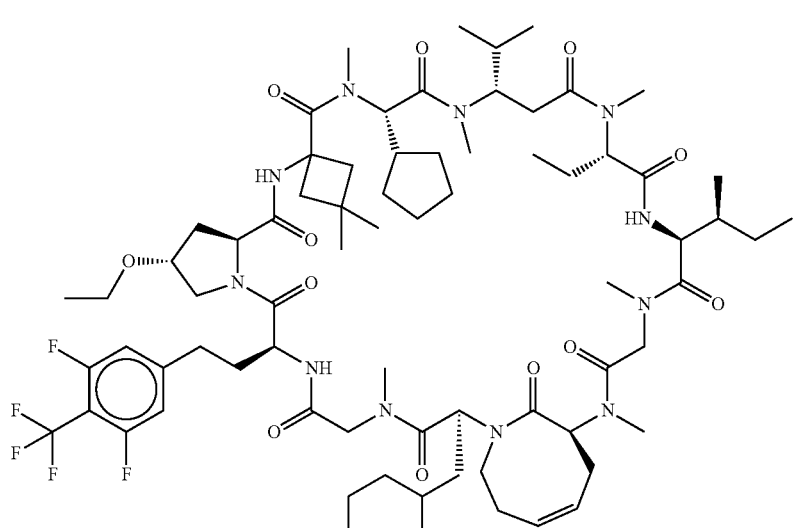 |

TABLE 38-continued
| Compound No. | Structural Formula |
|---|---|
| PP1605 | 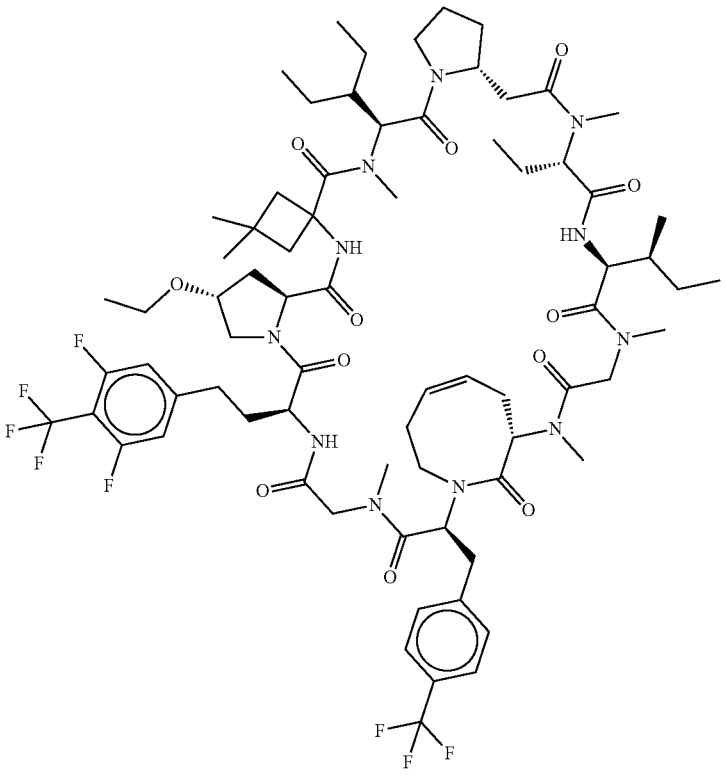 |
| PP1606 | 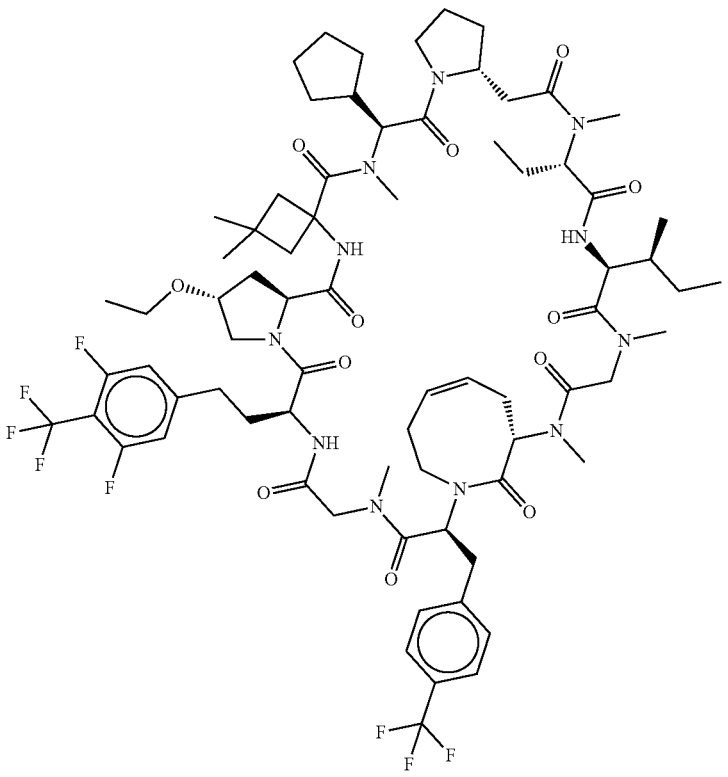 |

US 12,410,212 B2
TABLE 38-continued
| Compound No. | Structural Formula |
|---|---|
| PP1607 | 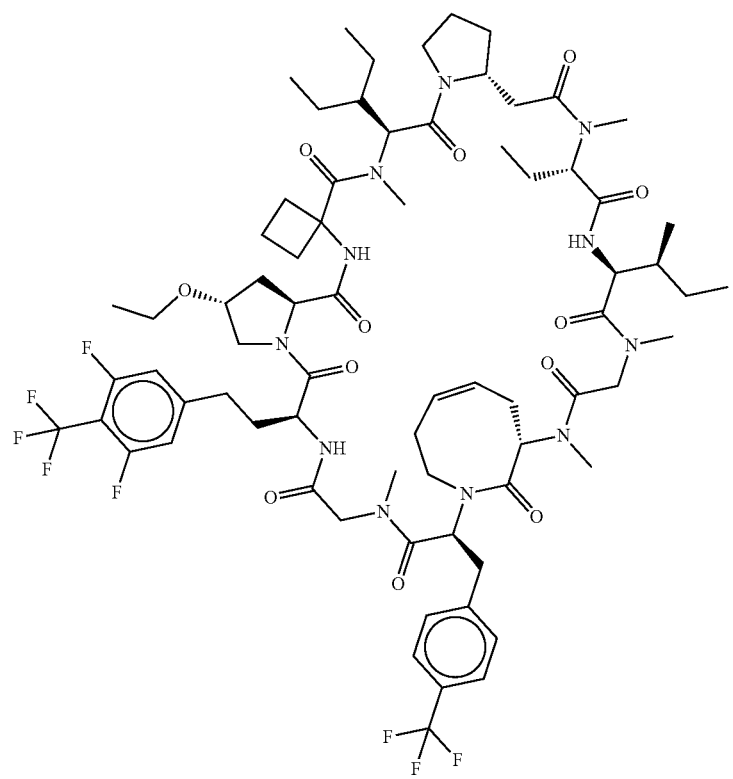 |
| PP1608 | 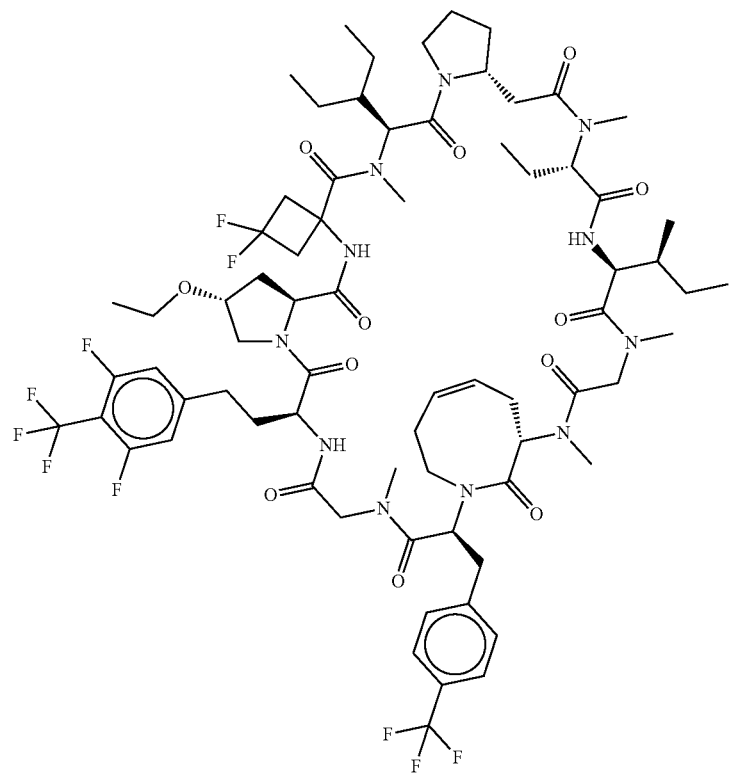 |

TABLE 38-continued
| Compound No. | Structural Formula |
|---|---|
PP1609
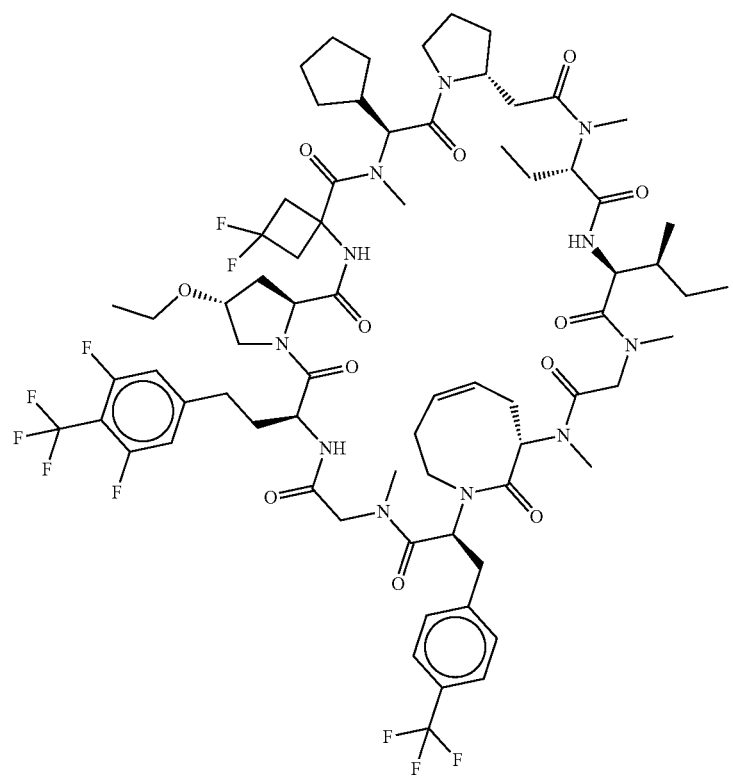
PP1610
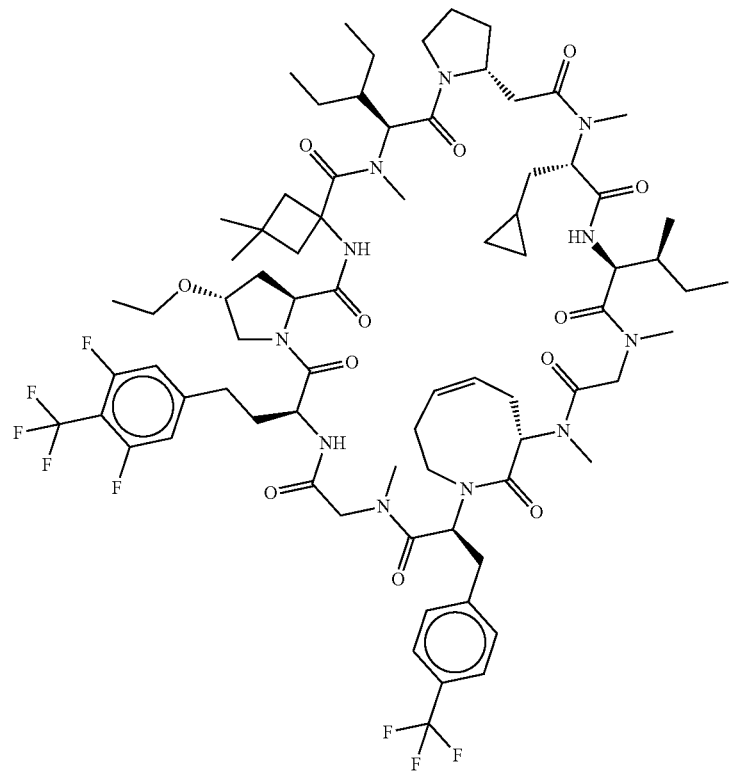

TABLE 38-continued
| Compound No. | Structural Formula |
|---|---|
| PP1611 | 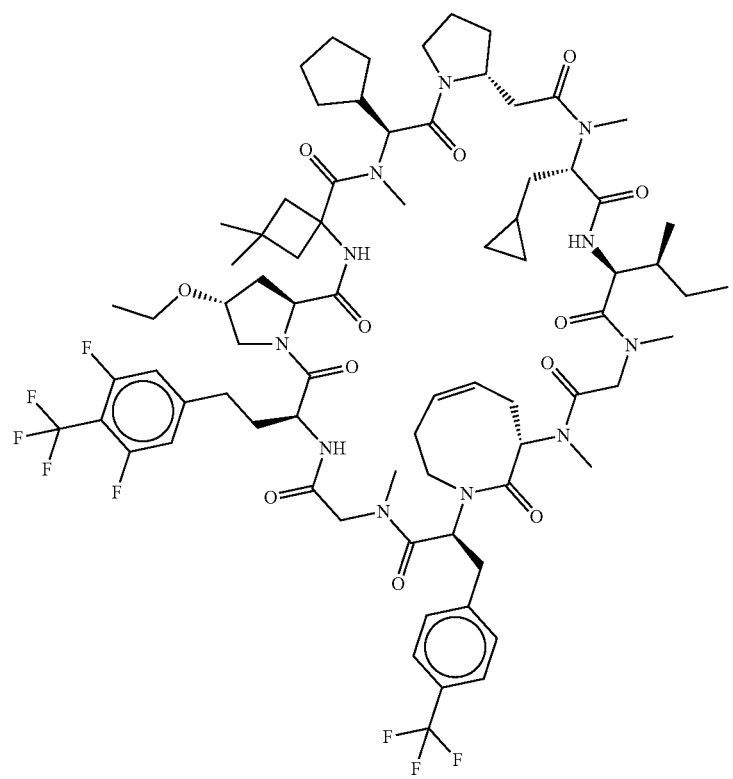 |
| PP1612 | 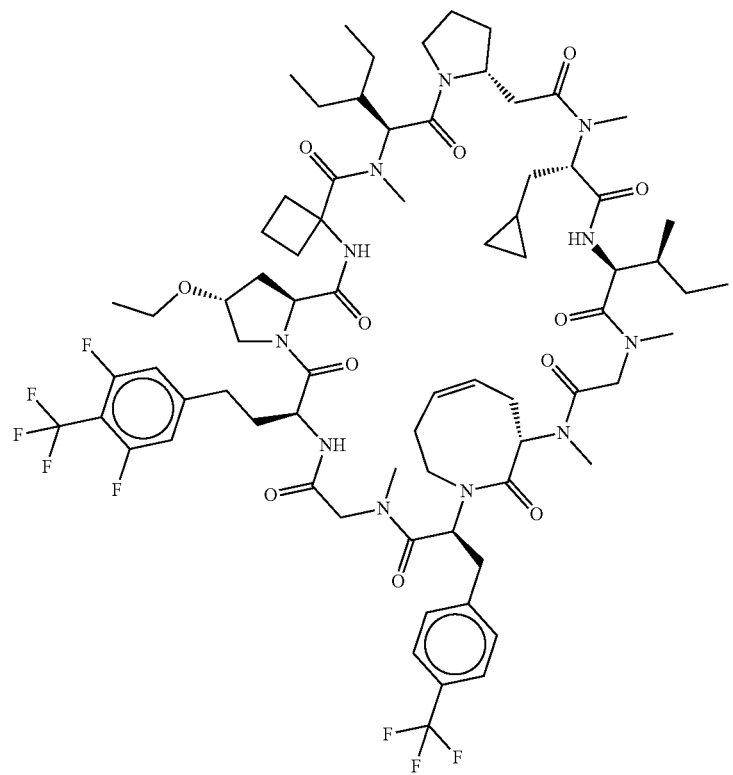 |

TABLE 38-continued
| Compound No. | Structural Formula |
|---|---|
| PP1613 | 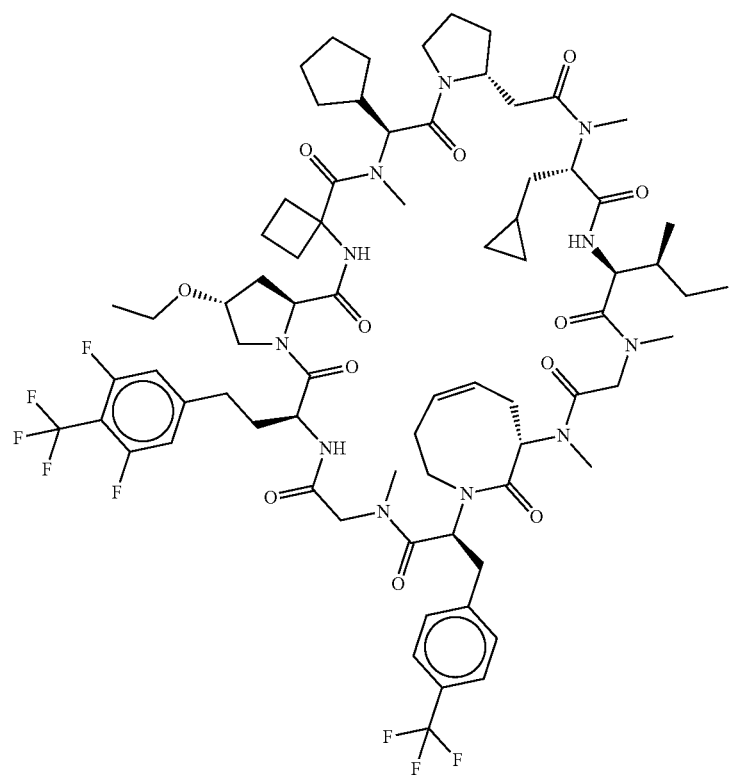 |
| PP1614 | 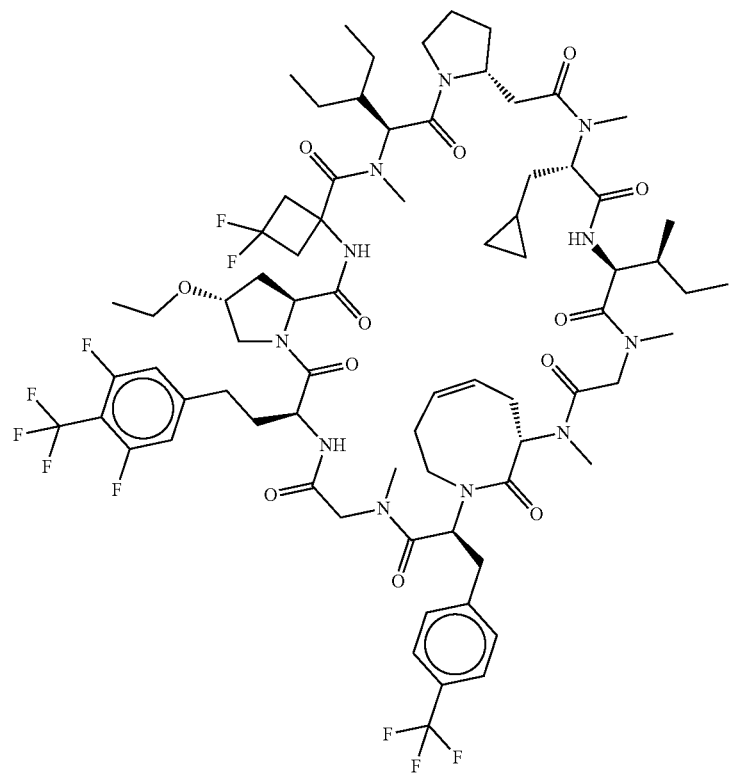 |

TABLE 38-continued
| Compound No. | Structural Formula |
|---|---|
| PP1615 | 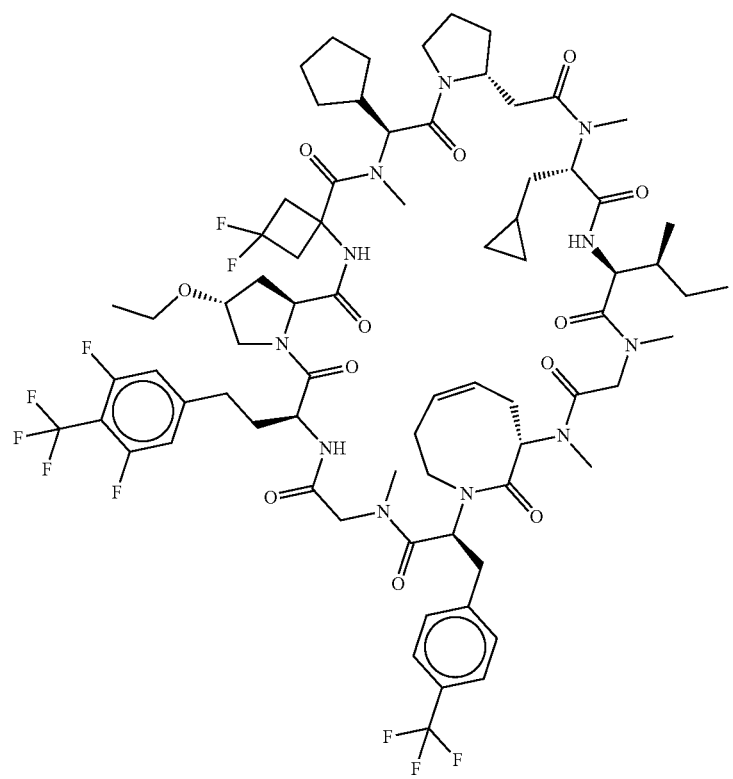 |
| PP1616 | 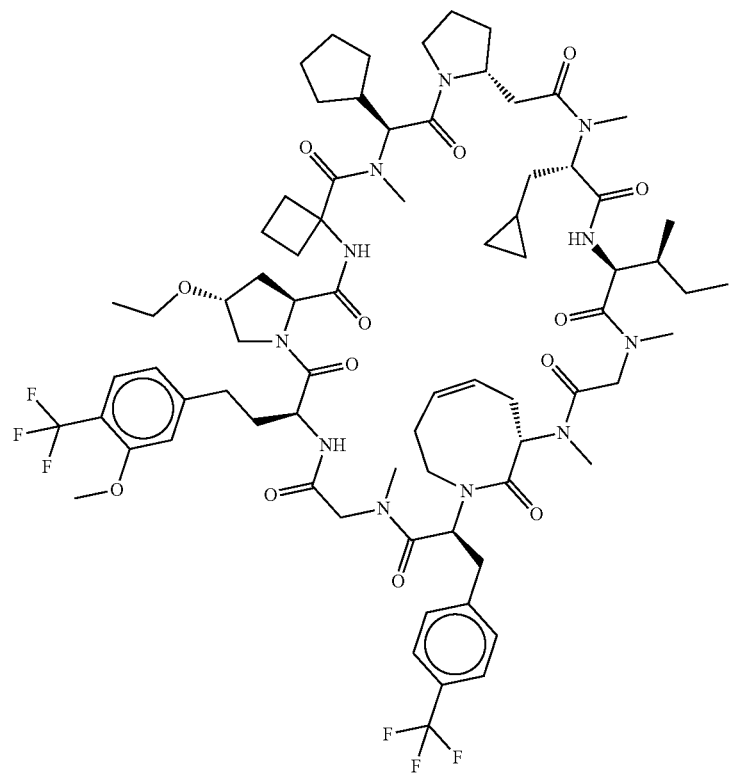 |

TABLE 38-continued
| Compound No. | Structural Formula |
|---|---|
| PP1617 | 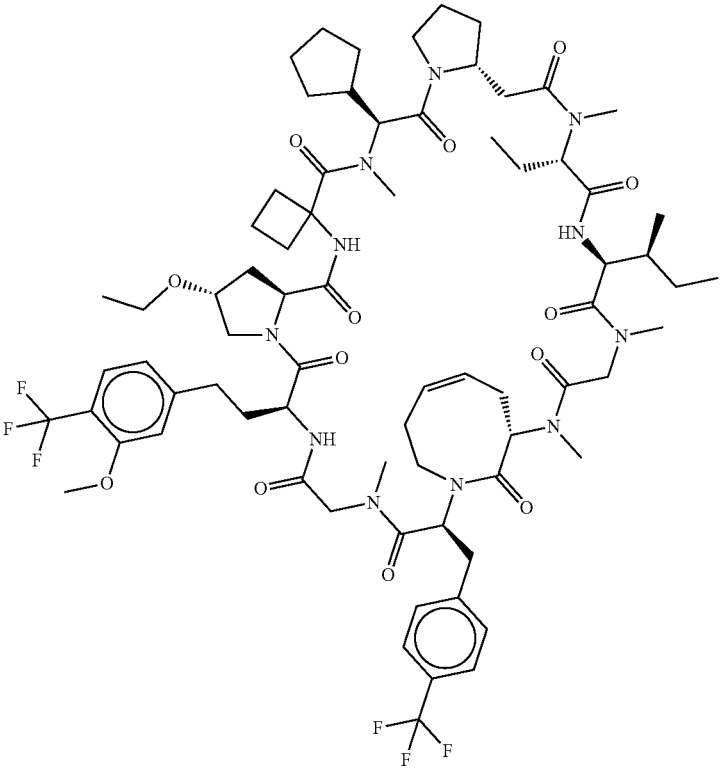 |
| PP1618 | 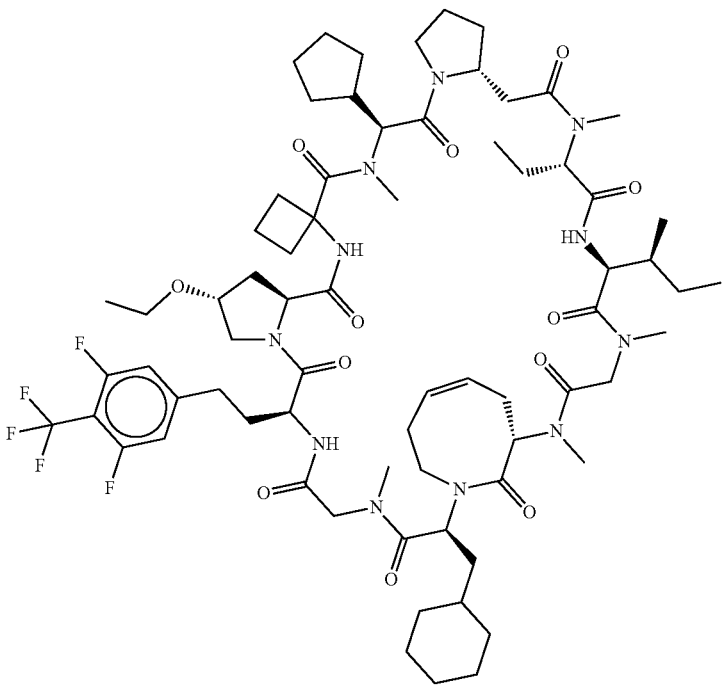 |

US 12,410,212 B2
2409                                                                                    2410
TABLE 38-continued
| Compound No. | Structural Formula |
|---|---|
| PP1619 | 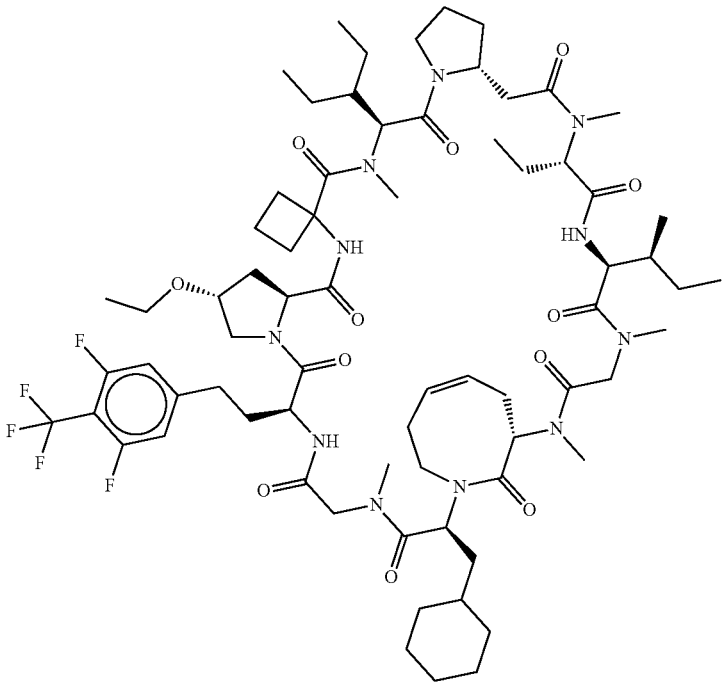 |
| PP1620 | 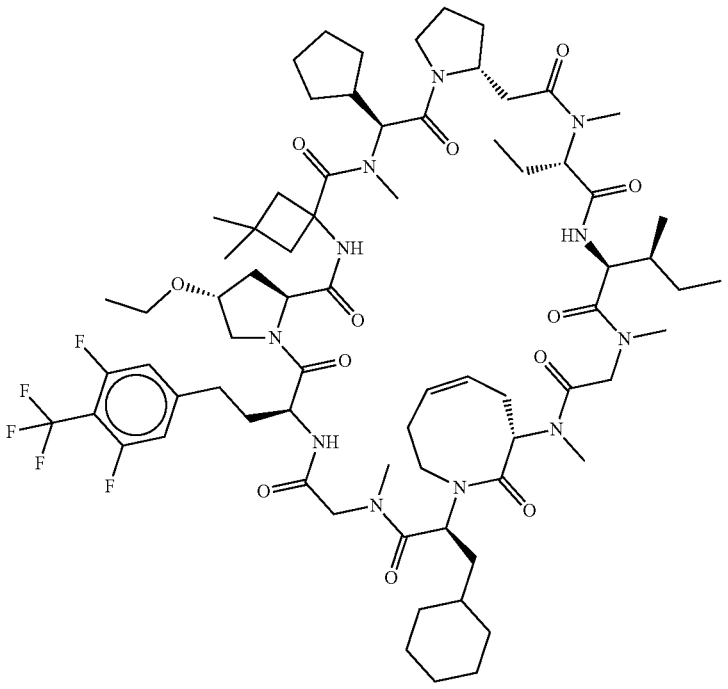 |

TABLE 38-continued

| Compound No. | Structural Formula |
|---|---|
| PP1622 | |
| PP1623 | |

TABLE 38-continued
| Compound No. | Structural Formula |
|---|---|
| PP1624 | 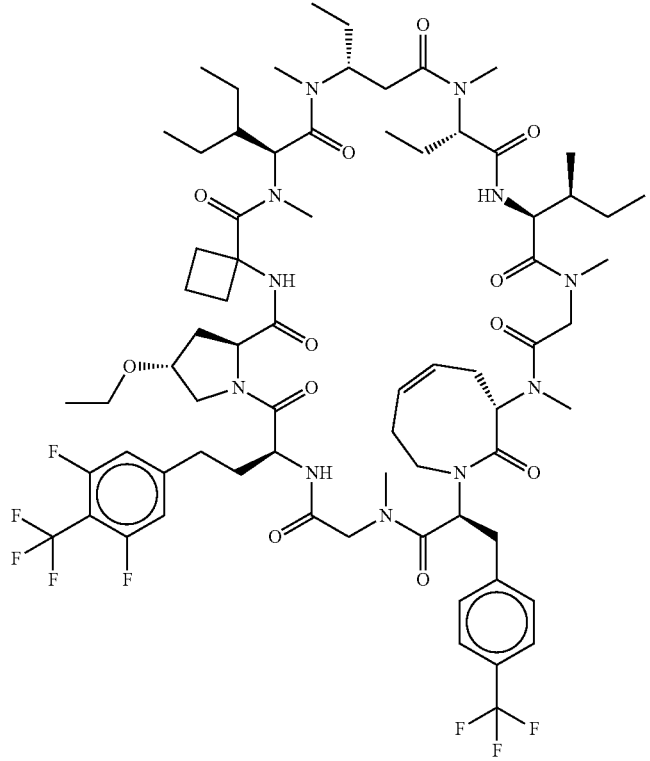 |
| PP1625 | 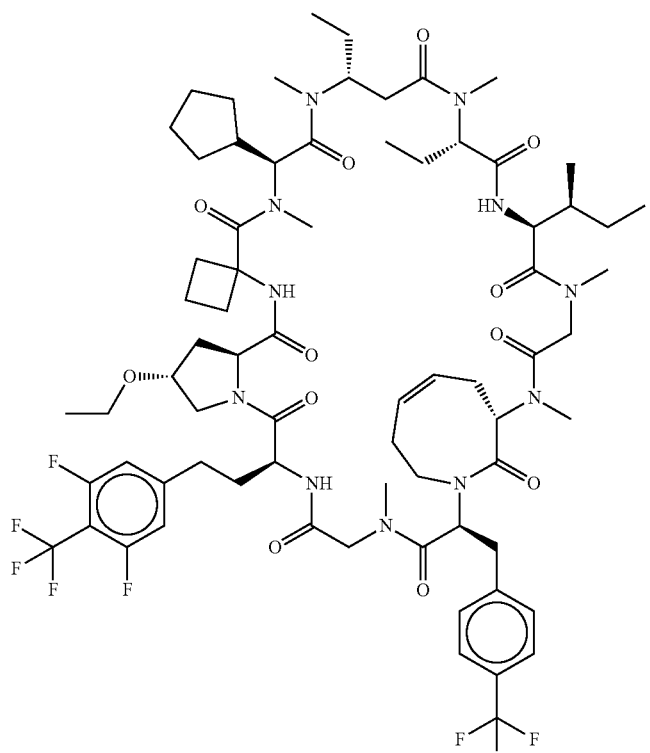 |

TABLE 38-continued
| Compound No. | Structural Formula |
|---|---|
| PP1626 | 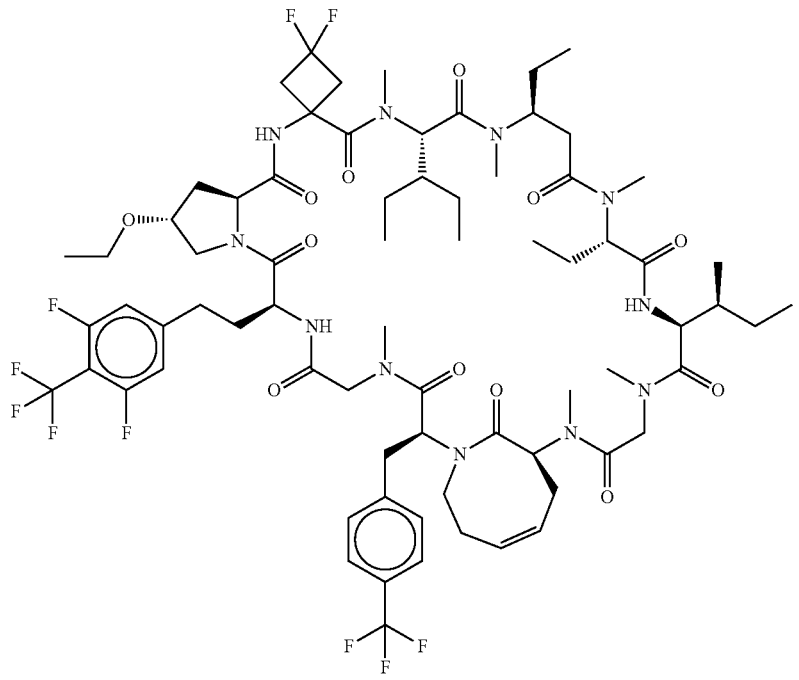 |
| PP1627 | 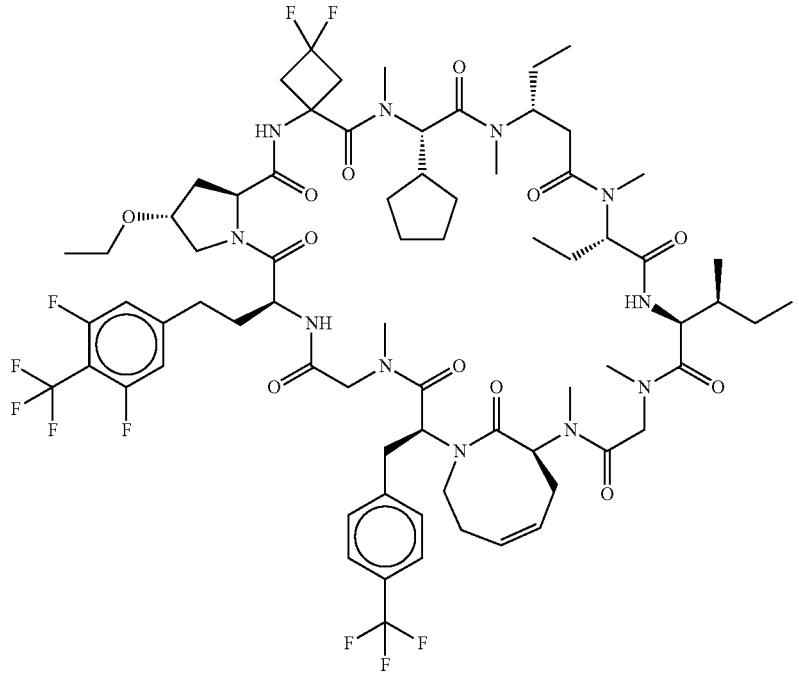 |

TABLE 38-continued
| Compound No. | Structural Formula |
|---|---|
| PP1628 | 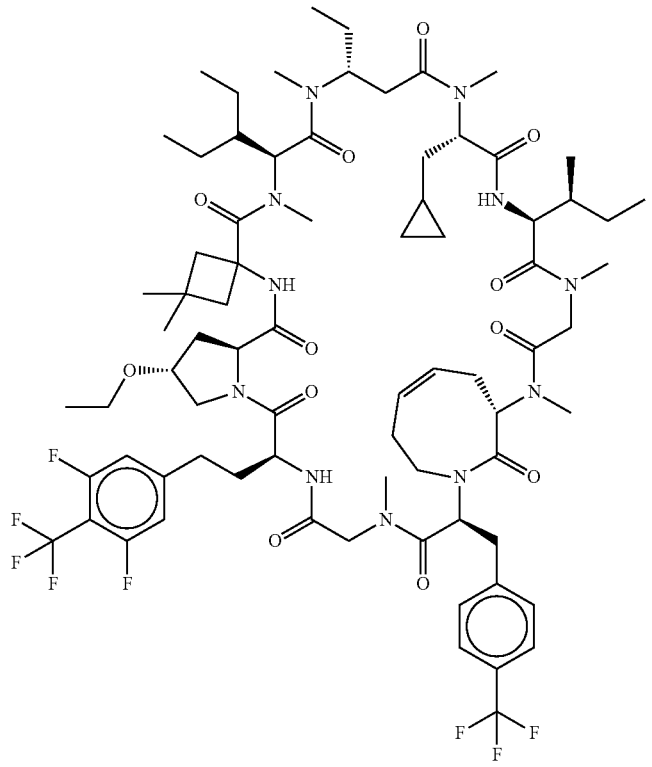 |
| PP1629 | 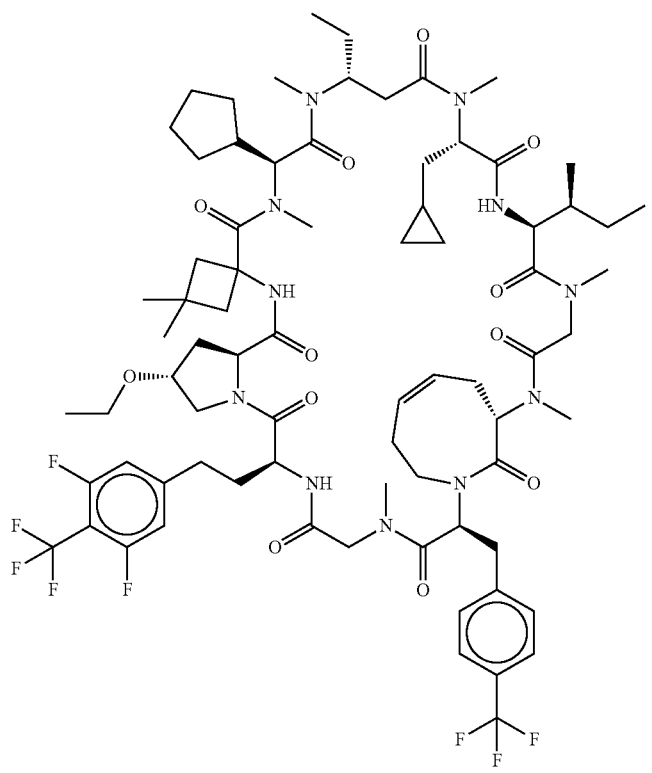 |

TABLE 38-continued
| Compound No. | Structural Formula |
|---|---|
| PP1630 | 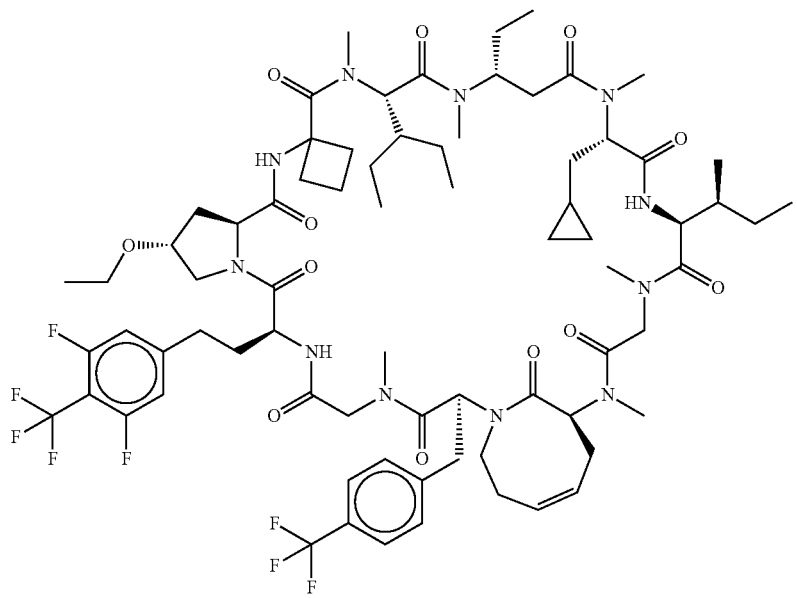 |
| PP1631 | 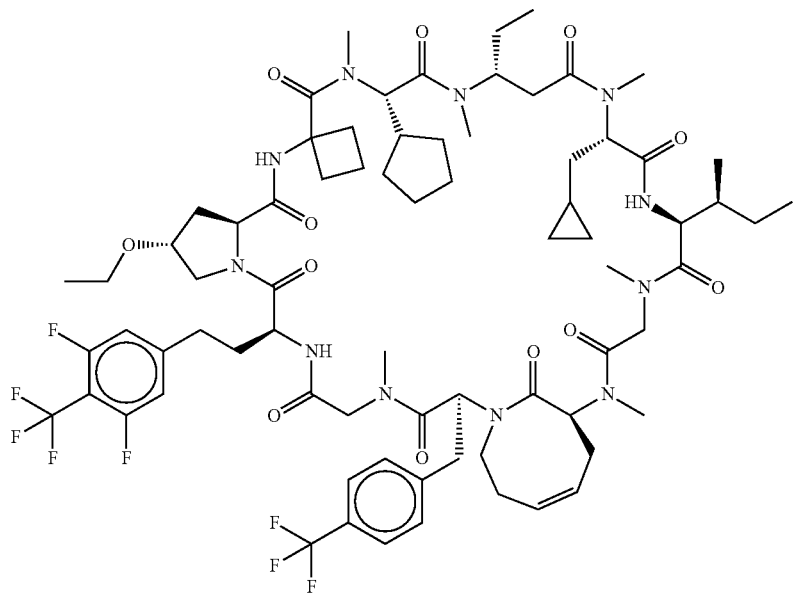 |

TABLE 38-continued
| Compound No. | Structural Formula |
|---|---|
| PP1632 | 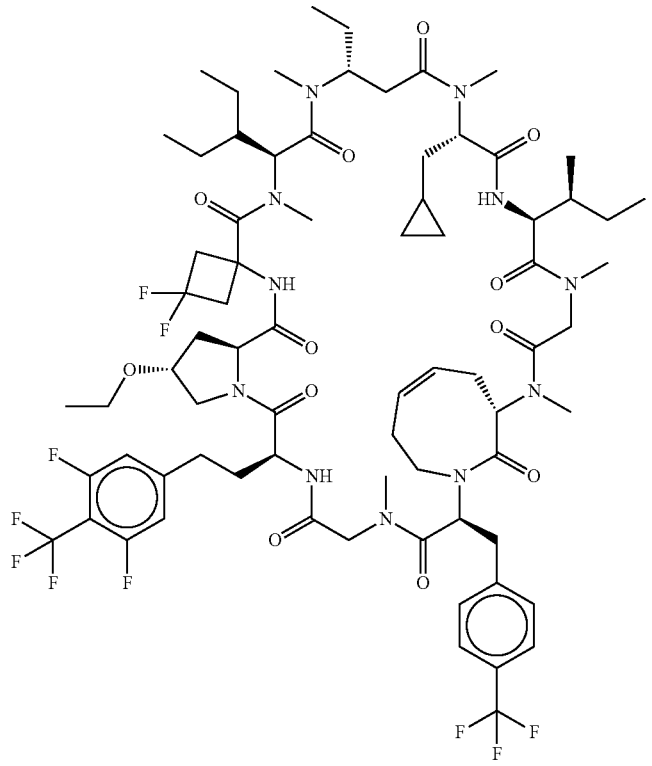 |
| PP1633 | 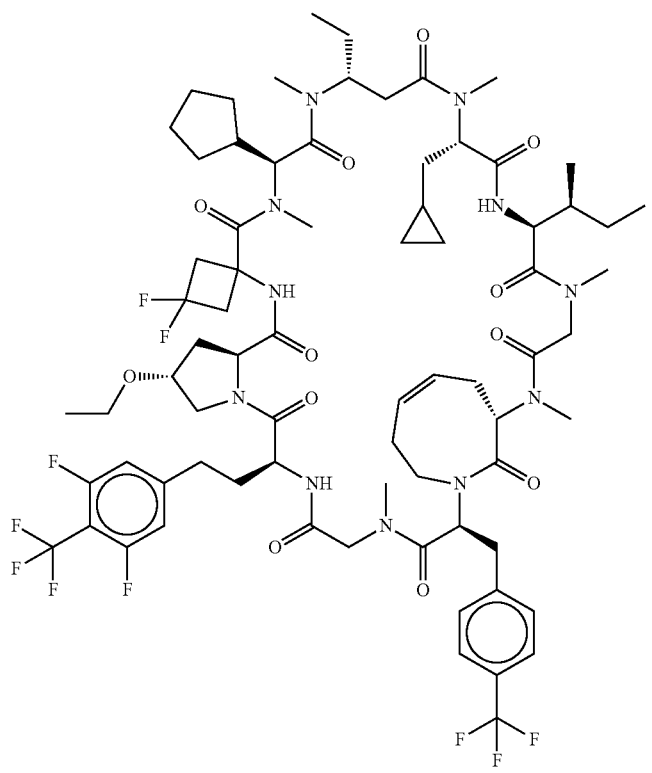 |

TABLE 38-continued
| Compound No. | Structural Formula |
|---|---|
| PP1634 | 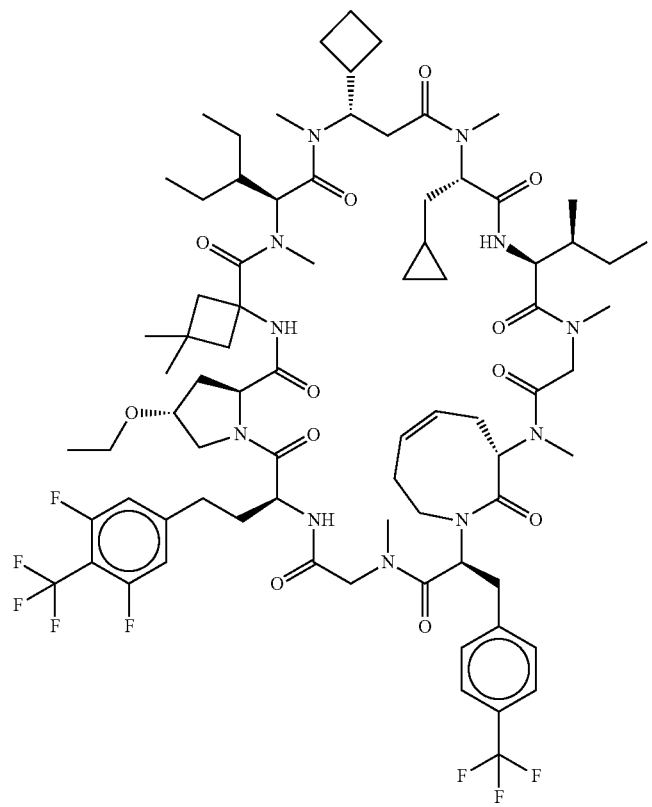 |
| PP1635 | 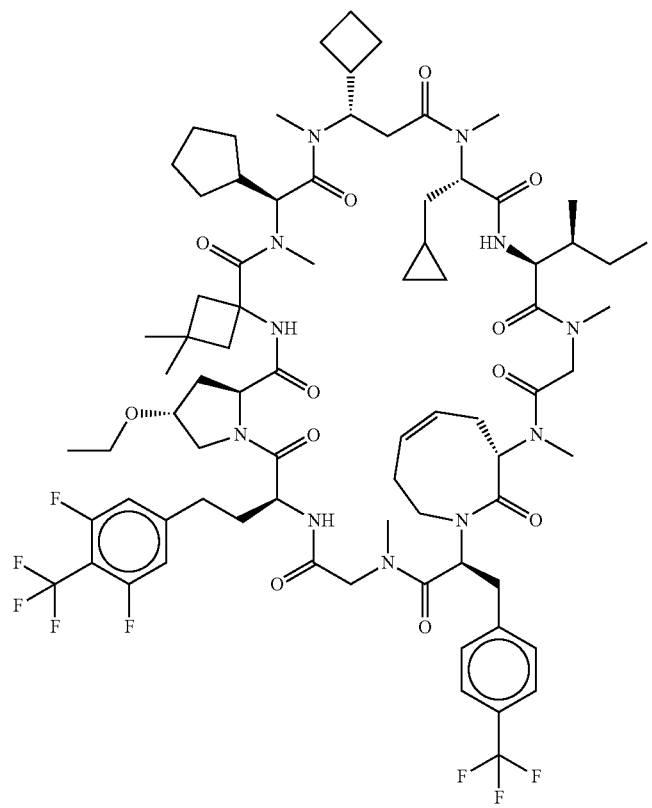 |

TABLE 38-continued
| Compound No. | Structural Formula |
|---|---|
| PP1636 | 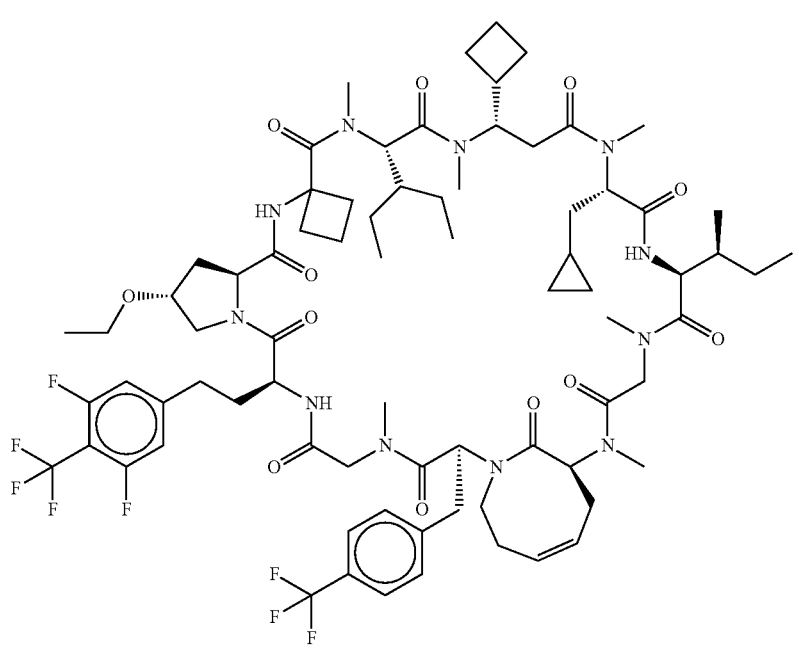 |
| PP1637 | 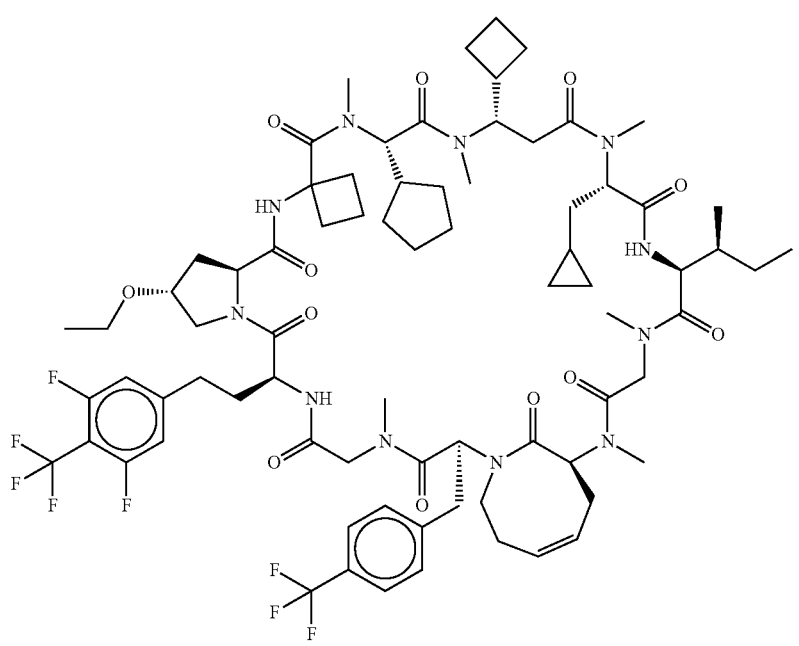 |

TABLE 38-continued
| Compound No. | Structural Formula |
|---|---|
| PP1638 | 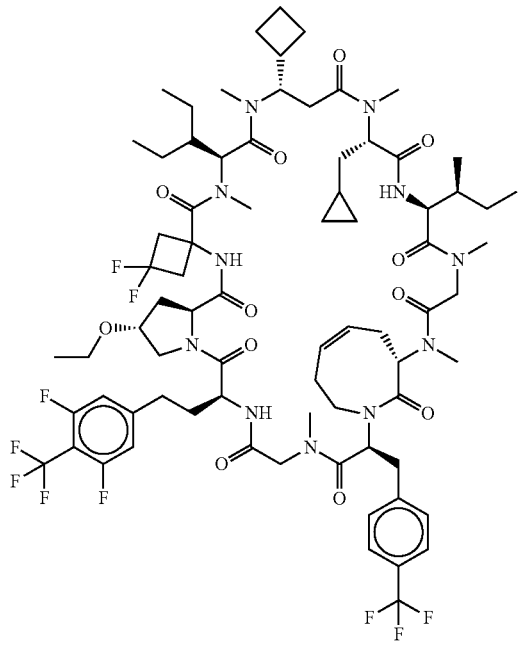 |
| PP1639 | 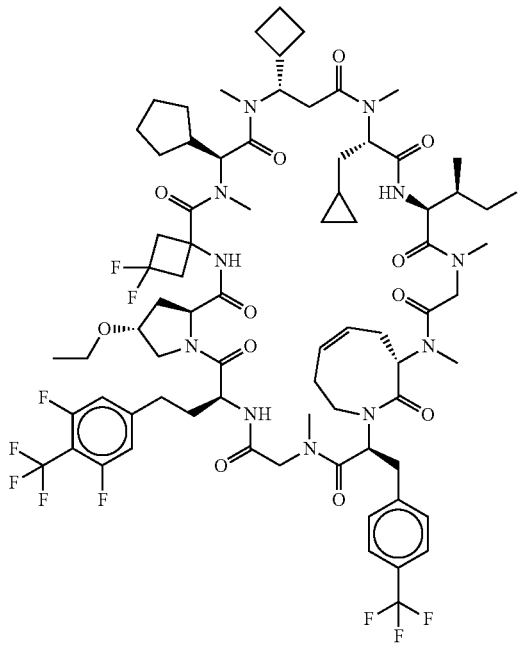 |

2429 2430
TABLE 38-continued
| Compound No. | Structural Formula |
|---|---|
| PP1640 | 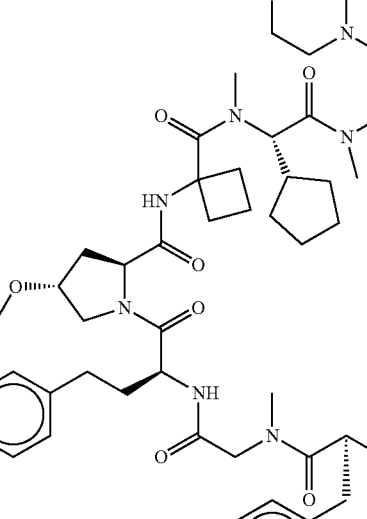 |
| PP1641 | 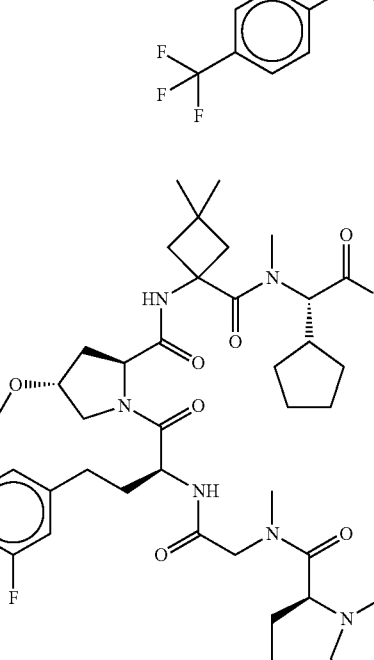 |

TABLE 38-continued
| Compound No. | Structural Formula |
|---|---|
| PP1643 | 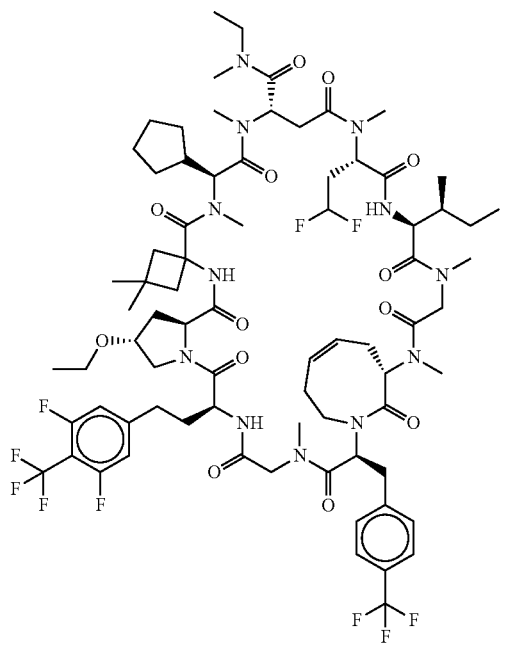 |
| PP1644 | 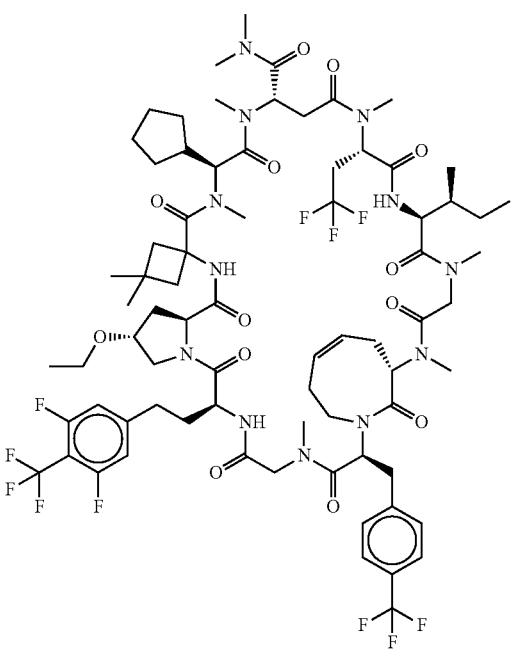 |

TABLE 38-continued
| Compound No. | Structural Formula |
|---|---|
| PP1645 | 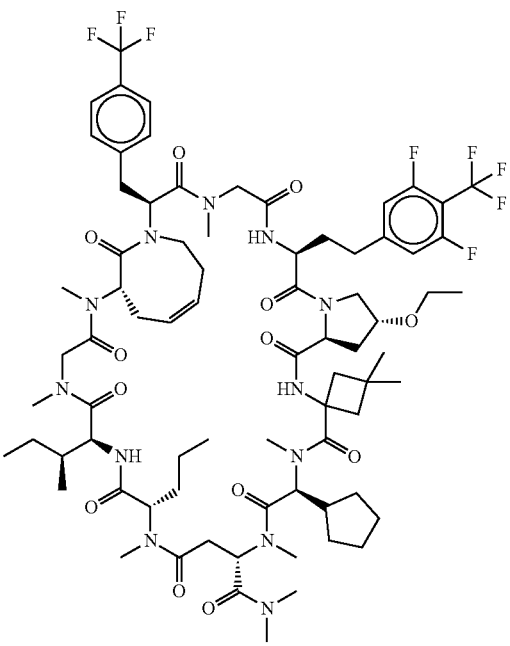 |
| PP1646 | 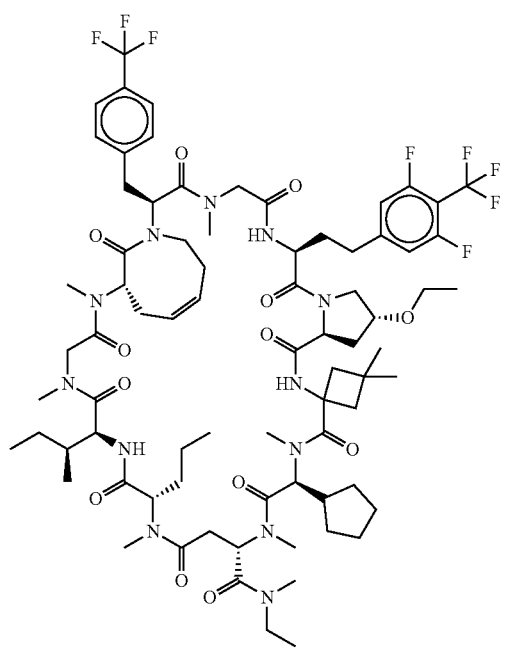 |

TABLE 38-continued
| Compound No. | Structural Formula |
|---|---|
| PP1648 | 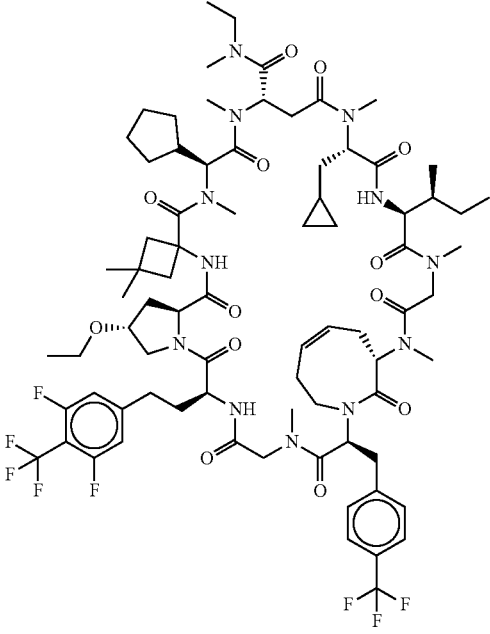 |
| PP1649 | 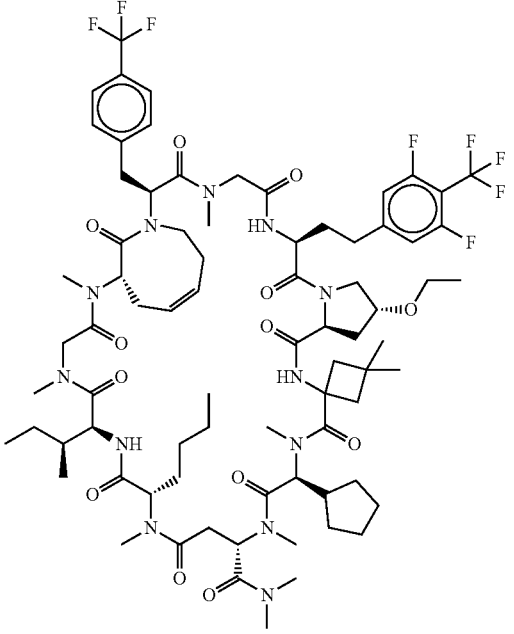 |

| Compound No. | Structural Formula |
| --- | --- |
| PP1650 | |
| PP1651 | |

TABLE 38-continued

| Compound No. | Structural Formula |
|---|---|
| PP1653 | |
| PP1654 | |

TABLE 38-continued
| Compound No. | Structural Formula |
|---|---|
| PP1655 | 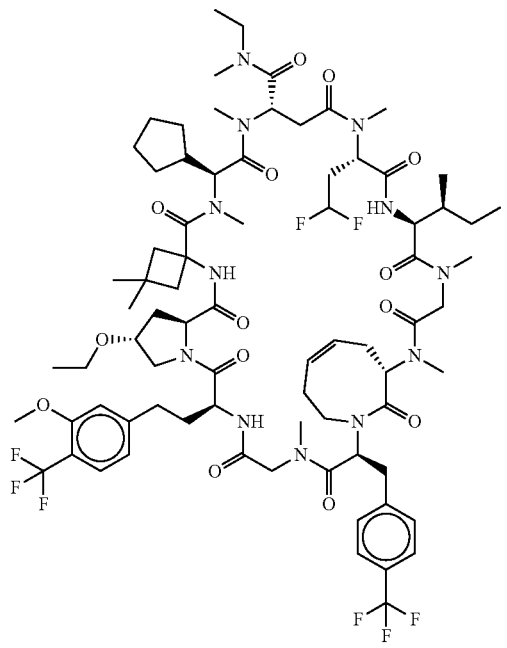 |
| PP1656 | 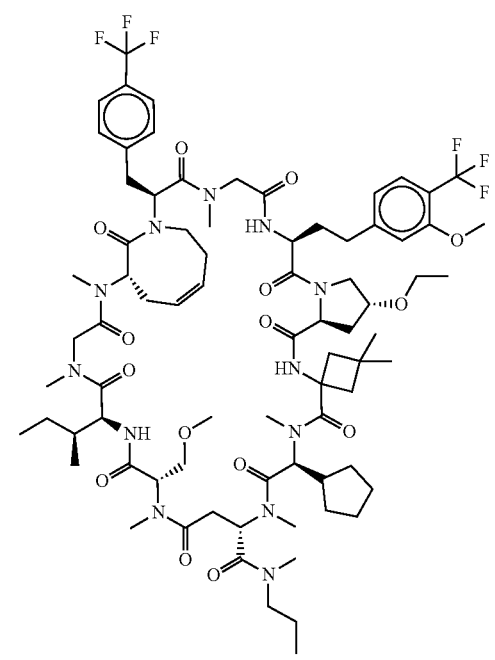 |

TABLE 38-continued

| Compound No. | Structural Formula |
|---|---|
| PP1657 | |
| PP1658 | |

TABLE 38-continued

| Compound No. | Structural Formula |
|---|---|
| PP1660 | |
| PP1661 | |

TABLE 38-continued

| Compound No. | Structural Formula |
|---|---|
| PP1662 | |
| PP1663 | |

TABLE 38-continued

| Compound No. | Structural Formula |
|---|---|
| PP1665 | |
| PP1666 | |

TABLE 38-continued

| Compound No. | Structural Formula |
|---|---|
| PP1667 | |
| PP1668 | |

TABLE 38-continued

| Compound No. | Structural Formula |
|---|---|
| PP1670 | |
| PP1671 | |

TABLE 38-continued

| Compound No. | Structural Formula |
|---|---|
| PP1672 | |
| PP1673 | |

TABLE 38-continued

| Compound No. | Structural Formula |
|---|---|
| PP1674 | |
| PP1675 | |

TABLE 38-continued

| Compound No. | Structural Formula |
|---|---|
| PP1676 | |
| PP1677 | |

TABLE 38-continued

| Compound No. | Structural Formula |
|---|---|
| PP1678 | |
| PP1679 | |

TABLE 38-continued

| Compound No. | Structural Formula |
|---|---|
| PP1682 | |
| PP1683 | |

TABLE 38-continued

| Compound No. | Structural Formula |
|---|---|
| PP1684 | |
| PP1687 | |

TABLE 38-continued
| Compound No. | Structural Formula |
|---|---|
| PP1688 | 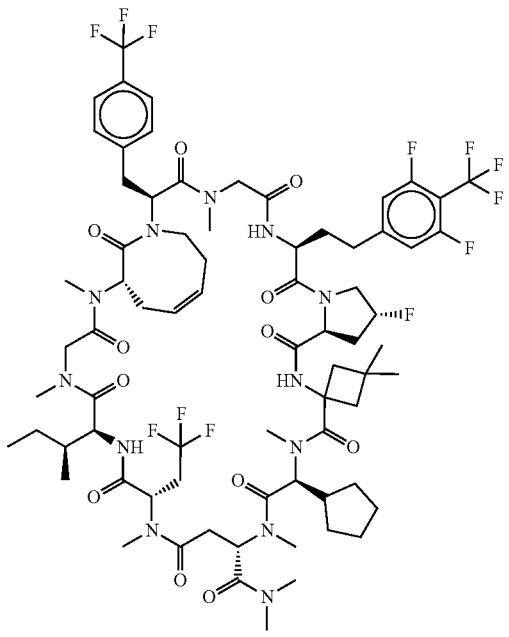 |
| PP1689 | 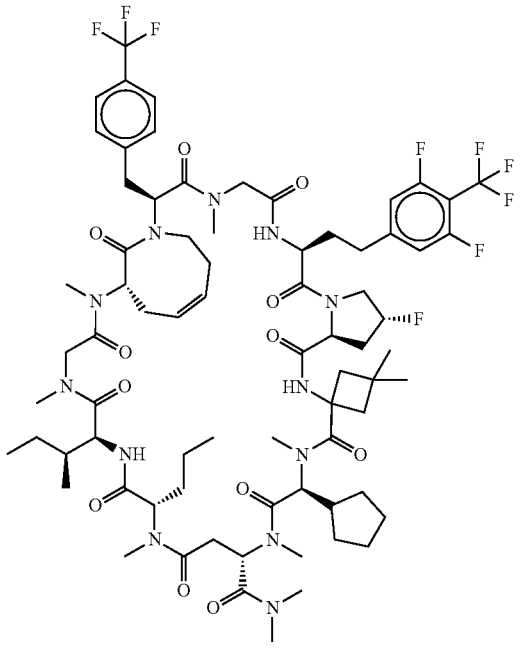 |

TABLE 38-continued

| Compound No. | Structural Formula |
|---|---|
| PP1691 | |
| PP1692 | |

TABLE 38-continued

| Compound No. | Structural Formula |
| --- | --- |
| PP1693 | |
| PP1694 | |

TABLE 38-continued

| Compound No. | Structural Formula |
|---|---|
| PP1696 | |
| PP1697 | |

TABLE 38-continued

| Compound No. | Structural Formula |
|---|---|
| PP1698 | |
| PP1699 | |

TABLE 38-continued

| Compound No. | Structural Formula |
|---|---|
| PP1700 | |
| PP1701 | |

TABLE 38-continued

| Compound No. | Structural Formula |
|---|---|
| PP1702 | |
| PP1703 | |

| Compound No. | Structural Formula |
| --- | --- |
| PP1704 | |
| PP1705 | |

TABLE 38-continued

| Compound No. | Structural Formula |
|---|---|
| PP1706 | |
| PP1707 | |

TABLE 38-continued
| Compound No. | Structural Formula |
| --- | --- |
| PP1709 | 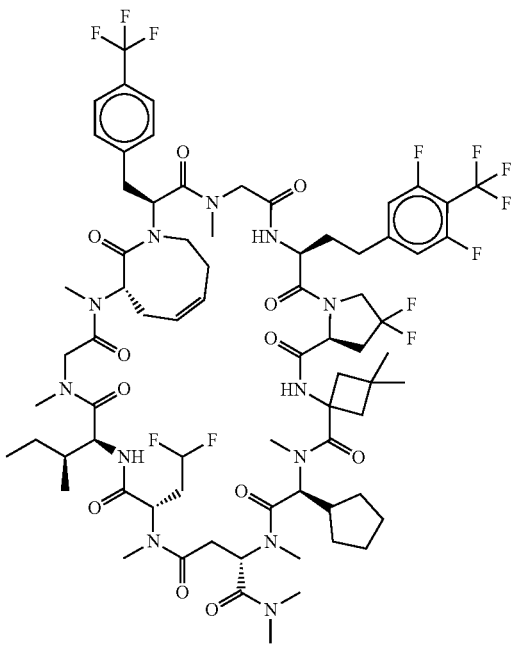 |
| PP1710 | 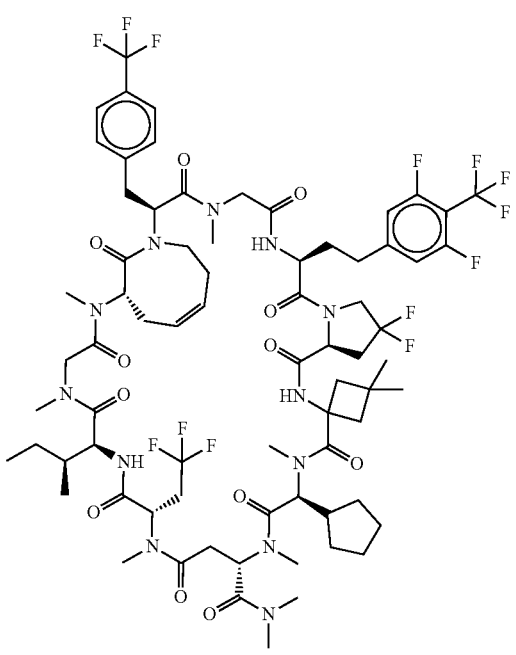 |

TABLE 38-continued
| Compound No. | Structural Formula |
|---|---|
| PP1711 | 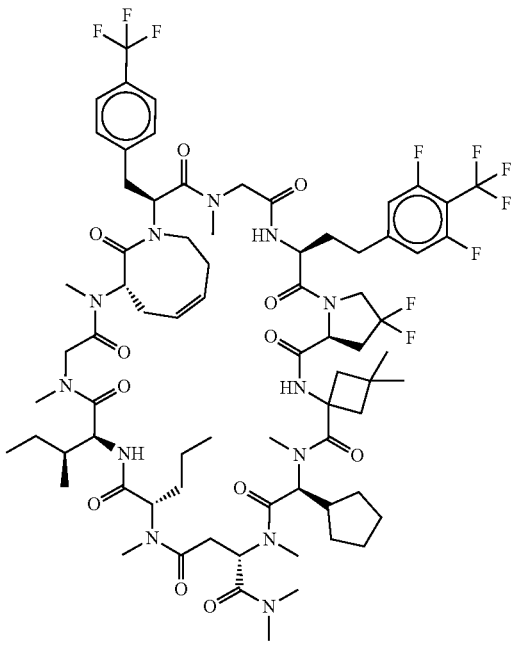 |
| PP1713 | 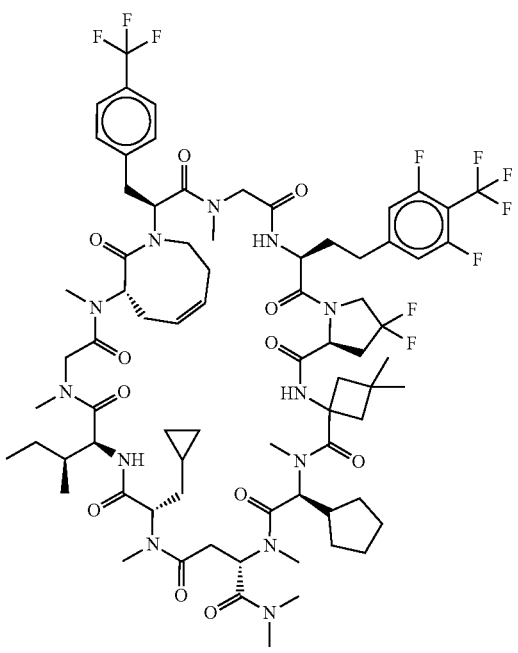 |

TABLE 38-continued

| Compound No. | Structural Formula |
| --- | --- |
| PP1714 | |
| PP1715 | |

TABLE 38-continued

| Compound No. | Structural Formula |
|---|---|
| PP1716 | |
| PP1717 | |

TABLE 38-continued
| Compound No. | Structural Formula |
|---|---|
| PP1718 | 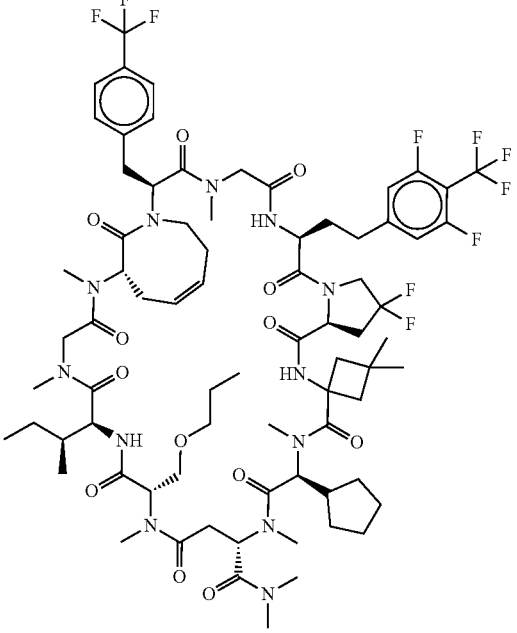 |
| PP1721 | 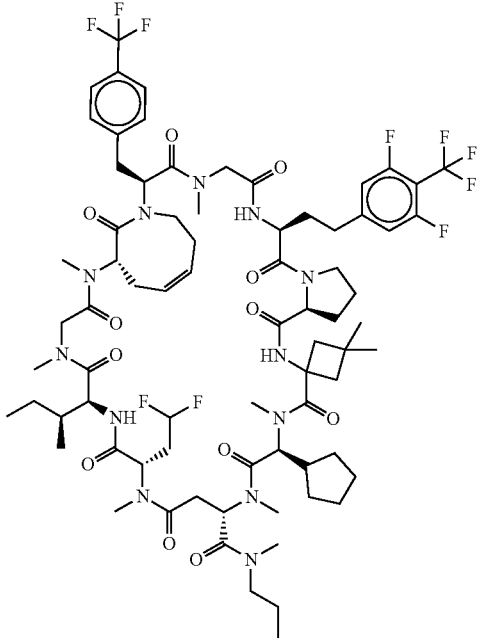 |

TABLE 38-continued
| Compound No. | Structural Formula |
|---|---|
| PP1722 | 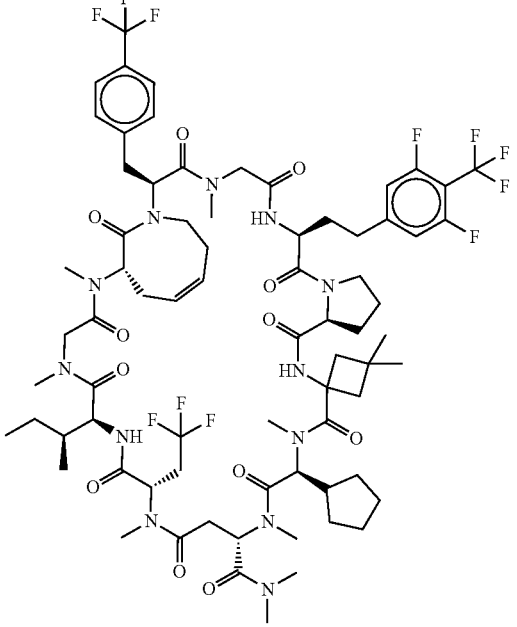 |
| PP1727 | 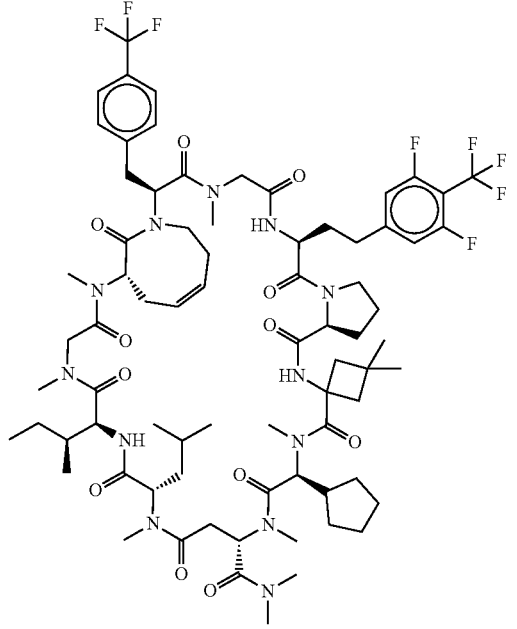 |

TABLE 38-continued

| Compound No. | Structural Formula |
|---|---|
| PP1728 | |
| PP1729 | |

TABLE 38-continued
| Compound No. | Structural Formula |
|---|---|
| PP1731 | 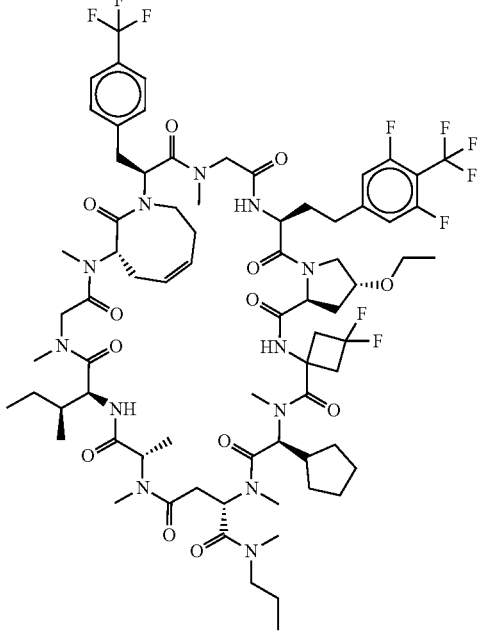 |
| PP1732 | 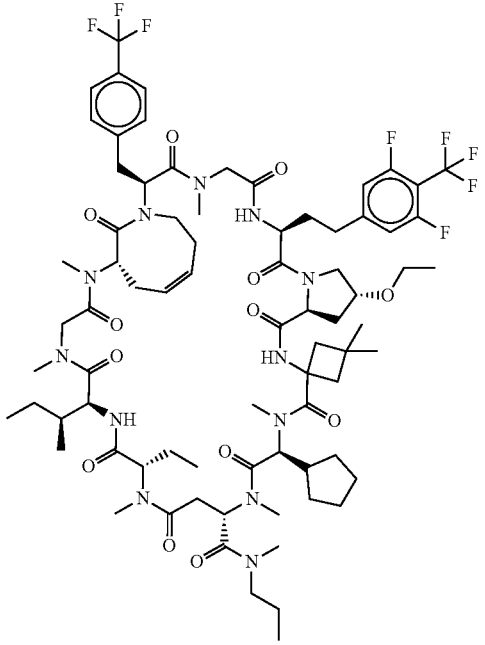 |

TABLE 38-continued
| Compound No. | Structural Formula |
|---|---|
| PP1733 | 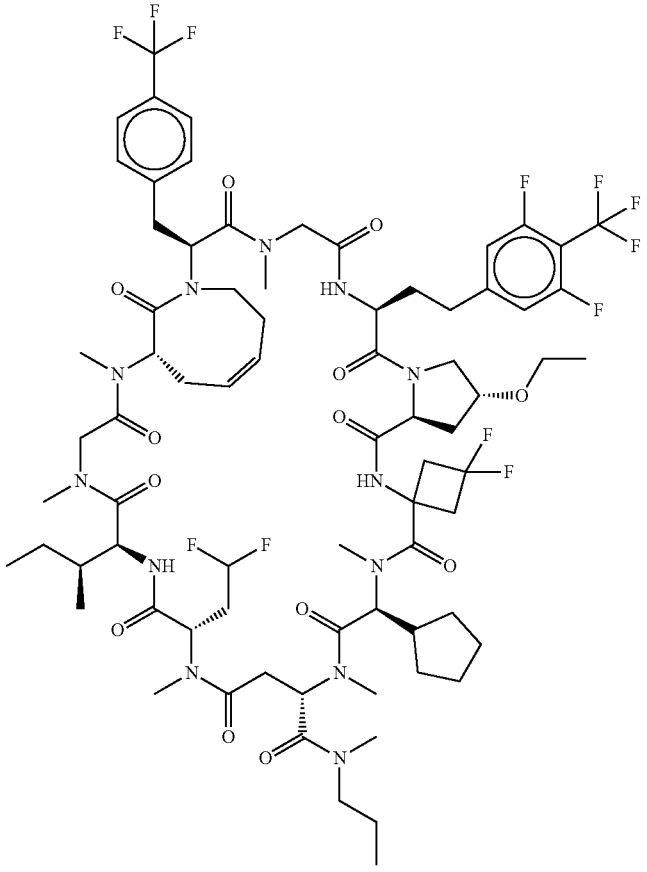 |
| PP1734 | 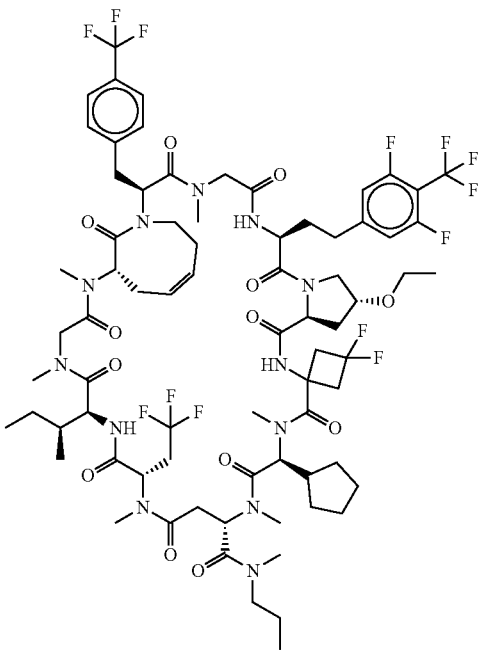 |

TABLE 38-continued
| Compound No. | Structural Formula |
|---|---|
| PP1735 | 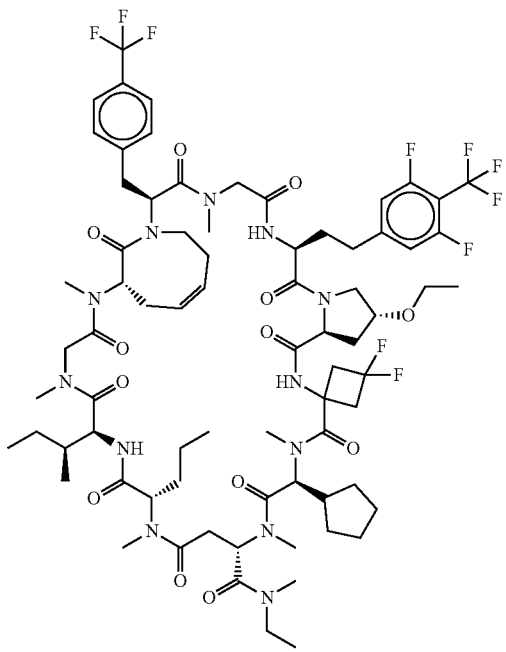 |
| PP1736 | 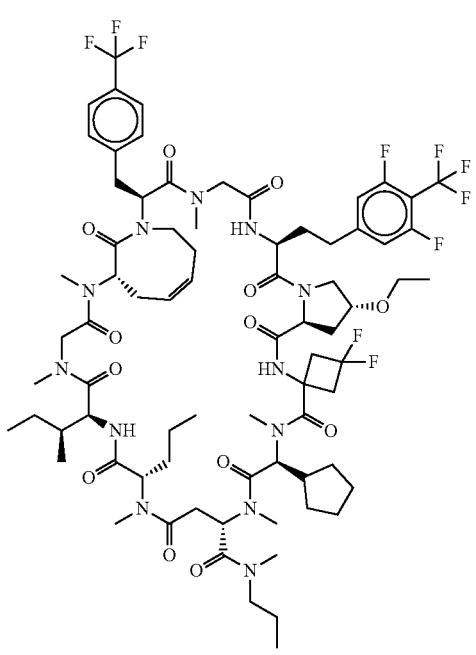 |

TABLE 38-continued

| Compound No. | Structural Formula |
|---|---|
| PP1737 | |
| PP1738 | |

TABLE 38-continued
| Compound No. | Structural Formula |
|---|---|
| PP1739 | 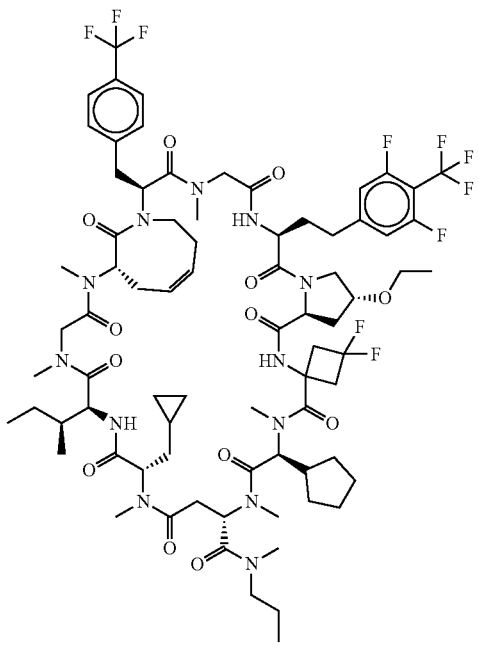 |
| PP1740 | 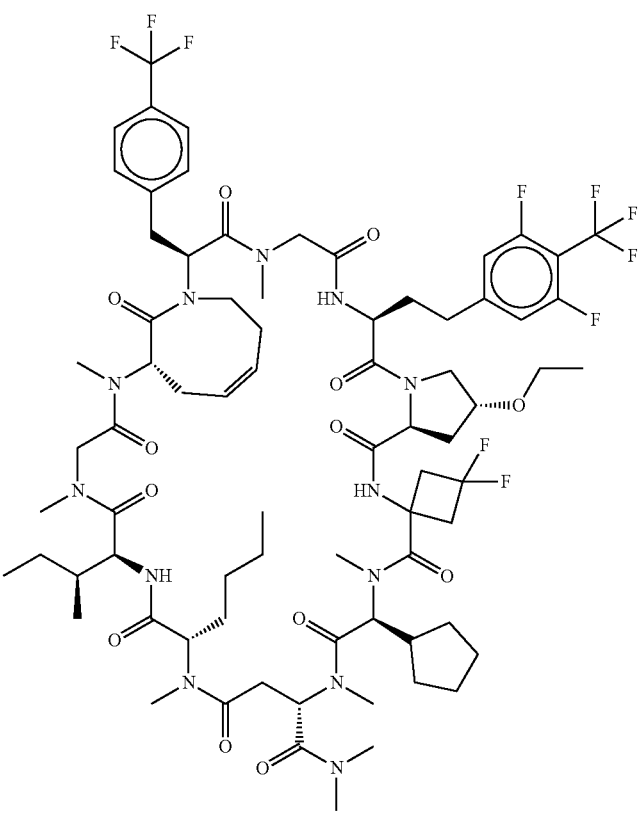 |

TABLE 38-continued
| Compound No. | Structural Formula |
|---|---|
| PP1741 | 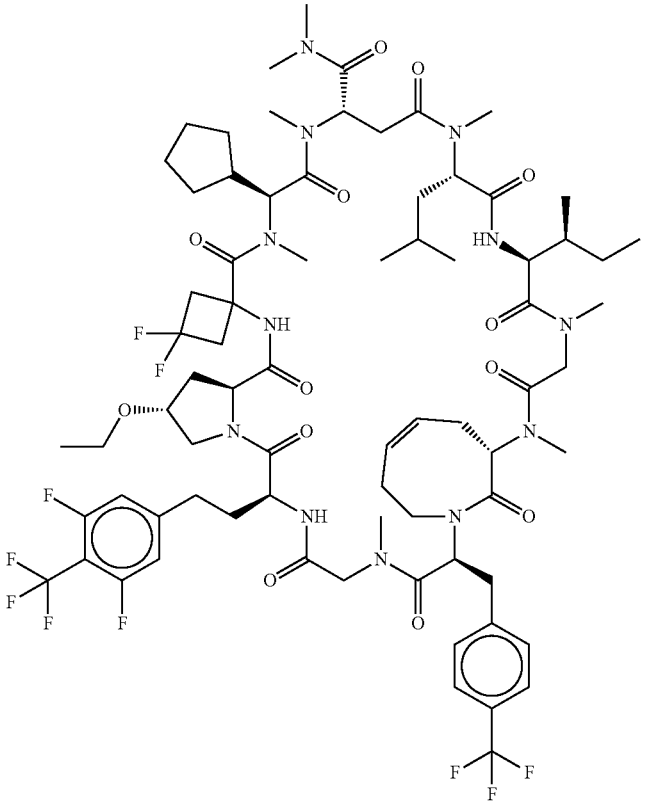 |
| PP1742 | 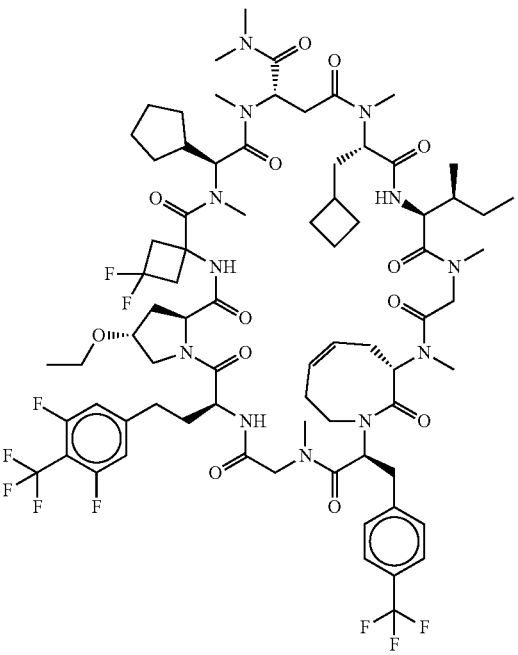 |

TABLE 38-continued
| Compound No. | Structural Formula |
|---|---|
| PP1743 | 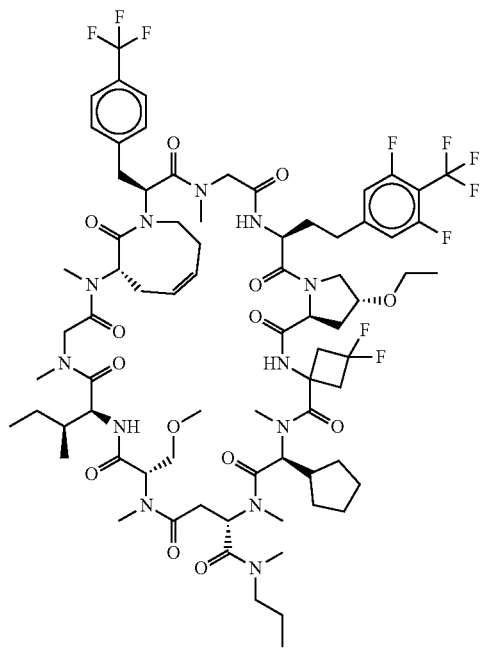 |
| PP1744 | 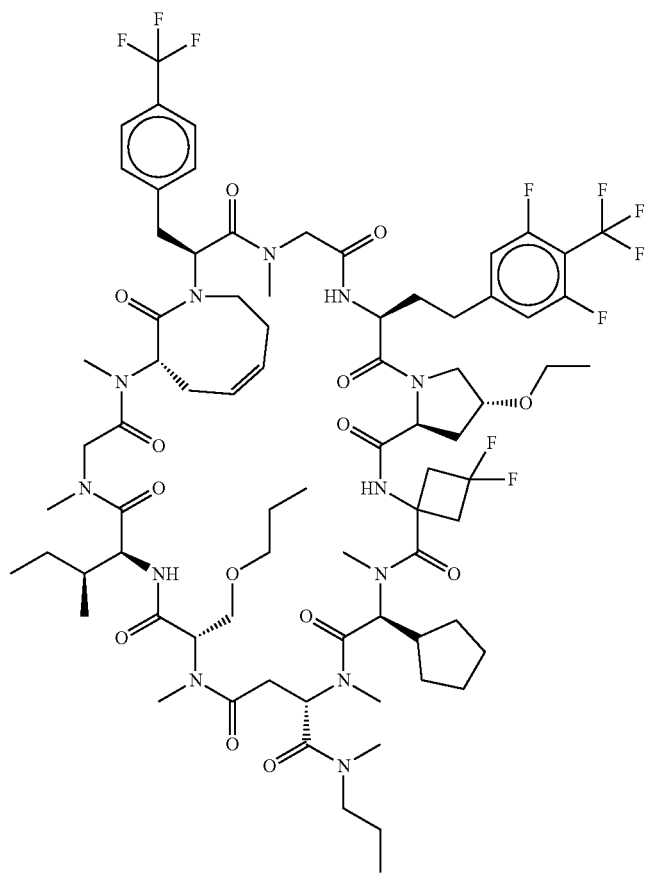 |

TABLE 38-continued
| Compound No. | Structural Formula |
|---|---|
| PP1746 | 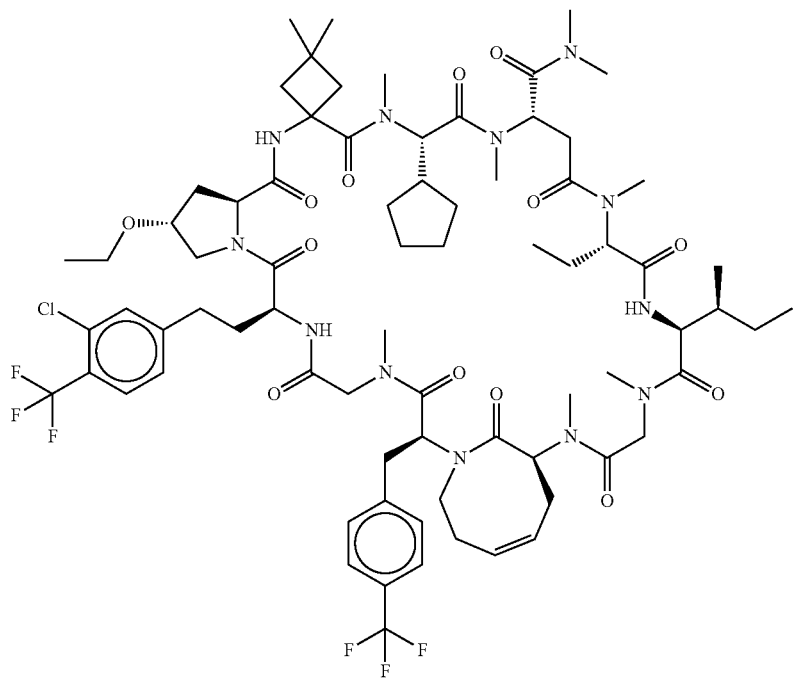 |
| PP1747 | 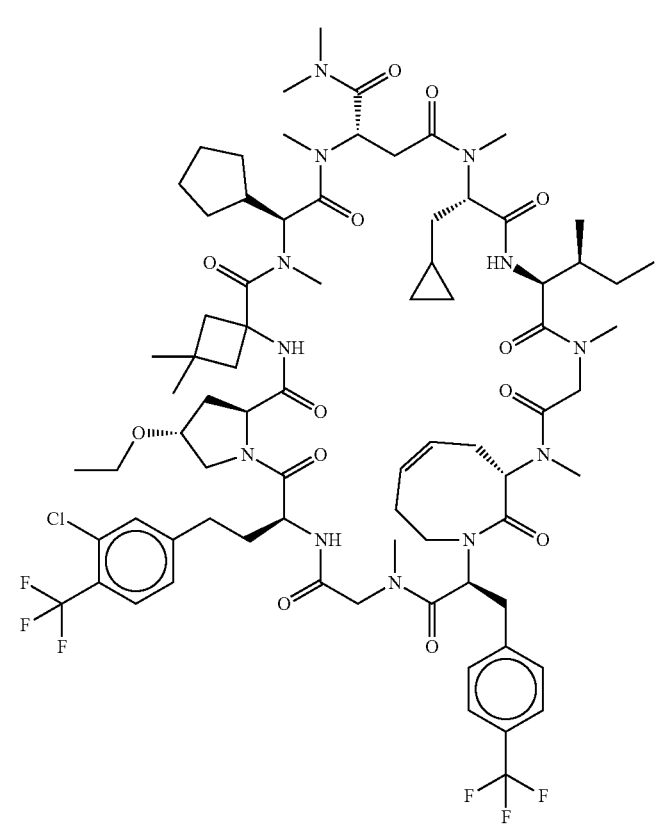 |

TABLE 38-continued
| Compound No. | Structural Formula |
|---|---|
| PP1748 | 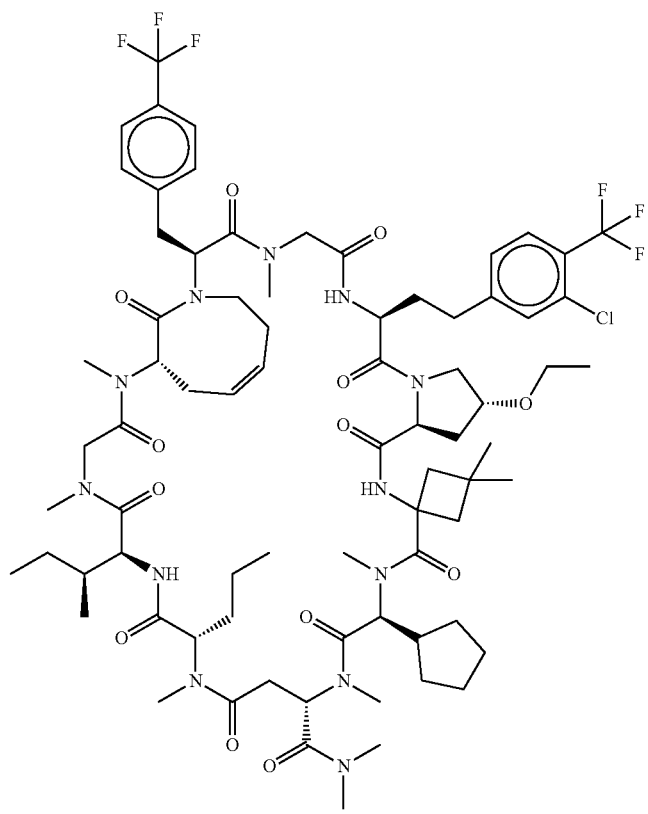 |
| PP1749 | 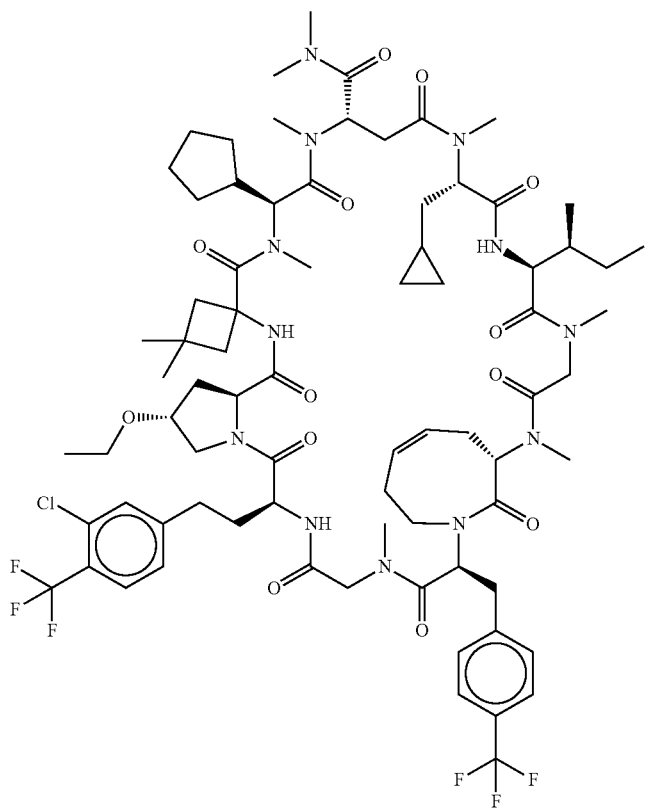 |

TABLE 38-continued
| Compound No. | Structural Formula |
|---|---|
| PP1750 | 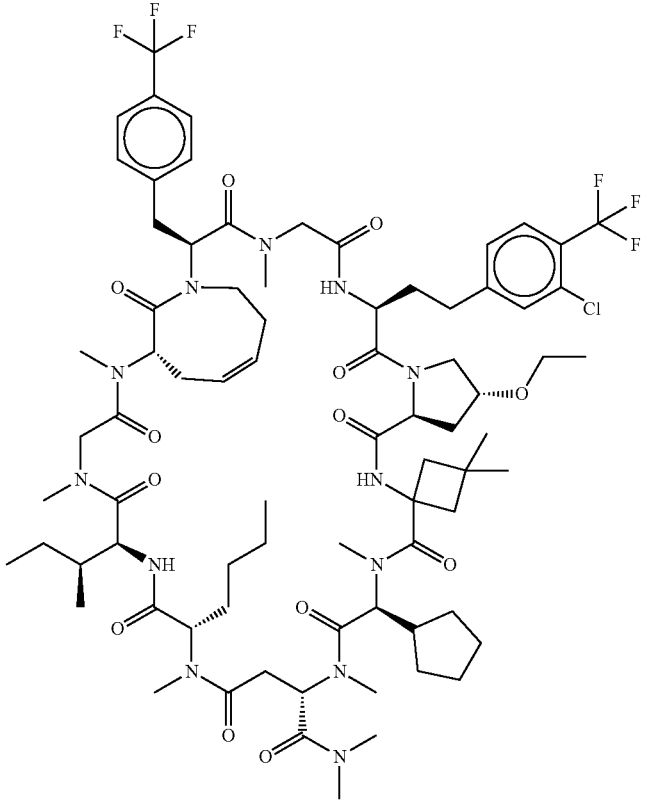 |

TABLE 38-continued
| Compound No. | Structural Formula |
|---|---|
| PP1751 | 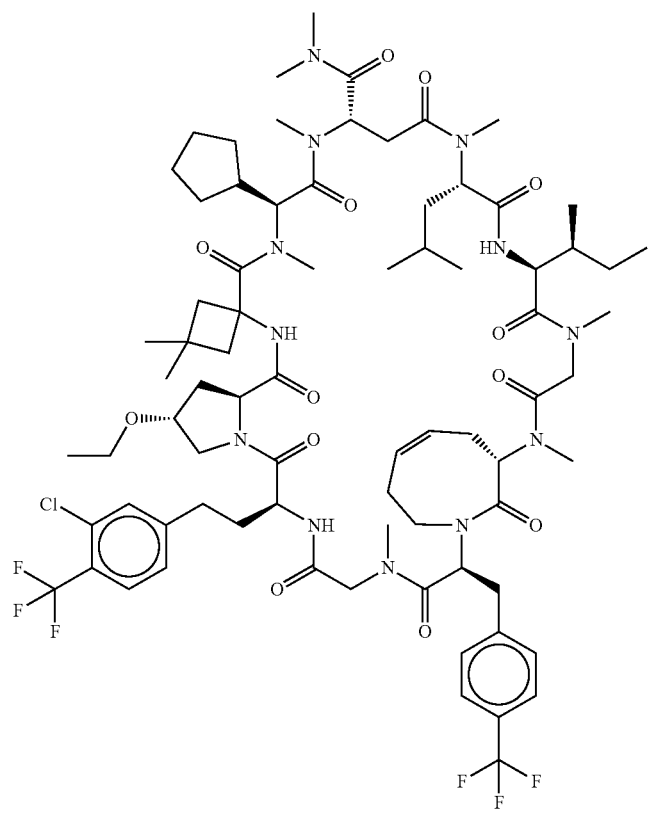 |
| PP1752 | 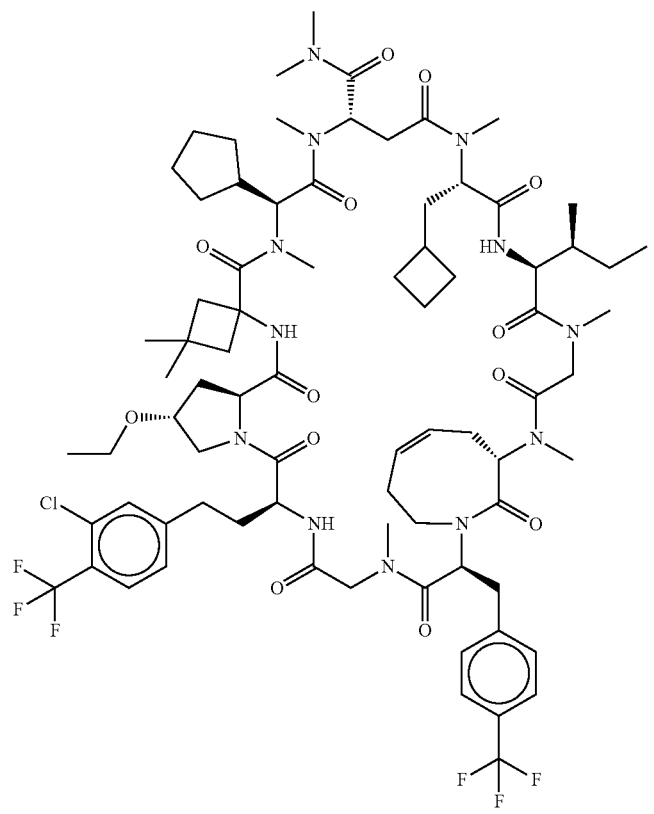 |

TABLE 38-continued
| Compound No. | Structural Formula |
|---|---|
| PP1753 | 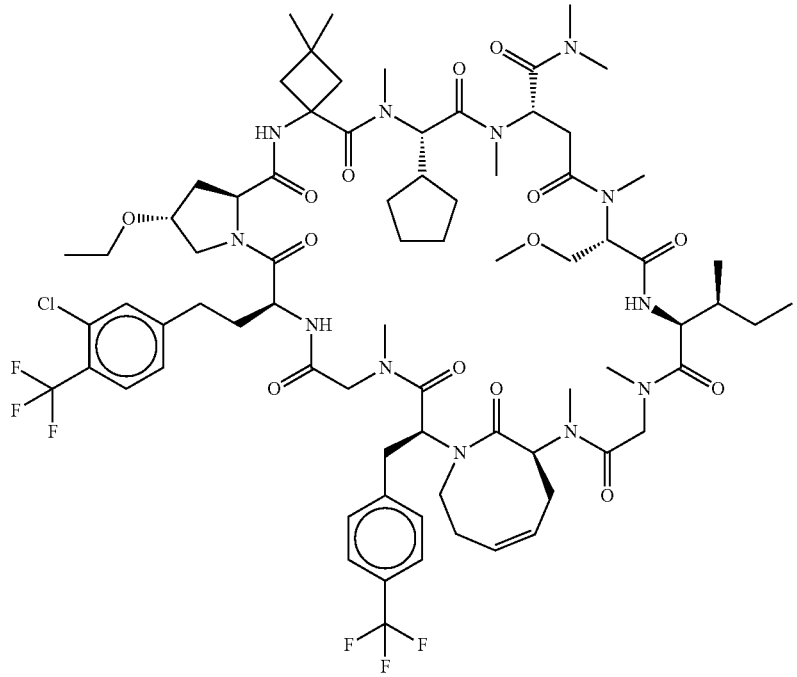 |
| PP1754 | 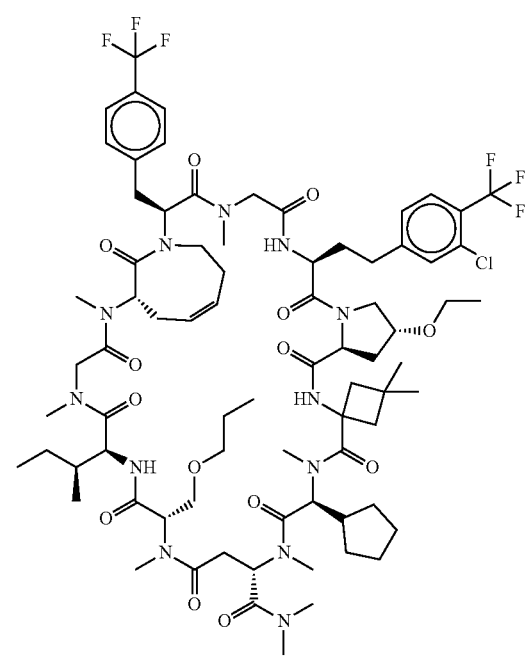 |

TABLE 38-continued
| Compound No. | Structural Formula |
|---|---|
| PP1757 | 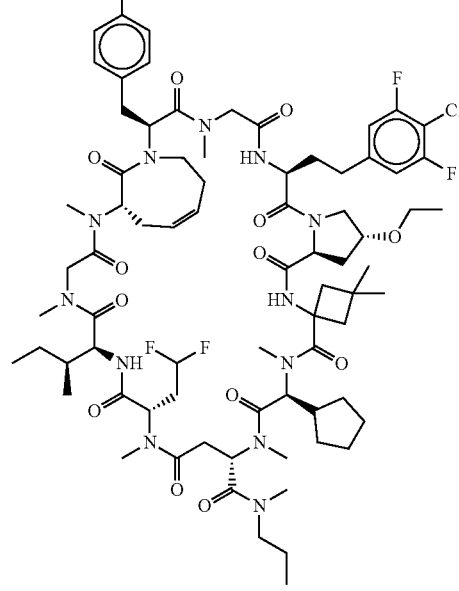 |
| PP1758 | 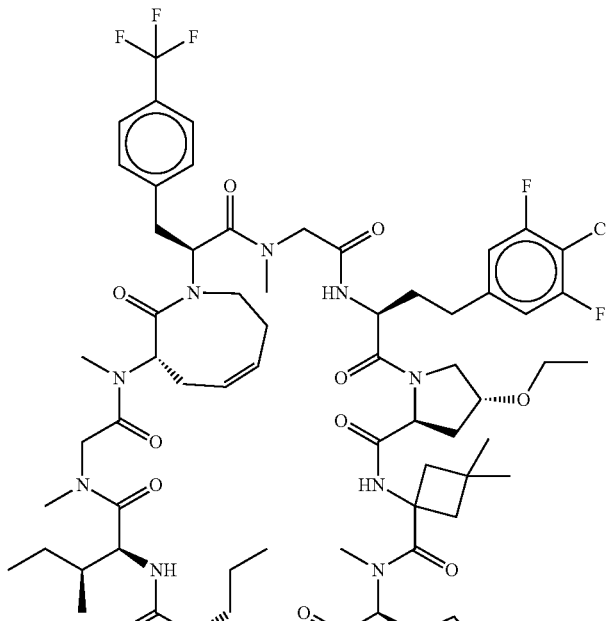 |

TABLE 38-continued

| Compound No. | Structural Formula |
|---|---|
| PP1759 | |
| PP1760 | |

TABLE 38-continued
| Compound No. | Structural Formula |
|---|---|
| PP1761 | 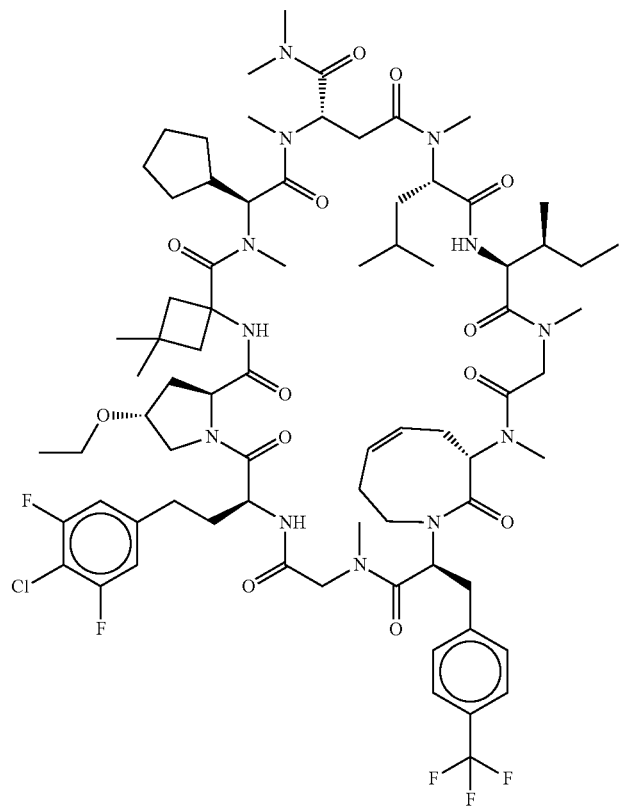 |
| PP1762 | 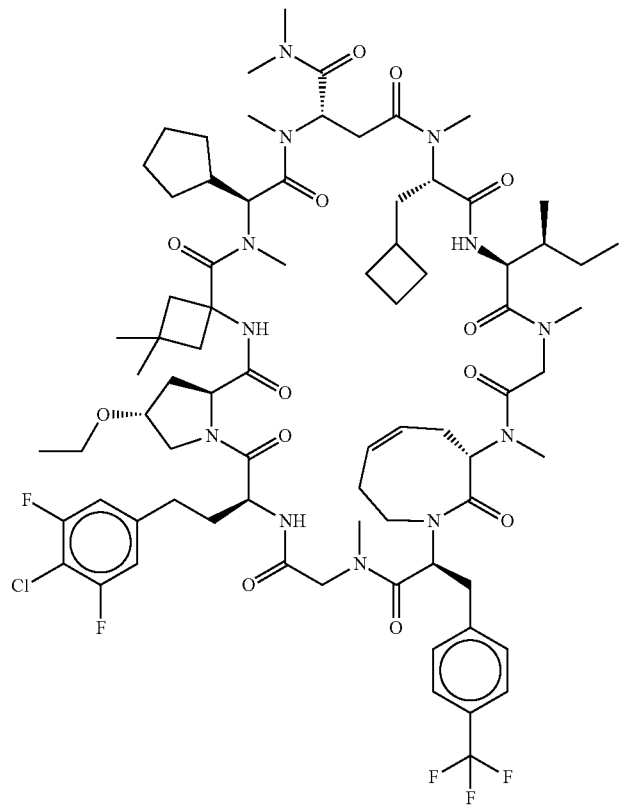 |

TABLE 38-continued
| Compound No. | Structural Formula |
|---|---|
| PP1763 | 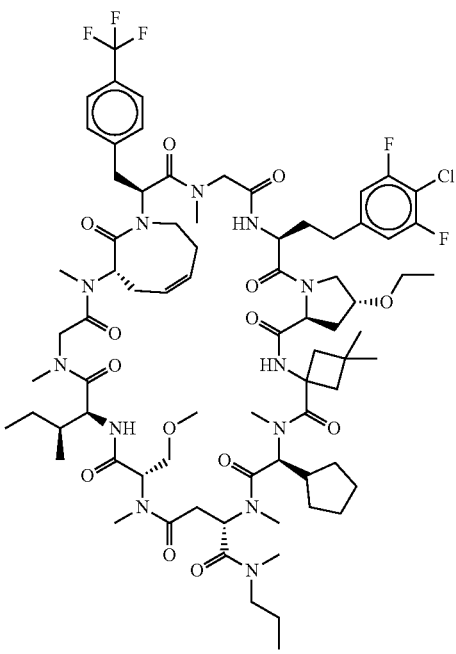 |
| PP1764 | 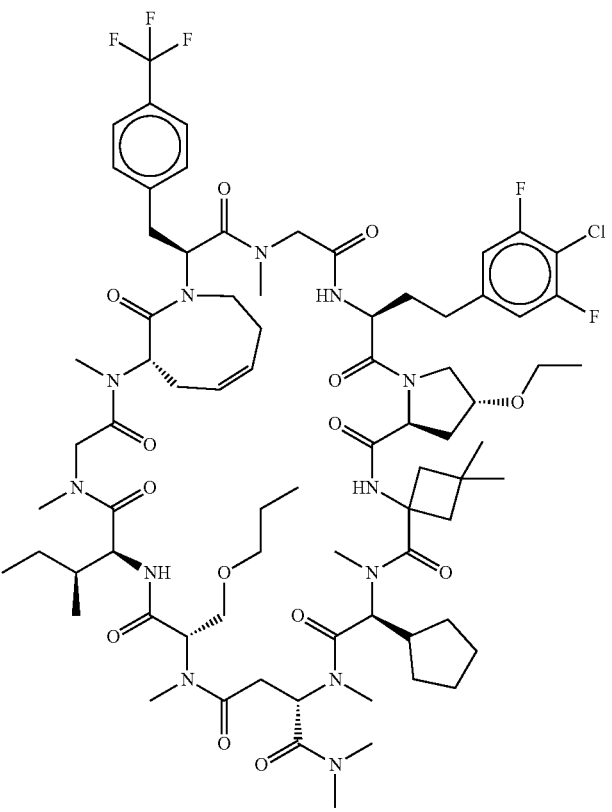 |

2531 TABLE 38-continued 2532
| Compound No. | Structural Formula |
| --- | --- |
| PP1765 | 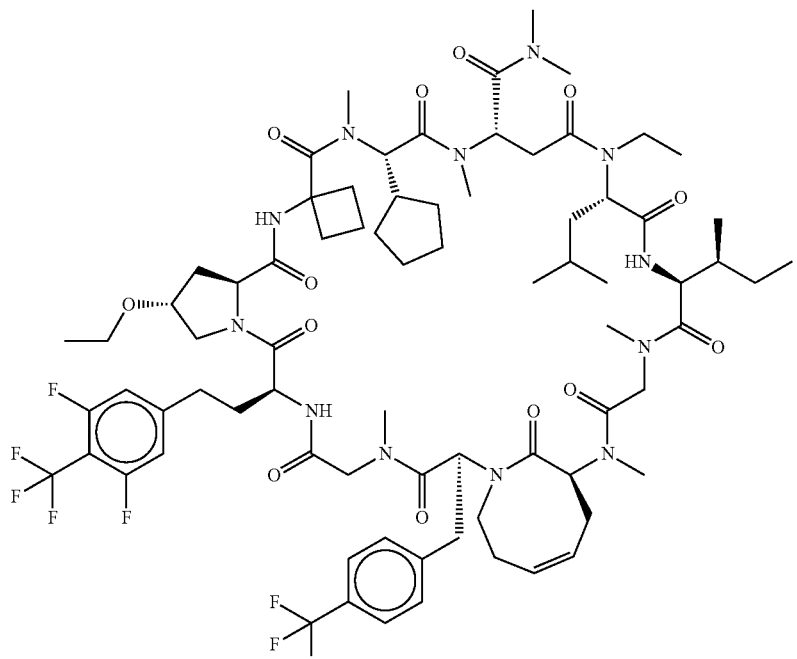 |
| PP1767 | 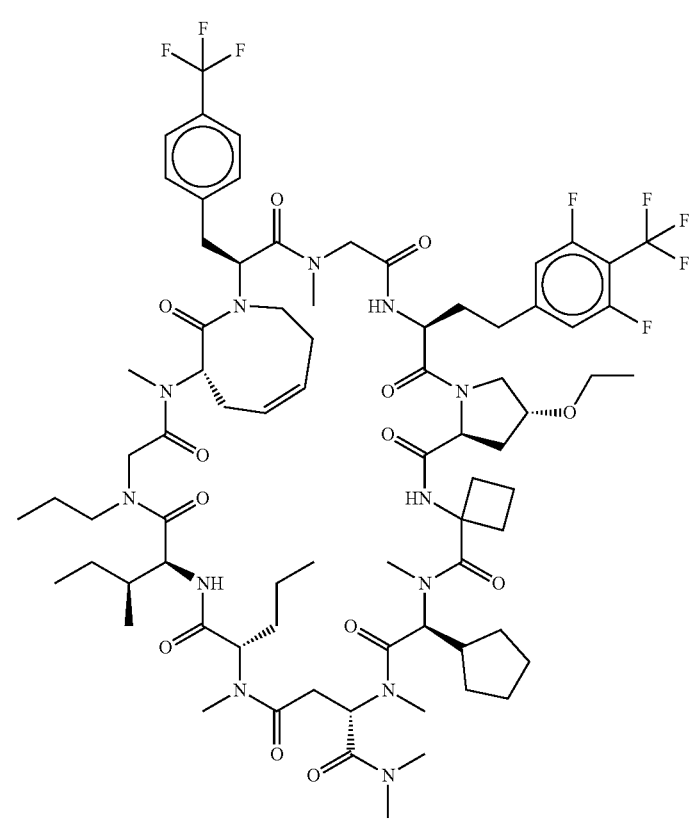 |

TABLE 38-continued
| Compound No. | Structural Formula |
|---|---|
| PP1768 | 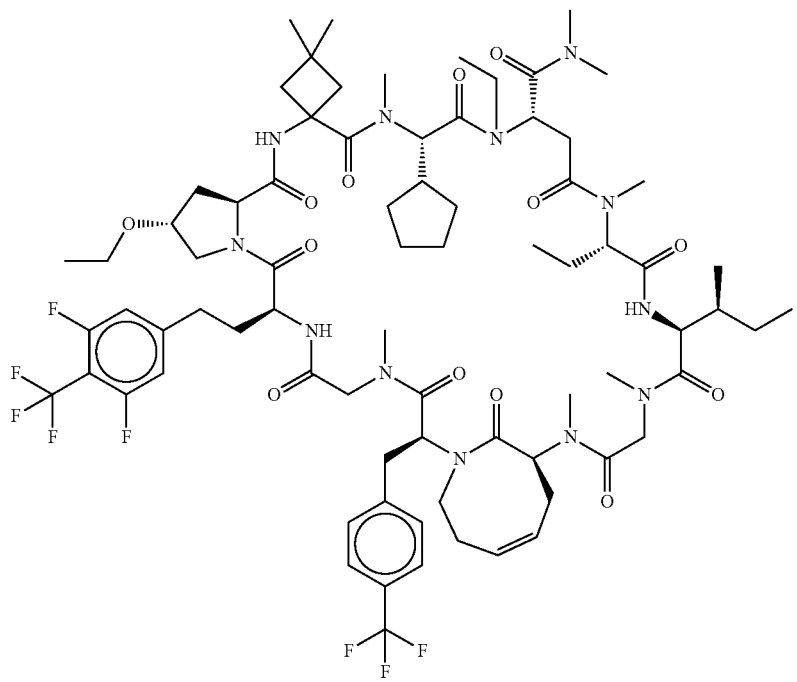 |
| PP1769 | 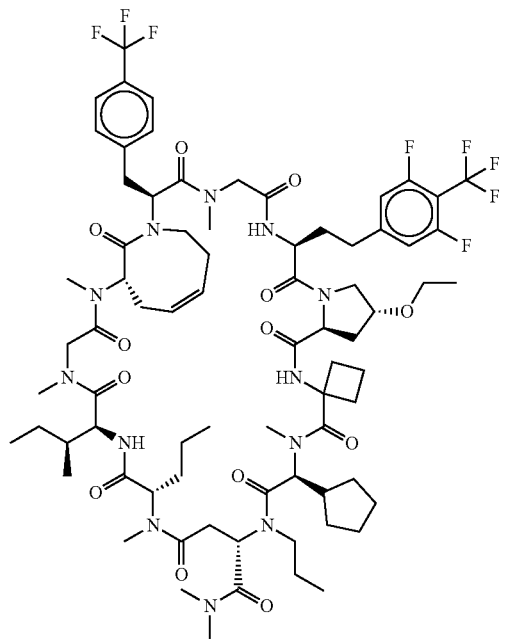 |

TABLE 38-continued
| Compound No. | Structural Formula |
|---|---|
| PP1771 | 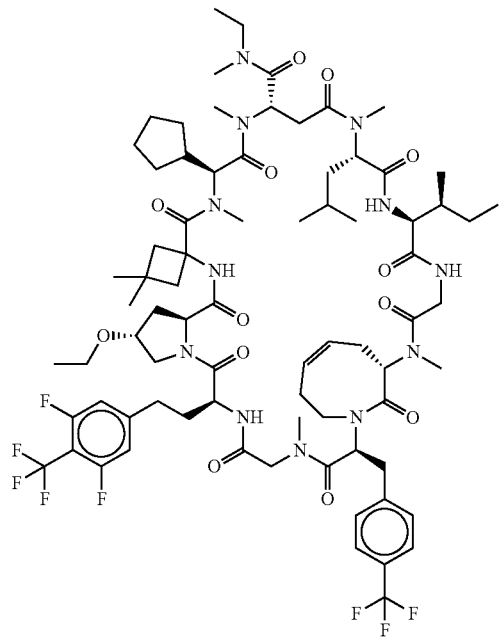 |
| PP1772 | 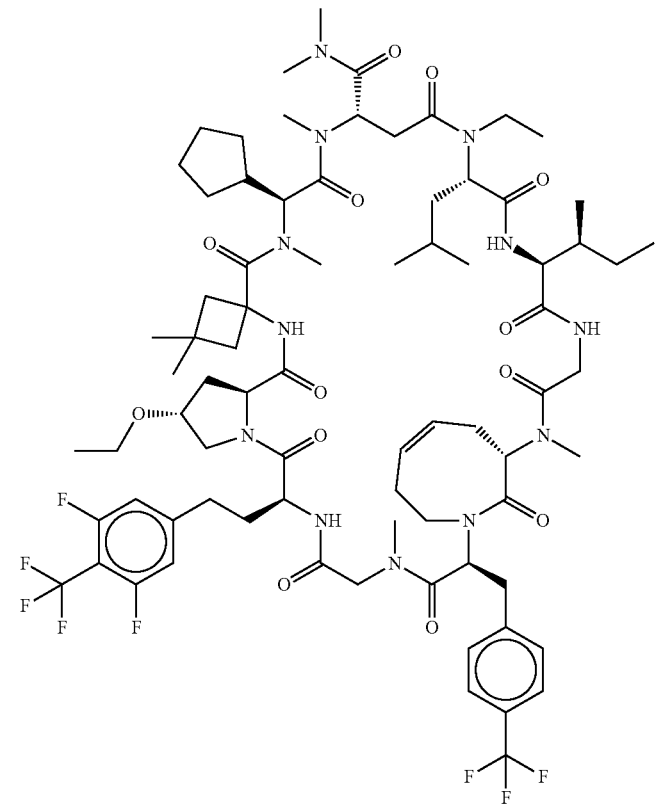 |

TABLE 38-continued
| Compound No. | Structural Formula |
|---|---|
| PP1773 | 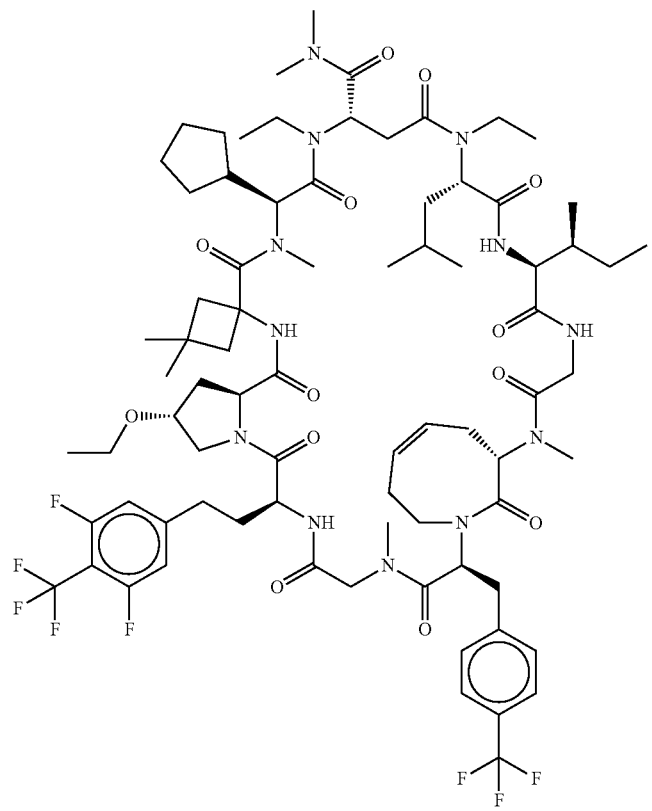 |
| PP1775 | 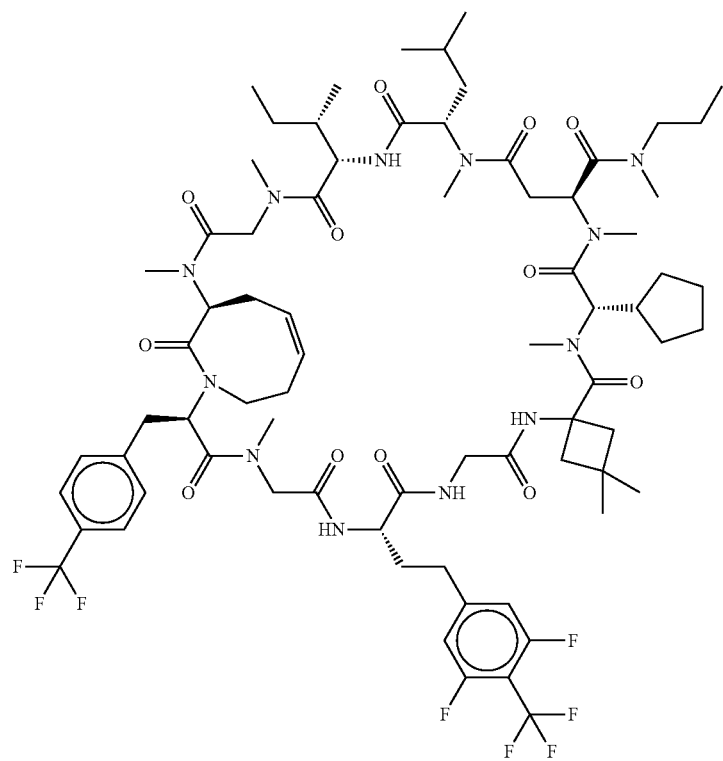 |

TABLE 38-continued
| Compound No. | Structural Formula |
|---|---|
| PP1776 | 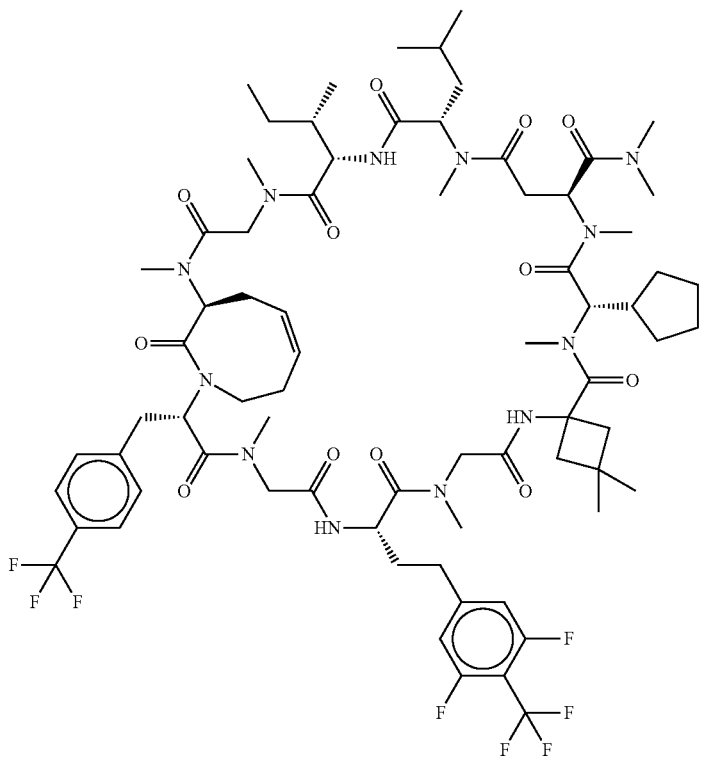 |
| PP1777 | 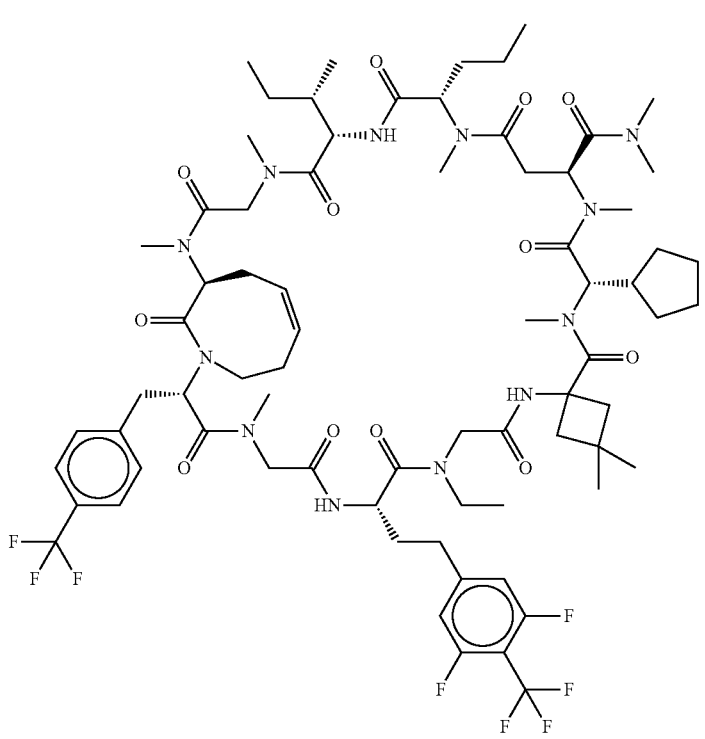 |

TABLE 38-continued

| Compound No. | Structural Formula |
|---|---|
| PP1779 | | ns
TABLE 38-continued
| Compound No. | Structural Formula |
|---|---|
| PP1780 | 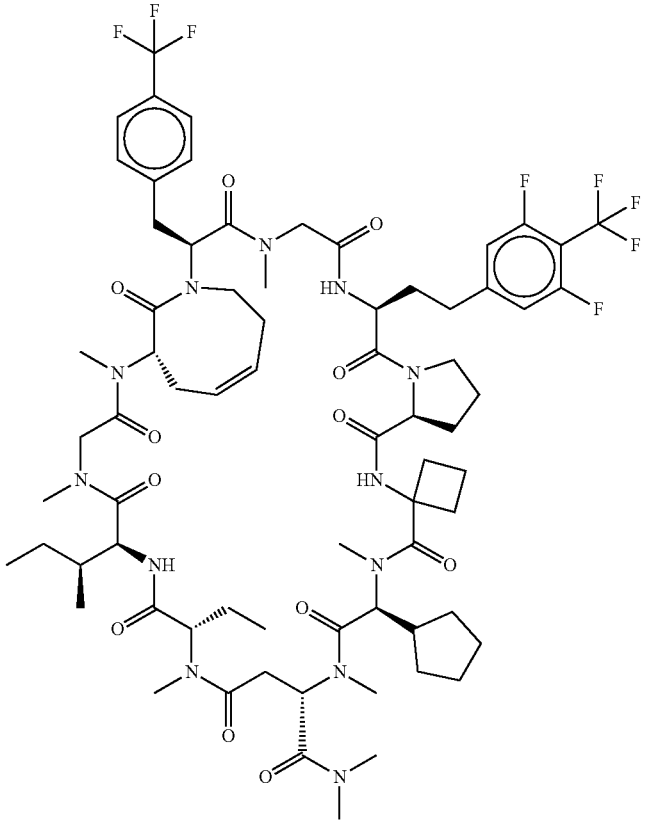 |
| PP1781 | 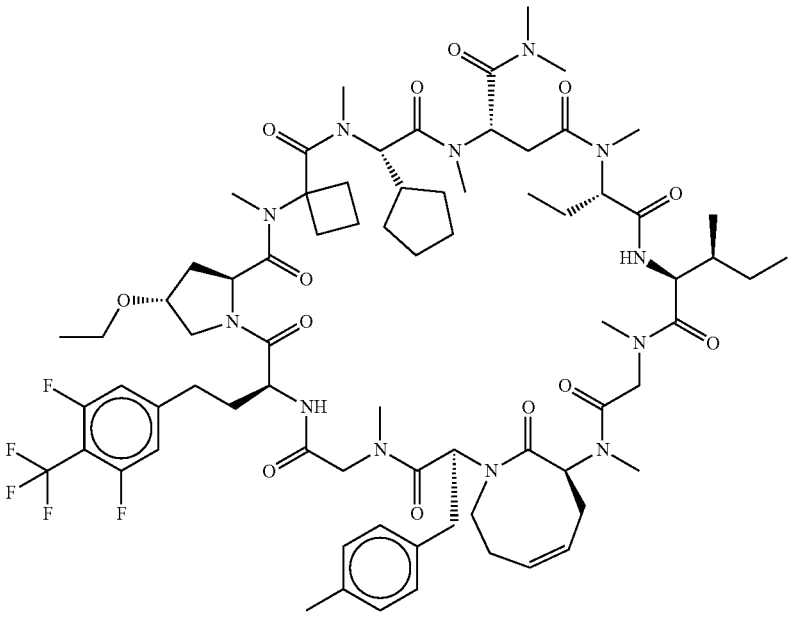 |

TABLE 38-continued

| Compound No. | Structural Formula |
|---|---|
| PP1782 | |
| PP1783 | |

TABLE 38-continued
| Compound No. | Structural Formula |
|---|---|
| PP1784 | 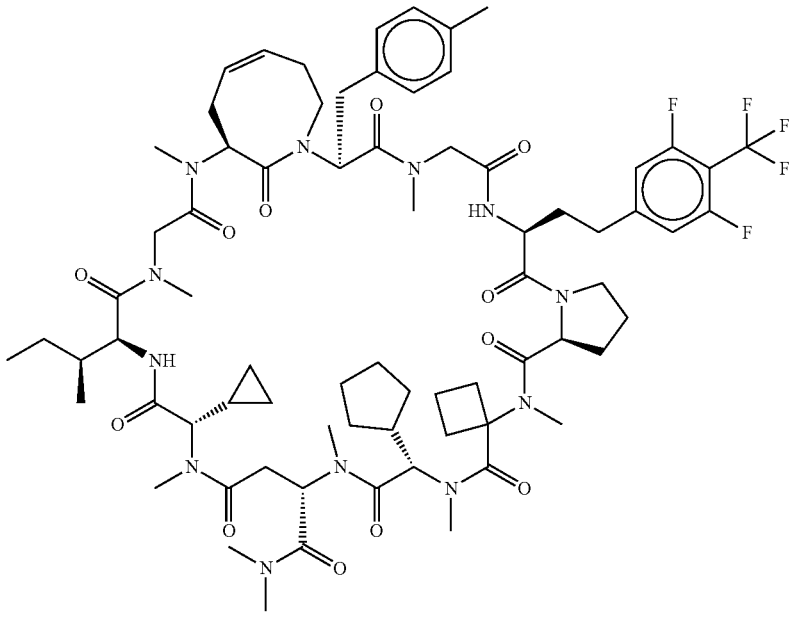 |
| PP1785 | 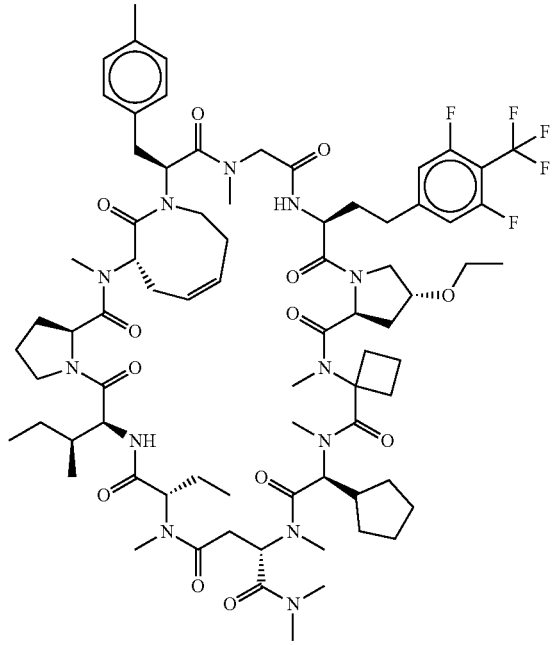 |

TABLE 38-continued

| Compound No. | Structural Formula |
|---|---|
| PP1786 | |
| PP1787 | |

TABLE 38-continued

| Compound No. | Structural Formula |
|---|---|
| PP1788 | |
| PP1789 | |

TABLE 38-continued
| Compound No. | Structural Formula |
| --- | --- |
| PP1790 | 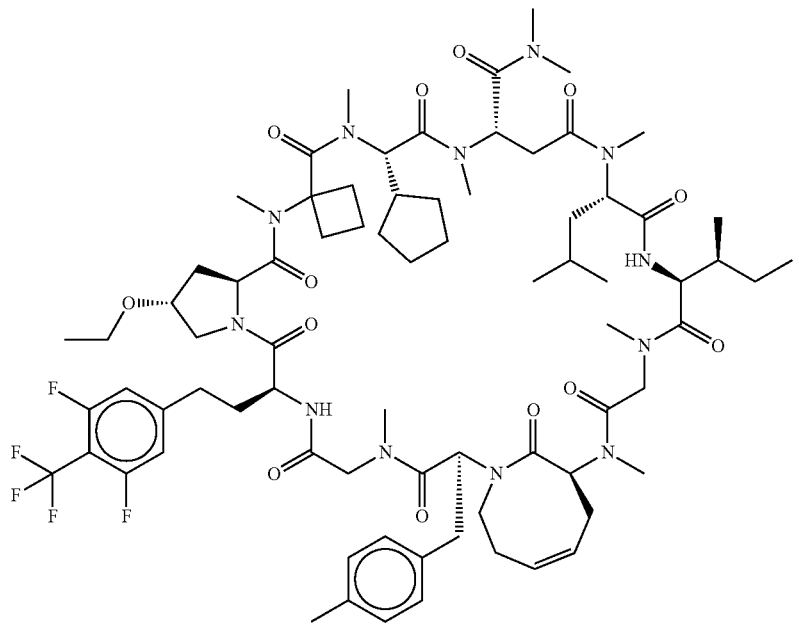 |
| PP1791 | 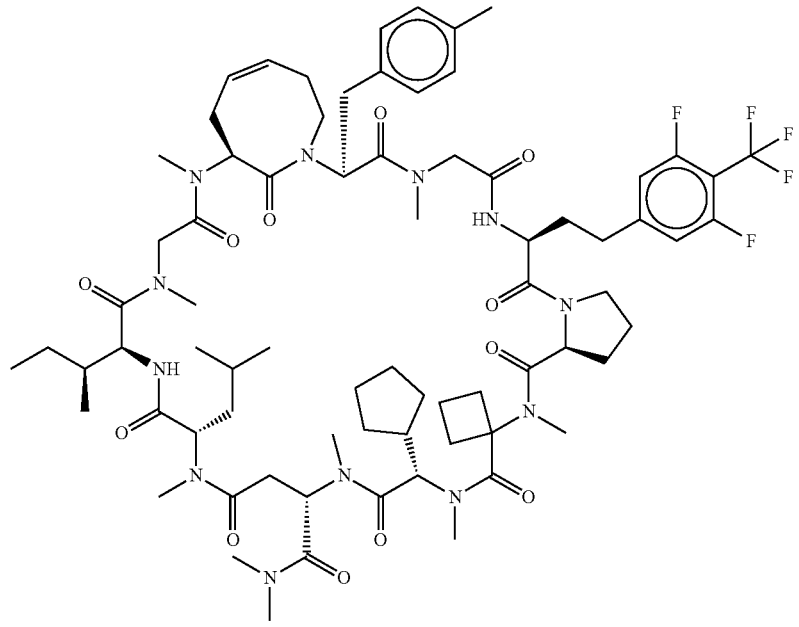 |

TABLE 38-continued

| Compound No. | Structural Formula |
|---|---|
| PP1792 | |
| PP1793 | |

| Compound No. | Structural Formula |
|---|---|
| PP1794 | 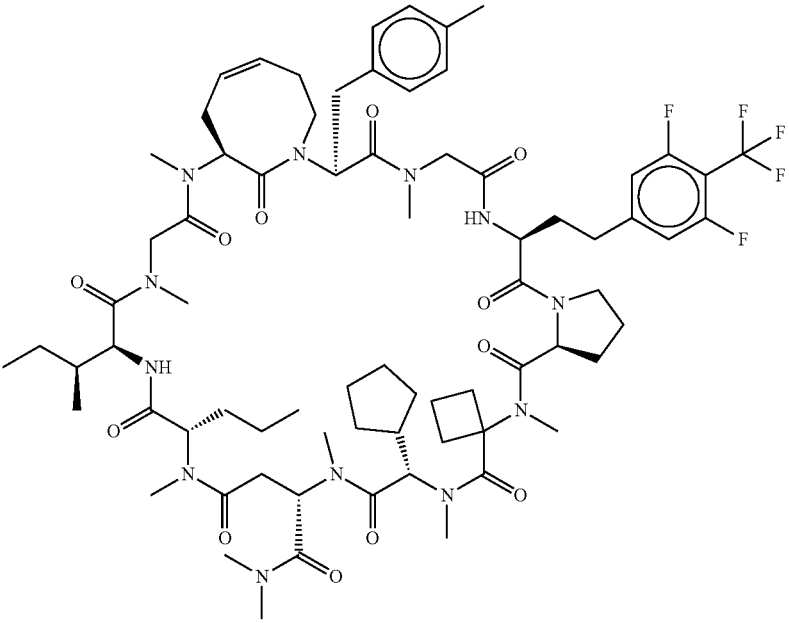 |
| PP1795 | 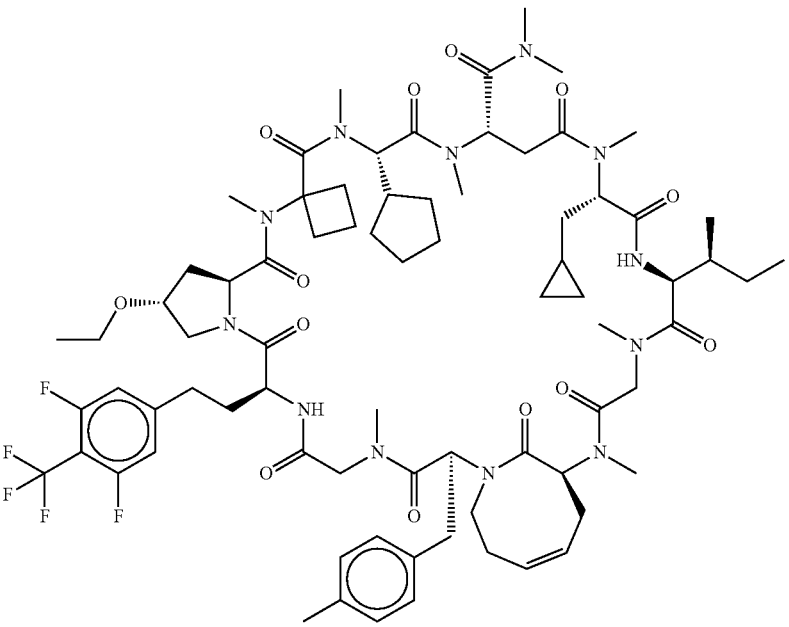 |

TABLE 38-continued

| Compound No. | Structural Formula |
|---|---|
| PP1796 | |
| PP1797 | |

TABLE 38-continued

| Compound No. | Structural Formula |
| --- | --- |
| PP1798 | |
| PP1799 | |

TABLE 38-continued

| Compound No. | Structural Formula |
|---|---|
| PP1800 | |
| PP1801 | |

TABLE 38-continued

| Compound No. | Structural Formula |
|---|---|
| PP1802 | |
| PP1803 | |

2567
TABLE 38-continued
| Compound No. | Structural Formula |
| --- | --- |
| PP1804 | 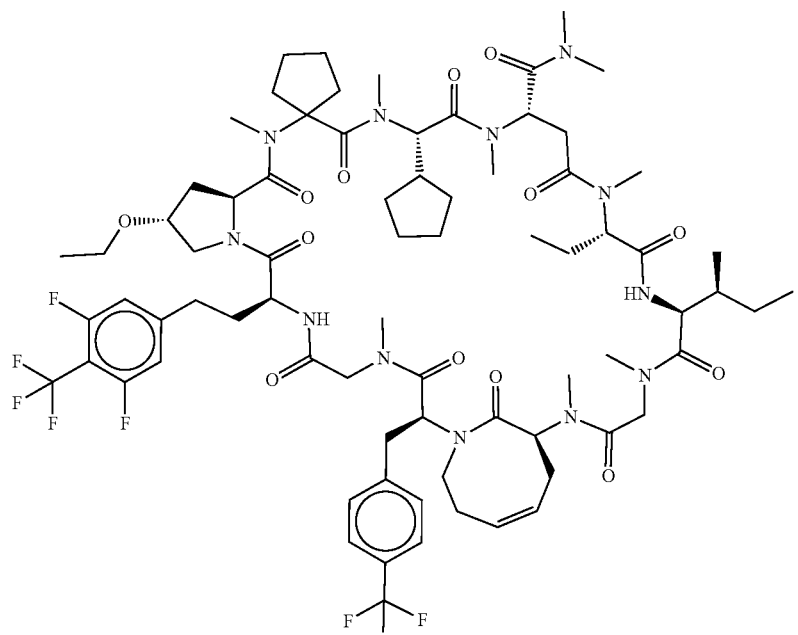 |
| PP1805 | 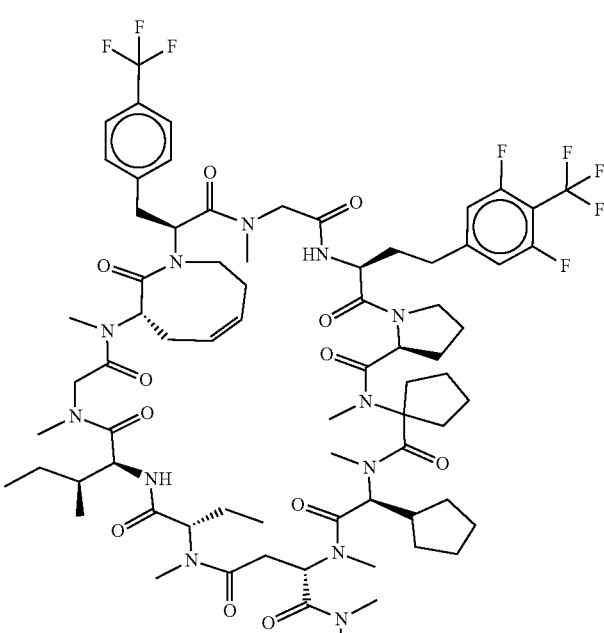 |

TABLE 38-continued

| Compound No. | Structural Formula |
|---|---|
| PP1806 | |
| PP1807 | |

TABLE 38-continued

| Compound No. | Structural Formula |
|---|---|
| PP1808 | |
| PP1809 | |

TABLE 38-continued

| Compound No. | Structural Formula |
|---|---|
| PP1810 | |
| PP1811 | |

TABLE 38-continued

| Compound No. | Structural Formula |
|---|---|
| PP1812 | |
| PP1813 | |

TABLE 38-continued

| Compound No. | Structural Formula |
|---|---|
| PP1814 | |
| PP1815 | |

TABLE 38-continued
| Compound No. | Structural Formula |
|---|---|
| PP1816 | 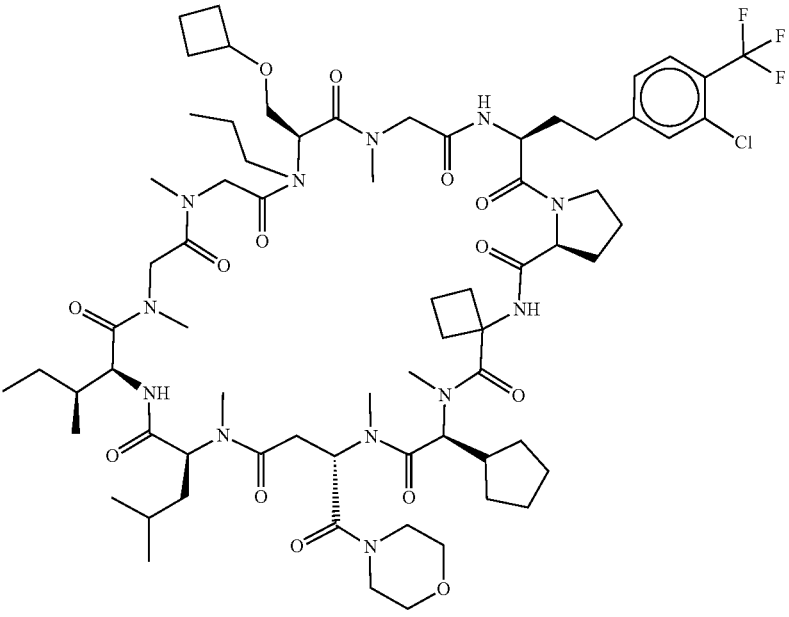 |
| PP1817 | 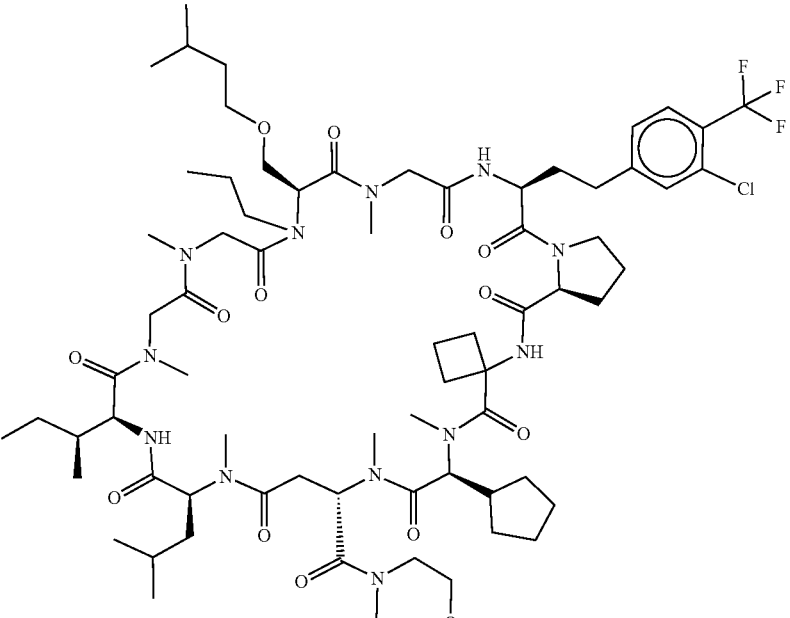 |

TABLE 38-continued

| Compound No. | Structural Formula |
|---|---|
| PP1818 | |
| PP1819 | |

TABLE 38-continued

| Compound No. | Structural Formula |
|---|---|
| PP1820 | |
| PP1821 | |

TABLE 38-continued

| Compound No. | Structural Formula |
|---|---|
| PP1822 | |
| PP1823 | |

TABLE 38-continued

| Compound No. | Structural Formula |
|---|---|
| PP1824 | |
| PP1825 | |

TABLE 38-continued

| Compound No. | Structural Formula |
|---|---|
| PP1826 | |
| PP1827 | |

TABLE 38-continued
| Compound No. | Structural Formula |
|---|---|
| PP1828 | 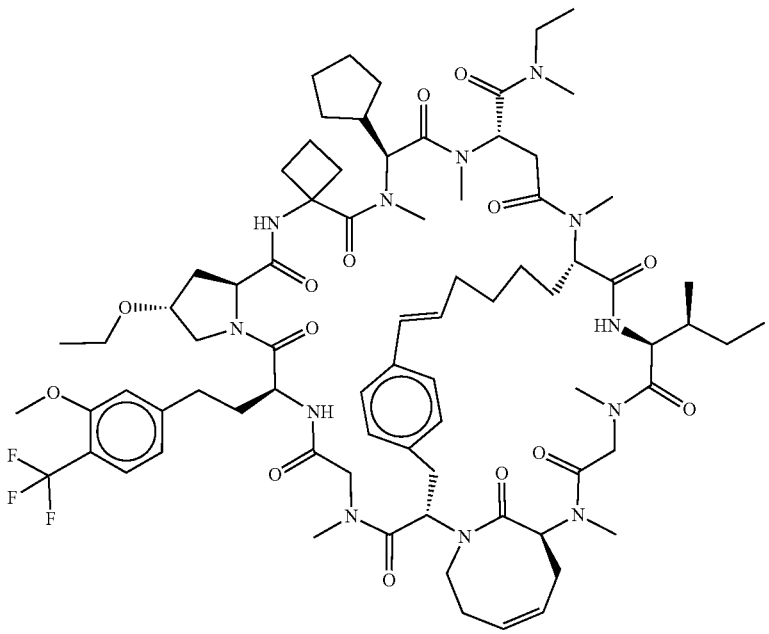 |
| PP1829 | 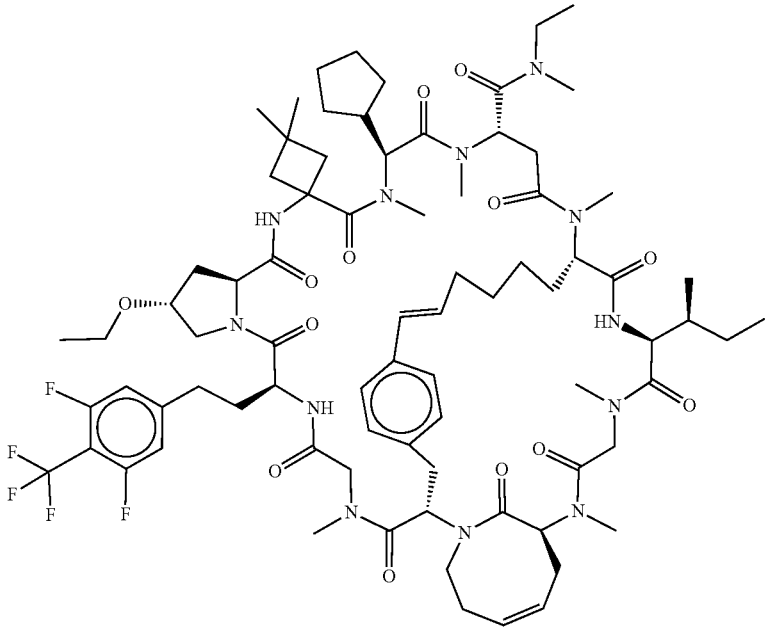 |

TABLE 38-continued
| Compound No. | Structural Formula |
|---|---|
| PP1830 | 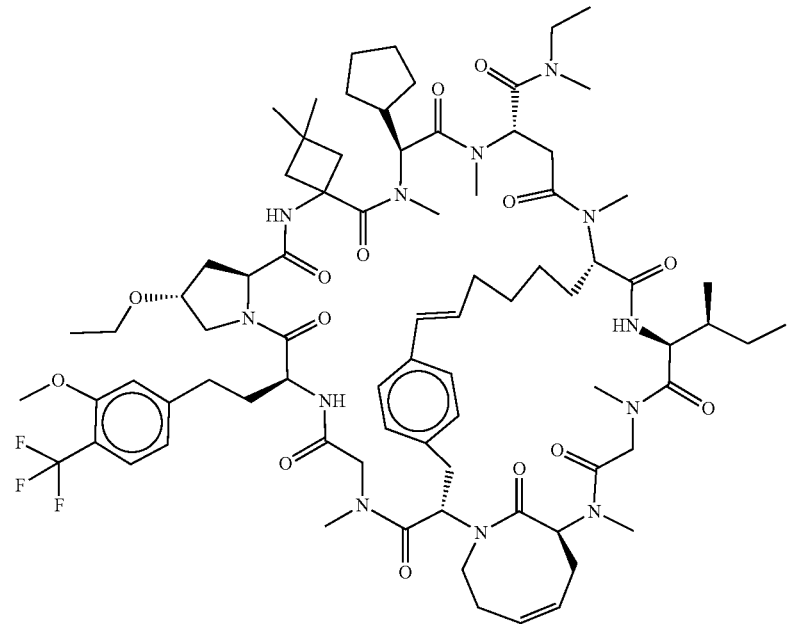 |
| PP1831 | 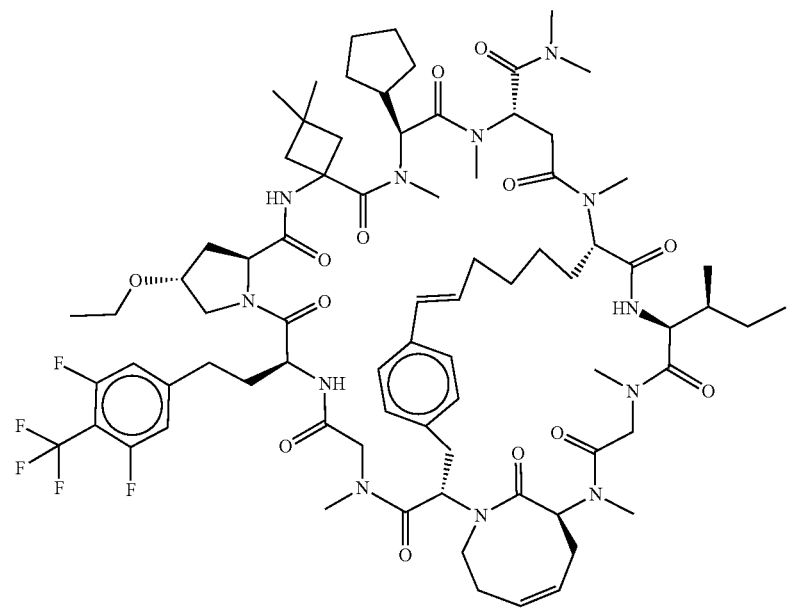 |

TABLE 38-continued
| Compound No. | Structural Formula |
|---|---|
| PP1832 | 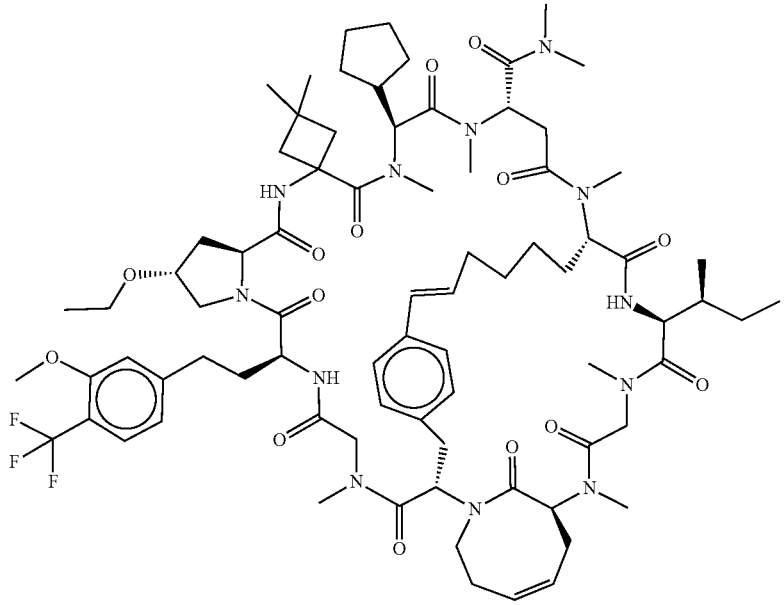 |
| PP1833 | 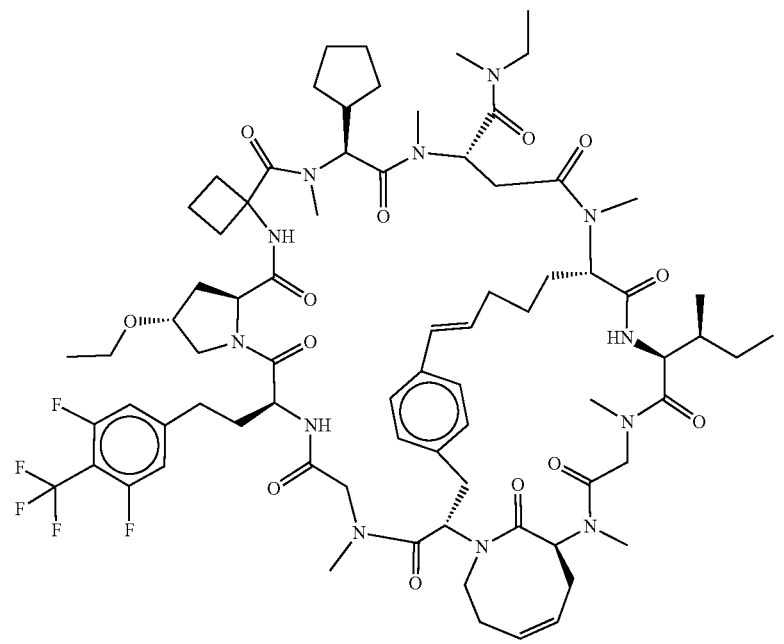 |

TABLE 38-continued

| Compound No. | Structural Formula |
| --- | --- |
| PP1834 | |
| PP1835 | |

TABLE 38-continued

| Compound No. | Structural Formula |
|---|---|
| PP1836 | |
| PP1837 | |

TABLE 38-continued

| Compound No. | Structural Formula |
|---|---|
| PP1838 | |
| PP1839 | |

TABLE 38-continued

| Compound No. | Structural Formula |
|---|---|
| PP1840 | |
| PP1841 | |

TABLE 38-continued

| Compound No. | Structural Formula |
|---|---|
| PP1842 | |
| PP1844 | |

TABLE 38-continued

| Compound No. | Structural Formula |
|---|---|
| PP1846 | |
| PP1848 | |

TABLE 38-continued

| Compound No. | Structural Formula |
|---|---|
| PP1849 | |
| PP1850 | |

TABLE 38-continued

| Compound No. | Structural Formula |
|---|---|
| PP1851 | |
| PP1852 | |

TABLE 38-continued

| Compound No. | Structural Formula |
|---|---|
| PP1853 | |
| PP1854 | |

TABLE 38-continued

| Compound No. | Structural Formula |
|---|---|
| PP1855 | |
| PP1856 | |

TABLE 38-continued
| Compound No. | Structural Formula |
|---|---|
| PP1857 | 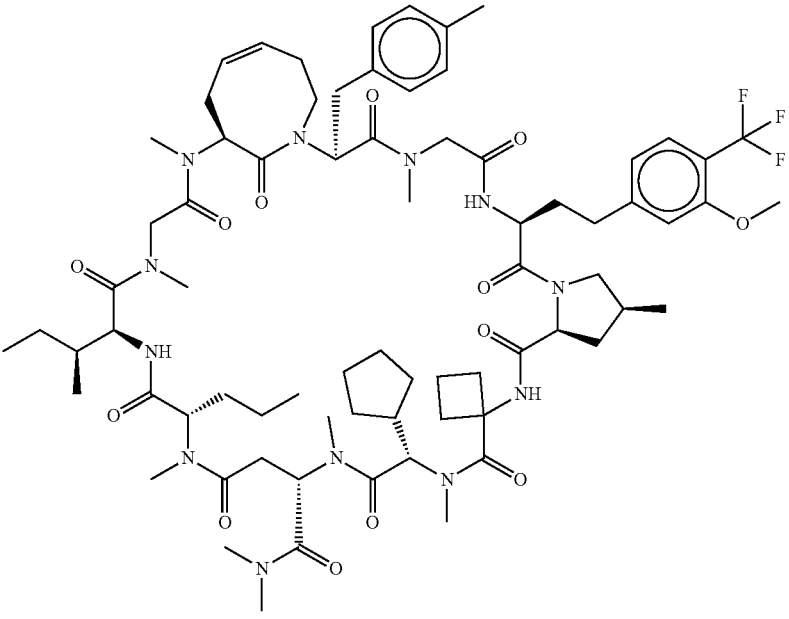 |
| PP1859 | 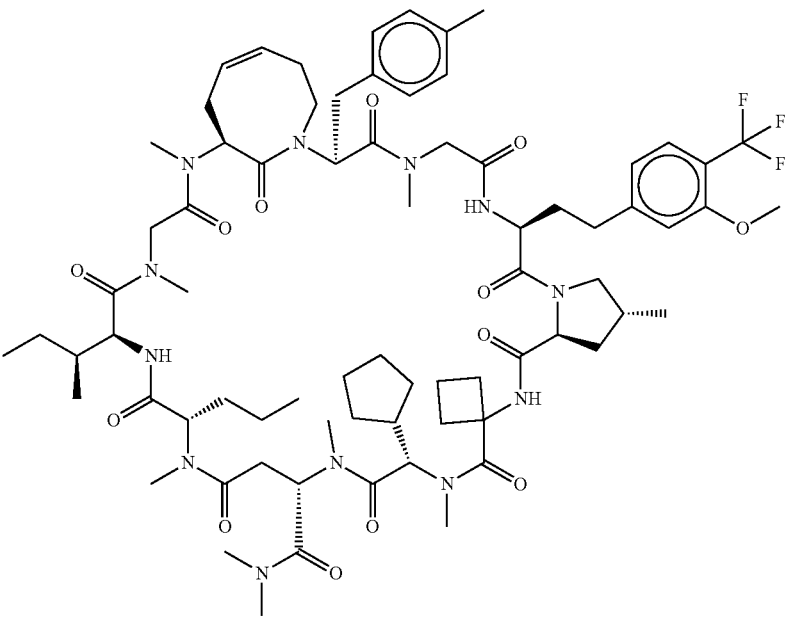 |

TABLE 38-continued
| Compound No. | Structural Formula |
|---|---|
| PP1860 | 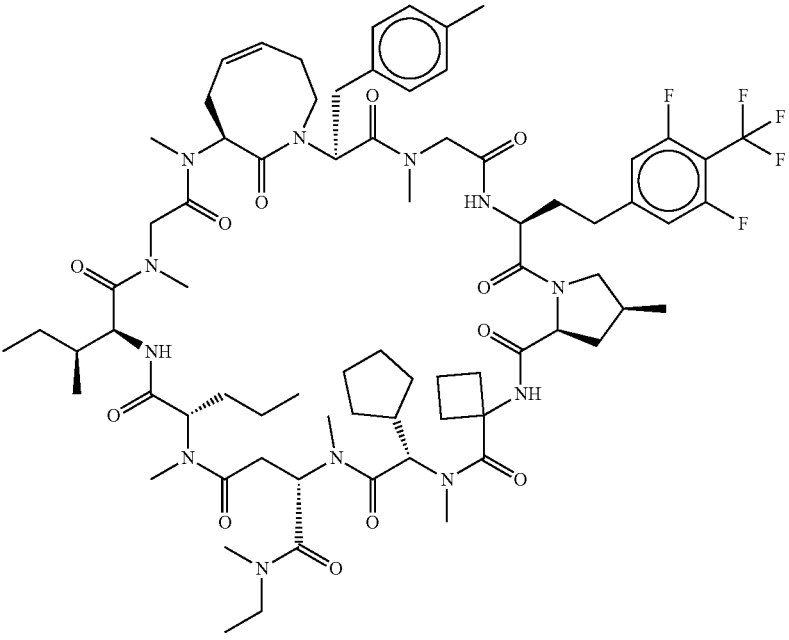 |
| PP1861 | 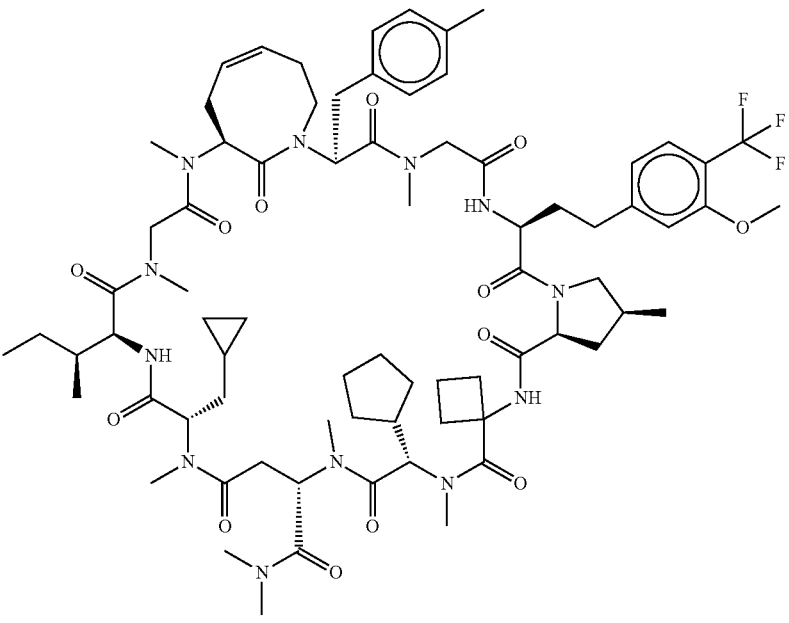 |

TABLE 38-continued

| Compound No. | Structural Formula |
|---|---|
| PP1862 | |
| PP1863 | |

TABLE 38-continued

| Compound No. | Structural Formula |
|---|---|
| PP1864 | |
| PP1865 | |

TABLE 38-continued

| Compound No. | Structural Formula |
|---|---|
| PP1866 | |
| PP1867 | |

TABLE 38-continued
| Compound No. | Structural Formula |
|---|---|
| PP1868 | 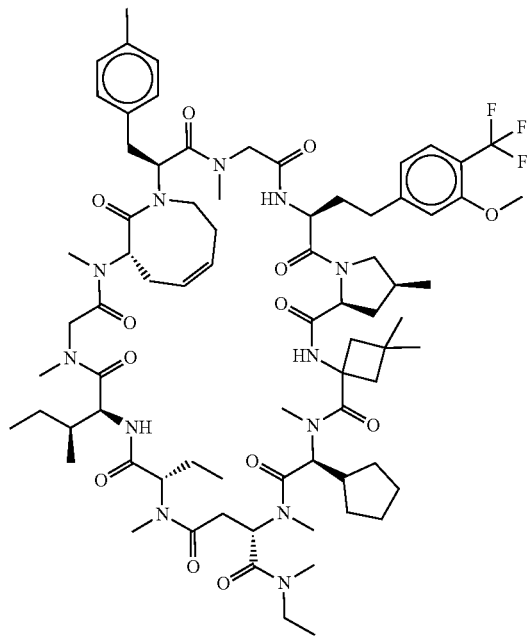 |
| PP1869 | 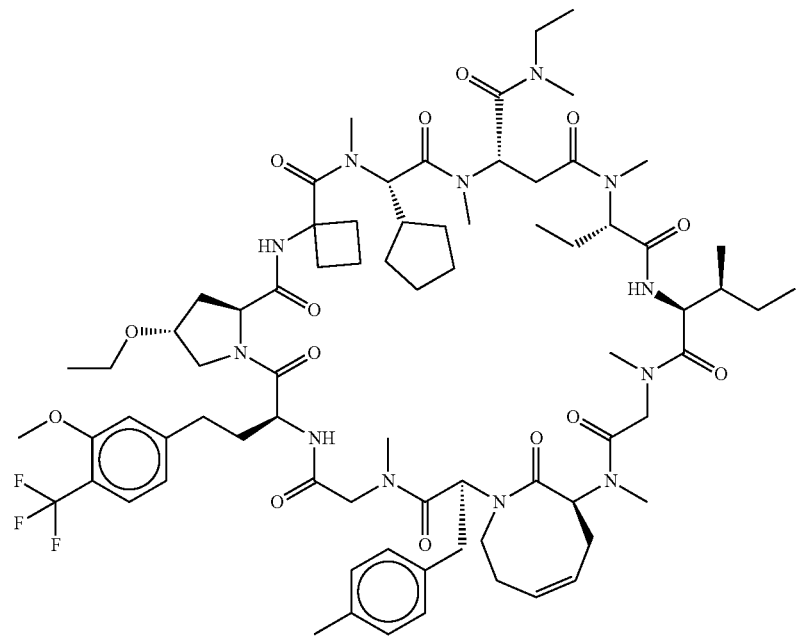 |

TABLE 38-continued
| Compound No. | Structural Formula |
|---|---|
| PP1870 | 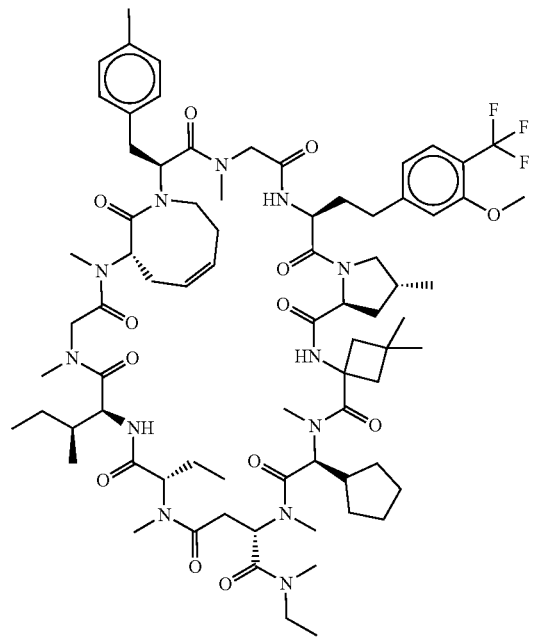 |
| PP1871 | 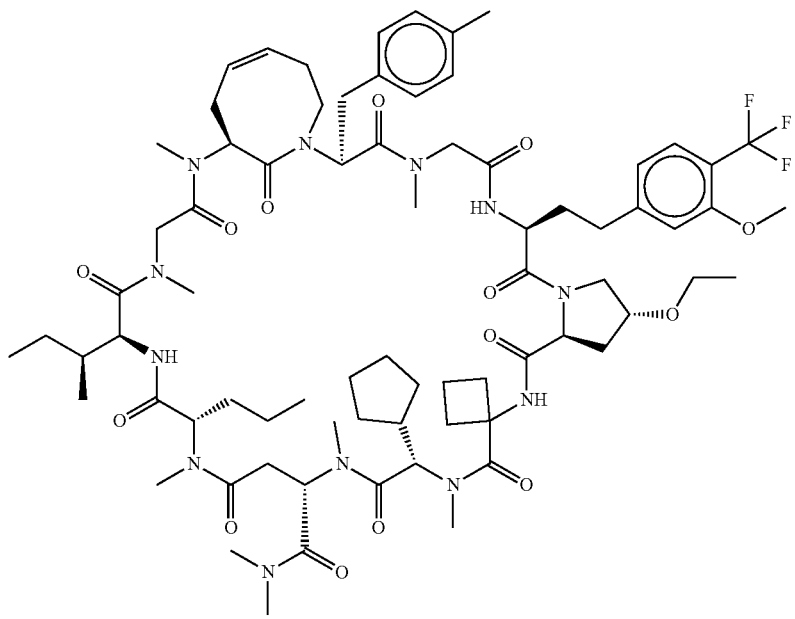 |

TABLE 38-continued
| Compound No. | Structural Formula |
|---|---|
| PP1872 | 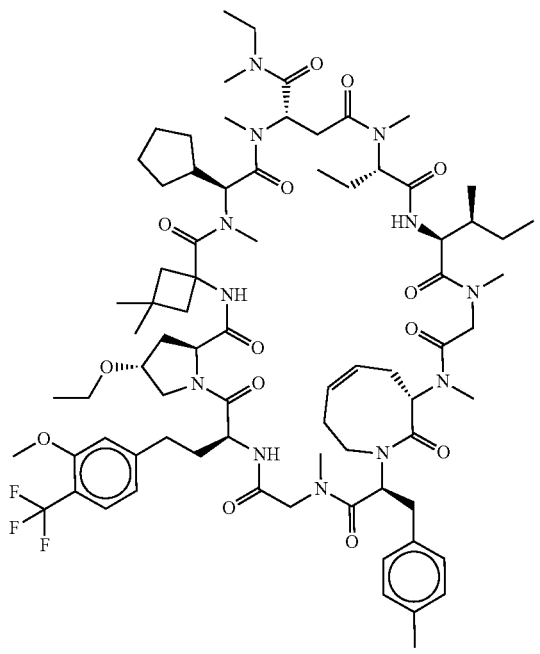 |
| PP1873 | 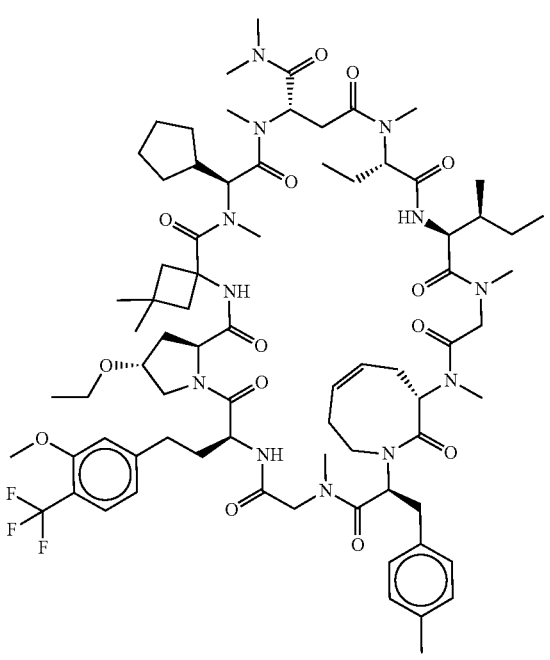 |

TABLE 38-continued

| Compound No. | Structural Formula |
| --- | --- |
| PP1874 | |
| PP1875 | |

TABLE 38-continued

| Compound No. | Structural Formula |
|---|---|
| PP1876 | |
| PP1877 | |

TABLE 38-continued
| Compound No. | Structural Formula |
|---|---|
| PP1878 | 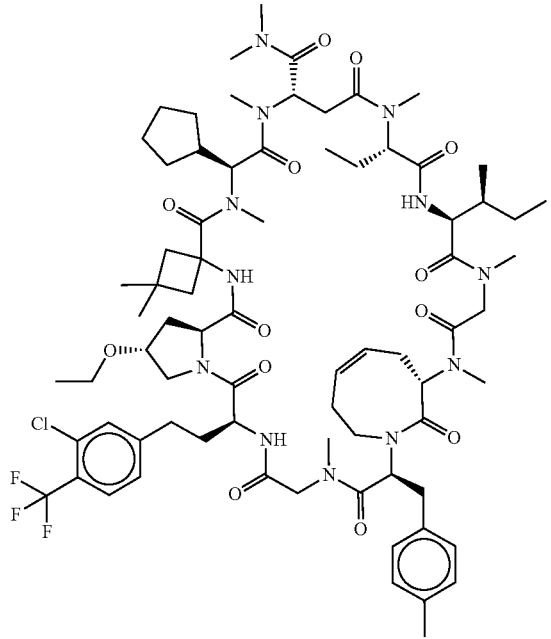 |
| PP1879 | 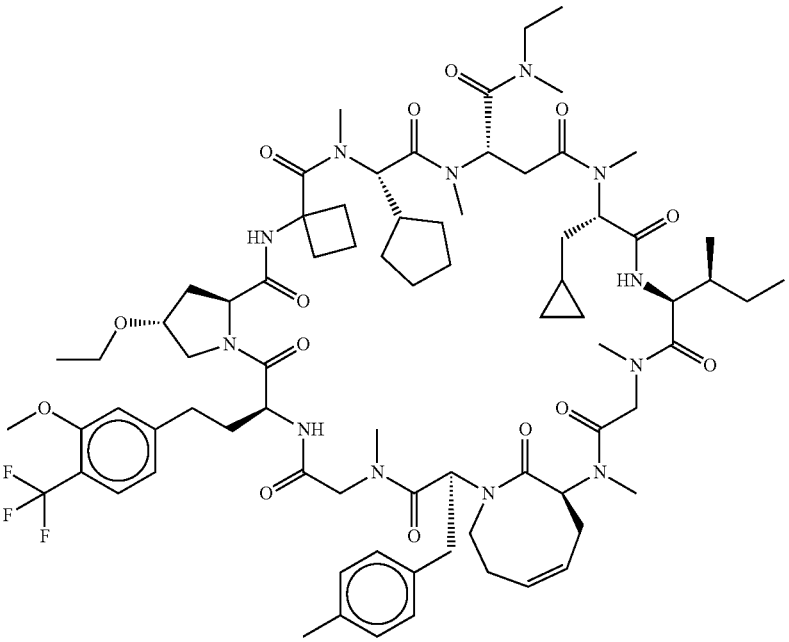 |

TABLE 38-continued

| Compound No. | Structural Formula |
|---|---|
| PP1880 | |
| PP1881 | |

TABLE 38-continued
| Compound No. | Structural Formula |
|---|---|
| PP1882 | 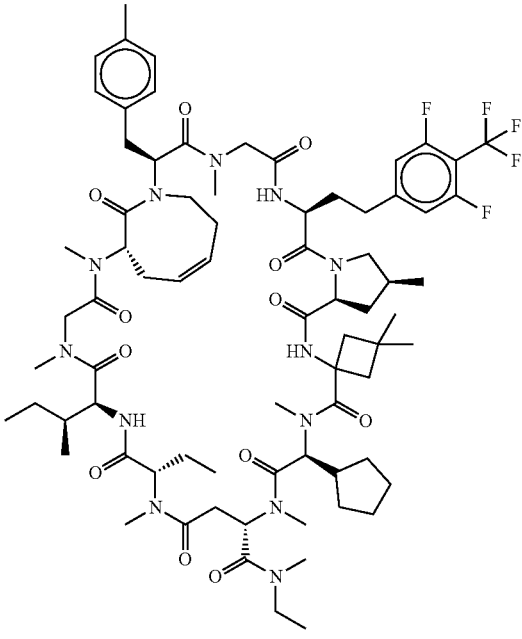 |
| PP1883 | 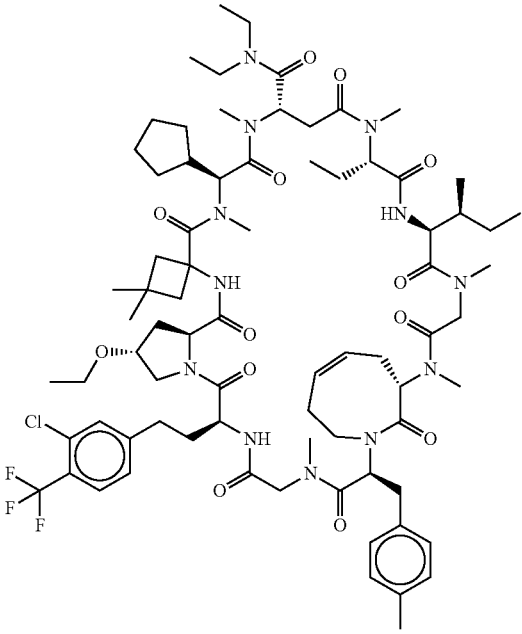 |

TABLE 38-continued

| Compound No. | Structural Formula |
|---|---|
| PP1884 | |
| PP1885 | |

TABLE 38-continued
| Compound No. | Structural Formula |
|---|---|
| PP1886 | 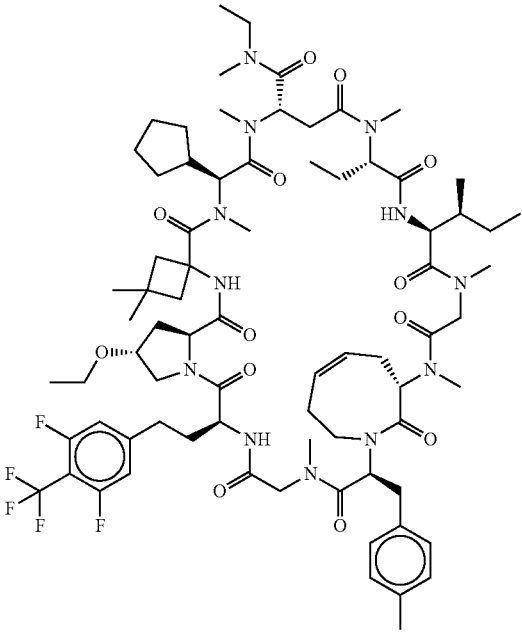 |
| PP1887 | 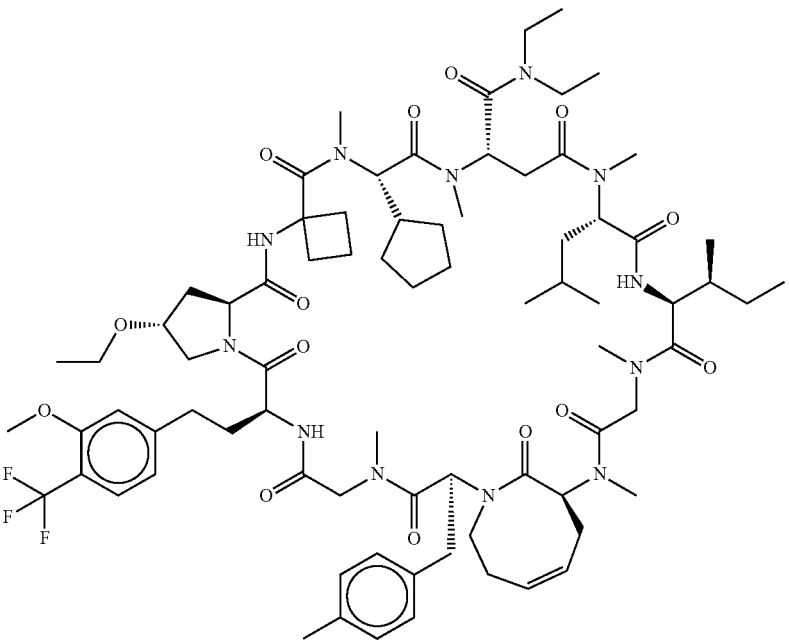 |

TABLE 38-continued
| Compound No. | Structural Formula |
|---|---|
| PP1888 | 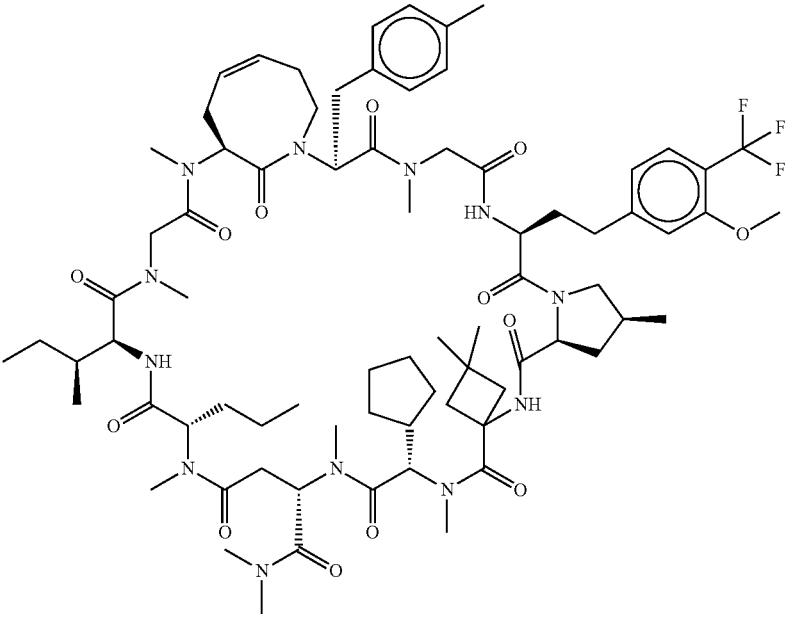 |
| PP1889 | 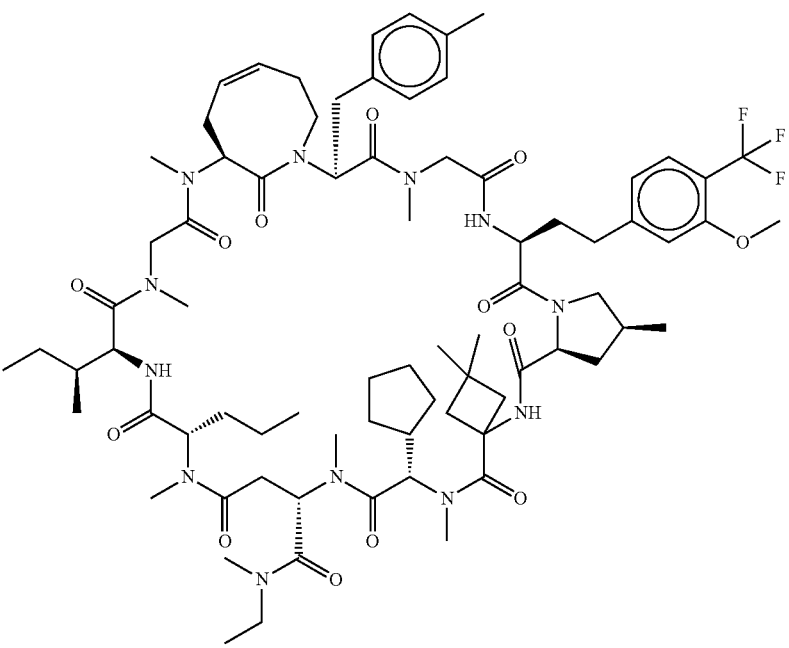 |

TABLE 38-continued

| Compound No. | Structural Formula |
|---|---|
| PP1890 | |
| PP1891 | |

TABLE 38-continued
| Compound No. | Structural Formula |
|---|---|
| PP1892 | 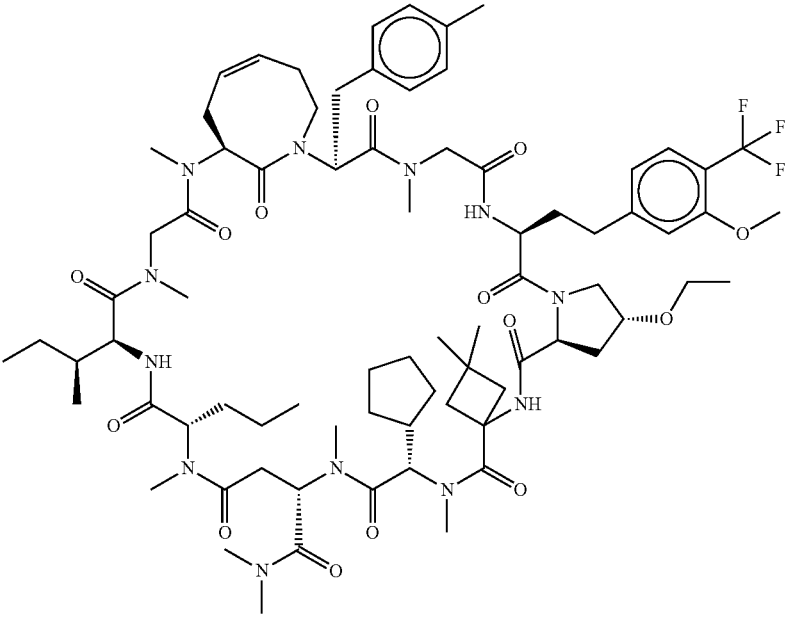 |
| PP1893 | 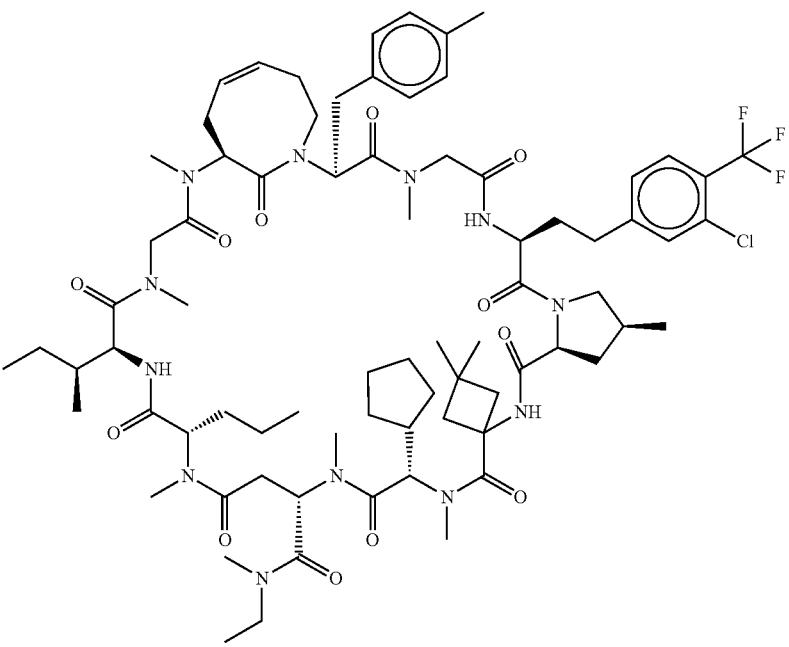 |

TABLE 38-continued

| Compound No. | Structural Formula |
|---|---|
| PP1894 | |
| PP1895 | |

TABLE 38-continued

| Compound No. | Structural Formula |
|---|---|
| PP1896 | |
| PP1897 | |

TABLE 38-continued
| Compound No. | Structural Formula |
|---|---|
| PP1898 | 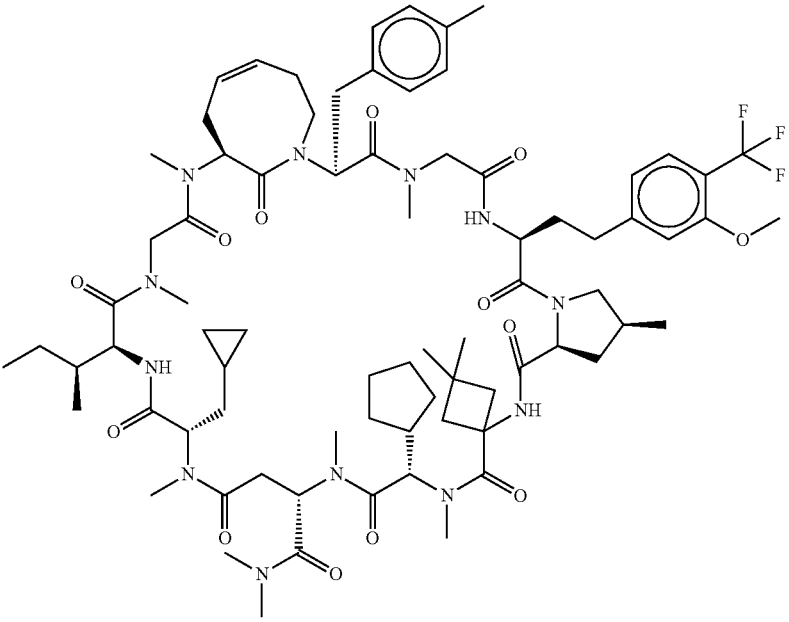 |
| PP1899 | 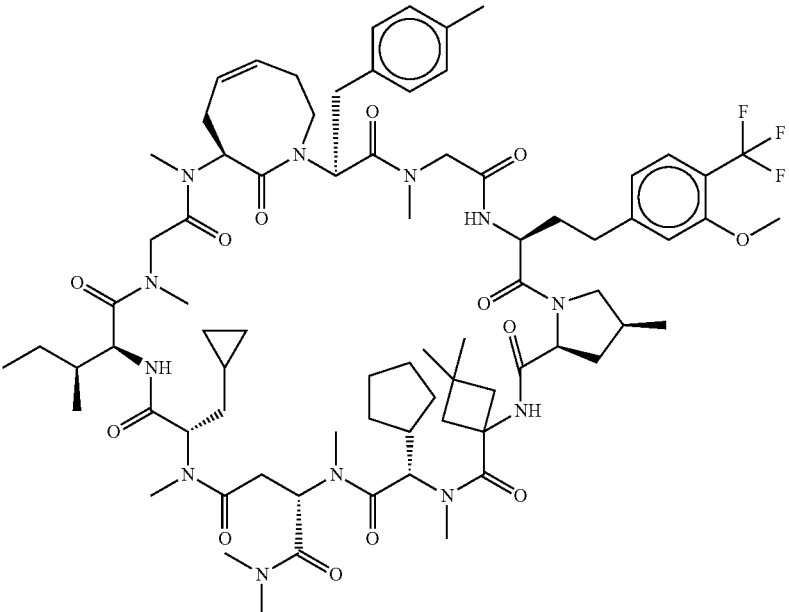 |

TABLE 38-continued

| Compound No. | Structural Formula |
|---|---|
| PP1900 | |
| PP1901 | |

TABLE 38-continued

| Compound No. | Structural Formula |
|---|---|
| PP1902 | |
| PP1903 | |

TABLE 38-continued

| Compound No. | Structural Formula |
|---|---|
| PP1904 | |
| PP1905 | |

TABLE 38-continued

| Compound No. | Structural Formula |
|---|---|
| PP1906 | |
| PP1907 | |

TABLE 38-continued

| Compound No. | Structural Formula |
|---|---|
| PP1908 | |
| PP1909 | |

TABLE 38-continued

| Compound No. | Structural Formula |
|---|---|
| PP1910 | |
| PP1911 | |

TABLE 38-continued
| Compound No. | Structural Formula |
|---|---|
| PP1912 | 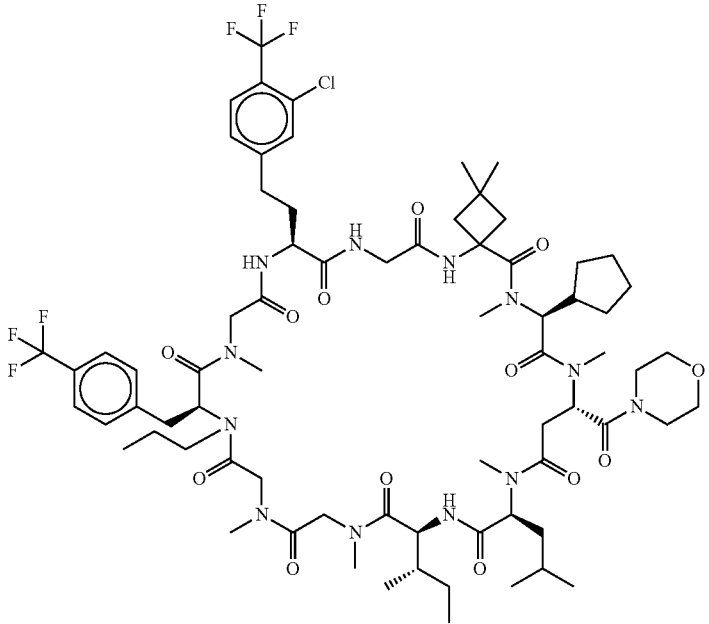 |
| PP1913 | 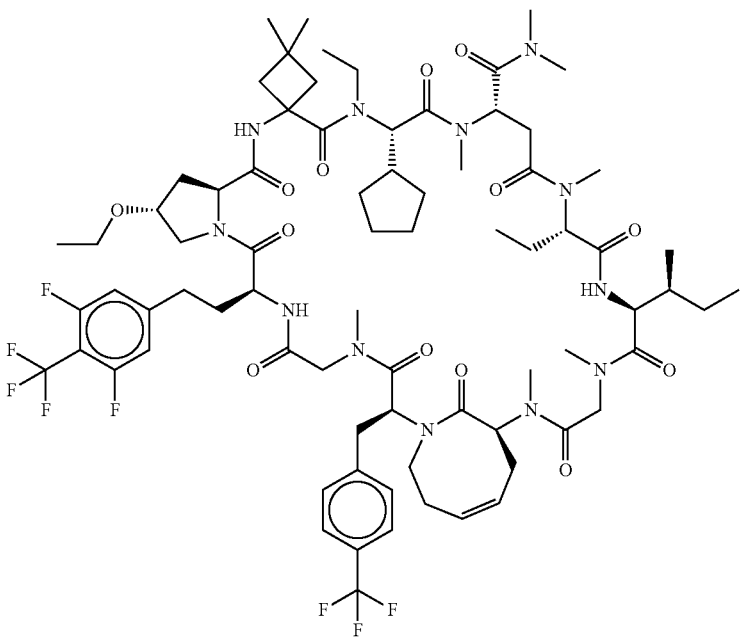 |

TABLE 38-continued
| Compound No. | Structural Formula |
|---|---|
| PP1914 | 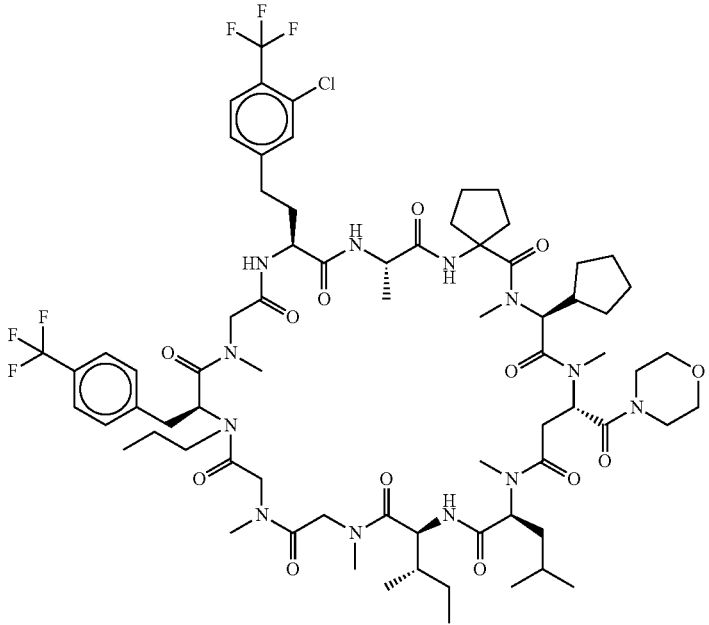 |
| PP1915 | 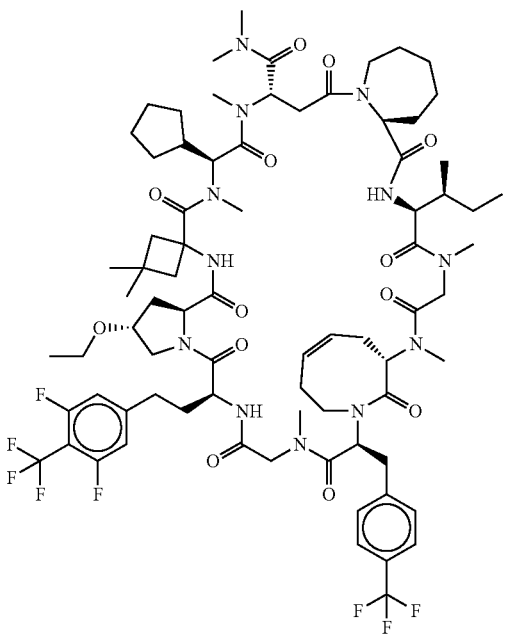 |

TABLE 38-continued

| Compound No. | Structural Formula |
|---|---|
| PP1916 | |
| PP1917 | |

TABLE 38-continued
| Compound No. | Structural Formula |
| --- | --- |
| PP1918 | 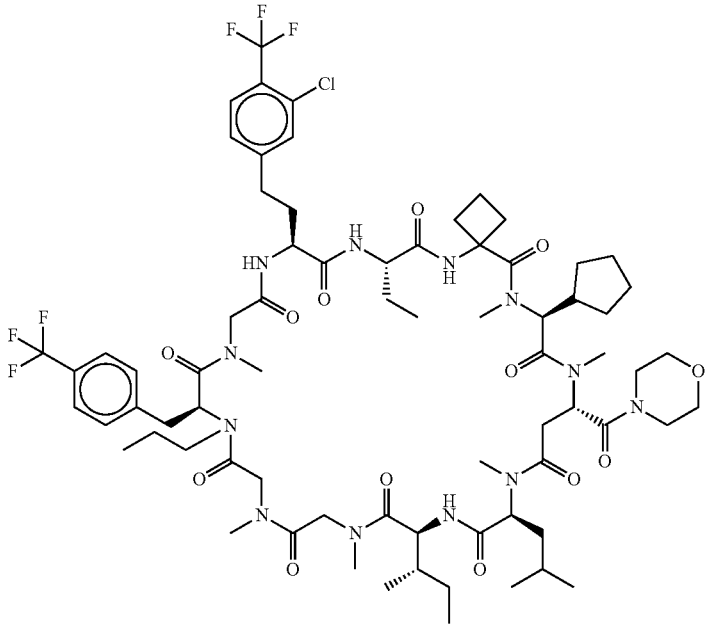 |
| PP1919 | 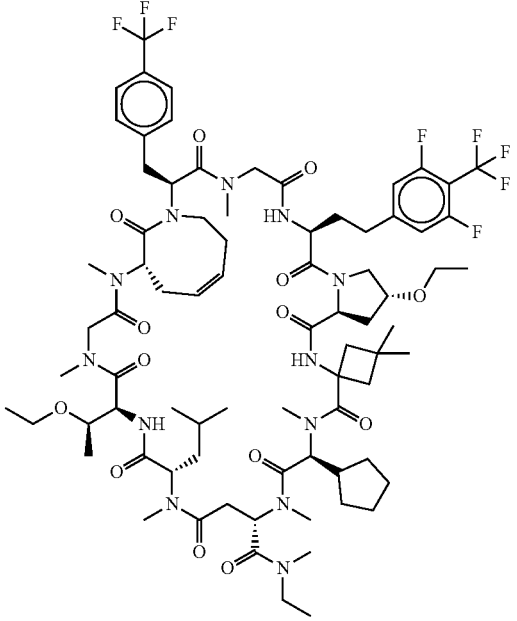 |

TABLE 38-continued
| Compound No. | Structural Formula |
|---|---|
| PP1920 | 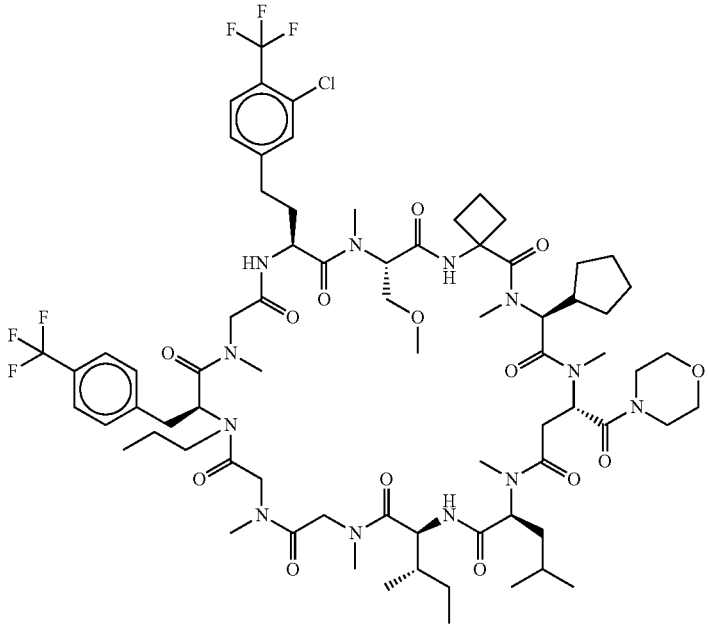 |
| PP1921 | 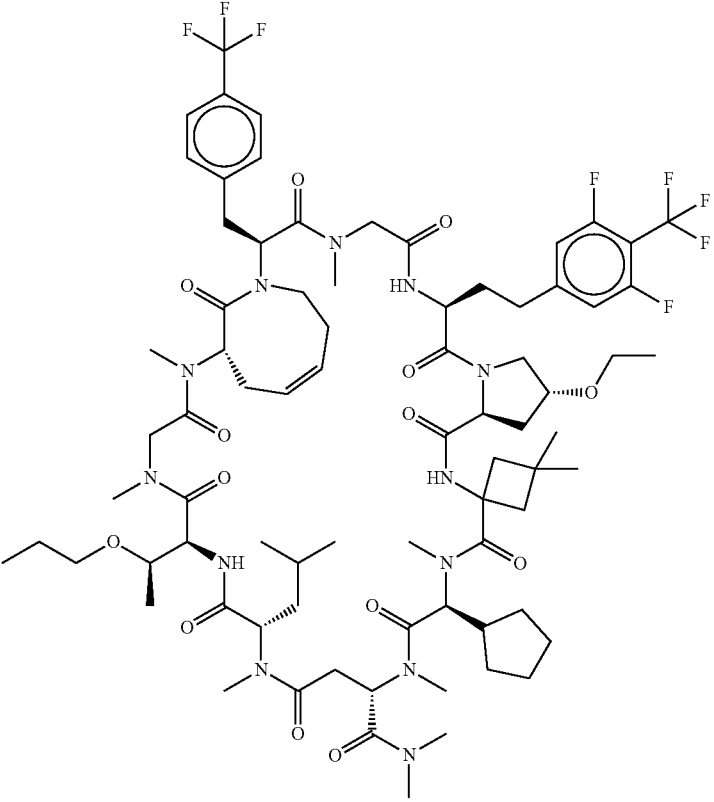 |

TABLE 38-continued
| Compound No. | Structural Formula |
| --- | --- |
| PP1922 | 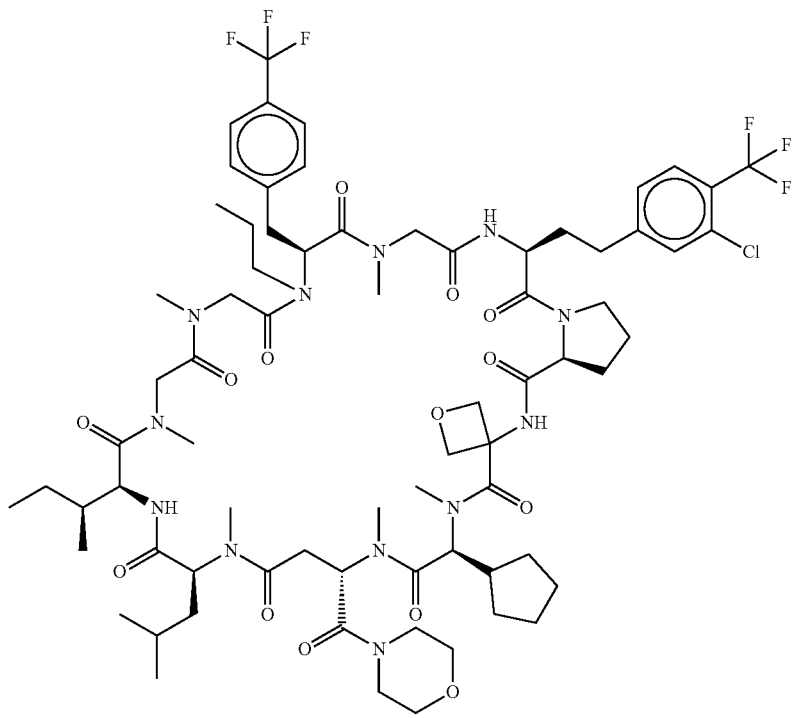 |
| PP1923 | 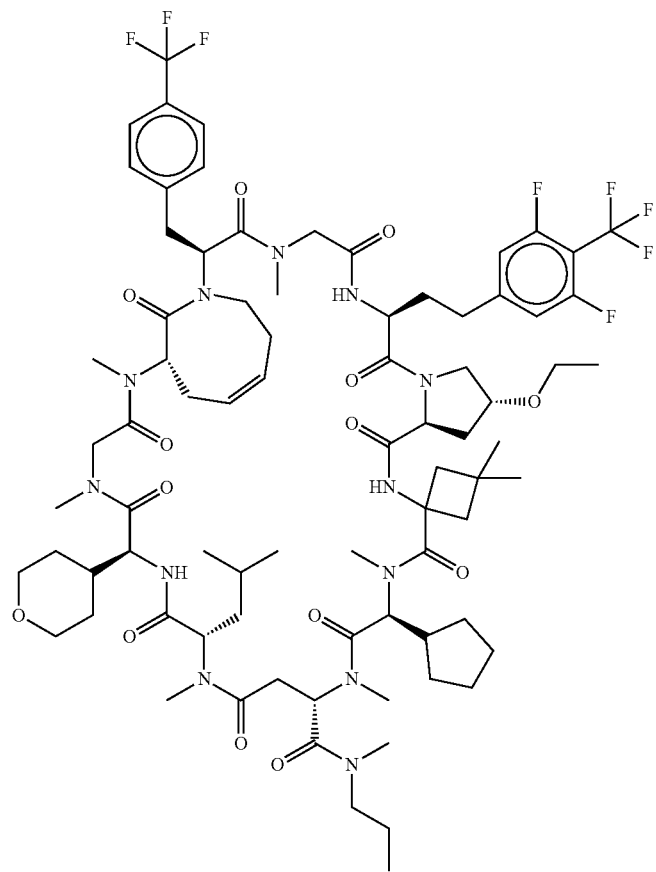 |

TABLE 38-continued

| Compound No. | Structural Formula |
| --- | --- |
| PP1924 | |
| PP1925 | |

TABLE 38-continued

| Compound No. | Structural Formula |
|---|---|
| PP1926 | |
| PP1927 | |

TABLE 38-continued
| Compound No. | Structural Formula |
|---|---|
| PP1928 | 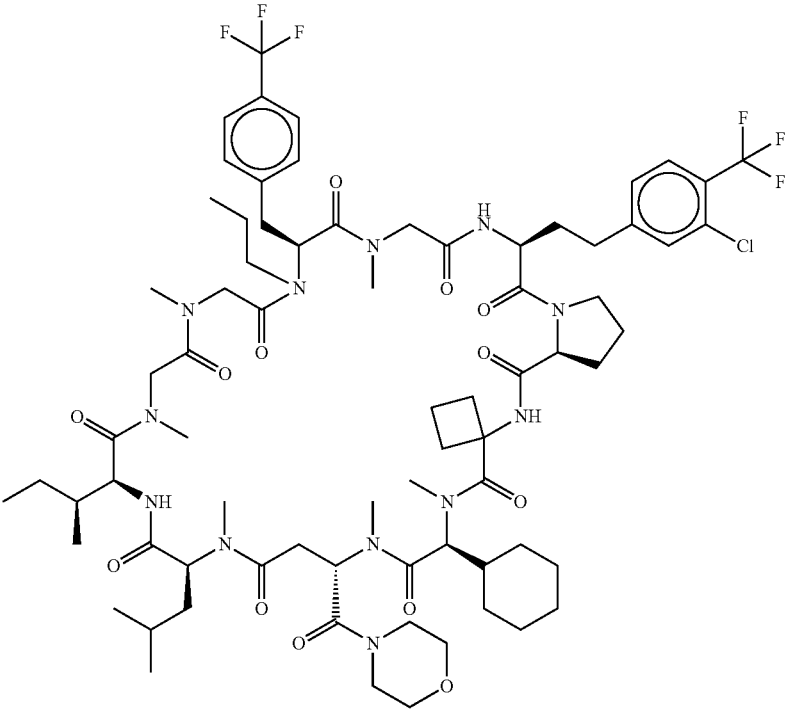 |
| PP1929 | 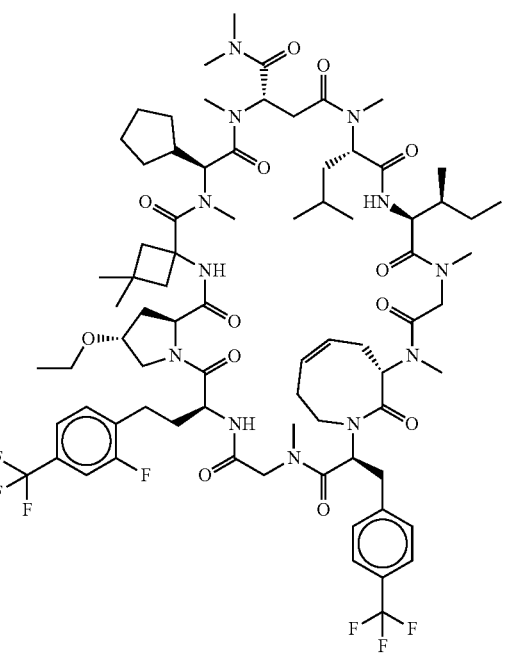 |

TABLE 38-continued

| Compound No. | Structural Formula |
|---|---|
| PP1930 | |
| PP1931 | |

TABLE 38-continued
| Compound No. | Structural Formula |
|---|---|
| PP1932 | 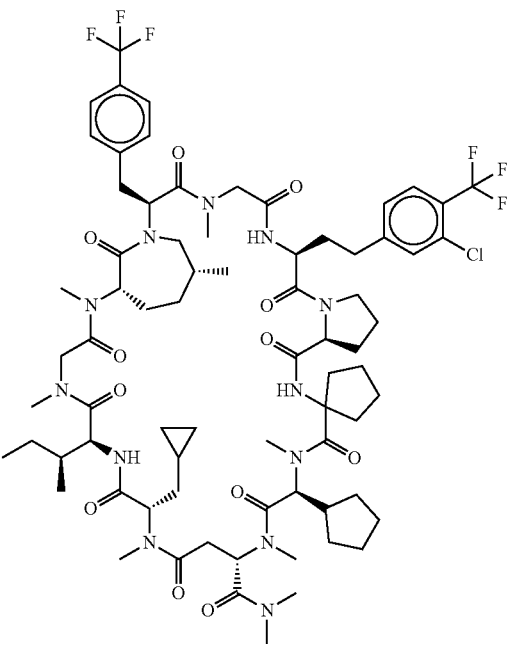 |
| PP1934 | 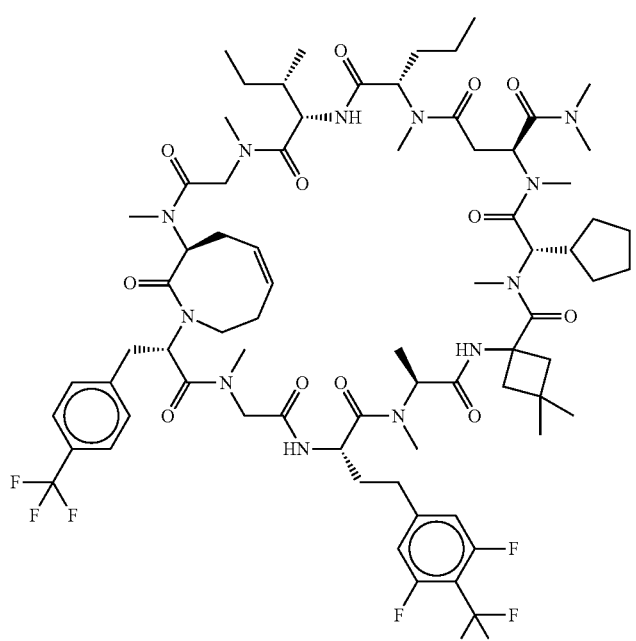 |

TABLE 38-continued
| Compound No. | Structural Formula |
|---|---|
| PP1935 | 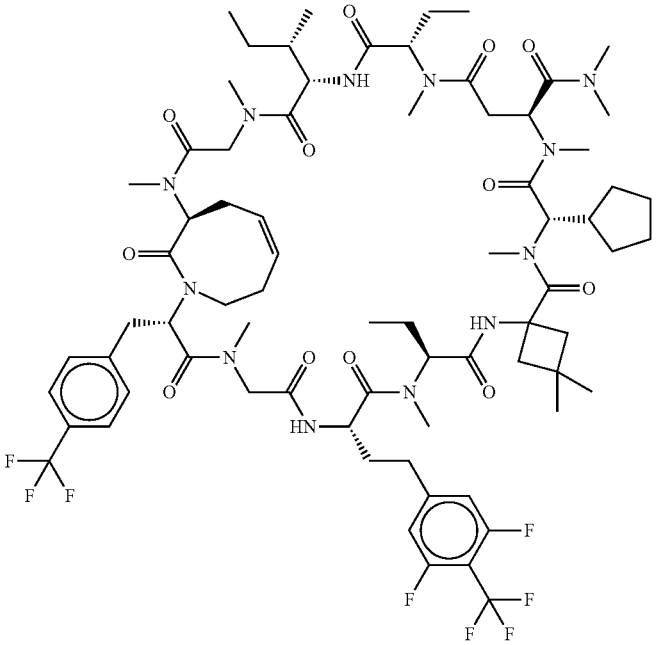 |
| PP1936 | 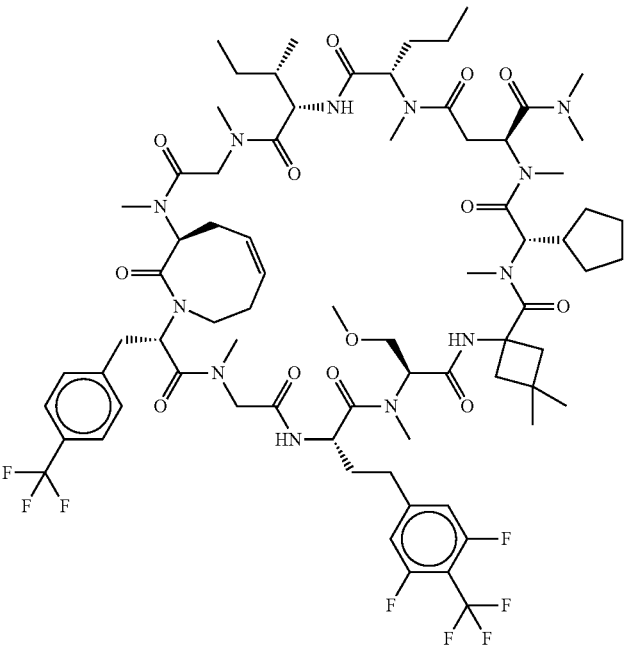 |

TABLE 38-continued

| Compound No. | Structural Formula |
|---|---|
| PP1937 | |
| PP1938 | |

TABLE 38-continued
| Compound No. | Structural Formula |
|---|---|
| PP1939 | 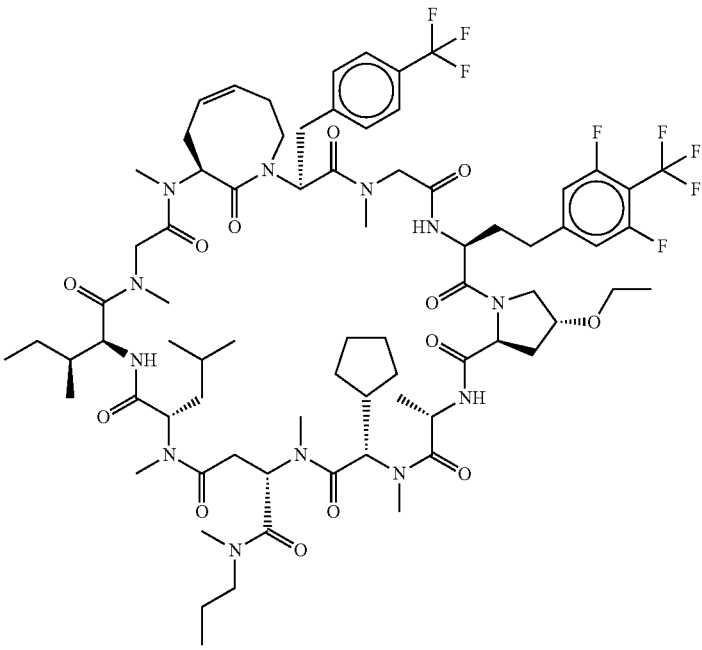 |
| PP1941 | 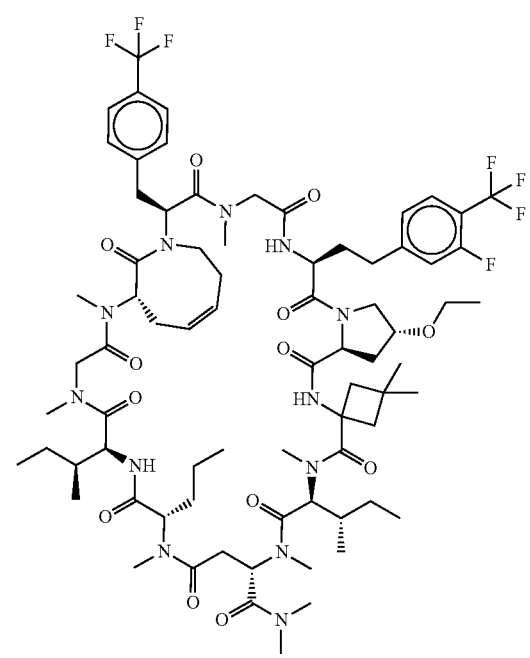 |

TABLE 38-continued

| Compound No. | Structural Formula |
|---|---|
| PP1942 | |
| PP1943 | |

TABLE 38-continued
| Compound No. | Structural Formula |
|---|---|
| PP1944 | 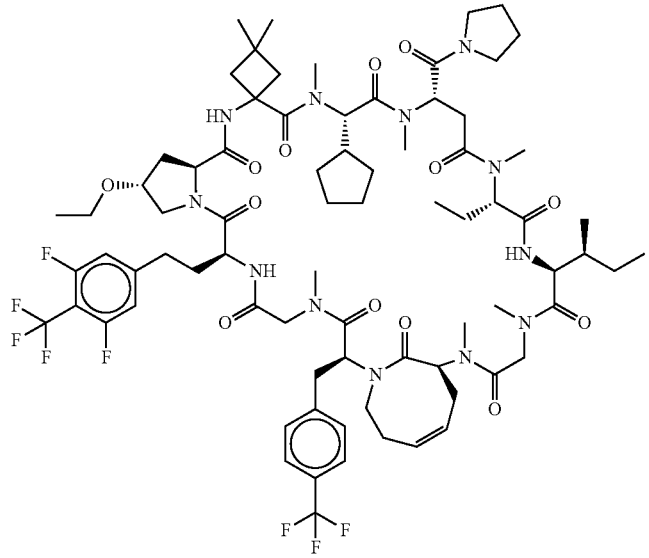 |
| PP1945 | 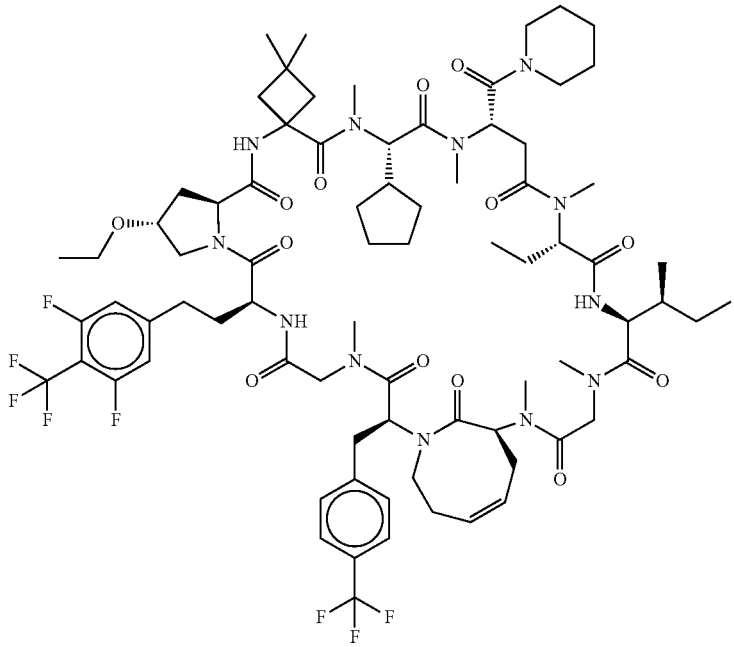 |

TABLE 38-continued
| Compound No. | Structural Formula |
|---|---|
| PP1946 | 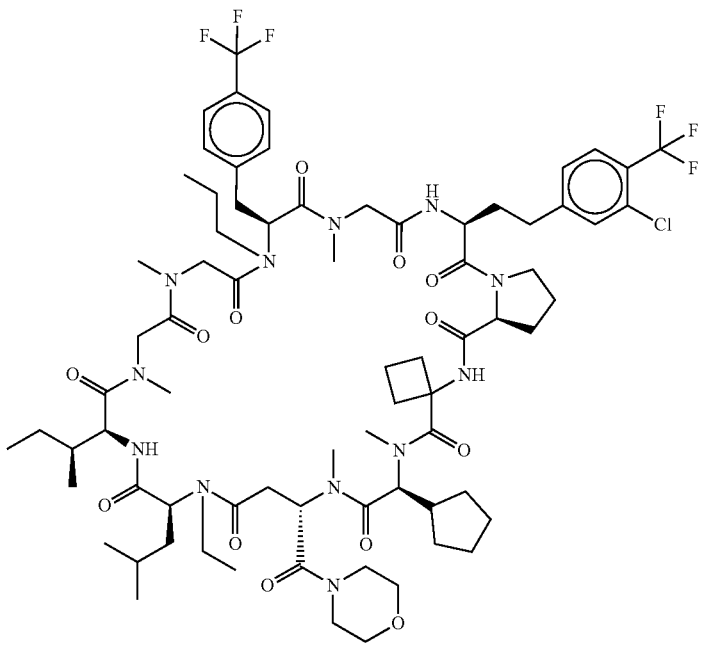 |
| PP1947 | 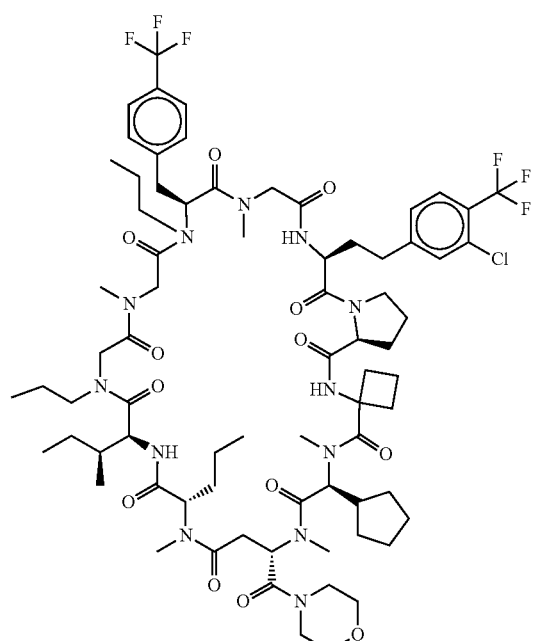 |

TABLE 38-continued
| Compound No. | Structural Formula |
|---|---|
| PP1948 | 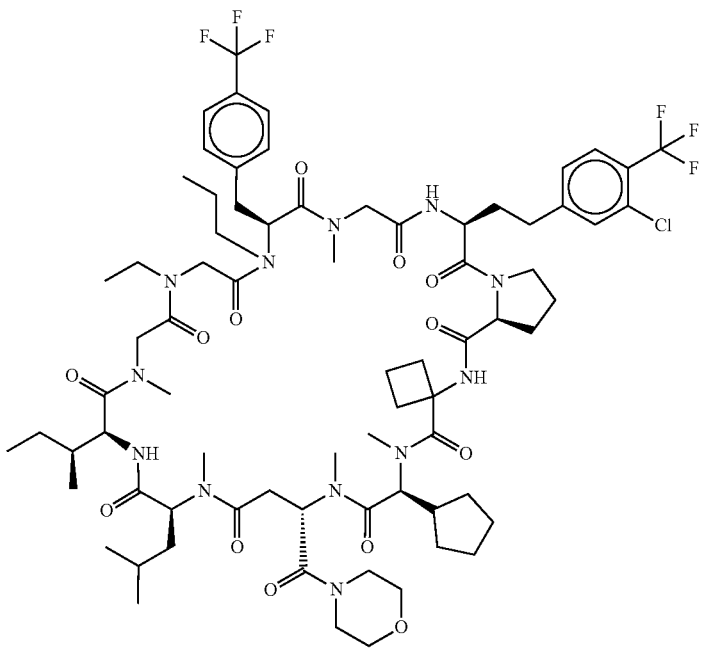 |
| PP1949 | 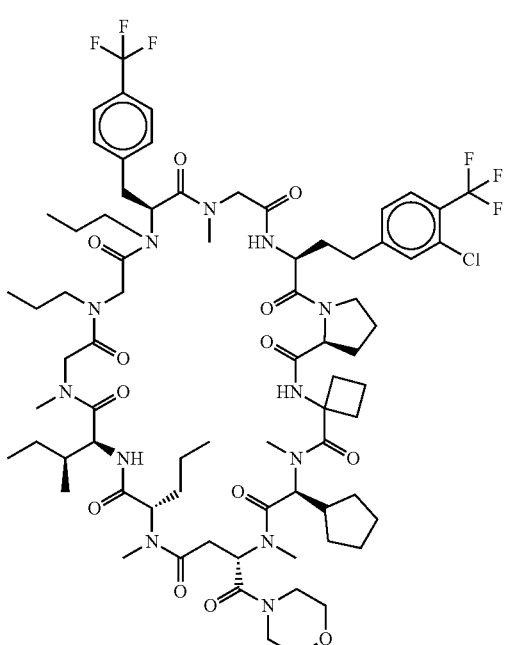 |

TABLE 38-continued

| Compound No. | Structural Formula |
|---|---|
| PP1950 | |
| PP1951 | |

TABLE 38-continued

| Compound No. | Structural Formula |
|---|---|
| PP1952 | |
| PP1953 | |

2711
TABLE 38-continued
| Compound No. | Structural Formula |
|---|---|
| PP1954 | 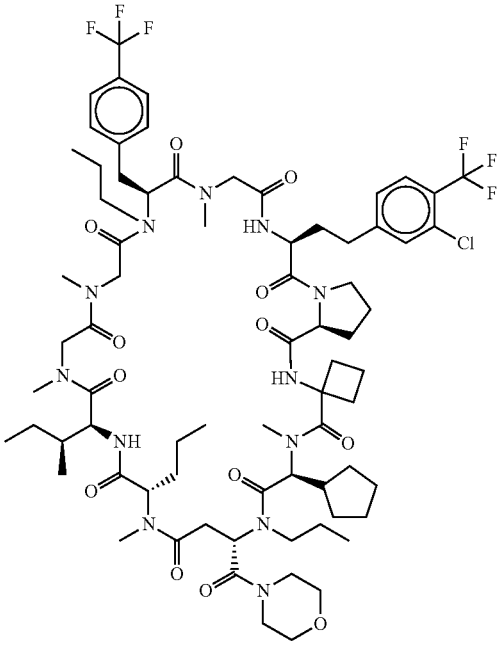 |
| PP1955 | 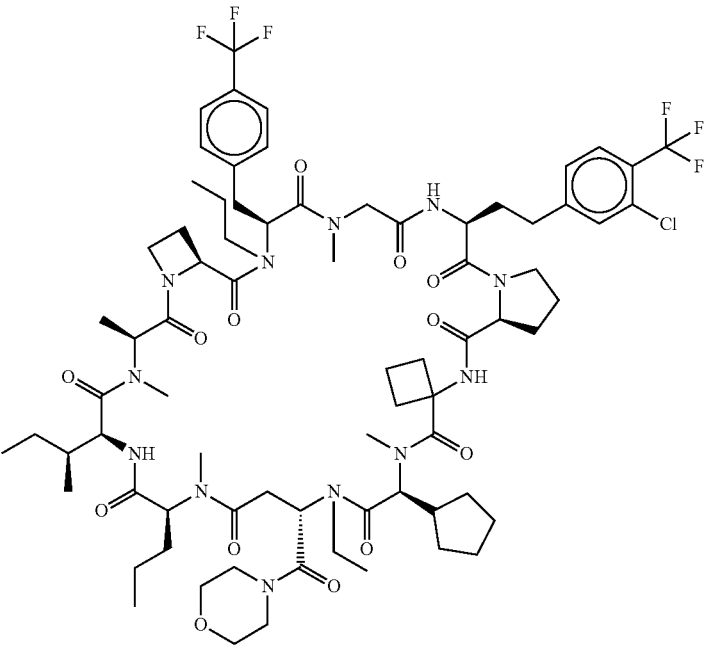 |

TABLE 38-continued

| Compound No. | Structural Formula |
|---|---|
| PP1956 | |
| PP1957 | |

TABLE 38-continued

| Compound No. | Structural Formula |
|---|---|
| PP1958 | |
| PP1959 | |

US 12,410,212 B2
TABLE 38-continued
| Compound No. | Structural Formula |
|---|---|
| PP1960 | 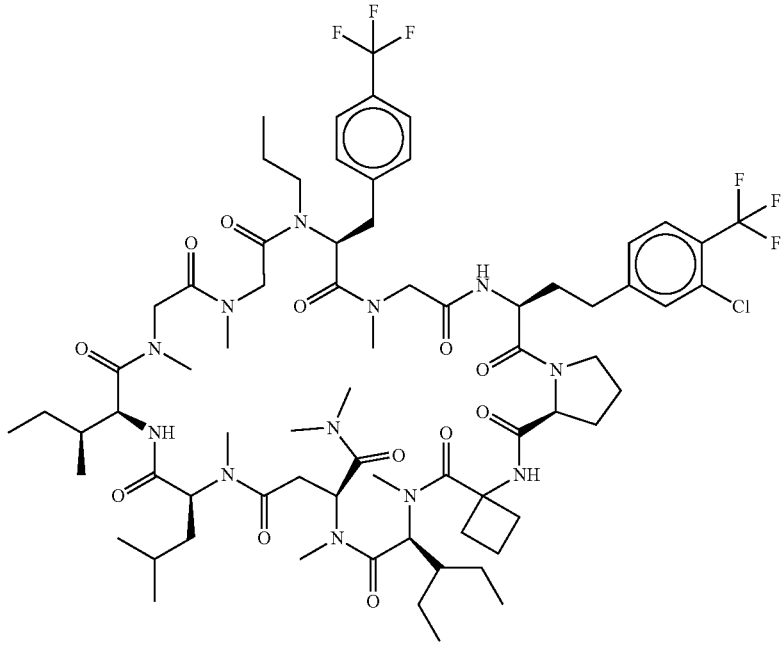 |
| PP1961 | 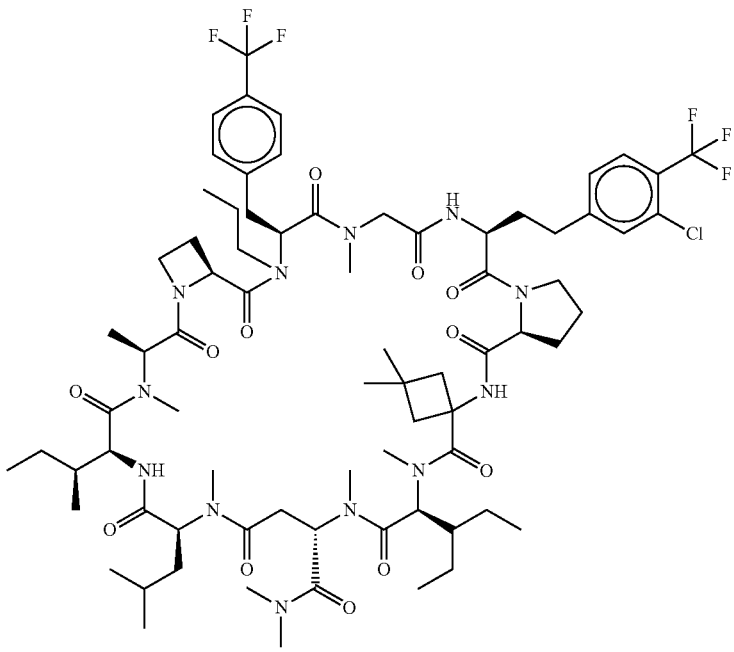 |

TABLE 38-continued
| Compound No. | Structural Formula |
|---|---|
| PP1963 | 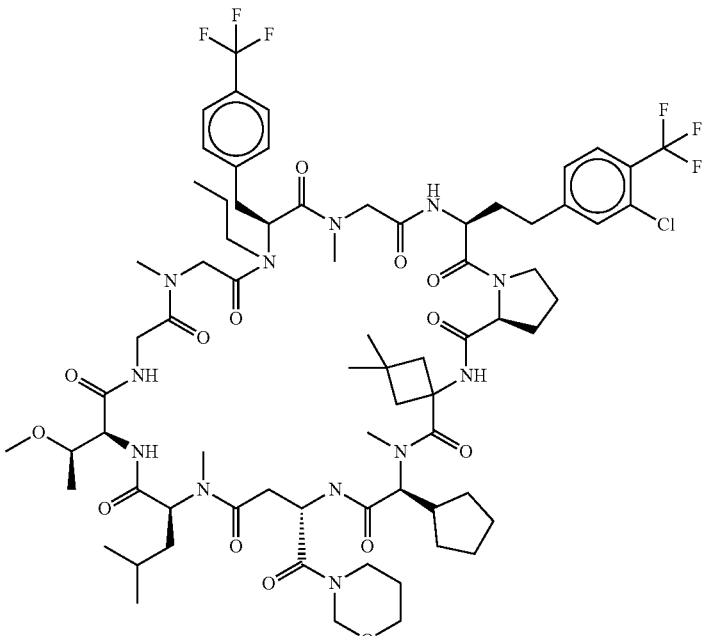 |
| PP1964 | 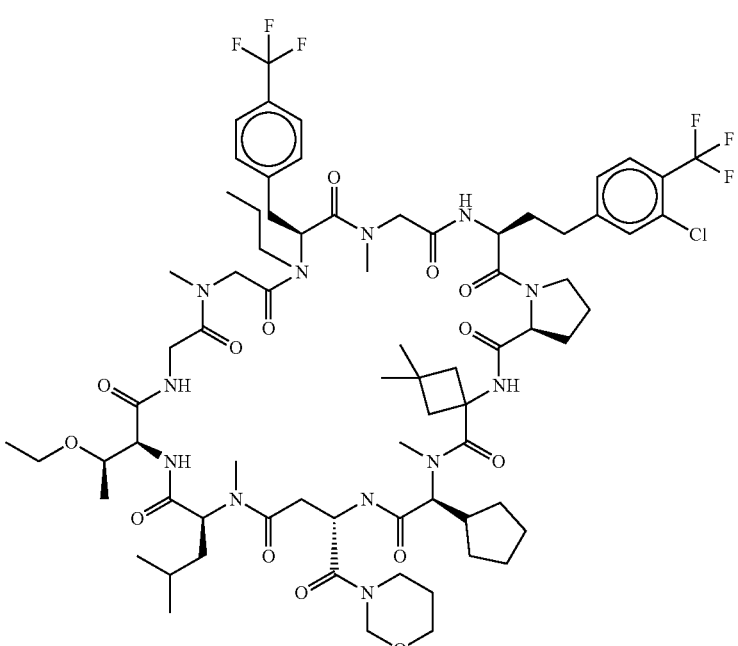 |

TABLE 38-continued
| Compound No. | Structural Formula |
|---|---|
| PP1965 | 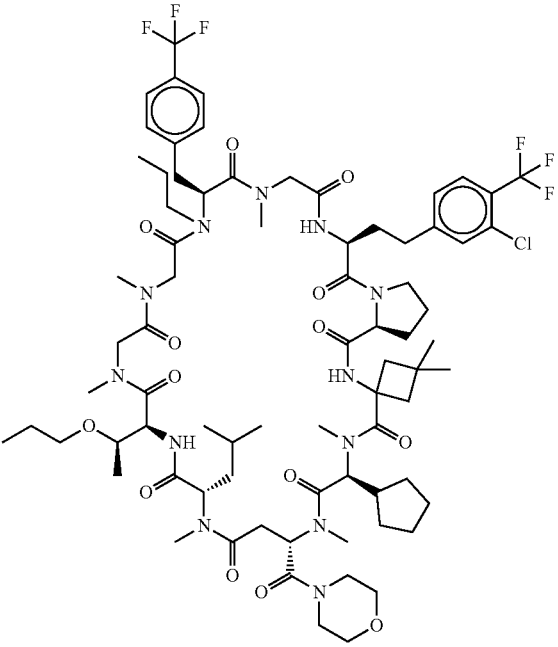 |
| PP1966 | 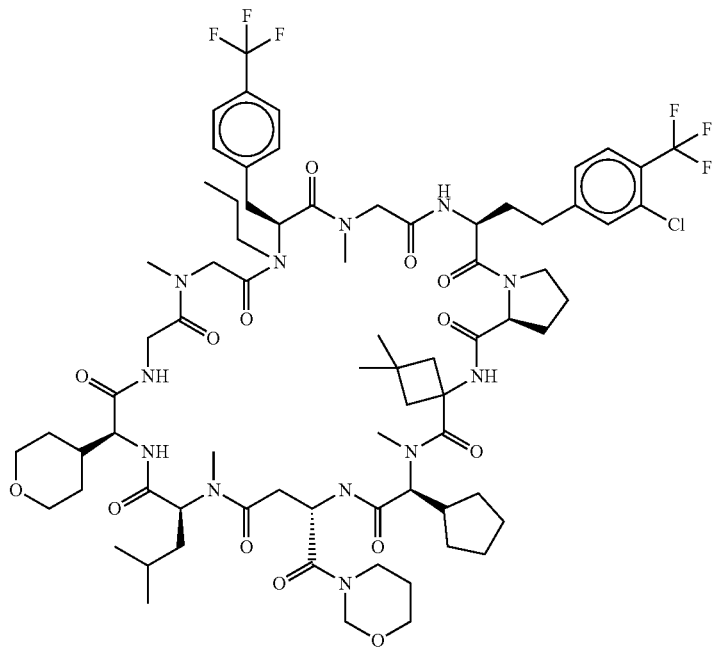 |

TABLE 38-continued

| Compound No. | Structural Formula |
|---|---|
| PP1967 | |
| PP1968 | |

TABLE 38-continued

| Compound No. | Structural Formula |
|---|---|
| PP1969 | |
| PP1970 | |

TABLE 38-continued
| Compound No. | Structural Formula |
|---|---|
| PP1971 | 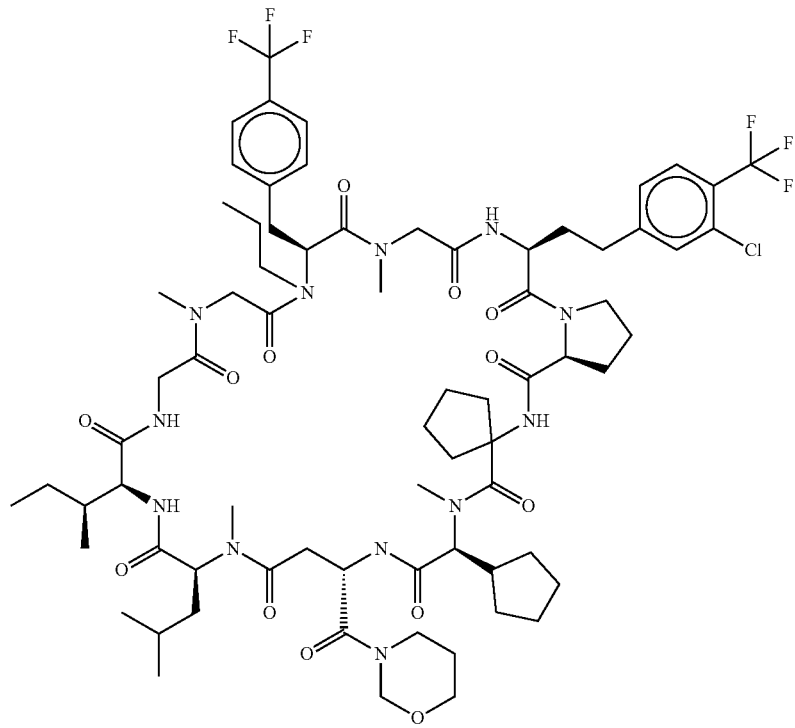 |
| PP1972 | 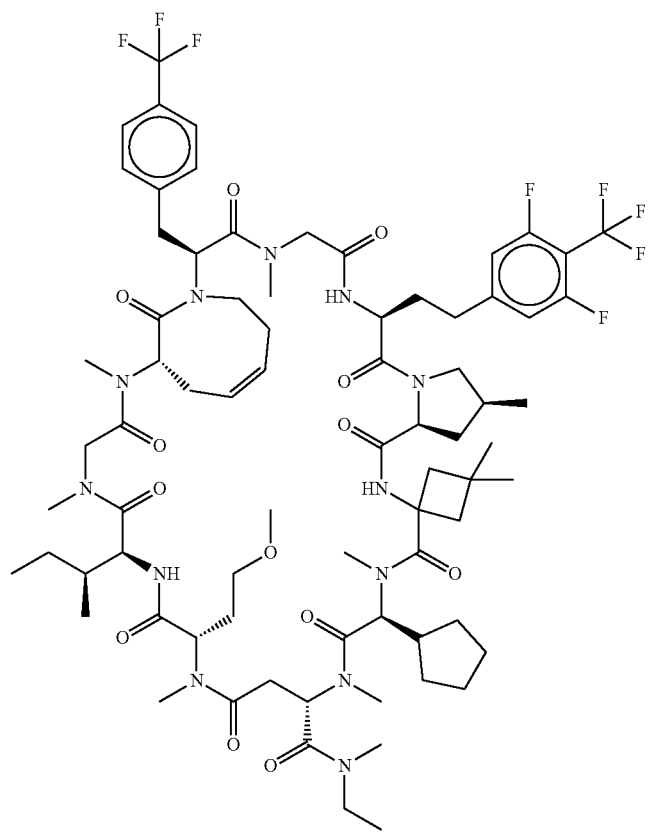 |

TABLE 38-continued

| Compound No. | Structural Formula |
|---|---|
| PP1973 | |
| PP1974 | |

TABLE 38-continued
| Compound No. | Structural Formula |
|---|---|
| PP1975 | 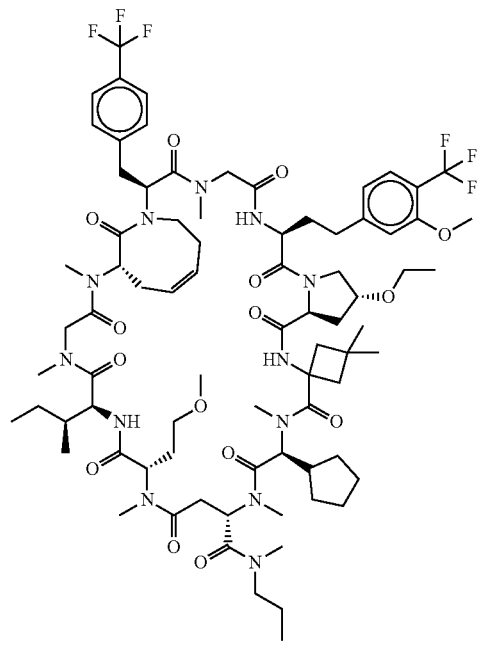 |
| PP1976 | 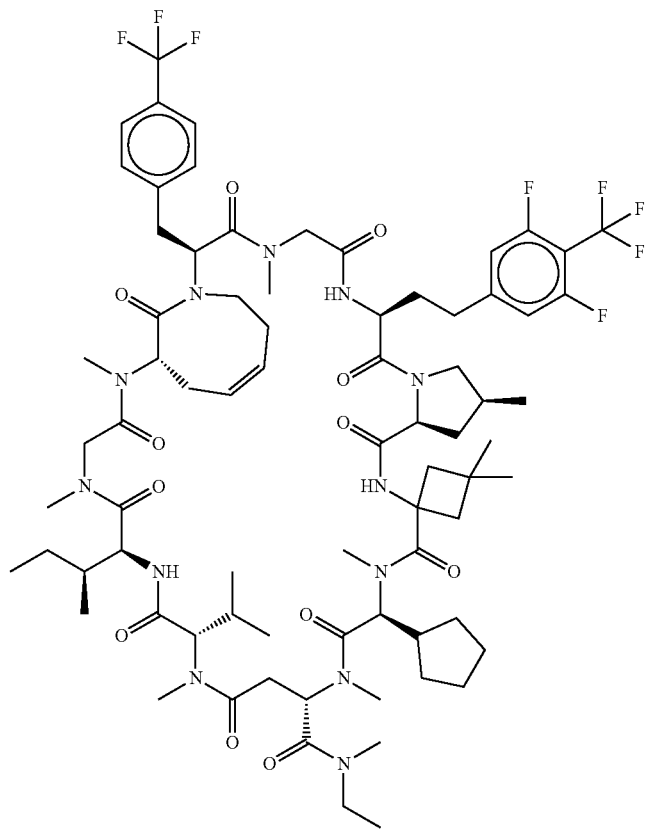 |

TABLE 38-continued
| Compound No. | Structural Formula |
|---|---|
| PP1977 | 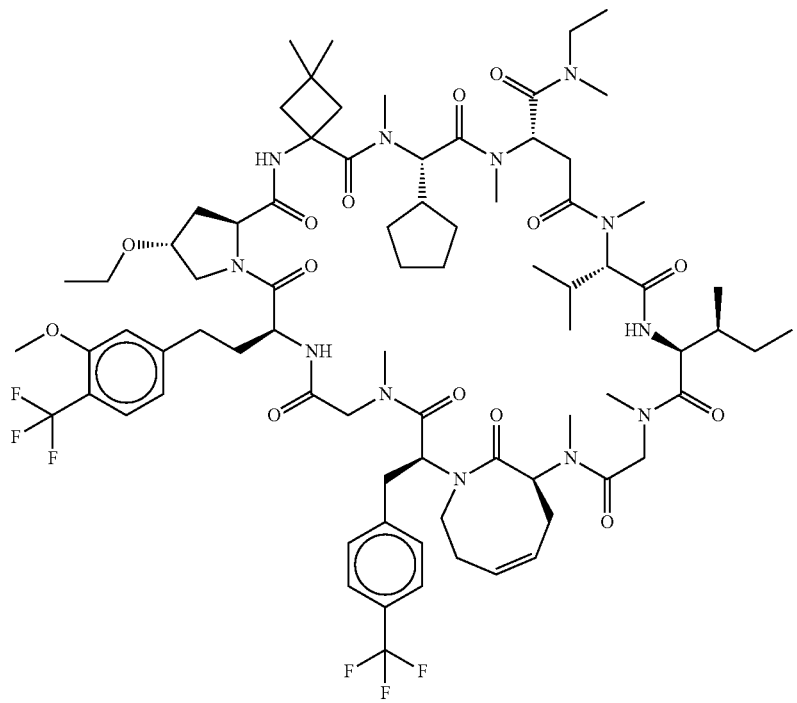 |
| PP1979 | 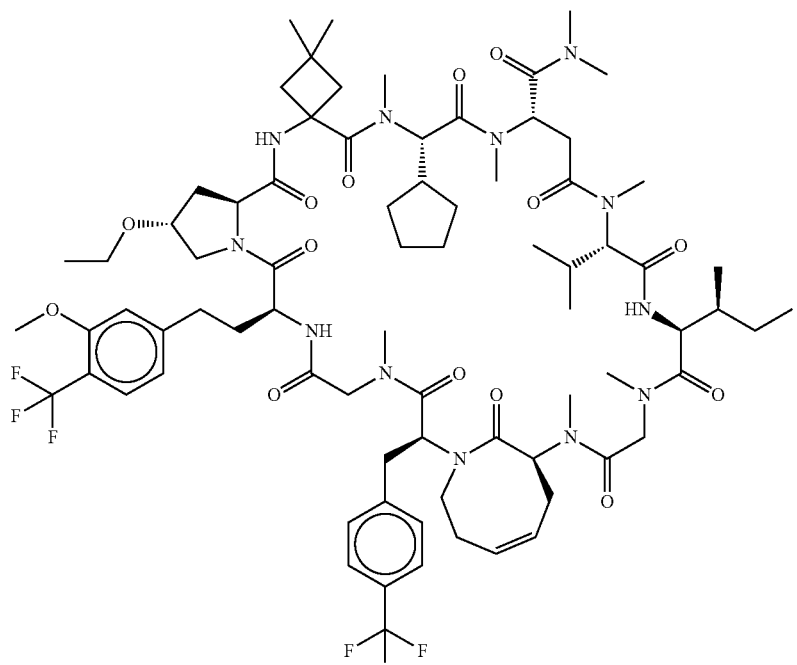 |

TABLE 38-continued
| Compound No. | Structural Formula |
|---|---|
| PP1980 | 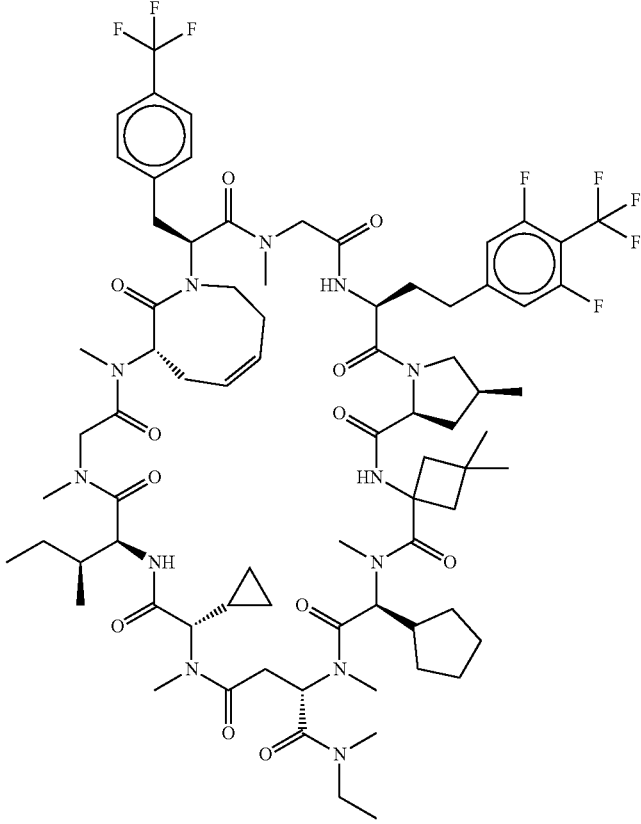 |
| PP1981 | 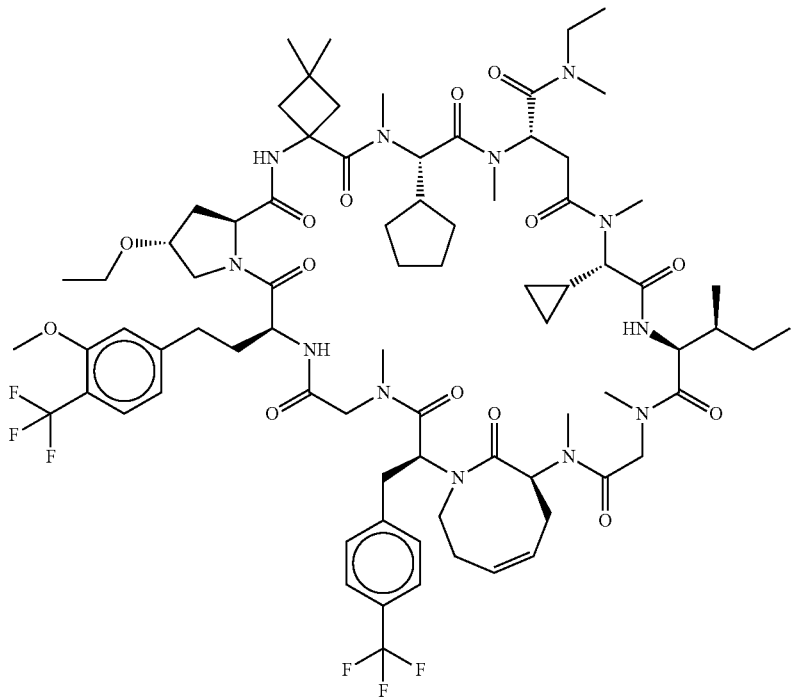 |

TABLE 38-continued
| Compound No. | Structural Formula |
|---|---|
| PP1983 | 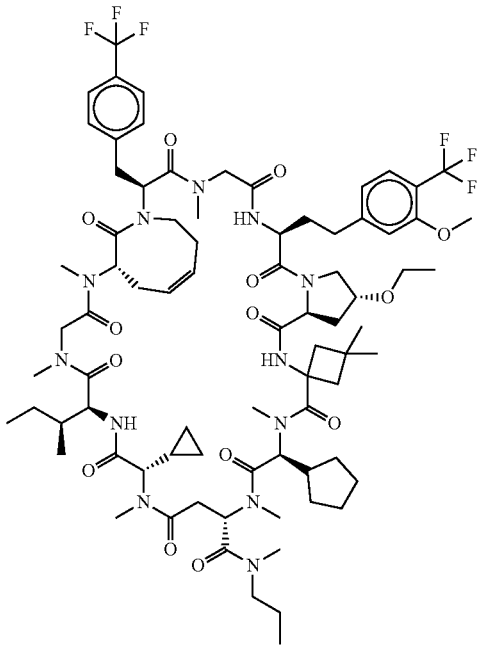 |
| PP1984 | 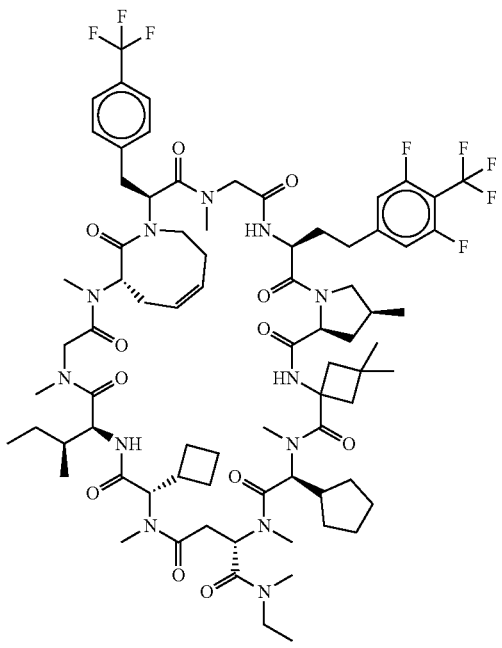 |

TABLE 38-continued

| Compound No. | Structural Formula |
|---|---|
| PP1985 | |
| PP1987 | |

TABLE 38-continued

| Compound No. | Structural Formula |
|---|---|
| PP1988 | |
| PP1989 | |

TABLE 38-continued
| Compound No. | Structural Formula |
|---|---|
| PP1990 | 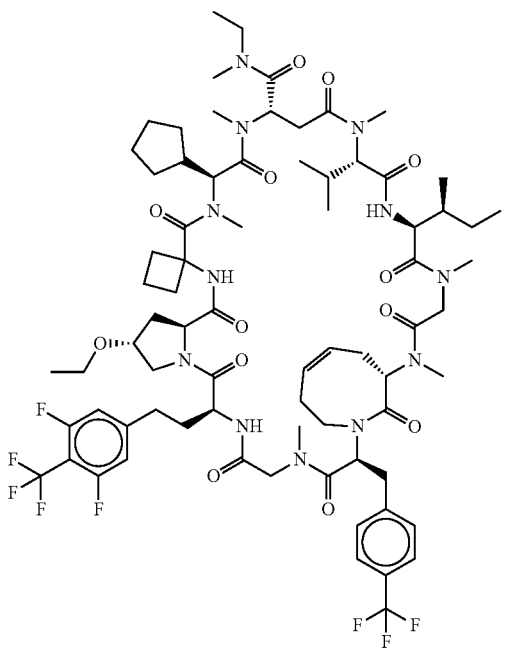 |
| PP1991 | 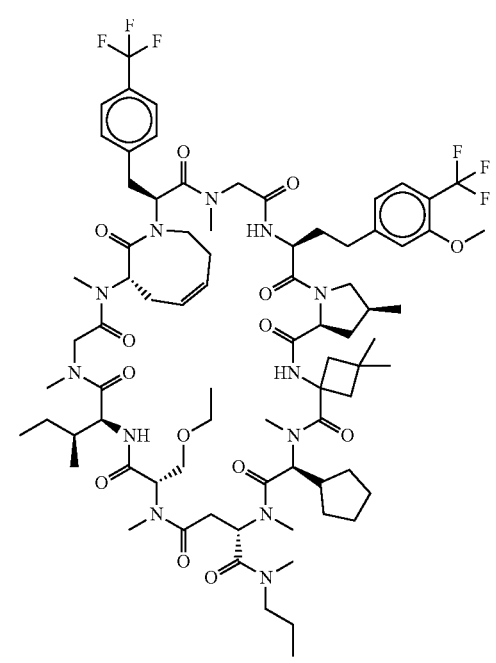 |

TABLE 38-continued

| Compound No. | Structural Formula |
| --- | --- |
| PP1992 | |
| PP1993 | |

TABLE 38-continued

| Compound No. | Structural Formula |
| --- | --- |
| PP1994 | |
| PP1995 | |

TABLE 38-continued

| Compound No. | Structural Formula |
|---|---|
| PP1996 | |
| PP1997 | |

TABLE 38-continued

| Compound No. | Structural Formula |
|---|---|
| PP1998 | |
| PP1999 | |

TABLE 38-continued

| Compound No. | Structural Formula |
|---|---|
| PP2000 | |
| PP2001 | |

TABLE 38-continued

| Compound No. | Structural Formula |
| --- | --- |
| PP2002 | |
| PP2003 | |

TABLE 38-continued
| Compound No. | Structural Formula |
|---|---|
| PP2004 | 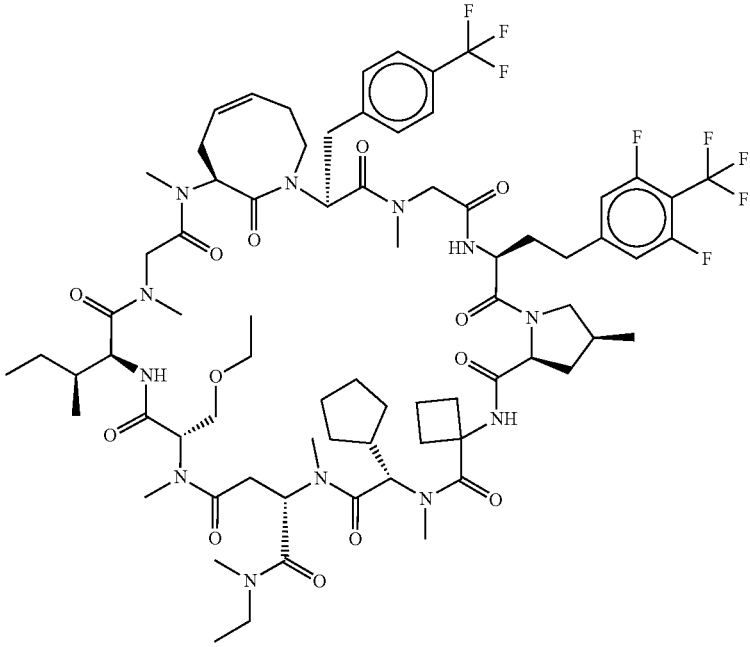 |
| PP2005 | 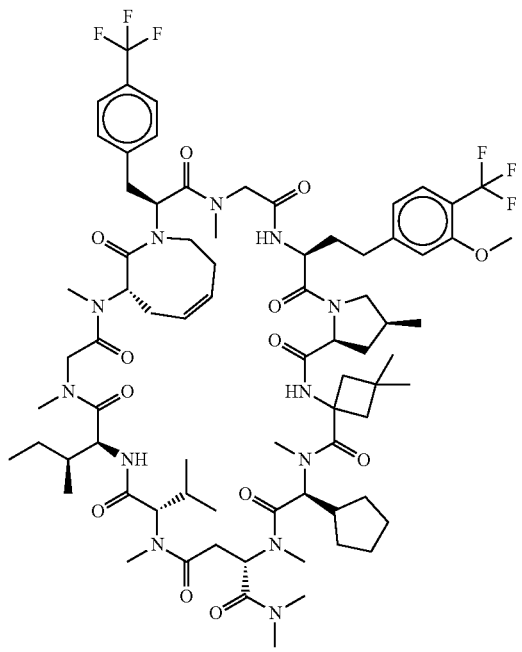 |

TABLE 38-continued

| Compound No. | Structural Formula |
|---|---|
| PP2006 | |
| PP2007 | |

TABLE 38-continued

| Compound No. | Structural Formula |
|---|---|
| PP2008 | |
| PP2009 | |

TABLE 38-continued

| Compound No. | Structural Formula |
|---|---|
| PP2010 | |
| PP2011 | |

TABLE 38-continued

| Compound No. | Structural Formula |
|---|---|
| PP2012 | |
| PP2013 | |

TABLE 38-continued
| Compound No. | Structural Formula |
|---|---|
| PP2014 | 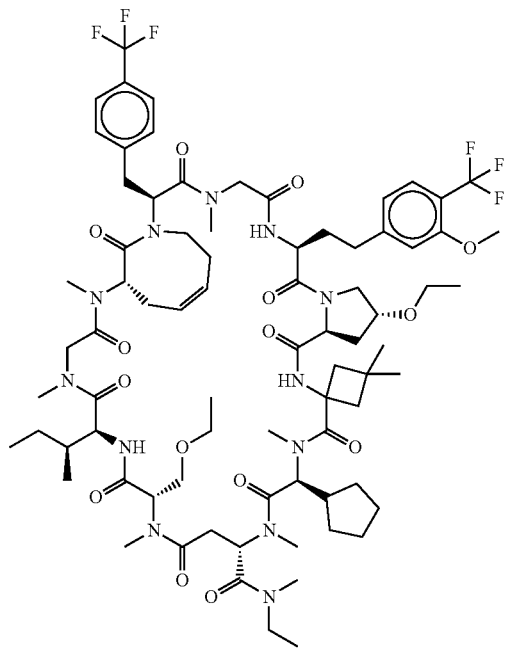 |
| PP2015 | 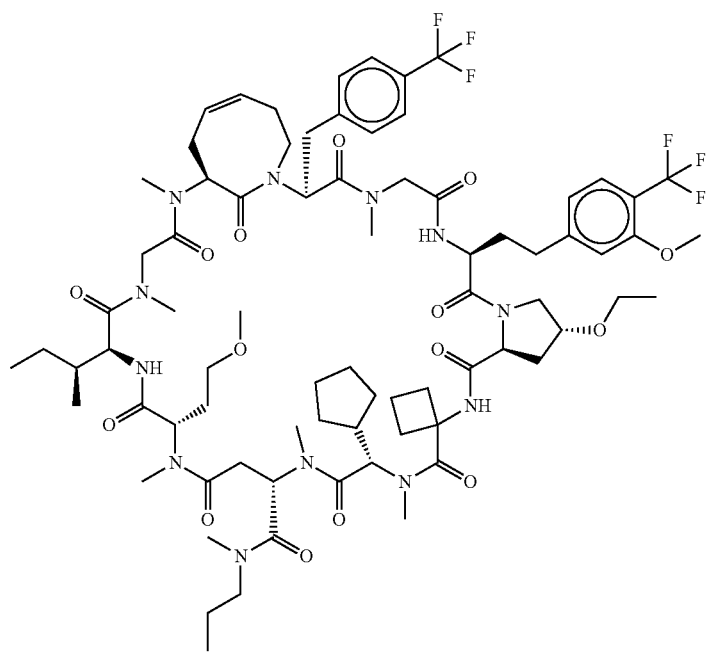 |

TABLE 38-continued

| Compound No. | Structural Formula |
|---|---|
| PP2016 | |
| PP2017 | |

TABLE 38-continued
| Compound No. | Structural Formula |
|---|---|
| PP2018 | 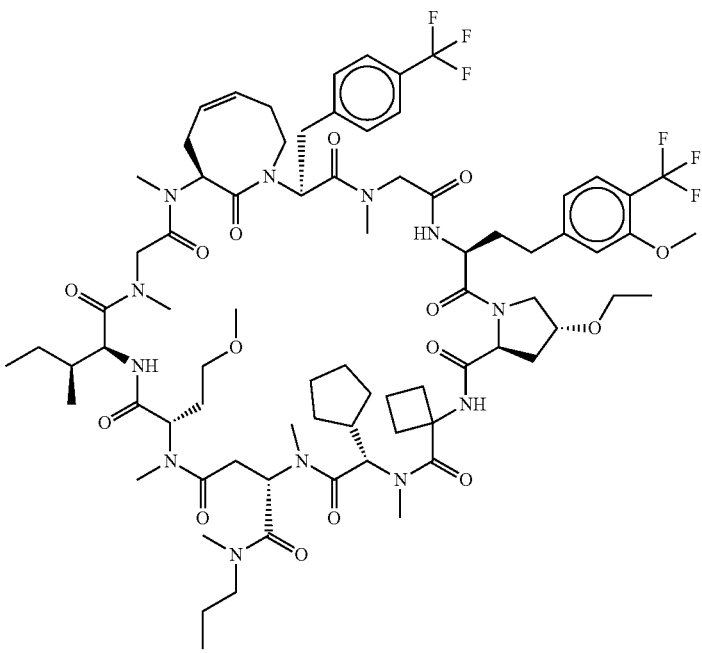 |
| PP2019 | 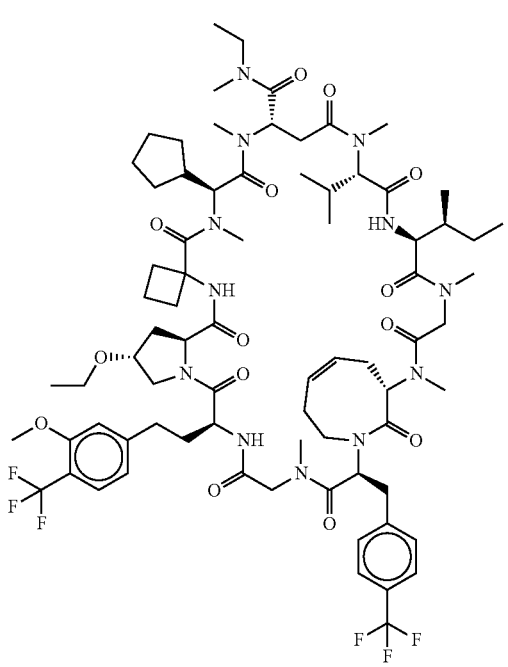 |

TABLE 38-continued
| Compound No. | Structural Formula |
|---|---|
| PP2020 | 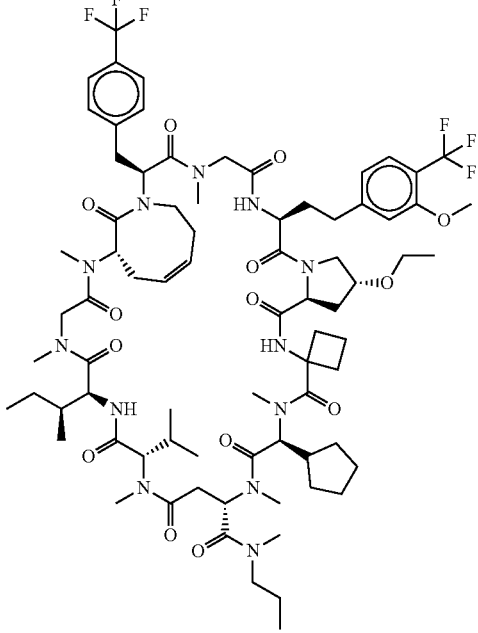 |
| PP2021 | 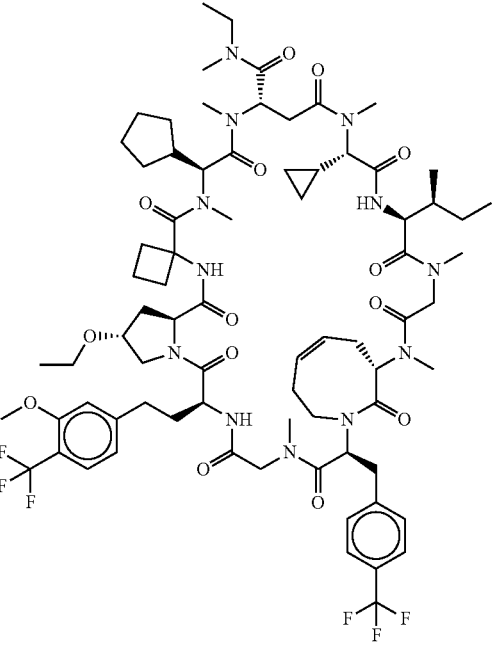 |

TABLE 38-continued

| Compound No. | Structural Formula |
|---|---|
| PP2022 | |
| PP2023 | |

TABLE 38-continued
| Compound No. | Structural Formula |
|---|---|
| PP2024 | 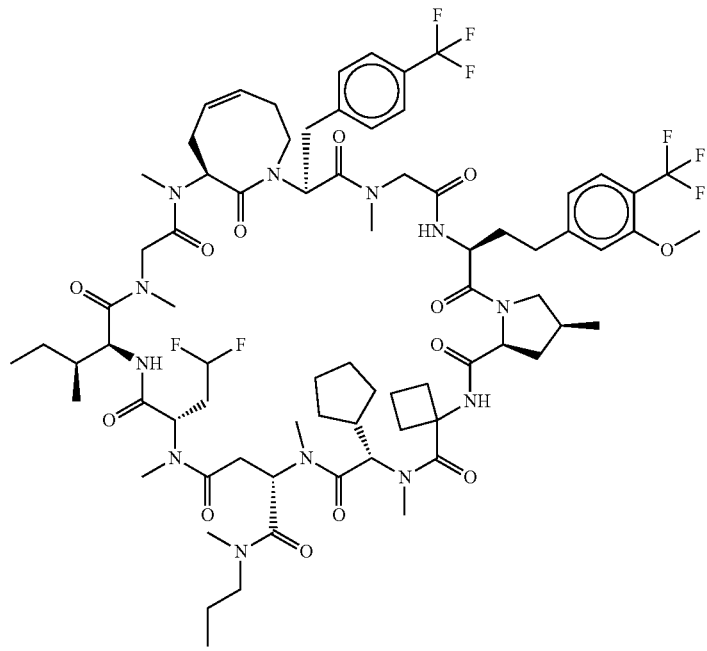 |
| PP2025 | 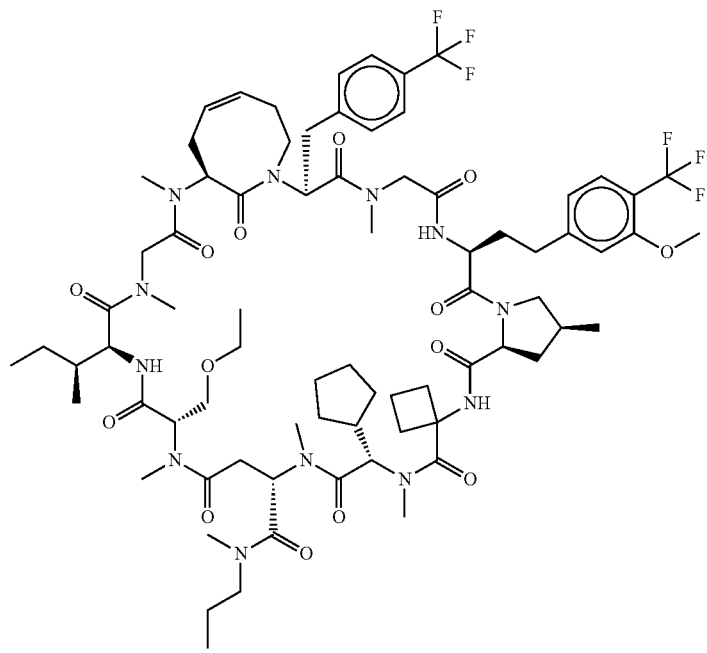 |

TABLE 38-continued

| Compound No. | Structural Formula |
|---|---|
| PP2026 | |
| PP2027 | |

TABLE 38-continued
| Compound No. | Structural Formula |
|---|---|
| PP2028 | 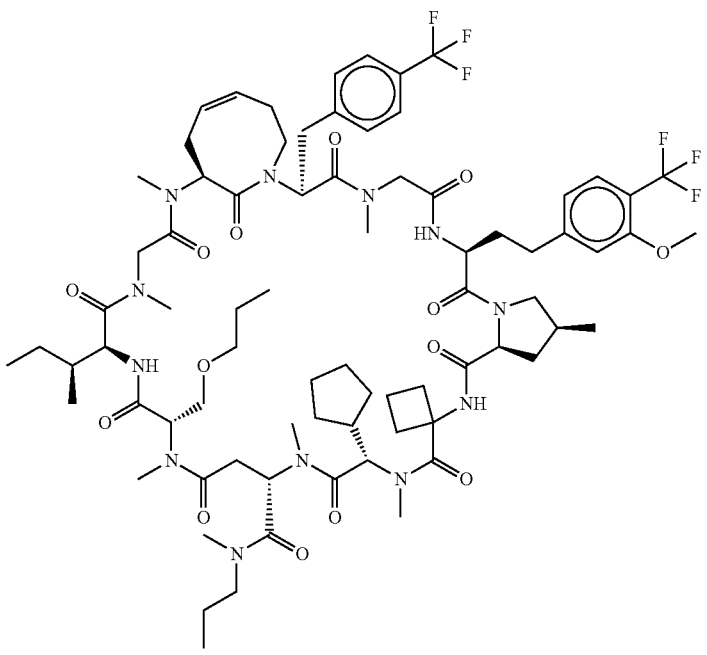 |
| PP2029 | 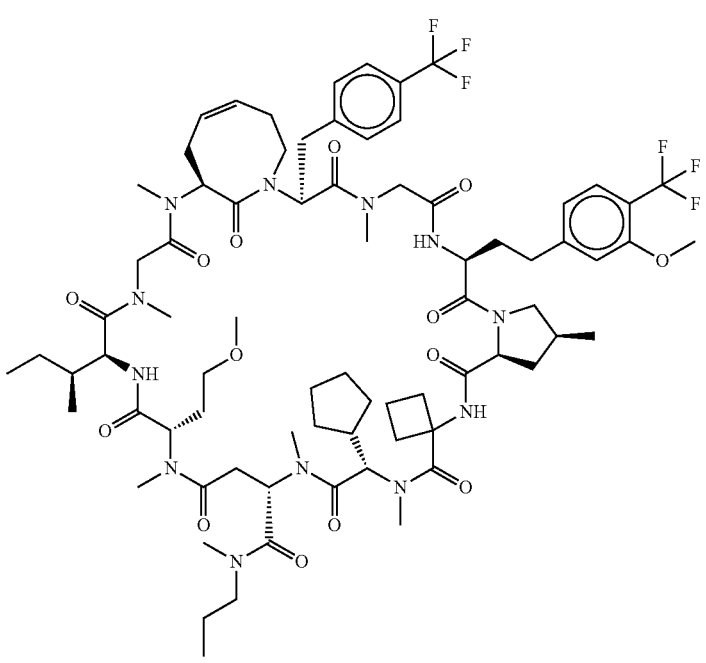 |

TABLE 38-continued

| Compound No. | Structural Formula |
| --- | --- |
| PP2030 | |
| PP2031 | |

TABLE 38-continued

| Compound No. | Structural Formula |
|---|---|
| PP2032 | |
| PP2033 | |

TABLE 38-continued
| Compound No. | Structural Formula |
|---|---|
| PP2034 | 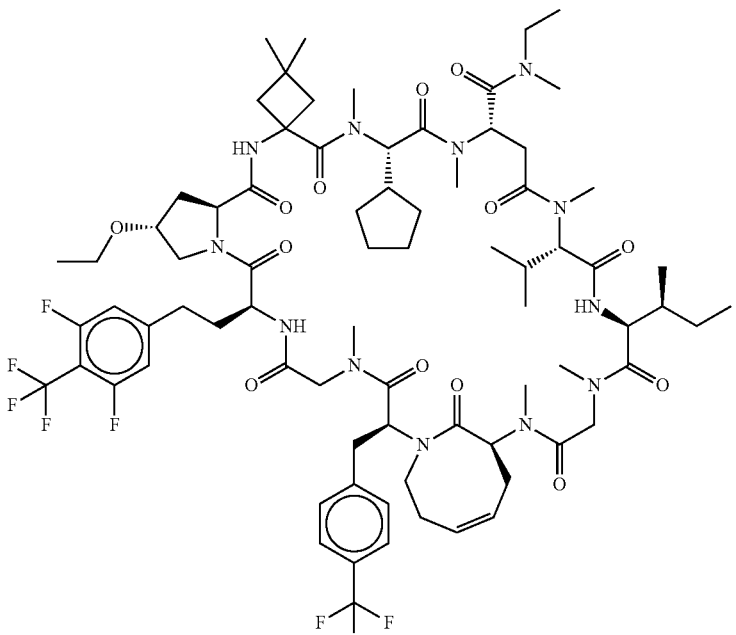 |
| PP2036 | 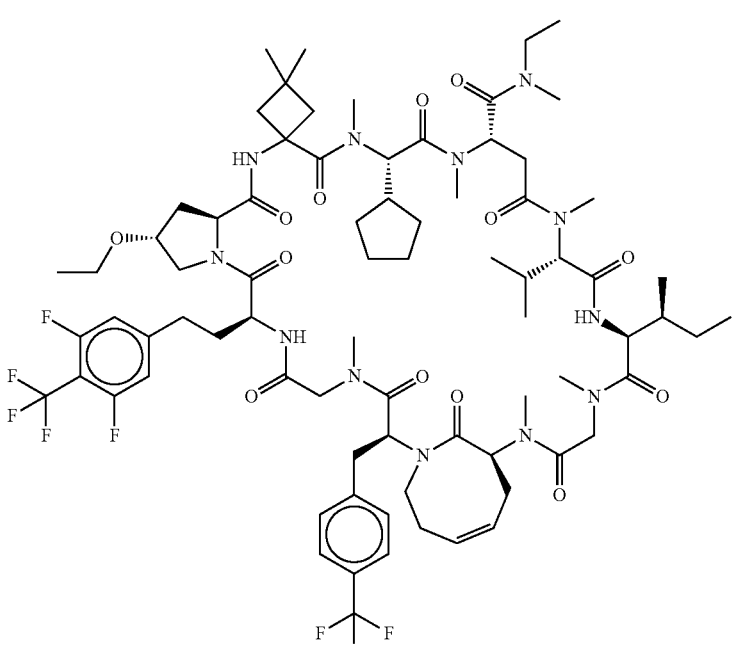 |

TABLE 38-continued

| Compound No. | Structural Formula |
|---|---|
| PP2037 | |
| PP2038 | |

TABLE 38-continued

| Compound No. | Structural Formula |
|---|---|
| PP2040 | |
| PP2041 | |

TABLE 38-continued

| Compound No. | Structural Formula |
|---|---|
| PP2042 | |
| PP2043 | |

TABLE 38-continued
| Compound No. | Structural Formula |
|---|---|
| PP2044 | 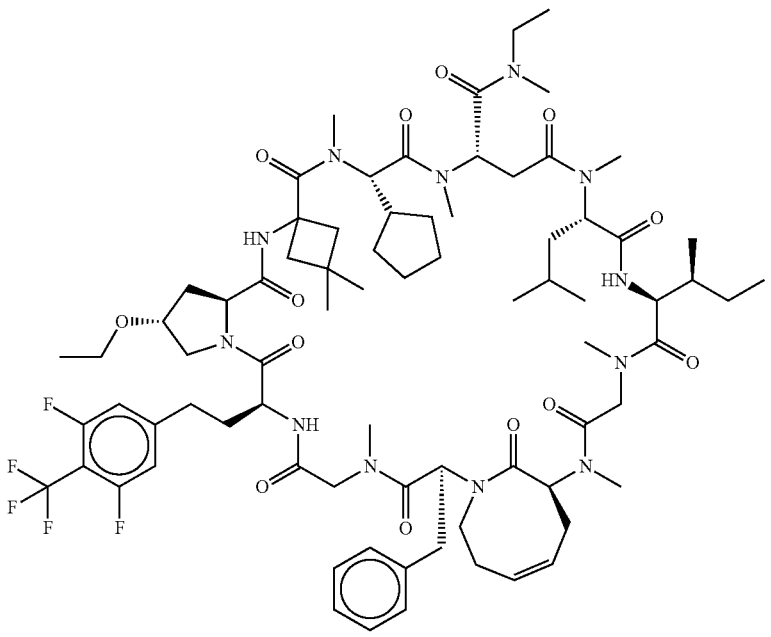 |
| PP2045 | 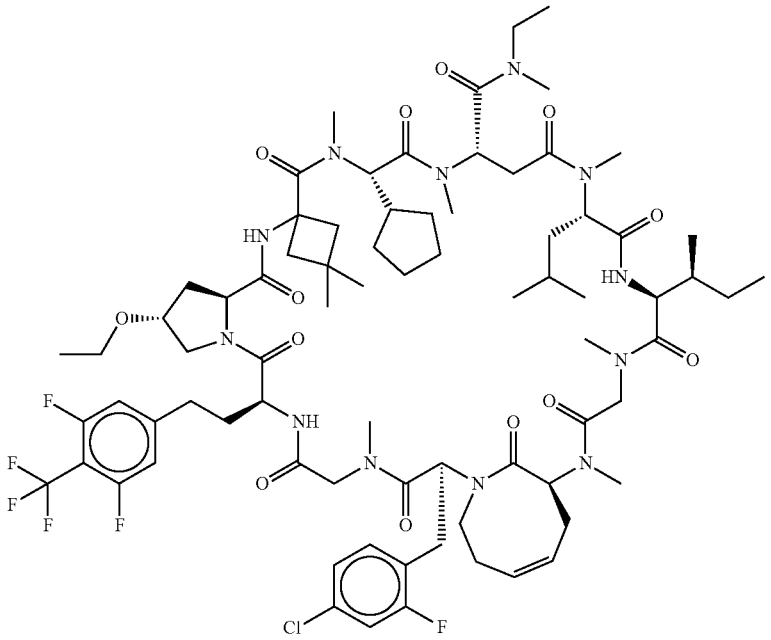 |

TABLE 38-continued
| Compound No. | Structural Formula |
|---|---|
| PP2046 | 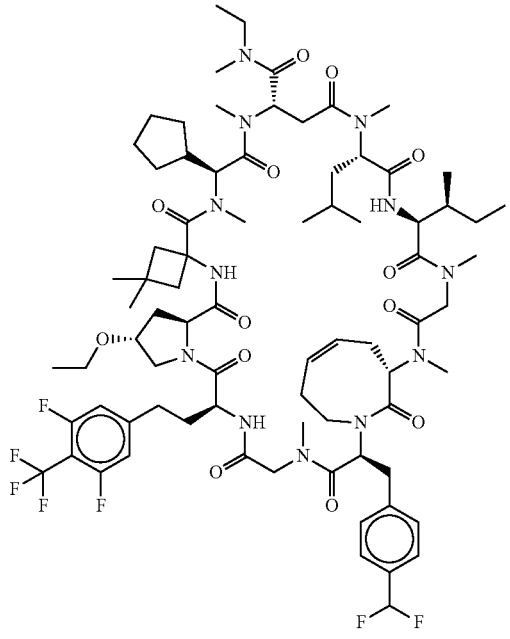 |
| PP2047 | 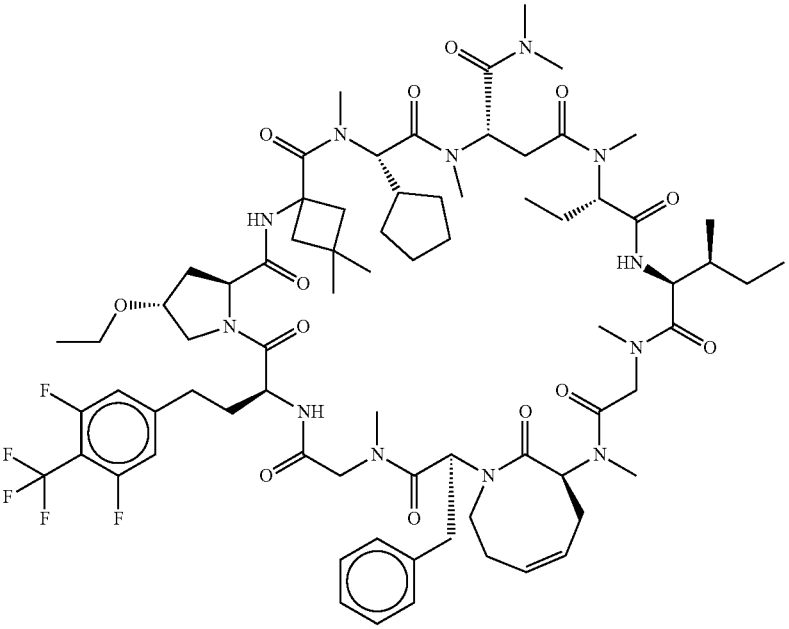 |

TABLE 38-continued
| Compound No. | Structural Formula |
|---|---|
| PP2048 | 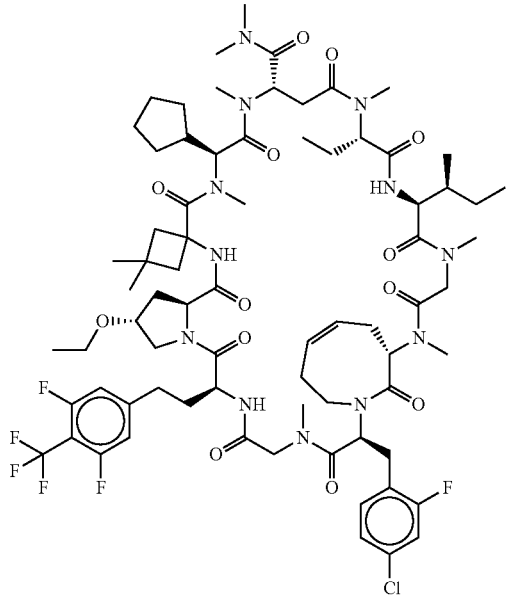 |
| PP2049 | 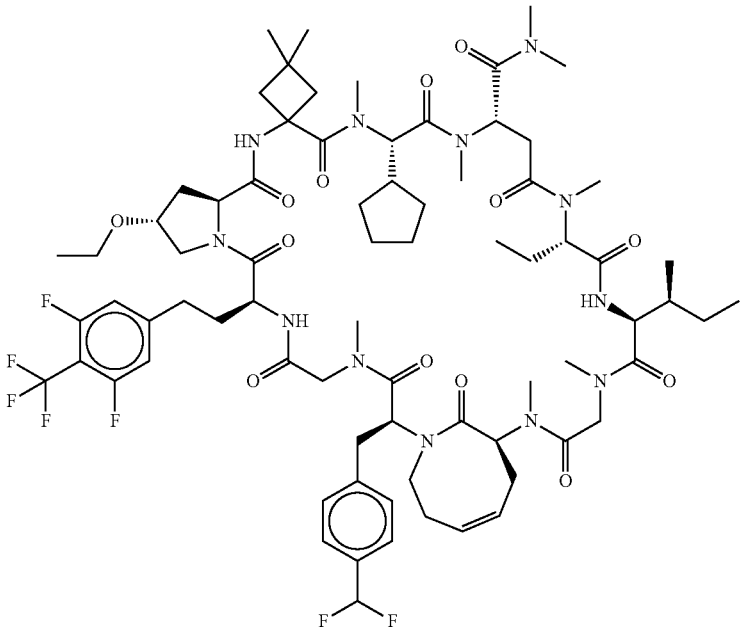 |

TABLE 38-continued
| Compound No. | Structural Formula |
|---|---|
| PP2050 | 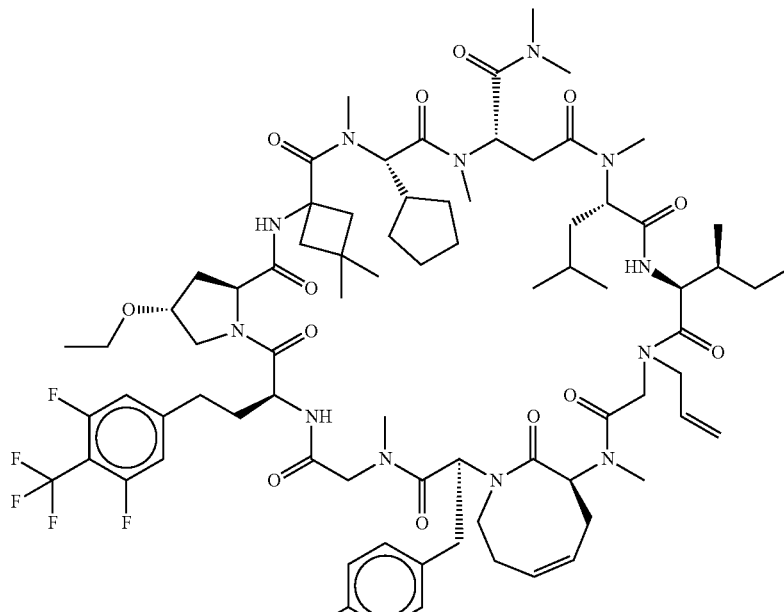 |
| PP2051 | 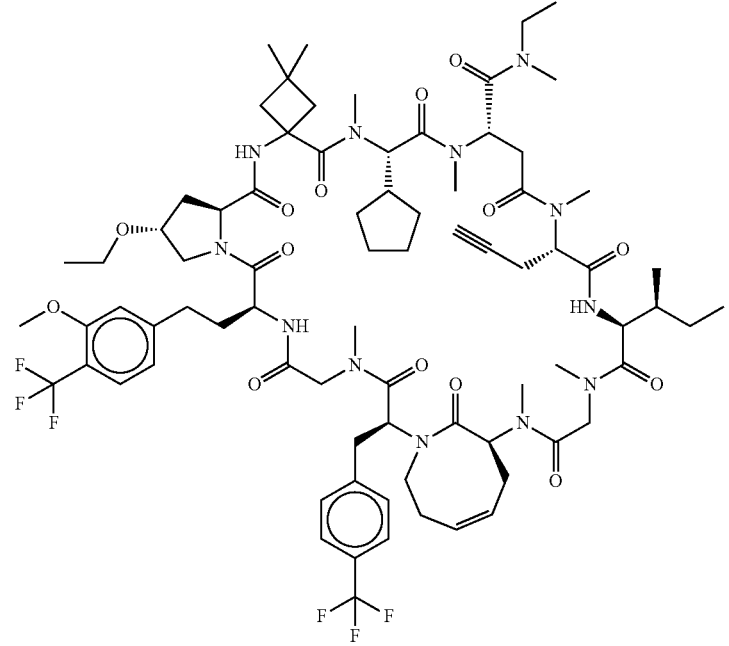 |

TABLE 38-continued

| Compound No. | Structural Formula |
|---|---|
| PP2052 | |
| PP2053 | |

TABLE 38-continued

| Compound No. | Structural Formula |
|---|---|
| PP2054 | |
| PP2055 | |

TABLE 38-continued
| Compound No. | Structural Formula |
|---|---|
| PP2056 | 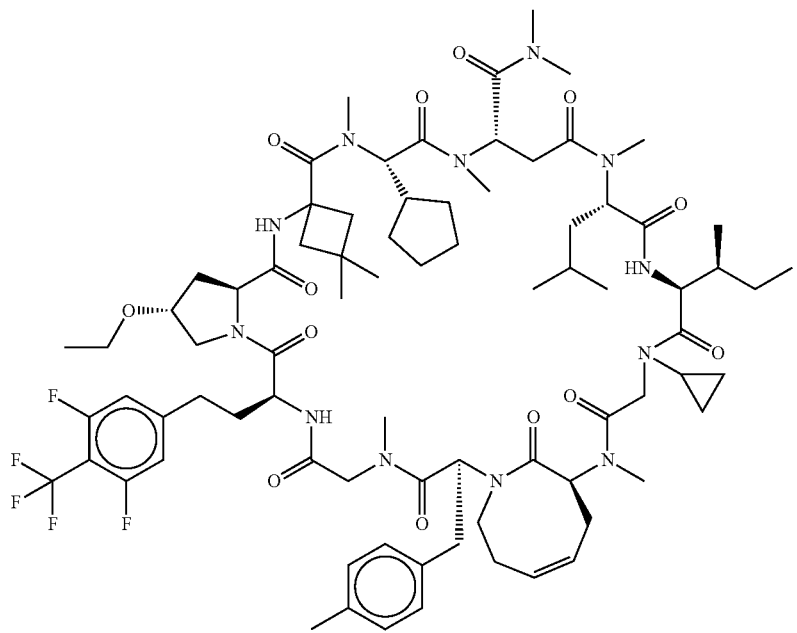 |
| PP2057 | 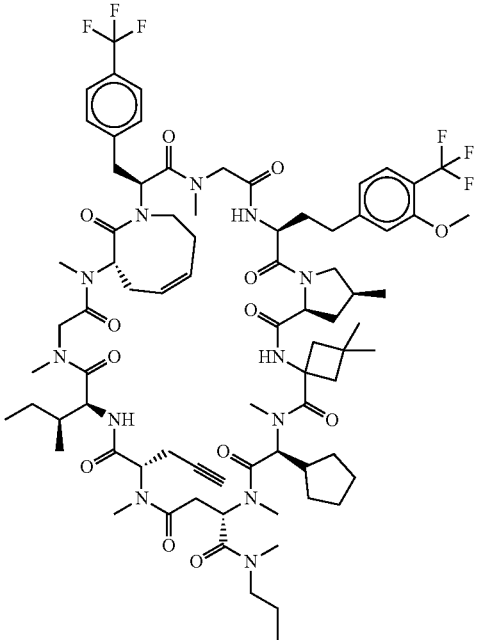 |

TABLE 38-continued
| Compound No. | Structural Formula |
|---|---|
| PP2058 | 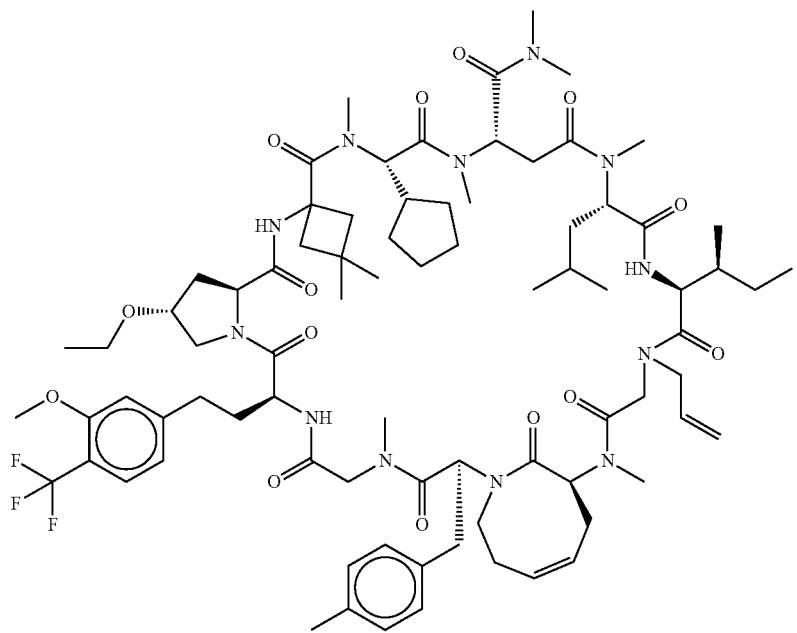 |
| PP2059 | 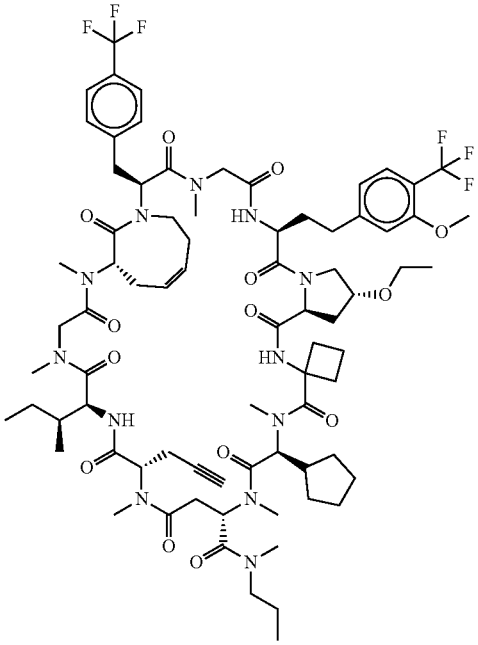 |

| Compound No. | Structural Formula |
|---|---|
| PP2060 | 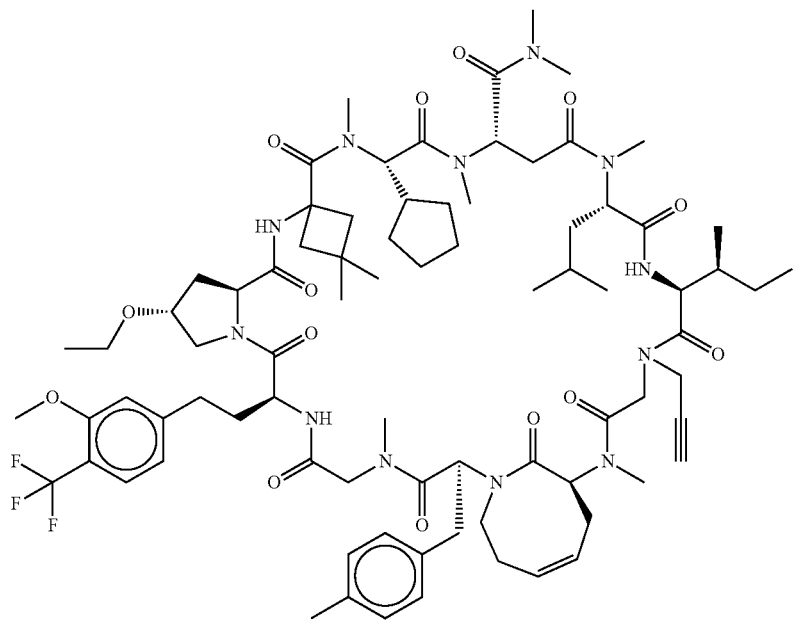 |
| PP2061 | 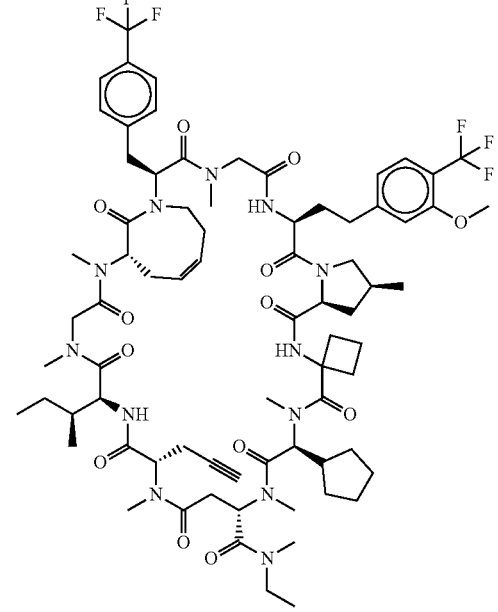 |

TABLE 38-continued

| Compound No. | Structural Formula |
|---|---|
| PP2062 | |
| PP2063 | |

TABLE 38-continued

| Compound No. | Structural Formula |
|---|---|
| PP2064 | |
| PP2065 | |

TABLE 38-continued

| Compound No. | Structural Formula |
|---|---|
| PP2066 | |
| PP2067 | |

TABLE 38-continued

| Compound No. | Structural Formula |
|---|---|
| PP2068 | |
| PP2069 | |

TABLE 38-continued

| Compound No. | Structural Formula |
|---|---|
| PP2070 | |
| PP2071 | |

TABLE 38-continued
| Compound No. | Structural Formula |
|---|---|
| PP2072 | 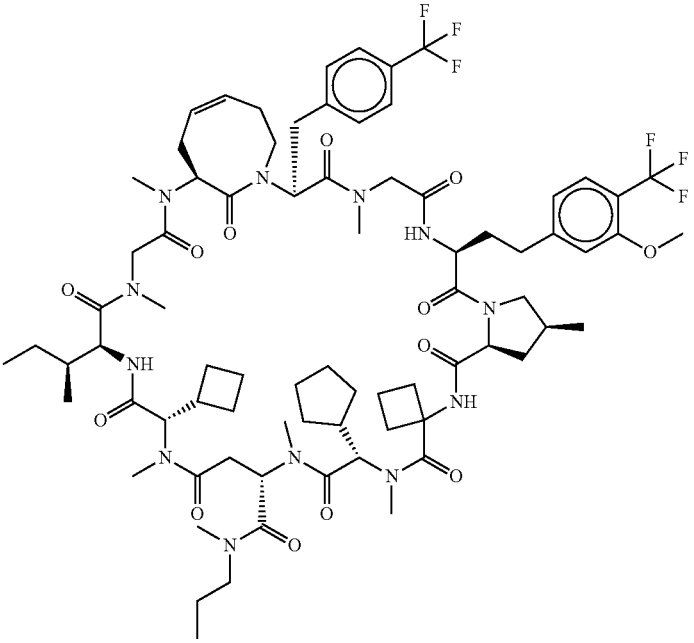 |
| PP2073 | 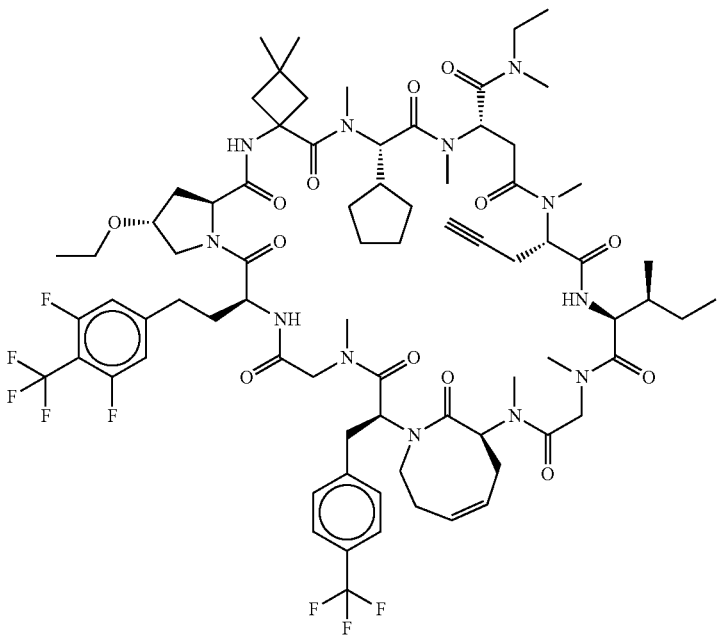 |

TABLE 38-continued

| Compound No. | Structural Formula |
|---|---|
| PP2074 | |
| PP2075 | |

TABLE 38-continued

| Compound No. | Structural Formula |
|---|---|
| PP2076 | |
| PP2077 | |

TABLE 38-continued
| Compound No. | Structural Formula |
|---|---|
| PP2078 | 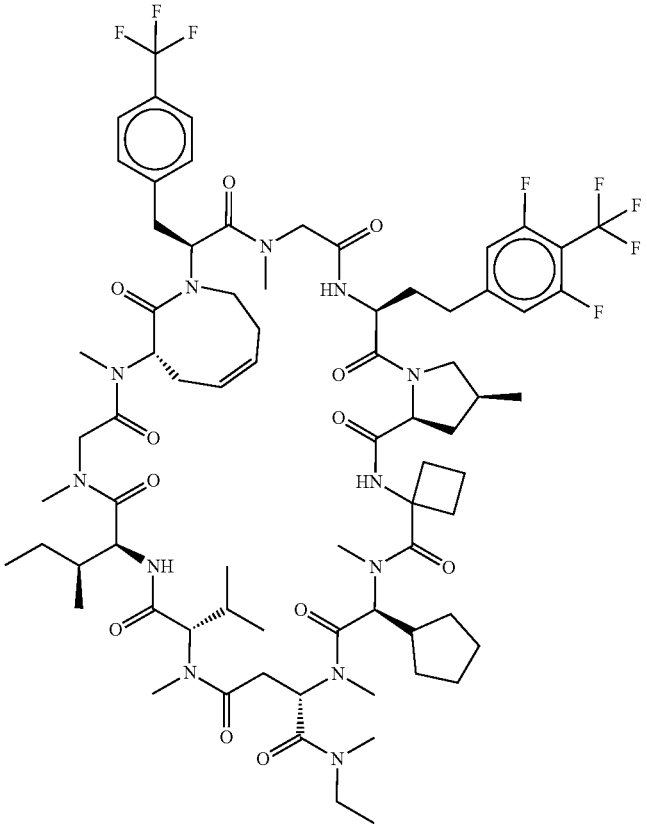 |
| PP2079 | 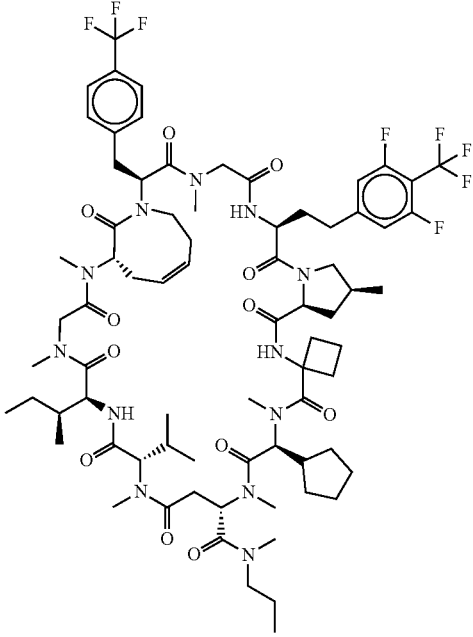 |

TABLE 38-continued

| Compound No. | Structural Formula |
|---|---|
| PP2080 | |
| PP2081 | |

TABLE 38-continued

| Compound No. | Structural Formula |
|---|---|
| PP2082 | |
| PP2083 | |

TABLE 38-continued
| Compound No. | Structural Formula |
|---|---|
| PP2087 | 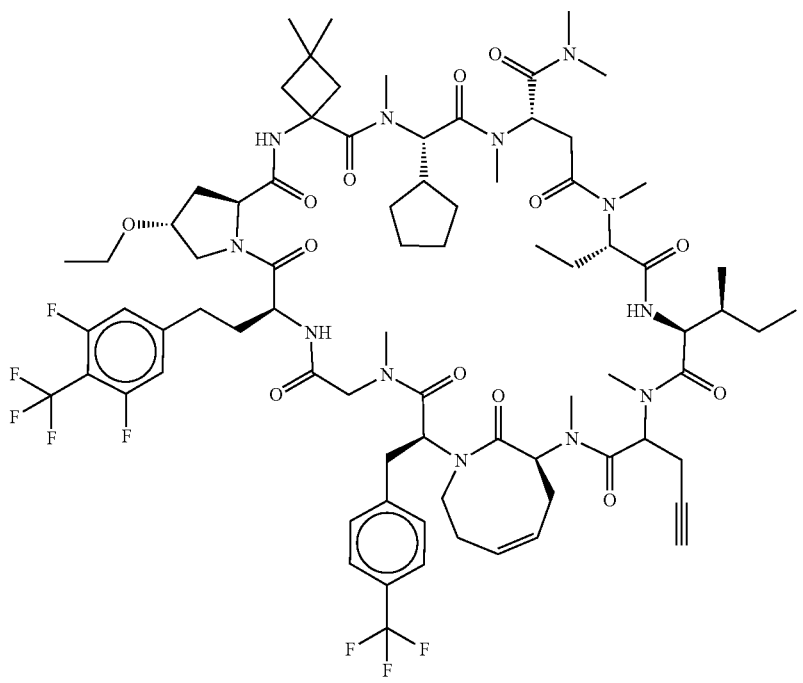 |
| PP2091 | 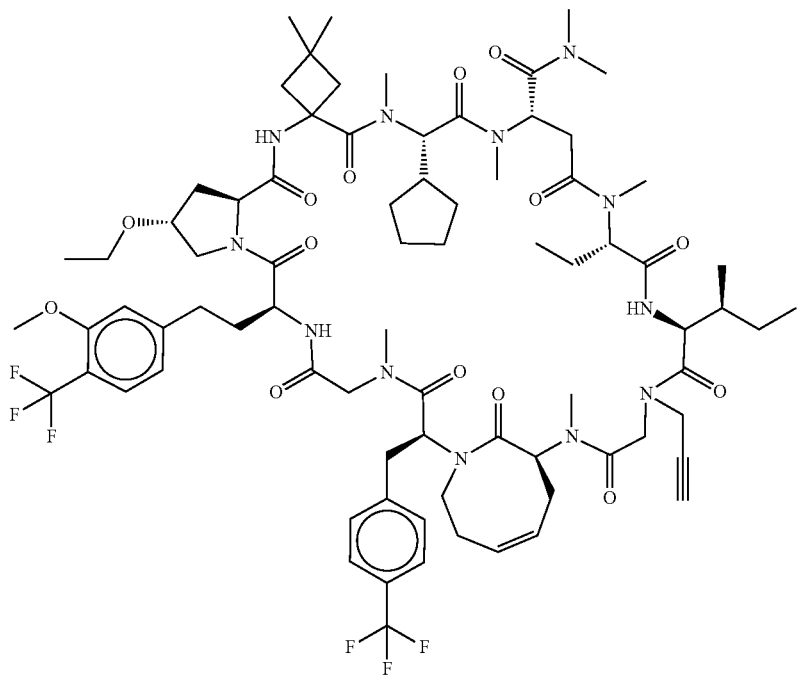 |

TABLE 38-continued
| Compound No. | Structural Formula |
|---|---|
| PP2093 | 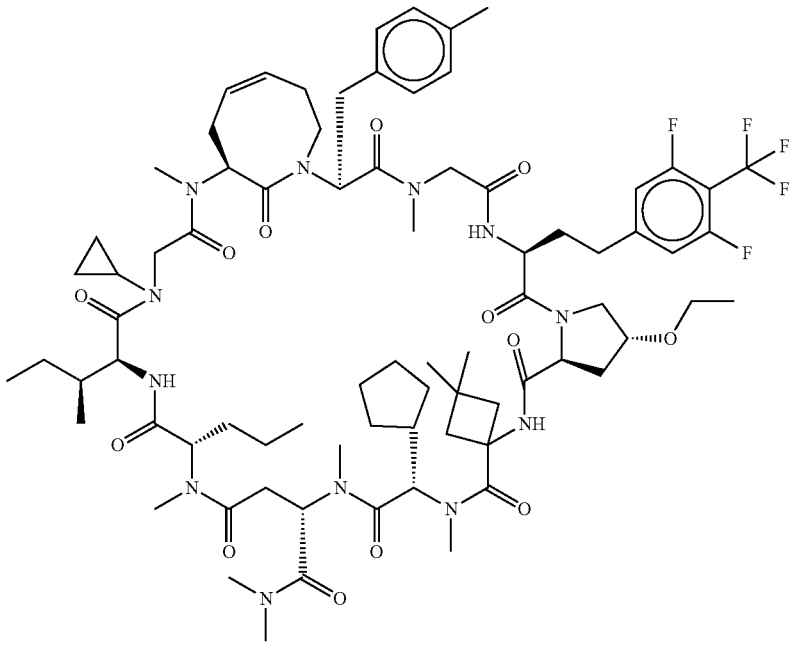 |
| PP2094 | 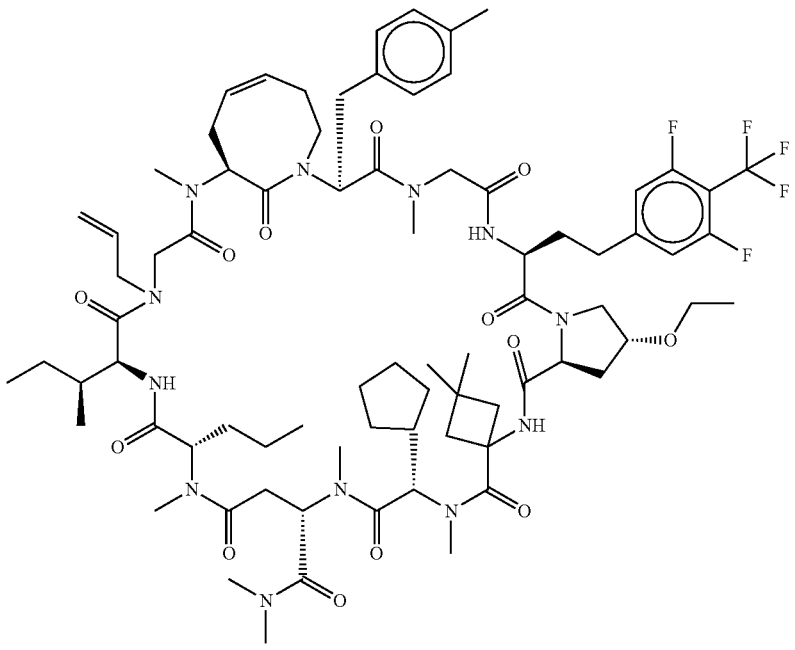 |

TABLE 38-continued

| Compound No. | Structural Formula |
|---|---|
| PP2095 | |
| PP2096 | |

TABLE 38-continued
| Compound No. | Structural Formula |
|---|---|
| PP2097 | 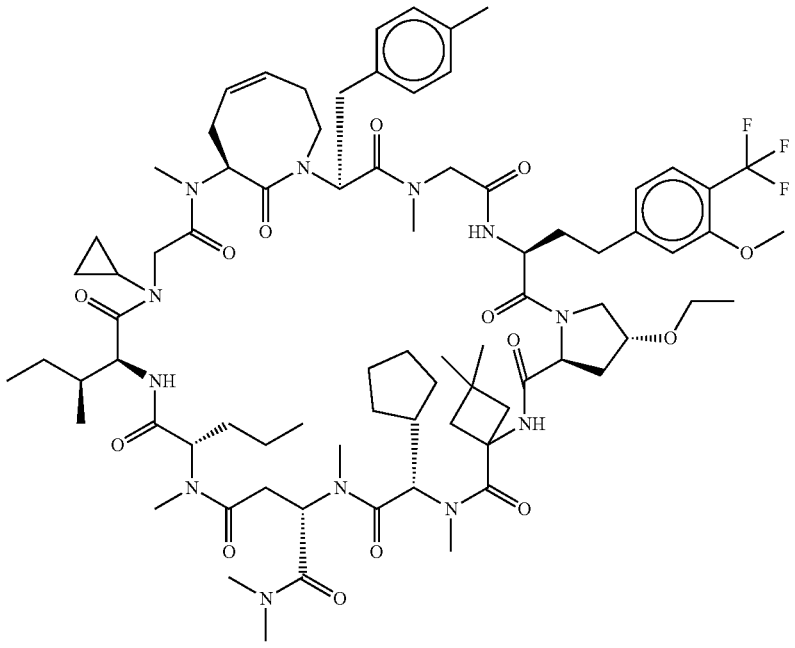 |
| PP2098 | 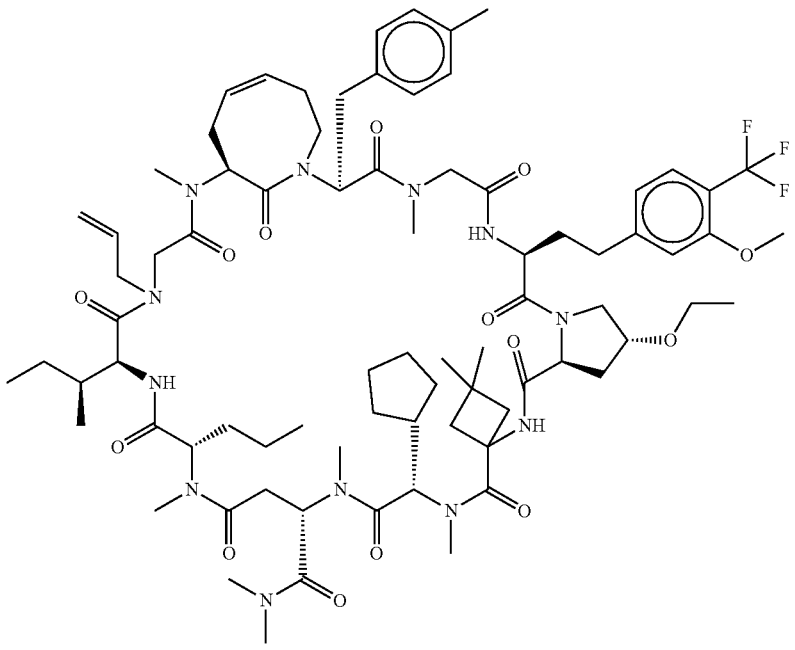 |

| Compound No. | Structural Formula |
|---|---|
| PP2099 | 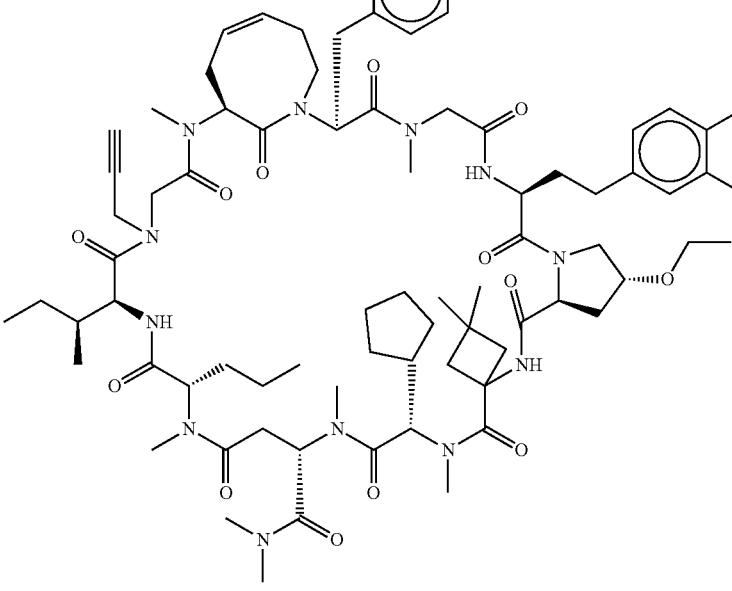 |
| PP2101 | 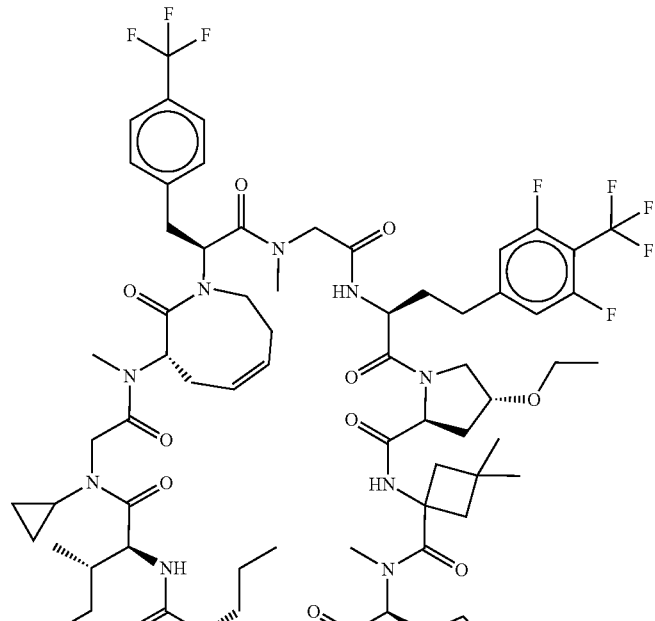 |

TABLE 38-continued
| Compound No. | Structural Formula |
|---|---|
| PP2102 | 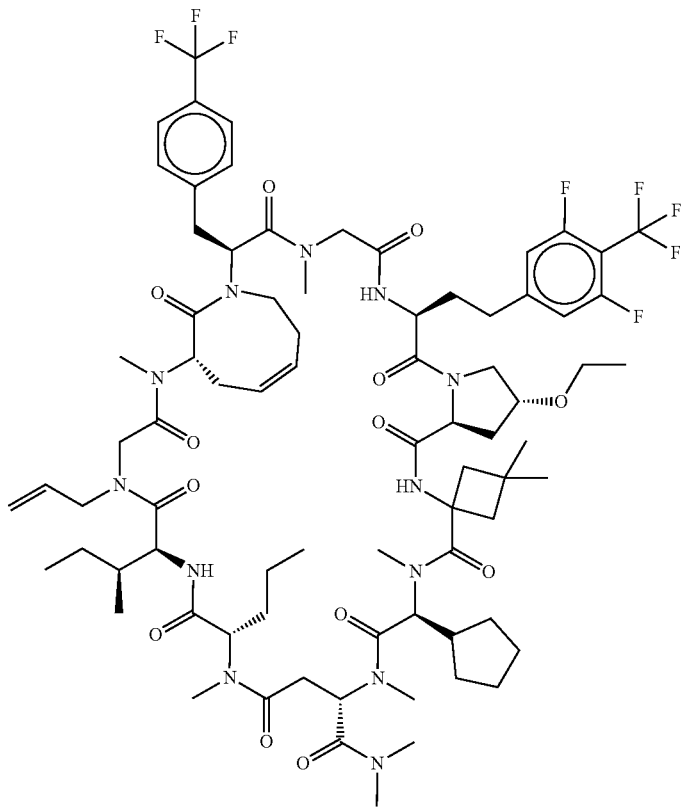 |
| PP2103 | 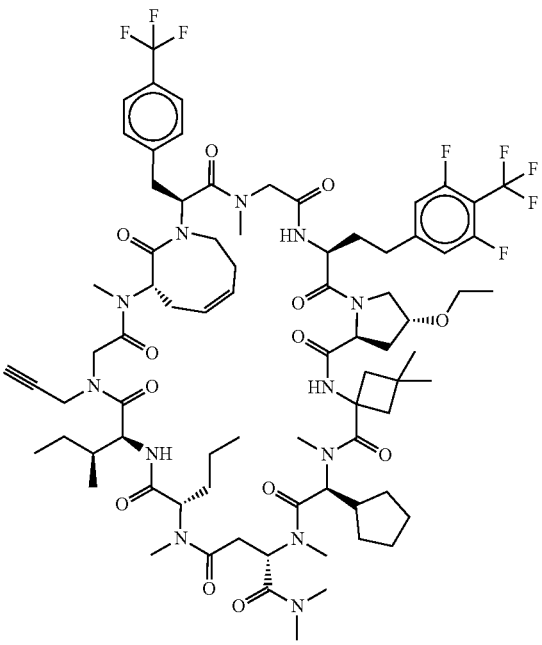 |

TABLE 38-continued
| Compound No. | Structural Formula |
|---|---|
| PP2105 | 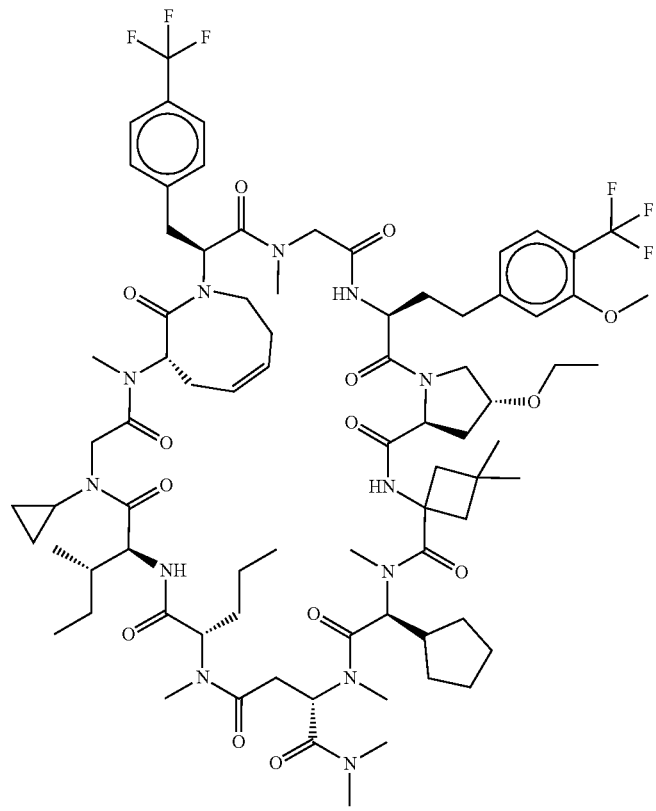 |
| PP2106 | 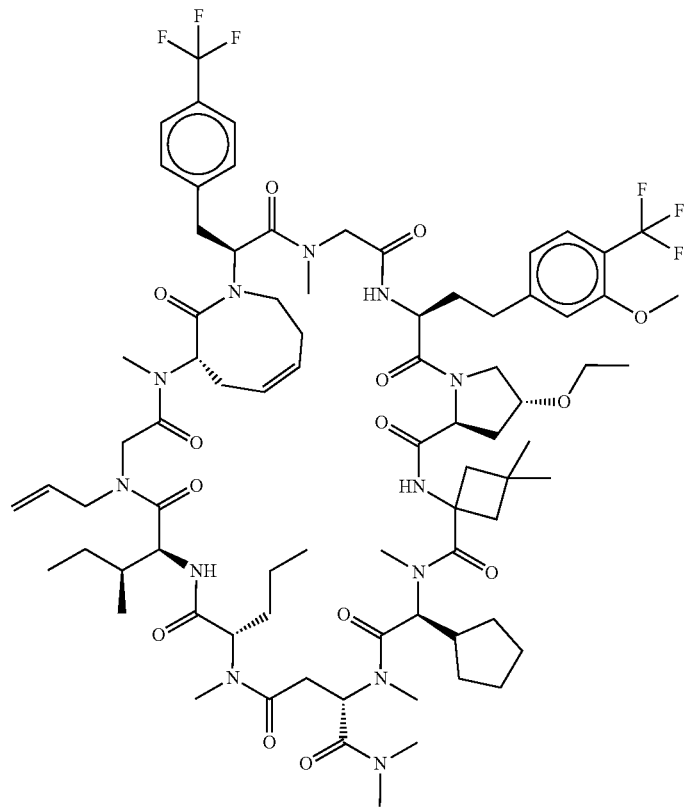 |

TABLE 38-continued

| Compound No. | Structural Formula |
| --- | --- |
| PP2107 | |
| PP2108 | |

TABLE 38-continued

| Compound No. | Structural Formula |
|---|---|
| PP2109 | |
| PP2110 | |

TABLE 38-continued

| Compound No. | Structural Formula |
|---|---|
| PP2111 | |
| PP2112 | |

TABLE 38-continued
| Compound No. | Structural Formula |
|---|---|
| PP2113 | 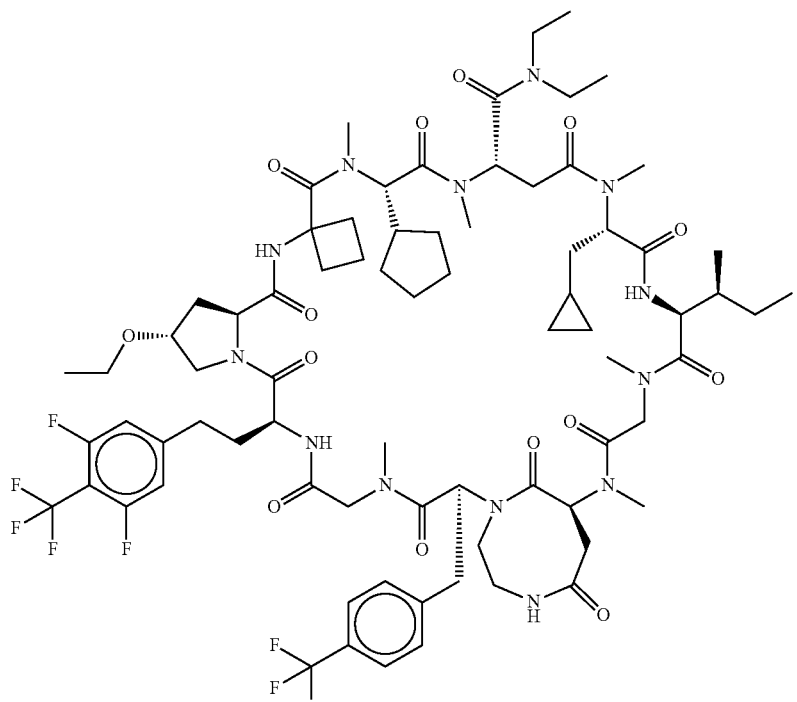 |
| PP2114 | 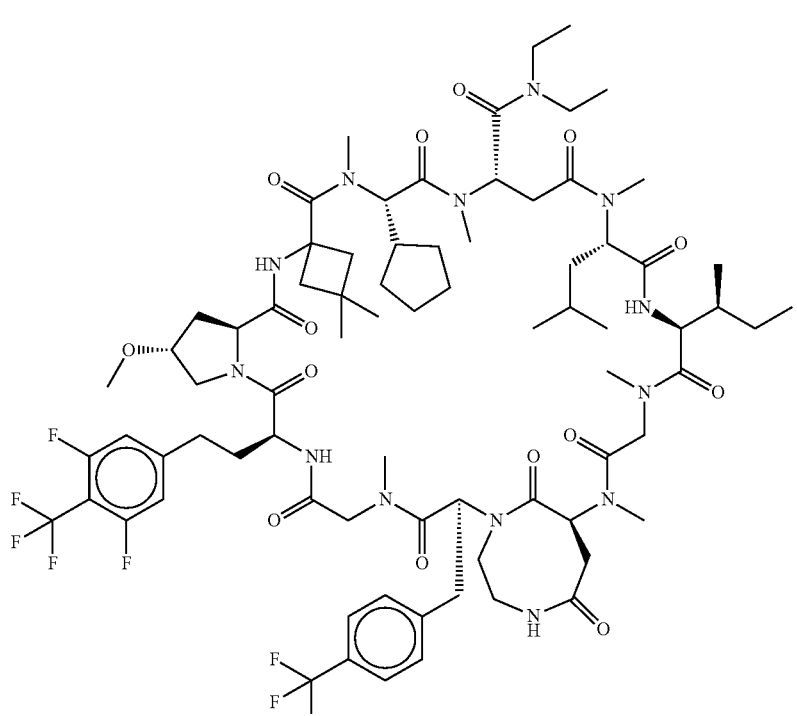 |

TABLE 38-continued
| Compound No. | Structural Formula |
|---|---|
| PP2115 | 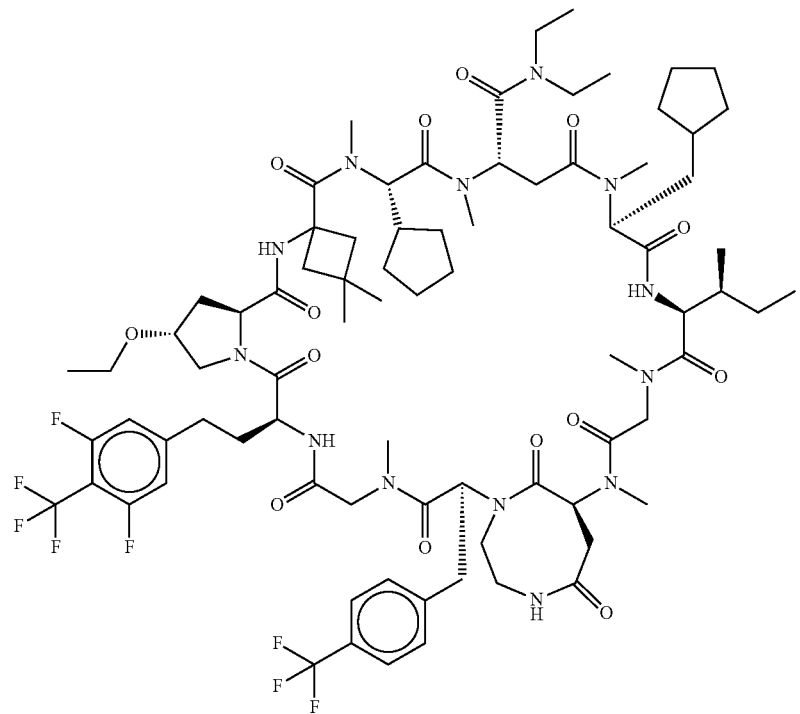 |
| PP2116 | 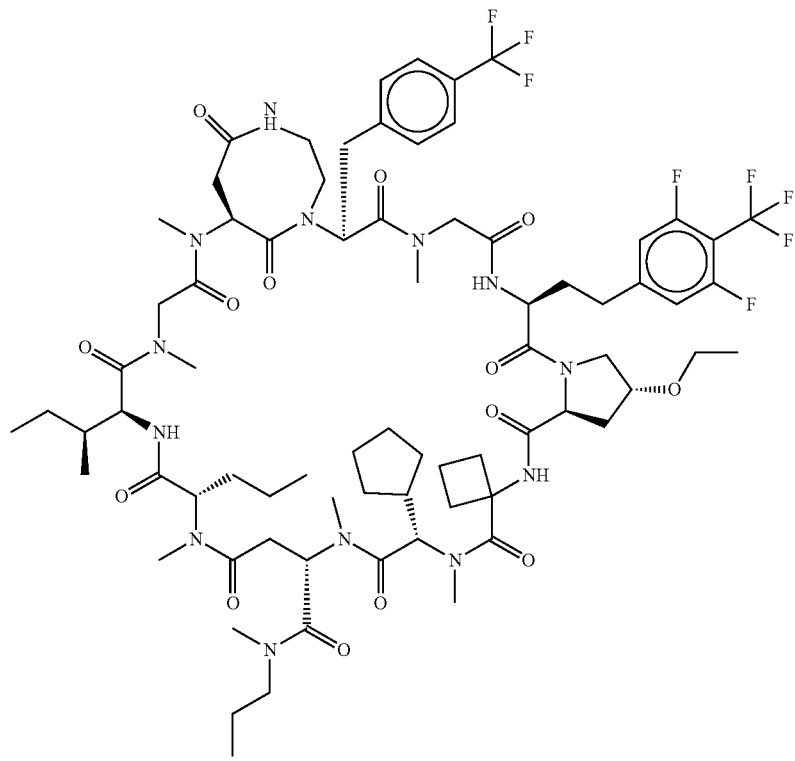 |

TABLE 38-continued

| Compound No. | Structural Formula |
| --- | --- |
| PP2117 | |
| PP2118 | |

TABLE 38-continued
| Compound No. | Structural Formula |
|---|---|
| PP2119 | 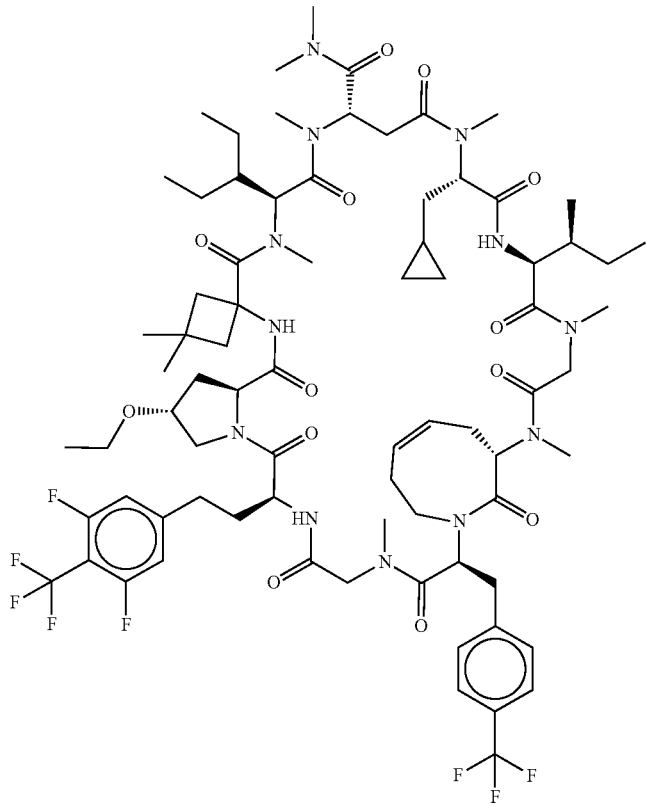 |
| PP2120 | 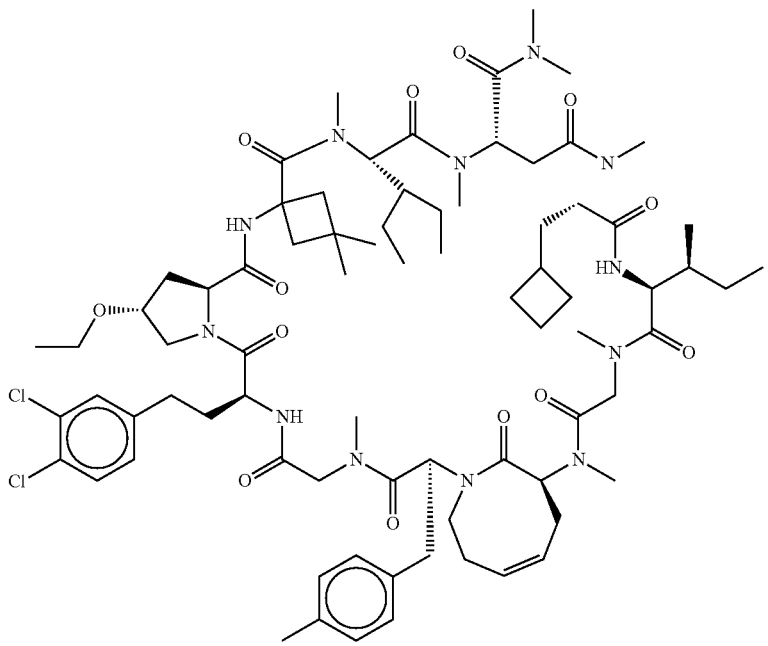 |

TABLE 38-continued

| Compound No. | Structural Formula |
|---|---|
| PP2121 | |
| PP2122 | |

TABLE 38-continued
| Compound No. | Structural Formula |
|---|---|
| PP2123 | 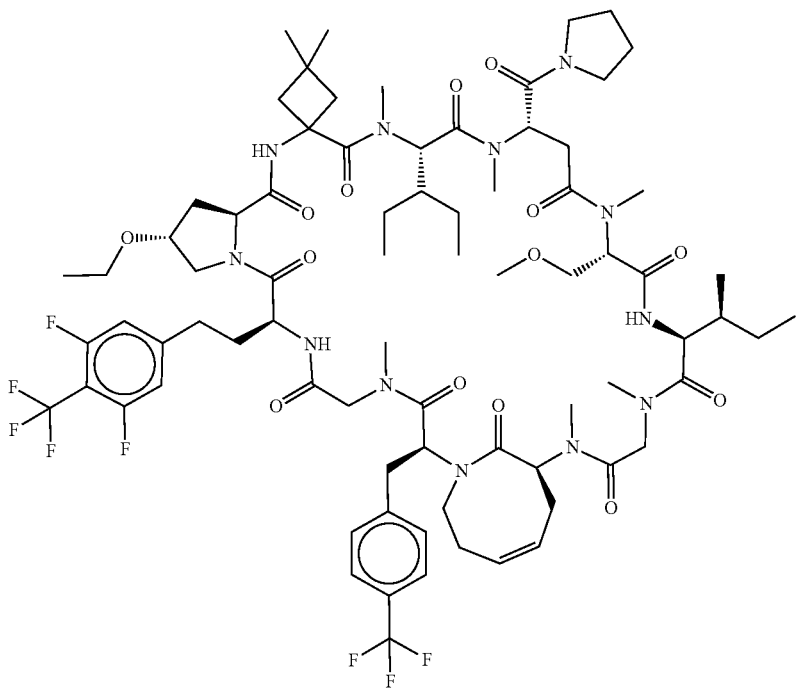 |
| PP2124 | 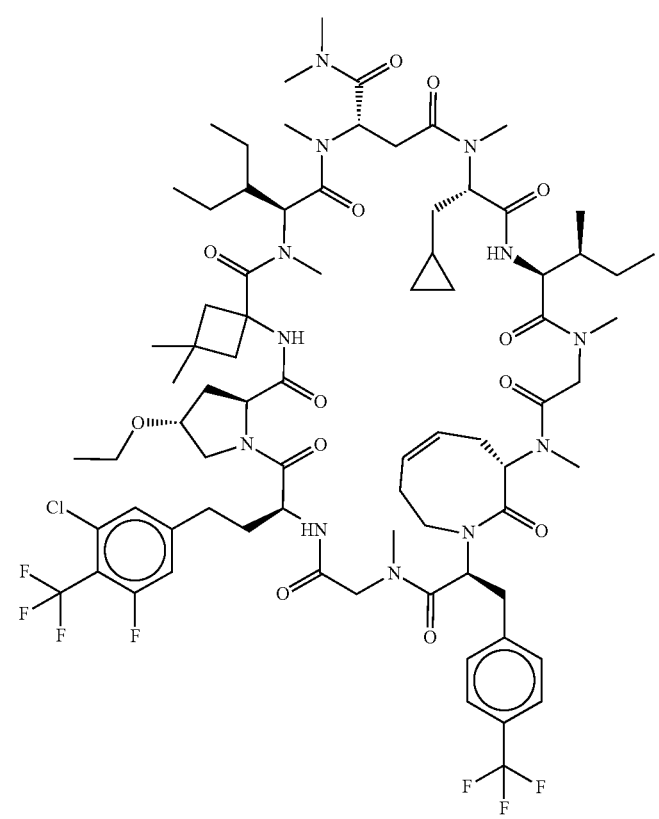 |

TABLE 38-continued

| Compound No. | Structural Formula |
| --- | --- |
| PP2125 | |
| PP2126 | |

TABLE 38-continued
| Compound No. | Structural Formula |
|---|---|
| PP2127 | 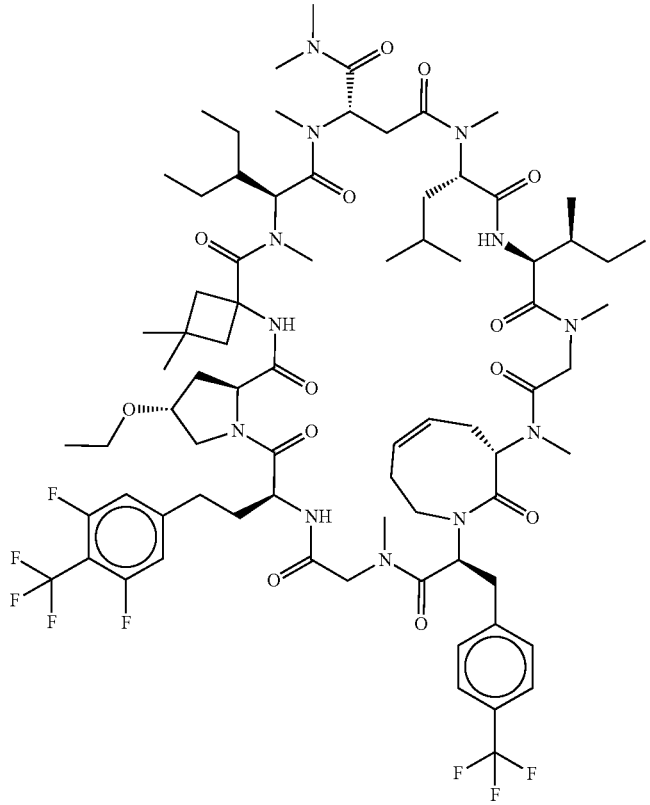 |
| PP2128 | 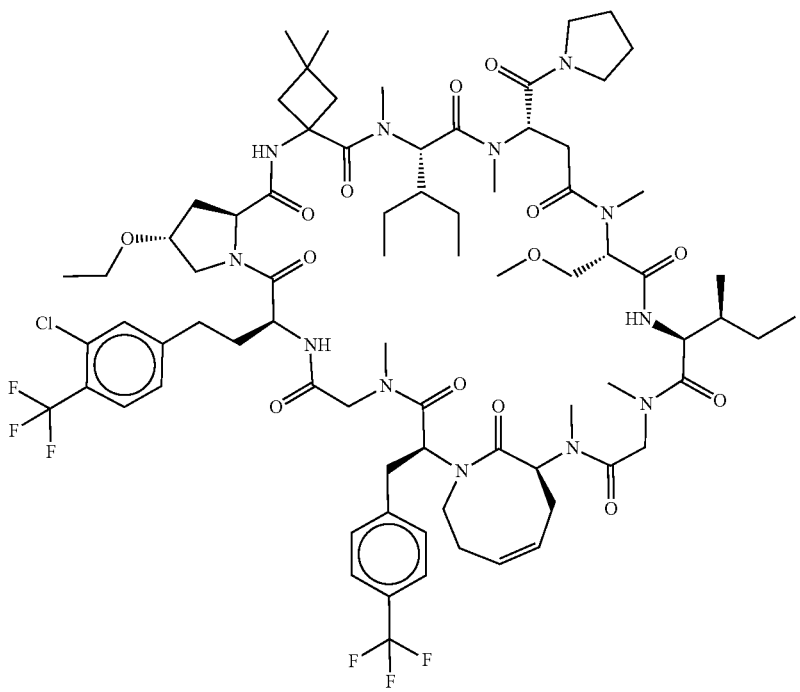 |

| Compound No. | Structural Formula |
|---|---|
| PP2130 | 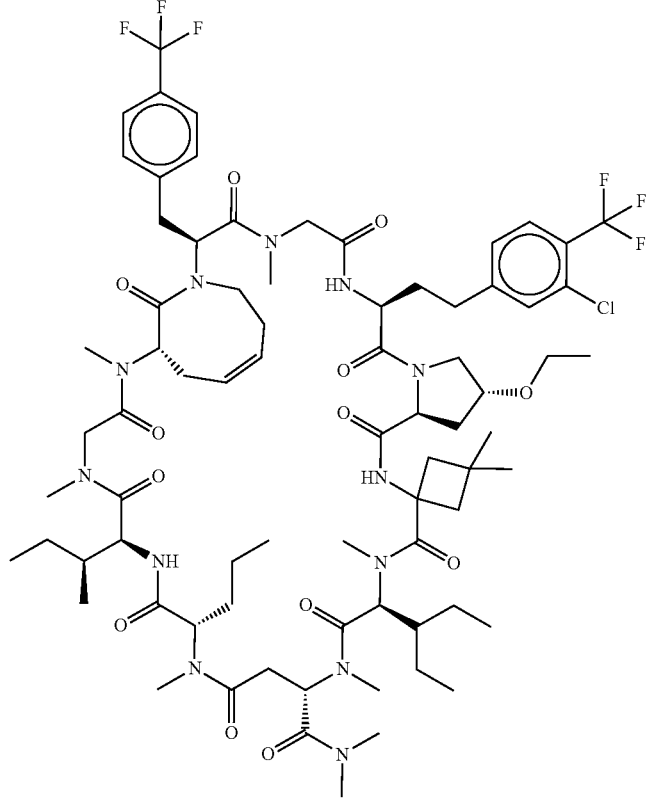 |
| PP2131 | 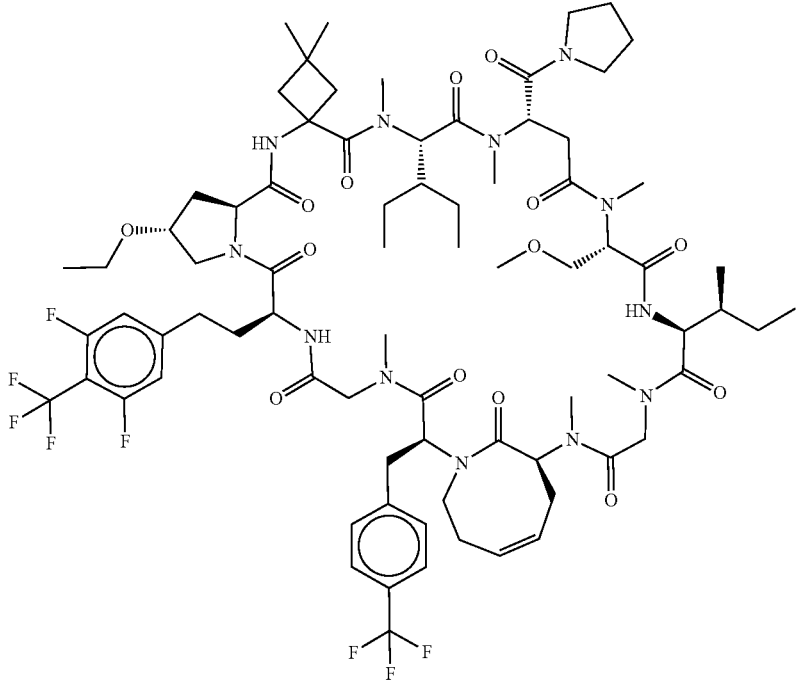 |

TABLE 38-continued

| Compound No. | Structural Formula |
|---|---|
| PP2132 | |
| PP2133 | |

TABLE 38-continued

| Compound No. | Structural Formula |
|---|---|
| PP2135 | |
| PP2137 | |

TABLE 38-continued
| Compound No. | Structural Formula |
|---|---|
| PP2138 | 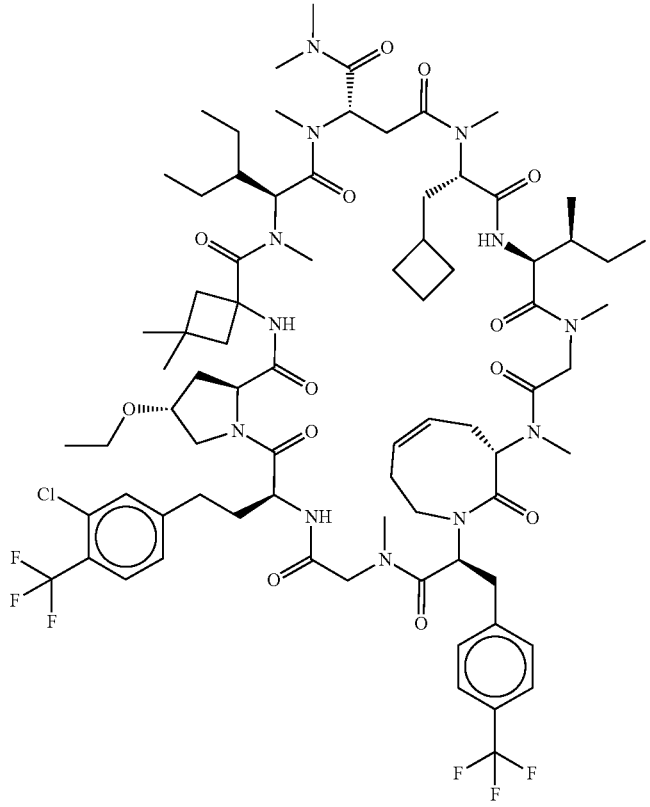 |
| PP2139 | 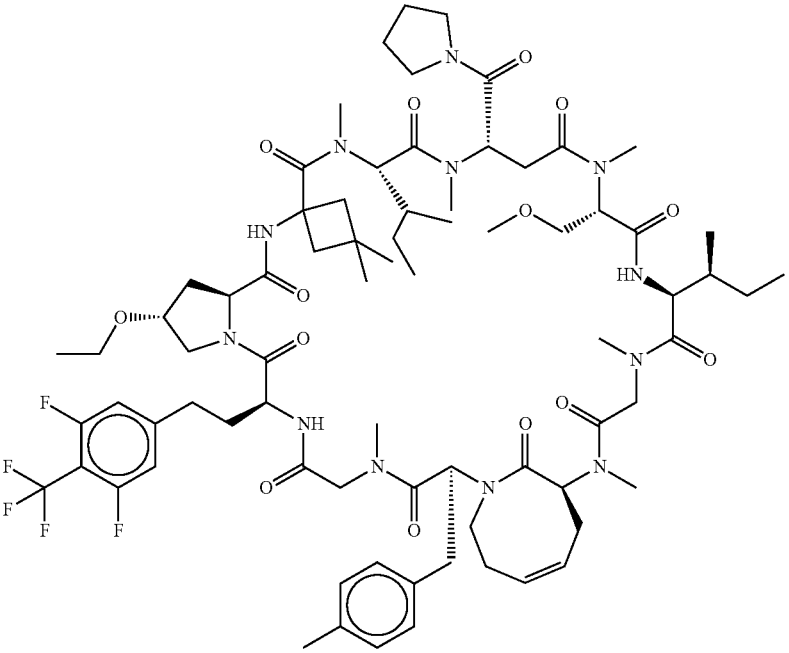 |

TABLE 38-continued

| Compound No. | Structural Formula |
|---|---|
| PP2140 | |
| PP2141 | |

TABLE 38-continued
| Compound No. | Structural Formula |
|---|---|
| PP2142 | 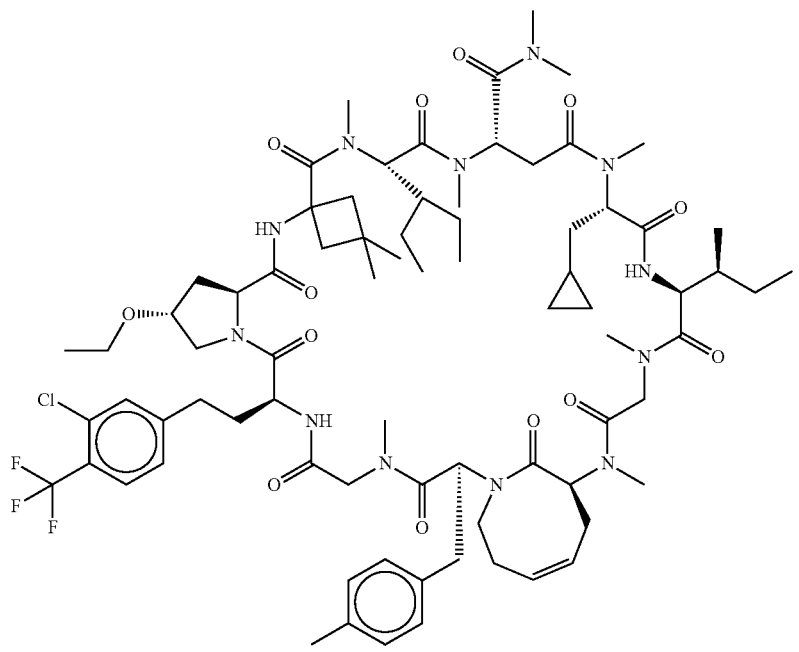 |
| PP2143 | 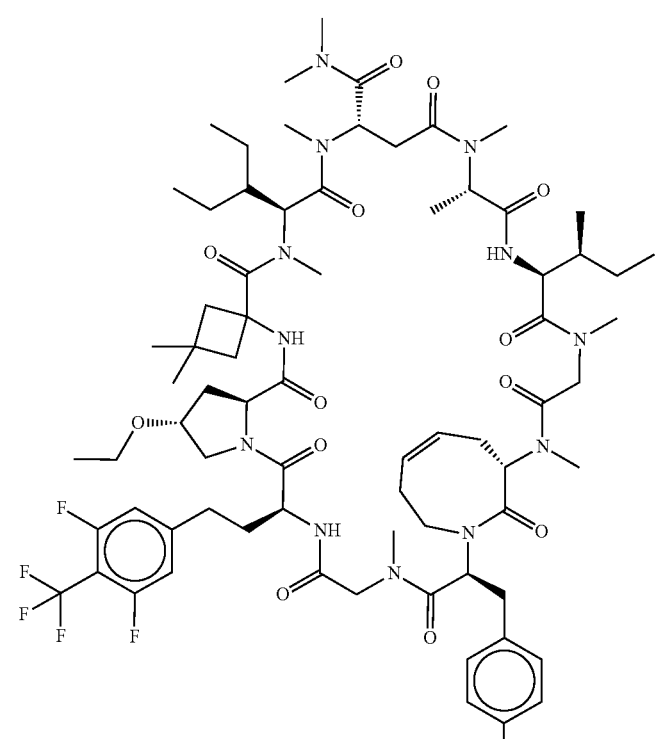 |

TABLE 38-continued
| Compound No. | Structural Formula |
|---|---|
| PP2144 | 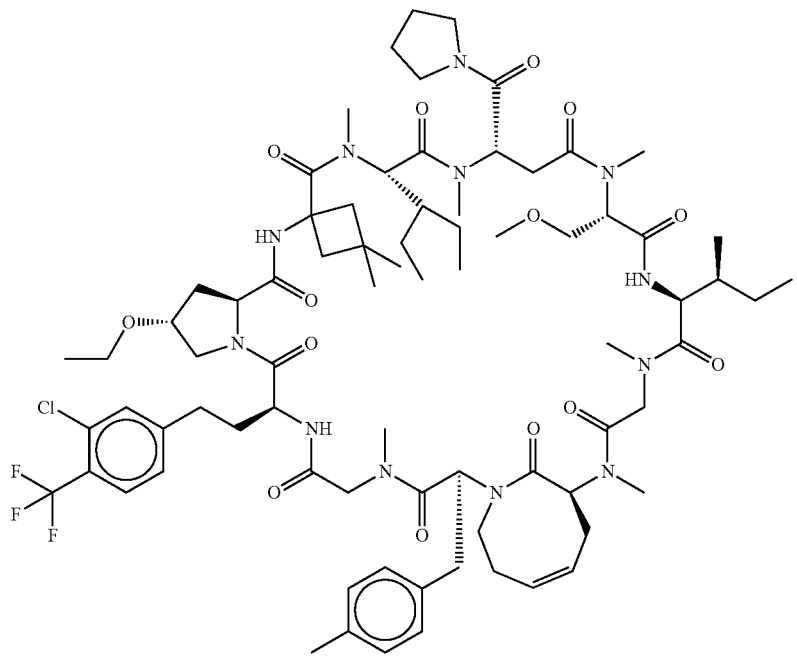 |
| PP2145 | 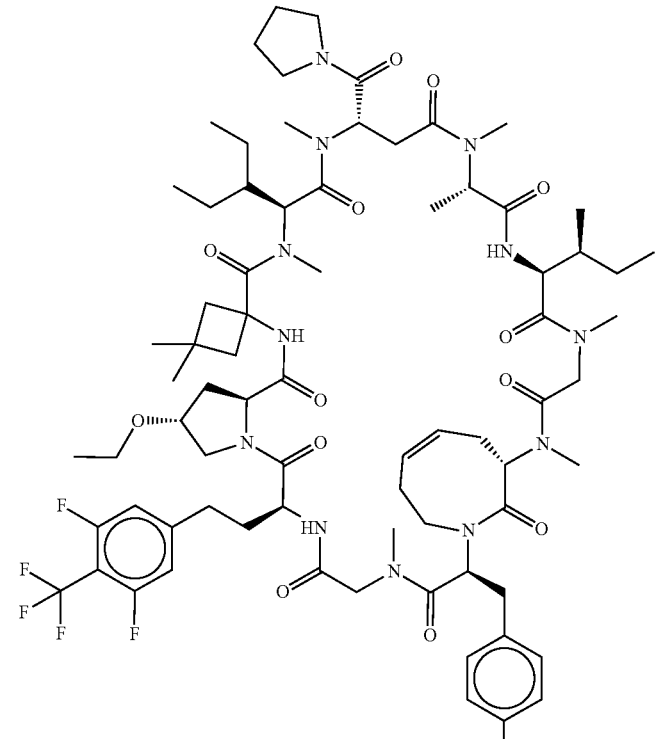 |

TABLE 38-continued

| Compound No. | Structural Formula |
|---|---|
| PP2146 | |
| PP2147 | |

TABLE 38-continued
| Compound No. | Structural Formula |
|---|---|
| PP2148 | 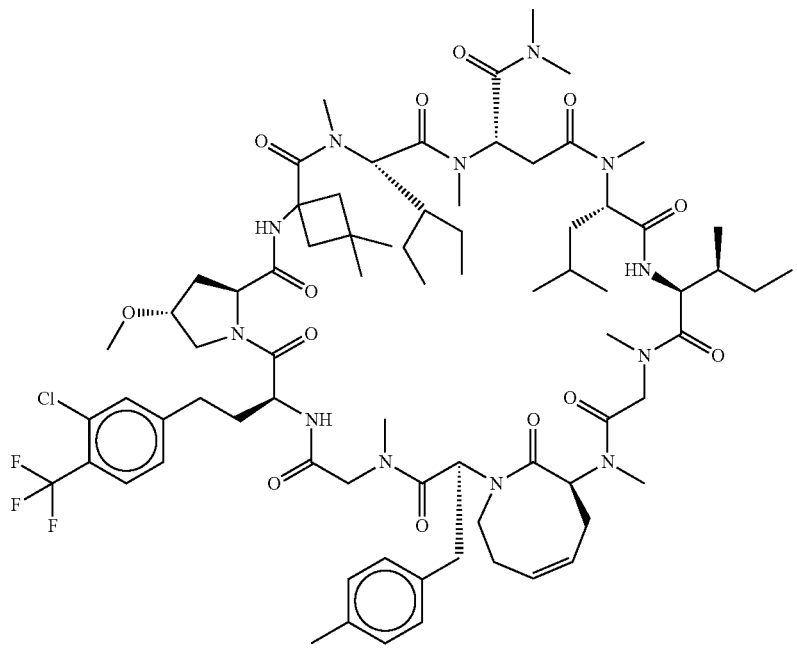 |
| PP2149 | 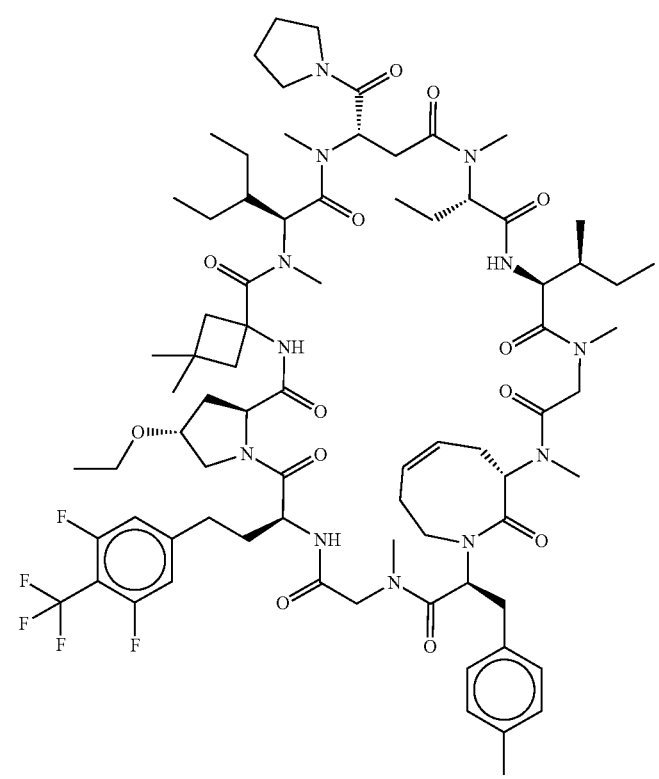 |

TABLE 38-continued

| Compound No. | Structural Formula |
|---|---|
| PP2150 | |
| PP2151 | |

TABLE 38-continued
| Compound No. | Structural Formula |
|---|---|
| PP2152 | 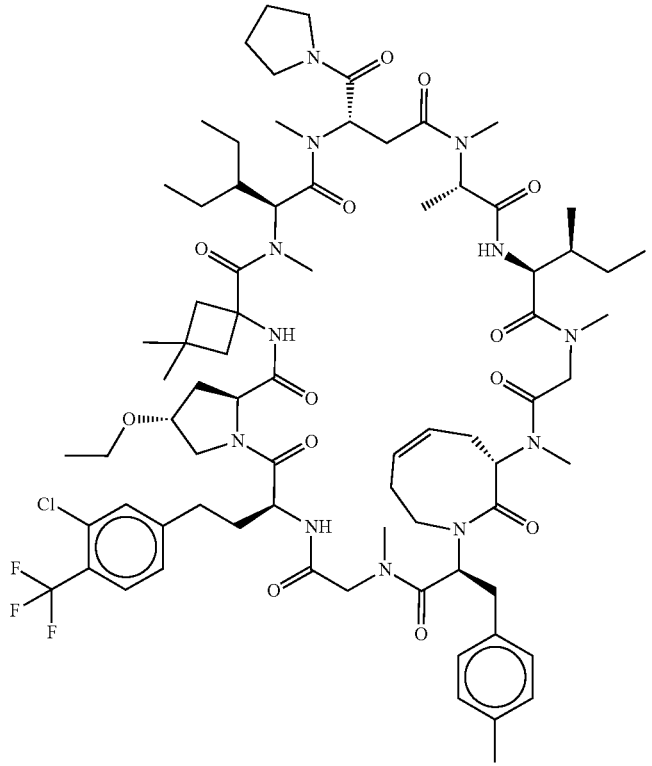 |
| PP2153 | 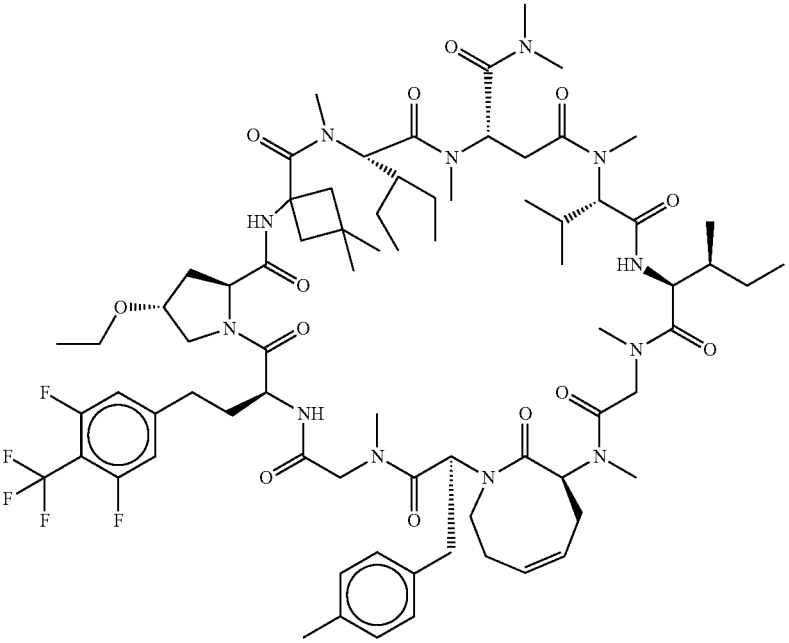 |

TABLE 38-continued
| Compound No. | Structural Formula |
|---|---|
| PP2154 | 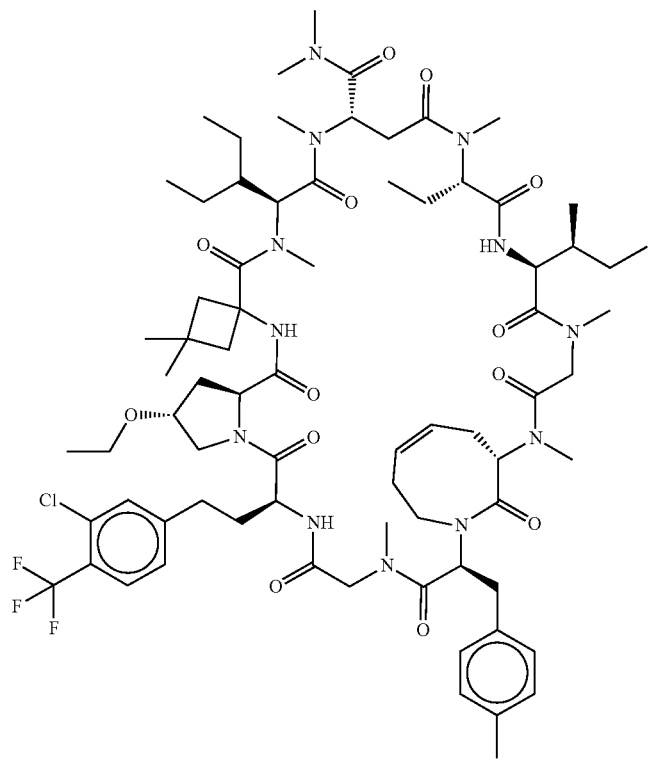 |
| PP2155 | 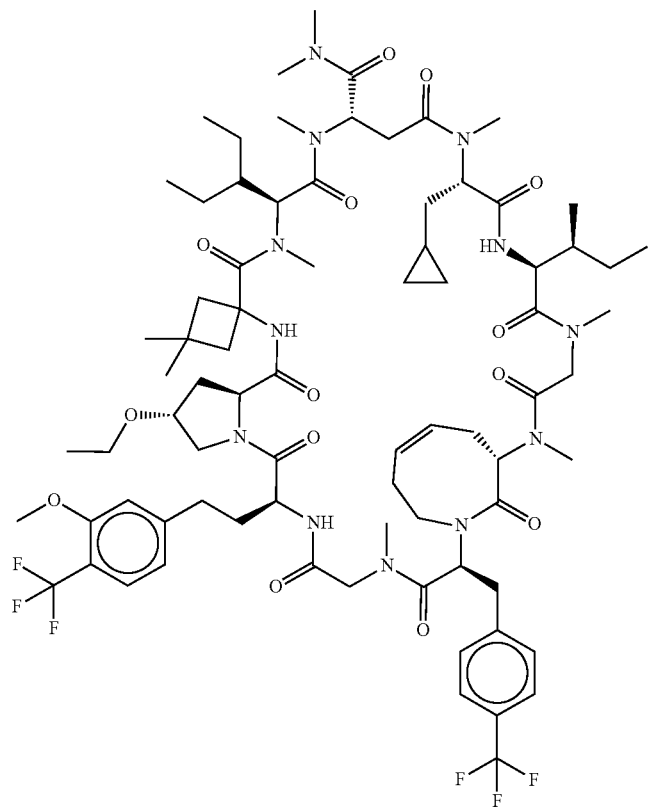 |

TABLE 38-continued
| Compound No. | Structural Formula |
|---|---|
| PP2156 | 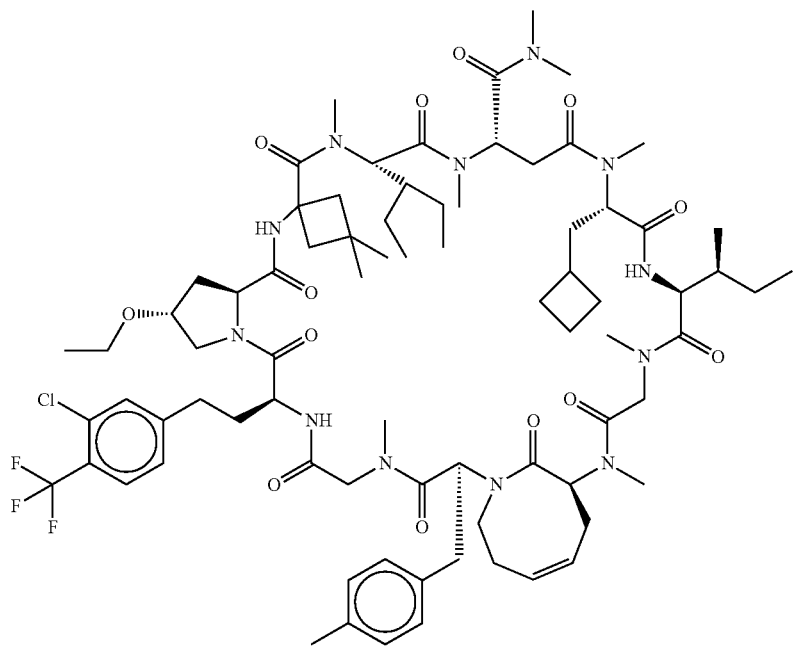 |
| PP2157 | 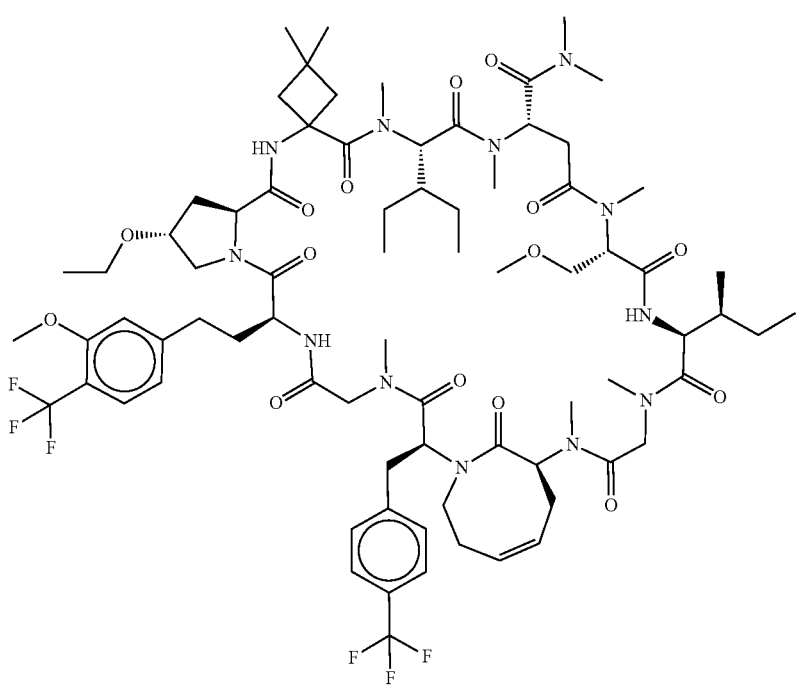 |

TABLE 38-continued
| Compound No. | Structural Formula |
| --- | --- |
| PP2158 | 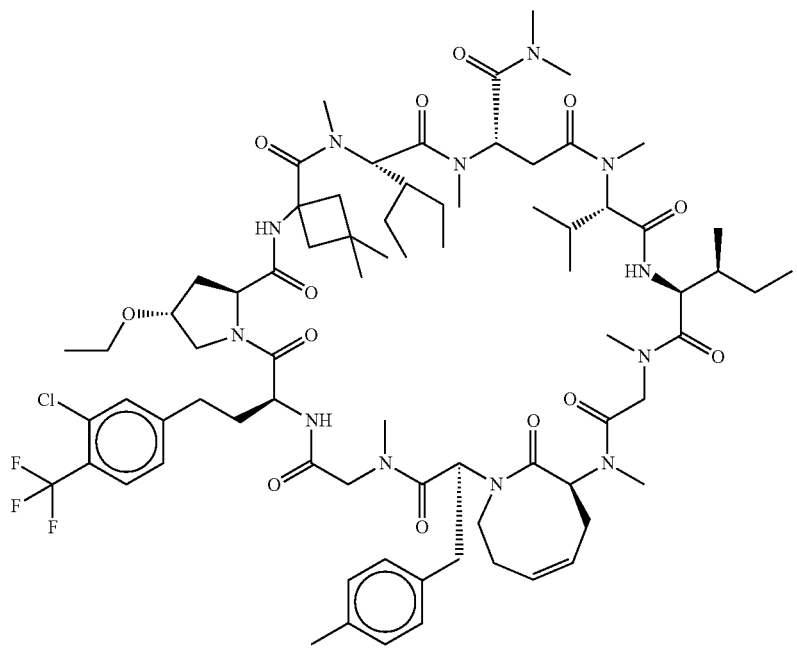 |
| PP2159 | 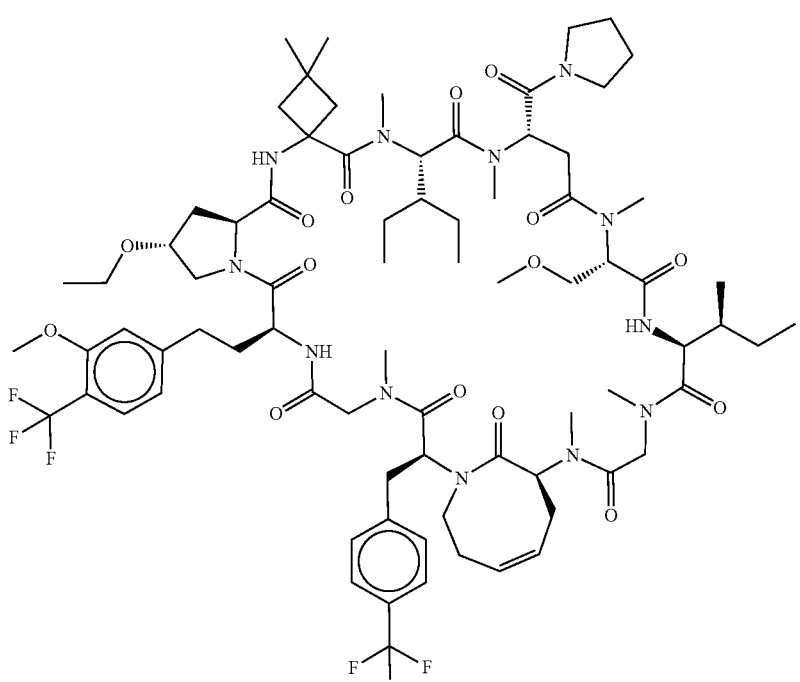 |

TABLE 38-continued
| Compound No. | Structural Formula |
|---|---|
| PP2160 | 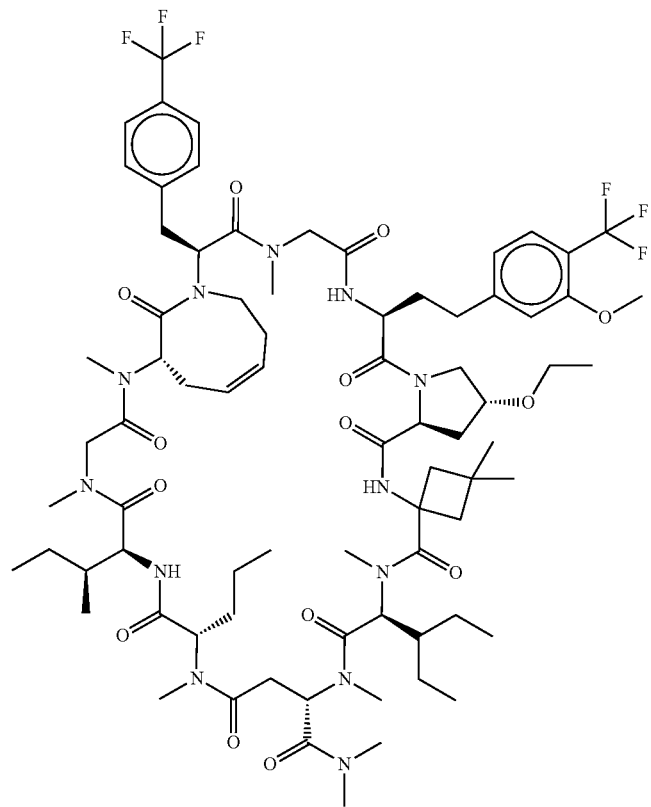 |
| PP2161 | 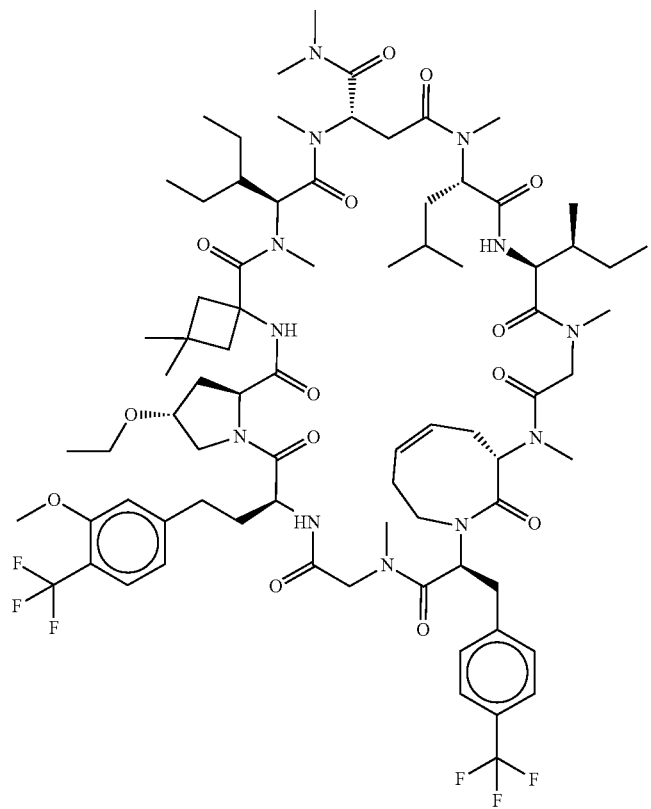 |

TABLE 38-continued
| Compound No. | Structural Formula |
|---|---|
| PP2163 | 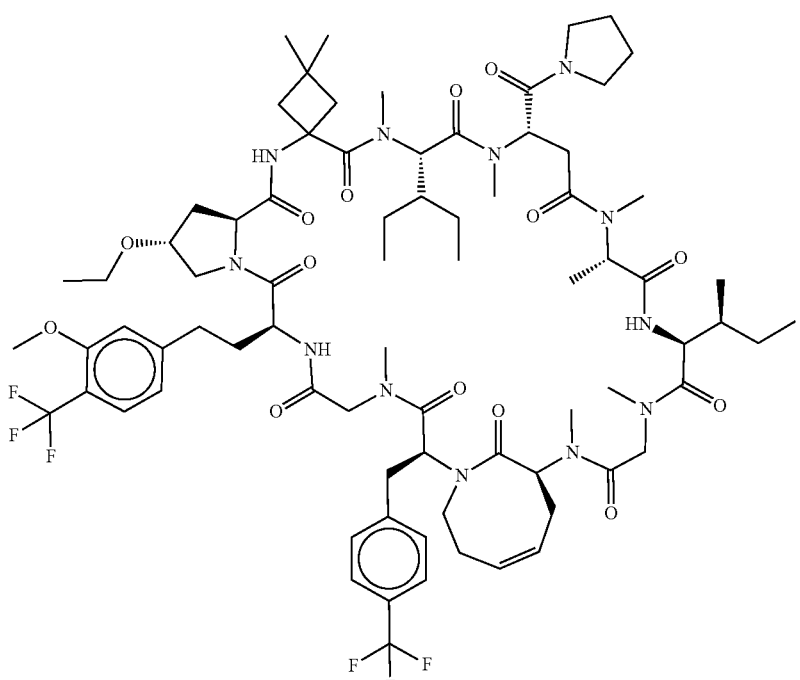 |
| PP2164 | 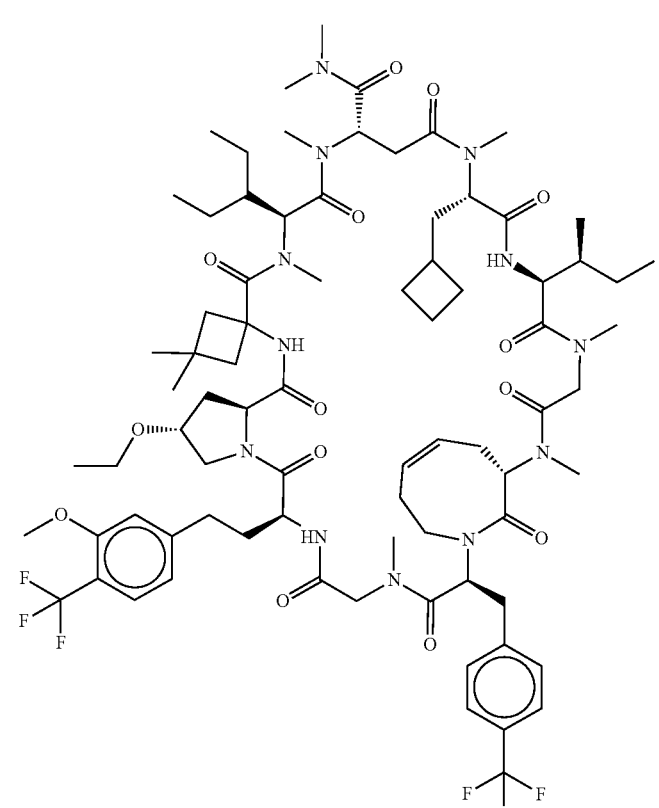 |

TABLE 38-continued
| Compound No. | Structural Formula |
|---|---|
| PP2165 | 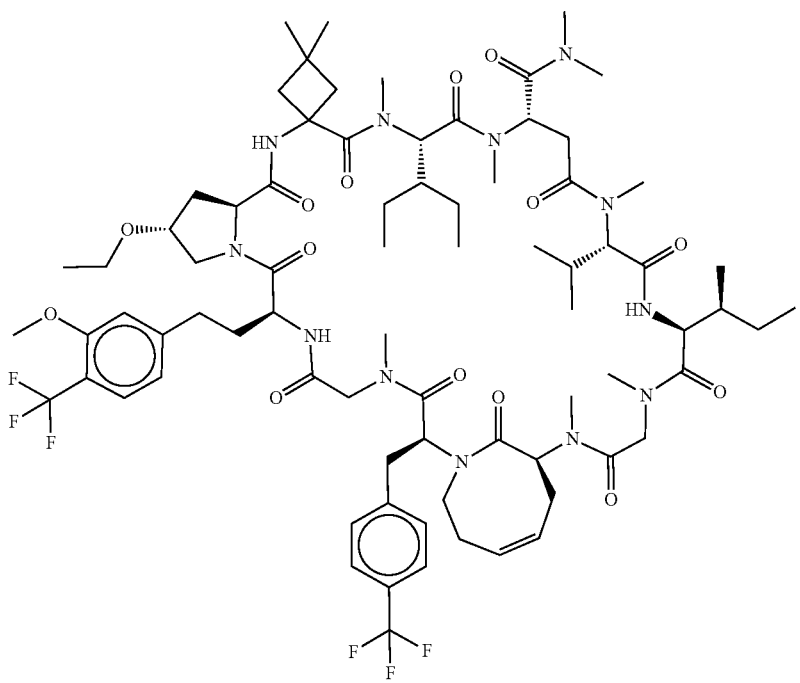 |
| PP2166 | 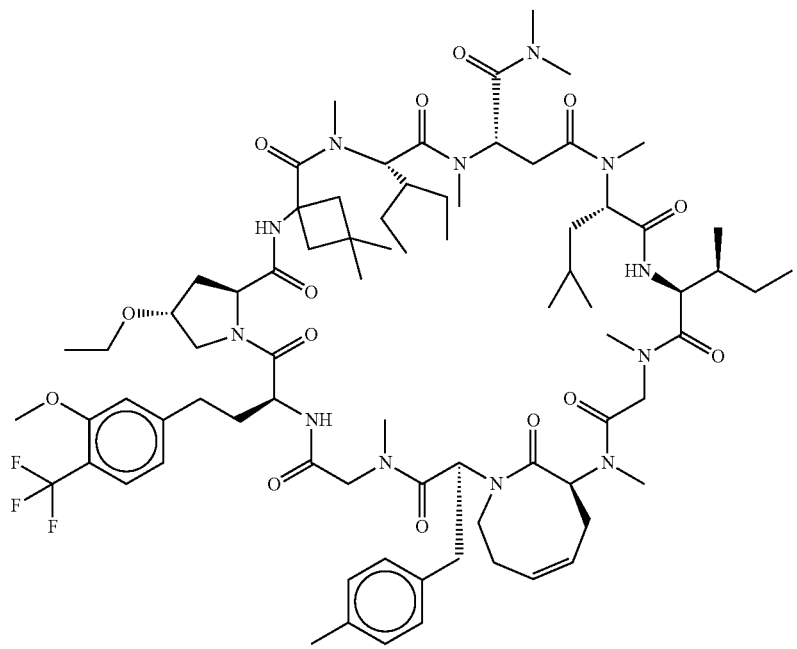 |

TABLE 38-continued
| Compound No. | Structural Formula |
|---|---|
| PP2167 | 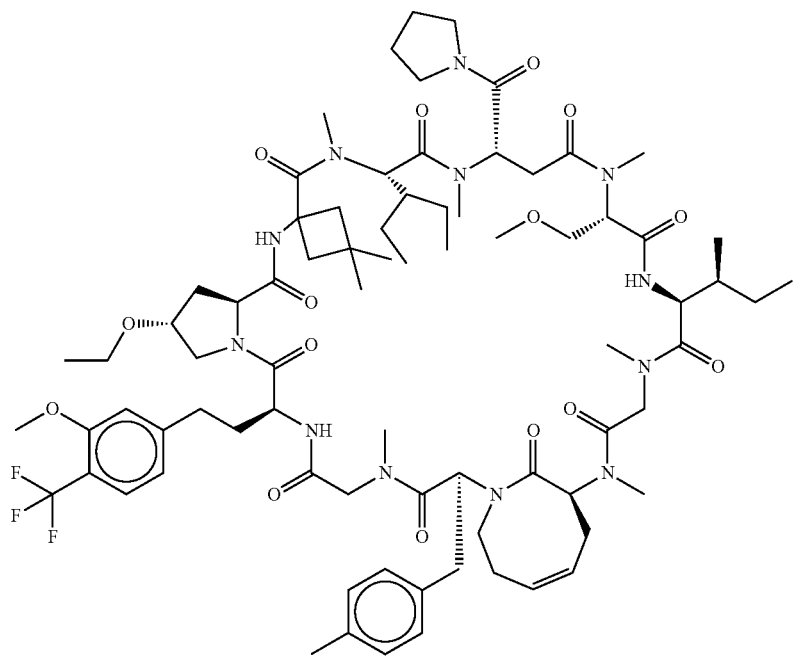 |
| PP2168 | 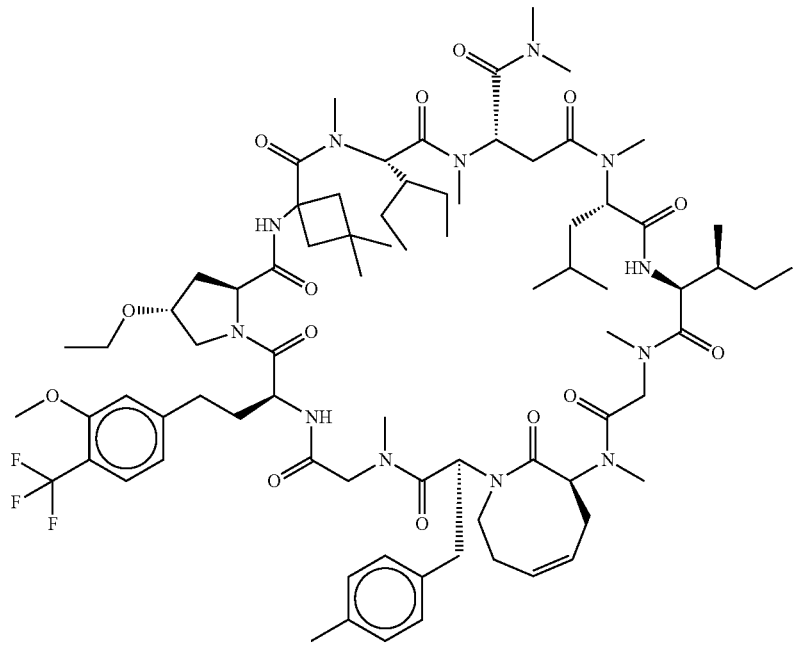 |

TABLE 38-continued
| Compound No. | Structural Formula |
|---|---|
| PP2169 | 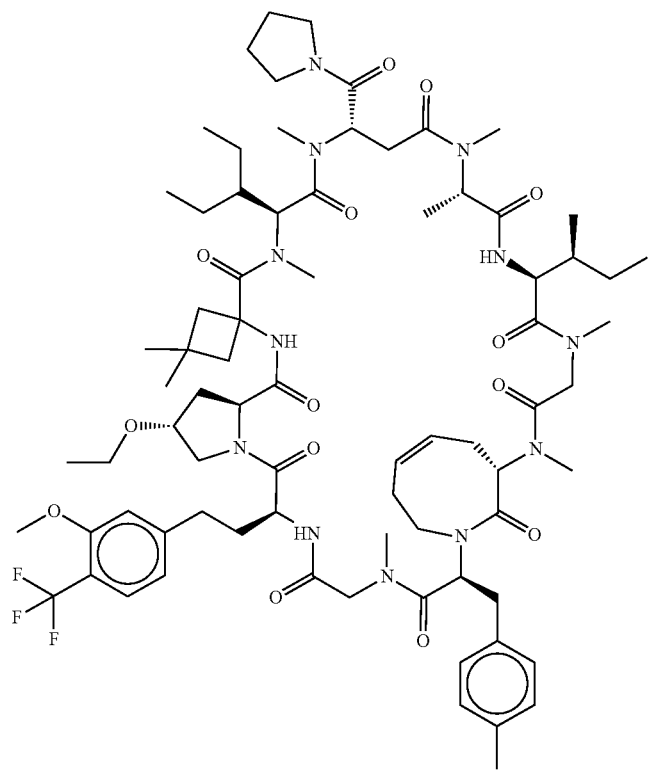 |
| PP2170 | 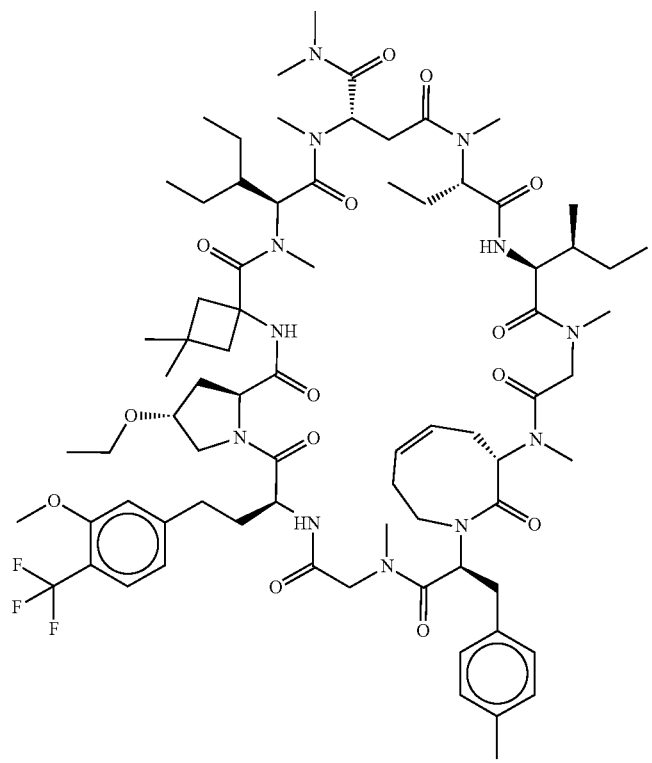 |

TABLE 38-continued

| Compound No. | Structural Formula |
|---|---|
| PP2171 | |
| PP2172 | |

TABLE 38-continued
| Compound No. | Structural Formula |
|---|---|
| PP2173 | 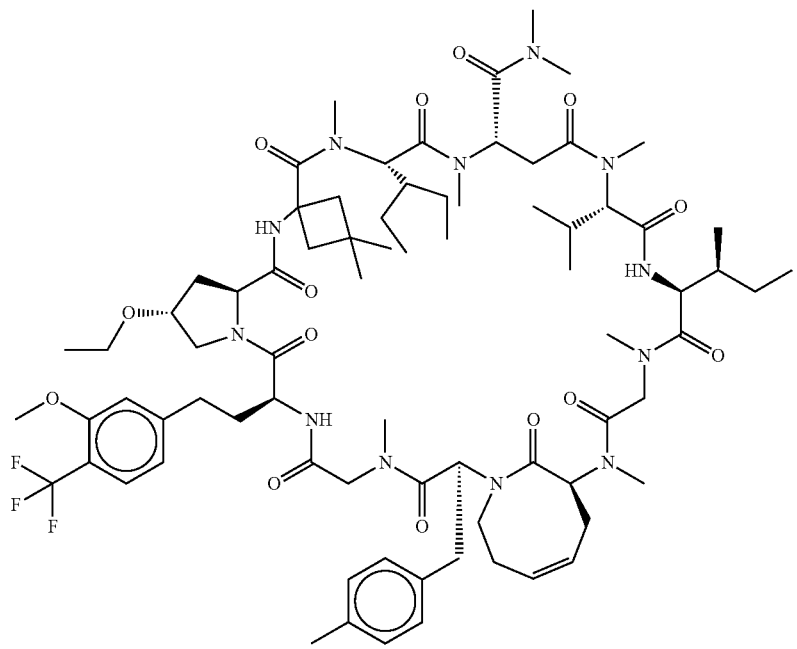 |
| PP2174 | 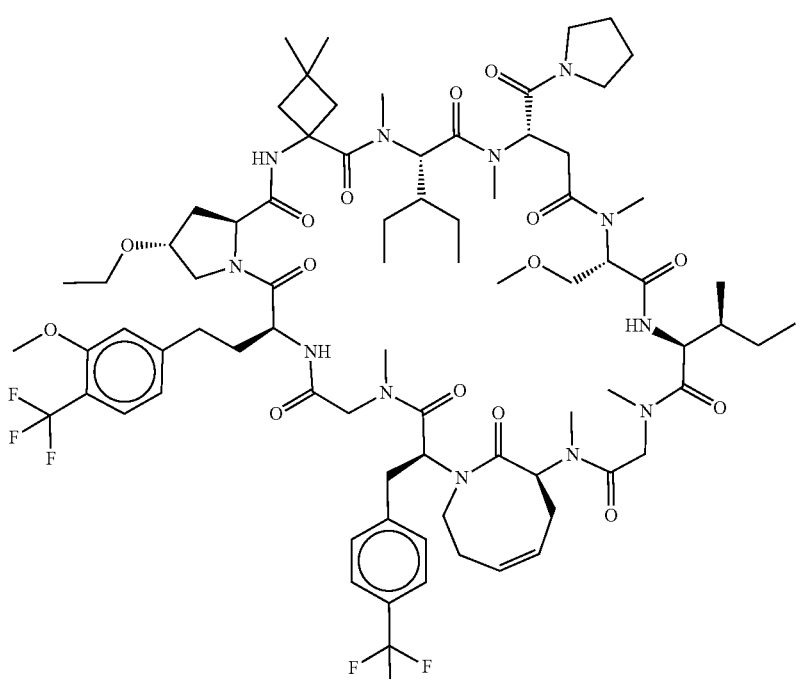 |

TABLE 38-continued
| Compound No. | Structural Formula |
|---|---|
| PP2175 | 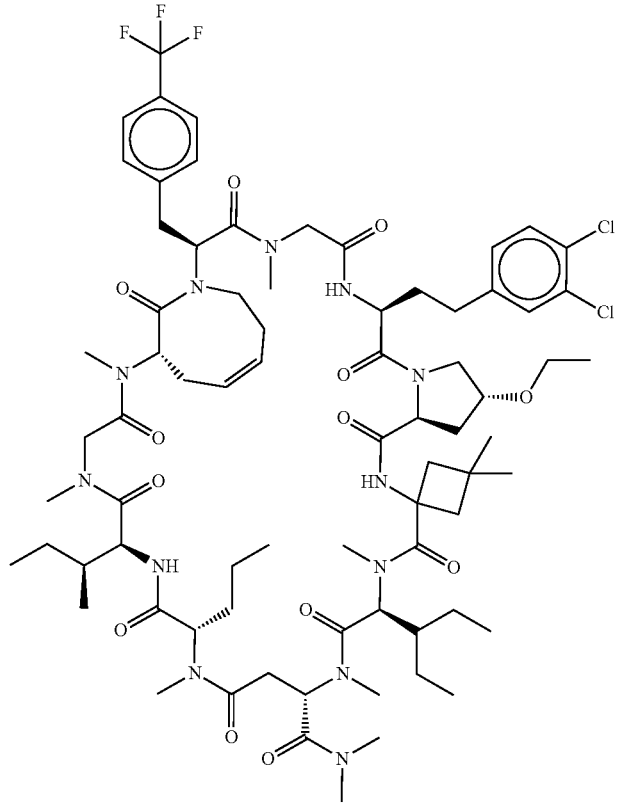 |
| PP2176 | 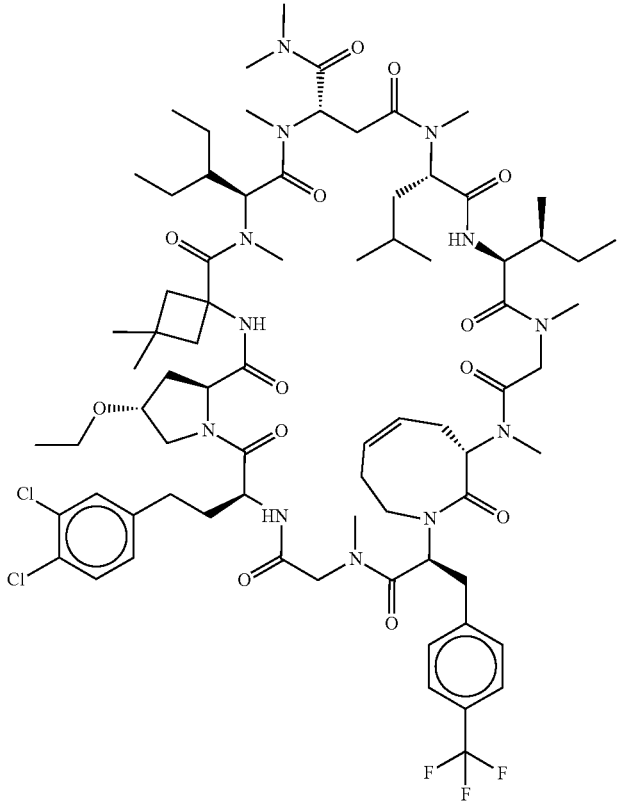 |

TABLE 38-continued

| Compound No. | Structural Formula |
|---|---|
| PP2178 | |
| PP2179 | |

TABLE 38-continued
| Compound No. | Structural Formula |
|---|---|
| PP2180 | 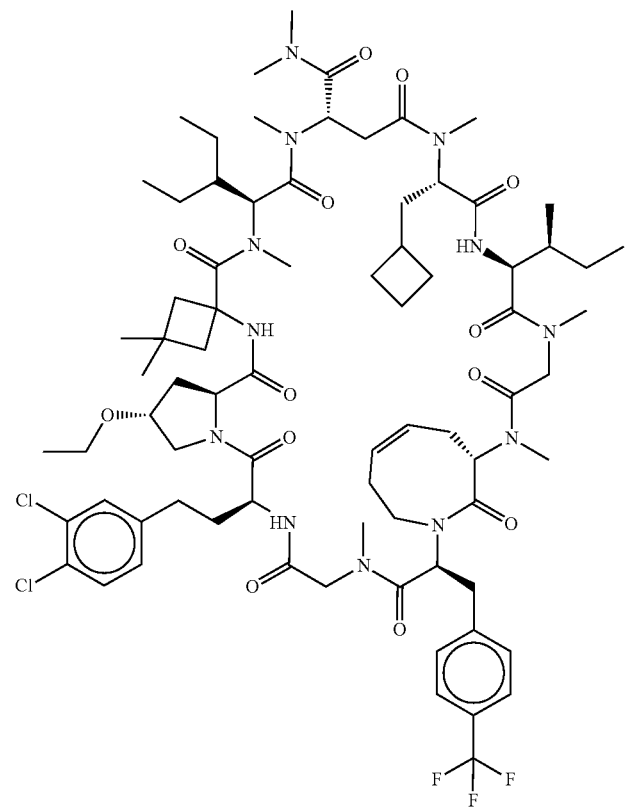 |
| PP2181 | 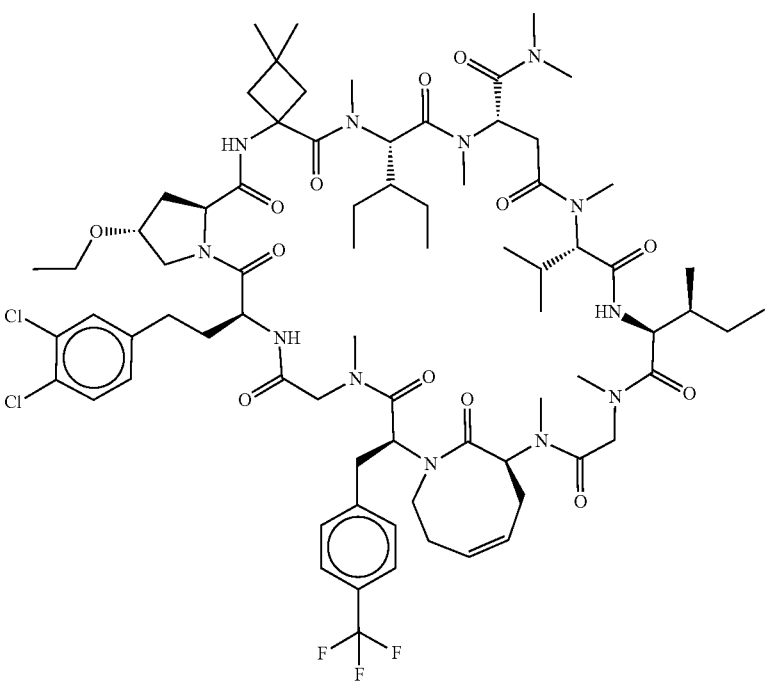 |

TABLE 38-continued
| Compound No. | Structural Formula |
|---|---|
| PP2182 | 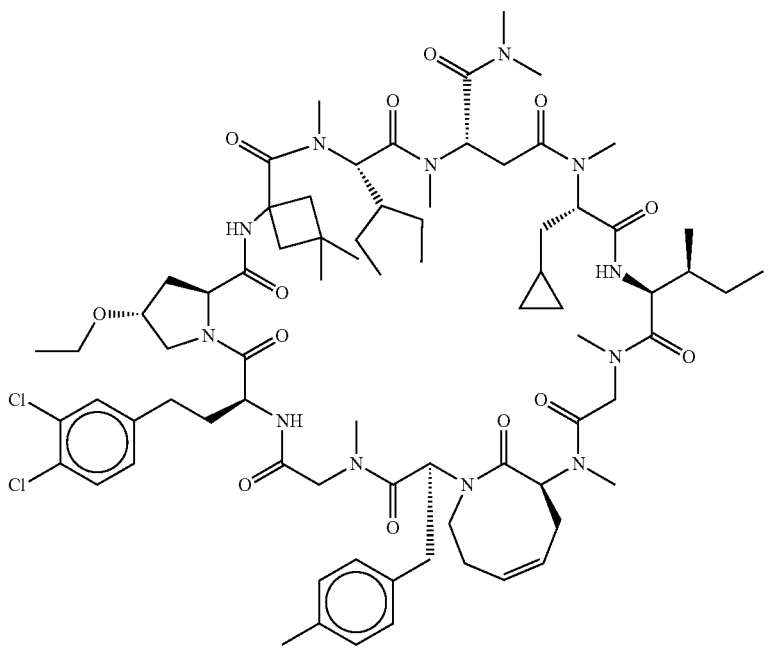 |
| PP2183 | 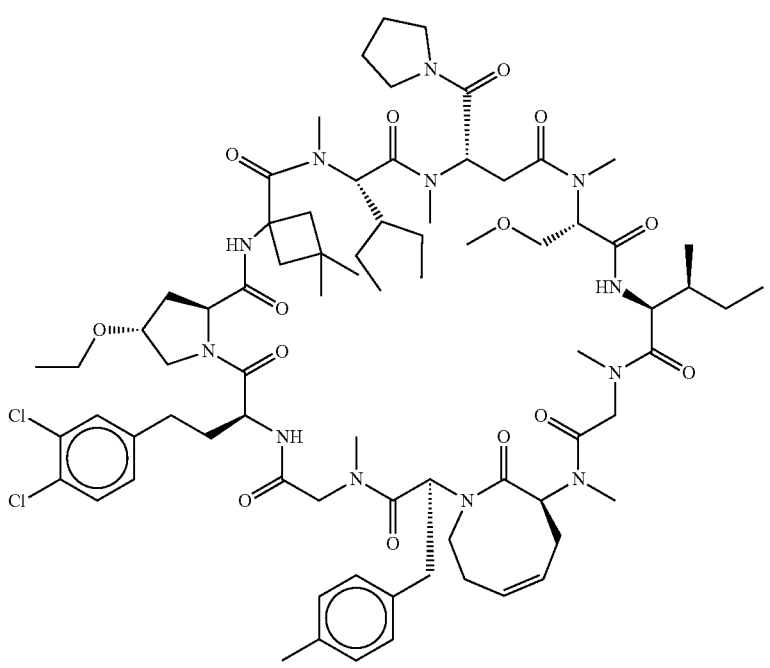 |

TABLE 38-continued

| Compound No. | Structural Formula |
|---|---|
| PP2184 | |
| PP2185 | |

TABLE 38-continued
| Compound No. | Structural Formula |
|---|---|
| PP2186 | 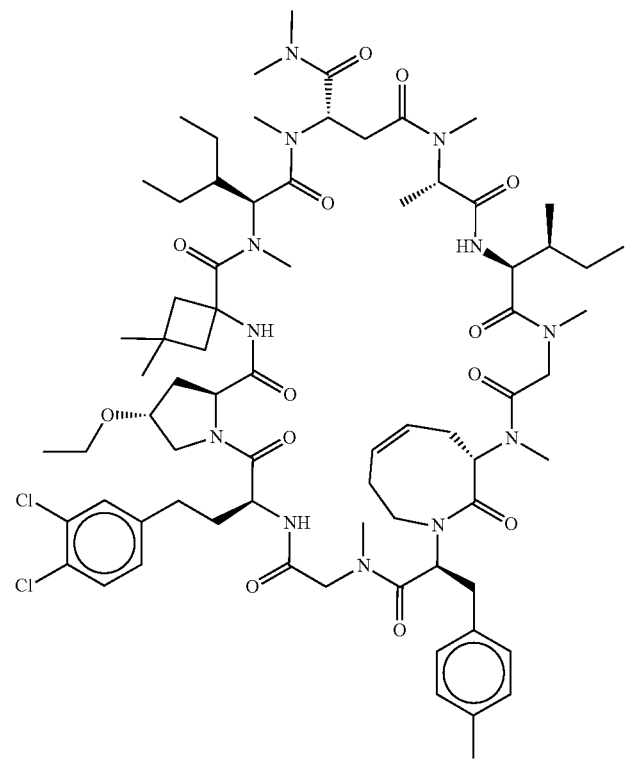 |
| PP2187 | 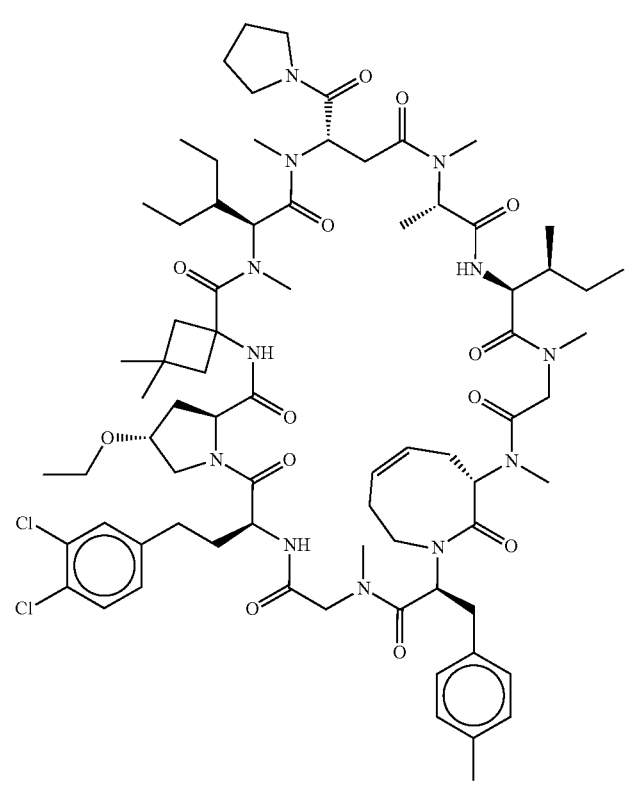 |

TABLE 38-continued

| Compound No. | Structural Formula |
|---|---|
| PP2188 | |
| PP2189 | |

TABLE 38-continued

| Compound No. | Structural Formula |
|---|---|
| PP2190 | |
| PP2191 | |

TABLE 38-continued

| Compound No. | Structural Formula |
|---|---|
| PP2192 | |
| PP2193 | |

TABLE 38-continued
| Compound No. | Structural Formula |
|---|---|
| PP2194 | 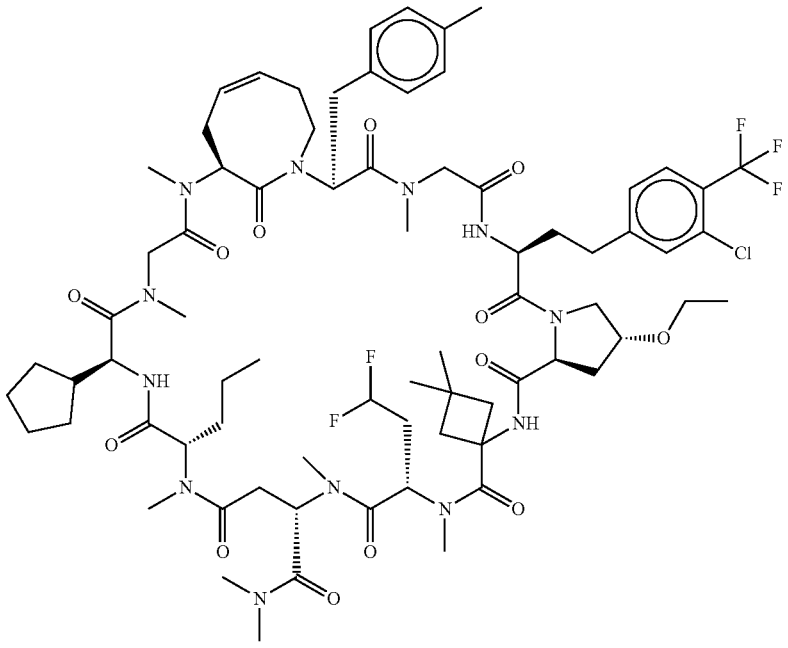 |
| PP2195 | 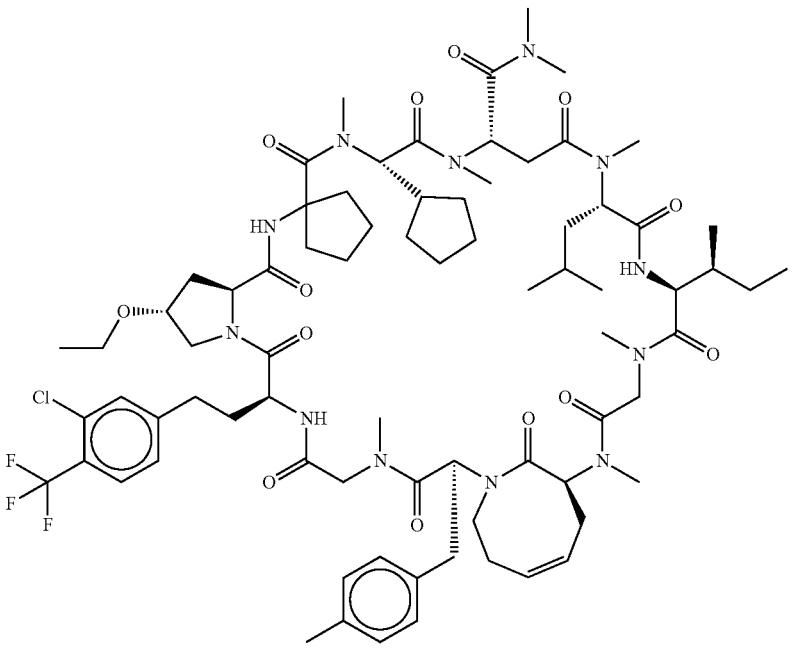 |

TABLE 38-continued

| Compound No. | Structural Formula |
|---|---|
| PP2196 | |
| PP2197 | |

TABLE 38-continued

| Compound No. | Structural Formula |
|---|---|
| PP2198 | |
| PP2199 | |

2937
TABLE 38-continued
| Compound No. | Structural Formula |
|---|---|
| PP2200 | 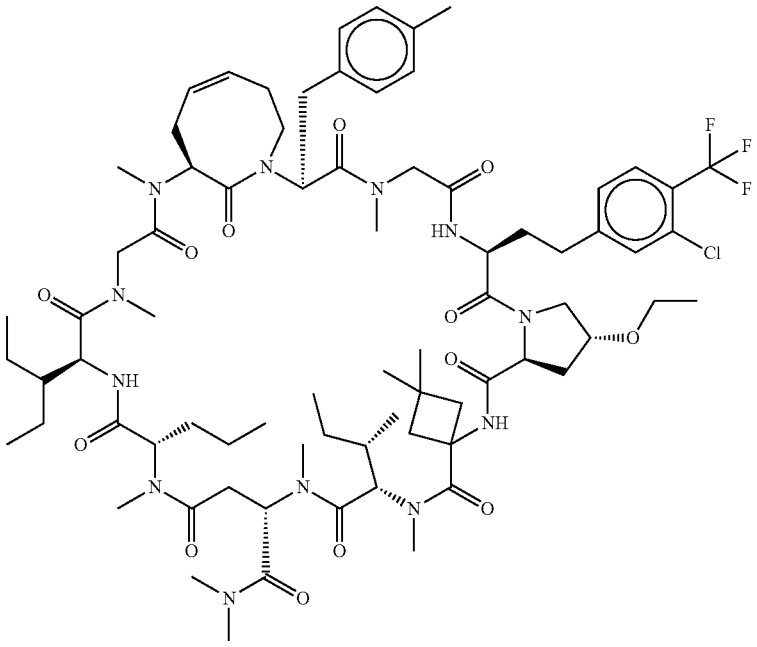 |
| PP2202 | 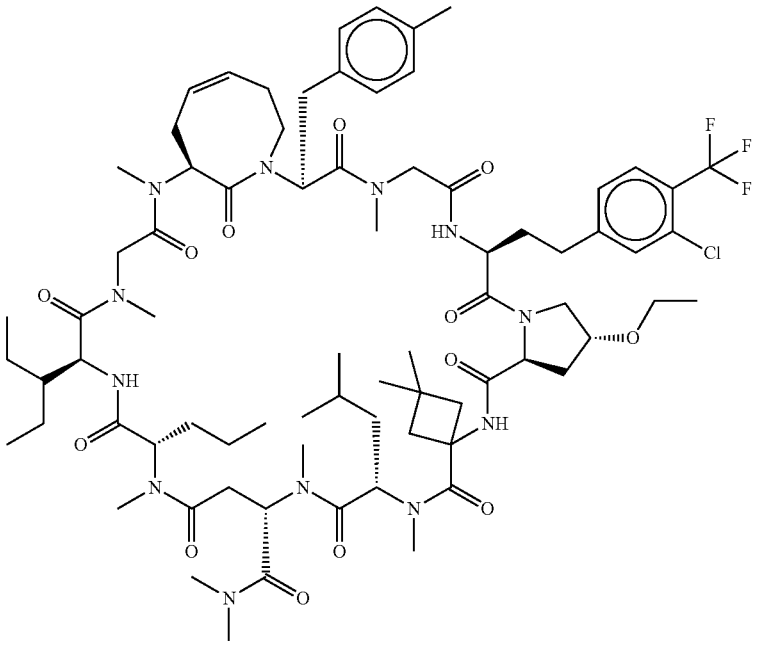 |

TABLE 38-continued
| Compound No. | Structural Formula |
|---|---|
| PP2203 |  |
| PP2204 |  |

TABLE 38-continued

| Compound No. | Structural Formula |
|---|---|
| PP2207 | |
| PP2208 | |

TABLE 38-continued

| Compound No. | Structural Formula |
|---|---|
| PP2209 | |
| PP2210 | |

TABLE 38-continued

| Compound No. | Structural Formula |
|---|---|
| PP2211 | |
| PP2212 | |

TABLE 38-continued
| Compound No. | Structural Formula |
|---|---|
| PP2214 | 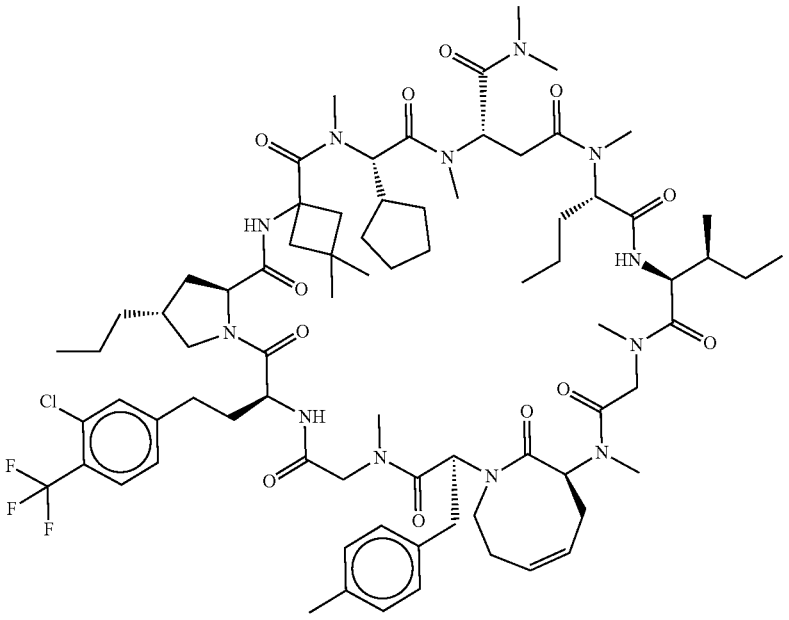 |
| PP2215 | 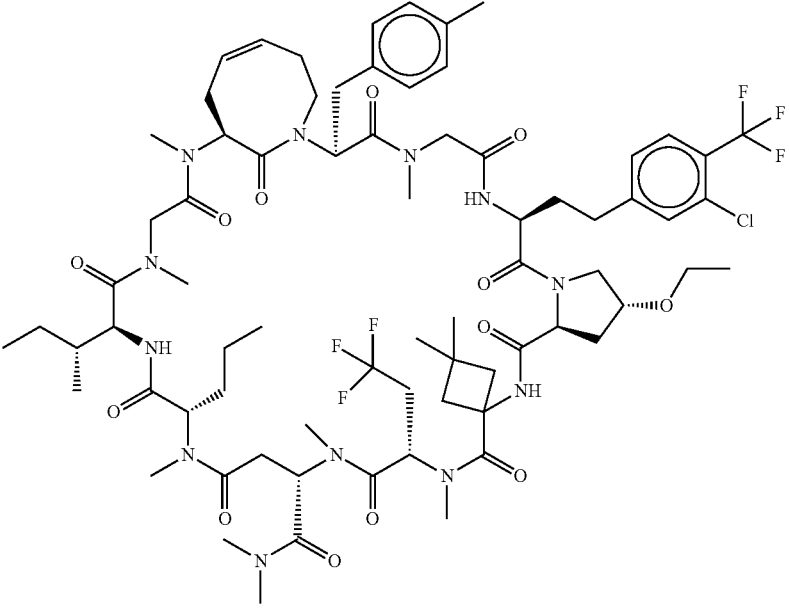 |

TABLE 38-continued

| Compound No. | Structural Formula |
| --- | --- |
| PP2216 | |
| PP2218 | |

TABLE 38-continued

| Compound No. | Structural Formula |
|---|---|
| PP2219 | |
| PP2220 | |

| Compound No. | Structural Formula |
|---|---|
| PP2221 | |
| PP2222 | |

TABLE 38-continued

| Compound No. | Structural Formula |
|---|---|
| PP2223 | |
| PP2224 | |

| Compound No. | Structural Formula |
|---|---|
| PP2225 | |
| PP2226 | |

TABLE 38-continued

| Compound No. | Structural Formula |
|---|---|
| PP2227 | |
| PP2228 | |

TABLE 38-continued
| Compound No. | Structural Formula |
|---|---|
| PP2229 | 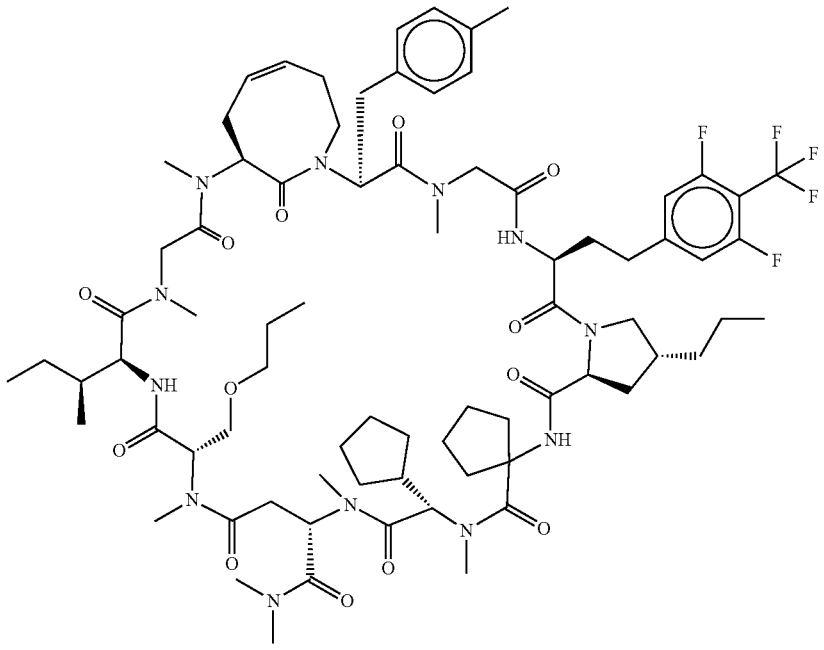 |
| PP2230 | 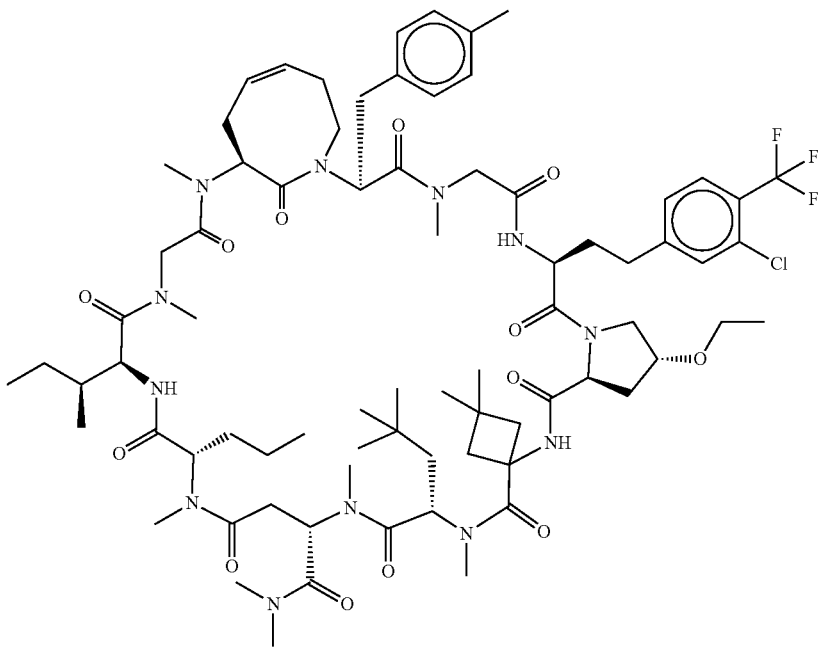 |

TABLE 38-continued

| Compound No. | Structural Formula |
|---|---|
| PP2231 | |
| PP2232 | |

TABLE 38-continued
| Compound No. | Structural Formula |
|---|---|
| PP2233 | 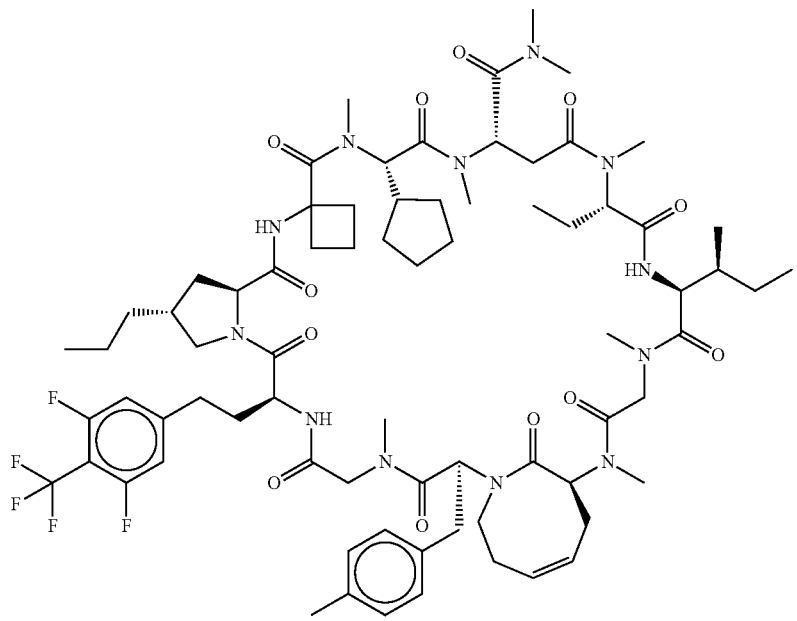 |
| PP2234 | 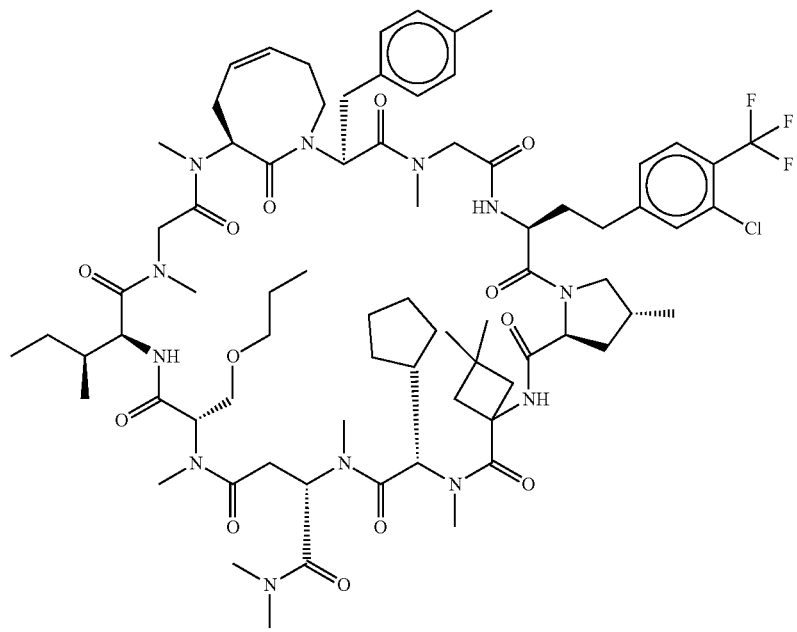 |

TABLE 38-continued

| Compound No. | Structural Formula |
|---|---|
| PP2235 | |
| PP2237 | |

TABLE 38-continued
| Compound No. | Structural Formula |
|---|---|
| PP2238 | 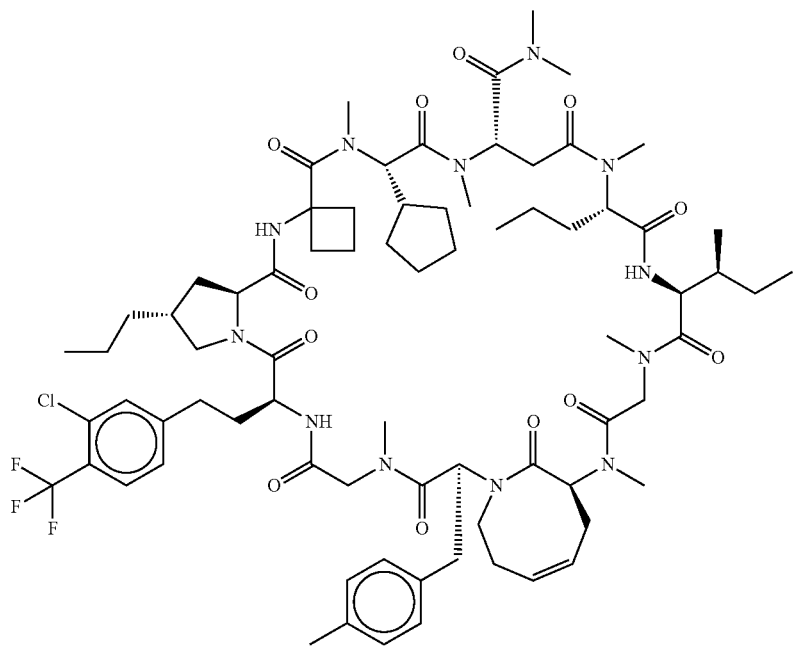 |
| PP2239 | 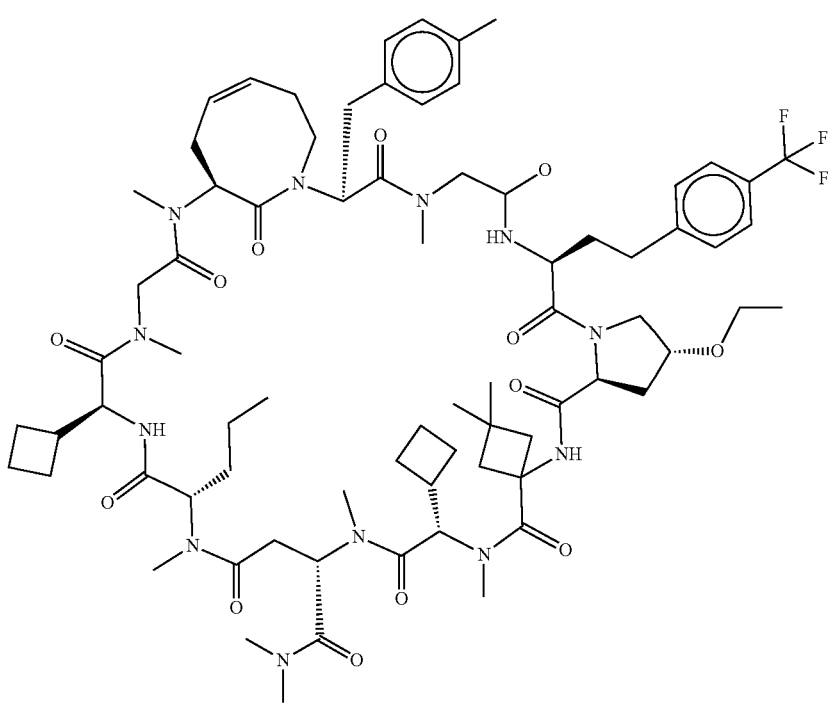 |

TABLE 38-continued
| Compound No. | Structural Formula |
| --- | --- |
| PP2241 | 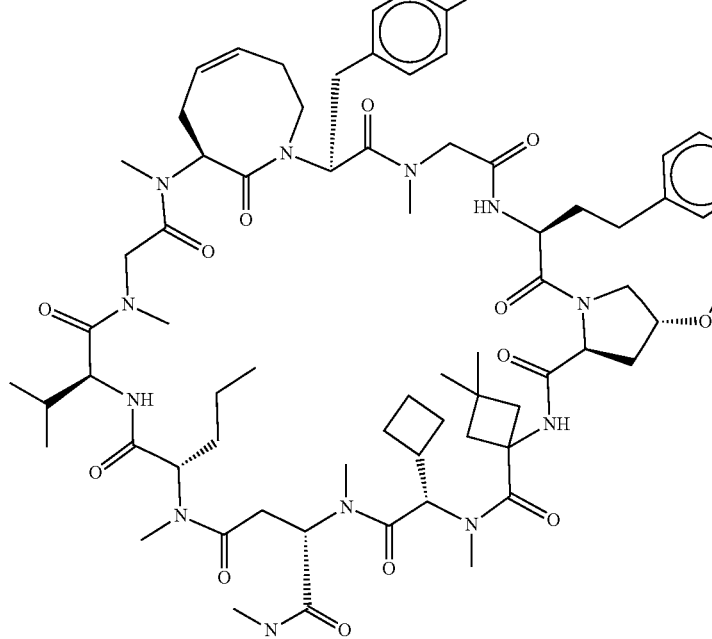 |
| PP2242 | 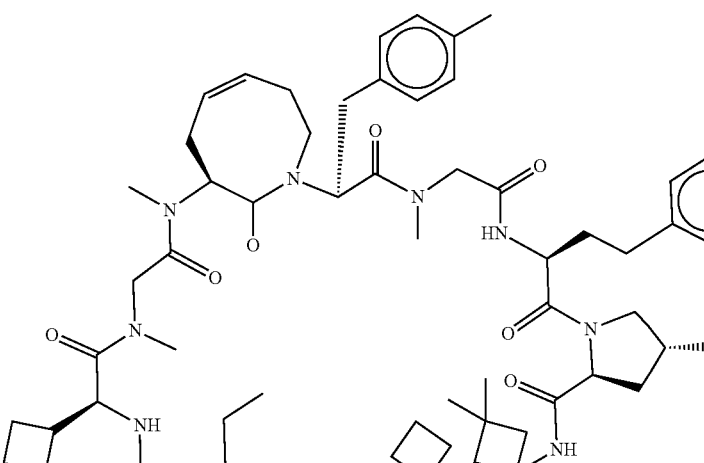 |

TABLE 38-continued

| Compound No. | Structural Formula |
|---|---|
| PP2244 | |
| PP2245 | |

TABLE 38-continued
| Compound No. | Structural Formula |
|---|---|
| PP2248 | 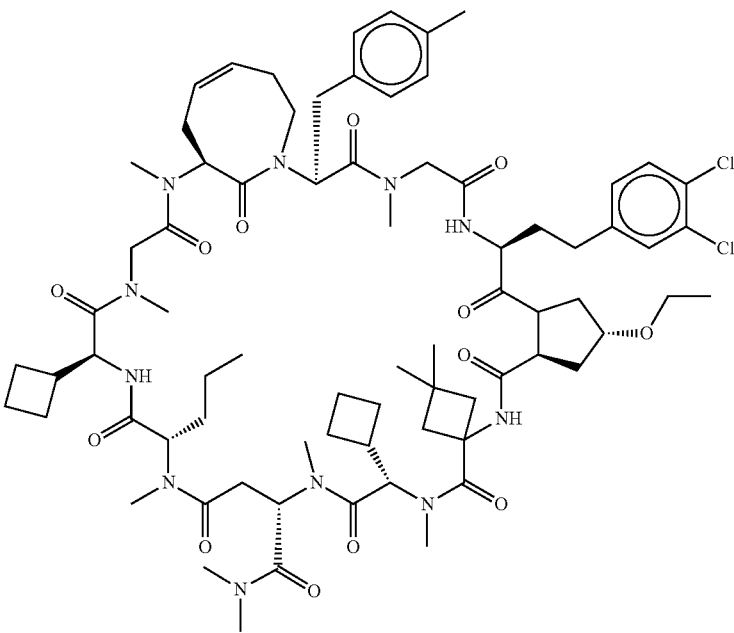 |
| PP2249 | 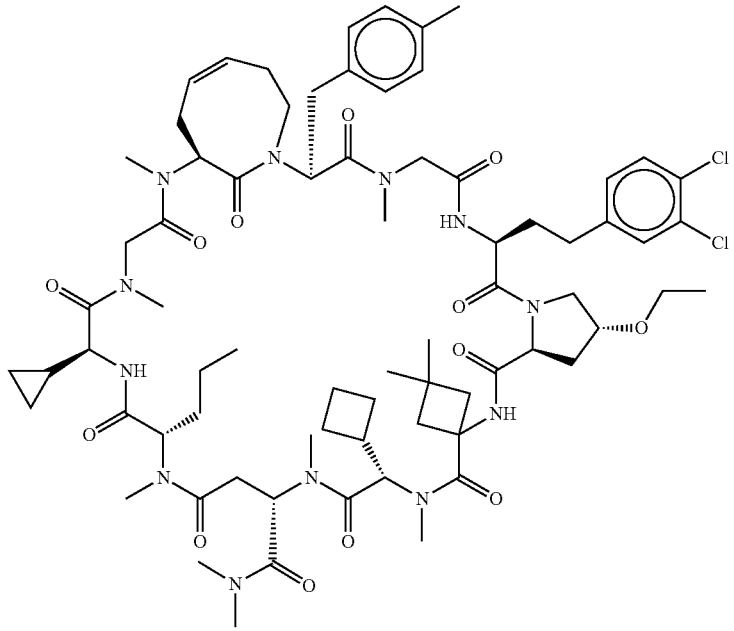 |

TABLE 38-continued
| Compound No. | Structural Formula |
|---|---|
| PP2250 | 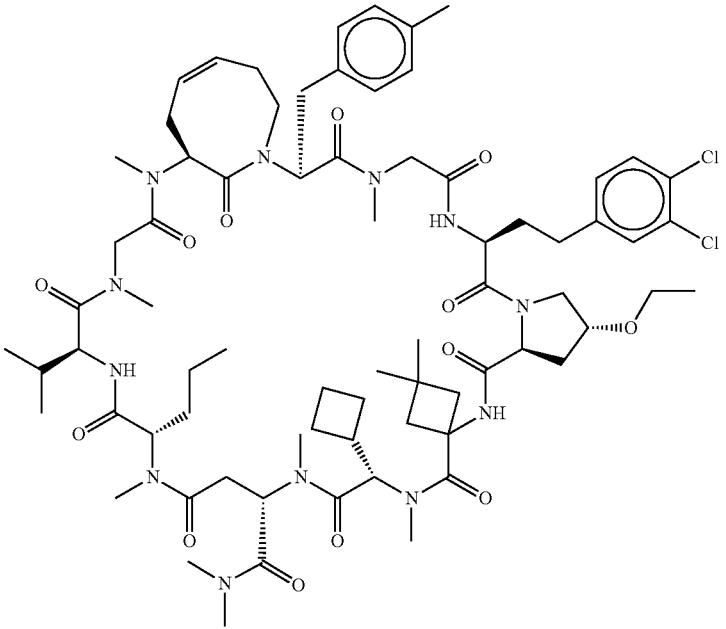 |
| PP2257 | 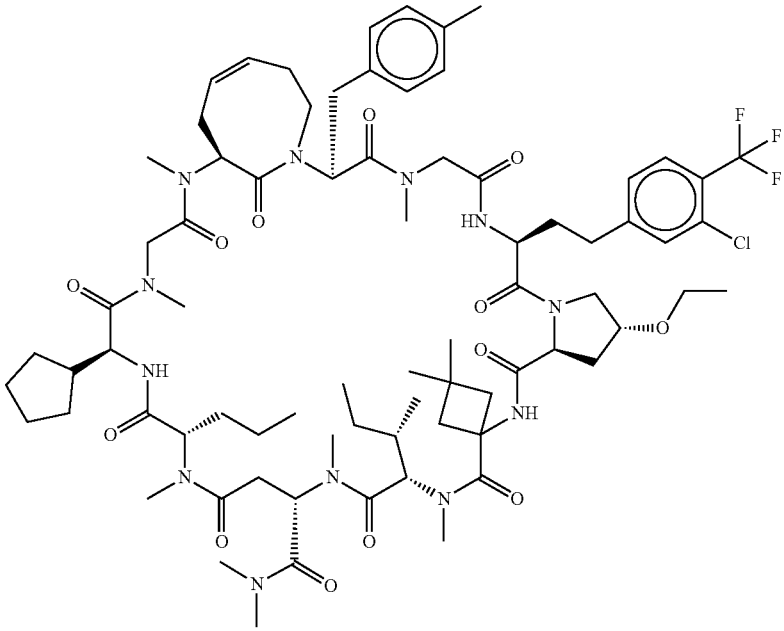 |

TABLE 38-continued

| Compound No. | Structural Formula |
| --- | --- |
| PP2258 | |
| PP2259 | |

TABLE 38-continued
| Compound No. | Structural Formula |
|---|---|
| PP2260 | 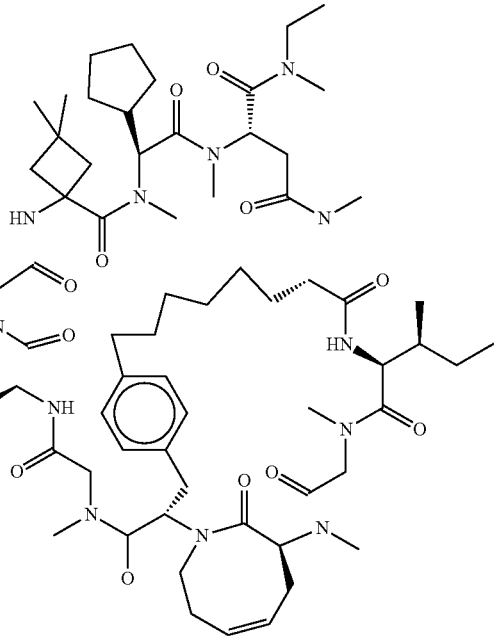 |
| PP2261 | 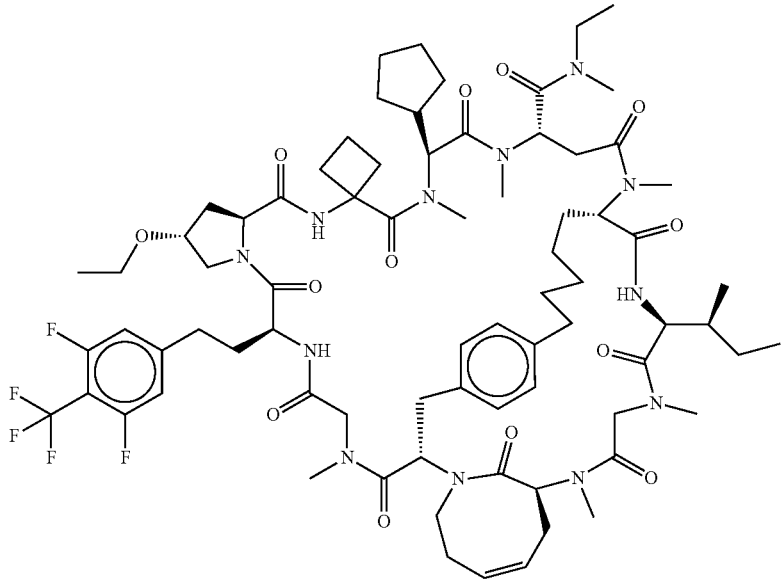 |

TABLE 38-continued

| Compound No. | Structural Formula |
|---|---|
| PP2262 | |
| PP2263 | |

TABLE 38-continued

| Compound No. | Structural Formula |
|---|---|
| PP2264 | |
| PP2265 | |

| Compound No. | Structural Formula |
|---|---|
| PP2266 | |
| PP2267 | |

TABLE 38-continued
| Compound No. | Structural Formula |
|---|---|
| PP2268 | 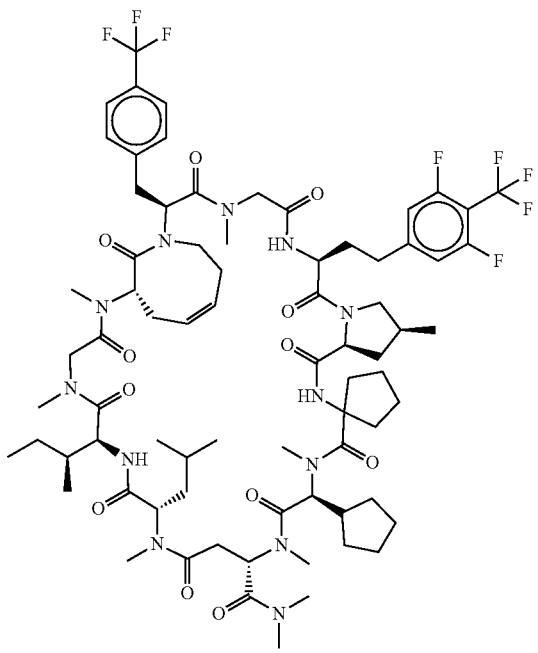 |
| PP2269 | 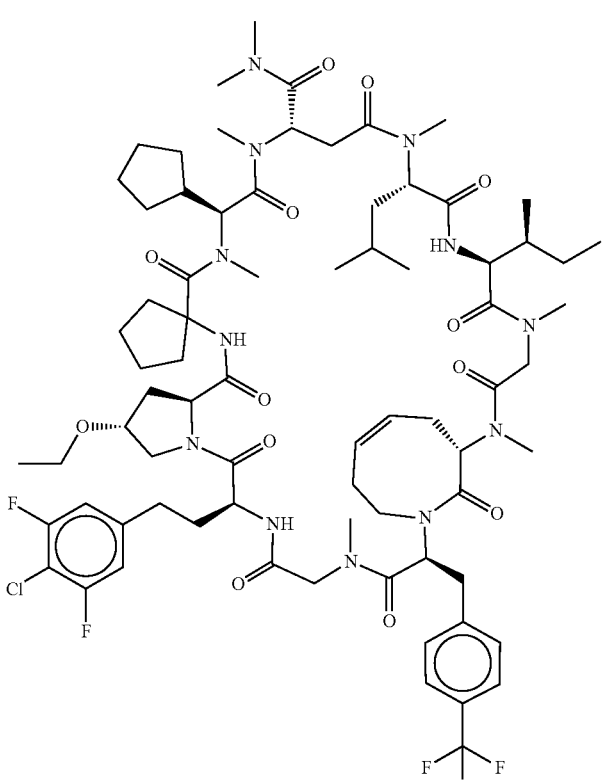 |

TABLE 38-continued
| Compound No. | Structural Formula |
|---|---|
| PP2270 | 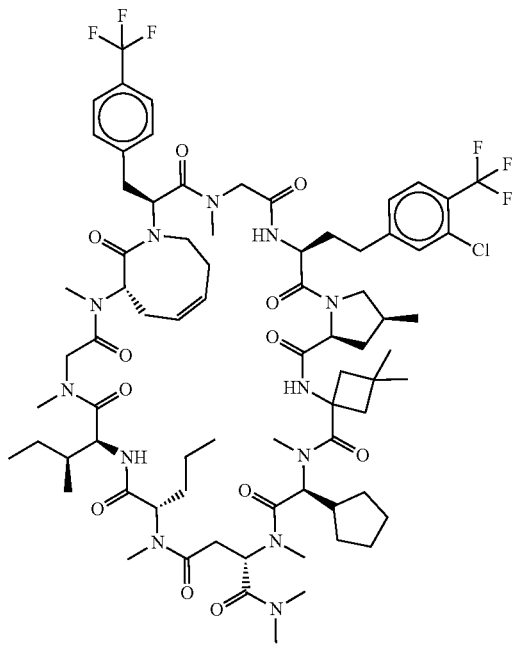 |
| PP2271 | 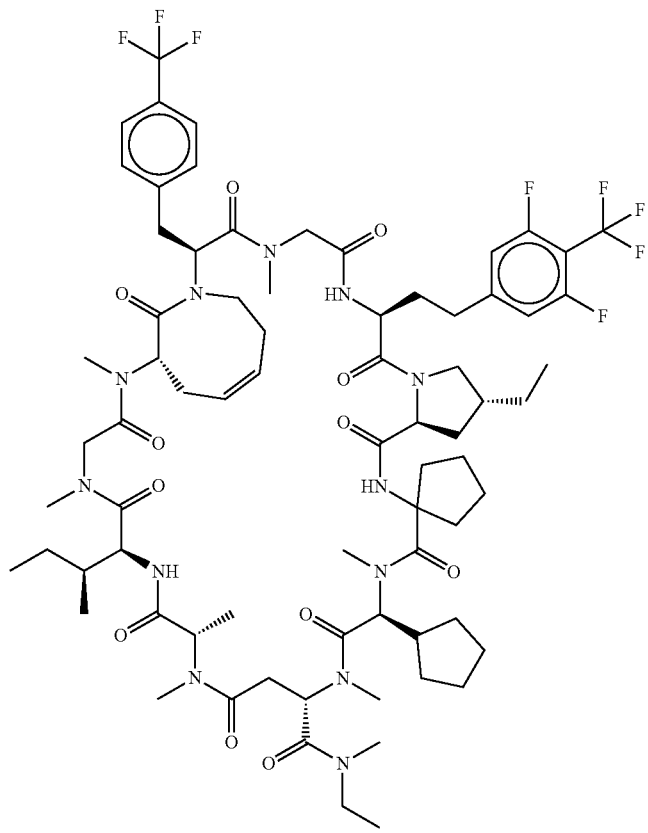 |

TABLE 38-continued

| Compound No. | Structural Formula |
|---|---|
| PP2272 | |
| PP2273 | |

TABLE 38-continued

| Compound No. | Structural Formula |
|---|---|
| PP2275 | |
| PP2312 | |

TABLE 38-continued
| Compound No. | Structural Formula |
|---|---|
| PP2313 | 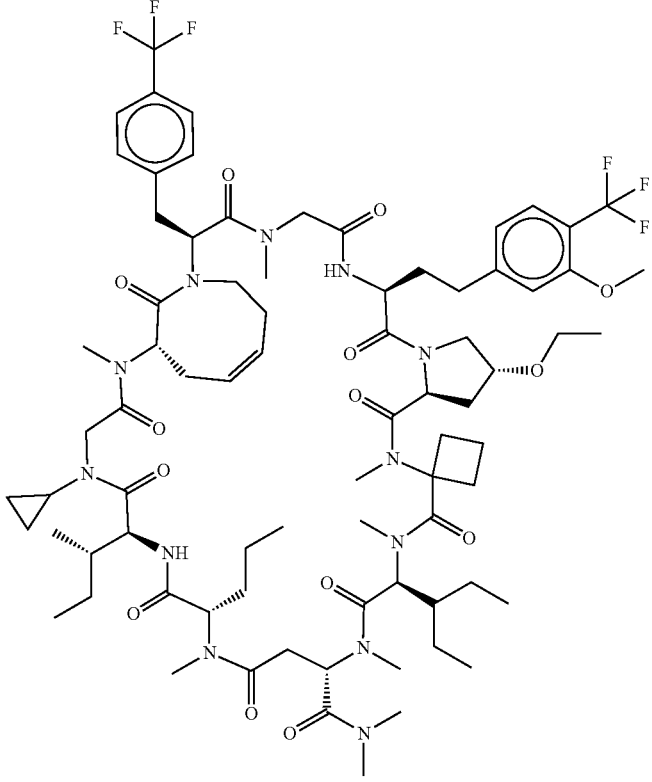 |
| PP2314 | 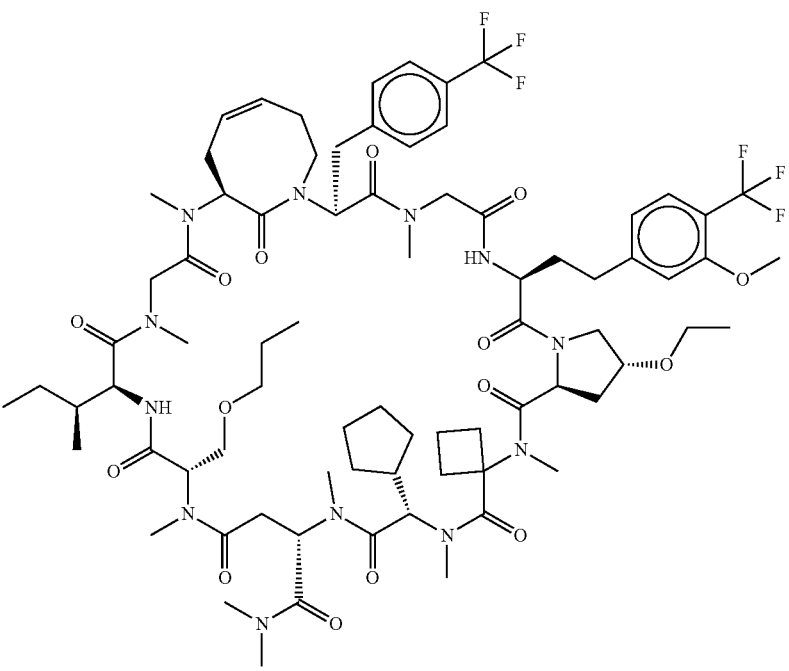 |

| Compound No. | Structural Formula |
|---|---|
| PP2315 | |
| PP2316 | |

| Compound No. | Structural Formula |
|---|---|
| PP2317 | |
| PP2318 | |

TABLE 38-continued
| Compound No. | Structural Formula |
|---|---|
| PP2319 | 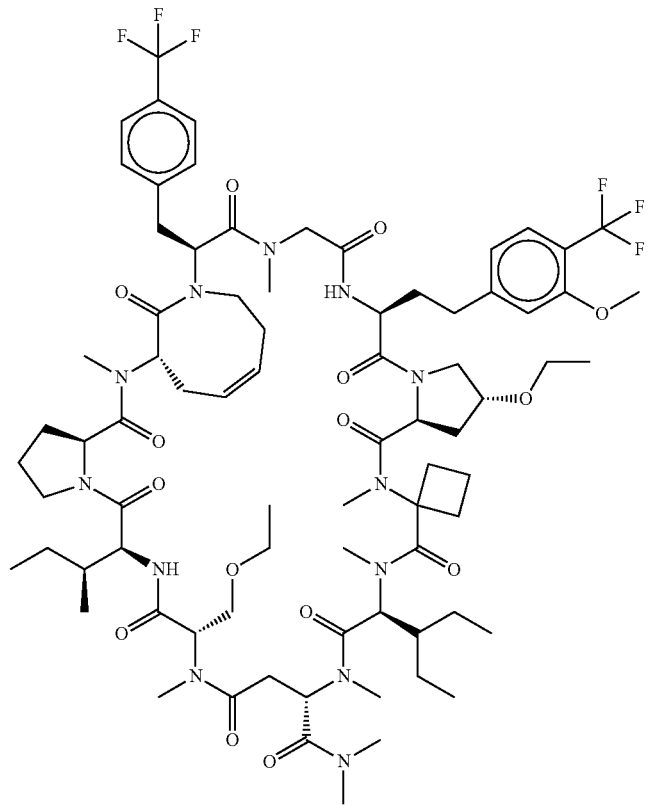 |
| PP2320 | 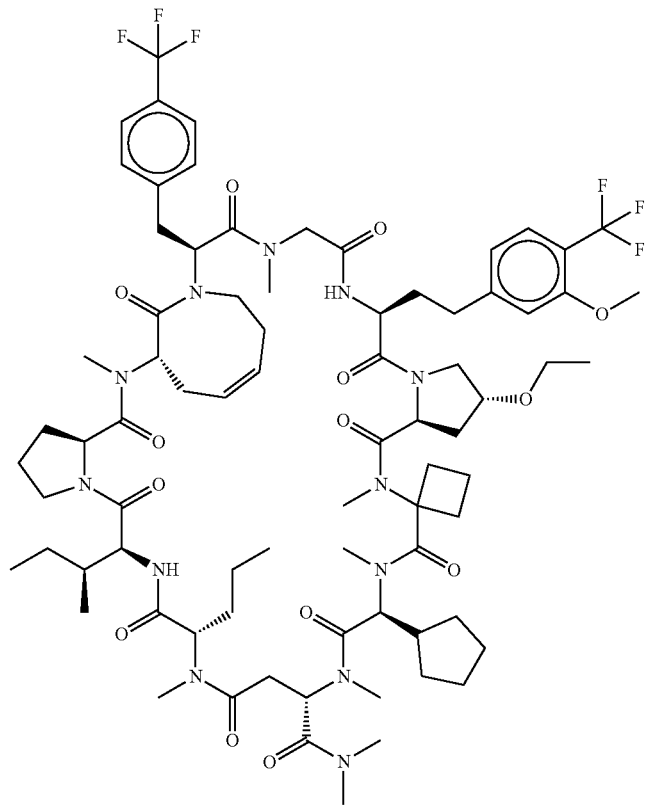 |

TABLE 38-continued
| Compound No. | Structural Formula |
|---|---|
| PP2322 | 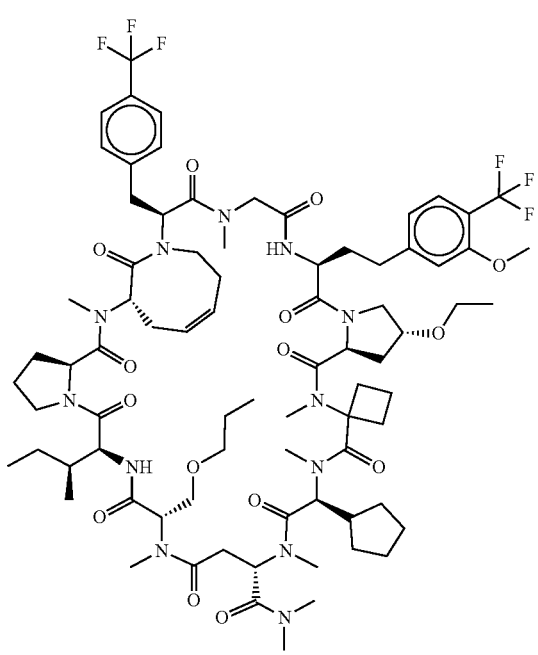 |
| PP2323 | 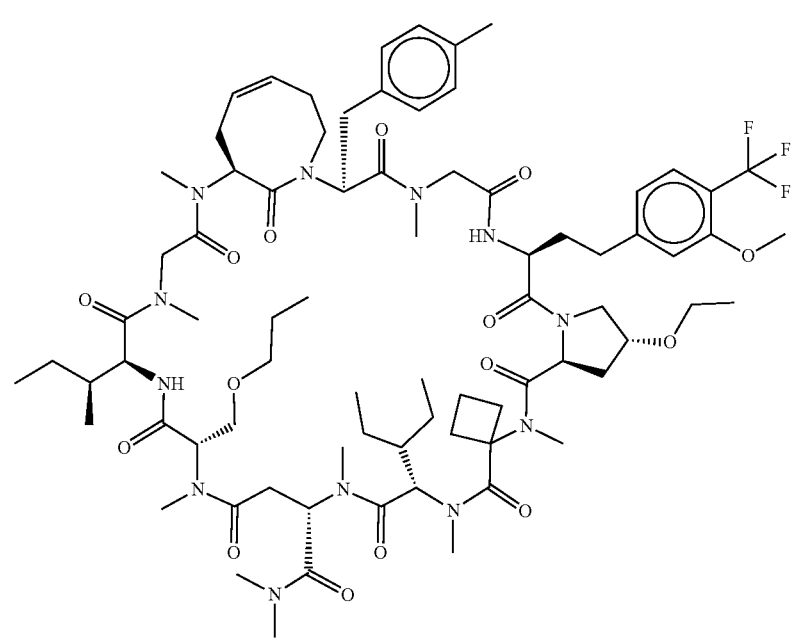 |

TABLE 38-continued

| Compound No. | Structural Formula |
|---|---|
| PP2325 | |
| PP2326 | |

TABLE 38-continued

| Compound No. | Structural Formula |
|---|---|
| PP2327 | |
| PP2328 | |

TABLE 38-continued

| Compound No. | Structural Formula |
|---|---|
| PP2329 | |
| PP2330 | |

TABLE 38-continued

| Compound No. | Structural Formula |
|---|---|
| PP2331 | |
| PP2332 | |

TABLE 38-continued

| Compound No. | Structural Formula |
|---|---|
| PP2333 | |
| PP2334 | |

TABLE 38-continued

| Compound No. | Structural Formula |
|---|---|
| PP2335 | |
| PP2336 | |

TABLE 38-continued
| Compound No. | Structural Formula |
|---|---|
| PP2337 | 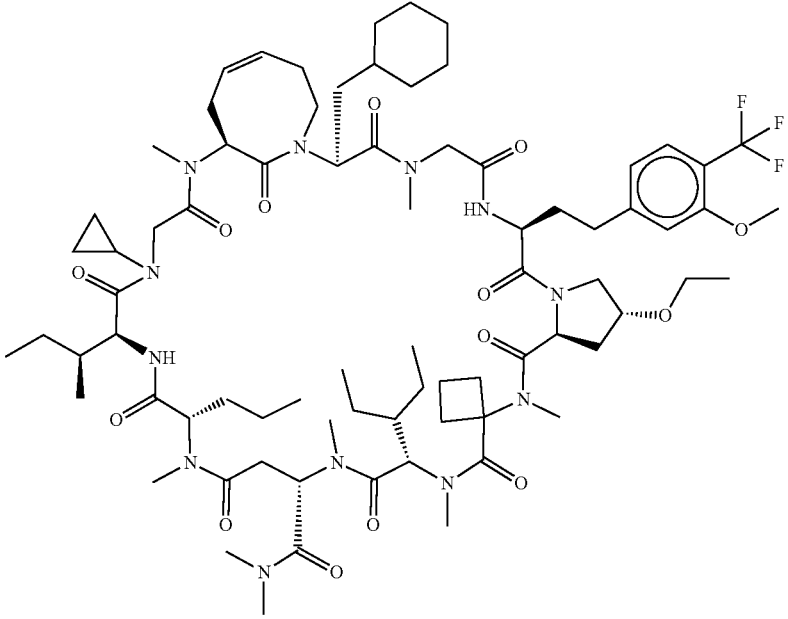 |
| PP2338 | 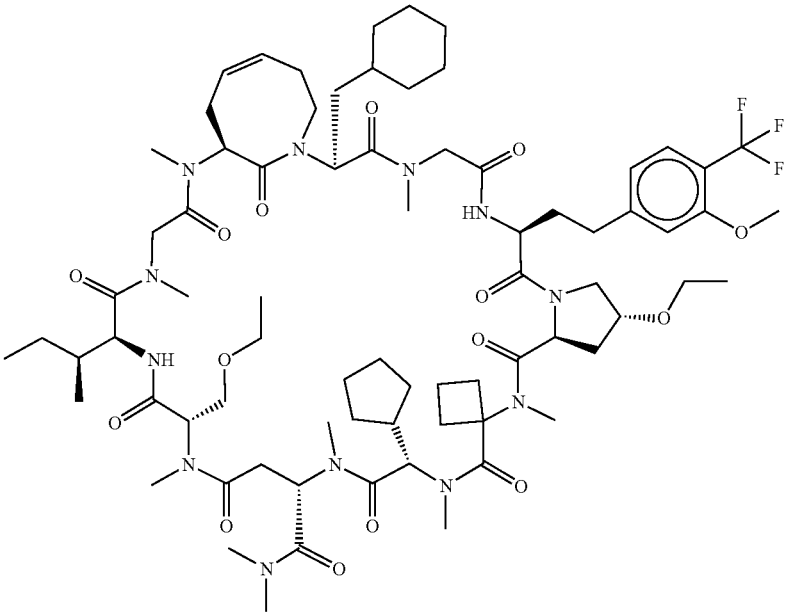 |

TABLE 38-continued
| Compound No. | Structural Formula |
|---|---|
| PP2339 | 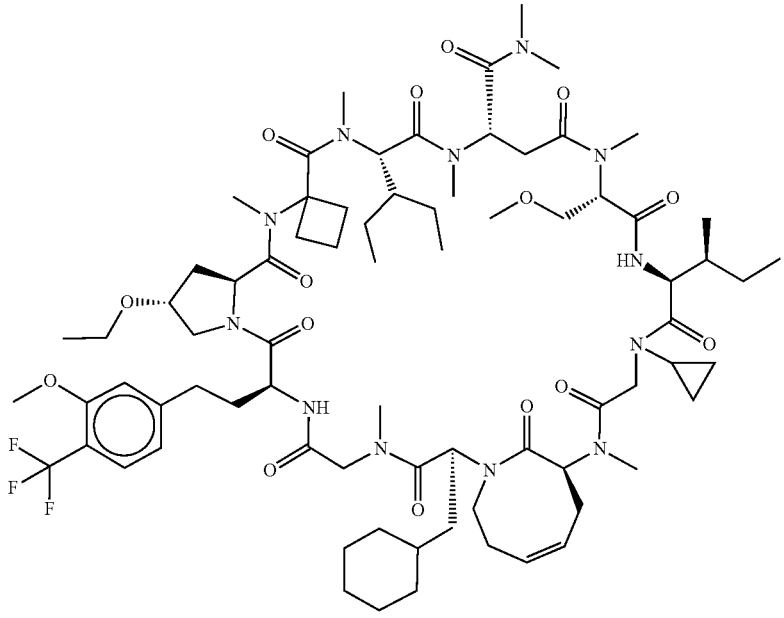 |
| PP2340 | 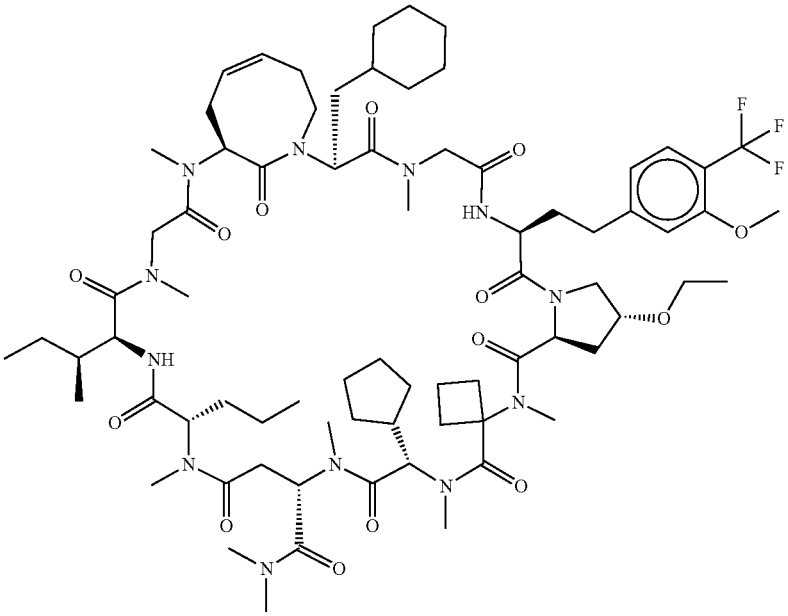 |

TABLE 38-continued
| Compound No. | Structural Formula |
|---|---|
| PP2341 | 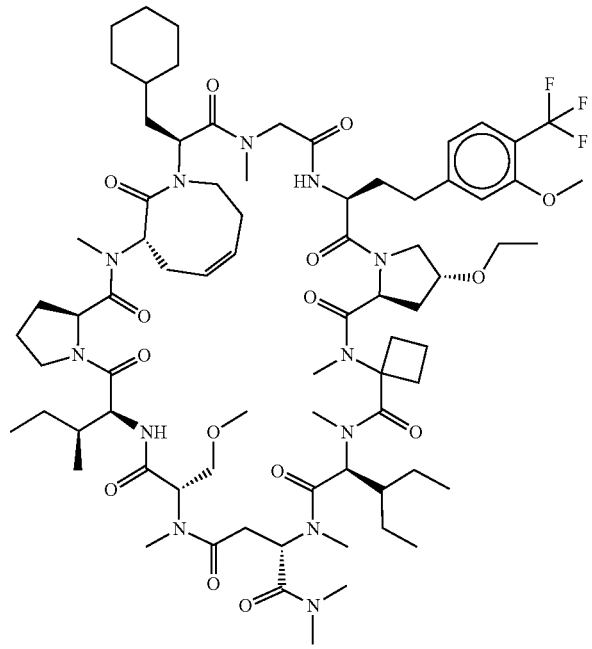 |
| PP2342 | 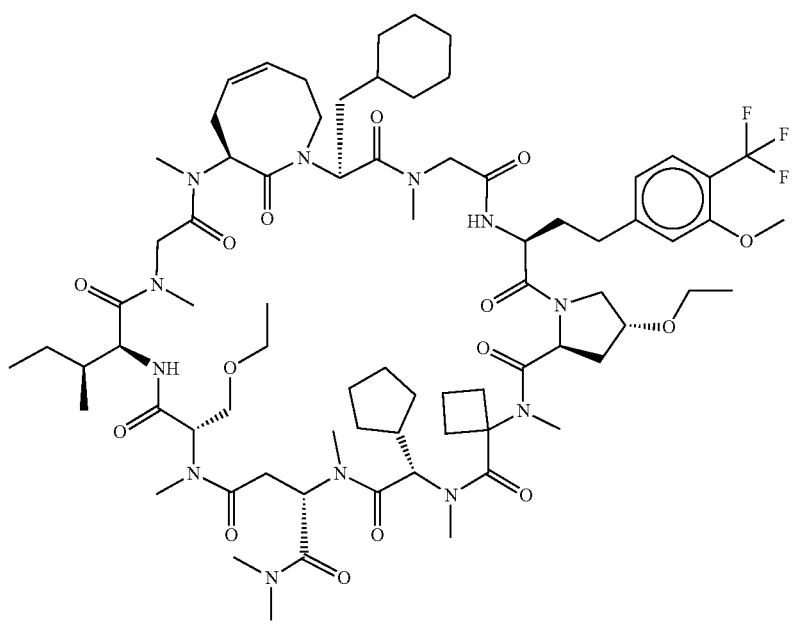 |

TABLE 38-continued
| Compound No. | Structural Formula |
|---|---|
| PP2343 | 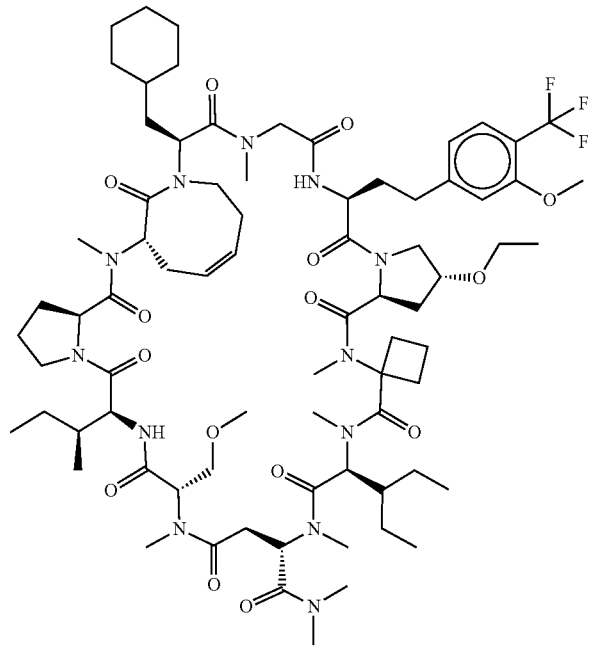 |
| PP2344 | 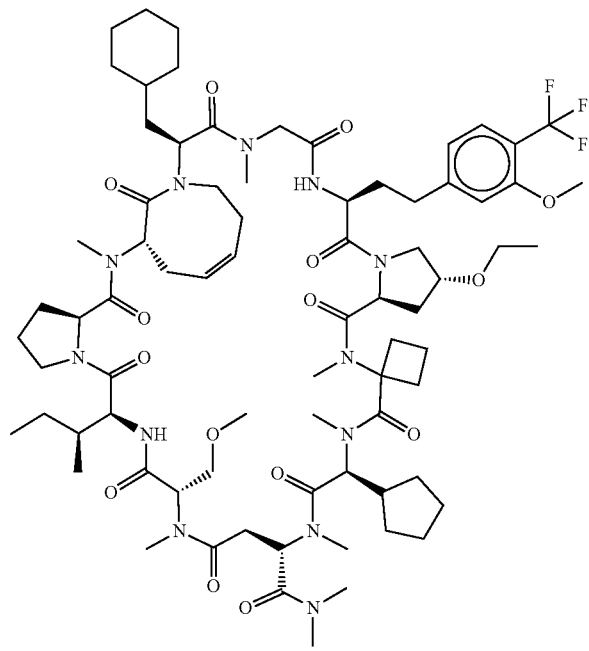 |

TABLE 38-continued

| Compound No. | Structural Formula |
|---|---|
| PP2345 | |
| PP2346 | |

TABLE 38-continued
| Compound No. | Structural Formula |
|---|---|
| PP2347 | 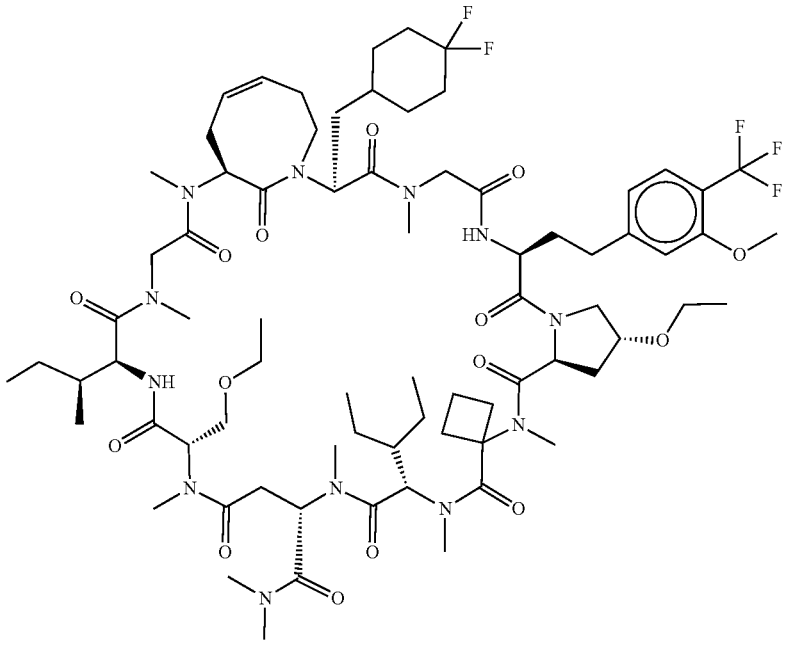 |
| PP2348 | 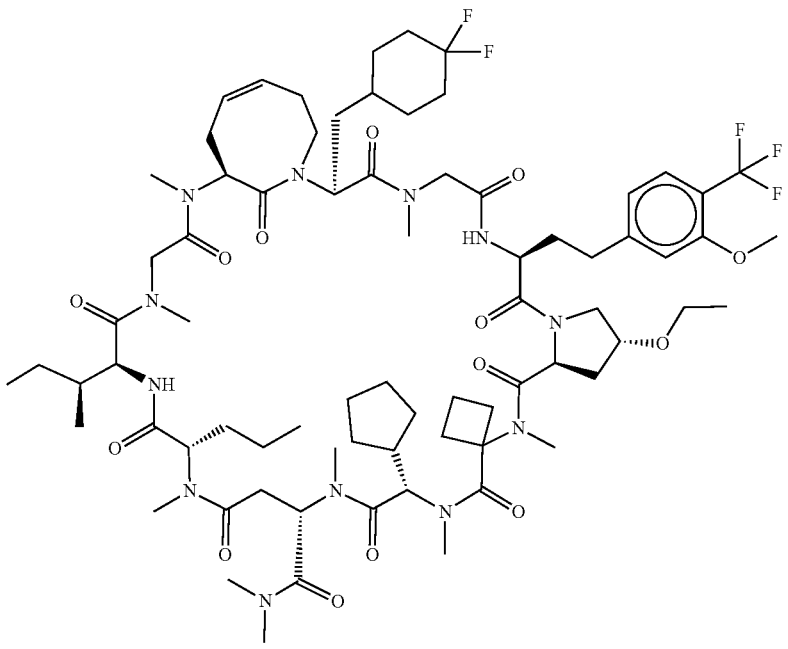 |

TABLE 38-continued
| Compound No. | Structural Formula |
|---|---|
| PP2349 | 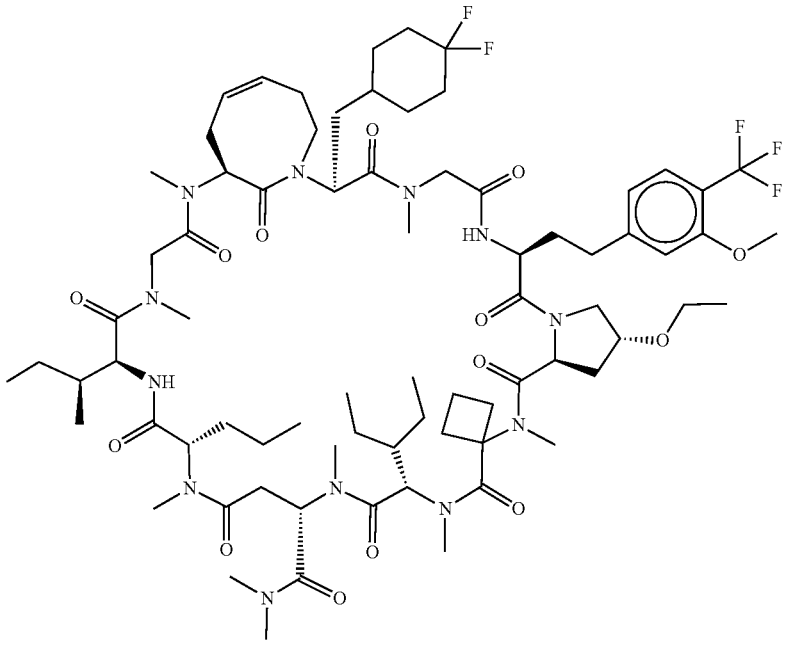 |
| PP2350 | 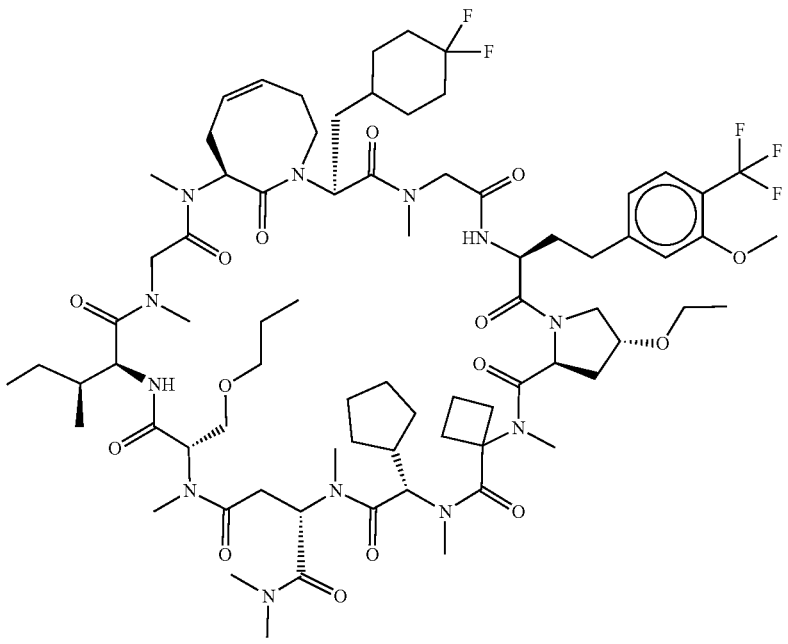 |

TABLE 38-continued

| Compound No. | Structural Formula |
| --- | --- |
| PP2351 | |
| PP2352 | |

TABLE 38-continued
| Compound No. | Structural Formula |
|---|---|
| PP2353 | 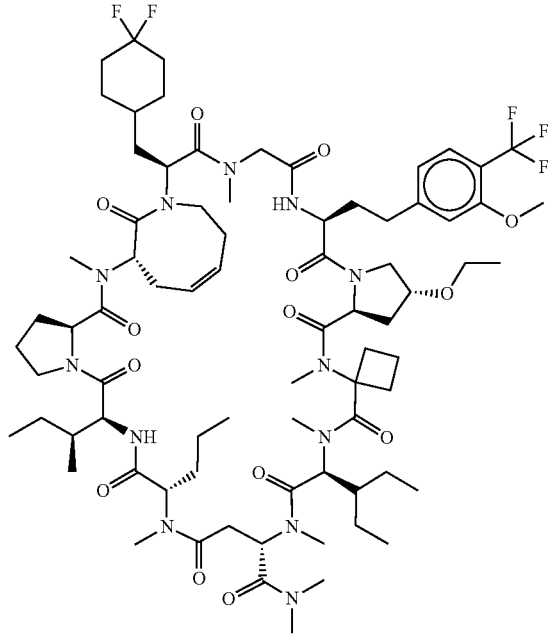 |
| PP2354 | 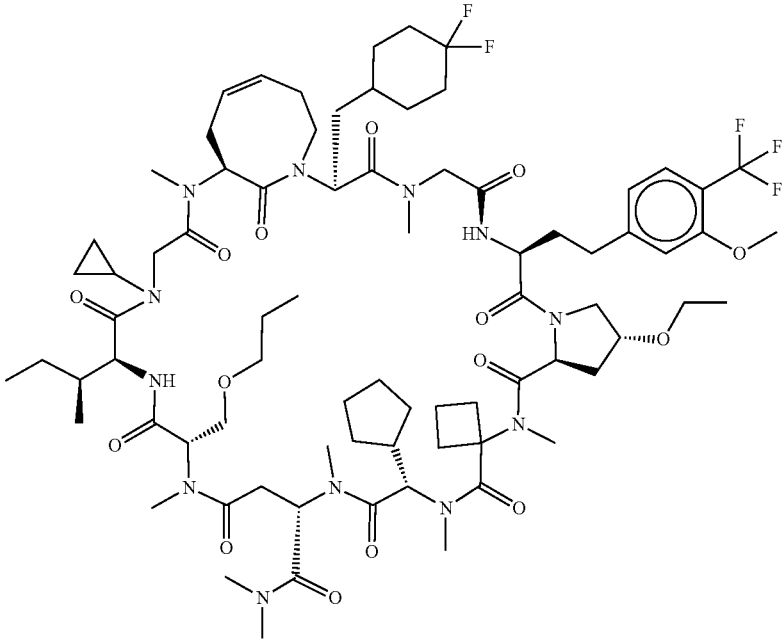 |

TABLE 38-continued

| Compound No. | Structural Formula |
|---|---|
| PP2355 | |
| PP2356 | |

TABLE 38-continued
| Compound No. | Structural Formula |
|---|---|
| PP2357 | 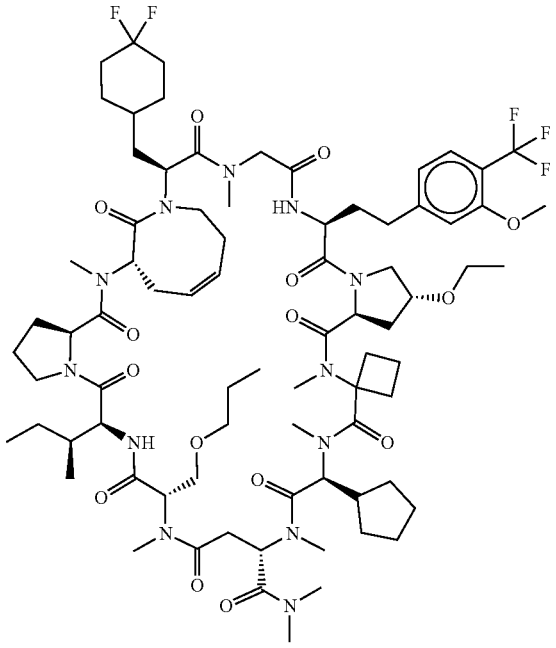 |
| PP2358 | 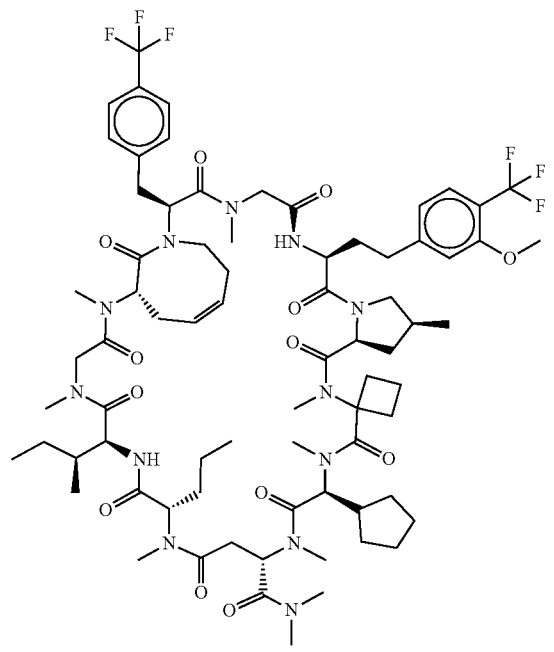 |

TABLE 38-continued

| Compound No. | Structural Formula |
|---|---|
| PP2359 | |
| PP2360 | |

TABLE 38-continued

| Compound No. | Structural Formula |
|---|---|
| PP2361 | |
| PP2362 | |

TABLE 38-continued
| Compound No. | Structural Formula |
| --- | --- |
| PP2363 | 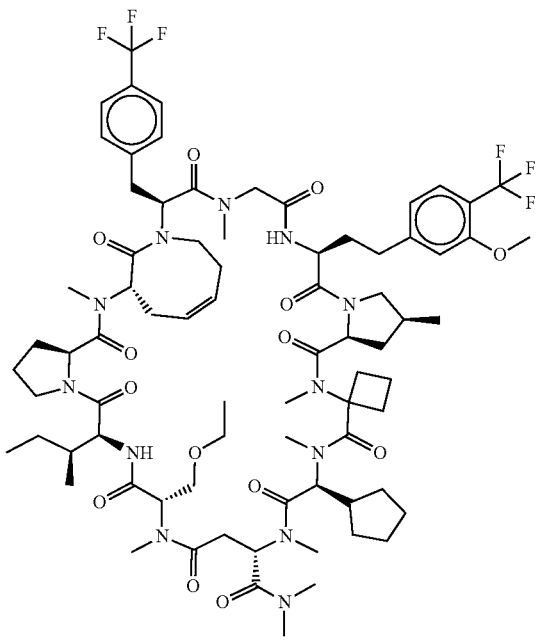 |
| PP2364 | 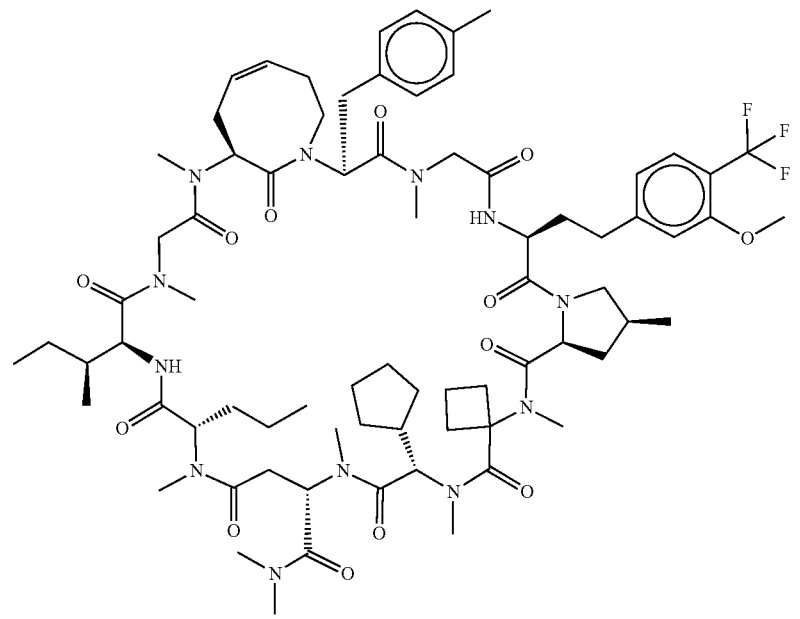 |

TABLE 38-continued

| Compound No. | Structural Formula |
|---|---|
| PP2365 | |
| PP2366 | |

TABLE 38-continued

| Compound No. | Structural Formula |
|---|---|
| PP2367 | |
| PP2368 | |

TABLE 38-continued

| Compound No. | Structural Formula |
|---|---|
| PP2369 | |
| PP2370 | |

TABLE 38-continued
| Compound No. | Structural Formula |
|---|---|
| PP2371 | 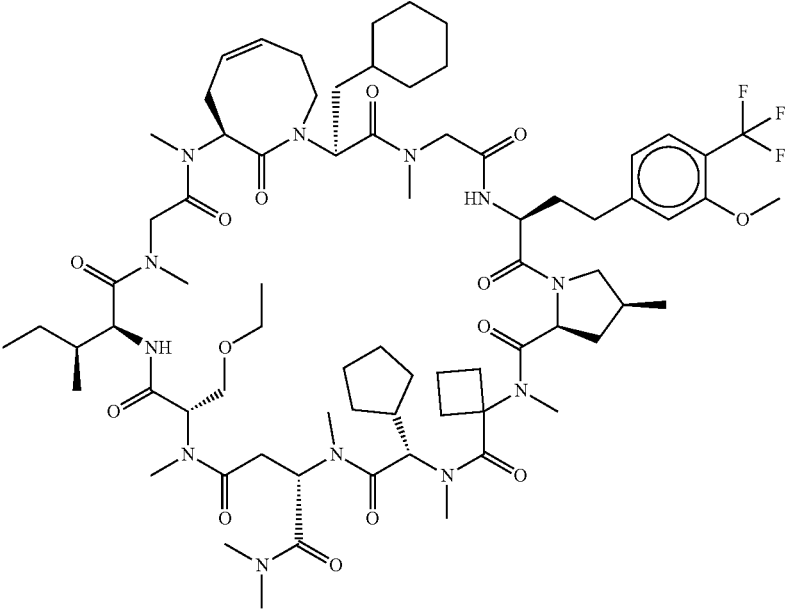 |
| PP2372 | 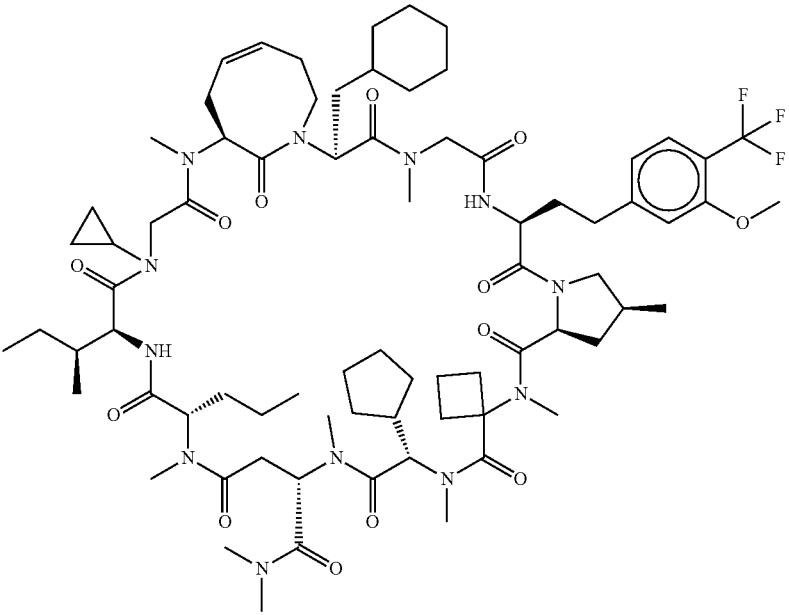 |

TABLE 38-continued

| Compound No. | Structural Formula |
|---|---|
| PP2373 | |
| PP2374 | |

TABLE 38-continued
| Compound No. | Structural Formula |
|---|---|
| PP2375 | 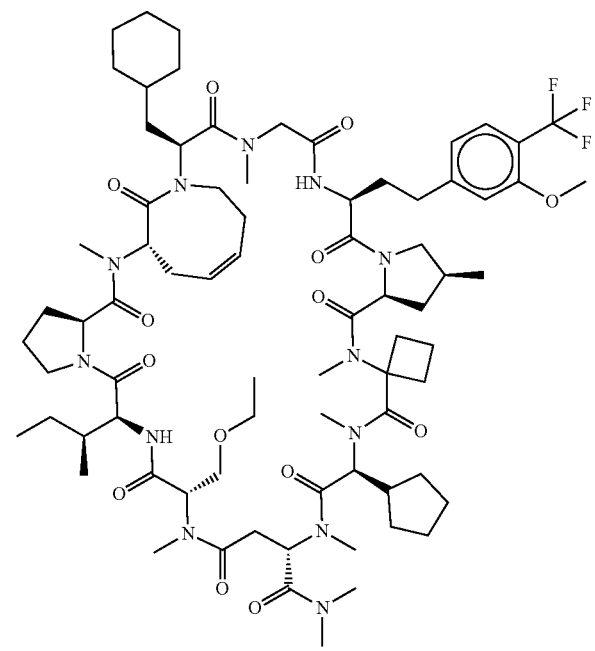 |
| PP2376 | 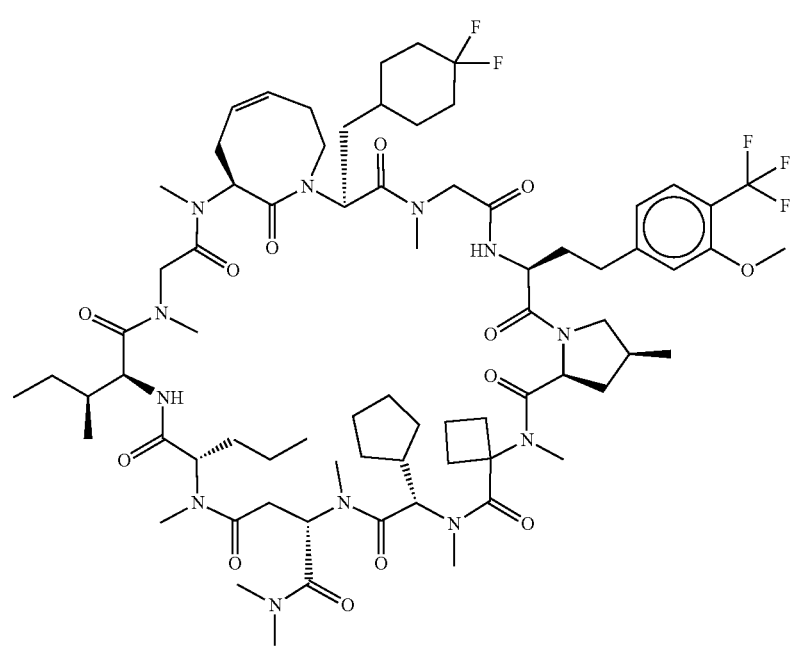 |

TABLE 38-continued
| Compound No. | Structural Formula |
|---|---|
| PP2377 | 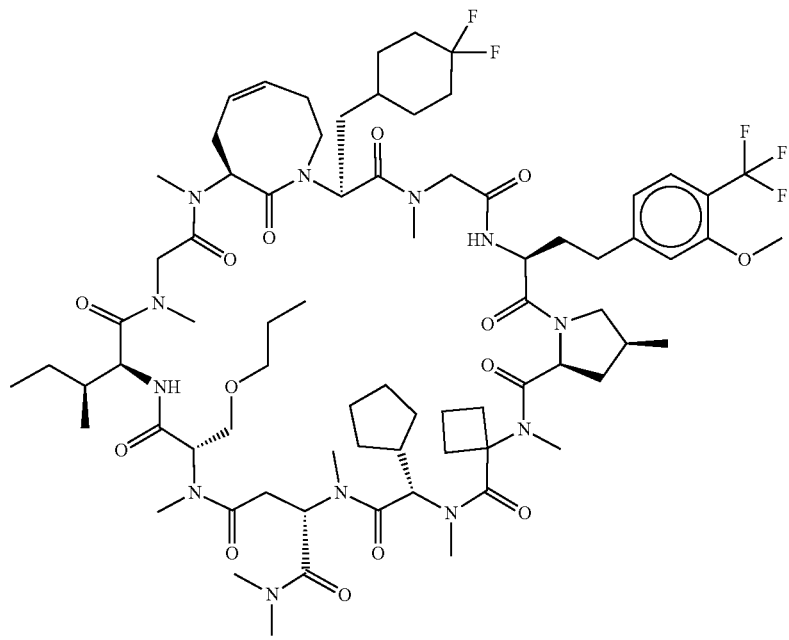 |
| PP2378 | 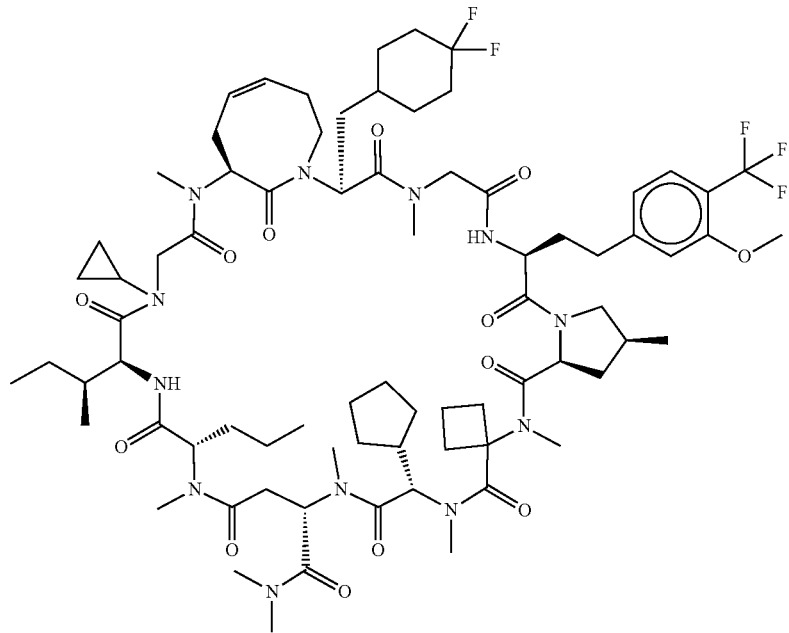 |

TABLE 38-continued

| Compound No. | Structural Formula |
|---|---|
| PP2379 | |
| PP2380 | |

TABLE 38-continued

| Compound No. | Structural Formula |
|---|---|
| PP2381 | (structure) |
| PP2382 | (structure) |

TABLE 38-continued
| Compound No. | Structural Formula |
| --- | --- |
| PP2383 | 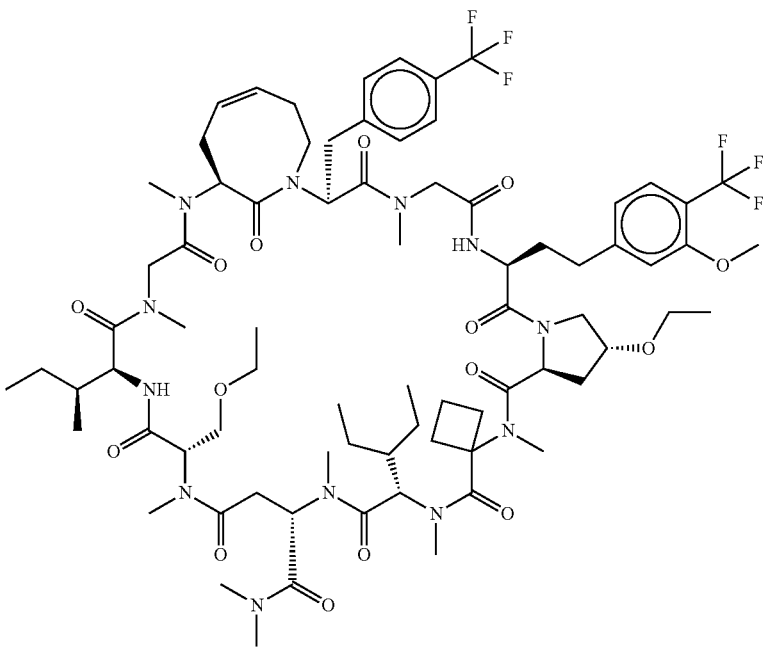 |
| PP2384 | 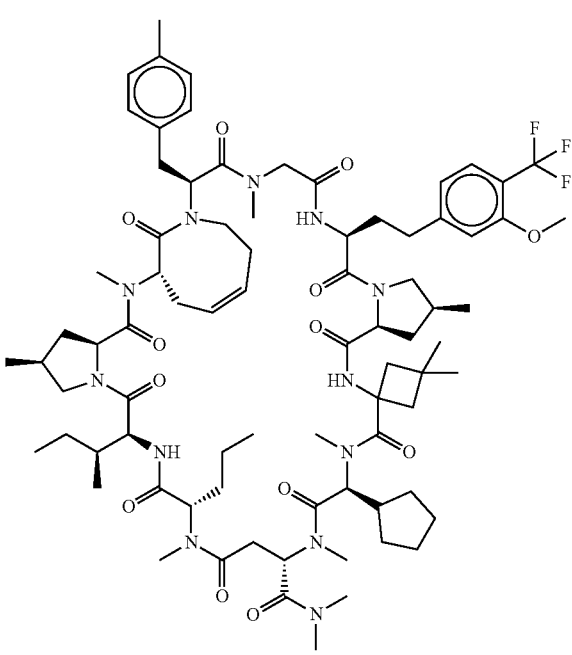 |

TABLE 38-continued

| Compound No. | Structural Formula |
|---|---|
| PP2385 | |
| PP2386 | |

TABLE 38-continued

| Compound No. | Structural Formula |
|---|---|
| PP2387 | |
| PP2388 | |

TABLE 38-continued
| Compound No. | Structural Formula |
|---|---|
| PP2389 | 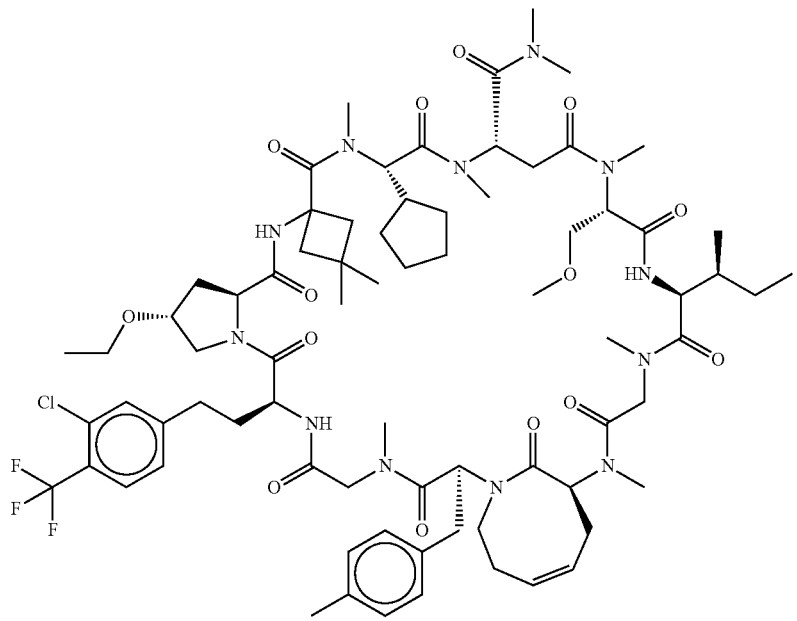 |
| PP2390 | 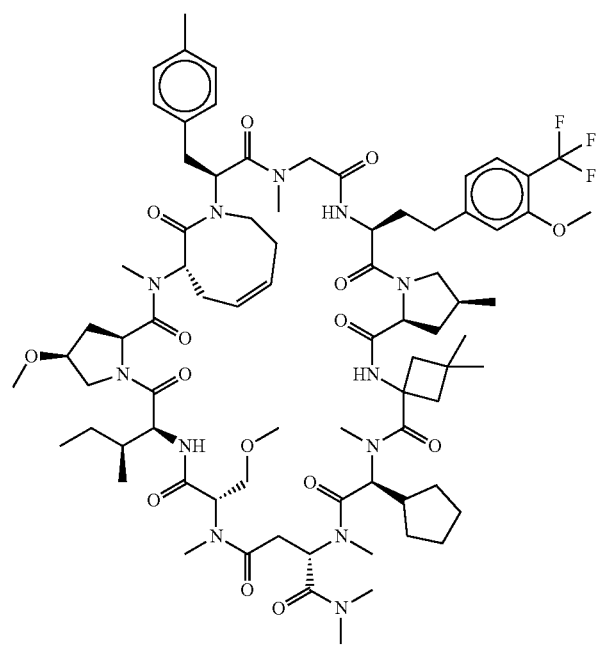 |

TABLE 38-continued
| Compound No. | Structural Formula |
|---|---|
| PP2391 | 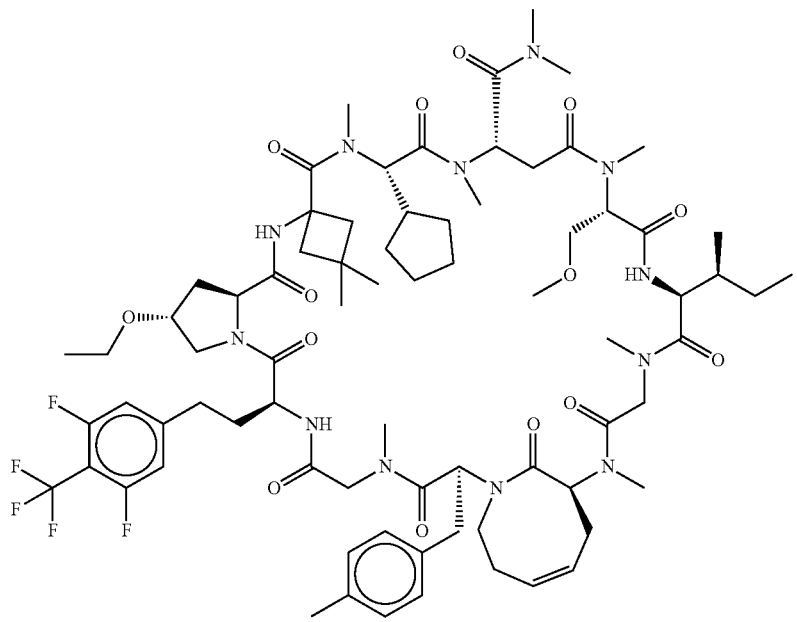 |
| PP2392 | 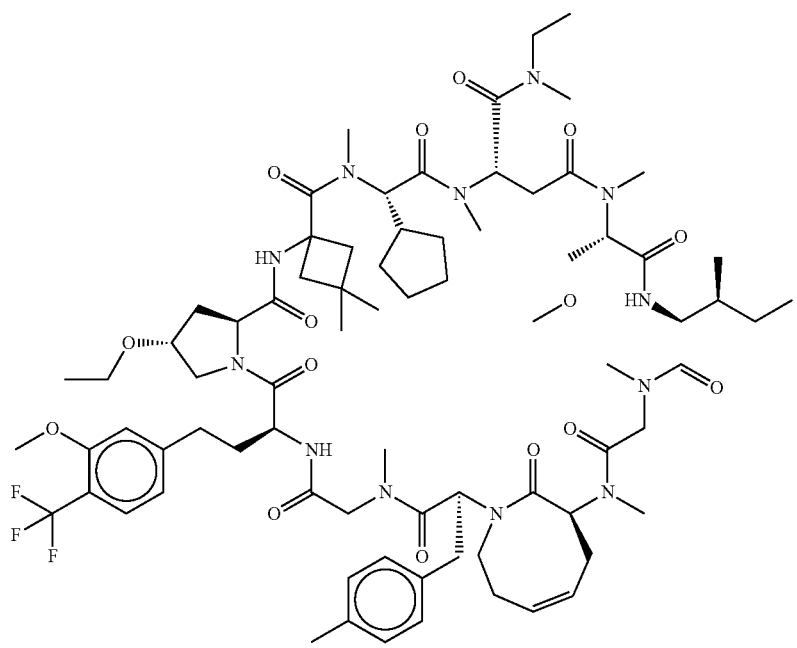 |

TABLE 38-continued

| Compound No. | Structural Formula |
|---|---|
| PP2393 | (structure) |
| PP2394 | (structure) |

TABLE 38-continued

| Compound No. | Structural Formula |
|---|---|
| PP2395 | |
| PP2396 | |

TABLE 38-continued
| Compound No. | Structural Formula |
|---|---|
| PP2397 | 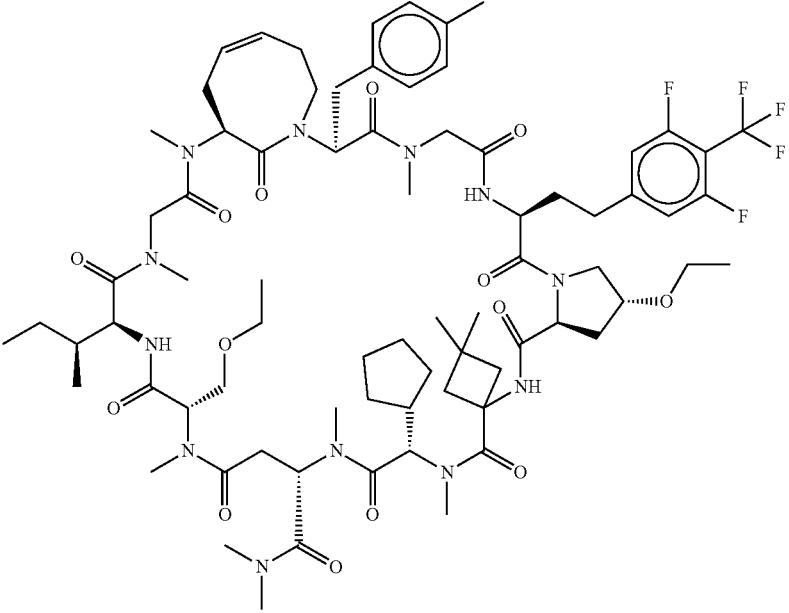 |
| PP2398 | 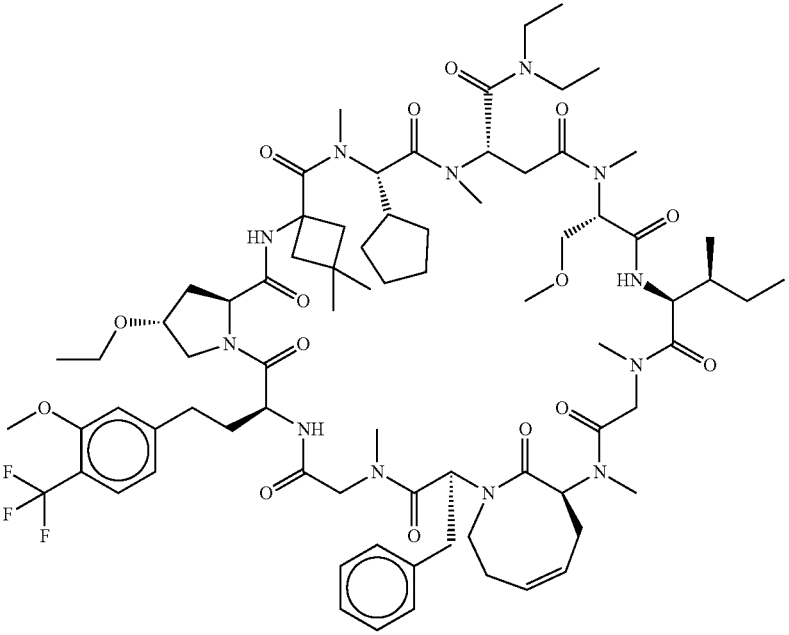 |

TABLE 38-continued

| Compound No. | Structural Formula |
|---|---|
| PP2399 | |
| PP2400 | |

TABLE 38-continued

| Compound No. | Structural Formula |
|---|---|
| PP2401 | |
| PP2402 | |

TABLE 38-continued

| Compound No. | Structural Formula |
|---|---|
| PP2403 | |
| PP2404 | |

TABLE 38-continued
| Compound No. | Structural Formula |
|---|---|
| PP2405 | 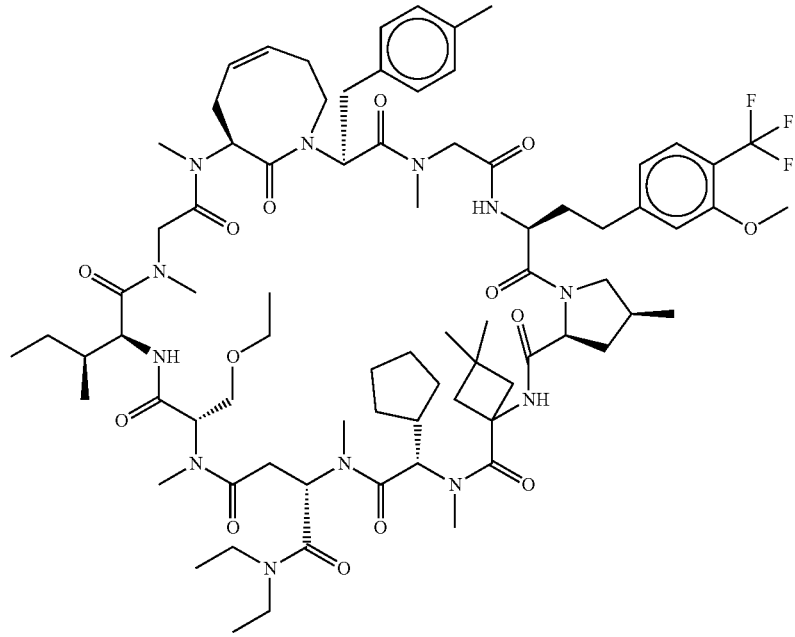 |
| PP2406 | 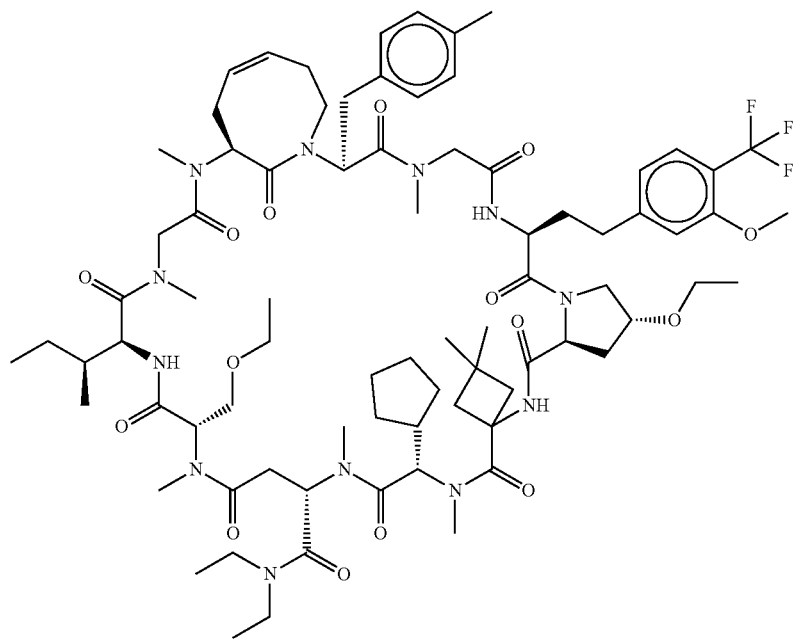 |

TABLE 38-continued

| Compound No. | Structural Formula |
|---|---|
| PP2407 | |
| PP2408 | |

TABLE 38-continued

| Compound No. | Structural Formula |
|---|---|
| PP2409 | |
| PP2410 | |

TABLE 38-continued
| Compound No. | Structural Formula |
|---|---|
| PP2411 | 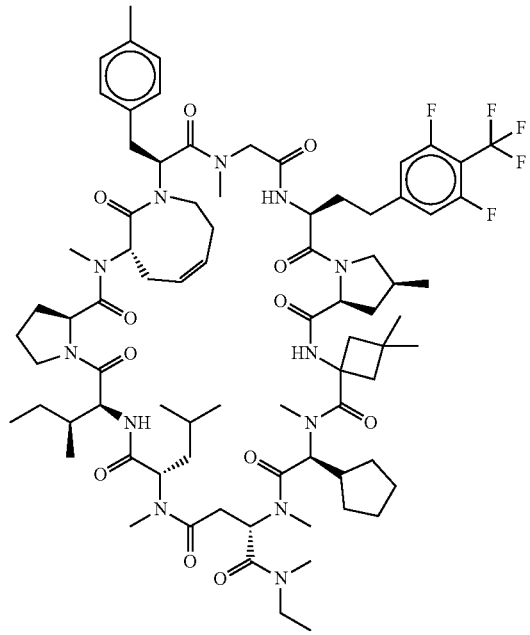 |
| PP2412 | 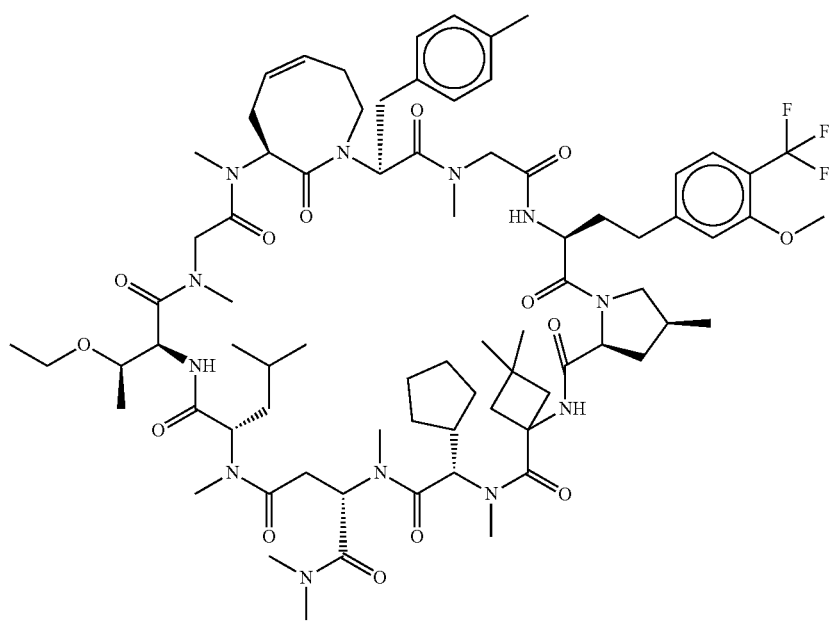 |

TABLE 38-continued
| Compound No. | Structural Formula |
|---|---|
| PP2413 | 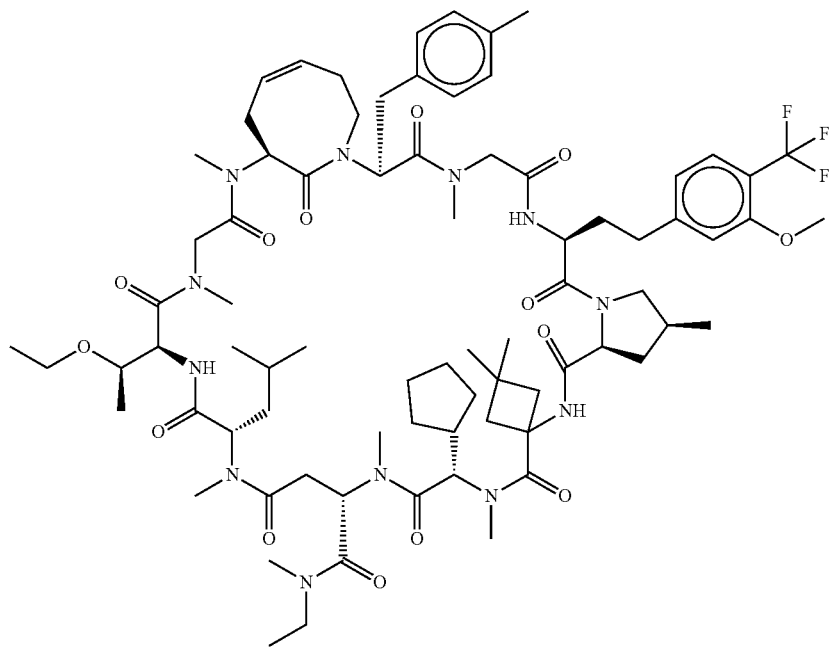 |
| PP2414 | 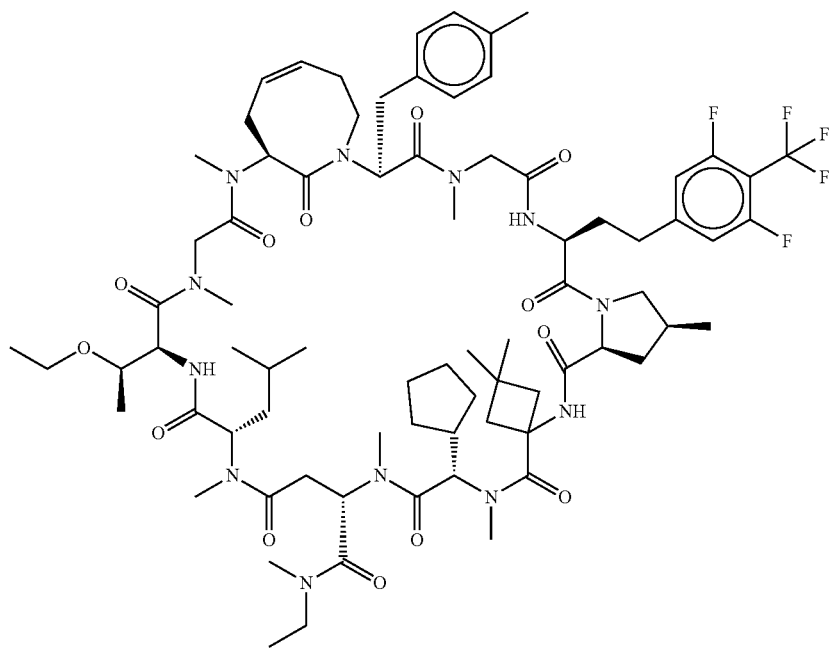 |

TABLE 38-continued
| Compound No. | Structural Formula |
|---|---|
| PP2415 | 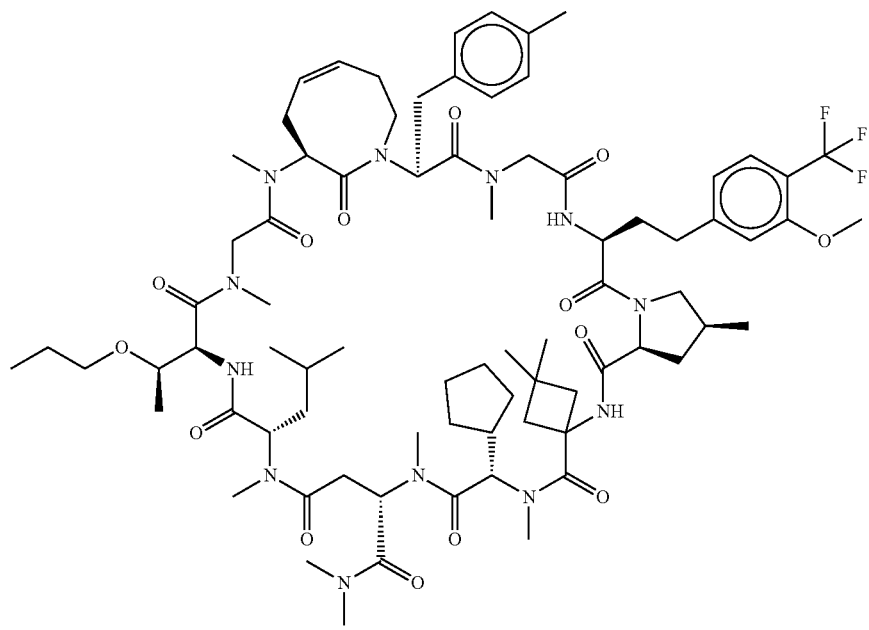 |
| PP2416 | 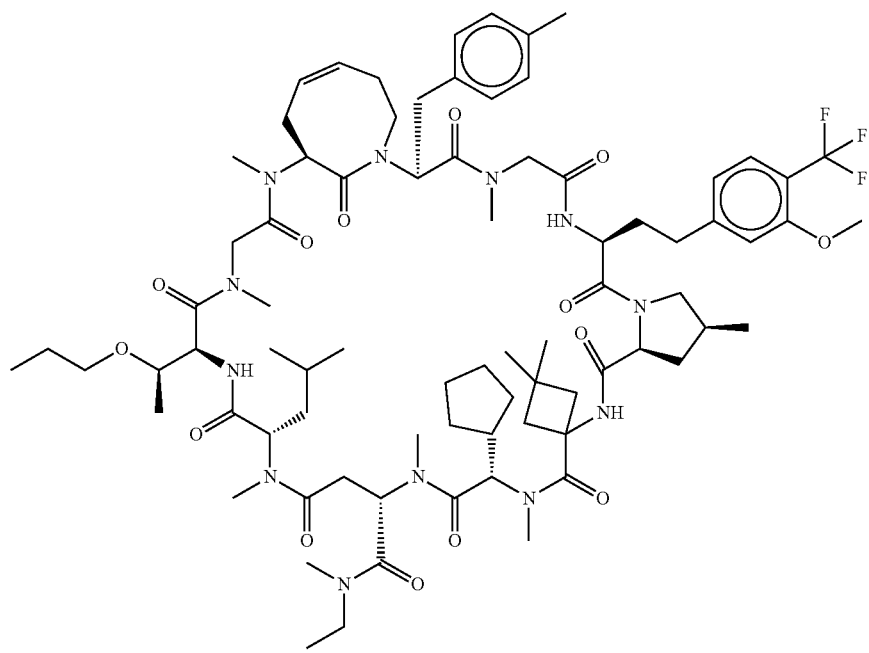 |

TABLE 38-continued

| Compound No. | Structural Formula |
|---|---|
| PP2417 | |
| PP2418 | |

TABLE 38-continued
| Compound No. | Structural Formula |
|---|---|
| PP2419 | 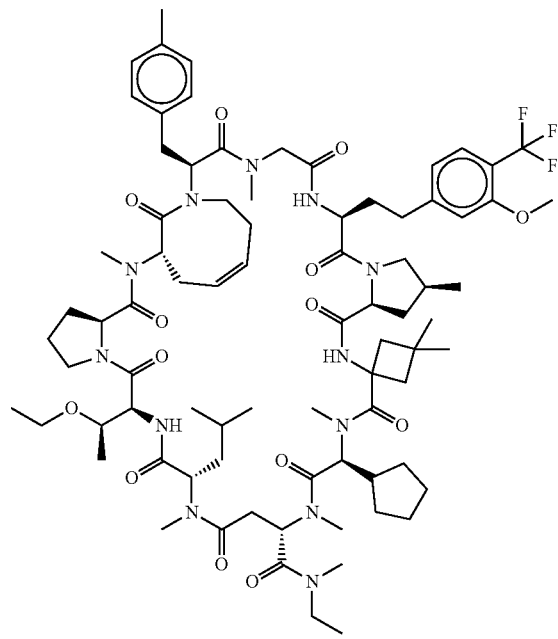 |
| PP2420 | 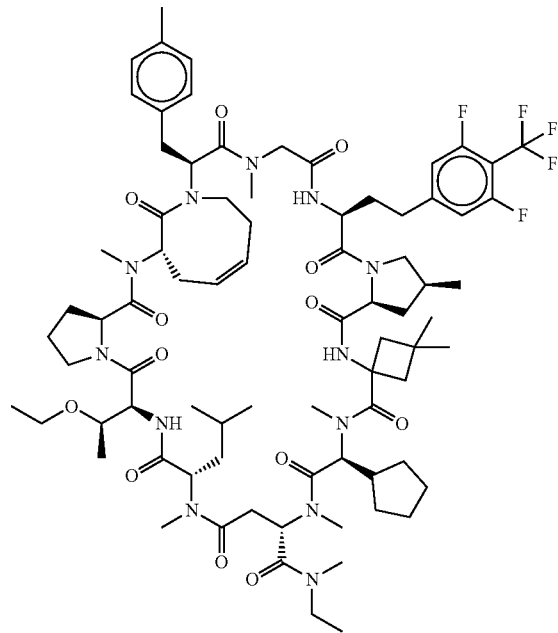 |

TABLE 38-continued

| Compound No. | Structural Formula |
|---|---|
| PP2421 | |
| PP2422 | |

TABLE 38-continued

| Compound No. | Structural Formula |
|---|---|
| PP2423 | |
| PP2424 | |

TABLE 38-continued
| Compound No. | Structural Formula |
|---|---|
| PP2425 | 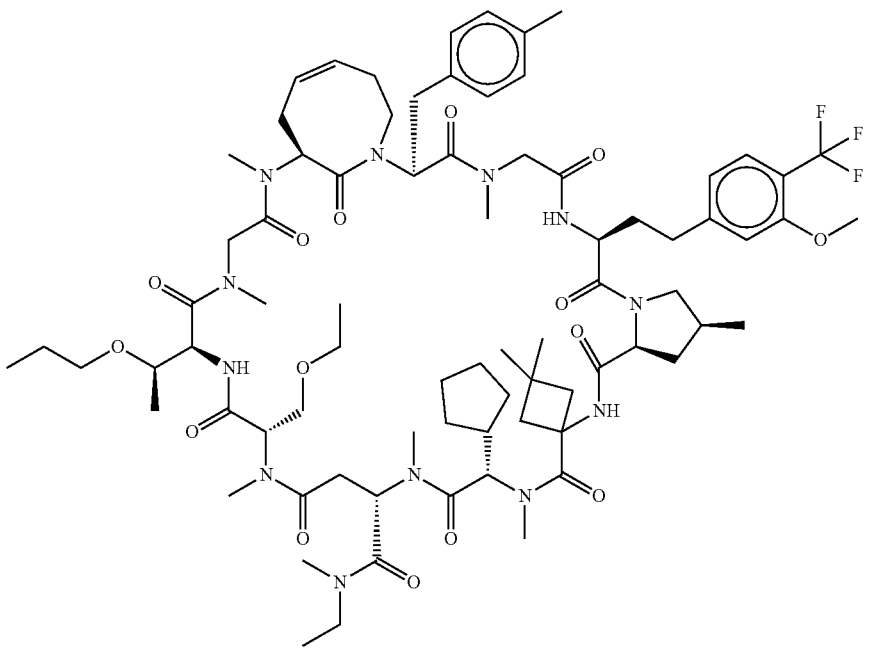 |
| PP2426 | 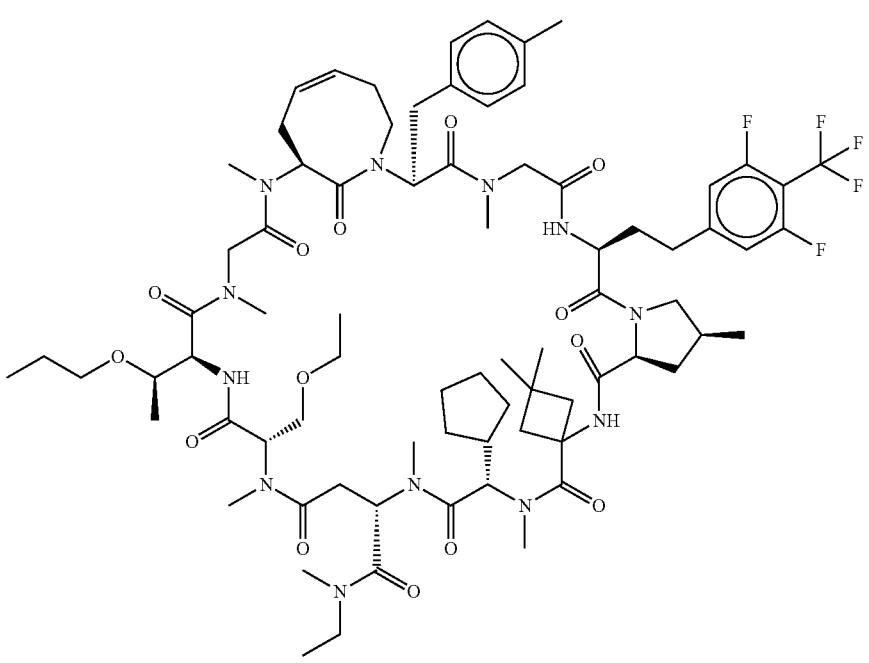 |

TABLE 38-continued

| Compound No. | Structural Formula |
|---|---|
| PP2427 | |
| PP2428 | |

TABLE 38-continued

| Compound No. | Structural Formula |
|---|---|
| PP2429 | |
| PP2430 | |

TABLE 38-continued

| Compound No. | Structural Formula |
|---|---|
| PP2431 | |
| PP2432 | |

TABLE 38-continued

| Compound No. | Structural Formula |
|---|---|
| PP2433 | |
| PP2434 | |

TABLE 38-continued

| Compound No. | Structural Formula |
|---|---|
| PP2435 | |
| PP2436 | |

TABLE 38-continued

| Compound No. | Structural Formula |
|---|---|
| PP2437 | |
| PP2438 | |

TABLE 38-continued

| Compound No. | Structural Formula |
|---|---|
| PP2439 | |
| PP2440 | |

TABLE 38-continued

| Compound No. | Structural Formula |
|---|---|
| PP2441 | |
| PP2442 | |

TABLE 38-continued
| Compound No. | Structural Formula |
|---|---|
| PP2443 | 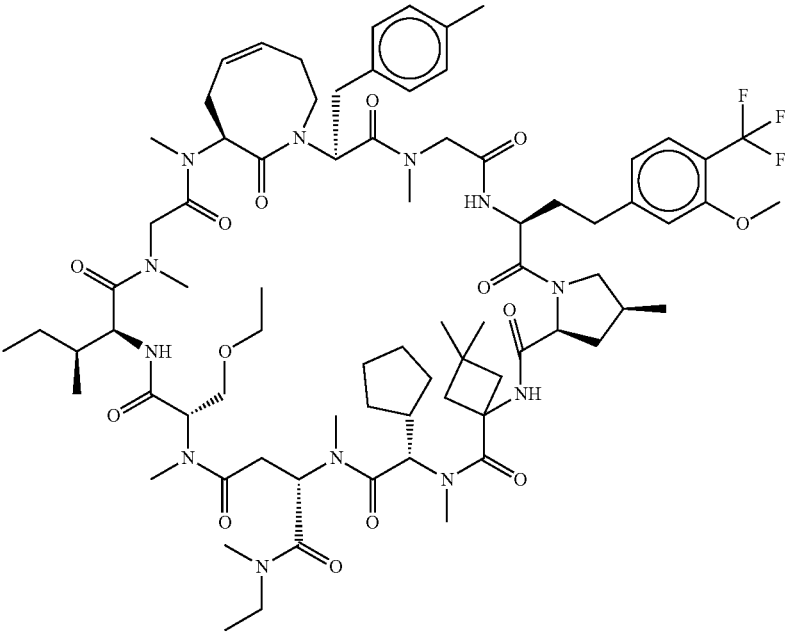 |
| PP2444 | 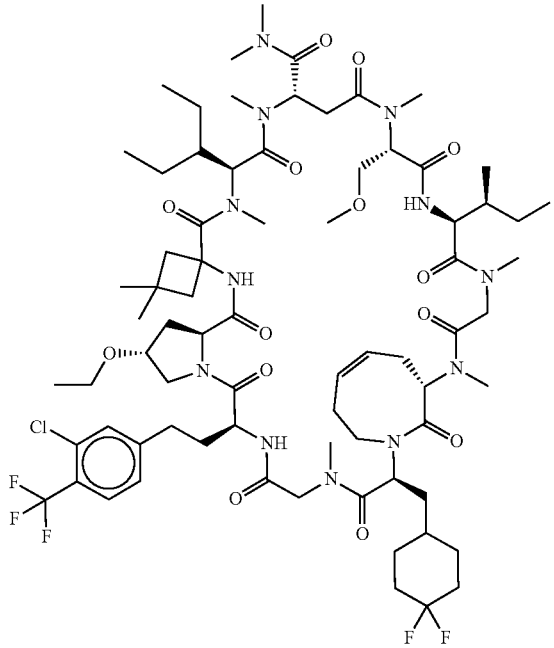 |

TABLE 38-continued
| Compound No. | Structural Formula |
|---|---|
| PP2445 | 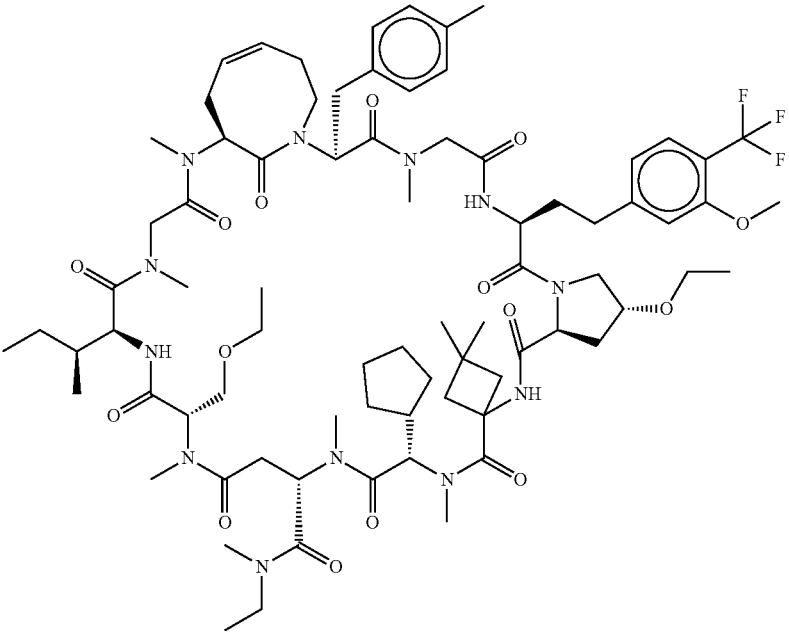 |
| PP2446 | 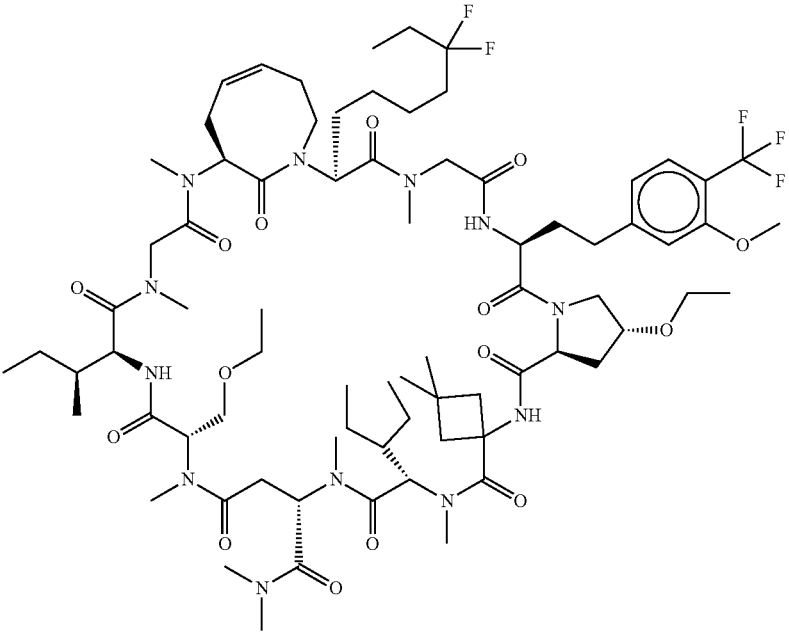 |

TABLE 38-continued

| Compound No. | Structural Formula |
| --- | --- |
| PP2447 | |
| PP2448 | |

TABLE 38-continued
| Compound No. | Structural Formula |
|---|---|
| PP2449 | 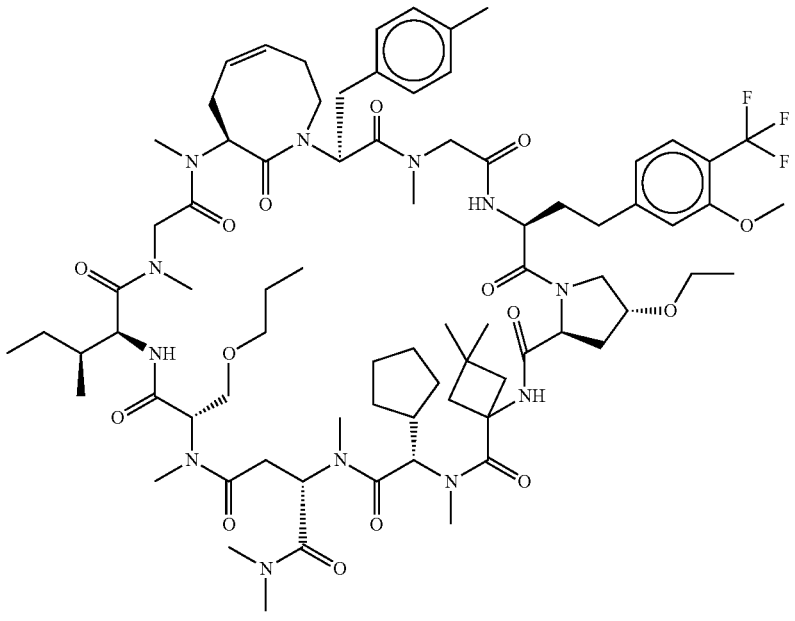 |
| PP2450 | 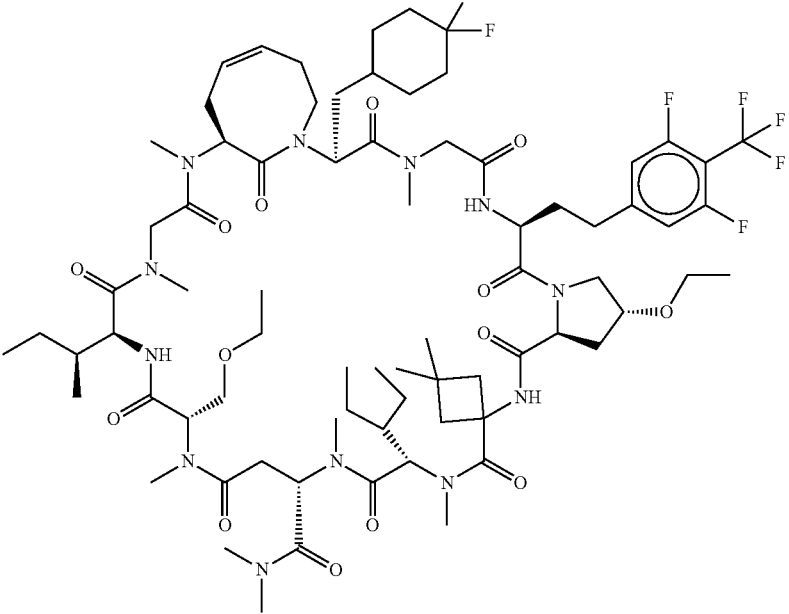 |

TABLE 38-continued

| Compound No. | Structural Formula |
|---|---|
| PP2451 | |
| PP2452 | |

TABLE 38-continued
| Compound No. | Structural Formula |
|---|---|
| PP2453 | 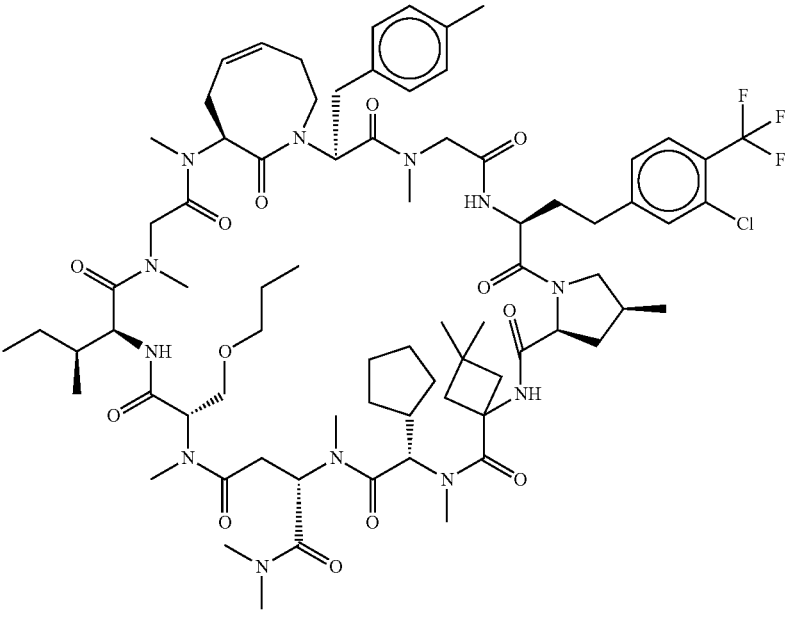 |
| PP2454 | 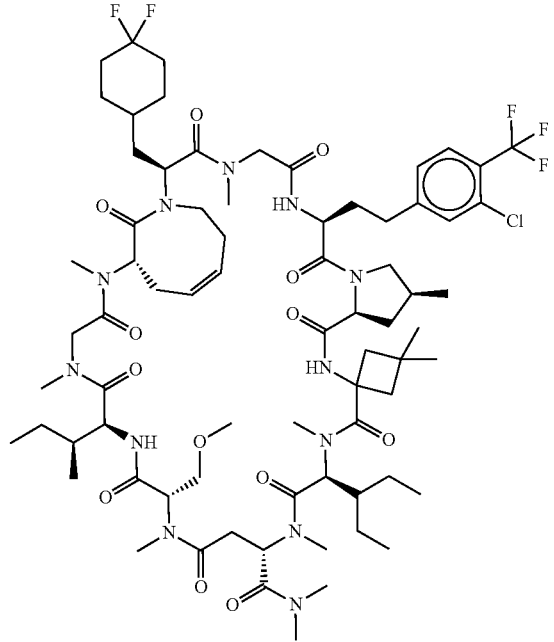 |

TABLE 38-continued

| Compound No. | Structural Formula |
|---|---|
| PP2455 | |
| PP2456 | |

TABLE 38-continued

| Compound No. | Structural Formula |
| --- | --- |
| PP2457 | |
| PP2458 | |

TABLE 38-continued
| Compound No. | Structural Formula |
|---|---|
| PP2460 | 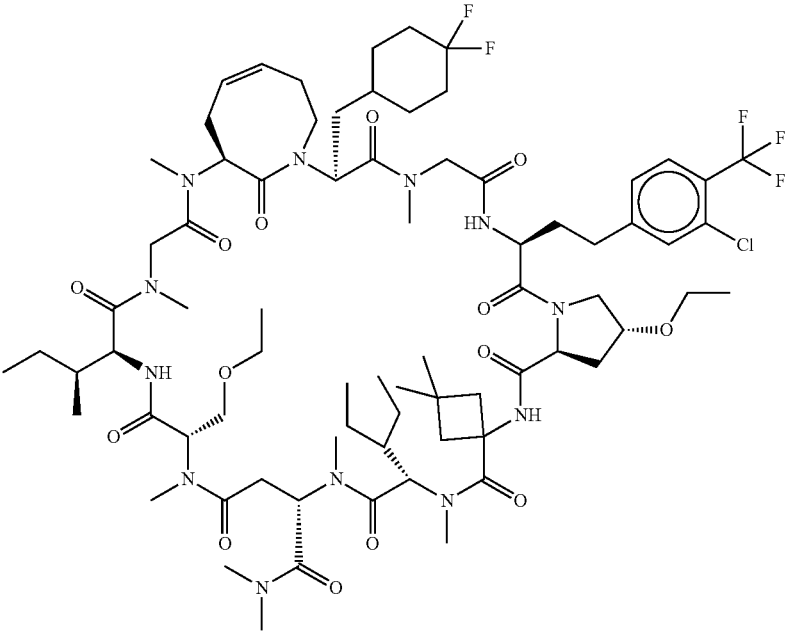 |
| PP2461 | 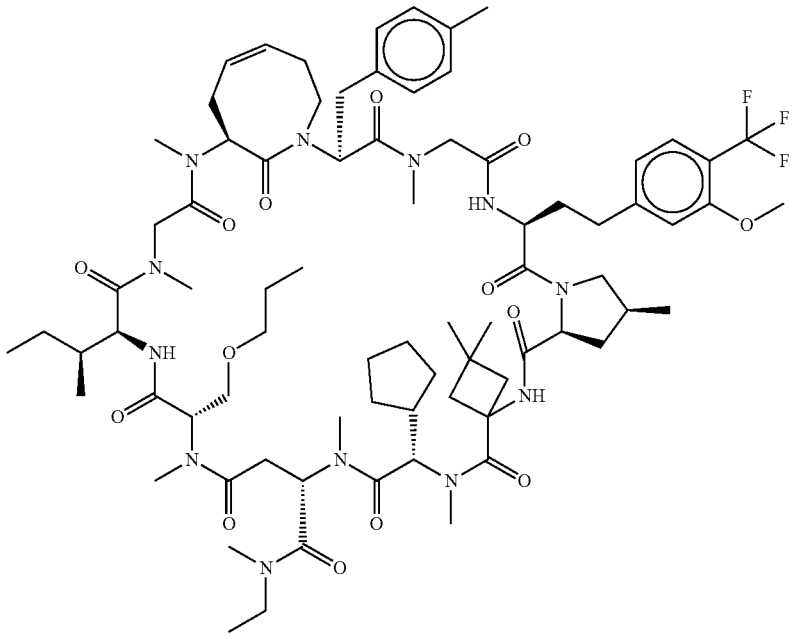 |

TABLE 38-continued
| Compound No. | Structural Formula |
|---|---|
| PP2462 | 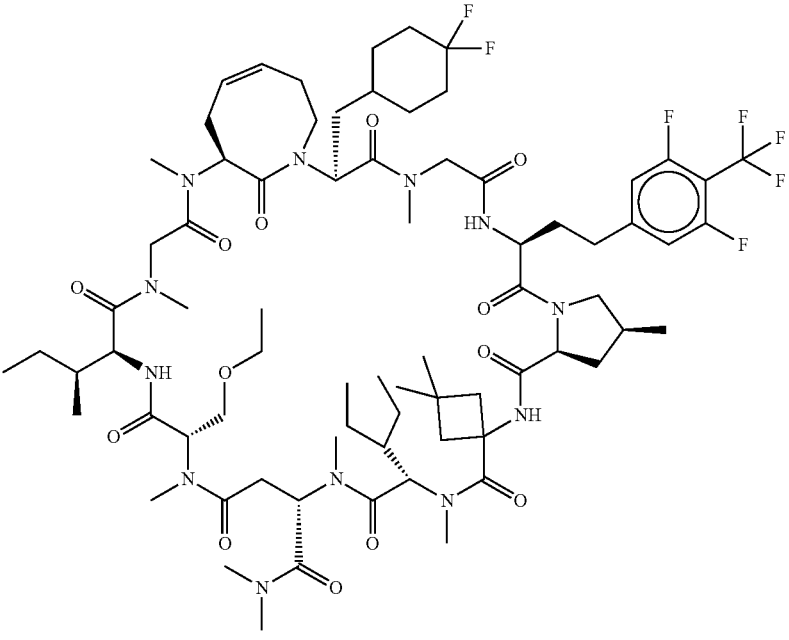 |
| PP2463 | 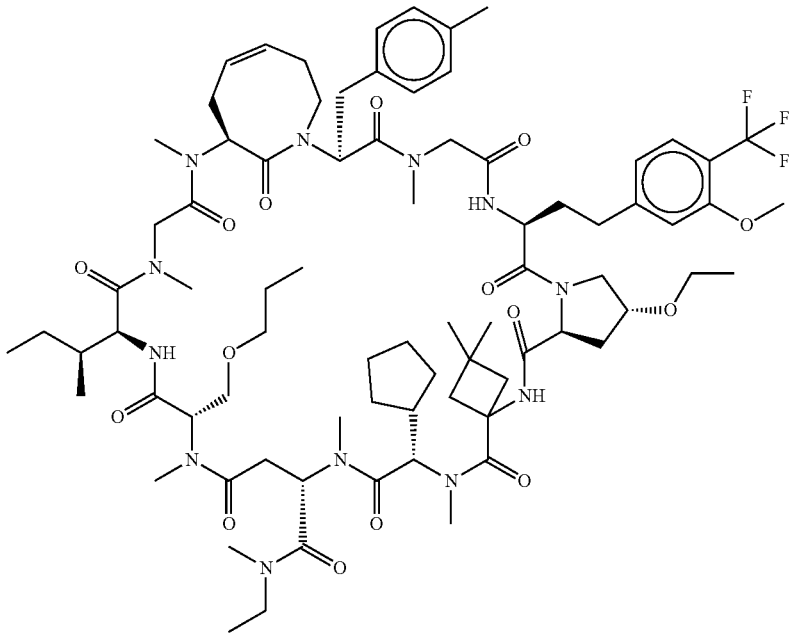 |

TABLE 38-continued
| Compound No. | Structural Formula |
|---|---|
| PP2464 | 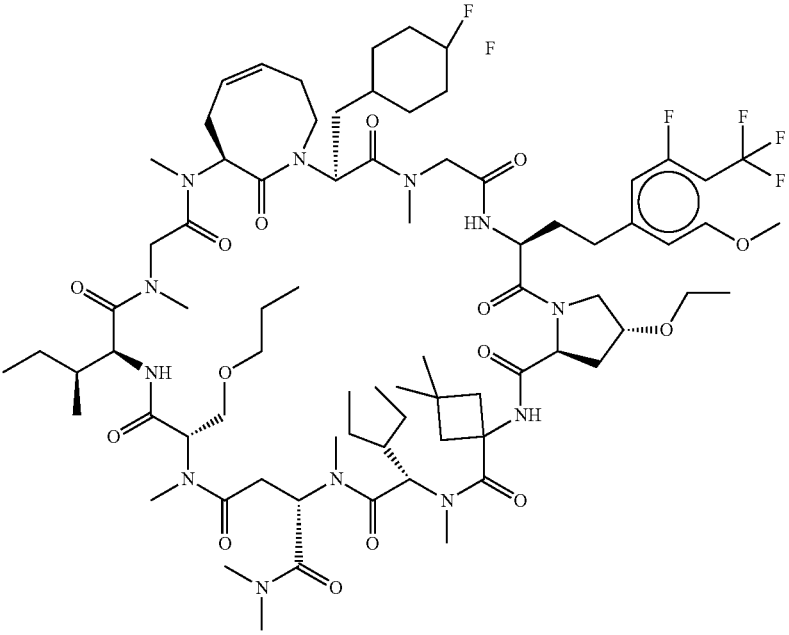 |
| PP2465 | 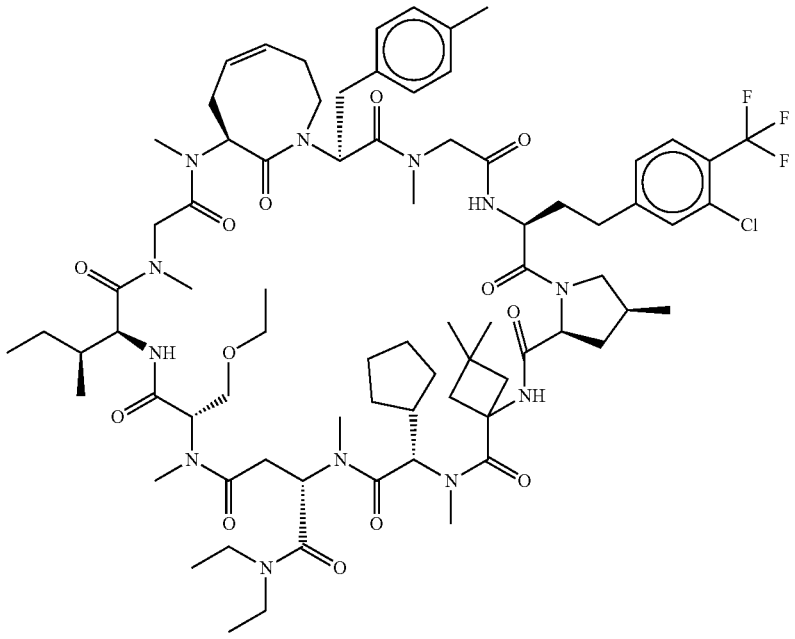 |

TABLE 38-continued
| Compound No. | Structural Formula |
|---|---|
| PP2466 | 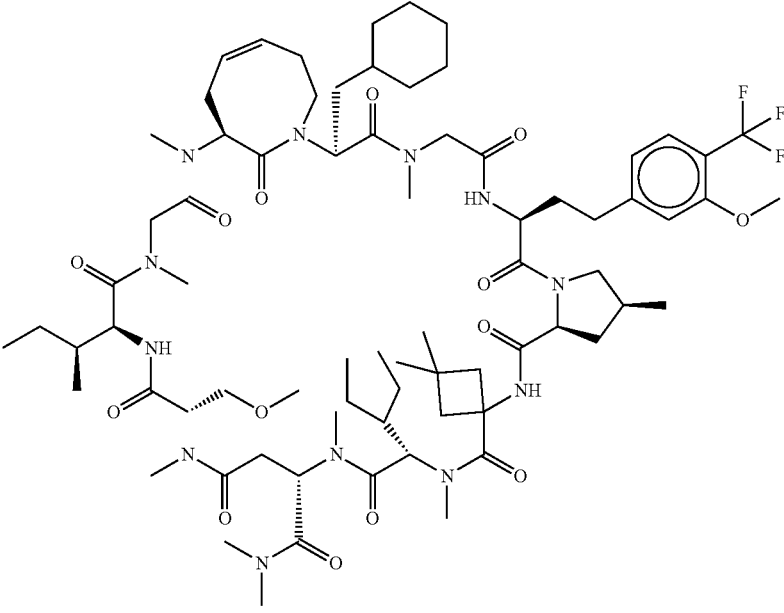 |
| PP2467 | 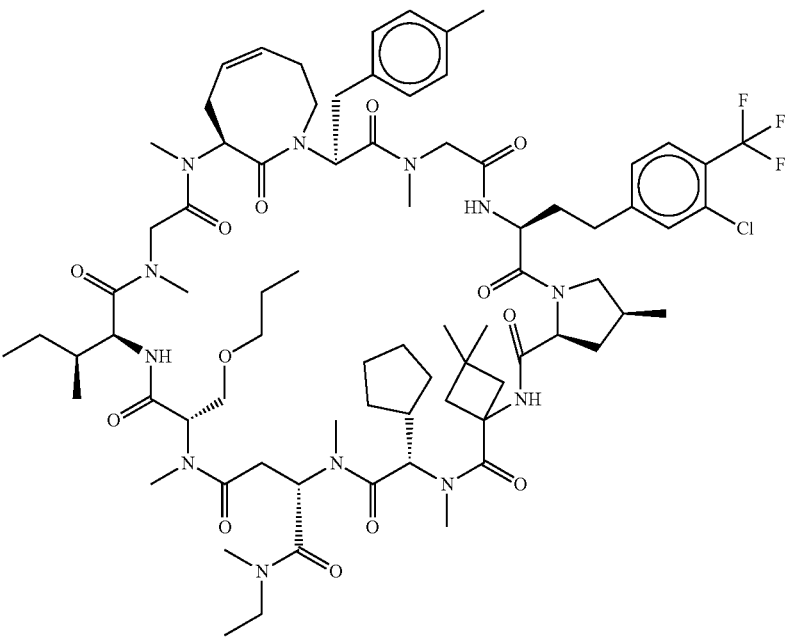 |

TABLE 38-continued

| Compound No. | Structural Formula |
|---|---|
| PP2468 | |
| PP2469 | |

TABLE 38-continued
| Compound No. | Structural Formula |
| --- | --- |
| PP2470 | 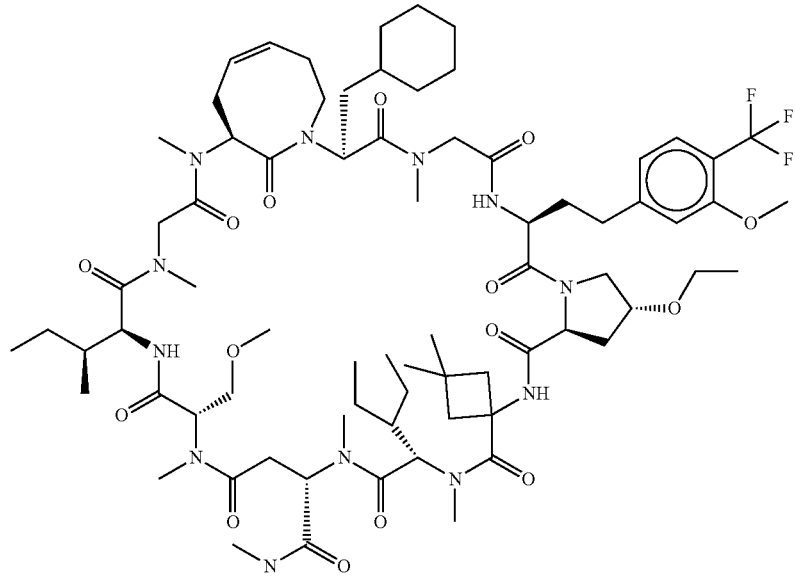 |
| PP2471 | 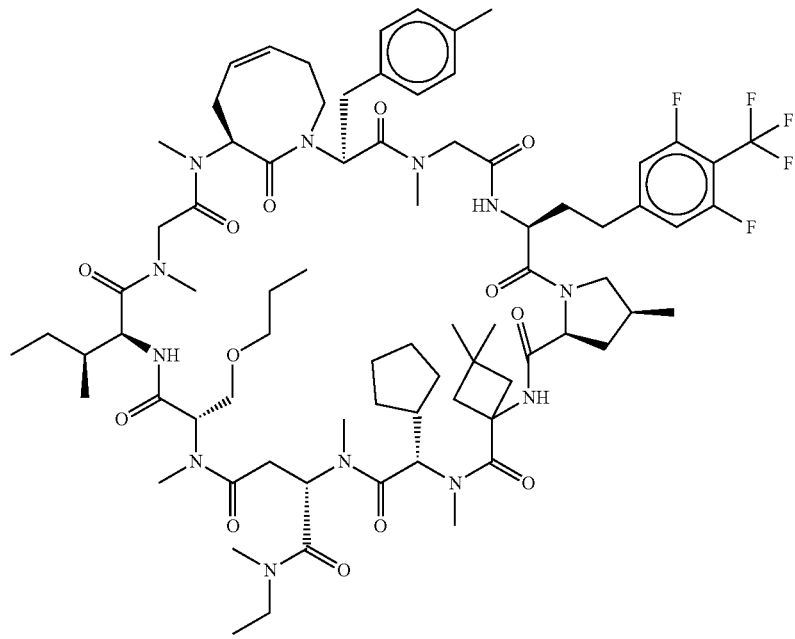 |

TABLE 38-continued
| Compound No. | Structural Formula |
|---|---|
| PP2472 | 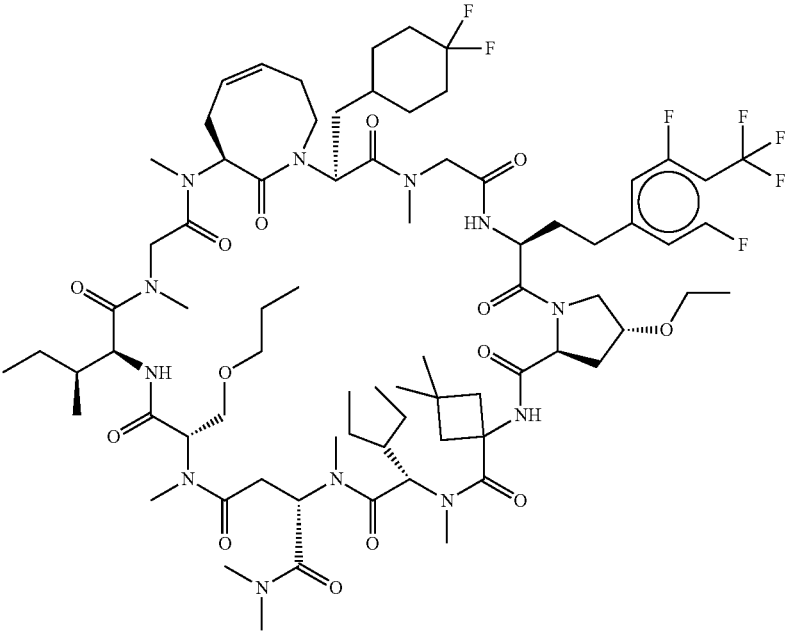 |
| PP2473 | 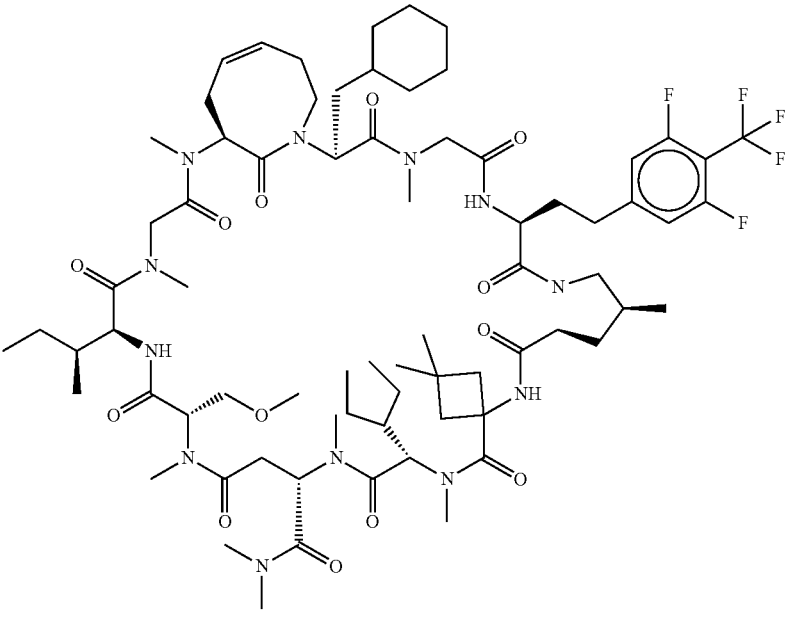 |

TABLE 38-continued
| Compound No. | Structural Formula |
|---|---|
| PP2475 | 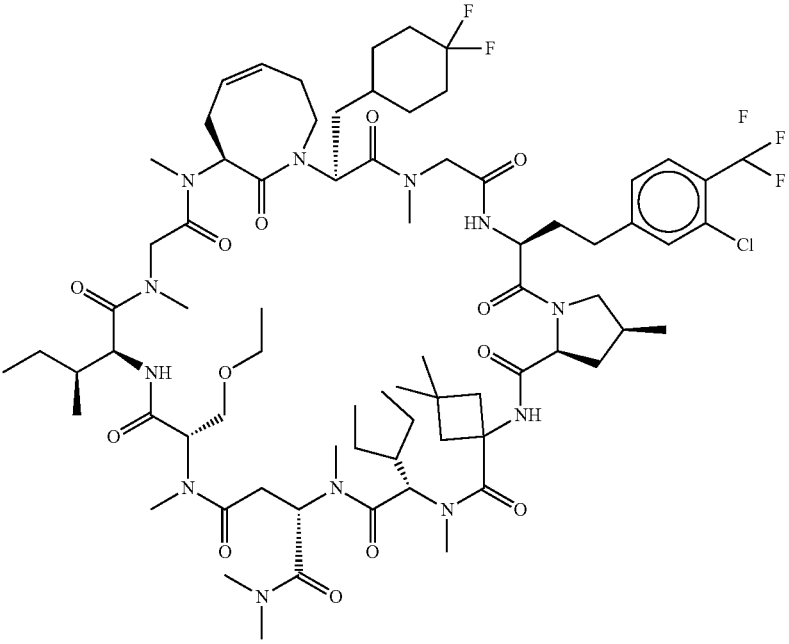 |
| PP2477 | 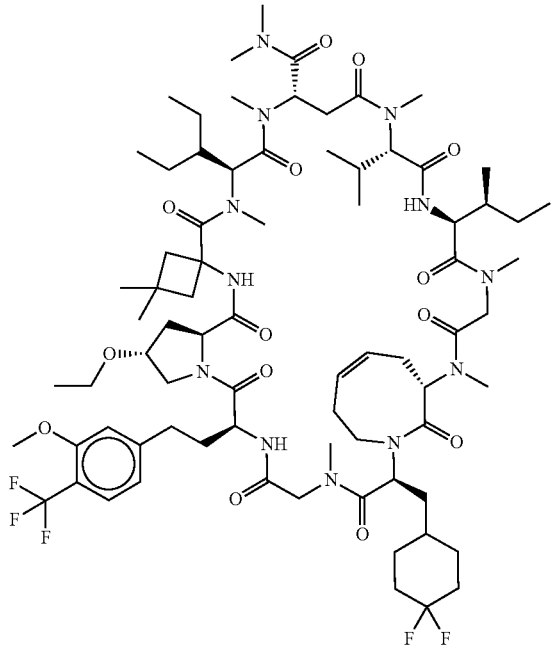 |

TABLE 38-continued
| Compound No. | Structural Formula |
|---|---|
| PP2479 | 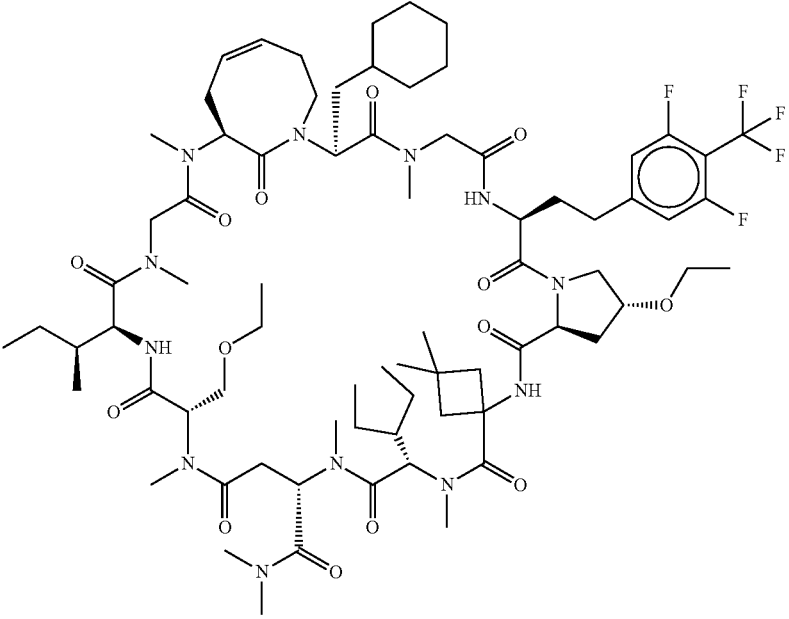 |
| PP2480 | 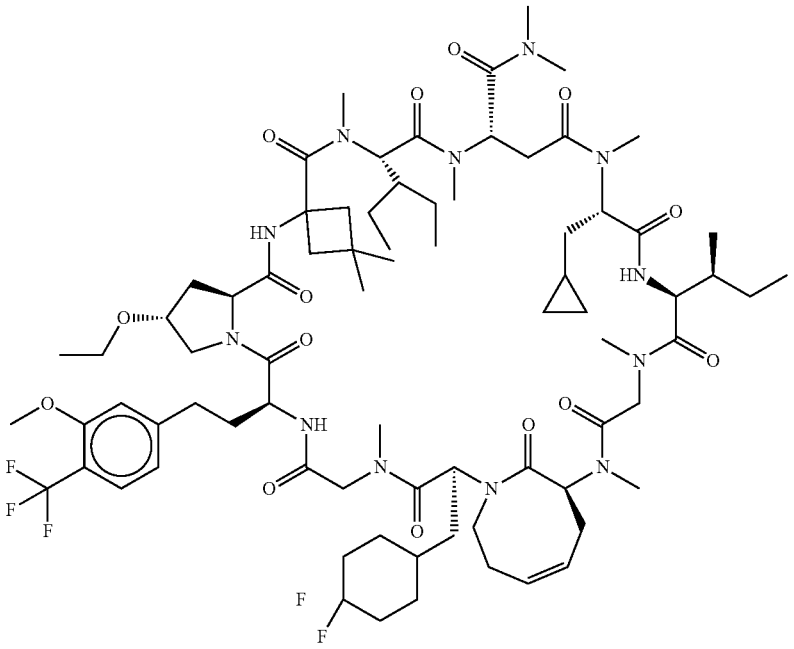 |

TABLE 38-continued

| Compound No. | Structural Formula |
|---|---|
| PP2481 | |
| PP2482 | |

TABLE 38-continued
| Compound No. | Structural Formula |
|---|---|
| PP2483 | 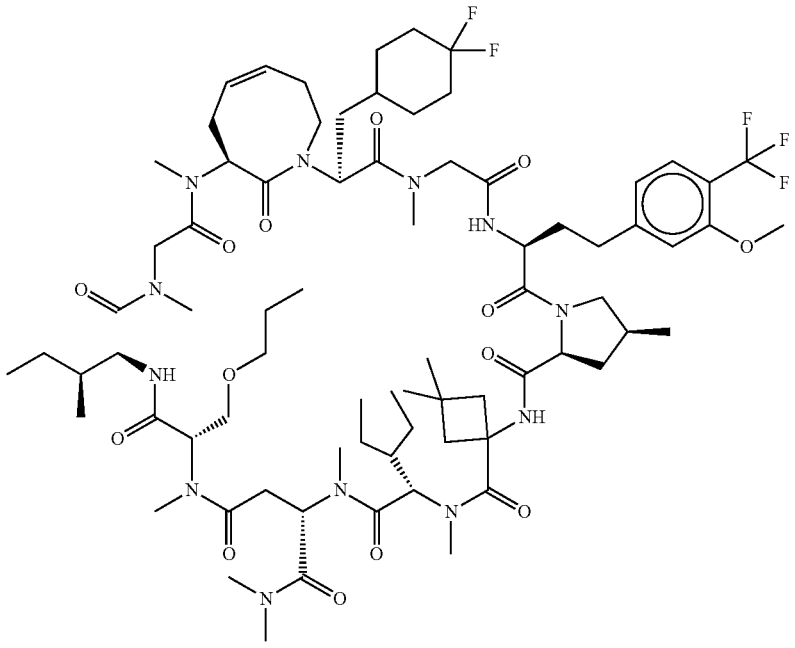 |
| PP2484 | 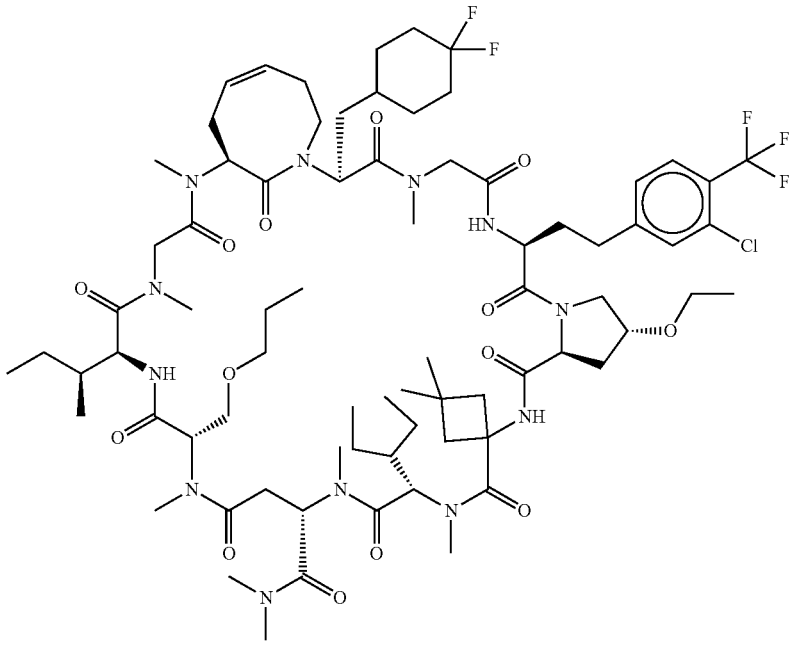 |

TABLE 38-continued
| Compound No. | Structural Formula |
|---|---|
| PP2485 | 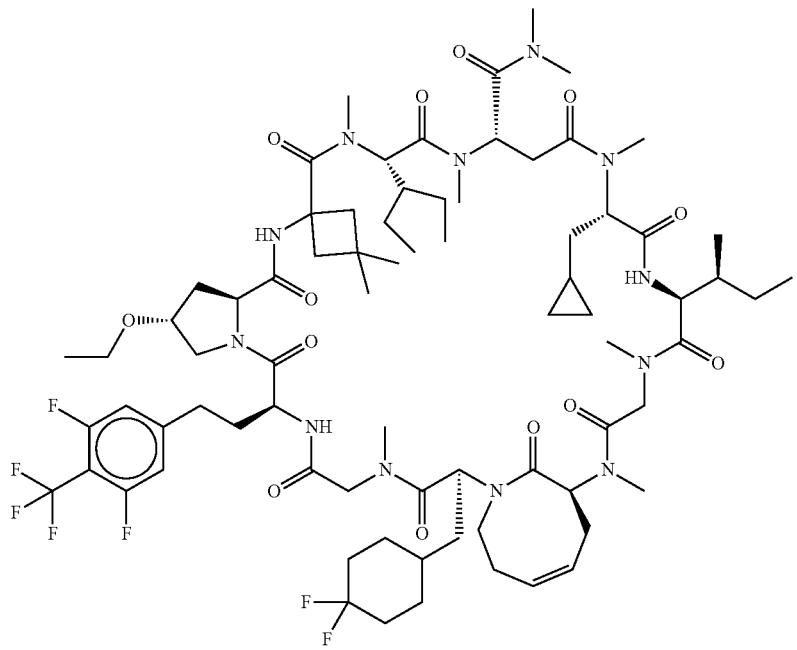 |
| PP2486 | 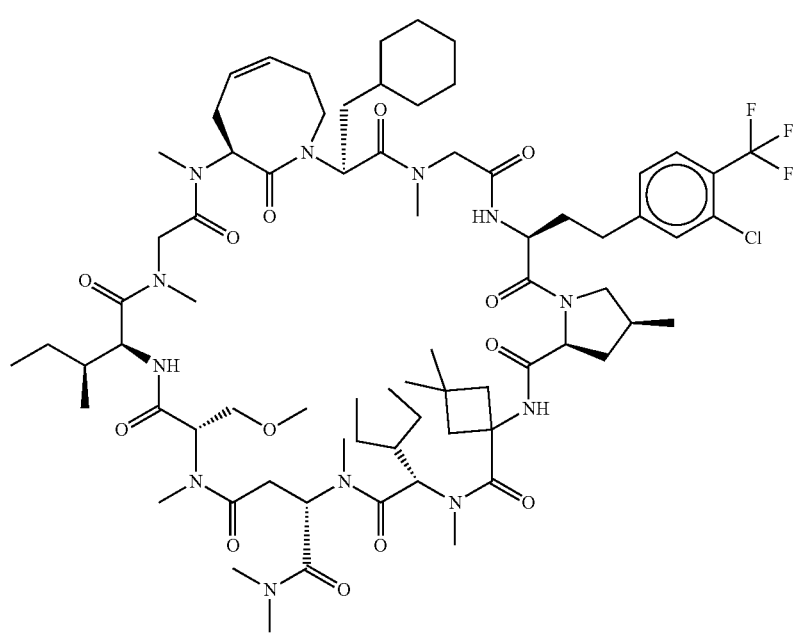 |

TABLE 38-continued
| Compound No. | Structural Formula |
|---|---|
| PP2487 | 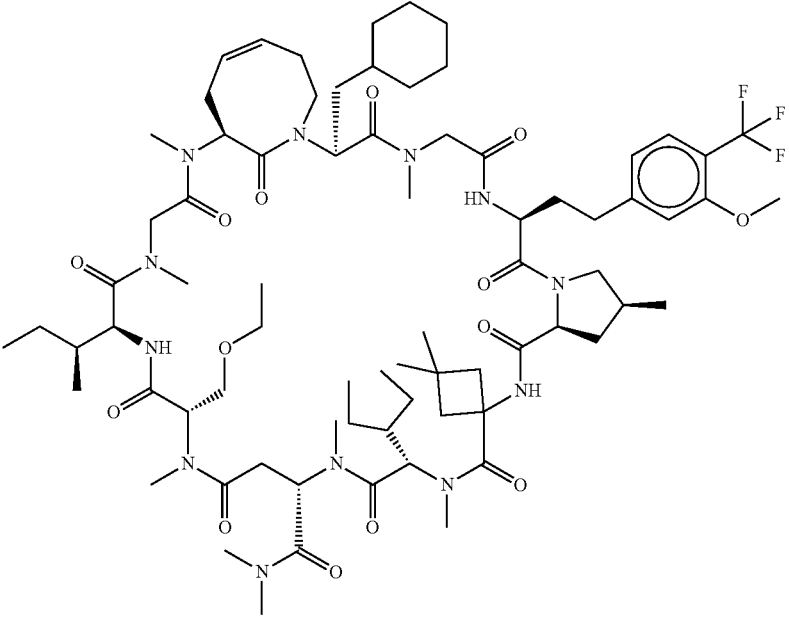 |
| PP2488 | 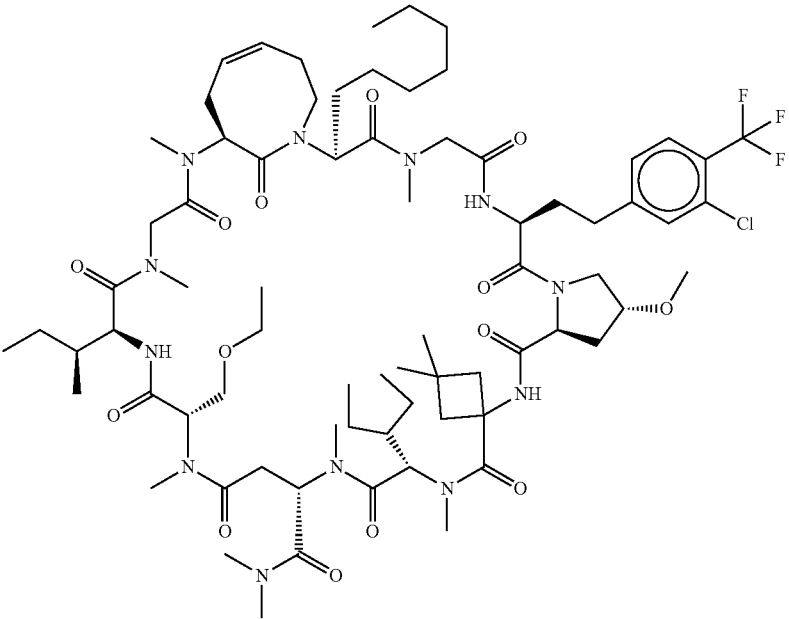 |

TABLE 38-continued

| Compound No. | Structural Formula |
| --- | --- |
| PP2489 | |
| PP2490 | |

TABLE 38-continued

| Compound No. | Structural Formula |
|---|---|
| PP2491 | |
| PP2492 | |

US 12,410,212 B2
3171 3172
TABLE 38-continued
| Compound No. | Structural Formula |
|---|---|
| PP2493 | 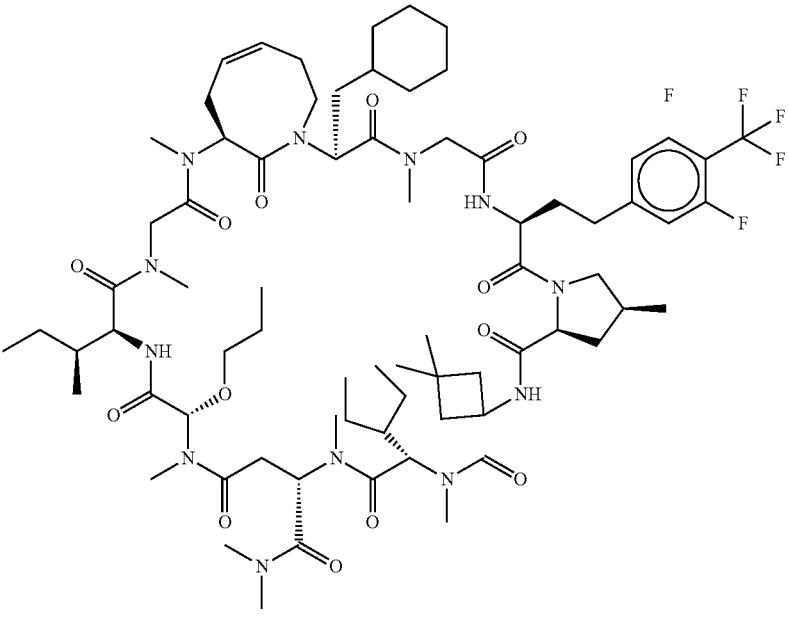 |
| PP2494 | 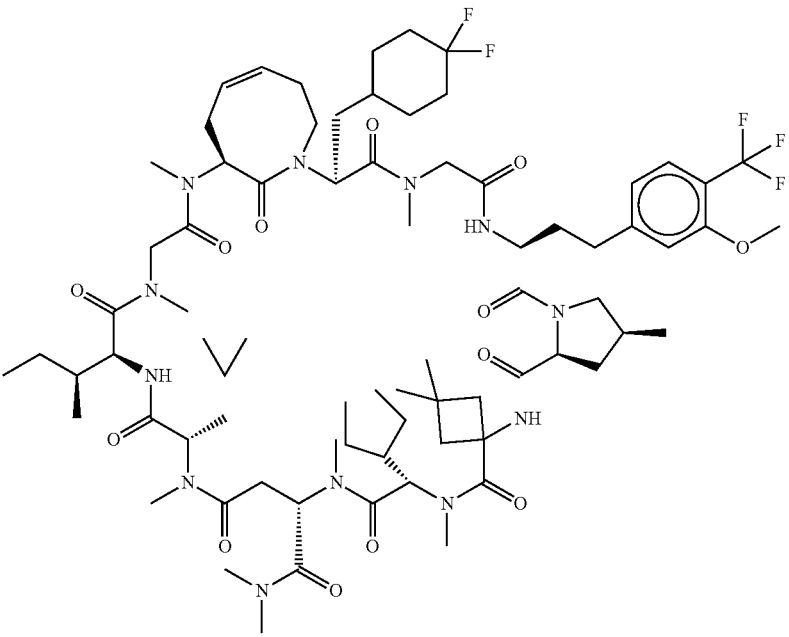 |

TABLE 38-continued
| Compound No. | Structural Formula |
|---|---|
| PP2495 | 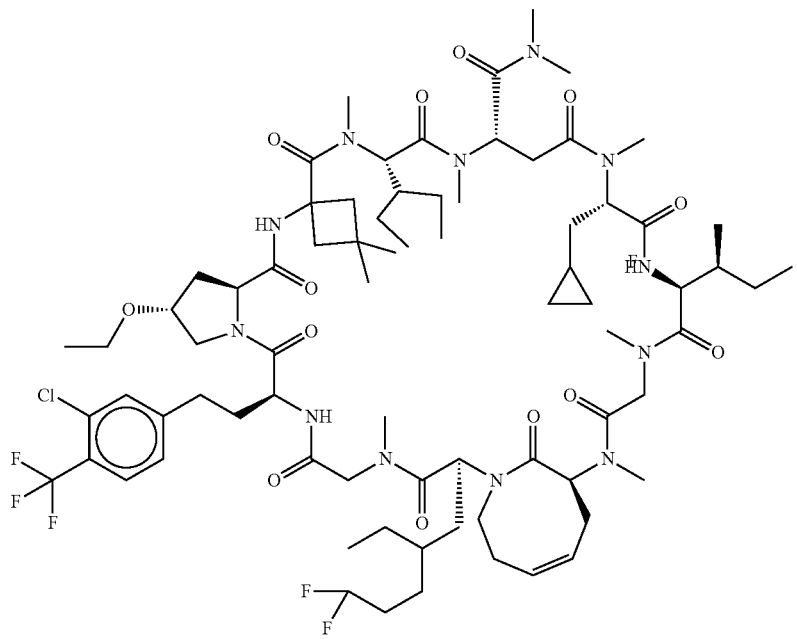 |
| PP2496 | 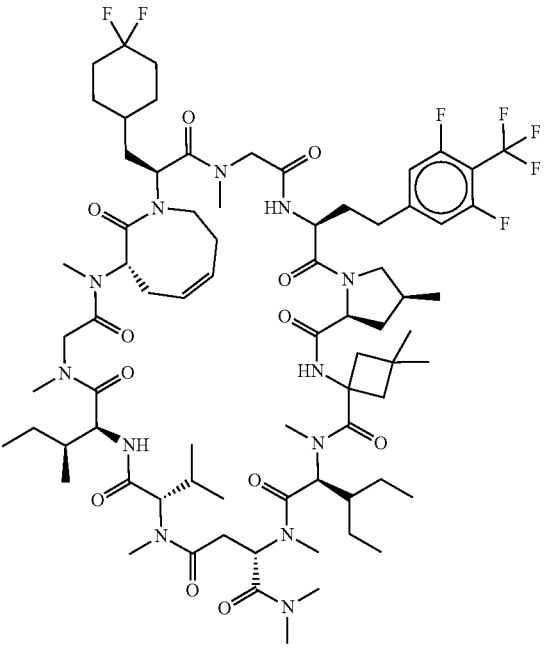 |

TABLE 38-continued
| Compound No. | Structural Formula |
|---|---|
| PP2497 | 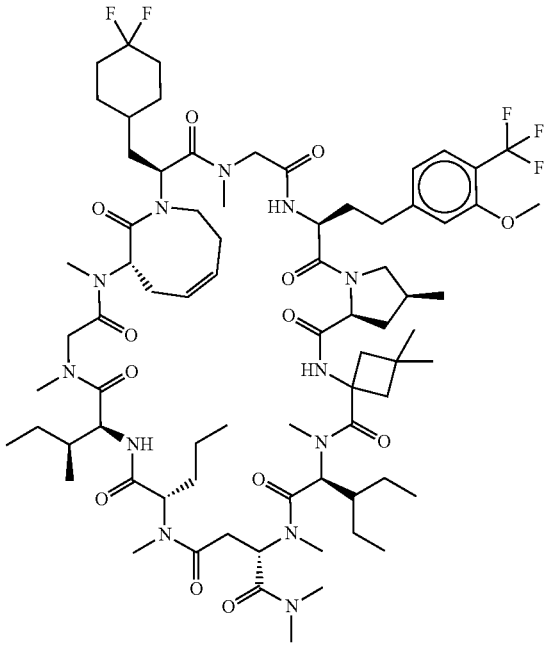 |
| PP2498 | 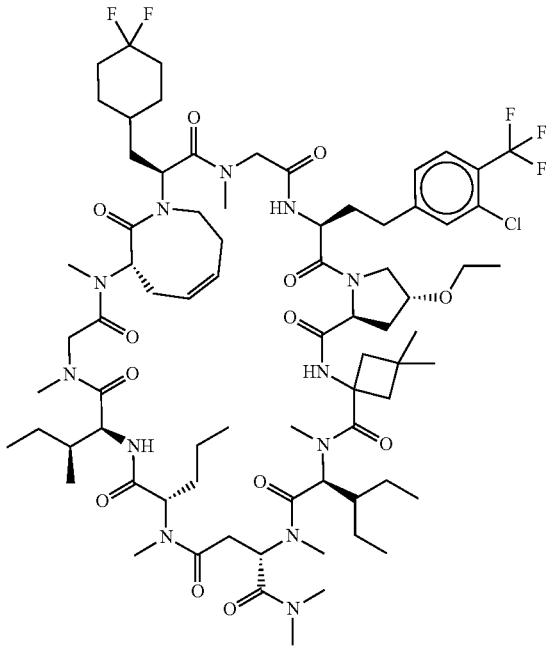 |

TABLE 38-continued
| Compound No. | Structural Formula |
|---|---|
| PP2499 | 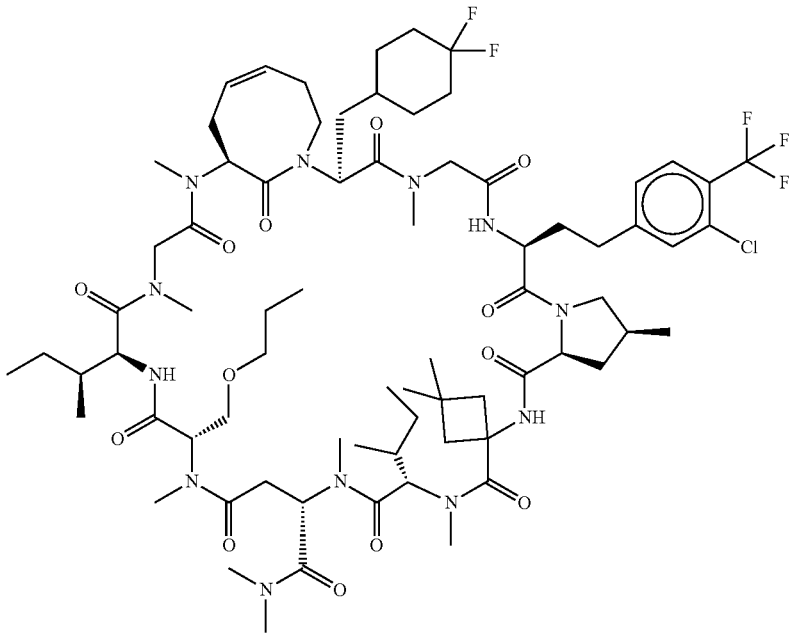 |
| PP2500 | 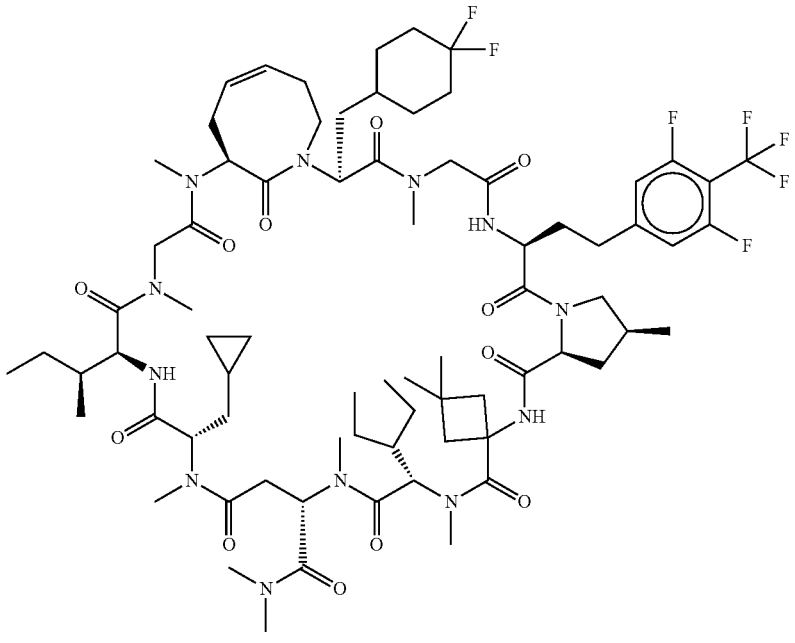 |

TABLE 38-continued
| Compound No. | Structural Formula |
|---|---|
| PP2501 | 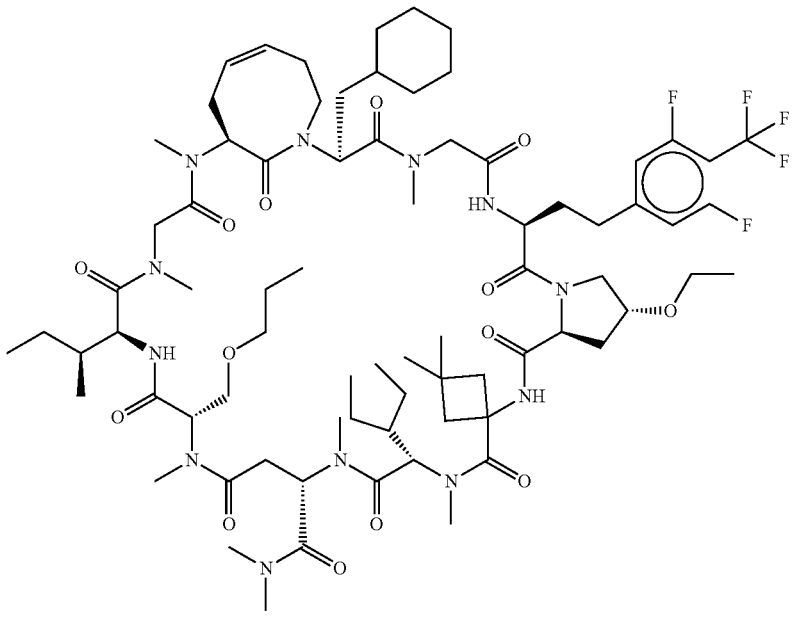 |
| PP2502 | 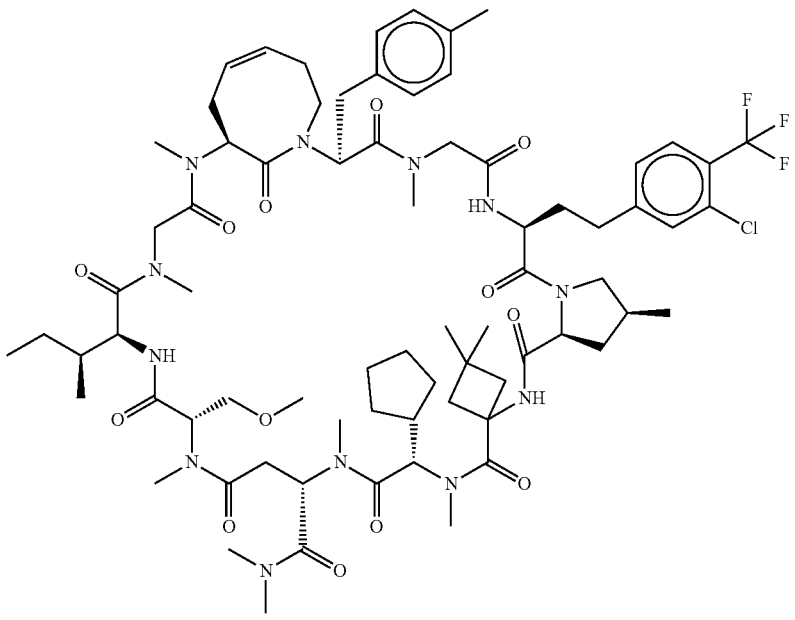 |

TABLE 38-continued

| Compound No. | Structural Formula |
|---|---|
| PP2504 | |
| PP2505 | |

TABLE 38-continued

| Compound No. | Structural Formula |
|---|---|
| PP2506 | |
| PP2507 | |

TABLE 38-continued

| Compound No. | Structural Formula |
|---|---|
| PP2508 | |
| PP2509 | |

TABLE 38-continued

| Compound No. | Structural Formula |
|---|---|
| PP2510 | |
| PP2511 | |

TABLE 38-continued

| Compound No. | Structural Formula |
|---|---|
| PP2512 | |
| PP2513 | |

TABLE 38-continued

| Compound No. | Structural Formula |
|---|---|
| PP2514 | |
| PP2515 | |

TABLE 38-continued

| Compound No. | Structural Formula |
|---|---|
| PP2516 | |
| PP2517 | |

TABLE 38-continued

| Compound No. | Structural Formula |
|---|---|
| PP2518 | |
| PP2519 | |

TABLE 38-continued

| Compound No. | Structural Formula |
|---|---|
| PP2520 | |
| PP2521 | |

TABLE 38-continued

| Compound No. | Structural Formula |
| --- | --- |
| PP2522 | |
| PP2523 | |

TABLE 38-continued

| Compound No. | Structural Formula |
| --- | --- |
| PP2524 | |
| PP2525 | |

TABLE 38-continued

| Compound No. | Structural Formula |
|---|---|
| PP2526 | |
| PP2527 | |

TABLE 38-continued

| Compound No. | Structural Formula |
|---|---|
| PP2528 | |
| PP2529 | |

TABLE 38-continued

| Compound No. | Structural Formula |
|---|---|
| PP2530 | |
| PP2531 | |

TABLE 38-continued
| Compound No. | Structural Formula |
|---|---|
| PP2532 | 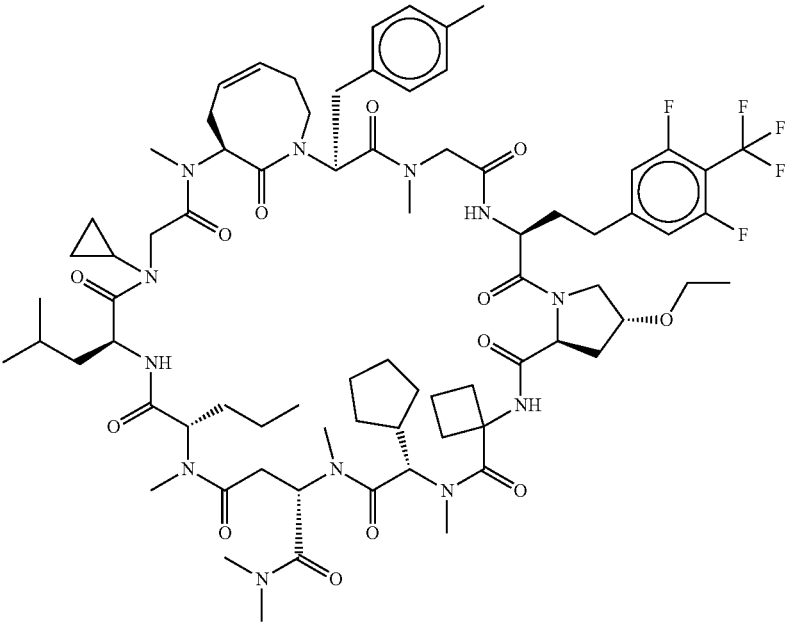 |
| PP2533 | 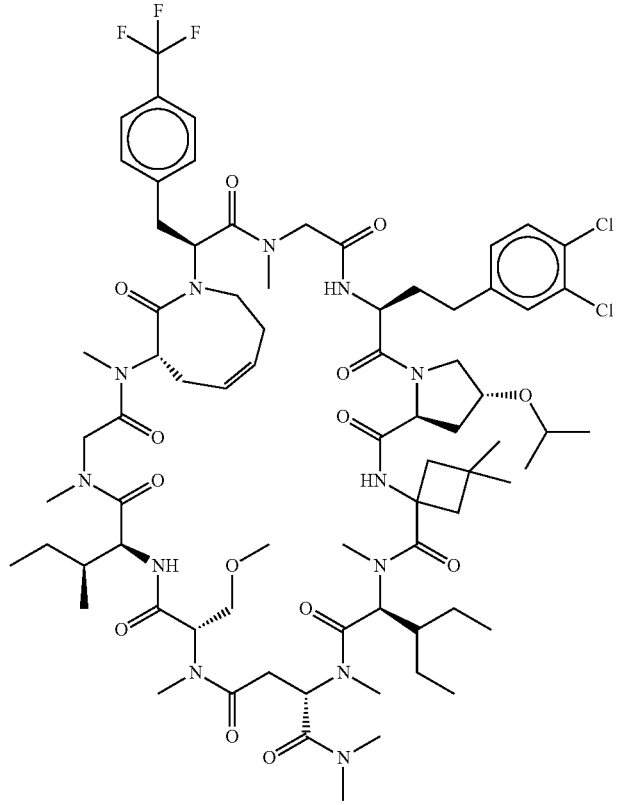 |

TABLE 38-continued
| Compound No. | Structural Formula |
|---|---|
| PP2534 | 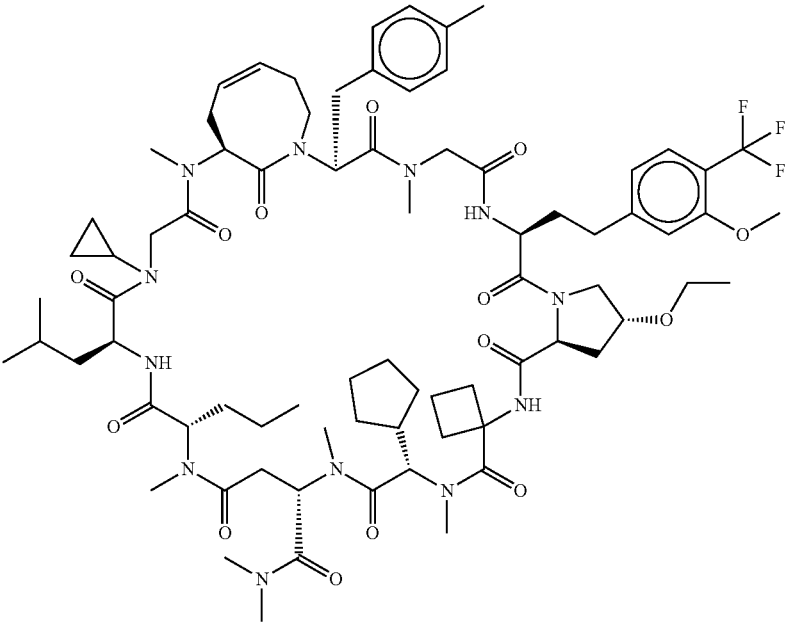 |
| PP2535 | 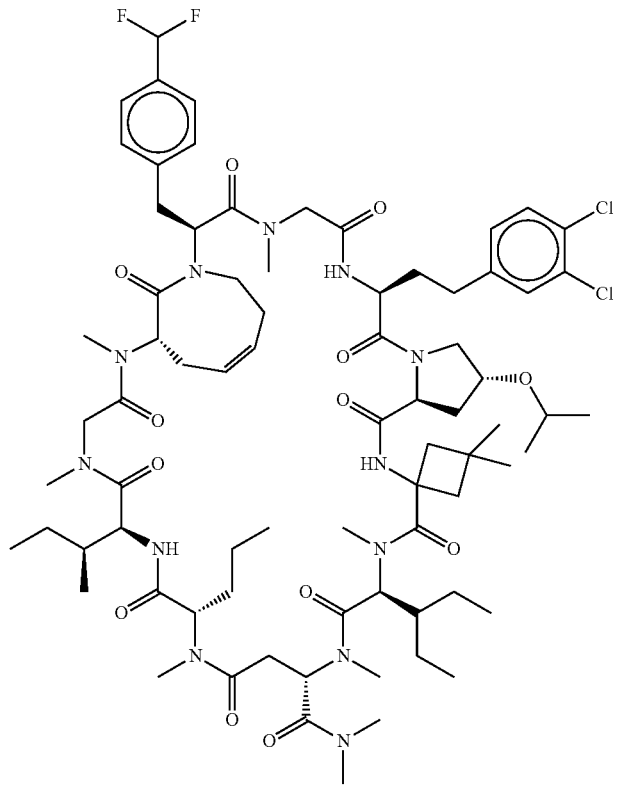 |

TABLE 38-continued

| Compound No. | Structural Formula |
|---|---|
| PP2536 | |
| PP2537 | |

TABLE 38-continued

| Compound No. | Structural Formula |
|---|---|
| PP2539 | |
| PP2540 | |

TABLE 38-continued

| Compound No. | Structural Formula |
|---|---|
| PP2541 | |
| PP2542 | |

TABLE 38-continued

| Compound No. | Structural Formula |
|---|---|
| PP2543 | |
| PP2545 | |

TABLE 38-continued

| Compound No. | Structural Formula |
| --- | --- |
| PP2546 | |
| PP2547 | |

TABLE 38-continued
| Compound No. | Structural Formula |
|---|---|
| PP2548 | 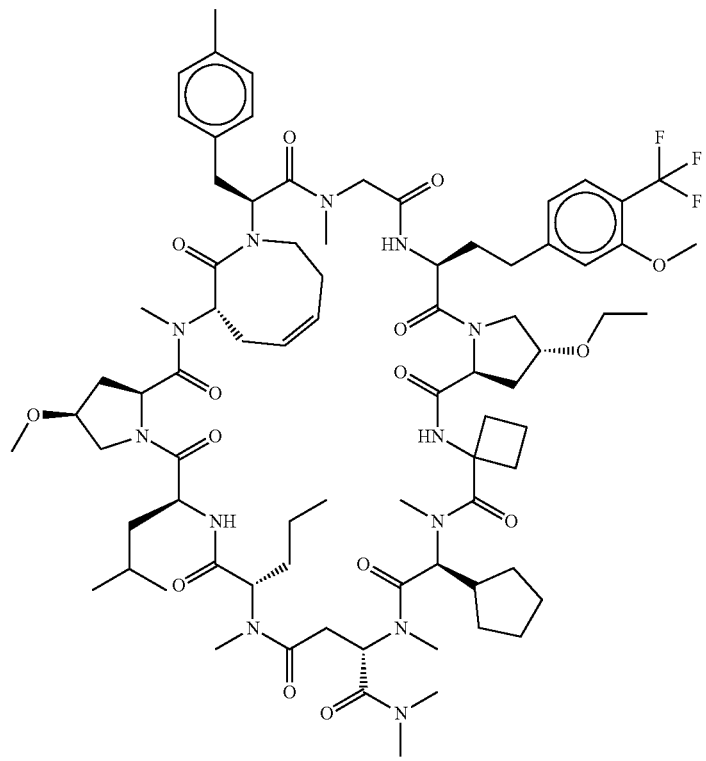 |
| PP2549 | 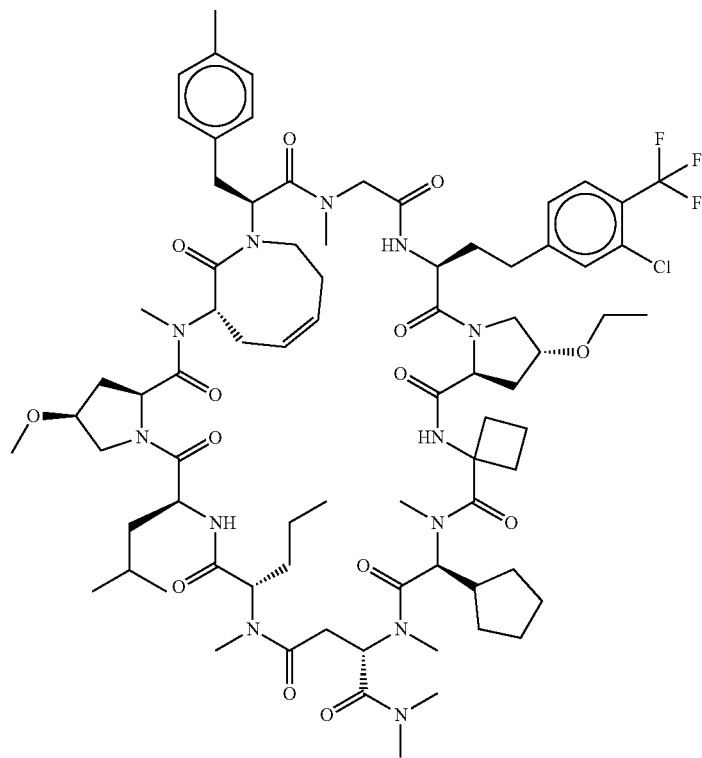 |

TABLE 38-continued
| Compound No. | Structural Formula |
|---|---|
| PP2550 | 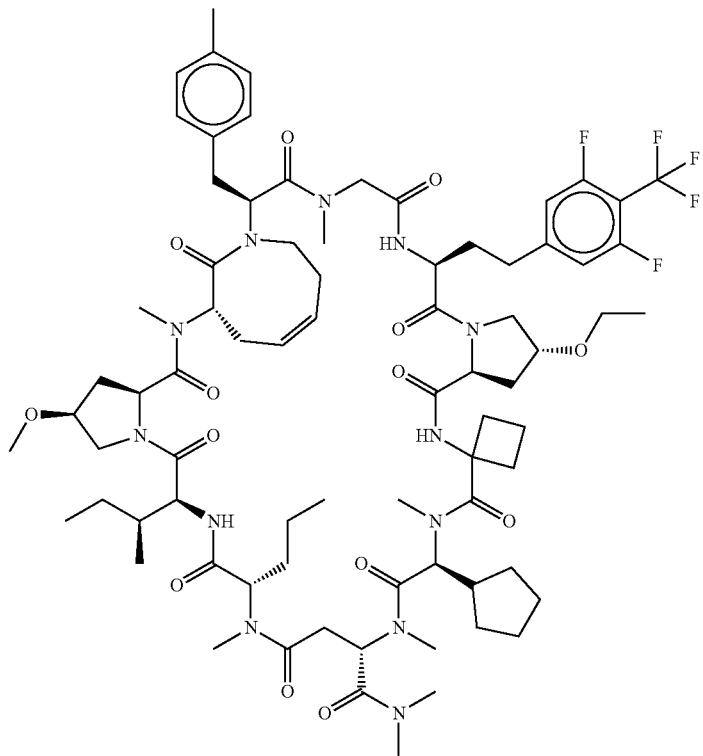 |
| PP2551 | 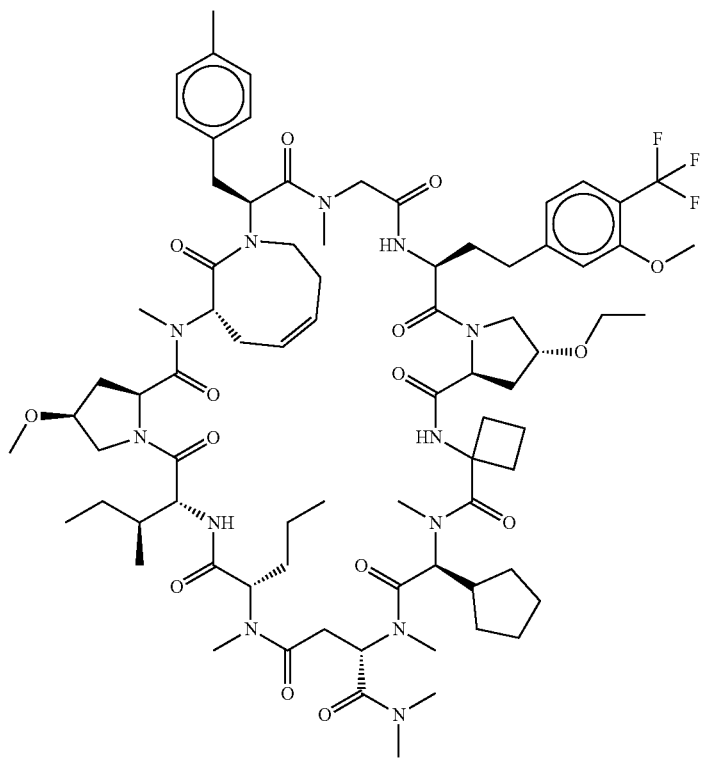 |

TABLE 38-continued
| Compound No. | Structural Formula |
|---|---|
| PP2552 | 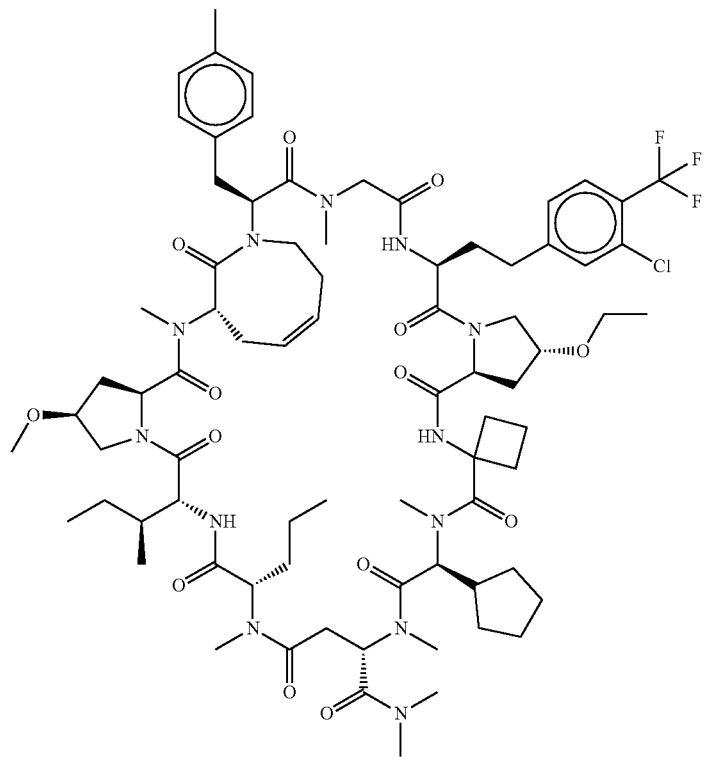 |
| PP2553 | 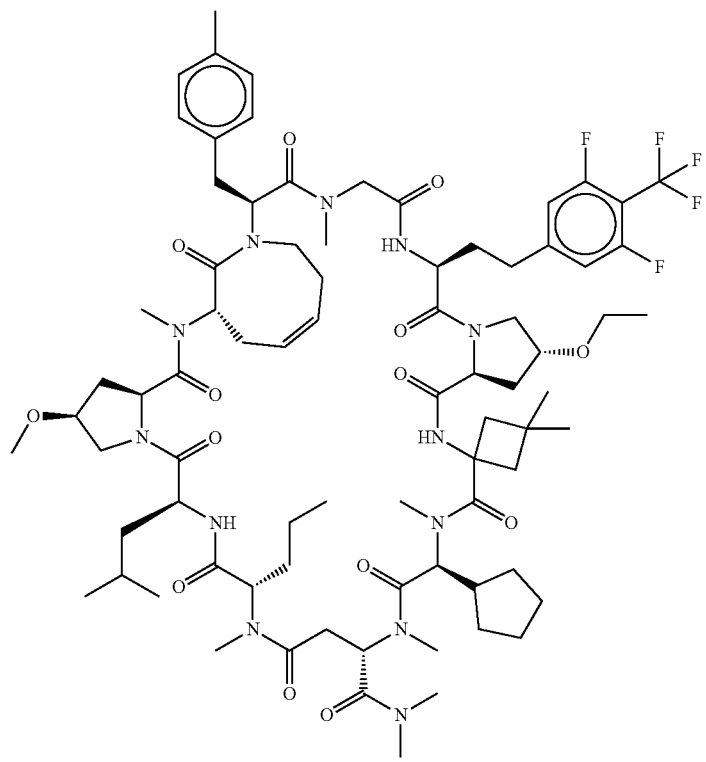 |

//
TABLE 38-continued
| Compound No. | Structural Formula |
|---|---|
| PP2554 | 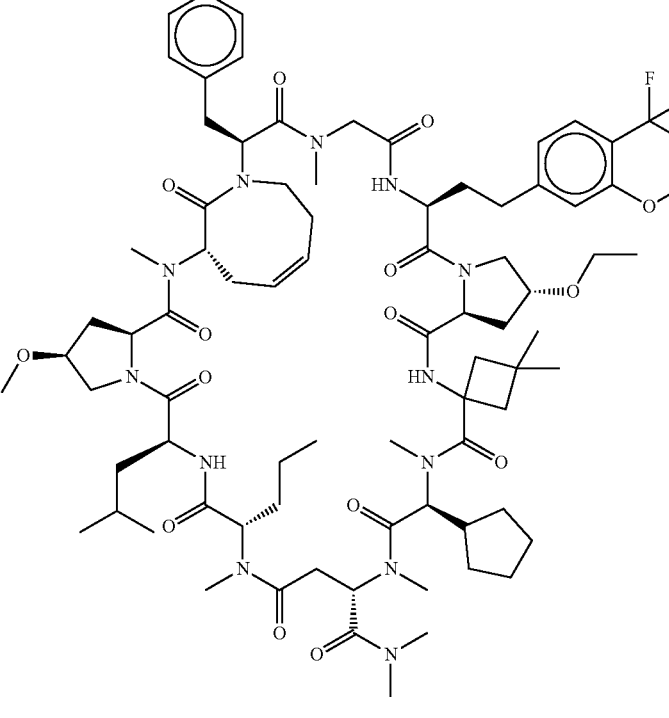 |
| PP2555 | 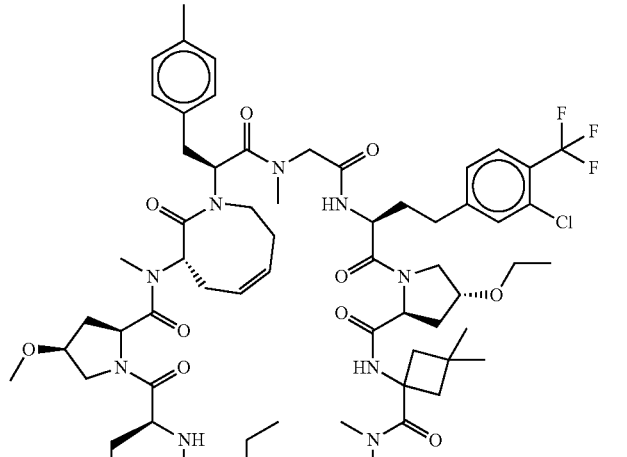 |

… TABLE 38-continued
| Compound No. | Structural Formula |
|---|---|
| PP2556 | 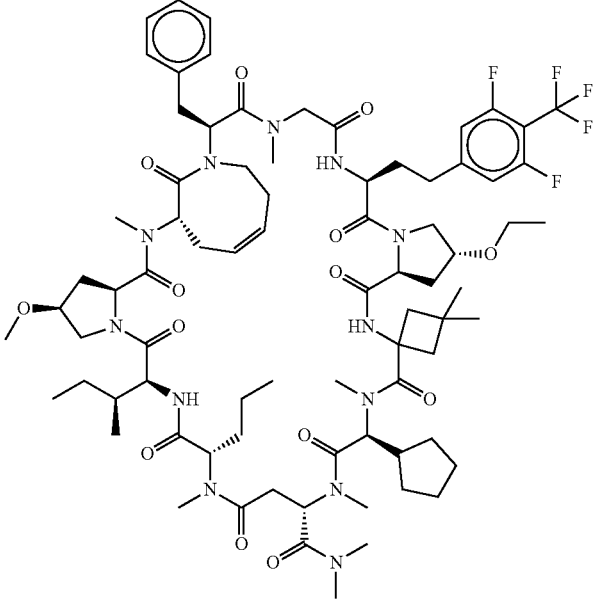 |
| PP2557 | 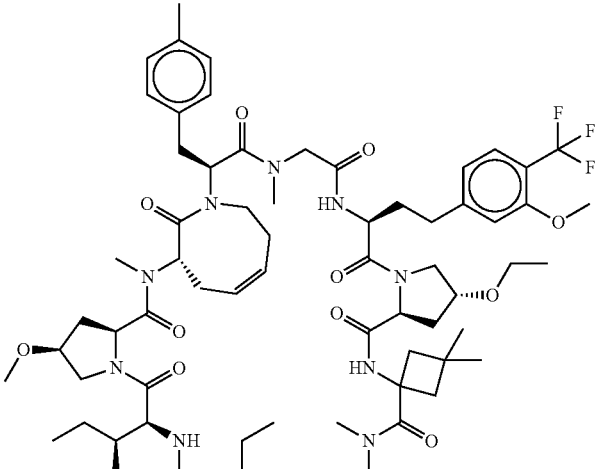 |

TABLE 38-continued

| Compound No. | Structural Formula |
|---|---|
| PP2558 | |
| PP2559 | |

TABLE 38-continued
| Compound No. | Structural Formula |
|---|---|
| PP2560 | 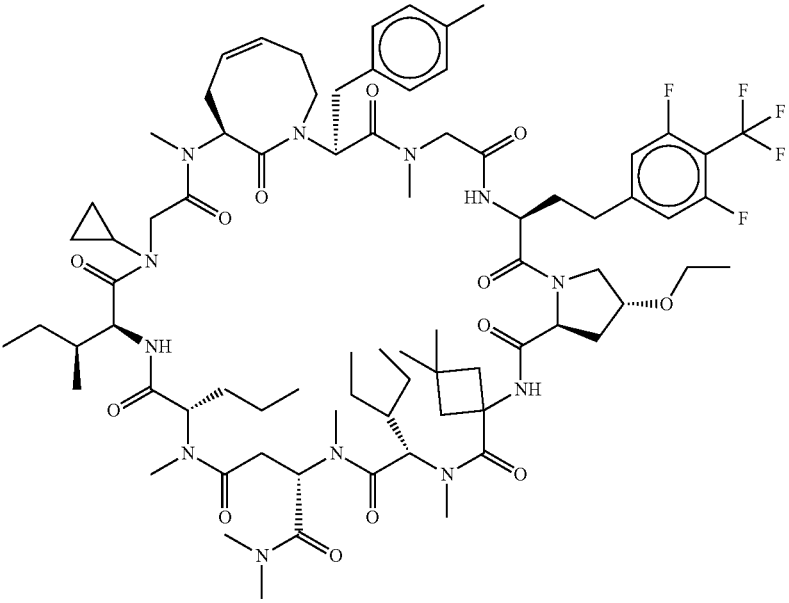 |
| PP2561 | 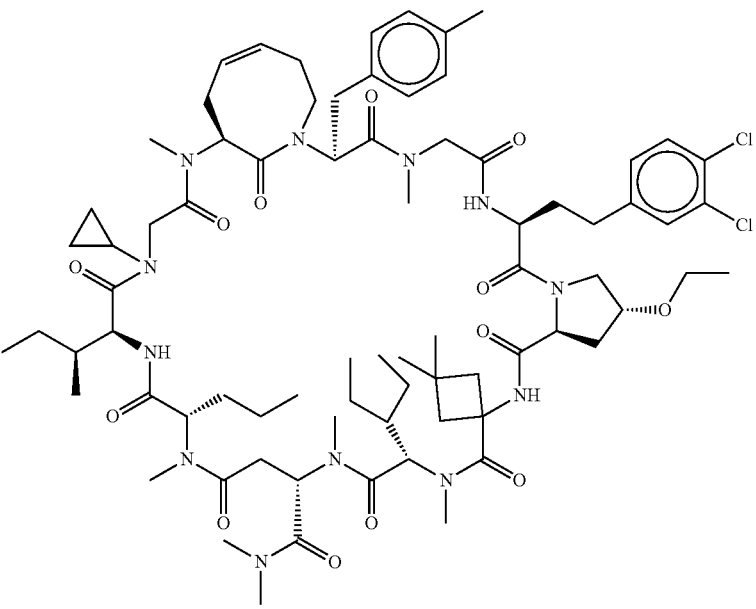 |

TABLE 38-continued
| Compound No. | Structural Formula |
|---|---|
| PP2562 | 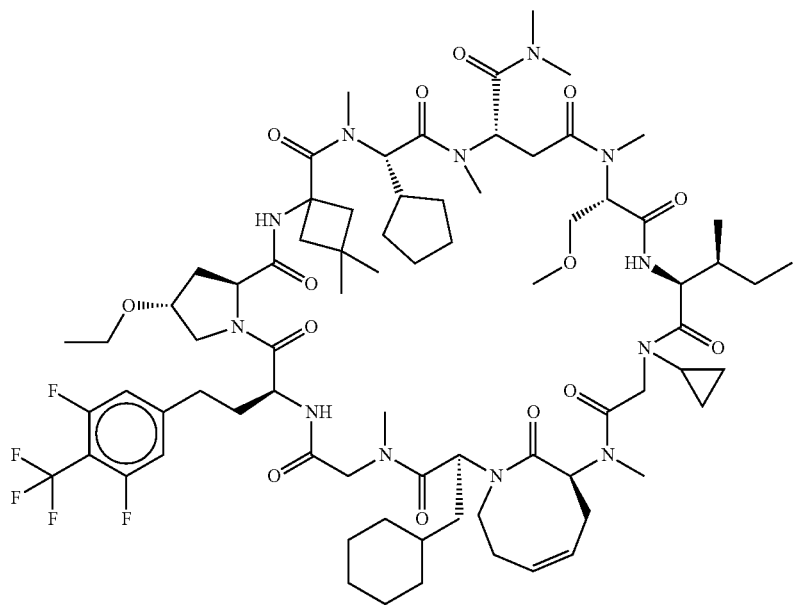 |
| PP2563 | 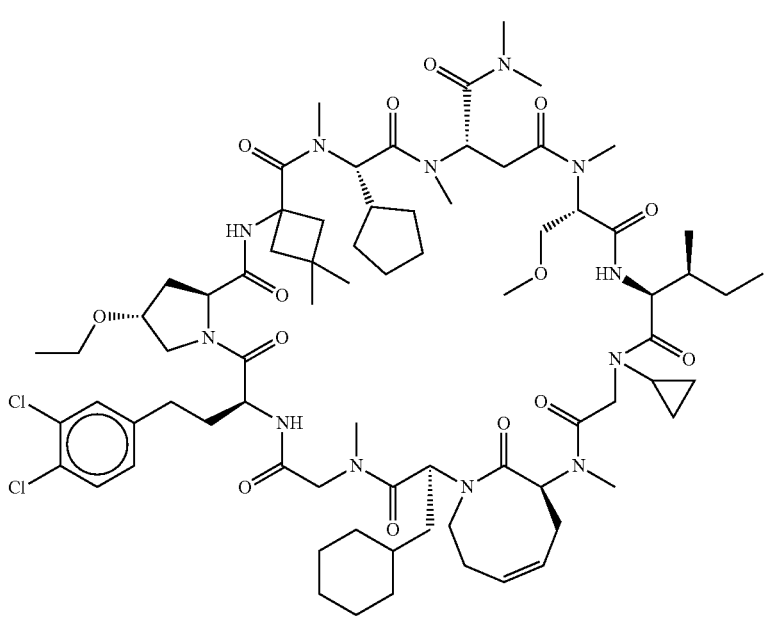 |

TABLE 38-continued
| Compound No. | Structural Formula |
|---|---|
| PP2564 | 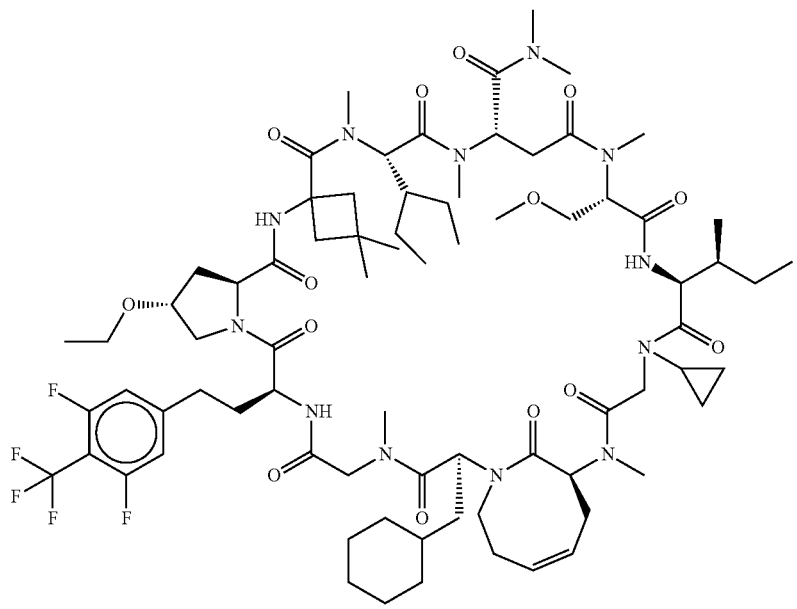 |
| PP2565 | 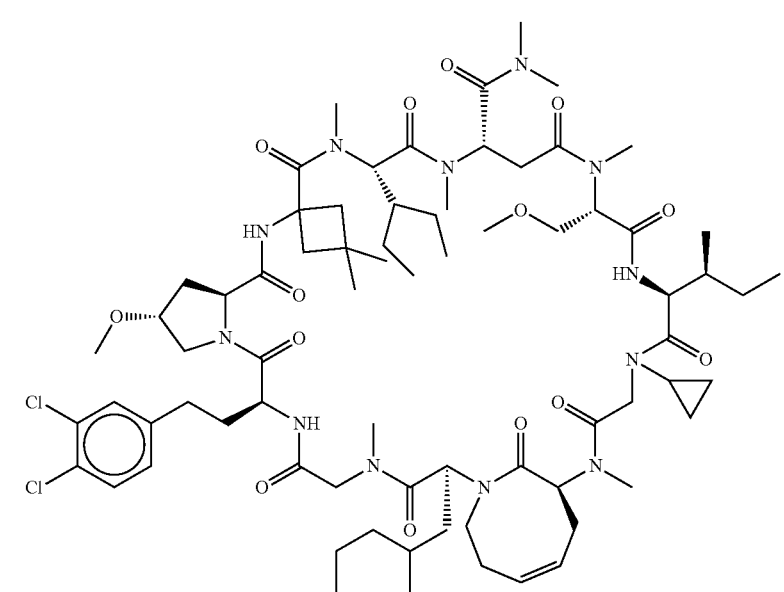 |

TABLE 38-continued
| Compound No. | Structural Formula |
|---|---|
| PP2566 | 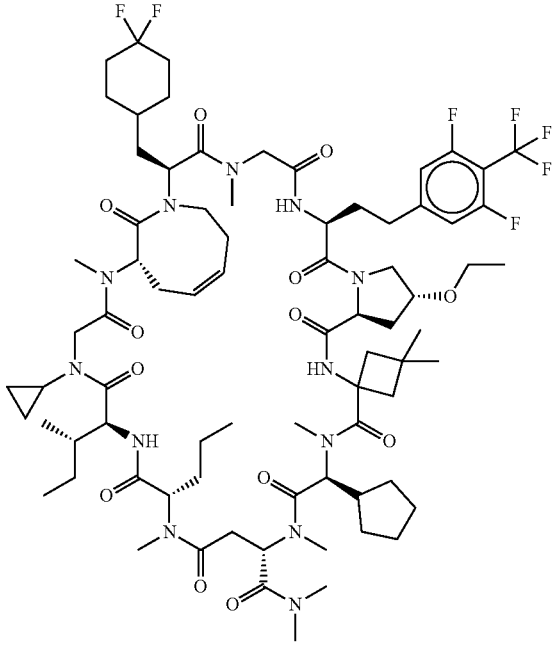 |
| PP2567 | 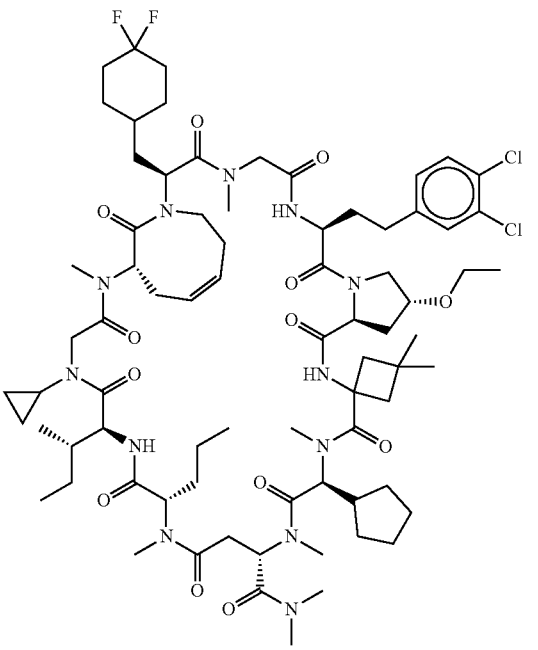 |

TABLE 38-continued
| Compound No. | Structural Formula |
|---|---|
| PP2568 | 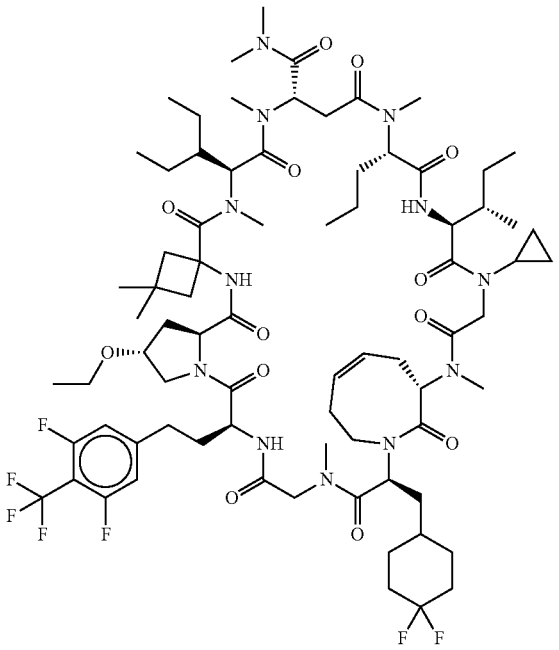 |
| PP2569 | 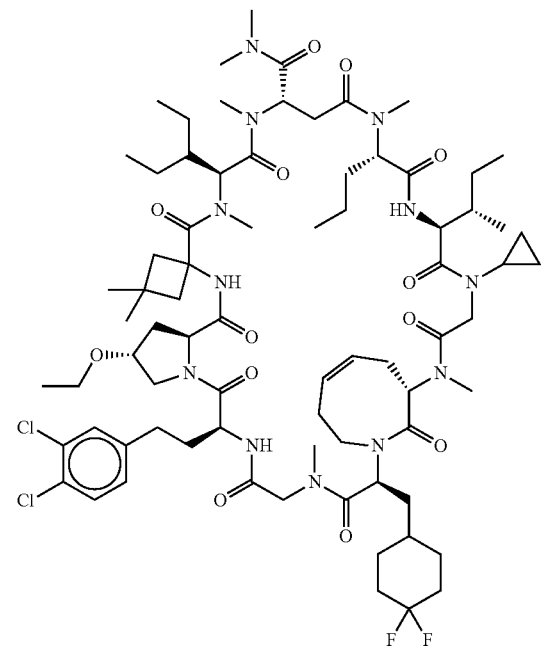 |

TABLE 38-continued
| Compound No. | Structural Formula |
| --- | --- |
| PP2570 | 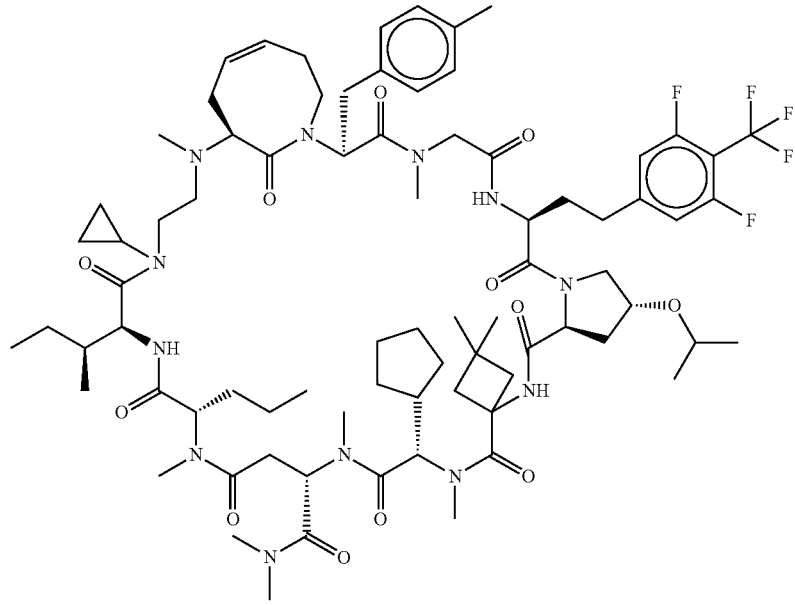 |
| PP2571 | 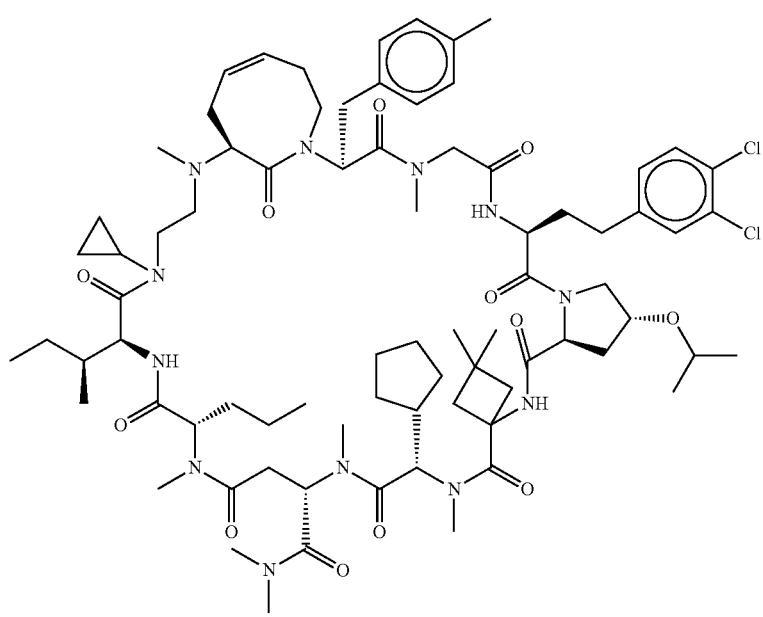 |

TABLE 38-continued
| Compound No. | Structural Formula |
|---|---|
| PP2572 | 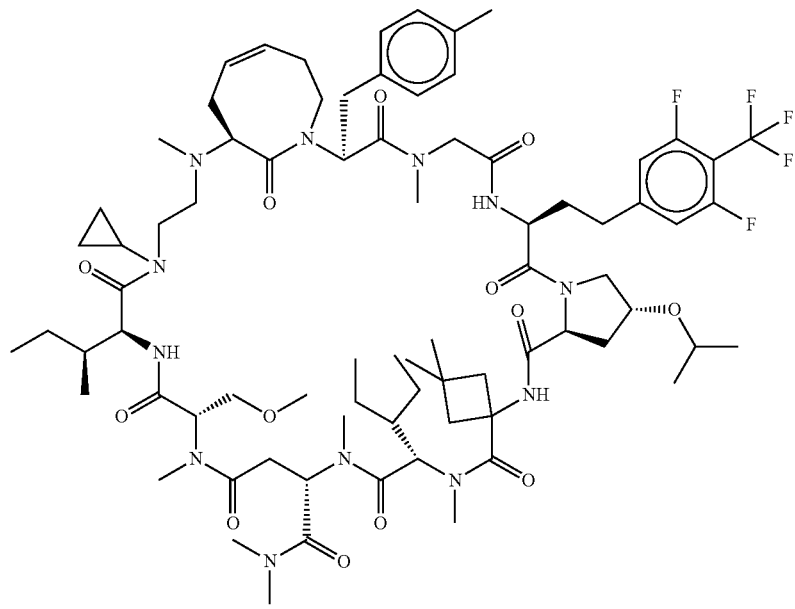 |
| PP2573 | 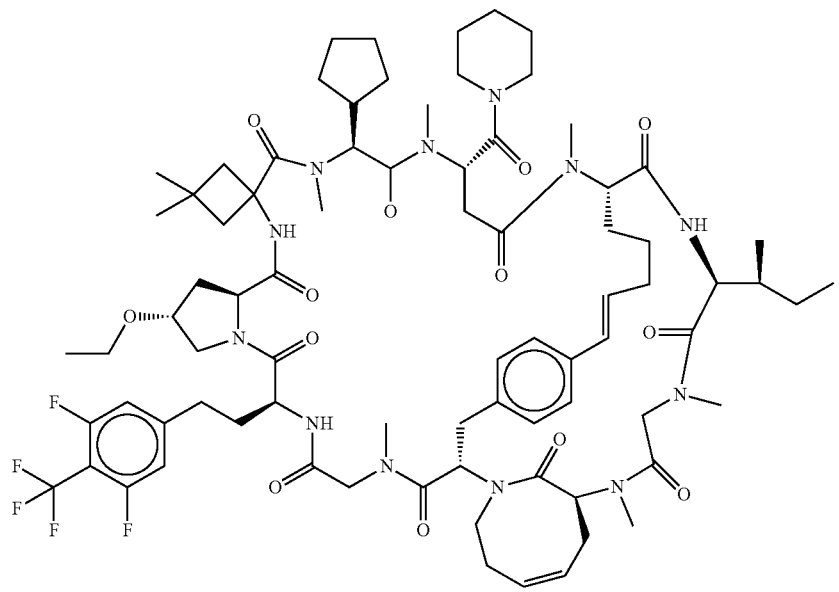 |

TABLE 38-continued
| Compound No. | Structural Formula |
|---|---|
| PP2574 | 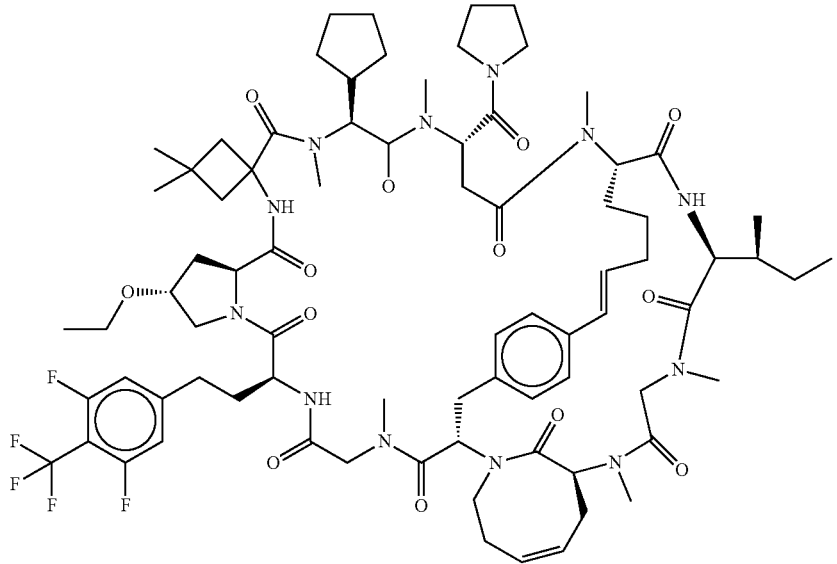 |
| PP2575 | 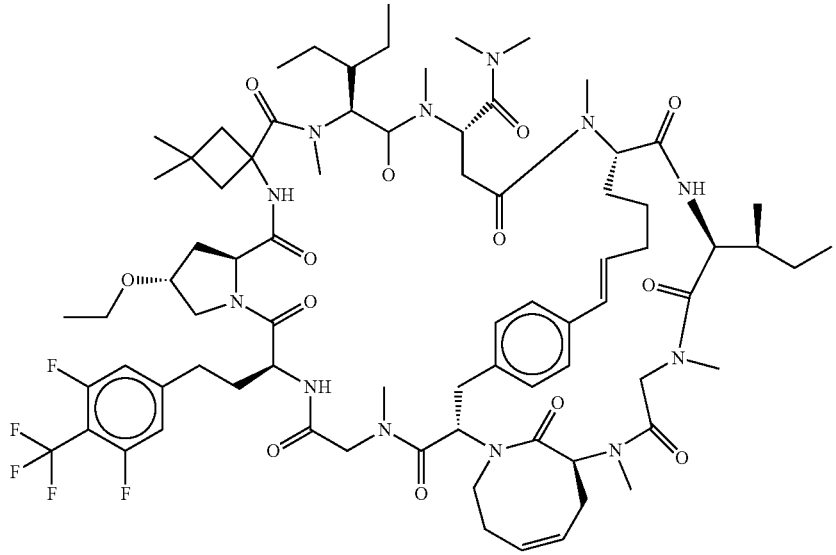 |

TABLE 38-continued
| Compound No. | Structural Formula |
|---|---|
| PP2576 | 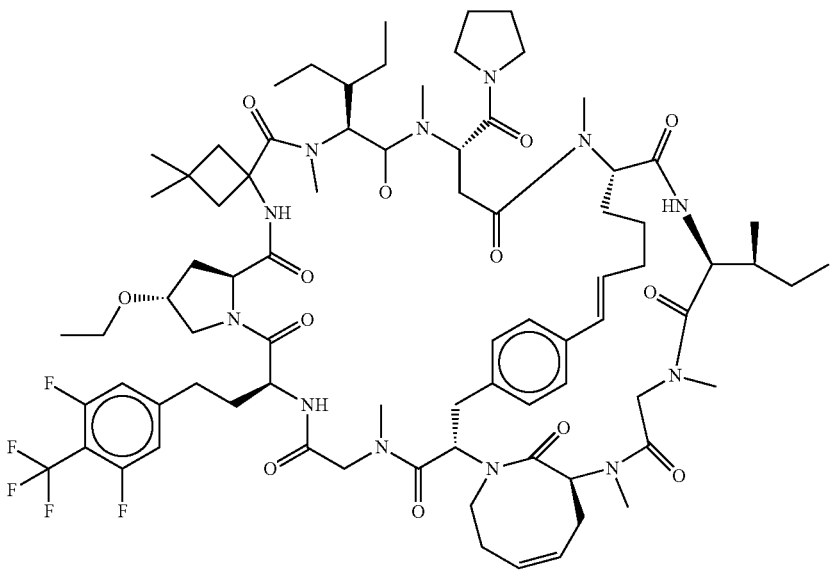 |
| PP2577 | 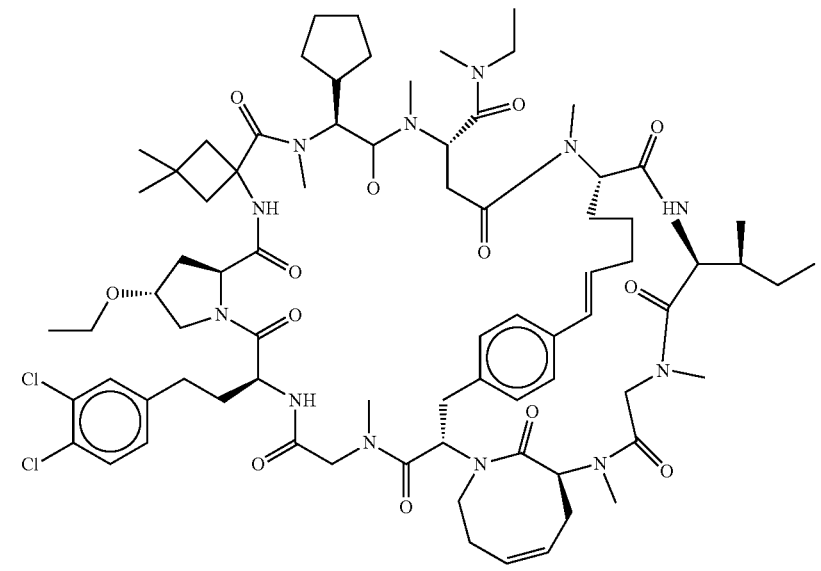 |

TABLE 38-continued

| Compound No. | Structural Formula |
| --- | --- |
| PP2578 | |
| PP2579 | |

TABLE 38-continued

| Compound No. | Structural Formula |
|---|---|
| PP2580 | |
| PP2581 | |

TABLE 38-continued
| Compound No. | Structural Formula |
|---|---|
| PP2583 | 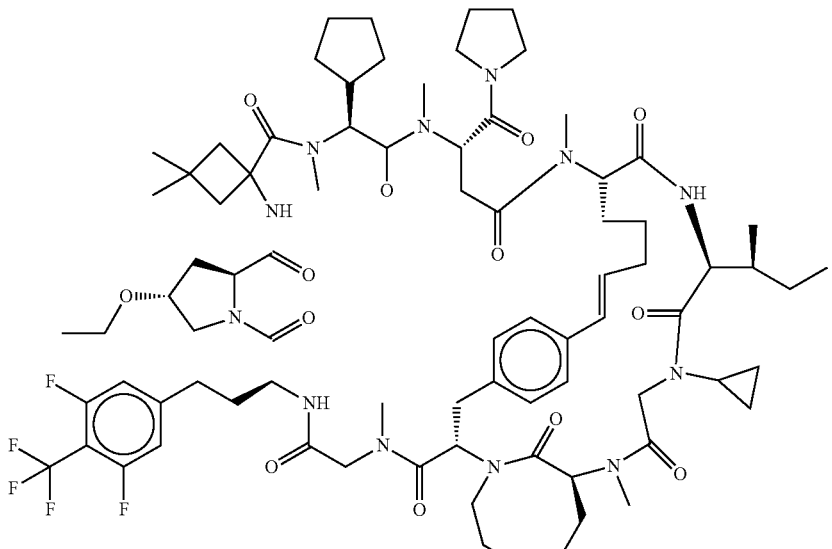 |
| PP2585 | 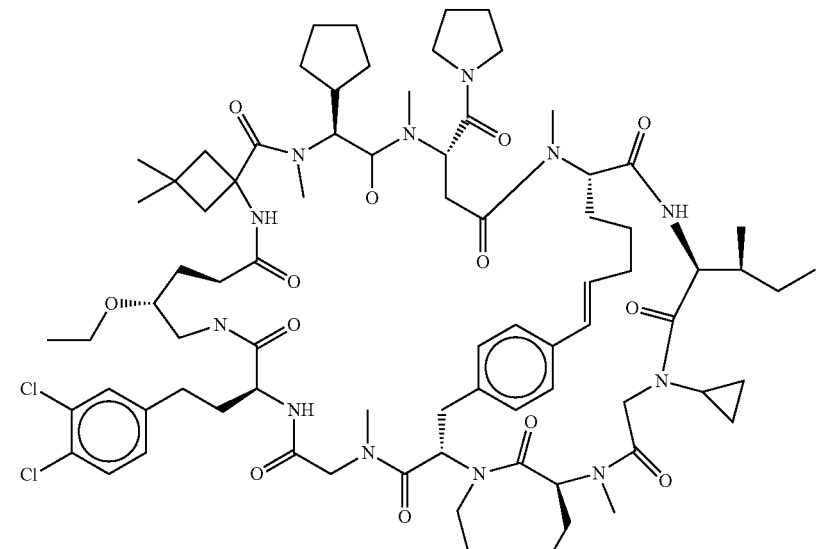 |

TABLE 38-continued
| Compound No. | Structural Formula |
|---|---|
| PP2586 | 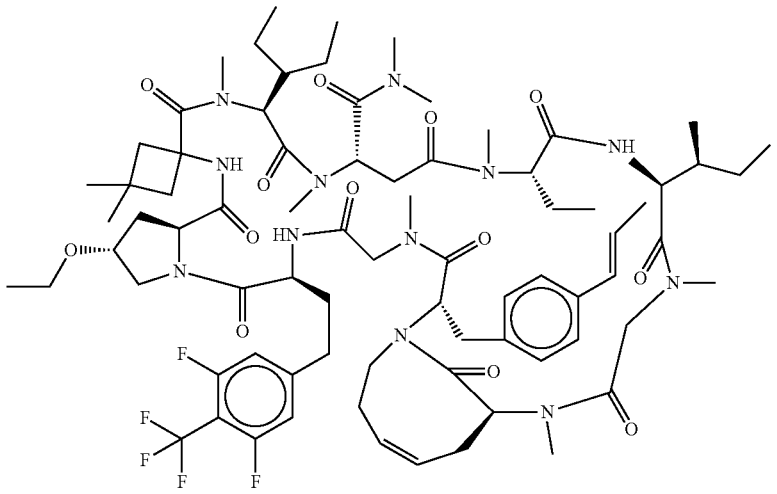 |
| PP2588 | 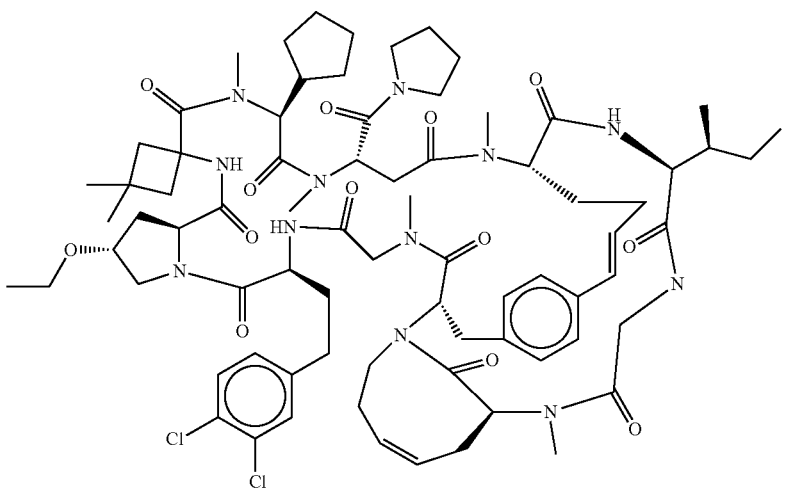 |
| PP2589 | 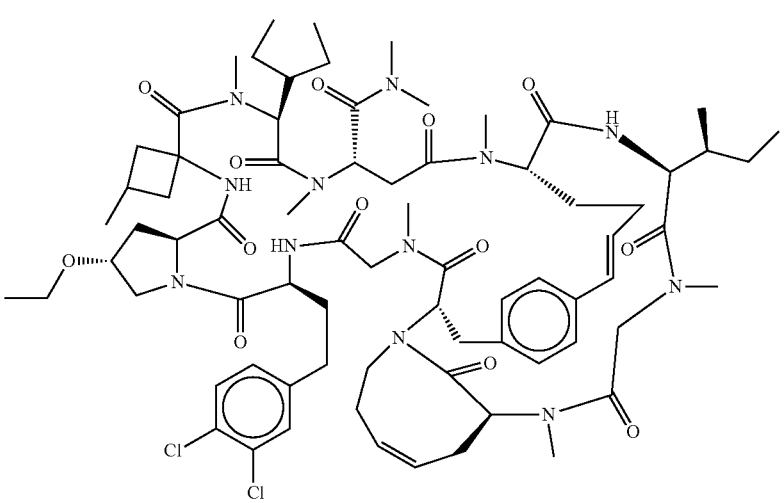 |

TABLE 38-continued

| Compound No. | Structural Formula |
|---|---|
| PP2590 | |
| PP2591 | |

TABLE 38-continued
| Compound No. | Structural Formula |
|---|---|
| PP2592 | 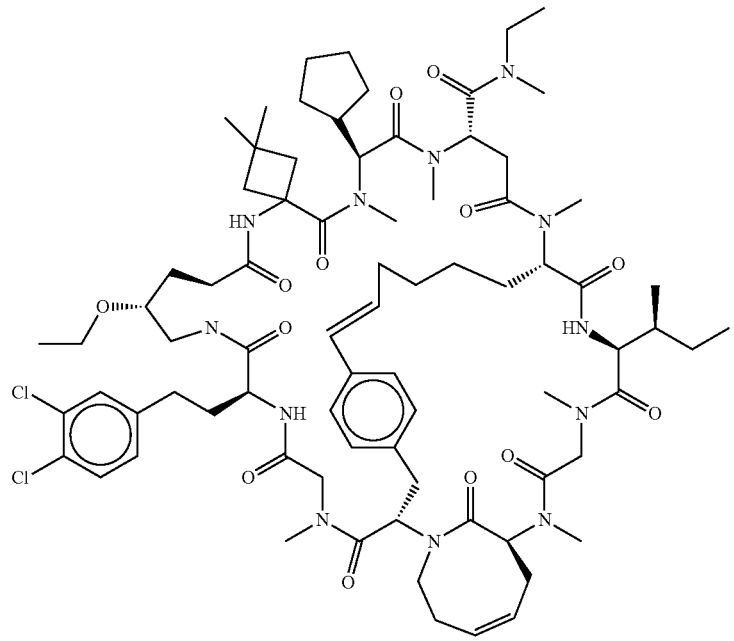 |
| PP2593 | 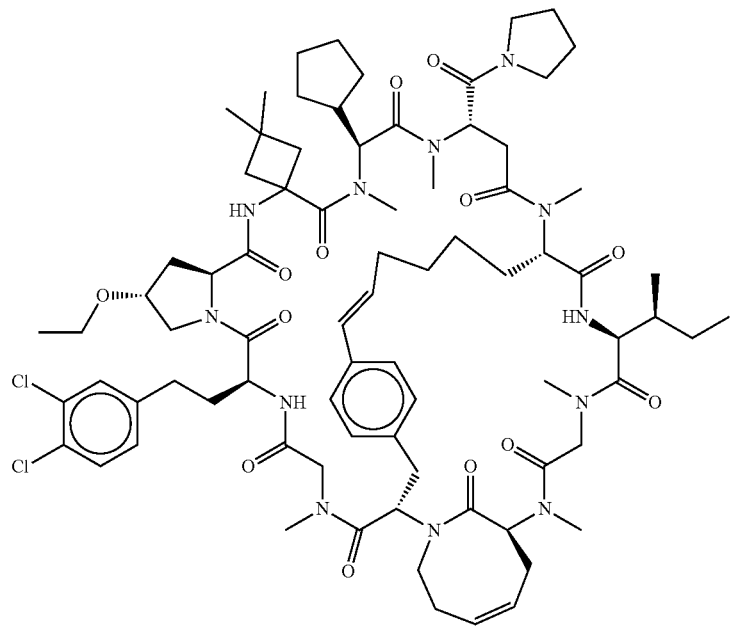 |

3265 3266
TABLE 38-continued
| Compound No. | Structural Formula |
|---|---|
| PP2594 | 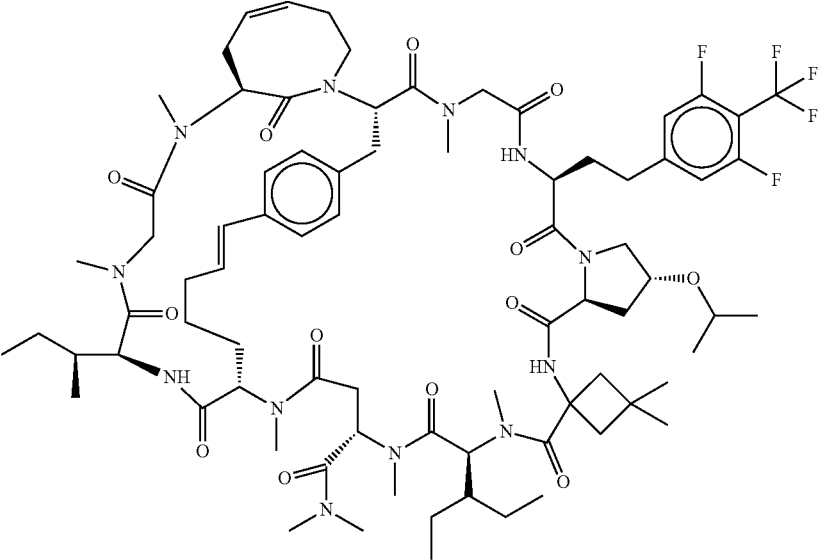 |
| PP2595 | 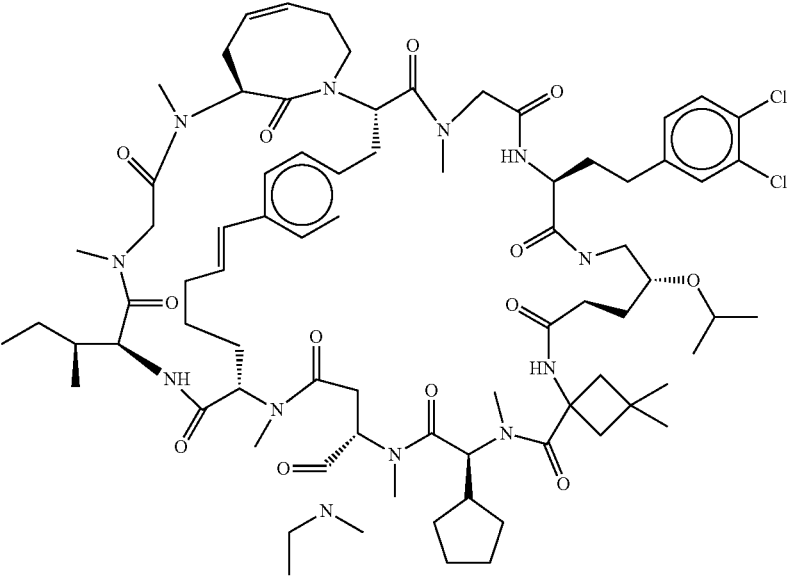 |

TABLE 38-continued
| Compound No. | Structural Formula |
|---|---|
| PP2596 | 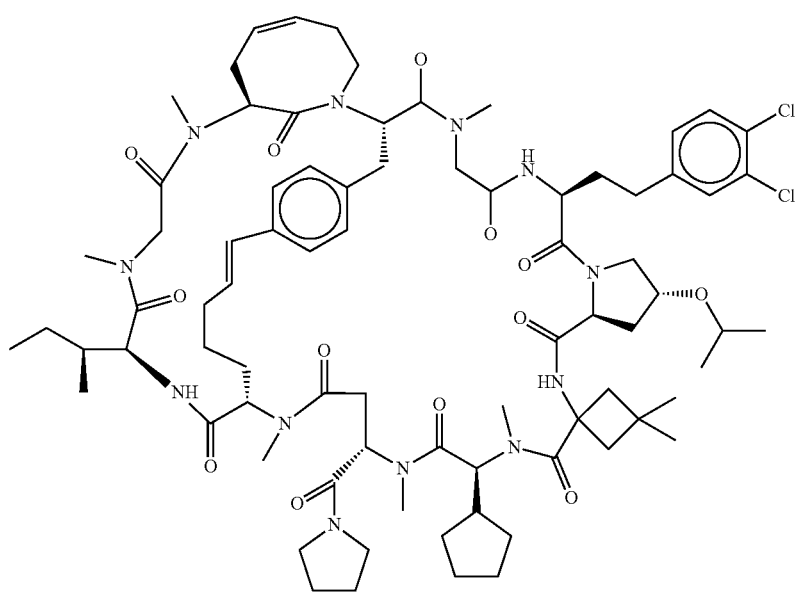 |
| PP2597 | 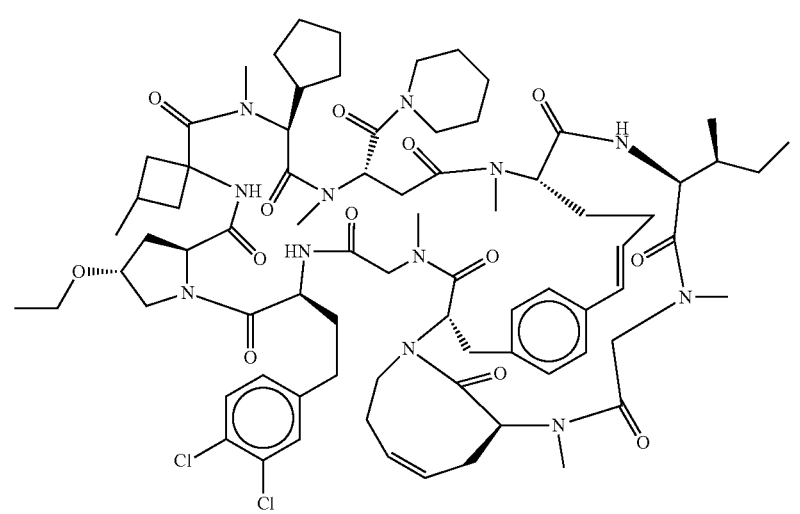 |

TABLE 38-continued
| Compound No. | Structural Formula |
|---|---|
| PP2598 | 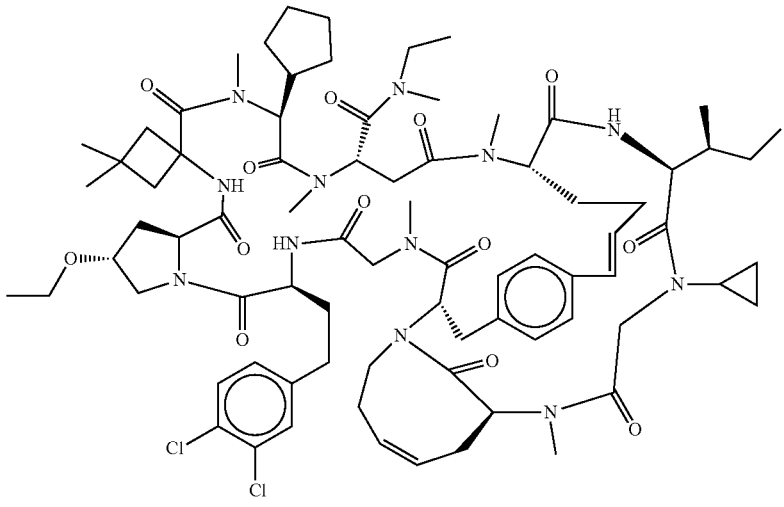 |
| PP2600 | 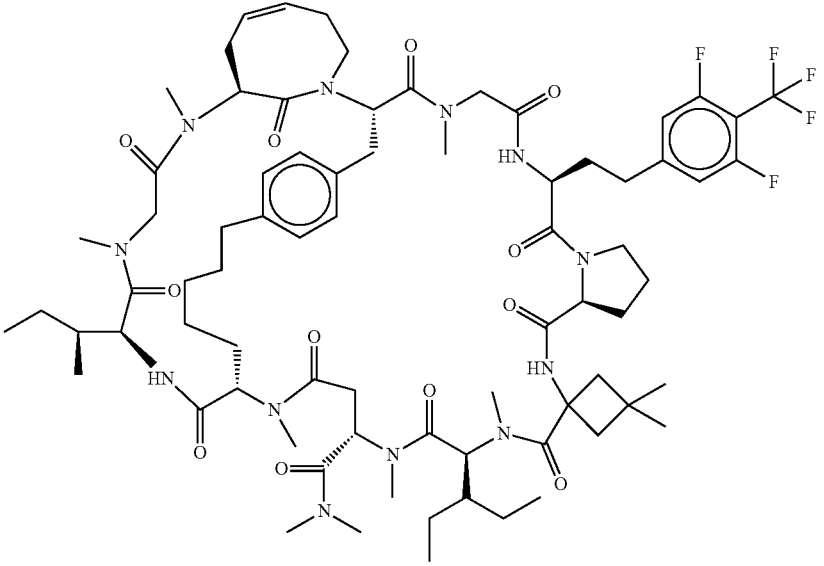 |

TABLE 38-continued
| Compound No. | Structural Formula |
|---|---|
| PP2601 | 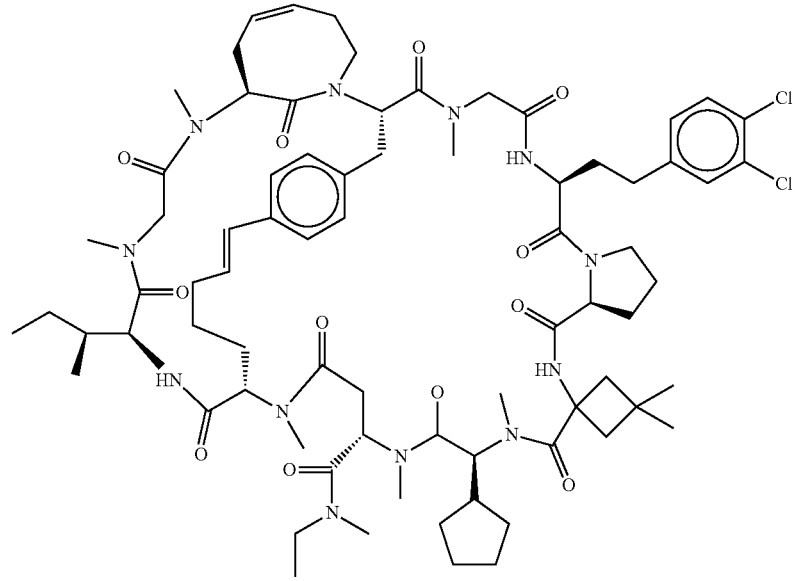 |
| PP2602 | 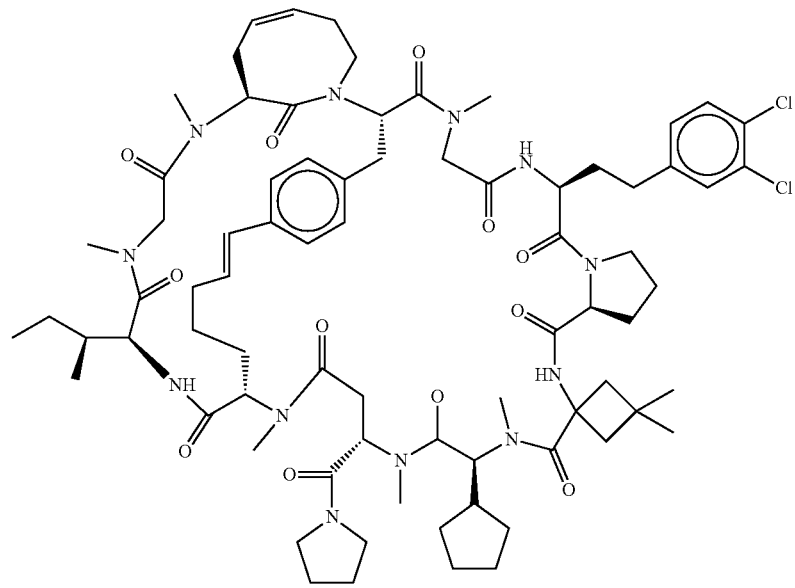 |

TABLE 38-continued
| Compound No. | Structural Formula |
|---|---|
| PP2603 | 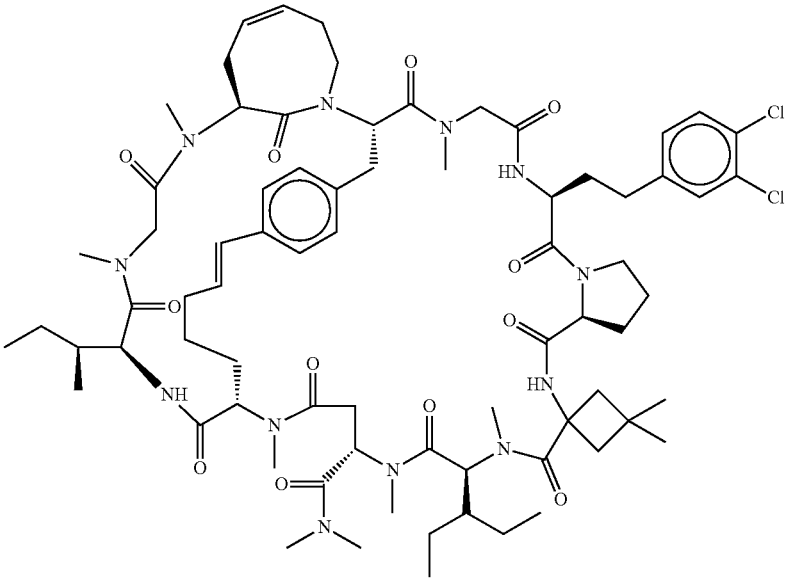 |
| PP2604 | 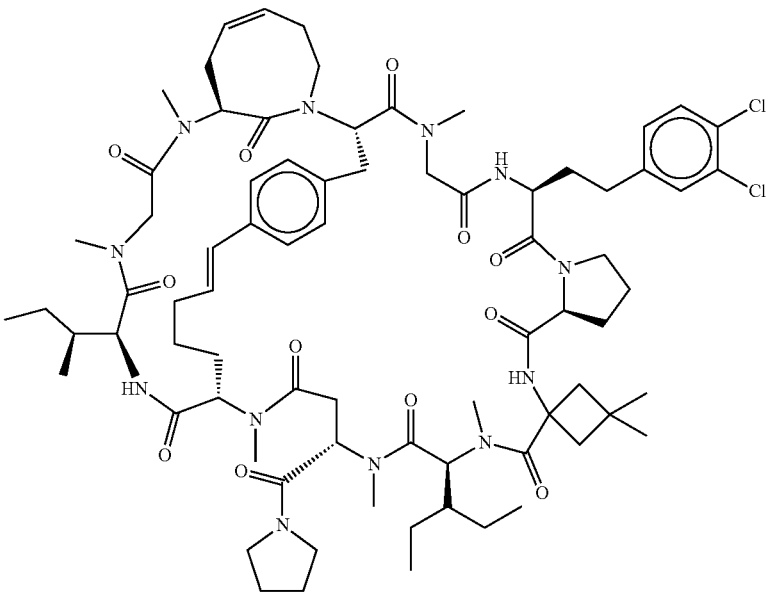 |

TABLE 38-continued
| Compound No. | Structural Formula |
|---|---|
| PP2605 | 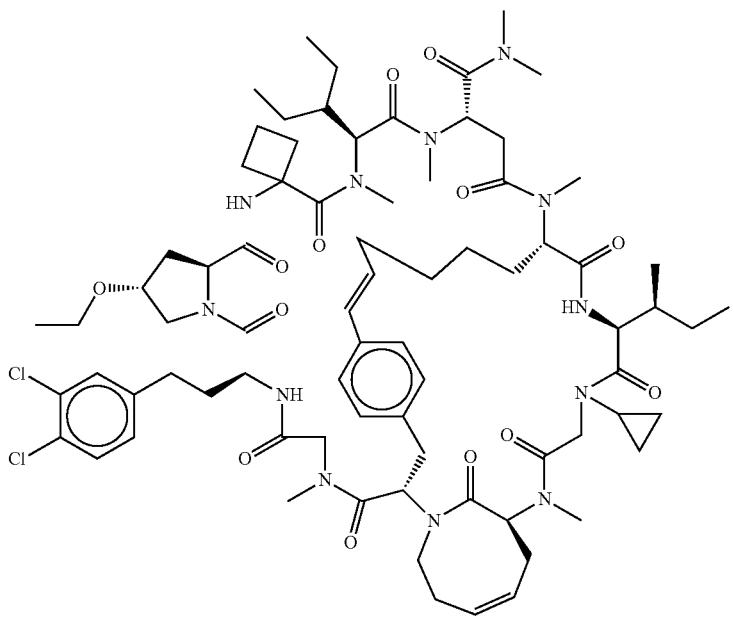 |
| PP2606 | 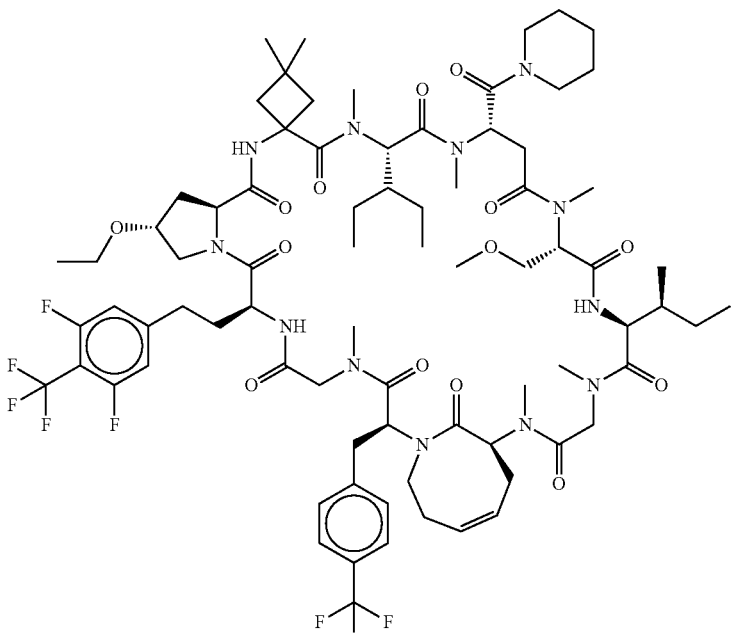 |

TABLE 38-continued

| Compound No. | Structural Formula |
|---|---|
| PP2608 | |
| PP2610 | |

TABLE 38-continued

| Compound No. | Structural Formula |
|---|---|
| PP2611 | |
| PP2612 | |

TABLE 38-continued
| Compound No. | Structural Formula |
|---|---|
| PP2614 | 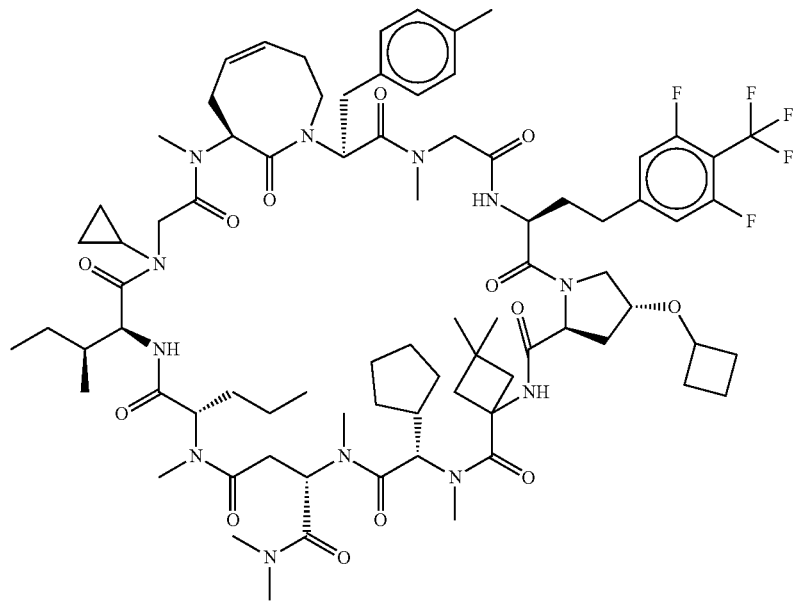 |
| PP2615 | 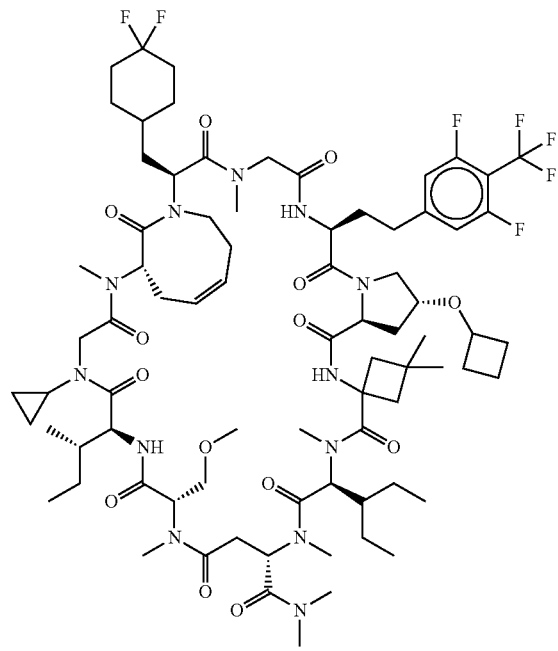 |

TABLE 38-continued
| Compound No. | Structural Formula |
|---|---|
| PP2616 | 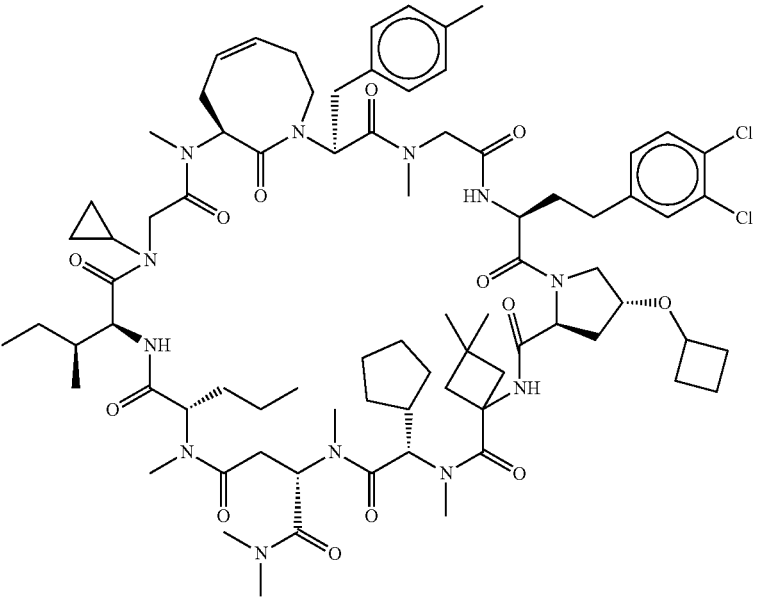 |
| PP2617 | 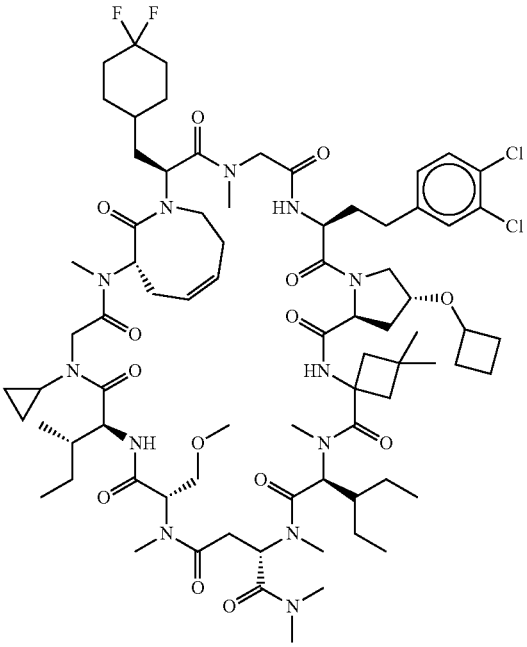 |

TABLE 38-continued
| Compound No. | Structural Formula |
| --- | --- |
| PP2618 | 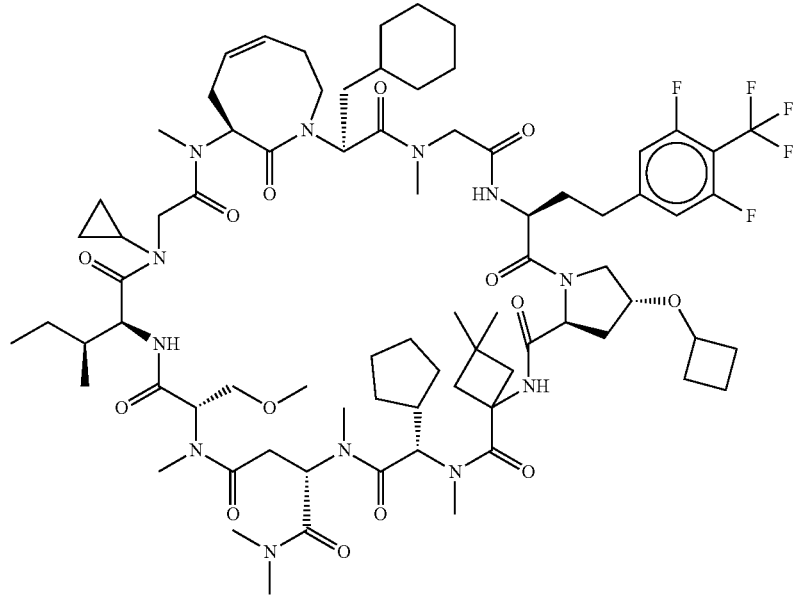 |
| PP2619 | 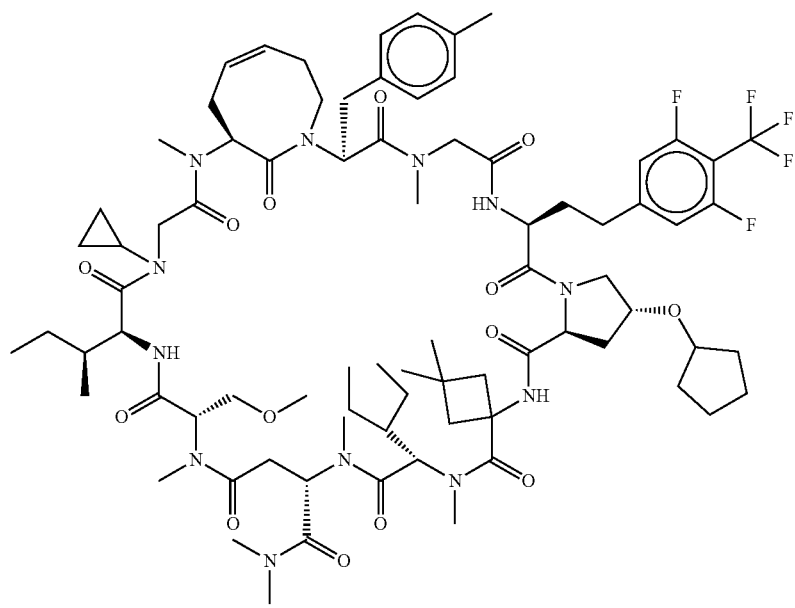 |

TABLE 38-continued

| Compound No. | Structural Formula |
|---|---|
| PP2620 | |
| PP2622 | |

| Compound No. | Structural Formula |
|---|---|
| PP2623 | 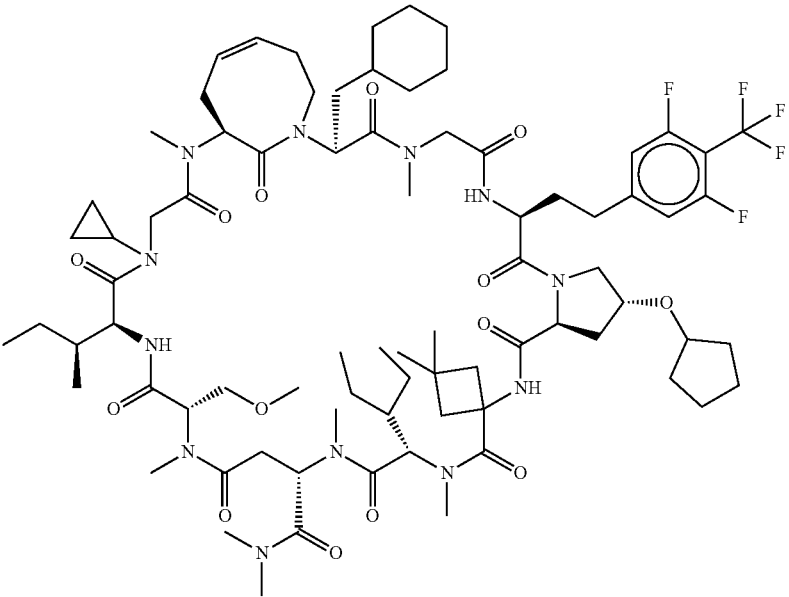 |
| PP2624 | 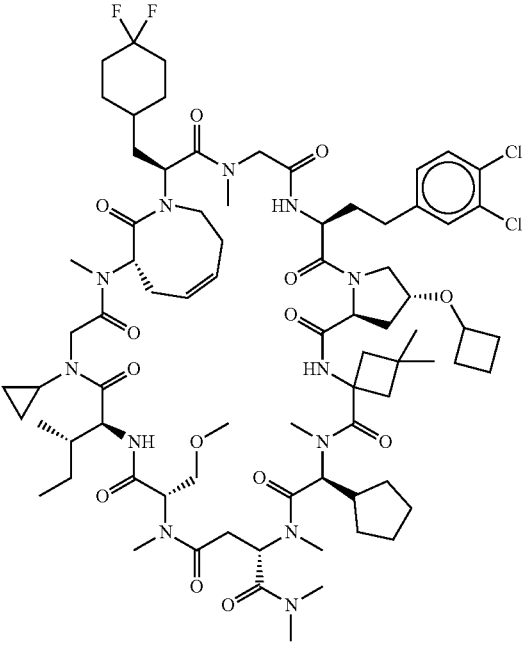 |

TABLE 38-continued

| Compound No. | Structural Formula |
| --- | --- |
| PP2626 | |
| PP2627 | |

TABLE 38-continued

| Compound No. | Structural Formula |
|---|---|
| PP2628 | |
| PP2629 | |

TABLE 38-continued

| Compound No. | Structural Formula |
|---|---|
| PP2630 | |
| PP2631 | |

TABLE 38-continued
| Compound No. | Structural Formula |
|---|---|
| PP2632 | 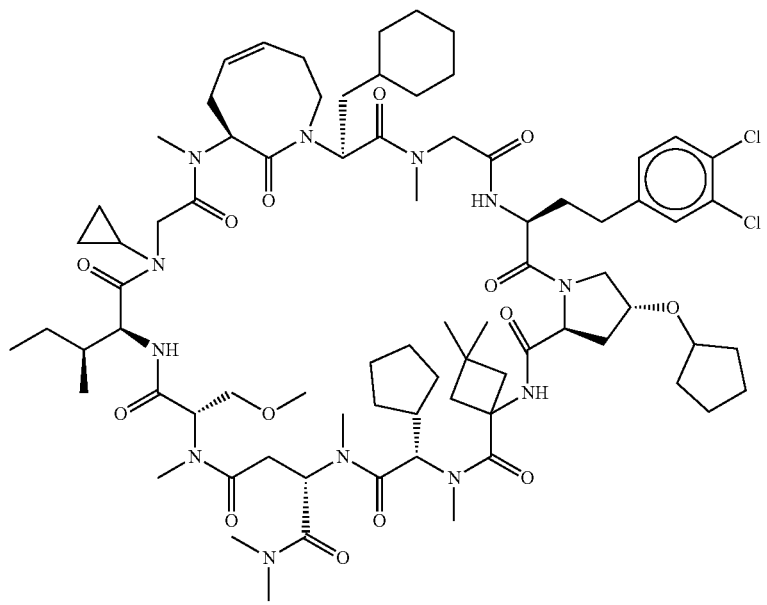 |
| PP2633 | 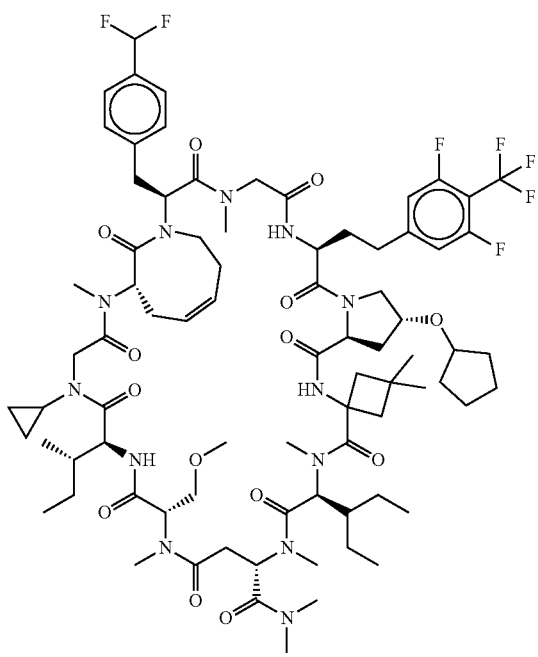 |

TABLE 38-continued

| Compound No. | Structural Formula |
|---|---|
| PP2634 | |
| PP2635 | |

TABLE 38-continued
| Compound No. | Structural Formula |
|---|---|
| PP2636 | 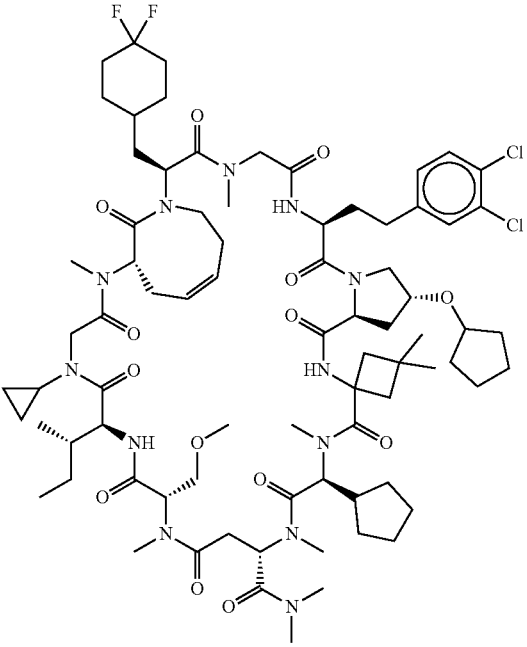 |
| PP2637 | 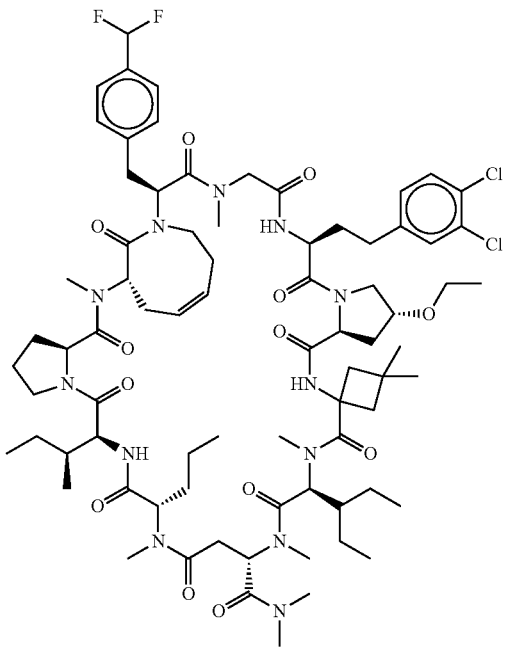 |

TABLE 38-continued
| Compound No. | Structural Formula |
|---|---|
| PP2638 | 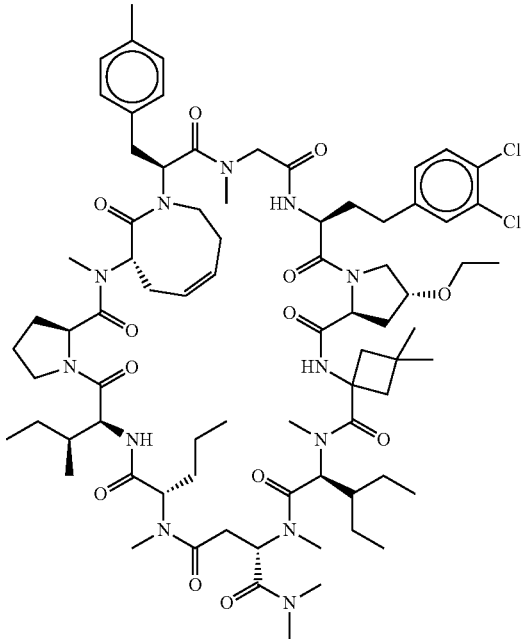 |
| PP2639 | 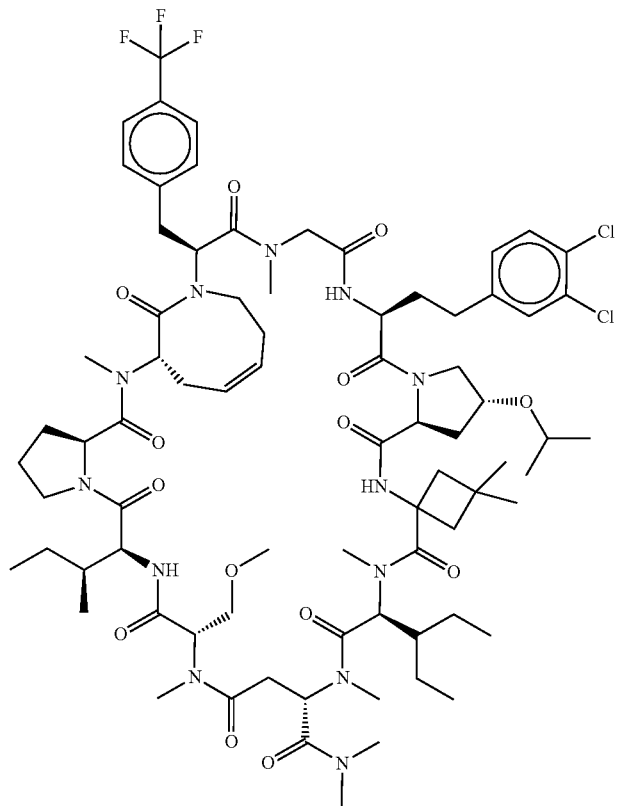 |

TABLE 38-continued
| Compound No. | Structural Formula |
|---|---|
| PP2640 | 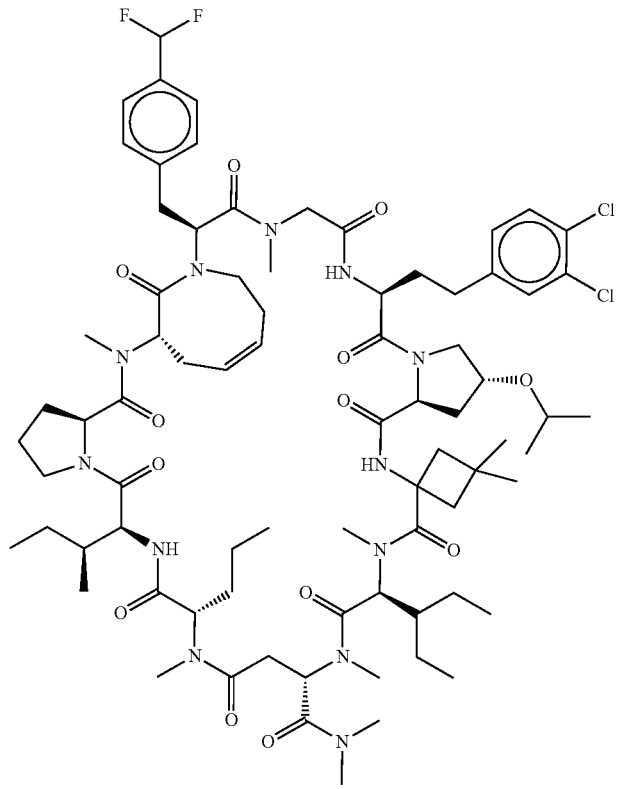 |
| PP2641 | 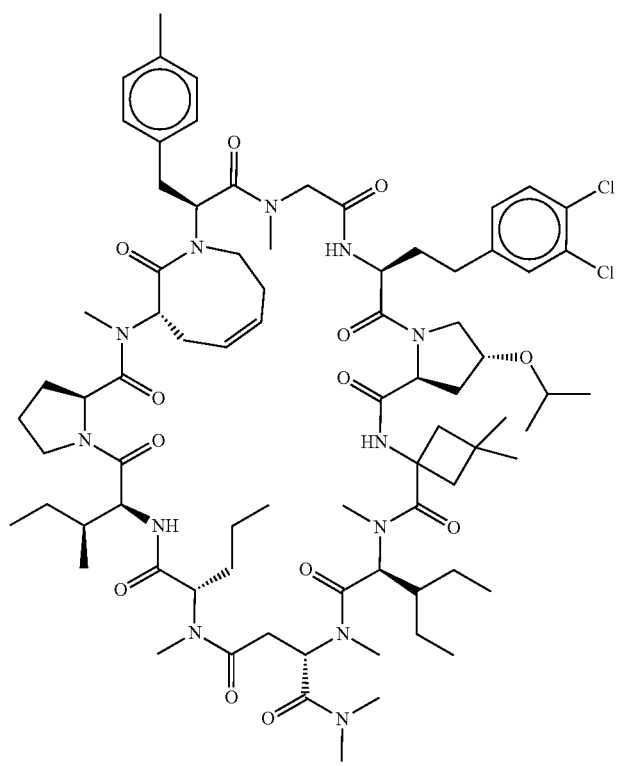 |

TABLE 38-continued
| Compound No. | Structural Formula |
|---|---|
| PP2642 | 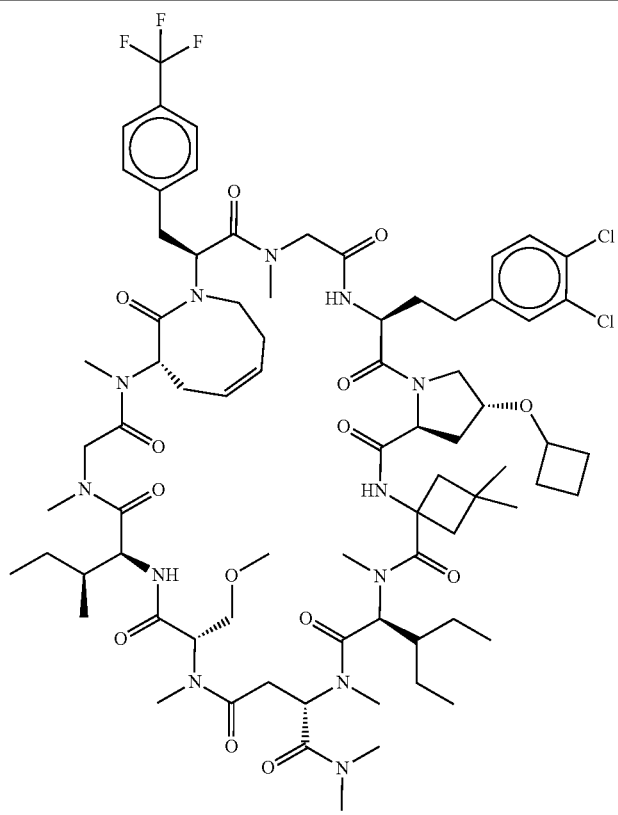 |
| PP2643 | 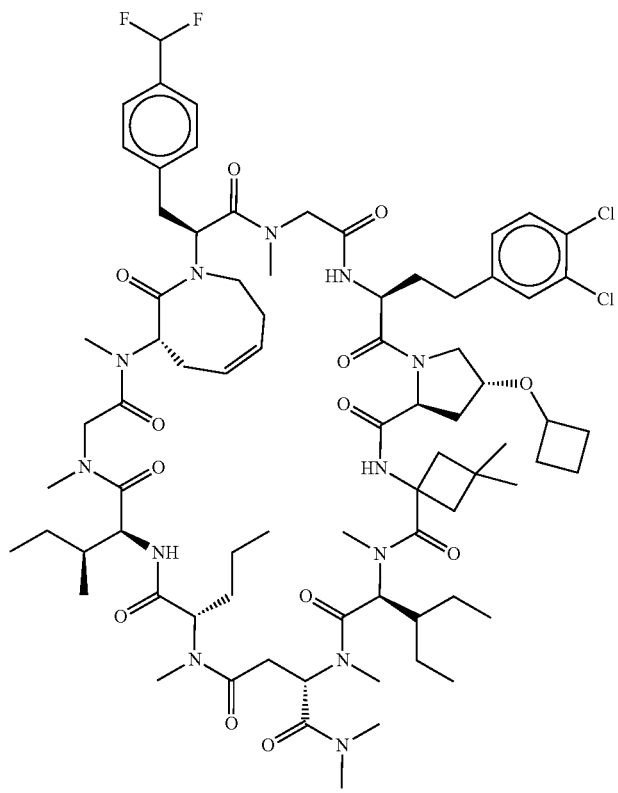 |

TABLE 38-continued

| Compound No. | Structural Formula |
|---|---|
| PP2644 | |
| PP2645 | |

TABLE 38-continued

| Compound No. | Structural Formula |
|---|---|
| PP2646 | |
| PP2647 | |

TABLE 38-continued
| Compound No. | Structural Formula |
|---|---|
| PP2648 | 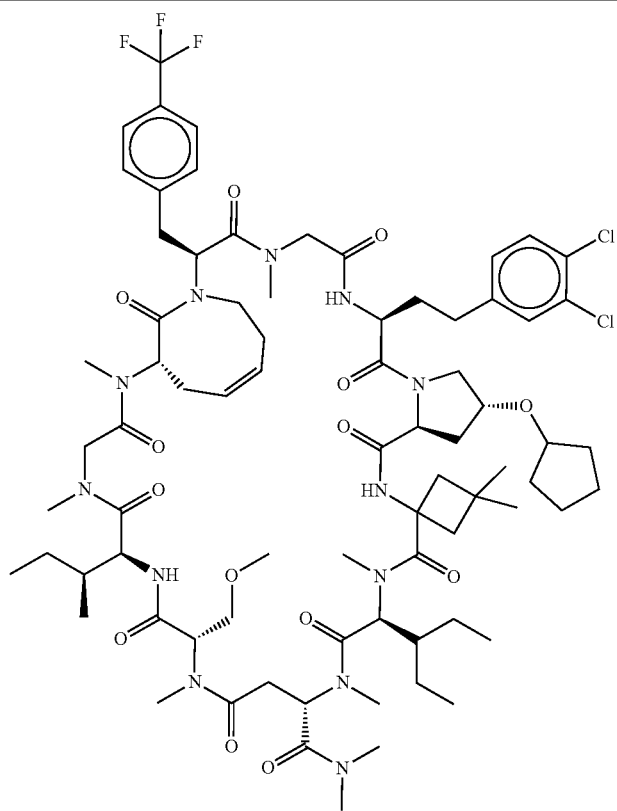 |
| PP2649 | 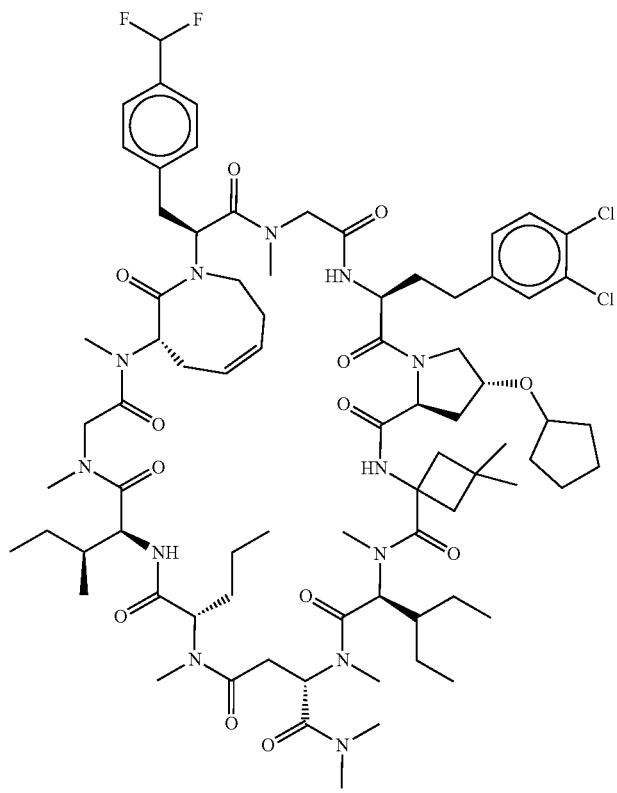 |

TABLE 38-continued

| Compound No. | Structural Formula |
|---|---|
| PP2650 | |
| PP2651 | |

TABLE 38-continued
| Compound No. | Structural Formula |
|---|---|
| PP2652 | 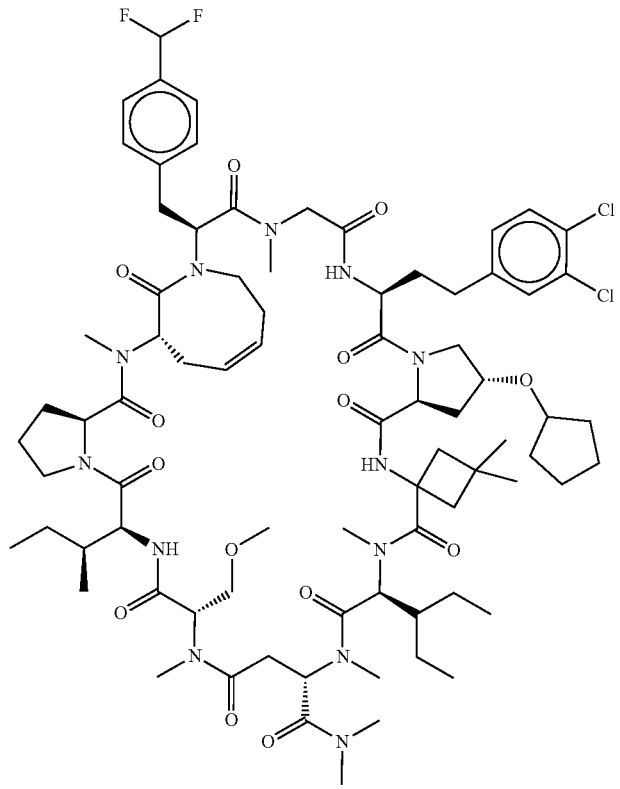 |
| PP2653 | 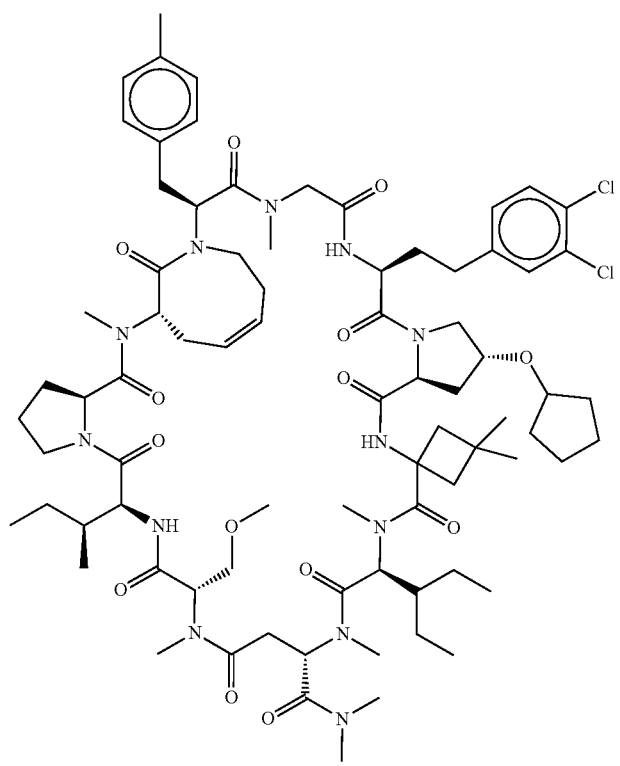 |

TABLE 38-continued
| Compound No. | Structural Formula |
|---|---|
| PP2654 | 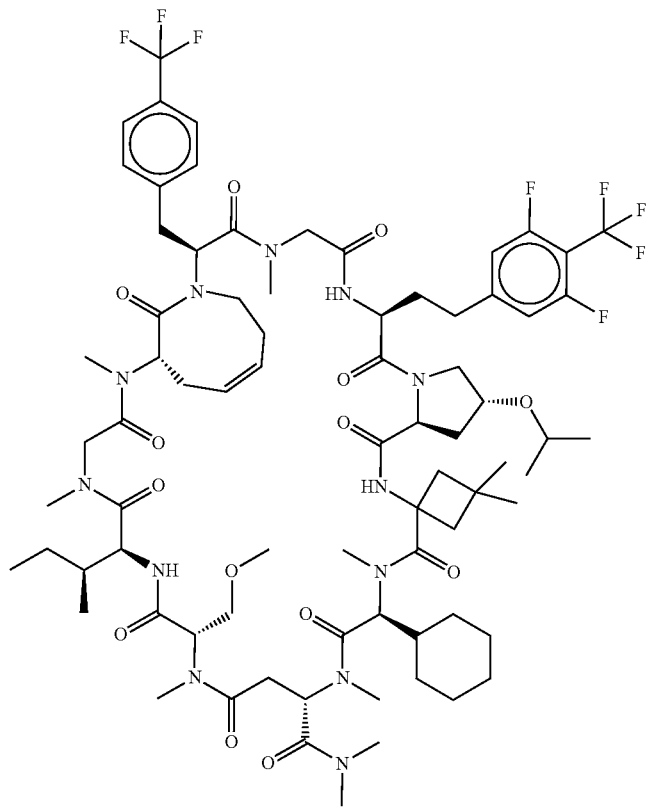 |
| PP2655 | 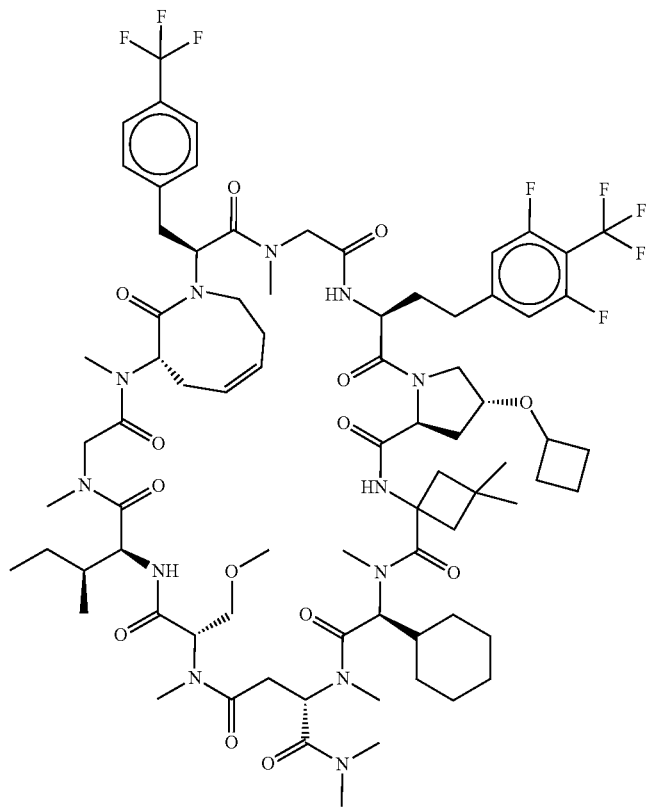 |

TABLE 38-continued
| Compound No. | Structural Formula |
|---|---|
| PP2656 | 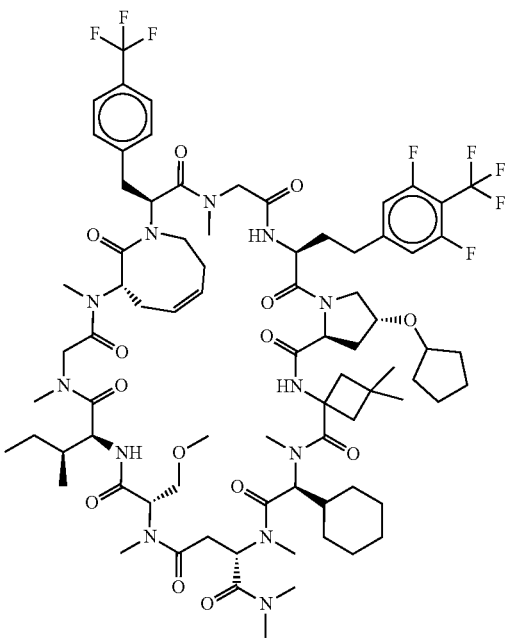 |
| PP2657 | 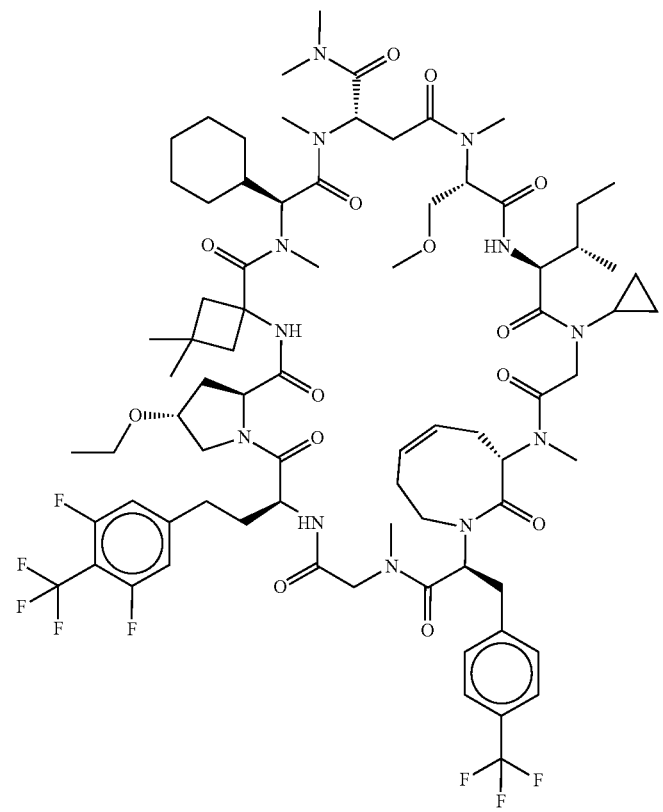 |

TABLE 38-continued

| Compound No. | Structural Formula |
|---|---|
| PP2659 | |
| PP2660 | |

TABLE 38-continued
| Compound No. | Structural Formula |
|---|---|
| PP2661 | 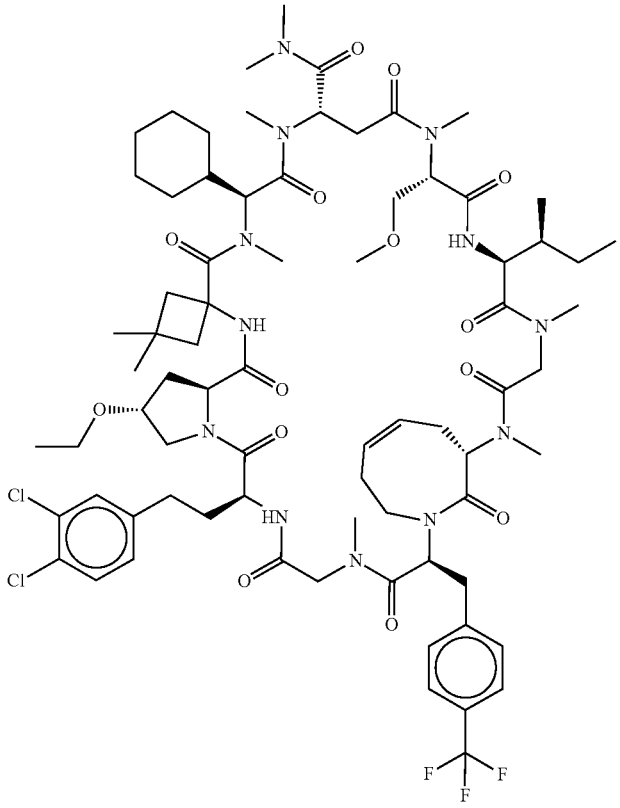 |
| PP2662 | 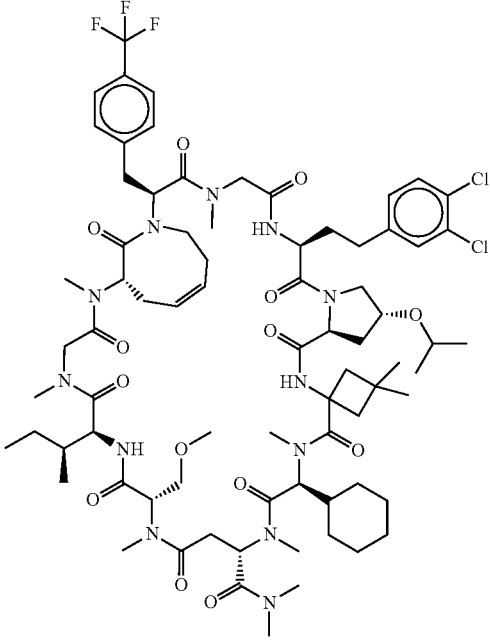 |

| Compound No. | Structural Formula |
|---|---|
| PP2663 | |
| PP2664 | |

TABLE 38-continued
| Compound No. | Structural Formula |
|---|---|
| PP2665 | 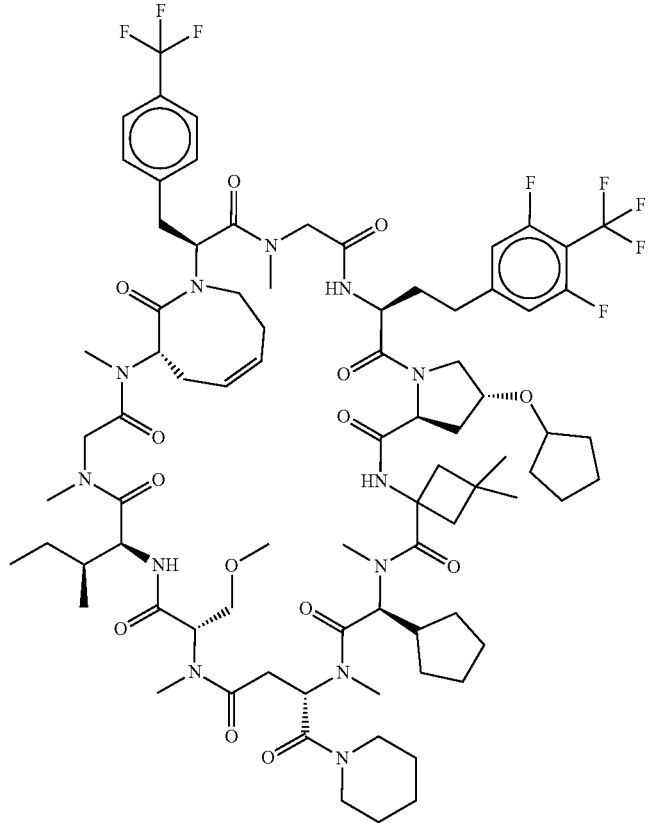 |
| PP2666 | 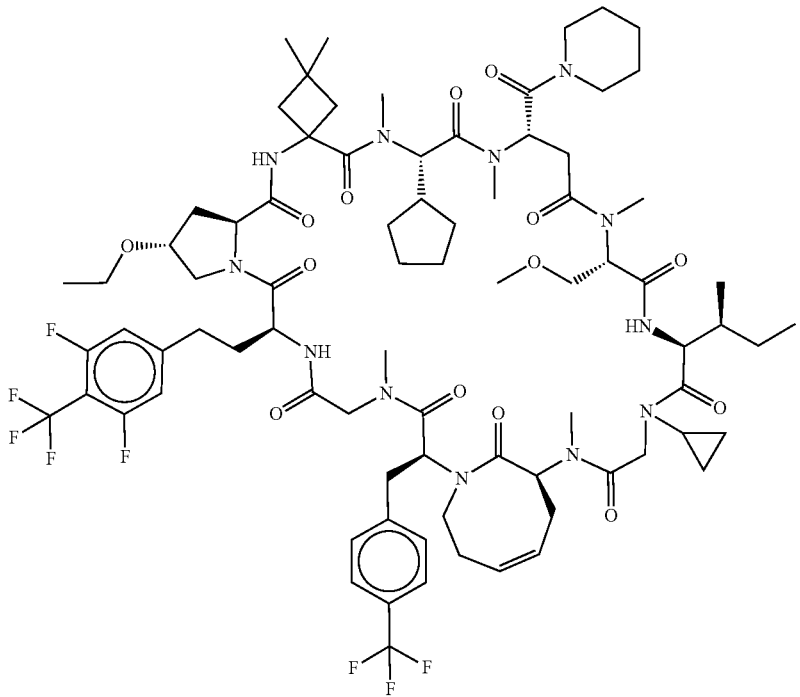 |

TABLE 38-continued
| Compound No. | Structural Formula |
|---|---|
| PP2667 | 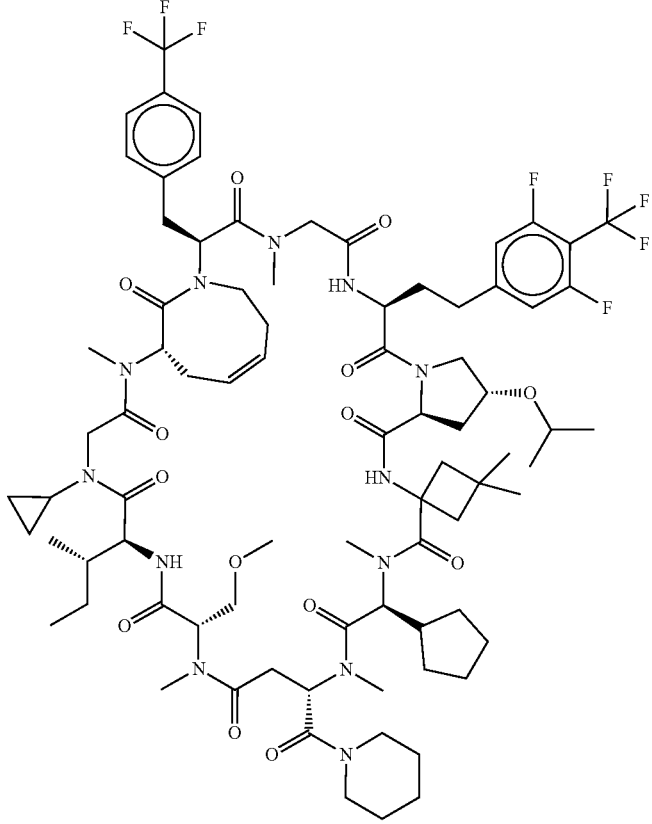 |
| PP2668 | 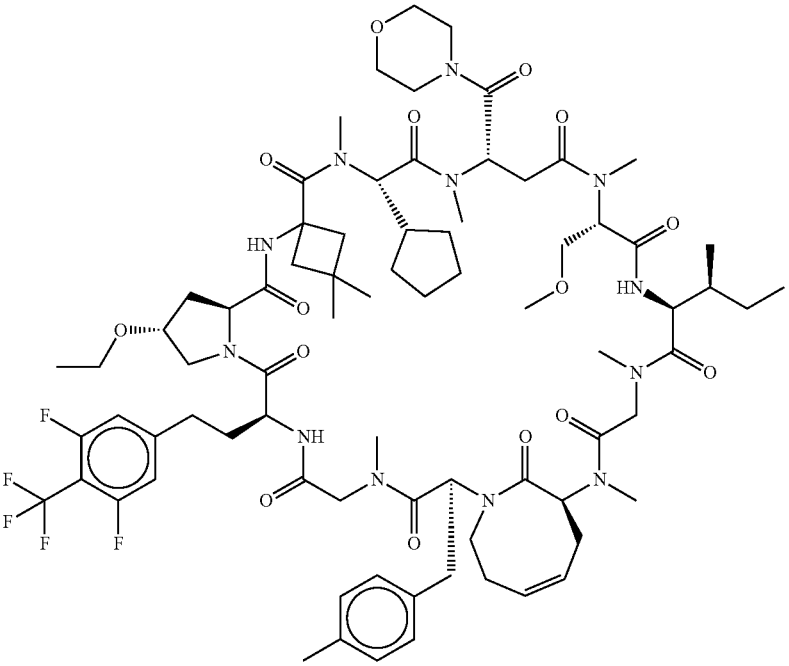 |

TABLE 38-continued

| Compound No. | Structural Formula |
|---|---|
| PP2669 | |
| PP2670 | |

TABLE 38-continued
| Compound No. | Structural Formula |
|---|---|
| PP2671 | 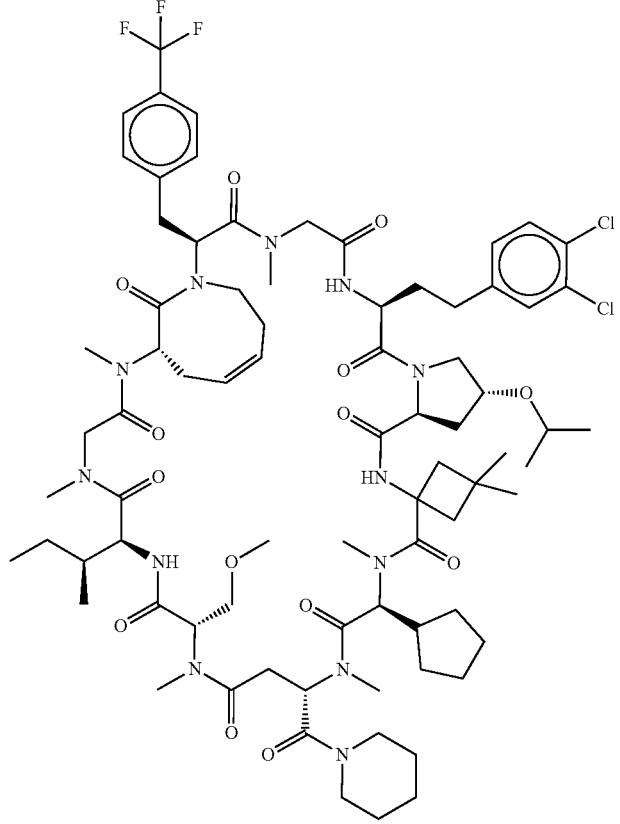 |
| PP2672 | 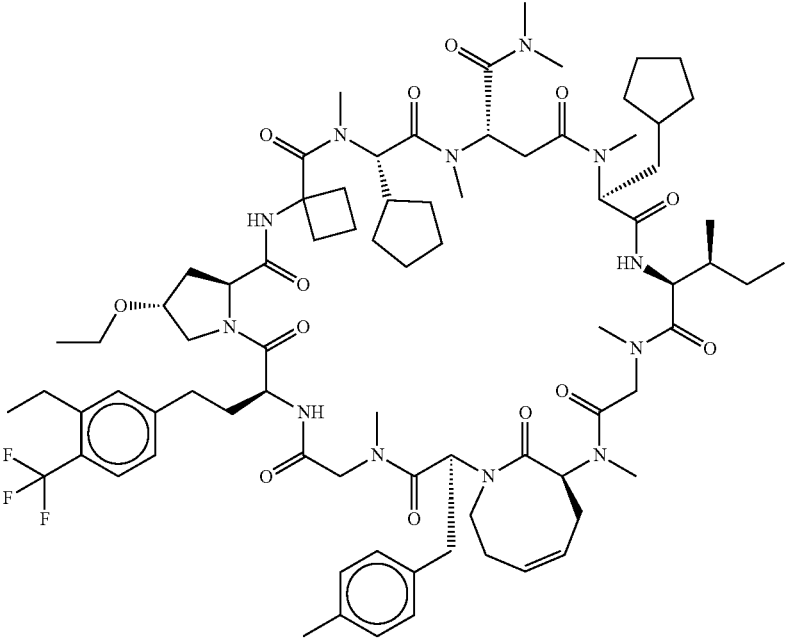 |

TABLE 38-continued
| Compound No. | Structural Formula |
|---|---|
| PP2673 | 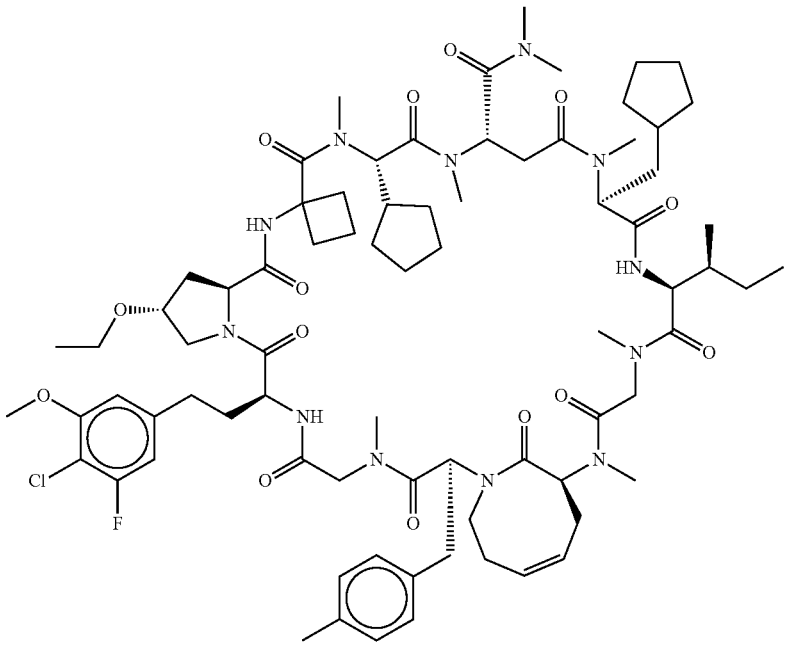 |
| PP2674 | 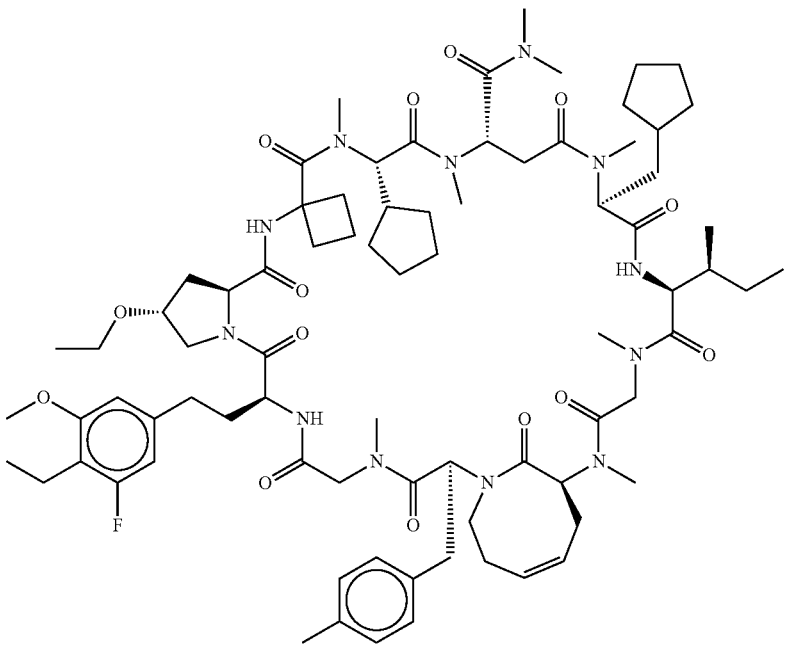 |

TABLE 38-continued
| Compound No. | Structural Formula |
|---|---|
| PP2675 | 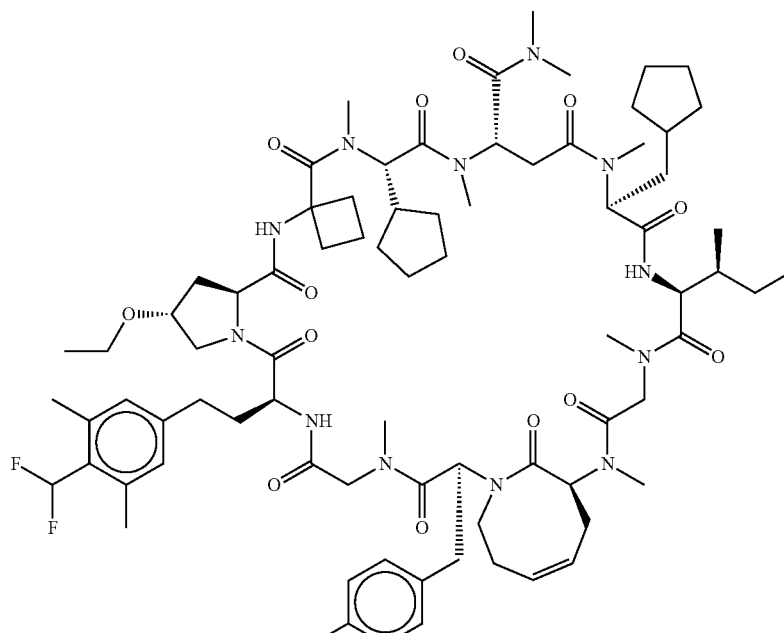 |
| PP2676 | 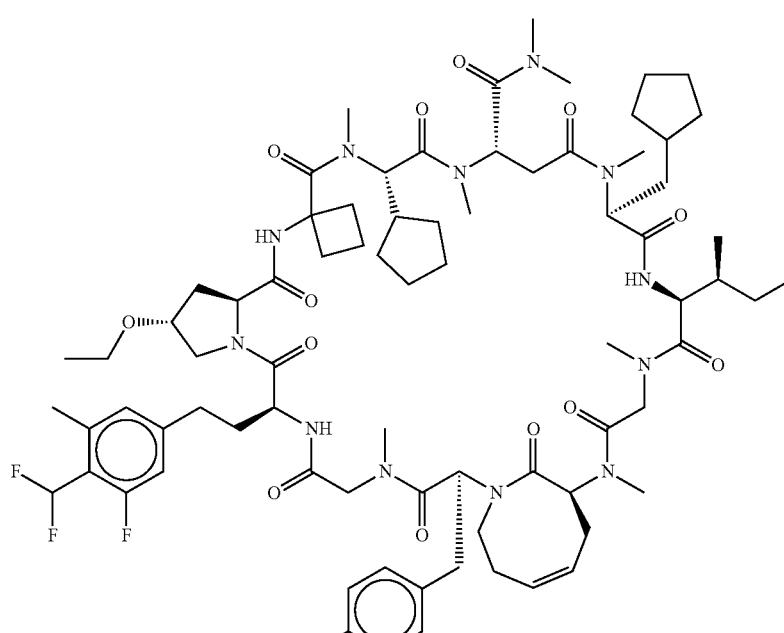 |

TABLE 38-continued
| Compound No. | Structural Formula |
|---|---|
| PP2677 | 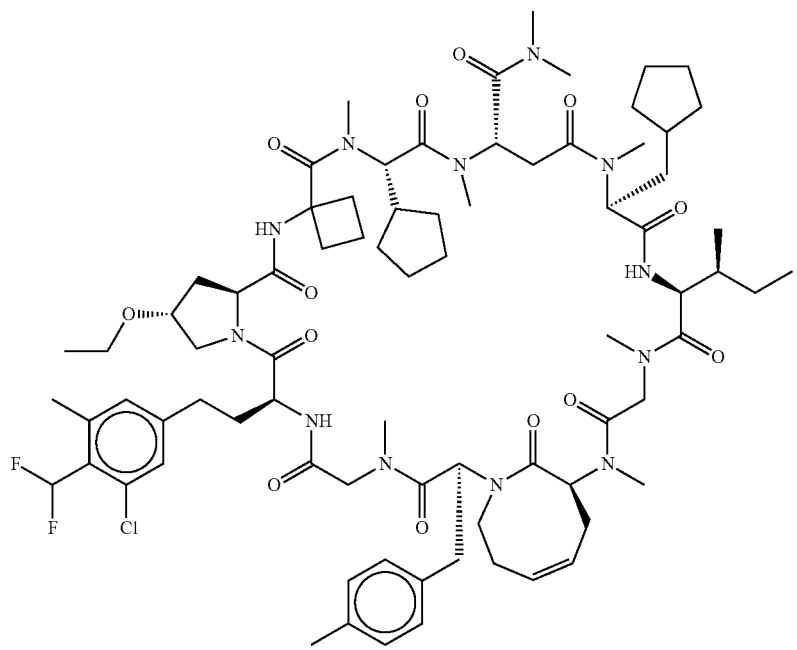 |
| PP2678 | 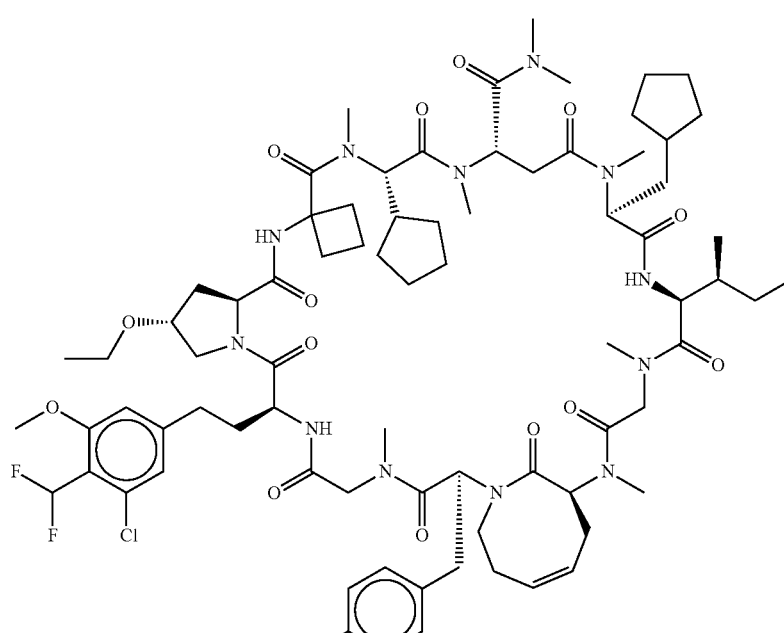 |

TABLE 38-continued
| Compound No. | Structural Formula |
|---|---|
| PP2679 | 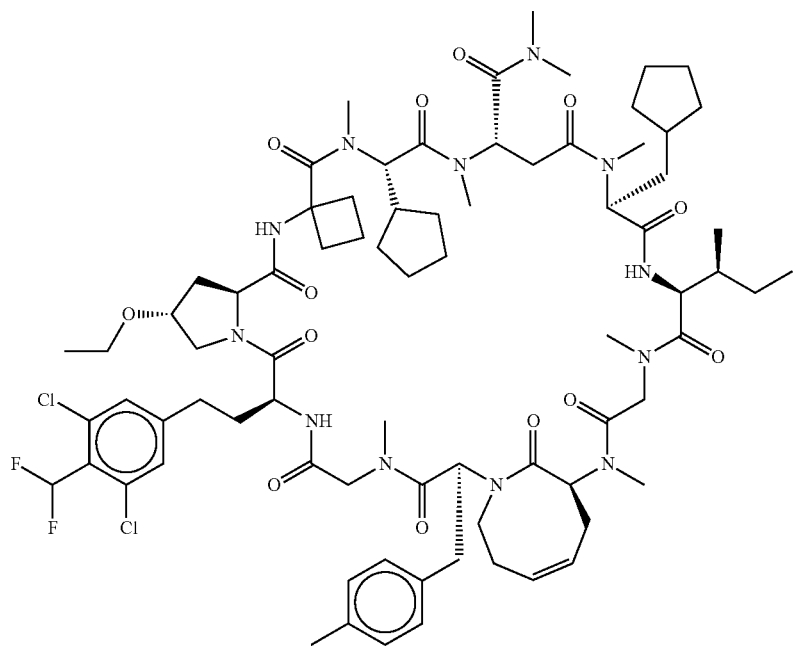 |
| PP2680 | 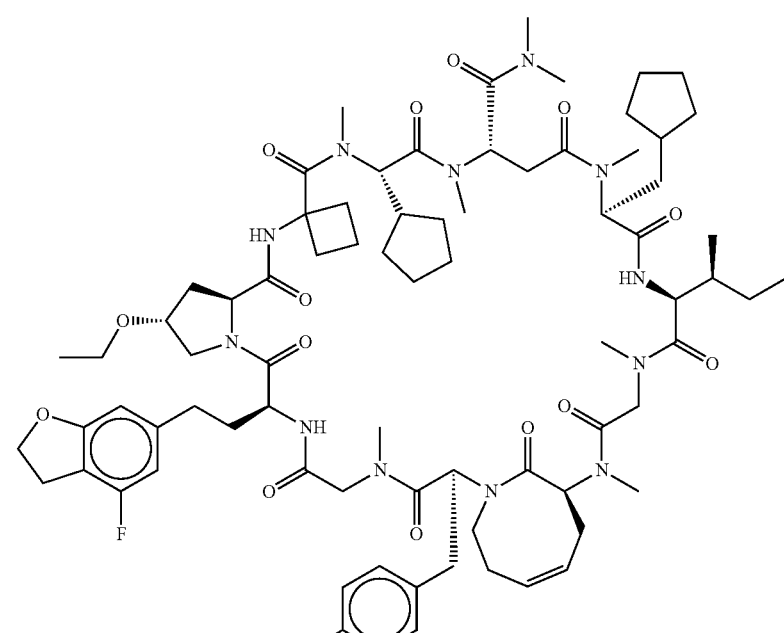 |

TABLE 38-continued
| Compound No. | Structural Formula |
|---|---|
| PP2681 | 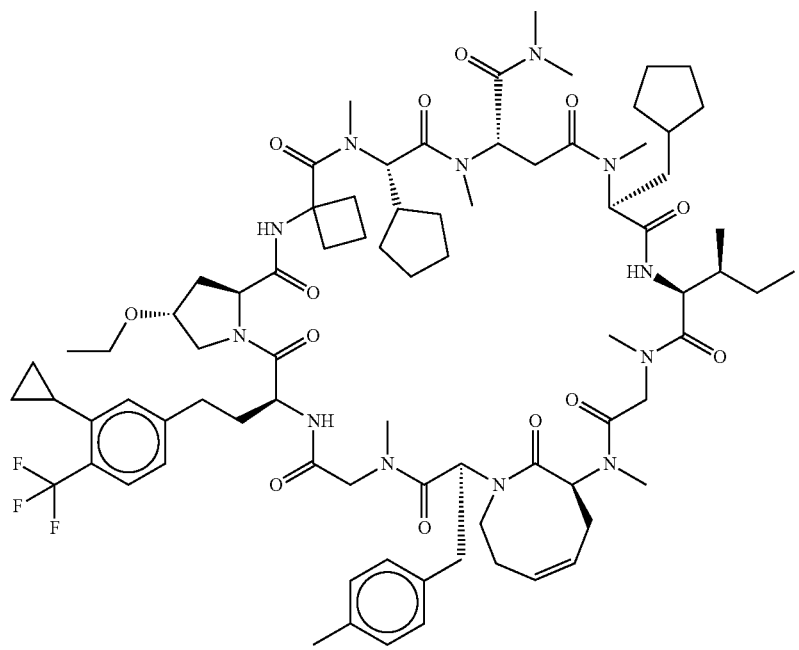 |
| PP2682 | 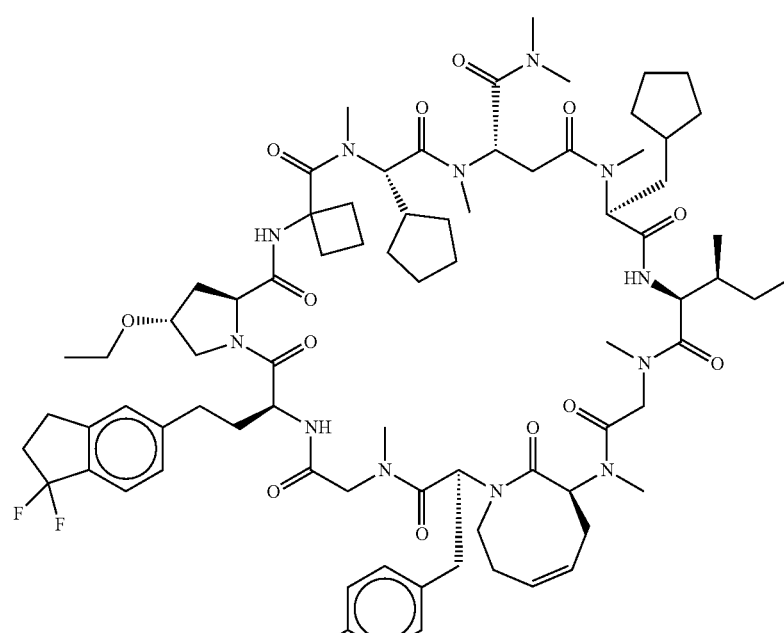 |

TABLE 38-continued

| Compound No. | Structural Formula |
|---|---|
| PP2683 | |
| PP2684 | |

TABLE 38-continued
| Compound No. | Structural Formula |
|---|---|
| PP2685 | 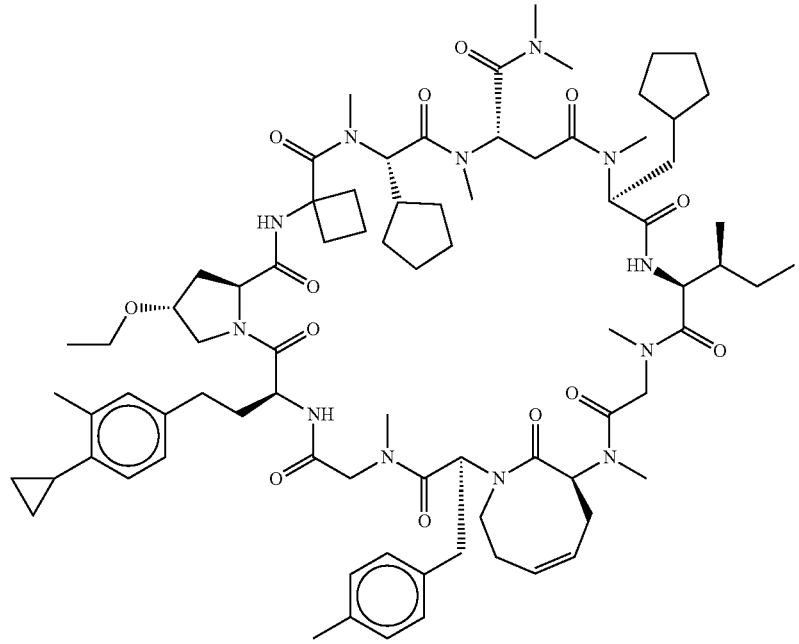 |
| PP2686 | 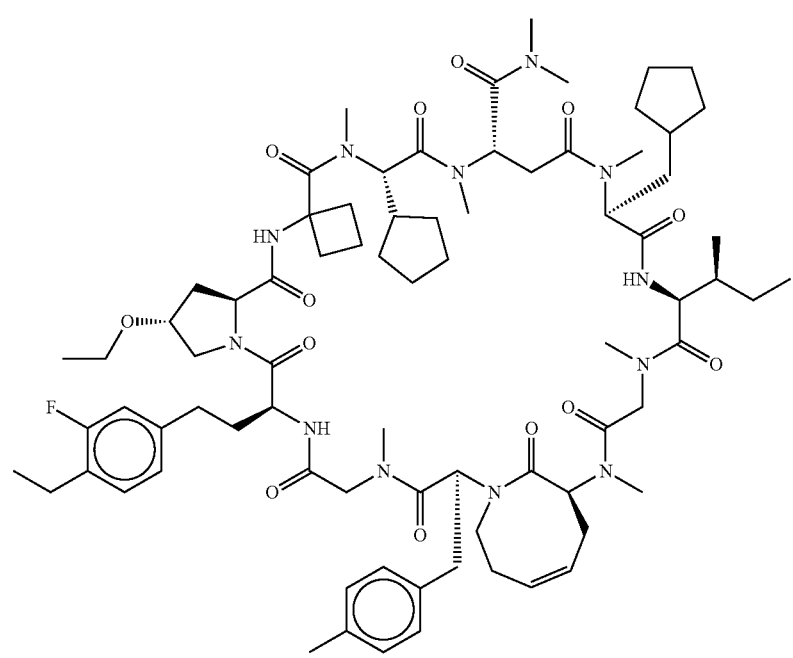 |

TABLE 38-continued
| Compound No. | Structural Formula |
|---|---|
| PP2687 | 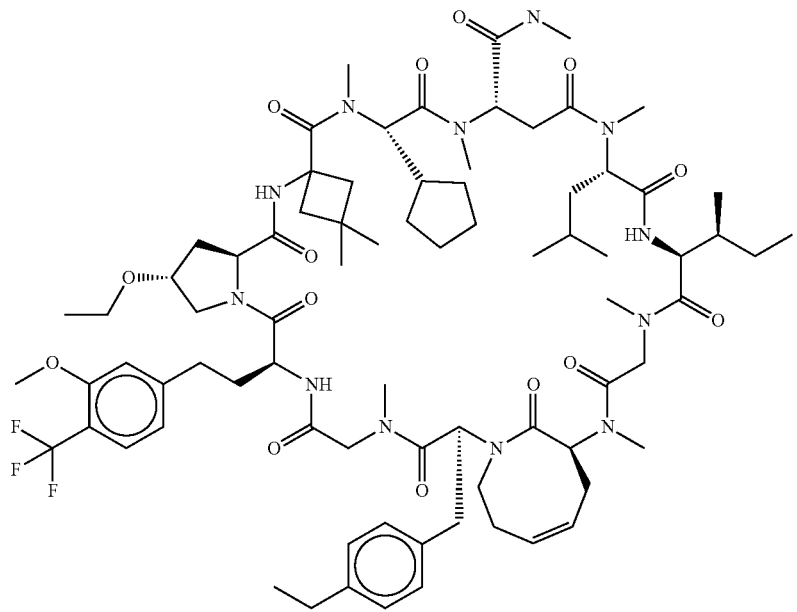 |
| PP2688 | 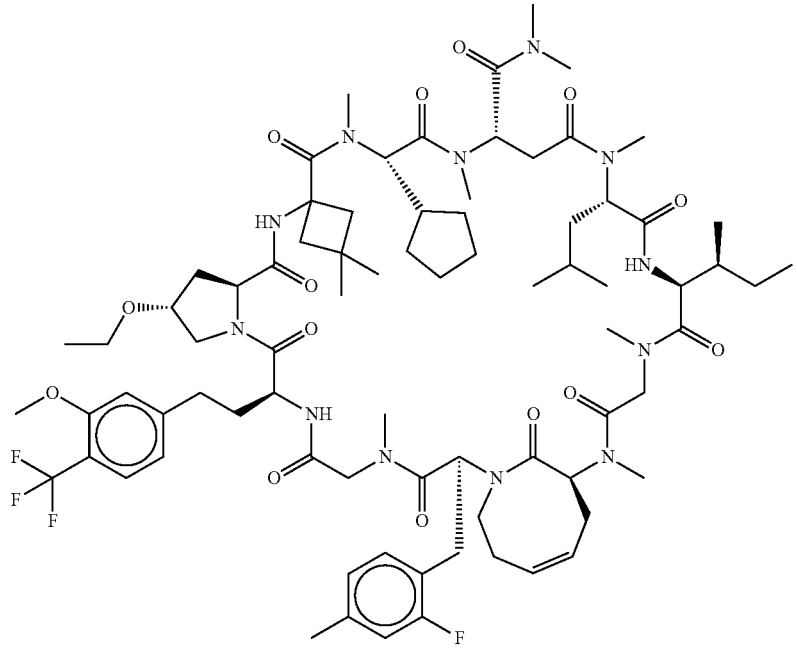 |

TABLE 38-continued
| Compound No. | Structural Formula |
|---|---|
| PP2689 | 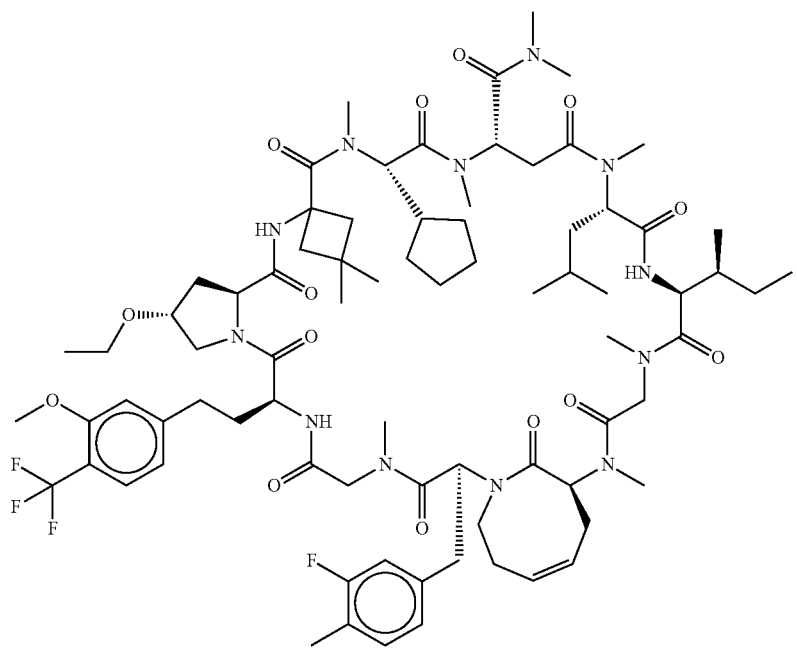 |
| PP2690 | 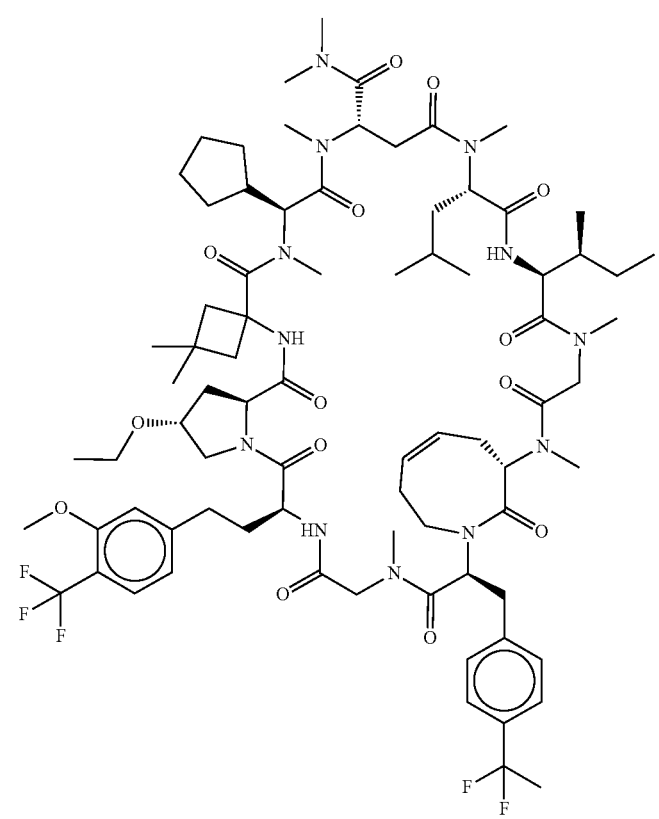 |

TABLE 38-continued
| Compound No. | Structural Formula |
|---|---|
| PP2691 | 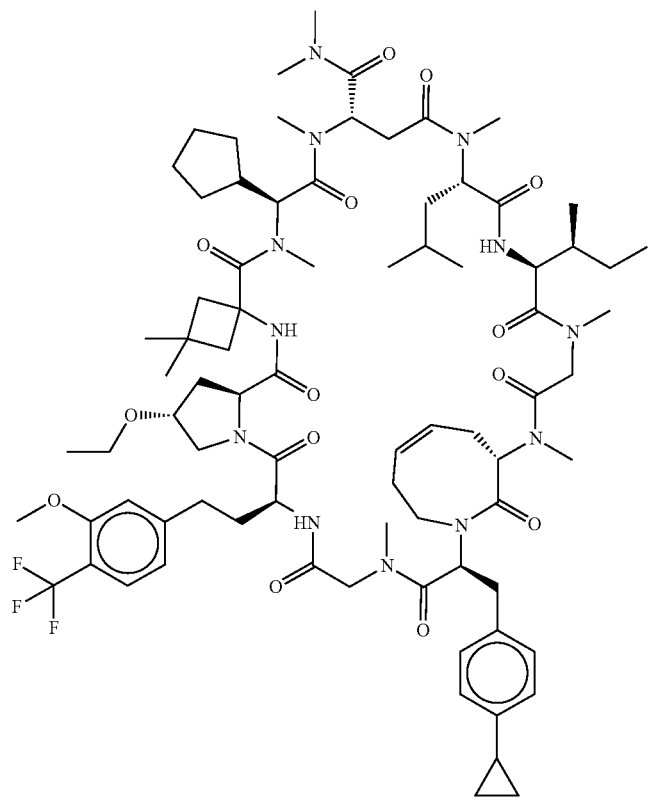 |
| PP2692 | 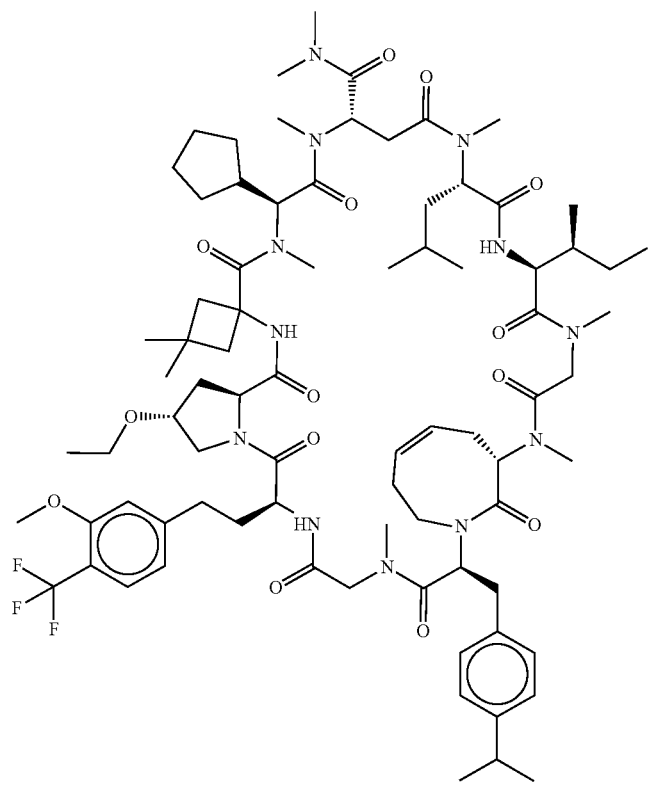 |

TABLE 38-continued
| Compound No. | Structural Formula |
| --- | --- |
| PP2693 | 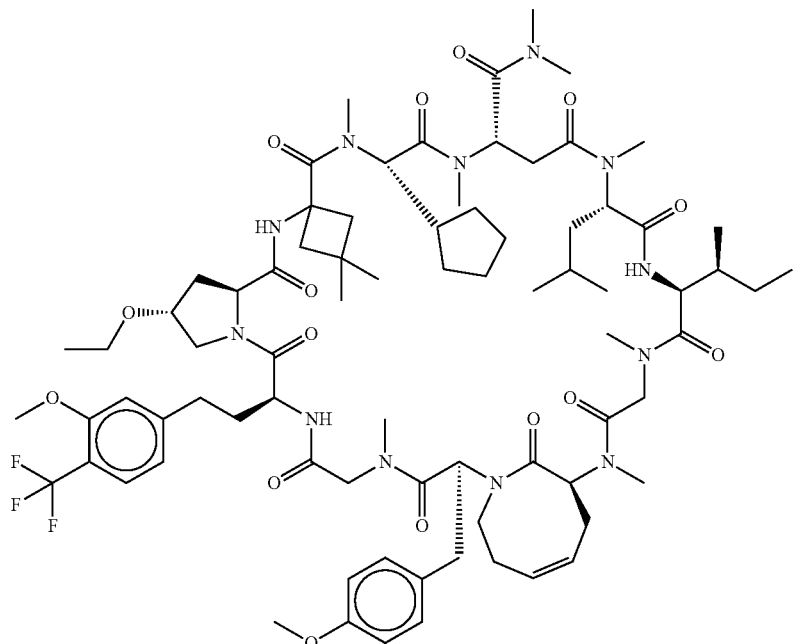 |
| PP2694 | 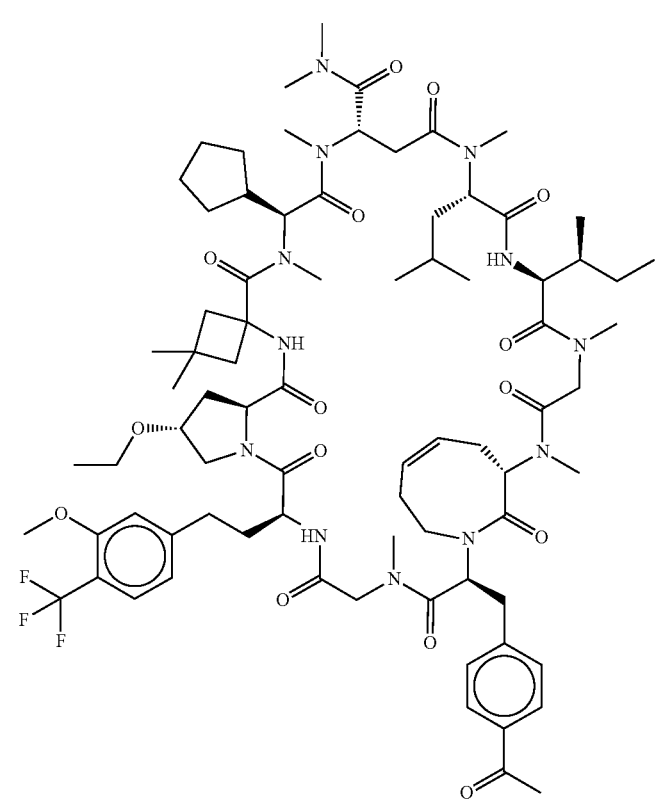 |

TABLE 38-continued
| Compound No. | Structural Formula |
|---|---|
| PP2695 | 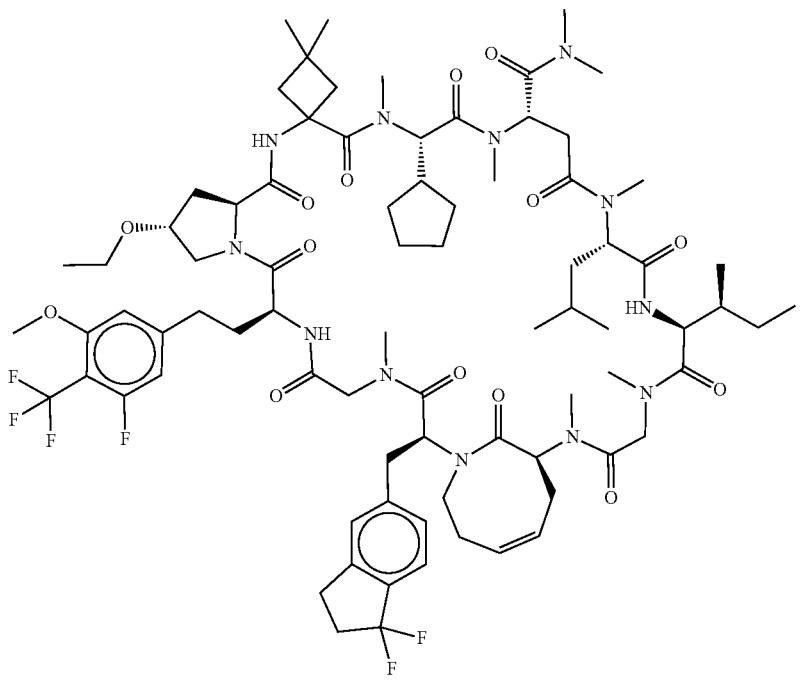 |
| PP2696 | 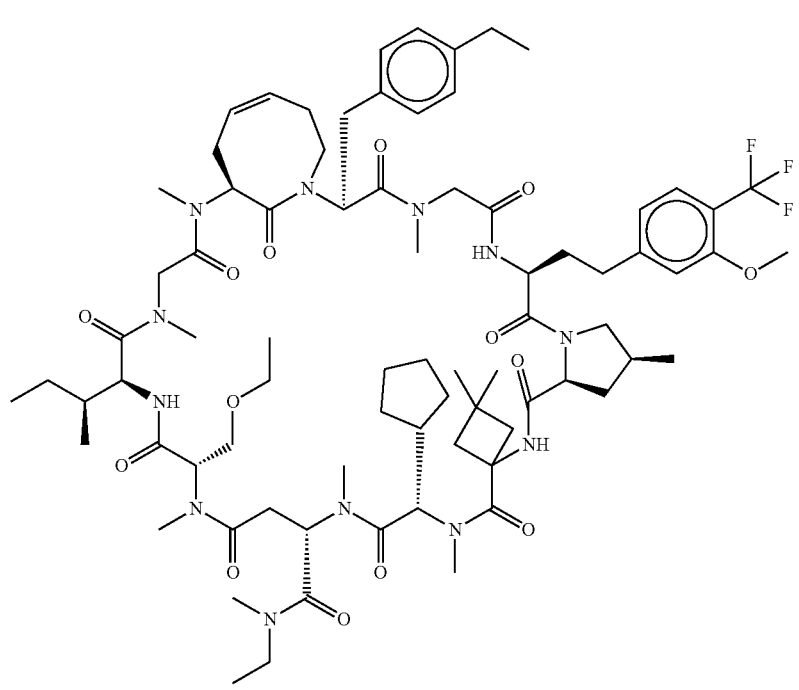 |

TABLE 38-continued

| Compound No. | Structural Formula |
|---|---|
| PP2697 | |
| PP2698 | |

TABLE 38-continued
| Compound No. | Structural Formula |
|---|---|
| PP2699 | 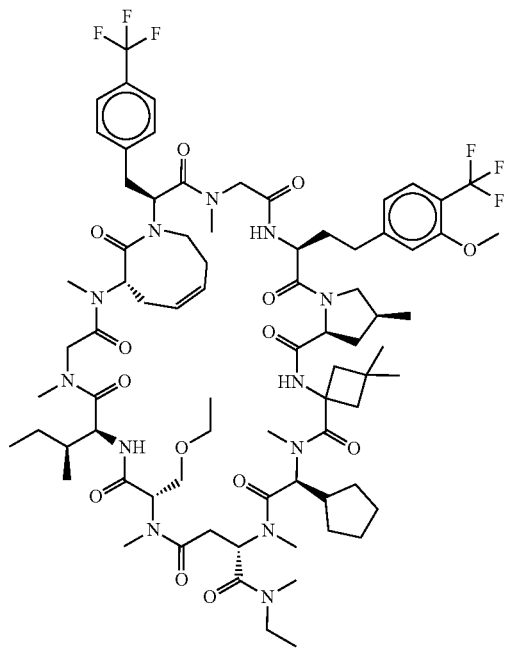 |
| PP2700 | 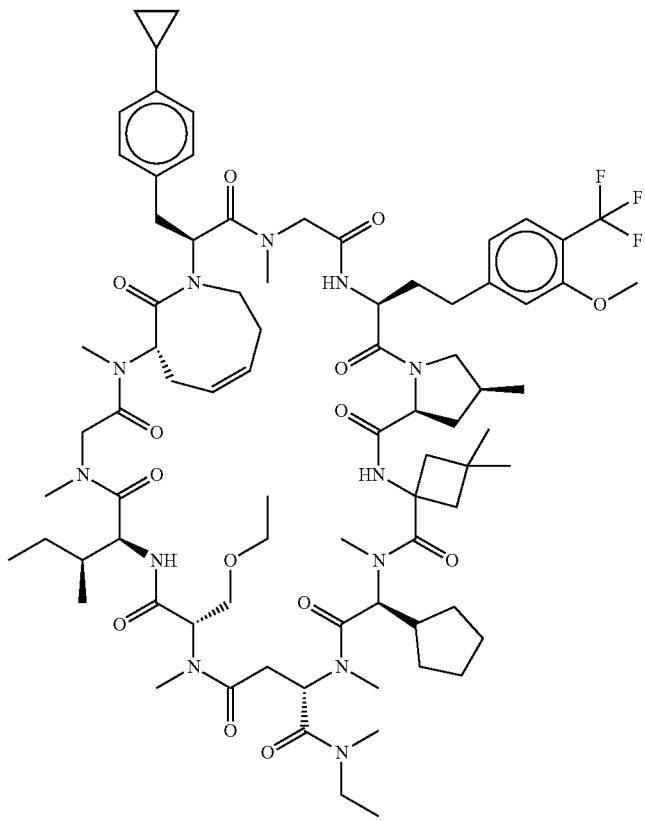 |

TABLE 38-continued

| Compound No. | Structural Formula |
|---|---|
| PP2701 | |
| PP2702 | |

3367 3368
TABLE 38-continued
| Compound No. | Structural Formula |
|---|---|
| PP2703 | 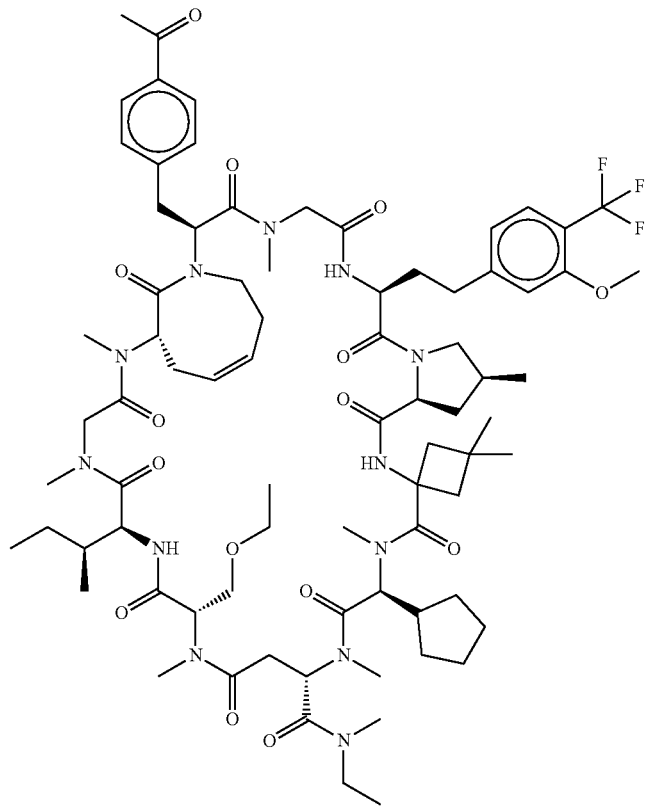 |

TABLE 38-continued

| Compound No. | Structural Formula |
|---|---|
| PP2704 | |
| PP2706 | |

TABLE 38-continued

| Compound No. | Structural Formula |
|---|---|
| PP2708 | |
| PP2710 | |

TABLE 38-continued
| Compound No. | Structural Formula |
|---|---|
| PP2712 | 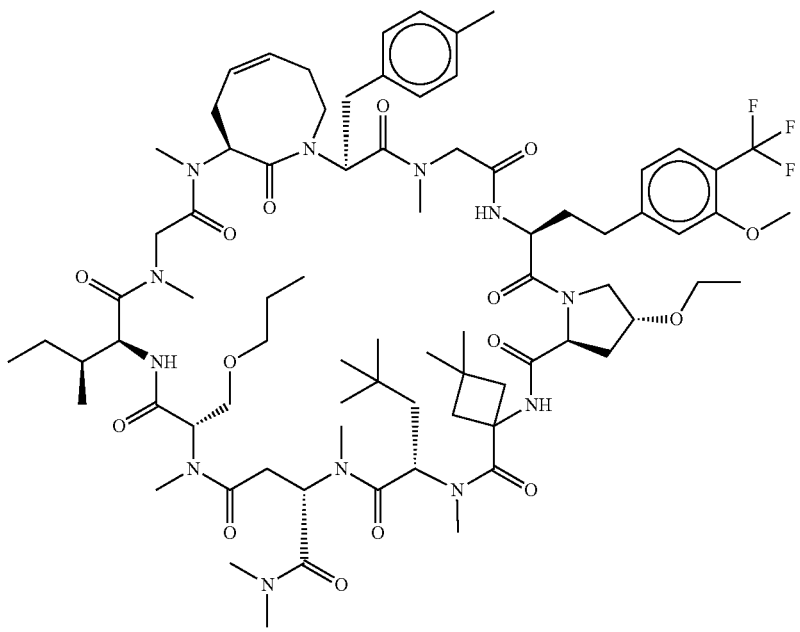 |
| PP2714 | 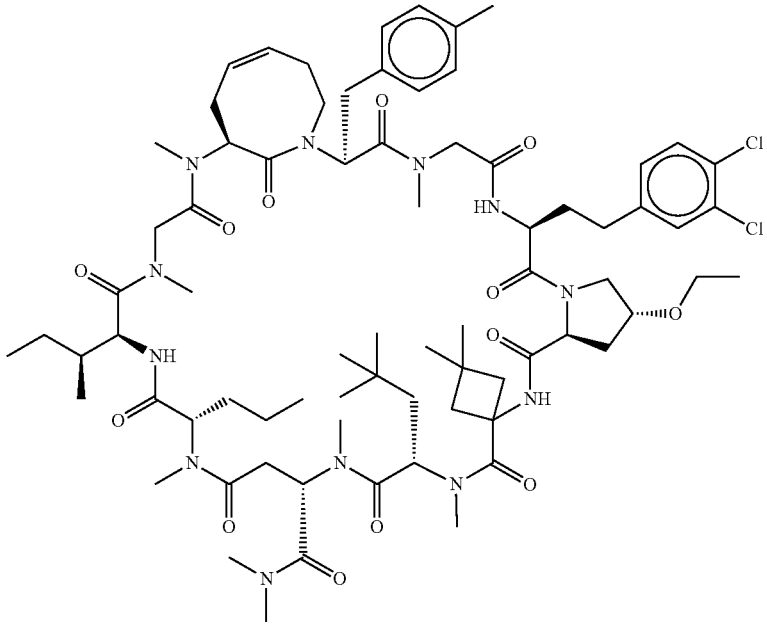 |

TABLE 38-continued
| Compound No. | Structural Formula |
| --- | --- |
| PP2716 | 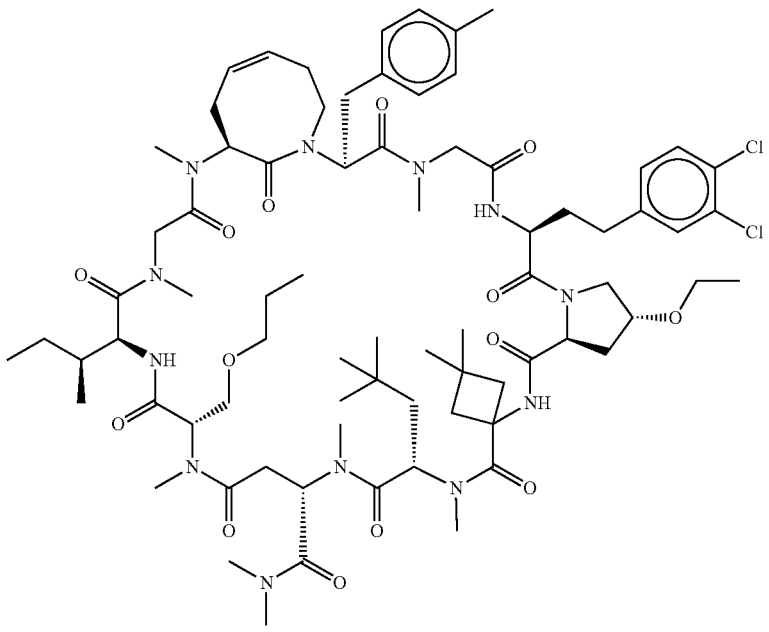 |
| PP2718 | 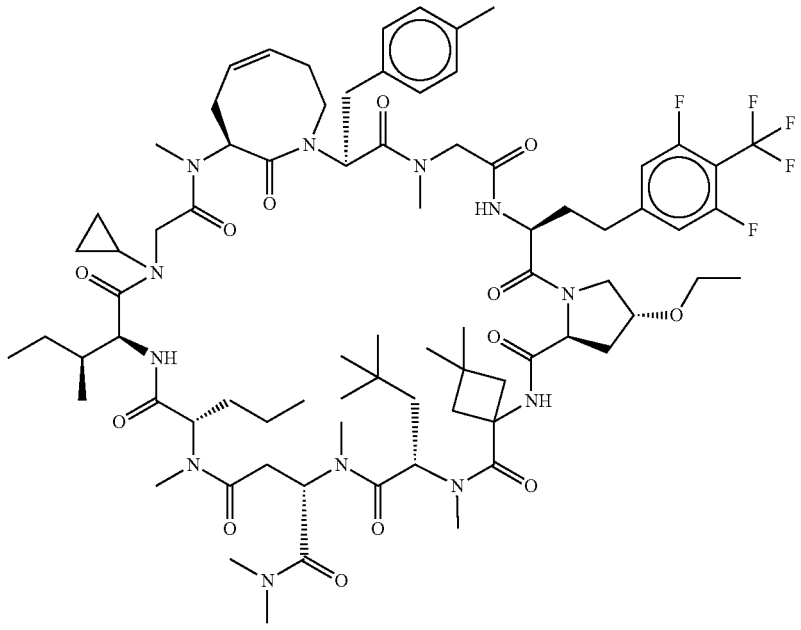 |

TABLE 38-continued

| Compound No. | Structural Formula |
|---|---|
| PP2720 | |
| PP2722 | |

TABLE 38-continued
| Compound No. | Structural Formula |
|---|---|
| PP2724 | 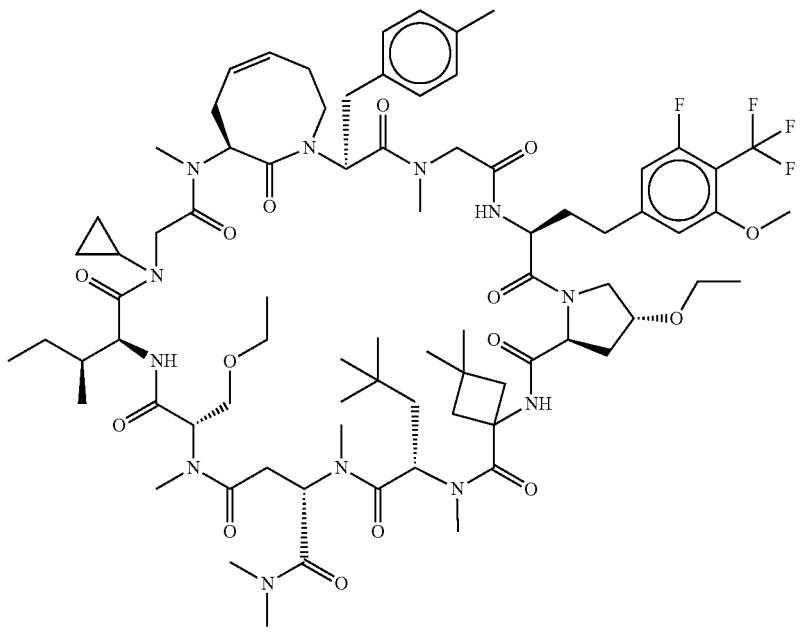 |
| PP2726 | 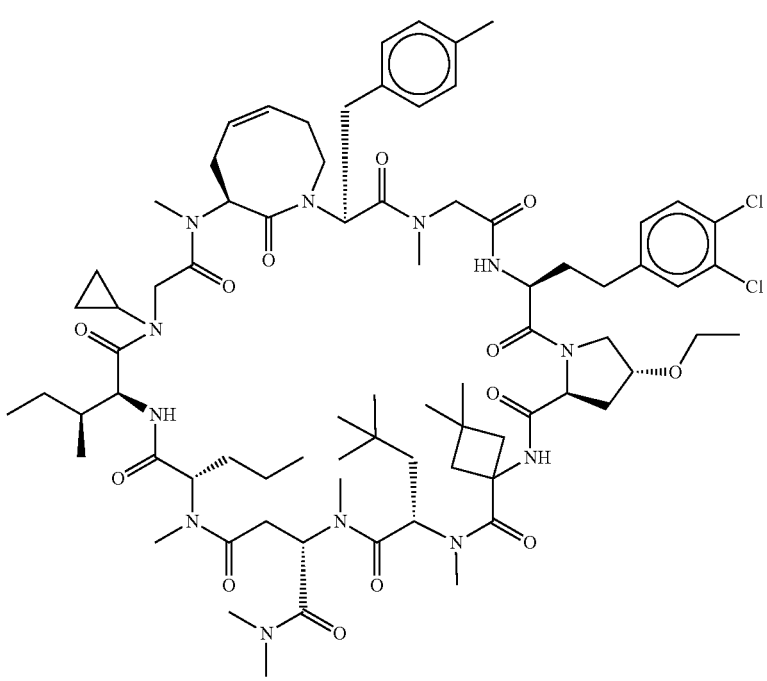 |

TABLE 38-continued
| Compound No. | Structural Formula |
| --- | --- |
| PP2728 | 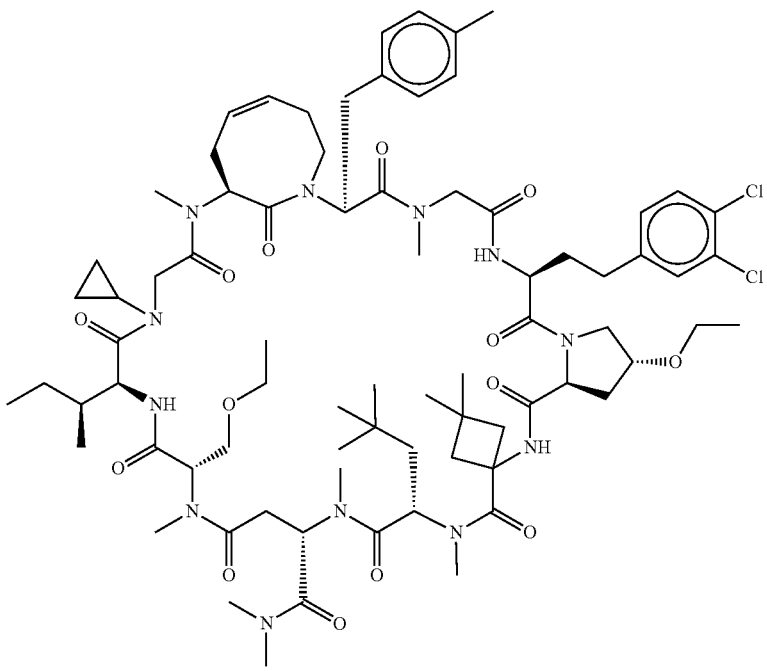 |
| PP2730 | 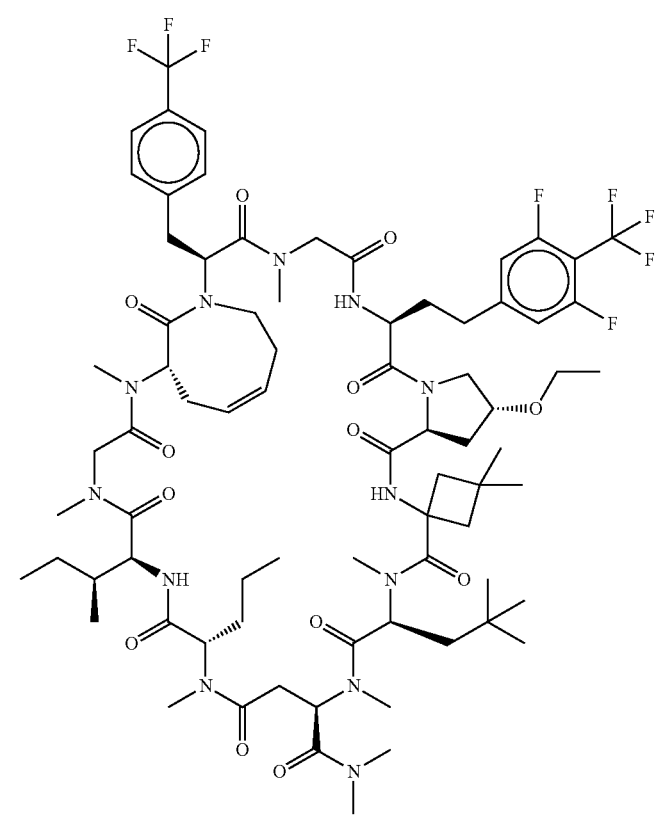 |

TABLE 38-continued
| Compound No. | Structural Formula |
|---|---|
| PP2732 | 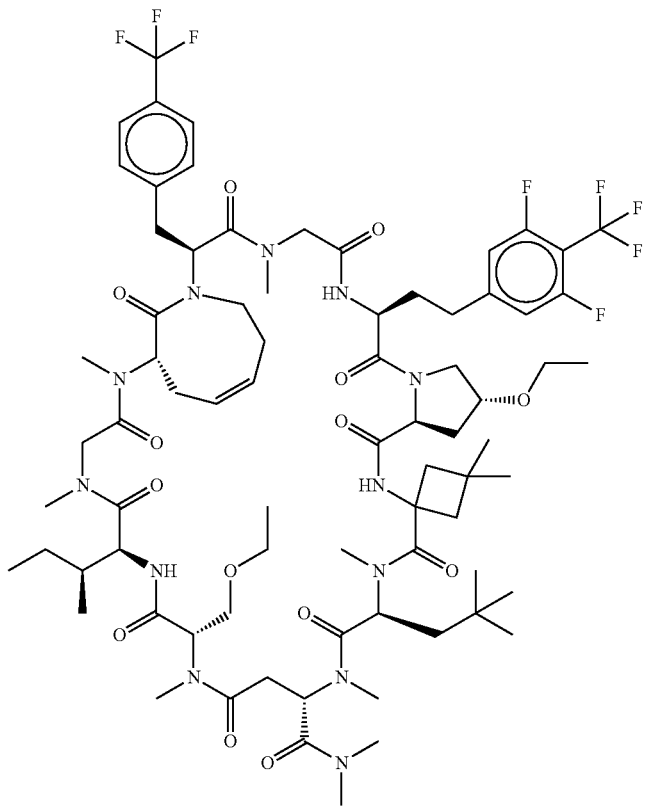 |
| PP2734 | 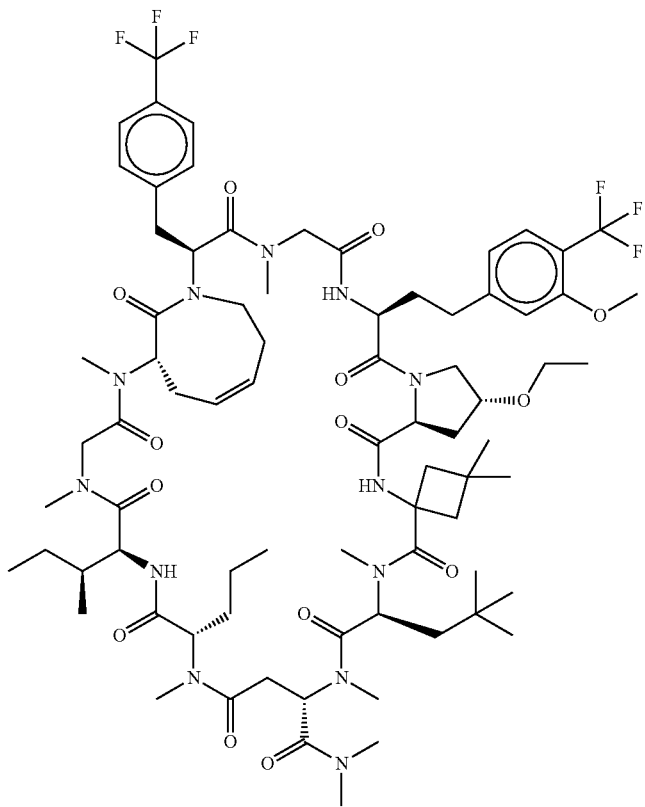 |

TABLE 38-continued
| Compound No. | Structural Formula |
|---|---|
| PP2736 | 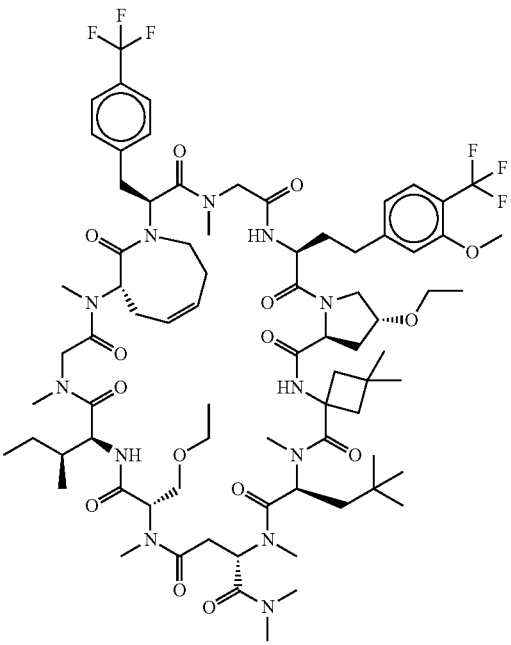 |
| PP2738 | 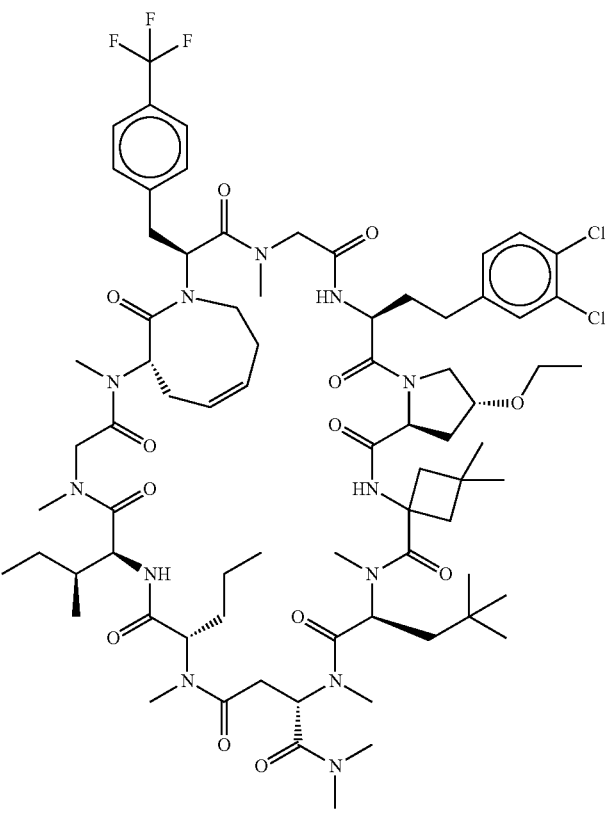 |

TABLE 38-continued
| Compound No. | Structural Formula |
|---|---|
| PP2740 | 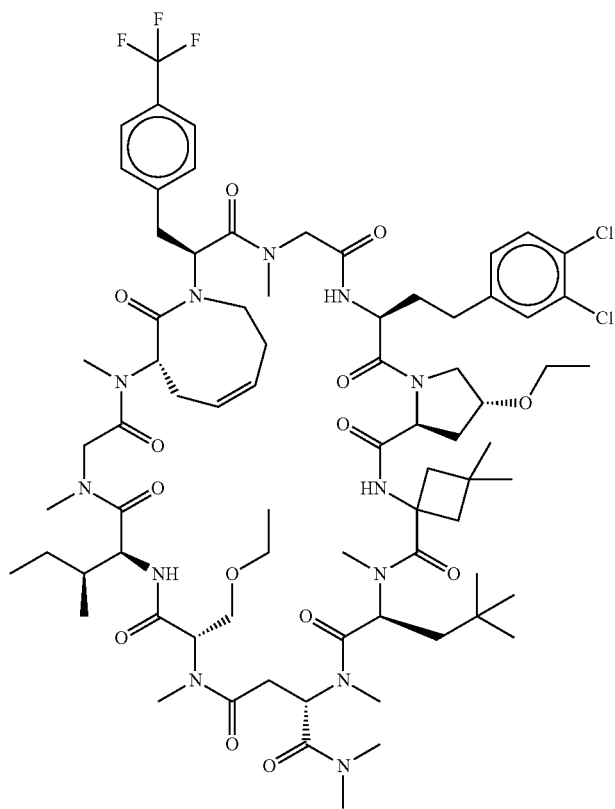 |
| PP2742 | 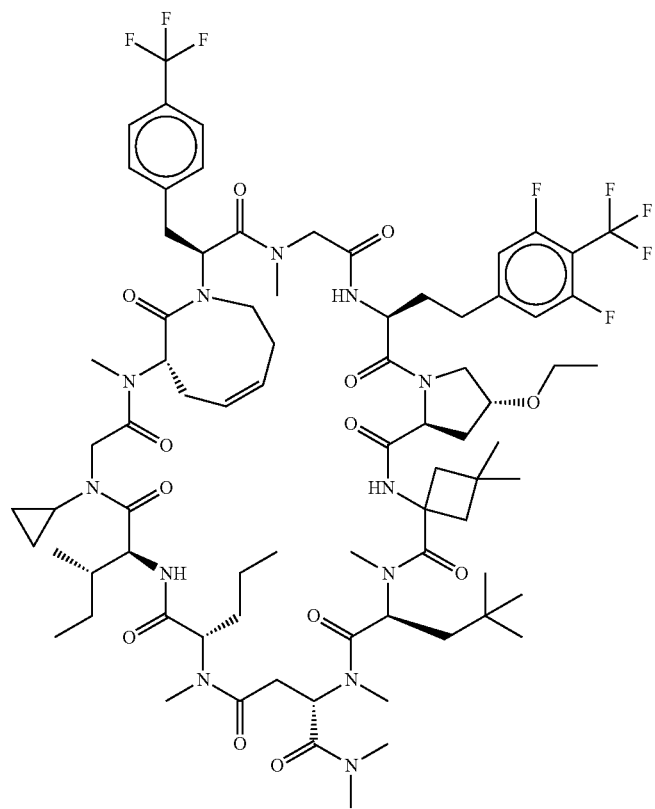 |

TABLE 38-continued
| Compound No. | Structural Formula |
| --- | --- |
| PP2744 | 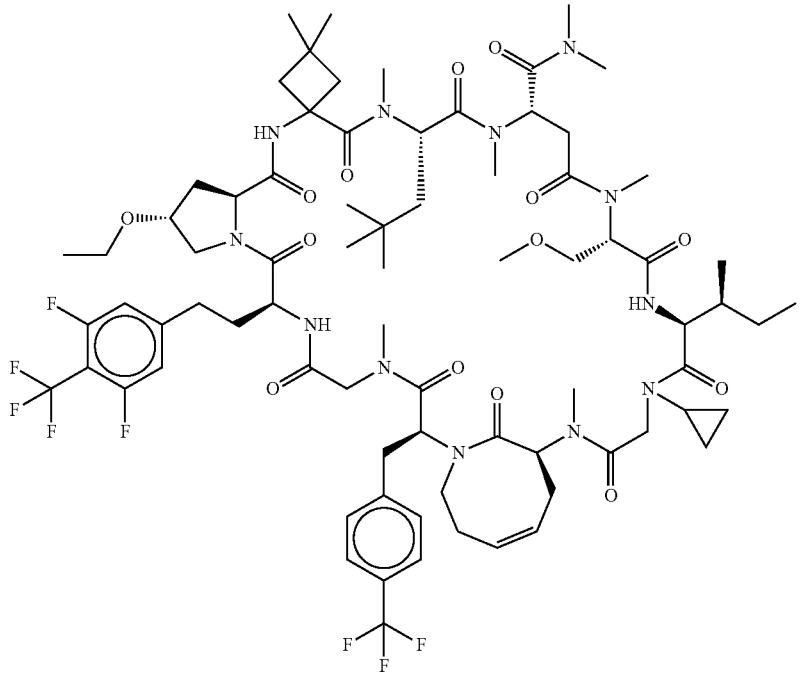 |
| PP2746 | 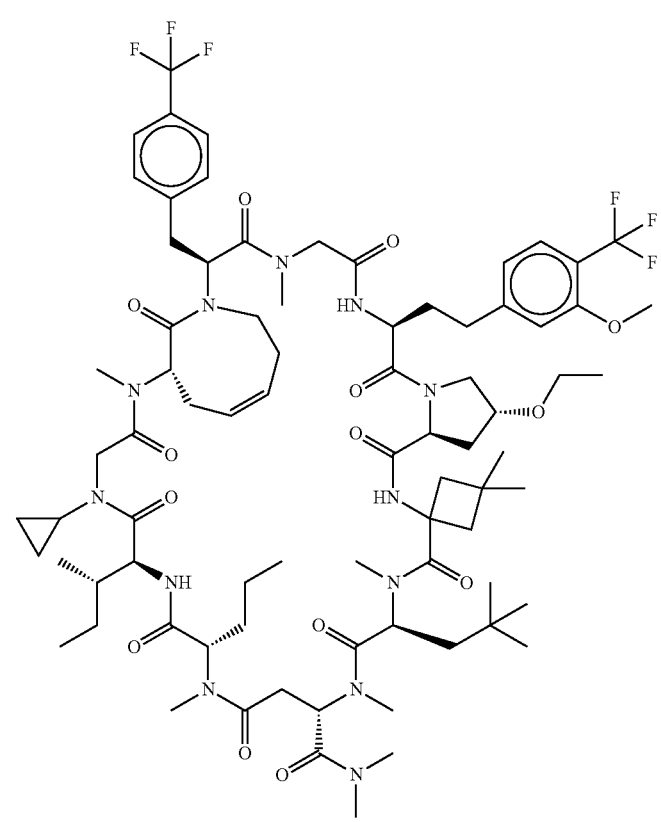 |

TABLE 38-continued

| Compound No. | Structural Formula |
| --- | --- |
| PP2748 | |
| PP2749 | |

TABLE 38-continued

| Compound No. | Structural Formula |
|---|---|
| PP2750 | |
| PP2751 | |

TABLE 38-continued

| Compound No. | Structural Formula |
|---|---|
| PP2752 | |
| PP2753 | |

TABLE 38-continued

| Compound No. | Structural Formula |
|---|---|
| PP2754 | |
| PP2755 | |

TABLE 38-continued

| Compound No. | Structural Formula |
|---|---|
| PP2756 | |
| PP2757 | |

TABLE 38-continued
| Compound No. | Structural Formula |
|---|---|
| PP2758 | 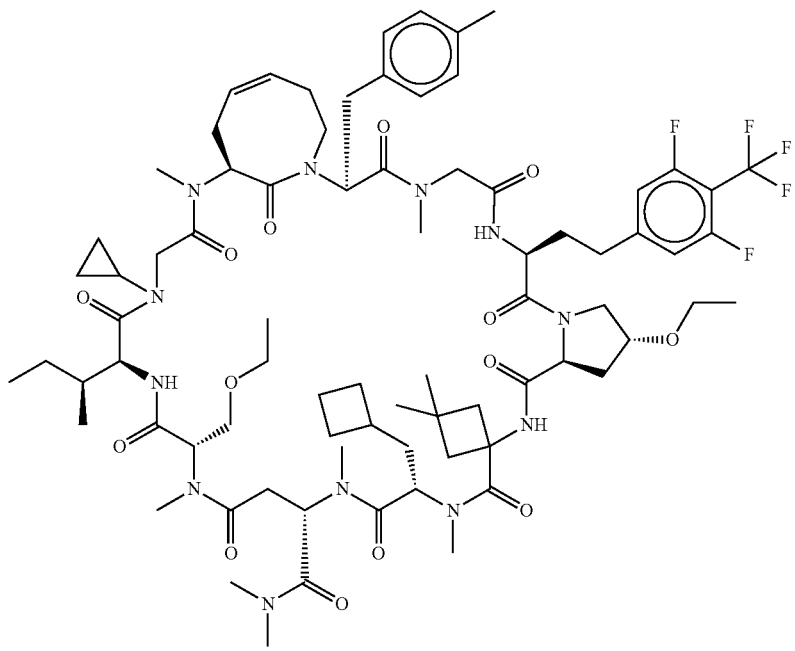 |
| PP2759 | 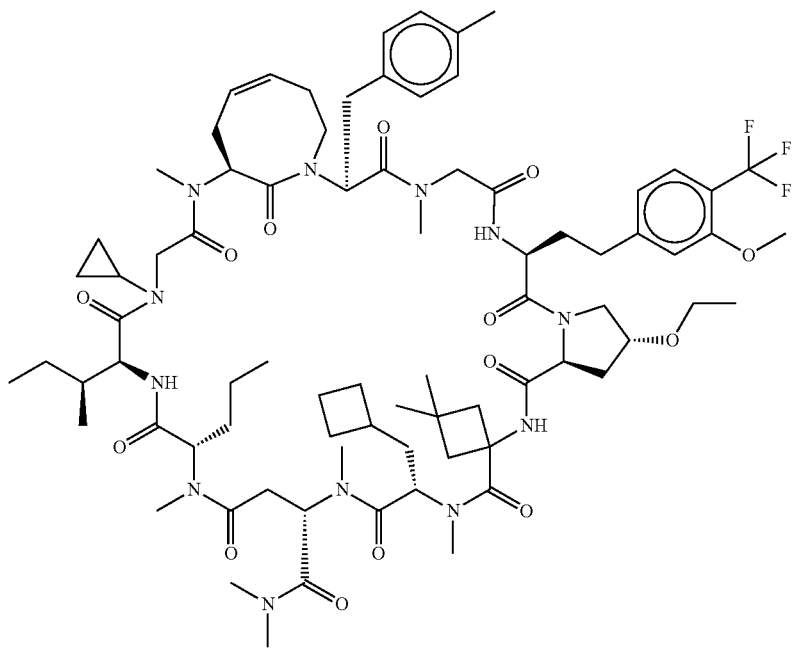 |

TABLE 38-continued
| Compound No. | Structural Formula |
|---|---|
| PP2760 | 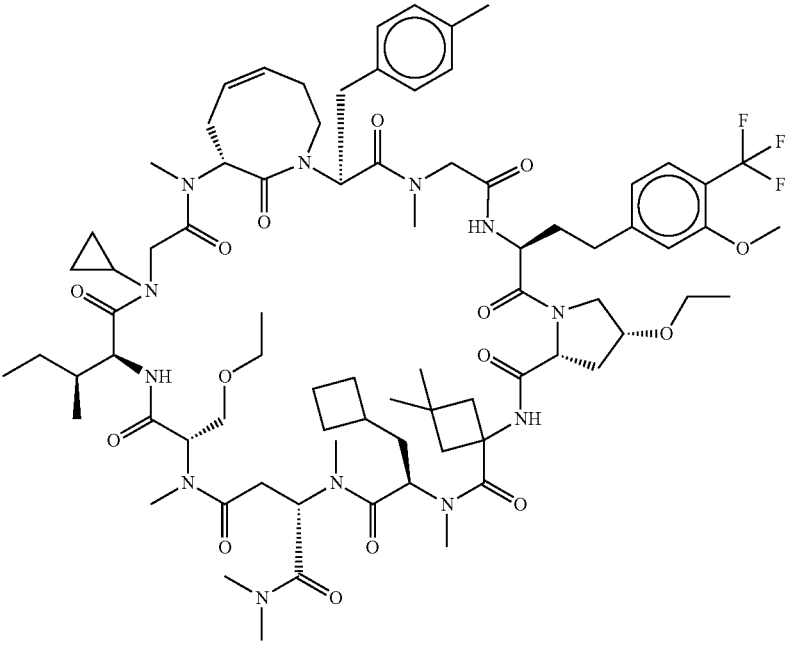 |
| PP2761 | 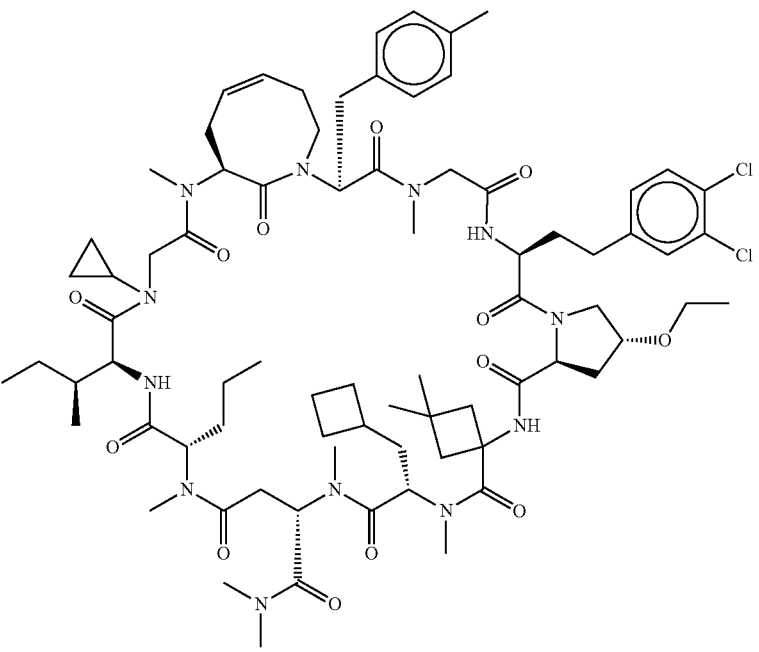 |

TABLE 38-continued
| Compound No. | Structural Formula |
|---|---|
| PP2762 | 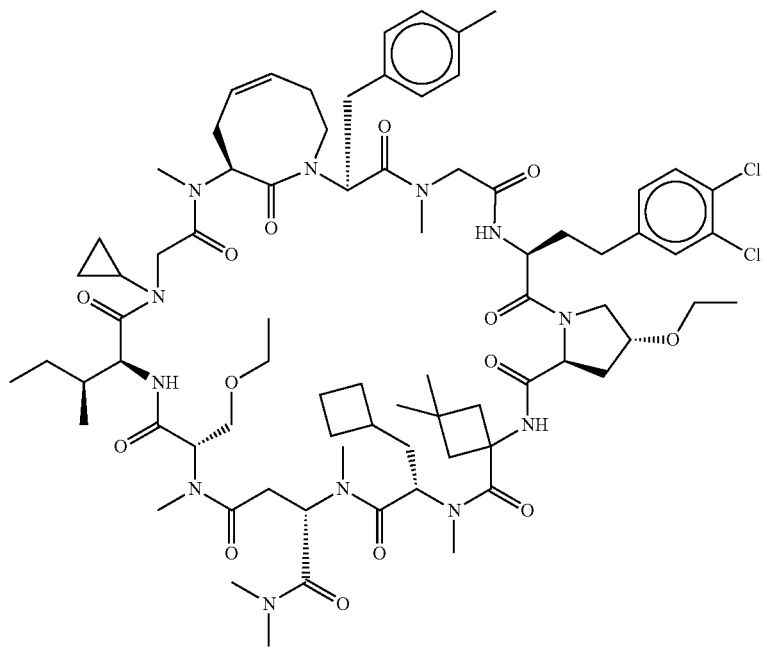 |
| PP2763 | 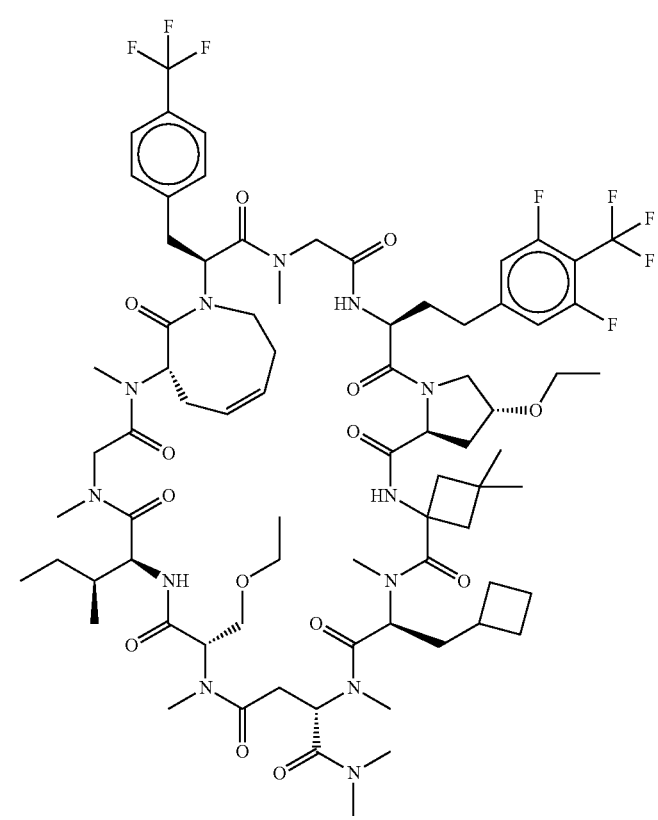 |

TABLE 38-continued
| Compound No. | Structural Formula |
|---|---|
| PP2764 | 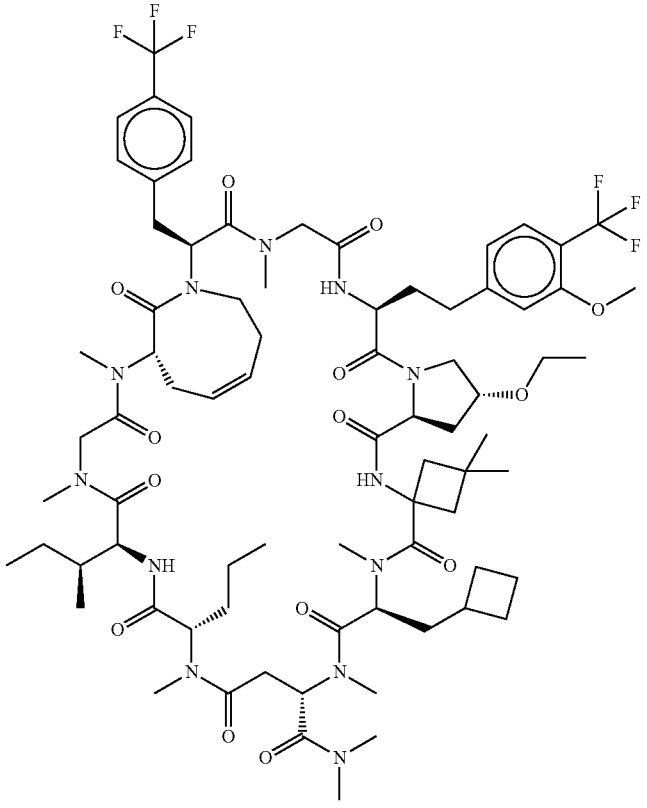 |
| PP2765 | 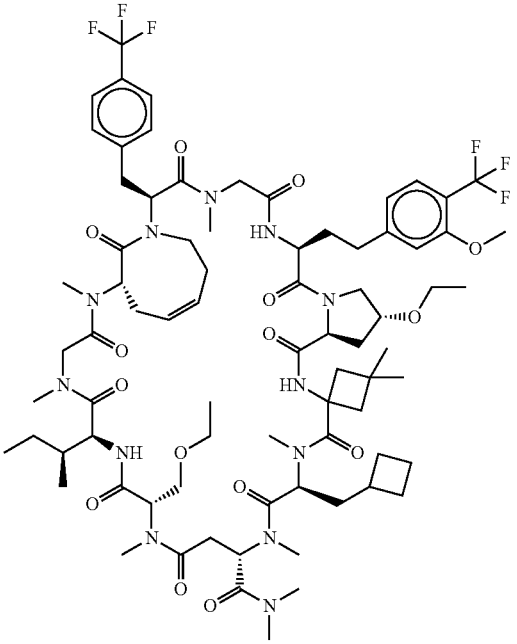 |

TABLE 38-continued
| Compound No. | Structural Formula |
|---|---|
| PP2766 | 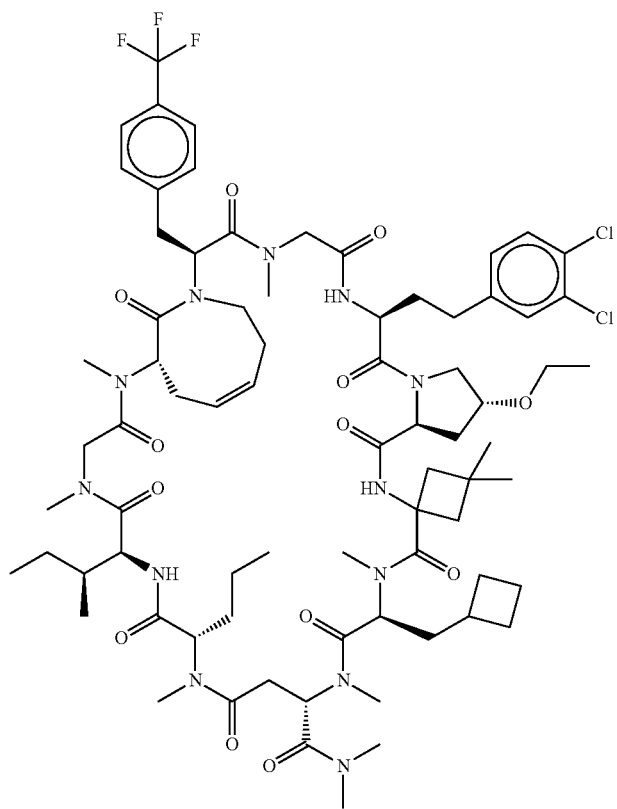 |
| PP2767 | 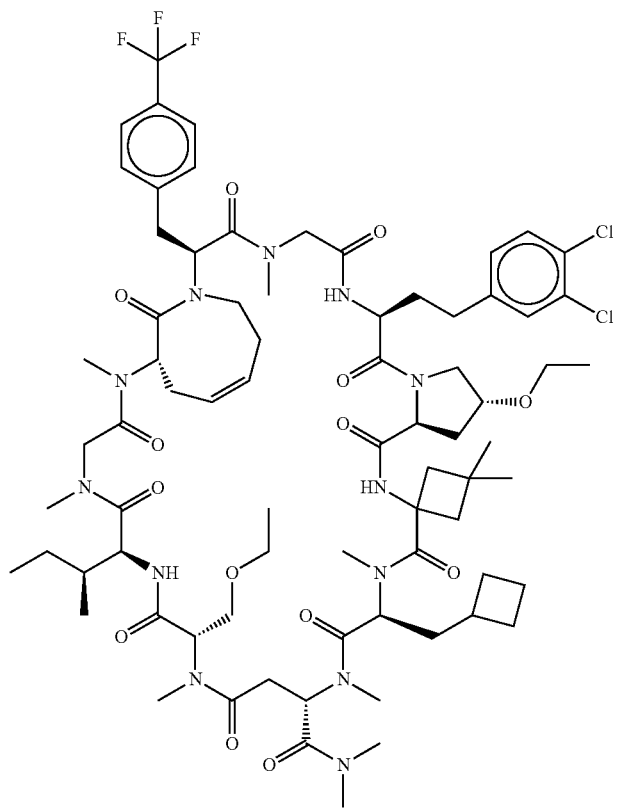 |

TABLE 38-continued

| Compound No. | Structural Formula |
| --- | --- |
| PP2768 | |
| PP2769 | |

TABLE 38-continued

| Compound No. | Structural Formula |
| --- | --- |
| PP2770 | |
| PP2771 | |

TABLE 38-continued
| Compound No. | Structural Formula |
|---|---|
| PP2772 | 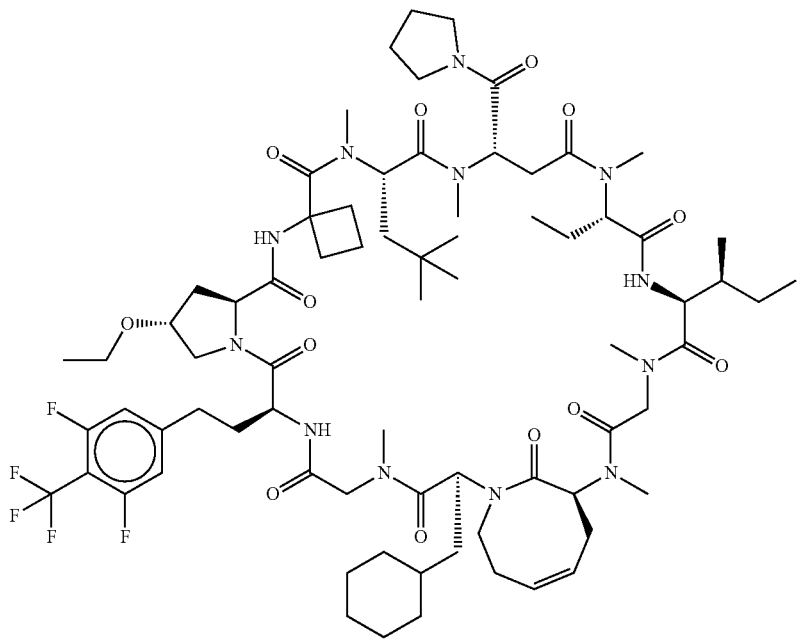 |
| PP2773 | 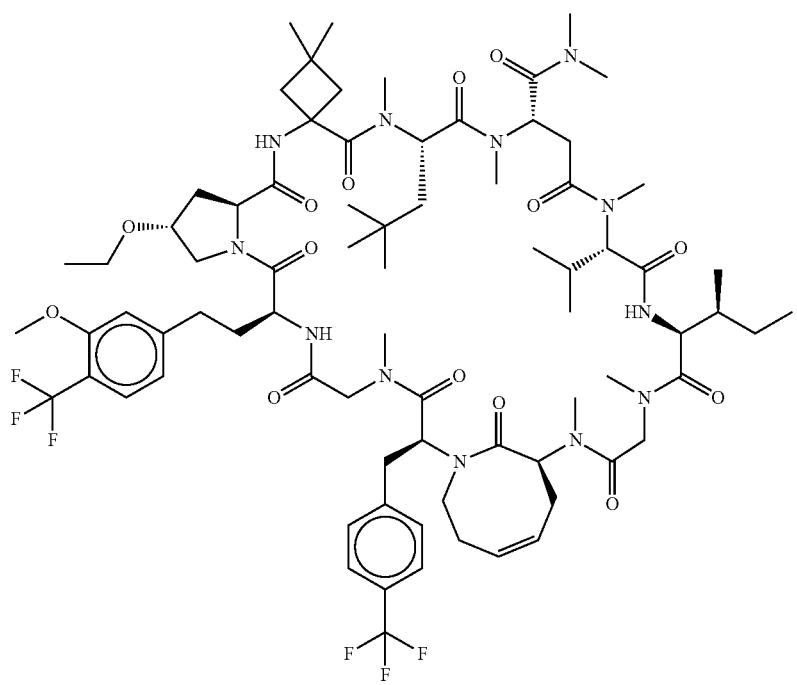 |

TABLE 38-continued
| Compound No. | Structural Formula |
| --- | --- |
| PP2776 | 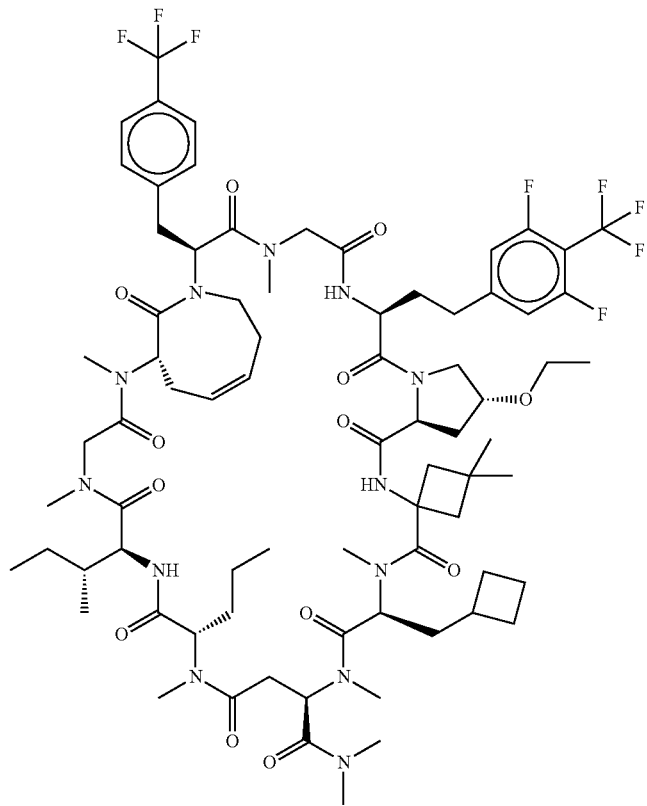 |
| PP2777 | 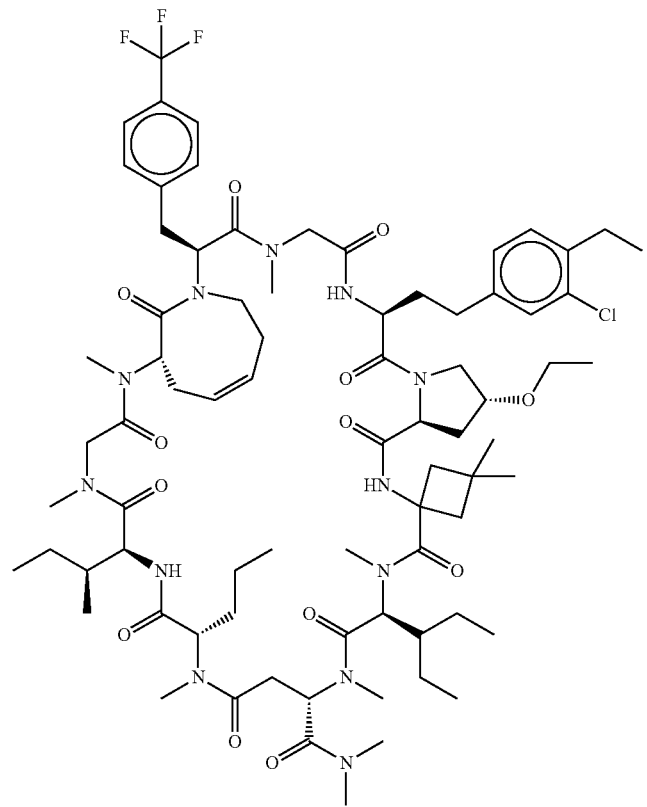 |

TABLE 38-continued

| Compound No. | Structural Formula |
|---|---|
| PP2778 | |
| PP2779 | |

TABLE 38-continued
| Compound No. | Structural Formula |
|---|---|
| PP2780 | 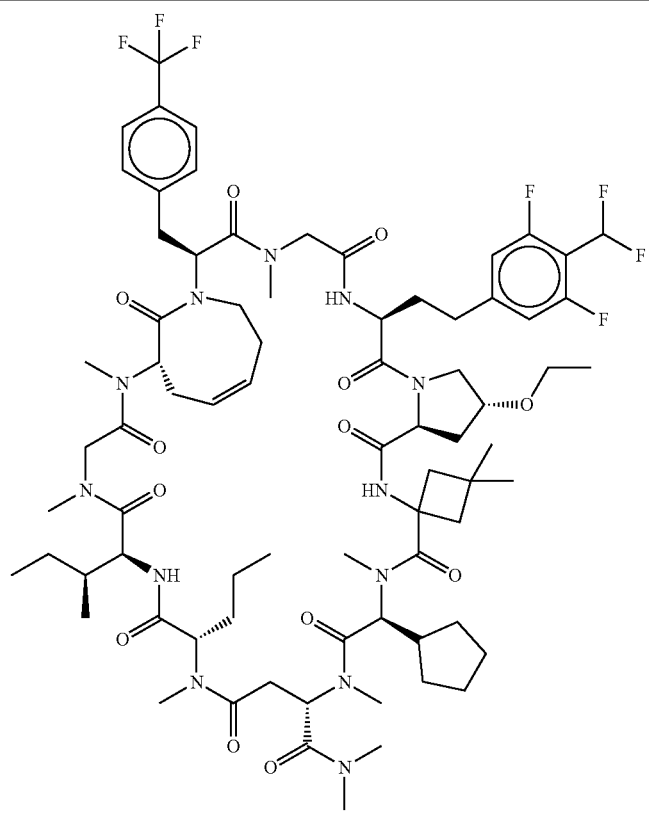 |
| PP2781 | 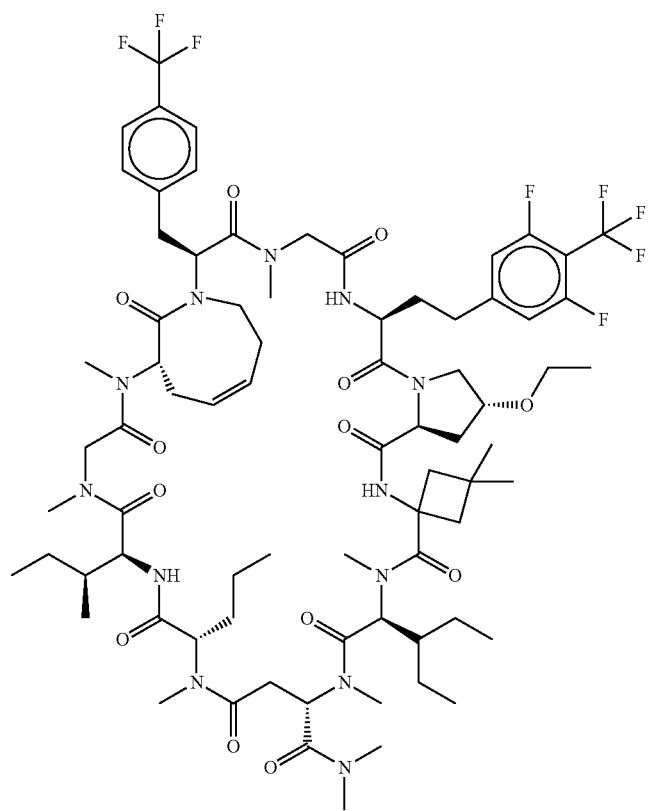 |

TABLE 38-continued

| Compound No. | Structural Formula |
|---|---|

PP2782

PP2783

TABLE 38-continued

| Compound No. | Structural Formula |
|---|---|
| PP2784 | |
| PP2785 | |

TABLE 38-continued
| Compound No. | Structural Formula |
|---|---|
| PP2786 | 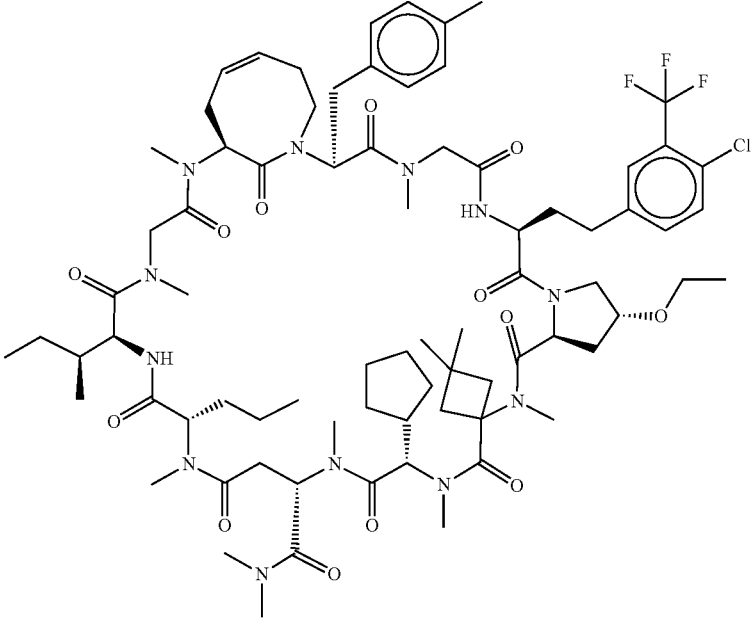 |
| PP2787 | 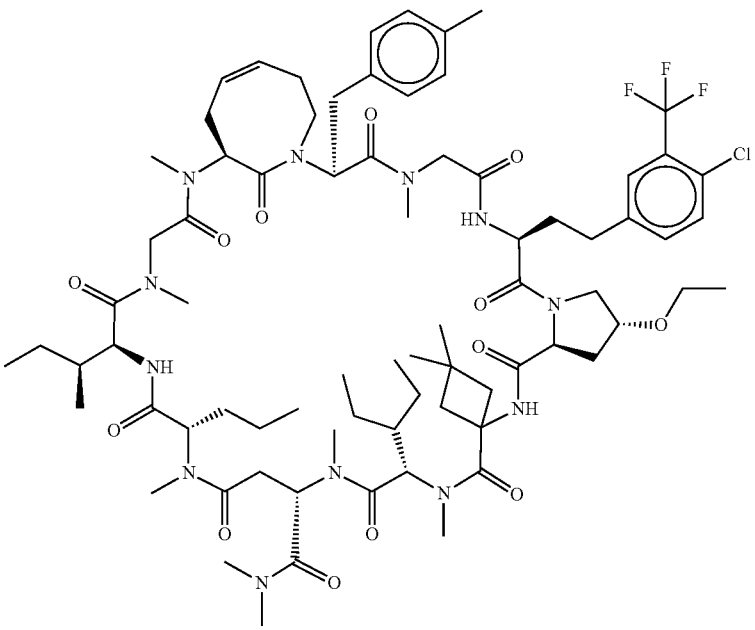 |

TABLE 38-continued

| Compound No. | Structural Formula |
|---|---|
| PP2788 | |
| PP2789 | |

TABLE 38-continued
| Compound No. | Structural Formula |
|---|---|
| PP2790 | 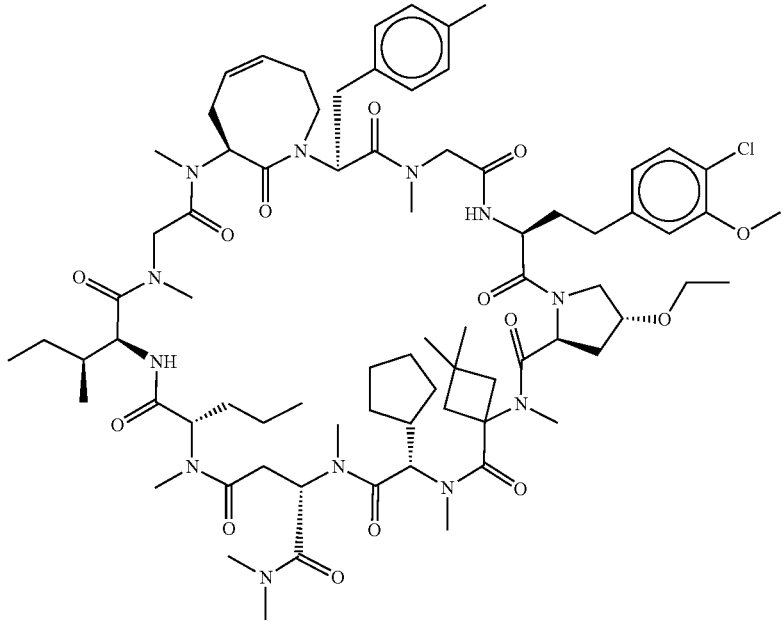 |
| PP2791 | 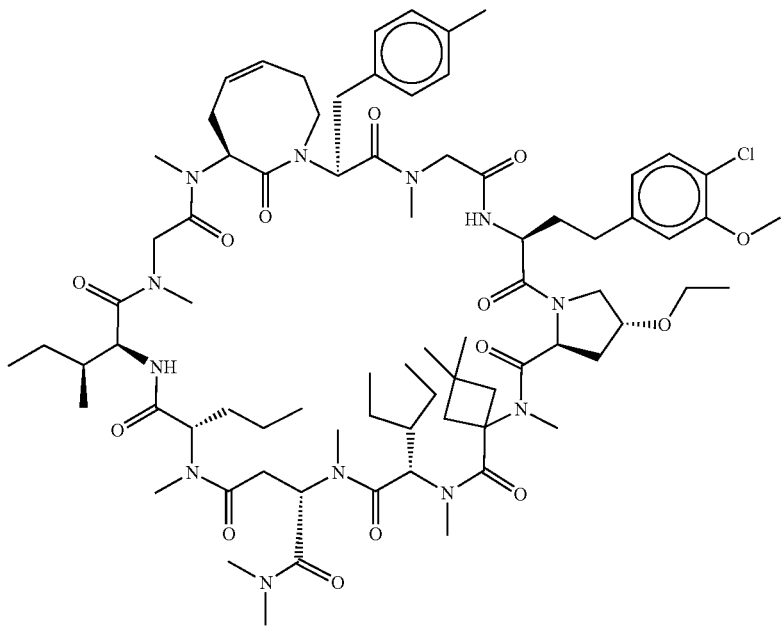 |

TABLE 38-continued

| Compound No. | Structural Formula |
|---|---|
| PP2796 | |
| PP2797 | |

TABLE 38-continued

| Compound No. | Structural Formula |
|---|---|
| PP2798 | |
| PP2799 | |

TABLE 38-continued

| Compound No. | Structural Formula |
|---|---|
| PP2800 | |
| PP2801 | |

TABLE 38-continued

| Compound No. | Structural Formula |
|---|---|
| PP2802 | |
| PP2803 | |

TABLE 38-continued

| Compound No. | Structural Formula |
|---|---|
| PP2804 | |
| PP2805 | |

TABLE 38-continued

| Compound No. | Structural Formula |
|---|---|
| PP2806 | |
| PP2807 | |

TABLE 38-continued

| Compound No. | Structural Formula |
|---|---|
| PP2808 | |
| PP2809 | |

TABLE 38-continued
| Compound No. | Structural Formula |
|---|---|
| PP2810 | 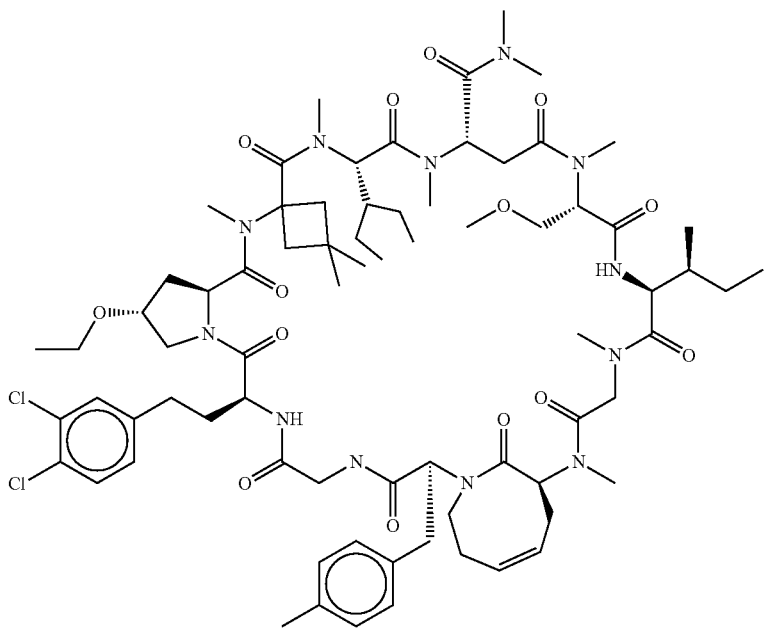 |
| PP2811 | 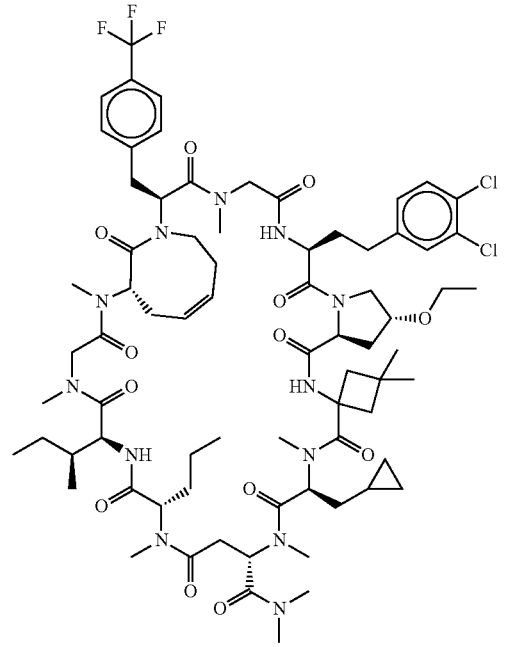 |

TABLE 38-continued

| Compound No. | Structural Formula |
|---|---|
| PP2812 | |
| PP2813 | |

TABLE 38-continued

| Compound No. | Structural Formula |
|---|---|
| PP2814 | |
| PP2815 | |

TABLE 38-continued

| Compound No. | Structural Formula |
|---|---|
| PP2816 | |
| PP2817 | |

TABLE 38-continued

| Compound No. | Structural Formula |
|---|---|
| PP2818 | |
| PP2819 | |

TABLE 38-continued

| Compound No. | Structural Formula |
|---|---|
| PP2820 | |
| PP2821 | |

TABLE 38-continued

| Compound No. | Structural Formula |
|---|---|
| PP2822 | |
| PP2823 | |

TABLE 38-continued
| Compound No. | Structural Formula |
|---|---|
| PP2824 | 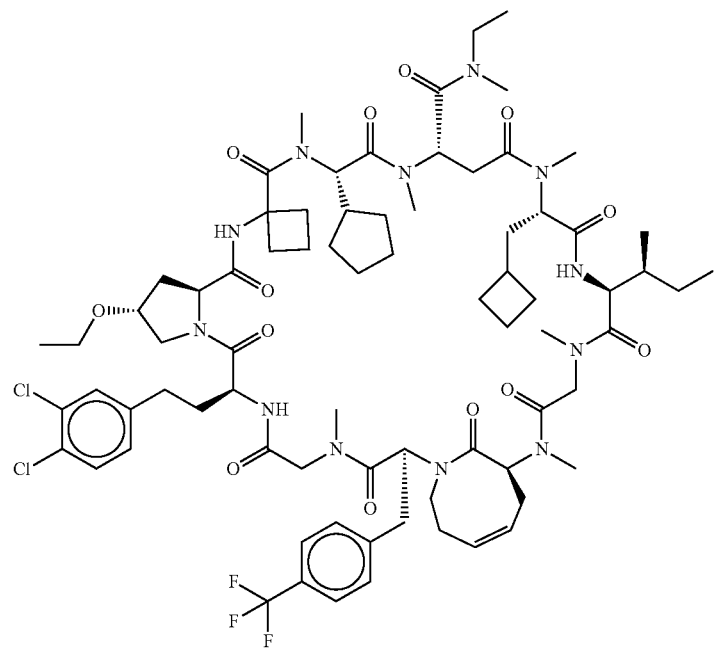 |
| PP2825 | 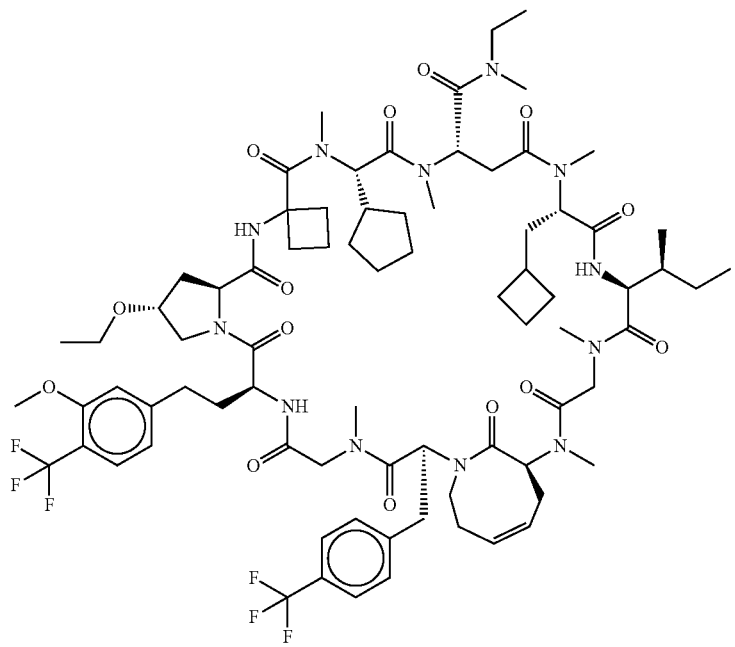 |

TABLE 38-continued

| Compound No. | Structural Formula |
|---|---|
| PP2826 | |
| PP2827 | |

TABLE 38-continued
| Compound No. | Structural Formula |
| --- | --- |
| PP2828 | 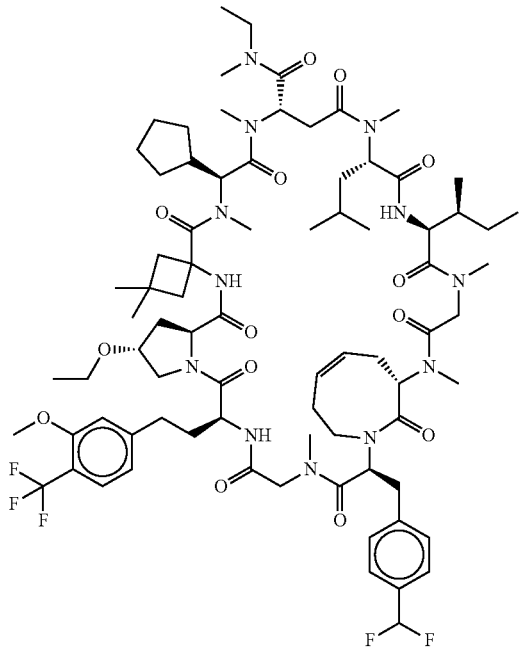 |
| PP2829 | 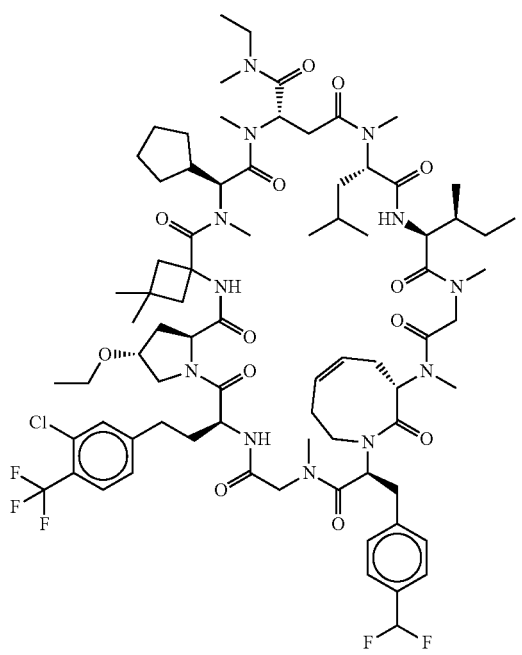 |

TABLE 38-continued
| Compound No. | Structural Formula |
|---|---|
| PP2830 | 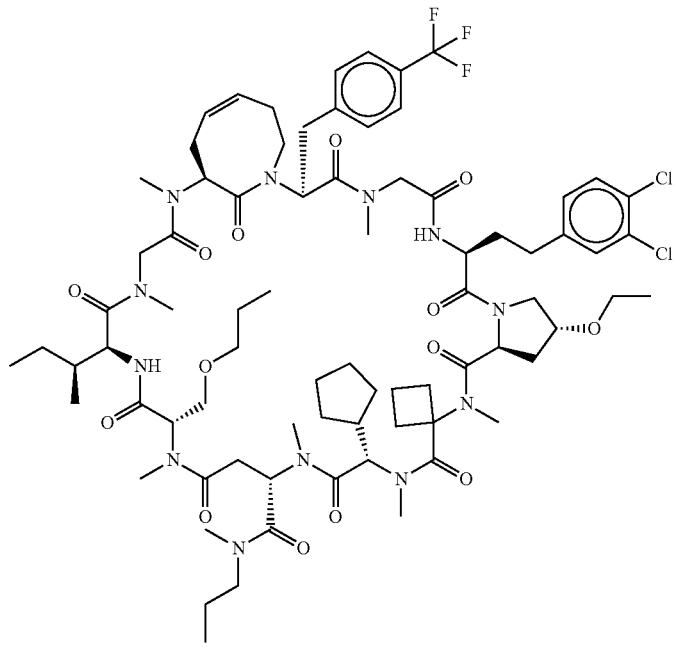 |
| PP2831 | 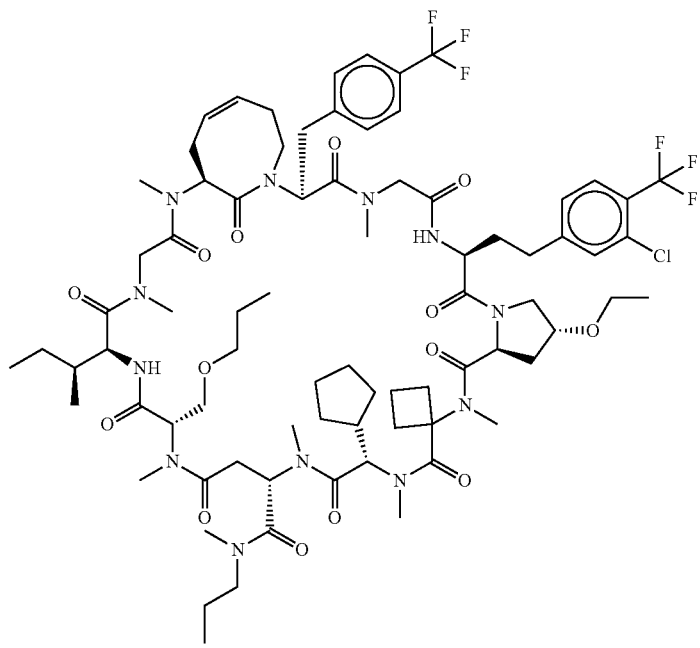 |

TABLE 38-continued
| Compound No. | Structural Formula |
|---|---|
| PP2832 | 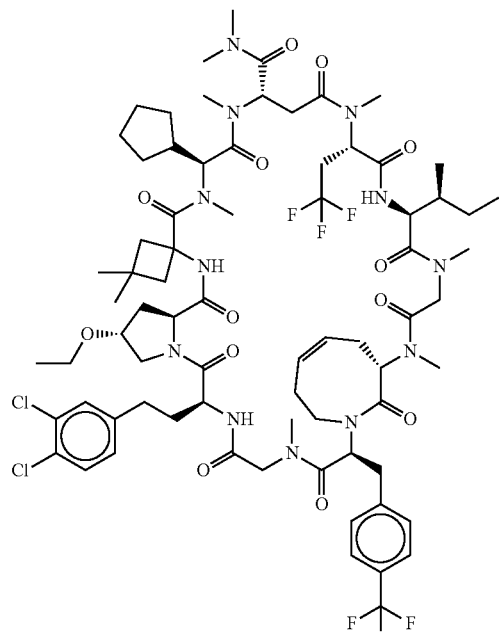 |
| PP2833 | 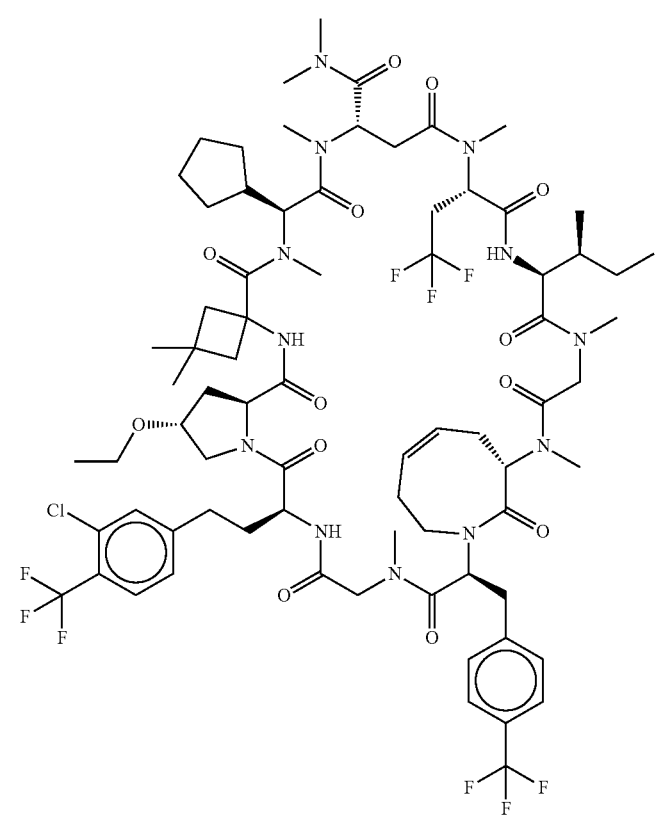 |

TABLE 38-continued

| Compound No. | Structural Formula |
| --- | --- |
| PP2834 | |
| PP2835 | |

TABLE 38-continued
| Compound No. | Structural Formula |
|---|---|
| PP2836 | 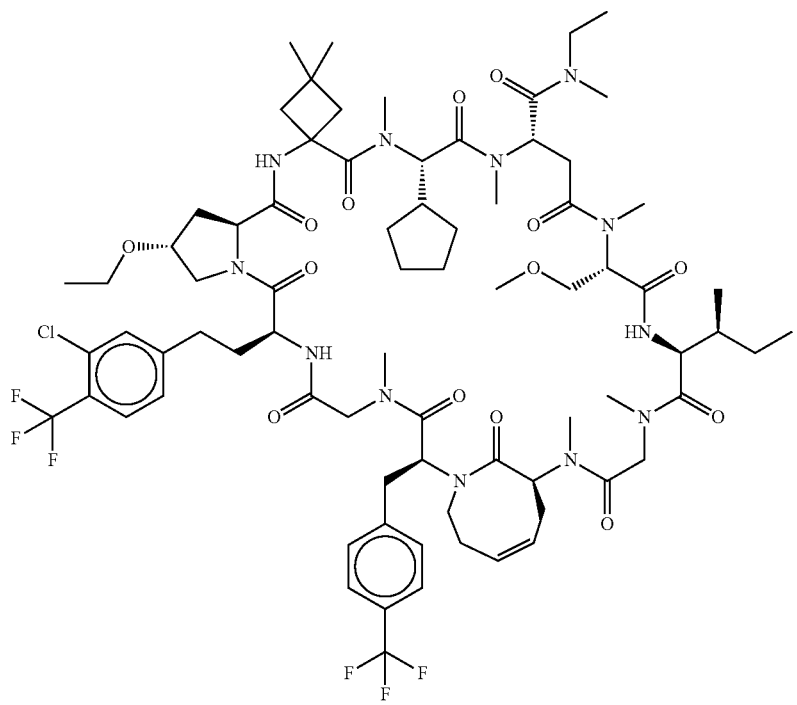 |
| PP2837 | 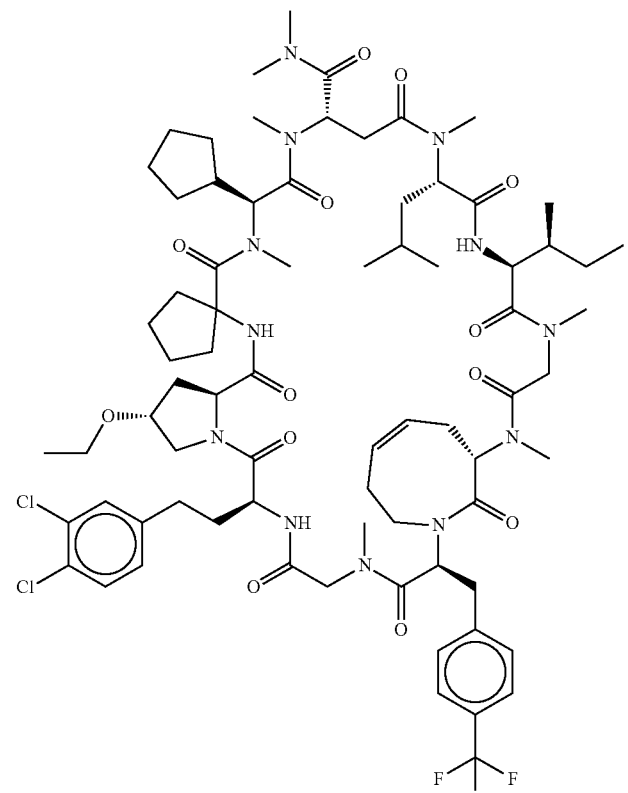 |

//
TABLE 38-continued
| Compound No. | Structural Formula |
|---|---|
| PP2838 | 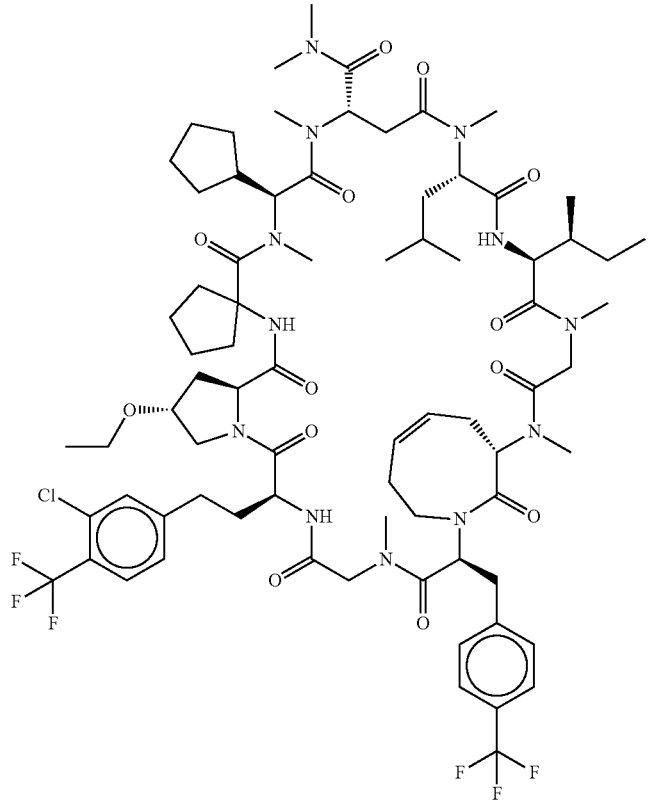 |
| PP2839 | 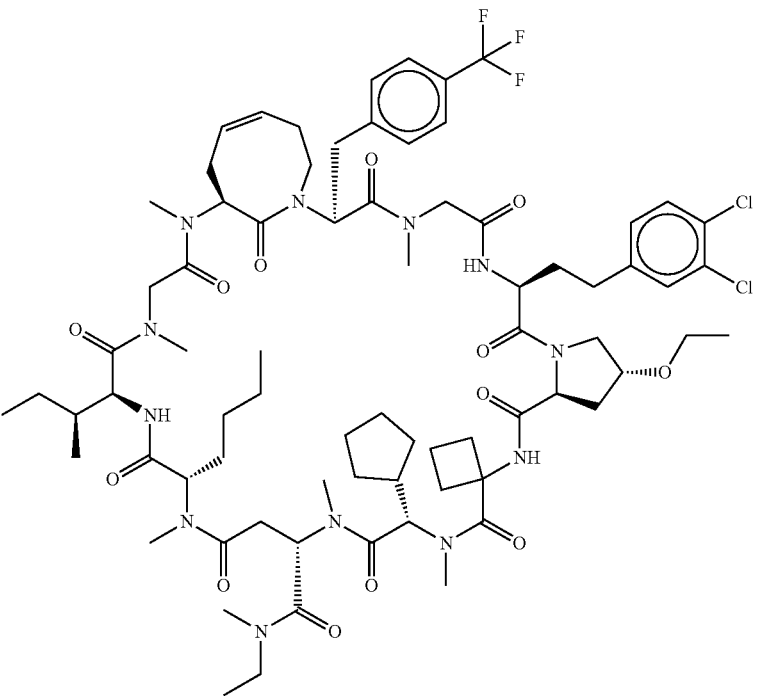 |

TABLE 38-continued

| Compound No. | Structural Formula |
|---|---|
| PP2840 | |
| PP2841 | |

TABLE 38-continued
| Compound No. | Structural Formula |
|---|---|
| PP2842 | 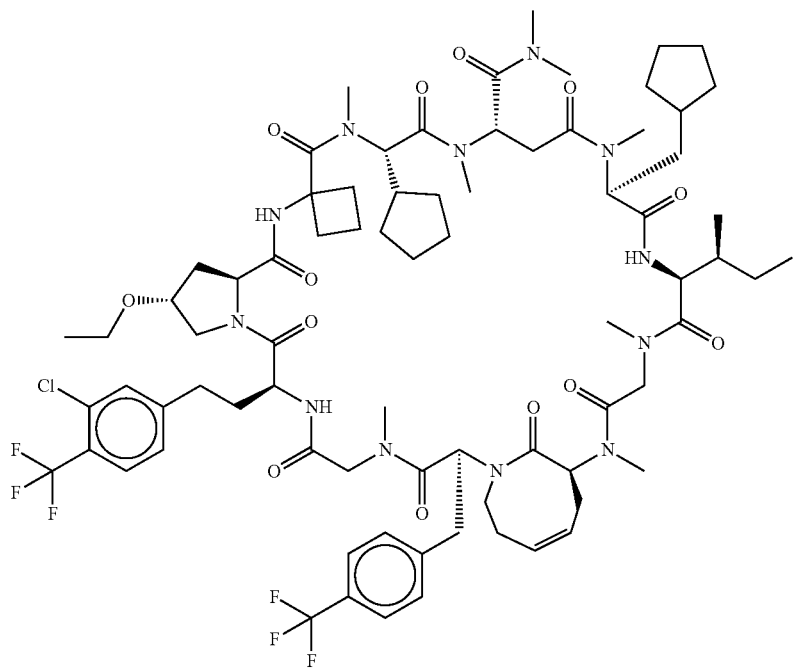 |
| PP2843 | 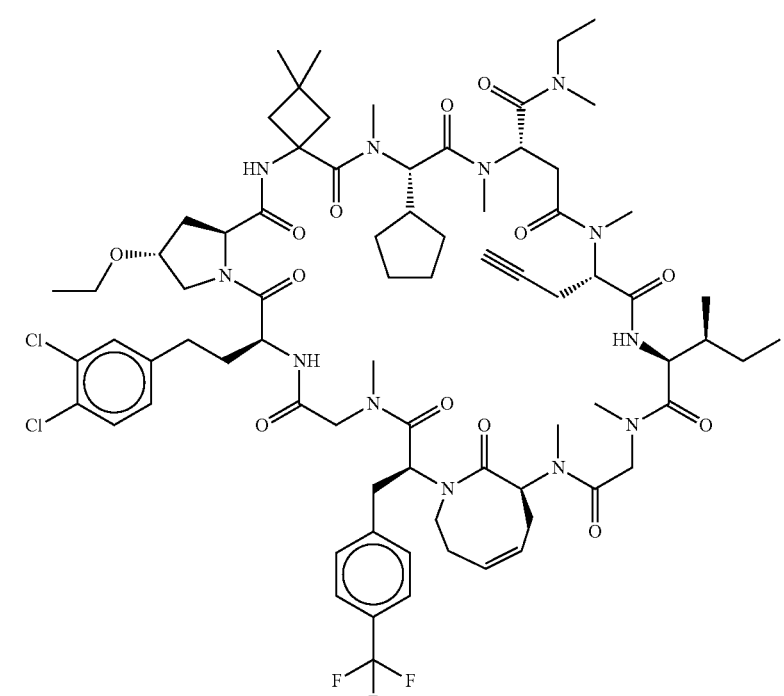 |

TABLE 38-continued
| Compound No. | Structural Formula |
| --- | --- |
| PP2844 | 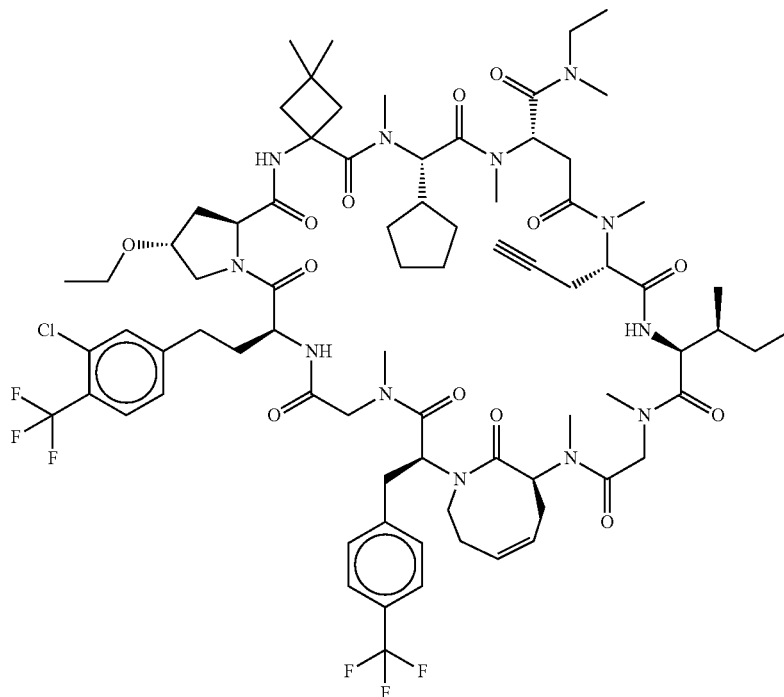 |
| PP2845 | 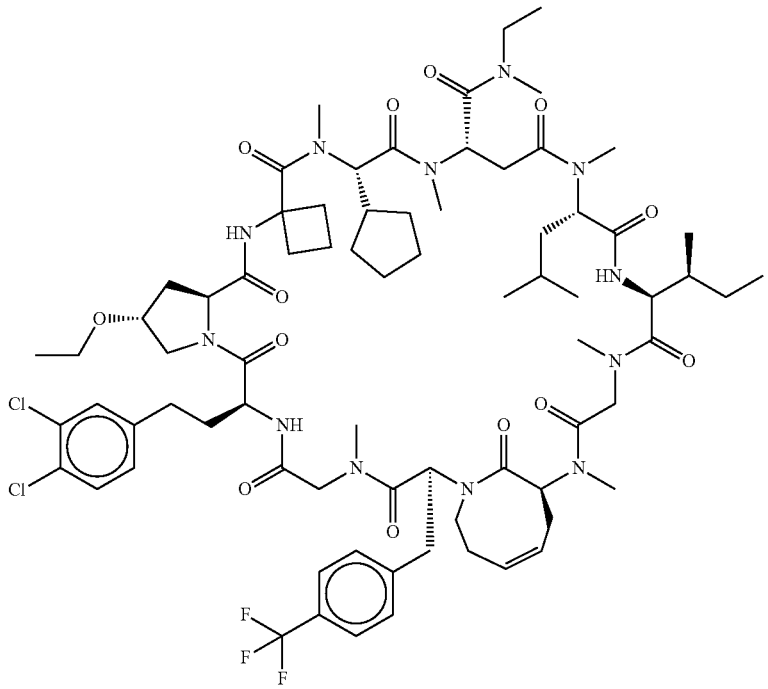 |

TABLE 38-continued
| Compound No. | Structural Formula |
|---|---|
| PP2846 | 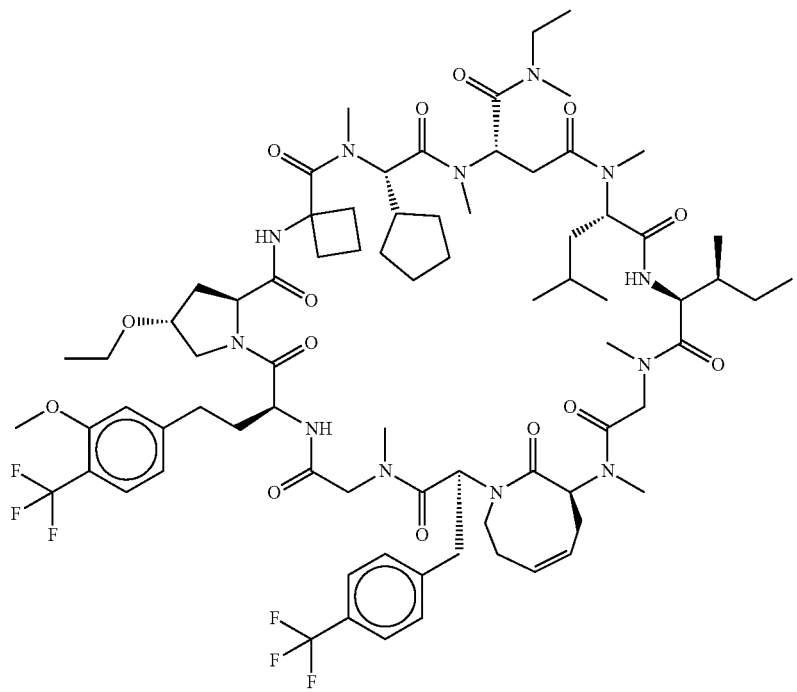 |
| PP2847 | 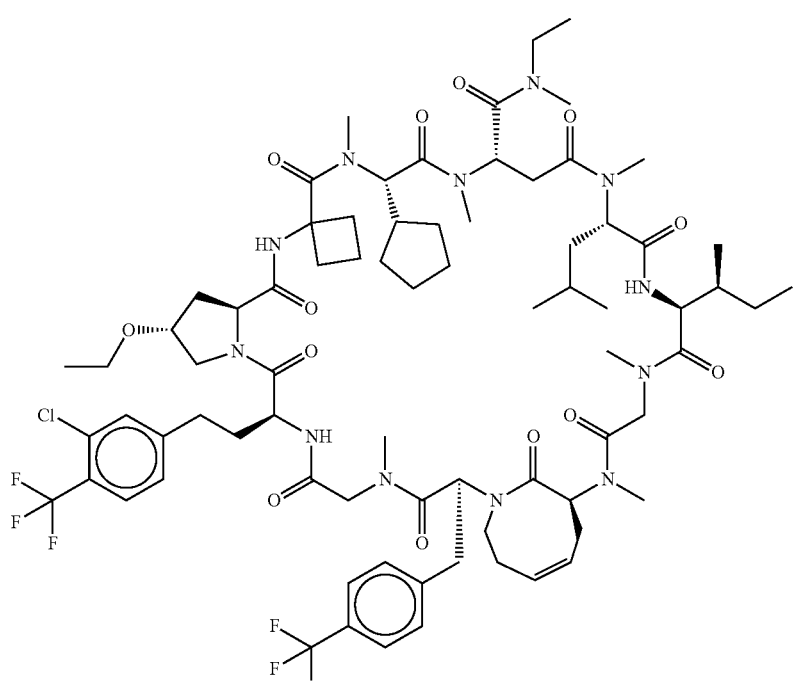 |

TABLE 38-continued
| Compound No. | Structural Formula |
|---|---|
| PP2848 | 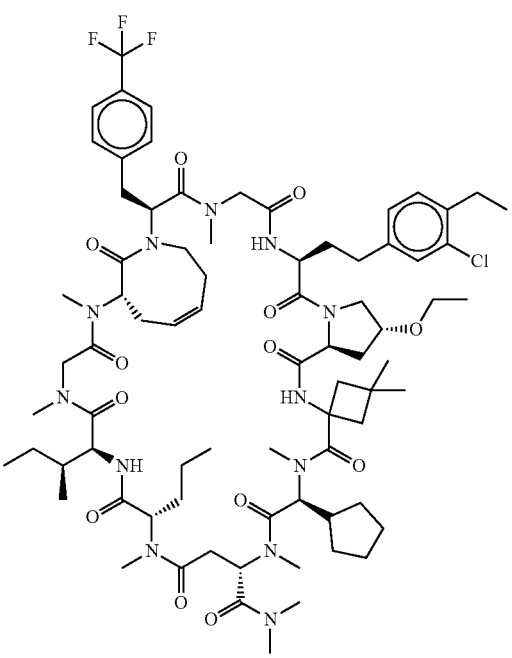 |
| PP2849 | 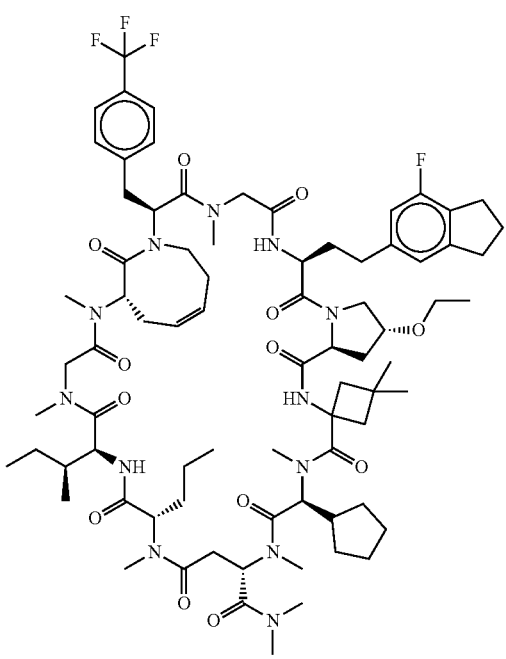 |

TABLE 38-continued

| Compound No. | Structural Formula |
|---|---|
| PP2850 | |
| PP2851 | |

TABLE 38-continued
| Compound No. | Structural Formula |
|---|---|
| PP2852 | 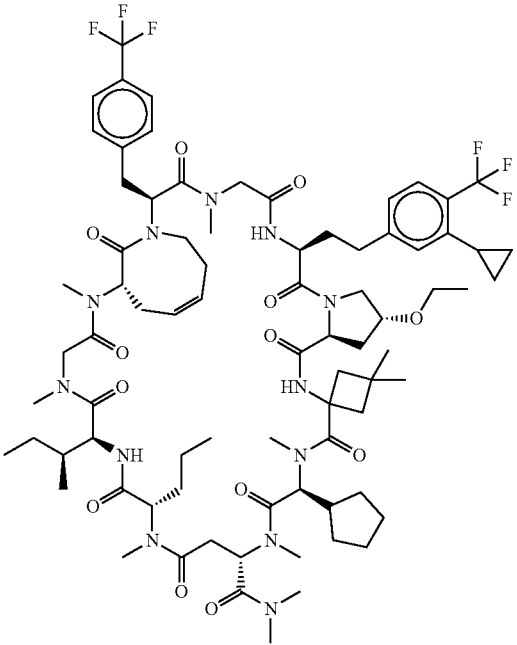 |
| PP2853 | 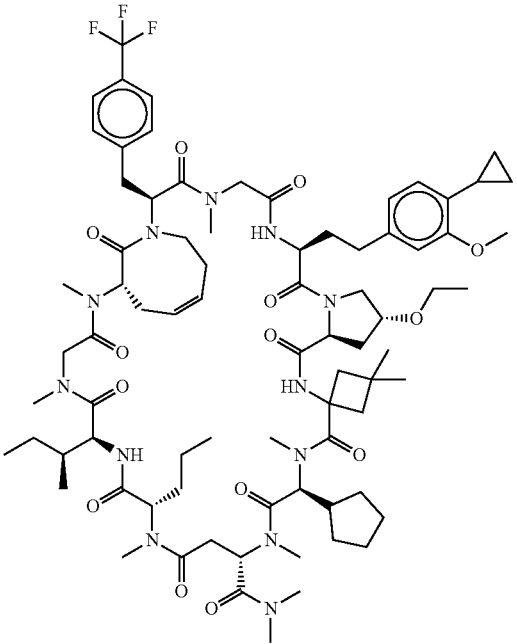 |

TABLE 38-continued

| Compound No. | Structural Formula |
|---|---|
| PP2854 | |
| PP2855 | |

TABLE 38-continued

| Compound No. | Structural Formula |
|---|---|
| PP2856 | |
| PP2857 | |

TABLE 38-continued
| Compound No. | Structural Formula |
|---|---|
| PP2858 | 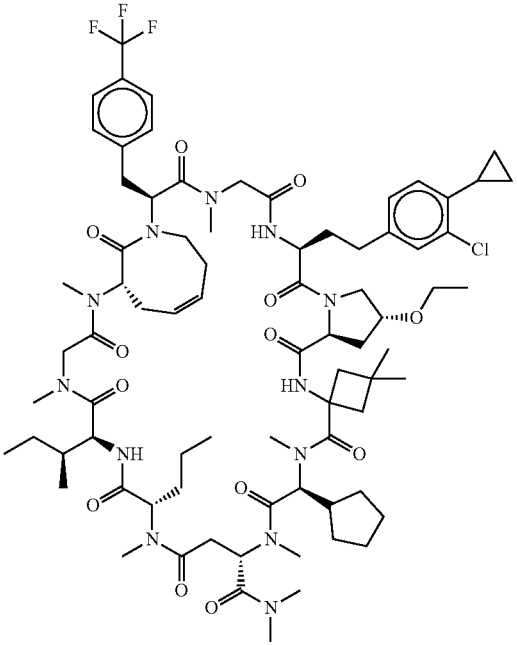 |
| PP2859 | 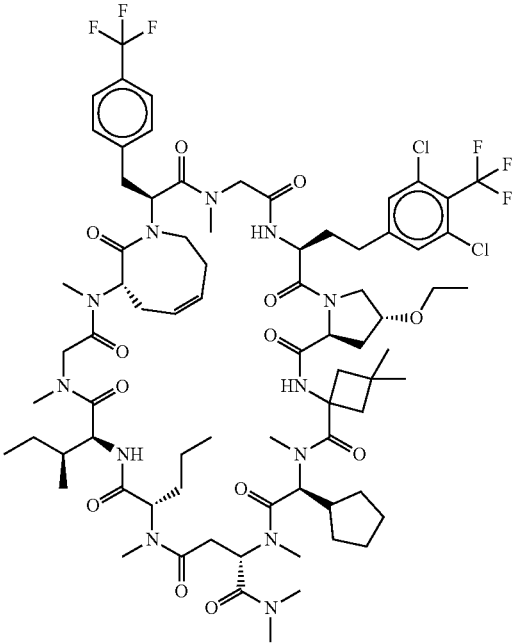 |

TABLE 38-continued
| Compound No. | Structural Formula |
|---|---|
| PP2860 | 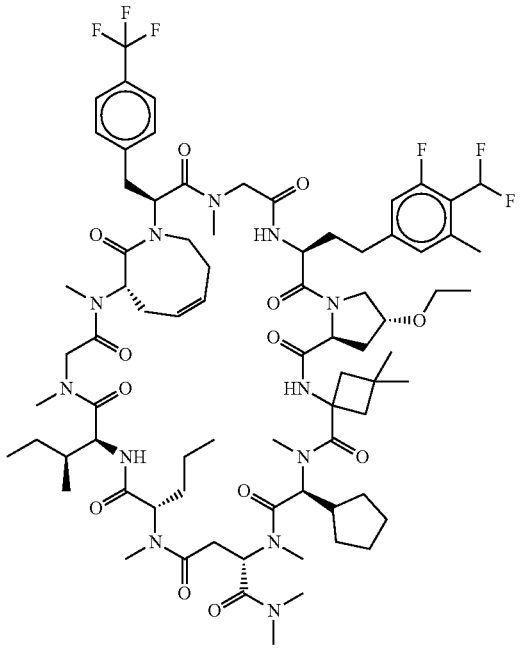 |
| PP2861 | 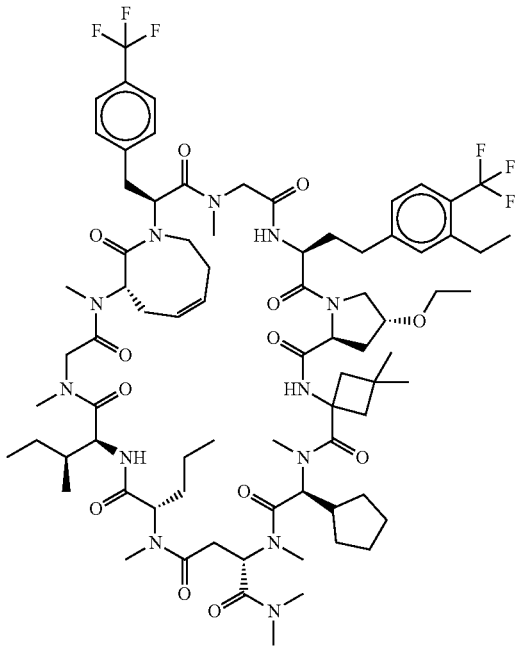 |

TABLE 38-continued

| Compound No. | Structural Formula |
|---|---|
| PP2862 | |
| PP2863 | |

TABLE 38-continued

| Compound No. | Structural Formula |
|---|---|
| PP2864 | |
| PP2865 | |

TABLE 38-continued

| Compound No. | Structural Formula |
|---|---|
| PP2866 | |
| PP2867 | |

TABLE 38-continued

| Compound No. | Structural Formula |
|---|---|
| PP2868 | |
| PP2869 | |

TABLE 38-continued
| Compound No. | Structural Formula |
|---|---|
| PP2870 | 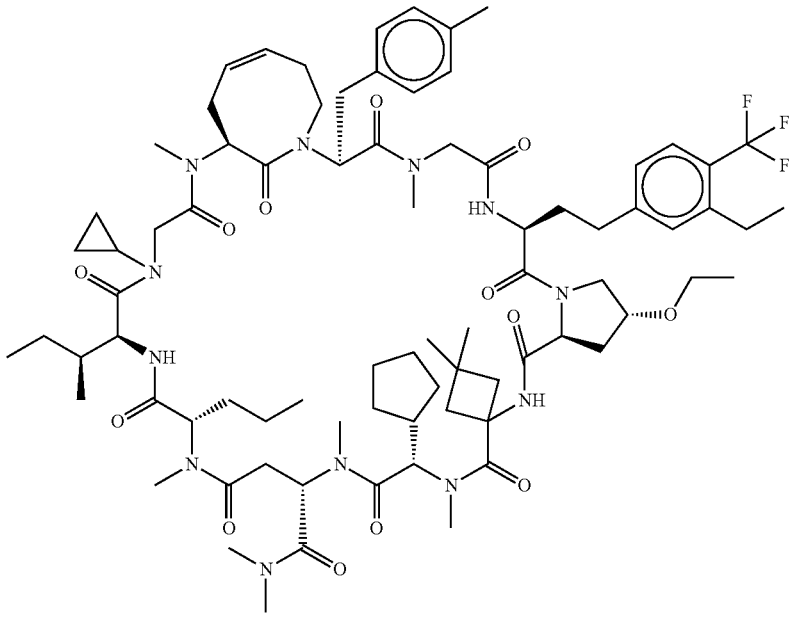 |
| PP2871 | 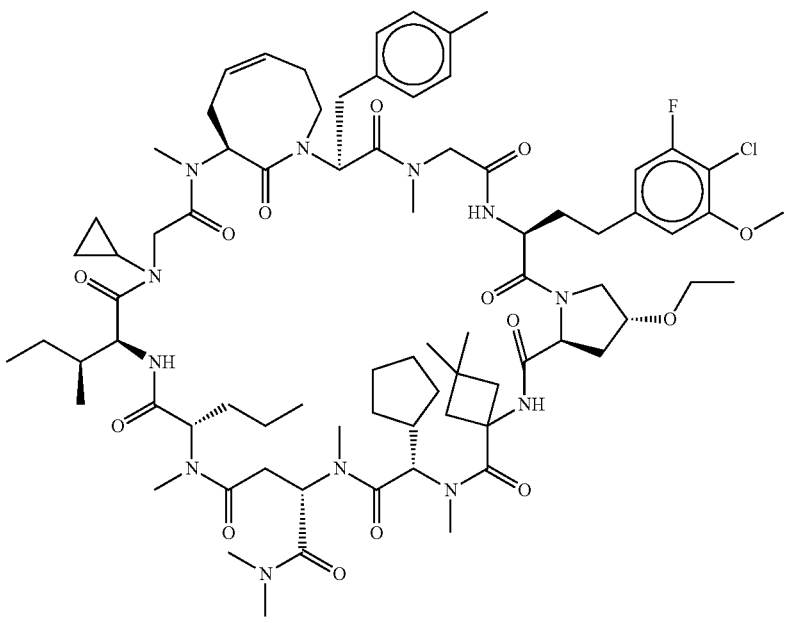 |

TABLE 38-continued

| Compound No. | Structural Formula |
|---|---|
| PP2872 | |
| PP2873 | |

TABLE 38-continued
| Compound No. | Structural Formula |
|---|---|
| PP2874 | 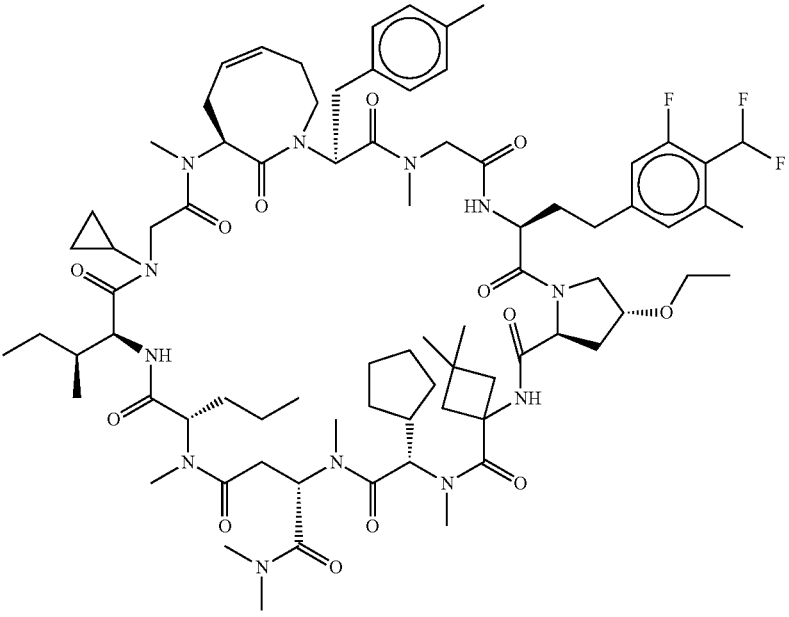 |
| PP2875 | 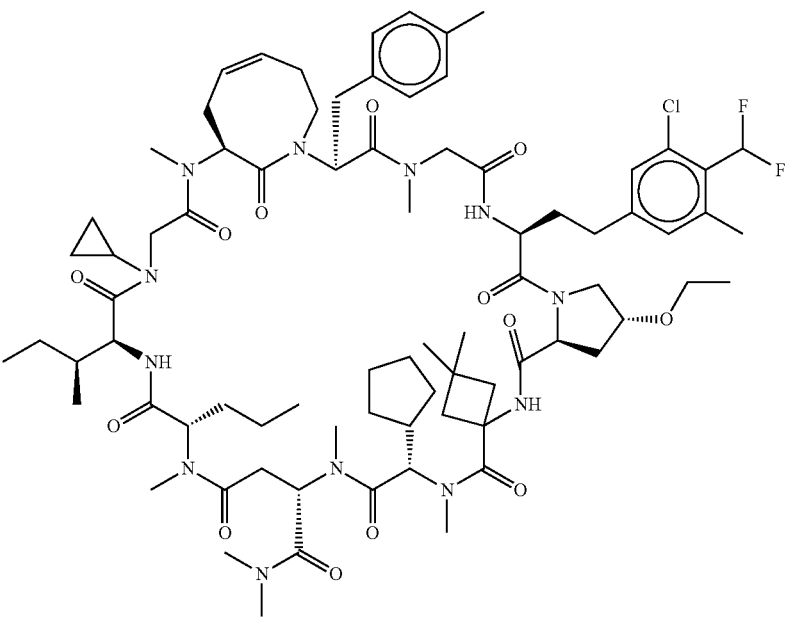 |

TABLE 38-continued
| Compound No. | Structural Formula |
|---|---|
| PP2876 | 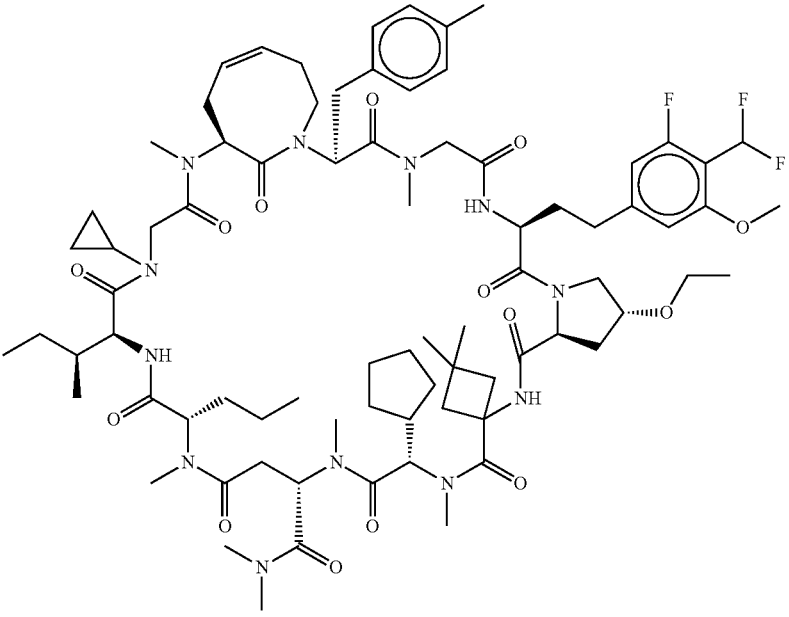 |
| PP2877 | 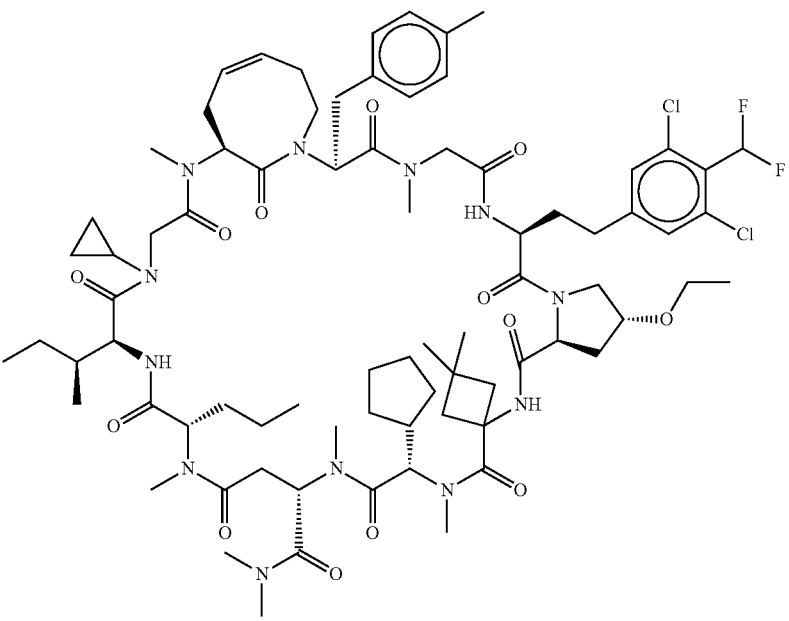 |

TABLE 38-continued
| Compound No. | Structural Formula |
|---|---|
| PP2878 | 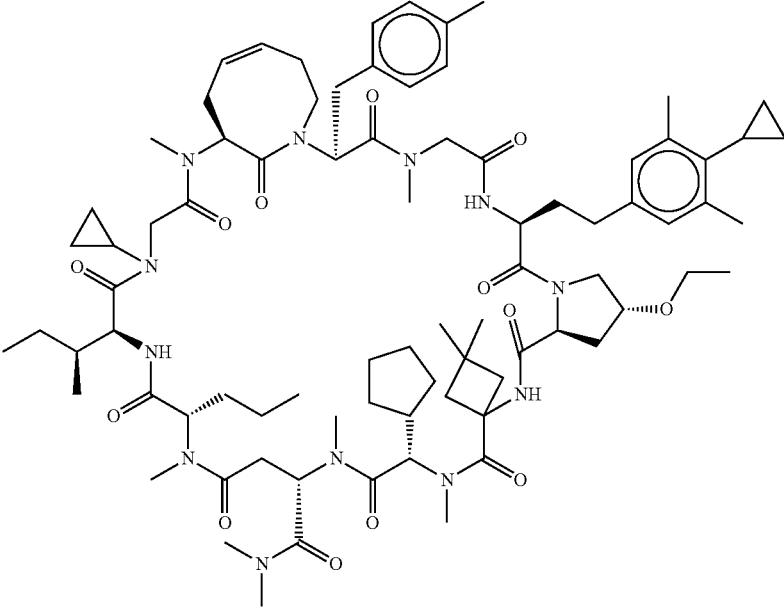 |
| PP2879 | 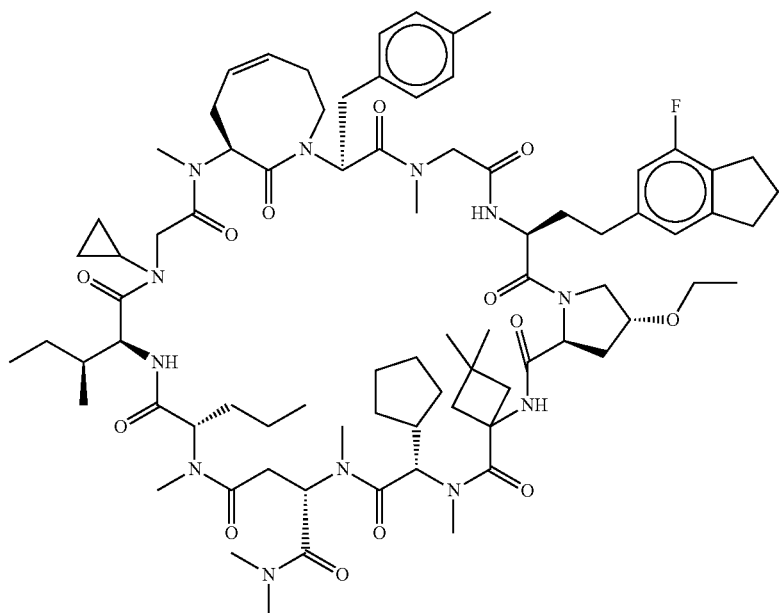 |

TABLE 38-continued

| Compound No. | Structural Formula |
|---|---|
| PP2880 | |
| PP2881 | |

TABLE 38-continued

| Compound No. | Structural Formula |
|---|---|
| PP2882 | |
| PP2883 | |

TABLE 38-continued

| Compound No. | Structural Formula |
| --- | --- |
| PP2884 | |
| PP2885 | |

TABLE 38-continued
| Compound No. | Structural Formula |
|---|---|
| PP2886 | 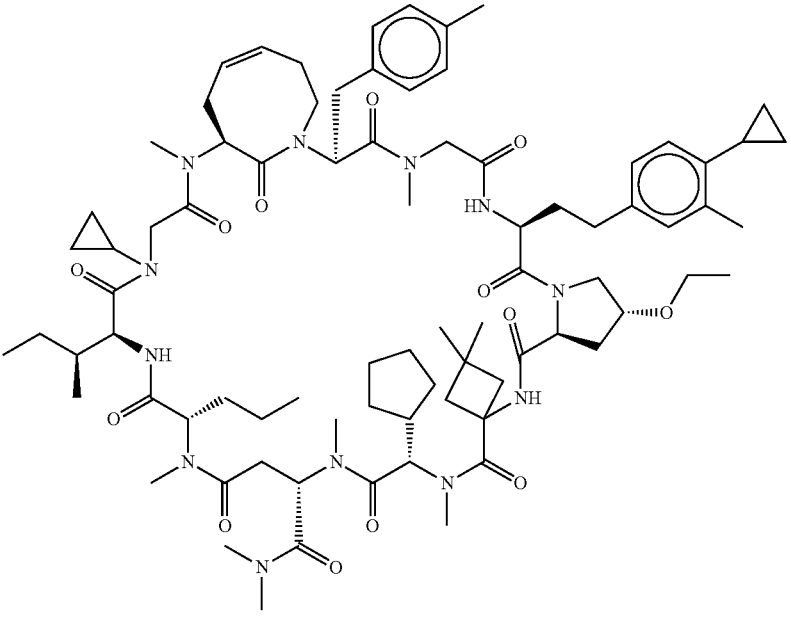 |
| PP2888 | 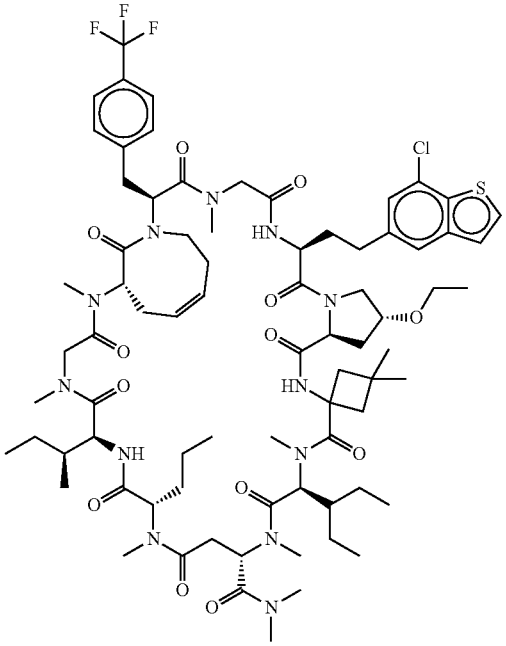 |

TABLE 38-continued

| Compound No. | Structural Formula |
|---|---|
| PP2889 | |
| PP2890 | |

TABLE 38-continued

| Compound No. | Structural Formula |
|---|---|
| PP2891 | |
| PP2892 | |

TABLE 38-continued

| Compound No. | Structural Formula |
|---|---|
| PP2893 | |
| PP2894 | |

TABLE 38-continued

| Compound No. | Structural Formula |
|---|---|
| PP2895 | |
| PP2896 | |

TABLE 38-continued
| Compound No. | Structural Formula |
|---|---|
| PP2897 | 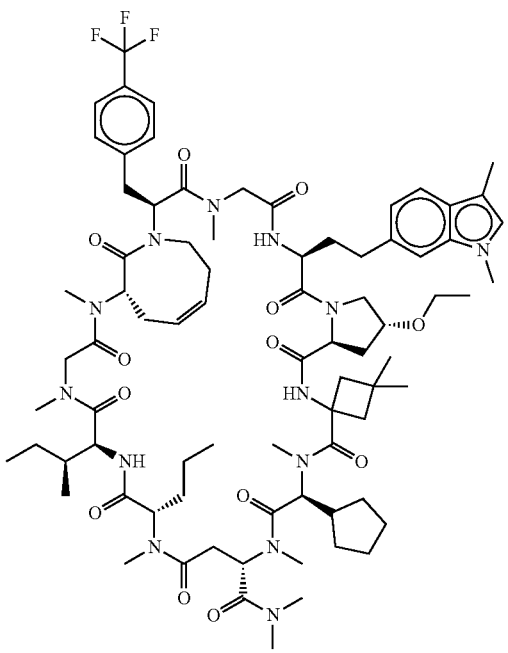 |
| PP2898 | 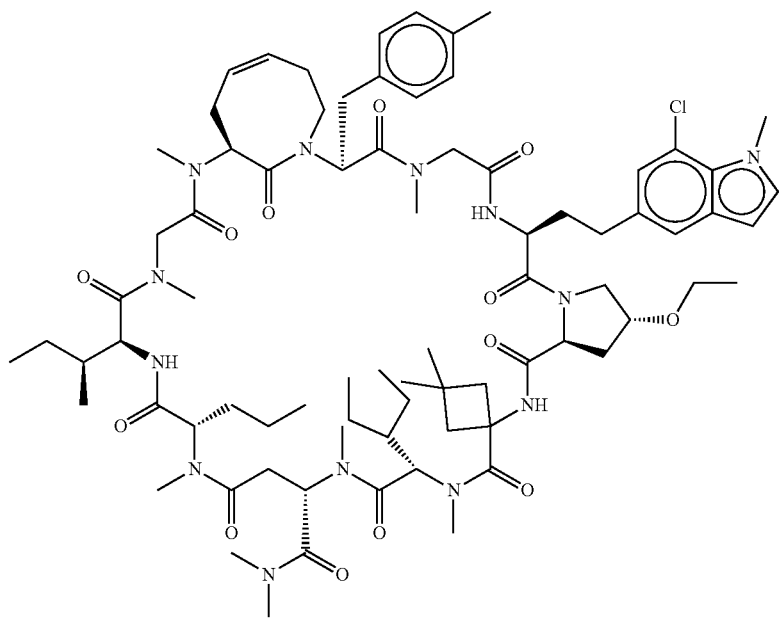 |

TABLE 38-continued

| Compound No. | Structural Formula |
|---|---|
| PP2899 | |
| PP2900 | |

TABLE 38-continued
| Compound No. | Structural Formula |
|---|---|
| PP2901 | 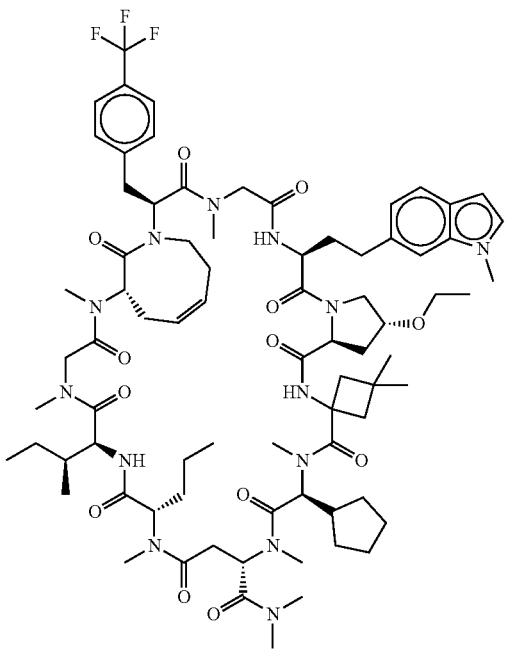 |
| PP2902 | 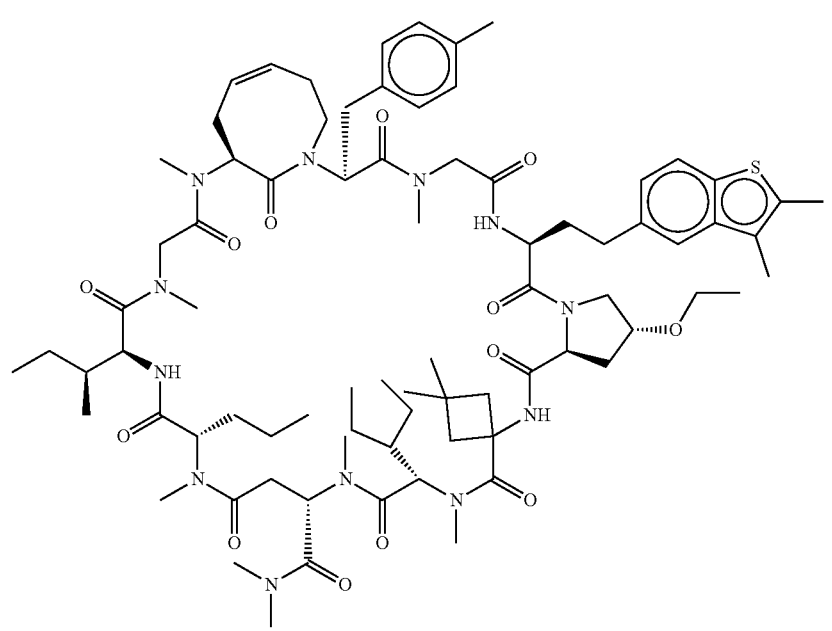 |

TABLE 38-continued

| Compound No. | Structural Formula |
|---|---|
| PP2904 | |
| PP2905 | |

TABLE 38-continued

| Compound No. | Structural Formula |
|---|---|
| PP2906 | |
| PP2907 | |

TABLE 38-continued

| Compound No. | Structural Formula |
|---|---|
| PP2908 | |
| PP2909 | |

TABLE 38-continued

| Compound No. | Structural Formula |
|---|---|
| PP2910 | |
| PP2911 | |

TABLE 38-continued

| Compound No. | Structural Formula |
|---|---|
| PP2912 | |
| PP2913 | |

TABLE 38-continued
| Compound No. | Structural Formula |
|---|---|
| PP2914 | 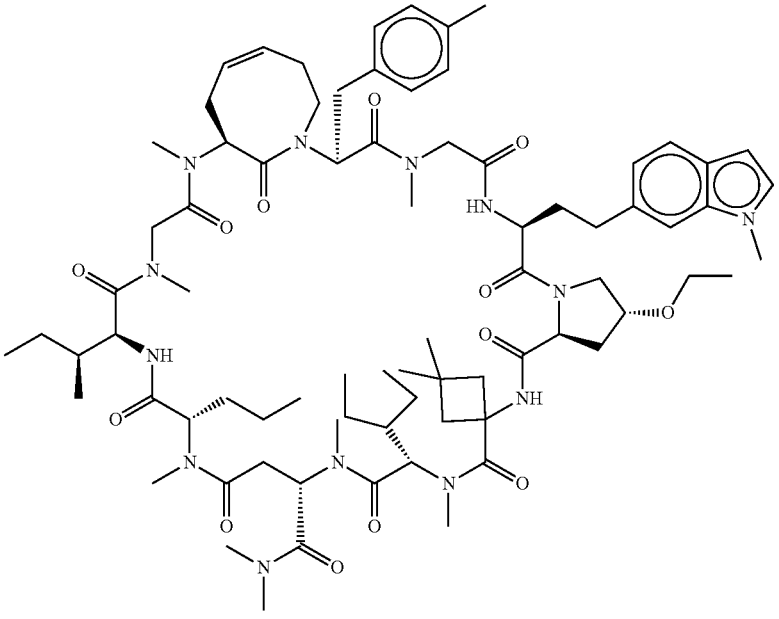 |
| PP2915 | 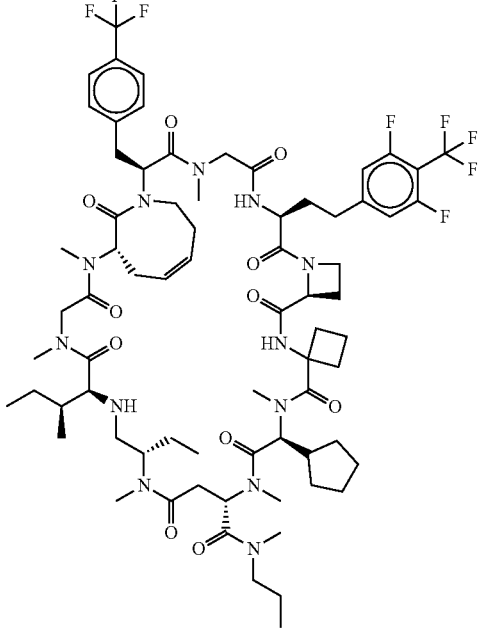 |

TABLE 38-continued

| Compound No. | Structural Formula |
|---|---|
| PP2916 | |
| PP2917 | |

TABLE 38-continued

| Compound No. | Structural Formula |
|---|---|
| PP2918 | |
| PP2919 | |

TABLE 38-continued
| Compound No. | Structural Formula |
|---|---|
| PP2920 | 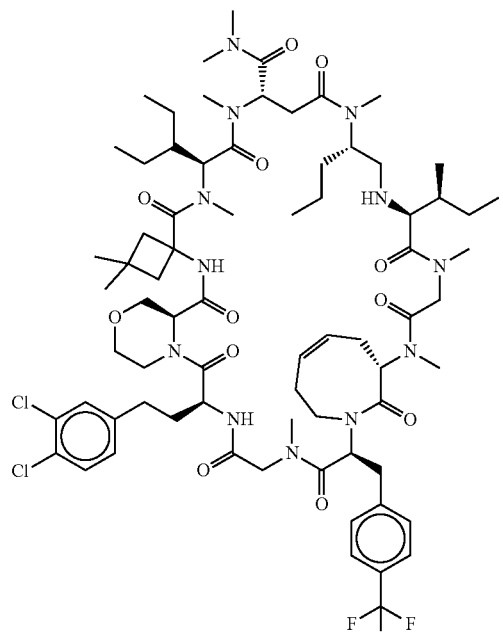 |
| PP2921 | 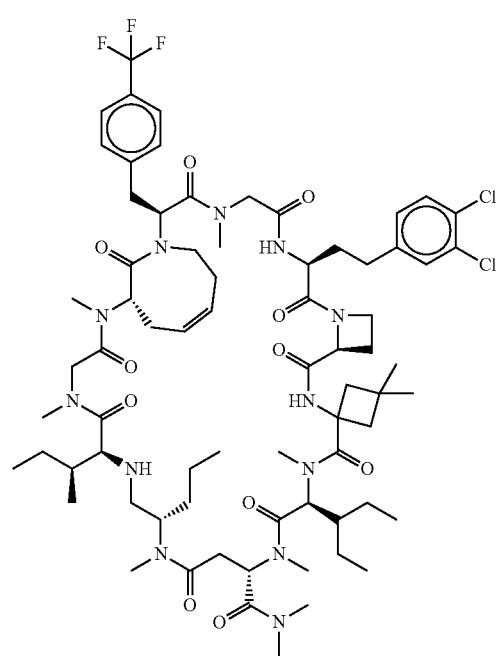 |

TABLE 38-continued
| Compound No. | Structural Formula |
|---|---|
| PP2922 | 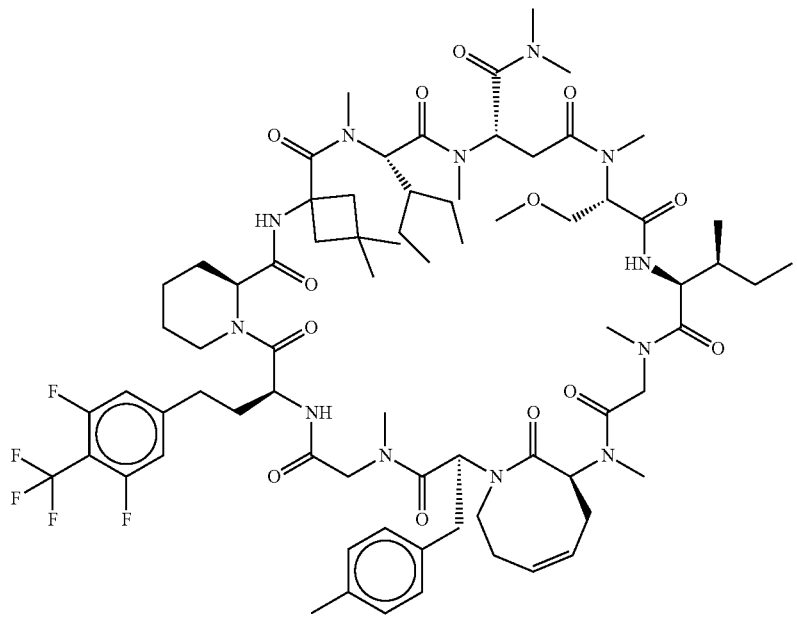 |
| PP2923 | 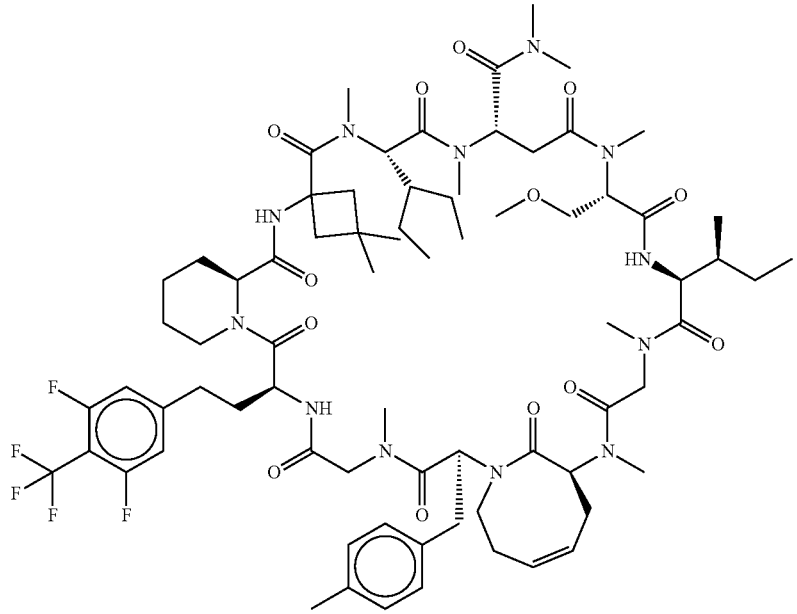 |

| Compound No. | Structural Formula |
|---|---|
| PP2928 | 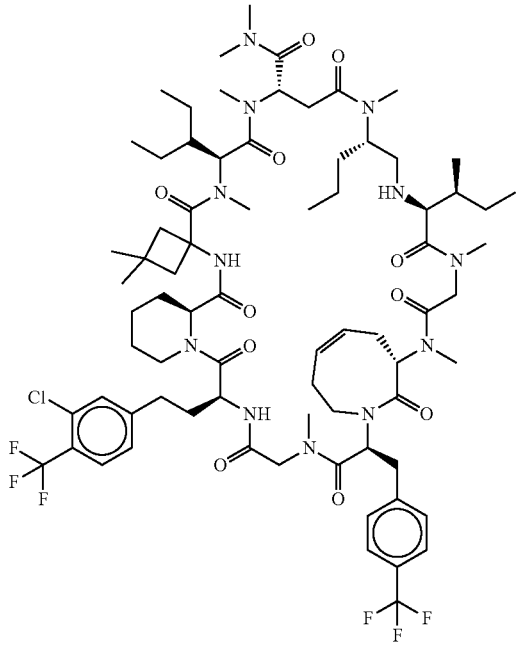 |
| PP2929 | 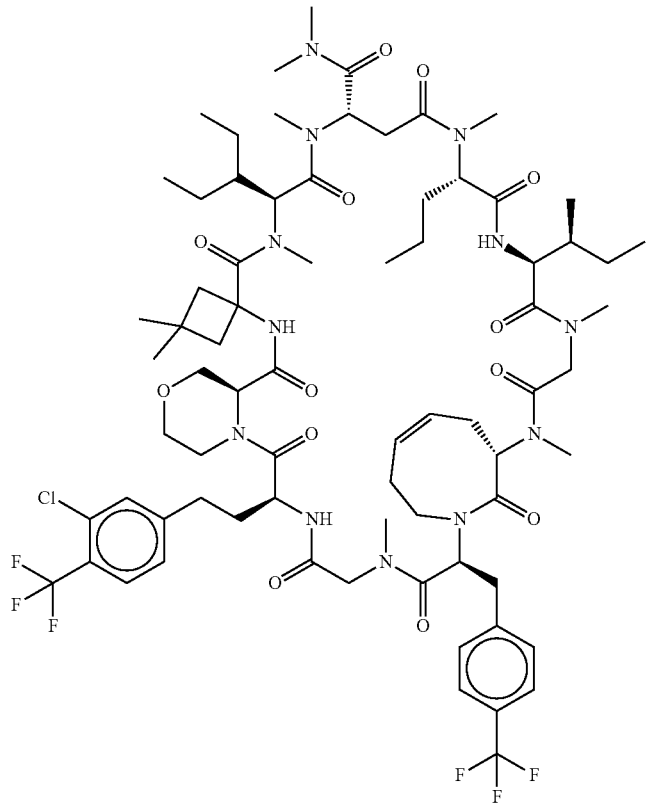 |

TABLE 38-continued
| Compound No. | Structural Formula |
|---|---|
| PP2931 | 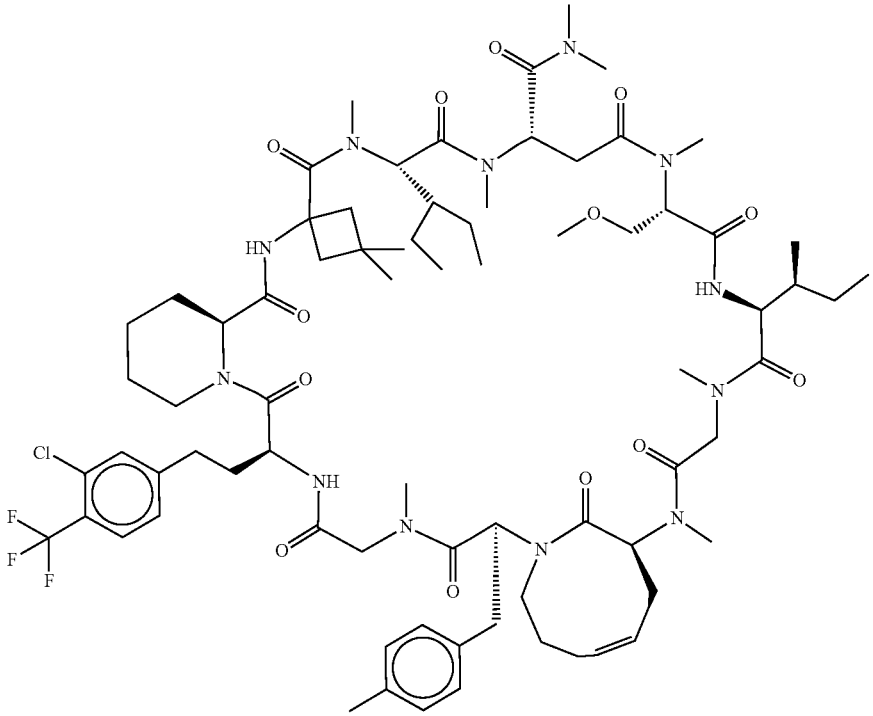 |
| PP2932 | 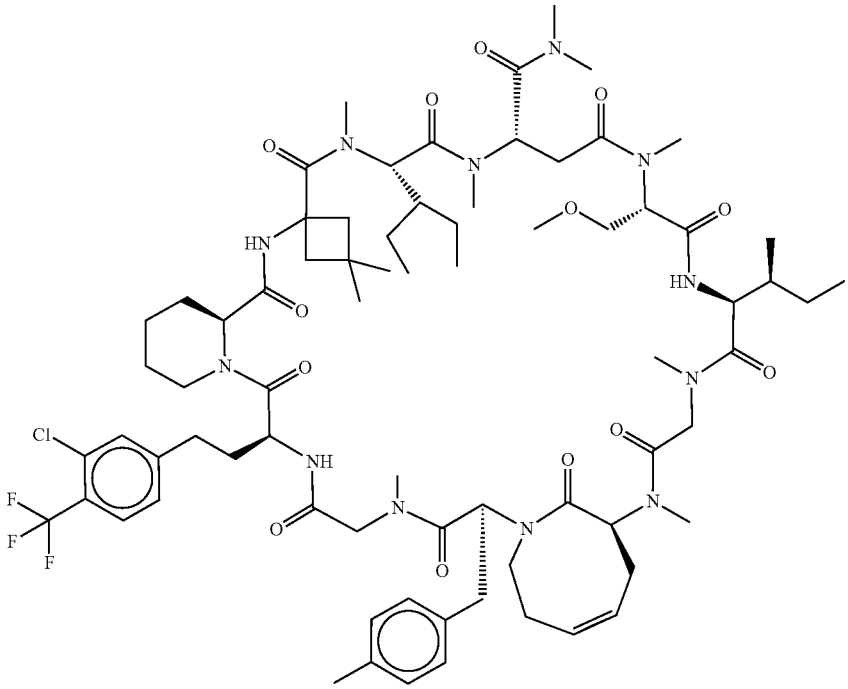 |

TABLE 38-continued
| Compound No. | Structural Formula |
|---|---|
| PP2934 | 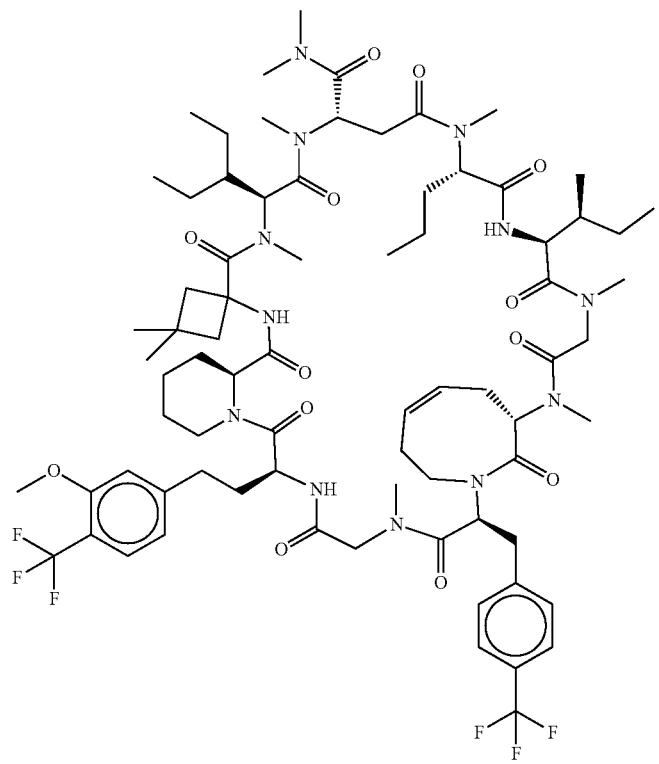 |
| PP2935 | 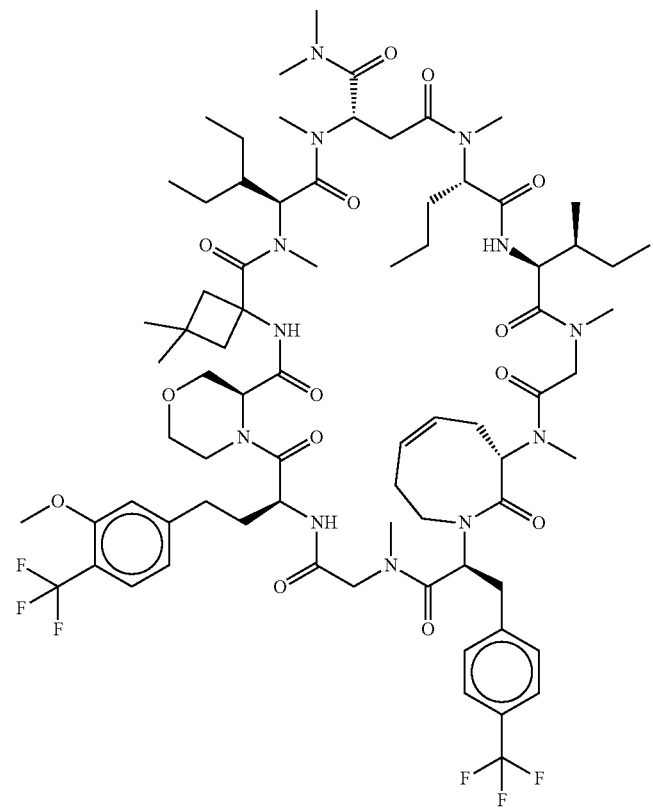 |

TABLE 38-continued
| Compound No. | Structural Formula |
|---|---|
| PP2936 | 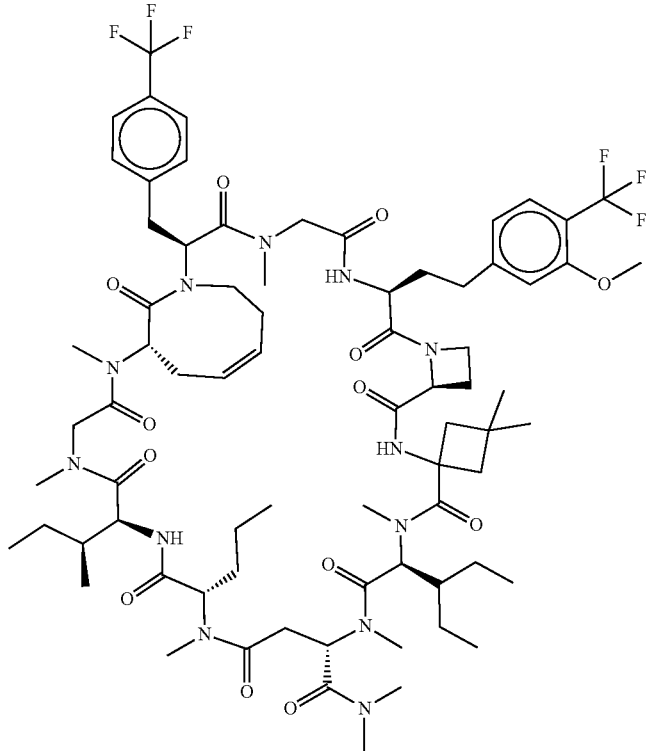 |
| PP2937 | 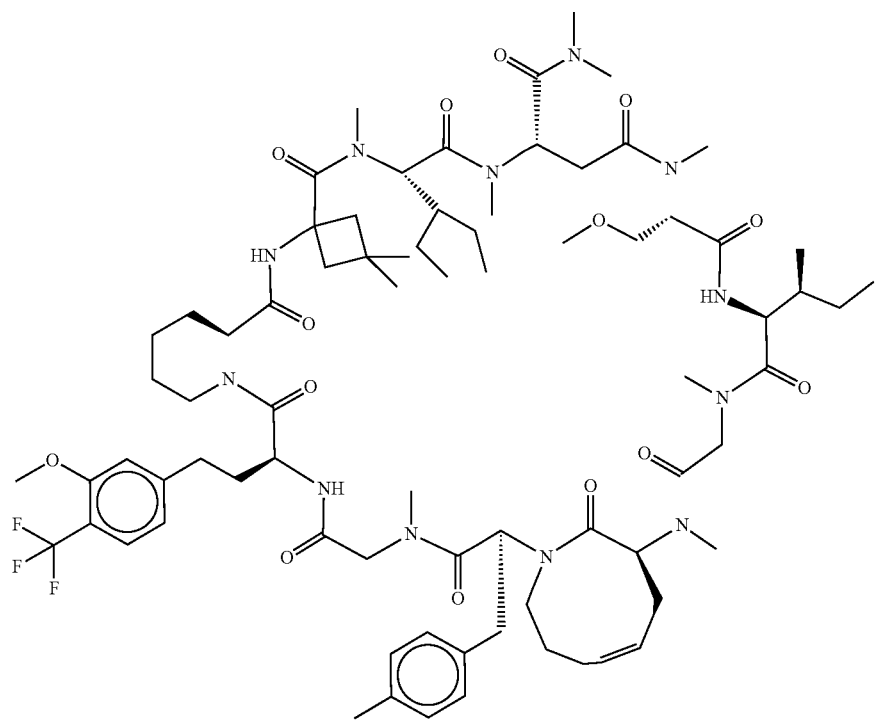 |

TABLE 38-continued
| Compound No. | Structural Formula |
|---|---|
| PP2938 | 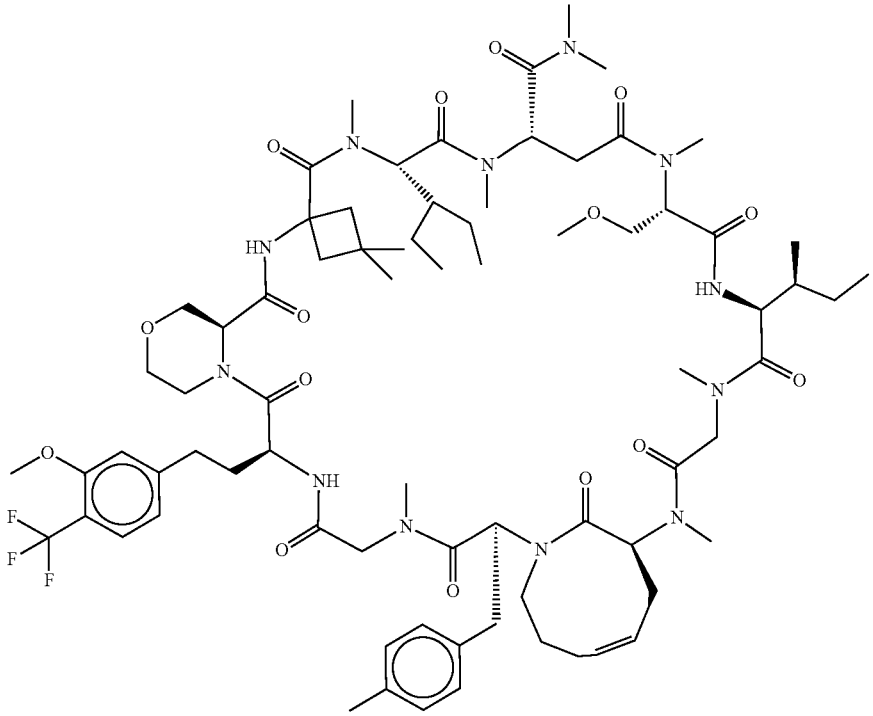 |
| PP2941 | 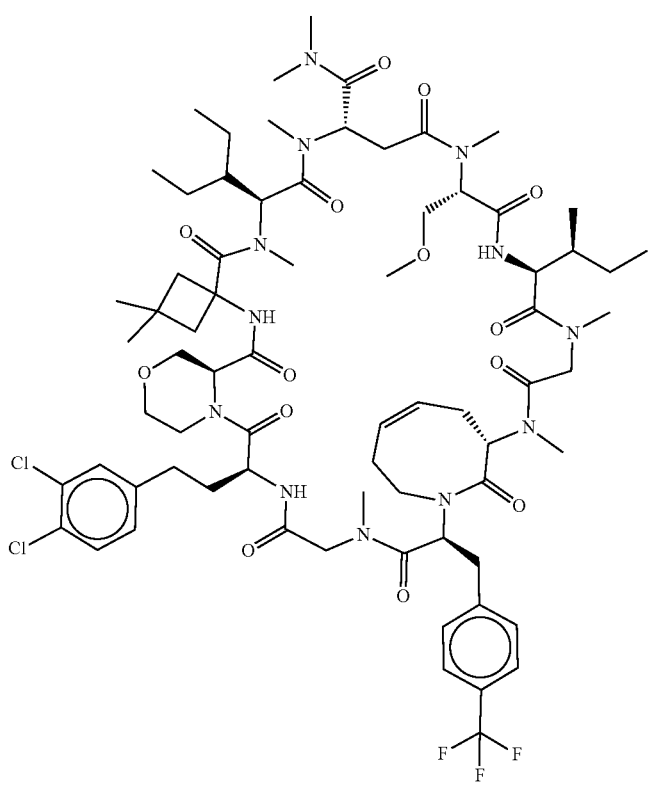 |

TABLE 38-continued
| Compound No. | Structural Formula |
|---|---|
| PP2946 | 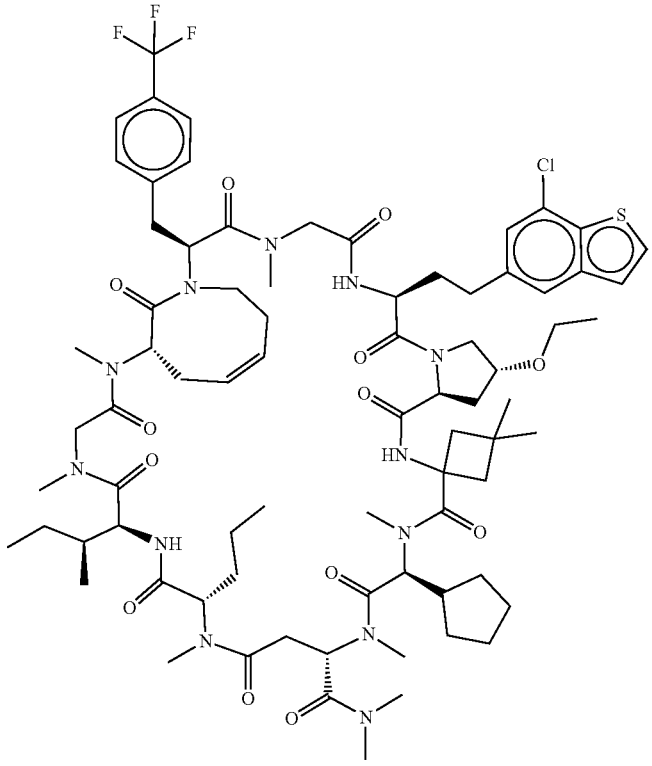 |
| PP2947 | 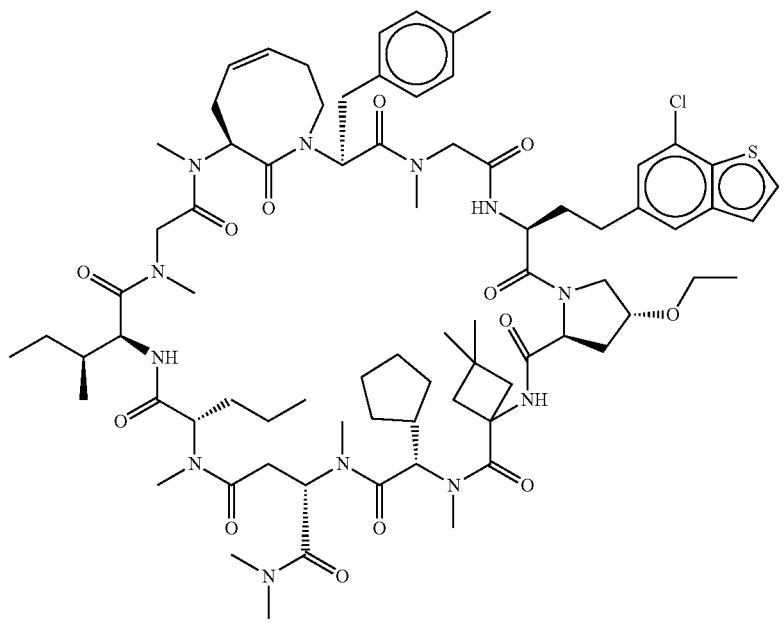 |

TABLE 38-continued
| Compound No. | Structural Formula |
| --- | --- |
| PP2948 | 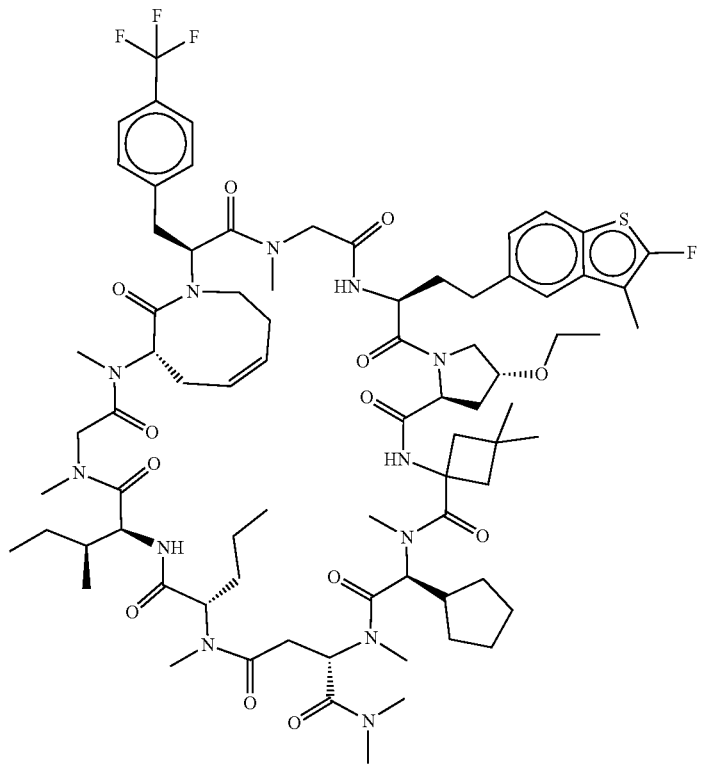 |
| PP2949 | 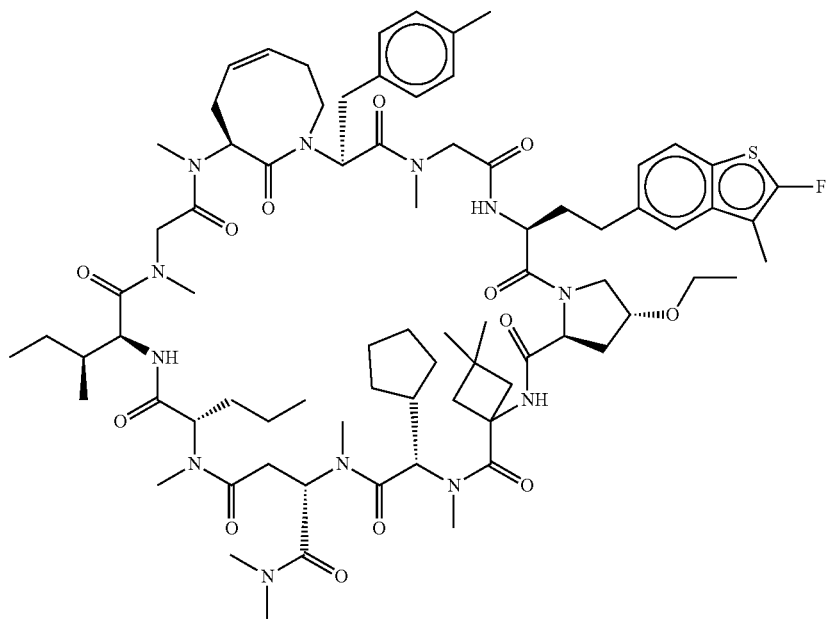 |

TABLE 38-continued

| Compound No. | Structural Formula |
|---|---|
| PP2950 | |
| PP2951 | |

TABLE 38-continued
| Compound No. | Structural Formula |
|---|---|
| PP2952 | 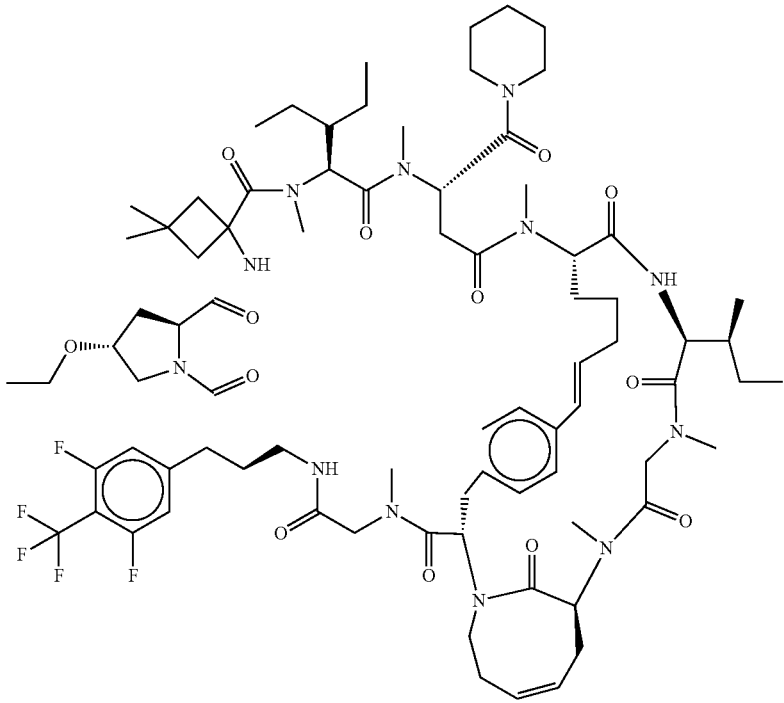 |
| PP2953 | 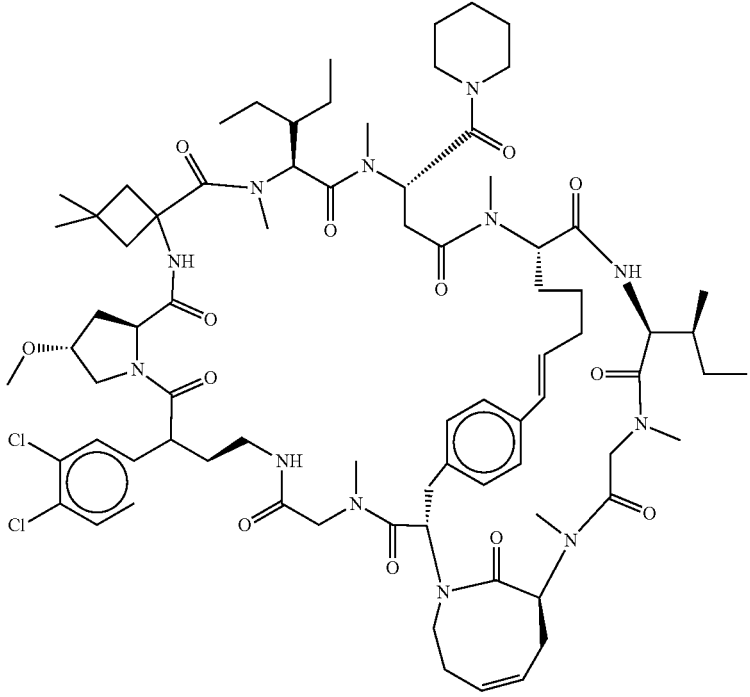 |

TABLE 38-continued
| Compound No. | Structural Formula |
|---|---|
| PP2954 | 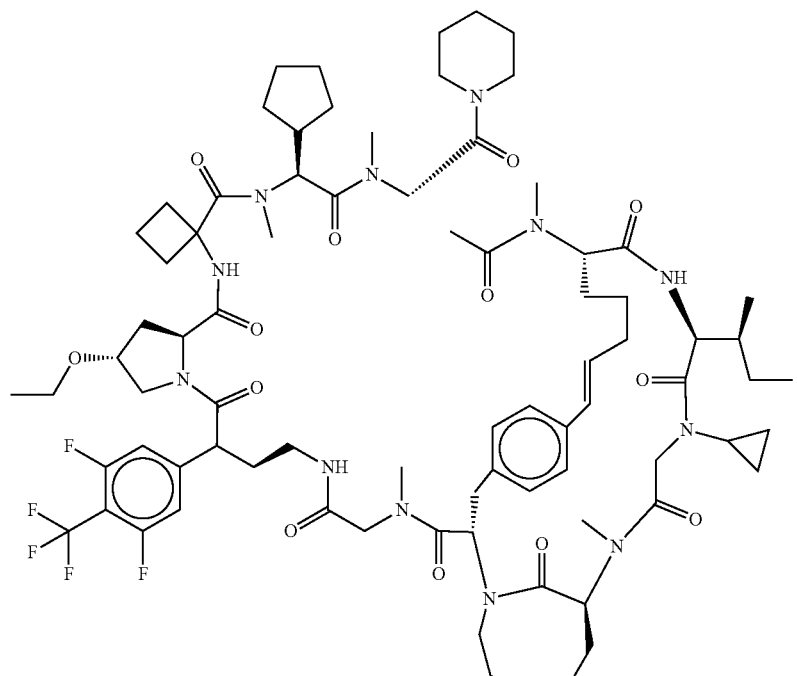 |
| PP2955 | 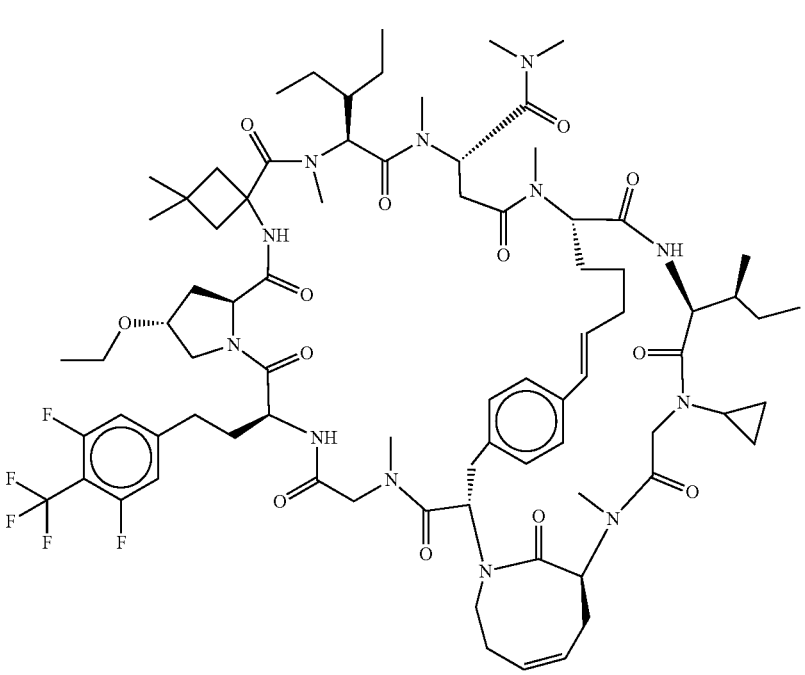 |

TABLE 38-continued
| Compound No. | Structural Formula |
|---|---|
| PP2956 | 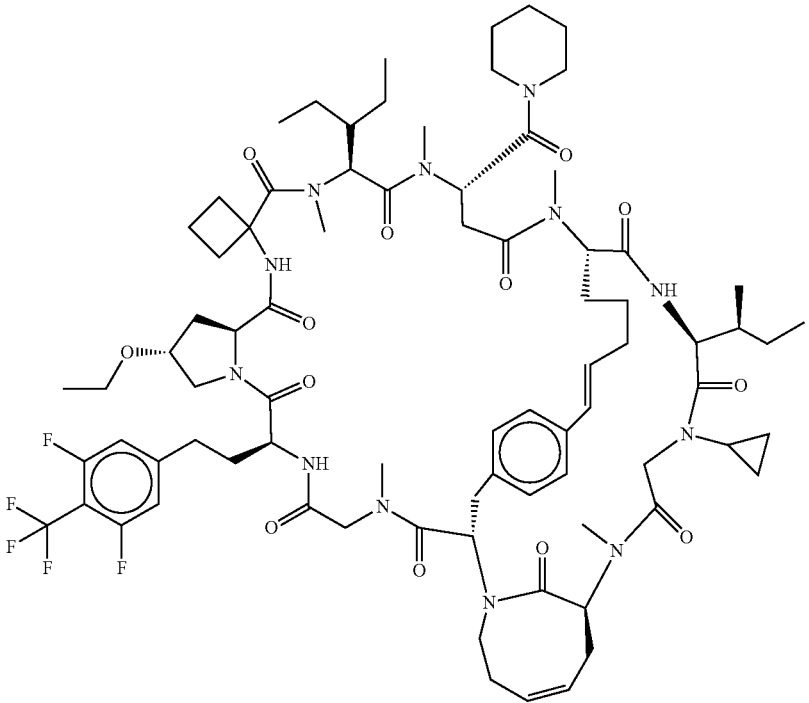 |
| PP2957 | 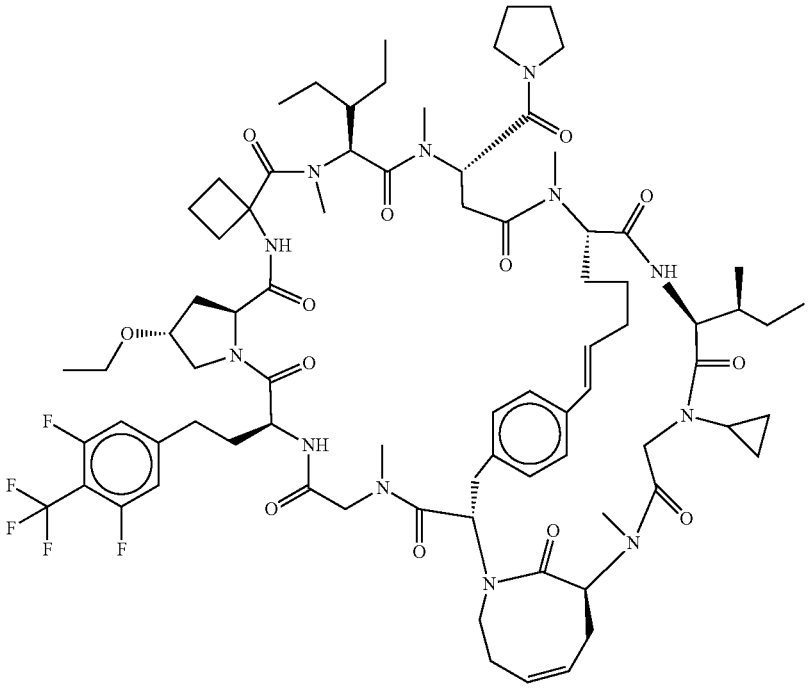 |

TABLE 38-continued
| Compound No. | Structural Formula |
|---|---|
| PP2958 | 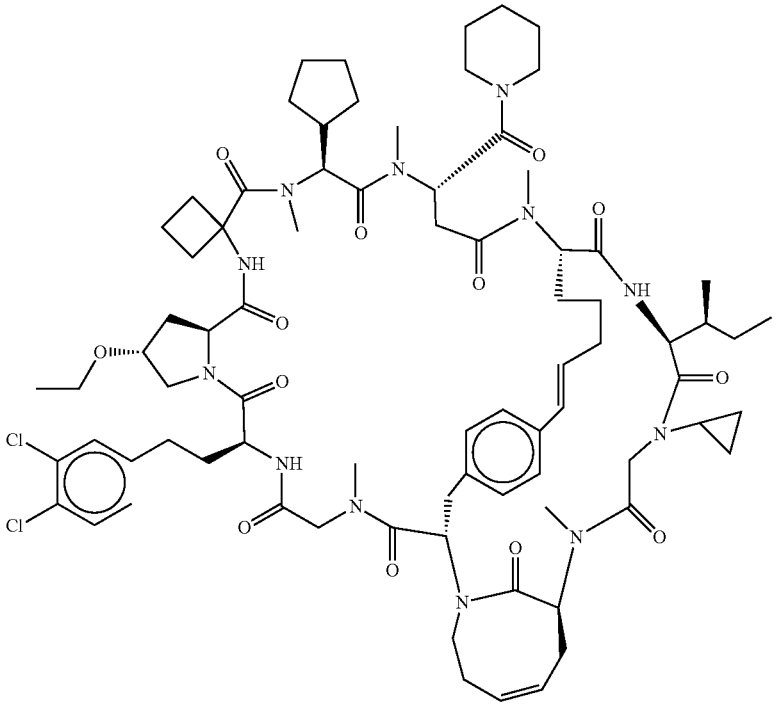 |
| PP2959 | 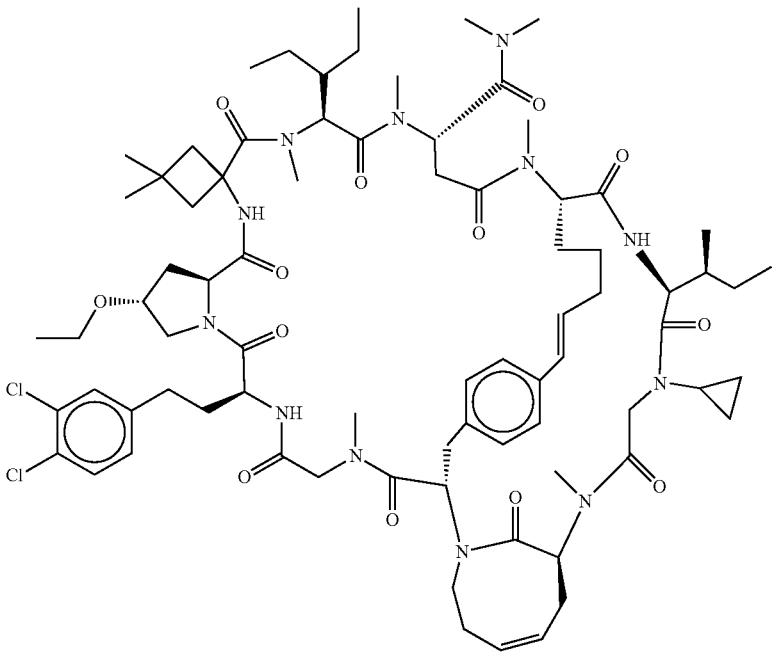 |

TABLE 38-continued

| Compound No. | Structural Formula |
|---|---|
| PP2960 | |
| PP2961 | |

TABLE 38-continued

| Compound No. | Structural Formula |
|---|---|
| PP2962 | |
| PP2963 | |

TABLE 38-continued
| Compound No. | Structural Formula |
|---|---|
| PP2964 | 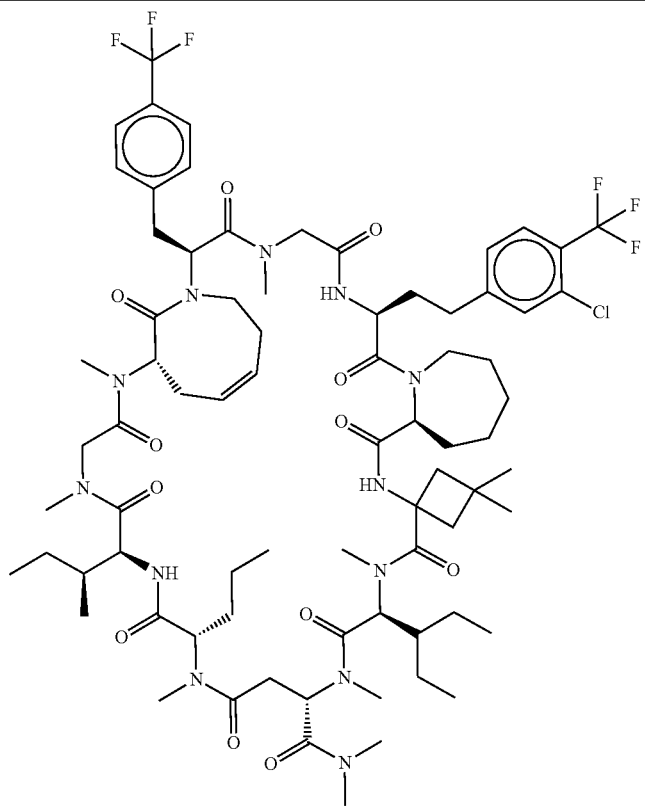 |
| PP2965 | 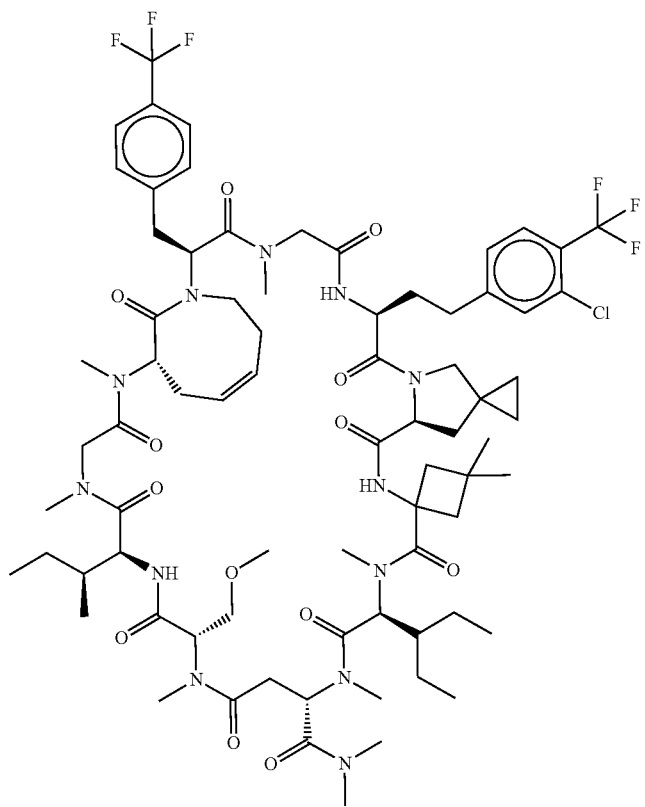 |

TABLE 38-continued

| Compound No. | Structural Formula |
|---|---|
| PP2966 | |
| PP2967 | |

TABLE 38-continued
| Compound No. | Structural Formula |
|---|---|
| PP2968 | 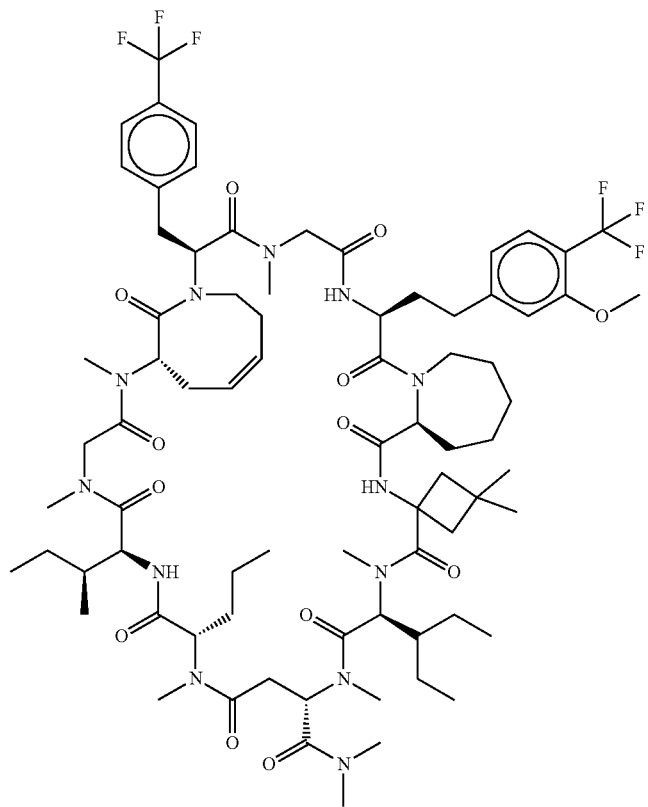 |
| PP2969 | 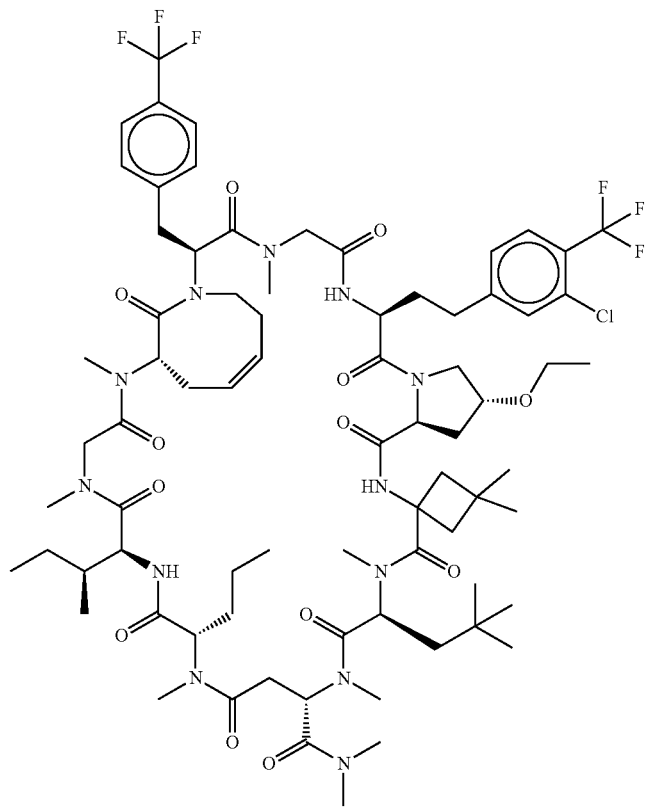 |

TABLE 38-continued

| Compound No. | Structural Formula |
|---|---|
| PP2970 | |
| PP2971 | |

TABLE 38-continued
| Compound No. | Structural Formula |
|---|---|
| PP2973 | 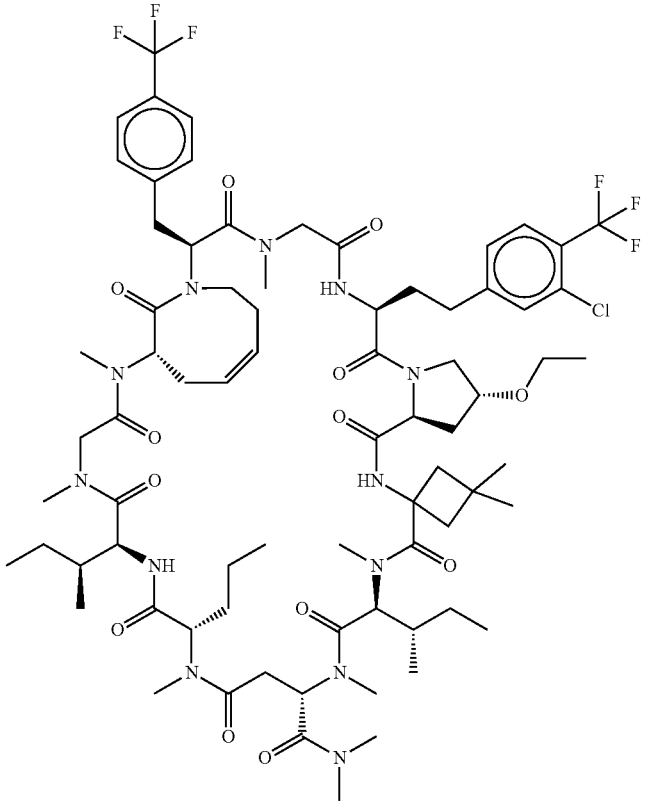 |
| PP2974 | 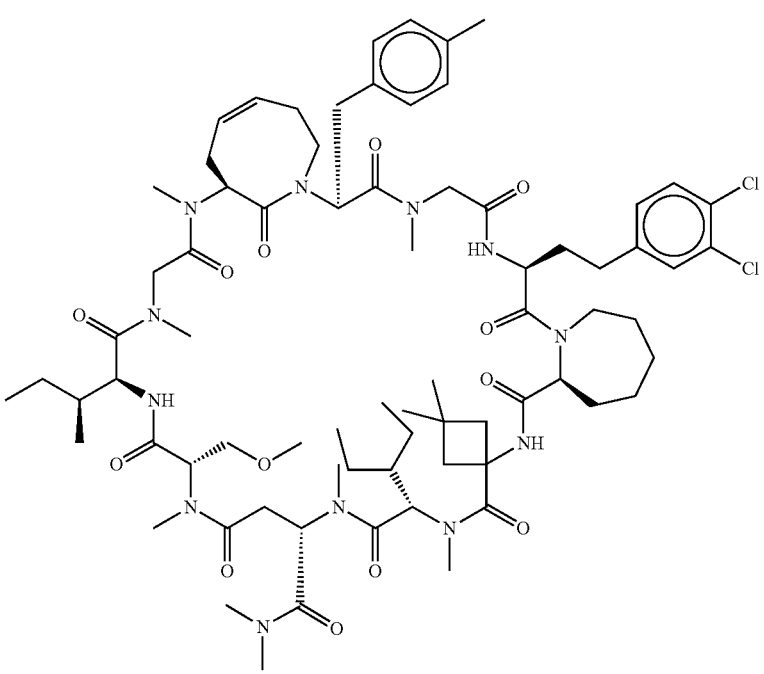 |

TABLE 38-continued
| Compound No. | Structural Formula |
|---|---|
| PP2975 | 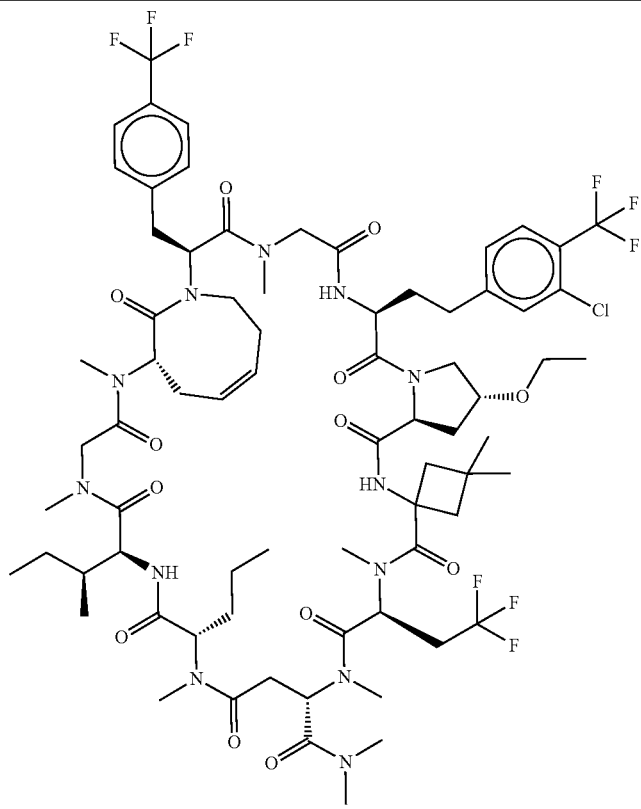 |
| PP2977 | 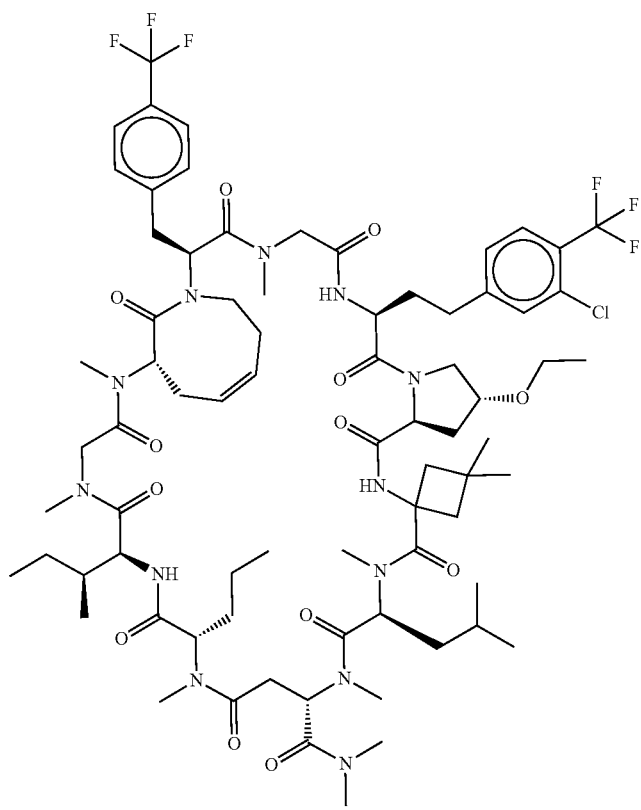 |

TABLE 38-continued

| Compound No. | Structural Formula |
|---|---|
| PP2978 | |
| PP2979 | |

TABLE 38-continued
| Compound No. | Structural Formula |
|---|---|
| PP2980 | 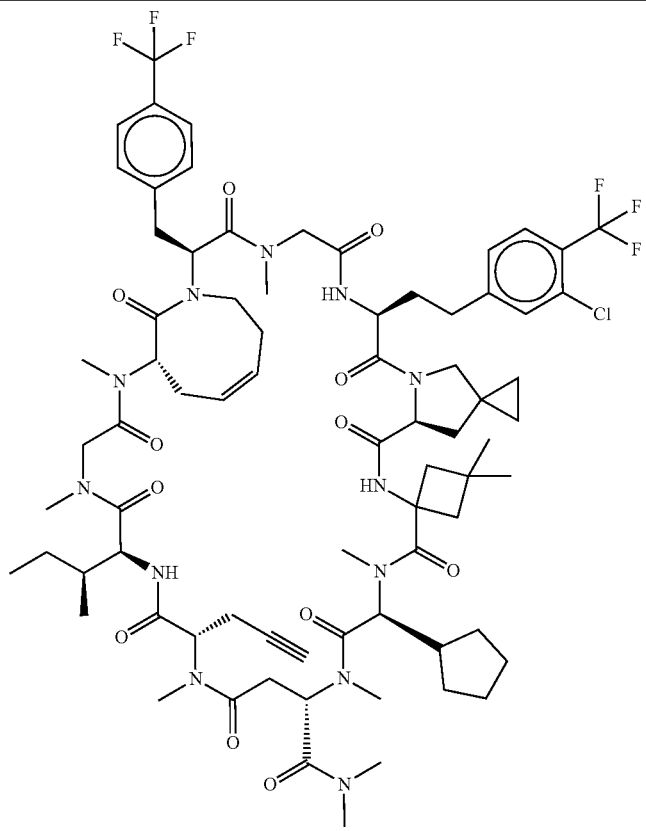 |
| PP2981 | 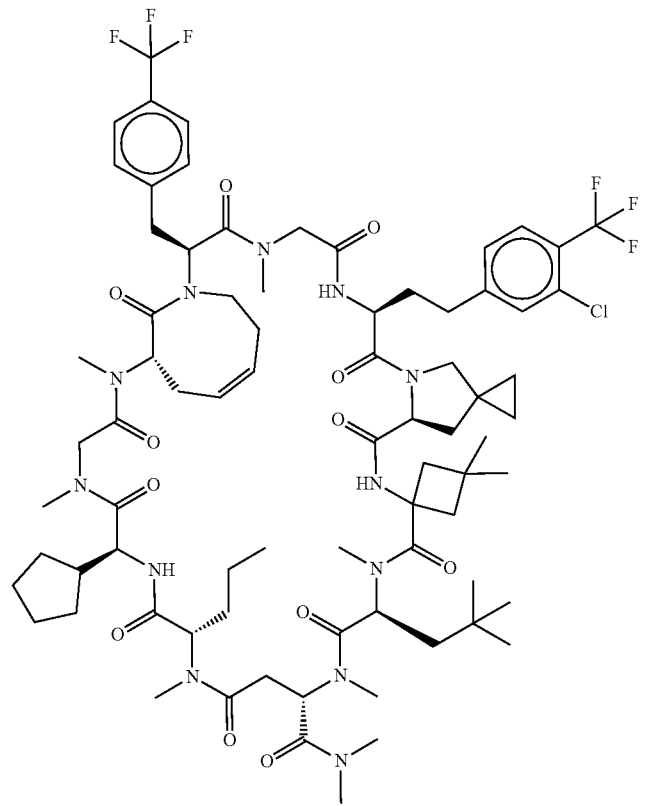 |

TABLE 38-continued
| Compound No. | Structural Formula |
|---|---|
| PP2982 | 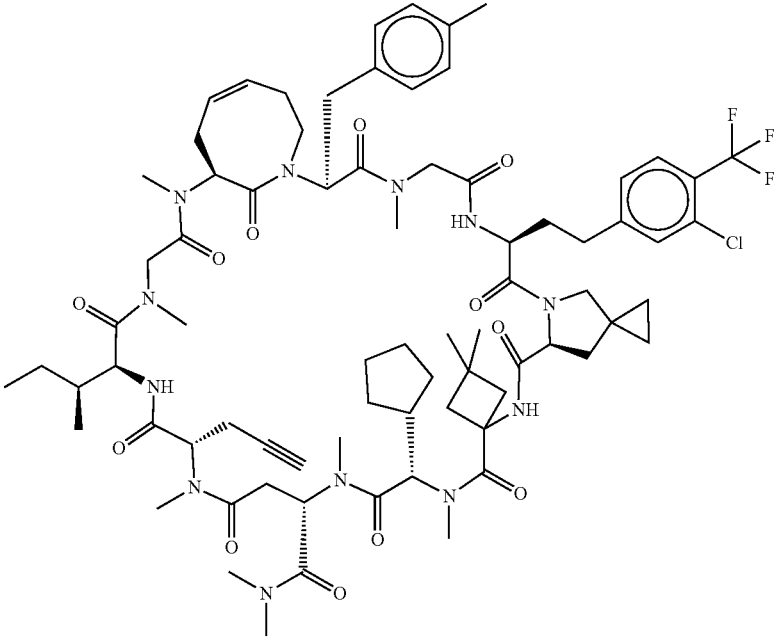 |
| PP2983 | 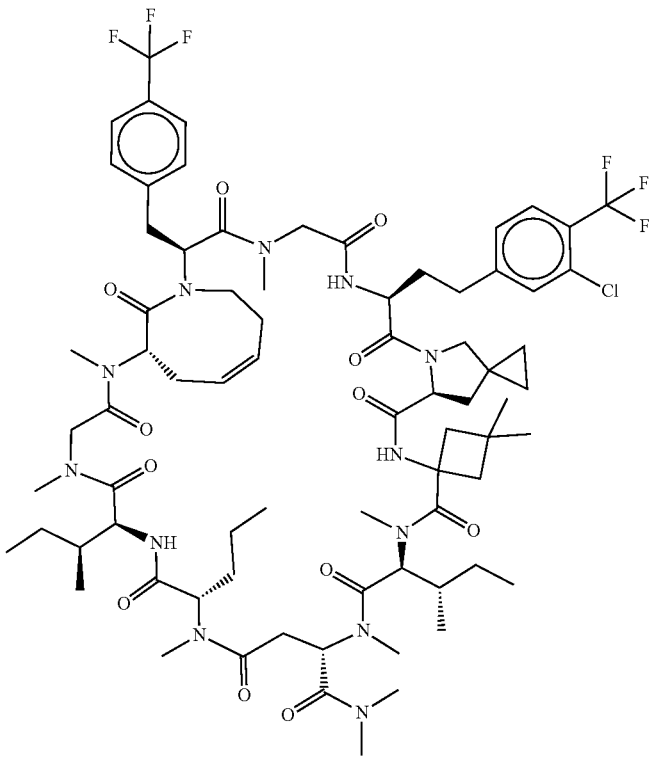 |

TABLE 38-continued
| Compound No. | Structural Formula |
|---|---|
| PP2984 | 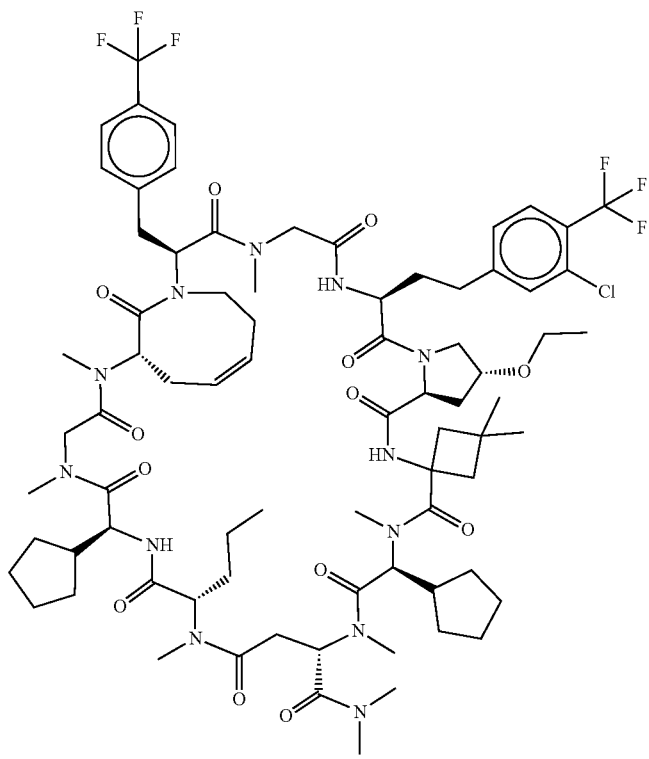 |
| PP2985 | 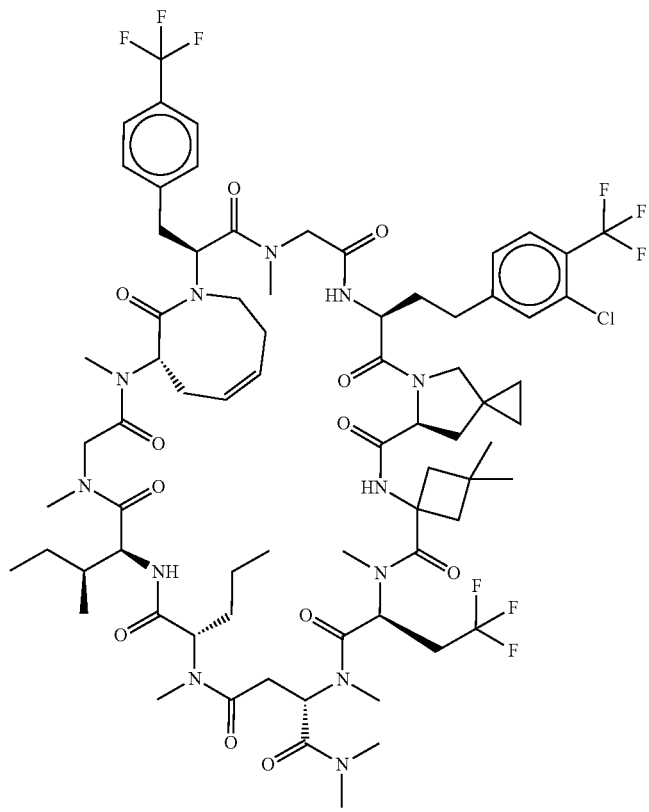 |

TABLE 38-continued
| Compound No. | Structural Formula |
|---|---|
| PP2986 | 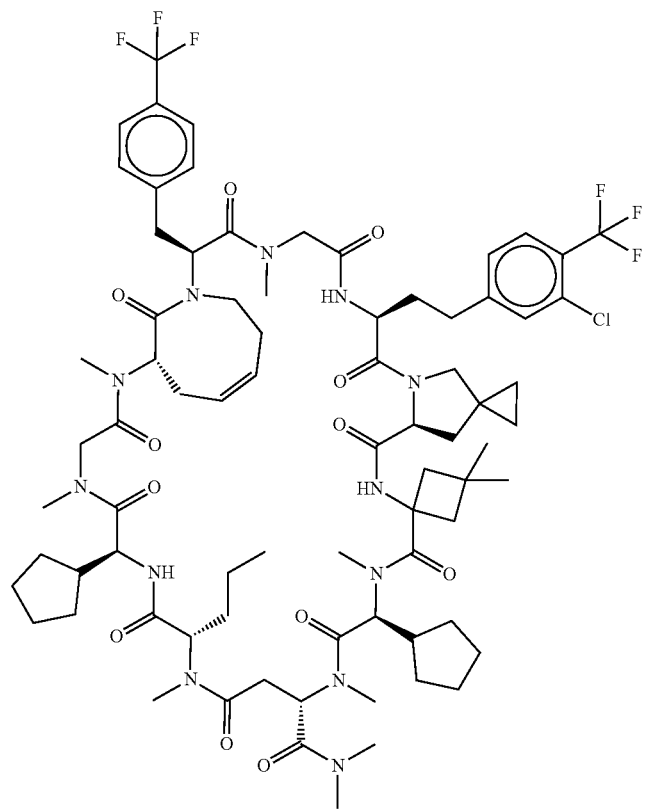 |
| PP2987 | 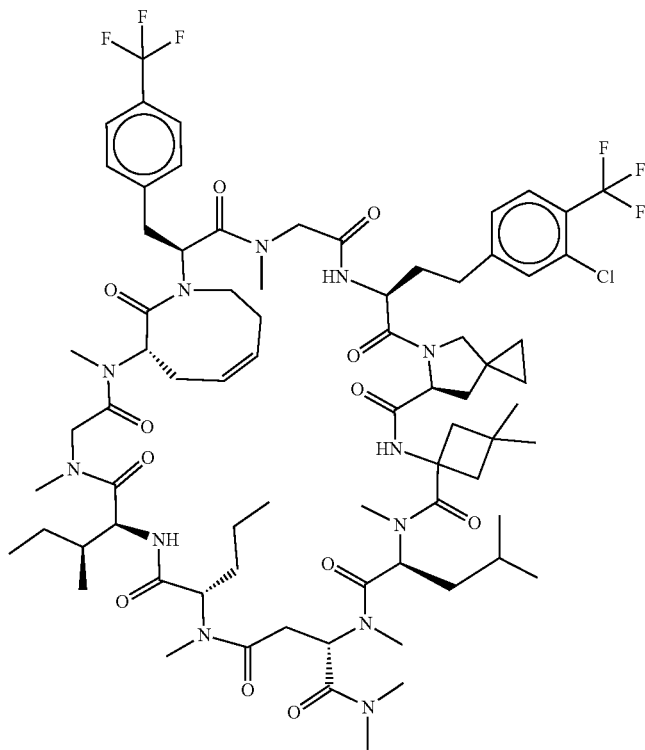 |

TABLE 38-continued

| Compound No. | Structural Formula |
|---|---|
| PP2988 | |
| PP2989 | |

TABLE 38-continued

| Compound No. | Structural Formula |
|---|---|
| PP2991 | |
| PP2992 | |

TABLE 38-continued

| Compound No. | Structural Formula |
|---|---|
| PP2993 | |
| PP2994 | |

TABLE 38-continued

| Compound No. | Structural Formula |
|---|---|
| PP2995 | |
| PP2996 | |

TABLE 38-continued

| Compound No. | Structural Formula |
|---|---|
| PP2997 | |
| PP2998 | |

TABLE 38-continued

| Compound No. | Structural Formula |
| --- | --- |
| PP2999 | |
| PP3000 | |

TABLE 38-continued

| Compound No. | Structural Formula |
|---|---|
| PP3001 | |
| PP3002 | |

TABLE 38-continued

| Compound No. | Structural Formula |
|---|---|
| PP3003 | |
| PP3004 | |

TABLE 38-continued
| Compound No. | Structural Formula |
|---|---|
| PP3005 | 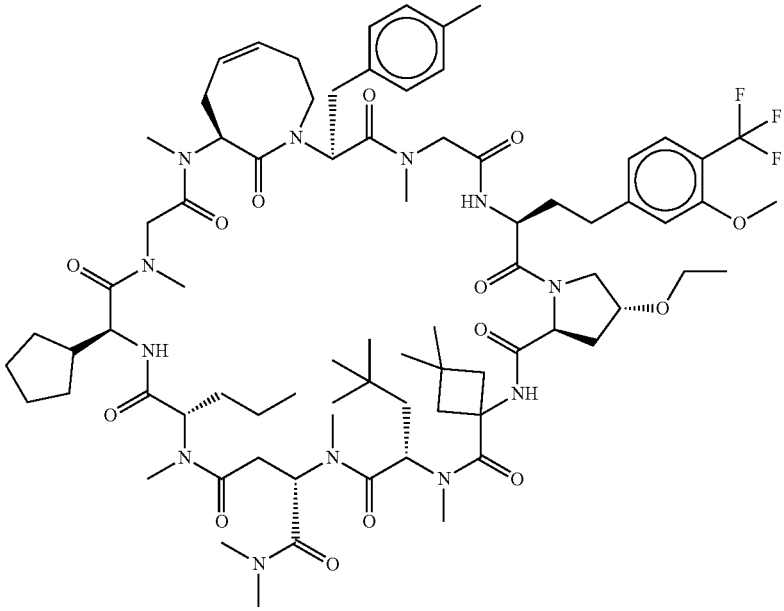 |
| PP3006 | 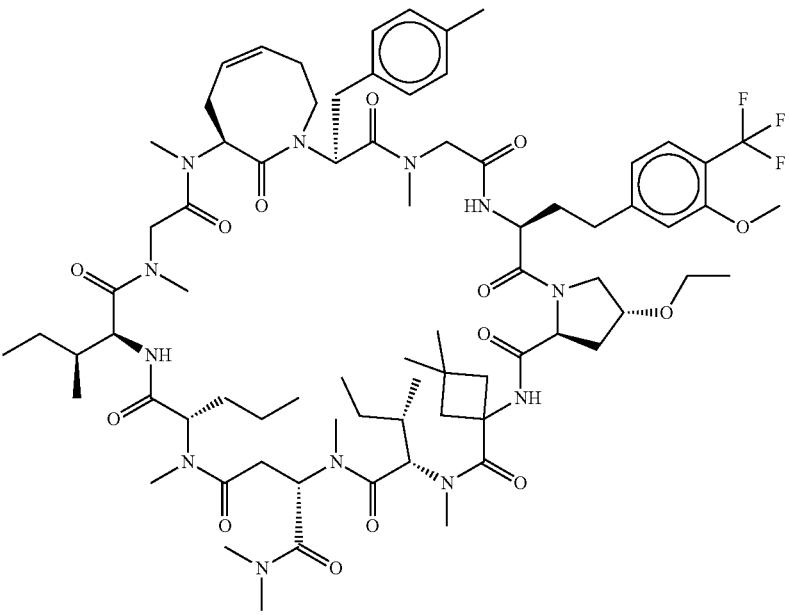 |

TABLE 38-continued

| Compound No. | Structural Formula |
|---|---|
| PP3007 | |
| PP3008 | |

TABLE 38-continued
| Compound No. | Structural Formula |
|---|---|
| PP3009 | 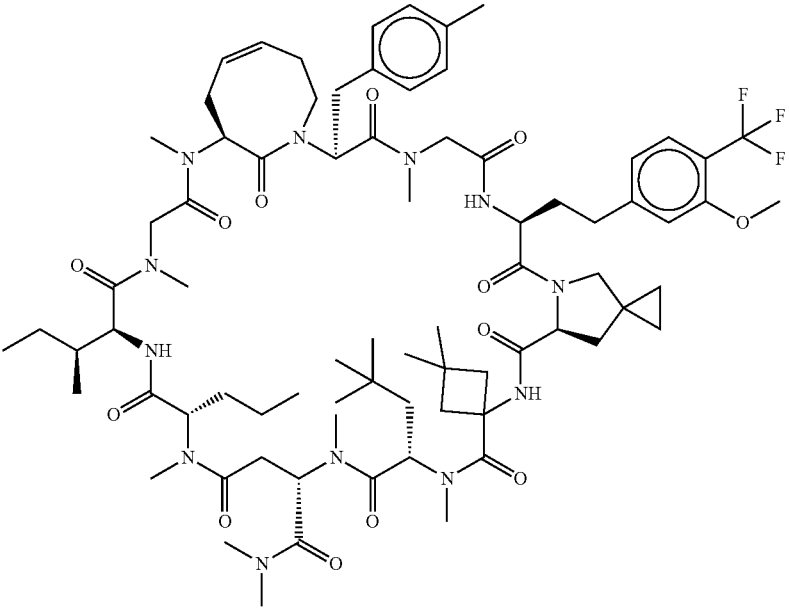 |
| PP3010 | 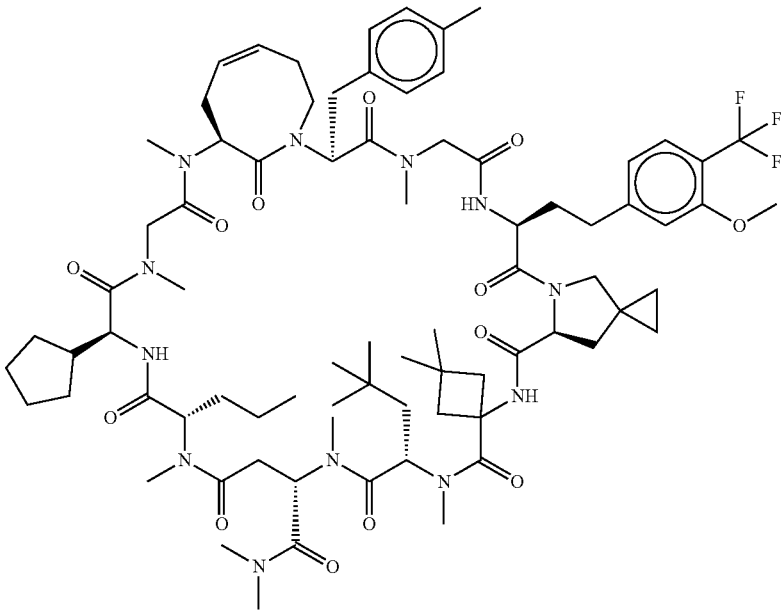 |

TABLE 38-continued

| Compound No. | Structural Formula |
|---|---|
| PP3011 | |
| PP3012 | |

TABLE 38-continued

| Compound No. | Structural Formula |
| --- | --- |
| PP3013 | |
| PP3014 | |

TABLE 38-continued
| Compound No. | Structural Formula |
|---|---|
| PP3015 | 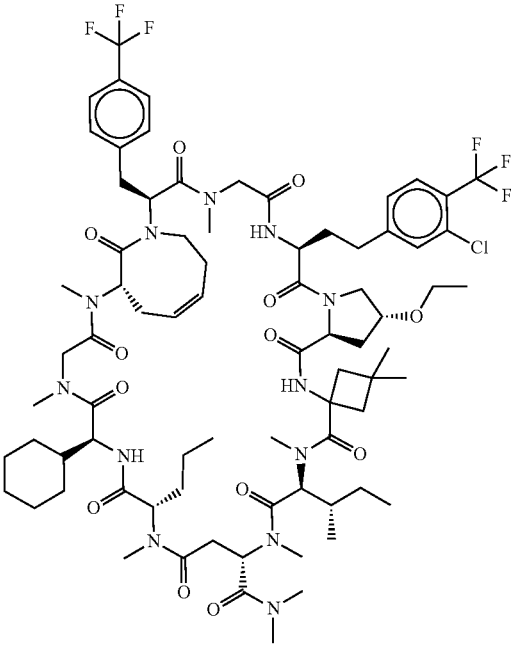 |
| PP3016 | 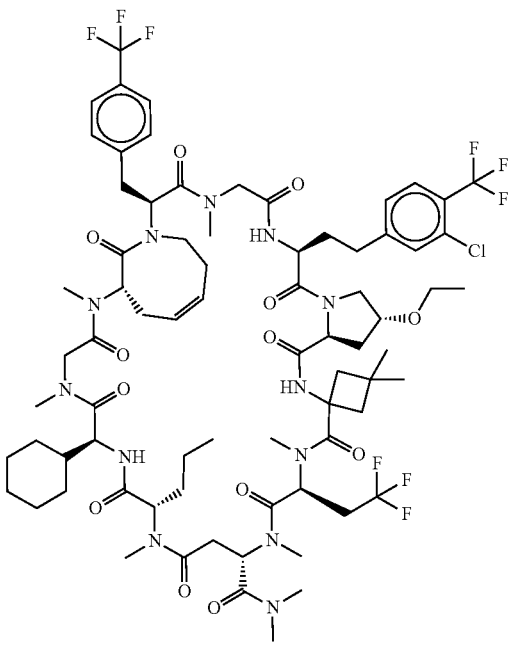 |

TABLE 38-continued

| Compound No. | Structural Formula |
|---|---|
| PP3017 | |
| PP3018 | |

TABLE 38-continued
| Compound No. | Structural Formula |
|---|---|
| PP3019 | 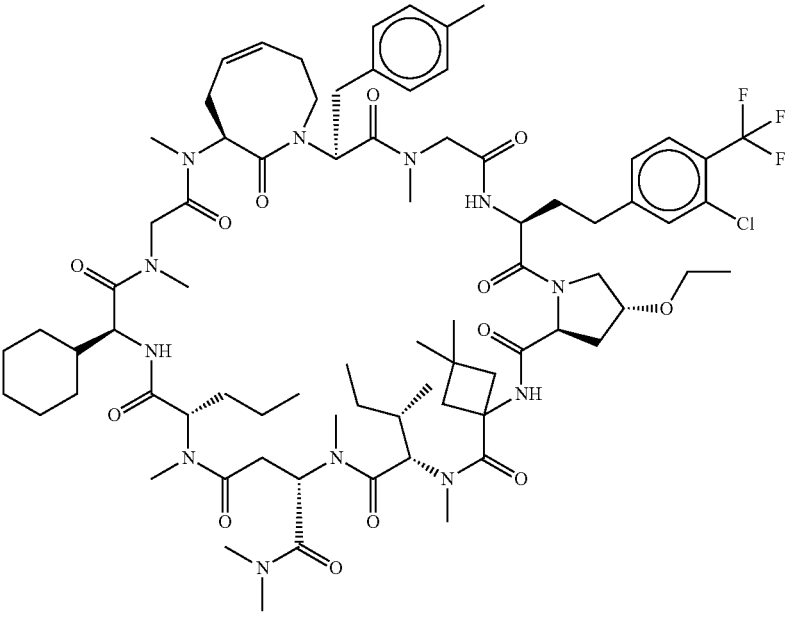 |
| PP3020 | 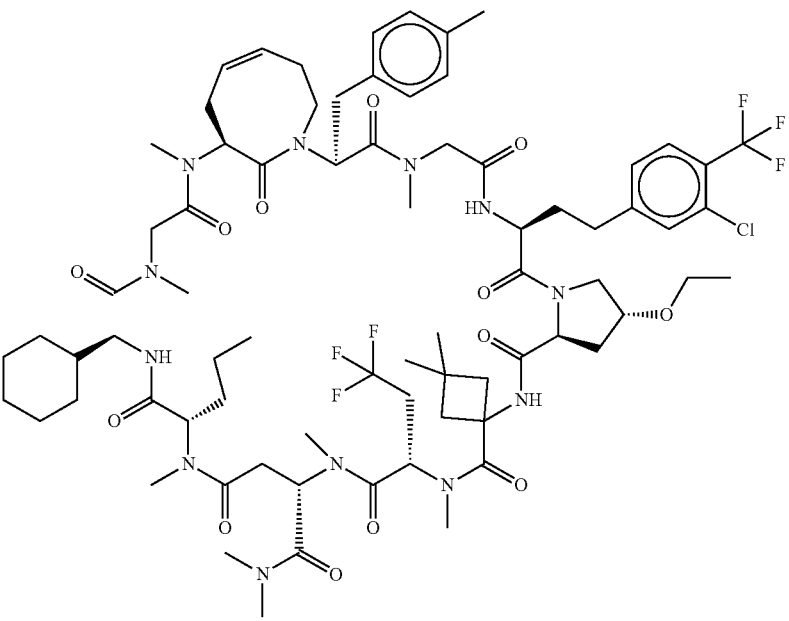 |

TABLE 38-continued

| Compound No. | Structural Formula |
|---|---|
| PP3021 | |
| PP3022 | |

TABLE 38-continued
| Compound No. | Structural Formula |
|---|---|
| PP3023 | 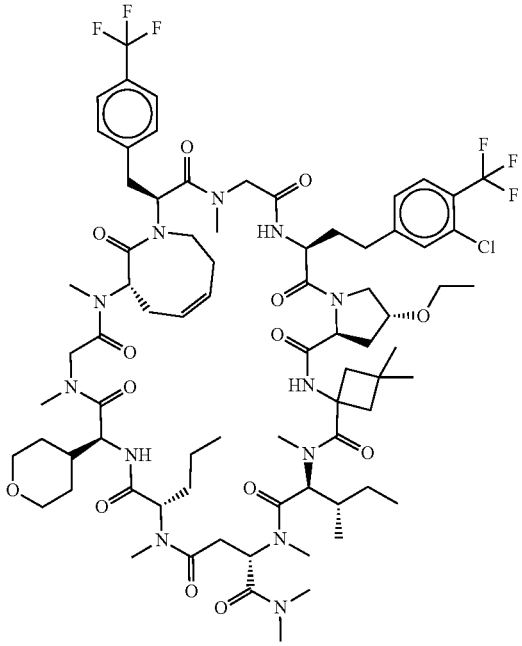 |
| PP3024 | 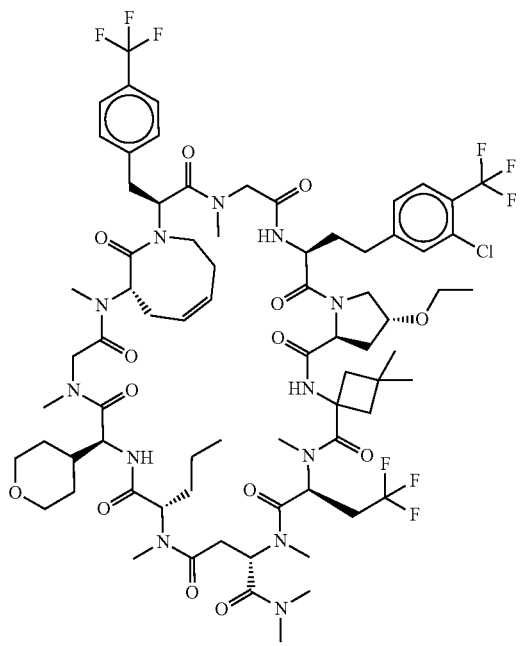 |

TABLE 38-continued

| Compound No. | Structural Formula |
|---|---|
| PP3025 | |
| PP3026 | |

TABLE 38-continued

| Compound No. | Structural Formula |
|---|---|
| PP3027 | |
| PP3028 | |

TABLE 38-continued

| Compound No. | Structural Formula |
|---|---|
| PP3029 | |
| PP3031 | |

TABLE 38-continued
| Compound No. | Structural Formula |
|---|---|
| PP3032 | 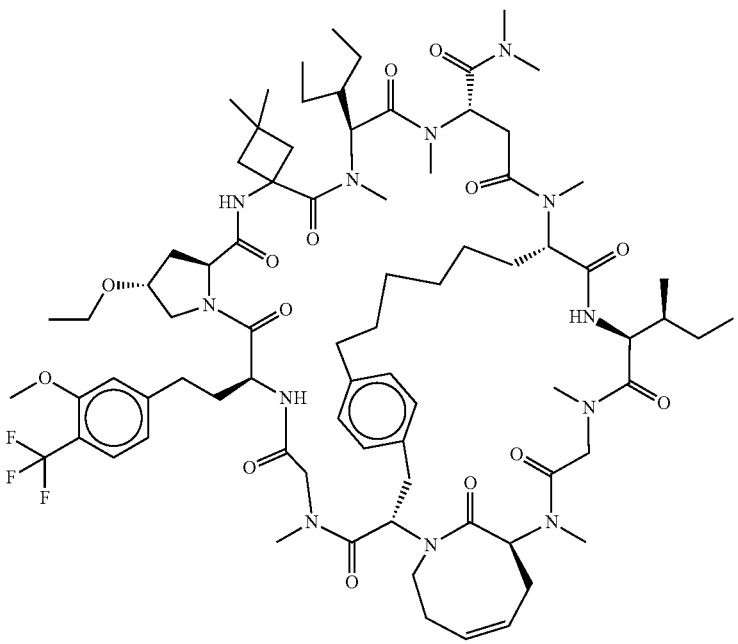 |
| PP3033 | 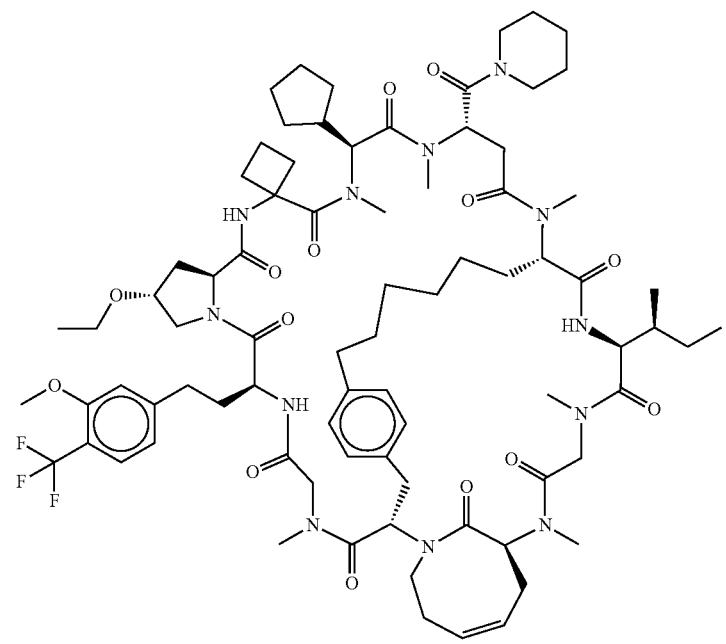 |

TABLE 38-continued
| Compound No. | Structural Formula |
|---|---|
| PP3034 | 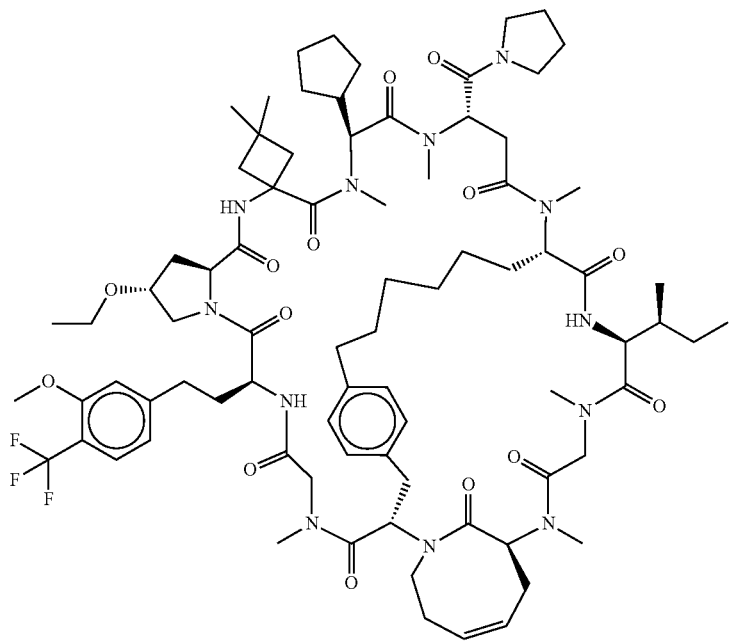 |
| PP3035 | 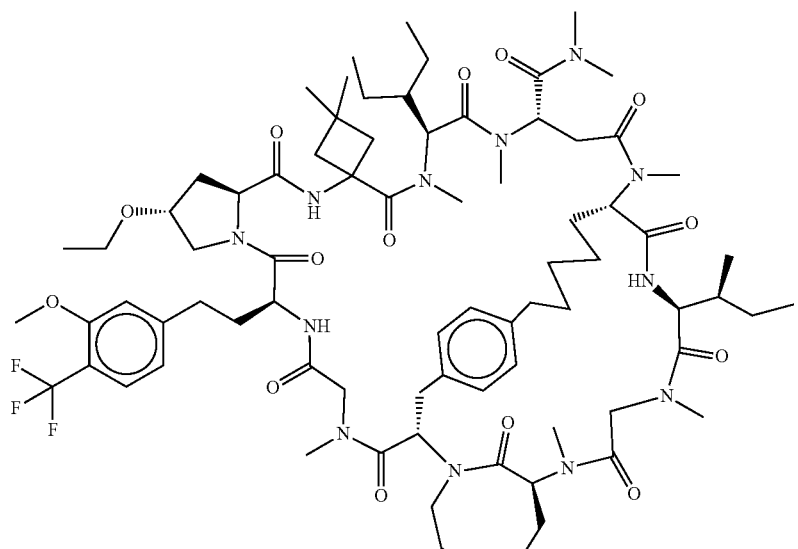 |

TABLE 38-continued

| Compound No. | Structural Formula |
|---|---|
| PP3036 | |
| PP3037 | |

TABLE 38-continued

| Compound No. | Structural Formula |
|---|---|
| PP3038 | |
| PP3039 | |

TABLE 38-continued
| Compound No. | Structural Formula |
|---|---|
| PP3040 | 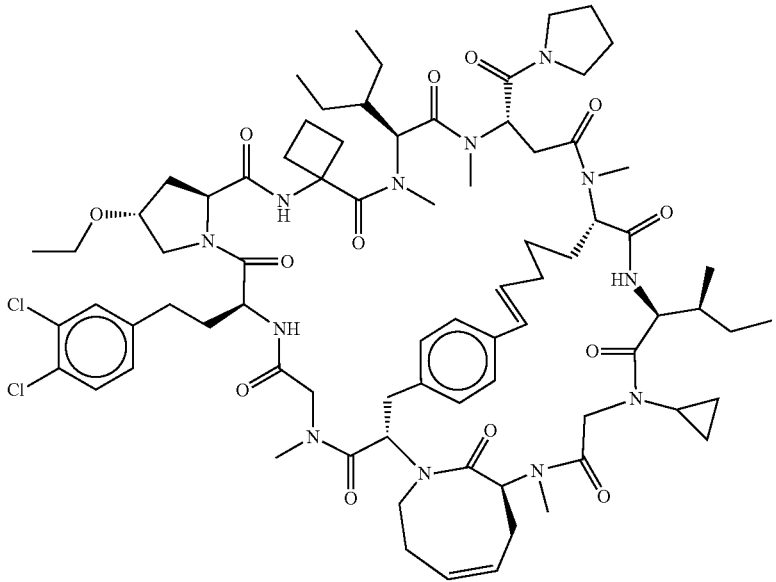 |
| PP3041 | 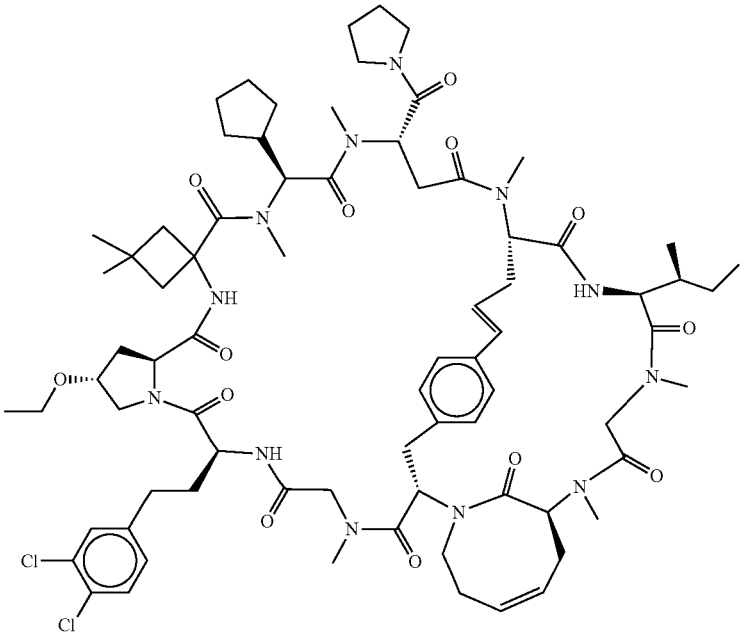 |

TABLE 38-continued
| Compound No. | Structural Formula |
|---|---|
| PP3042 | 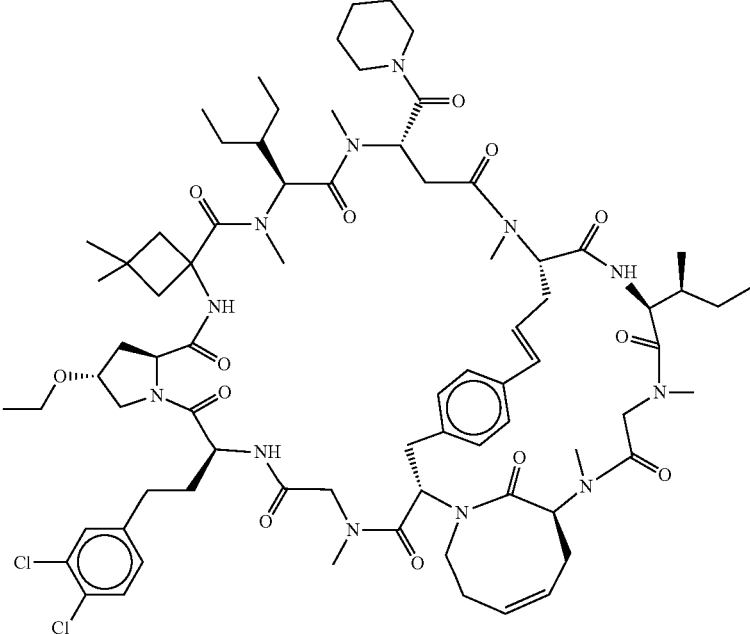 |
| PP3043 | 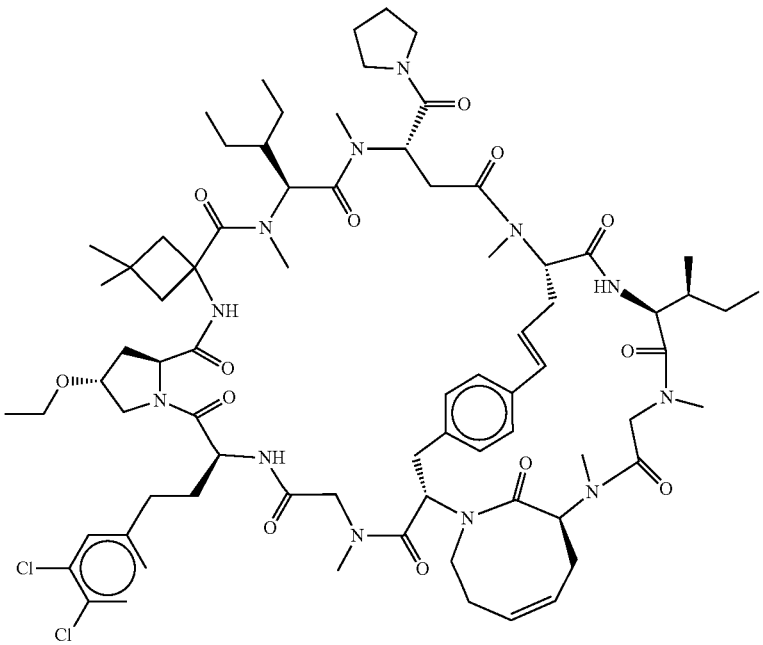 |

TABLE 38-continued

| Compound No. | Structural Formula |
|---|---|
| PP3044 | |
| PP3045 | |

TABLE 38-continued
| Compound No. | Structural Formula |
|---|---|
| PP3046 | 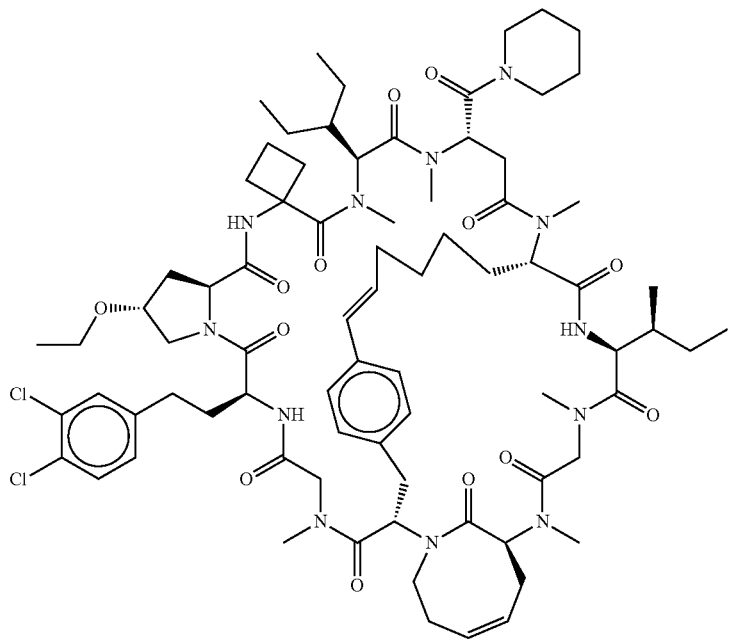 |
| PP3047 | 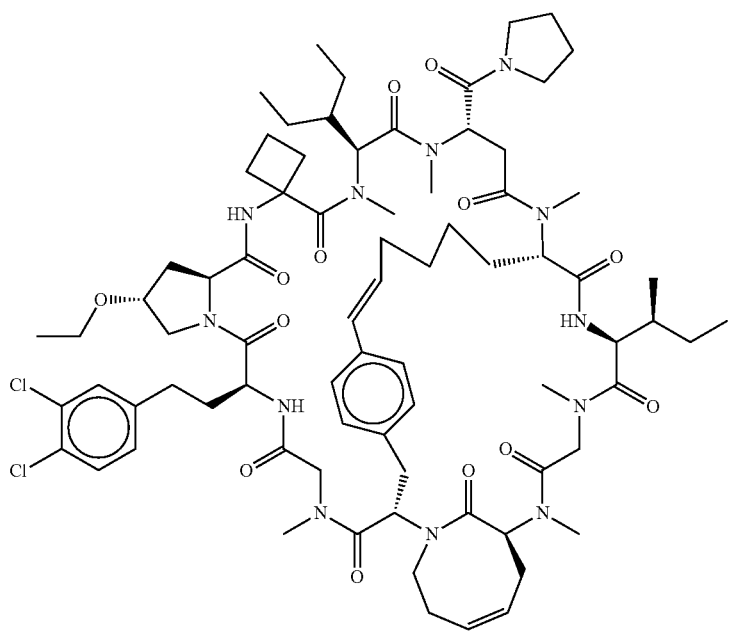 |

TABLE 38-continued

| Compound No. | Structural Formula |
|---|---|
| PP3048 | |
| PP3049 | |

TABLE 38-continued

| Compound No. | Structural Formula |
|---|---|
| PP3050 | |
| PP3051 | |

TABLE 38-continued
| Compound No. | Structural Formula |
| --- | --- |
| PP3052 | 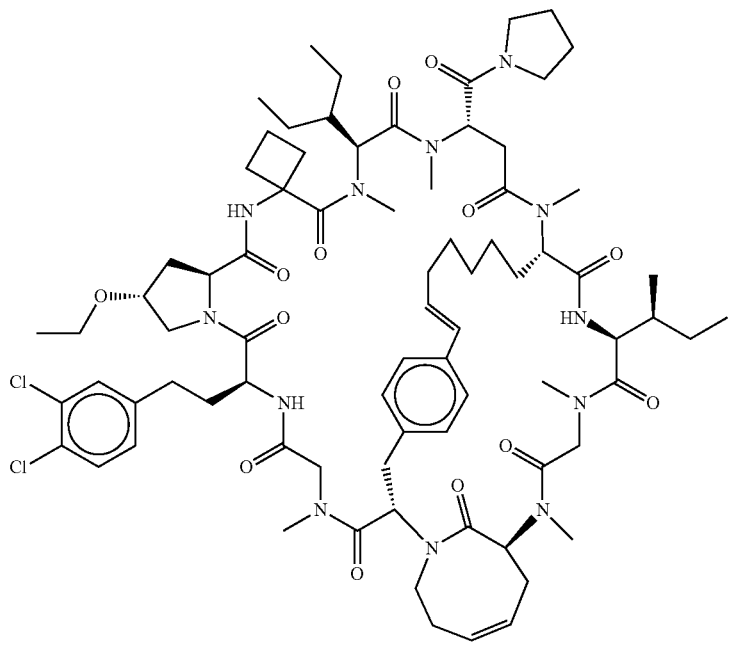 |
| PP3053 | 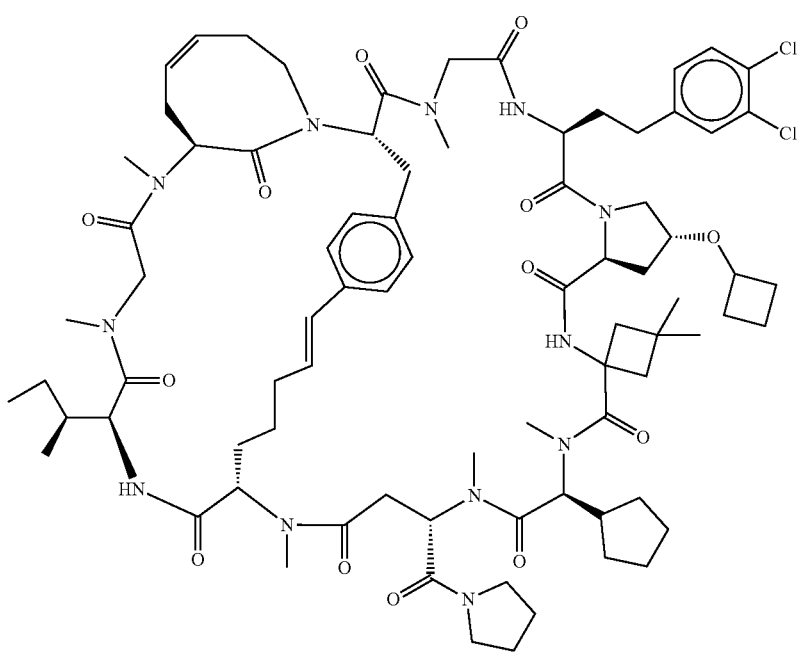 |

TABLE 38-continued
| Compound No. | Structural Formula |
|---|---|
| PP3054 | 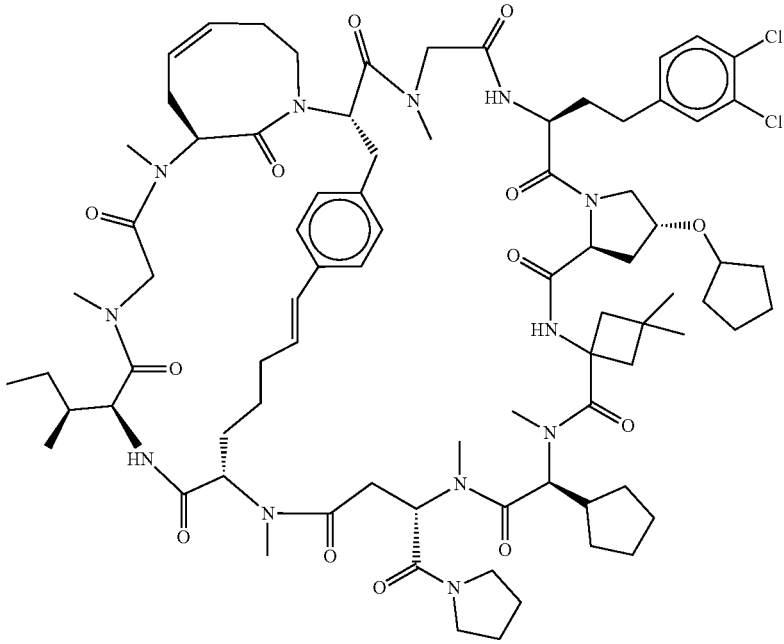 |
| PP3055 | 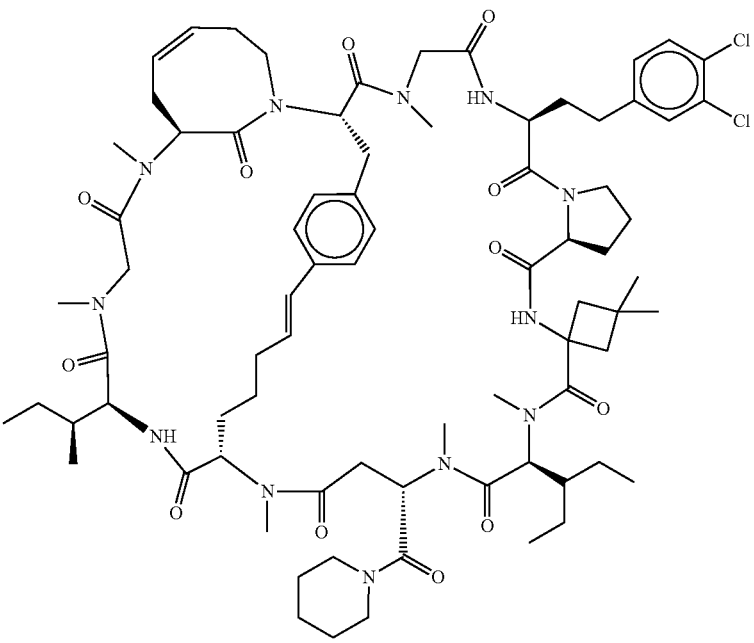 |

TABLE 38-continued
| Compound No. | Structural Formula |
|---|---|
| PP3056 | 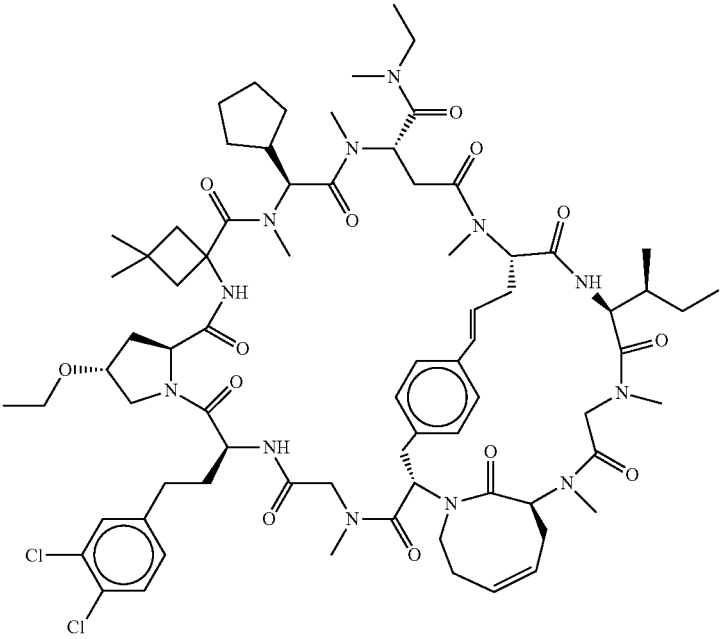 |
| PP3057 | 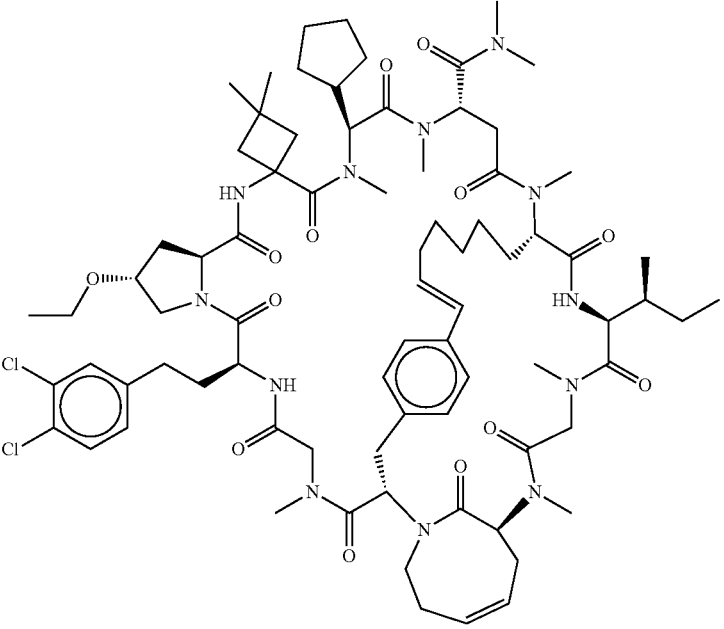 |

TABLE 38-continued
| Compound No. | Structural Formula |
| --- | --- |
| PP3058 | 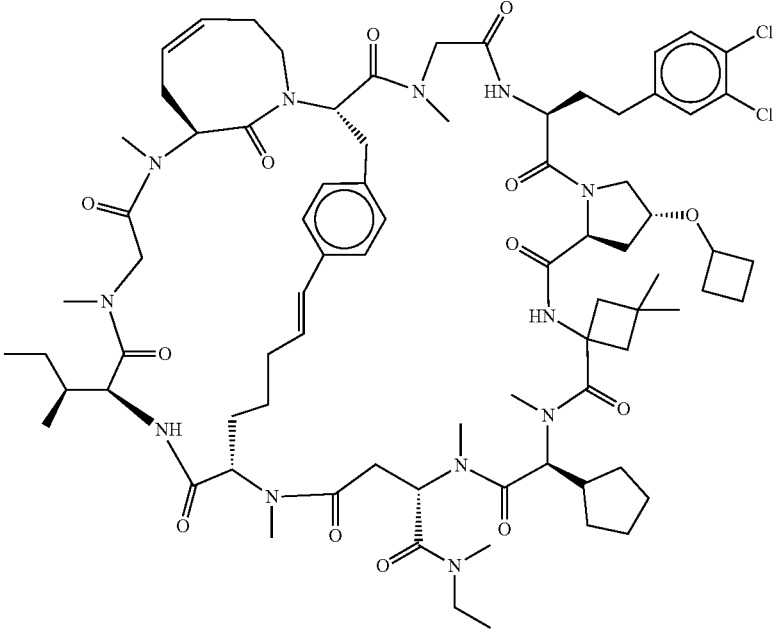 |
| PP3059 | 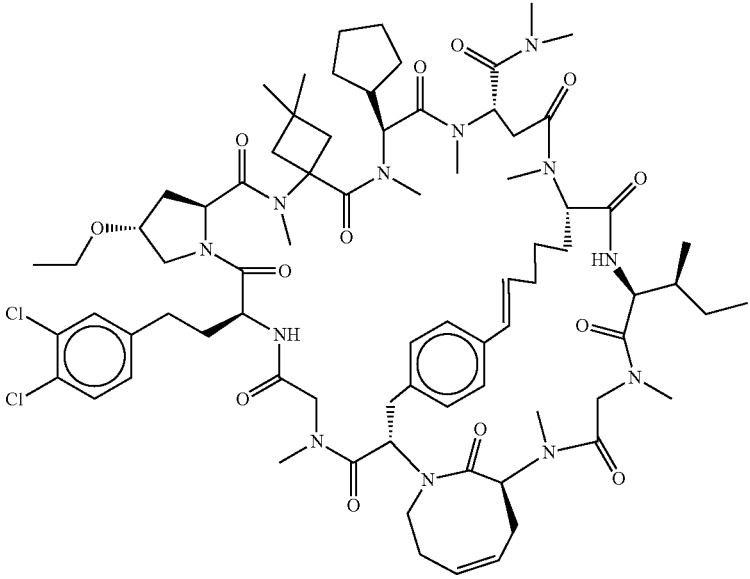 |

TABLE 38-continued

| Compound No. | Structural Formula |
|---|---|
| PP3060 | |
| PP3061 | |

TABLE 38-continued

| Compound No. | Structural Formula |
|---|---|
| PP3062 | |
| PP3063 | |

| Compound No. | Structural Formula |
|---|---|
| PP3064 | |
| PP3065 | |

TABLE 38-continued

| Compound No. | Structural Formula |
|---|---|
| PP3066 | |
| PP3067 | |

TABLE 38-continued
| Compound No. | Structural Formula |
|---|---|
| PP3068 | 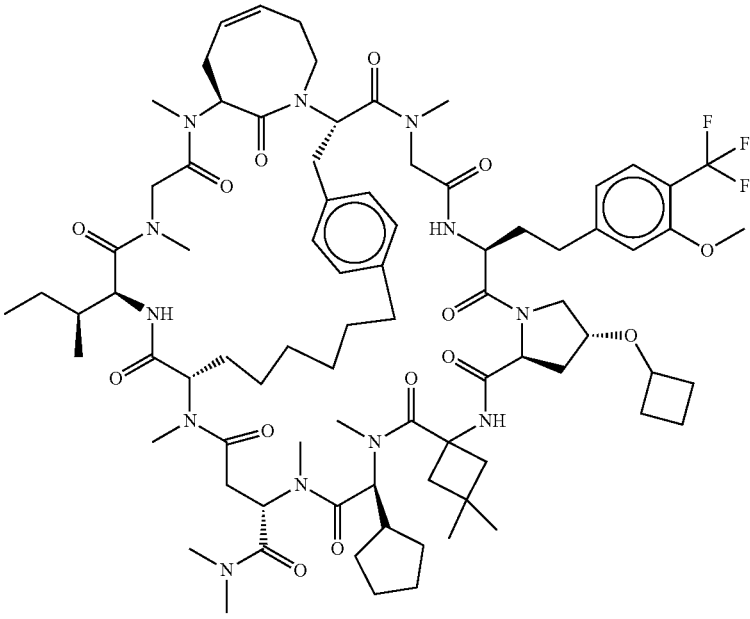 |
| PP3069 | 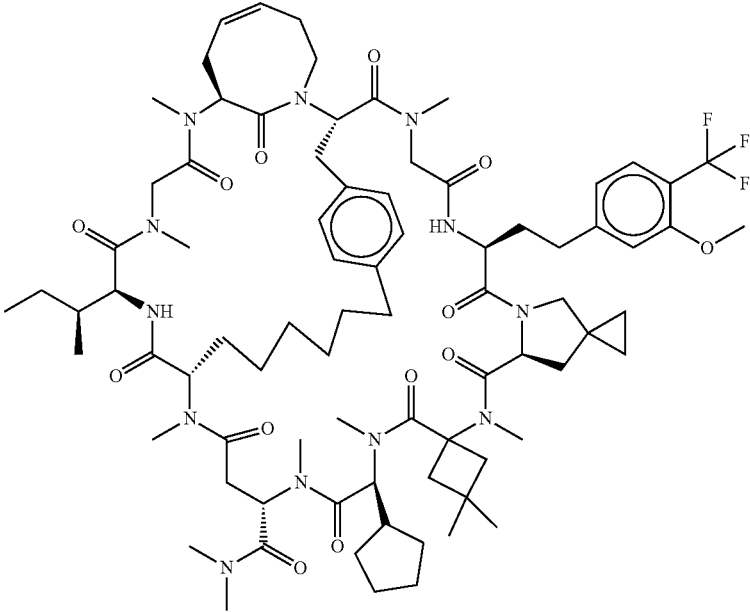 |

TABLE 38-continued

| Compound No. | Structural Formula |
| --- | --- |
| PP3071 | |
| PP3072 | |

TABLE 38-continued
| Compound No. | Structural Formula |
|---|---|
| PP3073 | 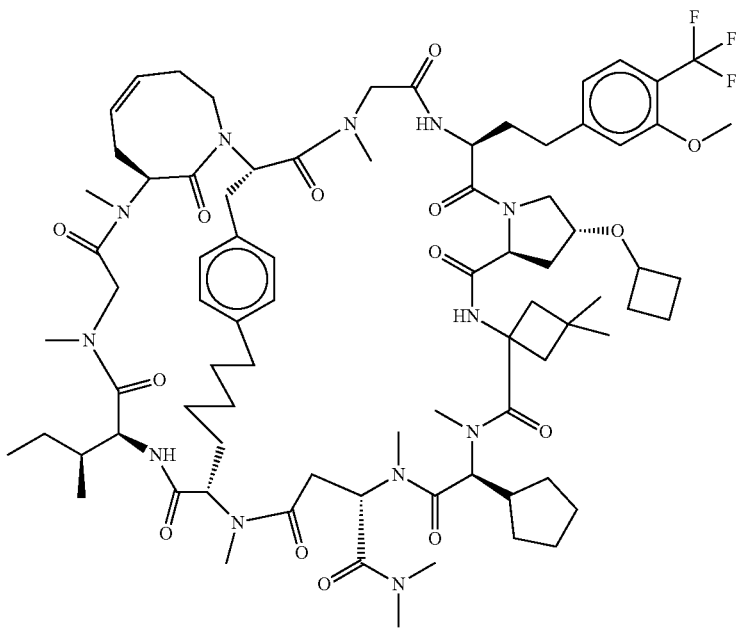 |
| PP3074 | 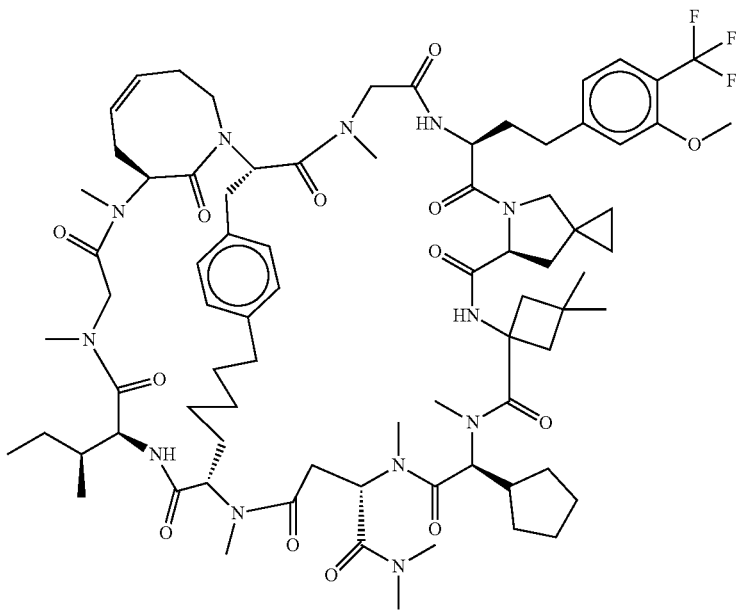 |

TABLE 38-continued
| Compound No. | Structural Formula |
|---|---|
| PP3076 | 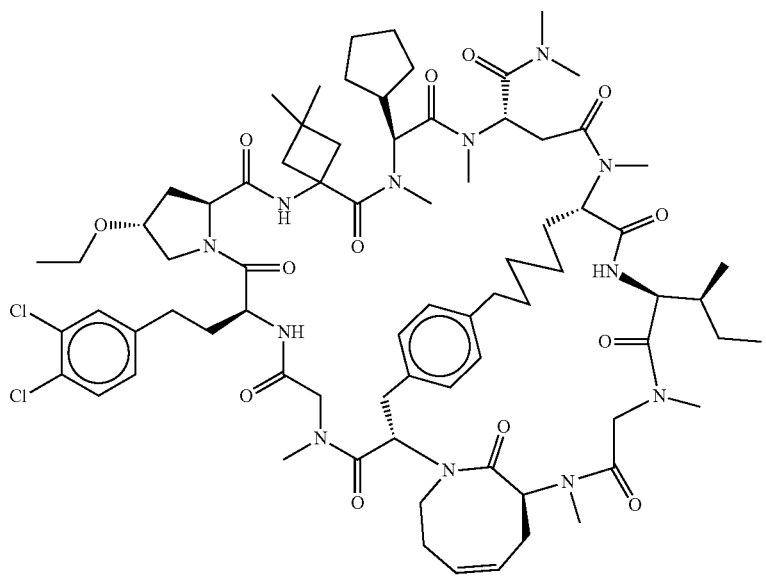 |
| PP3077 | 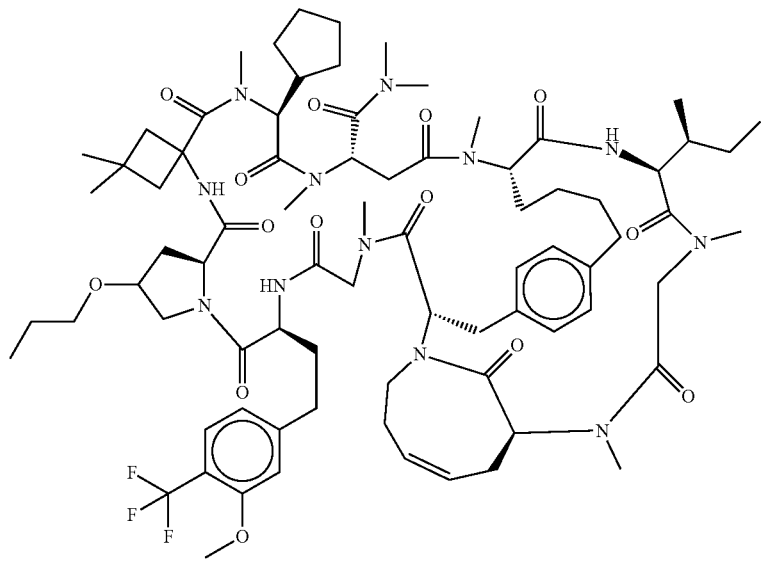 |

TABLE 38-continued

| Compound No. | Structural Formula |
| --- | --- |
| PP3078 | |
| PP3079 | |

TABLE 38-continued
| Compound No. | Structural Formula |
|---|---|
| PP3080 | 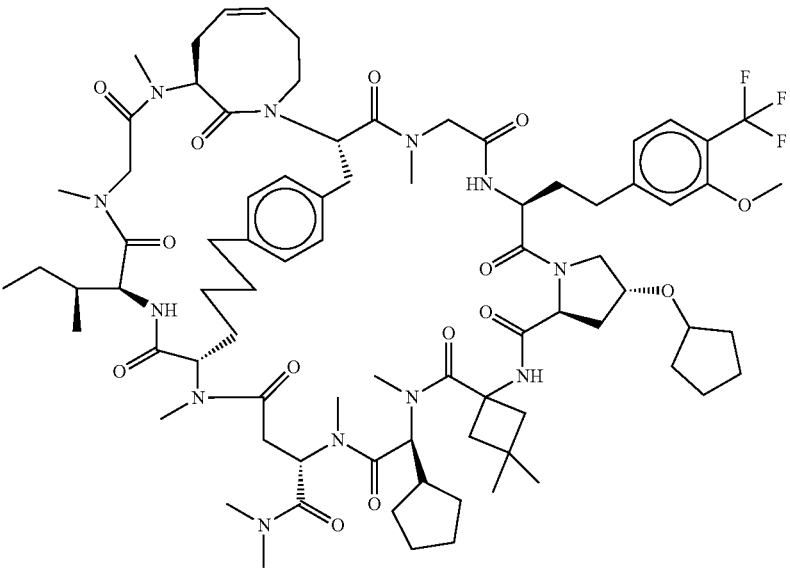 |
| PP3083 | 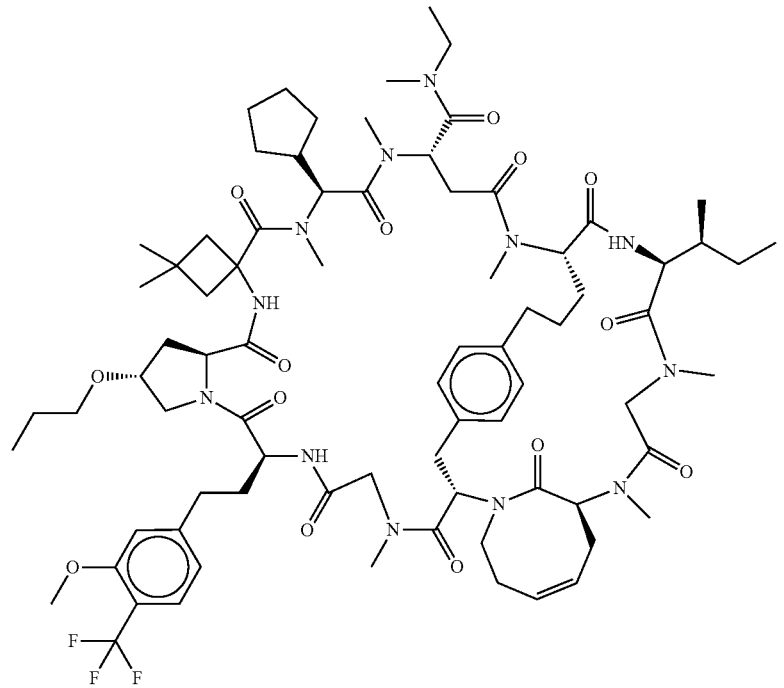 |

TABLE 38-continued

| Compound No. | Structural Formula |
|---|---|
| PP3084 | |
| PP3085 | |

TABLE 38-continued

| Compound No. | Structural Formula |
|---|---|
| PP3086 | |
| PP3087 | |

TABLE 38-continued

| Compound No. | Structural Formula |
|---|---|
| PP3088 | |
| PP3089 | |

TABLE 38-continued
| Compound No. | Structural Formula |
|---|---|
| PP3090 | 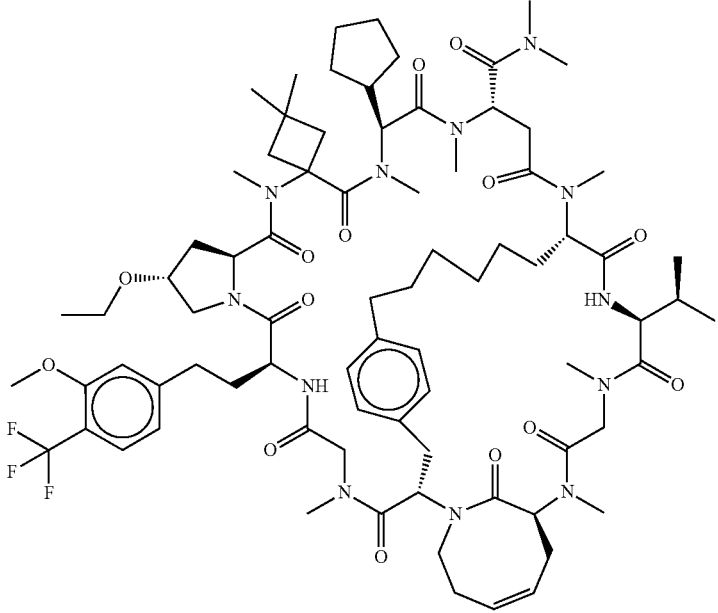 |
| PP3091 | 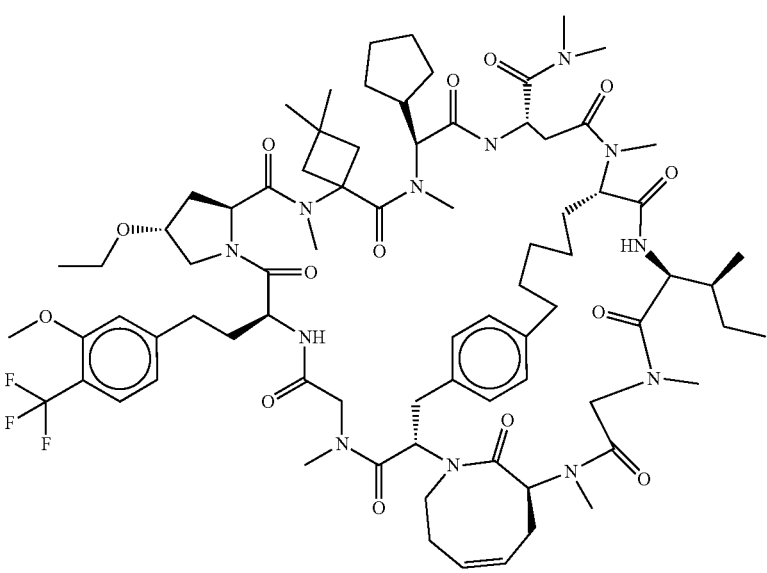 |

TABLE 38-continued
| Compound No. | Structural Formula |
|---|---|
| PP3092 | 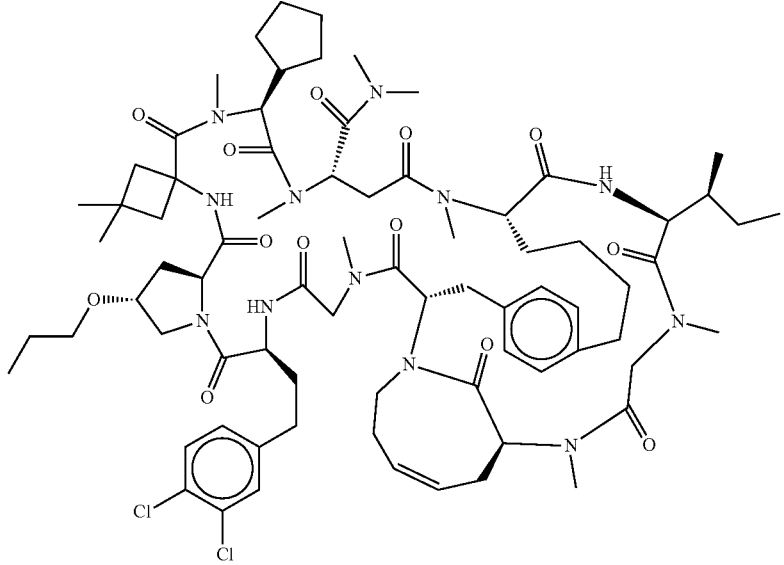 |
| PP3093 | 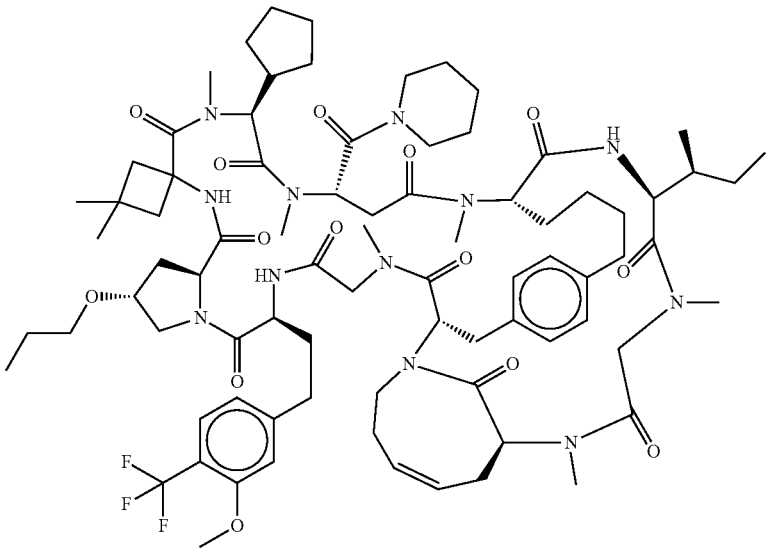 |

TABLE 38-continued
| Compound No. | Structural Formula |
|---|---|
| PP3094 | 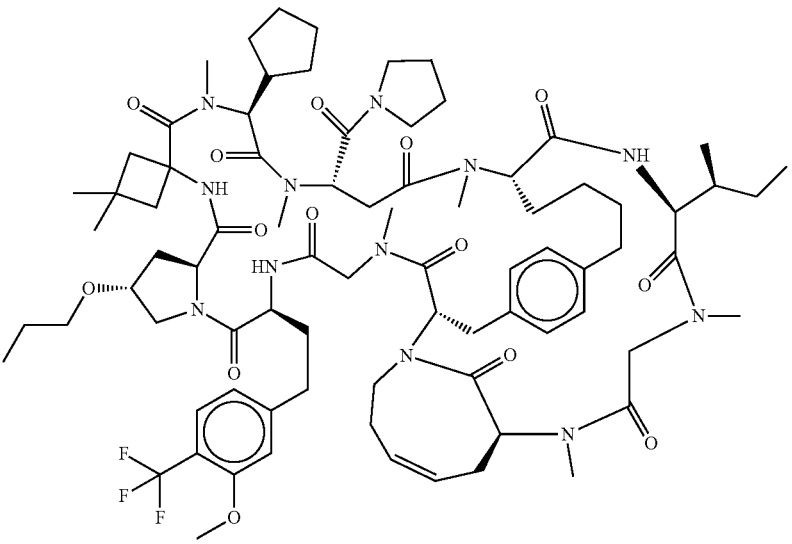 |
| PP3095 | 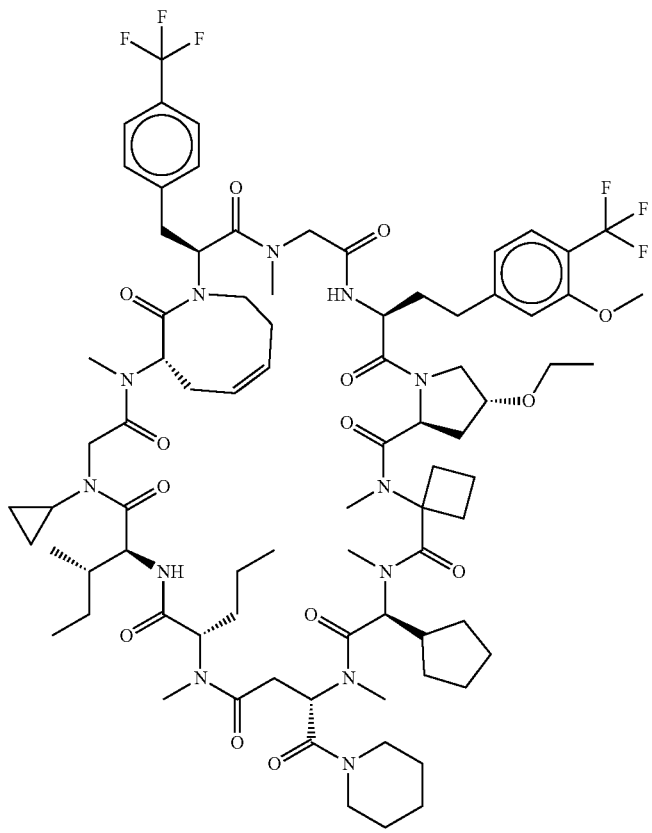 |

TABLE 38-continued

| Compound No. | Structural Formula |
|---|---|
| PP3096 | |
| PP3097 | |

TABLE 38-continued

| Compound No. | Structural Formula |
|---|---|
| PP3098 | |
| PP3099 | |

TABLE 38-continued
| Compound No. | Structural Formula |
|---|---|
| PP3100 | 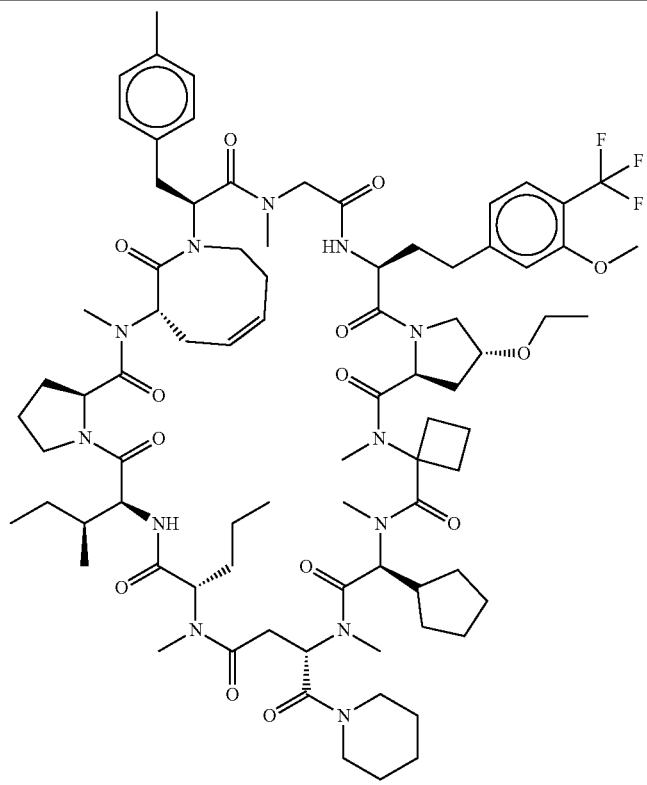 |
| PP3101 | 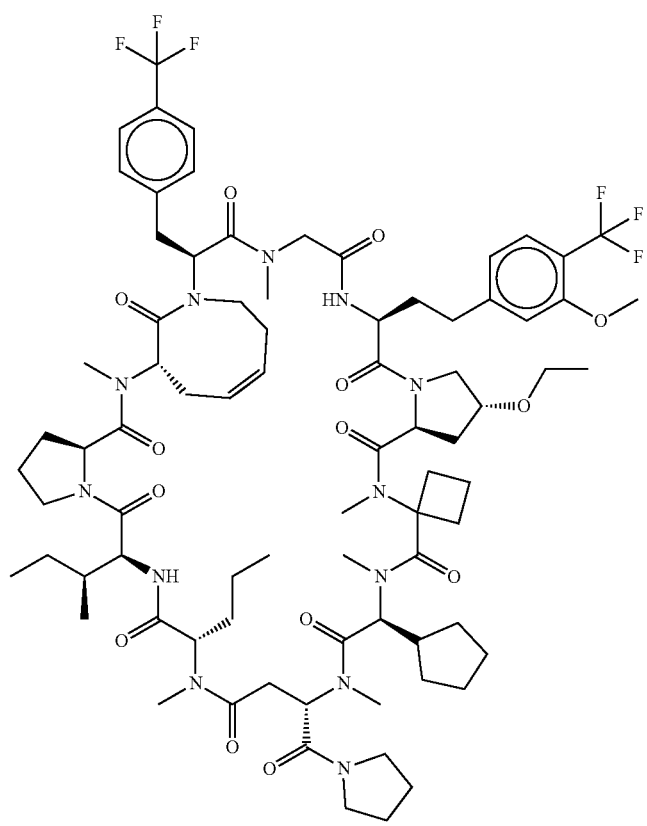 |

TABLE 38-continued
| Compound No. | Structural Formula |
|---|---|
| PP3102 | 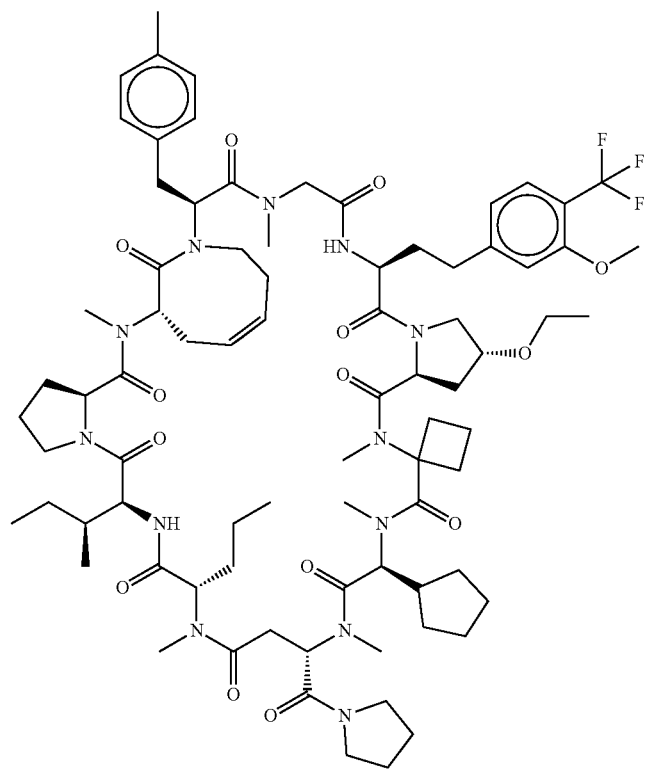 |
| PP3103 | 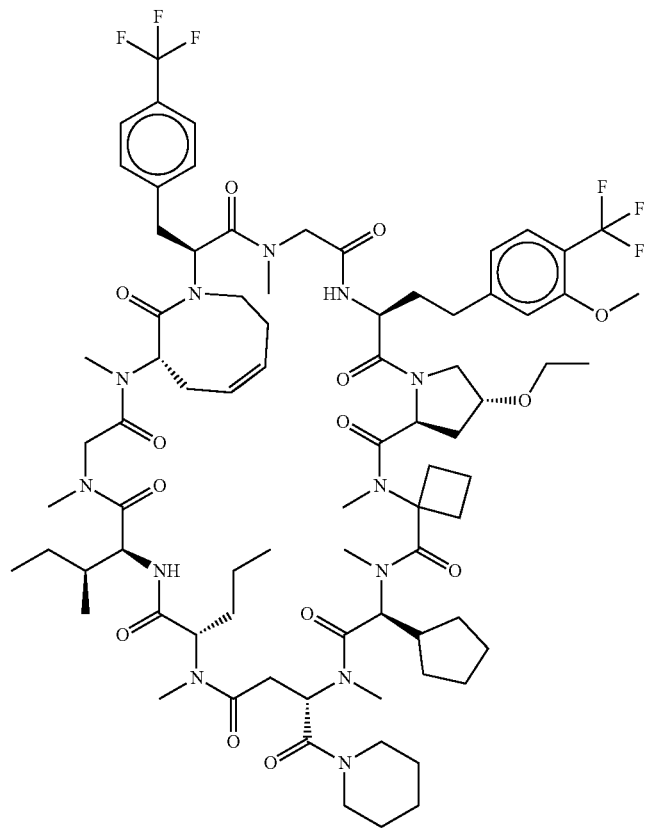 |

TABLE 38-continued
| Compound No. | Structural Formula |
|---|---|
| PP3104 | 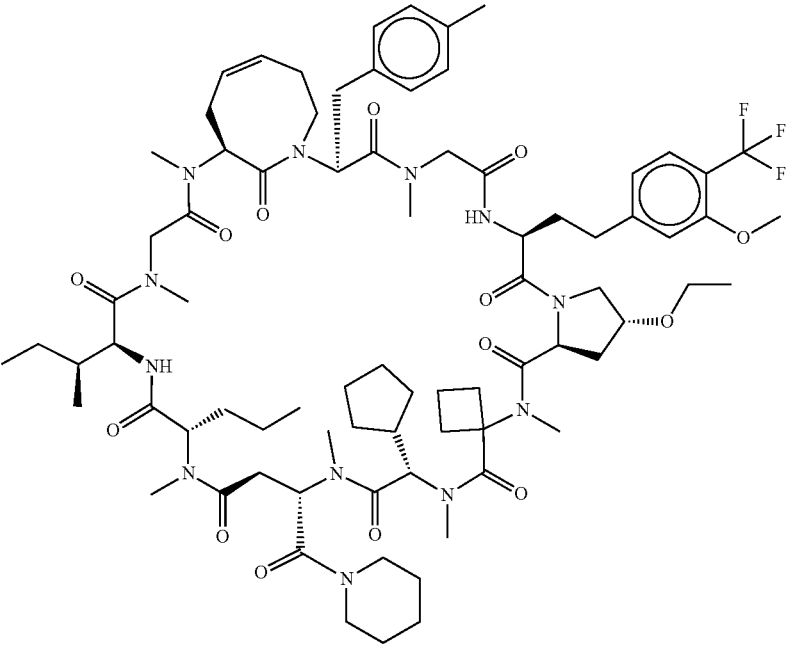 |
| PP3105 | 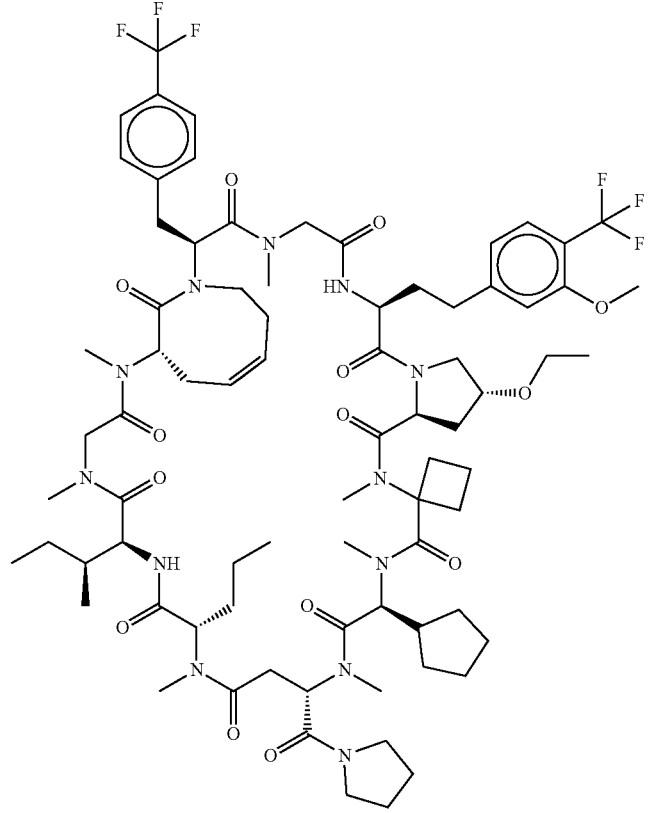 |

| Compound No. | Structural Formula |
|---|---|
| PP3106 | |
| PP3108 | |

TABLE 38-continued

| Compound No. | Structural Formula |
|---|---|
| PP3109 | |
| PP3110 | |

TABLE 38-continued

| Compound No. | Structural Formula |
| --- | --- |
| PP3111 | |
| PP3112 | |

TABLE 38-continued

| Compound No. | Structural Formula |
|---|---|
| PP3113 | |
| PP3114 | |

TABLE 38-continued
| Compound No. | Structural Formula |
|---|---|
| PP3115 | 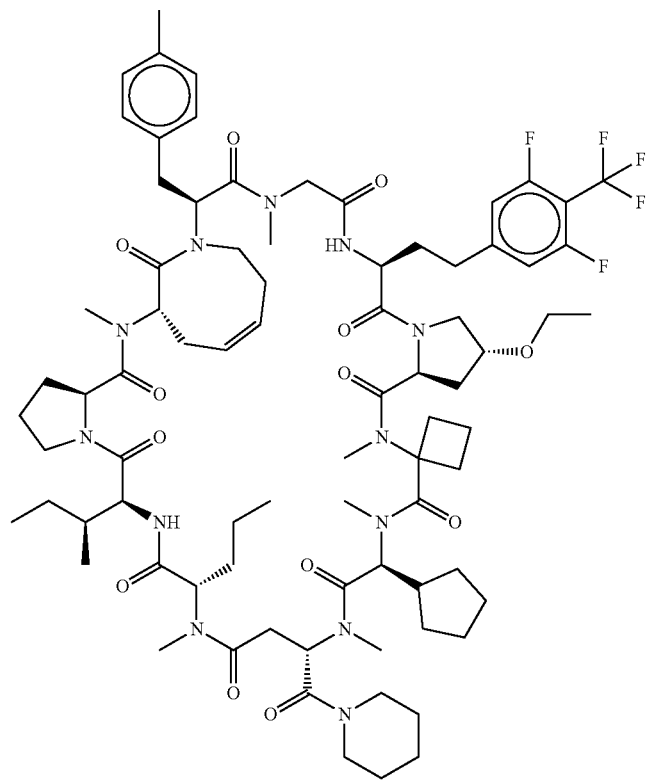 |
| PP3116 | 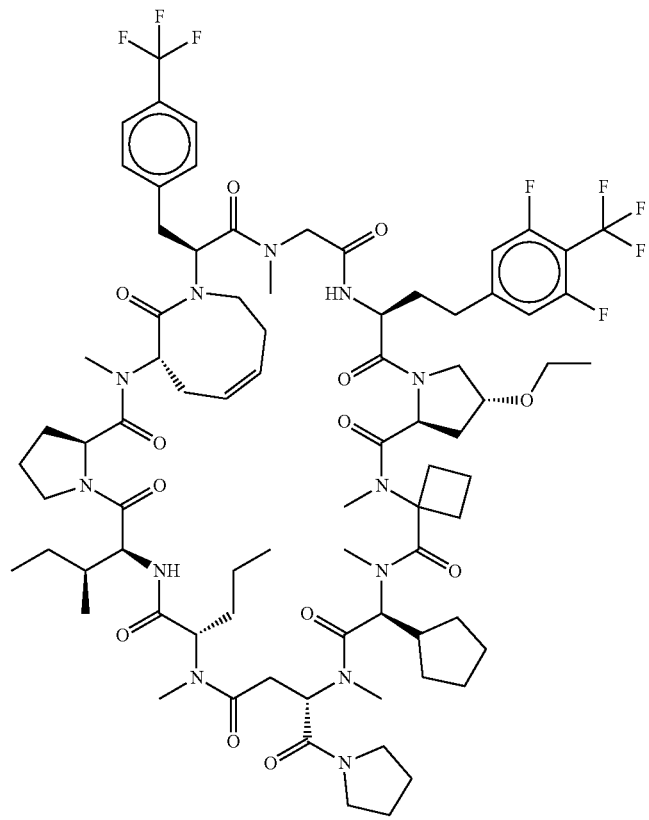 |

TABLE 38-continued
| Compound No. | Structural Formula |
|---|---|
| PP3117 | 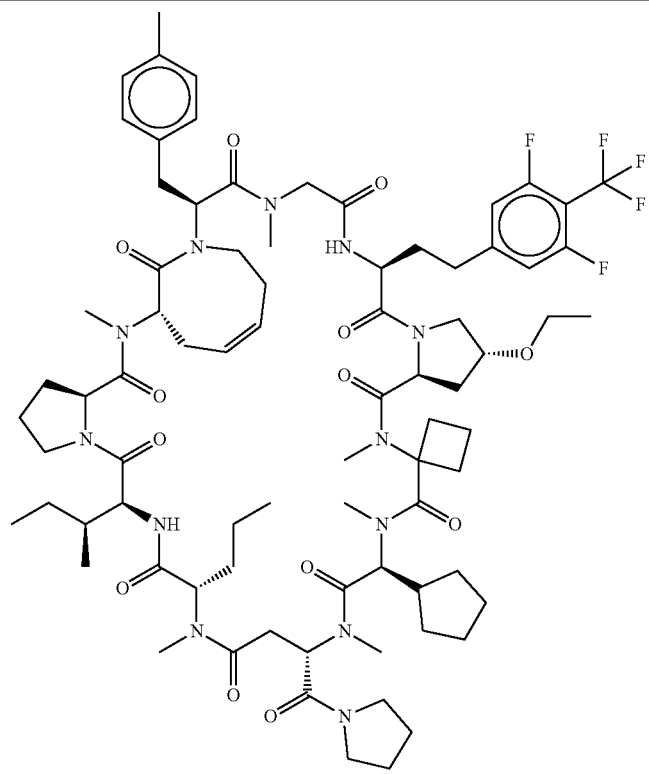 |
| PP3118 | 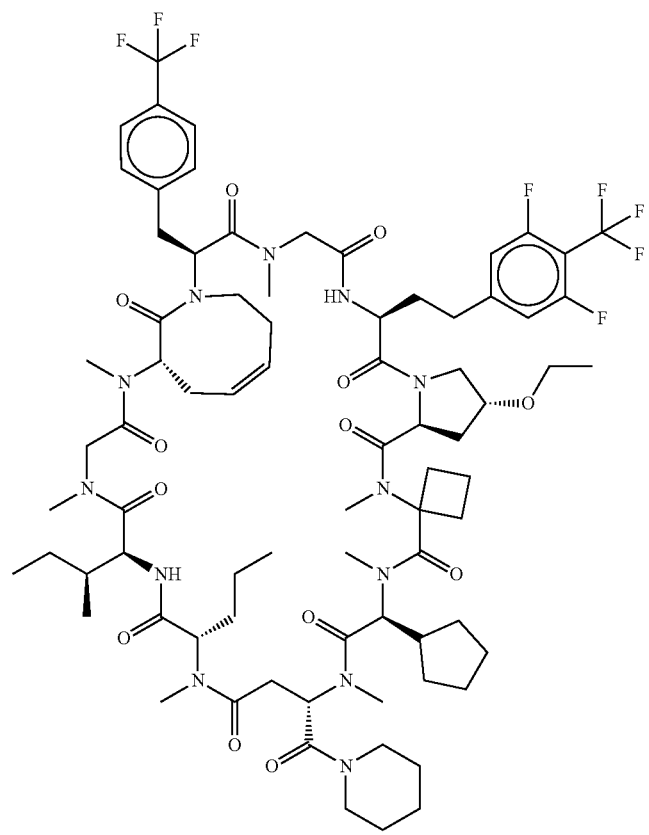 |

TABLE 38-continued

| Compound No. | Structural Formula |
|---|---|
| PP3119 | |
| PP3120 | |

TABLE 38-continued

| Compound No. | Structural Formula |
|---|---|
| PP3121 | 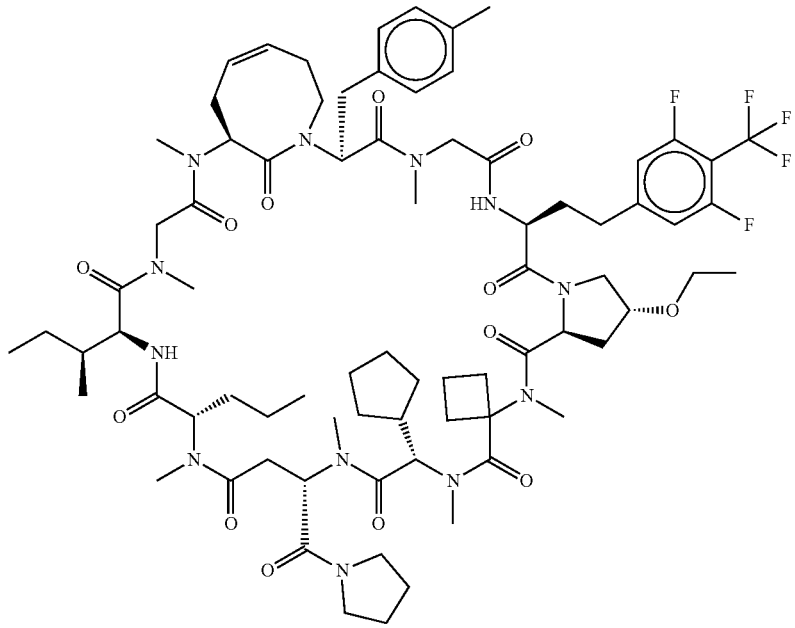 |

INDUSTRIAL APPLICABILITY

The present invention provides cyclic compounds that selectively inhibit KRAS.

```
                        SEQUENCE LISTING

Sequence total quantity: 3
SEQ ID NO: 1            moltype = AA  length = 189
FEATURE                 Location/Qualifiers
source                  1..189
                        mol_type = protein
                        organism = Homo sapiens
SEQUENCE: 1
MTEYKLVVVG AGGVGKSALT IQLIQNHFVD EYDPTIEDSY RKQVVIDGET CLLDILDTAG   60
QEEYSAMRDQ YMRTGEGFLC VFAINNSKSF ADINLYREQI KRVKDSDDVP MVLVGNKCDL  120
PTRTVDTKQA HELAKSYGIP FIETSAKTRQ GVEDAFYTLV REIRQYRMKK LNSSDDGTQG  180
CMGLPCVVM                                                          189

SEQ ID NO: 2            moltype = AA  length = 189
FEATURE                 Location/Qualifiers
source                  1..189
                        mol_type = protein
                        organism = Homo sapiens
SEQUENCE: 2
MTEYKLVVVG AGGVGKSALT IQLIQNHFVD EYDPTIEDSY RKQVVIDGET CLLDILDTAG   60
QEEYSAMRDQ YMRTGEGFLC VFAINNTKSF EDIHQYREQI KRVKDSDDVP MVLVGNKCDL  120
AARTVESRQA QDLARSYGIP YIETSAKTRQ GVEDAFYTLV REIRQHKLRK LNPPDESGPG  180
CMSCKCVLS                                                          189

SEQ ID NO: 3            moltype = AA  length = 189
FEATURE                 Location/Qualifiers
source                  1..189
                        mol_type = protein
                        organism = Homo sapiens
SEQUENCE: 3
MTEYKLVVVG AGGVGKSALT IQLIQNHFVD EYDPTIEDSY RKQVVIDGET CLLDILDTAG   60
QEEYSAMRDQ YMRTGEGFLC VFAINNTKSF EDIHHYREQI KRVKDSEDVP MVLVGNKCDL  120
PSRTVDTKQA QDLARSYGIP FIETSAKTRQ RVEDAFYTLV REIRQYRLKK ISKEEKTPGC  180
VKIKKCIIM                                                          189
```

The invention claimed is:

1. A compound, which is (1S,4S,10S,13S,17S,20S,26S,28R,32S,38S,42Z)-20-cyclopentyl-28-ethoxy-32-[2-[3-methoxy-4-(trifluoromethyl)phenyl]ethyl]-N,N,2,14,18,21,24,36-octamethyl-10-[(1S)-1-methylpropyl]-3,9,12,15,19,22,25,31,34,37,45-undecaoxo-13-propyl-38-[[4-(trifluoromethyl)phenyl]methyl]spiro[2,8,11,14,18,21,24,30,33,36,39-undecazatetracyclo [37.5.1.0$^{4,8}$.0$^{26,30}$] pentatetracont-42-ene-23,1'-cyclobutane]-17-carboxamide.

2. A pharmaceutical composition comprising the compound of claim 1.

3. A method of inhibiting KRAS in a subject, the method comprising administering to the subject a pharmaceutical composition comprising an effective amount of the compound of claim 1.

4. A method of treating or preventing cancer in a subject, the method comprising administering to the subject a pharmaceutical composition comprising an effective amount of the compound of claim 1.

5. The method of claim 4, wherein the cancer is lung cancer.

6. The method of claim 4, wherein the subject is human.

7. A solvate of (1S,4S,10S,13S,17S,20S,26S,28R,32S,38S,42Z)-20-cyclopentyl-28-ethoxy-32-[2-[3-methoxy-4-(trifluoromethyl)phenyl]ethyl]-N,N,2,14,18,21,24,36-octamethyl-10-[(1S)-1-methylpropyl]-3,9,12,15,19,22,25,31,34,37,45-undecaoxo-13-propyl-38-[[4-(trifluoromethyl)phenyl]methyl]spiro[2,8,11,14,18,21,24,30,33,36,39-undecazatetracyclo [37.5.1.0$^{4,8}$.0$^{26,30}$] pentatetracont-42-ene-23,1'-cyclobutane]-17-carboxamide.

8. A pharmaceutical composition comprising the solvate of claim 7.

9. A method of selectively inhibiting KRAS in a subject, the method comprising administering to the subject a pharmaceutical composition comprising an effective amount of the solvate of claim 7.

10. A method of treating or preventing cancer in a subject, the method comprising administering to the subject a pharmaceutical composition comprising an effective amount of the solvate of claim 7.

11. The method of claim 10, wherein the cancer is lung cancer.

12. The method of claim 10, wherein the subject is human.

13. The solvate according to claim 7, which is a hydrate.

14. A pharmaceutical composition comprising the solvate of claim 13.

15. A method of selectively inhibiting KRAS in a subject, the method comprising administering to the subject a pharmaceutical composition comprising an effective amount of the solvate of claim 13.

16. A method of treating or preventing cancer in a subject, the method comprising administering to the subject a pharmaceutical composition comprising an effective amount of the solvate of claim 13.

17. The method of claim 16, wherein the cancer is lung cancer.

18. The method of claim 16, wherein the subject is human.

19. A salt of (1S,4S,10S,13S,17S,20S,26S,28R,32S,38S,42Z)-20-cyclopentyl-28-ethoxy-32-[2-[3-methoxy-4-(trifluoromethyl)phenyl]ethyl]-N,N,2,14,18,21,24,36-octamethyl-10-[(1S)-1-methylpropyl]-3,9,12,15,19,22,25,31,34,37,45-undecaoxo-13-propyl-38-[[4-(trifluoromethyl)phenyl]methyl]spiro[2,8,11,14,18,21,24,30,33,36,39-undecazatetracyclo [37.5.1.0$^{4,8}$.0$^{26,30}$] pentatetracont-42-ene-23,1'-cyclobutane]-17-carboxamide, or a solvate thereof.

20. A pharmaceutical composition comprising the salt of claim 19, or a solvate thereof.

21. A method of inhibiting KRAS in a subject, the method comprising administering to the subject a pharmaceutical composition comprising an effective amount of the salt of claim 19, or a solvate thereof.

22. A method of treating or preventing cancer in a subject, the method comprising administering to the subject a pharmaceutical composition comprising an effective amount of the salt of claim 19, or a solvate thereof.

23. The method of claim 22, wherein the cancer is lung cancer.

24. The method of claim 22, wherein the subject is human.

* * * * *